(12) United States Patent
Aertgeerts et al.

(10) Patent No.: US 7,344,852 B1
(45) Date of Patent: Mar. 18, 2008

(54) CRYSTALLIZATION OF DIPEPTIDYL PEPTIDASE IV (DPPIV)

(75) Inventors: Kathleen Aertgeerts, San Diego, CA (US); Ciaran N. Cronin, San Diego, CA (US); David J. Hosfield, San Diego, CA (US); Mark W. Knuth, El Cajon, CA (US); Duncan E. McRee, San Diego, CA (US); Sridhar Prasad, San Diego, CA (US); Bi Ching Sang, San Diego, CA (US); Robert J. Skene, San Diego, CA (US); Robert A. Wijnands, Vista, CA (US); Sheng Ye, Allen, TX (US)

(73) Assignee: Takeda San Diego, Inc., San Diego, CA (US)

( * ) Notice: Subject to any disclaimer, the term of this patent is extended or adjusted under 35 U.S.C. 154(b) by 360 days.

(21) Appl. No.: 10/659,055

(22) Filed: Sep. 9, 2003

Related U.S. Application Data

(60) Provisional application No. 60/409,206, filed on Sep. 9, 2002.

(51) Int. Cl.
*C12Q 1/37* (2006.01)
*C12N 9/48* (2006.01)
(52) U.S. Cl. .......................................... 435/24; 435/12
(58) Field of Classification Search .................... None
See application file for complete search history.

(56) References Cited

U.S. PATENT DOCUMENTS

2005/0260732 A1* 11/2005 Hiramatsu et al. .......... 435/226

OTHER PUBLICATIONS

Wiencek et al. New strategies for protein crystal growth. Ann. Rev. Biomed. Eng. 1999, 1, 505-534.*
Gilliland et al. Crystallization of biological molecules for X-ray diffraction studies. Current Opinion in Structure Biology 1996, 6, 595-603.*
Ke et al. Crystallization of RNA and RNA-protein complexes. Methods 34, 2004, 408-414.*

* cited by examiner

*Primary Examiner*—Nashaat T. Nashed
(74) *Attorney, Agent, or Firm*—David J. Weitz

(57) ABSTRACT

Provided are crystals relating to DPPIV and its various uses.

12 Claims, 554 Drawing Sheets

FIGURE 1

Amino acid sequence for full-length human wild type DPPIV [SEQ ID NO: 1]

(Residues 39-766 are underlined)

```
MKTPWKVLLG LLGAAALVTI ITVPVVLLNK GTDDATADSR KTYTLTDYLK NTYRLKLYSL    60
RWISDHEYLY KQENNILVFN AEYGNSSVFL ENSTFDEFGH SINDYSISPD GQFILLEYNY   120
VKQWRHSYTA SYDIYDLNKR QLITEERIPN NTQWVTWSPV GHKLAYVWNN DIYVKIEPNL   180
PSYRITWTGK EDIIYNGITD WVYEEEVFSA YSALWWSPNG TFLAYAQFND TEVPLIEYSF   240
YSDESLQYPK TVRVPYPKAG AVNPTVKFFV VNTDSLSSVT NATSIQITAP ASMLIGDHYL   300
CDVTWATQER ISLQWLRRIQ NYSVMDICDY DESSGRWNCL VARQHIEMST TGWVGRFRPS   360
EPHFTLDGNS FYKIISNEEG YRHICYFQID KKDCTFITKG TWEVIGIEAL TSDYLYYISN   420
EYKGMPGGRN LYKIQLSDYT KVTCLSCELN PERCQYYSVS FSKEAKYYQL RCSGPGLPLY   480
TLHSSVNDKG LRVLEDNSAL DKMLQNVQMP SKKLDFIILN ETKFWYQMIL PPHFDKSKKY   540
PLLLDVYAGP CSQKADTVFR LNWATYLAST ENIIVASFDG RGSGYQGDKI MHAINRRLGT   600
FEVEDQIEAA RQFSKMGFVD NKRIAIWGWS YGGYVTSMVL GSGSGVFKCG IAVAPVSRWE   660
YYDSVYTERY MGLPTPEDNL DHYRNSTVMS RAENFKQVEY LLIHGTADDN VHFQQSAQIS   720
KALVDVGVDF QAMWYTDEDH GIASSTAHQH IYTHMSHFIK QCFSLP                  766
```

Amino acid sequence for residues 39-766 of DPPIV with a

N-terminal 6x-histidine tag [SEQ ID NO: 3]

(part of a gp67 signal sequence and a 6x-histidine tag is underlined)

```
ADPGGSHHHH HHSRKTYTLT DYLKNTYRLK LYSLRWISDH EYLYKQENNI LVFNAEYGNS    60
SVFLENSTFD EFGHSINDYS ISPDGQFILL EYNYVKQWRH SYTASYDIYD LNKRQLITEE   120
RIPNNTQWVT WSPVGHKLAY VWNNDIYVKI EPNLPSYRIT WTGKEDIIYN GITDWVYEEE   180
VFSAYSALWW SPNGTFLAYA QFNDTEVPLI EYSFYSDESL QYPKTVRVPY PKAGAVNPTV   240
KFFVVNTDSL SSVTNATSIQ ITAPASMLIG DHYLCDVTWA TQERISLQWL RRIQNYSVMD   300
ICDYDESSGR WNCLVARQHI EMSTTGWVGR FRPSEPHFTL DGNSFYKIIS NEEGYRHICY   360
FQIDKKDCTF ITKGTWEVIG IEALTSDYLY YISNEYKGMP GGRNLYKIQL SDYTKVTCLS   420
CELNPERCQY YSVSFSKEAK YYQLRCSGPG LPLYTLHSSV NDKGLRVLED NSALDKMLQN   480
VQMPSKKLDF IILNETKFWY QMILPPHFDK SKKYPLLLDV YAGPCSQKAD TVFRLNWATY   540
LASTENIIVA SFDGRGSGYQ GDKIMHAINR RLGTFEVEDQ IEAARQFSKM GFVDNKRIAI   600
WGWSYGGYVT SMVLGSGSGV FKCGIAVAPV SRWEYYDSVY TERYMGLPTP EDNLDHYRNS   660
TVMSRAENFK QVEYLLIHGT ADDNVHFQQS AQISKALVDV GVDFQAMWYT DEDHGIASST   720
AHQHIYTHMS HFIKQCFSLP                                               740
```

FIGURE 1 A

Human cDNA sequence encoding residues 39-766 of DPPIV [SEQ ID NO: 3]

```
AGTCGCAAAA CTTACACTCT AACTGATTAC TTAAAAAATA CTTATAGACT GAAGTTATAC    60
TCCTTAAGAT GGATTTCAGA TCATGAATAT CTCTACAAAC AAGAAAATAA TATCTTGGTA   120
TTCAATGCTG AAATATGGAA CAGCTCAGTT TTCTTGGAGA ACAGTACATT TGATGAGTTT   180
GGACATTCTA TCAATGATTA TTCAATATCT CCTGATGGGC AGTTTATTCT CTTAGAATAC   240
AACTACGTGA AGCAATGGAG GCATTCCTAC ACAGCTTCAT ATGACATTTA TGATTTAAAT   300
AAAAGGCAGC TGATTACAGA AGAGAGGATT CCAAACAACA CACAGTGGGT CACATGGTCA   360
CCAGTGGGTC ATAAATTGGC ATATGTTTGG AACAATGACA TTTATGTTAA AATTGAACCA   420
AATTTACCAA GTTACAGAAT CACATGGACG GGGAAGGAAG ATATAATATA TAATGGAATA   480
ACTGACTGGG TTTATGAAGA GGAAGTCTTC AGTGCCTACT CTGCTCTGTG GTGGTCTCCA   540
AACGGCACTT TTTTAGCATA TGCCCAATTT AACGACACAG AAGTCCCACT TATTGAATAC   600
TCCTTCTACT CTGATGAGTC ACTGCAGTAC CCAAAGACTG TACGGGTTCC ATATCCAAAG   660
GCAGGAGCTG TGAATCCAAC TGTAAAGTTC TTTGTTGTAA ATACAGACTC TCTCAGCTCA   720
GTCACCAATG CAACTTCCAT ACAAATCACT GCTCCTGCTT CTATGTTGAT AGGGGATCAC   780
TACTTGTGTG ATGTGACATG GCCAACACAA GAAAGAATTT CTTTGCAGTG GCTCAGGAGG   840
ATTCAGAACT ATTCGGTCAT GGATATTTGT GACTATGATG AATCCAGTGG AAGATGGAAC   900
TGCTTAGTGG CACGGCAACA CATTGAAATG AGTACTACTG GCTGGGTTGG AAGATTTAGG   960
CCTTCAGAAC CTCATTTTAC CCTTGATGGT AATAGCTTCT ACAAGATCAT CAGCAATGAA  1020
GAAGGTTACA GACACATTTG CTATTTCCAA ATAGATAAAA AAGACTGCAC ATTTATTACA  1080
AAAGGCACCT GGGAAGTCAT CGGGATAGAA GCTCTAACCA GTGATTATCT ATACTACATT  1140
AGTAATGAAT ATAAAGGAAT GCCAGGAGGA AGGAATCTTT ATAAAATCCA ACTTATTGAC  1200
TATACAAAAG TGACATGCCT CAGTTGTGAG CTGAATCCGG AAAGGTGTCA GTACTATTCT  1260
GTGTCATTCA GTAAAGAGGC GAAGTATTAT CAGCTAGAT GTTCCGGTCC TGGTCTGCCC  1320
CTCTATACTC TACACAGCAG CGTGAATGAT AAAGGGCTGA GAGTCCTGGA AGACAATTCA  1380
GCTTTGGATA AAATGCTGCA GAATGTCCAG ATGCCTCCA AAAAACTGGA CTTCATTATT  1440
TTGAATGAAA CAAAATTTTG GTATCAGATG ATCTTGCCTC CTCATTTTGA TAAATCCAAG  1500
AAATATCCTC TACTATTAGA TGTGTATGCA GGCCCATGTA GTCAAAAGC AGACACTGTC  1560
TTCAGACTGA ACTGGGCCAC TTACCTTGCA AGCACAGAAA ACATTATAGT AGCTAGCTTT  1620
GATGGCAGAG GAAGTGGTTA CCAAGGAGAT AAGATCATGC ATGCAATCAA CAGAAGACTG  1680
GGAACATTTG AAGTTGAAGA TCAAATTGAA GCAGCCAGAC AATTTTCAAA AATGGGATTT  1740
GTGGACAACA AACGAATTGC AATTTGGGGC TGGTCATATG GAGGGTACGT AACCTCAATG  1800
GTCCTGGGAT CGGGAAGTGG CGTGTTCAAG TGTGGAATAG CCGTGGCGCC TGTATCCCGG  1860
TGGGAGTACT ATGACTCAGT GTACACAGAA CGTTACATGG GTCTCCCAAC TCCAGAAGAC  1920
AACCTTGACC ATTACAGAAA TTCAACAGTC ATGAGCAGAG CTGAAAATTT TAAACAAGTT  1980
GAGTACCTCC TTATTCATGG AACAGCAGAT GATAACGTTC ACTTTCAGCA GTCAGCTCAG  2040
ATCTCCAAAG CCCTGGTCGA TGTTGGAGTG GATTTCCAGG CAATGTGGTA TACTGATGAA  2100
GACCATGGAA TAGCTAGCAG CACAGCACAC CAACATATAT ATACCCACAT GAGCCACTTC  2160
ATAAAACAAT GTTTCTCTTT ACCT                                          2184
```

FIGURE 3

LEGEND

Column headings from left to right are (A)'Atom Number', (B)'Atom Type', (C)'Amino Acid', (D)'Chain Identifier', (E)'Amino Acid Number' (reference to SEQ ID NO: 3), (F)'X Coordinate', (G)'Y Coordinate', (H)'Z Coordinate', (I)'Occupancy' (OCC) and (J)'B factor'.

| A | B | C | D | E | F | G | H | I | J |
|---|---|---|---|---|---|---|---|---|---|
| 1 | N | ARG | A | 14 | -78.499 | 25.732 | 64.898 | 1.00 | 51.08 |
| 2 | CA | ARG | A | 14 | -77.682 | 24.936 | 63.934 | 1.00 | 50.91 |
| 3 | CB | ARG | A | 14 | -76.853 | 25.895 | 63.064 | 1.00 | 51.59 |
| 4 | CG | ARG | A | 14 | -76.507 | 25.382 | 61.666 | 1.00 | 54.33 |
| 5 | CD | ARG | A | 14 | -76.170 | 26.503 | 60.678 | 1.00 | 58.00 |
| 6 | NE | ARG | A | 14 | -76.489 | 26.159 | 59.292 | 1.00 | 61.47 |
| 7 | CZ | ARG | A | 14 | -76.158 | 26.909 | 58.245 | 1.00 | 62.24 |
| 8 | NH1 | ARG | A | 14 | -75.492 | 28.043 | 58.429 | 1.00 | 61.77 |
| 9 | NH2 | ARG | A | 14 | -76.486 | 26.525 | 57.016 | 1.00 | 62.51 |
| 10 | C | ARG | A | 14 | -76.763 | 23.943 | 64.655 | 1.00 | 49.68 |
| 11 | O | ARG | A | 14 | -75.871 | 23.360 | 64.038 | 1.00 | 49.98 |
| 12 | N | LYS | A | 15 | -76.986 | 23.740 | 65.952 | 1.00 | 47.84 |
| 13 | CA | LYS | A | 15 | -76.091 | 22.892 | 66.731 | 1.00 | 46.49 |
| 14 | CB | LYS | A | 15 | -75.983 | 23.350 | 68.181 | 1.00 | 46.98 |
| 15 | CG | LYS | A | 15 | -77.288 | 23.731 | 68.859 | 1.00 | 49.99 |
| 16 | CD | LYS | A | 15 | -77.002 | 24.390 | 70.224 | 1.00 | 53.43 |
| 17 | CE | LYS | A | 15 | -78.085 | 25.406 | 70.605 | 1.00 | 55.57 |
| 18 | NZ | LYS | A | 15 | -77.642 | 26.378 | 71.671 | 1.00 | 57.35 |
| 19 | C | LYS | A | 15 | -76.358 | 21.398 | 66.670 | 1.00 | 44.72 |
| 20 | O | LYS | A | 15 | -77.487 | 20.943 | 66.476 | 1.00 | 44.71 |
| 21 | N | THR | A | 16 | -75.279 | 20.641 | 66.812 | 1.00 | 42.33 |
| 22 | CA | THR | A | 16 | -75.363 | 19.201 | 66.815 | 1.00 | 39.34 |
| 23 | CB | THR | A | 16 | -74.225 | 18.582 | 66.009 | 1.00 | 39.46 |
| 24 | OG1 | THR | A | 16 | -72.972 | 18.975 | 66.565 | 1.00 | 38.25 |
| 25 | CG2 | THR | A | 16 | -74.187 | 19.163 | 64.603 | 1.00 | 38.11 |
| 26 | C | THR | A | 16 | -75.295 | 18.761 | 68.251 | 1.00 | 37.67 |
| 27 | O | THR | A | 16 | -75.098 | 19.578 | 69.150 | 1.00 | 37.00 |
| 28 | N | TYR | A | 17 | -75.534 | 17.476 | 68.466 | 1.00 | 35.46 |
| 29 | CA | TYR | A | 17 | -75.439 | 16.896 | 69.785 | 1.00 | 33.88 |
| 30 | CB | TYR | A | 17 | -76.340 | 15.666 | 69.865 | 1.00 | 33.82 |
| 31 | CG | TYR | A | 17 | -76.311 | 14.944 | 71.179 | 1.00 | 32.28 |
| 32 | CD1 | TYR | A | 17 | -77.203 | 15.265 | 72.191 | 1.00 | 32.55 |
| 33 | CE1 | TYR | A | 17 | -77.170 | 14.603 | 73.411 | 1.00 | 32.32 |
| 34 | CZ | TYR | A | 17 | -76.248 | 13.588 | 73.600 | 1.00 | 31.27 |
| 35 | OH | TYR | A | 17 | -76.199 | 12.905 | 74.782 | 1.00 | 29.92 |
| 36 | CE2 | TYR | A | 17 | -75.366 | 13.257 | 72.606 | 1.00 | 30.87 |
| 37 | CD2 | TYR | A | 17 | -75.395 | 13.936 | 71.406 | 1.00 | 30.90 |
| 38 | C | TYR | A | 17 | -73.971 | 16.526 | 69.924 | 1.00 | 32.90 |
| 39 | O | TYR | A | 17 | -73.501 | 15.626 | 69.247 | 1.00 | 32.98 |
| 40 | N | THR | A | 18 | -73.247 | 17.244 | 70.776 | 1.00 | 31.58 |
| 41 | CA | THR | A | 18 | -71.792 | 17.060 | 70.901 | 1.00 | 30.40 |

FIGURE 3A

| A | B | C | D | E | F | G | H | I | J |
|---|---|---|---|---|---|---|---|---|---|
| 42 | CB | THR | A | 18 | -71.126 | 18.369 | 71.311 | 1.00 | 29.92 |
| 43 | OG1 | THR | A | 18 | -71.551 | 18.690 | 72.644 | 1.00 | 29.95 |
| 44 | CG2 | THR | A | 18 | -71.606 | 19.526 | 70.444 | 1.00 | 30.35 |
| 45 | C | THR | A | 18 | -71.353 | 16.053 | 71.937 | 1.00 | 29.51 |
| 46 | O | THR | A | 18 | -72.131 | 15.625 | 72.782 | 1.00 | 28.96 |
| 47 | N | LEU | A | 19 | -70.064 | 15.739 | 71.895 | 1.00 | 29.18 |
| 48 | CA | LEU | A | 19 | -69.454 | 14.841 | 72.858 | 1.00 | 29.40 |
| 49 | CB | LEU | A | 19 | -67.958 | 14.681 | 72.570 | 1.00 | 29.30 |
| 50 | CG | LEU | A | 19 | -67.186 | 13.725 | 73.475 | 1.00 | 29.28 |
| 51 | CD1 | LEU | A | 19 | -67.668 | 12.278 | 73.289 | 1.00 | 26.89 |
| 52 | CD2 | LEU | A | 19 | -65.706 | 13.844 | 73.171 | 1.00 | 29.54 |
| 53 | C | LEU | A | 19 | -69.668 | 15.422 | 74.247 | 1.00 | 29.40 |
| 54 | O | LEU | A | 19 | -70.014 | 14.702 | 75.174 | 1.00 | 29.52 |
| 55 | N | THR | A | 20 | -69.483 | 16.731 | 74.375 | 1.00 | 29.38 |
| 56 | CA | THR | A | 20 | -69.674 | 17.419 | 75.650 | 1.00 | 29.71 |
| 57 | CB | THR | A | 20 | -69.270 | 18.921 | 75.530 | 1.00 | 30.55 |
| 58 | OG1 | THR | A | 20 | -67.858 | 19.022 | 75.275 | 1.00 | 31.86 |
| 59 | CG2 | THR | A | 20 | -69.426 | 19.646 | 76.871 | 1.00 | 29.63 |
| 60 | C | THR | A | 20 | -71.095 | 17.286 | 76.152 | 1.00 | 29.39 |
| 61 | O | THR | A | 20 | -71.311 | 17.062 | 77.336 | 1.00 | 29.75 |
| 62 | N | ASP | A | 21 | -72.070 | 17.413 | 75.255 | 1.00 | 29.23 |
| 63 | CA | ASP | A | 21 | -73.467 | 17.237 | 75.640 | 1.00 | 28.50 |
| 64 | CB | ASP | A | 21 | -74.381 | 17.347 | 74.420 | 1.00 | 28.92 |
| 65 | CG | ASP | A | 21 | -74.390 | 18.740 | 73.824 | 1.00 | 30.30 |
| 66 | OD1 | ASP | A | 21 | -74.348 | 19.699 | 74.612 | 1.00 | 30.33 |
| 67 | OD2 | ASP | A | 21 | -74.419 | 18.969 | 72.588 | 1.00 | 31.62 |
| 68 | C | ASP | A | 21 | -73.635 | 15.871 | 76.288 | 1.00 | 28.19 |
| 69 | O | ASP | A | 21 | -74.255 | 15.737 | 77.363 | 1.00 | 27.07 |
| 70 | N | TYR | A | 22 | -73.067 | 14.854 | 75.635 | 1.00 | 28.18 |
| 71 | CA | TYR | A | 22 | -73.110 | 13.498 | 76.162 | 1.00 | 28.06 |
| 72 | CB | TYR | A | 22 | -72.478 | 12.503 | 75.180 | 1.00 | 28.13 |
| 73 | CG | TYR | A | 22 | -72.316 | 11.105 | 75.757 | 1.00 | 28.21 |
| 74 | CD1 | TYR | A | 22 | -73.381 | 10.473 | 76.387 | 1.00 | 27.52 |
| 75 | CE1 | TYR | A | 22 | -73.231 | 9.225 | 76.941 | 1.00 | 31.17 |
| 76 | CZ | TYR | A | 22 | -71.994 | 8.574 | 76.850 | 1.00 | 31.00 |
| 77 | OH | TYR | A | 22 | -71.855 | 7.320 | 77.396 | 1.00 | 33.09 |
| 78 | CE2 | TYR | A | 22 | -70.920 | 9.184 | 76.231 | 1.00 | 27.37 |
| 79 | CD2 | TYR | A | 22 | -71.086 | 10.444 | 75.703 | 1.00 | 27.39 |
| 80 | C | TYR | A | 22 | -72.400 | 13.430 | 77.507 | 1.00 | 28.37 |
| 81 | O | TYR | A | 22 | -72.966 | 12.974 | 78.504 | 1.00 | 28.20 |
| 82 | N | LEU | A | 23 | -71.160 | 13.894 | 77.544 | 1.00 | 29.10 |
| 83 | CA | LEU | A | 23 | -70.363 | 13.783 | 78.766 | 1.00 | 29.84 |
| 84 | CB | LEU | A | 23 | -68.895 | 14.060 | 78.490 | 1.00 | 29.67 |
| 85 | CG | LEU | A | 23 | -68.233 | 13.147 | 77.454 | 1.00 | 30.09 |
| 86 | CD1 | LEU | A | 23 | -66.745 | 13.421 | 77.442 | 1.00 | 27.93 |
| 87 | CD2 | LEU | A | 23 | -68.502 | 11.647 | 77.730 | 1.00 | 29.29 |
| 88 | C | LEU | A | 23 | -70.846 | 14.639 | 79.919 | 1.00 | 30.85 |
| 89 | O | LEU | A | 23 | -70.704 | 14.254 | 81.081 | 1.00 | 31.02 |
| 90 | N | LYS | A | 24 | -71.417 | 15.798 | 79.613 | 1.00 | 31.74 |
| 91 | CA | LYS | A | 24 | -71.909 | 16.658 | 80.669 | 1.00 | 33.11 |
| 92 | CB | LYS | A | 24 | -71.501 | 18.129 | 80.433 | 1.00 | 33.11 |

FIGURE 3B

| A | B | C | D | E | F | G | H | I | J |
|---|---|---|---|---|---|---|---|---|---|
| 93 | CG | LYS | A | 24 | -69.997 | 18.373 | 80.362 | 1.00 | 31.71 |
| 94 | CD | LYS | A | 24 | -69.297 | 17.906 | 81.648 | 1.00 | 32.14 |
| 95 | CE | LYS | A | 24 | -67.820 | 18.355 | 81.702 | 1.00 | 32.14 |
| 96 | NZ | LYS | A | 24 | -67.002 | 17.666 | 82.769 | 1.00 | 29.53 |
| 97 | C | LYS | A | 24 | -73.426 | 16.521 | 80.864 | 1.00 | 34.49 |
| 98 | O | LYS | A | 24 | -73.998 | 17.135 | 81.752 | 1.00 | 34.44 |
| 99 | N | ASN | A | 25 | -74.082 | 15.701 | 80.048 | 1.00 | 36.12 |
| 100 | CA | ASN | A | 25 | -75.517 | 15.506 | 80.214 | 1.00 | 37.50 |
| 101 | CB | ASN | A | 25 | -75.813 | 14.898 | 81.583 | 1.00 | 38.04 |
| 102 | CG | ASN | A | 25 | -75.397 | 13.437 | 81.686 | 1.00 | 42.36 |
| 103 | OD1 | ASN | A | 25 | -75.195 | 12.919 | 82.793 | 1.00 | 46.50 |
| 104 | ND2 | ASN | A | 25 | -75.285 | 12.753 | 80.534 | 1.00 | 46.18 |
| 105 | C | ASN | A | 25 | -76.312 | 16.808 | 80.032 | 1.00 | 37.71 |
| 106 | O | ASN | A | 25 | -77.122 | 17.187 | 80.870 | 1.00 | 37.63 |
| 107 | N | THR | A | 26 | -76.066 | 17.493 | 78.926 | 1.00 | 38.29 |
| 108 | CA | THR | A | 26 | -76.761 | 18.725 | 78.622 | 1.00 | 38.88 |
| 109 | CB | THR | A | 26 | -76.259 | 19.227 | 77.281 | 1.00 | 39.01 |
| 110 | OG1 | THR | A | 26 | -74.854 | 19.444 | 77.377 | 1.00 | 39.58 |
| 111 | CG2 | THR | A | 26 | -76.817 | 20.607 | 76.955 | 1.00 | 39.02 |
| 112 | C | THR | A | 26 | -78.271 | 18.476 | 78.551 | 1.00 | 39.19 |
| 113 | O | THR | A | 26 | -79.066 | 19.157 | 79.198 | 1.00 | 39.04 |
| 114 | N | TYR | A | 27 | -78.637 | 17.482 | 77.754 | 1.00 | 39.58 |
| 115 | CA | TYR | A | 27 | -80.017 | 17.110 | 77.518 | 1.00 | 39.93 |
| 116 | CB | TYR | A | 27 | -80.169 | 16.771 | 76.044 | 1.00 | 39.52 |
| 117 | CG | TYR | A | 27 | -79.698 | 17.921 | 75.211 | 1.00 | 38.77 |
| 118 | CD1 | TYR | A | 27 | -80.438 | 19.087 | 75.151 | 1.00 | 39.35 |
| 119 | CE1 | TYR | A | 27 | -80.006 | 20.166 | 74.431 | 1.00 | 39.27 |
| 120 | CZ | TYR | A | 27 | -78.817 | 20.093 | 73.765 | 1.00 | 38.78 |
| 121 | OH | TYR | A | 27 | -78.400 | 21.180 | 73.049 | 1.00 | 38.94 |
| 122 | CE2 | TYR | A | 27 | -78.051 | 18.947 | 73.817 | 1.00 | 38.83 |
| 123 | CD2 | TYR | A | 27 | -78.488 | 17.878 | 74.549 | 1.00 | 38.20 |
| 124 | C | TYR | A | 27 | -80.398 | 15.926 | 78.368 | 1.00 | 40.73 |
| 125 | O | TYR | A | 27 | -80.207 | 14.793 | 77.969 | 1.00 | 41.03 |
| 126 | N | ARG | A | 28 | -80.940 | 16.177 | 79.546 | 1.00 | 42.07 |
| 127 | CA | ARG | A | 28 | -81.271 | 15.065 | 80.420 | 1.00 | 43.55 |
| 128 | CB | ARG | A | 28 | -81.423 | 15.521 | 81.873 | 1.00 | 44.02 |
| 129 | CG | ARG | A | 28 | -80.996 | 14.454 | 82.878 | 1.00 | 47.22 |
| 130 | CD | ARG | A | 28 | -81.354 | 14.734 | 84.340 | 1.00 | 51.56 |
| 131 | NE | ARG | A | 28 | -82.668 | 14.202 | 84.699 | 1.00 | 55.65 |
| 132 | CZ | ARG | A | 28 | -83.559 | 14.845 | 85.448 | 1.00 | 57.92 |
| 133 | NH1 | ARG | A | 28 | -83.291 | 16.050 | 85.930 | 1.00 | 58.60 |
| 134 | NH2 | ARG | A | 28 | -84.725 | 14.279 | 85.715 | 1.00 | 60.08 |
| 135 | C | ARG | A | 28 | -82.534 | 14.355 | 79.951 | 1.00 | 43.77 |
| 136 | O | ARG | A | 28 | -83.352 | 14.918 | 79.221 | 1.00 | 44.23 |
| 137 | N | LEU | A | 29 | -82.669 | 13.097 | 80.338 | 1.00 | 43.66 |
| 138 | CA | LEU | A | 29 | -83.883 | 12.376 | 80.054 | 1.00 | 43.77 |
| 139 | CB | LEU | A | 29 | -83.602 | 10.950 | 79.602 | 1.00 | 43.85 |
| 140 | CG | LEU | A | 29 | -83.293 | 10.758 | 78.121 | 1.00 | 44.26 |
| 141 | CD1 | LEU | A | 29 | -82.836 | 9.324 | 77.850 | 1.00 | 45.40 |
| 142 | CD2 | LEU | A | 29 | -84.505 | 11.088 | 77.282 | 1.00 | 45.47 |
| 143 | C | LEU | A | 29 | -84.578 | 12.376 | 81.381 | 1.00 | 43.80 |

FIGURE 3C

| A | B | C | D | E | F | G | H | I | J |
|---|---|---|---|---|---|---|---|---|---|
| 144 | O | LEU | A | 29 | -83.983 | 12.028 | 82.397 | 1.00 | 43.27 |
| 145 | N | LYS | A | 30 | -85.831 | 12.804 | 81.393 | 1.00 | 43.83 |
| 146 | CA | LYS | A | 30 | -86.540 | 12.864 | 82.653 | 1.00 | 44.19 |
| 147 | CB | LYS | A | 30 | -87.558 | 13.999 | 82.623 | 1.00 | 44.45 |
| 148 | CG | LYS | A | 30 | -87.589 | 14.791 | 83.904 | 1.00 | 45.86 |
| 149 | CD | LYS | A | 30 | -87.585 | 16.278 | 83.631 | 1.00 | 48.33 |
| 150 | CE | LYS | A | 30 | -87.850 | 17.057 | 84.915 | 1.00 | 50.36 |
| 151 | NZ | LYS | A | 30 | -87.184 | 16.414 | 86.093 | 1.00 | 50.63 |
| 152 | C | LYS | A | 30 | -87.188 | 11.530 | 82.992 | 1.00 | 43.80 |
| 153 | O | LYS | A | 30 | -87.671 | 10.828 | 82.119 | 1.00 | 43.69 |
| 154 | N | LEU | A | 31 | -87.176 | 11.182 | 84.269 | 1.00 | 43.81 |
| 155 | CA | LEU | A | 31 | -87.756 | 9.930 | 84.734 | 1.00 | 43.79 |
| 156 | CB | LEU | A | 31 | -86.736 | 9.163 | 85.574 | 1.00 | 43.75 |
| 157 | CG | LEU | A | 31 | -85.603 | 8.328 | 84.969 | 1.00 | 44.56 |
| 158 | CD1 | LEU | A | 31 | -84.873 | 9.055 | 83.846 | 1.00 | 43.44 |
| 159 | CD2 | LEU | A | 31 | -84.628 | 7.930 | 86.096 | 1.00 | 44.48 |
| 160 | C | LEU | A | 31 | -88.977 | 10.156 | 85.617 | 1.00 | 43.68 |
| 161 | O | LEU | A | 31 | -89.333 | 11.277 | 85.963 | 1.00 | 43.78 |
| 162 | N | TYR | A | 32 | -89.615 | 9.065 | 85.996 | 1.00 | 43.53 |
| 163 | CA | TYR | A | 32 | -90.674 | 9.138 | 86.968 | 1.00 | 43.23 |
| 164 | CB | TYR | A | 32 | -92.052 | 9.303 | 86.338 | 1.00 | 43.05 |
| 165 | CG | TYR | A | 32 | -93.048 | 9.809 | 87.349 | 1.00 | 42.24 |
| 166 | CD1 | TYR | A | 32 | -93.511 | 8.981 | 88.365 | 1.00 | 40.80 |
| 167 | CE1 | TYR | A | 32 | -94.404 | 9.431 | 89.295 | 1.00 | 40.31 |
| 168 | CZ | TYR | A | 32 | -94.844 | 10.741 | 89.243 | 1.00 | 41.67 |
| 169 | OH | TYR | A | 32 | -95.739 | 11.185 | 90.191 | 1.00 | 43.57 |
| 170 | CE2 | TYR | A | 32 | -94.393 | 11.593 | 88.260 | 1.00 | 41.02 |
| 171 | CD2 | TYR | A | 32 | -93.490 | 11.127 | 87.321 | 1.00 | 41.49 |
| 172 | C | TYR | A | 32 | -90.607 | 7.874 | 87.767 | 1.00 | 43.22 |
| 173 | O | TYR | A | 32 | -91.398 | 6.966 | 87.573 | 1.00 | 43.16 |
| 174 | N | SER | A | 33 | -89.646 | 7.823 | 88.671 | 1.00 | 43.72 |
| 175 | CA | SER | A | 33 | -89.442 | 6.642 | 89.486 | 1.00 | 44.29 |
| 176 | CB | SER | A | 33 | -87.971 | 6.494 | 89.860 | 1.00 | 44.28 |
| 177 | OG | SER | A | 33 | -87.829 | 5.415 | 90.769 | 1.00 | 45.94 |
| 178 | C | SER | A | 33 | -90.255 | 6.707 | 90.749 | 1.00 | 44.40 |
| 179 | O | SER | A | 33 | -90.016 | 7.558 | 91.591 | 1.00 | 44.77 |
| 180 | N | LEU | A | 34 | -91.195 | 5.782 | 90.895 | 1.00 | 44.57 |
| 181 | CA | LEU | A | 34 | -92.057 | 5.761 | 92.058 | 1.00 | 44.62 |
| 182 | CB | LEU | A | 34 | -93.520 | 5.959 | 91.626 | 1.00 | 44.14 |
| 183 | CG | LEU | A | 34 | -94.125 | 4.942 | 90.643 | 1.00 | 43.66 |
| 184 | CD1 | LEU | A | 34 | -94.404 | 3.595 | 91.314 | 1.00 | 40.76 |
| 185 | CD2 | LEU | A | 34 | -95.392 | 5.481 | 89.957 | 1.00 | 41.85 |
| 186 | C | LEU | A | 34 | -91.893 | 4.444 | 92.788 | 1.00 | 45.36 |
| 187 | O | LEU | A | 34 | -91.354 | 3.490 | 92.236 | 1.00 | 45.44 |
| 188 | N | ARG | A | 35 | -92.332 | 4.398 | 94.038 | 1.00 | 46.33 |
| 189 | CA | ARG | A | 35 | -92.342 | 3.152 | 94.780 | 1.00 | 48.23 |
| 190 | CB | ARG | A | 35 | -91.397 | 3.171 | 95.983 | 1.00 | 48.19 |
| 191 | CG | ARG | A | 35 | -90.088 | 3.873 | 95.758 | 1.00 | 50.55 |
| 192 | CD | ARG | A | 35 | -89.158 | 3.812 | 96.952 | 1.00 | 52.14 |
| 193 | NE | ARG | A | 35 | -87.815 | 4.235 | 96.585 | 1.00 | 54.13 |
| 194 | CZ | ARG | A | 35 | -86.755 | 4.134 | 97.378 | 1.00 | 53.95 |

FIGURE 3D

| A | B | C | D | E | F | G | H | I | J |
|---|---|---|---|---|---|---|---|---|---|
| 195 | NH1 | ARG | A | 35 | -86.886 | 3.625 | 98.600 | 1.00 | 51.85 |
| 196 | NH2 | ARG | A | 35 | -85.569 | 4.552 | 96.942 | 1.00 | 53.73 |
| 197 | C | ARG | A | 35 | -93.743 | 3.011 | 95.297 | 1.00 | 48.75 |
| 198 | O | ARG | A | 35 | -94.246 | 3.909 | 95.958 | 1.00 | 49.28 |
| 199 | N | TRP | A | 36 | -94.381 | 1.891 | 95.009 | 1.00 | 49.62 |
| 200 | CA | TRP | A | 36 | -95.722 | 1.688 | 95.504 | 1.00 | 50.47 |
| 201 | CB | TRP | A | 36 | -96.409 | 0.550 | 94.751 | 1.00 | 50.15 |
| 202 | CG | TRP | A | 36 | -96.845 | 0.918 | 93.357 | 1.00 | 49.57 |
| 203 | CD1 | TRP | A | 36 | -96.282 | 0.500 | 92.191 | 1.00 | 48.94 |
| 204 | NE1 | TRP | A | 36 | -96.956 | 1.033 | 91.120 | 1.00 | 48.90 |
| 205 | CE2 | TRP | A | 36 | -97.985 | 1.813 | 91.581 | 1.00 | 48.49 |
| 206 | CD2 | TRP | A | 36 | -97.945 | 1.765 | 92.987 | 1.00 | 48.80 |
| 207 | CE3 | TRP | A | 36 | -98.902 | 2.490 | 93.704 | 1.00 | 48.56 |
| 208 | CZ3 | TRP | A | 36 | -99.857 | 3.220 | 93.005 | 1.00 | 49.05 |
| 209 | CH2 | TRP | A | 36 | -99.867 | 3.246 | 91.607 | 1.00 | 47.62 |
| 210 | CZ2 | TRP | A | 36 | -98.940 | 2.553 | 90.879 | 1.00 | 48.27 |
| 211 | C | TRP | A | 36 | -95.581 | 1.359 | 96.970 | 1.00 | 51.34 |
| 212 | O | TRP | A | 36 | -94.558 | 0.821 | 97.388 | 1.00 | 51.46 |
| 213 | N | ILE | A | 37 | -96.598 | 1.685 | 97.757 | 1.00 | 52.47 |
| 214 | CA | ILE | A | 37 | -96.559 | 1.421 | 99.191 | 1.00 | 53.41 |
| 215 | CB | ILE | A | 37 | -96.449 | 2.737 | 99.958 | 1.00 | 53.42 |
| 216 | CG1 | ILE | A | 37 | -94.987 | 3.025 | 100.270 | 1.00 | 53.87 |
| 217 | CD1 | ILE | A | 37 | -94.196 | 3.466 | 99.076 | 1.00 | 54.40 |
| 218 | CG2 | ILE | A | 37 | -97.246 | 2.685 | 101.244 | 1.00 | 54.45 |
| 219 | C | ILE | A | 37 | -97.793 | 0.648 | 99.612 | 1.00 | 53.93 |
| 220 | O | ILE | A | 37 | -97.812 | -0.066 | 100.617 | 1.00 | 53.82 |
| 221 | N | SER | A | 38 | -98.833 | 0.793 | 98.814 | 1.00 | 54.88 |
| 222 | CA | SER | A | 38 | -100.072 | 0.103 | 99.078 | 1.00 | 55.80 |
| 223 | CB | SER | A | 38 | -101.023 | 1.013 | 99.840 | 1.00 | 55.67 |
| 224 | OG | SER | A | 38 | -100.863 | 2.357 | 99.413 | 1.00 | 56.45 |
| 225 | C | SER | A | 38 | -100.650 | -0.235 | 97.731 | 1.00 | 56.36 |
| 226 | O | SER | A | 38 | -99.944 | -0.241 | 96.726 | 1.00 | 56.35 |
| 227 | N | ASP | A | 39 | -101.945 | -0.488 | 97.696 | 1.00 | 57.13 |
| 228 | CA | ASP | A | 39 | -102.560 | -0.803 | 96.435 | 1.00 | 57.78 |
| 229 | CB | ASP | A | 39 | -103.718 | -1.766 | 96.627 | 1.00 | 58.12 |
| 230 | CG | ASP | A | 39 | -103.988 | -2.578 | 95.392 | 1.00 | 59.53 |
| 231 | OD1 | ASP | A | 39 | -105.111 | -3.106 | 95.254 | 1.00 | 61.71 |
| 232 | OD2 | ASP | A | 39 | -103.127 | -2.745 | 94.500 | 1.00 | 61.65 |
| 233 | C | ASP | A | 39 | -103.046 | 0.452 | 95.753 | 1.00 | 57.97 |
| 234 | O | ASP | A | 39 | -103.764 | 0.363 | 94.767 | 1.00 | 58.27 |
| 235 | N | HIS | A | 40 | -102.660 | 1.620 | 96.261 | 1.00 | 58.00 |
| 236 | CA | HIS | A | 40 | -103.128 | 2.865 | 95.654 | 1.00 | 58.81 |
| 237 | CB | HIS | A | 40 | -104.625 | 3.072 | 95.920 | 1.00 | 59.47 |
| 238 | CG | HIS | A | 40 | -105.071 | 2.575 | 97.257 | 1.00 | 61.31 |
| 239 | ND1 | HIS | A | 40 | -106.098 | 1.666 | 97.409 | 1.00 | 62.92 |
| 240 | CE1 | HIS | A | 40 | -106.264 | 1.405 | 98.694 | 1.00 | 63.69 |
| 241 | NE2 | HIS | A | 40 | -105.379 | 2.107 | 99.380 | 1.00 | 63.55 |
| 242 | CD2 | HIS | A | 40 | -104.618 | 2.845 | 98.504 | 1.00 | 62.40 |
| 243 | C | HIS | A | 40 | -102.354 | 4.110 | 96.059 | 1.00 | 58.35 |
| 244 | O | HIS | A | 40 | -102.744 | 5.229 | 95.720 | 1.00 | 58.06 |
| 245 | N | GLU | A | 41 | -101.259 | 3.915 | 96.780 | 1.00 | 58.00 |

FIGURE 3E

| A | B | C | D | E | F | G | H | I | J |
|---|---|---|---|---|---|---|---|---|---|
| 246 | CA | GLU | A | 41 | -100.409 | 5.027 | 97.167 | 1.00 | 57.73 |
| 247 | CB | GLU | A | 41 | -100.372 | 5.162 | 98.690 | 1.00 | 57.77 |
| 248 | CG | GLU | A | 41 | -101.698 | 5.542 | 99.334 | 1.00 | 57.46 |
| 249 | CD | GLU | A | 41 | -101.505 | 6.168 | 100.703 | 1.00 | 56.70 |
| 250 | OE1 | GLU | A | 41 | -101.106 | 5.438 | 101.644 | 1.00 | 56.35 |
| 251 | OE2 | GLU | A | 41 | -101.736 | 7.391 | 100.832 | 1.00 | 55.22 |
| 252 | C | GLU | A | 41 | -99.002 | 4.787 | 96.645 | 1.00 | 57.49 |
| 253 | O | GLU | A | 41 | -98.593 | 3.642 | 96.493 | 1.00 | 57.77 |
| 254 | N | TYR | A | 42 | -98.256 | 5.849 | 96.370 | 1.00 | 57.25 |
| 255 | CA | TYR | A | 42 | -96.869 | 5.669 | 95.954 | 1.00 | 57.17 |
| 256 | CB | TYR | A | 42 | -96.776 | 5.319 | 94.471 | 1.00 | 56.71 |
| 257 | CG | TYR | A | 42 | -97.027 | 6.456 | 93.510 | 1.00 | 54.55 |
| 258 | CD1 | TYR | A | 42 | -96.053 | 7.407 | 93.272 | 1.00 | 52.96 |
| 259 | CE1 | TYR | A | 42 | -96.254 | 8.430 | 92.382 | 1.00 | 51.65 |
| 260 | CZ | TYR | A | 42 | -97.440 | 8.513 | 91.693 | 1.00 | 51.43 |
| 261 | OH | TYR | A | 42 | -97.622 | 9.545 | 90.803 | 1.00 | 49.55 |
| 262 | CE2 | TYR | A | 42 | -98.427 | 7.572 | 91.897 | 1.00 | 52.02 |
| 263 | CD2 | TYR | A | 42 | -98.215 | 6.546 | 92.802 | 1.00 | 53.03 |
| 264 | C | TYR | A | 42 | -95.948 | 6.837 | 96.294 | 1.00 | 57.82 |
| 265 | O | TYR | A | 42 | -96.333 | 8.003 | 96.191 | 1.00 | 57.89 |
| 266 | N | LEU | A | 43 | -94.723 | 6.510 | 96.688 | 1.00 | 58.48 |
| 267 | CA | LEU | A | 43 | -93.746 | 7.526 | 97.049 | 1.00 | 59.28 |
| 268 | CB | LEU | A | 43 | -92.773 | 6.996 | 98.103 | 1.00 | 59.23 |
| 269 | CG | LEU | A | 43 | -93.436 | 6.643 | 99.433 | 1.00 | 58.97 |
| 270 | CD1 | LEU | A | 43 | -92.447 | 6.044 | 100.404 | 1.00 | 57.55 |
| 271 | CD2 | LEU | A | 43 | -94.111 | 7.874 | 100.016 | 1.00 | 58.52 |
| 272 | C | LEU | A | 43 | -92.975 | 8.011 | 95.849 | 1.00 | 59.92 |
| 273 | O | LEU | A | 43 | -92.592 | 7.230 | 94.989 | 1.00 | 60.06 |
| 274 | N | TYR | A | 44 | -92.762 | 9.318 | 95.799 | 1.00 | 61.07 |
| 275 | CA | TYR | A | 44 | -91.976 | 9.941 | 94.749 | 1.00 | 62.31 |
| 276 | CB | TYR | A | 44 | -92.881 | 10.720 | 93.798 | 1.00 | 61.95 |
| 277 | CG | TYR | A | 44 | -92.187 | 11.345 | 92.608 | 1.00 | 61.54 |
| 278 | CD1 | TYR | A | 44 | -91.690 | 10.561 | 91.569 | 1.00 | 61.21 |
| 279 | CE1 | TYR | A | 44 | -91.058 | 11.136 | 90.474 | 1.00 | 60.70 |
| 280 | CZ | TYR | A | 44 | -90.923 | 12.508 | 90.414 | 1.00 | 61.23 |
| 281 | OH | TYR | A | 44 | -90.301 | 13.098 | 89.336 | 1.00 | 61.42 |
| 282 | CE2 | TYR | A | 44 | -91.411 | 13.303 | 91.433 | 1.00 | 60.86 |
| 283 | CD2 | TYR | A | 44 | -92.038 | 12.722 | 92.516 | 1.00 | 61.00 |
| 284 | C | TYR | A | 44 | -91.030 | 10.867 | 95.492 | 1.00 | 63.51 |
| 285 | O | TYR | A | 44 | -91.299 | 11.226 | 96.634 | 1.00 | 63.78 |
| 286 | N | LYS | A | 45 | -89.916 | 11.232 | 94.873 | 1.00 | 65.00 |
| 287 | CA | LYS | A | 45 | -88.948 | 12.098 | 95.532 | 1.00 | 66.61 |
| 288 | CB | LYS | A | 45 | -87.641 | 11.335 | 95.779 | 1.00 | 66.63 |
| 289 | CG | LYS | A | 45 | -86.657 | 12.048 | 96.701 | 1.00 | 67.24 |
| 290 | CD | LYS | A | 45 | -85.319 | 11.316 | 96.767 | 1.00 | 68.31 |
| 291 | CE | LYS | A | 45 | -84.269 | 12.139 | 97.509 | 1.00 | 68.73 |
| 292 | NZ | LYS | A | 45 | -84.810 | 12.690 | 98.791 | 1.00 | 69.48 |
| 293 | C | LYS | A | 45 | -88.702 | 13.332 | 94.671 | 1.00 | 67.68 |
| 294 | O | LYS | A | 45 | -88.234 | 13.207 | 93.540 | 1.00 | 67.83 |
| 295 | N | GLN | A | 46 | -89.017 | 14.518 | 95.198 | 1.00 | 69.00 |
| 296 | CA | GLN | A | 46 | -88.868 | 15.752 | 94.415 | 1.00 | 70.27 |

FIGURE 3F

| A | B | C | D | E | F | G | H | I | J |
|---|---|---|---|---|---|---|---|---|---|
| 297 | CB | GLN | A | 46 | -90.210 | 16.495 | 94.254 | 1.00 | 70.38 |
| 298 | CG | GLN | A | 46 | -90.189 | 17.523 | 93.118 | 1.00 | 71.49 |
| 299 | CD | GLN | A | 46 | -91.574 | 18.038 | 92.716 | 1.00 | 73.94 |
| 300 | OE1 | GLN | A | 46 | -92.566 | 17.300 | 92.755 | 1.00 | 74.29 |
| 301 | NE2 | GLN | A | 46 | -91.637 | 19.308 | 92.313 | 1.00 | 74.28 |
| 302 | C | GLN | A | 46 | -87.771 | 16.710 | 94.891 | 1.00 | 70.79 |
| 303 | O | GLN | A | 46 | -88.012 | 17.595 | 95.719 | 1.00 | 70.72 |
| 304 | N | GLU | A | 47 | -86.569 | 16.518 | 94.344 | 1.00 | 71.70 |
| 305 | CA | GLU | A | 47 | -85.413 | 17.393 | 94.580 | 1.00 | 72.37 |
| 306 | CB | GLU | A | 47 | -85.480 | 18.608 | 93.644 | 1.00 | 72.68 |
| 307 | CG | GLU | A | 47 | -85.040 | 18.336 | 92.211 | 1.00 | 73.91 |
| 308 | CD | GLU | A | 47 | -83.561 | 18.604 | 91.986 | 1.00 | 75.82 |
| 309 | OE1 | GLU | A | 47 | -83.116 | 19.761 | 92.179 | 1.00 | 76.43 |
| 310 | OE2 | GLU | A | 47 | -82.840 | 17.657 | 91.612 | 1.00 | 76.92 |
| 311 | C | GLU | A | 47 | -85.240 | 17.869 | 96.019 | 1.00 | 72.44 |
| 312 | O | GLU | A | 47 | -84.595 | 18.894 | 96.268 | 1.00 | 72.64 |
| 313 | N | ASN | A | 48 | -85.801 | 17.116 | 96.959 | 1.00 | 72.46 |
| 314 | CA | ASN | A | 48 | -85.737 | 17.471 | 98.368 | 1.00 | 72.28 |
| 315 | CB | ASN | A | 48 | -86.404 | 18.833 | 98.599 | 1.00 | 72.52 |
| 316 | CG | ASN | A | 48 | -85.409 | 19.943 | 98.933 | 1.00 | 73.27 |
| 317 | OD1 | ASN | A | 48 | -84.235 | 19.690 | 99.213 | 1.00 | 74.24 |
| 318 | ND2 | ASN | A | 48 | -85.890 | 21.185 | 98.919 | 1.00 | 73.24 |
| 319 | C | ASN | A | 48 | -86.443 | 16.444 | 99.243 | 1.00 | 72.00 |
| 320 | O | ASN | A | 48 | -85.861 | 15.902 | 100.186 | 1.00 | 72.38 |
| 321 | N | ASN | A | 49 | -87.695 | 16.158 | 98.902 | 1.00 | 71.24 |
| 322 | CA | ASN | A | 49 | -88.567 | 15.415 | 99.796 | 1.00 | 70.45 |
| 323 | CB | ASN | A | 49 | -89.521 | 16.417 | 100.442 | 1.00 | 70.52 |
| 324 | CG | ASN | A | 49 | -90.018 | 17.461 | 99.449 | 1.00 | 70.98 |
| 325 | OD1 | ASN | A | 49 | -90.640 | 18.460 | 99.828 | 1.00 | 70.94 |
| 326 | ND2 | ASN | A | 49 | -89.742 | 17.233 | 98.166 | 1.00 | 70.86 |
| 327 | C | ASN | A | 49 | -89.396 | 14.293 | 99.200 | 1.00 | 69.91 |
| 328 | O | ASN | A | 49 | -89.781 | 14.321 | 98.028 | 1.00 | 70.04 |
| 329 | N | ILE | A | 50 | -89.701 | 13.316 | 100.042 | 1.00 | 69.04 |
| 330 | CA | ILE | A | 50 | -90.539 | 12.205 | 99.641 | 1.00 | 68.26 |
| 331 | CB | ILE | A | 50 | -90.337 | 11.008 | 100.573 | 1.00 | 68.17 |
| 332 | CG1 | ILE | A | 50 | -88.957 | 10.390 | 100.357 | 1.00 | 68.29 |
| 333 | CD1 | ILE | A | 50 | -87.916 | 10.833 | 101.355 | 1.00 | 68.40 |
| 334 | CG2 | ILE | A | 50 | -91.408 | 9.974 | 100.328 | 1.00 | 68.21 |
| 335 | C | ILE | A | 50 | -92.001 | 12.622 | 99.655 | 1.00 | 67.54 |
| 336 | O | ILE | A | 50 | -92.544 | 12.984 | 100.696 | 1.00 | 67.50 |
| 337 | N | LEU | A | 51 | -92.628 | 12.586 | 98.488 | 1.00 | 66.76 |
| 338 | CA | LEU | A | 51 | -94.043 | 12.899 | 98.366 | 1.00 | 65.98 |
| 339 | CB | LEU | A | 51 | -94.323 | 13.580 | 97.024 | 1.00 | 66.02 |
| 340 | CG | LEU | A | 51 | -94.640 | 15.082 | 97.012 | 1.00 | 65.96 |
| 341 | CD1 | LEU | A | 51 | -93.931 | 15.820 | 98.139 | 1.00 | 65.12 |
| 342 | CD2 | LEU | A | 51 | -94.322 | 15.711 | 95.652 | 1.00 | 65.83 |
| 343 | C | LEU | A | 51 | -94.859 | 11.621 | 98.471 | 1.00 | 65.39 |
| 344 | O | LEU | A | 51 | -94.350 | 10.533 | 98.225 | 1.00 | 65.35 |
| 345 | N | VAL | A | 52 | -96.119 | 11.748 | 98.869 | 1.00 | 64.69 |
| 346 | CA | VAL | A | 52 | -97.026 | 10.608 | 98.869 | 1.00 | 63.91 |
| 347 | CB | VAL | A | 52 | -97.772 | 10.450 | 100.184 | 1.00 | 64.07 |

FIGURE 3G

| A | B | C | D | E | F | G | H | I | J |
|---|---|---|---|---|---|---|---|---|---|
| 348 | CG1 | VAL | A | 52 | -97.047 | 11.166 | 101.304 | 1.00 | 64.22 |
| 349 | CG2 | VAL | A | 52 | -98.002 | 8.966 | 100.488 | 1.00 | 63.60 |
| 350 | C | VAL | A | 52 | -98.082 | 10.913 | 97.839 | 1.00 | 63.33 |
| 351 | O | VAL | A | 52 | -98.626 | 12.013 | 97.823 | 1.00 | 63.43 |
| 352 | N | PHE | A | 53 | -98.383 | 9.949 | 96.981 | 1.00 | 62.56 |
| 353 | CA | PHE | A | 53 | -99.390 | 10.165 | 95.959 | 1.00 | 61.64 |
| 354 | CB | PHE | A | 53 | -98.778 | 10.047 | 94.569 | 1.00 | 61.67 |
| 355 | CG | PHE | A | 53 | -98.025 | 11.265 | 94.117 | 1.00 | 61.05 |
| 356 | CD1 | PHE | A | 53 | -96.751 | 11.523 | 94.586 | 1.00 | 61.29 |
| 357 | CE1 | PHE | A | 53 | -96.053 | 12.634 | 94.151 | 1.00 | 61.02 |
| 358 | CZ | PHE | A | 53 | -96.625 | 13.495 | 93.236 | 1.00 | 60.95 |
| 359 | CE2 | PHE | A | 53 | -97.892 | 13.244 | 92.756 | 1.00 | 60.57 |
| 360 | CD2 | PHE | A | 53 | -98.580 | 12.130 | 93.192 | 1.00 | 60.71 |
| 361 | C | PHE | A | 53 | -100.505 | 9.150 | 96.078 | 1.00 | 61.31 |
| 362 | O | PHE | A | 53 | -100.254 | 7.965 | 96.304 | 1.00 | 61.35 |
| 363 | N | ASN | A | 54 | -101.742 | 9.620 | 95.960 | 1.00 | 60.84 |
| 364 | CA | ASN | A | 54 | -102.876 | 8.717 | 95.857 | 1.00 | 60.32 |
| 365 | CB | ASN | A | 54 | -104.179 | 9.395 | 96.288 | 1.00 | 60.41 |
| 366 | CG | ASN | A | 54 | -105.340 | 8.409 | 96.429 | 1.00 | 60.97 |
| 367 | OD1 | ASN | A | 54 | -106.103 | 8.477 | 97.390 | 1.00 | 61.46 |
| 368 | ND2 | ASN | A | 54 | -105.477 | 7.493 | 95.470 | 1.00 | 60.70 |
| 369 | C | ASN | A | 54 | -102.936 | 8.393 | 94.382 | 1.00 | 59.76 |
| 370 | O | ASN | A | 54 | -102.896 | 9.295 | 93.543 | 1.00 | 59.60 |
| 371 | N | ALA | A | 55 | -103.004 | 7.115 | 94.047 | 1.00 | 59.38 |
| 372 | CA | ALA | A | 55 | -103.065 | 6.740 | 92.641 | 1.00 | 59.02 |
| 373 | CB | ALA | A | 55 | -102.952 | 5.237 | 92.488 | 1.00 | 59.06 |
| 374 | C | ALA | A | 55 | -104.322 | 7.276 | 91.937 | 1.00 | 58.71 |
| 375 | O | ALA | A | 55 | -104.242 | 7.767 | 90.816 | 1.00 | 58.09 |
| 376 | N | GLU | A | 56 | -105.473 | 7.195 | 92.598 | 1.00 | 58.94 |
| 377 | CA | GLU | A | 56 | -106.736 | 7.646 | 91.991 | 1.00 | 59.29 |
| 378 | CB | GLU | A | 56 | -107.930 | 7.354 | 92.906 | 1.00 | 59.17 |
| 379 | CG | GLU | A | 56 | -108.493 | 5.948 | 92.791 | 1.00 | 59.64 |
| 380 | CD | GLU | A | 56 | -109.508 | 5.794 | 91.670 | 1.00 | 59.62 |
| 381 | OE1 | GLU | A | 56 | -109.458 | 6.558 | 90.681 | 1.00 | 59.64 |
| 382 | OE2 | GLU | A | 56 | -110.371 | 4.904 | 91.782 | 1.00 | 59.77 |
| 383 | C | GLU | A | 56 | -106.787 | 9.115 | 91.563 | 1.00 | 59.42 |
| 384 | O | GLU | A | 56 | -107.172 | 9.421 | 90.434 | 1.00 | 59.29 |
| 385 | N | TYR | A | 57 | -106.388 | 10.023 | 92.448 | 1.00 | 59.76 |
| 386 | CA | TYR | A | 57 | -106.556 | 11.453 | 92.162 | 1.00 | 60.14 |
| 387 | CB | TYR | A | 57 | -107.191 | 12.151 | 93.365 | 1.00 | 60.19 |
| 388 | CG | TYR | A | 57 | -108.191 | 11.284 | 94.093 | 1.00 | 60.37 |
| 389 | CD1 | TYR | A | 57 | -109.455 | 11.059 | 93.565 | 1.00 | 60.93 |
| 390 | CE1 | TYR | A | 57 | -110.373 | 10.267 | 94.226 | 1.00 | 60.78 |
| 391 | CZ | TYR | A | 57 | -110.030 | 9.676 | 95.425 | 1.00 | 60.79 |
| 392 | OH | TYR | A | 57 | -110.941 | 8.877 | 96.072 | 1.00 | 60.43 |
| 393 | CE2 | TYR | A | 57 | -108.775 | 9.871 | 95.966 | 1.00 | 60.89 |
| 394 | CD2 | TYR | A | 57 | -107.865 | 10.677 | 95.299 | 1.00 | 60.70 |
| 395 | C | TYR | A | 57 | -105.297 | 12.200 | 91.743 | 1.00 | 60.44 |
| 396 | O | TYR | A | 57 | -105.382 | 13.286 | 91.170 | 1.00 | 60.16 |
| 397 | N | GLY | A | 58 | -104.132 | 11.630 | 92.037 | 1.00 | 60.85 |
| 398 | CA | GLY | A | 58 | -102.881 | 12.281 | 91.700 | 1.00 | 61.42 |

FIGURE 3H

| A | B | C | D | E | F | G | H | I | J |
|---|---|---|---|---|---|---|---|---|---|
| 399 | C | GLY | A | 58 | -102.555 | 13.377 | 92.690 | 1.00 | 61.93 |
| 400 | O | GLY | A | 58 | -101.717 | 14.243 | 92.431 | 1.00 | 61.57 |
| 401 | N | ASN | A | 59 | -103.239 | 13.348 | 93.829 | 1.00 | 62.68 |
| 402 | CA | ASN | A | 59 | -102.990 | 14.341 | 94.863 | 1.00 | 63.62 |
| 403 | CB | ASN | A | 59 | -104.259 | 14.646 | 95.659 | 1.00 | 63.34 |
| 404 | CG | ASN | A | 59 | -104.818 | 13.429 | 96.334 | 1.00 | 63.30 |
| 405 | OD1 | ASN | A | 59 | -105.016 | 12.395 | 95.695 | 1.00 | 63.69 |
| 406 | ND2 | ASN | A | 59 | -105.068 | 13.531 | 97.637 | 1.00 | 62.78 |
| 407 | C | ASN | A | 59 | -101.864 | 13.873 | 95.780 | 1.00 | 64.23 |
| 408 | O | ASN | A | 59 | -101.847 | 12.729 | 96.236 | 1.00 | 64.24 |
| 409 | N | SER | A | 60 | -100.918 | 14.764 | 96.038 | 1.00 | 65.01 |
| 410 | CA | SER | A | 60 | -99.784 | 14.433 | 96.884 | 1.00 | 65.72 |
| 411 | CB | SER | A | 60 | -98.506 | 14.431 | 96.057 | 1.00 | 65.53 |
| 412 | OG | SER | A | 60 | -98.315 | 15.697 | 95.455 | 1.00 | 65.16 |
| 413 | C | SER | A | 60 | -99.610 | 15.389 | 98.061 | 1.00 | 66.42 |
| 414 | O | SER | A | 60 | -99.840 | 16.597 | 97.949 | 1.00 | 66.14 |
| 415 | N | SER | A | 61 | -99.191 | 14.819 | 99.186 | 1.00 | 67.34 |
| 416 | CA | SER | A | 61 | -98.905 | 15.568 | 100.397 | 1.00 | 68.04 |
| 417 | CB | SER | A | 61 | -99.960 | 15.278 | 101.468 | 1.00 | 68.06 |
| 418 | OG | SER | A | 61 | -99.954 | 13.909 | 101.847 | 1.00 | 66.79 |
| 419 | C | SER | A | 61 | -97.538 | 15.109 | 100.878 | 1.00 | 68.90 |
| 420 | O | SER | A | 61 | -97.251 | 13.912 | 100.892 | 1.00 | 68.87 |
| 421 | N | VAL | A | 62 | -96.698 | 16.063 | 101.266 | 1.00 | 69.78 |
| 422 | CA | VAL | A | 62 | -95.341 | 15.763 | 101.717 | 1.00 | 70.58 |
| 423 | CB | VAL | A | 62 | -94.659 | 17.027 | 102.273 | 1.00 | 70.42 |
| 424 | CG1 | VAL | A | 62 | -93.293 | 16.697 | 102.833 | 1.00 | 70.70 |
| 425 | CG2 | VAL | A | 62 | -94.555 | 18.092 | 101.186 | 1.00 | 70.79 |
| 426 | C | VAL | A | 62 | -95.307 | 14.638 | 102.757 | 1.00 | 71.13 |
| 427 | O | VAL | A | 62 | -95.955 | 14.728 | 103.800 | 1.00 | 71.06 |
| 428 | N | PHE | A | 63 | -94.556 | 13.578 | 102.460 | 1.00 | 71.86 |
| 429 | CA | PHE | A | 63 | -94.441 | 12.438 | 103.370 | 1.00 | 72.69 |
| 430 | CB | PHE | A | 63 | -94.274 | 11.133 | 102.597 | 1.00 | 72.66 |
| 431 | CG | PHE | A | 63 | -94.030 | 9.946 | 103.481 | 1.00 | 73.06 |
| 432 | CD1 | PHE | A | 63 | -92.762 | 9.675 | 103.963 | 1.00 | 73.09 |
| 433 | CE1 | PHE | A | 63 | -92.538 | 8.597 | 104.789 | 1.00 | 73.04 |
| 434 | CZ | PHE | A | 63 | -93.585 | 7.766 | 105.142 | 1.00 | 73.31 |
| 435 | CE2 | PHE | A | 63 | -94.854 | 8.023 | 104.670 | 1.00 | 73.34 |
| 436 | CD2 | PHE | A | 63 | -95.074 | 9.113 | 103.848 | 1.00 | 73.44 |
| 437 | C | PHE | A | 63 | -93.258 | 12.583 | 104.312 | 1.00 | 73.13 |
| 438 | O | PHE | A | 63 | -93.321 | 12.214 | 105.486 | 1.00 | 73.11 |
| 439 | N | LEU | A | 64 | -92.161 | 13.083 | 103.764 | 1.00 | 73.76 |
| 440 | CA | LEU | A | 64 | -90.956 | 13.295 | 104.530 | 1.00 | 74.42 |
| 441 | CB | LEU | A | 64 | -90.051 | 12.073 | 104.452 | 1.00 | 74.35 |
| 442 | CG | LEU | A | 64 | -88.873 | 12.070 | 105.425 | 1.00 | 74.56 |
| 443 | CD1 | LEU | A | 64 | -89.369 | 11.956 | 106.859 | 1.00 | 74.40 |
| 444 | CD2 | LEU | A | 64 | -87.905 | 10.945 | 105.099 | 1.00 | 74.72 |
| 445 | C | LEU | A | 64 | -90.265 | 14.490 | 103.915 | 1.00 | 75.00 |
| 446 | O | LEU | A | 64 | -89.856 | 14.449 | 102.755 | 1.00 | 75.07 |
| 447 | N | GLU | A | 65 | -90.148 | 15.561 | 104.688 | 1.00 | 75.74 |
| 448 | CA | GLU | A | 65 | -89.515 | 16.766 | 104.187 | 1.00 | 76.40 |
| 449 | CB | GLU | A | 65 | -90.053 | 18.014 | 104.893 | 1.00 | 76.68 |

FIGURE 3I

| A | B | C | D | E | F | G | H | I | J |
|---|---|---|---|---|---|---|---|---|---|
| 450 | CG | GLU | A | 65 | -90.491 | 17.786 | 106.332 | 1.00 | 77.45 |
| 451 | CD | GLU | A | 65 | -91.151 | 19.011 | 106.948 | 1.00 | 79.22 |
| 452 | OE1 | GLU | A | 65 | -91.825 | 18.859 | 107.995 | 1.00 | 79.11 |
| 453 | OE2 | GLU | A | 65 | -90.999 | 20.127 | 106.388 | 1.00 | 79.23 |
| 454 | C | GLU | A | 65 | -88.008 | 16.674 | 104.299 | 1.00 | 76.69 |
| 455 | O | GLU | A | 65 | -87.468 | 16.077 | 105.232 | 1.00 | 76.64 |
| 456 | N | ASN | A | 66 | -87.351 | 17.253 | 103.304 | 1.00 | 77.07 |
| 457 | CA | ASN | A | 66 | -85.904 | 17.310 | 103.197 | 1.00 | 77.55 |
| 458 | CB | ASN | A | 66 | -85.569 | 18.446 | 102.232 | 1.00 | 77.84 |
| 459 | CG | ASN | A | 66 | -86.537 | 19.623 | 102.371 | 1.00 | 78.43 |
| 460 | OD1 | ASN | A | 66 | -86.832 | 20.063 | 103.482 | 1.00 | 79.16 |
| 461 | ND2 | ASN | A | 66 | -87.051 | 20.115 | 101.249 | 1.00 | 78.36 |
| 462 | C | ASN | A | 66 | -85.172 | 17.550 | 104.520 | 1.00 | 77.66 |
| 463 | O | ASN | A | 66 | -84.447 | 16.684 | 105.021 | 1.00 | 77.65 |
| 464 | N | SER | A | 67 | -85.387 | 18.742 | 105.068 | 1.00 | 77.67 |
| 465 | CA | SER | A | 67 | -84.712 | 19.231 | 106.268 | 1.00 | 77.74 |
| 466 | CB | SER | A | 67 | -85.318 | 20.579 | 106.671 | 1.00 | 77.78 |
| 467 | OG | SER | A | 67 | -86.727 | 20.481 | 106.792 | 1.00 | 77.45 |
| 468 | C | SER | A | 67 | -84.683 | 18.305 | 107.485 | 1.00 | 77.85 |
| 469 | O | SER | A | 67 | -83.734 | 18.349 | 108.278 | 1.00 | 77.93 |
| 470 | N | THR | A | 68 | -85.713 | 17.478 | 107.634 | 1.00 | 77.74 |
| 471 | CA | THR | A | 68 | -85.826 | 16.575 | 108.779 | 1.00 | 77.68 |
| 472 | CB | THR | A | 68 | -86.746 | 15.393 | 108.440 | 1.00 | 77.66 |
| 473 | OG1 | THR | A | 68 | -87.912 | 15.871 | 107.756 | 1.00 | 77.83 |
| 474 | CG2 | THR | A | 68 | -87.301 | 14.767 | 109.716 | 1.00 | 77.56 |
| 475 | C | THR | A | 68 | -84.488 | 16.043 | 109.302 | 1.00 | 77.67 |
| 476 | O | THR | A | 68 | -84.275 | 15.965 | 110.514 | 1.00 | 77.61 |
| 477 | N | PHE | A | 69 | -83.592 | 15.679 | 108.390 | 1.00 | 77.66 |
| 478 | CA | PHE | A | 69 | -82.309 | 15.108 | 108.786 | 1.00 | 77.63 |
| 479 | CB | PHE | A | 69 | -82.122 | 13.724 | 108.153 | 1.00 | 77.52 |
| 480 | CG | PHE | A | 69 | -83.287 | 12.804 | 108.352 | 1.00 | 76.97 |
| 481 | CD1 | PHE | A | 69 | -83.546 | 12.252 | 109.593 | 1.00 | 76.96 |
| 482 | CE1 | PHE | A | 69 | -84.621 | 11.405 | 109.780 | 1.00 | 77.06 |
| 483 | CZ | PHE | A | 69 | -85.453 | 11.101 | 108.719 | 1.00 | 77.00 |
| 484 | CE2 | PHE | A | 69 | -85.201 | 11.646 | 107.475 | 1.00 | 77.00 |
| 485 | CD2 | PHE | A | 69 | -84.123 | 12.492 | 107.296 | 1.00 | 76.74 |
| 486 | C | PHE | A | 69 | -81.113 | 15.985 | 108.430 | 1.00 | 77.81 |
| 487 | O | PHE | A | 69 | -79.985 | 15.492 | 108.362 | 1.00 | 77.86 |
| 488 | N | ASP | A | 70 | -81.332 | 17.277 | 108.204 | 1.00 | 77.78 |
| 489 | CA | ASP | A | 70 | -80.197 | 18.120 | 107.846 | 1.00 | 77.79 |
| 490 | CB | ASP | A | 70 | -80.632 | 19.465 | 107.261 | 1.00 | 78.10 |
| 491 | CG | ASP | A | 70 | -81.500 | 20.261 | 108.204 | 1.00 | 79.05 |
| 492 | OD1 | ASP | A | 70 | -82.274 | 21.113 | 107.713 | 1.00 | 79.76 |
| 493 | OD2 | ASP | A | 70 | -81.480 | 20.106 | 109.444 | 1.00 | 79.98 |
| 494 | C | ASP | A | 70 | -79.237 | 18.286 | 109.023 | 1.00 | 77.42 |
| 495 | O | ASP | A | 70 | -78.149 | 18.839 | 108.872 | 1.00 | 77.46 |
| 496 | N | GLU | A | 71 | -79.646 | 17.794 | 110.190 | 1.00 | 76.84 |
| 497 | CA | GLU | A | 71 | -78.791 | 17.824 | 111.370 | 1.00 | 76.39 |
| 498 | CB | GLU | A | 71 | -79.466 | 18.565 | 112.528 | 1.00 | 76.72 |
| 499 | CG | GLU | A | 71 | -79.637 | 20.061 | 112.283 | 1.00 | 77.81 |
| 500 | CD | GLU | A | 71 | -79.450 | 20.901 | 113.540 | 1.00 | 79.41 |

FIGURE 3J

| A | B | C | D | E | F | G | H | I | J |
|---|---|---|---|---|---|---|---|---|---|
| 501 | OE1 | GLU | A | 71 | -79.341 | 20.323 | 114.647 | 1.00 | 79.94 |
| 502 | OE2 | GLU | A | 71 | -79.402 | 22.147 | 113.420 | 1.00 | 79.88 |
| 503 | C | GLU | A | 71 | -78.434 | 16.398 | 111.765 | 1.00 | 75.74 |
| 504 | O | GLU | A | 71 | -77.956 | 16.139 | 112.876 | 1.00 | 75.50 |
| 505 | N | PHE | A | 72 | -78.679 | 15.479 | 110.833 | 1.00 | 74.83 |
| 506 | CA | PHE | A | 72 | -78.382 | 14.064 | 111.016 | 1.00 | 73.85 |
| 507 | CB | PHE | A | 72 | -78.782 | 13.290 | 109.760 | 1.00 | 74.04 |
| 508 | CG | PHE | A | 72 | -78.620 | 11.803 | 109.877 | 1.00 | 74.10 |
| 509 | CD1 | PHE | A | 72 | -77.575 | 11.159 | 109.234 | 1.00 | 73.80 |
| 510 | CE1 | PHE | A | 72 | -77.424 | 9.798 | 109.329 | 1.00 | 73.80 |
| 511 | CZ | PHE | A | 72 | -78.324 | 9.055 | 110.065 | 1.00 | 74.51 |
| 512 | CE2 | PHE | A | 72 | -79.377 | 9.680 | 110.708 | 1.00 | 74.63 |
| 513 | CD2 | PHE | A | 72 | -79.523 | 11.048 | 110.609 | 1.00 | 74.10 |
| 514 | C | PHE | A | 72 | -76.900 | 13.861 | 111.312 | 1.00 | 73.03 |
| 515 | O | PHE | A | 72 | -76.529 | 12.977 | 112.090 | 1.00 | 73.05 |
| 516 | N | GLY | A | 73 | -76.060 | 14.680 | 110.685 | 1.00 | 71.87 |
| 517 | CA | GLY | A | 73 | -74.625 | 14.612 | 110.895 | 1.00 | 70.69 |
| 518 | C | GLY | A | 73 | -73.888 | 14.010 | 109.719 | 1.00 | 69.83 |
| 519 | O | GLY | A | 73 | -72.656 | 14.057 | 109.642 | 1.00 | 69.87 |
| 520 | N | HIS | A | 74 | -74.650 | 13.439 | 108.794 | 1.00 | 68.75 |
| 521 | CA | HIS | A | 74 | -74.078 | 12.820 | 107.611 | 1.00 | 67.57 |
| 522 | CB | HIS | A | 74 | -74.037 | 11.303 | 107.776 | 1.00 | 67.49 |
| 523 | CG | HIS | A | 74 | -73.715 | 10.851 | 109.168 | 1.00 | 66.51 |
| 524 | ND1 | HIS | A | 74 | -72.437 | 10.527 | 109.570 | 1.00 | 66.10 |
| 525 | CE1 | HIS | A | 74 | -72.457 | 10.154 | 110.838 | 1.00 | 65.84 |
| 526 | NE2 | HIS | A | 74 | -73.703 | 10.227 | 111.274 | 1.00 | 65.59 |
| 527 | CD2 | HIS | A | 74 | -74.508 | 10.660 | 110.249 | 1.00 | 66.42 |
| 528 | C | HIS | A | 74 | -74.921 | 13.191 | 106.403 | 1.00 | 66.95 |
| 529 | O | HIS | A | 74 | -75.683 | 14.158 | 106.445 | 1.00 | 67.33 |
| 530 | N | SER | A | 75 | -74.772 | 12.446 | 105.315 | 1.00 | 65.79 |
| 531 | CA | SER | A | 75 | -75.580 | 12.690 | 104.125 | 1.00 | 64.59 |
| 532 | CB | SER | A | 75 | -74.735 | 13.253 | 102.981 | 1.00 | 64.75 |
| 533 | OG | SER | A | 75 | -73.941 | 12.249 | 102.382 | 1.00 | 64.91 |
| 534 | C | SER | A | 75 | -76.263 | 11.394 | 103.712 | 1.00 | 63.72 |
| 535 | O | SER | A | 75 | -75.625 | 10.347 | 103.606 | 1.00 | 63.44 |
| 536 | N | ILE | A | 76 | -77.563 | 11.471 | 103.477 | 1.00 | 62.64 |
| 537 | CA | ILE | A | 76 | -78.347 | 10.284 | 103.173 | 1.00 | 61.64 |
| 538 | CB | ILE | A | 76 | -79.801 | 10.503 | 103.594 | 1.00 | 61.65 |
| 539 | CG1 | ILE | A | 76 | -79.855 | 10.744 | 105.104 | 1.00 | 61.22 |
| 540 | CD1 | ILE | A | 76 | -79.505 | 9.531 | 105.916 | 1.00 | 60.30 |
| 541 | CG2 | ILE | A | 76 | -80.663 | 9.305 | 103.195 | 1.00 | 61.36 |
| 542 | C | ILE | A | 76 | -78.271 | 9.779 | 101.733 | 1.00 | 61.23 |
| 543 | O | ILE | A | 76 | -78.657 | 10.472 | 100.781 | 1.00 | 60.88 |
| 544 | N | ASN | A | 77 | -77.785 | 8.548 | 101.594 | 1.00 | 60.50 |
| 545 | CA | ASN | A | 77 | -77.660 | 7.915 | 100.289 | 1.00 | 59.70 |
| 546 | CB | ASN | A | 77 | -76.639 | 6.774 | 100.340 | 1.00 | 59.69 |
| 547 | CG | ASN | A | 77 | -76.557 | 6.000 | 99.035 | 1.00 | 59.77 |
| 548 | OD1 | ASN | A | 77 | -76.121 | 6.525 | 98.006 | 1.00 | 59.13 |
| 549 | ND2 | ASN | A | 77 | -76.973 | 4.742 | 99.075 | 1.00 | 59.64 |
| 550 | C | ASN | A | 77 | -79.010 | 7.410 | 99.810 | 1.00 | 59.12 |
| 551 | O | ASN | A | 77 | -79.378 | 7.590 | 98.648 | 1.00 | 58.95 |

FIGURE 3K

| A | B | C | D | E | F | G | H | I | J |
|---|---|---|---|---|---|---|---|---|---|
| 552 | N | ASP | A | 78 | -79.757 | 6.796 | 100.716 | 1.00 | 58.58 |
| 553 | CA | ASP | A | 78 | -81.071 | 6.269 | 100.371 | 1.00 | 58.27 |
| 554 | CB | ASP | A | 78 | -80.938 | 4.955 | 99.591 | 1.00 | 58.61 |
| 555 | CG | ASP | A | 78 | -81.948 | 4.838 | 98.455 | 1.00 | 60.42 |
| 556 | OD1 | ASP | A | 78 | -83.168 | 4.702 | 98.734 | 1.00 | 60.92 |
| 557 | OD2 | ASP | A | 78 | -81.607 | 4.867 | 97.246 | 1.00 | 61.79 |
| 558 | C | ASP | A | 78 | -81.911 | 6.045 | 101.624 | 1.00 | 57.52 |
| 559 | O | ASP | A | 78 | -81.425 | 6.129 | 102.750 | 1.00 | 57.00 |
| 560 | N | TYR | A | 79 | -83.182 | 5.748 | 101.407 | 1.00 | 56.98 |
| 561 | CA | TYR | A | 79 | -84.116 | 5.528 | 102.495 | 1.00 | 56.43 |
| 562 | CB | TYR | A | 79 | -85.053 | 6.735 | 102.638 | 1.00 | 56.46 |
| 563 | CG | TYR | A | 79 | -85.965 | 6.926 | 101.445 | 1.00 | 57.21 |
| 564 | CD1 | TYR | A | 79 | -85.548 | 7.647 | 100.338 | 1.00 | 58.14 |
| 565 | CE1 | TYR | A | 79 | -86.374 | 7.810 | 99.236 | 1.00 | 59.98 |
| 566 | CZ | TYR | A | 79 | -87.637 | 7.240 | 99.234 | 1.00 | 60.76 |
| 567 | OH | TYR | A | 79 | -88.464 | 7.398 | 98.139 | 1.00 | 61.91 |
| 568 | CE2 | TYR | A | 79 | -88.073 | 6.516 | 100.323 | 1.00 | 59.61 |
| 569 | CD2 | TYR | A | 79 | -87.237 | 6.365 | 101.421 | 1.00 | 58.25 |
| 570 | C | TYR | A | 79 | -84.931 | 4.275 | 102.206 | 1.00 | 55.67 |
| 571 | O | TYR | A | 79 | -85.059 | 3.853 | 101.067 | 1.00 | 55.35 |
| 572 | N | SER | A | 80 | -85.491 | 3.686 | 103.245 | 1.00 | 55.30 |
| 573 | CA | SER | A | 80 | -86.341 | 2.529 | 103.061 | 1.00 | 54.89 |
| 574 | CB | SER | A | 80 | -85.538 | 1.233 | 103.109 | 1.00 | 54.78 |
| 575 | OG | SER | A | 80 | -86.410 | 0.128 | 103.084 | 1.00 | 53.76 |
| 576 | C | SER | A | 80 | -87.416 | 2.518 | 104.129 | 1.00 | 54.94 |
| 577 | O | SER | A | 80 | -87.139 | 2.362 | 105.318 | 1.00 | 54.89 |
| 578 | N | ILE | A | 81 | -88.652 | 2.682 | 103.691 | 1.00 | 54.80 |
| 579 | CA | ILE | A | 81 | -89.765 | 2.695 | 104.604 | 1.00 | 54.71 |
| 580 | CB | ILE | A | 81 | -90.858 | 3.608 | 104.068 | 1.00 | 54.69 |
| 581 | CG1 | ILE | A | 81 | -90.223 | 4.877 | 103.504 | 1.00 | 55.47 |
| 582 | CD1 | ILE | A | 81 | -90.789 | 6.149 | 104.053 | 1.00 | 55.70 |
| 583 | CG2 | ILE | A | 81 | -91.889 | 3.891 | 105.149 | 1.00 | 55.04 |
| 584 | C | ILE | A | 81 | -90.326 | 1.309 | 104.827 | 1.00 | 54.66 |
| 585 | O | ILE | A | 81 | -90.635 | 0.582 | 103.879 | 1.00 | 54.51 |
| 586 | N | SER | A | 82 | -90.442 | 0.942 | 106.095 | 1.00 | 54.62 |
| 587 | CA | SER | A | 82 | -91.079 | -0.299 | 106.457 | 1.00 | 54.72 |
| 588 | CB | SER | A | 82 | -91.280 | -0.350 | 107.976 | 1.00 | 55.07 |
| 589 | OG | SER | A | 82 | -91.880 | -1.575 | 108.381 | 1.00 | 55.75 |
| 590 | C | SER | A | 82 | -92.433 | -0.340 | 105.750 | 1.00 | 54.55 |
| 591 | O | SER | A | 82 | -93.040 | 0.695 | 105.498 | 1.00 | 54.24 |
| 592 | N | PRO | A | 83 | -92.909 | -1.532 | 105.423 | 1.00 | 54.57 |
| 593 | CA | PRO | A | 83 | -94.216 | -1.669 | 104.784 | 1.00 | 54.68 |
| 594 | CB | PRO | A | 83 | -94.440 | -3.181 | 104.779 | 1.00 | 54.57 |
| 595 | CG | PRO | A | 83 | -93.083 | -3.768 | 104.845 | 1.00 | 54.64 |
| 596 | CD | PRO | A | 83 | -92.249 | -2.828 | 105.647 | 1.00 | 54.52 |
| 597 | C | PRO | A | 83 | -95.223 | -1.015 | 105.708 | 1.00 | 54.77 |
| 598 | O | PRO | A | 83 | -96.334 | -0.658 | 105.319 | 1.00 | 54.48 |
| 599 | N | ASP | A | 84 | -94.781 | -0.858 | 106.950 | 1.00 | 54.99 |
| 600 | CA | ASP | A | 84 | -95.563 | -0.294 | 108.040 | 1.00 | 55.12 |
| 601 | CB | ASP | A | 84 | -94.763 | -0.421 | 109.331 | 1.00 | 55.15 |
| 602 | CG | ASP | A | 84 | -95.363 | -1.402 | 110.258 | 1.00 | 55.64 |

FIGURE 3L

| A | B | C | D | E | F | G | H | I | J |
|---|---|---|---|---|---|---|---|---|---|
| 603 | OD1 | ASP | A | 84 | -94.765 | -1.671 | 111.312 | 1.00 | 56.59 |
| 604 | OD2 | ASP | A | 84 | -96.449 | -1.958 | 110.002 | 1.00 | 57.31 |
| 605 | C | ASP | A | 84 | -95.918 | 1.165 | 107.914 | 1.00 | 55.01 |
| 606 | O | ASP | A | 84 | -96.973 | 1.595 | 108.387 | 1.00 | 55.07 |
| 607 | N | GLY | A | 85 | -95.017 | 1.929 | 107.312 | 1.00 | 54.70 |
| 608 | CA | GLY | A | 85 | -95.158 | 3.366 | 107.279 | 1.00 | 54.30 |
| 609 | C | GLY | A | 85 | -94.753 | 3.893 | 108.647 | 1.00 | 54.01 |
| 610 | O | GLY | A | 85 | -94.739 | 5.098 | 108.871 | 1.00 | 54.26 |
| 611 | N | GLN | A | 86 | -94.407 | 2.979 | 109.554 | 1.00 | 53.65 |
| 612 | CA | GLN | A | 86 | -94.053 | 3.319 | 110.934 | 1.00 | 53.40 |
| 613 | CB | GLN | A | 86 | -94.536 | 2.226 | 111.889 | 1.00 | 53.22 |
| 614 | CG | GLN | A | 86 | -96.039 | 2.080 | 111.914 | 1.00 | 53.47 |
| 615 | CD | GLN | A | 86 | -96.486 | 0.894 | 112.723 | 1.00 | 53.71 |
| 616 | OE1 | GLN | A | 86 | -95.703 | 0.338 | 113.497 | 1.00 | 54.47 |
| 617 | NE2 | GLN | A | 86 | -97.740 | 0.490 | 112.546 | 1.00 | 52.64 |
| 618 | C | GLN | A | 86 | -92.571 | 3.581 | 111.179 | 1.00 | 53.30 |
| 619 | O | GLN | A | 86 | -92.183 | 3.988 | 112.270 | 1.00 | 53.42 |
| 620 | N | PHE | A | 87 | -91.733 | 3.329 | 110.183 | 1.00 | 53.22 |
| 621 | CA | PHE | A | 87 | -90.314 | 3.607 | 110.333 | 1.00 | 52.63 |
| 622 | CB | PHE | A | 87 | -89.601 | 2.456 | 111.038 | 1.00 | 52.99 |
| 623 | CG | PHE | A | 87 | -90.205 | 2.066 | 112.355 | 1.00 | 53.72 |
| 624 | CD1 | PHE | A | 87 | -89.882 | 2.751 | 113.515 | 1.00 | 54.78 |
| 625 | CE1 | PHE | A | 87 | -90.430 | 2.378 | 114.733 | 1.00 | 55.42 |
| 626 | CZ | PHE | A | 87 | -91.302 | 1.309 | 114.800 | 1.00 | 54.70 |
| 627 | CE2 | PHE | A | 87 | -91.623 | 0.619 | 113.652 | 1.00 | 54.87 |
| 628 | CD2 | PHE | A | 87 | -91.071 | 0.993 | 112.438 | 1.00 | 53.75 |
| 629 | C | PHE | A | 87 | -89.675 | 3.794 | 108.981 | 1.00 | 52.09 |
| 630 | O | PHE | A | 87 | -90.082 | 3.170 | 108.004 | 1.00 | 51.94 |
| 631 | N | ILE | A | 88 | -88.673 | 4.659 | 108.920 | 1.00 | 51.55 |
| 632 | CA | ILE | A | 88 | -87.891 | 4.799 | 107.704 | 1.00 | 51.12 |
| 633 | CB | ILE | A | 88 | -88.022 | 6.200 | 107.088 | 1.00 | 51.27 |
| 634 | CG1 | ILE | A | 88 | -87.101 | 6.316 | 105.869 | 1.00 | 52.21 |
| 635 | CD1 | ILE | A | 88 | -87.378 | 7.528 | 104.998 | 1.00 | 52.90 |
| 636 | CG2 | ILE | A | 88 | -87.682 | 7.279 | 108.103 | 1.00 | 51.87 |
| 637 | C | ILE | A | 88 | -86.431 | 4.442 | 107.991 | 1.00 | 50.47 |
| 638 | O | ILE | A | 88 | -85.828 | 4.932 | 108.948 | 1.00 | 50.53 |
| 639 | N | LEU | A | 89 | -85.877 | 3.551 | 107.182 | 1.00 | 49.59 |
| 640 | CA | LEU | A | 89 | -84.487 | 3.162 | 107.331 | 1.00 | 48.54 |
| 641 | CB | LEU | A | 89 | -84.263 | 1.793 | 106.705 | 1.00 | 48.62 |
| 642 | CG | LEU | A | 89 | -82.852 | 1.224 | 106.747 | 1.00 | 48.60 |
| 643 | CD1 | LEU | A | 89 | -82.590 | 0.405 | 105.497 | 1.00 | 49.00 |
| 644 | CD2 | LEU | A | 89 | -82.681 | 0.379 | 107.982 | 1.00 | 48.32 |
| 645 | C | LEU | A | 89 | -83.647 | 4.198 | 106.612 | 1.00 | 47.95 |
| 646 | O | LEU | A | 89 | -83.940 | 4.562 | 105.479 | 1.00 | 47.88 |
| 647 | N | LEU | A | 90 | -82.610 | 4.689 | 107.270 | 1.00 | 47.21 |
| 648 | CA | LEU | A | 90 | -81.755 | 5.692 | 106.656 | 1.00 | 46.75 |
| 649 | CB | LEU | A | 90 | -81.589 | 6.896 | 107.578 | 1.00 | 47.00 |
| 650 | CG | LEU | A | 90 | -82.872 | 7.713 | 107.691 | 1.00 | 47.93 |
| 651 | CD1 | LEU | A | 90 | -82.628 | 8.934 | 108.555 | 1.00 | 49.24 |
| 652 | CD2 | LEU | A | 90 | -83.339 | 8.118 | 106.301 | 1.00 | 48.21 |
| 653 | C | LEU | A | 90 | -80.407 | 5.089 | 106.335 | 1.00 | 45.87 |

FIGURE 3M

| A | B | C | D | E | F | G | H | I | J |
|---|---|---|---|---|---|---|---|---|---|
| 654 | O | LEU | A | 90 | -79.722 | 4.556 | 107.211 | 1.00 | 45.76 |
| 655 | N | GLU | A | 91 | -80.029 | 5.181 | 105.070 | 1.00 | 44.80 |
| 656 | CA | GLU | A | 91 | -78.790 | 4.584 | 104.613 | 1.00 | 43.70 |
| 657 | CB | GLU | A | 91 | -79.048 | 3.792 | 103.334 | 1.00 | 43.58 |
| 658 | CG | GLU | A | 91 | -77.796 | 3.334 | 102.611 | 1.00 | 43.64 |
| 659 | CD | GLU | A | 91 | -78.128 | 2.469 | 101.414 | 1.00 | 43.67 |
| 660 | OE1 | GLU | A | 91 | -77.745 | 2.853 | 100.295 | 1.00 | 43.86 |
| 661 | OE2 | GLU | A | 91 | -78.781 | 1.416 | 101.601 | 1.00 | 42.46 |
| 662 | C | GLU | A | 91 | -77.725 | 5.636 | 104.380 | 1.00 | 42.84 |
| 663 | O | GLU | A | 91 | -77.952 | 6.613 | 103.664 | 1.00 | 42.25 |
| 664 | N | TYR | A | 92 | -76.561 | 5.432 | 104.990 | 1.00 | 42.10 |
| 665 | CA | TYR | A | 92 | -75.464 | 6.369 | 104.811 | 1.00 | 41.77 |
| 666 | CB | TYR | A | 92 | -75.600 | 7.567 | 105.766 | 1.00 | 41.94 |
| 667 | CG | TYR | A | 92 | -75.429 | 7.233 | 107.222 | 1.00 | 40.43 |
| 668 | CD1 | TYR | A | 92 | -76.391 | 6.521 | 107.905 | 1.00 | 40.23 |
| 669 | CE1 | TYR | A | 92 | -76.221 | 6.212 | 109.242 | 1.00 | 41.40 |
| 670 | CZ | TYR | A | 92 | -75.087 | 6.638 | 109.895 | 1.00 | 40.80 |
| 671 | OH | TYR | A | 92 | -74.895 | 6.340 | 111.221 | 1.00 | 42.34 |
| 672 | CE2 | TYR | A | 92 | -74.121 | 7.340 | 109.225 | 1.00 | 39.74 |
| 673 | CD2 | TYR | A | 92 | -74.295 | 7.634 | 107.910 | 1.00 | 39.63 |
| 674 | C | TYR | A | 92 | -74.107 | 5.686 | 104.954 | 1.00 | 41.71 |
| 675 | O | TYR | A | 92 | -74.023 | 4.546 | 105.419 | 1.00 | 41.24 |
| 676 | N | ASN | A | 93 | -73.055 | 6.400 | 104.555 | 1.00 | 41.38 |
| 677 | CA | ASN | A | 93 | -71.706 | 5.859 | 104.543 | 1.00 | 41.55 |
| 678 | CB | ASN | A | 93 | -71.298 | 5.352 | 105.925 | 1.00 | 42.02 |
| 679 | CG | ASN | A | 93 | -71.043 | 6.482 | 106.901 | 1.00 | 43.73 |
| 680 | OD1 | ASN | A | 93 | -70.671 | 7.588 | 106.502 | 1.00 | 45.09 |
| 681 | ND2 | ASN | A | 93 | -71.249 | 6.213 | 108.189 | 1.00 | 44.17 |
| 682 | C | ASN | A | 93 | -71.606 | 4.747 | 103.507 | 1.00 | 40.94 |
| 683 | O | ASN | A | 93 | -70.962 | 3.725 | 103.722 | 1.00 | 40.20 |
| 684 | N | TYR | A | 94 | -72.274 | 4.976 | 102.386 | 1.00 | 40.86 |
| 685 | CA | TYR | A | 94 | -72.307 | 4.056 | 101.270 | 1.00 | 40.82 |
| 686 | CB | TYR | A | 94 | -73.217 | 4.620 | 100.179 | 1.00 | 41.16 |
| 687 | CG | TYR | A | 94 | -73.168 | 3.873 | 98.858 | 1.00 | 42.03 |
| 688 | CD1 | TYR | A | 94 | -73.912 | 2.716 | 98.667 | 1.00 | 41.93 |
| 689 | CE1 | TYR | A | 94 | -73.881 | 2.037 | 97.464 | 1.00 | 42.75 |
| 690 | CZ | TYR | A | 94 | -73.098 | 2.508 | 96.431 | 1.00 | 42.95 |
| 691 | OH | TYR | A | 94 | -73.071 | 1.818 | 95.239 | 1.00 | 45.07 |
| 692 | CE2 | TYR | A | 94 | -72.354 | 3.656 | 96.586 | 1.00 | 42.83 |
| 693 | CD2 | TYR | A | 94 | -72.394 | 4.340 | 97.797 | 1.00 | 41.85 |
| 694 | C | TYR | A | 94 | -70.924 | 3.788 | 100.686 | 1.00 | 40.68 |
| 695 | O | TYR | A | 94 | -70.237 | 4.702 | 100.231 | 1.00 | 41.17 |
| 696 | N | VAL | A | 95 | -70.506 | 2.530 | 100.722 | 1.00 | 39.96 |
| 697 | CA | VAL | A | 95 | -69.270 | 2.140 | 100.063 | 1.00 | 39.34 |
| 698 | CB | VAL | A | 95 | -68.164 | 1.733 | 101.047 | 1.00 | 39.31 |
| 699 | CG1 | VAL | A | 95 | -67.994 | 2.793 | 102.125 | 1.00 | 39.60 |
| 700 | CG2 | VAL | A | 95 | -68.486 | 0.402 | 101.674 | 1.00 | 40.76 |
| 701 | C | VAL | A | 95 | -69.614 | 0.999 | 99.095 | 1.00 | 38.41 |
| 702 | O | VAL | A | 95 | -69.979 | -0.115 | 99.499 | 1.00 | 38.29 |
| 703 | N | LYS | A | 96 | -69.545 | 1.317 | 97.812 | 1.00 | 37.32 |
| 704 | CA | LYS | A | 96 | -69.818 | 0.360 | 96.759 | 1.00 | 36.43 |

FIGURE 3N

| A | B | C | D | E | F | G | H | I | J |
|---|---|---|---|---|---|---|---|---|---|
| 705 | CB | LYS | A | 96 | -69.625 | 1.039 | 95.410 | 1.00 | 36.77 |
| 706 | CG | LYS | A | 96 | -69.569 | 0.073 | 94.248 | 1.00 | 37.54 |
| 707 | CD | LYS | A | 96 | -69.843 | 0.780 | 92.938 | 1.00 | 36.45 |
| 708 | CE | LYS | A | 96 | -69.948 | -0.234 | 91.800 | 1.00 | 36.87 |
| 709 | NZ | LYS | A | 96 | -68.755 | -1.131 | 91.791 | 1.00 | 34.18 |
| 710 | C | LYS | A | 96 | -68.866 | -0.820 | 96.820 | 1.00 | 35.47 |
| 711 | O | LYS | A | 96 | -67.672 | -0.634 | 97.073 | 1.00 | 34.98 |
| 712 | N | GLN | A | 97 | -69.385 | -2.035 | 96.634 | 1.00 | 33.71 |
| 713 | CA | GLN | A | 97 | -68.473 | -3.159 | 96.451 | 1.00 | 32.87 |
| 714 | CB | GLN | A | 97 | -68.746 | -4.338 | 97.387 | 1.00 | 33.00 |
| 715 | CG | GLN | A | 97 | -67.828 | -5.535 | 97.076 | 1.00 | 34.97 |
| 716 | CD | GLN | A | 97 | -67.804 | -6.613 | 98.149 | 1.00 | 36.12 |
| 717 | OE1 | GLN | A | 97 | -66.746 | -6.910 | 98.709 | 1.00 | 37.95 |
| 718 | NE2 | GLN | A | 97 | -68.951 | -7.218 | 98.414 | 1.00 | 37.01 |
| 719 | C | GLN | A | 97 | -68.519 | -3.570 | 94.969 | 1.00 | 31.95 |
| 720 | O | GLN | A | 97 | -67.883 | -2.926 | 94.108 | 1.00 | 30.84 |
| 721 | N | TRP | A | 98 | -69.303 | -4.601 | 94.670 | 1.00 | 30.50 |
| 722 | CA | TRP | A | 98 | -69.412 | -5.071 | 93.300 | 1.00 | 30.31 |
| 723 | CB | TRP | A | 98 | -69.458 | -6.607 | 93.235 | 1.00 | 29.81 |
| 724 | CG | TRP | A | 98 | -68.354 | -7.265 | 94.042 | 1.00 | 26.78 |
| 725 | CD1 | TRP | A | 98 | -68.487 | -8.325 | 94.896 | 1.00 | 25.79 |
| 726 | NE1 | TRP | A | 98 | -67.276 | -8.642 | 95.459 | 1.00 | 24.42 |
| 727 | CE2 | TRP | A | 98 | -66.318 | -7.793 | 94.961 | 1.00 | 24.75 |
| 728 | CD2 | TRP | A | 98 | -66.961 | -6.904 | 94.075 | 1.00 | 24.84 |
| 729 | CE3 | TRP | A | 98 | -66.190 | -5.931 | 93.433 | 1.00 | 22.20 |
| 730 | CZ3 | TRP | A | 98 | -64.840 | -5.866 | 93.696 | 1.00 | 21.42 |
| 731 | CH2 | TRP | A | 98 | -64.227 | -6.765 | 94.573 | 1.00 | 23.42 |
| 732 | CZ2 | TRP | A | 98 | -64.951 | -7.723 | 95.231 | 1.00 | 23.60 |
| 733 | C | TRP | A | 98 | -70.596 | -4.414 | 92.593 | 1.00 | 30.53 |
| 734 | O | TRP | A | 98 | -70.938 | -3.275 | 92.887 | 1.00 | 31.01 |
| 735 | N | ARG | A | 99 | -71.217 | -5.110 | 91.652 | 1.00 | 30.41 |
| 736 | CA | ARG | A | 99 | -72.287 | -4.486 | 90.884 | 1.00 | 29.78 |
| 737 | CB | ARG | A | 99 | -72.688 | -5.349 | 89.710 | 1.00 | 30.16 |
| 738 | CG | ARG | A | 99 | -73.689 | -4.661 | 88.806 | 1.00 | 30.00 |
| 739 | CD | ARG | A | 99 | -74.321 | -5.596 | 87.831 | 1.00 | 32.10 |
| 740 | NE | ARG | A | 99 | -73.349 | -6.235 | 86.953 | 1.00 | 31.79 |
| 741 | CZ | ARG | A | 99 | -72.956 | -5.724 | 85.795 | 1.00 | 35.74 |
| 742 | NH1 | ARG | A | 99 | -73.430 | -4.546 | 85.405 | 1.00 | 34.55 |
| 743 | NH2 | ARG | A | 99 | -72.078 | -6.379 | 85.022 | 1.00 | 36.45 |
| 744 | C | ARG | A | 99 | -73.530 | -4.164 | 91.691 | 1.00 | 29.82 |
| 745 | O | ARG | A | 99 | -74.207 | -3.157 | 91.452 | 1.00 | 29.36 |
| 746 | N | HIS | A | 100 | -73.852 | -5.028 | 92.634 | 1.00 | 29.79 |
| 747 | CA | HIS | A | 100 | -75.030 | -4.786 | 93.450 | 1.00 | 30.01 |
| 748 | CB | HIS | A | 100 | -76.027 | -5.943 | 93.328 | 1.00 | 29.65 |
| 749 | CG | HIS | A | 100 | -76.377 | -6.288 | 91.913 | 1.00 | 30.33 |
| 750 | ND1 | HIS | A | 100 | -77.319 | -5.587 | 91.188 | 1.00 | 29.96 |
| 751 | CE1 | HIS | A | 100 | -77.422 | -6.114 | 89.978 | 1.00 | 30.33 |
| 752 | NE2 | HIS | A | 100 | -76.571 | -7.122 | 89.889 | 1.00 | 31.44 |
| 753 | CD2 | HIS | A | 100 | -75.903 | -7.254 | 91.085 | 1.00 | 28.82 |
| 754 | C | HIS | A | 100 | -74.631 | -4.605 | 94.904 | 1.00 | 29.88 |
| 755 | O | HIS | A | 100 | -75.307 | -3.893 | 95.644 | 1.00 | 29.96 |

FIGURE 3O

| A | B | C | D | E | F | G | H | I | J |
|---|---|---|---|---|---|---|---|---|---|
| 756 | N | SER | A | 101 | -73.516 | -5.222 | 95.285 | 1.00 | 29.75 |
| 757 | CA | SER | A | 101 | -73.077 | -5.245 | 96.670 | 1.00 | 30.71 |
| 758 | CB | SER | A | 101 | -72.126 | -6.415 | 96.914 | 1.00 | 30.60 |
| 759 | OG | SER | A | 101 | -70.964 | -6.315 | 96.115 | 1.00 | 30.67 |
| 760 | C | SER | A | 101 | -72.463 | -3.951 | 97.192 | 1.00 | 31.43 |
| 761 | O | SER | A | 101 | -71.795 | -3.209 | 96.475 | 1.00 | 31.45 |
| 762 | N | TYR | A | 102 | -72.729 | -3.667 | 98.451 | 1.00 | 32.61 |
| 763 | CA | TYR | A | 102 | -72.153 | -2.489 | 99.073 | 1.00 | 34.02 |
| 764 | CB | TYR | A | 102 | -72.795 | -1.201 | 98.554 | 1.00 | 33.97 |
| 765 | CG | TYR | A | 102 | -74.265 | -1.034 | 98.891 | 1.00 | 34.51 |
| 766 | CD1 | TYR | A | 102 | -74.671 | -0.554 | 100.132 | 1.00 | 34.44 |
| 767 | CE1 | TYR | A | 102 | -76.017 | -0.393 | 100.436 | 1.00 | 34.19 |
| 768 | CZ | TYR | A | 102 | -76.968 | -0.688 | 99.482 | 1.00 | 36.01 |
| 769 | OH | TYR | A | 102 | -78.312 | -0.527 | 99.758 | 1.00 | 37.07 |
| 770 | CE2 | TYR | A | 102 | -76.590 | -1.153 | 98.230 | 1.00 | 35.53 |
| 771 | CD2 | TYR | A | 102 | -75.247 | -1.322 | 97.945 | 1.00 | 34.87 |
| 772 | C | TYR | A | 102 | -72.281 | -2.547 | 100.566 | 1.00 | 34.63 |
| 773 | O | TYR | A | 102 | -72.993 | -3.380 | 101.130 | 1.00 | 34.79 |
| 774 | N | THR | A | 103 | -71.571 | -1.640 | 101.200 | 1.00 | 35.57 |
| 775 | CA | THR | A | 103 | -71.584 | -1.535 | 102.632 | 1.00 | 36.51 |
| 776 | CB | THR | A | 103 | -70.182 | -1.745 | 103.149 | 1.00 | 36.49 |
| 777 | OG1 | THR | A | 103 | -70.038 | -3.123 | 103.533 | 1.00 | 37.55 |
| 778 | CG2 | THR | A | 103 | -69.993 | -0.988 | 104.434 | 1.00 | 37.30 |
| 779 | C | THR | A | 103 | -72.088 | -0.153 | 102.988 | 1.00 | 37.41 |
| 780 | O | THR | A | 103 | -71.922 | 0.800 | 102.214 | 1.00 | 36.93 |
| 781 | N | ALA | A | 104 | -72.696 | -0.041 | 104.161 | 1.00 | 38.57 |
| 782 | CA | ALA | A | 104 | -73.281 | 1.216 | 104.570 | 1.00 | 40.16 |
| 783 | CB | ALA | A | 104 | -74.518 | 1.506 | 103.702 | 1.00 | 39.76 |
| 784 | C | ALA | A | 104 | -73.661 | 1.229 | 106.054 | 1.00 | 41.38 |
| 785 | O | ALA | A | 104 | -73.799 | 0.181 | 106.696 | 1.00 | 41.40 |
| 786 | N | SER | A | 105 | -73.800 | 2.432 | 106.596 | 1.00 | 42.97 |
| 787 | CA | SER | A | 105 | -74.254 | 2.611 | 107.967 | 1.00 | 44.31 |
| 788 | CB | SER | A | 105 | -73.699 | 3.900 | 108.551 | 1.00 | 44.20 |
| 789 | OG | SER | A | 105 | -72.328 | 3.796 | 108.864 | 1.00 | 44.43 |
| 790 | C | SER | A | 105 | -75.769 | 2.709 | 107.928 | 1.00 | 45.32 |
| 791 | O | SER | A | 105 | -76.356 | 3.008 | 106.886 | 1.00 | 45.47 |
| 792 | N | TYR | A | 106 | -76.408 | 2.476 | 109.063 | 1.00 | 46.70 |
| 793 | CA | TYR | A | 106 | -77.859 | 2.545 | 109.112 | 1.00 | 47.94 |
| 794 | CB | TYR | A | 106 | -78.464 | 1.154 | 108.886 | 1.00 | 47.65 |
| 795 | CG | TYR | A | 106 | -78.255 | 0.642 | 107.477 | 1.00 | 48.49 |
| 796 | CD1 | TYR | A | 106 | -77.163 | -0.160 | 107.156 | 1.00 | 48.56 |
| 797 | CE1 | TYR | A | 106 | -76.959 | -0.606 | 105.861 | 1.00 | 48.75 |
| 798 | CZ | TYR | A | 106 | -77.854 | -0.258 | 104.870 | 1.00 | 48.53 |
| 799 | OH | TYR | A | 106 | -77.676 | -0.696 | 103.583 | 1.00 | 47.41 |
| 800 | CE2 | TYR | A | 106 | -78.936 | 0.541 | 105.164 | 1.00 | 49.52 |
| 801 | CD2 | TYR | A | 106 | -79.130 | 0.989 | 106.461 | 1.00 | 48.40 |
| 802 | C | TYR | A | 106 | -78.415 | 3.171 | 110.389 | 1.00 | 48.72 |
| 803 | O | TYR | A | 106 | -77.926 | 2.932 | 111.488 | 1.00 | 49.04 |
| 804 | N | ASP | A | 107 | -79.434 | 3.996 | 110.215 | 1.00 | 49.97 |
| 805 | CA | ASP | A | 107 | -80.176 | 4.552 | 111.330 | 1.00 | 51.26 |
| 806 | CB | ASP | A | 107 | -79.841 | 6.019 | 111.562 | 1.00 | 51.15 |

FIGURE 3P

| A | B | C | D | E | F | G | H | I | J |
|---|---|---|---|---|---|---|---|---|---|
| 807 | CG | ASP | A | 107 | -78.522 | 6.198 | 112.262 | 1.00 | 51.39 |
| 808 | OD1 | ASP | A | 107 | -78.343 | 5.617 | 113.347 | 1.00 | 50.59 |
| 809 | OD2 | ASP | A | 107 | -77.593 | 6.879 | 111.793 | 1.00 | 52.74 |
| 810 | C | ASP | A | 107 | -81.647 | 4.386 | 111.023 | 1.00 | 52.24 |
| 811 | O | ASP | A | 107 | -82.090 | 4.631 | 109.895 | 1.00 | 52.43 |
| 812 | N | ILE | A | 108 | -82.386 | 3.929 | 112.024 | 1.00 | 53.27 |
| 813 | CA | ILE | A | 108 | -83.814 | 3.747 | 111.907 | 1.00 | 54.46 |
| 814 | CB | ILE | A | 108 | -84.248 | 2.509 | 112.681 | 1.00 | 54.40 |
| 815 | CG1 | ILE | A | 108 | -83.414 | 1.300 | 112.263 | 1.00 | 54.06 |
| 816 | CD1 | ILE | A | 108 | -83.603 | 0.109 | 113.152 | 1.00 | 53.98 |
| 817 | CG2 | ILE | A | 108 | -85.731 | 2.262 | 112.466 | 1.00 | 54.24 |
| 818 | C | ILE | A | 108 | -84.495 | 4.949 | 112.510 | 1.00 | 55.70 |
| 819 | O | ILE | A | 108 | -84.175 | 5.358 | 113.625 | 1.00 | 56.05 |
| 820 | N | TYR | A | 109 | -85.452 | 5.508 | 111.786 | 1.00 | 56.99 |
| 821 | CA | TYR | A | 109 | -86.158 | 6.679 | 112.267 | 1.00 | 58.18 |
| 822 | CB | TYR | A | 109 | -86.000 | 7.808 | 111.258 | 1.00 | 58.13 |
| 823 | CG | TYR | A | 109 | -86.724 | 9.070 | 111.635 | 1.00 | 58.70 |
| 824 | CD1 | TYR | A | 109 | -86.180 | 9.951 | 112.551 | 1.00 | 58.38 |
| 825 | CE1 | TYR | A | 109 | -86.837 | 11.108 | 112.897 | 1.00 | 59.66 |
| 826 | CZ | TYR | A | 109 | -88.056 | 11.399 | 112.323 | 1.00 | 60.37 |
| 827 | OH | TYR | A | 109 | -88.707 | 12.557 | 112.673 | 1.00 | 61.64 |
| 828 | CE2 | TYR | A | 109 | -88.621 | 10.539 | 111.407 | 1.00 | 60.00 |
| 829 | CD2 | TYR | A | 109 | -87.956 | 9.381 | 111.071 | 1.00 | 59.25 |
| 830 | C | TYR | A | 109 | -87.636 | 6.381 | 112.503 | 1.00 | 59.21 |
| 831 | O | TYR | A | 109 | -88.353 | 5.994 | 111.578 | 1.00 | 59.31 |
| 832 | N | ASP | A | 110 | -88.084 | 6.563 | 113.745 | 1.00 | 60.39 |
| 833 | CA | ASP | A | 110 | -89.485 | 6.369 | 114.108 | 1.00 | 61.55 |
| 834 | CB | ASP | A | 110 | -89.647 | 6.365 | 115.626 | 1.00 | 61.48 |
| 835 | CG | ASP | A | 110 | -91.000 | 5.839 | 116.072 | 1.00 | 61.56 |
| 836 | OD1 | ASP | A | 110 | -92.038 | 6.409 | 115.667 | 1.00 | 61.84 |
| 837 | OD2 | ASP | A | 110 | -91.120 | 4.862 | 116.843 | 1.00 | 61.51 |
| 838 | C | ASP | A | 110 | -90.313 | 7.494 | 113.509 | 1.00 | 62.57 |
| 839 | O | ASP | A | 110 | -90.068 | 8.666 | 113.781 | 1.00 | 62.64 |
| 840 | N | LEU | A | 111 | -91.298 | 7.132 | 112.699 | 1.00 | 63.95 |
| 841 | CA | LEU | A | 111 | -92.101 | 8.117 | 111.991 | 1.00 | 65.62 |
| 842 | CB | LEU | A | 111 | -92.821 | 7.452 | 110.816 | 1.00 | 65.53 |
| 843 | CG | LEU | A | 111 | -91.945 | 7.211 | 109.587 | 1.00 | 65.20 |
| 844 | CD1 | LEU | A | 111 | -91.671 | 8.533 | 108.898 | 1.00 | 65.10 |
| 845 | CD2 | LEU | A | 111 | -92.590 | 6.243 | 108.625 | 1.00 | 64.19 |
| 846 | C | LEU | A | 111 | -93.105 | 8.869 | 112.863 | 1.00 | 66.86 |
| 847 | O | LEU | A | 111 | -93.350 | 10.061 | 112.649 | 1.00 | 67.09 |
| 848 | N | ASN | A | 112 | -93.699 | 8.175 | 113.829 | 1.00 | 68.18 |
| 849 | CA | ASN | A | 112 | -94.687 | 8.813 | 114.694 | 1.00 | 69.43 |
| 850 | CB | ASN | A | 112 | -95.815 | 7.847 | 115.063 | 1.00 | 69.91 |
| 851 | CG | ASN | A | 112 | -96.951 | 7.868 | 114.043 | 1.00 | 71.54 |
| 852 | OD1 | ASN | A | 112 | -97.853 | 8.716 | 114.111 | 1.00 | 73.34 |
| 853 | ND2 | ASN | A | 112 | -96.905 | 6.947 | 113.085 | 1.00 | 72.43 |
| 854 | C | ASN | A | 112 | -94.074 | 9.498 | 115.917 | 1.00 | 69.67 |
| 855 | O | ASN | A | 112 | -94.454 | 10.618 | 116.255 | 1.00 | 69.91 |
| 856 | N | LYS | A | 113 | -93.130 | 8.834 | 116.576 | 1.00 | 69.67 |
| 857 | CA | LYS | A | 113 | -92.411 | 9.467 | 117.666 | 1.00 | 69.79 |

FIGURE 3Q

| A | B | C | D | E | F | G | H | I | J |
|---|---|---|---|---|---|---|---|---|---|
| 858 | CB | LYS | A | 113 | -91.581 | 8.445 | 118.432 | 1.00 | 69.92 |
| 859 | CG | LYS | A | 113 | -92.323 | 7.474 | 119.317 | 1.00 | 71.09 |
| 860 | CD | LYS | A | 113 | -91.307 | 6.839 | 120.266 | 1.00 | 73.31 |
| 861 | CE | LYS | A | 113 | -91.738 | 5.475 | 120.779 | 1.00 | 74.59 |
| 862 | NZ | LYS | A | 113 | -92.421 | 5.556 | 122.104 | 1.00 | 75.40 |
| 863 | C | LYS | A | 113 | -91.429 | 10.414 | 116.999 | 1.00 | 69.62 |
| 864 | O | LYS | A | 113 | -90.600 | 11.044 | 117.657 | 1.00 | 69.51 |
| 865 | N | ARG | A | 114 | -91.531 | 10.490 | 115.676 | 1.00 | 69.50 |
| 866 | CA | ARG | A | 114 | -90.529 | 11.161 | 114.843 | 1.00 | 69.30 |
| 867 | CB | ARG | A | 114 | -91.101 | 12.337 | 114.026 | 1.00 | 69.52 |
| 868 | CG | ARG | A | 114 | -91.369 | 13.633 | 114.748 | 1.00 | 70.06 |
| 869 | CD | ARG | A | 114 | -91.489 | 14.829 | 113.791 | 1.00 | 71.10 |
| 870 | NE | ARG | A | 114 | -92.790 | 14.901 | 113.115 | 1.00 | 71.72 |
| 871 | CZ | ARG | A | 114 | -93.128 | 15.839 | 112.231 | 1.00 | 71.44 |
| 872 | NH1 | ARG | A | 114 | -94.333 | 15.827 | 111.677 | 1.00 | 71.11 |
| 873 | NH2 | ARG | A | 114 | -92.261 | 16.789 | 111.897 | 1.00 | 71.05 |
| 874 | C | ARG | A | 114 | -89.199 | 11.453 | 115.552 | 1.00 | 68.86 |
| 875 | O | ARG | A | 114 | -88.787 | 12.597 | 115.691 | 1.00 | 68.68 |
| 876 | N | GLN | A | 115 | -88.545 | 10.390 | 116.011 | 1.00 | 68.59 |
| 877 | CA | GLN | A | 115 | -87.224 | 10.501 | 116.619 | 1.00 | 68.27 |
| 878 | CB | GLN | A | 115 | -87.286 | 10.587 | 118.152 | 1.00 | 68.48 |
| 879 | CG | GLN | A | 115 | -87.726 | 9.325 | 118.890 | 1.00 | 68.71 |
| 880 | CD | GLN | A | 115 | -88.312 | 9.644 | 120.261 | 1.00 | 68.76 |
| 881 | OE1 | GLN | A | 115 | -89.533 | 9.723 | 120.413 | 1.00 | 69.09 |
| 882 | NE2 | GLN | A | 115 | -87.448 | 9.843 | 121.250 | 1.00 | 67.97 |
| 883 | C | GLN | A | 115 | -86.331 | 9.363 | 116.139 | 1.00 | 67.81 |
| 884 | O | GLN | A | 115 | -86.814 | 8.327 | 115.682 | 1.00 | 68.07 |
| 885 | N | LEU | A | 116 | -85.028 | 9.584 | 116.241 | 1.00 | 66.96 |
| 886 | CA | LEU | A | 116 | -84.010 | 8.666 | 115.760 | 1.00 | 66.14 |
| 887 | CB | LEU | A | 116 | -82.740 | 9.482 | 115.521 | 1.00 | 66.09 |
| 888 | CG | LEU | A | 116 | -81.798 | 9.189 | 114.366 | 1.00 | 66.06 |
| 889 | CD1 | LEU | A | 116 | -80.787 | 10.318 | 114.260 | 1.00 | 66.19 |
| 890 | CD2 | LEU | A | 116 | -82.573 | 9.043 | 113.070 | 1.00 | 66.04 |
| 891 | C | LEU | A | 116 | -83.713 | 7.592 | 116.798 | 1.00 | 65.84 |
| 892 | O | LEU | A | 116 | -83.144 | 7.894 | 117.852 | 1.00 | 65.90 |
| 893 | N | ILE | A | 117 | -84.085 | 6.344 | 116.527 | 1.00 | 65.02 |
| 894 | CA | ILE | A | 117 | -83.763 | 5.293 | 117.482 | 1.00 | 64.46 |
| 895 | CB | ILE | A | 117 | -84.102 | 3.901 | 116.942 | 1.00 | 64.31 |
| 896 | CG1 | ILE | A | 117 | -85.566 | 3.561 | 117.228 | 1.00 | 64.66 |
| 897 | CD1 | ILE | A | 117 | -86.567 | 4.342 | 116.400 | 1.00 | 64.28 |
| 898 | CG2 | ILE | A | 117 | -83.231 | 2.855 | 117.608 | 1.00 | 64.41 |
| 899 | C | ILE | A | 117 | -82.280 | 5.405 | 117.794 | 1.00 | 64.18 |
| 900 | O | ILE | A | 117 | -81.452 | 5.443 | 116.888 | 1.00 | 64.41 |
| 901 | N | THR | A | 118 | -81.945 | 5.509 | 119.073 | 1.00 | 63.78 |
| 902 | CA | THR | A | 118 | -80.549 | 5.628 | 119.469 | 1.00 | 63.43 |
| 903 | CB | THR | A | 118 | -80.305 | 6.903 | 120.294 | 1.00 | 63.51 |
| 904 | OG1 | THR | A | 118 | -81.158 | 6.899 | 121.446 | 1.00 | 63.30 |
| 905 | CG2 | THR | A | 118 | -80.750 | 8.131 | 119.519 | 1.00 | 64.33 |
| 906 | C | THR | A | 118 | -80.178 | 4.428 | 120.299 | 1.00 | 62.89 |
| 907 | O | THR | A | 118 | -79.093 | 4.363 | 120.865 | 1.00 | 63.13 |
| 908 | N | GLU | A | 119 | -81.095 | 3.483 | 120.404 | 1.00 | 62.19 |

FIGURE 3R

| A | B | C | D | E | F | G | H | I | J |
|---|---|---|---|---|---|---|---|---|---|
| 909 | CA | GLU | A | 119 | -80.789 | 2.302 | 121.179 | 1.00 | 61.90 |
| 910 | CB | GLU | A | 119 | -81.876 | 1.988 | 122.212 | 1.00 | 62.16 |
| 911 | CG | GLU | A | 119 | -83.295 | 2.021 | 121.682 | 1.00 | 63.42 |
| 912 | CD | GLU | A | 119 | -84.097 | 3.175 | 122.249 | 1.00 | 64.70 |
| 913 | OE1 | GLU | A | 119 | -85.216 | 2.925 | 122.752 | 1.00 | 65.29 |
| 914 | OE2 | GLU | A | 119 | -83.603 | 4.322 | 122.200 | 1.00 | 65.47 |
| 915 | C | GLU | A | 119 | -80.553 | 1.116 | 120.270 | 1.00 | 61.26 |
| 916 | O | GLU | A | 119 | -81.336 | 0.833 | 119.358 | 1.00 | 61.12 |
| 917 | N | GLU | A | 120 | -79.435 | 0.451 | 120.508 | 1.00 | 60.35 |
| 918 | CA | GLU | A | 120 | -79.112 | -0.751 | 119.782 | 1.00 | 59.58 |
| 919 | CB | GLU | A | 120 | -80.038 | -1.855 | 120.236 | 1.00 | 59.80 |
| 920 | CG | GLU | A | 120 | -79.656 | -2.395 | 121.592 | 1.00 | 60.94 |
| 921 | CD | GLU | A | 120 | -79.723 | -3.888 | 121.581 | 1.00 | 62.51 |
| 922 | OE1 | GLU | A | 120 | -80.436 | -4.398 | 120.697 | 1.00 | 62.86 |
| 923 | OE2 | GLU | A | 120 | -79.059 | -4.541 | 122.413 | 1.00 | 64.11 |
| 924 | C | GLU | A | 120 | -79.213 | -0.567 | 118.280 | 1.00 | 58.60 |
| 925 | O | GLU | A | 120 | -80.009 | -1.223 | 117.607 | 1.00 | 58.51 |
| 926 | N | ARG | A | 121 | -78.380 | 0.325 | 117.764 | 1.00 | 57.22 |
| 927 | CA | ARG | A | 121 | -78.379 | 0.646 | 116.351 | 1.00 | 55.90 |
| 928 | CB | ARG | A | 121 | -77.564 | 1.925 | 116.127 | 1.00 | 56.41 |
| 929 | CG | ARG | A | 121 | -78.211 | 3.159 | 116.755 | 1.00 | 58.26 |
| 930 | CD | ARG | A | 121 | -77.247 | 4.271 | 117.158 | 1.00 | 62.15 |
| 931 | NE | ARG | A | 121 | -76.774 | 5.071 | 116.030 | 1.00 | 64.53 |
| 932 | CZ | ARG | A | 121 | -75.558 | 5.604 | 115.961 | 1.00 | 66.45 |
| 933 | NH1 | ARG | A | 121 | -74.695 | 5.414 | 116.955 | 1.00 | 66.14 |
| 934 | NH2 | ARG | A | 121 | -75.201 | 6.323 | 114.901 | 1.00 | 67.16 |
| 935 | C | ARG | A | 121 | -77.839 | -0.499 | 115.494 | 1.00 | 54.28 |
| 936 | O | ARG | A | 121 | -77.194 | -1.427 | 115.988 | 1.00 | 53.50 |
| 937 | N | ILE | A | 122 | -78.151 | -0.437 | 114.206 | 1.00 | 52.62 |
| 938 | CA | ILE | A | 122 | -77.596 | -1.363 | 113.237 | 1.00 | 50.94 |
| 939 | CB | ILE | A | 122 | -78.290 | -1.160 | 111.893 | 1.00 | 50.64 |
| 940 | CG1 | ILE | A | 122 | -79.765 | -1.551 | 112.013 | 1.00 | 50.60 |
| 941 | CD1 | ILE | A | 122 | -80.633 | -1.119 | 110.847 | 1.00 | 49.17 |
| 942 | CG2 | ILE | A | 122 | -77.612 | -1.969 | 110.811 | 1.00 | 50.97 |
| 943 | C | ILE | A | 122 | -76.106 | -1.026 | 113.159 | 1.00 | 50.01 |
| 944 | O | ILE | A | 122 | -75.733 | 0.152 | 113.129 | 1.00 | 49.67 |
| 945 | N | PRO | A | 123 | -75.251 | -2.043 | 113.163 | 1.00 | 49.10 |
| 946 | CA | PRO | A | 123 | -73.802 | -1.814 | 113.145 | 1.00 | 48.58 |
| 947 | CB | PRO | A | 123 | -73.216 | -3.227 | 113.096 | 1.00 | 48.45 |
| 948 | CG | PRO | A | 123 | -74.298 | -4.112 | 113.584 | 1.00 | 48.91 |
| 949 | CD | PRO | A | 123 | -75.591 | -3.473 | 113.188 | 1.00 | 48.92 |
| 950 | C | PRO | A | 123 | -73.356 | -1.044 | 111.922 | 1.00 | 48.24 |
| 951 | O | PRO | A | 123 | -74.093 | -0.916 | 110.936 | 1.00 | 47.98 |
| 952 | N | ASN | A | 124 | -72.146 | -0.507 | 111.994 | 1.00 | 48.07 |
| 953 | CA | ASN | A | 124 | -71.560 | 0.145 | 110.831 | 1.00 | 47.49 |
| 954 | CB | ASN | A | 124 | -70.366 | 1.008 | 111.239 | 1.00 | 47.79 |
| 955 | CG | ASN | A | 124 | -70.770 | 2.223 | 112.062 | 1.00 | 49.27 |
| 956 | OD1 | ASN | A | 124 | -71.831 | 2.812 | 111.845 | 1.00 | 50.29 |
| 957 | ND2 | ASN | A | 124 | -69.912 | 2.614 | 113.004 | 1.00 | 49.78 |
| 958 | C | ASN | A | 124 | -71.092 | -0.982 | 109.924 | 1.00 | 46.23 |
| 959 | O | ASN | A | 124 | -70.885 | -2.101 | 110.389 | 1.00 | 45.94 |

FIGURE 3S

| A | B | C | D | E | F | G | H | I | J |
|---|---|---|---|---|---|---|---|---|---|
| 960 | N | ASN | A | 125 | -70.917 | -0.698 | 108.640 | 1.00 | 45.11 |
| 961 | CA | ASN | A | 125 | -70.441 | -1.722 | 107.723 | 1.00 | 44.23 |
| 962 | CB | ASN | A | 125 | -69.043 | -2.183 | 108.135 | 1.00 | 44.07 |
| 963 | CG | ASN | A | 125 | -68.077 | -1.040 | 108.229 | 1.00 | 43.99 |
| 964 | OD1 | ASN | A | 125 | -67.545 | -0.763 | 109.292 | 1.00 | 45.19 |
| 965 | ND2 | ASN | A | 125 | -67.855 | -0.353 | 107.115 | 1.00 | 43.79 |
| 966 | C | ASN | A | 125 | -71.376 | -2.927 | 107.635 | 1.00 | 43.28 |
| 967 | O | ASN | A | 125 | -70.931 | -4.071 | 107.510 | 1.00 | 43.08 |
| 968 | N | THR | A | 126 | -72.670 | -2.658 | 107.736 | 1.00 | 42.12 |
| 969 | CA | THR | A | 126 | -73.668 | -3.691 | 107.597 | 1.00 | 41.08 |
| 970 | CB | THR | A | 126 | -75.019 | -3.208 | 108.126 | 1.00 | 41.17 |
| 971 | OG1 | THR | A | 126 | -74.984 | -3.203 | 109.559 | 1.00 | 41.92 |
| 972 | CG2 | THR | A | 126 | -76.101 | -4.228 | 107.820 | 1.00 | 41.52 |
| 973 | C | THR | A | 126 | -73.713 | -3.966 | 106.111 | 1.00 | 39.94 |
| 974 | O | THR | A | 126 | -73.741 | -3.041 | 105.301 | 1.00 | 39.39 |
| 975 | N | GLN | A | 127 | -73.669 | -5.245 | 105.763 | 1.00 | 39.17 |
| 976 | CA | GLN | A | 127 | -73.550 | -5.662 | 104.375 | 1.00 | 38.23 |
| 977 | CB | GLN | A | 127 | -72.940 | -7.054 | 104.312 | 1.00 | 37.88 |
| 978 | CG | GLN | A | 127 | -71.446 | -7.014 | 104.569 | 1.00 | 36.17 |
| 979 | CD | GLN | A | 127 | -70.908 | -8.312 | 105.078 | 1.00 | 33.91 |
| 980 | OE1 | GLN | A | 127 | -69.921 | -8.823 | 104.552 | 1.00 | 34.78 |
| 981 | NE2 | GLN | A | 127 | -71.555 | -8.866 | 106.093 | 1.00 | 31.99 |
| 982 | C | GLN | A | 127 | -74.851 | -5.567 | 103.624 | 1.00 | 38.42 |
| 983 | O | GLN | A | 127 | -74.865 | -5.372 | 102.419 | 1.00 | 38.49 |
| 984 | N | TRP | A | 128 | -75.953 | -5.672 | 104.347 | 1.00 | 38.80 |
| 985 | CA | TRP | A | 128 | -77.253 | -5.597 | 103.716 | 1.00 | 39.06 |
| 986 | CB | TRP | A | 128 | -77.407 | -6.733 | 102.704 | 1.00 | 39.48 |
| 987 | CG | TRP | A | 128 | -78.784 | -6.870 | 102.181 | 1.00 | 40.32 |
| 988 | CD1 | TRP | A | 128 | -79.787 | -7.620 | 102.714 | 1.00 | 42.04 |
| 989 | NE1 | TRP | A | 128 | -80.930 | -7.482 | 101.963 | 1.00 | 43.55 |
| 990 | CE2 | TRP | A | 128 | -80.672 | -6.636 | 100.917 | 1.00 | 42.36 |
| 991 | CD2 | TRP | A | 128 | -79.328 | -6.231 | 101.026 | 1.00 | 41.21 |
| 992 | CE3 | TRP | A | 128 | -78.815 | -5.355 | 100.068 | 1.00 | 42.04 |
| 993 | CZ3 | TRP | A | 128 | -79.635 | -4.924 | 99.054 | 1.00 | 42.24 |
| 994 | CH2 | TRP | A | 128 | -80.968 | -5.348 | 98.973 | 1.00 | 44.12 |
| 995 | CZ2 | TRP | A | 128 | -81.502 | -6.206 | 99.893 | 1.00 | 42.48 |
| 996 | C | TRP | A | 128 | -78.340 | -5.668 | 104.763 | 1.00 | 39.04 |
| 997 | O | TRP | A | 128 | -78.176 | -6.312 | 105.797 | 1.00 | 39.07 |
| 998 | N | VAL | A | 129 | -79.449 | -4.993 | 104.501 | 1.00 | 39.22 |
| 999 | CA | VAL | A | 129 | -80.573 | -5.012 | 105.421 | 1.00 | 39.73 |
| 1000 | CB | VAL | A | 129 | -80.561 | -3.768 | 106.370 | 1.00 | 39.67 |
| 1001 | CG1 | VAL | A | 129 | -81.267 | -2.598 | 105.736 | 1.00 | 39.95 |
| 1002 | CG2 | VAL | A | 129 | -79.147 | -3.363 | 106.726 | 1.00 | 39.92 |
| 1003 | C | VAL | A | 129 | -81.874 | -4.996 | 104.638 | 1.00 | 39.96 |
| 1004 | O | VAL | A | 129 | -81.929 | -4.494 | 103.519 | 1.00 | 39.45 |
| 1005 | N | THR | A | 130 | -82.931 | -5.545 | 105.218 | 1.00 | 40.74 |
| 1006 | CA | THR | A | 130 | -84.229 | -5.427 | 104.584 | 1.00 | 41.45 |
| 1007 | CB | THR | A | 130 | -84.362 | -6.373 | 103.381 | 1.00 | 41.93 |
| 1008 | OG1 | THR | A | 130 | -85.650 | -6.188 | 102.773 | 1.00 | 43.29 |
| 1009 | CG2 | THR | A | 130 | -84.389 | -7.832 | 103.834 | 1.00 | 41.38 |
| 1010 | C | THR | A | 130 | -85.395 | -5.615 | 105.543 | 1.00 | 41.98 |

FIGURE 3T

| A | B | C | D | E | F | G | H | I | J |
|---|---|---|---|---|---|---|---|---|---|
| 1011 | O | THR | A | 130 | -85.339 | -6.402 | 106.496 | 1.00 | 41.50 |
| 1012 | N | TRP | A | 131 | -86.459 | -4.872 | 105.270 | 1.00 | 42.53 |
| 1013 | CA | TRP | A | 131 | -87.679 | -4.980 | 106.034 | 1.00 | 43.30 |
| 1014 | CB | TRP | A | 131 | -88.609 | -3.829 | 105.675 | 1.00 | 43.34 |
| 1015 | CG | TRP | A | 131 | -88.116 | -2.480 | 106.045 | 1.00 | 43.96 |
| 1016 | CD1 | TRP | A | 131 | -87.760 | -1.485 | 105.192 | 1.00 | 43.49 |
| 1017 | NE1 | TRP | A | 131 | -87.378 | -0.370 | 105.897 | 1.00 | 43.73 |
| 1018 | CE2 | TRP | A | 131 | -87.505 | -0.624 | 107.237 | 1.00 | 44.47 |
| 1019 | CD2 | TRP | A | 131 | -87.969 | -1.948 | 107.367 | 1.00 | 44.17 |
| 1020 | CE3 | TRP | A | 131 | -88.190 | -2.455 | 108.652 | 1.00 | 45.01 |
| 1021 | CZ3 | TRP | A | 131 | -87.926 | -1.639 | 109.752 | 1.00 | 45.89 |
| 1022 | CH2 | TRP | A | 131 | -87.454 | -0.328 | 109.586 | 1.00 | 44.65 |
| 1023 | CZ2 | TRP | A | 131 | -87.240 | 0.198 | 108.343 | 1.00 | 44.48 |
| 1024 | C | TRP | A | 131 | -88.390 | -6.275 | 105.670 | 1.00 | 43.74 |
| 1025 | O | TRP | A | 131 | -88.285 | -6.757 | 104.544 | 1.00 | 44.08 |
| 1026 | N | SER | A | 132 | -89.120 | -6.837 | 106.621 | 1.00 | 44.16 |
| 1027 | CA | SER | A | 132 | -89.949 | -7.983 | 106.335 | 1.00 | 44.80 |
| 1028 | CB | SER | A | 132 | -90.532 | -8.510 | 107.636 | 1.00 | 45.09 |
| 1029 | OG | SER | A | 132 | -90.894 | -7.434 | 108.493 | 1.00 | 46.47 |
| 1030 | C | SER | A | 132 | -91.033 | -7.442 | 105.411 | 1.00 | 44.95 |
| 1031 | O | SER | A | 132 | -91.272 | -6.243 | 105.413 | 1.00 | 45.46 |
| 1032 | N | PRO | A | 133 | -91.696 | -8.294 | 104.633 | 1.00 | 45.04 |
| 1033 | CA | PRO | A | 133 | -92.699 | -7.830 | 103.660 | 1.00 | 45.04 |
| 1034 | CB | PRO | A | 133 | -93.123 | -9.112 | 102.930 | 1.00 | 44.91 |
| 1035 | CG | PRO | A | 133 | -92.109 | -10.135 | 103.279 | 1.00 | 45.39 |
| 1036 | CD | PRO | A | 133 | -91.569 | -9.759 | 104.643 | 1.00 | 45.43 |
| 1037 | C | PRO | A | 133 | -93.913 | -7.165 | 104.314 | 1.00 | 45.29 |
| 1038 | O | PRO | A | 133 | -94.553 | -6.316 | 103.699 | 1.00 | 45.33 |
| 1039 | N | VAL | A | 134 | -94.253 | -7.565 | 105.533 | 1.00 | 45.55 |
| 1040 | CA | VAL | A | 134 | -95.300 | -6.868 | 106.271 | 1.00 | 45.72 |
| 1041 | CB | VAL | A | 134 | -96.563 | -7.734 | 106.505 | 1.00 | 45.84 |
| 1042 | CG1 | VAL | A | 134 | -96.933 | -8.533 | 105.245 | 1.00 | 46.77 |
| 1043 | CG2 | VAL | A | 134 | -96.358 | -8.668 | 107.670 | 1.00 | 46.13 |
| 1044 | C | VAL | A | 134 | -94.701 | -6.474 | 107.606 | 1.00 | 45.52 |
| 1045 | O | VAL | A | 134 | -93.721 | -7.075 | 108.034 | 1.00 | 45.73 |
| 1046 | N | GLY | A | 135 | -95.263 | -5.455 | 108.251 | 1.00 | 45.50 |
| 1047 | CA | GLY | A | 135 | -94.810 | -5.049 | 109.569 | 1.00 | 45.25 |
| 1048 | C | GLY | A | 135 | -93.524 | -4.252 | 109.564 | 1.00 | 45.44 |
| 1049 | O | GLY | A | 135 | -93.297 | -3.438 | 108.673 | 1.00 | 45.45 |
| 1050 | N | HIS | A | 136 | -92.680 | -4.471 | 110.568 | 1.00 | 45.65 |
| 1051 | CA | HIS | A | 136 | -91.403 | -3.758 | 110.635 | 1.00 | 45.56 |
| 1052 | CB | HIS | A | 136 | -91.539 | -2.444 | 111.416 | 1.00 | 45.75 |
| 1053 | CG | HIS | A | 136 | -92.231 | -2.597 | 112.735 | 1.00 | 47.21 |
| 1054 | ND1 | HIS | A | 136 | -93.566 | -2.303 | 112.912 | 1.00 | 47.51 |
| 1055 | CE1 | HIS | A | 136 | -93.903 | -2.538 | 114.168 | 1.00 | 48.81 |
| 1056 | NE2 | HIS | A | 136 | -92.835 | -2.981 | 114.811 | 1.00 | 48.63 |
| 1057 | CD2 | HIS | A | 136 | -91.776 | -3.030 | 113.936 | 1.00 | 47.97 |
| 1058 | C | HIS | A | 136 | -90.253 | -4.600 | 111.190 | 1.00 | 44.87 |
| 1059 | O | HIS | A | 136 | -89.287 | -4.065 | 111.725 | 1.00 | 44.84 |
| 1060 | N | LYS | A | 137 | -90.356 | -5.915 | 111.073 | 1.00 | 44.39 |
| 1061 | CA | LYS | A | 137 | -89.218 | -6.752 | 111.427 | 1.00 | 44.14 |

FIGURE 3U

| A | B | C | D | E | F | G | H | I | J |
|---|---|---|---|---|---|---|---|---|---|
| 1062 | CB | LYS | A | 137 | -89.525 | -8.234 | 111.221 | 1.00 | 44.38 |
| 1063 | CG | LYS | A | 137 | -90.517 | -8.825 | 112.212 | 1.00 | 45.40 |
| 1064 | CD | LYS | A | 137 | -90.881 | -10.260 | 111.834 | 1.00 | 46.13 |
| 1065 | CE | LYS | A | 137 | -91.885 | -10.860 | 112.803 | 1.00 | 47.44 |
| 1066 | NZ | LYS | A | 137 | -92.536 | -12.087 | 112.238 | 1.00 | 47.73 |
| 1067 | C | LYS | A | 137 | -88.063 | -6.341 | 110.522 | 1.00 | 43.33 |
| 1068 | O | LYS | A | 137 | -88.275 | -5.833 | 109.416 | 1.00 | 43.23 |
| 1069 | N | LEU | A | 138 | -86.840 | -6.568 | 110.979 | 1.00 | 42.68 |
| 1070 | CA | LEU | A | 138 | -85.671 | -6.153 | 110.218 | 1.00 | 41.52 |
| 1071 | CB | LEU | A | 138 | -85.018 | -4.982 | 110.930 | 1.00 | 41.84 |
| 1072 | CG | LEU | A | 138 | -84.322 | -3.909 | 110.108 | 1.00 | 42.22 |
| 1073 | CD1 | LEU | A | 138 | -85.154 | -3.506 | 108.898 | 1.00 | 42.38 |
| 1074 | CD2 | LEU | A | 138 | -84.088 | -2.720 | 111.016 | 1.00 | 42.71 |
| 1075 | C | LEU | A | 138 | -84.677 | -7.280 | 110.134 | 1.00 | 40.47 |
| 1076 | O | LEU | A | 138 | -84.405 | -7.932 | 111.138 | 1.00 | 41.40 |
| 1077 | N | ALA | A | 139 | -84.143 | -7.528 | 108.944 | 1.00 | 38.83 |
| 1078 | CA | ALA | A | 139 | -83.103 | -8.541 | 108.774 | 1.00 | 37.16 |
| 1079 | CB | ALA | A | 139 | -83.601 | -9.692 | 107.920 | 1.00 | 37.29 |
| 1080 | C | ALA | A | 139 | -81.885 | -7.898 | 108.139 | 1.00 | 36.17 |
| 1081 | O | ALA | A | 139 | -82.000 | -7.164 | 107.156 | 1.00 | 35.70 |
| 1082 | N | TYR | A | 140 | -80.715 | -8.129 | 108.709 | 1.00 | 35.24 |
| 1083 | CA | TYR | A | 140 | -79.522 | -7.555 | 108.115 | 1.00 | 35.08 |
| 1084 | CB | TYR | A | 140 | -79.210 | -6.175 | 108.690 | 1.00 | 35.34 |
| 1085 | CG | TYR | A | 140 | -78.885 | -6.181 | 110.155 | 1.00 | 37.69 |
| 1086 | CD1 | TYR | A | 140 | -77.596 | -6.445 | 110.597 | 1.00 | 38.79 |
| 1087 | CE1 | TYR | A | 140 | -77.286 | -6.450 | 111.949 | 1.00 | 40.18 |
| 1088 | CZ | TYR | A | 140 | -78.272 | -6.182 | 112.876 | 1.00 | 41.32 |
| 1089 | OH | TYR | A | 140 | -77.963 | -6.193 | 114.222 | 1.00 | 42.58 |
| 1090 | CE2 | TYR | A | 140 | -79.561 | -5.908 | 112.462 | 1.00 | 40.81 |
| 1091 | CD2 | TYR | A | 140 | -79.863 | -5.906 | 111.103 | 1.00 | 39.64 |
| 1092 | C | TYR | A | 140 | -78.356 | -8.485 | 108.275 | 1.00 | 34.37 |
| 1093 | O | TYR | A | 140 | -78.386 | -9.395 | 109.102 | 1.00 | 34.18 |
| 1094 | N | VAL | A | 141 | -77.334 | -8.257 | 107.458 | 1.00 | 34.13 |
| 1095 | CA | VAL | A | 141 | -76.134 | -9.082 | 107.468 | 1.00 | 33.48 |
| 1096 | CB | VAL | A | 141 | -75.896 | -9.751 | 106.106 | 1.00 | 33.42 |
| 1097 | CG1 | VAL | A | 141 | -77.211 | -10.262 | 105.541 | 1.00 | 31.77 |
| 1098 | CG2 | VAL | A | 141 | -74.877 | -10.893 | 106.245 | 1.00 | 32.42 |
| 1099 | C | VAL | A | 141 | -74.947 | -8.226 | 107.804 | 1.00 | 33.83 |
| 1100 | O | VAL | A | 141 | -74.775 | -7.150 | 107.251 | 1.00 | 33.33 |
| 1101 | N | TRP | A | 142 | -74.117 | -8.713 | 108.716 | 1.00 | 34.55 |
| 1102 | CA | TRP | A | 142 | -72.984 | -7.935 | 109.170 | 1.00 | 35.09 |
| 1103 | CB | TRP | A | 142 | -73.376 | -7.128 | 110.417 | 1.00 | 35.47 |
| 1104 | CG | TRP | A | 142 | -72.236 | -6.359 | 110.983 | 1.00 | 35.69 |
| 1105 | CD1 | TRP | A | 142 | -71.680 | -5.237 | 110.472 | 1.00 | 36.60 |
| 1106 | NE1 | TRP | A | 142 | -70.639 | -4.817 | 111.262 | 1.00 | 38.27 |
| 1107 | CE2 | TRP | A | 142 | -70.502 | -5.694 | 112.307 | 1.00 | 38.61 |
| 1108 | CD2 | TRP | A | 142 | -71.494 | -6.675 | 112.160 | 1.00 | 38.36 |
| 1109 | CE3 | TRP | A | 142 | -71.574 | -7.691 | 113.118 | 1.00 | 40.02 |
| 1110 | CZ3 | TRP | A | 142 | -70.677 | -7.690 | 114.170 | 1.00 | 40.38 |
| 1111 | CH2 | TRP | A | 142 | -69.704 | -6.702 | 114.284 | 1.00 | 40.24 |
| 1112 | CZ2 | TRP | A | 142 | -69.602 | -5.693 | 113.367 | 1.00 | 39.52 |

FIGURE 3V

| A | B | C | D | E | F | G | H | I | J |
|---|---|---|---|---|---|---|---|---|---|
| 1113 | C | TRP | A | 142 | -71.855 | -8.883 | 109.483 | 1.00 | 35.15 |
| 1114 | O | TRP | A | 142 | -72.018 | -9.831 | 110.256 | 1.00 | 35.26 |
| 1115 | N | ASN | A | 143 | -70.696 | -8.626 | 108.904 | 1.00 | 35.50 |
| 1116 | CA | ASN | A | 143 | -69.592 | -9.572 | 109.029 | 1.00 | 35.74 |
| 1117 | CB | ASN | A | 143 | -69.051 | -9.634 | 110.454 | 1.00 | 36.25 |
| 1118 | CG | ASN | A | 143 | -68.152 | -8.455 | 110.785 | 1.00 | 38.65 |
| 1119 | OD1 | ASN | A | 143 | -67.501 | -8.428 | 111.833 | 1.00 | 42.03 |
| 1120 | ND2 | ASN | A | 143 | -68.117 | -7.471 | 109.896 | 1.00 | 40.07 |
| 1121 | C | ASN | A | 143 | -70.033 | -10.954 | 108.566 | 1.00 | 35.13 |
| 1122 | O | ASN | A | 143 | -69.748 | -11.944 | 109.206 | 1.00 | 35.06 |
| 1123 | N | ASN | A | 144 | -70.750 | -11.001 | 107.448 | 1.00 | 34.94 |
| 1124 | CA | ASN | A | 144 | -71.161 | -12.263 | 106.866 | 1.00 | 34.63 |
| 1125 | CB | ASN | A | 144 | -69.933 | -13.086 | 106.519 | 1.00 | 34.01 |
| 1126 | CG | ASN | A | 144 | -69.222 | -12.572 | 105.289 | 1.00 | 35.19 |
| 1127 | OD1 | ASN | A | 144 | -68.829 | -13.363 | 104.432 | 1.00 | 36.37 |
| 1128 | ND2 | ASN | A | 144 | -69.058 | -11.243 | 105.182 | 1.00 | 32.83 |
| 1129 | C | ASN | A | 144 | -72.122 | -13.065 | 107.732 | 1.00 | 34.70 |
| 1130 | O | ASN | A | 144 | -72.353 | -14.247 | 107.491 | 1.00 | 34.50 |
| 1131 | N | ASP | A | 145 | -72.673 | -12.434 | 108.754 | 1.00 | 34.98 |
| 1132 | CA | ASP | A | 145 | -73.681 | -13.107 | 109.555 | 1.00 | 35.75 |
| 1133 | CB | ASP | A | 145 | -73.203 | -13.327 | 110.979 | 1.00 | 35.92 |
| 1134 | CG | ASP | A | 145 | -72.385 | -14.559 | 111.098 | 1.00 | 35.82 |
| 1135 | OD1 | ASP | A | 145 | -71.412 | -14.583 | 111.889 | 1.00 | 36.17 |
| 1136 | OD2 | ASP | A | 145 | -72.652 | -15.564 | 110.409 | 1.00 | 36.92 |
| 1137 | C | ASP | A | 145 | -75.016 | -12.394 | 109.516 | 1.00 | 36.02 |
| 1138 | O | ASP | A | 145 | -75.081 | -11.178 | 109.378 | 1.00 | 36.11 |
| 1139 | N | ILE | A | 146 | -76.085 | -13.170 | 109.600 | 1.00 | 36.79 |
| 1140 | CA | ILE | A | 146 | -77.428 | -12.627 | 109.525 | 1.00 | 37.78 |
| 1141 | CB | ILE | A | 146 | -78.338 | -13.631 | 108.844 | 1.00 | 37.37 |
| 1142 | CG1 | ILE | A | 146 | -79.711 | -13.033 | 108.630 | 1.00 | 37.36 |
| 1143 | CD1 | ILE | A | 146 | -80.724 | -13.594 | 109.517 | 1.00 | 36.92 |
| 1144 | CG2 | ILE | A | 146 | -78.474 | -14.842 | 109.711 | 1.00 | 38.98 |
| 1145 | C | ILE | A | 146 | -77.977 | -12.280 | 110.903 | 1.00 | 38.75 |
| 1146 | O | ILE | A | 146 | -77.698 | -12.958 | 111.885 | 1.00 | 38.28 |
| 1147 | N | TYR | A | 147 | -78.766 | -11.213 | 110.960 | 1.00 | 40.52 |
| 1148 | CA | TYR | A | 147 | -79.319 | -10.724 | 112.215 | 1.00 | 42.14 |
| 1149 | CB | TYR | A | 147 | -78.543 | -9.492 | 112.673 | 1.00 | 42.05 |
| 1150 | CG | TYR | A | 147 | -77.167 | -9.807 | 113.182 | 1.00 | 42.83 |
| 1151 | CD1 | TYR | A | 147 | -76.996 | -10.422 | 114.421 | 1.00 | 42.89 |
| 1152 | CE1 | TYR | A | 147 | -75.741 | -10.711 | 114.909 | 1.00 | 42.52 |
| 1153 | CZ | TYR | A | 147 | -74.634 | -10.393 | 114.161 | 1.00 | 42.62 |
| 1154 | OH | TYR | A | 147 | -73.397 | -10.697 | 114.656 | 1.00 | 41.49 |
| 1155 | CE2 | TYR | A | 147 | -74.772 | -9.784 | 112.916 | 1.00 | 42.72 |
| 1156 | CD2 | TYR | A | 147 | -76.035 | -9.492 | 112.438 | 1.00 | 42.13 |
| 1157 | C | TYR | A | 147 | -80.768 | -10.329 | 112.039 | 1.00 | 42.99 |
| 1158 | O | TYR | A | 147 | -81.113 | -9.685 | 111.052 | 1.00 | 42.95 |
| 1159 | N | VAL | A | 148 | -81.606 | -10.688 | 113.011 | 1.00 | 44.06 |
| 1160 | CA | VAL | A | 148 | -83.022 | -10.338 | 112.944 | 1.00 | 45.14 |
| 1161 | CB | VAL | A | 148 | -83.903 | -11.584 | 112.949 | 1.00 | 45.03 |
| 1162 | CG1 | VAL | A | 148 | -85.360 | -11.205 | 113.031 | 1.00 | 45.30 |
| 1163 | CG2 | VAL | A | 148 | -83.637 | -12.414 | 111.698 | 1.00 | 45.09 |

FIGURE 3W

| A | B | C | D | E | F | G | H | I | J |
|---|---|---|---|---|---|---|---|---|---|
| 1164 | C | VAL | A | 148 | -83.429 | -9.390 | 114.073 | 1.00 | 46.07 |
| 1165 | O | VAL | A | 148 | -83.252 | -9.689 | 115.258 | 1.00 | 46.32 |
| 1166 | N | LYS | A | 149 | -83.957 | -8.233 | 113.690 | 1.00 | 47.01 |
| 1167 | CA | LYS | A | 149 | -84.401 | -7.228 | 114.645 | 1.00 | 47.78 |
| 1168 | CB | LYS | A | 149 | -83.814 | -5.867 | 114.271 | 1.00 | 47.98 |
| 1169 | CG | LYS | A | 149 | -83.796 | -4.834 | 115.386 | 1.00 | 48.59 |
| 1170 | CD | LYS | A | 149 | -83.370 | -3.461 | 114.882 | 1.00 | 48.37 |
| 1171 | CE | LYS | A | 149 | -81.886 | -3.244 | 115.044 | 1.00 | 48.67 |
| 1172 | NZ | LYS | A | 149 | -81.544 | -3.000 | 116.472 | 1.00 | 50.63 |
| 1173 | C | LYS | A | 149 | -85.925 | -7.200 | 114.613 | 1.00 | 48.43 |
| 1174 | O | LYS | A | 149 | -86.530 | -6.861 | 113.594 | 1.00 | 48.72 |
| 1175 | N | ILE | A | 150 | -86.544 | -7.578 | 115.727 | 1.00 | 49.09 |
| 1176 | CA | ILE | A | 150 | -88.001 | -7.667 | 115.830 | 1.00 | 49.77 |
| 1177 | CB | ILE | A | 150 | -88.382 | -8.423 | 117.097 | 1.00 | 50.25 |
| 1178 | CG1 | ILE | A | 150 | -87.736 | -7.754 | 118.326 | 1.00 | 51.20 |
| 1179 | CD1 | ILE | A | 150 | -86.195 | -7.767 | 118.325 | 1.00 | 51.77 |
| 1180 | CG2 | ILE | A | 150 | -87.976 | -9.892 | 116.978 | 1.00 | 50.25 |
| 1181 | C | ILE | A | 150 | -88.671 | -6.312 | 115.862 | 1.00 | 49.79 |
| 1182 | O | ILE | A | 150 | -89.735 | -6.119 | 115.283 | 1.00 | 49.84 |
| 1183 | N | GLU | A | 151 | -88.046 | -5.390 | 116.577 | 1.00 | 50.04 |
| 1184 | CA | GLU | A | 151 | -88.513 | -4.023 | 116.697 | 1.00 | 50.13 |
| 1185 | CB | GLU | A | 151 | -89.149 | -3.780 | 118.071 | 1.00 | 50.27 |
| 1186 | CG | GLU | A | 151 | -90.371 | -4.640 | 118.362 | 1.00 | 49.88 |
| 1187 | CD | GLU | A | 151 | -91.618 | -4.118 | 117.678 | 1.00 | 49.38 |
| 1188 | OE1 | GLU | A | 151 | -91.578 | -2.989 | 117.156 | 1.00 | 48.43 |
| 1189 | OE2 | GLU | A | 151 | -92.644 | -4.827 | 117.676 | 1.00 | 49.86 |
| 1190 | C | GLU | A | 151 | -87.254 | -3.202 | 116.564 | 1.00 | 50.33 |
| 1191 | O | GLU | A | 151 | -86.206 | -3.577 | 117.077 | 1.00 | 50.83 |
| 1192 | N | PRO | A | 152 | -87.341 | -2.097 | 115.853 | 1.00 | 50.40 |
| 1193 | CA | PRO | A | 152 | -86.184 | -1.246 | 115.624 | 1.00 | 50.75 |
| 1194 | CB | PRO | A | 152 | -86.816 | 0.029 | 115.089 | 1.00 | 50.38 |
| 1195 | CG | PRO | A | 152 | -87.986 | -0.456 | 114.360 | 1.00 | 50.14 |
| 1196 | CD | PRO | A | 152 | -88.545 | -1.586 | 115.181 | 1.00 | 50.32 |
| 1197 | C | PRO | A | 152 | -85.340 | -0.953 | 116.859 | 1.00 | 51.47 |
| 1198 | O | PRO | A | 152 | -84.134 | -0.773 | 116.705 | 1.00 | 51.55 |
| 1199 | N | ASN | A | 153 | -85.933 | -0.918 | 118.052 | 1.00 | 52.26 |
| 1200 | CA | ASN | A | 153 | -85.167 | -0.520 | 119.237 | 1.00 | 53.02 |
| 1201 | CB | ASN | A | 153 | -85.897 | 0.580 | 120.019 | 1.00 | 53.29 |
| 1202 | CG | ASN | A | 153 | -87.350 | 0.223 | 120.327 | 1.00 | 54.92 |
| 1203 | OD1 | ASN | A | 153 | -88.248 | 1.060 | 120.183 | 1.00 | 56.44 |
| 1204 | ND2 | ASN | A | 153 | -87.589 | -1.019 | 120.753 | 1.00 | 55.59 |
| 1205 | C | ASN | A | 153 | -84.745 | -1.637 | 120.175 | 1.00 | 53.24 |
| 1206 | O | ASN | A | 153 | -84.162 | -1.387 | 121.234 | 1.00 | 53.24 |
| 1207 | N | LEU | A | 154 | -85.026 | -2.873 | 119.784 | 1.00 | 53.27 |
| 1208 | CA | LEU | A | 154 | -84.684 | -4.013 | 120.619 | 1.00 | 53.55 |
| 1209 | CB | LEU | A | 154 | -85.835 | -5.017 | 120.614 | 1.00 | 53.63 |
| 1210 | CG | LEU | A | 154 | -87.104 | -4.552 | 121.334 | 1.00 | 55.32 |
| 1211 | CD1 | LEU | A | 154 | -88.244 | -5.555 | 121.183 | 1.00 | 56.83 |
| 1212 | CD2 | LEU | A | 154 | -86.812 | -4.308 | 122.813 | 1.00 | 56.74 |
| 1213 | C | LEU | A | 154 | -83.387 | -4.689 | 120.181 | 1.00 | 53.55 |
| 1214 | O | LEU | A | 154 | -82.923 | -4.518 | 119.049 | 1.00 | 53.67 |

FIGURE 3X

| A | B | C | D | E | F | G | H | I | J |
|---|---|---|---|---|---|---|---|---|---|
| 1215 | N | PRO | A | 155 | -82.770 | -5.433 | 121.088 | 1.00 | 53.45 |
| 1216 | CA | PRO | A | 155 | -81.600 | -6.227 | 120.719 | 1.00 | 53.26 |
| 1217 | CB | PRO | A | 155 | -81.416 | -7.150 | 121.928 | 1.00 | 53.35 |
| 1218 | CG | PRO | A | 155 | -82.698 | -6.991 | 122.707 | 1.00 | 53.64 |
| 1219 | CD | PRO | A | 155 | -83.076 | -5.551 | 122.521 | 1.00 | 53.41 |
| 1220 | C | PRO | A | 155 | -81.952 | -7.036 | 119.483 | 1.00 | 52.99 |
| 1221 | O | PRO | A | 155 | -83.128 | -7.328 | 119.260 | 1.00 | 53.22 |
| 1222 | N | SER | A | 156 | -80.964 | -7.378 | 118.673 | 1.00 | 52.22 |
| 1223 | CA | SER | A | 156 | -81.253 | -8.170 | 117.498 | 1.00 | 51.46 |
| 1224 | CB | SER | A | 156 | -80.487 | -7.649 | 116.283 | 1.00 | 51.35 |
| 1225 | OG | SER | A | 156 | -79.093 | -7.686 | 116.501 | 1.00 | 51.78 |
| 1226 | C | SER | A | 156 | -80.888 | -9.603 | 117.802 | 1.00 | 51.06 |
| 1227 | O | SER | A | 156 | -80.056 | -9.871 | 118.665 | 1.00 | 51.10 |
| 1228 | N | TYR | A | 157 | -81.536 | -10.530 | 117.116 | 1.00 | 50.44 |
| 1229 | CA | TYR | A | 157 | -81.215 | -11.924 | 117.298 | 1.00 | 50.17 |
| 1230 | CB | TYR | A | 157 | -82.462 | -12.773 | 117.148 | 1.00 | 50.52 |
| 1231 | CG | TYR | A | 157 | -83.544 | -12.452 | 118.145 | 1.00 | 51.11 |
| 1232 | CD1 | TYR | A | 157 | -83.633 | -13.140 | 119.352 | 1.00 | 52.56 |
| 1233 | CE1 | TYR | A | 157 | -84.636 | -12.856 | 120.259 | 1.00 | 53.17 |
| 1234 | CZ | TYR | A | 157 | -85.561 | -11.867 | 119.964 | 1.00 | 53.50 |
| 1235 | OH | TYR | A | 157 | -86.574 | -11.553 | 120.858 | 1.00 | 52.91 |
| 1236 | CE2 | TYR | A | 157 | -85.479 | -11.182 | 118.768 | 1.00 | 52.57 |
| 1237 | CD2 | TYR | A | 157 | -84.484 | -11.474 | 117.876 | 1.00 | 51.02 |
| 1238 | C | TYR | A | 157 | -80.185 | -12.321 | 116.258 | 1.00 | 49.68 |
| 1239 | O | TYR | A | 157 | -80.292 | -11.948 | 115.089 | 1.00 | 50.00 |
| 1240 | N | ARG | A | 158 | -79.183 | -13.070 | 116.694 | 1.00 | 48.95 |
| 1241 | CA | ARG | A | 158 | -78.107 | -13.512 | 115.824 | 1.00 | 48.21 |
| 1242 | CB | ARG | A | 158 | -76.844 | -13.680 | 116.663 | 1.00 | 48.35 |
| 1243 | CG | ARG | A | 158 | -75.588 | -13.015 | 116.132 | 1.00 | 49.45 |
| 1244 | CD | ARG | A | 158 | -74.655 | -13.936 | 115.375 | 1.00 | 51.05 |
| 1245 | NE | ARG | A | 158 | -73.256 | -13.578 | 115.577 | 1.00 | 52.28 |
| 1246 | CZ | ARG | A | 158 | -72.238 | -14.324 | 115.177 | 1.00 | 52.78 |
| 1247 | NH1 | ARG | A | 158 | -72.468 | -15.459 | 114.543 | 1.00 | 53.84 |
| 1248 | NH2 | ARG | A | 158 | -70.992 | -13.941 | 115.402 | 1.00 | 52.41 |
| 1249 | C | ARG | A | 158 | -78.518 | -14.870 | 115.261 | 1.00 | 47.44 |
| 1250 | O | ARG | A | 158 | -78.593 | -15.854 | 116.005 | 1.00 | 47.08 |
| 1251 | N | ILE | A | 159 | -78.798 | -14.938 | 113.961 | 1.00 | 46.07 |
| 1252 | CA | ILE | A | 159 | -79.180 | -16.224 | 113.376 | 1.00 | 44.90 |
| 1253 | CB | ILE | A | 159 | -80.110 | -16.066 | 112.158 | 1.00 | 45.17 |
| 1254 | CG1 | ILE | A | 159 | -81.435 | -15.453 | 112.585 | 1.00 | 46.03 |
| 1255 | CD1 | ILE | A | 159 | -81.317 | -14.038 | 113.009 | 1.00 | 47.93 |
| 1256 | CG2 | ILE | A | 159 | -80.395 | -17.423 | 111.531 | 1.00 | 44.66 |
| 1257 | C | ILE | A | 159 | -78.000 | -17.117 | 113.031 | 1.00 | 43.77 |
| 1258 | O | ILE | A | 159 | -78.067 | -18.313 | 113.256 | 1.00 | 43.48 |
| 1259 | N | THR | A | 160 | -76.917 | -16.555 | 112.497 | 1.00 | 42.82 |
| 1260 | CA | THR | A | 160 | -75.777 | -17.395 | 112.119 | 1.00 | 41.89 |
| 1261 | CB | THR | A | 160 | -75.548 | -17.427 | 110.570 | 1.00 | 41.94 |
| 1262 | OG1 | THR | A | 160 | -75.171 | -16.126 | 110.080 | 1.00 | 40.16 |
| 1263 | CG2 | THR | A | 160 | -76.847 | -17.747 | 109.846 | 1.00 | 41.17 |
| 1264 | C | THR | A | 160 | -74.494 | -17.034 | 112.825 | 1.00 | 42.02 |
| 1265 | O | THR | A | 160 | -74.229 | -15.873 | 113.123 | 1.00 | 41.74 |

FIGURE 3Y

| A | B | C | D | E | F | G | H | I | J |
|---|---|---|---|---|---|---|---|---|---|
| 1266 | N | TRP | A | 161 | -73.685 | -18.049 | 113.070 | 1.00 | 42.13 |
| 1267 | CA | TRP | A | 161 | -72.431 | -17.864 | 113.757 | 1.00 | 42.46 |
| 1268 | CB | TRP | A | 161 | -72.458 | -18.640 | 115.066 | 1.00 | 42.91 |
| 1269 | CG | TRP | A | 161 | -73.561 | -18.191 | 115.971 | 1.00 | 44.48 |
| 1270 | CD1 | TRP | A | 161 | -74.871 | -18.537 | 115.890 | 1.00 | 44.57 |
| 1271 | NE1 | TRP | A | 161 | -75.586 | -17.916 | 116.885 | 1.00 | 46.73 |
| 1272 | CE2 | TRP | A | 161 | -74.736 | -17.139 | 117.628 | 1.00 | 46.56 |
| 1273 | CD2 | TRP | A | 161 | -73.451 | -17.286 | 117.077 | 1.00 | 45.80 |
| 1274 | CE3 | TRP | A | 161 | -72.389 | -16.594 | 117.667 | 1.00 | 47.87 |
| 1275 | CZ3 | TRP | A | 161 | -72.643 | -15.789 | 118.782 | 1.00 | 49.17 |
| 1276 | CH2 | TRP | A | 161 | -73.938 | -15.665 | 119.301 | 1.00 | 48.33 |
| 1277 | CZ2 | TRP | A | 161 | -74.993 | -16.332 | 118.740 | 1.00 | 47.92 |
| 1278 | C | TRP | A | 161 | -71.286 | -18.347 | 112.890 | 1.00 | 42.59 |
| 1279 | O | TRP | A | 161 | -70.146 | -18.424 | 113.348 | 1.00 | 42.82 |
| 1280 | N | THR | A | 162 | -71.579 | -18.648 | 111.628 | 1.00 | 42.13 |
| 1281 | CA | THR | A | 162 | -70.557 | -19.189 | 110.741 | 1.00 | 42.09 |
| 1282 | CB | THR | A | 162 | -71.126 | -20.358 | 109.952 | 1.00 | 42.15 |
| 1283 | OG1 | THR | A | 162 | -72.351 | -19.961 | 109.317 | 1.00 | 41.11 |
| 1284 | CG2 | THR | A | 162 | -71.548 | -21.460 | 110.933 | 1.00 | 41.82 |
| 1285 | C | THR | A | 162 | -69.919 | -18.173 | 109.806 | 1.00 | 42.26 |
| 1286 | O | THR | A | 162 | -68.869 | -18.436 | 109.230 | 1.00 | 42.12 |
| 1287 | N | GLY | A | 163 | -70.537 | -17.006 | 109.672 | 1.00 | 42.24 |
| 1288 | CA | GLY | A | 163 | -69.990 | -15.978 | 108.806 | 1.00 | 42.31 |
| 1289 | C | GLY | A | 163 | -68.489 | -15.837 | 108.924 | 1.00 | 42.51 |
| 1290 | O | GLY | A | 163 | -67.924 | -15.969 | 110.006 | 1.00 | 42.49 |
| 1291 | N | LYS | A | 164 | -67.834 | -15.565 | 107.802 | 1.00 | 42.68 |
| 1292 | CA | LYS | A | 164 | -66.386 | -15.370 | 107.790 | 1.00 | 42.76 |
| 1293 | CB | LYS | A | 164 | -65.663 | -16.688 | 108.049 | 1.00 | 42.94 |
| 1294 | CG | LYS | A | 164 | -64.159 | -16.547 | 108.226 | 1.00 | 44.49 |
| 1295 | CD | LYS | A | 164 | -63.494 | -17.917 | 108.351 | 1.00 | 46.77 |
| 1296 | CE | LYS | A | 164 | -61.994 | -17.787 | 108.548 | 1.00 | 49.88 |
| 1297 | NZ | LYS | A | 164 | -61.363 | -19.118 | 108.757 | 1.00 | 51.18 |
| 1298 | C | LYS | A | 164 | -65.932 | -14.762 | 106.464 | 1.00 | 42.70 |
| 1299 | O | LYS | A | 164 | -66.209 | -15.307 | 105.383 | 1.00 | 42.37 |
| 1300 | N | GLU | A | 165 | -65.232 | -13.635 | 106.560 | 1.00 | 42.30 |
| 1301 | CA | GLU | A | 165 | -64.758 | -12.920 | 105.387 | 1.00 | 42.55 |
| 1302 | CB | GLU | A | 165 | -63.728 | -11.860 | 105.775 | 1.00 | 43.00 |
| 1303 | CG | GLU | A | 165 | -63.508 | -10.805 | 104.693 | 1.00 | 47.10 |
| 1304 | CD | GLU | A | 165 | -63.223 | -9.423 | 105.267 | 1.00 | 51.85 |
| 1305 | OE1 | GLU | A | 165 | -62.996 | -9.330 | 106.500 | 1.00 | 53.85 |
| 1306 | OE2 | GLU | A | 165 | -63.240 | -8.431 | 104.492 | 1.00 | 52.18 |
| 1307 | C | GLU | A | 165 | -64.212 | -13.844 | 104.289 | 1.00 | 41.45 |
| 1308 | O | GLU | A | 165 | -63.462 | -14.780 | 104.562 | 1.00 | 41.15 |
| 1309 | N | ASN | A | 166 | -64.638 | -13.582 | 103.055 | 1.00 | 40.25 |
| 1310 | CA | ASN | A | 166 | -64.195 | -14.322 | 101.869 | 1.00 | 39.54 |
| 1311 | CB | ASN | A | 166 | -62.725 | -14.021 | 101.543 | 1.00 | 39.34 |
| 1312 | CG | ASN | A | 166 | -62.453 | -12.559 | 101.326 | 1.00 | 39.10 |
| 1313 | OD1 | ASN | A | 166 | -63.322 | -11.806 | 100.916 | 1.00 | 38.31 |
| 1314 | ND2 | ASN | A | 166 | -61.224 | -12.144 | 101.610 | 1.00 | 40.88 |
| 1315 | C | ASN | A | 166 | -64.339 | -15.836 | 101.932 | 1.00 | 39.07 |
| 1316 | O | ASN | A | 166 | -63.831 | -16.536 | 101.052 | 1.00 | 39.78 |

FIGURE 3Z

| A | B | C | D | E | F | G | H | I | J |
|---|---|---|---|---|---|---|---|---|---|
| 1317 | N | ILE | A | 167 | -64.993 | -16.358 | 102.960 | 1.00 | 38.18 |
| 1318 | CA | ILE | A | 167 | -65.041 | -17.803 | 103.129 | 1.00 | 37.29 |
| 1319 | CB | ILE | A | 167 | -64.205 | -18.247 | 104.321 | 1.00 | 37.48 |
| 1320 | CG1 | ILE | A | 167 | -62.734 | -18.297 | 103.934 | 1.00 | 38.20 |
| 1321 | CD1 | ILE | A | 167 | -62.063 | -16.953 | 103.935 | 1.00 | 41.85 |
| 1322 | CG2 | ILE | A | 167 | -64.622 | -19.638 | 104.744 | 1.00 | 37.49 |
| 1323 | C | ILE | A | 167 | -66.441 | -18.335 | 103.276 | 1.00 | 36.51 |
| 1324 | O | ILE | A | 167 | -66.846 | -19.231 | 102.536 | 1.00 | 36.19 |
| 1325 | N | ILE | A | 168 | -67.175 | -17.838 | 104.266 | 1.00 | 35.61 |
| 1326 | CA | ILE | A | 168 | -68.563 | -18.251 | 104.349 | 1.00 | 34.54 |
| 1327 | CB | ILE | A | 168 | -68.861 | -19.320 | 105.445 | 1.00 | 34.98 |
| 1328 | CG1 | ILE | A | 168 | -69.842 | -18.813 | 106.473 | 1.00 | 35.52 |
| 1329 | CD1 | ILE | A | 168 | -70.844 | -19.872 | 106.786 | 1.00 | 38.17 |
| 1330 | CG2 | ILE | A | 168 | -67.613 | -20.007 | 106.017 | 1.00 | 34.24 |
| 1331 | C | ILE | A | 168 | -69.510 | -17.076 | 104.402 | 1.00 | 33.59 |
| 1332 | O | ILE | A | 168 | -69.306 | -16.113 | 105.148 | 1.00 | 33.42 |
| 1333 | N | TYR | A | 169 | -70.536 | -17.145 | 103.566 | 1.00 | 32.42 |
| 1334 | CA | TYR | A | 169 | -71.483 | -16.057 | 103.451 | 1.00 | 31.27 |
| 1335 | CB | TYR | A | 169 | -71.541 | -15.535 | 102.006 | 1.00 | 31.08 |
| 1336 | CG | TYR | A | 169 | -70.223 | -15.218 | 101.327 | 1.00 | 29.82 |
| 1337 | CD1 | TYR | A | 169 | -69.321 | -16.224 | 100.988 | 1.00 | 29.95 |
| 1338 | CE1 | TYR | A | 169 | -68.132 | -15.930 | 100.344 | 1.00 | 26.98 |
| 1339 | CZ | TYR | A | 169 | -67.838 | -14.623 | 100.024 | 1.00 | 26.49 |
| 1340 | OH | TYR | A | 169 | -66.654 | -14.309 | 99.401 | 1.00 | 26.74 |
| 1341 | CE2 | TYR | A | 169 | -68.709 | -13.619 | 100.329 | 1.00 | 26.91 |
| 1342 | CD2 | TYR | A | 169 | -69.901 | -13.915 | 100.976 | 1.00 | 28.85 |
| 1343 | C | TYR | A | 169 | -72.867 | -16.542 | 103.833 | 1.00 | 31.21 |
| 1344 | O | TYR | A | 169 | -73.436 | -17.402 | 103.150 | 1.00 | 31.35 |
| 1345 | N | ASN | A | 170 | -73.425 | -15.995 | 104.910 | 1.00 | 30.37 |
| 1346 | CA | ASN | A | 170 | -74.810 | -16.300 | 105.252 | 1.00 | 29.55 |
| 1347 | CB | ASN | A | 170 | -74.973 | -16.591 | 106.741 | 1.00 | 29.56 |
| 1348 | CG | ASN | A | 170 | -74.100 | -17.721 | 107.210 | 1.00 | 30.27 |
| 1349 | OD1 | ASN | A | 170 | -74.377 | -18.895 | 106.942 | 1.00 | 33.44 |
| 1350 | ND2 | ASN | A | 170 | -73.017 | -17.382 | 107.883 | 1.00 | 27.98 |
| 1351 | C | ASN | A | 170 | -75.643 | -15.088 | 104.871 | 1.00 | 29.05 |
| 1352 | O | ASN | A | 170 | -75.271 | -13.982 | 105.169 | 1.00 | 28.88 |
| 1353 | N | GLY | A | 171 | -76.755 | -15.294 | 104.178 | 1.00 | 28.81 |
| 1354 | CA | GLY | A | 171 | -77.619 | -14.191 | 103.819 | 1.00 | 27.99 |
| 1355 | C | GLY | A | 171 | -77.125 | -13.255 | 102.730 | 1.00 | 27.59 |
| 1356 | O | GLY | A | 171 | -77.851 | -12.359 | 102.329 | 1.00 | 27.39 |
| 1357 | N | ILE | A | 172 | -75.892 | -13.443 | 102.270 | 1.00 | 27.17 |
| 1358 | CA | ILE | A | 172 | -75.353 | -12.650 | 101.167 | 1.00 | 26.43 |
| 1359 | CB | ILE | A | 172 | -74.426 | -11.503 | 101.670 | 1.00 | 26.40 |
| 1360 | CG1 | ILE | A | 172 | -73.386 | -12.055 | 102.647 | 1.00 | 25.64 |
| 1361 | CD1 | ILE | A | 172 | -72.402 | -11.015 | 103.223 | 1.00 | 26.18 |
| 1362 | CG2 | ILE | A | 172 | -75.255 | -10.351 | 102.259 | 1.00 | 24.00 |
| 1363 | C | ILE | A | 172 | -74.591 | -13.559 | 100.199 | 1.00 | 26.31 |
| 1364 | O | ILE | A | 172 | -74.102 | -14.608 | 100.599 | 1.00 | 26.82 |
| 1365 | N | THR | A | 173 | -74.482 | -13.137 | 98.946 | 1.00 | 25.63 |
| 1366 | CA | THR | A | 173 | -73.808 | -13.911 | 97.909 | 1.00 | 25.74 |
| 1367 | CB | THR | A | 173 | -74.403 | -13.579 | 96.500 | 1.00 | 25.82 |

FIGURE 3 AA

| A | B | C | D | E | F | G | H | I | J |
|---|---|---|---|---|---|---|---|---|---|
| 1368 | OG1 | THR | A | 173 | -74.590 | -12.161 | 96.348 | 1.00 | 25.46 |
| 1369 | CG2 | THR | A | 173 | -75.815 | -14.126 | 96.355 | 1.00 | 26.31 |
| 1370 | C | THR | A | 173 | -72.316 | -13.633 | 97.848 | 1.00 | 25.51 |
| 1371 | O | THR | A | 173 | -71.849 | -12.581 | 98.293 | 1.00 | 25.26 |
| 1372 | N | ASP | A | 174 | -71.564 | -14.579 | 97.286 | 1.00 | 24.69 |
| 1373 | CA | ASP | A | 174 | -70.169 | -14.323 | 96.987 | 1.00 | 23.44 |
| 1374 | CB | ASP | A | 174 | -69.342 | -15.601 | 97.037 | 1.00 | 23.91 |
| 1375 | CG | ASP | A | 174 | -69.644 | -16.559 | 95.889 | 1.00 | 23.96 |
| 1376 | OD1 | ASP | A | 174 | -68.810 | -17.441 | 95.624 | 1.00 | 24.39 |
| 1377 | OD2 | ASP | A | 174 | -70.665 | -16.512 | 95.188 | 1.00 | 24.49 |
| 1378 | C | ASP | A | 174 | -70.157 | -13.671 | 95.586 | 1.00 | 23.53 |
| 1379 | O | ASP | A | 174 | -71.220 | -13.371 | 95.010 | 1.00 | 22.50 |
| 1380 | N | TRP | A | 175 | -68.971 | -13.451 | 95.044 | 1.00 | 22.89 |
| 1381 | CA | TRP | A | 175 | -68.836 | -12.761 | 93.777 | 1.00 | 23.07 |
| 1382 | CB | TRP | A | 175 | -67.351 | -12.556 | 93.392 | 1.00 | 22.86 |
| 1383 | CG | TRP | A | 175 | -67.240 | -11.574 | 92.296 | 1.00 | 22.35 |
| 1384 | CD1 | TRP | A | 175 | -66.973 | -10.237 | 92.411 | 1.00 | 21.88 |
| 1385 | NE1 | TRP | A | 175 | -66.983 | -9.645 | 91.174 | 1.00 | 19.08 |
| 1386 | CE2 | TRP | A | 175 | -67.287 | -10.589 | 90.234 | 1.00 | 20.41 |
| 1387 | CD2 | TRP | A | 175 | -67.452 | -11.819 | 90.909 | 1.00 | 20.68 |
| 1388 | CE3 | TRP | A | 175 | -67.762 | -12.958 | 90.158 | 1.00 | 19.38 |
| 1389 | CZ3 | TRP | A | 175 | -67.904 | -12.840 | 88.789 | 1.00 | 18.17 |
| 1390 | CH2 | TRP | A | 175 | -67.739 | -11.602 | 88.152 | 1.00 | 18.32 |
| 1391 | CZ2 | TRP | A | 175 | -67.442 | -10.465 | 88.860 | 1.00 | 19.82 |
| 1392 | C | TRP | A | 175 | -69.674 | -13.335 | 92.629 | 1.00 | 23.58 |
| 1393 | O | TRP | A | 175 | -70.501 | -12.615 | 92.045 | 1.00 | 23.56 |
| 1394 | N | VAL | A | 176 | -69.508 | -14.620 | 92.305 | 1.00 | 24.17 |
| 1395 | CA | VAL | A | 176 | -70.285 | -15.171 | 91.183 | 1.00 | 24.60 |
| 1396 | CB | VAL | A | 176 | -69.889 | -16.608 | 90.758 | 1.00 | 24.92 |
| 1397 | CG1 | VAL | A | 176 | -69.363 | -17.391 | 91.915 | 1.00 | 24.13 |
| 1398 | CG2 | VAL | A | 176 | -68.944 | -16.592 | 89.570 | 1.00 | 26.39 |
| 1399 | C | VAL | A | 176 | -71.778 | -15.246 | 91.421 | 1.00 | 24.61 |
| 1400 | O | VAL | A | 176 | -72.561 | -15.120 | 90.497 | 1.00 | 24.85 |
| 1401 | N | TYR | A | 177 | -72.192 | -15.527 | 92.636 | 1.00 | 24.68 |
| 1402 | CA | TYR | A | 177 | -73.620 | -15.614 | 92.844 | 1.00 | 24.97 |
| 1403 | CB | TYR | A | 177 | -73.935 | -16.238 | 94.186 | 1.00 | 24.65 |
| 1404 | CG | TYR | A | 177 | -74.217 | -17.728 | 94.115 | 1.00 | 25.96 |
| 1405 | CD1 | TYR | A | 177 | -73.194 | -18.654 | 94.217 | 1.00 | 23.76 |
| 1406 | CE1 | TYR | A | 177 | -73.452 | -19.996 | 94.189 | 1.00 | 24.52 |
| 1407 | CZ | TYR | A | 177 | -74.742 | -20.445 | 94.054 | 1.00 | 25.24 |
| 1408 | OH | TYR | A | 177 | -74.997 | -21.797 | 94.034 | 1.00 | 25.72 |
| 1409 | CE2 | TYR | A | 177 | -75.781 | -19.557 | 93.946 | 1.00 | 25.19 |
| 1410 | CD2 | TYR | A | 177 | -75.517 | -18.201 | 93.976 | 1.00 | 25.89 |
| 1411 | C | TYR | A | 177 | -74.233 | -14.242 | 92.703 | 1.00 | 25.10 |
| 1412 | O | TYR | A | 177 | -75.323 | -14.097 | 92.154 | 1.00 | 25.83 |
| 1413 | N | GLU | A | 178 | -73.519 | -13.224 | 93.173 | 1.00 | 25.59 |
| 1414 | CA | GLU | A | 178 | -73.982 | -11.850 | 93.002 | 1.00 | 25.82 |
| 1415 | CB | GLU | A | 178 | -73.100 | -10.862 | 93.757 | 1.00 | 25.04 |
| 1416 | CG | GLU | A | 178 | -73.480 | -9.422 | 93.474 | 1.00 | 24.82 |
| 1417 | CD | GLU | A | 178 | -72.587 | -8.419 | 94.194 | 1.00 | 25.14 |
| 1418 | OE1 | GLU | A | 178 | -72.633 | -7.241 | 93.826 | 1.00 | 24.27 |

FIGURE 3 AB

| A | B | C | D | E | F | G | H | I | J |
|---|---|---|---|---|---|---|---|---|---|
| 1419 | OE2 | GLU | A | 178 | -71.830 | -8.803 | 95.113 | 1.00 | 24.44 |
| 1420 | C | GLU | A | 178 | -74.012 | -11.430 | 91.538 | 1.00 | 25.79 |
| 1421 | O | GLU | A | 178 | -74.999 | -10.894 | 91.055 | 1.00 | 26.81 |
| 1422 | N | GLU | A | 179 | -72.929 | -11.647 | 90.821 | 1.00 | 25.86 |
| 1423 | CA | GLU | A | 179 | -72.913 | -11.152 | 89.459 | 1.00 | 26.21 |
| 1424 | CB | GLU | A | 179 | -71.483 | -10.862 | 88.991 | 1.00 | 26.17 |
| 1425 | CG | GLU | A | 179 | -71.346 | -10.505 | 87.515 | 1.00 | 27.12 |
| 1426 | CD | GLU | A | 179 | -71.966 | -9.156 | 87.159 | 1.00 | 27.41 |
| 1427 | OE1 | GLU | A | 179 | -72.110 | -8.862 | 85.957 | 1.00 | 29.41 |
| 1428 | OE2 | GLU | A | 179 | -72.289 | -8.374 | 88.072 | 1.00 | 26.56 |
| 1429 | C | GLU | A | 179 | -73.640 | -12.048 | 88.466 | 1.00 | 26.94 |
| 1430 | O | GLU | A | 179 | -74.304 | -11.546 | 87.578 | 1.00 | 26.77 |
| 1431 | N | GLU | A | 180 | -73.576 | -13.363 | 88.651 | 1.00 | 27.47 |
| 1432 | CA | GLU | A | 180 | -74.085 | -14.253 | 87.624 | 1.00 | 29.07 |
| 1433 | CB | GLU | A | 180 | -72.977 | -15.211 | 87.157 | 1.00 | 28.09 |
| 1434 | CG | GLU | A | 180 | -71.662 | -14.511 | 86.822 | 1.00 | 27.82 |
| 1435 | CD | GLU | A | 180 | -71.669 | -13.738 | 85.506 | 1.00 | 26.85 |
| 1436 | OE1 | GLU | A | 180 | -72.753 | -13.533 | 84.925 | 1.00 | 24.69 |
| 1437 | OE2 | GLU | A | 180 | -70.562 | -13.360 | 85.039 | 1.00 | 27.42 |
| 1438 | C | GLU | A | 180 | -75.377 | -15.015 | 87.888 | 1.00 | 30.75 |
| 1439 | O | GLU | A | 180 | -76.032 | -15.435 | 86.936 | 1.00 | 30.84 |
| 1440 | N | VAL | A | 181 | -75.753 | -15.198 | 89.151 | 1.00 | 32.95 |
| 1441 | CA | VAL | A | 181 | -76.956 | -15.972 | 89.473 | 1.00 | 34.49 |
| 1442 | CB | VAL | A | 181 | -76.643 | -17.107 | 90.469 | 1.00 | 34.94 |
| 1443 | CG1 | VAL | A | 181 | -77.863 | -17.989 | 90.671 | 1.00 | 33.86 |
| 1444 | CG2 | VAL | A | 181 | -75.417 | -17.922 | 90.015 | 1.00 | 33.28 |
| 1445 | C | VAL | A | 181 | -78.122 | -15.150 | 90.030 | 1.00 | 36.05 |
| 1446 | O | VAL | A | 181 | -79.203 | -15.131 | 89.455 | 1.00 | 37.26 |
| 1447 | N | PHE | A | 182 | -77.931 | -14.484 | 91.158 | 1.00 | 37.27 |
| 1448 | CA | PHE | A | 182 | -79.033 | -13.720 | 91.749 | 1.00 | 37.97 |
| 1449 | CB | PHE | A | 182 | -78.914 | -13.713 | 93.277 | 1.00 | 38.33 |
| 1450 | CG | PHE | A | 182 | -78.971 | -15.084 | 93.908 | 1.00 | 39.37 |
| 1451 | CD1 | PHE | A | 182 | -79.625 | -16.123 | 93.290 | 1.00 | 40.82 |
| 1452 | CE1 | PHE | A | 182 | -79.679 | -17.376 | 93.870 | 1.00 | 41.48 |
| 1453 | CZ | PHE | A | 182 | -79.078 | -17.596 | 95.069 | 1.00 | 42.11 |
| 1454 | CE2 | PHE | A | 182 | -78.422 | -16.561 | 95.709 | 1.00 | 42.27 |
| 1455 | CD2 | PHE | A | 182 | -78.376 | -15.317 | 95.129 | 1.00 | 40.99 |
| 1456 | C | PHE | A | 182 | -79.151 | -12.266 | 91.271 | 1.00 | 38.47 |
| 1457 | O | PHE | A | 182 | -80.187 | -11.625 | 91.506 | 1.00 | 38.87 |
| 1458 | N | SER | A | 183 | -78.106 | -11.743 | 90.617 | 1.00 | 38.34 |
| 1459 | CA | SER | A | 183 | -78.064 | -10.332 | 90.246 | 1.00 | 37.82 |
| 1460 | CB | SER | A | 183 | -78.957 | -10.014 | 89.052 | 1.00 | 37.51 |
| 1461 | OG | SER | A | 183 | -78.362 | -10.464 | 87.848 | 1.00 | 37.83 |
| 1462 | C | SER | A | 183 | -78.467 | -9.503 | 91.451 | 1.00 | 37.91 |
| 1463 | O | SER | A | 183 | -79.187 | -8.506 | 91.341 | 1.00 | 38.19 |
| 1464 | N | ALA | A | 184 | -77.983 | -9.927 | 92.607 | 1.00 | 37.60 |
| 1465 | CA | ALA | A | 184 | -78.254 | -9.236 | 93.842 | 1.00 | 37.80 |
| 1466 | CB | ALA | A | 184 | -79.644 | -9.581 | 94.334 | 1.00 | 38.33 |
| 1467 | C | ALA | A | 184 | -77.231 | -9.657 | 94.862 | 1.00 | 37.85 |
| 1468 | O | ALA | A | 184 | -76.565 | -10.681 | 94.708 | 1.00 | 38.07 |
| 1469 | N | TYR | A | 185 | -77.111 | -8.853 | 95.908 | 1.00 | 37.60 |

FIGURE 3 AC

| A | B | C | D | E | F | G | H | I | J |
|---|---|---|---|---|---|---|---|---|---|
| 1470 | CA | TYR | A | 185 | -76.203 | -9.141 | 96.993 | 1.00 | 37.56 |
| 1471 | CB | TYR | A | 185 | -75.737 | -7.841 | 97.642 | 1.00 | 37.53 |
| 1472 | CG | TYR | A | 185 | -74.558 | -7.975 | 98.566 | 1.00 | 37.51 |
| 1473 | CD1 | TYR | A | 185 | -74.288 | -6.999 | 99.521 | 1.00 | 37.76 |
| 1474 | CE1 | TYR | A | 185 | -73.190 | -7.101 | 100.356 | 1.00 | 37.08 |
| 1475 | CZ | TYR | A | 185 | -72.363 | -8.181 | 100.256 | 1.00 | 37.06 |
| 1476 | OH | TYR | A | 185 | -71.271 | -8.278 | 101.094 | 1.00 | 38.04 |
| 1477 | CE2 | TYR | A | 185 | -72.610 | -9.166 | 99.323 | 1.00 | 35.91 |
| 1478 | CD2 | TYR | A | 185 | -73.701 | -9.058 | 98.484 | 1.00 | 36.85 |
| 1479 | C | TYR | A | 185 | -76.889 | -9.999 | 98.036 | 1.00 | 37.49 |
| 1480 | O | TYR | A | 185 | -76.252 | -10.862 | 98.651 | 1.00 | 37.79 |
| 1481 | N | SER | A | 186 | -78.184 | -9.776 | 98.238 | 1.00 | 37.29 |
| 1482 | CA | SER | A | 186 | -78.888 | -10.505 | 99.290 | 1.00 | 37.19 |
| 1483 | CB | SER | A | 186 | -80.144 | -9.775 | 99.744 | 1.00 | 36.89 |
| 1484 | OG | SER | A | 186 | -81.125 | -9.876 | 98.752 | 1.00 | 37.73 |
| 1485 | C | SER | A | 186 | -79.273 | -11.900 | 98.875 | 1.00 | 36.64 |
| 1486 | O | SER | A | 186 | -79.663 | -12.140 | 97.747 | 1.00 | 37.15 |
| 1487 | N | ALA | A | 187 | -79.113 | -12.812 | 99.812 | 1.00 | 36.04 |
| 1488 | CA | ALA | A | 187 | -79.509 | -14.190 | 99.666 | 1.00 | 35.72 |
| 1489 | CB | ALA | A | 187 | -78.284 | -15.085 | 99.693 | 1.00 | 35.34 |
| 1490 | C | ALA | A | 187 | -80.409 | -14.423 | 100.885 | 1.00 | 35.43 |
| 1491 | O | ALA | A | 187 | -80.196 | -15.326 | 101.690 | 1.00 | 34.90 |
| 1492 | N | LEU | A | 188 | -81.403 | -13.549 | 101.000 | 1.00 | 35.76 |
| 1493 | CA | LEU | A | 188 | -82.351 | -13.517 | 102.098 | 1.00 | 36.19 |
| 1494 | CB | LEU | A | 188 | -82.128 | -12.250 | 102.924 | 1.00 | 36.90 |
| 1495 | CG | LEU | A | 188 | -81.116 | -12.343 | 104.045 | 1.00 | 36.81 |
| 1496 | CD1 | LEU | A | 188 | -81.376 | -11.248 | 105.051 | 1.00 | 38.05 |
| 1497 | CD2 | LEU | A | 188 | -81.318 | -13.695 | 104.665 | 1.00 | 37.67 |
| 1498 | C | LEU | A | 188 | -83.752 | -13.449 | 101.555 | 1.00 | 36.16 |
| 1499 | O | LEU | A | 188 | -84.046 | -12.606 | 100.717 | 1.00 | 36.37 |
| 1500 | N | TRP | A | 189 | -84.643 | -14.288 | 102.060 | 1.00 | 36.46 |
| 1501 | CA | TRP | A | 189 | -86.019 | -14.279 | 101.560 | 1.00 | 36.62 |
| 1502 | CB | TRP | A | 189 | -86.216 | -15.367 | 100.495 | 1.00 | 36.23 |
| 1503 | CG | TRP | A | 189 | -85.307 | -15.185 | 99.351 | 1.00 | 34.41 |
| 1504 | CD1 | TRP | A | 189 | -85.514 | -14.389 | 98.264 | 1.00 | 33.31 |
| 1505 | NE1 | TRP | A | 189 | -84.434 | -14.455 | 97.419 | 1.00 | 35.56 |
| 1506 | CE2 | TRP | A | 189 | -83.496 | -15.297 | 97.965 | 1.00 | 35.21 |
| 1507 | CD2 | TRP | A | 189 | -84.019 | -15.772 | 99.184 | 1.00 | 33.94 |
| 1508 | CE3 | TRP | A | 189 | -83.247 | -16.664 | 99.939 | 1.00 | 35.24 |
| 1509 | CZ3 | TRP | A | 189 | -82.000 | -17.047 | 99.459 | 1.00 | 33.38 |
| 1510 | CH2 | TRP | A | 189 | -81.515 | -16.554 | 98.245 | 1.00 | 33.99 |
| 1511 | CZ2 | TRP | A | 189 | -82.242 | -15.678 | 97.487 | 1.00 | 34.09 |
| 1512 | C | TRP | A | 189 | -87.063 | -14.431 | 102.657 | 1.00 | 37.21 |
| 1513 | O | TRP | A | 189 | -87.299 | -15.528 | 103.147 | 1.00 | 37.31 |
| 1514 | N | TRP | A | 190 | -87.678 | -13.314 | 103.033 | 1.00 | 38.06 |
| 1515 | CA | TRP | A | 190 | -88.740 | -13.310 | 104.028 | 1.00 | 38.71 |
| 1516 | CB | TRP | A | 190 | -89.155 | -11.879 | 104.370 | 1.00 | 38.83 |
| 1517 | CG | TRP | A | 190 | -88.270 | -11.103 | 105.274 | 1.00 | 38.32 |
| 1518 | CD1 | TRP | A | 190 | -87.389 | -10.126 | 104.918 | 1.00 | 38.37 |
| 1519 | NE1 | TRP | A | 190 | -86.765 | -9.618 | 106.031 | 1.00 | 38.44 |
| 1520 | CE2 | TRP | A | 190 | -87.255 | -10.254 | 107.139 | 1.00 | 38.85 |

FIGURE 3 AD

| A | B | C | D | E | F | G | H | I | J |
|---|---|---|---|---|---|---|---|---|---|
| 1521 | CD2 | TRP | A | 190 | -88.218 | -11.188 | 106.697 | 1.00 | 39.00 |
| 1522 | CE3 | TRP | A | 190 | -88.875 | -11.971 | 107.648 | 1.00 | 38.63 |
| 1523 | CZ3 | TRP | A | 190 | -88.563 | -11.800 | 108.982 | 1.00 | 39.07 |
| 1524 | CH2 | TRP | A | 190 | -87.600 | -10.867 | 109.387 | 1.00 | 39.64 |
| 1525 | CZ2 | TRP | A | 190 | -86.939 | -10.084 | 108.480 | 1.00 | 38.67 |
| 1526 | C | TRP | A | 190 | -89.962 | -13.958 | 103.403 | 1.00 | 39.34 |
| 1527 | O | TRP | A | 190 | -90.298 | -13.652 | 102.260 | 1.00 | 38.94 |
| 1528 | N | SER | A | 191 | -90.640 | -14.825 | 104.148 | 1.00 | 40.07 |
| 1529 | CA | SER | A | 191 | -91.901 | -15.367 | 103.671 | 1.00 | 40.97 |
| 1530 | CB | SER | A | 191 | -92.399 | -16.496 | 104.568 | 1.00 | 41.50 |
| 1531 | OG | SER | A | 191 | -93.155 | -15.990 | 105.647 | 1.00 | 41.74 |
| 1532 | C | SER | A | 191 | -92.893 | -14.206 | 103.633 | 1.00 | 41.49 |
| 1533 | O | SER | A | 191 | -92.733 | -13.211 | 104.335 | 1.00 | 41.38 |
| 1534 | N | PRO | A | 192 | -93.949 | -14.364 | 102.857 | 1.00 | 41.99 |
| 1535 | CA | PRO | A | 192 | -94.829 | -13.253 | 102.500 | 1.00 | 42.66 |
| 1536 | CB | PRO | A | 192 | -96.010 | -13.954 | 101.810 | 1.00 | 42.51 |
| 1537 | CG | PRO | A | 192 | -95.436 | -15.217 | 101.309 | 1.00 | 42.06 |
| 1538 | CD | PRO | A | 192 | -94.443 | -15.649 | 102.342 | 1.00 | 41.94 |
| 1539 | C | PRO | A | 192 | -95.339 | -12.481 | 103.679 | 1.00 | 43.23 |
| 1540 | O | PRO | A | 192 | -95.655 | -11.293 | 103.555 | 1.00 | 43.70 |
| 1541 | N | ASN | A | 193 | -95.424 | -13.149 | 104.814 | 1.00 | 43.81 |
| 1542 | CA | ASN | A | 193 | -96.025 | -12.535 | 105.970 | 1.00 | 44.56 |
| 1543 | CB | ASN | A | 193 | -97.148 | -13.426 | 106.490 | 1.00 | 45.57 |
| 1544 | CG | ASN | A | 193 | -96.783 | -14.162 | 107.747 | 1.00 | 47.13 |
| 1545 | OD1 | ASN | A | 193 | -95.624 | -14.202 | 108.170 | 1.00 | 48.73 |
| 1546 | ND2 | ASN | A | 193 | -97.787 | -14.735 | 108.371 | 1.00 | 51.47 |
| 1547 | C | ASN | A | 193 | -95.042 | -12.163 | 107.065 | 1.00 | 44.28 |
| 1548 | O | ASN | A | 193 | -95.425 | -11.547 | 108.060 | 1.00 | 44.80 |
| 1549 | N | GLY | A | 194 | -93.779 | -12.534 | 106.885 | 1.00 | 43.59 |
| 1550 | CA | GLY | A | 194 | -92.746 | -12.158 | 107.832 | 1.00 | 42.90 |
| 1551 | C | GLY | A | 194 | -92.365 | -13.281 | 108.767 | 1.00 | 42.46 |
| 1552 | O | GLY | A | 194 | -91.286 | -13.275 | 109.355 | 1.00 | 41.89 |
| 1553 | N | THR | A | 195 | -93.255 | -14.257 | 108.894 | 1.00 | 42.23 |
| 1554 | CA | THR | A | 195 | -93.015 | -15.377 | 109.786 | 1.00 | 42.35 |
| 1555 | CB | THR | A | 195 | -94.105 | -16.441 | 109.621 | 1.00 | 42.51 |
| 1556 | OG1 | THR | A | 195 | -95.318 | -15.985 | 110.224 | 1.00 | 43.31 |
| 1557 | CG2 | THR | A | 195 | -93.759 | -17.663 | 110.444 | 1.00 | 42.51 |
| 1558 | C | THR | A | 195 | -91.640 | -16.016 | 109.579 | 1.00 | 41.99 |
| 1559 | O | THR | A | 195 | -90.813 | -16.045 | 110.492 | 1.00 | 41.82 |
| 1560 | N | PHE | A | 196 | -91.399 | -16.531 | 108.376 | 1.00 | 41.36 |
| 1561 | CA | PHE | A | 196 | -90.135 | -17.208 | 108.113 | 1.00 | 40.45 |
| 1562 | CB | PHE | A | 196 | -90.388 | -18.463 | 107.284 | 1.00 | 40.63 |
| 1563 | CG | PHE | A | 196 | -91.227 | -19.485 | 107.987 | 1.00 | 39.35 |
| 1564 | CD1 | PHE | A | 196 | -90.738 | -20.157 | 109.089 | 1.00 | 38.75 |
| 1565 | CE1 | PHE | A | 196 | -91.513 | -21.096 | 109.743 | 1.00 | 38.83 |
| 1566 | CZ | PHE | A | 196 | -92.777 | -21.373 | 109.290 | 1.00 | 37.56 |
| 1567 | CE2 | PHE | A | 196 | -93.272 | -20.708 | 108.199 | 1.00 | 36.97 |
| 1568 | CD2 | PHE | A | 196 | -92.503 | -19.767 | 107.554 | 1.00 | 37.96 |
| 1569 | C | PHE | A | 196 | -89.125 | -16.315 | 107.411 | 1.00 | 39.96 |
| 1570 | O | PHE | A | 196 | -89.479 | -15.356 | 106.723 | 1.00 | 40.12 |
| 1571 | N | LEU | A | 197 | -87.855 | -16.610 | 107.624 | 1.00 | 39.33 |

FIGURE 3 AE

| A | B | C | D | E | F | G | H | I | J |
|---|---|---|---|---|---|---|---|---|---|
| 1572 | CA  | LEU | A | 197 | -86.792 | -15.921 | 106.903 | 1.00 | 38.31 |
| 1573 | CB  | LEU | A | 197 | -85.943 | -15.070 | 107.831 | 1.00 | 38.53 |
| 1574 | CG  | LEU | A | 197 | -84.748 | -14.388 | 107.187 | 1.00 | 39.02 |
| 1575 | CD1 | LEU | A | 197 | -84.012 | -13.621 | 108.269 | 1.00 | 40.57 |
| 1576 | CD2 | LEU | A | 197 | -85.194 | -13.460 | 106.068 | 1.00 | 39.51 |
| 1577 | C   | LEU | A | 197 | -85.942 | -17.016 | 106.335 | 1.00 | 37.20 |
| 1578 | O   | LEU | A | 197 | -85.277 | -17.719 | 107.070 | 1.00 | 36.63 |
| 1579 | N   | ALA | A | 198 | -86.012 | -17.210 | 105.029 | 1.00 | 36.53 |
| 1580 | CA  | ALA | A | 198 | -85.174 | -18.231 | 104.416 | 1.00 | 35.68 |
| 1581 | CB  | ALA | A | 198 | -85.896 | -18.871 | 103.250 | 1.00 | 35.91 |
| 1582 | C   | ALA | A | 198 | -83.883 | -17.560 | 103.962 | 1.00 | 34.82 |
| 1583 | O   | ALA | A | 198 | -83.877 | -16.369 | 103.617 | 1.00 | 34.28 |
| 1584 | N   | TYR | A | 199 | -82.780 | -18.295 | 103.991 | 1.00 | 33.86 |
| 1585 | CA  | TYR | A | 199 | -81.533 | -17.730 | 103.485 | 1.00 | 33.19 |
| 1586 | CB  | TYR | A | 199 | -80.798 | -16.950 | 104.571 | 1.00 | 32.78 |
| 1587 | CG  | TYR | A | 199 | -80.354 | -17.816 | 105.727 | 1.00 | 33.58 |
| 1588 | CD1 | TYR | A | 199 | -79.074 | -18.358 | 105.773 | 1.00 | 32.56 |
| 1589 | CE1 | TYR | A | 199 | -78.676 | -19.153 | 106.840 | 1.00 | 32.70 |
| 1590 | CZ  | TYR | A | 199 | -79.566 | -19.409 | 107.867 | 1.00 | 32.39 |
| 1591 | OH  | TYR | A | 199 | -79.204 | -20.197 | 108.935 | 1.00 | 33.54 |
| 1592 | CE2 | TYR | A | 199 | -80.820 | -18.882 | 107.842 | 1.00 | 32.58 |
| 1593 | CD2 | TYR | A | 199 | -81.216 | -18.090 | 106.779 | 1.00 | 33.74 |
| 1594 | C   | TYR | A | 199 | -80.640 | -18.805 | 102.898 | 1.00 | 32.53 |
| 1595 | O   | TYR | A | 199 | -80.836 | -19.979 | 103.157 | 1.00 | 32.66 |
| 1596 | N   | ALA | A | 200 | -79.655 | -18.390 | 102.102 | 1.00 | 32.28 |
| 1597 | CA  | ALA | A | 200 | -78.700 | -19.319 | 101.509 | 1.00 | 31.66 |
| 1598 | CB  | ALA | A | 200 | -78.590 | -19.102 | 99.985  | 1.00 | 31.58 |
| 1599 | C   | ALA | A | 200 | -77.371 | -19.096 | 102.156 | 1.00 | 31.10 |
| 1600 | O   | ALA | A | 200 | -77.051 | -17.982 | 102.512 | 1.00 | 31.98 |
| 1601 | N   | GLN | A | 201 | -76.586 | -20.147 | 102.318 | 1.00 | 30.82 |
| 1602 | CA  | GLN | A | 201 | -75.253 | -19.974 | 102.864 | 1.00 | 30.37 |
| 1603 | CB  | GLN | A | 201 | -75.065 | -20.810 | 104.109 | 1.00 | 30.06 |
| 1604 | CG  | GLN | A | 201 | -73.659 | -20.886 | 104.511 | 1.00 | 29.92 |
| 1605 | CD  | GLN | A | 201 | -73.433 | -21.897 | 105.590 | 1.00 | 32.22 |
| 1606 | OE1 | GLN | A | 201 | -73.089 | -23.034 | 105.299 | 1.00 | 32.66 |
| 1607 | NE2 | GLN | A | 201 | -73.616 | -21.487 | 106.852 | 1.00 | 31.05 |
| 1608 | C   | GLN | A | 201 | -74.232 | -20.391 | 101.826 | 1.00 | 30.16 |
| 1609 | O   | GLN | A | 201 | -74.350 | -21.462 | 101.244 | 1.00 | 30.15 |
| 1610 | N   | PHE | A | 202 | -73.223 | -19.555 | 101.613 | 1.00 | 30.02 |
| 1611 | CA  | PHE | A | 202 | -72.236 | -19.831 | 100.581 | 1.00 | 30.30 |
| 1612 | CB  | PHE | A | 202 | -72.135 | -18.655 | 99.600  | 1.00 | 29.91 |
| 1613 | CG  | PHE | A | 202 | -73.389 | -18.412 | 98.844  | 1.00 | 28.40 |
| 1614 | CD1 | PHE | A | 202 | -73.806 | -19.310 | 97.870  | 1.00 | 26.83 |
| 1615 | CE1 | PHE | A | 202 | -74.966 | -19.103 | 97.177  | 1.00 | 25.09 |
| 1616 | CZ  | PHE | A | 202 | -75.732 | -18.000 | 97.447  | 1.00 | 26.35 |
| 1617 | CE2 | PHE | A | 202 | -75.338 | -17.100 | 98.439  | 1.00 | 26.18 |
| 1618 | CD2 | PHE | A | 202 | -74.175 | -17.312 | 99.124  | 1.00 | 27.09 |
| 1619 | C   | PHE | A | 202 | -70.878 | -20.118 | 101.165 | 1.00 | 30.53 |
| 1620 | O   | PHE | A | 202 | -70.402 | -19.384 | 102.030 | 1.00 | 30.67 |
| 1621 | N   | ASN | A | 203 | -70.247 | -21.173 | 100.656 | 1.00 | 30.49 |
| 1622 | CA  | ASN | A | 203 | -68.937 | -21.597 | 101.129 | 1.00 | 30.96 |

FIGURE 3 AF

| A | B | C | D | E | F | G | H | I | J |
|---|---|---|---|---|---|---|---|---|---|
| 1623 | CB | ASN | A | 203 | -69.048 | -23.008 | 101.735 | 1.00 | 31.11 |
| 1624 | CG | ASN | A | 203 | -67.778 | -23.455 | 102.411 | 1.00 | 31.34 |
| 1625 | OD1 | ASN | A | 203 | -66.727 | -22.836 | 102.238 | 1.00 | 31.57 |
| 1626 | ND2 | ASN | A | 203 | -67.860 | -24.543 | 103.180 | 1.00 | 34.70 |
| 1627 | C | ASN | A | 203 | -67.894 | -21.556 | 100.008 | 1.00 | 30.82 |
| 1628 | O | ASN | A | 203 | -67.928 | -22.369 | 99.081 | 1.00 | 30.86 |
| 1629 | N | ASP | A | 204 | -66.972 | -20.611 | 100.102 | 1.00 | 30.71 |
| 1630 | CA | ASP | A | 204 | -65.942 | -20.417 | 99.088 | 1.00 | 31.08 |
| 1631 | CB | ASP | A | 204 | -65.862 | -18.950 | 98.716 | 1.00 | 31.03 |
| 1632 | CG | ASP | A | 204 | -67.066 | -18.504 | 97.961 | 1.00 | 31.81 |
| 1633 | OD1 | ASP | A | 204 | -68.174 | -18.922 | 98.345 | 1.00 | 33.00 |
| 1634 | OD2 | ASP | A | 204 | -67.007 | -17.763 | 96.966 | 1.00 | 34.30 |
| 1635 | C | ASP | A | 204 | -64.579 | -20.874 | 99.524 | 1.00 | 31.17 |
| 1636 | O | ASP | A | 204 | -63.573 | -20.516 | 98.927 | 1.00 | 31.18 |
| 1637 | N | THR | A | 205 | -64.545 | -21.682 | 100.569 | 1.00 | 31.79 |
| 1638 | CA | THR | A | 205 | -63.289 | -22.139 | 101.113 | 1.00 | 31.97 |
| 1639 | CB | THR | A | 205 | -63.538 | -23.277 | 102.077 | 1.00 | 32.32 |
| 1640 | OG1 | THR | A | 205 | -64.383 | -22.792 | 103.118 | 1.00 | 32.88 |
| 1641 | CG2 | THR | A | 205 | -62.241 | -23.640 | 102.806 | 1.00 | 32.65 |
| 1642 | C | THR | A | 205 | -62.236 | -22.536 | 100.084 | 1.00 | 31.74 |
| 1643 | O | THR | A | 205 | -61.082 | -22.117 | 100.203 | 1.00 | 31.95 |
| 1644 | N | GLU | A | 206 | -62.602 | -23.335 | 99.088 | 1.00 | 31.47 |
| 1645 | CA | GLU | A | 206 | -61.583 | -23.766 | 98.125 | 1.00 | 31.78 |
| 1646 | CB | GLU | A | 206 | -61.602 | -25.289 | 97.923 | 1.00 | 32.33 |
| 1647 | CG | GLU | A | 206 | -61.422 | -26.118 | 99.188 | 1.00 | 35.48 |
| 1648 | CD | GLU | A | 206 | -61.709 | -27.596 | 98.948 | 1.00 | 41.10 |
| 1649 | OE1 | GLU | A | 206 | -60.726 | -28.382 | 98.864 | 1.00 | 42.82 |
| 1650 | OE2 | GLU | A | 206 | -62.907 | -27.972 | 98.817 | 1.00 | 40.88 |
| 1651 | C | GLU | A | 206 | -61.714 | -23.058 | 96.781 | 1.00 | 30.95 |
| 1652 | O | GLU | A | 206 | -61.169 | -23.514 | 95.774 | 1.00 | 30.73 |
| 1653 | N | VAL | A | 207 | -62.440 | -21.949 | 96.767 | 1.00 | 29.81 |
| 1654 | CA | VAL | A | 207 | -62.572 | -21.166 | 95.552 | 1.00 | 29.59 |
| 1655 | CB | VAL | A | 207 | -63.826 | -20.298 | 95.613 | 1.00 | 29.22 |
| 1656 | CG1 | VAL | A | 207 | -63.909 | -19.353 | 94.413 | 1.00 | 28.22 |
| 1657 | CG2 | VAL | A | 207 | -65.038 | -21.200 | 95.693 | 1.00 | 28.87 |
| 1658 | C | VAL | A | 207 | -61.314 | -20.333 | 95.427 | 1.00 | 29.48 |
| 1659 | O | VAL | A | 207 | -60.923 | -19.681 | 96.375 | 1.00 | 30.00 |
| 1660 | N | PRO | A | 208 | -60.639 | -20.406 | 94.289 | 1.00 | 29.75 |
| 1661 | CA | PRO | A | 208 | -59.374 | -19.669 | 94.092 | 1.00 | 29.54 |
| 1662 | CB | PRO | A | 208 | -58.871 | -20.156 | 92.724 | 1.00 | 29.39 |
| 1663 | CG | PRO | A | 208 | -59.699 | -21.403 | 92.435 | 1.00 | 30.24 |
| 1664 | CD | PRO | A | 208 | -61.023 | -21.200 | 93.109 | 1.00 | 29.62 |
| 1665 | C | PRO | A | 208 | -59.593 | -18.166 | 94.066 | 1.00 | 29.18 |
| 1666 | O | PRO | A | 208 | -60.687 | -17.701 | 93.796 | 1.00 | 29.26 |
| 1667 | N | LEU | A | 209 | -58.546 | -17.398 | 94.318 | 1.00 | 28.89 |
| 1668 | CA | LEU | A | 209 | -58.737 | -15.970 | 94.382 | 1.00 | 28.41 |
| 1669 | CB | LEU | A | 209 | -58.194 | -15.416 | 95.703 | 1.00 | 28.78 |
| 1670 | CG | LEU | A | 209 | -59.122 | -15.831 | 96.854 | 1.00 | 30.32 |
| 1671 | CD1 | LEU | A | 209 | -59.365 | -14.702 | 97.815 | 1.00 | 32.76 |
| 1672 | CD2 | LEU | A | 209 | -58.574 | -17.040 | 97.566 | 1.00 | 31.36 |
| 1673 | C | LEU | A | 209 | -58.105 | -15.245 | 93.231 | 1.00 | 27.31 |

FIGURE 3 AG

| A | B | C | D | E | F | G | H | I | J |
|---|---|---|---|---|---|---|---|---|---|
| 1674 | O | LEU | A | 209 | -56.957 | -15.507 | 92.907 | 1.00 | 28.03 |
| 1675 | N | ILE | A | 210 | -58.865 | -14.362 | 92.596 | 1.00 | 25.30 |
| 1676 | CA | ILE | A | 210 | -58.258 | -13.466 | 91.638 | 1.00 | 24.34 |
| 1677 | CB | ILE | A | 210 | -59.288 | -12.856 | 90.638 | 1.00 | 24.07 |
| 1678 | CG1 | ILE | A | 210 | -58.602 | -11.882 | 89.681 | 1.00 | 22.86 |
| 1679 | CD1 | ILE | A | 210 | -57.653 | -12.506 | 88.749 | 1.00 | 17.11 |
| 1680 | CG2 | ILE | A | 210 | -60.416 | -12.105 | 91.348 | 1.00 | 22.07 |
| 1681 | C | ILE | A | 210 | -57.611 | -12.379 | 92.484 | 1.00 | 24.74 |
| 1682 | O | ILE | A | 210 | -58.214 | -11.864 | 93.471 | 1.00 | 24.26 |
| 1683 | N | GLU | A | 211 | -56.367 | -12.071 | 92.140 | 1.00 | 24.06 |
| 1684 | CA | GLU | A | 211 | -55.636 | -11.012 | 92.804 | 1.00 | 23.86 |
| 1685 | CB | GLU | A | 211 | -54.373 | -11.555 | 93.468 | 1.00 | 23.56 |
| 1686 | CG | GLU | A | 211 | -54.595 | -12.856 | 94.218 | 1.00 | 25.96 |
| 1687 | CD | GLU | A | 211 | -53.497 | -13.180 | 95.221 | 1.00 | 26.55 |
| 1688 | OE1 | GLU | A | 211 | -53.806 | -13.788 | 96.242 | 1.00 | 29.23 |
| 1689 | OE2 | GLU | A | 211 | -52.328 | -12.837 | 94.997 | 1.00 | 29.08 |
| 1690 | C | GLU | A | 211 | -55.236 | -9.978 | 91.769 | 1.00 | 23.44 |
| 1691 | O | GLU | A | 211 | -54.834 | -10.328 | 90.666 | 1.00 | 23.22 |
| 1692 | N | TYR | A | 212 | -55.348 | -8.708 | 92.138 | 1.00 | 23.21 |
| 1693 | CA | TYR | A | 212 | -54.923 | -7.615 | 91.294 | 1.00 | 23.31 |
| 1694 | CB | TYR | A | 212 | -55.985 | -7.259 | 90.234 | 1.00 | 22.86 |
| 1695 | CG | TYR | A | 212 | -57.348 | -6.961 | 90.774 | 1.00 | 22.22 |
| 1696 | CD1 | TYR | A | 212 | -57.684 | -5.679 | 91.174 | 1.00 | 23.19 |
| 1697 | CE1 | TYR | A | 212 | -58.916 | -5.386 | 91.671 | 1.00 | 21.83 |
| 1698 | CZ | TYR | A | 212 | -59.858 | -6.368 | 91.791 | 1.00 | 22.04 |
| 1699 | OH | TYR | A | 212 | -61.092 | -6.029 | 92.302 | 1.00 | 22.37 |
| 1700 | CE2 | TYR | A | 212 | -59.563 | -7.660 | 91.420 | 1.00 | 23.02 |
| 1701 | CD2 | TYR | A | 212 | -58.301 | -7.953 | 90.910 | 1.00 | 22.36 |
| 1702 | C | TYR | A | 212 | -54.560 | -6.437 | 92.200 | 1.00 | 23.96 |
| 1703 | O | TYR | A | 212 | -54.968 | -6.388 | 93.355 | 1.00 | 24.35 |
| 1704 | N | SER | A | 213 | -53.735 | -5.531 | 91.698 | 1.00 | 24.43 |
| 1705 | CA | SER | A | 213 | -53.308 | -4.386 | 92.472 | 1.00 | 24.97 |
| 1706 | CB | SER | A | 213 | -52.023 | -3.810 | 91.898 | 1.00 | 24.59 |
| 1707 | OG | SER | A | 213 | -51.081 | -4.834 | 91.666 | 1.00 | 27.00 |
| 1708 | C | SER | A | 213 | -54.350 | -3.293 | 92.445 | 1.00 | 25.46 |
| 1709 | O | SER | A | 213 | -55.017 | -3.073 | 91.417 | 1.00 | 25.74 |
| 1710 | N | PHE | A | 214 | -54.484 | -2.612 | 93.581 | 1.00 | 25.16 |
| 1711 | CA | PHE | A | 214 | -55.314 | -1.424 | 93.686 | 1.00 | 25.20 |
| 1712 | CB | PHE | A | 214 | -56.482 | -1.643 | 94.650 | 1.00 | 24.90 |
| 1713 | CG | PHE | A | 214 | -57.523 | -0.566 | 94.571 | 1.00 | 25.71 |
| 1714 | CD1 | PHE | A | 214 | -57.441 | 0.549 | 95.390 | 1.00 | 24.81 |
| 1715 | CE1 | PHE | A | 214 | -58.361 | 1.557 | 95.302 | 1.00 | 25.33 |
| 1716 | CZ | PHE | A | 214 | -59.400 | 1.474 | 94.396 | 1.00 | 25.34 |
| 1717 | CE2 | PHE | A | 214 | -59.500 | 0.360 | 93.564 | 1.00 | 25.76 |
| 1718 | CD2 | PHE | A | 214 | -58.552 | -0.641 | 93.647 | 1.00 | 25.42 |
| 1719 | C | PHE | A | 214 | -54.356 | -0.312 | 94.145 | 1.00 | 25.52 |
| 1720 | O | PHE | A | 214 | -53.677 | -0.437 | 95.157 | 1.00 | 25.22 |
| 1721 | N | TYR | A | 215 | -54.261 | 0.766 | 93.385 | 1.00 | 25.88 |
| 1722 | CA | TYR | A | 215 | -53.219 | 1.734 | 93.670 | 1.00 | 25.86 |
| 1723 | CB | TYR | A | 215 | -52.675 | 2.327 | 92.367 | 1.00 | 25.83 |
| 1724 | CG | TYR | A | 215 | -52.158 | 1.223 | 91.478 | 1.00 | 25.90 |

FIGURE 3 AH

| A | B | C | D | E | F | G | H | I | J |
|---|---|---|---|---|---|---|---|---|---|
| 1725 | CD1 | TYR | A | 215 | -52.962 | 0.673 | 90.474 | 1.00 | 24.54 |
| 1726 | CE1 | TYR | A | 215 | -52.498 | -0.363 | 89.677 | 1.00 | 22.91 |
| 1727 | CZ | TYR | A | 215 | -51.224 | -0.874 | 89.891 | 1.00 | 23.93 |
| 1728 | OH | TYR | A | 215 | -50.772 | -1.912 | 89.118 | 1.00 | 23.07 |
| 1729 | CE2 | TYR | A | 215 | -50.412 | -0.362 | 90.891 | 1.00 | 22.24 |
| 1730 | CD2 | TYR | A | 215 | -50.883 | 0.682 | 91.676 | 1.00 | 23.91 |
| 1731 | C | TYR | A | 215 | -53.668 | 2.785 | 94.648 | 1.00 | 26.58 |
| 1732 | O | TYR | A | 215 | -52.848 | 3.371 | 95.382 | 1.00 | 26.13 |
| 1733 | N | SER | A | 216 | -54.975 | 3.003 | 94.656 | 1.00 | 26.91 |
| 1734 | CA | SER | A | 216 | -55.603 | 3.961 | 95.541 | 1.00 | 28.06 |
| 1735 | CB | SER | A | 216 | -55.359 | 3.596 | 97.006 | 1.00 | 28.14 |
| 1736 | OG | SER | A | 216 | -56.333 | 4.212 | 97.838 | 1.00 | 28.49 |
| 1737 | C | SER | A | 216 | -55.136 | 5.390 | 95.284 | 1.00 | 28.60 |
| 1738 | O | SER | A | 216 | -54.522 | 5.698 | 94.256 | 1.00 | 27.55 |
| 1739 | N | ASP | A | 217 | -55.438 | 6.256 | 96.245 | 1.00 | 29.85 |
| 1740 | CA | ASP | A | 217 | -55.048 | 7.658 | 96.150 | 1.00 | 31.23 |
| 1741 | CB | ASP | A | 217 | -55.684 | 8.468 | 97.306 | 1.00 | 32.03 |
| 1742 | CG | ASP | A | 217 | -57.235 | 8.517 | 97.212 | 1.00 | 36.76 |
| 1743 | OD1 | ASP | A | 217 | -57.792 | 8.879 | 96.126 | 1.00 | 37.66 |
| 1744 | OD2 | ASP | A | 217 | -57.985 | 8.184 | 98.171 | 1.00 | 41.02 |
| 1745 | C | ASP | A | 217 | -53.517 | 7.768 | 96.135 | 1.00 | 31.09 |
| 1746 | O | ASP | A | 217 | -52.792 | 6.883 | 96.615 | 1.00 | 30.94 |
| 1747 | N | GLU | A | 218 | -53.030 | 8.851 | 95.564 | 1.00 | 31.23 |
| 1748 | CA | GLU | A | 218 | -51.600 | 9.117 | 95.495 | 1.00 | 31.57 |
| 1749 | CB | GLU | A | 218 | -51.380 | 10.515 | 94.911 | 1.00 | 31.79 |
| 1750 | CG | GLU | A | 218 | -49.948 | 10.987 | 94.981 | 1.00 | 34.28 |
| 1751 | CD | GLU | A | 218 | -49.771 | 12.350 | 94.364 | 1.00 | 36.98 |
| 1752 | OE1 | GLU | A | 218 | -48.607 | 12.764 | 94.204 | 1.00 | 38.67 |
| 1753 | OE2 | GLU | A | 218 | -50.792 | 13.001 | 94.038 | 1.00 | 38.85 |
| 1754 | C | GLU | A | 218 | -50.831 | 8.923 | 96.823 | 1.00 | 31.30 |
| 1755 | O | GLU | A | 218 | -49.649 | 8.593 | 96.808 | 1.00 | 30.88 |
| 1756 | N | SER | A | 219 | -51.507 | 9.105 | 97.958 | 1.00 | 31.27 |
| 1757 | CA | SER | A | 219 | -50.917 | 8.889 | 99.300 | 1.00 | 31.15 |
| 1758 | CB | SER | A | 219 | -51.870 | 9.442 | 100.363 | 1.00 | 31.69 |
| 1759 | OG | SER | A | 219 | -52.089 | 10.817 | 100.141 | 1.00 | 35.63 |
| 1760 | C | SER | A | 219 | -50.580 | 7.447 | 99.723 | 1.00 | 30.25 |
| 1761 | O | SER | A | 219 | -49.831 | 7.254 | 100.690 | 1.00 | 29.72 |
| 1762 | N | LEU | A | 220 | -51.176 | 6.438 | 99.080 | 1.00 | 29.12 |
| 1763 | CA | LEU | A | 220 | -50.864 | 5.051 | 99.446 | 1.00 | 28.25 |
| 1764 | CB | LEU | A | 220 | -51.833 | 4.071 | 98.791 | 1.00 | 27.97 |
| 1765 | CG | LEU | A | 220 | -52.445 | 2.973 | 99.649 | 1.00 | 29.05 |
| 1766 | CD1 | LEU | A | 220 | -52.744 | 1.692 | 98.827 | 1.00 | 26.88 |
| 1767 | CD2 | LEU | A | 220 | -51.643 | 2.669 | 100.936 | 1.00 | 25.26 |
| 1768 | C | LEU | A | 220 | -49.494 | 4.801 | 98.856 | 1.00 | 27.67 |
| 1769 | O | LEU | A | 220 | -49.348 | 4.774 | 97.627 | 1.00 | 26.93 |
| 1770 | N | GLN | A | 221 | -48.487 | 4.604 | 99.693 | 1.00 | 27.07 |
| 1771 | CA | GLN | A | 221 | -47.165 | 4.439 | 99.115 | 1.00 | 27.05 |
| 1772 | CB | GLN | A | 221 | -46.035 | 4.916 | 100.051 | 1.00 | 26.55 |
| 1773 | CG | GLN | A | 221 | -45.174 | 3.856 | 100.608 | 1.00 | 27.44 |
| 1774 | CD | GLN | A | 221 | -44.153 | 4.353 | 101.649 | 1.00 | 27.15 |
| 1775 | OE1 | GLN | A | 221 | -44.189 | 3.907 | 102.788 | 1.00 | 26.51 |

FIGURE 3 AI

| A | B | C | D | E | F | G | H | I | J |
|---|---|---|---|---|---|---|---|---|---|
| 1776 | NE2 | GLN | A | 221 | -43.241 | 5.233 | 101.247 | 1.00 | 23.19 |
| 1777 | C | GLN | A | 221 | -46.963 | 3.043 | 98.505 | 1.00 | 26.56 |
| 1778 | O | GLN | A | 221 | -46.320 | 2.927 | 97.479 | 1.00 | 26.46 |
| 1779 | N | TYR | A | 222 | -47.558 | 2.016 | 99.111 | 1.00 | 26.45 |
| 1780 | CA | TYR | A | 222 | -47.486 | 0.640 | 98.598 | 1.00 | 26.17 |
| 1781 | CB | TYR | A | 222 | -47.095 | -0.367 | 99.687 | 1.00 | 25.55 |
| 1782 | CG | TYR | A | 222 | -45.625 | -0.320 | 100.069 | 1.00 | 26.44 |
| 1783 | CD1 | TYR | A | 222 | -44.698 | -1.208 | 99.510 | 1.00 | 23.84 |
| 1784 | CE1 | TYR | A | 222 | -43.347 | -1.155 | 99.870 | 1.00 | 25.81 |
| 1785 | CZ | TYR | A | 222 | -42.927 | -0.211 | 100.802 | 1.00 | 25.57 |
| 1786 | OH | TYR | A | 222 | -41.604 | -0.109 | 101.163 | 1.00 | 25.00 |
| 1787 | CE2 | TYR | A | 222 | -43.831 | 0.679 | 101.350 | 1.00 | 25.91 |
| 1788 | CD2 | TYR | A | 222 | -45.164 | 0.620 | 100.994 | 1.00 | 26.23 |
| 1789 | C | TYR | A | 222 | -48.854 | 0.235 | 98.078 | 1.00 | 26.17 |
| 1790 | O | TYR | A | 222 | -49.843 | 0.320 | 98.802 | 1.00 | 26.60 |
| 1791 | N | PRO | A | 223 | -48.931 | -0.186 | 96.825 | 1.00 | 25.52 |
| 1792 | CA | PRO | A | 223 | -50.208 | -0.638 | 96.309 | 1.00 | 24.97 |
| 1793 | CB | PRO | A | 223 | -49.861 | -1.139 | 94.894 | 1.00 | 24.57 |
| 1794 | CG | PRO | A | 223 | -48.696 | -0.323 | 94.484 | 1.00 | 24.47 |
| 1795 | CD | PRO | A | 223 | -47.873 | -0.199 | 95.791 | 1.00 | 25.38 |
| 1796 | C | PRO | A | 223 | -50.736 | -1.752 | 97.186 | 1.00 | 24.85 |
| 1797 | O | PRO | A | 223 | -49.977 | -2.469 | 97.821 | 1.00 | 23.95 |
| 1798 | N | LYS | A | 224 | -52.049 | -1.890 | 97.199 | 1.00 | 25.28 |
| 1799 | CA | LYS | A | 224 | -52.718 | -2.944 | 97.927 | 1.00 | 26.38 |
| 1800 | CB | LYS | A | 224 | -54.005 | -2.404 | 98.559 | 1.00 | 26.73 |
| 1801 | CG | LYS | A | 224 | -54.884 | -3.505 | 99.113 | 1.00 | 31.45 |
| 1802 | CD | LYS | A | 224 | -56.300 | -3.033 | 99.415 | 1.00 | 38.45 |
| 1803 | CE | LYS | A | 224 | -57.258 | -4.231 | 99.540 | 1.00 | 40.77 |
| 1804 | NZ | LYS | A | 224 | -58.666 | -3.805 | 99.861 | 1.00 | 43.53 |
| 1805 | C | LYS | A | 224 | -53.093 | -4.046 | 96.941 | 1.00 | 26.16 |
| 1806 | O | LYS | A | 224 | -53.346 | -3.787 | 95.770 | 1.00 | 26.68 |
| 1807 | N | THR | A | 225 | -53.150 | -5.277 | 97.413 | 1.00 | 25.90 |
| 1808 | CA | THR | A | 225 | -53.533 | -6.366 | 96.555 | 1.00 | 25.55 |
| 1809 | CB | THR | A | 225 | -52.553 | -7.532 | 96.751 | 1.00 | 25.37 |
| 1810 | OG1 | THR | A | 225 | -51.293 | -7.181 | 96.178 | 1.00 | 25.61 |
| 1811 | CG2 | THR | A | 225 | -52.972 | -8.742 | 95.937 | 1.00 | 25.25 |
| 1812 | C | THR | A | 225 | -54.955 | -6.775 | 96.912 | 1.00 | 25.60 |
| 1813 | O | THR | A | 225 | -55.212 | -7.167 | 98.029 | 1.00 | 25.34 |
| 1814 | N | VAL | A | 226 | -55.890 | -6.654 | 95.973 | 1.00 | 25.53 |
| 1815 | CA | VAL | A | 226 | -57.248 | -7.081 | 96.259 | 1.00 | 25.10 |
| 1816 | CB | VAL | A | 226 | -58.291 | -6.298 | 95.437 | 1.00 | 25.59 |
| 1817 | CG1 | VAL | A | 226 | -59.694 | -6.918 | 95.590 | 1.00 | 23.61 |
| 1818 | CG2 | VAL | A | 226 | -58.308 | -4.843 | 95.852 | 1.00 | 23.96 |
| 1819 | C | VAL | A | 226 | -57.326 | -8.554 | 95.912 | 1.00 | 25.63 |
| 1820 | O | VAL | A | 226 | -56.780 | -8.984 | 94.901 | 1.00 | 25.43 |
| 1821 | N | ARG | A | 227 | -57.982 | -9.327 | 96.766 | 1.00 | 26.04 |
| 1822 | CA | ARG | A | 227 | -58.085 | -10.752 | 96.574 | 1.00 | 26.89 |
| 1823 | CB | ARG | A | 227 | -57.274 | -11.497 | 97.636 | 1.00 | 27.10 |
| 1824 | CG | ARG | A | 227 | -55.813 | -11.080 | 97.664 | 1.00 | 29.19 |
| 1825 | CD | ARG | A | 227 | -54.920 | -11.828 | 98.648 | 1.00 | 31.64 |
| 1826 | NE | ARG | A | 227 | -53.504 | -11.567 | 98.358 | 1.00 | 35.93 |

FIGURE 3 AJ

| A | B | C | D | E | F | G | H | I | J |
|---|---|---|---|---|---|---|---|---|---|
| 1827 | CZ | ARG | A | 227 | -52.752 | -10.621 | 98.943 | 1.00 | 36.92 |
| 1828 | NH1 | ARG | A | 227 | -53.256 | -9.829 | 99.885 | 1.00 | 37.20 |
| 1829 | NH2 | ARG | A | 227 | -51.478 | -10.480 | 98.590 | 1.00 | 35.93 |
| 1830 | C | ARG | A | 227 | -59.535 | -11.122 | 96.677 | 1.00 | 27.13 |
| 1831 | O | ARG | A | 227 | -60.190 | -10.820 | 97.672 | 1.00 | 27.94 |
| 1832 | N | VAL | A | 228 | -60.071 | -11.751 | 95.641 | 1.00 | 26.85 |
| 1833 | CA | VAL | A | 228 | -61.466 | -12.133 | 95.722 | 1.00 | 26.24 |
| 1834 | CB | VAL | A | 228 | -62.430 | -11.041 | 95.174 | 1.00 | 26.15 |
| 1835 | CG1 | VAL | A | 228 | -63.649 | -11.665 | 94.551 | 1.00 | 26.07 |
| 1836 | CG2 | VAL | A | 228 | -61.738 | -10.114 | 94.239 | 1.00 | 26.89 |
| 1837 | C | VAL | A | 228 | -61.755 | -13.519 | 95.195 | 1.00 | 25.78 |
| 1838 | O | VAL | A | 228 | -61.321 | -13.887 | 94.111 | 1.00 | 26.53 |
| 1839 | N | PRO | A | 229 | -62.450 | -14.301 | 96.019 | 1.00 | 25.21 |
| 1840 | CA | PRO | A | 229 | -62.839 | -15.669 | 95.672 | 1.00 | 24.52 |
| 1841 | CB | PRO | A | 229 | -63.740 | -16.071 | 96.834 | 1.00 | 25.29 |
| 1842 | CG | PRO | A | 229 | -63.229 | -15.220 | 97.994 | 1.00 | 25.36 |
| 1843 | CD | PRO | A | 229 | -62.917 | -13.898 | 97.360 | 1.00 | 24.47 |
| 1844 | C | PRO | A | 229 | -63.612 | -15.616 | 94.375 | 1.00 | 24.65 |
| 1845 | O | PRO | A | 229 | -64.760 | -15.183 | 94.347 | 1.00 | 24.19 |
| 1846 | N | TYR | A | 230 | -62.964 | -16.027 | 93.289 | 1.00 | 24.36 |
| 1847 | CA | TYR | A | 230 | -63.563 | -15.911 | 91.983 | 1.00 | 23.77 |
| 1848 | CB | TYR | A | 230 | -63.007 | -14.676 | 91.319 | 1.00 | 24.05 |
| 1849 | CG | TYR | A | 230 | -63.489 | -14.382 | 89.923 | 1.00 | 23.33 |
| 1850 | CD1 | TYR | A | 230 | -64.134 | -13.189 | 89.647 | 1.00 | 19.84 |
| 1851 | CE1 | TYR | A | 230 | -64.565 | -12.895 | 88.384 | 1.00 | 19.63 |
| 1852 | CZ | TYR | A | 230 | -64.325 | -13.783 | 87.349 | 1.00 | 19.88 |
| 1853 | OH | TYR | A | 230 | -64.726 | -13.443 | 86.090 | 1.00 | 21.53 |
| 1854 | CE2 | TYR | A | 230 | -63.651 | -14.972 | 87.564 | 1.00 | 20.98 |
| 1855 | CD2 | TYR | A | 230 | -63.228 | -15.263 | 88.859 | 1.00 | 24.22 |
| 1856 | C | TYR | A | 230 | -63.199 | -17.142 | 91.200 | 1.00 | 24.08 |
| 1857 | O | TYR | A | 230 | -62.029 | -17.390 | 90.902 | 1.00 | 24.05 |
| 1858 | N | PRO | A | 231 | -64.222 | -17.915 | 90.868 | 1.00 | 23.61 |
| 1859 | CA | PRO | A | 231 | -64.049 | -19.161 | 90.144 | 1.00 | 23.30 |
| 1860 | CB | PRO | A | 231 | -65.316 | -19.934 | 90.491 | 1.00 | 23.32 |
| 1861 | CG | PRO | A | 231 | -66.190 | -18.985 | 91.237 | 1.00 | 24.17 |
| 1862 | CD | PRO | A | 231 | -65.630 | -17.626 | 91.155 | 1.00 | 23.35 |
| 1863 | C | PRO | A | 231 | -64.025 | -18.918 | 88.635 | 1.00 | 22.79 |
| 1864 | O | PRO | A | 231 | -65.050 | -18.539 | 88.061 | 1.00 | 22.19 |
| 1865 | N | LYS | A | 232 | -62.872 | -19.133 | 88.017 | 1.00 | 22.32 |
| 1866 | CA | LYS | A | 232 | -62.752 | -19.057 | 86.570 | 1.00 | 22.26 |
| 1867 | CB | LYS | A | 232 | -61.307 | -18.732 | 86.160 | 1.00 | 22.67 |
| 1868 | CG | LYS | A | 232 | -60.827 | -17.367 | 86.648 | 1.00 | 21.38 |
| 1869 | CD | LYS | A | 232 | -59.439 | -17.025 | 86.162 | 1.00 | 20.10 |
| 1870 | CE | LYS | A | 232 | -59.004 | -15.620 | 86.638 | 1.00 | 18.95 |
| 1871 | NZ | LYS | A | 232 | -59.287 | -14.578 | 85.598 | 1.00 | 17.84 |
| 1872 | C | LYS | A | 232 | -63.252 | -20.385 | 85.954 | 1.00 | 22.23 |
| 1873 | O | LYS | A | 232 | -63.507 | -21.348 | 86.672 | 1.00 | 22.23 |
| 1874 | N | ALA | A | 233 | -63.412 | -20.420 | 84.635 | 1.00 | 21.66 |
| 1875 | CA | ALA | A | 233 | -63.988 | -21.579 | 83.962 | 1.00 | 21.92 |
| 1876 | CB | ALA | A | 233 | -63.883 | -21.419 | 82.426 | 1.00 | 21.89 |
| 1877 | C | ALA | A | 233 | -63.335 | -22.874 | 84.428 | 1.00 | 21.87 |

FIGURE 3 AK

| A | B | C | D | E | F | G | H | I | J |
|---|---|---|---|---|---|---|---|---|---|
| 1878 | O | ALA | A | 233 | -62.128 | -22.988 | 84.387 | 1.00 | 21.97 |
| 1879 | N | GLY | A | 234 | -64.133 | -23.827 | 84.905 | 1.00 | 22.24 |
| 1880 | CA | GLY | A | 234 | -63.599 | -25.090 | 85.395 | 1.00 | 22.87 |
| 1881 | C | GLY | A | 234 | -62.986 | -25.160 | 86.806 | 1.00 | 23.76 |
| 1882 | O | GLY | A | 234 | -62.630 | -26.261 | 87.277 | 1.00 | 23.88 |
| 1883 | N | ALA | A | 235 | -62.850 | -24.023 | 87.486 | 1.00 | 23.23 |
| 1884 | CA | ALA | A | 235 | -62.237 | -24.007 | 88.821 | 1.00 | 23.51 |
| 1885 | CB | ALA | A | 235 | -61.771 | -22.575 | 89.206 | 1.00 | 22.75 |
| 1886 | C | ALA | A | 235 | -63.213 | -24.538 | 89.844 | 1.00 | 23.19 |
| 1887 | O | ALA | A | 235 | -64.340 | -24.820 | 89.510 | 1.00 | 23.52 |
| 1888 | N | VAL | A | 236 | -62.822 | -24.689 | 91.102 | 1.00 | 23.98 |
| 1889 | CA | VAL | A | 236 | -63.838 | -25.200 | 92.004 | 1.00 | 24.29 |
| 1890 | CB | VAL | A | 236 | -63.298 | -26.066 | 93.229 | 1.00 | 25.20 |
| 1891 | CG1 | VAL | A | 236 | -63.504 | -25.396 | 94.602 | 1.00 | 24.06 |
| 1892 | CG2 | VAL | A | 236 | -61.850 | -26.641 | 92.988 | 1.00 | 24.27 |
| 1893 | C | VAL | A | 236 | -64.771 | -24.075 | 92.379 | 1.00 | 24.63 |
| 1894 | O | VAL | A | 236 | -64.329 | -22.929 | 92.575 | 1.00 | 25.18 |
| 1895 | N | ASN | A | 237 | -66.062 | -24.394 | 92.436 | 1.00 | 24.56 |
| 1896 | CA | ASN | A | 237 | -67.118 | -23.434 | 92.743 | 1.00 | 24.60 |
| 1897 | CB | ASN | A | 237 | -68.394 | -23.824 | 92.004 | 1.00 | 24.56 |
| 1898 | CG | ASN | A | 237 | -68.445 | -23.246 | 90.600 | 1.00 | 25.34 |
| 1899 | OD1 | ASN | A | 237 | -67.634 | -22.392 | 90.273 | 1.00 | 27.31 |
| 1900 | ND2 | ASN | A | 237 | -69.406 | -23.683 | 89.782 | 1.00 | 23.82 |
| 1901 | C | ASN | A | 237 | -67.444 | -23.358 | 94.222 | 1.00 | 25.42 |
| 1902 | O | ASN | A | 237 | -67.070 | -24.222 | 94.991 | 1.00 | 25.69 |
| 1903 | N | PRO | A | 238 | -68.090 | -22.279 | 94.632 | 1.00 | 25.96 |
| 1904 | CA | PRO | A | 238 | -68.683 | -22.233 | 95.958 | 1.00 | 26.32 |
| 1905 | CB | PRO | A | 238 | -69.400 | -20.884 | 95.952 | 1.00 | 26.42 |
| 1906 | CG | PRO | A | 238 | -69.528 | -20.553 | 94.442 | 1.00 | 25.19 |
| 1907 | CD | PRO | A | 238 | -68.230 | -20.992 | 93.915 | 1.00 | 25.53 |
| 1908 | C | PRO | A | 238 | -69.727 | -23.344 | 96.060 | 1.00 | 27.23 |
| 1909 | O | PRO | A | 238 | -70.230 | -23.827 | 95.052 | 1.00 | 26.67 |
| 1910 | N | THR | A | 239 | -70.046 | -23.741 | 97.286 | 1.00 | 28.17 |
| 1911 | CA | THR | A | 239 | -71.105 | -24.692 | 97.512 | 1.00 | 28.46 |
| 1912 | CB | THR | A | 239 | -70.609 | -25.837 | 98.405 | 1.00 | 29.27 |
| 1913 | OG1 | THR | A | 239 | -69.917 | -25.283 | 99.532 | 1.00 | 29.54 |
| 1914 | CG2 | THR | A | 239 | -69.513 | -26.673 | 97.681 | 1.00 | 25.81 |
| 1915 | C | THR | A | 239 | -72.177 | -23.878 | 98.207 | 1.00 | 29.49 |
| 1916 | O | THR | A | 239 | -71.887 | -22.802 | 98.738 | 1.00 | 29.73 |
| 1917 | N | VAL | A | 240 | -73.411 | -24.373 | 98.197 | 1.00 | 29.98 |
| 1918 | CA | VAL | A | 240 | -74.530 | -23.672 | 98.804 | 1.00 | 30.90 |
| 1919 | CB | VAL | A | 240 | -75.606 | -23.309 | 97.775 | 1.00 | 30.78 |
| 1920 | CG1 | VAL | A | 240 | -75.900 | -21.829 | 97.760 | 1.00 | 31.50 |
| 1921 | CG2 | VAL | A | 240 | -75.293 | -23.920 | 96.427 | 1.00 | 30.72 |
| 1922 | C | VAL | A | 240 | -75.343 | -24.545 | 99.710 | 1.00 | 31.57 |
| 1923 | O | VAL | A | 240 | -75.595 | -25.727 | 99.407 | 1.00 | 31.33 |
| 1924 | N | LYS | A | 241 | -75.836 | -23.915 | 100.768 | 1.00 | 32.00 |
| 1925 | CA | LYS | A | 241 | -76.736 | -24.559 | 101.698 | 1.00 | 32.73 |
| 1926 | CB | LYS | A | 241 | -76.042 | -24.783 | 103.038 | 1.00 | 33.06 |
| 1927 | CG | LYS | A | 241 | -75.128 | -26.011 | 103.106 | 1.00 | 33.99 |
| 1928 | CD | LYS | A | 241 | -74.480 | -26.061 | 104.485 | 1.00 | 37.77 |

FIGURE 3 AL

| A | B | C | D | E | F | G | H | I | J |
|---|---|---|---|---|---|---|---|---|---|
| 1929 | CE | LYS | A | 241 | -73.908 | -27.425 | 104.833 | 1.00 | 39.21 |
| 1930 | NZ | LYS | A | 241 | -72.867 | -27.825 | 103.872 | 1.00 | 42.49 |
| 1931 | C | LYS | A | 241 | -77.963 | -23.675 | 101.872 | 1.00 | 33.02 |
| 1932 | O | LYS | A | 241 | -77.878 | -22.447 | 101.862 | 1.00 | 32.97 |
| 1933 | N | PHE | A | 242 | -79.116 | -24.304 | 101.997 | 1.00 | 33.38 |
| 1934 | CA | PHE | A | 242 | -80.327 | -23.553 | 102.201 | 1.00 | 34.14 |
| 1935 | CB | PHE | A | 242 | -81.364 | -23.875 | 101.138 | 1.00 | 33.59 |
| 1936 | CG | PHE | A | 242 | -82.379 | -22.804 | 100.980 | 1.00 | 32.07 |
| 1937 | CD1 | PHE | A | 242 | -82.064 | -21.641 | 100.303 | 1.00 | 30.58 |
| 1938 | CE1 | PHE | A | 242 | -82.995 | -20.652 | 100.165 | 1.00 | 29.57 |
| 1939 | CZ | PHE | A | 242 | -84.250 | -20.810 | 100.728 | 1.00 | 31.16 |
| 1940 | CE2 | PHE | A | 242 | -84.561 | -21.963 | 101.422 | 1.00 | 29.96 |
| 1941 | CD2 | PHE | A | 242 | -83.638 | -22.939 | 101.546 | 1.00 | 30.79 |
| 1942 | C | PHE | A | 242 | -80.901 | -23.790 | 103.595 | 1.00 | 35.20 |
| 1943 | O | PHE | A | 242 | -80.822 | -24.895 | 104.140 | 1.00 | 35.41 |
| 1944 | N | PHE | A | 243 | -81.480 | -22.742 | 104.164 | 1.00 | 36.01 |
| 1945 | CA | PHE | A | 243 | -81.978 | -22.807 | 105.527 | 1.00 | 36.78 |
| 1946 | CB | PHE | A | 243 | -80.936 | -22.289 | 106.516 | 1.00 | 35.91 |
| 1947 | CG | PHE | A | 243 | -79.667 | -23.077 | 106.568 | 1.00 | 35.81 |
| 1948 | CD1 | PHE | A | 243 | -78.541 | -22.647 | 105.870 | 1.00 | 34.72 |
| 1949 | CE1 | PHE | A | 243 | -77.356 | -23.344 | 105.936 | 1.00 | 33.39 |
| 1950 | CZ | PHE | A | 243 | -77.264 | -24.486 | 106.717 | 1.00 | 35.51 |
| 1951 | CE2 | PHE | A | 243 | -78.379 | -24.924 | 107.442 | 1.00 | 34.98 |
| 1952 | CD2 | PHE | A | 243 | -79.568 | -24.209 | 107.368 | 1.00 | 35.08 |
| 1953 | C | PHE | A | 243 | -83.152 | -21.875 | 105.645 | 1.00 | 37.64 |
| 1954 | O | PHE | A | 243 | -83.216 | -20.862 | 104.959 | 1.00 | 37.68 |
| 1955 | N | VAL | A | 244 | -84.086 | -22.221 | 106.516 | 1.00 | 38.88 |
| 1956 | CA | VAL | A | 244 | -85.180 | -21.315 | 106.819 | 1.00 | 39.81 |
| 1957 | CB | VAL | A | 244 | -86.448 | -21.629 | 106.011 | 1.00 | 39.73 |
| 1958 | CG1 | VAL | A | 244 | -86.663 | -23.099 | 105.909 | 1.00 | 40.45 |
| 1959 | CG2 | VAL | A | 244 | -87.660 | -20.917 | 106.589 | 1.00 | 39.49 |
| 1960 | C | VAL | A | 244 | -85.389 | -21.278 | 108.341 | 1.00 | 40.81 |
| 1961 | O | VAL | A | 244 | -85.360 | -22.311 | 109.025 | 1.00 | 40.73 |
| 1962 | N | VAL | A | 245 | -85.519 | -20.070 | 108.871 | 1.00 | 41.56 |
| 1963 | CA | VAL | A | 245 | -85.668 | -19.881 | 110.302 | 1.00 | 42.70 |
| 1964 | CB | VAL | A | 245 | -84.494 | -19.061 | 110.867 | 1.00 | 42.62 |
| 1965 | CG1 | VAL | A | 245 | -84.602 | -17.607 | 110.441 | 1.00 | 41.92 |
| 1966 | CG2 | VAL | A | 245 | -84.428 | -19.175 | 112.381 | 1.00 | 42.55 |
| 1967 | C | VAL | A | 245 | -86.982 | -19.178 | 110.619 | 1.00 | 43.50 |
| 1968 | O | VAL | A | 245 | -87.409 | -18.286 | 109.886 | 1.00 | 43.71 |
| 1969 | N | ASN | A | 246 | -87.627 | -19.607 | 111.700 | 1.00 | 44.67 |
| 1970 | CA | ASN | A | 246 | -88.873 | -19.005 | 112.169 | 1.00 | 45.89 |
| 1971 | CB | ASN | A | 246 | -89.574 | -19.983 | 113.106 | 1.00 | 45.69 |
| 1972 | CG | ASN | A | 246 | -91.029 | -19.629 | 113.356 | 1.00 | 45.83 |
| 1973 | OD1 | ASN | A | 246 | -91.391 | -18.460 | 113.496 | 1.00 | 44.42 |
| 1974 | ND2 | ASN | A | 246 | -91.873 | -20.653 | 113.433 | 1.00 | 45.15 |
| 1975 | C | ASN | A | 246 | -88.538 | -17.724 | 112.927 | 1.00 | 46.85 |
| 1976 | O | ASN | A | 246 | -87.882 | -17.765 | 113.956 | 1.00 | 46.79 |
| 1977 | N | THR | A | 247 | -88.964 | -16.578 | 112.427 | 1.00 | 48.25 |
| 1978 | CA | THR | A | 247 | -88.616 | -15.343 | 113.114 | 1.00 | 49.89 |
| 1979 | CB | THR | A | 247 | -88.520 | -14.175 | 112.123 | 1.00 | 49.75 |

FIGURE 3 AM

| A | B | C | D | E | F | G | H | I | J |
|---|---|---|---|---|---|---|---|---|---|
| 1980 | OG1 | THR | A | 247 | -89.810 | -13.910 | 111.561 | 1.00 | 49.26 |
| 1981 | CG2 | THR | A | 247 | -87.663 | -14.574 | 110.924 | 1.00 | 50.06 |
| 1982 | C | THR | A | 247 | -89.584 | -15.006 | 114.247 | 1.00 | 51.26 |
| 1983 | O | THR | A | 247 | -89.356 | -14.074 | 115.010 | 1.00 | 51.43 |
| 1984 | N | ASP | A | 248 | -90.668 | -15.765 | 114.349 | 1.00 | 52.69 |
| 1985 | CA | ASP | A | 248 | -91.657 | -15.527 | 115.382 | 1.00 | 54.07 |
| 1986 | CB | ASP | A | 248 | -93.049 | -15.935 | 114.897 | 1.00 | 54.08 |
| 1987 | CG | ASP | A | 248 | -93.630 | -14.952 | 113.906 | 1.00 | 54.15 |
| 1988 | OD1 | ASP | A | 248 | -93.169 | -13.792 | 113.876 | 1.00 | 54.84 |
| 1989 | OD2 | ASP | A | 248 | -94.558 | -15.245 | 113.123 | 1.00 | 55.03 |
| 1990 | C | ASP | A | 248 | -91.300 | -16.282 | 116.654 | 1.00 | 55.20 |
| 1991 | O | ASP | A | 248 | -91.787 | -15.952 | 117.740 | 1.00 | 55.47 |
| 1992 | N | SER | A | 249 | -90.448 | -17.293 | 116.520 | 1.00 | 56.35 |
| 1993 | CA | SER | A | 249 | -90.017 | -18.068 | 117.672 | 1.00 | 57.70 |
| 1994 | CB | SER | A | 249 | -90.022 | -19.562 | 117.349 | 1.00 | 57.84 |
| 1995 | OG | SER | A | 249 | -89.235 | -19.840 | 116.200 | 1.00 | 59.31 |
| 1996 | C | SER | A | 249 | -88.629 | -17.632 | 118.144 | 1.00 | 58.50 |
| 1997 | O | SER | A | 249 | -87.880 | -18.424 | 118.719 | 1.00 | 58.56 |
| 1998 | N | LEU | A | 250 | -88.283 | -16.370 | 117.907 | 1.00 | 59.41 |
| 1999 | CA | LEU | A | 250 | -86.969 | -15.897 | 118.321 | 1.00 | 60.16 |
| 2000 | CB | LEU | A | 250 | -86.665 | -14.493 | 117.798 | 1.00 | 60.09 |
| 2001 | CG | LEU | A | 250 | -85.728 | -14.558 | 116.581 | 1.00 | 59.67 |
| 2002 | CD1 | LEU | A | 250 | -86.148 | -13.589 | 115.488 | 1.00 | 59.18 |
| 2003 | CD2 | LEU | A | 250 | -85.660 | -15.967 | 116.025 | 1.00 | 59.15 |
| 2004 | C | LEU | A | 250 | -86.765 | -16.062 | 119.827 | 1.00 | 60.99 |
| 2005 | O | LEU | A | 250 | -87.638 | -15.750 | 120.644 | 1.00 | 60.90 |
| 2006 | N | SER | A | 251 | -85.573 | -16.550 | 120.150 | 1.00 | 61.75 |
| 2007 | CA | SER | A | 251 | -85.219 | -17.082 | 121.457 | 1.00 | 62.33 |
| 2008 | CB | SER | A | 251 | -84.058 | -18.045 | 121.231 | 1.00 | 62.77 |
| 2009 | OG | SER | A | 251 | -83.915 | -18.320 | 119.837 | 1.00 | 63.26 |
| 2010 | C | SER | A | 251 | -84.867 | -16.149 | 122.614 | 1.00 | 62.50 |
| 2011 | O | SER | A | 251 | -85.283 | -16.393 | 123.752 | 1.00 | 62.69 |
| 2012 | N | SER | A | 252 | -84.065 | -15.121 | 122.340 | 1.00 | 62.50 |
| 2013 | CA | SER | A | 252 | -83.643 | -14.154 | 123.364 | 1.00 | 62.28 |
| 2014 | CB | SER | A | 252 | -84.851 | -13.472 | 124.017 | 1.00 | 62.54 |
| 2015 | OG | SER | A | 252 | -85.366 | -12.425 | 123.206 | 1.00 | 62.89 |
| 2016 | C | SER | A | 252 | -82.742 | -14.754 | 124.439 | 1.00 | 62.02 |
| 2017 | O | SER | A | 252 | -82.110 | -14.029 | 125.199 | 1.00 | 62.19 |
| 2018 | N | VAL | A | 253 | -82.694 | -16.081 | 124.499 | 1.00 | 61.65 |
| 2019 | CA | VAL | A | 253 | -81.866 | -16.791 | 125.468 | 1.00 | 61.16 |
| 2020 | CB | VAL | A | 253 | -82.699 | -17.302 | 126.672 | 1.00 | 61.48 |
| 2021 | CG1 | VAL | A | 253 | -82.228 | -18.683 | 127.124 | 1.00 | 61.20 |
| 2022 | CG2 | VAL | A | 253 | -82.643 | -16.297 | 127.822 | 1.00 | 61.38 |
| 2023 | C | VAL | A | 253 | -81.155 | -17.955 | 124.795 | 1.00 | 60.70 |
| 2024 | O | VAL | A | 253 | -79.951 | -18.148 | 124.977 | 1.00 | 60.91 |
| 2025 | N | THR | A | 254 | -81.902 | -18.732 | 124.017 | 1.00 | 59.69 |
| 2026 | CA | THR | A | 254 | -81.305 | -19.823 | 123.259 | 1.00 | 58.90 |
| 2027 | CB | THR | A | 254 | -82.134 | -21.120 | 123.387 | 1.00 | 58.99 |
| 2028 | OG1 | THR | A | 254 | -82.206 | -21.764 | 122.111 | 1.00 | 59.03 |
| 2029 | CG2 | THR | A | 254 | -83.583 | -20.812 | 123.711 | 1.00 | 59.10 |
| 2030 | C | THR | A | 254 | -81.107 | -19.413 | 121.792 | 1.00 | 57.99 |

FIGURE 3 AN

| A | B | C | D | E | F | G | H | I | J |
|---|---|---|---|---|---|---|---|---|---|
| 2031 | O | THR | A | 254 | -81.825 | -18.557 | 121.284 | 1.00 | 57.99 |
| 2032 | N | ASN | A | 255 | -80.117 | -20.010 | 121.130 | 1.00 | 56.82 |
| 2033 | CA | ASN | A | 255 | -79.790 | -19.678 | 119.739 | 1.00 | 55.54 |
| 2034 | CB | ASN | A | 255 | -78.423 | -20.268 | 119.347 | 1.00 | 55.63 |
| 2035 | CG | ASN | A | 255 | -77.256 | -19.398 | 119.782 | 1.00 | 54.94 |
| 2036 | OD1 | ASN | A | 255 | -77.421 | -18.200 | 120.007 | 1.00 | 54.46 |
| 2037 | ND2 | ASN | A | 255 | -76.063 | -19.996 | 119.890 | 1.00 | 56.20 |
| 2038 | C | ASN | A | 255 | -80.848 | -20.155 | 118.753 | 1.00 | 54.80 |
| 2039 | O | ASN | A | 255 | -81.358 | -21.269 | 118.873 | 1.00 | 54.78 |
| 2040 | N | ALA | A | 256 | -81.173 | -19.304 | 117.783 | 1.00 | 53.80 |
| 2041 | CA | ALA | A | 256 | -82.132 | -19.648 | 116.727 | 1.00 | 52.60 |
| 2042 | CB | ALA | A | 256 | -82.250 | -18.515 | 115.745 | 1.00 | 52.50 |
| 2043 | C | ALA | A | 256 | -81.729 | -20.918 | 115.990 | 1.00 | 51.62 |
| 2044 | O | ALA | A | 256 | -80.553 | -21.133 | 115.702 | 1.00 | 51.68 |
| 2045 | N | THR | A | 257 | -82.706 | -21.760 | 115.682 | 1.00 | 50.47 |
| 2046 | CA | THR | A | 257 | -82.426 | -22.986 | 114.948 | 1.00 | 49.46 |
| 2047 | CB | THR | A | 257 | -83.070 | -24.201 | 115.644 | 1.00 | 49.75 |
| 2048 | OG1 | THR | A | 257 | -83.674 | -25.066 | 114.666 | 1.00 | 50.68 |
| 2049 | CG2 | THR | A | 257 | -84.245 | -23.764 | 116.501 | 1.00 | 50.21 |
| 2050 | C | THR | A | 257 | -82.874 | -22.858 | 113.489 | 1.00 | 48.15 |
| 2051 | O | THR | A | 257 | -84.012 | -22.517 | 113.205 | 1.00 | 48.05 |
| 2052 | N | SER | A | 258 | -81.958 | -23.115 | 112.568 | 1.00 | 46.76 |
| 2053 | CA | SER | A | 258 | -82.271 | -23.006 | 111.153 | 1.00 | 45.31 |
| 2054 | CB | SER | A | 258 | -81.125 | -22.358 | 110.393 | 1.00 | 45.03 |
| 2055 | OG | SER | A | 258 | -80.925 | -21.040 | 110.852 | 1.00 | 45.08 |
| 2056 | C | SER | A | 258 | -82.546 | -24.369 | 110.583 | 1.00 | 44.36 |
| 2057 | O | SER | A | 258 | -81.779 | -25.314 | 110.797 | 1.00 | 44.05 |
| 2058 | N | ILE | A | 259 | -83.659 | -24.475 | 109.877 | 1.00 | 43.32 |
| 2059 | CA | ILE | A | 259 | -83.992 | -25.729 | 109.256 | 1.00 | 42.61 |
| 2060 | CB | ILE | A | 259 | -85.500 | -25.945 | 109.171 | 1.00 | 42.56 |
| 2061 | CG1 | ILE | A | 259 | -86.160 | -25.643 | 110.516 | 1.00 | 42.51 |
| 2062 | CD1 | ILE | A | 259 | -85.716 | -26.579 | 111.630 | 1.00 | 42.12 |
| 2063 | CG2 | ILE | A | 259 | -85.770 | -27.386 | 108.768 | 1.00 | 41.83 |
| 2064 | C | ILE | A | 259 | -83.388 | -25.743 | 107.871 | 1.00 | 42.36 |
| 2065 | O | ILE | A | 259 | -83.662 | -24.861 | 107.039 | 1.00 | 42.04 |
| 2066 | N | GLN | A | 260 | -82.537 | -26.731 | 107.647 | 1.00 | 41.69 |
| 2067 | CA | GLN | A | 260 | -81.911 | -26.883 | 106.357 | 1.00 | 41.23 |
| 2068 | CB | GLN | A | 260 | -80.565 | -27.615 | 106.477 | 1.00 | 41.39 |
| 2069 | CG | GLN | A | 260 | -79.904 | -27.935 | 105.138 | 1.00 | 41.31 |
| 2070 | CD | GLN | A | 260 | -78.462 | -28.393 | 105.287 | 1.00 | 41.98 |
| 2071 | OE1 | GLN | A | 260 | -78.074 | -28.899 | 106.343 | 1.00 | 43.78 |
| 2072 | NE2 | GLN | A | 260 | -77.663 | -28.214 | 104.235 | 1.00 | 40.57 |
| 2073 | C | GLN | A | 260 | -82.833 | -27.666 | 105.454 | 1.00 | 40.52 |
| 2074 | O | GLN | A | 260 | -83.422 | -28.673 | 105.869 | 1.00 | 40.70 |
| 2075 | N | ILE | A | 261 | -82.973 | -27.160 | 104.234 | 1.00 | 39.49 |
| 2076 | CA | ILE | A | 261 | -83.652 | -27.838 | 103.147 | 1.00 | 38.43 |
| 2077 | CB | ILE | A | 261 | -84.569 | -26.861 | 102.417 | 1.00 | 38.11 |
| 2078 | CG1 | ILE | A | 261 | -85.706 | -26.408 | 103.340 | 1.00 | 37.92 |
| 2079 | CD1 | ILE | A | 261 | -86.700 | -25.455 | 102.677 | 1.00 | 35.89 |
| 2080 | CG2 | ILE | A | 261 | -85.151 | -27.501 | 101.180 | 1.00 | 37.85 |
| 2081 | C | ILE | A | 261 | -82.516 | -28.251 | 102.230 | 1.00 | 38.16 |

FIGURE 3 AO

| A | B | C | D | E | F | G | H | I | J |
|---|---|---|---|---|---|---|---|---|---|
| 2082 | O | ILE | A | 261 | -81.745 | -27.406 | 101.773 | 1.00 | 38.33 |
| 2083 | N | THR | A | 262 | -82.372 | -29.545 | 101.982 | 1.00 | 37.42 |
| 2084 | CA | THR | A | 262 | -81.274 | -30.000 | 101.141 | 1.00 | 37.01 |
| 2085 | CB | THR | A | 262 | -80.823 | -31.395 | 101.544 | 1.00 | 36.89 |
| 2086 | OG1 | THR | A | 262 | -81.978 | -32.203 | 101.791 | 1.00 | 38.71 |
| 2087 | CG2 | THR | A | 262 | -80.139 | -31.356 | 102.896 | 1.00 | 37.90 |
| 2088 | C | THR | A | 262 | -81.649 | -29.981 | 99.669 | 1.00 | 36.23 |
| 2089 | O | THR | A | 262 | -82.820 | -30.100 | 99.312 | 1.00 | 36.03 |
| 2090 | N | ALA | A | 263 | -80.649 | -29.809 | 98.815 | 1.00 | 35.27 |
| 2091 | CA | ALA | A | 263 | -80.904 | -29.827 | 97.379 | 1.00 | 34.96 |
| 2092 | CB | ALA | A | 263 | -79.639 | -29.484 | 96.600 | 1.00 | 34.39 |
| 2093 | C | ALA | A | 263 | -81.409 | -31.215 | 97.002 | 1.00 | 34.41 |
| 2094 | O | ALA | A | 263 | -81.124 | -32.193 | 97.687 | 1.00 | 34.45 |
| 2095 | N | PRO | A | 264 | -82.155 | -31.300 | 95.911 | 1.00 | 34.07 |
| 2096 | CA | PRO | A | 264 | -82.692 | -32.583 | 95.447 | 1.00 | 33.39 |
| 2097 | CB | PRO | A | 264 | -83.407 | -32.215 | 94.142 | 1.00 | 33.13 |
| 2098 | CG | PRO | A | 264 | -83.639 | -30.758 | 94.217 | 1.00 | 33.45 |
| 2099 | CD | PRO | A | 264 | -82.520 | -30.179 | 95.024 | 1.00 | 33.77 |
| 2100 | C | PRO | A | 264 | -81.561 | -33.552 | 95.146 | 1.00 | 32.55 |
| 2101 | O | PRO | A | 264 | -80.461 | -33.137 | 94.789 | 1.00 | 32.12 |
| 2102 | N | ALA | A | 265 | -81.832 | -34.838 | 95.306 | 1.00 | 32.44 |
| 2103 | CA | ALA | A | 265 | -80.849 | -35.882 | 95.013 | 1.00 | 31.81 |
| 2104 | CB | ALA | A | 265 | -81.474 | -37.267 | 95.230 | 1.00 | 31.65 |
| 2105 | C | ALA | A | 265 | -80.272 | -35.757 | 93.586 | 1.00 | 31.53 |
| 2106 | O | ALA | A | 265 | -79.090 | -35.999 | 93.363 | 1.00 | 31.62 |
| 2107 | N | SER | A | 266 | -81.108 | -35.379 | 92.629 | 1.00 | 31.21 |
| 2108 | CA | SER | A | 266 | -80.656 | -35.159 | 91.260 | 1.00 | 31.53 |
| 2109 | CB | SER | A | 266 | -81.848 | -34.821 | 90.386 | 1.00 | 31.72 |
| 2110 | OG | SER | A | 266 | -82.497 | -33.672 | 90.904 | 1.00 | 33.45 |
| 2111 | C | SER | A | 266 | -79.626 | -34.021 | 91.154 | 1.00 | 31.35 |
| 2112 | O | SER | A | 266 | -78.956 | -33.877 | 90.136 | 1.00 | 30.85 |
| 2113 | N | MET | A | 267 | -79.496 | -33.216 | 92.202 | 1.00 | 30.95 |
| 2114 | CA | MET | A | 267 | -78.508 | -32.155 | 92.178 | 1.00 | 31.20 |
| 2115 | CB | MET | A | 267 | -79.091 | -30.854 | 92.728 | 1.00 | 31.15 |
| 2116 | CG | MET | A | 267 | -80.123 | -30.228 | 91.823 | 1.00 | 31.38 |
| 2117 | SD | MET | A | 267 | -79.395 | -29.441 | 90.337 | 1.00 | 30.99 |
| 2118 | CE | MET | A | 267 | -80.646 | -29.917 | 89.134 | 1.00 | 26.89 |
| 2119 | C | MET | A | 267 | -77.279 | -32.519 | 92.970 | 1.00 | 31.38 |
| 2120 | O | MET | A | 267 | -76.169 | -32.137 | 92.603 | 1.00 | 31.24 |
| 2121 | N | LEU | A | 268 | -77.487 | -33.270 | 94.052 | 1.00 | 32.50 |
| 2122 | CA | LEU | A | 268 | -76.427 | -33.627 | 95.001 | 1.00 | 32.73 |
| 2123 | CB | LEU | A | 268 | -77.044 | -34.249 | 96.264 | 1.00 | 32.88 |
| 2124 | CG | LEU | A | 268 | -77.862 | -33.305 | 97.169 | 1.00 | 33.83 |
| 2125 | CD1 | LEU | A | 268 | -78.619 | -34.089 | 98.234 | 1.00 | 33.53 |
| 2126 | CD2 | LEU | A | 268 | -76.985 | -32.236 | 97.830 | 1.00 | 30.90 |
| 2127 | C | LEU | A | 268 | -75.375 | -34.554 | 94.409 | 1.00 | 32.58 |
| 2128 | O | LEU | A | 268 | -74.322 | -34.793 | 95.001 | 1.00 | 32.76 |
| 2129 | N | ILE | A | 269 | -75.662 | -35.073 | 93.232 | 1.00 | 32.48 |
| 2130 | CA | ILE | A | 269 | -74.761 | -36.006 | 92.566 | 1.00 | 32.76 |
| 2131 | CB | ILE | A | 269 | -75.552 | -36.774 | 91.474 | 1.00 | 32.89 |
| 2132 | CG1 | ILE | A | 269 | -74.923 | -38.139 | 91.213 | 1.00 | 35.72 |

FIGURE 3 AP

| A | B | C | D | E | F | G | H | I | J |
|---|---|---|---|---|---|---|---|---|---|
| 2133 | CD1 | ILE | A | 269 | -75.364 | -39.221 | 92.239 | 1.00 | 38.91 |
| 2134 | CG2 | ILE | A | 269 | -75.752 | -35.942 | 90.196 | 1.00 | 33.92 |
| 2135 | C | ILE | A | 269 | -73.495 | -35.326 | 92.017 | 1.00 | 32.19 |
| 2136 | O | ILE | A | 269 | -72.519 | -35.992 | 91.644 | 1.00 | 32.60 |
| 2137 | N | GLY | A | 270 | -73.501 | -33.996 | 91.994 | 1.00 | 31.07 |
| 2138 | CA | GLY | A | 270 | -72.343 | -33.237 | 91.559 | 1.00 | 29.95 |
| 2139 | C | GLY | A | 270 | -72.464 | -31.754 | 91.870 | 1.00 | 29.19 |
| 2140 | O | GLY | A | 270 | -73.311 | -31.339 | 92.661 | 1.00 | 28.83 |
| 2141 | N | ASP | A | 271 | -71.598 | -30.950 | 91.260 | 1.00 | 28.45 |
| 2142 | CA | ASP | A | 271 | -71.654 | -29.507 | 91.448 | 1.00 | 27.59 |
| 2143 | CB | ASP | A | 271 | -70.558 | -28.810 | 90.654 | 1.00 | 27.94 |
| 2144 | CG | ASP | A | 271 | -69.197 | -29.002 | 91.243 | 1.00 | 28.64 |
| 2145 | OD1 | ASP | A | 271 | -69.062 | -29.687 | 92.277 | 1.00 | 32.28 |
| 2146 | OD2 | ASP | A | 271 | -68.183 | -28.512 | 90.727 | 1.00 | 31.33 |
| 2147 | C | ASP | A | 271 | -73.009 | -29.009 | 90.969 | 1.00 | 26.80 |
| 2148 | O | ASP | A | 271 | -73.530 | -29.442 | 89.930 | 1.00 | 26.17 |
| 2149 | N | HIS | A | 272 | -73.579 | -28.099 | 91.734 | 1.00 | 25.81 |
| 2150 | CA | HIS | A | 272 | -74.869 | -27.549 | 91.397 | 1.00 | 26.04 |
| 2151 | CB | HIS | A | 272 | -75.983 | -28.440 | 91.976 | 1.00 | 26.06 |
| 2152 | CG | HIS | A | 272 | -75.857 | -28.670 | 93.449 | 1.00 | 26.86 |
| 2153 | ND1 | HIS | A | 272 | -75.037 | -29.641 | 93.982 | 1.00 | 28.32 |
| 2154 | CE1 | HIS | A | 272 | -75.114 | -29.605 | 95.303 | 1.00 | 28.38 |
| 2155 | NE2 | HIS | A | 272 | -75.948 | -28.641 | 95.646 | 1.00 | 27.58 |
| 2156 | CD2 | HIS | A | 272 | -76.429 | -28.040 | 94.504 | 1.00 | 26.93 |
| 2157 | C | HIS | A | 272 | -74.982 | -26.116 | 91.924 | 1.00 | 25.63 |
| 2158 | O | HIS | A | 272 | -74.096 | -25.620 | 92.622 | 1.00 | 25.67 |
| 2159 | N | TYR | A | 273 | -76.077 | -25.455 | 91.589 | 1.00 | 25.18 |
| 2160 | CA | TYR | A | 273 | -76.310 | -24.097 | 92.044 | 1.00 | 25.33 |
| 2161 | CB | TYR | A | 273 | -76.217 | -23.105 | 90.898 | 1.00 | 24.59 |
| 2162 | CG | TYR | A | 273 | -74.954 | -23.119 | 90.098 | 1.00 | 24.95 |
| 2163 | CD1 | TYR | A | 273 | -73.790 | -22.620 | 90.624 | 1.00 | 24.16 |
| 2164 | CE1 | TYR | A | 273 | -72.643 | -22.605 | 89.888 | 1.00 | 25.98 |
| 2165 | CZ | TYR | A | 273 | -72.636 | -23.089 | 88.598 | 1.00 | 25.36 |
| 2166 | OH | TYR | A | 273 | -71.449 | -23.042 | 87.899 | 1.00 | 26.59 |
| 2167 | CE2 | TYR | A | 273 | -73.788 | -23.593 | 88.028 | 1.00 | 23.35 |
| 2168 | CD2 | TYR | A | 273 | -74.939 | -23.605 | 88.774 | 1.00 | 25.51 |
| 2169 | C | TYR | A | 273 | -77.721 | -23.960 | 92.564 | 1.00 | 26.02 |
| 2170 | O | TYR | A | 273 | -78.628 | -24.701 | 92.175 | 1.00 | 26.79 |
| 2171 | N | LEU | A | 274 | -77.915 | -22.999 | 93.453 | 1.00 | 25.96 |
| 2172 | CA | LEU | A | 274 | -79.254 | -22.659 | 93.846 | 1.00 | 25.26 |
| 2173 | CB | LEU | A | 274 | -79.278 | -22.203 | 95.295 | 1.00 | 24.56 |
| 2174 | CG | LEU | A | 274 | -80.563 | -21.506 | 95.733 | 1.00 | 23.32 |
| 2175 | CD1 | LEU | A | 274 | -81.768 | -22.461 | 95.653 | 1.00 | 21.24 |
| 2176 | CD2 | LEU | A | 274 | -80.383 | -20.940 | 97.129 | 1.00 | 21.74 |
| 2177 | C | LEU | A | 274 | -79.496 | -21.499 | 92.902 | 1.00 | 25.98 |
| 2178 | O | LEU | A | 274 | -78.695 | -20.583 | 92.866 | 1.00 | 25.32 |
| 2179 | N | CYS | A | 275 | -80.567 | -21.523 | 92.114 | 1.00 | 27.06 |
| 2180 | CA | CYS | A | 275 | -80.734 | -20.447 | 91.155 | 1.00 | 28.60 |
| 2181 | CB | CYS | A | 275 | -80.616 | -20.952 | 89.714 | 1.00 | 28.81 |
| 2182 | SG | CYS | A | 275 | -81.862 | -22.181 | 89.283 | 1.00 | 32.54 |
| 2183 | C | CYS | A | 275 | -81.998 | -19.653 | 91.328 | 1.00 | 29.06 |

FIGURE 3 AQ

| A | B | C | D | E | F | G | H | I | J |
|---|---|---|---|---|---|---|---|---|---|
| 2184 | O | CYS | A | 313 | -82.135 | -18.580 | 90.750 | 1.00 | 29.63 |
| 2185 | N | ASP | A | 314 | -82.936 | -20.175 | 92.101 | 1.00 | 29.85 |
| 2186 | CA | ASP | A | 314 | -84.158 | -19.420 | 92.354 | 1.00 | 30.43 |
| 2187 | CB | ASP | A | 314 | -85.174 | -19.643 | 91.234 | 1.00 | 30.40 |
| 2188 | CG | ASP | A | 314 | -86.338 | -18.669 | 91.301 | 1.00 | 31.12 |
| 2189 | OD1 | ASP | A | 314 | -87.323 | -18.939 | 92.029 | 1.00 | 30.91 |
| 2190 | OD2 | ASP | A | 314 | -86.357 | -17.607 | 90.649 | 1.00 | 31.73 |
| 2191 | C | ASP | A | 314 | -84.799 | -19.731 | 93.711 | 1.00 | 30.92 |
| 2192 | O | ASP | A | 314 | -84.871 | -20.881 | 94.152 | 1.00 | 30.46 |
| 2193 | N | VAL | A | 315 | -85.280 | -18.682 | 94.358 | 1.00 | 31.55 |
| 2194 | CA | VAL | A | 315 | -85.982 | -18.824 | 95.607 | 1.00 | 32.23 |
| 2195 | CB | VAL | A | 315 | -85.148 | -18.298 | 96.806 | 1.00 | 32.71 |
| 2196 | CG1 | VAL | A | 315 | -85.968 | -18.350 | 98.104 | 1.00 | 32.58 |
| 2197 | CG2 | VAL | A | 315 | -83.877 | -19.085 | 96.965 | 1.00 | 30.85 |
| 2198 | C | VAL | A | 315 | -87.269 | -18.043 | 95.462 | 1.00 | 33.17 |
| 2199 | O | VAL | A | 315 | -87.252 | -16.844 | 95.163 | 1.00 | 33.74 |
| 2200 | N | THR | A | 316 | -88.400 | -18.720 | 95.615 | 1.00 | 33.72 |
| 2201 | CA | THR | A | 316 | -89.666 | -18.016 | 95.522 | 1.00 | 34.38 |
| 2202 | CB | THR | A | 316 | -90.194 | -18.040 | 94.077 | 1.00 | 34.88 |
| 2203 | OG1 | THR | A | 316 | -89.323 | -17.279 | 93.225 | 1.00 | 35.83 |
| 2204 | CG2 | THR | A | 316 | -91.545 | -17.310 | 93.983 | 1.00 | 33.77 |
| 2205 | C | THR | A | 316 | -90.711 | -18.599 | 96.480 | 1.00 | 35.24 |
| 2206 | O | THR | A | 316 | -91.060 | -19.804 | 96.406 | 1.00 | 34.88 |
| 2207 | N | TRP | A | 317 | -91.194 | -17.748 | 97.387 | 1.00 | 35.53 |
| 2208 | CA | TRP | A | 317 | -92.255 | -18.136 | 98.320 | 1.00 | 35.87 |
| 2209 | CB | TRP | A | 317 | -92.383 | -17.138 | 99.478 | 1.00 | 35.63 |
| 2210 | CG | TRP | A | 317 | -91.285 | -17.289 | 100.476 | 1.00 | 34.42 |
| 2211 | CD1 | TRP | A | 317 | -90.101 | -16.627 | 100.493 | 1.00 | 33.80 |
| 2212 | NE1 | TRP | A | 317 | -89.332 | -17.047 | 101.552 | 1.00 | 33.52 |
| 2213 | CE2 | TRP | A | 317 | -90.029 | -17.995 | 102.249 | 1.00 | 34.52 |
| 2214 | CD2 | TRP | A | 317 | -91.265 | -18.173 | 101.592 | 1.00 | 34.41 |
| 2215 | CE3 | TRP | A | 317 | -92.172 | -19.098 | 102.117 | 1.00 | 35.32 |
| 2216 | CZ3 | TRP | A | 317 | -91.817 | -19.809 | 103.256 | 1.00 | 34.69 |
| 2217 | CH2 | TRP | A | 317 | -90.585 | -19.608 | 103.878 | 1.00 | 34.85 |
| 2218 | CZ2 | TRP | A | 317 | -89.679 | -18.705 | 103.395 | 1.00 | 35.09 |
| 2219 | C | TRP | A | 317 | -93.588 | -18.263 | 97.602 | 1.00 | 36.53 |
| 2220 | O | TRP | A | 317 | -94.003 | -17.359 | 96.870 | 1.00 | 36.29 |
| 2221 | N | ALA | A | 318 | -94.258 | -19.393 | 97.809 | 1.00 | 37.43 |
| 2222 | CA | ALA | A | 318 | -95.545 | -19.612 | 97.179 | 1.00 | 38.74 |
| 2223 | CB | ALA | A | 318 | -95.691 | -21.044 | 96.784 | 1.00 | 39.19 |
| 2224 | C | ALA | A | 318 | -96.672 | -19.199 | 98.112 | 1.00 | 39.57 |
| 2225 | O | ALA | A | 318 | -97.656 | -18.627 | 97.667 | 1.00 | 39.87 |
| 2226 | N | THR | A | 319 | -96.518 | -19.506 | 99.400 | 1.00 | 40.41 |
| 2227 | CA | THR | A | 319 | -97.498 | -19.162 | 100.425 | 1.00 | 41.08 |
| 2228 | CB | THR | A | 319 | -98.475 | -20.305 | 100.666 | 1.00 | 41.30 |
| 2229 | OG1 | THR | A | 319 | -97.789 | -21.362 | 101.344 | 1.00 | 43.15 |
| 2230 | CG2 | THR | A | 319 | -98.932 | -20.944 | 99.378 | 1.00 | 41.56 |
| 2231 | C | THR | A | 319 | -96.742 | -18.960 | 101.730 | 1.00 | 41.45 |
| 2232 | O | THR | A | 319 | -95.506 | -18.961 | 101.730 | 1.00 | 41.57 |
| 2233 | N | GLN | A | 320 | -97.484 | -18.820 | 102.835 | 1.00 | 41.08 |
| 2234 | CA | GLN | A | 320 | -96.893 | -18.659 | 104.168 | 1.00 | 40.97 |

FIGURE 3 AR

| A | B | C | D | E | F | G | H | I | J |
|---|---|---|---|---|---|---|---|---|---|
| 2235 | CB | GLN | A | 282 | -97.982 | -18.477 | 105.241 | 1.00 | 40.89 |
| 2236 | CG | GLN | A | 282 | -99.022 | -17.407 | 104.967 | 1.00 | 40.19 |
| 2237 | CD | GLN | A | 282 | -98.423 | -16.039 | 104.810 | 1.00 | 40.46 |
| 2238 | OE1 | GLN | A | 282 | -97.218 | -15.842 | 105.021 | 1.00 | 41.48 |
| 2239 | NE2 | GLN | A | 282 | -99.250 | -15.084 | 104.438 | 1.00 | 40.81 |
| 2240 | C | GLN | A | 282 | -96.043 | -19.859 | 104.578 | 1.00 | 40.87 |
| 2241 | O | GLN | A | 282 | -95.065 | -19.712 | 105.312 | 1.00 | 40.98 |
| 2242 | N | GLU | A | 283 | -96.424 | -21.042 | 104.115 | 1.00 | 40.93 |
| 2243 | CA | GLU | A | 283 | -95.738 | -22.266 | 104.501 | 1.00 | 41.80 |
| 2244 | CB | GLU | A | 283 | -96.670 | -23.121 | 105.333 | 1.00 | 42.18 |
| 2245 | CG | GLU | A | 283 | -97.060 | -22.507 | 106.663 | 1.00 | 44.15 |
| 2246 | CD | GLU | A | 283 | -98.172 | -23.289 | 107.336 | 1.00 | 46.00 |
| 2247 | OE1 | GLU | A | 283 | -98.743 | -22.768 | 108.319 | 1.00 | 49.38 |
| 2248 | OE2 | GLU | A | 283 | -98.475 | -24.417 | 106.878 | 1.00 | 45.11 |
| 2249 | C | GLU | A | 283 | -95.249 | -23.103 | 103.314 | 1.00 | 41.89 |
| 2250 | O | GLU | A | 283 | -94.935 | -24.298 | 103.474 | 1.00 | 41.58 |
| 2251 | N | ARG | A | 284 | -95.210 | -22.479 | 102.136 | 1.00 | 41.31 |
| 2252 | CA | ARG | A | 284 | -94.719 | -23.125 | 100.931 | 1.00 | 41.03 |
| 2253 | CB | ARG | A | 284 | -95.883 | -23.492 | 100.003 | 1.00 | 41.52 |
| 2254 | CG | ARG | A | 284 | -95.473 | -23.871 | 98.571 | 1.00 | 42.57 |
| 2255 | CD | ARG | A | 284 | -96.620 | -24.489 | 97.747 | 1.00 | 44.25 |
| 2256 | NE | ARG | A | 284 | -97.243 | -25.575 | 98.498 | 1.00 | 46.10 |
| 2257 | CZ | ARG | A | 284 | -98.524 | -25.919 | 98.424 | 1.00 | 46.28 |
| 2258 | NH1 | ARG | A | 284 | -99.357 | -25.284 | 97.611 | 1.00 | 45.98 |
| 2259 | NH2 | ARG | A | 284 | -98.972 | -26.914 | 99.171 | 1.00 | 46.28 |
| 2260 | C | ARG | A | 284 | -93.716 | -22.245 | 100.192 | 1.00 | 40.44 |
| 2261 | O | ARG | A | 284 | -94.009 | -21.104 | 99.808 | 1.00 | 40.37 |
| 2262 | N | ILE | A | 285 | -92.528 | -22.789 | 99.987 | 1.00 | 39.75 |
| 2263 | CA | ILE | A | 285 | -91.486 | -22.074 | 99.278 | 1.00 | 39.15 |
| 2264 | CB | ILE | A | 285 | -90.341 | -21.711 | 100.244 | 1.00 | 39.31 |
| 2265 | CG1 | ILE | A | 285 | -89.264 | -20.934 | 99.496 | 1.00 | 38.61 |
| 2266 | CD1 | ILE | A | 285 | -88.269 | -20.302 | 100.384 | 1.00 | 39.48 |
| 2267 | CG2 | ILE | A | 285 | -89.752 | -22.965 | 100.864 | 1.00 | 38.79 |
| 2268 | C | ILE | A | 285 | -90.953 | -22.923 | 98.132 | 1.00 | 38.33 |
| 2269 | O | ILE | A | 285 | -90.785 | -24.132 | 98.280 | 1.00 | 38.22 |
| 2270 | N | SER | A | 286 | -90.713 | -22.297 | 96.985 | 1.00 | 37.40 |
| 2271 | CA | SER | A | 286 | -90.157 | -23.015 | 95.837 | 1.00 | 36.42 |
| 2272 | CB | SER | A | 286 | -90.917 | -22.711 | 94.562 | 1.00 | 36.26 |
| 2273 | OG | SER | A | 286 | -90.749 | -21.348 | 94.222 | 1.00 | 37.97 |
| 2274 | C | SER | A | 286 | -88.696 | -22.621 | 95.677 | 1.00 | 35.63 |
| 2275 | O | SER | A | 286 | -88.326 | -21.450 | 95.827 | 1.00 | 35.04 |
| 2276 | N | LEU | A | 287 | -87.887 | -23.623 | 95.366 | 1.00 | 34.71 |
| 2277 | CA | LEU | A | 287 | -86.456 | -23.505 | 95.287 | 1.00 | 34.27 |
| 2278 | CB | LEU | A | 287 | -85.870 | -24.346 | 96.417 | 1.00 | 34.37 |
| 2279 | CG | LEU | A | 287 | -84.891 | -23.735 | 97.417 | 1.00 | 36.11 |
| 2280 | CD1 | LEU | A | 287 | -84.773 | -24.619 | 98.643 | 1.00 | 34.38 |
| 2281 | CD2 | LEU | A | 287 | -85.340 | -22.317 | 97.814 | 1.00 | 36.34 |
| 2282 | C | LEU | A | 287 | -86.070 | -24.126 | 93.955 | 1.00 | 33.93 |
| 2283 | O | LEU | A | 287 | -86.444 | -25.266 | 93.682 | 1.00 | 34.02 |
| 2284 | N | GLN | A | 288 | -85.384 | -23.386 | 93.088 | 1.00 | 32.93 |
| 2285 | CA | GLN | A | 288 | -84.921 | -24.012 | 91.849 | 1.00 | 32.27 |

FIGURE 3 AS

| A | B | C | D | E | F | G | H | I | J |
|---|---|---|---|---|---|---|---|---|---|
| 2286 | CB | GLN | A | 288 | -85.272 | -23.219 | 90.586 | 1.00 | 32.03 |
| 2287 | CG | GLN | A | 288 | -86.749 | -23.070 | 90.314 | 1.00 | 32.25 |
| 2288 | CD | GLN | A | 288 | -87.036 | -22.297 | 89.034 | 1.00 | 33.56 |
| 2289 | OE1 | GLN | A | 288 | -86.678 | -22.736 | 87.928 | 1.00 | 32.25 |
| 2290 | NE2 | GLN | A | 288 | -87.674 | -21.140 | 89.177 | 1.00 | 33.25 |
| 2291 | C | GLN | A | 288 | -83.422 | -24.191 | 91.956 | 1.00 | 31.43 |
| 2292 | O | GLN | A | 288 | -82.717 | -23.312 | 92.448 | 1.00 | 31.50 |
| 2293 | N | TRP | A | 289 | -82.952 | -25.345 | 91.504 | 1.00 | 30.05 |
| 2294 | CA | TRP | A | 289 | -81.550 | -25.663 | 91.524 | 1.00 | 28.99 |
| 2295 | CB | TRP | A | 289 | -81.290 | -26.892 | 92.401 | 1.00 | 29.63 |
| 2296 | CG | TRP | A | 289 | -81.758 | -26.801 | 93.835 | 1.00 | 28.11 |
| 2297 | CD1 | TRP | A | 289 | -82.994 | -27.083 | 94.304 | 1.00 | 26.60 |
| 2298 | NE1 | TRP | A | 289 | -83.037 | -26.919 | 95.664 | 1.00 | 25.30 |
| 2299 | CE2 | TRP | A | 289 | -81.804 | -26.530 | 96.099 | 1.00 | 27.52 |
| 2300 | CD2 | TRP | A | 289 | -80.974 | -26.445 | 94.971 | 1.00 | 27.50 |
| 2301 | CE3 | TRP | A | 289 | -79.646 | -26.063 | 95.152 | 1.00 | 28.54 |
| 2302 | CZ3 | TRP | A | 289 | -79.203 | -25.784 | 96.419 | 1.00 | 28.35 |
| 2303 | CH2 | TRP | A | 289 | -80.060 | -25.868 | 97.518 | 1.00 | 29.89 |
| 2304 | CZ2 | TRP | A | 289 | -81.360 | -26.246 | 97.380 | 1.00 | 27.77 |
| 2305 | C | TRP | A | 289 | -81.142 | -25.973 | 90.106 | 1.00 | 28.22 |
| 2306 | O | TRP | A | 289 | -81.958 | -26.428 | 89.315 | 1.00 | 27.95 |
| 2307 | N | LEU | A | 290 | -79.863 | -25.771 | 89.807 | 1.00 | 28.05 |
| 2308 | CA | LEU | A | 290 | -79.318 | -25.937 | 88.465 | 1.00 | 27.10 |
| 2309 | CB | LEU | A | 290 | -78.901 | -24.561 | 87.940 | 1.00 | 27.24 |
| 2310 | CG | LEU | A | 290 | -79.195 | -24.003 | 86.546 | 1.00 | 27.54 |
| 2311 | CD1 | LEU | A | 290 | -78.330 | -22.756 | 86.272 | 1.00 | 22.78 |
| 2312 | CD2 | LEU | A | 290 | -79.105 | -25.028 | 85.422 | 1.00 | 25.82 |
| 2313 | C | LEU | A | 290 | -78.049 | -26.722 | 88.605 | 1.00 | 26.26 |
| 2314 | O | LEU | A | 290 | -77.204 | -26.365 | 89.390 | 1.00 | 25.73 |
| 2315 | N | ARG | A | 291 | -77.876 | -27.779 | 87.829 | 1.00 | 26.62 |
| 2316 | CA | ARG | A | 291 | -76.594 | -28.498 | 87.870 | 1.00 | 26.34 |
| 2317 | CB | ARG | A | 291 | -76.649 | -29.767 | 87.020 | 1.00 | 26.04 |
| 2318 | CG | ARG | A | 291 | -77.571 | -30.860 | 87.514 | 1.00 | 28.20 |
| 2319 | CD | ARG | A | 291 | -77.474 | -32.145 | 86.690 | 1.00 | 31.04 |
| 2320 | NE | ARG | A | 291 | -78.251 | -33.212 | 87.308 | 1.00 | 35.84 |
| 2321 | CZ | ARG | A | 291 | -78.782 | -34.239 | 86.656 | 1.00 | 34.28 |
| 2322 | NH1 | ARG | A | 291 | -79.480 | -35.139 | 87.329 | 1.00 | 31.91 |
| 2323 | NH2 | ARG | A | 291 | -78.611 | -34.364 | 85.345 | 1.00 | 32.21 |
| 2324 | C | ARG | A | 291 | -75.511 | -27.599 | 87.280 | 1.00 | 25.50 |
| 2325 | O | ARG | A | 291 | -75.818 | -26.696 | 86.502 | 1.00 | 24.87 |
| 2326 | N | ARG | A | 292 | -74.256 | -27.872 | 87.618 | 1.00 | 25.10 |
| 2327 | CA | ARG | A | 292 | -73.139 | -27.141 | 87.025 | 1.00 | 25.84 |
| 2328 | CB | ARG | A | 292 | -71.791 | -27.564 | 87.611 | 1.00 | 25.46 |
| 2329 | CG | ARG | A | 292 | -70.719 | -26.515 | 87.425 | 1.00 | 24.84 |
| 2330 | CD | ARG | A | 292 | -69.353 | -26.903 | 87.945 | 1.00 | 22.79 |
| 2331 | NE | ARG | A | 292 | -68.347 | -25.941 | 87.524 | 1.00 | 24.65 |
| 2332 | CZ | ARG | A | 292 | -67.209 | -25.716 | 88.186 | 1.00 | 27.61 |
| 2333 | NH1 | ARG | A | 292 | -66.354 | -24.806 | 87.735 | 1.00 | 23.20 |
| 2334 | NH2 | ARG | A | 292 | -66.926 | -26.406 | 89.301 | 1.00 | 25.07 |
| 2335 | C | ARG | A | 292 | -73.135 | -27.221 | 85.484 | 1.00 | 26.01 |
| 2336 | O | ARG | A | 292 | -72.722 | -26.272 | 84.810 | 1.00 | 26.29 |

FIGURE 3 AT

| A | B | C | D | E | F | G | H | I | J |
|---|---|---|---|---|---|---|---|---|---|
| 2337 | N | ILE | A | 293 | -73.582 | -28.336 | 84.916 | 1.00 | 26.05 |
| 2338 | CA | ILE | A | 293 | -73.810 | -28.337 | 83.482 | 1.00 | 25.78 |
| 2339 | CB | ILE | A | 293 | -73.613 | -29.693 | 82.855 | 1.00 | 26.60 |
| 2340 | CG1 | ILE | A | 293 | -72.135 | -30.125 | 83.029 | 1.00 | 27.40 |
| 2341 | CD1 | ILE | A | 293 | -71.960 | -31.641 | 83.184 | 1.00 | 31.38 |
| 2342 | CG2 | ILE | A | 293 | -73.939 | -29.589 | 81.383 | 1.00 | 24.44 |
| 2343 | C | ILE | A | 293 | -75.226 | -27.827 | 83.375 | 1.00 | 25.88 |
| 2344 | O | ILE | A | 293 | -76.195 | -28.521 | 83.690 | 1.00 | 25.88 |
| 2345 | N | GLN | A | 294 | -75.332 | -26.580 | 82.955 | 1.00 | 25.86 |
| 2346 | CA | GLN | A | 294 | -76.572 | -25.841 | 83.078 | 1.00 | 25.91 |
| 2347 | CB | GLN | A | 294 | -76.277 | -24.354 | 83.074 | 1.00 | 25.69 |
| 2348 | CG | GLN | A | 294 | -75.298 | -23.984 | 84.156 | 1.00 | 24.92 |
| 2349 | CD | GLN | A | 294 | -75.007 | -22.514 | 84.196 | 1.00 | 23.92 |
| 2350 | OE1 | GLN | A | 294 | -75.912 | -21.691 | 84.092 | 1.00 | 24.34 |
| 2351 | NE2 | GLN | A | 294 | -73.746 | -22.177 | 84.351 | 1.00 | 24.37 |
| 2352 | C | GLN | A | 294 | -77.679 | -26.146 | 82.115 | 1.00 | 26.78 |
| 2353 | O | GLN | A | 294 | -78.414 | -25.240 | 81.727 | 1.00 | 26.59 |
| 2354 | N | ASN | A | 295 | -77.825 | -27.414 | 81.746 | 1.00 | 27.52 |
| 2355 | CA | ASN | A | 295 | -78.920 | -27.774 | 80.868 | 1.00 | 28.56 |
| 2356 | CB | ASN | A | 295 | -78.416 | -28.489 | 79.607 | 1.00 | 29.50 |
| 2357 | CG | ASN | A | 295 | -77.712 | -29.809 | 79.903 | 1.00 | 31.49 |
| 2358 | OD1 | ASN | A | 295 | -77.614 | -30.243 | 81.051 | 1.00 | 32.33 |
| 2359 | ND2 | ASN | A | 295 | -77.212 | -30.450 | 78.849 | 1.00 | 38.02 |
| 2360 | C | ASN | A | 295 | -79.987 | -28.568 | 81.609 | 1.00 | 28.54 |
| 2361 | O | ASN | A | 295 | -80.899 | -29.110 | 81.017 | 1.00 | 27.88 |
| 2362 | N | TYR | A | 296 | -79.897 | -28.569 | 82.934 | 1.00 | 29.00 |
| 2363 | CA | TYR | A | 296 | -80.815 | -29.347 | 83.740 | 1.00 | 29.04 |
| 2364 | CB | TYR | A | 296 | -80.213 | -30.727 | 83.982 | 1.00 | 29.11 |
| 2365 | CG | TYR | A | 296 | -81.156 | -31.715 | 84.629 | 1.00 | 30.85 |
| 2366 | CD1 | TYR | A | 296 | -81.991 | -32.509 | 83.861 | 1.00 | 32.89 |
| 2367 | CE1 | TYR | A | 296 | -82.836 | -33.440 | 84.450 | 1.00 | 33.67 |
| 2368 | CZ | TYR | A | 296 | -82.840 | -33.561 | 85.817 | 1.00 | 34.54 |
| 2369 | OH | TYR | A | 296 | -83.671 | -34.467 | 86.421 | 1.00 | 37.48 |
| 2370 | CE2 | TYR | A | 296 | -82.019 | -32.784 | 86.590 | 1.00 | 32.41 |
| 2371 | CD2 | TYR | A | 296 | -81.187 | -31.874 | 85.999 | 1.00 | 31.07 |
| 2372 | C | TYR | A | 296 | -81.060 | -28.690 | 85.076 | 1.00 | 28.70 |
| 2373 | O | TYR | A | 296 | -80.162 | -28.592 | 85.900 | 1.00 | 29.09 |
| 2374 | N | SER | A | 297 | -82.287 | -28.272 | 85.313 | 1.00 | 28.63 |
| 2375 | CA | SER | A | 297 | -82.616 | -27.615 | 86.566 | 1.00 | 29.06 |
| 2376 | CB | SER | A | 297 | -82.919 | -26.147 | 86.316 | 1.00 | 28.05 |
| 2377 | OG | SER | A | 297 | -83.933 | -26.044 | 85.343 | 1.00 | 29.76 |
| 2378 | C | SER | A | 297 | -83.822 | -28.304 | 87.163 | 1.00 | 29.00 |
| 2379 | O | SER | A | 297 | -84.625 | -28.875 | 86.445 | 1.00 | 29.64 |
| 2380 | N | VAL | A | 298 | -83.955 | -28.260 | 88.478 | 1.00 | 29.88 |
| 2381 | CA | VAL | A | 298 | -85.105 | -28.897 | 89.118 | 1.00 | 30.60 |
| 2382 | CB | VAL | A | 298 | -84.704 | -30.153 | 89.923 | 1.00 | 30.18 |
| 2383 | CG1 | VAL | A | 298 | -84.147 | -31.222 | 89.018 | 1.00 | 30.05 |
| 2384 | CG2 | VAL | A | 298 | -85.915 | -30.714 | 90.653 | 1.00 | 31.51 |
| 2385 | C | VAL | A | 298 | -85.761 | -27.916 | 90.062 | 1.00 | 31.14 |
| 2386 | O | VAL | A | 298 | -85.074 | -27.194 | 90.772 | 1.00 | 30.60 |
| 2387 | N | MET | A | 299 | -87.089 | -27.881 | 90.062 | 1.00 | 32.41 |

FIGURE 3 AU

| A | B | C | D | E | F | G | H | I | J |
|---|---|---|---|---|---|---|---|---|---|
| 2388 | CA | MET | A | 299 | -87.798 | -27.045 | 91.009 | 1.00 | 34.10 |
| 2389 | CB | MET | A | 299 | -88.944 | -26.253 | 90.373 | 1.00 | 33.77 |
| 2390 | CG | MET | A | 299 | -89.640 | -25.335 | 91.396 | 1.00 | 34.32 |
| 2391 | SD | MET | A | 299 | -91.132 | -24.482 | 90.826 | 1.00 | 37.41 |
| 2392 | CE | MET | A | 299 | -92.237 | -25.756 | 90.878 | 1.00 | 38.42 |
| 2393 | C | MET | A | 299 | -88.365 | -27.877 | 92.148 | 1.00 | 35.43 |
| 2394 | O | MET | A | 299 | -89.218 | -28.731 | 91.934 | 1.00 | 35.56 |
| 2395 | N | ASP | A | 300 | -87.899 | -27.617 | 93.360 | 1.00 | 36.85 |
| 2396 | CA | ASP | A | 300 | -88.474 | -28.267 | 94.519 | 1.00 | 38.72 |
| 2397 | CB | ASP | A | 300 | -87.435 | -28.468 | 95.595 | 1.00 | 38.93 |
| 2398 | CG | ASP | A | 300 | -87.085 | -29.904 | 95.785 | 1.00 | 39.58 |
| 2399 | OD1 | ASP | A | 300 | -86.032 | -30.175 | 96.381 | 1.00 | 41.59 |
| 2400 | OD2 | ASP | A | 300 | -87.807 | -30.829 | 95.381 | 1.00 | 41.61 |
| 2401 | C | ASP | A | 300 | -89.580 | -27.428 | 95.104 | 1.00 | 40.22 |
| 2402 | O | ASP | A | 300 | -89.564 | -26.200 | 95.022 | 1.00 | 40.30 |
| 2403 | N | ILE | A | 301 | -90.548 | -28.096 | 95.709 | 1.00 | 41.62 |
| 2404 | CA | ILE | A | 301 | -91.593 | -27.392 | 96.422 | 1.00 | 43.20 |
| 2405 | CB | ILE | A | 301 | -92.921 | -27.522 | 95.686 | 1.00 | 43.15 |
| 2406 | CG1 | ILE | A | 301 | -92.843 | -26.694 | 94.394 | 1.00 | 43.52 |
| 2407 | CD1 | ILE | A | 301 | -93.976 | -26.916 | 93.432 | 1.00 | 42.31 |
| 2408 | CG2 | ILE | A | 301 | -94.046 | -27.036 | 96.549 | 1.00 | 43.80 |
| 2409 | C | ILE | A | 301 | -91.615 | -27.910 | 97.863 | 1.00 | 44.31 |
| 2410 | O | ILE | A | 301 | -91.919 | -29.074 | 98.139 | 1.00 | 44.63 |
| 2411 | N | CYS | A | 302 | -91.238 | -27.041 | 98.785 | 1.00 | 45.44 |
| 2412 | CA | CYS | A | 302 | -91.109 | -27.450 | 100.163 | 1.00 | 46.51 |
| 2413 | CB | CYS | A | 302 | -89.707 | -27.128 | 100.654 | 1.00 | 46.72 |
| 2414 | SG | CYS | A | 302 | -88.467 | -27.641 | 99.438 | 1.00 | 47.60 |
| 2415 | C | CYS | A | 302 | -92.180 | -26.867 | 101.070 | 1.00 | 47.22 |
| 2416 | O | CYS | A | 302 | -92.363 | -25.651 | 101.150 | 1.00 | 46.52 |
| 2417 | N | ASP | A | 303 | -92.901 | -27.759 | 101.739 | 1.00 | 48.46 |
| 2418 | CA | ASP | A | 303 | -93.955 | -27.336 | 102.643 | 1.00 | 50.03 |
| 2419 | CB | ASP | A | 303 | -95.231 | -28.129 | 102.384 | 1.00 | 50.42 |
| 2420 | CG | ASP | A | 303 | -95.793 | -27.862 | 101.013 | 1.00 | 51.83 |
| 2421 | OD1 | ASP | A | 303 | -94.992 | -27.833 | 100.055 | 1.00 | 53.94 |
| 2422 | OD2 | ASP | A | 303 | -97.004 | -27.653 | 100.789 | 1.00 | 53.82 |
| 2423 | C | ASP | A | 303 | -93.541 | -27.454 | 104.093 | 1.00 | 50.54 |
| 2424 | O | ASP | A | 303 | -92.888 | -28.424 | 104.495 | 1.00 | 50.52 |
| 2425 | N | TYR | A | 304 | -93.917 | -26.454 | 104.876 | 1.00 | 51.37 |
| 2426 | CA | TYR | A | 304 | -93.619 | -26.471 | 106.293 | 1.00 | 52.61 |
| 2427 | CB | TYR | A | 304 | -93.868 | -25.100 | 106.894 | 1.00 | 52.69 |
| 2428 | CG | TYR | A | 304 | -93.602 | -25.048 | 108.374 | 1.00 | 53.78 |
| 2429 | CD1 | TYR | A | 304 | -92.301 | -25.092 | 108.865 | 1.00 | 53.47 |
| 2430 | CE1 | TYR | A | 304 | -92.053 | -25.043 | 110.209 | 1.00 | 54.32 |
| 2431 | CZ | TYR | A | 304 | -93.111 | -24.954 | 111.097 | 1.00 | 54.60 |
| 2432 | OH | TYR | A | 304 | -92.863 | -24.905 | 112.447 | 1.00 | 54.22 |
| 2433 | CE2 | TYR | A | 304 | -94.409 | -24.908 | 110.636 | 1.00 | 54.38 |
| 2434 | CD2 | TYR | A | 304 | -94.649 | -24.960 | 109.282 | 1.00 | 53.62 |
| 2435 | C | TYR | A | 304 | -94.473 | -27.520 | 107.009 | 1.00 | 53.58 |
| 2436 | O | TYR | A | 304 | -95.697 | -27.576 | 106.838 | 1.00 | 53.17 |
| 2437 | N | ASP | A | 305 | -93.818 | -28.368 | 107.793 | 1.00 | 54.91 |
| 2438 | CA | ASP | A | 305 | -94.521 | -29.400 | 108.548 | 1.00 | 56.29 |

FIGURE 3 AV

| A | B | C | D | E | F | G | H | I | J |
|---|---|---|---|---|---|---|---|---|---|
| 2439 | CB | ASP | A | 305 | -93.736 | -30.711 | 108.534 | 1.00 | 56.44 |
| 2440 | CG | ASP | A | 305 | -94.559 | -31.884 | 109.015 | 1.00 | 57.27 |
| 2441 | OD1 | ASP | A | 305 | -95.392 | -31.680 | 109.924 | 1.00 | 58.51 |
| 2442 | OD2 | ASP | A | 305 | -94.445 | -33.042 | 108.547 | 1.00 | 57.28 |
| 2443 | C | ASP | A | 305 | -94.712 | -28.904 | 109.975 | 1.00 | 56.77 |
| 2444 | O | ASP | A | 305 | -93.772 | -28.914 | 110.768 | 1.00 | 56.54 |
| 2445 | N | GLU | A | 306 | -95.932 | -28.459 | 110.273 | 1.00 | 57.77 |
| 2446 | CA | GLU | A | 306 | -96.286 | -27.889 | 111.578 | 1.00 | 58.94 |
| 2447 | CB | GLU | A | 306 | -97.781 | -27.553 | 111.642 | 1.00 | 59.22 |
| 2448 | CG | GLU | A | 306 | -98.092 | -26.078 | 111.493 | 1.00 | 60.83 |
| 2449 | CD | GLU | A | 306 | -98.939 | -25.559 | 112.638 | 1.00 | 63.17 |
| 2450 | OE1 | GLU | A | 306 | -100.132 | -25.929 | 112.723 | 1.00 | 63.52 |
| 2451 | OE2 | GLU | A | 306 | -98.401 | -24.787 | 113.464 | 1.00 | 63.58 |
| 2452 | C | GLU | A | 306 | -95.926 | -28.739 | 112.792 | 1.00 | 59.24 |
| 2453 | O | GLU | A | 306 | -95.613 | -28.209 | 113.854 | 1.00 | 59.09 |
| 2454 | N | SER | A | 307 | -95.994 | -30.057 | 112.637 | 1.00 | 59.75 |
| 2455 | CA | SER | A | 307 | -95.678 | -30.957 | 113.734 | 1.00 | 60.26 |
| 2456 | CB | SER | A | 307 | -96.426 | -32.288 | 113.576 | 1.00 | 60.62 |
| 2457 | OG | SER | A | 307 | -96.398 | -32.746 | 112.229 | 1.00 | 61.31 |
| 2458 | C | SER | A | 307 | -94.173 | -31.181 | 113.858 | 1.00 | 60.30 |
| 2459 | O | SER | A | 307 | -93.601 | -30.988 | 114.931 | 1.00 | 60.62 |
| 2460 | N | SER | A | 308 | -93.540 | -31.575 | 112.754 | 1.00 | 60.12 |
| 2461 | CA | SER | A | 308 | -92.102 | -31.851 | 112.717 | 1.00 | 59.53 |
| 2462 | CB | SER | A | 308 | -91.703 | -32.378 | 111.334 | 1.00 | 59.77 |
| 2463 | OG | SER | A | 308 | -92.009 | -33.753 | 111.176 | 1.00 | 60.20 |
| 2464 | C | SER | A | 308 | -91.256 | -30.621 | 113.011 | 1.00 | 59.06 |
| 2465 | O | SER | A | 308 | -90.133 | -30.732 | 113.512 | 1.00 | 59.11 |
| 2466 | N | GLY | A | 309 | -91.790 | -29.451 | 112.680 | 1.00 | 58.26 |
| 2467 | CA | GLY | A | 309 | -91.049 | -28.211 | 112.821 | 1.00 | 57.16 |
| 2468 | C | GLY | A | 309 | -90.102 | -28.063 | 111.641 | 1.00 | 56.45 |
| 2469 | O | GLY | A | 309 | -89.250 | -27.177 | 111.614 | 1.00 | 56.64 |
| 2470 | N | ARG | A | 310 | -90.268 | -28.931 | 110.648 | 1.00 | 55.33 |
| 2471 | CA | ARG | A | 310 | -89.367 | -28.950 | 109.505 | 1.00 | 54.21 |
| 2472 | CB | ARG | A | 310 | -88.622 | -30.288 | 109.442 | 1.00 | 54.66 |
| 2473 | CG | ARG | A | 310 | -87.696 | -30.525 | 110.627 | 1.00 | 56.06 |
| 2474 | CD | ARG | A | 310 | -86.511 | -31.445 | 110.328 | 1.00 | 59.60 |
| 2475 | NE | ARG | A | 310 | -86.812 | -32.862 | 110.539 | 1.00 | 62.08 |
| 2476 | CZ | ARG | A | 310 | -87.479 | -33.632 | 109.680 | 1.00 | 63.36 |
| 2477 | NH1 | ARG | A | 310 | -87.929 | -33.132 | 108.532 | 1.00 | 63.22 |
| 2478 | NH2 | ARG | A | 310 | -87.696 | -34.911 | 109.970 | 1.00 | 63.95 |
| 2479 | C | ARG | A | 310 | -90.012 | -28.641 | 108.151 | 1.00 | 52.85 |
| 2480 | O | ARG | A | 310 | -91.212 | -28.369 | 108.057 | 1.00 | 52.44 |
| 2481 | N | TRP | A | 311 | -89.181 | -28.684 | 107.111 | 1.00 | 51.08 |
| 2482 | CA | TRP | A | 311 | -89.607 | -28.414 | 105.747 | 1.00 | 49.29 |
| 2483 | CB | TRP | A | 311 | -88.880 | -27.188 | 105.202 | 1.00 | 48.37 |
| 2484 | CG | TRP | A | 311 | -89.234 | -25.910 | 105.882 | 1.00 | 44.19 |
| 2485 | CD1 | TRP | A | 311 | -88.713 | -25.421 | 107.051 | 1.00 | 40.78 |
| 2486 | NE1 | TRP | A | 311 | -89.281 | -24.206 | 107.351 | 1.00 | 38.90 |
| 2487 | CE2 | TRP | A | 311 | -90.184 | -23.885 | 106.373 | 1.00 | 39.10 |
| 2488 | CD2 | TRP | A | 311 | -90.178 | -24.939 | 105.430 | 1.00 | 40.46 |
| 2489 | CE3 | TRP | A | 311 | -91.019 | -24.845 | 104.318 | 1.00 | 37.66 |

FIGURE 3 AW

| A | B | C | D | E | F | G | H | I | J |
|---|---|---|---|---|---|---|---|---|---|
| 2490 | CZ3 | TRP | A | 311 | -91.818 | -23.734 | 104.185 | 1.00 | 35.16 |
| 2491 | CH2 | TRP | A | 311 | -91.809 | -22.717 | 105.145 | 1.00 | 36.12 |
| 2492 | CZ2 | TRP | A | 311 | -90.997 | -22.771 | 106.239 | 1.00 | 36.29 |
| 2493 | C | TRP | A | 311 | -89.332 | -29.630 | 104.860 | 1.00 | 49.37 |
| 2494 | O | TRP | A | 311 | -88.208 | -30.128 | 104.785 | 1.00 | 49.14 |
| 2495 | N | ASN | A | 312 | -90.367 | -30.120 | 104.199 | 1.00 | 49.46 |
| 2496 | CA | ASN | A | 312 | -90.214 | -31.296 | 103.357 | 1.00 | 50.06 |
| 2497 | CB | ASN | A | 312 | -91.091 | -32.442 | 103.876 | 1.00 | 50.41 |
| 2498 | CG | ASN | A | 312 | -90.447 | -33.202 | 105.038 | 1.00 | 52.10 |
| 2499 | OD1 | ASN | A | 312 | -90.693 | -34.397 | 105.220 | 1.00 | 54.19 |
| 2500 | ND2 | ASN | A | 312 | -89.620 | -32.512 | 105.826 | 1.00 | 53.48 |
| 2501 | C | ASN | A | 312 | -90.504 | -31.010 | 101.883 | 1.00 | 49.73 |
| 2502 | O | ASN | A | 312 | -91.475 | -30.332 | 101.553 | 1.00 | 49.59 |
| 2503 | N | CYS | A | 313 | -89.643 | -31.515 | 101.005 | 1.00 | 49.61 |
| 2504 | CA | CYS | A | 313 | -89.821 | -31.332 | 99.565 | 1.00 | 49.32 |
| 2505 | CB | CYS | A | 313 | -88.549 | -30.778 | 98.921 | 1.00 | 49.21 |
| 2506 | SG | CYS | A | 313 | -87.730 | -29.487 | 99.875 | 1.00 | 48.98 |
| 2507 | C | CYS | A | 313 | -90.177 | -32.654 | 98.910 | 1.00 | 49.28 |
| 2508 | O | CYS | A | 313 | -89.299 | -33.428 | 98.557 | 1.00 | 49.40 |
| 2509 | N | LEU | A | 314 | -91.470 | -32.905 | 98.751 | 1.00 | 49.23 |
| 2510 | CA | LEU | A | 314 | -91.948 | -34.125 | 98.122 | 1.00 | 49.20 |
| 2511 | CB | LEU | A | 314 | -93.471 | -34.083 | 98.003 | 1.00 | 49.51 |
| 2512 | CG | LEU | A | 314 | -94.318 | -34.759 | 99.090 | 1.00 | 50.18 |
| 2513 | CD1 | LEU | A | 314 | -95.651 | -34.033 | 99.258 | 1.00 | 50.99 |
| 2514 | CD2 | LEU | A | 314 | -93.579 | -34.843 | 100.417 | 1.00 | 51.00 |
| 2515 | C | LEU | A | 314 | -91.328 | -34.364 | 96.742 | 1.00 | 49.05 |
| 2516 | O | LEU | A | 314 | -91.574 | -33.617 | 95.801 | 1.00 | 48.88 |
| 2517 | N | VAL | A | 315 | -90.522 | -35.415 | 96.633 | 1.00 | 49.03 |
| 2518 | CA | VAL | A | 315 | -89.916 | -35.793 | 95.370 | 1.00 | 48.83 |
| 2519 | CB | VAL | A | 315 | -89.304 | -37.207 | 95.454 | 1.00 | 48.97 |
| 2520 | CG1 | VAL | A | 315 | -89.162 | -37.824 | 94.070 | 1.00 | 49.30 |
| 2521 | CG2 | VAL | A | 315 | -87.955 | -37.170 | 96.165 | 1.00 | 48.31 |
| 2522 | C | VAL | A | 315 | -90.969 | -35.761 | 94.272 | 1.00 | 48.78 |
| 2523 | O | VAL | A | 315 | -90.692 | -35.398 | 93.125 | 1.00 | 49.03 |
| 2524 | N | ALA | A | 316 | -92.195 | -36.107 | 94.635 | 1.00 | 48.31 |
| 2525 | CA | ALA | A | 316 | -93.276 | -36.135 | 93.662 | 1.00 | 47.94 |
| 2526 | CB | ALA | A | 316 | -94.440 | -36.957 | 94.186 | 1.00 | 47.92 |
| 2527 | C | ALA | A | 316 | -93.762 | -34.757 | 93.246 | 1.00 | 47.64 |
| 2528 | O | ALA | A | 316 | -94.625 | -34.648 | 92.385 | 1.00 | 48.02 |
| 2529 | N | ARG | A | 317 | -93.238 | -33.707 | 93.864 | 1.00 | 47.02 |
| 2530 | CA | ARG | A | 317 | -93.675 | -32.359 | 93.515 | 1.00 | 46.41 |
| 2531 | CB | ARG | A | 317 | -94.189 | -31.620 | 94.749 | 1.00 | 46.68 |
| 2532 | CG | ARG | A | 317 | -95.340 | -32.365 | 95.405 | 1.00 | 48.25 |
| 2533 | CD | ARG | A | 317 | -96.471 | -31.507 | 95.915 | 1.00 | 49.42 |
| 2534 | NE | ARG | A | 317 | -96.072 | -30.749 | 97.088 | 1.00 | 52.62 |
| 2535 | CZ | ARG | A | 317 | -96.886 | -30.434 | 98.086 | 1.00 | 53.61 |
| 2536 | NH1 | ARG | A | 317 | -96.420 | -29.744 | 99.114 | 1.00 | 53.83 |
| 2537 | NH2 | ARG | A | 317 | -98.160 | -30.812 | 98.061 | 1.00 | 53.37 |
| 2538 | C | ARG | A | 317 | -92.588 | -31.574 | 92.780 | 1.00 | 45.51 |
| 2539 | O | ARG | A | 317 | -92.738 | -30.391 | 92.509 | 1.00 | 45.08 |
| 2540 | N | GLN | A | 318 | -91.502 | -32.268 | 92.452 | 1.00 | 44.70 |

FIGURE 3 AX

| A | B | C | D | E | F | G | H | I | J |
|---|---|---|---|---|---|---|---|---|---|
| 2541 | CA | GLN | A | 318 | -90.396 | -31.688 | 91.715 | 1.00 | 43.92 |
| 2542 | CB | GLN | A | 318 | -89.187 | -32.613 | 91.761 | 1.00 | 44.06 |
| 2543 | CG | GLN | A | 318 | -88.533 | -32.679 | 93.122 | 1.00 | 45.59 |
| 2544 | CD | GLN | A | 318 | -87.325 | -33.589 | 93.142 | 1.00 | 48.07 |
| 2545 | OE1 | GLN | A | 318 | -86.775 | -33.865 | 94.211 | 1.00 | 49.48 |
| 2546 | NE2 | GLN | A | 318 | -86.903 | -34.056 | 91.965 | 1.00 | 47.11 |
| 2547 | C | GLN | A | 318 | -90.791 | -31.467 | 90.273 | 1.00 | 43.00 |
| 2548 | O | GLN | A | 318 | -91.502 | -32.277 | 89.686 | 1.00 | 43.13 |
| 2549 | N | HIS | A | 319 | -90.345 | -30.349 | 89.718 | 1.00 | 41.42 |
| 2550 | CA | HIS | A | 319 | -90.590 | -30.044 | 88.331 | 1.00 | 40.05 |
| 2551 | CB | HIS | A | 319 | -91.456 | -28.811 | 88.197 | 1.00 | 39.89 |
| 2552 | CG | HIS | A | 319 | -92.885 | -29.064 | 88.549 | 1.00 | 41.96 |
| 2553 | ND1 | HIS | A | 319 | -93.310 | -29.243 | 89.849 | 1.00 | 43.05 |
| 2554 | CE1 | HIS | A | 319 | -94.612 | -29.459 | 89.856 | 1.00 | 42.55 |
| 2555 | NE2 | HIS | A | 319 | -95.044 | -29.439 | 88.608 | 1.00 | 42.08 |
| 2556 | CD2 | HIS | A | 319 | -93.984 | -29.196 | 87.770 | 1.00 | 41.11 |
| 2557 | C | HIS | A | 319 | -89.262 | -29.871 | 87.638 | 1.00 | 38.85 |
| 2558 | O | HIS | A | 319 | -88.434 | -29.079 | 88.056 | 1.00 | 38.75 |
| 2559 | N | ILE | A | 320 | -89.065 | -30.630 | 86.574 | 1.00 | 37.80 |
| 2560 | CA | ILE | A | 320 | -87.816 | -30.592 | 85.849 | 1.00 | 36.71 |
| 2561 | CB | ILE | A | 320 | -87.489 | -31.985 | 85.362 | 1.00 | 36.70 |
| 2562 | CG1 | ILE | A | 320 | -87.306 | -32.906 | 86.570 | 1.00 | 36.99 |
| 2563 | CD1 | ILE | A | 320 | -87.223 | -34.374 | 86.214 | 1.00 | 38.96 |
| 2564 | CG2 | ILE | A | 320 | -86.279 | -31.952 | 84.419 | 1.00 | 35.80 |
| 2565 | C | ILE | A | 320 | -87.867 | -29.637 | 84.659 | 1.00 | 36.24 |
| 2566 | O | ILE | A | 320 | -88.852 | -29.578 | 83.938 | 1.00 | 34.52 |
| 2567 | N | GLU | A | 321 | -86.790 | -28.877 | 84.486 | 1.00 | 36.11 |
| 2568 | CA | GLU | A | 321 | -86.664 | -28.005 | 83.330 | 1.00 | 36.25 |
| 2569 | CB | GLU | A | 321 | -86.914 | -26.553 | 83.702 | 1.00 | 35.46 |
| 2570 | CG | GLU | A | 321 | -87.255 | -25.694 | 82.512 | 1.00 | 37.29 |
| 2571 | CD | GLU | A | 321 | -87.300 | -24.224 | 82.859 | 1.00 | 39.57 |
| 2572 | OE1 | GLU | A | 321 | -87.550 | -23.910 | 84.050 | 1.00 | 41.03 |
| 2573 | OE2 | GLU | A | 321 | -87.084 | -23.388 | 81.944 | 1.00 | 40.17 |
| 2574 | C | GLU | A | 321 | -85.253 | -28.202 | 82.786 | 1.00 | 36.34 |
| 2575 | O | GLU | A | 321 | -84.269 | -27.822 | 83.419 | 1.00 | 36.18 |
| 2576 | N | MET | A | 322 | -85.176 | -28.826 | 81.618 | 1.00 | 35.99 |
| 2577 | CA | MET | A | 322 | -83.916 | -29.136 | 80.984 | 1.00 | 35.89 |
| 2578 | CB | MET | A | 322 | -83.664 | -30.649 | 81.007 | 1.00 | 36.45 |
| 2579 | CG | MET | A | 322 | -84.751 | -31.485 | 80.328 | 1.00 | 40.37 |
| 2580 | SD | MET | A | 322 | -84.281 | -33.246 | 80.076 | 1.00 | 49.26 |
| 2581 | CE | MET | A | 322 | -84.432 | -33.862 | 81.690 | 1.00 | 46.43 |
| 2582 | C | MET | A | 322 | -83.970 | -28.630 | 79.558 | 1.00 | 35.10 |
| 2583 | O | MET | A | 322 | -85.007 | -28.181 | 79.084 | 1.00 | 34.63 |
| 2584 | N | SER | A | 323 | -82.844 | -28.683 | 78.869 | 1.00 | 34.71 |
| 2585 | CA | SER | A | 323 | -82.823 | -28.255 | 77.475 | 1.00 | 34.46 |
| 2586 | CB | SER | A | 323 | -82.292 | -26.819 | 77.337 | 1.00 | 34.00 |
| 2587 | OG | SER | A | 323 | -82.045 | -26.519 | 75.971 | 1.00 | 34.22 |
| 2588 | C | SER | A | 323 | -81.936 | -29.205 | 76.713 | 1.00 | 33.99 |
| 2589 | O | SER | A | 323 | -80.885 | -29.587 | 77.196 | 1.00 | 33.94 |
| 2590 | N | THR | A | 324 | -82.356 | -29.575 | 75.515 | 1.00 | 34.42 |
| 2591 | CA | THR | A | 324 | -81.558 | -30.470 | 74.684 | 1.00 | 34.27 |

FIGURE 3 AY

| A | B | C | D | E | F | G | H | I | J |
|---|---|---|---|---|---|---|---|---|---|
| 2592 | CB | THR | A | 324 | -82.457 | -31.435 | 73.901 | 1.00 | 34.74 |
| 2593 | OG1 | THR | A | 324 | -83.248 | -30.697 | 72.960 | 1.00 | 35.02 |
| 2594 | CG2 | THR | A | 324 | -83.496 | -32.057 | 74.843 | 1.00 | 34.52 |
| 2595 | C | THR | A | 324 | -80.682 | -29.691 | 73.730 | 1.00 | 33.76 |
| 2596 | O | THR | A | 324 | -79.699 | -30.225 | 73.230 | 1.00 | 34.89 |
| 2597 | N | THR | A | 325 | -81.006 | -28.429 | 73.474 | 1.00 | 32.42 |
| 2598 | CA | THR | A | 325 | -80.173 | -27.662 | 72.553 | 1.00 | 31.29 |
| 2599 | CB | THR | A | 325 | -81.032 | -26.912 | 71.555 | 1.00 | 31.37 |
| 2600 | OG1 | THR | A | 325 | -81.947 | -26.079 | 72.275 | 1.00 | 30.65 |
| 2601 | CG2 | THR | A | 325 | -81.921 | -27.889 | 70.779 | 1.00 | 31.29 |
| 2602 | C | THR | A | 325 | -79.226 | -26.662 | 73.206 | 1.00 | 30.45 |
| 2603 | O | THR | A | 325 | -78.405 | -26.080 | 72.522 | 1.00 | 30.08 |
| 2604 | N | GLY | A | 326 | -79.361 | -26.433 | 74.505 | 1.00 | 29.74 |
| 2605 | CA | GLY | A | 326 | -78.501 | -25.480 | 75.183 | 1.00 | 29.11 |
| 2606 | C | GLY | A | 326 | -78.619 | -25.523 | 76.682 | 1.00 | 28.22 |
| 2607 | O | GLY | A | 326 | -78.786 | -26.595 | 77.250 | 1.00 | 29.13 |
| 2608 | N | TRP | A | 327 | -78.524 | -24.354 | 77.316 | 1.00 | 27.43 |
| 2609 | CA | TRP | A | 327 | -78.630 | -24.194 | 78.773 | 1.00 | 25.97 |
| 2610 | CB | TRP | A | 327 | -77.826 | -22.960 | 79.231 | 1.00 | 26.00 |
| 2611 | CG | TRP | A | 327 | -78.213 | -21.693 | 78.496 | 1.00 | 23.64 |
| 2612 | CD1 | TRP | A | 327 | -79.052 | -20.721 | 78.940 | 1.00 | 22.57 |
| 2613 | NE1 | TRP | A | 327 | -79.166 | -19.716 | 78.003 | 1.00 | 22.25 |
| 2614 | CE2 | TRP | A | 327 | -78.399 | -20.030 | 76.913 | 1.00 | 23.44 |
| 2615 | CD2 | TRP | A | 327 | -77.775 | -21.272 | 77.188 | 1.00 | 23.16 |
| 2616 | CE3 | TRP | A | 327 | -76.914 | -21.811 | 76.224 | 1.00 | 21.49 |
| 2617 | CZ3 | TRP | A | 327 | -76.714 | -21.108 | 75.030 | 1.00 | 21.48 |
| 2618 | CH2 | TRP | A | 327 | -77.367 | -19.888 | 74.777 | 1.00 | 17.89 |
| 2619 | CZ2 | TRP | A | 327 | -78.196 | -19.322 | 75.707 | 1.00 | 22.30 |
| 2620 | C | TRP | A | 327 | -80.095 | -23.965 | 79.056 | 1.00 | 25.40 |
| 2621 | O | TRP | A | 327 | -80.870 | -23.928 | 78.129 | 1.00 | 24.97 |
| 2622 | N | VAL | A | 328 | -80.484 | -23.809 | 80.318 | 1.00 | 25.17 |
| 2623 | CA | VAL | A | 328 | -81.888 | -23.555 | 80.632 | 1.00 | 26.17 |
| 2624 | CB | VAL | A | 328 | -82.437 | -24.498 | 81.750 | 1.00 | 26.11 |
| 2625 | CG1 | VAL | A | 328 | -81.397 | -24.780 | 82.760 | 1.00 | 27.28 |
| 2626 | CG2 | VAL | A | 328 | -83.660 | -23.883 | 82.430 | 1.00 | 26.46 |
| 2627 | C | VAL | A | 328 | -82.142 | -22.114 | 81.021 | 1.00 | 25.84 |
| 2628 | O | VAL | A | 328 | -81.375 | -21.534 | 81.763 | 1.00 | 27.58 |
| 2629 | N | GLY | A | 329 | -83.232 | -21.542 | 80.525 | 1.00 | 26.06 |
| 2630 | CA | GLY | A | 329 | -83.569 | -20.161 | 80.813 | 1.00 | 25.46 |
| 2631 | C | GLY | A | 329 | -82.736 | -19.201 | 79.984 | 1.00 | 25.11 |
| 2632 | O | GLY | A | 329 | -81.795 | -19.611 | 79.306 | 1.00 | 24.50 |
| 2633 | N | ARG | A | 330 | -83.071 | -17.918 | 80.041 | 1.00 | 25.08 |
| 2634 | CA | ARG | A | 330 | -82.344 | -16.953 | 79.236 | 1.00 | 25.69 |
| 2635 | CB | ARG | A | 330 | -83.132 | -15.640 | 79.068 | 1.00 | 26.08 |
| 2636 | CG | ARG | A | 330 | -84.259 | -15.839 | 78.002 | 1.00 | 26.77 |
| 2637 | CD | ARG | A | 330 | -84.897 | -14.595 | 77.357 | 1.00 | 26.77 |
| 2638 | NE | ARG | A | 330 | -86.029 | -14.276 | 78.180 | 1.00 | 32.62 |
| 2639 | CZ | ARG | A | 330 | -87.305 | -14.271 | 77.811 | 1.00 | 30.25 |
| 2640 | NH1 | ARG | A | 330 | -88.199 | -14.004 | 78.748 | 1.00 | 30.22 |
| 2641 | NH2 | ARG | A | 330 | -87.687 | -14.500 | 76.553 | 1.00 | 27.09 |
| 2642 | C | ARG | A | 330 | -80.933 | -16.836 | 79.781 | 1.00 | 25.65 |

FIGURE 3 AZ

| A | B | C | D | E | F | G | H | I | J |
|---|---|---|---|---|---|---|---|---|---|
| 2643 | O | ARG | A | 330 | -79.972 | -17.123 | 79.092 | 1.00 | 24.20 |
| 2644 | N | PHE | A | 331 | -80.828 | -16.476 | 81.052 | 1.00 | 26.79 |
| 2645 | CA | PHE | A | 331 | -79.551 | -16.493 | 81.721 | 1.00 | 27.54 |
| 2646 | CB | PHE | A | 331 | -79.146 | -15.097 | 82.172 | 1.00 | 26.96 |
| 2647 | CG | PHE | A | 331 | -78.881 | -14.155 | 81.036 | 1.00 | 27.24 |
| 2648 | CD1 | PHE | A | 331 | -77.597 | -13.961 | 80.559 | 1.00 | 27.56 |
| 2649 | CE1 | PHE | A | 331 | -77.369 | -13.070 | 79.515 | 1.00 | 28.57 |
| 2650 | CZ | PHE | A | 331 | -78.436 | -12.379 | 78.939 | 1.00 | 23.11 |
| 2651 | CE2 | PHE | A | 331 | -79.679 | -12.570 | 79.402 | 1.00 | 24.68 |
| 2652 | CD2 | PHE | A | 331 | -79.915 | -13.447 | 80.449 | 1.00 | 26.99 |
| 2653 | C | PHE | A | 331 | -79.621 | -17.467 | 82.892 | 1.00 | 28.01 |
| 2654 | O | PHE | A | 331 | -78.595 | -17.860 | 83.436 | 1.00 | 28.75 |
| 2655 | N | ARG | A | 332 | -80.838 | -17.869 | 83.242 | 1.00 | 28.70 |
| 2656 | CA | ARG | A | 332 | -81.105 | -18.772 | 84.369 | 1.00 | 29.58 |
| 2657 | CB | ARG | A | 332 | -80.890 | -18.059 | 85.712 | 1.00 | 29.72 |
| 2658 | CG | ARG | A | 332 | -81.986 | -17.027 | 86.029 | 1.00 | 32.07 |
| 2659 | CD | ARG | A | 332 | -81.631 | -15.977 | 87.078 | 1.00 | 39.24 |
| 2660 | NE | ARG | A | 332 | -81.351 | -14.675 | 86.443 | 1.00 | 43.86 |
| 2661 | CZ | ARG | A | 332 | -80.130 | -14.236 | 86.140 | 1.00 | 44.14 |
| 2662 | NH1 | ARG | A | 332 | -79.063 | -14.982 | 86.421 | 1.00 | 43.26 |
| 2663 | NH2 | ARG | A | 332 | -79.975 | -13.053 | 85.560 | 1.00 | 43.53 |
| 2664 | C | ARG | A | 332 | -82.569 | -19.138 | 84.260 | 1.00 | 29.56 |
| 2665 | O | ARG | A | 332 | -83.330 | -18.409 | 83.644 | 1.00 | 29.36 |
| 2666 | N | PRO | A | 333 | -82.977 | -20.250 | 84.858 | 1.00 | 29.98 |
| 2667 | CA | PRO | A | 333 | -84.391 | -20.636 | 84.821 | 1.00 | 30.22 |
| 2668 | CB | PRO | A | 333 | -84.457 | -21.870 | 85.729 | 1.00 | 30.22 |
| 2669 | CG | PRO | A | 333 | -83.042 | -22.375 | 85.822 | 1.00 | 30.06 |
| 2670 | CD | PRO | A | 333 | -82.134 | -21.218 | 85.583 | 1.00 | 29.85 |
| 2671 | C | PRO | A | 333 | -85.234 | -19.500 | 85.387 | 1.00 | 30.43 |
| 2672 | O | PRO | A | 333 | -84.814 | -18.797 | 86.314 | 1.00 | 30.71 |
| 2673 | N | SER | A | 334 | -86.404 | -19.329 | 84.803 | 1.00 | 30.67 |
| 2674 | CA | SER | A | 334 | -87.360 | -18.299 | 85.164 | 1.00 | 32.06 |
| 2675 | CB | SER | A | 334 | -88.538 | -18.335 | 84.182 | 1.00 | 32.08 |
| 2676 | OG | SER | A | 334 | -88.289 | -17.506 | 83.072 | 1.00 | 34.32 |
| 2677 | C | SER | A | 334 | -87.948 | -18.501 | 86.530 | 1.00 | 32.20 |
| 2678 | O | SER | A | 334 | -88.018 | -19.616 | 87.027 | 1.00 | 32.94 |
| 2679 | N | GLU | A | 335 | -88.425 | -17.411 | 87.110 | 1.00 | 32.23 |
| 2680 | CA | GLU | A | 335 | -89.071 | -17.466 | 88.392 | 1.00 | 32.12 |
| 2681 | CB | GLU | A | 335 | -88.936 | -16.108 | 89.108 | 1.00 | 32.09 |
| 2682 | CG | GLU | A | 335 | -89.910 | -15.015 | 88.686 | 1.00 | 31.46 |
| 2683 | CD | GLU | A | 335 | -89.628 | -14.410 | 87.302 | 1.00 | 33.59 |
| 2684 | OE1 | GLU | A | 335 | -88.509 | -14.579 | 86.758 | 1.00 | 32.65 |
| 2685 | OE2 | GLU | A | 335 | -90.546 | -13.745 | 86.754 | 1.00 | 33.53 |
| 2686 | C | GLU | A | 335 | -90.539 | -17.858 | 88.180 | 1.00 | 32.42 |
| 2687 | O | GLU | A | 335 | -91.144 | -17.504 | 87.181 | 1.00 | 31.80 |
| 2688 | N | PRO | A | 336 | -91.096 | -18.645 | 89.090 | 1.00 | 32.87 |
| 2689 | CA | PRO | A | 336 | -92.519 | -18.982 | 89.014 | 1.00 | 33.39 |
| 2690 | CB | PRO | A | 336 | -92.611 | -20.258 | 89.846 | 1.00 | 33.25 |
| 2691 | CG | PRO | A | 336 | -91.500 | -20.140 | 90.835 | 1.00 | 32.41 |
| 2692 | CD | PRO | A | 336 | -90.419 | -19.330 | 90.208 | 1.00 | 32.30 |
| 2693 | C | PRO | A | 336 | -93.408 | -17.899 | 89.642 | 1.00 | 33.76 |

FIGURE 3 BA

| A | B | C | D | E | F | G | H | I | J |
|---|---|---|---|---|---|---|---|---|---|
| 2694 | O | PRO | A | 336 | -92.997 | -17.222 | 90.593 | 1.00 | 33.37 |
| 2695 | N | HIS | A | 337 | -94.602 | -17.732 | 89.081 | 1.00 | 33.63 |
| 2696 | CA | HIS | A | 337 | -95.606 | -16.851 | 89.648 | 1.00 | 33.97 |
| 2697 | CB | HIS | A | 337 | -96.009 | -15.782 | 88.647 | 1.00 | 34.05 |
| 2698 | CG | HIS | A | 337 | -94.912 | -14.796 | 88.367 | 1.00 | 33.96 |
| 2699 | ND1 | HIS | A | 337 | -93.779 | -15.127 | 87.652 | 1.00 | 32.59 |
| 2700 | CE1 | HIS | A | 337 | -92.981 | -14.079 | 87.591 | 1.00 | 31.42 |
| 2701 | NE2 | HIS | A | 337 | -93.554 | -13.083 | 88.240 | 1.00 | 32.74 |
| 2702 | CD2 | HIS | A | 337 | -94.757 | -13.506 | 88.744 | 1.00 | 31.64 |
| 2703 | C | HIS | A | 337 | -96.785 | -17.726 | 90.075 | 1.00 | 34.33 |
| 2704 | O | HIS | A | 337 | -97.471 | -18.315 | 89.247 | 1.00 | 34.33 |
| 2705 | N | PHE | A | 338 | -96.977 | -17.802 | 91.388 | 1.00 | 34.78 |
| 2706 | CA | PHE | A | 338 | -97.942 | -18.660 | 92.053 | 1.00 | 34.88 |
| 2707 | CB | PHE | A | 338 | -97.402 | -18.999 | 93.443 | 1.00 | 34.38 |
| 2708 | CG | PHE | A | 338 | -96.348 | -20.069 | 93.448 | 1.00 | 33.53 |
| 2709 | CD1 | PHE | A | 338 | -95.016 | -19.742 | 93.607 | 1.00 | 30.96 |
| 2710 | CE1 | PHE | A | 338 | -94.060 | -20.719 | 93.622 | 1.00 | 30.30 |
| 2711 | CZ | PHE | A | 338 | -94.425 | -22.036 | 93.485 | 1.00 | 31.10 |
| 2712 | CE2 | PHE | A | 338 | -95.749 | -22.374 | 93.356 | 1.00 | 30.16 |
| 2713 | CD2 | PHE | A | 338 | -96.697 | -21.404 | 93.330 | 1.00 | 30.81 |
| 2714 | C | PHE | A | 338 | -99.318 | -18.062 | 92.269 | 1.00 | 35.84 |
| 2715 | O | PHE | A | 338 | -99.451 | -16.885 | 92.610 | 1.00 | 36.00 |
| 2716 | N | THR | A | 339 | -100.342 | -18.900 | 92.121 | 1.00 | 36.76 |
| 2717 | CA | THR | A | 339 | -101.703 | -18.497 | 92.436 | 1.00 | 37.70 |
| 2718 | CB | THR | A | 339 | -102.713 | -19.592 | 92.012 | 1.00 | 37.86 |
| 2719 | OG1 | THR | A | 339 | -102.243 | -20.875 | 92.445 | 1.00 | 37.50 |
| 2720 | CG2 | THR | A | 339 | -102.750 | -19.739 | 90.509 | 1.00 | 36.53 |
| 2721 | C | THR | A | 339 | -101.769 | -18.288 | 93.945 | 1.00 | 38.58 |
| 2722 | O | THR | A | 339 | -101.026 | -18.915 | 94.693 | 1.00 | 38.09 |
| 2723 | N | LEU | A | 340 | -102.654 | -17.402 | 94.386 | 1.00 | 40.19 |
| 2724 | CA | LEU | A | 340 | -102.786 | -17.077 | 95.800 | 1.00 | 41.82 |
| 2725 | CB | LEU | A | 340 | -104.125 | -16.373 | 96.066 | 1.00 | 42.49 |
| 2726 | CG | LEU | A | 340 | -104.246 | -15.436 | 97.286 | 1.00 | 44.34 |
| 2727 | CD1 | LEU | A | 340 | -104.163 | -13.956 | 96.871 | 1.00 | 46.76 |
| 2728 | CD2 | LEU | A | 340 | -103.221 | -15.745 | 98.373 | 1.00 | 44.87 |
| 2729 | C | LEU | A | 340 | -102.673 | -18.311 | 96.683 | 1.00 | 42.12 |
| 2730 | O | LEU | A | 340 | -101.925 | -18.308 | 97.652 | 1.00 | 42.46 |
| 2731 | N | ASP | A | 341 | -103.416 | -19.365 | 96.350 | 1.00 | 42.85 |
| 2732 | CA | ASP | A | 341 | -103.374 | -20.612 | 97.121 | 1.00 | 43.36 |
| 2733 | CB | ASP | A | 341 | -104.599 | -21.486 | 96.824 | 1.00 | 43.86 |
| 2734 | CG | ASP | A | 341 | -104.579 | -22.085 | 95.422 | 1.00 | 45.87 |
| 2735 | OD1 | ASP | A | 341 | -105.638 | -22.603 | 94.986 | 1.00 | 46.81 |
| 2736 | OD2 | ASP | A | 341 | -103.557 | -22.101 | 94.693 | 1.00 | 48.08 |
| 2737 | C | ASP | A | 341 | -102.087 | -21.407 | 96.885 | 1.00 | 43.25 |
| 2738 | O | ASP | A | 341 | -101.795 | -22.373 | 97.603 | 1.00 | 43.43 |
| 2739 | N | GLY | A | 342 | -101.340 | -21.015 | 95.858 | 1.00 | 42.65 |
| 2740 | CA | GLY | A | 342 | -100.061 | -21.630 | 95.561 | 1.00 | 42.59 |
| 2741 | C | GLY | A | 342 | -100.063 | -23.104 | 95.215 | 1.00 | 42.29 |
| 2742 | O | GLY | A | 342 | -99.062 | -23.789 | 95.427 | 1.00 | 42.17 |
| 2743 | N | ASN | A | 343 | -101.172 | -23.609 | 94.694 | 1.00 | 41.97 |
| 2744 | CA | ASN | A | 343 | -101.206 | -25.013 | 94.292 | 1.00 | 42.26 |

FIGURE 3 BB

| A | B | C | D | E | F | G | H | I | J |
|---|---|---|---|---|---|---|---|---|---|
| 2745 | CB | ASN | A | 343 | -102.560 | -25.638 | 94.604 | 1.00 | 42.41 |
| 2746 | CG | ASN | A | 343 | -102.826 | -25.720 | 96.077 | 1.00 | 42.16 |
| 2747 | OD1 | ASN | A | 343 | -102.034 | -26.277 | 96.829 | 1.00 | 40.86 |
| 2748 | ND2 | ASN | A | 343 | -103.942 | -25.152 | 96.504 | 1.00 | 42.66 |
| 2749 | C | ASN | A | 343 | -100.947 | -25.089 | 92.803 | 1.00 | 42.12 |
| 2750 | O | ASN | A | 343 | -100.891 | -26.164 | 92.198 | 1.00 | 42.06 |
| 2751 | N | SER | A | 344 | -100.784 | -23.912 | 92.225 | 1.00 | 41.63 |
| 2752 | CA | SER | A | 344 | -100.589 | -23.788 | 90.815 | 1.00 | 41.38 |
| 2753 | CB | SER | A | 344 | -101.937 | -23.488 | 90.185 | 1.00 | 41.06 |
| 2754 | OG | SER | A | 344 | -101.754 | -22.890 | 88.931 | 1.00 | 43.21 |
| 2755 | C | SER | A | 344 | -99.613 | -22.640 | 90.563 | 1.00 | 40.83 |
| 2756 | O | SER | A | 344 | -99.430 | -21.781 | 91.433 | 1.00 | 41.01 |
| 2757 | N | PHE | A | 345 | -98.980 | -22.626 | 89.389 | 1.00 | 39.99 |
| 2758 | CA | PHE | A | 345 | -98.089 | -21.515 | 89.041 | 1.00 | 39.11 |
| 2759 | CB | PHE | A | 345 | -96.775 | -21.574 | 89.824 | 1.00 | 38.62 |
| 2760 | CG | PHE | A | 345 | -95.877 | -22.708 | 89.430 | 1.00 | 38.69 |
| 2761 | CD1 | PHE | A | 345 | -95.012 | -22.585 | 88.362 | 1.00 | 39.64 |
| 2762 | CE1 | PHE | A | 345 | -94.174 | -23.607 | 88.011 | 1.00 | 39.61 |
| 2763 | CZ | PHE | A | 345 | -94.201 | -24.780 | 88.721 | 1.00 | 41.19 |
| 2764 | CE2 | PHE | A | 345 | -95.062 | -24.915 | 89.793 | 1.00 | 40.32 |
| 2765 | CD2 | PHE | A | 345 | -95.883 | -23.885 | 90.141 | 1.00 | 38.89 |
| 2766 | C | PHE | A | 345 | -97.811 | -21.336 | 87.545 | 1.00 | 38.58 |
| 2767 | O | PHE | A | 345 | -97.966 | -22.261 | 86.732 | 1.00 | 38.07 |
| 2768 | N | TYR | A | 346 | -97.405 | -20.119 | 87.203 | 1.00 | 37.74 |
| 2769 | CA | TYR | A | 346 | -97.022 | -19.792 | 85.845 | 1.00 | 37.17 |
| 2770 | CB | TYR | A | 346 | -97.808 | -18.584 | 85.370 | 1.00 | 37.10 |
| 2771 | CG | TYR | A | 346 | -99.309 | -18.733 | 85.534 | 1.00 | 37.95 |
| 2772 | CD1 | TYR | A | 346 | -100.101 | -19.168 | 84.484 | 1.00 | 36.89 |
| 2773 | CE1 | TYR | A | 346 | -101.466 | -19.299 | 84.627 | 1.00 | 37.37 |
| 2774 | CZ | TYR | A | 346 | -102.062 | -18.996 | 85.832 | 1.00 | 38.06 |
| 2775 | OH | TYR | A | 346 | -103.432 | -19.134 | 85.977 | 1.00 | 37.64 |
| 2776 | CE2 | TYR | A | 346 | -101.300 | -18.569 | 86.894 | 1.00 | 37.43 |
| 2777 | CD2 | TYR | A | 346 | -99.932 | -18.432 | 86.742 | 1.00 | 38.88 |
| 2778 | C | TYR | A | 346 | -95.530 | -19.489 | 85.795 | 1.00 | 36.89 |
| 2779 | O | TYR | A | 346 | -94.988 | -18.854 | 86.707 | 1.00 | 36.84 |
| 2780 | N | LYS | A | 347 | -94.852 | -20.020 | 84.779 | 1.00 | 36.40 |
| 2781 | CA | LYS | A | 347 | -93.465 | -19.644 | 84.497 | 1.00 | 35.95 |
| 2782 | CB | LYS | A | 347 | -92.414 | -20.410 | 85.313 | 1.00 | 36.20 |
| 2783 | CG | LYS | A | 347 | -92.486 | -21.884 | 85.218 | 1.00 | 37.74 |
| 2784 | CD | LYS | A | 347 | -91.106 | -22.494 | 85.091 | 1.00 | 38.65 |
| 2785 | CE | LYS | A | 347 | -90.068 | -21.885 | 85.997 | 1.00 | 39.61 |
| 2786 | NZ | LYS | A | 347 | -88.672 | -22.327 | 85.572 | 1.00 | 38.56 |
| 2787 | C | LYS | A | 347 | -93.157 | -19.717 | 83.017 | 1.00 | 35.02 |
| 2788 | O | LYS | A | 347 | -93.727 | -20.509 | 82.285 | 1.00 | 35.33 |
| 2789 | N | ILE | A | 348 | -92.265 | -18.853 | 82.582 | 1.00 | 34.11 |
| 2790 | CA | ILE | A | 348 | -91.862 | -18.819 | 81.193 | 1.00 | 33.67 |
| 2791 | CB | ILE | A | 348 | -91.230 | -17.448 | 80.894 | 1.00 | 33.81 |
| 2792 | CG1 | ILE | A | 348 | -92.251 | -16.348 | 81.224 | 1.00 | 31.92 |
| 2793 | CD1 | ILE | A | 348 | -91.740 | -14.952 | 81.028 | 1.00 | 31.88 |
| 2794 | CG2 | ILE | A | 348 | -90.719 | -17.392 | 79.449 | 1.00 | 33.28 |
| 2795 | C | ILE | A | 348 | -90.873 | -19.941 | 80.924 | 1.00 | 33.21 |

FIGURE 3 BC

| A | B | C | D | E | F | G | H | I | J |
|---|---|---|---|---|---|---|---|---|---|
| 2796 | O | ILE | A | 348 | -89.927 | -20.097 | 81.665 | 1.00 | 32.34 |
| 2797 | N | ILE | A | 349 | -91.135 | -20.753 | 79.903 | 1.00 | 33.04 |
| 2798 | CA | ILE | A | 349 | -90.210 | -21.816 | 79.501 | 1.00 | 33.61 |
| 2799 | CB | ILE | A | 349 | -90.548 | -23.176 | 80.157 | 1.00 | 33.58 |
| 2800 | CG1 | ILE | A | 349 | -91.881 | -23.716 | 79.650 | 1.00 | 34.71 |
| 2801 | CD1 | ILE | A | 349 | -92.226 | -25.061 | 80.207 | 1.00 | 35.03 |
| 2802 | CG2 | ILE | A | 349 | -90.598 | -23.043 | 81.680 | 1.00 | 35.71 |
| 2803 | C | ILE | A | 349 | -90.279 | -21.916 | 77.998 | 1.00 | 33.01 |
| 2804 | O | ILE | A | 349 | -91.234 | -21.434 | 77.401 | 1.00 | 32.93 |
| 2805 | N | SER | A | 350 | -89.267 | -22.484 | 77.364 | 1.00 | 32.79 |
| 2806 | CA | SER | A | 350 | -89.350 | -22.571 | 75.918 | 1.00 | 33.90 |
| 2807 | CB | SER | A | 350 | -87.979 | -22.676 | 75.246 | 1.00 | 33.49 |
| 2808 | OG | SER | A | 350 | -87.082 | -23.311 | 76.112 | 1.00 | 36.71 |
| 2809 | C | SER | A | 350 | -90.286 | -23.695 | 75.495 | 1.00 | 33.70 |
| 2810 | O | SER | A | 350 | -90.244 | -24.805 | 76.014 | 1.00 | 32.51 |
| 2811 | N | ASN | A | 351 | -91.143 | -23.384 | 74.546 | 1.00 | 34.29 |
| 2812 | CA | ASN | A | 351 | -92.076 | -24.373 | 74.092 | 1.00 | 35.48 |
| 2813 | CB | ASN | A | 351 | -93.260 | -23.708 | 73.405 | 1.00 | 35.01 |
| 2814 | CG | ASN | A | 351 | -92.873 | -23.061 | 72.120 | 1.00 | 34.86 |
| 2815 | OD1 | ASN | A | 351 | -91.799 | -23.339 | 71.587 | 1.00 | 33.30 |
| 2816 | ND2 | ASN | A | 351 | -93.736 | -22.187 | 71.605 | 1.00 | 32.56 |
| 2817 | C | ASN | A | 351 | -91.404 | -25.389 | 73.174 | 1.00 | 36.63 |
| 2818 | O | ASN | A | 351 | -90.170 | -25.466 | 73.081 | 1.00 | 36.74 |
| 2819 | N | GLU | A | 352 | -92.235 | -26.170 | 72.501 | 1.00 | 37.65 |
| 2820 | CA | GLU | A | 352 | -91.763 | -27.210 | 71.608 | 1.00 | 38.55 |
| 2821 | CB | GLU | A | 352 | -92.931 | -28.132 | 71.208 | 1.00 | 39.06 |
| 2822 | CG | GLU | A | 352 | -93.957 | -27.515 | 70.264 | 1.00 | 41.38 |
| 2823 | CD | GLU | A | 352 | -94.840 | -26.444 | 70.910 | 1.00 | 46.16 |
| 2824 | OE1 | GLU | A | 352 | -95.497 | -25.706 | 70.138 | 1.00 | 45.81 |
| 2825 | OE2 | GLU | A | 352 | -94.890 | -26.335 | 72.175 | 1.00 | 47.75 |
| 2826 | C | GLU | A | 352 | -91.058 | -26.629 | 70.373 | 1.00 | 38.16 |
| 2827 | O | GLU | A | 352 | -90.167 | -27.272 | 69.813 | 1.00 | 38.50 |
| 2828 | N | GLU | A | 353 | -91.453 | -25.425 | 69.958 | 1.00 | 37.12 |
| 2829 | CA | GLU | A | 353 | -90.826 | -24.766 | 68.818 | 1.00 | 36.69 |
| 2830 | CB | GLU | A | 353 | -91.739 | -23.695 | 68.189 | 1.00 | 37.21 |
| 2831 | CG | GLU | A | 353 | -93.211 | -23.990 | 67.932 | 1.00 | 40.63 |
| 2832 | CD | GLU | A | 353 | -93.980 | -22.710 | 67.572 | 1.00 | 44.93 |
| 2833 | OE1 | GLU | A | 353 | -94.581 | -22.664 | 66.481 | 1.00 | 46.68 |
| 2834 | OE2 | GLU | A | 353 | -93.976 | -21.730 | 68.374 | 1.00 | 46.88 |
| 2835 | C | GLU | A | 353 | -89.572 | -24.010 | 69.262 | 1.00 | 35.39 |
| 2836 | O | GLU | A | 353 | -88.890 | -23.403 | 68.442 | 1.00 | 35.44 |
| 2837 | N | GLY | A | 354 | -89.302 | -23.989 | 70.559 | 1.00 | 33.96 |
| 2838 | CA | GLY | A | 354 | -88.195 | -23.201 | 71.071 | 1.00 | 32.44 |
| 2839 | C | GLY | A | 354 | -88.505 | -21.733 | 71.367 | 1.00 | 31.46 |
| 2840 | O | GLY | A | 354 | -87.591 | -20.940 | 71.593 | 1.00 | 30.85 |
| 2841 | N | TYR | A | 355 | -89.778 | -21.345 | 71.339 | 1.00 | 30.91 |
| 2842 | CA | TYR | A | 355 | -90.122 | -19.981 | 71.726 | 1.00 | 30.80 |
| 2843 | CB | TYR | A | 355 | -91.209 | -19.401 | 70.829 | 1.00 | 30.63 |
| 2844 | CG | TYR | A | 355 | -90.695 | -19.107 | 69.445 | 1.00 | 32.02 |
| 2845 | CD1 | TYR | A | 355 | -90.762 | -20.063 | 68.434 | 1.00 | 32.17 |
| 2846 | CE1 | TYR | A | 355 | -90.278 | -19.799 | 67.179 | 1.00 | 31.62 |

FIGURE 3 BD

| A | B | C | D | E | F | G | H | I | J |
|---|---|---|---|---|---|---|---|---|---|
| 2847 | CZ | TYR | A | 355 | -89.707 | -18.571 | 66.920 | 1.00 | 31.90 |
| 2848 | OH | TYR | A | 355 | -89.213 | -18.276 | 65.670 | 1.00 | 33.67 |
| 2849 | CE2 | TYR | A | 355 | -89.625 | -17.622 | 67.900 | 1.00 | 32.64 |
| 2850 | CD2 | TYR | A | 355 | -90.111 | -17.893 | 69.154 | 1.00 | 32.64 |
| 2851 | C | TYR | A | 355 | -90.508 | -19.943 | 73.206 | 1.00 | 30.34 |
| 2852 | O | TYR | A | 355 | -91.203 | -20.837 | 73.693 | 1.00 | 30.13 |
| 2853 | N | ARG | A | 356 | -90.030 | -18.934 | 73.927 | 1.00 | 29.55 |
| 2854 | CA | ARG | A | 356 | -90.288 | -18.856 | 75.370 | 1.00 | 29.53 |
| 2855 | CB | ARG | A | 356 | -89.219 | -18.017 | 76.081 | 1.00 | 29.51 |
| 2856 | CG | ARG | A | 356 | -88.022 | -18.853 | 76.506 | 1.00 | 29.63 |
| 2857 | CD | ARG | A | 356 | -86.716 | -18.084 | 76.730 | 1.00 | 26.56 |
| 2858 | NE | ARG | A | 356 | -85.607 | -18.871 | 76.218 | 1.00 | 26.34 |
| 2859 | CZ | ARG | A | 356 | -85.111 | -19.949 | 76.817 | 1.00 | 26.06 |
| 2860 | NH1 | ARG | A | 356 | -85.589 | -20.367 | 77.982 | 1.00 | 24.33 |
| 2861 | NH2 | ARG | A | 356 | -84.128 | -20.614 | 76.244 | 1.00 | 25.83 |
| 2862 | C | ARG | A | 356 | -91.684 | -18.332 | 75.665 | 1.00 | 29.24 |
| 2863 | O | ARG | A | 356 | -92.032 | -17.226 | 75.267 | 1.00 | 29.37 |
| 2864 | N | HIS | A | 357 | -92.476 | -19.131 | 76.370 | 1.00 | 29.34 |
| 2865 | CA | HIS | A | 357 | -93.877 | -18.794 | 76.610 | 1.00 | 29.87 |
| 2866 | CB | HIS | A | 357 | -94.789 | -19.475 | 75.578 | 1.00 | 29.04 |
| 2867 | CG | HIS | A | 357 | -94.868 | -18.755 | 74.271 | 1.00 | 27.31 |
| 2868 | ND1 | HIS | A | 357 | -95.532 | -17.554 | 74.122 | 1.00 | 26.59 |
| 2869 | CE1 | HIS | A | 357 | -95.428 | -17.148 | 72.868 | 1.00 | 25.30 |
| 2870 | NE2 | HIS | A | 357 | -94.725 | -18.044 | 72.198 | 1.00 | 26.82 |
| 2871 | CD2 | HIS | A | 357 | -94.363 | -19.059 | 73.053 | 1.00 | 25.52 |
| 2872 | C | HIS | A | 357 | -94.303 | -19.205 | 77.996 | 1.00 | 31.03 |
| 2873 | O | HIS | A | 357 | -93.626 | -19.987 | 78.650 | 1.00 | 31.02 |
| 2874 | N | ILE | A | 358 | -95.450 | -18.684 | 78.432 | 1.00 | 32.92 |
| 2875 | CA | ILE | A | 358 | -95.956 | -18.941 | 79.778 | 1.00 | 33.30 |
| 2876 | CB | ILE | A | 358 | -96.939 | -17.868 | 80.182 | 1.00 | 32.95 |
| 2877 | CG1 | ILE | A | 358 | -96.295 | -16.492 | 80.092 | 1.00 | 32.51 |
| 2878 | CD1 | ILE | A | 358 | -97.298 | -15.334 | 80.019 | 1.00 | 31.79 |
| 2879 | CG2 | ILE | A | 358 | -97.423 | -18.132 | 81.607 | 1.00 | 33.53 |
| 2880 | C | ILE | A | 358 | -96.639 | -20.289 | 79.859 | 1.00 | 34.76 |
| 2881 | O | ILE | A | 358 | -97.518 | -20.607 | 79.068 | 1.00 | 34.56 |
| 2882 | N | CYS | A | 359 | -96.238 | -21.082 | 80.834 | 1.00 | 36.20 |
| 2883 | CA | CYS | A | 359 | -96.809 | -22.394 | 80.995 | 1.00 | 37.68 |
| 2884 | CB | CYS | A | 359 | -95.733 | -23.467 | 80.813 | 1.00 | 38.06 |
| 2885 | SG | CYS | A | 359 | -96.311 | -24.979 | 80.022 | 1.00 | 41.36 |
| 2886 | C | CYS | A | 359 | -97.420 | -22.443 | 82.389 | 1.00 | 38.10 |
| 2887 | O | CYS | A | 359 | -96.846 | -21.926 | 83.348 | 1.00 | 37.64 |
| 2888 | N | TYR | A | 360 | -98.600 | -23.044 | 82.465 | 1.00 | 38.74 |
| 2889 | CA | TYR | A | 360 | -99.376 | -23.151 | 83.677 | 1.00 | 39.80 |
| 2890 | CB | TYR | A | 360 | -100.848 | -23.059 | 83.298 | 1.00 | 40.29 |
| 2891 | CG | TYR | A | 360 | -101.824 | -23.098 | 84.444 | 1.00 | 41.20 |
| 2892 | CD1 | TYR | A | 360 | -103.034 | -23.758 | 84.315 | 1.00 | 40.57 |
| 2893 | CE1 | TYR | A | 360 | -103.933 | -23.804 | 85.353 | 1.00 | 42.25 |
| 2894 | CZ | TYR | A | 360 | -103.633 | -23.175 | 86.544 | 1.00 | 43.37 |
| 2895 | OH | TYR | A | 360 | -104.532 | -23.229 | 87.588 | 1.00 | 43.69 |
| 2896 | CE2 | TYR | A | 360 | -102.435 | -22.509 | 86.696 | 1.00 | 42.16 |
| 2897 | CD2 | TYR | A | 360 | -101.542 | -22.472 | 85.651 | 1.00 | 42.27 |

FIGURE 3 BE

| A | B | C | D | E | F | G | H | I | J |
|---|---|---|---|---|---|---|---|---|---|
| 2898 | C | TYR | A | 360 | -99.078 | -24.481 | 84.332 | 1.00 | 40.54 |
| 2899 | O | TYR | A | 360 | -99.267 | -25.529 | 83.738 | 1.00 | 41.09 |
| 2900 | N | PHE | A | 361 | -98.572 | -24.449 | 85.551 | 1.00 | 41.60 |
| 2901 | CA | PHE | A | 361 | -98.272 | -25.687 | 86.247 | 1.00 | 42.72 |
| 2902 | CB | PHE | A | 361 | -96.852 | -25.645 | 86.836 | 1.00 | 42.51 |
| 2903 | CG | PHE | A | 361 | -95.756 | -25.536 | 85.808 | 1.00 | 41.05 |
| 2904 | CD1 | PHE | A | 361 | -94.860 | -26.568 | 85.625 | 1.00 | 41.28 |
| 2905 | CE1 | PHE | A | 361 | -93.838 | -26.467 | 84.693 | 1.00 | 41.21 |
| 2906 | CZ | PHE | A | 361 | -93.715 | -25.322 | 83.937 | 1.00 | 40.10 |
| 2907 | CE2 | PHE | A | 361 | -94.603 | -24.290 | 84.116 | 1.00 | 38.79 |
| 2908 | CD2 | PHE | A | 361 | -95.612 | -24.397 | 85.046 | 1.00 | 39.46 |
| 2909 | C | PHE | A | 361 | -99.262 | -25.913 | 87.381 | 1.00 | 43.89 |
| 2910 | O | PHE | A | 361 | -99.809 | -24.964 | 87.931 | 1.00 | 43.81 |
| 2911 | N | GLN | A | 362 | -99.510 | -27.175 | 87.711 | 1.00 | 45.58 |
| 2912 | CA | GLN | A | 362 | -100.272 | -27.499 | 88.912 | 1.00 | 47.47 |
| 2913 | CB | GLN | A | 362 | -101.451 | -28.440 | 88.616 | 1.00 | 48.12 |
| 2914 | CG | GLN | A | 362 | -102.775 | -28.051 | 89.306 | 1.00 | 49.81 |
| 2915 | CD | GLN | A | 362 | -103.062 | -28.830 | 90.613 | 1.00 | 53.36 |
| 2916 | OE1 | GLN | A | 362 | -102.728 | -28.369 | 91.715 | 1.00 | 52.94 |
| 2917 | NE2 | GLN | A | 362 | -103.704 | -29.998 | 90.483 | 1.00 | 53.59 |
| 2918 | C | GLN | A | 362 | -99.247 | -28.158 | 89.821 | 1.00 | 48.25 |
| 2919 | O | GLN | A | 362 | -98.430 | -28.974 | 89.376 | 1.00 | 48.02 |
| 2920 | N | ILE | A | 363 | -99.252 | -27.778 | 91.087 | 1.00 | 49.55 |
| 2921 | CA | ILE | A | 363 | -98.246 | -28.286 | 92.008 | 1.00 | 51.02 |
| 2922 | CB | ILE | A | 363 | -98.629 | -27.965 | 93.479 | 1.00 | 51.02 |
| 2923 | CG1 | ILE | A | 363 | -98.133 | -26.571 | 93.851 | 1.00 | 51.54 |
| 2924 | CD1 | ILE | A | 363 | -96.885 | -26.159 | 93.127 | 1.00 | 51.02 |
| 2925 | CG2 | ILE | A | 363 | -98.007 | -28.949 | 94.436 | 1.00 | 50.93 |
| 2926 | C | ILE | A | 363 | -98.004 | -29.771 | 91.825 | 1.00 | 52.01 |
| 2927 | O | ILE | A | 363 | -96.858 | -30.214 | 91.808 | 1.00 | 52.17 |
| 2928 | N | ASP | A | 364 | -99.084 | -30.527 | 91.633 | 1.00 | 53.58 |
| 2929 | CA | ASP | A | 364 | -99.014 | -31.992 | 91.612 | 1.00 | 54.84 |
| 2930 | CB | ASP | A | 364 | -100.112 | -32.558 | 92.521 | 1.00 | 55.24 |
| 2931 | CG | ASP | A | 364 | -99.788 | -32.388 | 93.981 | 1.00 | 56.58 |
| 2932 | OD1 | ASP | A | 364 | -98.635 | -32.680 | 94.350 | 1.00 | 59.18 |
| 2933 | OD2 | ASP | A | 364 | -100.600 | -31.958 | 94.831 | 1.00 | 58.32 |
| 2934 | C | ASP | A | 364 | -99.037 | -32.757 | 90.276 | 1.00 | 55.38 |
| 2935 | O | ASP | A | 364 | -99.183 | -33.983 | 90.298 | 1.00 | 55.51 |
| 2936 | N | LYS | A | 365 | -98.917 | -32.080 | 89.131 | 1.00 | 55.78 |
| 2937 | CA | LYS | A | 365 | -98.863 | -32.809 | 87.855 | 1.00 | 56.42 |
| 2938 | CB | LYS | A | 365 | -100.170 | -32.712 | 87.048 | 1.00 | 56.40 |
| 2939 | CG | LYS | A | 365 | -100.577 | -31.309 | 86.667 | 1.00 | 57.92 |
| 2940 | CD | LYS | A | 365 | -101.169 | -31.221 | 85.252 | 1.00 | 60.34 |
| 2941 | CE | LYS | A | 365 | -102.600 | -31.746 | 85.151 | 1.00 | 61.89 |
| 2942 | NZ | LYS | A | 365 | -102.681 | -33.100 | 84.496 | 1.00 | 62.69 |
| 2943 | C | LYS | A | 365 | -97.652 | -32.444 | 86.992 | 1.00 | 56.62 |
| 2944 | O | LYS | A | 365 | -97.321 | -31.265 | 86.818 | 1.00 | 57.24 |
| 2945 | N | LYS | A | 366 | -97.006 | -33.465 | 86.437 | 1.00 | 56.42 |
| 2946 | CA | LYS | A | 366 | -95.798 | -33.277 | 85.641 | 1.00 | 55.99 |
| 2947 | CB | LYS | A | 366 | -95.240 | -34.629 | 85.170 | 1.00 | 56.58 |
| 2948 | CG | LYS | A | 366 | -94.036 | -34.533 | 84.209 | 1.00 | 57.83 |

FIGURE 3 BF

| A | B | C | D | E | F | G | H | I | J |
|---|---|---|---|---|---|---|---|---|---|
| 2949 | CD | LYS | A | 366 | -92.819 | -33.841 | 84.852 | 1.00 | 59.89 |
| 2950 | CE | LYS | A | 366 | -92.654 | -32.382 | 84.393 | 1.00 | 60.92 |
| 2951 | NZ | LYS | A | 366 | -91.681 | -31.585 | 85.205 | 1.00 | 60.11 |
| 2952 | C | LYS | A | 366 | -95.952 | -32.344 | 84.447 | 1.00 | 55.08 |
| 2953 | O | LYS | A | 366 | -95.009 | -31.666 | 84.068 | 1.00 | 55.04 |
| 2954 | N | ASP | A | 367 | -97.128 | -32.281 | 83.848 | 1.00 | 54.12 |
| 2955 | CA | ASP | A | 367 | -97.211 | -31.500 | 82.619 | 1.00 | 52.94 |
| 2956 | CB | ASP | A | 367 | -97.631 | -32.379 | 81.445 | 1.00 | 53.37 |
| 2957 | CG | ASP | A | 367 | -96.519 | -33.310 | 81.006 | 1.00 | 54.80 |
| 2958 | OD1 | ASP | A | 367 | -96.712 | -34.545 | 81.071 | 1.00 | 55.44 |
| 2959 | OD2 | ASP | A | 367 | -95.408 | -32.888 | 80.595 | 1.00 | 57.04 |
| 2960 | C | ASP | A | 367 | -98.010 | -30.203 | 82.673 | 1.00 | 51.72 |
| 2961 | O | ASP | A | 367 | -99.181 | -30.177 | 83.053 | 1.00 | 51.87 |
| 2962 | N | CYS | A | 368 | -97.349 | -29.129 | 82.263 | 1.00 | 49.45 |
| 2963 | CA | CYS | A | 368 | -97.957 | -27.827 | 82.275 | 1.00 | 47.42 |
| 2964 | CB | CYS | A | 368 | -96.888 | -26.771 | 82.554 | 1.00 | 47.41 |
| 2965 | SG | CYS | A | 368 | -95.730 | -26.542 | 81.198 | 1.00 | 46.58 |
| 2966 | C | CYS | A | 368 | -98.619 | -27.556 | 80.938 | 1.00 | 46.20 |
| 2967 | O | CYS | A | 368 | -98.368 | -28.249 | 79.948 | 1.00 | 45.93 |
| 2968 | N | THR | A | 369 | -99.490 | -26.559 | 80.907 | 1.00 | 44.12 |
| 2969 | CA | THR | A | 369 | -100.088 | -26.180 | 79.642 | 1.00 | 42.61 |
| 2970 | CB | THR | A | 369 | -101.619 | -26.518 | 79.577 | 1.00 | 42.64 |
| 2971 | OG1 | THR | A | 369 | -102.392 | -25.353 | 79.264 | 1.00 | 42.69 |
| 2972 | CG2 | THR | A | 369 | -102.149 | -26.942 | 80.929 | 1.00 | 43.54 |
| 2973 | C | THR | A | 369 | -99.712 | -24.733 | 79.317 | 1.00 | 41.02 |
| 2974 | O | THR | A | 369 | -99.563 | -23.908 | 80.203 | 1.00 | 40.88 |
| 2975 | N | PHE | A | 370 | -99.482 | -24.462 | 78.045 | 1.00 | 39.16 |
| 2976 | CA | PHE | A | 370 | -99.060 | -23.150 | 77.607 | 1.00 | 37.31 |
| 2977 | CB | PHE | A | 370 | -98.248 | -23.272 | 76.310 | 1.00 | 37.15 |
| 2978 | CG | PHE | A | 370 | -96.838 | -23.766 | 76.511 | 1.00 | 34.73 |
| 2979 | CD1 | PHE | A | 370 | -95.844 | -22.905 | 76.967 | 1.00 | 33.48 |
| 2980 | CE1 | PHE | A | 370 | -94.530 | -23.352 | 77.158 | 1.00 | 33.31 |
| 2981 | CZ | PHE | A | 370 | -94.208 | -24.678 | 76.875 | 1.00 | 32.49 |
| 2982 | CE2 | PHE | A | 370 | -95.201 | -25.543 | 76.416 | 1.00 | 32.47 |
| 2983 | CD2 | PHE | A | 370 | -96.505 | -25.079 | 76.233 | 1.00 | 33.08 |
| 2984 | C | PHE | A | 370 | -100.268 | -22.270 | 77.372 | 1.00 | 37.01 |
| 2985 | O | PHE | A | 370 | -101.214 | -22.663 | 76.673 | 1.00 | 36.86 |
| 2986 | N | ILE | A | 371 | -100.246 | -21.068 | 77.938 | 1.00 | 36.08 |
| 2987 | CA | ILE | A | 371 | -101.362 | -20.156 | 77.733 | 1.00 | 35.33 |
| 2988 | CB | ILE | A | 371 | -101.798 | -19.484 | 79.045 | 1.00 | 35.35 |
| 2989 | CG1 | ILE | A | 371 | -100.774 | -18.452 | 79.500 | 1.00 | 35.72 |
| 2990 | CD1 | ILE | A | 371 | -101.094 | -17.846 | 80.831 | 1.00 | 33.45 |
| 2991 | CG2 | ILE | A | 371 | -101.933 | -20.517 | 80.118 | 1.00 | 36.12 |
| 2992 | C | ILE | A | 371 | -101.061 | -19.154 | 76.637 | 1.00 | 34.47 |
| 2993 | O | ILE | A | 371 | -101.967 | -18.464 | 76.156 | 1.00 | 34.72 |
| 2994 | N | THR | A | 372 | -99.796 | -19.073 | 76.238 | 1.00 | 33.71 |
| 2995 | CA | THR | A | 372 | -99.413 | -18.250 | 75.081 | 1.00 | 33.23 |
| 2996 | CB | THR | A | 372 | -98.559 | -17.026 | 75.457 | 1.00 | 33.14 |
| 2997 | OG1 | THR | A | 372 | -97.327 | -17.458 | 76.046 | 1.00 | 31.70 |
| 2998 | CG2 | THR | A | 372 | -99.232 | -16.189 | 76.529 | 1.00 | 33.50 |
| 2999 | C | THR | A | 372 | -98.647 | -19.107 | 74.084 | 1.00 | 33.04 |

FIGURE 3 BG

| A | B | C | D | E | F | G | H | I | J |
|---|---|---|---|---|---|---|---|---|---|
| 3000 | O | THR | A | 372 | -98.098 | -20.149 | 74.442 | 1.00 | 32.62 |
| 3001 | N | LYS | A | 373 | -98.605 | -18.642 | 72.842 | 1.00 | 33.13 |
| 3002 | CA | LYS | A | 373 | -97.946 | -19.348 | 71.751 | 1.00 | 33.71 |
| 3003 | CB | LYS | A | 373 | -98.864 | -20.463 | 71.236 | 1.00 | 34.69 |
| 3004 | CG | LYS | A | 373 | -98.515 | -21.832 | 71.757 | 1.00 | 37.34 |
| 3005 | CD | LYS | A | 373 | -97.573 | -22.584 | 70.808 | 1.00 | 40.07 |
| 3006 | CE | LYS | A | 373 | -97.611 | -24.076 | 71.129 | 1.00 | 41.29 |
| 3007 | NZ | LYS | A | 373 | -97.392 | -24.331 | 72.596 | 1.00 | 39.51 |
| 3008 | C | LYS | A | 373 | -97.695 | -18.387 | 70.611 | 1.00 | 32.96 |
| 3009 | O | LYS | A | 373 | -98.313 | -17.327 | 70.532 | 1.00 | 33.22 |
| 3010 | N | GLY | A | 374 | -96.811 | -18.761 | 69.705 | 1.00 | 32.47 |
| 3011 | CA | GLY | A | 374 | -96.525 | -17.923 | 68.550 | 1.00 | 31.99 |
| 3012 | C | GLY | A | 374 | -95.031 | -17.795 | 68.293 | 1.00 | 31.37 |
| 3013 | O | GLY | A | 374 | -94.226 | -18.208 | 69.110 | 1.00 | 31.20 |
| 3014 | N | THR | A | 375 | -94.658 | -17.233 | 67.154 | 1.00 | 30.90 |
| 3015 | CA | THR | A | 375 | -93.246 | -17.004 | 66.875 | 1.00 | 30.93 |
| 3016 | CB | THR | A | 375 | -92.924 | -17.143 | 65.362 | 1.00 | 30.63 |
| 3017 | OG1 | THR | A | 375 | -93.906 | -16.440 | 64.590 | 1.00 | 31.31 |
| 3018 | CG2 | THR | A | 375 | -93.075 | -18.619 | 64.906 | 1.00 | 30.29 |
| 3019 | C | THR | A | 375 | -92.865 | -15.625 | 67.393 | 1.00 | 30.34 |
| 3020 | O | THR | A | 375 | -92.659 | -14.707 | 66.623 | 1.00 | 30.61 |
| 3021 | N | TRP | A | 376 | -92.856 | -15.498 | 68.715 | 1.00 | 29.89 |
| 3022 | CA | TRP | A | 376 | -92.439 | -14.299 | 69.434 | 1.00 | 29.59 |
| 3023 | CB | TRP | A | 376 | -93.478 | -13.173 | 69.372 | 1.00 | 29.71 |
| 3024 | CG | TRP | A | 376 | -94.880 | -13.619 | 69.599 | 1.00 | 30.29 |
| 3025 | CD1 | TRP | A | 376 | -95.776 | -14.017 | 68.647 | 1.00 | 29.32 |
| 3026 | NE1 | TRP | A | 376 | -96.965 | -14.362 | 69.241 | 1.00 | 28.96 |
| 3027 | CE2 | TRP | A | 376 | -96.862 | -14.203 | 70.594 | 1.00 | 27.80 |
| 3028 | CD2 | TRP | A | 376 | -95.561 | -13.728 | 70.860 | 1.00 | 29.24 |
| 3029 | CE3 | TRP | A | 376 | -95.201 | -13.473 | 72.190 | 1.00 | 28.12 |
| 3030 | CZ3 | TRP | A | 376 | -96.126 | -13.695 | 73.186 | 1.00 | 27.35 |
| 3031 | CH2 | TRP | A | 376 | -97.421 | -14.160 | 72.884 | 1.00 | 28.74 |
| 3032 | CZ2 | TRP | A | 376 | -97.804 | -14.412 | 71.595 | 1.00 | 29.31 |
| 3033 | C | TRP | A | 376 | -92.210 | -14.786 | 70.859 | 1.00 | 29.40 |
| 3034 | O | TRP | A | 376 | -92.395 | -15.971 | 71.140 | 1.00 | 28.98 |
| 3035 | N | GLU | A | 377 | -91.770 | -13.912 | 71.755 | 1.00 | 29.21 |
| 3036 | CA | GLU | A | 377 | -91.496 | -14.386 | 73.113 | 1.00 | 29.11 |
| 3037 | CB | GLU | A | 377 | -89.988 | -14.611 | 73.336 | 1.00 | 28.79 |
| 3038 | CG | GLU | A | 377 | -89.448 | -15.849 | 72.627 | 1.00 | 28.35 |
| 3039 | CD | GLU | A | 377 | -88.088 | -16.324 | 73.120 | 1.00 | 29.91 |
| 3040 | OE1 | GLU | A | 377 | -87.752 | -17.495 | 72.827 | 1.00 | 29.47 |
| 3041 | OE2 | GLU | A | 377 | -87.343 | -15.542 | 73.778 | 1.00 | 28.67 |
| 3042 | C | GLU | A | 377 | -92.099 | -13.561 | 74.240 | 1.00 | 28.79 |
| 3043 | O | GLU | A | 377 | -92.302 | -12.354 | 74.116 | 1.00 | 29.25 |
| 3044 | N | VAL | A | 378 | -92.412 | -14.237 | 75.332 | 1.00 | 28.38 |
| 3045 | CA | VAL | A | 378 | -92.837 | -13.569 | 76.541 | 1.00 | 27.65 |
| 3046 | CB | VAL | A | 378 | -93.646 | -14.519 | 77.439 | 1.00 | 27.88 |
| 3047 | CG1 | VAL | A | 378 | -93.804 | -13.925 | 78.830 | 1.00 | 26.50 |
| 3048 | CG2 | VAL | A | 378 | -95.027 | -14.836 | 76.800 | 1.00 | 26.31 |
| 3049 | C | VAL | A | 378 | -91.562 | -13.147 | 77.275 | 1.00 | 27.70 |
| 3050 | O | VAL | A | 378 | -90.718 | -13.976 | 77.593 | 1.00 | 27.32 |

FIGURE 3 BH

| A | B | C | D | E | F | G | H | I | J |
|---|---|---|---|---|---|---|---|---|---|
| 3051 | N | ILE | A | 379 | -91.406 | -11.854 | 77.523 | 1.00 | 27.85 |
| 3052 | CA | ILE | A | 379 | -90.224 | -11.362 | 78.202 | 1.00 | 27.66 |
| 3053 | CB | ILE | A | 379 | -90.085 | -9.875 | 77.966 | 1.00 | 27.68 |
| 3054 | CG1 | ILE | A | 379 | -90.094 | -9.569 | 76.475 | 1.00 | 27.06 |
| 3055 | CD1 | ILE | A | 379 | -88.982 | -10.254 | 75.698 | 1.00 | 27.23 |
| 3056 | CG2 | ILE | A | 379 | -88.821 | -9.343 | 78.633 | 1.00 | 27.37 |
| 3057 | C | ILE | A | 379 | -90.352 | -11.628 | 79.691 | 1.00 | 28.64 |
| 3058 | O | ILE | A | 379 | -89.436 | -12.159 | 80.328 | 1.00 | 28.55 |
| 3059 | N | GLY | A | 380 | -91.491 | -11.252 | 80.259 | 1.00 | 29.04 |
| 3060 | CA | GLY | A | 380 | -91.688 | -11.466 | 81.676 | 1.00 | 30.14 |
| 3061 | C | GLY | A | 380 | -93.133 | -11.491 | 82.135 | 1.00 | 31.28 |
| 3062 | O | GLY | A | 380 | -94.006 | -10.891 | 81.518 | 1.00 | 31.31 |
| 3063 | N | ILE | A | 381 | -93.390 | -12.246 | 83.199 | 1.00 | 32.45 |
| 3064 | CA | ILE | A | 381 | -94.683 | -12.201 | 83.851 | 1.00 | 33.24 |
| 3065 | CB | ILE | A | 381 | -94.985 | -13.501 | 84.587 | 1.00 | 33.27 |
| 3066 | CG1 | ILE | A | 381 | -95.241 | -14.628 | 83.585 | 1.00 | 33.10 |
| 3067 | CD1 | ILE | A | 381 | -95.018 | -16.022 | 84.135 | 1.00 | 31.40 |
| 3068 | CG2 | ILE | A | 381 | -96.196 | -13.313 | 85.485 | 1.00 | 32.88 |
| 3069 | C | ILE | A | 381 | -94.551 | -11.063 | 84.847 | 1.00 | 33.97 |
| 3070 | O | ILE | A | 381 | -93.729 | -11.109 | 85.766 | 1.00 | 33.63 |
| 3071 | N | GLU | A | 382 | -95.374 | -10.046 | 84.658 | 1.00 | 34.75 |
| 3072 | CA | GLU | A | 382 | -95.340 | -8.857 | 85.480 | 1.00 | 35.69 |
| 3073 | CB | GLU | A | 382 | -95.641 | -7.656 | 84.590 | 1.00 | 35.50 |
| 3074 | CG | GLU | A | 382 | -94.684 | -7.593 | 83.411 | 1.00 | 35.79 |
| 3075 | CD | GLU | A | 382 | -93.226 | -7.560 | 83.859 | 1.00 | 37.37 |
| 3076 | OE1 | GLU | A | 382 | -92.872 | -6.704 | 84.701 | 1.00 | 36.22 |
| 3077 | OE2 | GLU | A | 382 | -92.431 | -8.411 | 83.392 | 1.00 | 38.76 |
| 3078 | C | GLU | A | 382 | -96.282 | -8.924 | 86.694 | 1.00 | 36.12 |
| 3079 | O | GLU | A | 382 | -96.006 | -8.354 | 87.758 | 1.00 | 35.75 |
| 3080 | N | ALA | A | 383 | -97.392 | -9.631 | 86.550 | 1.00 | 36.81 |
| 3081 | CA | ALA | A | 383 | -98.295 | -9.773 | 87.689 | 1.00 | 36.98 |
| 3082 | CB | ALA | A | 383 | -98.881 | -8.420 | 88.082 | 1.00 | 36.65 |
| 3083 | C | ALA | A | 383 | -99.405 | -10.749 | 87.404 | 1.00 | 37.31 |
| 3084 | O | ALA | A | 383 | -99.725 | -11.042 | 86.253 | 1.00 | 37.00 |
| 3085 | N | LEU | A | 384 | -99.989 | -11.267 | 88.469 | 1.00 | 38.15 |
| 3086 | CA | LEU | A | 384 | -101.144 | -12.118 | 88.310 | 1.00 | 39.28 |
| 3087 | CB | LEU | A | 384 | -100.753 | -13.589 | 88.239 | 1.00 | 39.69 |
| 3088 | CG | LEU | A | 384 | -100.874 | -14.284 | 89.581 | 1.00 | 39.71 |
| 3089 | CD1 | LEU | A | 384 | -100.766 | -15.788 | 89.460 | 1.00 | 37.20 |
| 3090 | CD2 | LEU | A | 384 | -99.805 | -13.713 | 90.476 | 1.00 | 42.83 |
| 3091 | C | LEU | A | 384 | -102.148 | -11.884 | 89.434 | 1.00 | 39.71 |
| 3092 | O | LEU | A | 384 | -101.793 | -11.740 | 90.608 | 1.00 | 39.17 |
| 3093 | N | THR | A | 385 | -103.409 | -11.817 | 89.048 | 1.00 | 40.18 |
| 3094 | CA | THR | A | 385 | -104.482 | -11.699 | 90.010 | 1.00 | 40.86 |
| 3095 | CB | THR | A | 385 | -105.344 | -10.502 | 89.674 | 1.00 | 40.38 |
| 3096 | OG1 | THR | A | 385 | -105.753 | -10.581 | 88.300 | 1.00 | 39.61 |
| 3097 | CG2 | THR | A | 385 | -104.496 | -9.244 | 89.719 | 1.00 | 39.99 |
| 3098 | C | THR | A | 385 | -105.275 | -12.995 | 89.891 | 1.00 | 41.83 |
| 3099 | O | THR | A | 385 | -104.813 | -13.945 | 89.263 | 1.00 | 41.94 |
| 3100 | N | SER | A | 386 | -106.461 | -13.041 | 90.486 | 1.00 | 42.59 |
| 3101 | CA | SER | A | 386 | -107.291 | -14.228 | 90.383 | 1.00 | 43.17 |

FIGURE 3 BI

| A | B | C | D | E | F | G | H | I | J |
|---|---|---|---|---|---|---|---|---|---|
| 3102 | CB | SER | A | 386 | -108.434 | -14.179 | 91.393 | 1.00 | 43.36 |
| 3103 | OG | SER | A | 386 | -109.495 | -13.395 | 90.883 | 1.00 | 44.75 |
| 3104 | C | SER | A | 386 | -107.885 | -14.310 | 88.985 | 1.00 | 43.23 |
| 3105 | O | SER | A | 386 | -108.147 | -15.401 | 88.492 | 1.00 | 43.30 |
| 3106 | N | ASP | A | 387 | -108.074 | -13.151 | 88.352 | 1.00 | 43.17 |
| 3107 | CA | ASP | A | 387 | -108.713 | -13.063 | 87.040 | 1.00 | 43.23 |
| 3108 | CB | ASP | A | 387 | -109.678 | -11.866 | 87.012 | 1.00 | 43.76 |
| 3109 | CG | ASP | A | 387 | -110.811 | -11.981 | 88.036 | 1.00 | 46.84 |
| 3110 | OD1 | ASP | A | 387 | -111.477 | -13.043 | 88.092 | 1.00 | 47.87 |
| 3111 | OD2 | ASP | A | 387 | -111.118 | -11.046 | 88.825 | 1.00 | 49.98 |
| 3112 | C | ASP | A | 387 | -107.768 | -12.929 | 85.834 | 1.00 | 42.74 |
| 3113 | O | ASP | A | 387 | -108.107 | -13.366 | 84.733 | 1.00 | 42.73 |
| 3114 | N | TYR | A | 388 | -106.610 | -12.294 | 86.028 | 1.00 | 42.04 |
| 3115 | CA | TYR | A | 388 | -105.704 | -11.982 | 84.922 | 1.00 | 41.04 |
| 3116 | CB | TYR | A | 388 | -105.918 | -10.546 | 84.456 | 1.00 | 41.59 |
| 3117 | CG | TYR | A | 388 | -107.268 | -10.254 | 83.845 | 1.00 | 43.68 |
| 3118 | CD1 | TYR | A | 388 | -108.245 | -9.574 | 84.566 | 1.00 | 44.79 |
| 3119 | CE1 | TYR | A | 388 | -109.486 | -9.291 | 84.002 | 1.00 | 46.09 |
| 3120 | CZ | TYR | A | 388 | -109.756 | -9.689 | 82.705 | 1.00 | 46.54 |
| 3121 | OH | TYR | A | 388 | -110.995 | -9.415 | 82.144 | 1.00 | 47.67 |
| 3122 | CE2 | TYR | A | 388 | -108.797 | -10.364 | 81.973 | 1.00 | 45.96 |
| 3123 | CD2 | TYR | A | 388 | -107.565 | -10.639 | 82.537 | 1.00 | 44.99 |
| 3124 | C | TYR | A | 388 | -104.206 | -12.142 | 85.201 | 1.00 | 40.05 |
| 3125 | O | TYR | A | 388 | -103.714 | -11.973 | 86.322 | 1.00 | 39.45 |
| 3126 | N | LEU | A | 389 | -103.492 | -12.444 | 84.128 | 1.00 | 38.96 |
| 3127 | CA | LEU | A | 389 | -102.057 | -12.602 | 84.141 | 1.00 | 37.49 |
| 3128 | CB | LEU | A | 389 | -101.694 | -13.963 | 83.556 | 1.00 | 37.55 |
| 3129 | CG | LEU | A | 389 | -100.251 | -14.396 | 83.193 | 1.00 | 37.72 |
| 3130 | CD1 | LEU | A | 389 | -99.461 | -13.286 | 82.493 | 1.00 | 35.09 |
| 3131 | CD2 | LEU | A | 389 | -99.501 | -14.931 | 84.384 | 1.00 | 34.39 |
| 3132 | C | LEU | A | 389 | -101.581 | -11.482 | 83.248 | 1.00 | 36.68 |
| 3133 | O | LEU | A | 389 | -102.035 | -11.362 | 82.100 | 1.00 | 36.51 |
| 3134 | N | TYR | A | 390 | -100.734 | -10.610 | 83.790 | 1.00 | 35.56 |
| 3135 | CA | TYR | A | 390 | -100.152 | -9.537 | 82.990 | 1.00 | 34.84 |
| 3136 | CB | TYR | A | 390 | -100.160 | -8.216 | 83.753 | 1.00 | 34.98 |
| 3137 | CG | TYR | A | 390 | -101.548 | -7.768 | 84.149 | 1.00 | 36.76 |
| 3138 | CD1 | TYR | A | 390 | -102.314 | -6.971 | 83.307 | 1.00 | 37.18 |
| 3139 | CE1 | TYR | A | 390 | -103.579 | -6.561 | 83.671 | 1.00 | 37.10 |
| 3140 | CZ | TYR | A | 390 | -104.107 | -6.960 | 84.885 | 1.00 | 37.72 |
| 3141 | OH | TYR | A | 390 | -105.374 | -6.569 | 85.265 | 1.00 | 38.83 |
| 3142 | CE2 | TYR | A | 390 | -103.376 | -7.760 | 85.729 | 1.00 | 38.02 |
| 3143 | CD2 | TYR | A | 390 | -102.099 | -8.157 | 85.359 | 1.00 | 37.31 |
| 3144 | C | TYR | A | 390 | -98.725 | -9.921 | 82.584 | 1.00 | 33.82 |
| 3145 | O | TYR | A | 390 | -97.974 | -10.467 | 83.375 | 1.00 | 32.84 |
| 3146 | N | TYR | A | 391 | -98.363 | -9.653 | 81.338 | 1.00 | 33.20 |
| 3147 | CA | TYR | A | 391 | -97.034 | -10.012 | 80.877 | 1.00 | 32.69 |
| 3148 | CB | TYR | A | 391 | -96.995 | -11.454 | 80.357 | 1.00 | 32.36 |
| 3149 | CG | TYR | A | 391 | -97.691 | -11.673 | 79.027 | 1.00 | 32.00 |
| 3150 | CD1 | TYR | A | 391 | -97.027 | -11.474 | 77.833 | 1.00 | 31.00 |
| 3151 | CE1 | TYR | A | 391 | -97.656 | -11.683 | 76.617 | 1.00 | 32.29 |
| 3152 | CZ | TYR | A | 391 | -98.972 | -12.095 | 76.588 | 1.00 | 32.79 |

FIGURE 3 BJ

| A | B | C | D | E | F | G | H | I | J |
|---|---|---|---|---|---|---|---|---|---|
| 3153 | OH  | TYR | A | 391 | -99.612 | -12.306 | 75.378 | 1.00 | 33.27 |
| 3154 | CE2 | TYR | A | 391 | -99.654 | -12.295 | 77.765 | 1.00 | 33.23 |
| 3155 | CD2 | TYR | A | 391 | -99.013 | -12.094 | 78.976 | 1.00 | 32.20 |
| 3156 | C   | TYR | A | 391 | -96.563 | -9.085  | 79.792 | 1.00 | 32.29 |
| 3157 | O   | TYR | A | 391 | -97.361 | -8.453  | 79.099 | 1.00 | 32.50 |
| 3158 | N   | ILE | A | 392 | -95.251 | -9.014  | 79.639 | 1.00 | 31.52 |
| 3159 | CA  | ILE | A | 392 | -94.684 | -8.212  | 78.578 | 1.00 | 31.31 |
| 3160 | CB  | ILE | A | 392 | -93.557 | -7.329  | 79.140 | 1.00 | 31.30 |
| 3161 | CG1 | ILE | A | 392 | -94.180 | -6.177  | 79.933 | 1.00 | 31.92 |
| 3162 | CD1 | ILE | A | 392 | -93.211 | -5.162  | 80.474 | 1.00 | 34.62 |
| 3163 | CG2 | ILE | A | 392 | -92.688 | -6.823  | 78.006 | 1.00 | 31.62 |
| 3164 | C   | ILE | A | 392 | -94.162 | -9.167  | 77.520 | 1.00 | 30.76 |
| 3165 | O   | ILE | A | 392 | -93.658 | -10.223 | 77.860 | 1.00 | 31.24 |
| 3166 | N   | SER | A | 393 | -94.294 | -8.812  | 76.247 | 1.00 | 30.16 |
| 3167 | CA  | SER | A | 393 | -93.789 | -9.659  | 75.182 | 1.00 | 29.75 |
| 3168 | CB  | SER | A | 393 | -94.861 | -10.658 | 74.764 | 1.00 | 29.92 |
| 3169 | OG  | SER | A | 393 | -95.630 | -10.120 | 73.709 | 1.00 | 29.63 |
| 3170 | C   | SER | A | 393 | -93.417 | -8.846  | 73.959 | 1.00 | 29.79 |
| 3171 | O   | SER | A | 393 | -93.829 | -7.676  | 73.826 | 1.00 | 29.67 |
| 3172 | N   | ASN | A | 394 | -92.661 | -9.456  | 73.048 | 1.00 | 29.19 |
| 3173 | CA  | ASN | A | 394 | -92.342 | -8.766  | 71.805 | 1.00 | 29.62 |
| 3174 | CB  | ASN | A | 394 | -90.876 | -8.940  | 71.409 | 1.00 | 28.91 |
| 3175 | CG  | ASN | A | 394 | -90.438 | -10.380 | 71.413 | 1.00 | 28.75 |
| 3176 | OD1 | ASN | A | 394 | -91.266 | -11.293 | 71.323 | 1.00 | 29.80 |
| 3177 | ND2 | ASN | A | 394 | -89.132 | -10.601 | 71.531 | 1.00 | 23.61 |
| 3178 | C   | ASN | A | 394 | -93.246 | -9.200  | 70.654 | 1.00 | 30.28 |
| 3179 | O   | ASN | A | 394 | -92.810 | -9.244  | 69.510 | 1.00 | 30.27 |
| 3180 | N   | GLU | A | 395 | -94.501 | -9.513  | 70.959 | 1.00 | 31.07 |
| 3181 | CA  | GLU | A | 395 | -95.413 | -10.010 | 69.929 | 1.00 | 32.27 |
| 3182 | CB  | GLU | A | 395 | -96.656 | -10.646 | 70.552 | 1.00 | 32.41 |
| 3183 | CG  | GLU | A | 395 | -97.665 | -11.121 | 69.513 | 1.00 | 33.91 |
| 3184 | CD  | GLU | A | 395 | -98.992 | -11.565 | 70.112 | 1.00 | 36.35 |
| 3185 | OE1 | GLU | A | 395 | -99.798 | -12.148 | 69.363 | 1.00 | 38.35 |
| 3186 | OE2 | GLU | A | 395 | -99.242 | -11.336 | 71.320 | 1.00 | 35.05 |
| 3187 | C   | GLU | A | 395 | -95.831 | -8.960  | 68.911 | 1.00 | 32.44 |
| 3188 | O   | GLU | A | 395 | -95.924 | -9.246  | 67.725 | 1.00 | 32.39 |
| 3189 | N   | TYR | A | 396 | -96.046 | -7.737  | 69.372 | 1.00 | 32.94 |
| 3190 | CA  | TYR | A | 396 | -96.538 | -6.696  | 68.492 | 1.00 | 34.02 |
| 3191 | CB  | TYR | A | 396 | -96.678 | -5.376  | 69.238 | 1.00 | 34.28 |
| 3192 | CG  | TYR | A | 396 | -97.530 | -4.373  | 68.514 | 1.00 | 35.62 |
| 3193 | CD1 | TYR | A | 396 | -97.009 | -3.156  | 68.129 | 1.00 | 37.19 |
| 3194 | CE1 | TYR | A | 396 | -97.781 | -2.228  | 67.475 | 1.00 | 38.08 |
| 3195 | CZ  | TYR | A | 396 | -99.097 | -2.522  | 67.206 | 1.00 | 39.93 |
| 3196 | OH  | TYR | A | 396 | -99.869 | -1.596  | 66.549 | 1.00 | 43.01 |
| 3197 | CE2 | TYR | A | 396 | -99.641 | -3.733  | 67.573 | 1.00 | 36.99 |
| 3198 | CD2 | TYR | A | 396 | -98.864 | -4.643  | 68.220 | 1.00 | 36.76 |
| 3199 | C   | TYR | A | 396 | -95.757 | -6.485  | 67.198 | 1.00 | 34.70 |
| 3200 | O   | TYR | A | 396 | -94.589 | -6.043  | 67.195 | 1.00 | 34.91 |
| 3201 | N   | LYS | A | 397 | -96.446 | -6.799  | 66.107 | 1.00 | 34.92 |
| 3202 | CA  | LYS | A | 397 | -95.975 | -6.620  | 64.732 | 1.00 | 35.51 |
| 3203 | CB  | LYS | A | 397 | -95.805 | -5.142  | 64.382 | 1.00 | 36.04 |

FIGURE 3 BK

| A | B | C | D | E | F | G | H | I | J |
|---|---|---|---|---|---|---|---|---|---|
| 3204 | CG | LYS | A | 397 | -97.085 | -4.336 | 64.631 | 1.00 | 37.94 |
| 3205 | CD | LYS | A | 397 | -97.278 | -3.189 | 63.634 | 1.00 | 43.63 |
| 3206 | CE | LYS | A | 397 | -98.408 | -3.463 | 62.632 | 1.00 | 46.07 |
| 3207 | NZ | LYS | A | 397 | -99.674 | -2.736 | 62.990 | 1.00 | 48.66 |
| 3208 | C | LYS | A | 397 | -94.769 | -7.479 | 64.362 | 1.00 | 34.76 |
| 3209 | O | LYS | A | 397 | -94.146 | -7.318 | 63.314 | 1.00 | 35.69 |
| 3210 | N | GLY | A | 398 | -94.473 | -8.432 | 65.225 | 1.00 | 34.51 |
| 3211 | CA | GLY | A | 398 | -93.408 | -9.378 | 64.952 | 1.00 | 33.09 |
| 3212 | C | GLY | A | 398 | -92.027 | -8.789 | 65.139 | 1.00 | 31.76 |
| 3213 | O | GLY | A | 398 | -91.041 | -9.317 | 64.619 | 1.00 | 31.50 |
| 3214 | N | MET | A | 399 | -91.968 | -7.714 | 65.918 | 1.00 | 30.92 |
| 3215 | CA | MET | A | 399 | -90.729 | -6.974 | 66.156 | 1.00 | 29.83 |
| 3216 | CB | MET | A | 399 | -91.029 | -5.475 | 66.137 | 1.00 | 29.98 |
| 3217 | CG | MET | A | 399 | -91.629 | -5.021 | 64.837 | 1.00 | 29.96 |
| 3218 | SD | MET | A | 399 | -92.254 | -3.368 | 64.887 | 1.00 | 37.21 |
| 3219 | CE | MET | A | 399 | -90.784 | -2.469 | 65.436 | 1.00 | 33.01 |
| 3220 | C | MET | A | 399 | -90.118 | -7.371 | 67.487 | 1.00 | 29.01 |
| 3221 | O | MET | A | 399 | -90.572 | -6.920 | 68.538 | 1.00 | 28.71 |
| 3222 | N | PRO | A | 400 | -89.068 | -8.190 | 67.428 | 1.00 | 28.26 |
| 3223 | CA | PRO | A | 400 | -88.406 | -8.745 | 68.618 | 1.00 | 27.62 |
| 3224 | CB | PRO | A | 400 | -87.199 | -9.488 | 68.025 | 1.00 | 27.70 |
| 3225 | CG | PRO | A | 400 | -87.581 | -9.798 | 66.640 | 1.00 | 28.07 |
| 3226 | CD | PRO | A | 400 | -88.414 | -8.614 | 66.180 | 1.00 | 27.97 |
| 3227 | C | PRO | A | 400 | -87.878 | -7.677 | 69.570 | 1.00 | 27.75 |
| 3228 | O | PRO | A | 400 | -87.707 | -7.936 | 70.780 | 1.00 | 27.06 |
| 3229 | N | GLY | A | 401 | -87.595 | -6.504 | 69.004 | 1.00 | 27.25 |
| 3230 | CA | GLY | A | 401 | -86.997 | -5.409 | 69.729 | 1.00 | 27.34 |
| 3231 | C | GLY | A | 401 | -88.063 | -4.491 | 70.262 | 1.00 | 27.51 |
| 3232 | O | GLY | A | 401 | -87.769 | -3.419 | 70.752 | 1.00 | 28.06 |
| 3233 | N | GLY | A | 402 | -89.313 | -4.911 | 70.147 | 1.00 | 27.24 |
| 3234 | CA | GLY | A | 402 | -90.410 | -4.153 | 70.696 | 1.00 | 27.47 |
| 3235 | C | GLY | A | 402 | -90.847 | -4.818 | 71.989 | 1.00 | 28.19 |
| 3236 | O | GLY | A | 402 | -90.546 | -5.983 | 72.236 | 1.00 | 28.06 |
| 3237 | N | ARG | A | 403 | -91.577 | -4.088 | 72.815 | 1.00 | 28.82 |
| 3238 | CA | ARG | A | 403 | -91.957 | -4.588 | 74.117 | 1.00 | 29.49 |
| 3239 | CB | ARG | A | 403 | -90.939 | -4.061 | 75.132 | 1.00 | 30.06 |
| 3240 | CG | ARG | A | 403 | -90.202 | -5.072 | 75.981 | 1.00 | 30.95 |
| 3241 | CD | ARG | A | 403 | -89.633 | -6.206 | 75.194 | 1.00 | 33.17 |
| 3242 | NE | ARG | A | 403 | -88.254 | -6.580 | 75.530 | 1.00 | 33.21 |
| 3243 | CZ | ARG | A | 403 | -87.362 | -6.896 | 74.597 | 1.00 | 33.74 |
| 3244 | NH1 | ARG | A | 403 | -86.130 | -7.249 | 74.929 | 1.00 | 35.28 |
| 3245 | NH2 | ARG | A | 403 | -87.713 | -6.859 | 73.313 | 1.00 | 32.54 |
| 3246 | C | ARG | A | 403 | -93.338 | -3.999 | 74.426 | 1.00 | 29.90 |
| 3247 | O | ARG | A | 403 | -93.527 | -2.791 | 74.312 | 1.00 | 29.67 |
| 3248 | N | ASN | A | 404 | -94.300 | -4.841 | 74.795 | 1.00 | 30.17 |
| 3249 | CA | ASN | A | 404 | -95.632 | -4.357 | 75.172 | 1.00 | 31.02 |
| 3250 | CB | ASN | A | 404 | -96.585 | -4.346 | 73.976 | 1.00 | 30.84 |
| 3251 | CG | ASN | A | 404 | -96.411 | -3.123 | 73.107 | 1.00 | 31.54 |
| 3252 | OD1 | ASN | A | 404 | -95.945 | -3.227 | 71.993 | 1.00 | 34.51 |
| 3253 | ND2 | ASN | A | 404 | -96.790 | -1.962 | 73.613 | 1.00 | 31.54 |
| 3254 | C | ASN | A | 404 | -96.296 | -5.116 | 76.309 | 1.00 | 30.96 |

FIGURE 3 BL

| A | B | C | D | E | F | G | H | I | J |
|---|---|---|---|---|---|---|---|---|---|
| 3255 | O | ASN | A | 404 | -96.097 | -6.309 | 76.468 | 1.00 | 31.51 |
| 3256 | N | LEU | A | 405 | -97.108 | -4.416 | 77.087 | 1.00 | 31.43 |
| 3257 | CA | LEU | A | 405 | -97.824 | -5.044 | 78.183 | 1.00 | 31.86 |
| 3258 | CB | LEU | A | 405 | -98.169 | -4.011 | 79.262 | 1.00 | 31.55 |
| 3259 | CG | LEU | A | 405 | -99.055 | -4.538 | 80.406 | 1.00 | 32.11 |
| 3260 | CD1 | LEU | A | 405 | -98.305 | -5.562 | 81.269 | 1.00 | 29.98 |
| 3261 | CD2 | LEU | A | 405 | -99.584 | -3.421 | 81.287 | 1.00 | 31.87 |
| 3262 | C | LEU | A | 405 | -99.100 | -5.711 | 77.681 | 1.00 | 32.43 |
| 3263 | O | LEU | A | 405 | -99.890 | -5.096 | 76.980 | 1.00 | 31.29 |
| 3264 | N | TYR | A | 406 | -99.285 | -6.978 | 78.040 | 1.00 | 33.78 |
| 3265 | CA | TYR | A | 406 | -100.503 | -7.697 | 77.696 | 1.00 | 35.09 |
| 3266 | CB | TYR | A | 406 | -100.249 | -8.855 | 76.738 | 1.00 | 34.76 |
| 3267 | CG | TYR | A | 406 | -99.685 | -8.475 | 75.396 | 1.00 | 34.78 |
| 3268 | CD1 | TYR | A | 406 | -100.491 | -8.453 | 74.257 | 1.00 | 33.10 |
| 3269 | CE1 | TYR | A | 406 | -99.964 | -8.119 | 73.025 | 1.00 | 33.82 |
| 3270 | CZ | TYR | A | 406 | -98.611 | -7.819 | 72.920 | 1.00 | 32.85 |
| 3271 | OH | TYR | A | 406 | -98.060 | -7.478 | 71.705 | 1.00 | 31.33 |
| 3272 | CE2 | TYR | A | 406 | -97.805 | -7.845 | 74.033 | 1.00 | 32.74 |
| 3273 | CD2 | TYR | A | 406 | -98.337 | -8.171 | 75.256 | 1.00 | 33.14 |
| 3274 | C | TYR | A | 406 | -101.157 | -8.253 | 78.949 | 1.00 | 36.09 |
| 3275 | O | TYR | A | 406 | -100.559 | -8.302 | 80.014 | 1.00 | 35.94 |
| 3276 | N | LYS | A | 407 | -102.399 | -8.689 | 78.793 | 1.00 | 37.79 |
| 3277 | CA | LYS | A | 407 | -103.172 | -9.246 | 79.887 | 1.00 | 39.76 |
| 3278 | CB | LYS | A | 407 | -104.129 | -8.175 | 80.361 | 1.00 | 39.96 |
| 3279 | CG | LYS | A | 407 | -105.278 | -8.580 | 81.224 | 1.00 | 41.71 |
| 3280 | CD | LYS | A | 407 | -106.415 | -7.629 | 80.904 | 1.00 | 43.83 |
| 3281 | CE | LYS | A | 407 | -106.940 | -6.878 | 82.132 | 1.00 | 47.46 |
| 3282 | NZ | LYS | A | 407 | -108.000 | -5.875 | 81.719 | 1.00 | 46.10 |
| 3283 | C | LYS | A | 407 | -103.909 | -10.473 | 79.347 | 1.00 | 40.89 |
| 3284 | O | LYS | A | 407 | -104.532 | -10.429 | 78.301 | 1.00 | 40.99 |
| 3285 | N | ILE | A | 408 | -103.812 | -11.592 | 80.033 | 1.00 | 42.46 |
| 3286 | CA | ILE | A | 408 | -104.484 | -12.776 | 79.520 | 1.00 | 43.24 |
| 3287 | CB | ILE | A | 408 | -103.429 | -13.860 | 79.167 | 1.00 | 43.09 |
| 3288 | CG1 | ILE | A | 408 | -104.089 | -15.189 | 78.834 | 1.00 | 43.14 |
| 3289 | CD1 | ILE | A | 408 | -103.228 | -16.078 | 77.948 | 1.00 | 43.96 |
| 3290 | CG2 | ILE | A | 408 | -102.441 | -14.017 | 80.289 | 1.00 | 42.69 |
| 3291 | C | ILE | A | 408 | -105.575 | -13.266 | 80.478 | 1.00 | 43.91 |
| 3292 | O | ILE | A | 408 | -105.319 | -13.510 | 81.657 | 1.00 | 43.59 |
| 3293 | N | GLN | A | 409 | -106.804 | -13.364 | 79.964 | 1.00 | 45.17 |
| 3294 | CA | GLN | A | 409 | -107.937 | -13.837 | 80.757 | 1.00 | 46.28 |
| 3295 | CB | GLN | A | 409 | -109.236 | -13.845 | 79.943 | 1.00 | 46.51 |
| 3296 | CG | GLN | A | 409 | -110.039 | -12.546 | 79.986 | 1.00 | 48.80 |
| 3297 | CD | GLN | A | 409 | -111.528 | -12.792 | 80.225 | 1.00 | 51.08 |
| 3298 | OE1 | GLN | A | 409 | -112.384 | -12.134 | 79.628 | 1.00 | 52.08 |
| 3299 | NE2 | GLN | A | 409 | -111.834 | -13.732 | 81.107 | 1.00 | 51.58 |
| 3300 | C | GLN | A | 409 | -107.677 | -15.231 | 81.262 | 1.00 | 46.28 |
| 3301 | O | GLN | A | 409 | -107.680 | -16.175 | 80.488 | 1.00 | 46.64 |
| 3302 | N | LEU | A | 410 | -107.459 | -15.362 | 82.562 | 1.00 | 46.95 |
| 3303 | CA | LEU | A | 410 | -107.187 | -16.665 | 83.160 | 1.00 | 47.82 |
| 3304 | CB | LEU | A | 410 | -106.892 | -16.519 | 84.655 | 1.00 | 47.64 |
| 3305 | CG | LEU | A | 410 | -105.435 | -16.451 | 85.140 | 1.00 | 48.05 |

FIGURE 3 BM

| A | B | C | D | E | F | G | H | I | J |
|---|---|---|---|---|---|---|---|---|---|
| 3306 | CD1 | LEU | A | 410 | -104.508 | -15.825 | 84.122 | 1.00 | 47.02 |
| 3307 | CD2 | LEU | A | 410 | -105.342 | -15.730 | 86.480 | 1.00 | 47.28 |
| 3308 | C | LEU | A | 410 | -108.332 | -17.657 | 82.940 | 1.00 | 48.62 |
| 3309 | O | LEU | A | 410 | -108.114 | -18.871 | 82.926 | 1.00 | 49.20 |
| 3310 | N | SER | A | 411 | -109.551 | -17.151 | 82.763 | 1.00 | 49.21 |
| 3311 | CA | SER | A | 411 | -110.697 | -18.041 | 82.564 | 1.00 | 49.64 |
| 3312 | CB | SER | A | 411 | -111.998 | -17.443 | 83.113 | 1.00 | 49.66 |
| 3313 | OG | SER | A | 411 | -112.334 | -16.236 | 82.459 | 1.00 | 50.12 |
| 3314 | C | SER | A | 411 | -110.852 | -18.424 | 81.109 | 1.00 | 49.64 |
| 3315 | O | SER | A | 411 | -111.721 | -19.220 | 80.760 | 1.00 | 49.77 |
| 3316 | N | ASP | A | 412 | -110.004 | -17.846 | 80.264 | 1.00 | 49.70 |
| 3317 | CA | ASP | A | 412 | -109.974 | -18.183 | 78.844 | 1.00 | 49.32 |
| 3318 | CB | ASP | A | 412 | -111.249 | -17.754 | 78.129 | 1.00 | 49.31 |
| 3319 | CG | ASP | A | 412 | -111.118 | -17.858 | 76.631 | 1.00 | 49.86 |
| 3320 | OD1 | ASP | A | 412 | -111.620 | -16.960 | 75.925 | 1.00 | 51.20 |
| 3321 | OD2 | ASP | A | 412 | -110.505 | -18.795 | 76.069 | 1.00 | 49.93 |
| 3322 | C | ASP | A | 412 | -108.754 | -17.587 | 78.150 | 1.00 | 48.90 |
| 3323 | O | ASP | A | 412 | -108.737 | -16.405 | 77.808 | 1.00 | 48.74 |
| 3324 | N | TYR | A | 413 | -107.762 | -18.441 | 77.909 | 1.00 | 48.67 |
| 3325 | CA | TYR | A | 413 | -106.470 | -18.056 | 77.340 | 1.00 | 48.21 |
| 3326 | CB | TYR | A | 413 | -105.569 | -19.284 | 77.219 | 1.00 | 48.00 |
| 3327 | CG | TYR | A | 413 | -105.346 | -19.964 | 78.544 | 1.00 | 47.05 |
| 3328 | CD1 | TYR | A | 413 | -105.400 | -19.244 | 79.728 | 1.00 | 45.48 |
| 3329 | CE1 | TYR | A | 413 | -105.205 | -19.862 | 80.952 | 1.00 | 45.07 |
| 3330 | CZ | TYR | A | 413 | -104.948 | -21.218 | 81.004 | 1.00 | 45.31 |
| 3331 | OH | TYR | A | 413 | -104.737 | -21.830 | 82.228 | 1.00 | 45.70 |
| 3332 | CE2 | TYR | A | 413 | -104.885 | -21.957 | 79.841 | 1.00 | 45.59 |
| 3333 | CD2 | TYR | A | 413 | -105.087 | -21.329 | 78.616 | 1.00 | 46.71 |
| 3334 | C | TYR | A | 413 | -106.501 | -17.311 | 76.013 | 1.00 | 48.20 |
| 3335 | O | TYR | A | 413 | -105.594 | -16.536 | 75.726 | 1.00 | 48.44 |
| 3336 | N | THR | A | 414 | -107.520 | -17.541 | 75.197 | 1.00 | 47.87 |
| 3337 | CA | THR | A | 414 | -107.567 | -16.877 | 73.905 | 1.00 | 48.02 |
| 3338 | CB | THR | A | 414 | -108.516 | -17.616 | 72.932 | 1.00 | 48.47 |
| 3339 | OG1 | THR | A | 414 | -108.533 | -19.021 | 73.228 | 1.00 | 48.81 |
| 3340 | CG2 | THR | A | 414 | -107.962 | -17.563 | 71.507 | 1.00 | 49.08 |
| 3341 | C | THR | A | 414 | -107.979 | -15.408 | 74.061 | 1.00 | 47.92 |
| 3342 | O | THR | A | 414 | -107.921 | -14.624 | 73.104 | 1.00 | 47.40 |
| 3343 | N | LYS | A | 415 | -108.408 | -15.049 | 75.269 | 1.00 | 47.86 |
| 3344 | CA | LYS | A | 415 | -108.818 | -13.681 | 75.566 | 1.00 | 48.09 |
| 3345 | CB | LYS | A | 415 | -109.919 | -13.668 | 76.634 | 1.00 | 48.35 |
| 3346 | CG | LYS | A | 415 | -111.348 | -13.882 | 76.099 | 1.00 | 49.40 |
| 3347 | CD | LYS | A | 415 | -112.327 | -14.273 | 77.230 | 1.00 | 50.67 |
| 3348 | CE | LYS | A | 415 | -113.733 | -14.598 | 76.681 | 1.00 | 52.10 |
| 3349 | NZ | LYS | A | 415 | -114.681 | -15.192 | 77.678 | 1.00 | 50.50 |
| 3350 | C | LYS | A | 415 | -107.602 | -12.851 | 76.010 | 1.00 | 47.68 |
| 3351 | O | LYS | A | 415 | -107.281 | -12.758 | 77.211 | 1.00 | 47.60 |
| 3352 | N | VAL | A | 416 | -106.923 | -12.256 | 75.034 | 1.00 | 46.94 |
| 3353 | CA | VAL | A | 416 | -105.718 | -11.476 | 75.315 | 1.00 | 46.15 |
| 3354 | CB | VAL | A | 416 | -104.464 | -12.136 | 74.718 | 1.00 | 46.12 |
| 3355 | CG1 | VAL | A | 416 | -103.219 | -11.347 | 75.096 | 1.00 | 46.22 |
| 3356 | CG2 | VAL | A | 416 | -104.341 | -13.572 | 75.187 | 1.00 | 46.14 |

FIGURE 3 BN

| A | B | C | D | E | F | G | H | I | J |
|---|---|---|---|---|---|---|---|---|---|
| 3357 | C | VAL | A | 416 | -105.818 | -10.045 | 74.804 | 1.00 | 45.58 |
| 3358 | O | VAL | A | 416 | -106.069 | -9.810 | 73.624 | 1.00 | 45.12 |
| 3359 | N | THR | A | 417 | -105.614 | -9.094 | 75.708 | 1.00 | 44.95 |
| 3360 | CA | THR | A | 417 | -105.657 | -7.682 | 75.359 | 1.00 | 44.73 |
| 3361 | CB | THR | A | 417 | -106.527 | -6.897 | 76.374 | 1.00 | 44.76 |
| 3362 | OG1 | THR | A | 417 | -107.715 | -7.631 | 76.693 | 1.00 | 46.65 |
| 3363 | CG2 | THR | A | 417 | -107.050 | -5.622 | 75.752 | 1.00 | 45.28 |
| 3364 | C | THR | A | 417 | -104.260 | -7.097 | 75.426 | 1.00 | 44.13 |
| 3365 | O | THR | A | 417 | -103.505 | -7.382 | 76.362 | 1.00 | 44.42 |
| 3366 | N | CYS | A | 418 | -103.899 | -6.289 | 74.443 | 1.00 | 43.39 |
| 3367 | CA | CYS | A | 418 | -102.660 | -5.559 | 74.555 | 1.00 | 42.51 |
| 3368 | CB | CYS | A | 418 | -102.050 | -5.243 | 73.204 | 1.00 | 42.80 |
| 3369 | SG | CYS | A | 418 | -100.345 | -4.653 | 73.414 | 1.00 | 43.32 |
| 3370 | C | CYS | A | 418 | -103.005 | -4.275 | 75.271 | 1.00 | 42.18 |
| 3371 | O | CYS | A | 418 | -103.848 | -3.510 | 74.805 | 1.00 | 42.52 |
| 3372 | N | LEU | A | 419 | -102.356 | -4.030 | 76.399 | 1.00 | 41.41 |
| 3373 | CA | LEU | A | 419 | -102.669 | -2.859 | 77.201 | 1.00 | 41.03 |
| 3374 | CB | LEU | A | 419 | -102.488 | -3.161 | 78.699 | 1.00 | 40.49 |
| 3375 | CG | LEU | A | 419 | -103.396 | -4.295 | 79.176 | 1.00 | 41.05 |
| 3376 | CD1 | LEU | A | 419 | -103.204 | -4.655 | 80.641 | 1.00 | 38.62 |
| 3377 | CD2 | LEU | A | 419 | -104.864 | -3.955 | 78.871 | 1.00 | 41.03 |
| 3378 | C | LEU | A | 419 | -101.870 | -1.626 | 76.816 | 1.00 | 40.78 |
| 3379 | O | LEU | A | 419 | -102.157 | -0.536 | 77.303 | 1.00 | 40.62 |
| 3380 | N | SER | A | 420 | -100.884 | -1.788 | 75.933 | 1.00 | 40.62 |
| 3381 | CA | SER | A | 420 | -100.010 | -0.669 | 75.585 | 1.00 | 40.10 |
| 3382 | CB | SER | A | 420 | -98.646 | -0.815 | 76.277 | 1.00 | 39.89 |
| 3383 | OG | SER | A | 420 | -97.918 | -1.939 | 75.806 | 1.00 | 37.82 |
| 3384 | C | SER | A | 420 | -99.796 | -0.432 | 74.105 | 1.00 | 40.54 |
| 3385 | O | SER | A | 420 | -99.518 | 0.685 | 73.700 | 1.00 | 40.69 |
| 3386 | N | CYS | A | 421 | -99.901 | -1.479 | 73.302 | 1.00 | 41.40 |
| 3387 | CA | CYS | A | 421 | -99.666 | -1.371 | 71.862 | 1.00 | 42.61 |
| 3388 | CB | CYS | A | 421 | -100.293 | -2.554 | 71.128 | 1.00 | 42.55 |
| 3389 | SG | CYS | A | 421 | -99.620 | -4.145 | 71.597 | 1.00 | 43.99 |
| 3390 | C | CYS | A | 421 | -100.183 | -0.113 | 71.191 | 1.00 | 43.15 |
| 3391 | O | CYS | A | 421 | -99.529 | 0.427 | 70.305 | 1.00 | 43.48 |
| 3392 | N | GLU | A | 422 | -101.353 | 0.359 | 71.597 | 1.00 | 43.98 |
| 3393 | CA | GLU | A | 422 | -101.996 | 1.426 | 70.843 | 1.00 | 44.84 |
| 3394 | CB | GLU | A | 422 | -103.429 | 1.022 | 70.508 | 1.00 | 45.47 |
| 3395 | CG | GLU | A | 422 | -103.726 | 1.045 | 69.036 | 1.00 | 48.80 |
| 3396 | CD | GLU | A | 422 | -103.109 | -0.147 | 68.344 | 1.00 | 52.97 |
| 3397 | OE1 | GLU | A | 422 | -103.637 | -1.271 | 68.535 | 1.00 | 54.91 |
| 3398 | OE2 | GLU | A | 422 | -102.100 | 0.039 | 67.627 | 1.00 | 53.96 |
| 3399 | C | GLU | A | 422 | -102.050 | 2.752 | 71.539 | 1.00 | 44.63 |
| 3400 | O | GLU | A | 422 | -102.714 | 3.669 | 71.062 | 1.00 | 44.84 |
| 3401 | N | LEU | A | 423 | -101.379 | 2.863 | 72.673 | 1.00 | 44.63 |
| 3402 | CA | LEU | A | 423 | -101.424 | 4.104 | 73.422 | 1.00 | 44.36 |
| 3403 | CB | LEU | A | 423 | -100.722 | 3.945 | 74.756 | 1.00 | 43.74 |
| 3404 | CG | LEU | A | 423 | -101.432 | 2.861 | 75.547 | 1.00 | 43.47 |
| 3405 | CD1 | LEU | A | 423 | -100.700 | 2.545 | 76.833 | 1.00 | 42.34 |
| 3406 | CD2 | LEU | A | 423 | -102.885 | 3.275 | 75.831 | 1.00 | 45.13 |
| 3407 | C | LEU | A | 423 | -100.839 | 5.240 | 72.609 | 1.00 | 44.45 |

FIGURE 3 BO

| A | B | C | D | E | F | G | H | I | J |
|---|---|---|---|---|---|---|---|---|---|
| 3408 | O | LEU | A | 423 | -101.376 | 6.355 | 72.594 | 1.00 | 44.82 |
| 3409 | N | ASN | A | 424 | -99.760 | 4.937 | 71.903 | 1.00 | 44.24 |
| 3410 | CA | ASN | A | 424 | -99.068 | 5.917 | 71.077 | 1.00 | 44.12 |
| 3411 | CB | ASN | A | 424 | -98.281 | 6.898 | 71.945 | 1.00 | 43.83 |
| 3412 | CG | ASN | A | 424 | -98.116 | 8.260 | 71.288 | 1.00 | 45.15 |
| 3413 | OD1 | ASN | A | 424 | -97.775 | 8.360 | 70.105 | 1.00 | 45.08 |
| 3414 | ND2 | ASN | A | 424 | -98.376 | 9.320 | 72.052 | 1.00 | 45.29 |
| 3415 | C | ASN | A | 424 | -98.120 | 5.150 | 70.179 | 1.00 | 43.86 |
| 3416 | O | ASN | A | 424 | -96.910 | 5.190 | 70.369 | 1.00 | 44.50 |
| 3417 | N | PRO | A | 425 | -98.689 | 4.421 | 69.229 | 1.00 | 43.43 |
| 3418 | CA | PRO | A | 425 | -97.934 | 3.584 | 68.293 | 1.00 | 43.33 |
| 3419 | CB | PRO | A | 425 | -98.988 | 3.222 | 67.240 | 1.00 | 43.27 |
| 3420 | CG | PRO | A | 425 | -100.102 | 4.181 | 67.509 | 1.00 | 43.80 |
| 3421 | CD | PRO | A | 425 | -100.139 | 4.298 | 69.002 | 1.00 | 43.48 |
| 3422 | C | PRO | A | 425 | -96.724 | 4.217 | 67.616 | 1.00 | 42.94 |
| 3423 | O | PRO | A | 425 | -95.832 | 3.474 | 67.223 | 1.00 | 42.64 |
| 3424 | N | GLU | A | 426 | -96.679 | 5.532 | 67.465 | 1.00 | 42.90 |
| 3425 | CA | GLU | A | 426 | -95.533 | 6.133 | 66.790 | 1.00 | 43.44 |
| 3426 | CB | GLU | A | 426 | -95.929 | 7.421 | 66.051 | 1.00 | 44.34 |
| 3427 | CG | GLU | A | 426 | -94.800 | 8.077 | 65.250 | 1.00 | 47.87 |
| 3428 | CD | GLU | A | 426 | -95.015 | 9.579 | 65.003 | 1.00 | 52.11 |
| 3429 | OE1 | GLU | A | 426 | -95.896 | 9.949 | 64.193 | 1.00 | 54.48 |
| 3430 | OE2 | GLU | A | 426 | -94.297 | 10.411 | 65.610 | 1.00 | 53.42 |
| 3431 | C | GLU | A | 426 | -94.406 | 6.425 | 67.767 | 1.00 | 42.60 |
| 3432 | O | GLU | A | 426 | -93.236 | 6.290 | 67.432 | 1.00 | 42.84 |
| 3433 | N | ARG | A | 427 | -94.776 | 6.806 | 68.981 | 1.00 | 41.37 |
| 3434 | CA | ARG | A | 427 | -93.828 | 7.233 | 69.983 | 1.00 | 40.61 |
| 3435 | CB | ARG | A | 427 | -94.457 | 8.364 | 70.802 | 1.00 | 40.83 |
| 3436 | CG | ARG | A | 427 | -94.040 | 8.397 | 72.257 | 1.00 | 40.73 |
| 3437 | CD | ARG | A | 427 | -93.165 | 9.568 | 72.653 | 1.00 | 41.61 |
| 3438 | NE | ARG | A | 427 | -93.956 | 10.762 | 72.930 | 1.00 | 42.68 |
| 3439 | CZ | ARG | A | 427 | -93.810 | 11.543 | 73.997 | 1.00 | 41.39 |
| 3440 | NH1 | ARG | A | 427 | -94.599 | 12.605 | 74.148 | 1.00 | 39.72 |
| 3441 | NH2 | ARG | A | 427 | -92.885 | 11.276 | 74.907 | 1.00 | 40.19 |
| 3442 | C | ARG | A | 427 | -93.404 | 6.120 | 70.925 | 1.00 | 39.89 |
| 3443 | O | ARG | A | 427 | -92.274 | 6.089 | 71.397 | 1.00 | 39.68 |
| 3444 | N | CYS | A | 428 | -94.319 | 5.199 | 71.185 | 1.00 | 39.15 |
| 3445 | CA | CYS | A | 428 | -94.094 | 4.180 | 72.189 | 1.00 | 38.16 |
| 3446 | CB | CYS | A | 428 | -95.041 | 4.454 | 73.350 | 1.00 | 38.11 |
| 3447 | SG | CYS | A | 428 | -94.567 | 5.971 | 74.198 | 1.00 | 39.02 |
| 3448 | C | CYS | A | 428 | -94.228 | 2.757 | 71.677 | 1.00 | 37.54 |
| 3449 | O | CYS | A | 428 | -95.310 | 2.326 | 71.275 | 1.00 | 37.47 |
| 3450 | N | GLN | A | 429 | -93.112 | 2.026 | 71.701 | 1.00 | 36.94 |
| 3451 | CA | GLN | A | 429 | -93.058 | 0.639 | 71.217 | 1.00 | 35.60 |
| 3452 | CB | GLN | A | 429 | -92.486 | 0.589 | 69.796 | 1.00 | 35.44 |
| 3453 | CG | GLN | A | 429 | -93.417 | 1.184 | 68.724 | 1.00 | 35.62 |
| 3454 | CD | GLN | A | 429 | -92.719 | 1.477 | 67.396 | 1.00 | 38.22 |
| 3455 | OE1 | GLN | A | 429 | -93.227 | 2.261 | 66.592 | 1.00 | 40.96 |
| 3456 | NE2 | GLN | A | 429 | -91.551 | 0.881 | 67.176 | 1.00 | 38.12 |
| 3457 | C | GLN | A | 429 | -92.209 | -0.207 | 72.154 | 1.00 | 35.00 |
| 3458 | O | GLN | A | 429 | -91.854 | -1.355 | 71.853 | 1.00 | 34.86 |

FIGURE 3 BP

| A | B | C | D | E | F | G | H | I | J |
|---|---|---|---|---|---|---|---|---|---|
| 3459 | N | TYR | A | 430 | -91.878 | 0.358 | 73.305 | 1.00 | 33.75 |
| 3460 | CA | TYR | A | 430 | -91.023 | -0.352 | 74.234 | 1.00 | 32.81 |
| 3461 | CB | TYR | A | 430 | -89.564 | 0.064 | 74.034 | 1.00 | 32.27 |
| 3462 | CG | TYR | A | 430 | -88.572 | -0.952 | 74.548 | 1.00 | 32.27 |
| 3463 | CD1 | TYR | A | 430 | -88.372 | -1.136 | 75.912 | 1.00 | 31.41 |
| 3464 | CE1 | TYR | A | 430 | -87.458 | -2.055 | 76.375 | 1.00 | 30.09 |
| 3465 | CZ | TYR | A | 430 | -86.754 | -2.823 | 75.479 | 1.00 | 29.57 |
| 3466 | OH | TYR | A | 430 | -85.842 | -3.748 | 75.924 | 1.00 | 30.27 |
| 3467 | CE2 | TYR | A | 430 | -86.937 | -2.669 | 74.135 | 1.00 | 30.11 |
| 3468 | CD2 | TYR | A | 430 | -87.845 | -1.743 | 73.670 | 1.00 | 31.00 |
| 3469 | C | TYR | A | 430 | -91.460 | -0.001 | 75.616 | 1.00 | 32.40 |
| 3470 | O | TYR | A | 430 | -91.103 | 1.050 | 76.118 | 1.00 | 32.17 |
| 3471 | N | TYR | A | 431 | -92.212 | -0.893 | 76.252 | 1.00 | 32.42 |
| 3472 | CA | TYR | A | 431 | -92.767 | -0.577 | 77.562 | 1.00 | 32.06 |
| 3473 | CB | TYR | A | 431 | -94.292 | -0.733 | 77.539 | 1.00 | 32.42 |
| 3474 | CG | TYR | A | 431 | -95.081 | 0.337 | 76.833 | 1.00 | 31.65 |
| 3475 | CD1 | TYR | A | 431 | -95.581 | 1.422 | 77.540 | 1.00 | 32.43 |
| 3476 | CE1 | TYR | A | 431 | -96.316 | 2.407 | 76.939 | 1.00 | 30.12 |
| 3477 | CZ | TYR | A | 431 | -96.589 | 2.329 | 75.614 | 1.00 | 32.47 |
| 3478 | OH | TYR | A | 431 | -97.356 | 3.326 | 75.062 | 1.00 | 33.60 |
| 3479 | CE2 | TYR | A | 431 | -96.127 | 1.250 | 74.856 | 1.00 | 33.82 |
| 3480 | CD2 | TYR | A | 431 | -95.369 | 0.250 | 75.484 | 1.00 | 32.58 |
| 3481 | C | TYR | A | 431 | -92.287 | -1.480 | 78.661 | 1.00 | 31.67 |
| 3482 | O | TYR | A | 431 | -91.939 | -2.624 | 78.430 | 1.00 | 31.60 |
| 3483 | N | SER | A | 432 | -92.306 | -0.945 | 79.874 | 1.00 | 31.91 |
| 3484 | CA | SER | A | 432 | -92.099 | -1.718 | 81.078 | 1.00 | 31.56 |
| 3485 | CB | SER | A | 432 | -90.753 | -1.434 | 81.740 | 1.00 | 31.38 |
| 3486 | OG | SER | A | 432 | -90.655 | -0.102 | 82.176 | 1.00 | 31.53 |
| 3487 | C | SER | A | 432 | -93.243 | -1.288 | 81.969 | 1.00 | 31.64 |
| 3488 | O | SER | A | 432 | -93.897 | -0.290 | 81.701 | 1.00 | 31.32 |
| 3489 | N | VAL | A | 433 | -93.468 | -2.028 | 83.044 | 1.00 | 32.12 |
| 3490 | CA | VAL | A | 433 | -94.595 | -1.748 | 83.903 | 1.00 | 32.27 |
| 3491 | CB | VAL | A | 433 | -95.828 | -2.618 | 83.507 | 1.00 | 32.40 |
| 3492 | CG1 | VAL | A | 433 | -95.619 | -4.070 | 83.904 | 1.00 | 31.04 |
| 3493 | CG2 | VAL | A | 433 | -97.112 | -2.068 | 84.124 | 1.00 | 32.36 |
| 3494 | C | VAL | A | 433 | -94.274 | -1.963 | 85.369 | 1.00 | 32.44 |
| 3495 | O | VAL | A | 433 | -93.372 | -2.701 | 85.730 | 1.00 | 31.61 |
| 3496 | N | SER | A | 434 | -95.023 | -1.262 | 86.204 | 1.00 | 33.86 |
| 3497 | CA | SER | A | 434 | -94.922 | -1.386 | 87.639 | 1.00 | 34.71 |
| 3498 | CB | SER | A | 434 | -94.116 | -0.239 | 88.219 | 1.00 | 34.65 |
| 3499 | OG | SER | A | 434 | -93.846 | -0.483 | 89.584 | 1.00 | 36.01 |
| 3500 | C | SER | A | 434 | -96.338 | -1.348 | 88.172 | 1.00 | 35.48 |
| 3501 | O | SER | A | 434 | -97.036 | -0.342 | 88.049 | 1.00 | 35.33 |
| 3502 | N | PHE | A | 435 | -96.769 | -2.459 | 88.744 | 1.00 | 36.86 |
| 3503 | CA | PHE | A | 435 | -98.107 | -2.563 | 89.302 | 1.00 | 38.49 |
| 3504 | CB | PHE | A | 435 | -98.622 | -3.995 | 89.168 | 1.00 | 38.26 |
| 3505 | CG | PHE | A | 435 | -99.027 | -4.364 | 87.763 | 1.00 | 38.43 |
| 3506 | CD1 | PHE | A | 435 | -98.122 | -4.949 | 86.896 | 1.00 | 37.43 |
| 3507 | CE1 | PHE | A | 435 | -98.504 | -5.282 | 85.594 | 1.00 | 37.26 |
| 3508 | CZ | PHE | A | 435 | -99.785 | -5.029 | 85.169 | 1.00 | 37.65 |
| 3509 | CE2 | PHE | A | 435 | -100.696 | -4.457 | 86.027 | 1.00 | 37.28 |

FIGURE 3 BQ

| A | B | C | D | E | F | G | H | I | J |
|---|---|---|---|---|---|---|---|---|---|
| 3510 | CD2 | PHE | A | 435 | -100.321 | -4.125 | 87.313 | 1.00 | 37.90 |
| 3511 | C | PHE | A | 435 | -98.106 | -2.173 | 90.765 | 1.00 | 40.00 |
| 3512 | O | PHE | A | 435 | -97.077 | -2.255 | 91.437 | 1.00 | 40.12 |
| 3513 | N | SER | A | 436 | -99.263 | -1.743 | 91.258 | 1.00 | 41.50 |
| 3514 | CA | SER | A | 436 | -99.396 | -1.420 | 92.668 | 1.00 | 42.84 |
| 3515 | CB | SER | A | 436 | -100.668 | -0.616 | 92.945 | 1.00 | 42.51 |
| 3516 | OG | SER | A | 436 | -101.832 | -1.396 | 92.751 | 1.00 | 42.16 |
| 3517 | C | SER | A | 436 | -99.401 | -2.738 | 93.418 | 1.00 | 44.01 |
| 3518 | O | SER | A | 436 | -99.467 | -3.797 | 92.803 | 1.00 | 44.38 |
| 3519 | N | LYS | A | 437 | -99.349 | -2.673 | 94.742 | 1.00 | 45.22 |
| 3520 | CA | LYS | A | 437 | -99.231 | -3.868 | 95.563 | 1.00 | 46.58 |
| 3521 | CB | LYS | A | 437 | -99.519 | -3.534 | 97.022 | 1.00 | 47.47 |
| 3522 | CG | LYS | A | 437 | -98.703 | -4.324 | 98.032 | 1.00 | 49.42 |
| 3523 | CD | LYS | A | 437 | -97.423 | -3.575 | 98.403 | 1.00 | 53.36 |
| 3524 | CE | LYS | A | 437 | -96.292 | -3.911 | 97.451 | 1.00 | 54.76 |
| 3525 | NZ | LYS | A | 437 | -96.001 | -5.369 | 97.525 | 1.00 | 55.80 |
| 3526 | C | LYS | A | 437 | -100.119 | -5.016 | 95.119 | 1.00 | 46.93 |
| 3527 | O | LYS | A | 437 | -99.677 | -6.169 | 95.071 | 1.00 | 46.90 |
| 3528 | N | GLU | A | 438 | -101.372 | -4.706 | 94.805 | 1.00 | 47.53 |
| 3529 | CA | GLU | A | 438 | -102.327 | -5.732 | 94.398 | 1.00 | 47.90 |
| 3530 | CB | GLU | A | 438 | -103.535 | -5.759 | 95.349 | 1.00 | 48.13 |
| 3531 | CG | GLU | A | 438 | -103.670 | -7.012 | 96.205 | 1.00 | 50.29 |
| 3532 | CD | GLU | A | 438 | -103.291 | -6.804 | 97.667 | 1.00 | 54.05 |
| 3533 | OE1 | GLU | A | 438 | -102.553 | -5.838 | 97.971 | 1.00 | 54.69 |
| 3534 | OE2 | GLU | A | 438 | -103.741 | -7.613 | 98.523 | 1.00 | 55.47 |
| 3535 | C | GLU | A | 438 | -102.787 | -5.599 | 92.938 | 1.00 | 47.84 |
| 3536 | O | GLU | A | 438 | -103.721 | -6.277 | 92.513 | 1.00 | 47.88 |
| 3537 | N | ALA | A | 439 | -102.131 | -4.728 | 92.179 | 1.00 | 47.50 |
| 3538 | CA | ALA | A | 439 | -102.429 | -4.550 | 90.755 | 1.00 | 47.07 |
| 3539 | CB | ALA | A | 439 | -102.587 | -5.892 | 90.059 | 1.00 | 46.85 |
| 3540 | C | ALA | A | 439 | -103.625 | -3.638 | 90.459 | 1.00 | 47.11 |
| 3541 | O | ALA | A | 439 | -104.098 | -3.563 | 89.317 | 1.00 | 46.76 |
| 3542 | N | LYS | A | 440 | -104.113 | -2.942 | 91.478 | 1.00 | 46.83 |
| 3543 | CA | LYS | A | 440 | -105.192 | -1.995 | 91.258 | 1.00 | 46.68 |
| 3544 | CB | LYS | A | 440 | -105.515 | -1.250 | 92.544 | 1.00 | 47.03 |
| 3545 | CG | LYS | A | 440 | -106.782 | -1.688 | 93.236 | 1.00 | 48.96 |
| 3546 | CD | LYS | A | 440 | -107.510 | -0.456 | 93.794 | 1.00 | 51.04 |
| 3547 | CE | LYS | A | 440 | -108.953 | -0.764 | 94.181 | 1.00 | 52.01 |
| 3548 | NZ | LYS | A | 440 | -109.071 | -1.200 | 95.609 | 1.00 | 52.86 |
| 3549 | C | LYS | A | 440 | -104.740 | -0.996 | 90.203 | 1.00 | 46.22 |
| 3550 | O | LYS | A | 440 | -105.527 | -0.519 | 89.390 | 1.00 | 46.19 |
| 3551 | N | TYR | A | 441 | -103.456 | -0.665 | 90.224 | 1.00 | 45.65 |
| 3552 | CA | TYR | A | 441 | -102.930 | 0.273 | 89.247 | 1.00 | 44.75 |
| 3553 | CB | TYR | A | 441 | -102.638 | 1.618 | 89.887 | 1.00 | 45.05 |
| 3554 | CG | TYR | A | 441 | -103.757 | 2.132 | 90.719 | 1.00 | 46.12 |
| 3555 | CD1 | TYR | A | 441 | -103.946 | 1.675 | 92.008 | 1.00 | 47.00 |
| 3556 | CE1 | TYR | A | 441 | -104.978 | 2.143 | 92.768 | 1.00 | 49.02 |
| 3557 | CZ | TYR | A | 441 | -105.840 | 3.081 | 92.239 | 1.00 | 48.21 |
| 3558 | OH | TYR | A | 441 | -106.879 | 3.553 | 92.992 | 1.00 | 50.11 |
| 3559 | CE2 | TYR | A | 441 | -105.666 | 3.551 | 90.970 | 1.00 | 48.19 |
| 3560 | CD2 | TYR | A | 441 | -104.634 | 3.074 | 90.216 | 1.00 | 47.79 |

FIGURE 3 BR

| A | B | C | D | E | F | G | H | I | J |
|---|---|---|---|---|---|---|---|---|---|
| 3561 | C | TYR | A | 441 | -101.647 | -0.214 | 88.649 | 1.00 | 43.69 |
| 3562 | O | TYR | A | 441 | -101.063 | -1.199 | 89.091 | 1.00 | 43.95 |
| 3563 | N | TYR | A | 442 | -101.201 | 0.510 | 87.641 | 1.00 | 42.36 |
| 3564 | CA | TYR | A | 442 | -99.931 | 0.216 | 87.042 | 1.00 | 41.07 |
| 3565 | CB | TYR | A | 442 | -100.000 | -1.018 | 86.132 | 1.00 | 40.75 |
| 3566 | CG | TYR | A | 442 | -100.855 | -0.913 | 84.889 | 1.00 | 40.36 |
| 3567 | CD1 | TYR | A | 442 | -102.204 | -1.254 | 84.910 | 1.00 | 41.27 |
| 3568 | CE1 | TYR | A | 442 | -102.980 | -1.178 | 83.765 | 1.00 | 41.19 |
| 3569 | CZ | TYR | A | 442 | -102.399 | -0.780 | 82.579 | 1.00 | 41.57 |
| 3570 | OH | TYR | A | 442 | -103.143 | -0.689 | 81.413 | 1.00 | 43.14 |
| 3571 | CE2 | TYR | A | 442 | -101.067 | -0.462 | 82.544 | 1.00 | 40.67 |
| 3572 | CD2 | TYR | A | 442 | -100.305 | -0.540 | 83.687 | 1.00 | 39.41 |
| 3573 | C | TYR | A | 442 | -99.388 | 1.449 | 86.348 | 1.00 | 40.30 |
| 3574 | O | TYR | A | 442 | -100.133 | 2.210 | 85.738 | 1.00 | 40.22 |
| 3575 | N | GLN | A | 443 | -98.094 | 1.680 | 86.538 | 1.00 | 39.41 |
| 3576 | CA | GLN | A | 443 | -97.395 | 2.747 | 85.853 | 1.00 | 38.70 |
| 3577 | CB | GLN | A | 443 | -96.279 | 3.327 | 86.727 | 1.00 | 38.39 |
| 3578 | CG | GLN | A | 443 | -95.240 | 4.082 | 85.896 | 1.00 | 38.84 |
| 3579 | CD | GLN | A | 443 | -94.091 | 4.622 | 86.703 | 1.00 | 40.32 |
| 3580 | OE1 | GLN | A | 443 | -93.503 | 3.910 | 87.518 | 1.00 | 41.05 |
| 3581 | NE2 | GLN | A | 443 | -93.766 | 5.891 | 86.485 | 1.00 | 41.05 |
| 3582 | C | GLN | A | 443 | -96.764 | 2.131 | 84.610 | 1.00 | 38.01 |
| 3583 | O | GLN | A | 443 | -96.125 | 1.095 | 84.700 | 1.00 | 37.78 |
| 3584 | N | LEU | A | 444 | -96.940 | 2.771 | 83.467 | 1.00 | 37.74 |
| 3585 | CA | LEU | A | 444 | -96.355 | 2.296 | 82.222 | 1.00 | 37.77 |
| 3586 | CB | LEU | A | 444 | -97.366 | 2.380 | 81.085 | 1.00 | 37.13 |
| 3587 | CG | LEU | A | 444 | -98.305 | 1.201 | 80.831 | 1.00 | 37.70 |
| 3588 | CD1 | LEU | A | 444 | -97.554 | -0.119 | 80.598 | 1.00 | 36.82 |
| 3589 | CD2 | LEU | A | 444 | -99.127 | 1.538 | 79.619 | 1.00 | 37.81 |
| 3590 | C | LEU | A | 444 | -95.149 | 3.134 | 81.840 | 1.00 | 37.67 |
| 3591 | O | LEU | A | 444 | -95.249 | 4.354 | 81.787 | 1.00 | 37.66 |
| 3592 | N | ARG | A | 445 | -94.021 | 2.481 | 81.569 | 1.00 | 37.52 |
| 3593 | CA | ARG | A | 445 | -92.847 | 3.195 | 81.086 | 1.00 | 38.14 |
| 3594 | CB | ARG | A | 445 | -91.595 | 2.893 | 81.910 | 1.00 | 38.71 |
| 3595 | CG | ARG | A | 445 | -90.476 | 3.904 | 81.626 | 1.00 | 41.69 |
| 3596 | CD | ARG | A | 445 | -89.035 | 3.355 | 81.580 | 1.00 | 46.39 |
| 3597 | NE | ARG | A | 445 | -88.890 | 2.061 | 82.239 | 1.00 | 50.92 |
| 3598 | CZ | ARG | A | 445 | -87.728 | 1.532 | 82.600 | 1.00 | 53.29 |
| 3599 | NH1 | ARG | A | 445 | -87.692 | 0.347 | 83.187 | 1.00 | 54.23 |
| 3600 | NH2 | ARG | A | 445 | -86.597 | 2.191 | 82.378 | 1.00 | 56.43 |
| 3601 | C | ARG | A | 445 | -92.546 | 2.861 | 79.636 | 1.00 | 37.56 |
| 3602 | O | ARG | A | 445 | -92.251 | 1.711 | 79.310 | 1.00 | 37.23 |
| 3603 | N | CYS | A | 446 | -92.611 | 3.876 | 78.780 | 1.00 | 37.08 |
| 3604 | CA | CYS | A | 446 | -92.279 | 3.741 | 77.367 | 1.00 | 37.15 |
| 3605 | CB | CYS | A | 446 | -93.322 | 4.463 | 76.533 | 1.00 | 37.41 |
| 3606 | SG | CYS | A | 446 | -92.785 | 5.337 | 75.036 | 1.00 | 40.87 |
| 3607 | C | CYS | A | 446 | -90.898 | 4.336 | 77.132 | 1.00 | 36.37 |
| 3608 | O | CYS | A | 446 | -90.661 | 5.485 | 77.486 | 1.00 | 36.82 |
| 3609 | N | SER | A | 447 | -89.998 | 3.563 | 76.525 | 1.00 | 35.37 |
| 3610 | CA | SER | A | 447 | -88.610 | 3.991 | 76.336 | 1.00 | 34.30 |
| 3611 | CB | SER | A | 447 | -87.654 | 2.890 | 76.804 | 1.00 | 34.46 |

FIGURE 3 BS

| A | B | C | D | E | F | G | H | I | J |
|---|---|---|---|---|---|---|---|---|---|
| 3612 | OG | SER | A | 447 | -87.701 | 2.732 | 78.204 | 1.00 | 34.85 |
| 3613 | C | SER | A | 447 | -88.239 | 4.319 | 74.915 | 1.00 | 33.43 |
| 3614 | O | SER | A | 447 | -87.094 | 4.618 | 74.643 | 1.00 | 33.57 |
| 3615 | N | GLY | A | 448 | -89.182 | 4.234 | 73.992 | 1.00 | 32.46 |
| 3616 | CA | GLY | A | 448 | -88.852 | 4.502 | 72.609 | 1.00 | 31.79 |
| 3617 | C | GLY | A | 448 | -89.927 | 4.020 | 71.674 | 1.00 | 31.31 |
| 3618 | O | GLY | A | 448 | -90.811 | 3.283 | 72.087 | 1.00 | 31.10 |
| 3619 | N | PRO | A | 449 | -89.814 | 4.362 | 70.396 | 1.00 | 31.28 |
| 3620 | CA | PRO | A | 449 | -88.640 | 5.032 | 69.849 | 1.00 | 31.20 |
| 3621 | CB | PRO | A | 449 | -88.794 | 4.827 | 68.339 | 1.00 | 30.61 |
| 3622 | CG | PRO | A | 449 | -90.184 | 4.583 | 68.108 | 1.00 | 31.03 |
| 3623 | CD | PRO | A | 449 | -90.876 | 4.213 | 69.391 | 1.00 | 30.97 |
| 3624 | C | PRO | A | 449 | -88.635 | 6.528 | 70.115 | 1.00 | 31.96 |
| 3625 | O | PRO | A | 449 | -87.680 | 7.179 | 69.722 | 1.00 | 32.18 |
| 3626 | N | GLY | A | 450 | -89.682 | 7.061 | 70.738 | 1.00 | 32.70 |
| 3627 | CA | GLY | A | 450 | -89.753 | 8.483 | 71.013 | 1.00 | 32.98 |
| 3628 | C | GLY | A | 450 | -89.202 | 8.746 | 72.390 | 1.00 | 33.64 |
| 3629 | O | GLY | A | 450 | -88.690 | 7.825 | 73.035 | 1.00 | 34.15 |
| 3630 | N | LEU | A | 451 | -89.290 | 9.995 | 72.836 | 1.00 | 33.79 |
| 3631 | CA | LEU | A | 451 | -88.827 | 10.382 | 74.155 | 1.00 | 34.03 |
| 3632 | CB | LEU | A | 451 | -89.036 | 11.877 | 74.370 | 1.00 | 34.31 |
| 3633 | CG | LEU | A | 451 | -87.992 | 12.788 | 73.719 | 1.00 | 35.35 |
| 3634 | CD1 | LEU | A | 451 | -86.969 | 12.001 | 72.895 | 1.00 | 35.84 |
| 3635 | CD2 | LEU | A | 451 | -88.668 | 13.841 | 72.885 | 1.00 | 35.06 |
| 3636 | C | LEU | A | 451 | -89.641 | 9.597 | 75.152 | 1.00 | 34.16 |
| 3637 | O | LEU | A | 451 | -90.822 | 9.376 | 74.945 | 1.00 | 32.92 |
| 3638 | N | PRO | A | 452 | -89.006 | 9.168 | 76.234 | 1.00 | 34.62 |
| 3639 | CA | PRO | A | 452 | -89.692 | 8.365 | 77.239 | 1.00 | 35.26 |
| 3640 | CB | PRO | A | 452 | -88.680 | 8.295 | 78.378 | 1.00 | 35.14 |
| 3641 | CG | PRO | A | 452 | -87.367 | 8.452 | 77.700 | 1.00 | 35.39 |
| 3642 | CD | PRO | A | 452 | -87.601 | 9.421 | 76.585 | 1.00 | 34.60 |
| 3643 | C | PRO | A | 452 | -90.976 | 9.037 | 77.703 | 1.00 | 36.29 |
| 3644 | O | PRO | A | 452 | -91.033 | 10.267 | 77.861 | 1.00 | 35.67 |
| 3645 | N | LEU | A | 453 | -91.990 | 8.205 | 77.942 | 1.00 | 37.07 |
| 3646 | CA | LEU | A | 453 | -93.302 | 8.660 | 78.367 | 1.00 | 37.52 |
| 3647 | CB | LEU | A | 453 | -94.288 | 8.560 | 77.197 | 1.00 | 37.81 |
| 3648 | CG | LEU | A | 453 | -95.788 | 8.610 | 77.501 | 1.00 | 39.87 |
| 3649 | CD1 | LEU | A | 453 | -96.222 | 7.270 | 78.100 | 1.00 | 42.12 |
| 3650 | CD2 | LEU | A | 453 | -96.606 | 8.902 | 76.249 | 1.00 | 40.21 |
| 3651 | C | LEU | A | 453 | -93.766 | 7.839 | 79.557 | 1.00 | 37.68 |
| 3652 | O | LEU | A | 453 | -93.807 | 6.603 | 79.495 | 1.00 | 38.37 |
| 3653 | N | TYR | A | 454 | -94.105 | 8.512 | 80.650 | 1.00 | 37.49 |
| 3654 | CA | TYR | A | 454 | -94.533 | 7.817 | 81.851 | 1.00 | 38.10 |
| 3655 | CB | TYR | A | 454 | -93.640 | 8.189 | 83.048 | 1.00 | 38.22 |
| 3656 | CG | TYR | A | 454 | -92.176 | 7.767 | 82.915 | 1.00 | 37.53 |
| 3657 | CD1 | TYR | A | 454 | -91.644 | 6.727 | 83.688 | 1.00 | 38.56 |
| 3658 | CE1 | TYR | A | 454 | -90.297 | 6.357 | 83.572 | 1.00 | 37.18 |
| 3659 | CZ | TYR | A | 454 | -89.480 | 7.027 | 82.664 | 1.00 | 37.23 |
| 3660 | OH | TYR | A | 454 | -88.158 | 6.677 | 82.510 | 1.00 | 35.84 |
| 3661 | CE2 | TYR | A | 454 | -89.987 | 8.050 | 81.896 | 1.00 | 37.06 |
| 3662 | CD2 | TYR | A | 454 | -91.324 | 8.415 | 82.027 | 1.00 | 37.67 |

FIGURE 3 BT

| A | B | C | D | E | F | G | H | I | J |
|---|---|---|---|---|---|---|---|---|---|
| 3663 | C | TYR | A | 454 | -96.006 | 8.114 | 82.138 | 1.00 | 38.94 |
| 3664 | O | TYR | A | 454 | -96.412 | 9.285 | 82.250 | 1.00 | 39.17 |
| 3665 | N | THR | A | 455 | -96.809 | 7.053 | 82.236 | 1.00 | 39.20 |
| 3666 | CA | THR | A | 455 | -98.254 | 7.185 | 82.439 | 1.00 | 39.22 |
| 3667 | CB | THR | A | 455 | -99.019 | 6.835 | 81.162 | 1.00 | 39.25 |
| 3668 | OG1 | THR | A | 455 | -98.643 | 5.521 | 80.742 | 1.00 | 39.10 |
| 3669 | CG2 | THR | A | 455 | -98.623 | 7.722 | 80.004 | 1.00 | 38.59 |
| 3670 | C | THR | A | 455 | -98.765 | 6.266 | 83.525 | 1.00 | 39.36 |
| 3671 | O | THR | A | 455 | -98.164 | 5.233 | 83.805 | 1.00 | 39.52 |
| 3672 | N | LEU | A | 456 | -99.898 | 6.633 | 84.117 | 1.00 | 39.82 |
| 3673 | CA | LEU | A | 456 | -100.491 | 5.858 | 85.214 | 1.00 | 40.25 |
| 3674 | CB | LEU | A | 456 | -100.579 | 6.720 | 86.469 | 1.00 | 39.82 |
| 3675 | CG | LEU | A | 456 | -100.467 | 6.139 | 87.885 | 1.00 | 40.98 |
| 3676 | CD1 | LEU | A | 456 | -101.771 | 6.252 | 88.653 | 1.00 | 41.57 |
| 3677 | CD2 | LEU | A | 456 | -99.910 | 4.726 | 87.932 | 1.00 | 40.08 |
| 3678 | C | LEU | A | 456 | -101.868 | 5.350 | 84.786 | 1.00 | 40.38 |
| 3679 | O | LEU | A | 456 | -102.603 | 6.048 | 84.108 | 1.00 | 39.68 |
| 3680 | N | HIS | A | 457 | -102.194 | 4.119 | 85.158 | 1.00 | 41.17 |
| 3681 | CA | HIS | A | 457 | -103.444 | 3.502 | 84.730 | 1.00 | 41.91 |
| 3682 | CB | HIS | A | 457 | -103.180 | 2.582 | 83.539 | 1.00 | 41.62 |
| 3683 | CG | HIS | A | 457 | -102.392 | 3.219 | 82.446 | 1.00 | 40.45 |
| 3684 | ND1 | HIS | A | 457 | -102.923 | 3.478 | 81.203 | 1.00 | 40.12 |
| 3685 | CE1 | HIS | A | 457 | -102.000 | 4.042 | 80.444 | 1.00 | 40.89 |
| 3686 | NE2 | HIS | A | 457 | -100.887 | 4.148 | 81.149 | 1.00 | 39.27 |
| 3687 | CD2 | HIS | A | 457 | -101.105 | 3.634 | 82.401 | 1.00 | 39.96 |
| 3688 | C | HIS | A | 457 | -104.079 | 2.657 | 85.822 | 1.00 | 42.78 |
| 3689 | O | HIS | A | 457 | -103.378 | 2.136 | 86.677 | 1.00 | 43.02 |
| 3690 | N | SER | A | 458 | -105.402 | 2.505 | 85.786 | 1.00 | 43.95 |
| 3691 | CA | SER | A | 458 | -106.073 | 1.632 | 86.748 | 1.00 | 45.16 |
| 3692 | CB | SER | A | 458 | -107.379 | 2.246 | 87.258 | 1.00 | 45.17 |
| 3693 | OG | SER | A | 458 | -108.239 | 2.594 | 86.189 | 1.00 | 46.02 |
| 3694 | C | SER | A | 458 | -106.323 | 0.289 | 86.073 | 1.00 | 46.01 |
| 3695 | O | SER | A | 458 | -106.669 | 0.236 | 84.896 | 1.00 | 46.26 |
| 3696 | N | SER | A | 459 | -106.152 | -0.801 | 86.803 | 1.00 | 46.78 |
| 3697 | CA | SER | A | 459 | -106.269 | -2.091 | 86.161 | 1.00 | 48.21 |
| 3698 | CB | SER | A | 459 | -105.459 | -3.138 | 86.918 | 1.00 | 48.17 |
| 3699 | OG | SER | A | 459 | -106.311 | -3.969 | 87.687 | 1.00 | 50.02 |
| 3700 | C | SER | A | 459 | -107.720 | -2.557 | 85.981 | 1.00 | 48.79 |
| 3701 | O | SER | A | 459 | -107.998 | -3.424 | 85.163 | 1.00 | 48.63 |
| 3702 | N | VAL | A | 460 | -108.645 | -1.979 | 86.736 | 1.00 | 49.68 |
| 3703 | CA | VAL | A | 460 | -110.037 | -2.418 | 86.653 | 1.00 | 50.36 |
| 3704 | CB | VAL | A | 460 | -110.947 | -1.659 | 87.648 | 1.00 | 50.46 |
| 3705 | CG1 | VAL | A | 460 | -111.091 | -0.184 | 87.247 | 1.00 | 50.00 |
| 3706 | CG2 | VAL | A | 460 | -112.299 | -2.353 | 87.759 | 1.00 | 50.44 |
| 3707 | C | VAL | A | 460 | -110.590 | -2.367 | 85.222 | 1.00 | 50.55 |
| 3708 | O | VAL | A | 460 | -111.196 | -3.329 | 84.753 | 1.00 | 50.43 |
| 3709 | N | ASN | A | 461 | -110.347 | -1.263 | 84.525 | 1.00 | 51.08 |
| 3710 | CA | ASN | A | 461 | -110.790 | -1.098 | 83.141 | 1.00 | 51.75 |
| 3711 | CB | ASN | A | 461 | -111.875 | -0.044 | 83.087 | 1.00 | 52.15 |
| 3712 | CG | ASN | A | 461 | -111.562 | 1.131 | 83.977 | 1.00 | 52.89 |
| 3713 | OD1 | ASN | A | 461 | -110.392 | 1.480 | 84.174 | 1.00 | 54.11 |

FIGURE 3 BU

| A | B | C | D | E | F | G | H | I | J |
|---|---|---|---|---|---|---|---|---|---|
| 3714 | ND2 | ASN | A | 461 | -112.601 | 1.738 | 84.544 | 1.00 | 53.79 |
| 3715 | C | ASN | A | 461 | -109.650 | -0.651 | 82.237 | 1.00 | 51.86 |
| 3716 | O | ASN | A | 461 | -109.876 | -0.108 | 81.145 | 1.00 | 52.00 |
| 3717 | N | ASP | A | 462 | -108.424 | -0.873 | 82.703 | 1.00 | 51.87 |
| 3718 | CA | ASP | A | 462 | -107.239 | -0.449 | 81.967 | 1.00 | 51.68 |
| 3719 | CB | ASP | A | 462 | -106.868 | -1.472 | 80.893 | 1.00 | 51.24 |
| 3720 | CG | ASP | A | 462 | -106.742 | -2.872 | 81.454 | 1.00 | 50.98 |
| 3721 | OD1 | ASP | A | 462 | -107.424 | -3.789 | 80.942 | 1.00 | 49.36 |
| 3722 | OD2 | ASP | A | 462 | -105.997 | -3.149 | 82.421 | 1.00 | 50.64 |
| 3723 | C | ASP | A | 462 | -107.451 | 0.923 | 81.349 | 1.00 | 51.78 |
| 3724 | O | ASP | A | 462 | -107.266 | 1.101 | 80.150 | 1.00 | 52.32 |
| 3725 | N | LYS | A | 463 | -107.868 | 1.885 | 82.165 | 1.00 | 51.73 |
| 3726 | CA | LYS | A | 463 | -108.046 | 3.251 | 81.686 | 1.00 | 51.61 |
| 3727 | CB | LYS | A | 463 | -109.361 | 3.859 | 82.195 | 1.00 | 52.12 |
| 3728 | CG | LYS | A | 463 | -109.216 | 4.843 | 83.354 | 1.00 | 53.80 |
| 3729 | CD | LYS | A | 463 | -110.100 | 6.079 | 83.170 | 1.00 | 56.48 |
| 3730 | CE | LYS | A | 463 | -109.461 | 7.311 | 83.813 | 1.00 | 57.93 |
| 3731 | NZ | LYS | A | 463 | -110.082 | 8.604 | 83.381 | 1.00 | 58.60 |
| 3732 | C | LYS | A | 463 | -106.854 | 4.066 | 82.151 | 1.00 | 51.09 |
| 3733 | O | LYS | A | 463 | -106.292 | 3.796 | 83.217 | 1.00 | 50.60 |
| 3734 | N | GLY | A | 464 | -106.458 | 5.043 | 81.342 | 1.00 | 50.66 |
| 3735 | CA | GLY | A | 464 | -105.315 | 5.873 | 81.663 | 1.00 | 50.48 |
| 3736 | C | GLY | A | 464 | -105.686 | 7.064 | 82.518 | 1.00 | 50.28 |
| 3737 | O | GLY | A | 464 | -106.246 | 8.038 | 82.023 | 1.00 | 50.43 |
| 3738 | N | LEU | A | 465 | -105.370 | 6.978 | 83.803 | 1.00 | 49.88 |
| 3739 | CA | LEU | A | 465 | -105.637 | 8.055 | 84.743 | 1.00 | 49.61 |
| 3740 | CB | LEU | A | 465 | -105.217 | 7.662 | 86.155 | 1.00 | 49.71 |
| 3741 | CG | LEU | A | 465 | -105.779 | 6.366 | 86.731 | 1.00 | 50.27 |
| 3742 | CD1 | LEU | A | 465 | -105.786 | 6.448 | 88.253 | 1.00 | 51.84 |
| 3743 | CD2 | LEU | A | 465 | -107.180 | 6.079 | 86.222 | 1.00 | 51.27 |
| 3744 | C | LEU | A | 465 | -104.947 | 9.355 | 84.351 | 1.00 | 49.30 |
| 3745 | O | LEU | A | 465 | -105.589 | 10.412 | 84.341 | 1.00 | 49.57 |
| 3746 | N | ARG | A | 466 | -103.655 | 9.296 | 84.025 | 1.00 | 48.60 |
| 3747 | CA | ARG | A | 466 | -102.930 | 10.524 | 83.667 | 1.00 | 47.99 |
| 3748 | CB | ARG | A | 466 | -102.975 | 11.514 | 84.835 | 1.00 | 48.10 |
| 3749 | CG | ARG | A | 466 | -102.409 | 10.949 | 86.130 | 1.00 | 47.72 |
| 3750 | CD | ARG | A | 466 | -102.653 | 11.822 | 87.346 | 1.00 | 47.83 |
| 3751 | NE | ARG | A | 466 | -102.546 | 11.040 | 88.565 | 1.00 | 47.93 |
| 3752 | CZ | ARG | A | 466 | -103.555 | 10.397 | 89.137 | 1.00 | 47.98 |
| 3753 | NH1 | ARG | A | 466 | -103.345 | 9.694 | 90.240 | 1.00 | 48.67 |
| 3754 | NH2 | ARG | A | 466 | -104.774 | 10.460 | 88.618 | 1.00 | 47.58 |
| 3755 | C | ARG | A | 466 | -101.469 | 10.364 | 83.251 | 1.00 | 47.62 |
| 3756 | O | ARG | A | 466 | -100.840 | 9.318 | 83.454 | 1.00 | 47.46 |
| 3757 | N | VAL | A | 467 | -100.934 | 11.442 | 82.689 | 1.00 | 46.84 |
| 3758 | CA | VAL | A | 467 | -99.541 | 11.488 | 82.278 | 1.00 | 46.21 |
| 3759 | CB | VAL | A | 467 | -99.356 | 12.388 | 81.050 | 1.00 | 46.28 |
| 3760 | CG1 | VAL | A | 467 | -97.932 | 12.294 | 80.519 | 1.00 | 46.55 |
| 3761 | CG2 | VAL | A | 467 | -100.350 | 11.991 | 79.957 | 1.00 | 46.39 |
| 3762 | C | VAL | A | 467 | -98.669 | 11.969 | 83.440 | 1.00 | 45.53 |
| 3763 | O | VAL | A | 467 | -98.882 | 13.054 | 83.985 | 1.00 | 45.50 |
| 3764 | N | LEU | A | 468 | -97.699 | 11.140 | 83.825 | 1.00 | 44.68 |

FIGURE 3 BV

| A | B | C | D | E | F | G | H | I | J |
|---|---|---|---|---|---|---|---|---|---|
| 3765 | CA | LEU | A | 468 | -96.816 | 11.442 | 84.947 | 1.00 | 43.73 |
| 3766 | CB | LEU | A | 468 | -96.367 | 10.158 | 85.624 | 1.00 | 43.64 |
| 3767 | CG | LEU | A | 468 | -97.503 | 9.347 | 86.240 | 1.00 | 43.86 |
| 3768 | CD1 | LEU | A | 468 | -97.013 | 7.951 | 86.605 | 1.00 | 42.81 |
| 3769 | CD2 | LEU | A | 468 | -98.064 | 10.066 | 87.460 | 1.00 | 43.88 |
| 3770 | C | LEU | A | 468 | -95.607 | 12.258 | 84.520 | 1.00 | 43.12 |
| 3771 | O | LEU | A | 468 | -95.192 | 13.178 | 85.213 | 1.00 | 42.91 |
| 3772 | N | GLU | A | 469 | -95.043 | 11.918 | 83.371 | 1.00 | 42.82 |
| 3773 | CA | GLU | A | 469 | -93.899 | 12.649 | 82.844 | 1.00 | 42.57 |
| 3774 | CB | GLU | A | 469 | -92.594 | 12.183 | 83.504 | 1.00 | 42.47 |
| 3775 | CG | GLU | A | 469 | -91.348 | 12.813 | 82.900 | 1.00 | 41.72 |
| 3776 | CD | GLU | A | 469 | -91.356 | 14.324 | 82.998 | 1.00 | 42.26 |
| 3777 | OE1 | GLU | A | 469 | -91.186 | 14.994 | 81.955 | 1.00 | 43.08 |
| 3778 | OE2 | GLU | A | 469 | -91.525 | 14.845 | 84.124 | 1.00 | 43.00 |
| 3779 | C | GLU | A | 469 | -93.860 | 12.397 | 81.360 | 1.00 | 42.39 |
| 3780 | O | GLU | A | 469 | -93.973 | 11.263 | 80.929 | 1.00 | 42.87 |
| 3781 | N | ASP | A | 470 | -93.695 | 13.449 | 80.572 | 1.00 | 42.38 |
| 3782 | CA | ASP | A | 470 | -93.706 | 13.302 | 79.121 | 1.00 | 42.12 |
| 3783 | CB | ASP | A | 470 | -94.939 | 13.993 | 78.533 | 1.00 | 42.50 |
| 3784 | CG | ASP | A | 470 | -94.937 | 15.502 | 78.767 | 1.00 | 43.52 |
| 3785 | OD1 | ASP | A | 470 | -95.916 | 16.155 | 78.347 | 1.00 | 46.03 |
| 3786 | OD2 | ASP | A | 470 | -94.015 | 16.126 | 79.349 | 1.00 | 44.41 |
| 3787 | C | ASP | A | 470 | -92.479 | 13.881 | 78.454 | 1.00 | 41.72 |
| 3788 | O | ASP | A | 470 | -92.426 | 13.935 | 77.225 | 1.00 | 41.65 |
| 3789 | N | ASN | A | 471 | -91.512 | 14.334 | 79.250 | 1.00 | 41.45 |
| 3790 | CA | ASN | A | 471 | -90.291 | 14.954 | 78.717 | 1.00 | 41.38 |
| 3791 | CB | ASN | A | 471 | -89.345 | 13.921 | 78.111 | 1.00 | 41.20 |
| 3792 | CG | ASN | A | 471 | -88.528 | 13.213 | 79.158 | 1.00 | 41.48 |
| 3793 | OD1 | ASN | A | 471 | -87.686 | 13.822 | 79.813 | 1.00 | 42.74 |
| 3794 | ND2 | ASN | A | 471 | -88.792 | 11.927 | 79.350 | 1.00 | 41.64 |
| 3795 | C | ASN | A | 471 | -90.511 | 16.069 | 77.712 | 1.00 | 41.65 |
| 3796 | O | ASN | A | 471 | -89.706 | 16.254 | 76.792 | 1.00 | 42.56 |
| 3797 | N | SER | A | 472 | -91.589 | 16.821 | 77.876 | 1.00 | 41.59 |
| 3798 | CA | SER | A | 472 | -91.828 | 17.960 | 76.999 | 1.00 | 41.81 |
| 3799 | CB | SER | A | 472 | -93.152 | 18.654 | 77.354 | 1.00 | 41.60 |
| 3800 | OG | SER | A | 472 | -93.323 | 18.714 | 78.757 | 1.00 | 42.06 |
| 3801 | C | SER | A | 472 | -90.657 | 18.937 | 77.076 | 1.00 | 41.50 |
| 3802 | O | SER | A | 472 | -90.261 | 19.523 | 76.070 | 1.00 | 41.97 |
| 3803 | N | ALA | A | 473 | -90.101 | 19.111 | 78.268 | 1.00 | 41.56 |
| 3804 | CA | ALA | A | 473 | -88.939 | 19.980 | 78.430 | 1.00 | 41.91 |
| 3805 | CB | ALA | A | 473 | -88.488 | 20.016 | 79.885 | 1.00 | 41.64 |
| 3806 | C | ALA | A | 473 | -87.798 | 19.525 | 77.517 | 1.00 | 42.31 |
| 3807 | O | ALA | A | 473 | -87.299 | 20.313 | 76.702 | 1.00 | 42.61 |
| 3808 | N | LEU | A | 474 | -87.403 | 18.254 | 77.630 | 1.00 | 42.24 |
| 3809 | CA | LEU | A | 474 | -86.336 | 17.732 | 76.787 | 1.00 | 42.83 |
| 3810 | CB | LEU | A | 474 | -86.084 | 16.245 | 77.045 | 1.00 | 42.90 |
| 3811 | CG | LEU | A | 474 | -85.137 | 15.657 | 75.995 | 1.00 | 42.23 |
| 3812 | CD1 | LEU | A | 474 | -83.713 | 16.182 | 76.236 | 1.00 | 42.80 |
| 3813 | CD2 | LEU | A | 474 | -85.161 | 14.135 | 75.983 | 1.00 | 42.52 |
| 3814 | C | LEU | A | 474 | -86.709 | 17.899 | 75.336 | 1.00 | 43.59 |
| 3815 | O | LEU | A | 474 | -85.866 | 18.204 | 74.498 | 1.00 | 43.31 |

FIGURE 3 BW

| A | B | C | D | E | F | G | H | I | J |
|---|---|---|---|---|---|---|---|---|---|
| 3816 | N | ASP | A | 475 | -87.985 | 17.664 | 75.044 | 1.00 | 44.41 |
| 3817 | CA | ASP | A | 475 | -88.480 | 17.801 | 73.688 | 1.00 | 45.98 |
| 3818 | CB | ASP | A | 475 | -89.952 | 17.387 | 73.602 | 1.00 | 46.18 |
| 3819 | CG | ASP | A | 475 | -90.543 | 17.652 | 72.244 | 1.00 | 48.02 |
| 3820 | OD1 | ASP | A | 475 | -91.473 | 18.487 | 72.152 | 1.00 | 51.22 |
| 3821 | OD2 | ASP | A | 475 | -90.137 | 17.091 | 71.206 | 1.00 | 50.30 |
| 3822 | C | ASP | A | 475 | -88.280 | 19.218 | 73.159 | 1.00 | 46.17 |
| 3823 | O | ASP | A | 475 | -87.850 | 19.406 | 72.033 | 1.00 | 45.89 |
| 3824 | N | LYS | A | 476 | -88.574 | 20.215 | 73.980 | 1.00 | 47.41 |
| 3825 | CA | LYS | A | 476 | -88.398 | 21.599 | 73.546 | 1.00 | 48.69 |
| 3826 | CB | LYS | A | 476 | -88.885 | 22.580 | 74.618 | 1.00 | 48.90 |
| 3827 | CG | LYS | A | 476 | -88.932 | 24.039 | 74.148 | 1.00 | 51.61 |
| 3828 | CD | LYS | A | 476 | -88.942 | 25.030 | 75.327 | 1.00 | 55.33 |
| 3829 | CE | LYS | A | 476 | -90.345 | 25.232 | 75.925 | 1.00 | 56.83 |
| 3830 | NZ | LYS | A | 476 | -91.207 | 26.170 | 75.136 | 1.00 | 56.78 |
| 3831 | C | LYS | A | 476 | -86.937 | 21.881 | 73.186 | 1.00 | 48.82 |
| 3832 | O | LYS | A | 476 | -86.645 | 22.414 | 72.117 | 1.00 | 49.02 |
| 3833 | N | MET | A | 477 | -86.017 | 21.495 | 74.061 | 1.00 | 49.18 |
| 3834 | CA | MET | A | 477 | -84.605 | 21.775 | 73.815 | 1.00 | 49.80 |
| 3835 | CB | MET | A | 477 | -83.759 | 21.599 | 75.091 | 1.00 | 50.15 |
| 3836 | CG | MET | A | 477 | -84.365 | 20.657 | 76.117 | 1.00 | 52.66 |
| 3837 | SD | MET | A | 477 | -83.930 | 20.972 | 77.868 | 1.00 | 57.93 |
| 3838 | CE | MET | A | 477 | -82.154 | 21.420 | 77.749 | 1.00 | 56.32 |
| 3839 | C | MET | A | 477 | -84.024 | 21.028 | 72.613 | 1.00 | 49.47 |
| 3840 | O | MET | A | 477 | -83.227 | 21.592 | 71.867 | 1.00 | 49.69 |
| 3841 | N | LEU | A | 478 | -84.443 | 19.785 | 72.398 | 1.00 | 49.22 |
| 3842 | CA | LEU | A | 478 | -83.955 | 19.004 | 71.255 | 1.00 | 48.91 |
| 3843 | CB | LEU | A | 478 | -84.448 | 17.553 | 71.331 | 1.00 | 48.51 |
| 3844 | CG | LEU | A | 478 | -83.491 | 16.488 | 71.884 | 1.00 | 46.60 |
| 3845 | CD1 | LEU | A | 478 | -84.282 | 15.365 | 72.515 | 1.00 | 44.18 |
| 3846 | CD2 | LEU | A | 478 | -82.525 | 17.071 | 72.895 | 1.00 | 44.56 |
| 3847 | C | LEU | A | 478 | -84.288 | 19.589 | 69.880 | 1.00 | 49.49 |
| 3848 | O | LEU | A | 478 | -83.632 | 19.263 | 68.895 | 1.00 | 49.35 |
| 3849 | N | GLN | A | 479 | -85.313 | 20.431 | 69.801 | 1.00 | 50.36 |
| 3850 | CA | GLN | A | 479 | -85.698 | 21.039 | 68.519 | 1.00 | 51.25 |
| 3851 | CB | GLN | A | 479 | -86.907 | 21.951 | 68.702 | 1.00 | 51.64 |
| 3852 | CG | GLN | A | 479 | -88.131 | 21.283 | 69.315 | 1.00 | 53.72 |
| 3853 | CD | GLN | A | 479 | -89.118 | 22.298 | 69.853 | 1.00 | 55.89 |
| 3854 | OE1 | GLN | A | 479 | -90.320 | 22.222 | 69.574 | 1.00 | 56.61 |
| 3855 | NE2 | GLN | A | 479 | -88.613 | 23.261 | 70.619 | 1.00 | 57.98 |
| 3856 | C | GLN | A | 479 | -84.554 | 21.872 | 67.949 | 1.00 | 51.31 |
| 3857 | O | GLN | A | 479 | -84.451 | 22.073 | 66.736 | 1.00 | 51.16 |
| 3858 | N | ASN | A | 480 | -83.704 | 22.350 | 68.850 | 1.00 | 51.49 |
| 3859 | CA | ASN | A | 480 | -82.563 | 23.184 | 68.505 | 1.00 | 51.84 |
| 3860 | CB | ASN | A | 480 | -81.979 | 23.788 | 69.773 | 1.00 | 52.62 |
| 3861 | CG | ASN | A | 480 | -82.306 | 25.242 | 69.917 | 1.00 | 54.63 |
| 3862 | OD1 | ASN | A | 480 | -81.950 | 25.872 | 70.917 | 1.00 | 58.05 |
| 3863 | ND2 | ASN | A | 480 | -82.980 | 25.798 | 68.915 | 1.00 | 55.77 |
| 3864 | C | ASN | A | 480 | -81.440 | 22.454 | 67.805 | 1.00 | 51.02 |
| 3865 | O | ASN | A | 480 | -80.840 | 22.959 | 66.857 | 1.00 | 51.24 |
| 3866 | N | VAL | A | 481 | -81.162 | 21.254 | 68.276 | 1.00 | 49.80 |

FIGURE 3 BX

| A | B | C | D | E | F | G | H | I | J |
|---|---|---|---|---|---|---|---|---|---|
| 3867 | CA | VAL | A | 481 | -80.018 | 20.516 | 67.792 | 1.00 | 48.47 |
| 3868 | CB | VAL | A | 481 | -79.408 | 19.716 | 68.945 | 1.00 | 48.63 |
| 3869 | CG1 | VAL | A | 481 | -80.492 | 19.324 | 69.932 | 1.00 | 48.32 |
| 3870 | CG2 | VAL | A | 481 | -78.657 | 18.513 | 68.428 | 1.00 | 48.71 |
| 3871 | C | VAL | A | 481 | -80.327 | 19.612 | 66.612 | 1.00 | 47.73 |
| 3872 | O | VAL | A | 481 | -81.407 | 19.019 | 66.533 | 1.00 | 47.70 |
| 3873 | N | GLN | A | 482 | -79.385 | 19.549 | 65.674 | 1.00 | 46.58 |
| 3874 | CA | GLN | A | 482 | -79.503 | 18.657 | 64.527 | 1.00 | 45.60 |
| 3875 | CB | GLN | A | 482 | -78.431 | 18.950 | 63.478 | 1.00 | 45.89 |
| 3876 | CG | GLN | A | 482 | -78.803 | 20.048 | 62.491 | 1.00 | 46.68 |
| 3877 | CD | GLN | A | 482 | -77.632 | 20.450 | 61.610 | 1.00 | 49.12 |
| 3878 | OE1 | GLN | A | 482 | -77.532 | 20.021 | 60.449 | 1.00 | 49.65 |
| 3879 | NE2 | GLN | A | 482 | -76.731 | 21.264 | 62.162 | 1.00 | 48.59 |
| 3880 | C | GLN | A | 482 | -79.347 | 17.244 | 65.050 | 1.00 | 44.65 |
| 3881 | O | GLN | A | 482 | -78.237 | 16.712 | 65.161 | 1.00 | 44.89 |
| 3882 | N | MET | A | 483 | -80.464 | 16.620 | 65.381 | 1.00 | 43.19 |
| 3883 | CA | MET | A | 483 | -80.356 | 15.304 | 65.983 | 1.00 | 42.31 |
| 3884 | CB | MET | A | 483 | -81.138 | 15.223 | 67.283 | 1.00 | 42.74 |
| 3885 | CG | MET | A | 483 | -80.330 | 15.935 | 68.344 | 1.00 | 43.53 |
| 3886 | SD | MET | A | 483 | -80.291 | 15.168 | 69.912 | 1.00 | 43.97 |
| 3887 | CE | MET | A | 483 | -80.958 | 13.601 | 69.556 | 1.00 | 43.89 |
| 3888 | C | MET | A | 483 | -80.512 | 14.075 | 65.106 | 1.00 | 41.10 |
| 3889 | O | MET | A | 483 | -81.270 | 14.061 | 64.136 | 1.00 | 41.20 |
| 3890 | N | PRO | A | 484 | -79.762 | 13.046 | 65.477 | 1.00 | 39.61 |
| 3891 | CA | PRO | A | 484 | -79.678 | 11.822 | 64.695 | 1.00 | 38.67 |
| 3892 | CB | PRO | A | 484 | -78.724 | 10.954 | 65.528 | 1.00 | 38.29 |
| 3893 | CG | PRO | A | 484 | -78.928 | 11.443 | 66.883 | 1.00 | 37.49 |
| 3894 | CD | PRO | A | 484 | -78.952 | 12.943 | 66.700 | 1.00 | 39.37 |
| 3895 | C | PRO | A | 484 | -80.998 | 11.092 | 64.600 | 1.00 | 38.20 |
| 3896 | O | PRO | A | 484 | -81.895 | 11.222 | 65.441 | 1.00 | 38.10 |
| 3897 | N | SER | A | 485 | -81.057 | 10.237 | 63.587 | 1.00 | 37.51 |
| 3898 | CA | SER | A | 485 | -82.207 | 9.378 | 63.330 | 1.00 | 37.29 |
| 3899 | CB | SER | A | 485 | -82.556 | 9.425 | 61.842 | 1.00 | 37.14 |
| 3900 | OG | SER | A | 485 | -83.826 | 8.897 | 61.654 | 1.00 | 36.93 |
| 3901 | C | SER | A | 485 | -82.028 | 7.904 | 63.801 | 1.00 | 37.17 |
| 3902 | O | SER | A | 485 | -80.932 | 7.476 | 64.181 | 1.00 | 37.88 |
| 3903 | N | LYS | A | 486 | -83.109 | 7.128 | 63.766 | 1.00 | 36.73 |
| 3904 | CA | LYS | A | 486 | -83.062 | 5.746 | 64.240 | 1.00 | 35.49 |
| 3905 | CB | LYS | A | 486 | -83.647 | 5.664 | 65.654 | 1.00 | 35.57 |
| 3906 | CG | LYS | A | 486 | -82.929 | 4.686 | 66.621 | 1.00 | 36.30 |
| 3907 | CD | LYS | A | 486 | -83.481 | 3.262 | 66.571 | 1.00 | 33.64 |
| 3908 | CE | LYS | A | 486 | -82.682 | 2.328 | 67.460 | 1.00 | 31.92 |
| 3909 | NZ | LYS | A | 486 | -82.930 | 2.396 | 68.930 | 1.00 | 30.35 |
| 3910 | C | LYS | A | 486 | -83.822 | 4.812 | 63.315 | 1.00 | 34.74 |
| 3911 | O | LYS | A | 486 | -85.052 | 4.806 | 63.288 | 1.00 | 33.95 |
| 3912 | N | LYS | A | 487 | -83.084 | 4.014 | 62.554 | 1.00 | 34.07 |
| 3913 | CA | LYS | A | 487 | -83.705 | 3.036 | 61.684 | 1.00 | 33.42 |
| 3914 | CB | LYS | A | 487 | -83.121 | 3.101 | 60.286 | 1.00 | 33.59 |
| 3915 | CG | LYS | A | 487 | -83.425 | 1.862 | 59.468 | 1.00 | 36.69 |
| 3916 | CD | LYS | A | 487 | -83.800 | 2.226 | 58.045 | 1.00 | 41.28 |
| 3917 | CE | LYS | A | 487 | -83.653 | 1.024 | 57.111 | 1.00 | 43.84 |

FIGURE 3 BY

| A | B | C | D | E | F | G | H | I | J |
|---|---|---|---|---|---|---|---|---|---|
| 3918 | NZ | LYS | A | 487 | -84.134 | 1.338 | 55.736 | 1.00 | 43.68 |
| 3919 | C | LYS | A | 487 | -83.559 | 1.619 | 62.233 | 1.00 | 33.03 |
| 3920 | O | LYS | A | 487 | -82.439 | 1.136 | 62.414 | 1.00 | 32.66 |
| 3921 | N | LEU | A | 488 | -84.705 | 0.972 | 62.468 | 1.00 | 31.94 |
| 3922 | CA | LEU | A | 488 | -84.793 | -0.386 | 62.982 | 1.00 | 31.33 |
| 3923 | CB | LEU | A | 488 | -85.744 | -0.441 | 64.170 | 1.00 | 30.72 |
| 3924 | CG | LEU | A | 488 | -85.506 | -1.396 | 65.334 | 1.00 | 33.13 |
| 3925 | CD1 | LEU | A | 488 | -86.848 | -1.982 | 65.790 | 1.00 | 32.47 |
| 3926 | CD2 | LEU | A | 488 | -84.510 | -2.493 | 65.002 | 1.00 | 31.20 |
| 3927 | C | LEU | A | 488 | -85.387 | -1.281 | 61.905 | 1.00 | 30.55 |
| 3928 | O | LEU | A | 488 | -86.536 | -1.077 | 61.486 | 1.00 | 30.55 |
| 3929 | N | ASP | A | 489 | -84.646 | -2.308 | 61.503 | 1.00 | 29.06 |
| 3930 | CA | ASP | A | 489 | -85.097 | -3.154 | 60.413 | 1.00 | 29.01 |
| 3931 | CB | ASP | A | 489 | -84.799 | -2.467 | 59.076 | 1.00 | 29.47 |
| 3932 | CG | ASP | A | 489 | -85.758 | -2.870 | 57.976 | 1.00 | 30.99 |
| 3933 | OD1 | ASP | A | 489 | -85.810 | -2.167 | 56.953 | 1.00 | 34.83 |
| 3934 | OD2 | ASP | A | 489 | -86.511 | -3.858 | 58.036 | 1.00 | 33.27 |
| 3935 | C | ASP | A | 489 | -84.422 | -4.523 | 60.479 | 1.00 | 28.53 |
| 3936 | O | ASP | A | 489 | -83.693 | -4.825 | 61.442 | 1.00 | 27.88 |
| 3937 | N | PHE | A | 490 | -84.686 | -5.359 | 59.477 | 1.00 | 27.83 |
| 3938 | CA | PHE | A | 490 | -84.065 | -6.681 | 59.427 | 1.00 | 27.72 |
| 3939 | CB | PHE | A | 490 | -85.083 | -7.764 | 59.808 | 1.00 | 27.43 |
| 3940 | CG | PHE | A | 490 | -86.211 | -7.913 | 58.825 | 1.00 | 25.57 |
| 3941 | CD1 | PHE | A | 490 | -86.096 | -8.760 | 57.739 | 1.00 | 24.09 |
| 3942 | CE1 | PHE | A | 490 | -87.138 | -8.886 | 56.816 | 1.00 | 22.61 |
| 3943 | CZ | PHE | A | 490 | -88.284 | -8.191 | 56.981 | 1.00 | 20.58 |
| 3944 | CE2 | PHE | A | 490 | -88.416 | -7.338 | 58.057 | 1.00 | 24.85 |
| 3945 | CD2 | PHE | A | 490 | -87.384 | -7.207 | 58.984 | 1.00 | 24.52 |
| 3946 | C | PHE | A | 490 | -83.498 | -6.997 | 58.062 | 1.00 | 28.25 |
| 3947 | O | PHE | A | 490 | -83.920 | -6.426 | 57.066 | 1.00 | 28.31 |
| 3948 | N | ILE | A | 491 | -82.527 | -7.898 | 58.021 | 1.00 | 29.32 |
| 3949 | CA | ILE | A | 491 | -82.030 | -8.438 | 56.761 | 1.00 | 30.10 |
| 3950 | CB | ILE | A | 491 | -80.513 | -8.178 | 56.552 | 1.00 | 30.32 |
| 3951 | CG1 | ILE | A | 491 | -79.689 | -8.904 | 57.621 | 1.00 | 30.59 |
| 3952 | CD1 | ILE | A | 491 | -78.214 | -8.869 | 57.347 | 1.00 | 31.85 |
| 3953 | CG2 | ILE | A | 491 | -80.177 | -6.669 | 56.546 | 1.00 | 27.87 |
| 3954 | C | ILE | A | 491 | -82.302 | -9.943 | 56.825 | 1.00 | 31.72 |
| 3955 | O | ILE | A | 491 | -82.593 | -10.502 | 57.890 | 1.00 | 31.10 |
| 3956 | N | ILE | A | 492 | -82.223 | -10.608 | 55.684 | 1.00 | 33.72 |
| 3957 | CA | ILE | A | 492 | -82.437 | -12.039 | 55.670 | 1.00 | 35.18 |
| 3958 | CB | ILE | A | 492 | -83.369 | -12.471 | 54.533 | 1.00 | 35.31 |
| 3959 | CG1 | ILE | A | 492 | -84.794 | -11.984 | 54.782 | 1.00 | 35.48 |
| 3960 | CD1 | ILE | A | 492 | -85.413 | -12.485 | 56.062 | 1.00 | 33.16 |
| 3961 | CG2 | ILE | A | 492 | -83.373 | -13.990 | 54.431 | 1.00 | 36.28 |
| 3962 | C | ILE | A | 492 | -81.108 | -12.727 | 55.492 | 1.00 | 36.09 |
| 3963 | O | ILE | A | 492 | -80.309 | -12.335 | 54.660 | 1.00 | 36.32 |
| 3964 | N | LEU | A | 493 | -80.869 | -13.738 | 56.318 | 1.00 | 37.37 |
| 3965 | CA | LEU | A | 493 | -79.707 | -14.595 | 56.191 | 1.00 | 38.16 |
| 3966 | CB | LEU | A | 493 | -78.732 | -14.367 | 57.335 | 1.00 | 37.88 |
| 3967 | CG | LEU | A | 493 | -77.484 | -13.521 | 57.096 | 1.00 | 39.32 |
| 3968 | CD1 | LEU | A | 493 | -77.410 | -12.362 | 58.057 | 1.00 | 38.41 |

FIGURE 3 BZ

| A | B | C | D | E | F | G | H | I | J |
|---|---|---|---|---|---|---|---|---|---|
| 3969 | CD2 | LEU | A | 493 | -77.341 | -13.071 | 55.626 | 1.00 | 39.89 |
| 3970 | C | LEU | A | 493 | -80.233 | -16.002 | 56.305 | 1.00 | 38.84 |
| 3971 | O | LEU | A | 493 | -80.833 | -16.352 | 57.331 | 1.00 | 38.82 |
| 3972 | N | ASN | A | 494 | -80.031 | -16.812 | 55.271 | 1.00 | 39.50 |
| 3973 | CA | ASN | A | 494 | -80.453 | -18.206 | 55.338 | 1.00 | 40.92 |
| 3974 | CB | ASN | A | 494 | -79.600 | -18.967 | 56.361 | 1.00 | 41.46 |
| 3975 | CG | ASN | A | 494 | -78.358 | -19.602 | 55.741 | 1.00 | 45.04 |
| 3976 | OD1 | ASN | A | 494 | -77.243 | -19.575 | 56.319 | 1.00 | 46.86 |
| 3977 | ND2 | ASN | A | 494 | -78.544 | -20.210 | 54.567 | 1.00 | 47.43 |
| 3978 | C | ASN | A | 494 | -81.945 | -18.371 | 55.666 | 1.00 | 40.69 |
| 3979 | O | ASN | A | 494 | -82.331 | -19.235 | 56.461 | 1.00 | 41.21 |
| 3980 | N | GLU | A | 495 | -82.775 | -17.524 | 55.069 | 1.00 | 40.67 |
| 3981 | CA | GLU | A | 495 | -84.229 | -17.588 | 55.257 | 1.00 | 40.66 |
| 3982 | CB | GLU | A | 495 | -84.765 | -18.967 | 54.842 | 1.00 | 41.09 |
| 3983 | CG | GLU | A | 495 | -84.249 | -19.376 | 53.471 | 1.00 | 43.98 |
| 3984 | CD | GLU | A | 495 | -84.930 | -20.598 | 52.893 | 1.00 | 48.37 |
| 3985 | OE1 | GLU | A | 495 | -84.445 | -21.079 | 51.840 | 1.00 | 51.01 |
| 3986 | OE2 | GLU | A | 495 | -85.937 | -21.071 | 53.471 | 1.00 | 48.69 |
| 3987 | C | GLU | A | 495 | -84.658 | -17.227 | 56.678 | 1.00 | 39.77 |
| 3988 | O | GLU | A | 495 | -85.761 | -17.561 | 57.119 | 1.00 | 40.01 |
| 3989 | N | THR | A | 496 | -83.776 | -16.535 | 57.393 | 1.00 | 38.18 |
| 3990 | CA | THR | A | 496 | -84.084 | -16.095 | 58.738 | 1.00 | 36.33 |
| 3991 | CB | THR | A | 496 | -83.142 | -16.770 | 59.731 | 1.00 | 36.57 |
| 3992 | OG1 | THR | A | 496 | -83.225 | -18.189 | 59.564 | 1.00 | 38.87 |
| 3993 | CG2 | THR | A | 496 | -83.619 | -16.538 | 61.165 | 1.00 | 36.12 |
| 3994 | C | THR | A | 496 | -83.939 | -14.588 | 58.848 | 1.00 | 34.71 |
| 3995 | O | THR | A | 496 | -83.125 | -13.969 | 58.162 | 1.00 | 34.61 |
| 3996 | N | LYS | A | 497 | -84.731 | -14.003 | 59.723 | 1.00 | 32.91 |
| 3997 | CA | LYS | A | 497 | -84.633 | -12.587 | 59.997 | 1.00 | 31.43 |
| 3998 | CB | LYS | A | 497 | -85.966 | -12.072 | 60.503 | 1.00 | 31.44 |
| 3999 | CG | LYS | A | 497 | -86.894 | -11.560 | 59.455 | 1.00 | 33.48 |
| 4000 | CD | LYS | A | 497 | -88.294 | -11.975 | 59.816 | 1.00 | 37.59 |
| 4001 | CE | LYS | A | 497 | -89.300 | -10.902 | 59.526 | 1.00 | 39.41 |
| 4002 | NZ | LYS | A | 497 | -90.642 | -11.494 | 59.819 | 1.00 | 42.04 |
| 4003 | C | LYS | A | 497 | -83.617 | -12.393 | 61.106 | 1.00 | 29.99 |
| 4004 | O | LYS | A | 497 | -83.576 | -13.158 | 62.060 | 1.00 | 28.96 |
| 4005 | N | PHE | A | 498 | -82.775 | -11.384 | 60.942 | 1.00 | 28.58 |
| 4006 | CA | PHE | A | 498 | -81.866 | -10.940 | 61.989 | 1.00 | 27.19 |
| 4007 | CB | PHE | A | 498 | -80.440 | -11.404 | 61.688 | 1.00 | 26.62 |
| 4008 | CG | PHE | A | 498 | -80.286 | -12.894 | 61.723 | 1.00 | 26.36 |
| 4009 | CD1 | PHE | A | 498 | -80.208 | -13.578 | 62.936 | 1.00 | 24.73 |
| 4010 | CE1 | PHE | A | 498 | -80.079 | -14.973 | 62.967 | 1.00 | 23.81 |
| 4011 | CZ | PHE | A | 498 | -80.046 | -15.676 | 61.789 | 1.00 | 25.41 |
| 4012 | CE2 | PHE | A | 498 | -80.133 | -14.992 | 60.572 | 1.00 | 25.98 |
| 4013 | CD2 | PHE | A | 498 | -80.268 | -13.621 | 60.550 | 1.00 | 25.49 |
| 4014 | C | PHE | A | 498 | -82.017 | -9.418 | 62.009 | 1.00 | 26.34 |
| 4015 | O | PHE | A | 498 | -81.909 | -8.775 | 60.974 | 1.00 | 26.29 |
| 4016 | N | TRP | A | 499 | -82.291 | -8.842 | 63.170 | 1.00 | 26.02 |
| 4017 | CA | TRP | A | 499 | -82.577 | -7.424 | 63.230 | 1.00 | 24.99 |
| 4018 | CB | TRP | A | 499 | -83.673 | -7.166 | 64.260 | 1.00 | 24.90 |
| 4019 | CG | TRP | A | 499 | -84.981 | -7.748 | 63.838 | 1.00 | 25.23 |

FIGURE 3 CA

| A | B | C | D | E | F | G | H | I | J |
|---|---|---|---|---|---|---|---|---|---|
| 4020 | CD1 | TRP | A | 499 | -85.310 | -9.065 | 63.808 | 1.00 | 26.41 |
| 4021 | NE1 | TRP | A | 499 | -86.596 | -9.225 | 63.350 | 1.00 | 27.66 |
| 4022 | CE2 | TRP | A | 499 | -87.121 | -7.991 | 63.071 | 1.00 | 26.05 |
| 4023 | CD2 | TRP | A | 499 | -86.130 | -7.038 | 63.361 | 1.00 | 25.37 |
| 4024 | CE3 | TRP | A | 499 | -86.427 | -5.679 | 63.156 | 1.00 | 27.08 |
| 4025 | CZ3 | TRP | A | 499 | -87.688 | -5.330 | 62.669 | 1.00 | 26.31 |
| 4026 | CH2 | TRP | A | 499 | -88.643 | -6.314 | 62.400 | 1.00 | 26.65 |
| 4027 | CZ2 | TRP | A | 499 | -88.376 | -7.646 | 62.592 | 1.00 | 24.51 |
| 4028 | C | TRP | A | 499 | -81.345 | -6.567 | 63.474 | 1.00 | 25.20 |
| 4029 | O | TRP | A | 499 | -80.363 | -7.016 | 64.064 | 1.00 | 24.93 |
| 4030 | N | TYR | A | 500 | -81.405 | -5.332 | 62.988 | 1.00 | 25.23 |
| 4031 | CA | TYR | A | 500 | -80.306 | -4.401 | 63.128 | 1.00 | 25.42 |
| 4032 | CB | TYR | A | 500 | -79.424 | -4.413 | 61.876 | 1.00 | 25.54 |
| 4033 | CG | TYR | A | 500 | -80.043 | -3.753 | 60.649 | 1.00 | 26.64 |
| 4034 | CD1 | TYR | A | 500 | -79.967 | -2.374 | 60.467 | 1.00 | 26.40 |
| 4035 | CE1 | TYR | A | 500 | -80.512 | -1.757 | 59.350 | 1.00 | 26.86 |
| 4036 | CZ | TYR | A | 500 | -81.144 | -2.519 | 58.375 | 1.00 | 29.46 |
| 4037 | OH | TYR | A | 500 | -81.675 | -1.882 | 57.271 | 1.00 | 31.13 |
| 4038 | CE2 | TYR | A | 500 | -81.236 | -3.903 | 58.509 | 1.00 | 27.58 |
| 4039 | CD2 | TYR | A | 500 | -80.682 | -4.516 | 59.653 | 1.00 | 27.78 |
| 4040 | C | TYR | A | 500 | -80.888 | -3.015 | 63.316 | 1.00 | 25.49 |
| 4041 | O | TYR | A | 500 | -82.021 | -2.755 | 62.916 | 1.00 | 25.52 |
| 4042 | N | GLN | A | 501 | -80.125 | -2.115 | 63.926 | 1.00 | 25.60 |
| 4043 | CA | GLN | A | 501 | -80.560 | -0.734 | 64.056 | 1.00 | 25.35 |
| 4044 | CB | GLN | A | 501 | -80.978 | -0.393 | 65.490 | 1.00 | 24.51 |
| 4045 | CG | GLN | A | 501 | -79.863 | -0.443 | 66.506 | 1.00 | 23.61 |
| 4046 | CD | GLN | A | 501 | -80.323 | -0.032 | 67.887 | 1.00 | 22.31 |
| 4047 | OE1 | GLN | A | 501 | -81.444 | -0.365 | 68.298 | 1.00 | 22.73 |
| 4048 | NE2 | GLN | A | 501 | -79.454 | 0.672 | 68.625 | 1.00 | 22.12 |
| 4049 | C | GLN | A | 501 | -79.435 | 0.160 | 63.598 | 1.00 | 26.27 |
| 4050 | O | GLN | A | 501 | -78.257 | -0.165 | 63.762 | 1.00 | 26.85 |
| 4051 | N | MET | A | 502 | -79.808 | 1.270 | 62.979 | 1.00 | 26.86 |
| 4052 | CA | MET | A | 502 | -78.845 | 2.268 | 62.569 | 1.00 | 27.40 |
| 4053 | CB | MET | A | 502 | -78.806 | 2.401 | 61.057 | 1.00 | 26.94 |
| 4054 | CG | MET | A | 502 | -77.888 | 1.412 | 60.401 | 1.00 | 27.66 |
| 4055 | SD | MET | A | 502 | -78.030 | 1.525 | 58.635 | 1.00 | 28.81 |
| 4056 | CE | MET | A | 502 | -77.003 | 0.102 | 58.082 | 1.00 | 24.15 |
| 4057 | C | MET | A | 502 | -79.190 | 3.604 | 63.181 | 1.00 | 27.77 |
| 4058 | O | MET | A | 502 | -80.338 | 4.049 | 63.127 | 1.00 | 28.13 |
| 4059 | N | ILE | A | 503 | -78.190 | 4.233 | 63.781 | 1.00 | 28.03 |
| 4060 | CA | ILE | A | 503 | -78.334 | 5.584 | 64.271 | 1.00 | 27.84 |
| 4061 | CB | ILE | A | 503 | -77.488 | 5.792 | 65.531 | 1.00 | 27.52 |
| 4062 | CG1 | ILE | A | 503 | -77.796 | 4.709 | 66.570 | 1.00 | 27.03 |
| 4063 | CD1 | ILE | A | 503 | -79.208 | 4.770 | 67.149 | 1.00 | 25.17 |
| 4064 | CG2 | ILE | A | 503 | -77.738 | 7.178 | 66.120 | 1.00 | 28.26 |
| 4065 | C | ILE | A | 503 | -77.807 | 6.397 | 63.101 | 1.00 | 28.13 |
| 4066 | O | ILE | A | 503 | -76.624 | 6.346 | 62.789 | 1.00 | 28.71 |
| 4067 | N | LEU | A | 504 | -78.698 | 7.097 | 62.415 | 1.00 | 28.67 |
| 4068 | CA | LEU | A | 504 | -78.329 | 7.843 | 61.203 | 1.00 | 28.90 |
| 4069 | CB | LEU | A | 504 | -79.428 | 7.690 | 60.152 | 1.00 | 28.20 |
| 4070 | CG | LEU | A | 504 | -79.790 | 6.230 | 59.850 | 1.00 | 27.95 |

FIGURE 3 CB

| A | B | C | D | E | F | G | H | I | J |
|---|---|---|---|---|---|---|---|---|---|
| 4071 | CD1 | LEU | A | 504 | -81.155 | 6.123 | 59.168 | 1.00 | 26.23 |
| 4072 | CD2 | LEU | A | 504 | -78.690 | 5.603 | 58.982 | 1.00 | 27.03 |
| 4073 | C | LEU | A | 504 | -78.123 | 9.320 | 61.467 | 1.00 | 29.01 |
| 4074 | O | LEU | A | 504 | -78.904 | 9.931 | 62.178 | 1.00 | 28.73 |
| 4075 | N | PRO | A | 505 | -77.066 | 9.873 | 60.896 | 1.00 | 29.74 |
| 4076 | CA | PRO | A | 505 | -76.772 | 11.312 | 60.989 | 1.00 | 31.16 |
| 4077 | CB | PRO | A | 505 | -75.549 | 11.487 | 60.085 | 1.00 | 31.00 |
| 4078 | CG | PRO | A | 505 | -74.934 | 10.097 | 59.988 | 1.00 | 30.51 |
| 4079 | CD | PRO | A | 505 | -76.051 | 9.127 | 60.134 | 1.00 | 29.57 |
| 4080 | C | PRO | A | 505 | -77.904 | 12.176 | 60.441 | 1.00 | 32.28 |
| 4081 | O | PRO | A | 505 | -78.521 | 11.795 | 59.440 | 1.00 | 32.31 |
| 4082 | N | PRO | A | 506 | -78.141 | 13.323 | 61.075 | 1.00 | 33.17 |
| 4083 | CA | PRO | A | 506 | -79.180 | 14.272 | 60.656 | 1.00 | 34.45 |
| 4084 | CB | PRO | A | 506 | -78.816 | 15.543 | 61.445 | 1.00 | 34.54 |
| 4085 | CG | PRO | A | 506 | -77.406 | 15.283 | 61.936 | 1.00 | 33.29 |
| 4086 | CD | PRO | A | 506 | -77.405 | 13.821 | 62.252 | 1.00 | 33.00 |
| 4087 | C | PRO | A | 506 | -79.089 | 14.580 | 59.178 | 1.00 | 35.78 |
| 4088 | O | PRO | A | 506 | -77.982 | 14.612 | 58.641 | 1.00 | 35.88 |
| 4089 | N | HIS | A | 507 | -80.231 | 14.829 | 58.537 | 1.00 | 37.58 |
| 4090 | CA | HIS | A | 507 | -80.270 | 15.124 | 57.098 | 1.00 | 39.22 |
| 4091 | CB | HIS | A | 507 | -79.544 | 16.443 | 56.772 | 1.00 | 39.61 |
| 4092 | CG | HIS | A | 507 | -79.863 | 17.558 | 57.714 | 1.00 | 42.21 |
| 4093 | ND1 | HIS | A | 507 | -81.141 | 18.054 | 57.878 | 1.00 | 45.27 |
| 4094 | CE1 | HIS | A | 507 | -81.119 | 19.030 | 58.771 | 1.00 | 45.00 |
| 4095 | NE2 | HIS | A | 507 | -79.875 | 19.182 | 59.194 | 1.00 | 44.55 |
| 4096 | CD2 | HIS | A | 507 | -79.069 | 18.276 | 58.546 | 1.00 | 44.21 |
| 4097 | C | HIS | A | 507 | -79.615 | 14.001 | 56.319 | 1.00 | 39.45 |
| 4098 | O | HIS | A | 507 | -78.933 | 14.244 | 55.321 | 1.00 | 39.96 |
| 4099 | N | PHE | A | 508 | -79.816 | 12.774 | 56.784 | 1.00 | 39.94 |
| 4100 | CA | PHE | A | 508 | -79.205 | 11.603 | 56.160 | 1.00 | 40.03 |
| 4101 | CB | PHE | A | 508 | -79.652 | 10.328 | 56.870 | 1.00 | 40.09 |
| 4102 | CG | PHE | A | 508 | -79.126 | 9.095 | 56.238 | 1.00 | 39.51 |
| 4103 | CD1 | PHE | A | 508 | -77.812 | 8.718 | 56.435 | 1.00 | 38.08 |
| 4104 | CE1 | PHE | A | 508 | -77.318 | 7.584 | 55.838 | 1.00 | 39.51 |
| 4105 | CZ | PHE | A | 508 | -78.135 | 6.829 | 55.023 | 1.00 | 38.62 |
| 4106 | CE2 | PHE | A | 508 | -79.440 | 7.203 | 54.817 | 1.00 | 38.70 |
| 4107 | CD2 | PHE | A | 508 | -79.933 | 8.331 | 55.411 | 1.00 | 39.14 |
| 4108 | C | PHE | A | 508 | -79.514 | 11.488 | 54.678 | 1.00 | 40.20 |
| 4109 | O | PHE | A | 508 | -80.662 | 11.542 | 54.283 | 1.00 | 40.31 |
| 4110 | N | ASP | A | 509 | -78.484 | 11.302 | 53.862 | 1.00 | 40.70 |
| 4111 | CA | ASP | A | 509 | -78.648 | 11.250 | 52.417 | 1.00 | 40.84 |
| 4112 | CB | ASP | A | 509 | -77.932 | 12.445 | 51.793 | 1.00 | 41.19 |
| 4113 | CG | ASP | A | 509 | -78.043 | 12.470 | 50.282 | 1.00 | 41.42 |
| 4114 | OD1 | ASP | A | 509 | -78.683 | 11.570 | 49.705 | 1.00 | 41.34 |
| 4115 | OD2 | ASP | A | 509 | -77.511 | 13.354 | 49.588 | 1.00 | 43.36 |
| 4116 | C | ASP | A | 509 | -78.100 | 9.947 | 51.834 | 1.00 | 41.24 |
| 4117 | O | ASP | A | 509 | -76.887 | 9.784 | 51.664 | 1.00 | 40.75 |
| 4118 | N | LYS | A | 510 | -79.003 | 9.037 | 51.486 | 1.00 | 41.67 |
| 4119 | CA | LYS | A | 510 | -78.603 | 7.714 | 51.023 | 1.00 | 42.33 |
| 4120 | CB | LYS | A | 510 | -79.794 | 6.740 | 50.985 | 1.00 | 42.32 |
| 4121 | CG | LYS | A | 510 | -80.791 | 6.917 | 49.848 | 1.00 | 43.62 |

FIGURE 3 CC

| A | B | C | D | E | F | G | H | I | J |
|---|---|---|---|---|---|---|---|---|---|
| 4122 | CD | LYS | A | 510 | -82.090 | 6.159 | 50.171 | 1.00 | 45.42 |
| 4123 | CE | LYS | A | 510 | -82.783 | 5.623 | 48.925 | 1.00 | 47.10 |
| 4124 | NZ | LYS | A | 510 | -82.855 | 6.597 | 47.790 | 1.00 | 47.41 |
| 4125 | C | LYS | A | 510 | -77.819 | 7.743 | 49.722 | 1.00 | 42.64 |
| 4126 | O | LYS | A | 510 | -77.310 | 6.719 | 49.270 | 1.00 | 42.28 |
| 4127 | N | SER | A | 511 | -77.692 | 8.930 | 49.138 | 1.00 | 43.25 |
| 4128 | CA | SER | A | 511 | -76.883 | 9.063 | 47.932 | 1.00 | 43.68 |
| 4129 | CB | SER | A | 511 | -77.379 | 10.205 | 47.035 | 1.00 | 43.86 |
| 4130 | OG | SER | A | 511 | -76.905 | 11.463 | 47.490 | 1.00 | 44.84 |
| 4131 | C | SER | A | 511 | -75.422 | 9.286 | 48.310 | 1.00 | 43.23 |
| 4132 | O | SER | A | 511 | -74.537 | 9.182 | 47.463 | 1.00 | 43.76 |
| 4133 | N | LYS | A | 512 | -75.169 | 9.579 | 49.580 | 1.00 | 42.43 |
| 4134 | CA | LYS | A | 512 | -73.794 | 9.814 | 50.039 | 1.00 | 42.01 |
| 4135 | CB | LYS | A | 512 | -73.739 | 11.035 | 50.962 | 1.00 | 42.16 |
| 4136 | CG | LYS | A | 512 | -72.528 | 11.947 | 50.735 | 1.00 | 45.95 |
| 4137 | CD | LYS | A | 512 | -71.856 | 12.418 | 52.058 | 1.00 | 48.83 |
| 4138 | CE | LYS | A | 512 | -71.003 | 11.298 | 52.684 | 1.00 | 50.74 |
| 4139 | NZ | LYS | A | 512 | -70.193 | 11.690 | 53.896 | 1.00 | 50.48 |
| 4140 | C | LYS | A | 512 | -73.221 | 8.593 | 50.766 | 1.00 | 40.83 |
| 4141 | O | LYS | A | 512 | -73.963 | 7.736 | 51.244 | 1.00 | 40.45 |
| 4142 | N | LYS | A | 513 | -71.897 | 8.529 | 50.858 | 1.00 | 39.72 |
| 4143 | CA | LYS | A | 513 | -71.213 | 7.427 | 51.522 | 1.00 | 38.40 |
| 4144 | CB | LYS | A | 513 | -69.996 | 6.989 | 50.709 | 1.00 | 38.25 |
| 4145 | CG | LYS | A | 513 | -70.307 | 6.475 | 49.304 | 1.00 | 39.78 |
| 4146 | CD | LYS | A | 513 | -70.907 | 5.066 | 49.311 | 1.00 | 41.04 |
| 4147 | CE | LYS | A | 513 | -71.269 | 4.597 | 47.895 | 1.00 | 41.89 |
| 4148 | NZ | LYS | A | 513 | -72.232 | 5.519 | 47.227 | 1.00 | 41.74 |
| 4149 | C | LYS | A | 513 | -70.757 | 7.856 | 52.912 | 1.00 | 37.48 |
| 4150 | O | LYS | A | 513 | -69.953 | 8.789 | 53.048 | 1.00 | 37.92 |
| 4151 | N | TYR | A | 514 | -71.268 | 7.195 | 53.946 | 1.00 | 35.23 |
| 4152 | CA | TYR | A | 514 | -70.863 | 7.526 | 55.307 | 1.00 | 32.93 |
| 4153 | CB | TYR | A | 514 | -72.074 | 7.652 | 56.209 | 1.00 | 32.28 |
| 4154 | CG | TYR | A | 514 | -73.060 | 8.688 | 55.783 | 1.00 | 31.98 |
| 4155 | CD1 | TYR | A | 514 | -73.117 | 9.915 | 56.424 | 1.00 | 32.59 |
| 4156 | CE1 | TYR | A | 514 | -74.022 | 10.865 | 56.046 | 1.00 | 32.89 |
| 4157 | CZ | TYR | A | 514 | -74.887 | 10.595 | 55.002 | 1.00 | 32.35 |
| 4158 | OH | TYR | A | 514 | -75.793 | 11.546 | 54.617 | 1.00 | 32.72 |
| 4159 | CE2 | TYR | A | 514 | -74.842 | 9.393 | 54.348 | 1.00 | 30.78 |
| 4160 | CD2 | TYR | A | 514 | -73.935 | 8.447 | 54.742 | 1.00 | 31.30 |
| 4161 | C | TYR | A | 514 | -69.997 | 6.439 | 55.914 | 1.00 | 32.06 |
| 4162 | O | TYR | A | 514 | -70.142 | 5.254 | 55.583 | 1.00 | 31.54 |
| 4163 | N | PRO | A | 515 | -69.129 | 6.849 | 56.839 | 1.00 | 30.48 |
| 4164 | CA | PRO | A | 515 | -68.353 | 5.905 | 57.636 | 1.00 | 29.30 |
| 4165 | CB | PRO | A | 515 | -67.539 | 6.808 | 58.574 | 1.00 | 28.88 |
| 4166 | CG | PRO | A | 515 | -67.620 | 8.141 | 58.014 | 1.00 | 30.04 |
| 4167 | CD | PRO | A | 515 | -68.874 | 8.248 | 57.218 | 1.00 | 29.90 |
| 4168 | C | PRO | A | 515 | -69.334 | 5.150 | 58.500 | 1.00 | 28.02 |
| 4169 | O | PRO | A | 515 | -70.384 | 5.677 | 58.871 | 1.00 | 27.42 |
| 4170 | N | LEU | A | 516 | -68.986 | 3.937 | 58.869 | 1.00 | 27.30 |
| 4171 | CA | LEU | A | 516 | -69.880 | 3.186 | 59.722 | 1.00 | 26.37 |
| 4172 | CB | LEU | A | 516 | -70.689 | 2.172 | 58.915 | 1.00 | 26.70 |

FIGURE 3 CD

| A | B | C | D | E | F | G | H | I | J |
|---|---|---|---|---|---|---|---|---|---|
| 4173 | CG | LEU | A | 516 | -71.737 | 1.421 | 59.739 | 1.00 | 27.51 |
| 4174 | CD1 | LEU | A | 516 | -71.143 | 0.107 | 60.286 | 1.00 | 28.75 |
| 4175 | CD2 | LEU | A | 516 | -72.930 | 1.111 | 58.894 | 1.00 | 27.87 |
| 4176 | C | LEU | A | 516 | -69.103 | 2.517 | 60.836 | 1.00 | 25.59 |
| 4177 | O | LEU | A | 516 | -68.033 | 1.944 | 60.620 | 1.00 | 25.32 |
| 4178 | N | LEU | A | 517 | -69.632 | 2.648 | 62.041 | 1.00 | 24.37 |
| 4179 | CA | LEU | A | 517 | -69.042 | 2.020 | 63.180 | 1.00 | 24.38 |
| 4180 | CB | LEU | A | 517 | -68.763 | 3.039 | 64.260 | 1.00 | 24.08 |
| 4181 | CG | LEU | A | 517 | -68.512 | 2.477 | 65.647 | 1.00 | 23.33 |
| 4182 | CD1 | LEU | A | 517 | -68.693 | 3.643 | 66.634 | 1.00 | 20.78 |
| 4183 | CD2 | LEU | A | 517 | -67.124 | 1.899 | 65.722 | 1.00 | 19.85 |
| 4184 | C | LEU | A | 517 | -70.029 | 0.995 | 63.698 | 1.00 | 24.90 |
| 4185 | O | LEU | A | 517 | -71.158 | 1.350 | 64.038 | 1.00 | 24.55 |
| 4186 | N | LEU | A | 518 | -69.618 | -0.264 | 63.748 | 1.00 | 24.40 |
| 4187 | CA | LEU | A | 518 | -70.505 | -1.278 | 64.260 | 1.00 | 24.51 |
| 4188 | CB | LEU | A | 518 | -70.182 | -2.654 | 63.651 | 1.00 | 24.62 |
| 4189 | CG | LEU | A | 518 | -71.237 | -3.727 | 63.874 | 1.00 | 25.59 |
| 4190 | CD1 | LEU | A | 518 | -72.561 | -3.340 | 63.241 | 1.00 | 28.96 |
| 4191 | CD2 | LEU | A | 518 | -70.737 | -5.037 | 63.300 | 1.00 | 25.58 |
| 4192 | C | LEU | A | 518 | -70.385 | -1.348 | 65.773 | 1.00 | 24.18 |
| 4193 | O | LEU | A | 518 | -69.311 | -1.628 | 66.306 | 1.00 | 24.04 |
| 4194 | N | ASP | A | 519 | -71.491 | -1.098 | 66.451 | 1.00 | 23.23 |
| 4195 | CA | ASP | A | 519 | -71.551 | -1.161 | 67.897 | 1.00 | 23.29 |
| 4196 | CB | ASP | A | 519 | -72.561 | -0.129 | 68.393 | 1.00 | 22.64 |
| 4197 | CG | ASP | A | 519 | -72.754 | -0.154 | 69.871 | 1.00 | 22.90 |
| 4198 | OD1 | ASP | A | 519 | -73.392 | 0.798 | 70.357 | 1.00 | 22.35 |
| 4199 | OD2 | ASP | A | 519 | -72.329 | -1.057 | 70.641 | 1.00 | 22.78 |
| 4200 | C | ASP | A | 519 | -71.965 | -2.602 | 68.256 | 1.00 | 23.59 |
| 4201 | O | ASP | A | 519 | -73.074 | -3.029 | 67.947 | 1.00 | 23.11 |
| 4202 | N | VAL | A | 520 | -71.067 | -3.365 | 68.878 | 1.00 | 23.40 |
| 4203 | CA | VAL | A | 520 | -71.405 | -4.751 | 69.162 | 1.00 | 23.18 |
| 4204 | CB | VAL | A | 520 | -70.447 | -5.726 | 68.433 | 1.00 | 23.42 |
| 4205 | CG1 | VAL | A | 520 | -69.009 | -5.290 | 68.619 | 1.00 | 24.66 |
| 4206 | CG2 | VAL | A | 520 | -70.757 | -5.747 | 66.962 | 1.00 | 26.54 |
| 4207 | C | VAL | A | 520 | -71.415 | -5.157 | 70.621 | 1.00 | 22.20 |
| 4208 | O | VAL | A | 520 | -70.640 | -4.661 | 71.431 | 1.00 | 21.70 |
| 4209 | N | TYR | A | 521 | -72.314 | -6.074 | 70.946 | 1.00 | 21.43 |
| 4210 | CA | TYR | A | 521 | -72.241 | -6.747 | 72.222 | 1.00 | 20.51 |
| 4211 | CB | TYR | A | 521 | -73.386 | -6.371 | 73.173 | 1.00 | 20.48 |
| 4212 | CG | TYR | A | 521 | -73.188 | -7.015 | 74.510 | 1.00 | 20.85 |
| 4213 | CD1 | TYR | A | 521 | -73.942 | -8.121 | 74.875 | 1.00 | 22.44 |
| 4214 | CE1 | TYR | A | 521 | -73.749 | -8.749 | 76.081 | 1.00 | 21.90 |
| 4215 | CZ | TYR | A | 521 | -72.776 | -8.298 | 76.934 | 1.00 | 20.98 |
| 4216 | OH | TYR | A | 521 | -72.628 | -8.975 | 78.120 | 1.00 | 22.91 |
| 4217 | CE2 | TYR | A | 521 | -71.994 | -7.202 | 76.606 | 1.00 | 17.30 |
| 4218 | CD2 | TYR | A | 521 | -72.190 | -6.579 | 75.380 | 1.00 | 18.93 |
| 4219 | C | TYR | A | 521 | -72.245 | -8.204 | 71.802 | 1.00 | 20.17 |
| 4220 | O | TYR | A | 521 | -71.201 | -8.861 | 71.829 | 1.00 | 19.83 |
| 4221 | N | ALA | A | 522 | -73.418 | -8.699 | 71.398 | 1.00 | 19.73 |
| 4222 | CA | ALA | A | 522 | -73.560 | -10.023 | 70.790 | 1.00 | 19.27 |
| 4223 | CB | ALA | A | 522 | -72.675 | -10.150 | 69.568 | 1.00 | 18.32 |

FIGURE 3 CE

| A | B | C | D | E | F | G | H | I | J |
|---|---|---|---|---|---|---|---|---|---|
| 4224 | C | ALA | A | 522 | -73.331 | -11.219 | 71.682 | 1.00 | 19.90 |
| 4225 | O | ALA | A | 522 | -73.012 | -12.306 | 71.172 | 1.00 | 19.97 |
| 4226 | N | GLY | A | 523 | -73.464 | -11.032 | 72.990 | 1.00 | 19.34 |
| 4227 | CA | GLY | A | 523 | -73.369 | -12.135 | 73.907 | 1.00 | 19.32 |
| 4228 | C | GLY | A | 523 | -74.632 | -12.946 | 73.757 | 1.00 | 20.03 |
| 4229 | O | GLY | A | 523 | -75.568 | -12.532 | 73.091 | 1.00 | 20.55 |
| 4230 | N | PRO | A | 524 | -74.663 | -14.113 | 74.377 | 1.00 | 20.13 |
| 4231 | CA | PRO | A | 524 | -75.830 | -14.988 | 74.295 | 1.00 | 20.26 |
| 4232 | CB | PRO | A | 524 | -75.374 | -16.244 | 75.038 | 1.00 | 20.77 |
| 4233 | CG | PRO | A | 524 | -73.854 | -16.126 | 75.050 | 1.00 | 20.77 |
| 4234 | CD | PRO | A | 524 | -73.578 | -14.674 | 75.200 | 1.00 | 19.33 |
| 4235 | C | PRO | A | 524 | -77.058 | -14.366 | 74.956 | 1.00 | 20.74 |
| 4236 | O | PRO | A | 524 | -77.008 | -13.932 | 76.107 | 1.00 | 20.66 |
| 4237 | N | CYS | A | 525 | -78.149 | -14.328 | 74.197 | 1.00 | 20.18 |
| 4238 | CA | CYS | A | 525 | -79.388 | -13.695 | 74.587 | 1.00 | 20.82 |
| 4239 | CB | CYS | A | 525 | -79.949 | -14.220 | 75.910 | 1.00 | 20.83 |
| 4240 | SG | CYS | A | 525 | -81.741 | -13.933 | 76.063 | 1.00 | 22.40 |
| 4241 | C | CYS | A | 525 | -79.295 | -12.172 | 74.590 | 1.00 | 21.05 |
| 4242 | O | CYS | A | 525 | -80.100 | -11.502 | 75.207 | 1.00 | 21.55 |
| 4243 | N | SER | A | 526 | -78.337 | -11.617 | 73.874 | 1.00 | 21.27 |
| 4244 | CA | SER | A | 526 | -78.270 | -10.175 | 73.804 | 1.00 | 21.42 |
| 4245 | CB | SER | A | 526 | -76.872 | -9.726 | 73.409 | 1.00 | 21.05 |
| 4246 | OG | SER | A | 526 | -76.479 | -10.308 | 72.175 | 1.00 | 23.05 |
| 4247 | C | SER | A | 526 | -79.276 | -9.632 | 72.799 | 1.00 | 21.89 |
| 4248 | O | SER | A | 526 | -79.824 | -10.374 | 71.944 | 1.00 | 21.77 |
| 4249 | N | GLN | A | 527 | -79.518 | -8.333 | 72.903 | 1.00 | 21.46 |
| 4250 | CA | GLN | A | 527 | -80.321 | -7.637 | 71.925 | 1.00 | 22.06 |
| 4251 | CB | GLN | A | 527 | -81.803 | -7.630 | 72.305 | 1.00 | 22.11 |
| 4252 | CG | GLN | A | 527 | -82.670 | -6.928 | 71.305 | 1.00 | 20.73 |
| 4253 | CD | GLN | A | 527 | -84.138 | -7.223 | 71.507 | 1.00 | 22.19 |
| 4254 | OE1 | GLN | A | 527 | -84.795 | -6.589 | 72.323 | 1.00 | 25.90 |
| 4255 | NE2 | GLN | A | 527 | -84.652 | -8.177 | 70.774 | 1.00 | 20.97 |
| 4256 | C | GLN | A | 527 | -79.809 | -6.226 | 71.867 | 1.00 | 22.91 |
| 4257 | O | GLN | A | 527 | -79.926 | -5.473 | 72.839 | 1.00 | 23.38 |
| 4258 | N | LYS | A | 528 | -79.235 | -5.880 | 70.724 | 1.00 | 23.75 |
| 4259 | CA | LYS | A | 528 | -78.710 | -4.557 | 70.470 | 1.00 | 24.57 |
| 4260 | CB | LYS | A | 528 | -77.282 | -4.675 | 69.951 | 1.00 | 24.43 |
| 4261 | CG | LYS | A | 528 | -76.278 | -5.006 | 71.025 | 1.00 | 25.17 |
| 4262 | CD | LYS | A | 528 | -76.446 | -4.083 | 72.209 | 1.00 | 26.22 |
| 4263 | CE | LYS | A | 528 | -75.577 | -2.871 | 72.089 | 1.00 | 28.78 |
| 4264 | NZ | LYS | A | 528 | -74.300 | -3.184 | 71.422 | 1.00 | 30.11 |
| 4265 | C | LYS | A | 528 | -79.540 | -3.789 | 69.434 | 1.00 | 25.60 |
| 4266 | O | LYS | A | 528 | -79.317 | -2.603 | 69.228 | 1.00 | 25.41 |
| 4267 | N | ALA | A | 529 | -80.443 | -4.472 | 68.732 | 1.00 | 26.51 |
| 4268 | CA | ALA | A | 529 | -81.299 | -3.791 | 67.759 | 1.00 | 27.24 |
| 4269 | CB | ALA | A | 529 | -81.477 | -4.612 | 66.498 | 1.00 | 26.91 |
| 4270 | C | ALA | A | 529 | -82.603 | -3.585 | 68.489 | 1.00 | 27.74 |
| 4271 | O | ALA | A | 529 | -83.333 | -4.533 | 68.740 | 1.00 | 27.80 |
| 4272 | N | ASP | A | 530 | -82.887 | -2.324 | 68.814 | 1.00 | 28.77 |
| 4273 | CA | ASP | A | 530 | -83.936 | -1.953 | 69.769 | 1.00 | 28.97 |
| 4274 | CB | ASP | A | 530 | -83.238 | -1.319 | 71.013 | 1.00 | 29.38 |

FIGURE 3 CF

| A | B | C | D | E | F | G | H | I | J |
|---|---|---|---|---|---|---|---|---|---|
| 4275 | CG | ASP | A | 530 | -83.489 | -2.074 | 72.224 | 1.00 | 32.06 |
| 4276 | OD1 | ASP | A | 530 | -84.519 | -2.802 | 72.207 | 1.00 | 38.06 |
| 4277 | OD2 | ASP | A | 530 | -82.737 | -2.052 | 73.222 | 1.00 | 33.89 |
| 4278 | C | ASP | A | 530 | -84.882 | -0.874 | 69.325 | 1.00 | 28.27 |
| 4279 | O | ASP | A | 530 | -84.580 | -0.095 | 68.440 | 1.00 | 28.50 |
| 4280 | N | THR | A | 531 | -85.967 | -0.753 | 70.068 | 1.00 | 27.52 |
| 4281 | CA | THR | A | 531 | -86.940 | 0.280 | 69.847 | 1.00 | 28.07 |
| 4282 | CB | THR | A | 531 | -88.324 | -0.391 | 69.892 | 1.00 | 28.44 |
| 4283 | OG1 | THR | A | 531 | -89.032 | -0.192 | 68.645 | 1.00 | 30.33 |
| 4284 | CG2 | THR | A | 531 | -89.171 | 0.162 | 70.967 | 1.00 | 26.74 |
| 4285 | C | THR | A | 531 | -86.755 | 1.388 | 70.928 | 1.00 | 28.23 |
| 4286 | O | THR | A | 531 | -87.547 | 2.323 | 71.048 | 1.00 | 28.80 |
| 4287 | N | VAL | A | 532 | -85.679 | 1.288 | 71.695 | 1.00 | 27.21 |
| 4288 | CA | VAL | A | 532 | -85.408 | 2.263 | 72.741 | 1.00 | 26.82 |
| 4289 | CB | VAL | A | 532 | -84.515 | 1.645 | 73.848 | 1.00 | 26.35 |
| 4290 | CG1 | VAL | A | 532 | -84.117 | 2.683 | 74.881 | 1.00 | 25.52 |
| 4291 | CG2 | VAL | A | 532 | -85.231 | 0.453 | 74.497 | 1.00 | 24.22 |
| 4292 | C | VAL | A | 532 | -84.752 | 3.544 | 72.224 | 1.00 | 26.84 |
| 4293 | O | VAL | A | 532 | -83.931 | 3.506 | 71.319 | 1.00 | 26.29 |
| 4294 | N | PHE | A | 533 | -85.158 | 4.680 | 72.786 | 1.00 | 27.07 |
| 4295 | CA | PHE | A | 533 | -84.536 | 5.958 | 72.479 | 1.00 | 27.09 |
| 4296 | CB | PHE | A | 533 | -85.508 | 7.102 | 72.734 | 1.00 | 27.71 |
| 4297 | CG | PHE | A | 533 | -84.912 | 8.456 | 72.501 | 1.00 | 29.13 |
| 4298 | CD1 | PHE | A | 533 | -84.696 | 8.912 | 71.215 | 1.00 | 32.14 |
| 4299 | CE1 | PHE | A | 533 | -84.126 | 10.154 | 70.995 | 1.00 | 33.62 |
| 4300 | CZ | PHE | A | 533 | -83.766 | 10.949 | 72.073 | 1.00 | 31.19 |
| 4301 | CE2 | PHE | A | 533 | -83.974 | 10.499 | 73.354 | 1.00 | 30.70 |
| 4302 | CD2 | PHE | A | 533 | -84.534 | 9.261 | 73.568 | 1.00 | 29.48 |
| 4303 | C | PHE | A | 533 | -83.391 | 6.127 | 73.440 | 1.00 | 26.36 |
| 4304 | O | PHE | A | 533 | -83.572 | 5.944 | 74.631 | 1.00 | 25.98 |
| 4305 | N | ARG | A | 534 | -82.219 | 6.494 | 72.943 | 1.00 | 26.27 |
| 4306 | CA | ARG | A | 534 | -81.077 | 6.715 | 73.827 | 1.00 | 26.31 |
| 4307 | CB | ARG | A | 534 | -80.054 | 5.544 | 73.732 | 1.00 | 26.04 |
| 4308 | CG | ARG | A | 534 | -80.631 | 4.172 | 74.077 | 1.00 | 26.82 |
| 4309 | CD | ARG | A | 534 | -79.697 | 2.950 | 73.923 | 1.00 | 27.08 |
| 4310 | NE | ARG | A | 534 | -80.539 | 1.780 | 73.653 | 1.00 | 31.36 |
| 4311 | CZ | ARG | A | 534 | -80.795 | 0.855 | 74.552 | 1.00 | 31.52 |
| 4312 | NH1 | ARG | A | 534 | -80.229 | 0.938 | 75.755 | 1.00 | 36.57 |
| 4313 | NH2 | ARG | A | 534 | -81.598 | -0.147 | 74.268 | 1.00 | 25.14 |
| 4314 | C | ARG | A | 534 | -80.366 | 8.013 | 73.470 | 1.00 | 26.15 |
| 4315 | O | ARG | A | 534 | -80.453 | 8.471 | 72.345 | 1.00 | 26.29 |
| 4316 | N | LEU | A | 535 | -79.665 | 8.595 | 74.445 | 1.00 | 26.18 |
| 4317 | CA | LEU | A | 535 | -78.742 | 9.696 | 74.191 | 1.00 | 25.53 |
| 4318 | CB | LEU | A | 535 | -79.121 | 10.946 | 74.943 | 1.00 | 25.52 |
| 4319 | CG | LEU | A | 535 | -80.485 | 11.483 | 74.539 | 1.00 | 26.59 |
| 4320 | CD1 | LEU | A | 535 | -80.859 | 12.623 | 75.456 | 1.00 | 25.37 |
| 4321 | CD2 | LEU | A | 535 | -80.462 | 11.900 | 73.083 | 1.00 | 28.33 |
| 4322 | C | LEU | A | 535 | -77.434 | 9.149 | 74.709 | 1.00 | 25.14 |
| 4323 | O | LEU | A | 535 | -77.250 | 8.983 | 75.912 | 1.00 | 25.10 |
| 4324 | N | ASN | A | 536 | -76.537 | 8.833 | 73.791 | 1.00 | 24.32 |
| 4325 | CA | ASN | A | 536 | -75.314 | 8.160 | 74.164 | 1.00 | 24.10 |

FIGURE 3 CG

| A | B | C | D | E | F | G | H | I | J |
|---|---|---|---|---|---|---|---|---|---|
| 4326 | CB | ASN | A | 536 | -75.542 | 6.637 | 74.171 | 1.00 | 23.27 |
| 4327 | CG | ASN | A | 536 | -75.957 | 6.117 | 72.820 | 1.00 | 23.12 |
| 4328 | OD1 | ASN | A | 536 | -75.947 | 6.849 | 71.853 | 1.00 | 24.61 |
| 4329 | ND2 | ASN | A | 536 | -76.303 | 4.842 | 72.740 | 1.00 | 24.77 |
| 4330 | C | ASN | A | 536 | -74.237 | 8.537 | 73.187 | 1.00 | 23.67 |
| 4331 | O | ASN | A | 536 | -74.445 | 9.365 | 72.308 | 1.00 | 24.61 |
| 4332 | N | TRP | A | 537 | -73.090 | 7.908 | 73.320 | 1.00 | 23.30 |
| 4333 | CA | TRP | A | 537 | -71.958 | 8.210 | 72.460 | 1.00 | 22.74 |
| 4334 | CB | TRP | A | 537 | -70.858 | 7.203 | 72.740 | 1.00 | 22.48 |
| 4335 | CG | TRP | A | 537 | -69.576 | 7.552 | 72.158 | 1.00 | 22.46 |
| 4336 | CD1 | TRP | A | 537 | -68.950 | 8.775 | 72.196 | 1.00 | 22.69 |
| 4337 | NE1 | TRP | A | 537 | -67.734 | 8.697 | 71.564 | 1.00 | 21.09 |
| 4338 | CE2 | TRP | A | 537 | -67.535 | 7.405 | 71.150 | 1.00 | 21.17 |
| 4339 | CD2 | TRP | A | 537 | -68.693 | 6.667 | 71.490 | 1.00 | 21.98 |
| 4340 | CE3 | TRP | A | 537 | -68.736 | 5.299 | 71.187 | 1.00 | 20.10 |
| 4341 | CZ3 | TRP | A | 537 | -67.682 | 4.743 | 70.527 | 1.00 | 20.95 |
| 4342 | CH2 | TRP | A | 537 | -66.556 | 5.513 | 70.172 | 1.00 | 22.34 |
| 4343 | CZ2 | TRP | A | 537 | -66.468 | 6.843 | 70.474 | 1.00 | 18.72 |
| 4344 | C | TRP | A | 537 | -72.346 | 8.138 | 70.989 | 1.00 | 22.41 |
| 4345 | O | TRP | A | 537 | -71.956 | 9.001 | 70.194 | 1.00 | 22.36 |
| 4346 | N | ALA | A | 538 | -73.086 | 7.098 | 70.621 | 1.00 | 21.66 |
| 4347 | CA | ALA | A | 538 | -73.546 | 6.952 | 69.234 | 1.00 | 22.46 |
| 4348 | CB | ALA | A | 538 | -74.383 | 5.682 | 69.071 | 1.00 | 21.75 |
| 4349 | C | ALA | A | 538 | -74.351 | 8.187 | 68.780 | 1.00 | 22.98 |
| 4350 | O | ALA | A | 538 | -74.259 | 8.606 | 67.626 | 1.00 | 23.16 |
| 4351 | N | THR | A | 539 | -75.139 | 8.762 | 69.681 | 1.00 | 23.35 |
| 4352 | CA | THR | A | 539 | -75.881 | 9.972 | 69.340 | 1.00 | 24.60 |
| 4353 | CB | THR | A | 539 | -76.604 | 10.534 | 70.559 | 1.00 | 24.65 |
| 4354 | OG1 | THR | A | 539 | -77.309 | 9.493 | 71.232 | 1.00 | 23.63 |
| 4355 | CG2 | THR | A | 539 | -77.680 | 11.492 | 70.106 | 1.00 | 25.07 |
| 4356 | C | THR | A | 539 | -74.925 | 11.050 | 68.851 | 1.00 | 25.20 |
| 4357 | O | THR | A | 539 | -75.174 | 11.709 | 67.823 | 1.00 | 25.06 |
| 4358 | N | TYR | A | 540 | -73.834 | 11.225 | 69.598 | 1.00 | 25.14 |
| 4359 | CA | TYR | A | 540 | -72.796 | 12.190 | 69.231 | 1.00 | 25.58 |
| 4360 | CB | TYR | A | 540 | -71.786 | 12.369 | 70.379 | 1.00 | 25.49 |
| 4361 | CG | TYR | A | 540 | -70.389 | 12.592 | 69.877 | 1.00 | 26.80 |
| 4362 | CD1 | TYR | A | 540 | -69.411 | 11.604 | 69.993 | 1.00 | 27.83 |
| 4363 | CE1 | TYR | A | 540 | -68.131 | 11.813 | 69.515 | 1.00 | 28.04 |
| 4364 | CZ | TYR | A | 540 | -67.840 | 13.016 | 68.896 | 1.00 | 30.52 |
| 4365 | OH | TYR | A | 540 | -66.589 | 13.284 | 68.395 | 1.00 | 31.52 |
| 4366 | CE2 | TYR | A | 540 | -68.812 | 13.986 | 68.754 | 1.00 | 28.42 |
| 4367 | CD2 | TYR | A | 540 | -70.053 | 13.779 | 69.243 | 1.00 | 27.18 |
| 4368 | C | TYR | A | 540 | -72.076 | 11.825 | 67.935 | 1.00 | 25.78 |
| 4369 | O | TYR | A | 540 | -71.939 | 12.653 | 67.046 | 1.00 | 25.81 |
| 4370 | N | LEU | A | 541 | -71.590 | 10.593 | 67.820 | 1.00 | 26.96 |
| 4371 | CA | LEU | A | 541 | -70.898 | 10.186 | 66.590 | 1.00 | 27.12 |
| 4372 | CB | LEU | A | 541 | -70.495 | 8.711 | 66.645 | 1.00 | 27.08 |
| 4373 | CG | LEU | A | 541 | -69.503 | 8.443 | 67.781 | 1.00 | 26.42 |
| 4374 | CD1 | LEU | A | 541 | -69.291 | 6.967 | 67.989 | 1.00 | 23.43 |
| 4375 | CD2 | LEU | A | 541 | -68.189 | 9.168 | 67.503 | 1.00 | 23.14 |
| 4376 | C | LEU | A | 541 | -71.836 | 10.411 | 65.430 | 1.00 | 27.84 |

FIGURE 3 CH

| A | B | C | D | E | F | G | H | I | J |
|---|---|---|---|---|---|---|---|---|---|
| 4377 | O | LEU | A | 541 | -71.422 | 10.853 | 64.358 | 1.00 | 27.48 |
| 4378 | N | ALA | A | 542 | -73.114 | 10.125 | 65.656 | 1.00 | 28.30 |
| 4379 | CA | ALA | A | 542 | -74.115 | 10.352 | 64.627 | 1.00 | 29.47 |
| 4380 | CB | ALA | A | 542 | -75.380 | 9.549 | 64.914 | 1.00 | 28.86 |
| 4381 | C | ALA | A | 542 | -74.428 | 11.866 | 64.430 | 1.00 | 30.18 |
| 4382 | O | ALA | A | 542 | -74.312 | 12.373 | 63.326 | 1.00 | 30.01 |
| 4383 | N | SER | A | 543 | -74.808 | 12.565 | 65.492 | 1.00 | 30.73 |
| 4384 | CA | SER | A | 543 | -75.175 | 13.964 | 65.364 | 1.00 | 31.65 |
| 4385 | CB | SER | A | 543 | -75.760 | 14.473 | 66.678 | 1.00 | 31.70 |
| 4386 | OG | SER | A | 543 | -75.898 | 15.877 | 66.643 | 1.00 | 34.90 |
| 4387 | C | SER | A | 543 | -74.012 | 14.847 | 64.909 | 1.00 | 31.73 |
| 4388 | O | SER | A | 543 | -74.148 | 15.607 | 63.954 | 1.00 | 31.61 |
| 4389 | N | THR | A | 544 | -72.865 | 14.719 | 65.567 | 1.00 | 31.83 |
| 4390 | CA | THR | A | 544 | -71.720 | 15.573 | 65.256 | 1.00 | 31.83 |
| 4391 | CB | THR | A | 544 | -70.999 | 15.979 | 66.550 | 1.00 | 31.65 |
| 4392 | OG1 | THR | A | 544 | -71.915 | 16.668 | 67.412 | 1.00 | 33.07 |
| 4393 | CG2 | THR | A | 544 | -69.948 | 16.999 | 66.255 | 1.00 | 31.61 |
| 4394 | C | THR | A | 544 | -70.691 | 15.051 | 64.240 | 1.00 | 31.45 |
| 4395 | O | THR | A | 544 | -70.269 | 15.777 | 63.342 | 1.00 | 30.92 |
| 4396 | N | GLU | A | 545 | -70.259 | 13.806 | 64.369 | 1.00 | 31.31 |
| 4397 | CA | GLU | A | 545 | -69.229 | 13.351 | 63.448 | 1.00 | 30.80 |
| 4398 | CB | GLU | A | 545 | -68.293 | 12.348 | 64.124 | 1.00 | 30.72 |
| 4399 | CG | GLU | A | 545 | -67.769 | 12.799 | 65.480 | 1.00 | 30.89 |
| 4400 | CD | GLU | A | 545 | -67.024 | 14.130 | 65.432 | 1.00 | 32.37 |
| 4401 | OE1 | GLU | A | 545 | -66.896 | 14.781 | 66.495 | 1.00 | 33.28 |
| 4402 | OE2 | GLU | A | 545 | -66.547 | 14.506 | 64.341 | 1.00 | 30.39 |
| 4403 | C | GLU | A | 545 | -69.785 | 12.793 | 62.140 | 1.00 | 30.42 |
| 4404 | O | GLU | A | 545 | -69.031 | 12.460 | 61.252 | 1.00 | 30.29 |
| 4405 | N | ASN | A | 546 | -71.106 | 12.700 | 62.032 | 1.00 | 30.63 |
| 4406 | CA | ASN | A | 546 | -71.774 | 12.130 | 60.853 | 1.00 | 30.52 |
| 4407 | CB | ASN | A | 546 | -71.485 | 12.942 | 59.586 | 1.00 | 31.73 |
| 4408 | CG | ASN | A | 546 | -72.182 | 14.285 | 59.585 | 1.00 | 34.27 |
| 4409 | OD1 | ASN | A | 546 | -71.551 | 15.324 | 59.354 | 1.00 | 38.86 |
| 4410 | ND2 | ASN | A | 546 | -73.486 | 14.277 | 59.845 | 1.00 | 35.24 |
| 4411 | C | ASN | A | 546 | -71.436 | 10.667 | 60.587 | 1.00 | 29.32 |
| 4412 | O | ASN | A | 546 | -71.340 | 10.247 | 59.438 | 1.00 | 29.52 |
| 4413 | N | ILE | A | 547 | -71.243 | 9.890 | 61.637 | 1.00 | 27.84 |
| 4414 | CA | ILE | A | 547 | -70.946 | 8.482 | 61.450 | 1.00 | 26.64 |
| 4415 | CB | ILE | A | 547 | -69.911 | 8.034 | 62.500 | 1.00 | 26.27 |
| 4416 | CG1 | ILE | A | 547 | -68.565 | 8.719 | 62.236 | 1.00 | 26.48 |
| 4417 | CD1 | ILE | A | 547 | -67.665 | 8.765 | 63.449 | 1.00 | 26.42 |
| 4418 | CG2 | ILE | A | 547 | -69.759 | 6.518 | 62.502 | 1.00 | 24.99 |
| 4419 | C | ILE | A | 547 | -72.220 | 7.680 | 61.634 | 1.00 | 25.98 |
| 4420 | O | ILE | A | 547 | -72.941 | 7.939 | 62.561 | 1.00 | 26.13 |
| 4421 | N | ILE | A | 548 | -72.505 | 6.723 | 60.758 | 1.00 | 25.24 |
| 4422 | CA | ILE | A | 548 | -73.610 | 5.804 | 61.027 | 1.00 | 24.49 |
| 4423 | CB | ILE | A | 548 | -74.033 | 5.021 | 59.767 | 1.00 | 23.91 |
| 4424 | CG1 | ILE | A | 548 | -74.572 | 5.965 | 58.682 | 1.00 | 24.32 |
| 4425 | CD1 | ILE | A | 548 | -74.462 | 5.394 | 57.274 | 1.00 | 24.06 |
| 4426 | CG2 | ILE | A | 548 | -75.111 | 4.003 | 60.143 | 1.00 | 21.57 |
| 4427 | C | ILE | A | 548 | -73.119 | 4.803 | 62.051 | 1.00 | 24.50 |

FIGURE 3 CI

| A | B | C | D | E | F | G | H | I | J |
|---|---|---|---|---|---|---|---|---|---|
| 4428 | O | ILE | A | 548 | -72.060 | 4.207 | 61.885 | 1.00 | 24.29 |
| 4429 | N | VAL | A | 549 | -73.853 | 4.616 | 63.125 | 1.00 | 25.27 |
| 4430 | CA | VAL | A | 549 | -73.409 | 3.599 | 64.062 | 1.00 | 26.24 |
| 4431 | CB | VAL | A | 549 | -72.850 | 4.126 | 65.404 | 1.00 | 26.50 |
| 4432 | CG1 | VAL | A | 549 | -73.106 | 5.599 | 65.570 | 1.00 | 26.95 |
| 4433 | CG2 | VAL | A | 549 | -73.347 | 3.282 | 66.589 | 1.00 | 25.59 |
| 4434 | C | VAL | A | 549 | -74.476 | 2.539 | 64.188 | 1.00 | 26.57 |
| 4435 | O | VAL | A | 549 | -75.598 | 2.774 | 64.634 | 1.00 | 26.99 |
| 4436 | N | ALA | A | 550 | -74.095 | 1.333 | 63.782 | 1.00 | 26.46 |
| 4437 | CA | ALA | A | 550 | -75.041 | 0.273 | 63.625 | 1.00 | 25.36 |
| 4438 | CB | ALA | A | 550 | -74.866 | -0.307 | 62.236 | 1.00 | 25.10 |
| 4439 | C | ALA | A | 550 | -74.859 | -0.831 | 64.662 | 1.00 | 25.84 |
| 4440 | O | ALA | A | 550 | -73.787 | -0.974 | 65.245 | 1.00 | 25.55 |
| 4441 | N | SER | A | 551 | -75.911 | -1.618 | 64.883 | 1.00 | 25.67 |
| 4442 | CA | SER | A | 551 | -75.848 | -2.771 | 65.780 | 1.00 | 25.80 |
| 4443 | CB | SER | A | 551 | -76.385 | -2.448 | 67.169 | 1.00 | 25.63 |
| 4444 | OG | SER | A | 551 | -75.605 | -1.427 | 67.767 | 1.00 | 26.99 |
| 4445 | C | SER | A | 551 | -76.639 | -3.899 | 65.148 | 1.00 | 25.66 |
| 4446 | O | SER | A | 551 | -77.605 | -3.679 | 64.426 | 1.00 | 26.15 |
| 4447 | N | PHE | A | 552 | -76.233 | -5.119 | 65.415 | 1.00 | 25.15 |
| 4448 | CA | PHE | A | 552 | -76.852 | -6.229 | 64.729 | 1.00 | 23.89 |
| 4449 | CB | PHE | A | 552 | -76.036 | -6.571 | 63.486 | 1.00 | 22.93 |
| 4450 | CG | PHE | A | 552 | -76.510 | -7.793 | 62.761 | 1.00 | 22.92 |
| 4451 | CD1 | PHE | A | 552 | -77.566 | -7.723 | 61.863 | 1.00 | 23.12 |
| 4452 | CE1 | PHE | A | 552 | -77.982 | -8.855 | 61.194 | 1.00 | 23.52 |
| 4453 | CZ | PHE | A | 552 | -77.326 | -10.068 | 61.406 | 1.00 | 20.98 |
| 4454 | CE2 | PHE | A | 552 | -76.282 | -10.127 | 62.271 | 1.00 | 19.73 |
| 4455 | CD2 | PHE | A | 552 | -75.880 | -9.003 | 62.940 | 1.00 | 19.74 |
| 4456 | C | PHE | A | 552 | -76.972 | -7.425 | 65.656 | 1.00 | 23.86 |
| 4457 | O | PHE | A | 552 | -76.033 | -7.782 | 66.366 | 1.00 | 22.69 |
| 4458 | N | ASP | A | 553 | -78.165 | -7.999 | 65.666 | 1.00 | 23.23 |
| 4459 | CA | ASP | A | 553 | -78.432 | -9.135 | 66.484 | 1.00 | 23.30 |
| 4460 | CB | ASP | A | 553 | -79.772 | -8.961 | 67.171 | 1.00 | 22.96 |
| 4461 | CG | ASP | A | 553 | -79.765 | -7.861 | 68.211 | 1.00 | 24.34 |
| 4462 | OD1 | ASP | A | 553 | -78.682 | -7.518 | 68.751 | 1.00 | 22.95 |
| 4463 | OD2 | ASP | A | 553 | -80.830 | -7.297 | 68.565 | 1.00 | 24.54 |
| 4464 | C | ASP | A | 553 | -78.444 | -10.385 | 65.602 | 1.00 | 23.11 |
| 4465 | O | ASP | A | 553 | -79.450 | -10.696 | 64.959 | 1.00 | 23.44 |
| 4466 | N | GLY | A | 554 | -77.324 | -11.094 | 65.586 | 1.00 | 22.92 |
| 4467 | CA | GLY | A | 554 | -77.202 | -12.304 | 64.804 | 1.00 | 23.01 |
| 4468 | C | GLY | A | 554 | -77.458 | -13.510 | 65.656 | 1.00 | 23.19 |
| 4469 | O | GLY | A | 554 | -78.190 | -13.475 | 66.636 | 1.00 | 24.71 |
| 4470 | N | ARG | A | 555 | -76.852 | -14.605 | 65.271 | 1.00 | 22.95 |
| 4471 | CA | ARG | A | 555 | -77.042 | -15.828 | 66.009 | 1.00 | 22.74 |
| 4472 | CB | ARG | A | 555 | -76.322 | -16.959 | 65.298 | 1.00 | 22.40 |
| 4473 | CG | ARG | A | 555 | -77.096 | -17.432 | 64.085 | 1.00 | 22.64 |
| 4474 | CD | ARG | A | 555 | -76.412 | -18.535 | 63.298 | 1.00 | 21.05 |
| 4475 | NE | ARG | A | 555 | -75.340 | -17.971 | 62.495 | 1.00 | 21.39 |
| 4476 | CZ | ARG | A | 555 | -74.609 | -18.628 | 61.615 | 1.00 | 20.88 |
| 4477 | NH1 | ARG | A | 555 | -74.797 | -19.922 | 61.413 | 1.00 | 19.83 |
| 4478 | NH2 | ARG | A | 555 | -73.660 | -17.977 | 60.951 | 1.00 | 22.48 |

FIGURE 3 CJ

| A | B | C | D | E | F | G | H | I | J |
|---|---|---|---|---|---|---|---|---|---|
| 4479 | C | ARG | A | 555 | -76.548 | -15.698 | 67.438 | 1.00 | 22.46 |
| 4480 | O | ARG | A | 555 | -75.517 | -15.062 | 67.704 | 1.00 | 22.62 |
| 4481 | N | GLY | A | 556 | -77.261 | -16.343 | 68.344 | 1.00 | 21.79 |
| 4482 | CA | GLY | A | 556 | -76.940 | -16.274 | 69.752 | 1.00 | 22.02 |
| 4483 | C | GLY | A | 556 | -77.758 | -15.169 | 70.399 | 1.00 | 22.15 |
| 4484 | O | GLY | A | 556 | -77.910 | -15.150 | 71.614 | 1.00 | 22.08 |
| 4485 | N | SER | A | 557 | -78.266 | -14.248 | 69.581 | 1.00 | 22.09 |
| 4486 | CA | SER | A | 557 | -79.101 | -13.168 | 70.070 | 1.00 | 22.50 |
| 4487 | CB | SER | A | 557 | -79.369 | -12.109 | 68.983 | 1.00 | 22.77 |
| 4488 | OG | SER | A | 557 | -80.178 | -12.602 | 67.952 | 1.00 | 23.68 |
| 4489 | C | SER | A | 557 | -80.389 | -13.713 | 70.660 | 1.00 | 22.46 |
| 4490 | O | SER | A | 557 | -80.796 | -14.855 | 70.370 | 1.00 | 23.12 |
| 4491 | N | GLY | A | 558 | -81.031 | -12.903 | 71.495 | 1.00 | 21.95 |
| 4492 | CA | GLY | A | 558 | -82.172 | -13.372 | 72.244 | 1.00 | 21.91 |
| 4493 | C | GLY | A | 558 | -83.538 | -12.908 | 71.794 | 1.00 | 22.32 |
| 4494 | O | GLY | A | 558 | -83.681 | -12.138 | 70.843 | 1.00 | 22.48 |
| 4495 | N | TYR | A | 559 | -84.542 | -13.428 | 72.485 | 1.00 | 22.60 |
| 4496 | CA | TYR | A | 559 | -85.936 | -13.011 | 72.337 | 1.00 | 23.63 |
| 4497 | CB | TYR | A | 559 | -86.046 | -11.519 | 72.619 | 1.00 | 23.18 |
| 4498 | CG | TYR | A | 559 | -85.309 | -11.140 | 73.881 | 1.00 | 22.60 |
| 4499 | CD1 | TYR | A | 559 | -84.093 | -10.443 | 73.820 | 1.00 | 21.94 |
| 4500 | CE1 | TYR | A | 597 | -83.414 | -10.103 | 74.965 | 1.00 | 22.93 |
| 4501 | CZ | TYR | A | 597 | -83.944 | -10.442 | 76.206 | 1.00 | 22.63 |
| 4502 | OH | TYR | A | 597 | -83.250 | -10.095 | 77.353 | 1.00 | 25.67 |
| 4503 | CE2 | TYR | A | 597 | -85.142 | -11.122 | 76.293 | 1.00 | 20.25 |
| 4504 | CD2 | TYR | A | 597 | -85.812 | -11.484 | 75.126 | 1.00 | 19.76 |
| 4505 | C | TYR | A | 597 | -86.554 | -13.362 | 71.007 | 1.00 | 24.02 |
| 4506 | O | TYR | A | 597 | -87.590 | -12.798 | 70.612 | 1.00 | 24.15 |
| 4507 | N | GLN | A | 598 | -85.919 | -14.307 | 70.320 | 1.00 | 24.09 |
| 4508 | CA | GLN | A | 598 | -86.393 | -14.734 | 69.006 | 1.00 | 23.89 |
| 4509 | CB | GLN | A | 598 | -85.471 | -14.205 | 67.913 | 1.00 | 23.48 |
| 4510 | CG | GLN | A | 598 | -85.151 | -12.749 | 68.029 | 1.00 | 25.19 |
| 4511 | CD | GLN | A | 598 | -83.789 | -12.393 | 67.462 | 1.00 | 25.22 |
| 4512 | OE1 | GLN | A | 598 | -83.662 | -12.141 | 66.275 | 1.00 | 25.93 |
| 4513 | NE2 | GLN | A | 598 | -82.782 | -12.350 | 68.314 | 1.00 | 25.78 |
| 4514 | C | GLN | A | 598 | -86.458 | -16.259 | 68.938 | 1.00 | 23.85 |
| 4515 | O | GLN | A | 598 | -86.474 | -16.844 | 67.859 | 1.00 | 24.91 |
| 4516 | N | GLY | A | 599 | -86.484 | -16.906 | 70.089 | 1.00 | 23.84 |
| 4517 | CA | GLY | A | 599 | -86.520 | -18.351 | 70.119 | 1.00 | 23.61 |
| 4518 | C | GLY | A | 599 | -85.167 | -19.004 | 70.143 | 1.00 | 23.59 |
| 4519 | O | GLY | A | 599 | -84.167 | -18.411 | 69.753 | 1.00 | 24.02 |
| 4520 | N | ASP | A | 600 | -85.136 | -20.262 | 70.569 | 1.00 | 24.62 |
| 4521 | CA | ASP | A | 600 | -83.873 | -20.968 | 70.762 | 1.00 | 25.34 |
| 4522 | CB | ASP | A | 600 | -84.087 | -22.226 | 71.608 | 1.00 | 26.00 |
| 4523 | CG | ASP | A | 600 | -84.538 | -21.913 | 73.024 | 1.00 | 27.86 |
| 4524 | OD1 | ASP | A | 600 | -84.353 | -20.748 | 73.464 | 1.00 | 28.97 |
| 4525 | OD2 | ASP | A | 600 | -85.075 | -22.777 | 73.764 | 1.00 | 27.91 |
| 4526 | C | ASP | A | 600 | -83.094 | -21.335 | 69.497 | 1.00 | 25.39 |
| 4527 | O | ASP | A | 600 | -81.882 | -21.546 | 69.574 | 1.00 | 25.11 |
| 4528 | N | LYS | A | 601 | -83.748 | -21.442 | 68.348 | 1.00 | 25.53 |
| 4529 | CA | LYS | A | 601 | -82.980 | -21.863 | 67.173 | 1.00 | 26.86 |

FIGURE 3 CK

| A | B | C | D | E | F | G | H | I | J |
|---|---|---|---|---|---|---|---|---|---|
| 4530 | CB | LYS | A | 563 | -83.846 | -21.977 | 65.921 | 1.00 | 27.77 |
| 4531 | CG | LYS | A | 563 | -83.032 | -22.073 | 64.615 | 1.00 | 32.25 |
| 4532 | CD | LYS | A | 563 | -82.349 | -23.441 | 64.443 | 1.00 | 38.03 |
| 4533 | CE | LYS | A | 563 | -81.407 | -23.456 | 63.234 | 1.00 | 41.98 |
| 4534 | NZ | LYS | A | 563 | -81.007 | -24.894 | 62.897 | 1.00 | 42.27 |
| 4535 | C | LYS | A | 563 | -81.846 | -20.852 | 66.973 | 1.00 | 25.87 |
| 4536 | O | LYS | A | 563 | -80.723 | -21.211 | 66.659 | 1.00 | 25.10 |
| 4537 | N | ILE | A | 564 | -82.178 | -19.585 | 67.181 | 1.00 | 25.38 |
| 4538 | CA | ILE | A | 564 | -81.222 | -18.495 | 67.116 | 1.00 | 24.64 |
| 4539 | CB | ILE | A | 564 | -81.978 | -17.204 | 66.855 | 1.00 | 24.95 |
| 4540 | CG1 | ILE | A | 564 | -82.436 | -17.185 | 65.392 | 1.00 | 22.41 |
| 4541 | CD1 | ILE | A | 564 | -83.370 | -16.032 | 65.032 | 1.00 | 23.88 |
| 4542 | CG2 | ILE | A | 564 | -81.101 | -15.977 | 67.264 | 1.00 | 24.06 |
| 4543 | C | ILE | A | 564 | -80.378 | -18.371 | 68.401 | 1.00 | 24.04 |
| 4544 | O | ILE | A | 564 | -79.169 | -18.318 | 68.347 | 1.00 | 23.29 |
| 4545 | N | MET | A | 565 | -81.011 | -18.361 | 69.560 | 1.00 | 24.02 |
| 4546 | CA | MET | A | 565 | -80.231 | -18.205 | 70.781 | 1.00 | 24.07 |
| 4547 | CB | MET | A | 565 | -81.124 | -18.123 | 72.021 | 1.00 | 24.25 |
| 4548 | CG | MET | A | 565 | -80.342 | -17.586 | 73.226 | 1.00 | 23.18 |
| 4549 | SD | MET | A | 565 | -81.402 | -17.166 | 74.596 | 1.00 | 24.95 |
| 4550 | CE | MET | A | 565 | -81.912 | -18.826 | 75.177 | 1.00 | 18.04 |
| 4551 | C | MET | A | 565 | -79.213 | -19.307 | 70.983 | 1.00 | 23.98 |
| 4552 | O | MET | A | 565 | -78.067 | -19.051 | 71.322 | 1.00 | 23.77 |
| 4553 | N | HIS | A | 566 | -79.626 | -20.541 | 70.761 | 1.00 | 24.13 |
| 4554 | CA | HIS | A | 566 | -78.751 | -21.677 | 71.040 | 1.00 | 24.24 |
| 4555 | CB | HIS | A | 566 | -79.583 | -22.923 | 71.332 | 1.00 | 24.50 |
| 4556 | CG | HIS | A | 566 | -80.272 | -22.895 | 72.664 | 1.00 | 25.45 |
| 4557 | ND1 | HIS | A | 566 | -80.001 | -21.945 | 73.626 | 1.00 | 24.83 |
| 4558 | CE1 | HIS | A | 566 | -80.745 | -22.178 | 74.692 | 1.00 | 26.00 |
| 4559 | NE2 | HIS | A | 566 | -81.482 | -23.250 | 74.460 | 1.00 | 26.73 |
| 4560 | CD2 | HIS | A | 566 | -81.209 | -23.712 | 73.197 | 1.00 | 24.92 |
| 4561 | C | HIS | A | 566 | -77.758 | -21.982 | 69.930 | 1.00 | 24.42 |
| 4562 | O | HIS | A | 566 | -76.948 | -22.908 | 70.055 | 1.00 | 24.12 |
| 4563 | N | ALA | A | 567 | -77.799 | -21.206 | 68.850 | 1.00 | 24.23 |
| 4564 | CA | ALA | A | 567 | -76.884 | -21.470 | 67.754 | 1.00 | 24.02 |
| 4565 | CB | ALA | A | 567 | -77.084 | -20.502 | 66.634 | 1.00 | 23.70 |
| 4566 | C | ALA | A | 567 | -75.451 | -21.446 | 68.242 | 1.00 | 24.52 |
| 4567 | O | ALA | A | 567 | -74.596 | -22.139 | 67.679 | 1.00 | 24.73 |
| 4568 | N | ILE | A | 568 | -75.173 | -20.678 | 69.303 | 1.00 | 24.43 |
| 4569 | CA | ILE | A | 568 | -73.782 | -20.566 | 69.754 | 1.00 | 24.25 |
| 4570 | CB | ILE | A | 568 | -73.323 | -19.079 | 69.995 | 1.00 | 24.90 |
| 4571 | CG1 | ILE | A | 568 | -74.283 | -18.269 | 70.866 | 1.00 | 24.12 |
| 4572 | CD1 | ILE | A | 568 | -74.629 | -18.870 | 72.199 | 1.00 | 26.81 |
| 4573 | CG2 | ILE | A | 568 | -73.190 | -18.331 | 68.659 | 1.00 | 24.26 |
| 4574 | C | ILE | A | 568 | -73.355 | -21.488 | 70.893 | 1.00 | 24.48 |
| 4575 | O | ILE | A | 568 | -72.216 | -21.409 | 71.337 | 1.00 | 24.62 |
| 4576 | N | ASN | A | 569 | -74.254 | -22.368 | 71.332 | 1.00 | 24.30 |
| 4577 | CA | ASN | A | 569 | -73.985 | -23.324 | 72.406 | 1.00 | 24.74 |
| 4578 | CB | ASN | A | 569 | -75.171 | -24.288 | 72.582 | 1.00 | 25.22 |
| 4579 | CG | ASN | A | 569 | -74.954 | -25.288 | 73.711 | 1.00 | 27.56 |
| 4580 | OD1 | ASN | A | 569 | -74.955 | -26.518 | 73.490 | 1.00 | 30.92 |

FIGURE 3 CL

| A | B | C | D | E | F | G | H | I | J |
|---|---|---|---|---|---|---|---|---|---|
| 4581 | ND2 | ASN | A | 569 | -74.749 | -24.780 | 74.917 | 1.00 | 24.95 |
| 4582 | C | ASN | A | 569 | -72.709 | -24.117 | 72.207 | 1.00 | 25.11 |
| 4583 | O | ASN | A | 569 | -72.523 | -24.770 | 71.170 | 1.00 | 24.85 |
| 4584 | N | ARG | A | 570 | -71.840 | -24.050 | 73.216 | 1.00 | 25.17 |
| 4585 | CA | ARG | A | 570 | -70.553 | -24.717 | 73.226 | 1.00 | 25.82 |
| 4586 | CB | ARG | A | 570 | -70.736 | -26.230 | 73.022 | 1.00 | 26.02 |
| 4587 | CG | ARG | A | 570 | -71.375 | -26.931 | 74.213 | 1.00 | 27.93 |
| 4588 | CD | ARG | A | 570 | -71.675 | -28.402 | 73.966 | 1.00 | 31.13 |
| 4589 | NE | ARG | A | 570 | -70.452 | -29.132 | 73.648 | 1.00 | 32.29 |
| 4590 | CZ | ARG | A | 570 | -69.690 | -29.682 | 74.562 | 1.00 | 33.17 |
| 4591 | NH1 | ARG | A | 570 | -68.579 | -30.323 | 74.215 | 1.00 | 33.29 |
| 4592 | NH2 | ARG | A | 570 | -70.042 | -29.578 | 75.838 | 1.00 | 34.18 |
| 4593 | C | ARG | A | 570 | -69.628 | -24.134 | 72.167 | 1.00 | 26.12 |
| 4594 | O | ARG | A | 570 | -68.524 | -24.637 | 71.941 | 1.00 | 25.56 |
| 4595 | N | ARG | A | 571 | -70.060 | -23.043 | 71.553 | 1.00 | 26.31 |
| 4596 | CA | ARG | A | 571 | -69.362 | -22.561 | 70.384 | 1.00 | 27.64 |
| 4597 | CB | ARG | A | 571 | -70.152 | -23.020 | 69.150 | 1.00 | 27.88 |
| 4598 | CG | ARG | A | 571 | -69.302 | -23.654 | 68.055 | 1.00 | 33.59 |
| 4599 | CD | ARG | A | 571 | -69.041 | -25.192 | 68.139 | 1.00 | 38.10 |
| 4600 | NE | ARG | A | 571 | -68.118 | -25.568 | 69.192 | 1.00 | 42.59 |
| 4601 | CZ | ARG | A | 571 | -67.621 | -26.797 | 69.384 | 1.00 | 44.77 |
| 4602 | NH1 | ARG | A | 571 | -66.813 | -27.026 | 70.412 | 1.00 | 43.83 |
| 4603 | NH2 | ARG | A | 571 | -67.927 | -27.795 | 68.568 | 1.00 | 44.81 |
| 4604 | C | ARG | A | 571 | -69.154 | -21.035 | 70.397 | 1.00 | 26.90 |
| 4605 | O | ARG | A | 571 | -69.220 | -20.351 | 69.371 | 1.00 | 26.51 |
| 4606 | N | LEU | A | 572 | -68.901 | -20.509 | 71.580 | 1.00 | 26.30 |
| 4607 | CA | LEU | A | 572 | -68.638 | -19.081 | 71.726 | 1.00 | 25.74 |
| 4608 | CB | LEU | A | 572 | -68.273 | -18.761 | 73.180 | 1.00 | 25.20 |
| 4609 | CG | LEU | A | 572 | -69.414 | -18.145 | 73.987 | 1.00 | 24.72 |
| 4610 | CD1 | LEU | A | 572 | -69.184 | -18.128 | 75.494 | 1.00 | 24.38 |
| 4611 | CD2 | LEU | A | 572 | -70.753 | -18.727 | 73.627 | 1.00 | 22.29 |
| 4612 | C | LEU | A | 572 | -67.523 | -18.630 | 70.798 | 1.00 | 24.94 |
| 4613 | O | LEU | A | 572 | -66.514 | -19.328 | 70.620 | 1.00 | 25.41 |
| 4614 | N | GLY | A | 573 | -67.690 | -17.461 | 70.206 | 1.00 | 23.52 |
| 4615 | CA | GLY | A | 573 | -66.667 | -16.951 | 69.324 | 1.00 | 23.38 |
| 4616 | C | GLY | A | 573 | -66.708 | -17.500 | 67.913 | 1.00 | 23.07 |
| 4617 | O | GLY | A | 573 | -65.670 | -17.588 | 67.251 | 1.00 | 23.52 |
| 4618 | N | THR | A | 574 | -67.878 | -17.917 | 67.458 | 1.00 | 22.34 |
| 4619 | CA | THR | A | 574 | -67.989 | -18.402 | 66.090 | 1.00 | 22.60 |
| 4620 | CB | THR | A | 574 | -68.252 | -19.912 | 66.024 | 1.00 | 22.64 |
| 4621 | OG1 | THR | A | 574 | -69.451 | -20.210 | 66.750 | 1.00 | 22.61 |
| 4622 | CG2 | THR | A | 574 | -67.123 | -20.695 | 66.740 | 1.00 | 21.83 |
| 4623 | C | THR | A | 574 | -69.052 | -17.677 | 65.318 | 1.00 | 22.31 |
| 4624 | O | THR | A | 574 | -68.776 | -16.674 | 64.670 | 1.00 | 22.50 |
| 4625 | N | PHE | A | 575 | -70.274 | -18.175 | 65.388 | 1.00 | 23.15 |
| 4626 | CA | PHE | A | 575 | -71.341 | -17.610 | 64.562 | 1.00 | 24.35 |
| 4627 | CB | PHE | A | 575 | -72.613 | -18.479 | 64.579 | 1.00 | 25.15 |
| 4628 | CG | PHE | A | 575 | -72.396 | -19.952 | 64.170 | 1.00 | 26.50 |
| 4629 | CD1 | PHE | A | 575 | -71.768 | -20.288 | 62.975 | 1.00 | 28.79 |
| 4630 | CE1 | PHE | A | 575 | -71.591 | -21.620 | 62.598 | 1.00 | 30.18 |
| 4631 | CZ | PHE | A | 575 | -72.047 | -22.650 | 63.422 | 1.00 | 31.75 |

4632   CE2   PHE A 575   -72.684  -22.335  64.609  1.00  30.94
 4633   CD2   PHE A 575   -72.866  -20.969  64.973  1.00  27.57
 4634   C     PHE A 575   -71.675  -16.180  64.917  1.00  24.87
 4635   O     PHE A 575   -71.877  -15.359  64.024  1.00  26.10
 4636   N     GLU A 576   -71.723  -15.852  66.205  1.00  24.54
 4637   CA    GLU A 576   -72.023  -14.479  66.623  1.00  25.07
 4638   CB    GLU A 576   -71.966  -14.362  68.156  1.00  25.09
 4639   CG    GLU A 576   -70.588  -14.803  68.647  1.00  29.60
 4640   CD    GLU A 576   -70.568  -15.249  70.066  1.00  36.00
 4641   OE1   GLU A 576   -71.647  -15.191  70.738  1.00  41.48
 4642   OE2   GLU A 576   -69.472  -15.633  70.516  1.00  35.97
 4643   C     GLU A 576   -70.981  -13.564  66.016  1.00  24.36
 4644   O     GLU A 576   -71.282  -12.440  65.643  1.00  25.27
 4645   N     VAL A 577   -69.748  -14.049  65.920  1.00  24.26
 4646   CA    VAL A 577   -68.642  -13.263  65.372  1.00  24.64
 4647   CB    VAL A 577   -67.260  -13.920  65.687  1.00  24.48
 4648   CG1   VAL A 577   -67.002  -13.974  67.197  1.00  24.21
 4649   CG2   VAL A 577   -66.137  -13.209  64.978  1.00  22.74
 4650   C     VAL A 577   -68.786  -13.106  63.855  1.00  25.55
 4651   O     VAL A 577   -68.661  -12.000  63.319  1.00  24.62
 4652   N     GLU A 578   -69.052  -14.224  63.176  1.00  26.99
 4653   CA    GLU A 578   -69.236  -14.250  61.724  1.00  28.75
 4654   CB    GLU A 578   -69.516  -15.678  61.200  1.00  29.47
 4655   CG    GLU A 578   -69.474  -15.744  59.666  1.00  35.98
 4656   CD    GLU A 578   -70.678  -16.408  59.000  1.00  41.51
 4657   OE1   GLU A 578   -70.766  -17.667  59.027  1.00  43.85
 4658   OE2   GLU A 578   -71.528  -15.667  58.415  1.00  44.47
 4659   C     GLU A 578   -70.411  -13.385  61.326  1.00  28.18
 4660   O     GLU A 578   -70.366  -12.691  60.315  1.00  29.02
 4661   N     ASP A 579   -71.475  -13.432  62.115  1.00  27.29
 4662   CA    ASP A 579   -72.657  -12.664  61.770  1.00  26.74
 4663   CB    ASP A 579   -73.872  -13.085  62.610  1.00  26.84
 4664   CG    ASP A 579   -74.373  -14.482  62.252  1.00  27.08
 4665   OD1   ASP A 579   -73.862  -15.049  61.275  1.00  27.19
 4666   OD2   ASP A 579   -75.242  -15.106  62.901  1.00  26.42
 4667   C     ASP A 579   -72.434  -11.145  61.787  1.00  26.27
 4668   O     ASP A 579   -73.064  -10.435  61.016  1.00  26.65
 4669   N     GLN A 580   -71.529  -10.640  62.628  1.00  25.40
 4670   CA    GLN A 580   -71.254   -9.199  62.621  1.00  24.43
 4671   CB    GLN A 580   -70.470   -8.754  63.860  1.00  23.63
 4672   CG    GLN A 580   -71.186   -9.012  65.177  1.00  22.96
 4673   CD    GLN A 580   -72.359   -8.089  65.398  1.00  24.48
 4674   OE1   GLN A 580   -72.244   -6.880  65.175  1.00  23.51
 4675   NE2   GLN A 580   -73.487   -8.641  65.855  1.00  23.17
 4676   C     GLN A 580   -70.503   -8.829  61.357  1.00  24.33
 4677   O     GLN A 580   -70.728   -7.786  60.794  1.00  24.44
 4678   N     ILE A 581   -69.606   -9.698  60.910  1.00  25.25
 4679   CA    ILE A 581   -68.882   -9.459  59.670  1.00  25.47
 4680   CB    ILE A 581   -67.740  -10.503  59.505  1.00  25.79
 4681   CG1   ILE A 581   -66.747  -10.358  60.655  1.00  24.36
 4682   CD1   ILE A 581   -65.898  -11.571  60.849  1.00  26.09
```

FIGURE 3 CN

| A | B | C | D | E | F | G | H | I | J |
|---|---|---|---|---|---|---|---|---|---|
| 4683 | CG2 | ILE | A | 581 | -67.018 | -10.340 | 58.178 | 1.00 | 23.48 |
| 4684 | C | ILE | A | 581 | -69.848 | -9.479 | 58.495 | 1.00 | 25.99 |
| 4685 | O | ILE | A | 581 | -69.893 | -8.536 | 57.709 | 1.00 | 25.68 |
| 4686 | N | GLU | A | 582 | -70.655 | -10.535 | 58.400 | 1.00 | 26.98 |
| 4687 | CA | GLU | A | 582 | -71.627 | -10.649 | 57.310 | 1.00 | 27.56 |
| 4688 | CB | GLU | A | 582 | -72.440 | -11.943 | 57.439 | 1.00 | 27.57 |
| 4689 | CG | GLU | A | 582 | -72.756 | -12.676 | 56.125 | 1.00 | 32.74 |
| 4690 | CD | GLU | A | 582 | -72.859 | -11.779 | 54.910 | 1.00 | 36.03 |
| 4691 | OE1 | GLU | A | 582 | -72.301 | -10.677 | 54.938 | 1.00 | 43.19 |
| 4692 | OE2 | GLU | A | 582 | -73.505 | -12.152 | 53.922 | 1.00 | 38.32 |
| 4693 | C | GLU | A | 582 | -72.572 | -9.434 | 57.292 | 1.00 | 27.50 |
| 4694 | O | GLU | A | 582 | -72.824 | -8.846 | 56.245 | 1.00 | 27.08 |
| 4695 | N | ALA | A | 583 | -73.095 | -9.061 | 58.459 | 1.00 | 27.71 |
| 4696 | CA | ALA | A | 583 | -73.996 | -7.923 | 58.549 | 1.00 | 27.63 |
| 4697 | CB | ALA | A | 583 | -74.547 | -7.792 | 59.958 | 1.00 | 28.04 |
| 4698 | C | ALA | A | 583 | -73.307 | -6.633 | 58.108 | 1.00 | 27.53 |
| 4699 | O | ALA | A | 583 | -73.936 | -5.748 | 57.521 | 1.00 | 27.90 |
| 4700 | N | ALA | A | 584 | -72.016 | -6.518 | 58.376 | 1.00 | 27.00 |
| 4701 | CA | ALA | A | 584 | -71.264 | -5.351 | 57.884 | 1.00 | 27.08 |
| 4702 | CB | ALA | A | 584 | -69.876 | -5.302 | 58.478 | 1.00 | 26.37 |
| 4703 | C | ALA | A | 584 | -71.172 | -5.376 | 56.361 | 1.00 | 27.19 |
| 4704 | O | ALA | A | 584 | -71.324 | -4.340 | 55.709 | 1.00 | 26.53 |
| 4705 | N | ARG | A | 585 | -70.893 | -6.554 | 55.805 | 1.00 | 27.50 |
| 4706 | CA | ARG | A | 585 | -70.859 | -6.715 | 54.360 | 1.00 | 29.16 |
| 4707 | CB | ARG | A | 585 | -70.569 | -8.169 | 53.976 | 1.00 | 29.32 |
| 4708 | CG | ARG | A | 585 | -69.127 | -8.522 | 54.150 | 1.00 | 29.55 |
| 4709 | CD | ARG | A | 585 | -68.661 | -9.684 | 53.298 | 1.00 | 31.77 |
| 4710 | NE | ARG | A | 585 | -68.458 | -10.853 | 54.118 | 1.00 | 34.87 |
| 4711 | CZ | ARG | A | 585 | -67.285 | -11.288 | 54.515 | 1.00 | 37.82 |
| 4712 | NH1 | ARG | A | 585 | -66.172 | -10.666 | 54.124 | 1.00 | 39.98 |
| 4713 | NH2 | ARG | A | 585 | -67.224 | -12.361 | 55.294 | 1.00 | 38.69 |
| 4714 | C | ARG | A | 585 | -72.216 | -6.297 | 53.793 | 1.00 | 29.98 |
| 4715 | O | ARG | A | 585 | -72.286 | -5.577 | 52.788 | 1.00 | 29.89 |
| 4716 | N | GLN | A | 586 | -73.284 | -6.689 | 54.485 | 1.00 | 30.37 |
| 4717 | CA | GLN | A | 586 | -74.632 | -6.362 | 54.045 | 1.00 | 31.66 |
| 4718 | CB | GLN | A | 586 | -75.667 | -7.060 | 54.928 | 1.00 | 31.84 |
| 4719 | CG | GLN | A | 586 | -76.684 | -7.899 | 54.172 | 1.00 | 36.59 |
| 4720 | CD | GLN | A | 586 | -76.029 | -9.048 | 53.461 | 1.00 | 40.20 |
| 4721 | OE1 | GLN | A | 586 | -75.172 | -9.713 | 54.039 | 1.00 | 44.36 |
| 4722 | NE2 | GLN | A | 586 | -76.386 | -9.264 | 52.195 | 1.00 | 39.89 |
| 4723 | C | GLN | A | 586 | -74.840 | -4.854 | 54.080 | 1.00 | 31.69 |
| 4724 | O | GLN | A | 586 | -75.386 | -4.275 | 53.146 | 1.00 | 31.81 |
| 4725 | N | PHE | A | 587 | -74.422 | -4.217 | 55.174 | 1.00 | 31.91 |
| 4726 | CA | PHE | A | 587 | -74.562 | -2.776 | 55.285 | 1.00 | 31.85 |
| 4727 | CB | PHE | A | 587 | -74.022 | -2.248 | 56.610 | 1.00 | 31.23 |
| 4728 | CG | PHE | A | 587 | -74.724 | -2.795 | 57.804 | 1.00 | 30.64 |
| 4729 | CD1 | PHE | A | 587 | -76.040 | -3.231 | 57.711 | 1.00 | 29.81 |
| 4730 | CE1 | PHE | A | 587 | -76.699 | -3.757 | 58.824 | 1.00 | 28.57 |
| 4731 | CZ | PHE | A | 587 | -76.038 | -3.835 | 60.035 | 1.00 | 28.65 |
| 4732 | CE2 | PHE | A | 587 | -74.716 | -3.408 | 60.138 | 1.00 | 28.60 |
| 4733 | CD2 | PHE | A | 587 | -74.065 | -2.895 | 59.026 | 1.00 | 28.50 |

FIGURE 3 CO

| A | B | C | D | E | F | G | H | I | J |
|---|---|---|---|---|---|---|---|---|---|
| 4734 | C | PHE | A | 587 | -73.799 | -2.137 | 54.156 | 1.00 | 32.30 |
| 4735 | O | PHE | A | 587 | -74.278 | -1.195 | 53.544 | 1.00 | 32.07 |
| 4736 | N | SER | A | 588 | -72.610 | -2.646 | 53.862 | 1.00 | 33.09 |
| 4737 | CA | SER | A | 588 | -71.858 | -2.014 | 52.793 | 1.00 | 34.56 |
| 4738 | CB | SER | A | 588 | -70.401 | -2.484 | 52.698 | 1.00 | 33.97 |
| 4739 | OG | SER | A | 588 | -70.287 | -3.892 | 52.705 | 1.00 | 37.23 |
| 4740 | C | SER | A | 588 | -72.625 | -2.107 | 51.478 | 1.00 | 35.02 |
| 4741 | O | SER | A | 588 | -72.614 | -1.174 | 50.691 | 1.00 | 36.03 |
| 4742 | N | LYS | A | 589 | -73.338 | -3.205 | 51.259 | 1.00 | 35.40 |
| 4743 | CA | LYS | A | 589 | -74.123 | -3.325 | 50.030 | 1.00 | 35.48 |
| 4744 | CB | LYS | A | 589 | -74.426 | -4.792 | 49.693 | 1.00 | 35.59 |
| 4745 | CG | LYS | A | 589 | -73.147 | -5.576 | 49.328 | 1.00 | 36.84 |
| 4746 | CD | LYS | A | 589 | -73.398 | -6.653 | 48.284 | 1.00 | 38.33 |
| 4747 | CE | LYS | A | 589 | -73.575 | -8.012 | 48.911 | 1.00 | 39.71 |
| 4748 | NZ | LYS | A | 589 | -75.002 | -8.300 | 49.224 | 1.00 | 40.52 |
| 4749 | C | LYS | A | 589 | -75.394 | -2.480 | 50.042 | 1.00 | 35.12 |
| 4750 | O | LYS | A | 589 | -76.239 | -2.605 | 49.156 | 1.00 | 35.29 |
| 4751 | N | MET | A | 590 | -75.537 | -1.601 | 51.024 | 1.00 | 34.69 |
| 4752 | CA | MET | A | 590 | -76.740 | -0.767 | 51.048 | 1.00 | 33.79 |
| 4753 | CB | MET | A | 590 | -77.262 | -0.569 | 52.458 | 1.00 | 33.69 |
| 4754 | CG | MET | A | 590 | -77.937 | -1.755 | 53.037 | 1.00 | 31.72 |
| 4755 | SD | MET | A | 590 | -78.280 | -1.418 | 54.752 | 1.00 | 32.99 |
| 4756 | CE | MET | A | 590 | -78.912 | -3.103 | 55.209 | 1.00 | 29.27 |
| 4757 | C | MET | A | 590 | -76.563 | 0.589 | 50.368 | 1.00 | 33.45 |
| 4758 | O | MET | A | 590 | -77.516 | 1.365 | 50.296 | 1.00 | 33.67 |
| 4759 | N | GLY | A | 591 | -75.348 | 0.889 | 49.918 | 1.00 | 32.59 |
| 4760 | CA | GLY | A | 591 | -75.121 | 2.077 | 49.109 | 1.00 | 32.15 |
| 4761 | C | GLY | A | 591 | -74.686 | 3.369 | 49.788 | 1.00 | 31.95 |
| 4762 | O | GLY | A | 591 | -74.040 | 4.199 | 49.163 | 1.00 | 31.35 |
| 4763 | N | PHE | A | 592 | -75.040 | 3.552 | 51.055 | 1.00 | 31.61 |
| 4764 | CA | PHE | A | 592 | -74.670 | 4.767 | 51.752 | 1.00 | 31.68 |
| 4765 | CB | PHE | A | 592 | -75.899 | 5.387 | 52.405 | 1.00 | 31.22 |
| 4766 | CG | PHE | A | 592 | -76.687 | 4.424 | 53.230 | 1.00 | 31.65 |
| 4767 | CD1 | PHE | A | 592 | -77.873 | 3.889 | 52.750 | 1.00 | 31.62 |
| 4768 | CE1 | PHE | A | 592 | -78.608 | 3.008 | 53.518 | 1.00 | 30.54 |
| 4769 | CZ | PHE | A | 592 | -78.142 | 2.636 | 54.752 | 1.00 | 33.03 |
| 4770 | CE2 | PHE | A | 592 | -76.941 | 3.148 | 55.237 | 1.00 | 30.57 |
| 4771 | CD2 | PHE | A | 592 | -76.232 | 4.032 | 54.486 | 1.00 | 30.78 |
| 4772 | C | PHE | A | 592 | -73.544 | 4.549 | 52.774 | 1.00 | 31.58 |
| 4773 | O | PHE | A | 592 | -73.324 | 5.367 | 53.667 | 1.00 | 31.89 |
| 4774 | N | VAL | A | 593 | -72.813 | 3.462 | 52.620 | 1.00 | 31.73 |
| 4775 | CA | VAL | A | 593 | -71.753 | 3.134 | 53.559 | 1.00 | 31.79 |
| 4776 | CB | VAL | A | 593 | -72.012 | 1.740 | 54.213 | 1.00 | 32.37 |
| 4777 | CG1 | VAL | A | 593 | -70.799 | 1.260 | 54.986 | 1.00 | 32.98 |
| 4778 | CG2 | VAL | A | 593 | -73.242 | 1.798 | 55.119 | 1.00 | 31.20 |
| 4779 | C | VAL | A | 593 | -70.410 | 3.166 | 52.854 | 1.00 | 31.65 |
| 4780 | O | VAL | A | 593 | -70.260 | 2.579 | 51.800 | 1.00 | 31.88 |
| 4781 | N | ASP | A | 594 | -69.436 | 3.875 | 53.418 | 1.00 | 31.26 |
| 4782 | CA | ASP | A | 594 | -68.103 | 3.920 | 52.821 | 1.00 | 31.13 |
| 4783 | CB | ASP | A | 594 | -67.373 | 5.178 | 53.268 | 1.00 | 30.73 |
| 4784 | CG | ASP | A | 594 | -65.996 | 5.262 | 52.694 | 1.00 | 30.54 |

FIGURE 3 CP

| A | B | C | D | E | F | G | H | I | J |
|---|---|---|---|---|---|---|---|---|---|
| 4785 | OD1 | ASP | A | 594 | -65.298 | 6.276 | 52.932 | 1.00 | 31.10 |
| 4786 | OD2 | ASP | A | 594 | -65.535 | 4.351 | 51.980 | 1.00 | 29.73 |
| 4787 | C | ASP | A | 594 | -67.268 | 2.680 | 53.188 | 1.00 | 31.66 |
| 4788 | O | ASP | A | 594 | -66.721 | 2.589 | 54.288 | 1.00 | 31.47 |
| 4789 | N | ASN | A | 595 | -67.157 | 1.742 | 52.256 | 1.00 | 32.31 |
| 4790 | CA | ASN | A | 595 | -66.447 | 0.486 | 52.481 | 1.00 | 33.15 |
| 4791 | CB | ASN | A | 595 | -66.375 | -0.314 | 51.186 | 1.00 | 33.65 |
| 4792 | CG | ASN | A | 595 | -67.719 | -0.824 | 50.775 | 1.00 | 38.94 |
| 4793 | OD1 | ASN | A | 595 | -68.738 | -0.408 | 51.346 | 1.00 | 45.03 |
| 4794 | ND2 | ASN | A | 595 | -67.757 | -1.729 | 49.792 | 1.00 | 42.29 |
| 4795 | C | ASN | A | 595 | -65.056 | 0.630 | 53.059 | 1.00 | 32.62 |
| 4796 | O | ASN | A | 595 | -64.505 | -0.304 | 53.641 | 1.00 | 32.40 |
| 4797 | N | LYS | A | 596 | -64.484 | 1.805 | 52.897 | 1.00 | 32.33 |
| 4798 | CA | LYS | A | 596 | -63.135 | 2.024 | 53.333 | 1.00 | 32.38 |
| 4799 | CB | LYS | A | 596 | -62.454 | 3.010 | 52.387 | 1.00 | 33.19 |
| 4800 | CG | LYS | A | 596 | -62.424 | 2.514 | 50.961 | 1.00 | 35.40 |
| 4801 | CD | LYS | A | 596 | -61.092 | 2.823 | 50.317 | 1.00 | 40.22 |
| 4802 | CE | LYS | A | 596 | -60.853 | 4.328 | 50.276 | 1.00 | 42.88 |
| 4803 | NZ | LYS | A | 596 | -61.988 | 4.993 | 49.567 | 1.00 | 44.77 |
| 4804 | C | LYS | A | 596 | -63.064 | 2.516 | 54.763 | 1.00 | 31.21 |
| 4805 | O | LYS | A | 596 | -61.985 | 2.590 | 55.318 | 1.00 | 31.59 |
| 4806 | N | ARG | A | 597 | -64.217 | 2.841 | 55.338 | 1.00 | 29.75 |
| 4807 | CA | ARG | A | 597 | -64.313 | 3.364 | 56.695 | 1.00 | 28.43 |
| 4808 | CB | ARG | A | 597 | -64.513 | 4.888 | 56.671 | 1.00 | 28.70 |
| 4809 | CG | ARG | A | 597 | -63.307 | 5.654 | 56.103 | 1.00 | 28.99 |
| 4810 | CD | ARG | A | 597 | -63.447 | 7.156 | 56.153 | 1.00 | 28.51 |
| 4811 | NE | ARG | A | 597 | -64.579 | 7.588 | 55.339 | 1.00 | 33.03 |
| 4812 | CZ | ARG | A | 597 | -65.195 | 8.752 | 55.473 | 1.00 | 33.59 |
| 4813 | NH1 | ARG | A | 597 | -64.780 | 9.614 | 56.396 | 1.00 | 33.72 |
| 4814 | NH2 | ARG | A | 597 | -66.222 | 9.061 | 54.680 | 1.00 | 33.44 |
| 4815 | C | ARG | A | 597 | -65.426 | 2.701 | 57.510 | 1.00 | 27.19 |
| 4816 | O | ARG | A | 597 | -66.436 | 3.319 | 57.861 | 1.00 | 26.73 |
| 4817 | N | ILE | A | 598 | -65.230 | 1.427 | 57.799 | 1.00 | 25.80 |
| 4818 | CA | ILE | A | 598 | -66.137 | 0.688 | 58.639 | 1.00 | 24.49 |
| 4819 | CB | ILE | A | 598 | -66.617 | -0.567 | 57.916 | 1.00 | 24.74 |
| 4820 | CG1 | ILE | A | 598 | -67.481 | -0.187 | 56.706 | 1.00 | 24.85 |
| 4821 | CD1 | ILE | A | 598 | -67.704 | -1.335 | 55.743 | 1.00 | 24.67 |
| 4822 | CG2 | ILE | A | 598 | -67.430 | -1.444 | 58.857 | 1.00 | 24.93 |
| 4823 | C | ILE | A | 598 | -65.334 | 0.301 | 59.858 | 1.00 | 23.90 |
| 4824 | O | ILE | A | 598 | -64.272 | -0.279 | 59.744 | 1.00 | 23.23 |
| 4825 | N | ALA | A | 599 | -65.827 | 0.664 | 61.027 | 1.00 | 23.45 |
| 4826 | CA | ALA | A | 599 | -65.160 | 0.328 | 62.268 | 1.00 | 22.40 |
| 4827 | CB | ALA | A | 599 | -64.747 | 1.585 | 63.000 | 1.00 | 21.96 |
| 4828 | C | ALA | A | 599 | -66.121 | -0.500 | 63.113 | 1.00 | 22.02 |
| 4829 | O | ALA | A | 599 | -67.296 | -0.687 | 62.746 | 1.00 | 22.71 |
| 4830 | N | ILE | A | 600 | -65.622 | -0.960 | 64.257 | 1.00 | 20.97 |
| 4831 | CA | ILE | A | 600 | -66.371 | -1.826 | 65.137 | 1.00 | 20.54 |
| 4832 | CB | ILE | A | 600 | -66.192 | -3.232 | 64.592 | 1.00 | 20.86 |
| 4833 | CG1 | ILE | A | 600 | -67.310 | -4.181 | 65.027 | 1.00 | 22.29 |
| 4834 | CD1 | ILE | A | 600 | -66.944 | -5.045 | 66.119 | 1.00 | 26.19 |
| 4835 | CG2 | ILE | A | 600 | -64.791 | -3.770 | 64.878 | 1.00 | 18.98 |

FIGURE 3 CQ

| A | B | C | D | E | F | G | H | I | J |
|---|---|---|---|---|---|---|---|---|---|
| 4836 | C | ILE | A | 600 | -65.854 | -1.658 | 66.568 | 1.00 | 20.20 |
| 4837 | O | ILE | A | 600 | -64.666 | -1.479 | 66.779 | 1.00 | 20.38 |
| 4838 | N | TRP | A | 601 | -66.752 | -1.651 | 67.550 | 1.00 | 19.65 |
| 4839 | CA | TRP | A | 601 | -66.333 | -1.504 | 68.922 | 1.00 | 19.05 |
| 4840 | CB | TRP | A | 601 | -66.154 | -0.035 | 69.317 | 1.00 | 19.24 |
| 4841 | CG | TRP | A | 601 | -67.373 | 0.620 | 69.882 | 1.00 | 18.88 |
| 4842 | CD1 | TRP | A | 601 | -68.465 | 1.053 | 69.185 | 1.00 | 19.07 |
| 4843 | NE1 | TRP | A | 601 | -69.379 | 1.616 | 70.040 | 1.00 | 18.07 |
| 4844 | CE2 | TRP | A | 601 | -68.879 | 1.575 | 71.310 | 1.00 | 17.52 |
| 4845 | CD2 | TRP | A | 601 | -67.613 | 0.959 | 71.246 | 1.00 | 18.30 |
| 4846 | CE3 | TRP | A | 601 | -66.896 | 0.777 | 72.436 | 1.00 | 19.10 |
| 4847 | CZ3 | TRP | A | 601 | -67.446 | 1.212 | 73.619 | 1.00 | 17.74 |
| 4848 | CH2 | TRP | A | 601 | -68.711 | 1.825 | 73.652 | 1.00 | 18.95 |
| 4849 | CZ2 | TRP | A | 601 | -69.440 | 2.021 | 72.505 | 1.00 | 18.66 |
| 4850 | C | TRP | A | 601 | -67.344 | -2.152 | 69.821 | 1.00 | 18.80 |
| 4851 | O | TRP | A | 601 | -68.487 | -2.311 | 69.453 | 1.00 | 18.02 |
| 4852 | N | GLY | A | 602 | -66.890 | -2.500 | 71.018 | 1.00 | 18.67 |
| 4853 | CA | GLY | A | 602 | -67.697 | -3.197 | 71.990 | 1.00 | 18.53 |
| 4854 | C | GLY | A | 602 | -67.006 | -3.251 | 73.334 | 1.00 | 18.13 |
| 4855 | O | GLY | A | 602 | -65.801 | -3.056 | 73.416 | 1.00 | 17.50 |
| 4856 | N | TRP | A | 603 | -67.800 | -3.507 | 74.368 | 1.00 | 19.13 |
| 4857 | CA | TRP | A | 603 | -67.376 | -3.538 | 75.761 | 1.00 | 20.22 |
| 4858 | CB | TRP | A | 603 | -68.257 | -2.564 | 76.553 | 1.00 | 21.35 |
| 4859 | CG | TRP | A | 603 | -67.685 | -1.992 | 77.818 | 1.00 | 22.59 |
| 4860 | CD1 | TRP | A | 603 | -67.293 | -2.672 | 78.948 | 1.00 | 23.68 |
| 4861 | NE1 | TRP | A | 603 | -66.830 | -1.787 | 79.895 | 1.00 | 22.81 |
| 4862 | CE2 | TRP | A | 603 | -66.929 | -0.511 | 79.392 | 1.00 | 24.43 |
| 4863 | CD2 | TRP | A | 603 | -67.460 | -0.607 | 78.089 | 1.00 | 22.74 |
| 4864 | CE3 | TRP | A | 603 | -67.653 | 0.571 | 77.361 | 1.00 | 23.54 |
| 4865 | CZ3 | TRP | A | 603 | -67.305 | 1.788 | 77.942 | 1.00 | 22.90 |
| 4866 | CH2 | TRP | A | 603 | -66.799 | 1.851 | 79.227 | 1.00 | 22.27 |
| 4867 | CZ2 | TRP | A | 603 | -66.594 | 0.721 | 79.974 | 1.00 | 24.33 |
| 4868 | C | TRP | A | 603 | -67.653 | -4.927 | 76.283 | 1.00 | 20.37 |
| 4869 | O | TRP | A | 603 | -68.703 | -5.484 | 75.993 | 1.00 | 20.67 |
| 4870 | N | SER | A | 604 | -66.742 | -5.484 | 77.076 | 1.00 | 20.51 |
| 4871 | CA | SER | A | 604 | -66.990 | -6.793 | 77.672 | 1.00 | 20.36 |
| 4872 | CB | SER | A | 604 | -68.219 | -6.726 | 78.567 | 1.00 | 19.86 |
| 4873 | OG | SER | A | 604 | -68.161 | -7.730 | 79.566 | 1.00 | 20.74 |
| 4874 | C | SER | A | 604 | -67.154 | -7.862 | 76.583 | 1.00 | 20.12 |
| 4875 | O | SER | A | 604 | -66.245 | -8.073 | 75.784 | 1.00 | 20.16 |
| 4876 | N | TYR | A | 605 | -68.297 | -8.533 | 76.540 | 1.00 | 20.10 |
| 4877 | CA | TYR | A | 605 | -68.518 | -9.518 | 75.486 | 1.00 | 20.37 |
| 4878 | CB | TYR | A | 605 | -69.903 | -10.184 | 75.584 | 1.00 | 20.14 |
| 4879 | CG | TYR | A | 605 | -69.951 | -11.514 | 74.828 | 1.00 | 20.65 |
| 4880 | CD1 | TYR | A | 605 | -69.848 | -12.733 | 75.497 | 1.00 | 20.20 |
| 4881 | CE1 | TYR | A | 605 | -69.875 | -13.935 | 74.810 | 1.00 | 20.48 |
| 4882 | CZ | TYR | A | 605 | -69.989 | -13.923 | 73.430 | 1.00 | 22.31 |
| 4883 | OH | TYR | A | 605 | -70.006 | -15.103 | 72.698 | 1.00 | 19.08 |
| 4884 | CE2 | TYR | A | 605 | -70.074 | -12.714 | 72.759 | 1.00 | 20.96 |
| 4885 | CD2 | TYR | A | 605 | -70.029 | -11.537 | 73.447 | 1.00 | 19.30 |
| 4886 | C | TYR | A | 605 | -68.345 | -8.832 | 74.135 | 1.00 | 20.06 |

FIGURE 3 CR

| A | B | C | D | E | F | G | H | I | J |
|---|---|---|---|---|---|---|---|---|---|
| 4887 | O | TYR | A | 605 | -67.813 | -9.416 | 73.184 | 1.00 | 20.26 |
| 4888 | N | GLY | A | 606 | -68.772 | -7.576 | 74.063 | 1.00 | 19.47 |
| 4889 | CA | GLY | A | 606 | -68.587 | -6.807 | 72.859 | 1.00 | 19.08 |
| 4890 | C | GLY | A | 606 | -67.126 | -6.556 | 72.532 | 1.00 | 19.25 |
| 4891 | O | GLY | A | 606 | -66.784 | -6.410 | 71.375 | 1.00 | 19.90 |
| 4892 | N | GLY | A | 607 | -66.263 | -6.471 | 73.539 | 1.00 | 19.37 |
| 4893 | CA | GLY | A | 607 | -64.846 | -6.285 | 73.288 | 1.00 | 19.47 |
| 4894 | C | GLY | A | 607 | -64.241 | -7.557 | 72.736 | 1.00 | 19.64 |
| 4895 | O | GLY | A | 607 | -63.327 | -7.540 | 71.912 | 1.00 | 20.22 |
| 4896 | N | TYR | A | 608 | -64.789 | -8.677 | 73.180 | 1.00 | 19.76 |
| 4897 | CA | TYR | A | 608 | -64.337 | -9.971 | 72.733 | 1.00 | 19.82 |
| 4898 | CB | TYR | A | 608 | -65.032 | -11.051 | 73.555 | 1.00 | 20.02 |
| 4899 | CG | TYR | A | 608 | -64.816 | -12.453 | 73.029 | 1.00 | 19.56 |
| 4900 | CD1 | TYR | A | 608 | -65.881 | -13.193 | 72.561 | 1.00 | 18.04 |
| 4901 | CE1 | TYR | A | 608 | -65.710 | -14.481 | 72.069 | 1.00 | 18.41 |
| 4902 | CZ | TYR | A | 608 | -64.480 | -15.056 | 72.070 | 1.00 | 18.91 |
| 4903 | OH | TYR | A | 608 | -64.386 | -16.339 | 71.600 | 1.00 | 19.03 |
| 4904 | CE2 | TYR | A | 608 | -63.367 | -14.352 | 72.543 | 1.00 | 18.99 |
| 4905 | CD2 | TYR | A | 608 | -63.544 | -13.043 | 73.026 | 1.00 | 19.02 |
| 4906 | C | TYR | A | 608 | -64.647 | -10.165 | 71.268 | 1.00 | 19.33 |
| 4907 | O | TYR | A | 608 | -63.785 | -10.541 | 70.481 | 1.00 | 19.69 |
| 4908 | N | VAL | A | 609 | -65.884 | -9.891 | 70.899 | 1.00 | 19.79 |
| 4909 | CA | VAL | A | 609 | -66.332 | -10.058 | 69.509 | 1.00 | 19.80 |
| 4910 | CB | VAL | A | 609 | -67.851 | -9.966 | 69.441 | 1.00 | 19.50 |
| 4911 | CG1 | VAL | A | 609 | -68.363 | -9.936 | 67.988 | 1.00 | 17.59 |
| 4912 | CG2 | VAL | A | 609 | -68.423 | -11.129 | 70.204 | 1.00 | 18.52 |
| 4913 | C | VAL | A | 609 | -65.681 | -9.042 | 68.601 | 1.00 | 20.82 |
| 4914 | O | VAL | A | 609 | -65.329 | -9.340 | 67.455 | 1.00 | 21.36 |
| 4915 | N | THR | A | 610 | -65.480 | -7.837 | 69.121 | 1.00 | 20.90 |
| 4916 | CA | THR | A | 610 | -64.789 | -6.816 | 68.351 | 1.00 | 20.87 |
| 4917 | CB | THR | A | 610 | -64.740 | -5.495 | 69.167 | 1.00 | 20.91 |
| 4918 | OG1 | THR | A | 610 | -65.965 | -4.785 | 68.971 | 1.00 | 22.30 |
| 4919 | CG2 | THR | A | 610 | -63.707 | -4.544 | 68.630 | 1.00 | 21.50 |
| 4920 | C | THR | A | 610 | -63.394 | -7.313 | 68.007 | 1.00 | 20.98 |
| 4921 | O | THR | A | 610 | -62.941 | -7.194 | 66.860 | 1.00 | 22.27 |
| 4922 | N | SER | A | 611 | -62.709 | -7.876 | 68.996 | 1.00 | 20.87 |
| 4923 | CA | SER | A | 611 | -61.348 | -8.392 | 68.812 | 1.00 | 20.57 |
| 4924 | CB | SER | A | 611 | -60.729 | -8.720 | 70.176 | 1.00 | 20.33 |
| 4925 | OG | SER | A | 611 | -60.765 | -7.600 | 71.046 | 1.00 | 20.22 |
| 4926 | C | SER | A | 611 | -61.326 | -9.649 | 67.927 | 1.00 | 20.65 |
| 4927 | O | SER | A | 611 | -60.479 | -9.803 | 67.049 | 1.00 | 20.83 |
| 4928 | N | MET | A | 612 | -62.238 | -10.568 | 68.197 | 1.00 | 20.77 |
| 4929 | CA | MET | A | 612 | -62.367 | -11.751 | 67.370 | 1.00 | 21.12 |
| 4930 | CB | MET | A | 612 | -63.511 | -12.606 | 67.889 | 1.00 | 20.97 |
| 4931 | CG | MET | A | 612 | -63.193 | -13.164 | 69.283 | 1.00 | 21.19 |
| 4932 | SD | MET | A | 612 | -61.798 | -14.330 | 69.207 | 1.00 | 23.15 |
| 4933 | CE | MET | A | 612 | -62.568 | -15.751 | 68.577 | 1.00 | 22.70 |
| 4934 | C | MET | A | 612 | -62.618 | -11.310 | 65.931 | 1.00 | 21.34 |
| 4935 | O | MET | A | 612 | -61.983 | -11.787 | 64.992 | 1.00 | 20.82 |
| 4936 | N | VAL | A | 613 | -63.527 | -10.364 | 65.764 | 1.00 | 21.34 |
| 4937 | CA | VAL | A | 613 | -63.797 | -9.841 | 64.439 | 1.00 | 21.73 |

FIGURE 3 CS

| A | B | C | D | E | F | G | H | I | J |
|---|---|---|---|---|---|---|---|---|---|
| 4938 | CB | VAL | A | 613 | -64.908 | -8.765 | 64.483 | 1.00 | 22.08 |
| 4939 | CG1 | VAL | A | 613 | -64.827 | -7.843 | 63.272 | 1.00 | 20.14 |
| 4940 | CG2 | VAL | A | 613 | -66.283 | -9.398 | 64.590 | 1.00 | 20.64 |
| 4941 | C | VAL | A | 613 | -62.541 | -9.189 | 63.833 | 1.00 | 22.48 |
| 4942 | O | VAL | A | 613 | -62.172 | -9.483 | 62.709 | 1.00 | 23.29 |
| 4943 | N | LEU | A | 614 | -61.910 | -8.262 | 64.559 | 1.00 | 22.81 |
| 4944 | CA | LEU | A | 614 | -60.700 | -7.582 | 64.071 | 1.00 | 22.75 |
| 4945 | CB | LEU | A | 614 | -60.168 | -6.632 | 65.127 | 1.00 | 22.12 |
| 4946 | CG | LEU | A | 614 | -60.839 | -5.259 | 65.192 | 1.00 | 22.33 |
| 4947 | CD1 | LEU | A | 614 | -60.855 | -4.586 | 63.827 | 1.00 | 20.46 |
| 4948 | CD2 | LEU | A | 614 | -60.135 | -4.379 | 66.227 | 1.00 | 19.62 |
| 4949 | C | LEU | A | 614 | -59.576 | -8.562 | 63.696 | 1.00 | 23.50 |
| 4950 | O | LEU | A | 614 | -58.803 | -8.318 | 62.767 | 1.00 | 22.74 |
| 4951 | N | GLY | A | 615 | -59.469 | -9.679 | 64.411 | 1.00 | 24.16 |
| 4952 | CA | GLY | A | 615 | -58.389 | -10.598 | 64.125 | 1.00 | 24.56 |
| 4953 | C | GLY | A | 615 | -58.811 | -11.723 | 63.204 | 1.00 | 25.13 |
| 4954 | O | GLY | A | 615 | -58.144 | -12.750 | 63.121 | 1.00 | 25.78 |
| 4955 | N | SER | A | 616 | -59.914 | -11.516 | 62.493 | 1.00 | 24.85 |
| 4956 | CA | SER | A | 616 | -60.465 | -12.555 | 61.625 | 1.00 | 25.43 |
| 4957 | CB | SER | A | 616 | -61.980 | -12.439 | 61.552 | 1.00 | 24.54 |
| 4958 | OG | SER | A | 616 | -62.338 | -11.405 | 60.653 | 1.00 | 25.35 |
| 4959 | C | SER | A | 616 | -59.914 | -12.534 | 60.201 | 1.00 | 26.05 |
| 4960 | O | SER | A | 616 | -60.066 | -13.505 | 59.475 | 1.00 | 26.76 |
| 4961 | N | GLY | A | 617 | -59.319 | -11.418 | 59.790 | 1.00 | 26.16 |
| 4962 | CA | GLY | A | 617 | -58.770 | -11.308 | 58.458 | 1.00 | 26.91 |
| 4963 | C | GLY | A | 617 | -59.816 | -11.051 | 57.390 | 1.00 | 27.84 |
| 4964 | O | GLY | A | 617 | -59.518 | -11.116 | 56.198 | 1.00 | 28.65 |
| 4965 | N | SER | A | 618 | -61.041 | -10.746 | 57.806 | 1.00 | 27.72 |
| 4966 | CA | SER | A | 618 | -62.104 | -10.495 | 56.854 | 1.00 | 27.42 |
| 4967 | CB | SER | A | 618 | -63.412 | -10.148 | 57.573 | 1.00 | 27.27 |
| 4968 | OG | SER | A | 618 | -63.443 | -8.776 | 57.938 | 1.00 | 26.02 |
| 4969 | C | SER | A | 618 | -61.745 | -9.365 | 55.905 | 1.00 | 27.44 |
| 4970 | O | SER | A | 618 | -62.182 | -9.359 | 54.775 | 1.00 | 28.42 |
| 4971 | N | GLY | A | 619 | -60.958 | -8.402 | 56.368 | 1.00 | 27.41 |
| 4972 | CA | GLY | A | 619 | -60.626 | -7.237 | 55.561 | 1.00 | 26.48 |
| 4973 | C | GLY | A | 619 | -61.742 | -6.213 | 55.513 | 1.00 | 25.98 |
| 4974 | O | GLY | A | 619 | -61.645 | -5.190 | 54.857 | 1.00 | 26.95 |
| 4975 | N | VAL | A | 620 | -62.814 | -6.471 | 56.237 | 1.00 | 25.53 |
| 4976 | CA | VAL | A | 620 | -63.963 | -5.596 | 56.199 | 1.00 | 24.51 |
| 4977 | CB | VAL | A | 620 | -65.201 | -6.328 | 56.718 | 1.00 | 24.57 |
| 4978 | CG1 | VAL | A | 620 | -66.337 | -5.339 | 56.992 | 1.00 | 26.07 |
| 4979 | CG2 | VAL | A | 620 | -65.661 | -7.401 | 55.700 | 1.00 | 23.73 |
| 4980 | C | VAL | A | 620 | -63.745 | -4.355 | 57.033 | 1.00 | 24.42 |
| 4981 | O | VAL | A | 620 | -64.141 | -3.242 | 56.652 | 1.00 | 24.86 |
| 4982 | N | PHE | A | 621 | -63.075 | -4.535 | 58.159 | 1.00 | 23.10 |
| 4983 | CA | PHE | A | 621 | -62.945 | -3.473 | 59.115 | 1.00 | 23.04 |
| 4984 | CB | PHE | A | 621 | -63.239 | -4.007 | 60.528 | 1.00 | 22.40 |
| 4985 | CG | PHE | A | 621 | -64.635 | -4.567 | 60.673 | 1.00 | 22.15 |
| 4986 | CD1 | PHE | A | 621 | -64.936 | -5.855 | 60.234 | 1.00 | 21.19 |
| 4987 | CE1 | PHE | A | 621 | -66.213 | -6.367 | 60.360 | 1.00 | 19.39 |
| 4988 | CZ | PHE | A | 621 | -67.210 | -5.607 | 60.905 | 1.00 | 18.20 |

FIGURE 3 CT

| A | B | C | D | E | F | G | H | I | J |
|---|---|---|---|---|---|---|---|---|---|
| 4989 | CE2 | PHE | A | 621 | -66.930 | -4.325 | 61.341 | 1.00 | 21.85 |
| 4990 | CD2 | PHE | A | 621 | -65.646 | -3.810 | 61.220 | 1.00 | 20.24 |
| 4991 | C | PHE | A | 621 | -61.605 | -2.790 | 59.038 | 1.00 | 23.53 |
| 4992 | O | PHE | A | 621 | -60.574 | -3.434 | 58.902 | 1.00 | 23.71 |
| 4993 | N | LYS | A | 622 | -61.625 | -1.468 | 59.122 | 1.00 | 23.65 |
| 4994 | CA | LYS | A | 622 | -60.373 | -0.731 | 59.100 | 1.00 | 23.95 |
| 4995 | CB | LYS | A | 622 | -60.603 | 0.675 | 58.550 | 1.00 | 23.87 |
| 4996 | CG | LYS | A | 622 | -59.352 | 1.521 | 58.470 | 1.00 | 22.68 |
| 4997 | CD | LYS | A | 622 | -59.710 | 2.933 | 57.967 | 1.00 | 24.66 |
| 4998 | CE | LYS | A | 622 | -58.478 | 3.655 | 57.412 | 1.00 | 23.86 |
| 4999 | NZ | LYS | A | 622 | -57.624 | 4.200 | 58.507 | 1.00 | 28.09 |
| 5000 | C | LYS | A | 622 | -59.781 | -0.632 | 60.505 | 1.00 | 23.70 |
| 5001 | O | LYS | A | 622 | -58.566 | -0.661 | 60.684 | 1.00 | 23.21 |
| 5002 | N | CYS | A | 623 | -60.645 | -0.501 | 61.495 | 1.00 | 23.54 |
| 5003 | CA | CYS | A | 623 | -60.166 | -0.293 | 62.857 | 1.00 | 24.57 |
| 5004 | CB | CYS | A | 623 | -59.860 | 1.182 | 63.083 | 1.00 | 24.69 |
| 5005 | SG | CYS | A | 623 | -61.320 | 2.194 | 62.772 | 1.00 | 30.15 |
| 5006 | C | CYS | A | 623 | -61.243 | -0.698 | 63.840 | 1.00 | 23.59 |
| 5007 | O | CYS | A | 623 | -62.403 | -0.866 | 63.466 | 1.00 | 23.61 |
| 5008 | N | GLY | A | 624 | -60.862 | -0.871 | 65.099 | 1.00 | 22.96 |
| 5009 | CA | GLY | A | 624 | -61.840 | -1.187 | 66.120 | 1.00 | 21.96 |
| 5010 | C | GLY | A | 624 | -61.314 | -0.848 | 67.495 | 1.00 | 20.56 |
| 5011 | O | GLY | A | 624 | -60.132 | -0.635 | 67.653 | 1.00 | 20.22 |
| 5012 | N | ILE | A | 625 | -62.209 | -0.813 | 68.475 | 1.00 | 19.69 |
| 5013 | CA | ILE | A | 625 | -61.873 | -0.530 | 69.852 | 1.00 | 18.81 |
| 5014 | CB | ILE | A | 625 | -62.539 | 0.816 | 70.289 | 1.00 | 19.01 |
| 5015 | CG1 | ILE | A | 625 | -62.211 | 1.945 | 69.321 | 1.00 | 16.11 |
| 5016 | CD1 | ILE | A | 625 | -62.914 | 3.197 | 69.682 | 1.00 | 16.02 |
| 5017 | CG2 | ILE | A | 625 | -62.188 | 1.161 | 71.746 | 1.00 | 17.25 |
| 5018 | C | ILE | A | 625 | -62.497 | -1.616 | 70.714 | 1.00 | 18.34 |
| 5019 | O | ILE | A | 625 | -63.681 | -1.858 | 70.592 | 1.00 | 18.65 |
| 5020 | N | ALA | A | 626 | -61.729 | -2.222 | 71.610 | 1.00 | 17.80 |
| 5021 | CA | ALA | A | 626 | -62.288 | -3.197 | 72.543 | 1.00 | 17.73 |
| 5022 | CB | ALA | A | 626 | -61.597 | -4.520 | 72.443 | 1.00 | 17.61 |
| 5023 | C | ALA | A | 626 | -62.125 | -2.654 | 73.937 | 1.00 | 17.44 |
| 5024 | O | ALA | A | 626 | -61.050 | -2.290 | 74.309 | 1.00 | 17.61 |
| 5025 | N | VAL | A | 627 | -63.204 | -2.613 | 74.703 | 1.00 | 17.74 |
| 5026 | CA | VAL | A | 627 | -63.141 | -2.142 | 76.066 | 1.00 | 17.94 |
| 5027 | CB | VAL | A | 627 | -64.189 | -1.037 | 76.336 | 1.00 | 18.00 |
| 5028 | CG1 | VAL | A | 627 | -64.074 | -0.544 | 77.788 | 1.00 | 16.19 |
| 5029 | CG2 | VAL | A | 627 | -63.990 | 0.113 | 75.368 | 1.00 | 16.44 |
| 5030 | C | VAL | A | 627 | -63.416 | -3.319 | 76.992 | 1.00 | 18.36 |
| 5031 | O | VAL | A | 627 | -64.425 | -3.988 | 76.833 | 1.00 | 19.01 |
| 5032 | N | ALA | A | 628 | -62.528 | -3.539 | 77.963 | 1.00 | 17.77 |
| 5033 | CA | ALA | A | 628 | -62.620 | -4.654 | 78.907 | 1.00 | 17.24 |
| 5034 | CB | ALA | A | 628 | -63.491 | -4.281 | 80.065 | 1.00 | 17.08 |
| 5035 | C | ALA | A | 628 | -63.065 | -5.997 | 78.288 | 1.00 | 17.61 |
| 5036 | O | ALA | A | 628 | -63.979 | -6.666 | 78.806 | 1.00 | 17.63 |
| 5037 | N | PRO | A | 629 | -62.396 | -6.409 | 77.213 | 1.00 | 17.78 |
| 5038 | CA | PRO | A | 629 | -62.741 | -7.655 | 76.511 | 1.00 | 18.00 |
| 5039 | CB | PRO | A | 629 | -61.836 | -7.606 | 75.267 | 1.00 | 17.83 |

FIGURE 3 CU

| A | B | C | D | E | F | G | H | I | J |
|---|---|---|---|---|---|---|---|---|---|
| 5040 | CG | PRO | A | 629 | -60.617 | -6.764 | 75.745 | 1.00 | 18.80 |
| 5041 | CD | PRO | A | 629 | -61.279 | -5.681 | 76.557 | 1.00 | 18.05 |
| 5042 | C | PRO | A | 629 | -62.392 | -8.941 | 77.243 | 1.00 | 18.89 |
| 5043 | O | PRO | A | 629 | -61.370 | -9.040 | 77.919 | 1.00 | 19.33 |
| 5044 | N | VAL | A | 630 | -63.226 | -9.952 | 77.076 | 1.00 | 19.22 |
| 5045 | CA | VAL | A | 630 | -62.841 | -11.281 | 77.480 | 1.00 | 19.56 |
| 5046 | CB | VAL | A | 630 | -64.083 | -12.211 | 77.510 | 1.00 | 19.47 |
| 5047 | CG1 | VAL | A | 630 | -63.676 | -13.691 | 77.445 | 1.00 | 19.05 |
| 5048 | CG2 | VAL | A | 630 | -64.900 | -11.946 | 78.783 | 1.00 | 20.10 |
| 5049 | C | VAL | A | 630 | -61.865 | -11.663 | 76.369 | 1.00 | 20.33 |
| 5050 | O | VAL | A | 630 | -62.067 | -11.286 | 75.214 | 1.00 | 20.14 |
| 5051 | N | SER | A | 631 | -60.775 | -12.350 | 76.682 | 1.00 | 21.22 |
| 5052 | CA | SER | A | 631 | -59.829 | -12.710 | 75.615 | 1.00 | 20.43 |
| 5053 | CB | SER | A | 631 | -58.464 | -12.108 | 75.876 | 1.00 | 20.42 |
| 5054 | OG | SER | A | 631 | -57.862 | -12.676 | 77.020 | 1.00 | 18.57 |
| 5055 | C | SER | A | 631 | -59.726 | -14.227 | 75.476 | 1.00 | 21.06 |
| 5056 | O | SER | A | 631 | -59.361 | -14.750 | 74.420 | 1.00 | 20.72 |
| 5057 | N | ARG | A | 632 | -59.999 | -14.934 | 76.565 | 1.00 | 20.45 |
| 5058 | CA | ARG | A | 632 | -60.150 | -16.371 | 76.465 | 1.00 | 21.36 |
| 5059 | CB | ARG | A | 632 | -58.829 | -17.156 | 76.390 | 1.00 | 22.35 |
| 5060 | CG | ARG | A | 632 | -58.075 | -17.244 | 77.640 | 1.00 | 24.12 |
| 5061 | CD | ARG | A | 632 | -57.443 | -18.589 | 77.891 | 1.00 | 30.00 |
| 5062 | NE | ARG | A | 632 | -56.637 | -19.084 | 76.792 | 1.00 | 33.24 |
| 5063 | CZ | ARG | A | 632 | -55.772 | -20.100 | 76.890 | 1.00 | 34.46 |
| 5064 | NH1 | ARG | A | 632 | -55.082 | -20.470 | 75.814 | 1.00 | 31.79 |
| 5065 | NH2 | ARG | A | 632 | -55.584 | -20.728 | 78.063 | 1.00 | 33.30 |
| 5066 | C | ARG | A | 632 | -61.047 | -16.823 | 77.580 | 1.00 | 20.38 |
| 5067 | O | ARG | A | 632 | -60.965 | -16.333 | 78.714 | 1.00 | 20.35 |
| 5068 | N | TRP | A | 633 | -61.905 | -17.759 | 77.235 | 1.00 | 19.02 |
| 5069 | CA | TRP | A | 633 | -62.980 | -18.174 | 78.109 | 1.00 | 19.38 |
| 5070 | CB | TRP | A | 633 | -63.983 | -19.028 | 77.300 | 1.00 | 19.10 |
| 5071 | CG | TRP | A | 633 | -64.675 | -18.118 | 76.375 | 1.00 | 18.44 |
| 5072 | CD1 | TRP | A | 633 | -64.589 | -18.087 | 75.002 | 1.00 | 16.62 |
| 5073 | NE1 | TRP | A | 633 | -65.343 | -17.046 | 74.512 | 1.00 | 18.58 |
| 5074 | CE2 | TRP | A | 633 | -65.911 | -16.369 | 75.565 | 1.00 | 17.12 |
| 5075 | CD2 | TRP | A | 633 | -65.503 | -17.013 | 76.751 | 1.00 | 17.08 |
| 5076 | CE3 | TRP | A | 633 | -65.964 | -16.515 | 77.978 | 1.00 | 15.56 |
| 5077 | CZ3 | TRP | A | 633 | -66.798 | -15.409 | 77.981 | 1.00 | 17.56 |
| 5078 | CH2 | TRP | A | 633 | -67.182 | -14.793 | 76.790 | 1.00 | 18.04 |
| 5079 | CZ2 | TRP | A | 633 | -66.741 | -15.258 | 75.569 | 1.00 | 17.98 |
| 5080 | C | TRP | A | 633 | -62.545 | -18.770 | 79.450 | 1.00 | 20.13 |
| 5081 | O | TRP | A | 633 | -63.253 | -18.613 | 80.431 | 1.00 | 21.01 |
| 5082 | N | GLU | A | 634 | -61.352 | -19.353 | 79.527 | 1.00 | 20.46 |
| 5083 | CA | GLU | A | 634 | -60.849 | -19.887 | 80.802 | 1.00 | 21.33 |
| 5084 | CB | GLU | A | 634 | -59.596 | -20.758 | 80.564 | 1.00 | 21.47 |
| 5085 | CG | GLU | A | 634 | -59.904 | -22.204 | 80.183 | 1.00 | 23.57 |
| 5086 | CD | GLU | A | 634 | -58.822 | -22.837 | 79.320 | 1.00 | 27.27 |
| 5087 | OE1 | GLU | A | 634 | -58.809 | -22.583 | 78.094 | 1.00 | 28.36 |
| 5088 | OE2 | GLU | A | 634 | -57.985 | -23.598 | 79.860 | 1.00 | 30.14 |
| 5089 | C | GLU | A | 634 | -60.526 | -18.779 | 81.829 | 1.00 | 21.53 |
| 5090 | O | GLU | A | 634 | -60.366 | -19.037 | 83.021 | 1.00 | 20.99 |

FIGURE 3 CV

| A | B | C | D | E | F | G | H | I | J |
|---|---|---|---|---|---|---|---|---|---|
| 5091 | N | TYR | A | 635 | -60.419 | -17.542 | 81.364 | 1.00 | 22.11 |
| 5092 | CA | TYR | A | 635 | -60.123 | -16.417 | 82.257 | 1.00 | 21.19 |
| 5093 | CB | TYR | A | 635 | -59.517 | -15.251 | 81.478 | 1.00 | 20.79 |
| 5094 | CG | TYR | A | 635 | -58.133 | -15.492 | 80.919 | 1.00 | 21.12 |
| 5095 | CD1 | TYR | A | 635 | -57.333 | -16.509 | 81.406 | 1.00 | 20.15 |
| 5096 | CE1 | TYR | A | 635 | -56.071 | -16.727 | 80.897 | 1.00 | 20.96 |
| 5097 | CZ | TYR | A | 635 | -55.582 | -15.910 | 79.895 | 1.00 | 21.25 |
| 5098 | OH | TYR | A | 635 | -54.311 | -16.139 | 79.382 | 1.00 | 21.05 |
| 5099 | CE2 | TYR | A | 635 | -56.357 | -14.884 | 79.400 | 1.00 | 19.15 |
| 5100 | CD2 | TYR | A | 635 | -57.622 | -14.683 | 79.906 | 1.00 | 21.12 |
| 5101 | C | TYR | A | 635 | -61.397 | -15.929 | 82.864 | 1.00 | 21.28 |
| 5102 | O | TYR | A | 635 | -61.393 | -15.214 | 83.879 | 1.00 | 22.46 |
| 5103 | N | TYR | A | 636 | -62.514 | -16.299 | 82.267 | 1.00 | 21.33 |
| 5104 | CA | TYR | A | 636 | -63.761 | -15.712 | 82.736 | 1.00 | 21.39 |
| 5105 | CB | TYR | A | 636 | -64.659 | -15.289 | 81.570 | 1.00 | 20.83 |
| 5106 | CG | TYR | A | 636 | -65.723 | -14.318 | 82.011 | 1.00 | 20.13 |
| 5107 | CD1 | TYR | A | 636 | -65.380 | -13.145 | 82.657 | 1.00 | 20.12 |
| 5108 | CE1 | TYR | A | 636 | -66.347 | -12.264 | 83.101 | 1.00 | 21.74 |
| 5109 | CZ | TYR | A | 636 | -67.679 | -12.553 | 82.900 | 1.00 | 22.24 |
| 5110 | OH | TYR | A | 636 | -68.639 | -11.678 | 83.346 | 1.00 | 22.21 |
| 5111 | CE2 | TYR | A | 636 | -68.049 | -13.727 | 82.274 | 1.00 | 20.77 |
| 5112 | CD2 | TYR | A | 636 | -67.067 | -14.604 | 81.839 | 1.00 | 21.02 |
| 5113 | C | TYR | A | 636 | -64.475 | -16.571 | 83.786 | 1.00 | 22.12 |
| 5114 | O | TYR | A | 636 | -64.080 | -17.732 | 84.031 | 1.00 | 22.47 |
| 5115 | N | ASP | A | 637 | -65.493 | -16.015 | 84.440 | 1.00 | 21.83 |
| 5116 | CA | ASP | A | 637 | -66.088 | -16.761 | 85.542 | 1.00 | 22.58 |
| 5117 | CB | ASP | A | 637 | -66.937 | -15.866 | 86.464 | 1.00 | 22.18 |
| 5118 | CG | ASP | A | 637 | -68.218 | -15.407 | 85.826 | 1.00 | 22.98 |
| 5119 | OD1 | ASP | A | 637 | -69.139 | -16.233 | 85.659 | 1.00 | 22.99 |
| 5120 | OD2 | ASP | A | 637 | -68.426 | -14.222 | 85.505 | 1.00 | 24.25 |
| 5121 | C | ASP | A | 637 | -66.833 | -18.031 | 85.108 | 1.00 | 22.89 |
| 5122 | O | ASP | A | 637 | -67.375 | -18.135 | 84.001 | 1.00 | 22.92 |
| 5123 | N | SER | A | 638 | -66.876 | -18.990 | 86.019 | 1.00 | 23.10 |
| 5124 | CA | SER | A | 638 | -67.415 | -20.308 | 85.718 | 1.00 | 23.30 |
| 5125 | CB | SER | A | 638 | -67.152 | -21.254 | 86.906 | 1.00 | 23.90 |
| 5126 | OG | SER | A | 638 | -67.823 | -20.801 | 88.071 | 1.00 | 23.09 |
| 5127 | C | SER | A | 638 | -68.881 | -20.339 | 85.373 | 1.00 | 23.53 |
| 5128 | O | SER | A | 638 | -69.261 | -21.000 | 84.421 | 1.00 | 24.64 |
| 5129 | N | VAL | A | 639 | -69.734 | -19.648 | 86.118 | 1.00 | 23.29 |
| 5130 | CA | VAL | A | 639 | -71.145 | -19.850 | 85.835 | 1.00 | 23.29 |
| 5131 | CB | VAL | A | 639 | -72.089 | -19.592 | 87.067 | 1.00 | 24.01 |
| 5132 | CG1 | VAL | A | 639 | -73.131 | -18.523 | 86.842 | 1.00 | 22.27 |
| 5133 | CG2 | VAL | A | 639 | -71.293 | -19.459 | 88.367 | 1.00 | 23.50 |
| 5134 | C | VAL | A | 639 | -71.607 | -19.215 | 84.543 | 1.00 | 23.93 |
| 5135 | O | VAL | A | 639 | -72.505 | -19.725 | 83.879 | 1.00 | 23.23 |
| 5136 | N | TYR | A | 640 | -70.977 | -18.108 | 84.162 | 1.00 | 23.68 |
| 5137 | CA | TYR | A | 640 | -71.356 | -17.513 | 82.911 | 1.00 | 23.15 |
| 5138 | CB | TYR | A | 640 | -70.840 | -16.083 | 82.815 | 1.00 | 22.59 |
| 5139 | CG | TYR | A | 640 | -71.203 | -15.375 | 81.518 | 1.00 | 21.34 |
| 5140 | CD1 | TYR | A | 640 | -72.327 | -14.557 | 81.450 | 1.00 | 18.73 |
| 5141 | CE1 | TYR | A | 640 | -72.659 | -13.891 | 80.285 | 1.00 | 19.07 |

FIGURE 3 CW

| A | B | C | D | E | F | G | H | I | J |
|---|---|---|---|---|---|---|---|---|---|
| 5142 | CZ | TYR | A | 640 | -71.859 | -14.044 | 79.158 | 1.00 | 18.83 |
| 5143 | OH | TYR | A | 640 | -72.182 | -13.367 | 78.016 | 1.00 | 20.13 |
| 5144 | CE2 | TYR | A | 640 | -70.751 | -14.853 | 79.181 | 1.00 | 18.02 |
| 5145 | CD2 | TYR | A | 640 | -70.416 | -15.521 | 80.363 | 1.00 | 18.53 |
| 5146 | C | TYR | A | 640 | -70.772 | -18.361 | 81.788 | 1.00 | 23.14 |
| 5147 | O | TYR | A | 640 | -71.481 | -18.811 | 80.905 | 1.00 | 22.95 |
| 5148 | N | THR | A | 641 | -69.461 | -18.553 | 81.839 | 1.00 | 23.13 |
| 5149 | CA | THR | A | 641 | -68.728 | -19.262 | 80.805 | 1.00 | 22.36 |
| 5150 | CB | THR | A | 641 | -67.247 | -19.284 | 81.186 | 1.00 | 22.36 |
| 5151 | OG1 | THR | A | 641 | -66.793 | -17.930 | 81.327 | 1.00 | 21.49 |
| 5152 | CG2 | THR | A | 641 | -66.390 | -19.870 | 80.050 | 1.00 | 19.59 |
| 5153 | C | THR | A | 641 | -69.206 | -20.683 | 80.551 | 1.00 | 23.09 |
| 5154 | O | THR | A | 641 | -69.448 | -21.063 | 79.406 | 1.00 | 22.58 |
| 5155 | N | GLU | A | 642 | -69.318 | -21.476 | 81.614 | 1.00 | 23.11 |
| 5156 | CA | GLU | A | 642 | -69.665 | -22.884 | 81.449 | 1.00 | 23.47 |
| 5157 | CB | GLU | A | 642 | -69.489 | -23.619 | 82.775 | 1.00 | 23.64 |
| 5158 | CG | GLU | A | 642 | -68.054 | -23.600 | 83.260 | 1.00 | 21.61 |
| 5159 | CD | GLU | A | 642 | -67.941 | -24.019 | 84.701 | 1.00 | 23.47 |
| 5160 | OE1 | GLU | A | 642 | -68.965 | -24.442 | 85.266 | 1.00 | 24.23 |
| 5161 | OE2 | GLU | A | 642 | -66.830 | -23.920 | 85.270 | 1.00 | 24.27 |
| 5162 | C | GLU | A | 642 | -71.061 | -23.055 | 80.905 | 1.00 | 23.51 |
| 5163 | O | GLU | A | 642 | -71.372 | -24.027 | 80.202 | 1.00 | 24.20 |
| 5164 | N | ARG | A | 643 | -71.909 | -22.098 | 81.232 | 1.00 | 23.66 |
| 5165 | CA | ARG | A | 643 | -73.260 | -22.067 | 80.718 | 1.00 | 23.80 |
| 5166 | CB | ARG | A | 643 | -73.905 | -20.732 | 81.047 | 1.00 | 23.72 |
| 5167 | CG | ARG | A | 643 | -75.391 | -20.698 | 80.758 | 1.00 | 23.14 |
| 5168 | CD | ARG | A | 643 | -76.036 | -19.365 | 81.033 | 1.00 | 25.73 |
| 5169 | NE | ARG | A | 643 | -75.932 | -18.954 | 82.436 | 1.00 | 24.82 |
| 5170 | CZ | ARG | A | 643 | -75.662 | -17.718 | 82.842 | 1.00 | 22.95 |
| 5171 | NH1 | ARG | A | 643 | -75.437 | -16.746 | 81.978 | 1.00 | 20.65 |
| 5172 | NH2 | ARG | A | 643 | -75.612 | -17.454 | 84.131 | 1.00 | 24.06 |
| 5173 | C | ARG | A | 643 | -73.305 | -22.232 | 79.205 | 1.00 | 23.97 |
| 5174 | O | ARG | A | 643 | -74.177 | -22.902 | 78.674 | 1.00 | 24.18 |
| 5175 | N | TYR | A | 644 | -72.391 | -21.572 | 78.513 | 1.00 | 24.34 |
| 5176 | CA | TYR | A | 644 | -72.379 | -21.611 | 77.065 | 1.00 | 24.78 |
| 5177 | CB | TYR | A | 644 | -72.177 | -20.194 | 76.505 | 1.00 | 24.45 |
| 5178 | CG | TYR | A | 644 | -73.057 | -19.193 | 77.190 | 1.00 | 23.62 |
| 5179 | CD1 | TYR | A | 644 | -74.429 | -19.230 | 77.035 | 1.00 | 23.88 |
| 5180 | CE1 | TYR | A | 644 | -75.231 | -18.332 | 77.684 | 1.00 | 24.08 |
| 5181 | CZ | TYR | A | 644 | -74.651 | -17.399 | 78.527 | 1.00 | 24.09 |
| 5182 | OH | TYR | A | 644 | -75.414 | -16.507 | 79.204 | 1.00 | 23.00 |
| 5183 | CE2 | TYR | A | 644 | -73.302 | -17.357 | 78.705 | 1.00 | 23.96 |
| 5184 | CD2 | TYR | A | 644 | -72.515 | -18.255 | 78.047 | 1.00 | 24.31 |
| 5185 | C | TYR | A | 644 | -71.260 | -22.499 | 76.555 | 1.00 | 24.67 |
| 5186 | O | TYR | A | 644 | -71.304 | -22.959 | 75.429 | 1.00 | 24.91 |
| 5187 | N | MET | A | 645 | -70.276 | -22.764 | 77.393 | 1.00 | 24.31 |
| 5188 | CA | MET | A | 645 | -69.072 | -23.402 | 76.898 | 1.00 | 25.36 |
| 5189 | CB | MET | A | 645 | -67.863 | -22.477 | 77.129 | 1.00 | 25.32 |
| 5190 | CG | MET | A | 645 | -67.842 | -21.234 | 76.231 | 1.00 | 26.08 |
| 5191 | SD | MET | A | 645 | -67.399 | -21.710 | 74.533 | 1.00 | 29.71 |
| 5192 | CE | MET | A | 645 | -65.606 | -22.145 | 74.848 | 1.00 | 26.46 |

FIGURE 3 CX

| A | B | C | D | E | F | G | H | I | J |
|---|---|---|---|---|---|---|---|---|---|
| 5193 | C | MET | A | 645 | -68.769 | -24.767 | 77.478 | 1.00 | 25.69 |
| 5194 | O | MET | A | 645 | -67.845 | -25.421 | 77.017 | 1.00 | 25.66 |
| 5195 | N | GLY | A | 646 | -69.525 | -25.189 | 78.486 | 1.00 | 26.08 |
| 5196 | CA | GLY | A | 646 | -69.240 | -26.447 | 79.143 | 1.00 | 27.31 |
| 5197 | C | GLY | A | 646 | -67.941 | -26.242 | 79.871 | 1.00 | 28.29 |
| 5198 | O | GLY | A | 646 | -67.491 | -25.105 | 80.023 | 1.00 | 29.19 |
| 5199 | N | LEU | A | 647 | -67.324 | -27.327 | 80.308 | 1.00 | 29.08 |
| 5200 | CA | LEU | A | 647 | -66.032 | -27.261 | 80.998 | 1.00 | 29.38 |
| 5201 | CB | LEU | A | 647 | -65.865 | -28.482 | 81.901 | 1.00 | 29.39 |
| 5202 | CG | LEU | A | 647 | -66.459 | -28.411 | 83.288 | 1.00 | 31.66 |
| 5203 | CD1 | LEU | A | 647 | -67.215 | -27.097 | 83.510 | 1.00 | 31.73 |
| 5204 | CD2 | LEU | A | 647 | -67.322 | -29.637 | 83.525 | 1.00 | 32.56 |
| 5205 | C | LEU | A | 647 | -64.883 | -27.323 | 80.036 | 1.00 | 29.07 |
| 5206 | O | LEU | A | 647 | -64.983 | -27.965 | 79.000 | 1.00 | 28.84 |
| 5207 | N | PRO | A | 648 | -63.759 | -26.734 | 80.429 | 1.00 | 28.93 |
| 5208 | CA | PRO | A | 648 | -62.536 | -26.787 | 79.629 | 1.00 | 29.00 |
| 5209 | CB | PRO | A | 648 | -61.746 | -25.562 | 80.107 | 1.00 | 28.58 |
| 5210 | CG | PRO | A | 648 | -62.450 | -25.070 | 81.350 | 1.00 | 28.32 |
| 5211 | CD | PRO | A | 648 | -63.574 | -25.987 | 81.683 | 1.00 | 28.10 |
| 5212 | C | PRO | A | 648 | -61.694 | -28.026 | 79.932 | 1.00 | 29.46 |
| 5213 | O | PRO | A | 648 | -60.558 | -27.881 | 80.357 | 1.00 | 29.04 |
| 5214 | N | THR | A | 649 | -62.235 | -29.217 | 79.732 | 1.00 | 30.75 |
| 5215 | CA | THR | A | 649 | -61.468 | -30.441 | 79.940 | 1.00 | 31.30 |
| 5216 | CB | THR | A | 649 | -62.152 | -31.321 | 80.963 | 1.00 | 31.86 |
| 5217 | OG1 | THR | A | 649 | -63.534 | -31.470 | 80.599 | 1.00 | 31.50 |
| 5218 | CG2 | THR | A | 649 | -62.168 | -30.636 | 82.359 | 1.00 | 30.73 |
| 5219 | C | THR | A | 649 | -61.406 | -31.192 | 78.637 | 1.00 | 32.53 |
| 5220 | O | THR | A | 649 | -62.262 | -30.995 | 77.768 | 1.00 | 31.95 |
| 5221 | N | PRO | A | 650 | -60.396 | -32.053 | 78.496 | 1.00 | 33.40 |
| 5222 | CA | PRO | A | 650 | -60.216 | -32.849 | 77.284 | 1.00 | 33.88 |
| 5223 | CB | PRO | A | 650 | -59.140 | -33.846 | 77.699 | 1.00 | 33.91 |
| 5224 | CG | PRO | A | 650 | -58.350 | -33.098 | 78.655 | 1.00 | 33.82 |
| 5225 | CD | PRO | A | 650 | -59.337 | -32.327 | 79.480 | 1.00 | 33.44 |
| 5226 | C | PRO | A | 650 | -61.479 | -33.573 | 76.908 | 1.00 | 34.49 |
| 5227 | O | PRO | A | 650 | -61.748 | -33.726 | 75.715 | 1.00 | 35.35 |
| 5228 | N | GLU | A | 651 | -62.258 | -33.996 | 77.899 | 1.00 | 35.30 |
| 5229 | CA | GLU | A | 651 | -63.494 | -34.729 | 77.628 | 1.00 | 36.20 |
| 5230 | CB | GLU | A | 651 | -63.778 | -35.767 | 78.720 | 1.00 | 36.74 |
| 5231 | CG | GLU | A | 651 | -63.521 | -35.287 | 80.136 | 1.00 | 39.79 |
| 5232 | CD | GLU | A | 651 | -62.090 | -35.514 | 80.572 | 1.00 | 42.71 |
| 5233 | OE1 | GLU | A | 651 | -61.517 | -34.626 | 81.245 | 1.00 | 44.21 |
| 5234 | OE2 | GLU | A | 651 | -61.537 | -36.586 | 80.237 | 1.00 | 44.81 |
| 5235 | C | GLU | A | 651 | -64.723 | -33.845 | 77.424 | 1.00 | 35.94 |
| 5236 | O | GLU | A | 651 | -65.777 | -34.311 | 76.948 | 1.00 | 36.46 |
| 5237 | N | ASP | A | 652 | -64.645 | -32.577 | 77.800 | 1.00 | 34.99 |
| 5238 | CA | ASP | A | 652 | -65.807 | -31.756 | 77.496 | 1.00 | 33.48 |
| 5239 | CB | ASP | A | 652 | -66.374 | -30.988 | 78.691 | 1.00 | 33.35 |
| 5240 | CG | ASP | A | 652 | -67.736 | -30.388 | 78.377 | 1.00 | 33.12 |
| 5241 | OD1 | ASP | A | 652 | -68.406 | -29.842 | 79.273 | 1.00 | 34.89 |
| 5242 | OD2 | ASP | A | 652 | -68.230 | -30.430 | 77.238 | 1.00 | 32.30 |
| 5243 | C | ASP | A | 652 | -65.584 | -30.861 | 76.302 | 1.00 | 32.82 |

FIGURE 3 CY

| A | B | C | D | E | F | G | H | I | J |
|---|---|---|---|---|---|---|---|---|---|
| 5244 | O | ASP | A | 652 | -65.827 | -31.294 | 75.177 | 1.00 | 32.95 |
| 5245 | N | ASN | A | 653 | -65.098 | -29.634 | 76.527 | 1.00 | 31.69 |
| 5246 | CA | ASN | A | 653 | -65.034 | -28.649 | 75.448 | 1.00 | 30.86 |
| 5247 | CB | ASN | A | 653 | -66.223 | -27.682 | 75.585 | 1.00 | 30.19 |
| 5248 | CG | ASN | A | 653 | -66.639 | -27.043 | 74.251 | 1.00 | 28.23 |
| 5249 | OD1 | ASN | A | 653 | -66.427 | -27.619 | 73.190 | 1.00 | 25.84 |
| 5250 | ND2 | ASN | A | 653 | -67.217 | -25.839 | 74.312 | 1.00 | 24.02 |
| 5251 | C | ASN | A | 653 | -63.709 | -27.892 | 75.323 | 1.00 | 31.44 |
| 5252 | O | ASN | A | 653 | -63.656 | -26.819 | 74.711 | 1.00 | 32.23 |
| 5253 | N | LEU | A | 654 | -62.644 | -28.462 | 75.881 | 1.00 | 31.17 |
| 5254 | CA | LEU | A | 654 | -61.321 | -27.852 | 75.884 | 1.00 | 31.62 |
| 5255 | CB | LEU | A | 654 | -60.271 | -28.822 | 76.462 | 1.00 | 31.66 |
| 5256 | CG | LEU | A | 654 | -58.828 | -28.289 | 76.455 | 1.00 | 31.74 |
| 5257 | CD1 | LEU | A | 654 | -57.841 | -29.275 | 77.064 | 1.00 | 30.38 |
| 5258 | CD2 | LEU | A | 654 | -58.739 | -26.954 | 77.219 | 1.00 | 32.35 |
| 5259 | C | LEU | A | 654 | -60.871 | -27.367 | 74.515 | 1.00 | 31.37 |
| 5260 | O | LEU | A | 654 | -60.409 | -26.246 | 74.365 | 1.00 | 31.55 |
| 5261 | N | ASP | A | 655 | -60.982 | -28.223 | 73.515 | 1.00 | 31.42 |
| 5262 | CA | ASP | A | 655 | -60.583 | -27.836 | 72.175 | 1.00 | 31.41 |
| 5263 | CB | ASP | A | 655 | -60.917 | -28.930 | 71.141 | 1.00 | 31.61 |
| 5264 | CG | ASP | A | 655 | -60.034 | -30.181 | 71.290 | 1.00 | 33.09 |
| 5265 | OD1 | ASP | A | 655 | -58.976 | -30.116 | 71.981 | 1.00 | 32.53 |
| 5266 | OD2 | ASP | A | 655 | -60.336 | -31.282 | 70.762 | 1.00 | 35.23 |
| 5267 | C | ASP | A | 655 | -61.210 | -26.489 | 71.789 | 1.00 | 30.88 |
| 5268 | O | ASP | A | 655 | -60.506 | -25.592 | 71.318 | 1.00 | 31.25 |
| 5269 | N | HIS | A | 656 | -62.506 | -26.316 | 72.001 | 1.00 | 29.59 |
| 5270 | CA | HIS | A | 656 | -63.091 | -25.032 | 71.617 | 1.00 | 29.45 |
| 5271 | CB | HIS | A | 656 | -64.605 | -25.059 | 71.449 | 1.00 | 28.85 |
| 5272 | CG | HIS | A | 656 | -65.125 | -23.786 | 70.859 | 1.00 | 31.28 |
| 5273 | ND1 | HIS | A | 656 | -64.712 | -23.322 | 69.624 | 1.00 | 31.33 |
| 5274 | CE1 | HIS | A | 656 | -65.277 | -22.155 | 69.383 | 1.00 | 28.62 |
| 5275 | NE2 | HIS | A | 656 | -66.031 | -21.836 | 70.419 | 1.00 | 29.04 |
| 5276 | CD2 | HIS | A | 656 | -65.936 | -22.827 | 71.367 | 1.00 | 30.35 |
| 5277 | C | HIS | A | 656 | -62.658 | -23.841 | 72.496 | 1.00 | 28.95 |
| 5278 | O | HIS | A | 656 | -62.541 | -22.720 | 72.004 | 1.00 | 29.11 |
| 5279 | N | TYR | A | 657 | -62.403 | -24.075 | 73.778 | 1.00 | 28.25 |
| 5280 | CA | TYR | A | 657 | -61.906 | -23.001 | 74.630 | 1.00 | 27.73 |
| 5281 | CB | TYR | A | 657 | -61.625 | -23.496 | 76.052 | 1.00 | 27.06 |
| 5282 | CG | TYR | A | 657 | -62.764 | -23.445 | 77.047 | 1.00 | 24.81 |
| 5283 | CD1 | TYR | A | 657 | -62.891 | -22.382 | 77.930 | 1.00 | 21.97 |
| 5284 | CE1 | TYR | A | 657 | -63.895 | -22.348 | 78.863 | 1.00 | 19.46 |
| 5285 | CZ | TYR | A | 657 | -64.801 | -23.375 | 78.946 | 1.00 | 19.96 |
| 5286 | OH | TYR | A | 657 | -65.821 | -23.322 | 79.891 | 1.00 | 16.13 |
| 5287 | CE2 | TYR | A | 657 | -64.700 | -24.449 | 78.088 | 1.00 | 20.07 |
| 5288 | CD2 | TYR | A | 657 | -63.675 | -24.480 | 77.149 | 1.00 | 24.04 |
| 5289 | C | TYR | A | 657 | -60.595 | -22.545 | 74.056 | 1.00 | 28.50 |
| 5290 | O | TYR | A | 657 | -60.312 | -21.344 | 73.975 | 1.00 | 29.14 |
| 5291 | N | ARG | A | 658 | -59.771 | -23.505 | 73.658 | 1.00 | 29.19 |
| 5292 | CA | ARG | A | 658 | -58.437 | -23.163 | 73.181 | 1.00 | 30.10 |
| 5293 | CB | ARG | A | 658 | -57.508 | -24.378 | 73.186 | 1.00 | 30.86 |
| 5294 | CG | ARG | A | 658 | -57.024 | -24.776 | 74.559 | 1.00 | 34.28 |

FIGURE 3 CZ

| A | B | C | D | E | F | G | H | I | J |
|---|---|---|---|---|---|---|---|---|---|
| 5295 | CD | ARG | A | 658 | -55.835 | -25.746 | 74.525 | 1.00 | 43.28 |
| 5296 | NE | ARG | A | 658 | -56.163 | -27.019 | 73.882 | 1.00 | 46.55 |
| 5297 | CZ | ARG | A | 658 | -55.464 | -28.133 | 74.076 | 1.00 | 49.48 |
| 5298 | NH1 | ARG | A | 658 | -54.409 | -28.111 | 74.882 | 1.00 | 50.32 |
| 5299 | NH2 | ARG | A | 658 | -55.815 | -29.263 | 73.476 | 1.00 | 49.35 |
| 5300 | C | ARG | A | 658 | -58.464 | -22.560 | 71.813 | 1.00 | 29.69 |
| 5301 | O | ARG | A | 658 | -57.530 | -21.890 | 71.418 | 1.00 | 30.15 |
| 5302 | N | ASN | A | 659 | -59.553 | -22.769 | 71.099 | 1.00 | 29.67 |
| 5303 | CA | ASN | A | 659 | -59.633 | -22.288 | 69.745 | 1.00 | 30.12 |
| 5304 | CB | ASN | A | 659 | -60.348 | -23.342 | 68.894 | 1.00 | 31.51 |
| 5305 | CG | ASN | A | 659 | -59.577 | -23.688 | 67.669 | 1.00 | 35.72 |
| 5306 | OD1 | ASN | A | 659 | -58.687 | -24.537 | 67.721 | 1.00 | 39.51 |
| 5307 | ND2 | ASN | A | 659 | -59.876 | -23.008 | 66.551 | 1.00 | 38.70 |
| 5308 | C | ASN | A | 659 | -60.382 | -20.972 | 69.594 | 1.00 | 28.84 |
| 5309 | O | ASN | A | 659 | -60.415 | -20.416 | 68.506 | 1.00 | 28.71 |
| 5310 | N | SER | A | 660 | -61.018 | -20.503 | 70.664 | 1.00 | 27.17 |
| 5311 | CA | SER | A | 660 | -61.844 | -19.298 | 70.588 | 1.00 | 25.44 |
| 5312 | CB | SER | A | 660 | -63.198 | -19.580 | 71.215 | 1.00 | 24.98 |
| 5313 | OG | SER | A | 660 | -63.031 | -20.172 | 72.497 | 1.00 | 25.82 |
| 5314 | C | SER | A | 660 | -61.221 | -18.076 | 71.274 | 1.00 | 24.97 |
| 5315 | O | SER | A | 660 | -61.933 | -17.153 | 71.656 | 1.00 | 25.56 |
| 5316 | N | THR | A | 661 | -59.908 | -18.068 | 71.442 | 1.00 | 23.39 |
| 5317 | CA | THR | A | 661 | -59.247 | -16.941 | 72.075 | 1.00 | 23.16 |
| 5318 | CB | THR | A | 661 | -57.918 | -17.385 | 72.698 | 1.00 | 23.16 |
| 5319 | OG1 | THR | A | 661 | -56.957 | -17.511 | 71.654 | 1.00 | 23.43 |
| 5320 | CG2 | THR | A | 661 | -57.998 | -18.785 | 73.324 | 1.00 | 21.93 |
| 5321 | C | THR | A | 661 | -58.889 | -15.813 | 71.113 | 1.00 | 22.62 |
| 5322 | O | THR | A | 661 | -58.680 | -16.036 | 69.913 | 1.00 | 22.28 |
| 5323 | N | VAL | A | 662 | -58.754 | -14.595 | 71.624 | 1.00 | 22.12 |
| 5324 | CA | VAL | A | 662 | -58.285 | -13.567 | 70.698 | 1.00 | 21.74 |
| 5325 | CB | VAL | A | 662 | -58.738 | -12.098 | 70.979 | 1.00 | 21.98 |
| 5326 | CG1 | VAL | A | 662 | -59.891 | -12.035 | 71.964 | 1.00 | 21.08 |
| 5327 | CG2 | VAL | A | 662 | -57.565 | -11.238 | 71.384 | 1.00 | 22.47 |
| 5328 | C | VAL | A | 662 | -56.797 | -13.692 | 70.511 | 1.00 | 20.40 |
| 5329 | O | VAL | A | 662 | -56.296 | -13.411 | 69.441 | 1.00 | 19.95 |
| 5330 | N | MET | A | 663 | -56.087 | -14.152 | 71.527 | 1.00 | 20.78 |
| 5331 | CA | MET | A | 663 | -54.637 | -14.288 | 71.382 | 1.00 | 20.68 |
| 5332 | CB | MET | A | 663 | -53.975 | -14.914 | 72.625 | 1.00 | 20.17 |
| 5333 | CG | MET | A | 663 | -53.737 | -13.912 | 73.760 | 1.00 | 19.42 |
| 5334 | SD | MET | A | 663 | -55.332 | -13.456 | 74.451 | 1.00 | 20.98 |
| 5335 | CE | MET | A | 663 | -55.659 | -14.841 | 75.532 | 1.00 | 17.84 |
| 5336 | C | MET | A | 663 | -54.281 | -15.069 | 70.119 | 1.00 | 21.08 |
| 5337 | O | MET | A | 663 | -53.339 | -14.719 | 69.432 | 1.00 | 20.76 |
| 5338 | N | SER | A | 664 | -55.053 | -16.107 | 69.804 | 1.00 | 21.53 |
| 5339 | CA | SER | A | 664 | -54.755 | -16.933 | 68.632 | 1.00 | 22.75 |
| 5340 | CB | SER | A | 664 | -55.595 | -18.205 | 68.612 | 1.00 | 22.81 |
| 5341 | OG | SER | A | 664 | -56.965 | -17.921 | 68.354 | 1.00 | 24.70 |
| 5342 | C | SER | A | 664 | -54.902 | -16.199 | 67.310 | 1.00 | 23.01 |
| 5343 | O | SER | A | 664 | -54.343 | -16.623 | 66.291 | 1.00 | 24.23 |
| 5344 | N | ARG | A | 665 | -55.618 | -15.088 | 67.312 | 1.00 | 22.62 |
| 5345 | CA | ARG | A | 665 | -55.791 | -14.335 | 66.088 | 1.00 | 22.32 |

FIGURE 3 DA

| A | B | C | D | E | F | G | H | I | J |
|---|---|---|---|---|---|---|---|---|---|
| 5346 | CB | ARG | A | 665 | -57.232 | -13.903 | 65.980 | 1.00 | 23.29 |
| 5347 | CG | ARG | A | 665 | -58.141 | -15.116 | 66.007 | 1.00 | 23.73 |
| 5348 | CD | ARG | A | 665 | -59.572 | -14.808 | 66.178 | 1.00 | 26.81 |
| 5349 | NE | ARG | A | 665 | -60.402 | -15.948 | 65.794 | 1.00 | 27.93 |
| 5350 | CZ | ARG | A | 665 | -61.511 | -15.830 | 65.078 | 1.00 | 29.01 |
| 5351 | NH1 | ARG | A | 665 | -61.919 | -14.625 | 64.656 | 1.00 | 24.12 |
| 5352 | NH2 | ARG | A | 665 | -62.211 | -16.924 | 64.796 | 1.00 | 29.75 |
| 5353 | C | ARG | A | 665 | -54.844 | -13.159 | 65.964 | 1.00 | 22.41 |
| 5354 | O | ARG | A | 665 | -54.975 | -12.361 | 65.049 | 1.00 | 22.42 |
| 5355 | N | ALA | A | 666 | -53.859 | -13.094 | 66.855 | 1.00 | 21.95 |
| 5356 | CA | ALA | A | 666 | -52.920 | -11.974 | 66.912 | 1.00 | 23.05 |
| 5357 | CB | ALA | A | 666 | -51.776 | -12.291 | 67.873 | 1.00 | 22.46 |
| 5358 | C | ALA | A | 666 | -52.370 | -11.513 | 65.570 | 1.00 | 23.45 |
| 5359 | O | ALA | A | 666 | -52.439 | -10.321 | 65.232 | 1.00 | 23.40 |
| 5360 | N | GLU | A | 667 | -51.844 | -12.457 | 64.798 | 1.00 | 24.34 |
| 5361 | CA | GLU | A | 667 | -51.210 | -12.104 | 63.529 | 1.00 | 26.02 |
| 5362 | CB | GLU | A | 667 | -50.722 | -13.356 | 62.816 | 1.00 | 26.46 |
| 5363 | CG | GLU | A | 667 | -50.092 | -13.078 | 61.468 | 1.00 | 30.53 |
| 5364 | CD | GLU | A | 667 | -48.626 | -12.715 | 61.584 | 1.00 | 36.20 |
| 5365 | OE1 | GLU | A | 667 | -48.065 | -12.186 | 60.598 | 1.00 | 38.89 |
| 5366 | OE2 | GLU | A | 667 | -48.027 | -12.972 | 62.659 | 1.00 | 39.46 |
| 5367 | C | GLU | A | 667 | -52.072 | -11.259 | 62.580 | 1.00 | 25.57 |
| 5368 | O | GLU | A | 667 | -51.566 | -10.381 | 61.889 | 1.00 | 25.83 |
| 5369 | N | ASN | A | 668 | -53.371 | -11.517 | 62.561 | 1.00 | 25.39 |
| 5370 | CA | ASN | A | 668 | -54.257 | -10.785 | 61.668 | 1.00 | 25.55 |
| 5371 | CB | ASN | A | 668 | -55.585 | -11.516 | 61.495 | 1.00 | 25.59 |
| 5372 | CG | ASN | A | 668 | -55.426 | -12.848 | 60.788 | 1.00 | 27.16 |
| 5373 | OD1 | ASN | A | 668 | -54.536 | -13.024 | 59.946 | 1.00 | 29.15 |
| 5374 | ND2 | ASN | A | 668 | -56.277 | -13.797 | 61.135 | 1.00 | 26.82 |
| 5375 | C | ASN | A | 668 | -54.503 | -9.345 | 62.084 | 1.00 | 25.01 |
| 5376 | O | ASN | A | 668 | -55.031 | -8.562 | 61.298 | 1.00 | 25.54 |
| 5377 | N | PHE | A | 669 | -54.142 | -8.994 | 63.310 | 1.00 | 24.54 |
| 5378 | CA | PHE | A | 669 | -54.315 | -7.622 | 63.743 | 1.00 | 24.00 |
| 5379 | CB | PHE | A | 669 | -54.077 | -7.469 | 65.245 | 1.00 | 23.84 |
| 5380 | CG | PHE | A | 669 | -55.266 | -7.839 | 66.080 | 1.00 | 24.47 |
| 5381 | CD1 | PHE | A | 669 | -55.617 | -9.168 | 66.257 | 1.00 | 22.23 |
| 5382 | CE1 | PHE | A | 669 | -56.680 | -9.516 | 67.027 | 1.00 | 21.34 |
| 5383 | CZ | PHE | A | 669 | -57.459 | -8.528 | 67.625 | 1.00 | 22.55 |
| 5384 | CE2 | PHE | A | 669 | -57.132 | -7.194 | 67.447 | 1.00 | 23.64 |
| 5385 | CD2 | PHE | A | 669 | -56.043 | -6.854 | 66.680 | 1.00 | 24.33 |
| 5386 | C | PHE | A | 669 | -53.377 | -6.741 | 62.945 | 1.00 | 23.82 |
| 5387 | O | PHE | A | 669 | -53.424 | -5.536 | 63.067 | 1.00 | 22.53 |
| 5388 | N | LYS | A | 670 | -52.517 | -7.348 | 62.127 | 1.00 | 24.69 |
| 5389 | CA | LYS | A | 670 | -51.615 | -6.558 | 61.292 | 1.00 | 26.25 |
| 5390 | CB | LYS | A | 670 | -50.587 | -7.438 | 60.566 | 1.00 | 26.78 |
| 5391 | CG | LYS | A | 670 | -49.279 | -7.584 | 61.318 | 1.00 | 28.50 |
| 5392 | CD | LYS | A | 670 | -48.530 | -8.859 | 60.937 | 1.00 | 31.27 |
| 5393 | CE | LYS | A | 670 | -47.245 | -8.973 | 61.731 | 1.00 | 30.90 |
| 5394 | NZ | LYS | A | 670 | -46.732 | -10.369 | 61.735 | 1.00 | 34.92 |
| 5395 | C | LYS | A | 670 | -52.409 | -5.763 | 60.276 | 1.00 | 26.83 |
| 5396 | O | LYS | A | 670 | -51.940 | -4.740 | 59.777 | 1.00 | 27.69 |

FIGURE 3 DB

| A | B | C | D | E | F | G | H | I | J |
|---|---|---|---|---|---|---|---|---|---|
| 5397 | N | GLN | A | 671 | -53.620 | -6.217 | 59.986 | 1.00 | 26.93 |
| 5398 | CA | GLN | A | 671 | -54.414 | -5.571 | 58.959 | 1.00 | 27.96 |
| 5399 | CB | GLN | A | 671 | -55.258 | -6.606 | 58.208 | 1.00 | 28.50 |
| 5400 | CG | GLN | A | 671 | -54.473 | -7.775 | 57.642 | 1.00 | 30.95 |
| 5401 | CD | GLN | A | 671 | -55.378 | -8.962 | 57.268 | 1.00 | 34.31 |
| 5402 | OE1 | GLN | A | 671 | -55.012 | -10.121 | 57.502 | 1.00 | 36.61 |
| 5403 | NE2 | GLN | A | 671 | -56.532 | -8.675 | 56.663 | 1.00 | 33.79 |
| 5404 | C | GLN | A | 671 | -55.338 | -4.472 | 59.471 | 1.00 | 27.43 |
| 5405 | O | GLN | A | 671 | -56.012 | -3.837 | 58.677 | 1.00 | 27.84 |
| 5406 | N | VAL | A | 672 | -55.390 | -4.239 | 60.775 | 1.00 | 26.34 |
| 5407 | CA | VAL | A | 672 | -56.322 | -3.242 | 61.267 | 1.00 | 25.27 |
| 5408 | CB | VAL | A | 672 | -57.529 | -3.897 | 61.964 | 1.00 | 25.36 |
| 5409 | CG1 | VAL | A | 672 | -58.253 | -4.844 | 61.057 | 1.00 | 24.92 |
| 5410 | CG2 | VAL | A | 672 | -57.084 | -4.616 | 63.233 | 1.00 | 25.04 |
| 5411 | C | VAL | A | 672 | -55.722 | -2.294 | 62.291 | 1.00 | 25.60 |
| 5412 | O | VAL | A | 672 | -54.597 | -2.452 | 62.760 | 1.00 | 24.76 |
| 5413 | N | GLU | A | 673 | -56.510 | -1.303 | 62.662 | 1.00 | 25.82 |
| 5414 | CA | GLU | A | 673 | -56.108 | -0.426 | 63.734 | 1.00 | 26.21 |
| 5415 | CB | GLU | A | 673 | -56.278 | 1.027 | 63.307 | 1.00 | 26.66 |
| 5416 | CG | GLU | A | 673 | -55.093 | 1.493 | 62.474 | 1.00 | 32.84 |
| 5417 | CD | GLU | A | 673 | -55.499 | 2.115 | 61.157 | 1.00 | 38.58 |
| 5418 | OE1 | GLU | A | 673 | -56.193 | 3.152 | 61.183 | 1.00 | 39.09 |
| 5419 | OE2 | GLU | A | 673 | -55.135 | 1.543 | 60.091 | 1.00 | 43.37 |
| 5420 | C | GLU | A | 673 | -56.906 | -0.800 | 64.979 | 1.00 | 24.83 |
| 5421 | O | GLU | A | 673 | -58.126 | -0.930 | 64.925 | 1.00 | 24.87 |
| 5422 | N | TYR | A | 674 | -56.208 | -0.944 | 66.097 | 1.00 | 23.74 |
| 5423 | CA | TYR | A | 674 | -56.796 | -1.468 | 67.305 | 1.00 | 23.16 |
| 5424 | CB | TYR | A | 674 | -56.128 | -2.803 | 67.576 | 1.00 | 23.69 |
| 5425 | CG | TYR | A | 674 | -56.730 | -3.691 | 68.635 | 1.00 | 22.50 |
| 5426 | CD1 | TYR | A | 674 | -58.097 | -3.782 | 68.818 | 1.00 | 21.88 |
| 5427 | CE1 | TYR | A | 674 | -58.626 | -4.653 | 69.757 | 1.00 | 20.32 |
| 5428 | CZ | TYR | A | 674 | -57.776 | -5.446 | 70.510 | 1.00 | 20.63 |
| 5429 | OH | TYR | A | 674 | -58.278 | -6.317 | 71.470 | 1.00 | 19.71 |
| 5430 | CE2 | TYR | A | 674 | -56.419 | -5.349 | 70.355 | 1.00 | 19.78 |
| 5431 | CD2 | TYR | A | 674 | -55.909 | -4.494 | 69.419 | 1.00 | 22.86 |
| 5432 | C | TYR | A | 674 | -56.521 | -0.613 | 68.505 | 1.00 | 22.50 |
| 5433 | O | TYR | A | 674 | -55.378 | -0.217 | 68.761 | 1.00 | 22.76 |
| 5434 | N | LEU | A | 675 | -57.572 | -0.373 | 69.276 | 1.00 | 21.36 |
| 5435 | CA | LEU | A | 675 | -57.442 | 0.346 | 70.520 | 1.00 | 20.60 |
| 5436 | CB | LEU | A | 675 | -58.244 | 1.624 | 70.470 | 1.00 | 20.09 |
| 5437 | CG | LEU | A | 675 | -58.453 | 2.411 | 71.752 | 1.00 | 21.82 |
| 5438 | CD1 | LEU | A | 675 | -57.128 | 2.565 | 72.554 | 1.00 | 21.00 |
| 5439 | CD2 | LEU | A | 675 | -59.092 | 3.773 | 71.432 | 1.00 | 17.43 |
| 5440 | C | LEU | A | 675 | -57.943 | -0.620 | 71.576 | 1.00 | 20.21 |
| 5441 | O | LEU | A | 675 | -59.030 | -1.156 | 71.458 | 1.00 | 19.19 |
| 5442 | N | LEU | A | 676 | -57.110 | -0.868 | 72.584 | 1.00 | 20.43 |
| 5443 | CA | LEU | A | 676 | -57.418 | -1.836 | 73.615 | 1.00 | 20.25 |
| 5444 | CB | LEU | A | 676 | -56.354 | -2.928 | 73.589 | 1.00 | 20.35 |
| 5445 | CG | LEU | A | 676 | -56.403 | -3.988 | 74.699 | 1.00 | 21.03 |
| 5446 | CD1 | LEU | A | 676 | -55.232 | -4.949 | 74.527 | 1.00 | 20.07 |
| 5447 | CD2 | LEU | A | 676 | -57.710 | -4.750 | 74.712 | 1.00 | 15.68 |

FIGURE 3 DC

| A | B | C | D | E | F | G | H | I | J |
|---|---|---|---|---|---|---|---|---|---|
| 5448 | C | LEU | A | 676 | -57.443 | -1.106 | 74.963 | 1.00 | 20.14 |
| 5449 | O | LEU | A | 676 | -56.462 | -0.496 | 75.364 | 1.00 | 20.18 |
| 5450 | N | ILE | A | 677 | -58.565 | -1.186 | 75.665 | 1.00 | 19.62 |
| 5451 | CA | ILE | A | 677 | -58.738 | -0.410 | 76.869 | 1.00 | 18.78 |
| 5452 | CB | ILE | A | 677 | -59.777 | 0.703 | 76.578 | 1.00 | 19.27 |
| 5453 | CG1 | ILE | A | 677 | -59.247 | 1.648 | 75.487 | 1.00 | 18.01 |
| 5454 | CD1 | ILE | A | 677 | -60.282 | 2.598 | 74.961 | 1.00 | 19.97 |
| 5455 | CG2 | ILE | A | 677 | -60.155 | 1.467 | 77.858 | 1.00 | 17.07 |
| 5456 | C | ILE | A | 677 | -59.247 | -1.287 | 77.964 | 1.00 | 18.90 |
| 5457 | O | ILE | A | 677 | -60.118 | -2.124 | 77.732 | 1.00 | 19.18 |
| 5458 | N | HIS | A | 678 | -58.729 | -1.093 | 79.172 | 1.00 | 18.70 |
| 5459 | CA | HIS | A | 678 | -59.159 | -1.919 | 80.307 | 1.00 | 18.53 |
| 5460 | CB | HIS | A | 678 | -58.382 | -3.248 | 80.293 | 1.00 | 17.83 |
| 5461 | CG | HIS | A | 678 | -59.202 | -4.430 | 80.703 | 1.00 | 16.75 |
| 5462 | ND1 | HIS | A | 678 | -59.772 | -4.538 | 81.950 | 1.00 | 16.89 |
| 5463 | CE1 | HIS | A | 678 | -60.449 | -5.670 | 82.028 | 1.00 | 15.28 |
| 5464 | NE2 | HIS | A | 678 | -60.325 | -6.305 | 80.878 | 1.00 | 17.63 |
| 5465 | CD2 | HIS | A | 678 | -59.550 | -5.552 | 80.031 | 1.00 | 13.04 |
| 5466 | C | HIS | A | 678 | -58.927 | -1.205 | 81.638 | 1.00 | 18.25 |
| 5467 | O | HIS | A | 678 | -57.954 | -0.495 | 81.797 | 1.00 | 18.44 |
| 5468 | N | GLY | A | 679 | -59.814 | -1.413 | 82.599 | 1.00 | 18.83 |
| 5469 | CA | GLY | A | 679 | -59.635 | -0.847 | 83.926 | 1.00 | 18.61 |
| 5470 | C | GLY | A | 679 | -58.778 | -1.817 | 84.730 | 1.00 | 19.16 |
| 5471 | O | GLY | A | 679 | -59.034 | -3.026 | 84.694 | 1.00 | 18.63 |
| 5472 | N | THR | A | 680 | -57.786 | -1.307 | 85.462 | 1.00 | 19.32 |
| 5473 | CA | THR | A | 680 | -56.872 | -2.181 | 86.193 | 1.00 | 20.63 |
| 5474 | CB | THR | A | 680 | -55.611 | -1.449 | 86.652 | 1.00 | 20.52 |
| 5475 | OG1 | THR | A | 680 | -55.945 | -0.454 | 87.629 | 1.00 | 19.71 |
| 5476 | CG2 | THR | A | 680 | -54.998 | -0.692 | 85.487 | 1.00 | 19.76 |
| 5477 | C | THR | A | 680 | -57.503 | -2.854 | 87.369 | 1.00 | 21.04 |
| 5478 | O | THR | A | 680 | -56.991 | -3.857 | 87.844 | 1.00 | 21.57 |
| 5479 | N | ALA | A | 681 | -58.629 | -2.324 | 87.828 | 1.00 | 21.61 |
| 5480 | CA | ALA | A | 681 | -59.307 | -2.924 | 88.969 | 1.00 | 21.60 |
| 5481 | CB | ALA | A | 681 | -59.531 | -1.881 | 90.106 | 1.00 | 21.79 |
| 5482 | C | ALA | A | 681 | -60.612 | -3.564 | 88.560 | 1.00 | 21.42 |
| 5483 | O | ALA | A | 681 | -61.578 | -3.609 | 89.346 | 1.00 | 22.68 |
| 5484 | N | ASP | A | 682 | -60.662 | -4.057 | 87.331 | 1.00 | 20.59 |
| 5485 | CA | ASP | A | 682 | -61.843 | -4.783 | 86.874 | 1.00 | 19.76 |
| 5486 | CB | ASP | A | 682 | -61.781 | -4.986 | 85.369 | 1.00 | 19.79 |
| 5487 | CG | ASP | A | 682 | -63.096 | -5.370 | 84.787 | 1.00 | 19.27 |
| 5488 | OD1 | ASP | A | 682 | -63.365 | -4.926 | 83.648 | 1.00 | 18.05 |
| 5489 | OD2 | ASP | A | 682 | -63.924 | -6.116 | 85.384 | 1.00 | 20.65 |
| 5490 | C | ASP | A | 682 | -61.849 | -6.143 | 87.574 | 1.00 | 19.39 |
| 5491 | O | ASP | A | 682 | -60.920 | -6.949 | 87.388 | 1.00 | 20.06 |
| 5492 | N | ASP | A | 683 | -62.873 | -6.368 | 88.383 | 1.00 | 17.86 |
| 5493 | CA | ASP | A | 683 | -63.053 | -7.579 | 89.154 | 1.00 | 18.48 |
| 5494 | CB | ASP | A | 683 | -63.826 | -7.242 | 90.432 | 1.00 | 17.90 |
| 5495 | CG | ASP | A | 683 | -65.169 | -6.613 | 90.128 | 1.00 | 18.77 |
| 5496 | OD1 | ASP | A | 683 | -65.198 | -5.405 | 89.794 | 1.00 | 18.95 |
| 5497 | OD2 | ASP | A | 683 | -66.254 | -7.240 | 90.165 | 1.00 | 19.04 |
| 5498 | C | ASP | A | 683 | -63.903 | -8.579 | 88.399 | 1.00 | 18.58 |

FIGURE 3 DD

| A | B | C | D | E | F | G | H | I | J |
|---|---|---|---|---|---|---|---|---|---|
| 5499 | O | ASP | A | 683 | -64.084 | -9.715 | 88.837 | 1.00 | 18.03 |
| 5500 | N | ASN | A | 684 | -64.458 | -8.115 | 87.288 | 1.00 | 19.43 |
| 5501 | CA | ASN | A | 684 | -65.363 | -8.906 | 86.477 | 1.00 | 20.04 |
| 5502 | CB | ASN | A | 684 | -66.486 | -8.023 | 85.949 | 1.00 | 20.24 |
| 5503 | CG | ASN | A | 684 | -67.604 | -8.818 | 85.340 | 1.00 | 19.66 |
| 5504 | OD1 | ASN | A | 684 | -68.750 | -8.370 | 85.273 | 1.00 | 21.80 |
| 5505 | ND2 | ASN | A | 684 | -67.288 | -9.999 | 84.902 | 1.00 | 20.70 |
| 5506 | C | ASN | A | 684 | -64.596 | -9.559 | 85.343 | 1.00 | 19.82 |
| 5507 | O | ASN | A | 684 | -64.396 | -10.765 | 85.359 | 1.00 | 19.74 |
| 5508 | N | VAL | A | 685 | -64.199 | -8.779 | 84.343 | 1.00 | 20.03 |
| 5509 | CA | VAL | A | 685 | -63.270 | -9.312 | 83.354 | 1.00 | 20.08 |
| 5510 | CB | VAL | A | 685 | -63.752 | -9.284 | 81.849 | 1.00 | 20.03 |
| 5511 | CG1 | VAL | A | 685 | -64.884 | -8.373 | 81.618 | 1.00 | 20.16 |
| 5512 | CG2 | VAL | A | 685 | -62.583 | -9.198 | 80.825 | 1.00 | 19.81 |
| 5513 | C | VAL | A | 685 | -61.916 | -8.742 | 83.711 | 1.00 | 20.09 |
| 5514 | O | VAL | A | 685 | -61.650 | -7.544 | 83.611 | 1.00 | 20.35 |
| 5515 | N | HIS | A | 686 | -61.075 | -9.631 | 84.213 | 1.00 | 20.12 |
| 5516 | CA | HIS | A | 686 | -59.821 | -9.218 | 84.812 | 1.00 | 19.79 |
| 5517 | CB | HIS | A | 686 | -59.188 | -10.425 | 85.511 | 1.00 | 19.73 |
| 5518 | CG | HIS | A | 686 | -60.135 | -11.064 | 86.471 | 1.00 | 20.36 |
| 5519 | ND1 | HIS | A | 686 | -60.197 | -12.425 | 86.682 | 1.00 | 20.39 |
| 5520 | CE1 | HIS | A | 686 | -61.167 | -12.685 | 87.546 | 1.00 | 22.42 |
| 5521 | NE2 | HIS | A | 686 | -61.730 | -11.542 | 87.905 | 1.00 | 21.66 |
| 5522 | CD2 | HIS | A | 686 | -61.111 | -10.514 | 87.238 | 1.00 | 19.34 |
| 5523 | C | HIS | A | 686 | -58.934 | -8.539 | 83.811 | 1.00 | 19.06 |
| 5524 | O | HIS | A | 686 | -58.963 | -8.878 | 82.636 | 1.00 | 19.35 |
| 5525 | N | PHE | A | 687 | -58.200 | -7.543 | 84.268 | 1.00 | 17.93 |
| 5526 | CA | PHE | A | 687 | -57.250 | -6.840 | 83.421 | 1.00 | 18.46 |
| 5527 | CB | PHE | A | 687 | -56.450 | -5.821 | 84.258 | 1.00 | 17.73 |
| 5528 | CG | PHE | A | 687 | -55.409 | -5.065 | 83.474 | 1.00 | 16.73 |
| 5529 | CD1 | PHE | A | 687 | -55.747 | -3.918 | 82.766 | 1.00 | 17.46 |
| 5530 | CE1 | PHE | A | 687 | -54.778 | -3.202 | 82.024 | 1.00 | 17.04 |
| 5531 | CZ | PHE | A | 687 | -53.453 | -3.649 | 82.030 | 1.00 | 18.40 |
| 5532 | CE2 | PHE | A | 687 | -53.115 | -4.795 | 82.754 | 1.00 | 19.00 |
| 5533 | CD2 | PHE | A | 687 | -54.091 | -5.498 | 83.457 | 1.00 | 16.43 |
| 5534 | C | PHE | A | 687 | -56.320 | -7.855 | 82.761 | 1.00 | 19.20 |
| 5535 | O | PHE | A | 687 | -55.843 | -7.643 | 81.629 | 1.00 | 20.05 |
| 5536 | N | GLN | A | 688 | -56.056 | -8.946 | 83.485 | 1.00 | 19.16 |
| 5537 | CA | GLN | A | 688 | -55.316 | -10.095 | 82.956 | 1.00 | 19.67 |
| 5538 | CB | GLN | A | 688 | -55.745 | -11.339 | 83.745 | 1.00 | 18.80 |
| 5539 | CG | GLN | A | 688 | -55.330 | -12.648 | 83.117 | 1.00 | 18.72 |
| 5540 | CD | GLN | A | 688 | -56.070 | -13.822 | 83.682 | 1.00 | 19.04 |
| 5541 | OE1 | GLN | A | 688 | -57.240 | -13.709 | 84.032 | 1.00 | 21.89 |
| 5542 | NE2 | GLN | A | 688 | -55.409 | -14.963 | 83.756 | 1.00 | 19.69 |
| 5543 | C | GLN | A | 688 | -55.685 | -10.360 | 81.510 | 1.00 | 20.02 |
| 5544 | O | GLN | A | 688 | -54.869 | -10.617 | 80.628 | 1.00 | 20.99 |
| 5545 | N | GLN | A | 689 | -56.969 | -10.303 | 81.295 | 1.00 | 20.02 |
| 5546 | CA | GLN | A | 689 | -57.558 | -10.662 | 80.022 | 1.00 | 21.16 |
| 5547 | CB | GLN | A | 689 | -59.068 | -10.641 | 80.242 | 1.00 | 20.04 |
| 5548 | CG | GLN | A | 689 | -59.791 | -11.314 | 79.236 | 1.00 | 24.17 |
| 5549 | CD | GLN | A | 689 | -60.562 | -12.518 | 79.697 | 1.00 | 22.03 |

FIGURE 3 DE

| A | B | C | D | E | F | G | H | I | J |
|---|---|---|---|---|---|---|---|---|---|
| 5550 | OE1 | GLN | A | 689 | -60.625 | -13.434 | 78.941 | 1.00 | 23.32 |
| 5551 | NE2 | GLN | A | 689 | -61.210 | -12.487 | 80.877 | 1.00 | 18.54 |
| 5552 | C | GLN | A | 689 | -57.040 | -9.780 | 78.842 | 1.00 | 20.37 |
| 5553 | O | GLN | A | 689 | -56.679 | -10.282 | 77.769 | 1.00 | 19.90 |
| 5554 | N | SER | A | 690 | -56.914 | -8.477 | 79.070 | 1.00 | 20.07 |
| 5555 | CA | SER | A | 690 | -56.309 | -7.607 | 78.066 | 1.00 | 19.13 |
| 5556 | CB | SER | A | 690 | -56.806 | -6.175 | 78.221 | 1.00 | 19.29 |
| 5557 | OG | SER | A | 690 | -58.131 | -6.079 | 77.729 | 1.00 | 19.94 |
| 5558 | C | SER | A | 690 | -54.778 | -7.635 | 78.140 | 1.00 | 18.61 |
| 5559 | O | SER | A | 690 | -54.082 | -7.416 | 77.147 | 1.00 | 18.97 |
| 5560 | N | ALA | A | 691 | -54.241 | -7.901 | 79.309 | 1.00 | 17.44 |
| 5561 | CA | ALA | A | 691 | -52.808 | -8.011 | 79.391 | 1.00 | 18.16 |
| 5562 | CB | ALA | A | 691 | -52.344 | -8.171 | 80.835 | 1.00 | 17.77 |
| 5563 | C | ALA | A | 691 | -52.340 | -9.186 | 78.516 | 1.00 | 18.66 |
| 5564 | O | ALA | A | 691 | -51.245 | -9.157 | 77.964 | 1.00 | 18.93 |
| 5565 | N | GLN | A | 692 | -53.179 | -10.199 | 78.358 | 1.00 | 18.73 |
| 5566 | CA | GLN | A | 692 | -52.806 | -11.332 | 77.510 | 1.00 | 19.69 |
| 5567 | CB | GLN | A | 692 | -53.576 | -12.603 | 77.892 | 1.00 | 18.56 |
| 5568 | CG | GLN | A | 692 | -53.201 | -13.095 | 79.275 | 1.00 | 20.39 |
| 5569 | CD | GLN | A | 692 | -51.780 | -13.645 | 79.376 | 1.00 | 23.39 |
| 5570 | OE1 | GLN | A | 692 | -50.982 | -13.499 | 78.466 | 1.00 | 25.31 |
| 5571 | NE2 | GLN | A | 692 | -51.474 | -14.301 | 80.497 | 1.00 | 26.76 |
| 5572 | C | GLN | A | 692 | -52.949 | -11.005 | 76.036 | 1.00 | 20.10 |
| 5573 | O | GLN | A | 692 | -52.187 | -11.506 | 75.223 | 1.00 | 21.08 |
| 5574 | N | ILE | A | 693 | -53.886 | -10.130 | 75.692 | 1.00 | 20.67 |
| 5575 | CA | ILE | A | 693 | -54.047 | -9.709 | 74.305 | 1.00 | 20.84 |
| 5576 | CB | ILE | A | 693 | -55.325 | -8.836 | 74.151 | 1.00 | 20.74 |
| 5577 | CG1 | ILE | A | 693 | -56.601 | -9.653 | 74.369 | 1.00 | 21.91 |
| 5578 | CD1 | ILE | A | 693 | -57.898 | -8.813 | 74.261 | 1.00 | 20.81 |
| 5579 | CG2 | ILE | A | 693 | -55.353 | -8.152 | 72.786 | 1.00 | 19.56 |
| 5580 | C | ILE | A | 693 | -52.859 | -8.863 | 73.881 | 1.00 | 21.49 |
| 5581 | O | ILE | A | 693 | -52.344 | -8.991 | 72.758 | 1.00 | 22.44 |
| 5582 | N | SER | A | 694 | -52.441 | -7.955 | 74.766 | 1.00 | 21.62 |
| 5583 | CA | SER | A | 694 | -51.366 | -7.025 | 74.430 | 1.00 | 20.99 |
| 5584 | CB | SER | A | 694 | -51.237 | -5.936 | 75.509 | 1.00 | 21.40 |
| 5585 | OG | SER | A | 694 | -50.800 | -6.466 | 76.767 | 1.00 | 21.44 |
| 5586 | C | SER | A | 694 | -50.046 | -7.776 | 74.245 | 1.00 | 20.98 |
| 5587 | O | SER | A | 694 | -49.299 | -7.497 | 73.318 | 1.00 | 20.54 |
| 5588 | N | LYS | A | 695 | -49.788 | -8.757 | 75.108 | 1.00 | 20.70 |
| 5589 | CA | LYS | A | 695 | -48.558 | -9.527 | 75.042 | 1.00 | 21.06 |
| 5590 | CB | LYS | A | 695 | -48.450 | -10.469 | 76.253 | 1.00 | 21.11 |
| 5591 | CG | LYS | A | 695 | -47.228 | -11.380 | 76.223 | 1.00 | 19.11 |
| 5592 | CD | LYS | A | 695 | -46.817 | -11.821 | 77.621 | 1.00 | 17.75 |
| 5593 | CE | LYS | A | 695 | -47.969 | -12.543 | 78.326 | 1.00 | 22.33 |
| 5594 | NZ | LYS | A | 695 | -48.205 | -13.939 | 77.821 | 1.00 | 21.64 |
| 5595 | C | LYS | A | 695 | -48.480 | -10.325 | 73.744 | 1.00 | 21.90 |
| 5596 | O | LYS | A | 695 | -47.430 | -10.384 | 73.090 | 1.00 | 22.18 |
| 5597 | N | ALA | A | 696 | -49.605 | -10.923 | 73.367 | 1.00 | 21.75 |
| 5598 | CA | ALA | A | 696 | -49.674 | -11.701 | 72.152 | 1.00 | 22.10 |
| 5599 | CB | ALA | A | 696 | -51.026 | -12.427 | 72.071 | 1.00 | 22.32 |
| 5600 | C | ALA | A | 696 | -49.453 | -10.814 | 70.915 | 1.00 | 22.60 |

FIGURE 3 DF

| A | B | C | D | E | F | G | H | I | J |
|---|---|---|---|---|---|---|---|---|---|
| 5601 | O | ALA | A | 696 | -48.814 | -11.235 | 69.941 | 1.00 | 23.63 |
| 5602 | N | LEU | A | 697 | -49.980 | -9.596 | 70.945 | 1.00 | 21.62 |
| 5603 | CA | LEU | A | 697 | -49.785 | -8.680 | 69.833 | 1.00 | 21.54 |
| 5604 | CB | LEU | A | 697 | -50.685 | -7.455 | 69.976 | 1.00 | 20.89 |
| 5605 | CG | LEU | A | 697 | -52.164 | -7.826 | 69.864 | 1.00 | 20.86 |
| 5606 | CD1 | LEU | A | 697 | -53.084 | -6.621 | 70.175 | 1.00 | 20.00 |
| 5607 | CD2 | LEU | A | 697 | -52.411 | -8.383 | 68.457 | 1.00 | 19.20 |
| 5608 | C | LEU | A | 697 | -48.343 | -8.255 | 69.744 | 1.00 | 21.66 |
| 5609 | O | LEU | A | 697 | -47.749 | -8.208 | 68.671 | 1.00 | 22.68 |
| 5610 | N | VAL | A | 698 | -47.772 | -7.950 | 70.889 | 1.00 | 21.80 |
| 5611 | CA | VAL | A | 698 | -46.386 | -7.580 | 70.947 | 1.00 | 21.82 |
| 5612 | CB | VAL | A | 698 | -45.956 | -7.293 | 72.411 | 1.00 | 21.78 |
| 5613 | CG1 | VAL | A | 698 | -44.448 | -7.058 | 72.492 | 1.00 | 19.00 |
| 5614 | CG2 | VAL | A | 698 | -46.718 | -6.080 | 72.932 | 1.00 | 21.15 |
| 5615 | C | VAL | A | 698 | -45.543 | -8.695 | 70.373 | 1.00 | 22.31 |
| 5616 | O | VAL | A | 698 | -44.636 | -8.464 | 69.582 | 1.00 | 22.30 |
| 5617 | N | ASP | A | 699 | -45.837 | -9.912 | 70.793 | 1.00 | 23.20 |
| 5618 | CA | ASP | A | 699 | -45.087 | -11.066 | 70.341 | 1.00 | 24.23 |
| 5619 | CB | ASP | A | 699 | -45.472 | -12.288 | 71.163 | 1.00 | 24.60 |
| 5620 | CG | ASP | A | 699 | -44.916 | -12.227 | 72.576 | 1.00 | 28.11 |
| 5621 | OD1 | ASP | A | 699 | -45.394 | -13.002 | 73.438 | 1.00 | 31.21 |
| 5622 | OD2 | ASP | A | 699 | -44.003 | -11.428 | 72.913 | 1.00 | 29.15 |
| 5623 | C | ASP | A | 699 | -45.139 | -11.357 | 68.835 | 1.00 | 24.78 |
| 5624 | O | ASP | A | 699 | -44.295 | -12.089 | 68.344 | 1.00 | 25.40 |
| 5625 | N | VAL | A | 700 | -46.113 | -10.814 | 68.103 | 1.00 | 25.13 |
| 5626 | CA | VAL | A | 700 | -46.132 | -10.998 | 66.650 | 1.00 | 25.71 |
| 5627 | CB | VAL | A | 700 | -47.475 | -11.541 | 66.081 | 1.00 | 26.39 |
| 5628 | CG1 | VAL | A | 700 | -48.681 | -10.797 | 66.679 | 1.00 | 26.60 |
| 5629 | CG2 | VAL | A | 700 | -47.501 | -11.325 | 64.590 | 1.00 | 29.63 |
| 5630 | C | VAL | A | 700 | -45.819 | -9.673 | 65.980 | 1.00 | 25.45 |
| 5631 | O | VAL | A | 700 | -45.959 | -9.515 | 64.770 | 1.00 | 24.57 |
| 5632 | N | GLY | A | 701 | -45.410 | -8.696 | 66.779 | 1.00 | 25.84 |
| 5633 | CA | GLY | A | 701 | -44.989 | -7.427 | 66.221 | 1.00 | 25.28 |
| 5634 | C | GLY | A | 701 | -46.071 | -6.590 | 65.564 | 1.00 | 25.90 |
| 5635 | O | GLY | A | 701 | -45.807 | -5.945 | 64.545 | 1.00 | 26.61 |
| 5636 | N | VAL | A | 702 | -47.284 | -6.577 | 66.114 | 1.00 | 25.54 |
| 5637 | CA | VAL | A | 702 | -48.278 | -5.673 | 65.569 | 1.00 | 25.62 |
| 5638 | CB | VAL | A | 702 | -49.634 | -6.333 | 65.229 | 1.00 | 25.87 |
| 5639 | CG1 | VAL | A | 702 | -49.524 | -7.843 | 65.210 | 1.00 | 27.50 |
| 5640 | CG2 | VAL | A | 702 | -50.733 | -5.851 | 66.159 | 1.00 | 25.14 |
| 5641 | C | VAL | A | 702 | -48.462 | -4.476 | 66.487 | 1.00 | 25.24 |
| 5642 | O | VAL | A | 702 | -48.465 | -4.601 | 67.721 | 1.00 | 25.45 |
| 5643 | N | ASP | A | 703 | -48.572 | -3.298 | 65.897 | 1.00 | 25.10 |
| 5644 | CA | ASP | A | 703 | -48.762 | -2.146 | 66.727 | 1.00 | 25.76 |
| 5645 | CB | ASP | A | 703 | -47.982 | -0.927 | 66.251 | 1.00 | 26.50 |
| 5646 | CG | ASP | A | 703 | -47.352 | -0.205 | 67.422 | 1.00 | 29.15 |
| 5647 | OD1 | ASP | A | 703 | -47.844 | 0.867 | 67.752 | 1.00 | 27.65 |
| 5648 | OD2 | ASP | A | 703 | -46.386 | -0.691 | 68.098 | 1.00 | 34.54 |
| 5649 | C | ASP | A | 703 | -50.233 | -1.833 | 66.921 | 1.00 | 25.15 |
| 5650 | O | ASP | A | 703 | -51.064 | -2.154 | 66.089 | 1.00 | 25.14 |
| 5651 | N | PHE | A | 704 | -50.539 | -1.205 | 68.041 | 1.00 | 24.41 |

FIGURE 3 DG

| A | B | C | D | E | F | G | H | I | J |
|---|---|---|---|---|---|---|---|---|---|
| 5652 | CA | PHE | A | 704 | -51.918 | -0.982 | 68.392 | 1.00 | 23.98 |
| 5653 | CB | PHE | A | 704 | -52.511 | -2.289 | 68.902 | 1.00 | 23.42 |
| 5654 | CG | PHE | A | 704 | -51.854 | -2.793 | 70.144 | 1.00 | 21.87 |
| 5655 | CD1 | PHE | A | 704 | -52.307 | -2.394 | 71.390 | 1.00 | 20.47 |
| 5656 | CE1 | PHE | A | 704 | -51.689 | -2.862 | 72.555 | 1.00 | 20.10 |
| 5657 | CZ | PHE | A | 704 | -50.622 | -3.722 | 72.466 | 1.00 | 19.75 |
| 5658 | CE2 | PHE | A | 704 | -50.158 | -4.120 | 71.228 | 1.00 | 20.84 |
| 5659 | CD2 | PHE | A | 704 | -50.769 | -3.654 | 70.072 | 1.00 | 20.98 |
| 5660 | C | PHE | A | 704 | -51.944 | 0.064 | 69.481 | 1.00 | 23.79 |
| 5661 | O | PHE | A | 704 | -50.896 | 0.405 | 70.040 | 1.00 | 23.48 |
| 5662 | N | GLN | A | 705 | -53.135 | 0.573 | 69.776 | 1.00 | 23.59 |
| 5663 | CA | GLN | A | 705 | -53.276 | 1.629 | 70.780 | 1.00 | 23.77 |
| 5664 | CB | GLN | A | 705 | -54.343 | 2.639 | 70.368 | 1.00 | 24.73 |
| 5665 | CG | GLN | A | 705 | -54.119 | 3.225 | 69.034 | 1.00 | 27.99 |
| 5666 | CD | GLN | A | 705 | -52.835 | 3.950 | 69.005 | 1.00 | 34.84 |
| 5667 | OE1 | GLN | A | 705 | -51.939 | 3.604 | 68.216 | 1.00 | 39.07 |
| 5668 | NE2 | GLN | A | 705 | -52.703 | 4.957 | 69.874 | 1.00 | 34.12 |
| 5669 | C | GLN | A | 705 | -53.751 | 0.998 | 72.032 | 1.00 | 22.34 |
| 5670 | O | GLN | A | 705 | -54.492 | 0.039 | 71.989 | 1.00 | 22.88 |
| 5671 | N | ALA | A | 706 | -53.361 | 1.563 | 73.151 | 1.00 | 21.59 |
| 5672 | CA | ALA | A | 706 | -53.754 | 1.015 | 74.427 | 1.00 | 21.27 |
| 5673 | CB | ALA | A | 706 | -52.656 | 0.139 | 74.981 | 1.00 | 21.03 |
| 5674 | C | ALA | A | 706 | -54.076 | 2.096 | 75.417 | 1.00 | 21.31 |
| 5675 | O | ALA | A | 706 | -53.567 | 3.219 | 75.350 | 1.00 | 21.42 |
| 5676 | N | MET | A | 707 | -54.946 | 1.756 | 76.347 | 1.00 | 21.58 |
| 5677 | CA | MET | A | 707 | -55.193 | 2.650 | 77.456 | 1.00 | 21.80 |
| 5678 | CB | MET | A | 707 | -56.241 | 3.703 | 77.093 | 1.00 | 20.90 |
| 5679 | CG | MET | A | 707 | -56.551 | 4.628 | 78.247 | 1.00 | 23.88 |
| 5680 | SD | MET | A | 707 | -55.230 | 5.830 | 78.520 | 1.00 | 25.22 |
| 5681 | CE | MET | A | 707 | -55.541 | 6.235 | 80.200 | 1.00 | 31.39 |
| 5682 | C | MET | A | 707 | -55.670 | 1.827 | 78.638 | 1.00 | 21.25 |
| 5683 | O | MET | A | 707 | -56.672 | 1.152 | 78.542 | 1.00 | 22.25 |
| 5684 | N | TRP | A | 708 | -54.955 | 1.893 | 79.748 | 1.00 | 21.26 |
| 5685 | CA | TRP | A | 708 | -55.383 | 1.243 | 80.986 | 1.00 | 21.09 |
| 5686 | CB | TRP | A | 708 | -54.159 | 0.674 | 81.733 | 1.00 | 20.16 |
| 5687 | CG | TRP | A | 708 | -53.290 | 1.679 | 82.397 | 1.00 | 21.34 |
| 5688 | CD1 | TRP | A | 708 | -53.524 | 2.319 | 83.592 | 1.00 | 20.72 |
| 5689 | NE1 | TRP | A | 708 | -52.496 | 3.189 | 83.869 | 1.00 | 19.65 |
| 5690 | CE2 | TRP | A | 708 | -51.559 | 3.112 | 82.873 | 1.00 | 20.47 |
| 5691 | CD2 | TRP | A | 708 | -52.019 | 2.169 | 81.930 | 1.00 | 21.66 |
| 5692 | CE3 | TRP | A | 708 | -51.227 | 1.907 | 80.809 | 1.00 | 19.72 |
| 5693 | CZ3 | TRP | A | 708 | -50.039 | 2.560 | 80.675 | 1.00 | 20.65 |
| 5694 | CH2 | TRP | A | 708 | -49.610 | 3.499 | 81.630 | 1.00 | 20.89 |
| 5695 | CZ2 | TRP | A | 708 | -50.348 | 3.775 | 82.735 | 1.00 | 20.23 |
| 5696 | C | TRP | A | 708 | -56.063 | 2.326 | 81.826 | 1.00 | 20.98 |
| 5697 | O | TRP | A | 708 | -55.741 | 3.488 | 81.679 | 1.00 | 21.48 |
| 5698 | N | TYR | A | 709 | -57.015 | 1.973 | 82.678 | 1.00 | 20.79 |
| 5699 | CA | TYR | A | 709 | -57.582 | 2.972 | 83.596 | 1.00 | 19.76 |
| 5700 | CB | TYR | A | 709 | -59.065 | 3.279 | 83.313 | 1.00 | 19.02 |
| 5701 | CG | TYR | A | 709 | -59.226 | 4.211 | 82.143 | 1.00 | 17.81 |
| 5702 | CD1 | TYR | A | 709 | -59.054 | 5.604 | 82.282 | 1.00 | 15.94 |

FIGURE 3 DH

| A | B | C | D | E | F | G | H | I | J |
|---|---|---|---|---|---|---|---|---|---|
| 5703 | CE1 | TYR | A | 709 | -59.196 | 6.453 | 81.179 | 1.00 | 16.02 |
| 5704 | CZ | TYR | A | 709 | -59.480 | 5.894 | 79.914 | 1.00 | 18.36 |
| 5705 | OH | TYR | A | 709 | -59.627 | 6.670 | 78.773 | 1.00 | 19.00 |
| 5706 | CE2 | TYR | A | 709 | -59.626 | 4.525 | 79.768 | 1.00 | 15.11 |
| 5707 | CD2 | TYR | A | 709 | -59.502 | 3.699 | 80.871 | 1.00 | 16.48 |
| 5708 | C | TYR | A | 709 | -57.340 | 2.570 | 85.042 | 1.00 | 19.87 |
| 5709 | O | TYR | A | 709 | -57.962 | 1.669 | 85.575 | 1.00 | 19.67 |
| 5710 | N | THR | A | 710 | -56.400 | 3.253 | 85.664 | 1.00 | 20.79 |
| 5711 | CA | THR | A | 710 | -56.017 | 2.973 | 87.025 | 1.00 | 21.00 |
| 5712 | CB | THR | A | 710 | -55.062 | 4.049 | 87.479 | 1.00 | 21.32 |
| 5713 | OG1 | THR | A | 710 | -53.905 | 4.050 | 86.629 | 1.00 | 23.26 |
| 5714 | CG2 | THR | A | 710 | -54.539 | 3.759 | 88.852 | 1.00 | 20.93 |
| 5715 | C | THR | A | 710 | -57.225 | 2.988 | 87.934 | 1.00 | 21.30 |
| 5716 | O | THR | A | 710 | -57.931 | 3.991 | 87.991 | 1.00 | 21.23 |
| 5717 | N | ASP | A | 711 | -57.437 | 1.863 | 88.619 | 1.00 | 20.65 |
| 5718 | CA | ASP | A | 711 | -58.451 | 1.681 | 89.660 | 1.00 | 21.12 |
| 5719 | CB | ASP | A | 711 | -58.255 | 2.651 | 90.843 | 1.00 | 20.66 |
| 5720 | CG | ASP | A | 711 | -56.972 | 2.389 | 91.609 | 1.00 | 22.62 |
| 5721 | OD1 | ASP | A | 711 | -56.480 | 3.311 | 92.335 | 1.00 | 23.36 |
| 5722 | OD2 | ASP | A | 711 | -56.362 | 1.295 | 91.533 | 1.00 | 23.12 |
| 5723 | C | ASP | A | 711 | -59.887 | 1.669 | 89.176 | 1.00 | 21.05 |
| 5724 | O | ASP | A | 711 | -60.828 | 1.591 | 89.969 | 1.00 | 21.25 |
| 5725 | N | GLU | A | 712 | -60.071 | 1.733 | 87.872 | 1.00 | 21.35 |
| 5726 | CA | GLU | A | 712 | -61.418 | 1.654 | 87.347 | 1.00 | 21.45 |
| 5727 | CB | GLU | A | 712 | -61.489 | 2.370 | 86.016 | 1.00 | 21.52 |
| 5728 | CG | GLU | A | 712 | -61.321 | 3.874 | 86.177 | 1.00 | 23.03 |
| 5729 | CD | GLU | A | 712 | -62.496 | 4.500 | 86.923 | 1.00 | 25.84 |
| 5730 | OE1 | GLU | A | 712 | -62.284 | 5.209 | 87.913 | 1.00 | 28.25 |
| 5731 | OE2 | GLU | A | 712 | -63.650 | 4.274 | 86.528 | 1.00 | 29.59 |
| 5732 | C | GLU | A | 712 | -61.897 | 0.200 | 87.255 | 1.00 | 21.45 |
| 5733 | O | GLU | A | 712 | -61.091 | -0.707 | 87.054 | 1.00 | 21.45 |
| 5734 | N | ASP | A | 713 | -63.196 | -0.044 | 87.448 | 1.00 | 21.48 |
| 5735 | CA | ASP | A | 713 | -63.659 | -1.418 | 87.327 | 1.00 | 21.88 |
| 5736 | CB | ASP | A | 713 | -64.536 | -1.860 | 88.504 | 1.00 | 21.50 |
| 5737 | CG | ASP | A | 713 | -65.855 | -1.156 | 88.557 | 1.00 | 21.33 |
| 5738 | OD1 | ASP | A | 713 | -66.584 | -1.385 | 89.538 | 1.00 | 22.46 |
| 5739 | OD2 | ASP | A | 713 | -66.263 | -0.376 | 87.685 | 1.00 | 22.10 |
| 5740 | C | ASP | A | 713 | -64.265 | -1.709 | 85.963 | 1.00 | 22.03 |
| 5741 | O | ASP | A | 713 | -63.952 | -1.033 | 85.013 | 1.00 | 22.71 |
| 5742 | N | HIS | A | 714 | -65.111 | -2.719 | 85.858 | 1.00 | 22.81 |
| 5743 | CA | HIS | A | 714 | -65.653 | -3.106 | 84.562 | 1.00 | 23.58 |
| 5744 | CB | HIS | A | 714 | -66.471 | -4.389 | 84.669 | 1.00 | 23.35 |
| 5745 | CG | HIS | A | 714 | -66.651 | -5.079 | 83.359 | 1.00 | 23.79 |
| 5746 | ND1 | HIS | A | 714 | -65.593 | -5.358 | 82.523 | 1.00 | 25.47 |
| 5747 | CE1 | HIS | A | 714 | -66.042 | -5.947 | 81.429 | 1.00 | 23.28 |
| 5748 | NE2 | HIS | A | 714 | -67.349 | -6.067 | 81.533 | 1.00 | 23.63 |
| 5749 | CD2 | HIS | A | 714 | -67.758 | -5.520 | 82.723 | 1.00 | 23.05 |
| 5750 | C | HIS | A | 714 | -66.496 | -2.034 | 83.892 | 1.00 | 24.39 |
| 5751 | O | HIS | A | 714 | -66.584 | -1.985 | 82.668 | 1.00 | 24.97 |
| 5752 | N | GLY | A | 715 | -67.112 | -1.165 | 84.686 | 1.00 | 24.59 |
| 5753 | CA | GLY | A | 715 | -67.922 | -0.113 | 84.108 | 1.00 | 23.89 |

FIGURE 3 DI

| A | B | C | D | E | F | G | H | I | J |
|---|---|---|---|---|---|---|---|---|---|
| 5754 | C | GLY | A | 715 | -67.139 | 1.133 | 83.718 | 1.00 | 23.81 |
| 5755 | O | GLY | A | 715 | -67.711 | 2.028 | 83.102 | 1.00 | 23.91 |
| 5756 | N | ILE | A | 716 | -65.844 | 1.189 | 84.044 | 1.00 | 23.22 |
| 5757 | CA | ILE | A | 716 | -65.056 | 2.404 | 83.824 | 1.00 | 23.24 |
| 5758 | CB | ILE | A | 716 | -64.378 | 2.441 | 82.452 | 1.00 | 22.71 |
| 5759 | CG1 | ILE | A | 716 | -63.681 | 1.101 | 82.158 | 1.00 | 22.49 |
| 5760 | CD1 | ILE | A | 716 | -62.688 | 1.176 | 81.007 | 1.00 | 20.92 |
| 5761 | CG2 | ILE | A | 716 | -63.382 | 3.573 | 82.430 | 1.00 | 19.75 |
| 5762 | C | ILE | A | 716 | -65.990 | 3.594 | 83.988 | 1.00 | 24.33 |
| 5763 | O | ILE | A | 716 | -66.240 | 4.386 | 83.065 | 1.00 | 23.79 |
| 5764 | N | ALA | A | 717 | -66.500 | 3.740 | 85.193 | 1.00 | 25.20 |
| 5765 | CA | ALA | A | 717 | -67.605 | 4.648 | 85.317 | 1.00 | 26.42 |
| 5766 | CB | ALA | A | 717 | -68.916 | 3.843 | 85.641 | 1.00 | 25.98 |
| 5767 | C | ALA | A | 717 | -67.417 | 5.843 | 86.239 | 1.00 | 26.81 |
| 5768 | O | ALA | A | 717 | -68.328 | 6.653 | 86.343 | 1.00 | 28.31 |
| 5769 | N | SER | A | 718 | -66.283 | 5.967 | 86.923 | 1.00 | 26.76 |
| 5770 | CA | SER | A | 718 | -66.050 | 7.219 | 87.640 | 1.00 | 26.89 |
| 5771 | CB | SER | A | 718 | -64.600 | 7.418 | 88.008 | 1.00 | 25.63 |
| 5772 | OG | SER | A | 718 | -64.179 | 6.429 | 88.906 | 1.00 | 31.72 |
| 5773 | C | SER | A | 718 | -66.360 | 8.302 | 86.634 | 1.00 | 26.49 |
| 5774 | O | SER | A | 718 | -66.133 | 8.132 | 85.437 | 1.00 | 26.34 |
| 5775 | N | SER | A | 719 | -66.824 | 9.433 | 87.124 | 1.00 | 26.34 |
| 5776 | CA | SER | A | 719 | -67.100 | 10.557 | 86.253 | 1.00 | 26.36 |
| 5777 | CB | SER | A | 719 | -67.604 | 11.729 | 87.091 | 1.00 | 26.02 |
| 5778 | OG | SER | A | 719 | -67.345 | 12.944 | 86.446 | 1.00 | 28.60 |
| 5779 | C | SER | A | 719 | -65.895 | 10.944 | 85.377 | 1.00 | 25.43 |
| 5780 | O | SER | A | 719 | -66.030 | 11.113 | 84.188 | 1.00 | 24.62 |
| 5781 | N | THR | A | 720 | -64.703 | 11.052 | 85.943 | 1.00 | 25.44 |
| 5782 | CA | THR | A | 720 | -63.586 | 11.512 | 85.119 | 1.00 | 24.70 |
| 5783 | CB | THR | A | 720 | -62.452 | 11.979 | 85.988 | 1.00 | 25.07 |
| 5784 | OG1 | THR | A | 720 | -62.117 | 10.936 | 86.921 | 1.00 | 25.60 |
| 5785 | CG2 | THR | A | 720 | -62.931 | 13.171 | 86.835 | 1.00 | 24.75 |
| 5786 | C | THR | A | 720 | -63.076 | 10.478 | 84.137 | 1.00 | 24.15 |
| 5787 | O | THR | A | 720 | -62.635 | 10.828 | 83.042 | 1.00 | 23.77 |
| 5788 | N | ALA | A | 721 | -63.142 | 9.207 | 84.525 | 1.00 | 23.57 |
| 5789 | CA | ALA | A | 721 | -62.688 | 8.130 | 83.653 | 1.00 | 23.35 |
| 5790 | CB | ALA | A | 721 | -62.489 | 6.820 | 84.446 | 1.00 | 23.36 |
| 5791 | C | ALA | A | 721 | -63.684 | 7.926 | 82.532 | 1.00 | 22.88 |
| 5792 | O | ALA | A | 721 | -63.303 | 7.651 | 81.407 | 1.00 | 22.47 |
| 5793 | N | HIS | A | 722 | -64.966 | 8.075 | 82.855 | 1.00 | 23.03 |
| 5794 | CA | HIS | A | 722 | -66.029 | 7.955 | 81.872 | 1.00 | 22.95 |
| 5795 | CB | HIS | A | 722 | -67.403 | 8.167 | 82.521 | 1.00 | 22.90 |
| 5796 | CG | HIS | A | 722 | -68.525 | 8.292 | 81.527 | 1.00 | 23.87 |
| 5797 | ND1 | HIS | A | 722 | -68.953 | 7.237 | 80.747 | 1.00 | 24.64 |
| 5798 | CE1 | HIS | A | 722 | -69.931 | 7.639 | 79.956 | 1.00 | 24.39 |
| 5799 | NE2 | HIS | A | 722 | -70.157 | 8.917 | 80.197 | 1.00 | 26.13 |
| 5800 | CD2 | HIS | A | 722 | -69.291 | 9.351 | 81.174 | 1.00 | 23.85 |
| 5801 | C | HIS | A | 722 | -65.794 | 9.003 | 80.796 | 1.00 | 23.22 |
| 5802 | O | HIS | A | 722 | -65.777 | 8.709 | 79.609 | 1.00 | 22.74 |
| 5803 | N | GLN | A | 723 | -65.563 | 10.238 | 81.221 | 1.00 | 23.31 |
| 5804 | CA | GLN | A | 723 | -65.297 | 11.297 | 80.252 | 1.00 | 23.21 |

FIGURE 3 DJ

| A | B | C | D | E | F | G | H | I | J |
|---|---|---|---|---|---|---|---|---|---|
| 5805 | CB | GLN | A | 723 | -65.205 | 12.637 | 80.984 | 1.00 | 23.00 |
| 5806 | CG | GLN | A | 723 | -66.493 | 12.899 | 81.716 | 1.00 | 24.49 |
| 5807 | CD | GLN | A | 723 | -66.503 | 14.184 | 82.467 | 1.00 | 26.80 |
| 5808 | OE1 | GLN | A | 723 | -66.444 | 15.263 | 81.862 | 1.00 | 31.36 |
| 5809 | NE2 | GLN | A | 723 | -66.617 | 14.096 | 83.786 | 1.00 | 26.57 |
| 5810 | C | GLN | A | 723 | -64.028 | 11.036 | 79.477 | 1.00 | 22.62 |
| 5811 | O | GLN | A | 723 | -63.955 | 11.294 | 78.274 | 1.00 | 23.70 |
| 5812 | N | HIS | A | 724 | -63.014 | 10.541 | 80.168 | 1.00 | 21.60 |
| 5813 | CA | HIS | A | 724 | -61.728 | 10.320 | 79.535 | 1.00 | 21.22 |
| 5814 | CB | HIS | A | 724 | -60.666 | 9.958 | 80.594 | 1.00 | 20.83 |
| 5815 | CG | HIS | A | 724 | -59.267 | 10.092 | 80.087 | 1.00 | 22.39 |
| 5816 | ND1 | HIS | A | 724 | -58.678 | 9.140 | 79.285 | 1.00 | 23.74 |
| 5817 | CE1 | HIS | A | 724 | -57.464 | 9.546 | 78.950 | 1.00 | 26.52 |
| 5818 | NE2 | HIS | A | 724 | -57.260 | 10.740 | 79.480 | 1.00 | 24.52 |
| 5819 | CD2 | HIS | A | 724 | -58.375 | 11.108 | 80.188 | 1.00 | 22.62 |
| 5820 | C | HIS | A | 724 | -61.779 | 9.241 | 78.445 | 1.00 | 20.97 |
| 5821 | O | HIS | A | 724 | -61.273 | 9.432 | 77.325 | 1.00 | 21.47 |
| 5822 | N | ILE | A | 725 | -62.397 | 8.108 | 78.755 | 1.00 | 20.53 |
| 5823 | CA | ILE | A | 725 | -62.431 | 7.025 | 77.783 | 1.00 | 20.56 |
| 5824 | CB | ILE | A | 725 | -62.876 | 5.676 | 78.432 | 1.00 | 20.64 |
| 5825 | CG1 | ILE | A | 725 | -62.653 | 4.516 | 77.443 | 1.00 | 20.06 |
| 5826 | CD1 | ILE | A | 725 | -63.234 | 3.188 | 77.884 | 1.00 | 18.35 |
| 5827 | CG2 | ILE | A | 725 | -64.305 | 5.762 | 79.037 | 1.00 | 20.09 |
| 5828 | C | ILE | A | 725 | -63.197 | 7.402 | 76.512 | 1.00 | 20.84 |
| 5829 | O | ILE | A | 725 | -62.681 | 7.234 | 75.390 | 1.00 | 20.98 |
| 5830 | N | TYR | A | 726 | -64.388 | 7.977 | 76.667 | 1.00 | 20.87 |
| 5831 | CA | TYR | A | 726 | -65.165 | 8.387 | 75.492 | 1.00 | 21.00 |
| 5832 | CB | TYR | A | 726 | -66.601 | 8.782 | 75.872 | 1.00 | 21.09 |
| 5833 | CG | TYR | A | 726 | -67.449 | 7.551 | 76.078 | 1.00 | 19.03 |
| 5834 | CD1 | TYR | A | 726 | -67.720 | 7.098 | 77.347 | 1.00 | 18.31 |
| 5835 | CE1 | TYR | A | 726 | -68.452 | 5.972 | 77.540 | 1.00 | 20.53 |
| 5836 | CZ | TYR | A | 726 | -68.928 | 5.264 | 76.465 | 1.00 | 19.61 |
| 5837 | OH | TYR | A | 726 | -69.635 | 4.121 | 76.725 | 1.00 | 22.52 |
| 5838 | CE2 | TYR | A | 726 | -68.674 | 5.678 | 75.180 | 1.00 | 17.61 |
| 5839 | CD2 | TYR | A | 726 | -67.905 | 6.809 | 74.999 | 1.00 | 17.82 |
| 5840 | C | TYR | A | 726 | -64.454 | 9.461 | 74.696 | 1.00 | 21.37 |
| 5841 | O | TYR | A | 726 | -64.534 | 9.483 | 73.474 | 1.00 | 21.81 |
| 5842 | N | THR | A | 727 | -63.740 | 10.344 | 75.384 | 1.00 | 21.83 |
| 5843 | CA | THR | A | 727 | -62.950 | 11.345 | 74.681 | 1.00 | 22.39 |
| 5844 | CB | THR | A | 727 | -62.358 | 12.384 | 75.669 | 1.00 | 23.07 |
| 5845 | OG1 | THR | A | 727 | -63.404 | 13.181 | 76.228 | 1.00 | 23.65 |
| 5846 | CG2 | THR | A | 727 | -61.481 | 13.403 | 74.937 | 1.00 | 21.85 |
| 5847 | C | THR | A | 727 | -61.823 | 10.644 | 73.941 | 1.00 | 21.83 |
| 5848 | O | THR | A | 727 | -61.610 | 10.899 | 72.768 | 1.00 | 21.98 |
| 5849 | N | HIS | A | 728 | -61.088 | 9.762 | 74.623 | 1.00 | 22.21 |
| 5850 | CA | HIS | A | 728 | -60.003 | 9.012 | 73.950 | 1.00 | 21.80 |
| 5851 | CB | HIS | A | 728 | -59.321 | 8.026 | 74.910 | 1.00 | 21.58 |
| 5852 | CG | HIS | A | 728 | -57.937 | 7.619 | 74.486 | 1.00 | 21.56 |
| 5853 | ND1 | HIS | A | 728 | -56.913 | 8.526 | 74.327 | 1.00 | 21.82 |
| 5854 | CE1 | HIS | A | 728 | -55.815 | 7.887 | 73.959 | 1.00 | 23.13 |
| 5855 | NE2 | HIS | A | 728 | -56.093 | 6.600 | 73.864 | 1.00 | 21.39 |

FIGURE 3 DK

| A | B | C | D | E | F | G | H | I | J |
|---|---|---|---|---|---|---|---|---|---|
| 5856 | CD2 | HIS | A | 728 | -57.409 | 6.403 | 74.194 | 1.00 | 20.39 |
| 5857 | C | HIS | A | 728 | -60.517 | 8.229 | 72.749 | 1.00 | 21.57 |
| 5858 | O | HIS | A | 728 | -59.893 | 8.228 | 71.709 | 1.00 | 22.29 |
| 5859 | N | MET | A | 729 | -61.631 | 7.521 | 72.906 | 1.00 | 21.73 |
| 5860 | CA | MET | A | 729 | -62.177 | 6.730 | 71.804 | 1.00 | 22.18 |
| 5861 | CB | MET | A | 729 | -63.320 | 5.852 | 72.290 | 1.00 | 22.56 |
| 5862 | CG | MET | A | 729 | -62.924 | 4.760 | 73.272 | 1.00 | 23.17 |
| 5863 | SD | MET | A | 729 | -64.347 | 3.780 | 73.620 | 1.00 | 28.13 |
| 5864 | CE | MET | A | 729 | -63.749 | 2.731 | 74.810 | 1.00 | 30.85 |
| 5865 | C | MET | A | 729 | -62.676 | 7.610 | 70.649 | 1.00 | 22.60 |
| 5866 | O | MET | A | 729 | -62.588 | 7.209 | 69.490 | 1.00 | 22.83 |
| 5867 | N | SER | A | 730 | -63.195 | 8.802 | 70.948 | 1.00 | 22.21 |
| 5868 | CA | SER | A | 730 | -63.641 | 9.683 | 69.861 | 1.00 | 22.68 |
| 5869 | CB | SER | A | 730 | -64.395 | 10.912 | 70.390 | 1.00 | 22.47 |
| 5870 | OG | SER | A | 730 | -65.460 | 10.524 | 71.251 | 1.00 | 22.04 |
| 5871 | C | SER | A | 730 | -62.463 | 10.086 | 68.985 | 1.00 | 23.25 |
| 5872 | O | SER | A | 730 | -62.549 | 10.039 | 67.757 | 1.00 | 22.85 |
| 5873 | N | HIS | A | 731 | -61.348 | 10.449 | 69.615 | 1.00 | 24.04 |
| 5874 | CA | HIS | A | 731 | -60.145 | 10.818 | 68.863 | 1.00 | 24.99 |
| 5875 | CB | HIS | A | 731 | -58.973 | 11.158 | 69.803 | 1.00 | 25.06 |
| 5876 | CG | HIS | A | 731 | -59.135 | 12.454 | 70.530 | 1.00 | 27.51 |
| 5877 | ND1 | HIS | A | 731 | -59.577 | 13.600 | 69.910 | 1.00 | 28.84 |
| 5878 | CE1 | HIS | A | 731 | -59.617 | 14.585 | 70.791 | 1.00 | 30.70 |
| 5879 | NE2 | HIS | A | 731 | -59.205 | 14.122 | 71.957 | 1.00 | 29.03 |
| 5880 | CD2 | HIS | A | 731 | -58.894 | 12.792 | 71.821 | 1.00 | 28.48 |
| 5881 | C | HIS | A | 731 | -59.687 | 9.694 | 67.952 | 1.00 | 24.46 |
| 5882 | O | HIS | A | 731 | -59.246 | 9.921 | 66.828 | 1.00 | 24.53 |
| 5883 | N | PHE | A | 732 | -59.754 | 8.474 | 68.456 | 1.00 | 24.56 |
| 5884 | CA | PHE | A | 732 | -59.244 | 7.331 | 67.694 | 1.00 | 23.88 |
| 5885 | CB | PHE | A | 732 | -59.145 | 6.108 | 68.612 | 1.00 | 23.14 |
| 5886 | CG | PHE | A | 732 | -58.834 | 4.830 | 67.898 | 1.00 | 22.25 |
| 5887 | CD1 | PHE | A | 732 | -57.509 | 4.452 | 67.657 | 1.00 | 21.45 |
| 5888 | CE1 | PHE | A | 732 | -57.228 | 3.245 | 67.006 | 1.00 | 21.94 |
| 5889 | CZ | PHE | A | 732 | -58.271 | 2.414 | 66.588 | 1.00 | 18.68 |
| 5890 | CE2 | PHE | A | 732 | -59.583 | 2.784 | 66.838 | 1.00 | 20.26 |
| 5891 | CD2 | PHE | A | 732 | -59.861 | 3.985 | 67.481 | 1.00 | 18.97 |
| 5892 | C | PHE | A | 732 | -60.189 | 7.086 | 66.546 | 1.00 | 24.38 |
| 5893 | O | PHE | A | 732 | -59.767 | 6.846 | 65.422 | 1.00 | 23.91 |
| 5894 | N | ILE | A | 733 | -61.480 | 7.172 | 66.845 | 1.00 | 25.50 |
| 5895 | CA | ILE | A | 733 | -62.511 | 6.993 | 65.840 | 1.00 | 27.16 |
| 5896 | CB | ILE | A | 733 | -63.917 | 7.023 | 66.460 | 1.00 | 26.69 |
| 5897 | CG1 | ILE | A | 733 | -64.185 | 5.711 | 67.187 | 1.00 | 28.91 |
| 5898 | CD1 | ILE | A | 733 | -64.089 | 4.489 | 66.265 | 1.00 | 27.10 |
| 5899 | CG2 | ILE | A | 733 | -64.948 | 7.137 | 65.370 | 1.00 | 28.56 |
| 5900 | C | ILE | A | 733 | -62.388 | 8.018 | 64.719 | 1.00 | 27.71 |
| 5901 | O | ILE | A | 733 | -62.356 | 7.637 | 63.546 | 1.00 | 27.57 |
| 5902 | N | LYS | A | 734 | -62.306 | 9.298 | 65.054 | 1.00 | 28.63 |
| 5903 | CA | LYS | A | 734 | -62.162 | 10.276 | 63.981 | 1.00 | 30.59 |
| 5904 | CB | LYS | A | 734 | -62.542 | 11.695 | 64.392 | 1.00 | 31.04 |
| 5905 | CG | LYS | A | 734 | -62.810 | 11.899 | 65.853 | 1.00 | 32.63 |
| 5906 | CD | LYS | A | 734 | -63.776 | 13.051 | 66.071 | 1.00 | 34.40 |

FIGURE 3 DL

| A | B | C | D | E | F | G | H | I | J |
|---|---|---|---|---|---|---|---|---|---|
| 5907 | CE | LYS | A | 734 | -63.253 | 14.336 | 65.441 | 1.00 | 36.19 |
| 5908 | NZ | LYS | A | 734 | -64.229 | 15.456 | 65.549 | 1.00 | 38.15 |
| 5909 | C | LYS | A | 734 | -60.805 | 10.206 | 63.284 | 1.00 | 31.10 |
| 5910 | O | LYS | A | 734 | -60.723 | 10.519 | 62.107 | 1.00 | 31.08 |
| 5911 | N | GLN | A | 735 | -59.755 | 9.775 | 63.982 | 1.00 | 31.91 |
| 5912 | CA | GLN | A | 735 | -58.454 | 9.590 | 63.332 | 1.00 | 33.34 |
| 5913 | CB | GLN | A | 735 | -57.369 | 9.179 | 64.333 | 1.00 | 33.56 |
| 5914 | CG | GLN | A | 735 | -56.025 | 8.750 | 63.691 | 1.00 | 37.28 |
| 5915 | CD | GLN | A | 735 | -56.024 | 7.323 | 63.086 | 1.00 | 42.41 |
| 5916 | OE1 | GLN | A | 735 | -55.765 | 7.153 | 61.885 | 1.00 | 44.60 |
| 5917 | NE2 | GLN | A | 735 | -56.289 | 6.296 | 63.918 | 1.00 | 43.33 |
| 5918 | C | GLN | A | 735 | -58.567 | 8.521 | 62.252 | 1.00 | 33.22 |
| 5919 | O | GLN | A | 735 | -58.120 | 8.721 | 61.128 | 1.00 | 33.15 |
| 5920 | N | CYS | A | 736 | -59.170 | 7.389 | 62.610 | 1.00 | 33.22 |
| 5921 | CA | CYS | A | 736 | -59.358 | 6.263 | 61.693 | 1.00 | 33.79 |
| 5922 | CB | CYS | A | 736 | -59.968 | 5.072 | 62.462 | 1.00 | 33.73 |
| 5923 | SG | CYS | A | 736 | -60.727 | 3.713 | 61.519 | 1.00 | 37.10 |
| 5924 | C | CYS | A | 736 | -60.219 | 6.635 | 60.476 | 1.00 | 33.58 |
| 5925 | O | CYS | A | 736 | -59.961 | 6.173 | 59.368 | 1.00 | 33.62 |
| 5926 | N | PHE | A | 737 | -61.224 | 7.477 | 60.704 | 1.00 | 33.49 |
| 5927 | CA | PHE | A | 737 | -62.175 | 7.913 | 59.679 | 1.00 | 33.66 |
| 5928 | CB | PHE | A | 737 | -63.575 | 8.112 | 60.294 | 1.00 | 32.87 |
| 5929 | CG | PHE | A | 737 | -64.301 | 6.823 | 60.608 | 1.00 | 31.36 |
| 5930 | CD1 | PHE | A | 737 | -63.816 | 5.602 | 60.159 | 1.00 | 30.51 |
| 5931 | CE1 | PHE | A | 737 | -64.499 | 4.414 | 60.429 | 1.00 | 28.51 |
| 5932 | CZ | PHE | A | 737 | -65.662 | 4.441 | 61.166 | 1.00 | 27.07 |
| 5933 | CE2 | PHE | A | 737 | -66.154 | 5.651 | 61.625 | 1.00 | 28.45 |
| 5934 | CD2 | PHE | A | 737 | -65.477 | 6.834 | 61.340 | 1.00 | 29.14 |
| 5935 | C | PHE | A | 737 | -61.737 | 9.201 | 58.963 | 1.00 | 34.35 |
| 5936 | O | PHE | A | 737 | -62.460 | 9.741 | 58.130 | 1.00 | 33.54 |
| 5937 | N | SER | A | 738 | -60.544 | 9.685 | 59.283 | 1.00 | 35.95 |
| 5938 | CA | SER | A | 738 | -60.044 | 10.916 | 58.672 | 1.00 | 37.76 |
| 5939 | CB | SER | A | 738 | -59.792 | 10.712 | 57.171 | 1.00 | 37.83 |
| 5940 | OG | SER | A | 738 | -58.712 | 9.830 | 56.951 | 1.00 | 38.28 |
| 5941 | C | SER | A | 738 | -61.015 | 12.086 | 58.894 | 1.00 | 38.68 |
| 5942 | O | SER | A | 738 | -61.259 | 12.878 | 57.988 | 1.00 | 38.51 |
| 5943 | N | LEU | A | 739 | -61.568 | 12.171 | 60.100 | 1.00 | 40.18 |
| 5944 | CA | LEU | A | 739 | -62.470 | 13.246 | 60.482 | 1.00 | 41.75 |
| 5945 | CB | LEU | A | 739 | -63.629 | 12.697 | 61.306 | 1.00 | 41.38 |
| 5946 | CG | LEU | A | 739 | -64.564 | 11.738 | 60.567 | 1.00 | 40.93 |
| 5947 | CD1 | LEU | A | 739 | -65.640 | 11.206 | 61.492 | 1.00 | 37.09 |
| 5948 | CD2 | LEU | A | 739 | -65.168 | 12.452 | 59.354 | 1.00 | 41.52 |
| 5949 | C | LEU | A | 739 | -61.706 | 14.237 | 61.331 | 1.00 | 43.20 |
| 5950 | O | LEU | A | 739 | -61.526 | 14.013 | 62.518 | 1.00 | 44.19 |
| 5951 | N | PRO | A | 740 | -61.229 | 15.315 | 60.726 | 1.00 | 44.56 |
| 5952 | CA | PRO | A | 740 | -60.459 | 16.341 | 61.441 | 1.00 | 45.43 |
| 5953 | CB | PRO | A | 740 | -59.950 | 17.229 | 60.306 | 1.00 | 45.59 |
| 5954 | CG | PRO | A | 740 | -60.046 | 16.377 | 59.111 | 1.00 | 45.51 |
| 5955 | CD | PRO | A | 740 | -61.342 | 15.620 | 59.293 | 1.00 | 44.81 |
| 5956 | C | PRO | A | 740 | -61.297 | 17.178 | 62.414 | 1.00 | 46.06 |
| 5957 | O | PRO | A | 740 | -62.340 | 16.718 | 62.884 | 1.00 | 46.86 |

FIGURE 3 DM

| A | B | C D E | F | G | H | I | J |
|---|---|---|---|---|---|---|---|
| 5958 | O7 | NAG A2311 | -101.706 | -14.580 | 110.320 | 1.00 | 67.11 |
| 5959 | C7 | NAG A2311 | -100.699 | -13.892 | 110.433 | 1.00 | 65.56 |
| 5960 | C8 | NAG A2311 | -100.768 | -12.440 | 110.821 | 1.00 | 66.13 |
| 5961 | N2 | NAG A2311 | -99.477 | -14.405 | 110.302 | 1.00 | 63.69 |
| 5962 | C2 | NAG A2311 | -99.303 | -15.797 | 109.931 | 1.00 | 62.14 |
| 5963 | C1 | NAG A2311 | -98.045 | -15.994 | 109.103 | 1.00 | 59.33 |
| 5964 | C3 | NAG A2311 | -99.244 | -16.705 | 111.144 | 1.00 | 62.19 |
| 5965 | O3 | NAG A2311 | -100.505 | -16.634 | 111.819 | 1.00 | 63.22 |
| 5966 | C4 | NAG A2311 | -99.012 | -18.143 | 110.686 | 1.00 | 61.71 |
| 5967 | O4 | NAG A2311 | -98.700 | -18.975 | 111.811 | 1.00 | 61.69 |
| 5968 | C5 | NAG A2311 | -97.897 | -18.254 | 109.645 | 1.00 | 61.35 |
| 5969 | O5 | NAG A2311 | -98.061 | -17.312 | 108.593 | 1.00 | 60.20 |
| 5970 | C6 | NAG A2311 | -97.878 | -19.638 | 109.019 | 1.00 | 61.97 |
| 5971 | O6 | NAG A2311 | -96.587 | -20.208 | 109.275 | 1.00 | 62.68 |
| 5972 | O7 | NAG A2411 | -69.302 | -25.885 | 106.392 | 1.00 | 54.80 |
| 5973 | C7 | NAG A2411 | -68.758 | -24.803 | 106.510 | 1.00 | 53.76 |
| 5974 | C8 | NAG A2411 | -69.299 | -23.706 | 107.377 | 1.00 | 53.91 |
| 5975 | N2 | NAG A2411 | -67.596 | -24.564 | 105.931 | 1.00 | 52.61 |
| 5976 | C2 | NAG A2411 | -67.039 | -25.609 | 105.112 | 1.00 | 52.99 |
| 5977 | C1 | NAG A2411 | -66.605 | -25.068 | 103.764 | 1.00 | 47.58 |
| 5978 | C3 | NAG A2411 | -65.881 | -26.265 | 105.866 | 1.00 | 54.83 |
| 5979 | O3 | NAG A2411 | -66.372 | -26.917 | 107.043 | 1.00 | 56.64 |
| 5980 | C4 | NAG A2411 | -65.217 | -27.301 | 104.980 | 1.00 | 54.99 |
| 5981 | O4 | NAG A2411 | -64.057 | -27.834 | 105.639 | 1.00 | 59.91 |
| 5982 | C5 | NAG A2411 | -64.856 | -26.648 | 103.653 | 1.00 | 53.51 |
| 5983 | O5 | NAG A2411 | -66.038 | -26.142 | 103.026 | 1.00 | 52.24 |
| 5984 | C6 | NAG A2411 | -64.212 | -27.654 | 102.717 | 1.00 | 52.86 |
| 5985 | O6 | NAG A2411 | -65.229 | -28.130 | 101.831 | 1.00 | 52.85 |
| 5986 | O7 | NAG A2412 | -60.346 | -27.486 | 103.509 | 1.00 | 73.72 |
| 5987 | C7 | NAG A2412 | -60.841 | -27.680 | 104.609 | 1.00 | 73.68 |
| 5988 | C8 | NAG A2412 | -60.668 | -26.700 | 105.737 | 1.00 | 74.25 |
| 5989 | N2 | NAG A2412 | -61.635 | -28.724 | 104.846 | 1.00 | 72.89 |
| 5990 | C2 | NAG A2412 | -62.240 | -28.940 | 106.145 | 1.00 | 72.83 |
| 5991 | C1 | NAG A2412 | -63.747 | -29.127 | 106.017 | 1.00 | 69.76 |
| 5992 | C3 | NAG A2412 | -61.599 | -30.144 | 106.833 | 1.00 | 73.48 |
| 5993 | O3 | NAG A2412 | -60.208 | -29.879 | 107.077 | 1.00 | 74.07 |
| 5994 | C4 | NAG A2412 | -62.303 | -30.427 | 108.156 | 1.00 | 73.50 |
| 5995 | O4 | NAG A2412 | -61.792 | -31.648 | 108.718 | 1.00 | 74.51 |
| 5996 | C5 | NAG A2412 | -63.819 | -30.499 | 107.969 | 1.00 | 72.95 |
| 5997 | O5 | NAG A2412 | -64.303 | -29.319 | 107.318 | 1.00 | 72.24 |
| 5998 | C6 | NAG A2412 | -64.534 | -30.638 | 109.310 | 1.00 | 73.39 |
| 5999 | O6 | NAG A2412 | -64.246 | -29.499 | 110.139 | 1.00 | 73.37 |
| 6000 | O7 | NAG A2931 | -75.747 | -20.902 | 123.574 | 1.00 | 68.40 |
| 6001 | C7 | NAG A2931 | -75.833 | -19.694 | 123.389 | 1.00 | 68.47 |
| 6002 | C8 | NAG A2931 | -76.643 | -18.791 | 124.278 | 1.00 | 69.27 |
| 6003 | N2 | NAG A2931 | -75.142 | -19.086 | 122.428 | 1.00 | 66.82 |
| 6004 | C2 | NAG A2931 | -74.315 | -19.887 | 121.551 | 1.00 | 65.47 |
| 6005 | C1 | NAG A2931 | -74.614 | -19.648 | 120.071 | 1.00 | 62.57 |
| 6006 | C3 | NAG A2931 | -72.861 | -19.647 | 121.941 | 1.00 | 65.13 |
| 6007 | O3 | NAG A2931 | -72.643 | -20.270 | 123.214 | 1.00 | 66.03 |
| 6008 | C4 | NAG A2931 | -71.872 | -20.246 | 120.956 | 1.00 | 65.18 |

FIGURE 3 DN

| A | B | C | D | E | F | G | H | I | J |
|---|---|---|---|---|---|---|---|---|---|
| 6009 | O4 | NAG | A | 2931 | -70.586 | -19.657 | 121.232 | 1.00 | 64.70 |
| 6010 | C5 | NAG | A | 2931 | -72.320 | -20.032 | 119.502 | 1.00 | 64.87 |
| 6011 | O5 | NAG | A | 2931 | -73.686 | -20.431 | 119.318 | 1.00 | 63.71 |
| 6012 | C6 | NAG | A | 2931 | -71.412 | -20.759 | 118.501 | 1.00 | 65.29 |
| 6013 | O6 | NAG | A | 2931 | -71.670 | -22.169 | 118.463 | 1.00 | 66.16 |
| 6014 | O7 | NAG | A | 3331 | -79.456 | -32.271 | 76.813 | 1.00 | 56.81 |
| 6015 | C7 | NAG | A | 3331 | -79.475 | -32.704 | 77.949 | 1.00 | 55.21 |
| 6016 | C8 | NAG | A | 3331 | -80.758 | -33.009 | 78.655 | 1.00 | 56.21 |
| 6017 | N2 | NAG | A | 3331 | -78.353 | -32.997 | 78.595 | 1.00 | 54.94 |
| 6018 | C2 | NAG | A | 3331 | -77.071 | -32.724 | 77.972 | 1.00 | 53.94 |
| 6019 | C1 | NAG | A | 3331 | -76.352 | -31.662 | 78.803 | 1.00 | 50.83 |
| 6020 | C3 | NAG | A | 3331 | -76.224 | -33.980 | 77.825 | 1.00 | 54.42 |
| 6021 | O3 | NAG | A | 3331 | -76.891 | -34.893 | 76.937 | 1.00 | 54.46 |
| 6022 | C4 | NAG | A | 3331 | -74.846 | -33.570 | 77.300 | 1.00 | 55.36 |
| 6023 | O4 | NAG | A | 3331 | -73.959 | -34.698 | 77.202 | 1.00 | 57.49 |
| 6024 | C5 | NAG | A | 3331 | -74.246 | -32.498 | 78.211 | 1.00 | 55.58 |
| 6025 | O5 | NAG | A | 3331 | -75.095 | -31.348 | 78.212 | 1.00 | 54.08 |
| 6026 | C6 | NAG | A | 3331 | -72.862 | -32.063 | 77.761 | 1.00 | 56.37 |
| 6027 | O6 | NAG | A | 3331 | -73.020 | -31.081 | 76.723 | 1.00 | 57.36 |
| 6028 | N | HIS | B | 9 | -26.838 | 6.528 | 39.826 | 1.00 | 51.46 |
| 6029 | CA | HIS | B | 9 | -26.599 | 6.867 | 41.263 | 1.00 | 51.24 |
| 6030 | CB | HIS | B | 9 | -26.976 | 5.700 | 42.165 | 1.00 | 51.44 |
| 6031 | CG | HIS | B | 9 | -26.270 | 4.422 | 41.834 | 1.00 | 51.51 |
| 6032 | ND1 | HIS | B | 9 | -25.316 | 3.866 | 42.658 | 1.00 | 50.18 |
| 6033 | CE1 | HIS | B | 9 | -24.880 | 2.738 | 42.124 | 1.00 | 50.86 |
| 6034 | NE2 | HIS | B | 9 | -25.517 | 2.541 | 40.984 | 1.00 | 51.05 |
| 6035 | CD2 | HIS | B | 9 | -26.391 | 3.581 | 40.778 | 1.00 | 52.22 |
| 6036 | C | HIS | B | 9 | -25.161 | 7.276 | 41.507 | 1.00 | 50.92 |
| 6037 | O | HIS | B | 9 | -24.848 | 7.893 | 42.525 | 1.00 | 50.67 |
| 6038 | N | HIS | B | 10 | -24.284 | 6.929 | 40.568 | 1.00 | 50.91 |
| 6039 | CA | HIS | B | 10 | -22.879 | 7.326 | 40.655 | 1.00 | 50.79 |
| 6040 | CB | HIS | B | 10 | -22.735 | 8.812 | 40.314 | 1.00 | 51.37 |
| 6041 | CG | HIS | B | 10 | -23.356 | 9.188 | 39.001 | 1.00 | 53.62 |
| 6042 | ND1 | HIS | B | 10 | -22.705 | 9.950 | 38.055 | 1.00 | 55.54 |
| 6043 | CE1 | HIS | B | 10 | -23.489 | 10.111 | 37.003 | 1.00 | 56.51 |
| 6044 | NE2 | HIS | B | 10 | -24.624 | 9.476 | 37.231 | 1.00 | 57.01 |
| 6045 | CD2 | HIS | B | 10 | -24.568 | 8.895 | 38.475 | 1.00 | 55.21 |
| 6046 | C | HIS | B | 10 | -22.299 | 7.031 | 42.041 | 1.00 | 49.97 |
| 6047 | O | HIS | B | 10 | -21.543 | 7.823 | 42.590 | 1.00 | 50.21 |
| 6048 | N | HIS | B | 11 | -22.704 | 5.902 | 42.612 | 1.00 | 48.73 |
| 6049 | CA | HIS | B | 11 | -22.197 | 5.443 | 43.898 | 1.00 | 47.84 |
| 6050 | CB | HIS | B | 11 | -20.757 | 4.977 | 43.751 | 1.00 | 47.49 |
| 6051 | CG | HIS | B | 11 | -20.599 | 3.895 | 42.736 | 1.00 | 46.24 |
| 6052 | ND1 | HIS | B | 11 | -20.982 | 2.596 | 42.978 | 1.00 | 44.69 |
| 6053 | CE1 | HIS | B | 11 | -20.735 | 1.862 | 41.907 | 1.00 | 45.47 |
| 6054 | NE2 | HIS | B | 11 | -20.227 | 2.645 | 40.973 | 1.00 | 45.22 |
| 6055 | CD2 | HIS | B | 11 | -20.141 | 3.924 | 41.463 | 1.00 | 46.06 |
| 6056 | C | HIS | B | 11 | -22.359 | 6.382 | 45.085 | 1.00 | 47.55 |
| 6057 | O | HIS | B | 11 | -21.589 | 6.341 | 46.048 | 1.00 | 47.46 |
| 6058 | N | HIS | B | 12 | -23.371 | 7.229 | 45.028 | 1.00 | 47.24 |
| 6059 | CA | HIS | B | 12 | -23.628 | 8.090 | 46.164 | 1.00 | 47.40 |

FIGURE 3 DO

| A | B | C | D | E | F | G | H | I | J |
|---|---|---|---|---|---|---|---|---|---|
| 6060 | CB | HIS | B | 12 | -24.450 | 9.308 | 45.755 | 1.00 | 47.98 |
| 6061 | CG | HIS | B | 12 | -23.691 | 10.278 | 44.912 | 1.00 | 49.81 |
| 6062 | ND1 | HIS | B | 12 | -22.581 | 10.952 | 45.375 | 1.00 | 51.77 |
| 6063 | CE1 | HIS | B | 12 | -22.118 | 11.738 | 44.418 | 1.00 | 53.30 |
| 6064 | NE2 | HIS | B | 12 | -22.886 | 11.596 | 43.352 | 1.00 | 53.18 |
| 6065 | CD2 | HIS | B | 12 | -23.876 | 10.685 | 43.634 | 1.00 | 52.05 |
| 6066 | C | HIS | B | 12 | -24.335 | 7.308 | 47.261 | 1.00 | 46.64 |
| 6067 | O | HIS | B | 12 | -25.076 | 6.350 | 46.999 | 1.00 | 46.17 |
| 6068 | N | SER | B | 13 | -24.068 | 7.703 | 48.494 | 1.00 | 45.74 |
| 6069 | CA | SER | B | 13 | -24.696 | 7.067 | 49.621 | 1.00 | 45.17 |
| 6070 | CB | SER | B | 13 | -24.011 | 7.502 | 50.918 | 1.00 | 45.34 |
| 6071 | OG | SER | B | 13 | -22.627 | 7.208 | 50.873 | 1.00 | 44.84 |
| 6072 | C | SER | B | 13 | -26.154 | 7.486 | 49.610 | 1.00 | 44.76 |
| 6073 | O | SER | B | 13 | -26.474 | 8.666 | 49.801 | 1.00 | 44.75 |
| 6074 | N | ARG | B | 14 | -27.047 | 6.538 | 49.349 | 1.00 | 43.99 |
| 6075 | CA | ARG | B | 14 | -28.455 | 6.893 | 49.353 | 1.00 | 43.48 |
| 6076 | CB | ARG | B | 14 | -29.081 | 6.839 | 47.946 | 1.00 | 44.34 |
| 6077 | CG | ARG | B | 14 | -29.532 | 5.487 | 47.438 | 1.00 | 46.74 |
| 6078 | CD | ARG | B | 14 | -28.437 | 4.724 | 46.726 | 1.00 | 50.53 |
| 6079 | NE | ARG | B | 14 | -28.877 | 3.996 | 45.535 | 1.00 | 52.35 |
| 6080 | CZ | ARG | B | 14 | -28.334 | 2.846 | 45.150 | 1.00 | 54.53 |
| 6081 | NH1 | ARG | B | 14 | -27.358 | 2.316 | 45.879 | 1.00 | 56.16 |
| 6082 | NH2 | ARG | B | 14 | -28.753 | 2.220 | 44.054 | 1.00 | 53.87 |
| 6083 | C | ARG | B | 14 | -29.258 | 6.157 | 50.426 | 1.00 | 42.02 |
| 6084 | O | ARG | B | 14 | -30.411 | 6.493 | 50.684 | 1.00 | 42.18 |
| 6085 | N | LYS | B | 15 | -28.618 | 5.183 | 51.071 | 1.00 | 40.01 |
| 6086 | CA | LYS | B | 15 | -29.213 | 4.452 | 52.181 | 1.00 | 37.85 |
| 6087 | CB | LYS | B | 15 | -28.399 | 3.193 | 52.484 | 1.00 | 38.37 |
| 6088 | CG | LYS | B | 15 | -28.765 | 1.968 | 51.687 | 1.00 | 38.55 |
| 6089 | CD | LYS | B | 15 | -27.853 | 0.820 | 52.068 | 1.00 | 38.41 |
| 6090 | CE | LYS | B | 15 | -26.649 | 0.727 | 51.162 | 1.00 | 37.94 |
| 6091 | NZ | LYS | B | 15 | -25.836 | -0.495 | 51.508 | 1.00 | 38.06 |
| 6092 | C | LYS | B | 15 | -29.172 | 5.281 | 53.445 | 1.00 | 36.28 |
| 6093 | O | LYS | B | 15 | -28.301 | 6.137 | 53.613 | 1.00 | 35.80 |
| 6094 | N | THR | B | 16 | -30.105 | 5.005 | 54.349 | 1.00 | 34.29 |
| 6095 | CA | THR | B | 16 | -30.074 | 5.617 | 55.665 | 1.00 | 32.39 |
| 6096 | CB | THR | B | 16 | -31.240 | 6.588 | 55.881 | 1.00 | 32.78 |
| 6097 | OG1 | THR | B | 16 | -32.480 | 5.870 | 55.918 | 1.00 | 32.81 |
| 6098 | CG2 | THR | B | 16 | -31.389 | 7.522 | 54.692 | 1.00 | 32.16 |
| 6099 | C | THR | B | 16 | -30.131 | 4.493 | 56.671 | 1.00 | 31.47 |
| 6100 | O | THR | B | 16 | -30.352 | 3.335 | 56.315 | 1.00 | 30.96 |
| 6101 | N | TYR | B | 17 | -29.889 | 4.823 | 57.927 | 1.00 | 30.27 |
| 6102 | CA | TYR | B | 17 | -29.969 | 3.826 | 58.982 | 1.00 | 29.53 |
| 6103 | CB | TYR | B | 17 | -29.076 | 4.257 | 60.137 | 1.00 | 28.58 |
| 6104 | CG | TYR | B | 17 | -28.988 | 3.271 | 61.260 | 1.00 | 26.98 |
| 6105 | CD1 | TYR | B | 17 | -28.046 | 2.261 | 61.238 | 1.00 | 25.97 |
| 6106 | CE1 | TYR | B | 17 | -27.938 | 1.358 | 62.275 | 1.00 | 25.10 |
| 6107 | CZ | TYR | B | 17 | -28.788 | 1.473 | 63.364 | 1.00 | 26.59 |
| 6108 | OH | TYR | B | 17 | -28.689 | 0.564 | 64.394 | 1.00 | 25.76 |
| 6109 | CE2 | TYR | B | 17 | -29.741 | 2.474 | 63.411 | 1.00 | 25.68 |
| 6110 | CD2 | TYR | B | 17 | -29.835 | 3.364 | 62.366 | 1.00 | 26.27 |

FIGURE 3 DP

| A | B | C | D | E | F | G | H | I | J |
|---|---|---|---|---|---|---|---|---|---|
| 6111 | C | TYR | B | 17 | -31.433 | 3.772 | 59.419 | 1.00 | 29.18 |
| 6112 | O | TYR | B | 17 | -31.931 | 4.715 | 60.021 | 1.00 | 29.31 |
| 6113 | N | THR | B | 18 | -32.127 | 2.681 | 59.128 | 1.00 | 28.83 |
| 6114 | CA | THR | B | 18 | -33.577 | 2.650 | 59.393 | 1.00 | 28.33 |
| 6115 | CB | THR | B | 18 | -34.283 | 1.890 | 58.301 | 1.00 | 28.04 |
| 6116 | OG1 | THR | B | 18 | -33.843 | 0.532 | 58.361 | 1.00 | 27.49 |
| 6117 | CG2 | THR | B | 18 | -33.839 | 2.392 | 56.890 | 1.00 | 27.67 |
| 6118 | C | THR | B | 18 | -34.015 | 2.041 | 60.726 | 1.00 | 28.42 |
| 6119 | O | THR | B | 18 | -33.225 | 1.418 | 61.440 | 1.00 | 28.15 |
| 6120 | N | LEU | B | 19 | -35.296 | 2.214 | 61.032 | 1.00 | 28.13 |
| 6121 | CA | LEU | B | 19 | -35.874 | 1.645 | 62.235 | 1.00 | 28.62 |
| 6122 | CB | LEU | B | 19 | -37.370 | 1.958 | 62.310 | 1.00 | 28.69 |
| 6123 | CG | LEU | B | 19 | -38.090 | 1.439 | 63.555 | 1.00 | 30.29 |
| 6124 | CD1 | LEU | B | 19 | -37.459 | 2.049 | 64.794 | 1.00 | 30.06 |
| 6125 | CD2 | LEU | B | 19 | -39.565 | 1.788 | 63.486 | 1.00 | 29.50 |
| 6126 | C | LEU | B | 19 | -35.626 | 0.144 | 62.259 | 1.00 | 28.23 |
| 6127 | O | LEU | B | 19 | -35.243 | -0.409 | 63.287 | 1.00 | 28.68 |
| 6128 | N | THR | B | 20 | -35.826 | -0.501 | 61.114 | 1.00 | 28.11 |
| 6129 | CA | THR | B | 20 | -35.579 | -1.926 | 60.970 | 1.00 | 28.80 |
| 6130 | CB | THR | B | 20 | -36.145 | -2.409 | 59.644 | 1.00 | 29.13 |
| 6131 | OG1 | THR | B | 20 | -37.513 | -1.991 | 59.557 | 1.00 | 33.42 |
| 6132 | CG2 | THR | B | 20 | -36.249 | -3.899 | 59.638 | 1.00 | 28.42 |
| 6133 | C | THR | B | 20 | -34.089 | -2.274 | 61.057 | 1.00 | 28.68 |
| 6134 | O | THR | B | 20 | -33.731 | -3.372 | 61.494 | 1.00 | 28.68 |
| 6135 | N | ASP | B | 21 | -33.215 | -1.368 | 60.623 | 1.00 | 27.84 |
| 6136 | CA | ASP | B | 21 | -31.793 | -1.633 | 60.803 | 1.00 | 27.96 |
| 6137 | CB | ASP | B | 21 | -30.910 | -0.552 | 60.163 | 1.00 | 27.48 |
| 6138 | CG | ASP | B | 21 | -30.980 | -0.578 | 58.658 | 1.00 | 27.90 |
| 6139 | OD1 | ASP | B | 21 | -31.234 | -1.661 | 58.102 | 1.00 | 29.99 |
| 6140 | OD2 | ASP | B | 21 | -30.850 | 0.434 | 57.948 | 1.00 | 27.64 |
| 6141 | C | ASP | B | 21 | -31.500 | -1.746 | 62.292 | 1.00 | 27.47 |
| 6142 | O | ASP | B | 21 | -30.852 | -2.681 | 62.730 | 1.00 | 27.65 |
| 6143 | N | TYR | B | 22 | -31.990 | -0.786 | 63.066 | 1.00 | 27.56 |
| 6144 | CA | TYR | B | 22 | -31.798 | -0.786 | 64.511 | 1.00 | 27.07 |
| 6145 | CB | TYR | B | 22 | -32.387 | 0.496 | 65.095 | 1.00 | 27.26 |
| 6146 | CG | TYR | B | 22 | -32.479 | 0.536 | 66.603 | 1.00 | 25.76 |
| 6147 | CD1 | TYR | B | 22 | -31.354 | 0.327 | 67.390 | 1.00 | 25.07 |
| 6148 | CE1 | TYR | B | 22 | -31.437 | 0.361 | 68.771 | 1.00 | 26.02 |
| 6149 | CZ | TYR | B | 22 | -32.658 | 0.625 | 69.376 | 1.00 | 26.47 |
| 6150 | OH | TYR | B | 22 | -32.730 | 0.652 | 70.740 | 1.00 | 28.72 |
| 6151 | CE2 | TYR | B | 22 | -33.791 | 0.833 | 68.622 | 1.00 | 24.53 |
| 6152 | CD2 | TYR | B | 22 | -33.698 | 0.788 | 67.238 | 1.00 | 24.72 |
| 6153 | C | TYR | B | 22 | -32.462 | -1.990 | 65.152 | 1.00 | 27.28 |
| 6154 | O | TYR | B | 22 | -31.860 | -2.704 | 65.952 | 1.00 | 26.36 |
| 6155 | N | LEU | B | 23 | -33.717 | -2.218 | 64.787 | 1.00 | 28.09 |
| 6156 | CA | LEU | B | 23 | -34.463 | -3.332 | 65.374 | 1.00 | 28.86 |
| 6157 | CB | LEU | B | 23 | -35.959 | -3.162 | 65.148 | 1.00 | 28.70 |
| 6158 | CG | LEU | B | 23 | -36.527 | -1.946 | 65.867 | 1.00 | 28.01 |
| 6159 | CD1 | LEU | B | 23 | -38.043 | -1.974 | 65.769 | 1.00 | 27.16 |
| 6160 | CD2 | LEU | B | 23 | -36.049 | -1.928 | 67.336 | 1.00 | 27.83 |
| 6161 | C | LEU | B | 23 | -33.989 | -4.725 | 64.962 | 1.00 | 29.70 |

FIGURE 3 DQ

| A | B | C | D | E | F | G | H | I | J |
|---|---|---|---|---|---|---|---|---|---|
| 6162 | O | LEU | B | 23 | -34.043 | -5.656 | 65.771 | 1.00 | 29.97 |
| 6163 | N | LYS | B | 24 | -33.506 | -4.899 | 63.736 | 1.00 | 31.19 |
| 6164 | CA | LYS | B | 24 | -33.044 | -6.248 | 63.338 | 1.00 | 33.19 |
| 6165 | CB | LYS | B | 24 | -33.556 | -6.624 | 61.946 | 1.00 | 32.67 |
| 6166 | CG | LYS | B | 24 | -35.050 | -6.558 | 61.801 | 1.00 | 34.40 |
| 6167 | CD | LYS | B | 24 | -35.750 | -7.527 | 62.748 | 1.00 | 36.99 |
| 6168 | CE | LYS | B | 24 | -37.226 | -7.660 | 62.398 | 1.00 | 38.20 |
| 6169 | NZ | LYS | B | 24 | -37.985 | -8.390 | 63.451 | 1.00 | 39.33 |
| 6170 | C | LYS | B | 24 | -31.518 | -6.371 | 63.417 | 1.00 | 33.92 |
| 6171 | O | LYS | B | 24 | -30.911 | -7.210 | 62.753 | 1.00 | 34.63 |
| 6172 | N | ASN | B | 25 | -30.921 | -5.515 | 64.243 | 1.00 | 35.51 |
| 6173 | CA | ASN | B | 25 | -29.473 | -5.455 | 64.485 | 1.00 | 37.54 |
| 6174 | CB | ASN | B | 25 | -29.083 | -6.367 | 65.658 | 1.00 | 37.71 |
| 6175 | CG | ASN | B | 25 | -28.007 | -5.750 | 66.536 | 1.00 | 41.32 |
| 6176 | OD1 | ASN | B | 25 | -26.832 | -5.676 | 66.146 | 1.00 | 44.42 |
| 6177 | ND2 | ASN | B | 25 | -28.400 | -5.287 | 67.726 | 1.00 | 42.73 |
| 6178 | C | ASN | B | 25 | -28.577 | -5.684 | 63.250 | 1.00 | 37.43 |
| 6179 | O | ASN | B | 25 | -27.533 | -6.328 | 63.326 | 1.00 | 38.79 |
| 6180 | N | THR | B | 26 | -29.007 | -5.106 | 62.133 | 1.00 | 37.35 |
| 6181 | CA | THR | B | 26 | -28.351 | -5.149 | 60.825 | 1.00 | 37.43 |
| 6182 | CB | THR | B | 26 | -29.128 | -4.228 | 59.856 | 1.00 | 37.53 |
| 6183 | OG1 | THR | B | 26 | -30.456 | -4.736 | 59.653 | 1.00 | 38.93 |
| 6184 | CG2 | THR | B | 26 | -28.513 | -4.276 | 58.461 | 1.00 | 36.89 |
| 6185 | C | THR | B | 26 | -26.877 | -4.710 | 60.783 | 1.00 | 37.60 |
| 6186 | O | THR | B | 26 | -26.050 | -5.306 | 60.086 | 1.00 | 37.23 |
| 6187 | N | TYR | B | 27 | -26.571 | -3.625 | 61.480 | 1.00 | 37.59 |
| 6188 | CA | TYR | B | 27 | -25.217 | -3.115 | 61.540 | 1.00 | 37.80 |
| 6189 | CB | TYR | B | 27 | -25.188 | -1.630 | 61.243 | 1.00 | 37.38 |
| 6190 | CG | TYR | B | 27 | -25.714 | -1.301 | 59.872 | 1.00 | 37.50 |
| 6191 | CD1 | TYR | B | 27 | -24.993 | -1.628 | 58.730 | 1.00 | 38.34 |
| 6192 | CE1 | TYR | B | 27 | -25.484 | -1.313 | 57.460 | 1.00 | 38.30 |
| 6193 | CZ | TYR | B | 27 | -26.711 | -0.680 | 57.342 | 1.00 | 37.34 |
| 6194 | OH | TYR | B | 27 | -27.225 | -0.356 | 56.103 | 1.00 | 36.98 |
| 6195 | CE2 | TYR | B | 27 | -27.433 | -0.359 | 58.471 | 1.00 | 36.73 |
| 6196 | CD2 | TYR | B | 27 | -26.941 | -0.673 | 59.714 | 1.00 | 35.88 |
| 6197 | C | TYR | B | 27 | -24.732 | -3.405 | 62.929 | 1.00 | 38.00 |
| 6198 | O | TYR | B | 27 | -25.262 | -2.894 | 63.916 | 1.00 | 37.90 |
| 6199 | N | ARG | B | 28 | -23.715 | -4.246 | 62.998 | 1.00 | 38.99 |
| 6200 | CA | ARG | B | 28 | -23.300 | -4.776 | 64.275 | 1.00 | 39.79 |
| 6201 | CB | ARG | B | 28 | -23.452 | -6.296 | 64.269 | 1.00 | 40.10 |
| 6202 | CG | ARG | B | 28 | -23.869 | -6.872 | 65.611 | 1.00 | 43.94 |
| 6203 | CD | ARG | B | 28 | -24.428 | -8.312 | 65.544 | 1.00 | 47.66 |
| 6204 | NE | ARG | B | 28 | -25.551 | -8.447 | 64.616 | 1.00 | 50.54 |
| 6205 | CZ | ARG | B | 28 | -26.333 | -9.527 | 64.544 | 1.00 | 52.62 |
| 6206 | NH1 | ARG | B | 28 | -26.131 | -10.561 | 65.354 | 1.00 | 53.53 |
| 6207 | NH2 | ARG | B | 28 | -27.323 | -9.576 | 63.665 | 1.00 | 52.85 |
| 6208 | C | ARG | B | 28 | -21.906 | -4.396 | 64.721 | 1.00 | 39.43 |
| 6209 | O | ARG | B | 28 | -20.924 | -4.536 | 63.991 | 1.00 | 39.12 |
| 6210 | N | LEU | B | 29 | -21.856 | -3.924 | 65.957 | 1.00 | 39.68 |
| 6211 | CA | LEU | B | 29 | -20.637 | -3.556 | 66.620 | 1.00 | 39.80 |
| 6212 | CB | LEU | B | 29 | -21.008 | -2.766 | 67.868 | 1.00 | 39.92 |

FIGURE 3 DR

| A | B | C | D | E | F | G | H | I | J |
|---|---|---|---|---|---|---|---|---|---|
| 6213 | CG | LEU | B | 29 | -20.875 | -1.249 | 67.910 | 1.00 | 40.58 |
| 6214 | CD1 | LEU | B | 29 | -21.683 | -0.732 | 69.085 | 1.00 | 40.56 |
| 6215 | CD2 | LEU | B | 29 | -21.303 | -0.585 | 66.623 | 1.00 | 40.39 |
| 6216 | C | LEU | B | 29 | -19.945 | -4.842 | 67.035 | 1.00 | 39.84 |
| 6217 | O | LEU | B | 29 | -20.483 | -5.610 | 67.826 | 1.00 | 39.65 |
| 6218 | N | LYS | B | 30 | -18.768 | -5.108 | 66.495 | 1.00 | 40.26 |
| 6219 | CA | LYS | B | 30 | -18.047 | -6.297 | 66.931 | 1.00 | 40.77 |
| 6220 | CB | LYS | B | 30 | -17.055 | -6.779 | 65.885 | 1.00 | 41.21 |
| 6221 | CG | LYS | B | 30 | -17.720 | -7.358 | 64.650 | 1.00 | 43.51 |
| 6222 | CD | LYS | B | 30 | -16.815 | -8.350 | 63.947 | 1.00 | 45.58 |
| 6223 | CE | LYS | B | 30 | -17.202 | -9.800 | 64.271 | 1.00 | 48.08 |
| 6224 | NZ | LYS | B | 30 | -17.225 | -10.113 | 65.734 | 1.00 | 48.56 |
| 6225 | C | LYS | B | 30 | -17.347 | -5.997 | 68.237 | 1.00 | 40.39 |
| 6226 | O | LYS | B | 30 | -16.761 | -4.937 | 68.412 | 1.00 | 40.34 |
| 6227 | N | LEU | B | 31 | -17.461 | -6.920 | 69.174 | 1.00 | 40.68 |
| 6228 | CA | LEU | B | 31 | -16.810 | -6.774 | 70.456 | 1.00 | 41.26 |
| 6229 | CB | LEU | B | 31 | -17.755 | -7.188 | 71.583 | 1.00 | 41.72 |
| 6230 | CG | LEU | B | 31 | -18.821 | -6.197 | 72.049 | 1.00 | 43.90 |
| 6231 | CD1 | LEU | B | 31 | -19.901 | -5.995 | 70.972 | 1.00 | 45.00 |
| 6232 | CD2 | LEU | B | 31 | -19.443 | -6.679 | 73.365 | 1.00 | 44.09 |
| 6233 | C | LEU | B | 31 | -15.596 | -7.684 | 70.477 | 1.00 | 40.83 |
| 6234 | O | LEU | B | 31 | -15.402 | -8.491 | 69.568 | 1.00 | 40.77 |
| 6235 | N | TYR | B | 32 | -14.762 | -7.524 | 71.494 | 1.00 | 40.42 |
| 6236 | CA | TYR | B | 32 | -13.677 | -8.456 | 71.722 | 1.00 | 40.52 |
| 6237 | CB | TYR | B | 32 | -12.325 | -7.966 | 71.205 | 1.00 | 40.33 |
| 6238 | CG | TYR | B | 32 | -11.335 | -9.111 | 71.097 | 1.00 | 40.26 |
| 6239 | CD1 | TYR | B | 32 | -10.746 | -9.656 | 72.230 | 1.00 | 39.09 |
| 6240 | CE1 | TYR | B | 32 | -9.857 | -10.715 | 72.138 | 1.00 | 39.65 |
| 6241 | CZ | TYR | B | 32 | -9.555 | -11.253 | 70.901 | 1.00 | 40.53 |
| 6242 | OH | TYR | B | 32 | -8.659 | -12.305 | 70.802 | 1.00 | 41.54 |
| 6243 | CE2 | TYR | B | 32 | -10.131 | -10.733 | 69.762 | 1.00 | 40.34 |
| 6244 | CD2 | TYR | B | 32 | -11.024 | -9.676 | 69.863 | 1.00 | 40.59 |
| 6245 | C | TYR | B | 32 | -13.643 | -8.648 | 73.215 | 1.00 | 40.78 |
| 6246 | O | TYR | B | 32 | -12.922 | -7.954 | 73.935 | 1.00 | 40.51 |
| 6247 | N | SER | B | 33 | -14.447 | -9.590 | 73.675 | 1.00 | 41.07 |
| 6248 | CA | SER | B | 33 | -14.612 | -9.810 | 75.093 | 1.00 | 42.02 |
| 6249 | CB | SER | B | 33 | -16.088 | -10.092 | 75.391 | 1.00 | 42.31 |
| 6250 | OG | SER | B | 33 | -16.253 | -10.612 | 76.698 | 1.00 | 44.32 |
| 6251 | C | SER | B | 33 | -13.725 | -10.935 | 75.582 | 1.00 | 42.28 |
| 6252 | O | SER | B | 33 | -13.885 | -12.086 | 75.192 | 1.00 | 43.13 |
| 6253 | N | LEU | B | 34 | -12.774 | -10.607 | 76.441 | 1.00 | 42.35 |
| 6254 | CA | LEU | B | 34 | -11.872 | -11.626 | 76.933 | 1.00 | 42.22 |
| 6255 | CB | LEU | B | 34 | -10.449 | -11.343 | 76.456 | 1.00 | 41.83 |
| 6256 | CG | LEU | B | 34 | -9.857 | -9.991 | 76.829 | 1.00 | 40.59 |
| 6257 | CD1 | LEU | B | 34 | -9.349 | -10.059 | 78.253 | 1.00 | 38.90 |
| 6258 | CD2 | LEU | B | 34 | -8.755 | -9.608 | 75.849 | 1.00 | 38.10 |
| 6259 | C | LEU | B | 34 | -11.913 | -11.776 | 78.444 | 1.00 | 42.66 |
| 6260 | O | LEU | B | 34 | -12.320 | -10.864 | 79.166 | 1.00 | 42.16 |
| 6261 | N | ARG | B | 35 | -11.510 | -12.956 | 78.904 | 1.00 | 43.14 |
| 6262 | CA | ARG | B | 35 | -11.381 | -13.223 | 80.320 | 1.00 | 43.97 |
| 6263 | CB | ARG | B | 35 | -12.289 | -14.372 | 80.748 | 1.00 | 44.41 |

FIGURE 3 DS

| A | B | C | D | E | F | G | H | I | J |
|---|---|---|---|---|---|---|---|---|---|
| 6264 | CG | ARG | B | 35 | -13.748 | -14.178 | 80.430 | 1.00 | 46.96 |
| 6265 | CD | ARG | B | 35 | -14.457 | -15.498 | 80.199 | 1.00 | 51.91 |
| 6266 | NE | ARG | B | 35 | -15.907 | -15.361 | 80.144 | 1.00 | 54.36 |
| 6267 | CZ | ARG | B | 35 | -16.737 | -16.049 | 80.915 | 1.00 | 55.95 |
| 6268 | NH1 | ARG | B | 35 | -16.254 | -16.910 | 81.803 | 1.00 | 55.92 |
| 6269 | NH2 | ARG | B | 35 | -18.050 | -15.879 | 80.796 | 1.00 | 56.97 |
| 6270 | C | ARG | B | 35 | -9.937 | -13.613 | 80.582 | 1.00 | 43.91 |
| 6271 | O | ARG | B | 35 | -9.476 | -14.661 | 80.113 | 1.00 | 43.73 |
| 6272 | N | TRP | B | 36 | -9.219 | -12.775 | 81.314 | 1.00 | 43.77 |
| 6273 | CA | TRP | B | 36 | -7.841 | -13.093 | 81.648 | 1.00 | 44.42 |
| 6274 | CB | TRP | B | 36 | -7.142 | -11.895 | 82.283 | 1.00 | 43.77 |
| 6275 | CG | TRP | B | 36 | -6.864 | -10.747 | 81.372 | 1.00 | 41.88 |
| 6276 | CD1 | TRP | B | 36 | -7.506 | -9.547 | 81.356 | 1.00 | 41.08 |
| 6277 | NE1 | TRP | B | 36 | -6.960 | -8.727 | 80.399 | 1.00 | 37.93 |
| 6278 | CE2 | TRP | B | 36 | -5.935 | -9.393 | 79.785 | 1.00 | 38.72 |
| 6279 | CD2 | TRP | B | 36 | -5.845 | -10.665 | 80.377 | 1.00 | 39.63 |
| 6280 | CE3 | TRP | B | 36 | -4.859 | -11.545 | 79.920 | 1.00 | 40.34 |
| 6281 | CZ3 | TRP | B | 36 | -4.024 | -11.143 | 78.910 | 1.00 | 38.87 |
| 6282 | CH2 | TRP | B | 36 | -4.144 | -9.873 | 78.338 | 1.00 | 40.20 |
| 6283 | CZ2 | TRP | B | 36 | -5.085 | -8.981 | 78.765 | 1.00 | 38.43 |
| 6284 | C | TRP | B | 36 | -7.843 | -14.246 | 82.647 | 1.00 | 45.28 |
| 6285 | O | TRP | B | 36 | -8.602 | -14.223 | 83.605 | 1.00 | 45.67 |
| 6286 | N | ILE | B | 37 | -7.006 | -15.253 | 82.433 | 1.00 | 46.12 |
| 6287 | CA | ILE | B | 37 | -6.920 | -16.341 | 83.399 | 1.00 | 47.03 |
| 6288 | CB | ILE | B | 37 | -7.174 | -17.714 | 82.741 | 1.00 | 47.02 |
| 6289 | CG1 | ILE | B | 37 | -6.279 | -17.919 | 81.518 | 1.00 | 47.30 |
| 6290 | CD1 | ILE | B | 37 | -4.968 | -18.566 | 81.840 | 1.00 | 48.08 |
| 6291 | CG2 | ILE | B | 37 | -8.607 | -17.844 | 82.357 | 1.00 | 46.71 |
| 6292 | C | ILE | B | 37 | -5.583 | -16.314 | 84.128 | 1.00 | 47.70 |
| 6293 | O | ILE | B | 37 | -5.393 | -17.006 | 85.129 | 1.00 | 47.41 |
| 6294 | N | SER | B | 38 | -4.668 | -15.490 | 83.630 | 1.00 | 48.57 |
| 6295 | CA | SER | B | 38 | -3.357 | -15.353 | 84.246 | 1.00 | 49.53 |
| 6296 | CB | SER | B | 38 | -2.418 | -16.449 | 83.753 | 1.00 | 49.32 |
| 6297 | OG | SER | B | 38 | -1.954 | -16.147 | 82.451 | 1.00 | 48.71 |
| 6298 | C | SER | B | 38 | -2.758 | -14.007 | 83.886 | 1.00 | 50.44 |
| 6299 | O | SER | B | 38 | -3.457 | -13.106 | 83.428 | 1.00 | 51.01 |
| 6300 | N | ASP | B | 39 | -1.452 | -13.879 | 84.066 | 1.00 | 50.86 |
| 6301 | CA | ASP | B | 39 | -0.784 | -12.632 | 83.749 | 1.00 | 51.46 |
| 6302 | CB | ASP | B | 39 | 0.382 | -12.396 | 84.705 | 1.00 | 51.49 |
| 6303 | CG | ASP | B | 39 | 0.913 | -10.989 | 84.628 | 1.00 | 52.93 |
| 6304 | OD1 | ASP | B | 39 | 2.156 | -10.826 | 84.682 | 1.00 | 54.27 |
| 6305 | OD2 | ASP | B | 39 | 0.166 | -9.982 | 84.518 | 1.00 | 53.13 |
| 6306 | C | ASP | B | 39 | -0.279 | -12.631 | 82.321 | 1.00 | 51.44 |
| 6307 | O | ASP | B | 39 | 0.347 | -11.668 | 81.889 | 1.00 | 51.64 |
| 6308 | N | HIS | B | 40 | -0.573 | -13.697 | 81.582 | 1.00 | 51.62 |
| 6309 | CA | HIS | B | 40 | -0.059 | -13.849 | 80.227 | 1.00 | 51.91 |
| 6310 | CB | HIS | B | 40 | 1.104 | -14.850 | 80.213 | 1.00 | 52.32 |
| 6311 | CG | HIS | B | 40 | 1.618 | -15.200 | 81.576 | 1.00 | 54.08 |
| 6312 | ND1 | HIS | B | 40 | 2.452 | -14.370 | 82.297 | 1.00 | 54.07 |
| 6313 | CE1 | HIS | B | 40 | 2.738 | -14.939 | 83.456 | 1.00 | 55.31 |
| 6314 | NE2 | HIS | B | 40 | 2.113 | -16.103 | 83.516 | 1.00 | 55.18 |

FIGURE 3 DT

| A | B | C | D | E | F | G | H | I | J |
|---|---|---|---|---|---|---|---|---|---|
| 6315 | CD2 | HIS | B | 40 | 1.405 | -16.290 | 82.354 | 1.00 | 55.14 |
| 6316 | C | HIS | B | 40 | -1.106 | -14.346 | 79.247 | 1.00 | 51.73 |
| 6317 | O | HIS | B | 40 | -0.952 | -14.189 | 78.037 | 1.00 | 51.68 |
| 6318 | N | GLU | B | 41 | -2.162 | -14.966 | 79.755 | 1.00 | 51.57 |
| 6319 | CA | GLU | B | 41 | -3.165 | -15.525 | 78.863 | 1.00 | 51.93 |
| 6320 | CB | GLU | B | 41 | -3.110 | -17.053 | 78.913 | 1.00 | 52.01 |
| 6321 | CG | GLU | B | 41 | -1.830 | -17.658 | 78.355 | 1.00 | 53.18 |
| 6322 | CD | GLU | B | 41 | -1.681 | -19.133 | 78.686 | 1.00 | 54.96 |
| 6323 | OE1 | GLU | B | 41 | -1.048 | -19.464 | 79.720 | 1.00 | 55.10 |
| 6324 | OE2 | GLU | B | 41 | -2.195 | -19.962 | 77.906 | 1.00 | 55.09 |
| 6325 | C | GLU | B | 41 | -4.590 | -15.065 | 79.154 | 1.00 | 51.90 |
| 6326 | O | GLU | B | 41 | -4.940 | -14.762 | 80.299 | 1.00 | 51.84 |
| 6327 | N | TYR | B | 42 | -5.408 | -15.009 | 78.106 | 1.00 | 51.74 |
| 6328 | CA | TYR | B | 42 | -6.831 | -14.743 | 78.280 | 1.00 | 51.50 |
| 6329 | CB | TYR | B | 42 | -7.226 | -13.325 | 77.833 | 1.00 | 50.57 |
| 6330 | CG | TYR | B | 42 | -6.995 | -12.992 | 76.368 | 1.00 | 47.94 |
| 6331 | CD1 | TYR | B | 42 | -7.893 | -13.394 | 75.392 | 1.00 | 45.17 |
| 6332 | CE1 | TYR | B | 42 | -7.694 | -13.081 | 74.067 | 1.00 | 43.18 |
| 6333 | CZ | TYR | B | 42 | -6.592 | -12.343 | 73.699 | 1.00 | 43.34 |
| 6334 | OH | TYR | B | 42 | -6.389 | -12.031 | 72.371 | 1.00 | 41.78 |
| 6335 | CE2 | TYR | B | 42 | -5.691 | -11.921 | 74.651 | 1.00 | 43.45 |
| 6336 | CD2 | TYR | B | 42 | -5.896 | -12.242 | 75.972 | 1.00 | 44.84 |
| 6337 | C | TYR | B | 42 | -7.655 | -15.809 | 77.552 | 1.00 | 52.30 |
| 6338 | O | TYR | B | 42 | -7.148 | -16.489 | 76.658 | 1.00 | 52.29 |
| 6339 | N | LEU | B | 43 | -8.910 | -15.968 | 77.965 | 1.00 | 52.88 |
| 6340 | CA | LEU | B | 43 | -9.832 | -16.857 | 77.286 | 1.00 | 53.73 |
| 6341 | CB | LEU | B | 43 | -10.737 | -17.551 | 78.294 | 1.00 | 53.62 |
| 6342 | CG | LEU | B | 43 | -10.033 | -18.439 | 79.320 | 1.00 | 54.25 |
| 6343 | CD1 | LEU | B | 43 | -10.910 | -18.638 | 80.538 | 1.00 | 54.41 |
| 6344 | CD2 | LEU | B | 43 | -9.644 | -19.777 | 78.704 | 1.00 | 54.35 |
| 6345 | C | LEU | B | 43 | -10.671 | -16.031 | 76.311 | 1.00 | 54.45 |
| 6346 | O | LEU | B | 43 | -10.997 | -14.881 | 76.588 | 1.00 | 54.30 |
| 6347 | N | TYR | B | 44 | -11.006 | -16.613 | 75.166 | 1.00 | 55.68 |
| 6348 | CA | TYR | B | 44 | -11.817 | -15.923 | 74.171 | 1.00 | 57.26 |
| 6349 | CB | TYR | B | 44 | -10.930 | -15.157 | 73.178 | 1.00 | 57.10 |
| 6350 | CG | TYR | B | 44 | -11.671 | -14.398 | 72.091 | 1.00 | 57.59 |
| 6351 | CD1 | TYR | B | 44 | -12.356 | -13.221 | 72.372 | 1.00 | 58.09 |
| 6352 | CE1 | TYR | B | 44 | -13.030 | -12.516 | 71.369 | 1.00 | 58.19 |
| 6353 | CZ | TYR | B | 44 | -13.022 | -12.993 | 70.076 | 1.00 | 58.91 |
| 6354 | OH | TYR | B | 44 | -13.687 | -12.312 | 69.075 | 1.00 | 58.89 |
| 6355 | CE2 | TYR | B | 44 | -12.345 | -14.158 | 69.773 | 1.00 | 59.05 |
| 6356 | CD2 | TYR | B | 44 | -11.673 | -14.853 | 70.778 | 1.00 | 58.95 |
| 6357 | C | TYR | B | 44 | -12.730 | -16.925 | 73.470 | 1.00 | 58.24 |
| 6358 | O | TYR | B | 44 | -12.459 | -18.115 | 73.462 | 1.00 | 58.37 |
| 6359 | N | LYS | B | 45 | -13.828 | -16.435 | 72.910 | 1.00 | 59.96 |
| 6360 | CA | LYS | B | 45 | -14.817 | -17.274 | 72.236 | 1.00 | 61.44 |
| 6361 | CB | LYS | B | 45 | -16.173 | -17.124 | 72.920 | 1.00 | 61.57 |
| 6362 | CG | LYS | B | 45 | -16.230 | -16.025 | 73.991 | 1.00 | 62.26 |
| 6363 | CD | LYS | B | 45 | -15.996 | -14.613 | 73.431 | 1.00 | 62.59 |
| 6364 | CE | LYS | B | 45 | -16.607 | -13.542 | 74.347 | 1.00 | 63.16 |
| 6365 | NZ | LYS | B | 45 | -18.100 | -13.633 | 74.435 | 1.00 | 61.86 |

FIGURE 3 DU

| A | B | C | D | E | F | G | H | I | J |
|---|---|---|---|---|---|---|---|---|---|
| 6366 | C | LYS | B | 45 | -14.922 | -16.889 | 70.770 | 1.00 | 62.40 |
| 6367 | O | LYS | B | 45 | -15.245 | -15.751 | 70.455 | 1.00 | 62.63 |
| 6368 | N | GLN | B | 46 | -14.661 | -17.831 | 69.869 | 1.00 | 63.60 |
| 6369 | CA | GLN | B | 46 | -14.641 | -17.489 | 68.447 | 1.00 | 64.81 |
| 6370 | CB | GLN | B | 46 | -13.338 | -17.957 | 67.794 | 1.00 | 64.71 |
| 6371 | CG | GLN | B | 46 | -12.837 | -16.995 | 66.726 | 1.00 | 66.33 |
| 6372 | CD | GLN | B | 46 | -11.343 | -17.113 | 66.469 | 1.00 | 68.01 |
| 6373 | OE1 | GLN | B | 46 | -10.534 | -16.532 | 67.202 | 1.00 | 68.30 |
| 6374 | NE2 | GLN | B | 46 | -10.971 | -17.860 | 65.427 | 1.00 | 67.36 |
| 6375 | C | GLN | B | 46 | -15.862 | -17.981 | 67.668 | 1.00 | 65.41 |
| 6376 | O | GLN | B | 46 | -16.773 | -17.208 | 67.363 | 1.00 | 65.55 |
| 6377 | N | GLU | B | 47 | -15.866 | -19.260 | 67.314 | 1.00 | 65.98 |
| 6378 | CA | GLU | B | 47 | -17.036 | -19.846 | 66.675 | 1.00 | 66.56 |
| 6379 | CB | GLU | B | 47 | -16.703 | -20.456 | 65.307 | 1.00 | 66.89 |
| 6380 | CG | GLU | B | 47 | -17.220 | -19.640 | 64.120 | 1.00 | 68.68 |
| 6381 | CD | GLU | B | 47 | -16.237 | -18.599 | 63.590 | 1.00 | 71.16 |
| 6382 | OE1 | GLU | B | 47 | -16.247 | -17.434 | 64.076 | 1.00 | 72.38 |
| 6383 | OE2 | GLU | B | 47 | -15.473 | -18.943 | 62.656 | 1.00 | 70.88 |
| 6384 | C | GLU | B | 47 | -17.619 | -20.854 | 67.668 | 1.00 | 66.36 |
| 6385 | O | GLU | B | 47 | -17.660 | -22.064 | 67.430 | 1.00 | 66.62 |
| 6386 | N | ASN | B | 48 | -18.041 | -20.304 | 68.803 | 1.00 | 65.95 |
| 6387 | CA | ASN | B | 48 | -18.581 | -21.041 | 69.950 | 1.00 | 65.37 |
| 6388 | CB | ASN | B | 48 | -19.957 | -21.680 | 69.676 | 1.00 | 65.48 |
| 6389 | CG | ASN | B | 48 | -21.116 | -20.758 | 70.094 | 1.00 | 65.80 |
| 6390 | OD1 | ASN | B | 48 | -21.165 | -20.288 | 71.239 | 1.00 | 64.98 |
| 6391 | ND2 | ASN | B | 48 | -22.032 | -20.477 | 69.162 | 1.00 | 65.73 |
| 6392 | C | ASN | B | 48 | -17.616 | -21.941 | 70.736 | 1.00 | 64.81 |
| 6393 | O | ASN | B | 48 | -17.971 | -22.434 | 71.807 | 1.00 | 64.82 |
| 6394 | N | ASN | B | 49 | -16.400 | -22.138 | 70.226 | 1.00 | 63.93 |
| 6395 | CA | ASN | B | 49 | -15.387 | -22.856 | 70.993 | 1.00 | 63.05 |
| 6396 | CB | ASN | B | 49 | -14.321 | -23.493 | 70.101 | 1.00 | 63.20 |
| 6397 | CG | ASN | B | 49 | -14.676 | -23.455 | 68.628 | 1.00 | 63.85 |
| 6398 | OD1 | ASN | B | 49 | -14.554 | -22.414 | 67.976 | 1.00 | 65.23 |
| 6399 | ND2 | ASN | B | 49 | -15.092 | -24.596 | 68.087 | 1.00 | 63.26 |
| 6400 | C | ASN | B | 49 | -14.702 | -21.861 | 71.923 | 1.00 | 62.50 |
| 6401 | O | ASN | B | 49 | -14.864 | -20.649 | 71.780 | 1.00 | 62.26 |
| 6402 | N | ILE | B | 50 | -13.931 | -22.367 | 72.877 | 1.00 | 61.74 |
| 6403 | CA | ILE | B | 50 | -13.226 | -21.486 | 73.787 | 1.00 | 60.91 |
| 6404 | CB | ILE | B | 50 | -13.512 | -21.857 | 75.244 | 1.00 | 61.30 |
| 6405 | CG1 | ILE | B | 50 | -15.005 | -21.701 | 75.542 | 1.00 | 61.57 |
| 6406 | CD1 | ILE | B | 50 | -15.350 | -22.003 | 76.982 | 1.00 | 61.75 |
| 6407 | CG2 | ILE | B | 50 | -12.706 | -20.969 | 76.200 | 1.00 | 60.95 |
| 6408 | C | ILE | B | 50 | -11.742 | -21.534 | 73.500 | 1.00 | 60.12 |
| 6409 | O | ILE | B | 50 | -11.081 | -22.521 | 73.787 | 1.00 | 59.88 |
| 6410 | N | LEU | B | 51 | -11.239 | -20.458 | 72.909 | 1.00 | 59.28 |
| 6411 | CA | LEU | B | 51 | -9.831 | -20.335 | 72.572 | 1.00 | 58.43 |
| 6412 | CB | LEU | B | 51 | -9.658 | -19.391 | 71.381 | 1.00 | 58.12 |
| 6413 | CG | LEU | B | 51 | -9.703 | -20.085 | 70.019 | 1.00 | 58.00 |
| 6414 | CD1 | LEU | B | 51 | -10.759 | -21.167 | 70.027 | 1.00 | 57.14 |
| 6415 | CD2 | LEU | B | 51 | -9.933 | -19.103 | 68.885 | 1.00 | 57.24 |
| 6416 | C | LEU | B | 51 | -9.038 | -19.818 | 73.759 | 1.00 | 57.94 |

FIGURE 3 DV

| A | B | C | D | E | F | G | H | I | J |
|---|---|---|---|---|---|---|---|---|---|
| 6417 | O | LEU | B | 51 | -9.608 | -19.303 | 74.713 | 1.00 | 57.72 |
| 6418 | N | VAL | B | 52 | -7.723 | -19.986 | 73.712 | 1.00 | 57.43 |
| 6419 | CA | VAL | B | 52 | -6.860 | -19.429 | 74.746 | 1.00 | 56.95 |
| 6420 | CB | VAL | B | 52 | -6.370 | -20.478 | 75.756 | 1.00 | 57.02 |
| 6421 | CG1 | VAL | B | 52 | -5.285 | -19.891 | 76.638 | 1.00 | 56.40 |
| 6422 | CG2 | VAL | B | 52 | -5.866 | -21.719 | 75.049 | 1.00 | 56.93 |
| 6423 | C | VAL | B | 52 | -5.690 | -18.727 | 74.078 | 1.00 | 56.84 |
| 6424 | O | VAL | B | 52 | -4.989 | -19.301 | 73.248 | 1.00 | 56.50 |
| 6425 | N | PHE | B | 53 | -5.496 | -17.467 | 74.434 | 1.00 | 56.79 |
| 6426 | CA | PHE | B | 53 | -4.467 | -16.673 | 73.805 | 1.00 | 56.75 |
| 6427 | CB | PHE | B | 53 | -5.044 | -15.368 | 73.277 | 1.00 | 56.60 |
| 6428 | CG | PHE | B | 53 | -6.099 | -15.554 | 72.245 | 1.00 | 57.26 |
| 6429 | CD1 | PHE | B | 53 | -7.339 | -16.070 | 72.590 | 1.00 | 57.88 |
| 6430 | CE1 | PHE | B | 53 | -8.321 | -16.235 | 71.645 | 1.00 | 57.75 |
| 6431 | CZ | PHE | B | 53 | -8.077 | -15.889 | 70.336 | 1.00 | 58.84 |
| 6432 | CE2 | PHE | B | 53 | -6.844 | -15.375 | 69.973 | 1.00 | 58.70 |
| 6433 | CD2 | PHE | B | 53 | -5.862 | -15.209 | 70.927 | 1.00 | 57.58 |
| 6434 | C | PHE | B | 53 | -3.329 | -16.344 | 74.729 | 1.00 | 56.71 |
| 6435 | O | PHE | B | 53 | -3.484 | -16.262 | 75.941 | 1.00 | 56.63 |
| 6436 | N | ASN | B | 54 | -2.182 | -16.146 | 74.100 | 1.00 | 56.98 |
| 6437 | CA | ASN | B | 54 | -0.966 | -15.738 | 74.743 | 1.00 | 57.09 |
| 6438 | CB | ASN | B | 54 | 0.171 | -16.568 | 74.181 | 1.00 | 57.12 |
| 6439 | CG | ASN | B | 54 | 1.498 | -16.206 | 74.769 | 1.00 | 56.01 |
| 6440 | OD1 | ASN | B | 54 | 2.111 | -15.213 | 74.381 | 1.00 | 54.87 |
| 6441 | ND2 | ASN | B | 54 | 1.965 | -17.022 | 75.703 | 1.00 | 55.05 |
| 6442 | C | ASN | B | 54 | -0.799 | -14.286 | 74.342 | 1.00 | 57.73 |
| 6443 | O | ASN | B | 54 | -0.528 | -13.986 | 73.181 | 1.00 | 57.55 |
| 6444 | N | ALA | B | 55 | -0.994 | -13.383 | 75.292 | 1.00 | 58.43 |
| 6445 | CA | ALA | B | 55 | -0.932 | -11.960 | 75.000 | 1.00 | 59.29 |
| 6446 | CB | ALA | B | 55 | -1.108 | -11.160 | 76.277 | 1.00 | 59.33 |
| 6447 | C | ALA | B | 55 | 0.369 | -11.587 | 74.321 | 1.00 | 59.88 |
| 6448 | O | ALA | B | 55 | 0.419 | -10.651 | 73.524 | 1.00 | 60.04 |
| 6449 | N | GLU | B | 56 | 1.413 | -12.337 | 74.645 | 1.00 | 60.75 |
| 6450 | CA | GLU | B | 56 | 2.749 | -12.095 | 74.130 | 1.00 | 61.77 |
| 6451 | CB | GLU | B | 56 | 3.728 | -13.068 | 74.776 | 1.00 | 62.15 |
| 6452 | CG | GLU | B | 56 | 4.532 | -12.443 | 75.894 | 1.00 | 63.77 |
| 6453 | CD | GLU | B | 56 | 5.370 | -11.280 | 75.395 | 1.00 | 66.27 |
| 6454 | OE1 | GLU | B | 56 | 6.291 | -11.541 | 74.584 | 1.00 | 67.34 |
| 6455 | OE2 | GLU | B | 56 | 5.105 | -10.117 | 75.805 | 1.00 | 65.91 |
| 6456 | C | GLU | B | 56 | 2.883 | -12.139 | 72.607 | 1.00 | 62.06 |
| 6457 | O | GLU | B | 56 | 3.203 | -11.127 | 71.983 | 1.00 | 62.17 |
| 6458 | N | TYR | B | 57 | 2.673 | -13.311 | 72.013 | 1.00 | 62.35 |
| 6459 | CA | TYR | B | 57 | 2.769 | -13.431 | 70.560 | 1.00 | 62.74 |
| 6460 | CB | TYR | B | 57 | 3.508 | -14.701 | 70.125 | 1.00 | 63.09 |
| 6461 | CG | TYR | B | 57 | 4.429 | -15.295 | 71.152 | 1.00 | 64.05 |
| 6462 | CD1 | TYR | B | 57 | 5.027 | -14.509 | 72.119 | 1.00 | 65.43 |
| 6463 | CE1 | TYR | B | 57 | 5.864 | -15.056 | 73.061 | 1.00 | 66.27 |
| 6464 | CZ | TYR | B | 57 | 6.120 | -16.403 | 73.041 | 1.00 | 66.25 |
| 6465 | OH | TYR | B | 57 | 6.963 | -16.950 | 73.978 | 1.00 | 67.79 |
| 6466 | CE2 | TYR | B | 57 | 5.545 | -17.205 | 72.085 | 1.00 | 66.31 |
| 6467 | CD2 | TYR | B | 57 | 4.706 | -16.650 | 71.149 | 1.00 | 65.51 |

FIGURE 3 DW

| A | B | C | D | E | F | G | H | I | J |
|---|---|---|---|---|---|---|---|---|---|
| 6468 | C | TYR | B | 57 | 1.382 | -13.440 | 69.945 | 1.00 | 62.46 |
| 6469 | O | TYR | B | 57 | 1.233 | -13.316 | 68.733 | 1.00 | 62.46 |
| 6470 | N | GLY | B | 58 | 0.369 | -13.594 | 70.787 | 1.00 | 62.28 |
| 6471 | CA | GLY | B | 58 | -1.004 | -13.617 | 70.317 | 1.00 | 62.29 |
| 6472 | C | GLY | B | 58 | -1.392 | -14.950 | 69.710 | 1.00 | 62.12 |
| 6473 | O | GLY | B | 58 | -2.419 | -15.056 | 69.047 | 1.00 | 61.90 |
| 6474 | N | ASN | B | 59 | -0.560 | -15.966 | 69.928 | 1.00 | 62.10 |
| 6475 | CA | ASN | B | 59 | -0.838 | -17.299 | 69.409 | 1.00 | 62.12 |
| 6476 | CB | ASN | B | 59 | 0.426 | -18.160 | 69.412 | 1.00 | 62.09 |
| 6477 | CG | ASN | B | 59 | 0.910 | -18.464 | 70.815 | 1.00 | 62.18 |
| 6478 | OD1 | ASN | B | 59 | 1.191 | -17.553 | 71.586 | 1.00 | 60.82 |
| 6479 | ND2 | ASN | B | 59 | 0.993 | -19.748 | 71.160 | 1.00 | 64.54 |
| 6480 | C | ASN | B | 59 | -1.904 | -17.977 | 70.256 | 1.00 | 62.01 |
| 6481 | O | ASN | B | 59 | -1.908 | -17.865 | 71.484 | 1.00 | 62.06 |
| 6482 | N | SER | B | 60 | -2.804 | -18.691 | 69.605 | 1.00 | 61.92 |
| 6483 | CA | SER | B | 60 | -3.850 | -19.373 | 70.340 | 1.00 | 61.95 |
| 6484 | CB | SER | B | 60 | -5.204 | -18.728 | 70.056 | 1.00 | 61.91 |
| 6485 | OG | SER | B | 60 | -5.667 | -19.113 | 68.772 | 1.00 | 62.01 |
| 6486 | C | SER | B | 60 | -3.945 | -20.844 | 69.995 | 1.00 | 61.93 |
| 6487 | O | SER | B | 60 | -3.346 | -21.325 | 69.040 | 1.00 | 61.77 |
| 6488 | N | SER | B | 61 | -4.708 | -21.552 | 70.815 | 1.00 | 62.17 |
| 6489 | CA | SER | B | 61 | -5.069 | -22.932 | 70.555 | 1.00 | 62.30 |
| 6490 | CB | SER | B | 61 | -4.048 | -23.917 | 71.137 | 1.00 | 62.27 |
| 6491 | OG | SER | B | 61 | -3.943 | -23.803 | 72.538 | 1.00 | 62.62 |
| 6492 | C | SER | B | 61 | -6.455 | -23.110 | 71.158 | 1.00 | 62.28 |
| 6493 | O | SER | B | 61 | -6.931 | -22.250 | 71.904 | 1.00 | 62.54 |
| 6494 | N | VAL | B | 62 | -7.125 | -24.198 | 70.810 | 1.00 | 62.21 |
| 6495 | CA | VAL | B | 62 | -8.445 | -24.449 | 71.357 | 1.00 | 61.76 |
| 6496 | CB | VAL | B | 62 | -9.174 | -25.565 | 70.591 | 1.00 | 61.90 |
| 6497 | CG1 | VAL | B | 62 | -10.480 | -25.921 | 71.291 | 1.00 | 61.46 |
| 6498 | CG2 | VAL | B | 62 | -9.422 | -25.139 | 69.141 | 1.00 | 61.92 |
| 6499 | C | VAL | B | 62 | -8.277 | -24.855 | 72.807 | 1.00 | 61.57 |
| 6500 | O | VAL | B | 62 | -7.427 | -25.691 | 73.131 | 1.00 | 61.62 |
| 6501 | N | PHE | B | 63 | -9.067 | -24.244 | 73.683 | 1.00 | 60.96 |
| 6502 | CA | PHE | B | 63 | -9.010 | -24.560 | 75.098 | 1.00 | 60.46 |
| 6503 | CB | PHE | B | 63 | -9.159 | -23.290 | 75.932 | 1.00 | 60.45 |
| 6504 | CG | PHE | B | 63 | -9.346 | -23.553 | 77.399 | 1.00 | 60.16 |
| 6505 | CD1 | PHE | B | 63 | -10.613 | -23.705 | 77.931 | 1.00 | 59.55 |
| 6506 | CE1 | PHE | B | 63 | -10.788 | -23.956 | 79.270 | 1.00 | 59.59 |
| 6507 | CZ | PHE | B | 63 | -9.695 | -24.050 | 80.099 | 1.00 | 60.18 |
| 6508 | CE2 | PHE | B | 63 | -8.425 | -23.895 | 79.584 | 1.00 | 60.64 |
| 6509 | CD2 | PHE | B | 63 | -8.254 | -23.651 | 78.240 | 1.00 | 59.87 |
| 6510 | C | PHE | B | 63 | -10.137 | -25.515 | 75.425 | 1.00 | 60.33 |
| 6511 | O | PHE | B | 63 | -9.985 | -26.460 | 76.201 | 1.00 | 60.23 |
| 6512 | N | LEU | B | 64 | -11.283 | -25.244 | 74.824 | 1.00 | 60.21 |
| 6513 | CA | LEU | B | 64 | -12.467 | -26.039 | 75.041 | 1.00 | 60.12 |
| 6514 | CB | LEU | B | 64 | -13.212 | -25.543 | 76.274 | 1.00 | 60.27 |
| 6515 | CG | LEU | B | 64 | -14.335 | -26.436 | 76.790 | 1.00 | 60.44 |
| 6516 | CD1 | LEU | B | 64 | -13.765 | -27.490 | 77.728 | 1.00 | 59.69 |
| 6517 | CD2 | LEU | B | 64 | -15.378 | -25.585 | 77.495 | 1.00 | 60.61 |
| 6518 | C | LEU | B | 64 | -13.349 | -25.892 | 73.822 | 1.00 | 60.20 |

FIGURE 3 DX

| A | B | C | D | E | F | G | H | I | J |
|---|---|---|---|---|---|---|---|---|---|
| 6519 | O | LEU | B | 64 | -14.011 | -24.866 | 73.635 | 1.00 | 60.10 |
| 6520 | N | GLU | B | 65 | -13.328 | -26.906 | 72.968 | 1.00 | 60.28 |
| 6521 | CA | GLU | B | 65 | -14.175 | -26.897 | 71.791 | 1.00 | 60.35 |
| 6522 | CB | GLU | B | 65 | -13.674 | -27.905 | 70.760 | 1.00 | 60.68 |
| 6523 | CG | GLU | B | 65 | -13.138 | -29.193 | 71.362 | 1.00 | 61.58 |
| 6524 | CD | GLU | B | 65 | -12.352 | -30.009 | 70.355 | 1.00 | 63.25 |
| 6525 | OE1 | GLU | B | 65 | -12.038 | -31.190 | 70.647 | 1.00 | 62.40 |
| 6526 | OE2 | GLU | B | 65 | -12.044 | -29.457 | 69.271 | 1.00 | 63.97 |
| 6527 | C | GLU | B | 65 | -15.567 | -27.252 | 72.261 | 1.00 | 59.89 |
| 6528 | O | GLU | B | 65 | -15.727 | -28.072 | 73.162 | 1.00 | 59.64 |
| 6529 | N | ASN | B | 66 | -16.579 | -26.620 | 71.680 | 1.00 | 59.76 |
| 6530 | CA | ASN | B | 66 | -17.937 | -26.937 | 72.098 | 1.00 | 59.62 |
| 6531 | CB | ASN | B | 66 | -18.818 | -25.704 | 72.323 | 1.00 | 60.30 |
| 6532 | CG | ASN | B | 66 | -19.246 | -25.571 | 73.777 | 1.00 | 61.27 |
| 6533 | OD1 | ASN | B | 66 | -19.333 | -26.574 | 74.502 | 1.00 | 62.57 |
| 6534 | ND2 | ASN | B | 66 | -19.503 | -24.343 | 74.214 | 1.00 | 62.45 |
| 6535 | C | ASN | B | 66 | -18.652 | -28.005 | 71.308 | 1.00 | 58.77 |
| 6536 | O | ASN | B | 66 | -19.642 | -27.760 | 70.620 | 1.00 | 59.19 |
| 6537 | N | SER | B | 67 | -18.092 | -29.197 | 71.421 | 1.00 | 57.46 |
| 6538 | CA | SER | B | 67 | -18.703 | -30.416 | 70.970 | 1.00 | 56.01 |
| 6539 | CB | SER | B | 67 | -17.907 | -31.039 | 69.826 | 1.00 | 56.07 |
| 6540 | OG | SER | B | 67 | -16.517 | -31.116 | 70.123 | 1.00 | 56.11 |
| 6541 | C | SER | B | 67 | -18.569 | -31.213 | 72.262 | 1.00 | 55.06 |
| 6542 | O | SER | B | 67 | -19.113 | -32.303 | 72.415 | 1.00 | 54.84 |
| 6543 | N | THR | B | 68 | -17.836 | -30.618 | 73.202 | 1.00 | 53.88 |
| 6544 | CA | THR | B | 68 | -17.585 | -31.215 | 74.509 | 1.00 | 53.38 |
| 6545 | CB | THR | B | 68 | -16.723 | -30.287 | 75.380 | 1.00 | 53.52 |
| 6546 | OG1 | THR | B | 68 | -15.492 | -29.980 | 74.710 | 1.00 | 54.39 |
| 6547 | CG2 | THR | B | 68 | -16.279 | -31.019 | 76.639 | 1.00 | 52.84 |
| 6548 | C | THR | B | 68 | -18.858 | -31.530 | 75.280 | 1.00 | 52.69 |
| 6549 | O | THR | B | 68 | -18.966 | -32.595 | 75.885 | 1.00 | 52.90 |
| 6550 | N | PHE | B | 69 | -19.814 | -30.607 | 75.269 | 1.00 | 51.44 |
| 6551 | CA | PHE | B | 69 | -21.051 | -30.820 | 76.005 | 1.00 | 50.59 |
| 6552 | CB | PHE | B | 69 | -21.206 | -29.792 | 77.136 | 1.00 | 50.28 |
| 6553 | CG | PHE | B | 69 | -19.956 | -29.565 | 77.920 | 1.00 | 48.47 |
| 6554 | CD1 | PHE | B | 69 | -19.556 | -30.466 | 78.890 | 1.00 | 47.69 |
| 6555 | CE1 | PHE | B | 69 | -18.394 | -30.261 | 79.602 | 1.00 | 46.18 |
| 6556 | CZ | PHE | B | 69 | -17.622 | -29.155 | 79.347 | 1.00 | 45.66 |
| 6557 | CE2 | PHE | B | 69 | -18.014 | -28.248 | 78.379 | 1.00 | 46.23 |
| 6558 | CD2 | PHE | B | 69 | -19.170 | -28.457 | 77.675 | 1.00 | 46.14 |
| 6559 | C | PHE | B | 69 | -22.300 | -30.818 | 75.126 | 1.00 | 50.46 |
| 6560 | O | PHE | B | 69 | -23.347 | -30.320 | 75.538 | 1.00 | 50.05 |
| 6561 | N | ASP | B | 70 | -22.216 | -31.380 | 73.925 | 1.00 | 50.30 |
| 6562 | CA | ASP | B | 70 | -23.421 | -31.439 | 73.103 | 1.00 | 50.14 |
| 6563 | CB | ASP | B | 70 | -23.127 | -31.302 | 71.611 | 1.00 | 50.21 |
| 6564 | CG | ASP | B | 70 | -22.075 | -32.249 | 71.140 | 1.00 | 50.56 |
| 6565 | OD1 | ASP | B | 70 | -21.477 | -31.992 | 70.065 | 1.00 | 51.10 |
| 6566 | OD2 | ASP | B | 70 | -21.787 | -33.283 | 71.773 | 1.00 | 51.39 |
| 6567 | C | ASP | B | 70 | -24.263 | -32.666 | 73.439 | 1.00 | 49.78 |
| 6568 | O | ASP | B | 70 | -25.246 | -32.959 | 72.772 | 1.00 | 49.79 |
| 6569 | N | GLU | B | 71 | -23.864 | -33.362 | 74.499 | 1.00 | 49.75 |

FIGURE 3 DY

| A | B | C | D | E | F | G | H | I | J |
|---|---|---|---|---|---|---|---|---|---|
| 6570 | CA | GLU | B | 71 | -24.624 | -34.478 | 75.050 | 1.00 | 49.63 |
| 6571 | CB | GLU | B | 71 | -23.788 | -35.753 | 75.098 | 1.00 | 49.75 |
| 6572 | CG | GLU | B | 71 | -23.403 | -36.345 | 73.757 | 1.00 | 50.10 |
| 6573 | CD | GLU | B | 71 | -23.161 | -37.839 | 73.867 | 1.00 | 50.97 |
| 6574 | OE1 | GLU | B | 71 | -22.363 | -38.252 | 74.739 | 1.00 | 50.52 |
| 6575 | OE2 | GLU | B | 71 | -23.784 | -38.602 | 73.095 | 1.00 | 51.93 |
| 6576 | C | GLU | B | 71 | -24.996 | -34.103 | 76.479 | 1.00 | 49.34 |
| 6577 | O | GLU | B | 71 | -25.487 | -34.931 | 77.247 | 1.00 | 49.41 |
| 6578 | N | PHE | B | 72 | -24.736 | -32.856 | 76.844 | 1.00 | 48.96 |
| 6579 | CA | PHE | B | 72 | -25.026 | -32.391 | 78.194 | 1.00 | 48.61 |
| 6580 | CB | PHE | B | 72 | -24.496 | -30.976 | 78.397 | 1.00 | 48.58 |
| 6581 | CG | PHE | B | 72 | -24.533 | -30.534 | 79.814 | 1.00 | 48.54 |
| 6582 | CD1 | PHE | B | 72 | -23.728 | -31.149 | 80.756 | 1.00 | 48.14 |
| 6583 | CE1 | PHE | B | 72 | -23.758 | -30.754 | 82.060 | 1.00 | 48.48 |
| 6584 | CZ | PHE | B | 72 | -24.609 | -29.739 | 82.454 | 1.00 | 49.56 |
| 6585 | CE2 | PHE | B | 72 | -25.425 | -29.119 | 81.528 | 1.00 | 48.92 |
| 6586 | CD2 | PHE | B | 72 | -25.383 | -29.520 | 80.214 | 1.00 | 48.44 |
| 6587 | C | PHE | B | 72 | -26.512 | -32.472 | 78.568 | 1.00 | 48.44 |
| 6588 | O | PHE | B | 72 | -26.853 | -32.800 | 79.704 | 1.00 | 48.48 |
| 6589 | N | GLY | B | 73 | -27.393 | -32.167 | 77.620 | 1.00 | 48.19 |
| 6590 | CA | GLY | B | 73 | -28.821 | -32.283 | 77.859 | 1.00 | 48.01 |
| 6591 | C | GLY | B | 73 | -29.558 | -30.962 | 78.005 | 1.00 | 47.98 |
| 6592 | O | GLY | B | 73 | -30.791 | -30.921 | 78.038 | 1.00 | 47.82 |
| 6593 | N | HIS | B | 74 | -28.805 | -29.874 | 78.112 | 1.00 | 47.47 |
| 6594 | CA | HIS | B | 74 | -29.419 | -28.565 | 78.248 | 1.00 | 47.23 |
| 6595 | CB | HIS | B | 74 | -29.604 | -28.214 | 79.726 | 1.00 | 47.25 |
| 6596 | CG | HIS | B | 74 | -29.614 | -29.405 | 80.626 | 1.00 | 46.37 |
| 6597 | ND1 | HIS | B | 74 | -30.766 | -29.894 | 81.203 | 1.00 | 45.82 |
| 6598 | CE1 | HIS | B | 74 | -30.473 | -30.956 | 81.932 | 1.00 | 46.66 |
| 6599 | NE2 | HIS | B | 74 | -29.171 | -31.173 | 81.850 | 1.00 | 47.57 |
| 6600 | CD2 | HIS | B | 74 | -28.611 | -30.216 | 81.038 | 1.00 | 46.71 |
| 6601 | C | HIS | B | 74 | -28.451 | -27.600 | 77.631 | 1.00 | 46.90 |
| 6602 | O | HIS | B | 74 | -27.282 | -27.940 | 77.447 | 1.00 | 46.76 |
| 6603 | N | SER | B | 75 | -28.920 | -26.404 | 77.305 | 1.00 | 46.46 |
| 6604 | CA | SER | B | 75 | -28.026 | -25.408 | 76.738 | 1.00 | 46.32 |
| 6605 | CB | SER | B | 75 | -28.785 | -24.375 | 75.902 | 1.00 | 46.54 |
| 6606 | OG | SER | B | 75 | -29.882 | -23.847 | 76.622 | 1.00 | 47.39 |
| 6607 | C | SER | B | 75 | -27.268 | -24.732 | 77.872 | 1.00 | 46.25 |
| 6608 | O | SER | B | 75 | -27.832 | -24.414 | 78.933 | 1.00 | 45.78 |
| 6609 | N | ILE | B | 76 | -25.985 | -24.512 | 77.631 | 1.00 | 45.86 |
| 6610 | CA | ILE | B | 76 | -25.103 | -23.945 | 78.618 | 1.00 | 45.54 |
| 6611 | CB | ILE | B | 76 | -23.717 | -24.560 | 78.426 | 1.00 | 45.97 |
| 6612 | CG1 | ILE | B | 76 | -23.835 | -26.080 | 78.591 | 1.00 | 45.17 |
| 6613 | CD1 | ILE | B | 76 | -22.548 | -26.771 | 78.905 | 1.00 | 44.42 |
| 6614 | CG2 | ILE | B | 76 | -22.693 | -23.948 | 79.386 | 1.00 | 45.71 |
| 6615 | C | ILE | B | 76 | -25.096 | -22.432 | 78.520 | 1.00 | 45.32 |
| 6616 | O | ILE | B | 76 | -24.657 | -21.862 | 77.525 | 1.00 | 45.21 |
| 6617 | N | ASN | B | 77 | -25.608 | -21.779 | 79.561 | 1.00 | 44.93 |
| 6618 | CA | ASN | B | 77 | -25.697 | -20.332 | 79.556 | 1.00 | 44.21 |
| 6619 | CB | ASN | B | 77 | -26.619 | -19.827 | 80.652 | 1.00 | 44.24 |
| 6620 | CG | ASN | B | 77 | -26.976 | -18.376 | 80.453 | 1.00 | 45.26 |

FIGURE 3 DZ

| A | B | C | D | E | F | G | H | I | J |
|---|---|---|---|---|---|---|---|---|---|
| 6621 | OD1 | ASN | B | 77 | -27.574 | -18.024 | 79.439 | 1.00 | 46.47 |
| 6622 | ND2 | ASN | B | 77 | -26.574 | -17.515 | 81.390 | 1.00 | 45.50 |
| 6623 | C | ASN | B | 77 | -24.355 | -19.649 | 79.697 | 1.00 | 43.73 |
| 6624 | O | ASN | B | 77 | -24.052 | -18.705 | 78.983 | 1.00 | 43.48 |
| 6625 | N | ASP | B | 78 | -23.554 | -20.120 | 80.640 | 1.00 | 43.45 |
| 6626 | CA | ASP | B | 78 | -22.259 | -19.525 | 80.864 | 1.00 | 43.13 |
| 6627 | CB | ASP | B | 78 | -22.384 | -18.321 | 81.797 | 1.00 | 43.38 |
| 6628 | CG | ASP | B | 78 | -21.403 | -17.230 | 81.458 | 1.00 | 43.83 |
| 6629 | OD1 | ASP | B | 78 | -20.268 | -17.544 | 81.076 | 1.00 | 46.49 |
| 6630 | OD2 | ASP | B | 78 | -21.678 | -16.022 | 81.507 | 1.00 | 47.24 |
| 6631 | C | ASP | B | 78 | -21.324 | -20.559 | 81.455 | 1.00 | 42.89 |
| 6632 | O | ASP | B | 78 | -21.730 | -21.673 | 81.776 | 1.00 | 43.02 |
| 6633 | N | TYR | B | 79 | -20.061 | -20.201 | 81.571 | 1.00 | 42.54 |
| 6634 | CA | TYR | B | 79 | -19.096 | -21.116 | 82.128 | 1.00 | 42.96 |
| 6635 | CB | TYR | B | 79 | -18.338 | -21.875 | 81.032 | 1.00 | 43.09 |
| 6636 | CG | TYR | B | 79 | -17.394 | -20.992 | 80.273 | 1.00 | 44.00 |
| 6637 | CD1 | TYR | B | 79 | -17.779 | -20.393 | 79.074 | 1.00 | 45.46 |
| 6638 | CE1 | TYR | B | 79 | -16.913 | -19.560 | 78.384 | 1.00 | 45.52 |
| 6639 | CZ | TYR | B | 79 | -15.656 | -19.310 | 78.903 | 1.00 | 45.23 |
| 6640 | OH | TYR | B | 79 | -14.781 | -18.484 | 78.237 | 1.00 | 46.02 |
| 6641 | CE2 | TYR | B | 79 | -15.264 | -19.890 | 80.085 | 1.00 | 45.28 |
| 6642 | CD2 | TYR | B | 79 | -16.129 | -20.723 | 80.761 | 1.00 | 44.62 |
| 6643 | C | TYR | B | 79 | -18.138 | -20.313 | 82.965 | 1.00 | 42.84 |
| 6644 | O | TYR | B | 79 | -17.936 | -19.115 | 82.738 | 1.00 | 42.71 |
| 6645 | N | SER | B | 80 | -17.560 | -20.969 | 83.956 | 1.00 | 42.90 |
| 6646 | CA | SER | B | 80 | -16.600 | -20.299 | 84.798 | 1.00 | 43.31 |
| 6647 | CB | SER | B | 80 | -17.222 | -19.882 | 86.122 | 1.00 | 42.93 |
| 6648 | OG | SER | B | 80 | -16.279 | -19.122 | 86.845 | 1.00 | 43.95 |
| 6649 | C | SER | B | 80 | -15.433 | -21.211 | 85.040 | 1.00 | 43.25 |
| 6650 | O | SER | B | 80 | -15.581 | -22.303 | 85.566 | 1.00 | 43.48 |
| 6651 | N | ILE | B | 81 | -14.262 | -20.744 | 84.666 | 1.00 | 43.80 |
| 6652 | CA | ILE | B | 81 | -13.081 | -21.550 | 84.817 | 1.00 | 44.61 |
| 6653 | CB | ILE | B | 81 | -12.175 | -21.418 | 83.580 | 1.00 | 44.62 |
| 6654 | CG1 | ILE | B | 81 | -12.882 | -22.074 | 82.391 | 1.00 | 45.63 |
| 6655 | CD1 | ILE | B | 81 | -12.421 | -21.598 | 81.025 | 1.00 | 48.10 |
| 6656 | CG2 | ILE | B | 81 | -10.861 | -22.138 | 83.811 | 1.00 | 45.52 |
| 6657 | C | ILE | B | 81 | -12.347 | -21.291 | 86.125 | 1.00 | 44.73 |
| 6658 | O | ILE | B | 81 | -12.005 | -20.158 | 86.464 | 1.00 | 44.33 |
| 6659 | N | SER | B | 82 | -12.179 | -22.381 | 86.866 | 1.00 | 45.06 |
| 6660 | CA | SER | B | 82 | -11.396 | -22.434 | 88.085 | 1.00 | 45.20 |
| 6661 | CB | SER | B | 82 | -11.103 | -23.899 | 88.377 | 1.00 | 44.99 |
| 6662 | OG | SER | B | 82 | -10.305 | -24.031 | 89.520 | 1.00 | 47.54 |
| 6663 | C | SER | B | 82 | -10.087 | -21.672 | 87.890 | 1.00 | 44.93 |
| 6664 | O | SER | B | 82 | -9.421 | -21.833 | 86.869 | 1.00 | 44.86 |
| 6665 | N | PRO | B | 83 | -9.708 | -20.849 | 88.864 | 1.00 | 44.77 |
| 6666 | CA | PRO | B | 83 | -8.490 | -20.037 | 88.756 | 1.00 | 44.56 |
| 6667 | CB | PRO | B | 83 | -8.406 | -19.335 | 90.118 | 1.00 | 44.46 |
| 6668 | CG | PRO | B | 83 | -9.741 | -19.422 | 90.691 | 1.00 | 44.29 |
| 6669 | CD | PRO | B | 83 | -10.398 | -20.648 | 90.148 | 1.00 | 44.70 |
| 6670 | C | PRO | B | 83 | -7.248 | -20.897 | 88.554 | 1.00 | 44.43 |
| 6671 | O | PRO | B | 83 | -6.257 | -20.434 | 87.984 | 1.00 | 44.18 |

FIGURE 3 EA

| A | B | C | D | E | F | G | H | I | J |
|---|---|---|---|---|---|---|---|---|---|
| 6672 | N | ASP | B | 84 | -7.290 | -22.137 | 89.023 | 1.00 | 44.38 |
| 6673 | CA | ASP | B | 84 | -6.131 | -23.010 | 88.852 | 1.00 | 44.64 |
| 6674 | CB | ASP | B | 84 | -5.999 | -23.998 | 90.007 | 1.00 | 44.39 |
| 6675 | CG | ASP | B | 84 | -7.167 | -24.944 | 90.091 | 1.00 | 45.05 |
| 6676 | OD1 | ASP | B | 84 | -8.038 | -24.872 | 89.206 | 1.00 | 46.59 |
| 6677 | OD2 | ASP | B | 84 | -7.305 | -25.791 | 90.998 | 1.00 | 45.80 |
| 6678 | C | ASP | B | 84 | -6.214 | -23.744 | 87.520 | 1.00 | 44.63 |
| 6679 | O | ASP | B | 84 | -5.338 | -24.529 | 87.190 | 1.00 | 44.63 |
| 6680 | N | GLY | B | 85 | -7.272 | -23.471 | 86.760 | 1.00 | 44.63 |
| 6681 | CA | GLY | B | 85 | -7.465 | -24.078 | 85.453 | 1.00 | 44.80 |
| 6682 | C | GLY | B | 85 | -7.745 | -25.573 | 85.485 | 1.00 | 45.07 |
| 6683 | O | GLY | B | 85 | -7.631 | -26.239 | 84.455 | 1.00 | 45.53 |
| 6684 | N | GLN | B | 86 | -8.115 | -26.100 | 86.653 | 1.00 | 44.42 |
| 6685 | CA | GLN | B | 86 | -8.384 | -27.524 | 86.805 | 1.00 | 44.00 |
| 6686 | CB | GLN | B | 86 | -7.959 | -27.995 | 88.198 | 1.00 | 44.18 |
| 6687 | CG | GLN | B | 86 | -6.464 | -27.868 | 88.466 | 1.00 | 44.95 |
| 6688 | CD | GLN | B | 86 | -6.044 | -28.519 | 89.772 | 1.00 | 46.30 |
| 6689 | OE1 | GLN | B | 86 | -6.805 | -29.304 | 90.353 | 1.00 | 47.20 |
| 6690 | NE2 | GLN | B | 86 | -4.834 | -28.200 | 90.239 | 1.00 | 45.35 |
| 6691 | C | GLN | B | 86 | -9.849 | -27.901 | 86.566 | 1.00 | 43.84 |
| 6692 | O | GLN | B | 86 | -10.165 | -29.024 | 86.140 | 1.00 | 43.25 |
| 6693 | N | PHE | B | 87 | -10.750 | -26.965 | 86.837 | 1.00 | 43.39 |
| 6694 | CA | PHE | B | 87 | -12.166 | -27.251 | 86.687 | 1.00 | 43.01 |
| 6695 | CB | PHE | B | 87 | -12.822 | -27.432 | 88.060 | 1.00 | 43.23 |
| 6696 | CG | PHE | B | 87 | -12.291 | -28.599 | 88.840 | 1.00 | 43.82 |
| 6697 | CD1 | PHE | B | 87 | -12.865 | -29.850 | 88.709 | 1.00 | 43.21 |
| 6698 | CE1 | PHE | B | 87 | -12.386 | -30.920 | 89.427 | 1.00 | 44.46 |
| 6699 | CZ | PHE | B | 87 | -11.314 | -30.759 | 90.287 | 1.00 | 43.15 |
| 6700 | CE2 | PHE | B | 87 | -10.735 | -29.523 | 90.428 | 1.00 | 43.96 |
| 6701 | CD2 | PHE | B | 87 | -11.224 | -28.444 | 89.709 | 1.00 | 43.67 |
| 6702 | C | PHE | B | 87 | -12.906 | -26.161 | 85.945 | 1.00 | 42.92 |
| 6703 | O | PHE | B | 87 | -12.451 | -25.018 | 85.846 | 1.00 | 42.77 |
| 6704 | N | ILE | B | 88 | -14.074 | -26.521 | 85.436 | 1.00 | 42.65 |
| 6705 | CA | ILE | B | 88 | -14.914 | -25.560 | 84.770 | 1.00 | 42.40 |
| 6706 | CB | ILE | B | 88 | -14.816 | -25.705 | 83.247 | 1.00 | 42.76 |
| 6707 | CG1 | ILE | B | 88 | -15.921 | -24.882 | 82.576 | 1.00 | 43.27 |
| 6708 | CD1 | ILE | B | 88 | -15.661 | -24.609 | 81.115 | 1.00 | 43.05 |
| 6709 | CG2 | ILE | B | 88 | -14.948 | -27.143 | 82.845 | 1.00 | 42.96 |
| 6710 | C | ILE | B | 88 | -16.339 | -25.723 | 85.267 | 1.00 | 41.86 |
| 6711 | O | ILE | B | 88 | -16.853 | -26.835 | 85.410 | 1.00 | 41.80 |
| 6712 | N | LEU | B | 89 | -16.960 | -24.601 | 85.583 | 1.00 | 41.05 |
| 6713 | CA | LEU | B | 89 | -18.324 | -24.617 | 86.064 | 1.00 | 40.03 |
| 6714 | CB | LEU | B | 89 | -18.508 | -23.552 | 87.141 | 1.00 | 40.27 |
| 6715 | CG | LEU | B | 89 | -19.862 | -23.487 | 87.831 | 1.00 | 40.26 |
| 6716 | CD1 | LEU | B | 89 | -19.981 | -22.168 | 88.553 | 1.00 | 41.65 |
| 6717 | CD2 | LEU | B | 89 | -20.041 | -24.645 | 88.799 | 1.00 | 39.37 |
| 6718 | C | LEU | B | 89 | -19.227 | -24.319 | 84.889 | 1.00 | 39.65 |
| 6719 | O | LEU | B | 89 | -19.009 | -23.355 | 84.160 | 1.00 | 38.91 |
| 6720 | N | LEU | B | 90 | -20.232 | -25.160 | 84.697 | 1.00 | 39.35 |
| 6721 | CA | LEU | B | 90 | -21.187 | -24.955 | 83.635 | 1.00 | 39.46 |
| 6722 | CB | LEU | B | 90 | -21.404 | -26.247 | 82.845 | 1.00 | 39.49 |

FIGURE 3 EB

| A | B | C | D | E | F | G | H | I | J |
|---|---|---|---|---|---|---|---|---|---|
| 6723 | CG | LEU | B | 90 | -20.114 | -26.900 | 82.323 | 1.00 | 40.77 |
| 6724 | CD1 | LEU | B | 90 | -20.330 | -28.380 | 82.030 | 1.00 | 41.95 |
| 6725 | CD2 | LEU | B | 90 | -19.583 | -26.185 | 81.088 | 1.00 | 41.64 |
| 6726 | C | LEU | B | 90 | -22.490 | -24.458 | 84.232 | 1.00 | 39.06 |
| 6727 | O | LEU | B | 90 | -23.051 | -25.067 | 85.142 | 1.00 | 39.14 |
| 6728 | N | GLU | B | 91 | -22.965 | -23.335 | 83.721 | 1.00 | 38.70 |
| 6729 | CA | GLU | B | 91 | -24.212 | -22.751 | 84.196 | 1.00 | 38.30 |
| 6730 | CB | GLU | B | 91 | -24.028 | -21.242 | 84.349 | 1.00 | 37.90 |
| 6731 | CG | GLU | B | 91 | -25.179 | -20.482 | 84.977 | 1.00 | 37.84 |
| 6732 | CD | GLU | B | 91 | -24.851 | -19.007 | 85.130 | 1.00 | 38.88 |
| 6733 | OE1 | GLU | B | 91 | -25.310 | -18.200 | 84.279 | 1.00 | 39.94 |
| 6734 | OE2 | GLU | B | 91 | -24.127 | -18.656 | 86.092 | 1.00 | 37.39 |
| 6735 | C | GLU | B | 91 | -25.326 | -23.063 | 83.201 | 1.00 | 37.98 |
| 6736 | O | GLU | B | 91 | -25.174 | -22.818 | 82.007 | 1.00 | 38.03 |
| 6737 | N | TYR | B | 92 | -26.423 | -23.635 | 83.693 | 1.00 | 37.65 |
| 6738 | CA | TYR | B | 92 | -27.590 | -23.931 | 82.862 | 1.00 | 37.66 |
| 6739 | CB | TYR | B | 92 | -27.513 | -25.332 | 82.232 | 1.00 | 37.50 |
| 6740 | CG | TYR | B | 92 | -27.540 | -26.511 | 83.182 | 1.00 | 36.81 |
| 6741 | CD1 | TYR | B | 92 | -26.466 | -26.779 | 84.016 | 1.00 | 36.25 |
| 6742 | CE1 | TYR | B | 92 | -26.486 | -27.871 | 84.870 | 1.00 | 37.27 |
| 6743 | CZ | TYR | B | 92 | -27.586 | -28.708 | 84.887 | 1.00 | 36.87 |
| 6744 | OH | TYR | B | 92 | -27.602 | -29.787 | 85.745 | 1.00 | 37.50 |
| 6745 | CE2 | TYR | B | 92 | -28.662 | -28.468 | 84.049 | 1.00 | 35.25 |
| 6746 | CD2 | TYR | B | 92 | -28.632 | -27.380 | 83.209 | 1.00 | 35.06 |
| 6747 | C | TYR | B | 92 | -28.911 | -23.702 | 83.608 | 1.00 | 37.66 |
| 6748 | O | TYR | B | 92 | -28.907 | -23.378 | 84.790 | 1.00 | 37.77 |
| 6749 | N | ASN | B | 93 | -30.028 | -23.875 | 82.913 | 1.00 | 38.10 |
| 6750 | CA | ASN | B | 93 | -31.357 | -23.557 | 83.451 | 1.00 | 38.81 |
| 6751 | CB | ASN | B | 93 | -31.871 | -24.624 | 84.420 | 1.00 | 39.42 |
| 6752 | CG | ASN | B | 93 | -32.278 | -25.913 | 83.716 | 1.00 | 40.81 |
| 6753 | OD1 | ASN | B | 93 | -32.194 | -26.024 | 82.491 | 1.00 | 43.68 |
| 6754 | ND2 | ASN | B | 93 | -32.711 | -26.892 | 84.490 | 1.00 | 40.78 |
| 6755 | C | ASN | B | 93 | -31.394 | -22.166 | 84.099 | 1.00 | 38.86 |
| 6756 | O | ASN | B | 93 | -32.037 | -21.948 | 85.137 | 1.00 | 39.17 |
| 6757 | N | TYR | B | 94 | -30.686 | -21.243 | 83.464 | 1.00 | 38.00 |
| 6758 | CA | TYR | B | 94 | -30.645 | -19.861 | 83.856 | 1.00 | 37.85 |
| 6759 | CB | TYR | B | 94 | -29.830 | -19.090 | 82.822 | 1.00 | 37.50 |
| 6760 | CG | TYR | B | 94 | -29.996 | -17.591 | 82.885 | 1.00 | 37.18 |
| 6761 | CD1 | TYR | B | 94 | -29.226 | -16.832 | 83.760 | 1.00 | 35.96 |
| 6762 | CE1 | TYR | B | 94 | -29.359 | -15.461 | 83.831 | 1.00 | 34.63 |
| 6763 | CZ | TYR | B | 94 | -30.263 | -14.825 | 83.021 | 1.00 | 34.93 |
| 6764 | OH | TYR | B | 94 | -30.358 | -13.454 | 83.112 | 1.00 | 36.76 |
| 6765 | CE2 | TYR | B | 94 | -31.052 | -15.549 | 82.126 | 1.00 | 34.11 |
| 6766 | CD2 | TYR | B | 94 | -30.912 | -16.929 | 82.064 | 1.00 | 35.21 |
| 6767 | C | TYR | B | 94 | -32.059 | -19.294 | 83.923 | 1.00 | 37.99 |
| 6768 | O | TYR | B | 94 | -32.809 | -19.377 | 82.952 | 1.00 | 38.37 |
| 6769 | N | VAL | B | 95 | -32.427 | -18.748 | 85.081 | 1.00 | 37.75 |
| 6770 | CA | VAL | B | 95 | -33.712 | -18.077 | 85.251 | 1.00 | 37.49 |
| 6771 | CB | VAL | B | 95 | -34.715 | -18.902 | 86.100 | 1.00 | 37.70 |
| 6772 | CG1 | VAL | B | 95 | -36.058 | -18.167 | 86.237 | 1.00 | 37.67 |
| 6773 | CG2 | VAL | B | 95 | -34.960 | -20.290 | 85.471 | 1.00 | 37.86 |

FIGURE 3 EC

| A | B | C | D | E | F | G | H | I | J |
|---|---|---|---|---|---|---|---|---|---|
| 6774 | C | VAL | B | 95 | -33.419 | -16.716 | 85.885 | 1.00 | 37.08 |
| 6775 | O | VAL | B | 95 | -33.012 | -16.627 | 87.046 | 1.00 | 37.66 |
| 6776 | N | LYS | B | 96 | -33.583 | -15.663 | 85.097 | 1.00 | 36.23 |
| 6777 | CA | LYS | B | 96 | -33.286 | -14.309 | 85.554 | 1.00 | 35.28 |
| 6778 | CB | LYS | B | 96 | -33.368 | -13.312 | 84.392 | 1.00 | 35.17 |
| 6779 | CG | LYS | B | 96 | -33.139 | -11.886 | 84.831 | 1.00 | 35.12 |
| 6780 | CD | LYS | B | 96 | -33.255 | -10.901 | 83.677 | 1.00 | 36.00 |
| 6781 | CE | LYS | B | 96 | -33.274 | -9.465 | 84.177 | 1.00 | 35.60 |
| 6782 | NZ | LYS | B | 96 | -34.266 | -9.245 | 85.303 | 1.00 | 33.79 |
| 6783 | C | LYS | B | 96 | -34.190 | -13.831 | 86.676 | 1.00 | 34.41 |
| 6784 | O | LYS | B | 96 | -35.374 | -14.163 | 86.721 | 1.00 | 34.08 |
| 6785 | N | GLN | B | 97 | -33.608 | -13.074 | 87.600 | 1.00 | 33.47 |
| 6786 | CA | GLN | B | 97 | -34.378 | -12.439 | 88.655 | 1.00 | 32.58 |
| 6787 | CB | GLN | B | 97 | -33.836 | -12.785 | 90.027 | 1.00 | 32.88 |
| 6788 | CG | GLN | B | 97 | -34.818 | -12.535 | 91.138 | 1.00 | 35.20 |
| 6789 | CD | GLN | B | 97 | -34.220 | -12.791 | 92.519 | 1.00 | 38.14 |
| 6790 | OE1 | GLN | B | 97 | -34.839 | -13.460 | 93.339 | 1.00 | 39.28 |
| 6791 | NE2 | GLN | B | 97 | -33.020 | -12.250 | 92.776 | 1.00 | 38.20 |
| 6792 | C | GLN | B | 97 | -34.312 | -10.945 | 88.410 | 1.00 | 31.47 |
| 6793 | O | GLN | B | 97 | -34.973 | -10.451 | 87.516 | 1.00 | 30.40 |
| 6794 | N | TRP | B | 98 | -33.485 | -10.225 | 89.166 | 1.00 | 30.46 |
| 6795 | CA | TRP | B | 98 | -33.424 | -8.785 | 88.967 | 1.00 | 29.28 |
| 6796 | CB | TRP | B | 98 | -33.297 | -8.019 | 90.281 | 1.00 | 28.77 |
| 6797 | CG | TRP | B | 98 | -34.248 | -8.527 | 91.306 | 1.00 | 26.51 |
| 6798 | CD1 | TRP | B | 98 | -33.959 | -8.854 | 92.601 | 1.00 | 26.16 |
| 6799 | NE1 | TRP | B | 98 | -35.079 | -9.340 | 93.228 | 1.00 | 26.15 |
| 6800 | CE2 | TRP | B | 98 | -36.128 | -9.317 | 92.345 | 1.00 | 23.81 |
| 6801 | CD2 | TRP | B | 98 | -35.638 | -8.826 | 91.121 | 1.00 | 24.92 |
| 6802 | CE3 | TRP | B | 98 | -36.523 | -8.722 | 90.042 | 1.00 | 22.52 |
| 6803 | CZ3 | TRP | B | 98 | -37.826 | -9.097 | 90.222 | 1.00 | 22.86 |
| 6804 | CH2 | TRP | B | 98 | -38.283 | -9.577 | 91.456 | 1.00 | 22.77 |
| 6805 | CZ2 | TRP | B | 98 | -37.449 | -9.693 | 92.522 | 1.00 | 23.43 |
| 6806 | C | TRP | B | 98 | -32.365 | -8.427 | 87.951 | 1.00 | 29.53 |
| 6807 | O | TRP | B | 98 | -32.213 | -9.127 | 86.955 | 1.00 | 29.73 |
| 6808 | N | ARG | B | 99 | -31.652 | -7.333 | 88.168 | 1.00 | 29.39 |
| 6809 | CA | ARG | B | 99 | -30.689 | -6.910 | 87.182 | 1.00 | 29.98 |
| 6810 | CB | ARG | B | 99 | -30.312 | -5.467 | 87.417 | 1.00 | 30.83 |
| 6811 | CG | ARG | B | 99 | -29.466 | -4.866 | 86.315 | 1.00 | 31.29 |
| 6812 | CD | ARG | B | 99 | -28.821 | -3.579 | 86.759 | 1.00 | 33.85 |
| 6813 | NE | ARG | B | 99 | -29.819 | -2.565 | 87.063 | 1.00 | 35.27 |
| 6814 | CZ | ARG | B | 99 | -30.299 | -1.733 | 86.152 | 1.00 | 36.76 |
| 6815 | NH1 | ARG | B | 99 | -29.860 | -1.832 | 84.897 | 1.00 | 36.31 |
| 6816 | NH2 | ARG | B | 99 | -31.207 | -0.812 | 86.483 | 1.00 | 34.65 |
| 6817 | C | ARG | B | 99 | -29.428 | -7.755 | 87.182 | 1.00 | 30.65 |
| 6818 | O | ARG | B | 99 | -28.776 | -7.897 | 86.138 | 1.00 | 30.42 |
| 6819 | N | HIS | B | 100 | -29.068 | -8.302 | 88.348 | 1.00 | 30.49 |
| 6820 | CA | HIS | B | 100 | -27.835 | -9.080 | 88.446 | 1.00 | 30.33 |
| 6821 | CB | HIS | B | 100 | -26.832 | -8.458 | 89.439 | 1.00 | 29.88 |
| 6822 | CG | HIS | B | 100 | -26.496 | -7.031 | 89.151 | 1.00 | 30.52 |
| 6823 | ND1 | HIS | B | 100 | -25.635 | -6.657 | 88.142 | 1.00 | 31.38 |
| 6824 | CE1 | HIS | B | 100 | -25.526 | -5.338 | 88.124 | 1.00 | 30.86 |

FIGURE 3ED

| A | B | C | D | E | F | G | H | I | J |
|---|---|---|---|---|---|---|---|---|---|
| 6825 | NE2 | HIS | B | 138 | -26.284 | -4.844 | 89.087 | 1.00 | 30.38 |
| 6826 | CD2 | HIS | B | 138 | -26.903 | -5.881 | 89.744 | 1.00 | 30.25 |
| 6827 | C | HIS | B | 138 | -28.152 | -10.479 | 88.890 | 1.00 | 30.15 |
| 6828 | O | HIS | B | 138 | -27.505 | -11.423 | 88.467 | 1.00 | 30.34 |
| 6829 | N | SER | B | 139 | -29.149 | -10.603 | 89.753 | 1.00 | 30.24 |
| 6830 | CA | SER | B | 139 | -29.505 | -11.889 | 90.311 | 1.00 | 30.82 |
| 6831 | CB | SER | B | 139 | -30.405 | -11.711 | 91.531 | 1.00 | 30.55 |
| 6832 | OG | SER | B | 139 | -31.571 | -10.973 | 91.193 | 1.00 | 31.73 |
| 6833 | C | SER | B | 139 | -30.205 | -12.801 | 89.313 | 1.00 | 31.14 |
| 6834 | O | SER | B | 139 | -30.886 | -12.347 | 88.393 | 1.00 | 30.27 |
| 6835 | N | TYR | B | 140 | -30.039 | -14.097 | 89.536 | 1.00 | 32.33 |
| 6836 | CA | TYR | B | 140 | -30.678 | -15.117 | 88.726 | 1.00 | 33.64 |
| 6837 | CB | TYR | B | 140 | -30.112 | -15.152 | 87.308 | 1.00 | 33.16 |
| 6838 | CG | TYR | B | 140 | -28.653 | -15.523 | 87.213 | 1.00 | 32.32 |
| 6839 | CD1 | TYR | B | 140 | -28.248 | -16.854 | 87.199 | 1.00 | 31.87 |
| 6840 | CE1 | TYR | B | 140 | -26.908 | -17.191 | 87.082 | 1.00 | 31.29 |
| 6841 | CZ | TYR | B | 140 | -25.970 | -16.189 | 86.985 | 1.00 | 31.61 |
| 6842 | OH | TYR | B | 140 | -24.636 | -16.496 | 86.884 | 1.00 | 33.08 |
| 6843 | CE2 | TYR | B | 140 | -26.350 | -14.867 | 86.990 | 1.00 | 31.84 |
| 6844 | CD2 | TYR | B | 140 | -27.679 | -14.539 | 87.107 | 1.00 | 31.76 |
| 6845 | C | TYR | B | 140 | -30.451 | -16.455 | 89.376 | 1.00 | 34.99 |
| 6846 | O | TYR | B | 140 | -29.503 | -16.636 | 90.138 | 1.00 | 35.19 |
| 6847 | N | THR | B | 141 | -31.333 | -17.386 | 89.053 | 1.00 | 35.94 |
| 6848 | CA | THR | B | 141 | -31.259 | -18.732 | 89.557 | 1.00 | 37.26 |
| 6849 | CB | THR | B | 141 | -32.659 | -19.120 | 90.044 | 1.00 | 37.50 |
| 6850 | OG1 | THR | B | 141 | -32.692 | -18.991 | 91.474 | 1.00 | 39.59 |
| 6851 | CG2 | THR | B | 141 | -32.936 | -20.568 | 89.817 | 1.00 | 37.87 |
| 6852 | C | THR | B | 141 | -30.711 | -19.665 | 88.458 | 1.00 | 37.49 |
| 6853 | O | THR | B | 141 | -30.814 | -19.348 | 87.269 | 1.00 | 37.12 |
| 6854 | N | ALA | B | 142 | -30.094 | -20.785 | 88.845 | 1.00 | 37.83 |
| 6855 | CA | ALA | B | 142 | -29.508 | -21.679 | 87.849 | 1.00 | 38.47 |
| 6856 | CB | ALA | B | 142 | -28.405 | -20.973 | 87.096 | 1.00 | 38.13 |
| 6857 | C | ALA | B | 142 | -28.981 | -23.002 | 88.376 | 1.00 | 39.12 |
| 6858 | O | ALA | B | 142 | -28.700 | -23.158 | 89.569 | 1.00 | 40.13 |
| 6859 | N | SER | B | 143 | -28.844 | -23.958 | 87.463 | 1.00 | 39.45 |
| 6860 | CA | SER | B | 143 | -28.279 | -25.265 | 87.784 | 1.00 | 38.93 |
| 6861 | CB | SER | B | 143 | -28.967 | -26.388 | 87.000 | 1.00 | 38.72 |
| 6862 | OG | SER | B | 143 | -30.289 | -26.612 | 87.469 | 1.00 | 37.35 |
| 6863 | C | SER | B | 143 | -26.812 | -25.186 | 87.430 | 1.00 | 39.17 |
| 6864 | O | SER | B | 143 | -26.407 | -24.335 | 86.644 | 1.00 | 38.98 |
| 6865 | N | TYR | B | 144 | -26.017 | -26.061 | 88.030 | 1.00 | 39.50 |
| 6866 | CA | TYR | B | 144 | -24.587 | -26.032 | 87.826 | 1.00 | 40.02 |
| 6867 | CB | TYR | B | 144 | -23.906 | -25.222 | 88.939 | 1.00 | 39.62 |
| 6868 | CG | TYR | B | 144 | -24.238 | -23.756 | 88.900 | 1.00 | 37.80 |
| 6869 | CD1 | TYR | B | 144 | -25.313 | -23.249 | 89.613 | 1.00 | 35.67 |
| 6870 | CE1 | TYR | B | 144 | -25.624 | -21.926 | 89.563 | 1.00 | 34.50 |
| 6871 | CZ | TYR | B | 144 | -24.861 | -21.084 | 88.782 | 1.00 | 34.06 |
| 6872 | OH | TYR | B | 144 | -25.145 | -19.752 | 88.730 | 1.00 | 36.54 |
| 6873 | CE2 | TYR | B | 144 | -23.805 | -21.557 | 88.064 | 1.00 | 35.43 |
| 6874 | CD2 | TYR | B | 144 | -23.499 | -22.887 | 88.117 | 1.00 | 36.64 |
| 6875 | C | TYR | B | 144 | -23.996 | -27.418 | 87.828 | 1.00 | 40.90 |

FIGURE 3 EE

| A | B | C | D | E | F | G | H | I | J |
|---|---|---|---|---|---|---|---|---|---|
| 6876 | O | TYR | B | 144 | -24.373 | -28.273 | 88.614 | 1.00 | 40.67 |
| 6877 | N | ASP | B | 145 | -23.063 | -27.639 | 86.926 | 1.00 | 42.17 |
| 6878 | CA | ASP | B | 145 | -22.315 | -28.867 | 86.957 | 1.00 | 43.53 |
| 6879 | CB | ASP | B | 145 | -22.827 | -29.878 | 85.936 | 1.00 | 43.46 |
| 6880 | CG | ASP | B | 145 | -24.093 | -30.557 | 86.412 | 1.00 | 44.94 |
| 6881 | OD1 | ASP | B | 145 | -23.981 | -31.578 | 87.121 | 1.00 | 46.31 |
| 6882 | OD2 | ASP | B | 145 | -25.245 | -30.121 | 86.176 | 1.00 | 46.24 |
| 6883 | C | ASP | B | 145 | -20.869 | -28.474 | 86.785 | 1.00 | 44.26 |
| 6884 | O | ASP | B | 145 | -20.556 | -27.418 | 86.240 | 1.00 | 44.38 |
| 6885 | N | ILE | B | 146 | -19.998 | -29.304 | 87.324 | 1.00 | 45.38 |
| 6886 | CA | ILE | B | 146 | -18.583 | -29.033 | 87.323 | 1.00 | 46.41 |
| 6887 | CB | ILE | B | 146 | -18.060 | -29.125 | 88.771 | 1.00 | 46.40 |
| 6888 | CG1 | ILE | B | 146 | -18.833 | -28.147 | 89.671 | 1.00 | 45.78 |
| 6889 | CD1 | ILE | B | 146 | -18.561 | -28.314 | 91.151 | 1.00 | 44.16 |
| 6890 | CG2 | ILE | B | 146 | -16.566 | -28.900 | 88.811 | 1.00 | 45.32 |
| 6891 | C | ILE | B | 146 | -17.921 | -30.080 | 86.460 | 1.00 | 47.16 |
| 6892 | O | ILE | B | 146 | -18.187 | -31.264 | 86.609 | 1.00 | 47.27 |
| 6893 | N | TYR | B | 147 | -17.072 | -29.632 | 85.550 | 1.00 | 48.10 |
| 6894 | CA | TYR | B | 147 | -16.373 | -30.529 | 84.655 | 1.00 | 49.27 |
| 6895 | CB | TYR | B | 147 | -16.543 | -30.057 | 83.207 | 1.00 | 49.41 |
| 6896 | CG | TYR | B | 147 | -16.012 | -31.006 | 82.156 | 1.00 | 49.74 |
| 6897 | CD1 | TYR | B | 147 | -16.617 | -32.232 | 81.928 | 1.00 | 50.27 |
| 6898 | CE1 | TYR | B | 147 | -16.143 | -33.098 | 80.968 | 1.00 | 50.21 |
| 6899 | CZ | TYR | B | 147 | -15.052 | -32.742 | 80.213 | 1.00 | 50.72 |
| 6900 | OH | TYR | B | 147 | -14.575 | -33.604 | 79.255 | 1.00 | 51.51 |
| 6901 | CE2 | TYR | B | 147 | -14.435 | -31.529 | 80.410 | 1.00 | 51.16 |
| 6902 | CD2 | TYR | B | 147 | -14.917 | -30.667 | 81.380 | 1.00 | 50.92 |
| 6903 | C | TYR | B | 147 | -14.902 | -30.554 | 85.023 | 1.00 | 50.04 |
| 6904 | O | TYR | B | 147 | -14.260 | -29.504 | 85.144 | 1.00 | 49.43 |
| 6905 | N | ASP | B | 148 | -14.382 | -31.762 | 85.217 | 1.00 | 51.21 |
| 6906 | CA | ASP | B | 148 | -12.966 | -31.953 | 85.498 | 1.00 | 52.87 |
| 6907 | CB | ASP | B | 148 | -12.739 | -33.336 | 86.108 | 1.00 | 53.03 |
| 6908 | CG | ASP | B | 148 | -11.404 | -33.455 | 86.801 | 1.00 | 52.86 |
| 6909 | OD1 | ASP | B | 148 | -10.387 | -33.066 | 86.185 | 1.00 | 52.39 |
| 6910 | OD2 | ASP | B | 148 | -11.276 | -33.931 | 87.953 | 1.00 | 52.82 |
| 6911 | C | ASP | B | 148 | -12.228 | -31.823 | 84.170 | 1.00 | 53.82 |
| 6912 | O | ASP | B | 148 | -12.520 | -32.564 | 83.241 | 1.00 | 54.01 |
| 6913 | N | LEU | B | 149 | -11.296 | -30.878 | 84.071 | 1.00 | 55.10 |
| 6914 | CA | LEU | B | 149 | -10.588 | -30.636 | 82.813 | 1.00 | 56.51 |
| 6915 | CB | LEU | B | 149 | -9.883 | -29.279 | 82.828 | 1.00 | 56.48 |
| 6916 | CG | LEU | B | 149 | -10.773 | -28.033 | 82.785 | 1.00 | 56.39 |
| 6917 | CD1 | LEU | B | 149 | -11.350 | -27.840 | 81.411 | 1.00 | 55.96 |
| 6918 | CD2 | LEU | B | 149 | -9.981 | -26.811 | 83.194 | 1.00 | 56.60 |
| 6919 | C | LEU | B | 149 | -9.580 | -31.711 | 82.450 | 1.00 | 57.82 |
| 6920 | O | LEU | B | 149 | -9.385 | -32.009 | 81.270 | 1.00 | 58.49 |
| 6921 | N | ASN | B | 150 | -8.918 | -32.280 | 83.451 | 1.00 | 59.18 |
| 6922 | CA | ASN | B | 150 | -7.915 | -33.303 | 83.172 | 1.00 | 60.19 |
| 6923 | CB | ASN | B | 150 | -6.714 | -33.190 | 84.117 | 1.00 | 60.53 |
| 6924 | CG | ASN | B | 150 | -5.614 | -32.284 | 83.556 | 1.00 | 62.30 |
| 6925 | OD1 | ASN | B | 150 | -4.745 | -32.736 | 82.791 | 1.00 | 62.20 |
| 6926 | ND2 | ASN | B | 150 | -5.649 | -30.997 | 83.930 | 1.00 | 63.29 |

FIGURE 3 EF

| A | B | C | D | E | F | G | H | I | J |
|---|---|---|---|---|---|---|---|---|---|
| 6927 | C | ASN | B | 112 | -8.495 | -34.715 | 83.115 | 1.00 | 60.34 |
| 6928 | O | ASN | B | 112 | -8.107 | -35.511 | 82.264 | 1.00 | 60.68 |
| 6929 | N | LYS | B | 113 | -9.423 | -35.035 | 84.008 | 1.00 | 60.48 |
| 6930 | CA | LYS | B | 113 | -10.118 | -36.313 | 83.905 | 1.00 | 60.64 |
| 6931 | CB | LYS | B | 113 | -10.844 | -36.657 | 85.205 | 1.00 | 60.83 |
| 6932 | CG | LYS | B | 113 | -10.004 | -37.066 | 86.413 | 1.00 | 62.13 |
| 6933 | CD | LYS | B | 113 | -10.942 | -37.688 | 87.465 | 1.00 | 64.05 |
| 6934 | CE | LYS | B | 113 | -10.416 | -37.589 | 88.902 | 1.00 | 66.34 |
| 6935 | NZ | LYS | B | 113 | -9.645 | -38.801 | 89.354 | 1.00 | 67.59 |
| 6936 | C | LYS | B | 113 | -11.191 | -36.148 | 82.832 | 1.00 | 60.46 |
| 6937 | O | LYS | B | 113 | -11.993 | -37.053 | 82.601 | 1.00 | 60.41 |
| 6938 | N | ARG | B | 114 | -11.190 | -34.995 | 82.165 | 1.00 | 60.17 |
| 6939 | CA | ARG | B | 114 | -12.316 | -34.606 | 81.314 | 1.00 | 60.11 |
| 6940 | CB | ARG | B | 114 | -11.994 | -34.453 | 79.816 | 1.00 | 60.21 |
| 6941 | CG | ARG | B | 114 | -10.813 | -35.185 | 79.235 | 1.00 | 61.19 |
| 6942 | CD | ARG | B | 114 | -10.360 | -34.544 | 77.918 | 1.00 | 62.98 |
| 6943 | NE | ARG | B | 114 | -11.468 | -33.807 | 77.302 | 1.00 | 64.76 |
| 6944 | CZ | ARG | B | 114 | -11.630 | -32.481 | 77.350 | 1.00 | 65.35 |
| 6945 | NH1 | ARG | B | 114 | -10.744 | -31.708 | 77.969 | 1.00 | 66.06 |
| 6946 | NH2 | ARG | B | 114 | -12.685 | -31.923 | 76.771 | 1.00 | 64.96 |
| 6947 | C | ARG | B | 114 | -13.610 | -35.388 | 81.568 | 1.00 | 59.77 |
| 6948 | O | ARG | B | 114 | -14.127 | -36.073 | 80.692 | 1.00 | 59.60 |
| 6949 | N | GLN | B | 115 | -14.136 | -35.246 | 82.780 | 1.00 | 59.44 |
| 6950 | CA | GLN | B | 115 | -15.370 | -35.914 | 83.165 | 1.00 | 59.28 |
| 6951 | CB | GLN | B | 115 | -15.078 | -37.228 | 83.892 | 1.00 | 59.10 |
| 6952 | CG | GLN | B | 115 | -15.056 | -38.431 | 82.967 | 1.00 | 59.99 |
| 6953 | CD | GLN | B | 115 | -14.836 | -39.744 | 83.704 | 1.00 | 60.27 |
| 6954 | OE1 | GLN | B | 115 | -14.169 | -39.776 | 84.747 | 1.00 | 58.63 |
| 6955 | NE2 | GLN | B | 115 | -15.394 | -40.829 | 83.164 | 1.00 | 60.16 |
| 6956 | C | GLN | B | 115 | -16.287 | -35.036 | 84.009 | 1.00 | 58.99 |
| 6957 | O | GLN | B | 115 | -15.839 | -34.154 | 84.739 | 1.00 | 59.02 |
| 6958 | N | LEU | B | 116 | -17.581 | -35.297 | 83.903 | 1.00 | 58.68 |
| 6959 | CA | LEU | B | 116 | -18.575 | -34.542 | 84.632 | 1.00 | 58.46 |
| 6960 | CB | LEU | B | 116 | -19.923 | -34.710 | 83.942 | 1.00 | 58.33 |
| 6961 | CG | LEU | B | 116 | -20.862 | -33.510 | 83.813 | 1.00 | 58.73 |
| 6962 | CD1 | LEU | B | 116 | -21.899 | -33.821 | 82.741 | 1.00 | 57.81 |
| 6963 | CD2 | LEU | B | 116 | -20.089 | -32.234 | 83.466 | 1.00 | 57.82 |
| 6964 | C | LEU | B | 116 | -18.666 | -35.070 | 86.054 | 1.00 | 58.39 |
| 6965 | O | LEU | B | 116 | -19.117 | -36.195 | 86.274 | 1.00 | 58.73 |
| 6966 | N | ILE | B | 117 | -18.229 | -34.293 | 87.032 | 1.00 | 57.82 |
| 6967 | CA | ILE | B | 117 | -18.391 | -34.772 | 88.391 | 1.00 | 57.41 |
| 6968 | CB | ILE | B | 117 | -18.017 | -33.702 | 89.414 | 1.00 | 57.29 |
| 6969 | CG1 | ILE | B | 117 | -16.519 | -33.757 | 89.702 | 1.00 | 57.24 |
| 6970 | CD1 | ILE | B | 117 | -15.655 | -33.406 | 88.533 | 1.00 | 56.98 |
| 6971 | CG2 | ILE | B | 117 | -18.786 | -33.919 | 90.706 | 1.00 | 56.69 |
| 6972 | C | ILE | B | 117 | -19.858 | -35.143 | 88.508 | 1.00 | 57.25 |
| 6973 | O | ILE | B | 117 | -20.719 | -34.360 | 88.128 | 1.00 | 57.34 |
| 6974 | N | THR | B | 118 | -20.147 | -36.348 | 88.989 | 1.00 | 57.01 |
| 6975 | CA | THR | B | 118 | -21.532 | -36.788 | 89.134 | 1.00 | 56.55 |
| 6976 | CB | THR | B | 118 | -21.791 | -38.055 | 88.312 | 1.00 | 56.71 |
| 6977 | OG1 | THR | B | 118 | -20.921 | -39.100 | 88.771 | 1.00 | 56.05 |

FIGURE 3 EG

| A | B | C | D | E | F | G | H | I | J |
|---|---|---|---|---|---|---|---|---|---|
| 6978 | CG2 | THR | B | 118 | -21.387 | -37.839 | 86.857 | 1.00 | 56.38 |
| 6979 | C | THR | B | 118 | -21.827 | -37.078 | 90.586 | 1.00 | 56.40 |
| 6980 | O | THR | B | 118 | -22.859 | -37.649 | 90.926 | 1.00 | 56.71 |
| 6981 | N | GLU | B | 119 | -20.902 | -36.694 | 91.448 | 1.00 | 56.00 |
| 6982 | CA | GLU | B | 119 | -21.063 | -36.923 | 92.868 | 1.00 | 55.83 |
| 6983 | CB | GLU | B | 119 | -19.891 | -37.765 | 93.396 | 1.00 | 56.17 |
| 6984 | CG | GLU | B | 119 | -19.526 | -38.945 | 92.500 | 1.00 | 57.93 |
| 6985 | CD | GLU | B | 119 | -18.218 | -39.614 | 92.891 | 1.00 | 60.54 |
| 6986 | OE1 | GLU | B | 119 | -17.174 | -38.922 | 92.958 | 1.00 | 60.51 |
| 6987 | OE2 | GLU | B | 119 | -18.233 | -40.844 | 93.130 | 1.00 | 62.65 |
| 6988 | C | GLU | B | 119 | -21.108 | -35.570 | 93.569 | 1.00 | 55.02 |
| 6989 | O | GLU | B | 119 | -20.341 | -34.673 | 93.240 | 1.00 | 54.89 |
| 6990 | N | GLU | B | 120 | -22.021 | -35.419 | 94.517 | 1.00 | 54.26 |
| 6991 | CA | GLU | B | 120 | -22.074 | -34.198 | 95.304 | 1.00 | 53.96 |
| 6992 | CB | GLU | B | 120 | -20.765 | -34.036 | 96.075 | 1.00 | 54.29 |
| 6993 | CG | GLU | B | 120 | -20.763 | -34.643 | 97.469 | 1.00 | 56.02 |
| 6994 | CD | GLU | B | 120 | -22.065 | -35.326 | 97.851 | 1.00 | 58.53 |
| 6995 | OE1 | GLU | B | 120 | -22.027 | -36.523 | 98.226 | 1.00 | 58.50 |
| 6996 | OE2 | GLU | B | 120 | -23.129 | -34.659 | 97.806 | 1.00 | 59.72 |
| 6997 | C | GLU | B | 120 | -22.325 | -32.967 | 94.441 | 1.00 | 52.94 |
| 6998 | O | GLU | B | 120 | -21.706 | -31.922 | 94.634 | 1.00 | 53.11 |
| 6999 | N | ARG | B | 121 | -23.241 | -33.105 | 93.494 | 1.00 | 51.55 |
| 7000 | CA | ARG | B | 121 | -23.581 | -32.028 | 92.581 | 1.00 | 50.21 |
| 7001 | CB | ARG | B | 121 | -24.596 | -32.536 | 91.547 | 1.00 | 50.55 |
| 7002 | CG | ARG | B | 121 | -24.025 | -33.534 | 90.533 | 1.00 | 51.61 |
| 7003 | CD | ARG | B | 121 | -25.071 | -34.250 | 89.676 | 1.00 | 52.90 |
| 7004 | NE | ARG | B | 121 | -25.728 | -33.354 | 88.726 | 1.00 | 54.69 |
| 7005 | CZ | ARG | B | 121 | -26.849 | -33.649 | 88.072 | 1.00 | 55.41 |
| 7006 | NH1 | ARG | B | 121 | -27.442 | -34.821 | 88.261 | 1.00 | 56.17 |
| 7007 | NH2 | ARG | B | 121 | -27.383 | -32.774 | 87.229 | 1.00 | 55.38 |
| 7008 | C | ARG | B | 121 | -24.147 | -30.810 | 93.305 | 1.00 | 48.76 |
| 7009 | O | ARG | B | 121 | -24.804 | -30.932 | 94.329 | 1.00 | 48.32 |
| 7010 | N | ILE | B | 122 | -23.877 | -29.633 | 92.758 | 1.00 | 47.49 |
| 7011 | CA | ILE | B | 122 | -24.439 | -28.393 | 93.269 | 1.00 | 46.10 |
| 7012 | CB | ILE | B | 122 | -23.831 | -27.210 | 92.510 | 1.00 | 46.08 |
| 7013 | CG1 | ILE | B | 122 | -22.351 | -27.091 | 92.871 | 1.00 | 44.41 |
| 7014 | CD1 | ILE | B | 122 | -21.581 | -26.147 | 92.013 | 1.00 | 43.82 |
| 7015 | CG2 | ILE | B | 122 | -24.581 | -25.917 | 92.815 | 1.00 | 45.57 |
| 7016 | C | ILE | B | 122 | -25.942 | -28.472 | 93.058 | 1.00 | 45.48 |
| 7017 | O | ILE | B | 122 | -26.392 | -28.918 | 92.018 | 1.00 | 45.33 |
| 7018 | N | PRO | B | 123 | -26.725 | -28.056 | 94.044 | 1.00 | 45.04 |
| 7019 | CA | PRO | B | 123 | -28.186 | -28.200 | 93.968 | 1.00 | 44.70 |
| 7020 | CB | PRO | B | 123 | -28.668 | -27.694 | 95.333 | 1.00 | 44.69 |
| 7021 | CG | PRO | B | 123 | -27.444 | -27.543 | 96.176 | 1.00 | 44.44 |
| 7022 | CD | PRO | B | 123 | -26.281 | -27.390 | 95.277 | 1.00 | 44.63 |
| 7023 | C | PRO | B | 123 | -28.804 | -27.345 | 92.869 | 1.00 | 44.69 |
| 7024 | O | PRO | B | 123 | -28.191 | -26.384 | 92.411 | 1.00 | 44.61 |
| 7025 | N | ASN | B | 124 | -30.005 | -27.718 | 92.444 | 1.00 | 44.83 |
| 7026 | CA | ASN | B | 124 | -30.756 | -26.949 | 91.464 | 1.00 | 44.83 |
| 7027 | CB | ASN | B | 124 | -31.930 | -27.771 | 90.895 | 1.00 | 45.24 |
| 7028 | CG | ASN | B | 124 | -31.488 | -28.820 | 89.852 | 1.00 | 46.78 |

FIGURE 3 EH

| A | B | C | D | E | F | G | H | I | J |
|---|---|---|---|---|---|---|---|---|---|
| 7029 | OD1 | ASN | B | 124 | -30.545 | -28.609 | 89.086 | 1.00 | 46.82 |
| 7030 | ND2 | ASN | B | 124 | -32.183 | -29.951 | 89.826 | 1.00 | 51.91 |
| 7031 | C | ASN | B | 124 | -31.267 | -25.709 | 92.195 | 1.00 | 44.27 |
| 7032 | O | ASN | B | 124 | -31.258 | -25.674 | 93.435 | 1.00 | 44.24 |
| 7033 | N | ASN | B | 125 | -31.707 | -24.700 | 91.443 | 1.00 | 42.84 |
| 7034 | CA | ASN | B | 125 | -32.204 | -23.463 | 92.038 | 1.00 | 41.49 |
| 7035 | CB | ASN | B | 125 | -33.499 | -23.695 | 92.826 | 1.00 | 41.55 |
| 7036 | CG | ASN | B | 125 | -34.585 | -24.378 | 91.988 | 1.00 | 42.05 |
| 7037 | OD1 | ASN | B | 125 | -34.849 | -25.575 | 92.150 | 1.00 | 41.18 |
| 7038 | ND2 | ASN | B | 125 | -35.223 | -23.615 | 91.100 | 1.00 | 40.95 |
| 7039 | C | ASN | B | 125 | -31.160 | -22.801 | 92.926 | 1.00 | 40.69 |
| 7040 | O | ASN | B | 125 | -31.486 | -22.187 | 93.946 | 1.00 | 40.65 |
| 7041 | N | THR | B | 126 | -29.900 | -22.936 | 92.532 | 1.00 | 39.37 |
| 7042 | CA | THR | B | 126 | -28.803 | -22.297 | 93.234 | 1.00 | 37.95 |
| 7043 | CB | THR | B | 126 | -27.470 | -22.964 | 92.857 | 1.00 | 37.98 |
| 7044 | OG1 | THR | B | 126 | -27.427 | -24.281 | 93.425 | 1.00 | 38.33 |
| 7045 | CG2 | THR | B | 126 | -26.287 | -22.245 | 93.495 | 1.00 | 36.03 |
| 7046 | C | THR | B | 126 | -28.788 | -20.811 | 92.888 | 1.00 | 37.31 |
| 7047 | O | THR | B | 126 | -28.852 | -20.425 | 91.721 | 1.00 | 37.04 |
| 7048 | N | GLN | B | 127 | -28.688 | -19.988 | 93.922 | 1.00 | 36.34 |
| 7049 | CA | GLN | B | 127 | -28.750 | -18.553 | 93.786 | 1.00 | 34.92 |
| 7050 | CB | GLN | B | 127 | -29.300 | -17.967 | 95.080 | 1.00 | 34.94 |
| 7051 | CG | GLN | B | 127 | -30.650 | -18.559 | 95.437 | 1.00 | 33.55 |
| 7052 | CD | GLN | B | 127 | -30.989 | -18.453 | 96.916 | 1.00 | 32.92 |
| 7053 | OE1 | GLN | B | 127 | -30.300 | -19.048 | 97.761 | 1.00 | 31.14 |
| 7054 | NE2 | GLN | B | 127 | -32.066 | -17.725 | 97.232 | 1.00 | 26.86 |
| 7055 | C | GLN | B | 127 | -27.435 | -17.907 | 93.400 | 1.00 | 35.02 |
| 7056 | O | GLN | B | 127 | -27.420 | -16.786 | 92.882 | 1.00 | 35.11 |
| 7057 | N | TRP | B | 128 | -26.328 | -18.606 | 93.607 | 1.00 | 34.94 |
| 7058 | CA | TRP | B | 128 | -25.023 | -18.019 | 93.295 | 1.00 | 34.86 |
| 7059 | CB | TRP | B | 128 | -24.850 | -16.732 | 94.091 | 1.00 | 34.91 |
| 7060 | CG | TRP | B | 128 | -23.622 | -16.029 | 93.737 | 1.00 | 36.11 |
| 7061 | CD1 | TRP | B | 128 | -22.448 | -16.054 | 94.420 | 1.00 | 37.36 |
| 7062 | NE1 | TRP | B | 128 | -21.512 | -15.288 | 93.768 | 1.00 | 39.73 |
| 7063 | CE2 | TRP | B | 128 | -22.077 | -14.756 | 92.640 | 1.00 | 37.82 |
| 7064 | CD2 | TRP | B | 128 | -23.406 | -15.204 | 92.589 | 1.00 | 36.92 |
| 7065 | CE3 | TRP | B | 128 | -24.204 | -14.796 | 91.522 | 1.00 | 37.01 |
| 7066 | CZ3 | TRP | B | 128 | -23.664 | -13.971 | 90.566 | 1.00 | 37.97 |
| 7067 | CH2 | TRP | B | 128 | -22.337 | -13.547 | 90.642 | 1.00 | 38.55 |
| 7068 | CZ2 | TRP | B | 128 | -21.529 | -13.923 | 91.673 | 1.00 | 38.95 |
| 7069 | C | TRP | B | 128 | -23.831 | -18.947 | 93.580 | 1.00 | 34.89 |
| 7070 | O | TRP | B | 128 | -23.821 | -19.684 | 94.556 | 1.00 | 34.10 |
| 7071 | N | VAL | B | 129 | -22.814 | -18.878 | 92.735 | 1.00 | 35.22 |
| 7072 | CA | VAL | B | 129 | -21.641 | -19.718 | 92.894 | 1.00 | 36.27 |
| 7073 | CB | VAL | B | 129 | -21.650 | -20.924 | 91.923 | 1.00 | 36.44 |
| 7074 | CG1 | VAL | B | 129 | -22.979 | -21.647 | 91.958 | 1.00 | 35.53 |
| 7075 | CG2 | VAL | B | 129 | -20.506 | -21.876 | 92.259 | 1.00 | 36.07 |
| 7076 | C | VAL | B | 129 | -20.397 | -18.930 | 92.570 | 1.00 | 36.85 |
| 7077 | O | VAL | B | 129 | -20.363 | -18.203 | 91.590 | 1.00 | 36.67 |
| 7078 | N | THR | B | 130 | -19.365 | -19.070 | 93.391 | 1.00 | 38.07 |
| 7079 | CA | THR | B | 130 | -18.110 | -18.405 | 93.097 | 1.00 | 39.09 |

FIGURE 3 EI

| A | B | C | D | E | F | G | H | I | J |
|---|---|---|---|---|---|---|---|---|---|
| 7080 | CB | THR | B | 130 | -18.055 | -16.988 | 93.726 | 1.00 | 39.16 |
| 7081 | OG1 | THR | B | 130 | -16.698 | -16.512 | 93.767 | 1.00 | 39.50 |
| 7082 | CG2 | THR | B | 130 | -18.459 | -17.029 | 95.170 | 1.00 | 38.85 |
| 7083 | C | THR | B | 130 | -16.925 | -19.254 | 93.529 | 1.00 | 40.29 |
| 7084 | O | THR | B | 130 | -16.907 | -19.819 | 94.619 | 1.00 | 39.97 |
| 7085 | N | TRP | B | 131 | -15.949 | -19.351 | 92.633 | 1.00 | 41.63 |
| 7086 | CA | TRP | B | 131 | -14.710 | -20.056 | 92.894 | 1.00 | 42.33 |
| 7087 | CB | TRP | B | 131 | -13.844 | -20.063 | 91.629 | 1.00 | 42.18 |
| 7088 | CG | TRP | B | 131 | -14.321 | -20.989 | 90.566 | 1.00 | 42.06 |
| 7089 | CD1 | TRP | B | 131 | -14.758 | -20.654 | 89.322 | 1.00 | 41.70 |
| 7090 | NE1 | TRP | B | 131 | -15.122 | -21.782 | 88.630 | 1.00 | 41.69 |
| 7091 | CE2 | TRP | B | 131 | -14.902 | -22.880 | 89.423 | 1.00 | 40.84 |
| 7092 | CD2 | TRP | B | 131 | -14.399 | -22.415 | 90.650 | 1.00 | 40.74 |
| 7093 | CE3 | TRP | B | 131 | -14.093 | -23.348 | 91.644 | 1.00 | 39.43 |
| 7094 | CZ3 | TRP | B | 131 | -14.306 | -24.676 | 91.393 | 1.00 | 40.01 |
| 7095 | CH2 | TRP | B | 131 | -14.812 | -25.108 | 90.157 | 1.00 | 39.68 |
| 7096 | CZ2 | TRP | B | 131 | -15.112 | -24.226 | 89.164 | 1.00 | 38.53 |
| 7097 | C | TRP | B | 131 | -13.941 | -19.286 | 93.944 | 1.00 | 43.25 |
| 7098 | O | TRP | B | 131 | -14.234 | -18.124 | 94.224 | 1.00 | 43.84 |
| 7099 | N | SER | B | 132 | -12.945 | -19.947 | 94.513 | 1.00 | 43.68 |
| 7100 | CA | SER | B | 132 | -11.971 | -19.320 | 95.379 | 1.00 | 44.11 |
| 7101 | CB | SER | B | 132 | -11.098 | -20.425 | 95.960 | 1.00 | 44.06 |
| 7102 | OG | SER | B | 132 | -10.138 | -19.911 | 96.860 | 1.00 | 47.01 |
| 7103 | C | SER | B | 132 | -11.143 | -18.457 | 94.431 | 1.00 | 43.83 |
| 7104 | O | SER | B | 132 | -11.057 | -18.779 | 93.257 | 1.00 | 44.43 |
| 7105 | N | PRO | B | 133 | -10.527 | -17.374 | 94.887 | 1.00 | 43.67 |
| 7106 | CA | PRO | B | 133 | -9.717 | -16.553 | 93.985 | 1.00 | 43.66 |
| 7107 | CB | PRO | B | 133 | -9.345 | -15.348 | 94.850 | 1.00 | 43.91 |
| 7108 | CG | PRO | B | 133 | -10.322 | -15.376 | 95.955 | 1.00 | 43.41 |
| 7109 | CD | PRO | B | 133 | -10.555 | -16.824 | 96.247 | 1.00 | 43.61 |
| 7110 | C | PRO | B | 133 | -8.459 | -17.285 | 93.519 | 1.00 | 43.78 |
| 7111 | O | PRO | B | 133 | -7.808 | -16.837 | 92.583 | 1.00 | 43.86 |
| 7112 | N | VAL | B | 134 | -8.114 | -18.380 | 94.186 | 1.00 | 43.75 |
| 7113 | CA | VAL | B | 134 | -6.991 | -19.217 | 93.789 | 1.00 | 43.61 |
| 7114 | CB | VAL | B | 134 | -5.730 | -18.897 | 94.583 | 1.00 | 43.86 |
| 7115 | CG1 | VAL | B | 134 | -5.211 | -17.508 | 94.250 | 1.00 | 44.28 |
| 7116 | CG2 | VAL | B | 134 | -6.005 | -19.016 | 96.067 | 1.00 | 44.26 |
| 7117 | C | VAL | B | 134 | -7.381 | -20.653 | 94.072 | 1.00 | 43.56 |
| 7118 | O | VAL | B | 134 | -8.178 | -20.909 | 94.967 | 1.00 | 43.88 |
| 7119 | N | GLY | B | 135 | -6.834 | -21.597 | 93.314 | 1.00 | 43.50 |
| 7120 | CA | GLY | B | 135 | -7.178 | -22.990 | 93.506 | 1.00 | 42.57 |
| 7121 | C | GLY | B | 135 | -8.539 | -23.284 | 92.907 | 1.00 | 42.42 |
| 7122 | O | GLY | B | 135 | -8.846 | -22.832 | 91.806 | 1.00 | 42.51 |
| 7123 | N | HIS | B | 136 | -9.371 | -24.031 | 93.623 | 1.00 | 41.88 |
| 7124 | CA | HIS | B | 136 | -10.669 | -24.399 | 93.083 | 1.00 | 41.28 |
| 7125 | CB | HIS | B | 136 | -10.556 | -25.635 | 92.205 | 1.00 | 41.09 |
| 7126 | CG | HIS | B | 136 | -9.837 | -26.762 | 92.865 | 1.00 | 41.42 |
| 7127 | ND1 | HIS | B | 136 | -8.475 | -26.936 | 92.756 | 1.00 | 41.80 |
| 7128 | CE1 | HIS | B | 136 | -8.113 | -27.995 | 93.457 | 1.00 | 43.07 |
| 7129 | NE2 | HIS | B | 136 | -9.188 | -28.501 | 94.034 | 1.00 | 42.44 |
| 7130 | CD2 | HIS | B | 136 | -10.280 | -27.747 | 93.680 | 1.00 | 41.18 |

FIGURE 3 EJ

| A | B | C | D | E | F | G | H | I | J |
|---|---|---|---|---|---|---|---|---|---|
| 7131 | C | HIS | B | 136 | -11.668 | -24.674 | 94.168 | 1.00 | 41.24 |
| 7132 | O | HIS | B | 136 | -12.519 | -25.568 | 94.030 | 1.00 | 41.24 |
| 7133 | N | LYS | B | 137 | -11.558 | -23.930 | 95.262 | 1.00 | 41.14 |
| 7134 | CA | LYS | B | 137 | -12.547 | -24.032 | 96.320 | 1.00 | 41.09 |
| 7135 | CB | LYS | B | 137 | -12.096 | -23.305 | 97.583 | 1.00 | 41.89 |
| 7136 | CG | LYS | B | 137 | -11.586 | -24.250 | 98.657 | 1.00 | 43.47 |
| 7137 | CD | LYS | B | 137 | -10.276 | -23.772 | 99.244 | 1.00 | 46.36 |
| 7138 | CE | LYS | B | 137 | -10.460 | -22.700 | 100.280 | 1.00 | 48.20 |
| 7139 | NZ | LYS | B | 137 | -9.125 | -22.281 | 100.849 | 1.00 | 48.67 |
| 7140 | C | LYS | B | 137 | -13.805 | -23.420 | 95.762 | 1.00 | 40.13 |
| 7141 | O | LYS | B | 137 | -13.753 | -22.688 | 94.789 | 1.00 | 39.54 |
| 7142 | N | LEU | B | 138 | -14.928 | -23.702 | 96.401 | 1.00 | 39.56 |
| 7143 | CA | LEU | B | 138 | -16.208 | -23.294 | 95.882 | 1.00 | 38.74 |
| 7144 | CB | LEU | B | 138 | -16.834 | -24.522 | 95.237 | 1.00 | 39.10 |
| 7145 | CG | LEU | B | 138 | -17.667 | -24.421 | 93.977 | 1.00 | 38.93 |
| 7146 | CD1 | LEU | B | 138 | -17.088 | -23.365 | 93.050 | 1.00 | 38.82 |
| 7147 | CD2 | LEU | B | 138 | -17.641 | -25.774 | 93.319 | 1.00 | 38.89 |
| 7148 | C | LEU | B | 138 | -17.163 | -22.812 | 96.960 | 1.00 | 38.21 |
| 7149 | O | LEU | B | 138 | -17.330 | -23.470 | 97.984 | 1.00 | 38.26 |
| 7150 | N | ALA | B | 139 | -17.811 | -21.678 | 96.721 | 1.00 | 37.04 |
| 7151 | CA | ALA | B | 139 | -18.859 | -21.213 | 97.619 | 1.00 | 36.37 |
| 7152 | CB | ALA | B | 139 | -18.436 | -19.952 | 98.361 | 1.00 | 36.36 |
| 7153 | C | ALA | B | 139 | -20.131 | -20.948 | 96.819 | 1.00 | 36.06 |
| 7154 | O | ALA | B | 139 | -20.096 | -20.375 | 95.729 | 1.00 | 35.33 |
| 7155 | N | TYR | B | 140 | -21.259 | -21.370 | 97.360 | 1.00 | 35.69 |
| 7156 | CA | TYR | B | 140 | -22.506 | -21.084 | 96.698 | 1.00 | 35.56 |
| 7157 | CB | TYR | B | 140 | -22.873 | -22.217 | 95.734 | 1.00 | 35.62 |
| 7158 | CG | TYR | B | 140 | -23.103 | -23.556 | 96.382 | 1.00 | 35.36 |
| 7159 | CD1 | TYR | B | 140 | -24.330 | -23.875 | 96.914 | 1.00 | 34.83 |
| 7160 | CE1 | TYR | B | 140 | -24.558 | -25.095 | 97.495 | 1.00 | 35.07 |
| 7161 | CZ | TYR | B | 140 | -23.549 | -26.024 | 97.562 | 1.00 | 34.69 |
| 7162 | OH | TYR | B | 140 | -23.814 | -27.241 | 98.153 | 1.00 | 35.30 |
| 7163 | CE2 | TYR | B | 140 | -22.312 | -25.741 | 97.043 | 1.00 | 34.31 |
| 7164 | CD2 | TYR | B | 140 | -22.090 | -24.512 | 96.448 | 1.00 | 35.31 |
| 7165 | C | TYR | B | 140 | -23.604 | -20.800 | 97.718 | 1.00 | 35.80 |
| 7166 | O | TYR | B | 140 | -23.451 | -21.080 | 98.909 | 1.00 | 36.15 |
| 7167 | N | VAL | B | 141 | -24.685 | -20.189 | 97.256 | 1.00 | 35.67 |
| 7168 | CA | VAL | B | 141 | -25.833 | -19.930 | 98.099 | 1.00 | 35.40 |
| 7169 | CB | VAL | B | 141 | -26.234 | -18.454 | 98.082 | 1.00 | 35.38 |
| 7170 | CG1 | VAL | B | 141 | -25.072 | -17.591 | 98.465 | 1.00 | 33.53 |
| 7171 | CG2 | VAL | B | 141 | -27.423 | -18.215 | 99.009 | 1.00 | 35.48 |
| 7172 | C | VAL | B | 141 | -26.995 | -20.732 | 97.558 | 1.00 | 35.92 |
| 7173 | O | VAL | B | 141 | -27.207 | -20.794 | 96.351 | 1.00 | 35.98 |
| 7174 | N | TRP | B | 142 | -27.757 | -21.342 | 98.446 | 1.00 | 36.11 |
| 7175 | CA | TRP | B | 142 | -28.895 | -22.119 | 98.019 | 1.00 | 37.00 |
| 7176 | CB | TRP | B | 142 | -28.480 | -23.562 | 97.725 | 1.00 | 37.45 |
| 7177 | CG | TRP | B | 142 | -29.609 | -24.447 | 97.413 | 1.00 | 37.97 |
| 7178 | CD1 | TRP | B | 142 | -30.222 | -24.594 | 96.201 | 1.00 | 38.04 |
| 7179 | NE1 | TRP | B | 142 | -31.229 | -25.526 | 96.292 | 1.00 | 38.64 |
| 7180 | CE2 | TRP | B | 142 | -31.290 | -25.991 | 97.583 | 1.00 | 39.67 |
| 7181 | CD2 | TRP | B | 142 | -30.279 | -25.330 | 98.315 | 1.00 | 38.37 |

FIGURE 3 EK

| A | B | C | D | E | F | G | H | I | J |
|---|---|---|---|---|---|---|---|---|---|
| 7182 | CE3 | TRP | B | 142 | -30.124 | -25.638 | 99.669 | 1.00 | 39.69 |
| 7183 | CZ3 | TRP | B | 142 | -30.976 | -26.576 | 100.252 | 1.00 | 40.58 |
| 7184 | CH2 | TRP | B | 142 | -31.974 | -27.217 | 99.495 | 1.00 | 41.69 |
| 7185 | CZ2 | TRP | B | 142 | -32.148 | -26.935 | 98.162 | 1.00 | 40.31 |
| 7186 | C | TRP | B | 142 | -29.908 | -22.061 | 99.135 | 1.00 | 37.18 |
| 7187 | O | TRP | B | 142 | -29.584 | -22.362 | 100.293 | 1.00 | 37.62 |
| 7188 | N | ASN | B | 143 | -31.123 | -21.653 | 98.786 | 1.00 | 37.09 |
| 7189 | CA | ASN | B | 143 | -32.174 | -21.440 | 99.760 | 1.00 | 37.10 |
| 7190 | CB | ASN | B | 143 | -32.571 | -22.744 | 100.448 | 1.00 | 37.49 |
| 7191 | CG | ASN | B | 143 | -33.440 | -23.631 | 99.568 | 1.00 | 39.31 |
| 7192 | OD1 | ASN | B | 143 | -33.526 | -24.843 | 99.785 | 1.00 | 42.68 |
| 7193 | ND2 | ASN | B | 143 | -34.098 | -23.032 | 98.577 | 1.00 | 39.54 |
| 7194 | C | ASN | B | 143 | -31.722 | -20.398 | 100.773 | 1.00 | 36.82 |
| 7195 | O | ASN | B | 143 | -32.004 | -20.504 | 101.960 | 1.00 | 36.76 |
| 7196 | N | ASN | B | 144 | -31.021 | -19.387 | 100.277 | 1.00 | 36.79 |
| 7197 | CA | ASN | B | 144 | -30.531 | -18.280 | 101.093 | 1.00 | 37.18 |
| 7198 | CB | ASN | B | 144 | -31.686 | -17.568 | 101.805 | 1.00 | 37.04 |
| 7199 | CG | ASN | B | 144 | -32.527 | -16.720 | 100.861 | 1.00 | 36.49 |
| 7200 | OD1 | ASN | B | 144 | -32.660 | -17.030 | 99.683 | 1.00 | 36.40 |
| 7201 | ND2 | ASN | B | 144 | -33.097 | -15.648 | 101.384 | 1.00 | 33.59 |
| 7202 | C | ASN | B | 144 | -29.424 | -18.637 | 102.100 | 1.00 | 37.55 |
| 7203 | O | ASN | B | 144 | -29.026 | -17.798 | 102.899 | 1.00 | 38.80 |
| 7204 | N | ASP | B | 145 | -28.926 | -19.866 | 102.065 | 1.00 | 37.04 |
| 7205 | CA | ASP | B | 145 | -27.830 | -20.248 | 102.949 | 1.00 | 36.79 |
| 7206 | CB | ASP | B | 145 | -28.196 | -21.497 | 103.756 | 1.00 | 36.52 |
| 7207 | CG | ASP | B | 145 | -28.965 | -21.169 | 105.012 | 1.00 | 35.95 |
| 7208 | OD1 | ASP | B | 145 | -29.946 | -21.885 | 105.300 | 1.00 | 35.23 |
| 7209 | OD2 | ASP | B | 145 | -28.672 | -20.211 | 105.760 | 1.00 | 32.55 |
| 7210 | C | ASP | B | 145 | -26.527 | -20.488 | 102.172 | 1.00 | 36.81 |
| 7211 | O | ASP | B | 145 | -26.548 | -20.828 | 100.997 | 1.00 | 36.71 |
| 7212 | N | ILE | B | 146 | -25.398 | -20.304 | 102.843 | 1.00 | 37.17 |
| 7213 | CA | ILE | B | 146 | -24.088 | -20.514 | 102.234 | 1.00 | 37.41 |
| 7214 | CB | ILE | B | 146 | -23.088 | -19.527 | 102.804 | 1.00 | 37.34 |
| 7215 | CG1 | ILE | B | 146 | -23.598 | -18.102 | 102.588 | 1.00 | 36.66 |
| 7216 | CD1 | ILE | B | 146 | -22.768 | -17.054 | 103.237 | 1.00 | 34.03 |
| 7217 | CG2 | ILE | B | 146 | -21.717 | -19.733 | 102.183 | 1.00 | 37.74 |
| 7218 | C | ILE | B | 146 | -23.574 | -21.936 | 102.431 | 1.00 | 37.89 |
| 7219 | O | ILE | B | 146 | -23.890 | -22.610 | 103.415 | 1.00 | 37.80 |
| 7220 | N | TYR | B | 147 | -22.799 | -22.393 | 101.458 | 1.00 | 38.32 |
| 7221 | CA | TYR | B | 147 | -22.210 | -23.717 | 101.482 | 1.00 | 38.55 |
| 7222 | CB | TYR | B | 147 | -23.031 | -24.678 | 100.647 | 1.00 | 38.37 |
| 7223 | CG | TYR | B | 147 | -24.367 | -25.068 | 101.217 | 1.00 | 37.96 |
| 7224 | CD1 | TYR | B | 147 | -24.534 | -26.268 | 101.908 | 1.00 | 37.11 |
| 7225 | CE1 | TYR | B | 147 | -25.785 | -26.638 | 102.412 | 1.00 | 36.57 |
| 7226 | CZ | TYR | B | 147 | -26.874 | -25.799 | 102.213 | 1.00 | 36.57 |
| 7227 | OH | TYR | B | 147 | -28.122 | -26.146 | 102.695 | 1.00 | 38.30 |
| 7228 | CE2 | TYR | B | 147 | -26.728 | -24.622 | 101.523 | 1.00 | 34.92 |
| 7229 | CD2 | TYR | B | 147 | -25.486 | -24.265 | 101.022 | 1.00 | 37.48 |
| 7230 | C | TYR | B | 147 | -20.828 | -23.622 | 100.867 | 1.00 | 38.87 |
| 7231 | O | TYR | B | 147 | -20.585 | -22.784 | 100.002 | 1.00 | 39.06 |
| 7232 | N | VAL | B | 148 | -19.919 | -24.479 | 101.310 | 1.00 | 39.44 |

FIGURE 3 EL

| A | B | C | D | E | F | G | H | I | J |
|---|---|---|---|---|---|---|---|---|---|
| 7233 | CA | VAL | B | 148 | -18.588 | -24.488 | 100.737 | 1.00 | 39.71 |
| 7234 | CB | VAL | B | 148 | -17.509 | -24.035 | 101.718 | 1.00 | 39.96 |
| 7235 | CG1 | VAL | B | 148 | -16.147 | -24.369 | 101.142 | 1.00 | 39.51 |
| 7236 | CG2 | VAL | B | 148 | -17.633 | -22.535 | 102.015 | 1.00 | 39.81 |
| 7237 | C | VAL | B | 148 | -18.201 | -25.872 | 100.305 | 1.00 | 40.21 |
| 7238 | O | VAL | B | 148 | -18.543 | -26.857 | 100.956 | 1.00 | 40.48 |
| 7239 | N | LYS | B | 149 | -17.480 | -25.930 | 99.194 | 1.00 | 40.45 |
| 7240 | CA | LYS | B | 149 | -16.926 | -27.163 | 98.696 | 1.00 | 40.77 |
| 7241 | CB | LYS | B | 149 | -17.494 | -27.502 | 97.320 | 1.00 | 40.78 |
| 7242 | CG | LYS | B | 149 | -18.834 | -28.181 | 97.370 | 1.00 | 41.22 |
| 7243 | CD | LYS | B | 149 | -19.360 | -28.458 | 95.982 | 1.00 | 42.84 |
| 7244 | CE | LYS | B | 149 | -20.033 | -29.816 | 95.943 | 1.00 | 44.11 |
| 7245 | NZ | LYS | B | 149 | -20.861 | -30.062 | 97.161 | 1.00 | 44.71 |
| 7246 | C | LYS | B | 149 | -15.436 | -26.937 | 98.601 | 1.00 | 40.97 |
| 7247 | O | LYS | B | 149 | -14.981 | -26.041 | 97.888 | 1.00 | 41.10 |
| 7248 | N | ILE | B | 150 | -14.674 | -27.725 | 99.349 | 1.00 | 41.46 |
| 7249 | CA | ILE | B | 150 | -13.227 | -27.625 | 99.293 | 1.00 | 41.98 |
| 7250 | CB | ILE | B | 150 | -12.589 | -28.239 | 100.543 | 1.00 | 42.06 |
| 7251 | CG1 | ILE | B | 150 | -12.546 | -27.196 | 101.656 | 1.00 | 42.77 |
| 7252 | CD1 | ILE | B | 150 | -13.585 | -26.106 | 101.539 | 1.00 | 41.99 |
| 7253 | CG2 | ILE | B | 150 | -11.154 | -28.660 | 100.263 | 1.00 | 42.89 |
| 7254 | C | ILE | B | 150 | -12.790 | -28.312 | 98.018 | 1.00 | 41.88 |
| 7255 | O | ILE | B | 150 | -11.875 | -27.873 | 97.345 | 1.00 | 41.45 |
| 7256 | N | GLU | B | 151 | -13.488 | -29.379 | 97.669 | 1.00 | 42.89 |
| 7257 | CA | GLU | B | 151 | -13.240 | -30.049 | 96.401 | 1.00 | 44.16 |
| 7258 | CB | GLU | B | 151 | -12.493 | -31.373 | 96.603 | 1.00 | 44.31 |
| 7259 | CG | GLU | B | 151 | -11.200 | -31.253 | 97.409 | 1.00 | 45.63 |
| 7260 | CD | GLU | B | 151 | -10.025 | -30.739 | 96.600 | 1.00 | 48.28 |
| 7261 | OE1 | GLU | B | 151 | -10.010 | -30.951 | 95.373 | 1.00 | 50.02 |
| 7262 | OE2 | GLU | B | 151 | -9.108 | -30.119 | 97.191 | 1.00 | 50.10 |
| 7263 | C | GLU | B | 151 | -14.570 | -30.247 | 95.682 | 1.00 | 44.43 |
| 7264 | O | GLU | B | 151 | -15.577 | -30.594 | 96.289 | 1.00 | 44.13 |
| 7265 | N | PRO | B | 152 | -14.570 | -30.022 | 94.381 | 1.00 | 45.23 |
| 7266 | CA | PRO | B | 152 | -15.802 | -30.091 | 93.594 | 1.00 | 46.07 |
| 7267 | CB | PRO | B | 152 | -15.297 | -29.979 | 92.158 | 1.00 | 45.96 |
| 7268 | CG | PRO | B | 152 | -14.015 | -29.226 | 92.275 | 1.00 | 45.42 |
| 7269 | CD | PRO | B | 152 | -13.395 | -29.684 | 93.558 | 1.00 | 45.23 |
| 7270 | C | PRO | B | 152 | -16.602 | -31.381 | 93.794 | 1.00 | 47.12 |
| 7271 | O | PRO | B | 152 | -17.834 | -31.353 | 93.728 | 1.00 | 46.89 |
| 7272 | N | ASN | B | 153 | -15.919 | -32.492 | 94.057 | 1.00 | 48.20 |
| 7273 | CA | ASN | B | 153 | -16.609 | -33.771 | 94.186 | 1.00 | 49.06 |
| 7274 | CB | ASN | B | 153 | -15.790 | -34.881 | 93.532 | 1.00 | 49.32 |
| 7275 | CG | ASN | B | 153 | -14.711 | -35.406 | 94.437 | 1.00 | 50.49 |
| 7276 | OD1 | ASN | B | 153 | -13.528 | -35.102 | 94.267 | 1.00 | 51.24 |
| 7277 | ND2 | ASN | B | 153 | -15.111 | -36.197 | 95.420 | 1.00 | 53.07 |
| 7278 | C | ASN | B | 153 | -16.967 | -34.162 | 95.615 | 1.00 | 49.43 |
| 7279 | O | ASN | B | 153 | -17.598 | -35.188 | 95.842 | 1.00 | 49.74 |
| 7280 | N | LEU | B | 154 | -16.591 | -33.336 | 96.579 | 1.00 | 49.88 |
| 7281 | CA | LEU | B | 154 | -16.837 | -33.669 | 97.973 | 1.00 | 50.21 |
| 7282 | CB | LEU | B | 154 | -15.667 | -33.186 | 98.826 | 1.00 | 50.44 |
| 7283 | CG | LEU | B | 154 | -14.568 | -34.191 | 99.167 | 1.00 | 51.03 |

FIGURE 3 EM

| A | B | C | D | E | F | G | H | I | J |
|---|---|---|---|---|---|---|---|---|---|
| 7284 | CD1 | LEU | B | 154 | -14.481 | -35.297 | 98.128 | 1.00 | 52.56 |
| 7285 | CD2 | LEU | B | 154 | -13.248 | -33.473 | 99.285 | 1.00 | 52.12 |
| 7286 | C | LEU | B | 154 | -18.140 | -33.088 | 98.514 | 1.00 | 50.42 |
| 7287 | O | LEU | B | 154 | -18.656 | -32.090 | 98.007 | 1.00 | 50.74 |
| 7288 | N | PRO | B | 155 | -18.679 | -33.720 | 99.545 | 1.00 | 50.30 |
| 7289 | CA | PRO | B | 155 | -19.869 | -33.204 | 100.222 | 1.00 | 50.05 |
| 7290 | CB | PRO | B | 155 | -19.971 | -34.090 | 101.469 | 1.00 | 50.11 |
| 7291 | CG | PRO | B | 155 | -18.609 | -34.742 | 101.564 | 1.00 | 50.65 |
| 7292 | CD | PRO | B | 155 | -18.220 | -34.988 | 100.135 | 1.00 | 50.55 |
| 7293 | C | PRO | B | 155 | -19.633 | -31.748 | 100.608 | 1.00 | 49.51 |
| 7294 | O | PRO | B | 155 | -18.479 | -31.344 | 100.783 | 1.00 | 49.41 |
| 7295 | N | SER | B | 156 | -20.711 | -30.982 | 100.736 | 1.00 | 48.74 |
| 7296 | CA | SER | B | 156 | -20.619 | -29.547 | 101.005 | 1.00 | 48.18 |
| 7297 | CB | SER | B | 156 | -21.763 | -28.792 | 100.302 | 1.00 | 48.05 |
| 7298 | OG | SER | B | 156 | -21.415 | -28.458 | 98.966 | 1.00 | 48.05 |
| 7299 | C | SER | B | 156 | -20.640 | -29.189 | 102.486 | 1.00 | 47.66 |
| 7300 | O | SER | B | 156 | -21.240 | -29.875 | 103.312 | 1.00 | 47.05 |
| 7301 | N | TYR | B | 157 | -19.988 | -28.082 | 102.803 | 1.00 | 47.22 |
| 7302 | CA | TYR | B | 157 | -19.999 | -27.568 | 104.149 | 1.00 | 46.94 |
| 7303 | CB | TYR | B | 157 | -18.635 | -27.003 | 104.502 | 1.00 | 47.36 |
| 7304 | CG | TYR | B | 157 | -17.554 | -28.046 | 104.612 | 1.00 | 48.59 |
| 7305 | CD1 | TYR | B | 157 | -17.462 | -28.869 | 105.728 | 1.00 | 50.51 |
| 7306 | CE1 | TYR | B | 157 | -16.455 | -29.820 | 105.837 | 1.00 | 50.88 |
| 7307 | CZ | TYR | B | 157 | -15.540 | -29.944 | 104.823 | 1.00 | 50.85 |
| 7308 | OH | TYR | B | 157 | -14.535 | -30.872 | 104.903 | 1.00 | 53.46 |
| 7309 | CE2 | TYR | B | 157 | -15.616 | -29.137 | 103.710 | 1.00 | 51.19 |
| 7310 | CD2 | TYR | B | 157 | -16.613 | -28.198 | 103.610 | 1.00 | 49.46 |
| 7311 | C | TYR | B | 157 | -21.049 | -26.472 | 104.233 | 1.00 | 46.22 |
| 7312 | O | TYR | B | 157 | -20.942 | -25.441 | 103.572 | 1.00 | 45.77 |
| 7313 | N | ARG | B | 158 | -22.065 | -26.720 | 105.047 | 1.00 | 45.42 |
| 7314 | CA | ARG | B | 158 | -23.137 | -25.775 | 105.279 | 1.00 | 44.92 |
| 7315 | CB | ARG | B | 158 | -24.279 | -26.497 | 105.999 | 1.00 | 45.11 |
| 7316 | CG | ARG | B | 158 | -25.641 | -26.404 | 105.373 | 1.00 | 45.98 |
| 7317 | CD | ARG | B | 158 | -26.622 | -25.478 | 106.084 | 1.00 | 48.49 |
| 7318 | NE | ARG | B | 158 | -27.943 | -26.099 | 106.177 | 1.00 | 49.66 |
| 7319 | CZ | ARG | B | 158 | -29.096 | -25.446 | 106.138 | 1.00 | 50.00 |
| 7320 | NH1 | ARG | B | 158 | -29.117 | -24.134 | 106.009 | 1.00 | 50.42 |
| 7321 | NH2 | ARG | B | 158 | -30.235 | -26.114 | 106.235 | 1.00 | 49.94 |
| 7322 | C | ARG | B | 158 | -22.591 | -24.689 | 106.189 | 1.00 | 44.40 |
| 7323 | O | ARG | B | 158 | -22.266 | -24.964 | 107.341 | 1.00 | 44.02 |
| 7324 | N | ILE | B | 159 | -22.469 | -23.463 | 105.686 | 1.00 | 43.84 |
| 7325 | CA | ILE | B | 159 | -22.002 | -22.368 | 106.532 | 1.00 | 43.13 |
| 7326 | CB | ILE | B | 159 | -21.245 | -21.305 | 105.711 | 1.00 | 43.15 |
| 7327 | CG1 | ILE | B | 159 | -20.127 | -21.960 | 104.888 | 1.00 | 43.08 |
| 7328 | CD1 | ILE | B | 159 | -19.379 | -23.072 | 105.610 | 1.00 | 40.50 |
| 7329 | CG2 | ILE | B | 159 | -20.678 | -20.213 | 106.618 | 1.00 | 42.00 |
| 7330 | C | ILE | B | 159 | -23.138 | -21.742 | 107.356 | 1.00 | 43.24 |
| 7331 | O | ILE | B | 159 | -22.978 | -21.499 | 108.550 | 1.00 | 42.94 |
| 7332 | N | THR | B | 160 | -24.295 | -21.501 | 106.742 | 1.00 | 43.15 |
| 7333 | CA | THR | B | 160 | -25.395 | -20.882 | 107.485 | 1.00 | 43.07 |
| 7334 | CB | THR | B | 160 | -25.738 | -19.488 | 106.924 | 1.00 | 43.35 |

FIGURE 3 EN

| A | B | C | D | E | F | G | H | I | J |
|---|---|---|---|---|---|---|---|---|---|
| 7335 | OG1 | THR | B | 160 | -26.277 | -19.612 | 105.594 | 1.00 | 43.35 |
| 7336 | CG2 | THR | B | 160 | -24.468 | -18.671 | 106.732 | 1.00 | 42.11 |
| 7337 | C | THR | B | 160 | -26.640 | -21.743 | 107.564 | 1.00 | 43.24 |
| 7338 | O | THR | B | 160 | -26.858 | -22.633 | 106.747 | 1.00 | 43.71 |
| 7339 | N | TRP | B | 161 | -27.467 | -21.477 | 108.559 | 1.00 | 43.10 |
| 7340 | CA | TRP | B | 161 | -28.651 | -22.284 | 108.758 | 1.00 | 43.13 |
| 7341 | CB | TRP | B | 161 | -28.448 | -23.207 | 109.960 | 1.00 | 43.35 |
| 7342 | CG | TRP | B | 161 | -27.335 | -24.217 | 109.814 | 1.00 | 43.29 |
| 7343 | CD1 | TRP | B | 161 | -25.989 | -23.984 | 109.894 | 1.00 | 41.69 |
| 7344 | NE1 | TRP | B | 161 | -25.295 | -25.159 | 109.723 | 1.00 | 41.69 |
| 7345 | CE2 | TRP | B | 161 | -26.186 | -26.182 | 109.538 | 1.00 | 42.31 |
| 7346 | CD2 | TRP | B | 161 | -27.483 | -25.623 | 109.587 | 1.00 | 42.81 |
| 7347 | CE3 | TRP | B | 161 | -28.582 | -26.471 | 109.431 | 1.00 | 42.85 |
| 7348 | CZ3 | TRP | B | 161 | -28.356 | -27.825 | 109.217 | 1.00 | 44.59 |
| 7349 | CH2 | TRP | B | 161 | -27.050 | -28.345 | 109.167 | 1.00 | 43.07 |
| 7350 | CZ2 | TRP | B | 161 | -25.959 | -27.539 | 109.317 | 1.00 | 42.07 |
| 7351 | C | TRP | B | 161 | -29.854 | -21.399 | 109.020 | 1.00 | 43.23 |
| 7352 | O | TRP | B | 161 | -30.892 | -21.876 | 109.460 | 1.00 | 43.49 |
| 7353 | N | THR | B | 162 | -29.716 | -20.109 | 108.758 | 1.00 | 43.00 |
| 7354 | CA | THR | B | 162 | -30.786 | -19.171 | 109.071 | 1.00 | 43.22 |
| 7355 | CB | THR | B | 162 | -30.197 | -17.990 | 109.819 | 1.00 | 42.86 |
| 7356 | OG1 | THR | B | 162 | -29.199 | -17.384 | 108.996 | 1.00 | 43.09 |
| 7357 | CG2 | THR | B | 162 | -29.402 | -18.485 | 111.017 | 1.00 | 42.82 |
| 7358 | C | THR | B | 162 | -31.558 | -18.665 | 107.847 | 1.00 | 43.08 |
| 7359 | O | THR | B | 162 | -32.638 | -18.098 | 107.984 | 1.00 | 42.87 |
| 7360 | N | GLY | B | 163 | -30.984 | -18.860 | 106.665 | 1.00 | 43.22 |
| 7361 | CA | GLY | B | 163 | -31.609 | -18.446 | 105.429 | 1.00 | 43.32 |
| 7362 | C | GLY | B | 163 | -33.107 | -18.688 | 105.430 | 1.00 | 43.53 |
| 7363 | O | GLY | B | 163 | -33.571 | -19.799 | 105.714 | 1.00 | 43.50 |
| 7364 | N | LYS | B | 164 | -33.862 | -17.636 | 105.122 | 1.00 | 43.32 |
| 7365 | CA | LYS | B | 164 | -35.318 | -17.719 | 105.067 | 1.00 | 43.66 |
| 7366 | CB | LYS | B | 164 | -35.924 | -17.290 | 106.404 | 1.00 | 43.86 |
| 7367 | CG | LYS | B | 164 | -37.444 | -17.402 | 106.460 | 1.00 | 45.67 |
| 7368 | CD | LYS | B | 164 | -37.970 | -17.337 | 107.897 | 1.00 | 47.17 |
| 7369 | CE | LYS | B | 164 | -39.497 | -17.471 | 107.904 | 1.00 | 49.52 |
| 7370 | NZ | LYS | B | 164 | -40.097 | -17.520 | 109.267 | 1.00 | 48.85 |
| 7371 | C | LYS | B | 164 | -35.859 | -16.855 | 103.920 | 1.00 | 43.13 |
| 7372 | O | LYS | B | 164 | -35.777 | -15.629 | 103.963 | 1.00 | 42.90 |
| 7373 | N | GLU | B | 165 | -36.390 | -17.509 | 102.894 | 1.00 | 42.88 |
| 7374 | CA | GLU | B | 165 | -36.916 | -16.827 | 101.707 | 1.00 | 42.75 |
| 7375 | CB | GLU | B | 165 | -37.875 | -17.769 | 100.970 | 1.00 | 42.89 |
| 7376 | CG | GLU | B | 165 | -38.447 | -17.218 | 99.675 | 1.00 | 46.01 |
| 7377 | CD | GLU | B | 165 | -39.346 | -18.229 | 98.978 | 1.00 | 50.75 |
| 7378 | OE1 | GLU | B | 165 | -40.426 | -18.572 | 99.533 | 1.00 | 50.41 |
| 7379 | OE2 | GLU | B | 165 | -38.962 | -18.695 | 97.876 | 1.00 | 53.37 |
| 7380 | C | GLU | B | 165 | -37.602 | -15.488 | 102.044 | 1.00 | 41.49 |
| 7381 | O | GLU | B | 165 | -38.538 | -15.456 | 102.823 | 1.00 | 41.12 |
| 7382 | N | ASN | B | 166 | -37.108 | -14.392 | 101.473 | 1.00 | 40.30 |
| 7383 | CA | ASN | B | 166 | -37.662 | -13.053 | 101.719 | 1.00 | 39.57 |
| 7384 | CB | ASN | B | 166 | -39.179 | -13.017 | 101.491 | 1.00 | 39.43 |
| 7385 | CG | ASN | B | 166 | -39.571 | -13.312 | 100.046 | 1.00 | 38.77 |

FIGURE 3 EO

| A | B | C | D | E | F | G | H | I | J |
|---|---|---|---|---|---|---|---|---|---|
| 7386 | OD1 | ASN | B | 166 | -38.892 | -12.895 | 99.108 | 1.00 | 39.24 |
| 7387 | ND2 | ASN | B | 166 | -40.675 | -14.037 | 99.867 | 1.00 | 36.86 |
| 7388 | C | ASN | B | 166 | -37.363 | -12.425 | 103.084 | 1.00 | 39.44 |
| 7389 | O | ASN | B | 166 | -37.652 | -11.249 | 103.302 | 1.00 | 39.64 |
| 7390 | N | ILE | B | 167 | -36.804 | -13.194 | 104.010 | 1.00 | 38.55 |
| 7391 | CA | ILE | B | 167 | -36.523 | -12.651 | 105.326 | 1.00 | 37.72 |
| 7392 | CB | ILE | B | 167 | -37.297 | -13.426 | 106.415 | 1.00 | 38.14 |
| 7393 | CG1 | ILE | B | 167 | -38.801 | -13.239 | 106.216 | 1.00 | 38.62 |
| 7394 | CD1 | ILE | B | 167 | -39.452 | -14.349 | 105.474 | 1.00 | 40.55 |
| 7395 | CG2 | ILE | B | 167 | -36.927 | -12.924 | 107.796 | 1.00 | 37.27 |
| 7396 | C | ILE | B | 167 | -35.035 | -12.593 | 105.631 | 1.00 | 36.78 |
| 7397 | O | ILE | B | 167 | -34.502 | -11.529 | 105.876 | 1.00 | 37.09 |
| 7398 | N | ILE | B | 168 | -34.356 | -13.730 | 105.594 | 1.00 | 35.88 |
| 7399 | CA | ILE | B | 168 | -32.934 | -13.748 | 105.899 | 1.00 | 34.97 |
| 7400 | CB | ILE | B | 168 | -32.696 | -14.591 | 107.179 | 1.00 | 35.66 |
| 7401 | CG1 | ILE | B | 168 | -33.226 | -13.809 | 108.393 | 1.00 | 35.90 |
| 7402 | CD1 | ILE | B | 168 | -33.721 | -14.673 | 109.511 | 1.00 | 40.18 |
| 7403 | CG2 | ILE | B | 168 | -31.223 | -14.947 | 107.326 | 1.00 | 34.03 |
| 7404 | C | ILE | B | 168 | -32.105 | -14.239 | 104.730 | 1.00 | 34.18 |
| 7405 | O | ILE | B | 168 | -32.317 | -15.343 | 104.234 | 1.00 | 34.01 |
| 7406 | N | TYR | B | 169 | -31.193 | -13.391 | 104.265 | 1.00 | 33.65 |
| 7407 | CA | TYR | B | 169 | -30.309 | -13.715 | 103.147 | 1.00 | 33.38 |
| 7408 | CB | TYR | B | 169 | -30.335 | -12.621 | 102.083 | 1.00 | 33.36 |
| 7409 | CG | TYR | B | 169 | -31.679 | -12.194 | 101.564 | 1.00 | 34.51 |
| 7410 | CD1 | TYR | B | 169 | -32.566 | -11.521 | 102.382 | 1.00 | 35.15 |
| 7411 | CE1 | TYR | B | 169 | -33.790 | -11.087 | 101.908 | 1.00 | 36.27 |
| 7412 | CZ | TYR | B | 169 | -34.146 | -11.307 | 100.585 | 1.00 | 36.51 |
| 7413 | OH | TYR | B | 169 | -35.384 | -10.858 | 100.163 | 1.00 | 37.33 |
| 7414 | CE2 | TYR | B | 169 | -33.278 | -11.968 | 99.731 | 1.00 | 34.96 |
| 7415 | CD2 | TYR | B | 169 | -32.036 | -12.398 | 100.224 | 1.00 | 34.82 |
| 7416 | C | TYR | B | 169 | -28.860 | -13.828 | 103.622 | 1.00 | 33.08 |
| 7417 | O | TYR | B | 169 | -28.336 | -12.899 | 104.240 | 1.00 | 32.88 |
| 7418 | N | ASN | B | 170 | -28.217 | -14.952 | 103.321 | 1.00 | 32.60 |
| 7419 | CA | ASN | B | 170 | -26.826 | -15.171 | 103.688 | 1.00 | 32.11 |
| 7420 | CB | ASN | B | 170 | -26.657 | -16.482 | 104.471 | 1.00 | 32.23 |
| 7421 | CG | ASN | B | 170 | -27.415 | -16.513 | 105.776 | 1.00 | 32.33 |
| 7422 | OD1 | ASN | B | 170 | -28.356 | -17.289 | 105.932 | 1.00 | 33.34 |
| 7423 | ND2 | ASN | B | 170 | -26.990 | -15.703 | 106.735 | 1.00 | 30.14 |
| 7424 | C | ASN | B | 170 | -26.025 | -15.327 | 102.420 | 1.00 | 31.44 |
| 7425 | O | ASN | B | 170 | -26.245 | -16.282 | 101.685 | 1.00 | 31.22 |
| 7426 | N | GLY | B | 171 | -25.084 | -14.430 | 102.164 | 1.00 | 30.91 |
| 7427 | CA | GLY | B | 171 | -24.249 | -14.552 | 100.982 | 1.00 | 30.57 |
| 7428 | C | GLY | B | 171 | -24.806 | -13.905 | 99.713 | 1.00 | 30.67 |
| 7429 | O | GLY | B | 171 | -24.083 | -13.797 | 98.726 | 1.00 | 29.92 |
| 7430 | N | ILE | B | 172 | -26.080 | -13.487 | 99.746 | 1.00 | 30.45 |
| 7431 | CA | ILE | B | 172 | -26.711 | -12.764 | 98.642 | 1.00 | 30.45 |
| 7432 | CB | ILE | B | 172 | -27.703 | -13.666 | 97.892 | 1.00 | 30.43 |
| 7433 | CG1 | ILE | B | 172 | -28.635 | -14.358 | 98.899 | 1.00 | 29.88 |
| 7434 | CD1 | ILE | B | 172 | -29.746 | -15.140 | 98.262 | 1.00 | 28.11 |
| 7435 | CG2 | ILE | B | 172 | -26.966 | -14.647 | 97.004 | 1.00 | 28.79 |
| 7436 | C | ILE | B | 172 | -27.476 | -11.553 | 99.155 | 1.00 | 30.70 |

FIGURE 3 EP

| A | B | C | D | E | F | G | H | I | J |
|---|---|---|---|---|---|---|---|---|---|
| 7437 | O | ILE | B | 172 | -27.952 | -11.533 | 100.288 | 1.00 | 31.56 |
| 7438 | N | THR | B | 173 | -27.638 | -10.546 | 98.314 | 1.00 | 30.54 |
| 7439 | CA | THR | B | 173 | -28.366 | -9.353 | 98.730 | 1.00 | 30.17 |
| 7440 | CB | THR | B | 173 | -27.998 | -8.248 | 97.790 | 1.00 | 30.29 |
| 7441 | OG1 | THR | B | 173 | -27.995 | -8.776 | 96.451 | 1.00 | 30.15 |
| 7442 | CG2 | THR | B | 173 | -26.544 | -7.836 | 98.045 | 1.00 | 29.43 |
| 7443 | C | THR | B | 173 | -29.883 | -9.516 | 98.695 | 1.00 | 30.13 |
| 7444 | O | THR | B | 173 | -30.395 | -10.516 | 98.181 | 1.00 | 30.07 |
| 7445 | N | ASP | B | 174 | -30.603 | -8.531 | 99.245 | 1.00 | 29.15 |
| 7446 | CA | ASP | B | 174 | -32.053 | -8.480 | 99.078 | 1.00 | 28.13 |
| 7447 | CB | ASP | B | 174 | -32.750 | -7.944 | 100.324 | 1.00 | 28.31 |
| 7448 | CG | ASP | B | 174 | -32.454 | -6.485 | 100.570 | 1.00 | 29.05 |
| 7449 | OD1 | ASP | B | 174 | -33.182 | -5.855 | 101.372 | 1.00 | 30.08 |
| 7450 | OD2 | ASP | B | 174 | -31.529 | -5.875 | 99.997 | 1.00 | 28.42 |
| 7451 | C | ASP | B | 174 | -32.238 | -7.533 | 97.911 | 1.00 | 27.65 |
| 7452 | O | ASP | B | 174 | -31.253 | -7.141 | 97.298 | 1.00 | 27.19 |
| 7453 | N | TRP | B | 175 | -33.469 | -7.127 | 97.596 | 1.00 | 27.54 |
| 7454 | CA | TRP | B | 175 | -33.648 | -6.240 | 96.432 | 1.00 | 26.79 |
| 7455 | CB | TRP | B | 175 | -35.128 | -5.926 | 96.122 | 1.00 | 26.14 |
| 7456 | CG | TRP | B | 175 | -35.261 | -5.307 | 94.757 | 1.00 | 23.48 |
| 7457 | CD1 | TRP | B | 175 | -35.570 | -5.953 | 93.586 | 1.00 | 22.72 |
| 7458 | NE1 | TRP | B | 175 | -35.566 | -5.065 | 92.535 | 1.00 | 22.62 |
| 7459 | CE2 | TRP | B | 175 | -35.271 | -3.815 | 93.010 | 1.00 | 22.14 |
| 7460 | CD2 | TRP | B | 175 | -35.068 | -3.930 | 94.407 | 1.00 | 21.47 |
| 7461 | CE3 | TRP | B | 175 | -34.771 | -2.780 | 95.130 | 1.00 | 19.92 |
| 7462 | CZ3 | TRP | B | 175 | -34.657 | -1.568 | 94.456 | 1.00 | 20.93 |
| 7463 | CH2 | TRP | B | 175 | -34.855 | -1.484 | 93.079 | 1.00 | 20.31 |
| 7464 | CZ2 | TRP | B | 175 | -35.169 | -2.600 | 92.335 | 1.00 | 22.25 |
| 7465 | C | TRP | B | 175 | -32.834 | -4.947 | 96.415 | 1.00 | 27.04 |
| 7466 | O | TRP | B | 175 | -32.199 | -4.653 | 95.409 | 1.00 | 27.07 |
| 7467 | N | VAL | B | 176 | -32.878 | -4.141 | 97.481 | 1.00 | 27.37 |
| 7468 | CA | VAL | B | 176 | -32.150 | -2.856 | 97.437 | 1.00 | 27.70 |
| 7469 | CB | VAL | B | 176 | -32.408 | -1.918 | 98.659 | 1.00 | 27.94 |
| 7470 | CG1 | VAL | B | 176 | -32.922 | -2.697 | 99.840 | 1.00 | 29.41 |
| 7471 | CG2 | VAL | B | 176 | -33.313 | -0.812 | 98.284 | 1.00 | 27.83 |
| 7472 | C | VAL | B | 176 | -30.653 | -2.978 | 97.412 | 1.00 | 27.07 |
| 7473 | O | VAL | B | 176 | -29.988 | -2.183 | 96.788 | 1.00 | 27.17 |
| 7474 | N | TYR | B | 177 | -30.107 | -3.924 | 98.152 | 1.00 | 27.06 |
| 7475 | CA | TYR | B | 177 | -28.672 | -4.032 | 98.169 | 1.00 | 27.84 |
| 7476 | CB | TYR | B | 177 | -28.214 | -5.024 | 99.239 | 1.00 | 28.15 |
| 7477 | CG | TYR | B | 177 | -27.918 | -4.360 | 100.567 | 1.00 | 29.10 |
| 7478 | CD1 | TYR | B | 177 | -28.941 | -4.117 | 101.506 | 1.00 | 27.32 |
| 7479 | CE1 | TYR | B | 177 | -28.665 | -3.513 | 102.711 | 1.00 | 28.33 |
| 7480 | CZ | TYR | B | 177 | -27.354 | -3.134 | 102.987 | 1.00 | 29.96 |
| 7481 | OH | TYR | B | 177 | -27.032 | -2.521 | 104.161 | 1.00 | 30.14 |
| 7482 | CE2 | TYR | B | 177 | -26.343 | -3.360 | 102.081 | 1.00 | 29.19 |
| 7483 | CD2 | TYR | B | 177 | -26.630 | -3.964 | 100.877 | 1.00 | 27.15 |
| 7484 | C | TYR | B | 177 | -28.184 | -4.404 | 96.779 | 1.00 | 28.36 |
| 7485 | O | TYR | B | 177 | -27.234 | -3.808 | 96.246 | 1.00 | 28.11 |
| 7486 | N | GLU | B | 178 | -28.859 | -5.360 | 96.162 | 1.00 | 28.62 |
| 7487 | CA | GLU | B | 178 | -28.408 | -5.767 | 94.847 | 1.00 | 29.47 |

FIGURE 3 EQ

| A | B | C | D | E | F | G | H | I | J |
|---|---|---|---|---|---|---|---|---|---|
| 7488 | CB | GLU | B | 178 | -29.292 | -6.858 | 94.256 | 1.00 | 29.15 |
| 7489 | CG | GLU | B | 178 | -28.905 | -7.190 | 92.826 | 1.00 | 27.91 |
| 7490 | CD | GLU | B | 178 | -29.890 | -8.149 | 92.182 | 1.00 | 25.71 |
| 7491 | OE1 | GLU | B | 178 | -29.962 | -8.151 | 90.942 | 1.00 | 27.31 |
| 7492 | OE2 | GLU | B | 178 | -30.607 | -8.860 | 92.919 | 1.00 | 22.10 |
| 7493 | C | GLU | B | 178 | -28.376 | -4.584 | 93.908 | 1.00 | 29.85 |
| 7494 | O | GLU | B | 178 | -27.340 | -4.295 | 93.295 | 1.00 | 29.77 |
| 7495 | N | GLU | B | 179 | -29.507 | -3.881 | 93.833 | 1.00 | 30.44 |
| 7496 | CA | GLU | B | 179 | -29.677 | -2.804 | 92.872 | 1.00 | 31.04 |
| 7497 | CB | GLU | B | 179 | -31.182 | -2.541 | 92.624 | 1.00 | 31.33 |
| 7498 | CG | GLU | B | 179 | -31.470 | -1.322 | 91.739 | 1.00 | 30.44 |
| 7499 | CD | GLU | B | 179 | -31.039 | -1.563 | 90.307 | 1.00 | 30.62 |
| 7500 | OE1 | GLU | B | 179 | -30.843 | -2.753 | 89.978 | 1.00 | 31.34 |
| 7501 | OE2 | GLU | B | 179 | -30.893 | -0.592 | 89.518 | 1.00 | 30.02 |
| 7502 | C | GLU | B | 179 | -29.002 | -1.493 | 93.218 | 1.00 | 31.78 |
| 7503 | O | GLU | B | 179 | -28.433 | -0.844 | 92.353 | 1.00 | 31.90 |
| 7504 | N | GLU | B | 180 | -29.082 | -1.078 | 94.474 | 1.00 | 32.62 |
| 7505 | CA | GLU | B | 180 | -28.608 | 0.252 | 94.824 | 1.00 | 33.58 |
| 7506 | CB | GLU | B | 180 | -29.726 | 1.019 | 95.554 | 1.00 | 33.44 |
| 7507 | CG | GLU | B | 180 | -31.081 | 0.966 | 94.860 | 1.00 | 33.23 |
| 7508 | CD | GLU | B | 180 | -31.194 | 1.925 | 93.687 | 1.00 | 33.27 |
| 7509 | OE1 | GLU | B | 180 | -30.149 | 2.442 | 93.233 | 1.00 | 34.14 |
| 7510 | OE2 | GLU | B | 180 | -32.332 | 2.176 | 93.219 | 1.00 | 33.57 |
| 7511 | C | GLU | B | 180 | -27.326 | 0.323 | 95.644 | 1.00 | 34.47 |
| 7512 | O | GLU | B | 180 | -26.507 | 1.220 | 95.454 | 1.00 | 34.81 |
| 7513 | N | VAL | B | 181 | -27.164 | -0.586 | 96.590 | 1.00 | 35.56 |
| 7514 | CA | VAL | B | 181 | -25.974 | -0.539 | 97.430 | 1.00 | 36.34 |
| 7515 | CB | VAL | B | 181 | -26.227 | -1.164 | 98.786 | 1.00 | 36.64 |
| 7516 | CG1 | VAL | B | 181 | -25.010 | -0.997 | 99.674 | 1.00 | 37.55 |
| 7517 | CG2 | VAL | B | 181 | -27.453 | -0.505 | 99.439 | 1.00 | 36.85 |
| 7518 | C | VAL | B | 181 | -24.795 | -1.202 | 96.749 | 1.00 | 36.58 |
| 7519 | O | VAL | B | 181 | -23.817 | -0.538 | 96.422 | 1.00 | 37.02 |
| 7520 | N | PHE | B | 182 | -24.895 | -2.495 | 96.467 | 1.00 | 37.09 |
| 7521 | CA | PHE | B | 182 | -23.768 | -3.189 | 95.838 | 1.00 | 36.97 |
| 7522 | CB | PHE | B | 182 | -23.741 | -4.671 | 96.207 | 1.00 | 36.58 |
| 7523 | CG | PHE | B | 182 | -23.482 | -4.936 | 97.663 | 1.00 | 37.39 |
| 7524 | CD1 | PHE | B | 182 | -23.257 | -3.900 | 98.552 | 1.00 | 37.49 |
| 7525 | CE1 | PHE | B | 182 | -23.029 | -4.147 | 99.903 | 1.00 | 37.26 |
| 7526 | CZ | PHE | B | 182 | -23.019 | -5.423 | 100.375 | 1.00 | 36.96 |
| 7527 | CE2 | PHE | B | 182 | -23.237 | -6.474 | 99.499 | 1.00 | 39.17 |
| 7528 | CD2 | PHE | B | 182 | -23.467 | -6.225 | 98.147 | 1.00 | 38.10 |
| 7529 | C | PHE | B | 182 | -23.679 | -3.028 | 94.328 | 1.00 | 37.24 |
| 7530 | O | PHE | B | 182 | -22.641 | -2.621 | 93.814 | 1.00 | 38.18 |
| 7531 | N | SER | B | 183 | -24.778 | -3.319 | 93.632 | 1.00 | 37.49 |
| 7532 | CA | SER | B | 183 | -24.842 | -3.392 | 92.167 | 1.00 | 36.70 |
| 7533 | CB | SER | B | 183 | -23.933 | -2.400 | 91.452 | 1.00 | 36.88 |
| 7534 | OG | SER | B | 183 | -24.612 | -1.194 | 91.161 | 1.00 | 36.34 |
| 7535 | C | SER | B | 183 | -24.453 | -4.790 | 91.769 | 1.00 | 36.58 |
| 7536 | O | SER | B | 183 | -23.849 | -5.010 | 90.710 | 1.00 | 37.26 |
| 7537 | N | ALA | B | 184 | -24.798 | -5.738 | 92.627 | 1.00 | 35.60 |
| 7538 | CA | ALA | B | 184 | -24.502 | -7.127 | 92.372 | 1.00 | 34.98 |

FIGURE 3 ER

| A | B | C | D | E | F | G | H | I | J |
|---|---|---|---|---|---|---|---|---|---|
| 7539 | CB | ALA | B | 184 | -23.043 | -7.420 | 92.640 | 1.00 | 35.69 |
| 7540 | C | ALA | B | 184 | -25.358 | -7.935 | 93.300 | 1.00 | 34.68 |
| 7541 | O | ALA | B | 184 | -25.841 | -7.420 | 94.299 | 1.00 | 35.13 |
| 7542 | N | TYR | B | 185 | -25.535 | -9.203 | 92.969 | 1.00 | 33.68 |
| 7543 | CA | TYR | B | 185 | -26.319 | -10.103 | 93.784 | 1.00 | 33.79 |
| 7544 | CB | TYR | B | 185 | -26.744 | -11.285 | 92.938 | 1.00 | 32.72 |
| 7545 | CG | TYR | B | 185 | -27.789 | -12.180 | 93.562 | 1.00 | 32.50 |
| 7546 | CD1 | TYR | B | 185 | -27.894 | -13.511 | 93.171 | 1.00 | 29.63 |
| 7547 | CE1 | TYR | B | 185 | -28.841 | -14.325 | 93.684 | 1.00 | 28.92 |
| 7548 | CZ | TYR | B | 185 | -29.733 | -13.849 | 94.606 | 1.00 | 29.80 |
| 7549 | OH | TYR | B | 185 | -30.679 | -14.731 | 95.083 | 1.00 | 30.48 |
| 7550 | CE2 | TYR | B | 185 | -29.680 | -12.535 | 95.029 | 1.00 | 28.44 |
| 7551 | CD2 | TYR | B | 185 | -28.706 | -11.694 | 94.494 | 1.00 | 29.79 |
| 7552 | C | TYR | B | 185 | -25.489 | -10.648 | 94.934 | 1.00 | 34.13 |
| 7553 | O | TYR | B | 185 | -25.965 | -10.738 | 96.065 | 1.00 | 34.82 |
| 7554 | N | SER | B | 186 | -24.261 | -11.037 | 94.607 | 1.00 | 34.52 |
| 7555 | CA | SER | B | 186 | -23.329 | -11.672 | 95.530 | 1.00 | 34.83 |
| 7556 | CB | SER | B | 186 | -22.044 | -12.048 | 94.792 | 1.00 | 34.59 |
| 7557 | OG | SER | B | 186 | -21.192 | -12.841 | 95.610 | 1.00 | 35.38 |
| 7558 | C | SER | B | 186 | -22.962 | -10.808 | 96.719 | 1.00 | 35.02 |
| 7559 | O | SER | B | 186 | -22.658 | -9.625 | 96.571 | 1.00 | 34.94 |
| 7560 | N | ALA | B | 187 | -23.005 | -11.410 | 97.900 | 1.00 | 35.25 |
| 7561 | CA | ALA | B | 187 | -22.539 | -10.744 | 99.103 | 1.00 | 36.21 |
| 7562 | CB | ALA | B | 187 | -23.704 | -10.353 | 100.023 | 1.00 | 36.09 |
| 7563 | C | ALA | B | 187 | -21.576 | -11.691 | 99.809 | 1.00 | 36.77 |
| 7564 | O | ALA | B | 187 | -21.650 | -11.877 | 101.025 | 1.00 | 36.72 |
| 7565 | N | LEU | B | 188 | -20.699 | -12.302 | 99.014 | 1.00 | 37.09 |
| 7566 | CA | LEU | B | 188 | -19.643 | -13.173 | 99.496 | 1.00 | 37.64 |
| 7567 | CB | LEU | B | 188 | -19.822 | -14.586 | 98.934 | 1.00 | 38.66 |
| 7568 | CG | LEU | B | 188 | -20.919 | -15.422 | 99.586 | 1.00 | 38.66 |
| 7569 | CD1 | LEU | B | 188 | -21.101 | -16.710 | 98.849 | 1.00 | 40.07 |
| 7570 | CD2 | LEU | B | 188 | -20.528 | -15.704 | 100.998 | 1.00 | 40.71 |
| 7571 | C | LEU | B | 188 | -18.334 | -12.584 | 98.988 | 1.00 | 37.53 |
| 7572 | O | LEU | B | 188 | -18.279 | -12.115 | 97.854 | 1.00 | 38.18 |
| 7573 | N | TRP | B | 189 | -17.286 | -12.582 | 99.815 | 1.00 | 37.05 |
| 7574 | CA | TRP | B | 189 | -15.995 | -12.040 | 99.391 | 1.00 | 36.44 |
| 7575 | CB | TRP | B | 189 | -15.833 | -10.602 | 99.891 | 1.00 | 36.28 |
| 7576 | CG | TRP | B | 189 | -16.914 | -9.648 | 99.454 | 1.00 | 36.18 |
| 7577 | CD1 | TRP | B | 189 | -16.895 | -8.832 | 98.355 | 1.00 | 36.04 |
| 7578 | NE1 | TRP | B | 189 | -18.049 | -8.089 | 98.295 | 1.00 | 35.31 |
| 7579 | CE2 | TRP | B | 189 | -18.850 | -8.427 | 99.353 | 1.00 | 35.02 |
| 7580 | CD2 | TRP | B | 189 | -18.164 | -9.399 | 100.109 | 1.00 | 35.13 |
| 7581 | CE3 | TRP | B | 189 | -18.777 | -9.904 | 101.263 | 1.00 | 35.16 |
| 7582 | CZ3 | TRP | B | 189 | -20.025 | -9.422 | 101.624 | 1.00 | 34.26 |
| 7583 | CH2 | TRP | B | 189 | -20.674 | -8.449 | 100.853 | 1.00 | 35.25 |
| 7584 | CZ2 | TRP | B | 189 | -20.105 | -7.941 | 99.717 | 1.00 | 34.68 |
| 7585 | C | TRP | B | 189 | -14.826 | -12.892 | 99.899 | 1.00 | 36.59 |
| 7586 | O | TRP | B | 189 | -14.435 | -12.786 | 101.065 | 1.00 | 36.63 |
| 7587 | N | TRP | B | 190 | -14.280 | -13.746 | 99.034 | 1.00 | 36.22 |
| 7588 | CA | TRP | B | 190 | -13.158 | -14.614 | 99.411 | 1.00 | 35.36 |
| 7589 | CB | TRP | B | 190 | -12.765 | -15.539 | 98.260 | 1.00 | 34.95 |

FIGURE 3 ES

| A | B | C | D | E | F | G | H | I | J |
|---|---|---|---|---|---|---|---|---|---|
| 7590 | CG | TRP | B | 190 | -13.627 | -16.753 | 98.036 | 1.00 | 34.74 |
| 7591 | CD1 | TRP | B | 190 | -14.552 | -16.926 | 97.046 | 1.00 | 33.53 |
| 7592 | NE1 | TRP | B | 190 | -15.123 | -18.172 | 97.137 | 1.00 | 34.28 |
| 7593 | CE2 | TRP | B | 190 | -14.561 | -18.844 | 98.190 | 1.00 | 34.02 |
| 7594 | CD2 | TRP | B | 190 | -13.607 | -17.981 | 98.778 | 1.00 | 34.82 |
| 7595 | CE3 | TRP | B | 190 | -12.880 | -18.443 | 99.880 | 1.00 | 35.18 |
| 7596 | CZ3 | TRP | B | 190 | -13.135 | -19.714 | 100.363 | 1.00 | 35.47 |
| 7597 | CH2 | TRP | B | 190 | -14.094 | -20.542 | 99.753 | 1.00 | 36.43 |
| 7598 | CZ2 | TRP | B | 190 | -14.812 | -20.123 | 98.669 | 1.00 | 33.78 |
| 7599 | C | TRP | B | 190 | -11.921 | -13.810 | 99.731 | 1.00 | 35.35 |
| 7600 | O | TRP | B | 190 | -11.610 | -12.839 | 99.025 | 1.00 | 34.85 |
| 7601 | N | SER | B | 191 | -11.196 | -14.218 | 100.775 | 1.00 | 34.91 |
| 7602 | CA | SER | B | 191 | -9.906 | -13.599 | 101.044 | 1.00 | 35.16 |
| 7603 | CB | SER | B | 191 | -9.284 | -14.137 | 102.347 | 1.00 | 35.21 |
| 7604 | OG | SER | B | 191 | -9.135 | -15.553 | 102.340 | 1.00 | 33.94 |
| 7605 | C | SER | B | 191 | -9.052 | -13.923 | 99.805 | 1.00 | 35.52 |
| 7606 | O | SER | B | 191 | -9.329 | -14.893 | 99.097 | 1.00 | 34.63 |
| 7607 | N | PRO | B | 192 | -8.021 | -13.136 | 99.536 | 1.00 | 36.13 |
| 7608 | CA | PRO | B | 192 | -7.250 | -13.316 | 98.303 | 1.00 | 37.16 |
| 7609 | CB | PRO | B | 192 | -6.095 | -12.328 | 98.454 | 1.00 | 36.92 |
| 7610 | CG | PRO | B | 192 | -6.617 | -11.298 | 99.386 | 1.00 | 36.51 |
| 7611 | CD | PRO | B | 192 | -7.507 | -12.026 | 100.352 | 1.00 | 36.33 |
| 7612 | C | PRO | B | 192 | -6.757 | -14.741 | 98.054 | 1.00 | 37.97 |
| 7613 | O | PRO | B | 192 | -6.767 | -15.179 | 96.905 | 1.00 | 38.49 |
| 7614 | N | ASN | B | 193 | -6.357 | -15.471 | 99.080 | 1.00 | 38.89 |
| 7615 | CA | ASN | B | 193 | -5.880 | -16.828 | 98.821 | 1.00 | 39.87 |
| 7616 | CB | ASN | B | 193 | -4.494 | -17.080 | 99.435 | 1.00 | 40.26 |
| 7617 | CG | ASN | B | 193 | -4.543 | -17.313 | 100.926 | 1.00 | 41.85 |
| 7618 | OD1 | ASN | B | 193 | -5.612 | -17.455 | 101.519 | 1.00 | 42.23 |
| 7619 | ND2 | ASN | B | 193 | -3.366 | -17.365 | 101.543 | 1.00 | 48.05 |
| 7620 | C | ASN | B | 193 | -6.877 | -17.910 | 99.193 | 1.00 | 39.93 |
| 7621 | O | ASN | B | 193 | -6.537 | -19.100 | 99.236 | 1.00 | 40.09 |
| 7622 | N | GLY | B | 194 | -8.109 | -17.478 | 99.466 | 1.00 | 40.22 |
| 7623 | CA | GLY | B | 194 | -9.222 | -18.373 | 99.728 | 1.00 | 39.55 |
| 7624 | C | GLY | B | 194 | -9.309 | -18.912 | 101.137 | 1.00 | 39.45 |
| 7625 | O | GLY | B | 194 | -10.154 | -19.772 | 101.440 | 1.00 | 39.26 |
| 7626 | N | THR | B | 195 | -8.437 | -18.443 | 102.017 | 1.00 | 39.14 |
| 7627 | CA | THR | B | 195 | -8.505 | -18.953 | 103.382 | 1.00 | 39.39 |
| 7628 | CB | THR | B | 195 | -7.321 | -18.457 | 104.222 | 1.00 | 39.64 |
| 7629 | OG1 | THR | B | 195 | -6.129 | -19.138 | 103.795 | 1.00 | 41.03 |
| 7630 | CG2 | THR | B | 195 | -7.492 | -18.901 | 105.677 | 1.00 | 39.46 |
| 7631 | C | THR | B | 195 | -9.823 | -18.557 | 104.029 | 1.00 | 39.04 |
| 7632 | O | THR | B | 195 | -10.530 | -19.385 | 104.615 | 1.00 | 39.15 |
| 7633 | N | PHE | B | 196 | -10.170 | -17.286 | 103.914 | 1.00 | 38.64 |
| 7634 | CA | PHE | B | 196 | -11.400 | -16.837 | 104.541 | 1.00 | 38.73 |
| 7635 | CB | PHE | B | 196 | -11.143 | -15.571 | 105.365 | 1.00 | 39.12 |
| 7636 | CG | PHE | B | 196 | -10.179 | -15.766 | 106.515 | 1.00 | 38.78 |
| 7637 | CD1 | PHE | B | 196 | -10.581 | -16.387 | 107.677 | 1.00 | 39.07 |
| 7638 | CE1 | PHE | B | 196 | -9.695 | -16.552 | 108.745 | 1.00 | 39.69 |
| 7639 | CZ | PHE | B | 196 | -8.399 | -16.083 | 108.653 | 1.00 | 38.45 |
| 7640 | CE2 | PHE | B | 196 | -7.986 | -15.449 | 107.506 | 1.00 | 39.56 |

FIGURE 3 ET

| A | B | C | D | E | F | G | H | I | J |
|---|---|---|---|---|---|---|---|---|---|
| 7641 | CD2 | PHE | B | 196 | -8.876 | -15.294 | 106.436 | 1.00 | 40.57 |
| 7642 | C | PHE | B | 196 | -12.538 | -16.608 | 103.540 | 1.00 | 38.22 |
| 7643 | O | PHE | B | 196 | -12.301 | -16.341 | 102.359 | 1.00 | 37.99 |
| 7644 | N | LEU | B | 197 | -13.769 | -16.780 | 104.018 | 1.00 | 37.58 |
| 7645 | CA | LEU | B | 197 | -14.960 | -16.417 | 103.260 | 1.00 | 36.62 |
| 7646 | CB | LEU | B | 197 | -15.883 | -17.610 | 103.053 | 1.00 | 36.67 |
| 7647 | CG | LEU | B | 197 | -17.171 | -17.316 | 102.275 | 1.00 | 35.82 |
| 7648 | CD1 | LEU | B | 197 | -18.028 | -18.570 | 102.130 | 1.00 | 34.72 |
| 7649 | CD2 | LEU | B | 197 | -16.844 | -16.752 | 100.911 | 1.00 | 35.59 |
| 7650 | C | LEU | B | 197 | -15.681 | -15.359 | 104.074 | 1.00 | 36.35 |
| 7651 | O | LEU | B | 197 | -16.209 | -15.636 | 105.150 | 1.00 | 36.69 |
| 7652 | N | ALA | B | 198 | -15.672 | -14.131 | 103.592 | 1.00 | 35.96 |
| 7653 | CA | ALA | B | 198 | -16.378 | -13.076 | 104.291 | 1.00 | 35.46 |
| 7654 | CB | ALA | B | 198 | -15.689 | -11.744 | 104.069 | 1.00 | 34.80 |
| 7655 | C | ALA | B | 198 | -17.766 | -13.069 | 103.671 | 1.00 | 35.25 |
| 7656 | O | ALA | B | 198 | -17.911 | -13.417 | 102.504 | 1.00 | 35.46 |
| 7657 | N | TYR | B | 199 | -18.778 | -12.686 | 104.438 | 1.00 | 34.76 |
| 7658 | CA | TYR | B | 199 | -20.118 | -12.551 | 103.885 | 1.00 | 34.75 |
| 7659 | CB | TYR | B | 199 | -20.802 | -13.915 | 103.750 | 1.00 | 34.69 |
| 7660 | CG | TYR | B | 199 | -21.164 | -14.595 | 105.049 | 1.00 | 34.33 |
| 7661 | CD1 | TYR | B | 199 | -22.431 | -14.481 | 105.567 | 1.00 | 34.88 |
| 7662 | CE1 | TYR | B | 199 | -22.788 | -15.115 | 106.741 | 1.00 | 34.48 |
| 7663 | CZ | TYR | B | 199 | -21.863 | -15.868 | 107.414 | 1.00 | 34.51 |
| 7664 | OH | TYR | B | 199 | -22.249 | -16.492 | 108.574 | 1.00 | 34.37 |
| 7665 | CE2 | TYR | B | 199 | -20.587 | -16.002 | 106.917 | 1.00 | 33.81 |
| 7666 | CD2 | TYR | B | 199 | -20.244 | -15.371 | 105.742 | 1.00 | 33.39 |
| 7667 | C | TYR | B | 199 | -21.006 | -11.591 | 104.682 | 1.00 | 35.01 |
| 7668 | O | TYR | B | 199 | -20.736 | -11.302 | 105.857 | 1.00 | 34.69 |
| 7669 | N | ALA | B | 200 | -22.058 | -11.106 | 104.023 | 1.00 | 34.47 |
| 7670 | CA | ALA | B | 200 | -23.045 | -10.246 | 104.649 | 1.00 | 34.12 |
| 7671 | CB | ALA | B | 200 | -23.355 | -9.061 | 103.760 | 1.00 | 33.97 |
| 7672 | C | ALA | B | 200 | -24.290 | -11.077 | 104.852 | 1.00 | 34.39 |
| 7673 | O | ALA | B | 200 | -24.498 | -12.068 | 104.151 | 1.00 | 34.15 |
| 7674 | N | GLN | B | 201 | -25.096 | -10.704 | 105.841 | 1.00 | 34.40 |
| 7675 | CA | GLN | B | 201 | -26.373 | -11.356 | 106.069 | 1.00 | 33.96 |
| 7676 | CB | GLN | B | 201 | -26.377 | -12.167 | 107.352 | 1.00 | 34.46 |
| 7677 | CG | GLN | B | 201 | -27.724 | -12.772 | 107.659 | 1.00 | 32.51 |
| 7678 | CD | GLN | B | 201 | -27.834 | -13.283 | 109.076 | 1.00 | 33.53 |
| 7679 | OE1 | GLN | B | 201 | -27.775 | -14.507 | 109.314 | 1.00 | 33.56 |
| 7680 | NE2 | GLN | B | 201 | -28.019 | -12.361 | 110.028 | 1.00 | 31.19 |
| 7681 | C | GLN | B | 201 | -27.435 | -10.274 | 106.163 | 1.00 | 34.27 |
| 7682 | O | GLN | B | 201 | -27.296 | -9.334 | 106.945 | 1.00 | 34.41 |
| 7683 | N | PHE | B | 202 | -28.504 | -10.414 | 105.383 | 1.00 | 34.03 |
| 7684 | CA | PHE | B | 202 | -29.508 | -9.366 | 105.324 | 1.00 | 33.58 |
| 7685 | CB | PHE | B | 202 | -29.678 | -8.875 | 103.876 | 1.00 | 32.92 |
| 7686 | CG | PHE | B | 202 | -28.403 | -8.329 | 103.267 | 1.00 | 31.65 |
| 7687 | CD1 | PHE | B | 202 | -28.003 | -7.023 | 103.510 | 1.00 | 27.76 |
| 7688 | CE1 | PHE | B | 202 | -26.847 | -6.536 | 102.961 | 1.00 | 27.18 |
| 7689 | CZ | PHE | B | 202 | -26.045 | -7.356 | 102.164 | 1.00 | 26.78 |
| 7690 | CE2 | PHE | B | 202 | -26.429 | -8.647 | 101.922 | 1.00 | 27.05 |
| 7691 | CD2 | PHE | B | 202 | -27.597 | -9.133 | 102.468 | 1.00 | 29.82 |

FIGURE 3 EU

| A | B | C | D | E | F | G | H | I | J |
|---|---|---|---|---|---|---|---|---|---|
| 7692 | C | PHE | B | 202 | -30.814 | -9.819 | 105.953 | 1.00 | 33.86 |
| 7693 | O | PHE | B | 202 | -31.283 | -10.925 | 105.738 | 1.00 | 34.06 |
| 7694 | N | ASN | B | 203 | -31.382 | -8.956 | 106.771 | 1.00 | 34.76 |
| 7695 | CA | ASN | B | 203 | -32.612 | -9.267 | 107.473 | 1.00 | 35.42 |
| 7696 | CB | ASN | B | 203 | -32.397 | -9.046 | 108.975 | 1.00 | 35.36 |
| 7697 | CG | ASN | B | 203 | -33.549 | -9.565 | 109.817 | 1.00 | 38.08 |
| 7698 | OD1 | ASN | B | 203 | -34.646 | -9.813 | 109.311 | 1.00 | 39.09 |
| 7699 | ND2 | ASN | B | 203 | -33.308 | -9.729 | 111.117 | 1.00 | 44.51 |
| 7700 | C | ASN | B | 203 | -33.672 | -8.325 | 106.926 | 1.00 | 35.44 |
| 7701 | O | ASN | B | 203 | -33.517 | -7.113 | 107.046 | 1.00 | 35.12 |
| 7702 | N | ASP | B | 204 | -34.730 | -8.870 | 106.319 | 1.00 | 35.37 |
| 7703 | CA | ASP | B | 204 | -35.775 | -8.040 | 105.705 | 1.00 | 36.12 |
| 7704 | CB | ASP | B | 204 | -35.880 | -8.318 | 104.199 | 1.00 | 36.29 |
| 7705 | CG | ASP | B | 204 | -34.869 | -7.543 | 103.398 | 1.00 | 35.99 |
| 7706 | OD1 | ASP | B | 204 | -33.668 | -7.838 | 103.486 | 1.00 | 38.20 |
| 7707 | OD2 | ASP | B | 204 | -35.167 | -6.602 | 102.666 | 1.00 | 35.99 |
| 7708 | C | ASP | B | 204 | -37.135 | -8.243 | 106.354 | 1.00 | 36.77 |
| 7709 | O | ASP | B | 204 | -38.174 | -7.885 | 105.799 | 1.00 | 36.63 |
| 7710 | N | THR | B | 205 | -37.096 | -8.818 | 107.546 | 1.00 | 37.26 |
| 7711 | CA | THR | B | 205 | -38.255 | -9.136 | 108.367 | 1.00 | 37.48 |
| 7712 | CB | THR | B | 205 | -37.777 | -9.252 | 109.815 | 1.00 | 37.68 |
| 7713 | OG1 | THR | B | 205 | -36.589 | -10.057 | 109.849 | 1.00 | 39.08 |
| 7714 | CG2 | THR | B | 205 | -38.771 | -10.014 | 110.661 | 1.00 | 37.50 |
| 7715 | C | THR | B | 205 | -39.407 | -8.141 | 108.311 | 1.00 | 37.68 |
| 7716 | O | THR | B | 205 | -40.579 | -8.525 | 108.135 | 1.00 | 38.26 |
| 7717 | N | GLU | B | 206 | -39.102 | -6.866 | 108.477 | 1.00 | 37.06 |
| 7718 | CA | GLU | B | 206 | -40.190 | -5.900 | 108.498 | 1.00 | 37.10 |
| 7719 | CB | GLU | B | 206 | -40.222 | -5.132 | 109.826 | 1.00 | 37.62 |
| 7720 | CG | GLU | B | 206 | -40.662 | -5.969 | 111.015 | 1.00 | 41.16 |
| 7721 | CD | GLU | B | 206 | -40.329 | -5.306 | 112.341 | 1.00 | 46.39 |
| 7722 | OE1 | GLU | B | 206 | -41.202 | -4.586 | 112.887 | 1.00 | 47.55 |
| 7723 | OE2 | GLU | B | 206 | -39.190 | -5.502 | 112.838 | 1.00 | 48.96 |
| 7724 | C | GLU | B | 206 | -40.143 | -4.930 | 107.339 | 1.00 | 35.80 |
| 7725 | O | GLU | B | 206 | -40.781 | -3.870 | 107.398 | 1.00 | 35.31 |
| 7726 | N | VAL | B | 207 | -39.372 | -5.244 | 106.295 | 1.00 | 34.51 |
| 7727 | CA | VAL | B | 207 | -39.441 | -4.350 | 105.150 | 1.00 | 33.14 |
| 7728 | CB | VAL | B | 207 | -38.121 | -4.217 | 104.303 | 1.00 | 33.75 |
| 7729 | CG1 | VAL | B | 207 | -38.263 | -4.763 | 102.906 | 1.00 | 31.71 |
| 7730 | CG2 | VAL | B | 207 | -36.879 | -4.758 | 105.070 | 1.00 | 32.67 |
| 7731 | C | VAL | B | 207 | -40.709 | -4.733 | 104.390 | 1.00 | 32.32 |
| 7732 | O | VAL | B | 207 | -41.032 | -5.918 | 104.242 | 1.00 | 31.19 |
| 7733 | N | PRO | B | 208 | -41.486 | -3.726 | 104.025 | 1.00 | 31.87 |
| 7734 | CA | PRO | B | 208 | -42.766 | -3.964 | 103.348 | 1.00 | 31.42 |
| 7735 | CB | PRO | B | 208 | -43.375 | -2.560 | 103.229 | 1.00 | 31.29 |
| 7736 | CG | PRO | B | 208 | -42.630 | -1.733 | 104.287 | 1.00 | 31.48 |
| 7737 | CD | PRO | B | 208 | -41.219 | -2.291 | 104.239 | 1.00 | 31.46 |
| 7738 | C | PRO | B | 208 | -42.511 | -4.546 | 101.979 | 1.00 | 30.79 |
| 7739 | O | PRO | B | 208 | -41.451 | -4.334 | 101.378 | 1.00 | 29.86 |
| 7740 | N | LEU | B | 209 | -43.481 | -5.301 | 101.499 | 1.00 | 30.64 |
| 7741 | CA | LEU | B | 209 | -43.352 | -5.921 | 100.189 | 1.00 | 30.83 |
| 7742 | CB | LEU | B | 209 | -43.779 | -7.388 | 100.262 | 1.00 | 31.12 |

FIGURE 3 EV

| A | B | C | D | E | F | G | H | I | J |
|---|---|---|---|---|---|---|---|---|---|
| 7743 | CG | LEU | B | 209 | -42.801 | -8.162 | 101.171 | 1.00 | 33.07 |
| 7744 | CD1 | LEU | B | 209 | -42.617 | -9.617 | 100.757 | 1.00 | 33.85 |
| 7745 | CD2 | LEU | B | 209 | -43.238 | -8.066 | 102.620 | 1.00 | 34.18 |
| 7746 | C | LEU | B | 209 | -44.139 | -5.177 | 99.130 | 1.00 | 29.88 |
| 7747 | O | LEU | B | 209 | -45.274 | -4.782 | 99.353 | 1.00 | 30.00 |
| 7748 | N | ILE | B | 210 | -43.510 | -4.948 | 97.986 | 1.00 | 29.02 |
| 7749 | CA | ILE | B | 210 | -44.221 | -4.408 | 96.863 | 1.00 | 27.71 |
| 7750 | CB | ILE | B | 210 | -43.271 | -3.741 | 95.860 | 1.00 | 27.81 |
| 7751 | CG1 | ILE | B | 210 | -44.040 | -3.293 | 94.610 | 1.00 | 26.93 |
| 7752 | CD1 | ILE | B | 210 | -45.109 | -2.253 | 94.857 | 1.00 | 24.74 |
| 7753 | CG2 | ILE | B | 210 | -42.135 | -4.690 | 95.440 | 1.00 | 26.99 |
| 7754 | C | ILE | B | 210 | -44.911 | -5.632 | 96.263 | 1.00 | 27.48 |
| 7755 | O | ILE | B | 210 | -44.317 | -6.713 | 96.207 | 1.00 | 27.42 |
| 7756 | N | GLU | B | 211 | -46.163 | -5.467 | 95.851 | 1.00 | 26.30 |
| 7757 | CA | GLU | B | 211 | -46.941 | -6.555 | 95.265 | 1.00 | 25.53 |
| 7758 | CB | GLU | B | 211 | -48.157 | -6.895 | 96.134 | 1.00 | 25.38 |
| 7759 | CG | GLU | B | 211 | -47.839 | -7.241 | 97.577 | 1.00 | 27.67 |
| 7760 | CD | GLU | B | 211 | -49.085 | -7.608 | 98.369 | 1.00 | 30.61 |
| 7761 | OE1 | GLU | B | 211 | -49.242 | -8.789 | 98.686 | 1.00 | 30.31 |
| 7762 | OE2 | GLU | B | 211 | -49.927 | -6.717 | 98.673 | 1.00 | 34.16 |
| 7763 | C | GLU | B | 211 | -47.417 | -6.121 | 93.888 | 1.00 | 24.64 |
| 7764 | O | GLU | B | 211 | -47.874 | -4.997 | 93.713 | 1.00 | 23.65 |
| 7765 | N | TYR | B | 212 | -47.280 | -7.005 | 92.907 | 1.00 | 24.26 |
| 7766 | CA | TYR | B | 212 | -47.770 | -6.714 | 91.564 | 1.00 | 24.09 |
| 7767 | CB | TYR | B | 212 | -46.768 | -5.908 | 90.756 | 1.00 | 23.87 |
| 7768 | CG | TYR | B | 212 | -45.395 | -6.515 | 90.620 | 1.00 | 24.60 |
| 7769 | CD1 | TYR | B | 212 | -45.118 | -7.426 | 89.624 | 1.00 | 22.59 |
| 7770 | CE1 | TYR | B | 212 | -43.872 | -7.957 | 89.480 | 1.00 | 24.30 |
| 7771 | CZ | TYR | B | 212 | -42.857 | -7.574 | 90.333 | 1.00 | 25.32 |
| 7772 | OH | TYR | B | 212 | -41.608 | -8.119 | 90.198 | 1.00 | 23.27 |
| 7773 | CE2 | TYR | B | 212 | -43.094 | -6.658 | 91.332 | 1.00 | 26.02 |
| 7774 | CD2 | TYR | B | 212 | -44.362 | -6.135 | 91.471 | 1.00 | 25.60 |
| 7775 | C | TYR | B | 212 | -48.177 | -7.976 | 90.833 | 1.00 | 23.68 |
| 7776 | O | TYR | B | 212 | -47.716 | -9.062 | 91.158 | 1.00 | 24.00 |
| 7777 | N | SER | B | 213 | -49.080 | -7.833 | 89.879 | 1.00 | 23.67 |
| 7778 | CA | SER | B | 213 | -49.553 | -8.972 | 89.112 | 1.00 | 23.81 |
| 7779 | CB | SER | B | 213 | -50.856 | -8.639 | 88.400 | 1.00 | 23.52 |
| 7780 | OG | SER | B | 213 | -51.949 | -8.658 | 89.291 | 1.00 | 22.25 |
| 7781 | C | SER | B | 213 | -48.524 | -9.434 | 88.087 | 1.00 | 24.15 |
| 7782 | O | SER | B | 213 | -47.827 | -8.615 | 87.455 | 1.00 | 23.38 |
| 7783 | N | PHE | B | 214 | -48.395 | -10.755 | 87.980 | 1.00 | 24.01 |
| 7784 | CA | PHE | B | 214 | -47.565 | -11.359 | 86.938 | 1.00 | 23.87 |
| 7785 | CB | PHE | B | 214 | -46.350 | -12.083 | 87.486 | 1.00 | 23.47 |
| 7786 | CG | PHE | B | 214 | -45.334 | -12.351 | 86.441 | 1.00 | 22.91 |
| 7787 | CD1 | PHE | B | 214 | -45.334 | -13.555 | 85.750 | 1.00 | 21.91 |
| 7788 | CE1 | PHE | B | 214 | -44.426 | -13.780 | 84.733 | 1.00 | 22.86 |
| 7789 | CZ | PHE | B | 214 | -43.508 | -12.805 | 84.398 | 1.00 | 21.44 |
| 7790 | CE2 | PHE | B | 214 | -43.514 | -11.604 | 85.080 | 1.00 | 23.24 |
| 7791 | CD2 | PHE | B | 214 | -44.432 | -11.371 | 86.081 | 1.00 | 19.59 |
| 7792 | C | PHE | B | 214 | -48.471 | -12.308 | 86.185 | 1.00 | 24.16 |
| 7793 | O | PHE | B | 214 | -49.007 | -13.278 | 86.767 | 1.00 | 24.65 |

FIGURE 3 EW

| A | B | C | D | E | F | G | H | I | J |
|---|---|---|---|---|---|---|---|---|---|
| 7794 | N | TYR | B | 215 | -48.677 | -12.011 | 84.907 | 1.00 | 24.05 |
| 7795 | CA | TYR | B | 215 | -49.688 | -12.722 | 84.123 | 1.00 | 23.44 |
| 7796 | CB | TYR | B | 215 | -50.289 | -11.798 | 83.062 | 1.00 | 22.72 |
| 7797 | CG | TYR | B | 215 | -50.831 | -10.575 | 83.708 | 1.00 | 20.73 |
| 7798 | CD1 | TYR | B | 215 | -50.069 | -9.414 | 83.794 | 1.00 | 19.55 |
| 7799 | CE1 | TYR | B | 215 | -50.557 | -8.289 | 84.444 | 1.00 | 16.87 |
| 7800 | CZ | TYR | B | 215 | -51.825 | -8.330 | 85.006 | 1.00 | 17.23 |
| 7801 | OH | TYR | B | 215 | -52.336 | -7.212 | 85.644 | 1.00 | 17.71 |
| 7802 | CE2 | TYR | B | 215 | -52.590 | -9.457 | 84.924 | 1.00 | 15.78 |
| 7803 | CD2 | TYR | B | 215 | -52.096 | -10.578 | 84.285 | 1.00 | 19.58 |
| 7804 | C | TYR | B | 215 | -49.171 | -14.010 | 83.525 | 1.00 | 23.64 |
| 7805 | O | TYR | B | 215 | -49.915 | -14.987 | 83.417 | 1.00 | 23.38 |
| 7806 | N | SER | B | 216 | -47.904 | -13.998 | 83.131 | 1.00 | 23.88 |
| 7807 | CA | SER | B | 216 | -47.240 | -15.197 | 82.638 | 1.00 | 24.66 |
| 7808 | CB | SER | B | 216 | -47.407 | -16.327 | 83.648 | 1.00 | 24.13 |
| 7809 | OG | SER | B | 216 | -46.548 | -17.388 | 83.310 | 1.00 | 24.18 |
| 7810 | C | SER | B | 216 | -47.771 | -15.690 | 81.308 | 1.00 | 25.46 |
| 7811 | O | SER | B | 216 | -48.546 | -15.001 | 80.639 | 1.00 | 25.75 |
| 7812 | N | ASP | B | 217 | -47.370 | -16.903 | 80.936 | 1.00 | 25.82 |
| 7813 | CA | ASP | B | 217 | -47.908 | -17.500 | 79.722 | 1.00 | 27.15 |
| 7814 | CB | ASP | B | 217 | -47.469 | -18.956 | 79.581 | 1.00 | 28.06 |
| 7815 | CG | ASP | B | 217 | -47.928 | -19.551 | 78.282 | 1.00 | 31.35 |
| 7816 | OD1 | ASP | B | 217 | -47.258 | -19.269 | 77.274 | 1.00 | 37.45 |
| 7817 | OD2 | ASP | B | 217 | -48.963 | -20.255 | 78.141 | 1.00 | 34.61 |
| 7818 | C | ASP | B | 217 | -49.427 | -17.452 | 79.757 | 1.00 | 26.37 |
| 7819 | O | ASP | B | 217 | -50.027 | -17.399 | 80.827 | 1.00 | 26.98 |
| 7820 | N | GLU | B | 218 | -50.055 | -17.480 | 78.595 | 1.00 | 26.26 |
| 7821 | CA | GLU | B | 218 | -51.499 | -17.396 | 78.528 | 1.00 | 25.79 |
| 7822 | CB | GLU | B | 218 | -51.982 | -17.109 | 77.093 | 1.00 | 26.24 |
| 7823 | CG | GLU | B | 218 | -52.256 | -18.313 | 76.218 | 1.00 | 27.13 |
| 7824 | CD | GLU | B | 218 | -53.029 | -17.960 | 74.947 | 1.00 | 28.56 |
| 7825 | OE1 | GLU | B | 218 | -54.252 | -18.243 | 74.880 | 1.00 | 27.55 |
| 7826 | OE2 | GLU | B | 218 | -52.403 | -17.432 | 74.001 | 1.00 | 27.21 |
| 7827 | C | GLU | B | 218 | -52.169 | -18.614 | 79.157 | 1.00 | 25.85 |
| 7828 | O | GLU | B | 218 | -53.349 | -18.577 | 79.480 | 1.00 | 25.38 |
| 7829 | N | SER | B | 219 | -51.386 | -19.677 | 79.345 | 1.00 | 26.17 |
| 7830 | CA | SER | B | 219 | -51.771 | -20.896 | 80.078 | 1.00 | 25.81 |
| 7831 | CB | SER | B | 219 | -50.551 | -21.825 | 80.157 | 1.00 | 25.94 |
| 7832 | OG | SER | B | 219 | -50.585 | -22.694 | 79.064 | 1.00 | 29.48 |
| 7833 | C | SER | B | 219 | -52.174 | -20.654 | 81.531 | 1.00 | 24.81 |
| 7834 | O | SER | B | 219 | -53.011 | -21.363 | 82.081 | 1.00 | 24.67 |
| 7835 | N | LEU | B | 220 | -51.501 | -19.724 | 82.188 | 1.00 | 23.40 |
| 7836 | CA | LEU | B | 220 | -51.823 | -19.460 | 83.584 | 1.00 | 22.91 |
| 7837 | CB | LEU | B | 220 | -50.858 | -18.421 | 84.132 | 1.00 | 21.98 |
| 7838 | CG | LEU | B | 220 | -50.721 | -18.394 | 85.640 | 1.00 | 23.38 |
| 7839 | CD1 | LEU | B | 220 | -49.896 | -17.196 | 86.064 | 1.00 | 22.99 |
| 7840 | CD2 | LEU | B | 220 | -50.102 | -19.713 | 86.163 | 1.00 | 21.57 |
| 7841 | C | LEU | B | 220 | -53.263 | -18.942 | 83.686 | 1.00 | 22.46 |
| 7842 | O | LEU | B | 220 | -53.576 | -17.906 | 83.139 | 1.00 | 22.55 |
| 7843 | N | GLN | B | 221 | -54.128 | -19.674 | 84.370 | 1.00 | 21.97 |
| 7844 | CA | GLN | B | 221 | -55.515 | -19.276 | 84.522 | 1.00 | 21.93 |

FIGURE 3 EX

| A | B | C | D | E | F | G | H | I | J |
|---|---|---|---|---|---|---|---|---|---|
| 7845 | CB | GLN | B | 221 | -56.357 | -20.463 | 85.014 | 1.00 | 21.65 |
| 7846 | CG | GLN | B | 221 | -57.856 | -20.174 | 85.026 | 1.00 | 21.33 |
| 7847 | CD | GLN | B | 221 | -58.676 | -21.412 | 85.310 | 1.00 | 21.73 |
| 7848 | OE1 | GLN | B | 221 | -58.259 | -22.270 | 86.111 | 1.00 | 25.67 |
| 7849 | NE2 | GLN | B | 221 | -59.807 | -21.545 | 84.631 | 1.00 | 17.84 |
| 7850 | C | GLN | B | 221 | -55.714 | -18.070 | 85.454 | 1.00 | 22.01 |
| 7851 | O | GLN | B | 221 | -56.508 | -17.186 | 85.164 | 1.00 | 21.81 |
| 7852 | N | TYR | B | 222 | -54.978 | -18.055 | 86.565 | 1.00 | 21.99 |
| 7853 | CA | TYR | B | 222 | -55.059 | -16.993 | 87.563 | 1.00 | 21.65 |
| 7854 | CB | TYR | B | 222 | -55.367 | -17.582 | 88.938 | 1.00 | 21.50 |
| 7855 | CG | TYR | B | 222 | -56.785 | -18.003 | 89.152 | 1.00 | 20.25 |
| 7856 | CD1 | TYR | B | 222 | -57.710 | -17.138 | 89.750 | 1.00 | 19.35 |
| 7857 | CE1 | TYR | B | 222 | -59.009 | -17.526 | 89.972 | 1.00 | 16.76 |
| 7858 | CZ | TYR | B | 222 | -59.399 | -18.801 | 89.597 | 1.00 | 20.61 |
| 7859 | OH | TYR | B | 222 | -60.700 | -19.224 | 89.798 | 1.00 | 20.99 |
| 7860 | CE2 | TYR | B | 222 | -58.504 | -19.667 | 89.004 | 1.00 | 20.11 |
| 7861 | CD2 | TYR | B | 222 | -57.201 | -19.269 | 88.800 | 1.00 | 19.61 |
| 7862 | C | TYR | B | 222 | -53.702 | -16.343 | 87.673 | 1.00 | 21.62 |
| 7863 | O | TYR | B | 222 | -52.711 | -17.013 | 87.929 | 1.00 | 21.72 |
| 7864 | N | PRO | B | 223 | -53.654 | -15.037 | 87.512 | 1.00 | 22.12 |
| 7865 | CA | PRO | B | 223 | -52.388 | -14.320 | 87.587 | 1.00 | 22.77 |
| 7866 | CB | PRO | B | 223 | -52.808 | -12.855 | 87.468 | 1.00 | 22.52 |
| 7867 | CG | PRO | B | 223 | -54.135 | -12.919 | 86.728 | 1.00 | 23.29 |
| 7868 | CD | PRO | B | 223 | -54.801 | -14.151 | 87.238 | 1.00 | 21.98 |
| 7869 | C | PRO | B | 223 | -51.684 | -14.572 | 88.914 | 1.00 | 23.77 |
| 7870 | O | PRO | B | 223 | -52.296 | -14.940 | 89.935 | 1.00 | 23.36 |
| 7871 | N | LYS | B | 224 | -50.375 | -14.380 | 88.887 | 1.00 | 24.79 |
| 7872 | CA | LYS | B | 224 | -49.558 | -14.565 | 90.075 | 1.00 | 25.75 |
| 7873 | CB | LYS | B | 224 | -48.195 | -15.138 | 89.674 | 1.00 | 25.86 |
| 7874 | CG | LYS | B | 224 | -47.213 | -15.395 | 90.824 | 1.00 | 29.92 |
| 7875 | CD | LYS | B | 224 | -45.906 | -16.022 | 90.293 | 1.00 | 35.92 |
| 7876 | CE | LYS | B | 224 | -44.974 | -16.533 | 91.400 | 1.00 | 40.36 |
| 7877 | NZ | LYS | B | 224 | -44.164 | -17.744 | 90.943 | 1.00 | 42.83 |
| 7878 | C | LYS | B | 224 | -49.365 | -13.201 | 90.702 | 1.00 | 25.10 |
| 7879 | O | LYS | B | 224 | -49.345 | -12.184 | 90.006 | 1.00 | 25.60 |
| 7880 | N | THR | B | 225 | -49.256 | -13.162 | 92.017 | 1.00 | 25.06 |
| 7881 | CA | THR | B | 225 | -48.895 | -11.923 | 92.657 | 1.00 | 24.78 |
| 7882 | CB | THR | B | 225 | -49.696 | -11.694 | 93.905 | 1.00 | 24.99 |
| 7883 | OG1 | THR | B | 225 | -51.081 | -11.616 | 93.574 | 1.00 | 22.31 |
| 7884 | CG2 | THR | B | 225 | -49.345 | -10.303 | 94.475 | 1.00 | 23.65 |
| 7885 | C | THR | B | 225 | -47.456 | -12.046 | 93.069 | 1.00 | 25.30 |
| 7886 | O | THR | B | 225 | -47.127 | -12.865 | 93.904 | 1.00 | 25.31 |
| 7887 | N | VAL | B | 226 | -46.589 | -11.239 | 92.487 | 1.00 | 25.52 |
| 7888 | CA | VAL | B | 226 | -45.208 | -11.289 | 92.889 | 1.00 | 25.68 |
| 7889 | CB | VAL | B | 226 | -44.273 | -10.831 | 91.730 | 1.00 | 26.20 |
| 7890 | CG1 | VAL | B | 226 | -42.817 | -10.607 | 92.220 | 1.00 | 24.52 |
| 7891 | CG2 | VAL | B | 226 | -44.317 | -11.863 | 90.607 | 1.00 | 23.77 |
| 7892 | C | VAL | B | 226 | -45.075 | -10.421 | 94.150 | 1.00 | 26.34 |
| 7893 | O | VAL | B | 226 | -45.729 | -9.390 | 94.272 | 1.00 | 25.24 |
| 7894 | N | ARG | B | 227 | -44.277 | -10.868 | 95.111 | 1.00 | 26.87 |
| 7895 | CA | ARG | B | 227 | -44.108 | -10.087 | 96.335 | 1.00 | 28.00 |

FIGURE 3 EY

| A | B | C | D | E | F | G | H | I | J |
|---|---|---|---|---|---|---|---|---|---|
| 7896 | CB | ARG | B | 227 | -44.894 | -10.714 | 97.490 | 1.00 | 28.35 |
| 7897 | CG | ARG | B | 227 | -46.428 | -10.718 | 97.266 | 1.00 | 29.92 |
| 7898 | CD | ARG | B | 227 | -47.187 | -11.624 | 98.240 | 1.00 | 33.73 |
| 7899 | NE | ARG | B | 227 | -48.636 | -11.569 | 98.062 | 1.00 | 37.78 |
| 7900 | CZ | ARG | B | 227 | -49.380 | -12.556 | 97.553 | 1.00 | 39.98 |
| 7901 | NH1 | ARG | B | 227 | -48.828 | -13.696 | 97.132 | 1.00 | 41.04 |
| 7902 | NH2 | ARG | B | 227 | -50.687 | -12.397 | 97.457 | 1.00 | 41.02 |
| 7903 | C | ARG | B | 227 | -42.637 | -10.001 | 96.664 | 1.00 | 27.69 |
| 7904 | O | ARG | B | 227 | -41.974 | -11.022 | 96.801 | 1.00 | 28.57 |
| 7905 | N | VAL | B | 228 | -42.109 | -8.790 | 96.738 | 1.00 | 27.18 |
| 7906 | CA | VAL | B | 228 | -40.707 | -8.634 | 97.055 | 1.00 | 26.68 |
| 7907 | CB | VAL | B | 228 | -39.812 | -8.503 | 95.778 | 1.00 | 27.22 |
| 7908 | CG1 | VAL | B | 228 | -38.526 | -7.778 | 96.074 | 1.00 | 25.99 |
| 7909 | CG2 | VAL | B | 228 | -40.560 | -7.873 | 94.618 | 1.00 | 27.19 |
| 7910 | C | VAL | B | 228 | -40.431 | -7.560 | 98.110 | 1.00 | 26.47 |
| 7911 | O | VAL | B | 228 | -40.971 | -6.448 | 98.054 | 1.00 | 26.20 |
| 7912 | N | PRO | B | 229 | -39.645 | -7.937 | 99.118 | 1.00 | 25.68 |
| 7913 | CA | PRO | B | 229 | -39.241 | -6.997 | 100.165 | 1.00 | 25.11 |
| 7914 | CB | PRO | B | 229 | -38.229 | -7.803 | 100.985 | 1.00 | 25.52 |
| 7915 | CG | PRO | B | 229 | -38.704 | -9.213 | 100.850 | 1.00 | 24.51 |
| 7916 | CD | PRO | B | 229 | -39.129 | -9.300 | 99.361 | 1.00 | 25.37 |
| 7917 | C | PRO | B | 229 | -38.617 | -5.823 | 99.474 | 1.00 | 25.27 |
| 7918 | O | PRO | B | 229 | -37.656 | -5.953 | 98.720 | 1.00 | 25.93 |
| 7919 | N | TYR | B | 230 | -39.200 | -4.656 | 99.673 | 1.00 | 25.44 |
| 7920 | CA | TYR | B | 230 | -38.730 | -3.508 | 98.954 | 1.00 | 25.45 |
| 7921 | CB | TYR | B | 230 | -39.409 | -3.470 | 97.584 | 1.00 | 25.29 |
| 7922 | CG | TYR | B | 230 | -39.032 | -2.314 | 96.666 | 1.00 | 23.61 |
| 7923 | CD1 | TYR | B | 230 | -38.480 | -2.546 | 95.421 | 1.00 | 22.82 |
| 7924 | CE1 | TYR | B | 230 | -38.158 | -1.498 | 94.557 | 1.00 | 21.11 |
| 7925 | CZ | TYR | B | 230 | -38.413 | -0.211 | 94.939 | 1.00 | 22.06 |
| 7926 | OH | TYR | B | 230 | -38.103 | 0.850 | 94.111 | 1.00 | 20.01 |
| 7927 | CE2 | TYR | B | 230 | -38.974 | 0.044 | 96.172 | 1.00 | 23.04 |
| 7928 | CD2 | TYR | B | 230 | -39.283 | -1.009 | 97.026 | 1.00 | 24.33 |
| 7929 | C | TYR | B | 230 | -39.091 | -2.303 | 99.764 | 1.00 | 26.35 |
| 7930 | O | TYR | B | 230 | -40.270 | -2.016 | 99.975 | 1.00 | 26.45 |
| 7931 | N | PRO | B | 231 | -38.079 | -1.565 | 100.197 | 1.00 | 26.82 |
| 7932 | CA | PRO | B | 231 | -38.331 | -0.411 | 101.041 | 1.00 | 26.63 |
| 7933 | CB | PRO | B | 231 | -37.055 | -0.307 | 101.880 | 1.00 | 26.96 |
| 7934 | CG | PRO | B | 231 | -35.973 | -1.138 | 101.101 | 1.00 | 27.14 |
| 7935 | CD | PRO | B | 231 | -36.651 | -1.697 | 99.853 | 1.00 | 26.65 |
| 7936 | C | PRO | B | 231 | -38.467 | 0.834 | 100.175 | 1.00 | 26.53 |
| 7937 | O | PRO | B | 231 | -37.522 | 1.214 | 99.502 | 1.00 | 25.81 |
| 7938 | N | LYS | B | 232 | -39.636 | 1.459 | 100.198 | 1.00 | 26.67 |
| 7939 | CA | LYS | B | 232 | -39.768 | 2.742 | 99.550 | 1.00 | 27.57 |
| 7940 | CB | LYS | B | 232 | -41.228 | 2.982 | 99.120 | 1.00 | 27.68 |
| 7941 | CG | LYS | B | 232 | -41.742 | 1.919 | 98.113 | 1.00 | 27.32 |
| 7942 | CD | LYS | B | 232 | -43.216 | 2.092 | 97.786 | 1.00 | 27.71 |
| 7943 | CE | LYS | B | 232 | -43.735 | 1.092 | 96.706 | 1.00 | 25.66 |
| 7944 | NZ | LYS | B | 232 | -43.437 | 1.574 | 95.333 | 1.00 | 22.44 |
| 7945 | C | LYS | B | 232 | -39.235 | 3.799 | 100.541 | 1.00 | 28.03 |
| 7946 | O | LYS | B | 232 | -38.992 | 3.495 | 101.720 | 1.00 | 28.59 |

FIGURE 3 EZ

| A | B | C | D | E | F | G | H | I | J |
|---|---|---|---|---|---|---|---|---|---|
| 7947 | N | ALA | B | 233 | -38.994 | 5.008 | 100.064 | 1.00 | 28.09 |
| 7948 | CA | ALA | B | 233 | -38.473 | 6.064 | 100.926 | 1.00 | 29.37 |
| 7949 | CB | ALA | B | 233 | -38.667 | 7.408 | 100.269 | 1.00 | 28.92 |
| 7950 | C | ALA | B | 233 | -39.062 | 6.094 | 102.342 | 1.00 | 29.71 |
| 7951 | O | ALA | B | 233 | -40.270 | 6.032 | 102.518 | 1.00 | 30.57 |
| 7952 | N | GLY | B | 234 | -38.199 | 6.187 | 103.346 | 1.00 | 30.05 |
| 7953 | CA | GLY | B | 234 | -38.634 | 6.344 | 104.720 | 1.00 | 30.42 |
| 7954 | C | GLY | B | 234 | -39.279 | 5.141 | 105.356 | 1.00 | 31.45 |
| 7955 | O | GLY | B | 234 | -39.805 | 5.237 | 106.475 | 1.00 | 31.70 |
| 7956 | N | ALA | B | 235 | -39.245 | 4.007 | 104.654 | 1.00 | 31.70 |
| 7957 | CA | ALA | B | 235 | -39.823 | 2.762 | 105.149 | 1.00 | 31.68 |
| 7958 | CB | ALA | B | 235 | -40.331 | 1.930 | 103.975 | 1.00 | 31.98 |
| 7959 | C | ALA | B | 235 | -38.750 | 2.012 | 105.898 | 1.00 | 31.77 |
| 7960 | O | ALA | B | 235 | -37.587 | 2.375 | 105.804 | 1.00 | 31.93 |
| 7961 | N | VAL | B | 236 | -39.095 | 0.962 | 106.635 | 1.00 | 32.57 |
| 7962 | CA | VAL | B | 236 | -38.016 | 0.255 | 107.316 | 1.00 | 33.10 |
| 7963 | CB | VAL | B | 236 | -38.446 | -0.593 | 108.537 | 1.00 | 33.83 |
| 7964 | CG1 | VAL | B | 236 | -38.187 | -2.087 | 108.332 | 1.00 | 34.90 |
| 7965 | CG2 | VAL | B | 236 | -39.847 | -0.232 | 109.020 | 1.00 | 32.94 |
| 7966 | C | VAL | B | 236 | -37.147 | -0.525 | 106.338 | 1.00 | 32.85 |
| 7967 | O | VAL | B | 236 | -37.652 | -1.296 | 105.497 | 1.00 | 32.95 |
| 7968 | N | ASN | B | 237 | -35.842 | -0.265 | 106.442 | 1.00 | 32.00 |
| 7969 | CA | ASN | B | 237 | -34.813 | -0.837 | 105.588 | 1.00 | 31.06 |
| 7970 | CB | ASN | B | 237 | -33.595 | 0.081 | 105.559 | 1.00 | 30.94 |
| 7971 | CG | ASN | B | 237 | -33.662 | 1.080 | 104.448 | 1.00 | 29.99 |
| 7972 | OD1 | ASN | B | 237 | -34.492 | 0.950 | 103.567 | 1.00 | 30.71 |
| 7973 | ND2 | ASN | B | 237 | -32.790 | 2.079 | 104.470 | 1.00 | 28.91 |
| 7974 | C | ASN | B | 237 | -34.392 | -2.167 | 106.112 | 1.00 | 30.86 |
| 7975 | O | ASN | B | 237 | -34.726 | -2.508 | 107.224 | 1.00 | 31.35 |
| 7976 | N | PRO | B | 238 | -33.736 | -2.979 | 105.295 | 1.00 | 31.04 |
| 7977 | CA | PRO | B | 238 | -33.165 | -4.233 | 105.797 | 1.00 | 31.08 |
| 7978 | CB | PRO | B | 238 | -32.615 | -4.886 | 104.519 | 1.00 | 30.68 |
| 7979 | CG | PRO | B | 238 | -32.384 | -3.719 | 103.608 | 1.00 | 30.58 |
| 7980 | CD | PRO | B | 238 | -33.575 | -2.847 | 103.837 | 1.00 | 30.47 |
| 7981 | C | PRO | B | 238 | -32.007 | -3.944 | 106.781 | 1.00 | 31.59 |
| 7982 | O | PRO | B | 238 | -31.406 | -2.867 | 106.751 | 1.00 | 30.75 |
| 7983 | N | THR | B | 239 | -31.707 | -4.893 | 107.657 | 1.00 | 32.48 |
| 7984 | CA | THR | B | 239 | -30.552 | -4.737 | 108.524 | 1.00 | 33.35 |
| 7985 | CB | THR | B | 239 | -30.894 | -4.975 | 110.012 | 1.00 | 33.48 |
| 7986 | OG1 | THR | B | 239 | -31.549 | -6.238 | 110.171 | 1.00 | 33.78 |
| 7987 | CG2 | THR | B | 239 | -31.926 | -3.946 | 110.511 | 1.00 | 32.20 |
| 7988 | C | THR | B | 239 | -29.482 | -5.697 | 108.024 | 1.00 | 34.05 |
| 7989 | O | THR | B | 239 | -29.779 | -6.677 | 107.339 | 1.00 | 34.27 |
| 7990 | N | VAL | B | 240 | -28.235 | -5.402 | 108.349 | 1.00 | 34.30 |
| 7991 | CA | VAL | B | 240 | -27.128 | -6.198 | 107.853 | 1.00 | 34.60 |
| 7992 | CB | VAL | B | 240 | -26.404 | -5.449 | 106.730 | 1.00 | 34.08 |
| 7993 | CG1 | VAL | B | 240 | -25.321 | -6.329 | 106.094 | 1.00 | 33.81 |
| 7994 | CG2 | VAL | B | 240 | -25.830 | -4.149 | 107.263 | 1.00 | 33.77 |
| 7995 | C | VAL | B | 240 | -26.125 | -6.568 | 108.947 | 1.00 | 35.20 |
| 7996 | O | VAL | B | 240 | -25.862 | -5.793 | 109.872 | 1.00 | 34.33 |
| 7997 | N | LYS | B | 241 | -25.611 | -7.789 | 108.849 | 1.00 | 36.27 |

FIGURE 3 FA

| A | B | C | D | E | F | G | H | I | J |
|---|---|---|---|---|---|---|---|---|---|
| 7998 | CA | LYS | B | 241 | -24.549 | -8.253 | 109.727 | 1.00 | 37.18 |
| 7999 | CB | LYS | B | 241 | -25.018 | -9.402 | 110.599 | 1.00 | 36.94 |
| 8000 | CG | LYS | B | 241 | -25.460 | -8.988 | 112.005 | 1.00 | 37.33 |
| 8001 | CD | LYS | B | 241 | -26.948 | -9.027 | 112.191 | 1.00 | 37.13 |
| 8002 | CE | LYS | B | 241 | -27.329 | -9.127 | 113.668 | 1.00 | 37.02 |
| 8003 | NZ | LYS | B | 241 | -27.599 | -10.541 | 114.125 | 1.00 | 37.48 |
| 8004 | C | LYS | B | 241 | -23.419 | -8.704 | 108.830 | 1.00 | 38.02 |
| 8005 | O | LYS | B | 241 | -23.654 | -9.049 | 107.666 | 1.00 | 38.17 |
| 8006 | N | PHE | B | 242 | -22.191 | -8.695 | 109.345 | 1.00 | 38.53 |
| 8007 | CA | PHE | B | 242 | -21.060 | -9.112 | 108.538 | 1.00 | 38.67 |
| 8008 | CB | PHE | B | 242 | -20.150 | -7.919 | 108.261 | 1.00 | 38.63 |
| 8009 | CG | PHE | B | 242 | -19.066 | -8.205 | 107.257 | 1.00 | 39.51 |
| 8010 | CD1 | PHE | B | 242 | -19.311 | -8.073 | 105.900 | 1.00 | 38.66 |
| 8011 | CE1 | PHE | B | 242 | -18.322 | -8.335 | 104.974 | 1.00 | 40.21 |
| 8012 | CZ | PHE | B | 242 | -17.063 | -8.743 | 105.401 | 1.00 | 40.58 |
| 8013 | CE2 | PHE | B | 242 | -16.807 | -8.877 | 106.753 | 1.00 | 39.64 |
| 8014 | CD2 | PHE | B | 242 | -17.799 | -8.612 | 107.674 | 1.00 | 39.14 |
| 8015 | C | PHE | B | 242 | -20.307 | -10.232 | 109.243 | 1.00 | 39.45 |
| 8016 | O | PHE | B | 242 | -20.087 | -10.170 | 110.460 | 1.00 | 39.74 |
| 8017 | N | PHE | B | 243 | -19.929 | -11.264 | 108.494 | 1.00 | 39.56 |
| 8018 | CA | PHE | B | 243 | -19.220 | -12.394 | 109.075 | 1.00 | 40.01 |
| 8019 | CB | PHE | B | 243 | -20.144 | -13.583 | 109.252 | 1.00 | 40.24 |
| 8020 | CG | PHE | B | 243 | -21.400 | -13.294 | 110.005 | 1.00 | 39.63 |
| 8021 | CD1 | PHE | B | 243 | -22.480 | -12.702 | 109.375 | 1.00 | 38.78 |
| 8022 | CE1 | PHE | B | 243 | -23.652 | -12.455 | 110.063 | 1.00 | 38.28 |
| 8023 | CZ | PHE | B | 243 | -23.766 | -12.811 | 111.393 | 1.00 | 38.50 |
| 8024 | CE2 | PHE | B | 243 | -22.702 | -13.418 | 112.035 | 1.00 | 39.56 |
| 8025 | CD2 | PHE | B | 243 | -21.520 | -13.661 | 111.333 | 1.00 | 39.40 |
| 8026 | C | PHE | B | 243 | -18.059 | -12.891 | 108.222 | 1.00 | 40.72 |
| 8027 | O | PHE | B | 243 | -18.065 | -12.752 | 106.996 | 1.00 | 40.63 |
| 8028 | N | VAL | B | 244 | -17.060 | -13.474 | 108.879 | 1.00 | 41.01 |
| 8029 | CA | VAL | B | 244 | -15.986 | -14.142 | 108.164 | 1.00 | 41.48 |
| 8030 | CB | VAL | B | 244 | -14.733 | -13.267 | 107.963 | 1.00 | 41.57 |
| 8031 | CG1 | VAL | B | 244 | -14.658 | -12.196 | 108.984 | 1.00 | 42.82 |
| 8032 | CG2 | VAL | B | 244 | -13.483 | -14.109 | 107.935 | 1.00 | 41.56 |
| 8033 | C | VAL | B | 244 | -15.671 | -15.495 | 108.777 | 1.00 | 41.65 |
| 8034 | O | VAL | B | 244 | -15.418 | -15.620 | 109.978 | 1.00 | 42.00 |
| 8035 | N | VAL | B | 245 | -15.737 | -16.512 | 107.932 | 1.00 | 41.78 |
| 8036 | CA | VAL | B | 245 | -15.485 | -17.877 | 108.322 | 1.00 | 42.04 |
| 8037 | CB | VAL | B | 245 | -16.609 | -18.792 | 107.827 | 1.00 | 42.21 |
| 8038 | CG1 | VAL | B | 245 | -16.801 | -18.624 | 106.312 | 1.00 | 41.86 |
| 8039 | CG2 | VAL | B | 245 | -16.311 | -20.244 | 108.180 | 1.00 | 42.17 |
| 8040 | C | VAL | B | 245 | -14.175 | -18.351 | 107.702 | 1.00 | 42.59 |
| 8041 | O | VAL | B | 245 | -13.849 | -18.011 | 106.564 | 1.00 | 42.17 |
| 8042 | N | ASN | B | 246 | -13.408 | -19.115 | 108.470 | 1.00 | 43.43 |
| 8043 | CA | ASN | B | 246 | -12.168 | -19.689 | 107.967 | 1.00 | 44.19 |
| 8044 | CB | ASN | B | 246 | -11.195 | -19.985 | 109.115 | 1.00 | 44.00 |
| 8045 | CG | ASN | B | 246 | -9.854 | -20.526 | 108.628 | 1.00 | 43.62 |
| 8046 | OD1 | ASN | B | 246 | -9.806 | -21.419 | 107.792 | 1.00 | 43.78 |
| 8047 | ND2 | ASN | B | 246 | -8.767 | -19.998 | 109.168 | 1.00 | 40.49 |
| 8048 | C | ASN | B | 246 | -12.558 | -20.965 | 107.269 | 1.00 | 44.86 |

FIGURE 3 FB

| A | B | C | D | E | F | G | H | I | J |
|---|---|---|---|---|---|---|---|---|---|
| 8049 | O | ASN | B | 246 | -13.136 | -21.856 | 107.887 | 1.00 | 44.93 |
| 8050 | N | THR | B | 247 | -12.275 | -21.059 | 105.975 | 1.00 | 46.04 |
| 8051 | CA | THR | B | 247 | -12.670 | -22.261 | 105.260 | 1.00 | 46.94 |
| 8052 | CB | THR | B | 247 | -12.940 | -21.969 | 103.771 | 1.00 | 46.97 |
| 8053 | OG1 | THR | B | 247 | -11.731 | -21.577 | 103.112 | 1.00 | 46.64 |
| 8054 | CG2 | THR | B | 247 | -13.835 | -20.749 | 103.648 | 1.00 | 46.00 |
| 8055 | C | THR | B | 247 | -11.671 | -23.389 | 105.470 | 1.00 | 47.81 |
| 8056 | O | THR | B | 247 | -12.043 | -24.562 | 105.448 | 1.00 | 48.21 |
| 8057 | N | ASP | B | 248 | -10.412 | -23.037 | 105.718 | 1.00 | 48.70 |
| 8058 | CA | ASP | B | 248 | -9.395 | -24.055 | 105.986 | 1.00 | 49.91 |
| 8059 | CB | ASP | B | 248 | -7.994 | -23.433 | 106.092 | 1.00 | 49.97 |
| 8060 | CG | ASP | B | 248 | -7.490 | -22.889 | 104.767 | 1.00 | 50.78 |
| 8061 | OD1 | ASP | B | 248 | -7.971 | -23.358 | 103.712 | 1.00 | 50.27 |
| 8062 | OD2 | ASP | B | 248 | -6.610 | -21.995 | 104.683 | 1.00 | 52.28 |
| 8063 | C | ASP | B | 248 | -9.711 | -24.840 | 107.264 | 1.00 | 50.47 |
| 8064 | O | ASP | B | 248 | -9.239 | -25.958 | 107.441 | 1.00 | 50.52 |
| 8065 | N | SER | B | 249 | -10.519 | -24.270 | 108.154 | 1.00 | 51.46 |
| 8066 | CA | SER | B | 249 | -10.812 | -24.958 | 109.416 | 1.00 | 52.21 |
| 8067 | CB | SER | B | 249 | -10.593 | -24.021 | 110.612 | 1.00 | 52.18 |
| 8068 | OG | SER | B | 249 | -11.825 | -23.586 | 111.162 | 1.00 | 53.07 |
| 8069 | C | SER | B | 249 | -12.206 | -25.600 | 109.457 | 1.00 | 52.53 |
| 8070 | O | SER | B | 249 | -12.761 | -25.857 | 110.533 | 1.00 | 52.48 |
| 8071 | N | LEU | B | 250 | -12.761 | -25.854 | 108.277 | 1.00 | 52.90 |
| 8072 | CA | LEU | B | 250 | -14.057 | -26.504 | 108.156 | 1.00 | 53.25 |
| 8073 | CB | LEU | B | 250 | -14.514 | -26.511 | 106.695 | 1.00 | 52.98 |
| 8074 | CG | LEU | B | 250 | -15.635 | -25.572 | 106.239 | 1.00 | 52.88 |
| 8075 | CD1 | LEU | B | 250 | -15.304 | -24.970 | 104.871 | 1.00 | 52.20 |
| 8076 | CD2 | LEU | B | 250 | -15.905 | -24.471 | 107.244 | 1.00 | 51.68 |
| 8077 | C | LEU | B | 250 | -13.949 | -27.932 | 108.660 | 1.00 | 53.88 |
| 8078 | O | LEU | B | 250 | -12.888 | -28.552 | 108.555 | 1.00 | 53.74 |
| 8079 | N | SER | B | 251 | -15.046 | -28.447 | 109.211 | 1.00 | 54.40 |
| 8080 | CA | SER | B | 251 | -15.089 | -29.821 | 109.696 | 1.00 | 55.11 |
| 8081 | CB | SER | B | 251 | -14.851 | -29.891 | 111.198 | 1.00 | 55.26 |
| 8082 | OG | SER | B | 251 | -15.069 | -31.214 | 111.648 | 1.00 | 55.97 |
| 8083 | C | SER | B | 251 | -16.425 | -30.464 | 109.373 | 1.00 | 55.39 |
| 8084 | O | SER | B | 251 | -17.419 | -29.778 | 109.194 | 1.00 | 55.53 |
| 8085 | N | SER | B | 252 | -16.455 | -31.787 | 109.329 | 1.00 | 55.57 |
| 8086 | CA | SER | B | 252 | -17.669 | -32.477 | 108.931 | 1.00 | 55.82 |
| 8087 | CB | SER | B | 252 | -17.300 | -33.627 | 107.996 | 1.00 | 55.97 |
| 8088 | OG | SER | B | 252 | -16.172 | -33.253 | 107.217 | 1.00 | 56.43 |
| 8089 | C | SER | B | 252 | -18.469 | -32.977 | 110.128 | 1.00 | 55.76 |
| 8090 | O | SER | B | 252 | -19.536 | -33.572 | 109.982 | 1.00 | 55.88 |
| 8091 | N | VAL | B | 253 | -17.954 | -32.717 | 111.318 | 1.00 | 55.78 |
| 8092 | CA | VAL | B | 253 | -18.588 | -33.189 | 112.537 | 1.00 | 55.76 |
| 8093 | CB | VAL | B | 253 | -17.629 | -34.115 | 113.328 | 1.00 | 55.84 |
| 8094 | CG1 | VAL | B | 253 | -18.059 | -34.238 | 114.784 | 1.00 | 56.15 |
| 8095 | CG2 | VAL | B | 253 | -17.551 | -35.488 | 112.666 | 1.00 | 55.52 |
| 8096 | C | VAL | B | 253 | -18.999 | -32.004 | 113.388 | 1.00 | 55.72 |
| 8097 | O | VAL | B | 253 | -19.652 | -32.151 | 114.424 | 1.00 | 55.94 |
| 8098 | N | THR | B | 254 | -18.613 | -30.819 | 112.938 | 1.00 | 55.49 |
| 8099 | CA | THR | B | 254 | -18.944 | -29.606 | 113.658 | 1.00 | 55.35 |

FIGURE 3 FC

| A | B | C | D | E | F | G | H | I | J |
|---|---|---|---|---|---|---|---|---|---|
| 8100 | CB | THR | B | 254 | -17.771 | -29.199 | 114.577 | 1.00 | 55.43 |
| 8101 | OG1 | THR | B | 254 | -17.432 | -27.824 | 114.355 | 1.00 | 55.88 |
| 8102 | CG2 | THR | B | 254 | -16.519 | -29.920 | 114.165 | 1.00 | 56.14 |
| 8103 | C | THR | B | 254 | -19.358 | -28.463 | 112.731 | 1.00 | 54.81 |
| 8104 | O | THR | B | 254 | -18.762 | -28.239 | 111.674 | 1.00 | 54.88 |
| 8105 | N | ASN | B | 255 | -20.401 | -27.748 | 113.132 | 1.00 | 54.08 |
| 8106 | CA | ASN | B | 255 | -20.859 | -26.609 | 112.359 | 1.00 | 52.98 |
| 8107 | CB | ASN | B | 255 | -22.150 | -26.032 | 112.940 | 1.00 | 53.13 |
| 8108 | CG | ASN | B | 255 | -23.366 | -26.816 | 112.512 | 1.00 | 54.12 |
| 8109 | OD1 | ASN | B | 255 | -23.356 | -27.440 | 111.450 | 1.00 | 54.93 |
| 8110 | ND2 | ASN | B | 255 | -24.418 | -26.803 | 113.327 | 1.00 | 58.09 |
| 8111 | C | ASN | B | 255 | -19.747 | -25.592 | 112.339 | 1.00 | 52.05 |
| 8112 | O | ASN | B | 255 | -18.915 | -25.562 | 113.245 | 1.00 | 52.18 |
| 8113 | N | ALA | B | 256 | -19.704 | -24.791 | 111.284 | 1.00 | 50.74 |
| 8114 | CA | ALA | B | 256 | -18.674 | -23.787 | 111.133 | 1.00 | 49.28 |
| 8115 | CB | ALA | B | 256 | -18.558 | -23.386 | 109.680 | 1.00 | 49.39 |
| 8116 | C | ALA | B | 256 | -19.018 | -22.584 | 111.984 | 1.00 | 48.62 |
| 8117 | O | ALA | B | 256 | -20.192 | -22.248 | 112.153 | 1.00 | 48.43 |
| 8118 | N | THR | B | 257 | -18.005 | -21.940 | 112.542 | 1.00 | 47.61 |
| 8119 | CA | THR | B | 257 | -18.259 | -20.730 | 113.298 | 1.00 | 47.02 |
| 8120 | CB | THR | B | 257 | -17.503 | -20.703 | 114.659 | 1.00 | 47.32 |
| 8121 | OG1 | THR | B | 257 | -16.787 | -19.463 | 114.797 | 1.00 | 46.70 |
| 8122 | CG2 | THR | B | 257 | -16.407 | -21.743 | 114.681 | 1.00 | 47.86 |
| 8123 | C | THR | B | 257 | -17.935 | -19.518 | 112.444 | 1.00 | 46.26 |
| 8124 | O | THR | B | 257 | -16.844 | -19.385 | 111.888 | 1.00 | 46.32 |
| 8125 | N | SER | B | 258 | -18.912 | -18.643 | 112.320 | 1.00 | 45.20 |
| 8126 | CA | SER | B | 258 | -18.714 | -17.441 | 111.558 | 1.00 | 44.45 |
| 8127 | CB | SER | B | 258 | -20.003 | -17.070 | 110.816 | 1.00 | 44.73 |
| 8128 | OG | SER | B | 258 | -20.632 | -18.236 | 110.294 | 1.00 | 44.99 |
| 8129 | C | SER | B | 258 | -18.330 | -16.382 | 112.571 | 1.00 | 43.81 |
| 8130 | O | SER | B | 258 | -18.960 | -16.247 | 113.624 | 1.00 | 43.27 |
| 8131 | N | ILE | B | 259 | -17.262 | -15.661 | 112.281 | 1.00 | 42.93 |
| 8132 | CA | ILE | B | 259 | -16.837 | -14.633 | 113.191 | 1.00 | 42.31 |
| 8133 | CB | ILE | B | 259 | -15.313 | -14.454 | 113.162 | 1.00 | 42.54 |
| 8134 | CG1 | ILE | B | 259 | -14.643 | -15.714 | 113.695 | 1.00 | 42.45 |
| 8135 | CD1 | ILE | B | 259 | -15.288 | -16.235 | 114.960 | 1.00 | 42.58 |
| 8136 | CG2 | ILE | B | 259 | -14.914 | -13.273 | 114.016 | 1.00 | 42.31 |
| 8137 | C | ILE | B | 259 | -17.506 | -13.384 | 112.721 | 1.00 | 41.66 |
| 8138 | O | ILE | B | 259 | -17.317 | -12.970 | 111.590 | 1.00 | 41.40 |
| 8139 | N | GLN | B | 260 | -18.312 | -12.794 | 113.585 | 1.00 | 41.02 |
| 8140 | CA | GLN | B | 260 | -18.988 | -11.570 | 113.229 | 1.00 | 40.51 |
| 8141 | CB | GLN | B | 260 | -20.274 | -11.409 | 114.032 | 1.00 | 40.31 |
| 8142 | CG | GLN | B | 260 | -20.880 | -10.028 | 113.875 | 1.00 | 40.06 |
| 8143 | CD | GLN | B | 260 | -22.307 | -9.943 | 114.377 | 1.00 | 40.09 |
| 8144 | OE1 | GLN | B | 260 | -22.759 | -10.796 | 115.152 | 1.00 | 39.59 |
| 8145 | NE2 | GLN | B | 260 | -23.020 | -8.910 | 113.941 | 1.00 | 37.16 |
| 8146 | C | GLN | B | 260 | -18.096 | -10.372 | 113.465 | 1.00 | 40.37 |
| 8147 | O | GLN | B | 260 | -17.384 | -10.296 | 114.466 | 1.00 | 40.89 |
| 8148 | N | ILE | B | 261 | -18.122 | -9.452 | 112.512 | 1.00 | 40.18 |
| 8149 | CA | ILE | B | 261 | -17.454 | -8.168 | 112.618 | 1.00 | 39.30 |
| 8150 | CB | ILE | B | 261 | -16.673 | -7.873 | 111.353 | 1.00 | 39.07 |

FIGURE 3 FD

| A | B | C | D | E | F | G | H | I | J |
|---|---|---|---|---|---|---|---|---|---|
| 8151 | CG1 | ILE | B | 261 | -15.581 | -8.928 | 111.126 | 1.00 | 39.08 |
| 8152 | CD1 | ILE | B | 261 | -14.550 | -8.496 | 110.109 | 1.00 | 36.42 |
| 8153 | CG2 | ILE | B | 261 | -16.071 | -6.482 | 111.413 | 1.00 | 38.83 |
| 8154 | C | ILE | B | 261 | -18.594 | -7.173 | 112.726 | 1.00 | 39.53 |
| 8155 | O | ILE | B | 261 | -19.438 | -7.097 | 111.827 | 1.00 | 39.84 |
| 8156 | N | THR | B | 262 | -18.662 | -6.431 | 113.825 | 1.00 | 38.85 |
| 8157 | CA | THR | B | 262 | -19.733 | -5.457 | 113.961 | 1.00 | 38.23 |
| 8158 | CB | THR | B | 262 | -20.106 | -5.288 | 115.426 | 1.00 | 38.47 |
| 8159 | OG1 | THR | B | 262 | -18.910 | -5.066 | 116.169 | 1.00 | 37.80 |
| 8160 | CG2 | THR | B | 262 | -20.649 | -6.597 | 115.998 | 1.00 | 38.72 |
| 8161 | C | THR | B | 262 | -19.341 | -4.109 | 113.372 | 1.00 | 37.66 |
| 8162 | O | THR | B | 262 | -18.165 | -3.766 | 113.279 | 1.00 | 37.65 |
| 8163 | N | ALA | B | 263 | -20.344 | -3.343 | 112.981 | 1.00 | 37.26 |
| 8164 | CA | ALA | B | 263 | -20.136 | -2.017 | 112.422 | 1.00 | 36.78 |
| 8165 | CB | ALA | B | 263 | -21.413 | -1.555 | 111.830 | 1.00 | 37.01 |
| 8166 | C | ALA | B | 263 | -19.715 | -1.046 | 113.517 | 1.00 | 36.64 |
| 8167 | O | ALA | B | 263 | -19.971 | -1.282 | 114.688 | 1.00 | 36.85 |
| 8168 | N | PRO | B | 264 | -19.098 | 0.065 | 113.148 | 1.00 | 36.52 |
| 8169 | CA | PRO | B | 264 | -18.688 | 1.050 | 114.147 | 1.00 | 36.33 |
| 8170 | CB | PRO | B | 264 | -18.139 | 2.199 | 113.308 | 1.00 | 36.24 |
| 8171 | CG | PRO | B | 264 | -17.890 | 1.641 | 111.959 | 1.00 | 35.73 |
| 8172 | CD | PRO | B | 264 | -18.765 | 0.474 | 111.776 | 1.00 | 36.33 |
| 8173 | C | PRO | B | 264 | -19.901 | 1.545 | 114.926 | 1.00 | 37.00 |
| 8174 | O | PRO | B | 264 | -21.002 | 1.697 | 114.355 | 1.00 | 36.67 |
| 8175 | N | ALA | B | 265 | -19.697 | 1.794 | 116.220 | 1.00 | 37.13 |
| 8176 | CA | ALA | B | 265 | -20.729 | 2.350 | 117.086 | 1.00 | 37.00 |
| 8177 | CB | ALA | B | 265 | -20.136 | 2.696 | 118.461 | 1.00 | 37.56 |
| 8178 | C | ALA | B | 265 | -21.364 | 3.585 | 116.455 | 1.00 | 37.13 |
| 8179 | O | ALA | B | 265 | -22.561 | 3.824 | 116.609 | 1.00 | 36.95 |
| 8180 | N | SER | B | 266 | -20.577 | 4.369 | 115.726 | 1.00 | 37.15 |
| 8181 | CA | SER | B | 266 | -21.138 | 5.551 | 115.097 | 1.00 | 37.43 |
| 8182 | CB | SER | B | 266 | -20.047 | 6.469 | 114.592 | 1.00 | 37.04 |
| 8183 | OG | SER | B | 266 | -19.411 | 5.880 | 113.484 | 1.00 | 38.44 |
| 8184 | C | SER | B | 266 | -22.068 | 5.178 | 113.936 | 1.00 | 37.94 |
| 8185 | O | SER | B | 266 | -22.594 | 6.046 | 113.244 | 1.00 | 37.98 |
| 8186 | N | MET | B | 267 | -22.238 | 3.887 | 113.702 | 1.00 | 38.09 |
| 8187 | CA | MET | B | 267 | -23.175 | 3.443 | 112.688 | 1.00 | 38.48 |
| 8188 | CB | MET | B | 267 | -22.513 | 2.483 | 111.691 | 1.00 | 38.25 |
| 8189 | CG | MET | B | 267 | -21.512 | 3.168 | 110.770 | 1.00 | 38.46 |
| 8190 | SD | MET | B | 267 | -22.322 | 3.969 | 109.403 | 1.00 | 37.89 |
| 8191 | CE | MET | B | 267 | -21.184 | 5.222 | 108.957 | 1.00 | 34.81 |
| 8192 | C | MET | B | 267 | -24.285 | 2.747 | 113.437 | 1.00 | 38.49 |
| 8193 | O | MET | B | 267 | -25.454 | 2.946 | 113.144 | 1.00 | 38.45 |
| 8194 | N | LEU | B | 268 | -23.914 | 1.966 | 114.443 | 1.00 | 38.76 |
| 8195 | CA | LEU | B | 268 | -24.910 | 1.222 | 115.198 | 1.00 | 39.23 |
| 8196 | CB | LEU | B | 268 | -24.252 | 0.337 | 116.244 | 1.00 | 39.27 |
| 8197 | CG | LEU | B | 268 | -23.630 | -0.970 | 115.789 | 1.00 | 39.59 |
| 8198 | CD1 | LEU | B | 268 | -23.026 | -1.638 | 117.009 | 1.00 | 40.45 |
| 8199 | CD2 | LEU | B | 268 | -24.656 | -1.873 | 115.122 | 1.00 | 38.79 |
| 8200 | C | LEU | B | 268 | -25.874 | 2.155 | 115.884 | 1.00 | 39.28 |
| 8201 | O | LEU | B | 268 | -26.848 | 1.725 | 116.484 | 1.00 | 39.39 |

FIGURE 3 FE

| A | B | C | D | E | F | G | H | I | J |
|---|---|---|---|---|---|---|---|---|---|
| 8202 | N | ILE | B | 269 | -25.585 | 3.441 | 115.795 | 1.00 | 39.69 |
| 8203 | CA | ILE | B | 269 | -26.419 | 4.453 | 116.410 | 1.00 | 40.33 |
| 8204 | CB | ILE | B | 269 | -25.674 | 5.825 | 116.370 | 1.00 | 40.48 |
| 8205 | CG1 | ILE | B | 269 | -26.105 | 6.690 | 117.535 | 1.00 | 40.65 |
| 8206 | CD1 | ILE | B | 269 | -25.847 | 6.028 | 118.865 | 1.00 | 42.72 |
| 8207 | CG2 | ILE | B | 269 | -25.841 | 6.532 | 115.040 | 1.00 | 41.25 |
| 8208 | C | ILE | B | 269 | -27.827 | 4.498 | 115.770 | 1.00 | 40.34 |
| 8209 | O | ILE | B | 269 | -28.841 | 4.679 | 116.459 | 1.00 | 40.41 |
| 8210 | N | GLY | B | 270 | -27.890 | 4.288 | 114.459 | 1.00 | 39.85 |
| 8211 | CA | GLY | B | 270 | -29.164 | 4.285 | 113.751 | 1.00 | 39.12 |
| 8212 | C | GLY | B | 270 | -29.196 | 3.299 | 112.589 | 1.00 | 38.12 |
| 8213 | O | GLY | B | 270 | -28.502 | 2.277 | 112.616 | 1.00 | 37.74 |
| 8214 | N | ASP | B | 271 | -30.035 | 3.593 | 111.594 | 1.00 | 36.92 |
| 8215 | CA | ASP | B | 271 | -30.104 | 2.791 | 110.388 | 1.00 | 36.02 |
| 8216 | CB | ASP | B | 271 | -31.312 | 3.179 | 109.547 | 1.00 | 35.99 |
| 8217 | CG | ASP | B | 271 | -32.594 | 2.530 | 110.034 | 1.00 | 36.39 |
| 8218 | OD1 | ASP | B | 271 | -32.509 | 1.672 | 110.959 | 1.00 | 33.33 |
| 8219 | OD2 | ASP | B | 271 | -33.729 | 2.818 | 109.548 | 1.00 | 34.54 |
| 8220 | C | ASP | B | 271 | -28.831 | 3.069 | 109.608 | 1.00 | 35.29 |
| 8221 | O | ASP | B | 271 | -28.382 | 4.206 | 109.515 | 1.00 | 35.40 |
| 8222 | N | HIS | B | 272 | -28.223 | 2.031 | 109.065 | 1.00 | 33.91 |
| 8223 | CA | HIS | B | 272 | -27.004 | 2.248 | 108.305 | 1.00 | 33.12 |
| 8224 | CB | HIS | B | 272 | -25.795 | 2.096 | 109.227 | 1.00 | 31.99 |
| 8225 | CG | HIS | B | 272 | -25.746 | 0.772 | 109.899 | 1.00 | 30.02 |
| 8226 | ND1 | HIS | B | 272 | -26.486 | 0.489 | 111.028 | 1.00 | 30.83 |
| 8227 | CE1 | HIS | B | 272 | -26.273 | -0.764 | 111.388 | 1.00 | 29.81 |
| 8228 | NE2 | HIS | B | 272 | -25.427 | -1.303 | 110.530 | 1.00 | 30.16 |
| 8229 | CD2 | HIS | B | 272 | -25.097 | -0.368 | 109.578 | 1.00 | 28.42 |
| 8230 | C | HIS | B | 272 | -26.946 | 1.174 | 107.234 | 1.00 | 32.53 |
| 8231 | O | HIS | B | 272 | -27.816 | 0.337 | 107.186 | 1.00 | 32.22 |
| 8232 | N | TYR | B | 273 | -25.903 | 1.205 | 106.411 | 1.00 | 32.18 |
| 8233 | CA | TYR | B | 273 | -25.664 | 0.185 | 105.409 | 1.00 | 32.39 |
| 8234 | CB | TYR | B | 273 | -25.943 | 0.727 | 104.005 | 1.00 | 31.52 |
| 8235 | CG | TYR | B | 273 | -27.277 | 1.379 | 103.776 | 1.00 | 30.43 |
| 8236 | CD1 | TYR | B | 273 | -28.438 | 0.637 | 103.736 | 1.00 | 28.06 |
| 8237 | CE1 | TYR | B | 273 | -29.655 | 1.241 | 103.480 | 1.00 | 29.01 |
| 8238 | CZ | TYR | B | 273 | -29.708 | 2.587 | 103.242 | 1.00 | 28.63 |
| 8239 | OH | TYR | B | 273 | -30.907 | 3.211 | 102.998 | 1.00 | 29.60 |
| 8240 | CE2 | TYR | B | 273 | -28.562 | 3.339 | 103.265 | 1.00 | 30.14 |
| 8241 | CD2 | TYR | B | 273 | -27.357 | 2.735 | 103.523 | 1.00 | 29.36 |
| 8242 | C | TYR | B | 273 | -24.199 | -0.217 | 105.347 | 1.00 | 33.08 |
| 8243 | O | TYR | B | 273 | -23.299 | 0.567 | 105.694 | 1.00 | 32.62 |
| 8244 | N | LEU | B | 274 | -23.983 | -1.431 | 104.841 | 1.00 | 33.48 |
| 8245 | CA | LEU | B | 274 | -22.670 | -1.916 | 104.490 | 1.00 | 34.29 |
| 8246 | CB | LEU | B | 274 | -22.584 | -3.422 | 104.690 | 1.00 | 34.01 |
| 8247 | CG | LEU | B | 274 | -21.233 | -4.065 | 104.329 | 1.00 | 35.66 |
| 8248 | CD1 | LEU | B | 274 | -20.163 | -3.758 | 105.396 | 1.00 | 34.34 |
| 8249 | CD2 | LEU | B | 274 | -21.383 | -5.577 | 104.147 | 1.00 | 34.70 |
| 8250 | C | LEU | B | 274 | -22.592 | -1.570 | 103.022 | 1.00 | 35.14 |
| 8251 | O | LEU | B | 274 | -23.398 | -2.041 | 102.234 | 1.00 | 35.22 |
| 8252 | N | CYS | B | 275 | -21.633 | -0.743 | 102.637 | 1.00 | 36.49 |

FIGURE 3 FF

| A | B | C | D | E | F | G | H | I | J |
|---|---|---|---|---|---|---|---|---|---|
| 8253 | CA | CYS | B | 275 | -21.598 | -0.284 | 101.264 | 1.00 | 38.00 |
| 8254 | CB | CYS | B | 275 | -21.766 | 1.233 | 101.203 | 1.00 | 37.89 |
| 8255 | SG | CYS | B | 275 | -20.464 | 2.141 | 102.060 | 1.00 | 41.73 |
| 8256 | C | CYS | B | 275 | -20.365 | -0.738 | 100.485 | 1.00 | 38.60 |
| 8257 | O | CYS | B | 275 | -20.330 | -0.615 | 99.266 | 1.00 | 38.77 |
| 8258 | N | ASP | B | 276 | -19.350 | -1.246 | 101.175 | 1.00 | 39.13 |
| 8259 | CA | ASP | B | 276 | -18.185 | -1.764 | 100.469 | 1.00 | 39.49 |
| 8260 | CB | ASP | B | 276 | -17.294 | -0.654 | 99.942 | 1.00 | 39.64 |
| 8261 | CG | ASP | B | 276 | -16.074 | -1.199 | 99.235 | 1.00 | 41.05 |
| 8262 | OD1 | ASP | B | 276 | -15.992 | -1.067 | 98.000 | 1.00 | 43.44 |
| 8263 | OD2 | ASP | B | 276 | -15.153 | -1.800 | 99.829 | 1.00 | 42.89 |
| 8264 | C | ASP | B | 276 | -17.360 | -2.750 | 101.284 | 1.00 | 39.39 |
| 8265 | O | ASP | B | 276 | -17.216 | -2.592 | 102.493 | 1.00 | 39.54 |
| 8266 | N | VAL | B | 277 | -16.831 | -3.763 | 100.599 | 1.00 | 38.98 |
| 8267 | CA | VAL | B | 277 | -16.019 | -4.799 | 101.206 | 1.00 | 38.77 |
| 8268 | CB | VAL | B | 277 | -16.788 | -6.124 | 101.324 | 1.00 | 39.05 |
| 8269 | CG1 | VAL | B | 277 | -15.901 | -7.199 | 101.921 | 1.00 | 39.22 |
| 8270 | CG2 | VAL | B | 277 | -18.049 | -5.955 | 102.168 | 1.00 | 37.97 |
| 8271 | C | VAL | B | 277 | -14.786 | -5.042 | 100.355 | 1.00 | 39.05 |
| 8272 | O | VAL | B | 277 | -14.876 | -5.521 | 99.234 | 1.00 | 39.52 |
| 8273 | N | THR | B | 278 | -13.615 | -4.719 | 100.882 | 1.00 | 39.00 |
| 8274 | CA | THR | B | 278 | -12.413 | -4.928 | 100.116 | 1.00 | 37.98 |
| 8275 | CB | THR | B | 278 | -11.909 | -3.594 | 99.597 | 1.00 | 38.19 |
| 8276 | OG1 | THR | B | 278 | -12.815 | -3.088 | 98.603 | 1.00 | 38.23 |
| 8277 | CG2 | THR | B | 278 | -10.607 | -3.795 | 98.848 | 1.00 | 37.09 |
| 8278 | C | THR | B | 278 | -11.326 | -5.595 | 100.954 | 1.00 | 38.18 |
| 8279 | O | THR | B | 278 | -10.843 | -5.021 | 101.938 | 1.00 | 38.22 |
| 8280 | N | TRP | B | 279 | -10.936 | -6.804 | 100.564 | 1.00 | 37.09 |
| 8281 | CA | TRP | B | 279 | -9.850 | -7.486 | 101.250 | 1.00 | 36.31 |
| 8282 | CB | TRP | B | 279 | -9.733 | -8.923 | 100.759 | 1.00 | 35.92 |
| 8283 | CG | TRP | B | 279 | -10.672 | -9.858 | 101.423 | 1.00 | 34.21 |
| 8284 | CD1 | TRP | B | 279 | -11.853 | -10.320 | 100.938 | 1.00 | 33.31 |
| 8285 | NE1 | TRP | B | 279 | -12.438 | -11.178 | 101.841 | 1.00 | 32.80 |
| 8286 | CE2 | TRP | B | 279 | -11.618 | -11.285 | 102.933 | 1.00 | 33.27 |
| 8287 | CD2 | TRP | B | 279 | -10.502 | -10.461 | 102.704 | 1.00 | 33.83 |
| 8288 | CE3 | TRP | B | 279 | -9.509 | -10.394 | 103.683 | 1.00 | 33.15 |
| 8289 | CZ3 | TRP | B | 279 | -9.663 | -11.125 | 104.826 | 1.00 | 34.15 |
| 8290 | CH2 | TRP | B | 279 | -10.784 | -11.926 | 105.027 | 1.00 | 34.29 |
| 8291 | CZ2 | TRP | B | 279 | -11.772 | -12.021 | 104.092 | 1.00 | 34.17 |
| 8292 | C | TRP | B | 279 | -8.546 | -6.737 | 100.984 | 1.00 | 36.37 |
| 8293 | O | TRP | B | 279 | -8.279 | -6.313 | 99.861 | 1.00 | 35.97 |
| 8294 | N | ALA | B | 280 | -7.728 | -6.564 | 102.010 | 1.00 | 35.86 |
| 8295 | CA | ALA | B | 280 | -6.475 | -5.858 | 101.796 | 1.00 | 36.13 |
| 8296 | CB | ALA | B | 280 | -6.240 | -4.819 | 102.902 | 1.00 | 36.41 |
| 8297 | C | ALA | B | 280 | -5.298 | -6.821 | 101.703 | 1.00 | 35.57 |
| 8298 | O | ALA | B | 280 | -4.365 | -6.586 | 100.960 | 1.00 | 34.87 |
| 8299 | N | THR | B | 281 | -5.363 | -7.904 | 102.470 | 1.00 | 36.03 |
| 8300 | CA | THR | B | 281 | -4.296 | -8.899 | 102.519 | 1.00 | 36.43 |
| 8301 | CB | THR | B | 281 | -3.281 | -8.600 | 103.649 | 1.00 | 36.45 |
| 8302 | OG1 | THR | B | 281 | -3.806 | -9.079 | 104.897 | 1.00 | 35.74 |
| 8303 | CG2 | THR | B | 281 | -3.122 | -7.116 | 103.887 | 1.00 | 35.62 |

FIGURE 3 FG

| A | B | C | D | E | F | G | H | I | J |
|---|---|---|---|---|---|---|---|---|---|
| 8304 | C | THR | B | 281 | -4.950 | -10.211 | 102.852 | 1.00 | 36.84 |
| 8305 | O | THR | B | 281 | -6.161 | -10.304 | 102.902 | 1.00 | 37.00 |
| 8306 | N | GLN | B | 282 | -4.142 | -11.223 | 103.115 | 1.00 | 37.40 |
| 8307 | CA | GLN | B | 282 | -4.672 | -12.520 | 103.486 | 1.00 | 38.02 |
| 8308 | CB | GLN | B | 282 | -3.538 | -13.545 | 103.564 | 1.00 | 37.95 |
| 8309 | CG | GLN | B | 282 | -2.706 | -13.655 | 102.289 | 1.00 | 38.65 |
| 8310 | CD | GLN | B | 282 | -3.526 | -14.069 | 101.062 | 1.00 | 38.38 |
| 8311 | OE1 | GLN | B | 282 | -4.628 | -14.626 | 101.190 | 1.00 | 38.79 |
| 8312 | NE2 | GLN | B | 282 | -2.988 | -13.800 | 99.878 | 1.00 | 35.23 |
| 8313 | C | GLN | B | 282 | -5.338 | -12.437 | 104.840 | 1.00 | 38.28 |
| 8314 | O | GLN | B | 282 | -6.153 | -13.287 | 105.194 | 1.00 | 38.52 |
| 8315 | N | GLU | B | 283 | -4.986 | -11.412 | 105.604 | 1.00 | 38.86 |
| 8316 | CA | GLU | B | 283 | -5.453 | -11.328 | 106.976 | 1.00 | 39.52 |
| 8317 | CB | GLU | B | 283 | -4.291 | -11.653 | 107.925 | 1.00 | 39.66 |
| 8318 | CG | GLU | B | 283 | -3.972 | -13.137 | 108.032 | 1.00 | 41.29 |
| 8319 | CD | GLU | B | 283 | -2.684 | -13.415 | 108.804 | 1.00 | 44.21 |
| 8320 | OE1 | GLU | B | 283 | -2.355 | -14.604 | 109.007 | 1.00 | 44.57 |
| 8321 | OE2 | GLU | B | 283 | -1.994 | -12.444 | 109.197 | 1.00 | 45.27 |
| 8322 | C | GLU | B | 283 | -6.067 | -9.987 | 107.354 | 1.00 | 39.44 |
| 8323 | O | GLU | B | 283 | -6.421 | -9.763 | 108.518 | 1.00 | 39.54 |
| 8324 | N | ARG | B | 284 | -6.194 | -9.092 | 106.385 | 1.00 | 39.32 |
| 8325 | CA | ARG | B | 284 | -6.752 | -7.782 | 106.672 | 1.00 | 39.16 |
| 8326 | CB | ARG | B | 284 | -5.641 | -6.750 | 106.734 | 1.00 | 39.23 |
| 8327 | CG | ARG | B | 284 | -6.114 | -5.329 | 106.614 | 1.00 | 39.03 |
| 8328 | CD | ARG | B | 284 | -4.983 | -4.351 | 106.729 | 1.00 | 39.98 |
| 8329 | NE | ARG | B | 284 | -4.252 | -4.593 | 107.974 | 1.00 | 41.16 |
| 8330 | CZ | ARG | B | 284 | -2.970 | -4.328 | 108.146 | 1.00 | 41.27 |
| 8331 | NH1 | ARG | B | 284 | -2.397 | -4.579 | 109.316 | 1.00 | 42.14 |
| 8332 | NH2 | ARG | B | 284 | -2.263 | -3.803 | 107.157 | 1.00 | 39.73 |
| 8333 | C | ARG | B | 284 | -7.820 | -7.344 | 105.673 | 1.00 | 39.07 |
| 8334 | O | ARG | B | 284 | -7.554 | -7.152 | 104.484 | 1.00 | 39.65 |
| 8335 | N | ILE | B | 285 | -9.031 | -7.158 | 106.173 | 1.00 | 38.68 |
| 8336 | CA | ILE | B | 285 | -10.131 | -6.749 | 105.327 | 1.00 | 37.92 |
| 8337 | CB | ILE | B | 285 | -11.241 | -7.792 | 105.399 | 1.00 | 37.87 |
| 8338 | CG1 | ILE | B | 285 | -12.387 | -7.434 | 104.437 | 1.00 | 38.16 |
| 8339 | CD1 | ILE | B | 285 | -13.473 | -8.491 | 104.376 | 1.00 | 36.63 |
| 8340 | CG2 | ILE | B | 285 | -11.727 | -7.933 | 106.825 | 1.00 | 37.11 |
| 8341 | C | ILE | B | 285 | -10.671 | -5.393 | 105.731 | 1.00 | 37.86 |
| 8342 | O | ILE | B | 285 | -10.762 | -5.074 | 106.926 | 1.00 | 37.77 |
| 8343 | N | SER | B | 286 | -11.016 | -4.587 | 104.731 | 1.00 | 37.21 |
| 8344 | CA | SER | B | 286 | -11.661 | -3.313 | 104.994 | 1.00 | 37.35 |
| 8345 | CB | SER | B | 286 | -11.010 | -2.176 | 104.197 | 1.00 | 37.02 |
| 8346 | OG | SER | B | 286 | -11.201 | -2.342 | 102.812 | 1.00 | 37.16 |
| 8347 | C | SER | B | 286 | -13.167 | -3.376 | 104.709 | 1.00 | 37.41 |
| 8348 | O | SER | B | 286 | -13.595 | -3.962 | 103.703 | 1.00 | 37.72 |
| 8349 | N | LEU | B | 287 | -13.956 | -2.801 | 105.619 | 1.00 | 37.62 |
| 8350 | CA | LEU | B | 287 | -15.399 | -2.633 | 105.441 | 1.00 | 37.40 |
| 8351 | CB | LEU | B | 287 | -16.196 | -3.198 | 106.604 | 1.00 | 37.50 |
| 8352 | CG | LEU | B | 287 | -16.435 | -4.694 | 106.778 | 1.00 | 37.77 |
| 8353 | CD1 | LEU | B | 287 | -15.702 | -5.185 | 108.004 | 1.00 | 38.51 |
| 8354 | CD2 | LEU | B | 287 | -16.094 | -5.500 | 105.510 | 1.00 | 35.92 |

FIGURE 3 FH

| A | B | C | D | E | F | G | H | I | J |
|---|---|---|---|---|---|---|---|---|---|
| 8355 | C | LEU | B | 287 | -15.675 | -1.151 | 105.421 | 1.00 | 37.77 |
| 8356 | O | LEU | B | 287 | -15.028 | -0.384 | 106.145 | 1.00 | 37.69 |
| 8357 | N | GLN | B | 288 | -16.617 | -0.735 | 104.582 | 1.00 | 37.44 |
| 8358 | CA | GLN | B | 288 | -17.032 | 0.655 | 104.565 | 1.00 | 37.10 |
| 8359 | CB | GLN | B | 288 | -16.744 | 1.327 | 103.232 | 1.00 | 37.38 |
| 8360 | CG | GLN | B | 288 | -15.392 | 1.975 | 103.182 | 1.00 | 38.66 |
| 8361 | CD | GLN | B | 288 | -15.117 | 2.632 | 101.861 | 1.00 | 40.12 |
| 8362 | OE1 | GLN | B | 288 | -15.178 | 3.849 | 101.744 | 1.00 | 42.07 |
| 8363 | NE2 | GLN | B | 288 | -14.819 | 1.826 | 100.850 | 1.00 | 42.14 |
| 8364 | C | GLN | B | 288 | -18.507 | 0.684 | 104.889 | 1.00 | 36.53 |
| 8365 | O | GLN | B | 288 | -19.287 | -0.051 | 104.299 | 1.00 | 36.84 |
| 8366 | N | TRP | B | 289 | -18.878 | 1.520 | 105.851 | 1.00 | 35.59 |
| 8367 | CA | TRP | B | 289 | -20.241 | 1.586 | 106.310 | 1.00 | 34.92 |
| 8368 | CB | TRP | B | 289 | -20.327 | 1.326 | 107.815 | 1.00 | 34.68 |
| 8369 | CG | TRP | B | 289 | -19.831 | -0.019 | 108.238 | 1.00 | 33.12 |
| 8370 | CD1 | TRP | B | 289 | -18.556 | -0.359 | 108.516 | 1.00 | 31.84 |
| 8371 | NE1 | TRP | B | 289 | -18.483 | -1.685 | 108.873 | 1.00 | 31.97 |
| 8372 | CE2 | TRP | B | 289 | -19.738 | -2.223 | 108.837 | 1.00 | 31.75 |
| 8373 | CD2 | TRP | B | 289 | -20.615 | -1.201 | 108.444 | 1.00 | 32.72 |
| 8374 | CE3 | TRP | B | 289 | -21.974 | -1.501 | 108.326 | 1.00 | 32.48 |
| 8375 | CZ3 | TRP | B | 289 | -22.399 | -2.782 | 108.607 | 1.00 | 32.80 |
| 8376 | CH2 | TRP | B | 289 | -21.502 | -3.768 | 109.003 | 1.00 | 32.08 |
| 8377 | CZ2 | TRP | B | 289 | -20.169 | -3.507 | 109.131 | 1.00 | 31.47 |
| 8378 | C | TRP | B | 289 | -20.797 | 2.943 | 105.993 | 1.00 | 35.14 |
| 8379 | O | TRP | B | 289 | -20.059 | 3.909 | 105.856 | 1.00 | 35.72 |
| 8380 | N | LEU | B | 290 | -22.112 | 3.014 | 105.903 | 1.00 | 35.19 |
| 8381 | CA | LEU | B | 290 | -22.780 | 4.237 | 105.509 | 1.00 | 35.28 |
| 8382 | CB | LEU | B | 290 | -23.074 | 4.178 | 104.014 | 1.00 | 35.14 |
| 8383 | CG | LEU | B | 290 | -23.255 | 5.463 | 103.218 | 1.00 | 36.86 |
| 8384 | CD1 | LEU | B | 290 | -24.047 | 5.191 | 101.918 | 1.00 | 34.86 |
| 8385 | CD2 | LEU | B | 290 | -23.933 | 6.510 | 104.064 | 1.00 | 38.04 |
| 8386 | C | LEU | B | 290 | -24.086 | 4.385 | 106.277 | 1.00 | 34.83 |
| 8387 | O | LEU | B | 290 | -24.895 | 3.459 | 106.353 | 1.00 | 33.83 |
| 8388 | N | ARG | B | 291 | -24.276 | 5.562 | 106.854 | 1.00 | 35.32 |
| 8389 | CA | ARG | B | 291 | -25.508 | 5.874 | 107.578 | 1.00 | 35.73 |
| 8390 | CB | ARG | B | 291 | -25.315 | 7.156 | 108.375 | 1.00 | 36.02 |
| 8391 | CG | ARG | B | 291 | -24.458 | 7.008 | 109.591 | 1.00 | 37.90 |
| 8392 | CD | ARG | B | 291 | -24.452 | 8.252 | 110.451 | 1.00 | 39.63 |
| 8393 | NE | ARG | B | 291 | -23.770 | 8.015 | 111.708 | 1.00 | 38.90 |
| 8394 | CZ | ARG | B | 291 | -23.265 | 8.973 | 112.459 | 1.00 | 40.15 |
| 8395 | NH1 | ARG | B | 291 | -22.643 | 8.666 | 113.592 | 1.00 | 38.43 |
| 8396 | NH2 | ARG | B | 291 | -23.374 | 10.236 | 112.071 | 1.00 | 38.95 |
| 8397 | C | ARG | B | 291 | -26.677 | 6.090 | 106.617 | 1.00 | 35.27 |
| 8398 | O | ARG | B | 291 | -26.501 | 6.598 | 105.513 | 1.00 | 34.88 |
| 8399 | N | ARG | B | 292 | -27.880 | 5.741 | 107.058 | 1.00 | 35.74 |
| 8400 | CA | ARG | B | 292 | -29.075 | 5.944 | 106.239 | 1.00 | 35.22 |
| 8401 | CB | ARG | B | 292 | -30.348 | 5.581 | 107.007 | 1.00 | 35.20 |
| 8402 | CG | ARG | B | 292 | -31.498 | 5.216 | 106.064 | 1.00 | 34.72 |
| 8403 | CD | ARG | B | 292 | -32.801 | 4.879 | 106.741 | 1.00 | 33.40 |
| 8404 | NE | ARG | B | 292 | -33.919 | 4.915 | 105.804 | 1.00 | 34.54 |
| 8405 | CZ | ARG | B | 292 | -34.938 | 4.070 | 105.848 | 1.00 | 35.08 |

FIGURE 3 FI

| A | B | C | D | E | F | G | H | I | J |
|---|---|---|---|---|---|---|---|---|---|
| 8406 | NH1 | ARG | B | 292 | -35.929 | 4.151 | 104.958 | 1.00 | 35.28 |
| 8407 | NH2 | ARG | B | 292 | -34.961 | 3.126 | 106.779 | 1.00 | 34.28 |
| 8408 | C | ARG | B | 292 | -29.134 | 7.361 | 105.660 | 1.00 | 35.33 |
| 8409 | O | ARG | B | 292 | -29.630 | 7.568 | 104.557 | 1.00 | 35.36 |
| 8410 | N | ILE | B | 293 | -28.651 | 8.347 | 106.403 | 1.00 | 35.34 |
| 8411 | CA | ILE | B | 293 | -28.485 | 9.662 | 105.816 | 1.00 | 35.81 |
| 8412 | CB | ILE | B | 293 | -28.683 | 10.794 | 106.857 | 1.00 | 36.34 |
| 8413 | CG1 | ILE | B | 293 | -30.157 | 10.870 | 107.251 | 1.00 | 36.47 |
| 8414 | CD1 | ILE | B | 293 | -30.379 | 11.319 | 108.687 | 1.00 | 40.52 |
| 8415 | CG2 | ILE | B | 293 | -28.306 | 12.135 | 106.266 | 1.00 | 35.62 |
| 8416 | C | ILE | B | 293 | -27.077 | 9.574 | 105.265 | 1.00 | 36.01 |
| 8417 | O | ILE | B | 293 | -26.093 | 9.654 | 105.989 | 1.00 | 36.31 |
| 8418 | N | GLN | B | 294 | -27.001 | 9.346 | 103.965 | 1.00 | 36.43 |
| 8419 | CA | GLN | B | 294 | -25.757 | 9.005 | 103.287 | 1.00 | 36.06 |
| 8420 | CB | GLN | B | 294 | -26.093 | 8.349 | 101.938 | 1.00 | 36.08 |
| 8421 | CG | GLN | B | 294 | -26.959 | 7.108 | 102.114 | 1.00 | 34.91 |
| 8422 | CD | GLN | B | 294 | -27.491 | 6.560 | 100.809 | 1.00 | 34.61 |
| 8423 | OE1 | GLN | B | 294 | -26.843 | 6.672 | 99.768 | 1.00 | 33.16 |
| 8424 | NE2 | GLN | B | 294 | -28.679 | 5.959 | 100.863 | 1.00 | 35.21 |
| 8425 | C | GLN | B | 294 | -24.735 | 10.119 | 103.112 | 1.00 | 36.09 |
| 8426 | O | GLN | B | 294 | -24.142 | 10.264 | 102.044 | 1.00 | 35.47 |
| 8427 | N | ASN | B | 295 | -24.509 | 10.891 | 104.165 | 1.00 | 36.56 |
| 8428 | CA | ASN | B | 295 | -23.471 | 11.917 | 104.111 | 1.00 | 36.97 |
| 8429 | CB | ASN | B | 295 | -24.038 | 13.316 | 104.341 | 1.00 | 37.10 |
| 8430 | CG | ASN | B | 295 | -24.717 | 13.480 | 105.691 | 1.00 | 37.40 |
| 8431 | OD1 | ASN | B | 295 | -24.703 | 12.590 | 106.552 | 1.00 | 35.93 |
| 8432 | ND2 | ASN | B | 295 | -25.325 | 14.642 | 105.877 | 1.00 | 43.29 |
| 8433 | C | ASN | B | 295 | -22.326 | 11.614 | 105.073 | 1.00 | 37.07 |
| 8434 | O | ASN | B | 295 | -21.448 | 12.444 | 105.305 | 1.00 | 36.84 |
| 8435 | N | TYR | B | 296 | -22.337 | 10.400 | 105.610 | 1.00 | 37.36 |
| 8436 | CA | TYR | B | 296 | -21.336 | 9.978 | 106.580 | 1.00 | 37.65 |
| 8437 | CB | TYR | B | 296 | -21.884 | 10.220 | 107.987 | 1.00 | 37.75 |
| 8438 | CG | TYR | B | 296 | -20.871 | 10.152 | 109.109 | 1.00 | 39.31 |
| 8439 | CD1 | TYR | B | 296 | -20.027 | 11.220 | 109.373 | 1.00 | 41.42 |
| 8440 | CE1 | TYR | B | 296 | -19.116 | 11.181 | 110.409 | 1.00 | 42.77 |
| 8441 | CZ | TYR | B | 296 | -19.038 | 10.057 | 111.206 | 1.00 | 43.87 |
| 8442 | OH | TYR | B | 296 | -18.131 | 10.018 | 112.245 | 1.00 | 47.04 |
| 8443 | CE2 | TYR | B | 296 | -19.867 | 8.981 | 110.970 | 1.00 | 43.23 |
| 8444 | CD2 | TYR | B | 296 | -20.781 | 9.037 | 109.923 | 1.00 | 41.78 |
| 8445 | C | TYR | B | 296 | -20.998 | 8.498 | 106.417 | 1.00 | 37.35 |
| 8446 | O | TYR | B | 296 | -21.827 | 7.637 | 106.653 | 1.00 | 37.45 |
| 8447 | N | SER | B | 297 | -19.784 | 8.189 | 105.998 | 1.00 | 37.67 |
| 8448 | CA | SER | B | 297 | -19.400 | 6.787 | 105.913 | 1.00 | 37.97 |
| 8449 | CB | SER | B | 297 | -19.227 | 6.338 | 104.461 | 1.00 | 37.31 |
| 8450 | OG | SER | B | 297 | -18.367 | 7.212 | 103.779 | 1.00 | 37.00 |
| 8451 | C | SER | B | 297 | -18.118 | 6.569 | 106.677 | 1.00 | 38.36 |
| 8452 | O | SER | B | 297 | -17.285 | 7.462 | 106.771 | 1.00 | 39.01 |
| 8453 | N | VAL | B | 298 | -17.957 | 5.376 | 107.219 | 1.00 | 38.97 |
| 8454 | CA | VAL | B | 298 | -16.748 | 5.050 | 107.936 | 1.00 | 39.42 |
| 8455 | CB | VAL | B | 298 | -17.026 | 4.754 | 109.412 | 1.00 | 39.31 |
| 8456 | CG1 | VAL | B | 298 | -17.694 | 5.918 | 110.095 | 1.00 | 39.19 |

FIGURE 3 FJ

| A | B | C | D | E | F | G | H | I | J |
|---|---|---|---|---|---|---|---|---|---|
| 8457 | CG2 | VAL | B | 298 | -15.730 | 4.393 | 110.106 | 1.00 | 39.59 |
| 8458 | C | VAL | B | 298 | -16.116 | 3.788 | 107.379 | 1.00 | 39.78 |
| 8459 | O | VAL | B | 298 | -16.796 | 2.781 | 107.193 | 1.00 | 38.93 |
| 8460 | N | MET | B | 299 | -14.809 | 3.840 | 107.130 | 1.00 | 40.58 |
| 8461 | CA | MET | B | 299 | -14.084 | 2.641 | 106.752 | 1.00 | 41.10 |
| 8462 | CB | MET | B | 299 | -13.045 | 2.919 | 105.678 | 1.00 | 40.94 |
| 8463 | CG | MET | B | 299 | -12.122 | 1.725 | 105.482 | 1.00 | 42.37 |
| 8464 | SD | MET | B | 299 | -10.984 | 1.874 | 104.140 | 1.00 | 45.66 |
| 8465 | CE | MET | B | 299 | -10.533 | 3.507 | 104.278 | 1.00 | 45.39 |
| 8466 | C | MET | B | 299 | -13.390 | 2.037 | 107.961 | 1.00 | 41.61 |
| 8467 | O | MET | B | 299 | -12.568 | 2.691 | 108.603 | 1.00 | 42.63 |
| 8468 | N | ASP | B | 300 | -13.746 | 0.807 | 108.295 | 1.00 | 41.81 |
| 8469 | CA | ASP | B | 300 | -13.031 | 0.064 | 109.314 | 1.00 | 42.44 |
| 8470 | CB | ASP | B | 300 | -13.962 | -0.857 | 110.120 | 1.00 | 42.60 |
| 8471 | CG | ASP | B | 300 | -14.521 | -0.197 | 111.392 | 1.00 | 44.17 |
| 8472 | OD1 | ASP | B | 300 | -15.580 | -0.658 | 111.884 | 1.00 | 45.87 |
| 8473 | OD2 | ASP | B | 300 | -13.981 | 0.768 | 111.978 | 1.00 | 43.48 |
| 8474 | C | ASP | B | 300 | -12.001 | -0.789 | 108.567 | 1.00 | 42.81 |
| 8475 | O | ASP | B | 300 | -12.163 | -1.091 | 107.371 | 1.00 | 42.31 |
| 8476 | N | ILE | B | 301 | -10.939 | -1.161 | 109.271 | 1.00 | 42.82 |
| 8477 | CA | ILE | B | 301 | -9.903 | -2.013 | 108.719 | 1.00 | 43.40 |
| 8478 | CB | ILE | B | 301 | -8.680 | -1.170 | 108.381 | 1.00 | 43.02 |
| 8479 | CG1 | ILE | B | 301 | -9.016 | -0.280 | 107.189 | 1.00 | 41.96 |
| 8480 | CD1 | ILE | B | 301 | -8.020 | 0.789 | 106.904 | 1.00 | 41.81 |
| 8481 | CG2 | ILE | B | 301 | -7.495 | -2.049 | 108.043 | 1.00 | 43.20 |
| 8482 | C | ILE | B | 301 | -9.642 | -3.065 | 109.775 | 1.00 | 44.39 |
| 8483 | O | ILE | B | 301 | -9.149 | -2.756 | 110.853 | 1.00 | 44.81 |
| 8484 | N | CYS | B | 302 | -10.023 | -4.303 | 109.488 | 1.00 | 45.55 |
| 8485 | CA | CYS | B | 302 | -9.973 | -5.363 | 110.497 | 1.00 | 46.76 |
| 8486 | CB | CYS | B | 302 | -11.351 | -6.028 | 110.644 | 1.00 | 46.70 |
| 8487 | SG | CYS | B | 302 | -12.758 | -4.879 | 110.687 | 1.00 | 49.41 |
| 8488 | C | CYS | B | 302 | -8.911 | -6.438 | 110.260 | 1.00 | 47.31 |
| 8489 | O | CYS | B | 302 | -8.980 | -7.221 | 109.299 | 1.00 | 47.48 |
| 8490 | N | ASP | B | 303 | -7.934 | -6.483 | 111.158 | 1.00 | 47.98 |
| 8491 | CA | ASP | B | 303 | -6.888 | -7.484 | 111.093 | 1.00 | 48.36 |
| 8492 | CB | ASP | B | 303 | -5.607 | -6.955 | 111.734 | 1.00 | 48.96 |
| 8493 | CG | ASP | B | 303 | -4.750 | -6.172 | 110.758 | 1.00 | 50.88 |
| 8494 | OD1 | ASP | B | 303 | -5.265 | -5.232 | 110.121 | 1.00 | 53.09 |
| 8495 | OD2 | ASP | B | 303 | -3.543 | -6.424 | 110.554 | 1.00 | 54.16 |
| 8496 | C | ASP | B | 303 | -7.363 | -8.755 | 111.786 | 1.00 | 48.00 |
| 8497 | O | ASP | B | 303 | -8.117 | -8.692 | 112.743 | 1.00 | 47.91 |
| 8498 | N | TYR | B | 304 | -6.950 | -9.908 | 111.269 | 1.00 | 48.08 |
| 8499 | CA | TYR | B | 304 | -7.288 | -11.200 | 111.857 | 1.00 | 47.82 |
| 8500 | CB | TYR | B | 304 | -7.167 | -12.283 | 110.794 | 1.00 | 47.24 |
| 8501 | CG | TYR | B | 304 | -7.213 | -13.681 | 111.340 | 1.00 | 45.86 |
| 8502 | CD1 | TYR | B | 304 | -8.400 | -14.218 | 111.796 | 1.00 | 44.73 |
| 8503 | CE1 | TYR | B | 304 | -8.458 | -15.489 | 112.298 | 1.00 | 44.26 |
| 8504 | CZ | TYR | B | 304 | -7.317 | -16.256 | 112.356 | 1.00 | 43.75 |
| 8505 | OH | TYR | B | 304 | -7.406 | -17.528 | 112.858 | 1.00 | 45.04 |
| 8506 | CE2 | TYR | B | 304 | -6.118 | -15.757 | 111.916 | 1.00 | 43.24 |
| 8507 | CD2 | TYR | B | 304 | -6.069 | -14.463 | 111.413 | 1.00 | 44.57 |

FIGURE 3 FK

| A | B | C | D | E | F | G | H | I | J |
|---|---|---|---|---|---|---|---|---|---|
| 8508 | C | TYR | B | 304 | -6.313 | -11.488 | 113.012 | 1.00 | 48.33 |
| 8509 | O | TYR | B | 304 | -5.176 | -11.027 | 112.975 | 1.00 | 47.62 |
| 8510 | N | ASP | B | 305 | -6.753 | -12.255 | 114.014 | 1.00 | 49.23 |
| 8511 | CA | ASP | B | 305 | -5.940 | -12.534 | 115.209 | 1.00 | 50.27 |
| 8512 | CB | ASP | B | 305 | -6.649 | -12.078 | 116.498 | 1.00 | 50.05 |
| 8513 | CG | ASP | B | 305 | -5.713 | -12.053 | 117.732 | 1.00 | 50.37 |
| 8514 | OD1 | ASP | B | 305 | -5.369 | -13.129 | 118.279 | 1.00 | 49.56 |
| 8515 | OD2 | ASP | B | 305 | -5.288 | -10.996 | 118.240 | 1.00 | 49.17 |
| 8516 | C | ASP | B | 305 | -5.571 | -13.996 | 115.331 | 1.00 | 51.26 |
| 8517 | O | ASP | B | 305 | -6.420 | -14.832 | 115.627 | 1.00 | 51.15 |
| 8518 | N | GLU | B | 306 | -4.288 | -14.281 | 115.108 | 1.00 | 52.94 |
| 8519 | CA | GLU | B | 306 | -3.722 | -15.619 | 115.228 | 1.00 | 54.25 |
| 8520 | CB | GLU | B | 306 | -2.197 | -15.522 | 115.380 | 1.00 | 54.85 |
| 8521 | CG | GLU | B | 306 | -1.438 | -15.115 | 114.130 | 1.00 | 56.89 |
| 8522 | CD | GLU | B | 306 | -0.657 | -16.271 | 113.543 | 1.00 | 59.93 |
| 8523 | OE1 | GLU | B | 306 | 0.528 | -16.072 | 113.180 | 1.00 | 61.01 |
| 8524 | OE2 | GLU | B | 306 | -1.227 | -17.384 | 113.460 | 1.00 | 61.35 |
| 8525 | C | GLU | B | 306 | -4.268 | -16.341 | 116.447 | 1.00 | 54.31 |
| 8526 | O | GLU | B | 306 | -4.751 | -17.460 | 116.342 | 1.00 | 54.14 |
| 8527 | N | SER | B | 307 | -4.182 | -15.699 | 117.609 | 1.00 | 54.55 |
| 8528 | CA | SER | B | 307 | -4.638 | -16.342 | 118.842 | 1.00 | 54.92 |
| 8529 | CB | SER | B | 307 | -3.919 | -15.790 | 120.090 | 1.00 | 54.93 |
| 8530 | OG | SER | B | 307 | -3.686 | -14.391 | 120.021 | 1.00 | 54.98 |
| 8531 | C | SER | B | 307 | -6.155 | -16.344 | 119.016 | 1.00 | 54.94 |
| 8532 | O | SER | B | 307 | -6.747 | -17.396 | 119.262 | 1.00 | 55.07 |
| 8533 | N | SER | B | 308 | -6.787 | -15.180 | 118.896 | 1.00 | 55.09 |
| 8534 | CA | SER | B | 308 | -8.242 | -15.116 | 119.028 | 1.00 | 55.20 |
| 8535 | CB | SER | B | 308 | -8.760 | -13.703 | 118.753 | 1.00 | 55.20 |
| 8536 | OG | SER | B | 308 | -8.050 | -12.698 | 119.459 | 1.00 | 56.52 |
| 8537 | C | SER | B | 308 | -8.907 | -16.064 | 118.028 | 1.00 | 54.99 |
| 8538 | O | SER | B | 308 | -9.639 | -16.985 | 118.394 | 1.00 | 55.23 |
| 8539 | N | GLY | B | 309 | -8.624 | -15.839 | 116.752 | 1.00 | 54.51 |
| 8540 | CA | GLY | B | 309 | -9.302 | -16.561 | 115.692 | 1.00 | 53.83 |
| 8541 | C | GLY | B | 309 | -10.396 | -15.596 | 115.279 | 1.00 | 52.94 |
| 8542 | O | GLY | B | 309 | -11.165 | -15.839 | 114.348 | 1.00 | 53.23 |
| 8543 | N | ARG | B | 310 | -10.440 | -14.481 | 116.001 | 1.00 | 51.75 |
| 8544 | CA | ARG | B | 310 | -11.400 | -13.416 | 115.773 | 1.00 | 50.58 |
| 8545 | CB | ARG | B | 310 | -11.784 | -12.752 | 117.092 | 1.00 | 50.88 |
| 8546 | CG | ARG | B | 310 | -12.907 | -13.443 | 117.792 | 1.00 | 54.09 |
| 8547 | CD | ARG | B | 310 | -12.707 | -13.618 | 119.270 | 1.00 | 59.77 |
| 8548 | NE | ARG | B | 310 | -13.888 | -14.230 | 119.871 | 1.00 | 64.94 |
| 8549 | CZ | ARG | B | 310 | -14.863 | -13.542 | 120.464 | 1.00 | 67.93 |
| 8550 | NH1 | ARG | B | 310 | -14.792 | -12.215 | 120.536 | 1.00 | 68.66 |
| 8551 | NH2 | ARG | B | 310 | -15.910 | -14.178 | 120.985 | 1.00 | 68.59 |
| 8552 | C | ARG | B | 310 | -10.793 | -12.367 | 114.899 | 1.00 | 48.86 |
| 8553 | O | ARG | B | 310 | -9.614 | -12.413 | 114.581 | 1.00 | 48.77 |
| 8554 | N | TRP | B | 311 | -11.623 | -11.401 | 114.541 | 1.00 | 47.08 |
| 8555 | CA | TRP | B | 311 | -11.215 | -10.279 | 113.733 | 1.00 | 45.09 |
| 8556 | CB | TRP | B | 311 | -12.079 | -10.231 | 112.477 | 1.00 | 44.10 |
| 8557 | CG | TRP | B | 311 | -11.753 | -11.328 | 111.540 | 1.00 | 40.23 |
| 8558 | CD1 | TRP | B | 311 | -12.191 | -12.618 | 111.588 | 1.00 | 37.52 |

FIGURE 3 FL

| A | B | C | D | E | F | G | H | I | J |
|---|---|---|---|---|---|---|---|---|---|
| 8559 | NE1 | TRP | B | 311 | -11.646 | -13.342 | 110.554 | 1.00 | 35.32 |
| 8560 | CE2 | TRP | B | 311 | -10.842 | -12.511 | 109.815 | 1.00 | 34.42 |
| 8561 | CD2 | TRP | B | 311 | -10.883 | -11.242 | 110.415 | 1.00 | 36.23 |
| 8562 | CE3 | TRP | B | 311 | -10.135 | -10.212 | 109.847 | 1.00 | 35.26 |
| 8563 | CZ3 | TRP | B | 311 | -9.388 | -10.477 | 108.730 | 1.00 | 35.47 |
| 8564 | CH2 | TRP | B | 311 | -9.371 | -11.744 | 108.158 | 1.00 | 34.18 |
| 8565 | CZ2 | TRP | B | 311 | -10.092 | -12.771 | 108.684 | 1.00 | 34.45 |
| 8566 | C | TRP | B | 311 | -11.373 | -9.005 | 114.551 | 1.00 | 44.85 |
| 8567 | O | TRP | B | 311 | -12.338 | -8.859 | 115.290 | 1.00 | 44.57 |
| 8568 | N | ASN | B | 312 | -10.435 | -8.083 | 114.409 | 1.00 | 44.33 |
| 8569 | CA | ASN | B | 312 | -10.464 | -6.862 | 115.187 | 1.00 | 44.71 |
| 8570 | CB | ASN | B | 312 | -9.411 | -6.911 | 116.303 | 1.00 | 44.96 |
| 8571 | CG | ASN | B | 312 | -9.768 | -7.883 | 117.398 | 1.00 | 44.98 |
| 8572 | OD1 | ASN | B | 312 | -10.562 | -7.564 | 118.281 | 1.00 | 46.84 |
| 8573 | ND2 | ASN | B | 312 | -9.172 | -9.072 | 117.361 | 1.00 | 43.43 |
| 8574 | C | ASN | B | 312 | -10.179 | -5.663 | 114.322 | 1.00 | 44.80 |
| 8575 | O | ASN | B | 312 | -9.282 | -5.690 | 113.496 | 1.00 | 44.20 |
| 8576 | N | CYS | B | 313 | -10.933 | -4.600 | 114.557 | 1.00 | 45.52 |
| 8577 | CA | CYS | B | 313 | -10.814 | -3.376 | 113.800 | 1.00 | 46.35 |
| 8578 | CB | CYS | B | 313 | -12.188 | -3.018 | 113.208 | 1.00 | 46.62 |
| 8579 | SG | CYS | B | 313 | -13.193 | -4.443 | 112.629 | 1.00 | 46.14 |
| 8580 | C | CYS | B | 313 | -10.324 | -2.266 | 114.724 | 1.00 | 47.10 |
| 8581 | O | CYS | B | 313 | -11.070 | -1.801 | 115.576 | 1.00 | 47.66 |
| 8582 | N | LEU | B | 314 | -9.078 | -1.834 | 114.564 | 1.00 | 47.75 |
| 8583 | CA | LEU | B | 314 | -8.548 | -0.787 | 115.433 | 1.00 | 48.41 |
| 8584 | CB | LEU | B | 314 | -7.026 | -0.667 | 115.314 | 1.00 | 48.43 |
| 8585 | CG | LEU | B | 314 | -6.124 | -1.561 | 116.168 | 1.00 | 48.67 |
| 8586 | CD1 | LEU | B | 314 | -5.616 | -2.768 | 115.399 | 1.00 | 50.57 |
| 8587 | CD2 | LEU | B | 314 | -6.808 | -1.971 | 117.463 | 1.00 | 49.11 |
| 8588 | C | LEU | B | 314 | -9.187 | 0.558 | 115.132 | 1.00 | 48.75 |
| 8589 | O | LEU | B | 314 | -9.092 | 1.062 | 114.018 | 1.00 | 48.76 |
| 8590 | N | VAL | B | 315 | -9.801 | 1.149 | 116.151 | 1.00 | 49.18 |
| 8591 | CA | VAL | B | 315 | -10.499 | 2.421 | 116.018 | 1.00 | 49.37 |
| 8592 | CB | VAL | B | 315 | -11.083 | 2.893 | 117.372 | 1.00 | 49.62 |
| 8593 | CG1 | VAL | B | 315 | -11.938 | 4.144 | 117.179 | 1.00 | 50.08 |
| 8594 | CG2 | VAL | B | 315 | -11.919 | 1.786 | 117.997 | 1.00 | 49.65 |
| 8595 | C | VAL | B | 315 | -9.654 | 3.525 | 115.398 | 1.00 | 49.37 |
| 8596 | O | VAL | B | 315 | -10.187 | 4.429 | 114.752 | 1.00 | 49.79 |
| 8597 | N | ALA | B | 316 | -8.341 | 3.444 | 115.583 | 1.00 | 49.29 |
| 8598 | CA | ALA | B | 316 | -7.413 | 4.427 | 115.030 | 1.00 | 48.81 |
| 8599 | CB | ALA | B | 316 | -6.150 | 4.498 | 115.880 | 1.00 | 49.17 |
| 8600 | C | ALA | B | 316 | -7.066 | 4.074 | 113.591 | 1.00 | 48.87 |
| 8601 | O | ALA | B | 316 | -6.333 | 4.802 | 112.908 | 1.00 | 48.88 |
| 8602 | N | ARG | B | 317 | -7.574 | 2.935 | 113.131 | 1.00 | 48.37 |
| 8603 | CA | ARG | B | 317 | -7.394 | 2.577 | 111.738 | 1.00 | 47.78 |
| 8604 | CB | ARG | B | 317 | -6.927 | 1.122 | 111.575 | 1.00 | 47.56 |
| 8605 | CG | ARG | B | 317 | -5.690 | 0.780 | 112.408 | 1.00 | 47.78 |
| 8606 | CD | ARG | B | 317 | -4.586 | -0.009 | 111.677 | 1.00 | 47.51 |
| 8607 | NE | ARG | B | 317 | -4.763 | -1.451 | 111.784 | 1.00 | 47.32 |
| 8608 | CZ | ARG | B | 317 | -3.766 | -2.328 | 111.773 | 1.00 | 48.74 |
| 8609 | NH1 | ARG | B | 317 | -4.025 | -3.627 | 111.879 | 1.00 | 47.96 |

FIGURE 3 FM

| A | B | C | D | E | F | G | H | I | J |
|---|---|---|---|---|---|---|---|---|---|
| 8610 | NH2 | ARG | B | 317 | -2.506 | -1.911 | 111.658 | 1.00 | 48.95 |
| 8611 | C | ARG | B | 317 | -8.705 | 2.868 | 110.996 | 1.00 | 47.39 |
| 8612 | O | ARG | B | 317 | -8.864 | 2.486 | 109.840 | 1.00 | 47.78 |
| 8613 | N | GLN | B | 318 | -9.634 | 3.547 | 111.672 | 1.00 | 46.34 |
| 8614 | CA | GLN | B | 318 | -10.901 | 3.950 | 111.065 | 1.00 | 45.47 |
| 8615 | CB | GLN | B | 318 | -11.967 | 4.243 | 112.118 | 1.00 | 45.18 |
| 8616 | CG | GLN | B | 318 | -12.715 | 3.030 | 112.621 | 1.00 | 44.04 |
| 8617 | CD | GLN | B | 318 | -13.832 | 3.384 | 113.596 | 1.00 | 43.62 |
| 8618 | OE1 | GLN | B | 318 | -14.374 | 2.495 | 114.270 | 1.00 | 43.11 |
| 8619 | NE2 | GLN | B | 318 | -14.172 | 4.679 | 113.685 | 1.00 | 41.17 |
| 8620 | C | GLN | B | 318 | -10.729 | 5.197 | 110.232 | 1.00 | 45.42 |
| 8621 | O | GLN | B | 318 | -10.027 | 6.119 | 110.625 | 1.00 | 45.28 |
| 8622 | N | HIS | B | 319 | -11.380 | 5.234 | 109.075 | 1.00 | 45.21 |
| 8623 | CA | HIS | B | 319 | -11.326 | 6.430 | 108.251 | 1.00 | 44.70 |
| 8624 | CB | HIS | B | 319 | -10.573 | 6.159 | 106.953 | 1.00 | 44.42 |
| 8625 | CG | HIS | B | 319 | -9.144 | 5.768 | 107.164 | 1.00 | 44.37 |
| 8626 | ND1 | HIS | B | 319 | -8.777 | 4.603 | 107.805 | 1.00 | 43.47 |
| 8627 | CE1 | HIS | B | 319 | -7.460 | 4.525 | 107.853 | 1.00 | 44.31 |
| 8628 | NE2 | HIS | B | 319 | -6.958 | 5.602 | 107.271 | 1.00 | 44.70 |
| 8629 | CD2 | HIS | B | 319 | -7.990 | 6.400 | 106.840 | 1.00 | 43.53 |
| 8630 | C | HIS | B | 319 | -12.745 | 6.937 | 108.001 | 1.00 | 44.84 |
| 8631 | O | HIS | B | 319 | -13.652 | 6.170 | 107.666 | 1.00 | 44.74 |
| 8632 | N | ILE | B | 320 | -12.939 | 8.232 | 108.195 | 1.00 | 44.88 |
| 8633 | CA | ILE | B | 320 | -14.245 | 8.819 | 108.005 | 1.00 | 44.83 |
| 8634 | CB | ILE | B | 320 | -14.574 | 9.781 | 109.152 | 1.00 | 45.25 |
| 8635 | CG1 | ILE | B | 320 | -14.665 | 9.023 | 110.477 | 1.00 | 45.63 |
| 8636 | CD1 | ILE | B | 320 | -14.781 | 9.948 | 111.666 | 1.00 | 48.51 |
| 8637 | CG2 | ILE | B | 320 | -15.872 | 10.531 | 108.868 | 1.00 | 44.08 |
| 8638 | C | ILE | B | 320 | -14.273 | 9.566 | 106.699 | 1.00 | 44.62 |
| 8639 | O | ILE | B | 320 | -13.342 | 10.288 | 106.375 | 1.00 | 44.36 |
| 8640 | N | GLU | B | 321 | -15.338 | 9.357 | 105.936 | 1.00 | 44.42 |
| 8641 | CA | GLU | B | 321 | -15.548 | 10.101 | 104.704 | 1.00 | 44.18 |
| 8642 | CB | GLU | B | 321 | -15.402 | 9.201 | 103.472 | 1.00 | 44.12 |
| 8643 | CG | GLU | B | 321 | -15.275 | 9.966 | 102.163 | 1.00 | 43.27 |
| 8644 | CD | GLU | B | 321 | -15.257 | 9.052 | 100.951 | 1.00 | 43.57 |
| 8645 | OE1 | GLU | B | 321 | -14.829 | 7.884 | 101.090 | 1.00 | 43.88 |
| 8646 | OE2 | GLU | B | 321 | -15.670 | 9.502 | 99.857 | 1.00 | 43.47 |
| 8647 | C | GLU | B | 321 | -16.945 | 10.714 | 104.786 | 1.00 | 44.02 |
| 8648 | O | GLU | B | 321 | -17.956 | 10.000 | 104.813 | 1.00 | 44.24 |
| 8649 | N | MET | B | 322 | -16.971 | 12.043 | 104.825 | 1.00 | 43.51 |
| 8650 | CA | MET | B | 322 | -18.170 | 12.840 | 105.001 | 1.00 | 42.63 |
| 8651 | CB | MET | B | 322 | -17.965 | 13.755 | 106.206 | 1.00 | 43.28 |
| 8652 | CG | MET | B | 322 | -18.418 | 13.265 | 107.548 | 1.00 | 45.74 |
| 8653 | SD | MET | B | 322 | -17.791 | 14.488 | 108.767 | 1.00 | 52.31 |
| 8654 | CE | MET | B | 322 | -17.696 | 15.985 | 107.722 | 1.00 | 51.74 |
| 8655 | C | MET | B | 322 | -18.349 | 13.779 | 103.829 | 1.00 | 41.53 |
| 8656 | O | MET | B | 322 | -17.427 | 14.007 | 103.064 | 1.00 | 41.26 |
| 8657 | N | SER | B | 323 | -19.533 | 14.368 | 103.729 | 1.00 | 40.61 |
| 8658 | CA | SER | B | 323 | -19.809 | 15.388 | 102.728 | 1.00 | 40.06 |
| 8659 | CB | SER | B | 323 | -20.495 | 14.804 | 101.495 | 1.00 | 39.82 |
| 8660 | OG | SER | B | 323 | -20.860 | 15.850 | 100.604 | 1.00 | 39.09 |

FIGURE 3 FN

| A | B | C | D | E | F | G | H | I | J |
|---|---|---|---|---|---|---|---|---|---|
| 8661 | C | SER | B | 323 | -20.730 | 16.421 | 103.350 | 1.00 | 39.95 |
| 8662 | O | SER | B | 323 | -21.649 | 16.074 | 104.081 | 1.00 | 39.28 |
| 8663 | N | THR | B | 324 | -20.493 | 17.690 | 103.068 | 1.00 | 40.39 |
| 8664 | CA | THR | B | 324 | -21.361 | 18.719 | 103.634 | 1.00 | 40.95 |
| 8665 | CB | THR | B | 324 | -20.553 | 19.794 | 104.399 | 1.00 | 41.44 |
| 8666 | OG1 | THR | B | 324 | -19.536 | 20.339 | 103.544 | 1.00 | 43.72 |
| 8667 | CG2 | THR | B | 324 | -19.757 | 19.151 | 105.520 | 1.00 | 41.41 |
| 8668 | C | THR | B | 324 | -22.203 | 19.344 | 102.548 | 1.00 | 40.11 |
| 8669 | O | THR | B | 324 | -23.164 | 20.032 | 102.842 | 1.00 | 40.55 |
| 8670 | N | THR | B | 325 | -21.835 | 19.094 | 101.293 | 1.00 | 39.33 |
| 8671 | CA | THR | B | 325 | -22.586 | 19.587 | 100.141 | 1.00 | 38.58 |
| 8672 | CB | THR | B | 325 | -21.634 | 19.908 | 98.977 | 1.00 | 38.55 |
| 8673 | OG1 | THR | B | 325 | -20.674 | 18.849 | 98.844 | 1.00 | 38.96 |
| 8674 | CG2 | THR | B | 325 | -20.770 | 21.122 | 99.305 | 1.00 | 40.01 |
| 8675 | C | THR | B | 325 | -23.631 | 18.578 | 99.638 | 1.00 | 37.87 |
| 8676 | O | THR | B | 325 | -24.496 | 18.934 | 98.859 | 1.00 | 38.08 |
| 8677 | N | GLY | B | 326 | -23.534 | 17.321 | 100.063 | 1.00 | 37.04 |
| 8678 | CA | GLY | B | 326 | -24.430 | 16.294 | 99.578 | 1.00 | 35.41 |
| 8679 | C | GLY | B | 326 | -24.145 | 14.931 | 100.169 | 1.00 | 34.41 |
| 8680 | O | GLY | B | 326 | -23.908 | 14.818 | 101.362 | 1.00 | 34.80 |
| 8681 | N | TRP | B | 327 | -24.190 | 13.890 | 99.339 | 1.00 | 33.13 |
| 8682 | CA | TRP | B | 327 | -23.973 | 12.527 | 99.803 | 1.00 | 31.83 |
| 8683 | CB | TRP | B | 327 | -24.906 | 11.567 | 99.049 | 1.00 | 31.57 |
| 8684 | CG | TRP | B | 327 | -24.661 | 11.606 | 97.556 | 1.00 | 29.42 |
| 8685 | CD1 | TRP | B | 327 | -23.879 | 10.756 | 96.840 | 1.00 | 27.20 |
| 8686 | NE1 | TRP | B | 327 | -23.846 | 11.133 | 95.523 | 1.00 | 26.93 |
| 8687 | CE2 | TRP | B | 327 | -24.626 | 12.246 | 95.361 | 1.00 | 27.08 |
| 8688 | CD2 | TRP | B | 327 | -25.146 | 12.579 | 96.627 | 1.00 | 27.38 |
| 8689 | CE3 | TRP | B | 327 | -25.991 | 13.693 | 96.729 | 1.00 | 27.46 |
| 8690 | CZ3 | TRP | B | 327 | -26.273 | 14.432 | 95.588 | 1.00 | 23.17 |
| 8691 | CH2 | TRP | B | 327 | -25.728 | 14.078 | 94.347 | 1.00 | 26.08 |
| 8692 | CZ2 | TRP | B | 327 | -24.915 | 12.985 | 94.209 | 1.00 | 26.03 |
| 8693 | C | TRP | B | 327 | -22.505 | 12.175 | 99.551 | 1.00 | 31.86 |
| 8694 | O | TRP | B | 327 | -21.758 | 12.966 | 98.982 | 1.00 | 31.37 |
| 8695 | N | VAL | B | 328 | -22.076 | 10.995 | 99.975 | 1.00 | 32.34 |
| 8696 | CA | VAL | B | 328 | -20.684 | 10.613 | 99.737 | 1.00 | 32.69 |
| 8697 | CB | VAL | B | 328 | -20.008 | 10.076 | 101.002 | 1.00 | 32.65 |
| 8698 | CG1 | VAL | B | 328 | -20.961 | 9.213 | 101.787 | 1.00 | 34.01 |
| 8699 | CG2 | VAL | B | 328 | -18.748 | 9.308 | 100.656 | 1.00 | 32.32 |
| 8700 | C | VAL | B | 328 | -20.556 | 9.605 | 98.596 | 1.00 | 32.55 |
| 8701 | O | VAL | B | 328 | -21.282 | 8.627 | 98.536 | 1.00 | 32.19 |
| 8702 | N | GLY | B | 329 | -19.602 | 9.859 | 97.714 | 1.00 | 32.82 |
| 8703 | CA | GLY | B | 329 | -19.337 | 9.004 | 96.583 | 1.00 | 33.09 |
| 8704 | C | GLY | B | 329 | -20.211 | 9.452 | 95.439 | 1.00 | 33.00 |
| 8705 | O | GLY | B | 329 | -21.127 | 10.267 | 95.620 | 1.00 | 33.18 |
| 8706 | N | ARG | B | 330 | -19.919 | 8.952 | 94.252 | 1.00 | 32.66 |
| 8707 | CA | ARG | B | 330 | -20.744 | 9.287 | 93.113 | 1.00 | 32.38 |
| 8708 | CB | ARG | B | 330 | -20.031 | 8.938 | 91.811 | 1.00 | 32.77 |
| 8709 | CG | ARG | B | 330 | -18.974 | 9.987 | 91.488 | 1.00 | 34.36 |
| 8710 | CD | ARG | B | 330 | -18.411 | 9.943 | 90.087 | 1.00 | 34.91 |
| 8711 | NE | ARG | B | 330 | -17.190 | 9.165 | 90.101 | 1.00 | 37.09 |

FIGURE 3 FO

| A | B | C | D | E | F | G | H | I | J |
|---|---|---|---|---|---|---|---|---|---|
| 8712 | CZ | ARG | B | 330 | -16.013 | 9.583 | 89.674 | 1.00 | 36.34 |
| 8713 | NH1 | ARG | B | 330 | -15.001 | 8.751 | 89.760 | 1.00 | 39.45 |
| 8714 | NH2 | ARG | B | 330 | -15.844 | 10.792 | 89.147 | 1.00 | 34.94 |
| 8715 | C | ARG | B | 330 | -22.103 | 8.612 | 93.302 | 1.00 | 31.87 |
| 8716 | O | ARG | B | 330 | -23.128 | 9.229 | 93.100 | 1.00 | 32.19 |
| 8717 | N | PHE | B | 331 | -22.105 | 7.364 | 93.746 | 1.00 | 31.31 |
| 8718 | CA | PHE | B | 331 | -23.333 | 6.687 | 94.119 | 1.00 | 31.39 |
| 8719 | CB | PHE | B | 331 | -23.792 | 5.693 | 93.043 | 1.00 | 30.66 |
| 8720 | CG | PHE | B | 331 | -24.187 | 6.347 | 91.758 | 1.00 | 28.41 |
| 8721 | CD1 | PHE | B | 331 | -25.503 | 6.715 | 91.530 | 1.00 | 26.38 |
| 8722 | CE1 | PHE | B | 331 | -25.873 | 7.333 | 90.339 | 1.00 | 27.31 |
| 8723 | CZ | PHE | B | 331 | -24.910 | 7.608 | 89.371 | 1.00 | 25.31 |
| 8724 | CE2 | PHE | B | 331 | -23.600 | 7.260 | 89.598 | 1.00 | 27.02 |
| 8725 | CD2 | PHE | B | 331 | -23.238 | 6.631 | 90.790 | 1.00 | 26.92 |
| 8726 | C | PHE | B | 331 | -23.120 | 5.997 | 95.461 | 1.00 | 32.56 |
| 8727 | O | PHE | B | 331 | -24.067 | 5.720 | 96.193 | 1.00 | 33.56 |
| 8728 | N | ARG | B | 332 | -21.865 | 5.712 | 95.782 | 1.00 | 33.38 |
| 8729 | CA | ARG | B | 332 | -21.520 | 5.072 | 97.044 | 1.00 | 33.89 |
| 8730 | CB | ARG | B | 332 | -21.739 | 3.555 | 96.970 | 1.00 | 34.01 |
| 8731 | CG | ARG | B | 332 | -20.838 | 2.816 | 95.989 | 1.00 | 34.01 |
| 8732 | CD | ARG | B | 332 | -21.325 | 1.427 | 95.626 | 1.00 | 36.66 |
| 8733 | NE | ARG | B | 332 | -22.754 | 1.443 | 95.271 | 1.00 | 39.82 |
| 8734 | CZ | ARG | B | 332 | -23.231 | 1.668 | 94.046 | 1.00 | 39.18 |
| 8735 | NH1 | ARG | B | 332 | -22.403 | 1.884 | 93.028 | 1.00 | 37.21 |
| 8736 | NH2 | ARG | B | 332 | -24.542 | 1.682 | 93.841 | 1.00 | 39.54 |
| 8737 | C | ARG | B | 332 | -20.067 | 5.368 | 97.324 | 1.00 | 34.48 |
| 8738 | O | ARG | B | 332 | -19.296 | 5.630 | 96.401 | 1.00 | 34.41 |
| 8739 | N | PRO | B | 333 | -19.684 | 5.348 | 98.595 | 1.00 | 35.25 |
| 8740 | CA | PRO | B | 333 | -18.285 | 5.587 | 98.952 | 1.00 | 35.46 |
| 8741 | CB | PRO | B | 333 | -18.184 | 5.045 | 100.382 | 1.00 | 35.54 |
| 8742 | CG | PRO | B | 333 | -19.574 | 5.147 | 100.936 | 1.00 | 36.38 |
| 8743 | CD | PRO | B | 333 | -20.542 | 5.116 | 99.772 | 1.00 | 35.16 |
| 8744 | C | PRO | B | 333 | -17.409 | 4.763 | 98.033 | 1.00 | 35.43 |
| 8745 | O | PRO | B | 333 | -17.645 | 3.585 | 97.878 | 1.00 | 36.30 |
| 8746 | N | SER | B | 334 | -16.399 | 5.360 | 97.435 | 1.00 | 35.72 |
| 8747 | CA | SER | B | 334 | -15.526 | 4.607 | 96.552 | 1.00 | 36.00 |
| 8748 | CB | SER | B | 334 | -14.561 | 5.533 | 95.844 | 1.00 | 36.20 |
| 8749 | OG | SER | B | 334 | -14.557 | 5.196 | 94.469 | 1.00 | 38.91 |
| 8750 | C | SER | B | 334 | -14.749 | 3.472 | 97.217 | 1.00 | 35.87 |
| 8751 | O | SER | B | 334 | -14.614 | 3.403 | 98.458 | 1.00 | 35.58 |
| 8752 | N | GLU | B | 335 | -14.227 | 2.587 | 96.373 | 1.00 | 35.21 |
| 8753 | CA | GLU | B | 335 | -13.488 | 1.443 | 96.862 | 1.00 | 34.87 |
| 8754 | CB | GLU | B | 335 | -13.756 | 0.208 | 96.003 | 1.00 | 35.20 |
| 8755 | CG | GLU | B | 335 | -12.934 | 0.113 | 94.729 | 1.00 | 36.16 |
| 8756 | CD | GLU | B | 335 | -13.390 | 1.083 | 93.659 | 1.00 | 39.30 |
| 8757 | OE1 | GLU | B | 335 | -14.592 | 1.443 | 93.662 | 1.00 | 41.87 |
| 8758 | OE2 | GLU | B | 335 | -12.550 | 1.484 | 92.810 | 1.00 | 39.58 |
| 8759 | C | GLU | B | 335 | -11.989 | 1.760 | 96.926 | 1.00 | 34.43 |
| 8760 | O | GLU | B | 335 | -11.448 | 2.475 | 96.078 | 1.00 | 33.63 |
| 8761 | N | PRO | B | 336 | -11.334 | 1.232 | 97.951 | 1.00 | 34.00 |
| 8762 | CA | PRO | B | 336 | -9.905 | 1.450 | 98.140 | 1.00 | 34.58 |

FIGURE 3 FP

| A | B | C | D | E | F | G | H | I | J |
|---|---|---|---|---|---|---|---|---|---|
| 8763 | CB | PRO | B | 336 | -9.767 | 1.320 | 99.651 | 1.00 | 34.64 |
| 8764 | CG | PRO | B | 336 | -10.730 | 0.199 | 99.975 | 1.00 | 34.28 |
| 8765 | CD | PRO | B | 336 | -11.901 | 0.390 | 99.021 | 1.00 | 33.04 |
| 8766 | C | PRO | B | 336 | -9.079 | 0.364 | 97.449 | 1.00 | 35.06 |
| 8767 | O | PRO | B | 336 | -9.509 | -0.787 | 97.352 | 1.00 | 34.53 |
| 8768 | N | HIS | B | 337 | -7.907 | 0.758 | 96.970 | 1.00 | 35.64 |
| 8769 | CA | HIS | B | 337 | -6.964 | -0.148 | 96.345 | 1.00 | 36.77 |
| 8770 | CB | HIS | B | 337 | -6.699 | 0.280 | 94.915 | 1.00 | 36.73 |
| 8771 | CG | HIS | B | 337 | -7.931 | 0.289 | 94.073 | 1.00 | 39.21 |
| 8772 | ND1 | HIS | B | 337 | -8.265 | -0.754 | 93.238 | 1.00 | 41.51 |
| 8773 | CE1 | HIS | B | 337 | -9.405 | -0.477 | 92.629 | 1.00 | 41.54 |
| 8774 | NE2 | HIS | B | 337 | -9.830 | 0.699 | 93.054 | 1.00 | 41.98 |
| 8775 | CD2 | HIS | B | 337 | -8.926 | 1.201 | 93.957 | 1.00 | 40.47 |
| 8776 | C | HIS | B | 337 | -5.678 | -0.177 | 97.169 | 1.00 | 36.72 |
| 8777 | O | HIS | B | 337 | -4.917 | 0.780 | 97.208 | 1.00 | 36.00 |
| 8778 | N | PHE | B | 338 | -5.460 | -1.301 | 97.822 | 1.00 | 37.60 |
| 8779 | CA | PHE | B | 338 | -4.348 | -1.477 | 98.735 | 1.00 | 38.65 |
| 8780 | CB | PHE | B | 338 | -4.719 | -2.573 | 99.715 | 1.00 | 38.15 |
| 8781 | CG | PHE | B | 338 | -5.756 | -2.160 | 100.697 | 1.00 | 38.45 |
| 8782 | CD1 | PHE | B | 338 | -7.101 | -2.326 | 100.416 | 1.00 | 38.31 |
| 8783 | CE1 | PHE | B | 338 | -8.057 | -1.942 | 101.328 | 1.00 | 36.65 |
| 8784 | CZ | PHE | B | 338 | -7.685 | -1.381 | 102.517 | 1.00 | 36.84 |
| 8785 | CE2 | PHE | B | 338 | -6.346 | -1.206 | 102.812 | 1.00 | 37.23 |
| 8786 | CD2 | PHE | B | 338 | -5.394 | -1.598 | 101.908 | 1.00 | 38.29 |
| 8787 | C | PHE | B | 338 | -3.016 | -1.826 | 98.088 | 1.00 | 39.48 |
| 8788 | O | PHE | B | 338 | -2.961 | -2.497 | 97.063 | 1.00 | 40.08 |
| 8789 | N | THR | B | 339 | -1.936 | -1.363 | 98.704 | 1.00 | 40.67 |
| 8790 | CA | THR | B | 339 | -0.603 | -1.718 | 98.258 | 1.00 | 41.39 |
| 8791 | CB | THR | B | 339 | 0.438 | -0.866 | 98.951 | 1.00 | 41.43 |
| 8792 | OG1 | THR | B | 339 | 0.165 | -0.881 | 100.357 | 1.00 | 41.21 |
| 8793 | CG2 | THR | B | 339 | 0.302 | 0.588 | 98.559 | 1.00 | 40.00 |
| 8794 | C | THR | B | 339 | -0.422 | -3.128 | 98.744 | 1.00 | 42.42 |
| 8795 | O | THR | B | 339 | -1.115 | -3.563 | 99.659 | 1.00 | 42.69 |
| 8796 | N | LEU | B | 340 | 0.531 | -3.831 | 98.156 | 1.00 | 43.57 |
| 8797 | CA | LEU | B | 340 | 0.808 | -5.214 | 98.528 | 1.00 | 44.63 |
| 8798 | CB | LEU | B | 340 | 2.094 | -5.680 | 97.841 | 1.00 | 44.77 |
| 8799 | CG | LEU | B | 340 | 2.175 | -7.175 | 97.554 | 1.00 | 45.78 |
| 8800 | CD1 | LEU | B | 340 | 0.971 | -7.604 | 96.719 | 1.00 | 45.59 |
| 8801 | CD2 | LEU | B | 340 | 2.274 | -7.983 | 98.841 | 1.00 | 46.02 |
| 8802 | C | LEU | B | 340 | 0.906 | -5.461 | 100.041 | 1.00 | 44.89 |
| 8803 | O | LEU | B | 340 | 0.349 | -6.434 | 100.547 | 1.00 | 44.86 |
| 8804 | N | ASP | B | 341 | 1.625 | -4.612 | 100.769 | 1.00 | 45.45 |
| 8805 | CA | ASP | B | 341 | 1.764 | -4.846 | 102.213 | 1.00 | 46.18 |
| 8806 | CB | ASP | B | 341 | 2.986 | -4.126 | 102.789 | 1.00 | 46.25 |
| 8807 | CG | ASP | B | 341 | 2.823 | -2.616 | 102.818 | 1.00 | 47.91 |
| 8808 | OD1 | ASP | B | 341 | 3.832 | -1.924 | 103.116 | 1.00 | 47.25 |
| 8809 | OD2 | ASP | B | 341 | 1.738 | -2.033 | 102.562 | 1.00 | 48.84 |
| 8810 | C | ASP | B | 341 | 0.495 | -4.530 | 103.026 | 1.00 | 46.03 |
| 8811 | O | ASP | B | 341 | 0.415 | -4.827 | 104.221 | 1.00 | 46.41 |
| 8812 | N | GLY | B | 342 | -0.488 | -3.919 | 102.379 | 1.00 | 45.84 |
| 8813 | CA | GLY | B | 342 | -1.758 | -3.626 | 103.021 | 1.00 | 45.65 |

FIGURE 3 FQ

| A | B | C | D | E | F | G | H | I | J |
|---|---|---|---|---|---|---|---|---|---|
| 8814 | C | GLY | B | 342 | -1.731 | -2.603 | 104.143 | 1.00 | 45.30 |
| 8815 | O | GLY | B | 342 | -2.662 | -2.529 | 104.947 | 1.00 | 45.37 |
| 8816 | N | ASN | B | 343 | -0.676 | -1.807 | 104.219 | 1.00 | 44.73 |
| 8817 | CA | ASN | B | 343 | -0.629 | -0.800 | 105.271 | 1.00 | 44.46 |
| 8818 | CB | ASN | B | 343 | 0.774 | -0.661 | 105.862 | 1.00 | 44.15 |
| 8819 | CG | ASN | B | 343 | 1.336 | -1.968 | 106.356 | 1.00 | 44.36 |
| 8820 | OD1 | ASN | B | 343 | 0.704 | -2.684 | 107.138 | 1.00 | 44.47 |
| 8821 | ND2 | ASN | B | 343 | 2.548 | -2.285 | 105.911 | 1.00 | 44.77 |
| 8822 | C | ASN | B | 343 | -1.054 | 0.523 | 104.675 | 1.00 | 44.12 |
| 8823 | O | ASN | B | 343 | -1.257 | 1.507 | 105.381 | 1.00 | 43.99 |
| 8824 | N | SER | B | 344 | -1.184 | 0.534 | 103.358 | 1.00 | 43.76 |
| 8825 | CA | SER | B | 344 | -1.531 | 1.752 | 102.652 | 1.00 | 43.78 |
| 8826 | CB | SER | B | 344 | -0.274 | 2.306 | 102.002 | 1.00 | 43.62 |
| 8827 | OG | SER | B | 344 | -0.444 | 3.664 | 101.675 | 1.00 | 45.00 |
| 8828 | C | SER | B | 344 | -2.609 | 1.496 | 101.588 | 1.00 | 43.53 |
| 8829 | O | SER | B | 344 | -2.904 | 0.334 | 101.262 | 1.00 | 43.57 |
| 8830 | N | PHE | B | 345 | -3.204 | 2.564 | 101.051 | 1.00 | 43.02 |
| 8831 | CA | PHE | B | 345 | -4.193 | 2.404 | 99.982 | 1.00 | 42.73 |
| 8832 | CB | PHE | B | 345 | -5.463 | 1.708 | 100.477 | 1.00 | 42.42 |
| 8833 | CG | PHE | B | 345 | -6.288 | 2.536 | 101.424 | 1.00 | 42.37 |
| 8834 | CD1 | PHE | B | 345 | -7.127 | 3.534 | 100.950 | 1.00 | 40.54 |
| 8835 | CE1 | PHE | B | 345 | -7.890 | 4.283 | 101.808 | 1.00 | 39.15 |
| 8836 | CZ | PHE | B | 345 | -7.834 | 4.047 | 103.150 | 1.00 | 39.99 |
| 8837 | CE2 | PHE | B | 345 | -7.009 | 3.041 | 103.647 | 1.00 | 40.96 |
| 8838 | CD2 | PHE | B | 345 | -6.247 | 2.294 | 102.787 | 1.00 | 41.13 |
| 8839 | C | PHE | B | 345 | -4.560 | 3.670 | 99.229 | 1.00 | 42.73 |
| 8840 | O | PHE | B | 345 | -4.367 | 4.784 | 99.718 | 1.00 | 42.82 |
| 8841 | N | TYR | B | 346 | -5.094 | 3.475 | 98.028 | 1.00 | 42.41 |
| 8842 | CA | TYR | B | 346 | -5.538 | 4.575 | 97.186 | 1.00 | 42.60 |
| 8843 | CB | TYR | B | 346 | -4.828 | 4.545 | 95.832 | 1.00 | 42.55 |
| 8844 | CG | TYR | B | 346 | -3.336 | 4.654 | 95.945 | 1.00 | 42.22 |
| 8845 | CD1 | TYR | B | 346 | -2.692 | 5.861 | 95.724 | 1.00 | 41.32 |
| 8846 | CE1 | TYR | B | 346 | -1.325 | 5.965 | 95.832 | 1.00 | 42.58 |
| 8847 | CZ | TYR | B | 346 | -0.579 | 4.854 | 96.173 | 1.00 | 42.02 |
| 8848 | OH | TYR | B | 346 | 0.789 | 4.953 | 96.290 | 1.00 | 42.68 |
| 8849 | CE2 | TYR | B | 346 | -1.196 | 3.651 | 96.411 | 1.00 | 42.43 |
| 8850 | CD2 | TYR | B | 346 | -2.570 | 3.557 | 96.293 | 1.00 | 43.21 |
| 8851 | C | TYR | B | 346 | -7.030 | 4.478 | 96.968 | 1.00 | 42.36 |
| 8852 | O | TYR | B | 346 | -7.555 | 3.384 | 96.723 | 1.00 | 42.86 |
| 8853 | N | LYS | B | 347 | -7.716 | 5.610 | 97.088 | 1.00 | 42.04 |
| 8854 | CA | LYS | B | 347 | -9.150 | 5.665 | 96.822 | 1.00 | 41.82 |
| 8855 | CB | LYS | B | 347 | -9.987 | 5.164 | 98.006 | 1.00 | 42.17 |
| 8856 | CG | LYS | B | 347 | -10.372 | 6.206 | 99.028 | 1.00 | 43.16 |
| 8857 | CD | LYS | B | 347 | -11.873 | 6.369 | 99.137 | 1.00 | 43.24 |
| 8858 | CE | LYS | B | 347 | -12.459 | 5.513 | 100.242 | 1.00 | 41.92 |
| 8859 | NZ | LYS | B | 347 | -13.922 | 5.833 | 100.429 | 1.00 | 41.44 |
| 8860 | C | LYS | B | 347 | -9.550 | 7.062 | 96.421 | 1.00 | 41.46 |
| 8861 | O | LYS | B | 347 | -9.000 | 8.045 | 96.922 | 1.00 | 41.71 |
| 8862 | N | ILE | B | 348 | -10.490 | 7.130 | 95.482 | 1.00 | 40.49 |
| 8863 | CA | ILE | B | 348 | -11.010 | 8.373 | 94.970 | 1.00 | 39.65 |
| 8864 | CB | ILE | B | 348 | -11.719 | 8.109 | 93.658 | 1.00 | 39.99 |

FIGURE 3 FR

| A | B | C | D | E | F | G | H | I | J |
|---|---|---|---|---|---|---|---|---|---|
| 8865 | CG1 | ILE | B | 348 | -10.751 | 7.503 | 92.647 | 1.00 | 40.33 |
| 8866 | CD1 | ILE | B | 348 | -11.423 | 7.141 | 91.328 | 1.00 | 42.02 |
| 8867 | CG2 | ILE | B | 348 | -12.336 | 9.373 | 93.106 | 1.00 | 40.21 |
| 8868 | C | ILE | B | 348 | -11.974 | 8.990 | 95.977 | 1.00 | 39.56 |
| 8869 | O | ILE | B | 348 | -12.813 | 8.294 | 96.551 | 1.00 | 39.35 |
| 8870 | N | ILE | B | 349 | -11.795 | 10.286 | 96.219 | 1.00 | 39.00 |
| 8871 | CA | ILE | B | 349 | -12.626 | 11.081 | 97.108 | 1.00 | 39.16 |
| 8872 | CB | ILE | B | 349 | -12.082 | 11.126 | 98.552 | 1.00 | 39.04 |
| 8873 | CG1 | ILE | B | 349 | -10.612 | 11.520 | 98.585 | 1.00 | 39.64 |
| 8874 | CD1 | ILE | B | 349 | -10.139 | 11.936 | 99.982 | 1.00 | 39.54 |
| 8875 | CG2 | ILE | B | 349 | -12.281 | 9.819 | 99.263 | 1.00 | 39.93 |
| 8876 | C | ILE | B | 349 | -12.639 | 12.488 | 96.547 | 1.00 | 39.03 |
| 8877 | O | ILE | B | 349 | -11.775 | 12.846 | 95.746 | 1.00 | 39.19 |
| 8878 | N | SER | B | 350 | -13.617 | 13.293 | 96.938 | 1.00 | 39.08 |
| 8879 | CA | SER | B | 350 | -13.647 | 14.653 | 96.434 | 1.00 | 39.74 |
| 8880 | CB | SER | B | 350 | -15.039 | 15.257 | 96.516 | 1.00 | 39.37 |
| 8881 | OG | SER | B | 350 | -15.721 | 14.721 | 97.617 | 1.00 | 40.57 |
| 8882 | C | SER | B | 350 | -12.652 | 15.487 | 97.206 | 1.00 | 40.13 |
| 8883 | O | SER | B | 350 | -12.518 | 15.327 | 98.421 | 1.00 | 39.82 |
| 8884 | N | ASN | B | 351 | -11.956 | 16.363 | 96.487 | 1.00 | 40.90 |
| 8885 | CA | ASN | B | 351 | -10.946 | 17.212 | 97.094 | 1.00 | 42.48 |
| 8886 | CB | ASN | B | 351 | -9.810 | 17.506 | 96.111 | 1.00 | 41.86 |
| 8887 | CG | ASN | B | 351 | -10.220 | 18.438 | 95.019 | 1.00 | 40.95 |
| 8888 | OD1 | ASN | B | 351 | -11.304 | 19.019 | 95.058 | 1.00 | 40.08 |
| 8889 | ND2 | ASN | B | 351 | -9.352 | 18.598 | 94.024 | 1.00 | 40.40 |
| 8890 | C | ASN | B | 351 | -11.525 | 18.503 | 97.656 | 1.00 | 43.74 |
| 8891 | O | ASN | B | 351 | -12.732 | 18.743 | 97.573 | 1.00 | 44.49 |
| 8892 | N | GLU | B | 352 | -10.650 | 19.325 | 98.227 | 1.00 | 45.07 |
| 8893 | CA | GLU | B | 352 | -11.040 | 20.589 | 98.853 | 1.00 | 46.08 |
| 8894 | CB | GLU | B | 352 | -9.803 | 21.451 | 99.160 | 1.00 | 46.33 |
| 8895 | CG | GLU | B | 352 | -8.980 | 21.843 | 97.933 | 1.00 | 48.13 |
| 8896 | CD | GLU | B | 352 | -8.169 | 20.681 | 97.364 | 1.00 | 50.83 |
| 8897 | OE1 | GLU | B | 352 | -7.816 | 20.729 | 96.157 | 1.00 | 50.33 |
| 8898 | OE2 | GLU | B | 352 | -7.884 | 19.713 | 98.125 | 1.00 | 51.22 |
| 8899 | C | GLU | B | 352 | -12.017 | 21.378 | 97.999 | 1.00 | 46.10 |
| 8900 | O | GLU | B | 352 | -12.918 | 22.038 | 98.517 | 1.00 | 46.29 |
| 8901 | N | GLU | B | 353 | -11.847 | 21.307 | 96.686 | 1.00 | 46.18 |
| 8902 | CA | GLU | B | 353 | -12.728 | 22.052 | 95.808 | 1.00 | 46.03 |
| 8903 | CB | GLU | B | 353 | -11.936 | 22.862 | 94.784 | 1.00 | 46.58 |
| 8904 | CG | GLU | B | 353 | -10.661 | 22.220 | 94.278 | 1.00 | 49.12 |
| 8905 | CD | GLU | B | 353 | -10.141 | 22.953 | 93.063 | 1.00 | 53.08 |
| 8906 | OE1 | GLU | B | 353 | -10.498 | 24.144 | 92.921 | 1.00 | 54.96 |
| 8907 | OE2 | GLU | B | 353 | -9.408 | 22.346 | 92.241 | 1.00 | 55.30 |
| 8908 | C | GLU | B | 353 | -13.824 | 21.223 | 95.132 | 1.00 | 45.23 |
| 8909 | O | GLU | B | 353 | -14.458 | 21.690 | 94.186 | 1.00 | 45.19 |
| 8910 | N | GLY | B | 354 | -14.048 | 20.004 | 95.609 | 1.00 | 44.03 |
| 8911 | CA | GLY | B | 354 | -15.155 | 19.210 | 95.103 | 1.00 | 42.61 |
| 8912 | C | GLY | B | 354 | -14.896 | 18.382 | 93.857 | 1.00 | 41.84 |
| 8913 | O | GLY | B | 354 | -15.818 | 17.772 | 93.292 | 1.00 | 41.34 |
| 8914 | N | TYR | B | 355 | -13.647 | 18.366 | 93.407 | 1.00 | 40.95 |
| 8915 | CA | TYR | B | 355 | -13.290 | 17.519 | 92.280 | 1.00 | 39.61 |

FIGURE 3 FS

| A | B | C | D | E | F | G | H | I | J |
|---|---|---|---|---|---|---|---|---|---|
| 8916 | CB | TYR | B | 355 | -12.291 | 18.191 | 91.363 | 1.00 | 39.28 |
| 8917 | CG | TYR | B | 355 | -12.919 | 19.335 | 90.611 | 1.00 | 38.85 |
| 8918 | CD1 | TYR | B | 355 | -12.950 | 20.610 | 91.156 | 1.00 | 38.45 |
| 8919 | CE1 | TYR | B | 355 | -13.539 | 21.664 | 90.483 | 1.00 | 37.46 |
| 8920 | CZ | TYR | B | 355 | -14.109 | 21.448 | 89.248 | 1.00 | 37.71 |
| 8921 | OH | TYR | B | 355 | -14.690 | 22.508 | 88.578 | 1.00 | 35.87 |
| 8922 | CE2 | TYR | B | 355 | -14.103 | 20.178 | 88.689 | 1.00 | 37.54 |
| 8923 | CD2 | TYR | B | 355 | -13.517 | 19.135 | 89.375 | 1.00 | 38.66 |
| 8924 | C | TYR | B | 355 | -12.795 | 16.207 | 92.830 | 1.00 | 38.85 |
| 8925 | O | TYR | B | 355 | -12.126 | 16.172 | 93.859 | 1.00 | 38.81 |
| 8926 | N | ARG | B | 356 | -13.195 | 15.119 | 92.183 | 1.00 | 37.98 |
| 8927 | CA | ARG | B | 356 | -12.839 | 13.791 | 92.672 | 1.00 | 36.90 |
| 8928 | CB | ARG | B | 356 | -13.934 | 12.771 | 92.344 | 1.00 | 36.89 |
| 8929 | CG | ARG | B | 356 | -15.072 | 12.844 | 93.340 | 1.00 | 36.55 |
| 8930 | CD | ARG | B | 356 | -16.371 | 12.194 | 92.916 | 1.00 | 35.78 |
| 8931 | NE | ARG | B | 356 | -17.475 | 12.940 | 93.499 | 1.00 | 37.53 |
| 8932 | CZ | ARG | B | 356 | -17.933 | 12.767 | 94.735 | 1.00 | 37.72 |
| 8933 | NH1 | ARG | B | 356 | -17.421 | 11.829 | 95.514 | 1.00 | 36.53 |
| 8934 | NH2 | ARG | B | 356 | -18.924 | 13.530 | 95.186 | 1.00 | 38.36 |
| 8935 | C | ARG | B | 356 | -11.477 | 13.346 | 92.182 | 1.00 | 35.86 |
| 8936 | O | ARG | B | 356 | -11.201 | 13.308 | 90.989 | 1.00 | 35.34 |
| 8937 | N | HIS | B | 357 | -10.622 | 13.013 | 93.129 | 1.00 | 35.61 |
| 8938 | CA | HIS | B | 357 | -9.268 | 12.639 | 92.797 | 1.00 | 35.35 |
| 8939 | CB | HIS | B | 357 | -8.361 | 13.854 | 92.922 | 1.00 | 34.69 |
| 8940 | CG | HIS | B | 357 | -8.491 | 14.797 | 91.777 | 1.00 | 31.97 |
| 8941 | ND1 | HIS | B | 357 | -7.876 | 14.577 | 90.569 | 1.00 | 29.99 |
| 8942 | CE1 | HIS | B | 357 | -8.186 | 15.552 | 89.734 | 1.00 | 30.81 |
| 8943 | NE2 | HIS | B | 357 | -8.992 | 16.392 | 90.357 | 1.00 | 30.84 |
| 8944 | CD2 | HIS | B | 357 | -9.207 | 15.936 | 91.635 | 1.00 | 31.68 |
| 8945 | C | HIS | B | 357 | -8.772 | 11.511 | 93.666 | 1.00 | 36.43 |
| 8946 | O | HIS | B | 357 | -9.428 | 11.110 | 94.634 | 1.00 | 35.70 |
| 8947 | N | ILE | B | 358 | -7.602 | 11.000 | 93.307 | 1.00 | 37.92 |
| 8948 | CA | ILE | B | 358 | -7.014 | 9.897 | 94.041 | 1.00 | 39.58 |
| 8949 | CB | ILE | B | 358 | -6.043 | 9.143 | 93.142 | 1.00 | 39.62 |
| 8950 | CG1 | ILE | B | 358 | -6.726 | 8.773 | 91.823 | 1.00 | 39.16 |
| 8951 | CD1 | ILE | B | 358 | -5.780 | 8.118 | 90.858 | 1.00 | 40.18 |
| 8952 | CG2 | ILE | B | 358 | -5.518 | 7.925 | 93.865 | 1.00 | 38.65 |
| 8953 | C | ILE | B | 358 | -6.285 | 10.376 | 95.284 | 1.00 | 40.60 |
| 8954 | O | ILE | B | 358 | -5.345 | 11.143 | 95.200 | 1.00 | 40.23 |
| 8955 | N | CYS | B | 359 | -6.728 | 9.911 | 96.440 | 1.00 | 42.66 |
| 8956 | CA | CYS | B | 359 | -6.073 | 10.277 | 97.677 | 1.00 | 44.79 |
| 8957 | CB | CYS | B | 359 | -7.078 | 10.791 | 98.712 | 1.00 | 44.98 |
| 8958 | SG | CYS | B | 359 | -6.425 | 12.181 | 99.684 | 1.00 | 50.06 |
| 8959 | C | CYS | B | 359 | -5.301 | 9.070 | 98.201 | 1.00 | 45.23 |
| 8960 | O | CYS | B | 359 | -5.806 | 7.945 | 98.200 | 1.00 | 44.97 |
| 8961 | N | TYR | B | 360 | -4.068 | 9.313 | 98.633 | 1.00 | 45.97 |
| 8962 | CA | TYR | B | 360 | -3.203 | 8.253 | 99.133 | 1.00 | 46.80 |
| 8963 | CB | TYR | B | 360 | -1.767 | 8.506 | 98.666 | 1.00 | 47.14 |
| 8964 | CG | TYR | B | 360 | -0.755 | 7.530 | 99.201 | 1.00 | 48.65 |
| 8965 | CD1 | TYR | B | 360 | 0.432 | 7.978 | 99.778 | 1.00 | 50.02 |
| 8966 | CE1 | TYR | B | 360 | 1.363 | 7.089 | 100.275 | 1.00 | 50.74 |

FIGURE 3 FT

| A | B | C | D | E | F | G | H | I | J |
|---|---|---|---|---|---|---|---|---|---|
| 8967 | CZ | TYR | B | 360 | 1.109 | 5.737 | 100.199 | 1.00 | 50.96 |
| 8968 | OH | TYR | B | 360 | 2.029 | 4.836 | 100.683 | 1.00 | 52.69 |
| 8969 | CE2 | TYR | B | 360 | -0.059 | 5.273 | 99.629 | 1.00 | 50.11 |
| 8970 | CD2 | TYR | B | 360 | -0.981 | 6.166 | 99.138 | 1.00 | 48.61 |
| 8971 | C | TYR | B | 360 | -3.308 | 8.163 | 100.652 | 1.00 | 47.03 |
| 8972 | O | TYR | B | 360 | -3.100 | 9.141 | 101.356 | 1.00 | 47.17 |
| 8973 | N | PHE | B | 361 | -3.662 | 6.990 | 101.157 | 1.00 | 47.69 |
| 8974 | CA | PHE | B | 361 | -3.859 | 6.826 | 102.586 | 1.00 | 48.63 |
| 8975 | CB | PHE | B | 361 | -5.237 | 6.219 | 102.892 | 1.00 | 48.62 |
| 8976 | CG | PHE | B | 361 | -6.400 | 7.123 | 102.573 | 1.00 | 49.54 |
| 8977 | CD1 | PHE | B | 361 | -7.191 | 7.635 | 103.592 | 1.00 | 49.80 |
| 8978 | CE1 | PHE | B | 361 | -8.276 | 8.459 | 103.306 | 1.00 | 50.81 |
| 8979 | CZ | PHE | B | 361 | -8.580 | 8.775 | 101.993 | 1.00 | 50.87 |
| 8980 | CE2 | PHE | B | 361 | -7.799 | 8.264 | 100.965 | 1.00 | 50.72 |
| 8981 | CD2 | PHE | B | 361 | -6.719 | 7.439 | 101.259 | 1.00 | 49.46 |
| 8982 | C | PHE | B | 361 | -2.836 | 5.907 | 103.210 | 1.00 | 49.27 |
| 8983 | O | PHE | B | 361 | -2.396 | 4.934 | 102.607 | 1.00 | 48.69 |
| 8984 | N | GLN | B | 362 | -2.490 | 6.222 | 104.448 | 1.00 | 50.41 |
| 8985 | CA | GLN | B | 362 | -1.643 | 5.375 | 105.249 | 1.00 | 51.46 |
| 8986 | CB | GLN | B | 362 | -0.577 | 6.206 | 105.952 | 1.00 | 51.57 |
| 8987 | CG | GLN | B | 362 | 0.828 | 5.671 | 105.793 | 1.00 | 54.18 |
| 8988 | CD | GLN | B | 362 | 1.518 | 6.183 | 104.530 | 1.00 | 56.47 |
| 8989 | OE1 | GLN | B | 362 | 2.745 | 6.357 | 104.512 | 1.00 | 57.84 |
| 8990 | NE2 | GLN | B | 362 | 0.740 | 6.420 | 103.478 | 1.00 | 54.93 |
| 8991 | C | GLN | B | 362 | -2.634 | 4.828 | 106.247 | 1.00 | 51.84 |
| 8992 | O | GLN | B | 362 | -3.385 | 5.587 | 106.855 | 1.00 | 51.72 |
| 8993 | N | ILE | B | 363 | -2.656 | 3.515 | 106.408 | 1.00 | 52.75 |
| 8994 | CA | ILE | B | 363 | -3.628 | 2.874 | 107.281 | 1.00 | 53.94 |
| 8995 | CB | ILE | B | 363 | -3.340 | 1.358 | 107.355 | 1.00 | 53.90 |
| 8996 | CG1 | ILE | B | 363 | -4.581 | 0.564 | 106.966 | 1.00 | 54.08 |
| 8997 | CD1 | ILE | B | 363 | -4.854 | 0.624 | 105.495 | 1.00 | 53.92 |
| 8998 | CG2 | ILE | B | 363 | -2.799 | 0.943 | 108.702 | 1.00 | 53.69 |
| 8999 | C | ILE | B | 363 | -3.723 | 3.488 | 108.684 | 1.00 | 55.21 |
| 9000 | O | ILE | B | 363 | -4.779 | 3.426 | 109.317 | 1.00 | 55.01 |
| 9001 | N | ASP | B | 364 | -2.626 | 4.094 | 109.151 | 1.00 | 56.58 |
| 9002 | CA | ASP | B | 364 | -2.559 | 4.663 | 110.502 | 1.00 | 57.94 |
| 9003 | CB | ASP | B | 364 | -1.217 | 4.311 | 111.183 | 1.00 | 58.15 |
| 9004 | CG | ASP | B | 364 | -1.056 | 2.813 | 111.450 | 1.00 | 59.41 |
| 9005 | OD1 | ASP | B | 364 | -1.482 | 2.339 | 112.531 | 1.00 | 60.00 |
| 9006 | OD2 | ASP | B | 364 | -0.506 | 2.032 | 110.642 | 1.00 | 60.28 |
| 9007 | C | ASP | B | 364 | -2.755 | 6.178 | 110.550 | 1.00 | 58.51 |
| 9008 | O | ASP | B | 364 | -2.919 | 6.744 | 111.631 | 1.00 | 58.72 |
| 9009 | N | LYS | B | 365 | -2.724 | 6.840 | 109.394 | 1.00 | 59.16 |
| 9010 | CA | LYS | B | 365 | -2.862 | 8.299 | 109.349 | 1.00 | 59.70 |
| 9011 | CB | LYS | B | 365 | -1.759 | 8.913 | 108.487 | 1.00 | 59.92 |
| 9012 | CG | LYS | B | 365 | -0.397 | 9.007 | 109.174 | 1.00 | 62.07 |
| 9013 | CD | LYS | B | 365 | -0.328 | 10.203 | 110.136 | 1.00 | 64.42 |
| 9014 | CE | LYS | B | 365 | 0.943 | 10.173 | 110.991 | 1.00 | 65.81 |
| 9015 | NZ | LYS | B | 365 | 1.022 | 11.341 | 111.931 | 1.00 | 66.10 |
| 9016 | C | LYS | B | 365 | -4.228 | 8.788 | 108.854 | 1.00 | 59.90 |
| 9017 | O | LYS | B | 365 | -4.772 | 8.291 | 107.858 | 1.00 | 59.90 |

FIGURE 3 FU

| A | B | C | D | E | F | G | H | I | J |
|---|---|---|---|---|---|---|---|---|---|
| 9018 | N | LYS | B | 366 | -4.769 | 9.783 | 109.545 | 1.00 | 59.96 |
| 9019 | CA | LYS | B | 366 | -6.048 | 10.358 | 109.164 | 1.00 | 59.95 |
| 9020 | CB | LYS | B | 366 | -6.607 | 11.213 | 110.303 | 1.00 | 60.59 |
| 9021 | CG | LYS | B | 366 | -7.629 | 12.266 | 109.865 | 1.00 | 62.10 |
| 9022 | CD | LYS | B | 366 | -6.953 | 13.597 | 109.519 | 1.00 | 64.53 |
| 9023 | CE | LYS | B | 366 | -6.364 | 14.256 | 110.756 | 1.00 | 65.27 |
| 9024 | NZ | LYS | B | 366 | -5.765 | 15.580 | 110.433 | 1.00 | 66.91 |
| 9025 | C | LYS | B | 366 | -5.900 | 11.200 | 107.910 | 1.00 | 59.37 |
| 9026 | O | LYS | B | 366 | -6.807 | 11.275 | 107.080 | 1.00 | 59.74 |
| 9027 | N | ASP | B | 367 | -4.752 | 11.842 | 107.770 | 1.00 | 58.44 |
| 9028 | CA | ASP | B | 367 | -4.535 | 12.692 | 106.614 | 1.00 | 57.48 |
| 9029 | CB | ASP | B | 367 | -3.555 | 13.824 | 106.935 | 1.00 | 58.05 |
| 9030 | CG | ASP | B | 367 | -4.231 | 15.009 | 107.618 | 1.00 | 59.15 |
| 9031 | OD1 | ASP | B | 367 | -3.784 | 15.393 | 108.727 | 1.00 | 59.86 |
| 9032 | OD2 | ASP | B | 367 | -5.209 | 15.616 | 107.118 | 1.00 | 59.70 |
| 9033 | C | ASP | B | 367 | -4.061 | 11.898 | 105.400 | 1.00 | 56.40 |
| 9034 | O | ASP | B | 367 | -3.011 | 11.244 | 105.423 | 1.00 | 56.27 |
| 9035 | N | CYS | B | 368 | -4.863 | 11.943 | 104.345 | 1.00 | 54.53 |
| 9036 | CA | CYS | B | 368 | -4.486 | 11.319 | 103.103 | 1.00 | 52.77 |
| 9037 | CB | CYS | B | 368 | -5.716 | 10.731 | 102.402 | 1.00 | 52.82 |
| 9038 | SG | CYS | B | 368 | -6.823 | 11.959 | 101.664 | 1.00 | 51.25 |
| 9039 | C | CYS | B | 368 | -3.892 | 12.434 | 102.268 | 1.00 | 51.66 |
| 9040 | O | CYS | B | 368 | -4.100 | 13.609 | 102.567 | 1.00 | 51.26 |
| 9041 | N | THR | B | 369 | -3.137 | 12.074 | 101.241 | 1.00 | 50.24 |
| 9042 | CA | THR | B | 369 | -2.620 | 13.074 | 100.325 | 1.00 | 49.06 |
| 9043 | CB | THR | B | 369 | -1.098 | 13.303 | 100.515 | 1.00 | 49.33 |
| 9044 | OG1 | THR | B | 369 | -0.448 | 13.415 | 99.240 | 1.00 | 48.47 |
| 9045 | CG2 | THR | B | 369 | -0.447 | 12.091 | 101.165 | 1.00 | 49.87 |
| 9046 | C | THR | B | 369 | -3.000 | 12.708 | 98.894 | 1.00 | 48.47 |
| 9047 | O | THR | B | 369 | -3.044 | 11.532 | 98.524 | 1.00 | 48.29 |
| 9048 | N | PHE | B | 370 | -3.300 | 13.733 | 98.109 | 1.00 | 47.18 |
| 9049 | CA | PHE | B | 370 | -3.771 | 13.572 | 96.754 | 1.00 | 46.08 |
| 9050 | CB | PHE | B | 370 | -4.613 | 14.792 | 96.362 | 1.00 | 46.44 |
| 9051 | CG | PHE | B | 370 | -5.991 | 14.800 | 96.976 | 1.00 | 47.55 |
| 9052 | CD1 | PHE | B | 370 | -7.072 | 14.236 | 96.298 | 1.00 | 48.39 |
| 9053 | CE1 | PHE | B | 370 | -8.344 | 14.241 | 96.860 | 1.00 | 49.07 |
| 9054 | CZ | PHE | B | 370 | -8.538 | 14.810 | 98.115 | 1.00 | 49.41 |
| 9055 | CE2 | PHE | B | 370 | -7.465 | 15.375 | 98.792 | 1.00 | 47.58 |
| 9056 | CD2 | PHE | B | 370 | -6.207 | 15.364 | 98.225 | 1.00 | 46.62 |
| 9057 | C | PHE | B | 370 | -2.639 | 13.430 | 95.769 | 1.00 | 45.28 |
| 9058 | O | PHE | B | 370 | -1.699 | 14.227 | 95.770 | 1.00 | 45.61 |
| 9059 | N | ILE | B | 371 | -2.733 | 12.440 | 94.895 | 1.00 | 43.59 |
| 9060 | CA | ILE | B | 371 | -1.695 | 12.272 | 93.893 | 1.00 | 41.93 |
| 9061 | CB | ILE | B | 371 | -1.279 | 10.801 | 93.805 | 1.00 | 42.22 |
| 9062 | CG1 | ILE | B | 371 | -2.310 | 9.971 | 93.032 | 1.00 | 42.14 |
| 9063 | CD1 | ILE | B | 371 | -1.929 | 8.470 | 92.932 | 1.00 | 39.82 |
| 9064 | CG2 | ILE | B | 371 | -1.126 | 10.253 | 95.214 | 1.00 | 40.79 |
| 9065 | C | ILE | B | 371 | -2.106 | 12.876 | 92.553 | 1.00 | 40.92 |
| 9066 | O | ILE | B | 371 | -1.269 | 13.061 | 91.657 | 1.00 | 40.67 |
| 9067 | N | THR | B | 372 | -3.398 | 13.202 | 92.443 | 1.00 | 39.48 |
| 9068 | CA | THR | B | 372 | -3.965 | 13.860 | 91.264 | 1.00 | 38.02 |

FIGURE 3 FV

| A | B | C | D | E | F | G | H | I | J |
|---|---|---|---|---|---|---|---|---|---|
| 9069 | CB | THR | B | 372 | -4.930 | 12.909 | 90.508 | 1.00 | 38.39 |
| 9070 | OG1 | THR | B | 372 | -6.046 | 12.579 | 91.356 | 1.00 | 35.81 |
| 9071 | CG2 | THR | B | 372 | -4.244 | 11.564 | 90.227 | 1.00 | 36.59 |
| 9072 | C | THR | B | 372 | -4.749 | 15.086 | 91.706 | 1.00 | 37.61 |
| 9073 | O | THR | B | 372 | -5.222 | 15.155 | 92.834 | 1.00 | 37.09 |
| 9074 | N | LYS | B | 373 | -4.937 | 16.030 | 90.799 | 1.00 | 37.10 |
| 9075 | CA | LYS | B | 373 | -5.635 | 17.252 | 91.137 | 1.00 | 37.18 |
| 9076 | CB | LYS | B | 373 | -4.728 | 18.190 | 91.964 | 1.00 | 37.58 |
| 9077 | CG | LYS | B | 373 | -3.943 | 19.181 | 91.082 | 1.00 | 39.33 |
| 9078 | CD | LYS | B | 373 | -3.308 | 20.349 | 91.870 | 1.00 | 43.81 |
| 9079 | CE | LYS | B | 373 | -1.808 | 20.142 | 92.085 | 1.00 | 45.57 |
| 9080 | NZ | LYS | B | 373 | -1.128 | 21.397 | 92.530 | 1.00 | 48.26 |
| 9081 | C | LYS | B | 373 | -5.981 | 17.959 | 89.852 | 1.00 | 36.51 |
| 9082 | O | LYS | B | 373 | -5.413 | 17.653 | 88.805 | 1.00 | 35.99 |
| 9083 | N | GLY | B | 374 | -6.884 | 18.935 | 89.949 | 1.00 | 36.28 |
| 9084 | CA | GLY | B | 374 | -7.294 | 19.723 | 88.808 | 1.00 | 36.50 |
| 9085 | C | GLY | B | 374 | -8.799 | 19.722 | 88.614 | 1.00 | 36.62 |
| 9086 | O | GLY | B | 374 | -9.537 | 19.005 | 89.301 | 1.00 | 35.95 |
| 9087 | N | THR | B | 375 | -9.250 | 20.530 | 87.662 | 1.00 | 36.75 |
| 9088 | CA | THR | B | 375 | -10.665 | 20.637 | 87.352 | 1.00 | 36.95 |
| 9089 | CB | THR | B | 375 | -11.011 | 22.056 | 86.901 | 1.00 | 37.51 |
| 9090 | OG1 | THR | B | 375 | -10.248 | 22.382 | 85.736 | 1.00 | 38.55 |
| 9091 | CG2 | THR | B | 375 | -10.524 | 23.079 | 87.944 | 1.00 | 38.45 |
| 9092 | C | THR | B | 375 | -11.106 | 19.615 | 86.302 | 1.00 | 36.41 |
| 9093 | O | THR | B | 375 | -11.529 | 19.961 | 85.190 | 1.00 | 36.63 |
| 9094 | N | TRP | B | 376 | -10.989 | 18.352 | 86.679 | 1.00 | 35.22 |
| 9095 | CA | TRP | B | 376 | -11.459 | 17.236 | 85.889 | 1.00 | 34.47 |
| 9096 | CB | TRP | B | 376 | -10.487 | 16.856 | 84.778 | 1.00 | 34.23 |
| 9097 | CG | TRP | B | 376 | -9.065 | 16.821 | 85.198 | 1.00 | 34.19 |
| 9098 | CD1 | TRP | B | 376 | -8.170 | 17.864 | 85.178 | 1.00 | 33.41 |
| 9099 | NE1 | TRP | B | 376 | -6.949 | 17.445 | 85.650 | 1.00 | 33.46 |
| 9100 | CE2 | TRP | B | 376 | -7.030 | 16.122 | 85.986 | 1.00 | 32.59 |
| 9101 | CD2 | TRP | B | 376 | -8.357 | 15.696 | 85.708 | 1.00 | 32.41 |
| 9102 | CE3 | TRP | B | 376 | -8.702 | 14.365 | 85.963 | 1.00 | 29.42 |
| 9103 | CZ3 | TRP | B | 376 | -7.749 | 13.523 | 86.462 | 1.00 | 29.49 |
| 9104 | CH2 | TRP | B | 376 | -6.431 | 13.976 | 86.726 | 1.00 | 31.96 |
| 9105 | CZ2 | TRP | B | 376 | -6.058 | 15.266 | 86.488 | 1.00 | 30.16 |
| 9106 | C | TRP | B | 376 | -11.535 | 16.185 | 86.958 | 1.00 | 34.44 |
| 9107 | O | TRP | B | 376 | -11.211 | 16.483 | 88.104 | 1.00 | 33.98 |
| 9108 | N | GLU | B | 377 | -11.994 | 14.979 | 86.641 | 1.00 | 34.14 |
| 9109 | CA | GLU | B | 377 | -12.082 | 13.977 | 87.690 | 1.00 | 33.77 |
| 9110 | CB | GLU | B | 377 | -13.526 | 13.797 | 88.152 | 1.00 | 34.05 |
| 9111 | CG | GLU | B | 377 | -14.158 | 15.039 | 88.743 | 1.00 | 35.06 |
| 9112 | CD | GLU | B | 377 | -15.413 | 14.728 | 89.525 | 1.00 | 35.00 |
| 9113 | OE1 | GLU | B | 377 | -15.679 | 15.462 | 90.487 | 1.00 | 36.61 |
| 9114 | OE2 | GLU | B | 377 | -16.121 | 13.753 | 89.190 | 1.00 | 33.99 |
| 9115 | C | GLU | B | 377 | -11.518 | 12.624 | 87.319 | 1.00 | 33.35 |
| 9116 | O | GLU | B | 377 | -11.294 | 12.327 | 86.150 | 1.00 | 33.34 |
| 9117 | N | VAL | B | 378 | -11.316 | 11.812 | 88.351 | 1.00 | 32.77 |
| 9118 | CA | VAL | B | 378 | -10.835 | 10.463 | 88.215 | 1.00 | 32.24 |
| 9119 | CB | VAL | B | 378 | -9.905 | 10.082 | 89.378 | 1.00 | 32.21 |

FIGURE 3 FW

| A | B | C | D | E | F | G | H | I | J |
|---|---|---|---|---|---|---|---|---|---|
| 9120 | CG1 | VAL | B | 378 | -9.514 | 8.606 | 89.265 | 1.00 | 32.33 |
| 9121 | CG2 | VAL | B | 378 | -8.655 | 10.997 | 89.392 | 1.00 | 32.04 |
| 9122 | C | VAL | B | 378 | -12.057 | 9.555 | 88.236 | 1.00 | 32.33 |
| 9123 | O | VAL | B | 378 | -12.786 | 9.491 | 89.222 | 1.00 | 31.70 |
| 9124 | N | ILE | B | 379 | -12.276 | 8.858 | 87.130 | 1.00 | 32.28 |
| 9125 | CA | ILE | B | 379 | -13.425 | 7.996 | 86.973 | 1.00 | 31.43 |
| 9126 | CB | ILE | B | 379 | -13.538 | 7.615 | 85.479 | 1.00 | 31.71 |
| 9127 | CG1 | ILE | B | 379 | -13.463 | 8.877 | 84.611 | 1.00 | 31.03 |
| 9128 | CD1 | ILE | B | 379 | -14.552 | 9.908 | 84.894 | 1.00 | 32.63 |
| 9129 | CG2 | ILE | B | 379 | -14.755 | 6.766 | 85.214 | 1.00 | 29.10 |
| 9130 | C | ILE | B | 379 | -13.217 | 6.762 | 87.827 | 1.00 | 31.87 |
| 9131 | O | ILE | B | 379 | -14.068 | 6.411 | 88.661 | 1.00 | 31.76 |
| 9132 | N | GLY | B | 380 | -12.078 | 6.103 | 87.633 | 1.00 | 31.93 |
| 9133 | CA | GLY | B | 380 | -11.779 | 4.922 | 88.418 | 1.00 | 33.11 |
| 9134 | C | GLY | B | 380 | -10.320 | 4.533 | 88.511 | 1.00 | 33.83 |
| 9135 | O | GLY | B | 380 | -9.510 | 4.874 | 87.664 | 1.00 | 34.19 |
| 9136 | N | ILE | B | 381 | -9.979 | 3.808 | 89.565 | 1.00 | 34.81 |
| 9137 | CA | ILE | B | 381 | -8.635 | 3.268 | 89.690 | 1.00 | 35.36 |
| 9138 | CB | ILE | B | 381 | -8.191 | 3.255 | 91.143 | 1.00 | 35.26 |
| 9139 | CG1 | ILE | B | 381 | -7.923 | 4.694 | 91.613 | 1.00 | 35.36 |
| 9140 | CD1 | ILE | B | 381 | -7.818 | 4.864 | 93.143 | 1.00 | 33.27 |
| 9141 | CG2 | ILE | B | 419 | -6.952 | 2.379 | 91.275 | 1.00 | 36.08 |
| 9142 | C | ILE | B | 419 | -8.661 | 1.854 | 89.122 | 1.00 | 35.57 |
| 9143 | O | ILE | B | 419 | -9.324 | 0.978 | 89.662 | 1.00 | 35.74 |
| 9144 | N | GLU | B | 420 | -7.929 | 1.646 | 88.036 | 1.00 | 36.13 |
| 9145 | CA | GLU | B | 420 | -7.940 | 0.385 | 87.300 | 1.00 | 36.98 |
| 9146 | CB | GLU | B | 420 | -7.780 | 0.670 | 85.802 | 1.00 | 37.12 |
| 9147 | CG | GLU | B | 420 | -8.783 | 1.692 | 85.284 | 1.00 | 38.08 |
| 9148 | CD | GLU | B | 420 | -10.204 | 1.374 | 85.714 | 1.00 | 39.72 |
| 9149 | OE1 | GLU | B | 420 | -10.645 | 0.217 | 85.552 | 1.00 | 41.76 |
| 9150 | OE2 | GLU | B | 420 | -10.881 | 2.275 | 86.235 | 1.00 | 41.40 |
| 9151 | C | GLU | B | 420 | -6.918 | -0.664 | 87.727 | 1.00 | 37.28 |
| 9152 | O | GLU | B | 420 | -7.170 | -1.853 | 87.580 | 1.00 | 37.66 |
| 9153 | N | ALA | B | 421 | -5.766 | -0.239 | 88.233 | 1.00 | 37.71 |
| 9154 | CA | ALA | B | 421 | -4.754 | -1.197 | 88.656 | 1.00 | 38.20 |
| 9155 | CB | ALA | B | 421 | -4.275 | -2.047 | 87.475 | 1.00 | 38.00 |
| 9156 | C | ALA | B | 421 | -3.574 | -0.537 | 89.359 | 1.00 | 38.59 |
| 9157 | O | ALA | B | 421 | -3.209 | 0.615 | 89.100 | 1.00 | 39.16 |
| 9158 | N | LEU | B | 422 | -2.948 | -1.301 | 90.230 | 1.00 | 38.97 |
| 9159 | CA | LEU | B | 422 | -1.912 | -0.757 | 91.071 | 1.00 | 39.32 |
| 9160 | CB | LEU | B | 422 | -2.474 | -0.631 | 92.491 | 1.00 | 39.02 |
| 9161 | CG | LEU | B | 422 | -1.928 | 0.375 | 93.520 | 1.00 | 38.78 |
| 9162 | CD1 | LEU | B | 422 | -0.764 | 1.182 | 93.029 | 1.00 | 36.84 |
| 9163 | CD2 | LEU | B | 422 | -1.610 | -0.315 | 94.847 | 1.00 | 36.07 |
| 9164 | C | LEU | B | 422 | -0.754 | -1.726 | 91.120 | 1.00 | 39.56 |
| 9165 | O | LEU | B | 422 | -0.951 | -2.891 | 91.452 | 1.00 | 39.19 |
| 9166 | N | THR | B | 423 | 0.442 | -1.258 | 90.772 | 1.00 | 39.91 |
| 9167 | CA | THR | B | 423 | 1.646 | -2.050 | 91.019 | 1.00 | 40.60 |
| 9168 | CB | THR | B | 423 | 2.463 | -2.312 | 89.756 | 1.00 | 40.20 |
| 9169 | OG1 | THR | B | 423 | 2.864 | -1.060 | 89.193 | 1.00 | 40.20 |
| 9170 | CG2 | THR | B | 423 | 1.622 | -2.960 | 88.685 | 1.00 | 40.73 |

FIGURE 3 FX

| A | B | C | D | E | F | G | H | I | J |
|---|---|---|---|---|---|---|---|---|---|
| 9171 | C | THR | B | 385 | 2.499 | -1.252 | 91.994 | 1.00 | 41.37 |
| 9172 | O | THR | B | 385 | 2.147 | -0.128 | 92.362 | 1.00 | 41.22 |
| 9173 | N | SER | B | 386 | 3.641 | -1.821 | 92.374 | 1.00 | 42.02 |
| 9174 | CA | SER | B | 386 | 4.524 | -1.206 | 93.350 | 1.00 | 42.34 |
| 9175 | CB | SER | B | 386 | 5.639 | -2.181 | 93.739 | 1.00 | 42.96 |
| 9176 | OG | SER | B | 386 | 6.026 | -2.983 | 92.630 | 1.00 | 44.13 |
| 9177 | C | SER | B | 386 | 5.107 | 0.094 | 92.849 | 1.00 | 42.48 |
| 9178 | O | SER | B | 386 | 5.543 | 0.923 | 93.646 | 1.00 | 42.77 |
| 9179 | N | ASP | B | 387 | 5.099 | 0.285 | 91.532 | 1.00 | 42.54 |
| 9180 | CA | ASP | B | 387 | 5.655 | 1.497 | 90.940 | 1.00 | 42.32 |
| 9181 | CB | ASP | B | 387 | 6.782 | 1.137 | 89.976 | 1.00 | 42.67 |
| 9182 | CG | ASP | B | 387 | 7.871 | 0.327 | 90.651 | 1.00 | 43.48 |
| 9183 | OD1 | ASP | B | 387 | 8.732 | 0.932 | 91.321 | 1.00 | 44.23 |
| 9184 | OD2 | ASP | B | 387 | 7.924 | -0.918 | 90.599 | 1.00 | 45.16 |
| 9185 | C | ASP | B | 387 | 4.619 | 2.352 | 90.227 | 1.00 | 42.29 |
| 9186 | O | ASP | B | 387 | 4.841 | 3.543 | 89.988 | 1.00 | 42.49 |
| 9187 | N | TYR | B | 388 | 3.481 | 1.754 | 89.893 | 1.00 | 41.64 |
| 9188 | CA | TYR | B | 388 | 2.468 | 2.488 | 89.153 | 1.00 | 40.99 |
| 9189 | CB | TYR | B | 388 | 2.595 | 2.189 | 87.661 | 1.00 | 41.59 |
| 9190 | CG | TYR | B | 388 | 3.849 | 2.764 | 87.044 | 1.00 | 42.34 |
| 9191 | CD1 | TYR | B | 388 | 4.858 | 1.939 | 86.558 | 1.00 | 42.79 |
| 9192 | CE1 | TYR | B | 388 | 6.006 | 2.468 | 85.987 | 1.00 | 44.62 |
| 9193 | CZ | TYR | B | 388 | 6.159 | 3.845 | 85.910 | 1.00 | 46.09 |
| 9194 | OH | TYR | B | 388 | 7.287 | 4.403 | 85.352 | 1.00 | 48.13 |
| 9195 | CE2 | TYR | B | 388 | 5.170 | 4.680 | 86.380 | 1.00 | 46.23 |
| 9196 | CD2 | TYR | B | 388 | 4.018 | 4.133 | 86.945 | 1.00 | 45.16 |
| 9197 | C | TYR | B | 388 | 1.024 | 2.288 | 89.616 | 1.00 | 39.94 |
| 9198 | O | TYR | B | 388 | 0.648 | 1.252 | 90.157 | 1.00 | 39.85 |
| 9199 | N | LEU | B | 389 | 0.237 | 3.331 | 89.408 | 1.00 | 39.01 |
| 9200 | CA | LEU | B | 389 | -1.186 | 3.335 | 89.689 | 1.00 | 37.62 |
| 9201 | CB | LEU | B | 389 | -1.499 | 4.401 | 90.724 | 1.00 | 37.52 |
| 9202 | CG | LEU | B | 389 | -2.940 | 4.749 | 91.121 | 1.00 | 37.00 |
| 9203 | CD1 | LEU | B | 389 | -3.837 | 4.911 | 89.923 | 1.00 | 35.57 |
| 9204 | CD2 | LEU | B | 389 | -3.503 | 3.738 | 92.076 | 1.00 | 36.02 |
| 9205 | C | LEU | B | 389 | -1.815 | 3.701 | 88.360 | 1.00 | 36.86 |
| 9206 | O | LEU | B | 389 | -1.472 | 4.733 | 87.779 | 1.00 | 36.59 |
| 9207 | N | TYR | B | 390 | -2.698 | 2.845 | 87.849 | 1.00 | 35.64 |
| 9208 | CA | TYR | B | 390 | -3.348 | 3.139 | 86.585 | 1.00 | 34.51 |
| 9209 | CB | TYR | B | 390 | -3.358 | 1.918 | 85.672 | 1.00 | 34.68 |
| 9210 | CG | TYR | B | 390 | -1.998 | 1.432 | 85.283 | 1.00 | 35.76 |
| 9211 | CD1 | TYR | B | 390 | -1.472 | 1.725 | 84.043 | 1.00 | 35.57 |
| 9212 | CE1 | TYR | B | 390 | -0.231 | 1.290 | 83.690 | 1.00 | 38.07 |
| 9213 | CZ | TYR | B | 390 | 0.505 | 0.535 | 84.575 | 1.00 | 37.51 |
| 9214 | OH | TYR | B | 390 | 1.747 | 0.089 | 84.205 | 1.00 | 40.72 |
| 9215 | CE2 | TYR | B | 390 | 0.011 | 0.234 | 85.816 | 1.00 | 36.63 |
| 9216 | CD2 | TYR | B | 390 | -1.231 | 0.680 | 86.165 | 1.00 | 36.53 |
| 9217 | C | TYR | B | 390 | -4.774 | 3.597 | 86.823 | 1.00 | 33.58 |
| 9218 | O | TYR | B | 390 | -5.513 | 3.013 | 87.602 | 1.00 | 32.85 |
| 9219 | N | TYR | B | 391 | -5.186 | 4.626 | 86.112 | 1.00 | 32.64 |
| 9220 | CA | TYR | B | 391 | -6.520 | 5.104 | 86.333 | 1.00 | 32.08 |
| 9221 | CB | TYR | B | 391 | -6.524 | 6.142 | 87.460 | 1.00 | 31.85 |

FIGURE 3 FY

| A | B | C | D | E | F | G | H | I | J |
|---|---|---|---|---|---|---|---|---|---|
| 9222 | CG | TYR | B | 391 | -5.809 | 7.414 | 87.109 | 1.00 | 32.71 |
| 9223 | CD1 | TYR | B | 391 | -6.491 | 8.465 | 86.496 | 1.00 | 34.03 |
| 9224 | CE1 | TYR | B | 391 | -5.853 | 9.642 | 86.183 | 1.00 | 35.77 |
| 9225 | CZ | TYR | B | 391 | -4.510 | 9.789 | 86.475 | 1.00 | 35.74 |
| 9226 | OH | TYR | B | 391 | -3.879 | 10.974 | 86.145 | 1.00 | 37.71 |
| 9227 | CE2 | TYR | B | 391 | -3.810 | 8.762 | 87.064 | 1.00 | 34.02 |
| 9228 | CD2 | TYR | B | 391 | -4.461 | 7.576 | 87.384 | 1.00 | 32.38 |
| 9229 | C | TYR | B | 391 | -7.104 | 5.665 | 85.066 | 1.00 | 31.15 |
| 9230 | O | TYR | B | 391 | -6.387 | 5.894 | 84.094 | 1.00 | 30.75 |
| 9231 | N | ILE | B | 392 | -8.419 | 5.869 | 85.085 | 1.00 | 30.53 |
| 9232 | CA | ILE | B | 392 | -9.120 | 6.464 | 83.951 | 1.00 | 29.73 |
| 9233 | CB | ILE | B | 392 | -10.341 | 5.621 | 83.588 | 1.00 | 29.87 |
| 9234 | CG1 | ILE | B | 392 | -9.924 | 4.221 | 83.109 | 1.00 | 29.10 |
| 9235 | CD1 | ILE | B | 392 | -9.997 | 4.037 | 81.626 | 1.00 | 28.29 |
| 9236 | CG2 | ILE | B | 392 | -11.199 | 6.372 | 82.574 | 1.00 | 29.17 |
| 9237 | C | ILE | B | 392 | -9.615 | 7.840 | 84.375 | 1.00 | 29.55 |
| 9238 | O | ILE | B | 392 | -10.098 | 8.012 | 85.496 | 1.00 | 29.03 |
| 9239 | N | SER | B | 393 | -9.528 | 8.817 | 83.489 | 1.00 | 29.09 |
| 9240 | CA | SER | B | 393 | -9.995 | 10.120 | 83.869 | 1.00 | 30.52 |
| 9241 | CB | SER | B | 393 | -8.868 | 10.916 | 84.529 | 1.00 | 30.15 |
| 9242 | OG | SER | B | 393 | -8.127 | 11.567 | 83.519 | 1.00 | 30.36 |
| 9243 | C | SER | B | 393 | -10.501 | 10.873 | 82.660 | 1.00 | 31.45 |
| 9244 | O | SER | B | 393 | -10.301 | 10.464 | 81.525 | 1.00 | 31.45 |
| 9245 | N | ASN | B | 394 | -11.166 | 11.986 | 82.910 | 1.00 | 32.96 |
| 9246 | CA | ASN | B | 394 | -11.640 | 12.805 | 81.819 | 1.00 | 34.79 |
| 9247 | CB | ASN | B | 394 | -13.131 | 13.121 | 81.993 | 1.00 | 34.52 |
| 9248 | CG | ASN | B | 394 | -13.448 | 13.719 | 83.359 | 1.00 | 35.56 |
| 9249 | OD1 | ASN | B | 394 | -12.543 | 14.092 | 84.109 | 1.00 | 37.73 |
| 9250 | ND2 | ASN | B | 394 | -14.729 | 13.823 | 83.682 | 1.00 | 35.03 |
| 9251 | C | ASN | B | 394 | -10.806 | 14.084 | 81.735 | 1.00 | 36.01 |
| 9252 | O | ASN | B | 394 | -11.332 | 15.149 | 81.449 | 1.00 | 36.25 |
| 9253 | N | GLU | B | 395 | -9.502 | 13.984 | 81.995 | 1.00 | 37.46 |
| 9254 | CA | GLU | B | 395 | -8.661 | 15.170 | 81.909 | 1.00 | 38.43 |
| 9255 | CB | GLU | B | 395 | -7.333 | 15.003 | 82.657 | 1.00 | 38.65 |
| 9256 | CG | GLU | B | 395 | -6.412 | 16.203 | 82.463 | 1.00 | 40.19 |
| 9257 | CD | GLU | B | 395 | -5.069 | 16.107 | 83.176 | 1.00 | 42.90 |
| 9258 | OE1 | GLU | B | 395 | -4.430 | 17.176 | 83.354 | 1.00 | 44.92 |
| 9259 | OE2 | GLU | B | 395 | -4.634 | 14.997 | 83.551 | 1.00 | 41.19 |
| 9260 | C | GLU | B | 395 | -8.402 | 15.547 | 80.462 | 1.00 | 38.83 |
| 9261 | O | GLU | B | 395 | -8.514 | 16.707 | 80.084 | 1.00 | 39.14 |
| 9262 | N | TYR | B | 396 | -8.061 | 14.575 | 79.633 | 1.00 | 39.51 |
| 9263 | CA | TYR | B | 396 | -7.753 | 14.923 | 78.257 | 1.00 | 40.26 |
| 9264 | CB | TYR | B | 396 | -7.789 | 13.723 | 77.316 | 1.00 | 40.51 |
| 9265 | CG | TYR | B | 396 | -7.015 | 14.016 | 76.048 | 1.00 | 41.76 |
| 9266 | CD1 | TYR | B | 396 | -7.560 | 13.779 | 74.793 | 1.00 | 43.07 |
| 9267 | CE1 | TYR | B | 396 | -6.844 | 14.055 | 73.640 | 1.00 | 43.54 |
| 9268 | CZ | TYR | B | 396 | -5.574 | 14.593 | 73.737 | 1.00 | 45.08 |
| 9269 | OH | TYR | B | 396 | -4.845 | 14.882 | 72.598 | 1.00 | 47.21 |
| 9270 | CE2 | TYR | B | 396 | -5.014 | 14.838 | 74.971 | 1.00 | 43.68 |
| 9271 | CD2 | TYR | B | 396 | -5.732 | 14.549 | 76.115 | 1.00 | 42.90 |
| 9272 | C | TYR | B | 396 | -8.668 | 15.992 | 77.697 | 1.00 | 40.44 |

FIGURE 3 FZ

| A | B | C | D | E | F | G | H | I | J |
|---|---|---|---|---|---|---|---|---|---|
| 9273 | O | TYR | B | 396 | -9.867 | 15.759 | 77.530 | 1.00 | 40.96 |
| 9274 | N | LYS | B | 397 | -8.080 | 17.150 | 77.398 | 1.00 | 40.48 |
| 9275 | CA | LYS | B | 397 | -8.744 | 18.277 | 76.728 | 1.00 | 39.95 |
| 9276 | CB | LYS | B | 397 | -9.266 | 17.862 | 75.356 | 1.00 | 40.33 |
| 9277 | CG | LYS | B | 397 | -8.177 | 17.582 | 74.339 | 1.00 | 42.20 |
| 9278 | CD | LYS | B | 397 | -8.772 | 16.975 | 73.082 | 1.00 | 45.22 |
| 9279 | CE | LYS | B | 397 | -7.754 | 16.878 | 71.950 | 1.00 | 47.51 |
| 9280 | NZ | LYS | B | 397 | -8.449 | 16.664 | 70.631 | 1.00 | 48.01 |
| 9281 | C | LYS | B | 397 | -9.861 | 18.932 | 77.500 | 1.00 | 39.35 |
| 9282 | O | LYS | B | 397 | -10.658 | 19.672 | 76.927 | 1.00 | 38.89 |
| 9283 | N | GLY | B | 398 | -9.918 | 18.678 | 78.800 | 1.00 | 38.74 |
| 9284 | CA | GLY | B | 398 | -10.986 | 19.241 | 79.604 | 1.00 | 38.23 |
| 9285 | C | GLY | B | 398 | -12.361 | 18.833 | 79.094 | 1.00 | 37.91 |
| 9286 | O | GLY | B | 398 | -13.316 | 19.605 | 79.202 | 1.00 | 38.46 |
| 9287 | N | MET | B | 399 | -12.464 | 17.639 | 78.510 | 1.00 | 36.88 |
| 9288 | CA | MET | B | 399 | -13.754 | 17.115 | 78.037 | 1.00 | 36.07 |
| 9289 | CB | MET | B | 399 | -13.597 | 16.470 | 76.680 | 1.00 | 36.62 |
| 9290 | CG | MET | B | 399 | -13.082 | 17.399 | 75.632 | 1.00 | 38.67 |
| 9291 | SD | MET | B | 399 | -12.656 | 16.504 | 74.157 | 1.00 | 45.06 |
| 9292 | CE | MET | B | 399 | -14.281 | 16.188 | 73.424 | 1.00 | 42.92 |
| 9293 | C | MET | B | 399 | -14.266 | 16.076 | 79.018 | 1.00 | 34.89 |
| 9294 | O | MET | B | 399 | -13.810 | 14.937 | 79.012 | 1.00 | 34.49 |
| 9295 | N | PRO | B | 400 | -15.220 | 16.470 | 79.852 | 1.00 | 33.87 |
| 9296 | CA | PRO | B | 400 | -15.733 | 15.620 | 80.938 | 1.00 | 33.31 |
| 9297 | CB | PRO | B | 400 | -16.821 | 16.487 | 81.579 | 1.00 | 33.52 |
| 9298 | CG | PRO | B | 400 | -16.546 | 17.877 | 81.129 | 1.00 | 33.75 |
| 9299 | CD | PRO | B | 400 | -15.900 | 17.772 | 79.781 | 1.00 | 33.90 |
| 9300 | C | PRO | B | 400 | -16.362 | 14.310 | 80.463 | 1.00 | 33.03 |
| 9301 | O | PRO | B | 400 | -16.481 | 13.367 | 81.239 | 1.00 | 32.45 |
| 9302 | N | GLY | B | 401 | -16.788 | 14.272 | 79.209 | 1.00 | 32.82 |
| 9303 | CA | GLY | B | 401 | -17.378 | 13.077 | 78.644 | 1.00 | 33.58 |
| 9304 | C | GLY | B | 401 | -16.364 | 12.345 | 77.791 | 1.00 | 33.84 |
| 9305 | O | GLY | B | 401 | -16.715 | 11.575 | 76.891 | 1.00 | 33.48 |
| 9306 | N | GLY | B | 402 | -15.089 | 12.601 | 78.062 | 1.00 | 33.60 |
| 9307 | CA | GLY | B | 402 | -14.025 | 11.926 | 77.345 | 1.00 | 33.73 |
| 9308 | C | GLY | B | 402 | -13.471 | 10.992 | 78.383 | 1.00 | 34.35 |
| 9309 | O | GLY | B | 402 | -13.734 | 11.168 | 79.573 | 1.00 | 34.65 |
| 9310 | N | ARG | B | 403 | -12.684 | 10.019 | 77.963 | 1.00 | 34.43 |
| 9311 | CA | ARG | B | 403 | -12.236 | 8.996 | 78.886 | 1.00 | 34.51 |
| 9312 | CB | ARG | B | 403 | -13.301 | 7.889 | 78.914 | 1.00 | 34.75 |
| 9313 | CG | ARG | B | 403 | -14.006 | 7.629 | 80.231 | 1.00 | 36.23 |
| 9314 | CD | ARG | B | 403 | -14.361 | 8.847 | 81.041 | 1.00 | 38.13 |
| 9315 | NE | ARG | B | 403 | -15.671 | 8.737 | 81.693 | 1.00 | 38.92 |
| 9316 | CZ | ARG | B | 403 | -16.562 | 9.728 | 81.708 | 1.00 | 39.23 |
| 9317 | NH1 | ARG | B | 403 | -17.729 | 9.578 | 82.317 | 1.00 | 38.64 |
| 9318 | NH2 | ARG | B | 403 | -16.282 | 10.878 | 81.099 | 1.00 | 37.76 |
| 9319 | C | ARG | B | 403 | -10.919 | 8.434 | 78.353 | 1.00 | 34.08 |
| 9320 | O | ARG | B | 403 | -10.853 | 8.032 | 77.198 | 1.00 | 33.75 |
| 9321 | N | ASN | B | 404 | -9.876 | 8.432 | 79.185 | 1.00 | 34.22 |
| 9322 | CA | ASN | B | 404 | -8.551 | 7.927 | 78.790 | 1.00 | 33.84 |
| 9323 | CB | ASN | B | 404 | -7.671 | 9.057 | 78.262 | 1.00 | 33.63 |

FIGURE 3 GA

| A | B | C | D | E | F | G | H | I | J |
|---|---|---|---|---|---|---|---|---|---|
| 9324 | CG | ASN | B | 404 | -8.034 | 9.472 | 76.878 | 1.00 | 33.22 |
| 9325 | OD1 | ASN | B | 404 | -8.649 | 10.515 | 76.686 | 1.00 | 33.41 |
| 9326 | ND2 | ASN | B | 404 | -7.662 | 8.659 | 75.889 | 1.00 | 32.71 |
| 9327 | C | ASN | B | 404 | -7.822 | 7.263 | 79.951 | 1.00 | 33.53 |
| 9328 | O | ASN | B | 404 | -8.082 | 7.581 | 81.097 | 1.00 | 32.56 |
| 9329 | N | LEU | B | 405 | -6.912 | 6.341 | 79.635 | 1.00 | 33.69 |
| 9330 | CA | LEU | B | 405 | -6.123 | 5.631 | 80.641 | 1.00 | 33.92 |
| 9331 | CB | LEU | B | 405 | -5.784 | 4.245 | 80.117 | 1.00 | 33.85 |
| 9332 | CG | LEU | B | 405 | -4.928 | 3.321 | 80.968 | 1.00 | 34.67 |
| 9333 | CD1 | LEU | B | 405 | -5.558 | 3.125 | 82.345 | 1.00 | 34.97 |
| 9334 | CD2 | LEU | B | 405 | -4.747 | 2.000 | 80.249 | 1.00 | 34.55 |
| 9335 | C | LEU | B | 405 | -4.825 | 6.397 | 80.967 | 1.00 | 34.30 |
| 9336 | O | LEU | B | 405 | -4.103 | 6.824 | 80.073 | 1.00 | 33.84 |
| 9337 | N | TYR | B | 406 | -4.548 | 6.594 | 82.249 | 1.00 | 35.07 |
| 9338 | CA | TYR | B | 406 | -3.324 | 7.281 | 82.656 | 1.00 | 35.88 |
| 9339 | CB | TYR | B | 406 | -3.607 | 8.618 | 83.337 | 1.00 | 35.36 |
| 9340 | CG | TYR | B | 406 | -4.211 | 9.656 | 82.428 | 1.00 | 35.76 |
| 9341 | CD1 | TYR | B | 406 | -3.443 | 10.691 | 81.932 | 1.00 | 35.18 |
| 9342 | CE1 | TYR | B | 406 | -3.994 | 11.654 | 81.101 | 1.00 | 37.36 |
| 9343 | CZ | TYR | B | 406 | -5.336 | 11.577 | 80.770 | 1.00 | 36.65 |
| 9344 | OH | TYR | B | 406 | -5.870 | 12.530 | 79.941 | 1.00 | 39.75 |
| 9345 | CE2 | TYR | B | 406 | -6.126 | 10.555 | 81.252 | 1.00 | 34.01 |
| 9346 | CD2 | TYR | B | 406 | -5.573 | 9.606 | 82.075 | 1.00 | 33.96 |
| 9347 | C | TYR | B | 406 | -2.522 | 6.427 | 83.603 | 1.00 | 36.60 |
| 9348 | O | TYR | B | 406 | -3.066 | 5.575 | 84.321 | 1.00 | 36.45 |
| 9349 | N | LYS | B | 407 | -1.222 | 6.692 | 83.615 | 1.00 | 37.42 |
| 9350 | CA | LYS | B | 407 | -0.297 | 5.990 | 84.484 | 1.00 | 38.56 |
| 9351 | CB | LYS | B | 407 | 0.597 | 5.082 | 83.633 | 1.00 | 38.56 |
| 9352 | CG | LYS | B | 407 | 1.995 | 4.805 | 84.154 | 1.00 | 38.49 |
| 9353 | CD | LYS | B | 407 | 2.579 | 3.634 | 83.370 | 1.00 | 38.76 |
| 9354 | CE | LYS | B | 407 | 4.038 | 3.832 | 82.997 | 1.00 | 39.60 |
| 9355 | NZ | LYS | B | 407 | 4.362 | 3.057 | 81.748 | 1.00 | 39.08 |
| 9356 | C | LYS | B | 407 | 0.519 | 6.999 | 85.294 | 1.00 | 38.99 |
| 9357 | O | LYS | B | 407 | 1.195 | 7.867 | 84.733 | 1.00 | 39.39 |
| 9358 | N | ILE | B | 408 | 0.430 | 6.889 | 86.614 | 1.00 | 39.35 |
| 9359 | CA | ILE | B | 408 | 1.155 | 7.776 | 87.511 | 1.00 | 39.42 |
| 9360 | CB | ILE | B | 408 | 0.161 | 8.552 | 88.403 | 1.00 | 39.46 |
| 9361 | CG1 | ILE | B | 408 | 0.914 | 9.500 | 89.347 | 1.00 | 40.00 |
| 9362 | CD1 | ILE | B | 408 | 0.022 | 10.521 | 90.018 | 1.00 | 39.47 |
| 9363 | CG2 | ILE | B | 408 | -0.733 | 7.591 | 89.194 | 1.00 | 37.63 |
| 9364 | C | ILE | B | 408 | 2.175 | 7.018 | 88.368 | 1.00 | 39.81 |
| 9365 | O | ILE | B | 408 | 1.853 | 6.018 | 89.016 | 1.00 | 39.29 |
| 9366 | N | GLN | B | 409 | 3.412 | 7.508 | 88.353 | 1.00 | 40.51 |
| 9367 | CA | GLN | B | 409 | 4.507 | 6.923 | 89.129 | 1.00 | 40.64 |
| 9368 | CB | GLN | B | 409 | 5.841 | 7.512 | 88.649 | 1.00 | 40.42 |
| 9369 | CG | GLN | B | 409 | 7.090 | 6.901 | 89.267 | 1.00 | 41.41 |
| 9370 | CD | GLN | B | 409 | 8.361 | 7.664 | 88.884 | 1.00 | 41.94 |
| 9371 | OE1 | GLN | B | 409 | 8.638 | 7.861 | 87.707 | 1.00 | 43.52 |
| 9372 | NE2 | GLN | B | 409 | 9.117 | 8.096 | 89.878 | 1.00 | 39.59 |
| 9373 | C | GLN | B | 409 | 4.290 | 7.215 | 90.608 | 1.00 | 40.92 |
| 9374 | O | GLN | B | 409 | 4.192 | 8.379 | 91.003 | 1.00 | 41.00 |

FIGURE 3 GB

| A | B | C | D | E | F | G | H | I | J |
|---|---|---|---|---|---|---|---|---|---|
| 9375 | N | LEU | B | 410 | 4.193 | 6.163 | 91.418 | 1.00 | 41.42 |
| 9376 | CA | LEU | B | 410 | 3.981 | 6.300 | 92.857 | 1.00 | 42.64 |
| 9377 | CB | LEU | B | 410 | 3.837 | 4.924 | 93.508 | 1.00 | 42.69 |
| 9378 | CG | LEU | B | 410 | 2.492 | 4.197 | 93.447 | 1.00 | 43.09 |
| 9379 | CD1 | LEU | B | 410 | 1.736 | 4.560 | 92.189 | 1.00 | 42.37 |
| 9380 | CD2 | LEU | B | 410 | 2.721 | 2.707 | 93.530 | 1.00 | 42.61 |
| 9381 | C | LEU | B | 410 | 5.092 | 7.041 | 93.599 | 1.00 | 43.77 |
| 9382 | O | LEU | B | 410 | 4.931 | 7.370 | 94.777 | 1.00 | 44.22 |
| 9383 | N | SER | B | 411 | 6.220 | 7.282 | 92.936 | 1.00 | 44.48 |
| 9384 | CA | SER | B | 411 | 7.336 | 7.946 | 93.592 | 1.00 | 45.35 |
| 9385 | CB | SER | B | 411 | 8.661 | 7.209 | 93.324 | 1.00 | 45.03 |
| 9386 | OG | SER | B | 411 | 9.035 | 7.308 | 91.961 | 1.00 | 43.76 |
| 9387 | C | SER | B | 411 | 7.429 | 9.396 | 93.156 | 1.00 | 46.24 |
| 9388 | O | SER | B | 411 | 8.186 | 10.182 | 93.738 | 1.00 | 46.61 |
| 9389 | N | ASP | B | 412 | 6.659 | 9.760 | 92.137 | 1.00 | 46.78 |
| 9390 | CA | ASP | B | 412 | 6.678 | 11.143 | 91.665 | 1.00 | 47.56 |
| 9391 | CB | ASP | B | 412 | 7.915 | 11.407 | 90.801 | 1.00 | 47.90 |
| 9392 | CG | ASP | B | 412 | 8.105 | 12.876 | 90.501 | 1.00 | 50.22 |
| 9393 | OD1 | ASP | B | 412 | 8.902 | 13.203 | 89.592 | 1.00 | 53.28 |
| 9394 | OD2 | ASP | B | 412 | 7.502 | 13.781 | 91.124 | 1.00 | 51.81 |
| 9395 | C | ASP | B | 412 | 5.384 | 11.530 | 90.933 | 1.00 | 47.35 |
| 9396 | O | ASP | B | 412 | 5.277 | 11.438 | 89.706 | 1.00 | 47.12 |
| 9397 | N | TYR | B | 413 | 4.420 | 11.979 | 91.730 | 1.00 | 47.17 |
| 9398 | CA | TYR | B | 413 | 3.089 | 12.378 | 91.294 | 1.00 | 46.56 |
| 9399 | CB | TYR | B | 413 | 2.360 | 13.009 | 92.477 | 1.00 | 45.92 |
| 9400 | CG | TYR | B | 413 | 2.276 | 12.066 | 93.659 | 1.00 | 43.46 |
| 9401 | CD1 | TYR | B | 413 | 2.309 | 10.697 | 93.462 | 1.00 | 40.02 |
| 9402 | CE1 | TYR | B | 413 | 2.214 | 9.818 | 94.514 | 1.00 | 39.75 |
| 9403 | CZ | TYR | B | 413 | 2.108 | 10.288 | 95.793 | 1.00 | 38.66 |
| 9404 | OH | TYR | B | 413 | 2.025 | 9.382 | 96.805 | 1.00 | 39.90 |
| 9405 | CE2 | TYR | B | 413 | 2.085 | 11.637 | 96.042 | 1.00 | 40.62 |
| 9406 | CD2 | TYR | B | 413 | 2.162 | 12.535 | 94.964 | 1.00 | 41.96 |
| 9407 | C | TYR | B | 413 | 3.144 | 13.343 | 90.134 | 1.00 | 47.27 |
| 9408 | O | TYR | B | 413 | 2.156 | 13.554 | 89.436 | 1.00 | 47.56 |
| 9409 | N | THR | B | 414 | 4.315 | 13.918 | 89.915 | 1.00 | 47.67 |
| 9410 | CA | THR | B | 414 | 4.484 | 14.850 | 88.824 | 1.00 | 48.13 |
| 9411 | CB | THR | B | 414 | 5.683 | 15.764 | 89.103 | 1.00 | 48.45 |
| 9412 | OG1 | THR | B | 414 | 6.839 | 14.958 | 89.386 | 1.00 | 48.02 |
| 9413 | CG2 | THR | B | 414 | 5.463 | 16.548 | 90.399 | 1.00 | 49.00 |
| 9414 | C | THR | B | 414 | 4.715 | 14.059 | 87.549 | 1.00 | 48.31 |
| 9415 | O | THR | B | 414 | 4.715 | 14.614 | 86.451 | 1.00 | 48.30 |
| 9416 | N | LYS | B | 415 | 4.932 | 12.760 | 87.696 | 1.00 | 48.57 |
| 9417 | CA | LYS | B | 415 | 5.173 | 11.919 | 86.536 | 1.00 | 49.01 |
| 9418 | CB | LYS | B | 415 | 6.399 | 11.024 | 86.740 | 1.00 | 49.32 |
| 9419 | CG | LYS | B | 415 | 7.717 | 11.805 | 86.908 | 1.00 | 51.05 |
| 9420 | CD | LYS | B | 415 | 8.860 | 11.204 | 86.085 | 1.00 | 54.34 |
| 9421 | CE | LYS | B | 415 | 8.896 | 11.775 | 84.661 | 1.00 | 57.13 |
| 9422 | NZ | LYS | B | 415 | 9.791 | 11.003 | 83.720 | 1.00 | 58.80 |
| 9423 | C | LYS | B | 415 | 3.937 | 11.103 | 86.202 | 1.00 | 48.84 |
| 9424 | O | LYS | B | 415 | 3.742 | 9.991 | 86.705 | 1.00 | 49.14 |
| 9425 | N | VAL | B | 416 | 3.092 | 11.682 | 85.361 | 1.00 | 48.53 |

FIGURE 3 GC

| A | B | C | D | E | F | G | H | I | J |
|---|---|---|---|---|---|---|---|---|---|
| 9426 | CA  | VAL | B | 416 | 1.879  | 11.024 | 84.907 | 1.00 | 48.03 |
| 9427 | CB  | VAL | B | 416 | 0.631  | 11.859 | 85.237 | 1.00 | 47.91 |
| 9428 | CG1 | VAL | B | 416 | -0.630 | 11.172 | 84.714 | 1.00 | 47.97 |
| 9429 | CG2 | VAL | B | 416 | 0.519  | 12.079 | 86.717 | 1.00 | 48.17 |
| 9430 | C   | VAL | B | 416 | 1.936  | 10.869 | 83.398 | 1.00 | 47.87 |
| 9431 | O   | VAL | B | 416 | 2.175  | 11.844 | 82.682 | 1.00 | 47.53 |
| 9432 | N   | THR | B | 417 | 1.703  | 9.650  | 82.915 | 1.00 | 47.45 |
| 9433 | CA  | THR | B | 417 | 1.698  | 9.403  | 81.478 | 1.00 | 47.54 |
| 9434 | CB  | THR | B | 417 | 2.700  | 8.274  | 81.121 | 1.00 | 47.46 |
| 9435 | OG1 | THR | B | 417 | 4.026  | 8.632  | 81.546 | 1.00 | 48.55 |
| 9436 | CG2 | THR | B | 417 | 2.832  | 8.139  | 79.619 | 1.00 | 47.28 |
| 9437 | C   | THR | B | 417 | 0.306  | 8.999  | 81.006 | 1.00 | 47.33 |
| 9438 | O   | THR | B | 417 | -0.344 | 8.159  | 81.624 | 1.00 | 47.27 |
| 9439 | N   | CYS | B | 418 | -0.168 | 9.596  | 79.920 | 1.00 | 47.47 |
| 9440 | CA  | CYS | B | 418 | -1.438 | 9.141  | 79.363 | 1.00 | 47.29 |
| 9441 | CB  | CYS | B | 418 | -2.240 | 10.250 | 78.697 | 1.00 | 47.44 |
| 9442 | SG  | CYS | B | 418 | -3.920 | 9.687  | 78.237 | 1.00 | 47.35 |
| 9443 | C   | CYS | B | 418 | -1.164 | 8.056  | 78.356 | 1.00 | 47.04 |
| 9444 | O   | CYS | B | 418 | -0.508 | 8.293  | 77.345 | 1.00 | 47.45 |
| 9445 | N   | LEU | B | 419 | -1.685 | 6.868  | 78.631 | 1.00 | 46.68 |
| 9446 | CA  | LEU | B | 419 | -1.483 | 5.706  | 77.771 | 1.00 | 46.41 |
| 9447 | CB  | LEU | B | 419 | -1.611 | 4.441  | 78.609 | 1.00 | 46.32 |
| 9448 | CG  | LEU | B | 419 | -0.833 | 4.462  | 79.918 | 1.00 | 46.29 |
| 9449 | CD1 | LEU | B | 419 | -1.130 | 3.222  | 80.736 | 1.00 | 46.26 |
| 9450 | CD2 | LEU | B | 419 | 0.653  | 4.575  | 79.610 | 1.00 | 46.66 |
| 9451 | C   | LEU | B | 419 | -2.424 | 5.578  | 76.571 | 1.00 | 46.43 |
| 9452 | O   | LEU | B | 419 | -2.205 | 4.728  | 75.709 | 1.00 | 46.90 |
| 9453 | N   | SER | B | 420 | -3.472 | 6.388  | 76.495 | 1.00 | 46.32 |
| 9454 | CA  | SER | B | 420 | -4.432 | 6.219  | 75.395 | 1.00 | 46.23 |
| 9455 | CB  | SER | B | 420 | -5.740 | 5.617  | 75.915 | 1.00 | 45.90 |
| 9456 | OG  | SER | B | 420 | -6.426 | 6.523  | 76.755 | 1.00 | 45.99 |
| 9457 | C   | SER | B | 420 | -4.740 | 7.475  | 74.611 | 1.00 | 46.02 |
| 9458 | O   | SER | B | 420 | -5.144 | 7.405  | 73.452 | 1.00 | 46.35 |
| 9459 | N   | CYS | B | 421 | -4.536 | 8.621  | 75.240 | 1.00 | 46.04 |
| 9460 | CA  | CYS | B | 421 | -4.882 | 9.905  | 74.644 | 1.00 | 46.50 |
| 9461 | CB  | CYS | B | 421 | -4.250 | 11.057 | 75.440 | 1.00 | 46.49 |
| 9462 | SG  | CYS | B | 421 | -4.787 | 11.169 | 77.167 | 1.00 | 47.72 |
| 9463 | C   | CYS | B | 421 | -4.522 | 10.062 | 73.173 | 1.00 | 46.81 |
| 9464 | O   | CYS | B | 421 | -5.298 | 10.615 | 72.401 | 1.00 | 46.67 |
| 9465 | N   | GLU | B | 422 | -3.347 | 9.581  | 72.786 | 1.00 | 47.35 |
| 9466 | CA  | GLU | B | 422 | -2.831 | 9.850  | 71.446 | 1.00 | 47.86 |
| 9467 | CB  | GLU | B | 422 | -1.472 | 10.570 | 71.544 | 1.00 | 47.88 |
| 9468 | CG  | GLU | B | 422 | -1.433 | 11.997 | 71.002 | 1.00 | 50.00 |
| 9469 | CD  | GLU | B | 422 | -2.245 | 13.011 | 71.808 | 1.00 | 53.03 |
| 9470 | OE1 | GLU | B | 422 | -2.082 | 13.091 | 73.046 | 1.00 | 53.34 |
| 9471 | OE2 | GLU | B | 422 | -3.043 | 13.757 | 71.189 | 1.00 | 54.03 |
| 9472 | C   | GLU | B | 422 | -2.736 | 8.640  | 70.517 | 1.00 | 47.69 |
| 9473 | O   | GLU | B | 422 | -2.197 | 8.749  | 69.421 | 1.00 | 47.87 |
| 9474 | N   | LEU | B | 423 | -3.274 | 7.501  | 70.938 | 1.00 | 47.64 |
| 9475 | CA  | LEU | B | 423 | -3.241 | 6.288  | 70.113 | 1.00 | 47.92 |
| 9476 | CB  | LEU | B | 423 | -3.915 | 5.128  | 70.841 | 1.00 | 47.08 |

FIGURE 3 GD

| A | B | C | D | E | F | G | H | I | J |
|---|---|---|---|---|---|---|---|---|---|
| 9477 | CG | LEU | B | 423 | -3.146 | 4.584 | 72.043 | 1.00 | 47.38 |
| 9478 | CD1 | LEU | B | 423 | -3.918 | 3.471 | 72.729 | 1.00 | 46.19 |
| 9479 | CD2 | LEU | B | 423 | -1.744 | 4.100 | 71.638 | 1.00 | 46.08 |
| 9480 | C | LEU | B | 423 | -3.904 | 6.492 | 68.748 | 1.00 | 48.36 |
| 9481 | O | LEU | B | 423 | -3.318 | 6.187 | 67.705 | 1.00 | 48.49 |
| 9482 | N | ASN | B | 424 | -5.134 | 6.999 | 68.782 | 1.00 | 48.71 |
| 9483 | CA | ASN | B | 424 | -5.939 | 7.302 | 67.608 | 1.00 | 49.05 |
| 9484 | CB | ASN | B | 424 | -6.833 | 6.108 | 67.237 | 1.00 | 49.54 |
| 9485 | CG | ASN | B | 424 | -6.105 | 4.995 | 66.455 | 1.00 | 51.63 |
| 9486 | OD1 | ASN | B | 424 | -5.835 | 5.123 | 65.252 | 1.00 | 53.95 |
| 9487 | ND2 | ASN | B | 424 | -5.848 | 3.871 | 67.129 | 1.00 | 52.35 |
| 9488 | C | ASN | B | 424 | -6.854 | 8.459 | 68.025 | 1.00 | 48.74 |
| 9489 | O | ASN | B | 424 | -8.043 | 8.254 | 68.251 | 1.00 | 49.07 |
| 9490 | N | PRO | B | 425 | -6.302 | 9.660 | 68.164 | 1.00 | 48.43 |
| 9491 | CA | PRO | B | 425 | -7.054 | 10.847 | 68.617 | 1.00 | 48.02 |
| 9492 | CB | PRO | B | 425 | -6.050 | 11.989 | 68.404 | 1.00 | 47.86 |
| 9493 | CG | PRO | B | 425 | -5.023 | 11.403 | 67.490 | 1.00 | 48.40 |
| 9494 | CD | PRO | B | 425 | -4.879 | 9.982 | 67.959 | 1.00 | 48.45 |
| 9495 | C | PRO | B | 425 | -8.381 | 11.199 | 67.918 | 1.00 | 47.59 |
| 9496 | O | PRO | B | 425 | -9.222 | 11.842 | 68.540 | 1.00 | 46.93 |
| 9497 | N | GLU | B | 426 | -8.561 | 10.827 | 66.660 | 1.00 | 47.18 |
| 9498 | CA | GLU | B | 426 | -9.802 | 11.166 | 65.971 | 1.00 | 46.96 |
| 9499 | CB | GLU | B | 426 | -9.535 | 11.492 | 64.501 | 1.00 | 47.53 |
| 9500 | CG | GLU | B | 426 | -8.931 | 12.870 | 64.268 | 1.00 | 50.42 |
| 9501 | CD | GLU | B | 426 | -8.861 | 13.226 | 62.797 | 1.00 | 55.18 |
| 9502 | OE1 | GLU | B | 426 | -9.438 | 12.456 | 61.982 | 1.00 | 58.05 |
| 9503 | OE2 | GLU | B | 426 | -8.235 | 14.264 | 62.451 | 1.00 | 55.78 |
| 9504 | C | GLU | B | 426 | -10.844 | 10.055 | 66.088 | 1.00 | 45.85 |
| 9505 | O | GLU | B | 426 | -12.048 | 10.310 | 66.056 | 1.00 | 46.07 |
| 9506 | N | ARG | B | 427 | -10.372 | 8.824 | 66.218 | 1.00 | 44.60 |
| 9507 | CA | ARG | B | 427 | -11.245 | 7.669 | 66.346 | 1.00 | 43.20 |
| 9508 | CB | ARG | B | 427 | -10.545 | 6.432 | 65.742 | 1.00 | 43.19 |
| 9509 | CG | ARG | B | 427 | -11.100 | 5.047 | 66.136 | 1.00 | 42.79 |
| 9510 | CD | ARG | B | 427 | -11.837 | 4.273 | 65.033 | 1.00 | 42.22 |
| 9511 | NE | ARG | B | 427 | -10.961 | 3.411 | 64.240 | 1.00 | 43.75 |
| 9512 | CZ | ARG | B | 427 | -11.117 | 2.095 | 64.123 | 1.00 | 43.04 |
| 9513 | NH1 | ARG | B | 427 | -10.278 | 1.382 | 63.381 | 1.00 | 41.93 |
| 9514 | NH2 | ARG | B | 427 | -12.111 | 1.484 | 64.752 | 1.00 | 42.41 |
| 9515 | C | ARG | B | 427 | -11.555 | 7.448 | 67.825 | 1.00 | 42.54 |
| 9516 | O | ARG | B | 427 | -12.665 | 7.066 | 68.198 | 1.00 | 41.81 |
| 9517 | N | CYS | B | 428 | -10.578 | 7.736 | 68.678 | 1.00 | 41.68 |
| 9518 | CA | CYS | B | 428 | -10.702 | 7.308 | 70.059 | 1.00 | 40.78 |
| 9519 | CB | CYS | B | 428 | -9.771 | 6.114 | 70.280 | 1.00 | 40.84 |
| 9520 | SG | CYS | B | 428 | -10.305 | 4.676 | 69.310 | 1.00 | 40.30 |
| 9521 | C | CYS | B | 428 | -10.513 | 8.331 | 71.156 | 1.00 | 40.51 |
| 9522 | O | CYS | B | 428 | -9.447 | 8.941 | 71.285 | 1.00 | 40.62 |
| 9523 | N | GLN | B | 429 | -11.566 | 8.524 | 71.945 | 1.00 | 39.36 |
| 9524 | CA | GLN | B | 429 | -11.482 | 9.414 | 73.078 | 1.00 | 38.88 |
| 9525 | CB | GLN | B | 429 | -11.630 | 10.883 | 72.658 | 1.00 | 39.13 |
| 9526 | CG | GLN | B | 429 | -12.909 | 11.232 | 71.952 | 1.00 | 41.45 |
| 9527 | CD | GLN | B | 429 | -12.815 | 12.506 | 71.135 | 1.00 | 42.09 |

FIGURE 3 GE

| A | B | C | D | E | F | G | H | I | J |
|---|---|---|---|---|---|---|---|---|---|
| 9528 | OE1 | GLN | B | 429 | -12.231 | 12.518 | 70.052 | 1.00 | 42.86 |
| 9529 | NE2 | GLN | B | 429 | -13.410 | 13.571 | 71.637 | 1.00 | 43.57 |
| 9530 | C | GLN | B | 429 | -12.407 | 9.030 | 74.230 | 1.00 | 38.04 |
| 9531 | O | GLN | B | 429 | -12.768 | 9.873 | 75.025 | 1.00 | 38.38 |
| 9532 | N | TYR | B | 430 | -12.775 | 7.747 | 74.301 | 1.00 | 36.73 |
| 9533 | CA | TYR | B | 430 | -13.530 | 7.164 | 75.421 | 1.00 | 35.62 |
| 9534 | CB | TYR | B | 430 | -15.036 | 7.101 | 75.130 | 1.00 | 35.47 |
| 9535 | CG | TYR | B | 430 | -15.935 | 6.976 | 76.345 | 1.00 | 33.00 |
| 9536 | CD1 | TYR | B | 430 | -16.190 | 5.741 | 76.928 | 1.00 | 30.65 |
| 9537 | CE1 | TYR | B | 430 | -17.013 | 5.634 | 78.036 | 1.00 | 31.86 |
| 9538 | CZ | TYR | B | 430 | -17.612 | 6.776 | 78.569 | 1.00 | 32.82 |
| 9539 | OH | TYR | B | 430 | -18.456 | 6.680 | 79.661 | 1.00 | 32.17 |
| 9540 | CE2 | TYR | B | 430 | -17.380 | 8.009 | 77.996 | 1.00 | 31.47 |
| 9541 | CD2 | TYR | B | 430 | -16.546 | 8.103 | 76.898 | 1.00 | 32.86 |
| 9542 | C | TYR | B | 430 | -13.000 | 5.747 | 75.573 | 1.00 | 35.39 |
| 9543 | O | TYR | B | 430 | -13.337 | 4.876 | 74.766 | 1.00 | 36.02 |
| 9544 | N | TYR | B | 431 | -12.178 | 5.514 | 76.595 | 1.00 | 34.48 |
| 9545 | CA | TYR | B | 431 | -11.521 | 4.228 | 76.768 | 1.00 | 33.97 |
| 9546 | CB | TYR | B | 431 | -9.993 | 4.411 | 76.819 | 1.00 | 34.10 |
| 9547 | CG | TYR | B | 431 | -9.288 | 4.635 | 75.502 | 1.00 | 33.35 |
| 9548 | CD1 | TYR | B | 431 | -8.782 | 3.568 | 74.780 | 1.00 | 33.82 |
| 9549 | CE1 | TYR | B | 431 | -8.126 | 3.764 | 73.577 | 1.00 | 32.81 |
| 9550 | CZ | TYR | B | 431 | -7.975 | 5.024 | 73.089 | 1.00 | 32.09 |
| 9551 | OH | TYR | B | 431 | -7.317 | 5.210 | 71.884 | 1.00 | 34.18 |
| 9552 | CE2 | TYR | B | 431 | -8.474 | 6.106 | 73.790 | 1.00 | 32.54 |
| 9553 | CD2 | TYR | B | 431 | -9.109 | 5.909 | 74.994 | 1.00 | 31.95 |
| 9554 | C | TYR | B | 431 | -11.893 | 3.521 | 78.054 | 1.00 | 33.98 |
| 9555 | O | TYR | B | 431 | -12.132 | 4.149 | 79.085 | 1.00 | 33.82 |
| 9556 | N | SER | B | 432 | -11.916 | 2.201 | 77.992 | 1.00 | 33.64 |
| 9557 | CA | SER | B | 432 | -11.991 | 1.400 | 79.197 | 1.00 | 33.67 |
| 9558 | CB | SER | B | 432 | -13.336 | 0.693 | 79.344 | 1.00 | 33.69 |
| 9559 | OG | SER | B | 432 | -13.557 | -0.209 | 78.285 | 1.00 | 35.22 |
| 9560 | C | SER | B | 432 | -10.831 | 0.417 | 79.082 | 1.00 | 33.30 |
| 9561 | O | SER | B | 432 | -10.242 | 0.260 | 78.000 | 1.00 | 32.90 |
| 9562 | N | VAL | B | 433 | -10.493 | -0.252 | 80.171 | 1.00 | 33.35 |
| 9563 | CA | VAL | B | 433 | -9.318 | -1.105 | 80.138 | 1.00 | 33.52 |
| 9564 | CB | VAL | B | 433 | -8.066 | -0.355 | 80.689 | 1.00 | 33.67 |
| 9565 | CG1 | VAL | B | 433 | -8.301 | 0.133 | 82.113 | 1.00 | 31.86 |
| 9566 | CG2 | VAL | B | 433 | -6.806 | -1.245 | 80.621 | 1.00 | 33.10 |
| 9567 | C | VAL | B | 433 | -9.482 | -2.396 | 80.898 | 1.00 | 34.40 |
| 9568 | O | VAL | B | 433 | -10.216 | -2.469 | 81.876 | 1.00 | 34.34 |
| 9569 | N | SER | B | 434 | -8.792 | -3.429 | 80.434 | 1.00 | 35.52 |
| 9570 | CA | SER | B | 434 | -8.774 | -4.692 | 81.155 | 1.00 | 36.83 |
| 9571 | CB | SER | B | 434 | -9.631 | -5.760 | 80.476 | 1.00 | 36.32 |
| 9572 | OG | SER | B | 434 | -9.797 | -6.868 | 81.354 | 1.00 | 36.59 |
| 9573 | C | SER | B | 434 | -7.340 | -5.180 | 81.297 | 1.00 | 37.75 |
| 9574 | O | SER | B | 434 | -6.682 | -5.530 | 80.307 | 1.00 | 37.42 |
| 9575 | N | PHE | B | 435 | -6.874 | -5.205 | 82.541 | 1.00 | 39.26 |
| 9576 | CA | PHE | B | 435 | -5.519 | -5.633 | 82.862 | 1.00 | 40.71 |
| 9577 | CB | PHE | B | 435 | -4.987 | -4.889 | 84.093 | 1.00 | 40.80 |
| 9578 | CG | PHE | B | 435 | -4.566 | -3.480 | 83.812 | 1.00 | 41.50 |

FIGURE 3 GF

| A | B | C | D | E | F | G | H | I | J |
|---|---|---|---|---|---|---|---|---|---|
| 9579 | CD1 | PHE | B | 435 | -5.471 | -2.434 | 83.929 | 1.00 | 41.05 |
| 9580 | CE1 | PHE | B | 435 | -5.087 | -1.145 | 83.671 | 1.00 | 40.57 |
| 9581 | CZ | PHE | B | 435 | -3.800 | -0.870 | 83.289 | 1.00 | 41.39 |
| 9582 | CE2 | PHE | B | 435 | -2.883 | -1.889 | 83.177 | 1.00 | 42.17 |
| 9583 | CD2 | PHE | B | 435 | -3.273 | -3.197 | 83.434 | 1.00 | 41.94 |
| 9584 | C | PHE | B | 435 | -5.458 | -7.119 | 83.137 | 1.00 | 41.74 |
| 9585 | O | PHE | B | 435 | -6.432 | -7.728 | 83.595 | 1.00 | 41.77 |
| 9586 | N | SER | B | 436 | -4.301 | -7.691 | 82.836 | 1.00 | 42.94 |
| 9587 | CA | SER | B | 436 | -4.026 | -9.085 | 83.112 | 1.00 | 44.64 |
| 9588 | CB | SER | B | 436 | -2.789 | -9.541 | 82.334 | 1.00 | 44.86 |
| 9589 | OG | SER | B | 436 | -1.630 | -8.835 | 82.763 | 1.00 | 44.90 |
| 9590 | C | SER | B | 436 | -3.757 | -9.218 | 84.600 | 1.00 | 45.60 |
| 9591 | O | SER | B | 436 | -3.373 | -8.250 | 85.260 | 1.00 | 45.77 |
| 9592 | N | LYS | B | 437 | -3.928 | -10.429 | 85.112 | 1.00 | 46.66 |
| 9593 | CA | LYS | B | 437 | -3.755 | -10.726 | 86.533 | 1.00 | 48.13 |
| 9594 | CB | LYS | B | 437 | -3.491 | -12.223 | 86.714 | 1.00 | 48.28 |
| 9595 | CG | LYS | B | 437 | -3.311 | -12.681 | 88.151 | 1.00 | 50.57 |
| 9596 | CD | LYS | B | 437 | -3.547 | -14.195 | 88.281 | 1.00 | 52.46 |
| 9597 | CE | LYS | B | 437 | -2.772 | -14.796 | 89.461 | 1.00 | 54.80 |
| 9598 | NZ | LYS | B | 437 | -1.407 | -15.274 | 89.067 | 1.00 | 55.25 |
| 9599 | C | LYS | B | 437 | -2.720 | -9.873 | 87.295 | 1.00 | 48.47 |
| 9600 | O | LYS | B | 437 | -2.975 | -9.483 | 88.435 | 1.00 | 48.75 |
| 9601 | N | GLU | B | 438 | -1.571 | -9.576 | 86.685 | 1.00 | 48.91 |
| 9602 | CA | GLU | B | 438 | -0.564 | -8.733 | 87.342 | 1.00 | 49.40 |
| 9603 | CB | GLU | B | 438 | 0.713 | -9.513 | 87.677 | 1.00 | 50.14 |
| 9604 | CG | GLU | B | 438 | 0.969 | -9.700 | 89.171 | 1.00 | 53.11 |
| 9605 | CD | GLU | B | 438 | 0.538 | -11.062 | 89.687 | 1.00 | 57.76 |
| 9606 | OE1 | GLU | B | 438 | -0.628 | -11.447 | 89.431 | 1.00 | 59.42 |
| 9607 | OE2 | GLU | B | 438 | 1.365 | -11.747 | 90.350 | 1.00 | 58.90 |
| 9608 | C | GLU | B | 438 | -0.218 | -7.527 | 86.489 | 1.00 | 48.92 |
| 9609 | O | GLU | B | 438 | 0.873 | -6.972 | 86.588 | 1.00 | 48.64 |
| 9610 | N | ALA | B | 439 | -1.154 | -7.138 | 85.632 | 1.00 | 48.41 |
| 9611 | CA | ALA | B | 439 | -0.976 | -5.969 | 84.791 | 1.00 | 47.44 |
| 9612 | CB | ALA | B | 439 | -0.928 | -4.714 | 85.638 | 1.00 | 47.48 |
| 9613 | C | ALA | B | 439 | 0.245 | -6.057 | 83.892 | 1.00 | 46.91 |
| 9614 | O | ALA | B | 439 | 0.861 | -5.046 | 83.582 | 1.00 | 47.27 |
| 9615 | N | LYS | B | 440 | 0.599 | -7.261 | 83.467 | 1.00 | 46.22 |
| 9616 | CA | LYS | B | 440 | 1.685 | -7.401 | 82.514 | 1.00 | 45.42 |
| 9617 | CB | LYS | B | 440 | 2.114 | -8.865 | 82.382 | 1.00 | 45.72 |
| 9618 | CG | LYS | B | 440 | 3.629 | -9.085 | 82.271 | 1.00 | 48.39 |
| 9619 | CD | LYS | B | 440 | 4.001 | -10.582 | 82.337 | 1.00 | 51.54 |
| 9620 | CE | LYS | B | 440 | 5.446 | -10.819 | 82.828 | 1.00 | 54.11 |
| 9621 | NZ | LYS | B | 440 | 5.569 | -11.261 | 84.272 | 1.00 | 55.44 |
| 9622 | C | LYS | B | 440 | 1.133 | -6.879 | 81.203 | 1.00 | 44.23 |
| 9623 | O | LYS | B | 440 | 1.822 | -6.199 | 80.446 | 1.00 | 44.04 |
| 9624 | N | TYR | B | 441 | -0.137 | -7.172 | 80.943 | 1.00 | 42.93 |
| 9625 | CA | TYR | B | 441 | -0.770 | -6.680 | 79.723 | 1.00 | 41.53 |
| 9626 | CB | TYR | B | 441 | -1.017 | -7.819 | 78.736 | 1.00 | 41.51 |
| 9627 | CG | TYR | B | 441 | 0.183 | -8.690 | 78.517 | 1.00 | 42.29 |
| 9628 | CD1 | TYR | B | 441 | 0.450 | -9.747 | 79.362 | 1.00 | 44.21 |
| 9629 | CE1 | TYR | B | 441 | 1.560 | -10.548 | 79.177 | 1.00 | 45.77 |

FIGURE 3 GG

| A | B | C | D | E | F | G | H | I | J |
|---|---|---|---|---|---|---|---|---|---|
| 9630 | CZ | TYR | B | 441 | 2.410 | -10.297 | 78.129 | 1.00 | 45.67 |
| 9631 | OH | TYR | B | 441 | 3.508 | -11.105 | 77.952 | 1.00 | 48.44 |
| 9632 | CE2 | TYR | B | 441 | 2.170 | -9.252 | 77.268 | 1.00 | 45.14 |
| 9633 | CD2 | TYR | B | 441 | 1.057 | -8.453 | 77.466 | 1.00 | 44.36 |
| 9634 | C | TYR | B | 441 | -2.086 | -5.999 | 80.034 | 1.00 | 40.43 |
| 9635 | O | TYR | B | 441 | -2.644 | -6.162 | 81.116 | 1.00 | 39.93 |
| 9636 | N | TYR | B | 442 | -2.575 | -5.224 | 79.076 | 1.00 | 39.24 |
| 9637 | CA | TYR | B | 442 | -3.888 | -4.622 | 79.204 | 1.00 | 38.12 |
| 9638 | CB | TYR | B | 442 | -3.860 | -3.272 | 79.937 | 1.00 | 37.79 |
| 9639 | CG | TYR | B | 442 | -3.000 | -2.211 | 79.308 | 1.00 | 36.99 |
| 9640 | CD1 | TYR | B | 442 | -1.625 | -2.194 | 79.505 | 1.00 | 37.49 |
| 9641 | CE1 | TYR | B | 442 | -0.833 | -1.212 | 78.931 | 1.00 | 37.66 |
| 9642 | CZ | TYR | B | 442 | -1.422 | -0.227 | 78.170 | 1.00 | 38.20 |
| 9643 | OH | TYR | B | 442 | -0.647 | 0.754 | 77.596 | 1.00 | 38.96 |
| 9644 | CE2 | TYR | B | 442 | -2.784 | -0.228 | 77.961 | 1.00 | 36.90 |
| 9645 | CD2 | TYR | B | 442 | -3.560 | -1.211 | 78.537 | 1.00 | 36.42 |
| 9646 | C | TYR | B | 442 | -4.563 | -4.490 | 77.858 | 1.00 | 37.75 |
| 9647 | O | TYR | B | 442 | -3.913 | -4.278 | 76.823 | 1.00 | 37.67 |
| 9648 | N | GLN | B | 443 | -5.878 | -4.659 | 77.874 | 1.00 | 36.72 |
| 9649 | CA | GLN | B | 443 | -6.651 | -4.475 | 76.672 | 1.00 | 36.23 |
| 9650 | CB | GLN | B | 443 | -7.711 | -5.553 | 76.518 | 1.00 | 36.03 |
| 9651 | CG | GLN | B | 443 | -8.658 | -5.236 | 75.375 | 1.00 | 35.04 |
| 9652 | CD | GLN | B | 443 | -9.951 | -5.958 | 75.506 | 1.00 | 34.59 |
| 9653 | OE1 | GLN | B | 443 | -10.484 | -6.080 | 76.606 | 1.00 | 36.36 |
| 9654 | NE2 | GLN | B | 443 | -10.460 | -6.464 | 74.397 | 1.00 | 34.60 |
| 9655 | C | GLN | B | 443 | -7.337 | -3.127 | 76.756 | 1.00 | 36.34 |
| 9656 | O | GLN | B | 443 | -8.010 | -2.816 | 77.743 | 1.00 | 35.78 |
| 9657 | N | LEU | B | 444 | -7.147 | -2.326 | 75.723 | 1.00 | 36.43 |
| 9658 | CA | LEU | B | 444 | -7.787 | -1.044 | 75.651 | 1.00 | 37.01 |
| 9659 | CB | LEU | B | 444 | -6.858 | -0.040 | 75.005 | 1.00 | 37.61 |
| 9660 | CG | LEU | B | 444 | -6.263 | 1.006 | 75.933 | 1.00 | 38.23 |
| 9661 | CD1 | LEU | B | 444 | -6.423 | 0.575 | 77.361 | 1.00 | 38.86 |
| 9662 | CD2 | LEU | B | 444 | -4.808 | 1.225 | 75.567 | 1.00 | 38.29 |
| 9663 | C | LEU | B | 444 | -9.023 | -1.169 | 74.802 | 1.00 | 37.52 |
| 9664 | O | LEU | B | 444 | -9.020 | -1.861 | 73.777 | 1.00 | 37.47 |
| 9665 | N | ARG | B | 445 | -10.074 | -0.480 | 75.223 | 1.00 | 37.73 |
| 9666 | CA | ARG | B | 445 | -11.310 | -0.474 | 74.482 | 1.00 | 38.31 |
| 9667 | CB | ARG | B | 445 | -12.346 | -1.350 | 75.178 | 1.00 | 38.87 |
| 9668 | CG | ARG | B | 445 | -13.533 | -1.688 | 74.303 | 1.00 | 42.76 |
| 9669 | CD | ARG | B | 445 | -14.843 | -1.000 | 74.669 | 1.00 | 47.80 |
| 9670 | NE | ARG | B | 445 | -15.287 | -1.361 | 76.013 | 1.00 | 51.94 |
| 9671 | CZ | ARG | B | 445 | -16.556 | -1.532 | 76.353 | 1.00 | 54.29 |
| 9672 | NH1 | ARG | B | 445 | -16.873 | -1.853 | 77.599 | 1.00 | 54.15 |
| 9673 | NH2 | ARG | B | 445 | -17.511 | -1.384 | 75.440 | 1.00 | 56.63 |
| 9674 | C | ARG | B | 445 | -11.835 | 0.939 | 74.338 | 1.00 | 37.77 |
| 9675 | O | ARG | B | 445 | -12.249 | 1.556 | 75.312 | 1.00 | 37.63 |
| 9676 | N | CYS | B | 446 | -11.790 | 1.470 | 73.128 | 1.00 | 37.48 |
| 9677 | CA | CYS | B | 446 | -12.403 | 2.759 | 72.914 | 1.00 | 37.98 |
| 9678 | CB | CYS | B | 446 | -11.512 | 3.700 | 72.094 | 1.00 | 38.50 |
| 9679 | SG | CYS | B | 446 | -11.923 | 3.914 | 70.361 | 1.00 | 39.17 |
| 9680 | C | CYS | B | 446 | -13.755 | 2.520 | 72.262 | 1.00 | 37.44 |

FIGURE 3 GH

| A | B | C | D | E | F | G | H | I | J |
|---|---|---|---|---|---|---|---|---|---|
| 9681 | O | CYS | B | 446 | -13.878 | 1.724 | 71.325 | 1.00 | 37.58 |
| 9682 | N | SER | B | 447 | -14.770 | 3.181 | 72.801 | 1.00 | 36.87 |
| 9683 | CA | SER | B | 447 | -16.121 | 3.056 | 72.295 | 1.00 | 36.06 |
| 9684 | CB | SER | B | 447 | -17.122 | 2.929 | 73.438 | 1.00 | 36.12 |
| 9685 | OG | SER | B | 447 | -16.507 | 2.481 | 74.615 | 1.00 | 37.23 |
| 9686 | C | SER | B | 447 | -16.522 | 4.275 | 71.515 | 1.00 | 35.55 |
| 9687 | O | SER | B | 447 | -17.706 | 4.497 | 71.328 | 1.00 | 36.20 |
| 9688 | N | GLY | B | 448 | -15.581 | 5.099 | 71.087 | 1.00 | 35.02 |
| 9689 | CA | GLY | B | 448 | -15.976 | 6.242 | 70.284 | 1.00 | 35.18 |
| 9690 | C | GLY | B | 448 | -14.985 | 7.371 | 70.326 | 1.00 | 35.66 |
| 9691 | O | GLY | B | 448 | -14.066 | 7.358 | 71.159 | 1.00 | 35.53 |
| 9692 | N | PRO | B | 449 | -15.225 | 8.399 | 69.513 | 1.00 | 35.54 |
| 9693 | CA | PRO | B | 449 | -16.452 | 8.519 | 68.730 | 1.00 | 36.01 |
| 9694 | CB | PRO | B | 449 | -16.529 | 10.019 | 68.437 | 1.00 | 35.79 |
| 9695 | CG | PRO | B | 449 | -15.303 | 10.613 | 69.029 | 1.00 | 35.21 |
| 9696 | CD | PRO | B | 449 | -14.330 | 9.538 | 69.289 | 1.00 | 35.44 |
| 9697 | C | PRO | B | 449 | -16.445 | 7.763 | 67.420 | 1.00 | 36.31 |
| 9698 | O | PRO | B | 449 | -17.496 | 7.669 | 66.801 | 1.00 | 36.67 |
| 9699 | N | GLY | B | 450 | -15.291 | 7.273 | 66.985 | 1.00 | 36.24 |
| 9700 | CA | GLY | B | 450 | -15.233 | 6.492 | 65.763 | 1.00 | 35.98 |
| 9701 | C | GLY | B | 450 | -15.727 | 5.092 | 66.085 | 1.00 | 35.94 |
| 9702 | O | GLY | B | 450 | -16.284 | 4.881 | 67.157 | 1.00 | 35.95 |
| 9703 | N | LEU | B | 451 | -15.508 | 4.134 | 65.187 | 1.00 | 35.82 |
| 9704 | CA | LEU | B | 451 | -15.958 | 2.775 | 65.409 | 1.00 | 35.69 |
| 9705 | CB | LEU | B | 451 | -15.798 | 1.942 | 64.138 | 1.00 | 35.37 |
| 9706 | CG | LEU | B | 451 | -16.637 | 2.364 | 62.934 | 1.00 | 36.88 |
| 9707 | CD1 | LEU | B | 451 | -18.043 | 2.722 | 63.371 | 1.00 | 39.09 |
| 9708 | CD2 | LEU | B | 451 | -16.684 | 1.242 | 61.902 | 1.00 | 36.51 |
| 9709 | C | LEU | B | 451 | -15.163 | 2.145 | 66.532 | 1.00 | 35.78 |
| 9710 | O | LEU | B | 451 | -13.961 | 2.287 | 66.602 | 1.00 | 35.77 |
| 9711 | N | PRO | B | 452 | -15.841 | 1.442 | 67.418 | 1.00 | 36.02 |
| 9712 | CA | PRO | B | 452 | -15.164 | 0.787 | 68.530 | 1.00 | 36.49 |
| 9713 | CB | PRO | B | 452 | -16.214 | -0.211 | 69.018 | 1.00 | 36.60 |
| 9714 | CG | PRO | B | 452 | -17.502 | 0.466 | 68.737 | 1.00 | 36.28 |
| 9715 | CD | PRO | B | 452 | -17.298 | 1.227 | 67.442 | 1.00 | 35.76 |
| 9716 | C | PRO | B | 452 | -13.907 | 0.071 | 68.048 | 1.00 | 36.91 |
| 9717 | O | PRO | B | 452 | -13.890 | -0.497 | 66.961 | 1.00 | 37.14 |
| 9718 | N | LEU | B | 453 | -12.861 | 0.103 | 68.860 | 1.00 | 37.38 |
| 9719 | CA | LEU | B | 453 | -11.595 | -0.518 | 68.509 | 1.00 | 37.79 |
| 9720 | CB | LEU | B | 453 | -10.662 | 0.548 | 67.909 | 1.00 | 38.09 |
| 9721 | CG | LEU | B | 453 | -9.130 | 0.424 | 67.895 | 1.00 | 39.23 |
| 9722 | CD1 | LEU | B | 453 | -8.581 | 0.806 | 69.245 | 1.00 | 41.73 |
| 9723 | CD2 | LEU | B | 453 | -8.527 | 1.356 | 66.877 | 1.00 | 38.74 |
| 9724 | C | LEU | B | 453 | -11.009 | -1.163 | 69.761 | 1.00 | 37.97 |
| 9725 | O | LEU | B | 453 | -10.954 | -0.529 | 70.810 | 1.00 | 38.14 |
| 9726 | N | TYR | B | 454 | -10.614 | -2.431 | 69.664 | 1.00 | 38.19 |
| 9727 | CA | TYR | B | 454 | -10.018 | -3.156 | 70.792 | 1.00 | 38.49 |
| 9728 | CB | TYR | B | 454 | -10.786 | -4.451 | 71.099 | 1.00 | 38.13 |
| 9729 | CG | TYR | B | 454 | -12.241 | -4.232 | 71.417 | 1.00 | 38.60 |
| 9730 | CD1 | TYR | B | 454 | -12.725 | -4.381 | 72.711 | 1.00 | 38.94 |
| 9731 | CE1 | TYR | B | 454 | -14.068 | -4.170 | 73.001 | 1.00 | 37.86 |

FIGURE 3 GI

| A | B | C | D | E | F | G | H | I | J |
|---|---|---|---|---|---|---|---|---|---|
| 9732 | CZ | TYR | B | 454 | -14.920 | -3.799 | 71.988 | 1.00 | 39.51 |
| 9733 | OH | TYR | B | 454 | -16.261 | -3.584 | 72.236 | 1.00 | 40.91 |
| 9734 | CE2 | TYR | B | 454 | -14.452 | -3.651 | 70.698 | 1.00 | 39.29 |
| 9735 | CD2 | TYR | B | 454 | -13.135 | -3.864 | 70.422 | 1.00 | 38.35 |
| 9736 | C | TYR | B | 454 | -8.543 | -3.484 | 70.539 | 1.00 | 38.72 |
| 9737 | O | TYR | B | 454 | -8.198 | -4.055 | 69.504 | 1.00 | 38.95 |
| 9738 | N | THR | B | 455 | -7.680 | -3.133 | 71.488 | 1.00 | 38.84 |
| 9739 | CA | THR | B | 455 | -6.247 | -3.378 | 71.332 | 1.00 | 38.93 |
| 9740 | CB | THR | B | 455 | -5.498 | -2.084 | 71.007 | 1.00 | 38.87 |
| 9741 | OG1 | THR | B | 455 | -5.832 | -1.074 | 71.970 | 1.00 | 38.92 |
| 9742 | CG2 | THR | B | 455 | -5.949 | -1.515 | 69.675 | 1.00 | 38.16 |
| 9743 | C | THR | B | 455 | -5.612 | -4.010 | 72.552 | 1.00 | 39.32 |
| 9744 | O | THR | B | 455 | -6.117 | -3.875 | 73.669 | 1.00 | 39.52 |
| 9745 | N | LEU | B | 456 | -4.499 | -4.703 | 72.326 | 1.00 | 39.79 |
| 9746 | CA | LEU | B | 456 | -3.757 | -5.353 | 73.399 | 1.00 | 40.44 |
| 9747 | CB | LEU | B | 456 | -3.461 | -6.798 | 73.042 | 1.00 | 40.42 |
| 9748 | CG | LEU | B | 456 | -3.868 | -7.892 | 74.030 | 1.00 | 42.00 |
| 9749 | CD1 | LEU | B | 456 | -2.769 | -8.937 | 74.072 | 1.00 | 42.32 |
| 9750 | CD2 | LEU | B | 456 | -4.161 | -7.367 | 75.430 | 1.00 | 42.07 |
| 9751 | C | LEU | B | 456 | -2.443 | -4.600 | 73.573 | 1.00 | 40.92 |
| 9752 | O | LEU | B | 456 | -1.850 | -4.143 | 72.590 | 1.00 | 41.11 |
| 9753 | N | HIS | B | 457 | -1.989 | -4.467 | 74.814 | 1.00 | 41.21 |
| 9754 | CA | HIS | B | 457 | -0.764 | -3.742 | 75.089 | 1.00 | 41.70 |
| 9755 | CB | HIS | B | 457 | -1.076 | -2.289 | 75.445 | 1.00 | 41.48 |
| 9756 | CG | HIS | B | 457 | -2.119 | -1.676 | 74.576 | 1.00 | 39.95 |
| 9757 | ND1 | HIS | B | 457 | -1.832 | -0.706 | 73.645 | 1.00 | 38.88 |
| 9758 | CE1 | HIS | B | 457 | -2.941 | -0.363 | 73.016 | 1.00 | 38.91 |
| 9759 | NE2 | HIS | B | 457 | -3.938 | -1.077 | 73.509 | 1.00 | 37.88 |
| 9760 | CD2 | HIS | B | 457 | -3.449 | -1.910 | 74.482 | 1.00 | 38.62 |
| 9761 | C | HIS | B | 457 | -0.015 | -4.360 | 76.244 | 1.00 | 42.55 |
| 9762 | O | HIS | B | 457 | -0.616 | -4.954 | 77.146 | 1.00 | 42.69 |
| 9763 | N | SER | B | 458 | 1.304 | -4.206 | 76.232 | 1.00 | 43.43 |
| 9764 | CA | SER | B | 458 | 2.094 | -4.676 | 77.356 | 1.00 | 44.71 |
| 9765 | CB | SER | B | 458 | 3.357 | -5.398 | 76.897 | 1.00 | 44.67 |
| 9766 | OG | SER | B | 458 | 4.135 | -4.566 | 76.061 | 1.00 | 45.67 |
| 9767 | C | SER | B | 458 | 2.424 | -3.460 | 78.205 | 1.00 | 45.51 |
| 9768 | O | SER | B | 458 | 2.696 | -2.379 | 77.682 | 1.00 | 44.86 |
| 9769 | N | SER | B | 459 | 2.395 | -3.636 | 79.520 | 1.00 | 46.90 |
| 9770 | CA | SER | B | 459 | 2.622 | -2.509 | 80.408 | 1.00 | 48.50 |
| 9771 | CB | SER | B | 459 | 1.924 | -2.735 | 81.747 | 1.00 | 48.28 |
| 9772 | OG | SER | B | 459 | 2.207 | -4.021 | 82.264 | 1.00 | 49.98 |
| 9773 | C | SER | B | 459 | 4.100 | -2.126 | 80.590 | 1.00 | 49.47 |
| 9774 | O | SER | B | 459 | 4.407 | -1.007 | 80.992 | 1.00 | 49.61 |
| 9775 | N | VAL | B | 460 | 5.011 | -3.035 | 80.255 | 1.00 | 50.94 |
| 9776 | CA | VAL | B | 460 | 6.439 | -2.775 | 80.445 | 1.00 | 51.98 |
| 9777 | CB | VAL | B | 460 | 7.315 | -3.923 | 79.914 | 1.00 | 52.10 |
| 9778 | CG1 | VAL | B | 460 | 8.782 | -3.620 | 80.154 | 1.00 | 52.94 |
| 9779 | CG2 | VAL | B | 460 | 6.938 | -5.221 | 80.594 | 1.00 | 52.80 |
| 9780 | C | VAL | B | 460 | 6.874 | -1.456 | 79.829 | 1.00 | 52.32 |
| 9781 | O | VAL | B | 460 | 7.412 | -0.595 | 80.518 | 1.00 | 52.84 |
| 9782 | N | ASN | B | 461 | 6.655 | -1.294 | 78.534 | 1.00 | 52.98 |

FIGURE 3 GJ

| A | B | C | D | E | F | G | H | I | J |
|---|---|---|---|---|---|---|---|---|---|
| 9783 | CA | ASN | B | 461 | 7.001 | -0.038 | 77.875 | 1.00 | 53.52 |
| 9784 | CB | ASN | B | 461 | 8.271 | -0.176 | 77.034 | 1.00 | 53.99 |
| 9785 | CG | ASN | B | 461 | 9.539 | 0.100 | 77.842 | 1.00 | 55.10 |
| 9786 | OD1 | ASN | B | 461 | 9.873 | 1.259 | 78.116 | 1.00 | 55.97 |
| 9787 | ND2 | ASN | B | 461 | 10.246 | -0.963 | 78.230 | 1.00 | 55.66 |
| 9788 | C | ASN | B | 461 | 5.839 | 0.487 | 77.052 | 1.00 | 53.51 |
| 9789 | O | ASN | B | 461 | 6.019 | 1.187 | 76.053 | 1.00 | 53.38 |
| 9790 | N | ASP | B | 462 | 4.641 | 0.127 | 77.502 | 1.00 | 53.66 |
| 9791 | CA | ASP | B | 462 | 3.388 | 0.542 | 76.880 | 1.00 | 53.73 |
| 9792 | CB | ASP | B | 462 | 2.902 | 1.862 | 77.479 | 1.00 | 53.78 |
| 9793 | CG | ASP | B | 462 | 2.632 | 1.752 | 78.955 | 1.00 | 54.43 |
| 9794 | OD1 | ASP | B | 462 | 3.211 | 2.549 | 79.731 | 1.00 | 55.45 |
| 9795 | OD2 | ASP | B | 462 | 1.863 | 0.890 | 79.431 | 1.00 | 54.43 |
| 9796 | C | ASP | B | 462 | 3.438 | 0.648 | 75.368 | 1.00 | 53.40 |
| 9797 | O | ASP | B | 462 | 3.141 | 1.703 | 74.811 | 1.00 | 53.36 |
| 9798 | N | LYS | B | 463 | 3.816 | -0.436 | 74.702 | 1.00 | 52.90 |
| 9799 | CA | LYS | B | 463 | 3.768 | -0.435 | 73.251 | 1.00 | 52.73 |
| 9800 | CB | LYS | B | 463 | 5.080 | -0.926 | 72.633 | 1.00 | 53.15 |
| 9801 | CG | LYS | B | 463 | 5.195 | -2.435 | 72.468 | 1.00 | 55.06 |
| 9802 | CD | LYS | B | 463 | 6.260 | -2.758 | 71.435 | 1.00 | 57.55 |
| 9803 | CE | LYS | B | 463 | 5.943 | -4.039 | 70.664 | 1.00 | 59.47 |
| 9804 | NZ | LYS | B | 463 | 6.763 | -4.144 | 69.409 | 1.00 | 59.87 |
| 9805 | C | LYS | B | 463 | 2.573 | -1.270 | 72.787 | 1.00 | 51.90 |
| 9806 | O | LYS | B | 463 | 2.077 | -2.139 | 73.507 | 1.00 | 51.86 |
| 9807 | N | GLY | B | 464 | 2.091 | -0.985 | 71.591 | 1.00 | 50.93 |
| 9808 | CA | GLY | B | 464 | 0.976 | -1.733 | 71.063 | 1.00 | 49.76 |
| 9809 | C | GLY | B | 464 | 1.427 | -3.098 | 70.591 | 1.00 | 48.51 |
| 9810 | O | GLY | B | 464 | 2.409 | -3.214 | 69.874 | 1.00 | 48.50 |
| 9811 | N | LEU | B | 465 | 0.729 | -4.140 | 71.016 | 1.00 | 47.52 |
| 9812 | CA | LEU | B | 465 | 1.030 | -5.469 | 70.523 | 1.00 | 46.73 |
| 9813 | CB | LEU | B | 465 | 0.649 | -6.530 | 71.555 | 1.00 | 46.55 |
| 9814 | CG | LEU | B | 465 | 1.474 | -6.509 | 72.848 | 1.00 | 46.30 |
| 9815 | CD1 | LEU | B | 465 | 0.704 | -7.128 | 73.979 | 1.00 | 43.80 |
| 9816 | CD2 | LEU | B | 465 | 2.822 | -7.213 | 72.666 | 1.00 | 45.01 |
| 9817 | C | LEU | B | 465 | 0.258 | -5.683 | 69.222 | 1.00 | 46.37 |
| 9818 | O | LEU | B | 465 | 0.848 | -5.950 | 68.169 | 1.00 | 46.31 |
| 9819 | N | ARG | B | 466 | -1.062 | -5.521 | 69.289 | 1.00 | 45.36 |
| 9820 | CA | ARG | B | 466 | -1.897 | -5.788 | 68.128 | 1.00 | 44.30 |
| 9821 | CB | ARG | B | 466 | -1.915 | -7.287 | 67.854 | 1.00 | 44.34 |
| 9822 | CG | ARG | B | 466 | -2.567 | -8.082 | 68.969 | 1.00 | 44.74 |
| 9823 | CD | ARG | B | 466 | -2.273 | -9.569 | 68.931 | 1.00 | 44.86 |
| 9824 | NE | ARG | B | 466 | -0.847 | -9.831 | 69.115 | 1.00 | 44.16 |
| 9825 | CZ | ARG | B | 466 | -0.291 | -10.154 | 70.271 | 1.00 | 44.48 |
| 9826 | NH1 | ARG | B | 466 | 1.017 | -10.375 | 70.344 | 1.00 | 44.39 |
| 9827 | NH2 | ARG | B | 466 | -1.041 | -10.261 | 71.361 | 1.00 | 45.27 |
| 9828 | C | ARG | B | 466 | -3.340 | -5.332 | 68.252 | 1.00 | 43.59 |
| 9829 | O | ARG | B | 466 | -3.863 | -5.072 | 69.338 | 1.00 | 43.21 |
| 9830 | N | VAL | B | 467 | -3.980 | -5.268 | 67.097 | 1.00 | 42.75 |
| 9831 | CA | VAL | B | 467 | -5.369 | -4.922 | 67.005 | 1.00 | 41.90 |
| 9832 | CB | VAL | B | 467 | -5.664 | -4.313 | 65.637 | 1.00 | 42.12 |
| 9833 | CG1 | VAL | B | 467 | -7.081 | -3.744 | 65.597 | 1.00 | 42.48 |

FIGURE 3 GK

| A | B | C | D | E | F | G | H | I | J |
|---|---|---|---|---|---|---|---|---|---|
| 9834 | CG2 | VAL | B | 467 | -4.650 | -3.202 | 65.333 | 1.00 | 42.81 |
| 9835 | C | VAL | B | 467 | -6.170 | -6.201 | 67.196 | 1.00 | 41.22 |
| 9836 | O | VAL | B | 467 | -6.039 | -7.142 | 66.417 | 1.00 | 41.01 |
| 9837 | N | LEU | B | 468 | -6.982 | -6.243 | 68.246 | 1.00 | 40.12 |
| 9838 | CA | LEU | B | 468 | -7.828 | -7.399 | 68.505 | 1.00 | 39.35 |
| 9839 | CB | LEU | B | 468 | -8.260 | -7.431 | 69.972 | 1.00 | 39.22 |
| 9840 | CG | LEU | B | 468 | -7.149 | -7.616 | 71.012 | 1.00 | 39.50 |
| 9841 | CD1 | LEU | B | 468 | -7.722 | -7.565 | 72.418 | 1.00 | 39.92 |
| 9842 | CD2 | LEU | B | 468 | -6.424 | -8.935 | 70.794 | 1.00 | 39.93 |
| 9843 | C | LEU | B | 468 | -9.067 | -7.355 | 67.616 | 1.00 | 38.66 |
| 9844 | O | LEU | B | 468 | -9.380 | -8.299 | 66.893 | 1.00 | 38.22 |
| 9845 | N | GLU | B | 469 | -9.776 | -6.240 | 67.678 | 1.00 | 38.22 |
| 9846 | CA | GLU | B | 469 | -11.001 | -6.078 | 66.908 | 1.00 | 37.30 |
| 9847 | CB | GLU | B | 469 | -12.214 | -6.450 | 67.742 | 1.00 | 37.22 |
| 9848 | CG | GLU | B | 469 | -13.526 | -6.249 | 67.005 | 1.00 | 37.38 |
| 9849 | CD | GLU | B | 469 | -13.602 | -7.106 | 65.761 | 1.00 | 37.88 |
| 9850 | OE1 | GLU | B | 469 | -13.746 | -6.562 | 64.643 | 1.00 | 34.63 |
| 9851 | OE2 | GLU | B | 469 | -13.507 | -8.340 | 65.913 | 1.00 | 39.57 |
| 9852 | C | GLU | B | 469 | -11.111 | -4.642 | 66.478 | 1.00 | 36.92 |
| 9853 | O | GLU | B | 469 | -11.158 | -3.739 | 67.311 | 1.00 | 36.60 |
| 9854 | N | ASP | B | 470 | -11.151 | -4.428 | 65.173 | 1.00 | 36.62 |
| 9855 | CA | ASP | B | 470 | -11.196 | -3.073 | 64.657 | 1.00 | 36.74 |
| 9856 | CB | ASP | B | 470 | -10.052 | -2.824 | 63.674 | 1.00 | 36.90 |
| 9857 | CG | ASP | B | 470 | -10.163 | -3.682 | 62.436 | 1.00 | 39.20 |
| 9858 | OD1 | ASP | B | 470 | -9.253 | -3.593 | 61.570 | 1.00 | 41.35 |
| 9859 | OD2 | ASP | B | 470 | -11.124 | -4.474 | 62.251 | 1.00 | 38.62 |
| 9860 | C | ASP | B | 470 | -12.516 | -2.688 | 64.001 | 1.00 | 36.27 |
| 9861 | O | ASP | B | 470 | -12.692 | -1.535 | 63.617 | 1.00 | 36.08 |
| 9862 | N | ASN | B | 471 | -13.432 | -3.636 | 63.851 | 1.00 | 35.57 |
| 9863 | CA | ASN | B | 471 | -14.730 | -3.329 | 63.260 | 1.00 | 34.94 |
| 9864 | CB | ASN | B | 471 | -15.398 | -2.204 | 64.052 | 1.00 | 34.49 |
| 9865 | CG | ASN | B | 471 | -16.283 | -2.724 | 65.145 | 1.00 | 34.14 |
| 9866 | OD1 | ASN | B | 471 | -17.202 | -3.497 | 64.874 | 1.00 | 33.71 |
| 9867 | ND2 | ASN | B | 471 | -15.998 | -2.349 | 66.392 | 1.00 | 33.93 |
| 9868 | C | ASN | B | 471 | -14.664 | -2.921 | 61.793 | 1.00 | 35.06 |
| 9869 | O | ASN | B | 471 | -15.390 | -2.014 | 61.353 | 1.00 | 34.47 |
| 9870 | N | SER | B | 472 | -13.787 | -3.559 | 61.024 | 1.00 | 34.95 |
| 9871 | CA | SER | B | 472 | -13.676 | -3.163 | 59.634 | 1.00 | 34.75 |
| 9872 | CB | SER | B | 472 | -12.326 | -3.557 | 59.016 | 1.00 | 34.94 |
| 9873 | OG | SER | B | 472 | -12.115 | -4.949 | 59.129 | 1.00 | 38.29 |
| 9874 | C | SER | B | 472 | -14.866 | -3.691 | 58.856 | 1.00 | 33.94 |
| 9875 | O | SER | B | 472 | -15.292 | -3.077 | 57.880 | 1.00 | 33.88 |
| 9876 | N | ALA | B | 473 | -15.434 | -4.809 | 59.304 | 1.00 | 33.57 |
| 9877 | CA | ALA | B | 473 | -16.598 | -5.340 | 58.613 | 1.00 | 33.41 |
| 9878 | CB | ALA | B | 473 | -17.064 | -6.637 | 59.228 | 1.00 | 33.35 |
| 9879 | C | ALA | B | 473 | -17.718 | -4.301 | 58.636 | 1.00 | 33.49 |
| 9880 | O | ALA | B | 473 | -18.344 | -4.025 | 57.615 | 1.00 | 32.91 |
| 9881 | N | LEU | B | 474 | -17.953 | -3.720 | 59.805 | 1.00 | 33.55 |
| 9882 | CA | LEU | B | 474 | -19.018 | -2.745 | 59.955 | 1.00 | 33.99 |
| 9883 | CB | LEU | B | 474 | -19.268 | -2.456 | 61.428 | 1.00 | 34.22 |
| 9884 | CG | LEU | B | 474 | -20.243 | -1.312 | 61.748 | 1.00 | 35.30 |

FIGURE 3 GL

| A | B | C | D | E | F | G | H | I | J |
|---|---|---|---|---|---|---|---|---|---|
| 9885 | CD1 | LEU | B | 474 | -21.642 | -1.617 | 61.238 | 1.00 | 34.21 |
| 9886 | CD2 | LEU | B | 474 | -20.264 | -1.083 | 63.245 | 1.00 | 34.84 |
| 9887 | C | LEU | B | 474 | -18.651 | -1.475 | 59.223 | 1.00 | 33.97 |
| 9888 | O | LEU | B | 474 | -19.490 | -0.847 | 58.599 | 1.00 | 33.99 |
| 9889 | N | ASP | B | 475 | -17.381 | -1.110 | 59.286 | 1.00 | 34.46 |
| 9890 | CA | ASP | B | 475 | -16.914 | 0.051 | 58.566 | 1.00 | 35.26 |
| 9891 | CB | ASP | B | 475 | -15.419 | 0.234 | 58.764 | 1.00 | 34.89 |
| 9892 | CG | ASP | B | 475 | -14.904 | 1.486 | 58.114 | 1.00 | 34.68 |
| 9893 | OD1 | ASP | B | 475 | -14.294 | 1.378 | 57.024 | 1.00 | 36.50 |
| 9894 | OD2 | ASP | B | 475 | -15.073 | 2.621 | 58.605 | 1.00 | 33.48 |
| 9895 | C | ASP | B | 475 | -17.235 | -0.155 | 57.100 | 1.00 | 36.26 |
| 9896 | O | ASP | B | 475 | -17.695 | 0.760 | 56.422 | 1.00 | 36.57 |
| 9897 | N | LYS | B | 476 | -17.009 | -1.373 | 56.619 | 1.00 | 37.51 |
| 9898 | CA | LYS | B | 476 | -17.307 | -1.702 | 55.235 | 1.00 | 38.64 |
| 9899 | CB | LYS | B | 476 | -16.864 | -3.133 | 54.895 | 1.00 | 39.35 |
| 9900 | CG | LYS | B | 476 | -16.867 | -3.452 | 53.387 | 1.00 | 42.66 |
| 9901 | CD | LYS | B | 476 | -16.549 | -4.930 | 53.071 | 1.00 | 46.42 |
| 9902 | CE | LYS | B | 476 | -15.146 | -5.353 | 53.556 | 1.00 | 49.78 |
| 9903 | NZ | LYS | B | 476 | -14.011 | -5.112 | 52.586 | 1.00 | 50.22 |
| 9904 | C | LYS | B | 476 | -18.785 | -1.515 | 54.913 | 1.00 | 38.54 |
| 9905 | O | LYS | B | 476 | -19.136 | -0.832 | 53.950 | 1.00 | 38.36 |
| 9906 | N | MET | B | 477 | -19.682 | -2.082 | 55.705 | 1.00 | 38.82 |
| 9907 | CA | MET | B | 477 | -21.081 | -1.959 | 55.285 | 1.00 | 39.10 |
| 9908 | CB | MET | B | 477 | -21.981 | -3.097 | 55.807 | 1.00 | 39.28 |
| 9909 | CG | MET | B | 477 | -21.886 | -3.480 | 57.261 | 1.00 | 41.02 |
| 9910 | SD | MET | B | 477 | -23.103 | -4.821 | 57.689 | 1.00 | 46.02 |
| 9911 | CE | MET | B | 477 | -24.462 | -4.449 | 56.569 | 1.00 | 44.10 |
| 9912 | C | MET | B | 477 | -21.666 | -0.546 | 55.451 | 1.00 | 39.01 |
| 9913 | O | MET | B | 477 | -22.680 | -0.194 | 54.852 | 1.00 | 38.91 |
| 9914 | N | LEU | B | 478 | -20.965 | 0.287 | 56.207 | 1.00 | 39.11 |
| 9915 | CA | LEU | B | 478 | -21.407 | 1.642 | 56.466 | 1.00 | 38.82 |
| 9916 | CB | LEU | B | 478 | -20.855 | 2.085 | 57.823 | 1.00 | 38.62 |
| 9917 | CG | LEU | B | 478 | -21.755 | 2.331 | 59.045 | 1.00 | 38.51 |
| 9918 | CD1 | LEU | B | 478 | -20.964 | 2.105 | 60.317 | 1.00 | 37.08 |
| 9919 | CD2 | LEU | B | 478 | -23.047 | 1.502 | 59.055 | 1.00 | 35.88 |
| 9920 | C | LEU | B | 478 | -21.008 | 2.678 | 55.408 | 1.00 | 39.38 |
| 9921 | O | LEU | B | 478 | -21.552 | 3.785 | 55.413 | 1.00 | 38.90 |
| 9922 | N | GLN | B | 479 | -20.090 | 2.358 | 54.492 | 1.00 | 39.91 |
| 9923 | CA | GLN | B | 479 | -19.596 | 3.450 | 53.631 | 1.00 | 40.99 |
| 9924 | CB | GLN | B | 479 | -18.147 | 3.261 | 53.104 | 1.00 | 42.19 |
| 9925 | CG | GLN | B | 479 | -17.943 | 2.372 | 51.893 | 1.00 | 44.87 |
| 9926 | CD | GLN | B | 479 | -17.624 | 0.962 | 52.297 | 1.00 | 47.18 |
| 9927 | OE1 | GLN | B | 479 | -16.774 | 0.305 | 51.699 | 1.00 | 46.75 |
| 9928 | NE2 | GLN | B | 479 | -18.309 | 0.487 | 53.326 | 1.00 | 50.12 |
| 9929 | C | GLN | B | 479 | -20.543 | 4.123 | 52.618 | 1.00 | 40.45 |
| 9930 | O | GLN | B | 479 | -20.297 | 5.250 | 52.195 | 1.00 | 40.42 |
| 9931 | N | ASN | B | 480 | -21.628 | 3.450 | 52.257 | 1.00 | 39.75 |
| 9932 | CA | ASN | B | 480 | -22.617 | 4.071 | 51.395 | 1.00 | 39.17 |
| 9933 | CB | ASN | B | 480 | -22.810 | 3.303 | 50.079 | 1.00 | 39.07 |
| 9934 | CG | ASN | B | 480 | -23.389 | 1.934 | 50.283 | 1.00 | 38.34 |
| 9935 | OD1 | ASN | B | 480 | -23.675 | 1.532 | 51.405 | 1.00 | 39.33 |

FIGURE 3 GM

| A | B | C | D | E | F | G | H | I | J |
|---|---|---|---|---|---|---|---|---|---|
| 9936 | ND2 | ASN | B | 480 | -23.562 | 1.197 | 49.195 | 1.00 | 37.35 |
| 9937 | C | ASN | B | 480 | -23.952 | 4.292 | 52.122 | 1.00 | 38.84 |
| 9938 | O | ASN | B | 480 | -25.018 | 4.289 | 51.492 | 1.00 | 38.34 |
| 9939 | N | VAL | B | 481 | -23.884 | 4.458 | 53.445 | 1.00 | 37.77 |
| 9940 | CA | VAL | B | 481 | -25.073 | 4.817 | 54.206 | 1.00 | 37.02 |
| 9941 | CB | VAL | B | 481 | -25.599 | 3.678 | 55.168 | 1.00 | 37.04 |
| 9942 | CG1 | VAL | B | 481 | -24.615 | 2.580 | 55.334 | 1.00 | 36.01 |
| 9943 | CG2 | VAL | B | 481 | -26.077 | 4.215 | 56.508 | 1.00 | 36.67 |
| 9944 | C | VAL | B | 481 | -24.946 | 6.178 | 54.875 | 1.00 | 36.63 |
| 9945 | O | VAL | B | 481 | -23.948 | 6.503 | 55.486 | 1.00 | 36.05 |
| 9946 | N | GLN | B | 482 | -25.978 | 6.987 | 54.718 | 1.00 | 36.78 |
| 9947 | CA | GLN | B | 482 | -25.988 | 8.333 | 55.258 | 1.00 | 36.69 |
| 9948 | CB | GLN | B | 482 | -27.107 | 9.136 | 54.611 | 1.00 | 36.71 |
| 9949 | CG | GLN | B | 482 | -26.914 | 9.252 | 53.108 | 1.00 | 38.91 |
| 9950 | CD | GLN | B | 482 | -28.133 | 9.801 | 52.401 | 1.00 | 40.62 |
| 9951 | OE1 | GLN | B | 482 | -28.209 | 11.003 | 52.113 | 1.00 | 40.56 |
| 9952 | NE2 | GLN | B | 482 | -29.095 | 8.929 | 52.125 | 1.00 | 40.90 |
| 9953 | C | GLN | B | 482 | -26.137 | 8.298 | 56.763 | 1.00 | 36.68 |
| 9954 | O | GLN | B | 482 | -27.238 | 8.346 | 57.293 | 1.00 | 36.60 |
| 9955 | N | MET | B | 483 | -25.008 | 8.205 | 57.451 | 1.00 | 36.67 |
| 9956 | CA | MET | B | 483 | -25.026 | 8.136 | 58.892 | 1.00 | 36.98 |
| 9957 | CB | MET | B | 483 | -23.818 | 7.349 | 59.397 | 1.00 | 36.93 |
| 9958 | CG | MET | B | 483 | -23.898 | 5.889 | 59.020 | 1.00 | 37.27 |
| 9959 | SD | MET | B | 483 | -25.324 | 5.098 | 59.799 | 1.00 | 39.21 |
| 9960 | CE | MET | B | 483 | -24.718 | 5.123 | 61.489 | 1.00 | 37.40 |
| 9961 | C | MET | B | 483 | -25.048 | 9.517 | 59.487 | 1.00 | 37.15 |
| 9962 | O | MET | B | 483 | -24.606 | 10.476 | 58.881 | 1.00 | 37.52 |
| 9963 | N | PRO | B | 484 | -25.605 | 9.631 | 60.677 | 1.00 | 37.78 |
| 9964 | CA | PRO | B | 484 | -25.653 | 10.925 | 61.363 | 1.00 | 37.84 |
| 9965 | CB | PRO | B | 484 | -26.616 | 10.652 | 62.510 | 1.00 | 37.77 |
| 9966 | CG | PRO | B | 484 | -26.409 | 9.174 | 62.777 | 1.00 | 37.96 |
| 9967 | CD | PRO | B | 484 | -26.285 | 8.558 | 61.429 | 1.00 | 37.09 |
| 9968 | C | PRO | B | 484 | -24.281 | 11.285 | 61.920 | 1.00 | 37.92 |
| 9969 | O | PRO | B | 484 | -23.396 | 10.446 | 61.933 | 1.00 | 38.22 |
| 9970 | N | SER | B | 485 | -24.099 | 12.517 | 62.378 | 1.00 | 38.27 |
| 9971 | CA | SER | B | 485 | -22.843 | 12.863 | 63.023 | 1.00 | 38.32 |
| 9972 | CB | SER | B | 485 | -22.113 | 13.991 | 62.285 | 1.00 | 38.62 |
| 9973 | OG | SER | B | 485 | -22.789 | 15.229 | 62.422 | 1.00 | 38.59 |
| 9974 | C | SER | B | 485 | -23.140 | 13.254 | 64.449 | 1.00 | 38.06 |
| 9975 | O | SER | B | 485 | -24.299 | 13.373 | 64.844 | 1.00 | 38.12 |
| 9976 | N | LYS | B | 486 | -22.094 | 13.397 | 65.242 | 1.00 | 38.14 |
| 9977 | CA | LYS | B | 486 | -22.291 | 13.834 | 66.598 | 1.00 | 37.92 |
| 9978 | CB | LYS | B | 486 | -21.804 | 12.788 | 67.589 | 1.00 | 37.32 |
| 9979 | CG | LYS | B | 486 | -22.295 | 13.064 | 68.988 | 1.00 | 36.10 |
| 9980 | CD | LYS | B | 486 | -21.626 | 12.167 | 69.984 | 1.00 | 35.39 |
| 9981 | CE | LYS | B | 486 | -22.623 | 11.437 | 70.825 | 1.00 | 33.81 |
| 9982 | NZ | LYS | B | 486 | -21.933 | 10.471 | 71.696 | 1.00 | 31.22 |
| 9983 | C | LYS | B | 486 | -21.549 | 15.125 | 66.827 | 1.00 | 38.55 |
| 9984 | O | LYS | B | 486 | -20.406 | 15.277 | 66.404 | 1.00 | 38.40 |
| 9985 | N | LYS | B | 487 | -22.213 | 16.080 | 67.460 | 1.00 | 39.41 |
| 9986 | CA | LYS | B | 487 | -21.515 | 17.277 | 67.882 | 1.00 | 40.37 |

FIGURE 3 GN

| A | B | C | D | E | F | G | H | I | J |
|---|---|---|---|---|---|---|---|---|---|
| 9987 | CB | LYS | B | 487 | -22.202 | 18.552 | 67.416 | 1.00 | 40.73 |
| 9988 | CG | LYS | B | 487 | -21.733 | 19.785 | 68.194 | 1.00 | 42.32 |
| 9989 | CD | LYS | B | 487 | -21.414 | 20.922 | 67.260 | 1.00 | 45.83 |
| 9990 | CE | LYS | B | 487 | -21.483 | 22.276 | 67.946 | 1.00 | 48.42 |
| 9991 | NZ | LYS | B | 487 | -21.094 | 23.380 | 67.002 | 1.00 | 49.56 |
| 9992 | C | LYS | B | 487 | -21.461 | 17.245 | 69.385 | 1.00 | 40.25 |
| 9993 | O | LYS | B | 487 | -22.481 | 17.046 | 70.034 | 1.00 | 40.45 |
| 9994 | N | LEU | B | 488 | -20.262 | 17.395 | 69.931 | 1.00 | 40.48 |
| 9995 | CA | LEU | B | 488 | -20.063 | 17.425 | 71.371 | 1.00 | 40.70 |
| 9996 | CB | LEU | B | 488 | -19.056 | 16.371 | 71.791 | 1.00 | 40.34 |
| 9997 | CG | LEU | B | 488 | -19.267 | 15.608 | 73.101 | 1.00 | 40.39 |
| 9998 | CD1 | LEU | B | 488 | -17.932 | 15.099 | 73.580 | 1.00 | 38.50 |
| 9999 | CD2 | LEU | B | 488 | -19.939 | 16.422 | 74.200 | 1.00 | 38.59 |
| 10000 | C | LEU | B | 488 | -19.501 | 18.807 | 71.635 | 1.00 | 41.34 |
| 10001 | O | LEU | B | 488 | -18.436 | 19.152 | 71.134 | 1.00 | 41.42 |
| 10002 | N | ASP | B | 489 | -20.234 | 19.602 | 72.400 | 1.00 | 42.14 |
| 10003 | CA | ASP | B | 489 | -19.851 | 20.970 | 72.681 | 1.00 | 42.96 |
| 10004 | CB | ASP | B | 489 | -20.318 | 21.886 | 71.555 | 1.00 | 43.27 |
| 10005 | CG | ASP | B | 489 | -19.303 | 22.972 | 71.216 | 1.00 | 45.38 |
| 10006 | OD1 | ASP | B | 489 | -18.123 | 22.647 | 70.974 | 1.00 | 47.86 |
| 10007 | OD2 | ASP | B | 489 | -19.597 | 24.181 | 71.142 | 1.00 | 48.46 |
| 10008 | C | ASP | B | 489 | -20.491 | 21.382 | 74.001 | 1.00 | 43.31 |
| 10009 | O | ASP | B | 489 | -21.108 | 20.563 | 74.682 | 1.00 | 43.06 |
| 10010 | N | PHE | B | 490 | -20.347 | 22.650 | 74.359 | 1.00 | 43.92 |
| 10011 | CA | PHE | B | 490 | -20.862 | 23.128 | 75.627 | 1.00 | 44.57 |
| 10012 | CB | PHE | B | 490 | -19.730 | 23.186 | 76.655 | 1.00 | 44.71 |
| 10013 | CG | PHE | B | 490 | -18.628 | 24.148 | 76.295 | 1.00 | 45.17 |
| 10014 | CD1 | PHE | B | 490 | -18.728 | 25.493 | 76.610 | 1.00 | 45.54 |
| 10015 | CE1 | PHE | B | 490 | -17.717 | 26.378 | 76.276 | 1.00 | 46.24 |
| 10016 | CZ | PHE | B | 490 | -16.592 | 25.925 | 75.610 | 1.00 | 46.81 |
| 10017 | CE2 | PHE | B | 490 | -16.480 | 24.588 | 75.279 | 1.00 | 46.81 |
| 10018 | CD2 | PHE | B | 490 | -17.496 | 23.706 | 75.623 | 1.00 | 46.16 |
| 10019 | C | PHE | B | 490 | -21.491 | 24.505 | 75.500 | 1.00 | 45.08 |
| 10020 | O | PHE | B | 490 | -21.269 | 25.211 | 74.516 | 1.00 | 44.51 |
| 10021 | N | ILE | B | 491 | -22.308 | 24.862 | 76.487 | 1.00 | 45.90 |
| 10022 | CA | ILE | B | 491 | -22.814 | 26.224 | 76.601 | 1.00 | 47.24 |
| 10023 | CB | ILE | B | 491 | -24.325 | 26.364 | 76.291 | 1.00 | 47.15 |
| 10024 | CG1 | ILE | B | 491 | -25.148 | 25.408 | 77.147 | 1.00 | 47.50 |
| 10025 | CD1 | ILE | B | 491 | -26.606 | 25.519 | 76.910 | 1.00 | 48.34 |
| 10026 | CG2 | ILE | B | 491 | -24.606 | 26.135 | 74.806 | 1.00 | 47.94 |
| 10027 | C | ILE | B | 491 | -22.512 | 26.699 | 78.008 | 1.00 | 48.15 |
| 10028 | O | ILE | B | 491 | -22.203 | 25.899 | 78.893 | 1.00 | 47.96 |
| 10029 | N | ILE | B | 492 | -22.580 | 28.013 | 78.191 | 1.00 | 49.85 |
| 10030 | CA | ILE | B | 492 | -22.314 | 28.653 | 79.468 | 1.00 | 50.95 |
| 10031 | CB | ILE | B | 492 | -21.274 | 29.775 | 79.286 | 1.00 | 51.11 |
| 10032 | CG1 | ILE | B | 492 | -20.066 | 29.250 | 78.507 | 1.00 | 51.12 |
| 10033 | CD1 | ILE | B | 492 | -18.792 | 30.041 | 78.745 | 1.00 | 52.47 |
| 10034 | CG2 | ILE | B | 492 | -20.844 | 30.363 | 80.648 | 1.00 | 51.24 |
| 10035 | C | ILE | B | 492 | -23.622 | 29.220 | 79.971 | 1.00 | 51.58 |
| 10036 | O | ILE | B | 492 | -24.331 | 29.896 | 79.235 | 1.00 | 52.23 |
| 10037 | N | LEU | B | 493 | -23.962 | 28.943 | 81.219 | 1.00 | 52.29 |

FIGURE 3 GO

| A | B | C | D | E | F | G | H | I | J |
|---|---|---|---|---|---|---|---|---|---|
| 10038 | CA | LEU | B | 493 | -25.233 | 29.413 | 81.737 | 1.00 | 52.84 |
| 10039 | CB | LEU | B | 493 | -26.069 | 28.229 | 82.221 | 1.00 | 52.51 |
| 10040 | CG | LEU | B | 493 | -27.200 | 27.831 | 81.266 | 1.00 | 52.66 |
| 10041 | CD1 | LEU | B | 493 | -27.650 | 26.412 | 81.500 | 1.00 | 49.42 |
| 10042 | CD2 | LEU | B | 493 | -26.803 | 28.028 | 79.806 | 1.00 | 53.67 |
| 10043 | C | LEU | B | 493 | -25.098 | 30.481 | 82.828 | 1.00 | 53.43 |
| 10044 | O | LEU | B | 493 | -25.801 | 31.503 | 82.822 | 1.00 | 53.94 |
| 10045 | N | ASN | B | 494 | -24.172 | 30.261 | 83.745 | 1.00 | 53.60 |
| 10046 | CA | ASN | B | 494 | -24.003 | 31.154 | 84.875 | 1.00 | 53.59 |
| 10047 | CB | ASN | B | 494 | -24.875 | 30.649 | 86.023 | 1.00 | 53.96 |
| 10048 | CG | ASN | B | 494 | -25.182 | 31.711 | 87.060 | 1.00 | 55.31 |
| 10049 | OD1 | ASN | B | 494 | -26.350 | 31.975 | 87.354 | 1.00 | 57.50 |
| 10050 | ND2 | ASN | B | 494 | -24.143 | 32.297 | 87.649 | 1.00 | 55.83 |
| 10051 | C | ASN | B | 494 | -22.545 | 31.072 | 85.254 | 1.00 | 53.34 |
| 10052 | O | ASN | B | 494 | -22.205 | 30.710 | 86.373 | 1.00 | 53.44 |
| 10053 | N | GLU | B | 495 | -21.678 | 31.370 | 84.294 | 1.00 | 53.22 |
| 10054 | CA | GLU | B | 495 | -20.240 | 31.296 | 84.519 | 1.00 | 53.15 |
| 10055 | CB | GLU | B | 495 | -19.865 | 32.021 | 85.817 | 1.00 | 53.73 |
| 10056 | CG | GLU | B | 495 | -19.640 | 33.515 | 85.586 | 1.00 | 56.37 |
| 10057 | CD | GLU | B | 495 | -20.186 | 34.399 | 86.692 | 1.00 | 59.67 |
| 10058 | OE1 | GLU | B | 495 | -21.297 | 34.110 | 87.211 | 1.00 | 61.56 |
| 10059 | OE2 | GLU | B | 495 | -19.507 | 35.399 | 87.023 | 1.00 | 60.11 |
| 10060 | C | GLU | B | 495 | -19.684 | 29.864 | 84.461 | 1.00 | 52.30 |
| 10061 | O | GLU | B | 495 | -18.467 | 29.658 | 84.522 | 1.00 | 52.40 |
| 10062 | N | THR | B | 496 | -20.574 | 28.884 | 84.304 | 1.00 | 50.82 |
| 10063 | CA | THR | B | 496 | -20.168 | 27.480 | 84.229 | 1.00 | 49.32 |
| 10064 | CB | THR | B | 496 | -20.859 | 26.684 | 85.331 | 1.00 | 49.61 |
| 10065 | OG1 | THR | B | 496 | -22.249 | 27.008 | 85.319 | 1.00 | 51.05 |
| 10066 | CG2 | THR | B | 496 | -20.425 | 27.182 | 86.702 | 1.00 | 50.12 |
| 10067 | C | THR | B | 496 | -20.488 | 26.845 | 82.882 | 1.00 | 47.62 |
| 10068 | O | THR | B | 496 | -21.502 | 27.161 | 82.258 | 1.00 | 47.49 |
| 10069 | N | LYS | B | 497 | -19.609 | 25.954 | 82.438 | 1.00 | 45.55 |
| 10070 | CA | LYS | B | 497 | -19.807 | 25.223 | 81.198 | 1.00 | 43.78 |
| 10071 | CB | LYS | B | 497 | -18.479 | 24.646 | 80.715 | 1.00 | 44.12 |
| 10072 | CG | LYS | B | 497 | -17.656 | 25.556 | 79.813 | 1.00 | 45.88 |
| 10073 | CD | LYS | B | 497 | -16.173 | 25.423 | 80.161 | 1.00 | 48.55 |
| 10074 | CE | LYS | B | 497 | -15.283 | 25.386 | 78.934 | 1.00 | 50.48 |
| 10075 | NZ | LYS | B | 497 | -13.839 | 25.324 | 79.336 | 1.00 | 52.98 |
| 10076 | C | LYS | B | 497 | -20.778 | 24.064 | 81.422 | 1.00 | 41.98 |
| 10077 | O | LYS | B | 497 | -20.770 | 23.433 | 82.474 | 1.00 | 41.37 |
| 10078 | N | PHE | B | 498 | -21.612 | 23.785 | 80.431 | 1.00 | 40.01 |
| 10079 | CA | PHE | B | 498 | -22.533 | 22.650 | 80.515 | 1.00 | 38.10 |
| 10080 | CB | PHE | B | 498 | -23.934 | 23.108 | 80.887 | 1.00 | 37.53 |
| 10081 | CG | PHE | B | 498 | -24.057 | 23.520 | 82.322 | 1.00 | 35.93 |
| 10082 | CD1 | PHE | B | 498 | -24.063 | 22.569 | 83.326 | 1.00 | 34.06 |
| 10083 | CE1 | PHE | B | 498 | -24.157 | 22.943 | 84.646 | 1.00 | 33.01 |
| 10084 | CZ | PHE | B | 498 | -24.237 | 24.280 | 84.980 | 1.00 | 31.46 |
| 10085 | CE2 | PHE | B | 498 | -24.230 | 25.229 | 83.986 | 1.00 | 32.07 |
| 10086 | CD2 | PHE | B | 498 | -24.123 | 24.857 | 82.672 | 1.00 | 33.44 |
| 10087 | C | PHE | B | 498 | -22.504 | 21.958 | 79.177 | 1.00 | 37.48 |
| 10088 | O | PHE | B | 498 | -22.656 | 22.595 | 78.134 | 1.00 | 38.07 |

FIGURE 3 GP

| A | B | C | D | E | F | G | H | I | J |
|---|---|---|---|---|---|---|---|---|---|
| 10089 | N | TRP | B | 499 | -22.289 | 20.654 | 79.192 | 1.00 | 36.11 |
| 10090 | CA | TRP | B | 499 | -22.099 | 19.941 | 77.944 | 1.00 | 35.50 |
| 10091 | CB | TRP | B | 499 | -21.059 | 18.840 | 78.145 | 1.00 | 35.08 |
| 10092 | CG | TRP | B | 499 | -19.720 | 19.429 | 78.446 | 1.00 | 35.03 |
| 10093 | CD1 | TRP | B | 499 | -19.285 | 19.925 | 79.646 | 1.00 | 32.74 |
| 10094 | NE1 | TRP | B | 499 | -18.009 | 20.413 | 79.510 | 1.00 | 34.52 |
| 10095 | CE2 | TRP | B | 499 | -17.598 | 20.242 | 78.211 | 1.00 | 34.52 |
| 10096 | CD2 | TRP | B | 499 | -18.655 | 19.636 | 77.513 | 1.00 | 34.41 |
| 10097 | CE3 | TRP | B | 499 | -18.481 | 19.344 | 76.156 | 1.00 | 34.27 |
| 10098 | CZ3 | TRP | B | 499 | -17.291 | 19.669 | 75.554 | 1.00 | 35.89 |
| 10099 | CH2 | TRP | B | 499 | -16.256 | 20.275 | 76.277 | 1.00 | 35.53 |
| 10100 | CZ2 | TRP | B | 499 | -16.393 | 20.567 | 77.604 | 1.00 | 34.90 |
| 10101 | C | TRP | B | 499 | -23.376 | 19.375 | 77.348 | 1.00 | 35.10 |
| 10102 | O | TRP | B | 499 | -24.303 | 19.022 | 78.059 | 1.00 | 34.98 |
| 10103 | N | TYR | B | 500 | -23.404 | 19.278 | 76.027 | 1.00 | 34.63 |
| 10104 | CA | TYR | B | 500 | -24.515 | 18.652 | 75.356 | 1.00 | 34.16 |
| 10105 | CB | TYR | B | 500 | -25.501 | 19.714 | 74.887 | 1.00 | 34.31 |
| 10106 | CG | TYR | B | 500 | -24.938 | 20.604 | 73.821 | 1.00 | 34.73 |
| 10107 | CD1 | TYR | B | 500 | -25.082 | 20.289 | 72.479 | 1.00 | 35.98 |
| 10108 | CE1 | TYR | B | 500 | -24.560 | 21.113 | 71.494 | 1.00 | 37.75 |
| 10109 | CZ | TYR | B | 500 | -23.879 | 22.261 | 71.853 | 1.00 | 37.36 |
| 10110 | OH | TYR | B | 500 | -23.362 | 23.085 | 70.876 | 1.00 | 40.04 |
| 10111 | CE2 | TYR | B | 500 | -23.715 | 22.587 | 73.171 | 1.00 | 36.68 |
| 10112 | CD2 | TYR | B | 500 | -24.251 | 21.763 | 74.152 | 1.00 | 36.43 |
| 10113 | C | TYR | B | 500 | -23.976 | 17.918 | 74.157 | 1.00 | 33.95 |
| 10114 | O | TYR | B | 500 | -22.852 | 18.188 | 73.709 | 1.00 | 33.81 |
| 10115 | N | GLN | B | 501 | -24.774 | 16.993 | 73.637 | 1.00 | 33.20 |
| 10116 | CA | GLN | B | 501 | -24.457 | 16.357 | 72.372 | 1.00 | 33.45 |
| 10117 | CB | GLN | B | 501 | -23.984 | 14.895 | 72.526 | 1.00 | 33.76 |
| 10118 | CG | GLN | B | 501 | -25.024 | 13.939 | 73.127 | 1.00 | 33.49 |
| 10119 | CD | GLN | B | 501 | -24.548 | 12.494 | 73.163 | 1.00 | 34.53 |
| 10120 | OE1 | GLN | B | 501 | -23.433 | 12.198 | 73.632 | 1.00 | 33.50 |
| 10121 | NE2 | GLN | B | 501 | -25.388 | 11.588 | 72.670 | 1.00 | 31.69 |
| 10122 | C | GLN | B | 501 | -25.696 | 16.436 | 71.492 | 1.00 | 33.81 |
| 10123 | O | GLN | B | 501 | -26.832 | 16.526 | 71.978 | 1.00 | 33.93 |
| 10124 | N | MET | B | 502 | -25.471 | 16.441 | 70.188 | 1.00 | 33.70 |
| 10125 | CA | MET | B | 502 | -26.562 | 16.410 | 69.250 | 1.00 | 33.82 |
| 10126 | CB | MET | B | 502 | -26.696 | 17.734 | 68.516 | 1.00 | 33.95 |
| 10127 | CG | MET | B | 502 | -27.329 | 18.801 | 69.342 | 1.00 | 33.05 |
| 10128 | SD | MET | B | 502 | -27.201 | 20.315 | 68.472 | 1.00 | 33.25 |
| 10129 | CE | MET | B | 502 | -28.235 | 21.312 | 69.478 | 1.00 | 30.68 |
| 10130 | C | MET | B | 502 | -26.216 | 15.356 | 68.261 | 1.00 | 33.95 |
| 10131 | O | MET | B | 502 | -25.117 | 15.363 | 67.716 | 1.00 | 34.17 |
| 10132 | N | ILE | B | 503 | -27.129 | 14.419 | 68.065 | 1.00 | 33.81 |
| 10133 | CA | ILE | B | 503 | -26.933 | 13.433 | 67.031 | 1.00 | 33.50 |
| 10134 | CB | ILE | B | 503 | -27.669 | 12.136 | 67.366 | 1.00 | 32.92 |
| 10135 | CG1 | ILE | B | 503 | -27.106 | 11.523 | 68.663 | 1.00 | 31.39 |
| 10136 | CD1 | ILE | B | 503 | -25.613 | 11.166 | 68.615 | 1.00 | 27.70 |
| 10137 | CG2 | ILE | B | 503 | -27.564 | 11.150 | 66.215 | 1.00 | 32.58 |
| 10138 | C | ILE | B | 503 | -27.488 | 14.161 | 65.824 | 1.00 | 34.30 |
| 10139 | O | ILE | B | 503 | -28.673 | 14.513 | 65.776 | 1.00 | 34.09 |

FIGURE 3GQ

| A | B | C | D | E | F | G | H | I | J |
|---|---|---|---|---|---|---|---|---|---|
| 10140 | N | LEU | B | 504 | -26.609 | 14.440 | 64.872 | 1.00 | 35.45 |
| 10141 | CA | LEU | B | 504 | -26.972 | 15.267 | 63.726 | 1.00 | 36.12 |
| 10142 | CB | LEU | B | 504 | -25.885 | 16.316 | 63.475 | 1.00 | 36.38 |
| 10143 | CG | LEU | B | 504 | -25.567 | 17.341 | 64.570 | 1.00 | 36.67 |
| 10144 | CD1 | LEU | B | 504 | -24.221 | 17.993 | 64.288 | 1.00 | 35.93 |
| 10145 | CD2 | LEU | B | 504 | -26.659 | 18.404 | 64.706 | 1.00 | 35.45 |
| 10146 | C | LEU | B | 504 | -27.216 | 14.484 | 62.445 | 1.00 | 37.22 |
| 10147 | O | LEU | B | 504 | -26.401 | 13.645 | 62.058 | 1.00 | 37.27 |
| 10148 | N | PRO | B | 505 | -28.351 | 14.760 | 61.799 | 1.00 | 37.60 |
| 10149 | CA | PRO | B | 505 | -28.702 | 14.166 | 60.511 | 1.00 | 38.16 |
| 10150 | CB | PRO | B | 505 | -29.913 | 14.990 | 60.069 | 1.00 | 38.11 |
| 10151 | CG | PRO | B | 505 | -30.500 | 15.517 | 61.311 | 1.00 | 37.73 |
| 10152 | CD | PRO | B | 505 | -29.397 | 15.663 | 62.302 | 1.00 | 37.25 |
| 10153 | C | PRO | B | 505 | -27.595 | 14.368 | 59.486 | 1.00 | 39.24 |
| 10154 | O | PRO | B | 505 | -26.853 | 15.340 | 59.575 | 1.00 | 39.35 |
| 10155 | N | PRO | B | 506 | -27.505 | 13.468 | 58.513 | 1.00 | 39.76 |
| 10156 | CA | PRO | B | 506 | -26.495 | 13.573 | 57.456 | 1.00 | 40.19 |
| 10157 | CB | PRO | B | 506 | -26.768 | 12.367 | 56.548 | 1.00 | 40.20 |
| 10158 | CG | PRO | B | 506 | -27.981 | 11.665 | 57.081 | 1.00 | 40.90 |
| 10159 | CD | PRO | B | 506 | -28.377 | 12.292 | 58.380 | 1.00 | 39.97 |
| 10160 | C | PRO | B | 506 | -26.705 | 14.857 | 56.683 | 1.00 | 40.43 |
| 10161 | O | PRO | B | 506 | -27.818 | 15.365 | 56.687 | 1.00 | 40.64 |
| 10162 | N | HIS | B | 507 | -25.662 | 15.372 | 56.035 | 1.00 | 41.02 |
| 10163 | CA | HIS | B | 507 | -25.761 | 16.622 | 55.288 | 1.00 | 41.46 |
| 10164 | CB | HIS | B | 507 | -26.592 | 16.427 | 54.020 | 1.00 | 41.76 |
| 10165 | CG | HIS | B | 507 | -26.332 | 15.126 | 53.331 | 1.00 | 42.08 |
| 10166 | ND1 | HIS | B | 507 | -25.069 | 14.733 | 52.936 | 1.00 | 42.83 |
| 10167 | CE1 | HIS | B | 507 | -25.138 | 13.543 | 52.366 | 1.00 | 43.44 |
| 10168 | NE2 | HIS | B | 507 | -26.400 | 13.147 | 52.381 | 1.00 | 43.74 |
| 10169 | CD2 | HIS | B | 507 | -27.166 | 14.118 | 52.984 | 1.00 | 42.93 |
| 10170 | C | HIS | B | 507 | -26.387 | 17.696 | 56.157 | 1.00 | 41.97 |
| 10171 | O | HIS | B | 507 | -27.146 | 18.535 | 55.681 | 1.00 | 42.17 |
| 10172 | N | PHE | B | 508 | -26.086 | 17.664 | 57.445 | 1.00 | 42.32 |
| 10173 | CA | PHE | B | 508 | -26.630 | 18.665 | 58.330 | 1.00 | 43.43 |
| 10174 | CB | PHE | B | 508 | -25.972 | 18.611 | 59.698 | 1.00 | 43.24 |
| 10175 | CG | PHE | B | 508 | -26.444 | 19.684 | 60.620 | 1.00 | 44.63 |
| 10176 | CD1 | PHE | B | 508 | -27.774 | 19.754 | 60.990 | 1.00 | 44.60 |
| 10177 | CE1 | PHE | B | 508 | -28.222 | 20.744 | 61.833 | 1.00 | 43.08 |
| 10178 | CZ | PHE | B | 508 | -27.358 | 21.678 | 62.304 | 1.00 | 43.80 |
| 10179 | CE2 | PHE | B | 508 | -26.027 | 21.634 | 61.937 | 1.00 | 44.80 |
| 10180 | CD2 | PHE | B | 508 | -25.574 | 20.643 | 61.095 | 1.00 | 44.57 |
| 10181 | C | PHE | B | 508 | -26.427 | 20.036 | 57.701 | 1.00 | 43.83 |
| 10182 | O | PHE | B | 508 | -25.386 | 20.313 | 57.116 | 1.00 | 44.39 |
| 10183 | N | ASP | B | 509 | -27.421 | 20.896 | 57.828 | 1.00 | 44.40 |
| 10184 | CA | ASP | B | 509 | -27.363 | 22.203 | 57.188 | 1.00 | 44.75 |
| 10185 | CB | ASP | B | 509 | -28.127 | 22.155 | 55.868 | 1.00 | 44.72 |
| 10186 | CG | ASP | B | 509 | -28.252 | 23.510 | 55.212 | 1.00 | 45.91 |
| 10187 | OD1 | ASP | B | 509 | -27.683 | 24.497 | 55.732 | 1.00 | 46.23 |
| 10188 | OD2 | ASP | B | 509 | -28.913 | 23.679 | 54.164 | 1.00 | 47.63 |
| 10189 | C | ASP | B | 509 | -27.936 | 23.261 | 58.108 | 1.00 | 44.61 |
| 10190 | O | ASP | B | 509 | -29.127 | 23.274 | 58.374 | 1.00 | 44.66 |

FIGURE 3 GR

| A | B | C | D | E | F | G | H | I | J |
|---|---|---|---|---|---|---|---|---|---|
| 10191 | N | LYS | B | 510 | -27.072 | 24.143 | 58.589 | 1.00 | 44.90 |
| 10192 | CA | LYS | B | 510 | -27.465 | 25.188 | 59.521 | 1.00 | 45.59 |
| 10193 | CB | LYS | B | 510 | -26.255 | 26.041 | 59.907 | 1.00 | 45.82 |
| 10194 | CG | LYS | B | 510 | -25.350 | 25.406 | 60.973 | 1.00 | 48.45 |
| 10195 | CD | LYS | B | 510 | -24.164 | 26.314 | 61.353 | 1.00 | 50.98 |
| 10196 | CE | LYS | B | 510 | -23.114 | 25.548 | 62.160 | 1.00 | 54.17 |
| 10197 | NZ | LYS | B | 510 | -21.726 | 26.131 | 62.006 | 1.00 | 56.04 |
| 10198 | C | LYS | B | 510 | -28.601 | 26.078 | 59.002 | 1.00 | 45.45 |
| 10199 | O | LYS | B | 510 | -29.243 | 26.788 | 59.777 | 1.00 | 45.44 |
| 10200 | N | SER | B | 511 | -28.847 | 26.042 | 57.699 | 1.00 | 45.26 |
| 10201 | CA | SER | B | 511 | -29.916 | 26.848 | 57.118 | 1.00 | 45.33 |
| 10202 | CB | SER | B | 511 | -29.769 | 26.907 | 55.599 | 1.00 | 45.41 |
| 10203 | OG | SER | B | 511 | -28.785 | 27.866 | 55.242 | 1.00 | 47.44 |
| 10204 | C | SER | B | 511 | -31.302 | 26.332 | 57.482 | 1.00 | 44.83 |
| 10205 | O | SER | B | 511 | -32.235 | 27.106 | 57.662 | 1.00 | 44.80 |
| 10206 | N | LYS | B | 512 | -31.430 | 25.016 | 57.606 | 1.00 | 44.34 |
| 10207 | CA | LYS | B | 512 | -32.727 | 24.407 | 57.881 | 1.00 | 43.64 |
| 10208 | CB | LYS | B | 512 | -32.697 | 22.921 | 57.507 | 1.00 | 43.69 |
| 10209 | CG | LYS | B | 512 | -33.042 | 22.624 | 56.053 | 1.00 | 45.86 |
| 10210 | CD | LYS | B | 512 | -32.208 | 23.433 | 55.078 | 1.00 | 49.67 |
| 10211 | CE | LYS | B | 512 | -32.465 | 23.007 | 53.615 | 1.00 | 52.34 |
| 10212 | NZ | LYS | B | 512 | -33.916 | 23.051 | 53.239 | 1.00 | 52.55 |
| 10213 | C | LYS | B | 512 | -33.176 | 24.551 | 59.332 | 1.00 | 42.70 |
| 10214 | O | LYS | B | 512 | -32.418 | 24.980 | 60.200 | 1.00 | 42.13 |
| 10215 | N | LYS | B | 513 | -34.430 | 24.187 | 59.573 | 1.00 | 41.79 |
| 10216 | CA | LYS | B | 513 | -34.991 | 24.138 | 60.913 | 1.00 | 40.90 |
| 10217 | CB | LYS | B | 513 | -36.204 | 25.061 | 61.041 | 1.00 | 40.56 |
| 10218 | CG | LYS | B | 513 | -35.900 | 26.538 | 60.747 | 1.00 | 42.83 |
| 10219 | CD | LYS | B | 513 | -34.975 | 27.148 | 61.804 | 1.00 | 44.80 |
| 10220 | CE | LYS | B | 513 | -34.335 | 28.445 | 61.310 | 1.00 | 47.34 |
| 10221 | NZ | LYS | B | 513 | -33.346 | 28.208 | 60.191 | 1.00 | 48.84 |
| 10222 | C | LYS | B | 513 | -35.403 | 22.688 | 61.160 | 1.00 | 39.90 |
| 10223 | O | LYS | B | 513 | -36.470 | 22.255 | 60.723 | 1.00 | 40.55 |
| 10224 | N | TYR | B | 514 | -34.559 | 21.930 | 61.842 | 1.00 | 38.20 |
| 10225 | CA | TYR | B | 514 | -34.866 | 20.529 | 62.111 | 1.00 | 36.29 |
| 10226 | CB | TYR | B | 514 | -33.594 | 19.733 | 62.310 | 1.00 | 36.16 |
| 10227 | CG | TYR | B | 514 | -32.702 | 19.673 | 61.100 | 1.00 | 36.91 |
| 10228 | CD1 | TYR | B | 514 | -32.789 | 18.618 | 60.213 | 1.00 | 36.68 |
| 10229 | CE1 | TYR | B | 514 | -31.979 | 18.555 | 59.116 | 1.00 | 38.01 |
| 10230 | CZ | TYR | B | 514 | -31.049 | 19.551 | 58.894 | 1.00 | 37.95 |
| 10231 | OH | TYR | B | 514 | -30.245 | 19.466 | 57.794 | 1.00 | 40.53 |
| 10232 | CE2 | TYR | B | 514 | -30.928 | 20.610 | 59.757 | 1.00 | 37.42 |
| 10233 | CD2 | TYR | B | 514 | -31.741 | 20.667 | 60.863 | 1.00 | 37.50 |
| 10234 | C | TYR | B | 514 | -35.681 | 20.389 | 63.370 | 1.00 | 35.23 |
| 10235 | O | TYR | B | 514 | -35.557 | 21.194 | 64.295 | 1.00 | 34.65 |
| 10236 | N | PRO | B | 515 | -36.525 | 19.371 | 63.401 | 1.00 | 34.07 |
| 10237 | CA | PRO | B | 515 | -37.268 | 19.055 | 64.613 | 1.00 | 33.42 |
| 10238 | CB | PRO | B | 515 | -38.158 | 17.891 | 64.197 | 1.00 | 33.93 |
| 10239 | CG | PRO | B | 515 | -38.038 | 17.776 | 62.714 | 1.00 | 33.47 |
| 10240 | CD | PRO | B | 515 | -36.819 | 18.460 | 62.287 | 1.00 | 33.86 |
| 10241 | C | PRO | B | 515 | -36.213 | 18.584 | 65.596 | 1.00 | 32.62 |

FIGURE 3 GS

| A | B | C | D | E | F | G | H | I | J |
|---|---|---|---|---|---|---|---|---|---|
| 10242 | O | PRO | B | 515 | -35.150 | 18.138 | 65.180 | 1.00 | 31.56 |
| 10243 | N | LEU | B | 516 | -36.473 | 18.708 | 66.882 | 1.00 | 31.86 |
| 10244 | CA | LEU | B | 516 | -35.468 | 18.323 | 67.834 | 1.00 | 31.62 |
| 10245 | CB | LEU | B | 516 | -34.798 | 19.553 | 68.440 | 1.00 | 31.58 |
| 10246 | CG | LEU | B | 516 | -33.658 | 19.190 | 69.396 | 1.00 | 32.56 |
| 10247 | CD1 | LEU | B | 516 | -34.157 | 19.079 | 70.822 | 1.00 | 33.59 |
| 10248 | CD2 | LEU | B | 516 | -32.496 | 20.191 | 69.315 | 1.00 | 32.53 |
| 10249 | C | LEU | B | 516 | -36.059 | 17.476 | 68.932 | 1.00 | 30.89 |
| 10250 | O | LEU | B | 516 | -37.063 | 17.844 | 69.537 | 1.00 | 31.00 |
| 10251 | N | LEU | B | 517 | -35.420 | 16.345 | 69.182 | 1.00 | 30.15 |
| 10252 | CA | LEU | B | 517 | -35.787 | 15.490 | 70.293 | 1.00 | 29.98 |
| 10253 | CB | LEU | B | 517 | -35.843 | 14.026 | 69.852 | 1.00 | 30.15 |
| 10254 | CG | LEU | B | 517 | -36.336 | 13.035 | 70.903 | 1.00 | 29.99 |
| 10255 | CD1 | LEU | B | 517 | -36.296 | 11.620 | 70.333 | 1.00 | 30.41 |
| 10256 | CD2 | LEU | B | 517 | -37.741 | 13.368 | 71.320 | 1.00 | 29.68 |
| 10257 | C | LEU | B | 517 | -34.748 | 15.631 | 71.389 | 1.00 | 29.32 |
| 10258 | O | LEU | B | 517 | -33.571 | 15.417 | 71.150 | 1.00 | 29.44 |
| 10259 | N | LEU | B | 518 | -35.184 | 16.005 | 72.585 | 1.00 | 29.05 |
| 10260 | CA | LEU | B | 518 | -34.300 | 16.059 | 73.734 | 1.00 | 28.73 |
| 10261 | CB | LEU | B | 518 | -34.741 | 17.159 | 74.703 | 1.00 | 28.96 |
| 10262 | CG | LEU | B | 518 | -33.841 | 17.523 | 75.885 | 1.00 | 29.85 |
| 10263 | CD1 | LEU | B | 518 | -32.389 | 17.709 | 75.444 | 1.00 | 29.17 |
| 10264 | CD2 | LEU | B | 518 | -34.365 | 18.774 | 76.613 | 1.00 | 29.61 |
| 10265 | C | LEU | B | 518 | -34.346 | 14.689 | 74.398 | 1.00 | 28.44 |
| 10266 | O | LEU | B | 518 | -35.366 | 14.284 | 74.941 | 1.00 | 28.38 |
| 10267 | N | ASP | B | 519 | -33.245 | 13.955 | 74.310 | 1.00 | 28.13 |
| 10268 | CA | ASP | B | 519 | -33.141 | 12.639 | 74.920 | 1.00 | 27.66 |
| 10269 | CB | ASP | B | 519 | -32.203 | 11.782 | 74.053 | 1.00 | 27.46 |
| 10270 | CG | ASP | B | 519 | -31.791 | 10.492 | 74.719 | 1.00 | 28.03 |
| 10271 | OD1 | ASP | B | 519 | -31.132 | 9.700 | 74.021 | 1.00 | 25.81 |
| 10272 | OD2 | ASP | B | 519 | -32.072 | 10.188 | 75.924 | 1.00 | 27.65 |
| 10273 | C | ASP | B | 519 | -32.558 | 12.898 | 76.305 | 1.00 | 27.39 |
| 10274 | O | ASP | B | 519 | -31.413 | 13.291 | 76.423 | 1.00 | 27.33 |
| 10275 | N | VAL | B | 520 | -33.335 | 12.683 | 77.359 | 1.00 | 27.69 |
| 10276 | CA | VAL | B | 520 | -32.869 | 13.044 | 78.687 | 1.00 | 27.22 |
| 10277 | CB | VAL | B | 520 | -33.750 | 14.180 | 79.309 | 1.00 | 28.16 |
| 10278 | CG1 | VAL | B | 520 | -35.117 | 13.662 | 79.702 | 1.00 | 28.43 |
| 10279 | CG2 | VAL | B | 520 | -33.916 | 15.325 | 78.315 | 1.00 | 29.01 |
| 10280 | C | VAL | B | 520 | -32.805 | 11.920 | 79.676 | 1.00 | 26.59 |
| 10281 | O | VAL | B | 520 | -33.569 | 10.970 | 79.594 | 1.00 | 26.43 |
| 10282 | N | TYR | B | 521 | -31.841 | 12.018 | 80.588 | 1.00 | 26.09 |
| 10283 | CA | TYR | B | 521 | -31.785 | 11.154 | 81.746 | 1.00 | 26.06 |
| 10284 | CB | TYR | B | 521 | -30.607 | 10.166 | 81.703 | 1.00 | 26.25 |
| 10285 | CG | TYR | B | 521 | -30.722 | 9.201 | 82.845 | 1.00 | 26.80 |
| 10286 | CD1 | TYR | B | 521 | -29.919 | 9.323 | 83.962 | 1.00 | 27.78 |
| 10287 | CE1 | TYR | B | 521 | -30.055 | 8.459 | 85.041 | 1.00 | 28.23 |
| 10288 | CZ | TYR | B | 521 | -31.026 | 7.491 | 85.020 | 1.00 | 27.94 |
| 10289 | OH | TYR | B | 521 | -31.163 | 6.653 | 86.098 | 1.00 | 28.80 |
| 10290 | CE2 | TYR | B | 521 | -31.862 | 7.369 | 83.929 | 1.00 | 25.85 |
| 10291 | CD2 | TYR | B | 521 | -31.706 | 8.225 | 82.852 | 1.00 | 26.01 |
| 10292 | C | TYR | B | 521 | -31.747 | 12.111 | 82.962 | 1.00 | 26.26 |

FIGURE 3 GT

| A | B | C | D | E | F | G | H | I | J |
|---|---|---|---|---|---|---|---|---|---|
| 10293 | O | TYR | B | 521 | -32.742 | 12.272 | 83.694 | 1.00 | 25.89 |
| 10294 | N | ALA | B | 522 | -30.606 | 12.765 | 83.163 | 1.00 | 26.30 |
| 10295 | CA | ALA | B | 522 | -30.495 | 13.860 | 84.125 | 1.00 | 26.18 |
| 10296 | CB | ALA | B | 522 | -31.546 | 14.942 | 83.835 | 1.00 | 25.81 |
| 10297 | C | ALA | B | 522 | -30.498 | 13.539 | 85.594 | 1.00 | 26.17 |
| 10298 | O | ALA | B | 522 | -30.602 | 14.440 | 86.425 | 1.00 | 26.60 |
| 10299 | N | GLY | B | 523 | -30.401 | 12.274 | 85.937 | 1.00 | 26.31 |
| 10300 | CA | GLY | B | 523 | -30.338 | 11.921 | 87.335 | 1.00 | 27.13 |
| 10301 | C | GLY | B | 523 | -29.029 | 12.405 | 87.919 | 1.00 | 27.75 |
| 10302 | O | GLY | B | 523 | -28.157 | 12.886 | 87.200 | 1.00 | 28.22 |
| 10303 | N | PRO | B | 524 | -28.886 | 12.278 | 89.228 | 1.00 | 28.62 |
| 10304 | CA | PRO | B | 524 | -27.662 | 12.695 | 89.924 | 1.00 | 28.81 |
| 10305 | CB | PRO | B | 524 | -27.983 | 12.390 | 91.385 | 1.00 | 28.77 |
| 10306 | CG | PRO | B | 524 | -29.455 | 12.370 | 91.450 | 1.00 | 29.35 |
| 10307 | CD | PRO | B | 524 | -29.901 | 11.744 | 90.150 | 1.00 | 28.51 |
| 10308 | C | PRO | B | 524 | -26.425 | 11.909 | 89.470 | 1.00 | 29.28 |
| 10309 | O | PRO | B | 524 | -26.421 | 10.682 | 89.522 | 1.00 | 30.13 |
| 10310 | N | CYS | B | 525 | -25.397 | 12.631 | 89.028 | 1.00 | 29.43 |
| 10311 | CA | CYS | B | 525 | -24.117 | 12.091 | 88.536 | 1.00 | 29.13 |
| 10312 | CB | CYS | B | 525 | -23.443 | 11.139 | 89.530 | 1.00 | 29.46 |
| 10313 | SG | CYS | B | 525 | -21.704 | 10.843 | 89.134 | 1.00 | 30.55 |
| 10314 | C | CYS | B | 525 | -24.244 | 11.431 | 87.187 | 1.00 | 29.15 |
| 10315 | O | CYS | B | 525 | -23.481 | 10.528 | 86.845 | 1.00 | 28.81 |
| 10316 | N | SER | B | 526 | -25.207 | 11.889 | 86.398 | 1.00 | 28.96 |
| 10317 | CA | SER | B | 526 | -25.404 | 11.293 | 85.092 | 1.00 | 28.33 |
| 10318 | CB | SER | B | 526 | -26.889 | 11.309 | 84.702 | 1.00 | 28.66 |
| 10319 | OG | SER | B | 526 | -27.392 | 12.622 | 84.545 | 1.00 | 28.53 |
| 10320 | C | SER | B | 526 | -24.583 | 12.037 | 84.075 | 1.00 | 28.00 |
| 10321 | O | SER | B | 526 | -24.109 | 13.141 | 84.343 | 1.00 | 28.49 |
| 10322 | N | GLN | B | 527 | -24.400 | 11.407 | 82.924 | 1.00 | 27.24 |
| 10323 | CA | GLN | B | 527 | -23.727 | 11.993 | 81.789 | 1.00 | 27.34 |
| 10324 | CB | GLN | B | 527 | -22.260 | 11.587 | 81.733 | 1.00 | 27.44 |
| 10325 | CG | GLN | B | 527 | -21.465 | 12.350 | 80.679 | 1.00 | 27.08 |
| 10326 | CD | GLN | B | 527 | -19.965 | 12.274 | 80.926 | 1.00 | 29.58 |
| 10327 | OE1 | GLN | B | 527 | -19.366 | 11.178 | 80.858 | 1.00 | 31.47 |
| 10328 | NE2 | GLN | B | 527 | -19.353 | 13.421 | 81.239 | 1.00 | 25.86 |
| 10329 | C | GLN | B | 527 | -24.394 | 11.465 | 80.545 | 1.00 | 27.56 |
| 10330 | O | GLN | B | 527 | -24.386 | 10.254 | 80.293 | 1.00 | 27.51 |
| 10331 | N | LYS | B | 528 | -24.954 | 12.377 | 79.769 | 1.00 | 27.53 |
| 10332 | CA | LYS | B | 528 | -25.605 | 12.032 | 78.532 | 1.00 | 28.34 |
| 10333 | CB | LYS | B | 528 | -27.076 | 12.468 | 78.572 | 1.00 | 28.03 |
| 10334 | CG | LYS | B | 528 | -27.939 | 11.562 | 79.420 | 1.00 | 26.85 |
| 10335 | CD | LYS | B | 528 | -28.288 | 10.281 | 78.656 | 1.00 | 26.78 |
| 10336 | CE | LYS | B | 528 | -29.609 | 10.442 | 77.855 | 1.00 | 27.00 |
| 10337 | NZ | LYS | B | 528 | -29.895 | 9.276 | 76.941 | 1.00 | 25.88 |
| 10338 | C | LYS | B | 528 | -24.887 | 12.715 | 77.403 | 1.00 | 28.93 |
| 10339 | O | LYS | B | 528 | -25.200 | 12.509 | 76.242 | 1.00 | 29.39 |
| 10340 | N | ALA | B | 529 | -23.930 | 13.554 | 77.751 | 1.00 | 30.32 |
| 10341 | CA | ALA | B | 529 | -23.156 | 14.276 | 76.752 | 1.00 | 31.84 |
| 10342 | CB | ALA | B | 529 | -22.910 | 15.703 | 77.219 | 1.00 | 32.18 |
| 10343 | C | ALA | B | 529 | -21.859 | 13.507 | 76.669 | 1.00 | 32.41 |

FIGURE 3 GU

| A | B | C | D | E | F | G | H | I | J |
|---|---|---|---|---|---|---|---|---|---|
| 10344 | O | ALA | B | 529 | -21.059 | 13.567 | 77.600 | 1.00 | 33.03 |
| 10345 | N | ASP | B | 530 | -21.653 | 12.815 | 75.549 | 1.00 | 32.75 |
| 10346 | CA | ASP | B | 530 | -20.595 | 11.810 | 75.425 | 1.00 | 33.61 |
| 10347 | CB | ASP | B | 530 | -21.257 | 10.422 | 75.322 | 1.00 | 34.27 |
| 10348 | CG | ASP | B | 530 | -21.175 | 9.709 | 76.570 | 1.00 | 36.90 |
| 10349 | OD1 | ASP | B | 530 | -20.366 | 10.203 | 77.388 | 1.00 | 42.89 |
| 10350 | OD2 | ASP | B | 530 | -21.849 | 8.710 | 76.862 | 1.00 | 38.24 |
| 10351 | C | ASP | B | 530 | -19.677 | 11.829 | 74.237 | 1.00 | 33.01 |
| 10352 | O | ASP | B | 530 | -19.952 | 12.402 | 73.201 | 1.00 | 33.23 |
| 10353 | N | THR | B | 531 | -18.634 | 11.045 | 74.378 | 1.00 | 31.98 |
| 10354 | CA | THR | B | 531 | -17.716 | 10.815 | 73.309 | 1.00 | 31.94 |
| 10355 | CB | THR | B | 531 | -16.300 | 10.963 | 73.904 | 1.00 | 32.42 |
| 10356 | OG1 | THR | B | 531 | -15.716 | 12.177 | 73.405 | 1.00 | 32.61 |
| 10357 | CG2 | THR | B | 531 | -15.397 | 9.869 | 73.441 | 1.00 | 31.77 |
| 10358 | C | THR | B | 531 | -17.994 | 9.423 | 72.682 | 1.00 | 31.71 |
| 10359 | O | THR | B | 531 | -17.361 | 9.020 | 71.711 | 1.00 | 32.01 |
| 10360 | N | VAL | B | 532 | -18.993 | 8.716 | 73.209 | 1.00 | 31.31 |
| 10361 | CA | VAL | B | 532 | -19.307 | 7.354 | 72.763 | 1.00 | 30.28 |
| 10362 | CB | VAL | B | 532 | -20.103 | 6.599 | 73.846 | 1.00 | 30.52 |
| 10363 | CG1 | VAL | B | 532 | -20.431 | 5.169 | 73.390 | 1.00 | 28.75 |
| 10364 | CG2 | VAL | B | 532 | -19.338 | 6.602 | 75.166 | 1.00 | 28.66 |
| 10365 | C | VAL | B | 532 | -20.057 | 7.203 | 71.437 | 1.00 | 30.03 |
| 10366 | O | VAL | B | 532 | -21.003 | 7.939 | 71.145 | 1.00 | 29.85 |
| 10367 | N | PHE | B | 533 | -19.628 | 6.225 | 70.643 | 1.00 | 29.69 |
| 10368 | CA | PHE | B | 533 | -20.300 | 5.885 | 69.393 | 1.00 | 29.92 |
| 10369 | CB | PHE | B | 533 | -19.333 | 5.270 | 68.387 | 1.00 | 29.69 |
| 10370 | CG | PHE | B | 533 | -20.000 | 4.842 | 67.109 | 1.00 | 30.85 |
| 10371 | CD1 | PHE | B | 533 | -20.391 | 5.783 | 66.164 | 1.00 | 31.21 |
| 10372 | CE1 | PHE | B | 533 | -21.010 | 5.391 | 64.992 | 1.00 | 31.70 |
| 10373 | CZ | PHE | B | 533 | -21.244 | 4.055 | 64.754 | 1.00 | 31.59 |
| 10374 | CE2 | PHE | B | 533 | -20.863 | 3.119 | 65.685 | 1.00 | 32.15 |
| 10375 | CD2 | PHE | B | 533 | -20.251 | 3.511 | 66.855 | 1.00 | 30.29 |
| 10376 | C | PHE | B | 533 | -21.438 | 4.892 | 69.624 | 1.00 | 29.79 |
| 10377 | O | PHE | B | 533 | -21.234 | 3.836 | 70.234 | 1.00 | 29.95 |
| 10378 | N | ARG | B | 534 | -22.629 | 5.217 | 69.116 | 1.00 | 29.94 |
| 10379 | CA | ARG | B | 534 | -23.802 | 4.355 | 69.313 | 1.00 | 29.47 |
| 10380 | CB | ARG | B | 534 | -24.746 | 4.941 | 70.382 | 1.00 | 29.69 |
| 10381 | CG | ARG | B | 534 | -24.083 | 5.232 | 71.717 | 1.00 | 30.30 |
| 10382 | CD | ARG | B | 534 | -25.055 | 5.408 | 72.882 | 1.00 | 30.50 |
| 10383 | NE | ARG | B | 534 | -24.534 | 6.379 | 73.830 | 1.00 | 33.78 |
| 10384 | CZ | ARG | B | 534 | -23.814 | 6.069 | 74.886 | 1.00 | 34.14 |
| 10385 | NH1 | ARG | B | 534 | -23.566 | 4.795 | 75.163 | 1.00 | 38.43 |
| 10386 | NH2 | ARG | B | 534 | -23.360 | 7.015 | 75.673 | 1.00 | 28.76 |
| 10387 | C | ARG | B | 534 | -24.615 | 4.101 | 68.052 | 1.00 | 29.10 |
| 10388 | O | ARG | B | 534 | -24.753 | 4.958 | 67.182 | 1.00 | 28.45 |
| 10389 | N | LEU | B | 535 | -25.160 | 2.897 | 67.971 | 1.00 | 28.76 |
| 10390 | CA | LEU | B | 535 | -26.099 | 2.562 | 66.924 | 1.00 | 28.27 |
| 10391 | CB | LEU | B | 535 | -25.647 | 1.339 | 66.162 | 1.00 | 27.84 |
| 10392 | CG | LEU | B | 535 | -24.323 | 1.513 | 65.428 | 1.00 | 28.86 |
| 10393 | CD1 | LEU | B | 535 | -23.984 | 0.272 | 64.628 | 1.00 | 27.87 |
| 10394 | CD2 | LEU | B | 535 | -24.397 | 2.736 | 64.523 | 1.00 | 28.04 |

FIGURE 3 GV

| A | B | C | D | E | F | G | H | I | J |
|---|---|---|---|---|---|---|---|---|---|
| 10395 | C | LEU | B | 535 | -27.354 | 2.269 | 67.707 | 1.00 | 28.36 |
| 10396 | O | LEU | B | 535 | -27.497 | 1.183 | 68.281 | 1.00 | 28.59 |
| 10397 | N | ASN | B | 536 | -28.239 | 3.258 | 67.771 | 1.00 | 27.55 |
| 10398 | CA | ASN | B | 536 | -29.443 | 3.159 | 68.578 | 1.00 | 27.33 |
| 10399 | CB | ASN | B | 536 | -29.183 | 3.733 | 69.983 | 1.00 | 27.21 |
| 10400 | CG | ASN | B | 536 | -28.799 | 5.208 | 69.946 | 1.00 | 26.48 |
| 10401 | OD1 | ASN | B | 536 | -28.718 | 5.803 | 68.880 | 1.00 | 26.35 |
| 10402 | ND2 | ASN | B | 536 | -28.564 | 5.800 | 71.113 | 1.00 | 25.63 |
| 10403 | C | ASN | B | 536 | -30.620 | 3.883 | 67.953 | 1.00 | 27.21 |
| 10404 | O | ASN | B | 536 | -30.562 | 4.331 | 66.817 | 1.00 | 27.61 |
| 10405 | N | TRP | B | 537 | -31.698 | 4.006 | 68.706 | 1.00 | 27.52 |
| 10406 | CA | TRP | B | 537 | -32.875 | 4.680 | 68.190 | 1.00 | 27.56 |
| 10407 | CB | TRP | B | 537 | -33.956 | 4.692 | 69.254 | 1.00 | 27.37 |
| 10408 | CG | TRP | B | 537 | -35.300 | 5.118 | 68.741 | 1.00 | 26.25 |
| 10409 | CD1 | TRP | B | 537 | -35.942 | 4.662 | 67.625 | 1.00 | 25.40 |
| 10410 | NE1 | TRP | B | 537 | -37.153 | 5.291 | 67.485 | 1.00 | 24.25 |
| 10411 | CE2 | TRP | B | 537 | -37.318 | 6.163 | 68.524 | 1.00 | 24.30 |
| 10412 | CD2 | TRP | B | 537 | -36.158 | 6.078 | 69.333 | 1.00 | 25.96 |
| 10413 | CE3 | TRP | B | 537 | -36.078 | 6.880 | 70.487 | 1.00 | 24.95 |
| 10414 | CZ3 | TRP | B | 537 | -37.135 | 7.719 | 70.782 | 1.00 | 23.71 |
| 10415 | CH2 | TRP | B | 537 | -38.275 | 7.768 | 69.953 | 1.00 | 24.08 |
| 10416 | CZ2 | TRP | B | 537 | -38.382 | 6.994 | 68.828 | 1.00 | 22.33 |
| 10417 | C | TRP | B | 537 | -32.542 | 6.113 | 67.731 | 1.00 | 27.79 |
| 10418 | O | TRP | B | 537 | -33.000 | 6.557 | 66.687 | 1.00 | 28.32 |
| 10419 | N | ALA | B | 538 | -31.727 | 6.829 | 68.498 | 1.00 | 27.68 |
| 10420 | CA | ALA | B | 538 | -31.332 | 8.186 | 68.094 | 1.00 | 27.27 |
| 10421 | CB | ALA | B | 538 | -30.361 | 8.803 | 69.110 | 1.00 | 26.36 |
| 10422 | C | ALA | B | 538 | -30.701 | 8.143 | 66.714 | 1.00 | 27.27 |
| 10423 | O | ALA | B | 538 | -30.956 | 8.991 | 65.878 | 1.00 | 27.73 |
| 10424 | N | THR | B | 539 | -29.882 | 7.138 | 66.456 | 1.00 | 27.11 |
| 10425 | CA | THR | B | 539 | -29.237 | 7.056 | 65.158 | 1.00 | 27.29 |
| 10426 | CB | THR | B | 539 | -28.390 | 5.777 | 65.095 | 1.00 | 27.30 |
| 10427 | OG1 | THR | B | 539 | -27.573 | 5.698 | 66.270 | 1.00 | 27.43 |
| 10428 | CG2 | THR | B | 539 | -27.383 | 5.866 | 63.962 | 1.00 | 26.66 |
| 10429 | C | THR | B | 539 | -30.253 | 7.059 | 64.013 | 1.00 | 27.41 |
| 10430 | O | THR | B | 539 | -30.097 | 7.794 | 63.041 | 1.00 | 28.14 |
| 10431 | N | TYR | B | 540 | -31.270 | 6.202 | 64.121 | 1.00 | 27.11 |
| 10432 | CA | TYR | B | 540 | -32.339 | 6.125 | 63.122 | 1.00 | 26.32 |
| 10433 | CB | TYR | B | 540 | -33.311 | 4.961 | 63.466 | 1.00 | 25.83 |
| 10434 | CG | TYR | B | 540 | -34.783 | 5.253 | 63.168 | 1.00 | 24.15 |
| 10435 | CD1 | TYR | B | 540 | -35.706 | 5.430 | 64.193 | 1.00 | 22.96 |
| 10436 | CE1 | TYR | B | 540 | -37.043 | 5.678 | 63.919 | 1.00 | 22.68 |
| 10437 | CZ | TYR | B | 540 | -37.464 | 5.787 | 62.608 | 1.00 | 23.79 |
| 10438 | OH | TYR | B | 540 | -38.765 | 6.064 | 62.302 | 1.00 | 23.93 |
| 10439 | CE2 | TYR | B | 540 | -36.568 | 5.643 | 61.577 | 1.00 | 25.15 |
| 10440 | CD2 | TYR | B | 540 | -35.228 | 5.376 | 61.864 | 1.00 | 23.64 |
| 10441 | C | TYR | B | 540 | -33.107 | 7.447 | 62.980 | 1.00 | 26.37 |
| 10442 | O | TYR | B | 540 | -33.390 | 7.891 | 61.871 | 1.00 | 26.82 |
| 10443 | N | LEU | B | 541 | -33.455 | 8.067 | 64.105 | 1.00 | 26.28 |
| 10444 | CA | LEU | B | 541 | -34.247 | 9.293 | 64.091 | 1.00 | 26.66 |
| 10445 | CB | LEU | B | 541 | -34.497 | 9.784 | 65.513 | 1.00 | 26.15 |

FIGURE 3 GW

| A | B | C | D | E | F | G | H | I | J |
|---|---|---|---|---|---|---|---|---|---|
| 10446 | CG | LEU | B | 541 | -35.466 | 9.000 | 66.378 | 1.00 | 26.10 |
| 10447 | CD1 | LEU | B | 541 | -35.727 | 9.782 | 67.649 | 1.00 | 26.75 |
| 10448 | CD2 | LEU | B | 541 | -36.758 | 8.750 | 65.620 | 1.00 | 25.54 |
| 10449 | C | LEU | B | 541 | -33.578 | 10.405 | 63.299 | 1.00 | 27.47 |
| 10450 | O | LEU | B | 541 | -34.229 | 11.154 | 62.571 | 1.00 | 27.24 |
| 10451 | N | ALA | B | 542 | -32.268 | 10.518 | 63.466 | 1.00 | 28.12 |
| 10452 | CA | ALA | B | 542 | -31.500 | 11.526 | 62.769 | 1.00 | 29.58 |
| 10453 | CB | ALA | B | 542 | -30.172 | 11.751 | 63.478 | 1.00 | 29.49 |
| 10454 | C | ALA | B | 542 | -31.261 | 11.144 | 61.325 | 1.00 | 30.14 |
| 10455 | O | ALA | B | 542 | -31.455 | 11.962 | 60.423 | 1.00 | 30.83 |
| 10456 | N | SER | B | 543 | -30.869 | 9.891 | 61.114 | 1.00 | 30.58 |
| 10457 | CA | SER | B | 543 | -30.534 | 9.403 | 59.784 | 1.00 | 30.83 |
| 10458 | CB | SER | B | 543 | -29.899 | 8.028 | 59.867 | 1.00 | 30.44 |
| 10459 | OG | SER | B | 543 | -29.501 | 7.617 | 58.576 | 1.00 | 31.51 |
| 10460 | C | SER | B | 543 | -31.668 | 9.326 | 58.797 | 1.00 | 31.21 |
| 10461 | O | SER | B | 543 | -31.550 | 9.789 | 57.670 | 1.00 | 31.31 |
| 10462 | N | THR | B | 544 | -32.759 | 8.687 | 59.205 | 1.00 | 32.02 |
| 10463 | CA | THR | B | 544 | -33.885 | 8.473 | 58.308 | 1.00 | 31.66 |
| 10464 | CB | THR | B | 544 | -34.515 | 7.100 | 58.611 | 1.00 | 32.14 |
| 10465 | OG1 | THR | B | 544 | -33.545 | 6.064 | 58.384 | 1.00 | 32.56 |
| 10466 | CG2 | THR | B | 544 | -35.623 | 6.774 | 57.635 | 1.00 | 31.12 |
| 10467 | C | THR | B | 544 | -34.930 | 9.559 | 58.428 | 1.00 | 31.54 |
| 10468 | O | THR | B | 544 | -35.516 | 9.973 | 57.428 | 1.00 | 32.90 |
| 10469 | N | GLU | B | 545 | -35.171 | 10.028 | 59.645 | 1.00 | 30.93 |
| 10470 | CA | GLU | B | 545 | -36.245 | 10.990 | 59.883 | 1.00 | 30.44 |
| 10471 | CB | GLU | B | 545 | -37.056 | 10.607 | 61.121 | 1.00 | 30.22 |
| 10472 | CG | GLU | B | 545 | -37.476 | 9.154 | 61.168 | 1.00 | 31.17 |
| 10473 | CD | GLU | B | 545 | -38.478 | 8.816 | 60.102 | 1.00 | 31.65 |
| 10474 | OE1 | GLU | B | 545 | -38.805 | 7.626 | 59.945 | 1.00 | 33.03 |
| 10475 | OE2 | GLU | B | 545 | -38.948 | 9.745 | 59.428 | 1.00 | 33.96 |
| 10476 | C | GLU | B | 545 | -35.803 | 12.436 | 60.017 | 1.00 | 30.28 |
| 10477 | O | GLU | B | 545 | -36.647 | 13.314 | 60.231 | 1.00 | 29.86 |
| 10478 | N | ASN | B | 546 | -34.497 | 12.671 | 59.906 | 1.00 | 29.77 |
| 10479 | CA | ASN | B | 546 | -33.925 | 14.024 | 59.972 | 1.00 | 29.94 |
| 10480 | CB | ASN | B | 546 | -34.234 | 14.834 | 58.725 | 1.00 | 29.97 |
| 10481 | CG | ASN | B | 546 | -33.620 | 14.232 | 57.488 | 1.00 | 31.87 |
| 10482 | OD1 | ASN | B | 546 | -34.321 | 13.778 | 56.591 | 1.00 | 33.83 |
| 10483 | ND2 | ASN | B | 546 | -32.299 | 14.218 | 57.434 | 1.00 | 35.28 |
| 10484 | C | ASN | B | 546 | -34.281 | 14.807 | 61.213 | 1.00 | 29.50 |
| 10485 | O | ASN | B | 546 | -34.498 | 16.019 | 61.169 | 1.00 | 30.14 |
| 10486 | N | ILE | B | 547 | -34.333 | 14.100 | 62.326 | 1.00 | 29.19 |
| 10487 | CA | ILE | B | 547 | -34.577 | 14.721 | 63.609 | 1.00 | 28.81 |
| 10488 | CB | ILE | B | 547 | -35.426 | 13.787 | 64.492 | 1.00 | 28.59 |
| 10489 | CG1 | ILE | B | 547 | -36.751 | 13.460 | 63.803 | 1.00 | 26.88 |
| 10490 | CD1 | ILE | B | 547 | -37.627 | 12.520 | 64.592 | 1.00 | 25.63 |
| 10491 | CG2 | ILE | B | 547 | -35.654 | 14.432 | 65.856 | 1.00 | 26.86 |
| 10492 | C | ILE | B | 547 | -33.225 | 14.903 | 64.264 | 1.00 | 28.95 |
| 10493 | O | ILE | B | 547 | -32.350 | 14.055 | 64.125 | 1.00 | 29.39 |
| 10494 | N | ILE | B | 548 | -33.032 | 16.009 | 64.960 | 1.00 | 29.52 |
| 10495 | CA | ILE | B | 548 | -31.813 | 16.163 | 65.719 | 1.00 | 29.91 |
| 10496 | CB | ILE | B | 548 | -31.404 | 17.636 | 65.803 | 1.00 | 30.67 |

FIGURE 3 GX

| A | B | C | D | E | F | G | H | I | J |
|---|---|---|---|---|---|---|---|---|---|
| 10497 | CG1 | ILE | B | 548 | -31.059 | 18.186 | 64.416 | 1.00 | 31.31 |
| 10498 | CD1 | ILE | B | 548 | -30.815 | 19.719 | 64.396 | 1.00 | 32.35 |
| 10499 | CG2 | ILE | B | 548 | -30.218 | 17.811 | 66.750 | 1.00 | 29.86 |
| 10500 | C | ILE | B | 548 | -32.144 | 15.633 | 67.093 | 1.00 | 29.97 |
| 10501 | O | ILE | B | 548 | -33.183 | 15.963 | 67.645 | 1.00 | 30.56 |
| 10502 | N | VAL | B | 549 | -31.303 | 14.770 | 67.642 | 1.00 | 30.13 |
| 10503 | CA | VAL | B | 549 | -31.552 | 14.325 | 68.995 | 1.00 | 30.10 |
| 10504 | CB | VAL | B | 549 | -31.926 | 12.818 | 69.104 | 1.00 | 30.19 |
| 10505 | CG1 | VAL | B | 549 | -31.532 | 12.071 | 67.867 | 1.00 | 31.17 |
| 10506 | CG2 | VAL | B | 549 | -31.387 | 12.201 | 70.375 | 1.00 | 29.16 |
| 10507 | C | VAL | B | 549 | -30.419 | 14.746 | 69.899 | 1.00 | 30.23 |
| 10508 | O | VAL | B | 549 | -29.253 | 14.390 | 69.700 | 1.00 | 30.38 |
| 10509 | N | ALA | B | 550 | -30.788 | 15.535 | 70.894 | 1.00 | 30.33 |
| 10510 | CA | ALA | B | 550 | -29.828 | 16.148 | 71.775 | 1.00 | 30.46 |
| 10511 | CB | ALA | B | 550 | -30.010 | 17.661 | 71.769 | 1.00 | 30.64 |
| 10512 | C | ALA | B | 550 | -29.939 | 15.652 | 73.177 | 1.00 | 30.61 |
| 10513 | O | ALA | B | 550 | -30.982 | 15.179 | 73.619 | 1.00 | 30.50 |
| 10514 | N | SER | B | 551 | -28.834 | 15.772 | 73.889 | 1.00 | 31.06 |
| 10515 | CA | SER | B | 551 | -28.846 | 15.444 | 75.286 | 1.00 | 31.88 |
| 10516 | CB | SER | B | 551 | -28.313 | 14.033 | 75.517 | 1.00 | 31.90 |
| 10517 | OG | SER | B | 551 | -28.920 | 13.138 | 74.581 | 1.00 | 31.37 |
| 10518 | C | SER | B | 551 | -28.035 | 16.516 | 75.969 | 1.00 | 32.32 |
| 10519 | O | SER | B | 551 | -27.148 | 17.120 | 75.368 | 1.00 | 32.04 |
| 10520 | N | PHE | B | 552 | -28.363 | 16.760 | 77.231 | 1.00 | 32.70 |
| 10521 | CA | PHE | B | 552 | -27.749 | 17.840 | 77.955 | 1.00 | 32.31 |
| 10522 | CB | PHE | B | 552 | -28.668 | 19.055 | 77.881 | 1.00 | 32.17 |
| 10523 | CG | PHE | B | 552 | -28.124 | 20.257 | 78.572 | 1.00 | 32.00 |
| 10524 | CD1 | PHE | B | 552 | -27.188 | 21.067 | 77.939 | 1.00 | 32.75 |
| 10525 | CE1 | PHE | B | 552 | -26.670 | 22.170 | 78.575 | 1.00 | 31.83 |
| 10526 | CZ | PHE | B | 552 | -27.080 | 22.476 | 79.847 | 1.00 | 30.43 |
| 10527 | CE2 | PHE | B | 552 | -28.010 | 21.672 | 80.490 | 1.00 | 32.93 |
| 10528 | CD2 | PHE | B | 552 | -28.528 | 20.573 | 79.852 | 1.00 | 30.89 |
| 10529 | C | PHE | B | 552 | -27.508 | 17.453 | 79.401 | 1.00 | 32.19 |
| 10530 | O | PHE | B | 552 | -28.389 | 16.917 | 80.075 | 1.00 | 32.10 |
| 10531 | N | ASP | B | 553 | -26.293 | 17.702 | 79.862 | 1.00 | 32.28 |
| 10532 | CA | ASP | B | 553 | -25.929 | 17.440 | 81.244 | 1.00 | 32.29 |
| 10533 | CB | ASP | B | 553 | -24.550 | 16.815 | 81.336 | 1.00 | 32.17 |
| 10534 | CG | ASP | B | 553 | -24.469 | 15.471 | 80.649 | 1.00 | 32.77 |
| 10535 | OD1 | ASP | B | 553 | -25.436 | 14.686 | 80.753 | 1.00 | 32.37 |
| 10536 | OD2 | ASP | B | 553 | -23.471 | 15.114 | 79.983 | 1.00 | 33.13 |
| 10537 | C | ASP | B | 553 | -25.939 | 18.777 | 81.963 | 1.00 | 32.26 |
| 10538 | O | ASP | B | 553 | -25.033 | 19.601 | 81.802 | 1.00 | 32.17 |
| 10539 | N | GLY | B | 554 | -26.985 | 19.010 | 82.732 | 1.00 | 31.93 |
| 10540 | CA | GLY | B | 554 | -27.085 | 20.260 | 83.448 | 1.00 | 32.51 |
| 10541 | C | GLY | B | 554 | -26.731 | 20.065 | 84.900 | 1.00 | 32.51 |
| 10542 | O | GLY | B | 554 | -25.998 | 19.146 | 85.268 | 1.00 | 31.81 |
| 10543 | N | ARG | B | 555 | -27.235 | 20.946 | 85.746 | 1.00 | 32.88 |
| 10544 | CA | ARG | B | 555 | -26.933 | 20.781 | 87.146 | 1.00 | 33.51 |
| 10545 | CB | ARG | B | 555 | -27.632 | 21.834 | 87.979 | 1.00 | 33.65 |
| 10546 | CG | ARG | B | 555 | -26.887 | 23.165 | 87.886 | 1.00 | 35.20 |
| 10547 | CD | ARG | B | 555 | -27.614 | 24.317 | 88.459 | 1.00 | 35.52 |

FIGURE 3 GY

| A | B | C | D | E | F | G | H | I | J |
|---|---|---|---|---|---|---|---|---|---|
| 10548 | NE | ARG | B | 555 | -28.703 | 24.722 | 87.584 | 1.00 | 36.97 |
| 10549 | CZ | ARG | B | 555 | -29.567 | 25.663 | 87.907 | 1.00 | 36.91 |
| 10550 | NH1 | ARG | B | 555 | -29.435 | 26.274 | 89.082 | 1.00 | 35.24 |
| 10551 | NH2 | ARG | B | 555 | -30.544 | 25.998 | 87.065 | 1.00 | 35.09 |
| 10552 | C | ARG | B | 555 | -27.318 | 19.374 | 87.515 | 1.00 | 33.51 |
| 10553 | O | ARG | B | 555 | -28.183 | 18.759 | 86.856 | 1.00 | 33.65 |
| 10554 | N | GLY | B | 556 | -26.640 | 18.845 | 88.526 | 1.00 | 33.18 |
| 10555 | CA | GLY | B | 556 | -26.839 | 17.473 | 88.946 | 1.00 | 32.38 |
| 10556 | C | GLY | B | 556 | -25.990 | 16.476 | 88.169 | 1.00 | 32.39 |
| 10557 | O | GLY | B | 556 | -25.766 | 15.373 | 88.644 | 1.00 | 32.12 |
| 10558 | N | SER | B | 557 | -25.513 | 16.843 | 86.981 | 1.00 | 32.66 |
| 10559 | CA | SER | B | 557 | -24.705 | 15.901 | 86.198 | 1.00 | 33.46 |
| 10560 | CB | SER | B | 557 | -24.502 | 16.376 | 84.760 | 1.00 | 33.48 |
| 10561 | OG | SER | B | 557 | -24.336 | 17.779 | 84.695 | 1.00 | 36.23 |
| 10562 | C | SER | B | 557 | -23.372 | 15.544 | 86.871 | 1.00 | 32.98 |
| 10563 | O | SER | B | 557 | -22.917 | 16.247 | 87.775 | 1.00 | 33.03 |
| 10564 | N | GLY | B | 558 | -22.754 | 14.448 | 86.433 | 1.00 | 32.64 |
| 10565 | CA | GLY | B | 558 | -21.533 | 13.973 | 87.058 | 1.00 | 31.98 |
| 10566 | C | GLY | B | 558 | -20.212 | 14.257 | 86.369 | 1.00 | 31.63 |
| 10567 | O | GLY | B | 558 | -20.162 | 14.804 | 85.272 | 1.00 | 30.81 |
| 10568 | N | TYR | B | 559 | -19.122 | 13.907 | 87.051 | 1.00 | 32.06 |
| 10569 | CA | TYR | B | 559 | -17.795 | 13.984 | 86.445 | 1.00 | 32.31 |
| 10570 | CB | TYR | B | 559 | -17.816 | 13.166 | 85.150 | 1.00 | 31.85 |
| 10571 | CG | TYR | B | 559 | -18.466 | 11.824 | 85.389 | 1.00 | 31.91 |
| 10572 | CD1 | TYR | B | 559 | -19.691 | 11.486 | 84.793 | 1.00 | 31.67 |
| 10573 | CE1 | TYR | B | 559 | -20.290 | 10.252 | 85.038 | 1.00 | 31.06 |
| 10574 | CZ | TYR | B | 559 | -19.671 | 9.361 | 85.896 | 1.00 | 31.51 |
| 10575 | OH | TYR | B | 559 | -20.234 | 8.141 | 86.176 | 1.00 | 29.87 |
| 10576 | CE2 | TYR | B | 559 | -18.474 | 9.695 | 86.507 | 1.00 | 32.01 |
| 10577 | CD2 | TYR | B | 559 | -17.887 | 10.918 | 86.251 | 1.00 | 30.62 |
| 10578 | C | TYR | B | 559 | -17.313 | 15.415 | 86.184 | 1.00 | 32.86 |
| 10579 | O | TYR | B | 559 | -16.400 | 15.627 | 85.384 | 1.00 | 33.13 |
| 10580 | N | GLN | B | 560 | -17.931 | 16.392 | 86.843 | 1.00 | 33.01 |
| 10581 | CA | GLN | B | 560 | -17.527 | 17.777 | 86.663 | 1.00 | 33.99 |
| 10582 | CB | GLN | B | 560 | -18.528 | 18.546 | 85.815 | 1.00 | 34.05 |
| 10583 | CG | GLN | B | 560 | -18.688 | 18.047 | 84.421 | 1.00 | 34.49 |
| 10584 | CD | GLN | B | 560 | -20.057 | 18.380 | 83.874 | 1.00 | 35.71 |
| 10585 | OE1 | GLN | B | 560 | -20.234 | 19.389 | 83.187 | 1.00 | 36.71 |
| 10586 | NE2 | GLN | B | 560 | -21.034 | 17.543 | 84.190 | 1.00 | 35.92 |
| 10587 | C | GLN | B | 560 | -17.337 | 18.507 | 87.971 | 1.00 | 34.22 |
| 10588 | O | GLN | B | 560 | -17.092 | 19.703 | 87.973 | 1.00 | 34.78 |
| 10589 | N | GLY | B | 561 | -17.433 | 17.788 | 89.082 | 1.00 | 34.69 |
| 10590 | CA | GLY | B | 561 | -17.258 | 18.397 | 90.381 | 1.00 | 34.77 |
| 10591 | C | GLY | B | 561 | -18.543 | 18.417 | 91.179 | 1.00 | 35.33 |
| 10592 | O | GLY | B | 561 | -19.642 | 18.421 | 90.607 | 1.00 | 35.93 |
| 10593 | N | ASP | B | 562 | -18.396 | 18.398 | 92.500 | 1.00 | 35.27 |
| 10594 | CA | ASP | B | 562 | -19.506 | 18.442 | 93.425 | 1.00 | 35.86 |
| 10595 | CB | ASP | B | 562 | -18.993 | 18.303 | 94.866 | 1.00 | 35.66 |
| 10596 | CG | ASP | B | 562 | -18.734 | 16.849 | 95.272 | 1.00 | 37.04 |
| 10597 | OD1 | ASP | B | 562 | -18.796 | 15.958 | 94.392 | 1.00 | 38.30 |
| 10598 | OD2 | ASP | B | 562 | -18.478 | 16.489 | 96.456 | 1.00 | 37.08 |

FIGURE 3 GZ

| A | B | C | D | E | F | G | H | I | J |
|---|---|---|---|---|---|---|---|---|---|
| 10599 | C | ASP | B | 562 | -20.319 | 19.736 | 93.257 | 1.00 | 36.45 |
| 10600 | O | ASP | B | 562 | -21.482 | 19.807 | 93.643 | 1.00 | 36.43 |
| 10601 | N | LYS | B | 563 | -19.723 | 20.760 | 92.661 | 1.00 | 37.15 |
| 10602 | CA | LYS | B | 563 | -20.461 | 22.004 | 92.485 | 1.00 | 37.86 |
| 10603 | CB | LYS | B | 563 | -19.570 | 23.108 | 91.925 | 1.00 | 37.97 |
| 10604 | CG | LYS | B | 563 | -20.311 | 24.262 | 91.289 | 1.00 | 40.44 |
| 10605 | CD | LYS | B | 563 | -21.242 | 24.999 | 92.266 | 1.00 | 44.52 |
| 10606 | CE | LYS | B | 563 | -21.799 | 26.278 | 91.615 | 1.00 | 46.39 |
| 10607 | NZ | LYS | B | 563 | -23.034 | 26.785 | 92.282 | 1.00 | 48.60 |
| 10608 | C | LYS | B | 563 | -21.674 | 21.750 | 91.600 | 1.00 | 37.60 |
| 10609 | O | LYS | B | 563 | -22.795 | 22.130 | 91.937 | 1.00 | 37.35 |
| 10610 | N | ILE | B | 564 | -21.441 | 21.095 | 90.473 | 1.00 | 37.54 |
| 10611 | CA | ILE | B | 564 | -22.521 | 20.740 | 89.574 | 1.00 | 36.89 |
| 10612 | CB | ILE | B | 564 | -21.958 | 20.391 | 88.203 | 1.00 | 37.38 |
| 10613 | CG1 | ILE | B | 564 | -21.528 | 21.665 | 87.475 | 1.00 | 36.18 |
| 10614 | CD1 | ILE | B | 564 | -20.505 | 21.393 | 86.420 | 1.00 | 37.37 |
| 10615 | CG2 | ILE | B | 564 | -22.990 | 19.622 | 87.382 | 1.00 | 36.46 |
| 10616 | C | ILE | B | 564 | -23.328 | 19.570 | 90.135 | 1.00 | 36.51 |
| 10617 | O | ILE | B | 564 | -24.539 | 19.668 | 90.286 | 1.00 | 36.37 |
| 10618 | N | MET | B | 565 | -22.649 | 18.492 | 90.509 | 1.00 | 35.66 |
| 10619 | CA | MET | B | 565 | -23.346 | 17.291 | 90.945 | 1.00 | 35.05 |
| 10620 | CB | MET | B | 565 | -22.362 | 16.141 | 91.183 | 1.00 | 35.47 |
| 10621 | CG | MET | B | 565 | -23.040 | 14.771 | 91.292 | 1.00 | 34.19 |
| 10622 | SD | MET | B | 565 | -21.862 | 13.428 | 91.484 | 1.00 | 33.63 |
| 10623 | CE | MET | B | 565 | -21.356 | 13.686 | 93.122 | 1.00 | 32.47 |
| 10624 | C | MET | B | 565 | -24.221 | 17.446 | 92.176 | 1.00 | 35.16 |
| 10625 | O | MET | B | 565 | -25.284 | 16.843 | 92.252 | 1.00 | 34.87 |
| 10626 | N | HIS | B | 566 | -23.783 | 18.235 | 93.151 | 1.00 | 35.16 |
| 10627 | CA | HIS | B | 566 | -24.552 | 18.368 | 94.387 | 1.00 | 35.53 |
| 10628 | CB | HIS | B | 566 | -23.617 | 18.551 | 95.591 | 1.00 | 35.78 |
| 10629 | CG | HIS | B | 566 | -22.923 | 17.293 | 96.018 | 1.00 | 38.07 |
| 10630 | ND1 | HIS | B | 566 | -23.198 | 16.063 | 95.456 | 1.00 | 39.45 |
| 10631 | CE1 | HIS | B | 566 | -22.451 | 15.140 | 96.038 | 1.00 | 39.87 |
| 10632 | NE2 | HIS | B | 566 | -21.704 | 15.726 | 96.959 | 1.00 | 39.19 |
| 10633 | CD2 | HIS | B | 566 | -21.982 | 17.071 | 96.968 | 1.00 | 38.79 |
| 10634 | C | HIS | B | 566 | -25.609 | 19.480 | 94.351 | 1.00 | 35.11 |
| 10635 | O | HIS | B | 566 | -26.342 | 19.695 | 95.320 | 1.00 | 35.67 |
| 10636 | N | ALA | B | 567 | -25.701 | 20.193 | 93.245 | 1.00 | 34.61 |
| 10637 | CA | ALA | B | 567 | -26.676 | 21.273 | 93.166 | 1.00 | 34.81 |
| 10638 | CB | ALA | B | 567 | -26.582 | 21.946 | 91.832 | 1.00 | 34.30 |
| 10639 | C | ALA | B | 567 | -28.129 | 20.828 | 93.455 | 1.00 | 35.03 |
| 10640 | O | ALA | B | 567 | -28.921 | 21.603 | 93.973 | 1.00 | 35.23 |
| 10641 | N | ILE | B | 568 | -28.464 | 19.577 | 93.149 | 1.00 | 34.76 |
| 10642 | CA | ILE | B | 568 | -29.834 | 19.098 | 93.279 | 1.00 | 34.48 |
| 10643 | CB | ILE | B | 568 | -30.242 | 18.257 | 92.020 | 1.00 | 34.57 |
| 10644 | CG1 | ILE | B | 568 | -29.180 | 17.203 | 91.676 | 1.00 | 33.61 |
| 10645 | CD1 | ILE | B | 568 | -28.959 | 16.175 | 92.728 | 1.00 | 34.77 |
| 10646 | CG2 | ILE | B | 568 | -30.396 | 19.155 | 90.803 | 1.00 | 32.25 |
| 10647 | C | ILE | B | 568 | -30.056 | 18.319 | 94.565 | 1.00 | 35.25 |
| 10648 | O | ILE | B | 568 | -31.076 | 17.649 | 94.730 | 1.00 | 35.69 |
| 10649 | N | ASN | B | 569 | -29.093 | 18.413 | 95.472 | 1.00 | 35.41 |

FIGURE 3 HA

| A | B | C | D | E | F | G | H | I | J |
|---|---|---|---|---|---|---|---|---|---|
| 10650 | CA | ASN | B | 569 | -29.154 | 17.734 | 96.759 | 1.00 | 36.04 |
| 10651 | CB | ASN | B | 569 | -27.907 | 18.065 | 97.590 | 1.00 | 36.33 |
| 10652 | CG | ASN | B | 569 | -27.894 | 17.371 | 98.934 | 1.00 | 37.79 |
| 10653 | OD1 | ASN | B | 569 | -27.682 | 18.013 | 99.962 | 1.00 | 42.19 |
| 10654 | ND2 | ASN | B | 569 | -28.108 | 16.061 | 98.943 | 1.00 | 37.45 |
| 10655 | C | ASN | B | 569 | -30.413 | 18.126 | 97.504 | 1.00 | 36.25 |
| 10656 | O | ASN | B | 569 | -30.705 | 19.311 | 97.643 | 1.00 | 36.62 |
| 10657 | N | ARG | B | 570 | -31.169 | 17.123 | 97.952 | 1.00 | 36.24 |
| 10658 | CA | ARG | B | 570 | -32.410 | 17.337 | 98.682 | 1.00 | 36.46 |
| 10659 | CB | ARG | B | 570 | -32.151 | 18.128 | 99.973 | 1.00 | 36.84 |
| 10660 | CG | ARG | B | 570 | -31.252 | 17.434 | 101.001 | 1.00 | 37.76 |
| 10661 | CD | ARG | B | 570 | -31.041 | 18.262 | 102.276 | 1.00 | 40.27 |
| 10662 | NE | ARG | B | 570 | -32.317 | 18.656 | 102.880 | 1.00 | 40.70 |
| 10663 | CZ | ARG | B | 570 | -32.968 | 17.917 | 103.763 | 1.00 | 40.23 |
| 10664 | NH1 | ARG | B | 570 | -32.459 | 16.754 | 104.151 | 1.00 | 39.98 |
| 10665 | NH2 | ARG | B | 570 | -34.125 | 18.336 | 104.258 | 1.00 | 40.21 |
| 10666 | C | ARG | B | 570 | -33.459 | 18.052 | 97.837 | 1.00 | 36.25 |
| 10667 | O | ARG | B | 570 | -34.534 | 18.389 | 98.325 | 1.00 | 35.95 |
| 10668 | N | ARG | B | 571 | -33.159 | 18.258 | 96.560 | 1.00 | 36.43 |
| 10669 | CA | ARG | B | 571 | -34.050 | 19.022 | 95.702 | 1.00 | 36.27 |
| 10670 | CB | ARG | B | 571 | -33.518 | 20.446 | 95.568 | 1.00 | 37.14 |
| 10671 | CG | ARG | B | 571 | -34.595 | 21.519 | 95.634 | 1.00 | 40.76 |
| 10672 | CD | ARG | B | 571 | -34.789 | 22.148 | 97.013 | 1.00 | 44.21 |
| 10673 | NE | ARG | B | 571 | -35.108 | 21.171 | 98.043 | 1.00 | 45.29 |
| 10674 | CZ | ARG | B | 571 | -35.243 | 21.471 | 99.330 | 1.00 | 46.29 |
| 10675 | NH1 | ARG | B | 571 | -35.531 | 20.517 | 100.218 | 1.00 | 44.37 |
| 10676 | NH2 | ARG | B | 571 | -35.081 | 22.726 | 99.730 | 1.00 | 46.11 |
| 10677 | C | ARG | B | 571 | -34.207 | 18.388 | 94.327 | 1.00 | 35.45 |
| 10678 | O | ARG | B | 571 | -34.071 | 19.048 | 93.298 | 1.00 | 35.23 |
| 10679 | N | LEU | B | 572 | -34.481 | 17.091 | 94.307 | 1.00 | 35.01 |
| 10680 | CA | LEU | B | 572 | -34.735 | 16.401 | 93.045 | 1.00 | 34.53 |
| 10681 | CB | LEU | B | 572 | -34.969 | 14.913 | 93.293 | 1.00 | 34.67 |
| 10682 | CG | LEU | B | 572 | -33.819 | 13.949 | 93.040 | 1.00 | 34.88 |
| 10683 | CD1 | LEU | B | 572 | -33.944 | 12.764 | 93.977 | 1.00 | 34.07 |
| 10684 | CD2 | LEU | B | 572 | -32.479 | 14.628 | 93.169 | 1.00 | 33.53 |
| 10685 | C | LEU | B | 572 | -35.977 | 16.984 | 92.389 | 1.00 | 33.75 |
| 10686 | O | LEU | B | 572 | -36.930 | 17.368 | 93.062 | 1.00 | 33.76 |
| 10687 | N | GLY | B | 573 | -35.964 | 17.065 | 91.073 | 1.00 | 32.83 |
| 10688 | CA | GLY | B | 573 | -37.100 | 17.588 | 90.353 | 1.00 | 32.59 |
| 10689 | C | GLY | B | 573 | -37.106 | 19.087 | 90.209 | 1.00 | 32.24 |
| 10690 | O | GLY | B | 573 | -38.161 | 19.662 | 89.947 | 1.00 | 32.58 |
| 10691 | N | THR | B | 574 | -35.954 | 19.728 | 90.375 | 1.00 | 31.52 |
| 10692 | CA | THR | B | 574 | -35.867 | 21.193 | 90.230 | 1.00 | 31.33 |
| 10693 | CB | THR | B | 574 | -35.477 | 21.880 | 91.591 | 1.00 | 31.68 |
| 10694 | OG1 | THR | B | 574 | -34.339 | 21.214 | 92.153 | 1.00 | 29.87 |
| 10695 | CG2 | THR | B | 574 | -36.555 | 21.646 | 92.658 | 1.00 | 30.59 |
| 10696 | C | THR | B | 574 | -34.902 | 21.659 | 89.136 | 1.00 | 31.34 |
| 10697 | O | THR | B | 574 | -35.268 | 21.766 | 87.971 | 1.00 | 30.98 |
| 10698 | N | PHE | B | 575 | -33.661 | 21.931 | 89.531 | 1.00 | 31.94 |
| 10699 | CA | PHE | B | 575 | -32.640 | 22.450 | 88.621 | 1.00 | 32.58 |
| 10700 | CB | PHE | B | 575 | -31.329 | 22.632 | 89.387 | 1.00 | 32.81 |

FIGURE 3 HB

| A | B | C | D | E | F | G | H | I | J |
|---|---|---|---|---|---|---|---|---|---|
| 10701 | CG | PHE | B | 575 | -31.386 | 23.712 | 90.438 | 1.00 | 33.47 |
| 10702 | CD1 | PHE | B | 575 | -32.083 | 24.893 | 90.204 | 1.00 | 34.26 |
| 10703 | CE1 | PHE | B | 575 | -32.127 | 25.899 | 91.155 | 1.00 | 34.50 |
| 10704 | CZ | PHE | B | 575 | -31.479 | 25.732 | 92.374 | 1.00 | 34.35 |
| 10705 | CE2 | PHE | B | 575 | -30.793 | 24.557 | 92.627 | 1.00 | 35.05 |
| 10706 | CD2 | PHE | B | 575 | -30.747 | 23.551 | 91.656 | 1.00 | 34.35 |
| 10707 | C | PHE | B | 575 | -32.438 | 21.579 | 87.374 | 1.00 | 33.10 |
| 10708 | O | PHE | B | 575 | -32.447 | 22.076 | 86.240 | 1.00 | 33.70 |
| 10709 | N | GLU | B | 576 | -32.223 | 20.288 | 87.609 | 1.00 | 32.96 |
| 10710 | CA | GLU | B | 576 | -32.090 | 19.264 | 86.576 | 1.00 | 33.38 |
| 10711 | CB | GLU | B | 576 | -32.298 | 17.936 | 87.279 | 1.00 | 33.76 |
| 10712 | CG | GLU | B | 576 | -33.338 | 18.161 | 88.384 | 1.00 | 36.02 |
| 10713 | CD | GLU | B | 576 | -33.855 | 16.885 | 88.957 | 1.00 | 38.90 |
| 10714 | OE1 | GLU | B | 576 | -33.478 | 15.815 | 88.461 | 1.00 | 40.73 |
| 10715 | OE2 | GLU | B | 576 | -34.625 | 16.950 | 89.918 | 1.00 | 43.20 |
| 10716 | C | GLU | B | 576 | -33.210 | 19.390 | 85.559 | 1.00 | 32.87 |
| 10717 | O | GLU | B | 576 | -32.994 | 19.354 | 84.354 | 1.00 | 32.82 |
| 10718 | N | VAL | B | 577 | -34.430 | 19.496 | 86.067 | 1.00 | 32.68 |
| 10719 | CA | VAL | B | 577 | -35.588 | 19.679 | 85.225 | 1.00 | 32.75 |
| 10720 | CB | VAL | B | 577 | -36.880 | 19.669 | 86.074 | 1.00 | 32.71 |
| 10721 | CG1 | VAL | B | 577 | -37.068 | 18.331 | 86.760 | 1.00 | 33.07 |
| 10722 | CG2 | VAL | B | 577 | -38.082 | 19.995 | 85.235 | 1.00 | 31.84 |
| 10723 | C | VAL | B | 577 | -35.436 | 21.032 | 84.533 | 1.00 | 33.08 |
| 10724 | O | VAL | B | 577 | -35.497 | 21.124 | 83.315 | 1.00 | 32.79 |
| 10725 | N | GLU | B | 578 | -35.194 | 22.077 | 85.325 | 1.00 | 33.64 |
| 10726 | CA | GLU | B | 578 | -35.077 | 23.436 | 84.793 | 1.00 | 34.20 |
| 10727 | CB | GLU | B | 578 | -34.875 | 24.444 | 85.931 | 1.00 | 34.96 |
| 10728 | CG | GLU | B | 578 | -36.095 | 24.555 | 86.849 | 1.00 | 38.55 |
| 10729 | CD | GLU | B | 578 | -35.791 | 25.183 | 88.209 | 1.00 | 43.37 |
| 10730 | OE1 | GLU | B | 578 | -36.143 | 24.559 | 89.232 | 1.00 | 45.40 |
| 10731 | OE2 | GLU | B | 578 | -35.214 | 26.296 | 88.269 | 1.00 | 44.63 |
| 10732 | C | GLU | B | 578 | -33.992 | 23.575 | 83.740 | 1.00 | 33.39 |
| 10733 | O | GLU | B | 578 | -34.157 | 24.326 | 82.789 | 1.00 | 33.04 |
| 10734 | N | ASP | B | 579 | -32.904 | 22.816 | 83.881 | 1.00 | 33.17 |
| 10735 | CA | ASP | B | 579 | -31.781 | 22.940 | 82.952 | 1.00 | 32.69 |
| 10736 | CB | ASP | B | 579 | -30.491 | 22.411 | 83.587 | 1.00 | 33.66 |
| 10737 | CG | ASP | B | 579 | -29.996 | 23.282 | 84.751 | 1.00 | 34.52 |
| 10738 | OD1 | ASP | B | 579 | -30.589 | 24.347 | 85.036 | 1.00 | 35.69 |
| 10739 | OD2 | ASP | B | 579 | -29.012 | 22.975 | 85.449 | 1.00 | 37.32 |
| 10740 | C | ASP | B | 579 | -32.040 | 22.329 | 81.566 | 1.00 | 32.13 |
| 10741 | O | ASP | B | 579 | -31.517 | 22.815 | 80.568 | 1.00 | 32.02 |
| 10742 | N | GLN | B | 580 | -32.852 | 21.272 | 81.498 | 1.00 | 31.39 |
| 10743 | CA | GLN | B | 580 | -33.224 | 20.686 | 80.208 | 1.00 | 30.77 |
| 10744 | CB | GLN | B | 580 | -33.987 | 19.364 | 80.402 | 1.00 | 30.25 |
| 10745 | CG | GLN | B | 580 | -33.192 | 18.302 | 81.128 | 1.00 | 28.35 |
| 10746 | CD | GLN | B | 580 | -32.087 | 17.731 | 80.274 | 1.00 | 25.57 |
| 10747 | OE1 | GLN | B | 580 | -32.331 | 17.356 | 79.135 | 1.00 | 26.87 |
| 10748 | NE2 | GLN | B | 580 | -30.874 | 17.673 | 80.811 | 1.00 | 22.34 |
| 10749 | C | GLN | B | 580 | -34.096 | 21.661 | 79.425 | 1.00 | 31.03 |
| 10750 | O | GLN | B | 580 | -33.985 | 21.772 | 78.213 | 1.00 | 31.52 |
| 10751 | N | ILE | B | 581 | -34.991 | 22.360 | 80.110 | 1.00 | 31.20 |

FIGURE 3 HC

| A | B | C | D | E | F | G | H | I | J |
|---|---|---|---|---|---|---|---|---|---|
| 10752 | CA | ILE | B | 581 | -35.801 | 23.342 | 79.417 | 1.00 | 31.85 |
| 10753 | CB | ILE | B | 581 | -36.861 | 23.940 | 80.365 | 1.00 | 32.05 |
| 10754 | CG1 | ILE | B | 581 | -37.834 | 22.858 | 80.832 | 1.00 | 31.00 |
| 10755 | CD1 | ILE | B | 581 | -38.632 | 23.258 | 82.037 | 1.00 | 30.97 |
| 10756 | CG2 | ILE | B | 581 | -37.597 | 25.053 | 79.678 | 1.00 | 30.17 |
| 10757 | C | ILE | B | 581 | -34.891 | 24.446 | 78.870 | 1.00 | 32.71 |
| 10758 | O | ILE | B | 581 | -34.969 | 24.809 | 77.701 | 1.00 | 33.46 |
| 10759 | N | GLU | B | 582 | -34.012 | 24.966 | 79.723 | 1.00 | 33.21 |
| 10760 | CA | GLU | B | 582 | -33.097 | 26.018 | 79.315 | 1.00 | 33.79 |
| 10761 | CB | GLU | B | 582 | -32.262 | 26.491 | 80.517 | 1.00 | 34.12 |
| 10762 | CG | GLU | B | 582 | -31.310 | 27.651 | 80.234 | 1.00 | 36.22 |
| 10763 | CD | GLU | B | 582 | -32.004 | 28.887 | 79.664 | 1.00 | 39.46 |
| 10764 | OE1 | GLU | B | 582 | -31.339 | 29.644 | 78.914 | 1.00 | 40.85 |
| 10765 | OE2 | GLU | B | 582 | -33.204 | 29.105 | 79.959 | 1.00 | 39.16 |
| 10766 | C | GLU | B | 582 | -32.216 | 25.536 | 78.160 | 1.00 | 33.82 |
| 10767 | O | GLU | B | 582 | -31.911 | 26.296 | 77.252 | 1.00 | 33.39 |
| 10768 | N | ALA | B | 583 | -31.827 | 24.264 | 78.195 | 1.00 | 33.90 |
| 10769 | CA | ALA | B | 583 | -31.024 | 23.688 | 77.123 | 1.00 | 34.37 |
| 10770 | CB | ALA | B | 583 | -30.724 | 22.211 | 77.411 | 1.00 | 33.98 |
| 10771 | C | ALA | B | 583 | -31.757 | 23.810 | 75.803 | 1.00 | 34.95 |
| 10772 | O | ALA | B | 583 | -31.205 | 24.290 | 74.824 | 1.00 | 35.07 |
| 10773 | N | ALA | B | 584 | -33.011 | 23.366 | 75.797 | 1.00 | 35.74 |
| 10774 | CA | ALA | B | 584 | -33.850 | 23.412 | 74.607 | 1.00 | 36.83 |
| 10775 | CB | ALA | B | 584 | -35.240 | 22.854 | 74.916 | 1.00 | 36.57 |
| 10776 | C | ALA | B | 584 | -33.966 | 24.826 | 74.068 | 1.00 | 37.33 |
| 10777 | O | ALA | B | 584 | -33.833 | 25.049 | 72.865 | 1.00 | 37.77 |
| 10778 | N | ARG | B | 585 | -34.243 | 25.774 | 74.954 | 1.00 | 38.17 |
| 10779 | CA | ARG | B | 585 | -34.320 | 27.180 | 74.561 | 1.00 | 39.25 |
| 10780 | CB | ARG | B | 585 | -34.476 | 28.072 | 75.792 | 1.00 | 38.94 |
| 10781 | CG | ARG | B | 585 | -35.733 | 27.835 | 76.597 | 1.00 | 39.58 |
| 10782 | CD | ARG | B | 585 | -36.191 | 29.063 | 77.366 | 1.00 | 40.42 |
| 10783 | NE | ARG | B | 585 | -36.713 | 28.721 | 78.685 | 1.00 | 41.24 |
| 10784 | CZ | ARG | B | 585 | -37.988 | 28.809 | 79.028 | 1.00 | 42.41 |
| 10785 | NH1 | ARG | B | 585 | -38.892 | 29.226 | 78.145 | 1.00 | 43.90 |
| 10786 | NH2 | ARG | B | 585 | -38.367 | 28.480 | 80.255 | 1.00 | 42.34 |
| 10787 | C | ARG | B | 585 | -33.040 | 27.585 | 73.835 | 1.00 | 39.97 |
| 10788 | O | ARG | B | 585 | -33.074 | 28.246 | 72.788 | 1.00 | 40.01 |
| 10789 | N | GLN | B | 586 | -31.910 | 27.184 | 74.416 | 1.00 | 40.89 |
| 10790 | CA | GLN | B | 586 | -30.606 | 27.495 | 73.865 | 1.00 | 41.76 |
| 10791 | CB | GLN | B | 586 | -29.514 | 27.026 | 74.826 | 1.00 | 41.88 |
| 10792 | CG | GLN | B | 586 | -29.546 | 27.743 | 76.154 | 1.00 | 44.21 |
| 10793 | CD | GLN | B | 586 | -29.185 | 29.209 | 76.023 | 1.00 | 48.06 |
| 10794 | OE1 | GLN | B | 586 | -28.453 | 29.581 | 75.106 | 1.00 | 49.53 |
| 10795 | NE2 | GLN | B | 586 | -29.688 | 30.047 | 76.941 | 1.00 | 48.56 |
| 10796 | C | GLN | B | 586 | -30.466 | 26.822 | 72.516 | 1.00 | 41.89 |
| 10797 | O | GLN | B | 586 | -30.032 | 27.439 | 71.542 | 1.00 | 41.76 |
| 10798 | N | PHE | B | 587 | -30.839 | 25.546 | 72.453 | 1.00 | 42.18 |
| 10799 | CA | PHE | B | 587 | -30.792 | 24.845 | 71.181 | 1.00 | 42.60 |
| 10800 | CB | PHE | B | 587 | -31.264 | 23.404 | 71.333 | 1.00 | 42.25 |
| 10801 | CG | PHE | B | 587 | -30.377 | 22.576 | 72.206 | 1.00 | 43.51 |
| 10802 | CD1 | PHE | B | 587 | -29.069 | 22.966 | 72.452 | 1.00 | 44.12 |

FIGURE 3 HD

| A | B | C | D | E | F | G | H | I | J |
|---|---|---|---|---|---|---|---|---|---|
| 10803 | CE1 | PHE | B | 587 | -28.242 | 22.209 | 73.266 | 1.00 | 44.69 |
| 10804 | CZ | PHE | B | 587 | -28.719 | 21.058 | 73.847 | 1.00 | 43.72 |
| 10805 | CE2 | PHE | B | 587 | -30.026 | 20.664 | 73.616 | 1.00 | 44.68 |
| 10806 | CD2 | PHE | B | 587 | -30.847 | 21.415 | 72.797 | 1.00 | 42.78 |
| 10807 | C | PHE | B | 587 | -31.587 | 25.605 | 70.101 | 1.00 | 42.70 |
| 10808 | O | PHE | B | 587 | -31.130 | 25.726 | 68.971 | 1.00 | 42.70 |
| 10809 | N | SER | B | 588 | -32.766 | 26.120 | 70.430 | 1.00 | 43.04 |
| 10810 | CA | SER | B | 588 | -33.493 | 26.881 | 69.415 | 1.00 | 44.12 |
| 10811 | CB | SER | B | 588 | -34.931 | 27.233 | 69.838 | 1.00 | 43.98 |
| 10812 | OG | SER | B | 588 | -35.115 | 27.130 | 71.241 | 1.00 | 44.78 |
| 10813 | C | SER | B | 588 | -32.717 | 28.125 | 69.020 | 1.00 | 44.46 |
| 10814 | O | SER | B | 588 | -32.516 | 28.385 | 67.841 | 1.00 | 44.86 |
| 10815 | N | LYS | B | 589 | -32.254 | 28.891 | 69.997 | 1.00 | 44.92 |
| 10816 | CA | LYS | B | 589 | -31.522 | 30.106 | 69.670 | 1.00 | 45.30 |
| 10817 | CB | LYS | B | 589 | -31.057 | 30.815 | 70.937 | 1.00 | 45.99 |
| 10818 | CG | LYS | B | 589 | -32.115 | 31.744 | 71.537 | 1.00 | 48.60 |
| 10819 | CD | LYS | B | 589 | -32.288 | 31.524 | 73.046 | 1.00 | 52.25 |
| 10820 | CE | LYS | B | 589 | -33.778 | 31.463 | 73.447 | 1.00 | 54.10 |
| 10821 | NZ | LYS | B | 589 | -33.964 | 31.373 | 74.926 | 1.00 | 54.99 |
| 10822 | C | LYS | B | 589 | -30.340 | 29.836 | 68.733 | 1.00 | 44.98 |
| 10823 | O | LYS | B | 589 | -29.896 | 30.742 | 68.015 | 1.00 | 45.18 |
| 10824 | N | MET | B | 590 | -29.849 | 28.596 | 68.726 | 1.00 | 43.88 |
| 10825 | CA | MET | B | 590 | -28.717 | 28.220 | 67.870 | 1.00 | 43.03 |
| 10826 | CB | MET | B | 590 | -28.229 | 26.810 | 68.177 | 1.00 | 43.06 |
| 10827 | CG | MET | B | 590 | -27.241 | 26.785 | 69.297 | 1.00 | 43.29 |
| 10828 | SD | MET | B | 590 | -26.855 | 25.139 | 69.824 | 1.00 | 42.52 |
| 10829 | CE | MET | B | 590 | -26.228 | 25.512 | 71.454 | 1.00 | 40.60 |
| 10830 | C | MET | B | 590 | -28.946 | 28.364 | 66.372 | 1.00 | 42.27 |
| 10831 | O | MET | B | 590 | -27.989 | 28.366 | 65.604 | 1.00 | 42.05 |
| 10832 | N | GLY | B | 591 | -30.209 | 28.408 | 65.955 | 1.00 | 41.68 |
| 10833 | CA | GLY | B | 591 | -30.531 | 28.683 | 64.565 | 1.00 | 40.28 |
| 10834 | C | GLY | B | 591 | -30.969 | 27.606 | 63.595 | 1.00 | 39.89 |
| 10835 | O | GLY | B | 591 | -31.449 | 27.930 | 62.510 | 1.00 | 39.69 |
| 10836 | N | PHE | B | 592 | -30.807 | 26.336 | 63.955 | 1.00 | 39.16 |
| 10837 | CA | PHE | B | 592 | -31.180 | 25.258 | 63.051 | 1.00 | 38.88 |
| 10838 | CB | PHE | B | 592 | -29.943 | 24.481 | 62.631 | 1.00 | 39.01 |
| 10839 | CG | PHE | B | 592 | -28.947 | 24.311 | 63.734 | 1.00 | 39.41 |
| 10840 | CD1 | PHE | B | 592 | -27.733 | 24.973 | 63.702 | 1.00 | 39.01 |
| 10841 | CE1 | PHE | B | 592 | -26.820 | 24.811 | 64.720 | 1.00 | 38.57 |
| 10842 | CZ | PHE | B | 592 | -27.118 | 23.993 | 65.791 | 1.00 | 38.32 |
| 10843 | CE2 | PHE | B | 592 | -28.327 | 23.326 | 65.834 | 1.00 | 39.40 |
| 10844 | CD2 | PHE | B | 592 | -29.233 | 23.494 | 64.813 | 1.00 | 38.42 |
| 10845 | C | PHE | B | 592 | -32.202 | 24.329 | 63.702 | 1.00 | 38.46 |
| 10846 | O | PHE | B | 592 | -32.220 | 23.113 | 63.457 | 1.00 | 38.09 |
| 10847 | N | VAL | B | 593 | -33.049 | 24.922 | 64.536 | 1.00 | 37.77 |
| 10848 | CA | VAL | B | 593 | -34.079 | 24.181 | 65.245 | 1.00 | 37.24 |
| 10849 | CB | VAL | B | 593 | -33.778 | 24.100 | 66.746 | 1.00 | 37.03 |
| 10850 | CG1 | VAL | B | 593 | -34.960 | 23.481 | 67.475 | 1.00 | 38.18 |
| 10851 | CG2 | VAL | B | 593 | -32.525 | 23.289 | 66.993 | 1.00 | 35.08 |
| 10852 | C | VAL | B | 593 | -35.469 | 24.780 | 65.049 | 1.00 | 36.99 |
| 10853 | O | VAL | B | 593 | -35.669 | 25.975 | 65.183 | 1.00 | 37.00 |

FIGURE 3 HE

| A | B | C | D | E | F | G | H | I | J |
|---|---|---|---|---|---|---|---|---|---|
| 10854 | N | ASP | B | 594 | -36.425 | 23.921 | 64.718 | 1.00 | 36.94 |
| 10855 | CA | ASP | B | 594 | -37.811 | 24.326 | 64.546 | 1.00 | 36.41 |
| 10856 | CB | ASP | B | 594 | -38.534 | 23.374 | 63.598 | 1.00 | 36.50 |
| 10857 | CG | ASP | B | 594 | -39.998 | 23.712 | 63.447 | 1.00 | 35.85 |
| 10858 | OD1 | ASP | B | 594 | -40.682 | 23.044 | 62.656 | 1.00 | 35.54 |
| 10859 | OD2 | ASP | B | 594 | -40.553 | 24.641 | 64.073 | 1.00 | 37.18 |
| 10860 | C | ASP | B | 594 | -38.531 | 24.370 | 65.891 | 1.00 | 36.63 |
| 10861 | O | ASP | B | 594 | -38.871 | 23.337 | 66.479 | 1.00 | 35.76 |
| 10862 | N | ASN | B | 595 | -38.763 | 25.592 | 66.346 | 1.00 | 37.09 |
| 10863 | CA | ASN | B | 595 | -39.398 | 25.888 | 67.619 | 1.00 | 37.40 |
| 10864 | CB | ASN | B | 595 | -39.615 | 27.392 | 67.730 | 1.00 | 38.21 |
| 10865 | CG | ASN | B | 595 | -38.442 | 28.077 | 68.326 | 1.00 | 41.32 |
| 10866 | OD1 | ASN | B | 595 | -37.398 | 27.463 | 68.486 | 1.00 | 44.68 |
| 10867 | ND2 | ASN | B | 595 | -38.596 | 29.353 | 68.683 | 1.00 | 44.83 |
| 10868 | C | ASN | B | 595 | -40.732 | 25.238 | 67.829 | 1.00 | 36.33 |
| 10869 | O | ASN | B | 595 | -41.198 | 25.121 | 68.963 | 1.00 | 35.77 |
| 10870 | N | LYS | B | 596 | -41.370 | 24.862 | 66.736 | 1.00 | 35.44 |
| 10871 | CA | LYS | B | 596 | -42.703 | 24.292 | 66.840 | 1.00 | 35.17 |
| 10872 | CB | LYS | B | 596 | -43.531 | 24.635 | 65.604 | 1.00 | 35.40 |
| 10873 | CG | LYS | B | 596 | -43.862 | 26.079 | 65.433 | 1.00 | 37.84 |
| 10874 | CD | LYS | B | 596 | -44.459 | 26.298 | 64.051 | 1.00 | 41.84 |
| 10875 | CE | LYS | B | 596 | -43.501 | 25.866 | 62.928 | 1.00 | 45.03 |
| 10876 | NZ | LYS | B | 596 | -42.146 | 26.569 | 62.900 | 1.00 | 43.27 |
| 10877 | C | LYS | B | 596 | -42.643 | 22.780 | 66.988 | 1.00 | 33.77 |
| 10878 | O | LYS | B | 596 | -43.663 | 22.133 | 67.193 | 1.00 | 33.83 |
| 10879 | N | ARG | B | 597 | -41.446 | 22.222 | 66.880 | 1.00 | 32.37 |
| 10880 | CA | ARG | B | 597 | -41.292 | 20.776 | 66.926 | 1.00 | 30.79 |
| 10881 | CB | ARG | B | 597 | -41.179 | 20.224 | 65.519 | 1.00 | 30.90 |
| 10882 | CG | ARG | B | 597 | -42.481 | 20.303 | 64.742 | 1.00 | 31.54 |
| 10883 | CD | ARG | B | 597 | -42.440 | 19.570 | 63.422 | 1.00 | 31.38 |
| 10884 | NE | ARG | B | 597 | -41.509 | 20.240 | 62.528 | 1.00 | 31.70 |
| 10885 | CZ | ARG | B | 597 | -41.056 | 19.731 | 61.392 | 1.00 | 33.10 |
| 10886 | NH1 | ARG | B | 597 | -41.448 | 18.529 | 61.003 | 1.00 | 32.23 |
| 10887 | NH2 | ARG | B | 597 | -40.197 | 20.422 | 60.646 | 1.00 | 31.81 |
| 10888 | C | ARG | B | 597 | -40.107 | 20.354 | 67.760 | 1.00 | 29.86 |
| 10889 | O | ARG | B | 597 | -39.109 | 19.869 | 67.261 | 1.00 | 29.51 |
| 10890 | N | ILE | B | 598 | -40.229 | 20.566 | 69.053 | 1.00 | 28.96 |
| 10891 | CA | ILE | B | 598 | -39.206 | 20.150 | 69.976 | 1.00 | 28.37 |
| 10892 | CB | ILE | B | 598 | -38.662 | 21.337 | 70.754 | 1.00 | 28.00 |
| 10893 | CG1 | ILE | B | 598 | -38.116 | 22.376 | 69.796 | 1.00 | 27.47 |
| 10894 | CD1 | ILE | B | 598 | -37.625 | 23.614 | 70.485 | 1.00 | 27.15 |
| 10895 | CG2 | ILE | B | 598 | -37.567 | 20.886 | 71.693 | 1.00 | 28.30 |
| 10896 | C | ILE | B | 598 | -39.869 | 19.173 | 70.923 | 1.00 | 28.08 |
| 10897 | O | ILE | B | 598 | -40.916 | 19.457 | 71.495 | 1.00 | 27.15 |
| 10898 | N | ALA | B | 599 | -39.260 | 18.010 | 71.084 | 1.00 | 28.09 |
| 10899 | CA | ALA | B | 599 | -39.843 | 17.015 | 71.960 | 1.00 | 27.94 |
| 10900 | CB | ALA | B | 599 | -40.346 | 15.821 | 71.150 | 1.00 | 27.68 |
| 10901 | C | ALA | B | 599 | -38.834 | 16.582 | 72.997 | 1.00 | 27.63 |
| 10902 | O | ALA | B | 599 | -37.686 | 16.985 | 72.969 | 1.00 | 28.42 |
| 10903 | N | ILE | B | 600 | -39.262 | 15.761 | 73.931 | 1.00 | 27.13 |
| 10904 | CA | ILE | B | 600 | -38.343 | 15.288 | 74.931 | 1.00 | 26.72 |

FIGURE 3 HF

| A | B | C | D | E | F | G | H | I | J |
|---|---|---|---|---|---|---|---|---|---|
| 10905 | CB | ILE | B | 600 | -38.429 | 16.187 | 76.192 | 1.00 | 26.71 |
| 10906 | CG1 | ILE | B | 600 | -37.506 | 15.685 | 77.298 | 1.00 | 27.36 |
| 10907 | CD1 | ILE | B | 600 | -37.320 | 16.685 | 78.503 | 1.00 | 30.58 |
| 10908 | CG2 | ILE | B | 600 | -39.884 | 16.280 | 76.672 | 1.00 | 25.85 |
| 10909 | C | ILE | B | 600 | -38.722 | 13.854 | 75.260 | 1.00 | 26.65 |
| 10910 | O | ILE | B | 600 | -39.891 | 13.491 | 75.239 | 1.00 | 25.57 |
| 10911 | N | TRP | B | 601 | -37.726 | 13.028 | 75.558 | 1.00 | 26.24 |
| 10912 | CA | TRP | B | 601 | -38.055 | 11.691 | 75.979 | 1.00 | 25.83 |
| 10913 | CB | TRP | B | 601 | -38.241 | 10.779 | 74.768 | 1.00 | 25.63 |
| 10914 | CG | TRP | B | 601 | -37.071 | 9.993 | 74.383 | 1.00 | 23.01 |
| 10915 | CD1 | TRP | B | 601 | -36.013 | 10.407 | 73.628 | 1.00 | 20.91 |
| 10916 | NE1 | TRP | B | 601 | -35.137 | 9.367 | 73.438 | 1.00 | 21.35 |
| 10917 | CE2 | TRP | B | 601 | -35.619 | 8.251 | 74.067 | 1.00 | 21.02 |
| 10918 | CD2 | TRP | B | 601 | -36.850 | 8.610 | 74.664 | 1.00 | 22.98 |
| 10919 | CE3 | TRP | B | 601 | -37.553 | 7.641 | 75.378 | 1.00 | 21.50 |
| 10920 | CZ3 | TRP | B | 601 | -37.008 | 6.354 | 75.478 | 1.00 | 24.97 |
| 10921 | CH2 | TRP | B | 601 | -35.784 | 6.036 | 74.864 | 1.00 | 23.82 |
| 10922 | CZ2 | TRP | B | 601 | -35.079 | 6.974 | 74.161 | 1.00 | 22.00 |
| 10923 | C | TRP | B | 601 | -37.006 | 11.166 | 76.929 | 1.00 | 25.90 |
| 10924 | O | TRP | B | 601 | -35.868 | 11.619 | 76.919 | 1.00 | 25.94 |
| 10925 | N | GLY | B | 602 | -37.405 | 10.239 | 77.782 | 1.00 | 25.43 |
| 10926 | CA | GLY | B | 602 | -36.463 | 9.646 | 78.697 | 1.00 | 25.31 |
| 10927 | C | GLY | B | 602 | -37.041 | 8.405 | 79.332 | 1.00 | 25.50 |
| 10928 | O | GLY | B | 602 | -38.250 | 8.187 | 79.274 | 1.00 | 25.17 |
| 10929 | N | TRP | B | 603 | -36.172 | 7.645 | 80.000 | 1.00 | 25.72 |
| 10930 | CA | TRP | B | 603 | -36.507 | 6.372 | 80.626 | 1.00 | 25.45 |
| 10931 | CB | TRP | B | 603 | -35.667 | 5.293 | 79.902 | 1.00 | 25.49 |
| 10932 | CG | TRP | B | 603 | -36.141 | 3.874 | 79.984 | 1.00 | 25.45 |
| 10933 | CD1 | TRP | B | 603 | -36.340 | 3.148 | 81.105 | 1.00 | 25.41 |
| 10934 | NE1 | TRP | B | 603 | -36.768 | 1.882 | 80.783 | 1.00 | 25.87 |
| 10935 | CE2 | TRP | B | 603 | -36.821 | 1.764 | 79.418 | 1.00 | 25.67 |
| 10936 | CD2 | TRP | B | 603 | -36.437 | 2.999 | 78.881 | 1.00 | 25.16 |
| 10937 | CE3 | TRP | B | 603 | -36.400 | 3.134 | 77.488 | 1.00 | 24.78 |
| 10938 | CZ3 | TRP | B | 603 | -36.765 | 2.058 | 76.694 | 1.00 | 22.45 |
| 10939 | CH2 | TRP | B | 603 | -37.130 | 0.842 | 77.257 | 1.00 | 22.60 |
| 10940 | CZ2 | TRP | B | 603 | -37.174 | 0.671 | 78.613 | 1.00 | 23.90 |
| 10941 | C | TRP | B | 603 | -36.147 | 6.445 | 82.119 | 1.00 | 25.53 |
| 10942 | O | TRP | B | 603 | -35.051 | 6.864 | 82.475 | 1.00 | 25.25 |
| 10943 | N | SER | B | 604 | -37.050 | 6.032 | 83.003 | 1.00 | 26.12 |
| 10944 | CA | SER | B | 604 | -36.732 | 6.008 | 84.438 | 1.00 | 26.35 |
| 10945 | CB | SER | B | 604 | -35.447 | 5.196 | 84.688 | 1.00 | 26.35 |
| 10946 | OG | SER | B | 604 | -35.397 | 4.684 | 86.014 | 1.00 | 25.82 |
| 10947 | C | SER | B | 604 | -36.608 | 7.436 | 85.002 | 1.00 | 26.75 |
| 10948 | O | SER | B | 604 | -37.573 | 8.185 | 84.947 | 1.00 | 27.00 |
| 10949 | N | TYR | B | 605 | -35.436 | 7.822 | 85.526 | 1.00 | 26.70 |
| 10950 | CA | TYR | B | 605 | -35.241 | 9.209 | 85.985 | 1.00 | 26.20 |
| 10951 | CB | TYR | B | 605 | -33.807 | 9.479 | 86.481 | 1.00 | 25.85 |
| 10952 | CG | TYR | B | 605 | -33.693 | 10.715 | 87.352 | 1.00 | 26.33 |
| 10953 | CD1 | TYR | B | 605 | -33.605 | 10.611 | 88.730 | 1.00 | 26.80 |
| 10954 | CE1 | TYR | B | 605 | -33.505 | 11.730 | 89.520 | 1.00 | 27.25 |
| 10955 | CZ | TYR | B | 605 | -33.525 | 12.982 | 88.947 | 1.00 | 26.52 |

FIGURE 3 HG

| A | B | C | D | E | F | G | H | I | J |
|---|---|---|---|---|---|---|---|---|---|
| 10956 | OH | TYR | B | 605 | -33.450 | 14.116 | 89.750 | 1.00 | 27.45 |
| 10957 | CE2 | TYR | B | 605 | -33.625 | 13.113 | 87.595 | 1.00 | 26.09 |
| 10958 | CD2 | TYR | B | 605 | -33.703 | 11.983 | 86.801 | 1.00 | 27.69 |
| 10959 | C | TYR | B | 605 | -35.529 | 10.132 | 84.824 | 1.00 | 25.82 |
| 10960 | O | TYR | B | 605 | -36.026 | 11.251 | 84.994 | 1.00 | 25.93 |
| 10961 | N | GLY | B | 606 | -35.167 | 9.676 | 83.636 | 1.00 | 25.68 |
| 10962 | CA | GLY | B | 606 | -35.444 | 10.437 | 82.428 | 1.00 | 26.10 |
| 10963 | C | GLY | B | 606 | -36.936 | 10.453 | 82.106 | 1.00 | 26.32 |
| 10964 | O | GLY | B | 606 | -37.385 | 11.275 | 81.328 | 1.00 | 27.10 |
| 10965 | N | GLY | B | 607 | -37.709 | 9.539 | 82.682 | 1.00 | 26.64 |
| 10966 | CA | GLY | B | 607 | -39.140 | 9.550 | 82.448 | 1.00 | 26.70 |
| 10967 | C | GLY | B | 607 | -39.700 | 10.611 | 83.370 | 1.00 | 27.06 |
| 10968 | O | GLY | B | 607 | -40.596 | 11.410 | 83.015 | 1.00 | 26.72 |
| 10969 | N | TYR | B | 608 | -39.146 | 10.602 | 84.580 | 1.00 | 26.75 |
| 10970 | CA | TYR | B | 608 | -39.489 | 11.552 | 85.607 | 1.00 | 26.74 |
| 10971 | CB | TYR | B | 608 | -38.608 | 11.314 | 86.820 | 1.00 | 26.39 |
| 10972 | CG | TYR | B | 608 | -38.776 | 12.343 | 87.904 | 1.00 | 26.42 |
| 10973 | CD1 | TYR | B | 608 | -37.744 | 13.222 | 88.216 | 1.00 | 25.46 |
| 10974 | CE1 | TYR | B | 608 | -37.879 | 14.167 | 89.206 | 1.00 | 24.73 |
| 10975 | CZ | TYR | B | 608 | -39.065 | 14.254 | 89.900 | 1.00 | 26.75 |
| 10976 | OH | TYR | B | 608 | -39.201 | 15.189 | 90.899 | 1.00 | 26.44 |
| 10977 | CE2 | TYR | B | 608 | -40.122 | 13.399 | 89.602 | 1.00 | 26.14 |
| 10978 | CD2 | TYR | B | 608 | -39.970 | 12.445 | 88.615 | 1.00 | 25.22 |
| 10979 | C | TYR | B | 608 | -39.269 | 12.957 | 85.057 | 1.00 | 26.97 |
| 10980 | O | TYR | B | 608 | -40.213 | 13.741 | 84.948 | 1.00 | 27.41 |
| 10981 | N | VAL | B | 609 | -38.036 | 13.252 | 84.658 | 1.00 | 26.42 |
| 10982 | CA | VAL | B | 609 | -37.717 | 14.578 | 84.132 | 1.00 | 26.01 |
| 10983 | CB | VAL | B | 609 | -36.209 | 14.741 | 83.824 | 1.00 | 24.91 |
| 10984 | CG1 | VAL | B | 609 | -35.959 | 16.013 | 83.018 | 1.00 | 25.28 |
| 10985 | CG2 | VAL | B | 609 | -35.447 | 14.811 | 85.117 | 1.00 | 26.19 |
| 10986 | C | VAL | B | 609 | -38.559 | 14.977 | 82.925 | 1.00 | 26.13 |
| 10987 | O | VAL | B | 609 | -39.048 | 16.119 | 82.853 | 1.00 | 26.91 |
| 10988 | N | THR | B | 610 | -38.699 | 14.064 | 81.963 | 1.00 | 25.25 |
| 10989 | CA | THR | B | 610 | -39.546 | 14.317 | 80.802 | 1.00 | 24.57 |
| 10990 | CB | THR | B | 610 | -39.698 | 13.047 | 79.957 | 1.00 | 24.19 |
| 10991 | OG1 | THR | B | 610 | -38.462 | 12.760 | 79.320 | 1.00 | 23.32 |
| 10992 | CG2 | THR | B | 610 | -40.641 | 13.302 | 78.786 | 1.00 | 23.39 |
| 10993 | C | THR | B | 610 | -40.937 | 14.748 | 81.244 | 1.00 | 24.41 |
| 10994 | O | THR | B | 610 | -41.488 | 15.737 | 80.752 | 1.00 | 24.36 |
| 10995 | N | SER | B | 611 | -41.515 | 13.966 | 82.150 | 1.00 | 24.64 |
| 10996 | CA | SER | B | 611 | -42.832 | 14.262 | 82.697 | 1.00 | 24.92 |
| 10997 | CB | SER | B | 611 | -43.291 | 13.129 | 83.607 | 1.00 | 24.80 |
| 10998 | OG | SER | B | 611 | -43.361 | 11.912 | 82.885 | 1.00 | 27.23 |
| 10999 | C | SER | B | 611 | -42.845 | 15.579 | 83.479 | 1.00 | 24.77 |
| 11000 | O | SER | B | 611 | -43.781 | 16.356 | 83.378 | 1.00 | 24.75 |
| 11001 | N | MET | B | 612 | -41.819 | 15.828 | 84.275 | 1.00 | 24.95 |
| 11002 | CA | MET | B | 612 | -41.794 | 17.078 | 85.027 | 1.00 | 25.17 |
| 11003 | CB | MET | B | 612 | -40.673 | 17.095 | 86.025 | 1.00 | 24.49 |
| 11004 | CG | MET | B | 612 | -40.860 | 16.104 | 87.098 | 1.00 | 25.36 |
| 11005 | SD | MET | B | 612 | -42.043 | 16.655 | 88.288 | 1.00 | 27.85 |
| 11006 | CE | MET | B | 612 | -41.102 | 18.007 | 89.180 | 1.00 | 24.85 |

FIGURE 3 HH

| A | B | C | D | E | F | G | H | I | J |
|---|---|---|---|---|---|---|---|---|---|
| 11007 | C | MET | B | 612 | -41.647 | 18.231 | 84.060 | 1.00 | 25.26 |
| 11008 | O | MET | B | 612 | -42.230 | 19.284 | 84.262 | 1.00 | 24.69 |
| 11009 | N | VAL | B | 651 | -40.899 | 18.005 | 82.986 | 1.00 | 25.69 |
| 11010 | CA | VAL | B | 613 | -40.714 | 19.038 | 81.985 | 1.00 | 26.51 |
| 11011 | CB | VAL | B | 613 | -39.604 | 18.667 | 81.009 | 1.00 | 26.40 |
| 11012 | CG1 | VAL | B | 613 | -39.745 | 19.468 | 79.724 | 1.00 | 24.53 |
| 11013 | CG2 | VAL | B | 613 | -38.235 | 18.893 | 81.665 | 1.00 | 26.78 |
| 11014 | C | VAL | B | 613 | -41.995 | 19.280 | 81.206 | 1.00 | 27.69 |
| 11015 | O | VAL | B | 613 | -42.360 | 20.421 | 80.922 | 1.00 | 29.31 |
| 11016 | N | LEU | B | 614 | -42.693 | 18.213 | 80.852 | 1.00 | 28.17 |
| 11017 | CA | LEU | B | 614 | -43.923 | 18.390 | 80.108 | 1.00 | 28.42 |
| 11018 | CB | LEU | B | 614 | -44.466 | 17.047 | 79.603 | 1.00 | 28.18 |
| 11019 | CG | LEU | B | 614 | -43.650 | 16.395 | 78.490 | 1.00 | 28.05 |
| 11020 | CD1 | LEU | B | 614 | -43.707 | 17.176 | 77.182 | 1.00 | 27.46 |
| 11021 | CD2 | LEU | B | 614 | -44.096 | 14.942 | 78.285 | 1.00 | 28.59 |
| 11022 | C | LEU | B | 614 | -44.965 | 19.075 | 80.959 | 1.00 | 28.54 |
| 11023 | O | LEU | B | 614 | -45.823 | 19.756 | 80.437 | 1.00 | 28.75 |
| 11024 | N | GLY | B | 615 | -44.921 | 18.872 | 82.270 | 1.00 | 28.67 |
| 11025 | CA | GLY | B | 615 | -45.909 | 19.506 | 83.115 | 1.00 | 29.23 |
| 11026 | C | GLY | B | 615 | -45.456 | 20.827 | 83.730 | 1.00 | 29.40 |
| 11027 | O | GLY | B | 615 | -46.066 | 21.303 | 84.691 | 1.00 | 29.24 |
| 11028 | N | SER | B | 616 | -44.401 | 21.423 | 83.176 | 1.00 | 29.38 |
| 11029 | CA | SER | B | 616 | -43.844 | 22.656 | 83.739 | 1.00 | 29.93 |
| 11030 | CB | SER | B | 616 | -42.377 | 22.809 | 83.354 | 1.00 | 29.44 |
| 11031 | OG | SER | B | 616 | -42.242 | 22.899 | 81.947 | 1.00 | 30.22 |
| 11032 | C | SER | B | 616 | -44.601 | 23.914 | 83.311 | 1.00 | 30.00 |
| 11033 | O | SER | B | 616 | -44.522 | 24.942 | 83.975 | 1.00 | 30.74 |
| 11034 | N | GLY | B | 617 | -45.311 | 23.825 | 82.196 | 1.00 | 30.15 |
| 11035 | CA | GLY | B | 617 | -46.071 | 24.932 | 81.667 | 1.00 | 30.00 |
| 11036 | C | GLY | B | 617 | -45.196 | 25.825 | 80.830 | 1.00 | 30.41 |
| 11037 | O | GLY | B | 617 | -45.622 | 26.895 | 80.410 | 1.00 | 30.44 |
| 11038 | N | SER | B | 618 | -43.982 | 25.364 | 80.541 | 1.00 | 30.40 |
| 11039 | CA | SER | B | 618 | -42.996 | 26.188 | 79.834 | 1.00 | 30.05 |
| 11040 | CB | SER | B | 618 | -41.633 | 25.510 | 79.886 | 1.00 | 29.77 |
| 11041 | OG | SER | B | 618 | -41.508 | 24.580 | 78.840 | 1.00 | 29.76 |
| 11042 | C | SER | B | 618 | -43.326 | 26.550 | 78.384 | 1.00 | 30.09 |
| 11043 | O | SER | B | 618 | -42.786 | 27.507 | 77.839 | 1.00 | 30.10 |
| 11044 | N | GLY | B | 619 | -44.179 | 25.759 | 77.745 | 1.00 | 29.77 |
| 11045 | CA | GLY | B | 619 | -44.522 | 25.998 | 76.361 | 1.00 | 28.92 |
| 11046 | C | GLY | B | 619 | -43.446 | 25.601 | 75.376 | 1.00 | 28.97 |
| 11047 | O | GLY | B | 619 | -43.663 | 25.666 | 74.177 | 1.00 | 28.88 |
| 11048 | N | VAL | B | 620 | -42.285 | 25.166 | 75.847 | 1.00 | 29.59 |
| 11049 | CA | VAL | B | 620 | -41.209 | 24.853 | 74.901 | 1.00 | 30.18 |
| 11050 | CB | VAL | B | 620 | -39.800 | 24.867 | 75.558 | 1.00 | 30.73 |
| 11051 | CG1 | VAL | B | 620 | -38.724 | 24.512 | 74.524 | 1.00 | 31.72 |
| 11052 | CG2 | VAL | B | 620 | -39.488 | 26.236 | 76.143 | 1.00 | 30.75 |
| 11053 | C | VAL | B | 620 | -41.418 | 23.545 | 74.153 | 1.00 | 29.98 |
| 11054 | O | VAL | B | 620 | -41.136 | 23.448 | 72.957 | 1.00 | 30.00 |
| 11055 | N | PHE | B | 621 | -41.955 | 22.553 | 74.850 | 1.00 | 30.04 |
| 11056 | CA | PHE | B | 621 | -42.115 | 21.218 | 74.277 | 1.00 | 29.81 |
| 11057 | CB | PHE | B | 621 | -41.692 | 20.169 | 75.296 | 1.00 | 29.63 |

FIGURE 3 HI

| A | B | C | D | E | F | G | H | I | J |
|---|---|---|---|---|---|---|---|---|---|
| 11058 | CG | PHE | B | 621 | -40.263 | 20.303 | 75.720 | 1.00 | 31.06 |
| 11059 | CD1 | PHE | B | 621 | -39.912 | 21.150 | 76.763 | 1.00 | 31.31 |
| 11060 | CE1 | PHE | B | 621 | -38.601 | 21.288 | 77.144 | 1.00 | 31.62 |
| 11061 | CZ | PHE | B | 621 | -37.611 | 20.572 | 76.479 | 1.00 | 31.98 |
| 11062 | CE2 | PHE | B | 621 | -37.951 | 19.720 | 75.439 | 1.00 | 30.14 |
| 11063 | CD2 | PHE | B | 621 | -39.262 | 19.592 | 75.064 | 1.00 | 30.15 |
| 11064 | C | PHE | B | 621 | -43.508 | 20.923 | 73.760 | 1.00 | 29.14 |
| 11065 | O | PHE | B | 621 | -44.501 | 21.078 | 74.458 | 1.00 | 29.64 |
| 11066 | N | LYS | B | 622 | -43.578 | 20.494 | 72.518 | 1.00 | 28.38 |
| 11067 | CA | LYS | B | 622 | -44.846 | 20.142 | 71.936 | 1.00 | 28.57 |
| 11068 | CB | LYS | B | 622 | -44.684 | 20.107 | 70.423 | 1.00 | 28.30 |
| 11069 | CG | LYS | B | 622 | -45.972 | 19.819 | 69.654 | 1.00 | 27.32 |
| 11070 | CD | LYS | B | 622 | -45.679 | 19.304 | 68.262 | 1.00 | 25.74 |
| 11071 | CE | LYS | B | 622 | -46.812 | 19.629 | 67.312 | 1.00 | 29.17 |
| 11072 | NZ | LYS | B | 622 | -47.880 | 18.607 | 67.329 | 1.00 | 30.08 |
| 11073 | C | LYS | B | 622 | -45.188 | 18.733 | 72.361 | 1.00 | 28.90 |
| 11074 | O | LYS | B | 622 | -46.338 | 18.321 | 72.364 | 1.00 | 29.01 |
| 11075 | N | CYS | B | 623 | -44.174 | 18.049 | 72.846 | 1.00 | 29.41 |
| 11076 | CA | CYS | B | 623 | -44.163 | 16.621 | 72.777 | 1.00 | 30.38 |
| 11077 | CB | CYS | B | 623 | -43.343 | 16.450 | 71.526 | 1.00 | 32.05 |
| 11078 | SG | CYS | B | 623 | -43.925 | 15.263 | 70.415 | 1.00 | 35.26 |
| 11079 | C | CYS | B | 623 | -43.342 | 15.871 | 73.804 | 1.00 | 28.85 |
| 11080 | O | CYS | B | 623 | -42.237 | 16.278 | 74.078 | 1.00 | 28.04 |
| 11081 | N | GLY | B | 624 | -43.819 | 14.718 | 74.270 | 1.00 | 27.34 |
| 11082 | CA | GLY | B | 624 | -43.032 | 13.943 | 75.200 | 1.00 | 26.09 |
| 11083 | C | GLY | B | 624 | -43.401 | 12.492 | 75.416 | 1.00 | 25.41 |
| 11084 | O | GLY | B | 624 | -44.578 | 12.120 | 75.383 | 1.00 | 25.44 |
| 11085 | N | ILE | B | 625 | -42.381 | 11.671 | 75.649 | 1.00 | 24.38 |
| 11086 | CA | ILE | B | 625 | -42.577 | 10.258 | 75.933 | 1.00 | 23.41 |
| 11087 | CB | ILE | B | 625 | -42.016 | 9.342 | 74.813 | 1.00 | 23.54 |
| 11088 | CG1 | ILE | B | 625 | -42.540 | 9.730 | 73.439 | 1.00 | 22.37 |
| 11089 | CD1 | ILE | B | 625 | -41.874 | 8.957 | 72.293 | 1.00 | 22.74 |
| 11090 | CG2 | ILE | B | 625 | -42.374 | 7.889 | 75.106 | 1.00 | 21.80 |
| 11091 | C | ILE | B | 625 | -41.854 | 9.902 | 77.214 | 1.00 | 23.00 |
| 11092 | O | ILE | B | 625 | -40.641 | 10.039 | 77.294 | 1.00 | 22.97 |
| 11093 | N | ALA | B | 626 | -42.596 | 9.434 | 78.208 | 1.00 | 21.99 |
| 11094 | CA | ALA | B | 626 | -41.996 | 8.965 | 79.446 | 1.00 | 21.51 |
| 11095 | CB | ALA | B | 626 | -42.714 | 9.591 | 80.626 | 1.00 | 21.45 |
| 11096 | C | ALA | B | 626 | -42.059 | 7.426 | 79.530 | 1.00 | 21.24 |
| 11097 | O | ALA | B | 626 | -43.151 | 6.840 | 79.462 | 1.00 | 20.87 |
| 11098 | N | VAL | B | 627 | -40.899 | 6.776 | 79.673 | 1.00 | 21.44 |
| 11099 | CA | VAL | B | 627 | -40.835 | 5.310 | 79.805 | 1.00 | 21.61 |
| 11100 | CB | VAL | B | 627 | -39.898 | 4.661 | 78.757 | 1.00 | 21.50 |
| 11101 | CG1 | VAL | B | 627 | -40.092 | 3.155 | 78.747 | 1.00 | 21.19 |
| 11102 | CG2 | VAL | B | 627 | -40.143 | 5.231 | 77.357 | 1.00 | 21.77 |
| 11103 | C | VAL | B | 627 | -40.394 | 4.892 | 81.214 | 1.00 | 21.72 |
| 11104 | O | VAL | B | 627 | -39.311 | 5.258 | 81.658 | 1.00 | 21.89 |
| 11105 | N | ALA | B | 628 | -41.236 | 4.127 | 81.907 | 1.00 | 21.55 |
| 11106 | CA | ALA | B | 628 | -40.969 | 3.667 | 83.285 | 1.00 | 21.74 |
| 11107 | CB | ALA | B | 628 | -39.960 | 2.585 | 83.289 | 1.00 | 21.90 |
| 11108 | C | ALA | B | 628 | -40.539 | 4.778 | 84.233 | 1.00 | 22.31 |

FIGURE 3 HJ

| A | B | C | D | E | F | G | H | I | J |
|---|---|---|---|---|---|---|---|---|---|
| 11109 | O | ALA | B | 628 | -39.577 | 4.649 | 84.990 | 1.00 | 21.95 |
| 11110 | N | PRO | B | 629 | -41.309 | 5.851 | 84.239 | 1.00 | 22.62 |
| 11111 | CA | PRO | B | 629 | -40.939 | 7.052 | 84.984 | 1.00 | 22.22 |
| 11112 | CB | PRO | B | 629 | -41.924 | 8.114 | 84.462 | 1.00 | 22.59 |
| 11113 | CG | PRO | B | 629 | -42.917 | 7.396 | 83.615 | 1.00 | 22.96 |
| 11114 | CD | PRO | B | 629 | -42.638 | 5.947 | 83.610 | 1.00 | 22.34 |
| 11115 | C | PRO | B | 629 | -41.201 | 6.916 | 86.448 | 1.00 | 21.88 |
| 11116 | O | PRO | B | 629 | -42.170 | 6.250 | 86.852 | 1.00 | 22.12 |
| 11117 | N | VAL | B | 630 | -40.369 | 7.576 | 87.241 | 1.00 | 21.25 |
| 11118 | CA | VAL | B | 630 | -40.671 | 7.744 | 88.646 | 1.00 | 20.98 |
| 11119 | CB | VAL | B | 630 | -39.392 | 8.151 | 89.447 | 1.00 | 21.62 |
| 11120 | CG1 | VAL | B | 630 | -39.740 | 8.765 | 90.795 | 1.00 | 20.24 |
| 11121 | CG2 | VAL | B | 630 | -38.505 | 6.943 | 89.645 | 1.00 | 20.74 |
| 11122 | C | VAL | B | 630 | -41.686 | 8.877 | 88.630 | 1.00 | 20.94 |
| 11123 | O | VAL | B | 630 | -41.624 | 9.758 | 87.766 | 1.00 | 20.42 |
| 11124 | N | SER | B | 631 | -42.654 | 8.866 | 89.533 | 1.00 | 21.29 |
| 11125 | CA | SER | B | 631 | -43.641 | 9.950 | 89.500 | 1.00 | 22.20 |
| 11126 | CB | SER | B | 631 | -45.016 | 9.426 | 89.102 | 1.00 | 21.51 |
| 11127 | OG | SER | B | 631 | -45.506 | 8.572 | 90.108 | 1.00 | 21.79 |
| 11128 | C | SER | B | 631 | -43.715 | 10.708 | 90.826 | 1.00 | 22.31 |
| 11129 | O | SER | B | 631 | -44.127 | 11.857 | 90.875 | 1.00 | 22.12 |
| 11130 | N | ARG | B | 632 | -43.369 | 10.028 | 91.902 | 1.00 | 22.84 |
| 11131 | CA | ARG | B | 632 | -43.251 | 10.676 | 93.178 | 1.00 | 24.48 |
| 11132 | CB | ARG | B | 632 | -44.570 | 10.749 | 93.938 | 1.00 | 24.78 |
| 11133 | CG | ARG | B | 632 | -44.772 | 9.608 | 94.859 | 1.00 | 28.29 |
| 11134 | CD | ARG | B | 632 | -45.406 | 9.963 | 96.172 | 1.00 | 33.49 |
| 11135 | NE | ARG | B | 632 | -46.447 | 10.954 | 96.047 | 1.00 | 35.71 |
| 11136 | CZ | ARG | B | 632 | -47.196 | 11.363 | 97.060 | 1.00 | 38.06 |
| 11137 | NH1 | ARG | B | 632 | -48.111 | 12.306 | 96.862 | 1.00 | 36.08 |
| 11138 | NH2 | ARG | B | 632 | -47.033 | 10.826 | 98.272 | 1.00 | 38.76 |
| 11139 | C | ARG | B | 632 | -42.224 | 9.873 | 93.932 | 1.00 | 24.25 |
| 11140 | O | ARG | B | 632 | -42.271 | 8.637 | 93.923 | 1.00 | 24.75 |
| 11141 | N | TRP | B | 633 | -41.314 | 10.582 | 94.592 | 1.00 | 24.41 |
| 11142 | CA | TRP | B | 633 | -40.159 | 9.974 | 95.258 | 1.00 | 24.82 |
| 11143 | CB | TRP | B | 633 | -39.121 | 11.050 | 95.606 | 1.00 | 24.74 |
| 11144 | CG | TRP | B | 633 | -38.523 | 11.596 | 94.366 | 1.00 | 23.36 |
| 11145 | CD1 | TRP | B | 633 | -38.728 | 12.816 | 93.828 | 1.00 | 21.42 |
| 11146 | NE1 | TRP | B | 633 | -38.047 | 12.927 | 92.637 | 1.00 | 20.50 |
| 11147 | CE2 | TRP | B | 633 | -37.376 | 11.759 | 92.394 | 1.00 | 20.18 |
| 11148 | CD2 | TRP | B | 633 | -37.666 | 10.888 | 93.449 | 1.00 | 22.71 |
| 11149 | CE3 | TRP | B | 633 | -37.107 | 9.598 | 93.428 | 1.00 | 21.96 |
| 11150 | CZ3 | TRP | B | 633 | -36.286 | 9.239 | 92.375 | 1.00 | 20.82 |
| 11151 | CH2 | TRP | B | 633 | -36.010 | 10.133 | 91.345 | 1.00 | 22.31 |
| 11152 | CZ2 | TRP | B | 633 | -36.545 | 11.398 | 91.331 | 1.00 | 22.59 |
| 11153 | C | TRP | B | 633 | -40.485 | 9.045 | 96.420 | 1.00 | 25.58 |
| 11154 | O | TRP | B | 633 | -39.739 | 8.128 | 96.714 | 1.00 | 26.20 |
| 11155 | N | GLU | B | 634 | -41.623 | 9.234 | 97.059 | 1.00 | 26.51 |
| 11156 | CA | GLU | B | 634 | -41.974 | 8.321 | 98.127 | 1.00 | 27.59 |
| 11157 | CB | GLU | B | 634 | -43.173 | 8.852 | 98.923 | 1.00 | 28.41 |
| 11158 | CG | GLU | B | 634 | -42.875 | 10.009 | 99.859 | 1.00 | 30.31 |
| 11159 | CD | GLU | B | 634 | -43.883 | 11.137 | 99.660 | 1.00 | 34.65 |

FIGURE 3 HK

| A | B | C | D | E | F | G | H | I | J |
|---|---|---|---|---|---|---|---|---|---|
| 11160 | OE1 | GLU | B | 634 | -44.789 | 11.313 | 100.508 | 1.00 | 35.00 |
| 11161 | OE2 | GLU | B | 634 | -43.789 | 11.829 | 98.616 | 1.00 | 37.30 |
| 11162 | C | GLU | B | 634 | -42.260 | 6.898 | 97.602 | 1.00 | 27.46 |
| 11163 | O | GLU | B | 634 | -42.306 | 5.961 | 98.389 | 1.00 | 27.14 |
| 11164 | N | TYR | B | 635 | -42.454 | 6.752 | 96.285 | 1.00 | 27.23 |
| 11165 | CA | TYR | B | 635 | -42.699 | 5.441 | 95.655 | 1.00 | 27.06 |
| 11166 | CB | TYR | B | 635 | -43.411 | 5.595 | 94.309 | 1.00 | 26.89 |
| 11167 | CG | TYR | B | 635 | -44.817 | 6.153 | 94.352 | 1.00 | 26.76 |
| 11168 | CD1 | TYR | B | 635 | -45.628 | 5.992 | 95.474 | 1.00 | 23.71 |
| 11169 | CE1 | TYR | B | 635 | -46.906 | 6.487 | 95.498 | 1.00 | 24.06 |
| 11170 | CZ | TYR | B | 635 | -47.394 | 7.155 | 94.396 | 1.00 | 25.50 |
| 11171 | OH | TYR | B | 635 | -48.675 | 7.661 | 94.391 | 1.00 | 26.00 |
| 11172 | CE2 | TYR | B | 635 | -46.609 | 7.334 | 93.273 | 1.00 | 26.24 |
| 11173 | CD2 | TYR | B | 635 | -45.335 | 6.831 | 93.251 | 1.00 | 25.67 |
| 11174 | C | TYR | B | 635 | -41.427 | 4.681 | 95.322 | 1.00 | 27.02 |
| 11175 | O | TYR | B | 635 | -41.461 | 3.479 | 95.123 | 1.00 | 27.59 |
| 11176 | N | TYR | B | 636 | -40.314 | 5.388 | 95.200 | 1.00 | 27.04 |
| 11177 | CA | TYR | B | 636 | -39.083 | 4.743 | 94.808 | 1.00 | 26.78 |
| 11178 | CB | TYR | B | 636 | -38.226 | 5.682 | 93.990 | 1.00 | 26.50 |
| 11179 | CG | TYR | B | 636 | -37.243 | 4.930 | 93.178 | 1.00 | 25.84 |
| 11180 | CD1 | TYR | B | 636 | -37.633 | 3.778 | 92.512 | 1.00 | 24.02 |
| 11181 | CE1 | TYR | B | 636 | -36.735 | 3.060 | 91.765 | 1.00 | 25.85 |
| 11182 | CZ | TYR | B | 636 | -35.442 | 3.480 | 91.663 | 1.00 | 26.22 |
| 11183 | OH | TYR | B | 636 | -34.578 | 2.738 | 90.901 | 1.00 | 29.04 |
| 11184 | CE2 | TYR | B | 636 | -35.014 | 4.638 | 92.318 | 1.00 | 27.07 |
| 11185 | CD2 | TYR | B | 636 | -35.917 | 5.350 | 93.076 | 1.00 | 25.48 |
| 11186 | C | TYR | B | 636 | -38.320 | 4.168 | 95.995 | 1.00 | 26.99 |
| 11187 | O | TYR | B | 636 | -38.723 | 4.348 | 97.133 | 1.00 | 26.78 |
| 11188 | N | ASP | B | 637 | -37.233 | 3.451 | 95.727 | 1.00 | 27.76 |
| 11189 | CA | ASP | B | 637 | -36.554 | 2.749 | 96.793 | 1.00 | 28.64 |
| 11190 | CB | ASP | B | 637 | -35.692 | 1.581 | 96.265 | 1.00 | 29.22 |
| 11191 | CG | ASP | B | 637 | -34.457 | 2.038 | 95.509 | 1.00 | 29.73 |
| 11192 | OD1 | ASP | B | 637 | -33.618 | 2.766 | 96.088 | 1.00 | 30.15 |
| 11193 | OD2 | ASP | B | 637 | -34.223 | 1.679 | 94.339 | 1.00 | 27.88 |
| 11194 | C | ASP | B | 637 | -35.796 | 3.678 | 97.742 | 1.00 | 28.58 |
| 11195 | O | ASP | B | 637 | -35.351 | 4.759 | 97.355 | 1.00 | 27.81 |
| 11196 | N | SER | B | 638 | -35.687 | 3.252 | 98.993 | 1.00 | 28.79 |
| 11197 | CA | SER | B | 638 | -35.047 | 4.070 | 100.021 | 1.00 | 29.71 |
| 11198 | CB | SER | B | 638 | -35.147 | 3.364 | 101.363 | 1.00 | 30.02 |
| 11199 | OG | SER | B | 638 | -34.538 | 2.089 | 101.298 | 1.00 | 31.85 |
| 11200 | C | SER | B | 638 | -33.586 | 4.472 | 99.757 | 1.00 | 29.51 |
| 11201 | O | SER | B | 638 | -33.218 | 5.666 | 99.859 | 1.00 | 29.46 |
| 11202 | N | VAL | B | 639 | -32.739 | 3.515 | 99.398 | 1.00 | 29.23 |
| 11203 | CA | VAL | B | 639 | -31.328 | 3.893 | 99.293 | 1.00 | 28.76 |
| 11204 | CB | VAL | B | 639 | -30.347 | 2.708 | 99.372 | 1.00 | 28.62 |
| 11205 | CG1 | VAL | B | 639 | -29.415 | 2.664 | 98.191 | 1.00 | 30.17 |
| 11206 | CG2 | VAL | B | 639 | -31.069 | 1.434 | 99.627 | 1.00 | 27.57 |
| 11207 | C | VAL | B | 639 | -31.024 | 4.879 | 98.183 | 1.00 | 28.25 |
| 11208 | O | VAL | B | 639 | -30.274 | 5.825 | 98.383 | 1.00 | 28.61 |
| 11209 | N | TYR | B | 640 | -31.623 | 4.702 | 97.022 | 1.00 | 27.85 |
| 11210 | CA | TYR | B | 640 | -31.400 | 5.680 | 95.979 | 1.00 | 27.17 |

FIGURE 3 HL

| A | B | C | D | E | F | G | H | I | J |
|---|---|---|---|---|---|---|---|---|---|
| 11211 | CB | TYR | B | 640 | -31.926 | 5.154 | 94.654 | 1.00 | 27.16 |
| 11212 | CG | TYR | B | 640 | -31.729 | 6.093 | 93.481 | 1.00 | 25.27 |
| 11213 | CD1 | TYR | B | 640 | -30.704 | 5.885 | 92.568 | 1.00 | 23.80 |
| 11214 | CE1 | TYR | B | 640 | -30.523 | 6.752 | 91.487 | 1.00 | 24.47 |
| 11215 | CZ | TYR | B | 640 | -31.386 | 7.814 | 91.306 | 1.00 | 22.75 |
| 11216 | OH | TYR | B | 640 | -31.212 | 8.651 | 90.229 | 1.00 | 23.63 |
| 11217 | CE2 | TYR | B | 640 | -32.420 | 8.028 | 92.191 | 1.00 | 21.55 |
| 11218 | CD2 | TYR | B | 640 | -32.579 | 7.175 | 93.280 | 1.00 | 23.20 |
| 11219 | C | TYR | B | 640 | -32.081 | 7.018 | 96.335 | 1.00 | 27.36 |
| 11220 | O | TYR | B | 640 | -31.454 | 8.072 | 96.309 | 1.00 | 27.20 |
| 11221 | N | THR | B | 641 | -33.358 | 6.975 | 96.680 | 1.00 | 27.02 |
| 11222 | CA | THR | B | 641 | -34.083 | 8.216 | 96.969 | 1.00 | 27.70 |
| 11223 | CB | THR | B | 641 | -35.588 | 7.934 | 97.220 | 1.00 | 27.48 |
| 11224 | OG1 | THR | B | 641 | -36.098 | 7.085 | 96.180 | 1.00 | 26.79 |
| 11225 | CG2 | THR | B | 641 | -36.385 | 9.217 | 97.118 | 1.00 | 26.28 |
| 11226 | C | THR | B | 641 | -33.546 | 9.032 | 98.146 | 1.00 | 27.73 |
| 11227 | O | THR | B | 641 | -33.308 | 10.233 | 98.017 | 1.00 | 27.27 |
| 11228 | N | GLU | B | 642 | -33.421 | 8.387 | 99.301 | 1.00 | 28.13 |
| 11229 | CA | GLU | B | 642 | -32.970 | 9.069 | 100.519 | 1.00 | 28.83 |
| 11230 | CB | GLU | B | 642 | -33.056 | 8.144 | 101.740 | 1.00 | 28.92 |
| 11231 | CG | GLU | B | 642 | -34.464 | 7.610 | 102.007 | 1.00 | 27.27 |
| 11232 | CD | GLU | B | 642 | -34.479 | 6.484 | 103.020 | 1.00 | 28.72 |
| 11233 | OE1 | GLU | B | 642 | -33.413 | 6.218 | 103.605 | 1.00 | 30.14 |
| 11234 | OE2 | GLU | B | 642 | -35.540 | 5.860 | 103.241 | 1.00 | 24.56 |
| 11235 | C | GLU | B | 642 | -31.571 | 9.647 | 100.339 | 1.00 | 29.65 |
| 11236 | O | GLU | B | 642 | -31.209 | 10.617 | 100.998 | 1.00 | 29.85 |
| 11237 | N | ARG | B | 643 | -30.816 | 9.105 | 99.385 | 1.00 | 30.34 |
| 11238 | CA | ARG | B | 643 | -29.468 | 9.582 | 99.124 | 1.00 | 30.99 |
| 11239 | CB | ARG | B | 643 | -28.754 | 8.700 | 98.088 | 1.00 | 30.95 |
| 11240 | CG | ARG | B | 643 | -27.281 | 9.049 | 97.868 | 1.00 | 29.73 |
| 11241 | CD | ARG | B | 643 | -26.599 | 8.237 | 96.755 | 1.00 | 29.27 |
| 11242 | NE | ARG | B | 643 | -26.793 | 6.805 | 96.945 | 1.00 | 27.98 |
| 11243 | CZ | ARG | B | 643 | -27.111 | 5.957 | 95.974 | 1.00 | 27.57 |
| 11244 | NH1 | ARG | B | 643 | -27.282 | 4.687 | 96.257 | 1.00 | 26.22 |
| 11245 | NH2 | ARG | B | 643 | -27.274 | 6.379 | 94.720 | 1.00 | 26.92 |
| 11246 | C | ARG | B | 643 | -29.502 | 11.017 | 98.643 | 1.00 | 31.73 |
| 11247 | O | ARG | B | 643 | -28.590 | 11.813 | 98.920 | 1.00 | 31.73 |
| 11248 | N | TYR | B | 644 | -30.566 | 11.348 | 97.927 | 1.00 | 32.09 |
| 11249 | CA | TYR | B | 644 | -30.703 | 12.671 | 97.353 | 1.00 | 32.36 |
| 11250 | CB | TYR | B | 644 | -30.970 | 12.547 | 95.847 | 1.00 | 32.58 |
| 11251 | CG | TYR | B | 644 | -30.084 | 11.532 | 95.149 | 1.00 | 32.51 |
| 11252 | CD1 | TYR | B | 644 | -28.726 | 11.777 | 94.954 | 1.00 | 33.05 |
| 11253 | CE1 | TYR | B | 644 | -27.910 | 10.845 | 94.313 | 1.00 | 31.76 |
| 11254 | CZ | TYR | B | 644 | -28.456 | 9.660 | 93.857 | 1.00 | 30.48 |
| 11255 | OH | TYR | B | 644 | -27.665 | 8.733 | 93.237 | 1.00 | 29.23 |
| 11256 | CE2 | TYR | B | 644 | -29.794 | 9.393 | 94.037 | 1.00 | 32.14 |
| 11257 | CD2 | TYR | B | 644 | -30.604 | 10.326 | 94.682 | 1.00 | 32.61 |
| 11258 | C | TYR | B | 644 | -31.811 | 13.488 | 98.006 | 1.00 | 32.48 |
| 11259 | O | TYR | B | 644 | -31.833 | 14.699 | 97.889 | 1.00 | 32.79 |
| 11260 | N | MET | B | 645 | -32.704 | 12.837 | 98.731 | 1.00 | 33.14 |
| 11261 | CA | MET | B | 645 | -33.878 | 13.525 | 99.259 | 1.00 | 33.84 |

FIGURE 3 HM

| A | B | C | D | E | F | G | H | I | J |
|---|---|---|---|---|---|---|---|---|---|
| 11262 | CB | MET | B | 645 | -35.143 | 12.910 | 98.652 | 1.00 | 33.47 |
| 11263 | CG | MET | B | 645 | -35.302 | 13.175 | 97.165 | 1.00 | 32.72 |
| 11264 | SD | MET | B | 645 | -35.747 | 14.897 | 96.878 | 1.00 | 35.29 |
| 11265 | CE | MET | B | 645 | -37.378 | 14.900 | 97.690 | 1.00 | 31.46 |
| 11266 | C | MET | B | 645 | -34.006 | 13.492 | 100.774 | 1.00 | 34.80 |
| 11267 | O | MET | B | 645 | -34.934 | 14.071 | 101.329 | 1.00 | 35.04 |
| 11268 | N | GLY | B | 646 | -33.089 | 12.810 | 101.446 | 1.00 | 35.50 |
| 11269 | CA | GLY | B | 646 | -33.198 | 12.669 | 102.879 | 1.00 | 36.25 |
| 11270 | C | GLY | B | 646 | -34.489 | 11.931 | 103.173 | 1.00 | 37.10 |
| 11271 | O | GLY | B | 646 | -35.018 | 11.221 | 102.312 | 1.00 | 37.45 |
| 11272 | N | LEU | B | 647 | -35.003 | 12.092 | 104.385 | 1.00 | 37.37 |
| 11273 | CA | LEU | B | 647 | -36.213 | 11.405 | 104.784 | 1.00 | 37.69 |
| 11274 | CB | LEU | B | 647 | -36.164 | 11.134 | 106.280 | 1.00 | 37.94 |
| 11275 | CG | LEU | B | 647 | -35.666 | 9.750 | 106.672 | 1.00 | 39.05 |
| 11276 | CD1 | LEU | B | 647 | -34.972 | 9.031 | 105.508 | 1.00 | 39.78 |
| 11277 | CD2 | LEU | B | 647 | -34.766 | 9.832 | 107.891 | 1.00 | 42.00 |
| 11278 | C | LEU | B | 647 | -37.449 | 12.204 | 104.435 | 1.00 | 37.87 |
| 11279 | O | LEU | B | 647 | -37.431 | 13.433 | 104.478 | 1.00 | 38.26 |
| 11280 | N | PRO | B | 648 | -38.522 | 11.513 | 104.057 | 1.00 | 37.85 |
| 11281 | CA | PRO | B | 648 | -39.791 | 12.171 | 103.763 | 1.00 | 38.05 |
| 11282 | CB | PRO | B | 648 | -40.468 | 11.169 | 102.821 | 1.00 | 37.86 |
| 11283 | CG | PRO | B | 648 | -40.047 | 9.848 | 103.376 | 1.00 | 37.20 |
| 11284 | CD | PRO | B | 648 | -38.617 | 10.052 | 103.861 | 1.00 | 37.95 |
| 11285 | C | PRO | B | 648 | -40.594 | 12.382 | 105.051 | 1.00 | 38.12 |
| 11286 | O | PRO | B | 648 | -41.737 | 11.967 | 105.186 | 1.00 | 37.94 |
| 11287 | N | THR | B | 649 | -39.963 | 13.033 | 106.013 | 1.00 | 39.12 |
| 11288 | CA | THR | B | 649 | -40.621 | 13.361 | 107.265 | 1.00 | 39.41 |
| 11289 | CB | THR | B | 649 | -39.795 | 12.811 | 108.432 | 1.00 | 39.84 |
| 11290 | OG1 | THR | B | 649 | -38.439 | 13.266 | 108.316 | 1.00 | 40.07 |
| 11291 | CG2 | THR | B | 649 | -39.676 | 11.284 | 108.333 | 1.00 | 38.96 |
| 11292 | C | THR | B | 649 | -40.766 | 14.878 | 107.369 | 1.00 | 39.87 |
| 11293 | O | THR | B | 649 | -40.027 | 15.625 | 106.739 | 1.00 | 39.52 |
| 11294 | N | PRO | B | 650 | -41.738 | 15.347 | 108.136 | 1.00 | 40.74 |
| 11295 | CA | PRO | B | 650 | -41.866 | 16.789 | 108.358 | 1.00 | 41.41 |
| 11296 | CB | PRO | B | 650 | -43.029 | 16.888 | 109.344 | 1.00 | 41.77 |
| 11297 | CG | PRO | B | 650 | -43.830 | 15.638 | 109.075 | 1.00 | 40.96 |
| 11298 | CD | PRO | B | 650 | -42.788 | 14.576 | 108.826 | 1.00 | 40.74 |
| 11299 | C | PRO | B | 650 | -40.573 | 17.295 | 108.986 | 1.00 | 42.00 |
| 11300 | O | PRO | B | 650 | -40.084 | 18.370 | 108.630 | 1.00 | 42.19 |
| 11301 | N | GLU | B | 651 | -39.998 | 16.503 | 109.884 | 1.00 | 42.27 |
| 11302 | CA | GLU | B | 651 | -38.750 | 16.900 | 110.517 | 1.00 | 43.04 |
| 11303 | CB | GLU | B | 651 | -38.437 | 16.013 | 111.731 | 1.00 | 43.65 |
| 11304 | CG | GLU | B | 651 | -38.960 | 14.581 | 111.639 | 1.00 | 46.27 |
| 11305 | CD | GLU | B | 651 | -40.428 | 14.450 | 112.031 | 1.00 | 48.91 |
| 11306 | OE1 | GLU | B | 651 | -41.001 | 13.348 | 111.860 | 1.00 | 49.45 |
| 11307 | OE2 | GLU | B | 651 | -41.012 | 15.447 | 112.519 | 1.00 | 50.85 |
| 11308 | C | GLU | B | 651 | -37.580 | 16.920 | 109.530 | 1.00 | 42.60 |
| 11309 | O | GLU | B | 651 | -36.536 | 17.501 | 109.803 | 1.00 | 42.70 |
| 11310 | N | ASP | B | 652 | -37.751 | 16.301 | 108.366 | 1.00 | 41.94 |
| 11311 | CA | ASP | B | 652 | -36.658 | 16.284 | 107.398 | 1.00 | 40.34 |
| 11312 | CB | ASP | B | 652 | -36.195 | 14.849 | 107.140 | 1.00 | 40.56 |

FIGURE 3 HN

| A | B | C | D | E | F | G | H | I | J |
|---|---|---|---|---|---|---|---|---|---|
| 11313 | CG | ASP | B | 652 | -34.881 | 14.782 | 106.389 | 1.00 | 41.32 |
| 11314 | OD1 | ASP | B | 652 | -34.287 | 13.686 | 106.351 | 1.00 | 42.94 |
| 11315 | OD2 | ASP | B | 652 | -34.360 | 15.761 | 105.807 | 1.00 | 43.08 |
| 11316 | C | ASP | B | 652 | -36.974 | 17.009 | 106.090 | 1.00 | 39.16 |
| 11317 | O | ASP | B | 652 | -36.784 | 18.210 | 105.976 | 1.00 | 38.18 |
| 11318 | N | ASN | B | 653 | -37.481 | 16.278 | 105.102 | 1.00 | 38.59 |
| 11319 | CA | ASN | B | 653 | -37.642 | 16.866 | 103.777 | 1.00 | 37.75 |
| 11320 | CB | ASN | B | 653 | -36.497 | 16.372 | 102.884 | 1.00 | 37.56 |
| 11321 | CG | ASN | B | 653 | -36.285 | 17.237 | 101.693 | 1.00 | 36.92 |
| 11322 | OD1 | ASN | B | 653 | -36.601 | 18.411 | 101.720 | 1.00 | 37.91 |
| 11323 | ND2 | ASN | B | 653 | -35.757 | 16.661 | 100.621 | 1.00 | 38.45 |
| 11324 | C | ASN | B | 653 | -38.991 | 16.603 | 103.116 | 1.00 | 37.39 |
| 11325 | O | ASN | B | 653 | -39.155 | 16.811 | 101.906 | 1.00 | 37.19 |
| 11326 | N | LEU | B | 654 | -39.959 | 16.160 | 103.908 | 1.00 | 36.97 |
| 11327 | CA | LEU | B | 654 | -41.278 | 15.848 | 103.377 | 1.00 | 37.08 |
| 11328 | CB | LEU | B | 654 | -42.278 | 15.570 | 104.491 | 1.00 | 37.28 |
| 11329 | CG | LEU | B | 654 | -43.666 | 15.180 | 103.971 | 1.00 | 38.01 |
| 11330 | CD1 | LEU | B | 654 | -44.662 | 15.116 | 105.102 | 1.00 | 38.44 |
| 11331 | CD2 | LEU | B | 654 | -43.632 | 13.847 | 103.197 | 1.00 | 36.04 |
| 11332 | C | LEU | B | 654 | -41.850 | 16.909 | 102.450 | 1.00 | 36.99 |
| 11333 | O | LEU | B | 654 | -42.491 | 16.578 | 101.458 | 1.00 | 37.11 |
| 11334 | N | ASP | B | 655 | -41.626 | 18.184 | 102.743 | 1.00 | 36.71 |
| 11335 | CA | ASP | B | 655 | -42.205 | 19.200 | 101.874 | 1.00 | 37.08 |
| 11336 | CB | ASP | B | 655 | -41.923 | 20.620 | 102.360 | 1.00 | 37.80 |
| 11337 | CG | ASP | B | 655 | -42.766 | 21.000 | 103.567 | 1.00 | 40.19 |
| 11338 | OD1 | ASP | B | 655 | -43.653 | 20.200 | 103.963 | 1.00 | 41.54 |
| 11339 | OD2 | ASP | B | 655 | -42.599 | 22.073 | 104.188 | 1.00 | 43.81 |
| 11340 | C | ASP | B | 655 | -41.756 | 19.040 | 100.439 | 1.00 | 36.43 |
| 11341 | O | ASP | B | 655 | -42.586 | 19.062 | 99.534 | 1.00 | 36.62 |
| 11342 | N | HIS | B | 656 | -40.456 | 18.864 | 100.221 | 1.00 | 35.68 |
| 11343 | CA | HIS | B | 656 | -39.984 | 18.756 | 98.851 | 1.00 | 34.84 |
| 11344 | CB | HIS | B | 656 | -38.497 | 19.045 | 98.675 | 1.00 | 34.52 |
| 11345 | CG | HIS | B | 656 | -38.088 | 19.053 | 97.238 | 1.00 | 34.18 |
| 11346 | ND1 | HIS | B | 656 | -38.490 | 20.039 | 96.364 | 1.00 | 34.46 |
| 11347 | CE1 | HIS | B | 656 | -38.037 | 19.763 | 95.153 | 1.00 | 35.30 |
| 11348 | NE2 | HIS | B | 656 | -37.380 | 18.617 | 95.206 | 1.00 | 34.69 |
| 11349 | CD2 | HIS | B | 656 | -37.413 | 18.144 | 96.496 | 1.00 | 32.87 |
| 11350 | C | HIS | B | 656 | -40.376 | 17.440 | 98.192 | 1.00 | 34.46 |
| 11351 | O | HIS | B | 656 | -40.547 | 17.385 | 96.987 | 1.00 | 34.36 |
| 11352 | N | TYR | B | 657 | -40.533 | 16.392 | 98.985 | 1.00 | 34.15 |
| 11353 | CA | TYR | B | 657 | -41.034 | 15.135 | 98.459 | 1.00 | 34.15 |
| 11354 | CB | TYR | B | 657 | -41.248 | 14.128 | 99.578 | 1.00 | 33.67 |
| 11355 | CG | TYR | B | 657 | -40.122 | 13.151 | 99.774 | 1.00 | 34.12 |
| 11356 | CD1 | TYR | B | 657 | -40.111 | 11.918 | 99.109 | 1.00 | 32.26 |
| 11357 | CE1 | TYR | B | 657 | -39.073 | 11.019 | 99.310 | 1.00 | 32.46 |
| 11358 | CZ | TYR | B | 657 | -38.026 | 11.364 | 100.171 | 1.00 | 32.01 |
| 11359 | OH | TYR | B | 657 | -36.988 | 10.500 | 100.408 | 1.00 | 28.40 |
| 11360 | CE2 | TYR | B | 657 | -38.021 | 12.576 | 100.814 | 1.00 | 31.61 |
| 11361 | CD2 | TYR | B | 657 | -39.059 | 13.461 | 100.610 | 1.00 | 32.78 |
| 11362 | C | TYR | B | 657 | -42.371 | 15.374 | 97.810 | 1.00 | 34.51 |
| 11363 | O | TYR | B | 657 | -42.598 | 14.969 | 96.663 | 1.00 | 35.46 |

FIGURE 3 HO

| A | B | C | D | E | F | G | H | I | J |
|---|---|---|---|---|---|---|---|---|---|
| 11364 | N | ARG | B | 658 | -43.257 | 16.041 | 98.548 | 1.00 | 34.34 |
| 11365 | CA | ARG | B | 658 | -44.621 | 16.309 | 98.078 | 1.00 | 34.28 |
| 11366 | CB | ARG | B | 658 | -45.533 | 16.710 | 99.251 | 1.00 | 33.97 |
| 11367 | CG | ARG | B | 658 | -45.624 | 15.670 | 100.366 | 1.00 | 33.52 |
| 11368 | CD | ARG | B | 658 | -46.558 | 14.482 | 100.053 | 1.00 | 32.99 |
| 11369 | NE | ARG | B | 658 | -46.162 | 13.262 | 100.760 | 1.00 | 31.06 |
| 11370 | CZ | ARG | B | 658 | -46.732 | 12.811 | 101.868 | 1.00 | 30.92 |
| 11371 | NH1 | ARG | B | 658 | -47.741 | 13.466 | 102.423 | 1.00 | 30.91 |
| 11372 | NH2 | ARG | B | 658 | -46.284 | 11.697 | 102.431 | 1.00 | 31.55 |
| 11373 | C | ARG | B | 658 | -44.696 | 17.381 | 96.998 | 1.00 | 34.35 |
| 11374 | O | ARG | B | 658 | -45.724 | 17.517 | 96.329 | 1.00 | 34.58 |
| 11375 | N | ASN | B | 659 | -43.616 | 18.130 | 96.810 | 1.00 | 33.88 |
| 11376 | CA | ASN | B | 659 | -43.632 | 19.228 | 95.846 | 1.00 | 34.13 |
| 11377 | CB | ASN | B | 659 | -42.758 | 20.375 | 96.365 | 1.00 | 35.28 |
| 11378 | CG | ASN | B | 659 | -43.468 | 21.707 | 96.337 | 1.00 | 39.53 |
| 11379 | OD1 | ASN | B | 659 | -44.314 | 21.978 | 97.202 | 1.00 | 45.44 |
| 11380 | ND2 | ASN | B | 659 | -43.140 | 22.552 | 95.351 | 1.00 | 42.35 |
| 11381 | C | ASN | B | 659 | -43.073 | 18.811 | 94.507 | 1.00 | 32.93 |
| 11382 | O | ASN | B | 659 | -43.151 | 19.554 | 93.535 | 1.00 | 32.81 |
| 11383 | N | SER | B | 660 | -42.486 | 17.626 | 94.462 | 1.00 | 31.18 |
| 11384 | CA | SER | B | 660 | -41.767 | 17.196 | 93.275 | 1.00 | 30.39 |
| 11385 | CB | SER | B | 660 | -40.329 | 16.884 | 93.676 | 1.00 | 29.81 |
| 11386 | OG | SER | B | 660 | -40.358 | 15.885 | 94.689 | 1.00 | 29.23 |
| 11387 | C | SER | B | 660 | -42.386 | 15.943 | 92.642 | 1.00 | 29.69 |
| 11388 | O | SER | B | 660 | -41.685 | 15.002 | 92.263 | 1.00 | 29.31 |
| 11389 | N | THR | B | 661 | -43.699 | 15.913 | 92.568 | 1.00 | 28.50 |
| 11390 | CA | THR | B | 661 | -44.355 | 14.767 | 91.984 | 1.00 | 28.29 |
| 11391 | CB | THR | B | 661 | -45.546 | 14.366 | 92.818 | 1.00 | 27.45 |
| 11392 | OG1 | THR | B | 661 | -46.535 | 15.387 | 92.715 | 1.00 | 29.47 |
| 11393 | CG2 | THR | B | 661 | -45.191 | 14.390 | 94.278 | 1.00 | 28.51 |
| 11394 | C | THR | B | 661 | -44.840 | 15.193 | 90.634 | 1.00 | 27.58 |
| 11395 | O | THR | B | 661 | -45.141 | 16.360 | 90.433 | 1.00 | 26.38 |
| 11396 | N | VAL | B | 662 | -44.937 | 14.255 | 89.699 | 1.00 | 27.71 |
| 11397 | CA | VAL | B | 662 | -45.468 | 14.649 | 88.413 | 1.00 | 27.87 |
| 11398 | CB | VAL | B | 662 | -45.105 | 13.696 | 87.244 | 1.00 | 28.03 |
| 11399 | CG1 | VAL | B | 662 | -43.870 | 12.889 | 87.559 | 1.00 | 27.47 |
| 11400 | CG2 | VAL | B | 662 | -46.276 | 12.834 | 86.853 | 1.00 | 28.38 |
| 11401 | C | VAL | B | 662 | -46.960 | 14.882 | 88.540 | 1.00 | 27.13 |
| 11402 | O | VAL | B | 662 | -47.479 | 15.797 | 87.962 | 1.00 | 27.77 |
| 11403 | N | MET | B | 663 | -47.633 | 14.082 | 89.342 | 1.00 | 27.99 |
| 11404 | CA | MET | B | 663 | -49.089 | 14.201 | 89.497 | 1.00 | 28.23 |
| 11405 | CB | MET | B | 663 | -49.606 | 13.268 | 90.587 | 1.00 | 27.98 |
| 11406 | CG | MET | B | 663 | -49.700 | 11.811 | 90.119 | 1.00 | 29.16 |
| 11407 | SD | MET | B | 663 | -48.064 | 11.094 | 89.939 | 1.00 | 28.55 |
| 11408 | CE | MET | B | 663 | -47.730 | 10.581 | 91.585 | 1.00 | 25.42 |
| 11409 | C | MET | B | 663 | -49.568 | 15.598 | 89.801 | 1.00 | 28.71 |
| 11410 | O | MET | B | 663 | -50.646 | 15.979 | 89.386 | 1.00 | 28.82 |
| 11411 | N | SER | B | 664 | -48.782 | 16.368 | 90.547 | 1.00 | 29.20 |
| 11412 | CA | SER | B | 664 | -49.234 | 17.699 | 90.904 | 1.00 | 29.56 |
| 11413 | CB | SER | B | 664 | -48.417 | 18.268 | 92.069 | 1.00 | 29.71 |
| 11414 | OG | SER | B | 664 | -47.127 | 18.659 | 91.638 | 1.00 | 30.83 |

FIGURE 3 HP

| A | B | C | D | E | F | G | H | I | J |
|---|---|---|---|---|---|---|---|---|---|
| 11415 | C | SER | B | 664 | -49.201 | 18.630 | 89.690 | 1.00 | 29.03 |
| 11416 | O | SER | B | 664 | -49.812 | 19.694 | 89.691 | 1.00 | 29.19 |
| 11417 | N | ARG | B | 665 | -48.511 | 18.223 | 88.642 | 1.00 | 28.31 |
| 11418 | CA | ARG | B | 665 | -48.440 | 19.072 | 87.452 | 1.00 | 27.87 |
| 11419 | CB | ARG | B | 665 | -47.017 | 19.073 | 86.876 | 1.00 | 28.19 |
| 11420 | CG | ARG | B | 665 | -45.941 | 19.442 | 87.920 | 1.00 | 27.90 |
| 11421 | CD | ARG | B | 665 | -44.509 | 19.413 | 87.389 | 1.00 | 30.07 |
| 11422 | NE | ARG | B | 665 | -43.613 | 20.173 | 88.261 | 1.00 | 30.26 |
| 11423 | CZ | ARG | B | 665 | -42.526 | 20.811 | 87.849 | 1.00 | 29.50 |
| 11424 | NH1 | ARG | B | 665 | -42.166 | 20.784 | 86.574 | 1.00 | 25.52 |
| 11425 | NH2 | ARG | B | 665 | -41.786 | 21.479 | 88.730 | 1.00 | 32.36 |
| 11426 | C | ARG | B | 665 | -49.448 | 18.636 | 86.408 | 1.00 | 27.44 |
| 11427 | O | ARG | B | 665 | -49.492 | 19.183 | 85.330 | 1.00 | 26.97 |
| 11428 | N | ALA | B | 666 | -50.289 | 17.675 | 86.755 | 1.00 | 27.53 |
| 11429 | CA | ALA | B | 666 | -51.249 | 17.122 | 85.789 | 1.00 | 28.54 |
| 11430 | CB | ALA | B | 666 | -52.321 | 16.312 | 86.519 | 1.00 | 27.96 |
| 11431 | C | ALA | B | 666 | -51.902 | 18.154 | 84.876 | 1.00 | 28.92 |
| 11432 | O | ALA | B | 666 | -51.965 | 17.975 | 83.656 | 1.00 | 28.75 |
| 11433 | N | GLU | B | 667 | -52.402 | 19.226 | 85.483 | 1.00 | 29.98 |
| 11434 | CA | GLU | B | 667 | -53.146 | 20.267 | 84.772 | 1.00 | 31.08 |
| 11435 | CB | GLU | B | 667 | -53.572 | 21.367 | 85.753 | 1.00 | 31.61 |
| 11436 | CG | GLU | B | 667 | -54.269 | 22.549 | 85.102 | 1.00 | 35.39 |
| 11437 | CD | GLU | B | 667 | -55.606 | 22.180 | 84.483 | 1.00 | 41.19 |
| 11438 | OE1 | GLU | B | 667 | -55.922 | 22.736 | 83.410 | 1.00 | 43.54 |
| 11439 | OE2 | GLU | B | 667 | -56.348 | 21.345 | 85.070 | 1.00 | 43.87 |
| 11440 | C | GLU | B | 667 | -52.391 | 20.848 | 83.587 | 1.00 | 30.55 |
| 11441 | O | GLU | B | 667 | -52.954 | 21.052 | 82.530 | 1.00 | 31.52 |
| 11442 | N | ASN | B | 668 | -51.107 | 21.090 | 83.752 | 1.00 | 30.46 |
| 11443 | CA | ASN | B | 668 | -50.293 | 21.592 | 82.659 | 1.00 | 30.47 |
| 11444 | CB | ASN | B | 668 | -48.925 | 21.999 | 83.174 | 1.00 | 30.94 |
| 11445 | CG | ASN | B | 668 | -48.975 | 23.254 | 84.007 | 1.00 | 31.79 |
| 11446 | OD1 | ASN | B | 668 | -49.999 | 23.935 | 84.059 | 1.00 | 31.89 |
| 11447 | ND2 | ASN | B | 668 | -47.871 | 23.559 | 84.679 | 1.00 | 33.36 |
| 11448 | C | ASN | B | 668 | -50.078 | 20.672 | 81.467 | 1.00 | 30.20 |
| 11449 | O | ASN | B | 668 | -49.478 | 21.104 | 80.491 | 1.00 | 29.59 |
| 11450 | N | PHE | B | 669 | -50.523 | 19.416 | 81.548 | 1.00 | 30.18 |
| 11451 | CA | PHE | B | 669 | -50.333 | 18.472 | 80.449 | 1.00 | 30.59 |
| 11452 | CB | PHE | B | 669 | -50.454 | 17.016 | 80.922 | 1.00 | 30.47 |
| 11453 | CG | PHE | B | 669 | -49.197 | 16.461 | 81.550 | 1.00 | 30.43 |
| 11454 | CD1 | PHE | B | 669 | -48.851 | 16.784 | 82.853 | 1.00 | 29.28 |
| 11455 | CE1 | PHE | B | 669 | -47.707 | 16.268 | 83.431 | 1.00 | 29.56 |
| 11456 | CZ | PHE | B | 669 | -46.886 | 15.411 | 82.708 | 1.00 | 29.46 |
| 11457 | CE2 | PHE | B | 669 | -47.223 | 15.084 | 81.404 | 1.00 | 31.42 |
| 11458 | CD2 | PHE | B | 669 | -48.367 | 15.604 | 80.834 | 1.00 | 29.78 |
| 11459 | C | PHE | B | 669 | -51.341 | 18.778 | 79.351 | 1.00 | 31.27 |
| 11460 | O | PHE | B | 669 | -51.230 | 18.280 | 78.237 | 1.00 | 30.77 |
| 11461 | N | LYS | B | 670 | -52.311 | 19.634 | 79.670 | 1.00 | 32.49 |
| 11462 | CA | LYS | B | 670 | -53.277 | 20.102 | 78.686 | 1.00 | 33.59 |
| 11463 | CB | LYS | B | 670 | -54.122 | 21.234 | 79.263 | 1.00 | 34.38 |
| 11464 | CG | LYS | B | 670 | -55.602 | 20.927 | 79.421 | 1.00 | 36.88 |
| 11465 | CD | LYS | B | 670 | -55.941 | 20.640 | 80.878 | 1.00 | 38.81 |

FIGURE 3 HQ

| A | B | C | D | E | F | G | H | I | J |
|---|---|---|---|---|---|---|---|---|---|
| 11466 | CE | LYS | B | 708 | -57.403 | 20.289 | 81.032 | 1.00 | 40.91 |
| 11467 | NZ | LYS | B | 708 | -57.968 | 20.918 | 82.253 | 1.00 | 42.43 |
| 11468 | C | LYS | B | 708 | -52.578 | 20.668 | 77.480 | 1.00 | 33.88 |
| 11469 | O | LYS | B | 708 | -53.119 | 20.639 | 76.377 | 1.00 | 34.54 |
| 11470 | N | GLN | B | 709 | -51.377 | 21.196 | 77.695 | 1.00 | 33.98 |
| 11471 | CA | GLN | B | 709 | -50.638 | 21.898 | 76.651 | 1.00 | 34.19 |
| 11472 | CB | GLN | B | 709 | -49.692 | 22.932 | 77.284 | 1.00 | 34.36 |
| 11473 | CG | GLN | B | 709 | -50.340 | 23.839 | 78.322 | 1.00 | 37.40 |
| 11474 | CD | GLN | B | 709 | -49.355 | 24.829 | 78.946 | 1.00 | 42.07 |
| 11475 | OE1 | GLN | B | 709 | -48.527 | 25.430 | 78.238 | 1.00 | 43.94 |
| 11476 | NE2 | GLN | B | 709 | -49.447 | 25.008 | 80.267 | 1.00 | 42.23 |
| 11477 | C | GLN | B | 709 | -49.808 | 21.013 | 75.732 | 1.00 | 33.69 |
| 11478 | O | GLN | B | 709 | -49.307 | 21.488 | 74.713 | 1.00 | 34.21 |
| 11479 | N | VAL | B | 710 | -49.633 | 19.745 | 76.091 | 1.00 | 32.52 |
| 11480 | CA | VAL | B | 710 | -48.741 | 18.901 | 75.328 | 1.00 | 31.33 |
| 11481 | CB | VAL | B | 710 | -47.445 | 18.642 | 76.125 | 1.00 | 32.01 |
| 11482 | CG1 | VAL | B | 710 | -46.686 | 19.941 | 76.396 | 1.00 | 30.83 |
| 11483 | CG2 | VAL | B | 710 | -47.759 | 17.933 | 77.421 | 1.00 | 31.20 |
| 11484 | C | VAL | B | 710 | -49.321 | 17.542 | 74.964 | 1.00 | 30.81 |
| 11485 | O | VAL | B | 710 | -50.338 | 17.100 | 75.516 | 1.00 | 29.98 |
| 11486 | N | GLU | B | 711 | -48.662 | 16.901 | 74.005 | 1.00 | 30.01 |
| 11487 | CA | GLU | B | 711 | -48.973 | 15.532 | 73.616 | 1.00 | 29.65 |
| 11488 | CB | GLU | B | 711 | -48.823 | 15.371 | 72.104 | 1.00 | 30.55 |
| 11489 | CG | GLU | B | 711 | -50.015 | 15.902 | 71.314 | 1.00 | 35.63 |
| 11490 | CD | GLU | B | 711 | -49.669 | 16.234 | 69.871 | 1.00 | 42.70 |
| 11491 | OE1 | GLU | B | 711 | -49.877 | 15.365 | 68.986 | 1.00 | 44.03 |
| 11492 | OE2 | GLU | B | 711 | -49.190 | 17.373 | 69.620 | 1.00 | 45.75 |
| 11493 | C | GLU | B | 711 | -48.000 | 14.638 | 74.379 | 1.00 | 27.71 |
| 11494 | O | GLU | B | 711 | -46.790 | 14.775 | 74.266 | 1.00 | 27.36 |
| 11495 | N | TYR | B | 712 | -48.543 | 13.725 | 75.161 | 1.00 | 26.17 |
| 11496 | CA | TYR | B | 712 | -47.763 | 12.905 | 76.068 | 1.00 | 24.90 |
| 11497 | CB | TYR | B | 712 | -48.220 | 13.252 | 77.458 | 1.00 | 23.69 |
| 11498 | CG | TYR | B | 712 | -47.605 | 12.551 | 78.626 | 1.00 | 22.24 |
| 11499 | CD1 | TYR | B | 712 | -46.241 | 12.562 | 78.849 | 1.00 | 21.50 |
| 11500 | CE1 | TYR | B | 712 | -45.699 | 11.983 | 79.987 | 1.00 | 19.22 |
| 11501 | CZ | TYR | B | 712 | -46.521 | 11.404 | 80.909 | 1.00 | 20.30 |
| 11502 | OH | TYR | B | 712 | -46.015 | 10.826 | 82.039 | 1.00 | 21.46 |
| 11503 | CE2 | TYR | B | 712 | -47.875 | 11.386 | 80.719 | 1.00 | 22.28 |
| 11504 | CD2 | TYR | B | 712 | -48.411 | 11.974 | 79.591 | 1.00 | 22.47 |
| 11505 | C | TYR | B | 712 | -48.043 | 11.435 | 75.866 | 1.00 | 24.60 |
| 11506 | O | TYR | B | 712 | -49.207 | 11.039 | 75.779 | 1.00 | 24.93 |
| 11507 | N | LEU | B | 713 | -46.978 | 10.637 | 75.847 | 1.00 | 23.30 |
| 11508 | CA | LEU | B | 713 | -47.082 | 9.193 | 75.696 | 1.00 | 22.85 |
| 11509 | CB | LEU | B | 713 | -46.382 | 8.722 | 74.417 | 1.00 | 22.22 |
| 11510 | CG | LEU | B | 713 | -46.110 | 7.220 | 74.296 | 1.00 | 21.35 |
| 11511 | CD1 | LEU | B | 713 | -47.389 | 6.386 | 74.450 | 1.00 | 19.40 |
| 11512 | CD2 | LEU | B | 713 | -45.445 | 6.946 | 72.952 | 1.00 | 20.50 |
| 11513 | C | LEU | B | 713 | -46.438 | 8.553 | 76.914 | 1.00 | 22.62 |
| 11514 | O | LEU | B | 713 | -45.286 | 8.794 | 77.185 | 1.00 | 22.85 |
| 11515 | N | LEU | B | 714 | -47.210 | 7.749 | 77.641 | 1.00 | 22.40 |
| 11516 | CA | LEU | B | 714 | -46.799 | 7.165 | 78.892 | 1.00 | 22.33 |

FIGURE 3 HR

| A | B | C | D | E | F | G | H | I | J |
|---|---|---|---|---|---|---|---|---|---|
| 11517 | CB | LEU | B | 676 | -47.836 | 7.535 | 79.959 | 1.00 | 21.80 |
| 11518 | CG | LEU | B | 676 | -47.637 | 6.916 | 81.355 | 1.00 | 22.36 |
| 11519 | CD1 | LEU | B | 676 | -48.763 | 7.329 | 82.268 | 1.00 | 22.97 |
| 11520 | CD2 | LEU | B | 676 | -46.293 | 7.293 | 81.973 | 1.00 | 19.55 |
| 11521 | C | LEU | B | 676 | -46.651 | 5.633 | 78.748 | 1.00 | 22.40 |
| 11522 | O | LEU | B | 676 | -47.599 | 4.936 | 78.368 | 1.00 | 23.59 |
| 11523 | N | ILE | B | 677 | -45.465 | 5.119 | 79.034 | 1.00 | 21.89 |
| 11524 | CA | ILE | B | 677 | -45.191 | 3.694 | 78.857 | 1.00 | 21.46 |
| 11525 | CB | ILE | B | 677 | -44.180 | 3.514 | 77.735 | 1.00 | 21.56 |
| 11526 | CG1 | ILE | B | 677 | -44.697 | 4.172 | 76.463 | 1.00 | 20.48 |
| 11527 | CD1 | ILE | B | 677 | -43.713 | 4.108 | 75.327 | 1.00 | 22.71 |
| 11528 | CG2 | ILE | B | 677 | -43.876 | 2.041 | 77.544 | 1.00 | 19.66 |
| 11529 | C | ILE | B | 677 | -44.608 | 3.055 | 80.089 | 1.00 | 21.16 |
| 11530 | O | ILE | B | 677 | -43.749 | 3.632 | 80.729 | 1.00 | 22.03 |
| 11531 | N | HIS | B | 678 | -45.056 | 1.859 | 80.422 | 1.00 | 21.16 |
| 11532 | CA | HIS | B | 678 | -44.548 | 1.208 | 81.613 | 1.00 | 21.16 |
| 11533 | CB | HIS | B | 678 | -45.262 | 1.774 | 82.848 | 1.00 | 20.85 |
| 11534 | CG | HIS | B | 678 | -44.387 | 1.869 | 84.052 | 1.00 | 20.59 |
| 11535 | ND1 | HIS | B | 678 | -43.817 | 0.764 | 84.642 | 1.00 | 22.12 |
| 11536 | CE1 | HIS | B | 678 | -43.087 | 1.145 | 85.676 | 1.00 | 23.15 |
| 11537 | NE2 | HIS | B | 678 | -43.158 | 2.462 | 85.771 | 1.00 | 25.82 |
| 11538 | CD2 | HIS | B | 678 | -43.971 | 2.940 | 84.770 | 1.00 | 21.07 |
| 11539 | C | HIS | B | 678 | -44.767 | -0.298 | 81.548 | 1.00 | 21.06 |
| 11540 | O | HIS | B | 678 | -45.797 | -0.750 | 81.051 | 1.00 | 21.04 |
| 11541 | N | GLY | B | 679 | -43.818 | -1.073 | 82.072 | 1.00 | 20.72 |
| 11542 | CA | GLY | B | 679 | -43.981 | -2.512 | 82.086 | 1.00 | 20.65 |
| 11543 | C | GLY | B | 679 | -44.753 | -2.895 | 83.326 | 1.00 | 21.24 |
| 11544 | O | GLY | B | 679 | -44.522 | -2.338 | 84.403 | 1.00 | 21.36 |
| 11545 | N | THR | B | 680 | -45.656 | -3.858 | 83.216 | 1.00 | 21.21 |
| 11546 | CA | THR | B | 680 | -46.439 | -4.189 | 84.384 | 1.00 | 21.71 |
| 11547 | CB | THR | B | 680 | -47.714 | -4.958 | 84.010 | 1.00 | 22.25 |
| 11548 | OG1 | THR | B | 680 | -47.377 | -6.256 | 83.499 | 1.00 | 20.42 |
| 11549 | CG2 | THR | B | 680 | -48.435 | -4.238 | 82.863 | 1.00 | 20.27 |
| 11550 | C | THR | B | 680 | -45.659 | -4.920 | 85.468 | 1.00 | 22.64 |
| 11551 | O | THR | B | 680 | -46.084 | -4.924 | 86.646 | 1.00 | 23.38 |
| 11552 | N | ALA | B | 681 | -44.535 | -5.536 | 85.094 | 1.00 | 22.23 |
| 11553 | CA | ALA | B | 681 | -43.735 | -6.284 | 86.057 | 1.00 | 21.88 |
| 11554 | CB | ALA | B | 681 | -43.446 | -7.693 | 85.517 | 1.00 | 22.40 |
| 11555 | C | ALA | B | 681 | -42.425 | -5.557 | 86.396 | 1.00 | 22.23 |
| 11556 | O | ALA | B | 681 | -41.370 | -6.188 | 86.623 | 1.00 | 21.47 |
| 11557 | N | ASP | B | 682 | -42.484 | -4.230 | 86.378 | 1.00 | 21.85 |
| 11558 | CA | ASP | B | 682 | -41.322 | -3.435 | 86.711 | 1.00 | 22.43 |
| 11559 | CB | ASP | B | 682 | -41.469 | -2.007 | 86.192 | 1.00 | 22.15 |
| 11560 | CG | ASP | B | 682 | -40.188 | -1.243 | 86.262 | 1.00 | 22.54 |
| 11561 | OD1 | ASP | B | 682 | -39.992 | -0.307 | 85.432 | 1.00 | 19.13 |
| 11562 | OD2 | ASP | B | 682 | -39.315 | -1.527 | 87.131 | 1.00 | 24.17 |
| 11563 | C | ASP | B | 682 | -41.107 | -3.488 | 88.226 | 1.00 | 22.44 |
| 11564 | O | ASP | B | 682 | -41.922 | -2.991 | 88.997 | 1.00 | 22.84 |
| 11565 | N | ASP | B | 683 | -40.036 | -4.161 | 88.635 | 1.00 | 22.29 |
| 11566 | CA | ASP | B | 683 | -39.717 | -4.368 | 90.044 | 1.00 | 22.46 |
| 11567 | CB | ASP | B | 683 | -38.888 | -5.636 | 90.193 | 1.00 | 22.70 |

FIGURE 3 HS

| A | B | C | D | E | F | G | H | I | J |
|---|---|---|---|---|---|---|---|---|---|
| 11568 | CG | ASP | B | 683 | -37.609 | -5.580 | 89.379 | 1.00 | 21.98 |
| 11569 | OD1 | ASP | B | 683 | -37.661 | -5.817 | 88.142 | 1.00 | 21.50 |
| 11570 | OD2 | ASP | B | 683 | -36.515 | -5.289 | 89.890 | 1.00 | 19.87 |
| 11571 | C | ASP | B | 683 | -38.892 | -3.221 | 90.593 | 1.00 | 22.43 |
| 11572 | O | ASP | B | 683 | -38.692 | -3.113 | 91.800 | 1.00 | 22.89 |
| 11573 | N | ASN | B | 684 | -38.416 | -2.377 | 89.691 | 1.00 | 22.67 |
| 11574 | CA | ASN | B | 684 | -37.600 | -1.224 | 90.030 | 1.00 | 22.77 |
| 11575 | CB | ASN | B | 684 | -36.557 | -1.018 | 88.946 | 1.00 | 22.51 |
| 11576 | CG | ASN | B | 684 | -35.395 | -0.215 | 89.429 | 1.00 | 24.70 |
| 11577 | OD1 | ASN | B | 684 | -34.256 | -0.429 | 89.002 | 1.00 | 25.50 |
| 11578 | ND2 | ASN | B | 684 | -35.664 | 0.720 | 90.342 | 1.00 | 25.07 |
| 11579 | C | ASN | B | 684 | -38.447 | 0.051 | 90.211 | 1.00 | 22.72 |
| 11580 | O | ASN | B | 684 | -38.626 | 0.521 | 91.326 | 1.00 | 21.14 |
| 11581 | N | VAL | B | 685 | -38.927 | 0.647 | 89.118 | 1.00 | 22.57 |
| 11582 | CA | VAL | B | 685 | -39.903 | 1.715 | 89.304 | 1.00 | 22.58 |
| 11583 | CB | VAL | B | 685 | -39.587 | 3.007 | 88.549 | 1.00 | 22.83 |
| 11584 | CG1 | VAL | B | 685 | -38.130 | 3.053 | 88.203 | 1.00 | 21.94 |
| 11585 | CG2 | VAL | B | 685 | -40.443 | 3.173 | 87.359 | 1.00 | 24.06 |
| 11586 | C | VAL | B | 685 | -41.259 | 1.097 | 89.001 | 1.00 | 22.01 |
| 11587 | O | VAL | B | 685 | -41.574 | 0.713 | 87.893 | 1.00 | 22.70 |
| 11588 | N | HIS | B | 686 | -42.024 | 0.935 | 90.050 | 1.00 | 21.89 |
| 11589 | CA | HIS | B | 686 | -43.258 | 0.196 | 89.990 | 1.00 | 22.12 |
| 11590 | CB | HIS | B | 686 | -43.769 | -0.013 | 91.408 | 1.00 | 21.20 |
| 11591 | CG | HIS | B | 686 | -42.743 | -0.645 | 92.284 | 1.00 | 21.37 |
| 11592 | ND1 | HIS | B | 686 | -42.659 | -0.411 | 93.640 | 1.00 | 21.73 |
| 11593 | CE1 | HIS | B | 686 | -41.641 | -1.096 | 94.136 | 1.00 | 22.17 |
| 11594 | NE2 | HIS | B | 686 | -41.052 | -1.750 | 93.147 | 1.00 | 20.29 |
| 11595 | CD2 | HIS | B | 686 | -41.718 | -1.479 | 91.977 | 1.00 | 20.36 |
| 11596 | C | HIS | B | 686 | -44.270 | 0.798 | 89.059 | 1.00 | 21.76 |
| 11597 | O | HIS | B | 686 | -44.334 | 2.003 | 88.897 | 1.00 | 21.68 |
| 11598 | N | PHE | B | 687 | -45.026 | -0.078 | 88.413 | 1.00 | 22.26 |
| 11599 | CA | PHE | B | 687 | -46.042 | 0.330 | 87.460 | 1.00 | 22.39 |
| 11600 | CB | PHE | B | 687 | -46.831 | -0.887 | 87.014 | 1.00 | 22.17 |
| 11601 | CG | PHE | B | 687 | -47.881 | -0.572 | 86.006 | 1.00 | 22.72 |
| 11602 | CD1 | PHE | B | 687 | -47.545 | -0.436 | 84.666 | 1.00 | 21.38 |
| 11603 | CE1 | PHE | B | 687 | -48.499 | -0.142 | 83.740 | 1.00 | 21.54 |
| 11604 | CZ | PHE | B | 687 | -49.826 | 0.044 | 84.141 | 1.00 | 21.45 |
| 11605 | CE2 | PHE | B | 687 | -50.172 | -0.076 | 85.467 | 1.00 | 21.25 |
| 11606 | CD2 | PHE | B | 687 | -49.203 | -0.393 | 86.398 | 1.00 | 21.37 |
| 11607 | C | PHE | B | 687 | -46.957 | 1.328 | 88.139 | 1.00 | 22.85 |
| 11608 | O | PHE | B | 687 | -47.563 | 2.191 | 87.485 | 1.00 | 22.91 |
| 11609 | N | GLN | B | 688 | -47.007 | 1.191 | 89.466 | 1.00 | 23.57 |
| 11610 | CA | GLN | B | 688 | -47.739 | 2.049 | 90.391 | 1.00 | 24.37 |
| 11611 | CB | GLN | B | 688 | -47.237 | 1.790 | 91.824 | 1.00 | 24.04 |
| 11612 | CG | GLN | B | 688 | -47.775 | 2.791 | 92.861 | 1.00 | 25.68 |
| 11613 | CD | GLN | B | 688 | -46.957 | 2.851 | 94.149 | 1.00 | 26.71 |
| 11614 | OE1 | GLN | B | 688 | -45.749 | 2.652 | 94.143 | 1.00 | 27.21 |
| 11615 | NE2 | GLN | B | 688 | -47.625 | 3.115 | 95.252 | 1.00 | 28.39 |
| 11616 | C | GLN | B | 688 | -47.489 | 3.501 | 90.050 | 1.00 | 24.16 |
| 11617 | O | GLN | B | 688 | -48.390 | 4.319 | 89.960 | 1.00 | 24.28 |
| 11618 | N | GLN | B | 689 | -46.227 | 3.780 | 89.833 | 1.00 | 24.39 |

FIGURE 3 HT

| A | B | C | D | E | F | G | H | I | J |
|---|---|---|---|---|---|---|---|---|---|
| 11619 | CA | GLN | B | 689 | -45.716 | 5.111 | 89.555 | 1.00 | 24.90 |
| 11620 | CB | GLN | B | 689 | -44.213 | 4.921 | 89.380 | 1.00 | 24.89 |
| 11621 | CG | GLN | B | 689 | -43.351 | 6.093 | 89.446 | 1.00 | 29.13 |
| 11622 | CD | GLN | B | 689 | -42.643 | 6.286 | 90.782 | 1.00 | 30.33 |
| 11623 | OE1 | GLN | B | 689 | -42.614 | 7.396 | 91.266 | 1.00 | 34.56 |
| 11624 | NE2 | GLN | B | 689 | -42.031 | 5.245 | 91.333 | 1.00 | 30.33 |
| 11625 | C | GLN | B | 689 | -46.420 | 5.690 | 88.312 | 1.00 | 24.89 |
| 11626 | O | GLN | B | 689 | -46.926 | 6.817 | 88.322 | 1.00 | 24.56 |
| 11627 | N | SER | B | 690 | -46.503 | 4.910 | 87.241 | 1.00 | 24.52 |
| 11628 | CA | SER | B | 690 | -47.227 | 5.386 | 86.062 | 1.00 | 24.06 |
| 11629 | CB | SER | B | 690 | -46.801 | 4.653 | 84.797 | 1.00 | 23.60 |
| 11630 | OG | SER | B | 690 | -45.753 | 5.350 | 84.176 | 1.00 | 24.82 |
| 11631 | C | SER | B | 690 | -48.742 | 5.262 | 86.250 | 1.00 | 23.47 |
| 11632 | O | SER | B | 690 | -49.495 | 6.037 | 85.702 | 1.00 | 23.46 |
| 11633 | N | ALA | B | 691 | -49.188 | 4.297 | 87.035 | 1.00 | 22.97 |
| 11634 | CA | ALA | B | 691 | -50.622 | 4.206 | 87.320 | 1.00 | 23.09 |
| 11635 | CB | ALA | B | 691 | -50.913 | 2.993 | 88.171 | 1.00 | 21.96 |
| 11636 | C | ALA | B | 691 | -51.164 | 5.490 | 87.992 | 1.00 | 23.33 |
| 11637 | O | ALA | B | 691 | -52.297 | 5.891 | 87.758 | 1.00 | 23.06 |
| 11638 | N | GLN | B | 692 | -50.358 | 6.115 | 88.848 | 1.00 | 23.59 |
| 11639 | CA | GLN | B | 692 | -50.767 | 7.358 | 89.479 | 1.00 | 23.92 |
| 11640 | CB | GLN | B | 692 | -50.005 | 7.608 | 90.777 | 1.00 | 23.48 |
| 11641 | CG | GLN | B | 692 | -50.201 | 6.512 | 91.794 | 1.00 | 24.15 |
| 11642 | CD | GLN | B | 692 | -51.483 | 6.655 | 92.580 | 1.00 | 23.96 |
| 11643 | OE1 | GLN | B | 692 | -52.332 | 7.479 | 92.254 | 1.00 | 23.98 |
| 11644 | NE2 | GLN | B | 692 | -51.630 | 5.845 | 93.618 | 1.00 | 24.58 |
| 11645 | C | GLN | B | 692 | -50.637 | 8.540 | 88.539 | 1.00 | 23.75 |
| 11646 | O | GLN | B | 692 | -51.447 | 9.466 | 88.600 | 1.00 | 24.89 |
| 11647 | N | ILE | B | 693 | -49.661 | 8.534 | 87.646 | 1.00 | 23.63 |
| 11648 | CA | ILE | B | 693 | -49.625 | 9.635 | 86.695 | 1.00 | 23.61 |
| 11649 | CB | ILE | B | 693 | -48.448 | 9.547 | 85.729 | 1.00 | 23.53 |
| 11650 | CG1 | ILE | B | 693 | -47.132 | 9.755 | 86.446 | 1.00 | 22.66 |
| 11651 | CD1 | ILE | B | 693 | -45.967 | 9.319 | 85.588 | 1.00 | 19.56 |
| 11652 | CG2 | ILE | B | 693 | -48.568 | 10.607 | 84.642 | 1.00 | 22.24 |
| 11653 | C | ILE | B | 693 | -50.908 | 9.594 | 85.898 | 1.00 | 24.18 |
| 11654 | O | ILE | B | 693 | -51.605 | 10.579 | 85.813 | 1.00 | 24.84 |
| 11655 | N | SER | B | 694 | -51.234 | 8.429 | 85.338 | 1.00 | 24.50 |
| 11656 | CA | SER | B | 694 | -52.399 | 8.319 | 84.456 | 1.00 | 24.84 |
| 11657 | CB | SER | B | 694 | -52.510 | 6.927 | 83.814 | 1.00 | 24.09 |
| 11658 | OG | SER | B | 694 | -52.933 | 5.961 | 84.765 | 1.00 | 23.12 |
| 11659 | C | SER | B | 694 | -53.683 | 8.687 | 85.172 | 1.00 | 24.78 |
| 11660 | O | SER | B | 694 | -54.517 | 9.362 | 84.618 | 1.00 | 24.83 |
| 11661 | N | LYS | B | 695 | -53.841 | 8.224 | 86.400 | 1.00 | 25.10 |
| 11662 | CA | LYS | B | 695 | -55.038 | 8.536 | 87.162 | 1.00 | 25.16 |
| 11663 | CB | LYS | B | 695 | -55.053 | 7.777 | 88.494 | 1.00 | 24.97 |
| 11664 | CG | LYS | B | 695 | -56.173 | 8.181 | 89.449 | 1.00 | 24.11 |
| 11665 | CD | LYS | B | 695 | -56.591 | 7.037 | 90.321 | 1.00 | 23.85 |
| 11666 | CE | LYS | B | 695 | -55.439 | 6.603 | 91.228 | 1.00 | 26.36 |
| 11667 | NZ | LYS | B | 695 | -54.961 | 7.687 | 92.144 | 1.00 | 26.44 |
| 11668 | C | LYS | B | 695 | -55.132 | 10.048 | 87.387 | 1.00 | 25.98 |
| 11669 | O | LYS | B | 695 | -56.220 | 10.615 | 87.364 | 1.00 | 26.20 |

FIGURE 3 HU

| A | B | C | D | E | F | G | H | I | J |
|---|---|---|---|---|---|---|---|---|---|
| 11670 | N | ALA | B | 696 | -53.990 | 10.704 | 87.581 | 1.00 | 26.38 |
| 11671 | CA | ALA | B | 696 | -53.991 | 12.151 | 87.789 | 1.00 | 26.38 |
| 11672 | CB | ALA | B | 696 | -52.647 | 12.643 | 88.343 | 1.00 | 26.31 |
| 11673 | C | ALA | B | 696 | -54.330 | 12.902 | 86.528 | 1.00 | 26.34 |
| 11674 | O | ALA | B | 696 | -54.947 | 13.963 | 86.581 | 1.00 | 26.21 |
| 11675 | N | LEU | B | 697 | -53.897 | 12.378 | 85.388 | 1.00 | 26.74 |
| 11676 | CA | LEU | B | 697 | -54.185 | 13.035 | 84.123 | 1.00 | 26.97 |
| 11677 | CB | LEU | B | 697 | -53.319 | 12.465 | 83.009 | 1.00 | 26.55 |
| 11678 | CG | LEU | B | 697 | -51.812 | 12.726 | 83.104 | 1.00 | 27.21 |
| 11679 | CD1 | LEU | B | 697 | -51.087 | 11.965 | 82.023 | 1.00 | 26.23 |
| 11680 | CD2 | LEU | B | 697 | -51.490 | 14.191 | 82.979 | 1.00 | 25.07 |
| 11681 | C | LEU | B | 697 | -55.676 | 12.884 | 83.783 | 1.00 | 27.52 |
| 11682 | O | LEU | B | 697 | -56.294 | 13.756 | 83.155 | 1.00 | 27.46 |
| 11683 | N | VAL | B | 698 | -56.255 | 11.774 | 84.221 | 1.00 | 27.87 |
| 11684 | CA | VAL | B | 698 | -57.650 | 11.501 | 83.937 | 1.00 | 27.55 |
| 11685 | CB | VAL | B | 698 | -57.975 | 10.027 | 84.251 | 1.00 | 27.83 |
| 11686 | CG1 | VAL | B | 698 | -59.498 | 9.805 | 84.293 | 1.00 | 25.37 |
| 11687 | CG2 | VAL | B | 698 | -57.290 | 9.114 | 83.225 | 1.00 | 24.42 |
| 11688 | C | VAL | B | 698 | -58.495 | 12.392 | 84.806 | 1.00 | 28.67 |
| 11689 | O | VAL | B | 698 | -59.501 | 12.963 | 84.358 | 1.00 | 29.44 |
| 11690 | N | ASP | B | 699 | -58.071 | 12.508 | 86.053 | 1.00 | 28.50 |
| 11691 | CA | ASP | B | 699 | -58.772 | 13.302 | 87.028 | 1.00 | 29.88 |
| 11692 | CB | ASP | B | 699 | -58.153 | 13.104 | 88.414 | 1.00 | 29.83 |
| 11693 | CG | ASP | B | 699 | -58.526 | 11.756 | 89.028 | 1.00 | 32.75 |
| 11694 | OD1 | ASP | B | 699 | -57.905 | 11.360 | 90.047 | 1.00 | 35.84 |
| 11695 | OD2 | ASP | B | 699 | -59.424 | 11.013 | 88.551 | 1.00 | 34.23 |
| 11696 | C | ASP | B | 699 | -58.883 | 14.785 | 86.656 | 1.00 | 29.99 |
| 11697 | O | ASP | B | 699 | -59.751 | 15.470 | 87.180 | 1.00 | 29.61 |
| 11698 | N | VAL | B | 700 | -58.032 | 15.267 | 85.746 | 1.00 | 29.98 |
| 11699 | CA | VAL | B | 700 | -58.128 | 16.666 | 85.306 | 1.00 | 30.33 |
| 11700 | CB | VAL | B | 700 | -56.844 | 17.521 | 85.627 | 1.00 | 31.00 |
| 11701 | CG1 | VAL | B | 700 | -56.511 | 17.481 | 87.115 | 1.00 | 29.84 |
| 11702 | CG2 | VAL | B | 700 | -55.641 | 17.066 | 84.795 | 1.00 | 30.71 |
| 11703 | C | VAL | B | 700 | -58.490 | 16.807 | 83.821 | 1.00 | 30.05 |
| 11704 | O | VAL | B | 700 | -58.385 | 17.888 | 83.250 | 1.00 | 30.40 |
| 11705 | N | GLY | B | 701 | -58.915 | 15.720 | 83.191 | 1.00 | 29.65 |
| 11706 | CA | GLY | B | 701 | -59.385 | 15.797 | 81.816 | 1.00 | 28.66 |
| 11707 | C | GLY | B | 701 | -58.343 | 16.017 | 80.740 | 1.00 | 28.50 |
| 11708 | O | GLY | B | 701 | -58.616 | 16.656 | 79.710 | 1.00 | 29.25 |
| 11709 | N | VAL | B | 702 | -57.144 | 15.497 | 80.938 | 1.00 | 27.69 |
| 11710 | CA | VAL | B | 702 | -56.148 | 15.614 | 79.882 | 1.00 | 27.99 |
| 11711 | CB | VAL | B | 702 | -54.795 | 16.145 | 80.393 | 1.00 | 27.91 |
| 11712 | CG1 | VAL | B | 702 | -54.651 | 15.831 | 81.835 | 1.00 | 30.45 |
| 11713 | CG2 | VAL | B | 702 | -53.636 | 15.576 | 79.583 | 1.00 | 27.98 |
| 11714 | C | VAL | B | 702 | -56.008 | 14.286 | 79.157 | 1.00 | 27.58 |
| 11715 | O | VAL | B | 702 | -55.928 | 13.218 | 79.777 | 1.00 | 27.62 |
| 11716 | N | ASP | B | 703 | -56.035 | 14.362 | 77.838 | 1.00 | 26.84 |
| 11717 | CA | ASP | B | 703 | -55.941 | 13.191 | 77.009 | 1.00 | 27.00 |
| 11718 | CB | ASP | B | 703 | -56.685 | 13.401 | 75.689 | 1.00 | 26.61 |
| 11719 | CG | ASP | B | 703 | -56.669 | 12.151 | 74.820 | 1.00 | 28.36 |
| 11720 | OD1 | ASP | B | 703 | -56.231 | 12.229 | 73.648 | 1.00 | 29.70 |

FIGURE 3 HV

| A | B | C | D | E | F | G | H | I | J |
|---|---|---|---|---|---|---|---|---|---|
| 11721 | OD2 | ASP | B | 703 | -57.050 | 11.037 | 75.242 | 1.00 | 28.34 |
| 11722 | C | ASP | B | 703 | -54.468 | 12.927 | 76.741 | 1.00 | 26.68 |
| 11723 | O | ASP | B | 703 | -53.685 | 13.868 | 76.562 | 1.00 | 27.08 |
| 11724 | N | PHE | B | 704 | -54.086 | 11.656 | 76.706 | 1.00 | 25.57 |
| 11725 | CA | PHE | B | 704 | -52.683 | 11.307 | 76.492 | 1.00 | 25.16 |
| 11726 | CB | PHE | B | 704 | -51.912 | 11.325 | 77.829 | 1.00 | 24.13 |
| 11727 | CG | PHE | B | 704 | -52.535 | 10.459 | 78.873 | 1.00 | 23.39 |
| 11728 | CD1 | PHE | B | 704 | -52.062 | 9.175 | 79.101 | 1.00 | 21.02 |
| 11729 | CE1 | PHE | B | 704 | -52.640 | 8.371 | 80.034 | 1.00 | 20.61 |
| 11730 | CZ | PHE | B | 704 | -53.741 | 8.822 | 80.761 | 1.00 | 20.93 |
| 11731 | CE2 | PHE | B | 704 | -54.237 | 10.090 | 80.538 | 1.00 | 21.66 |
| 11732 | CD2 | PHE | B | 704 | -53.638 | 10.905 | 79.590 | 1.00 | 21.85 |
| 11733 | C | PHE | B | 704 | -52.655 | 9.919 | 75.907 | 1.00 | 25.36 |
| 11734 | O | PHE | B | 704 | -53.671 | 9.236 | 75.908 | 1.00 | 25.18 |
| 11735 | N | GLN | B | 705 | -51.496 | 9.505 | 75.406 | 1.00 | 25.90 |
| 11736 | CA | GLN | B | 705 | -51.319 | 8.160 | 74.871 | 1.00 | 26.19 |
| 11737 | CB | GLN | B | 705 | -50.410 | 8.200 | 73.660 | 1.00 | 26.63 |
| 11738 | CG | GLN | B | 705 | -50.825 | 9.215 | 72.654 | 1.00 | 30.83 |
| 11739 | CD | GLN | B | 705 | -52.008 | 8.760 | 71.880 | 1.00 | 34.97 |
| 11740 | OE1 | GLN | B | 705 | -53.039 | 9.419 | 71.884 | 1.00 | 37.84 |
| 11741 | NE2 | GLN | B | 705 | -51.870 | 7.627 | 71.194 | 1.00 | 38.25 |
| 11742 | C | GLN | B | 705 | -50.667 | 7.261 | 75.904 | 1.00 | 25.75 |
| 11743 | O | GLN | B | 705 | -49.761 | 7.691 | 76.617 | 1.00 | 25.97 |
| 11744 | N | ALA | B | 706 | -51.104 | 6.010 | 75.973 | 1.00 | 24.70 |
| 11745 | CA | ALA | B | 706 | -50.492 | 5.076 | 76.906 | 1.00 | 24.31 |
| 11746 | CB | ALA | B | 706 | -51.415 | 4.830 | 78.101 | 1.00 | 23.90 |
| 11747 | C | ALA | B | 706 | -50.139 | 3.746 | 76.240 | 1.00 | 23.82 |
| 11748 | O | ALA | B | 706 | -50.665 | 3.390 | 75.192 | 1.00 | 23.72 |
| 11749 | N | MET | B | 707 | -49.202 | 3.041 | 76.851 | 1.00 | 23.07 |
| 11750 | CA | MET | B | 707 | -48.905 | 1.680 | 76.481 | 1.00 | 21.51 |
| 11751 | CB | MET | B | 707 | -47.860 | 1.633 | 75.378 | 1.00 | 22.13 |
| 11752 | CG | MET | B | 707 | -47.485 | 0.215 | 74.945 | 1.00 | 21.18 |
| 11753 | SD | MET | B | 707 | -48.900 | -0.708 | 74.359 | 1.00 | 21.84 |
| 11754 | CE | MET | B | 707 | -49.333 | 0.205 | 72.848 | 1.00 | 20.68 |
| 11755 | C | MET | B | 707 | -48.381 | 0.983 | 77.711 | 1.00 | 21.21 |
| 11756 | O | MET | B | 707 | -47.397 | 1.420 | 78.309 | 1.00 | 20.81 |
| 11757 | N | TRP | B | 708 | -49.043 | -0.092 | 78.124 | 1.00 | 20.75 |
| 11758 | CA | TRP | B | 708 | -48.482 | -0.906 | 79.182 | 1.00 | 20.19 |
| 11759 | CB | TRP | B | 708 | -49.562 | -1.433 | 80.127 | 1.00 | 19.59 |
| 11760 | CG | TRP | B | 708 | -50.393 | -2.489 | 79.545 | 1.00 | 20.81 |
| 11761 | CD1 | TRP | B | 708 | -50.052 | -3.802 | 79.386 | 1.00 | 21.15 |
| 11762 | NE1 | TRP | B | 708 | -51.083 | -4.485 | 78.793 | 1.00 | 20.70 |
| 11763 | CE2 | TRP | B | 708 | -52.116 | -3.615 | 78.552 | 1.00 | 19.88 |
| 11764 | CD2 | TRP | B | 708 | -51.716 | -2.350 | 79.011 | 1.00 | 20.38 |
| 11765 | CE3 | TRP | B | 708 | -52.614 | -1.275 | 78.884 | 1.00 | 19.56 |
| 11766 | CZ3 | TRP | B | 708 | -53.837 | -1.500 | 78.317 | 1.00 | 19.59 |
| 11767 | CH2 | TRP | B | 708 | -54.209 | -2.782 | 77.868 | 1.00 | 19.43 |
| 11768 | CZ2 | TRP | B | 708 | -53.368 | -3.845 | 77.979 | 1.00 | 19.34 |
| 11769 | C | TRP | B | 708 | -47.779 | -2.035 | 78.447 | 1.00 | 20.09 |
| 11770 | O | TRP | B | 708 | -48.099 | -2.289 | 77.290 | 1.00 | 19.23 |
| 11771 | N | TYR | B | 709 | -46.797 | -2.667 | 79.093 | 1.00 | 20.28 |

FIGURE 3 HW

| A | B | C | D | E | F | G | H | I | J |
|---|---|---|---|---|---|---|---|---|---|
| 11772 | CA  | TYR | B | 709 | -46.100 | -3.838  | 78.526 | 1.00 | 20.63 |
| 11773 | CB  | TYR | B | 709 | -44.627 | -3.558  | 78.185 | 1.00 | 20.56 |
| 11774 | CG  | TYR | B | 709 | -44.559 | -2.898  | 76.860 | 1.00 | 19.84 |
| 11775 | CD1 | TYR | B | 709 | -44.767 | -3.636  | 75.697 | 1.00 | 20.28 |
| 11776 | CE1 | TYR | B | 709 | -44.775 | -3.035  | 74.461 | 1.00 | 19.85 |
| 11777 | CZ  | TYR | B | 709 | -44.565 | -1.685  | 74.371 | 1.00 | 19.86 |
| 11778 | OH  | TYR | B | 709 | -44.574 | -1.101  | 73.136 | 1.00 | 22.81 |
| 11779 | CE2 | TYR | B | 709 | -44.349 | -0.923  | 75.504 | 1.00 | 20.72 |
| 11780 | CD2 | TYR | B | 709 | -44.356 | -1.533  | 76.750 | 1.00 | 20.59 |
| 11781 | C   | TYR | B | 709 | -46.226 | -4.983  | 79.484 | 1.00 | 20.70 |
| 11782 | O   | TYR | B | 709 | -45.549 | -5.038  | 80.518 | 1.00 | 21.14 |
| 11783 | N   | THR | B | 710 | -47.137 | -5.883  | 79.141 | 1.00 | 21.25 |
| 11784 | CA  | THR | B | 710 | -47.445 | -7.024  | 79.962 | 1.00 | 21.25 |
| 11785 | CB  | THR | B | 710 | -48.380 | -7.953  | 79.229 | 1.00 | 21.37 |
| 11786 | OG1 | THR | B | 710 | -49.648 | -7.307  | 79.012 | 1.00 | 23.03 |
| 11787 | CG2 | THR | B | 710 | -48.689 | -9.129  | 80.132 | 1.00 | 20.84 |
| 11788 | C   | THR | B | 710 | -46.209 | -7.831  | 80.348 | 1.00 | 21.64 |
| 11789 | O   | THR | B | 710 | -45.524 | -8.376  | 79.485 | 1.00 | 20.62 |
| 11790 | N   | ASP | B | 711 | -45.962 | -7.910  | 81.658 | 1.00 | 21.81 |
| 11791 | CA  | ASP | B | 711 | -44.898 | -8.742  | 82.220 | 1.00 | 21.69 |
| 11792 | CB  | ASP | B | 711 | -45.033 | -10.195 | 81.760 | 1.00 | 21.54 |
| 11793 | CG  | ASP | B | 711 | -46.143 | -10.910 | 82.466 | 1.00 | 22.07 |
| 11794 | OD1 | ASP | B | 711 | -46.391 | -12.086 | 82.139 | 1.00 | 25.01 |
| 11795 | OD2 | ASP | B | 711 | -46.829 | -10.388 | 83.367 | 1.00 | 22.35 |
| 11796 | C   | ASP | B | 711 | -43.514 | -8.254  | 81.928 | 1.00 | 21.52 |
| 11797 | O   | ASP | B | 711 | -42.540 | -8.946  | 82.237 | 1.00 | 21.95 |
| 11798 | N   | GLU | B | 712 | -43.391 | -7.084  | 81.320 | 1.00 | 21.74 |
| 11799 | CA  | GLU | B | 712 | -42.044 | -6.549  | 81.114 | 1.00 | 22.19 |
| 11800 | CB  | GLU | B | 712 | -41.981 | -5.609  | 79.929 | 1.00 | 22.12 |
| 11801 | CG  | GLU | B | 712 | -42.177 | -6.311  | 78.603 | 1.00 | 23.30 |
| 11802 | CD  | GLU | B | 712 | -41.056 | -7.288  | 78.295 | 1.00 | 24.89 |
| 11803 | OE1 | GLU | B | 712 | -41.288 | -8.517  | 78.332 | 1.00 | 24.79 |
| 11804 | OE2 | GLU | B | 712 | -39.940 | -6.828  | 77.996 | 1.00 | 26.46 |
| 11805 | C   | GLU | B | 712 | -41.557 | -5.842  | 82.378 | 1.00 | 22.56 |
| 11806 | O   | GLU | B | 712 | -42.365 | -5.440  | 83.211 | 1.00 | 22.17 |
| 11807 | N   | ASP | B | 713 | -40.237 | -5.715  | 82.529 | 1.00 | 23.00 |
| 11808 | CA  | ASP | B | 713 | -39.697 | -5.030  | 83.696 | 1.00 | 23.22 |
| 11809 | CB  | ASP | B | 713 | -38.779 | -5.928  | 84.524 | 1.00 | 22.79 |
| 11810 | CG  | ASP | B | 713 | -37.508 | -6.282  | 83.814 | 1.00 | 23.44 |
| 11811 | OD1 | ASP | B | 713 | -36.781 | -7.146  | 84.337 | 1.00 | 26.49 |
| 11812 | OD2 | ASP | B | 713 | -37.115 | -5.729  | 82.771 | 1.00 | 23.72 |
| 11813 | C   | ASP | B | 713 | -39.069 | -3.705  | 83.306 | 1.00 | 23.04 |
| 11814 | O   | ASP | B | 713 | -39.365 | -3.180  | 82.246 | 1.00 | 22.35 |
| 11815 | N   | HIS | B | 714 | -38.218 | -3.163  | 84.168 | 1.00 | 23.71 |
| 11816 | CA  | HIS | B | 714 | -37.661 | -1.825  | 83.958 | 1.00 | 24.48 |
| 11817 | CB  | HIS | B | 714 | -36.754 | -1.429  | 85.132 | 1.00 | 24.46 |
| 11818 | CG  | HIS | B | 714 | -36.548 | 0.048   | 85.238 | 1.00 | 25.34 |
| 11819 | ND1 | HIS | B | 714 | -37.591 | 0.944   | 85.168 | 1.00 | 26.61 |
| 11820 | CE1 | HIS | B | 714 | -37.126 | 2.171   | 85.268 | 1.00 | 25.20 |
| 11821 | NE2 | HIS | B | 714 | -35.816 | 2.107   | 85.401 | 1.00 | 27.88 |
| 11822 | CD2 | HIS | B | 714 | -35.426 | 0.790   | 85.370 | 1.00 | 27.76 |

FIGURE 3 HX

| A | B | C | D | E | F | G | H | I | J |
|---|---|---|---|---|---|---|---|---|---|
| 11823 | C | HIS | B | 714 | -36.938 | -1.613 | 82.639 | 1.00 | 24.78 |
| 11824 | O | HIS | B | 714 | -36.947 | -0.524 | 82.089 | 1.00 | 25.49 |
| 11825 | N | GLY | B | 715 | -36.297 | -2.653 | 82.123 | 1.00 | 25.54 |
| 11826 | CA | GLY | B | 715 | -35.611 | -2.519 | 80.855 | 1.00 | 25.38 |
| 11827 | C | GLY | B | 715 | -36.467 | -2.725 | 79.611 | 1.00 | 25.11 |
| 11828 | O | GLY | B | 715 | -36.037 | -2.346 | 78.533 | 1.00 | 24.63 |
| 11829 | N | ILE | B | 716 | -37.669 | -3.297 | 79.762 | 1.00 | 25.14 |
| 11830 | CA | ILE | B | 716 | -38.542 | -3.599 | 78.625 | 1.00 | 25.32 |
| 11831 | CB | ILE | B | 716 | -39.311 | -2.336 | 78.151 | 1.00 | 25.99 |
| 11832 | CG1 | ILE | B | 716 | -40.025 | -1.689 | 79.353 | 1.00 | 25.69 |
| 11833 | CD1 | ILE | B | 716 | -40.970 | -0.580 | 78.995 | 1.00 | 25.63 |
| 11834 | CG2 | ILE | B | 716 | -40.290 | -2.705 | 77.023 | 1.00 | 22.30 |
| 11835 | C | ILE | B | 716 | -37.675 | -4.115 | 77.519 | 1.00 | 26.05 |
| 11836 | O | ILE | B | 716 | -37.685 | -3.606 | 76.395 | 1.00 | 26.00 |
| 11837 | N | ALA | B | 717 | -36.932 | -5.159 | 77.851 | 1.00 | 27.17 |
| 11838 | CA | ALA | B | 717 | -35.891 | -5.655 | 76.982 | 1.00 | 28.36 |
| 11839 | CB | ALA | B | 717 | -34.554 | -5.691 | 77.758 | 1.00 | 29.30 |
| 11840 | C | ALA | B | 717 | -36.146 | -6.995 | 76.307 | 1.00 | 29.08 |
| 11841 | O | ALA | B | 717 | -35.255 | -7.502 | 75.629 | 1.00 | 29.47 |
| 11842 | N | SER | B | 718 | -37.314 | -7.604 | 76.511 | 1.00 | 28.91 |
| 11843 | CA | SER | B | 718 | -37.601 | -8.795 | 75.737 | 1.00 | 29.39 |
| 11844 | CB | SER | B | 718 | -39.074 | -9.196 | 75.878 | 1.00 | 29.52 |
| 11845 | OG | SER | B | 718 | -39.357 | -9.608 | 77.204 | 1.00 | 34.20 |
| 11846 | C | SER | B | 718 | -37.356 | -8.409 | 74.293 | 1.00 | 28.23 |
| 11847 | O | SER | B | 718 | -37.622 | -7.288 | 73.891 | 1.00 | 29.25 |
| 11848 | N | SER | B | 719 | -36.893 | -9.333 | 73.482 | 1.00 | 27.65 |
| 11849 | CA | SER | B | 719 | -36.711 | -9.023 | 72.065 | 1.00 | 27.04 |
| 11850 | CB | SER | B | 719 | -36.265 | -10.261 | 71.277 | 1.00 | 27.06 |
| 11851 | OG | SER | B | 719 | -36.278 | -9.967 | 69.882 | 1.00 | 29.49 |
| 11852 | C | SER | B | 719 | -37.959 | -8.400 | 71.411 | 1.00 | 25.40 |
| 11853 | O | SER | B | 719 | -37.870 | -7.392 | 70.750 | 1.00 | 25.93 |
| 11854 | N | THR | B | 720 | -39.123 | -8.993 | 71.585 | 1.00 | 24.04 |
| 11855 | CA | THR | B | 720 | -40.297 | -8.452 | 70.913 | 1.00 | 22.83 |
| 11856 | CB | THR | B | 720 | -41.410 | -9.492 | 70.864 | 1.00 | 23.35 |
| 11857 | OG1 | THR | B | 720 | -41.764 | -9.841 | 72.211 | 1.00 | 21.44 |
| 11858 | CG2 | THR | B | 720 | -40.905 | -10.789 | 70.212 | 1.00 | 21.97 |
| 11859 | C | THR | B | 720 | -40.859 | -7.182 | 71.539 | 1.00 | 22.49 |
| 11860 | O | THR | B | 720 | -41.493 | -6.385 | 70.854 | 1.00 | 21.74 |
| 11861 | N | ALA | B | 721 | -40.657 | -7.006 | 72.837 | 1.00 | 21.92 |
| 11862 | CA | ALA | B | 721 | -41.153 | -5.822 | 73.494 | 1.00 | 21.78 |
| 11863 | CB | ALA | B | 721 | -41.192 | -6.010 | 74.993 | 1.00 | 21.88 |
| 11864 | C | ALA | B | 721 | -40.238 | -4.687 | 73.135 | 1.00 | 21.73 |
| 11865 | O | ALA | B | 721 | -40.673 | -3.570 | 72.946 | 1.00 | 22.65 |
| 11866 | N | HIS | B | 722 | -38.954 | -4.972 | 73.026 | 1.00 | 21.57 |
| 11867 | CA | HIS | B | 722 | -38.021 | -3.930 | 72.682 | 1.00 | 21.04 |
| 11868 | CB | HIS | B | 722 | -36.600 | -4.479 | 72.664 | 1.00 | 21.05 |
| 11869 | CG | HIS | B | 722 | -35.612 | -3.558 | 72.039 | 1.00 | 19.68 |
| 11870 | ND1 | HIS | B | 722 | -35.006 | -2.538 | 72.737 | 1.00 | 22.51 |
| 11871 | CE1 | HIS | B | 722 | -34.161 | -1.902 | 71.937 | 1.00 | 21.88 |
| 11872 | NE2 | HIS | B | 722 | -34.209 | -2.469 | 70.744 | 1.00 | 21.58 |
| 11873 | CD2 | HIS | B | 722 | -35.105 | -3.511 | 70.783 | 1.00 | 21.16 |

FIGURE 3 HY

| A | B | C | D | E | F | G | H | I | J |
|---|---|---|---|---|---|---|---|---|---|
| 11874 | C | HIS | B | 722 | -38.358 | -3.346 | 71.324 | 1.00 | 20.87 |
| 11875 | O | HIS | B | 722 | -38.406 | -2.134 | 71.153 | 1.00 | 19.87 |
| 11876 | N | GLN | B | 723 | -38.578 | -4.225 | 70.352 | 1.00 | 21.21 |
| 11877 | CA | GLN | B | 723 | -38.908 | -3.790 | 69.000 | 1.00 | 21.55 |
| 11878 | CB | GLN | B | 723 | -38.942 | -4.997 | 68.076 | 1.00 | 21.92 |
| 11879 | CG | GLN | B | 723 | -37.624 | -5.736 | 68.007 | 1.00 | 22.78 |
| 11880 | CD | GLN | B | 723 | -37.721 | -6.987 | 67.167 | 1.00 | 24.29 |
| 11881 | OE1 | GLN | B | 723 | -38.058 | -6.918 | 65.984 | 1.00 | 27.58 |
| 11882 | NE2 | GLN | B | 723 | -37.435 | -8.132 | 67.769 | 1.00 | 21.70 |
| 11883 | C | GLN | B | 723 | -40.249 | -3.057 | 68.943 | 1.00 | 21.47 |
| 11884 | O | GLN | B | 723 | -40.413 | -2.103 | 68.184 | 1.00 | 21.50 |
| 11885 | N | HIS | B | 724 | -41.188 | -3.491 | 69.778 | 1.00 | 20.78 |
| 11886 | CA | HIS | B | 724 | -42.523 | -2.911 | 69.812 | 1.00 | 20.65 |
| 11887 | CB | HIS | B | 724 | -43.445 | -3.800 | 70.654 | 1.00 | 20.00 |
| 11888 | CG | HIS | B | 724 | -44.902 | -3.560 | 70.418 | 1.00 | 18.84 |
| 11889 | ND1 | HIS | B | 724 | -45.612 | -2.569 | 71.064 | 1.00 | 19.92 |
| 11890 | CE1 | HIS | B | 724 | -46.866 | -2.585 | 70.645 | 1.00 | 17.53 |
| 11891 | NE2 | HIS | B | 724 | -46.996 | -3.565 | 69.771 | 1.00 | 17.21 |
| 11892 | CD2 | HIS | B | 724 | -45.787 | -4.191 | 69.615 | 1.00 | 15.78 |
| 11893 | C | HIS | B | 724 | -42.533 | -1.503 | 70.409 | 1.00 | 21.09 |
| 11894 | O | HIS | B | 724 | -43.173 | -0.603 | 69.870 | 1.00 | 21.79 |
| 11895 | N | ILE | B | 725 | -41.853 | -1.306 | 71.533 | 1.00 | 20.56 |
| 11896 | CA | ILE | B | 725 | -41.890 | 0.014 | 72.136 | 1.00 | 20.54 |
| 11897 | CB | ILE | B | 725 | -41.319 | 0.009 | 73.561 | 1.00 | 20.29 |
| 11898 | CG1 | ILE | B | 725 | -41.542 | 1.368 | 74.222 | 1.00 | 18.92 |
| 11899 | CD1 | ILE | B | 725 | -40.936 | 1.452 | 75.618 | 1.00 | 20.02 |
| 11900 | CG2 | ILE | B | 725 | -39.827 | -0.372 | 73.551 | 1.00 | 20.46 |
| 11901 | C | ILE | B | 725 | -41.211 | 1.045 | 71.221 | 1.00 | 20.60 |
| 11902 | O | ILE | B | 725 | -41.759 | 2.115 | 70.991 | 1.00 | 20.39 |
| 11903 | N | TYR | B | 726 | -40.055 | 0.702 | 70.661 | 1.00 | 20.43 |
| 11904 | CA | TYR | B | 726 | -39.371 | 1.603 | 69.741 | 1.00 | 20.55 |
| 11905 | CB | TYR | B | 726 | -37.958 | 1.100 | 69.426 | 1.00 | 20.49 |
| 11906 | CG | TYR | B | 726 | -37.053 | 1.454 | 70.565 | 1.00 | 21.28 |
| 11907 | CD1 | TYR | B | 726 | -36.745 | 0.525 | 71.568 | 1.00 | 20.93 |
| 11908 | CE1 | TYR | B | 726 | -35.961 | 0.897 | 72.636 | 1.00 | 22.34 |
| 11909 | CZ | TYR | B | 726 | -35.494 | 2.211 | 72.700 | 1.00 | 22.45 |
| 11910 | OH | TYR | B | 726 | -34.705 | 2.628 | 73.723 | 1.00 | 24.15 |
| 11911 | CE2 | TYR | B | 726 | -35.813 | 3.128 | 71.742 | 1.00 | 20.64 |
| 11912 | CD2 | TYR | B | 726 | -36.594 | 2.765 | 70.706 | 1.00 | 19.99 |
| 11913 | C | TYR | B | 726 | -40.195 | 1.857 | 68.482 | 1.00 | 20.85 |
| 11914 | O | TYR | B | 726 | -40.174 | 2.961 | 67.917 | 1.00 | 21.68 |
| 11915 | N | THR | B | 727 | -40.940 | 0.844 | 68.065 | 1.00 | 20.74 |
| 11916 | CA | THR | B | 727 | -41.820 | 0.970 | 66.927 | 1.00 | 20.32 |
| 11917 | CB | THR | B | 727 | -42.397 | -0.412 | 66.508 | 1.00 | 20.53 |
| 11918 | OG1 | THR | B | 727 | -41.372 | -1.229 | 65.929 | 1.00 | 20.62 |
| 11919 | CG2 | THR | B | 727 | -43.383 | -0.250 | 65.341 | 1.00 | 18.90 |
| 11920 | C | THR | B | 727 | -42.943 | 1.913 | 67.344 | 1.00 | 20.94 |
| 11921 | O | THR | B | 727 | -43.314 | 2.827 | 66.605 | 1.00 | 20.27 |
| 11922 | N | HIS | B | 728 | -43.480 | 1.698 | 68.545 | 1.00 | 21.17 |
| 11923 | CA | HIS | B | 728 | -44.569 | 2.530 | 69.002 | 1.00 | 21.72 |
| 11924 | CB | HIS | B | 728 | -45.181 | 1.959 | 70.268 | 1.00 | 21.45 |

FIGURE 3 HZ

| A | B | C | D | E | F | G | H | I | J |
|---|---|---|---|---|---|---|---|---|---|
| 11925 | CG | HIS | B | 728 | -46.580 | 2.430 | 70.509 | 1.00 | 21.44 |
| 11926 | ND1 | HIS | B | 728 | -47.604 | 2.170 | 69.625 | 1.00 | 20.01 |
| 11927 | CE1 | HIS | B | 728 | -48.719 | 2.716 | 70.075 | 1.00 | 19.80 |
| 11928 | NE2 | HIS | B | 728 | -48.451 | 3.329 | 71.218 | 1.00 | 19.19 |
| 11929 | CD2 | HIS | B | 728 | -47.117 | 3.179 | 71.503 | 1.00 | 19.94 |
| 11930 | C | HIS | B | 728 | -44.111 | 3.986 | 69.219 | 1.00 | 22.77 |
| 11931 | O | HIS | B | 728 | -44.811 | 4.943 | 68.879 | 1.00 | 23.12 |
| 11932 | N | MET | B | 729 | -42.919 | 4.158 | 69.772 | 1.00 | 23.36 |
| 11933 | CA | MET | B | 729 | -42.424 | 5.505 | 69.999 | 1.00 | 23.86 |
| 11934 | CB | MET | B | 729 | -41.213 | 5.471 | 70.930 | 1.00 | 23.04 |
| 11935 | CG | MET | B | 729 | -41.611 | 5.015 | 72.310 | 1.00 | 24.70 |
| 11936 | SD | MET | B | 729 | -40.337 | 5.244 | 73.518 | 1.00 | 27.86 |
| 11937 | CE | MET | B | 729 | -39.049 | 4.336 | 72.788 | 1.00 | 24.03 |
| 11938 | C | MET | B | 729 | -42.133 | 6.255 | 68.699 | 1.00 | 23.07 |
| 11939 | O | MET | B | 729 | -42.338 | 7.458 | 68.616 | 1.00 | 23.08 |
| 11940 | N | SER | B | 730 | -41.654 | 5.554 | 67.685 | 1.00 | 23.19 |
| 11941 | CA | SER | B | 730 | -41.398 | 6.236 | 66.430 | 1.00 | 23.64 |
| 11942 | CB | SER | B | 730 | -40.686 | 5.335 | 65.445 | 1.00 | 23.27 |
| 11943 | OG | SER | B | 730 | -39.613 | 4.679 | 66.084 | 1.00 | 22.94 |
| 11944 | C | SER | B | 730 | -42.665 | 6.817 | 65.805 | 1.00 | 24.48 |
| 11945 | O | SER | B | 730 | -42.638 | 7.933 | 65.276 | 1.00 | 25.05 |
| 11946 | N | HIS | B | 731 | -43.772 | 6.082 | 65.871 | 1.00 | 25.18 |
| 11947 | CA | HIS | B | 731 | -45.017 | 6.579 | 65.300 | 1.00 | 26.18 |
| 11948 | CB | HIS | B | 731 | -46.156 | 5.573 | 65.425 | 1.00 | 26.41 |
| 11949 | CG | HIS | B | 731 | -46.022 | 4.376 | 64.543 | 1.00 | 29.11 |
| 11950 | ND1 | HIS | B | 731 | -46.233 | 3.095 | 65.005 | 1.00 | 31.92 |
| 11951 | CE1 | HIS | B | 731 | -46.058 | 2.234 | 64.018 | 1.00 | 32.79 |
| 11952 | NE2 | HIS | B | 731 | -45.750 | 2.913 | 62.927 | 1.00 | 34.46 |
| 11953 | CD2 | HIS | B | 731 | -45.725 | 4.256 | 63.229 | 1.00 | 32.74 |
| 11954 | C | HIS | B | 731 | -45.443 | 7.792 | 66.064 | 1.00 | 25.82 |
| 11955 | O | HIS | B | 731 | -45.874 | 8.763 | 65.485 | 1.00 | 26.25 |
| 11956 | N | PHE | B | 732 | -45.378 | 7.708 | 67.380 | 1.00 | 26.04 |
| 11957 | CA | PHE | B | 732 | -45.778 | 8.826 | 68.192 | 1.00 | 26.42 |
| 11958 | CB | PHE | B | 732 | -45.669 | 8.494 | 69.667 | 1.00 | 26.65 |
| 11959 | CG | PHE | B | 732 | -46.009 | 9.643 | 70.557 | 1.00 | 26.39 |
| 11960 | CD1 | PHE | B | 732 | -47.320 | 9.903 | 70.889 | 1.00 | 24.34 |
| 11961 | CE1 | PHE | B | 732 | -47.638 | 10.966 | 71.694 | 1.00 | 26.55 |
| 11962 | CZ | PHE | B | 732 | -46.651 | 11.795 | 72.190 | 1.00 | 25.55 |
| 11963 | CE2 | PHE | B | 732 | -45.338 | 11.553 | 71.869 | 1.00 | 26.82 |
| 11964 | CD2 | PHE | B | 732 | -45.020 | 10.481 | 71.037 | 1.00 | 26.49 |
| 11965 | C | PHE | B | 732 | -44.879 | 10.002 | 67.868 | 1.00 | 26.82 |
| 11966 | O | PHE | B | 732 | -45.351 | 11.105 | 67.691 | 1.00 | 26.14 |
| 11967 | N | ILE | B | 733 | -43.579 | 9.767 | 67.777 | 1.00 | 27.54 |
| 11968 | CA | ILE | B | 733 | -42.705 | 10.880 | 67.455 | 1.00 | 28.71 |
| 11969 | CB | ILE | B | 733 | -41.221 | 10.540 | 67.691 | 1.00 | 28.65 |
| 11970 | CG1 | ILE | B | 733 | -40.882 | 10.734 | 69.165 | 1.00 | 29.46 |
| 11971 | CD1 | ILE | B | 733 | -40.854 | 12.189 | 69.598 | 1.00 | 31.65 |
| 11972 | CG2 | ILE | B | 733 | -40.335 | 11.474 | 66.899 | 1.00 | 28.29 |
| 11973 | C | ILE | B | 733 | -42.954 | 11.426 | 66.042 | 1.00 | 29.24 |
| 11974 | O | ILE | B | 733 | -42.991 | 12.636 | 65.855 | 1.00 | 29.00 |
| 11975 | N | LYS | B | 734 | -43.150 | 10.560 | 65.053 | 1.00 | 30.15 |

FIGURE 3 IA

| A | B | C | D | E | F | G | H | I | J |
|---|---|---|---|---|---|---|---|---|---|
| 11976 | CA | LYS | B | 734 | -43.375 | 11.048 | 63.689 | 1.00 | 31.39 |
| 11977 | CB | LYS | B | 734 | -43.367 | 9.915 | 62.657 | 1.00 | 31.04 |
| 11978 | CG | LYS | B | 734 | -42.257 | 8.908 | 62.869 | 1.00 | 32.61 |
| 11979 | CD | LYS | B | 734 | -41.564 | 8.476 | 61.598 | 1.00 | 33.79 |
| 11980 | CE | LYS | B | 734 | -42.532 | 8.011 | 60.537 | 1.00 | 37.05 |
| 11981 | NZ | LYS | B | 734 | -41.851 | 7.565 | 59.261 | 1.00 | 36.85 |
| 11982 | C | LYS | B | 734 | -44.657 | 11.880 | 63.568 | 1.00 | 32.09 |
| 11983 | O | LYS | B | 734 | -44.669 | 12.949 | 62.951 | 1.00 | 31.80 |
| 11984 | N | GLN | B | 735 | -45.731 | 11.405 | 64.182 | 1.00 | 32.99 |
| 11985 | CA | GLN | B | 735 | -47.008 | 12.096 | 64.082 | 1.00 | 34.22 |
| 11986 | CB | GLN | B | 735 | -48.157 | 11.198 | 64.554 | 1.00 | 34.31 |
| 11987 | CG | GLN | B | 735 | -48.815 | 11.597 | 65.853 | 1.00 | 37.67 |
| 11988 | CD | GLN | B | 735 | -49.816 | 12.716 | 65.650 | 1.00 | 42.32 |
| 11989 | OE1 | GLN | B | 735 | -50.280 | 12.941 | 64.531 | 1.00 | 45.22 |
| 11990 | NE2 | GLN | B | 735 | -50.142 | 13.428 | 66.720 | 1.00 | 43.62 |
| 11991 | C | GLN | B | 735 | -46.972 | 13.435 | 64.809 | 1.00 | 34.36 |
| 11992 | O | GLN | B | 735 | -47.587 | 14.399 | 64.353 | 1.00 | 34.67 |
| 11993 | N | CYS | B | 736 | -46.249 | 13.518 | 65.923 | 1.00 | 34.24 |
| 11994 | CA | CYS | B | 736 | -46.107 | 14.813 | 66.584 | 1.00 | 35.23 |
| 11995 | CB | CYS | B | 736 | -45.595 | 14.666 | 68.020 | 1.00 | 35.10 |
| 11996 | SG | CYS | B | 736 | -44.743 | 16.115 | 68.740 | 1.00 | 38.88 |
| 11997 | C | CYS | B | 736 | -45.234 | 15.789 | 65.772 | 1.00 | 34.41 |
| 11998 | O | CYS | B | 736 | -45.438 | 16.984 | 65.840 | 1.00 | 34.31 |
| 11999 | N | PHE | B | 737 | -44.294 | 15.273 | 64.983 | 1.00 | 34.75 |
| 12000 | CA | PHE | B | 737 | -43.450 | 16.131 | 64.139 | 1.00 | 34.40 |
| 12001 | CB | PHE | B | 737 | -42.009 | 15.601 | 64.095 | 1.00 | 33.38 |
| 12002 | CG | PHE | B | 737 | -41.208 | 15.857 | 65.349 | 1.00 | 30.63 |
| 12003 | CD1 | PHE | B | 737 | -41.683 | 16.682 | 66.341 | 1.00 | 28.24 |
| 12004 | CE1 | PHE | B | 737 | -40.943 | 16.919 | 67.481 | 1.00 | 25.79 |
| 12005 | CZ | PHE | B | 737 | -39.713 | 16.328 | 67.645 | 1.00 | 25.71 |
| 12006 | CE2 | PHE | B | 737 | -39.217 | 15.496 | 66.664 | 1.00 | 26.36 |
| 12007 | CD2 | PHE | B | 737 | -39.968 | 15.263 | 65.520 | 1.00 | 28.45 |
| 12008 | C | PHE | B | 737 | -43.978 | 16.240 | 62.696 | 1.00 | 35.34 |
| 12009 | O | PHE | B | 737 | -43.315 | 16.777 | 61.816 | 1.00 | 35.69 |
| 12010 | N | SER | B | 738 | -45.170 | 15.721 | 62.442 | 1.00 | 36.90 |
| 12011 | CA | SER | B | 738 | -45.736 | 15.701 | 61.090 | 1.00 | 38.41 |
| 12012 | CB | SER | B | 738 | -46.161 | 17.102 | 60.619 | 1.00 | 38.34 |
| 12013 | OG | SER | B | 738 | -46.998 | 17.693 | 61.588 | 1.00 | 37.87 |
| 12014 | C | SER | B | 738 | -44.820 | 15.049 | 60.060 | 1.00 | 39.26 |
| 12015 | O | SER | B | 738 | -44.673 | 15.545 | 58.945 | 1.00 | 39.61 |
| 12016 | N | LEU | B | 739 | -44.204 | 13.941 | 60.442 | 1.00 | 40.66 |
| 12017 | CA | LEU | B | 739 | -43.374 | 13.172 | 59.531 | 1.00 | 41.94 |
| 12018 | CB | LEU | B | 739 | -42.096 | 12.730 | 60.227 | 1.00 | 41.77 |
| 12019 | CG | LEU | B | 739 | -41.228 | 13.891 | 60.718 | 1.00 | 41.94 |
| 12020 | CD1 | LEU | B | 739 | -39.947 | 13.388 | 61.369 | 1.00 | 40.29 |
| 12021 | CD2 | LEU | B | 739 | -40.923 | 14.844 | 59.564 | 1.00 | 41.86 |
| 12022 | C | LEU | B | 739 | -44.197 | 11.967 | 59.085 | 1.00 | 43.28 |
| 12023 | O | LEU | B | 739 | -44.712 | 11.203 | 59.920 | 1.00 | 44.06 |
| 12024 | N | PRO | B | 740 | -44.325 | 11.801 | 57.772 | 1.00 | 43.94 |
| 12025 | CA | PRO | B | 740 | -45.178 | 10.760 | 57.190 | 1.00 | 44.31 |
| 12026 | CB | PRO | B | 740 | -45.276 | 11.180 | 55.711 | 1.00 | 44.53 |

FIGURE 3 IB

| A | B | C | D | E | F | G | H | I | J |
|---|---|---|---|---|---|---|---|---|---|
| 12027 | CG | PRO | B | 740 | -44.718 | 12.605 | 55.676 | 1.00 | 44.79 |
| 12028 | CD | PRO | B | 740 | -43.652 | 12.609 | 56.739 | 1.00 | 44.27 |
| 12029 | C | PRO | B | 740 | -44.593 | 9.358 | 57.300 | 1.00 | 44.50 |
| 12030 | O | PRO | B | 740 | -43.439 | 9.146 | 56.939 | 1.00 | 44.74 |
| 12031 | O7 | NAG | B | 971 | -1.496 | -23.139 | 73.513 | 1.00 | 72.40 |
| 12032 | C7 | NAG | B | 971 | -1.548 | -21.927 | 73.306 | 1.00 | 72.39 |
| 12033 | C8 | NAG | B | 971 | -2.801 | -21.131 | 73.509 | 1.00 | 72.68 |
| 12034 | N2 | NAG | B | 971 | -0.504 | -21.175 | 72.970 | 1.00 | 71.31 |
| 12035 | C2 | NAG | B | 971 | 0.827 | -21.683 | 72.727 | 1.00 | 71.53 |
| 12036 | C1 | NAG | B | 971 | 1.680 | -20.515 | 72.241 | 1.00 | 69.94 |
| 12037 | C3 | NAG | B | 971 | 1.423 | -22.304 | 73.992 | 1.00 | 72.07 |
| 12038 | O3 | NAG | B | 971 | 0.785 | -23.540 | 74.358 | 1.00 | 72.11 |
| 12039 | C4 | NAG | B | 971 | 2.888 | -22.628 | 73.783 | 1.00 | 72.70 |
| 12040 | O4 | NAG | B | 971 | 3.429 | -23.019 | 75.052 | 1.00 | 74.28 |
| 12041 | C5 | NAG | B | 971 | 3.672 | -21.451 | 73.212 | 1.00 | 72.39 |
| 12042 | O5 | NAG | B | 971 | 3.036 | -20.925 | 72.042 | 1.00 | 71.59 |
| 12043 | C6 | NAG | B | 971 | 5.082 | -21.916 | 72.857 | 1.00 | 73.22 |
| 12044 | O6 | NAG | B | 971 | 5.405 | -21.573 | 71.499 | 1.00 | 73.48 |
| 12045 | O7 | NAG | B1621 | | -28.592 | -31.215 | 89.895 | 1.00 | 69.71 |
| 12046 | C7 | NAG | B1621 | | -28.880 | -31.667 | 90.994 | 1.00 | 68.34 |
| 12047 | C8 | NAG | B1621 | | -27.985 | -31.492 | 92.185 | 1.00 | 69.03 |
| 12048 | N2 | NAG | B1621 | | -30.029 | -32.286 | 91.257 | 1.00 | 66.17 |
| 12049 | C2 | NAG | B1621 | | -31.055 | -32.550 | 90.263 | 1.00 | 65.21 |
| 12050 | C1 | NAG | B1621 | | -31.508 | -31.261 | 89.569 | 1.00 | 62.67 |
| 12051 | C3 | NAG | B1621 | | -30.675 | -33.599 | 89.210 | 1.00 | 65.79 |
| 12052 | O3 | NAG | B1621 | | -30.191 | -34.840 | 89.756 | 1.00 | 65.25 |
| 12053 | C4 | NAG | B1621 | | -31.936 | -33.851 | 88.395 | 1.00 | 66.12 |
| 12054 | O4 | NAG | B1621 | | -31.714 | -34.873 | 87.412 | 1.00 | 67.57 |
| 12055 | C5 | NAG | B1621 | | -32.398 | -32.545 | 87.742 | 1.00 | 65.66 |
| 12056 | O5 | NAG | B1621 | | -32.641 | -31.542 | 88.736 | 1.00 | 65.08 |
| 12057 | C6 | NAG | B1621 | | -33.668 | -32.766 | 86.925 | 1.00 | 65.94 |
| 12058 | O6 | NAG | B1621 | | -34.816 | -32.262 | 87.628 | 1.00 | 65.92 |
| 12059 | O7 | NAG | B2311 | | -0.221 | -18.701 | 100.763 | 1.00 | 65.86 |
| 12060 | C7 | NAG | B2311 | | -1.001 | -19.645 | 100.882 | 1.00 | 65.25 |
| 12061 | C8 | NAG | B2311 | | -1.035 | -20.782 | 99.900 | 1.00 | 64.98 |
| 12062 | N2 | NAG | B2311 | | -1.828 | -19.772 | 101.926 | 1.00 | 63.88 |
| 12063 | C2 | NAG | B2311 | | -1.895 | -18.773 | 102.980 | 1.00 | 62.57 |
| 12064 | C1 | NAG | B2311 | | -3.171 | -17.935 | 102.898 | 1.00 | 59.08 |
| 12065 | C3 | NAG | B2311 | | -1.797 | -19.460 | 104.340 | 1.00 | 62.63 |
| 12066 | O3 | NAG | B2311 | | -0.532 | -20.133 | 104.439 | 1.00 | 63.27 |
| 12067 | C4 | NAG | B2311 | | -1.973 | -18.451 | 105.477 | 1.00 | 62.24 |
| 12068 | O4 | NAG | B2311 | | -2.095 | -19.163 | 106.722 | 1.00 | 62.14 |
| 12069 | C5 | NAG | B2311 | | -3.204 | -17.560 | 105.246 | 1.00 | 61.89 |
| 12070 | O5 | NAG | B2311 | | -3.193 | -16.957 | 103.943 | 1.00 | 60.57 |
| 12071 | C6 | NAG | B2311 | | -3.305 | -16.457 | 106.294 | 1.00 | 62.05 |
| 12072 | O6 | NAG | B2311 | | -2.385 | -15.410 | 105.960 | 1.00 | 62.89 |
| 12073 | O7 | NAG | B2411 | | -31.170 | -12.163 | 112.789 | 1.00 | 53.05 |
| 12074 | C7 | NAG | B2411 | | -31.967 | -13.042 | 112.519 | 1.00 | 53.48 |
| 12075 | C8 | NAG | B2411 | | -31.539 | -14.432 | 112.162 | 1.00 | 53.33 |
| 12076 | N2 | NAG | B2411 | | -33.271 | -12.817 | 112.600 | 1.00 | 53.74 |
| 12077 | C2 | NAG | B2411 | | -33.726 | -11.504 | 112.997 | 1.00 | 55.17 |

FIGURE 3 IC

| A | B | C D E | F | G | H | I | J |
|---|---|---|---|---|---|---|---|
| 12078 | C1 | NAG B2411 | -34.243 | -10.613 | 111.876 | 1.00 | 52.90 |
| 12079 | C3 | NAG B2411 | -34.820 | -11.730 | 114.021 | 1.00 | 57.59 |
| 12080 | O3 | NAG B2411 | -34.303 | -12.454 | 115.133 | 1.00 | 59.38 |
| 12081 | C4 | NAG B2411 | -35.323 | -10.405 | 114.540 | 1.00 | 59.18 |
| 12082 | O4 | NAG B2411 | -36.434 | -10.680 | 115.399 | 1.00 | 65.63 |
| 12083 | C5 | NAG B2411 | -35.736 | -9.513 | 113.375 | 1.00 | 57.72 |
| 12084 | O5 | NAG B2411 | -34.649 | -9.370 | 112.457 | 1.00 | 54.84 |
| 12085 | C6 | NAG B2411 | -36.157 | -8.144 | 113.878 | 1.00 | 57.33 |
| 12086 | O6 | NAG B2411 | -36.390 | -7.301 | 112.749 | 1.00 | 58.35 |
| 12087 | O7 | NAG B2412 | -39.628 | -7.940 | 114.970 | 1.00 | 82.70 |
| 12088 | C7 | NAG B2412 | -39.201 | -8.987 | 115.428 | 1.00 | 82.55 |
| 12089 | C8 | NAG B2412 | -39.649 | -10.325 | 114.904 | 1.00 | 82.82 |
| 12090 | N2 | NAG B2412 | -38.250 | -9.010 | 116.361 | 1.00 | 81.55 |
| 12091 | C2 | NAG B2412 | -37.736 | -10.262 | 116.879 | 1.00 | 80.85 |
| 12092 | C1 | NAG B2412 | -36.220 | -10.326 | 116.723 | 1.00 | 77.61 |
| 12093 | C3 | NAG B2412 | -38.144 | -10.408 | 118.339 | 1.00 | 81.59 |
| 12094 | O3 | NAG B2412 | -39.575 | -10.458 | 118.443 | 1.00 | 82.35 |
| 12095 | C4 | NAG B2412 | -37.514 | -11.666 | 118.926 | 1.00 | 81.41 |
| 12096 | O4 | NAG B2412 | -37.862 | -11.805 | 120.313 | 1.00 | 81.61 |
| 12097 | C5 | NAG B2412 | -36.003 | -11.573 | 118.748 | 1.00 | 80.50 |
| 12098 | O5 | NAG B2412 | -35.713 | -11.506 | 117.351 | 1.00 | 80.11 |
| 12099 | C6 | NAG B2412 | -35.302 | -12.783 | 119.349 | 1.00 | 80.52 |
| 12100 | O6 | NAG B2412 | -35.982 | -13.973 | 118.934 | 1.00 | 79.91 |
| 12101 | O7 | NAG B2931 | -24.335 | -30.051 | 115.266 | 1.00 | 75.19 |
| 12102 | C7 | NAG B2931 | -24.419 | -30.370 | 114.085 | 1.00 | 74.43 |
| 12103 | C8 | NAG B2931 | -23.672 | -31.529 | 113.485 | 1.00 | 75.00 |
| 12104 | N2 | NAG B2931 | -25.246 | -29.735 | 113.262 | 1.00 | 72.23 |
| 12105 | C2 | NAG B2931 | -26.042 | -28.629 | 113.752 | 1.00 | 70.22 |
| 12106 | C1 | NAG B2931 | -25.770 | -27.339 | 112.982 | 1.00 | 66.92 |
| 12107 | C3 | NAG B2931 | -27.493 | -29.073 | 113.627 | 1.00 | 69.93 |
| 12108 | O3 | NAG B2931 | -27.724 | -30.212 | 114.460 | 1.00 | 70.63 |
| 12109 | C4 | NAG B2931 | -28.425 | -27.952 | 114.027 | 1.00 | 69.60 |
| 12110 | O4 | NAG B2931 | -29.789 | -28.385 | 113.890 | 1.00 | 70.12 |
| 12111 | C5 | NAG B2931 | -28.126 | -26.758 | 113.134 | 1.00 | 68.85 |
| 12112 | O5 | NAG B2931 | -26.762 | -26.347 | 113.283 | 1.00 | 68.61 |
| 12113 | C6 | NAG B2931 | -29.024 | -25.590 | 113.510 | 1.00 | 68.50 |
| 12114 | O6 | NAG B2931 | -28.254 | -24.638 | 114.253 | 1.00 | 67.60 |
| 12115 | O7 | NAG B3331 | -23.192 | 17.701 | 106.780 | 1.00 | 62.25 |
| 12116 | C7 | NAG B3331 | -23.032 | 16.659 | 107.397 | 1.00 | 61.75 |
| 12117 | C8 | NAG B3331 | -21.667 | 16.169 | 107.783 | 1.00 | 62.11 |
| 12118 | N2 | NAG B3331 | -24.062 | 15.939 | 107.838 | 1.00 | 60.45 |
| 12119 | C2 | NAG B3331 | -25.414 | 16.360 | 107.514 | 1.00 | 59.68 |
| 12120 | C1 | NAG B3331 | -26.201 | 15.190 | 106.947 | 1.00 | 55.92 |
| 12121 | C3 | NAG B3331 | -26.163 | 16.929 | 108.717 | 1.00 | 60.28 |
| 12122 | O3 | NAG B3331 | -25.494 | 18.113 | 109.169 | 1.00 | 60.01 |
| 12123 | C4 | NAG B3331 | -27.609 | 17.272 | 108.333 | 1.00 | 60.83 |
| 12124 | O4 | NAG B3331 | -28.395 | 17.557 | 109.504 | 1.00 | 61.83 |
| 12125 | C5 | NAG B3331 | -28.283 | 16.161 | 107.520 | 1.00 | 60.34 |
| 12126 | O5 | NAG B3331 | -27.431 | 15.710 | 106.467 | 1.00 | 58.70 |
| 12127 | C6 | NAG B3331 | -29.573 | 16.667 | 106.876 | 1.00 | 61.21 |
| 12128 | O6 | NAG B3331 | -30.483 | 15.574 | 106.667 | 1.00 | 63.30 |

FIGURE 3 ID

| A | B | C | D | E | F | G | H | I | J |
|---|---|---|---|---|---|---|---|---|---|
| 12129 | N | ARG | C | 14 | -56.594 | -17.508 | 55.235 | 1.00 | 59.31 |
| 12130 | CA | ARG | C | 14 | -57.330 | -18.684 | 54.673 | 1.00 | 59.15 |
| 12131 | CB | ARG | C | 14 | -57.826 | -19.576 | 55.819 | 1.00 | 59.77 |
| 12132 | CG | ARG | C | 14 | -58.370 | -20.947 | 55.414 | 1.00 | 61.80 |
| 12133 | CD | ARG | C | 14 | -57.914 | -22.079 | 56.340 | 1.00 | 65.74 |
| 12134 | NE | ARG | C | 14 | -58.993 | -23.002 | 56.706 | 1.00 | 68.29 |
| 12135 | CZ | ARG | C | 14 | -59.063 | -23.632 | 57.878 | 1.00 | 70.05 |
| 12136 | NH1 | ARG | C | 14 | -58.114 | -23.443 | 58.789 | 1.00 | 71.17 |
| 12137 | NH2 | ARG | C | 14 | -60.071 | -24.455 | 58.145 | 1.00 | 70.83 |
| 12138 | C | ARG | C | 14 | -58.489 | -18.232 | 53.774 | 1.00 | 58.04 |
| 12139 | O | ARG | C | 14 | -59.531 | -18.887 | 53.706 | 1.00 | 58.12 |
| 12140 | N | LYS | C | 15 | -58.301 | -17.117 | 53.069 | 1.00 | 56.51 |
| 12141 | CA | LYS | C | 15 | -59.362 | -16.601 | 52.209 | 1.00 | 54.97 |
| 12142 | CB | LYS | C | 15 | -59.460 | -15.067 | 52.267 | 1.00 | 55.35 |
| 12143 | CG | LYS | C | 15 | -58.142 | -14.308 | 52.404 | 1.00 | 56.79 |
| 12144 | CD | LYS | C | 15 | -58.366 | -12.811 | 52.183 | 1.00 | 59.18 |
| 12145 | CE | LYS | C | 15 | -57.194 | -11.957 | 52.677 | 1.00 | 60.92 |
| 12146 | NZ | LYS | C | 15 | -57.343 | -11.519 | 54.106 | 1.00 | 61.81 |
| 12147 | C | LYS | C | 15 | -59.268 | -17.071 | 50.766 | 1.00 | 53.63 |
| 12148 | O | LYS | C | 15 | -58.213 | -17.484 | 50.292 | 1.00 | 53.86 |
| 12149 | N | THR | C | 16 | -60.391 | -17.003 | 50.067 | 1.00 | 51.93 |
| 12150 | CA | THR | C | 16 | -60.428 | -17.371 | 48.663 | 1.00 | 50.01 |
| 12151 | CB | THR | C | 16 | -61.491 | -18.445 | 48.422 | 1.00 | 50.09 |
| 12152 | OG1 | THR | C | 16 | -62.747 | -17.988 | 48.938 | 1.00 | 50.53 |
| 12153 | CG2 | THR | C | 16 | -61.190 | -19.676 | 49.260 | 1.00 | 49.69 |
| 12154 | C | THR | C | 16 | -60.767 | -16.130 | 47.877 | 1.00 | 48.35 |
| 12155 | O | THR | C | 16 | -61.000 | -15.073 | 48.455 | 1.00 | 48.10 |
| 12156 | N | TYR | C | 17 | -60.770 | -16.256 | 46.559 | 1.00 | 46.31 |
| 12157 | CA | TYR | C | 17 | -61.136 | -15.154 | 45.694 | 1.00 | 44.36 |
| 12158 | CB | TYR | C | 17 | -60.450 | -15.330 | 44.340 | 1.00 | 44.44 |
| 12159 | CG | TYR | C | 17 | -60.674 | -14.211 | 43.357 | 1.00 | 43.09 |
| 12160 | CD1 | TYR | C | 17 | -59.936 | -13.045 | 43.432 | 1.00 | 43.17 |
| 12161 | CE1 | TYR | C | 17 | -60.135 | -12.013 | 42.537 | 1.00 | 42.32 |
| 12162 | CZ | TYR | C | 17 | -61.079 | -12.148 | 41.547 | 1.00 | 42.01 |
| 12163 | OH | TYR | C | 17 | -61.274 | -11.122 | 40.655 | 1.00 | 40.75 |
| 12164 | CE2 | TYR | C | 17 | -61.820 | -13.306 | 41.446 | 1.00 | 42.15 |
| 12165 | CD2 | TYR | C | 17 | -61.614 | -14.327 | 42.349 | 1.00 | 41.90 |
| 12166 | C | TYR | C | 17 | -62.658 | -15.203 | 45.568 | 1.00 | 43.53 |
| 12167 | O | TYR | C | 17 | -63.202 | -16.089 | 44.922 | 1.00 | 43.35 |
| 12168 | N | THR | C | 18 | -63.347 | -14.258 | 46.196 | 1.00 | 42.57 |
| 12169 | CA | THR | C | 18 | -64.811 | -14.259 | 46.211 | 1.00 | 41.95 |
| 12170 | CB | THR | C | 18 | -65.323 | -13.527 | 47.451 | 1.00 | 41.87 |
| 12171 | OG1 | THR | C | 18 | -65.053 | -12.127 | 47.308 | 1.00 | 42.07 |
| 12172 | CG2 | THR | C | 18 | -64.537 | -13.949 | 48.699 | 1.00 | 42.05 |
| 12173 | C | THR | C | 18 | -65.501 | -13.628 | 45.010 | 1.00 | 41.61 |
| 12174 | O | THR | C | 18 | -64.872 | -13.041 | 44.132 | 1.00 | 41.43 |
| 12175 | N | LEU | C | 19 | -66.824 | -13.748 | 45.011 | 1.00 | 41.36 |
| 12176 | CA | LEU | C | 19 | -67.656 | -13.138 | 43.993 | 1.00 | 41.21 |
| 12177 | CB | LEU | C | 19 | -69.106 | -13.630 | 44.091 | 1.00 | 40.58 |
| 12178 | CG | LEU | C | 19 | -70.049 | -12.956 | 43.083 | 1.00 | 40.27 |
| 12179 | CD1 | LEU | C | 19 | -69.561 | -13.169 | 41.653 | 1.00 | 37.72 |

FIGURE 3 IE

| A | B | C | D | E | F | G | H | I | J |
|---|---|---|---|---|---|---|---|---|---|
| 12180 | CD2 | LEU | C | 19 | -71.488 | -13.411 | 43.242 | 1.00 | 38.11 |
| 12181 | C | LEU | C | 19 | -67.599 | -11.634 | 44.210 | 1.00 | 41.21 |
| 12182 | O | LEU | C | 19 | -67.565 | -10.861 | 43.260 | 1.00 | 41.21 |
| 12183 | N | THR | C | 20 | -67.591 | -11.233 | 45.474 | 1.00 | 41.41 |
| 12184 | CA | THR | C | 20 | -67.487 | -9.830 | 45.815 | 1.00 | 41.76 |
| 12185 | CB | THR | C | 20 | -67.676 | -9.631 | 47.295 | 1.00 | 41.53 |
| 12186 | OG1 | THR | C | 20 | -69.038 | -9.903 | 47.632 | 1.00 | 42.25 |
| 12187 | CG2 | THR | C | 20 | -67.539 | -8.183 | 47.627 | 1.00 | 41.82 |
| 12188 | C | THR | C | 20 | -66.134 | -9.283 | 45.388 | 1.00 | 42.26 |
| 12189 | O | THR | C | 20 | -66.060 | -8.192 | 44.817 | 1.00 | 42.44 |
| 12190 | N | ASP | C | 21 | -65.066 | -10.037 | 45.653 | 1.00 | 42.41 |
| 12191 | CA | ASP | C | 21 | -63.732 | -9.609 | 45.235 | 1.00 | 42.96 |
| 12192 | CB | ASP | C | 21 | -62.702 | -10.721 | 45.435 | 1.00 | 43.01 |
| 12193 | CG | ASP | C | 21 | -62.481 | -11.056 | 46.890 | 1.00 | 43.39 |
| 12194 | OD1 | ASP | C | 21 | -62.627 | -10.156 | 47.740 | 1.00 | 44.65 |
| 12195 | OD2 | ASP | C | 21 | -62.170 | -12.201 | 47.277 | 1.00 | 43.27 |
| 12196 | C | ASP | C | 21 | -63.754 | -9.208 | 43.769 | 1.00 | 43.05 |
| 12197 | O | ASP | C | 21 | -63.363 | -8.101 | 43.419 | 1.00 | 43.10 |
| 12198 | N | TYR | C | 22 | -64.217 | -10.124 | 42.922 | 1.00 | 43.50 |
| 12199 | CA | TYR | C | 22 | -64.325 | -9.900 | 41.481 | 1.00 | 43.70 |
| 12200 | CB | TYR | C | 22 | -64.818 | -11.179 | 40.792 | 1.00 | 43.69 |
| 12201 | CG | TYR | C | 22 | -65.288 | -10.957 | 39.370 | 1.00 | 43.01 |
| 12202 | CD1 | TYR | C | 22 | -64.396 | -10.569 | 38.376 | 1.00 | 43.15 |
| 12203 | CE1 | TYR | C | 22 | -64.826 | -10.350 | 37.070 | 1.00 | 43.76 |
| 12204 | CZ | TYR | C | 22 | -66.169 | -10.523 | 36.756 | 1.00 | 43.72 |
| 12205 | OH | TYR | C | 22 | -66.602 | -10.311 | 35.465 | 1.00 | 43.80 |
| 12206 | CE2 | TYR | C | 22 | -67.071 | -10.910 | 37.732 | 1.00 | 42.34 |
| 12207 | CD2 | TYR | C | 22 | -66.627 | -11.122 | 39.027 | 1.00 | 42.14 |
| 12208 | C | TYR | C | 22 | -65.259 | -8.749 | 41.112 | 1.00 | 44.08 |
| 12209 | O | TYR | C | 22 | -65.041 | -8.045 | 40.122 | 1.00 | 44.19 |
| 12210 | N | LEU | C | 23 | -66.305 | -8.557 | 41.896 | 1.00 | 44.48 |
| 12211 | CA | LEU | C | 23 | -67.267 | -7.525 | 41.562 | 1.00 | 45.38 |
| 12212 | CB | LEU | C | 23 | -68.628 | -7.829 | 42.189 | 1.00 | 44.86 |
| 12213 | CG | LEU | C | 23 | -69.390 | -9.010 | 41.584 | 1.00 | 44.42 |
| 12214 | CD1 | LEU | C | 23 | -70.828 | -9.061 | 42.101 | 1.00 | 42.61 |
| 12215 | CD2 | LEU | C | 23 | -69.361 | -8.937 | 40.062 | 1.00 | 42.28 |
| 12216 | C | LEU | C | 23 | -66.780 | -6.148 | 41.974 | 1.00 | 46.45 |
| 12217 | O | LEU | C | 23 | -67.070 | -5.157 | 41.313 | 1.00 | 46.55 |
| 12218 | N | LYS | C | 24 | -66.035 | -6.097 | 43.069 | 1.00 | 47.86 |
| 12219 | CA | LYS | C | 24 | -65.533 | -4.843 | 43.608 | 1.00 | 49.31 |
| 12220 | CB | LYS | C | 24 | -65.686 | -4.828 | 45.131 | 1.00 | 49.40 |
| 12221 | CG | LYS | C | 24 | -67.133 | -4.939 | 45.604 | 1.00 | 50.38 |
| 12222 | CD | LYS | C | 24 | -68.020 | -3.875 | 44.940 | 1.00 | 50.86 |
| 12223 | CE | LYS | C | 24 | -69.486 | -4.085 | 45.310 | 1.00 | 51.18 |
| 12224 | NZ | LYS | C | 24 | -70.403 | -3.015 | 44.800 | 1.00 | 50.26 |
| 12225 | C | LYS | C | 24 | -64.076 | -4.617 | 43.235 | 1.00 | 50.34 |
| 12226 | O | LYS | C | 24 | -63.490 | -3.592 | 43.585 | 1.00 | 50.81 |
| 12227 | N | ASN | C | 25 | -63.480 | -5.575 | 42.539 | 1.00 | 51.21 |
| 12228 | CA | ASN | C | 25 | -62.108 | -5.414 | 42.105 | 1.00 | 52.48 |
| 12229 | CB | ASN | C | 25 | -61.998 | -4.186 | 41.201 | 1.00 | 52.83 |
| 12230 | CG | ASN | C | 25 | -62.701 | -4.385 | 39.871 | 1.00 | 54.31 |

FIGURE 3 IF

| A | B | C | D | E | F | G | H | I | J |
|---|---|---|---|---|---|---|---|---|---|
| 12231 | OD1 | ASN | C | 25 | -62.588 | -5.444 | 39.257 | 1.00 | 56.23 |
| 12232 | ND2 | ASN | C | 25 | -63.436 | -3.374 | 39.425 | 1.00 | 55.37 |
| 12233 | C | ASN | C | 25 | -61.105 | -5.318 | 43.256 | 1.00 | 53.03 |
| 12234 | O | ASN | C | 25 | -60.083 | -4.651 | 43.141 | 1.00 | 52.96 |
| 12235 | N | THR | C | 26 | -61.402 | -5.988 | 44.363 | 1.00 | 53.73 |
| 12236 | CA | THR | C | 26 | -60.494 | -6.011 | 45.494 | 1.00 | 54.61 |
| 12237 | CB | THR | C | 26 | -60.865 | -7.157 | 46.438 | 1.00 | 54.70 |
| 12238 | OG1 | THR | C | 26 | -62.056 | -6.812 | 47.158 | 1.00 | 55.46 |
| 12239 | CG2 | THR | C | 26 | -59.817 | -7.314 | 47.540 | 1.00 | 54.55 |
| 12240 | C | THR | C | 26 | -59.048 | -6.165 | 45.017 | 1.00 | 55.09 |
| 12241 | O | THR | C | 26 | -58.162 | -5.427 | 45.447 | 1.00 | 55.02 |
| 12242 | N | TYR | C | 27 | -58.821 | -7.111 | 44.111 | 1.00 | 55.59 |
| 12243 | CA | TYR | C | 27 | -57.484 | -7.356 | 43.584 | 1.00 | 56.25 |
| 12244 | CB | TYR | C | 27 | -57.151 | -8.849 | 43.652 | 1.00 | 55.96 |
| 12245 | CG | TYR | C | 27 | -57.406 | -9.426 | 45.028 | 1.00 | 54.73 |
| 12246 | CD1 | TYR | C | 27 | -56.587 | -9.101 | 46.105 | 1.00 | 54.43 |
| 12247 | CE1 | TYR | C | 27 | -56.827 | -9.618 | 47.369 | 1.00 | 52.54 |
| 12248 | CZ | TYR | C | 27 | -57.900 | -10.451 | 47.561 | 1.00 | 52.34 |
| 12249 | OH | TYR | C | 27 | -58.160 | -10.972 | 48.805 | 1.00 | 53.22 |
| 12250 | CE2 | TYR | C | 27 | -58.731 | -10.774 | 46.513 | 1.00 | 52.33 |
| 12251 | CD2 | TYR | C | 27 | -58.481 | -10.261 | 45.260 | 1.00 | 53.00 |
| 12252 | C | TYR | C | 27 | -57.304 | -6.783 | 42.180 | 1.00 | 56.99 |
| 12253 | O | TYR | C | 27 | -57.593 | -7.432 | 41.185 | 1.00 | 56.86 |
| 12254 | N | ARG | C | 28 | -56.798 | -5.555 | 42.134 | 1.00 | 58.45 |
| 12255 | CA | ARG | C | 28 | -56.603 | -4.798 | 40.899 | 1.00 | 59.78 |
| 12256 | CB | ARG | C | 28 | -56.602 | -3.298 | 41.215 | 1.00 | 60.24 |
| 12257 | CG | ARG | C | 28 | -57.785 | -2.515 | 40.686 | 1.00 | 62.82 |
| 12258 | CD | ARG | C | 28 | -57.932 | -1.118 | 41.292 | 1.00 | 66.38 |
| 12259 | NE | ARG | C | 28 | -58.666 | -1.151 | 42.558 | 1.00 | 69.47 |
| 12260 | CZ | ARG | C | 28 | -59.184 | -0.082 | 43.160 | 1.00 | 70.68 |
| 12261 | NH1 | ARG | C | 28 | -59.050 | 1.125 | 42.615 | 1.00 | 70.81 |
| 12262 | NH2 | ARG | C | 28 | -59.839 | -0.220 | 44.310 | 1.00 | 70.59 |
| 12263 | C | ARG | C | 28 | -55.302 | -5.109 | 40.191 | 1.00 | 60.06 |
| 12264 | O | ARG | C | 28 | -54.233 | -5.064 | 40.791 | 1.00 | 59.89 |
| 12265 | N | LEU | C | 29 | -55.395 | -5.399 | 38.900 | 1.00 | 60.70 |
| 12266 | CA | LEU | C | 29 | -54.210 | -5.618 | 38.097 | 1.00 | 61.41 |
| 12267 | CB | LEU | C | 29 | -54.540 | -6.421 | 36.844 | 1.00 | 61.17 |
| 12268 | CG | LEU | C | 29 | -54.629 | -7.932 | 37.038 | 1.00 | 61.39 |
| 12269 | CD1 | LEU | C | 29 | -55.261 | -8.591 | 35.823 | 1.00 | 61.58 |
| 12270 | CD2 | LEU | C | 29 | -53.252 | -8.499 | 37.298 | 1.00 | 61.27 |
| 12271 | C | LEU | C | 29 | -53.699 | -4.250 | 37.699 | 1.00 | 62.14 |
| 12272 | O | LEU | C | 29 | -54.407 | -3.481 | 37.048 | 1.00 | 62.24 |
| 12273 | N | LYS | C | 30 | -52.484 | -3.927 | 38.121 | 1.00 | 62.82 |
| 12274 | CA | LYS | C | 30 | -51.889 | -2.660 | 37.741 | 1.00 | 63.41 |
| 12275 | CB | LYS | C | 30 | -50.628 | -2.383 | 38.567 | 1.00 | 63.28 |
| 12276 | CG | LYS | C | 30 | -50.533 | -0.964 | 39.122 | 1.00 | 64.04 |
| 12277 | CD | LYS | C | 30 | -50.132 | -0.957 | 40.598 | 1.00 | 64.72 |
| 12278 | CE | LYS | C | 30 | -50.252 | 0.440 | 41.214 | 1.00 | 65.38 |
| 12279 | NZ | LYS | C | 30 | -51.623 | 1.024 | 41.080 | 1.00 | 65.09 |
| 12280 | C | LYS | C | 30 | -51.552 | -2.737 | 36.260 | 1.00 | 63.67 |
| 12281 | O | LYS | C | 30 | -51.233 | -3.805 | 35.745 | 1.00 | 63.57 |

FIGURE 3 IG

| A | B | C | D | E | F | G | H | I | J |
|---|---|---|---|---|---|---|---|---|---|
| 12282 | N | LEU | C | 31 | -51.653 | -1.608 | 35.575 | 1.00 | 64.38 |
| 12283 | CA | LEU | C | 31 | -51.292 | -1.534 | 34.167 | 1.00 | 65.35 |
| 12284 | CB | LEU | C | 31 | -52.499 | -1.151 | 33.299 | 1.00 | 65.22 |
| 12285 | CG | LEU | C | 31 | -53.869 | -1.831 | 33.385 | 1.00 | 65.26 |
| 12286 | CD1 | LEU | C | 31 | -54.681 | -1.328 | 34.576 | 1.00 | 64.95 |
| 12287 | CD2 | LEU | C | 31 | -54.628 | -1.569 | 32.102 | 1.00 | 65.03 |
| 12288 | C | LEU | C | 31 | -50.235 | -0.441 | 34.024 | 1.00 | 66.02 |
| 12289 | O | LEU | C | 31 | -50.043 | 0.369 | 34.935 | 1.00 | 66.11 |
| 12290 | N | TYR | C | 32 | -49.543 | -0.422 | 32.893 | 1.00 | 66.68 |
| 12291 | CA | TYR | C | 32 | -48.619 | 0.667 | 32.621 | 1.00 | 67.59 |
| 12292 | CB | TYR | C | 32 | -47.159 | 0.282 | 32.874 | 1.00 | 67.51 |
| 12293 | CG | TYR | C | 32 | -46.281 | 1.495 | 33.113 | 1.00 | 67.22 |
| 12294 | CD1 | TYR | C | 32 | -45.767 | 2.223 | 32.053 | 1.00 | 67.11 |
| 12295 | CE1 | TYR | C | 32 | -44.976 | 3.336 | 32.269 | 1.00 | 68.00 |
| 12296 | CZ | TYR | C | 32 | -44.703 | 3.737 | 33.559 | 1.00 | 67.92 |
| 12297 | OH | TYR | C | 32 | -43.919 | 4.845 | 33.780 | 1.00 | 68.81 |
| 12298 | CE2 | TYR | C | 32 | -45.207 | 3.032 | 34.629 | 1.00 | 67.41 |
| 12299 | CD2 | TYR | C | 32 | -45.994 | 1.924 | 34.402 | 1.00 | 66.89 |
| 12300 | C | TYR | C | 32 | -48.819 | 1.121 | 31.192 | 1.00 | 68.31 |
| 12301 | O | TYR | C | 32 | -48.103 | 0.705 | 30.285 | 1.00 | 68.18 |
| 12302 | N | SER | C | 33 | -49.818 | 1.972 | 31.000 | 1.00 | 69.60 |
| 12303 | CA | SER | C | 33 | -50.153 | 2.457 | 29.672 | 1.00 | 70.73 |
| 12304 | CB | SER | C | 33 | -51.666 | 2.619 | 29.515 | 1.00 | 70.72 |
| 12305 | OG | SER | C | 33 | -52.008 | 2.979 | 28.181 | 1.00 | 71.44 |
| 12306 | C | SER | C | 33 | -49.459 | 3.773 | 29.395 | 1.00 | 71.43 |
| 12307 | O | SER | C | 33 | -49.712 | 4.778 | 30.059 | 1.00 | 71.71 |
| 12308 | N | LEU | C | 34 | -48.567 | 3.754 | 28.416 | 1.00 | 72.35 |
| 12309 | CA | LEU | C | 34 | -47.866 | 4.956 | 28.015 | 1.00 | 73.17 |
| 12310 | CB | LEU | C | 34 | -46.359 | 4.733 | 28.064 | 1.00 | 72.95 |
| 12311 | CG | LEU | C | 34 | -45.856 | 3.406 | 27.505 | 1.00 | 72.50 |
| 12312 | CD1 | LEU | C | 34 | -45.844 | 3.422 | 25.989 | 1.00 | 71.40 |
| 12313 | CD2 | LEU | C | 34 | -44.472 | 3.128 | 28.047 | 1.00 | 72.03 |
| 12314 | C | LEU | C | 34 | -48.300 | 5.318 | 26.609 | 1.00 | 73.94 |
| 12315 | O | LEU | C | 34 | -48.922 | 4.514 | 25.917 | 1.00 | 73.98 |
| 12316 | N | ARG | C | 35 | -47.988 | 6.538 | 26.201 | 1.00 | 74.87 |
| 12317 | CA | ARG | C | 35 | -48.303 | 6.988 | 24.857 | 1.00 | 75.88 |
| 12318 | CB | ARG | C | 35 | -49.614 | 7.789 | 24.823 | 1.00 | 75.99 |
| 12319 | CG | ARG | C | 35 | -49.811 | 8.762 | 25.979 | 1.00 | 76.62 |
| 12320 | CD | ARG | C | 35 | -51.037 | 9.673 | 25.839 | 1.00 | 77.67 |
| 12321 | NE | ARG | C | 35 | -52.302 | 8.939 | 25.882 | 1.00 | 78.08 |
| 12322 | CZ | ARG | C | 35 | -53.497 | 9.504 | 25.748 | 1.00 | 78.24 |
| 12323 | NH1 | ARG | C | 35 | -53.598 | 10.815 | 25.566 | 1.00 | 77.92 |
| 12324 | NH2 | ARG | C | 35 | -54.596 | 8.761 | 25.799 | 1.00 | 77.84 |
| 12325 | C | ARG | C | 35 | -47.124 | 7.798 | 24.336 | 1.00 | 76.42 |
| 12326 | O | ARG | C | 35 | -46.803 | 8.861 | 24.866 | 1.00 | 76.47 |
| 12327 | N | TRP | C | 36 | -46.470 | 7.269 | 23.307 | 1.00 | 77.18 |
| 12328 | CA | TRP | C | 36 | -45.283 | 7.894 | 22.741 | 1.00 | 77.77 |
| 12329 | CB | TRP | C | 36 | -44.548 | 6.913 | 21.828 | 1.00 | 77.64 |
| 12330 | CG | TRP | C | 36 | -44.025 | 5.709 | 22.539 | 1.00 | 78.06 |
| 12331 | CD1 | TRP | C | 36 | -44.588 | 4.466 | 22.571 | 1.00 | 78.41 |
| 12332 | NE1 | TRP | C | 36 | -43.813 | 3.612 | 23.318 | 1.00 | 78.31 |

FIGURE 3 IH

| A | B | C | D | E | F | G | H | I | J |
|---|---|---|---|---|---|---|---|---|---|
| 12333 | CE2 | TRP | C | 36 | -42.728 | 4.299 | 23.794 | 1.00 | 78.48 |
| 12334 | CD2 | TRP | C | 36 | -42.829 | 5.624 | 23.319 | 1.00 | 78.27 |
| 12335 | CE3 | TRP | C | 36 | -41.828 | 6.535 | 23.668 | 1.00 | 78.05 |
| 12336 | CZ3 | TRP | C | 36 | -40.785 | 6.106 | 24.465 | 1.00 | 78.20 |
| 12337 | CH2 | TRP | C | 36 | -40.714 | 4.784 | 24.919 | 1.00 | 78.05 |
| 12338 | CZ2 | TRP | C | 36 | -41.673 | 3.869 | 24.597 | 1.00 | 78.18 |
| 12339 | C | TRP | C | 36 | -45.586 | 9.174 | 21.974 | 1.00 | 78.25 |
| 12340 | O | TRP | C | 36 | -46.190 | 9.149 | 20.900 | 1.00 | 78.31 |
| 12341 | N | ILE | C | 37 | -45.155 | 10.297 | 22.532 | 1.00 | 78.82 |
| 12342 | CA | ILE | C | 37 | -45.307 | 11.573 | 21.858 | 1.00 | 79.44 |
| 12343 | CB | ILE | C | 37 | -45.381 | 12.717 | 22.889 | 1.00 | 79.40 |
| 12344 | CG1 | ILE | C | 37 | -45.439 | 14.085 | 22.195 | 1.00 | 79.66 |
| 12345 | CD1 | ILE | C | 37 | -44.087 | 14.770 | 22.021 | 1.00 | 79.61 |
| 12346 | CG2 | ILE | C | 37 | -44.220 | 12.621 | 23.864 | 1.00 | 79.60 |
| 12347 | C | ILE | C | 37 | -44.135 | 11.751 | 20.897 | 1.00 | 79.77 |
| 12348 | O | ILE | C | 37 | -44.213 | 12.511 | 19.937 | 1.00 | 79.90 |
| 12349 | N | SER | C | 38 | -43.061 | 11.008 | 21.145 | 1.00 | 80.29 |
| 12350 | CA | SER | C | 38 | -41.858 | 11.087 | 20.327 | 1.00 | 80.82 |
| 12351 | CB | SER | C | 38 | -40.873 | 12.072 | 20.956 | 1.00 | 80.90 |
| 12352 | OG | SER | C | 38 | -40.539 | 11.670 | 22.276 | 1.00 | 80.77 |
| 12353 | C | SER | C | 38 | -41.186 | 9.727 | 20.207 | 1.00 | 81.18 |
| 12354 | O | SER | C | 38 | -41.839 | 8.686 | 20.283 | 1.00 | 81.24 |
| 12355 | N | ASP | C | 39 | -39.871 | 9.744 | 20.018 | 1.00 | 81.60 |
| 12356 | CA | ASP | C | 39 | -39.097 | 8.517 | 19.958 | 1.00 | 82.00 |
| 12357 | CB | ASP | C | 39 | -38.289 | 8.452 | 18.669 | 1.00 | 82.03 |
| 12358 | CG | ASP | C | 39 | -37.866 | 7.041 | 18.323 | 1.00 | 82.10 |
| 12359 | OD1 | ASP | C | 39 | -38.078 | 6.629 | 17.171 | 1.00 | 82.27 |
| 12360 | OD2 | ASP | C | 39 | -37.322 | 6.265 | 19.132 | 1.00 | 81.97 |
| 12361 | C | ASP | C | 39 | -38.163 | 8.433 | 21.161 | 1.00 | 82.36 |
| 12362 | O | ASP | C | 39 | -37.227 | 7.639 | 21.179 | 1.00 | 82.27 |
| 12363 | N | HIS | C | 40 | -38.419 | 9.259 | 22.167 | 1.00 | 82.93 |
| 12364 | CA | HIS | C | 40 | -37.577 | 9.283 | 23.356 | 1.00 | 83.59 |
| 12365 | CB | HIS | C | 40 | -36.573 | 10.440 | 23.285 | 1.00 | 83.80 |
| 12366 | CG | HIS | C | 40 | -36.336 | 10.960 | 21.900 | 1.00 | 84.44 |
| 12367 | ND1 | HIS | C | 40 | -36.976 | 12.078 | 21.409 | 1.00 | 84.78 |
| 12368 | CE1 | HIS | C | 40 | -36.574 | 12.303 | 20.170 | 1.00 | 85.23 |
| 12369 | NE2 | HIS | C | 40 | -35.695 | 11.373 | 19.841 | 1.00 | 85.24 |
| 12370 | CD2 | HIS | C | 40 | -35.526 | 10.522 | 20.906 | 1.00 | 84.75 |
| 12371 | C | HIS | C | 40 | -38.439 | 9.467 | 24.593 | 1.00 | 83.84 |
| 12372 | O | HIS | C | 40 | -38.143 | 8.944 | 25.667 | 1.00 | 83.91 |
| 12373 | N | GLU | C | 41 | -39.507 | 10.234 | 24.437 | 1.00 | 84.11 |
| 12374 | CA | GLU | C | 41 | -40.387 | 10.515 | 25.551 | 1.00 | 84.28 |
| 12375 | CB | GLU | C | 41 | -40.523 | 12.026 | 25.743 | 1.00 | 84.27 |
| 12376 | CG | GLU | C | 41 | -39.215 | 12.726 | 26.072 | 1.00 | 84.40 |
| 12377 | CD | GLU | C | 41 | -39.278 | 14.225 | 25.843 | 1.00 | 84.96 |
| 12378 | OE1 | GLU | C | 41 | -39.163 | 14.651 | 24.672 | 1.00 | 85.40 |
| 12379 | OE2 | GLU | C | 41 | -39.440 | 14.977 | 26.830 | 1.00 | 84.60 |
| 12380 | C | GLU | C | 41 | -41.754 | 9.892 | 25.337 | 1.00 | 84.47 |
| 12381 | O | GLU | C | 41 | -42.182 | 9.674 | 24.203 | 1.00 | 84.46 |
| 12382 | N | TYR | C | 42 | -42.421 | 9.586 | 26.441 | 1.00 | 84.64 |
| 12383 | CA | TYR | C | 42 | -43.774 | 9.068 | 26.408 | 1.00 | 84.87 |

FIGURE 3 II

| A | B | C | D | E | F | G | H | I | J |
|---|---|---|---|---|---|---|---|---|---|
| 12384 | CB | TYR | C | 42 | -43.796 | 7.532 | 26.438 | 1.00 | 84.80 |
| 12385 | CG | TYR | C | 42 | -43.306 | 6.902 | 27.726 | 1.00 | 84.02 |
| 12386 | CD1 | TYR | C | 42 | -43.977 | 7.109 | 28.924 | 1.00 | 83.42 |
| 12387 | CE1 | TYR | C | 42 | -43.541 | 6.537 | 30.097 | 1.00 | 82.96 |
| 12388 | CZ | TYR | C | 42 | -42.422 | 5.739 | 30.089 | 1.00 | 82.88 |
| 12389 | OH | TYR | C | 42 | -41.993 | 5.170 | 31.265 | 1.00 | 82.70 |
| 12390 | CE2 | TYR | C | 42 | -41.736 | 5.510 | 28.913 | 1.00 | 83.03 |
| 12391 | CD2 | TYR | C | 42 | -42.182 | 6.089 | 27.740 | 1.00 | 83.23 |
| 12392 | C | TYR | C | 42 | -44.494 | 9.660 | 27.605 | 1.00 | 85.34 |
| 12393 | O | TYR | C | 42 | -43.858 | 10.056 | 28.579 | 1.00 | 85.32 |
| 12394 | N | LEU | C | 43 | -45.816 | 9.741 | 27.532 | 1.00 | 85.95 |
| 12395 | CA | LEU | C | 43 | -46.584 | 10.321 | 28.624 | 1.00 | 86.61 |
| 12396 | CB | LEU | C | 43 | -47.702 | 11.209 | 28.080 | 1.00 | 86.53 |
| 12397 | CG | LEU | C | 43 | -47.305 | 12.660 | 27.813 | 1.00 | 86.47 |
| 12398 | CD1 | LEU | C | 43 | -45.798 | 12.823 | 27.843 | 1.00 | 86.41 |
| 12399 | CD2 | LEU | C | 43 | -47.885 | 13.154 | 26.497 | 1.00 | 86.63 |
| 12400 | C | LEU | C | 43 | -47.151 | 9.264 | 29.552 | 1.00 | 87.14 |
| 12401 | O | LEU | C | 43 | -47.387 | 8.129 | 29.149 | 1.00 | 87.11 |
| 12402 | N | TYR | C | 44 | -47.358 | 9.650 | 30.803 | 1.00 | 88.04 |
| 12403 | CA | TYR | C | 44 | -47.915 | 8.759 | 31.808 | 1.00 | 88.99 |
| 12404 | CB | TYR | C | 44 | -46.805 | 8.153 | 32.656 | 1.00 | 88.86 |
| 12405 | CG | TYR | C | 44 | -47.257 | 7.016 | 33.533 | 1.00 | 88.89 |
| 12406 | CD1 | TYR | C | 44 | -47.742 | 5.840 | 32.979 | 1.00 | 88.78 |
| 12407 | CE1 | TYR | C | 44 | -48.155 | 4.793 | 33.778 | 1.00 | 88.68 |
| 12408 | CZ | TYR | C | 44 | -48.083 | 4.914 | 35.148 | 1.00 | 88.89 |
| 12409 | OH | TYR | C | 44 | -48.492 | 3.872 | 35.950 | 1.00 | 89.26 |
| 12410 | CE2 | TYR | C | 44 | -47.605 | 6.073 | 35.722 | 1.00 | 88.83 |
| 12411 | CD2 | TYR | C | 44 | -47.197 | 7.115 | 34.916 | 1.00 | 88.84 |
| 12412 | C | TYR | C | 44 | -48.863 | 9.567 | 32.677 | 1.00 | 89.77 |
| 12413 | O | TYR | C | 44 | -48.695 | 10.776 | 32.821 | 1.00 | 89.89 |
| 12414 | N | LYS | C | 45 | -49.860 | 8.908 | 33.256 | 1.00 | 90.81 |
| 12415 | CA | LYS | C | 45 | -50.869 | 9.620 | 34.036 | 1.00 | 91.87 |
| 12416 | CB | LYS | C | 45 | -52.221 | 9.590 | 33.310 | 1.00 | 91.78 |
| 12417 | CG | LYS | C | 45 | -52.164 | 9.914 | 31.814 | 1.00 | 92.08 |
| 12418 | CD | LYS | C | 45 | -51.805 | 8.692 | 30.972 | 1.00 | 92.16 |
| 12419 | CE | LYS | C | 45 | -52.201 | 8.877 | 29.519 | 1.00 | 92.01 |
| 12420 | NZ | LYS | C | 45 | -52.202 | 7.591 | 28.766 | 1.00 | 92.72 |
| 12421 | C | LYS | C | 45 | -51.032 | 9.060 | 35.447 | 1.00 | 92.57 |
| 12422 | O | LYS | C | 45 | -51.927 | 8.253 | 35.694 | 1.00 | 92.69 |
| 12423 | N | GLN | C | 46 | -50.186 | 9.511 | 36.372 | 1.00 | 93.38 |
| 12424 | CA | GLN | C | 46 | -50.218 | 9.015 | 37.749 | 1.00 | 94.22 |
| 12425 | CB | GLN | C | 46 | -48.913 | 9.366 | 38.475 | 1.00 | 94.24 |
| 12426 | CG | GLN | C | 46 | -48.374 | 8.268 | 39.395 | 1.00 | 94.78 |
| 12427 | CD | GLN | C | 46 | -49.139 | 8.143 | 40.705 | 1.00 | 95.16 |
| 12428 | OE1 | GLN | C | 46 | -50.366 | 8.068 | 40.710 | 1.00 | 95.31 |
| 12429 | NE2 | GLN | C | 46 | -48.411 | 8.107 | 41.816 | 1.00 | 95.41 |
| 12430 | C | GLN | C | 46 | -51.418 | 9.548 | 38.536 | 1.00 | 94.68 |
| 12431 | O | GLN | C | 46 | -51.269 | 10.449 | 39.363 | 1.00 | 94.77 |
| 12432 | N | GLU | C | 47 | -52.593 | 8.973 | 38.279 | 1.00 | 95.27 |
| 12433 | CA | GLU | C | 47 | -53.851 | 9.343 | 38.944 | 1.00 | 95.80 |
| 12434 | CB | GLU | C | 47 | -54.120 | 8.441 | 40.156 | 1.00 | 95.88 |

FIGURE 3 IJ

| A | B | C | D | E | F | G | H | I | J |
|---|---|---|---|---|---|---|---|---|---|
| 12435 | CG | GLU | C | 47 | -55.588 | 8.386 | 40.563 | 1.00 | 96.18 |
| 12436 | CD | GLU | C | 47 | -55.795 | 8.516 | 42.063 | 1.00 | 96.41 |
| 12437 | OE1 | GLU | C | 47 | -55.740 | 9.655 | 42.577 | 1.00 | 96.51 |
| 12438 | OE2 | GLU | C | 47 | -56.020 | 7.484 | 42.730 | 1.00 | 96.50 |
| 12439 | C | GLU | C | 47 | -53.914 | 10.806 | 39.377 | 1.00 | 96.06 |
| 12440 | O | GLU | C | 47 | -54.466 | 11.135 | 40.426 | 1.00 | 96.06 |
| 12441 | N | ASN | C | 48 | -53.350 | 11.683 | 38.561 | 1.00 | 96.45 |
| 12442 | CA | ASN | C | 48 | -53.325 | 13.096 | 38.883 | 1.00 | 96.79 |
| 12443 | CB | ASN | C | 48 | -52.344 | 13.362 | 40.031 | 1.00 | 96.76 |
| 12444 | CG | ASN | C | 48 | -52.768 | 14.526 | 40.920 | 1.00 | 96.79 |
| 12445 | OD1 | ASN | C | 48 | -53.812 | 15.143 | 40.707 | 1.00 | 96.55 |
| 12446 | ND2 | ASN | C | 48 | -51.954 | 14.822 | 41.929 | 1.00 | 96.67 |
| 12447 | C | ASN | C | 48 | -52.901 | 13.870 | 37.650 | 1.00 | 97.05 |
| 12448 | O | ASN | C | 48 | -53.737 | 14.337 | 36.874 | 1.00 | 97.18 |
| 12449 | N | ASN | C | 49 | -51.593 | 13.967 | 37.454 | 1.00 | 97.25 |
| 12450 | CA | ASN | C | 49 | -51.052 | 14.748 | 36.359 | 1.00 | 97.43 |
| 12451 | CB | ASN | C | 49 | -50.086 | 15.790 | 36.912 | 1.00 | 97.48 |
| 12452 | CG | ASN | C | 49 | -50.143 | 15.890 | 38.424 | 1.00 | 97.66 |
| 12453 | OD1 | ASN | C | 49 | -49.374 | 15.232 | 39.130 | 1.00 | 97.35 |
| 12454 | ND2 | ASN | C | 49 | -51.054 | 16.714 | 38.931 | 1.00 | 97.85 |
| 12455 | C | ASN | C | 49 | -50.315 | 13.901 | 35.342 | 1.00 | 97.54 |
| 12456 | O | ASN | C | 49 | -49.948 | 12.758 | 35.614 | 1.00 | 97.56 |
| 12457 | N | ILE | C | 50 | -50.084 | 14.484 | 34.173 | 1.00 | 97.73 |
| 12458 | CA | ILE | C | 50 | -49.359 | 13.809 | 33.113 | 1.00 | 97.89 |
| 12459 | CB | ILE | C | 50 | -49.779 | 14.357 | 31.748 | 1.00 | 97.92 |
| 12460 | CG1 | ILE | C | 50 | -51.246 | 14.025 | 31.480 | 1.00 | 98.05 |
| 12461 | CD1 | ILE | C | 50 | -51.904 | 14.956 | 30.490 | 1.00 | 98.30 |
| 12462 | CG2 | ILE | C | 50 | -48.889 | 13.791 | 30.654 | 1.00 | 97.72 |
| 12463 | C | ILE | C | 50 | -47.861 | 13.978 | 33.298 | 1.00 | 98.00 |
| 12464 | O | ILE | C | 50 | -47.334 | 15.086 | 33.239 | 1.00 | 97.98 |
| 12465 | N | LEU | C | 51 | -47.180 | 12.866 | 33.536 | 1.00 | 98.19 |
| 12466 | CA | LEU | C | 51 | -45.738 | 12.881 | 33.684 | 1.00 | 98.33 |
| 12467 | CB | LEU | C | 51 | -45.289 | 11.771 | 34.634 | 1.00 | 98.39 |
| 12468 | CG | LEU | C | 51 | -45.481 | 11.940 | 36.144 | 1.00 | 98.49 |
| 12469 | CD1 | LEU | C | 51 | -46.875 | 12.447 | 36.481 | 1.00 | 98.70 |
| 12470 | CD2 | LEU | C | 51 | -45.191 | 10.627 | 36.870 | 1.00 | 98.48 |
| 12471 | C | LEU | C | 51 | -45.096 | 12.665 | 32.324 | 1.00 | 98.41 |
| 12472 | O | LEU | C | 51 | -45.553 | 11.837 | 31.536 | 1.00 | 98.34 |
| 12473 | N | VAL | C | 52 | -44.050 | 13.429 | 32.039 | 1.00 | 98.58 |
| 12474 | CA | VAL | C | 52 | -43.288 | 13.222 | 30.821 | 1.00 | 98.83 |
| 12475 | CB | VAL | C | 52 | -42.650 | 14.528 | 30.308 | 1.00 | 98.82 |
| 12476 | CG1 | VAL | C | 52 | -41.491 | 14.951 | 31.200 | 1.00 | 98.92 |
| 12477 | CG2 | VAL | C | 52 | -42.191 | 14.368 | 28.863 | 1.00 | 98.68 |
| 12478 | C | VAL | C | 52 | -42.216 | 12.212 | 31.204 | 1.00 | 98.95 |
| 12479 | O | VAL | C | 52 | -41.835 | 12.139 | 32.367 | 1.00 | 99.00 |
| 12480 | N | PHE | C | 53 | -41.748 | 11.415 | 30.252 | 1.00 | 99.11 |
| 12481 | CA | PHE | C | 53 | -40.745 | 10.404 | 30.563 | 1.00 | 99.34 |
| 12482 | CB | PHE | C | 53 | -41.399 | 9.033 | 30.736 | 1.00 | 99.28 |
| 12483 | CG | PHE | C | 53 | -41.855 | 8.734 | 32.137 | 1.00 | 99.21 |
| 12484 | CD1 | PHE | C | 53 | -43.035 | 9.264 | 32.629 | 1.00 | 99.25 |
| 12485 | CE1 | PHE | C | 53 | -43.460 | 8.973 | 33.912 | 1.00 | 99.14 |

FIGURE 3 IK

| A | B | C | D | E | F | G | H | I | J |
|---|---|---|---|---|---|---|---|---|---|
| 12486 | CZ | PHE | C | 53 | -42.713 | 8.138 | 34.714 | 1.00 | 99.13 |
| 12487 | CE2 | PHE | C | 53 | -41.542 | 7.595 | 34.232 | 1.00 | 99.16 |
| 12488 | CD2 | PHE | C | 53 | -41.121 | 7.888 | 32.949 | 1.00 | 99.08 |
| 12489 | C | PHE | C | 53 | -39.698 | 10.292 | 29.472 | 1.00 | 99.62 |
| 12490 | O | PHE | C | 53 | -40.028 | 10.241 | 28.289 | 1.00 | 99.62 |
| 12491 | N | ASN | C | 54 | -38.433 | 10.242 | 29.875 | 1.00 | 99.97 |
| 12492 | CA | ASN | C | 54 | -37.352 | 10.043 | 28.926 | 1.00 | 100.28 |
| 12493 | CB | ASN | C | 54 | -36.065 | 10.704 | 29.423 | 1.00 | 100.27 |
| 12494 | CG | ASN | C | 54 | -35.132 | 11.099 | 28.288 | 1.00 | 100.22 |
| 12495 | OD1 | ASN | C | 54 | -34.615 | 12.215 | 28.259 | 1.00 | 99.74 |
| 12496 | ND2 | ASN | C | 54 | -34.918 | 10.185 | 27.343 | 1.00 | 100.19 |
| 12497 | C | ASN | C | 54 | -37.151 | 8.544 | 28.768 | 1.00 | 100.54 |
| 12498 | O | ASN | C | 54 | -36.831 | 7.853 | 29.732 | 1.00 | 100.56 |
| 12499 | N | ALA | C | 55 | -37.348 | 8.039 | 27.557 | 1.00 | 100.95 |
| 12500 | CA | ALA | C | 55 | -37.216 | 6.607 | 27.311 | 1.00 | 101.44 |
| 12501 | CB | ALA | C | 55 | -37.472 | 6.294 | 25.851 | 1.00 | 101.38 |
| 12502 | C | ALA | C | 55 | -35.863 | 6.051 | 27.738 | 1.00 | 101.82 |
| 12503 | O | ALA | C | 55 | -35.786 | 4.955 | 28.291 | 1.00 | 101.88 |
| 12504 | N | GLU | C | 56 | -34.800 | 6.808 | 27.491 | 1.00 | 102.32 |
| 12505 | CA | GLU | C | 56 | -33.451 | 6.341 | 27.793 | 1.00 | 102.83 |
| 12506 | CB | GLU | C | 56 | -32.410 | 7.212 | 27.085 | 1.00 | 102.82 |
| 12507 | CG | GLU | C | 56 | -31.007 | 6.628 | 27.113 | 1.00 | 103.08 |
| 12508 | CD | GLU | C | 56 | -30.007 | 7.452 | 26.323 | 1.00 | 103.39 |
| 12509 | OE1 | GLU | C | 56 | -30.419 | 8.137 | 25.361 | 1.00 | 103.42 |
| 12510 | OE2 | GLU | C | 56 | -28.806 | 7.414 | 26.666 | 1.00 | 103.35 |
| 12511 | C | GLU | C | 56 | -33.125 | 6.244 | 29.286 | 1.00 | 103.16 |
| 12512 | O | GLU | C | 56 | -32.614 | 5.223 | 29.747 | 1.00 | 103.16 |
| 12513 | N | TYR | C | 57 | -33.429 | 7.296 | 30.039 | 1.00 | 103.60 |
| 12514 | CA | TYR | C | 57 | -33.060 | 7.339 | 31.452 | 1.00 | 104.14 |
| 12515 | CB | TYR | C | 57 | -32.274 | 8.618 | 31.741 | 1.00 | 104.26 |
| 12516 | CG | TYR | C | 57 | -31.538 | 9.154 | 30.534 | 1.00 | 104.73 |
| 12517 | CD1 | TYR | C | 57 | -30.284 | 8.670 | 30.187 | 1.00 | 105.05 |
| 12518 | CE1 | TYR | C | 57 | -29.612 | 9.157 | 29.086 | 1.00 | 105.39 |
| 12519 | CZ | TYR | C | 57 | -30.198 | 10.136 | 28.309 | 1.00 | 105.58 |
| 12520 | OH | TYR | C | 57 | -29.536 | 10.624 | 27.207 | 1.00 | 105.78 |
| 12521 | CE2 | TYR | C | 57 | -31.443 | 10.631 | 28.631 | 1.00 | 105.37 |
| 12522 | CD2 | TYR | C | 57 | -32.105 | 10.140 | 29.735 | 1.00 | 105.19 |
| 12523 | C | TYR | C | 57 | -34.241 | 7.233 | 32.413 | 1.00 | 104.42 |
| 12524 | O | TYR | C | 57 | -34.054 | 7.177 | 33.631 | 1.00 | 104.31 |
| 12525 | N | GLY | C | 58 | -35.453 | 7.220 | 31.869 | 1.00 | 104.74 |
| 12526 | CA | GLY | C | 58 | -36.646 | 7.090 | 32.684 | 1.00 | 105.14 |
| 12527 | C | GLY | C | 58 | -36.773 | 8.136 | 33.772 | 1.00 | 105.47 |
| 12528 | O | GLY | C | 58 | -37.237 | 7.842 | 34.876 | 1.00 | 105.45 |
| 12529 | N | ASN | C | 59 | -36.336 | 9.355 | 33.475 | 1.00 | 105.72 |
| 12530 | CA | ASN | C | 59 | -36.499 | 10.451 | 34.417 | 1.00 | 105.99 |
| 12531 | CB | ASN | C | 59 | -35.227 | 11.296 | 34.550 | 1.00 | 106.00 |
| 12532 | CG | ASN | C | 59 | -34.740 | 11.844 | 33.222 | 1.00 | 106.06 |
| 12533 | OD1 | ASN | C | 59 | -34.088 | 11.140 | 32.450 | 1.00 | 106.14 |
| 12534 | ND2 | ASN | C | 59 | -35.043 | 13.111 | 32.955 | 1.00 | 105.82 |
| 12535 | C | ASN | C | 59 | -37.689 | 11.279 | 33.967 | 1.00 | 106.15 |
| 12536 | O | ASN | C | 59 | -37.896 | 11.489 | 32.769 | 1.00 | 106.13 |

FIGURE 3 IL

| A | B | C | D | E | F | G | H | I | J |
|---|---|---|---|---|---|---|---|---|---|
| 12537 | N | SER | C | 60 | -38.480 | 11.741 | 34.926 | 1.00 | 106.33 |
| 12538 | CA | SER | C | 60 | -39.705 | 12.440 | 34.587 | 1.00 | 106.60 |
| 12539 | CB | SER | C | 60 | -40.912 | 11.583 | 34.988 | 1.00 | 106.65 |
| 12540 | OG | SER | C | 60 | -40.861 | 11.233 | 36.362 | 1.00 | 106.66 |
| 12541 | C | SER | C | 60 | -39.843 | 13.834 | 35.183 | 1.00 | 106.76 |
| 12542 | O | SER | C | 60 | -38.986 | 14.306 | 35.931 | 1.00 | 106.80 |
| 12543 | N | SER | C | 61 | -40.947 | 14.478 | 34.818 | 1.00 | 106.91 |
| 12544 | CA | SER | C | 61 | -41.322 | 15.800 | 35.296 | 1.00 | 107.07 |
| 12545 | CB | SER | C | 61 | -40.470 | 16.890 | 34.641 | 1.00 | 107.10 |
| 12546 | OG | SER | C | 61 | -40.763 | 17.021 | 33.260 | 1.00 | 107.07 |
| 12547 | C | SER | C | 61 | -42.787 | 15.987 | 34.932 | 1.00 | 107.16 |
| 12548 | O | SER | C | 61 | -43.277 | 15.379 | 33.980 | 1.00 | 107.20 |
| 12549 | N | VAL | C | 62 | -43.499 | 16.812 | 35.686 | 1.00 | 107.27 |
| 12550 | CA | VAL | C | 62 | -44.905 | 17.029 | 35.386 | 1.00 | 107.37 |
| 12551 | CB | VAL | C | 62 | -45.621 | 17.788 | 36.516 | 1.00 | 107.41 |
| 12552 | CG1 | VAL | C | 62 | -47.112 | 17.875 | 36.229 | 1.00 | 107.33 |
| 12553 | CG2 | VAL | C | 62 | -45.372 | 17.101 | 37.853 | 1.00 | 107.53 |
| 12554 | C | VAL | C | 62 | -45.059 | 17.773 | 34.060 | 1.00 | 107.38 |
| 12555 | O | VAL | C | 62 | -44.532 | 18.872 | 33.889 | 1.00 | 107.30 |
| 12556 | N | PHE | C | 63 | -45.767 | 17.151 | 33.122 | 1.00 | 107.40 |
| 12557 | CA | PHE | C | 63 | -46.012 | 17.738 | 31.811 | 1.00 | 107.44 |
| 12558 | CB | PHE | C | 63 | -46.185 | 16.632 | 30.769 | 1.00 | 107.53 |
| 12559 | CG | PHE | C | 63 | -46.688 | 17.119 | 29.446 | 1.00 | 107.98 |
| 12560 | CD1 | PHE | C | 63 | -48.046 | 17.259 | 29.218 | 1.00 | 108.50 |
| 12561 | CE1 | PHE | C | 63 | -48.516 | 17.711 | 28.002 | 1.00 | 108.98 |
| 12562 | CZ | PHE | C | 63 | -47.626 | 18.022 | 26.988 | 1.00 | 109.22 |
| 12563 | CE2 | PHE | C | 63 | -46.267 | 17.883 | 27.200 | 1.00 | 109.05 |
| 12564 | CD2 | PHE | C | 63 | -45.804 | 17.432 | 28.425 | 1.00 | 108.65 |
| 12565 | C | PHE | C | 63 | -47.257 | 18.611 | 31.867 | 1.00 | 107.39 |
| 12566 | O | PHE | C | 63 | -47.290 | 19.710 | 31.313 | 1.00 | 107.31 |
| 12567 | N | LEU | C | 64 | -48.283 | 18.104 | 32.541 | 1.00 | 107.33 |
| 12568 | CA | LEU | C | 64 | -49.533 | 18.826 | 32.710 | 1.00 | 107.32 |
| 12569 | CB | LEU | C | 64 | -50.454 | 18.603 | 31.511 | 1.00 | 107.38 |
| 12570 | CG | LEU | C | 64 | -51.803 | 19.325 | 31.585 | 1.00 | 107.60 |
| 12571 | CD1 | LEU | C | 64 | -51.705 | 20.730 | 31.002 | 1.00 | 107.80 |
| 12572 | CD2 | LEU | C | 64 | -52.876 | 18.526 | 30.875 | 1.00 | 107.46 |
| 12573 | C | LEU | C | 64 | -50.220 | 18.352 | 33.983 | 1.00 | 107.27 |
| 12574 | O | LEU | C | 64 | -50.797 | 17.265 | 34.017 | 1.00 | 107.32 |
| 12575 | N | GLU | C | 65 | -50.149 | 19.166 | 35.029 | 1.00 | 107.21 |
| 12576 | CA | GLU | C | 65 | -50.766 | 18.826 | 36.306 | 1.00 | 107.13 |
| 12577 | CB | GLU | C | 65 | -50.091 | 19.587 | 37.453 | 1.00 | 107.24 |
| 12578 | CG | GLU | C | 65 | -49.785 | 21.044 | 37.142 | 1.00 | 107.67 |
| 12579 | CD | GLU | C | 65 | -48.961 | 21.713 | 38.229 | 1.00 | 108.31 |
| 12580 | OE1 | GLU | C | 65 | -48.763 | 22.946 | 38.151 | 1.00 | 108.55 |
| 12581 | OE2 | GLU | C | 65 | -48.511 | 21.010 | 39.160 | 1.00 | 108.38 |
| 12582 | C | GLU | C | 65 | -52.260 | 19.113 | 36.283 | 1.00 | 106.88 |
| 12583 | O | GLU | C | 65 | -52.698 | 20.108 | 35.707 | 1.00 | 106.98 |
| 12584 | N | ASN | C | 66 | -53.046 | 18.238 | 36.899 | 1.00 | 106.55 |
| 12585 | CA | ASN | C | 66 | -54.489 | 18.448 | 36.924 | 1.00 | 106.23 |
| 12586 | CB | ASN | C | 66 | -55.279 | 17.144 | 36.781 | 1.00 | 106.30 |
| 12587 | CG | ASN | C | 66 | -56.035 | 17.076 | 35.468 | 1.00 | 106.39 |

FIGURE 3 IM

| A | B | C | D | E | F | G | H | I | J |
|---|---|---|---|---|---|---|---|---|---|
| 12588 | OD1 | ASN | C | 66 | -56.375 | 18.109 | 34.892 | 1.00 | 106.86 |
| 12589 | ND2 | ASN | C | 66 | -56.300 | 15.866 | 34.988 | 1.00 | 106.05 |
| 12590 | C | ASN | C | 66 | -54.993 | 19.297 | 38.085 | 1.00 | 105.93 |
| 12591 | O | ASN | C | 66 | -55.491 | 18.796 | 39.095 | 1.00 | 105.90 |
| 12592 | N | SER | C | 67 | -54.824 | 20.598 | 37.906 | 1.00 | 105.45 |
| 12593 | CA | SER | C | 67 | -55.311 | 21.626 | 38.804 | 1.00 | 104.97 |
| 12594 | CB | SER | C | 67 | -54.271 | 21.980 | 39.867 | 1.00 | 105.03 |
| 12595 | OG | SER | C | 67 | -53.194 | 22.714 | 39.310 | 1.00 | 105.01 |
| 12596 | C | SER | C | 67 | -55.478 | 22.757 | 37.811 | 1.00 | 104.56 |
| 12597 | O | SER | C | 67 | -56.058 | 23.808 | 38.100 | 1.00 | 104.55 |
| 12598 | N | THR | C | 68 | -54.952 | 22.489 | 36.618 | 1.00 | 103.87 |
| 12599 | CA | THR | C | 68 | -55.016 | 23.391 | 35.483 | 1.00 | 103.13 |
| 12600 | CB | THR | C | 68 | -54.311 | 22.743 | 34.276 | 1.00 | 103.09 |
| 12601 | OG1 | THR | C | 68 | -52.994 | 22.322 | 34.651 | 1.00 | 103.00 |
| 12602 | CG2 | THR | C | 68 | -54.058 | 23.764 | 33.186 | 1.00 | 102.99 |
| 12603 | C | THR | C | 68 | -56.469 | 23.640 | 35.126 | 1.00 | 102.68 |
| 12604 | O | THR | C | 68 | -56.892 | 24.782 | 34.947 | 1.00 | 102.68 |
| 12605 | N | PHE | C | 69 | -57.235 | 22.558 | 35.041 | 1.00 | 101.95 |
| 12606 | CA | PHE | C | 69 | -58.630 | 22.644 | 34.638 | 1.00 | 101.21 |
| 12607 | CB | PHE | C | 69 | -58.892 | 21.651 | 33.509 | 1.00 | 101.21 |
| 12608 | CG | PHE | C | 69 | -57.711 | 21.444 | 32.609 | 1.00 | 101.05 |
| 12609 | CD1 | PHE | C | 69 | -57.397 | 22.370 | 31.635 | 1.00 | 100.92 |
| 12610 | CE1 | PHE | C | 69 | -56.309 | 22.181 | 30.808 | 1.00 | 100.82 |
| 12611 | CZ | PHE | C | 69 | -55.520 | 21.067 | 30.952 | 1.00 | 100.87 |
| 12612 | CE2 | PHE | C | 69 | -55.818 | 20.138 | 31.924 | 1.00 | 100.79 |
| 12613 | CD2 | PHE | C | 69 | -56.905 | 20.328 | 32.747 | 1.00 | 100.90 |
| 12614 | C | PHE | C | 69 | -59.590 | 22.384 | 35.792 | 1.00 | 100.70 |
| 12615 | O | PHE | C | 69 | -60.725 | 21.964 | 35.577 | 1.00 | 100.64 |
| 12616 | N | ASP | C | 70 | -59.138 | 22.627 | 37.017 | 1.00 | 99.98 |
| 12617 | CA | ASP | C | 70 | -60.006 | 22.424 | 38.169 | 1.00 | 99.27 |
| 12618 | CB | ASP | C | 70 | -59.197 | 22.271 | 39.460 | 1.00 | 99.39 |
| 12619 | CG | ASP | C | 70 | -59.854 | 21.318 | 40.455 | 1.00 | 99.76 |
| 12620 | OD1 | ASP | C | 70 | -60.924 | 20.756 | 40.134 | 1.00 | 100.03 |
| 12621 | OD2 | ASP | C | 70 | -59.370 | 21.062 | 41.579 | 1.00 | 100.24 |
| 12622 | C | ASP | C | 70 | -60.985 | 23.591 | 38.257 | 1.00 | 98.57 |
| 12623 | O | ASP | C | 70 | -61.959 | 23.550 | 39.009 | 1.00 | 98.63 |
| 12624 | N | GLU | C | 71 | -60.716 | 24.634 | 37.477 | 1.00 | 97.63 |
| 12625 | CA | GLU | C | 71 | -61.603 | 25.787 | 37.407 | 1.00 | 96.63 |
| 12626 | CB | GLU | C | 71 | -60.820 | 27.095 | 37.545 | 1.00 | 96.82 |
| 12627 | CG | GLU | C | 71 | -61.652 | 28.260 | 38.068 | 1.00 | 97.17 |
| 12628 | CD | GLU | C | 71 | -60.900 | 29.580 | 38.045 | 1.00 | 97.32 |
| 12629 | OE1 | GLU | C | 71 | -59.666 | 29.558 | 37.847 | 1.00 | 97.16 |
| 12630 | OE2 | GLU | C | 71 | -61.545 | 30.639 | 38.223 | 1.00 | 97.07 |
| 12631 | C | GLU | C | 71 | -62.320 | 25.722 | 36.066 | 1.00 | 95.71 |
| 12632 | O | GLU | C | 71 | -63.229 | 26.504 | 35.787 | 1.00 | 95.56 |
| 12633 | N | PHE | C | 72 | -61.888 | 24.770 | 35.244 | 1.00 | 94.60 |
| 12634 | CA | PHE | C | 72 | -62.489 | 24.502 | 33.942 | 1.00 | 93.53 |
| 12635 | CB | PHE | C | 72 | -61.793 | 23.297 | 33.307 | 1.00 | 93.60 |
| 12636 | CG | PHE | C | 72 | -62.130 | 23.076 | 31.864 | 1.00 | 93.81 |
| 12637 | CD1 | PHE | C | 72 | -63.054 | 22.116 | 31.498 | 1.00 | 94.04 |
| 12638 | CE1 | PHE | C | 72 | -63.360 | 21.900 | 30.169 | 1.00 | 94.09 |

FIGURE 3 IN

| A | B | C | D | E | F | G | H | I | J |
|---|---|---|---|---|---|---|---|---|---|
| 12639 | CZ | PHE | C | 72 | -62.731 | 22.638 | 29.188 | 1.00 | 94.38 |
| 12640 | CE2 | PHE | C | 72 | -61.799 | 23.593 | 29.540 | 1.00 | 94.21 |
| 12641 | CD2 | PHE | C | 72 | -61.499 | 23.804 | 30.872 | 1.00 | 94.21 |
| 12642 | C | PHE | C | 72 | -63.978 | 24.214 | 34.113 | 1.00 | 92.54 |
| 12643 | O | PHE | C | 72 | -64.765 | 24.388 | 33.184 | 1.00 | 92.47 |
| 12644 | N | GLY | C | 73 | -64.352 | 23.775 | 35.313 | 1.00 | 91.41 |
| 12645 | CA | GLY | C | 73 | -65.739 | 23.499 | 35.647 | 1.00 | 89.90 |
| 12646 | C | GLY | C | 73 | -66.365 | 22.381 | 34.840 | 1.00 | 88.74 |
| 12647 | O | GLY | C | 73 | -67.552 | 22.428 | 34.515 | 1.00 | 88.78 |
| 12648 | N | HIS | C | 74 | -65.564 | 21.374 | 34.511 | 1.00 | 87.47 |
| 12649 | CA | HIS | C | 74 | -66.043 | 20.227 | 33.751 | 1.00 | 86.07 |
| 12650 | CB | HIS | C | 74 | -65.966 | 20.498 | 32.247 | 1.00 | 86.28 |
| 12651 | CG | HIS | C | 74 | -66.952 | 21.516 | 31.762 | 1.00 | 86.53 |
| 12652 | ND1 | HIS | C | 74 | -68.316 | 21.327 | 31.839 | 1.00 | 86.89 |
| 12653 | CE1 | HIS | C | 74 | -68.934 | 22.380 | 31.335 | 1.00 | 87.10 |
| 12654 | NE2 | HIS | C | 74 | -68.020 | 23.248 | 30.937 | 1.00 | 87.04 |
| 12655 | CD2 | HIS | C | 74 | -66.772 | 22.731 | 31.192 | 1.00 | 86.82 |
| 12656 | C | HIS | C | 74 | -65.234 | 18.986 | 34.092 | 1.00 | 84.97 |
| 12657 | O | HIS | C | 74 | -64.086 | 19.079 | 34.526 | 1.00 | 84.75 |
| 12658 | N | SER | C | 75 | -65.843 | 17.823 | 33.895 | 1.00 | 83.51 |
| 12659 | CA | SER | C | 75 | -65.185 | 16.557 | 34.172 | 1.00 | 82.03 |
| 12660 | CB | SER | C | 75 | -66.208 | 15.523 | 34.642 | 1.00 | 82.15 |
| 12661 | OG | SER | C | 75 | -65.578 | 14.437 | 35.298 | 1.00 | 82.05 |
| 12662 | C | SER | C | 75 | -64.474 | 16.083 | 32.912 | 1.00 | 80.94 |
| 12663 | O | SER | C | 75 | -65.112 | 15.751 | 31.917 | 1.00 | 80.85 |
| 12664 | N | ILE | C | 76 | -63.148 | 16.057 | 32.957 | 1.00 | 79.56 |
| 12665 | CA | ILE | C | 76 | -62.351 | 15.692 | 31.795 | 1.00 | 78.15 |
| 12666 | CB | ILE | C | 76 | -60.919 | 16.208 | 31.960 | 1.00 | 78.25 |
| 12667 | CG1 | ILE | C | 76 | -60.926 | 17.721 | 32.212 | 1.00 | 77.94 |
| 12668 | CD1 | ILE | C | 76 | -61.795 | 18.505 | 31.254 | 1.00 | 77.53 |
| 12669 | CG2 | ILE | C | 76 | -60.069 | 15.826 | 30.750 | 1.00 | 78.05 |
| 12670 | C | ILE | C | 76 | -62.334 | 14.190 | 31.566 | 1.00 | 77.39 |
| 12671 | O | ILE | C | 76 | -61.799 | 13.437 | 32.384 | 1.00 | 77.16 |
| 12672 | N | ASN | C | 77 | -62.907 | 13.759 | 30.445 | 1.00 | 76.15 |
| 12673 | CA | ASN | C | 77 | -62.969 | 12.338 | 30.128 | 1.00 | 74.99 |
| 12674 | CB | ASN | C | 77 | -64.094 | 12.040 | 29.141 | 1.00 | 74.99 |
| 12675 | CG | ASN | C | 77 | -64.190 | 10.560 | 28.802 | 1.00 | 74.36 |
| 12676 | OD1 | ASN | C | 77 | -64.458 | 9.727 | 29.672 | 1.00 | 73.41 |
| 12677 | ND2 | ASN | C | 77 | -63.964 | 10.226 | 27.534 | 1.00 | 73.07 |
| 12678 | C | ASN | C | 77 | -61.663 | 11.829 | 29.565 | 1.00 | 74.31 |
| 12679 | O | ASN | C | 77 | -61.214 | 10.735 | 29.901 | 1.00 | 74.25 |
| 12680 | N | ASP | C | 78 | -61.063 | 12.627 | 28.693 | 1.00 | 73.48 |
| 12681 | CA | ASP | C | 78 | -59.792 | 12.264 | 28.092 | 1.00 | 72.65 |
| 12682 | CB | ASP | C | 78 | -59.991 | 11.266 | 26.944 | 1.00 | 72.58 |
| 12683 | CG | ASP | C | 78 | -58.753 | 10.412 | 26.688 | 1.00 | 72.38 |
| 12684 | OD1 | ASP | C | 78 | -57.701 | 10.679 | 27.312 | 1.00 | 72.10 |
| 12685 | OD2 | ASP | C | 78 | -58.737 | 9.450 | 25.890 | 1.00 | 71.29 |
| 12686 | C | ASP | C | 78 | -59.084 | 13.504 | 27.580 | 1.00 | 72.15 |
| 12687 | O | ASP | C | 78 | -59.661 | 14.589 | 27.507 | 1.00 | 72.00 |
| 12688 | N | TYR | C | 79 | -57.821 | 13.333 | 27.231 | 1.00 | 71.66 |
| 12689 | CA | TYR | C | 79 | -57.038 | 14.421 | 26.690 | 1.00 | 71.20 |

FIGURE 3 IO

| A | B | C | D | E | F | G | H | I | J |
|---|---|---|---|---|---|---|---|---|---|
| 12690 | CB | TYR | C | 79 | -56.058 | 14.959 | 27.736 | 1.00 | 71.18 |
| 12691 | CG | TYR | C | 79 | -54.920 | 14.014 | 28.038 | 1.00 | 70.81 |
| 12692 | CD1 | TYR | C | 79 | -54.943 | 13.210 | 29.167 | 1.00 | 70.70 |
| 12693 | CE1 | TYR | C | 79 | -53.906 | 12.342 | 29.440 | 1.00 | 70.91 |
| 12694 | CZ | TYR | C | 79 | -52.830 | 12.272 | 28.580 | 1.00 | 70.37 |
| 12695 | OH | TYR | C | 79 | -51.793 | 11.415 | 28.852 | 1.00 | 70.04 |
| 12696 | CE2 | TYR | C | 79 | -52.787 | 13.059 | 27.457 | 1.00 | 70.54 |
| 12697 | CD2 | TYR | C | 79 | -53.825 | 13.923 | 27.192 | 1.00 | 70.46 |
| 12698 | C | TYR | C | 79 | -56.280 | 13.905 | 25.488 | 1.00 | 70.82 |
| 12699 | O | TYR | C | 79 | -55.973 | 12.721 | 25.393 | 1.00 | 70.72 |
| 12700 | N | SER | C | 80 | -55.995 | 14.800 | 24.559 | 1.00 | 70.61 |
| 12701 | CA | SER | C | 80 | -55.210 | 14.442 | 23.398 | 1.00 | 70.59 |
| 12702 | CB | SER | C | 80 | -56.082 | 14.333 | 22.151 | 1.00 | 70.42 |
| 12703 | OG | SER | C | 80 | -55.362 | 13.702 | 21.112 | 1.00 | 70.29 |
| 12704 | C | SER | C | 80 | -54.155 | 15.516 | 23.218 | 1.00 | 70.56 |
| 12705 | O | SER | C | 80 | -54.443 | 16.711 | 23.345 | 1.00 | 70.59 |
| 12706 | N | ILE | C | 81 | -52.929 | 15.088 | 22.948 | 1.00 | 70.28 |
| 12707 | CA | ILE | C | 81 | -51.834 | 16.025 | 22.760 | 1.00 | 69.94 |
| 12708 | CB | ILE | C | 81 | -50.641 | 15.660 | 23.667 | 1.00 | 69.93 |
| 12709 | CG1 | ILE | C | 81 | -50.812 | 16.325 | 25.029 | 1.00 | 69.77 |
| 12710 | CD1 | ILE | C | 81 | -50.407 | 15.458 | 26.182 | 1.00 | 69.81 |
| 12711 | CG2 | ILE | C | 81 | -49.330 | 16.115 | 23.051 | 1.00 | 69.84 |
| 12712 | C | ILE | C | 81 | -51.419 | 16.065 | 21.306 | 1.00 | 69.71 |
| 12713 | O | ILE | C | 81 | -51.019 | 15.050 | 20.739 | 1.00 | 69.64 |
| 12714 | N | SER | C | 82 | -51.548 | 17.240 | 20.702 | 1.00 | 69.37 |
| 12715 | CA | SER | C | 82 | -51.118 | 17.436 | 19.333 | 1.00 | 69.33 |
| 12716 | CB | SER | C | 82 | -51.173 | 18.922 | 18.975 | 1.00 | 69.47 |
| 12717 | OG | SER | C | 82 | -50.602 | 19.156 | 17.699 | 1.00 | 69.91 |
| 12718 | C | SER | C | 82 | -49.686 | 16.953 | 19.252 | 1.00 | 68.99 |
| 12719 | O | SER | C | 82 | -48.955 | 17.046 | 20.232 | 1.00 | 69.07 |
| 12720 | N | PRO | C | 83 | -49.284 | 16.418 | 18.106 | 1.00 | 68.64 |
| 12721 | CA | PRO | C | 83 | -47.905 | 15.953 | 17.926 | 1.00 | 68.48 |
| 12722 | CB | PRO | C | 83 | -47.888 | 15.476 | 16.473 | 1.00 | 68.45 |
| 12723 | CG | PRO | C | 83 | -49.319 | 15.151 | 16.179 | 1.00 | 68.52 |
| 12724 | CD | PRO | C | 83 | -50.107 | 16.202 | 16.905 | 1.00 | 68.55 |
| 12725 | C | PRO | C | 83 | -46.929 | 17.111 | 18.142 | 1.00 | 68.19 |
| 12726 | O | PRO | C | 83 | -45.824 | 16.919 | 18.637 | 1.00 | 68.33 |
| 12727 | N | ASP | C | 84 | -47.359 | 18.308 | 17.769 | 1.00 | 67.84 |
| 12728 | CA | ASP | C | 84 | -46.595 | 19.523 | 17.987 | 1.00 | 67.58 |
| 12729 | CB | ASP | C | 84 | -47.529 | 20.723 | 17.854 | 1.00 | 67.54 |
| 12730 | CG | ASP | C | 84 | -47.266 | 21.528 | 16.622 | 1.00 | 68.01 |
| 12731 | OD1 | ASP | C | 84 | -47.959 | 22.548 | 16.437 | 1.00 | 68.19 |
| 12732 | OD2 | ASP | C | 84 | -46.389 | 21.225 | 15.787 | 1.00 | 68.92 |
| 12733 | C | ASP | C | 84 | -46.036 | 19.584 | 19.394 | 1.00 | 67.29 |
| 12734 | O | ASP | C | 84 | -44.822 | 19.566 | 19.615 | 1.00 | 67.36 |
| 12735 | N | GLY | C | 85 | -46.964 | 19.672 | 20.341 | 1.00 | 66.79 |
| 12736 | CA | GLY | C | 85 | -46.658 | 19.891 | 21.738 | 1.00 | 66.22 |
| 12737 | C | GLY | C | 85 | -47.167 | 21.291 | 22.043 | 1.00 | 65.77 |
| 12738 | O | GLY | C | 85 | -46.934 | 21.835 | 23.125 | 1.00 | 65.89 |
| 12739 | N | GLN | C | 86 | -47.868 | 21.869 | 21.068 | 1.00 | 65.07 |
| 12740 | CA | GLN | C | 86 | -48.405 | 23.228 | 21.169 | 1.00 | 64.48 |

FIGURE 3 IP

| A | B | C | D | E | F | G | H | I | J |
|---|---|---|---|---|---|---|---|---|---|
| 12741 | CB | GLN | C | 86 | -48.405 | 23.908 | 19.793 | 1.00 | 64.40 |
| 12742 | CG | GLN | C | 86 | -47.240 | 24.862 | 19.572 | 1.00 | 64.45 |
| 12743 | CD | GLN | C | 86 | -46.995 | 25.174 | 18.106 | 1.00 | 64.57 |
| 12744 | OE1 | GLN | C | 86 | -47.669 | 26.033 | 17.519 | 1.00 | 64.14 |
| 12745 | NE2 | GLN | C | 86 | -46.025 | 24.483 | 17.511 | 1.00 | 63.31 |
| 12746 | C | GLN | C | 86 | -49.800 | 23.306 | 21.787 | 1.00 | 64.13 |
| 12747 | O | GLN | C | 86 | -50.129 | 24.272 | 22.482 | 1.00 | 63.89 |
| 12748 | N | PHE | C | 87 | -50.629 | 22.303 | 21.518 | 1.00 | 63.78 |
| 12749 | CA | PHE | C | 87 | -51.977 | 22.289 | 22.071 | 1.00 | 63.29 |
| 12750 | CB | PHE | C | 87 | -52.997 | 22.764 | 21.033 | 1.00 | 63.41 |
| 12751 | CG | PHE | C | 87 | -52.694 | 24.116 | 20.460 | 1.00 | 63.48 |
| 12752 | CD1 | PHE | C | 87 | -53.320 | 25.247 | 20.951 | 1.00 | 63.92 |
| 12753 | CE1 | PHE | C | 87 | -53.038 | 26.494 | 20.429 | 1.00 | 64.03 |
| 12754 | CZ | PHE | C | 87 | -52.123 | 26.620 | 19.405 | 1.00 | 64.22 |
| 12755 | CE2 | PHE | C | 87 | -51.493 | 25.496 | 18.905 | 1.00 | 63.52 |
| 12756 | CD2 | PHE | C | 87 | -51.781 | 24.256 | 19.429 | 1.00 | 63.35 |
| 12757 | C | PHE | C | 87 | -52.370 | 20.914 | 22.589 | 1.00 | 62.81 |
| 12758 | O | PHE | C | 87 | -51.969 | 19.889 | 22.041 | 1.00 | 63.11 |
| 12759 | N | ILE | C | 88 | -53.144 | 20.903 | 23.667 | 1.00 | 62.10 |
| 12760 | CA | ILE | C | 88 | -53.679 | 19.668 | 24.209 | 1.00 | 61.22 |
| 12761 | CB | ILE | C | 88 | -53.349 | 19.519 | 25.715 | 1.00 | 61.25 |
| 12762 | CG1 | ILE | C | 88 | -53.520 | 18.066 | 26.166 | 1.00 | 61.28 |
| 12763 | CD1 | ILE | C | 88 | -52.939 | 17.792 | 27.538 | 1.00 | 60.54 |
| 12764 | CG2 | ILE | C | 88 | -54.207 | 20.428 | 26.559 | 1.00 | 60.74 |
| 12765 | C | ILE | C | 88 | -55.178 | 19.709 | 23.962 | 1.00 | 60.82 |
| 12766 | O | ILE | C | 88 | -55.808 | 20.763 | 24.090 | 1.00 | 60.91 |
| 12767 | N | LEU | C | 89 | -55.743 | 18.575 | 23.567 | 1.00 | 60.14 |
| 12768 | CA | LEU | C | 89 | -57.174 | 18.502 | 23.277 | 1.00 | 59.40 |
| 12769 | CB | LEU | C | 89 | -57.413 | 17.581 | 22.085 | 1.00 | 59.54 |
| 12770 | CG | LEU | C | 89 | -58.811 | 17.434 | 21.502 | 1.00 | 59.68 |
| 12771 | CD1 | LEU | C | 89 | -58.678 | 16.746 | 20.158 | 1.00 | 59.51 |
| 12772 | CD2 | LEU | C | 89 | -59.491 | 18.786 | 21.345 | 1.00 | 60.01 |
| 12773 | C | LEU | C | 89 | -57.903 | 17.987 | 24.505 | 1.00 | 58.58 |
| 12774 | O | LEU | C | 89 | -57.472 | 17.014 | 25.113 | 1.00 | 58.15 |
| 12775 | N | LEU | C | 90 | -58.995 | 18.650 | 24.874 | 1.00 | 57.83 |
| 12776 | CA | LEU | C | 90 | -59.740 | 18.279 | 26.075 | 1.00 | 57.34 |
| 12777 | CB | LEU | C | 90 | -59.841 | 19.466 | 27.038 | 1.00 | 57.40 |
| 12778 | CG | LEU | C | 90 | -58.615 | 19.701 | 27.921 | 1.00 | 57.46 |
| 12779 | CD1 | LEU | C | 90 | -58.963 | 20.637 | 29.065 | 1.00 | 57.90 |
| 12780 | CD2 | LEU | C | 90 | -58.116 | 18.375 | 28.456 | 1.00 | 57.26 |
| 12781 | C | LEU | C | 90 | -61.127 | 17.701 | 25.801 | 1.00 | 56.84 |
| 12782 | O | LEU | C | 90 | -62.034 | 18.411 | 25.373 | 1.00 | 56.74 |
| 12783 | N | GLU | C | 91 | -61.280 | 16.410 | 26.089 | 1.00 | 56.21 |
| 12784 | CA | GLU | C | 91 | -62.530 | 15.683 | 25.858 | 1.00 | 55.36 |
| 12785 | CB | GLU | C | 91 | -62.202 | 14.265 | 25.407 | 1.00 | 55.13 |
| 12786 | CG | GLU | C | 91 | -63.379 | 13.434 | 24.921 | 1.00 | 55.49 |
| 12787 | CD | GLU | C | 91 | -62.941 | 12.049 | 24.461 | 1.00 | 55.86 |
| 12788 | OE1 | GLU | C | 91 | -62.638 | 11.198 | 25.323 | 1.00 | 55.96 |
| 12789 | OE2 | GLU | C | 91 | -62.877 | 11.811 | 23.239 | 1.00 | 56.22 |
| 12790 | C | GLU | C | 91 | -63.419 | 15.640 | 27.104 | 1.00 | 54.78 |
| 12791 | O | GLU | C | 91 | -62.987 | 15.205 | 28.172 | 1.00 | 55.13 |

FIGURE 3 IQ

| A | B | C | D | E | F | G | H | I | J |
|---|---|---|---|---|---|---|---|---|---|
| 12792 | N | TYR | C | 92 | -64.657 | 16.098 | 26.960 | 1.00 | 53.96 |
| 12793 | CA | TYR | C | 92 | -65.634 | 16.063 | 28.047 | 1.00 | 53.29 |
| 12794 | CB | TYR | C | 92 | -65.451 | 17.234 | 29.024 | 1.00 | 53.45 |
| 12795 | CG | TYR | C | 92 | -65.739 | 18.600 | 28.444 | 1.00 | 52.87 |
| 12796 | CD1 | TYR | C | 92 | -64.948 | 19.124 | 27.428 | 1.00 | 52.94 |
| 12797 | CE1 | TYR | C | 92 | -65.196 | 20.372 | 26.907 | 1.00 | 52.73 |
| 12798 | CZ | TYR | C | 92 | -66.246 | 21.113 | 27.395 | 1.00 | 52.65 |
| 12799 | OH | TYR | C | 92 | -66.495 | 22.352 | 26.857 | 1.00 | 54.21 |
| 12800 | CE2 | TYR | C | 92 | -67.046 | 20.619 | 28.405 | 1.00 | 51.62 |
| 12801 | CD2 | TYR | C | 92 | -66.788 | 19.372 | 28.925 | 1.00 | 51.67 |
| 12802 | C | TYR | C | 92 | -67.059 | 16.007 | 27.503 | 1.00 | 52.56 |
| 12803 | O | TYR | C | 92 | -67.261 | 15.962 | 26.295 | 1.00 | 52.30 |
| 12804 | N | ASN | C | 93 | -68.044 | 16.006 | 28.395 | 1.00 | 51.97 |
| 12805 | CA | ASN | C | 93 | -69.439 | 15.858 | 27.974 | 1.00 | 51.25 |
| 12806 | CB | ASN | C | 93 | -69.919 | 17.086 | 27.211 | 1.00 | 51.25 |
| 12807 | CG | ASN | C | 93 | -70.276 | 18.237 | 28.131 | 1.00 | 51.22 |
| 12808 | OD1 | ASN | C | 93 | -70.130 | 18.137 | 29.348 | 1.00 | 50.55 |
| 12809 | ND2 | ASN | C | 93 | -70.758 | 19.334 | 27.554 | 1.00 | 51.19 |
| 12810 | C | ASN | C | 93 | -69.609 | 14.592 | 27.129 | 1.00 | 50.67 |
| 12811 | O | ASN | C | 93 | -70.381 | 14.547 | 26.188 | 1.00 | 50.59 |
| 12812 | N | TYR | C | 94 | -68.861 | 13.566 | 27.499 | 1.00 | 50.06 |
| 12813 | CA | TYR | C | 94 | -68.848 | 12.295 | 26.808 | 1.00 | 49.66 |
| 12814 | CB | TYR | C | 94 | -67.625 | 11.511 | 27.290 | 1.00 | 49.61 |
| 12815 | CG | TYR | C | 94 | -67.635 | 10.039 | 26.969 | 1.00 | 50.89 |
| 12816 | CD1 | TYR | C | 94 | -66.979 | 9.553 | 25.851 | 1.00 | 50.78 |
| 12817 | CE1 | TYR | C | 94 | -66.978 | 8.206 | 25.552 | 1.00 | 51.62 |
| 12818 | CZ | TYR | C | 94 | -67.631 | 7.321 | 26.375 | 1.00 | 52.07 |
| 12819 | OH | TYR | C | 94 | -67.624 | 5.973 | 26.066 | 1.00 | 53.02 |
| 12820 | CE2 | TYR | C | 94 | -68.285 | 7.777 | 27.503 | 1.00 | 51.93 |
| 12821 | CD2 | TYR | C | 94 | -68.280 | 9.126 | 27.799 | 1.00 | 51.61 |
| 12822 | C | TYR | C | 94 | -70.116 | 11.467 | 27.040 | 1.00 | 49.15 |
| 12823 | O | TYR | C | 94 | -70.529 | 11.258 | 28.183 | 1.00 | 49.10 |
| 12824 | N | VAL | C | 95 | -70.745 | 11.027 | 25.955 | 1.00 | 47.85 |
| 12825 | CA | VAL | C | 95 | -71.845 | 10.072 | 26.056 | 1.00 | 47.07 |
| 12826 | CB | VAL | C | 95 | -73.258 | 10.703 | 25.945 | 1.00 | 47.35 |
| 12827 | CG1 | VAL | C | 95 | -73.203 | 12.217 | 26.129 | 1.00 | 47.00 |
| 12828 | CG2 | VAL | C | 95 | -73.929 | 10.329 | 24.639 | 1.00 | 47.41 |
| 12829 | C | VAL | C | 95 | -71.643 | 8.972 | 25.012 | 1.00 | 46.09 |
| 12830 | O | VAL | C | 95 | -71.511 | 9.236 | 23.822 | 1.00 | 45.81 |
| 12831 | N | LYS | C | 96 | -71.587 | 7.736 | 25.486 | 1.00 | 45.36 |
| 12832 | CA | LYS | C | 96 | -71.331 | 6.581 | 24.631 | 1.00 | 44.41 |
| 12833 | CB | LYS | C | 96 | -71.034 | 5.352 | 25.501 | 1.00 | 44.27 |
| 12834 | CG | LYS | C | 96 | -70.908 | 4.033 | 24.759 | 1.00 | 43.31 |
| 12835 | CD | LYS | C | 96 | -70.429 | 2.911 | 25.690 | 1.00 | 41.68 |
| 12836 | CE | LYS | C | 96 | -70.680 | 1.537 | 25.060 | 1.00 | 41.73 |
| 12837 | NZ | LYS | C | 96 | -72.135 | 1.379 | 24.701 | 1.00 | 40.16 |
| 12838 | C | LYS | C | 96 | -72.472 | 6.269 | 23.677 | 1.00 | 43.96 |
| 12839 | O | LYS | C | 96 | -73.655 | 6.418 | 24.012 | 1.00 | 43.57 |
| 12840 | N | GLN | C | 97 | -72.105 | 5.852 | 22.474 | 1.00 | 43.47 |
| 12841 | CA | GLN | C | 97 | -73.094 | 5.341 | 21.536 | 1.00 | 43.11 |
| 12842 | CB | GLN | C | 97 | -72.990 | 6.010 | 20.162 | 1.00 | 43.52 |

FIGURE 3 IR

| A | B | C | D | E | F | G | H | I | J |
|---|---|---|---|---|---|---|---|---|---|
| 12843 | CG | GLN | C | 97 | -74.137 | 5.683 | 19.214 | 1.00 | 45.18 |
| 12844 | CD | GLN | C | 97 | -74.129 | 6.546 | 17.944 | 1.00 | 48.17 |
| 12845 | OE1 | GLN | C | 97 | -75.119 | 7.220 | 17.635 | 1.00 | 49.06 |
| 12846 | NE2 | GLN | C | 97 | -73.015 | 6.523 | 17.211 | 1.00 | 47.49 |
| 12847 | C | GLN | C | 97 | -72.856 | 3.841 | 21.463 | 1.00 | 42.21 |
| 12848 | O | GLN | C | 97 | -73.284 | 3.105 | 22.353 | 1.00 | 42.31 |
| 12849 | N | TRP | C | 98 | -72.130 | 3.381 | 20.452 | 1.00 | 40.98 |
| 12850 | CA | TRP | C | 98 | -71.914 | 1.946 | 20.320 | 1.00 | 40.00 |
| 12851 | CB | TRP | C | 98 | -72.023 | 1.491 | 18.865 | 1.00 | 39.57 |
| 12852 | CG | TRP | C | 98 | -73.243 | 2.019 | 18.198 | 1.00 | 37.44 |
| 12853 | CD1 | TRP | C | 98 | -73.310 | 2.611 | 16.979 | 1.00 | 36.49 |
| 12854 | NE1 | TRP | C | 98 | -74.605 | 2.979 | 16.697 | 1.00 | 34.62 |
| 12855 | CE2 | TRP | C | 98 | -75.404 | 2.641 | 17.756 | 1.00 | 35.69 |
| 12856 | CD2 | TRP | C | 98 | -74.579 | 2.034 | 18.723 | 1.00 | 35.77 |
| 12857 | CE3 | TRP | C | 98 | -75.168 | 1.583 | 19.911 | 1.00 | 33.97 |
| 12858 | CZ3 | TRP | C | 98 | -76.523 | 1.750 | 20.089 | 1.00 | 32.14 |
| 12859 | CH2 | TRP | C | 98 | -77.313 | 2.354 | 19.116 | 1.00 | 34.11 |
| 12860 | CZ2 | TRP | C | 98 | -76.779 | 2.807 | 17.940 | 1.00 | 35.02 |
| 12861 | C | TRP | C | 98 | -70.606 | 1.510 | 20.935 | 1.00 | 39.85 |
| 12862 | O | TRP | C | 98 | -70.169 | 2.087 | 21.922 | 1.00 | 40.10 |
| 12863 | N | ARG | C | 99 | -69.988 | 0.486 | 20.366 | 1.00 | 39.89 |
| 12864 | CA | ARG | C | 99 | -68.743 | -0.035 | 20.917 | 1.00 | 40.14 |
| 12865 | CB | ARG | C | 99 | -68.310 | -1.305 | 20.189 | 1.00 | 40.11 |
| 12866 | CG | ARG | C | 99 | -67.364 | -2.170 | 21.017 | 1.00 | 40.05 |
| 12867 | CD | ARG | C | 99 | -66.735 | -3.348 | 20.285 | 1.00 | 38.41 |
| 12868 | NE | ARG | C | 99 | -67.679 | -4.417 | 19.962 | 1.00 | 40.14 |
| 12869 | CZ | ARG | C | 99 | -68.053 | -5.383 | 20.801 | 1.00 | 41.00 |
| 12870 | NH1 | ARG | C | 99 | -67.585 | -5.415 | 22.045 | 1.00 | 42.47 |
| 12871 | NH2 | ARG | C | 99 | -68.902 | -6.321 | 20.402 | 1.00 | 39.62 |
| 12872 | C | ARG | C | 99 | -67.606 | 0.987 | 20.916 | 1.00 | 40.49 |
| 12873 | O | ARG | C | 99 | -66.840 | 1.085 | 21.887 | 1.00 | 40.62 |
| 12874 | N | HIS | C | 100 | -67.501 | 1.756 | 19.841 | 1.00 | 40.70 |
| 12875 | CA | HIS | C | 100 | -66.421 | 2.734 | 19.722 | 1.00 | 41.29 |
| 12876 | CB | HIS | C | 100 | -65.599 | 2.459 | 18.469 | 1.00 | 40.60 |
| 12877 | CG | HIS | C | 100 | -65.231 | 1.020 | 18.299 | 1.00 | 38.97 |
| 12878 | ND1 | HIS | C | 100 | -64.288 | 0.395 | 19.086 | 1.00 | 37.10 |
| 12879 | CE1 | HIS | C | 100 | -64.175 | -0.867 | 18.713 | 1.00 | 35.78 |
| 12880 | NE2 | HIS | C | 100 | -65.013 | -1.082 | 17.715 | 1.00 | 35.69 |
| 12881 | CD2 | HIS | C | 100 | -65.686 | 0.081 | 17.439 | 1.00 | 35.77 |
| 12882 | C | HIS | C | 100 | -66.976 | 4.139 | 19.652 | 1.00 | 42.16 |
| 12883 | O | HIS | C | 100 | -66.473 | 5.054 | 20.307 | 1.00 | 42.53 |
| 12884 | N | SER | C | 101 | -68.032 | 4.297 | 18.869 | 1.00 | 43.15 |
| 12885 | CA | SER | C | 101 | -68.658 | 5.593 | 18.680 | 1.00 | 44.52 |
| 12886 | CB | SER | C | 101 | -69.843 | 5.486 | 17.723 | 1.00 | 44.35 |
| 12887 | OG | SER | C | 101 | -70.720 | 4.438 | 18.086 | 1.00 | 45.12 |
| 12888 | C | SER | C | 101 | -69.100 | 6.274 | 19.973 | 1.00 | 45.50 |
| 12889 | O | SER | C | 101 | -69.524 | 5.623 | 20.934 | 1.00 | 46.06 |
| 12890 | N | TYR | C | 102 | -68.986 | 7.595 | 19.979 | 1.00 | 46.20 |
| 12891 | CA | TYR | C | 102 | -69.420 | 8.399 | 21.091 | 1.00 | 46.87 |
| 12892 | CB | TYR | C | 102 | -68.534 | 8.212 | 22.318 | 1.00 | 46.91 |
| 12893 | CG | TYR | C | 102 | -67.088 | 8.668 | 22.209 | 1.00 | 46.66 |

FIGURE 3 IS

| A | B | C | D | E | F | G | H | I | J |
|---|---|---|---|---|---|---|---|---|---|
| 12894 | CD1 | TYR | C | 102 | -66.716 | 9.954 | 22.573 | 1.00 | 46.77 |
| 12895 | CE1 | TYR | C | 102 | -65.389 | 10.366 | 22.518 | 1.00 | 47.77 |
| 12896 | CZ | TYR | C | 102 | -64.410 | 9.478 | 22.104 | 1.00 | 48.33 |
| 12897 | OH | TYR | C | 102 | -63.093 | 9.887 | 22.044 | 1.00 | 48.76 |
| 12898 | CE2 | TYR | C | 102 | -64.750 | 8.188 | 21.751 | 1.00 | 47.47 |
| 12899 | CD2 | TYR | C | 102 | -66.086 | 7.787 | 21.813 | 1.00 | 47.17 |
| 12900 | C | TYR | C | 102 | -69.457 | 9.848 | 20.679 | 1.00 | 47.85 |
| 12901 | O | TYR | C | 102 | -68.892 | 10.239 | 19.661 | 1.00 | 48.16 |
| 12902 | N | THR | C | 103 | -70.129 | 10.639 | 21.495 | 1.00 | 48.55 |
| 12903 | CA | THR | C | 103 | -70.290 | 12.046 | 21.250 | 1.00 | 49.29 |
| 12904 | CB | THR | C | 103 | -71.797 | 12.334 | 21.160 | 1.00 | 49.45 |
| 12905 | OG1 | THR | C | 103 | -72.180 | 12.433 | 19.778 | 1.00 | 49.34 |
| 12906 | CG2 | THR | C | 103 | -72.137 | 13.680 | 21.736 | 1.00 | 49.38 |
| 12907 | C | THR | C | 103 | -69.615 | 12.779 | 22.401 | 1.00 | 50.01 |
| 12908 | O | THR | C | 103 | -69.586 | 12.265 | 23.527 | 1.00 | 49.63 |
| 12909 | N | ALA | C | 104 | -69.031 | 13.948 | 22.122 | 1.00 | 51.05 |
| 12910 | CA | ALA | C | 104 | -68.338 | 14.713 | 23.173 | 1.00 | 52.17 |
| 12911 | CB | ALA | C | 104 | -67.017 | 14.049 | 23.529 | 1.00 | 52.10 |
| 12912 | C | ALA | C | 104 | -68.108 | 16.189 | 22.875 | 1.00 | 53.01 |
| 12913 | O | ALA | C | 104 | -68.158 | 16.621 | 21.722 | 1.00 | 52.89 |
| 12914 | N | SER | C | 105 | -67.868 | 16.957 | 23.940 | 1.00 | 54.39 |
| 12915 | CA | SER | C | 105 | -67.531 | 18.383 | 23.840 | 1.00 | 55.36 |
| 12916 | CB | SER | C | 105 | -68.091 | 19.173 | 25.024 | 1.00 | 55.27 |
| 12917 | OG | SER | C | 105 | -69.443 | 19.526 | 24.819 | 1.00 | 54.42 |
| 12918 | C | SER | C | 105 | -66.013 | 18.517 | 23.819 | 1.00 | 56.28 |
| 12919 | O | SER | C | 105 | -65.304 | 17.631 | 24.296 | 1.00 | 56.13 |
| 12920 | N | TYR | C | 106 | -65.512 | 19.623 | 23.276 | 1.00 | 57.55 |
| 12921 | CA | TYR | C | 106 | -64.067 | 19.808 | 23.170 | 1.00 | 58.72 |
| 12922 | CB | TYR | C | 106 | -63.559 | 19.248 | 21.847 | 1.00 | 58.56 |
| 12923 | CG | TYR | C | 106 | -63.817 | 17.779 | 21.663 | 1.00 | 58.33 |
| 12924 | CD1 | TYR | C | 106 | -64.997 | 17.329 | 21.092 | 1.00 | 58.17 |
| 12925 | CE1 | TYR | C | 106 | -65.234 | 15.981 | 20.921 | 1.00 | 58.20 |
| 12926 | CZ | TYR | C | 106 | -64.286 | 15.068 | 21.322 | 1.00 | 58.18 |
| 12927 | OH | TYR | C | 106 | -64.516 | 13.726 | 21.154 | 1.00 | 59.07 |
| 12928 | CE2 | TYR | C | 106 | -63.104 | 15.489 | 21.889 | 1.00 | 58.09 |
| 12929 | CD2 | TYR | C | 106 | -62.875 | 16.837 | 22.055 | 1.00 | 58.36 |
| 12930 | C | TYR | C | 106 | -63.571 | 21.246 | 23.326 | 1.00 | 59.83 |
| 12931 | O | TYR | C | 106 | -64.215 | 22.210 | 22.889 | 1.00 | 59.62 |
| 12932 | N | ASP | C | 107 | -62.405 | 21.362 | 23.954 | 1.00 | 61.22 |
| 12933 | CA | ASP | C | 107 | -61.728 | 22.637 | 24.140 | 1.00 | 62.67 |
| 12934 | CB | ASP | C | 107 | -62.012 | 23.218 | 25.518 | 1.00 | 62.73 |
| 12935 | CG | ASP | C | 107 | -63.321 | 23.943 | 25.569 | 1.00 | 63.36 |
| 12936 | OD1 | ASP | C | 107 | -63.625 | 24.676 | 24.607 | 1.00 | 64.09 |
| 12937 | OD2 | ASP | C | 107 | -64.117 | 23.839 | 26.522 | 1.00 | 65.12 |
| 12938 | C | ASP | C | 107 | -60.242 | 22.424 | 23.980 | 1.00 | 63.58 |
| 12939 | O | ASP | C | 107 | -59.662 | 21.539 | 24.604 | 1.00 | 63.69 |
| 12940 | N | ILE | C | 108 | -59.628 | 23.229 | 23.126 | 1.00 | 64.96 |
| 12941 | CA | ILE | C | 108 | -58.202 | 23.121 | 22.893 | 1.00 | 66.25 |
| 12942 | CB | ILE | C | 108 | -57.879 | 23.481 | 21.443 | 1.00 | 65.94 |
| 12943 | CG1 | ILE | C | 108 | -58.709 | 22.609 | 20.500 | 1.00 | 65.80 |
| 12944 | CD1 | ILE | C | 108 | -58.971 | 23.240 | 19.159 | 1.00 | 65.86 |

FIGURE 3 IT

| A | B | C | D | E | F | G | H | I | J |
|---|---|---|---|---|---|---|---|---|---|
| 12945 | CG2 | ILE | C | 108 | -56.401 | 23.306 | 21.181 | 1.00 | 65.68 |
| 12946 | C | ILE | C | 108 | -57.478 | 24.054 | 23.839 | 1.00 | 67.51 |
| 12947 | O | ILE | C | 108 | -57.905 | 25.188 | 24.043 | 1.00 | 67.62 |
| 12948 | N | TYR | C | 109 | -56.398 | 23.572 | 24.437 | 1.00 | 69.30 |
| 12949 | CA | TYR | C | 109 | -55.617 | 24.417 | 25.321 | 1.00 | 71.29 |
| 12950 | CB | TYR | C | 109 | -55.408 | 23.777 | 26.692 | 1.00 | 71.59 |
| 12951 | CG | TYR | C | 109 | -56.374 | 24.280 | 27.738 | 1.00 | 73.01 |
| 12952 | CD1 | TYR | C | 109 | -55.963 | 24.502 | 29.048 | 1.00 | 74.40 |
| 12953 | CE1 | TYR | C | 109 | -56.852 | 24.970 | 30.009 | 1.00 | 74.66 |
| 12954 | CZ | TYR | C | 109 | -58.166 | 25.218 | 29.663 | 1.00 | 75.26 |
| 12955 | OH | TYR | C | 109 | -59.062 | 25.682 | 30.608 | 1.00 | 75.96 |
| 12956 | CE2 | TYR | C | 109 | -58.590 | 25.009 | 28.367 | 1.00 | 75.10 |
| 12957 | CD2 | TYR | C | 109 | -57.697 | 24.546 | 27.414 | 1.00 | 74.15 |
| 12958 | C | TYR | C | 109 | -54.288 | 24.747 | 24.696 | 1.00 | 72.29 |
| 12959 | O | TYR | C | 109 | -53.488 | 23.857 | 24.403 | 1.00 | 72.28 |
| 12960 | N | ASP | C | 110 | -54.079 | 26.042 | 24.478 | 1.00 | 73.72 |
| 12961 | CA | ASP | C | 110 | -52.831 | 26.553 | 23.947 | 1.00 | 75.06 |
| 12962 | CB | ASP | C | 110 | -52.958 | 28.051 | 23.675 | 1.00 | 75.46 |
| 12963 | CG | ASP | C | 110 | -51.890 | 28.569 | 22.727 | 1.00 | 76.76 |
| 12964 | OD1 | ASP | C | 110 | -50.784 | 27.976 | 22.687 | 1.00 | 77.78 |
| 12965 | OD2 | ASP | C | 110 | -52.074 | 29.563 | 21.983 | 1.00 | 77.35 |
| 12966 | C | ASP | C | 110 | -51.790 | 26.318 | 25.013 | 1.00 | 75.66 |
| 12967 | O | ASP | C | 110 | -51.772 | 27.018 | 26.029 | 1.00 | 75.84 |
| 12968 | N | LEU | C | 111 | -50.935 | 25.324 | 24.793 | 1.00 | 76.33 |
| 12969 | CA | LEU | C | 111 | -49.922 | 24.963 | 25.776 | 1.00 | 77.04 |
| 12970 | CB | LEU | C | 111 | -49.176 | 23.692 | 25.349 | 1.00 | 77.25 |
| 12971 | CG | LEU | C | 111 | -50.057 | 22.435 | 25.344 | 1.00 | 77.29 |
| 12972 | CD1 | LEU | C | 111 | -50.657 | 22.202 | 26.721 | 1.00 | 77.62 |
| 12973 | CD2 | LEU | C | 111 | -49.292 | 21.211 | 24.895 | 1.00 | 77.54 |
| 12974 | C | LEU | C | 111 | -48.958 | 26.109 | 26.072 | 1.00 | 77.48 |
| 12975 | O | LEU | C | 111 | -47.799 | 25.885 | 26.437 | 1.00 | 77.49 |
| 12976 | N | ASN | C | 112 | -49.460 | 27.335 | 25.920 | 1.00 | 77.89 |
| 12977 | CA | ASN | C | 112 | -48.705 | 28.548 | 26.222 | 1.00 | 78.28 |
| 12978 | CB | ASN | C | 112 | -49.549 | 29.800 | 25.933 | 1.00 | 78.48 |
| 12979 | CG | ASN | C | 112 | -49.420 | 30.283 | 24.491 | 1.00 | 79.52 |
| 12980 | OD1 | ASN | C | 112 | -48.766 | 29.644 | 23.656 | 1.00 | 79.74 |
| 12981 | ND2 | ASN | C | 112 | -50.042 | 31.426 | 24.194 | 1.00 | 80.43 |
| 12982 | C | ASN | C | 112 | -48.242 | 28.572 | 27.672 | 1.00 | 78.15 |
| 12983 | O | ASN | C | 112 | -47.801 | 27.558 | 28.215 | 1.00 | 78.08 |
| 12984 | N | LEU | C | 116 | -57.788 | 28.279 | 27.447 | 1.00 | 72.85 |
| 12985 | CA | LEU | C | 116 | -58.622 | 27.775 | 26.320 | 1.00 | 73.03 |
| 12986 | CB | LEU | C | 116 | -60.118 | 27.840 | 26.658 | 1.00 | 73.20 |
| 12987 | CG | LEU | C | 116 | -60.755 | 27.158 | 27.865 | 1.00 | 73.68 |
| 12988 | CD1 | LEU | C | 116 | -60.610 | 28.027 | 29.102 | 1.00 | 74.21 |
| 12989 | CD2 | LEU | C | 116 | -62.232 | 26.880 | 27.580 | 1.00 | 74.11 |
| 12990 | C | LEU | C | 116 | -58.417 | 28.597 | 25.061 | 1.00 | 72.91 |
| 12991 | O | LEU | C | 116 | -58.267 | 29.816 | 25.128 | 1.00 | 73.02 |
| 12992 | N | ILE | C | 117 | -58.421 | 27.928 | 23.912 | 1.00 | 72.67 |
| 12993 | CA | ILE | C | 117 | -58.425 | 28.618 | 22.632 | 1.00 | 72.45 |
| 12994 | CB | ILE | C | 117 | -57.975 | 27.683 | 21.504 | 1.00 | 72.61 |
| 12995 | CG1 | ILE | C | 117 | -56.454 | 27.512 | 21.518 | 1.00 | 73.05 |

FIGURE 3 IU

| A | B | C | D | E | F | G | H | I | J |
|---|---|---|---|---|---|---|---|---|---|
| 12996 | CD1 | ILE | C | 117 | -55.705 | 28.625 | 20.803 | 1.00 | 74.03 |
| 12997 | CG2 | ILE | C | 117 | -58.392 | 28.244 | 20.176 | 1.00 | 72.78 |
| 12998 | C | ILE | C | 117 | -59.878 | 29.039 | 22.447 | 1.00 | 72.09 |
| 12999 | O | ILE | C | 117 | -60.611 | 28.510 | 21.611 | 1.00 | 72.22 |
| 13000 | N | THR | C | 118 | -60.260 | 30.018 | 23.255 | 1.00 | 71.59 |
| 13001 | CA | THR | C | 118 | -61.625 | 30.525 | 23.406 | 1.00 | 70.99 |
| 13002 | CB | THR | C | 118 | -61.581 | 31.705 | 24.411 | 1.00 | 71.18 |
| 13003 | OG1 | THR | C | 118 | -60.444 | 32.533 | 24.120 | 1.00 | 71.21 |
| 13004 | CG2 | THR | C | 118 | -61.300 | 31.209 | 25.827 | 1.00 | 71.20 |
| 13005 | C | THR | C | 118 | -62.466 | 30.982 | 22.205 | 1.00 | 70.46 |
| 13006 | O | THR | C | 118 | -63.677 | 31.133 | 22.345 | 1.00 | 70.38 |
| 13007 | N | GLU | C | 119 | -61.878 | 31.205 | 21.037 | 1.00 | 69.97 |
| 13008 | CA | GLU | C | 119 | -62.673 | 31.849 | 19.983 | 1.00 | 69.55 |
| 13009 | CB | GLU | C | 119 | -61.932 | 33.047 | 19.367 | 1.00 | 69.69 |
| 13010 | CG | GLU | C | 119 | -60.421 | 32.915 | 19.326 | 1.00 | 70.24 |
| 13011 | CD | GLU | C | 119 | -59.737 | 33.583 | 20.506 | 1.00 | 70.72 |
| 13012 | OE1 | GLU | C | 119 | -59.435 | 32.886 | 21.500 | 1.00 | 70.24 |
| 13013 | OE2 | GLU | C | 119 | -59.490 | 34.808 | 20.430 | 1.00 | 71.20 |
| 13014 | C | GLU | C | 119 | -63.362 | 31.014 | 18.891 | 1.00 | 69.00 |
| 13015 | O | GLU | C | 119 | -64.503 | 31.305 | 18.540 | 1.00 | 69.14 |
| 13016 | N | GLU | C | 120 | -62.703 | 30.021 | 18.313 | 1.00 | 68.21 |
| 13017 | CA | GLU | C | 120 | -63.401 | 29.246 | 17.282 | 1.00 | 67.56 |
| 13018 | CB | GLU | C | 120 | -62.805 | 29.470 | 15.893 | 1.00 | 67.51 |
| 13019 | CG | GLU | C | 120 | -63.862 | 29.756 | 14.832 | 1.00 | 68.37 |
| 13020 | CD | GLU | C | 120 | -64.326 | 31.210 | 14.806 | 1.00 | 69.69 |
| 13021 | OE1 | GLU | C | 120 | -64.261 | 31.841 | 13.732 | 1.00 | 69.90 |
| 13022 | OE2 | GLU | C | 120 | -64.769 | 31.733 | 15.851 | 1.00 | 70.32 |
| 13023 | C | GLU | C | 120 | -63.460 | 27.778 | 17.670 | 1.00 | 66.68 |
| 13024 | O | GLU | C | 120 | -62.815 | 26.917 | 17.068 | 1.00 | 66.69 |
| 13025 | N | ARG | C | 121 | -64.275 | 27.522 | 18.685 | 1.00 | 65.57 |
| 13026 | CA | ARG | C | 121 | -64.354 | 26.222 | 19.335 | 1.00 | 64.49 |
| 13027 | CB | ARG | C | 121 | -65.061 | 26.364 | 20.689 | 1.00 | 64.55 |
| 13028 | CG | ARG | C | 121 | -64.452 | 27.442 | 21.585 | 1.00 | 64.75 |
| 13029 | CD | ARG | C | 121 | -65.300 | 27.805 | 22.800 | 1.00 | 65.21 |
| 13030 | NE | ARG | C | 121 | -65.021 | 26.952 | 23.950 | 1.00 | 65.00 |
| 13031 | CZ | ARG | C | 121 | -65.920 | 26.630 | 24.877 | 1.00 | 66.10 |
| 13032 | NH1 | ARG | C | 121 | -67.163 | 27.087 | 24.789 | 1.00 | 65.99 |
| 13033 | NH2 | ARG | C | 121 | -65.582 | 25.845 | 25.894 | 1.00 | 65.23 |
| 13034 | C | ARG | C | 121 | -65.012 | 25.111 | 18.538 | 1.00 | 63.57 |
| 13035 | O | ARG | C | 121 | -65.839 | 25.345 | 17.660 | 1.00 | 63.20 |
| 13036 | N | ILE | C | 122 | -64.598 | 23.890 | 18.855 | 1.00 | 62.51 |
| 13037 | CA | ILE | C | 122 | -65.208 | 22.702 | 18.308 | 1.00 | 61.37 |
| 13038 | CB | ILE | C | 122 | -64.399 | 21.478 | 18.736 | 1.00 | 61.26 |
| 13039 | CG1 | ILE | C | 122 | -62.913 | 21.829 | 18.716 | 1.00 | 60.66 |
| 13040 | CD1 | ILE | C | 122 | -62.009 | 20.698 | 19.115 | 1.00 | 60.52 |
| 13041 | CG2 | ILE | C | 122 | -64.685 | 20.295 | 17.815 | 1.00 | 61.13 |
| 13042 | C | ILE | C | 122 | -66.597 | 22.694 | 18.928 | 1.00 | 60.55 |
| 13043 | O | ILE | C | 122 | -66.759 | 23.084 | 20.080 | 1.00 | 60.58 |
| 13044 | N | PRO | C | 123 | -67.604 | 22.276 | 18.174 | 1.00 | 59.69 |
| 13045 | CA | PRO | C | 123 | -68.977 | 22.310 | 18.676 | 1.00 | 59.11 |
| 13046 | CB | PRO | C | 123 | -69.817 | 22.019 | 17.426 | 1.00 | 58.99 |

FIGURE 3 IV

| A | B | C | D | E | F | G | H | I | J |
|---|---|---|---|---|---|---|---|---|---|
| 13047 | CG | PRO | C | 123 | -68.870 | 22.088 | 16.277 | 1.00 | 59.33 |
| 13048 | CD | PRO | C | 123 | -67.523 | 21.724 | 16.813 | 1.00 | 59.59 |
| 13049 | C | PRO | C | 123 | -69.231 | 21.228 | 19.706 | 1.00 | 58.59 |
| 13050 | O | PRO | C | 123 | -68.406 | 20.341 | 19.924 | 1.00 | 58.31 |
| 13051 | N | ASN | C | 124 | -70.373 | 21.325 | 20.363 | 1.00 | 58.45 |
| 13052 | CA | ASN | C | 124 | -70.813 | 20.269 | 21.245 | 1.00 | 58.10 |
| 13053 | CB | ASN | C | 124 | -71.924 | 20.760 | 22.162 | 1.00 | 58.65 |
| 13054 | CG | ASN | C | 124 | -71.466 | 21.851 | 23.095 | 1.00 | 59.63 |
| 13055 | OD1 | ASN | C | 124 | -70.567 | 21.649 | 23.906 | 1.00 | 59.75 |
| 13056 | ND2 | ASN | C | 124 | -72.091 | 23.019 | 22.990 | 1.00 | 64.70 |
| 13057 | C | ASN | C | 124 | -71.344 | 19.177 | 20.333 | 1.00 | 57.46 |
| 13058 | O | ASN | C | 124 | -71.618 | 19.433 | 19.163 | 1.00 | 57.30 |
| 13059 | N | ASN | C | 125 | -71.480 | 17.969 | 20.863 | 1.00 | 56.89 |
| 13060 | CA | ASN | C | 125 | -71.981 | 16.833 | 20.094 | 1.00 | 56.19 |
| 13061 | CB | ASN | C | 125 | -73.430 | 17.064 | 19.680 | 1.00 | 56.17 |
| 13062 | CG | ASN | C | 125 | -74.289 | 17.504 | 20.846 | 1.00 | 56.48 |
| 13063 | OD1 | ASN | C | 125 | -74.937 | 18.551 | 20.798 | 1.00 | 56.88 |
| 13064 | ND2 | ASN | C | 125 | -74.284 | 16.710 | 21.915 | 1.00 | 56.45 |
| 13065 | C | ASN | C | 125 | -71.098 | 16.504 | 18.900 | 1.00 | 55.61 |
| 13066 | O | ASN | C | 125 | -71.574 | 16.143 | 17.833 | 1.00 | 55.57 |
| 13067 | N | THR | C | 126 | -69.797 | 16.644 | 19.100 | 1.00 | 55.23 |
| 13068 | CA | THR | C | 126 | -68.830 | 16.329 | 18.073 | 1.00 | 54.84 |
| 13069 | CB | THR | C | 126 | -67.497 | 17.039 | 18.363 | 1.00 | 54.72 |
| 13070 | OG1 | THR | C | 126 | -67.605 | 18.412 | 17.970 | 1.00 | 54.23 |
| 13071 | CG2 | THR | C | 126 | -66.397 | 16.517 | 17.471 | 1.00 | 54.53 |
| 13072 | C | THR | C | 126 | -68.667 | 14.819 | 18.042 | 1.00 | 54.86 |
| 13073 | O | THR | C | 126 | -68.356 | 14.185 | 19.050 | 1.00 | 54.70 |
| 13074 | N | GLN | C | 127 | -68.894 | 14.240 | 16.877 | 1.00 | 54.60 |
| 13075 | CA | GLN | C | 127 | -68.852 | 12.803 | 16.762 | 1.00 | 54.57 |
| 13076 | CB | GLN | C | 127 | -69.593 | 12.375 | 15.503 | 1.00 | 54.28 |
| 13077 | CG | GLN | C | 127 | -71.073 | 12.662 | 15.594 | 1.00 | 53.62 |
| 13078 | CD | GLN | C | 127 | -71.724 | 12.794 | 14.246 | 1.00 | 52.92 |
| 13079 | OE1 | GLN | C | 127 | -72.550 | 11.963 | 13.865 | 1.00 | 52.32 |
| 13080 | NE2 | GLN | C | 127 | -71.354 | 13.837 | 13.509 | 1.00 | 52.15 |
| 13081 | C | GLN | C | 127 | -67.428 | 12.273 | 16.775 | 1.00 | 54.94 |
| 13082 | O | GLN | C | 127 | -67.185 | 11.131 | 17.157 | 1.00 | 54.88 |
| 13083 | N | TRP | C | 128 | -66.482 | 13.113 | 16.381 | 1.00 | 55.24 |
| 13084 | CA | TRP | C | 128 | -65.099 | 12.676 | 16.320 | 1.00 | 55.48 |
| 13085 | CB | TRP | C | 128 | -64.951 | 11.596 | 15.251 | 1.00 | 55.52 |
| 13086 | CG | TRP | C | 128 | -63.633 | 10.934 | 15.266 | 1.00 | 56.77 |
| 13087 | CD1 | TRP | C | 128 | -62.667 | 11.014 | 14.313 | 1.00 | 58.86 |
| 13088 | NE1 | TRP | C | 128 | -61.577 | 10.259 | 14.677 | 1.00 | 59.53 |
| 13089 | CE2 | TRP | C | 128 | -61.828 | 9.677 | 15.890 | 1.00 | 58.49 |
| 13090 | CD2 | TRP | C | 128 | -63.115 | 10.080 | 16.289 | 1.00 | 57.94 |
| 13091 | CE3 | TRP | C | 128 | -63.611 | 9.612 | 17.509 | 1.00 | 58.71 |
| 13092 | CZ3 | TRP | C | 128 | -62.824 | 8.774 | 18.271 | 1.00 | 59.78 |
| 13093 | CH2 | TRP | C | 128 | -61.551 | 8.395 | 17.847 | 1.00 | 59.92 |
| 13094 | CZ2 | TRP | C | 128 | -61.035 | 8.835 | 16.660 | 1.00 | 59.64 |
| 13095 | C | TRP | C | 128 | -64.156 | 13.823 | 15.992 | 1.00 | 55.45 |
| 13096 | O | TRP | C | 128 | -64.452 | 14.658 | 15.136 | 1.00 | 55.42 |
| 13097 | N | VAL | C | 129 | -63.018 | 13.843 | 16.671 | 1.00 | 55.32 |

FIGURE 3 IW

| A | B | C | D | E | F | G | H | I | J |
|---|---|---|---|---|---|---|---|---|---|
| 13098 | CA | VAL | C | 129 | -61.986 | 14.829 | 16.422 | 1.00 | 55.59 |
| 13099 | CB | VAL | C | 129 | -61.949 | 15.905 | 17.531 | 1.00 | 55.60 |
| 13100 | CG1 | VAL | C | 129 | -61.742 | 15.267 | 18.884 | 1.00 | 55.55 |
| 13101 | CG2 | VAL | C | 129 | -60.864 | 16.940 | 17.255 | 1.00 | 56.02 |
| 13102 | C | VAL | C | 129 | -60.653 | 14.095 | 16.335 | 1.00 | 55.72 |
| 13103 | O | VAL | C | 129 | -60.476 | 13.047 | 16.954 | 1.00 | 55.44 |
| 13104 | N | THR | C | 130 | -59.729 | 14.625 | 15.538 | 1.00 | 56.17 |
| 13105 | CA | THR | C | 130 | -58.405 | 14.023 | 15.409 | 1.00 | 56.54 |
| 13106 | CB | THR | C | 130 | -58.451 | 12.757 | 14.530 | 1.00 | 56.52 |
| 13107 | OG1 | THR | C | 130 | -57.128 | 12.217 | 14.393 | 1.00 | 56.16 |
| 13108 | CG2 | THR | C | 130 | -58.830 | 13.111 | 13.109 | 1.00 | 56.50 |
| 13109 | C | THR | C | 130 | -57.358 | 15.001 | 14.878 | 1.00 | 56.96 |
| 13110 | O | THR | C | 130 | -57.617 | 15.783 | 13.956 | 1.00 | 56.86 |
| 13111 | N | TRP | C | 131 | -56.174 | 14.946 | 15.482 | 1.00 | 57.31 |
| 13112 | CA | TRP | C | 131 | -55.056 | 15.785 | 15.081 | 1.00 | 57.40 |
| 13113 | CB | TRP | C | 131 | -53.959 | 15.760 | 16.151 | 1.00 | 57.50 |
| 13114 | CG | TRP | C | 131 | -54.317 | 16.396 | 17.461 | 1.00 | 58.30 |
| 13115 | CD1 | TRP | C | 131 | -54.499 | 15.762 | 18.664 | 1.00 | 58.41 |
| 13116 | NE1 | TRP | C | 131 | -54.807 | 16.681 | 19.639 | 1.00 | 58.17 |
| 13117 | CE2 | TRP | C | 131 | -54.818 | 17.934 | 19.083 | 1.00 | 58.67 |
| 13118 | CD2 | TRP | C | 131 | -54.506 | 17.793 | 17.716 | 1.00 | 58.57 |
| 13119 | CE3 | TRP | C | 131 | -54.453 | 18.946 | 16.921 | 1.00 | 58.81 |
| 13120 | CZ3 | TRP | C | 131 | -54.711 | 20.166 | 17.499 | 1.00 | 58.54 |
| 13121 | CH2 | TRP | C | 131 | -55.016 | 20.273 | 18.859 | 1.00 | 59.18 |
| 13122 | CZ2 | TRP | C | 131 | -55.072 | 19.173 | 19.667 | 1.00 | 59.24 |
| 13123 | C | TRP | C | 131 | -54.446 | 15.275 | 13.784 | 1.00 | 57.38 |
| 13124 | O | TRP | C | 131 | -54.501 | 14.082 | 13.486 | 1.00 | 56.87 |
| 13125 | N | SER | C | 132 | -53.862 | 16.188 | 13.015 | 1.00 | 57.38 |
| 13126 | CA | SER | C | 132 | -53.080 | 15.789 | 11.863 | 1.00 | 57.68 |
| 13127 | CB | SER | C | 132 | -52.697 | 17.005 | 11.005 | 1.00 | 57.84 |
| 13128 | OG | SER | C | 132 | -52.495 | 18.182 | 11.784 | 1.00 | 58.32 |
| 13129 | C | SER | C | 132 | -51.849 | 15.095 | 12.449 | 1.00 | 57.53 |
| 13130 | O | SER | C | 132 | -51.420 | 15.430 | 13.546 | 1.00 | 57.64 |
| 13131 | N | PRO | C | 133 | -51.296 | 14.111 | 11.749 | 1.00 | 57.57 |
| 13132 | CA | PRO | C | 133 | -50.139 | 13.365 | 12.266 | 1.00 | 57.76 |
| 13133 | CB | PRO | C | 133 | -49.718 | 12.509 | 11.069 | 1.00 | 57.70 |
| 13134 | CG | PRO | C | 133 | -50.994 | 12.317 | 10.311 | 1.00 | 57.42 |
| 13135 | CD | PRO | C | 133 | -51.724 | 13.626 | 10.426 | 1.00 | 57.16 |
| 13136 | C | PRO | C | 133 | -48.996 | 14.279 | 12.736 | 1.00 | 57.88 |
| 13137 | O | PRO | C | 133 | -48.184 | 13.874 | 13.572 | 1.00 | 57.68 |
| 13138 | N | VAL | C | 134 | -48.937 | 15.491 | 12.191 | 1.00 | 57.83 |
| 13139 | CA | VAL | C | 134 | -47.950 | 16.480 | 12.610 | 1.00 | 57.77 |
| 13140 | CB | VAL | C | 134 | -46.685 | 16.463 | 11.728 | 1.00 | 57.86 |
| 13141 | CG1 | VAL | C | 134 | -45.978 | 15.112 | 11.823 | 1.00 | 58.17 |
| 13142 | CG2 | VAL | C | 134 | -47.035 | 16.790 | 10.300 | 1.00 | 58.15 |
| 13143 | C | VAL | C | 134 | -48.583 | 17.867 | 12.595 | 1.00 | 57.57 |
| 13144 | O | VAL | C | 134 | -49.660 | 18.063 | 12.039 | 1.00 | 57.41 |
| 13145 | N | GLY | C | 135 | -47.914 | 18.829 | 13.214 | 1.00 | 57.66 |
| 13146 | CA | GLY | C | 135 | -48.456 | 20.169 | 13.302 | 1.00 | 57.49 |
| 13147 | C | GLY | C | 135 | -49.556 | 20.207 | 14.343 | 1.00 | 57.41 |
| 13148 | O | GLY | C | 135 | -49.412 | 19.628 | 15.415 | 1.00 | 57.15 |

FIGURE 3 IX

| A | B | C | D | E | F | G | H | I | J |
|---|---|---|---|---|---|---|---|---|---|
| 13149 | N | HIS | C | 136 | -50.668 | 20.865 | 14.020 | 1.00 | 57.40 |
| 13150 | CA | HIS | C | 136 | -51.773 | 20.985 | 14.958 | 1.00 | 57.21 |
| 13151 | CB | HIS | C | 136 | -51.468 | 22.047 | 16.021 | 1.00 | 57.41 |
| 13152 | CG | HIS | C | 136 | -51.200 | 23.405 | 15.453 | 1.00 | 57.87 |
| 13153 | ND1 | HIS | C | 136 | -50.000 | 24.059 | 15.629 | 1.00 | 58.41 |
| 13154 | CE1 | HIS | C | 136 | -50.047 | 25.231 | 15.020 | 1.00 | 59.02 |
| 13155 | NE2 | HIS | C | 136 | -51.233 | 25.359 | 14.452 | 1.00 | 59.14 |
| 13156 | CD2 | HIS | C | 136 | -51.973 | 24.229 | 14.707 | 1.00 | 58.12 |
| 13157 | C | HIS | C | 136 | -53.084 | 21.319 | 14.266 | 1.00 | 57.18 |
| 13158 | O | HIS | C | 136 | -53.943 | 22.003 | 14.832 | 1.00 | 56.92 |
| 13159 | N | LYS | C | 137 | -53.244 | 20.863 | 13.032 | 1.00 | 57.03 |
| 13160 | CA | LYS | C | 137 | -54.523 | 21.054 | 12.380 | 1.00 | 56.76 |
| 13161 | CB | LYS | C | 137 | -54.452 | 20.687 | 10.901 | 1.00 | 57.13 |
| 13162 | CG | LYS | C | 137 | -53.463 | 21.525 | 10.120 | 1.00 | 57.71 |
| 13163 | CD | LYS | C | 137 | -52.546 | 20.632 | 9.315 | 1.00 | 58.82 |
| 13164 | CE | LYS | C | 137 | -53.113 | 20.322 | 7.953 | 1.00 | 59.49 |
| 13165 | NZ | LYS | C | 137 | -52.678 | 21.354 | 6.968 | 1.00 | 60.71 |
| 13166 | C | LYS | C | 137 | -55.475 | 20.127 | 13.105 | 1.00 | 56.27 |
| 13167 | O | LYS | C | 137 | -55.052 | 19.210 | 13.814 | 1.00 | 56.04 |
| 13168 | N | LEU | C | 138 | -56.765 | 20.364 | 12.937 | 1.00 | 55.81 |
| 13169 | CA | LEU | C | 138 | -57.748 | 19.530 | 13.597 | 1.00 | 55.19 |
| 13170 | CB | LEU | C | 138 | -58.337 | 20.289 | 14.789 | 1.00 | 55.17 |
| 13171 | CG | LEU | C | 138 | -58.471 | 19.443 | 16.051 | 1.00 | 56.07 |
| 13172 | CD1 | LEU | C | 138 | -57.533 | 18.247 | 15.967 | 1.00 | 56.68 |
| 13173 | CD2 | LEU | C | 138 | -58.210 | 20.259 | 17.306 | 1.00 | 55.13 |
| 13174 | C | LEU | C | 138 | -58.847 | 19.111 | 12.630 | 1.00 | 54.43 |
| 13175 | O | LEU | C | 138 | -59.386 | 19.938 | 11.905 | 1.00 | 54.06 |
| 13176 | N | ALA | C | 139 | -59.151 | 17.819 | 12.608 | 1.00 | 53.92 |
| 13177 | CA | ALA | C | 139 | -60.272 | 17.307 | 11.824 | 1.00 | 53.53 |
| 13178 | CB | ALA | C | 139 | -59.821 | 16.214 | 10.843 | 1.00 | 53.27 |
| 13179 | C | ALA | C | 139 | -61.313 | 16.761 | 12.790 | 1.00 | 53.15 |
| 13180 | O | ALA | C | 139 | -60.997 | 15.958 | 13.665 | 1.00 | 53.00 |
| 13181 | N | TYR | C | 140 | -62.549 | 17.225 | 12.656 | 1.00 | 53.01 |
| 13182 | CA | TYR | C | 140 | -63.622 | 16.731 | 13.504 | 1.00 | 52.78 |
| 13183 | CB | TYR | C | 140 | -63.869 | 17.665 | 14.700 | 1.00 | 53.01 |
| 13184 | CG | TYR | C | 140 | -64.420 | 19.026 | 14.342 | 1.00 | 52.54 |
| 13185 | CD1 | TYR | C | 140 | -65.787 | 19.241 | 14.228 | 1.00 | 52.06 |
| 13186 | CE1 | TYR | C | 140 | -66.291 | 20.492 | 13.904 | 1.00 | 51.90 |
| 13187 | CZ | TYR | C | 140 | -65.413 | 21.552 | 13.696 | 1.00 | 51.95 |
| 13188 | OH | TYR | C | 140 | -65.882 | 22.805 | 13.368 | 1.00 | 50.71 |
| 13189 | CE2 | TYR | C | 140 | -64.059 | 21.359 | 13.814 | 1.00 | 51.61 |
| 13190 | CD2 | TYR | C | 140 | -63.568 | 20.102 | 14.136 | 1.00 | 52.80 |
| 13191 | C | TYR | C | 140 | -64.906 | 16.535 | 12.718 | 1.00 | 52.60 |
| 13192 | O | TYR | C | 140 | -65.132 | 17.186 | 11.698 | 1.00 | 52.33 |
| 13193 | N | VAL | C | 141 | -65.749 | 15.628 | 13.208 | 1.00 | 52.44 |
| 13194 | CA | VAL | C | 141 | -67.033 | 15.354 | 12.574 | 1.00 | 51.54 |
| 13195 | CB | VAL | C | 141 | -67.191 | 13.870 | 12.258 | 1.00 | 51.37 |
| 13196 | CG1 | VAL | C | 141 | -66.079 | 13.422 | 11.339 | 1.00 | 50.66 |
| 13197 | CG2 | VAL | C | 141 | -68.543 | 13.601 | 11.623 | 1.00 | 50.88 |
| 13198 | C | VAL | C | 141 | -68.169 | 15.835 | 13.466 | 1.00 | 51.43 |
| 13199 | O | VAL | C | 141 | -68.195 | 15.557 | 14.663 | 1.00 | 51.69 |

FIGURE 3 IY

| A | B | C | D | E | F | G | H | I | J |
|---|---|---|---|---|---|---|---|---|---|
| 13200 | N | TRP | C | 142 | -69.103 | 16.572 | 12.883 | 1.00 | 51.26 |
| 13201 | CA | TRP | C | 142 | -70.212 | 17.114 | 13.645 | 1.00 | 51.37 |
| 13202 | CB | TRP | C | 142 | -69.836 | 18.493 | 14.207 | 1.00 | 51.31 |
| 13203 | CG | TRP | C | 142 | -70.943 | 19.180 | 14.912 | 1.00 | 50.43 |
| 13204 | CD1 | TRP | C | 142 | -71.326 | 18.997 | 16.205 | 1.00 | 49.84 |
| 13205 | NE1 | TRP | C | 142 | -72.393 | 19.809 | 16.502 | 1.00 | 49.98 |
| 13206 | CE2 | TRP | C | 142 | -72.717 | 20.540 | 15.388 | 1.00 | 50.22 |
| 13207 | CD2 | TRP | C | 142 | -71.823 | 20.165 | 14.367 | 1.00 | 50.21 |
| 13208 | CE3 | TRP | C | 142 | -71.950 | 20.771 | 13.112 | 1.00 | 51.31 |
| 13209 | CZ3 | TRP | C | 142 | -72.947 | 21.722 | 12.920 | 1.00 | 51.29 |
| 13210 | CH2 | TRP | C | 142 | -73.819 | 22.069 | 13.956 | 1.00 | 51.73 |
| 13211 | CZ2 | TRP | C | 142 | -73.722 | 21.490 | 15.196 | 1.00 | 50.71 |
| 13212 | C | TRP | C | 142 | -71.474 | 17.190 | 12.798 | 1.00 | 51.49 |
| 13213 | O | TRP | C | 142 | -71.536 | 17.924 | 11.810 | 1.00 | 51.84 |
| 13214 | N | ASN | C | 143 | -72.488 | 16.433 | 13.200 | 1.00 | 51.64 |
| 13215 | CA | ASN | C | 143 | -73.736 | 16.351 | 12.453 | 1.00 | 51.37 |
| 13216 | CB | ASN | C | 143 | -74.291 | 17.737 | 12.150 | 1.00 | 51.75 |
| 13217 | CG | ASN | C | 143 | -75.197 | 18.258 | 13.241 | 1.00 | 52.46 |
| 13218 | OD1 | ASN | C | 143 | -75.867 | 19.277 | 13.062 | 1.00 | 53.41 |
| 13219 | ND2 | ASN | C | 143 | -75.230 | 17.565 | 14.376 | 1.00 | 53.62 |
| 13220 | C | ASN | C | 143 | -73.513 | 15.575 | 11.167 | 1.00 | 51.06 |
| 13221 | O | ASN | C | 143 | -74.200 | 15.785 | 10.172 | 1.00 | 50.49 |
| 13222 | N | ASN | C | 144 | -72.523 | 14.691 | 11.209 | 1.00 | 51.08 |
| 13223 | CA | ASN | C | 144 | -72.202 | 13.797 | 10.101 | 1.00 | 51.15 |
| 13224 | CB | ASN | C | 144 | -73.462 | 13.126 | 9.555 | 1.00 | 50.84 |
| 13225 | CG | ASN | C | 144 | -73.999 | 12.047 | 10.484 | 1.00 | 50.29 |
| 13226 | OD1 | ASN | C | 144 | -74.584 | 11.063 | 10.036 | 1.00 | 50.27 |
| 13227 | ND2 | ASN | C | 144 | -73.805 | 12.230 | 11.778 | 1.00 | 48.07 |
| 13228 | C | ASN | C | 144 | -71.404 | 14.447 | 8.973 | 1.00 | 51.59 |
| 13229 | O | ASN | C | 144 | -71.328 | 13.904 | 7.866 | 1.00 | 51.44 |
| 13230 | N | ASP | C | 145 | -70.813 | 15.604 | 9.260 | 1.00 | 51.81 |
| 13231 | CA | ASP | C | 145 | -69.983 | 16.296 | 8.283 | 1.00 | 52.26 |
| 13232 | CB | ASP | C | 145 | -70.640 | 17.601 | 7.815 | 1.00 | 52.15 |
| 13233 | CG | ASP | C | 145 | -71.764 | 17.362 | 6.811 | 1.00 | 50.96 |
| 13234 | OD1 | ASP | C | 145 | -72.810 | 18.029 | 6.926 | 1.00 | 50.59 |
| 13235 | OD2 | ASP | C | 145 | -71.699 | 16.526 | 5.884 | 1.00 | 48.94 |
| 13236 | C | ASP | C | 145 | -68.578 | 16.547 | 8.819 | 1.00 | 52.86 |
| 13237 | O | ASP | C | 145 | -68.357 | 16.618 | 10.023 | 1.00 | 52.66 |
| 13238 | N | ILE | C | 146 | -67.622 | 16.666 | 7.908 | 1.00 | 53.67 |
| 13239 | CA | ILE | C | 146 | -66.237 | 16.889 | 8.285 | 1.00 | 53.87 |
| 13240 | CB | ILE | C | 146 | -65.327 | 16.195 | 7.286 | 1.00 | 53.95 |
| 13241 | CG1 | ILE | C | 146 | -65.826 | 14.767 | 7.057 | 1.00 | 53.11 |
| 13242 | CD1 | ILE | C | 146 | -64.983 | 13.990 | 6.120 | 1.00 | 52.39 |
| 13243 | CG2 | ILE | C | 146 | -63.868 | 16.250 | 7.748 | 1.00 | 53.60 |
| 13244 | C | ILE | C | 146 | -65.895 | 18.368 | 8.334 | 1.00 | 54.42 |
| 13245 | O | ILE | C | 146 | -66.372 | 19.153 | 7.528 | 1.00 | 54.37 |
| 13246 | N | TYR | C | 147 | -65.086 | 18.742 | 9.311 | 1.00 | 55.14 |
| 13247 | CA | TYR | C | 147 | -64.598 | 20.102 | 9.414 | 1.00 | 55.88 |
| 13248 | CB | TYR | C | 147 | -65.287 | 20.852 | 10.551 | 1.00 | 55.87 |
| 13249 | CG | TYR | C | 147 | -66.776 | 21.024 | 10.347 | 1.00 | 55.84 |
| 13250 | CD1 | TYR | C | 147 | -67.291 | 22.200 | 9.819 | 1.00 | 54.69 |

FIGURE 3 IZ

| A | B | C | D | E | F | G | H | I | J |
|---|---|---|---|---|---|---|---|---|---|
| 13251 | CE1 | TYR | C | 147 | -68.644 | 22.366 | 9.628 | 1.00 | 54.24 |
| 13252 | CZ | TYR | C | 147 | -69.512 | 21.345 | 9.957 | 1.00 | 55.37 |
| 13253 | OH | TYR | C | 147 | -70.872 | 21.513 | 9.764 | 1.00 | 55.23 |
| 13254 | CE2 | TYR | C | 147 | -69.028 | 20.162 | 10.489 | 1.00 | 55.28 |
| 13255 | CD2 | TYR | C | 147 | -67.667 | 20.007 | 10.679 | 1.00 | 55.21 |
| 13256 | C | TYR | C | 147 | -63.093 | 20.057 | 9.630 | 1.00 | 56.38 |
| 13257 | O | TYR | C | 147 | -62.556 | 19.073 | 10.150 | 1.00 | 56.37 |
| 13258 | N | VAL | C | 148 | -62.406 | 21.106 | 9.192 | 1.00 | 57.10 |
| 13259 | CA | VAL | C | 148 | -60.964 | 21.201 | 9.402 | 1.00 | 57.64 |
| 13260 | CB | VAL | C | 148 | -60.166 | 21.037 | 8.104 | 1.00 | 57.56 |
| 13261 | CG1 | VAL | C | 148 | -58.687 | 21.228 | 8.389 | 1.00 | 57.70 |
| 13262 | CG2 | VAL | C | 148 | -60.425 | 19.678 | 7.478 | 1.00 | 57.68 |
| 13263 | C | VAL | C | 148 | -60.570 | 22.533 | 10.033 | 1.00 | 57.92 |
| 13264 | O | VAL | C | 148 | -60.899 | 23.598 | 9.516 | 1.00 | 58.05 |
| 13265 | N | LYS | C | 149 | -59.891 | 22.464 | 11.170 | 1.00 | 58.25 |
| 13266 | CA | LYS | C | 149 | -59.353 | 23.654 | 11.792 | 1.00 | 58.62 |
| 13267 | CB | LYS | C | 149 | -59.876 | 23.826 | 13.220 | 1.00 | 58.69 |
| 13268 | CG | LYS | C | 149 | -61.085 | 24.741 | 13.265 | 1.00 | 58.34 |
| 13269 | CD | LYS | C | 149 | -61.901 | 24.600 | 14.520 | 1.00 | 59.13 |
| 13270 | CE | LYS | C | 149 | -63.294 | 25.159 | 14.274 | 1.00 | 60.03 |
| 13271 | NZ | LYS | C | 149 | -64.079 | 25.410 | 15.511 | 1.00 | 60.87 |
| 13272 | C | LYS | C | 149 | -57.832 | 23.592 | 11.721 | 1.00 | 58.96 |
| 13273 | O | LYS | C | 149 | -57.202 | 22.747 | 12.369 | 1.00 | 58.81 |
| 13274 | N | ILE | C | 150 | -57.257 | 24.462 | 10.887 | 1.00 | 59.42 |
| 13275 | CA | ILE | C | 150 | -55.812 | 24.515 | 10.680 | 1.00 | 59.81 |
| 13276 | CB | ILE | C | 150 | -55.467 | 25.272 | 9.379 | 1.00 | 60.08 |
| 13277 | CG1 | ILE | C | 150 | -56.066 | 24.556 | 8.159 | 1.00 | 59.91 |
| 13278 | CD1 | ILE | C | 150 | -55.435 | 23.217 | 7.867 | 1.00 | 59.08 |
| 13279 | CG2 | ILE | C | 150 | -53.949 | 25.425 | 9.212 | 1.00 | 60.27 |
| 13280 | C | ILE | C | 150 | -55.180 | 25.174 | 11.893 | 1.00 | 60.09 |
| 13281 | O | ILE | C | 150 | -54.076 | 24.829 | 12.301 | 1.00 | 60.07 |
| 13282 | N | GLU | C | 151 | -55.894 | 26.127 | 12.473 | 1.00 | 60.72 |
| 13283 | CA | GLU | C | 151 | -55.458 | 26.743 | 13.719 | 1.00 | 61.36 |
| 13284 | CB | GLU | C | 151 | -54.933 | 28.171 | 13.509 | 1.00 | 61.42 |
| 13285 | CG | GLU | C | 151 | -53.838 | 28.331 | 12.458 | 1.00 | 61.94 |
| 13286 | CD | GLU | C | 151 | -52.553 | 27.587 | 12.785 | 1.00 | 62.45 |
| 13287 | OE1 | GLU | C | 151 | -52.356 | 27.199 | 13.953 | 1.00 | 62.15 |
| 13288 | OE2 | GLU | C | 151 | -51.733 | 27.386 | 11.860 | 1.00 | 63.16 |
| 13289 | C | GLU | C | 151 | -56.628 | 26.732 | 14.703 | 1.00 | 61.64 |
| 13290 | O | GLU | C | 151 | -57.732 | 27.179 | 14.380 | 1.00 | 61.23 |
| 13291 | N | PRO | C | 152 | -56.381 | 26.193 | 15.892 | 1.00 | 62.04 |
| 13292 | CA | PRO | C | 152 | -57.387 | 26.113 | 16.954 | 1.00 | 62.45 |
| 13293 | CB | PRO | C | 152 | -56.541 | 25.854 | 18.196 | 1.00 | 62.32 |
| 13294 | CG | PRO | C | 152 | -55.401 | 25.044 | 17.678 | 1.00 | 62.48 |
| 13295 | CD | PRO | C | 152 | -55.102 | 25.586 | 16.300 | 1.00 | 62.14 |
| 13296 | C | PRO | C | 152 | -58.233 | 27.378 | 17.136 | 1.00 | 62.92 |
| 13297 | O | PRO | C | 152 | -59.417 | 27.267 | 17.461 | 1.00 | 62.99 |
| 13298 | N | ASN | C | 153 | -57.654 | 28.558 | 16.945 | 1.00 | 63.19 |
| 13299 | CA | ASN | C | 153 | -58.444 | 29.781 | 17.090 | 1.00 | 63.80 |
| 13300 | CB | ASN | C | 153 | -57.665 | 30.896 | 17.815 | 1.00 | 63.84 |
| 13301 | CG | ASN | C | 153 | -56.339 | 31.231 | 17.150 | 1.00 | 64.51 |

FIGURE 3 JA

| A | B | C | D | E | F | G | H | I | J |
|---|---|---|---|---|---|---|---|---|---|
| 13302 | OD1 | ASN | C | 153 | -55.695 | 32.218 | 17.507 | 1.00 | 64.68 |
| 13303 | ND2 | ASN | C | 153 | -55.921 | 30.409 | 16.188 | 1.00 | 65.33 |
| 13304 | C | ASN | C | 153 | -59.087 | 30.284 | 15.790 | 1.00 | 63.87 |
| 13305 | O | ASN | C | 153 | -59.859 | 31.238 | 15.806 | 1.00 | 64.01 |
| 13306 | N | LEU | C | 154 | -58.790 | 29.616 | 14.679 | 1.00 | 63.96 |
| 13307 | CA | LEU | C | 154 | -59.337 | 29.993 | 13.376 | 1.00 | 64.19 |
| 13308 | CB | LEU | C | 154 | -58.359 | 29.605 | 12.259 | 1.00 | 64.36 |
| 13309 | CG | LEU | C | 154 | -57.491 | 30.702 | 11.634 | 1.00 | 64.94 |
| 13310 | CD1 | LEU | C | 154 | -57.018 | 31.723 | 12.664 | 1.00 | 66.40 |
| 13311 | CD2 | LEU | C | 154 | -56.308 | 30.091 | 10.902 | 1.00 | 66.34 |
| 13312 | C | LEU | C | 154 | -60.701 | 29.373 | 13.075 | 1.00 | 64.11 |
| 13313 | O | LEU | C | 154 | -61.042 | 28.318 | 13.606 | 1.00 | 63.97 |
| 13314 | N | PRO | C | 155 | -61.485 | 30.052 | 12.238 | 1.00 | 64.06 |
| 13315 | CA | PRO | C | 155 | -62.754 | 29.510 | 11.750 | 1.00 | 64.03 |
| 13316 | CB | PRO | C | 155 | -63.240 | 30.578 | 10.765 | 1.00 | 64.17 |
| 13317 | CG | PRO | C | 155 | -62.588 | 31.833 | 11.221 | 1.00 | 64.13 |
| 13318 | CD | PRO | C | 155 | -61.239 | 31.415 | 11.738 | 1.00 | 64.18 |
| 13319 | C | PRO | C | 155 | -62.516 | 28.199 | 11.016 | 1.00 | 63.94 |
| 13320 | O | PRO | C | 155 | -61.470 | 28.006 | 10.389 | 1.00 | 63.61 |
| 13321 | N | SER | C | 156 | -63.501 | 27.311 | 11.084 | 1.00 | 63.72 |
| 13322 | CA | SER | C | 156 | -63.365 | 25.985 | 10.508 | 1.00 | 63.40 |
| 13323 | CB | SER | C | 156 | -64.247 | 25.008 | 11.278 | 1.00 | 63.45 |
| 13324 | OG | SER | C | 156 | -63.555 | 23.796 | 11.492 | 1.00 | 64.22 |
| 13325 | C | SER | C | 156 | -63.694 | 25.920 | 9.018 | 1.00 | 62.88 |
| 13326 | O | SER | C | 156 | -64.485 | 26.711 | 8.512 | 1.00 | 62.47 |
| 13327 | N | TYR | C | 157 | -63.065 | 24.970 | 8.330 | 1.00 | 62.46 |
| 13328 | CA | TYR | C | 157 | -63.328 | 24.714 | 6.918 | 1.00 | 62.31 |
| 13329 | CB | TYR | C | 157 | -62.032 | 24.383 | 6.172 | 1.00 | 62.70 |
| 13330 | CG | TYR | C | 157 | -61.109 | 25.556 | 5.981 | 1.00 | 63.80 |
| 13331 | CD1 | TYR | C | 157 | -61.433 | 26.574 | 5.099 | 1.00 | 64.98 |
| 13332 | CE1 | TYR | C | 157 | -60.595 | 27.657 | 4.919 | 1.00 | 66.09 |
| 13333 | CZ | TYR | C | 157 | -59.418 | 27.732 | 5.627 | 1.00 | 66.66 |
| 13334 | OH | TYR | C | 157 | -58.588 | 28.810 | 5.444 | 1.00 | 67.19 |
| 13335 | CE2 | TYR | C | 157 | -59.069 | 26.729 | 6.512 | 1.00 | 66.54 |
| 13336 | CD2 | TYR | C | 157 | -59.916 | 25.649 | 6.685 | 1.00 | 64.83 |
| 13337 | C | TYR | C | 157 | -64.270 | 23.522 | 6.807 | 1.00 | 61.61 |
| 13338 | O | TYR | C | 157 | -63.955 | 22.428 | 7.271 | 1.00 | 61.25 |
| 13339 | N | ARG | C | 158 | -65.419 | 23.726 | 6.181 | 1.00 | 60.98 |
| 13340 | CA | ARG | C | 158 | -66.393 | 22.647 | 6.057 | 1.00 | 60.38 |
| 13341 | CB | ARG | C | 158 | -67.811 | 23.194 | 6.220 | 1.00 | 60.32 |
| 13342 | CG | ARG | C | 158 | -68.887 | 22.148 | 6.067 | 1.00 | 60.13 |
| 13343 | CD | ARG | C | 158 | -70.289 | 22.689 | 6.231 | 1.00 | 60.55 |
| 13344 | NE | ARG | C | 158 | -71.293 | 21.657 | 6.004 | 1.00 | 59.93 |
| 13345 | CZ | ARG | C | 158 | -72.528 | 21.705 | 6.481 | 1.00 | 60.15 |
| 13346 | NH1 | ARG | C | 158 | -73.379 | 20.719 | 6.216 | 1.00 | 59.78 |
| 13347 | NH2 | ARG | C | 158 | -72.918 | 22.741 | 7.218 | 1.00 | 58.83 |
| 13348 | C | ARG | C | 158 | -66.266 | 21.865 | 4.749 | 1.00 | 59.75 |
| 13349 | O | ARG | C | 158 | -66.643 | 22.354 | 3.693 | 1.00 | 59.93 |
| 13350 | N | ILE | C | 159 | -65.749 | 20.643 | 4.838 | 1.00 | 59.20 |
| 13351 | CA | ILE | C | 159 | -65.558 | 19.775 | 3.671 | 1.00 | 58.45 |
| 13352 | CB | ILE | C | 159 | -64.607 | 18.600 | 4.017 | 1.00 | 58.57 |

FIGURE 3 JB

| A | B | C | D | E | F | G | H | I | J |
|---|---|---|---|---|---|---|---|---|---|
| 13353 | CG1 | ILE | C | 159 | -63.287 | 19.122 | 4.592 | 1.00 | 58.50 |
| 13354 | CD1 | ILE | C | 159 | -63.306 | 19.304 | 6.083 | 1.00 | 58.48 |
| 13355 | CG2 | ILE | C | 159 | -64.353 | 17.719 | 2.800 | 1.00 | 58.49 |
| 13356 | C | ILE | C | 159 | -66.866 | 19.241 | 3.083 | 1.00 | 57.81 |
| 13357 | O | ILE | C | 159 | -67.053 | 19.271 | 1.866 | 1.00 | 58.16 |
| 13358 | N | THR | C | 160 | -67.771 | 18.759 | 3.936 | 1.00 | 57.01 |
| 13359 | CA | THR | C | 160 | -69.032 | 18.178 | 3.450 | 1.00 | 56.14 |
| 13360 | CB | THR | C | 160 | -69.153 | 16.680 | 3.827 | 1.00 | 56.00 |
| 13361 | OG1 | THR | C | 160 | -69.057 | 16.522 | 5.250 | 1.00 | 56.18 |
| 13362 | CG2 | THR | C | 160 | -67.977 | 15.890 | 3.296 | 1.00 | 55.80 |
| 13363 | C | THR | C | 160 | -70.298 | 18.921 | 3.886 | 1.00 | 55.68 |
| 13364 | O | THR | C | 160 | -70.305 | 19.655 | 4.873 | 1.00 | 55.61 |
| 13365 | N | TRP | C | 161 | -71.375 | 18.694 | 3.142 | 1.00 | 54.98 |
| 13366 | CA | TRP | C | 161 | -72.648 | 19.349 | 3.390 | 1.00 | 54.68 |
| 13367 | CB | TRP | C | 161 | -72.805 | 20.553 | 2.461 | 1.00 | 55.08 |
| 13368 | CG | TRP | C | 161 | -71.580 | 21.354 | 2.378 | 1.00 | 55.56 |
| 13369 | CD1 | TRP | C | 161 | -70.367 | 20.951 | 1.897 | 1.00 | 55.52 |
| 13370 | NE1 | TRP | C | 161 | -69.459 | 21.977 | 2.003 | 1.00 | 55.96 |
| 13371 | CE2 | TRP | C | 161 | -70.081 | 23.064 | 2.562 | 1.00 | 56.02 |
| 13372 | CD2 | TRP | C | 161 | -71.418 | 22.701 | 2.811 | 1.00 | 55.85 |
| 13373 | CE3 | TRP | C | 161 | -72.274 | 23.648 | 3.389 | 1.00 | 56.89 |
| 13374 | CZ3 | TRP | C | 161 | -71.779 | 24.904 | 3.690 | 1.00 | 57.47 |
| 13375 | CH2 | TRP | C | 161 | -70.448 | 25.234 | 3.428 | 1.00 | 57.78 |
| 13376 | CZ2 | TRP | C | 161 | -69.582 | 24.329 | 2.869 | 1.00 | 57.05 |
| 13377 | C | TRP | C | 161 | -73.802 | 18.401 | 3.137 | 1.00 | 53.98 |
| 13378 | O | TRP | C | 161 | -74.955 | 18.812 | 3.138 | 1.00 | 53.75 |
| 13379 | N | THR | C | 162 | -73.489 | 17.135 | 2.903 | 1.00 | 53.53 |
| 13380 | CA | THR | C | 162 | -74.520 | 16.139 | 2.644 | 1.00 | 52.88 |
| 13381 | CB | THR | C | 162 | -74.123 | 15.294 | 1.420 | 1.00 | 53.01 |
| 13382 | OG1 | THR | C | 162 | -72.734 | 14.954 | 1.507 | 1.00 | 52.69 |
| 13383 | CG2 | THR | C | 162 | -74.176 | 16.134 | 0.155 | 1.00 | 53.59 |
| 13384 | C | THR | C | 162 | -74.789 | 15.248 | 3.869 | 1.00 | 52.40 |
| 13385 | O | THR | C | 162 | -75.542 | 14.287 | 3.792 | 1.00 | 52.03 |
| 13386 | N | GLY | C | 163 | -74.169 | 15.575 | 5.000 | 1.00 | 52.20 |
| 13387 | CA | GLY | C | 163 | -74.321 | 14.780 | 6.213 | 1.00 | 51.36 |
| 13388 | C | GLY | C | 163 | -75.720 | 14.812 | 6.799 | 1.00 | 50.71 |
| 13389 | O | GLY | C | 163 | -76.276 | 15.893 | 7.019 | 1.00 | 50.76 |
| 13390 | N | LYS | C | 164 | -76.288 | 13.632 | 7.051 | 1.00 | 49.94 |
| 13391 | CA | LYS | C | 164 | -77.642 | 13.528 | 7.599 | 1.00 | 49.15 |
| 13392 | CB | LYS | C | 164 | -78.682 | 13.626 | 6.478 | 1.00 | 49.20 |
| 13393 | CG | LYS | C | 164 | -80.096 | 13.243 | 6.890 | 1.00 | 50.16 |
| 13394 | CD | LYS | C | 164 | -81.170 | 14.082 | 6.179 | 1.00 | 52.16 |
| 13395 | CE | LYS | C | 164 | -81.338 | 15.453 | 6.868 | 1.00 | 54.24 |
| 13396 | NZ | LYS | C | 164 | -82.688 | 16.088 | 6.672 | 1.00 | 54.51 |
| 13397 | C | LYS | C | 164 | -77.888 | 12.290 | 8.495 | 1.00 | 48.51 |
| 13398 | O | LYS | C | 164 | -77.695 | 11.140 | 8.082 | 1.00 | 47.95 |
| 13399 | N | GLU | C | 165 | -78.326 | 12.559 | 9.723 | 1.00 | 47.71 |
| 13400 | CA | GLU | C | 165 | -78.614 | 11.536 | 10.727 | 1.00 | 47.19 |
| 13401 | CB | GLU | C | 165 | -79.580 | 12.099 | 11.776 | 1.00 | 47.47 |
| 13402 | CG | GLU | C | 165 | -79.630 | 11.332 | 13.092 | 1.00 | 49.01 |
| 13403 | CD | GLU | C | 165 | -79.997 | 12.232 | 14.260 | 1.00 | 51.41 |

FIGURE 3 JC

| A | B | C | D | E | F | G | H | I | J |
|---|---|---|---|---|---|---|---|---|---|
| 13404 | OE1 | GLU | C | 165 | -81.175 | 12.615 | 14.381 | 1.00 | 52.87 |
| 13405 | OE2 | GLU | C | 165 | -79.102 | 12.589 | 15.048 | 1.00 | 53.74 |
| 13406 | C | GLU | C | 165 | -79.180 | 10.243 | 10.155 | 1.00 | 46.25 |
| 13407 | O | GLU | C | 165 | -80.220 | 10.249 | 9.504 | 1.00 | 45.87 |
| 13408 | N | ASN | C | 166 | -78.481 | 9.141 | 10.423 | 1.00 | 45.49 |
| 13409 | CA | ASN | C | 166 | -78.891 | 7.800 | 9.999 | 1.00 | 45.03 |
| 13410 | CB | ASN | C | 166 | -80.239 | 7.395 | 10.612 | 1.00 | 45.31 |
| 13411 | CG | ASN | C | 166 | -80.312 | 7.640 | 12.103 | 1.00 | 45.21 |
| 13412 | OD1 | ASN | C | 166 | -79.403 | 7.285 | 12.858 | 1.00 | 44.24 |
| 13413 | ND2 | ASN | C | 166 | -81.409 | 8.251 | 12.538 | 1.00 | 45.18 |
| 13414 | C | ASN | C | 166 | -78.982 | 7.583 | 8.501 | 1.00 | 44.76 |
| 13415 | O | ASN | C | 166 | -79.366 | 6.503 | 8.062 | 1.00 | 44.58 |
| 13416 | N | ILE | C | 167 | -78.643 | 8.596 | 7.710 | 1.00 | 44.44 |
| 13417 | CA | ILE | C | 167 | -78.720 | 8.461 | 6.262 | 1.00 | 43.81 |
| 13418 | CB | ILE | C | 167 | -79.562 | 9.586 | 5.680 | 1.00 | 43.95 |
| 13419 | CG1 | ILE | C | 167 | -81.010 | 9.436 | 6.156 | 1.00 | 43.48 |
| 13420 | CD1 | ILE | C | 167 | -81.642 | 8.087 | 5.791 | 1.00 | 43.86 |
| 13421 | CG2 | ILE | C | 167 | -79.482 | 9.575 | 4.163 | 1.00 | 42.86 |
| 13422 | C | ILE | C | 167 | -77.349 | 8.393 | 5.590 | 1.00 | 43.65 |
| 13423 | O | ILE | C | 167 | -77.022 | 7.423 | 4.909 | 1.00 | 43.28 |
| 13424 | N | ILE | C | 168 | -76.552 | 9.438 | 5.756 | 1.00 | 43.61 |
| 13425 | CA | ILE | C | 168 | -75.218 | 9.420 | 5.181 | 1.00 | 43.23 |
| 13426 | CB | ILE | C | 168 | -75.126 | 10.230 | 3.843 | 1.00 | 43.69 |
| 13427 | CG1 | ILE | C | 168 | -74.691 | 11.666 | 4.102 | 1.00 | 42.79 |
| 13428 | CD1 | ILE | C | 168 | -73.217 | 11.872 | 3.887 | 1.00 | 42.78 |
| 13429 | CG2 | ILE | C | 168 | -76.413 | 10.127 | 2.985 | 1.00 | 42.05 |
| 13430 | C | ILE | C | 168 | -74.177 | 9.881 | 6.197 | 1.00 | 43.21 |
| 13431 | O | ILE | C | 168 | -74.377 | 10.860 | 6.930 | 1.00 | 42.93 |
| 13432 | N | TYR | C | 169 | -73.065 | 9.156 | 6.236 | 1.00 | 42.75 |
| 13433 | CA | TYR | C | 169 | -72.011 | 9.450 | 7.180 | 1.00 | 42.82 |
| 13434 | CB | TYR | C | 169 | -71.712 | 8.229 | 8.064 | 1.00 | 43.22 |
| 13435 | CG | TYR | C | 169 | -72.924 | 7.570 | 8.671 | 1.00 | 44.10 |
| 13436 | CD1 | TYR | C | 169 | -73.862 | 6.936 | 7.870 | 1.00 | 45.21 |
| 13437 | CE1 | TYR | C | 169 | -74.973 | 6.331 | 8.416 | 1.00 | 46.11 |
| 13438 | CZ | TYR | C | 169 | -75.157 | 6.339 | 9.788 | 1.00 | 46.33 |
| 13439 | OH | TYR | C | 169 | -76.267 | 5.719 | 10.311 | 1.00 | 46.34 |
| 13440 | CE2 | TYR | C | 169 | -74.237 | 6.959 | 10.615 | 1.00 | 45.49 |
| 13441 | CD2 | TYR | C | 169 | -73.125 | 7.570 | 10.051 | 1.00 | 45.20 |
| 13442 | C | TYR | C | 169 | -70.724 | 9.893 | 6.491 | 1.00 | 42.51 |
| 13443 | O | TYR | C | 169 | -70.168 | 9.170 | 5.659 | 1.00 | 41.77 |
| 13444 | N | ASN | C | 170 | -70.250 | 11.077 | 6.872 | 1.00 | 42.19 |
| 13445 | CA | ASN | C | 170 | -68.988 | 11.592 | 6.377 | 1.00 | 42.04 |
| 13446 | CB | ASN | C | 170 | -69.160 | 13.017 | 5.853 | 1.00 | 41.71 |
| 13447 | CG | ASN | C | 170 | -70.039 | 13.079 | 4.609 | 1.00 | 42.53 |
| 13448 | OD1 | ASN | C | 170 | -69.808 | 12.350 | 3.646 | 1.00 | 42.46 |
| 13449 | ND2 | ASN | C | 170 | -71.059 | 13.941 | 4.631 | 1.00 | 41.76 |
| 13450 | C | ASN | C | 170 | -67.935 | 11.547 | 7.482 | 1.00 | 42.00 |
| 13451 | O | ASN | C | 170 | -68.083 | 12.198 | 8.515 | 1.00 | 42.30 |
| 13452 | N | GLY | C | 171 | -66.886 | 10.759 | 7.273 | 1.00 | 41.64 |
| 13453 | CA | GLY | C | 171 | -65.807 | 10.670 | 8.236 | 1.00 | 41.13 |
| 13454 | C | GLY | C | 171 | -66.058 | 9.727 | 9.399 | 1.00 | 40.95 |

FIGURE 3 JD

| A | B | C | D | E | F | G | H | I | J |
|---|---|---|---|---|---|---|---|---|---|
| 13455 | O | GLY | C | 171 | -65.154 | 9.461 | 10.193 | 1.00 | 40.62 |
| 13456 | N | ILE | C | 172 | -67.286 | 9.228 | 9.516 | 1.00 | 40.57 |
| 13457 | CA | ILE | C | 172 | -67.624 | 8.289 | 10.578 | 1.00 | 39.79 |
| 13458 | CB | ILE | C | 172 | -68.451 | 8.973 | 11.661 | 1.00 | 39.90 |
| 13459 | CG1 | ILE | C | 172 | -69.562 | 9.796 | 11.022 | 1.00 | 39.26 |
| 13460 | CD1 | ILE | C | 172 | -70.532 | 10.354 | 12.003 | 1.00 | 38.29 |
| 13461 | CG2 | ILE | C | 172 | -67.563 | 9.856 | 12.540 | 1.00 | 39.02 |
| 13462 | C | ILE | C | 172 | -68.404 | 7.136 | 9.996 | 1.00 | 39.77 |
| 13463 | O | ILE | C | 172 | -69.107 | 7.300 | 9.002 | 1.00 | 39.81 |
| 13464 | N | THR | C | 173 | -68.276 | 5.971 | 10.619 | 1.00 | 39.50 |
| 13465 | CA | THR | C | 173 | -68.964 | 4.773 | 10.169 | 1.00 | 39.42 |
| 13466 | CB | THR | C | 173 | -68.200 | 3.524 | 10.633 | 1.00 | 39.64 |
| 13467 | OG1 | THR | C | 173 | -67.854 | 3.665 | 12.014 | 1.00 | 40.82 |
| 13468 | CG2 | THR | C | 173 | -66.831 | 3.421 | 9.955 | 1.00 | 39.55 |
| 13469 | C | THR | C | 173 | -70.394 | 4.703 | 10.709 | 1.00 | 39.41 |
| 13470 | O | THR | C | 173 | -70.742 | 5.398 | 11.666 | 1.00 | 39.69 |
| 13471 | N | ASP | C | 174 | -71.218 | 3.875 | 10.068 | 1.00 | 39.14 |
| 13472 | CA | ASP | C | 174 | -72.564 | 3.584 | 10.531 | 1.00 | 39.00 |
| 13473 | CB | ASP | C | 174 | -73.484 | 3.230 | 9.355 | 1.00 | 39.09 |
| 13474 | CG | ASP | C | 174 | -73.069 | 1.954 | 8.662 | 1.00 | 38.75 |
| 13475 | OD1 | ASP | C | 174 | -73.925 | 1.261 | 8.079 | 1.00 | 39.17 |
| 13476 | OD2 | ASP | C | 174 | -71.899 | 1.549 | 8.661 | 1.00 | 39.00 |
| 13477 | C | ASP | C | 174 | -72.423 | 2.377 | 11.458 | 1.00 | 38.90 |
| 13478 | O | ASP | C | 174 | -71.294 | 1.956 | 11.755 | 1.00 | 38.94 |
| 13479 | N | TRP | C | 175 | -73.548 | 1.788 | 11.874 | 1.00 | 38.32 |
| 13480 | CA | TRP | C | 175 | -73.495 | 0.669 | 12.826 | 1.00 | 37.39 |
| 13481 | CB | TRP | C | 175 | -74.881 | 0.130 | 13.249 | 1.00 | 36.66 |
| 13482 | CG | TRP | C | 175 | -74.755 | -0.781 | 14.444 | 1.00 | 34.76 |
| 13483 | CD1 | TRP | C | 175 | -74.894 | -0.437 | 15.767 | 1.00 | 33.61 |
| 13484 | NE1 | TRP | C | 175 | -74.656 | -1.529 | 16.570 | 1.00 | 32.83 |
| 13485 | CE2 | TRP | C | 175 | -74.338 | -2.603 | 15.781 | 1.00 | 33.34 |
| 13486 | CD2 | TRP | C | 175 | -74.393 | -2.168 | 14.435 | 1.00 | 33.17 |
| 13487 | CE3 | TRP | C | 175 | -74.102 | -3.089 | 13.426 | 1.00 | 33.10 |
| 13488 | CZ3 | TRP | C | 175 | -73.784 | -4.403 | 13.778 | 1.00 | 35.95 |
| 13489 | CH2 | TRP | C | 175 | -73.749 | -4.808 | 15.131 | 1.00 | 33.36 |
| 13490 | CZ2 | TRP | C | 175 | -74.021 | -3.923 | 16.139 | 1.00 | 33.92 |
| 13491 | C | TRP | C | 175 | -72.602 | -0.481 | 12.405 | 1.00 | 37.52 |
| 13492 | O | TRP | C | 175 | -71.697 | -0.811 | 13.137 | 1.00 | 37.46 |
| 13493 | N | VAL | C | 176 | -72.860 | -1.120 | 11.265 | 1.00 | 38.02 |
| 13494 | CA | VAL | C | 176 | -72.031 | -2.269 | 10.873 | 1.00 | 38.72 |
| 13495 | CB | VAL | C | 176 | -72.546 | -3.046 | 9.649 | 1.00 | 38.61 |
| 13496 | CG1 | VAL | C | 176 | -72.889 | -2.113 | 8.498 | 1.00 | 38.51 |
| 13497 | CG2 | VAL | C | 176 | -73.685 | -3.927 | 10.027 | 1.00 | 40.15 |
| 13498 | C | VAL | C | 176 | -70.568 | -1.972 | 10.591 | 1.00 | 38.82 |
| 13499 | O | VAL | C | 176 | -69.719 | -2.795 | 10.886 | 1.00 | 38.67 |
| 13500 | N | TYR | C | 177 | -70.277 | -0.833 | 9.979 | 1.00 | 39.42 |
| 13501 | CA | TYR | C | 177 | -68.887 | -0.495 | 9.698 | 1.00 | 40.38 |
| 13502 | CB | TYR | C | 177 | -68.762 | 0.747 | 8.802 | 1.00 | 40.37 |
| 13503 | CG | TYR | C | 177 | -68.581 | 0.387 | 7.356 | 1.00 | 42.38 |
| 13504 | CD1 | TYR | C | 177 | -69.664 | 0.341 | 6.491 | 1.00 | 42.20 |
| 13505 | CE1 | TYR | C | 177 | -69.499 | -0.006 | 5.164 | 1.00 | 43.28 |

FIGURE 3 JE

| A | B | C | D | E | F | G | H | I | J |
|---|---|---|---|---|---|---|---|---|---|
| 13506 | CZ | TYR | C | 177 | -68.245 | -0.330 | 4.690 | 1.00 | 44.13 |
| 13507 | OH | TYR | C | 177 | -68.083 | -0.679 | 3.366 | 1.00 | 44.97 |
| 13508 | CE2 | TYR | C | 177 | -67.152 | -0.300 | 5.528 | 1.00 | 44.63 |
| 13509 | CD2 | TYR | C | 177 | -67.323 | 0.054 | 6.857 | 1.00 | 43.88 |
| 13510 | C | TYR | C | 177 | -68.126 | -0.296 | 10.991 | 1.00 | 40.39 |
| 13511 | O | TYR | C | 177 | -66.966 | -0.692 | 11.092 | 1.00 | 40.42 |
| 13512 | N | GLU | C | 178 | -68.784 | 0.323 | 11.973 | 1.00 | 40.72 |
| 13513 | CA | GLU | C | 178 | -68.159 | 0.550 | 13.264 | 1.00 | 40.73 |
| 13514 | CB | GLU | C | 178 | -69.032 | 1.401 | 14.184 | 1.00 | 40.68 |
| 13515 | CG | GLU | C | 178 | -68.530 | 1.344 | 15.622 | 1.00 | 41.20 |
| 13516 | CD | GLU | C | 178 | -69.296 | 2.227 | 16.588 | 1.00 | 42.64 |
| 13517 | OE1 | GLU | C | 178 | -70.257 | 2.912 | 16.159 | 1.00 | 43.45 |
| 13518 | OE2 | GLU | C | 178 | -68.924 | 2.237 | 17.785 | 1.00 | 41.11 |
| 13519 | C | GLU | C | 178 | -67.864 | -0.749 | 13.985 | 1.00 | 41.01 |
| 13520 | O | GLU | C | 178 | -66.825 | -0.888 | 14.632 | 1.00 | 41.00 |
| 13521 | N | GLU | C | 179 | -68.783 | -1.701 | 13.879 | 1.00 | 40.73 |
| 13522 | CA | GLU | C | 179 | -68.669 | -2.926 | 14.658 | 1.00 | 40.70 |
| 13523 | CB | GLU | C | 179 | -70.059 | -3.363 | 15.140 | 1.00 | 40.46 |
| 13524 | CG | GLU | C | 179 | -70.098 | -4.669 | 15.914 | 1.00 | 40.01 |
| 13525 | CD | GLU | C | 179 | -69.334 | -4.596 | 17.216 | 1.00 | 39.94 |
| 13526 | OE1 | GLU | C | 179 | -68.845 | -5.642 | 17.661 | 1.00 | 40.92 |
| 13527 | OE2 | GLU | C | 179 | -69.212 | -3.498 | 17.796 | 1.00 | 40.49 |
| 13528 | C | GLU | C | 179 | -67.987 | -4.086 | 13.948 | 1.00 | 40.96 |
| 13529 | O | GLU | C | 179 | -67.259 | -4.848 | 14.577 | 1.00 | 40.57 |
| 13530 | N | GLU | C | 180 | -68.210 | -4.226 | 12.646 | 1.00 | 41.08 |
| 13531 | CA | GLU | C | 180 | -67.698 | -5.399 | 11.957 | 1.00 | 41.75 |
| 13532 | CB | GLU | C | 180 | -68.853 | -6.198 | 11.366 | 1.00 | 41.10 |
| 13533 | CG | GLU | C | 180 | -69.966 | -6.475 | 12.351 | 1.00 | 41.62 |
| 13534 | CD | GLU | C | 180 | -69.577 | -7.514 | 13.391 | 1.00 | 41.25 |
| 13535 | OE1 | GLU | C | 180 | -68.369 | -7.684 | 13.650 | 1.00 | 41.50 |
| 13536 | OE2 | GLU | C | 180 | -70.482 | -8.167 | 13.937 | 1.00 | 41.06 |
| 13537 | C | GLU | C | 180 | -66.619 | -5.186 | 10.895 | 1.00 | 42.58 |
| 13538 | O | GLU | C | 180 | -65.956 | -6.142 | 10.476 | 1.00 | 43.00 |
| 13539 | N | VAL | C | 181 | -66.435 | -3.958 | 10.445 | 1.00 | 43.43 |
| 13540 | CA | VAL | C | 181 | -65.456 | -3.729 | 9.398 | 1.00 | 43.85 |
| 13541 | CB | VAL | C | 181 | -66.074 | -3.018 | 8.188 | 1.00 | 44.18 |
| 13542 | CG1 | VAL | C | 181 | -64.996 | -2.678 | 7.174 | 1.00 | 44.20 |
| 13543 | CG2 | VAL | C | 181 | -67.141 | -3.893 | 7.557 | 1.00 | 43.81 |
| 13544 | C | VAL | C | 181 | -64.269 | -2.943 | 9.898 | 1.00 | 44.14 |
| 13545 | O | VAL | C | 181 | -63.135 | -3.408 | 9.816 | 1.00 | 44.39 |
| 13546 | N | PHE | C | 182 | -64.519 | -1.755 | 10.433 | 1.00 | 44.37 |
| 13547 | CA | PHE | C | 182 | -63.422 | -0.908 | 10.887 | 1.00 | 44.60 |
| 13548 | CB | PHE | C | 182 | -63.721 | 0.567 | 10.595 | 1.00 | 44.50 |
| 13549 | CG | PHE | C | 182 | -63.745 | 0.919 | 9.124 | 1.00 | 45.31 |
| 13550 | CD1 | PHE | C | 182 | -63.304 | 0.026 | 8.165 | 1.00 | 45.26 |
| 13551 | CE1 | PHE | C | 182 | -63.321 | 0.356 | 6.829 | 1.00 | 45.23 |
| 13552 | CZ | PHE | C | 182 | -63.783 | 1.585 | 6.421 | 1.00 | 45.77 |
| 13553 | CE2 | PHE | C | 182 | -64.227 | 2.489 | 7.358 | 1.00 | 45.85 |
| 13554 | CD2 | PHE | C | 182 | -64.200 | 2.157 | 8.707 | 1.00 | 45.64 |
| 13555 | C | PHE | C | 182 | -63.093 | -1.057 | 12.379 | 1.00 | 45.09 |
| 13556 | O | PHE | C | 182 | -62.014 | -0.636 | 12.820 | 1.00 | 45.26 |

FIGURE 3 JF

| A | B | C | D | E | F | G | H | I | J |
|---|---|---|---|---|---|---|---|---|---|
| 13557 | N | SER | C | 183 | -64.010 | -1.629 | 13.162 | 1.00 | 44.85 |
| 13558 | CA | SER | C | 183 | -63.802 | -1.710 | 14.602 | 1.00 | 44.77 |
| 13559 | CB | SER | C | 183 | -62.708 | -2.716 | 14.966 | 1.00 | 44.65 |
| 13560 | OG | SER | C | 183 | -63.239 | -4.027 | 15.116 | 1.00 | 44.40 |
| 13561 | C | SER | C | 183 | -63.430 | -0.338 | 15.129 | 1.00 | 44.82 |
| 13562 | O | SER | C | 183 | -62.626 | -0.206 | 16.043 | 1.00 | 45.17 |
| 13563 | N | ALA | C | 184 | -64.012 | 0.690 | 14.541 | 1.00 | 45.06 |
| 13564 | CA | ALA | C | 184 | -63.747 | 2.049 | 14.981 | 1.00 | 45.29 |
| 13565 | CB | ALA | C | 184 | -62.417 | 2.538 | 14.442 | 1.00 | 45.24 |
| 13566 | C | ALA | C | 184 | -64.866 | 2.912 | 14.458 | 1.00 | 45.50 |
| 13567 | O | ALA | C | 184 | -65.577 | 2.504 | 13.544 | 1.00 | 44.92 |
| 13568 | N | TYR | C | 185 | -65.025 | 4.095 | 15.050 | 1.00 | 45.78 |
| 13569 | CA | TYR | C | 185 | -66.040 | 5.035 | 14.623 | 1.00 | 45.98 |
| 13570 | CB | TYR | C | 185 | -66.378 | 5.986 | 15.762 | 1.00 | 45.75 |
| 13571 | CG | TYR | C | 185 | -67.643 | 6.790 | 15.544 | 1.00 | 44.28 |
| 13572 | CD1 | TYR | C | 185 | -67.828 | 8.011 | 16.175 | 1.00 | 43.24 |
| 13573 | CE1 | TYR | C | 185 | -68.987 | 8.731 | 15.997 | 1.00 | 42.97 |
| 13574 | CZ | TYR | C | 185 | -69.973 | 8.234 | 15.175 | 1.00 | 42.29 |
| 13575 | OH | TYR | C | 185 | -71.129 | 8.947 | 14.990 | 1.00 | 43.54 |
| 13576 | CE2 | TYR | C | 185 | -69.808 | 7.042 | 14.532 | 1.00 | 42.00 |
| 13577 | CD2 | TYR | C | 185 | -68.650 | 6.322 | 14.718 | 1.00 | 42.34 |
| 13578 | C | TYR | C | 185 | -65.482 | 5.853 | 13.487 | 1.00 | 46.74 |
| 13579 | O | TYR | C | 185 | -66.169 | 6.132 | 12.500 | 1.00 | 46.83 |
| 13580 | N | SER | C | 186 | -64.220 | 6.242 | 13.653 | 1.00 | 47.74 |
| 13581 | CA | SER | C | 186 | -63.517 | 7.088 | 12.700 | 1.00 | 48.47 |
| 13582 | CB | SER | C | 186 | -62.090 | 7.356 | 13.178 | 1.00 | 48.70 |
| 13583 | OG | SER | C | 186 | -61.384 | 8.148 | 12.229 | 1.00 | 49.39 |
| 13584 | C | SER | C | 186 | -63.458 | 6.498 | 11.311 | 1.00 | 48.68 |
| 13585 | O | SER | C | 186 | -63.246 | 5.304 | 11.143 | 1.00 | 49.06 |
| 13586 | N | ALA | C | 187 | -63.661 | 7.353 | 10.323 | 1.00 | 49.12 |
| 13587 | CA | ALA | C | 187 | -63.509 | 6.983 | 8.924 | 1.00 | 50.17 |
| 13588 | CB | ALA | C | 187 | -64.866 | 6.728 | 8.260 | 1.00 | 49.98 |
| 13589 | C | ALA | C | 187 | -62.778 | 8.141 | 8.255 | 1.00 | 50.51 |
| 13590 | O | ALA | C | 187 | -63.133 | 8.573 | 7.164 | 1.00 | 50.64 |
| 13591 | N | LEU | C | 188 | -61.764 | 8.644 | 8.955 | 1.00 | 51.24 |
| 13592 | CA | LEU | C | 188 | -60.936 | 9.746 | 8.491 | 1.00 | 51.93 |
| 13593 | CB | LEU | C | 188 | -61.135 | 10.969 | 9.376 | 1.00 | 51.74 |
| 13594 | CG | LEU | C | 188 | -62.347 | 11.804 | 9.026 | 1.00 | 51.76 |
| 13595 | CD1 | LEU | C | 188 | -62.507 | 12.930 | 10.028 | 1.00 | 52.13 |
| 13596 | CD2 | LEU | C | 188 | -62.173 | 12.337 | 7.622 | 1.00 | 52.08 |
| 13597 | C | LEU | C | 188 | -59.482 | 9.331 | 8.573 | 1.00 | 52.48 |
| 13598 | O | LEU | C | 188 | -59.059 | 8.751 | 9.570 | 1.00 | 52.33 |
| 13599 | N | TRP | C | 189 | -58.719 | 9.639 | 7.528 | 1.00 | 53.20 |
| 13600 | CA | TRP | C | 189 | -57.304 | 9.285 | 7.481 | 1.00 | 53.81 |
| 13601 | CB | TRP | C | 189 | -57.094 | 8.045 | 6.615 | 1.00 | 53.83 |
| 13602 | CG | TRP | C | 189 | -57.881 | 6.857 | 7.072 | 1.00 | 54.47 |
| 13603 | CD1 | TRP | C | 189 | -57.503 | 5.930 | 8.004 | 1.00 | 54.57 |
| 13604 | NE1 | TRP | C | 189 | -58.490 | 4.986 | 8.159 | 1.00 | 53.87 |
| 13605 | CE2 | TRP | C | 189 | -59.531 | 5.292 | 7.326 | 1.00 | 54.72 |
| 13606 | CD2 | TRP | C | 189 | -59.182 | 6.468 | 6.629 | 1.00 | 54.66 |
| 13607 | CE3 | TRP | C | 189 | -60.092 | 6.988 | 5.702 | 1.00 | 55.32 |

FIGURE 3 JG

| A | B | C | D | E | F | G | H | I | J |
|---|---|---|---|---|---|---|---|---|---|
| 13608 | CZ3 | TRP | C | 189 | -61.297 | 6.330 | 5.504 | 1.00 | 54.99 |
| 13609 | CH2 | TRP | C | 189 | -61.613 | 5.168 | 6.213 | 1.00 | 54.89 |
| 13610 | CZ2 | TRP | C | 189 | -60.748 | 4.634 | 7.128 | 1.00 | 55.32 |
| 13611 | C | TRP | C | 189 | -56.453 | 10.440 | 6.952 | 1.00 | 54.18 |
| 13612 | O | TRP | C | 189 | -56.533 | 10.799 | 5.775 | 1.00 | 53.89 |
| 13613 | N | TRP | C | 190 | -55.660 | 11.031 | 7.841 | 1.00 | 54.56 |
| 13614 | CA | TRP | C | 190 | -54.733 | 12.091 | 7.479 | 1.00 | 54.79 |
| 13615 | CB | TRP | C | 190 | -54.220 | 12.786 | 8.730 | 1.00 | 54.74 |
| 13616 | CG | TRP | C | 190 | -55.093 | 13.804 | 9.370 | 1.00 | 54.58 |
| 13617 | CD1 | TRP | C | 190 | -55.765 | 13.672 | 10.547 | 1.00 | 54.42 |
| 13618 | NE1 | TRP | C | 190 | -56.433 | 14.834 | 10.845 | 1.00 | 53.90 |
| 13619 | CE2 | TRP | C | 190 | -56.184 | 15.752 | 9.861 | 1.00 | 53.77 |
| 13620 | CD2 | TRP | C | 190 | -55.332 | 15.139 | 8.921 | 1.00 | 53.97 |
| 13621 | CE3 | TRP | C | 190 | -54.923 | 15.879 | 7.809 | 1.00 | 54.28 |
| 13622 | CZ3 | TRP | C | 190 | -55.374 | 17.181 | 7.672 | 1.00 | 54.18 |
| 13623 | CH2 | TRP | C | 190 | -56.215 | 17.763 | 8.628 | 1.00 | 54.05 |
| 13624 | CZ2 | TRP | C | 190 | -56.627 | 17.067 | 9.729 | 1.00 | 53.74 |
| 13625 | C | TRP | C | 190 | -53.514 | 11.461 | 6.835 | 1.00 | 55.15 |
| 13626 | O | TRP | C | 190 | -53.066 | 10.405 | 7.266 | 1.00 | 55.18 |
| 13627 | N | SER | C | 191 | -52.961 | 12.113 | 5.819 | 1.00 | 55.91 |
| 13628 | CA | SER | C | 191 | -51.713 | 11.653 | 5.221 | 1.00 | 56.59 |
| 13629 | CB | SER | C | 191 | -51.420 | 12.415 | 3.926 | 1.00 | 56.56 |
| 13630 | OG | SER | C | 191 | -51.541 | 13.816 | 4.111 | 1.00 | 56.03 |
| 13631 | C | SER | C | 191 | -50.593 | 11.893 | 6.234 | 1.00 | 57.42 |
| 13632 | O | SER | C | 191 | -50.714 | 12.750 | 7.118 | 1.00 | 56.98 |
| 13633 | N | PRO | C | 192 | -49.512 | 11.133 | 6.110 | 1.00 | 58.15 |
| 13634 | CA | PRO | C | 192 | -48.376 | 11.246 | 7.026 | 1.00 | 59.14 |
| 13635 | CB | PRO | C | 192 | -47.262 | 10.537 | 6.268 | 1.00 | 59.27 |
| 13636 | CG | PRO | C | 192 | -47.978 | 9.502 | 5.455 | 1.00 | 58.36 |
| 13637 | CD | PRO | C | 192 | -49.300 | 10.101 | 5.082 | 1.00 | 58.19 |
| 13638 | C | PRO | C | 192 | -48.002 | 12.701 | 7.273 | 1.00 | 60.19 |
| 13639 | O | PRO | C | 192 | -47.788 | 13.104 | 8.415 | 1.00 | 60.18 |
| 13640 | N | ASN | C | 193 | -47.952 | 13.480 | 6.198 | 1.00 | 61.32 |
| 13641 | CA | ASN | C | 193 | -47.593 | 14.889 | 6.272 | 1.00 | 62.17 |
| 13642 | CB | ASN | C | 193 | -47.418 | 15.438 | 4.862 | 1.00 | 62.99 |
| 13643 | CG | ASN | C | 193 | -46.484 | 16.616 | 4.810 | 1.00 | 65.90 |
| 13644 | OD1 | ASN | C | 193 | -46.803 | 17.693 | 5.313 | 1.00 | 68.50 |
| 13645 | ND2 | ASN | C | 193 | -45.318 | 16.425 | 4.192 | 1.00 | 72.02 |
| 13646 | C | ASN | C | 193 | -48.633 | 15.733 | 6.972 | 1.00 | 61.82 |
| 13647 | O | ASN | C | 193 | -48.300 | 16.679 | 7.675 | 1.00 | 61.97 |
| 13648 | N | GLY | C | 194 | -49.901 | 15.407 | 6.751 | 1.00 | 61.60 |
| 13649 | CA | GLY | C | 194 | -50.994 | 16.172 | 7.315 | 1.00 | 60.80 |
| 13650 | C | GLY | C | 194 | -51.556 | 17.052 | 6.222 | 1.00 | 60.44 |
| 13651 | O | GLY | C | 194 | -52.471 | 17.853 | 6.434 | 1.00 | 60.77 |
| 13652 | N | THR | C | 195 | -50.996 | 16.899 | 5.032 | 1.00 | 59.75 |
| 13653 | CA | THR | C | 195 | -51.421 | 17.694 | 3.897 | 1.00 | 58.98 |
| 13654 | CB | THR | C | 195 | -50.386 | 17.572 | 2.761 | 1.00 | 59.11 |
| 13655 | OG1 | THR | C | 195 | -49.064 | 17.669 | 3.310 | 1.00 | 59.07 |
| 13656 | CG2 | THR | C | 195 | -50.474 | 18.769 | 1.825 | 1.00 | 59.07 |
| 13657 | C | THR | C | 195 | -52.790 | 17.214 | 3.434 | 1.00 | 58.49 |
| 13658 | O | THR | C | 195 | -53.727 | 18.007 | 3.310 | 1.00 | 58.20 |

FIGURE 3 JH

| A | B | C | D | E | F | G | H | I | J |
|---|---|---|---|---|---|---|---|---|---|
| 13659 | N | PHE | C | 196 | -52.900 | 15.907 | 3.201 | 1.00 | 57.69 |
| 13660 | CA | PHE | C | 196 | -54.143 | 15.308 | 2.719 | 1.00 | 57.12 |
| 13661 | CB | PHE | C | 196 | -53.843 | 14.217 | 1.691 | 1.00 | 57.33 |
| 13662 | CG | PHE | C | 196 | -53.296 | 14.739 | 0.402 | 1.00 | 58.36 |
| 13663 | CD1 | PHE | C | 196 | -54.017 | 15.660 | -0.347 | 1.00 | 59.58 |
| 13664 | CE1 | PHE | C | 196 | -53.517 | 16.147 | -1.542 | 1.00 | 59.97 |
| 13665 | CZ | PHE | C | 196 | -52.281 | 15.722 | -1.991 | 1.00 | 59.29 |
| 13666 | CE2 | PHE | C | 196 | -51.550 | 14.813 | -1.249 | 1.00 | 58.84 |
| 13667 | CD2 | PHE | C | 196 | -52.059 | 14.322 | -0.061 | 1.00 | 58.77 |
| 13668 | C | PHE | C | 196 | -55.040 | 14.725 | 3.813 | 1.00 | 56.35 |
| 13669 | O | PHE | C | 196 | -54.570 | 14.126 | 4.787 | 1.00 | 56.19 |
| 13670 | N | LEU | C | 197 | -56.340 | 14.908 | 3.633 | 1.00 | 55.17 |
| 13671 | CA | LEU | C | 197 | -57.329 | 14.338 | 4.528 | 1.00 | 54.16 |
| 13672 | CB | LEU | C | 197 | -58.172 | 15.424 | 5.178 | 1.00 | 54.23 |
| 13673 | CG | LEU | C | 197 | -59.355 | 14.877 | 5.971 | 1.00 | 54.29 |
| 13674 | CD1 | LEU | C | 197 | -60.191 | 16.016 | 6.550 | 1.00 | 54.27 |
| 13675 | CD2 | LEU | C | 197 | -58.862 | 13.939 | 7.058 | 1.00 | 53.50 |
| 13676 | C | LEU | C | 197 | -58.229 | 13.417 | 3.729 | 1.00 | 53.33 |
| 13677 | O | LEU | C | 197 | -58.955 | 13.865 | 2.844 | 1.00 | 52.98 |
| 13678 | N | ALA | C | 198 | -58.169 | 12.131 | 4.044 | 1.00 | 52.27 |
| 13679 | CA | ALA | C | 198 | -58.999 | 11.133 | 3.385 | 1.00 | 51.25 |
| 13680 | CB | ALA | C | 198 | -58.167 | 9.921 | 3.006 | 1.00 | 51.09 |
| 13681 | C | ALA | C | 198 | -60.143 | 10.707 | 4.296 | 1.00 | 50.59 |
| 13682 | O | ALA | C | 198 | -59.993 | 10.636 | 5.513 | 1.00 | 50.77 |
| 13683 | N | TYR | C | 199 | -61.287 | 10.408 | 3.697 | 1.00 | 49.68 |
| 13684 | CA | TYR | C | 199 | -62.434 | 9.951 | 4.450 | 1.00 | 48.67 |
| 13685 | CB | TYR | C | 199 | -63.223 | 11.136 | 4.986 | 1.00 | 48.41 |
| 13686 | CG | TYR | C | 199 | -63.804 | 12.031 | 3.915 | 1.00 | 48.64 |
| 13687 | CD1 | TYR | C | 199 | -65.078 | 11.804 | 3.410 | 1.00 | 48.03 |
| 13688 | CE1 | TYR | C | 199 | -65.617 | 12.625 | 2.436 | 1.00 | 48.60 |
| 13689 | CZ | TYR | C | 199 | -64.884 | 13.692 | 1.957 | 1.00 | 48.61 |
| 13690 | OH | TYR | C | 199 | -65.418 | 14.514 | 0.990 | 1.00 | 49.11 |
| 13691 | CE2 | TYR | C | 199 | -63.618 | 13.948 | 2.445 | 1.00 | 47.99 |
| 13692 | CD2 | TYR | C | 199 | -63.083 | 13.117 | 3.414 | 1.00 | 48.38 |
| 13693 | C | TYR | C | 199 | -63.347 | 9.104 | 3.586 | 1.00 | 48.19 |
| 13694 | O | TYR | C | 199 | -63.399 | 9.266 | 2.366 | 1.00 | 47.72 |
| 13695 | N | ALA | C | 200 | -64.072 | 8.200 | 4.233 | 1.00 | 47.53 |
| 13696 | CA | ALA | C | 200 | -65.050 | 7.391 | 3.528 | 1.00 | 46.94 |
| 13697 | CB | ALA | C | 200 | -65.052 | 5.972 | 4.064 | 1.00 | 46.49 |
| 13698 | C | ALA | C | 200 | -66.412 | 8.041 | 3.713 | 1.00 | 46.41 |
| 13699 | O | ALA | C | 200 | -66.598 | 8.876 | 4.594 | 1.00 | 46.78 |
| 13700 | N | GLN | C | 201 | -67.356 | 7.685 | 2.862 | 1.00 | 45.99 |
| 13701 | CA | GLN | C | 201 | -68.718 | 8.167 | 3.005 | 1.00 | 45.83 |
| 13702 | CB | GLN | C | 201 | -69.100 | 9.126 | 1.879 | 1.00 | 46.18 |
| 13703 | CG | GLN | C | 201 | -70.533 | 9.627 | 1.991 | 1.00 | 47.72 |
| 13704 | CD | GLN | C | 201 | -70.782 | 10.903 | 1.214 | 1.00 | 49.96 |
| 13705 | OE1 | GLN | C | 201 | -71.164 | 10.859 | 0.048 | 1.00 | 50.58 |
| 13706 | NE2 | GLN | C | 201 | -70.579 | 12.042 | 1.861 | 1.00 | 51.42 |
| 13707 | C | GLN | C | 201 | -69.640 | 6.958 | 3.015 | 1.00 | 45.21 |
| 13708 | O | GLN | C | 201 | -69.473 | 6.025 | 2.220 | 1.00 | 45.15 |
| 13709 | N | PHE | C | 202 | -70.595 | 6.946 | 3.936 | 1.00 | 44.23 |

FIGURE 3 JI

| A | B | C | D | E | F | G | H | I | J |
|---|---|---|---|---|---|---|---|---|---|
| 13710 | CA | PHE | C | 202 | -71.488 | 5.800 | 4.021 | 1.00 | 43.33 |
| 13711 | CB | PHE | C | 202 | -71.336 | 5.064 | 5.352 | 1.00 | 42.94 |
| 13712 | CG | PHE | C | 202 | -69.931 | 4.660 | 5.658 | 1.00 | 41.85 |
| 13713 | CD1 | PHE | C | 202 | -69.400 | 3.496 | 5.127 | 1.00 | 40.26 |
| 13714 | CE1 | PHE | C | 202 | -68.094 | 3.117 | 5.404 | 1.00 | 38.51 |
| 13715 | CZ | PHE | C | 202 | -67.306 | 3.906 | 6.219 | 1.00 | 39.69 |
| 13716 | CE2 | PHE | C | 202 | -67.823 | 5.076 | 6.756 | 1.00 | 40.28 |
| 13717 | CD2 | PHE | C | 202 | -69.132 | 5.446 | 6.480 | 1.00 | 40.55 |
| 13718 | C | PHE | C | 202 | -72.915 | 6.226 | 3.807 | 1.00 | 43.20 |
| 13719 | O | PHE | C | 202 | -73.340 | 7.277 | 4.287 | 1.00 | 43.16 |
| 13720 | N | ASN | C | 203 | -73.650 | 5.406 | 3.072 | 1.00 | 42.90 |
| 13721 | CA | ASN | C | 203 | -75.030 | 5.709 | 2.782 | 1.00 | 43.29 |
| 13722 | CB | ASN | C | 203 | -75.214 | 5.928 | 1.292 | 1.00 | 43.65 |
| 13723 | CG | ASN | C | 203 | -76.412 | 6.778 | 0.984 | 1.00 | 44.58 |
| 13724 | OD1 | ASN | C | 203 | -77.425 | 6.734 | 1.686 | 1.00 | 43.23 |
| 13725 | ND2 | ASN | C | 203 | -76.298 | 7.588 | -0.059 | 1.00 | 47.95 |
| 13726 | C | ASN | C | 203 | -75.914 | 4.578 | 3.224 | 1.00 | 43.26 |
| 13727 | O | ASN | C | 203 | -75.774 | 3.463 | 2.743 | 1.00 | 43.22 |
| 13728 | N | ASP | C | 204 | -76.847 | 4.876 | 4.119 | 1.00 | 43.47 |
| 13729 | CA | ASP | C | 204 | -77.716 | 3.852 | 4.694 | 1.00 | 43.66 |
| 13730 | CB | ASP | C | 204 | -77.613 | 3.891 | 6.216 | 1.00 | 43.84 |
| 13731 | CG | ASP | C | 204 | -76.289 | 3.374 | 6.707 | 1.00 | 44.94 |
| 13732 | OD1 | ASP | C | 204 | -75.256 | 3.827 | 6.172 | 1.00 | 45.47 |
| 13733 | OD2 | ASP | C | 204 | -76.182 | 2.503 | 7.598 | 1.00 | 46.16 |
| 13734 | C | ASP | C | 204 | -79.164 | 4.018 | 4.301 | 1.00 | 43.16 |
| 13735 | O | ASP | C | 204 | -80.031 | 3.315 | 4.814 | 1.00 | 43.63 |
| 13736 | N | THR | C | 205 | -79.415 | 4.947 | 3.391 | 1.00 | 42.34 |
| 13737 | CA | THR | C | 205 | -80.767 | 5.257 | 2.933 | 1.00 | 42.11 |
| 13738 | CB | THR | C | 205 | -80.713 | 5.917 | 1.544 | 1.00 | 42.01 |
| 13739 | OG1 | THR | C | 205 | -80.207 | 7.253 | 1.668 | 1.00 | 42.98 |
| 13740 | CG2 | THR | C | 205 | -82.117 | 6.131 | 1.002 | 1.00 | 41.81 |
| 13741 | C | THR | C | 205 | -81.734 | 4.072 | 2.887 | 1.00 | 41.53 |
| 13742 | O | THR | C | 205 | -82.896 | 4.187 | 3.303 | 1.00 | 41.51 |
| 13743 | N | GLU | C | 206 | -81.260 | 2.939 | 2.388 | 1.00 | 40.50 |
| 13744 | CA | GLU | C | 206 | -82.146 | 1.797 | 2.234 | 1.00 | 40.04 |
| 13745 | CB | GLU | C | 206 | -82.134 | 1.324 | 0.774 | 1.00 | 40.07 |
| 13746 | CG | GLU | C | 206 | -82.438 | 2.480 | -0.172 | 1.00 | 41.65 |
| 13747 | CD | GLU | C | 206 | -82.268 | 2.161 | -1.646 | 1.00 | 44.80 |
| 13748 | OE1 | GLU | C | 206 | -83.236 | 2.363 | -2.414 | 1.00 | 46.76 |
| 13749 | OE2 | GLU | C | 206 | -81.166 | 1.743 | -2.054 | 1.00 | 46.59 |
| 13750 | C | GLU | C | 206 | -81.891 | 0.645 | 3.224 | 1.00 | 38.87 |
| 13751 | O | GLU | C | 206 | -82.511 | -0.420 | 3.133 | 1.00 | 37.95 |
| 13752 | N | VAL | C | 207 | -80.976 | 0.863 | 4.165 | 1.00 | 37.68 |
| 13753 | CA | VAL | C | 207 | -80.731 | -0.138 | 5.205 | 1.00 | 36.62 |
| 13754 | CB | VAL | C | 207 | -79.429 | 0.141 | 5.967 | 1.00 | 36.79 |
| 13755 | CG1 | VAL | C | 207 | -79.170 | -0.944 | 7.031 | 1.00 | 36.88 |
| 13756 | CG2 | VAL | C | 207 | -78.272 | 0.251 | 5.003 | 1.00 | 36.84 |
| 13757 | C | VAL | C | 207 | -81.882 | -0.074 | 6.193 | 1.00 | 35.27 |
| 13758 | O | VAL | C | 207 | -82.170 | 0.986 | 6.724 | 1.00 | 35.26 |
| 13759 | N | PRO | C | 208 | -82.565 | -1.193 | 6.406 | 1.00 | 34.54 |
| 13760 | CA | PRO | C | 208 | -83.661 | -1.253 | 7.386 | 1.00 | 34.29 |

FIGURE 3 JJ

| A | B | C | D | E | F | G | H | I | J |
|---|---|---|---|---|---|---|---|---|---|
| 13761 | CB | PRO | C | 208 | -84.179 | -2.684 | 7.259 | 1.00 | 34.13 |
| 13762 | CG | PRO | C | 208 | -83.709 | -3.132 | 5.895 | 1.00 | 34.34 |
| 13763 | CD | PRO | C | 208 | -82.366 | -2.475 | 5.708 | 1.00 | 33.97 |
| 13764 | C | PRO | C | 208 | -83.203 | -0.978 | 8.813 | 1.00 | 33.90 |
| 13765 | O | PRO | C | 208 | -82.027 | -1.118 | 9.157 | 1.00 | 34.41 |
| 13766 | N | LEU | C | 209 | -84.145 | -0.574 | 9.648 | 1.00 | 33.81 |
| 13767 | CA | LEU | C | 209 | -83.820 | -0.198 | 11.005 | 1.00 | 33.49 |
| 13768 | CB | LEU | C | 209 | -84.518 | 1.112 | 11.347 | 1.00 | 33.96 |
| 13769 | CG | LEU | C | 209 | -84.559 | 2.182 | 10.248 | 1.00 | 35.02 |
| 13770 | CD1 | LEU | C | 209 | -83.316 | 3.015 | 10.268 | 1.00 | 34.09 |
| 13771 | CD2 | LEU | C | 209 | -85.796 | 3.058 | 10.413 | 1.00 | 36.67 |
| 13772 | C | LEU | C | 209 | -84.240 | -1.254 | 11.999 | 1.00 | 33.03 |
| 13773 | O | LEU | C | 209 | -85.336 | -1.812 | 11.901 | 1.00 | 33.09 |
| 13774 | N | ILE | C | 210 | -83.355 | -1.569 | 12.939 | 1.00 | 32.05 |
| 13775 | CA | ILE | C | 210 | -83.777 | -2.428 | 14.038 | 1.00 | 31.09 |
| 13776 | CB | ILE | C | 210 | -82.587 | -3.139 | 14.735 | 1.00 | 30.96 |
| 13777 | CG1 | ILE | C | 210 | -83.083 | -3.992 | 15.904 | 1.00 | 29.69 |
| 13778 | CD1 | ILE | C | 210 | -84.158 | -4.994 | 15.566 | 1.00 | 28.62 |
| 13779 | CG2 | ILE | C | 210 | -81.570 | -2.128 | 15.243 | 1.00 | 30.43 |
| 13780 | C | ILE | C | 210 | -84.488 | -1.464 | 14.968 | 1.00 | 29.87 |
| 13781 | O | ILE | C | 210 | -84.049 | -0.341 | 15.128 | 1.00 | 29.51 |
| 13781 | O | ILE | C | 248 | -84.049 | -0.341 | 15.128 | 1.00 | 29.51 |
| 13782 | N | GLU | C | 249 | -85.609 | -1.884 | 15.531 | 1.00 | 29.61 |
| 13783 | CA | GLU | C | 249 | -86.387 | -1.015 | 16.414 | 1.00 | 29.40 |
| 13784 | CB | GLU | C | 249 | -87.755 | -0.709 | 15.798 | 1.00 | 29.74 |
| 13785 | CG | GLU | C | 249 | -87.698 | -0.227 | 14.343 | 1.00 | 31.91 |
| 13786 | CD | GLU | C | 249 | -88.879 | 0.642 | 13.947 | 1.00 | 34.50 |
| 13787 | OE1 | GLU | C | 249 | -88.669 | 1.699 | 13.324 | 1.00 | 36.73 |
| 13788 | OE2 | GLU | C | 249 | -90.026 | 0.266 | 14.234 | 1.00 | 36.55 |
| 13789 | C | GLU | C | 249 | -86.568 | -1.727 | 17.740 | 1.00 | 29.26 |
| 13790 | O | GLU | C | 249 | -86.836 | -2.916 | 17.762 | 1.00 | 29.47 |
| 13791 | N | TYR | C | 250 | -86.373 | -1.014 | 18.847 | 1.00 | 28.74 |
| 13792 | CA | TYR | C | 250 | -86.548 | -1.604 | 20.163 | 1.00 | 27.93 |
| 13793 | CB | TYR | C | 250 | -85.322 | -2.427 | 20.596 | 1.00 | 27.74 |
| 13794 | CG | TYR | C | 250 | -83.982 | -1.700 | 20.561 | 1.00 | 28.43 |
| 13795 | CD1 | TYR | C | 250 | -83.541 | -0.972 | 21.648 | 1.00 | 29.03 |
| 13796 | CE1 | TYR | C | 250 | -82.337 | -0.318 | 21.633 | 1.00 | 28.97 |
| 13797 | CZ | TYR | C | 250 | -81.525 | -0.380 | 20.528 | 1.00 | 28.02 |
| 13798 | OH | TYR | C | 250 | -80.316 | 0.283 | 20.565 | 1.00 | 26.76 |
| 13799 | CE2 | TYR | C | 250 | -81.912 | -1.109 | 19.430 | 1.00 | 26.95 |
| 13800 | CD2 | TYR | C | 250 | -83.148 | -1.769 | 19.449 | 1.00 | 28.64 |
| 13801 | C | TYR | C | 250 | -86.877 | -0.530 | 21.185 | 1.00 | 27.25 |
| 13802 | O | TYR | C | 250 | -86.524 | 0.623 | 21.013 | 1.00 | 27.62 |
| 13803 | N | SER | C | 251 | -87.586 | -0.906 | 22.239 | 1.00 | 26.40 |
| 13804 | CA | SER | C | 251 | -87.924 | 0.050 | 23.255 | 1.00 | 25.34 |
| 13805 | CB | SER | C | 251 | -88.994 | -0.495 | 24.182 | 1.00 | 25.35 |
| 13806 | OG | SER | C | 251 | -90.180 | -0.736 | 23.464 | 1.00 | 25.27 |
| 13807 | C | SER | C | 251 | -86.726 | 0.418 | 24.075 | 1.00 | 24.88 |
| 13808 | O | SER | C | 251 | -85.792 | -0.381 | 24.268 | 1.00 | 25.16 |
| 13809 | N | PHE | C | 252 | -86.731 | 1.660 | 24.528 | 1.00 | 23.79 |
| 13810 | CA | PHE | C | 252 | -85.758 | 2.089 | 25.489 | 1.00 | 23.02 |
| 13811 | CB | PHE | C | 252 | -84.758 | 3.070 | 24.904 | 1.00 | 21.59 |

FIGURE 3 JK

| A | B | C | D | E | F | G | H | I | J |
|---|---|---|---|---|---|---|---|---|---|
| 13812 | CG | PHE | C | 214 | -83.581 | 3.303 | 25.797 | 1.00 | 22.14 |
| 13813 | CD1 | PHE | C | 214 | -83.545 | 4.395 | 26.643 | 1.00 | 20.47 |
| 13814 | CE1 | PHE | C | 214 | -82.474 | 4.602 | 27.495 | 1.00 | 21.26 |
| 13815 | CZ | PHE | C | 214 | -81.416 | 3.713 | 27.509 | 1.00 | 21.13 |
| 13816 | CE2 | PHE | C | 214 | -81.451 | 2.599 | 26.684 | 1.00 | 22.44 |
| 13817 | CD2 | PHE | C | 214 | -82.527 | 2.393 | 25.835 | 1.00 | 21.49 |
| 13818 | C | PHE | C | 214 | -86.610 | 2.728 | 26.563 | 1.00 | 23.30 |
| 13819 | O | PHE | C | 214 | -87.362 | 3.663 | 26.302 | 1.00 | 23.83 |
| 13820 | N | TYR | C | 215 | -86.491 | 2.237 | 27.780 | 1.00 | 23.67 |
| 13821 | CA | TYR | C | 215 | -87.366 | 2.694 | 28.839 | 1.00 | 23.72 |
| 13822 | CB | TYR | C | 215 | -87.613 | 1.520 | 29.770 | 1.00 | 23.53 |
| 13823 | CG | TYR | C | 215 | -88.190 | 0.383 | 28.997 | 1.00 | 22.91 |
| 13824 | CD1 | TYR | C | 215 | -87.384 | -0.632 | 28.505 | 1.00 | 21.36 |
| 13825 | CE1 | TYR | C | 215 | -87.929 | -1.668 | 27.768 | 1.00 | 21.11 |
| 13826 | CZ | TYR | C | 215 | -89.287 | -1.690 | 27.518 | 1.00 | 22.99 |
| 13827 | OH | TYR | C | 215 | -89.842 | -2.706 | 26.779 | 1.00 | 26.40 |
| 13828 | CE2 | TYR | C | 215 | -90.099 | -0.697 | 27.972 | 1.00 | 21.80 |
| 13829 | CD2 | TYR | C | 215 | -89.553 | 0.346 | 28.703 | 1.00 | 23.70 |
| 13830 | C | TYR | C | 215 | -86.891 | 3.927 | 29.591 | 1.00 | 24.24 |
| 13831 | O | TYR | C | 215 | -87.703 | 4.683 | 30.109 | 1.00 | 24.59 |
| 13832 | N | SER | C | 216 | -85.586 | 4.126 | 29.640 | 1.00 | 25.17 |
| 13833 | CA | SER | C | 216 | -84.986 | 5.301 | 30.267 | 1.00 | 26.77 |
| 13834 | CB | SER | C | 216 | -85.482 | 6.590 | 29.593 | 1.00 | 26.93 |
| 13835 | OG | SER | C | 216 | -84.636 | 7.712 | 29.858 | 1.00 | 25.11 |
| 13836 | C | SER | C | 216 | -85.253 | 5.358 | 31.761 | 1.00 | 28.05 |
| 13837 | O | SER | C | 216 | -85.719 | 4.371 | 32.378 | 1.00 | 28.16 |
| 13838 | N | ASP | C | 217 | -84.952 | 6.513 | 32.338 | 1.00 | 28.88 |
| 13839 | CA | ASP | C | 217 | -85.229 | 6.764 | 33.741 | 1.00 | 30.64 |
| 13840 | CB | ASP | C | 217 | -84.914 | 8.209 | 34.133 | 1.00 | 31.51 |
| 13841 | CG | ASP | C | 217 | -83.512 | 8.379 | 34.648 | 1.00 | 37.46 |
| 13842 | OD1 | ASP | C | 217 | -83.233 | 7.952 | 35.810 | 1.00 | 41.26 |
| 13843 | OD2 | ASP | C | 217 | -82.618 | 8.931 | 33.953 | 1.00 | 43.60 |
| 13844 | C | ASP | C | 217 | -86.694 | 6.534 | 33.993 | 1.00 | 30.10 |
| 13845 | O | ASP | C | 217 | -87.520 | 6.621 | 33.088 | 1.00 | 30.15 |
| 13846 | N | GLU | C | 218 | -87.006 | 6.265 | 35.246 | 1.00 | 29.91 |
| 13847 | CA | GLU | C | 218 | -88.366 | 6.038 | 35.687 | 1.00 | 30.08 |
| 13848 | CB | GLU | C | 218 | -88.318 | 5.820 | 37.198 | 1.00 | 30.34 |
| 13849 | CG | GLU | C | 218 | -89.642 | 5.457 | 37.808 | 1.00 | 30.57 |
| 13850 | CD | GLU | C | 218 | -89.569 | 5.448 | 39.314 | 1.00 | 31.50 |
| 13851 | OE1 | GLU | C | 218 | -90.653 | 5.454 | 39.929 | 1.00 | 30.19 |
| 13852 | OE2 | GLU | C | 218 | -88.440 | 5.447 | 39.862 | 1.00 | 29.16 |
| 13853 | C | GLU | C | 218 | -89.301 | 7.221 | 35.337 | 1.00 | 30.15 |
| 13854 | O | GLU | C | 218 | -90.509 | 7.036 | 35.126 | 1.00 | 30.19 |
| 13855 | N | SER | C | 219 | -88.742 | 8.425 | 35.272 | 1.00 | 29.61 |
| 13856 | CA | SER | C | 219 | -89.499 | 9.629 | 34.911 | 1.00 | 30.11 |
| 13857 | CB | SER | C | 219 | -88.603 | 10.862 | 34.990 | 1.00 | 29.74 |
| 13858 | OG | SER | C | 219 | -88.685 | 11.435 | 36.276 | 1.00 | 34.17 |
| 13859 | C | SER | C | 219 | -90.098 | 9.629 | 33.513 | 1.00 | 29.25 |
| 13860 | O | SER | C | 219 | -91.072 | 10.316 | 33.273 | 1.00 | 29.39 |
| 13861 | N | LEU | C | 220 | -89.477 | 8.929 | 32.576 | 1.00 | 28.72 |
| 13862 | CA | LEU | C | 220 | -89.981 | 8.925 | 31.203 | 1.00 | 28.94 |

FIGURE 3 JL

| A | B | C | D | E | F | G | H | I | J |
|---|---|---|---|---|---|---|---|---|---|
| 13863 | CB | LEU | C | 220 | -88.996 | 8.217 | 30.286 | 1.00 | 28.81 |
| 13864 | CG | LEU | C | 220 | -88.787 | 8.724 | 28.853 | 1.00 | 30.91 |
| 13865 | CD1 | LEU | C | 220 | -88.739 | 7.557 | 27.884 | 1.00 | 28.91 |
| 13866 | CD2 | LEU | C | 220 | -89.816 | 9.778 | 28.417 | 1.00 | 30.79 |
| 13867 | C | LEU | C | 220 | -91.297 | 8.168 | 31.180 | 1.00 | 28.69 |
| 13868 | O | LEU | C | 220 | -91.309 | 6.955 | 31.379 | 1.00 | 28.71 |
| 13869 | N | GLN | C | 221 | -92.402 | 8.860 | 30.924 | 1.00 | 28.48 |
| 13870 | CA | GLN | C | 221 | -93.676 | 8.187 | 31.000 | 1.00 | 28.74 |
| 13871 | CB | GLN | C | 221 | -94.816 | 9.140 | 31.424 | 1.00 | 29.01 |
| 13872 | CG | GLN | C | 221 | -95.741 | 9.573 | 30.392 | 1.00 | 30.12 |
| 13873 | CD | GLN | C | 221 | -96.905 | 10.394 | 30.935 | 1.00 | 31.70 |
| 13874 | OE1 | GLN | C | 221 | -97.183 | 11.478 | 30.426 | 1.00 | 33.47 |
| 13875 | NE2 | GLN | C | 221 | -97.612 | 9.863 | 31.926 | 1.00 | 29.51 |
| 13876 | C | GLN | C | 221 | -93.999 | 7.275 | 29.823 | 1.00 | 28.55 |
| 13877 | O | GLN | C | 221 | -94.591 | 6.220 | 30.015 | 1.00 | 28.97 |
| 13878 | N | TYR | C | 222 | -93.611 | 7.666 | 28.613 | 1.00 | 28.68 |
| 13879 | CA | TYR | C | 222 | -93.738 | 6.792 | 27.448 | 1.00 | 27.87 |
| 13880 | CB | TYR | C | 222 | -94.384 | 7.540 | 26.292 | 1.00 | 27.58 |
| 13881 | CG | TYR | C | 222 | -95.873 | 7.788 | 26.422 | 1.00 | 25.09 |
| 13882 | CD1 | TYR | C | 222 | -96.792 | 6.896 | 25.875 | 1.00 | 23.08 |
| 13883 | CE1 | TYR | C | 222 | -98.141 | 7.116 | 25.976 | 1.00 | 22.99 |
| 13884 | CZ | TYR | C | 222 | -98.605 | 8.235 | 26.636 | 1.00 | 23.45 |
| 13885 | OH | TYR | C | 222 | -99.971 | 8.460 | 26.706 | 1.00 | 22.97 |
| 13886 | CE2 | TYR | C | 222 | -97.706 | 9.128 | 27.187 | 1.00 | 23.41 |
| 13887 | CD2 | TYR | C | 222 | -96.351 | 8.897 | 27.077 | 1.00 | 20.70 |
| 13888 | C | TYR | C | 222 | -92.332 | 6.389 | 27.028 | 1.00 | 28.24 |
| 13889 | O | TYR | C | 222 | -91.489 | 7.247 | 26.827 | 1.00 | 28.57 |
| 13890 | N | PRO | C | 223 | -92.071 | 5.099 | 26.884 | 1.00 | 28.60 |
| 13891 | CA | PRO | C | 223 | -90.749 | 4.635 | 26.448 | 1.00 | 29.15 |
| 13892 | CB | PRO | C | 223 | -90.902 | 3.112 | 26.380 | 1.00 | 28.83 |
| 13893 | CG | PRO | C | 223 | -92.158 | 2.790 | 27.107 | 1.00 | 29.05 |
| 13894 | CD | PRO | C | 223 | -93.020 | 3.994 | 27.098 | 1.00 | 28.79 |
| 13895 | C | PRO | C | 223 | -90.428 | 5.145 | 25.037 | 1.00 | 29.93 |
| 13896 | O | PRO | C | 223 | -91.359 | 5.358 | 24.232 | 1.00 | 29.83 |
| 13897 | N | LYS | C | 224 | -89.140 | 5.316 | 24.751 | 1.00 | 30.03 |
| 13898 | CA | LYS | C | 224 | -88.680 | 5.720 | 23.435 | 1.00 | 31.06 |
| 13899 | CB | LYS | C | 224 | -87.387 | 6.546 | 23.532 | 1.00 | 31.64 |
| 13900 | CG | LYS | C | 224 | -86.592 | 6.552 | 22.204 | 1.00 | 35.58 |
| 13901 | CD | LYS | C | 224 | -85.428 | 7.565 | 22.147 | 1.00 | 40.48 |
| 13902 | CE | LYS | C | 224 | -84.847 | 7.650 | 20.713 | 1.00 | 44.08 |
| 13903 | NZ | LYS | C | 224 | -83.356 | 7.924 | 20.640 | 1.00 | 45.90 |
| 13904 | C | LYS | C | 224 | -88.419 | 4.502 | 22.549 | 1.00 | 31.01 |
| 13905 | O | LYS | C | 224 | -88.009 | 3.440 | 23.032 | 1.00 | 30.81 |
| 13906 | N | THR | C | 225 | -88.669 | 4.651 | 21.253 | 1.00 | 30.57 |
| 13907 | CA | THR | C | 225 | -88.321 | 3.610 | 20.319 | 1.00 | 30.52 |
| 13908 | CB | THR | C | 225 | -89.414 | 3.434 | 19.277 | 1.00 | 30.58 |
| 13909 | OG1 | THR | C | 225 | -90.594 | 2.957 | 19.913 | 1.00 | 30.75 |
| 13910 | CG2 | THR | C | 225 | -89.071 | 2.285 | 18.342 | 1.00 | 31.23 |
| 13911 | C | THR | C | 225 | -86.999 | 3.984 | 19.646 | 1.00 | 30.64 |
| 13912 | O | THR | C | 225 | -86.906 | 4.988 | 18.937 | 1.00 | 29.95 |
| 13913 | N | VAL | C | 226 | -85.975 | 3.176 | 19.881 | 1.00 | 30.60 |

FIGURE 3 JM

| A | B | C | D | E | F | G | H | I | J |
|---|---|---|---|---|---|---|---|---|---|
| 13914 | CA | VAL | C | 226 | -84.683 | 3.400 | 19.251 | 1.00 | 30.79 |
| 13915 | CB | VAL | C | 226 | -83.556 | 2.748 | 20.065 | 1.00 | 30.79 |
| 13916 | CG1 | VAL | C | 226 | -82.233 | 2.876 | 19.354 | 1.00 | 30.14 |
| 13917 | CG2 | VAL | C | 226 | -83.464 | 3.369 | 21.450 | 1.00 | 30.56 |
| 13918 | C | VAL | C | 226 | -84.697 | 2.817 | 17.835 | 1.00 | 31.13 |
| 13919 | O | VAL | C | 226 | -85.176 | 1.709 | 17.616 | 1.00 | 30.73 |
| 13920 | N | ARG | C | 227 | -84.177 | 3.572 | 16.872 | 1.00 | 31.64 |
| 13921 | CA | ARG | C | 227 | -84.173 | 3.127 | 15.484 | 1.00 | 32.37 |
| 13922 | CB | ARG | C | 227 | -85.163 | 3.952 | 14.663 | 1.00 | 32.33 |
| 13923 | CG | ARG | C | 227 | -86.637 | 3.727 | 15.061 | 1.00 | 33.95 |
| 13924 | CD | ARG | C | 227 | -87.646 | 4.587 | 14.293 | 1.00 | 36.77 |
| 13925 | NE | ARG | C | 227 | -89.029 | 4.442 | 14.763 | 1.00 | 40.59 |
| 13926 | CZ | ARG | C | 227 | -89.528 | 5.000 | 15.878 | 1.00 | 43.38 |
| 13927 | NH1 | ARG | C | 227 | -88.759 | 5.732 | 16.683 | 1.00 | 43.86 |
| 13928 | NH2 | ARG | C | 227 | -90.804 | 4.817 | 16.199 | 1.00 | 43.10 |
| 13929 | C | ARG | C | 227 | -82.775 | 3.204 | 14.882 | 1.00 | 32.34 |
| 13930 | O | ARG | C | 227 | -82.188 | 4.279 | 14.761 | 1.00 | 32.84 |
| 13931 | N | VAL | C | 228 | -82.210 | 2.070 | 14.512 | 1.00 | 31.89 |
| 13932 | CA | VAL | C | 228 | -80.858 | 2.152 | 13.996 | 1.00 | 31.57 |
| 13933 | CB | VAL | C | 228 | -79.787 | 1.736 | 15.034 | 1.00 | 31.19 |
| 13934 | CG1 | VAL | C | 228 | -79.014 | 0.559 | 14.566 | 1.00 | 31.60 |
| 13935 | CG2 | VAL | C | 228 | -80.394 | 1.556 | 16.441 | 1.00 | 31.18 |
| 13936 | C | VAL | C | 228 | -80.703 | 1.364 | 12.723 | 1.00 | 31.43 |
| 13937 | O | VAL | C | 228 | -81.181 | 0.230 | 12.630 | 1.00 | 31.40 |
| 13938 | N | PRO | C | 229 | -80.090 | 2.004 | 11.731 | 1.00 | 31.15 |
| 13939 | CA | PRO | C | 229 | -79.833 | 1.383 | 10.439 | 1.00 | 31.51 |
| 13940 | CB | PRO | C | 229 | -79.116 | 2.490 | 9.645 | 1.00 | 31.83 |
| 13941 | CG | PRO | C | 229 | -79.540 | 3.747 | 10.291 | 1.00 | 31.61 |
| 13942 | CD | PRO | C | 229 | -79.613 | 3.395 | 11.775 | 1.00 | 31.91 |
| 13943 | C | PRO | C | 229 | -78.895 | 0.253 | 10.723 | 1.00 | 31.66 |
| 13944 | O | PRO | C | 229 | -77.752 | 0.492 | 11.119 | 1.00 | 31.94 |
| 13945 | N | TYR | C | 230 | -79.391 | -0.960 | 10.518 | 1.00 | 31.57 |
| 13946 | CA | TYR | C | 230 | -78.683 | -2.164 | 10.856 | 1.00 | 31.68 |
| 13947 | CB | TYR | C | 230 | -79.085 | -2.562 | 12.286 | 1.00 | 31.52 |
| 13948 | CG | TYR | C | 230 | -78.506 | -3.857 | 12.828 | 1.00 | 30.56 |
| 13949 | CD1 | TYR | C | 230 | -77.802 | -3.864 | 14.020 | 1.00 | 30.11 |
| 13950 | CE1 | TYR | C | 230 | -77.294 | -5.046 | 14.548 | 1.00 | 30.51 |
| 13951 | CZ | TYR | C | 230 | -77.497 | -6.236 | 13.890 | 1.00 | 28.91 |
| 13952 | OH | TYR | C | 230 | -76.971 | -7.391 | 14.434 | 1.00 | 27.93 |
| 13953 | CE2 | TYR | C | 230 | -78.200 | -6.262 | 12.697 | 1.00 | 28.65 |
| 13954 | CD2 | TYR | C | 230 | -78.698 | -5.075 | 12.175 | 1.00 | 29.51 |
| 13955 | C | TYR | C | 230 | -79.125 | -3.224 | 9.879 | 1.00 | 31.77 |
| 13956 | O | TYR | C | 230 | -80.296 | -3.560 | 9.827 | 1.00 | 32.09 |
| 13957 | N | PRO | C | 231 | -78.192 | -3.727 | 9.086 | 1.00 | 32.17 |
| 13958 | CA | PRO | C | 231 | -78.488 | -4.767 | 8.097 | 1.00 | 32.64 |
| 13959 | CB | PRO | C | 231 | -77.405 | -4.565 | 7.030 | 1.00 | 32.47 |
| 13960 | CG | PRO | C | 231 | -76.395 | -3.609 | 7.636 | 1.00 | 32.79 |
| 13961 | CD | PRO | C | 231 | -76.791 | -3.289 | 9.043 | 1.00 | 32.22 |
| 13962 | C | PRO | C | 231 | -78.354 | -6.169 | 8.654 | 1.00 | 32.90 |
| 13963 | O | PRO | C | 231 | -77.261 | -6.626 | 8.996 | 1.00 | 32.61 |
| 13964 | N | LYS | C | 232 | -79.469 | -6.863 | 8.731 | 1.00 | 33.36 |

FIGURE 3 JN

| A | B | C | D | E | F | G | H | I | J |
|---|---|---|---|---|---|---|---|---|---|
| 13965 | CA | LYS | C | 232 | -79.428 | -8.228 | 9.165 | 1.00 | 34.36 |
| 13966 | CB | LYS | C | 232 | -80.804 | -8.664 | 9.664 | 1.00 | 34.43 |
| 13967 | CG | LYS | C | 232 | -81.156 | -8.056 | 11.023 | 1.00 | 34.61 |
| 13968 | CD | LYS | C | 232 | -82.582 | -8.402 | 11.485 | 1.00 | 34.22 |
| 13969 | CE | LYS | C | 232 | -82.888 | -7.773 | 12.872 | 1.00 | 34.56 |
| 13970 | NZ | LYS | C | 232 | -82.178 | -8.420 | 14.033 | 1.00 | 30.83 |
| 13971 | C | LYS | C | 232 | -78.971 | -9.004 | 7.949 | 1.00 | 35.12 |
| 13972 | O | LYS | C | 232 | -78.910 | -8.453 | 6.855 | 1.00 | 35.75 |
| 13973 | N | ALA | C | 233 | -78.636 | -10.274 | 8.117 | 1.00 | 35.80 |
| 13974 | CA | ALA | C | 233 | -78.116 | -11.039 | 6.989 | 1.00 | 36.32 |
| 13975 | CB | ALA | C | 233 | -77.928 | -12.488 | 7.368 | 1.00 | 35.65 |
| 13976 | C | ALA | C | 233 | -79.052 | -10.917 | 5.790 | 1.00 | 36.79 |
| 13977 | O | ALA | C | 233 | -80.263 | -10.969 | 5.948 | 1.00 | 37.65 |
| 13978 | N | GLY | C | 234 | -78.481 | -10.736 | 4.603 | 1.00 | 37.33 |
| 13979 | CA | GLY | C | 234 | -79.248 | -10.663 | 3.365 | 1.00 | 37.38 |
| 13980 | C | GLY | C | 234 | -79.966 | -9.377 | 3.008 | 1.00 | 37.11 |
| 13981 | O | GLY | C | 234 | -80.513 | -9.255 | 1.913 | 1.00 | 37.80 |
| 13982 | N | ALA | C | 235 | -79.965 | -8.407 | 3.910 | 1.00 | 37.21 |
| 13983 | CA | ALA | C | 235 | -80.694 | -7.159 | 3.683 | 1.00 | 36.87 |
| 13984 | CB | ALA | C | 235 | -81.111 | -6.552 | 5.020 | 1.00 | 36.57 |
| 13985 | C | ALA | C | 235 | -79.842 | -6.174 | 2.897 | 1.00 | 36.89 |
| 13986 | O | ALA | C | 235 | -78.673 | -6.440 | 2.628 | 1.00 | 37.64 |
| 13987 | N | VAL | C | 236 | -80.388 | -5.019 | 2.542 | 1.00 | 36.71 |
| 13988 | CA | VAL | C | 236 | -79.549 | -4.094 | 1.819 | 1.00 | 36.90 |
| 13989 | CB | VAL | C | 236 | -80.339 | -2.952 | 1.117 | 1.00 | 36.83 |
| 13990 | CG1 | VAL | C | 236 | -80.547 | -1.787 | 2.050 | 1.00 | 37.74 |
| 13991 | CG2 | VAL | C | 236 | -81.660 | -3.457 | 0.544 | 1.00 | 35.33 |
| 13992 | C | VAL | C | 236 | -78.526 | -3.486 | 2.779 | 1.00 | 37.52 |
| 13993 | O | VAL | C | 236 | -78.868 | -3.043 | 3.893 | 1.00 | 37.13 |
| 13994 | N | ASN | C | 237 | -77.275 | -3.480 | 2.335 | 1.00 | 37.50 |
| 13995 | CA | ASN | C | 237 | -76.168 | -2.904 | 3.077 | 1.00 | 38.17 |
| 13996 | CB | ASN | C | 237 | -74.876 | -3.663 | 2.750 | 1.00 | 38.39 |
| 13997 | CG | ASN | C | 237 | -74.640 | -4.852 | 3.651 | 1.00 | 38.73 |
| 13998 | OD1 | ASN | C | 237 | -73.833 | -5.720 | 3.341 | 1.00 | 38.98 |
| 13999 | ND2 | ASN | C | 237 | -75.327 | -4.886 | 4.779 | 1.00 | 38.15 |
| 14000 | C | ASN | C | 237 | -75.965 | -1.469 | 2.644 | 1.00 | 38.26 |
| 14001 | O | ASN | C | 237 | -76.470 | -1.049 | 1.603 | 1.00 | 38.10 |
| 14002 | N | PRO | C | 238 | -75.232 | -0.714 | 3.448 | 1.00 | 38.87 |
| 14003 | CA | PRO | C | 238 | -74.833 | 0.638 | 3.059 | 1.00 | 39.39 |
| 14004 | CB | PRO | C | 238 | -74.032 | 1.132 | 4.279 | 1.00 | 39.41 |
| 14005 | CG | PRO | C | 238 | -73.607 | -0.122 | 4.988 | 1.00 | 38.23 |
| 14006 | CD | PRO | C | 238 | -74.774 | -1.050 | 4.812 | 1.00 | 39.00 |
| 14007 | C | PRO | C | 238 | -73.929 | 0.572 | 1.830 | 1.00 | 40.28 |
| 14008 | O | PRO | C | 238 | -73.554 | -0.542 | 1.383 | 1.00 | 40.34 |
| 14009 | N | THR | C | 239 | -73.610 | 1.754 | 1.294 | 1.00 | 40.95 |
| 14010 | CA | THR | C | 239 | -72.726 | 1.884 | 0.145 | 1.00 | 41.78 |
| 14011 | CB | THR | C | 239 | -73.497 | 2.412 | -1.092 | 1.00 | 42.17 |
| 14012 | OG1 | THR | C | 239 | -74.131 | 3.663 | -0.773 | 1.00 | 41.20 |
| 14013 | CG2 | THR | C | 239 | -74.644 | 1.482 | -1.470 | 1.00 | 40.36 |
| 14014 | C | THR | C | 239 | -71.600 | 2.850 | 0.512 | 1.00 | 43.18 |
| 14015 | O | THR | C | 239 | -71.805 | 3.775 | 1.302 | 1.00 | 42.77 |

FIGURE 3 JO

| A | B | C | D | E | F | G | H | I | J |
|---|---|---|---|---|---|---|---|---|---|
| 14016 | N | VAL | C | 240 | -70.418 | 2.653 | -0.065 | 1.00 | 44.55 |
| 14017 | CA | VAL | C | 240 | -69.279 | 3.499 | 0.287 | 1.00 | 45.93 |
| 14018 | CB | VAL | C | 240 | -68.159 | 2.683 | 0.955 | 1.00 | 45.40 |
| 14019 | CG1 | VAL | C | 240 | -68.513 | 2.392 | 2.389 | 1.00 | 46.36 |
| 14020 | CG2 | VAL | C | 240 | -67.896 | 1.400 | 0.183 | 1.00 | 45.22 |
| 14021 | C | VAL | C | 240 | -68.667 | 4.274 | -0.863 | 1.00 | 46.82 |
| 14022 | O | VAL | C | 240 | -68.697 | 3.838 | -2.008 | 1.00 | 46.51 |
| 14023 | N | LYS | C | 241 | -68.094 | 5.420 | -0.518 | 1.00 | 48.42 |
| 14024 | CA | LYS | C | 241 | -67.441 | 6.308 | -1.460 | 1.00 | 50.07 |
| 14025 | CB | LYS | C | 241 | -68.340 | 7.511 | -1.757 | 1.00 | 49.74 |
| 14026 | CG | LYS | C | 241 | -69.445 | 7.279 | -2.786 | 1.00 | 50.25 |
| 14027 | CD | LYS | C | 241 | -70.292 | 8.538 | -2.923 | 1.00 | 49.63 |
| 14028 | CE | LYS | C | 241 | -71.065 | 8.574 | -4.227 | 1.00 | 50.24 |
| 14029 | NZ | LYS | C | 241 | -71.910 | 7.371 | -4.440 | 1.00 | 49.74 |
| 14030 | C | LYS | C | 241 | -66.171 | 6.823 | -0.802 | 1.00 | 51.37 |
| 14031 | O | LYS | C | 241 | -66.224 | 7.370 | 0.305 | 1.00 | 51.62 |
| 14032 | N | PHE | C | 242 | -65.027 | 6.641 | -1.453 | 1.00 | 52.68 |
| 14033 | CA | PHE | C | 242 | -63.797 | 7.171 | -0.883 | 1.00 | 54.02 |
| 14034 | CB | PHE | C | 242 | -62.614 | 6.199 | -0.980 | 1.00 | 54.09 |
| 14035 | CG | PHE | C | 242 | -61.393 | 6.690 | -0.249 | 1.00 | 55.54 |
| 14036 | CD1 | PHE | C | 242 | -60.987 | 6.107 | 0.940 | 1.00 | 56.76 |
| 14037 | CE1 | PHE | C | 242 | -59.880 | 6.599 | 1.617 | 1.00 | 57.97 |
| 14038 | CZ | PHE | C | 242 | -59.178 | 7.689 | 1.110 | 1.00 | 57.90 |
| 14039 | CE2 | PHE | C | 242 | -59.583 | 8.278 | -0.061 | 1.00 | 56.86 |
| 14040 | CD2 | PHE | C | 242 | -60.683 | 7.783 | -0.730 | 1.00 | 56.12 |
| 14041 | C | PHE | C | 242 | -63.451 | 8.512 | -1.516 | 1.00 | 54.71 |
| 14042 | O | PHE | C | 242 | -63.628 | 8.708 | -2.712 | 1.00 | 54.36 |
| 14043 | N | PHE | C | 243 | -62.975 | 9.430 | -0.682 | 1.00 | 55.72 |
| 14044 | CA | PHE | C | 243 | -62.602 | 10.763 | -1.111 | 1.00 | 56.89 |
| 14045 | CB | PHE | C | 243 | -63.699 | 11.777 | -0.755 | 1.00 | 56.82 |
| 14046 | CG | PHE | C | 243 | -64.992 | 11.565 | -1.486 | 1.00 | 57.69 |
| 14047 | CD1 | PHE | C | 243 | -66.010 | 10.808 | -0.921 | 1.00 | 57.77 |
| 14048 | CE1 | PHE | C | 243 | -67.209 | 10.621 | -1.590 | 1.00 | 57.00 |
| 14049 | CZ | PHE | C | 243 | -67.400 | 11.193 | -2.824 | 1.00 | 57.21 |
| 14050 | CE2 | PHE | C | 243 | -66.395 | 11.956 | -3.399 | 1.00 | 57.20 |
| 14051 | CD2 | PHE | C | 243 | -65.204 | 12.142 | -2.732 | 1.00 | 57.47 |
| 14052 | C | PHE | C | 243 | -61.334 | 11.194 | -0.396 | 1.00 | 57.53 |
| 14053 | O | PHE | C | 243 | -60.980 | 10.652 | 0.651 | 1.00 | 57.70 |
| 14054 | N | VAL | C | 244 | -60.653 | 12.176 | -0.966 | 1.00 | 58.09 |
| 14055 | CA | VAL | C | 244 | -59.506 | 12.770 | -0.313 | 1.00 | 58.87 |
| 14056 | CB | VAL | C | 244 | -58.169 | 12.138 | -0.731 | 1.00 | 58.76 |
| 14057 | CG1 | VAL | C | 244 | -58.293 | 11.448 | -2.070 | 1.00 | 58.84 |
| 14058 | CG2 | VAL | C | 244 | -57.057 | 13.186 | -0.731 | 1.00 | 58.56 |
| 14059 | C | VAL | C | 244 | -59.519 | 14.245 | -0.613 | 1.00 | 59.44 |
| 14060 | O | VAL | C | 244 | -59.866 | 14.668 | -1.715 | 1.00 | 59.55 |
| 14061 | N | VAL | C | 245 | -59.170 | 15.028 | 0.391 | 1.00 | 60.36 |
| 14062 | CA | VAL | C | 245 | -59.155 | 16.459 | 0.235 | 1.00 | 61.31 |
| 14063 | CB | VAL | C | 245 | -60.258 | 17.107 | 1.093 | 1.00 | 61.05 |
| 14064 | CG1 | VAL | C | 245 | -59.992 | 16.895 | 2.571 | 1.00 | 61.29 |
| 14065 | CG2 | VAL | C | 245 | -60.390 | 18.584 | 0.770 | 1.00 | 61.48 |
| 14066 | C | VAL | C | 245 | -57.769 | 17.010 | 0.571 | 1.00 | 61.85 |

FIGURE 3 JP

| A | B | C | D | E | F | G | H | I | J |
|---|---|---|---|---|---|---|---|---|---|
| 14067 | O | VAL | C | 245 | -57.064 | 16.477 | 1.430 | 1.00 | 61.82 |
| 14068 | N | ASN | C | 246 | -57.384 | 18.064 | -0.143 | 1.00 | 62.81 |
| 14069 | CA | ASN | C | 246 | -56.110 | 18.750 | 0.056 | 1.00 | 63.66 |
| 14070 | CB | ASN | C | 246 | -55.588 | 19.263 | -1.289 | 1.00 | 63.75 |
| 14071 | CG | ASN | C | 246 | -54.250 | 19.973 | -1.174 | 1.00 | 64.57 |
| 14072 | OD1 | ASN | C | 246 | -53.191 | 19.372 | -1.384 | 1.00 | 65.06 |
| 14073 | ND2 | ASN | C | 246 | -54.289 | 21.265 | -0.859 | 1.00 | 64.15 |
| 14074 | C | ASN | C | 246 | -56.328 | 19.899 | 1.030 | 1.00 | 64.22 |
| 14075 | O | ASN | C | 246 | -57.011 | 20.865 | 0.705 | 1.00 | 64.23 |
| 14076 | N | THR | C | 247 | -55.750 | 19.798 | 2.224 | 1.00 | 65.16 |
| 14077 | CA | THR | C | 247 | -56.007 | 20.795 | 3.263 | 1.00 | 66.53 |
| 14078 | CB | THR | C | 247 | -55.968 | 20.165 | 4.679 | 1.00 | 66.37 |
| 14079 | OG1 | THR | C | 247 | -54.741 | 19.447 | 4.864 | 1.00 | 66.45 |
| 14080 | CG2 | THR | C | 247 | -57.047 | 19.092 | 4.820 | 1.00 | 66.38 |
| 14081 | C | THR | C | 247 | -55.177 | 22.082 | 3.225 | 1.00 | 67.57 |
| 14082 | O | THR | C | 247 | -55.466 | 23.017 | 3.973 | 1.00 | 68.02 |
| 14083 | N | ASP | C | 248 | -54.158 | 22.151 | 2.376 | 1.00 | 68.75 |
| 14084 | CA | ASP | C | 248 | -53.390 | 23.389 | 2.263 | 1.00 | 69.81 |
| 14085 | CB | ASP | C | 248 | -51.950 | 23.115 | 1.833 | 1.00 | 69.78 |
| 14086 | CG | ASP | C | 248 | -51.197 | 22.270 | 2.838 | 1.00 | 70.26 |
| 14087 | OD1 | ASP | C | 248 | -50.312 | 21.494 | 2.420 | 1.00 | 70.80 |
| 14088 | OD2 | ASP | C | 248 | -51.423 | 22.316 | 4.068 | 1.00 | 70.35 |
| 14089 | C | ASP | C | 248 | -54.075 | 24.341 | 1.286 | 1.00 | 70.64 |
| 14090 | O | ASP | C | 248 | -54.036 | 25.565 | 1.453 | 1.00 | 70.76 |
| 14091 | N | SER | C | 249 | -54.718 | 23.763 | 0.274 | 1.00 | 71.41 |
| 14092 | CA | SER | C | 249 | -55.424 | 24.542 | -0.738 | 1.00 | 72.19 |
| 14093 | CB | SER | C | 249 | -55.500 | 23.774 | -2.065 | 1.00 | 72.21 |
| 14094 | OG | SER | C | 249 | -56.273 | 22.590 | -1.945 | 1.00 | 71.64 |
| 14095 | C | SER | C | 249 | -56.827 | 24.938 | -0.279 | 1.00 | 72.92 |
| 14096 | O | SER | C | 249 | -57.689 | 25.270 | -1.100 | 1.00 | 73.16 |
| 14097 | N | LEU | C | 250 | -57.057 | 24.900 | 1.030 | 1.00 | 73.60 |
| 14098 | CA | LEU | C | 250 | -58.360 | 25.263 | 1.568 | 1.00 | 74.16 |
| 14099 | CB | LEU | C | 250 | -58.530 | 24.787 | 3.016 | 1.00 | 74.23 |
| 14100 | CG | LEU | C | 250 | -58.793 | 23.297 | 3.247 | 1.00 | 74.48 |
| 14101 | CD1 | LEU | C | 250 | -58.989 | 23.012 | 4.724 | 1.00 | 74.84 |
| 14102 | CD2 | LEU | C | 250 | -59.995 | 22.812 | 2.447 | 1.00 | 74.30 |
| 14103 | C | LEU | C | 250 | -58.552 | 26.759 | 1.504 | 1.00 | 74.46 |
| 14104 | O | LEU | C | 250 | -57.832 | 27.513 | 2.154 | 1.00 | 74.68 |
| 14105 | N | SER | C | 251 | -59.513 | 27.183 | 0.696 | 1.00 | 74.74 |
| 14106 | CA | SER | C | 251 | -59.874 | 28.587 | 0.619 | 1.00 | 74.97 |
| 14107 | CB | SER | C | 251 | -60.143 | 28.985 | -0.831 | 1.00 | 74.98 |
| 14108 | OG | SER | C | 251 | -60.339 | 27.830 | -1.635 | 1.00 | 75.33 |
| 14109 | C | SER | C | 251 | -61.108 | 28.778 | 1.494 | 1.00 | 75.02 |
| 14110 | O | SER | C | 251 | -61.910 | 27.853 | 1.646 | 1.00 | 75.26 |
| 14111 | N | SER | C | 252 | -61.248 | 29.958 | 2.090 | 1.00 | 75.01 |
| 14112 | CA | SER | C | 252 | -62.381 | 30.230 | 2.974 | 1.00 | 75.02 |
| 14113 | CB | SER | C | 252 | -61.977 | 31.178 | 4.114 | 1.00 | 75.12 |
| 14114 | OG | SER | C | 252 | -61.536 | 32.438 | 3.632 | 1.00 | 74.96 |
| 14115 | C | SER | C | 252 | -63.589 | 30.779 | 2.221 | 1.00 | 75.05 |
| 14116 | O | SER | C | 252 | -64.675 | 30.932 | 2.785 | 1.00 | 75.18 |
| 14117 | N | VAL | C | 253 | -63.398 | 31.061 | 0.939 | 1.00 | 74.92 |

FIGURE 3 JQ

| A | B | C | D | E | F | G | H | I | J |
|---|---|---|---|---|---|---|---|---|---|
| 14118 | CA | VAL | C | 253 | -64.463 | 31.625 | 0.121 | 1.00 | 74.78 |
| 14119 | CB | VAL | C | 253 | -63.973 | 32.869 | -0.635 | 1.00 | 74.98 |
| 14120 | CG1 | VAL | C | 253 | -65.068 | 33.409 | -1.549 | 1.00 | 75.28 |
| 14121 | CG2 | VAL | C | 253 | -63.507 | 33.942 | 0.345 | 1.00 | 75.20 |
| 14122 | C | VAL | C | 253 | -64.983 | 30.619 | -0.893 | 1.00 | 74.54 |
| 14123 | O | VAL | C | 253 | -65.985 | 30.854 | -1.577 | 1.00 | 74.56 |
| 14124 | N | THR | C | 254 | -64.291 | 29.493 | -0.992 | 1.00 | 74.00 |
| 14125 | CA | THR | C | 254 | -64.680 | 28.472 | -1.941 | 1.00 | 73.39 |
| 14126 | CB | THR | C | 254 | -63.672 | 28.420 | -3.090 | 1.00 | 73.52 |
| 14127 | OG1 | THR | C | 254 | -63.590 | 29.716 | -3.695 | 1.00 | 73.59 |
| 14128 | CG2 | THR | C | 254 | -64.191 | 27.533 | -4.212 | 1.00 | 73.80 |
| 14129 | C | THR | C | 254 | -64.782 | 27.121 | -1.257 | 1.00 | 72.75 |
| 14130 | O | THR | C | 254 | -63.789 | 26.602 | -0.731 | 1.00 | 72.46 |
| 14131 | N | ASN | C | 255 | -65.994 | 26.570 | -1.249 | 1.00 | 71.75 |
| 14132 | CA | ASN | C | 255 | -66.223 | 25.262 | -0.662 | 1.00 | 70.61 |
| 14133 | CB | ASN | C | 255 | -67.600 | 24.710 | -1.048 | 1.00 | 70.63 |
| 14134 | CG | ASN | C | 255 | -68.724 | 25.334 | -0.243 | 1.00 | 71.20 |
| 14135 | OD1 | ASN | C | 255 | -68.487 | 25.955 | 0.794 | 1.00 | 71.73 |
| 14136 | ND2 | ASN | C | 255 | -69.957 | 25.174 | -0.718 | 1.00 | 72.81 |
| 14137 | C | ASN | C | 255 | -65.119 | 24.324 | -1.124 | 1.00 | 69.67 |
| 14138 | O | ASN | C | 255 | -64.680 | 24.384 | -2.274 | 1.00 | 69.53 |
| 14139 | N | ALA | C | 256 | -64.655 | 23.475 | -0.219 | 1.00 | 68.42 |
| 14140 | CA | ALA | C | 256 | -63.585 | 22.549 | -0.542 | 1.00 | 67.23 |
| 14141 | CB | ALA | C | 256 | -63.119 | 21.826 | 0.709 | 1.00 | 67.12 |
| 14142 | C | ALA | C | 256 | -64.039 | 21.554 | -1.599 | 1.00 | 66.42 |
| 14143 | O | ALA | C | 256 | -65.197 | 21.138 | -1.617 | 1.00 | 66.17 |
| 14144 | N | THR | C | 257 | -63.127 | 21.195 | -2.495 | 1.00 | 65.41 |
| 14145 | CA | THR | C | 257 | -63.431 | 20.214 | -3.521 | 1.00 | 64.47 |
| 14146 | CB | THR | C | 257 | -62.896 | 20.652 | -4.908 | 1.00 | 64.80 |
| 14147 | OG1 | THR | C | 257 | -63.358 | 19.737 | -5.917 | 1.00 | 65.37 |
| 14148 | CG2 | THR | C | 257 | -61.375 | 20.542 | -4.977 | 1.00 | 64.56 |
| 14149 | C | THR | C | 257 | -62.797 | 18.923 | -3.056 | 1.00 | 63.52 |
| 14150 | O | THR | C | 257 | -61.685 | 18.922 | -2.530 | 1.00 | 63.59 |
| 14151 | N | SER | C | 258 | -63.512 | 17.821 | -3.209 | 1.00 | 62.13 |
| 14152 | CA | SER | C | 258 | -63.002 | 16.557 | -2.718 | 1.00 | 60.62 |
| 14153 | CB | SER | C | 258 | -63.951 | 15.986 | -1.666 | 1.00 | 60.88 |
| 14154 | OG | SER | C | 258 | -64.412 | 17.019 | -0.806 | 1.00 | 61.43 |
| 14155 | C | SER | C | 258 | -62.821 | 15.585 | -3.861 | 1.00 | 59.48 |
| 14156 | O | SER | C | 258 | -63.725 | 15.397 | -4.679 | 1.00 | 58.94 |
| 14157 | N | ILE | C | 259 | -61.647 | 14.965 | -3.903 | 1.00 | 58.18 |
| 14158 | CA | ILE | C | 259 | -61.323 | 14.032 | -4.967 | 1.00 | 56.94 |
| 14159 | CB | ILE | C | 259 | -59.813 | 14.045 | -5.284 | 1.00 | 57.27 |
| 14160 | CG1 | ILE | C | 259 | -59.326 | 15.480 | -5.529 | 1.00 | 57.02 |
| 14161 | CD1 | ILE | C | 259 | -60.191 | 16.268 | -6.503 | 1.00 | 57.66 |
| 14162 | CG2 | ILE | C | 259 | -59.512 | 13.112 | -6.467 | 1.00 | 56.47 |
| 14163 | C | ILE | C | 259 | -61.749 | 12.631 | -4.614 | 1.00 | 56.04 |
| 14164 | O | ILE | C | 259 | -61.228 | 12.020 | -3.680 | 1.00 | 55.73 |
| 14165 | N | GLN | C | 260 | -62.701 | 12.121 | -5.382 | 1.00 | 54.99 |
| 14166 | CA | GLN | C | 260 | -63.181 | 10.771 | -5.182 | 1.00 | 53.54 |
| 14167 | CB | GLN | C | 260 | -64.550 | 10.602 | -5.834 | 1.00 | 53.37 |
| 14168 | CG | GLN | C | 260 | -65.003 | 9.173 | -5.955 | 1.00 | 52.83 |

FIGURE 3 JR

| A | B | C | D | E | F | G | H | I | J |
|---|---|---|---|---|---|---|---|---|---|
| 14169 | CD | GLN | C | 260 | -66.501 | 9.062 | -6.058 | 1.00 | 52.58 |
| 14170 | OE1 | GLN | C | 260 | -67.165 | 9.987 | -6.523 | 1.00 | 52.38 |
| 14171 | NE2 | GLN | C | 260 | -67.044 | 7.941 | -5.604 | 1.00 | 51.95 |
| 14172 | C | GLN | C | 260 | -62.216 | 9.772 | -5.772 | 1.00 | 52.72 |
| 14173 | O | GLN | C | 260 | -61.633 | 10.012 | -6.821 | 1.00 | 52.95 |
| 14174 | N | ILE | C | 261 | -62.024 | 8.666 | -5.069 | 1.00 | 51.88 |
| 14175 | CA | ILE | C | 261 | -61.265 | 7.540 | -5.592 | 1.00 | 50.87 |
| 14176 | CB | ILE | C | 261 | -60.093 | 7.154 | -4.682 | 1.00 | 50.78 |
| 14177 | CG1 | ILE | C | 261 | -59.054 | 8.276 | -4.640 | 1.00 | 50.76 |
| 14178 | CD1 | ILE | C | 261 | -57.869 | 7.981 | -3.754 | 1.00 | 50.25 |
| 14179 | CG2 | ILE | C | 261 | -59.457 | 5.856 | -5.164 | 1.00 | 50.19 |
| 14180 | C | ILE | C | 261 | -62.268 | 6.416 | -5.632 | 1.00 | 50.47 |
| 14181 | O | ILE | C | 261 | -62.616 | 5.852 | -4.602 | 1.00 | 50.34 |
| 14182 | N | THR | C | 262 | -62.771 | 6.123 | -6.818 | 1.00 | 50.10 |
| 14183 | CA | THR | C | 262 | -63.742 | 5.059 | -6.976 | 1.00 | 49.78 |
| 14184 | CB | THR | C | 262 | -64.232 | 4.987 | -8.436 | 1.00 | 50.03 |
| 14185 | OG1 | THR | C | 262 | -64.633 | 3.638 | -8.732 | 1.00 | 51.14 |
| 14186 | CG2 | THR | C | 262 | -63.079 | 5.206 | -9.389 | 1.00 | 49.30 |
| 14187 | C | THR | C | 262 | -63.111 | 3.742 | -6.614 | 1.00 | 49.16 |
| 14188 | O | THR | C | 262 | -61.903 | 3.645 | -6.486 | 1.00 | 49.47 |
| 14189 | N | ALA | C | 263 | -63.940 | 2.725 | -6.461 | 1.00 | 48.84 |
| 14190 | CA | ALA | C | 263 | -63.459 | 1.384 | -6.187 | 1.00 | 48.32 |
| 14191 | CB | ALA | C | 263 | -64.470 | 0.632 | -5.318 | 1.00 | 48.02 |
| 14192 | C | ALA | C | 263 | -63.258 | 0.660 | -7.516 | 1.00 | 47.91 |
| 14193 | O | ALA | C | 263 | -63.867 | 1.019 | -8.523 | 1.00 | 47.60 |
| 14194 | N | PRO | C | 264 | -62.412 | -0.364 | -7.516 | 1.00 | 47.56 |
| 14195 | CA | PRO | C | 264 | -62.154 | -1.157 | -8.724 | 1.00 | 47.36 |
| 14196 | CB | PRO | C | 264 | -61.143 | -2.204 | -8.247 | 1.00 | 47.26 |
| 14197 | CG | PRO | C | 264 | -60.533 | -1.599 | -7.027 | 1.00 | 47.84 |
| 14198 | CD | PRO | C | 264 | -61.624 | -0.830 | -6.368 | 1.00 | 47.47 |
| 14199 | C | PRO | C | 264 | -63.403 | -1.840 | -9.275 | 1.00 | 46.88 |
| 14200 | O | PRO | C | 264 | -64.324 | -2.197 | -8.530 | 1.00 | 46.44 |
| 14201 | N | ALA | C | 265 | -63.408 | -2.036 | -10.590 | 1.00 | 46.60 |
| 14202 | CA | ALA | C | 265 | -64.536 | -2.655 | -11.280 | 1.00 | 45.96 |
| 14203 | CB | ALA | C | 265 | -64.222 | -2.851 | -12.761 | 1.00 | 46.10 |
| 14204 | C | ALA | C | 265 | -64.925 | -3.975 | -10.650 | 1.00 | 45.47 |
| 14205 | O | ALA | C | 265 | -66.106 | -4.271 | -10.503 | 1.00 | 45.40 |
| 14206 | N | SER | C | 266 | -63.932 | -4.776 | -10.282 | 1.00 | 45.07 |
| 14207 | CA | SER | C | 266 | -64.211 | -6.087 | -9.691 | 1.00 | 44.62 |
| 14208 | CB | SER | C | 266 | -62.923 | -6.865 | -9.440 | 1.00 | 44.26 |
| 14209 | OG | SER | C | 266 | -61.973 | -6.047 | -8.785 | 1.00 | 43.86 |
| 14210 | C | SER | C | 266 | -65.033 | -5.945 | -8.410 | 1.00 | 44.41 |
| 14211 | O | SER | C | 266 | -65.690 | -6.890 | -7.978 | 1.00 | 44.20 |
| 14212 | N | MET | C | 267 | -64.993 | -4.755 | -7.815 | 1.00 | 44.50 |
| 14213 | CA | MET | C | 267 | -65.825 | -4.451 | -6.650 | 1.00 | 44.69 |
| 14214 | CB | MET | C | 267 | -65.112 | -3.477 | -5.701 | 1.00 | 44.90 |
| 14215 | CG | MET | C | 267 | -63.871 | -4.043 | -5.042 | 1.00 | 45.44 |
| 14216 | SD | MET | C | 267 | -64.293 | -5.235 | -3.769 | 1.00 | 47.95 |
| 14217 | CE | MET | C | 267 | -63.329 | -6.664 | -4.304 | 1.00 | 46.70 |
| 14218 | C | MET | C | 267 | -67.157 | -3.828 | -7.083 | 1.00 | 44.34 |
| 14219 | O | MET | C | 267 | -68.213 | -4.219 | -6.597 | 1.00 | 44.15 |

FIGURE 3 JS

| A | B | C | D | E | F | G | H | I | J |
|---|---|---|---|---|---|---|---|---|---|
| 14220 | N | LEU | C | 268 | -67.093 | -2.873 | -8.012 | 1.00 | 44.09 |
| 14221 | CA | LEU | C | 268 | -68.274 | -2.116 | -8.432 | 1.00 | 44.09 |
| 14222 | CB | LEU | C | 268 | -67.906 | -1.030 | -9.443 | 1.00 | 44.01 |
| 14223 | CG | LEU | C | 268 | -67.101 | 0.162 | -8.937 | 1.00 | 44.40 |
| 14224 | CD1 | LEU | C | 268 | -66.979 | 1.237 | -10.015 | 1.00 | 43.41 |
| 14225 | CD2 | LEU | C | 268 | -67.709 | 0.730 | -7.642 | 1.00 | 45.00 |
| 14226 | C | LEU | C | 268 | -69.409 | -2.958 | -8.996 | 1.00 | 44.07 |
| 14227 | O | LEU | C | 268 | -70.566 | -2.567 | -8.890 | 1.00 | 44.00 |
| 14228 | N | ILE | C | 269 | -69.083 | -4.114 | -9.569 | 1.00 | 44.00 |
| 14229 | CA | ILE | C | 269 | -70.101 | -4.985 | -10.159 | 1.00 | 44.30 |
| 14230 | CB | ILE | C | 269 | -69.451 | -6.166 | -10.928 | 1.00 | 44.31 |
| 14231 | CG1 | ILE | C | 269 | -68.630 | -7.021 | -9.969 | 1.00 | 45.18 |
| 14232 | CD1 | ILE | C | 269 | -68.240 | -8.361 | -10.530 | 1.00 | 46.09 |
| 14233 | CG2 | ILE | C | 269 | -68.585 | -5.669 | -12.087 | 1.00 | 43.57 |
| 14234 | C | ILE | C | 269 | -71.072 | -5.555 | -9.131 | 1.00 | 44.44 |
| 14235 | O | ILE | C | 269 | -72.051 | -6.214 | -9.494 | 1.00 | 44.73 |
| 14236 | N | GLY | C | 270 | -70.790 | -5.345 | -7.851 | 1.00 | 43.90 |
| 14237 | CA | GLY | C | 270 | -71.658 | -5.871 | -6.818 | 1.00 | 43.72 |
| 14238 | C | GLY | C | 270 | -71.495 | -5.190 | -5.475 | 1.00 | 43.60 |
| 14239 | O | GLY | C | 270 | -70.819 | -4.167 | -5.345 | 1.00 | 43.14 |
| 14240 | N | ASP | C | 271 | -72.119 | -5.775 | -4.465 | 1.00 | 43.63 |
| 14241 | CA | ASP | C | 271 | -72.050 | -5.223 | -3.128 | 1.00 | 43.31 |
| 14242 | CB | ASP | C | 271 | -73.116 | -5.842 | -2.245 | 1.00 | 43.86 |
| 14243 | CG | ASP | C | 271 | -74.481 | -5.241 | -2.505 | 1.00 | 44.75 |
| 14244 | OD1 | ASP | C | 271 | -74.521 | -4.094 | -3.004 | 1.00 | 45.20 |
| 14245 | OD2 | ASP | C | 271 | -75.550 | -5.826 | -2.246 | 1.00 | 45.69 |
| 14246 | C | ASP | C | 271 | -70.660 | -5.439 | -2.585 | 1.00 | 42.91 |
| 14247 | O | ASP | C | 271 | -70.074 | -6.490 | -2.786 | 1.00 | 43.04 |
| 14248 | N | HIS | C | 272 | -70.130 | -4.427 | -1.915 | 1.00 | 42.37 |
| 14249 | CA | HIS | C | 272 | -68.750 | -4.475 | -1.460 | 1.00 | 41.96 |
| 14250 | CB | HIS | C | 272 | -67.844 | -4.054 | -2.623 | 1.00 | 41.32 |
| 14251 | CG | HIS | C | 272 | -68.232 | -2.746 | -3.240 | 1.00 | 38.55 |
| 14252 | ND1 | HIS | C | 272 | -69.211 | -2.640 | -4.203 | 1.00 | 34.97 |
| 14253 | CE1 | HIS | C | 272 | -69.344 | -1.373 | -4.556 | 1.00 | 34.24 |
| 14254 | NE2 | HIS | C | 272 | -68.491 | -0.651 | -3.851 | 1.00 | 35.77 |
| 14255 | CD2 | HIS | C | 272 | -67.781 | -1.487 | -3.021 | 1.00 | 36.40 |
| 14256 | C | HIS | C | 272 | -68.518 | -3.566 | -0.255 | 1.00 | 42.07 |
| 14257 | O | HIS | C | 272 | -69.423 | -2.842 | 0.172 | 1.00 | 42.07 |
| 14258 | N | TYR | C | 273 | -67.300 | -3.588 | 0.278 | 1.00 | 42.29 |
| 14259 | CA | TYR | C | 273 | -66.963 | -2.765 | 1.439 | 1.00 | 42.72 |
| 14260 | CB | TYR | C | 273 | -66.970 | -3.606 | 2.716 | 1.00 | 42.37 |
| 14261 | CG | TYR | C | 273 | -68.138 | -4.548 | 2.907 | 1.00 | 41.64 |
| 14262 | CD1 | TYR | C | 273 | -69.362 | -4.080 | 3.368 | 1.00 | 41.07 |
| 14263 | CE1 | TYR | C | 273 | -70.424 | -4.942 | 3.574 | 1.00 | 40.67 |
| 14264 | CZ | TYR | C | 273 | -70.271 | -6.290 | 3.330 | 1.00 | 40.24 |
| 14265 | OH | TYR | C | 273 | -71.343 | -7.133 | 3.535 | 1.00 | 40.59 |
| 14266 | CE2 | TYR | C | 273 | -69.058 | -6.788 | 2.884 | 1.00 | 40.36 |
| 14267 | CD2 | TYR | C | 273 | -67.999 | -5.919 | 2.682 | 1.00 | 40.82 |
| 14268 | C | TYR | C | 273 | -65.577 | -2.124 | 1.355 | 1.00 | 43.60 |
| 14269 | O | TYR | C | 273 | -64.675 | -2.678 | 0.730 | 1.00 | 43.62 |
| 14270 | N | LEU | C | 274 | -65.402 | -0.970 | 1.994 | 1.00 | 44.77 |

FIGURE 3 JT

| A | B | C | D | E | F | G | H | I | J |
|---|---|---|---|---|---|---|---|---|---|
| 14271 | CA | LEU | C | 274 | -64.067 | -0.416 | 2.155 | 1.00 | 46.15 |
| 14272 | CB | LEU | C | 274 | -64.114 | 1.092 | 2.343 | 1.00 | 46.18 |
| 14273 | CG | LEU | C | 274 | -62.768 | 1.700 | 2.732 | 1.00 | 46.97 |
| 14274 | CD1 | LEU | C | 274 | -61.658 | 1.166 | 1.829 | 1.00 | 47.57 |
| 14275 | CD2 | LEU | C | 274 | -62.832 | 3.229 | 2.702 | 1.00 | 47.38 |
| 14276 | C | LEU | C | 274 | -63.553 | -1.092 | 3.422 | 1.00 | 47.02 |
| 14277 | O | LEU | C | 274 | -64.112 | -0.883 | 4.492 | 1.00 | 46.97 |
| 14278 | N | CYS | C | 275 | -62.528 | -1.930 | 3.317 | 1.00 | 48.36 |
| 14279 | CA | CYS | C | 275 | -62.078 | -2.649 | 4.506 | 1.00 | 50.35 |
| 14280 | CB | CYS | C | 275 | -62.272 | -4.153 | 4.347 | 1.00 | 50.01 |
| 14281 | SG | CYS | C | 275 | -61.346 | -4.890 | 2.996 | 1.00 | 52.51 |
| 14282 | C | CYS | C | 275 | -60.651 | -2.360 | 4.956 | 1.00 | 51.53 |
| 14283 | O | CYS | C | 275 | -60.147 | -2.998 | 5.888 | 1.00 | 52.17 |
| 14284 | N | ASP | C | 276 | -59.998 | -1.413 | 4.297 | 1.00 | 52.41 |
| 14285 | CA | ASP | C | 276 | -58.664 | -1.032 | 4.702 | 1.00 | 53.27 |
| 14286 | CB | ASP | C | 276 | -57.677 | -2.175 | 4.511 | 1.00 | 53.57 |
| 14287 | CG | ASP | C | 276 | -56.311 | -1.848 | 5.074 | 1.00 | 54.87 |
| 14288 | OD1 | ASP | C | 276 | -55.310 | -2.096 | 4.365 | 1.00 | 56.47 |
| 14289 | OD2 | ASP | C | 276 | -56.143 | -1.328 | 6.204 | 1.00 | 54.19 |
| 14290 | C | ASP | C | 276 | -58.174 | 0.203 | 3.977 | 1.00 | 53.65 |
| 14291 | O | ASP | C | 276 | -58.278 | 0.318 | 2.757 | 1.00 | 53.84 |
| 14292 | N | VAL | C | 277 | -57.641 | 1.125 | 4.763 | 1.00 | 53.91 |
| 14293 | CA | VAL | C | 277 | -57.106 | 2.371 | 4.273 | 1.00 | 54.34 |
| 14294 | CB | VAL | C | 277 | -58.036 | 3.548 | 4.625 | 1.00 | 54.24 |
| 14295 | CG1 | VAL | C | 277 | -57.453 | 4.869 | 4.134 | 1.00 | 54.06 |
| 14296 | CG2 | VAL | C | 277 | -59.414 | 3.324 | 4.048 | 1.00 | 54.19 |
| 14297 | C | VAL | C | 277 | -55.757 | 2.574 | 4.958 | 1.00 | 54.98 |
| 14298 | O | VAL | C | 277 | -55.683 | 2.734 | 6.188 | 1.00 | 54.79 |
| 14299 | N | THR | C | 278 | -54.692 | 2.527 | 4.164 | 1.00 | 55.50 |
| 14300 | CA | THR | C | 278 | -53.345 | 2.735 | 4.670 | 1.00 | 55.69 |
| 14301 | CB | THR | C | 278 | -52.566 | 1.423 | 4.684 | 1.00 | 55.79 |
| 14302 | OG1 | THR | C | 278 | -53.233 | 0.472 | 5.523 | 1.00 | 55.96 |
| 14303 | CG2 | THR | C | 278 | -51.210 | 1.624 | 5.357 | 1.00 | 55.85 |
| 14304 | C | THR | C | 278 | -52.622 | 3.741 | 3.786 | 1.00 | 55.98 |
| 14305 | O | THR | C | 278 | -52.516 | 3.557 | 2.574 | 1.00 | 55.78 |
| 14306 | N | TRP | C | 279 | -52.142 | 4.816 | 4.395 | 1.00 | 56.25 |
| 14307 | CA | TRP | C | 279 | -51.394 | 5.828 | 3.674 | 1.00 | 56.54 |
| 14308 | CB | TRP | C | 279 | -51.375 | 7.120 | 4.475 | 1.00 | 56.35 |
| 14309 | CG | TRP | C | 279 | -52.436 | 8.091 | 4.107 | 1.00 | 55.30 |
| 14310 | CD1 | TRP | C | 279 | -53.543 | 8.416 | 4.838 | 1.00 | 53.48 |
| 14311 | NE1 | TRP | C | 279 | -54.278 | 9.373 | 4.183 | 1.00 | 52.45 |
| 14312 | CE2 | TRP | C | 279 | -53.651 | 9.683 | 3.004 | 1.00 | 53.78 |
| 14313 | CD2 | TRP | C | 279 | -52.484 | 8.897 | 2.928 | 1.00 | 54.42 |
| 14314 | CE3 | TRP | C | 279 | -51.662 | 9.031 | 1.805 | 1.00 | 54.58 |
| 14315 | CZ3 | TRP | C | 279 | -52.021 | 9.938 | 0.821 | 1.00 | 53.93 |
| 14316 | CH2 | TRP | C | 279 | -53.189 | 10.694 | 0.927 | 1.00 | 53.45 |
| 14317 | CZ2 | TRP | C | 279 | -54.015 | 10.580 | 2.007 | 1.00 | 54.14 |
| 14318 | C | TRP | C | 279 | -49.966 | 5.349 | 3.480 | 1.00 | 57.14 |
| 14319 | O | TRP | C | 279 | -49.249 | 5.127 | 4.455 | 1.00 | 57.29 |
| 14320 | N | ALA | C | 280 | -49.561 | 5.172 | 2.227 | 1.00 | 57.66 |
| 14321 | CA | ALA | C | 280 | -48.199 | 4.760 | 1.914 | 1.00 | 58.20 |

FIGURE 3 JU

| A | B | C | D | E | F | G | H | I | J |
|---|---|---|---|---|---|---|---|---|---|
| 14322 | CB | ALA | C | 280 | -48.136 | 4.169 | 0.526 | 1.00 | 57.88 |
| 14323 | C | ALA | C | 280 | -47.247 | 5.952 | 2.028 | 1.00 | 58.89 |
| 14324 | O | ALA | C | 280 | -46.257 | 5.897 | 2.758 | 1.00 | 59.08 |
| 14325 | N | THR | C | 281 | -47.538 | 7.023 | 1.293 | 1.00 | 59.60 |
| 14326 | CA | THR | C | 281 | -46.702 | 8.222 | 1.346 | 1.00 | 60.36 |
| 14327 | CB | THR | C | 281 | -45.701 | 8.253 | 0.193 | 1.00 | 60.29 |
| 14328 | OG1 | THR | C | 281 | -46.287 | 8.976 | -0.896 | 1.00 | 60.03 |
| 14329 | CG2 | THR | C | 281 | -45.461 | 6.863 | -0.364 | 1.00 | 60.47 |
| 14330 | C | THR | C | 281 | -47.481 | 9.522 | 1.247 | 1.00 | 60.88 |
| 14331 | O | THR | C | 281 | -48.709 | 9.550 | 1.202 | 1.00 | 61.43 |
| 14332 | N | GLN | C | 282 | -46.733 | 10.607 | 1.170 | 1.00 | 61.16 |
| 14333 | CA | GLN | C | 282 | -47.343 | 11.904 | 1.032 | 1.00 | 61.59 |
| 14334 | CB | GLN | C | 282 | -46.272 | 12.974 | 0.816 | 1.00 | 61.79 |
| 14335 | CG | GLN | C | 282 | -45.423 | 13.237 | 2.038 | 1.00 | 63.16 |
| 14336 | CD | GLN | C | 282 | -46.258 | 13.608 | 3.244 | 1.00 | 65.36 |
| 14337 | OE1 | GLN | C | 282 | -45.763 | 13.591 | 4.376 | 1.00 | 65.87 |
| 14338 | NE2 | GLN | C | 282 | -47.527 | 13.954 | 3.009 | 1.00 | 65.20 |
| 14339 | C | GLN | C | 282 | -48.314 | 11.911 | -0.135 | 1.00 | 61.32 |
| 14340 | O | GLN | C | 282 | -49.249 | 12.711 | -0.158 | 1.00 | 61.40 |
| 14341 | N | GLU | C | 283 | -48.103 | 11.015 | -1.095 | 1.00 | 61.05 |
| 14342 | CA | GLU | C | 283 | -48.911 | 11.013 | -2.314 | 1.00 | 60.95 |
| 14343 | CB | GLU | C | 283 | -48.185 | 11.798 | -3.420 | 1.00 | 61.02 |
| 14344 | CG | GLU | C | 283 | -47.517 | 13.073 | -2.913 | 1.00 | 61.35 |
| 14345 | CD | GLU | C | 283 | -47.018 | 13.989 | -4.019 | 1.00 | 61.87 |
| 14346 | OE1 | GLU | C | 283 | -46.959 | 15.219 | -3.784 | 1.00 | 62.48 |
| 14347 | OE2 | GLU | C | 283 | -46.679 | 13.492 | -5.114 | 1.00 | 61.70 |
| 14348 | C | GLU | C | 283 | -49.276 | 9.606 | -2.792 | 1.00 | 60.60 |
| 14349 | O | GLU | C | 283 | -49.792 | 9.421 | -3.889 | 1.00 | 60.67 |
| 14350 | N | ARG | C | 284 | -48.988 | 8.610 | -1.974 | 1.00 | 60.31 |
| 14351 | CA | ARG | C | 284 | -49.396 | 7.257 | -2.296 | 1.00 | 60.24 |
| 14352 | CB | ARG | C | 284 | -48.186 | 6.333 | -2.405 | 1.00 | 60.38 |
| 14353 | CG | ARG | C | 284 | -48.513 | 4.966 | -2.975 | 1.00 | 61.76 |
| 14354 | CD | ARG | C | 284 | -47.297 | 4.070 | -3.220 | 1.00 | 64.45 |
| 14355 | NE | ARG | C | 284 | -47.024 | 3.849 | -4.642 | 1.00 | 66.08 |
| 14356 | CZ | ARG | C | 284 | -45.907 | 4.217 | -5.258 | 1.00 | 67.07 |
| 14357 | NH1 | ARG | C | 284 | -44.946 | 4.839 | -4.587 | 1.00 | 67.77 |
| 14358 | NH2 | ARG | C | 284 | -45.751 | 3.969 | -6.549 | 1.00 | 67.48 |
| 14359 | C | ARG | C | 284 | -50.354 | 6.789 | -1.198 | 1.00 | 59.88 |
| 14360 | O | ARG | C | 284 | -50.088 | 6.980 | -0.006 | 1.00 | 59.99 |
| 14361 | N | ILE | C | 285 | -51.479 | 6.205 | -1.598 | 1.00 | 59.05 |
| 14362 | CA | ILE | C | 285 | -52.471 | 5.739 | -0.637 | 1.00 | 58.17 |
| 14363 | CB | ILE | C | 285 | -53.586 | 6.808 | -0.433 | 1.00 | 58.15 |
| 14364 | CG1 | ILE | C | 285 | -54.385 | 6.519 | 0.837 | 1.00 | 57.95 |
| 14365 | CD1 | ILE | C | 285 | -55.586 | 7.413 | 1.014 | 1.00 | 57.24 |
| 14366 | CG2 | ILE | C | 285 | -54.504 | 6.886 | -1.639 | 1.00 | 57.93 |
| 14367 | C | ILE | C | 285 | -53.034 | 4.375 | -1.054 | 1.00 | 57.55 |
| 14368 | O | ILE | C | 285 | -53.385 | 4.164 | -2.213 | 1.00 | 57.33 |
| 14369 | N | SER | C | 286 | -53.090 | 3.447 | -0.102 | 1.00 | 56.84 |
| 14370 | CA | SER | C | 286 | -53.557 | 2.086 | -0.372 | 1.00 | 56.29 |
| 14371 | CB | SER | C | 286 | -52.597 | 1.062 | 0.222 | 1.00 | 56.12 |
| 14372 | OG | SER | C | 286 | -52.516 | 1.218 | 1.626 | 1.00 | 56.72 |

FIGURE 3 JV

| A | B | C | D | E | F | G | H | I | J |
|---|---|---|---|---|---|---|---|---|---|
| 14373 | C | SER | C | 286 | -54.957 | 1.842 | 0.172 | 1.00 | 55.84 |
| 14374 | O | SER | C | 286 | -55.284 | 2.240 | 1.290 | 1.00 | 55.91 |
| 14375 | N | LEU | C | 287 | -55.769 | 1.162 | -0.626 | 1.00 | 55.13 |
| 14376 | CA | LEU | C | 287 | -57.155 | 0.907 | -0.288 | 1.00 | 54.33 |
| 14377 | CB | LEU | C | 287 | -58.076 | 1.754 | -1.173 | 1.00 | 54.49 |
| 14378 | CG | LEU | C | 287 | -58.644 | 3.098 | -0.714 | 1.00 | 54.81 |
| 14379 | CD1 | LEU | C | 287 | -59.270 | 3.804 | -1.904 | 1.00 | 54.83 |
| 14380 | CD2 | LEU | C | 287 | -57.608 | 4.013 | -0.054 | 1.00 | 56.22 |
| 14381 | C | LEU | C | 287 | -57.466 | -0.544 | -0.541 | 1.00 | 53.83 |
| 14382 | O | LEU | C | 287 | -57.085 | -1.090 | -1.570 | 1.00 | 53.38 |
| 14383 | N | GLN | C | 288 | -58.152 | -1.173 | 0.409 | 1.00 | 53.46 |
| 14384 | CA | GLN | C | 288 | -58.595 | -2.548 | 0.241 | 1.00 | 52.63 |
| 14385 | CB | GLN | C | 288 | -58.025 | -3.456 | 1.322 | 1.00 | 53.22 |
| 14386 | CG | GLN | C | 288 | -56.586 | -3.842 | 1.052 | 1.00 | 54.49 |
| 14387 | CD | GLN | C | 288 | -56.334 | -5.335 | 1.246 | 1.00 | 57.06 |
| 14388 | OE1 | GLN | C | 288 | -55.607 | -5.726 | 2.159 | 1.00 | 55.92 |
| 14389 | NE2 | GLN | C | 288 | -56.933 | -6.171 | 0.388 | 1.00 | 57.21 |
| 14390 | C | GLN | C | 288 | -60.115 | -2.596 | 0.208 | 1.00 | 51.78 |
| 14391 | O | GLN | C | 288 | -60.792 | -1.917 | 0.992 | 1.00 | 51.73 |
| 14392 | N | TRP | C | 289 | -60.638 | -3.380 | -0.730 | 1.00 | 50.66 |
| 14393 | CA | TRP | C | 289 | -62.070 | -3.483 | -0.950 | 1.00 | 49.28 |
| 14394 | CB | TRP | C | 289 | -62.453 | -2.905 | -2.320 | 1.00 | 48.86 |
| 14395 | CG | TRP | C | 289 | -62.150 | -1.443 | -2.541 | 1.00 | 46.49 |
| 14396 | CD1 | TRP | C | 289 | -60.994 | -0.910 | -3.041 | 1.00 | 44.92 |
| 14397 | NE1 | TRP | C | 289 | -61.092 | 0.460 | -3.118 | 1.00 | 42.33 |
| 14398 | CE2 | TRP | C | 289 | -62.324 | 0.844 | -2.670 | 1.00 | 43.12 |
| 14399 | CD2 | TRP | C | 289 | -63.023 | -0.330 | -2.298 | 1.00 | 44.71 |
| 14400 | CE3 | TRP | C | 289 | -64.326 | -0.202 | -1.813 | 1.00 | 44.04 |
| 14401 | CZ3 | TRP | C | 289 | -64.884 | 1.068 | -1.710 | 1.00 | 43.97 |
| 14402 | CH2 | TRP | C | 289 | -64.164 | 2.209 | -2.083 | 1.00 | 44.51 |
| 14403 | CZ2 | TRP | C | 289 | -62.884 | 2.118 | -2.567 | 1.00 | 43.61 |
| 14404 | C | TRP | C | 289 | -62.454 | -4.948 | -0.881 | 1.00 | 49.19 |
| 14405 | O | TRP | C | 289 | -61.822 | -5.794 | -1.489 | 1.00 | 49.31 |
| 14406 | N | LEU | C | 290 | -63.508 | -5.238 | -0.139 | 1.00 | 49.21 |
| 14407 | CA | LEU | C | 290 | -63.944 | -6.594 | 0.090 | 1.00 | 48.60 |
| 14408 | CB | LEU | C | 290 | -64.100 | -6.792 | 1.599 | 1.00 | 48.59 |
| 14409 | CG | LEU | C | 290 | -63.826 | -8.152 | 2.246 | 1.00 | 49.04 |
| 14410 | CD1 | LEU | C | 290 | -64.605 | -8.255 | 3.553 | 1.00 | 47.77 |
| 14411 | CD2 | LEU | C | 290 | -64.197 | -9.270 | 1.312 | 1.00 | 49.22 |
| 14412 | C | LEU | C | 290 | -65.293 | -6.758 | -0.575 | 1.00 | 48.40 |
| 14413 | O | LEU | C | 290 | -66.150 | -5.885 | -0.442 | 1.00 | 48.12 |
| 14414 | N | ARG | C | 291 | -65.477 | -7.860 | -1.295 | 1.00 | 48.24 |
| 14415 | CA | ARG | C | 291 | -66.765 | -8.158 | -1.896 | 1.00 | 49.00 |
| 14416 | CB | ARG | C | 291 | -66.652 | -9.306 | -2.897 | 1.00 | 48.99 |
| 14417 | CG | ARG | C | 291 | -66.392 | -8.880 | -4.335 | 1.00 | 49.44 |
| 14418 | CD | ARG | C | 291 | -66.639 | -10.001 | -5.336 | 1.00 | 50.02 |
| 14419 | NE | ARG | C | 291 | -66.123 | -9.677 | -6.661 | 1.00 | 50.57 |
| 14420 | CZ | ARG | C | 291 | -65.444 | -10.526 | -7.417 | 1.00 | 50.24 |
| 14421 | NH1 | ARG | C | 291 | -65.011 | -10.144 | -8.609 | 1.00 | 51.60 |
| 14422 | NH2 | ARG | C | 291 | -65.196 | -11.754 | -6.981 | 1.00 | 48.39 |
| 14423 | C | ARG | C | 291 | -67.718 | -8.579 | -0.797 | 1.00 | 49.32 |

FIGURE 3 JW

| A | B | C | D | E | F | G | H | I | J |
|---|---|---|---|---|---|---|---|---|---|
| 14424 | O | ARG | C | 291 | -67.283 | -9.066 | 0.248 | 1.00 | 49.42 |
| 14425 | N | ARG | C | 292 | -69.017 | -8.406 | -1.026 | 1.00 | 49.72 |
| 14426 | CA | ARG | C | 292 | -69.996 | -8.832 | -0.034 | 1.00 | 49.95 |
| 14427 | CB | ARG | C | 292 | -71.424 | -8.540 | -0.471 | 1.00 | 49.71 |
| 14428 | CG | ARG | C | 292 | -72.395 | -8.432 | 0.704 | 1.00 | 50.13 |
| 14429 | CD | ARG | C | 292 | -73.849 | -8.224 | 0.297 | 1.00 | 50.49 |
| 14430 | NE | ARG | C | 292 | -74.792 | -8.583 | 1.355 | 1.00 | 50.03 |
| 14431 | CZ | ARG | C | 292 | -75.740 | -7.764 | 1.797 | 1.00 | 50.25 |
| 14432 | NH1 | ARG | C | 292 | -76.568 | -8.146 | 2.758 | 1.00 | 49.95 |
| 14433 | NH2 | ARG | C | 292 | -75.862 | -6.554 | 1.273 | 1.00 | 49.66 |
| 14434 | C | ARG | C | 292 | -69.787 | -10.311 | 0.214 | 1.00 | 50.22 |
| 14435 | O | ARG | C | 292 | -69.910 | -10.789 | 1.343 | 1.00 | 50.41 |
| 14436 | N | ILE | C | 293 | -69.483 | -11.052 | -0.840 | 1.00 | 50.37 |
| 14437 | CA | ILE | C | 293 | -69.056 | -12.418 | -0.612 | 1.00 | 51.22 |
| 14438 | CB | ILE | C | 293 | -69.220 | -13.291 | -1.847 | 1.00 | 51.01 |
| 14439 | CG1 | ILE | C | 293 | -70.706 | -13.390 | -2.208 | 1.00 | 52.32 |
| 14440 | CD1 | ILE | C | 293 | -71.002 | -14.244 | -3.455 | 1.00 | 53.85 |
| 14441 | CG2 | ILE | C | 293 | -68.682 | -14.666 | -1.560 | 1.00 | 50.54 |
| 14442 | C | ILE | C | 293 | -67.599 | -12.232 | -0.212 | 1.00 | 51.23 |
| 14443 | O | ILE | C | 293 | -66.733 | -12.001 | -1.051 | 1.00 | 51.38 |
| 14444 | N | GLN | C | 294 | -67.347 | -12.302 | 1.087 | 1.00 | 51.66 |
| 14445 | CA | GLN | C | 294 | -66.048 | -11.932 | 1.639 | 1.00 | 51.94 |
| 14446 | CB | GLN | C | 294 | -66.199 | -11.628 | 3.134 | 1.00 | 51.50 |
| 14447 | CG | GLN | C | 294 | -67.131 | -10.461 | 3.407 | 1.00 | 50.67 |
| 14448 | CD | GLN | C | 294 | -67.444 | -10.269 | 4.878 | 1.00 | 50.57 |
| 14449 | OE1 | GLN | C | 294 | -66.543 | -10.300 | 5.730 | 1.00 | 48.42 |
| 14450 | NE2 | GLN | C | 294 | -68.726 | -10.060 | 5.183 | 1.00 | 50.20 |
| 14451 | C | GLN | C | 294 | -64.920 | -12.937 | 1.396 | 1.00 | 52.57 |
| 14452 | O | GLN | C | 294 | -64.089 | -13.160 | 2.275 | 1.00 | 52.39 |
| 14453 | N | ASN | C | 295 | -64.884 | -13.530 | 0.205 | 1.00 | 53.31 |
| 14454 | CA | ASN | C | 295 | -63.834 | -14.485 | -0.145 | 1.00 | 54.10 |
| 14455 | CB | ASN | C | 295 | -64.446 | -15.774 | -0.677 | 1.00 | 54.21 |
| 14456 | CG | ASN | C | 295 | -65.217 | -15.549 | -1.949 | 1.00 | 55.01 |
| 14457 | OD1 | ASN | C | 295 | -65.245 | -14.438 | -2.475 | 1.00 | 54.76 |
| 14458 | ND2 | ASN | C | 295 | -65.857 | -16.593 | -2.449 | 1.00 | 59.35 |
| 14459 | C | ASN | C | 295 | -62.904 | -13.923 | -1.211 | 1.00 | 54.26 |
| 14460 | O | ASN | C | 295 | -62.172 | -14.673 | -1.856 | 1.00 | 54.15 |
| 14461 | N | TYR | C | 296 | -62.943 | -12.607 | -1.394 | 1.00 | 54.51 |
| 14462 | CA | TYR | C | 296 | -62.166 | -11.957 | -2.438 | 1.00 | 54.91 |
| 14463 | CB | TYR | C | 296 | -62.951 | -12.018 | -3.744 | 1.00 | 54.96 |
| 14464 | CG | TYR | C | 296 | -62.203 | -11.583 | -4.996 | 1.00 | 55.31 |
| 14465 | CD1 | TYR | C | 296 | -61.633 | -12.525 | -5.847 | 1.00 | 56.36 |
| 14466 | CE1 | TYR | C | 296 | -60.971 | -12.145 | -7.005 | 1.00 | 56.44 |
| 14467 | CZ | TYR | C | 296 | -60.882 | -10.808 | -7.330 | 1.00 | 55.82 |
| 14468 | OH | TYR | C | 296 | -60.226 | -10.438 | -8.480 | 1.00 | 55.06 |
| 14469 | CE2 | TYR | C | 296 | -61.452 | -9.855 | -6.509 | 1.00 | 55.37 |
| 14470 | CD2 | TYR | C | 296 | -62.113 | -10.246 | -5.353 | 1.00 | 54.88 |
| 14471 | C | TYR | C | 296 | -61.914 | -10.508 | -2.088 | 1.00 | 55.31 |
| 14472 | O | TYR | C | 296 | -62.845 | -9.725 | -1.961 | 1.00 | 55.31 |
| 14473 | N | SER | C | 297 | -60.654 | -10.143 | -1.931 | 1.00 | 56.14 |
| 14474 | CA | SER | C | 297 | -60.323 | -8.759 | -1.650 | 1.00 | 57.08 |

FIGURE 3 JX

| A | B | C | D | E | F | G | H | I | J |
|---|---|---|---|---|---|---|---|---|---|
| 14475 | CB | SER | C | 297 | -59.656 | -8.624 | -0.284 | 1.00 | 56.99 |
| 14476 | OG | SER | C | 297 | -58.256 | -8.741 | -0.402 | 1.00 | 57.32 |
| 14477 | C | SER | C | 297 | -59.394 | -8.250 | -2.732 | 1.00 | 57.41 |
| 14478 | O | SER | C | 297 | -58.746 | -9.038 | -3.407 | 1.00 | 57.69 |
| 14479 | N | VAL | C | 298 | -59.348 | -6.934 | -2.903 | 1.00 | 58.11 |
| 14480 | CA | VAL | C | 298 | -58.458 | -6.313 | -3.873 | 1.00 | 58.76 |
| 14481 | CB | VAL | C | 298 | -59.208 | -5.851 | -5.134 | 1.00 | 58.70 |
| 14482 | CG1 | VAL | C | 298 | -59.782 | -7.035 | -5.887 | 1.00 | 58.20 |
| 14483 | CG2 | VAL | C | 298 | -58.272 | -5.043 | -6.032 | 1.00 | 58.65 |
| 14484 | C | VAL | C | 298 | -57.790 | -5.085 | -3.273 | 1.00 | 59.55 |
| 14485 | O | VAL | C | 298 | -58.458 | -4.224 | -2.692 | 1.00 | 59.52 |
| 14486 | N | MET | C | 299 | -56.472 | -4.996 | -3.426 | 1.00 | 60.53 |
| 14487 | CA | MET | C | 299 | -55.732 | -3.841 | -2.939 | 1.00 | 61.43 |
| 14488 | CB | MET | C | 299 | -54.404 | -4.265 | -2.299 | 1.00 | 61.43 |
| 14489 | CG | MET | C | 299 | -53.588 | -3.093 | -1.740 | 1.00 | 62.27 |
| 14490 | SD | MET | C | 299 | -52.139 | -3.591 | -0.768 | 1.00 | 63.50 |
| 14491 | CE | MET | C | 299 | -52.924 | -4.583 | 0.481 | 1.00 | 63.92 |
| 14492 | C | MET | C | 299 | -55.480 | -2.849 | -4.070 | 1.00 | 62.24 |
| 14493 | O | MET | C | 299 | -55.001 | -3.218 | -5.142 | 1.00 | 62.05 |
| 14494 | N | ASP | C | 300 | -55.823 | -1.590 | -3.828 | 1.00 | 63.35 |
| 14495 | CA | ASP | C | 300 | -55.572 | -0.526 | -4.785 | 1.00 | 64.62 |
| 14496 | CB | ASP | C | 300 | -56.854 | 0.233 | -5.100 | 1.00 | 64.66 |
| 14497 | CG | ASP | C | 300 | -57.238 | 0.136 | -6.555 | 1.00 | 65.00 |
| 14498 | OD1 | ASP | C | 300 | -57.940 | 1.045 | -7.043 | 1.00 | 65.37 |
| 14499 | OD2 | ASP | C | 300 | -56.880 | -0.812 | -7.283 | 1.00 | 65.18 |
| 14500 | C | ASP | C | 300 | -54.534 | 0.461 | -4.272 | 1.00 | 65.56 |
| 14501 | O | ASP | C | 300 | -54.591 | 0.902 | -3.128 | 1.00 | 65.55 |
| 14502 | N | ILE | C | 301 | -53.586 | 0.814 | -5.128 | 1.00 | 66.70 |
| 14503 | CA | ILE | C | 301 | -52.578 | 1.792 | -4.755 | 1.00 | 67.95 |
| 14504 | CB | ILE | C | 301 | -51.176 | 1.182 | -4.850 | 1.00 | 68.00 |
| 14505 | CG1 | ILE | C | 301 | -50.968 | 0.198 | -3.694 | 1.00 | 68.09 |
| 14506 | CD1 | ILE | C | 301 | -50.287 | -1.091 | -4.094 | 1.00 | 68.21 |
| 14507 | CG2 | ILE | C | 301 | -50.120 | 2.275 | -4.814 | 1.00 | 68.27 |
| 14508 | C | ILE | C | 301 | -52.730 | 3.001 | -5.657 | 1.00 | 68.62 |
| 14509 | O | ILE | C | 301 | -52.661 | 2.890 | -6.872 | 1.00 | 68.88 |
| 14510 | N | CYS | C | 302 | -52.957 | 4.155 | -5.052 | 1.00 | 69.66 |
| 14511 | CA | CYS | C | 302 | -53.219 | 5.362 | -5.809 | 1.00 | 70.78 |
| 14512 | CB | CYS | C | 302 | -54.618 | 5.874 | -5.474 | 1.00 | 71.02 |
| 14513 | SG | CYS | C | 302 | -55.849 | 4.561 | -5.295 | 1.00 | 72.11 |
| 14514 | C | CYS | C | 302 | -52.193 | 6.446 | -5.524 | 1.00 | 71.37 |
| 14515 | O | CYS | C | 302 | -51.959 | 6.798 | -4.371 | 1.00 | 71.38 |
| 14516 | N | ASP | C | 303 | -51.586 | 6.973 | -6.583 | 1.00 | 72.29 |
| 14517 | CA | ASP | C | 303 | -50.606 | 8.043 | -6.456 | 1.00 | 73.14 |
| 14518 | CB | ASP | C | 303 | -49.437 | 7.831 | -7.420 | 1.00 | 73.42 |
| 14519 | CG | ASP | C | 303 | -48.692 | 6.532 | -7.171 | 1.00 | 74.20 |
| 14520 | OD1 | ASP | C | 303 | -49.189 | 5.462 | -7.587 | 1.00 | 75.36 |
| 14521 | OD2 | ASP | C | 303 | -47.590 | 6.490 | -6.586 | 1.00 | 75.49 |
| 14522 | C | ASP | C | 303 | -51.274 | 9.376 | -6.760 | 1.00 | 73.50 |
| 14523 | O | ASP | C | 303 | -52.187 | 9.448 | -7.582 | 1.00 | 73.48 |
| 14524 | N | TYR | C | 304 | -50.829 | 10.430 | -6.090 | 1.00 | 74.11 |
| 14525 | CA | TYR | C | 304 | -51.378 | 11.755 | -6.342 | 1.00 | 74.88 |

FIGURE 3 JY

| A | B | C | D | E | F | G | H | I | J |
|---|---|---|---|---|---|---|---|---|---|
| 14526 | CB | TYR | C | 304 | -51.098 | 12.695 | -5.170 | 1.00 | 74.65 |
| 14527 | CG | TYR | C | 304 | -51.672 | 14.089 | -5.334 | 1.00 | 74.89 |
| 14528 | CD1 | TYR | C | 304 | -53.040 | 14.309 | -5.278 | 1.00 | 75.03 |
| 14529 | CE1 | TYR | C | 304 | -53.572 | 15.579 | -5.424 | 1.00 | 75.07 |
| 14530 | CZ | TYR | C | 304 | -52.737 | 16.655 | -5.624 | 1.00 | 75.03 |
| 14531 | OH | TYR | C | 304 | -53.276 | 17.918 | -5.765 | 1.00 | 74.20 |
| 14532 | CE2 | TYR | C | 304 | -51.369 | 16.468 | -5.682 | 1.00 | 75.20 |
| 14533 | CD2 | TYR | C | 304 | -50.845 | 15.187 | -5.537 | 1.00 | 75.32 |
| 14534 | C | TYR | C | 304 | -50.756 | 12.318 | -7.607 | 1.00 | 75.54 |
| 14535 | O | TYR | C | 304 | -49.532 | 12.397 | -7.725 | 1.00 | 75.44 |
| 14536 | N | ASP | C | 305 | -51.602 | 12.694 | -8.559 | 1.00 | 76.52 |
| 14537 | CA | ASP | C | 305 | -51.126 | 13.292 | -9.802 | 1.00 | 77.39 |
| 14538 | CB | ASP | C | 305 | -52.033 | 12.904 | -10.970 | 1.00 | 77.39 |
| 14539 | CG | ASP | C | 305 | -51.512 | 13.404 | -12.302 | 1.00 | 78.00 |
| 14540 | OD1 | ASP | C | 305 | -51.085 | 14.580 | -12.374 | 1.00 | 77.50 |
| 14541 | OD2 | ASP | C | 305 | -51.492 | 12.688 | -13.328 | 1.00 | 78.32 |
| 14542 | C | ASP | C | 305 | -51.074 | 14.810 | -9.641 | 1.00 | 77.83 |
| 14543 | O | ASP | C | 305 | -52.108 | 15.483 | -9.674 | 1.00 | 77.69 |
| 14544 | N | GLU | C | 306 | -49.866 | 15.341 | -9.460 | 1.00 | 78.37 |
| 14545 | CA | GLU | C | 306 | -49.677 | 16.779 | -9.271 | 1.00 | 79.01 |
| 14546 | CB | GLU | C | 306 | -48.192 | 17.126 | -9.151 | 1.00 | 79.19 |
| 14547 | CG | GLU | C | 306 | -47.653 | 17.082 | -7.734 | 1.00 | 80.36 |
| 14548 | CD | GLU | C | 306 | -46.824 | 18.307 | -7.408 | 1.00 | 82.35 |
| 14549 | OE1 | GLU | C | 306 | -45.628 | 18.334 | -7.777 | 1.00 | 82.84 |
| 14550 | OE2 | GLU | C | 306 | -47.375 | 19.250 | -6.794 | 1.00 | 82.87 |
| 14551 | C | GLU | C | 306 | -50.306 | 17.627 | -10.376 | 1.00 | 79.06 |
| 14552 | O | GLU | C | 306 | -50.726 | 18.762 | -10.134 | 1.00 | 78.86 |
| 14553 | N | SER | C | 307 | -50.360 | 17.074 | -11.585 | 1.00 | 79.18 |
| 14554 | CA | SER | C | 307 | -50.917 | 17.786 | -12.731 | 1.00 | 79.30 |
| 14555 | CB | SER | C | 307 | -50.448 | 17.143 | -14.041 | 1.00 | 79.47 |
| 14556 | OG | SER | C | 307 | -51.240 | 16.008 | -14.375 | 1.00 | 79.74 |
| 14557 | C | SER | C | 307 | -52.439 | 17.793 | -12.687 | 1.00 | 79.20 |
| 14558 | O | SER | C | 307 | -53.067 | 18.852 | -12.620 | 1.00 | 79.19 |
| 14559 | N | SER | C | 308 | -53.020 | 16.597 | -12.741 | 1.00 | 78.99 |
| 14560 | CA | SER | C | 308 | -54.467 | 16.424 | -12.713 | 1.00 | 78.74 |
| 14561 | CB | SER | C | 308 | -54.816 | 14.933 | -12.653 | 1.00 | 78.75 |
| 14562 | OG | SER | C | 308 | -54.502 | 14.263 | -13.860 | 1.00 | 79.19 |
| 14563 | C | SER | C | 308 | -55.098 | 17.119 | -11.513 | 1.00 | 78.50 |
| 14564 | O | SER | C | 308 | -56.164 | 17.732 | -11.624 | 1.00 | 78.44 |
| 14565 | N | GLY | C | 309 | -54.418 | 17.034 | -10.371 | 1.00 | 78.09 |
| 14566 | CA | GLY | C | 309 | -54.973 | 17.502 | -9.115 | 1.00 | 77.62 |
| 14567 | C | GLY | C | 309 | -55.847 | 16.336 | -8.694 | 1.00 | 77.27 |
| 14568 | O | GLY | C | 309 | -56.798 | 16.474 | -7.922 | 1.00 | 77.29 |
| 14569 | N | ARG | C | 310 | -55.471 | 15.170 | -9.215 | 1.00 | 76.75 |
| 14570 | CA | ARG | C | 310 | -56.234 | 13.938 | -9.097 | 1.00 | 76.29 |
| 14571 | CB | ARG | C | 310 | -56.544 | 13.446 | -10.510 | 1.00 | 76.67 |
| 14572 | CG | ARG | C | 310 | -57.716 | 12.506 | -10.657 | 1.00 | 77.82 |
| 14573 | CD | ARG | C | 310 | -58.190 | 12.440 | -12.089 | 1.00 | 80.25 |
| 14574 | NE | ARG | C | 310 | -58.131 | 13.769 | -12.695 | 1.00 | 81.85 |
| 14575 | CZ | ARG | C | 310 | -58.417 | 14.032 | -13.964 | 1.00 | 82.78 |
| 14576 | NH1 | ARG | C | 310 | -58.789 | 13.056 | -14.783 | 1.00 | 83.05 |

FIGURE 3 JZ

| A | B | C | D | E | F | G | H | I | J |
|---|---|---|---|---|---|---|---|---|---|
| 14577 | NH2 | ARG | C | 310 | -58.331 | 15.278 | -14.416 | 1.00 | 83.30 |
| 14578 | C | ARG | C | 310 | -55.499 | 12.830 | -8.350 | 1.00 | 75.51 |
| 14579 | O | ARG | C | 310 | -54.401 | 13.028 | -7.831 | 1.00 | 75.33 |
| 14580 | N | TRP | C | 311 | -56.128 | 11.658 | -8.324 | 1.00 | 74.65 |
| 14581 | CA | TRP | C | 311 | -55.597 | 10.470 | -7.673 | 1.00 | 73.84 |
| 14582 | CB | TRP | C | 311 | -56.315 | 10.231 | -6.345 | 1.00 | 73.24 |
| 14583 | CG | TRP | C | 311 | -55.866 | 11.152 | -5.275 | 1.00 | 70.69 |
| 14584 | CD1 | TRP | C | 311 | -56.414 | 12.352 | -4.943 | 1.00 | 69.05 |
| 14585 | NE1 | TRP | C | 311 | -55.718 | 12.921 | -3.905 | 1.00 | 67.69 |
| 14586 | CE2 | TRP | C | 311 | -54.691 | 12.087 | -3.553 | 1.00 | 67.62 |
| 14587 | CD2 | TRP | C | 311 | -54.756 | 10.962 | -4.399 | 1.00 | 68.33 |
| 14588 | CE3 | TRP | C | 311 | -53.808 | 9.949 | -4.237 | 1.00 | 67.52 |
| 14589 | CZ3 | TRP | C | 311 | -52.842 | 10.091 | -3.259 | 1.00 | 67.20 |
| 14590 | CH2 | TRP | C | 311 | -52.804 | 11.224 | -2.435 | 1.00 | 66.27 |
| 14591 | CZ2 | TRP | C | 311 | -53.716 | 12.228 | -2.565 | 1.00 | 66.28 |
| 14592 | C | TRP | C | 311 | -55.791 | 9.263 | -8.578 | 1.00 | 74.16 |
| 14593 | O | TRP | C | 311 | -56.922 | 8.852 | -8.834 | 1.00 | 74.25 |
| 14594 | N | ASN | C | 312 | -54.694 | 8.682 | -9.051 | 1.00 | 74.33 |
| 14595 | CA | ASN | C | 312 | -54.797 | 7.543 | -9.957 | 1.00 | 74.55 |
| 14596 | CB | ASN | C | 312 | -54.113 | 7.859 | -11.290 | 1.00 | 74.95 |
| 14597 | CG | ASN | C | 312 | -54.852 | 8.918 | -12.076 | 1.00 | 75.92 |
| 14598 | OD1 | ASN | C | 312 | -55.937 | 8.663 | -12.611 | 1.00 | 77.19 |
| 14599 | ND2 | ASN | C | 312 | -54.282 | 10.121 | -12.139 | 1.00 | 76.28 |
| 14600 | C | ASN | C | 312 | -54.282 | 6.225 | -9.398 | 1.00 | 74.28 |
| 14601 | O | ASN | C | 312 | -53.158 | 6.140 | -8.905 | 1.00 | 74.15 |
| 14602 | N | CYS | C | 313 | -55.124 | 5.201 | -9.485 | 1.00 | 74.00 |
| 14603 | CA | CYS | C | 313 | -54.764 | 3.868 | -9.035 | 1.00 | 73.85 |
| 14604 | CB | CYS | C | 313 | -55.885 | 3.253 | -8.189 | 1.00 | 73.88 |
| 14605 | SG | CYS | C | 313 | -56.783 | 4.380 | -7.095 | 1.00 | 73.03 |
| 14606 | C | CYS | C | 313 | -54.536 | 3.006 | -10.269 | 1.00 | 73.87 |
| 14607 | O | CYS | C | 313 | -55.456 | 2.811 | -11.064 | 1.00 | 73.94 |
| 14608 | N | LEU | C | 314 | -53.317 | 2.497 | -10.431 | 1.00 | 73.68 |
| 14609 | CA | LEU | C | 314 | -52.974 | 1.682 | -11.594 | 1.00 | 73.63 |
| 14610 | CB | LEU | C | 314 | -51.464 | 1.691 | -11.831 | 1.00 | 73.72 |
| 14611 | CG | LEU | C | 314 | -50.863 | 2.884 | -12.568 | 1.00 | 74.13 |
| 14612 | CD1 | LEU | C | 314 | -50.760 | 4.092 | -11.651 | 1.00 | 74.86 |
| 14613 | CD2 | LEU | C | 314 | -51.679 | 3.202 | -13.812 | 1.00 | 74.62 |
| 14614 | C | LEU | C | 314 | -53.437 | 0.242 | -11.454 | 1.00 | 73.50 |
| 14615 | O | LEU | C | 314 | -53.186 | -0.393 | -10.433 | 1.00 | 73.75 |
| 14616 | N | VAL | C | 315 | -54.096 | -0.277 | -12.487 | 1.00 | 73.13 |
| 14617 | CA | VAL | C | 315 | -54.551 | -1.662 | -12.486 | 1.00 | 72.90 |
| 14618 | CB | VAL | C | 315 | -55.179 | -2.055 | -13.840 | 1.00 | 72.97 |
| 14619 | CG1 | VAL | C | 315 | -55.332 | -3.567 | -13.946 | 1.00 | 73.14 |
| 14620 | CG2 | VAL | C | 315 | -56.518 | -1.357 | -14.039 | 1.00 | 73.14 |
| 14621 | C | VAL | C | 315 | -53.383 | -2.599 | -12.204 | 1.00 | 72.68 |
| 14622 | O | VAL | C | 315 | -53.522 | -3.597 | -11.489 | 1.00 | 72.80 |
| 14623 | N | ALA | C | 316 | -52.228 | -2.267 | -12.771 | 1.00 | 72.27 |
| 14624 | CA | ALA | C | 316 | -51.020 | -3.067 | -12.593 | 1.00 | 71.78 |
| 14625 | CB | ALA | C | 316 | -49.902 | -2.548 | -13.490 | 1.00 | 71.86 |
| 14626 | C | ALA | C | 316 | -50.570 | -3.092 | -11.131 | 1.00 | 71.30 |
| 14627 | O | ALA | C | 316 | -49.776 | -3.940 | -10.730 | 1.00 | 71.34 |

FIGURE 3 KA

| A | B | C | D | E | F | G | H | I | J |
|---|---|---|---|---|---|---|---|---|---|
| 14628 | N | ARG | C | 317 | -51.081 | -2.159 | -10.338 | 1.00 | 70.48 |
| 14629 | CA | ARG | C | 317 | -50.722 | -2.099 | -8.931 | 1.00 | 69.90 |
| 14630 | CB | ARG | C | 317 | -50.824 | -0.668 | -8.414 | 1.00 | 70.05 |
| 14631 | CG | ARG | C | 317 | -50.086 | 0.350 | -9.252 | 1.00 | 70.18 |
| 14632 | CD | ARG | C | 317 | -48.609 | 0.430 | -8.972 | 1.00 | 69.99 |
| 14633 | NE | ARG | C | 317 | -48.159 | 1.815 | -9.004 | 1.00 | 70.37 |
| 14634 | CZ | ARG | C | 317 | -46.948 | 2.204 | -9.370 | 1.00 | 70.67 |
| 14635 | NH1 | ARG | C | 317 | -46.641 | 3.496 | -9.362 | 1.00 | 70.79 |
| 14636 | NH2 | ARG | C | 317 | -46.042 | 1.306 | -9.739 | 1.00 | 70.73 |
| 14637 | C | ARG | C | 317 | -51.642 | -2.998 | -8.115 | 1.00 | 69.33 |
| 14638 | O | ARG | C | 317 | -51.354 | -3.308 | -6.954 | 1.00 | 69.23 |
| 14639 | N | GLN | C | 318 | -52.752 | -3.403 | -8.729 | 1.00 | 68.24 |
| 14640 | CA | GLN | C | 318 | -53.723 | -4.252 | -8.060 | 1.00 | 67.00 |
| 14641 | CB | GLN | C | 318 | -54.900 | -4.585 | -8.981 | 1.00 | 66.95 |
| 14642 | CG | GLN | C | 318 | -56.048 | -3.608 | -8.865 | 1.00 | 66.42 |
| 14643 | CD | GLN | C | 318 | -57.239 | -4.009 | -9.693 | 1.00 | 65.40 |
| 14644 | OE1 | GLN | C | 318 | -58.024 | -3.158 | -10.102 | 1.00 | 65.29 |
| 14645 | NE2 | GLN | C | 318 | -57.378 | -5.306 | -9.948 | 1.00 | 64.83 |
| 14646 | C | GLN | C | 318 | -53.088 | -5.530 | -7.571 | 1.00 | 66.38 |
| 14647 | O | GLN | C | 318 | -52.285 | -6.149 | -8.272 | 1.00 | 66.39 |
| 14648 | N | HIS | C | 319 | -53.443 | -5.903 | -6.349 | 1.00 | 65.28 |
| 14649 | CA | HIS | C | 319 | -53.007 | -7.156 | -5.767 | 1.00 | 64.24 |
| 14650 | CB | HIS | C | 319 | -52.045 | -6.920 | -4.600 | 1.00 | 64.22 |
| 14651 | CG | HIS | C | 319 | -50.725 | -6.343 | -5.009 | 1.00 | 63.32 |
| 14652 | ND1 | HIS | C | 319 | -50.474 | -4.987 | -5.018 | 1.00 | 62.54 |
| 14653 | CE1 | HIS | C | 319 | -49.234 | -4.772 | -5.420 | 1.00 | 62.04 |
| 14654 | NE2 | HIS | C | 319 | -48.672 | -5.940 | -5.674 | 1.00 | 62.83 |
| 14655 | CD2 | HIS | C | 319 | -49.582 | -6.939 | -5.424 | 1.00 | 62.88 |
| 14656 | C | HIS | C | 319 | -54.268 | -7.851 | -5.296 | 1.00 | 63.78 |
| 14657 | O | HIS | C | 319 | -55.200 | -7.210 | -4.804 | 1.00 | 63.69 |
| 14658 | N | ILE | C | 320 | -54.311 | -9.163 | -5.442 | 1.00 | 63.04 |
| 14659 | CA | ILE | C | 320 | -55.508 | -9.884 | -5.066 | 1.00 | 62.66 |
| 14660 | CB | ILE | C | 320 | -56.010 | -10.737 | -6.250 | 1.00 | 62.59 |
| 14661 | CG1 | ILE | C | 320 | -56.427 | -9.832 | -7.410 | 1.00 | 62.72 |
| 14662 | CD1 | ILE | C | 320 | -56.905 | -10.589 | -8.650 | 1.00 | 62.92 |
| 14663 | CG2 | ILE | C | 320 | -57.159 | -11.635 | -5.814 | 1.00 | 62.38 |
| 14664 | C | ILE | C | 320 | -55.307 | -10.760 | -3.843 | 1.00 | 62.36 |
| 14665 | O | ILE | C | 320 | -54.356 | -11.543 | -3.776 | 1.00 | 62.58 |
| 14666 | N | GLU | C | 321 | -56.191 | -10.607 | -2.866 | 1.00 | 61.71 |
| 14667 | CA | GLU | C | 321 | -56.195 | -11.502 | -1.723 | 1.00 | 61.58 |
| 14668 | CB | GLU | C | 321 | -56.042 | -10.754 | -0.400 | 1.00 | 61.42 |
| 14669 | CG | GLU | C | 321 | -55.740 | -11.662 | 0.786 | 1.00 | 61.79 |
| 14670 | CD | GLU | C | 321 | -55.353 | -10.882 | 2.033 | 1.00 | 62.23 |
| 14671 | OE1 | GLU | C | 321 | -54.974 | -9.696 | 1.902 | 1.00 | 61.08 |
| 14672 | OE2 | GLU | C | 321 | -55.421 | -11.465 | 3.143 | 1.00 | 62.69 |
| 14673 | C | GLU | C | 321 | -57.514 | -12.261 | -1.793 | 1.00 | 61.44 |
| 14674 | O | GLU | C | 321 | -58.592 | -11.661 | -1.816 | 1.00 | 61.59 |
| 14675 | N | MET | C | 322 | -57.425 | -13.583 | -1.839 | 1.00 | 60.93 |
| 14676 | CA | MET | C | 322 | -58.609 | -14.408 | -2.000 | 1.00 | 60.65 |
| 14677 | CB | MET | C | 322 | -58.808 | -14.696 | -3.488 | 1.00 | 60.72 |
| 14678 | CG | MET | C | 322 | -59.663 | -15.880 | -3.816 | 1.00 | 61.69 |

FIGURE 3 KB

| A | B | C | D | E | F | G | H | I | J |
|---|---|---|---|---|---|---|---|---|---|
| 14679 | SD | MET | C | 322 | -59.103 | -16.592 | -5.370 | 1.00 | 65.83 |
| 14680 | CE | MET | C | 322 | -58.571 | -15.104 | -6.250 | 1.00 | 64.68 |
| 14681 | C | MET | C | 322 | -58.472 | -15.702 | -1.204 | 1.00 | 60.20 |
| 14682 | O | MET | C | 322 | -57.398 | -16.007 | -0.685 | 1.00 | 60.11 |
| 14683 | N | SER | C | 323 | -59.567 | -16.450 | -1.105 | 1.00 | 59.52 |
| 14684 | CA | SER | C | 323 | -59.584 | -17.701 | -0.374 | 1.00 | 58.94 |
| 14685 | CB | SER | C | 323 | -59.984 | -17.455 | 1.080 | 1.00 | 58.92 |
| 14686 | OG | SER | C | 323 | -59.899 | -18.644 | 1.845 | 1.00 | 59.19 |
| 14687 | C | SER | C | 323 | -60.575 | -18.632 | -1.048 | 1.00 | 58.47 |
| 14688 | O | SER | C | 323 | -61.602 | -18.189 | -1.536 | 1.00 | 58.18 |
| 14689 | N | THR | C | 324 | -60.267 | -19.921 | -1.067 | 1.00 | 58.22 |
| 14690 | CA | THR | C | 324 | -61.105 | -20.903 | -1.749 | 1.00 | 58.08 |
| 14691 | CB | THR | C | 324 | -60.265 | -21.616 | -2.823 | 1.00 | 58.38 |
| 14692 | OG1 | THR | C | 324 | -59.069 | -22.130 | -2.223 | 1.00 | 58.37 |
| 14693 | CG2 | THR | C | 324 | -59.725 | -20.599 | -3.832 | 1.00 | 57.98 |
| 14694 | C | THR | C | 324 | -61.706 | -21.929 | -0.788 | 1.00 | 57.73 |
| 14695 | O | THR | C | 324 | -62.491 | -22.789 | -1.187 | 1.00 | 58.01 |
| 14696 | N | THR | C | 325 | -61.315 | -21.830 | 0.479 | 1.00 | 57.33 |
| 14697 | CA | THR | C | 325 | -61.807 | -22.697 | 1.536 | 1.00 | 56.80 |
| 14698 | CB | THR | C | 325 | -60.625 | -23.225 | 2.364 | 1.00 | 56.93 |
| 14699 | OG1 | THR | C | 325 | -59.795 | -22.120 | 2.753 | 1.00 | 56.79 |
| 14700 | CG2 | THR | C | 325 | -59.701 | -24.066 | 1.499 | 1.00 | 57.13 |
| 14701 | C | THR | C | 325 | -62.741 | -21.882 | 2.434 | 1.00 | 56.16 |
| 14702 | O | THR | C | 325 | -63.568 | -22.450 | 3.148 | 1.00 | 56.08 |
| 14703 | N | GLY | C | 326 | -62.614 | -20.556 | 2.400 | 1.00 | 55.15 |
| 14704 | CA | GLY | C | 326 | -63.452 | -19.713 | 3.233 | 1.00 | 54.06 |
| 14705 | C | GLY | C | 326 | -63.409 | -18.222 | 2.951 | 1.00 | 53.15 |
| 14706 | O | GLY | C | 326 | -63.574 | -17.767 | 1.815 | 1.00 | 53.35 |
| 14707 | N | TRP | C | 327 | -63.191 | -17.449 | 4.001 | 1.00 | 51.92 |
| 14708 | CA | TRP | C | 327 | -63.186 | -16.005 | 3.863 | 1.00 | 50.85 |
| 14709 | CB | TRP | C | 327 | -63.990 | -15.366 | 4.993 | 1.00 | 50.43 |
| 14710 | CG | TRP | C | 327 | -63.464 | -15.641 | 6.357 | 1.00 | 47.77 |
| 14711 | CD1 | TRP | C | 327 | -62.665 | -14.831 | 7.097 | 1.00 | 46.59 |
| 14712 | NE1 | TRP | C | 327 | -62.401 | -15.406 | 8.318 | 1.00 | 46.11 |
| 14713 | CE2 | TRP | C | 327 | -63.038 | -16.615 | 8.381 | 1.00 | 46.40 |
| 14714 | CD2 | TRP | C | 327 | -63.724 | -16.790 | 7.164 | 1.00 | 45.95 |
| 14715 | CE3 | TRP | C | 327 | -64.469 | -17.954 | 6.984 | 1.00 | 45.56 |
| 14716 | CZ3 | TRP | C | 327 | -64.503 | -18.887 | 7.996 | 1.00 | 45.26 |
| 14717 | CH2 | TRP | C | 327 | -63.806 | -18.688 | 9.192 | 1.00 | 46.26 |
| 14718 | CZ2 | TRP | C | 327 | -63.072 | -17.560 | 9.406 | 1.00 | 46.57 |
| 14719 | C | TRP | C | 327 | -61.775 | -15.463 | 3.840 | 1.00 | 50.69 |
| 14720 | O | TRP | C | 327 | -60.816 | -16.207 | 4.030 | 1.00 | 51.11 |
| 14721 | N | VAL | C | 328 | -61.640 | -14.164 | 3.628 | 1.00 | 50.50 |
| 14722 | CA | VAL | C | 328 | -60.314 | -13.580 | 3.535 | 1.00 | 50.67 |
| 14723 | CB | VAL | C | 328 | -60.181 | -12.646 | 2.309 | 1.00 | 50.76 |
| 14724 | CG1 | VAL | C | 328 | -61.431 | -11.816 | 2.136 | 1.00 | 51.20 |
| 14725 | CG2 | VAL | C | 328 | -58.935 | -11.786 | 2.422 | 1.00 | 50.20 |
| 14726 | C | VAL | C | 328 | -59.895 | -12.853 | 4.796 | 1.00 | 50.73 |
| 14727 | O | VAL | C | 328 | -60.503 | -11.853 | 5.188 | 1.00 | 51.04 |
| 14728 | N | GLY | C | 329 | -58.834 | -13.359 | 5.420 | 1.00 | 50.69 |
| 14729 | CA | GLY | C | 329 | -58.316 | -12.780 | 6.647 | 1.00 | 50.34 |

FIGURE 3 KC

| A | B | C | D | E | F | G | H | I | J |
|---|---|---|---|---|---|---|---|---|---|
| 14730 | C | GLY | C | 329 | -58.965 | -13.429 | 7.851 | 1.00 | 50.30 |
| 14731 | O | GLY | C | 329 | -59.818 | -14.303 | 7.716 | 1.00 | 49.99 |
| 14732 | N | ARG | C | 330 | -58.554 | -13.019 | 9.038 | 1.00 | 50.33 |
| 14733 | CA | ARG | C | 330 | -59.147 | -13.577 | 10.237 | 1.00 | 50.67 |
| 14734 | CB | ARG | C | 330 | -58.247 | -13.335 | 11.448 | 1.00 | 50.93 |
| 14735 | CG | ARG | C | 330 | -56.997 | -14.226 | 11.391 | 1.00 | 51.71 |
| 14736 | CD | ARG | C | 330 | -56.341 | -14.515 | 12.738 | 1.00 | 52.29 |
| 14737 | NE | ARG | C | 330 | -55.139 | -13.724 | 12.905 | 1.00 | 53.20 |
| 14738 | CZ | ARG | C | 330 | -53.919 | -14.186 | 12.697 | 1.00 | 52.11 |
| 14739 | NH1 | ARG | C | 330 | -52.879 | -13.381 | 12.851 | 1.00 | 51.07 |
| 14740 | NH2 | ARG | C | 330 | -53.744 | -15.450 | 12.338 | 1.00 | 51.36 |
| 14741 | C | ARG | C | 330 | -60.551 | -13.016 | 10.407 | 1.00 | 50.42 |
| 14742 | O | ARG | C | 330 | -61.517 | -13.770 | 10.488 | 1.00 | 50.23 |
| 14743 | N | PHE | C | 331 | -60.666 | -11.693 | 10.431 | 1.00 | 50.29 |
| 14744 | CA | PHE | C | 331 | -61.981 | -11.060 | 10.452 | 1.00 | 50.57 |
| 14745 | CB | PHE | C | 331 | -62.243 | -10.347 | 11.779 | 1.00 | 50.22 |
| 14746 | CG | PHE | C | 331 | -62.313 | -11.282 | 12.953 | 1.00 | 50.45 |
| 14747 | CD1 | PHE | C | 331 | -63.487 | -11.959 | 13.248 | 1.00 | 50.48 |
| 14748 | CE1 | PHE | C | 331 | -63.551 | -12.834 | 14.314 | 1.00 | 50.64 |
| 14749 | CZ | PHE | C | 331 | -62.434 | -13.042 | 15.099 | 1.00 | 51.01 |
| 14750 | CE2 | PHE | C | 331 | -61.253 | -12.374 | 14.809 | 1.00 | 50.31 |
| 14751 | CD2 | PHE | C | 331 | -61.198 | -11.507 | 13.741 | 1.00 | 49.57 |
| 14752 | C | PHE | C | 331 | -62.082 | -10.119 | 9.252 | 1.00 | 51.11 |
| 14753 | O | PHE | C | 331 | -63.177 | -9.807 | 8.779 | 1.00 | 50.96 |
| 14754 | N | ARG | C | 332 | -60.917 | -9.698 | 8.761 | 1.00 | 51.50 |
| 14755 | CA | ARG | C | 332 | -60.807 | -8.871 | 7.567 | 1.00 | 52.05 |
| 14756 | CB | ARG | C | 332 | -61.194 | -7.413 | 7.853 | 1.00 | 52.13 |
| 14757 | CG | ARG | C | 332 | -60.272 | -6.643 | 8.791 | 1.00 | 53.45 |
| 14758 | CD | ARG | C | 332 | -61.021 | -5.621 | 9.644 | 1.00 | 56.29 |
| 14759 | NE | ARG | C | 332 | -62.130 | -6.284 | 10.342 | 1.00 | 58.60 |
| 14760 | CZ | ARG | C | 332 | -62.363 | -6.215 | 11.651 | 1.00 | 58.73 |
| 14761 | NH1 | ARG | C | 332 | -61.596 | -5.477 | 12.438 | 1.00 | 58.14 |
| 14762 | NH2 | ARG | C | 332 | -63.385 | -6.879 | 12.172 | 1.00 | 59.72 |
| 14763 | C | ARG | C | 332 | -59.394 | -8.957 | 6.980 | 1.00 | 52.20 |
| 14764 | O | ARG | C | 332 | -58.442 | -9.343 | 7.668 | 1.00 | 51.62 |
| 14765 | N | PRO | C | 333 | -59.277 | -8.651 | 5.690 | 1.00 | 52.39 |
| 14766 | CA | PRO | C | 333 | -57.977 | -8.575 | 5.020 | 1.00 | 52.50 |
| 14767 | CB | PRO | C | 333 | -58.293 | -7.762 | 3.772 | 1.00 | 52.48 |
| 14768 | CG | PRO | C | 333 | -59.696 | -8.168 | 3.439 | 1.00 | 52.79 |
| 14769 | CD | PRO | C | 333 | -60.394 | -8.407 | 4.762 | 1.00 | 52.36 |
| 14770 | C | PRO | C | 333 | -56.990 | -7.822 | 5.889 | 1.00 | 52.82 |
| 14771 | O | PRO | C | 333 | -57.359 | -6.809 | 6.497 | 1.00 | 52.91 |
| 14772 | N | SER | C | 334 | -55.754 | -8.306 | 5.944 | 1.00 | 52.91 |
| 14773 | CA | SER | C | 334 | -54.743 | -7.715 | 6.808 | 1.00 | 53.30 |
| 14774 | CB | SER | C | 334 | -53.532 | -8.646 | 6.917 | 1.00 | 53.34 |
| 14775 | OG | SER | C | 334 | -52.712 | -8.294 | 8.018 | 1.00 | 54.15 |
| 14776 | C | SER | C | 334 | -54.324 | -6.342 | 6.302 | 1.00 | 53.54 |
| 14777 | O | SER | C | 334 | -54.462 | -6.046 | 5.117 | 1.00 | 53.24 |
| 14778 | N | GLU | C | 335 | -53.840 | -5.497 | 7.209 | 1.00 | 53.95 |
| 14779 | CA | GLU | C | 335 | -53.382 | -4.169 | 6.832 | 1.00 | 54.84 |
| 14780 | CB | GLU | C | 335 | -53.582 | -3.161 | 7.970 | 1.00 | 54.79 |

FIGURE 3 KD

| A | B | C | D | E | F | G | H | I | J |
|---|---|---|---|---|---|---|---|---|---|
| 14781 | CG | GLU | C | 335 | -52.526 | -3.173 | 9.074 | 1.00 | 55.64 |
| 14782 | CD | GLU | C | 335 | -52.545 | -4.432 | 9.939 | 1.00 | 56.05 |
| 14783 | OE1 | GLU | C | 335 | -53.529 | -5.203 | 9.903 | 1.00 | 55.12 |
| 14784 | OE2 | GLU | C | 335 | -51.556 | -4.649 | 10.664 | 1.00 | 57.44 |
| 14785 | C | GLU | C | 335 | -51.921 | -4.248 | 6.400 | 1.00 | 55.51 |
| 14786 | O | GLU | C | 335 | -51.161 | -5.072 | 6.915 | 1.00 | 55.48 |
| 14787 | N | PRO | C | 336 | -51.542 | -3.410 | 5.435 | 1.00 | 56.22 |
| 14788 | CA | PRO | C | 336 | -50.186 | -3.396 | 4.879 | 1.00 | 56.76 |
| 14789 | CB | PRO | C | 336 | -50.443 | -2.846 | 3.488 | 1.00 | 56.76 |
| 14790 | CG | PRO | C | 336 | -51.425 | -1.743 | 3.801 | 1.00 | 56.17 |
| 14791 | CD | PRO | C | 336 | -52.401 | -2.421 | 4.755 | 1.00 | 56.21 |
| 14792 | C | PRO | C | 336 | -49.246 | -2.436 | 5.600 | 1.00 | 57.44 |
| 14793 | O | PRO | C | 336 | -49.669 | -1.389 | 6.103 | 1.00 | 57.27 |
| 14794 | N | HIS | C | 337 | -47.968 | -2.787 | 5.640 | 1.00 | 58.37 |
| 14795 | CA | HIS | C | 337 | -46.973 | -1.896 | 6.234 | 1.00 | 59.44 |
| 14796 | CB | HIS | C | 337 | -46.302 | -2.541 | 7.440 | 1.00 | 59.29 |
| 14797 | CG | HIS | C | 337 | -47.224 | -2.719 | 8.601 | 1.00 | 60.00 |
| 14798 | ND1 | HIS | C | 337 | -48.054 | -3.812 | 8.730 | 1.00 | 60.63 |
| 14799 | CE1 | HIS | C | 337 | -48.759 | -3.694 | 9.840 | 1.00 | 61.42 |
| 14800 | NE2 | HIS | C | 337 | -48.422 | -2.560 | 10.431 | 1.00 | 61.34 |
| 14801 | CD2 | HIS | C | 337 | -47.470 | -1.928 | 9.671 | 1.00 | 60.58 |
| 14802 | C | HIS | C | 337 | -45.961 | -1.515 | 5.175 | 1.00 | 59.88 |
| 14803 | O | HIS | C | 337 | -45.146 | -2.336 | 4.760 | 1.00 | 59.79 |
| 14804 | N | PHE | C | 338 | -46.031 | -0.264 | 4.741 | 1.00 | 60.83 |
| 14805 | CA | PHE | C | 338 | -45.199 | 0.224 | 3.647 | 1.00 | 61.83 |
| 14806 | CB | PHE | C | 338 | -45.886 | 1.403 | 2.963 | 1.00 | 61.84 |
| 14807 | CG | PHE | C | 338 | -47.182 | 1.041 | 2.305 | 1.00 | 62.19 |
| 14808 | CD1 | PHE | C | 338 | -48.387 | 1.244 | 2.957 | 1.00 | 61.45 |
| 14809 | CE1 | PHE | C | 338 | -49.576 | 0.907 | 2.350 | 1.00 | 62.03 |
| 14810 | CZ | PHE | C | 338 | -49.572 | 0.333 | 1.087 | 1.00 | 62.44 |
| 14811 | CE2 | PHE | C | 338 | -48.381 | 0.124 | 0.430 | 1.00 | 63.09 |
| 14812 | CD2 | PHE | C | 338 | -47.194 | 0.477 | 1.039 | 1.00 | 63.13 |
| 14813 | C | PHE | C | 338 | -43.792 | 0.629 | 4.046 | 1.00 | 62.61 |
| 14814 | O | PHE | C | 338 | -43.585 | 1.302 | 5.059 | 1.00 | 62.69 |
| 14815 | N | THR | C | 339 | -42.822 | 0.202 | 3.243 | 1.00 | 63.56 |
| 14816 | CA | THR | C | 339 | -41.450 | 0.643 | 3.429 | 1.00 | 64.18 |
| 14817 | CB | THR | C | 339 | -40.504 | -0.087 | 2.470 | 1.00 | 64.13 |
| 14818 | OG1 | THR | C | 339 | -40.739 | 0.365 | 1.128 | 1.00 | 64.53 |
| 14819 | CG2 | THR | C | 339 | -40.841 | -1.555 | 2.422 | 1.00 | 64.14 |
| 14820 | C | THR | C | 339 | -41.465 | 2.125 | 3.104 | 1.00 | 64.46 |
| 14821 | O | THR | C | 339 | -42.241 | 2.569 | 2.261 | 1.00 | 64.54 |
| 14822 | N | LEU | C | 340 | -40.601 | 2.875 | 3.770 | 1.00 | 65.17 |
| 14823 | CA | LEU | C | 340 | -40.517 | 4.324 | 3.625 | 1.00 | 65.83 |
| 14824 | CB | LEU | C | 340 | -39.205 | 4.826 | 4.230 | 1.00 | 66.16 |
| 14825 | CG | LEU | C | 340 | -38.916 | 6.328 | 4.240 | 1.00 | 66.50 |
| 14826 | CD1 | LEU | C | 340 | -40.027 | 7.111 | 4.935 | 1.00 | 67.20 |
| 14827 | CD2 | LEU | C | 340 | -37.580 | 6.568 | 4.927 | 1.00 | 67.69 |
| 14828 | C | LEU | C | 340 | -40.674 | 4.872 | 2.209 | 1.00 | 66.08 |
| 14829 | O | LEU | C | 340 | -41.340 | 5.889 | 2.016 | 1.00 | 66.20 |
| 14830 | N | ASP | C | 341 | -40.063 | 4.226 | 1.220 | 1.00 | 66.47 |
| 14831 | CA | ASP | C | 341 | -40.159 | 4.747 | -0.142 | 1.00 | 66.83 |

FIGURE 3 KE

| A | B | C | D | E | F | G | H | I | J |
|---|---|---|---|---|---|---|---|---|---|
| 14832 | CB | ASP | C | 341 | -39.072 | 4.165 | -1.050 | 1.00 | 66.88 |
| 14833 | CG | ASP | C | 341 | -39.254 | 2.686 | -1.306 | 1.00 | 67.29 |
| 14834 | OD1 | ASP | C | 341 | -38.389 | 2.086 | -1.981 | 1.00 | 67.46 |
| 14835 | OD2 | ASP | C | 341 | -40.232 | 2.041 | -0.879 | 1.00 | 68.13 |
| 14836 | C | ASP | C | 341 | -41.567 | 4.540 | -0.709 | 1.00 | 67.00 |
| 14837 | O | ASP | C | 341 | -42.017 | 5.279 | -1.590 | 1.00 | 66.86 |
| 14838 | N | GLY | C | 342 | -42.255 | 3.531 | -0.180 | 1.00 | 67.15 |
| 14839 | CA | GLY | C | 342 | -43.631 | 3.242 | -0.546 | 1.00 | 67.47 |
| 14840 | C | GLY | C | 342 | -43.832 | 2.363 | -1.766 | 1.00 | 67.62 |
| 14841 | O | GLY | C | 342 | -44.958 | 2.186 | -2.228 | 1.00 | 67.62 |
| 14842 | N | ASN | C | 343 | -42.750 | 1.812 | -2.297 | 1.00 | 67.70 |
| 14843 | CA | ASN | C | 343 | -42.856 | 0.967 | -3.476 | 1.00 | 67.94 |
| 14844 | CB | ASN | C | 343 | -41.730 | 1.290 | -4.451 | 1.00 | 68.36 |
| 14845 | CG | ASN | C | 343 | -41.353 | 2.761 | -4.424 | 1.00 | 69.30 |
| 14846 | OD1 | ASN | C | 343 | -42.196 | 3.639 | -4.640 | 1.00 | 70.24 |
| 14847 | ND2 | ASN | C | 343 | -40.088 | 3.039 | -4.136 | 1.00 | 69.74 |
| 14848 | C | ASN | C | 343 | -42.834 | -0.497 | -3.073 | 1.00 | 67.71 |
| 14849 | O | ASN | C | 343 | -42.850 | -1.399 | -3.915 | 1.00 | 67.91 |
| 14850 | N | SER | C | 344 | -42.807 | -0.718 | -1.765 | 1.00 | 67.27 |
| 14851 | CA | SER | C | 344 | -42.812 | -2.054 | -1.198 | 1.00 | 66.98 |
| 14852 | CB | SER | C | 344 | -41.386 | -2.493 | -0.882 | 1.00 | 67.02 |
| 14853 | OG | SER | C | 344 | -41.383 | -3.483 | 0.127 | 1.00 | 66.88 |
| 14854 | C | SER | C | 344 | -43.647 | -2.057 | 0.075 | 1.00 | 66.84 |
| 14855 | O | SER | C | 344 | -43.882 | -1.004 | 0.671 | 1.00 | 66.80 |
| 14856 | N | PHE | C | 345 | -44.101 | -3.236 | 0.490 | 1.00 | 66.62 |
| 14857 | CA | PHE | C | 345 | -44.883 | -3.348 | 1.718 | 1.00 | 66.60 |
| 14858 | CB | PHE | C | 345 | -46.257 | -2.682 | 1.565 | 1.00 | 66.55 |
| 14859 | CG | PHE | C | 345 | -47.204 | -3.421 | 0.659 | 1.00 | 66.13 |
| 14860 | CD1 | PHE | C | 345 | -47.889 | -4.536 | 1.105 | 1.00 | 66.16 |
| 14861 | CE1 | PHE | C | 345 | -48.764 | -5.209 | 0.276 | 1.00 | 65.55 |
| 14862 | CZ | PHE | C | 345 | -48.974 | -4.764 | -1.008 | 1.00 | 65.27 |
| 14863 | CE2 | PHE | C | 345 | -48.308 | -3.650 | -1.464 | 1.00 | 66.07 |
| 14864 | CD2 | PHE | C | 345 | -47.431 | -2.979 | -0.630 | 1.00 | 66.28 |
| 14865 | C | PHE | C | 345 | -45.040 | -4.789 | 2.181 | 1.00 | 66.56 |
| 14866 | O | PHE | C | 345 | -44.968 | -5.718 | 1.379 | 1.00 | 66.80 |
| 14867 | N | TYR | C | 346 | -45.255 | -4.968 | 3.481 | 1.00 | 66.39 |
| 14868 | CA | TYR | C | 346 | -45.433 | -6.298 | 4.058 | 1.00 | 66.27 |
| 14869 | CB | TYR | C | 346 | -44.439 | -6.540 | 5.199 | 1.00 | 66.30 |
| 14870 | CG | TYR | C | 346 | -42.979 | -6.360 | 4.849 | 1.00 | 66.10 |
| 14871 | CD1 | TYR | C | 346 | -42.160 | -7.457 | 4.635 | 1.00 | 66.33 |
| 14872 | CE1 | TYR | C | 346 | -40.823 | -7.298 | 4.328 | 1.00 | 66.82 |
| 14873 | CZ | TYR | C | 346 | -40.286 | -6.030 | 4.237 | 1.00 | 66.97 |
| 14874 | OH | TYR | C | 346 | -38.949 | -5.870 | 3.920 | 1.00 | 67.38 |
| 14875 | CE2 | TYR | C | 346 | -41.082 | -4.925 | 4.449 | 1.00 | 66.61 |
| 14876 | CD2 | TYR | C | 346 | -42.416 | -5.095 | 4.758 | 1.00 | 65.95 |
| 14877 | C | TYR | C | 346 | -46.841 | -6.438 | 4.621 | 1.00 | 66.27 |
| 14878 | O | TYR | C | 346 | -47.456 | -5.446 | 5.031 | 1.00 | 66.28 |
| 14879 | N | LYS | C | 347 | -47.342 | -7.671 | 4.655 | 1.00 | 66.10 |
| 14880 | CA | LYS | C | 347 | -48.659 | -7.939 | 5.220 | 1.00 | 66.03 |
| 14881 | CB | LYS | C | 347 | -49.759 | -7.368 | 4.327 | 1.00 | 66.14 |
| 14882 | CG | LYS | C | 347 | -50.027 | -8.200 | 3.100 | 1.00 | 66.48 |

FIGURE 3 KF

| A | B | C | D | E | F | G | H | I | J |
|---|---|---|---|---|---|---|---|---|---|
| 14883 | CD | LYS | C | 347 | -51.517 | -8.351 | 2.866 | 1.00 | 66.66 |
| 14884 | CE | LYS | C | 347 | -52.218 | -7.008 | 2.779 | 1.00 | 67.11 |
| 14885 | NZ | LYS | C | 347 | -53.687 | -7.213 | 2.633 | 1.00 | 67.50 |
| 14886 | C | LYS | C | 347 | -48.909 | -9.430 | 5.453 | 1.00 | 65.79 |
| 14887 | O | LYS | C | 347 | -48.432 | -10.277 | 4.695 | 1.00 | 65.82 |
| 14888 | N | ILE | C | 348 | -49.670 | -9.738 | 6.502 | 1.00 | 65.44 |
| 14889 | CA | ILE | C | 348 | -49.997 | -11.118 | 6.842 | 1.00 | 65.31 |
| 14890 | CB | ILE | C | 348 | -50.481 | -11.223 | 8.312 | 1.00 | 65.30 |
| 14891 | CG1 | ILE | C | 348 | -49.332 | -10.980 | 9.297 | 1.00 | 65.22 |
| 14892 | CD1 | ILE | C | 348 | -49.331 | -9.614 | 9.940 | 1.00 | 64.91 |
| 14893 | CG2 | ILE | C | 348 | -51.115 | -12.582 | 8.564 | 1.00 | 64.62 |
| 14894 | C | ILE | C | 348 | -51.073 | -11.684 | 5.924 | 1.00 | 65.15 |
| 14895 | O | ILE | C | 348 | -52.147 | -11.109 | 5.797 | 1.00 | 65.21 |
| 14896 | N | ILE | C | 349 | -50.777 | -12.809 | 5.282 | 1.00 | 65.19 |
| 14897 | CA | ILE | C | 349 | -51.745 | -13.496 | 4.432 | 1.00 | 65.26 |
| 14898 | CB | ILE | C | 349 | -51.525 | -13.182 | 2.943 | 1.00 | 65.13 |
| 14899 | CG1 | ILE | C | 349 | -50.110 | -13.564 | 2.511 | 1.00 | 64.92 |
| 14900 | CD1 | ILE | C | 349 | -49.995 | -13.839 | 1.030 | 1.00 | 64.34 |
| 14901 | CG2 | ILE | C | 349 | -51.805 | -11.750 | 2.646 | 1.00 | 65.13 |
| 14902 | C | ILE | C | 349 | -51.612 | -14.993 | 4.617 | 1.00 | 65.53 |
| 14903 | O | ILE | C | 349 | -50.617 | -15.467 | 5.153 | 1.00 | 65.52 |
| 14904 | N | SER | C | 350 | -52.609 | -15.739 | 4.152 | 1.00 | 66.02 |
| 14905 | CA | SER | C | 350 | -52.567 | -17.192 | 4.247 | 1.00 | 66.59 |
| 14906 | CB | SER | C | 350 | -53.958 | -17.790 | 4.044 | 1.00 | 66.61 |
| 14907 | OG | SER | C | 350 | -53.891 | -19.204 | 3.976 | 1.00 | 66.59 |
| 14908 | C | SER | C | 350 | -51.607 | -17.742 | 3.200 | 1.00 | 67.03 |
| 14909 | O | SER | C | 350 | -51.184 | -17.017 | 2.298 | 1.00 | 67.24 |
| 14910 | N | ASN | C | 351 | -51.260 | -19.020 | 3.316 | 1.00 | 67.27 |
| 14911 | CA | ASN | C | 351 | -50.343 | -19.628 | 2.357 | 1.00 | 67.38 |
| 14912 | CB | ASN | C | 351 | -48.954 | -19.826 | 2.973 | 1.00 | 67.28 |
| 14913 | CG | ASN | C | 351 | -48.891 | -21.010 | 3.909 | 1.00 | 66.52 |
| 14914 | OD1 | ASN | C | 351 | -49.590 | -21.999 | 3.721 | 1.00 | 65.01 |
| 14915 | ND2 | ASN | C | 351 | -48.031 | -20.921 | 4.916 | 1.00 | 66.38 |
| 14916 | C | ASN | C | 351 | -50.873 | -20.921 | 1.748 | 1.00 | 67.65 |
| 14917 | O | ASN | C | 351 | -52.049 | -21.252 | 1.898 | 1.00 | 67.66 |
| 14918 | N | GLU | C | 352 | -49.997 | -21.641 | 1.057 | 1.00 | 68.00 |
| 14919 | CA | GLU | C | 352 | -50.377 | -22.875 | 0.396 | 1.00 | 68.26 |
| 14920 | CB | GLU | C | 352 | -49.253 | -23.357 | -0.532 | 1.00 | 68.64 |
| 14921 | CG | GLU | C | 352 | -48.040 | -23.953 | 0.176 | 1.00 | 69.60 |
| 14922 | CD | GLU | C | 352 | -47.205 | -22.926 | 0.922 | 1.00 | 70.82 |
| 14923 | OE1 | GLU | C | 352 | -46.343 | -23.349 | 1.723 | 1.00 | 71.80 |
| 14924 | OE2 | GLU | C | 352 | -47.402 | -21.706 | 0.709 | 1.00 | 70.61 |
| 14925 | C | GLU | C | 352 | -50.722 | -23.930 | 1.430 | 1.00 | 68.05 |
| 14926 | O | GLU | C | 352 | -51.538 | -24.812 | 1.170 | 1.00 | 68.26 |
| 14927 | N | GLU | C | 353 | -50.106 | -23.840 | 2.606 | 1.00 | 67.86 |
| 14928 | CA | GLU | C | 353 | -50.360 | -24.809 | 3.672 | 1.00 | 67.65 |
| 14929 | CB | GLU | C | 353 | -49.065 | -25.161 | 4.419 | 1.00 | 67.87 |
| 14930 | CG | GLU | C | 353 | -48.117 | -26.062 | 3.634 | 1.00 | 68.50 |
| 14931 | CD | GLU | C | 353 | -48.356 | -27.542 | 3.892 | 1.00 | 69.62 |
| 14932 | OE1 | GLU | C | 353 | -47.364 | -28.307 | 3.971 | 1.00 | 69.66 |
| 14933 | OE2 | GLU | C | 353 | -49.534 | -27.942 | 4.023 | 1.00 | 69.65 |

FIGURE 3 KG

| A | B | C | D | E | F | G | H | I | J |
|---|---|---|---|---|---|---|---|---|---|
| 14934 | C | GLU | C | 353 | -51.422 | -24.278 | 4.629 | 1.00 | 67.08 |
| 14935 | O | GLU | C | 353 | -51.915 | -25.003 | 5.492 | 1.00 | 66.87 |
| 14936 | N | GLY | C | 354 | -51.753 | -22.998 | 4.472 | 1.00 | 66.52 |
| 14937 | CA | GLY | C | 354 | -52.818 | -22.375 | 5.232 | 1.00 | 65.69 |
| 14938 | C | GLY | C | 354 | -52.420 | -21.564 | 6.444 | 1.00 | 65.14 |
| 14939 | O | GLY | C | 354 | -53.274 | -21.089 | 7.185 | 1.00 | 65.63 |
| 14940 | N | TYR | C | 355 | -51.134 | -21.383 | 6.668 | 1.00 | 64.36 |
| 14941 | CA | TYR | C | 355 | -50.734 | -20.623 | 7.839 | 1.00 | 63.70 |
| 14942 | CB | TYR | C | 355 | -49.549 | -21.285 | 8.541 | 1.00 | 63.55 |
| 14943 | CG | TYR | C | 355 | -49.924 | -22.646 | 9.084 | 1.00 | 63.58 |
| 14944 | CD1 | TYR | C | 355 | -50.245 | -23.688 | 8.226 | 1.00 | 62.90 |
| 14945 | CE1 | TYR | C | 355 | -50.602 | -24.928 | 8.708 | 1.00 | 63.30 |
| 14946 | CZ | TYR | C | 355 | -50.652 | -25.142 | 10.066 | 1.00 | 63.76 |
| 14947 | OH | TYR | C | 355 | -51.011 | -26.383 | 10.549 | 1.00 | 64.11 |
| 14948 | CE2 | TYR | C | 355 | -50.347 | -24.121 | 10.941 | 1.00 | 63.99 |
| 14949 | CD2 | TYR | C | 355 | -49.990 | -22.880 | 10.449 | 1.00 | 63.60 |
| 14950 | C | TYR | C | 355 | -50.472 | -19.184 | 7.462 | 1.00 | 63.29 |
| 14951 | O | TYR | C | 355 | -50.000 | -18.895 | 6.368 | 1.00 | 63.27 |
| 14952 | N | ARG | C | 356 | -50.803 | -18.276 | 8.367 | 1.00 | 62.80 |
| 14953 | CA | ARG | C | 356 | -50.681 | -16.860 | 8.069 | 1.00 | 62.47 |
| 14954 | CB | ARG | C | 356 | -51.798 | -16.077 | 8.766 | 1.00 | 62.13 |
| 14955 | CG | ARG | C | 356 | -53.127 | -16.782 | 8.586 | 1.00 | 60.75 |
| 14956 | CD | ARG | C | 356 | -54.368 | -16.005 | 8.951 | 1.00 | 57.23 |
| 14957 | NE | ARG | C | 356 | -55.511 | -16.694 | 8.369 | 1.00 | 55.24 |
| 14958 | CZ | ARG | C | 356 | -56.241 | -16.218 | 7.374 | 1.00 | 53.37 |
| 14959 | NH1 | ARG | C | 356 | -55.978 | -15.012 | 6.864 | 1.00 | 50.50 |
| 14960 | NH2 | ARG | C | 356 | -57.245 | -16.944 | 6.898 | 1.00 | 51.24 |
| 14961 | C | ARG | C | 356 | -49.292 | -16.334 | 8.392 | 1.00 | 62.56 |
| 14962 | O | ARG | C | 356 | -48.883 | -16.250 | 9.556 | 1.00 | 62.37 |
| 14963 | N | HIS | C | 357 | -48.562 | -15.997 | 7.337 | 1.00 | 62.62 |
| 14964 | CA | HIS | C | 357 | -47.199 | -15.524 | 7.496 | 1.00 | 62.90 |
| 14965 | CB | HIS | C | 357 | -46.203 | -16.576 | 7.013 | 1.00 | 62.31 |
| 14966 | CG | HIS | C | 357 | -46.150 | -17.783 | 7.892 | 1.00 | 60.17 |
| 14967 | ND1 | HIS | C | 357 | -45.494 | -17.787 | 9.103 | 1.00 | 58.55 |
| 14968 | CE1 | HIS | C | 357 | -45.627 | -18.972 | 9.670 | 1.00 | 58.54 |
| 14969 | NE2 | HIS | C | 357 | -46.349 | -19.737 | 8.870 | 1.00 | 58.37 |
| 14970 | CD2 | HIS | C | 357 | -46.696 | -19.013 | 7.755 | 1.00 | 58.71 |
| 14971 | C | HIS | C | 357 | -46.980 | -14.201 | 6.801 | 1.00 | 63.76 |
| 14972 | O | HIS | C | 357 | -47.716 | -13.837 | 5.879 | 1.00 | 63.54 |
| 14973 | N | ILE | C | 358 | -45.979 | -13.471 | 7.275 | 1.00 | 64.84 |
| 14974 | CA | ILE | C | 358 | -45.676 | -12.179 | 6.702 | 1.00 | 66.26 |
| 14975 | CB | ILE | C | 358 | -44.607 | -11.448 | 7.517 | 1.00 | 65.95 |
| 14976 | CG1 | ILE | C | 358 | -45.120 | -11.189 | 8.933 | 1.00 | 66.20 |
| 14977 | CD1 | ILE | C | 358 | -44.100 | -10.576 | 9.867 | 1.00 | 65.33 |
| 14978 | CG2 | ILE | C | 358 | -44.247 | -10.138 | 6.841 | 1.00 | 65.73 |
| 14979 | C | ILE | C | 358 | -45.210 | -12.369 | 5.275 | 1.00 | 67.47 |
| 14980 | O | ILE | C | 358 | -44.450 | -13.288 | 4.967 | 1.00 | 67.57 |
| 14981 | N | CYS | C | 359 | -45.693 | -11.516 | 4.389 | 1.00 | 69.11 |
| 14982 | CA | CYS | C | 359 | -45.241 | -11.591 | 3.023 | 1.00 | 70.84 |
| 14983 | CB | CYS | C | 359 | -46.330 | -12.095 | 2.103 | 1.00 | 70.96 |
| 14984 | SG | CYS | C | 359 | -45.668 | -12.166 | 0.445 | 1.00 | 73.62 |

FIGURE 3 KH

| A | B | C | D | E | F | G | H | I | J |
|---|---|---|---|---|---|---|---|---|---|
| 14985 | C | CYS | C | 359 | -44.700 | -10.266 | 2.513 | 1.00 | 71.46 |
| 14986 | O | CYS | C | 359 | -45.218 | -9.198 | 2.842 | 1.00 | 71.59 |
| 14987 | N | TYR | C | 360 | -43.646 | -10.354 | 1.710 | 1.00 | 72.46 |
| 14988 | CA | TYR | C | 360 | -43.033 | -9.181 | 1.115 | 1.00 | 73.46 |
| 14989 | CB | TYR | C | 360 | -41.522 | -9.371 | 0.985 | 1.00 | 73.67 |
| 14990 | CG | TYR | C | 360 | -40.782 | -8.135 | 0.549 | 1.00 | 74.14 |
| 14991 | CD1 | TYR | C | 360 | -40.284 | -8.016 | -0.741 | 1.00 | 74.81 |
| 14992 | CE1 | TYR | C | 360 | -39.606 | -6.882 | -1.137 | 1.00 | 75.14 |
| 14993 | CZ | TYR | C | 360 | -39.419 | -5.847 | -0.238 | 1.00 | 75.23 |
| 14994 | OH | TYR | C | 360 | -38.745 | -4.711 | -0.622 | 1.00 | 75.50 |
| 14995 | CE2 | TYR | C | 360 | -39.905 | -5.944 | 1.044 | 1.00 | 75.19 |
| 14996 | CD2 | TYR | C | 360 | -40.580 | -7.088 | 1.429 | 1.00 | 74.65 |
| 14997 | C | TYR | C | 360 | -43.653 | -8.940 | -0.250 | 1.00 | 74.04 |
| 14998 | O | TYR | C | 360 | -43.665 | -9.823 | -1.114 | 1.00 | 74.02 |
| 14999 | N | PHE | C | 361 | -44.186 | -7.738 | -0.424 | 1.00 | 74.72 |
| 15000 | CA | PHE | C | 361 | -44.819 | -7.341 | -1.666 | 1.00 | 75.53 |
| 15001 | CB | PHE | C | 361 | -46.286 | -6.970 | -1.414 | 1.00 | 75.32 |
| 15002 | CG | PHE | C | 361 | -47.231 | -8.146 | -1.357 | 1.00 | 75.18 |
| 15003 | CD1 | PHE | C | 361 | -47.857 | -8.607 | -2.504 | 1.00 | 75.00 |
| 15004 | CE1 | PHE | C | 361 | -48.736 | -9.679 | -2.457 | 1.00 | 74.71 |
| 15005 | CZ | PHE | C | 361 | -49.011 | -10.289 | -1.254 | 1.00 | 74.46 |
| 15006 | CE2 | PHE | C | 361 | -48.404 | -9.833 | -0.099 | 1.00 | 75.01 |
| 15007 | CD2 | PHE | C | 361 | -47.524 | -8.762 | -0.153 | 1.00 | 74.85 |
| 15008 | C | PHE | C | 361 | -44.108 | -6.110 | -2.215 | 1.00 | 76.21 |
| 15009 | O | PHE | C | 361 | -43.591 | -5.292 | -1.459 | 1.00 | 76.39 |
| 15010 | N | GLN | C | 362 | -44.073 | -5.985 | -3.534 | 1.00 | 77.02 |
| 15011 | CA | GLN | C | 362 | -43.550 | -4.778 | -4.155 | 1.00 | 77.85 |
| 15012 | CB | GLN | C | 362 | -42.231 | -5.034 | -4.883 | 1.00 | 78.01 |
| 15013 | CG | GLN | C | 362 | -41.033 | -4.401 | -4.179 | 1.00 | 78.37 |
| 15014 | CD | GLN | C | 362 | -39.840 | -5.335 | -4.085 | 1.00 | 78.51 |
| 15015 | OE1 | GLN | C | 362 | -38.808 | -4.970 | -3.523 | 1.00 | 79.17 |
| 15016 | NE2 | GLN | C | 362 | -39.984 | -6.545 | -4.616 | 1.00 | 78.28 |
| 15017 | C | GLN | C | 362 | -44.596 | -4.185 | -5.081 | 1.00 | 78.28 |
| 15018 | O | GLN | C | 362 | -45.181 | -4.883 | -5.908 | 1.00 | 78.29 |
| 15019 | N | ILE | C | 363 | -44.827 | -2.891 | -4.914 | 1.00 | 78.94 |
| 15020 | CA | ILE | C | 363 | -45.822 | -2.141 | -5.675 | 1.00 | 79.80 |
| 15021 | CB | ILE | C | 363 | -45.522 | -0.624 | -5.530 | 1.00 | 79.78 |
| 15022 | CG1 | ILE | C | 363 | -45.905 | -0.145 | -4.130 | 1.00 | 79.68 |
| 15023 | CD1 | ILE | C | 363 | -47.258 | -0.584 | -3.695 | 1.00 | 79.04 |
| 15024 | CG2 | ILE | C | 363 | -46.248 | 0.197 | -6.569 | 1.00 | 79.98 |
| 15025 | C | ILE | C | 363 | -46.005 | -2.533 | -7.156 | 1.00 | 80.30 |
| 15026 | O | ILE | C | 363 | -46.978 | -2.126 | -7.782 | 1.00 | 80.38 |
| 15027 | N | ASP | C | 364 | -45.110 | -3.345 | -7.710 | 1.00 | 80.94 |
| 15028 | CA | ASP | C | 364 | -45.197 | -3.666 | -9.136 | 1.00 | 81.68 |
| 15029 | CB | ASP | C | 364 | -43.931 | -3.201 | -9.857 | 1.00 | 81.66 |
| 15030 | CG | ASP | C | 364 | -44.057 | -1.795 | -10.395 | 1.00 | 82.02 |
| 15031 | OD1 | ASP | C | 364 | -44.820 | -1.609 | -11.370 | 1.00 | 82.04 |
| 15032 | OD2 | ASP | C | 364 | -43.440 | -0.819 | -9.911 | 1.00 | 81.88 |
| 15033 | C | ASP | C | 364 | -45.495 | -5.109 | -9.540 | 1.00 | 82.16 |
| 15034 | O | ASP | C | 364 | -46.036 | -5.344 | -10.623 | 1.00 | 82.07 |
| 15035 | N | LYS | C | 365 | -45.148 | -6.072 | -8.690 | 1.00 | 82.73 |

FIGURE 3 KI

| A | B | C | D | E | F | G | H | I | J |
|---|---|---|---|---|---|---|---|---|---|
| 15036 | CA | LYS | C | 365 | -45.289 | -7.479 | -9.065 | 1.00 | 83.29 |
| 15037 | CB | LYS | C | 365 | -43.984 | -8.227 | -8.806 | 1.00 | 83.44 |
| 15038 | CG | LYS | C | 365 | -42.759 | -7.538 | -9.376 | 1.00 | 84.51 |
| 15039 | CD | LYS | C | 365 | -41.613 | -8.533 | -9.512 | 1.00 | 86.86 |
| 15040 | CE | LYS | C | 365 | -40.252 | -7.873 | -9.311 | 1.00 | 87.71 |
| 15041 | NZ | LYS | C | 365 | -39.224 | -8.880 | -8.916 | 1.00 | 88.36 |
| 15042 | C | LYS | C | 365 | -46.455 | -8.219 | -8.411 | 1.00 | 83.34 |
| 15043 | O | LYS | C | 365 | -46.762 | -8.019 | -7.235 | 1.00 | 83.50 |
| 15044 | N | LYS | C | 366 | -47.075 | -9.106 | -9.183 | 1.00 | 83.35 |
| 15045 | CA | LYS | C | 366 | -48.243 | -9.844 | -8.721 | 1.00 | 83.39 |
| 15046 | CB | LYS | C | 366 | -49.036 | -10.411 | -9.910 | 1.00 | 83.60 |
| 15047 | CG | LYS | C | 366 | -48.626 | -11.814 | -10.355 | 1.00 | 84.31 |
| 15048 | CD | LYS | C | 366 | -47.487 | -11.797 | -11.371 | 1.00 | 85.61 |
| 15049 | CE | LYS | C | 366 | -47.186 | -13.206 | -11.897 | 1.00 | 86.23 |
| 15050 | NZ | LYS | C | 366 | -48.397 | -13.882 | -12.470 | 1.00 | 86.15 |
| 15051 | C | LYS | C | 366 | -47.941 | -10.962 | -7.725 | 1.00 | 83.10 |
| 15052 | O | LYS | C | 366 | -48.848 | -11.444 | -7.045 | 1.00 | 83.31 |
| 15053 | N | ASP | C | 367 | -46.685 | -11.381 | -7.615 | 1.00 | 82.61 |
| 15054 | CA | ASP | C | 367 | -46.419 | -12.516 | -6.734 | 1.00 | 82.00 |
| 15055 | CB | ASP | C | 367 | -46.002 | -13.772 | -7.508 | 1.00 | 82.19 |
| 15056 | CG | ASP | C | 367 | -47.194 | -14.657 | -7.854 | 1.00 | 82.72 |
| 15057 | OD1 | ASP | C | 367 | -48.236 | -14.113 | -8.284 | 1.00 | 83.37 |
| 15058 | OD2 | ASP | C | 367 | -47.190 | -15.901 | -7.718 | 1.00 | 82.87 |
| 15059 | C | ASP | C | 367 | -45.579 | -12.312 | -5.479 | 1.00 | 81.38 |
| 15060 | O | ASP | C | 367 | -44.378 | -12.034 | -5.507 | 1.00 | 81.42 |
| 15061 | N | CYS | C | 368 | -46.292 | -12.472 | -4.377 | 1.00 | 80.38 |
| 15062 | CA | CYS | C | 368 | -45.807 | -12.363 | -3.024 | 1.00 | 79.24 |
| 15063 | CB | CYS | C | 368 | -47.032 | -12.575 | -2.134 | 1.00 | 79.05 |
| 15064 | SG | CYS | C | 368 | -46.742 | -13.495 | -0.629 | 1.00 | 77.56 |
| 15065 | C | CYS | C | 368 | -44.721 | -13.385 | -2.660 | 1.00 | 78.87 |
| 15066 | O | CYS | C | 368 | -44.689 | -14.494 | -3.196 | 1.00 | 78.67 |
| 15067 | N | THR | C | 369 | -43.835 | -13.000 | -1.745 | 1.00 | 78.25 |
| 15068 | CA | THR | C | 369 | -42.818 | -13.914 | -1.221 | 1.00 | 77.82 |
| 15069 | CB | THR | C | 369 | -41.409 | -13.544 | -1.732 | 1.00 | 77.94 |
| 15070 | OG1 | THR | C | 369 | -40.422 | -14.081 | -0.842 | 1.00 | 77.58 |
| 15071 | CG2 | THR | C | 369 | -41.180 | -12.037 | -1.653 | 1.00 | 78.12 |
| 15072 | C | THR | C | 369 | -42.863 | -13.925 | 0.310 | 1.00 | 77.36 |
| 15073 | O | THR | C | 369 | -42.684 | -12.883 | 0.953 | 1.00 | 77.28 |
| 15074 | N | PHE | C | 370 | -43.109 | -15.100 | 0.887 | 1.00 | 76.69 |
| 15075 | CA | PHE | C | 370 | -43.253 | -15.235 | 2.338 | 1.00 | 76.14 |
| 15076 | CB | PHE | C | 370 | -43.971 | -16.542 | 2.675 | 1.00 | 76.21 |
| 15077 | CG | PHE | C | 370 | -45.367 | -16.628 | 2.130 | 1.00 | 76.75 |
| 15078 | CD1 | PHE | C | 370 | -46.356 | -15.777 | 2.593 | 1.00 | 76.78 |
| 15079 | CE1 | PHE | C | 370 | -47.642 | -15.858 | 2.100 | 1.00 | 77.24 |
| 15080 | CZ | PHE | C | 370 | -47.957 | -16.789 | 1.129 | 1.00 | 77.79 |
| 15081 | CE2 | PHE | C | 370 | -46.984 | -17.652 | 0.660 | 1.00 | 77.95 |
| 15082 | CD2 | PHE | C | 370 | -45.694 | -17.568 | 1.161 | 1.00 | 77.40 |
| 15083 | C | PHE | C | 370 | -41.930 | -15.178 | 3.100 | 1.00 | 75.59 |
| 15084 | O | PHE | C | 370 | -41.067 | -16.023 | 2.905 | 1.00 | 75.56 |
| 15085 | N | ILE | C | 371 | -41.781 | -14.197 | 3.987 | 1.00 | 75.00 |
| 15086 | CA | ILE | C | 371 | -40.553 | -14.074 | 4.774 | 1.00 | 74.48 |

FIGURE 3 KJ

| A | B | C | D | E | F | G | H | I | J |
|---|---|---|---|---|---|---|---|---|---|
| 15087 | CB | ILE | C | 371 | -40.224 | -12.604 | 5.080 | 1.00 | 74.45 |
| 15088 | CG1 | ILE | C | 371 | -41.075 | -12.081 | 6.237 | 1.00 | 74.44 |
| 15089 | CD1 | ILE | C | 371 | -40.671 | -10.690 | 6.691 | 1.00 | 73.38 |
| 15090 | CG2 | ILE | C | 371 | -40.398 | -11.753 | 3.840 | 1.00 | 74.48 |
| 15091 | C | ILE | C | 371 | -40.547 | -14.910 | 6.062 | 1.00 | 74.18 |
| 15092 | O | ILE | C | 371 | -39.534 | -14.971 | 6.765 | 1.00 | 74.17 |
| 15093 | N | THR | C | 372 | -41.679 | -15.541 | 6.368 | 1.00 | 73.78 |
| 15094 | CA | THR | C | 372 | -41.783 | -16.474 | 7.491 | 1.00 | 73.26 |
| 15095 | CB | THR | C | 372 | -42.432 | -15.824 | 8.737 | 1.00 | 73.15 |
| 15096 | OG1 | THR | C | 372 | -43.538 | -15.007 | 8.343 | 1.00 | 73.10 |
| 15097 | CG2 | THR | C | 372 | -41.487 | -14.838 | 9.395 | 1.00 | 72.71 |
| 15098 | C | THR | C | 372 | -42.599 | -17.682 | 7.046 | 1.00 | 73.15 |
| 15099 | O | THR | C | 372 | -43.320 | -17.617 | 6.048 | 1.00 | 73.30 |
| 15100 | N | LYS | C | 373 | -42.484 | -18.783 | 7.780 | 1.00 | 72.86 |
| 15101 | CA | LYS | C | 373 | -43.240 | -19.997 | 7.470 | 1.00 | 72.65 |
| 15102 | CB | LYS | C | 373 | -42.706 | -20.661 | 6.196 | 1.00 | 72.82 |
| 15103 | CG | LYS | C | 373 | -42.761 | -22.185 | 6.182 | 1.00 | 73.44 |
| 15104 | CD | LYS | C | 373 | -41.522 | -22.784 | 6.853 | 1.00 | 74.34 |
| 15105 | CE | LYS | C | 373 | -41.593 | -24.304 | 6.916 | 1.00 | 74.49 |
| 15106 | NZ | LYS | C | 373 | -40.471 | -24.867 | 7.718 | 1.00 | 74.69 |
| 15107 | C | LYS | C | 373 | -43.227 | -20.958 | 8.655 | 1.00 | 72.30 |
| 15108 | O | LYS | C | 373 | -42.544 | -20.710 | 9.651 | 1.00 | 72.41 |
| 15109 | N | GLY | C | 374 | -43.992 | -22.041 | 8.560 | 1.00 | 71.83 |
| 15110 | CA | GLY | C | 374 | -44.054 | -23.018 | 9.634 | 1.00 | 71.28 |
| 15111 | C | GLY | C | 374 | -45.459 | -23.178 | 10.180 | 1.00 | 70.87 |
| 15112 | O | GLY | C | 374 | -46.300 | -22.297 | 10.010 | 1.00 | 70.98 |
| 15113 | N | THR | C | 375 | -45.716 | -24.297 | 10.850 | 1.00 | 70.35 |
| 15114 | CA | THR | C | 375 | -47.050 | -24.575 | 11.379 | 1.00 | 69.61 |
| 15115 | CB | THR | C | 375 | -47.231 | -26.072 | 11.641 | 1.00 | 69.71 |
| 15116 | OG1 | THR | C | 375 | -46.343 | -26.482 | 12.688 | 1.00 | 70.00 |
| 15117 | CG2 | THR | C | 375 | -46.773 | -26.879 | 10.431 | 1.00 | 69.74 |
| 15118 | C | THR | C | 375 | -47.392 | -23.773 | 12.633 | 1.00 | 69.01 |
| 15119 | O | THR | C | 375 | -47.752 | -24.331 | 13.673 | 1.00 | 68.90 |
| 15120 | N | TRP | C | 376 | -47.248 | -22.459 | 12.516 | 1.00 | 68.03 |
| 15121 | CA | TRP | C | 376 | -47.659 | -21.514 | 13.541 | 1.00 | 67.27 |
| 15122 | CB | TRP | C | 376 | -46.492 | -21.080 | 14.432 | 1.00 | 67.25 |
| 15123 | CG | TRP | C | 376 | -45.221 | -20.789 | 13.707 | 1.00 | 67.49 |
| 15124 | CD1 | TRP | C | 376 | -44.318 | -21.700 | 13.240 | 1.00 | 67.72 |
| 15125 | NE1 | TRP | C | 376 | -43.264 | -21.055 | 12.639 | 1.00 | 67.99 |
| 15126 | CE2 | TRP | C | 376 | -43.468 | -19.704 | 12.713 | 1.00 | 67.87 |
| 15127 | CD2 | TRP | C | 376 | -44.689 | -19.500 | 13.386 | 1.00 | 67.80 |
| 15128 | CE3 | TRP | C | 376 | -45.123 | -18.188 | 13.596 | 1.00 | 68.37 |
| 15129 | CZ3 | TRP | C | 376 | -44.338 | -17.143 | 13.137 | 1.00 | 69.05 |
| 15130 | CH2 | TRP | C | 376 | -43.129 | -17.381 | 12.475 | 1.00 | 68.72 |
| 15131 | CZ2 | TRP | C | 376 | -42.680 | -18.652 | 12.251 | 1.00 | 68.56 |
| 15132 | C | TRP | C | 376 | -48.247 | -20.340 | 12.772 | 1.00 | 66.68 |
| 15133 | O | TRP | C | 376 | -48.629 | -20.503 | 11.614 | 1.00 | 66.63 |
| 15134 | N | GLU | C | 377 | -48.329 | -19.165 | 13.385 | 1.00 | 65.79 |
| 15135 | CA | GLU | C | 377 | -48.887 | -18.012 | 12.678 | 1.00 | 64.99 |
| 15136 | CB | GLU | C | 377 | -50.419 | -18.010 | 12.746 | 1.00 | 64.86 |
| 15137 | CG | GLU | C | 377 | -51.109 | -18.870 | 11.705 | 1.00 | 64.15 |

FIGURE 3 KK

| A | B | C | D | E | F | G | H | I | J |
|---|---|---|---|---|---|---|---|---|---|
| 15138 | CD | GLU | C | 377 | -52.598 | -18.594 | 11.611 | 1.00 | 63.47 |
| 15139 | OE1 | GLU | C | 377 | -53.272 | -19.248 | 10.792 | 1.00 | 62.60 |
| 15140 | OE2 | GLU | C | 377 | -53.094 | -17.719 | 12.351 | 1.00 | 63.07 |
| 15141 | C | GLU | C | 377 | -48.381 | -16.689 | 13.209 | 1.00 | 64.51 |
| 15142 | O | GLU | C | 377 | -48.070 | -16.556 | 14.388 | 1.00 | 64.50 |
| 15143 | N | VAL | C | 378 | -48.299 | -15.709 | 12.321 | 1.00 | 64.08 |
| 15144 | CA | VAL | C | 378 | -47.929 | -14.365 | 12.710 | 1.00 | 63.89 |
| 15145 | CB | VAL | C | 378 | -47.246 | -13.617 | 11.563 | 1.00 | 63.89 |
| 15146 | CG1 | VAL | C | 378 | -46.862 | -12.223 | 12.004 | 1.00 | 64.19 |
| 15147 | CG2 | VAL | C | 378 | -46.029 | -14.377 | 11.089 | 1.00 | 64.23 |
| 15148 | C | VAL | C | 378 | -49.215 | -13.640 | 13.083 | 1.00 | 63.81 |
| 15149 | O | VAL | C | 378 | -50.144 | -13.555 | 12.279 | 1.00 | 63.51 |
| 15150 | N | ILE | C | 379 | -49.281 | -13.137 | 14.307 | 1.00 | 63.71 |
| 15151 | CA | ILE | C | 379 | -50.478 | -12.447 | 14.751 | 1.00 | 63.80 |
| 15152 | CB | ILE | C | 379 | -50.504 | -12.332 | 16.275 | 1.00 | 63.89 |
| 15153 | CG1 | ILE | C | 379 | -50.146 | -13.676 | 16.922 | 1.00 | 63.72 |
| 15154 | CD1 | ILE | C | 379 | -51.032 | -14.813 | 16.502 | 1.00 | 63.32 |
| 15155 | CG2 | ILE | C | 379 | -51.863 | -11.835 | 16.732 | 1.00 | 63.72 |
| 15156 | C | ILE | C | 379 | -50.597 | -11.068 | 14.113 | 1.00 | 63.94 |
| 15157 | O | ILE | C | 379 | -51.646 | -10.711 | 13.578 | 1.00 | 63.80 |
| 15158 | N | GLY | C | 380 | -49.517 | -10.296 | 14.160 | 1.00 | 64.02 |
| 15159 | CA | GLY | C | 380 | -49.534 | -8.968 | 13.578 | 1.00 | 64.29 |
| 15160 | C | GLY | C | 380 | -48.179 | -8.302 | 13.415 | 1.00 | 64.54 |
| 15161 | O | GLY | C | 380 | -47.232 | -8.570 | 14.162 | 1.00 | 64.54 |
| 15162 | N | ILE | C | 381 | -48.089 | -7.428 | 12.421 | 1.00 | 64.57 |
| 15163 | CA | ILE | C | 381 | -46.873 | -6.676 | 12.192 | 1.00 | 64.84 |
| 15164 | CB | ILE | C | 381 | -46.717 | -6.344 | 10.707 | 1.00 | 64.72 |
| 15165 | CG1 | ILE | C | 381 | -46.552 | -7.631 | 9.899 | 1.00 | 64.80 |
| 15166 | CD1 | ILE | C | 381 | -46.571 | -7.435 | 8.394 | 1.00 | 64.65 |
| 15167 | CG2 | ILE | C | 381 | -45.519 | -5.436 | 10.498 | 1.00 | 64.95 |
| 15168 | C | ILE | C | 381 | -46.907 | -5.421 | 13.059 | 1.00 | 65.21 |
| 15169 | O | ILE | C | 381 | -47.781 | -4.563 | 12.907 | 1.00 | 65.15 |
| 15170 | N | GLU | C | 382 | -45.956 | -5.329 | 13.979 | 1.00 | 65.60 |
| 15171 | CA | GLU | C | 382 | -45.921 | -4.231 | 14.935 | 1.00 | 66.17 |
| 15172 | CB | GLU | C | 382 | -45.389 | -4.731 | 16.278 | 1.00 | 66.09 |
| 15173 | CG | GLU | C | 382 | -46.177 | -5.902 | 16.839 | 1.00 | 65.95 |
| 15174 | CD | GLU | C | 382 | -47.639 | -5.561 | 17.052 | 1.00 | 65.14 |
| 15175 | OE1 | GLU | C | 382 | -48.503 | -6.320 | 16.566 | 1.00 | 65.03 |
| 15176 | OE2 | GLU | C | 382 | -47.920 | -4.529 | 17.700 | 1.00 | 64.58 |
| 15177 | C | GLU | C | 382 | -45.093 | -3.047 | 14.464 | 1.00 | 66.69 |
| 15178 | O | GLU | C | 382 | -45.406 | -1.896 | 14.773 | 1.00 | 66.74 |
| 15179 | N | ALA | C | 383 | -44.029 | -3.327 | 13.726 | 1.00 | 67.53 |
| 15180 | CA | ALA | C | 383 | -43.170 | -2.266 | 13.233 | 1.00 | 68.34 |
| 15181 | CB | ALA | C | 383 | -42.480 | -1.559 | 14.388 | 1.00 | 68.30 |
| 15182 | C | ALA | C | 383 | -42.145 | -2.820 | 12.270 | 1.00 | 69.06 |
| 15183 | O | ALA | C | 383 | -41.887 | -4.025 | 12.243 | 1.00 | 68.99 |
| 15184 | N | LEU | C | 384 | -41.574 | -1.931 | 11.466 | 1.00 | 70.07 |
| 15185 | CA | LEU | C | 384 | -40.537 | -2.322 | 10.529 | 1.00 | 71.18 |
| 15186 | CB | LEU | C | 384 | -41.134 | -2.985 | 9.283 | 1.00 | 71.08 |
| 15187 | CG | LEU | C | 384 | -41.598 | -2.215 | 8.050 | 1.00 | 70.73 |
| 15188 | CD1 | LEU | C | 384 | -42.255 | -0.893 | 8.410 | 1.00 | 71.00 |

FIGURE 3 KL

| A | B | C | D | E | F | G | H | I | J |
|---|---|---|---|---|---|---|---|---|---|
| 15189 | CD2 | LEU | C | 384 | -40.432 | -2.013 | 7.115 | 1.00 | 70.62 |
| 15190 | C | LEU | C | 384 | -39.638 | -1.147 | 10.175 | 1.00 | 72.11 |
| 15191 | O | LEU | C | 384 | -40.065 | 0.013 | 10.174 | 1.00 | 72.11 |
| 15192 | N | THR | C | 385 | -38.375 | -1.459 | 9.908 | 1.00 | 73.22 |
| 15193 | CA | THR | C | 385 | -37.399 | -0.450 | 9.537 | 1.00 | 74.09 |
| 15194 | CB | THR | C | 385 | -36.324 | -0.313 | 10.622 | 1.00 | 74.18 |
| 15195 | OG1 | THR | C | 385 | -35.765 | -1.604 | 10.900 | 1.00 | 74.54 |
| 15196 | CG2 | THR | C | 385 | -36.942 | 0.105 | 11.952 | 1.00 | 74.19 |
| 15197 | C | THR | C | 385 | -36.739 | -0.886 | 8.250 | 1.00 | 74.71 |
| 15198 | O | THR | C | 385 | -37.142 | -1.878 | 7.633 | 1.00 | 74.71 |
| 15199 | N | SER | C | 386 | -35.714 | -0.141 | 7.852 | 1.00 | 75.39 |
| 15200 | CA | SER | C | 386 | -34.951 | -0.481 | 6.666 | 1.00 | 75.74 |
| 15201 | CB | SER | C | 386 | -33.885 | 0.581 | 6.409 | 1.00 | 75.89 |
| 15202 | OG | SER | C | 386 | -33.049 | 0.745 | 7.543 | 1.00 | 76.23 |
| 15203 | C | SER | C | 386 | -34.299 | -1.844 | 6.871 | 1.00 | 75.84 |
| 15204 | O | SER | C | 386 | -34.289 | -2.679 | 5.965 | 1.00 | 75.99 |
| 15205 | N | ASP | C | 387 | -33.787 | -2.070 | 8.080 | 1.00 | 75.87 |
| 15206 | CA | ASP | C | 387 | -33.075 | -3.304 | 8.412 | 1.00 | 75.91 |
| 15207 | CB | ASP | C | 387 | -31.965 | -3.012 | 9.423 | 1.00 | 75.99 |
| 15208 | CG | ASP | C | 387 | -30.943 | -2.022 | 8.902 | 1.00 | 76.35 |
| 15209 | OD1 | ASP | C | 387 | -30.150 | -2.397 | 8.007 | 1.00 | 76.07 |
| 15210 | OD2 | ASP | C | 387 | -30.858 | -0.851 | 9.335 | 1.00 | 76.17 |
| 15211 | C | ASP | C | 387 | -33.956 | -4.409 | 8.986 | 1.00 | 75.86 |
| 15212 | O | ASP | C | 387 | -33.943 | -5.543 | 8.504 | 1.00 | 75.84 |
| 15213 | N | TYR | C | 388 | -34.710 | -4.071 | 10.028 | 1.00 | 75.74 |
| 15214 | CA | TYR | C | 388 | -35.521 | -5.052 | 10.742 | 1.00 | 75.46 |
| 15215 | CB | TYR | C | 388 | -35.201 | -4.996 | 12.238 | 1.00 | 75.65 |
| 15216 | CG | TYR | C | 388 | -33.825 | -5.486 | 12.616 | 1.00 | 76.32 |
| 15217 | CD1 | TYR | C | 388 | -32.846 | -4.601 | 13.056 | 1.00 | 76.99 |
| 15218 | CE1 | TYR | C | 388 | -31.584 | -5.046 | 13.417 | 1.00 | 77.33 |
| 15219 | CZ | TYR | C | 388 | -31.291 | -6.394 | 13.340 | 1.00 | 77.96 |
| 15220 | OH | TYR | C | 388 | -30.037 | -6.857 | 13.690 | 1.00 | 77.89 |
| 15221 | CE2 | TYR | C | 388 | -32.254 | -7.289 | 12.909 | 1.00 | 77.82 |
| 15222 | CD2 | TYR | C | 388 | -33.508 | -6.834 | 12.550 | 1.00 | 76.98 |
| 15223 | C | TYR | C | 388 | -37.026 | -4.869 | 10.578 | 1.00 | 74.96 |
| 15224 | O | TYR | C | 388 | -37.511 | -3.766 | 10.309 | 1.00 | 75.20 |
| 15225 | N | LEU | C | 389 | -37.750 | -5.972 | 10.746 | 1.00 | 74.08 |
| 15226 | CA | LEU | C | 389 | -39.207 | -5.977 | 10.767 | 1.00 | 73.25 |
| 15227 | CB | LEU | C | 389 | -39.778 | -6.765 | 9.582 | 1.00 | 73.17 |
| 15228 | CG | LEU | C | 389 | -41.282 | -7.089 | 9.609 | 1.00 | 73.03 |
| 15229 | CD1 | LEU | C | 389 | -42.102 | -5.935 | 9.072 | 1.00 | 73.08 |
| 15230 | CD2 | LEU | C | 389 | -41.589 | -8.335 | 8.808 | 1.00 | 72.28 |
| 15231 | C | LEU | C | 389 | -39.594 | -6.648 | 12.082 | 1.00 | 72.63 |
| 15232 | O | LEU | C | 389 | -39.166 | -7.765 | 12.362 | 1.00 | 72.66 |
| 15233 | N | TYR | C | 390 | -40.388 | -5.971 | 12.898 | 1.00 | 71.77 |
| 15234 | CA | TYR | C | 390 | -40.778 | -6.532 | 14.181 | 1.00 | 71.08 |
| 15235 | CB | TYR | C | 390 | -40.611 | -5.495 | 15.283 | 1.00 | 71.26 |
| 15236 | CG | TYR | C | 390 | -39.202 | -4.979 | 15.456 | 1.00 | 71.69 |
| 15237 | CD1 | TYR | C | 390 | -38.352 | -5.537 | 16.399 | 1.00 | 72.61 |
| 15238 | CE1 | TYR | C | 390 | -37.063 | -5.063 | 16.574 | 1.00 | 73.10 |
| 15239 | CZ | TYR | C | 390 | -36.610 | -4.017 | 15.802 | 1.00 | 73.31 |

FIGURE 3 KM

| A | B | C | D | E | F | G | H | I | J |
|---|---|---|---|---|---|---|---|---|---|
| 15240 | OH | TYR | C | 390 | -35.328 | -3.552 | 15.981 | 1.00 | 74.22 |
| 15241 | CE2 | TYR | C | 390 | -37.437 | -3.442 | 14.857 | 1.00 | 72.86 |
| 15242 | CD2 | TYR | C | 390 | -38.726 | -3.922 | 14.692 | 1.00 | 72.23 |
| 15243 | C | TYR | C | 390 | -42.222 | -7.014 | 14.153 | 1.00 | 70.54 |
| 15244 | O | TYR | C | 390 | -43.129 | -6.248 | 13.827 | 1.00 | 70.53 |
| 15245 | N | TYR | C | 391 | -42.433 | -8.280 | 14.505 | 1.00 | 69.72 |
| 15246 | CA | TYR | C | 391 | -43.770 | -8.862 | 14.511 | 1.00 | 68.92 |
| 15247 | CB | TYR | C | 391 | -43.988 | -9.684 | 13.244 | 1.00 | 68.70 |
| 15248 | CG | TYR | C | 391 | -43.251 | -11.002 | 13.247 | 1.00 | 68.25 |
| 15249 | CD1 | TYR | C | 391 | -43.823 | -12.136 | 13.805 | 1.00 | 67.77 |
| 15250 | CE1 | TYR | C | 391 | -43.157 | -13.340 | 13.813 | 1.00 | 67.68 |
| 15251 | CZ | TYR | C | 391 | -41.894 | -13.430 | 13.256 | 1.00 | 68.06 |
| 15252 | OH | TYR | C | 391 | -41.228 | -14.637 | 13.262 | 1.00 | 67.59 |
| 15253 | CE2 | TYR | C | 391 | -41.301 | -12.318 | 12.693 | 1.00 | 67.91 |
| 15254 | CD2 | TYR | C | 391 | -41.982 | -11.111 | 12.694 | 1.00 | 68.53 |
| 15255 | C | TYR | C | 391 | -44.015 | -9.749 | 15.733 | 1.00 | 68.50 |
| 15256 | O | TYR | C | 391 | -43.085 | -10.115 | 16.442 | 1.00 | 68.48 |
| 15257 | N | ILE | C | 392 | -45.280 | -10.090 | 15.971 | 1.00 | 67.95 |
| 15258 | CA | ILE | C | 392 | -45.644 | -10.989 | 17.060 | 1.00 | 67.42 |
| 15259 | CB | ILE | C | 392 | -46.625 | -10.305 | 18.021 | 1.00 | 67.47 |
| 15260 | CG1 | ILE | C | 392 | -45.847 | -9.569 | 19.109 | 1.00 | 67.27 |
| 15261 | CD1 | ILE | C | 392 | -46.609 | -8.451 | 19.751 | 1.00 | 67.55 |
| 15262 | CG2 | ILE | C | 392 | -47.575 | -11.322 | 18.647 | 1.00 | 67.28 |
| 15263 | C | ILE | C | 392 | -46.238 | -12.254 | 16.462 | 1.00 | 67.12 |
| 15264 | O | ILE | C | 392 | -46.812 | -12.214 | 15.379 | 1.00 | 67.16 |
| 15265 | N | SER | C | 393 | -46.082 | -13.379 | 17.147 | 1.00 | 66.70 |
| 15266 | CA | SER | C | 393 | -46.593 | -14.640 | 16.626 | 1.00 | 66.57 |
| 15267 | CB | SER | C | 393 | -45.690 | -15.151 | 15.503 | 1.00 | 66.66 |
| 15268 | OG | SER | C | 393 | -44.423 | -15.548 | 16.003 | 1.00 | 67.01 |
| 15269 | C | SER | C | 393 | -46.703 | -15.696 | 17.717 | 1.00 | 66.31 |
| 15270 | O | SER | C | 393 | -46.386 | -15.438 | 18.871 | 1.00 | 66.19 |
| 15271 | N | ASN | C | 394 | -47.155 | -16.888 | 17.348 | 1.00 | 66.35 |
| 15272 | CA | ASN | C | 394 | -47.292 | -17.972 | 18.319 | 1.00 | 66.39 |
| 15273 | CB | ASN | C | 394 | -48.750 | -18.444 | 18.407 | 1.00 | 66.16 |
| 15274 | CG | ASN | C | 394 | -49.319 | -18.846 | 17.066 | 1.00 | 65.56 |
| 15275 | OD1 | ASN | C | 394 | -48.593 | -18.981 | 16.086 | 1.00 | 65.23 |
| 15276 | ND2 | ASN | C | 394 | -50.629 | -19.040 | 17.016 | 1.00 | 65.22 |
| 15277 | C | ASN | C | 394 | -46.356 | -19.157 | 18.052 | 1.00 | 66.50 |
| 15278 | O | ASN | C | 394 | -46.687 | -20.300 | 18.368 | 1.00 | 66.51 |
| 15279 | N | GLU | C | 395 | -45.185 | -18.875 | 17.482 | 1.00 | 66.64 |
| 15280 | CA | GLU | C | 395 | -44.230 | -19.924 | 17.142 | 1.00 | 66.67 |
| 15281 | CB | GLU | C | 395 | -43.072 | -19.370 | 16.307 | 1.00 | 66.82 |
| 15282 | CG | GLU | C | 395 | -42.122 | -20.459 | 15.822 | 1.00 | 67.70 |
| 15283 | CD | GLU | C | 395 | -40.949 | -19.930 | 15.020 | 1.00 | 68.12 |
| 15284 | OE1 | GLU | C | 395 | -40.322 | -20.728 | 14.288 | 1.00 | 68.71 |
| 15285 | OE2 | GLU | C | 395 | -40.651 | -18.723 | 15.121 | 1.00 | 68.27 |
| 15286 | C | GLU | C | 395 | -43.671 | -20.641 | 18.362 | 1.00 | 66.42 |
| 15287 | O | GLU | C | 395 | -43.648 | -21.873 | 18.412 | 1.00 | 66.27 |
| 15288 | N | TYR | C | 396 | -43.225 | -19.866 | 19.342 | 1.00 | 66.28 |
| 15289 | CA | TYR | C | 396 | -42.606 | -20.436 | 20.531 | 1.00 | 66.48 |
| 15290 | CB | TYR | C | 396 | -42.505 | -19.408 | 21.659 | 1.00 | 66.75 |

FIGURE 3 KN

| A | B | C | D | E | F | G | H | I | J |
|---|---|---|---|---|---|---|---|---|---|
| 15291 | CG | TYR | C | 396 | -41.531 | -19.826 | 22.736 | 1.00 | 67.82 |
| 15292 | CD1 | TYR | C | 396 | -41.874 | -19.764 | 24.081 | 1.00 | 68.27 |
| 15293 | CE1 | TYR | C | 396 | -40.981 | -20.158 | 25.063 | 1.00 | 69.27 |
| 15294 | CZ | TYR | C | 396 | -39.731 | -20.626 | 24.704 | 1.00 | 69.93 |
| 15295 | OH | TYR | C | 396 | -38.833 | -21.021 | 25.674 | 1.00 | 70.35 |
| 15296 | CE2 | TYR | C | 396 | -39.372 | -20.701 | 23.373 | 1.00 | 69.62 |
| 15297 | CD2 | TYR | C | 396 | -40.269 | -20.305 | 22.401 | 1.00 | 68.57 |
| 15298 | C | TYR | C | 396 | -43.299 | -21.704 | 21.019 | 1.00 | 66.20 |
| 15299 | O | TYR | C | 396 | -44.528 | -21.795 | 21.038 | 1.00 | 66.42 |
| 15300 | N | LYS | C | 397 | -42.488 | -22.691 | 21.384 | 1.00 | 65.75 |
| 15301 | CA | LYS | C | 397 | -42.971 | -23.970 | 21.900 | 1.00 | 65.28 |
| 15302 | CB | LYS | C | 397 | -43.252 | -23.873 | 23.400 | 1.00 | 65.42 |
| 15303 | CG | LYS | C | 397 | -42.018 | -23.960 | 24.289 | 1.00 | 65.46 |
| 15304 | CD | LYS | C | 397 | -42.305 | -23.373 | 25.669 | 1.00 | 66.31 |
| 15305 | CE | LYS | C | 397 | -41.350 | -23.920 | 26.725 | 1.00 | 66.99 |
| 15306 | NZ | LYS | C | 397 | -39.955 | -24.025 | 26.215 | 1.00 | 67.31 |
| 15307 | C | LYS | C | 397 | -44.204 | -24.501 | 21.186 | 1.00 | 64.87 |
| 15308 | O | LYS | C | 397 | -44.865 | -25.410 | 21.688 | 1.00 | 64.77 |
| 15309 | N | GLY | C | 398 | -44.513 | -23.939 | 20.021 | 1.00 | 64.29 |
| 15310 | CA | GLY | C | 398 | -45.661 | -24.389 | 19.254 | 1.00 | 63.76 |
| 15311 | C | GLY | C | 398 | -46.945 | -24.313 | 20.057 | 1.00 | 63.30 |
| 15312 | O | GLY | C | 398 | -47.739 | -25.256 | 20.076 | 1.00 | 63.47 |
| 15313 | N | MET | C | 399 | -47.133 | -23.188 | 20.738 | 1.00 | 62.72 |
| 15314 | CA | MET | C | 399 | -48.319 | -22.965 | 21.547 | 1.00 | 61.97 |
| 15315 | CB | MET | C | 399 | -47.931 | -22.537 | 22.963 | 1.00 | 61.89 |
| 15316 | CG | MET | C | 399 | -46.667 | -23.173 | 23.498 | 1.00 | 62.45 |
| 15317 | SD | MET | C | 399 | -46.535 | -23.090 | 25.306 | 1.00 | 62.64 |
| 15318 | CE | MET | C | 399 | -47.375 | -24.588 | 25.754 | 1.00 | 62.36 |
| 15319 | C | MET | C | 399 | -49.156 | -21.867 | 20.902 | 1.00 | 61.45 |
| 15320 | O | MET | C | 399 | -48.801 | -20.691 | 20.967 | 1.00 | 61.30 |
| 15321 | N | PRO | C | 400 | -50.255 | -22.252 | 20.266 | 1.00 | 60.94 |
| 15322 | CA | PRO | C | 400 | -51.156 | -21.294 | 19.612 | 1.00 | 60.42 |
| 15323 | CB | PRO | C | 400 | -52.332 | -22.169 | 19.192 | 1.00 | 60.57 |
| 15324 | CG | PRO | C | 400 | -51.728 | -23.522 | 19.009 | 1.00 | 60.79 |
| 15325 | CD | PRO | C | 400 | -50.699 | -23.644 | 20.094 | 1.00 | 60.71 |
| 15326 | C | PRO | C | 400 | -51.633 | -20.192 | 20.552 | 1.00 | 60.01 |
| 15327 | O | PRO | C | 400 | -51.817 | -19.057 | 20.123 | 1.00 | 59.89 |
| 15328 | N | GLY | C | 401 | -51.821 | -20.524 | 21.825 | 1.00 | 59.54 |
| 15329 | CA | GLY | C | 401 | -52.283 | -19.561 | 22.806 | 1.00 | 58.92 |
| 15330 | C | GLY | C | 401 | -51.167 | -18.736 | 23.410 | 1.00 | 58.69 |
| 15331 | O | GLY | C | 401 | -51.384 | -17.964 | 24.340 | 1.00 | 58.61 |
| 15332 | N | GLY | C | 402 | -49.960 | -18.906 | 22.889 | 1.00 | 58.52 |
| 15333 | CA | GLY | C | 402 | -48.831 | -18.135 | 23.358 | 1.00 | 58.25 |
| 15334 | C | GLY | C | 402 | -48.493 | -17.041 | 22.373 | 1.00 | 58.21 |
| 15335 | O | GLY | C | 402 | -48.727 | -17.185 | 21.175 | 1.00 | 57.66 |
| 15336 | N | ARG | C | 403 | -47.940 | -15.947 | 22.885 | 1.00 | 58.56 |
| 15337 | CA | ARG | C | 403 | -47.571 | -14.794 | 22.068 | 1.00 | 59.11 |
| 15338 | CB | ARG | C | 403 | -48.529 | -13.631 | 22.334 | 1.00 | 59.24 |
| 15339 | CG | ARG | C | 403 | -49.540 | -13.330 | 21.236 | 1.00 | 59.55 |
| 15340 | CD | ARG | C | 403 | -50.288 | -14.530 | 20.729 | 1.00 | 59.11 |
| 15341 | NE | ARG | C | 403 | -51.619 | -14.189 | 20.246 | 1.00 | 58.74 |

FIGURE 3 KO

| A | B | C | D | E | F | G | H | I | J |
|---|---|---|---|---|---|---|---|---|---|
| 15342 | CZ | ARG | C | 403 | -52.564 | -15.090 | 20.013 | 1.00 | 59.71 |
| 15343 | NH1 | ARG | C | 403 | -53.761 | -14.713 | 19.577 | 1.00 | 60.37 |
| 15344 | NH2 | ARG | C | 403 | -52.311 | -16.379 | 20.214 | 1.00 | 59.35 |
| 15345 | C | ARG | C | 403 | -46.163 | -14.328 | 22.396 | 1.00 | 59.34 |
| 15346 | O | ARG | C | 403 | -45.799 | -14.214 | 23.557 | 1.00 | 59.25 |
| 15347 | N | ASN | C | 404 | -45.373 | -14.048 | 21.370 | 1.00 | 60.20 |
| 15348 | CA | ASN | C | 404 | -44.026 | -13.535 | 21.571 | 1.00 | 60.98 |
| 15349 | CB | ASN | C | 404 | -43.009 | -14.672 | 21.692 | 1.00 | 60.61 |
| 15350 | CG | ASN | C | 404 | -42.957 | -15.252 | 23.081 | 1.00 | 59.51 |
| 15351 | OD1 | ASN | C | 404 | -43.361 | -16.392 | 23.302 | 1.00 | 58.86 |
| 15352 | ND2 | ASN | C | 404 | -42.473 | -14.465 | 24.034 | 1.00 | 56.75 |
| 15353 | C | ASN | C | 404 | -43.604 | -12.578 | 20.477 | 1.00 | 61.92 |
| 15354 | O | ASN | C | 404 | -44.037 | -12.692 | 19.330 | 1.00 | 62.03 |
| 15355 | N | LEU | C | 405 | -42.751 | -11.634 | 20.850 | 1.00 | 63.31 |
| 15356 | CA | LEU | C | 405 | -42.228 | -10.646 | 19.921 | 1.00 | 64.62 |
| 15357 | CB | LEU | C | 405 | -41.855 | -9.375 | 20.678 | 1.00 | 64.50 |
| 15358 | CG | LEU | C | 405 | -41.271 | -8.234 | 19.852 | 1.00 | 64.07 |
| 15359 | CD1 | LEU | C | 405 | -42.203 | -7.902 | 18.707 | 1.00 | 64.27 |
| 15360 | CD2 | LEU | C | 405 | -41.044 | -7.020 | 20.725 | 1.00 | 63.89 |
| 15361 | C | LEU | C | 405 | -41.003 | -11.188 | 19.186 | 1.00 | 65.74 |
| 15362 | O | LEU | C | 405 | -40.084 | -11.726 | 19.799 | 1.00 | 65.57 |
| 15363 | N | TYR | C | 406 | -40.996 | -11.044 | 17.867 | 1.00 | 67.23 |
| 15364 | CA | TYR | C | 406 | -39.878 | -11.515 | 17.066 | 1.00 | 68.66 |
| 15365 | CB | TYR | C | 406 | -40.300 | -12.700 | 16.199 | 1.00 | 68.64 |
| 15366 | CG | TYR | C | 406 | -40.543 | -13.966 | 16.981 | 1.00 | 69.15 |
| 15367 | CD1 | TYR | C | 406 | -39.603 | -14.985 | 16.994 | 1.00 | 69.73 |
| 15368 | CE1 | TYR | C | 406 | -39.816 | -16.145 | 17.707 | 1.00 | 69.38 |
| 15369 | CZ | TYR | C | 406 | -40.977 | -16.299 | 18.424 | 1.00 | 69.23 |
| 15370 | OH | TYR | C | 406 | -41.180 | -17.457 | 19.137 | 1.00 | 70.18 |
| 15371 | CE2 | TYR | C | 406 | -41.927 | -15.304 | 18.432 | 1.00 | 69.38 |
| 15372 | CD2 | TYR | C | 406 | -41.707 | -14.142 | 17.713 | 1.00 | 69.55 |
| 15373 | C | TYR | C | 406 | -39.323 | -10.405 | 16.189 | 1.00 | 69.60 |
| 15374 | O | TYR | C | 406 | -40.053 | -9.504 | 15.776 | 1.00 | 69.80 |
| 15375 | N | LYS | C | 407 | -38.024 | -10.479 | 15.916 | 1.00 | 70.75 |
| 15376 | CA | LYS | C | 407 | -37.349 | -9.527 | 15.040 | 1.00 | 71.87 |
| 15377 | CB | LYS | C | 407 | -36.271 | -8.765 | 15.816 | 1.00 | 71.82 |
| 15378 | CG | LYS | C | 407 | -35.043 | -8.425 | 15.001 | 1.00 | 72.36 |
| 15379 | CD | LYS | C | 407 | -33.811 | -8.216 | 15.882 | 1.00 | 73.33 |
| 15380 | CE | LYS | C | 407 | -33.870 | -6.892 | 16.648 | 1.00 | 73.70 |
| 15381 | NZ | LYS | C | 407 | -32.523 | -6.458 | 17.135 | 1.00 | 72.93 |
| 15382 | C | LYS | C | 407 | -36.730 | -10.275 | 13.859 | 1.00 | 72.57 |
| 15383 | O | LYS | C | 407 | -35.918 | -11.184 | 14.049 | 1.00 | 72.66 |
| 15384 | N | ILE | C | 408 | -37.134 | -9.920 | 12.642 | 1.00 | 73.55 |
| 15385 | CA | ILE | C | 408 | -36.574 | -10.569 | 11.457 | 1.00 | 74.61 |
| 15386 | CB | ILE | C | 408 | -37.675 | -11.197 | 10.573 | 1.00 | 74.55 |
| 15387 | CG1 | ILE | C | 408 | -37.061 | -11.771 | 9.292 | 1.00 | 74.57 |
| 15388 | CD1 | ILE | C | 408 | -37.993 | -12.675 | 8.518 | 1.00 | 74.07 |
| 15389 | CG2 | ILE | C | 408 | -38.743 | -10.177 | 10.235 | 1.00 | 74.38 |
| 15390 | C | ILE | C | 408 | -35.690 | -9.619 | 10.650 | 1.00 | 75.36 |
| 15391 | O | ILE | C | 408 | -36.025 | -8.444 | 10.458 | 1.00 | 75.35 |
| 15392 | N | GLN | C | 409 | -34.550 | -10.134 | 10.195 | 1.00 | 76.31 |

FIGURE 3 KP

| A | B | C | D | E | F | G | H | I | J |
|---|---|---|---|---|---|---|---|---|---|
| 15393 | CA | GLN | C | 409 | -33.606 | -9.332 | 9.429 | 1.00 | 77.25 |
| 15394 | CB | GLN | C | 409 | -32.189 | -9.896 | 9.536 | 1.00 | 77.43 |
| 15395 | CG | GLN | C | 409 | -31.403 | -9.345 | 10.712 | 1.00 | 78.15 |
| 15396 | CD | GLN | C | 409 | -29.901 | -9.363 | 10.486 | 1.00 | 79.40 |
| 15397 | OE1 | GLN | C | 409 | -29.187 | -10.134 | 11.130 | 1.00 | 79.63 |
| 15398 | NE2 | GLN | C | 409 | -29.416 | -8.511 | 9.578 | 1.00 | 79.37 |
| 15399 | C | GLN | C | 409 | -34.006 | -9.209 | 7.971 | 1.00 | 77.64 |
| 15400 | O | GLN | C | 409 | -33.949 | -10.183 | 7.217 | 1.00 | 77.63 |
| 15401 | N | LEU | C | 410 | -34.408 | -8.004 | 7.579 | 1.00 | 78.26 |
| 15402 | CA | LEU | C | 410 | -34.802 | -7.746 | 6.199 | 1.00 | 78.91 |
| 15403 | CB | LEU | C | 410 | -35.204 | -6.283 | 6.024 | 1.00 | 78.97 |
| 15404 | CG | LEU | C | 410 | -36.688 | -5.972 | 6.239 | 1.00 | 79.51 |
| 15405 | CD1 | LEU | C | 410 | -37.403 | -7.109 | 6.947 | 1.00 | 79.61 |
| 15406 | CD2 | LEU | C | 410 | -36.862 | -4.665 | 6.994 | 1.00 | 80.14 |
| 15407 | C | LEU | C | 410 | -33.657 | -8.103 | 5.261 | 1.00 | 79.27 |
| 15408 | O | LEU | C | 410 | -33.875 | -8.460 | 4.100 | 1.00 | 79.38 |
| 15409 | N | SER | C | 411 | -32.436 | -8.010 | 5.781 | 1.00 | 79.62 |
| 15410 | CA | SER | C | 411 | -31.244 | -8.354 | 5.024 | 1.00 | 79.96 |
| 15411 | CB | SER | C | 411 | -29.989 | -7.847 | 5.741 | 1.00 | 80.09 |
| 15412 | OG | SER | C | 411 | -29.988 | -8.221 | 7.110 | 1.00 | 80.33 |
| 15413 | C | SER | C | 411 | -31.179 | -9.862 | 4.828 | 1.00 | 80.08 |
| 15414 | O | SER | C | 411 | -30.775 | -10.346 | 3.773 | 1.00 | 80.06 |
| 15415 | N | ASP | C | 412 | -31.573 | -10.603 | 5.857 | 1.00 | 80.29 |
| 15416 | CA | ASP | C | 412 | -31.625 | -12.057 | 5.755 | 1.00 | 80.44 |
| 15417 | CB | ASP | C | 412 | -30.365 | -12.717 | 6.306 | 1.00 | 80.22 |
| 15418 | CG | ASP | C | 412 | -30.399 | -14.225 | 6.157 | 1.00 | 80.04 |
| 15419 | OD1 | ASP | C | 412 | -30.016 | -14.927 | 7.110 | 1.00 | 80.13 |
| 15420 | OD2 | ASP | C | 412 | -30.811 | -14.800 | 5.126 | 1.00 | 79.50 |
| 15421 | C | ASP | C | 412 | -32.857 | -12.602 | 6.463 | 1.00 | 80.53 |
| 15422 | O | ASP | C | 412 | -32.962 | -12.544 | 7.691 | 1.00 | 80.55 |
| 15423 | N | TYR | C | 413 | -33.778 | -13.144 | 5.674 | 1.00 | 80.65 |
| 15424 | CA | TYR | C | 413 | -35.044 | -13.647 | 6.194 | 1.00 | 80.70 |
| 15425 | CB | TYR | C | 413 | -35.984 | -14.005 | 5.042 | 1.00 | 80.44 |
| 15426 | CG | TYR | C | 413 | -36.379 | -12.802 | 4.215 | 1.00 | 79.98 |
| 15427 | CD1 | TYR | C | 413 | -36.263 | -11.517 | 4.729 | 1.00 | 79.54 |
| 15428 | CE1 | TYR | C | 413 | -36.619 | -10.410 | 3.981 | 1.00 | 79.47 |
| 15429 | CZ | TYR | C | 413 | -37.099 | -10.576 | 2.698 | 1.00 | 79.40 |
| 15430 | OH | TYR | C | 413 | -37.452 | -9.468 | 1.957 | 1.00 | 79.09 |
| 15431 | CE2 | TYR | C | 413 | -37.223 | -11.845 | 2.162 | 1.00 | 79.68 |
| 15432 | CD2 | TYR | C | 413 | -36.864 | -12.947 | 2.921 | 1.00 | 79.74 |
| 15433 | C | TYR | C | 413 | -34.894 | -14.810 | 7.177 | 1.00 | 80.94 |
| 15434 | O | TYR | C | 413 | -35.840 | -15.149 | 7.889 | 1.00 | 80.92 |
| 15435 | N | THR | C | 414 | -33.704 | -15.406 | 7.227 | 1.00 | 81.10 |
| 15436 | CA | THR | C | 414 | -33.453 | -16.504 | 8.157 | 1.00 | 81.25 |
| 15437 | CB | THR | C | 414 | -32.565 | -17.590 | 7.518 | 1.00 | 81.48 |
| 15438 | OG1 | THR | C | 414 | -31.803 | -17.025 | 6.439 | 1.00 | 81.83 |
| 15439 | CG2 | THR | C | 414 | -33.431 | -18.634 | 6.821 | 1.00 | 81.92 |
| 15440 | C | THR | C | 414 | -32.851 | -16.016 | 9.469 | 1.00 | 81.06 |
| 15441 | O | THR | C | 414 | -32.724 | -16.777 | 10.423 | 1.00 | 81.18 |
| 15442 | N | LYS | C | 415 | -32.486 | -14.741 | 9.515 | 1.00 | 80.87 |
| 15443 | CA | LYS | C | 415 | -31.943 | -14.154 | 10.733 | 1.00 | 80.89 |

FIGURE 3 KQ

| A | B | C | D | E | F | G | H | I | J |
|---|---|---|---|---|---|---|---|---|---|
| 15444 | CB | LYS | C | 415 | -30.975 | -13.014 | 10.404 | 1.00 | 81.12 |
| 15445 | CG | LYS | C | 415 | -29.561 | -13.471 | 10.050 | 1.00 | 81.84 |
| 15446 | CD | LYS | C | 415 | -28.767 | -12.345 | 9.387 | 1.00 | 82.89 |
| 15447 | CE | LYS | C | 415 | -27.362 | -12.798 | 8.990 | 1.00 | 83.68 |
| 15448 | NZ | LYS | C | 415 | -26.719 | -11.844 | 8.034 | 1.00 | 83.60 |
| 15449 | C | LYS | C | 415 | -33.077 | -13.663 | 11.632 | 1.00 | 80.55 |
| 15450 | O | LYS | C | 415 | -33.450 | -12.486 | 11.603 | 1.00 | 80.52 |
| 15451 | N | VAL | C | 416 | -33.612 | -14.574 | 12.442 | 1.00 | 80.08 |
| 15452 | CA | VAL | C | 416 | -34.762 | -14.268 | 13.284 | 1.00 | 79.53 |
| 15453 | CB | VAL | C | 416 | -35.938 | -15.185 | 12.937 | 1.00 | 79.55 |
| 15454 | CG1 | VAL | C | 416 | -37.215 | -14.650 | 13.551 | 1.00 | 79.50 |
| 15455 | CG2 | VAL | C | 416 | -36.074 | -15.318 | 11.424 | 1.00 | 79.34 |
| 15456 | C | VAL | C | 416 | -34.495 | -14.380 | 14.783 | 1.00 | 79.19 |
| 15457 | O | VAL | C | 416 | -34.178 | -15.455 | 15.294 | 1.00 | 79.08 |
| 15458 | N | THR | C | 417 | -34.651 | -13.262 | 15.483 | 1.00 | 78.72 |
| 15459 | CA | THR | C | 417 | -34.447 | -13.218 | 16.926 | 1.00 | 78.33 |
| 15460 | CB | THR | C | 417 | -33.597 | -11.975 | 17.298 | 1.00 | 78.39 |
| 15461 | OG1 | THR | C | 417 | -32.352 | -12.003 | 16.587 | 1.00 | 78.51 |
| 15462 | CG2 | THR | C | 417 | -33.171 | -12.022 | 18.760 | 1.00 | 78.40 |
| 15463 | C | THR | C | 417 | -35.785 | -13.144 | 17.657 | 1.00 | 77.84 |
| 15464 | O | THR | C | 417 | -36.691 | -12.438 | 17.214 | 1.00 | 77.89 |
| 15465 | N | CYS | C | 418 | -35.918 | -13.882 | 18.760 | 1.00 | 77.08 |
| 15466 | CA | CYS | C | 418 | -37.108 | -13.774 | 19.604 | 1.00 | 76.44 |
| 15467 | CB | CYS | C | 418 | -37.616 | -15.138 | 20.090 | 1.00 | 76.39 |
| 15468 | SG | CYS | C | 418 | -39.136 | -14.966 | 21.077 | 1.00 | 75.10 |
| 15469 | C | CYS | C | 418 | -36.766 | -12.909 | 20.809 | 1.00 | 76.30 |
| 15470 | O | CYS | C | 418 | -36.133 | -13.371 | 21.758 | 1.00 | 76.29 |
| 15471 | N | LEU | C | 419 | -37.191 | -11.656 | 20.791 | 1.00 | 75.89 |
| 15472 | CA | LEU | C | 419 | -36.823 | -10.766 | 21.879 | 1.00 | 75.66 |
| 15473 | CB | LEU | C | 419 | -36.706 | -9.322 | 21.388 | 1.00 | 75.74 |
| 15474 | CG | LEU | C | 419 | -37.311 | -8.998 | 20.022 | 1.00 | 75.92 |
| 15475 | CD1 | LEU | C | 419 | -37.369 | -7.485 | 19.819 | 1.00 | 75.85 |
| 15476 | CD2 | LEU | C | 419 | -36.510 | -9.663 | 18.916 | 1.00 | 75.49 |
| 15477 | C | LEU | C | 419 | -37.710 | -10.840 | 23.113 | 1.00 | 75.43 |
| 15478 | O | LEU | C | 419 | -37.682 | -9.932 | 23.940 | 1.00 | 75.59 |
| 15479 | N | SER | C | 420 | -38.468 | -11.922 | 23.267 | 1.00 | 75.00 |
| 15480 | CA | SER | C | 420 | -39.344 | -12.032 | 24.435 | 1.00 | 74.63 |
| 15481 | CB | SER | C | 420 | -40.748 | -11.494 | 24.115 | 1.00 | 74.69 |
| 15482 | OG | SER | C | 420 | -41.363 | -12.236 | 23.073 | 1.00 | 74.18 |
| 15483 | C | SER | C | 420 | -39.437 | -13.424 | 25.056 | 1.00 | 74.41 |
| 15484 | O | SER | C | 420 | -39.605 | -13.550 | 26.268 | 1.00 | 74.04 |
| 15485 | N | CYS | C | 421 | -39.319 | -14.459 | 24.229 | 1.00 | 74.36 |
| 15486 | CA | CYS | C | 421 | -39.451 | -15.845 | 24.691 | 1.00 | 74.56 |
| 15487 | CB | CYS | C | 421 | -39.029 | -16.843 | 23.601 | 1.00 | 74.55 |
| 15488 | SG | CYS | C | 421 | -39.795 | -16.675 | 21.974 | 1.00 | 75.47 |
| 15489 | C | CYS | C | 421 | -38.677 | -16.178 | 25.973 | 1.00 | 74.43 |
| 15490 | O | CYS | C | 421 | -39.183 | -16.900 | 26.837 | 1.00 | 74.45 |
| 15491 | N | GLU | C | 422 | -37.459 | -15.658 | 26.100 | 1.00 | 74.20 |
| 15492 | CA | GLU | C | 422 | -36.601 | -16.038 | 27.223 | 1.00 | 73.99 |
| 15493 | CB | GLU | C | 422 | -35.238 | -16.521 | 26.706 | 1.00 | 74.21 |
| 15494 | CG | GLU | C | 422 | -35.018 | -18.026 | 26.809 | 1.00 | 75.59 |

FIGURE 3 KR

| A | B | C | D | E | F | G | H | I | J |
|---|---|---|---|---|---|---|---|---|---|
| 15495 | CD | GLU | C | 422 | -35.460 | -18.796 | 25.575 | 1.00 | 77.17 |
| 15496 | OE1 | GLU | C | 422 | -35.065 | -18.406 | 24.455 | 1.00 | 77.82 |
| 15497 | OE2 | GLU | C | 422 | -36.185 | -19.806 | 25.728 | 1.00 | 78.01 |
| 15498 | C | GLU | C | 422 | -36.395 | -15.021 | 28.345 | 1.00 | 73.45 |
| 15499 | O | GLU | C | 422 | -35.564 | -15.235 | 29.228 | 1.00 | 73.43 |
| 15500 | N | LEU | C | 423 | -37.140 | -13.922 | 28.329 | 1.00 | 72.79 |
| 15501 | CA | LEU | C | 423 | -36.977 | -12.903 | 29.363 | 1.00 | 72.14 |
| 15502 | CB | LEU | C | 423 | -37.689 | -11.611 | 28.963 | 1.00 | 72.15 |
| 15503 | CG | LEU | C | 423 | -37.469 | -11.097 | 27.539 | 1.00 | 72.52 |
| 15504 | CD1 | LEU | C | 423 | -38.348 | -9.879 | 27.276 | 1.00 | 72.06 |
| 15505 | CD2 | LEU | C | 423 | -36.000 | -10.769 | 27.297 | 1.00 | 72.84 |
| 15506 | C | LEU | C | 423 | -37.516 | -13.381 | 30.708 | 1.00 | 71.58 |
| 15507 | O | LEU | C | 423 | -37.027 | -12.987 | 31.769 | 1.00 | 71.53 |
| 15508 | N | ASN | C | 424 | -38.535 | -14.227 | 30.638 | 1.00 | 70.83 |
| 15509 | CA | ASN | C | 424 | -39.222 | -14.756 | 31.804 | 1.00 | 70.18 |
| 15510 | CB | ASN | C | 424 | -40.111 | -13.680 | 32.435 | 1.00 | 70.20 |
| 15511 | CG | ASN | C | 424 | -39.465 | -13.000 | 33.636 | 1.00 | 70.68 |
| 15512 | OD1 | ASN | C | 424 | -39.510 | -13.518 | 34.755 | 1.00 | 70.96 |
| 15513 | ND2 | ASN | C | 424 | -38.882 | -11.825 | 33.414 | 1.00 | 70.15 |
| 15514 | C | ASN | C | 424 | -40.096 | -15.898 | 31.319 | 1.00 | 69.55 |
| 15515 | O | ASN | C | 424 | -41.312 | -15.856 | 31.464 | 1.00 | 69.47 |
| 15516 | N | PRO | C | 425 | -39.475 | -16.906 | 30.719 | 1.00 | 68.95 |
| 15517 | CA | PRO | C | 425 | -40.203 | -18.033 | 30.125 | 1.00 | 68.32 |
| 15518 | CB | PRO | C | 425 | -39.083 | -19.008 | 29.749 | 1.00 | 68.30 |
| 15519 | CG | PRO | C | 425 | -37.914 | -18.540 | 30.568 | 1.00 | 68.97 |
| 15520 | CD | PRO | C | 425 | -38.021 | -17.048 | 30.548 | 1.00 | 68.93 |
| 15521 | C | PRO | C | 425 | -41.197 | -18.699 | 31.068 | 1.00 | 67.68 |
| 15522 | O | PRO | C | 425 | -42.075 | -19.419 | 30.590 | 1.00 | 67.66 |
| 15523 | N | GLU | C | 426 | -41.067 | -18.483 | 32.374 | 1.00 | 66.88 |
| 15524 | CA | GLU | C | 426 | -42.016 | -19.071 | 33.317 | 1.00 | 66.13 |
| 15525 | CB | GLU | C | 426 | -41.349 | -19.432 | 34.647 | 1.00 | 66.25 |
| 15526 | CG | GLU | C | 426 | -41.287 | -20.931 | 34.915 | 1.00 | 66.77 |
| 15527 | CD | GLU | C | 426 | -40.397 | -21.685 | 33.936 | 1.00 | 67.43 |
| 15528 | OE1 | GLU | C | 426 | -40.744 | -22.833 | 33.574 | 1.00 | 67.25 |
| 15529 | OE2 | GLU | C | 426 | -39.344 | -21.141 | 33.538 | 1.00 | 67.61 |
| 15530 | C | GLU | C | 426 | -43.256 | -18.206 | 33.550 | 1.00 | 65.45 |
| 15531 | O | GLU | C | 426 | -44.382 | -18.709 | 33.516 | 1.00 | 65.35 |
| 15532 | N | ARG | C | 427 | -43.060 | -16.909 | 33.767 | 1.00 | 64.39 |
| 15533 | CA | ARG | C | 427 | -44.195 | -16.040 | 34.035 | 1.00 | 63.52 |
| 15534 | CB | ARG | C | 427 | -43.862 | -15.025 | 35.134 | 1.00 | 63.40 |
| 15535 | CG | ARG | C | 427 | -43.537 | -13.633 | 34.636 | 1.00 | 62.75 |
| 15536 | CD | ARG | C | 427 | -44.289 | -12.525 | 35.377 | 1.00 | 62.46 |
| 15537 | NE | ARG | C | 427 | -43.531 | -11.960 | 36.487 | 1.00 | 62.08 |
| 15538 | CZ | ARG | C | 427 | -43.906 | -10.893 | 37.183 | 1.00 | 62.69 |
| 15539 | NH1 | ARG | C | 427 | -43.146 | -10.443 | 38.178 | 1.00 | 62.97 |
| 15540 | NH2 | ARG | C | 427 | -45.040 | -10.271 | 36.887 | 1.00 | 61.77 |
| 15541 | C | ARG | C | 427 | -44.741 | -15.331 | 32.792 | 1.00 | 63.08 |
| 15542 | O | ARG | C | 427 | -45.852 | -14.803 | 32.818 | 1.00 | 62.99 |
| 15543 | N | CYS | C | 428 | -43.985 | -15.344 | 31.699 | 1.00 | 62.40 |
| 15544 | CA | CYS | C | 428 | -44.394 | -14.605 | 30.505 | 1.00 | 61.91 |
| 15545 | CB | CYS | C | 428 | -43.562 | -13.330 | 30.381 | 1.00 | 61.92 |

FIGURE 3 KS

| A | B | C | D | E | F | G | H | I | J |
|---|---|---|---|---|---|---|---|---|---|
| 15546 | SG | CYS | C | 428 | -43.944 | -12.035 | 31.581 | 1.00 | 62.74 |
| 15547 | C | CYS | C | 428 | -44.307 | -15.357 | 29.183 | 1.00 | 61.46 |
| 15548 | O | CYS | C | 428 | -43.222 | -15.555 | 28.658 | 1.00 | 61.37 |
| 15549 | N | GLN | C | 429 | -45.451 | -15.752 | 28.632 | 1.00 | 61.12 |
| 15550 | CA | GLN | C | 429 | -45.469 | -16.369 | 27.306 | 1.00 | 60.67 |
| 15551 | CB | GLN | C | 429 | -45.514 | -17.898 | 27.382 | 1.00 | 60.76 |
| 15552 | CG | GLN | C | 429 | -46.496 | -18.460 | 28.367 | 1.00 | 61.52 |
| 15553 | CD | GLN | C | 429 | -46.191 | -19.899 | 28.709 | 1.00 | 63.25 |
| 15554 | OE1 | GLN | C | 429 | -47.054 | -20.772 | 28.599 | 1.00 | 64.26 |
| 15555 | NE2 | GLN | C | 429 | -44.959 | -20.155 | 29.122 | 1.00 | 63.65 |
| 15556 | C | GLN | C | 429 | -46.594 | -15.800 | 26.430 | 1.00 | 60.28 |
| 15557 | O | GLN | C | 429 | -47.020 | -16.423 | 25.457 | 1.00 | 60.09 |
| 15558 | N | TYR | C | 430 | -47.061 | -14.608 | 26.793 | 1.00 | 59.73 |
| 15559 | CA | TYR | C | 430 | -48.094 | -13.903 | 26.042 | 1.00 | 59.11 |
| 15560 | CB | TYR | C | 430 | -49.463 | -14.121 | 26.675 | 1.00 | 58.89 |
| 15561 | CG | TYR | C | 430 | -50.613 | -13.846 | 25.738 | 1.00 | 57.34 |
| 15562 | CD1 | TYR | C | 430 | -51.038 | -12.543 | 25.497 | 1.00 | 55.45 |
| 15563 | CE1 | TYR | C | 430 | -52.096 | -12.284 | 24.638 | 1.00 | 54.59 |
| 15564 | CZ | TYR | C | 430 | -52.742 | -13.332 | 24.011 | 1.00 | 54.07 |
| 15565 | OH | TYR | C | 430 | -53.790 | -13.067 | 23.157 | 1.00 | 52.94 |
| 15566 | CE2 | TYR | C | 430 | -52.335 | -14.637 | 24.232 | 1.00 | 54.36 |
| 15567 | CD2 | TYR | C | 430 | -51.275 | -14.886 | 25.091 | 1.00 | 56.11 |
| 15568 | C | TYR | C | 430 | -47.754 | -12.422 | 26.035 | 1.00 | 59.11 |
| 15569 | O | TYR | C | 430 | -48.080 | -11.695 | 26.974 | 1.00 | 58.98 |
| 15570 | N | TYR | C | 431 | -47.112 | -11.981 | 24.961 | 1.00 | 59.30 |
| 15571 | CA | TYR | C | 431 | -46.578 | -10.623 | 24.879 | 1.00 | 59.63 |
| 15572 | CB | TYR | C | 431 | -45.076 | -10.671 | 24.531 | 1.00 | 59.24 |
| 15573 | CG | TYR | C | 431 | -44.149 | -10.882 | 25.720 | 1.00 | 58.79 |
| 15574 | CD1 | TYR | C | 431 | -43.723 | -9.805 | 26.492 | 1.00 | 58.19 |
| 15575 | CE1 | TYR | C | 431 | -42.888 | -9.986 | 27.579 | 1.00 | 57.16 |
| 15576 | CZ | TYR | C | 431 | -42.461 | -11.250 | 27.907 | 1.00 | 56.79 |
| 15577 | OH | TYR | C | 431 | -41.625 | -11.415 | 28.994 | 1.00 | 56.52 |
| 15578 | CE2 | TYR | C | 431 | -42.868 | -12.340 | 27.156 | 1.00 | 56.46 |
| 15579 | CD2 | TYR | C | 431 | -43.704 | -12.152 | 26.071 | 1.00 | 57.27 |
| 15580 | C | TYR | C | 431 | -47.280 | -9.706 | 23.881 | 1.00 | 60.12 |
| 15581 | O | TYR | C | 431 | -47.754 | -10.150 | 22.833 | 1.00 | 59.87 |
| 15582 | N | SER | C | 432 | -47.336 | -8.424 | 24.234 | 1.00 | 60.66 |
| 15583 | CA | SER | C | 432 | -47.800 | -7.371 | 23.338 | 1.00 | 61.67 |
| 15584 | CB | SER | C | 432 | -49.197 | -6.866 | 23.714 | 1.00 | 61.67 |
| 15585 | OG | SER | C | 432 | -49.153 | -5.919 | 24.767 | 1.00 | 61.26 |
| 15586 | C | SER | C | 432 | -46.759 | -6.249 | 23.428 | 1.00 | 62.43 |
| 15587 | O | SER | C | 432 | -46.048 | -6.134 | 24.438 | 1.00 | 62.68 |
| 15588 | N | VAL | C | 433 | -46.667 | -5.421 | 22.394 | 1.00 | 63.14 |
| 15589 | CA | VAL | C | 433 | -45.611 | -4.414 | 22.345 | 1.00 | 63.65 |
| 15590 | CB | VAL | C | 433 | -44.420 | -4.916 | 21.500 | 1.00 | 63.64 |
| 15591 | CG1 | VAL | C | 433 | -44.830 | -5.065 | 20.041 | 1.00 | 62.88 |
| 15592 | CG2 | VAL | C | 433 | -43.248 | -3.975 | 21.617 | 1.00 | 63.51 |
| 15593 | C | VAL | C | 433 | -46.038 | -3.071 | 21.778 | 1.00 | 64.30 |
| 15594 | O | VAL | C | 433 | -46.864 | -2.989 | 20.864 | 1.00 | 64.16 |
| 15595 | N | SER | C | 434 | -45.438 | -2.021 | 22.323 | 1.00 | 65.16 |
| 15596 | CA | SER | C | 434 | -45.701 | -0.658 | 21.897 | 1.00 | 66.07 |

FIGURE 3 KT

| A | B | C | D | E | F | G | H | I | J |
|---|---|---|---|---|---|---|---|---|---|
| 15597 | CB | SER | C | 434 | -46.480 | 0.088 | 22.986 | 1.00 | 65.84 |
| 15598 | OG | SER | C | 434 | -46.523 | 1.483 | 22.745 | 1.00 | 65.86 |
| 15599 | C | SER | C | 434 | -44.370 | 0.032 | 21.631 | 1.00 | 66.81 |
| 15600 | O | SER | C | 434 | -43.549 | 0.178 | 22.538 | 1.00 | 67.02 |
| 15601 | N | PHE | C | 435 | -44.151 | 0.445 | 20.386 | 1.00 | 67.72 |
| 15602 | CA | PHE | C | 435 | -42.912 | 1.130 | 20.020 | 1.00 | 68.43 |
| 15603 | CB | PHE | C | 435 | -42.485 | 0.763 | 18.601 | 1.00 | 68.25 |
| 15604 | CG | PHE | C | 435 | -42.050 | -0.662 | 18.443 | 1.00 | 67.79 |
| 15605 | CD1 | PHE | C | 435 | -42.975 | -1.657 | 18.183 | 1.00 | 66.96 |
| 15606 | CE1 | PHE | C | 435 | -42.573 | -2.968 | 18.028 | 1.00 | 66.98 |
| 15607 | CZ | PHE | C | 435 | -41.238 | -3.297 | 18.125 | 1.00 | 66.90 |
| 15608 | CE2 | PHE | C | 435 | -40.306 | -2.319 | 18.374 | 1.00 | 66.90 |
| 15609 | CD2 | PHE | C | 435 | -40.712 | -1.005 | 18.532 | 1.00 | 67.60 |
| 15610 | C | PHE | C | 435 | -43.039 | 2.644 | 20.117 | 1.00 | 69.13 |
| 15611 | O | PHE | C | 435 | -44.137 | 3.183 | 20.253 | 1.00 | 68.97 |
| 15612 | N | SER | C | 436 | -41.896 | 3.318 | 20.048 | 1.00 | 70.15 |
| 15613 | CA | SER | C | 436 | -41.842 | 4.772 | 20.053 | 1.00 | 71.10 |
| 15614 | CB | SER | C | 436 | -40.538 | 5.252 | 20.686 | 1.00 | 71.07 |
| 15615 | OG | SER | C | 436 | -39.414 | 4.665 | 20.047 | 1.00 | 71.13 |
| 15616 | C | SER | C | 436 | -41.935 | 5.240 | 18.605 | 1.00 | 71.89 |
| 15617 | O | SER | C | 436 | -41.803 | 4.431 | 17.688 | 1.00 | 71.91 |
| 15618 | N | LYS | C | 437 | -42.148 | 6.539 | 18.401 | 1.00 | 72.83 |
| 15619 | CA | LYS | C | 437 | -42.320 | 7.101 | 17.057 | 1.00 | 73.87 |
| 15620 | CB | LYS | C | 437 | -42.066 | 8.611 | 17.051 | 1.00 | 73.91 |
| 15621 | CG | LYS | C | 437 | -43.330 | 9.472 | 16.895 | 1.00 | 74.68 |
| 15622 | CD | LYS | C | 437 | -44.300 | 9.337 | 18.071 | 1.00 | 75.43 |
| 15623 | CE | LYS | C | 437 | -45.331 | 8.225 | 17.854 | 1.00 | 76.20 |
| 15624 | NZ | LYS | C | 437 | -46.410 | 8.606 | 16.898 | 1.00 | 76.22 |
| 15625 | C | LYS | C | 437 | -41.532 | 6.423 | 15.930 | 1.00 | 74.48 |
| 15626 | O | LYS | C | 437 | -42.113 | 6.054 | 14.907 | 1.00 | 74.53 |
| 15627 | N | GLU | C | 438 | -40.222 | 6.264 | 16.107 | 1.00 | 75.26 |
| 15628 | CA | GLU | C | 438 | -39.393 | 5.674 | 15.051 | 1.00 | 76.16 |
| 15629 | CB | GLU | C | 438 | -38.279 | 6.641 | 14.624 | 1.00 | 76.38 |
| 15630 | CG | GLU | C | 438 | -38.111 | 6.795 | 13.117 | 1.00 | 77.93 |
| 15631 | CD | GLU | C | 438 | -38.580 | 8.152 | 12.618 | 1.00 | 79.88 |
| 15632 | OE1 | GLU | C | 438 | -39.345 | 8.827 | 13.346 | 1.00 | 80.51 |
| 15633 | OE2 | GLU | C | 438 | -38.170 | 8.552 | 11.503 | 1.00 | 80.50 |
| 15634 | C | GLU | C | 438 | -38.792 | 4.309 | 15.411 | 1.00 | 76.21 |
| 15635 | O | GLU | C | 438 | -37.980 | 3.768 | 14.656 | 1.00 | 76.39 |
| 15636 | N | ALA | C | 439 | -39.163 | 3.776 | 16.570 | 1.00 | 76.32 |
| 15637 | CA | ALA | C | 439 | -38.745 | 2.428 | 16.968 | 1.00 | 76.52 |
| 15638 | CB | ALA | C | 439 | -38.634 | 1.520 | 15.740 | 1.00 | 76.33 |
| 15639 | C | ALA | C | 439 | -37.481 | 2.305 | 17.833 | 1.00 | 76.63 |
| 15640 | O | ALA | C | 439 | -37.087 | 1.194 | 18.186 | 1.00 | 76.76 |
| 15641 | N | LYS | C | 440 | -36.848 | 3.420 | 18.180 | 1.00 | 76.64 |
| 15642 | CA | LYS | C | 440 | -35.648 | 3.350 | 19.017 | 1.00 | 76.67 |
| 15643 | CB | LYS | C | 440 | -35.168 | 4.746 | 19.423 | 1.00 | 76.79 |
| 15644 | CG | LYS | C | 440 | -34.297 | 5.447 | 18.384 | 1.00 | 77.61 |
| 15645 | CD | LYS | C | 440 | -33.503 | 6.584 | 19.027 | 1.00 | 78.97 |
| 15646 | CE | LYS | C | 440 | -32.505 | 7.221 | 18.049 | 1.00 | 79.50 |
| 15647 | NZ | LYS | C | 440 | -33.162 | 8.106 | 17.037 | 1.00 | 78.84 |

FIGURE 3 KU

| A | B | C | D | E | F | G | H | I | J |
|---|---|---|---|---|---|---|---|---|---|
| 15648 | C | LYS | C | 440 | -35.870 | 2.487 | 20.262 | 1.00 | 76.42 |
| 15649 | O | LYS | C | 440 | -34.972 | 1.768 | 20.703 | 1.00 | 76.42 |
| 15650 | N | TYR | C | 441 | -37.072 | 2.560 | 20.822 | 1.00 | 76.10 |
| 15651 | CA | TYR | C | 441 | -37.405 | 1.784 | 22.007 | 1.00 | 75.67 |
| 15652 | CB | TYR | C | 441 | -37.616 | 2.699 | 23.210 | 1.00 | 75.88 |
| 15653 | CG | TYR | C | 441 | -36.514 | 3.703 | 23.465 | 1.00 | 76.85 |
| 15654 | CD1 | TYR | C | 441 | -36.457 | 4.895 | 22.757 | 1.00 | 77.32 |
| 15655 | CE1 | TYR | C | 441 | -35.460 | 5.824 | 22.999 | 1.00 | 78.17 |
| 15656 | CZ | TYR | C | 441 | -34.508 | 5.574 | 23.969 | 1.00 | 78.56 |
| 15657 | OH | TYR | C | 441 | -33.516 | 6.498 | 24.214 | 1.00 | 78.85 |
| 15658 | CE2 | TYR | C | 441 | -34.546 | 4.401 | 24.694 | 1.00 | 78.20 |
| 15659 | CD2 | TYR | C | 441 | -35.550 | 3.475 | 24.441 | 1.00 | 78.08 |
| 15660 | C | TYR | C | 441 | -38.675 | 0.979 | 21.786 | 1.00 | 75.10 |
| 15661 | O | TYR | C | 441 | -39.273 | 1.031 | 20.710 | 1.00 | 75.17 |
| 15662 | N | TYR | C | 442 | -39.078 | 0.239 | 22.816 | 1.00 | 74.20 |
| 15663 | CA | TYR | C | 442 | -40.307 | -0.549 | 22.780 | 1.00 | 73.30 |
| 15664 | CB | TYR | C | 442 | -40.235 | -1.673 | 21.735 | 1.00 | 73.19 |
| 15665 | CG | TYR | C | 442 | -39.195 | -2.740 | 21.994 | 1.00 | 73.21 |
| 15666 | CD1 | TYR | C | 442 | -37.919 | -2.644 | 21.448 | 1.00 | 73.11 |
| 15667 | CE1 | TYR | C | 442 | -36.967 | -3.624 | 21.677 | 1.00 | 72.43 |
| 15668 | CZ | TYR | C | 442 | -37.289 | -4.721 | 22.452 | 1.00 | 72.27 |
| 15669 | OH | TYR | C | 442 | -36.352 | -5.700 | 22.686 | 1.00 | 71.61 |
| 15670 | CE2 | TYR | C | 442 | -38.550 | -4.842 | 22.997 | 1.00 | 72.28 |
| 15671 | CD2 | TYR | C | 442 | -39.494 | -3.859 | 22.763 | 1.00 | 72.75 |
| 15672 | C | TYR | C | 442 | -40.649 | -1.102 | 24.159 | 1.00 | 72.68 |
| 15673 | O | TYR | C | 442 | -39.770 | -1.547 | 24.893 | 1.00 | 72.50 |
| 15674 | N | GLN | C | 443 | -41.929 | -1.048 | 24.515 | 1.00 | 71.97 |
| 15675 | CA | GLN | C | 443 | -42.377 | -1.569 | 25.801 | 1.00 | 71.05 |
| 15676 | CB | GLN | C | 443 | -43.354 | -0.612 | 26.496 | 1.00 | 71.05 |
| 15677 | CG | GLN | C | 443 | -44.812 | -0.793 | 26.104 | 1.00 | 71.02 |
| 15678 | CD | GLN | C | 443 | -45.784 | -0.282 | 27.161 | 1.00 | 70.77 |
| 15679 | OE1 | GLN | C | 443 | -45.447 | -0.204 | 28.341 | 1.00 | 70.62 |
| 15680 | NE2 | GLN | C | 443 | -46.994 | 0.051 | 26.738 | 1.00 | 71.00 |
| 15681 | C | GLN | C | 443 | -43.015 | -2.930 | 25.598 | 1.00 | 70.47 |
| 15682 | O | GLN | C | 443 | -43.828 | -3.125 | 24.703 | 1.00 | 70.56 |
| 15683 | N | LEU | C | 444 | -42.612 | -3.890 | 26.411 | 1.00 | 69.79 |
| 15684 | CA | LEU | C | 444 | -43.178 | -5.213 | 26.315 | 1.00 | 68.88 |
| 15685 | CB | LEU | C | 444 | -42.095 | -6.271 | 26.453 | 1.00 | 68.90 |
| 15686 | CG | LEU | C | 444 | -41.491 | -6.683 | 25.119 | 1.00 | 69.17 |
| 15687 | CD1 | LEU | C | 444 | -42.600 | -7.053 | 24.141 | 1.00 | 69.11 |
| 15688 | CD2 | LEU | C | 444 | -40.524 | -7.838 | 25.312 | 1.00 | 69.33 |
| 15689 | C | LEU | C | 444 | -44.214 | -5.376 | 27.399 | 1.00 | 68.42 |
| 15690 | O | LEU | C | 444 | -44.084 | -4.823 | 28.489 | 1.00 | 68.41 |
| 15691 | N | ARG | C | 445 | -45.258 | -6.124 | 27.089 | 1.00 | 67.87 |
| 15692 | CA | ARG | C | 445 | -46.306 | -6.379 | 28.054 | 1.00 | 67.18 |
| 15693 | CB | ARG | C | 445 | -47.481 | -5.440 | 27.816 | 1.00 | 67.37 |
| 15694 | CG | ARG | C | 445 | -48.838 | -6.033 | 28.162 | 1.00 | 68.00 |
| 15695 | CD | ARG | C | 445 | -49.992 | -5.085 | 27.891 | 1.00 | 68.96 |
| 15696 | NE | ARG | C | 445 | -51.213 | -5.778 | 27.495 | 1.00 | 69.80 |
| 15697 | CZ | ARG | C | 445 | -52.236 | -5.186 | 26.893 | 1.00 | 70.42 |
| 15698 | NH1 | ARG | C | 445 | -53.311 | -5.890 | 26.566 | 1.00 | 71.22 |

FIGURE 3 KV

| A | B | C | D | E | F | G | H | I | J |
|---|---|---|---|---|---|---|---|---|---|
| 15699 | NH2 | ARG | C | 445 | -52.186 | -3.887 | 26.617 | 1.00 | 70.18 |
| 15700 | C | ARG | C | 445 | -46.749 | -7.810 | 27.905 | 1.00 | 66.40 |
| 15701 | O | ARG | C | 445 | -47.305 | -8.182 | 26.878 | 1.00 | 66.41 |
| 15702 | N | CYS | C | 446 | -46.458 | -8.630 | 28.906 | 1.00 | 65.62 |
| 15703 | CA | CYS | C | 446 | -46.937 | -10.002 | 28.883 | 1.00 | 64.89 |
| 15704 | CB | CYS | C | 446 | -45.875 | -10.995 | 29.358 | 1.00 | 64.87 |
| 15705 | SG | CYS | C | 446 | -45.775 | -11.242 | 31.141 | 1.00 | 64.37 |
| 15706 | C | CYS | C | 446 | -48.173 | -10.040 | 29.764 | 1.00 | 64.31 |
| 15707 | O | CYS | C | 446 | -48.257 | -9.318 | 30.759 | 1.00 | 64.14 |
| 15708 | N | SER | C | 447 | -49.133 | -10.874 | 29.394 | 1.00 | 63.60 |
| 15709 | CA | SER | C | 447 | -50.404 | -10.907 | 30.101 | 1.00 | 62.98 |
| 15710 | CB | SER | C | 447 | -51.554 | -10.828 | 29.096 | 1.00 | 62.83 |
| 15711 | OG | SER | C | 447 | -51.335 | -9.777 | 28.172 | 1.00 | 62.79 |
| 15712 | C | SER | C | 447 | -50.557 | -12.146 | 30.954 | 1.00 | 62.53 |
| 15713 | O | SER | C | 447 | -51.598 | -12.349 | 31.572 | 1.00 | 62.13 |
| 15714 | N | GLY | C | 448 | -49.516 | -12.971 | 30.986 | 1.00 | 62.30 |
| 15715 | CA | GLY | C | 448 | -49.543 | -14.203 | 31.753 | 1.00 | 62.09 |
| 15716 | C | GLY | C | 448 | -48.497 | -15.176 | 31.252 | 1.00 | 62.13 |
| 15717 | O | GLY | C | 448 | -47.730 | -14.849 | 30.345 | 1.00 | 62.20 |
| 15718 | N | PRO | C | 449 | -48.485 | -16.389 | 31.798 | 1.00 | 62.06 |
| 15719 | CA | PRO | C | 449 | -49.471 | -16.837 | 32.792 | 1.00 | 61.94 |
| 15720 | CB | PRO | C | 449 | -49.279 | -18.354 | 32.816 | 1.00 | 61.99 |
| 15721 | CG | PRO | C | 449 | -47.884 | -18.576 | 32.356 | 1.00 | 62.06 |
| 15722 | CD | PRO | C | 449 | -47.495 | -17.429 | 31.480 | 1.00 | 61.96 |
| 15723 | C | PRO | C | 449 | -49.269 | -16.287 | 34.191 | 1.00 | 61.82 |
| 15724 | O | PRO | C | 449 | -50.119 | -16.515 | 35.047 | 1.00 | 61.98 |
| 15725 | N | GLY | C | 450 | -48.169 | -15.587 | 34.429 | 1.00 | 61.77 |
| 15726 | CA | GLY | C | 450 | -47.941 | -14.994 | 35.728 | 1.00 | 61.81 |
| 15727 | C | GLY | C | 450 | -48.527 | -13.603 | 35.696 | 1.00 | 62.02 |
| 15728 | O | GLY | C | 450 | -49.132 | -13.208 | 34.701 | 1.00 | 62.11 |
| 15729 | N | LEU | C | 451 | -48.361 | -12.853 | 36.776 | 1.00 | 62.12 |
| 15730 | CA | LEU | C | 451 | -48.865 | -11.495 | 36.807 | 1.00 | 62.43 |
| 15731 | CB | LEU | C | 451 | -48.475 | -10.814 | 38.111 | 1.00 | 62.43 |
| 15732 | CG | LEU | C | 451 | -49.483 | -11.010 | 39.237 | 1.00 | 62.12 |
| 15733 | CD1 | LEU | C | 451 | -50.198 | -12.339 | 39.086 | 1.00 | 61.65 |
| 15734 | CD2 | LEU | C | 451 | -48.799 | -10.894 | 40.595 | 1.00 | 62.13 |
| 15735 | C | LEU | C | 451 | -48.287 | -10.744 | 35.622 | 1.00 | 62.97 |
| 15736 | O | LEU | C | 451 | -47.156 | -11.006 | 35.216 | 1.00 | 63.03 |
| 15737 | N | PRO | C | 452 | -49.062 | -9.829 | 35.050 | 1.00 | 63.39 |
| 15738 | CA | PRO | C | 452 | -48.603 | -9.061 | 33.894 | 1.00 | 63.77 |
| 15739 | CB | PRO | C | 452 | -49.781 | -8.138 | 33.597 | 1.00 | 63.68 |
| 15740 | CG | PRO | C | 452 | -50.941 | -8.821 | 34.201 | 1.00 | 63.81 |
| 15741 | CD | PRO | C | 452 | -50.423 | -9.453 | 35.457 | 1.00 | 63.48 |
| 15742 | C | PRO | C | 452 | -47.373 | -8.255 | 34.269 | 1.00 | 64.20 |
| 15743 | O | PRO | C | 452 | -47.258 | -7.794 | 35.405 | 1.00 | 64.11 |
| 15744 | N | LEU | C | 453 | -46.463 | -8.105 | 33.317 | 1.00 | 64.70 |
| 15745 | CA | LEU | C | 453 | -45.218 | -7.400 | 33.545 | 1.00 | 65.40 |
| 15746 | CB | LEU | C | 453 | -44.075 | -8.404 | 33.714 | 1.00 | 65.43 |
| 15747 | CG | LEU | C | 453 | -42.643 | -8.059 | 33.305 | 1.00 | 65.83 |
| 15748 | CD1 | LEU | C | 453 | -42.512 | -7.958 | 31.783 | 1.00 | 66.51 |
| 15749 | CD2 | LEU | C | 453 | -41.709 | -9.131 | 33.827 | 1.00 | 66.40 |

FIGURE 3 KW

| A | B | C | D | E | F | G | H | I | J |
|---|---|---|---|---|---|---|---|---|---|
| 15750 | C | LEU | C | 453 | -44.947 | -6.429 | 32.409 | 1.00 | 65.83 |
| 15751 | O | LEU | C | 453 | -45.025 | -6.778 | 31.231 | 1.00 | 65.92 |
| 15752 | N | TYR | C | 454 | -44.629 | -5.200 | 32.775 | 1.00 | 66.42 |
| 15753 | CA | TYR | C | 454 | -44.380 | -4.169 | 31.796 | 1.00 | 67.31 |
| 15754 | CB | TYR | C | 454 | -45.315 | -2.997 | 32.064 | 1.00 | 67.28 |
| 15755 | CG | TYR | C | 454 | -46.767 | -3.315 | 31.791 | 1.00 | 67.79 |
| 15756 | CD1 | TYR | C | 454 | -47.348 | -2.994 | 30.569 | 1.00 | 67.78 |
| 15757 | CE1 | TYR | C | 454 | -48.672 | -3.278 | 30.309 | 1.00 | 68.12 |
| 15758 | CZ | TYR | C | 454 | -49.438 | -3.901 | 31.272 | 1.00 | 68.30 |
| 15759 | OH | TYR | C | 454 | -50.760 | -4.182 | 31.007 | 1.00 | 67.89 |
| 15760 | CE2 | TYR | C | 454 | -48.885 | -4.237 | 32.493 | 1.00 | 68.45 |
| 15761 | CD2 | TYR | C | 454 | -47.556 | -3.942 | 32.747 | 1.00 | 68.05 |
| 15762 | C | TYR | C | 454 | -42.920 | -3.730 | 31.839 | 1.00 | 67.94 |
| 15763 | O | TYR | C | 454 | -42.432 | -3.270 | 32.869 | 1.00 | 68.23 |
| 15764 | N | THR | C | 455 | -42.224 | -3.881 | 30.715 | 1.00 | 68.86 |
| 15765 | CA | THR | C | 455 | -40.806 | -3.535 | 30.625 | 1.00 | 69.72 |
| 15766 | CB | THR | C | 455 | -39.944 | -4.807 | 30.654 | 1.00 | 69.58 |
| 15767 | OG1 | THR | C | 455 | -40.429 | -5.742 | 29.680 | 1.00 | 69.76 |
| 15768 | CG2 | THR | C | 455 | -40.113 | -5.545 | 31.972 | 1.00 | 69.53 |
| 15769 | C | THR | C | 455 | -40.489 | -2.763 | 29.353 | 1.00 | 70.50 |
| 15770 | O | THR | C | 455 | -40.896 | -3.161 | 28.265 | 1.00 | 70.60 |
| 15771 | N | LEU | C | 456 | -39.751 | -1.667 | 29.494 | 1.00 | 71.35 |
| 15772 | CA | LEU | C | 456 | -39.348 | -0.865 | 28.347 | 1.00 | 72.19 |
| 15773 | CB | LEU | C | 456 | -39.356 | 0.618 | 28.705 | 1.00 | 72.26 |
| 15774 | CG | LEU | C | 456 | -39.810 | 1.623 | 27.644 | 1.00 | 72.39 |
| 15775 | CD1 | LEU | C | 456 | -39.333 | 3.017 | 28.027 | 1.00 | 73.23 |
| 15776 | CD2 | LEU | C | 456 | -39.311 | 1.258 | 26.263 | 1.00 | 72.51 |
| 15777 | C | LEU | C | 456 | -37.943 | -1.268 | 27.931 | 1.00 | 72.89 |
| 15778 | O | LEU | C | 456 | -37.017 | -1.235 | 28.743 | 1.00 | 72.93 |
| 15779 | N | HIS | C | 457 | -37.795 | -1.652 | 26.667 | 1.00 | 73.68 |
| 15780 | CA | HIS | C | 457 | -36.510 | -2.063 | 26.121 | 1.00 | 74.39 |
| 15781 | CB | HIS | C | 457 | -36.627 | -3.454 | 25.503 | 1.00 | 74.53 |
| 15782 | CG | HIS | C | 457 | -37.266 | -4.468 | 26.400 | 1.00 | 75.22 |
| 15783 | ND1 | HIS | C | 457 | -36.673 | -5.677 | 26.697 | 1.00 | 75.59 |
| 15784 | CE1 | HIS | C | 457 | -37.460 | -6.366 | 27.504 | 1.00 | 75.51 |
| 15785 | NE2 | HIS | C | 457 | -38.546 | -5.650 | 27.736 | 1.00 | 75.75 |
| 15786 | CD2 | HIS | C | 457 | -38.451 | -4.460 | 27.056 | 1.00 | 75.56 |
| 15787 | C | HIS | C | 457 | -36.039 | -1.082 | 25.050 | 1.00 | 74.92 |
| 15788 | O | HIS | C | 457 | -36.765 | -0.161 | 24.683 | 1.00 | 74.94 |
| 15789 | N | SER | C | 458 | -34.818 | -1.288 | 24.556 | 1.00 | 75.63 |
| 15790 | CA | SER | C | 458 | -34.252 | -0.470 | 23.482 | 1.00 | 76.21 |
| 15791 | CB | SER | C | 458 | -32.946 | 0.179 | 23.927 | 1.00 | 76.35 |
| 15792 | OG | SER | C | 458 | -31.836 | -0.522 | 23.385 | 1.00 | 76.31 |
| 15793 | C | SER | C | 458 | -33.969 | -1.353 | 22.277 | 1.00 | 76.66 |
| 15794 | O | SER | C | 458 | -33.361 | -2.410 | 22.415 | 1.00 | 76.64 |
| 15795 | N | SER | C | 459 | -34.384 | -0.906 | 21.094 | 1.00 | 77.37 |
| 15796 | CA | SER | C | 459 | -34.227 | -1.704 | 19.880 | 1.00 | 78.06 |
| 15797 | CB | SER | C | 459 | -35.029 | -1.100 | 18.723 | 1.00 | 78.08 |
| 15798 | OG | SER | C | 459 | -34.251 | -0.175 | 17.978 | 1.00 | 78.13 |
| 15799 | C | SER | C | 459 | -32.772 | -1.899 | 19.455 | 1.00 | 78.51 |
| 15800 | O | SER | C | 459 | -32.366 | -3.009 | 19.113 | 1.00 | 78.48 |

FIGURE 3 KX

| A | B | C | D | E | F | G | H | I | J |
|---|---|---|---|---|---|---|---|---|---|
| 15801 | N | VAL | C | 460 | -31.998 | -0.819 | 19.478 | 1.00 | 79.13 |
| 15802 | CA | VAL | C | 460 | -30.602 | -0.858 | 19.040 | 1.00 | 79.90 |
| 15803 | CB | VAL | C | 460 | -29.736 | 0.163 | 19.792 | 1.00 | 79.91 |
| 15804 | CG1 | VAL | C | 460 | -28.318 | 0.173 | 19.222 | 1.00 | 80.28 |
| 15805 | CG2 | VAL | C | 460 | -30.360 | 1.548 | 19.718 | 1.00 | 80.14 |
| 15806 | C | VAL | C | 460 | -29.963 | -2.238 | 19.166 | 1.00 | 80.28 |
| 15807 | O | VAL | C | 460 | -29.514 | -2.810 | 18.176 | 1.00 | 80.25 |
| 15808 | N | ASN | C | 461 | -29.925 | -2.769 | 20.383 | 1.00 | 80.95 |
| 15809 | CA | ASN | C | 461 | -29.330 | -4.082 | 20.619 | 1.00 | 81.65 |
| 15810 | CB | ASN | C | 461 | -28.024 | -3.933 | 21.393 | 1.00 | 81.78 |
| 15811 | CG | ASN | C | 461 | -28.135 | -2.928 | 22.517 | 1.00 | 82.56 |
| 15812 | OD1 | ASN | C | 461 | -27.865 | -1.738 | 22.333 | 1.00 | 83.29 |
| 15813 | ND2 | ASN | C | 461 | -28.544 | -3.399 | 23.693 | 1.00 | 83.11 |
| 15814 | C | ASN | C | 461 | -30.259 | -5.050 | 21.353 | 1.00 | 81.83 |
| 15815 | O | ASN | C | 461 | -29.916 | -6.220 | 21.551 | 1.00 | 81.87 |
| 15816 | N | ASP | C | 462 | -31.431 | -4.553 | 21.750 | 1.00 | 81.95 |
| 15817 | CA | ASP | C | 462 | -32.423 | -5.352 | 22.472 | 1.00 | 81.99 |
| 15818 | CB | ASP | C | 462 | -32.740 | -6.648 | 21.728 | 1.00 | 82.05 |
| 15819 | CG | ASP | C | 462 | -33.324 | -6.399 | 20.367 | 1.00 | 82.51 |
| 15820 | OD1 | ASP | C | 462 | -33.222 | -7.298 | 19.507 | 1.00 | 83.46 |
| 15821 | OD2 | ASP | C | 462 | -33.898 | -5.331 | 20.064 | 1.00 | 83.21 |
| 15822 | C | ASP | C | 462 | -31.988 | -5.676 | 23.892 | 1.00 | 81.95 |
| 15823 | O | ASP | C | 462 | -31.728 | -6.836 | 24.226 | 1.00 | 81.98 |
| 15824 | N | LYS | C | 463 | -31.902 | -4.650 | 24.726 | 1.00 | 81.70 |
| 15825 | CA | LYS | C | 463 | -31.552 | -4.867 | 26.118 | 1.00 | 81.59 |
| 15826 | CB | LYS | C | 463 | -30.126 | -4.390 | 26.423 | 1.00 | 81.72 |
| 15827 | CG | LYS | C | 463 | -29.991 | -2.932 | 26.824 | 1.00 | 82.48 |
| 15828 | CD | LYS | C | 463 | -30.056 | -2.752 | 28.339 | 1.00 | 83.36 |
| 15829 | CE | LYS | C | 463 | -29.847 | -1.288 | 28.725 | 1.00 | 84.04 |
| 15830 | NZ | LYS | C | 463 | -30.056 | -1.042 | 30.183 | 1.00 | 84.21 |
| 15831 | C | LYS | C | 463 | -32.585 | -4.194 | 27.005 | 1.00 | 81.24 |
| 15832 | O | LYS | C | 463 | -33.152 | -3.157 | 26.652 | 1.00 | 81.27 |
| 15833 | N | GLY | C | 464 | -32.840 | -4.803 | 28.152 | 1.00 | 80.82 |
| 15834 | CA | GLY | C | 464 | -33.824 | -4.280 | 29.072 | 1.00 | 80.31 |
| 15835 | C | GLY | C | 464 | -33.284 | -3.134 | 29.892 | 1.00 | 79.81 |
| 15836 | O | GLY | C | 464 | -32.374 | -3.321 | 30.698 | 1.00 | 79.89 |
| 15837 | N | LEU | C | 465 | -33.841 | -1.947 | 29.676 | 1.00 | 79.34 |
| 15838 | CA | LEU | C | 465 | -33.459 | -0.775 | 30.444 | 1.00 | 78.86 |
| 15839 | CB | LEU | C | 465 | -34.036 | 0.504 | 29.839 | 1.00 | 78.85 |
| 15840 | CG | LEU | C | 465 | -34.193 | 0.662 | 28.329 | 1.00 | 78.87 |
| 15841 | CD1 | LEU | C | 465 | -34.575 | 2.102 | 28.023 | 1.00 | 78.99 |
| 15842 | CD2 | LEU | C | 465 | -32.930 | 0.278 | 27.581 | 1.00 | 79.34 |
| 15843 | C | LEU | C | 465 | -33.998 | -0.938 | 31.854 | 1.00 | 78.63 |
| 15844 | O | LEU | C | 465 | -33.233 | -1.099 | 32.812 | 1.00 | 78.68 |
| 15845 | N | ARG | C | 466 | -35.322 | -0.901 | 31.986 | 1.00 | 78.11 |
| 15846 | CA | ARG | C | 466 | -35.924 | -1.029 | 33.305 | 1.00 | 77.56 |
| 15847 | CB | ARG | C | 466 | -36.070 | 0.343 | 33.963 | 1.00 | 77.73 |
| 15848 | CG | ARG | C | 466 | -36.849 | 1.341 | 33.141 | 1.00 | 78.08 |
| 15849 | CD | ARG | C | 466 | -36.820 | 2.753 | 33.701 | 1.00 | 78.74 |
| 15850 | NE | ARG | C | 466 | -36.959 | 3.743 | 32.637 | 1.00 | 79.35 |
| 15851 | CZ | ARG | C | 466 | -36.049 | 3.957 | 31.696 | 1.00 | 79.03 |

FIGURE 3 KY

| A | B | C | D | E | F | G | H | I | J |
|---|---|---|---|---|---|---|---|---|---|
| 15852 | NH1 | ARG | C | 466 | -36.264 | 4.874 | 30.764 | 1.00 | 79.06 |
| 15853 | NH2 | ARG | C | 466 | -34.922 | 3.257 | 31.683 | 1.00 | 78.58 |
| 15854 | C | ARG | C | 466 | -37.263 | -1.734 | 33.344 | 1.00 | 77.07 |
| 15855 | O | ARG | C | 466 | -37.818 | -2.141 | 32.322 | 1.00 | 77.09 |
| 15856 | N | VAL | C | 467 | -37.760 | -1.873 | 34.565 | 1.00 | 76.41 |
| 15857 | CA | VAL | C | 467 | -39.040 | -2.484 | 34.836 | 1.00 | 75.67 |
| 15858 | CB | VAL | C | 467 | -38.961 | -3.345 | 36.106 | 1.00 | 75.78 |
| 15859 | CG1 | VAL | C | 467 | -40.344 | -3.819 | 36.532 | 1.00 | 75.88 |
| 15860 | CG2 | VAL | C | 467 | -38.010 | -4.527 | 35.892 | 1.00 | 76.01 |
| 15861 | C | VAL | C | 467 | -40.032 | -1.355 | 35.054 | 1.00 | 75.09 |
| 15862 | O | VAL | C | 467 | -39.787 | -0.464 | 35.864 | 1.00 | 75.04 |
| 15863 | N | LEU | C | 468 | -41.142 | -1.382 | 34.321 | 1.00 | 74.19 |
| 15864 | CA | LEU | C | 468 | -42.159 | -0.344 | 34.443 | 1.00 | 73.37 |
| 15865 | CB | LEU | C | 468 | -42.886 | -0.161 | 33.116 | 1.00 | 73.36 |
| 15866 | CG | LEU | C | 468 | -42.007 | 0.456 | 32.037 | 1.00 | 73.52 |
| 15867 | CD1 | LEU | C | 468 | -42.744 | 0.538 | 30.717 | 1.00 | 73.69 |
| 15868 | CD2 | LEU | C | 468 | -41.547 | 1.832 | 32.497 | 1.00 | 74.21 |
| 15869 | C | LEU | C | 468 | -43.153 | -0.684 | 35.541 | 1.00 | 72.83 |
| 15870 | O | LEU | C | 468 | -43.418 | 0.118 | 36.435 | 1.00 | 72.50 |
| 15871 | N | GLU | C | 469 | -43.711 | -1.883 | 35.456 | 1.00 | 72.20 |
| 15872 | CA | GLU | C | 469 | -44.636 | -2.365 | 36.464 | 1.00 | 71.43 |
| 15873 | CB | GLU | C | 469 | -46.070 | -1.983 | 36.107 | 1.00 | 71.50 |
| 15874 | CG | GLU | C | 469 | -47.100 | -2.496 | 37.094 | 1.00 | 71.46 |
| 15875 | CD | GLU | C | 469 | -46.816 | -2.036 | 38.505 | 1.00 | 71.67 |
| 15876 | OE1 | GLU | C | 469 | -46.582 | -2.900 | 39.375 | 1.00 | 71.29 |
| 15877 | OE2 | GLU | C | 469 | -46.827 | -0.809 | 38.742 | 1.00 | 72.31 |
| 15878 | C | GLU | C | 469 | -44.481 | -3.873 | 36.546 | 1.00 | 70.80 |
| 15879 | O | GLU | C | 469 | -44.445 | -4.551 | 35.526 | 1.00 | 70.65 |
| 15880 | N | ASP | C | 470 | -44.364 | -4.398 | 37.757 | 1.00 | 70.21 |
| 15881 | CA | ASP | C | 470 | -44.177 | -5.830 | 37.921 | 1.00 | 69.68 |
| 15882 | CB | ASP | C | 470 | -42.830 | -6.124 | 38.580 | 1.00 | 69.85 |
| 15883 | CG | ASP | C | 470 | -42.690 | -5.476 | 39.945 | 1.00 | 70.85 |
| 15884 | OD1 | ASP | C | 470 | -41.553 | -5.454 | 40.467 | 1.00 | 71.98 |
| 15885 | OD2 | ASP | C | 470 | -43.650 | -4.968 | 40.573 | 1.00 | 71.66 |
| 15886 | C | ASP | C | 470 | -45.312 | -6.432 | 38.726 | 1.00 | 68.96 |
| 15887 | O | ASP | C | 470 | -45.356 | -7.641 | 38.952 | 1.00 | 68.81 |
| 15888 | N | ASN | C | 471 | -46.223 | -5.568 | 39.159 | 1.00 | 68.21 |
| 15889 | CA | ASN | C | 471 | -47.381 | -5.977 | 39.942 | 1.00 | 67.52 |
| 15890 | CB | ASN | C | 471 | -48.323 | -6.862 | 39.118 | 1.00 | 67.33 |
| 15891 | CG | ASN | C | 471 | -49.373 | -6.053 | 38.364 | 1.00 | 66.65 |
| 15892 | OD1 | ASN | C | 471 | -50.247 | -5.433 | 38.976 | 1.00 | 65.67 |
| 15893 | ND2 | ASN | C | 471 | -49.287 | -6.051 | 37.034 | 1.00 | 64.42 |
| 15894 | C | ASN | C | 471 | -47.021 | -6.643 | 41.261 | 1.00 | 67.42 |
| 15895 | O | ASN | C | 471 | -47.802 | -7.423 | 41.806 | 1.00 | 67.41 |
| 15896 | N | SER | C | 472 | -45.839 | -6.325 | 41.779 | 1.00 | 67.15 |
| 15897 | CA | SER | C | 472 | -45.422 | -6.872 | 43.059 | 1.00 | 66.97 |
| 15898 | CB | SER | C | 472 | -44.074 | -6.287 | 43.496 | 1.00 | 67.26 |
| 15899 | OG | SER | C | 472 | -44.206 | -4.939 | 43.929 | 1.00 | 67.21 |
| 15900 | C | SER | C | 472 | -46.507 | -6.570 | 44.093 | 1.00 | 66.57 |
| 15901 | O | SER | C | 472 | -46.830 | -7.413 | 44.930 | 1.00 | 66.63 |
| 15902 | N | ALA | C | 473 | -47.076 | -5.369 | 44.022 | 1.00 | 65.88 |

FIGURE 3 KZ

| A | B | C | D | E | F | G | H | I | J |
|---|---|---|---|---|---|---|---|---|---|
| 15903 | CA | ALA | C | 473 | -48.153 | -4.986 | 44.929 | 1.00 | 65.34 |
| 15904 | CB | ALA | C | 473 | -48.726 | -3.633 | 44.537 | 1.00 | 65.11 |
| 15905 | C | ALA | C | 473 | -49.256 | -6.046 | 44.945 | 1.00 | 65.07 |
| 15906 | O | ALA | C | 473 | -49.640 | -6.545 | 46.007 | 1.00 | 64.90 |
| 15907 | N | LEU | C | 474 | -49.754 | -6.384 | 43.758 | 1.00 | 64.62 |
| 15908 | CA | LEU | C | 474 | -50.807 | -7.379 | 43.619 | 1.00 | 64.36 |
| 15909 | CB | LEU | C | 474 | -51.247 | -7.500 | 42.160 | 1.00 | 64.23 |
| 15910 | CG | LEU | C | 474 | -52.333 | -8.548 | 41.927 | 1.00 | 64.01 |
| 15911 | CD1 | LEU | C | 474 | -53.688 | -7.987 | 42.297 | 1.00 | 64.03 |
| 15912 | CD2 | LEU | C | 474 | -52.330 | -9.023 | 40.495 | 1.00 | 64.25 |
| 15913 | C | LEU | C | 474 | -50.307 | -8.725 | 44.108 | 1.00 | 64.22 |
| 15914 | O | LEU | C | 474 | -51.001 | -9.431 | 44.843 | 1.00 | 64.04 |
| 15915 | N | ASP | C | 475 | -49.094 | -9.068 | 43.690 | 1.00 | 64.12 |
| 15916 | CA | ASP | C | 475 | -48.474 | -10.321 | 44.079 | 1.00 | 64.14 |
| 15917 | CB | ASP | C | 475 | -47.013 | -10.344 | 43.627 | 1.00 | 64.15 |
| 15918 | CG | ASP | C | 475 | -46.445 | -11.744 | 43.570 | 1.00 | 64.36 |
| 15919 | OD1 | ASP | C | 475 | -45.977 | -12.156 | 42.483 | 1.00 | 63.82 |
| 15920 | OD2 | ASP | C | 475 | -46.423 | -12.504 | 44.563 | 1.00 | 64.34 |
| 15921 | C | ASP | C | 475 | -48.565 | -10.495 | 45.590 | 1.00 | 64.15 |
| 15922 | O | ASP | C | 475 | -48.811 | -11.593 | 46.086 | 1.00 | 64.06 |
| 15923 | N | LYS | C | 476 | -48.396 | -9.393 | 46.313 | 1.00 | 64.14 |
| 15924 | CA | LYS | C | 476 | -48.389 | -9.428 | 47.765 | 1.00 | 64.39 |
| 15925 | CB | LYS | C | 476 | -47.965 | -8.075 | 48.336 | 1.00 | 64.59 |
| 15926 | CG | LYS | C | 476 | -47.947 | -8.027 | 49.855 | 1.00 | 66.02 |
| 15927 | CD | LYS | C | 476 | -47.125 | -6.847 | 50.368 | 1.00 | 68.48 |
| 15928 | CE | LYS | C | 476 | -45.676 | -6.905 | 49.867 | 1.00 | 69.19 |
| 15929 | NZ | LYS | C | 476 | -44.857 | -5.764 | 50.383 | 1.00 | 70.07 |
| 15930 | C | LYS | C | 476 | -49.722 | -9.847 | 48.361 | 1.00 | 64.23 |
| 15931 | O | LYS | C | 476 | -49.774 | -10.760 | 49.186 | 1.00 | 63.98 |
| 15932 | N | MET | C | 477 | -50.800 | -9.182 | 47.958 | 1.00 | 64.16 |
| 15933 | CA | MET | C | 477 | -52.107 | -9.517 | 48.516 | 1.00 | 63.91 |
| 15934 | CB | MET | C | 477 | -53.136 | -8.409 | 48.273 | 1.00 | 64.19 |
| 15935 | CG | MET | C | 477 | -53.177 | -7.856 | 46.863 | 1.00 | 65.27 |
| 15936 | SD | MET | C | 477 | -53.849 | -6.168 | 46.854 | 1.00 | 66.51 |
| 15937 | CE | MET | C | 477 | -54.919 | -6.231 | 48.286 | 1.00 | 67.00 |
| 15938 | C | MET | C | 477 | -52.610 | -10.877 | 48.047 | 1.00 | 63.33 |
| 15939 | O | MET | C | 477 | -53.440 | -11.492 | 48.709 | 1.00 | 63.47 |
| 15940 | N | LEU | C | 478 | -52.079 | -11.359 | 46.930 | 1.00 | 62.62 |
| 15941 | CA | LEU | C | 478 | -52.457 | -12.668 | 46.419 | 1.00 | 62.15 |
| 15942 | CB | LEU | C | 478 | -52.065 | -12.807 | 44.947 | 1.00 | 62.00 |
| 15943 | CG | LEU | C | 478 | -53.148 | -12.549 | 43.894 | 1.00 | 61.31 |
| 15944 | CD1 | LEU | C | 478 | -52.507 | -12.236 | 42.565 | 1.00 | 60.38 |
| 15945 | CD2 | LEU | C | 478 | -54.119 | -11.432 | 44.297 | 1.00 | 60.55 |
| 15946 | C | LEU | C | 478 | -51.859 | -13.806 | 47.249 | 1.00 | 62.27 |
| 15947 | O | LEU | C | 478 | -52.221 | -14.973 | 47.074 | 1.00 | 62.11 |
| 15948 | N | GLN | C | 479 | -50.941 | -13.467 | 48.150 | 1.00 | 62.31 |
| 15949 | CA | GLN | C | 479 | -50.316 | -14.468 | 49.010 | 1.00 | 62.41 |
| 15950 | CB | GLN | C | 479 | -49.098 | -13.887 | 49.719 | 1.00 | 62.77 |
| 15951 | CG | GLN | C | 479 | -47.967 | -13.458 | 48.804 | 1.00 | 63.97 |
| 15952 | CD | GLN | C | 479 | -47.054 | -12.472 | 49.497 | 1.00 | 65.85 |
| 15953 | OE1 | GLN | C | 479 | -47.482 | -11.786 | 50.429 | 1.00 | 66.54 |

FIGURE 3 LA

| A | B | C | D | E | F | G | H | I | J |
|---|---|---|---|---|---|---|---|---|---|
| 15954 | NE2 | GLN | C | 479 | -45.795 | -12.403 | 49.061 | 1.00 | 66.37 |
| 15955 | C | GLN | C | 479 | -51.320 | -14.933 | 50.045 | 1.00 | 62.03 |
| 15956 | O | GLN | C | 479 | -51.306 | -16.084 | 50.469 | 1.00 | 62.09 |
| 15957 | N | ASN | C | 480 | -52.184 | -14.015 | 50.459 | 1.00 | 61.68 |
| 15958 | CA | ASN | C | 480 | -53.247 | -14.328 | 51.397 | 1.00 | 61.21 |
| 15959 | CB | ASN | C | 480 | -53.958 | -13.047 | 51.833 | 1.00 | 61.41 |
| 15960 | CG | ASN | C | 480 | -53.719 | -12.709 | 53.288 | 1.00 | 62.10 |
| 15961 | OD1 | ASN | C | 480 | -53.740 | -11.536 | 53.674 | 1.00 | 62.88 |
| 15962 | ND2 | ASN | C | 480 | -53.501 | -13.736 | 54.111 | 1.00 | 61.27 |
| 15963 | C | ASN | C | 480 | -54.283 | -15.271 | 50.798 | 1.00 | 60.56 |
| 15964 | O | ASN | C | 480 | -54.806 | -16.145 | 51.482 | 1.00 | 60.74 |
| 15965 | N | VAL | C | 481 | -54.569 | -15.111 | 49.513 | 1.00 | 59.62 |
| 15966 | CA | VAL | C | 481 | -55.651 | -15.887 | 48.912 | 1.00 | 58.54 |
| 15967 | CB | VAL | C | 481 | -56.485 | -15.018 | 47.945 | 1.00 | 58.59 |
| 15968 | CG1 | VAL | C | 481 | -55.593 | -14.052 | 47.191 | 1.00 | 58.52 |
| 15969 | CG2 | VAL | C | 481 | -57.285 | -15.887 | 46.999 | 1.00 | 58.15 |
| 15970 | C | VAL | C | 481 | -55.289 | -17.213 | 48.234 | 1.00 | 57.70 |
| 15971 | O | VAL | C | 481 | -54.312 | -17.315 | 47.495 | 1.00 | 57.10 |
| 15972 | N | GLN | C | 482 | -56.111 | -18.221 | 48.507 | 1.00 | 56.94 |
| 15973 | CA | GLN | C | 482 | -56.004 | -19.522 | 47.866 | 1.00 | 56.22 |
| 15974 | CB | GLN | C | 482 | -56.893 | -20.542 | 48.580 | 1.00 | 56.27 |
| 15975 | CG | GLN | C | 482 | -56.552 | -20.768 | 50.044 | 1.00 | 56.54 |
| 15976 | CD | GLN | C | 482 | -57.309 | -21.947 | 50.642 | 1.00 | 57.87 |
| 15977 | OE1 | GLN | C | 482 | -56.993 | -23.102 | 50.357 | 1.00 | 58.06 |
| 15978 | NE2 | GLN | C | 482 | -58.308 | -21.657 | 51.472 | 1.00 | 58.38 |
| 15979 | C | GLN | C | 482 | -56.438 | -19.381 | 46.408 | 1.00 | 55.57 |
| 15980 | O | GLN | C | 482 | -57.605 | -19.551 | 46.068 | 1.00 | 55.85 |
| 15981 | N | MET | C | 483 | -55.487 | -19.071 | 45.544 | 1.00 | 54.50 |
| 15982 | CA | MET | C | 483 | -55.784 | -18.836 | 44.150 | 1.00 | 53.23 |
| 15983 | CB | MET | C | 483 | -54.779 | -17.845 | 43.570 | 1.00 | 53.29 |
| 15984 | CG | MET | C | 483 | -54.907 | -16.464 | 44.187 | 1.00 | 53.22 |
| 15985 | SD | MET | C | 483 | -56.530 | -15.752 | 43.876 | 1.00 | 52.60 |
| 15986 | CE | MET | C | 483 | -56.296 | -15.080 | 42.219 | 1.00 | 53.38 |
| 15987 | C | MET | C | 483 | -55.823 | -20.101 | 43.310 | 1.00 | 52.57 |
| 15988 | O | MET | C | 483 | -55.125 | -21.074 | 43.579 | 1.00 | 52.37 |
| 15989 | N | PRO | C | 484 | -56.669 | -20.074 | 42.291 | 1.00 | 51.80 |
| 15990 | CA | PRO | C | 484 | -56.800 | -21.187 | 41.358 | 1.00 | 51.37 |
| 15991 | CB | PRO | C | 484 | -57.964 | -20.735 | 40.471 | 1.00 | 51.37 |
| 15992 | CG | PRO | C | 484 | -57.908 | -19.250 | 40.546 | 1.00 | 50.94 |
| 15993 | CD | PRO | C | 484 | -57.598 | -18.972 | 41.973 | 1.00 | 51.64 |
| 15994 | C | PRO | C | 484 | -55.533 | -21.275 | 40.525 | 1.00 | 51.05 |
| 15995 | O | PRO | C | 484 | -54.730 | -20.353 | 40.549 | 1.00 | 50.71 |
| 15996 | N | SER | C | 485 | -55.346 | -22.367 | 39.801 | 1.00 | 51.12 |
| 15997 | CA | SER | C | 485 | -54.179 | -22.481 | 38.945 | 1.00 | 51.50 |
| 15998 | CB | SER | C | 485 | -53.292 | -23.659 | 39.358 | 1.00 | 51.29 |
| 15999 | OG | SER | C | 485 | -53.758 | -24.877 | 38.803 | 1.00 | 51.36 |
| 16000 | C | SER | C | 485 | -54.669 | -22.643 | 37.525 | 1.00 | 51.92 |
| 16001 | O | SER | C | 485 | -55.870 | -22.675 | 37.284 | 1.00 | 51.86 |
| 16002 | N | LYS | C | 486 | -53.748 | -22.766 | 36.579 | 1.00 | 52.76 |
| 16003 | CA | LYS | C | 486 | -54.147 | -22.853 | 35.185 | 1.00 | 53.23 |
| 16004 | CB | LYS | C | 486 | -53.849 | -21.528 | 34.483 | 1.00 | 52.93 |

FIGURE 3 LB

| A | B | C | D | E | F | G | H | I | J |
|---|---|---|---|---|---|---|---|---|---|
| 16005 | CG | LYS | C | 486 | -55.017 | -20.990 | 33.676 | 1.00 | 53.08 |
| 16006 | CD | LYS | C | 486 | -54.749 | -20.868 | 32.183 | 1.00 | 50.23 |
| 16007 | CE | LYS | C | 486 | -55.425 | -19.603 | 31.673 | 1.00 | 47.65 |
| 16008 | NZ | LYS | C | 486 | -55.334 | -19.383 | 30.214 | 1.00 | 47.00 |
| 16009 | C | LYS | C | 486 | -53.442 | -23.972 | 34.457 | 1.00 | 53.74 |
| 16010 | O | LYS | C | 486 | -52.215 | -24.070 | 34.477 | 1.00 | 53.99 |
| 16011 | N | LYS | C | 487 | -54.222 | -24.826 | 33.819 | 1.00 | 54.39 |
| 16012 | CA | LYS | C | 487 | -53.658 | -25.861 | 32.984 | 1.00 | 55.08 |
| 16013 | CB | LYS | C | 487 | -54.298 | -27.215 | 33.276 | 1.00 | 55.38 |
| 16014 | CG | LYS | C | 487 | -54.163 | -28.228 | 32.130 | 1.00 | 56.35 |
| 16015 | CD | LYS | C | 487 | -53.045 | -29.243 | 32.348 | 1.00 | 57.73 |
| 16016 | CE | LYS | C | 487 | -53.613 | -30.628 | 32.640 | 1.00 | 58.57 |
| 16017 | NZ | LYS | C | 487 | -52.613 | -31.699 | 32.343 | 1.00 | 58.44 |
| 16018 | C | LYS | C | 487 | -53.914 | -25.465 | 31.541 | 1.00 | 55.57 |
| 16019 | O | LYS | C | 487 | -55.055 | -25.266 | 31.133 | 1.00 | 55.38 |
| 16020 | N | LEU | C | 488 | -52.842 | -25.308 | 30.782 | 1.00 | 56.17 |
| 16021 | CA | LEU | C | 488 | -52.954 | -25.045 | 29.362 | 1.00 | 56.86 |
| 16022 | CB | LEU | C | 488 | -52.169 | -23.798 | 28.971 | 1.00 | 56.87 |
| 16023 | CG | LEU | C | 488 | -52.661 | -23.069 | 27.720 | 1.00 | 56.32 |
| 16024 | CD1 | LEU | C | 488 | -51.490 | -22.755 | 26.814 | 1.00 | 54.85 |
| 16025 | CD2 | LEU | C | 488 | -53.696 | -23.886 | 26.991 | 1.00 | 55.36 |
| 16026 | C | LEU | C | 488 | -52.338 | -26.249 | 28.697 | 1.00 | 57.42 |
| 16027 | O | LEU | C | 488 | -51.132 | -26.465 | 28.772 | 1.00 | 57.62 |
| 16028 | N | ASP | C | 489 | -53.165 | -27.057 | 28.061 | 1.00 | 58.31 |
| 16029 | CA | ASP | C | 489 | -52.663 | -28.255 | 27.426 | 1.00 | 59.02 |
| 16030 | CB | ASP | C | 489 | -52.723 | -29.427 | 28.401 | 1.00 | 59.14 |
| 16031 | CG | ASP | C | 489 | -51.569 | -30.384 | 28.223 | 1.00 | 59.63 |
| 16032 | OD1 | ASP | C | 489 | -50.608 | -30.292 | 29.014 | 1.00 | 59.73 |
| 16033 | OD2 | ASP | C | 489 | -51.529 | -31.243 | 27.314 | 1.00 | 60.12 |
| 16034 | C | ASP | C | 489 | -53.513 | -28.543 | 26.215 | 1.00 | 59.39 |
| 16035 | O | ASP | C | 489 | -54.373 | -27.752 | 25.854 | 1.00 | 59.48 |
| 16036 | N | PHE | C | 490 | -53.278 | -29.681 | 25.585 | 1.00 | 60.01 |
| 16037 | CA | PHE | C | 490 | -54.052 | -30.028 | 24.413 | 1.00 | 60.71 |
| 16038 | CB | PHE | C | 490 | -53.238 | -29.782 | 23.139 | 1.00 | 60.85 |
| 16039 | CG | PHE | C | 490 | -52.154 | -30.798 | 22.909 | 1.00 | 61.45 |
| 16040 | CD1 | PHE | C | 490 | -52.440 | -32.010 | 22.294 | 1.00 | 61.76 |
| 16041 | CE1 | PHE | C | 490 | -51.442 | -32.953 | 22.082 | 1.00 | 61.88 |
| 16042 | CZ | PHE | C | 490 | -50.147 | -32.689 | 22.488 | 1.00 | 61.87 |
| 16043 | CE2 | PHE | C | 490 | -49.850 | -31.482 | 23.106 | 1.00 | 62.01 |
| 16044 | CD2 | PHE | C | 490 | -50.851 | -30.546 | 23.313 | 1.00 | 61.78 |
| 16045 | C | PHE | C | 490 | -54.474 | -31.477 | 24.466 | 1.00 | 60.98 |
| 16046 | O | PHE | C | 490 | -53.859 | -32.294 | 25.157 | 1.00 | 61.02 |
| 16047 | N | ILE | C | 491 | -55.559 | -31.769 | 23.760 | 1.00 | 61.36 |
| 16048 | CA | ILE | C | 491 | -56.009 | -33.128 | 23.546 | 1.00 | 61.73 |
| 16049 | CB | ILE | C | 491 | -57.454 | -33.356 | 24.026 | 1.00 | 61.89 |
| 16050 | CG1 | ILE | C | 491 | -58.450 | -32.595 | 23.145 | 1.00 | 61.68 |
| 16051 | CD1 | ILE | C | 491 | -59.860 | -33.123 | 23.241 | 1.00 | 61.32 |
| 16052 | CG2 | ILE | C | 491 | -57.611 | -32.989 | 25.490 | 1.00 | 61.93 |
| 16053 | C | ILE | C | 491 | -55.945 | -33.280 | 22.042 | 1.00 | 62.11 |
| 16054 | O | ILE | C | 491 | -55.856 | -32.290 | 21.311 | 1.00 | 61.87 |
| 16055 | N | ILE | C | 492 | -55.980 | -34.514 | 21.569 | 1.00 | 62.65 |

FIGURE 3 LC

| A | B | C | D | E | F | G | H | I | J |
|---|---|---|---|---|---|---|---|---|---|
| 16056 | CA | ILE | C | 492 | -55.924 | -34.732 | 20.141 | 1.00 | 63.29 |
| 16057 | CB | ILE | C | 492 | -54.531 | -35.289 | 19.712 | 1.00 | 63.35 |
| 16058 | CG1 | ILE | C | 492 | -54.568 | -35.859 | 18.290 | 1.00 | 63.18 |
| 16059 | CD1 | ILE | C | 492 | -55.163 | -37.252 | 18.191 | 1.00 | 63.21 |
| 16060 | CG2 | ILE | C | 492 | -54.045 | -36.338 | 20.688 | 1.00 | 64.14 |
| 16061 | C | ILE | C | 492 | -57.069 | -35.617 | 19.690 | 1.00 | 63.51 |
| 16062 | O | ILE | C | 492 | -57.331 | -36.664 | 20.282 | 1.00 | 63.49 |
| 16063 | N | LEU | C | 493 | -57.776 | -35.155 | 18.665 | 1.00 | 63.86 |
| 16064 | CA | LEU | C | 493 | -58.839 | -35.926 | 18.044 | 1.00 | 64.34 |
| 16065 | CB | LEU | C | 493 | -60.210 | -35.294 | 18.293 | 1.00 | 64.32 |
| 16066 | CG | LEU | C | 493 | -60.434 | -34.562 | 19.613 | 1.00 | 64.33 |
| 16067 | CD1 | LEU | C | 493 | -59.652 | -33.272 | 19.614 | 1.00 | 64.78 |
| 16068 | CD2 | LEU | C | 493 | -61.912 | -34.273 | 19.822 | 1.00 | 64.93 |
| 16069 | C | LEU | C | 493 | -58.536 | -35.939 | 16.556 | 1.00 | 64.54 |
| 16070 | O | LEU | C | 493 | -58.189 | -34.904 | 15.978 | 1.00 | 64.41 |
| 16071 | N | ASN | C | 494 | -58.635 | -37.118 | 15.948 | 1.00 | 64.97 |
| 16072 | CA | ASN | C | 494 | -58.389 | -37.277 | 14.517 | 1.00 | 65.48 |
| 16073 | CB | ASN | C | 494 | -59.589 | -36.784 | 13.696 | 1.00 | 65.63 |
| 16074 | CG | ASN | C | 494 | -60.760 | -37.758 | 13.723 | 1.00 | 66.99 |
| 16075 | OD1 | ASN | C | 494 | -61.556 | -37.826 | 12.775 | 1.00 | 68.83 |
| 16076 | ND2 | ASN | C | 494 | -60.870 | -38.520 | 14.806 | 1.00 | 67.19 |
| 16077 | C | ASN | C | 494 | -57.116 | -36.590 | 14.036 | 1.00 | 65.35 |
| 16078 | O | ASN | C | 494 | -57.177 | -35.604 | 13.302 | 1.00 | 65.52 |
| 16079 | N | GLU | C | 495 | -55.967 | -37.100 | 14.470 | 1.00 | 65.25 |
| 16080 | CA | GLU | C | 495 | -54.674 | -36.585 | 14.020 | 1.00 | 64.93 |
| 16081 | CB | GLU | C | 495 | -54.560 | -36.705 | 12.491 | 1.00 | 65.49 |
| 16082 | CG | GLU | C | 495 | -53.807 | -37.941 | 12.017 | 1.00 | 67.35 |
| 16083 | CD | GLU | C | 495 | -54.299 | -38.479 | 10.680 | 1.00 | 69.98 |
| 16084 | OE1 | GLU | C | 495 | -55.497 | -38.832 | 10.576 | 1.00 | 70.27 |
| 16085 | OE2 | GLU | C | 495 | -53.481 | -38.574 | 9.733 | 1.00 | 71.37 |
| 16086 | C | GLU | C | 495 | -54.387 | -35.149 | 14.438 | 1.00 | 64.05 |
| 16087 | O | GLU | C | 495 | -53.246 | -34.695 | 14.370 | 1.00 | 63.96 |
| 16088 | N | THR | C | 496 | -55.413 | -34.426 | 14.870 | 1.00 | 62.94 |
| 16089 | CA | THR | C | 496 | -55.225 | -33.013 | 15.194 | 1.00 | 61.53 |
| 16090 | CB | THR | C | 496 | -56.283 | -32.162 | 14.478 | 1.00 | 61.59 |
| 16091 | OG1 | THR | C | 496 | -57.185 | -33.028 | 13.778 | 1.00 | 61.93 |
| 16092 | CG2 | THR | C | 496 | -55.650 | -31.363 | 13.367 | 1.00 | 61.66 |
| 16093 | C | THR | C | 496 | -55.244 | -32.708 | 16.676 | 1.00 | 60.16 |
| 16094 | O | THR | C | 496 | -56.003 | -33.313 | 17.428 | 1.00 | 60.01 |
| 16095 | N | LYS | C | 497 | -54.392 | -31.784 | 17.105 | 1.00 | 58.57 |
| 16096 | CA | LYS | C | 497 | -54.466 | -31.359 | 18.494 | 1.00 | 57.26 |
| 16097 | CB | LYS | C | 497 | -53.105 | -31.245 | 19.178 | 1.00 | 57.60 |
| 16098 | CG | LYS | C | 497 | -52.059 | -30.444 | 18.445 | 1.00 | 59.58 |
| 16099 | CD | LYS | C | 497 | -50.898 | -31.345 | 18.064 | 1.00 | 62.33 |
| 16100 | CE | LYS | C | 497 | -49.588 | -30.719 | 18.490 | 1.00 | 63.93 |
| 16101 | NZ | LYS | C | 497 | -49.605 | -29.244 | 18.260 | 1.00 | 64.60 |
| 16102 | C | LYS | C | 497 | -55.251 | -30.075 | 18.636 | 1.00 | 55.50 |
| 16103 | O | LYS | C | 497 | -55.053 | -29.108 | 17.910 | 1.00 | 55.06 |
| 16104 | N | PHE | C | 498 | -56.177 | -30.098 | 19.573 | 1.00 | 53.90 |
| 16105 | CA | PHE | C | 498 | -56.971 | -28.938 | 19.888 | 1.00 | 52.01 |
| 16106 | CB | PHE | C | 498 | -58.442 | -29.255 | 19.716 | 1.00 | 51.89 |

FIGURE 3 LD

| A | B | C | D | E | F | G | H | I | J |
|---|---|---|---|---|---|---|---|---|---|
| 16107 | CG | PHE | C | 536 | -58.820 | -29.570 | 18.303 | 1.00 | 51.20 |
| 16108 | CD1 | PHE | C | 536 | -59.215 | -28.558 | 17.436 | 1.00 | 50.32 |
| 16109 | CE1 | PHE | C | 536 | -59.564 | -28.837 | 16.145 | 1.00 | 49.58 |
| 16110 | CZ | PHE | C | 536 | -59.519 | -30.143 | 15.689 | 1.00 | 50.88 |
| 16111 | CE2 | PHE | C | 536 | -59.118 | -31.164 | 16.545 | 1.00 | 50.61 |
| 16112 | CD2 | PHE | C | 536 | -58.773 | -30.872 | 17.837 | 1.00 | 50.35 |
| 16113 | C | PHE | C | 536 | -56.645 | -28.589 | 21.318 | 1.00 | 51.06 |
| 16114 | O | PHE | C | 536 | -56.639 | -29.448 | 22.199 | 1.00 | 50.81 |
| 16115 | N | TRP | C | 537 | -56.354 | -27.323 | 21.544 | 1.00 | 49.84 |
| 16116 | CA | TRP | C | 537 | -55.939 | -26.886 | 22.856 | 1.00 | 48.82 |
| 16117 | CB | TRP | C | 537 | -55.087 | -25.628 | 22.733 | 1.00 | 48.86 |
| 16118 | CG | TRP | C | 537 | -53.770 | -25.927 | 22.082 | 1.00 | 49.76 |
| 16119 | CD1 | TRP | C | 537 | -53.523 | -26.076 | 20.746 | 1.00 | 49.81 |
| 16120 | NE1 | TRP | C | 537 | -52.193 | -26.358 | 20.541 | 1.00 | 49.80 |
| 16121 | CE2 | TRP | C | 537 | -51.557 | -26.405 | 21.753 | 1.00 | 49.67 |
| 16122 | CD2 | TRP | C | 537 | -52.521 | -26.145 | 22.745 | 1.00 | 49.62 |
| 16123 | CE3 | TRP | C | 537 | -52.115 | -26.130 | 24.082 | 1.00 | 50.04 |
| 16124 | CZ3 | TRP | C | 537 | -50.790 | -26.379 | 24.378 | 1.00 | 50.07 |
| 16125 | CH2 | TRP | C | 537 | -49.859 | -26.638 | 23.371 | 1.00 | 49.52 |
| 16126 | CZ2 | TRP | C | 537 | -50.220 | -26.658 | 22.055 | 1.00 | 49.89 |
| 16127 | C | TRP | C | 537 | -57.089 | -26.684 | 23.825 | 1.00 | 48.03 |
| 16128 | O | TRP | C | 537 | -58.258 | -26.631 | 23.440 | 1.00 | 47.76 |
| 16129 | N | TYR | C | 538 | -56.743 | -26.607 | 25.101 | 1.00 | 46.94 |
| 16130 | CA | TYR | C | 538 | -57.738 | -26.376 | 26.120 | 1.00 | 46.15 |
| 16131 | CB | TYR | C | 538 | -58.486 | -27.665 | 26.459 | 1.00 | 46.44 |
| 16132 | CG | TYR | C | 538 | -57.762 | -28.647 | 27.355 | 1.00 | 47.01 |
| 16133 | CD1 | TYR | C | 538 | -57.761 | -28.486 | 28.735 | 1.00 | 48.06 |
| 16134 | CE1 | TYR | C | 538 | -57.120 | -29.387 | 29.560 | 1.00 | 49.18 |
| 16135 | CZ | TYR | C | 538 | -56.482 | -30.483 | 29.012 | 1.00 | 50.19 |
| 16136 | OH | TYR | C | 538 | -55.851 | -31.385 | 29.846 | 1.00 | 51.72 |
| 16137 | CE2 | TYR | C | 538 | -56.482 | -30.677 | 27.647 | 1.00 | 48.35 |
| 16138 | CD2 | TYR | C | 538 | -57.123 | -29.760 | 26.828 | 1.00 | 47.62 |
| 16139 | C | TYR | C | 538 | -57.084 | -25.789 | 27.340 | 1.00 | 45.05 |
| 16140 | O | TYR | C | 538 | -55.877 | -25.884 | 27.518 | 1.00 | 45.34 |
| 16141 | N | GLN | C | 539 | -57.883 | -25.145 | 28.166 | 1.00 | 43.83 |
| 16142 | CA | GLN | C | 539 | -57.379 | -24.617 | 29.407 | 1.00 | 42.63 |
| 16143 | CB | GLN | C | 539 | -57.179 | -23.104 | 29.341 | 1.00 | 42.52 |
| 16144 | CG | GLN | C | 539 | -58.457 | -22.266 | 29.213 | 1.00 | 41.27 |
| 16145 | CD | GLN | C | 539 | -58.184 | -20.777 | 29.426 | 1.00 | 39.84 |
| 16146 | OE1 | GLN | C | 539 | -57.168 | -20.256 | 28.953 | 1.00 | 40.31 |
| 16147 | NE2 | GLN | C | 539 | -59.071 | -20.101 | 30.140 | 1.00 | 37.77 |
| 16148 | C | GLN | C | 539 | -58.362 | -24.992 | 30.491 | 1.00 | 42.38 |
| 16149 | O | GLN | C | 539 | -59.542 | -25.217 | 30.224 | 1.00 | 42.21 |
| 16150 | N | MET | C | 540 | -57.862 | -25.117 | 31.708 | 1.00 | 41.97 |
| 16151 | CA | MET | C | 540 | -58.732 | -25.387 | 32.824 | 1.00 | 41.86 |
| 16152 | CB | MET | C | 540 | -58.582 | -26.827 | 33.306 | 1.00 | 41.95 |
| 16153 | CG | MET | C | 540 | -59.272 | -27.858 | 32.442 | 1.00 | 41.45 |
| 16154 | SD | MET | C | 540 | -59.183 | -29.494 | 33.189 | 1.00 | 42.36 |
| 16155 | CE | MET | C | 540 | -60.321 | -30.356 | 32.234 | 1.00 | 39.76 |
| 16156 | C | MET | C | 540 | -58.357 | -24.427 | 33.922 | 1.00 | 41.70 |
| 16157 | O | MET | C | 540 | -57.186 | -24.155 | 34.118 | 1.00 | 41.42 |

FIGURE 3 LE

| A | B | C | D | E | F | G | H | I | J |
|---|---|---|---|---|---|---|---|---|---|
| 16158 | N | ILE | C | 503 | -59.354 | -23.856 | 34.588 | 1.00 | 41.92 |
| 16159 | CA | ILE | C | 503 | -59.075 | -23.054 | 35.763 | 1.00 | 42.01 |
| 16160 | CB | ILE | C | 503 | -59.994 | -21.826 | 35.854 | 1.00 | 42.23 |
| 16161 | CG1 | ILE | C | 503 | -59.842 | -20.963 | 34.598 | 1.00 | 41.89 |
| 16162 | CD1 | ILE | C | 503 | -58.508 | -20.286 | 34.511 | 1.00 | 42.23 |
| 16163 | CG2 | ILE | C | 503 | -59.641 | -20.979 | 37.071 | 1.00 | 41.21 |
| 16164 | C | ILE | C | 503 | -59.308 | -24.045 | 36.887 | 1.00 | 42.28 |
| 16165 | O | ILE | C | 503 | -60.428 | -24.470 | 37.135 | 1.00 | 41.93 |
| 16166 | N | LEU | C | 504 | -58.224 | -24.470 | 37.518 | 1.00 | 43.06 |
| 16167 | CA | LEU | C | 504 | -58.304 | -25.502 | 38.543 | 1.00 | 43.54 |
| 16168 | CB | LEU | C | 504 | -57.080 | -26.414 | 38.449 | 1.00 | 43.91 |
| 16169 | CG | LEU | C | 504 | -57.009 | -27.263 | 37.176 | 1.00 | 44.82 |
| 16170 | CD1 | LEU | C | 504 | -55.578 | -27.642 | 36.816 | 1.00 | 46.01 |
| 16171 | CD2 | LEU | C | 504 | -57.869 | -28.502 | 37.314 | 1.00 | 45.64 |
| 16172 | C | LEU | C | 504 | -58.424 | -24.904 | 39.925 | 1.00 | 43.21 |
| 16173 | O | LEU | C | 504 | -57.735 | -23.959 | 40.249 | 1.00 | 43.43 |
| 16174 | N | PRO | C | 505 | -59.333 | -25.425 | 40.731 | 1.00 | 43.54 |
| 16175 | CA | PRO | C | 505 | -59.478 | -24.952 | 42.112 | 1.00 | 44.26 |
| 16176 | CB | PRO | C | 505 | -60.571 | -25.860 | 42.676 | 1.00 | 44.09 |
| 16177 | CG | PRO | C | 505 | -61.320 | -26.330 | 41.467 | 1.00 | 43.90 |
| 16178 | CD | PRO | C | 505 | -60.299 | -26.482 | 40.392 | 1.00 | 43.18 |
| 16179 | C | PRO | C | 505 | -58.167 | -25.154 | 42.878 | 1.00 | 44.94 |
| 16180 | O | PRO | C | 505 | -57.382 | -26.049 | 42.544 | 1.00 | 45.02 |
| 16181 | N | PRO | C | 506 | -57.916 | -24.322 | 43.876 | 1.00 | 45.64 |
| 16182 | CA | PRO | C | 506 | -56.703 | -24.454 | 44.689 | 1.00 | 46.49 |
| 16183 | CB | PRO | C | 506 | -56.956 | -23.461 | 45.832 | 1.00 | 46.41 |
| 16184 | CG | PRO | C | 506 | -58.453 | -23.247 | 45.787 | 1.00 | 45.84 |
| 16185 | CD | PRO | C | 506 | -58.762 | -23.205 | 44.329 | 1.00 | 45.32 |
| 16186 | C | PRO | C | 506 | -56.624 | -25.876 | 45.234 | 1.00 | 47.23 |
| 16187 | O | PRO | C | 506 | -57.660 | -26.522 | 45.340 | 1.00 | 47.08 |
| 16188 | N | HIS | C | 507 | -55.425 | -26.369 | 45.540 | 1.00 | 48.57 |
| 16189 | CA | HIS | C | 507 | -55.282 | -27.707 | 46.120 | 1.00 | 49.66 |
| 16190 | CB | HIS | C | 507 | -55.917 | -27.749 | 47.509 | 1.00 | 49.52 |
| 16191 | CG | HIS | C | 507 | -55.425 | -26.672 | 48.420 | 1.00 | 50.26 |
| 16192 | ND1 | HIS | C | 507 | -54.085 | -26.392 | 48.579 | 1.00 | 51.83 |
| 16193 | CE1 | HIS | C | 507 | -53.943 | -25.393 | 49.433 | 1.00 | 52.49 |
| 16194 | NE2 | HIS | C | 507 | -55.145 | -25.009 | 49.827 | 1.00 | 52.30 |
| 16195 | CD2 | HIS | C | 507 | -56.089 | -25.793 | 49.205 | 1.00 | 51.46 |
| 16196 | C | HIS | C | 507 | -55.918 | -28.763 | 45.243 | 1.00 | 50.46 |
| 16197 | O | HIS | C | 507 | -56.417 | -29.783 | 45.732 | 1.00 | 50.36 |
| 16198 | N | PHE | C | 508 | -55.900 | -28.505 | 43.942 | 1.00 | 51.48 |
| 16199 | CA | PHE | C | 508 | -56.486 | -29.414 | 42.972 | 1.00 | 52.60 |
| 16200 | CB | PHE | C | 508 | -56.038 | -29.044 | 41.562 | 1.00 | 52.56 |
| 16201 | CG | PHE | C | 508 | -56.543 | -29.978 | 40.512 | 1.00 | 53.20 |
| 16202 | CD1 | PHE | C | 508 | -57.872 | -30.365 | 40.500 | 1.00 | 53.20 |
| 16203 | CE1 | PHE | C | 508 | -58.347 | -31.232 | 39.547 | 1.00 | 52.98 |
| 16204 | CZ | PHE | C | 508 | -57.498 | -31.727 | 38.584 | 1.00 | 54.15 |
| 16205 | CE2 | PHE | C | 508 | -56.170 | -31.352 | 38.577 | 1.00 | 54.47 |
| 16206 | CD2 | PHE | C | 508 | -55.693 | -30.478 | 39.543 | 1.00 | 54.09 |
| 16207 | C | PHE | C | 508 | -56.100 | -30.855 | 43.280 | 1.00 | 53.25 |
| 16208 | O | PHE | C | 508 | -54.935 | -31.218 | 43.230 | 1.00 | 53.57 |

FIGURE 3 LF

| A | B | C | D | E | F | G | H | I | J |
|---|---|---|---|---|---|---|---|---|---|
| 16209 | N | ASP | C | 509 | -57.094 | -31.672 | 43.591 | 1.00 | 54.01 |
| 16210 | CA | ASP | C | 509 | -56.864 | -33.065 | 43.923 | 1.00 | 54.47 |
| 16211 | CB | ASP | C | 509 | -57.562 | -33.383 | 45.244 | 1.00 | 54.61 |
| 16212 | CG | ASP | C | 509 | -57.124 | -34.710 | 45.830 | 1.00 | 55.69 |
| 16213 | OD1 | ASP | C | 509 | -56.496 | -35.515 | 45.096 | 1.00 | 55.73 |
| 16214 | OD2 | ASP | C | 509 | -57.358 | -35.026 | 47.019 | 1.00 | 56.78 |
| 16215 | C | ASP | C | 509 | -57.446 | -33.946 | 42.834 | 1.00 | 54.50 |
| 16216 | O | ASP | C | 509 | -58.631 | -34.255 | 42.870 | 1.00 | 54.41 |
| 16217 | N | LYS | C | 510 | -56.633 | -34.377 | 41.878 | 1.00 | 54.71 |
| 16218 | CA | LYS | C | 510 | -57.194 | -35.163 | 40.787 | 1.00 | 55.19 |
| 16219 | CB | LYS | C | 510 | -56.290 | -35.182 | 39.550 | 1.00 | 55.52 |
| 16220 | CG | LYS | C | 510 | -55.265 | -36.277 | 39.491 | 1.00 | 57.13 |
| 16221 | CD | LYS | C | 510 | -54.371 | -36.077 | 38.265 | 1.00 | 59.98 |
| 16222 | CE | LYS | C | 510 | -53.381 | -37.232 | 38.092 | 1.00 | 61.73 |
| 16223 | NZ | LYS | C | 510 | -52.692 | -37.631 | 39.371 | 1.00 | 62.38 |
| 16224 | C | LYS | C | 510 | -57.660 | -36.551 | 41.217 | 1.00 | 55.14 |
| 16225 | O | LYS | C | 510 | -58.029 | -37.382 | 40.385 | 1.00 | 55.40 |
| 16226 | N | SER | C | 511 | -57.662 | -36.790 | 42.524 | 1.00 | 54.73 |
| 16227 | CA | SER | C | 511 | -58.232 | -38.018 | 43.054 | 1.00 | 54.59 |
| 16228 | CB | SER | C | 511 | -57.539 | -38.443 | 44.358 | 1.00 | 54.85 |
| 16229 | OG | SER | C | 511 | -57.882 | -37.597 | 45.448 | 1.00 | 54.26 |
| 16230 | C | SER | C | 511 | -59.714 | -37.768 | 43.299 | 1.00 | 54.35 |
| 16231 | O | SER | C | 511 | -60.493 | -38.700 | 43.493 | 1.00 | 55.12 |
| 16232 | N | LYS | C | 512 | -60.101 | -36.499 | 43.258 | 1.00 | 53.65 |
| 16233 | CA | LYS | C | 512 | -61.468 | -36.078 | 43.552 | 1.00 | 52.82 |
| 16234 | CB | LYS | C | 512 | -61.403 | -34.763 | 44.331 | 1.00 | 53.04 |
| 16235 | CG | LYS | C | 512 | -62.099 | -34.771 | 45.667 | 1.00 | 54.26 |
| 16236 | CD | LYS | C | 512 | -62.383 | -33.345 | 46.125 | 1.00 | 56.92 |
| 16237 | CE | LYS | C | 512 | -63.344 | -32.629 | 45.158 | 1.00 | 56.98 |
| 16238 | NZ | LYS | C | 512 | -63.916 | -31.389 | 45.767 | 1.00 | 57.79 |
| 16239 | C | LYS | C | 512 | -62.325 | -35.882 | 42.290 | 1.00 | 51.91 |
| 16240 | O | LYS | C | 512 | -61.808 | -35.821 | 41.177 | 1.00 | 51.79 |
| 16241 | N | LYS | C | 513 | -63.640 | -35.797 | 42.457 | 1.00 | 50.85 |
| 16242 | CA | LYS | C | 513 | -64.516 | -35.506 | 41.321 | 1.00 | 50.07 |
| 16243 | CB | LYS | C | 513 | -65.636 | -36.534 | 41.193 | 1.00 | 50.55 |
| 16244 | CG | LYS | C | 513 | -65.517 | -37.440 | 39.973 | 1.00 | 51.47 |
| 16245 | CD | LYS | C | 513 | -64.311 | -38.346 | 40.038 | 1.00 | 52.82 |
| 16246 | CE | LYS | C | 513 | -64.352 | -39.369 | 38.912 | 1.00 | 55.30 |
| 16247 | NZ | LYS | C | 513 | -63.323 | -40.430 | 39.099 | 1.00 | 56.62 |
| 16248 | C | LYS | C | 513 | -65.106 | -34.104 | 41.440 | 1.00 | 49.11 |
| 16249 | O | LYS | C | 513 | -65.999 | -33.861 | 42.265 | 1.00 | 48.91 |
| 16250 | N | TYR | C | 514 | -64.592 | -33.190 | 40.616 | 1.00 | 47.40 |
| 16251 | CA | TYR | C | 514 | -65.022 | -31.796 | 40.625 | 1.00 | 45.99 |
| 16252 | CB | TYR | C | 514 | -63.823 | -30.876 | 40.349 | 1.00 | 46.37 |
| 16253 | CG | TYR | C | 514 | -62.751 | -30.847 | 41.425 | 1.00 | 46.45 |
| 16254 | CD1 | TYR | C | 514 | -62.653 | -29.772 | 42.299 | 1.00 | 45.90 |
| 16255 | CE1 | TYR | C | 514 | -61.682 | -29.725 | 43.274 | 1.00 | 45.89 |
| 16256 | CZ | TYR | C | 514 | -60.775 | -30.760 | 43.391 | 1.00 | 46.54 |
| 16257 | OH | TYR | C | 514 | -59.813 | -30.702 | 44.370 | 1.00 | 46.03 |
| 16258 | CE2 | TYR | C | 514 | -60.833 | -31.837 | 42.527 | 1.00 | 46.37 |
| 16259 | CD2 | TYR | C | 514 | -61.821 | -31.876 | 41.545 | 1.00 | 46.34 |

FIGURE 3 LG

| A | B | C | D | E | F | G | H | I | J |
|---|---|---|---|---|---|---|---|---|---|
| 16260 | C | TYR | C | 514 | -66.110 | -31.490 | 39.586 | 1.00 | 44.66 |
| 16261 | O | TYR | C | 514 | -66.156 | -32.084 | 38.506 | 1.00 | 44.11 |
| 16262 | N | PRO | C | 515 | -66.994 | -30.558 | 39.924 | 1.00 | 43.58 |
| 16263 | CA | PRO | C | 515 | -67.989 | -30.075 | 38.966 | 1.00 | 42.42 |
| 16264 | CB | PRO | C | 515 | -68.864 | -29.137 | 39.796 | 1.00 | 42.57 |
| 16265 | CG | PRO | C | 515 | -68.510 | -29.388 | 41.201 | 1.00 | 43.62 |
| 16266 | CD | PRO | C | 515 | -67.116 | -29.917 | 41.242 | 1.00 | 43.47 |
| 16267 | C | PRO | C | 515 | -67.227 | -29.269 | 37.926 | 1.00 | 41.29 |
| 16268 | O | PRO | C | 515 | -66.223 | -28.628 | 38.255 | 1.00 | 41.28 |
| 16269 | N | LEU | C | 516 | -67.688 | -29.305 | 36.690 | 1.00 | 39.64 |
| 16270 | CA | LEU | C | 516 | -66.989 | -28.641 | 35.611 | 1.00 | 38.46 |
| 16271 | CB | LEU | C | 516 | -66.460 | -29.692 | 34.635 | 1.00 | 38.67 |
| 16272 | CG | LEU | C | 516 | -65.667 | -29.255 | 33.401 | 1.00 | 38.05 |
| 16273 | CD1 | LEU | C | 516 | -64.209 | -29.124 | 33.739 | 1.00 | 36.52 |
| 16274 | CD2 | LEU | C | 516 | -65.827 | -30.283 | 32.308 | 1.00 | 37.46 |
| 16275 | C | LEU | C | 516 | -67.940 | -27.682 | 34.889 | 1.00 | 37.84 |
| 16276 | O | LEU | C | 516 | -69.102 | -28.014 | 34.635 | 1.00 | 37.36 |
| 16277 | N | LEU | C | 517 | -67.443 | -26.486 | 34.593 | 1.00 | 36.52 |
| 16278 | CA | LEU | C | 517 | -68.210 | -25.490 | 33.877 | 1.00 | 35.89 |
| 16279 | CB | LEU | C | 517 | -68.404 | -24.238 | 34.727 | 1.00 | 35.94 |
| 16280 | CG | LEU | C | 517 | -68.978 | -23.022 | 34.005 | 1.00 | 35.16 |
| 16281 | CD1 | LEU | C | 517 | -68.996 | -21.860 | 34.950 | 1.00 | 33.43 |
| 16282 | CD2 | LEU | C | 517 | -70.380 | -23.317 | 33.475 | 1.00 | 34.88 |
| 16283 | C | LEU | C | 517 | -67.465 | -25.156 | 32.608 | 1.00 | 35.87 |
| 16284 | O | LEU | C | 517 | -66.327 | -24.682 | 32.647 | 1.00 | 35.50 |
| 16285 | N | LEU | C | 518 | -68.106 | -25.432 | 31.481 | 1.00 | 35.95 |
| 16286 | CA | LEU | C | 518 | -67.500 | -25.207 | 30.188 | 1.00 | 36.30 |
| 16287 | CB | LEU | C | 518 | -68.041 | -26.207 | 29.181 | 1.00 | 36.73 |
| 16288 | CG | LEU | C | 518 | -67.282 | -26.325 | 27.869 | 1.00 | 37.04 |
| 16289 | CD1 | LEU | C | 518 | -65.811 | -26.590 | 28.134 | 1.00 | 35.63 |
| 16290 | CD2 | LEU | C | 518 | -67.905 | -27.421 | 27.014 | 1.00 | 37.45 |
| 16291 | C | LEU | C | 518 | -67.791 | -23.787 | 29.735 | 1.00 | 36.65 |
| 16292 | O | LEU | C | 518 | -68.924 | -23.447 | 29.387 | 1.00 | 36.65 |
| 16293 | N | ASP | C | 519 | -66.749 | -22.967 | 29.771 | 1.00 | 36.55 |
| 16294 | CA | ASP | C | 519 | -66.805 | -21.572 | 29.402 | 1.00 | 36.82 |
| 16295 | CB | ASP | C | 519 | -65.752 | -20.816 | 30.212 | 1.00 | 36.79 |
| 16296 | CG | ASP | C | 519 | -65.709 | -19.360 | 29.894 | 1.00 | 38.12 |
| 16297 | OD1 | ASP | C | 519 | -65.070 | -18.613 | 30.668 | 1.00 | 39.34 |
| 16298 | OD2 | ASP | C | 519 | -66.275 | -18.868 | 28.887 | 1.00 | 40.62 |
| 16299 | C | ASP | C | 519 | -66.522 | -21.496 | 27.917 | 1.00 | 36.75 |
| 16300 | O | ASP | C | 519 | -65.403 | -21.757 | 27.486 | 1.00 | 37.25 |
| 16301 | N | VAL | C | 520 | -67.529 | -21.141 | 27.125 | 1.00 | 36.58 |
| 16302 | CA | VAL | C | 520 | -67.366 | -21.164 | 25.677 | 1.00 | 36.22 |
| 16303 | CB | VAL | C | 520 | -68.311 | -22.213 | 25.027 | 1.00 | 36.82 |
| 16304 | CG1 | VAL | C | 520 | -69.765 | -21.780 | 25.170 | 1.00 | 36.54 |
| 16305 | CG2 | VAL | C | 520 | -67.986 | -22.386 | 23.548 | 1.00 | 35.85 |
| 16306 | C | VAL | C | 520 | -67.613 | -19.853 | 24.926 | 1.00 | 35.93 |
| 16307 | O | VAL | C | 520 | -68.394 | -19.002 | 25.342 | 1.00 | 35.87 |
| 16308 | N | TYR | C | 521 | -66.905 | -19.711 | 23.816 | 1.00 | 35.45 |
| 16309 | CA | TYR | C | 521 | -67.209 | -18.693 | 22.839 | 1.00 | 35.17 |
| 16310 | CB | TYR | C | 521 | -66.073 | -17.707 | 22.647 | 1.00 | 35.08 |

FIGURE 3 LH

| A | B | C | D | E | F | G | H | I | J |
|---|---|---|---|---|---|---|---|---|---|
| 16311 | CG | TYR | C | 521 | -66.482 | -16.546 | 21.785 | 1.00 | 36.28 |
| 16312 | CD1 | TYR | C | 521 | -65.839 | -16.284 | 20.581 | 1.00 | 37.58 |
| 16313 | CE1 | TYR | C | 521 | -66.213 | -15.203 | 19.789 | 1.00 | 37.96 |
| 16314 | CZ | TYR | C | 521 | -67.242 | -14.385 | 20.193 | 1.00 | 37.65 |
| 16315 | OH | TYR | C | 521 | -67.625 | -13.317 | 19.397 | 1.00 | 39.32 |
| 16316 | CE2 | TYR | C | 521 | -67.900 | -14.631 | 21.385 | 1.00 | 36.97 |
| 16317 | CD2 | TYR | C | 521 | -67.524 | -15.709 | 22.168 | 1.00 | 36.92 |
| 16318 | C | TYR | C | 521 | -67.416 | -19.499 | 21.576 | 1.00 | 34.87 |
| 16319 | O | TYR | C | 521 | -68.549 | -19.667 | 21.123 | 1.00 | 34.35 |
| 16320 | N | ALA | C | 522 | -66.302 | -20.002 | 21.035 | 1.00 | 34.36 |
| 16321 | CA | ALA | C | 522 | -66.267 | -20.860 | 19.849 | 1.00 | 34.66 |
| 16322 | CB | ALA | C | 522 | -67.105 | -22.122 | 20.053 | 1.00 | 34.03 |
| 16323 | C | ALA | C | 522 | -66.639 | -20.174 | 18.538 | 1.00 | 35.15 |
| 16324 | O | ALA | C | 522 | -67.042 | -20.828 | 17.590 | 1.00 | 35.80 |
| 16325 | N | GLY | C | 523 | -66.513 | -18.863 | 18.476 | 1.00 | 35.90 |
| 16326 | CA | GLY | C | 523 | -66.770 | -18.161 | 17.237 | 1.00 | 37.37 |
| 16327 | C | GLY | C | 523 | -65.615 | -18.337 | 16.264 | 1.00 | 38.19 |
| 16328 | O | GLY | C | 523 | -64.519 | -18.759 | 16.643 | 1.00 | 38.72 |
| 16329 | N | PRO | C | 524 | -65.854 | -18.030 | 14.999 | 1.00 | 38.51 |
| 16330 | CA | PRO | C | 524 | -64.820 | -18.193 | 13.978 | 1.00 | 38.34 |
| 16331 | CB | PRO | C | 524 | -65.494 | -17.648 | 12.718 | 1.00 | 38.73 |
| 16332 | CG | PRO | C | 524 | -66.940 | -17.914 | 12.957 | 1.00 | 37.95 |
| 16333 | CD | PRO | C | 524 | -67.132 | -17.573 | 14.425 | 1.00 | 38.47 |
| 16334 | C | PRO | C | 524 | -63.549 | -17.440 | 14.314 | 1.00 | 38.47 |
| 16335 | O | PRO | C | 524 | -63.571 | -16.247 | 14.616 | 1.00 | 37.52 |
| 16336 | N | CYS | C | 525 | -62.436 | -18.171 | 14.255 | 1.00 | 38.84 |
| 16337 | CA | CYS | C | 525 | -61.123 | -17.626 | 14.562 | 1.00 | 38.88 |
| 16338 | CB | CYS | C | 525 | -60.759 | -16.485 | 13.612 | 1.00 | 38.85 |
| 16339 | SG | CYS | C | 525 | -59.060 | -15.880 | 13.830 | 1.00 | 40.62 |
| 16340 | C | CYS | C | 525 | -61.048 | -17.158 | 16.004 | 1.00 | 38.44 |
| 16341 | O | CYS | C | 525 | -60.417 | -16.146 | 16.313 | 1.00 | 38.85 |
| 16342 | N | SER | C | 526 | -61.704 | -17.884 | 16.895 | 1.00 | 38.38 |
| 16343 | CA | SER | C | 526 | -61.654 | -17.526 | 18.311 | 1.00 | 38.62 |
| 16344 | CB | SER | C | 526 | -62.996 | -17.809 | 18.994 | 1.00 | 38.49 |
| 16345 | OG | SER | C | 526 | -63.435 | -19.140 | 18.774 | 1.00 | 37.11 |
| 16346 | C | SER | C | 526 | -60.542 | -18.264 | 19.058 | 1.00 | 39.03 |
| 16347 | O | SER | C | 526 | -60.001 | -19.258 | 18.584 | 1.00 | 39.34 |
| 16348 | N | GLN | C | 527 | -60.196 | -17.755 | 20.230 | 1.00 | 39.54 |
| 16349 | CA | GLN | C | 527 | -59.257 | -18.434 | 21.100 | 1.00 | 39.53 |
| 16350 | CB | GLN | C | 527 | -57.821 | -17.977 | 20.862 | 1.00 | 39.36 |
| 16351 | CG | GLN | C | 527 | -56.804 | -18.894 | 21.539 | 1.00 | 38.55 |
| 16352 | CD | GLN | C | 527 | -55.382 | -18.582 | 21.129 | 1.00 | 36.93 |
| 16353 | OE1 | GLN | C | 527 | -54.818 | -17.568 | 21.549 | 1.00 | 36.25 |
| 16354 | NE2 | GLN | C | 527 | -54.802 | -19.443 | 20.301 | 1.00 | 35.31 |
| 16355 | C | GLN | C | 527 | -59.632 | -18.203 | 22.547 | 1.00 | 40.01 |
| 16356 | O | GLN | C | 527 | -59.517 | -17.087 | 23.057 | 1.00 | 39.96 |
| 16357 | N | LYS | C | 528 | -60.052 | -19.279 | 23.202 | 1.00 | 40.79 |
| 16358 | CA | LYS | C | 528 | -60.438 | -19.258 | 24.607 | 1.00 | 41.63 |
| 16359 | CB | LYS | C | 528 | -61.821 | -19.893 | 24.777 | 1.00 | 41.25 |
| 16360 | CG | LYS | C | 528 | -62.964 | -19.061 | 24.242 | 1.00 | 42.03 |
| 16361 | CD | LYS | C | 528 | -62.998 | -17.679 | 24.871 | 1.00 | 41.88 |

FIGURE 3 LI

| A | B | C | D | E | F | G | H | I | J |
|---|---|---|---|---|---|---|---|---|---|
| 16362 | CE  | LYS | C | 528 | -63.410 | -17.733 | 26.334 | 1.00 | 43.10 |
| 16363 | NZ  | LYS | C | 528 | -64.595 | -18.591 | 26.552 | 1.00 | 43.01 |
| 16364 | C   | LYS | C | 528 | -59.435 | -20.019 | 25.490 | 1.00 | 42.21 |
| 16365 | O   | LYS | C | 528 | -59.585 | -20.041 | 26.707 | 1.00 | 42.08 |
| 16366 | N   | ALA | C | 529 | -58.452 | -20.679 | 24.878 | 1.00 | 43.14 |
| 16367 | CA  | ALA | C | 529 | -57.400 | -21.380 | 25.637 | 1.00 | 44.01 |
| 16368 | CB  | ALA | C | 529 | -57.263 | -22.810 | 25.193 | 1.00 | 43.72 |
| 16369 | C   | ALA | C | 529 | -56.101 | -20.621 | 25.426 | 1.00 | 44.60 |
| 16370 | O   | ALA | C | 529 | -55.393 | -20.825 | 24.434 | 1.00 | 44.85 |
| 16371 | N   | ASP | C | 530 | -55.813 | -19.742 | 26.381 | 1.00 | 45.15 |
| 16372 | CA  | ASP | C | 530 | -54.731 | -18.776 | 26.297 | 1.00 | 45.16 |
| 16373 | CB  | ASP | C | 530 | -55.279 | -17.374 | 26.611 | 1.00 | 45.38 |
| 16374 | CG  | ASP | C | 530 | -56.191 | -16.835 | 25.547 | 1.00 | 47.53 |
| 16375 | OD1 | ASP | C | 530 | -56.389 | -17.511 | 24.514 | 1.00 | 51.33 |
| 16376 | OD2 | ASP | C | 530 | -56.760 | -15.725 | 25.653 | 1.00 | 49.13 |
| 16377 | C   | ASP | C | 530 | -53.650 | -18.996 | 27.336 | 1.00 | 44.93 |
| 16378 | O   | ASP | C | 530 | -53.765 | -19.821 | 28.244 | 1.00 | 44.54 |
| 16379 | N   | THR | C | 531 | -52.623 | -18.171 | 27.211 | 1.00 | 44.51 |
| 16380 | CA  | THR | C | 531 | -51.547 | -18.105 | 28.162 | 1.00 | 44.63 |
| 16381 | CB  | THR | C | 531 | -50.218 | -17.958 | 27.403 | 1.00 | 44.73 |
| 16382 | OG1 | THR | C | 531 | -49.571 | -19.236 | 27.328 | 1.00 | 44.91 |
| 16383 | CG2 | THR | C | 531 | -49.257 | -17.124 | 28.184 | 1.00 | 44.96 |
| 16384 | C   | THR | C | 531 | -51.813 | -16.877 | 29.014 | 1.00 | 44.29 |
| 16385 | O   | THR | C | 531 | -51.008 | -16.521 | 29.875 | 1.00 | 44.87 |
| 16386 | N   | VAL | C | 532 | -52.951 | -16.227 | 28.775 | 1.00 | 43.80 |
| 16387 | CA  | VAL | C | 532 | -53.306 | -15.010 | 29.511 | 1.00 | 43.27 |
| 16388 | CB  | VAL | C | 532 | -54.450 | -14.236 | 28.829 | 1.00 | 43.34 |
| 16389 | CG1 | VAL | C | 532 | -54.672 | -12.897 | 29.531 | 1.00 | 42.91 |
| 16390 | CG2 | VAL | C | 532 | -54.165 | -14.035 | 27.338 | 1.00 | 43.20 |
| 16391 | C   | VAL | C | 532 | -53.732 | -15.267 | 30.955 | 1.00 | 42.83 |
| 16392 | O   | VAL | C | 532 | -54.409 | -16.261 | 31.248 | 1.00 | 42.85 |
| 16393 | N   | PHE | C | 533 | -53.329 | -14.361 | 31.843 | 1.00 | 41.98 |
| 16394 | CA  | PHE | C | 533 | -53.702 | -14.411 | 33.249 | 1.00 | 41.36 |
| 16395 | CB  | PHE | C | 533 | -52.565 | -13.918 | 34.138 | 1.00 | 41.44 |
| 16396 | CG  | PHE | C | 533 | -52.964 | -13.784 | 35.574 | 1.00 | 41.43 |
| 16397 | CD1 | PHE | C | 533 | -52.925 | -14.879 | 36.418 | 1.00 | 41.07 |
| 16398 | CE1 | PHE | C | 533 | -53.322 | -14.766 | 37.732 | 1.00 | 40.00 |
| 16399 | CZ  | PHE | C | 533 | -53.775 | -13.549 | 38.210 | 1.00 | 39.72 |
| 16400 | CE2 | PHE | C | 533 | -53.838 | -12.457 | 37.372 | 1.00 | 38.97 |
| 16401 | CD2 | PHE | C | 533 | -53.437 | -12.576 | 36.067 | 1.00 | 40.26 |
| 16402 | C   | PHE | C | 533 | -54.924 | -13.537 | 33.524 | 1.00 | 41.00 |
| 16403 | O   | PHE | C | 533 | -54.880 | -12.332 | 33.323 | 1.00 | 40.50 |
| 16404 | N   | ARG | C | 534 | -55.993 | -14.128 | 34.049 | 1.00 | 40.90 |
| 16405 | CA  | ARG | C | 534 | -57.228 | -13.371 | 34.249 | 1.00 | 40.66 |
| 16406 | CB  | ARG | C | 534 | -58.307 | -13.855 | 33.279 | 1.00 | 40.29 |
| 16407 | CG  | ARG | C | 534 | -57.986 | -13.583 | 31.820 | 1.00 | 40.64 |
| 16408 | CD  | ARG | C | 534 | -58.970 | -14.213 | 30.847 | 1.00 | 41.30 |
| 16409 | NE  | ARG | C | 534 | -58.329 | -14.682 | 29.619 | 1.00 | 41.87 |
| 16410 | CZ  | ARG | C | 534 | -58.104 | -13.910 | 28.572 | 1.00 | 42.89 |
| 16411 | NH1 | ARG | C | 534 | -58.468 | -12.627 | 28.616 | 1.00 | 46.10 |
| 16412 | NH2 | ARG | C | 534 | -57.520 | -14.401 | 27.485 | 1.00 | 39.05 |

FIGURE 3 LJ

| A | B | C | D | E | F | G | H | I | J |
|---|---|---|---|---|---|---|---|---|---|
| 16413 | C | ARG | C | 534 | -57.777 | -13.400 | 35.655 | 1.00 | 40.25 |
| 16414 | O | ARG | C | 534 | -57.635 | -14.379 | 36.373 | 1.00 | 41.51 |
| 16415 | N | LEU | C | 535 | -58.399 | -12.302 | 36.043 | 1.00 | 39.84 |
| 16416 | CA | LEU | C | 535 | -59.089 | -12.207 | 37.319 | 1.00 | 39.11 |
| 16417 | CB | LEU | C | 535 | -58.534 | -11.054 | 38.151 | 1.00 | 39.17 |
| 16418 | CG | LEU | C | 535 | -57.104 | -11.299 | 38.668 | 1.00 | 39.51 |
| 16419 | CD1 | LEU | C | 535 | -56.585 | -10.129 | 39.483 | 1.00 | 39.68 |
| 16420 | CD2 | LEU | C | 535 | -57.045 | -12.577 | 39.505 | 1.00 | 38.92 |
| 16421 | C | LEU | C | 535 | -60.559 | -11.998 | 36.957 | 1.00 | 38.90 |
| 16422 | O | LEU | C | 535 | -61.010 | -10.871 | 36.702 | 1.00 | 38.84 |
| 16423 | N | ASN | C | 536 | -61.301 | -13.099 | 36.897 | 1.00 | 37.75 |
| 16424 | CA | ASN | C | 536 | -62.671 | -13.028 | 36.438 | 1.00 | 36.92 |
| 16425 | CB | ASN | C | 536 | -62.702 | -13.400 | 34.975 | 1.00 | 36.91 |
| 16426 | CG | ASN | C | 536 | -62.185 | -14.767 | 34.752 | 1.00 | 36.93 |
| 16427 | OD1 | ASN | C | 536 | -61.905 | -15.481 | 35.716 | 1.00 | 35.89 |
| 16428 | ND2 | ASN | C | 536 | -62.046 | -15.161 | 33.490 | 1.00 | 37.09 |
| 16429 | C | ASN | C | 536 | -63.616 | -13.931 | 37.234 | 1.00 | 35.92 |
| 16430 | O | ASN | C | 536 | -63.264 | -14.411 | 38.309 | 1.00 | 36.04 |
| 16431 | N | TRP | C | 537 | -64.812 | -14.147 | 36.697 | 1.00 | 34.35 |
| 16432 | CA | TRP | C | 537 | -65.828 | -14.943 | 37.363 | 1.00 | 33.16 |
| 16433 | CB | TRP | C | 537 | -67.137 | -14.928 | 36.556 | 1.00 | 32.12 |
| 16434 | CG | TRP | C | 537 | -68.354 | -15.634 | 37.166 | 1.00 | 27.97 |
| 16435 | CD1 | TRP | C | 537 | -68.867 | -15.481 | 38.426 | 1.00 | 25.01 |
| 16436 | NE1 | TRP | C | 537 | -69.975 | -16.286 | 38.592 | 1.00 | 23.18 |
| 16437 | CE2 | TRP | C | 537 | -70.212 | -16.965 | 37.427 | 1.00 | 24.61 |
| 16438 | CD2 | TRP | C | 537 | -69.212 | -16.582 | 36.507 | 1.00 | 25.62 |
| 16439 | CE3 | TRP | C | 537 | -69.241 | -17.136 | 35.221 | 1.00 | 25.93 |
| 16440 | CZ3 | TRP | C | 537 | -70.241 | -18.058 | 34.901 | 1.00 | 27.22 |
| 16441 | CH2 | TRP | C | 537 | -71.227 | -18.408 | 35.838 | 1.00 | 28.01 |
| 16442 | CZ2 | TRP | C | 537 | -71.231 | -17.871 | 37.101 | 1.00 | 26.78 |
| 16443 | C | TRP | C | 537 | -65.290 | -16.348 | 37.581 | 1.00 | 33.67 |
| 16444 | O | TRP | C | 537 | -65.401 | -16.888 | 38.672 | 1.00 | 34.23 |
| 16445 | N | ALA | C | 538 | -64.684 | -16.913 | 36.549 | 1.00 | 33.80 |
| 16446 | CA | ALA | C | 538 | -64.071 | -18.229 | 36.633 | 1.00 | 34.55 |
| 16447 | CB | ALA | C | 538 | -63.438 | -18.591 | 35.314 | 1.00 | 34.48 |
| 16448 | C | ALA | C | 538 | -63.043 | -18.346 | 37.768 | 1.00 | 34.94 |
| 16449 | O | ALA | C | 538 | -62.919 | -19.403 | 38.384 | 1.00 | 35.21 |
| 16450 | N | THR | C | 539 | -62.320 | -17.266 | 38.045 | 1.00 | 35.22 |
| 16451 | CA | THR | C | 539 | -61.351 | -17.253 | 39.135 | 1.00 | 35.66 |
| 16452 | CB | THR | C | 539 | -60.624 | -15.886 | 39.212 | 1.00 | 35.58 |
| 16453 | OG1 | THR | C | 539 | -60.016 | -15.575 | 37.951 | 1.00 | 35.55 |
| 16454 | CG2 | THR | C | 539 | -59.446 | -15.946 | 40.150 | 1.00 | 35.53 |
| 16455 | C | THR | C | 539 | -62.098 | -17.496 | 40.434 | 1.00 | 36.37 |
| 16456 | O | THR | C | 539 | -61.663 | -18.275 | 41.287 | 1.00 | 36.93 |
| 16457 | N | TYR | C | 540 | -63.236 | -16.823 | 40.582 | 1.00 | 36.55 |
| 16458 | CA | TYR | C | 540 | -64.051 | -16.956 | 41.780 | 1.00 | 36.24 |
| 16459 | CB | TYR | C | 540 | -65.113 | -15.866 | 41.820 | 1.00 | 35.97 |
| 16460 | CG | TYR | C | 540 | -66.446 | -16.363 | 42.341 | 1.00 | 35.62 |
| 16461 | CD1 | TYR | C | 540 | -67.475 | -16.697 | 41.470 | 1.00 | 34.83 |
| 16462 | CE1 | TYR | C | 540 | -68.690 | -17.151 | 41.949 | 1.00 | 34.16 |
| 16463 | CZ | TYR | C | 540 | -68.878 | -17.277 | 43.314 | 1.00 | 34.62 |

FIGURE 3 LK

| A | B | C | D | E | F | G | H | I | J |
|---|---|---|---|---|---|---|---|---|---|
| 16464 | OH | TYR | C | 540 | -70.076 | -17.736 | 43.812 | 1.00 | 34.31 |
| 16465 | CE2 | TYR | C | 540 | -67.867 | -16.960 | 44.194 | 1.00 | 33.49 |
| 16466 | CD2 | TYR | C | 540 | -66.666 | -16.515 | 43.708 | 1.00 | 34.96 |
| 16467 | C | TYR | C | 540 | -64.736 | -18.313 | 41.848 | 1.00 | 36.61 |
| 16468 | O | TYR | C | 540 | -64.882 | -18.898 | 42.916 | 1.00 | 36.80 |
| 16469 | N | LEU | C | 541 | -65.183 | -18.809 | 40.709 | 1.00 | 36.87 |
| 16470 | CA | LEU | C | 541 | -65.856 | -20.092 | 40.700 | 1.00 | 37.25 |
| 16471 | CB | LEU | C | 541 | -66.355 | -20.415 | 39.291 | 1.00 | 36.93 |
| 16472 | CG | LEU | C | 541 | -67.566 | -19.587 | 38.829 | 1.00 | 38.22 |
| 16473 | CD1 | LEU | C | 541 | -67.862 | -19.803 | 37.343 | 1.00 | 39.05 |
| 16474 | CD2 | LEU | C | 541 | -68.801 | -19.873 | 39.668 | 1.00 | 36.20 |
| 16475 | C | LEU | C | 541 | -64.930 | -21.203 | 41.203 | 1.00 | 37.67 |
| 16476 | O | LEU | C | 541 | -65.363 | -22.101 | 41.915 | 1.00 | 37.33 |
| 16477 | N | ALA | C | 542 | -63.657 | -21.142 | 40.821 | 1.00 | 38.09 |
| 16478 | CA | ALA | C | 542 | -62.717 | -22.187 | 41.203 | 1.00 | 39.00 |
| 16479 | CB | ALA | C | 542 | -61.599 | -22.347 | 40.155 | 1.00 | 39.20 |
| 16480 | C | ALA | C | 542 | -62.143 | -21.960 | 42.595 | 1.00 | 39.15 |
| 16481 | O | ALA | C | 542 | -62.083 | -22.888 | 43.389 | 1.00 | 40.14 |
| 16482 | N | SER | C | 543 | -61.747 | -20.731 | 42.901 | 1.00 | 39.21 |
| 16483 | CA | SER | C | 543 | -61.203 | -20.426 | 44.217 | 1.00 | 39.14 |
| 16484 | CB | SER | C | 543 | -60.750 | -18.971 | 44.292 | 1.00 | 39.34 |
| 16485 | OG | SER | C | 543 | -60.583 | -18.543 | 45.636 | 1.00 | 39.58 |
| 16486 | C | SER | C | 543 | -62.203 | -20.699 | 45.328 | 1.00 | 39.36 |
| 16487 | O | SER | C | 543 | -61.878 | -21.352 | 46.316 | 1.00 | 39.08 |
| 16488 | N | THR | C | 544 | -63.426 | -20.206 | 45.157 | 1.00 | 39.58 |
| 16489 | CA | THR | C | 544 | -64.447 | -20.320 | 46.187 | 1.00 | 39.54 |
| 16490 | CB | THR | C | 544 | -65.295 | -19.044 | 46.203 | 1.00 | 39.71 |
| 16491 | OG1 | THR | C | 544 | -64.494 | -17.943 | 46.641 | 1.00 | 40.26 |
| 16492 | CG2 | THR | C | 544 | -66.392 | -19.126 | 47.256 | 1.00 | 39.12 |
| 16493 | C | THR | C | 544 | -65.378 | -21.526 | 46.089 | 1.00 | 39.77 |
| 16494 | O | THR | C | 544 | -65.692 | -22.152 | 47.097 | 1.00 | 40.00 |
| 16495 | N | GLU | C | 545 | -65.842 | -21.860 | 44.892 | 1.00 | 39.52 |
| 16496 | CA | GLU | C | 545 | -66.839 | -22.916 | 44.797 | 1.00 | 39.27 |
| 16497 | CB | GLU | C | 545 | -67.973 | -22.502 | 43.856 | 1.00 | 39.57 |
| 16498 | CG | GLU | C | 545 | -68.526 | -21.111 | 44.110 | 1.00 | 40.23 |
| 16499 | CD | GLU | C | 545 | -69.258 | -21.007 | 45.431 | 1.00 | 42.68 |
| 16500 | OE1 | GLU | C | 545 | -69.710 | -19.890 | 45.776 | 1.00 | 42.51 |
| 16501 | OE2 | GLU | C | 545 | -69.390 | -22.047 | 46.119 | 1.00 | 44.25 |
| 16502 | C | GLU | C | 545 | -66.252 | -24.254 | 44.381 | 1.00 | 38.97 |
| 16503 | O | GLU | C | 545 | -66.964 | -25.242 | 44.272 | 1.00 | 38.95 |
| 16504 | N | ASN | C | 546 | -64.946 | -24.273 | 44.153 | 1.00 | 38.74 |
| 16505 | CA | ASN | C | 546 | -64.246 | -25.494 | 43.770 | 1.00 | 38.27 |
| 16506 | CB | ASN | C | 546 | -64.178 | -26.487 | 44.943 | 1.00 | 37.92 |
| 16507 | CG | ASN | C | 546 | -63.585 | -25.855 | 46.201 | 1.00 | 38.77 |
| 16508 | OD1 | ASN | C | 546 | -64.262 | -25.721 | 47.206 | 1.00 | 41.06 |
| 16509 | ND2 | ASN | C | 546 | -62.329 | -25.421 | 46.126 | 1.00 | 39.38 |
| 16510 | C | ASN | C | 546 | -64.809 | -26.113 | 42.500 | 1.00 | 37.64 |
| 16511 | O | ASN | C | 546 | -64.896 | -27.337 | 42.356 | 1.00 | 37.60 |
| 16512 | N | ILE | C | 547 | -65.180 | -25.245 | 41.572 | 1.00 | 36.89 |
| 16513 | CA | ILE | C | 547 | -65.659 | -25.683 | 40.281 | 1.00 | 36.08 |
| 16514 | CB | ILE | C | 547 | -66.820 | -24.790 | 39.801 | 1.00 | 36.37 |

FIGURE 3 LL

| A | B | C | D | E | F | G | H | I | J |
|---|---|---|---|---|---|---|---|---|---|
| 16515 | CG1 | ILE | C | 547 | -68.037 | -24.967 | 40.700 | 1.00 | 36.20 |
| 16516 | CD1 | ILE | C | 547 | -69.000 | -23.815 | 40.631 | 1.00 | 36.43 |
| 16517 | CG2 | ILE | C | 547 | -67.170 | -25.094 | 38.334 | 1.00 | 34.81 |
| 16518 | C | ILE | C | 547 | -64.528 | -25.580 | 39.288 | 1.00 | 35.90 |
| 16519 | O | ILE | C | 547 | -63.727 | -24.658 | 39.336 | 1.00 | 35.90 |
| 16520 | N | ILE | C | 548 | -64.448 | -26.542 | 38.385 | 1.00 | 35.87 |
| 16521 | CA | ILE | C | 548 | -63.467 | -26.450 | 37.333 | 1.00 | 35.53 |
| 16522 | CB | ILE | C | 548 | -63.015 | -27.852 | 36.888 | 1.00 | 35.11 |
| 16523 | CG1 | ILE | C | 548 | -62.111 | -28.490 | 37.955 | 1.00 | 35.15 |
| 16524 | CD1 | ILE | C | 548 | -61.816 | -29.953 | 37.701 | 1.00 | 33.64 |
| 16525 | CG2 | ILE | C | 548 | -62.263 | -27.773 | 35.562 | 1.00 | 34.96 |
| 16526 | C | ILE | C | 548 | -64.132 | -25.716 | 36.178 | 1.00 | 36.13 |
| 16527 | O | ILE | C | 548 | -65.292 | -25.979 | 35.849 | 1.00 | 35.24 |
| 16528 | N | VAL | C | 549 | -63.421 | -24.769 | 35.576 | 1.00 | 36.68 |
| 16529 | CA | VAL | C | 549 | -63.981 | -24.120 | 34.404 | 1.00 | 37.61 |
| 16530 | CB | VAL | C | 549 | -64.516 | -22.681 | 34.676 | 1.00 | 38.02 |
| 16531 | CG1 | VAL | C | 549 | -63.886 | -22.104 | 35.895 | 1.00 | 37.21 |
| 16532 | CG2 | VAL | C | 549 | -64.381 | -21.778 | 33.434 | 1.00 | 37.91 |
| 16533 | C | VAL | C | 549 | -63.011 | -24.249 | 33.263 | 1.00 | 37.87 |
| 16534 | O | VAL | C | 549 | -61.891 | -23.741 | 33.298 | 1.00 | 38.40 |
| 16535 | N | ALA | C | 550 | -63.452 | -24.988 | 32.260 | 1.00 | 38.59 |
| 16536 | CA | ALA | C | 550 | -62.616 | -25.330 | 31.136 | 1.00 | 39.07 |
| 16537 | CB | ALA | C | 550 | -62.653 | -26.838 | 30.910 | 1.00 | 38.57 |
| 16538 | C | ALA | C | 550 | -63.101 | -24.605 | 29.903 | 1.00 | 39.64 |
| 16539 | O | ALA | C | 550 | -64.266 | -24.236 | 29.816 | 1.00 | 39.78 |
| 16540 | N | SER | C | 551 | -62.186 | -24.401 | 28.962 | 1.00 | 40.23 |
| 16541 | CA | SER | C | 551 | -62.492 | -23.794 | 27.675 | 1.00 | 40.47 |
| 16542 | CB | SER | C | 551 | -61.945 | -22.376 | 27.608 | 1.00 | 40.26 |
| 16543 | OG | SER | C | 551 | -62.591 | -21.553 | 28.569 | 1.00 | 40.15 |
| 16544 | C | SER | C | 551 | -61.858 | -24.676 | 26.613 | 1.00 | 40.84 |
| 16545 | O | SER | C | 551 | -60.957 | -25.464 | 26.913 | 1.00 | 40.72 |
| 16546 | N | PHE | C | 552 | -62.317 | -24.555 | 25.374 | 1.00 | 41.26 |
| 16547 | CA | PHE | C | 552 | -61.836 | -25.446 | 24.336 | 1.00 | 41.74 |
| 16548 | CB | PHE | C | 552 | -62.672 | -26.712 | 24.352 | 1.00 | 41.97 |
| 16549 | CG | PHE | C | 552 | -62.180 | -27.772 | 23.431 | 1.00 | 43.86 |
| 16550 | CD1 | PHE | C | 552 | -60.964 | -28.398 | 23.664 | 1.00 | 45.27 |
| 16551 | CE1 | PHE | C | 552 | -60.510 | -29.397 | 22.814 | 1.00 | 46.32 |
| 16552 | CZ | PHE | C | 552 | -61.275 | -29.781 | 21.722 | 1.00 | 45.55 |
| 16553 | CE2 | PHE | C | 552 | -62.485 | -29.161 | 21.482 | 1.00 | 45.75 |
| 16554 | CD2 | PHE | C | 552 | -62.935 | -28.162 | 22.337 | 1.00 | 44.84 |
| 16555 | C | PHE | C | 552 | -61.884 | -24.836 | 22.951 | 1.00 | 41.94 |
| 16556 | O | PHE | C | 552 | -62.936 | -24.373 | 22.496 | 1.00 | 41.67 |
| 16557 | N | ASP | C | 553 | -60.732 | -24.844 | 22.283 | 1.00 | 42.13 |
| 16558 | CA | ASP | C | 553 | -60.617 | -24.339 | 20.924 | 1.00 | 41.89 |
| 16559 | CB | ASP | C | 553 | -59.281 | -23.658 | 20.737 | 1.00 | 42.09 |
| 16560 | CG | ASP | C | 553 | -59.159 | -22.394 | 21.538 | 1.00 | 43.48 |
| 16561 | OD1 | ASP | C | 553 | -60.196 | -21.795 | 21.894 | 1.00 | 45.76 |
| 16562 | OD2 | ASP | C | 553 | -58.058 | -21.906 | 21.845 | 1.00 | 45.69 |
| 16563 | C | ASP | C | 553 | -60.743 | -25.500 | 19.951 | 1.00 | 41.77 |
| 16564 | O | ASP | C | 553 | -59.754 | -26.158 | 19.594 | 1.00 | 41.88 |
| 16565 | N | GLY | C | 554 | -61.969 | -25.773 | 19.542 | 1.00 | 41.29 |

FIGURE 3 LM

| A | B | C | D | E | F | G | H | I | J |
|---|---|---|---|---|---|---|---|---|---|
| 16566 | CA | GLY | C | 554 | -62.220 | -26.845 | 18.609 | 1.00 | 40.93 |
| 16567 | C | GLY | C | 554 | -62.193 | -26.316 | 17.197 | 1.00 | 40.83 |
| 16568 | O | GLY | C | 554 | -61.634 | -25.250 | 16.917 | 1.00 | 40.52 |
| 16569 | N | ARG | C | 555 | -62.808 | -27.069 | 16.301 | 1.00 | 40.99 |
| 16570 | CA | ARG | C | 555 | -62.866 | -26.677 | 14.908 | 1.00 | 41.49 |
| 16571 | CB | ARG | C | 555 | -63.601 | -27.740 | 14.102 | 1.00 | 41.66 |
| 16572 | CG | ARG | C | 555 | -62.760 | -28.989 | 13.875 | 1.00 | 41.22 |
| 16573 | CD | ARG | C | 555 | -63.476 | -30.097 | 13.156 | 1.00 | 40.78 |
| 16574 | NE | ARG | C | 555 | -64.442 | -30.770 | 14.014 | 1.00 | 41.22 |
| 16575 | CZ | ARG | C | 555 | -65.264 | -31.714 | 13.583 | 1.00 | 41.18 |
| 16576 | NH1 | ARG | C | 555 | -65.220 | -32.087 | 12.309 | 1.00 | 41.17 |
| 16577 | NH2 | ARG | C | 555 | -66.122 | -32.291 | 14.416 | 1.00 | 40.16 |
| 16578 | C | ARG | C | 555 | -63.521 | -25.311 | 14.728 | 1.00 | 41.79 |
| 16579 | O | ARG | C | 555 | -64.683 | -25.107 | 15.074 | 1.00 | 41.79 |
| 16580 | N | GLY | C | 556 | -62.760 | -24.380 | 14.177 | 1.00 | 41.99 |
| 16581 | CA | GLY | C | 556 | -63.256 | -23.047 | 13.921 | 1.00 | 41.94 |
| 16582 | C | GLY | C | 556 | -62.359 | -22.071 | 14.646 | 1.00 | 42.39 |
| 16583 | O | GLY | C | 556 | -62.303 | -20.893 | 14.290 | 1.00 | 42.40 |
| 16584 | N | SER | C | 557 | -61.647 | -22.557 | 15.663 | 1.00 | 42.64 |
| 16585 | CA | SER | C | 557 | -60.792 | -21.667 | 16.441 | 1.00 | 43.31 |
| 16586 | CB | SER | C | 557 | -60.216 | -22.349 | 17.693 | 1.00 | 43.59 |
| 16587 | OG | SER | C | 557 | -59.333 | -23.428 | 17.384 | 1.00 | 45.63 |
| 16588 | C | SER | C | 557 | -59.719 | -21.121 | 15.527 | 1.00 | 43.00 |
| 16589 | O | SER | C | 557 | -59.514 | -21.630 | 14.435 | 1.00 | 43.42 |
| 16590 | N | GLY | C | 558 | -59.065 | -20.054 | 15.945 | 1.00 | 43.19 |
| 16591 | CA | GLY | C | 558 | -58.071 | -19.441 | 15.102 | 1.00 | 43.61 |
| 16592 | C | GLY | C | 558 | -56.649 | -19.654 | 15.571 | 1.00 | 44.19 |
| 16593 | O | GLY | C | 558 | -56.392 | -20.332 | 16.583 | 1.00 | 43.85 |
| 16594 | N | TYR | C | 559 | -55.730 | -19.073 | 14.808 | 1.00 | 44.51 |
| 16595 | CA | TYR | C | 559 | -54.319 | -19.058 | 15.148 | 1.00 | 45.17 |
| 16596 | CB | TYR | C | 559 | -54.153 | -18.507 | 16.562 | 1.00 | 44.88 |
| 16597 | CG | TYR | C | 559 | -54.891 | -17.195 | 16.723 | 1.00 | 45.50 |
| 16598 | CD1 | TYR | C | 559 | -56.035 | -17.095 | 17.522 | 1.00 | 46.07 |
| 16599 | CE1 | TYR | C | 559 | -56.723 | -15.890 | 17.650 | 1.00 | 44.38 |
| 16600 | CZ | TYR | C | 559 | -56.268 | -14.775 | 16.969 | 1.00 | 45.26 |
| 16601 | OH | TYR | C | 559 | -56.927 | -13.574 | 17.077 | 1.00 | 46.25 |
| 16602 | CE2 | TYR | C | 559 | -55.149 | -14.853 | 16.167 | 1.00 | 45.07 |
| 16603 | CD2 | TYR | C | 559 | -54.474 | -16.060 | 16.040 | 1.00 | 45.53 |
| 16604 | C | TYR | C | 559 | -53.640 | -20.408 | 14.959 | 1.00 | 45.74 |
| 16605 | O | TYR | C | 559 | -52.617 | -20.695 | 15.583 | 1.00 | 45.64 |
| 16606 | N | GLN | C | 560 | -54.200 | -21.214 | 14.064 | 1.00 | 46.65 |
| 16607 | CA | GLN | C | 560 | -53.680 | -22.550 | 13.796 | 1.00 | 47.75 |
| 16608 | CB | GLN | C | 560 | -54.429 | -23.579 | 14.648 | 1.00 | 47.67 |
| 16609 | CG | GLN | C | 560 | -54.543 | -23.198 | 16.114 | 1.00 | 47.93 |
| 16610 | CD | GLN | C | 560 | -55.769 | -23.791 | 16.774 | 1.00 | 48.39 |
| 16611 | OE1 | GLN | C | 560 | -55.814 | -24.992 | 17.049 | 1.00 | 48.11 |
| 16612 | NE2 | GLN | C | 560 | -56.772 | -22.950 | 17.029 | 1.00 | 48.26 |
| 16613 | C | GLN | C | 560 | -53.809 | -22.932 | 12.324 | 1.00 | 48.53 |
| 16614 | O | GLN | C | 560 | -53.763 | -24.118 | 11.981 | 1.00 | 48.91 |
| 16615 | N | GLY | C | 561 | -53.990 | -21.940 | 11.458 | 1.00 | 49.30 |
| 16616 | CA | GLY | C | 561 | -54.115 | -22.201 | 10.033 | 1.00 | 50.32 |

FIGURE 3 LN

| A | B | C | D | E | F | G | H | I | J |
|---|---|---|---|---|---|---|---|---|---|
| 16617 | C | GLY | C | 561 | -55.525 | -22.504 | 9.566 | 1.00 | 50.96 |
| 16618 | O | GLY | C | 561 | -56.317 | -23.069 | 10.318 | 1.00 | 51.27 |
| 16619 | N | ASP | C | 562 | -55.818 | -22.155 | 8.310 | 1.00 | 51.66 |
| 16620 | CA | ASP | C | 562 | -57.157 | -22.286 | 7.713 | 1.00 | 52.41 |
| 16621 | CB | ASP | C | 562 | -57.138 | -21.884 | 6.238 | 1.00 | 52.90 |
| 16622 | CG | ASP | C | 562 | -56.800 | -20.439 | 6.035 | 1.00 | 54.58 |
| 16623 | OD1 | ASP | C | 562 | -56.684 | -19.702 | 7.044 | 1.00 | 57.97 |
| 16624 | OD2 | ASP | C | 562 | -56.622 | -19.953 | 4.900 | 1.00 | 56.06 |
| 16625 | C | ASP | C | 562 | -57.814 | -23.650 | 7.778 | 1.00 | 52.25 |
| 16626 | O | ASP | C | 562 | -59.020 | -23.755 | 7.594 | 1.00 | 52.28 |
| 16627 | N | LYS | C | 563 | -57.036 | -24.696 | 7.996 | 1.00 | 52.37 |
| 16628 | CA | LYS | C | 563 | -57.602 | -26.041 | 7.977 | 1.00 | 52.51 |
| 16629 | CB | LYS | C | 563 | -56.501 | -27.099 | 8.107 | 1.00 | 52.84 |
| 16630 | CG | LYS | C | 563 | -57.007 | -28.505 | 8.419 | 1.00 | 53.34 |
| 16631 | CD | LYS | C | 563 | -57.820 | -29.095 | 7.274 | 1.00 | 55.29 |
| 16632 | CE | LYS | C | 563 | -58.334 | -30.493 | 7.624 | 1.00 | 56.52 |
| 16633 | NZ | LYS | C | 563 | -57.237 | -31.397 | 8.106 | 1.00 | 56.44 |
| 16634 | C | LYS | C | 563 | -58.630 | -26.212 | 9.081 | 1.00 | 52.27 |
| 16635 | O | LYS | C | 563 | -59.670 | -26.843 | 8.887 | 1.00 | 51.73 |
| 16636 | N | ILE | C | 564 | -58.337 | -25.639 | 10.241 | 1.00 | 51.93 |
| 16637 | CA | ILE | C | 564 | -59.230 | -25.784 | 11.373 | 1.00 | 52.01 |
| 16638 | CB | ILE | C | 564 | -58.426 | -26.018 | 12.652 | 1.00 | 52.00 |
| 16639 | CG1 | ILE | C | 564 | -59.364 | -26.344 | 13.811 | 1.00 | 52.03 |
| 16640 | CD1 | ILE | C | 564 | -59.619 | -25.180 | 14.719 | 1.00 | 52.08 |
| 16641 | CG2 | ILE | C | 564 | -57.582 | -24.794 | 12.970 | 1.00 | 52.27 |
| 16642 | C | ILE | C | 564 | -60.147 | -24.577 | 11.528 | 1.00 | 51.91 |
| 16643 | O | ILE | C | 564 | -61.282 | -24.701 | 11.987 | 1.00 | 51.73 |
| 16644 | N | MET | C | 565 | -59.657 | -23.409 | 11.140 | 1.00 | 51.61 |
| 16645 | CA | MET | C | 565 | -60.458 | -22.212 | 11.282 | 1.00 | 51.47 |
| 16646 | CB | MET | C | 565 | -59.615 | -20.955 | 11.073 | 1.00 | 51.54 |
| 16647 | CG | MET | C | 565 | -60.460 | -19.705 | 10.934 | 1.00 | 51.13 |
| 16648 | SD | MET | C | 565 | -59.551 | -18.180 | 11.173 | 1.00 | 51.56 |
| 16649 | CE | MET | C | 565 | -58.922 | -17.890 | 9.531 | 1.00 | 50.91 |
| 16650 | C | MET | C | 565 | -61.629 | -22.224 | 10.310 | 1.00 | 51.27 |
| 16651 | O | MET | C | 565 | -62.723 | -21.778 | 10.647 | 1.00 | 51.17 |
| 16652 | N | HIS | C | 566 | -61.395 | -22.746 | 9.109 | 1.00 | 51.02 |
| 16653 | CA | HIS | C | 566 | -62.420 | -22.778 | 8.073 | 1.00 | 50.69 |
| 16654 | CB | HIS | C | 566 | -61.799 | -22.574 | 6.695 | 1.00 | 50.92 |
| 16655 | CG | HIS | C | 566 | -61.310 | -21.179 | 6.461 | 1.00 | 51.05 |
| 16656 | ND1 | HIS | C | 566 | -60.921 | -20.724 | 5.221 | 1.00 | 51.62 |
| 16657 | CE1 | HIS | C | 566 | -60.554 | -19.457 | 5.313 | 1.00 | 52.72 |
| 16658 | NE2 | HIS | C | 566 | -60.690 | -19.074 | 6.571 | 1.00 | 52.74 |
| 16659 | CD2 | HIS | C | 566 | -61.160 | -20.134 | 7.310 | 1.00 | 51.36 |
| 16660 | C | HIS | C | 566 | -63.215 | -24.058 | 8.111 | 1.00 | 50.68 |
| 16661 | O | HIS | C | 566 | -64.132 | -24.261 | 7.319 | 1.00 | 50.92 |
| 16662 | N | ALA | C | 567 | -62.868 | -24.930 | 9.042 | 1.00 | 50.62 |
| 16663 | CA | ALA | C | 567 | -63.605 | -26.161 | 9.197 | 1.00 | 50.77 |
| 16664 | CB | ALA | C | 567 | -63.204 | -26.855 | 10.475 | 1.00 | 50.79 |
| 16665 | C | ALA | C | 567 | -65.101 | -25.859 | 9.194 | 1.00 | 51.11 |
| 16666 | O | ALA | C | 567 | -65.896 | -26.641 | 8.655 | 1.00 | 51.22 |
| 16667 | N | ILE | C | 568 | -65.482 | -24.720 | 9.777 | 1.00 | 50.95 |

FIGURE 3 LO

| A | B | C | D | E | F | G | H | I | J |
|---|---|---|---|---|---|---|---|---|---|
| 16668 | CA | ILE | C | 568 | -66.899 | -24.356 | 9.856 | 1.00 | 51.05 |
| 16669 | CB | ILE | C | 568 | -67.262 | -23.718 | 11.226 | 1.00 | 50.91 |
| 16670 | CG1 | ILE | C | 568 | -66.195 | -22.723 | 11.692 | 1.00 | 50.96 |
| 16671 | CD1 | ILE | C | 568 | -66.179 | -21.411 | 10.952 | 1.00 | 51.13 |
| 16672 | CG2 | ILE | C | 568 | -67.441 | -24.789 | 12.263 | 1.00 | 50.84 |
| 16673 | C | ILE | C | 568 | -67.447 | -23.488 | 8.734 | 1.00 | 51.22 |
| 16674 | O | ILE | C | 568 | -68.620 | -23.153 | 8.759 | 1.00 | 51.53 |
| 16675 | N | ASN | C | 569 | -66.628 | -23.117 | 7.757 | 1.00 | 51.43 |
| 16676 | CA | ASN | C | 569 | -67.126 | -22.276 | 6.669 | 1.00 | 51.48 |
| 16677 | CB | ASN | C | 569 | -66.137 | -22.263 | 5.501 | 1.00 | 51.32 |
| 16678 | CG | ASN | C | 569 | -66.540 | -21.291 | 4.406 | 1.00 | 51.63 |
| 16679 | OD1 | ASN | C | 569 | -67.048 | -21.694 | 3.357 | 1.00 | 51.78 |
| 16680 | ND2 | ASN | C | 569 | -66.310 | -20.005 | 4.640 | 1.00 | 51.32 |
| 16681 | C | ASN | C | 569 | -68.516 | -22.721 | 6.193 | 1.00 | 51.53 |
| 16682 | O | ASN | C | 569 | -68.763 | -23.907 | 6.002 | 1.00 | 51.32 |
| 16683 | N | ARG | C | 570 | -69.429 | -21.765 | 6.035 | 1.00 | 51.74 |
| 16684 | CA | ARG | C | 570 | -70.792 | -22.055 | 5.595 | 1.00 | 51.88 |
| 16685 | CB | ARG | C | 570 | -70.791 | -22.635 | 4.184 | 1.00 | 52.09 |
| 16686 | CG | ARG | C | 570 | -70.401 | -21.654 | 3.093 | 1.00 | 53.46 |
| 16687 | CD | ARG | C | 570 | -70.372 | -22.291 | 1.704 | 1.00 | 55.35 |
| 16688 | NE | ARG | C | 570 | -71.603 | -23.028 | 1.415 | 1.00 | 55.87 |
| 16689 | CZ | ARG | C | 570 | -72.720 | -22.465 | 0.958 | 1.00 | 56.49 |
| 16690 | NH1 | ARG | C | 570 | -73.787 | -23.221 | 0.731 | 1.00 | 56.98 |
| 16691 | NH2 | ARG | C | 570 | -72.775 | -21.153 | 0.725 | 1.00 | 54.90 |
| 16692 | C | ARG | C | 570 | -71.503 | -23.032 | 6.513 | 1.00 | 51.76 |
| 16693 | O | ARG | C | 570 | -72.614 | -23.468 | 6.224 | 1.00 | 51.59 |
| 16694 | N | ARG | C | 571 | -70.865 | -23.372 | 7.623 | 1.00 | 51.82 |
| 16695 | CA | ARG | C | 571 | -71.421 | -24.371 | 8.519 | 1.00 | 51.99 |
| 16696 | CB | ARG | C | 571 | -70.737 | -25.716 | 8.274 | 1.00 | 52.37 |
| 16697 | CG | ARG | C | 571 | -71.638 | -26.790 | 7.659 | 1.00 | 54.66 |
| 16698 | CD | ARG | C | 571 | -71.790 | -26.743 | 6.144 | 1.00 | 57.11 |
| 16699 | NE | ARG | C | 571 | -73.091 | -26.227 | 5.721 | 1.00 | 59.49 |
| 16700 | CZ | ARG | C | 571 | -73.691 | -26.552 | 4.577 | 1.00 | 60.45 |
| 16701 | NH1 | ARG | C | 571 | -74.875 | -26.034 | 4.274 | 1.00 | 60.04 |
| 16702 | NH2 | ARG | C | 571 | -73.113 | -27.396 | 3.733 | 1.00 | 60.76 |
| 16703 | C | ARG | C | 571 | -71.361 | -24.016 | 10.004 | 1.00 | 51.39 |
| 16704 | O | ARG | C | 571 | -70.995 | -24.843 | 10.830 | 1.00 | 51.58 |
| 16705 | N | LEU | C | 572 | -71.719 | -22.785 | 10.337 | 1.00 | 50.60 |
| 16706 | CA | LEU | C | 572 | -71.820 | -22.375 | 11.733 | 1.00 | 49.53 |
| 16707 | CB | LEU | C | 572 | -72.217 | -20.899 | 11.815 | 1.00 | 49.15 |
| 16708 | CG | LEU | C | 572 | -71.108 | -19.868 | 12.017 | 1.00 | 49.38 |
| 16709 | CD1 | LEU | C | 572 | -71.494 | -18.543 | 11.413 | 1.00 | 50.08 |
| 16710 | CD2 | LEU | C | 572 | -69.767 | -20.325 | 11.479 | 1.00 | 48.95 |
| 16711 | C | LEU | C | 572 | -72.871 | -23.250 | 12.427 | 1.00 | 48.87 |
| 16712 | O | LEU | C | 572 | -73.839 | -23.669 | 11.800 | 1.00 | 48.51 |
| 16713 | N | GLY | C | 573 | -72.673 | -23.530 | 13.714 | 1.00 | 48.27 |
| 16714 | CA | GLY | C | 573 | -73.602 | -24.350 | 14.474 | 1.00 | 47.83 |
| 16715 | C | GLY | C | 573 | -73.434 | -25.842 | 14.258 | 1.00 | 47.81 |
| 16716 | O | GLY | C | 573 | -74.372 | -26.620 | 14.437 | 1.00 | 47.71 |
| 16717 | N | THR | C | 574 | -72.234 | -26.248 | 13.860 | 1.00 | 48.01 |
| 16718 | CA | THR | C | 574 | -71.951 | -27.657 | 13.630 | 1.00 | 48.12 |

FIGURE 3 LP

| A | B | C | D | E | F | G | H | I | J |
|---|---|---|---|---|---|---|---|---|---|
| 16719 | CB | THR | C | 574 | -71.755 | -27.943 | 12.125 | 1.00 | 48.42 |
| 16720 | OG1 | THR | C | 574 | -70.599 | -27.240 | 11.643 | 1.00 | 48.49 |
| 16721 | CG2 | THR | C | 574 | -72.907 | -27.360 | 11.312 | 1.00 | 48.11 |
| 16722 | C | THR | C | 574 | -70.728 | -28.126 | 14.410 | 1.00 | 48.05 |
| 16723 | O | THR | C | 574 | -70.813 | -28.392 | 15.614 | 1.00 | 47.93 |
| 16724 | N | PHE | C | 575 | -69.596 | -28.212 | 13.716 | 1.00 | 47.66 |
| 16725 | CA | PHE | C | 575 | -68.352 | -28.731 | 14.291 | 1.00 | 47.46 |
| 16726 | CB | PHE | C | 575 | -67.211 | -28.654 | 13.266 | 1.00 | 47.51 |
| 16727 | CG | PHE | C | 575 | -67.502 | -29.384 | 11.987 | 1.00 | 46.95 |
| 16728 | CD1 | PHE | C | 575 | -68.111 | -30.628 | 12.012 | 1.00 | 46.47 |
| 16729 | CE1 | PHE | C | 575 | -68.391 | -31.305 | 10.848 | 1.00 | 45.87 |
| 16730 | CZ | PHE | C | 575 | -68.069 | -30.742 | 9.628 | 1.00 | 47.21 |
| 16731 | CE2 | PHE | C | 575 | -67.463 | -29.493 | 9.582 | 1.00 | 48.25 |
| 16732 | CD2 | PHE | C | 575 | -67.185 | -28.821 | 10.763 | 1.00 | 47.21 |
| 16733 | C | PHE | C | 575 | -67.943 | -28.056 | 15.598 | 1.00 | 47.31 |
| 16734 | O | PHE | C | 575 | -67.533 | -28.728 | 16.545 | 1.00 | 47.09 |
| 16735 | N | GLU | C | 576 | -68.043 | -26.729 | 15.629 | 1.00 | 47.40 |
| 16736 | CA | GLU | C | 576 | -67.730 | -25.922 | 16.811 | 1.00 | 47.37 |
| 16737 | CB | GLU | C | 576 | -68.087 | -24.469 | 16.528 | 1.00 | 47.70 |
| 16738 | CG | GLU | C | 576 | -69.396 | -24.370 | 15.753 | 1.00 | 49.50 |
| 16739 | CD | GLU | C | 576 | -69.845 | -22.955 | 15.543 | 1.00 | 51.64 |
| 16740 | OE1 | GLU | C | 576 | -69.110 | -22.041 | 15.962 | 1.00 | 55.10 |
| 16741 | OE2 | GLU | C | 576 | -70.926 | -22.754 | 14.962 | 1.00 | 52.07 |
| 16742 | C | GLU | C | 576 | -68.582 | -26.392 | 17.972 | 1.00 | 46.69 |
| 16743 | O | GLU | C | 576 | -68.115 | -26.518 | 19.099 | 1.00 | 46.67 |
| 16744 | N | VAL | C | 577 | -69.849 | -26.637 | 17.679 | 1.00 | 46.14 |
| 16745 | CA | VAL | C | 577 | -70.809 | -27.068 | 18.681 | 1.00 | 45.80 |
| 16746 | CB | VAL | C | 577 | -72.238 | -26.956 | 18.142 | 1.00 | 45.30 |
| 16747 | CG1 | VAL | C | 577 | -72.543 | -25.522 | 17.833 | 1.00 | 45.07 |
| 16748 | CG2 | VAL | C | 577 | -73.227 | -27.513 | 19.128 | 1.00 | 45.15 |
| 16749 | C | VAL | C | 577 | -70.525 | -28.491 | 19.143 | 1.00 | 46.01 |
| 16750 | O | VAL | C | 577 | -70.573 | -28.778 | 20.342 | 1.00 | 45.34 |
| 16751 | N | GLU | C | 578 | -70.234 | -29.378 | 18.193 | 1.00 | 46.47 |
| 16752 | CA | GLU | C | 578 | -69.909 | -30.756 | 18.540 | 1.00 | 47.41 |
| 16753 | CB | GLU | C | 578 | -69.719 | -31.645 | 17.306 | 1.00 | 47.95 |
| 16754 | CG | GLU | C | 578 | -69.566 | -33.119 | 17.691 | 1.00 | 51.44 |
| 16755 | CD | GLU | C | 578 | -68.335 | -33.802 | 17.088 | 1.00 | 55.56 |
| 16756 | OE1 | GLU | C | 578 | -68.189 | -33.801 | 15.833 | 1.00 | 56.75 |
| 16757 | OE2 | GLU | C | 578 | -67.517 | -34.352 | 17.876 | 1.00 | 55.92 |
| 16758 | C | GLU | C | 578 | -68.633 | -30.821 | 19.356 | 1.00 | 46.76 |
| 16759 | O | GLU | C | 578 | -68.595 | -31.442 | 20.418 | 1.00 | 46.81 |
| 16760 | N | ASP | C | 579 | -67.591 | -30.176 | 18.844 | 1.00 | 46.10 |
| 16761 | CA | ASP | C | 579 | -66.289 | -30.233 | 19.472 | 1.00 | 45.83 |
| 16762 | CB | ASP | C | 579 | -65.262 | -29.446 | 18.657 | 1.00 | 45.86 |
| 16763 | CG | ASP | C | 579 | -65.005 | -30.070 | 17.284 | 1.00 | 46.12 |
| 16764 | OD1 | ASP | C | 579 | -65.534 | -31.169 | 17.008 | 1.00 | 45.17 |
| 16765 | OD2 | ASP | C | 579 | -64.283 | -29.535 | 16.416 | 1.00 | 47.24 |
| 16766 | C | ASP | C | 579 | -66.323 | -29.809 | 20.941 | 1.00 | 45.70 |
| 16767 | O | ASP | C | 579 | -65.476 | -30.234 | 21.736 | 1.00 | 45.44 |
| 16768 | N | GLN | C | 580 | -67.313 | -29.000 | 21.307 | 1.00 | 45.21 |
| 16769 | CA | GLN | C | 580 | -67.453 | -28.576 | 22.693 | 1.00 | 44.84 |

FIGURE 3 LQ

| A | B | C | D | E | F | G | H | I | J |
|---|---|---|---|---|---|---|---|---|---|
| 16770 | CB | GLN | C | 580 | -68.332 | -27.324 | 22.808 | 1.00 | 44.58 |
| 16771 | CG | GLN | C | 580 | -67.720 | -26.056 | 22.257 | 1.00 | 43.48 |
| 16772 | CD | GLN | C | 580 | -66.564 | -25.539 | 23.095 | 1.00 | 43.32 |
| 16773 | OE1 | GLN | C | 580 | -66.543 | -25.717 | 24.315 | 1.00 | 43.34 |
| 16774 | NE2 | GLN | C | 580 | -65.607 | -24.888 | 22.448 | 1.00 | 41.53 |
| 16775 | C | GLN | C | 580 | -68.058 | -29.721 | 23.497 | 1.00 | 44.86 |
| 16776 | O | GLN | C | 580 | -67.748 | -29.910 | 24.678 | 1.00 | 45.10 |
| 16777 | N | ILE | C | 581 | -68.924 | -30.487 | 22.857 | 1.00 | 45.08 |
| 16778 | CA | ILE | C | 581 | -69.565 | -31.615 | 23.525 | 1.00 | 45.76 |
| 16779 | CB | ILE | C | 581 | -70.768 | -32.100 | 22.722 | 1.00 | 45.76 |
| 16780 | CG1 | ILE | C | 581 | -71.763 | -30.949 | 22.540 | 1.00 | 45.11 |
| 16781 | CD1 | ILE | C | 581 | -72.866 | -31.243 | 21.562 | 1.00 | 45.04 |
| 16782 | CG2 | ILE | C | 581 | -71.426 | -33.284 | 23.420 | 1.00 | 45.93 |
| 16783 | C | ILE | C | 581 | -68.577 | -32.752 | 23.785 | 1.00 | 46.32 |
| 16784 | O | ILE | C | 581 | -68.519 | -33.288 | 24.891 | 1.00 | 46.68 |
| 16785 | N | GLU | C | 582 | -67.793 | -33.113 | 22.777 | 1.00 | 46.90 |
| 16786 | CA | GLU | C | 582 | -66.762 | -34.135 | 22.964 | 1.00 | 47.45 |
| 16787 | CB | GLU | C | 582 | -66.044 | -34.455 | 21.642 | 1.00 | 47.64 |
| 16788 | CG | GLU | C | 582 | -66.515 | -35.742 | 20.969 | 1.00 | 48.90 |
| 16789 | CD | GLU | C | 582 | -65.940 | -36.988 | 21.616 | 1.00 | 49.74 |
| 16790 | OE1 | GLU | C | 582 | -64.704 | -37.109 | 21.679 | 1.00 | 51.84 |
| 16791 | OE2 | GLU | C | 582 | -66.718 | -37.855 | 22.059 | 1.00 | 50.95 |
| 16792 | C | GLU | C | 582 | -65.756 | -33.663 | 23.998 | 1.00 | 47.32 |
| 16793 | O | GLU | C | 582 | -65.335 | -34.426 | 24.874 | 1.00 | 47.48 |
| 16794 | N | ALA | C | 583 | -65.367 | -32.400 | 23.891 | 1.00 | 47.24 |
| 16795 | CA | ALA | C | 583 | -64.426 | -31.830 | 24.835 | 1.00 | 47.16 |
| 16796 | CB | ALA | C | 583 | -64.344 | -30.327 | 24.660 | 1.00 | 47.11 |
| 16797 | C | ALA | C | 583 | -64.897 | -32.181 | 26.228 | 1.00 | 47.26 |
| 16798 | O | ALA | C | 583 | -64.154 | -32.744 | 27.020 | 1.00 | 47.22 |
| 16799 | N | ALA | C | 584 | -66.155 | -31.869 | 26.516 | 1.00 | 47.82 |
| 16800 | CA | ALA | C | 584 | -66.711 | -32.163 | 27.826 | 1.00 | 48.16 |
| 16801 | CB | ALA | C | 584 | -68.161 | -31.743 | 27.910 | 1.00 | 48.18 |
| 16802 | C | ALA | C | 584 | -66.557 | -33.639 | 28.128 | 1.00 | 48.51 |
| 16803 | O | ALA | C | 584 | -66.142 | -33.995 | 29.225 | 1.00 | 48.47 |
| 16804 | N | ARG | C | 585 | -66.891 | -34.491 | 27.160 | 1.00 | 49.12 |
| 16805 | CA | ARG | C | 585 | -66.724 | -35.929 | 27.336 | 1.00 | 50.18 |
| 16806 | CB | ARG | C | 585 | -67.079 | -36.700 | 26.063 | 1.00 | 50.00 |
| 16807 | CG | ARG | C | 585 | -68.501 | -36.548 | 25.532 | 1.00 | 50.05 |
| 16808 | CD | ARG | C | 585 | -68.884 | -37.673 | 24.566 | 1.00 | 50.16 |
| 16809 | NE | ARG | C | 585 | -69.641 | -37.219 | 23.399 | 1.00 | 50.86 |
| 16810 | CZ | ARG | C | 585 | -70.968 | -37.202 | 23.331 | 1.00 | 51.91 |
| 16811 | NH1 | ARG | C | 585 | -71.697 | -37.606 | 24.374 | 1.00 | 51.70 |
| 16812 | NH2 | ARG | C | 585 | -71.569 | -36.783 | 22.222 | 1.00 | 51.06 |
| 16813 | C | ARG | C | 585 | -65.263 | -36.202 | 27.657 | 1.00 | 50.87 |
| 16814 | O | ARG | C | 585 | -64.944 | -36.843 | 28.647 | 1.00 | 50.99 |
| 16815 | N | GLN | C | 586 | -64.380 | -35.704 | 26.799 | 1.00 | 52.00 |
| 16816 | CA | GLN | C | 586 | -62.949 | -35.898 | 26.966 | 1.00 | 53.14 |
| 16817 | CB | GLN | C | 586 | -62.172 | -35.141 | 25.885 | 1.00 | 53.53 |
| 16818 | CG | GLN | C | 586 | -62.158 | -35.834 | 24.536 | 1.00 | 54.41 |
| 16819 | CD | GLN | C | 586 | -61.109 | -36.929 | 24.459 | 1.00 | 56.50 |
| 16820 | OE1 | GLN | C | 586 | -61.412 | -38.104 | 24.680 | 1.00 | 58.23 |

FIGURE 3 LR

| A | B | C | D | E | F | G | H | I | J |
|---|---|---|---|---|---|---|---|---|---|
| 16821 | NE2 | GLN | C | 586 | -59.874 | -36.549 | 24.146 | 1.00 | 56.63 |
| 16822 | C | GLN | C | 586 | -62.483 | -35.472 | 28.349 | 1.00 | 53.50 |
| 16823 | O | GLN | C | 586 | -61.595 | -36.100 | 28.924 | 1.00 | 53.86 |
| 16824 | N | PHE | C | 587 | -63.078 | -34.412 | 28.889 | 1.00 | 53.98 |
| 16825 | CA | PHE | C | 587 | -62.709 | -33.969 | 30.228 | 1.00 | 54.32 |
| 16826 | CB | PHE | C | 587 | -63.286 | -32.591 | 30.550 | 1.00 | 54.34 |
| 16827 | CG | PHE | C | 587 | -62.729 | -31.495 | 29.701 | 1.00 | 54.30 |
| 16828 | CD1 | PHE | C | 587 | -61.388 | -31.477 | 29.371 | 1.00 | 54.33 |
| 16829 | CE1 | PHE | C | 587 | -60.866 | -30.469 | 28.582 | 1.00 | 54.45 |
| 16830 | CZ | PHE | C | 587 | -61.689 | -29.473 | 28.113 | 1.00 | 54.28 |
| 16831 | CE2 | PHE | C | 587 | -63.035 | -29.486 | 28.426 | 1.00 | 54.02 |
| 16832 | CD2 | PHE | C | 587 | -63.548 | -30.490 | 29.219 | 1.00 | 53.89 |
| 16833 | C | PHE | C | 587 | -63.160 | -34.986 | 31.259 | 1.00 | 54.60 |
| 16834 | O | PHE | C | 587 | -62.455 | -35.243 | 32.232 | 1.00 | 54.81 |
| 16835 | N | SER | C | 588 | -64.330 | -35.572 | 31.040 | 1.00 | 54.74 |
| 16836 | CA | SER | C | 588 | -64.847 | -36.578 | 31.958 | 1.00 | 55.47 |
| 16837 | CB | SER | C | 588 | -66.258 | -36.997 | 31.548 | 1.00 | 55.46 |
| 16838 | OG | SER | C | 588 | -67.012 | -35.864 | 31.159 | 1.00 | 56.80 |
| 16839 | C | SER | C | 588 | -63.939 | -37.810 | 32.042 | 1.00 | 55.46 |
| 16840 | O | SER | C | 588 | -63.824 | -38.439 | 33.090 | 1.00 | 55.32 |
| 16841 | N | LYS | C | 589 | -63.288 | -38.152 | 30.939 | 1.00 | 55.66 |
| 16842 | CA | LYS | C | 589 | -62.434 | -39.334 | 30.935 | 1.00 | 56.05 |
| 16843 | CB | LYS | C | 589 | -62.231 | -39.875 | 29.514 | 1.00 | 56.24 |
| 16844 | CG | LYS | C | 589 | -63.528 | -40.019 | 28.709 | 1.00 | 57.14 |
| 16845 | CD | LYS | C | 589 | -64.678 | -40.529 | 29.589 | 1.00 | 58.46 |
| 16846 | CE | LYS | C | 589 | -66.029 | -40.028 | 29.084 | 1.00 | 58.38 |
| 16847 | NZ | LYS | C | 589 | -67.151 | -40.300 | 30.036 | 1.00 | 57.94 |
| 16848 | C | LYS | C | 589 | -61.100 | -39.042 | 31.601 | 1.00 | 55.88 |
| 16849 | O | LYS | C | 589 | -60.267 | -39.929 | 31.763 | 1.00 | 56.10 |
| 16850 | N | MET | C | 590 | -60.904 | -37.791 | 31.996 | 1.00 | 55.61 |
| 16851 | CA | MET | C | 590 | -59.666 | -37.405 | 32.649 | 1.00 | 55.00 |
| 16852 | CB | MET | C | 590 | -59.411 | -35.909 | 32.499 | 1.00 | 55.18 |
| 16853 | CG | MET | C | 590 | -59.012 | -35.507 | 31.093 | 1.00 | 56.25 |
| 16854 | SD | MET | C | 590 | -58.735 | -33.724 | 30.931 | 1.00 | 57.90 |
| 16855 | CE | MET | C | 590 | -58.014 | -33.669 | 29.300 | 1.00 | 57.21 |
| 16856 | C | MET | C | 590 | -59.685 | -37.808 | 34.110 | 1.00 | 54.11 |
| 16857 | O | MET | C | 590 | -58.660 | -37.740 | 34.776 | 1.00 | 54.39 |
| 16858 | N | GLY | C | 591 | -60.856 | -38.192 | 34.613 | 1.00 | 53.15 |
| 16859 | CA | GLY | C | 591 | -60.976 | -38.744 | 35.956 | 1.00 | 51.80 |
| 16860 | C | GLY | C | 591 | -61.267 | -37.884 | 37.175 | 1.00 | 51.13 |
| 16861 | O | GLY | C | 591 | -61.609 | -38.416 | 38.223 | 1.00 | 51.07 |
| 16862 | N | PHE | C | 592 | -61.133 | -36.569 | 37.068 | 1.00 | 50.63 |
| 16863 | CA | PHE | C | 592 | -61.378 | -35.693 | 38.218 | 1.00 | 49.98 |
| 16864 | CB | PHE | C | 592 | -60.184 | -34.765 | 38.436 | 1.00 | 50.10 |
| 16865 | CG | PHE | C | 592 | -59.627 | -34.200 | 37.166 | 1.00 | 50.12 |
| 16866 | CD1 | PHE | C | 592 | -58.446 | -34.691 | 36.635 | 1.00 | 50.15 |
| 16867 | CE1 | PHE | C | 592 | -57.935 | -34.173 | 35.464 | 1.00 | 50.40 |
| 16868 | CZ | PHE | C | 592 | -58.612 | -33.154 | 34.803 | 1.00 | 50.89 |
| 16869 | CE2 | PHE | C | 592 | -59.789 | -32.664 | 35.320 | 1.00 | 49.57 |
| 16870 | CD2 | PHE | C | 592 | -60.291 | -33.187 | 36.496 | 1.00 | 49.76 |
| 16871 | C | PHE | C | 592 | -62.659 | -34.867 | 38.062 | 1.00 | 49.40 |

FIGURE 3 LS

| A | B | C | D | E | F | G | H | I | J |
|---|---|---|---|---|---|---|---|---|---|
| 16872 | O | PHE | C | 592 | -62.833 | -33.825 | 38.703 | 1.00 | 48.85 |
| 16873 | N | VAL | C | 593 | -63.564 | -35.350 | 37.221 | 1.00 | 48.83 |
| 16874 | CA | VAL | C | 593 | -64.791 | -34.621 | 36.942 | 1.00 | 48.30 |
| 16875 | CB | VAL | C | 593 | -64.862 | -34.235 | 35.457 | 1.00 | 48.35 |
| 16876 | CG1 | VAL | C | 593 | -66.216 | -33.655 | 35.127 | 1.00 | 48.07 |
| 16877 | CG2 | VAL | C | 593 | -63.752 | -33.253 | 35.106 | 1.00 | 48.30 |
| 16878 | C | VAL | C | 593 | -66.054 | -35.391 | 37.288 | 1.00 | 48.19 |
| 16879 | O | VAL | C | 593 | -66.199 | -36.569 | 36.939 | 1.00 | 48.02 |
| 16880 | N | ASP | C | 594 | -66.970 | -34.723 | 37.981 | 1.00 | 47.98 |
| 16881 | CA | ASP | C | 594 | -68.253 | -35.324 | 38.280 | 1.00 | 47.68 |
| 16882 | CB | ASP | C | 594 | -68.964 | -34.588 | 39.413 | 1.00 | 47.47 |
| 16883 | CG | ASP | C | 594 | -70.240 | -35.290 | 39.853 | 1.00 | 47.21 |
| 16884 | OD1 | ASP | C | 594 | -70.722 | -35.011 | 40.970 | 1.00 | 46.89 |
| 16885 | OD2 | ASP | C | 594 | -70.835 | -36.135 | 39.147 | 1.00 | 45.92 |
| 16886 | C | ASP | C | 594 | -69.087 | -35.250 | 37.019 | 1.00 | 48.03 |
| 16887 | O | ASP | C | 594 | -69.548 | -34.175 | 36.639 | 1.00 | 48.06 |
| 16888 | N | ASN | C | 595 | -69.272 | -36.395 | 36.367 | 1.00 | 48.29 |
| 16889 | CA | ASN | C | 595 | -70.065 | -36.476 | 35.149 | 1.00 | 48.38 |
| 16890 | CB | ASN | C | 595 | -70.120 | -37.922 | 34.650 | 1.00 | 48.96 |
| 16891 | CG | ASN | C | 595 | -68.845 | -38.346 | 33.948 | 1.00 | 51.36 |
| 16892 | OD1 | ASN | C | 595 | -67.808 | -37.685 | 34.071 | 1.00 | 53.72 |
| 16893 | ND2 | ASN | C | 595 | -68.912 | -39.454 | 33.205 | 1.00 | 51.67 |
| 16894 | C | ASN | C | 595 | -71.489 | -35.954 | 35.334 | 1.00 | 47.73 |
| 16895 | O | ASN | C | 595 | -72.152 | -35.582 | 34.367 | 1.00 | 47.69 |
| 16896 | N | LYS | C | 596 | -71.965 | -35.942 | 36.572 | 1.00 | 46.77 |
| 16897 | CA | LYS | C | 596 | -73.324 | -35.497 | 36.841 | 1.00 | 46.12 |
| 16898 | CB | LYS | C | 596 | -73.893 | -36.200 | 38.076 | 1.00 | 46.38 |
| 16899 | CG | LYS | C | 596 | -74.107 | -37.693 | 37.888 | 1.00 | 48.36 |
| 16900 | CD | LYS | C | 596 | -74.951 | -38.294 | 39.009 | 1.00 | 52.00 |
| 16901 | CE | LYS | C | 596 | -74.335 | -38.064 | 40.384 | 1.00 | 53.52 |
| 16902 | NZ | LYS | C | 596 | -73.053 | -38.801 | 40.581 | 1.00 | 55.00 |
| 16903 | C | LYS | C | 596 | -73.422 | -33.982 | 37.010 | 1.00 | 45.21 |
| 16904 | O | LYS | C | 596 | -74.524 | -33.428 | 37.026 | 1.00 | 45.12 |
| 16905 | N | ARG | C | 597 | -72.279 | -33.315 | 37.144 | 1.00 | 43.57 |
| 16906 | CA | ARG | C | 597 | -72.288 | -31.864 | 37.296 | 1.00 | 42.14 |
| 16907 | CB | ARG | C | 597 | -71.996 | -31.471 | 38.742 | 1.00 | 42.29 |
| 16908 | CG | ARG | C | 597 | -73.052 | -32.015 | 39.692 | 1.00 | 43.16 |
| 16909 | CD | ARG | C | 597 | -72.836 | -31.675 | 41.134 | 1.00 | 44.23 |
| 16910 | NE | ARG | C | 597 | -71.517 | -32.101 | 41.566 | 1.00 | 46.92 |
| 16911 | CZ | ARG | C | 597 | -70.867 | -31.580 | 42.594 | 1.00 | 46.35 |
| 16912 | NH1 | ARG | C | 597 | -71.419 | -30.606 | 43.296 | 1.00 | 47.28 |
| 16913 | NH2 | ARG | C | 597 | -69.663 | -32.028 | 42.915 | 1.00 | 46.60 |
| 16914 | C | ARG | C | 597 | -71.376 | -31.145 | 36.302 | 1.00 | 40.92 |
| 16915 | O | ARG | C | 597 | -70.379 | -30.553 | 36.668 | 1.00 | 40.12 |
| 16916 | N | ILE | C | 598 | -71.746 | -31.226 | 35.028 | 1.00 | 39.93 |
| 16917 | CA | ILE | C | 598 | -71.036 | -30.549 | 33.961 | 1.00 | 38.82 |
| 16918 | CB | ILE | C | 598 | -70.729 | -31.530 | 32.836 | 1.00 | 38.90 |
| 16919 | CG1 | ILE | C | 598 | -69.771 | -32.620 | 33.329 | 1.00 | 39.16 |
| 16920 | CD1 | ILE | C | 598 | -69.535 | -33.711 | 32.314 | 1.00 | 39.45 |
| 16921 | CG2 | ILE | C | 598 | -70.150 | -30.804 | 31.638 | 1.00 | 37.40 |
| 16922 | C | ILE | C | 598 | -71.959 | -29.449 | 33.450 | 1.00 | 38.43 |

FIGURE 3 LT

| A | B | C | D | E | F | G | H | I | J |
|---|---|---|---|---|---|---|---|---|---|
| 16923 | O | ILE | C | 598 | -73.123 | -29.697 | 33.143 | 1.00 | 38.10 |
| 16924 | N | ALA | C | 599 | -71.440 | -28.232 | 33.369 | 1.00 | 37.43 |
| 16925 | CA | ALA | C | 599 | -72.240 | -27.108 | 32.938 | 1.00 | 36.53 |
| 16926 | CB | ALA | C | 599 | -72.361 | -26.093 | 34.057 | 1.00 | 36.78 |
| 16927 | C | ALA | C | 599 | -71.625 | -26.475 | 31.721 | 1.00 | 35.94 |
| 16928 | O | ALA | C | 599 | -70.489 | -26.786 | 31.354 | 1.00 | 36.54 |
| 16929 | N | ILE | C | 600 | -72.375 | -25.571 | 31.107 | 1.00 | 34.62 |
| 16930 | CA | ILE | C | 600 | -71.947 | -24.904 | 29.893 | 1.00 | 33.64 |
| 16931 | CB | ILE | C | 600 | -72.403 | -25.754 | 28.652 | 1.00 | 33.18 |
| 16932 | CG1 | ILE | C | 600 | -71.601 | -25.455 | 27.388 | 1.00 | 33.22 |
| 16933 | CD1 | ILE | C | 600 | -71.251 | -24.046 | 27.210 | 1.00 | 34.49 |
| 16934 | CG2 | ILE | C | 600 | -73.909 | -25.698 | 28.423 | 1.00 | 33.99 |
| 16935 | C | ILE | C | 600 | -72.540 | -23.492 | 29.926 | 1.00 | 33.11 |
| 16936 | O | ILE | C | 600 | -73.693 | -23.313 | 30.307 | 1.00 | 33.14 |
| 16937 | N | TRP | C | 601 | -71.726 | -22.488 | 29.607 | 1.00 | 32.41 |
| 16938 | CA | TRP | C | 601 | -72.182 | -21.108 | 29.586 | 1.00 | 32.23 |
| 16939 | CB | TRP | C | 601 | -72.082 | -20.448 | 30.967 | 1.00 | 31.82 |
| 16940 | CG | TRP | C | 601 | -70.841 | -19.600 | 31.208 | 1.00 | 31.38 |
| 16941 | CD1 | TRP | C | 601 | -69.596 | -20.050 | 31.531 | 1.00 | 31.05 |
| 16942 | NE1 | TRP | C | 601 | -68.738 | -18.994 | 31.711 | 1.00 | 30.87 |
| 16943 | CE2 | TRP | C | 601 | -69.421 | -17.825 | 31.515 | 1.00 | 30.19 |
| 16944 | CD2 | TRP | C | 601 | -70.751 | -18.167 | 31.193 | 1.00 | 30.23 |
| 16945 | CE3 | TRP | C | 601 | -71.659 | -17.135 | 30.935 | 1.00 | 29.79 |
| 16946 | CZ3 | TRP | C | 601 | -71.218 | -15.813 | 31.001 | 1.00 | 29.38 |
| 16947 | CH2 | TRP | C | 601 | -69.884 | -15.510 | 31.324 | 1.00 | 29.36 |
| 16948 | CZ2 | TRP | C | 601 | -68.972 | -16.502 | 31.574 | 1.00 | 29.88 |
| 16949 | C | TRP | C | 601 | -71.386 | -20.297 | 28.590 | 1.00 | 31.88 |
| 16950 | O | TRP | C | 601 | -70.202 | -20.543 | 28.373 | 1.00 | 32.27 |
| 16951 | N | GLY | C | 602 | -72.043 | -19.327 | 27.988 | 1.00 | 31.47 |
| 16952 | CA | GLY | C | 602 | -71.370 | -18.457 | 27.045 | 1.00 | 31.55 |
| 16953 | C | GLY | C | 602 | -72.167 | -17.193 | 26.784 | 1.00 | 31.15 |
| 16954 | O | GLY | C | 602 | -73.370 | -17.166 | 26.989 | 1.00 | 31.09 |
| 16955 | N | TRP | C | 603 | -71.477 | -16.165 | 26.307 | 1.00 | 31.43 |
| 16956 | CA | TRP | C | 603 | -72.052 | -14.869 | 25.979 | 1.00 | 31.67 |
| 16957 | CB | TRP | C | 603 | -71.208 | -13.797 | 26.675 | 1.00 | 31.79 |
| 16958 | CG | TRP | C | 603 | -71.834 | -12.459 | 26.918 | 1.00 | 30.21 |
| 16959 | CD1 | TRP | C | 603 | -72.414 | -11.632 | 26.003 | 1.00 | 28.51 |
| 16960 | NE1 | TRP | C | 603 | -72.847 | -10.476 | 26.615 | 1.00 | 27.71 |
| 16961 | CE2 | TRP | C | 603 | -72.554 | -10.542 | 27.951 | 1.00 | 28.88 |
| 16962 | CD2 | TRP | C | 603 | -71.903 | -11.776 | 28.176 | 1.00 | 29.70 |
| 16963 | CE3 | TRP | C | 603 | -71.483 | -12.086 | 29.477 | 1.00 | 28.49 |
| 16964 | CZ3 | TRP | C | 603 | -71.716 | -11.176 | 30.487 | 1.00 | 30.03 |
| 16965 | CH2 | TRP | C | 603 | -72.354 | -9.945 | 30.222 | 1.00 | 30.46 |
| 16966 | CZ2 | TRP | C | 603 | -72.780 | -9.617 | 28.968 | 1.00 | 29.02 |
| 16967 | C | TRP | C | 603 | -71.935 | -14.679 | 24.472 | 1.00 | 32.12 |
| 16968 | O | TRP | C | 603 | -70.895 | -14.982 | 23.900 | 1.00 | 32.12 |
| 16969 | N | SER | C | 604 | -72.992 | -14.178 | 23.833 | 1.00 | 32.82 |
| 16970 | CA | SER | C | 604 | -72.987 | -13.888 | 22.388 | 1.00 | 33.24 |
| 16971 | CB | SER | C | 604 | -71.887 | -12.871 | 22.049 | 1.00 | 33.52 |
| 16972 | OG | SER | C | 604 | -72.264 | -12.037 | 20.949 | 1.00 | 35.24 |
| 16973 | C | SER | C | 604 | -72.857 | -15.162 | 21.550 | 1.00 | 33.18 |

FIGURE 3 LU

| A | B | C | D | E | F | G | H | I | J |
|---|---|---|---|---|---|---|---|---|---|
| 16974 | O | SER | C | 604 | -73.732 | -16.037 | 21.600 | 1.00 | 33.25 |
| 16975 | N | TYR | C | 605 | -71.784 | -15.276 | 20.773 | 1.00 | 33.40 |
| 16976 | CA | TYR | C | 605 | -71.550 | -16.501 | 20.015 | 1.00 | 33.41 |
| 16977 | CB | TYR | C | 605 | -70.240 | -16.454 | 19.221 | 1.00 | 33.56 |
| 16978 | CG | TYR | C | 605 | -70.234 | -17.447 | 18.081 | 1.00 | 33.91 |
| 16979 | CD1 | TYR | C | 605 | -70.399 | -17.028 | 16.768 | 1.00 | 33.65 |
| 16980 | CE1 | TYR | C | 605 | -70.426 | -17.937 | 15.725 | 1.00 | 34.31 |
| 16981 | CZ | TYR | C | 605 | -70.288 | -19.282 | 15.979 | 1.00 | 34.30 |
| 16982 | OH | TYR | C | 605 | -70.304 | -20.178 | 14.925 | 1.00 | 34.05 |
| 16983 | CE2 | TYR | C | 605 | -70.128 | -19.734 | 17.273 | 1.00 | 33.84 |
| 16984 | CD2 | TYR | C | 605 | -70.108 | -18.815 | 18.320 | 1.00 | 35.11 |
| 16985 | C | TYR | C | 605 | -71.500 | -17.643 | 21.010 | 1.00 | 33.18 |
| 16986 | O | TYR | C | 605 | -71.911 | -18.761 | 20.717 | 1.00 | 33.99 |
| 16987 | N | GLY | C | 606 | -71.006 | -17.357 | 22.202 | 1.00 | 33.02 |
| 16988 | CA | GLY | C | 606 | -70.955 | -18.367 | 23.243 | 1.00 | 32.79 |
| 16989 | C | GLY | C | 606 | -72.326 | -18.701 | 23.802 | 1.00 | 32.74 |
| 16990 | O | GLY | C | 606 | -72.539 | -19.787 | 24.353 | 1.00 | 32.95 |
| 16991 | N | GLY | C | 607 | -73.260 | -17.762 | 23.694 | 1.00 | 32.42 |
| 16992 | CA | GLY | C | 607 | -74.621 | -18.026 | 24.128 | 1.00 | 32.80 |
| 16993 | C | GLY | C | 607 | -75.277 | -18.928 | 23.101 | 1.00 | 32.99 |
| 16994 | O | GLY | C | 607 | -76.028 | -19.860 | 23.424 | 1.00 | 33.21 |
| 16995 | N | TYR | C | 608 | -74.968 | -18.647 | 21.846 | 1.00 | 32.78 |
| 16996 | CA | TYR | C | 608 | -75.458 | -19.452 | 20.749 | 1.00 | 33.55 |
| 16997 | CB | TYR | C | 608 | -74.975 | -18.856 | 19.422 | 1.00 | 33.33 |
| 16998 | CG | TYR | C | 608 | -75.255 | -19.701 | 18.208 | 1.00 | 34.41 |
| 16999 | CD1 | TYR | C | 608 | -74.218 | -20.272 | 17.489 | 1.00 | 34.39 |
| 17000 | CE1 | TYR | C | 608 | -74.459 | -21.028 | 16.378 | 1.00 | 33.71 |
| 17001 | CZ | TYR | C | 608 | -75.738 | -21.227 | 15.968 | 1.00 | 33.92 |
| 17002 | OH | TYR | C | 608 | -75.965 | -21.986 | 14.845 | 1.00 | 35.42 |
| 17003 | CE2 | TYR | C | 608 | -76.795 | -20.671 | 16.658 | 1.00 | 34.18 |
| 17004 | CD2 | TYR | C | 608 | -76.550 | -19.908 | 17.760 | 1.00 | 34.86 |
| 17005 | C | TYR | C | 608 | -74.970 | -20.891 | 20.934 | 1.00 | 33.89 |
| 17006 | O | TYR | C | 608 | -75.778 | -21.819 | 21.019 | 1.00 | 33.91 |
| 17007 | N | VAL | C | 609 | -73.650 | -21.071 | 21.027 | 1.00 | 34.10 |
| 17008 | CA | VAL | C | 609 | -73.083 | -22.418 | 21.168 | 1.00 | 34.52 |
| 17009 | CB | VAL | C | 609 | -71.525 | -22.410 | 21.147 | 1.00 | 34.97 |
| 17010 | CG1 | VAL | C | 609 | -70.956 | -23.796 | 21.469 | 1.00 | 35.13 |
| 17011 | CG2 | VAL | C | 609 | -71.028 | -21.918 | 19.800 | 1.00 | 34.79 |
| 17012 | C | VAL | C | 609 | -73.617 | -23.106 | 22.413 | 1.00 | 34.10 |
| 17013 | O | VAL | C | 609 | -73.993 | -24.264 | 22.359 | 1.00 | 34.11 |
| 17014 | N | THR | C | 610 | -73.687 | -22.384 | 23.529 | 1.00 | 34.16 |
| 17015 | CA | THR | C | 610 | -74.262 | -22.954 | 24.750 | 1.00 | 33.60 |
| 17016 | CB | THR | C | 610 | -74.406 | -21.878 | 25.846 | 1.00 | 33.65 |
| 17017 | OG1 | THR | C | 610 | -73.128 | -21.568 | 26.398 | 1.00 | 34.10 |
| 17018 | CG2 | THR | C | 610 | -75.163 | -22.406 | 27.037 | 1.00 | 32.30 |
| 17019 | C | THR | C | 610 | -75.630 | -23.516 | 24.449 | 1.00 | 33.87 |
| 17020 | O | THR | C | 610 | -75.936 | -24.666 | 24.768 | 1.00 | 34.43 |
| 17021 | N | SER | C | 611 | -76.465 | -22.697 | 23.824 | 1.00 | 34.11 |
| 17022 | CA | SER | C | 611 | -77.837 | -23.092 | 23.552 | 1.00 | 34.11 |
| 17023 | CB | SER | C | 611 | -78.598 | -21.929 | 22.920 | 1.00 | 34.29 |
| 17024 | OG | SER | C | 611 | -78.484 | -20.766 | 23.711 | 1.00 | 33.66 |

FIGURE 3 LV

| A | B | C | D | E | F | G | H | I | J |
|---|---|---|---|---|---|---|---|---|---|
| 17025 | C | SER | C | 611 | -77.886 | -24.281 | 22.618 | 1.00 | 34.42 |
| 17026 | O | SER | C | 611 | -78.688 | -25.198 | 22.797 | 1.00 | 34.17 |
| 17027 | N | MET | C | 612 | -77.029 | -24.250 | 21.605 | 1.00 | 35.04 |
| 17028 | CA | MET | C | 612 | -76.975 | -25.326 | 20.630 | 1.00 | 35.38 |
| 17029 | CB | MET | C | 612 | -76.049 | -24.947 | 19.480 | 1.00 | 35.10 |
| 17030 | CG | MET | C | 612 | -76.579 | -23.795 | 18.669 | 1.00 | 33.97 |
| 17031 | SD | MET | C | 612 | -78.125 | -24.240 | 17.800 | 1.00 | 35.94 |
| 17032 | CE | MET | C | 612 | -77.390 | -25.206 | 16.334 | 1.00 | 32.83 |
| 17033 | C | MET | C | 612 | -76.530 | -26.606 | 21.329 | 1.00 | 36.08 |
| 17034 | O | MET | C | 612 | -77.085 | -27.684 | 21.082 | 1.00 | 36.72 |
| 17035 | N | VAL | C | 613 | -75.557 | -26.492 | 22.227 | 1.00 | 35.96 |
| 17036 | CA | VAL | C | 613 | -75.130 | -27.666 | 22.978 | 1.00 | 36.62 |
| 17037 | CB | VAL | C | 613 | -73.917 | -27.375 | 23.899 | 1.00 | 36.20 |
| 17038 | CG1 | VAL | C | 613 | -73.677 | -28.526 | 24.828 | 1.00 | 35.73 |
| 17039 | CG2 | VAL | C | 613 | -72.683 | -27.109 | 23.082 | 1.00 | 35.75 |
| 17040 | C | VAL | C | 613 | -76.305 | -28.136 | 23.813 | 1.00 | 37.29 |
| 17041 | O | VAL | C | 613 | -76.727 | -29.276 | 23.719 | 1.00 | 38.04 |
| 17042 | N | LEU | C | 614 | -76.851 | -27.236 | 24.618 | 1.00 | 38.36 |
| 17043 | CA | LEU | C | 614 | -77.979 | -27.571 | 25.484 | 1.00 | 39.09 |
| 17044 | CB | LEU | C | 614 | -78.514 | -26.315 | 26.166 | 1.00 | 38.88 |
| 17045 | CG | LEU | C | 614 | -77.630 | -25.883 | 27.322 | 1.00 | 38.68 |
| 17046 | CD1 | LEU | C | 614 | -77.362 | -27.100 | 28.172 | 1.00 | 38.39 |
| 17047 | CD2 | LEU | C | 614 | -78.308 | -24.807 | 28.134 | 1.00 | 36.78 |
| 17048 | C | LEU | C | 614 | -79.110 | -28.255 | 24.753 | 1.00 | 39.45 |
| 17049 | O | LEU | C | 614 | -79.832 | -29.048 | 25.338 | 1.00 | 39.17 |
| 17050 | N | GLY | C | 615 | -79.272 | -27.932 | 23.473 | 1.00 | 40.51 |
| 17051 | CA | GLY | C | 615 | -80.341 | -28.504 | 22.676 | 1.00 | 40.87 |
| 17052 | C | GLY | C | 615 | -79.888 | -29.653 | 21.795 | 1.00 | 41.58 |
| 17053 | O | GLY | C | 615 | -80.673 | -30.168 | 20.986 | 1.00 | 41.90 |
| 17054 | N | SER | C | 616 | -78.630 | -30.062 | 21.951 | 1.00 | 41.72 |
| 17055 | CA | SER | C | 616 | -78.069 | -31.152 | 21.151 | 1.00 | 41.97 |
| 17056 | CB | SER | C | 616 | -76.561 | -31.195 | 21.314 | 1.00 | 41.68 |
| 17057 | OG | SER | C | 616 | -76.249 | -31.654 | 22.616 | 1.00 | 42.65 |
| 17058 | C | SER | C | 616 | -78.633 | -32.532 | 21.495 | 1.00 | 42.07 |
| 17059 | O | SER | C | 616 | -78.662 | -33.418 | 20.646 | 1.00 | 42.08 |
| 17060 | N | GLY | C | 617 | -79.062 | -32.719 | 22.740 | 1.00 | 42.26 |
| 17061 | CA | GLY | C | 617 | -79.603 | -33.997 | 23.173 | 1.00 | 42.25 |
| 17062 | C | GLY | C | 617 | -78.494 | -34.925 | 23.627 | 1.00 | 42.59 |
| 17063 | O | GLY | C | 617 | -78.714 | -36.110 | 23.901 | 1.00 | 42.33 |
| 17064 | N | SER | C | 618 | -77.296 | -34.359 | 23.739 | 1.00 | 42.64 |
| 17065 | CA | SER | C | 618 | -76.098 | -35.111 | 24.076 | 1.00 | 42.59 |
| 17066 | CB | SER | C | 618 | -74.862 | -34.216 | 23.969 | 1.00 | 42.56 |
| 17067 | OG | SER | C | 618 | -74.743 | -33.380 | 25.112 | 1.00 | 43.35 |
| 17068 | C | SER | C | 618 | -76.138 | -35.771 | 25.451 | 1.00 | 42.60 |
| 17069 | O | SER | C | 618 | -75.524 | -36.819 | 25.642 | 1.00 | 42.76 |
| 17070 | N | GLY | C | 619 | -76.823 | -35.152 | 26.413 | 1.00 | 42.31 |
| 17071 | CA | GLY | C | 619 | -76.921 | -35.706 | 27.759 | 1.00 | 41.39 |
| 17072 | C | GLY | C | 619 | -75.720 | -35.422 | 28.646 | 1.00 | 41.22 |
| 17073 | O | GLY | C | 619 | -75.721 | -35.717 | 29.839 | 1.00 | 41.55 |
| 17074 | N | VAL | C | 620 | -74.690 | -34.822 | 28.069 | 1.00 | 40.74 |
| 17075 | CA | VAL | C | 620 | -73.464 | -34.522 | 28.799 | 1.00 | 39.86 |

FIGURE 3 LW

| A | B | C | D | E | F | G | H | I | J |
|---|---|---|---|---|---|---|---|---|---|
| 17076 | CB | VAL | C | 620 | -72.388 | -34.083 | 27.811 | 1.00 | 39.67 |
| 17077 | CG1 | VAL | C | 620 | -71.107 | -33.745 | 28.537 | 1.00 | 39.38 |
| 17078 | CG2 | VAL | C | 620 | -72.169 | -35.168 | 26.779 | 1.00 | 39.20 |
| 17079 | C | VAL | C | 620 | -73.625 | -33.398 | 29.820 | 1.00 | 39.94 |
| 17080 | O | VAL | C | 620 | -73.079 | -33.439 | 30.932 | 1.00 | 39.36 |
| 17081 | N | PHE | C | 621 | -74.372 | -32.379 | 29.423 | 1.00 | 39.77 |
| 17082 | CA | PHE | C | 621 | -74.543 | -31.215 | 30.259 | 1.00 | 39.49 |
| 17083 | CB | PHE | C | 621 | -74.423 | -29.974 | 29.394 | 1.00 | 39.71 |
| 17084 | CG | PHE | C | 621 | -73.097 | -29.865 | 28.685 | 1.00 | 39.12 |
| 17085 | CD1 | PHE | C | 621 | -72.905 | -30.470 | 27.454 | 1.00 | 39.23 |
| 17086 | CE1 | PHE | C | 621 | -71.685 | -30.371 | 26.803 | 1.00 | 38.37 |
| 17087 | CZ | PHE | C | 621 | -70.658 | -29.655 | 27.380 | 1.00 | 37.67 |
| 17088 | CE2 | PHE | C | 621 | -70.838 | -29.053 | 28.612 | 1.00 | 37.11 |
| 17089 | CD2 | PHE | C | 621 | -72.043 | -29.160 | 29.257 | 1.00 | 36.87 |
| 17090 | C | PHE | C | 621 | -75.856 | -31.244 | 31.018 | 1.00 | 39.47 |
| 17091 | O | PHE | C | 621 | -76.893 | -31.674 | 30.521 | 1.00 | 39.87 |
| 17092 | N | LYS | C | 622 | -75.803 | -30.798 | 32.250 | 1.00 | 39.38 |
| 17093 | CA | LYS | C | 622 | -76.977 | -30.819 | 33.086 | 1.00 | 39.26 |
| 17094 | CB | LYS | C | 622 | -76.521 | -31.210 | 34.490 | 1.00 | 39.00 |
| 17095 | CG | LYS | C | 622 | -77.546 | -31.051 | 35.594 | 1.00 | 39.56 |
| 17096 | CD | LYS | C | 622 | -76.865 | -31.106 | 36.951 | 1.00 | 40.55 |
| 17097 | CE | LYS | C | 622 | -77.826 | -31.472 | 38.067 | 1.00 | 41.54 |
| 17098 | NZ | LYS | C | 622 | -78.564 | -30.300 | 38.587 | 1.00 | 43.09 |
| 17099 | C | LYS | C | 622 | -77.480 | -29.403 | 33.136 | 1.00 | 38.96 |
| 17100 | O | LYS | C | 622 | -78.568 | -29.125 | 33.632 | 1.00 | 38.86 |
| 17101 | N | CYS | C | 623 | -76.704 | -28.523 | 32.527 | 1.00 | 38.77 |
| 17102 | CA | CYS | C | 623 | -76.767 | -27.148 | 32.913 | 1.00 | 38.86 |
| 17103 | CB | CYS | C | 623 | -75.829 | -27.102 | 34.099 | 1.00 | 40.12 |
| 17104 | SG | CYS | C | 623 | -76.401 | -26.181 | 35.452 | 1.00 | 43.70 |
| 17105 | C | CYS | C | 623 | -76.116 | -26.210 | 31.958 | 1.00 | 37.46 |
| 17106 | O | CYS | C | 623 | -75.035 | -26.509 | 31.446 | 1.00 | 37.36 |
| 17107 | N | GLY | C | 624 | -76.702 | -25.027 | 31.806 | 1.00 | 36.02 |
| 17108 | CA | GLY | C | 624 | -76.106 | -24.025 | 30.953 | 1.00 | 34.25 |
| 17109 | C | GLY | C | 624 | -76.740 | -22.657 | 31.009 | 1.00 | 32.76 |
| 17110 | O | GLY | C | 624 | -77.937 | -22.514 | 31.265 | 1.00 | 32.76 |
| 17111 | N | ILE | C | 625 | -75.916 | -21.649 | 30.757 | 1.00 | 31.31 |
| 17112 | CA | ILE | C | 625 | -76.359 | -20.271 | 30.753 | 1.00 | 29.91 |
| 17113 | CB | ILE | C | 625 | -75.690 | -19.477 | 31.867 | 1.00 | 29.76 |
| 17114 | CG1 | ILE | C | 625 | -75.939 | -20.154 | 33.218 | 1.00 | 29.14 |
| 17115 | CD1 | ILE | C | 625 | -75.396 | -19.370 | 34.398 | 1.00 | 30.29 |
| 17116 | CG2 | ILE | C | 625 | -76.190 | -18.033 | 31.844 | 1.00 | 27.52 |
| 17117 | C | ILE | C | 625 | -75.992 | -19.629 | 29.444 | 1.00 | 29.26 |
| 17118 | O | ILE | C | 625 | -74.817 | -19.590 | 29.087 | 1.00 | 29.27 |
| 17119 | N | ALA | C | 626 | -76.998 | -19.140 | 28.731 | 1.00 | 28.47 |
| 17120 | CA | ALA | C | 626 | -76.773 | -18.382 | 27.509 | 1.00 | 28.34 |
| 17121 | CB | ALA | C | 626 | -77.692 | -18.864 | 26.379 | 1.00 | 27.97 |
| 17122 | C | ALA | C | 626 | -77.034 | -16.920 | 27.804 | 1.00 | 28.30 |
| 17123 | O | ALA | C | 626 | -78.106 | -16.548 | 28.293 | 1.00 | 28.46 |
| 17124 | N | VAL | C | 627 | -76.042 | -16.088 | 27.527 | 1.00 | 28.44 |
| 17125 | CA | VAL | C | 627 | -76.198 | -14.657 | 27.699 | 1.00 | 28.35 |
| 17126 | CB | VAL | C | 627 | -75.099 | -14.081 | 28.587 | 1.00 | 28.72 |

FIGURE 3 LX

| A | B | C | D | E | F | G | H | I | J |
|---|---|---|---|---|---|---|---|---|---|
| 17127 | CG1 | VAL | C | 627 | -75.289 | -12.579 | 28.744 | 1.00 | 27.70 |
| 17128 | CG2 | VAL | C | 627 | -75.069 | -14.806 | 29.950 | 1.00 | 28.15 |
| 17129 | C | VAL | C | 627 | -76.095 | -13.988 | 26.331 | 1.00 | 28.29 |
| 17130 | O | VAL | C | 627 | -75.111 | -14.178 | 25.614 | 1.00 | 28.29 |
| 17131 | N | ALA | C | 628 | -77.119 | -13.223 | 25.974 | 1.00 | 27.39 |
| 17132 | CA | ALA | C | 628 | -77.144 | -12.475 | 24.713 | 1.00 | 26.74 |
| 17133 | CB | ALA | C | 628 | -76.253 | -11.263 | 24.813 | 1.00 | 26.49 |
| 17134 | C | ALA | C | 628 | -76.772 | -13.325 | 23.510 | 1.00 | 26.29 |
| 17135 | O | ALA | C | 628 | -75.975 | -12.941 | 22.674 | 1.00 | 25.93 |
| 17136 | N | PRO | C | 629 | -77.404 | -14.474 | 23.400 | 1.00 | 26.54 |
| 17137 | CA | PRO | C | 629 | -77.091 | -15.421 | 22.347 | 1.00 | 26.91 |
| 17138 | CB | PRO | C | 629 | -77.784 | -16.671 | 22.874 | 1.00 | 26.98 |
| 17139 | CG | PRO | C | 629 | -79.035 | -16.108 | 23.393 | 1.00 | 25.93 |
| 17140 | CD | PRO | C | 629 | -78.485 | -14.985 | 24.256 | 1.00 | 26.49 |
| 17141 | C | PRO | C | 629 | -77.716 | -15.068 | 21.005 | 1.00 | 27.71 |
| 17142 | O | PRO | C | 629 | -78.839 | -14.531 | 20.928 | 1.00 | 27.00 |
| 17143 | N | VAL | C | 630 | -76.982 | -15.368 | 19.941 | 1.00 | 28.10 |
| 17144 | CA | VAL | C | 630 | -77.574 | -15.331 | 18.630 | 1.00 | 28.32 |
| 17145 | CB | VAL | C | 630 | -76.514 | -15.487 | 17.535 | 1.00 | 28.26 |
| 17146 | CG1 | VAL | C | 630 | -77.167 | -15.871 | 16.205 | 1.00 | 27.63 |
| 17147 | CG2 | VAL | C | 630 | -75.705 | -14.228 | 17.378 | 1.00 | 27.55 |
| 17148 | C | VAL | C | 630 | -78.424 | -16.600 | 18.698 | 1.00 | 28.99 |
| 17149 | O | VAL | C | 630 | -78.030 | -17.549 | 19.367 | 1.00 | 29.78 |
| 17150 | N | SER | C | 631 | -79.584 | -16.614 | 18.055 | 1.00 | 29.40 |
| 17151 | CA | SER | C | 631 | -80.460 | -17.785 | 18.043 | 1.00 | 29.82 |
| 17152 | CB | SER | C | 631 | -81.768 | -17.481 | 18.752 | 1.00 | 29.67 |
| 17153 | OG | SER | C | 631 | -82.450 | -16.468 | 18.067 | 1.00 | 28.41 |
| 17154 | C | SER | C | 631 | -80.762 | -18.255 | 16.620 | 1.00 | 30.66 |
| 17155 | O | SER | C | 631 | -81.152 | -19.396 | 16.413 | 1.00 | 30.31 |
| 17156 | N | ARG | C | 632 | -80.625 | -17.353 | 15.651 | 1.00 | 31.60 |
| 17157 | CA | ARG | C | 632 | -80.727 | -17.726 | 14.252 | 1.00 | 33.04 |
| 17158 | CB | ARG | C | 632 | -82.170 | -17.890 | 13.790 | 1.00 | 33.95 |
| 17159 | CG | ARG | C | 632 | -82.839 | -16.622 | 13.450 | 1.00 | 35.70 |
| 17160 | CD | ARG | C | 632 | -83.911 | -16.736 | 12.385 | 1.00 | 40.20 |
| 17161 | NE | ARG | C | 632 | -84.374 | -18.089 | 12.152 | 1.00 | 42.40 |
| 17162 | CZ | ARG | C | 632 | -85.235 | -18.397 | 11.185 | 1.00 | 45.70 |
| 17163 | NH1 | ARG | C | 632 | -85.622 | -19.658 | 11.002 | 1.00 | 43.76 |
| 17164 | NH2 | ARG | C | 632 | -85.718 | -17.430 | 10.397 | 1.00 | 45.81 |
| 17165 | C | ARG | C | 632 | -79.981 | -16.692 | 13.426 | 1.00 | 33.22 |
| 17166 | O | ARG | C | 632 | -80.112 | -15.485 | 13.638 | 1.00 | 33.56 |
| 17167 | N | TRP | C | 633 | -79.195 | -17.166 | 12.472 | 1.00 | 33.29 |
| 17168 | CA | TRP | C | 633 | -78.300 | -16.276 | 11.763 | 1.00 | 33.58 |
| 17169 | CB | TRP | C | 633 | -77.226 | -17.071 | 11.000 | 1.00 | 33.49 |
| 17170 | CG | TRP | C | 633 | -76.340 | -17.724 | 12.012 | 1.00 | 33.94 |
| 17171 | CD1 | TRP | C | 633 | -76.351 | -19.030 | 12.398 | 1.00 | 33.15 |
| 17172 | NE1 | TRP | C | 633 | -75.434 | -19.231 | 13.400 | 1.00 | 34.18 |
| 17173 | CE2 | TRP | C | 633 | -74.813 | -18.039 | 13.679 | 1.00 | 33.45 |
| 17174 | CD2 | TRP | C | 633 | -75.374 | -17.069 | 12.840 | 1.00 | 33.32 |
| 17175 | CE3 | TRP | C | 633 | -74.910 | -15.753 | 12.937 | 1.00 | 34.06 |
| 17176 | CZ3 | TRP | C | 633 | -73.930 | -15.455 | 13.850 | 1.00 | 33.46 |
| 17177 | CH2 | TRP | C | 633 | -73.388 | -16.446 | 14.668 | 1.00 | 34.25 |

FIGURE 3 LY

| A | B | C | D | E | F | G | H | I | J |
|---|---|---|---|---|---|---|---|---|---|
| 17178 | CZ2 | TRP | C | 633 | -73.819 | -17.741 | 14.599 | 1.00 | 33.75 |
| 17179 | C | TRP | C | 633 | -78.943 | -15.144 | 10.967 | 1.00 | 33.52 |
| 17180 | O | TRP | C | 633 | -78.325 | -14.102 | 10.782 | 1.00 | 34.23 |
| 17181 | N | GLU | C | 634 | -80.180 | -15.324 | 10.532 | 1.00 | 33.78 |
| 17182 | CA | GLU | C | 634 | -80.861 | -14.253 | 9.806 | 1.00 | 34.16 |
| 17183 | CB | GLU | C | 634 | -82.202 | -14.717 | 9.255 | 1.00 | 34.07 |
| 17184 | CG | GLU | C | 634 | -82.108 | -15.639 | 8.054 | 1.00 | 36.42 |
| 17185 | CD | GLU | C | 634 | -82.418 | -17.078 | 8.414 | 1.00 | 39.31 |
| 17186 | OE1 | GLU | C | 634 | -83.359 | -17.642 | 7.807 | 1.00 | 38.59 |
| 17187 | OE2 | GLU | C | 634 | -81.735 | -17.627 | 9.322 | 1.00 | 40.88 |
| 17188 | C | GLU | C | 634 | -81.081 | -13.009 | 10.671 | 1.00 | 33.84 |
| 17189 | O | GLU | C | 634 | -81.339 | -11.922 | 10.151 | 1.00 | 33.64 |
| 17190 | N | TYR | C | 635 | -80.983 | -13.163 | 11.989 | 1.00 | 32.97 |
| 17191 | CA | TYR | C | 635 | -81.240 | -12.039 | 12.867 | 1.00 | 32.19 |
| 17192 | CB | TYR | C | 635 | -81.641 | -12.530 | 14.252 | 1.00 | 32.26 |
| 17193 | CG | TYR | C | 635 | -82.968 | -13.267 | 14.341 | 1.00 | 31.06 |
| 17194 | CD1 | TYR | C | 635 | -84.000 | -13.015 | 13.451 | 1.00 | 31.62 |
| 17195 | CE1 | TYR | C | 635 | -85.217 | -13.688 | 13.555 | 1.00 | 30.68 |
| 17196 | CZ | TYR | C | 635 | -85.386 | -14.602 | 14.550 | 1.00 | 28.71 |
| 17197 | OH | TYR | C | 635 | -86.559 | -15.277 | 14.674 | 1.00 | 29.34 |
| 17198 | CE2 | TYR | C | 635 | -84.385 | -14.845 | 15.446 | 1.00 | 30.12 |
| 17199 | CD2 | TYR | C | 635 | -83.183 | -14.187 | 15.334 | 1.00 | 28.26 |
| 17200 | C | TYR | C | 635 | -80.014 | -11.184 | 13.045 | 1.00 | 32.11 |
| 17201 | O | TYR | C | 635 | -80.118 | -10.059 | 13.495 | 1.00 | 32.11 |
| 17202 | N | TYR | C | 636 | -78.849 | -11.725 | 12.718 | 1.00 | 31.77 |
| 17203 | CA | TYR | C | 636 | -77.602 | -11.031 | 13.008 | 1.00 | 32.19 |
| 17204 | CB | TYR | C | 636 | -76.530 | -12.012 | 13.549 | 1.00 | 31.98 |
| 17205 | CG | TYR | C | 636 | -75.428 | -11.293 | 14.289 | 1.00 | 31.71 |
| 17206 | CD1 | TYR | C | 636 | -75.727 | -10.444 | 15.340 | 1.00 | 30.05 |
| 17207 | CE1 | TYR | C | 636 | -74.741 | -9.739 | 15.991 | 1.00 | 28.81 |
| 17208 | CZ | TYR | C | 636 | -73.434 | -9.888 | 15.598 | 1.00 | 27.74 |
| 17209 | OH | TYR | C | 636 | -72.454 | -9.194 | 16.241 | 1.00 | 25.92 |
| 17210 | CE2 | TYR | C | 636 | -73.104 | -10.722 | 14.556 | 1.00 | 28.79 |
| 17211 | CD2 | TYR | C | 636 | -74.096 | -11.420 | 13.904 | 1.00 | 30.86 |
| 17212 | C | TYR | C | 636 | -77.117 | -10.207 | 11.827 | 1.00 | 32.70 |
| 17213 | O | TYR | C | 636 | -77.584 | -10.390 | 10.700 | 1.00 | 32.60 |
| 17214 | N | ASP | C | 637 | -76.191 | -9.288 | 12.094 | 1.00 | 34.23 |
| 17215 | CA | ASP | C | 637 | -75.706 | -8.349 | 11.081 | 1.00 | 34.69 |
| 17216 | CB | ASP | C | 637 | -74.807 | -7.272 | 11.686 | 1.00 | 34.90 |
| 17217 | CG | ASP | C | 637 | -73.408 | -7.769 | 12.010 | 1.00 | 36.72 |
| 17218 | OD1 | ASP | C | 637 | -72.629 | -8.121 | 11.087 | 1.00 | 37.39 |
| 17219 | OD2 | ASP | C | 637 | -72.977 | -7.786 | 13.182 | 1.00 | 39.27 |
| 17220 | C | ASP | C | 637 | -75.029 | -9.002 | 9.887 | 1.00 | 35.51 |
| 17221 | O | ASP | C | 637 | -74.316 | -10.016 | 10.011 | 1.00 | 35.91 |
| 17222 | N | SER | C | 638 | -75.250 | -8.378 | 8.735 | 1.00 | 35.24 |
| 17223 | CA | SER | C | 638 | -74.774 | -8.863 | 7.445 | 1.00 | 35.54 |
| 17224 | CB | SER | C | 638 | -75.170 | -7.854 | 6.358 | 1.00 | 35.16 |
| 17225 | OG | SER | C | 638 | -74.367 | -6.697 | 6.489 | 1.00 | 33.95 |
| 17226 | C | SER | C | 638 | -73.271 | -9.144 | 7.346 | 1.00 | 35.66 |
| 17227 | O | SER | C | 638 | -72.873 | -10.247 | 7.023 | 1.00 | 35.12 |
| 17228 | N | VAL | C | 639 | -72.444 | -8.137 | 7.597 | 1.00 | 36.79 |

FIGURE 3 LZ

| A | B | C | D | E | F | G | H | I | J |
|---|---|---|---|---|---|---|---|---|---|
| 17229 | CA | VAL | C | 639 | -71.006 | -8.313 | 7.433 | 1.00 | 37.50 |
| 17230 | CB | VAL | C | 639 | -70.204 | -6.982 | 7.587 | 1.00 | 37.62 |
| 17231 | CG1 | VAL | C | 639 | -68.771 | -7.243 | 7.990 | 1.00 | 36.07 |
| 17232 | CG2 | VAL | C | 639 | -70.860 | -6.060 | 8.554 | 1.00 | 37.50 |
| 17233 | C | VAL | C | 639 | -70.442 | -9.478 | 8.249 | 1.00 | 38.49 |
| 17234 | O | VAL | C | 639 | -69.700 | -10.305 | 7.712 | 1.00 | 39.33 |
| 17235 | N | TYR | C | 640 | -70.821 | -9.593 | 9.516 | 1.00 | 39.06 |
| 17236 | CA | TYR | C | 640 | -70.324 | -10.709 | 10.327 | 1.00 | 39.24 |
| 17237 | CB | TYR | C | 640 | -70.677 | -10.533 | 11.794 | 1.00 | 39.23 |
| 17238 | CG | TYR | C | 640 | -70.104 | -11.611 | 12.689 | 1.00 | 39.59 |
| 17239 | CD1 | TYR | C | 640 | -68.868 | -11.439 | 13.299 | 1.00 | 40.35 |
| 17240 | CE1 | TYR | C | 640 | -68.331 | -12.411 | 14.123 | 1.00 | 40.39 |
| 17241 | CZ | TYR | C | 640 | -69.035 | -13.575 | 14.354 | 1.00 | 40.21 |
| 17242 | OH | TYR | C | 640 | -68.490 | -14.526 | 15.188 | 1.00 | 40.53 |
| 17243 | CE2 | TYR | C | 640 | -70.270 | -13.773 | 13.767 | 1.00 | 38.88 |
| 17244 | CD2 | TYR | C | 640 | -70.798 | -12.792 | 12.937 | 1.00 | 39.33 |
| 17245 | C | TYR | C | 640 | -70.906 | -12.022 | 9.879 | 1.00 | 39.48 |
| 17246 | O | TYR | C | 640 | -70.180 | -12.999 | 9.674 | 1.00 | 39.99 |
| 17247 | N | THR | C | 641 | -72.224 | -12.057 | 9.744 | 1.00 | 39.54 |
| 17248 | CA | THR | C | 641 | -72.906 | -13.295 | 9.404 | 1.00 | 39.60 |
| 17249 | CB | THR | C | 641 | -74.422 | -13.083 | 9.439 | 1.00 | 39.84 |
| 17250 | OG1 | THR | C | 641 | -74.832 | -12.695 | 10.759 | 1.00 | 38.30 |
| 17251 | CG2 | THR | C | 641 | -75.174 | -14.412 | 9.166 | 1.00 | 39.08 |
| 17252 | C | THR | C | 641 | -72.481 | -13.894 | 8.054 | 1.00 | 40.26 |
| 17253 | O | THR | C | 641 | -71.993 | -15.020 | 7.999 | 1.00 | 40.38 |
| 17254 | N | GLU | C | 642 | -72.670 | -13.137 | 6.979 | 1.00 | 40.73 |
| 17255 | CA | GLU | C | 642 | -72.374 | -13.600 | 5.620 | 1.00 | 41.55 |
| 17256 | CB | GLU | C | 642 | -72.769 | -12.504 | 4.629 | 1.00 | 41.64 |
| 17257 | CG | GLU | C | 642 | -74.212 | -12.058 | 4.818 | 1.00 | 41.31 |
| 17258 | CD | GLU | C | 642 | -74.503 | -10.705 | 4.223 | 1.00 | 40.79 |
| 17259 | OE1 | GLU | C | 642 | -73.554 | -10.053 | 3.752 | 1.00 | 41.89 |
| 17260 | OE2 | GLU | C | 642 | -75.684 | -10.290 | 4.239 | 1.00 | 40.01 |
| 17261 | C | GLU | C | 642 | -70.919 | -14.050 | 5.413 | 1.00 | 42.17 |
| 17262 | O | GLU | C | 642 | -70.633 | -15.006 | 4.685 | 1.00 | 42.48 |
| 17263 | N | ARG | C | 643 | -70.006 | -13.348 | 6.066 | 1.00 | 42.70 |
| 17264 | CA | ARG | C | 643 | -68.597 | -13.698 | 6.064 | 1.00 | 42.56 |
| 17265 | CB | ARG | C | 643 | -67.893 | -12.953 | 7.199 | 1.00 | 42.28 |
| 17266 | CG | ARG | C | 643 | -66.442 | -13.299 | 7.370 | 1.00 | 41.76 |
| 17267 | CD | ARG | C | 643 | -65.778 | -12.557 | 8.516 | 1.00 | 41.43 |
| 17268 | NE | ARG | C | 643 | -66.051 | -11.127 | 8.492 | 1.00 | 40.24 |
| 17269 | CZ | ARG | C | 643 | -66.102 | -10.357 | 9.574 | 1.00 | 39.75 |
| 17270 | NH1 | ARG | C | 643 | -66.364 | -9.051 | 9.452 | 1.00 | 37.41 |
| 17271 | NH2 | ARG | C | 643 | -65.892 | -10.891 | 10.779 | 1.00 | 37.15 |
| 17272 | C | ARG | C | 643 | -68.405 | -15.188 | 6.265 | 1.00 | 42.95 |
| 17273 | O | ARG | C | 643 | -67.512 | -15.797 | 5.658 | 1.00 | 43.32 |
| 17274 | N | TYR | C | 644 | -69.230 | -15.776 | 7.126 | 1.00 | 42.77 |
| 17275 | CA | TYR | C | 644 | -69.121 | -17.204 | 7.412 | 1.00 | 43.05 |
| 17276 | CB | TYR | C | 644 | -69.031 | -17.458 | 8.925 | 1.00 | 42.61 |
| 17277 | CG | TYR | C | 644 | -68.128 | -16.507 | 9.650 | 1.00 | 41.89 |
| 17278 | CD1 | TYR | C | 644 | -66.789 | -16.402 | 9.312 | 1.00 | 41.82 |
| 17279 | CE1 | TYR | C | 644 | -65.960 | -15.529 | 9.962 | 1.00 | 40.56 |

FIGURE 3 MA

| A | B | C | D | E | F | G | H | I | J |
|---|---|---|---|---|---|---|---|---|---|
| 17280 | CZ | TYR | C | 644 | -66.462 | -14.748 | 10.966 | 1.00 | 40.93 |
| 17281 | OH | TYR | C | 644 | -65.636 | -13.869 | 11.616 | 1.00 | 42.11 |
| 17282 | CE2 | TYR | C | 644 | -67.790 | -14.825 | 11.319 | 1.00 | 41.34 |
| 17283 | CD2 | TYR | C | 644 | -68.614 | -15.699 | 10.661 | 1.00 | 41.55 |
| 17284 | C | TYR | C | 644 | -70.294 | -18.009 | 6.892 | 1.00 | 43.28 |
| 17285 | O | TYR | C | 644 | -70.234 | -19.233 | 6.856 | 1.00 | 43.75 |
| 17286 | N | MET | C | 645 | -71.373 | -17.351 | 6.502 | 1.00 | 43.62 |
| 17287 | CA | MET | C | 645 | -72.560 | -18.125 | 6.152 | 1.00 | 44.32 |
| 17288 | CB | MET | C | 645 | -73.691 | -17.847 | 7.158 | 1.00 | 44.38 |
| 17289 | CG | MET | C | 645 | -73.467 | -18.442 | 8.534 | 1.00 | 43.62 |
| 17290 | SD | MET | C | 645 | -74.103 | -20.120 | 8.619 | 1.00 | 44.50 |
| 17291 | CE | MET | C | 645 | -75.862 | -19.820 | 8.342 | 1.00 | 41.22 |
| 17292 | C | MET | C | 645 | -73.071 | -17.907 | 4.740 | 1.00 | 44.74 |
| 17293 | O | MET | C | 645 | -73.955 | -18.633 | 4.294 | 1.00 | 44.86 |
| 17294 | N | GLY | C | 646 | -72.524 | -16.926 | 4.036 | 1.00 | 45.12 |
| 17295 | CA | GLY | C | 646 | -73.048 | -16.599 | 2.721 | 1.00 | 46.52 |
| 17296 | C | GLY | C | 646 | -74.415 | -15.956 | 2.893 | 1.00 | 47.23 |
| 17297 | O | GLY | C | 646 | -74.722 | -15.437 | 3.965 | 1.00 | 47.68 |
| 17298 | N | LEU | C | 647 | -75.252 | -15.992 | 1.865 | 1.00 | 47.94 |
| 17299 | CA | LEU | C | 647 | -76.563 | -15.359 | 1.976 | 1.00 | 48.69 |
| 17300 | CB | LEU | C | 647 | -76.905 | -14.568 | 0.710 | 1.00 | 48.71 |
| 17301 | CG | LEU | C | 647 | -75.854 | -13.625 | 0.133 | 1.00 | 49.78 |
| 17302 | CD1 | LEU | C | 647 | -75.447 | -12.544 | 1.152 | 1.00 | 50.66 |
| 17303 | CD2 | LEU | C | 647 | -74.641 | -14.387 | -0.374 | 1.00 | 50.76 |
| 17304 | C | LEU | C | 647 | -77.683 | -16.343 | 2.294 | 1.00 | 48.89 |
| 17305 | O | LEU | C | 647 | -77.620 | -17.510 | 1.932 | 1.00 | 48.43 |
| 17306 | N | PRO | C | 648 | -78.710 | -15.845 | 2.976 | 1.00 | 49.42 |
| 17307 | CA | PRO | C | 648 | -79.881 | -16.644 | 3.332 | 1.00 | 50.21 |
| 17308 | CB | PRO | C | 648 | -80.548 | -15.814 | 4.434 | 1.00 | 49.80 |
| 17309 | CG | PRO | C | 648 | -79.631 | -14.702 | 4.706 | 1.00 | 49.54 |
| 17310 | CD | PRO | C | 648 | -78.833 | -14.467 | 3.470 | 1.00 | 49.59 |
| 17311 | C | PRO | C | 648 | -80.865 | -16.811 | 2.169 | 1.00 | 50.95 |
| 17312 | O | PRO | C | 648 | -82.052 | -16.998 | 2.424 | 1.00 | 51.46 |
| 17313 | N | THR | C | 649 | -80.401 | -16.718 | 0.926 | 1.00 | 51.64 |
| 17314 | CA | THR | C | 649 | -81.271 | -16.987 | -0.222 | 1.00 | 52.36 |
| 17315 | CB | THR | C | 649 | -80.887 | -16.118 | -1.421 | 1.00 | 52.18 |
| 17316 | OG1 | THR | C | 649 | -79.719 | -16.663 | -2.043 | 1.00 | 53.23 |
| 17317 | CG2 | THR | C | 649 | -80.432 | -14.743 | -0.972 | 1.00 | 52.56 |
| 17318 | C | THR | C | 649 | -81.130 | -18.449 | -0.617 | 1.00 | 52.58 |
| 17319 | O | THR | C | 649 | -80.092 | -19.058 | -0.375 | 1.00 | 52.70 |
| 17320 | N | PRO | C | 650 | -82.172 | -19.005 | -1.228 | 1.00 | 53.12 |
| 17321 | CA | PRO | C | 650 | -82.174 | -20.401 | -1.683 | 1.00 | 53.38 |
| 17322 | CB | PRO | C | 650 | -83.490 | -20.500 | -2.457 | 1.00 | 53.46 |
| 17323 | CG | PRO | C | 650 | -84.370 | -19.497 | -1.820 | 1.00 | 52.99 |
| 17324 | CD | PRO | C | 650 | -83.456 | -18.338 | -1.503 | 1.00 | 53.43 |
| 17325 | C | PRO | C | 650 | -81.004 | -20.780 | -2.603 | 1.00 | 53.75 |
| 17326 | O | PRO | C | 650 | -80.548 | -21.925 | -2.594 | 1.00 | 53.62 |
| 17327 | N | GLU | C | 651 | -80.519 | -19.829 | -3.388 | 1.00 | 53.94 |
| 17328 | CA | GLU | C | 651 | -79.435 | -20.122 | -4.312 | 1.00 | 54.28 |
| 17329 | CB | GLU | C | 651 | -79.485 | -19.166 | -5.506 | 1.00 | 54.69 |
| 17330 | CG | GLU | C | 651 | -79.984 | -17.767 | -5.166 | 1.00 | 56.36 |

FIGURE 3 MB

| A | B | C | D | E | F | G | H | I | J |
|---|---|---|---|---|---|---|---|---|---|
| 17331 | CD | GLU | C | 651 | -81.499 | -17.698 | -5.036 | 1.00 | 58.57 |
| 17332 | OE1 | GLU | C | 651 | -82.025 | -16.628 | -4.646 | 1.00 | 59.40 |
| 17333 | OE2 | GLU | C | 651 | -82.169 | -18.714 | -5.335 | 1.00 | 59.57 |
| 17334 | C | GLU | C | 651 | -78.065 | -20.076 | -3.636 | 1.00 | 54.06 |
| 17335 | O | GLU | C | 651 | -77.039 | -20.329 | -4.276 | 1.00 | 54.13 |
| 17336 | N | ASP | C | 652 | -78.039 | -19.750 | -2.347 | 1.00 | 53.63 |
| 17337 | CA | ASP | C | 652 | -76.768 | -19.721 | -1.626 | 1.00 | 53.20 |
| 17338 | CB | ASP | C | 652 | -76.393 | -18.299 | -1.180 | 1.00 | 53.09 |
| 17339 | CG | ASP | C | 652 | -74.964 | -18.204 | -0.671 | 1.00 | 53.49 |
| 17340 | OD1 | ASP | C | 652 | -74.409 | -17.082 | -0.630 | 1.00 | 52.38 |
| 17341 | OD2 | ASP | C | 652 | -74.308 | -19.198 | -0.287 | 1.00 | 55.11 |
| 17342 | C | ASP | C | 652 | -76.764 | -20.689 | -0.459 | 1.00 | 52.74 |
| 17343 | O | ASP | C | 652 | -76.537 | -21.877 | -0.650 | 1.00 | 52.89 |
| 17344 | N | ASN | C | 653 | -77.058 | -20.195 | 0.740 | 1.00 | 52.38 |
| 17345 | CA | ASN | C | 653 | -76.958 | -21.015 | 1.947 | 1.00 | 51.91 |
| 17346 | CB | ASN | C | 653 | -75.732 | -20.560 | 2.746 | 1.00 | 51.79 |
| 17347 | CG | ASN | C | 653 | -75.163 | -21.652 | 3.633 | 1.00 | 51.84 |
| 17348 | OD1 | ASN | C | 653 | -75.298 | -22.846 | 3.345 | 1.00 | 50.92 |
| 17349 | ND2 | ASN | C | 653 | -74.511 | -21.242 | 4.722 | 1.00 | 51.55 |
| 17350 | C | ASN | C | 653 | -78.197 | -21.036 | 2.858 | 1.00 | 51.68 |
| 17351 | O | ASN | C | 653 | -78.134 | -21.541 | 3.974 | 1.00 | 51.25 |
| 17352 | N | LEU | C | 654 | -79.323 | -20.509 | 2.381 | 1.00 | 51.80 |
| 17353 | CA | LEU | C | 654 | -80.551 | -20.457 | 3.188 | 1.00 | 51.68 |
| 17354 | CB | LEU | C | 654 | -81.763 | -20.065 | 2.332 | 1.00 | 51.72 |
| 17355 | CG | LEU | C | 654 | -83.106 | -19.868 | 3.052 | 1.00 | 51.87 |
| 17356 | CD1 | LEU | C | 654 | -84.130 | -19.231 | 2.120 | 1.00 | 51.14 |
| 17357 | CD2 | LEU | C | 654 | -82.949 | -19.028 | 4.314 | 1.00 | 50.32 |
| 17358 | C | LEU | C | 654 | -80.852 | -21.739 | 3.965 | 1.00 | 51.39 |
| 17359 | O | LEU | C | 654 | -81.305 | -21.686 | 5.104 | 1.00 | 51.54 |
| 17360 | N | ASP | C | 655 | -80.593 | -22.886 | 3.355 | 1.00 | 51.05 |
| 17361 | CA | ASP | C | 655 | -80.874 | -24.168 | 3.998 | 1.00 | 50.87 |
| 17362 | CB | ASP | C | 655 | -80.578 | -25.345 | 3.053 | 1.00 | 51.10 |
| 17363 | CG | ASP | C | 655 | -81.760 | -25.680 | 2.161 | 1.00 | 52.25 |
| 17364 | OD1 | ASP | C | 655 | -82.465 | -24.714 | 1.761 | 1.00 | 52.48 |
| 17365 | OD2 | ASP | C | 655 | -82.058 | -26.860 | 1.827 | 1.00 | 53.32 |
| 17366 | C | ASP | C | 655 | -80.147 | -24.373 | 5.319 | 1.00 | 50.12 |
| 17367 | O | ASP | C | 655 | -80.720 | -24.894 | 6.279 | 1.00 | 50.29 |
| 17368 | N | HIS | C | 656 | -78.882 | -23.999 | 5.384 | 1.00 | 49.10 |
| 17369 | CA | HIS | C | 656 | -78.208 | -24.179 | 6.657 | 1.00 | 48.21 |
| 17370 | CB | HIS | C | 656 | -76.698 | -24.334 | 6.535 | 1.00 | 47.87 |
| 17371 | CG | HIS | C | 656 | -76.060 | -24.652 | 7.844 | 1.00 | 48.13 |
| 17372 | ND1 | HIS | C | 656 | -76.313 | -25.826 | 8.519 | 1.00 | 48.39 |
| 17373 | CE1 | HIS | C | 656 | -75.669 | -25.814 | 9.671 | 1.00 | 48.27 |
| 17374 | NE2 | HIS | C | 656 | -75.019 | -24.667 | 9.774 | 1.00 | 48.51 |
| 17375 | CD2 | HIS | C | 656 | -75.264 | -23.913 | 8.653 | 1.00 | 48.48 |
| 17376 | C | HIS | C | 656 | -78.573 | -23.069 | 7.647 | 1.00 | 47.37 |
| 17377 | O | HIS | C | 656 | -78.608 | -23.291 | 8.852 | 1.00 | 46.92 |
| 17378 | N | TYR | C | 657 | -78.830 | -21.875 | 7.122 | 1.00 | 46.50 |
| 17379 | CA | TYR | C | 657 | -79.300 | -20.771 | 7.939 | 1.00 | 45.81 |
| 17380 | CB | TYR | C | 657 | -79.815 | -19.648 | 7.067 | 1.00 | 45.25 |
| 17381 | CG | TYR | C | 657 | -78.849 | -18.536 | 6.805 | 1.00 | 43.24 |

FIGURE 3 MC

| A | B | C | D | E | F | G | H | I | J |
|---|---|---|---|---|---|---|---|---|---|
| 17382 | CD1 | TYR | C | 657 | -78.766 | -17.443 | 7.660 | 1.00 | 41.96 |
| 17383 | CE1 | TYR | C | 657 | -77.898 | -16.411 | 7.404 | 1.00 | 39.72 |
| 17384 | CZ | TYR | C | 657 | -77.112 | -16.464 | 6.282 | 1.00 | 40.47 |
| 17385 | OH | TYR | C | 657 | -76.239 | -15.455 | 5.988 | 1.00 | 41.83 |
| 17386 | CE2 | TYR | C | 657 | -77.187 | -17.533 | 5.425 | 1.00 | 40.94 |
| 17387 | CD2 | TYR | C | 657 | -78.054 | -18.550 | 5.685 | 1.00 | 40.78 |
| 17388 | C | TYR | C | 657 | -80.469 | -21.254 | 8.748 | 1.00 | 45.87 |
| 17389 | O | TYR | C | 657 | -80.565 | -20.961 | 9.930 | 1.00 | 46.43 |
| 17390 | N | ARG | C | 658 | -81.356 | -21.994 | 8.094 | 1.00 | 45.67 |
| 17391 | CA | ARG | C | 658 | -82.578 | -22.486 | 8.710 | 1.00 | 45.95 |
| 17392 | CB | ARG | C | 658 | -83.594 | -22.896 | 7.631 | 1.00 | 46.28 |
| 17393 | CG | ARG | C | 658 | -84.217 | -21.740 | 6.844 | 1.00 | 49.14 |
| 17394 | CD | ARG | C | 658 | -85.595 | -22.064 | 6.211 | 1.00 | 53.51 |
| 17395 | NE | ARG | C | 658 | -85.507 | -23.075 | 5.154 | 1.00 | 56.60 |
| 17396 | CZ | ARG | C | 658 | -86.363 | -23.193 | 4.136 | 1.00 | 57.79 |
| 17397 | NH1 | ARG | C | 658 | -87.397 | -22.363 | 4.020 | 1.00 | 56.87 |
| 17398 | NH2 | ARG | C | 658 | -86.183 | -24.152 | 3.232 | 1.00 | 57.59 |
| 17399 | C | ARG | C | 658 | -82.364 | -23.675 | 9.627 | 1.00 | 45.54 |
| 17400 | O | ARG | C | 658 | -83.191 | -23.934 | 10.508 | 1.00 | 45.95 |
| 17401 | N | ASN | C | 659 | -81.275 | -24.411 | 9.417 | 1.00 | 44.74 |
| 17402 | CA | ASN | C | 659 | -81.036 | -25.635 | 10.176 | 1.00 | 44.08 |
| 17403 | CB | ASN | C | 659 | -80.447 | -26.724 | 9.272 | 1.00 | 44.64 |
| 17404 | CG | ASN | C | 659 | -81.224 | -28.033 | 9.352 | 1.00 | 46.95 |
| 17405 | OD1 | ASN | C | 659 | -82.133 | -28.278 | 8.542 | 1.00 | 49.62 |
| 17406 | ND2 | ASN | C | 659 | -80.877 | -28.882 | 10.327 | 1.00 | 47.89 |
| 17407 | C | ASN | C | 659 | -80.141 | -25.434 | 11.382 | 1.00 | 42.91 |
| 17408 | O | ASN | C | 659 | -79.922 | -26.354 | 12.171 | 1.00 | 42.51 |
| 17409 | N | SER | C | 660 | -79.623 | -24.227 | 11.534 | 1.00 | 41.70 |
| 17410 | CA | SER | C | 660 | -78.737 | -23.962 | 12.648 | 1.00 | 40.66 |
| 17411 | CB | SER | C | 660 | -77.410 | -23.428 | 12.128 | 1.00 | 40.52 |
| 17412 | OG | SER | C | 660 | -77.629 | -22.383 | 11.198 | 1.00 | 40.66 |
| 17413 | C | SER | C | 660 | -79.327 | -23.003 | 13.685 | 1.00 | 40.04 |
| 17414 | O | SER | C | 660 | -78.578 | -22.306 | 14.360 | 1.00 | 39.96 |
| 17415 | N | THR | C | 661 | -80.655 | -22.943 | 13.797 | 1.00 | 39.09 |
| 17416 | CA | THR | C | 661 | -81.268 | -22.085 | 14.811 | 1.00 | 38.03 |
| 17417 | CB | THR | C | 661 | -82.651 | -21.556 | 14.384 | 1.00 | 37.96 |
| 17418 | OG1 | THR | C | 661 | -83.595 | -22.625 | 14.403 | 1.00 | 36.52 |
| 17419 | CG2 | THR | C | 661 | -82.645 | -21.050 | 12.935 | 1.00 | 37.45 |
| 17420 | C | THR | C | 661 | -81.429 | -22.900 | 16.071 | 1.00 | 37.79 |
| 17421 | O | THR | C | 661 | -81.553 | -24.124 | 16.002 | 1.00 | 37.47 |
| 17422 | N | VAL | C | 662 | -81.454 | -22.238 | 17.223 | 1.00 | 37.13 |
| 17423 | CA | VAL | C | 662 | -81.608 | -22.985 | 18.462 | 1.00 | 36.62 |
| 17424 | CB | VAL | C | 662 | -80.973 | -22.272 | 19.710 | 1.00 | 36.83 |
| 17425 | CG1 | VAL | C | 662 | -79.942 | -21.246 | 19.294 | 1.00 | 34.84 |
| 17426 | CG2 | VAL | C | 662 | -82.033 | -21.661 | 20.611 | 1.00 | 35.45 |
| 17427 | C | VAL | C | 662 | -83.070 | -23.278 | 18.691 | 1.00 | 36.93 |
| 17428 | O | VAL | C | 662 | -83.415 | -24.280 | 19.310 | 1.00 | 37.33 |
| 17429 | N | MET | C | 663 | -83.935 | -22.405 | 18.186 | 1.00 | 36.78 |
| 17430 | CA | MET | C | 663 | -85.360 | -22.594 | 18.354 | 1.00 | 36.89 |
| 17431 | CB | MET | C | 663 | -86.158 | -21.560 | 17.547 | 1.00 | 36.76 |
| 17432 | CG | MET | C | 663 | -86.341 | -20.212 | 18.227 | 1.00 | 35.06 |

FIGURE 3 MD

| A | B | C | D | E | F | G | H | I | J |
|---|---|---|---|---|---|---|---|---|---|
| 17433 | SD | MET | C | 663 | -84.846 | -19.194 | 18.177 | 1.00 | 35.84 |
| 17434 | CE | MET | C | 663 | -84.752 | -18.696 | 16.489 | 1.00 | 33.06 |
| 17435 | C | MET | C | 663 | -85.745 | -23.991 | 17.901 | 1.00 | 37.82 |
| 17436 | O | MET | C | 663 | -86.563 | -24.653 | 18.542 | 1.00 | 37.81 |
| 17437 | N | SER | C | 664 | -85.164 | -24.434 | 16.785 | 1.00 | 38.23 |
| 17438 | CA | SER | C | 664 | -85.488 | -25.742 | 16.245 | 1.00 | 38.98 |
| 17439 | CB | SER | C | 664 | -84.933 | -25.914 | 14.823 | 1.00 | 39.11 |
| 17440 | OG | SER | C | 664 | -83.603 | -26.398 | 14.846 | 1.00 | 40.80 |
| 17441 | C | SER | C | 664 | -85.023 | -26.867 | 17.174 | 1.00 | 39.18 |
| 17442 | O | SER | C | 664 | -85.478 | -28.007 | 17.063 | 1.00 | 39.51 |
| 17443 | N | ARG | C | 665 | -84.141 | -26.553 | 18.114 | 1.00 | 39.11 |
| 17444 | CA | ARG | C | 665 | -83.720 | -27.572 | 19.072 | 1.00 | 39.15 |
| 17445 | CB | ARG | C | 665 | -82.228 | -27.470 | 19.368 | 1.00 | 39.15 |
| 17446 | CG | ARG | C | 665 | -81.342 | -27.778 | 18.183 | 1.00 | 40.16 |
| 17447 | CD | ARG | C | 665 | -79.919 | -27.302 | 18.347 | 1.00 | 41.92 |
| 17448 | NE | ARG | C | 665 | -79.079 | -27.770 | 17.256 | 1.00 | 44.94 |
| 17449 | CZ | ARG | C | 665 | -77.992 | -28.514 | 17.413 | 1.00 | 46.14 |
| 17450 | NH1 | ARG | C | 665 | -77.605 | -28.882 | 18.631 | 1.00 | 44.85 |
| 17451 | NH2 | ARG | C | 665 | -77.290 | -28.891 | 16.346 | 1.00 | 47.15 |
| 17452 | C | ARG | C | 665 | -84.509 | -27.516 | 20.382 | 1.00 | 38.90 |
| 17453 | O | ARG | C | 665 | -84.120 | -28.159 | 21.351 | 1.00 | 38.81 |
| 17454 | N | ALA | C | 666 | -85.628 | -26.791 | 20.390 | 1.00 | 38.39 |
| 17455 | CA | ALA | C | 666 | -86.407 | -26.563 | 21.611 | 1.00 | 38.76 |
| 17456 | CB | ALA | C | 666 | -87.659 | -25.746 | 21.305 | 1.00 | 38.34 |
| 17457 | C | ALA | C | 666 | -86.776 | -27.789 | 22.453 | 1.00 | 39.08 |
| 17458 | O | ALA | C | 666 | -86.478 | -27.836 | 23.641 | 1.00 | 38.98 |
| 17459 | N | GLU | C | 667 | -87.440 | -28.760 | 21.836 | 1.00 | 39.50 |
| 17460 | CA | GLU | C | 667 | -87.873 | -29.976 | 22.514 | 1.00 | 40.65 |
| 17461 | CB | GLU | C | 667 | -88.408 | -30.972 | 21.471 | 1.00 | 41.61 |
| 17462 | CG | GLU | C | 667 | -88.745 | -32.358 | 22.006 | 1.00 | 44.39 |
| 17463 | CD | GLU | C | 667 | -90.028 | -32.388 | 22.815 | 1.00 | 48.67 |
| 17464 | OE1 | GLU | C | 667 | -90.139 | -33.247 | 23.720 | 1.00 | 50.22 |
| 17465 | OE2 | GLU | C | 667 | -90.929 | -31.559 | 22.545 | 1.00 | 50.72 |
| 17466 | C | GLU | C | 667 | -86.790 | -30.632 | 23.386 | 1.00 | 40.22 |
| 17467 | O | GLU | C | 667 | -87.086 | -31.230 | 24.414 | 1.00 | 40.14 |
| 17468 | N | ASN | C | 668 | -85.537 | -30.516 | 22.971 | 1.00 | 40.21 |
| 17469 | CA | ASN | C | 668 | -84.435 | -31.109 | 23.713 | 1.00 | 40.53 |
| 17470 | CB | ASN | C | 668 | -83.204 | -31.267 | 22.810 | 1.00 | 40.59 |
| 17471 | CG | ASN | C | 668 | -83.375 | -32.380 | 21.780 | 1.00 | 41.30 |
| 17472 | OD1 | ASN | C | 668 | -84.167 | -33.307 | 21.972 | 1.00 | 41.08 |
| 17473 | ND2 | ASN | C | 668 | -82.626 | -32.296 | 20.683 | 1.00 | 41.87 |
| 17474 | C | ASN | C | 668 | -84.068 | -30.395 | 25.022 | 1.00 | 40.58 |
| 17475 | O | ASN | C | 668 | -83.437 | -30.997 | 25.891 | 1.00 | 40.44 |
| 17476 | N | PHE | C | 669 | -84.473 | -29.132 | 25.182 | 1.00 | 40.23 |
| 17477 | CA | PHE | C | 669 | -84.150 | -28.393 | 26.411 | 1.00 | 39.62 |
| 17478 | CB | PHE | C | 669 | -84.467 | -26.897 | 26.290 | 1.00 | 39.21 |
| 17479 | CG | PHE | C | 669 | -83.445 | -26.097 | 25.512 | 1.00 | 37.04 |
| 17480 | CD1 | PHE | C | 669 | -83.406 | -26.150 | 24.136 | 1.00 | 34.24 |
| 17481 | CE1 | PHE | C | 669 | -82.488 | -25.404 | 23.421 | 1.00 | 33.36 |
| 17482 | CZ | PHE | C | 669 | -81.601 | -24.571 | 24.080 | 1.00 | 33.94 |
| 17483 | CE2 | PHE | C | 669 | -81.641 | -24.493 | 25.464 | 1.00 | 34.78 |

FIGURE 3 ME

| A | B | C | D | E | F | G | H | I | J |
|---|---|---|---|---|---|---|---|---|---|
| 17484 | CD2 | PHE | C | 669 | -82.558 | -25.253 | 26.169 | 1.00 | 35.44 |
| 17485 | C | PHE | C | 669 | -84.881 | -28.965 | 27.617 | 1.00 | 40.05 |
| 17486 | O | PHE | C | 669 | -84.696 | -28.506 | 28.741 | 1.00 | 40.11 |
| 17487 | N | LYS | C | 670 | -85.713 | -29.970 | 27.382 | 1.00 | 40.60 |
| 17488 | CA | LYS | C | 670 | -86.452 | -30.631 | 28.450 | 1.00 | 41.14 |
| 17489 | CB | LYS | C | 670 | -87.490 | -31.589 | 27.861 | 1.00 | 41.62 |
| 17490 | CG | LYS | C | 670 | -88.734 | -30.912 | 27.277 | 1.00 | 43.99 |
| 17491 | CD | LYS | C | 670 | -89.758 | -31.942 | 26.814 | 1.00 | 46.81 |
| 17492 | CE | LYS | C | 670 | -91.001 | -31.283 | 26.206 | 1.00 | 48.27 |
| 17493 | NZ | LYS | C | 670 | -91.853 | -32.250 | 25.435 | 1.00 | 49.01 |
| 17494 | C | LYS | C | 670 | -85.528 | -31.419 | 29.376 | 1.00 | 41.34 |
| 17495 | O | LYS | C | 670 | -85.868 | -31.681 | 30.533 | 1.00 | 41.27 |
| 17496 | N | GLN | C | 671 | -84.367 | -31.817 | 28.871 | 1.00 | 41.18 |
| 17497 | CA | GLN | C | 671 | -83.448 | -32.589 | 29.693 | 1.00 | 41.40 |
| 17498 | CB | GLN | C | 671 | -82.691 | -33.620 | 28.855 | 1.00 | 42.05 |
| 17499 | CG | GLN | C | 671 | -83.356 | -34.066 | 27.565 | 1.00 | 44.40 |
| 17500 | CD | GLN | C | 671 | -82.400 | -34.873 | 26.710 | 1.00 | 47.75 |
| 17501 | OE1 | GLN | C | 671 | -82.691 | -35.160 | 25.549 | 1.00 | 50.22 |
| 17502 | NE2 | GLN | C | 671 | -81.250 | -35.242 | 27.284 | 1.00 | 48.69 |
| 17503 | C | GLN | C | 671 | -82.412 | -31.717 | 30.384 | 1.00 | 40.78 |
| 17504 | O | GLN | C | 671 | -81.516 | -32.236 | 31.045 | 1.00 | 41.50 |
| 17505 | N | VAL | C | 672 | -82.495 | -30.403 | 30.226 | 1.00 | 39.33 |
| 17506 | CA | VAL | C | 672 | -81.478 | -29.549 | 30.833 | 1.00 | 38.19 |
| 17507 | CB | VAL | C | 672 | -80.542 | -28.961 | 29.768 | 1.00 | 38.30 |
| 17508 | CG1 | VAL | C | 672 | -79.882 | -30.075 | 28.934 | 1.00 | 36.38 |
| 17509 | CG2 | VAL | C | 672 | -81.313 | -27.976 | 28.882 | 1.00 | 37.82 |
| 17510 | C | VAL | C | 672 | -82.057 | -28.387 | 31.620 | 1.00 | 37.37 |
| 17511 | O | VAL | C | 672 | -83.206 | -28.031 | 31.442 | 1.00 | 37.61 |
| 17512 | N | GLU | C | 673 | -81.259 | -27.822 | 32.518 | 1.00 | 36.29 |
| 17513 | CA | GLU | C | 673 | -81.635 | -26.591 | 33.205 | 1.00 | 35.13 |
| 17514 | CB | GLU | C | 673 | -81.137 | -26.602 | 34.641 | 1.00 | 35.55 |
| 17515 | CG | GLU | C | 673 | -81.748 | -27.713 | 35.474 | 1.00 | 40.14 |
| 17516 | CD | GLU | C | 673 | -80.782 | -28.223 | 36.524 | 1.00 | 44.05 |
| 17517 | OE1 | GLU | C | 673 | -80.411 | -27.437 | 37.418 | 1.00 | 46.78 |
| 17518 | OE2 | GLU | C | 673 | -80.376 | -29.399 | 36.443 | 1.00 | 46.49 |
| 17519 | C | GLU | C | 673 | -80.975 | -25.457 | 32.426 | 1.00 | 32.91 |
| 17520 | O | GLU | C | 673 | -79.753 | -25.409 | 32.315 | 1.00 | 32.53 |
| 17521 | N | TYR | C | 674 | -81.795 | -24.561 | 31.891 | 1.00 | 30.56 |
| 17522 | CA | TYR | C | 674 | -81.354 | -23.462 | 31.042 | 1.00 | 28.55 |
| 17523 | CB | TYR | C | 674 | -82.203 | -23.496 | 29.777 | 1.00 | 28.68 |
| 17524 | CG | TYR | C | 674 | -81.799 | -22.619 | 28.620 | 1.00 | 27.46 |
| 17525 | CD1 | TYR | C | 674 | -80.477 | -22.501 | 28.220 | 1.00 | 27.52 |
| 17526 | CE1 | TYR | C | 674 | -80.129 | -21.718 | 27.117 | 1.00 | 26.33 |
| 17527 | CZ | TYR | C | 674 | -81.114 | -21.069 | 26.404 | 1.00 | 25.65 |
| 17528 | OH | TYR | C | 674 | -80.791 | -20.293 | 25.309 | 1.00 | 26.32 |
| 17529 | CE2 | TYR | C | 674 | -82.423 | -21.172 | 26.787 | 1.00 | 26.23 |
| 17530 | CD2 | TYR | C | 674 | -82.759 | -21.945 | 27.887 | 1.00 | 28.21 |
| 17531 | C | TYR | C | 674 | -81.584 | -22.108 | 31.674 | 1.00 | 27.22 |
| 17532 | O | TYR | C | 674 | -82.644 | -21.855 | 32.225 | 1.00 | 26.63 |
| 17533 | N | LEU | C | 675 | -80.598 | -21.230 | 31.572 | 1.00 | 26.37 |
| 17534 | CA | LEU | C | 675 | -80.766 | -19.844 | 32.000 | 1.00 | 26.14 |

17535     CB    LEU  C  675    -79.854  -19.479   33.176  1.00  25.90
17536     CG    LEU  C  675    -79.814  -18.010   33.651  1.00  25.75
17537    CD1    LEU  C  675    -81.192  -17.476   34.109  1.00  23.89
17538    CD2    LEU  C  675    -78.801  -17.849   34.762  1.00  23.32
17539     C     LEU  C  675    -80.516  -18.947   30.791  1.00  26.05
17540     O     LEU  C  675    -79.430  -18.948   30.224  1.00  25.78
17541     N     LEU  C  676    -81.551  -18.199   30.414  1.00  25.92
17542     CA    LEU  C  676    -81.547  -17.303   29.263  1.00  26.02
17543     CB    LEU  C  676    -82.843  -17.524   28.471  1.00  25.45
17544     CG    LEU  C  676    -82.988  -16.741   27.177  1.00  25.45
17545    CD1    LEU  C  676    -84.319  -17.043   26.501  1.00  24.33
17546    CD2    LEU  C  676    -81.837  -17.036   26.271  1.00  23.72
17547     C     LEU  C  676    -81.463  -15.830   29.705  1.00  26.01
17548     O     LEU  C  676    -82.329  -15.366   30.429  1.00  26.52
17549     N     ILE  C  677    -80.443  -15.091   29.267  1.00  25.95
17550     CA    ILE  C  677    -80.273  -13.703   29.732  1.00  25.55
17551     CB    ILE  C  677    -79.085  -13.584   30.744  1.00  25.04
17552    CG1    ILE  C  677    -79.263  -14.532   31.939  1.00  24.66
17553    CD1    ILE  C  677    -78.014  -14.600   32.855  1.00  21.13
17554    CG2    ILE  C  677    -78.936  -12.157   31.230  1.00  24.45
17555     C     ILE  C  677    -80.017  -12.749   28.576  1.00  25.74
17556     O     ILE  C  677    -79.213  -13.041   27.708  1.00  26.49
17557     N     HIS  C  678    -80.657  -11.587   28.587  1.00  25.43
17558     CA    HIS  C  678    -80.484  -10.653   27.490  1.00  25.10
17559     CB    HIS  C  678    -81.390  -11.077   26.329  1.00  24.83
17560     CG    HIS  C  678    -80.800  -10.815   24.981  1.00  25.90
17561    ND1    HIS  C  678    -80.685  -11.796   24.018  1.00  25.45
17562    CE1    HIS  C  678    -80.113  -11.291   22.943  1.00  25.72
17563    NE2    HIS  C  678    -79.859  -10.014   23.167  1.00  28.31
17564    CD2    HIS  C  678    -80.283   -9.689   24.436  1.00  26.49
17565     C     HIS  C  678    -80.835   -9.221   27.892  1.00  25.15
17566     O     HIS  C  678    -81.818   -8.990   28.623  1.00  24.65
17567     N     GLY  C  679    -80.041   -8.268   27.398  1.00  25.01
17568     CA    GLY  C  679    -80.289   -6.856   27.617  1.00  25.20
17569     C     GLY  C  679    -81.352   -6.436   26.628  1.00  25.68
17570     O     GLY  C  679    -81.296   -6.852   25.474  1.00  26.27
17571     N     THR  C  680    -82.322   -5.625   27.053  1.00  25.67
17572     CA    THR  C  680    -83.406   -5.219   26.152  1.00  25.30
17573     CB    THR  C  680    -84.598   -4.632   26.924  1.00  25.15
17574    OG1    THR  C  680    -84.156   -3.505   27.700  1.00  27.27
17575    CG2    THR  C  680    -85.109   -5.604   27.952  1.00  23.02
17576     C     THR  C  680    -82.964   -4.206   25.114  1.00  25.68
17577     O     THR  C  680    -83.602   -4.054   24.088  1.00  25.49
17578     N     ALA  C  681    -81.886   -3.493   25.396  1.00  26.40
17579     CA    ALA  C  681    -81.379   -2.484   24.475  1.00  26.65
17580     CB    ALA  C  681    -81.199   -1.160   25.181  1.00  26.53
17581     C     ALA  C  681    -80.078   -2.942   23.815  1.00  26.92
17582     O     ALA  C  681    -79.188   -2.152   23.521  1.00  26.88
17583     N     ASP  C  682    -79.979   -4.238   23.591  1.00  27.70
17584     CA    ASP  C  682    -78.839   -4.781   22.880  1.00  28.44
17585     CB    ASP  C  682    -78.769   -6.280   23.087  1.00  27.96
```

FIGURE 3 MG

| A | B | C | D | E | F | G | H | I | J |
|---|---|---|---|---|---|---|---|---|---|
| 17586 | CG | ASP | C | 682 | -77.418 | -6.859 | 22.733 | 1.00 | 29.07 |
| 17587 | OD1 | ASP | C | 682 | -77.059 | -7.902 | 23.346 | 1.00 | 28.45 |
| 17588 | OD2 | ASP | C | 682 | -76.662 | -6.367 | 21.855 | 1.00 | 28.76 |
| 17589 | C | ASP | C | 682 | -78.996 | -4.442 | 21.391 | 1.00 | 28.76 |
| 17590 | O | ASP | C | 682 | -79.898 | -4.943 | 20.696 | 1.00 | 28.70 |
| 17591 | N | ASP | C | 683 | -78.110 | -3.577 | 20.930 | 1.00 | 28.86 |
| 17592 | CA | ASP | C | 683 | -78.116 | -3.078 | 19.567 | 1.00 | 29.85 |
| 17593 | CB | ASP | C | 683 | -77.472 | -1.694 | 19.577 | 1.00 | 29.46 |
| 17594 | CG | ASP | C | 683 | -76.040 | -1.732 | 20.090 | 1.00 | 30.36 |
| 17595 | OD1 | ASP | C | 683 | -75.831 | -1.561 | 21.316 | 1.00 | 30.25 |
| 17596 | OD2 | ASP | C | 683 | -75.057 | -1.956 | 19.347 | 1.00 | 30.48 |
| 17597 | C | ASP | C | 683 | -77.301 | -3.976 | 18.652 | 1.00 | 30.02 |
| 17598 | O | ASP | C | 683 | -77.297 | -3.794 | 17.437 | 1.00 | 30.19 |
| 17599 | N | ASN | C | 684 | -76.586 | -4.923 | 19.249 | 1.00 | 30.21 |
| 17600 | CA | ASN | C | 684 | -75.705 | -5.821 | 18.516 | 1.00 | 30.64 |
| 17601 | CB | ASN | C | 684 | -74.425 | -6.048 | 19.310 | 1.00 | 31.17 |
| 17602 | CG | ASN | C | 684 | -73.311 | -6.646 | 18.486 | 1.00 | 30.89 |
| 17603 | OD1 | ASN | C | 684 | -72.141 | -6.385 | 18.748 | 1.00 | 34.62 |
| 17604 | ND2 | ASN | C | 684 | -73.655 | -7.450 | 17.504 | 1.00 | 28.71 |
| 17605 | C | ASN | C | 684 | -76.449 | -7.120 | 18.279 | 1.00 | 30.65 |
| 17606 | O | ASN | C | 684 | -76.910 | -7.377 | 17.168 | 1.00 | 31.03 |
| 17607 | N | VAL | C | 685 | -76.561 | -7.954 | 19.308 | 1.00 | 30.46 |
| 17608 | CA | VAL | C | 685 | -77.431 | -9.106 | 19.183 | 1.00 | 29.55 |
| 17609 | CB | VAL | C | 685 | -76.821 | -10.424 | 19.695 | 1.00 | 30.12 |
| 17610 | CG1 | VAL | C | 685 | -75.287 | -10.408 | 19.554 | 1.00 | 28.95 |
| 17611 | CG2 | VAL | C | 685 | -77.222 | -10.686 | 21.089 | 1.00 | 31.47 |
| 17612 | C | VAL | C | 685 | -78.721 | -8.703 | 19.869 | 1.00 | 29.67 |
| 17613 | O | VAL | C | 685 | -78.827 | -8.572 | 21.102 | 1.00 | 29.52 |
| 17614 | N | HIS | C | 686 | -79.703 | -8.459 | 19.019 | 1.00 | 29.13 |
| 17615 | CA | HIS | C | 686 | -80.995 | -7.959 | 19.423 | 1.00 | 28.34 |
| 17616 | CB | HIS | C | 686 | -81.817 | -7.666 | 18.168 | 1.00 | 27.30 |
| 17617 | CG | HIS | C | 686 | -81.095 | -6.768 | 17.212 | 1.00 | 26.65 |
| 17618 | ND1 | HIS | C | 686 | -81.297 | -6.794 | 15.849 | 1.00 | 26.45 |
| 17619 | CE1 | HIS | C | 686 | -80.513 | -5.902 | 15.269 | 1.00 | 24.28 |
| 17620 | NE2 | HIS | C | 686 | -79.800 | -5.307 | 16.207 | 1.00 | 26.49 |
| 17621 | CD2 | HIS | C | 686 | -80.150 | -5.828 | 17.430 | 1.00 | 26.11 |
| 17622 | C | HIS | C | 686 | -81.720 | -8.843 | 20.414 | 1.00 | 27.58 |
| 17623 | O | HIS | C | 686 | -81.643 | -10.053 | 20.341 | 1.00 | 28.29 |
| 17624 | N | PHE | C | 687 | -82.400 | -8.213 | 21.362 | 1.00 | 26.85 |
| 17625 | CA | PHE | C | 687 | -83.188 | -8.934 | 22.350 | 1.00 | 26.05 |
| 17626 | CB | PHE | C | 687 | -83.982 | -7.932 | 23.208 | 1.00 | 25.87 |
| 17627 | CG | PHE | C | 687 | -84.810 | -8.586 | 24.268 | 1.00 | 23.93 |
| 17628 | CD1 | PHE | C | 687 | -84.232 | -8.972 | 25.468 | 1.00 | 23.35 |
| 17629 | CE1 | PHE | C | 687 | -84.968 | -9.601 | 26.438 | 1.00 | 22.69 |
| 17630 | CZ | PHE | C | 687 | -86.301 | -9.861 | 26.217 | 1.00 | 24.49 |
| 17631 | CE2 | PHE | C | 687 | -86.892 | -9.493 | 25.005 | 1.00 | 23.18 |
| 17632 | CD2 | PHE | C | 687 | -86.143 | -8.860 | 24.045 | 1.00 | 20.96 |
| 17633 | C | PHE | C | 687 | -84.124 | -9.928 | 21.655 | 1.00 | 25.82 |
| 17634 | O | PHE | C | 687 | -84.494 | -10.967 | 22.208 | 1.00 | 25.58 |
| 17635 | N | GLN | C | 688 | -84.510 | -9.572 | 20.427 | 1.00 | 26.01 |
| 17636 | CA | GLN | C | 688 | -85.330 | -10.402 | 19.548 | 1.00 | 25.30 |

FIGURE 3 MH

| A | B | C | D | E | F | G | H | I | J |
|---|---|---|---|---|---|---|---|---|---|
| 17637 | CB | GLN | C | 688 | -85.229 | -9.846 | 18.120 | 1.00 | 25.52 |
| 17638 | CG | GLN | C | 688 | -85.657 | -10.801 | 16.992 | 1.00 | 25.68 |
| 17639 | CD | GLN | C | 688 | -85.124 | -10.356 | 15.619 | 1.00 | 28.02 |
| 17640 | OE1 | GLN | C | 688 | -83.984 | -9.922 | 15.503 | 1.00 | 29.89 |
| 17641 | NE2 | GLN | C | 688 | -85.947 | -10.472 | 14.593 | 1.00 | 27.05 |
| 17642 | C | GLN | C | 688 | -84.852 | -11.849 | 19.540 | 1.00 | 25.27 |
| 17643 | O | GLN | C | 688 | -85.654 | -12.780 | 19.593 | 1.00 | 24.54 |
| 17644 | N | GLN | C | 689 | -83.536 | -12.023 | 19.445 | 1.00 | 25.10 |
| 17645 | CA | GLN | C | 689 | -82.945 | -13.359 | 19.370 | 1.00 | 25.76 |
| 17646 | CB | GLN | C | 689 | -81.419 | -13.274 | 19.192 | 1.00 | 24.96 |
| 17647 | CG | GLN | C | 689 | -81.019 | -12.322 | 18.067 | 1.00 | 25.21 |
| 17648 | CD | GLN | C | 689 | -80.000 | -12.901 | 17.089 | 1.00 | 25.38 |
| 17649 | OE1 | GLN | C | 689 | -79.153 | -12.171 | 16.570 | 1.00 | 27.69 |
| 17650 | NE2 | GLN | C | 689 | -80.099 | -14.182 | 16.816 | 1.00 | 20.61 |
| 17651 | C | GLN | C | 689 | -83.311 | -14.251 | 20.559 | 1.00 | 26.02 |
| 17652 | O | GLN | C | 689 | -83.661 | -15.408 | 20.368 | 1.00 | 26.06 |
| 17653 | N | SER | C | 690 | -83.217 | -13.718 | 21.779 | 1.00 | 26.14 |
| 17654 | CA | SER | C | 690 | -83.577 | -14.484 | 22.962 | 1.00 | 26.18 |
| 17655 | CB | SER | C | 690 | -82.993 | -13.857 | 24.225 | 1.00 | 26.51 |
| 17656 | OG | SER | C | 690 | -81.621 | -14.170 | 24.368 | 1.00 | 28.14 |
| 17657 | C | SER | C | 690 | -85.090 | -14.513 | 23.085 | 1.00 | 26.21 |
| 17658 | O | SER | C | 690 | -85.655 | -15.447 | 23.665 | 1.00 | 26.92 |
| 17659 | N | ALA | C | 691 | -85.750 | -13.481 | 22.565 | 1.00 | 25.38 |
| 17660 | CA | ALA | C | 691 | -87.203 | -13.466 | 22.609 | 1.00 | 25.80 |
| 17661 | CB | ALA | C | 691 | -87.771 | -12.131 | 22.083 | 1.00 | 25.47 |
| 17662 | C | ALA | C | 691 | -87.757 | -14.626 | 21.794 | 1.00 | 26.13 |
| 17663 | O | ALA | C | 691 | -88.828 | -15.138 | 22.104 | 1.00 | 25.66 |
| 17664 | N | GLN | C | 692 | -87.040 | -15.014 | 20.737 | 1.00 | 26.50 |
| 17665 | CA | GLN | C | 692 | -87.507 | -16.121 | 19.890 | 1.00 | 27.59 |
| 17666 | CB | GLN | C | 692 | -86.966 | -16.053 | 18.447 | 1.00 | 27.83 |
| 17667 | CG | GLN | C | 692 | -87.450 | -14.848 | 17.606 | 1.00 | 28.11 |
| 17668 | CD | GLN | C | 692 | -88.916 | -14.910 | 17.205 | 1.00 | 29.70 |
| 17669 | OE1 | GLN | C | 692 | -89.616 | -15.847 | 17.555 | 1.00 | 32.56 |
| 17670 | NE2 | GLN | C | 692 | -89.381 | -13.900 | 16.452 | 1.00 | 30.95 |
| 17671 | C | GLN | C | 692 | -87.158 | -17.447 | 20.520 | 1.00 | 27.38 |
| 17672 | O | GLN | C | 692 | -87.885 | -18.403 | 20.354 | 1.00 | 27.47 |
| 17673 | N | ILE | C | 693 | -86.053 | -17.503 | 21.255 | 1.00 | 27.61 |
| 17674 | CA | ILE | C | 693 | -85.713 | -18.725 | 21.963 | 1.00 | 27.65 |
| 17675 | CB | ILE | C | 693 | -84.362 | -18.585 | 22.673 | 1.00 | 27.94 |
| 17676 | CG1 | ILE | C | 693 | -83.261 | -18.320 | 21.663 | 1.00 | 28.29 |
| 17677 | CD1 | ILE | C | 693 | -81.881 | -18.316 | 22.267 | 1.00 | 28.15 |
| 17678 | CG2 | ILE | C | 693 | -84.046 | -19.841 | 23.471 | 1.00 | 27.85 |
| 17679 | C | ILE | C | 693 | -86.795 | -18.969 | 22.996 | 1.00 | 27.38 |
| 17680 | O | ILE | C | 693 | -87.400 | -20.036 | 23.049 | 1.00 | 27.53 |
| 17681 | N | SER | C | 694 | -87.078 | -17.954 | 23.804 | 1.00 | 27.00 |
| 17682 | CA | SER | C | 694 | -88.065 | -18.136 | 24.858 | 1.00 | 26.27 |
| 17683 | CB | SER | C | 694 | -88.193 | -16.873 | 25.705 | 1.00 | 26.31 |
| 17684 | OG | SER | C | 694 | -88.964 | -15.889 | 25.035 | 1.00 | 26.46 |
| 17685 | C | SER | C | 694 | -89.419 | -18.542 | 24.273 | 1.00 | 25.86 |
| 17686 | O | SER | C | 694 | -90.097 | -19.421 | 24.806 | 1.00 | 24.83 |
| 17687 | N | LYS | C | 695 | -89.825 | -17.897 | 23.185 | 1.00 | 25.80 |

FIGURE 3 MI

| A | B | C | D | E | F | G | H | I | J |
|---|---|---|---|---|---|---|---|---|---|
| 17688 | CA | LYS | C | 695 | -91.109 | -18.256 | 22.587 | 1.00 | 26.44 |
| 17689 | CB | LYS | C | 695 | -91.500 | -17.304 | 21.459 | 1.00 | 25.78 |
| 17690 | CG | LYS | C | 695 | -92.907 | -17.555 | 20.937 | 1.00 | 25.78 |
| 17691 | CD | LYS | C | 695 | -93.483 | -16.335 | 20.241 | 1.00 | 24.53 |
| 17692 | CE | LYS | C | 695 | -92.450 | -15.682 | 19.306 | 1.00 | 26.21 |
| 17693 | NZ | LYS | C | 695 | -92.287 | -16.427 | 18.002 | 1.00 | 26.98 |
| 17694 | C | LYS | C | 695 | -91.083 | -19.721 | 22.121 | 1.00 | 27.05 |
| 17695 | O | LYS | C | 695 | -91.994 | -20.476 | 22.388 | 1.00 | 26.52 |
| 17696 | N | ALA | C | 696 | -90.006 | -20.126 | 21.462 | 1.00 | 28.36 |
| 17697 | CA | ALA | C | 696 | -89.865 | -21.514 | 21.061 | 1.00 | 29.59 |
| 17698 | CB | ALA | C | 696 | -88.533 | -21.722 | 20.366 | 1.00 | 29.41 |
| 17699 | C | ALA | C | 696 | -90.000 | -22.472 | 22.255 | 1.00 | 30.35 |
| 17700 | O | ALA | C | 696 | -90.708 | -23.468 | 22.181 | 1.00 | 31.17 |
| 17701 | N | LEU | C | 697 | -89.337 | -22.165 | 23.362 | 1.00 | 30.96 |
| 17702 | CA | LEU | C | 697 | -89.378 | -23.047 | 24.526 | 1.00 | 31.34 |
| 17703 | CB | LEU | C | 697 | -88.329 | -22.621 | 25.552 | 1.00 | 31.32 |
| 17704 | CG | LEU | C | 697 | -86.858 | -22.719 | 25.121 | 1.00 | 31.13 |
| 17705 | CD1 | LEU | C | 697 | -85.926 | -22.158 | 26.197 | 1.00 | 31.53 |
| 17706 | CD2 | LEU | C | 697 | -86.500 | -24.153 | 24.871 | 1.00 | 31.83 |
| 17707 | C | LEU | C | 697 | -90.767 | -23.139 | 25.167 | 1.00 | 31.83 |
| 17708 | O | LEU | C | 697 | -91.170 | -24.196 | 25.664 | 1.00 | 31.72 |
| 17709 | N | VAL | C | 698 | -91.498 | -22.030 | 25.164 | 1.00 | 32.33 |
| 17710 | CA | VAL | C | 698 | -92.842 | -22.016 | 25.718 | 1.00 | 32.77 |
| 17711 | CB | VAL | C | 698 | -93.420 | -20.600 | 25.686 | 1.00 | 32.93 |
| 17712 | CG1 | VAL | C | 698 | -94.941 | -20.627 | 25.869 | 1.00 | 31.70 |
| 17713 | CG2 | VAL | C | 698 | -92.732 | -19.714 | 26.746 | 1.00 | 33.84 |
| 17714 | C | VAL | C | 698 | -93.731 | -22.908 | 24.858 | 1.00 | 33.39 |
| 17715 | O | VAL | C | 698 | -94.497 | -23.747 | 25.354 | 1.00 | 32.98 |
| 17716 | N | ASP | C | 699 | -93.612 | -22.709 | 23.553 | 1.00 | 33.72 |
| 17717 | CA | ASP | C | 699 | -94.399 | -23.454 | 22.596 | 1.00 | 34.90 |
| 17718 | CB | ASP | C | 699 | -94.157 | -22.922 | 21.178 | 1.00 | 34.75 |
| 17719 | CG | ASP | C | 699 | -94.846 | -21.577 | 20.955 | 1.00 | 35.90 |
| 17720 | OD1 | ASP | C | 699 | -94.559 | -20.876 | 19.952 | 1.00 | 35.34 |
| 17721 | OD2 | ASP | C | 699 | -95.703 | -21.144 | 21.765 | 1.00 | 36.30 |
| 17722 | C | ASP | C | 699 | -94.241 | -24.976 | 22.715 | 1.00 | 35.14 |
| 17723 | O | ASP | C | 699 | -95.145 | -25.710 | 22.348 | 1.00 | 35.87 |
| 17724 | N | VAL | C | 700 | -93.126 | -25.456 | 23.263 | 1.00 | 35.25 |
| 17725 | CA | VAL | C | 700 | -92.996 | -26.895 | 23.462 | 1.00 | 35.16 |
| 17726 | CB | VAL | C | 700 | -91.711 | -27.475 | 22.851 | 1.00 | 35.42 |
| 17727 | CG1 | VAL | C | 700 | -91.681 | -27.247 | 21.332 | 1.00 | 35.45 |
| 17728 | CG2 | VAL | C | 700 | -90.500 | -26.889 | 23.517 | 1.00 | 35.54 |
| 17729 | C | VAL | C | 700 | -93.087 | -27.310 | 24.922 | 1.00 | 34.88 |
| 17730 | O | VAL | C | 700 | -92.844 | -28.472 | 25.253 | 1.00 | 35.23 |
| 17731 | N | GLY | C | 701 | -93.427 | -26.369 | 25.797 | 1.00 | 34.29 |
| 17732 | CA | GLY | C | 701 | -93.599 | -26.667 | 27.209 | 1.00 | 33.43 |
| 17733 | C | GLY | C | 701 | -92.340 | -26.962 | 28.011 | 1.00 | 33.58 |
| 17734 | O | GLY | C | 701 | -92.350 | -27.800 | 28.909 | 1.00 | 33.64 |
| 17735 | N | VAL | C | 702 | -91.239 | -26.285 | 27.719 | 1.00 | 33.38 |
| 17736 | CA | VAL | C | 702 | -90.047 | -26.548 | 28.504 | 1.00 | 33.15 |
| 17737 | CB | VAL | C | 702 | -88.798 | -26.788 | 27.635 | 1.00 | 33.65 |
| 17738 | CG1 | VAL | C | 702 | -88.959 | -26.133 | 26.305 | 1.00 | 33.89 |

FIGURE 3 MJ

| A | B | C | D | E | F | G | H | I | J |
|---|---|---|---|---|---|---|---|---|---|
| 17739 | CG2 | VAL | C | 702 | -87.524 | -26.329 | 28.350 | 1.00 | 32.46 |
| 17740 | C | VAL | C | 702 | -89.804 | -25.426 | 29.455 | 1.00 | 32.77 |
| 17741 | O | VAL | C | 702 | -89.693 | -24.278 | 29.047 | 1.00 | 33.10 |
| 17742 | N | ASP | C | 703 | -89.769 | -25.758 | 30.735 | 1.00 | 32.24 |
| 17743 | CA | ASP | C | 703 | -89.481 | -24.775 | 31.743 | 1.00 | 31.92 |
| 17744 | CB | ASP | C | 703 | -89.839 | -25.293 | 33.128 | 1.00 | 32.34 |
| 17745 | CG | ASP | C | 703 | -89.866 | -24.176 | 34.157 | 1.00 | 33.18 |
| 17746 | OD1 | ASP | C | 703 | -89.185 | -24.287 | 35.188 | 1.00 | 35.21 |
| 17747 | OD2 | ASP | C | 703 | -90.527 | -23.137 | 33.996 | 1.00 | 32.34 |
| 17748 | C | ASP | C | 703 | -88.003 | -24.443 | 31.699 | 1.00 | 31.72 |
| 17749 | O | ASP | C | 703 | -87.171 | -25.328 | 31.441 | 1.00 | 31.69 |
| 17750 | N | PHE | C | 704 | -87.686 | -23.180 | 31.977 | 1.00 | 30.47 |
| 17751 | CA | PHE | C | 704 | -86.319 | -22.671 | 31.956 | 1.00 | 29.79 |
| 17752 | CB | PHE | C | 704 | -85.893 | -22.354 | 30.526 | 1.00 | 29.50 |
| 17753 | CG | PHE | C | 704 | -86.694 | -21.234 | 29.895 | 1.00 | 29.13 |
| 17754 | CD1 | PHE | C | 704 | -86.176 | -19.959 | 29.809 | 1.00 | 28.22 |
| 17755 | CE1 | PHE | C | 704 | -86.924 | -18.908 | 29.241 | 1.00 | 29.08 |
| 17756 | CZ | PHE | C | 704 | -88.201 | -19.140 | 28.772 | 1.00 | 28.41 |
| 17757 | CE2 | PHE | C | 704 | -88.733 | -20.426 | 28.854 | 1.00 | 29.66 |
| 17758 | CD2 | PHE | C | 704 | -87.980 | -21.460 | 29.425 | 1.00 | 29.03 |
| 17759 | C | PHE | C | 704 | -86.316 | -21.374 | 32.767 | 1.00 | 30.00 |
| 17760 | O | PHE | C | 704 | -87.365 | -20.923 | 33.225 | 1.00 | 30.00 |
| 17761 | N | GLN | C | 705 | -85.151 | -20.765 | 32.942 | 1.00 | 29.66 |
| 17762 | CA | GLN | C | 705 | -85.083 | -19.532 | 33.706 | 1.00 | 30.04 |
| 17763 | CB | GLN | C | 705 | -84.028 | -19.633 | 34.797 | 1.00 | 30.23 |
| 17764 | CG | GLN | C | 705 | -84.073 | -20.898 | 35.599 | 1.00 | 33.52 |
| 17765 | CD | GLN | C | 705 | -85.252 | -20.943 | 36.513 | 1.00 | 38.13 |
| 17766 | OE1 | GLN | C | 705 | -85.556 | -19.950 | 37.174 | 1.00 | 41.13 |
| 17767 | NE2 | GLN | C | 705 | -85.929 | -22.095 | 36.569 | 1.00 | 39.09 |
| 17768 | C | GLN | C | 705 | -84.693 | -18.412 | 32.780 | 1.00 | 29.39 |
| 17769 | O | GLN | C | 705 | -83.908 | -18.613 | 31.857 | 1.00 | 29.61 |
| 17770 | N | ALA | C | 706 | -85.225 | -17.223 | 33.040 | 1.00 | 28.88 |
| 17771 | CA | ALA | C | 706 | -84.885 | -16.062 | 32.231 | 1.00 | 27.87 |
| 17772 | CB | ALA | C | 706 | -86.051 | -15.688 | 31.325 | 1.00 | 27.66 |
| 17773 | C | ALA | C | 706 | -84.516 | -14.877 | 33.085 | 1.00 | 26.99 |
| 17774 | O | ALA | C | 706 | -84.879 | -14.800 | 34.252 | 1.00 | 27.04 |
| 17775 | N | MET | C | 707 | -83.794 | -13.947 | 32.480 | 1.00 | 26.11 |
| 17776 | CA | MET | C | 707 | -83.530 | -12.656 | 33.099 | 1.00 | 25.44 |
| 17777 | CB | MET | C | 707 | -82.276 | -12.693 | 33.961 | 1.00 | 25.00 |
| 17778 | CG | MET | C | 707 | -81.984 | -11.399 | 34.675 | 1.00 | 25.79 |
| 17779 | SD | MET | C | 707 | -83.350 | -10.765 | 35.649 | 1.00 | 26.16 |
| 17780 | CE | MET | C | 707 | -83.436 | -11.896 | 37.012 | 1.00 | 26.20 |
| 17781 | C | MET | C | 707 | -83.356 | -11.674 | 31.960 | 1.00 | 24.58 |
| 17782 | O | MET | C | 707 | -82.564 | -11.919 | 31.055 | 1.00 | 25.30 |
| 17783 | N | TRP | C | 708 | -84.147 | -10.613 | 31.948 | 1.00 | 23.19 |
| 17784 | CA | TRP | C | 708 | -83.934 | -9.580 | 30.966 | 1.00 | 22.70 |
| 17785 | CB | TRP | C | 708 | -85.261 | -9.058 | 30.368 | 1.00 | 22.20 |
| 17786 | CG | TRP | C | 708 | -86.096 | -8.244 | 31.314 | 1.00 | 21.68 |
| 17787 | CD1 | TRP | C | 708 | -85.885 | -6.947 | 31.694 | 1.00 | 22.05 |
| 17788 | NE1 | TRP | C | 708 | -86.843 | -6.559 | 32.600 | 1.00 | 21.32 |
| 17789 | CE2 | TRP | C | 708 | -87.702 | -7.605 | 32.814 | 1.00 | 21.26 |

FIGURE 3 MK

| A | B | C | D | E | F | G | H | I | J |
|---|---|---|---|---|---|---|---|---|---|
| 17790 | CD2 | TRP | C | 708 | -87.268 | -8.676 | 32.021 | 1.00 | 21.80 |
| 17791 | CE3 | TRP | C | 708 | -87.985 | -9.882 | 32.081 | 1.00 | 22.63 |
| 17792 | CZ3 | TRP | C | 708 | -89.088 | -9.965 | 32.904 | 1.00 | 20.42 |
| 17793 | CH2 | TRP | C | 708 | -89.503 | -8.880 | 33.651 | 1.00 | 21.01 |
| 17794 | CZ2 | TRP | C | 708 | -88.829 | -7.687 | 33.617 | 1.00 | 21.36 |
| 17795 | C | TRP | C | 708 | -83.229 | -8.493 | 31.750 | 1.00 | 22.73 |
| 17796 | O | TRP | C | 708 | -83.390 | -8.421 | 32.977 | 1.00 | 22.31 |
| 17797 | N | TYR | C | 709 | -82.421 | -7.687 | 31.074 | 1.00 | 22.44 |
| 17798 | CA | TYR | C | 709 | -81.810 | -6.522 | 31.729 | 1.00 | 23.23 |
| 17799 | CB | TYR | C | 709 | -80.284 | -6.642 | 31.842 | 1.00 | 22.71 |
| 17800 | CG | TYR | C | 709 | -79.877 | -7.542 | 33.000 | 1.00 | 23.98 |
| 17801 | CD1 | TYR | C | 709 | -79.779 | -7.046 | 34.305 | 1.00 | 24.20 |
| 17802 | CE1 | TYR | C | 709 | -79.423 | -7.880 | 35.368 | 1.00 | 23.62 |
| 17803 | CZ | TYR | C | 709 | -79.190 | -9.216 | 35.126 | 1.00 | 24.37 |
| 17804 | OH | TYR | C | 709 | -78.840 | -10.061 | 36.143 | 1.00 | 25.39 |
| 17805 | CE2 | TYR | C | 709 | -79.279 | -9.717 | 33.851 | 1.00 | 24.05 |
| 17806 | CD2 | TYR | C | 709 | -79.628 | -8.885 | 32.800 | 1.00 | 23.27 |
| 17807 | C | TYR | C | 709 | -82.261 | -5.221 | 31.061 | 1.00 | 23.07 |
| 17808 | O | TYR | C | 709 | -81.802 | -4.854 | 29.972 | 1.00 | 23.48 |
| 17809 | N | THR | C | 710 | -83.185 | -4.543 | 31.713 | 1.00 | 23.18 |
| 17810 | CA | THR | C | 710 | -83.740 | -3.310 | 31.172 | 1.00 | 23.50 |
| 17811 | CB | THR | C | 710 | -84.575 | -2.617 | 32.218 | 1.00 | 23.16 |
| 17812 | OG1 | THR | C | 710 | -85.625 | -3.490 | 32.656 | 1.00 | 22.78 |
| 17813 | CG2 | THR | C | 710 | -85.289 | -1.428 | 31.594 | 1.00 | 22.97 |
| 17814 | C | THR | C | 710 | -82.662 | -2.325 | 30.732 | 1.00 | 24.18 |
| 17815 | O | THR | C | 710 | -81.822 | -1.929 | 31.543 | 1.00 | 23.64 |
| 17816 | N | ASP | C | 711 | -82.702 | -1.941 | 29.452 | 1.00 | 24.46 |
| 17817 | CA | ASP | C | 711 | -81.825 | -0.904 | 28.903 | 1.00 | 24.95 |
| 17818 | CB | ASP | C | 711 | -82.046 | 0.427 | 29.611 | 1.00 | 25.38 |
| 17819 | CG | ASP | C | 711 | -83.420 | 1.020 | 29.321 | 1.00 | 25.45 |
| 17820 | OD1 | ASP | C | 711 | -83.787 | 2.039 | 29.948 | 1.00 | 25.43 |
| 17821 | OD2 | ASP | C | 711 | -84.191 | 0.526 | 28.481 | 1.00 | 24.04 |
| 17822 | C | ASP | C | 711 | -80.334 | -1.209 | 28.849 | 1.00 | 25.77 |
| 17823 | O | ASP | C | 711 | -79.517 | -0.303 | 28.624 | 1.00 | 25.57 |
| 17824 | N | GLU | C | 712 | -79.963 | -2.466 | 29.077 | 1.00 | 26.14 |
| 17825 | CA | GLU | C | 712 | -78.567 | -2.830 | 28.956 | 1.00 | 26.35 |
| 17826 | CB | GLU | C | 712 | -78.214 | -3.959 | 29.921 | 1.00 | 26.53 |
| 17827 | CG | GLU | C | 712 | -78.190 | -3.542 | 31.385 | 1.00 | 27.05 |
| 17828 | CD | GLU | C | 712 | -77.122 | -2.507 | 31.678 | 1.00 | 27.01 |
| 17829 | OE1 | GLU | C | 712 | -77.472 | -1.366 | 32.024 | 1.00 | 28.43 |
| 17830 | OE2 | GLU | C | 712 | -75.928 | -2.824 | 31.546 | 1.00 | 28.74 |
| 17831 | C | GLU | C | 712 | -78.309 | -3.256 | 27.512 | 1.00 | 26.60 |
| 17832 | O | GLU | C | 712 | -79.199 | -3.769 | 26.852 | 1.00 | 26.39 |
| 17833 | N | ASP | C | 713 | -77.097 | -3.011 | 27.022 | 1.00 | 27.38 |
| 17834 | CA | ASP | C | 713 | -76.722 | -3.453 | 25.697 | 1.00 | 27.89 |
| 17835 | CB | ASP | C | 713 | -75.939 | -2.383 | 24.925 | 1.00 | 27.56 |
| 17836 | CG | ASP | C | 713 | -74.608 | -2.075 | 25.537 | 1.00 | 29.75 |
| 17837 | OD1 | ASP | C | 713 | -74.141 | -0.940 | 25.322 | 1.00 | 30.11 |
| 17838 | OD2 | ASP | C | 713 | -73.951 | -2.892 | 26.239 | 1.00 | 31.92 |
| 17839 | C | ASP | C | 713 | -75.958 | -4.768 | 25.788 | 1.00 | 28.33 |
| 17840 | O | ASP | C | 713 | -75.948 | -5.418 | 26.828 | 1.00 | 28.12 |

FIGURE 3 ML

| A | B | C | D | E | F | G | H | I | J |
|---|---|---|---|---|---|---|---|---|---|
| 17841 | N | HIS | C | 714 | -75.318 | -5.146 | 24.689 | 1.00 | 28.83 |
| 17842 | CA | HIS | C | 714 | -74.668 | -6.444 | 24.576 | 1.00 | 28.96 |
| 17843 | CB | HIS | C | 714 | -74.001 | -6.578 | 23.222 | 1.00 | 28.89 |
| 17844 | CG | HIS | C | 714 | -73.825 | -7.994 | 22.791 | 1.00 | 29.25 |
| 17845 | ND1 | HIS | C | 714 | -74.833 | -8.923 | 22.886 | 1.00 | 28.93 |
| 17846 | CE1 | HIS | C | 714 | -74.395 | -10.089 | 22.445 | 1.00 | 30.34 |
| 17847 | NE2 | HIS | C | 714 | -73.142 | -9.943 | 22.054 | 1.00 | 29.84 |
| 17848 | CD2 | HIS | C | 714 | -72.756 | -8.645 | 22.275 | 1.00 | 29.24 |
| 17849 | C | HIS | C | 714 | -73.656 | -6.746 | 25.653 | 1.00 | 28.97 |
| 17850 | O | HIS | C | 714 | -73.418 | -7.907 | 25.980 | 1.00 | 28.89 |
| 17851 | N | GLY | C | 715 | -73.041 | -5.702 | 26.189 | 1.00 | 29.24 |
| 17852 | CA | GLY | C | 715 | -72.060 | -5.883 | 27.236 | 1.00 | 29.03 |
| 17853 | C | GLY | C | 715 | -72.655 | -6.055 | 28.631 | 1.00 | 28.99 |
| 17854 | O | GLY | C | 715 | -71.976 | -6.593 | 29.506 | 1.00 | 29.44 |
| 17855 | N | ILE | C | 716 | -73.906 | -5.627 | 28.832 | 1.00 | 28.74 |
| 17856 | CA | ILE | C | 716 | -74.546 | -5.643 | 30.150 | 1.00 | 28.60 |
| 17857 | CB | ILE | C | 716 | -75.097 | -7.061 | 30.482 | 1.00 | 28.61 |
| 17858 | CG1 | ILE | C | 716 | -76.012 | -7.553 | 29.352 | 1.00 | 27.50 |
| 17859 | CD1 | ILE | C | 716 | -76.567 | -8.976 | 29.526 | 1.00 | 24.05 |
| 17860 | CG2 | ILE | C | 716 | -75.850 | -7.081 | 31.828 | 1.00 | 27.56 |
| 17861 | C | ILE | C | 716 | -73.488 | -5.180 | 31.155 | 1.00 | 29.55 |
| 17862 | O | ILE | C | 716 | -73.229 | -5.844 | 32.162 | 1.00 | 29.67 |
| 17863 | N | ALA | C | 717 | -72.888 | -4.028 | 30.859 | 1.00 | 30.13 |
| 17864 | CA | ALA | C | 717 | -71.721 | -3.519 | 31.579 | 1.00 | 30.84 |
| 17865 | CB | ALA | C | 717 | -70.617 | -3.146 | 30.601 | 1.00 | 32.01 |
| 17866 | C | ALA | C | 717 | -71.929 | -2.365 | 32.515 | 1.00 | 31.09 |
| 17867 | O | ALA | C | 717 | -70.972 | -1.892 | 33.079 | 1.00 | 30.83 |
| 17868 | N | SER | C | 718 | -73.148 | -1.867 | 32.655 | 1.00 | 31.83 |
| 17869 | CA | SER | C | 718 | -73.378 | -0.873 | 33.679 | 1.00 | 32.40 |
| 17870 | CB | SER | C | 718 | -74.872 | -0.600 | 33.812 | 1.00 | 32.62 |
| 17871 | OG | SER | C | 718 | -75.432 | -0.369 | 32.525 | 1.00 | 36.75 |
| 17872 | C | SER | C | 718 | -72.862 | -1.516 | 34.967 | 1.00 | 32.11 |
| 17873 | O | SER | C | 718 | -72.781 | -2.734 | 35.070 | 1.00 | 32.36 |
| 17874 | N | SER | C | 719 | -72.544 | -0.697 | 35.953 | 1.00 | 31.52 |
| 17875 | CA | SER | C | 719 | -72.051 | -1.187 | 37.220 | 1.00 | 31.73 |
| 17876 | CB | SER | C | 719 | -71.735 | -0.003 | 38.137 | 1.00 | 31.98 |
| 17877 | OG | SER | C | 719 | -70.603 | -0.283 | 38.913 | 1.00 | 33.29 |
| 17878 | C | SER | C | 719 | -73.044 | -2.107 | 37.920 | 1.00 | 30.80 |
| 17879 | O | SER | C | 719 | -72.718 | -3.211 | 38.321 | 1.00 | 30.97 |
| 17880 | N | THR | C | 720 | -74.268 | -1.647 | 38.072 | 1.00 | 30.15 |
| 17881 | CA | THR | C | 720 | -75.241 | -2.431 | 38.805 | 1.00 | 29.08 |
| 17882 | CB | THR | C | 720 | -76.425 | -1.559 | 39.178 | 1.00 | 28.68 |
| 17883 | OG1 | THR | C | 720 | -76.876 | -0.883 | 38.011 | 1.00 | 29.40 |
| 17884 | CG2 | THR | C | 720 | -75.951 | -0.421 | 40.044 | 1.00 | 28.86 |
| 17885 | C | THR | C | 720 | -75.682 | -3.669 | 38.048 | 1.00 | 28.58 |
| 17886 | O | THR | C | 720 | -75.903 | -4.717 | 38.656 | 1.00 | 28.42 |
| 17887 | N | ALA | C | 721 | -75.796 | -3.576 | 36.728 | 1.00 | 27.86 |
| 17888 | CA | ALA | C | 721 | -76.220 | -4.752 | 35.969 | 1.00 | 27.51 |
| 17889 | CB | ALA | C | 721 | -76.701 | -4.383 | 34.573 | 1.00 | 26.20 |
| 17890 | C | ALA | C | 721 | -75.134 | -5.826 | 35.929 | 1.00 | 27.48 |
| 17891 | O | ALA | C | 721 | -75.423 | -7.014 | 36.031 | 1.00 | 27.71 |

FIGURE 3 MM

| A | B | C | D | E | F | G | H | I | J |
|---|---|---|---|---|---|---|---|---|---|
| 17892 | N | HIS | C | 722 | -73.884 | -5.399 | 35.804 | 1.00 | 27.93 |
| 17893 | CA | HIS | C | 722 | -72.759 | -6.323 | 35.762 | 1.00 | 28.17 |
| 17894 | CB | HIS | C | 722 | -71.460 | -5.543 | 35.564 | 1.00 | 28.11 |
| 17895 | CG | HIS | C | 722 | -70.221 | -6.339 | 35.837 | 1.00 | 27.63 |
| 17896 | ND1 | HIS | C | 722 | -69.750 | -7.304 | 34.975 | 1.00 | 28.33 |
| 17897 | CE1 | HIS | C | 722 | -68.646 | -7.830 | 35.471 | 1.00 | 28.63 |
| 17898 | NE2 | HIS | C | 722 | -68.389 | -7.247 | 36.628 | 1.00 | 26.63 |
| 17899 | CD2 | HIS | C | 722 | -69.354 | -6.306 | 36.875 | 1.00 | 26.02 |
| 17900 | C | HIS | C | 722 | -72.701 | -7.128 | 37.058 | 1.00 | 28.52 |
| 17901 | O | HIS | C | 722 | -72.442 | -8.324 | 37.050 | 1.00 | 29.60 |
| 17902 | N | GLN | C | 723 | -72.954 | -6.470 | 38.176 | 1.00 | 28.29 |
| 17903 | CA | GLN | C | 723 | -72.929 | -7.149 | 39.455 | 1.00 | 27.90 |
| 17904 | CB | GLN | C | 723 | -72.910 | -6.117 | 40.584 | 1.00 | 28.20 |
| 17905 | CG | GLN | C | 723 | -71.681 | -5.219 | 40.515 | 1.00 | 29.47 |
| 17906 | CD | GLN | C | 723 | -71.570 | -4.211 | 41.657 | 1.00 | 31.92 |
| 17907 | OE1 | GLN | C | 723 | -71.558 | -4.583 | 42.829 | 1.00 | 35.27 |
| 17908 | NE2 | GLN | C | 723 | -71.454 | -2.941 | 41.309 | 1.00 | 31.36 |
| 17909 | C | GLN | C | 723 | -74.119 | -8.113 | 39.556 | 1.00 | 27.19 |
| 17910 | O | GLN | C | 723 | -73.969 | -9.253 | 39.991 | 1.00 | 26.28 |
| 17911 | N | HIS | C | 724 | -75.283 | -7.651 | 39.110 | 1.00 | 26.35 |
| 17912 | CA | HIS | C | 724 | -76.505 | -8.445 | 39.140 | 1.00 | 25.52 |
| 17913 | CB | HIS | C | 724 | -77.701 | -7.599 | 38.709 | 1.00 | 25.20 |
| 17914 | CG | HIS | C | 724 | -79.023 | -8.157 | 39.137 | 1.00 | 22.05 |
| 17915 | ND1 | HIS | C | 724 | -79.711 | -9.096 | 38.397 | 1.00 | 20.91 |
| 17916 | CE1 | HIS | C | 724 | -80.844 | -9.392 | 39.008 | 1.00 | 19.99 |
| 17917 | NE2 | HIS | C | 724 | -80.909 | -8.687 | 40.127 | 1.00 | 20.84 |
| 17918 | CD2 | HIS | C | 724 | -79.781 | -7.910 | 40.230 | 1.00 | 19.60 |
| 17919 | C | HIS | C | 724 | -76.461 | -9.691 | 38.265 | 1.00 | 26.07 |
| 17920 | O | HIS | C | 724 | -76.941 | -10.749 | 38.656 | 1.00 | 26.47 |
| 17921 | N | ILE | C | 725 | -75.896 | -9.582 | 37.073 | 1.00 | 26.44 |
| 17922 | CA | ILE | C | 725 | -75.903 | -10.737 | 36.192 | 1.00 | 25.82 |
| 17923 | CB | ILE | C | 725 | -75.534 | -10.358 | 34.755 | 1.00 | 25.39 |
| 17924 | CG1 | ILE | C | 725 | -75.616 | -11.601 | 33.850 | 1.00 | 24.74 |
| 17925 | CD1 | ILE | C | 725 | -75.653 | -11.305 | 32.353 | 1.00 | 19.42 |
| 17926 | CG2 | ILE | C | 725 | -74.155 | -9.741 | 34.712 | 1.00 | 25.19 |
| 17927 | C | ILE | C | 725 | -74.976 | -11.805 | 36.733 | 1.00 | 25.91 |
| 17928 | O | ILE | C | 725 | -75.273 | -12.998 | 36.669 | 1.00 | 26.39 |
| 17929 | N | TYR | C | 726 | -73.839 | -11.385 | 37.258 | 1.00 | 26.22 |
| 17930 | CA | TYR | C | 726 | -72.905 | -12.356 | 37.820 | 1.00 | 26.09 |
| 17931 | CB | TYR | C | 726 | -71.484 | -11.788 | 37.888 | 1.00 | 25.95 |
| 17932 | CG | TYR | C | 726 | -70.842 | -11.862 | 36.538 | 1.00 | 25.39 |
| 17933 | CD1 | TYR | C | 726 | -70.768 | -10.742 | 35.727 | 1.00 | 26.52 |
| 17934 | CE1 | TYR | C | 726 | -70.207 | -10.807 | 34.470 | 1.00 | 26.04 |
| 17935 | CZ | TYR | C | 726 | -69.732 | -12.019 | 34.000 | 1.00 | 27.86 |
| 17936 | OH | TYR | C | 726 | -69.183 | -12.076 | 32.736 | 1.00 | 31.21 |
| 17937 | CE2 | TYR | C | 726 | -69.800 | -13.155 | 34.785 | 1.00 | 25.02 |
| 17938 | CD2 | TYR | C | 726 | -70.376 | -13.074 | 36.038 | 1.00 | 25.01 |
| 17939 | C | TYR | C | 726 | -73.389 | -12.933 | 39.142 | 1.00 | 25.98 |
| 17940 | O | TYR | C | 726 | -73.091 | -14.079 | 39.473 | 1.00 | 25.65 |
| 17941 | N | THR | C | 727 | -74.152 | -12.151 | 39.893 | 1.00 | 26.17 |
| 17942 | CA | THR | C | 727 | -74.722 | -12.673 | 41.113 | 1.00 | 26.92 |

FIGURE 3 MN

| A | B | C | D | E | F | G | H | I | J |
|---|---|---|---|---|---|---|---|---|---|
| 17943 | CB | THR | C | 727 | -75.344 | -11.554 | 41.938 | 1.00 | 27.07 |
| 17944 | OG1 | THR | C | 727 | -74.316 | -10.635 | 42.327 | 1.00 | 28.30 |
| 17945 | CG2 | THR | C | 727 | -75.834 | -12.089 | 43.262 | 1.00 | 26.08 |
| 17946 | C | THR | C | 727 | -75.787 | -13.696 | 40.743 | 1.00 | 26.93 |
| 17947 | O | THR | C | 727 | -75.851 | -14.775 | 41.292 | 1.00 | 27.40 |
| 17948 | N | HIS | C | 728 | -76.612 | -13.343 | 39.773 | 1.00 | 27.18 |
| 17949 | CA | HIS | C | 728 | -77.702 | -14.192 | 39.376 | 1.00 | 26.26 |
| 17950 | CB | HIS | C | 728 | -78.578 | -13.490 | 38.344 | 1.00 | 26.06 |
| 17951 | CG | HIS | C | 728 | -79.934 | -14.097 | 38.205 | 1.00 | 23.30 |
| 17952 | ND1 | HIS | C | 728 | -80.849 | -14.101 | 39.232 | 1.00 | 22.47 |
| 17953 | CE1 | HIS | C | 728 | -81.948 | -14.716 | 38.836 | 1.00 | 25.26 |
| 17954 | NE2 | HIS | C | 728 | -81.779 | -15.106 | 37.584 | 1.00 | 23.59 |
| 17955 | CD2 | HIS | C | 728 | -80.517 | -14.752 | 37.177 | 1.00 | 23.11 |
| 17956 | C | HIS | C | 728 | -77.207 | -15.494 | 38.822 | 1.00 | 26.77 |
| 17957 | O | HIS | C | 728 | -77.769 | -16.540 | 39.132 | 1.00 | 27.34 |
| 17958 | N | MET | C | 729 | -76.175 | -15.437 | 37.988 | 1.00 | 27.12 |
| 17959 | CA | MET | C | 729 | -75.628 | -16.642 | 37.365 | 1.00 | 27.80 |
| 17960 | CB | MET | C | 729 | -74.648 | -16.286 | 36.234 | 1.00 | 27.69 |
| 17961 | CG | MET | C | 729 | -75.263 | -15.546 | 35.049 | 1.00 | 28.59 |
| 17962 | SD | MET | C | 729 | -74.201 | -15.459 | 33.591 | 1.00 | 30.95 |
| 17963 | CE | MET | C | 729 | -72.729 | -14.769 | 34.257 | 1.00 | 29.21 |
| 17964 | C | MET | C | 729 | -74.908 | -17.520 | 38.397 | 1.00 | 28.32 |
| 17965 | O | MET | C | 729 | -74.869 | -18.747 | 38.253 | 1.00 | 28.43 |
| 17966 | N | SER | C | 730 | -74.314 | -16.888 | 39.405 | 1.00 | 28.25 |
| 17967 | CA | SER | C | 730 | -73.630 | -17.619 | 40.453 | 1.00 | 29.48 |
| 17968 | CB | SER | C | 730 | -72.883 | -16.676 | 41.394 | 1.00 | 29.23 |
| 17969 | OG | SER | C | 730 | -71.845 | -16.002 | 40.707 | 1.00 | 30.09 |
| 17970 | C | SER | C | 730 | -74.662 | -18.420 | 41.226 | 1.00 | 29.98 |
| 17971 | O | SER | C | 730 | -74.448 | -19.586 | 41.524 | 1.00 | 29.82 |
| 17972 | N | HIS | C | 731 | -75.798 | -17.806 | 41.529 | 1.00 | 30.81 |
| 17973 | CA | HIS | C | 731 | -76.848 | -18.559 | 42.211 | 1.00 | 32.19 |
| 17974 | CB | HIS | C | 731 | -78.043 | -17.671 | 42.564 | 1.00 | 32.39 |
| 17975 | CG | HIS | C | 731 | -77.797 | -16.752 | 43.720 | 1.00 | 34.04 |
| 17976 | ND1 | HIS | C | 731 | -78.328 | -15.476 | 43.789 | 1.00 | 35.75 |
| 17977 | CE1 | HIS | C | 731 | -77.952 | -14.905 | 44.921 | 1.00 | 34.64 |
| 17978 | NE2 | HIS | C | 731 | -77.207 | -15.768 | 45.593 | 1.00 | 35.49 |
| 17979 | CD2 | HIS | C | 731 | -77.092 | -16.927 | 44.862 | 1.00 | 34.24 |
| 17980 | C | HIS | C | 731 | -77.299 | -19.740 | 41.346 | 1.00 | 32.33 |
| 17981 | O | HIS | C | 731 | -77.464 | -20.857 | 41.831 | 1.00 | 31.91 |
| 17982 | N | PHE | C | 732 | -77.467 | -19.499 | 40.053 | 1.00 | 32.72 |
| 17983 | CA | PHE | C | 732 | -77.942 | -20.559 | 39.177 | 1.00 | 33.08 |
| 17984 | CB | PHE | C | 732 | -78.275 | -20.011 | 37.789 | 1.00 | 32.39 |
| 17985 | CG | PHE | C | 732 | -78.750 | -21.053 | 36.823 | 1.00 | 30.50 |
| 17986 | CD1 | PHE | C | 732 | -80.094 | -21.375 | 36.739 | 1.00 | 29.46 |
| 17987 | CE1 | PHE | C | 732 | -80.546 | -22.336 | 35.850 | 1.00 | 30.06 |
| 17988 | CZ | PHE | C | 732 | -79.639 | -22.993 | 35.019 | 1.00 | 30.53 |
| 17989 | CE2 | PHE | C | 732 | -78.291 | -22.675 | 35.092 | 1.00 | 29.92 |
| 17990 | CD2 | PHE | C | 732 | -77.858 | -21.701 | 35.998 | 1.00 | 29.63 |
| 17991 | C | PHE | C | 732 | -76.959 | -21.743 | 39.100 | 1.00 | 33.93 |
| 17992 | O | PHE | C | 732 | -77.356 | -22.888 | 39.250 | 1.00 | 34.04 |
| 17993 | N | ILE | C | 733 | -75.687 | -21.469 | 38.863 | 1.00 | 35.09 |

FIGURE 3 MO

| A | B | C | D | E | F | G | H | I | J |
|---|---|---|---|---|---|---|---|---|---|
| 17994 | CA | ILE | C | 733 | -74.708 | -22.541 | 38.781 | 1.00 | 36.47 |
| 17995 | CB | ILE | C | 733 | -73.334 | -21.993 | 38.433 | 1.00 | 36.03 |
| 17996 | CG1 | ILE | C | 733 | -73.352 | -21.375 | 37.038 | 1.00 | 36.78 |
| 17997 | CD1 | ILE | C | 733 | -73.673 | -22.355 | 35.938 | 1.00 | 37.16 |
| 17998 | CG2 | ILE | C | 733 | -72.312 | -23.105 | 38.511 | 1.00 | 36.12 |
| 17999 | C | ILE | C | 733 | -74.618 | -23.311 | 40.094 | 1.00 | 37.68 |
| 18000 | O | ILE | C | 733 | -74.568 | -24.539 | 40.097 | 1.00 | 37.96 |
| 18001 | N | LYS | C | 734 | -74.614 | -22.589 | 41.209 | 1.00 | 39.05 |
| 18002 | CA | LYS | C | 734 | -74.487 | -23.239 | 42.512 | 1.00 | 40.56 |
| 18003 | CB | LYS | C | 734 | -74.345 | -22.199 | 43.625 | 1.00 | 40.35 |
| 18004 | CG | LYS | C | 734 | -73.340 | -21.120 | 43.293 | 1.00 | 39.62 |
| 18005 | CD | LYS | C | 734 | -72.498 | -20.779 | 44.472 | 1.00 | 39.88 |
| 18006 | CE | LYS | C | 734 | -73.333 | -20.568 | 45.699 | 1.00 | 40.60 |
| 18007 | NZ | LYS | C | 734 | -72.622 | -21.094 | 46.881 | 1.00 | 41.45 |
| 18008 | C | LYS | C | 734 | -75.613 | -24.209 | 42.840 | 1.00 | 41.64 |
| 18009 | O | LYS | C | 734 | -75.367 | -25.308 | 43.330 | 1.00 | 42.54 |
| 18010 | N | GLN | C | 735 | -76.846 | -23.808 | 42.588 | 1.00 | 42.61 |
| 18011 | CA | GLN | C | 735 | -77.975 | -24.673 | 42.885 | 1.00 | 43.80 |
| 18012 | CB | GLN | C | 735 | -79.298 | -23.889 | 42.813 | 1.00 | 43.93 |
| 18013 | CG | GLN | C | 735 | -80.478 | -24.618 | 43.486 | 1.00 | 46.68 |
| 18014 | CD | GLN | C | 735 | -81.636 | -23.693 | 43.845 | 1.00 | 49.78 |
| 18015 | OE1 | GLN | C | 735 | -82.014 | -23.587 | 45.020 | 1.00 | 50.01 |
| 18016 | NE2 | GLN | C | 735 | -82.210 | -23.033 | 42.834 | 1.00 | 50.27 |
| 18017 | C | GLN | C | 735 | -77.997 | -25.883 | 41.943 | 1.00 | 43.79 |
| 18018 | O | GLN | C | 735 | -78.464 | -26.960 | 42.307 | 1.00 | 43.94 |
| 18019 | N | CYS | C | 736 | -77.496 | -25.700 | 40.729 | 1.00 | 43.82 |
| 18020 | CA | CYS | C | 736 | -77.455 | -26.783 | 39.764 | 1.00 | 44.07 |
| 18021 | CB | CYS | C | 736 | -77.213 | -26.217 | 38.370 | 1.00 | 44.15 |
| 18022 | SG | CYS | C | 736 | -76.430 | -27.305 | 37.152 | 1.00 | 45.75 |
| 18023 | C | CYS | C | 736 | -76.374 | -27.790 | 40.155 | 1.00 | 44.17 |
| 18024 | O | CYS | C | 736 | -76.455 | -28.968 | 39.814 | 1.00 | 44.51 |
| 18025 | N | PHE | C | 737 | -75.382 | -27.311 | 40.897 | 1.00 | 43.85 |
| 18026 | CA | PHE | C | 737 | -74.290 | -28.127 | 41.378 | 1.00 | 43.48 |
| 18027 | CB | PHE | C | 737 | -72.997 | -27.358 | 41.219 | 1.00 | 43.04 |
| 18028 | CG | PHE | C | 737 | -72.486 | -27.348 | 39.836 | 1.00 | 40.98 |
| 18029 | CD1 | PHE | C | 737 | -73.101 | -28.112 | 38.864 | 1.00 | 39.10 |
| 18030 | CE1 | PHE | C | 737 | -72.633 | -28.121 | 37.592 | 1.00 | 37.35 |
| 18031 | CZ | PHE | C | 737 | -71.532 | -27.363 | 37.263 | 1.00 | 39.57 |
| 18032 | CE2 | PHE | C | 737 | -70.905 | -26.598 | 38.223 | 1.00 | 38.73 |
| 18033 | CD2 | PHE | C | 737 | -71.387 | -26.592 | 39.503 | 1.00 | 39.14 |
| 18034 | C | PHE | C | 737 | -74.463 | -28.459 | 42.848 | 1.00 | 44.22 |
| 18035 | O | PHE | C | 737 | -73.541 | -28.962 | 43.501 | 1.00 | 44.19 |
| 18036 | N | SER | C | 738 | -75.639 | -28.172 | 43.380 | 1.00 | 44.96 |
| 18037 | CA | SER | C | 738 | -75.876 | -28.410 | 44.792 | 1.00 | 45.92 |
| 18038 | CB | SER | C | 738 | -75.921 | -29.916 | 45.084 | 1.00 | 46.15 |
| 18039 | OG | SER | C | 738 | -76.830 | -30.586 | 44.219 | 1.00 | 44.65 |
| 18040 | C | SER | C | 738 | -74.777 | -27.751 | 45.627 | 1.00 | 47.06 |
| 18041 | O | SER | C | 738 | -74.360 | -28.307 | 46.648 | 1.00 | 47.75 |
| 18042 | N | LEU | C | 739 | -74.289 | -26.586 | 45.197 | 1.00 | 47.53 |
| 18043 | CA | LEU | C | 739 | -73.290 | -25.862 | 45.983 | 1.00 | 48.35 |
| 18044 | CB | LEU | C | 739 | -72.264 | -25.170 | 45.090 | 1.00 | 48.05 |

FIGURE 3 MP

| A | B | C | D | E | F | G | H | I | J |
|---|---|---|---|---|---|---|---|---|---|
| 18045 | CG  | LEU | C | 739   | -71.381 | -26.056 | 44.218 | 1.00 | 47.85 |
| 18046 | CD1 | LEU | C | 739   | -70.391 | -25.195 | 43.483 | 1.00 | 46.49 |
| 18047 | CD2 | LEU | C | 739   | -70.661 | -27.136 | 45.048 | 1.00 | 48.24 |
| 18048 | C   | LEU | C | 739   | -73.953 | -24.835 | 46.908 | 1.00 | 49.10 |
| 18049 | O   | LEU | C | 739   | -74.413 | -23.778 | 46.458 | 1.00 | 49.35 |
| 18050 | N   | PRO | C | 740   | -73.984 | -25.156 | 48.198 | 1.00 | 49.55 |
| 18051 | CA  | PRO | C | 740   | -74.608 | -24.312 | 49.227 | 1.00 | 49.80 |
| 18052 | CB  | PRO | C | 740   | -74.296 | -25.073 | 50.527 | 1.00 | 50.11 |
| 18053 | CG  | PRO | C | 740   | -74.110 | -26.505 | 50.086 | 1.00 | 50.01 |
| 18054 | CD  | PRO | C | 740   | -73.399 | -26.383 | 48.766 | 1.00 | 49.91 |
| 18055 | C   | PRO | C | 740   | -74.065 | -22.873 | 49.312 | 1.00 | 49.76 |
| 18056 | O   | PRO | C | 740   | -72.926 | -22.583 | 48.946 | 1.00 | 49.69 |
| 18057 | O7  | NAG | C | 1621  | -69.324 |  24.781 | 23.484 | 1.00 | 77.15 |
| 18058 | C7  | NAG | C | 1621  | -69.609 |  25.335 | 22.437 | 1.00 | 77.32 |
| 18059 | C8  | NAG | C | 1621  | -68.637 |  25.427 | 21.299 | 1.00 | 77.63 |
| 18060 | N2  | NAG | C | 1621  | -70.814 |  25.855 | 22.191 | 1.00 | 76.74 |
| 18061 | C2  | NAG | C | 1621  | -71.897 |  25.849 | 23.162 | 1.00 | 76.77 |
| 18062 | C1  | NAG | C | 1621  | -72.310 |  24.411 | 23.483 | 1.00 | 74.60 |
| 18063 | C3  | NAG | C | 1621  | -71.539 |  26.601 | 24.442 | 1.00 | 77.28 |
| 18064 | O3  | NAG | C | 1621  | -71.306 |  27.990 | 24.170 | 1.00 | 77.20 |
| 18065 | C4  | NAG | C | 1621  | -72.695 |  26.489 | 25.427 | 1.00 | 78.05 |
| 18066 | O4  | NAG | C | 1621  | -72.324 |  27.130 | 26.658 | 1.00 | 78.54 |
| 18067 | C5  | NAG | C | 1621  | -73.094 |  25.023 | 25.647 | 1.00 | 77.85 |
| 18068 | O5  | NAG | C | 1621  | -73.407 |  24.398 | 24.400 | 1.00 | 76.82 |
| 18069 | C6  | NAG | C | 1621  | -74.296 |  24.902 | 26.587 | 1.00 | 78.69 |
| 18070 | O6  | NAG | C | 1621  | -75.394 |  24.202 | 25.975 | 1.00 | 78.53 |
| 18071 | O7  | NAG | C | 2311  | -45.119 |  20.326 |  4.123 | 1.00 | 86.50 |
| 18072 | C7  | NAG | C | 2311  | -44.308 |  19.536 |  4.596 | 1.00 | 86.26 |
| 18073 | C8  | NAG | C | 2311  | -43.692 |  19.775 |  5.943 | 1.00 | 86.73 |
| 18074 | N2  | NAG | C | 2311  | -43.959 |  18.387 |  4.020 | 1.00 | 85.54 |
| 18075 | C2  | NAG | C | 2311  | -44.431 |  17.941 |  2.719 | 1.00 | 85.11 |
| 18076 | C1  | NAG | C | 2311  | -45.605 |  16.977 |  2.834 | 1.00 | 82.08 |
| 18077 | C3  | NAG | C | 2311  | -44.838 |  19.103 |  1.819 | 1.00 | 85.85 |
| 18078 | O3  | NAG | C | 2311  | -43.800 |  20.090 |  1.711 | 1.00 | 86.58 |
| 18079 | C4  | NAG | C | 2311  | -45.187 |  18.534 |  0.452 | 1.00 | 86.28 |
| 18080 | O4  | NAG | C | 2311  | -45.625 |  19.593 | -0.408 | 1.00 | 86.86 |
| 18081 | C5  | NAG | C | 2311  | -46.284 |  17.482 |  0.590 | 1.00 | 85.68 |
| 18082 | O5  | NAG | C | 2311  | -45.899 |  16.472 |  1.529 | 1.00 | 84.80 |
| 18083 | C6  | NAG | C | 2311  | -46.572 |  16.841 | -0.763 | 1.00 | 86.43 |
| 18084 | O6  | NAG | C | 2311  | -47.501 |  15.757 | -0.613 | 1.00 | 86.77 |
| 18085 | O7  | NAG | C | 2411  | -75.042 |  10.172 | -2.240 | 1.00 | 55.28 |
| 18086 | C7  | NAG | C | 2411  | -75.585 |  10.527 | -1.211 | 1.00 | 55.28 |
| 18087 | C8  | NAG | C | 2411  | -75.084 |  11.660 | -0.359 | 1.00 | 55.62 |
| 18088 | N2  | NAG | C | 2411  | -76.717 |   9.971 | -0.818 | 1.00 | 55.77 |
| 18089 | C2  | NAG | C | 2411  | -77.290 |   8.882 | -1.569 | 1.00 | 55.90 |
| 18090 | C1  | NAG | C | 2411  | -77.656 |   7.748 | -0.640 | 1.00 | 54.04 |
| 18091 | C3  | NAG | C | 2411  | -78.557 |   9.352 | -2.254 | 1.00 | 58.50 |
| 18092 | O3  | NAG | C | 2411  | -78.217 |  10.393 | -3.177 | 1.00 | 60.48 |
| 18093 | C4  | NAG | C | 2411  | -79.242 |   8.184 | -2.960 | 1.00 | 57.98 |
| 18094 | O4  | NAG | C | 2411  | -80.546 |   8.586 | -3.368 | 1.00 | 61.94 |
| 18095 | C5  | NAG | C | 2411  | -79.378 |   6.976 | -2.034 | 1.00 | 57.21 |

FIGURE 3 MQ

| A | B | C | D E | F | G | H | I | J |
|---|---|---|---|---|---|---|---|---|
| 18096 | O5 | NAG | C2411 | -78.125 | 6.674 | -1.437 | 1.00 | 54.85 |
| 18097 | C6 | NAG | C2411 | -79.857 | 5.738 | -2.785 | 1.00 | 57.15 |
| 18098 | O6 | NAG | C2411 | -80.816 | 5.047 | -1.985 | 1.00 | 57.43 |
| 18099 | O7 | NAG | C2412 | -84.036 | 5.860 | -2.398 | 1.00 | 72.47 |
| 18100 | C7 | NAG | C2412 | -83.715 | 6.962 | -2.822 | 1.00 | 73.43 |
| 18101 | C8 | NAG | C2412 | -83.913 | 8.216 | -2.018 | 1.00 | 72.70 |
| 18102 | N2 | NAG | C2412 | -83.090 | 7.125 | -3.991 | 1.00 | 73.75 |
| 18103 | C2 | NAG | C2412 | -82.715 | 8.448 | -4.452 | 1.00 | 74.18 |
| 18104 | C1 | NAG | C2412 | -81.205 | 8.630 | -4.581 | 1.00 | 71.93 |
| 18105 | C3 | NAG | C2412 | -83.383 | 8.739 | -5.788 | 1.00 | 75.49 |
| 18106 | O3 | NAG | C2412 | -84.803 | 8.644 | -5.651 | 1.00 | 75.59 |
| 18107 | C4 | NAG | C2412 | -83.000 | 10.149 | -6.210 | 1.00 | 76.52 |
| 18108 | O4 | NAG | C2412 | -83.608 | 10.490 | -7.457 | 1.00 | 80.35 |
| 18109 | C5 | NAG | C2412 | -81.486 | 10.249 | -6.315 | 1.00 | 75.48 |
| 18110 | O5 | NAG | C2412 | -80.920 | 9.961 | -5.032 | 1.00 | 73.95 |
| 18111 | C6 | NAG | C2412 | -81.064 | 11.638 | -6.789 | 1.00 | 75.01 |
| 18112 | O6 | NAG | C2412 | -81.555 | 12.632 | -5.880 | 1.00 | 74.46 |
| 18113 | O6 | MAN | C2413 | -86.351 | 13.692 | -8.034 | 1.00 | 93.60 |
| 18114 | C6 | MAN | C2413 | -86.318 | 13.247 | -9.396 | 1.00 | 92.70 |
| 18115 | C5 | MAN | C2413 | -85.247 | 12.175 | -9.548 | 1.00 | 91.67 |
| 18116 | O5 | MAN | C2413 | -85.404 | 11.229 | -8.490 | 1.00 | 90.56 |
| 18117 | C4 | MAN | C2413 | -85.365 | 11.486 | -10.905 | 1.00 | 91.36 |
| 18118 | O4 | MAN | C2413 | -85.075 | 12.418 | -11.949 | 1.00 | 92.46 |
| 18119 | C3 | MAN | C2413 | -84.399 | 10.313 | -11.010 | 1.00 | 90.86 |
| 18120 | O3 | MAN | C2413 | -84.652 | 9.578 | -12.211 | 1.00 | 91.25 |
| 18121 | C2 | MAN | C2413 | -84.545 | 9.392 | -9.811 | 1.00 | 90.25 |
| 18122 | O2 | MAN | C2413 | -85.824 | 8.748 | -9.848 | 1.00 | 89.98 |
| 18123 | C1 | MAN | C2413 | -84.419 | 10.199 | -8.528 | 1.00 | 88.38 |
| 18124 | O6 | MAN | C2414 | -80.241 | 11.930 | -11.940 | 1.00 | 99.01 |
| 18125 | C6 | MAN | C2414 | -80.791 | 10.937 | -12.810 | 1.00 | 98.42 |
| 18126 | C5 | MAN | C2414 | -82.264 | 11.255 | -13.029 | 1.00 | 97.98 |
| 18127 | O5 | MAN | C2414 | -82.550 | 12.540 | -12.479 | 1.00 | 97.59 |
| 18128 | C4 | MAN | C2414 | -82.631 | 11.205 | -14.509 | 1.00 | 97.88 |
| 18129 | O4 | MAN | C2414 | -82.502 | 9.856 | -14.966 | 1.00 | 97.78 |
| 18130 | C3 | MAN | C2414 | -84.059 | 11.686 | -14.745 | 1.00 | 97.54 |
| 18131 | O3 | MAN | C2414 | -84.269 | 11.881 | -16.144 | 1.00 | 97.99 |
| 18132 | C2 | MAN | C2414 | -84.314 | 13.003 | -14.031 | 1.00 | 97.34 |
| 18133 | O2 | MAN | C2414 | -83.531 | 14.032 | -14.649 | 1.00 | 97.01 |
| 18134 | C1 | MAN | C2414 | -83.931 | 12.879 | -12.564 | 1.00 | 96.30 |
| 18135 | O7 | NAG | C2931 | -70.567 | 28.515 | -2.283 | 1.00 | 81.63 |
| 18136 | C7 | NAG | C2931 | -70.247 | 28.468 | -1.106 | 1.00 | 80.91 |
| 18137 | C8 | NAG | C2931 | -69.337 | 29.480 | -0.477 | 1.00 | 81.17 |
| 18138 | N2 | NAG | C2931 | -70.757 | 27.564 | -0.280 | 1.00 | 79.93 |
| 18139 | C2 | NAG | C2931 | -71.665 | 26.557 | -0.785 | 1.00 | 79.07 |
| 18140 | C1 | NAG | C2931 | -71.355 | 25.188 | -0.191 | 1.00 | 77.34 |
| 18141 | C3 | NAG | C2931 | -73.096 | 26.975 | -0.471 | 1.00 | 79.10 |
| 18142 | O3 | NAG | C2931 | -73.375 | 28.245 | -1.078 | 1.00 | 79.59 |
| 18143 | C4 | NAG | C2931 | -74.057 | 25.910 | -0.984 | 1.00 | 79.26 |
| 18144 | O4 | NAG | C2931 | -75.420 | 26.257 | -0.675 | 1.00 | 79.01 |
| 18145 | C5 | NAG | C2931 | -73.676 | 24.559 | -0.376 | 1.00 | 78.61 |
| 18146 | O5 | NAG | C2931 | -72.309 | 24.237 | -0.674 | 1.00 | 78.29 |

FIGURE 3 MR

| A | B | C | D | E | F | G | H | I | J |
|---|---|---|---|---|---|---|---|---|---|
| 18147 | C6 | NAG | C | 2931 | -74.600 | 23.456 | -0.894 | 1.00 | 78.34 |
| 18148 | O6 | NAG | C | 2931 | -74.017 | 22.784 | -2.020 | 1.00 | 77.59 |
| 18149 | O7 | NAG | C | 3331 | -63.689 | -19.851 | -4.727 | 1.00 | 74.43 |
| 18150 | C7 | NAG | C | 3331 | -63.690 | -18.636 | -4.805 | 1.00 | 73.65 |
| 18151 | C8 | NAG | C | 3331 | -62.493 | -17.871 | -5.291 | 1.00 | 74.34 |
| 18152 | N2 | NAG | C | 3331 | -64.780 | -17.909 | -4.552 | 1.00 | 72.43 |
| 18153 | C2 | NAG | C | 3331 | -66.007 | -18.533 | -4.085 | 1.00 | 70.84 |
| 18154 | C1 | NAG | C | 3331 | -66.710 | -17.632 | -3.082 | 1.00 | 67.96 |
| 18155 | C3 | NAG | C | 3331 | -66.970 | -18.879 | -5.213 | 1.00 | 70.62 |
| 18156 | O3 | NAG | C | 3331 | -66.363 | -19.827 | -6.102 | 1.00 | 71.81 |
| 18157 | C4 | NAG | C | 3331 | -68.250 | -19.480 | -4.633 | 1.00 | 70.09 |
| 18158 | O4 | NAG | C | 3331 | -69.255 | -19.587 | -5.653 | 1.00 | 69.60 |
| 18159 | C5 | NAG | C | 3331 | -68.788 | -18.652 | -3.465 | 1.00 | 69.57 |
| 18160 | O5 | NAG | C | 3331 | -67.764 | -18.390 | -2.505 | 1.00 | 69.44 |
| 18161 | C6 | NAG | C | 3331 | -69.918 | -19.382 | -2.753 | 1.00 | 69.16 |
| 18162 | O6 | NAG | C | 3331 | -69.339 | -20.318 | -1.841 | 1.00 | 68.15 |
| 18163 | N | SER | D | 13 | -110.740 | -42.363 | 47.327 | 1.00 | 61.36 |
| 18164 | CA | SER | D | 13 | -110.386 | -40.918 | 47.415 | 1.00 | 60.89 |
| 18165 | CB | SER | D | 13 | -111.292 | -40.205 | 48.428 | 1.00 | 60.96 |
| 18166 | OG | SER | D | 13 | -111.799 | -38.984 | 47.896 | 1.00 | 60.88 |
| 18167 | C | SER | D | 13 | -108.908 | -40.766 | 47.785 | 1.00 | 60.77 |
| 18168 | O | SER | D | 13 | -108.553 | -40.477 | 48.951 | 1.00 | 60.94 |
| 18169 | N | ARG | D | 14 | -108.048 | -40.983 | 46.789 | 1.00 | 60.00 |
| 18170 | CA | ARG | D | 14 | -106.597 | -40.869 | 46.975 | 1.00 | 59.08 |
| 18171 | CB | ARG | D | 14 | -105.977 | -42.260 | 47.149 | 1.00 | 59.38 |
| 18172 | CG | ARG | D | 14 | -104.493 | -42.396 | 46.898 | 1.00 | 60.79 |
| 18173 | CD | ARG | D | 14 | -104.176 | -43.165 | 45.625 | 1.00 | 64.29 |
| 18174 | NE | ARG | D | 14 | -103.070 | -44.107 | 45.797 | 1.00 | 66.91 |
| 18175 | CZ | ARG | D | 14 | -101.994 | -44.143 | 45.018 | 1.00 | 67.92 |
| 18176 | NH1 | ARG | D | 14 | -101.871 | -43.288 | 44.013 | 1.00 | 67.83 |
| 18177 | NH2 | ARG | D | 14 | -101.039 | -45.034 | 45.240 | 1.00 | 68.22 |
| 18178 | C | ARG | D | 14 | -105.942 | -40.037 | 45.857 | 1.00 | 57.85 |
| 18179 | O | ARG | D | 14 | -104.736 | -39.753 | 45.891 | 1.00 | 57.68 |
| 18180 | N | LYS | D | 15 | -106.753 | -39.639 | 44.878 | 1.00 | 56.24 |
| 18181 | CA | LYS | D | 15 | -106.303 | -38.729 | 43.833 | 1.00 | 54.85 |
| 18182 | CB | LYS | D | 15 | -107.112 | -38.919 | 42.556 | 1.00 | 55.33 |
| 18183 | CG | LYS | D | 15 | -106.495 | -39.829 | 41.516 | 1.00 | 56.61 |
| 18184 | CD | LYS | D | 15 | -107.496 | -40.065 | 40.380 | 1.00 | 58.88 |
| 18185 | CE | LYS | D | 15 | -108.832 | -40.572 | 40.922 | 1.00 | 59.93 |
| 18186 | NZ | LYS | D | 15 | -109.924 | -40.572 | 39.890 | 1.00 | 61.34 |
| 18187 | C | LYS | D | 15 | -106.508 | -37.296 | 44.300 | 1.00 | 53.25 |
| 18188 | O | LYS | D | 15 | -107.446 | -37.009 | 45.041 | 1.00 | 53.26 |
| 18189 | N | THR | D | 16 | -105.625 | -36.401 | 43.878 | 1.00 | 51.06 |
| 18190 | CA | THR | D | 16 | -105.809 | -34.980 | 44.147 | 1.00 | 48.79 |
| 18191 | CB | THR | D | 16 | -104.599 | -34.376 | 44.883 | 1.00 | 48.98 |
| 18192 | OG1 | THR | D | 16 | -103.392 | -34.665 | 44.159 | 1.00 | 48.23 |
| 18193 | CG2 | THR | D | 16 | -104.384 | -35.058 | 46.233 | 1.00 | 49.02 |
| 18194 | C | THR | D | 16 | -105.968 | -34.292 | 42.811 | 1.00 | 47.23 |
| 18195 | O | THR | D | 16 | -105.633 | -34.853 | 41.775 | 1.00 | 46.86 |
| 18196 | N | TYR | D | 17 | -106.504 | -33.082 | 42.834 | 1.00 | 45.40 |
| 18197 | CA | TYR | D | 17 | -106.595 | -32.276 | 41.634 | 1.00 | 43.29 |

FIGURE 3 MS

| A | B | C | D | E | F | G | H | I | J |
|---|---|---|---|---|---|---|---|---|---|
| 18198 | CB | TYR | D | 17 | -107.591 | -31.146 | 41.877 | 1.00 | 42.92 |
| 18199 | CG | TYR | D | 17 | -107.813 | -30.211 | 40.708 | 1.00 | 41.77 |
| 18200 | CD1 | TYR | D | 17 | -108.774 | -30.484 | 39.736 | 1.00 | 39.19 |
| 18201 | CE1 | TYR | D | 17 | -108.983 | -29.624 | 38.683 | 1.00 | 38.15 |
| 18202 | CZ | TYR | D | 17 | -108.224 | -28.465 | 38.588 | 1.00 | 39.21 |
| 18203 | OH | TYR | D | 17 | -108.399 | -27.580 | 37.546 | 1.00 | 36.44 |
| 18204 | CE2 | TYR | D | 17 | -107.270 | -28.179 | 39.541 | 1.00 | 39.84 |
| 18205 | CD2 | TYR | D | 17 | -107.072 | -29.044 | 40.589 | 1.00 | 40.04 |
| 18206 | C | TYR | D | 17 | -105.182 | -31.736 | 41.387 | 1.00 | 42.57 |
| 18207 | O | TYR | D | 17 | -104.624 | -31.033 | 42.228 | 1.00 | 42.04 |
| 18208 | N | THR | D | 18 | -104.598 | -32.090 | 40.247 | 1.00 | 41.76 |
| 18209 | CA | THR | D | 18 | -103.219 | -31.709 | 39.939 | 1.00 | 41.00 |
| 18210 | CB | THR | D | 18 | -102.514 | -32.825 | 39.187 | 1.00 | 40.40 |
| 18211 | OG1 | THR | D | 18 | -103.228 | -33.053 | 37.972 | 1.00 | 40.49 |
| 18212 | CG2 | THR | D | 18 | -102.598 | -34.114 | 39.935 | 1.00 | 40.17 |
| 18213 | C | THR | D | 18 | -103.117 | -30.500 | 39.038 | 1.00 | 40.59 |
| 18214 | O | THR | D | 18 | -104.111 | -29.972 | 38.569 | 1.00 | 40.76 |
| 18215 | N | LEU | D | 19 | -101.878 | -30.118 | 38.759 | 1.00 | 40.02 |
| 18216 | CA | LEU | D | 19 | -101.592 | -29.002 | 37.889 | 1.00 | 39.77 |
| 18217 | CB | LEU | D | 19 | -100.111 | -28.637 | 37.974 | 1.00 | 39.21 |
| 18218 | CG | LEU | D | 19 | -99.648 | -27.489 | 37.095 | 1.00 | 37.71 |
| 18219 | CD1 | LEU | D | 19 | -100.422 | -26.230 | 37.454 | 1.00 | 35.69 |
| 18220 | CD2 | LEU | D | 19 | -98.144 | -27.279 | 37.279 | 1.00 | 37.86 |
| 18221 | C | LEU | D | 19 | -101.959 | -29.364 | 36.470 | 1.00 | 39.98 |
| 18222 | O | LEU | D | 19 | -102.630 | -28.601 | 35.784 | 1.00 | 39.95 |
| 18223 | N | THR | D | 20 | -101.514 | -30.535 | 36.026 | 1.00 | 40.46 |
| 18224 | CA | THR | D | 20 | -101.875 | -30.988 | 34.698 | 1.00 | 41.26 |
| 18225 | CB | THR | D | 20 | -101.332 | -32.419 | 34.420 | 1.00 | 41.48 |
| 18226 | OG1 | THR | D | 20 | -99.923 | -32.461 | 34.690 | 1.00 | 43.06 |
| 18227 | CG2 | THR | D | 20 | -101.372 | -32.730 | 32.938 | 1.00 | 41.78 |
| 18228 | C | THR | D | 20 | -103.395 | -30.921 | 34.594 | 1.00 | 41.40 |
| 18229 | O | THR | D | 20 | -103.926 | -30.375 | 33.636 | 1.00 | 42.00 |
| 18230 | N | ASP | D | 21 | -104.101 | -31.419 | 35.604 | 1.00 | 41.61 |
| 18231 | CA | ASP | D | 21 | -105.559 | -31.373 | 35.570 | 1.00 | 42.18 |
| 18232 | CB | ASP | D | 21 | -106.169 | -31.803 | 36.912 | 1.00 | 42.36 |
| 18233 | CG | ASP | D | 21 | -105.920 | -33.278 | 37.234 | 1.00 | 43.15 |
| 18234 | OD1 | ASP | D | 21 | -105.803 | -34.096 | 36.290 | 1.00 | 43.47 |
| 18235 | OD2 | ASP | D | 21 | -105.830 | -33.709 | 38.407 | 1.00 | 43.92 |
| 18236 | C | ASP | D | 21 | -106.039 | -29.977 | 35.204 | 1.00 | 42.09 |
| 18237 | O | ASP | D | 21 | -106.884 | -29.814 | 34.319 | 1.00 | 41.58 |
| 18238 | N | TYR | D | 22 | -105.495 | -28.972 | 35.895 | 1.00 | 42.01 |
| 18239 | CA | TYR | D | 22 | -105.861 | -27.586 | 35.649 | 1.00 | 41.53 |
| 18240 | CB | TYR | D | 22 | -105.252 | -26.665 | 36.710 | 1.00 | 41.76 |
| 18241 | CG | TYR | D | 22 | -105.377 | -25.196 | 36.396 | 1.00 | 39.80 |
| 18242 | CD1 | TYR | D | 22 | -106.612 | -24.614 | 36.140 | 1.00 | 39.04 |
| 18243 | CE1 | TYR | D | 22 | -106.717 | -23.265 | 35.839 | 1.00 | 38.61 |
| 18244 | CZ | TYR | D | 22 | -105.574 | -22.490 | 35.815 | 1.00 | 38.02 |
| 18245 | OH | TYR | D | 22 | -105.641 | -21.142 | 35.529 | 1.00 | 38.34 |
| 18246 | CE2 | TYR | D | 22 | -104.348 | -23.050 | 36.070 | 1.00 | 37.72 |
| 18247 | CD2 | TYR | D | 22 | -104.254 | -24.386 | 36.357 | 1.00 | 39.58 |
| 18248 | C | TYR | D | 22 | -105.405 | -27.147 | 34.287 | 1.00 | 41.60 |

FIGURE 3 MT

| A | B | C | D | E | F | G | H | I | J |
|---|---|---|---|---|---|---|---|---|---|
| 18249 | O | TYR | D | 22 | -106.168 | -26.553 | 33.540 | 1.00 | 41.54 |
| 18250 | N | LEU | D | 23 | -104.162 | -27.455 | 33.949 | 1.00 | 42.15 |
| 18251 | CA | LEU | D | 23 | -103.614 | -27.034 | 32.658 | 1.00 | 42.86 |
| 18252 | CB | LEU | D | 23 | -102.097 | -27.209 | 32.617 | 1.00 | 42.53 |
| 18253 | CG | LEU | D | 23 | -101.334 | -26.426 | 33.688 | 1.00 | 42.98 |
| 18254 | CD1 | LEU | D | 23 | -99.842 | -26.401 | 33.402 | 1.00 | 40.18 |
| 18255 | CD2 | LEU | D | 23 | -101.895 | -25.010 | 33.790 | 1.00 | 42.48 |
| 18256 | C | LEU | D | 23 | -104.252 | -27.732 | 31.465 | 1.00 | 43.63 |
| 18257 | O | LEU | D | 23 | -104.326 | -27.165 | 30.384 | 1.00 | 43.71 |
| 18258 | N | LYS | D | 24 | -104.718 | -28.962 | 31.656 | 1.00 | 44.61 |
| 18259 | CA | LYS | D | 24 | -105.307 | -29.703 | 30.547 | 1.00 | 45.83 |
| 18260 | CB | LYS | D | 24 | -104.703 | -31.103 | 30.447 | 1.00 | 45.69 |
| 18261 | CG | LYS | D | 24 | -103.186 | -31.110 | 30.303 | 1.00 | 45.41 |
| 18262 | CD | LYS | D | 24 | -102.735 | -30.517 | 28.978 | 1.00 | 44.15 |
| 18263 | CE | LYS | D | 24 | -101.218 | -30.572 | 28.859 | 1.00 | 43.82 |
| 18264 | NZ | LYS | D | 24 | -100.717 | -30.178 | 27.505 | 1.00 | 44.06 |
| 18265 | C | LYS | D | 24 | -106.827 | -29.779 | 30.626 | 1.00 | 46.53 |
| 18266 | O | LYS | D | 24 | -107.458 | -30.475 | 29.835 | 1.00 | 46.70 |
| 18267 | N | ASN | D | 25 | -107.410 | -29.064 | 31.582 | 1.00 | 47.48 |
| 18268 | CA | ASN | D | 25 | -108.861 | -29.017 | 31.719 | 1.00 | 48.45 |
| 18269 | CB | ASN | D | 25 | -109.482 | -28.246 | 30.558 | 1.00 | 48.72 |
| 18270 | CG | ASN | D | 25 | -110.641 | -27.378 | 30.999 | 1.00 | 51.15 |
| 18271 | OD1 | ASN | D | 25 | -111.797 | -27.803 | 30.980 | 1.00 | 52.66 |
| 18272 | ND2 | ASN | D | 25 | -110.335 | -26.144 | 31.413 | 1.00 | 53.94 |
| 18273 | C | ASN | D | 25 | -109.437 | -30.422 | 31.780 | 1.00 | 48.69 |
| 18274 | O | ASN | D | 25 | -110.334 | -30.786 | 31.017 | 1.00 | 48.74 |
| 18275 | N | THR | D | 26 | -108.896 | -31.211 | 32.693 | 1.00 | 48.91 |
| 18276 | CA | THR | D | 26 | -109.313 | -32.583 | 32.857 | 1.00 | 49.28 |
| 18277 | CB | THR | D | 26 | -108.374 | -33.283 | 33.827 | 1.00 | 49.12 |
| 18278 | OG1 | THR | D | 26 | -107.087 | -33.419 | 33.212 | 1.00 | 48.89 |
| 18279 | CG2 | THR | D | 26 | -108.821 | -34.718 | 34.060 | 1.00 | 49.93 |
| 18280 | C | THR | D | 26 | -110.743 | -32.621 | 33.360 | 1.00 | 49.63 |
| 18281 | O | THR | D | 26 | -111.600 | -33.295 | 32.786 | 1.00 | 49.55 |
| 18282 | N | TYR | D | 27 | -111.001 | -31.889 | 34.433 | 1.00 | 49.75 |
| 18283 | CA | TYR | D | 27 | -112.341 | -31.832 | 34.976 | 1.00 | 50.33 |
| 18284 | CB | TYR | D | 27 | -112.300 | -31.858 | 36.497 | 1.00 | 50.13 |
| 18285 | CG | TYR | D | 27 | -111.493 | -33.013 | 37.032 | 1.00 | 50.17 |
| 18286 | CD1 | TYR | D | 27 | -112.074 | -34.262 | 37.225 | 1.00 | 50.65 |
| 18287 | CE1 | TYR | D | 27 | -111.338 | -35.324 | 37.711 | 1.00 | 50.13 |
| 18288 | CZ | TYR | D | 27 | -109.999 | -35.147 | 38.002 | 1.00 | 50.51 |
| 18289 | OH | TYR | D | 27 | -109.254 | -36.199 | 38.482 | 1.00 | 49.41 |
| 18290 | CE2 | TYR | D | 27 | -109.399 | -33.916 | 37.816 | 1.00 | 50.11 |
| 18291 | CD2 | TYR | D | 27 | -110.146 | -32.863 | 37.328 | 1.00 | 50.05 |
| 18292 | C | TYR | D | 27 | -113.015 | -30.583 | 34.437 | 1.00 | 50.72 |
| 18293 | O | TYR | D | 27 | -112.845 | -29.491 | 34.963 | 1.00 | 51.02 |
| 18294 | N | ARG | D | 28 | -113.770 | -30.759 | 33.363 | 1.00 | 51.36 |
| 18295 | CA | ARG | D | 28 | -114.399 | -29.642 | 32.675 | 1.00 | 51.80 |
| 18296 | CB | ARG | D | 28 | -114.632 | -29.994 | 31.207 | 1.00 | 52.11 |
| 18297 | CG | ARG | D | 28 | -114.695 | -28.786 | 30.286 | 1.00 | 54.37 |
| 18298 | CD | ARG | D | 28 | -114.251 | -29.082 | 28.857 | 1.00 | 58.10 |
| 18299 | NE | ARG | D | 28 | -113.024 | -29.880 | 28.828 | 1.00 | 60.38 |

FIGURE 3 MU

| A | B | C | D | E | F | G | H | I | J |
|---|---|---|---|---|---|---|---|---|---|
| 18300 | CZ | ARG | D | 28 | -112.573 | -30.513 | 27.749 | 1.00 | 62.20 |
| 18301 | NH1 | ARG | D | 28 | -113.246 | -30.433 | 26.601 | 1.00 | 61.96 |
| 18302 | NH2 | ARG | D | 28 | -111.448 | -31.225 | 27.812 | 1.00 | 62.10 |
| 18303 | C | ARG | D | 28 | -115.705 | -29.216 | 33.328 | 1.00 | 51.52 |
| 18304 | O | ARG | D | 28 | -116.432 | -30.033 | 33.891 | 1.00 | 51.32 |
| 18305 | N | LEU | D | 29 | -115.985 | -27.924 | 33.246 | 1.00 | 51.44 |
| 18306 | CA | LEU | D | 29 | -117.184 | -27.352 | 33.823 | 1.00 | 51.71 |
| 18307 | CB | LEU | D | 29 | -116.862 | -26.001 | 34.464 | 1.00 | 51.76 |
| 18308 | CG | LEU | D | 29 | -117.397 | -25.689 | 35.863 | 1.00 | 51.86 |
| 18309 | CD1 | LEU | D | 29 | -117.174 | -24.219 | 36.199 | 1.00 | 52.54 |
| 18310 | CD2 | LEU | D | 29 | -116.725 | -26.560 | 36.896 | 1.00 | 50.90 |
| 18311 | C | LEU | D | 29 | -118.175 | -27.166 | 32.695 | 1.00 | 51.86 |
| 18312 | O | LEU | D | 29 | -117.829 | -26.644 | 31.636 | 1.00 | 51.83 |
| 18313 | N | LYS | D | 30 | -119.410 | -27.601 | 32.907 | 1.00 | 52.21 |
| 18314 | CA | LYS | D | 30 | -120.423 | -27.456 | 31.867 | 1.00 | 52.67 |
| 18315 | CB | LYS | D | 30 | -121.306 | -28.710 | 31.761 | 1.00 | 53.06 |
| 18316 | CG | LYS | D | 30 | -120.826 | -29.719 | 30.716 | 1.00 | 54.05 |
| 18317 | CD | LYS | D | 30 | -121.616 | -31.021 | 30.788 | 1.00 | 55.73 |
| 18318 | CE | LYS | D | 30 | -121.273 | -31.910 | 29.608 | 1.00 | 56.45 |
| 18319 | NZ | LYS | D | 30 | -121.142 | -31.078 | 28.371 | 1.00 | 56.95 |
| 18320 | C | LYS | D | 30 | -121.271 | -26.206 | 32.038 | 1.00 | 52.47 |
| 18321 | O | LYS | D | 30 | -121.777 | -25.921 | 33.119 | 1.00 | 52.14 |
| 18322 | N | LEU | D | 31 | -121.423 | -25.487 | 30.934 | 1.00 | 52.69 |
| 18323 | CA | LEU | D | 31 | -122.201 | -24.263 | 30.863 | 1.00 | 52.74 |
| 18324 | CB | LEU | D | 31 | -121.416 | -23.188 | 30.098 | 1.00 | 52.95 |
| 18325 | CG | LEU | D | 31 | -120.111 | -22.585 | 30.623 | 1.00 | 53.54 |
| 18326 | CD1 | LEU | D | 31 | -119.004 | -23.622 | 30.673 | 1.00 | 53.94 |
| 18327 | CD2 | LEU | D | 31 | -119.696 | -21.403 | 29.736 | 1.00 | 54.17 |
| 18328 | C | LEU | D | 31 | -123.465 | -24.528 | 30.069 | 1.00 | 52.59 |
| 18329 | O | LEU | D | 31 | -123.580 | -25.535 | 29.388 | 1.00 | 52.54 |
| 18330 | N | TYR | D | 32 | -124.417 | -23.613 | 30.138 | 1.00 | 52.53 |
| 18331 | CA | TYR | D | 32 | -125.577 | -23.720 | 29.271 | 1.00 | 52.53 |
| 18332 | CB | TYR | D | 32 | -126.797 | -24.261 | 30.009 | 1.00 | 52.27 |
| 18333 | CG | TYR | D | 32 | -127.864 | -24.763 | 29.075 | 1.00 | 52.18 |
| 18334 | CD1 | TYR | D | 32 | -128.703 | -23.877 | 28.419 | 1.00 | 52.00 |
| 18335 | CE1 | TYR | D | 32 | -129.685 | -24.324 | 27.558 | 1.00 | 52.36 |
| 18336 | CZ | TYR | D | 32 | -129.841 | -25.676 | 27.340 | 1.00 | 52.56 |
| 18337 | OH | TYR | D | 32 | -130.833 | -26.103 | 26.477 | 1.00 | 53.81 |
| 18338 | CE2 | TYR | D | 32 | -129.017 | -26.583 | 27.975 | 1.00 | 52.66 |
| 18339 | CD2 | TYR | D | 32 | -128.029 | -26.123 | 28.839 | 1.00 | 52.25 |
| 18340 | C | TYR | D | 32 | -125.834 | -22.348 | 28.680 | 1.00 | 52.56 |
| 18341 | O | TYR | D | 32 | -126.610 | -21.563 | 29.206 | 1.00 | 52.46 |
| 18342 | N | SER | D | 33 | -125.158 | -22.062 | 27.579 | 1.00 | 52.86 |
| 18343 | CA | SER | D | 33 | -125.251 | -20.755 | 26.964 | 1.00 | 53.35 |
| 18344 | CB | SER | D | 33 | -123.942 | -20.435 | 26.249 | 1.00 | 53.42 |
| 18345 | OG | SER | D | 33 | -123.580 | -19.079 | 26.443 | 1.00 | 55.27 |
| 18346 | C | SER | D | 33 | -126.415 | -20.695 | 25.986 | 1.00 | 53.35 |
| 18347 | O | SER | D | 33 | -126.497 | -21.499 | 25.061 | 1.00 | 53.27 |
| 18348 | N | LEU | D | 34 | -127.318 | -19.745 | 26.191 | 1.00 | 53.41 |
| 18349 | CA | LEU | D | 34 | -128.459 | -19.602 | 25.299 | 1.00 | 53.44 |
| 18350 | CB | LEU | D | 34 | -129.746 | -20.092 | 25.968 | 1.00 | 53.10 |

FIGURE 3 MV

| A | B | C | D | E | F | G | H | I | J |
|---|---|---|---|---|---|---|---|---|---|
| 18351 | CG | LEU | D | 34 | -130.225 | -19.356 | 27.220 | 1.00 | 53.46 |
| 18352 | CD1 | LEU | D | 34 | -130.978 | -18.081 | 26.859 | 1.00 | 52.97 |
| 18353 | CD2 | LEU | D | 34 | -131.099 | -20.262 | 28.066 | 1.00 | 53.49 |
| 18354 | C | LEU | D | 34 | -128.632 | -18.172 | 24.835 | 1.00 | 53.80 |
| 18355 | O | LEU | D | 34 | -128.063 | -17.245 | 25.406 | 1.00 | 53.33 |
| 18356 | N | ARG | D | 35 | -129.430 | -18.008 | 23.787 | 1.00 | 54.56 |
| 18357 | CA | ARG | D | 35 | -129.723 | -16.701 | 23.237 | 1.00 | 55.37 |
| 18358 | CB | ARG | D | 35 | -129.021 | -16.528 | 21.894 | 1.00 | 55.72 |
| 18359 | CG | ARG | D | 35 | -127.543 | -16.885 | 21.931 | 1.00 | 58.21 |
| 18360 | CD | ARG | D | 35 | -126.992 | -17.461 | 20.630 | 1.00 | 62.08 |
| 18361 | NE | ARG | D | 35 | -125.559 | -17.203 | 20.496 | 1.00 | 64.78 |
| 18362 | CZ | ARG | D | 35 | -125.028 | -16.391 | 19.585 | 1.00 | 65.80 |
| 18363 | NH1 | ARG | D | 35 | -125.808 | -15.760 | 18.711 | 1.00 | 65.88 |
| 18364 | NH2 | ARG | D | 35 | -123.714 | -16.211 | 19.546 | 1.00 | 65.79 |
| 18365 | C | ARG | D | 35 | -131.221 | -16.596 | 23.050 | 1.00 | 55.34 |
| 18366 | O | ARG | D | 35 | -131.800 | -17.317 | 22.245 | 1.00 | 55.67 |
| 18367 | N | TRP | D | 36 | -131.861 | -15.716 | 23.804 | 1.00 | 55.45 |
| 18368 | CA | TRP | D | 36 | -133.284 | -15.519 | 23.625 | 1.00 | 55.58 |
| 18369 | CB | TRP | D | 36 | -133.866 | -14.634 | 24.720 | 1.00 | 55.11 |
| 18370 | CG | TRP | D | 36 | -133.847 | -15.281 | 26.054 | 1.00 | 54.04 |
| 18371 | CD1 | TRP | D | 36 | -133.009 | -14.999 | 27.088 | 1.00 | 53.20 |
| 18372 | NE1 | TRP | D | 36 | -133.290 | -15.811 | 28.158 | 1.00 | 52.47 |
| 18373 | CE2 | TRP | D | 36 | -134.321 | -16.646 | 27.825 | 1.00 | 52.20 |
| 18374 | CD2 | TRP | D | 36 | -134.699 | -16.337 | 26.506 | 1.00 | 52.88 |
| 18375 | CE3 | TRP | D | 36 | -135.748 | -17.058 | 25.926 | 1.00 | 52.40 |
| 18376 | CZ3 | TRP | D | 36 | -136.372 | -18.036 | 26.669 | 1.00 | 52.17 |
| 18377 | CH2 | TRP | D | 36 | -135.974 | -18.315 | 27.982 | 1.00 | 51.24 |
| 18378 | CZ2 | TRP | D | 36 | -134.954 | -17.634 | 28.574 | 1.00 | 51.41 |
| 18379 | C | TRP | D | 36 | -133.487 | -14.890 | 22.256 | 1.00 | 56.26 |
| 18380 | O | TRP | D | 36 | -132.865 | -13.884 | 21.915 | 1.00 | 55.84 |
| 18381 | N | ILE | D | 37 | -134.349 | -15.516 | 21.468 | 1.00 | 57.29 |
| 18382 | CA | ILE | D | 37 | -134.644 | -15.056 | 20.127 | 1.00 | 58.06 |
| 18383 | CB | ILE | D | 37 | -134.766 | -16.271 | 19.205 | 1.00 | 58.19 |
| 18384 | CG1 | ILE | D | 37 | -133.814 | -16.136 | 18.020 | 1.00 | 58.92 |
| 18385 | CD1 | ILE | D | 37 | -132.371 | -16.010 | 18.440 | 1.00 | 59.40 |
| 18386 | CG2 | ILE | D | 37 | -136.215 | -16.523 | 18.801 | 1.00 | 58.85 |
| 18387 | C | ILE | D | 37 | -135.953 | -14.300 | 20.209 | 1.00 | 58.33 |
| 18388 | O | ILE | D | 37 | -136.236 | -13.417 | 19.400 | 1.00 | 58.56 |
| 18389 | N | SER | D | 38 | -136.740 | -14.647 | 21.220 | 1.00 | 58.68 |
| 18390 | CA | SER | D | 38 | -138.021 | -14.010 | 21.463 | 1.00 | 59.15 |
| 18391 | CB | SER | D | 38 | -139.119 | -14.682 | 20.650 | 1.00 | 59.13 |
| 18392 | OG | SER | D | 38 | -139.579 | -15.848 | 21.320 | 1.00 | 59.77 |
| 18393 | C | SER | D | 38 | -138.357 | -14.171 | 22.928 | 1.00 | 59.35 |
| 18394 | O | SER | D | 38 | -137.491 | -14.467 | 23.745 | 1.00 | 59.50 |
| 18395 | N | ASP | D | 39 | -139.637 | -14.019 | 23.245 | 1.00 | 59.53 |
| 18396 | CA | ASP | D | 39 | -140.113 | -14.136 | 24.609 | 1.00 | 59.49 |
| 18397 | CB | ASP | D | 39 | -141.367 | -13.290 | 24.788 | 1.00 | 59.39 |
| 18398 | CG | ASP | D | 39 | -141.507 | -12.757 | 26.187 | 1.00 | 60.15 |
| 18399 | OD1 | ASP | D | 39 | -142.625 | -12.337 | 26.550 | 1.00 | 61.22 |
| 18400 | OD2 | ASP | D | 39 | -140.558 | -12.714 | 27.000 | 1.00 | 61.27 |
| 18401 | C | ASP | D | 39 | -140.410 | -15.573 | 25.009 | 1.00 | 59.56 |

FIGURE 3 MW

| A | B | C | D | E | F | G | H | I | J |
|---|---|---|---|---|---|---|---|---|---|
| 18402 | O | ASP | D | 39 | -140.781 | -15.837 | 26.145 | 1.00 | 59.26 |
| 18403 | N | HIS | D | 40 | -140.245 | -16.512 | 24.090 | 1.00 | 60.02 |
| 18404 | CA | HIS | D | 40 | -140.571 | -17.891 | 24.420 | 1.00 | 60.67 |
| 18405 | CB | HIS | D | 40 | -141.962 | -18.228 | 23.895 | 1.00 | 61.24 |
| 18406 | CG | HIS | D | 40 | -142.679 | -17.050 | 23.323 | 1.00 | 62.71 |
| 18407 | ND1 | HIS | D | 40 | -143.549 | -16.279 | 24.064 | 1.00 | 64.36 |
| 18408 | CE1 | HIS | D | 40 | -144.022 | -15.304 | 23.307 | 1.00 | 65.09 |
| 18409 | NE2 | HIS | D | 40 | -143.480 | -15.408 | 22.106 | 1.00 | 65.07 |
| 18410 | CD2 | HIS | D | 40 | -142.634 | -16.490 | 22.091 | 1.00 | 64.38 |
| 18411 | C | HIS | D | 40 | -139.571 | -18.893 | 23.892 | 1.00 | 60.71 |
| 18412 | O | HIS | D | 40 | -139.655 | -20.077 | 24.207 | 1.00 | 60.52 |
| 18413 | N | GLU | D | 41 | -138.621 | -18.427 | 23.091 | 1.00 | 61.04 |
| 18414 | CA | GLU | D | 41 | -137.649 | -19.340 | 22.507 | 1.00 | 61.44 |
| 18415 | CB | GLU | D | 41 | -138.019 | -19.651 | 21.055 | 1.00 | 61.41 |
| 18416 | CG | GLU | D | 41 | -139.515 | -19.665 | 20.776 | 1.00 | 62.32 |
| 18417 | CD | GLU | D | 41 | -139.826 | -19.695 | 19.291 | 1.00 | 63.01 |
| 18418 | OE1 | GLU | D | 41 | -140.062 | -18.609 | 18.701 | 1.00 | 62.19 |
| 18419 | OE2 | GLU | D | 41 | -139.823 | -20.808 | 18.719 | 1.00 | 62.93 |
| 18420 | C | GLU | D | 41 | -136.213 | -18.831 | 22.559 | 1.00 | 61.54 |
| 18421 | O | GLU | D | 41 | -135.950 | -17.629 | 22.439 | 1.00 | 61.16 |
| 18422 | N | TYR | D | 42 | -135.290 | -19.776 | 22.719 | 1.00 | 61.94 |
| 18423 | CA | TYR | D | 80 | -133.865 | -19.482 | 22.726 | 1.00 | 62.41 |
| 18424 | CB | TYR | D | 80 | -133.316 | -19.474 | 24.158 | 1.00 | 61.91 |
| 18425 | CG | TYR | D | 80 | -133.498 | -20.769 | 24.922 | 1.00 | 60.62 |
| 18426 | CD1 | TYR | D | 80 | -132.702 | -21.873 | 24.658 | 1.00 | 58.59 |
| 18427 | CE1 | TYR | D | 80 | -132.859 | -23.046 | 25.360 | 1.00 | 57.20 |
| 18428 | CZ | TYR | D | 80 | -133.816 | -23.131 | 26.337 | 1.00 | 56.65 |
| 18429 | OH | TYR | D | 80 | -133.975 | -24.302 | 27.028 | 1.00 | 55.96 |
| 18430 | CE2 | TYR | D | 80 | -134.616 | -22.055 | 26.627 | 1.00 | 57.99 |
| 18431 | CD2 | TYR | D | 80 | -134.456 | -20.879 | 25.921 | 1.00 | 59.62 |
| 18432 | C | TYR | D | 80 | -133.114 | -20.489 | 21.855 | 1.00 | 63.24 |
| 18433 | O | TYR | D | 80 | -133.634 | -21.562 | 21.556 | 1.00 | 63.26 |
| 18434 | N | LEU | D | 81 | -131.894 | -20.142 | 21.457 | 1.00 | 64.36 |
| 18435 | CA | LEU | D | 81 | -131.079 | -21.021 | 20.625 | 1.00 | 65.66 |
| 18436 | CB | LEU | D | 81 | -130.453 | -20.244 | 19.466 | 1.00 | 65.62 |
| 18437 | CG | LEU | D | 81 | -131.386 | -19.504 | 18.506 | 1.00 | 65.31 |
| 18438 | CD1 | LEU | D | 81 | -130.580 | -18.624 | 17.571 | 1.00 | 65.28 |
| 18439 | CD2 | LEU | D | 81 | -132.247 | -20.480 | 17.719 | 1.00 | 65.16 |
| 18440 | C | LEU | D | 81 | -129.974 | -21.688 | 21.429 | 1.00 | 66.80 |
| 18441 | O | LEU | D | 81 | -129.435 | -21.098 | 22.362 | 1.00 | 66.97 |
| 18442 | N | TYR | D | 82 | -129.633 | -22.916 | 21.049 | 1.00 | 68.34 |
| 18443 | CA | TYR | D | 82 | -128.584 | -23.672 | 21.722 | 1.00 | 69.82 |
| 18444 | CB | TYR | D | 82 | -129.186 | -24.540 | 22.828 | 1.00 | 69.95 |
| 18445 | CG | TYR | D | 82 | -128.161 | -25.139 | 23.767 | 1.00 | 70.66 |
| 18446 | CD1 | TYR | D | 82 | -127.468 | -24.340 | 24.665 | 1.00 | 71.01 |
| 18447 | CE1 | TYR | D | 82 | -126.533 | -24.873 | 25.525 | 1.00 | 71.12 |
| 18448 | CZ | TYR | D | 82 | -126.275 | -26.226 | 25.500 | 1.00 | 71.46 |
| 18449 | OH | TYR | D | 82 | -125.335 | -26.752 | 26.360 | 1.00 | 71.77 |
| 18450 | CE2 | TYR | D | 82 | -126.949 | -27.049 | 24.619 | 1.00 | 71.57 |
| 18451 | CD2 | TYR | D | 82 | -127.888 | -26.503 | 23.758 | 1.00 | 71.27 |
| 18452 | C | TYR | D | 82 | -127.848 | -24.549 | 20.717 | 1.00 | 70.76 |

FIGURE 3 MX

| A | B | C | D | E | F | G | H | I | J |
|---|---|---|---|---|---|---|---|---|---|
| 18453 | O | TYR | D | 44 | -128.317 | -24.735 | 19.597 | 1.00 | 70.90 |
| 18454 | N | LYS | D | 45 | -126.699 | -25.088 | 21.114 | 1.00 | 72.12 |
| 18455 | CA | LYS | D | 45 | -125.926 | -25.955 | 20.228 | 1.00 | 73.44 |
| 18456 | CB | LYS | D | 45 | -124.755 | -25.192 | 19.599 | 1.00 | 73.38 |
| 18457 | CG | LYS | D | 45 | -123.953 | -24.337 | 20.555 | 1.00 | 73.74 |
| 18458 | CD | LYS | D | 45 | -122.947 | -23.474 | 19.795 | 1.00 | 74.29 |
| 18459 | CE | LYS | D | 45 | -121.734 | -24.277 | 19.331 | 1.00 | 74.20 |
| 18460 | NZ | LYS | D | 45 | -120.701 | -23.434 | 18.637 | 1.00 | 73.99 |
| 18461 | C | LYS | D | 45 | -125.431 | -27.230 | 20.912 | 1.00 | 74.32 |
| 18462 | O | LYS | D | 45 | -125.079 | -27.211 | 22.090 | 1.00 | 74.42 |
| 18463 | N | GLN | D | 46 | -125.406 | -28.331 | 20.159 | 1.00 | 75.53 |
| 18464 | CA | GLN | D | 46 | -124.943 | -29.626 | 20.670 | 1.00 | 76.63 |
| 18465 | CB | GLN | D | 46 | -126.032 | -30.688 | 20.521 | 1.00 | 76.65 |
| 18466 | CG | GLN | D | 46 | -126.706 | -31.000 | 21.844 | 1.00 | 77.46 |
| 18467 | CD | GLN | D | 46 | -128.140 | -31.440 | 21.695 | 1.00 | 77.98 |
| 18468 | OE1 | GLN | D | 46 | -128.996 | -31.048 | 22.492 | 1.00 | 78.63 |
| 18469 | NE2 | GLN | D | 46 | -128.413 | -32.259 | 20.685 | 1.00 | 78.04 |
| 18470 | C | GLN | D | 46 | -123.618 | -30.101 | 20.060 | 1.00 | 77.22 |
| 18471 | O | GLN | D | 46 | -122.543 | -29.752 | 20.564 | 1.00 | 77.30 |
| 18472 | N | GLU | D | 47 | -123.698 | -30.922 | 19.012 | 1.00 | 77.93 |
| 18473 | CA | GLU | D | 47 | -122.513 | -31.367 | 18.277 | 1.00 | 78.65 |
| 18474 | CB | GLU | D | 47 | -122.956 | -32.049 | 16.974 | 1.00 | 78.73 |
| 18475 | CG | GLU | D | 47 | -121.979 | -33.038 | 16.340 | 1.00 | 79.60 |
| 18476 | CD | GLU | D | 47 | -122.658 | -33.943 | 15.310 | 1.00 | 80.37 |
| 18477 | OE1 | GLU | D | 47 | -122.905 | -35.134 | 15.618 | 1.00 | 80.34 |
| 18478 | OE2 | GLU | D | 47 | -122.958 | -33.464 | 14.193 | 1.00 | 79.84 |
| 18479 | C | GLU | D | 47 | -121.810 | -30.060 | 17.963 | 1.00 | 78.87 |
| 18480 | O | GLU | D | 47 | -120.766 | -29.714 | 18.522 | 1.00 | 78.95 |
| 18481 | N | ASN | D | 48 | -122.439 | -29.340 | 17.051 | 1.00 | 79.03 |
| 18482 | CA | ASN | D | 48 | -122.106 | -27.980 | 16.693 | 1.00 | 79.17 |
| 18483 | CB | ASN | D | 48 | -120.796 | -27.853 | 15.913 | 1.00 | 79.39 |
| 18484 | CG | ASN | D | 48 | -120.312 | -26.396 | 15.808 | 1.00 | 79.85 |
| 18485 | OD1 | ASN | D | 48 | -120.890 | -25.488 | 16.415 | 1.00 | 79.96 |
| 18486 | ND2 | ASN | D | 48 | -119.253 | -26.176 | 15.032 | 1.00 | 79.80 |
| 18487 | C | ASN | D | 48 | -123.322 | -27.634 | 15.864 | 1.00 | 79.05 |
| 18488 | O | ASN | D | 48 | -123.317 | -26.721 | 15.043 | 1.00 | 79.01 |
| 18489 | N | ASN | D | 49 | -124.364 | -28.437 | 16.078 | 1.00 | 78.88 |
| 18490 | CA | ASN | D | 49 | -125.670 | -28.187 | 15.507 | 1.00 | 78.77 |
| 18491 | CB | ASN | D | 49 | -126.641 | -29.306 | 15.883 | 1.00 | 79.00 |
| 18492 | CG | ASN | D | 49 | -126.655 | -30.451 | 14.886 | 1.00 | 79.55 |
| 18493 | OD1 | ASN | D | 49 | -126.781 | -31.610 | 15.275 | 1.00 | 80.11 |
| 18494 | ND2 | ASN | D | 49 | -126.556 | -30.133 | 13.599 | 1.00 | 80.29 |
| 18495 | C | ASN | D | 49 | -126.137 | -26.947 | 16.219 | 1.00 | 78.53 |
| 18496 | O | ASN | D | 49 | -125.639 | -26.640 | 17.299 | 1.00 | 78.67 |
| 18497 | N | ILE | D | 50 | -127.087 | -26.227 | 15.644 | 1.00 | 78.07 |
| 18498 | CA | ILE | D | 50 | -127.646 | -25.083 | 16.352 | 1.00 | 77.53 |
| 18499 | CB | ILE | D | 50 | -127.129 | -23.744 | 15.787 | 1.00 | 77.63 |
| 18500 | CG1 | ILE | D | 50 | -125.938 | -23.273 | 16.632 | 1.00 | 77.74 |
| 18501 | CD1 | ILE | D | 50 | -124.959 | -22.387 | 15.900 | 1.00 | 78.44 |
| 18502 | CG2 | ILE | D | 50 | -128.215 | -22.684 | 15.817 | 1.00 | 77.47 |
| 18503 | C | ILE | D | 50 | -129.164 | -25.189 | 16.423 | 1.00 | 77.15 |

FIGURE 3 MY

| A | B | C | D | E | F | G | H | I | J |
|---|---|---|---|---|---|---|---|---|---|
| 18504 | O | ILE | D | 50 | -129.877 | -24.945 | 15.449 | 1.00 | 77.13 |
| 18505 | N | LEU | D | 51 | -129.637 | -25.585 | 17.600 | 1.00 | 76.58 |
| 18506 | CA | LEU | D | 51 | -131.051 | -25.847 | 17.832 | 1.00 | 76.10 |
| 18507 | CB | LEU | D | 51 | -131.215 | -26.917 | 18.917 | 1.00 | 75.99 |
| 18508 | CG | LEU | D | 51 | -130.782 | -28.350 | 18.608 | 1.00 | 75.89 |
| 18509 | CD1 | LEU | D | 51 | -129.381 | -28.391 | 18.026 | 1.00 | 75.81 |
| 18510 | CD2 | LEU | D | 51 | -130.866 | -29.205 | 19.865 | 1.00 | 75.82 |
| 18511 | C | LEU | D | 51 | -131.871 | -24.626 | 18.228 | 1.00 | 75.75 |
| 18512 | O | LEU | D | 51 | -131.384 | -23.499 | 18.258 | 1.00 | 75.75 |
| 18513 | N | VAL | D | 52 | -133.137 | -24.888 | 18.523 | 1.00 | 75.24 |
| 18514 | CA | VAL | D | 52 | -134.077 | -23.883 | 18.982 | 1.00 | 74.85 |
| 18515 | CB | VAL | D | 52 | -134.992 | -23.372 | 17.851 | 1.00 | 74.86 |
| 18516 | CG1 | VAL | D | 52 | -135.927 | -22.293 | 18.365 | 1.00 | 74.39 |
| 18517 | CG2 | VAL | D | 52 | -135.792 | -24.519 | 17.250 | 1.00 | 75.16 |
| 18518 | C | VAL | D | 52 | -134.926 | -24.584 | 20.021 | 1.00 | 74.56 |
| 18519 | O | VAL | D | 52 | -135.341 | -25.730 | 19.825 | 1.00 | 74.55 |
| 18520 | N | PHE | D | 53 | -135.172 | -23.908 | 21.135 | 1.00 | 74.03 |
| 18521 | CA | PHE | D | 53 | -135.937 | -24.512 | 22.206 | 1.00 | 73.50 |
| 18522 | CB | PHE | D | 53 | -135.085 | -24.629 | 23.467 | 1.00 | 73.31 |
| 18523 | CG | PHE | D | 53 | -134.127 | -25.783 | 23.454 | 1.00 | 72.34 |
| 18524 | CD1 | PHE | D | 53 | -132.980 | -25.745 | 22.677 | 1.00 | 71.52 |
| 18525 | CE1 | PHE | D | 53 | -132.094 | -26.806 | 22.673 | 1.00 | 71.38 |
| 18526 | CZ | PHE | D | 53 | -132.349 | -27.920 | 23.454 | 1.00 | 71.45 |
| 18527 | CE2 | PHE | D | 53 | -133.490 | -27.965 | 24.237 | 1.00 | 71.06 |
| 18528 | CD2 | PHE | D | 53 | -134.367 | -26.901 | 24.237 | 1.00 | 71.23 |
| 18529 | C | PHE | D | 53 | -137.189 | -23.727 | 22.533 | 1.00 | 73.55 |
| 18530 | O | PHE | D | 53 | -137.224 | -22.503 | 22.436 | 1.00 | 73.37 |
| 18531 | N | ASN | D | 54 | -138.229 | -24.452 | 22.911 | 1.00 | 73.74 |
| 18532 | CA | ASN | D | 54 | -139.442 | -23.828 | 23.393 | 1.00 | 74.00 |
| 18533 | CB | ASN | D | 54 | -140.656 | -24.691 | 23.059 | 1.00 | 73.94 |
| 18534 | CG | ASN | D | 54 | -141.966 | -23.973 | 23.303 | 1.00 | 73.93 |
| 18535 | OD1 | ASN | D | 54 | -142.492 | -23.295 | 22.414 | 1.00 | 74.01 |
| 18536 | ND2 | ASN | D | 54 | -142.503 | -24.115 | 24.511 | 1.00 | 73.20 |
| 18537 | C | ASN | D | 54 | -139.237 | -23.743 | 24.896 | 1.00 | 74.19 |
| 18538 | O | ASN | D | 54 | -138.985 | -24.757 | 25.543 | 1.00 | 74.23 |
| 18539 | N | ALA | D | 55 | -139.306 | -22.543 | 25.454 | 1.00 | 74.39 |
| 18540 | CA | ALA | D | 55 | -139.037 | -22.393 | 26.876 | 1.00 | 74.79 |
| 18541 | CB | ALA | D | 55 | -138.990 | -20.924 | 27.270 | 1.00 | 74.66 |
| 18542 | C | ALA | D | 55 | -140.082 | -23.128 | 27.687 | 1.00 | 75.07 |
| 18543 | O | ALA | D | 55 | -139.766 | -23.828 | 28.650 | 1.00 | 74.91 |
| 18544 | N | GLU | D | 56 | -141.330 | -22.981 | 27.271 | 1.00 | 75.59 |
| 18545 | CA | GLU | D | 56 | -142.441 | -23.583 | 27.981 | 1.00 | 76.20 |
| 18546 | CB | GLU | D | 56 | -143.759 | -23.051 | 27.421 | 1.00 | 76.39 |
| 18547 | CG | GLU | D | 56 | -144.987 | -23.506 | 28.187 | 1.00 | 77.36 |
| 18548 | CD | GLU | D | 56 | -145.964 | -22.373 | 28.429 | 1.00 | 78.96 |
| 18549 | OE1 | GLU | D | 56 | -146.895 | -22.191 | 27.608 | 1.00 | 78.93 |
| 18550 | OE2 | GLU | D | 56 | -145.789 | -21.659 | 29.445 | 1.00 | 79.50 |
| 18551 | C | GLU | D | 56 | -142.420 | -25.105 | 27.940 | 1.00 | 76.45 |
| 18552 | O | GLU | D | 56 | -142.755 | -25.758 | 28.929 | 1.00 | 76.46 |
| 18553 | N | TYR | D | 57 | -142.010 | -25.672 | 26.808 | 1.00 | 76.74 |
| 18554 | CA | TYR | D | 57 | -142.025 | -27.128 | 26.646 | 1.00 | 77.16 |

FIGURE 3 MZ

| A | B | C | D | E | F | G | H | I | J |
|---|---|---|---|---|---|---|---|---|---|
| 18555 | CB | TYR | D | 57 | -142.721 | -27.512 | 25.338 | 1.00 | 77.31 |
| 18556 | CG | TYR | D | 57 | -144.107 | -26.930 | 25.186 | 1.00 | 77.56 |
| 18557 | CD1 | TYR | D | 57 | -144.962 | -26.823 | 26.276 | 1.00 | 78.01 |
| 18558 | CE1 | TYR | D | 57 | -146.233 | -26.290 | 26.140 | 1.00 | 78.45 |
| 18559 | CZ | TYR | D | 57 | -146.661 | -25.857 | 24.899 | 1.00 | 78.98 |
| 18560 | OH | TYR | D | 57 | -147.924 | -25.329 | 24.753 | 1.00 | 79.47 |
| 18561 | CE2 | TYR | D | 57 | -145.827 | -25.952 | 23.803 | 1.00 | 78.89 |
| 18562 | CD2 | TYR | D | 57 | -144.560 | -26.488 | 23.951 | 1.00 | 78.24 |
| 18563 | C | TYR | D | 57 | -140.649 | -27.788 | 26.704 | 1.00 | 77.30 |
| 18564 | O | TYR | D | 57 | -140.448 | -28.750 | 27.451 | 1.00 | 77.24 |
| 18565 | N | GLY | D | 58 | -139.713 | -27.286 | 25.902 | 1.00 | 77.50 |
| 18566 | CA | GLY | D | 58 | -138.367 | -27.836 | 25.867 | 1.00 | 77.58 |
| 18567 | C | GLY | D | 58 | -137.942 | -28.299 | 24.486 | 1.00 | 77.47 |
| 18568 | O | GLY | D | 58 | -137.676 | -29.481 | 24.271 | 1.00 | 77.49 |
| 18569 | N | VAL | D | 62 | -133.961 | -29.159 | 15.079 | 1.00 | 83.22 |
| 18570 | CA | VAL | D | 62 | -132.871 | -28.300 | 14.537 | 1.00 | 83.38 |
| 18571 | CB | VAL | D | 62 | -132.081 | -29.032 | 13.430 | 1.00 | 83.34 |
| 18572 | CG1 | VAL | D | 62 | -130.908 | -28.195 | 12.960 | 1.00 | 83.33 |
| 18573 | CG2 | VAL | D | 62 | -131.602 | -30.384 | 13.928 | 1.00 | 83.42 |
| 18574 | C | VAL | D | 62 | -133.424 | -26.981 | 13.990 | 1.00 | 83.44 |
| 18575 | O | VAL | D | 62 | -134.581 | -26.903 | 13.581 | 1.00 | 83.40 |
| 18576 | N | PHE | D | 63 | -132.591 | -25.947 | 14.008 | 1.00 | 83.48 |
| 18577 | CA | PHE | D | 63 | -132.954 | -24.638 | 13.484 | 1.00 | 83.59 |
| 18578 | CB | PHE | D | 63 | -132.846 | -23.575 | 14.581 | 1.00 | 83.53 |
| 18579 | CG | PHE | D | 63 | -132.810 | -22.160 | 14.063 | 1.00 | 83.01 |
| 18580 | CD1 | PHE | D | 63 | -131.605 | -21.553 | 13.744 | 1.00 | 82.34 |
| 18581 | CE1 | PHE | D | 63 | -131.571 | -20.258 | 13.270 | 1.00 | 82.12 |
| 18582 | CZ | PHE | D | 63 | -132.746 | -19.549 | 13.116 | 1.00 | 82.46 |
| 18583 | CE2 | PHE | D | 63 | -133.952 | -20.137 | 13.434 | 1.00 | 82.52 |
| 18584 | CD2 | PHE | D | 63 | -133.980 | -21.436 | 13.904 | 1.00 | 82.81 |
| 18585 | C | PHE | D | 63 | -131.984 | -24.325 | 12.360 | 1.00 | 83.79 |
| 18586 | O | PHE | D | 63 | -132.303 | -23.604 | 11.413 | 1.00 | 83.64 |
| 18587 | N | LEU | D | 64 | -130.791 | -24.892 | 12.487 | 1.00 | 84.09 |
| 18588 | CA | LEU | D | 64 | -129.728 | -24.728 | 11.513 | 1.00 | 84.53 |
| 18589 | CB | LEU | D | 64 | -129.156 | -23.315 | 11.593 | 1.00 | 84.49 |
| 18590 | CG | LEU | D | 64 | -128.367 | -22.810 | 10.387 | 1.00 | 84.86 |
| 18591 | CD1 | LEU | D | 64 | -126.883 | -23.100 | 10.544 | 1.00 | 85.36 |
| 18592 | CD2 | LEU | D | 64 | -128.912 | -23.405 | 9.098 | 1.00 | 85.27 |
| 18593 | C | LEU | D | 64 | -128.676 | -25.771 | 11.857 | 1.00 | 84.75 |
| 18594 | O | LEU | D | 64 | -128.028 | -25.688 | 12.897 | 1.00 | 84.83 |
| 18595 | N | GLU | D | 65 | -128.530 | -26.773 | 10.999 | 1.00 | 85.08 |
| 18596 | CA | GLU | D | 65 | -127.599 | -27.863 | 11.270 | 1.00 | 85.31 |
| 18597 | CB | GLU | D | 65 | -128.250 | -29.215 | 10.961 | 1.00 | 85.43 |
| 18598 | CG | GLU | D | 65 | -128.834 | -29.335 | 9.559 | 1.00 | 85.81 |
| 18599 | CD | GLU | D | 65 | -128.974 | -30.781 | 9.108 | 1.00 | 86.74 |
| 18600 | OE1 | GLU | D | 65 | -129.157 | -31.019 | 7.890 | 1.00 | 86.19 |
| 18601 | OE2 | GLU | D | 65 | -128.892 | -31.682 | 9.973 | 1.00 | 87.10 |
| 18602 | C | GLU | D | 65 | -126.310 | -27.720 | 10.482 | 1.00 | 85.36 |
| 18603 | O | GLU | D | 65 | -126.332 | -27.649 | 9.255 | 1.00 | 85.27 |
| 18604 | N | ASN | D | 66 | -125.177 | -27.682 | 11.172 | 1.00 | 85.66 |
| 18605 | CA | ASN | D | 66 | -123.935 | -27.549 | 10.429 | 1.00 | 85.86 |

FIGURE 3 NA

| A | B | C | D | E | F | G | H | I | J |
|---|---|---|---|---|---|---|---|---|---|
| 18606 | CB  | ASN | D | 66 | -122.739 | -27.089 | 11.261 | 1.00 | 85.95 |
| 18607 | CG  | ASN | D | 66 | -121.740 | -26.298 | 10.423 | 1.00 | 86.51 |
| 18608 | OD1 | ASN | D | 66 | -121.971 | -26.056 |  9.231 | 1.00 | 86.46 |
| 18609 | ND2 | ASN | D | 66 | -120.634 | -25.886 | 11.038 | 1.00 | 86.95 |
| 18610 | C   | ASN | D | 66 | -123.632 | -28.797 |  9.625 | 1.00 | 85.77 |
| 18611 | O   | ASN | D | 66 | -123.426 | -29.897 | 10.150 | 1.00 | 85.83 |
| 18612 | N   | SER | D | 67 | -123.642 | -28.560 |  8.325 | 1.00 | 85.60 |
| 18613 | CA  | SER | D | 67 | -123.456 | -29.518 |  7.266 | 1.00 | 85.38 |
| 18614 | CB  | SER | D | 67 | -124.434 | -30.681 |  7.392 | 1.00 | 85.46 |
| 18615 | OG  | SER | D | 67 | -125.754 | -30.273 |  7.079 | 1.00 | 85.72 |
| 18616 | C   | SER | D | 67 | -123.911 | -28.552 |  6.207 | 1.00 | 85.18 |
| 18617 | O   | SER | D | 67 | -123.708 | -28.739 |  5.006 | 1.00 | 85.31 |
| 18618 | N   | THR | D | 68 | -124.525 | -27.487 |  6.721 | 1.00 | 84.81 |
| 18619 | CA  | THR | D | 68 | -125.035 | -26.374 |  5.946 | 1.00 | 84.50 |
| 18620 | CB  | THR | D | 68 | -125.882 | -25.472 |  6.856 | 1.00 | 84.49 |
| 18621 | OG1 | THR | D | 68 | -126.882 | -26.254 |  7.520 | 1.00 | 84.48 |
| 18622 | CG2 | THR | D | 68 | -126.690 | -24.480 |  6.034 | 1.00 | 84.49 |
| 18623 | C   | THR | D | 68 | -123.864 | -25.567 |  5.426 | 1.00 | 84.31 |
| 18624 | O   | THR | D | 68 | -123.836 | -25.145 |  4.271 | 1.00 | 84.14 |
| 18625 | N   | PHE | D | 69 | -122.893 | -25.352 |  6.301 | 1.00 | 84.23 |
| 18626 | CA  | PHE | D | 69 | -121.712 | -24.591 |  5.944 | 1.00 | 84.08 |
| 18627 | CB  | PHE | D | 69 | -121.579 | -23.375 |  6.855 | 1.00 | 83.82 |
| 18628 | CG  | PHE | D | 69 | -122.827 | -22.544 |  6.934 | 1.00 | 82.91 |
| 18629 | CD1 | PHE | D | 69 | -123.228 | -21.771 |  5.856 | 1.00 | 82.28 |
| 18630 | CE1 | PHE | D | 69 | -124.377 | -21.001 |  5.923 | 1.00 | 81.61 |
| 18631 | CZ  | PHE | D | 69 | -125.137 | -21.000 |  7.070 | 1.00 | 81.37 |
| 18632 | CE2 | PHE | D | 69 | -124.748 | -21.769 |  8.152 | 1.00 | 81.68 |
| 18633 | CD2 | PHE | D | 69 | -123.600 | -22.535 |  8.081 | 1.00 | 81.88 |
| 18634 | C   | PHE | D | 69 | -120.481 | -25.474 |  6.026 | 1.00 | 84.24 |
| 18635 | O   | PHE | D | 69 | -119.565 | -25.219 |  6.806 | 1.00 | 84.37 |
| 18636 | N   | ASP | D | 70 | -120.470 | -26.525 |  5.216 | 1.00 | 84.43 |
| 18637 | CA  | ASP | D | 70 | -119.340 | -27.443 |  5.202 | 1.00 | 84.64 |
| 18638 | CB  | ASP | D | 70 | -119.796 | -28.881 |  5.472 | 1.00 | 84.75 |
| 18639 | CG  | ASP | D | 70 | -120.033 | -29.147 |  6.958 | 1.00 | 85.27 |
| 18640 | OD1 | ASP | D | 70 | -119.480 | -28.400 |  7.797 | 1.00 | 85.62 |
| 18641 | OD2 | ASP | D | 70 | -120.749 | -30.077 |  7.387 | 1.00 | 85.61 |
| 18642 | C   | ASP | D | 70 | -118.503 | -27.333 |  3.927 | 1.00 | 84.52 |
| 18643 | O   | ASP | D | 70 | -117.520 | -28.050 |  3.763 | 1.00 | 84.45 |
| 18644 | N   | GLU | D | 71 | -118.898 | -26.430 |  3.032 | 1.00 | 84.45 |
| 18645 | CA  | GLU | D | 71 | -118.112 | -26.151 |  1.830 | 1.00 | 84.41 |
| 18646 | CB  | GLU | D | 71 | -118.313 | -27.217 |  0.733 | 1.00 | 84.55 |
| 18647 | CG  | GLU | D | 71 | -119.445 | -26.955 | -0.245 | 1.00 | 85.22 |
| 18648 | CD  | GLU | D | 71 | -119.026 | -27.195 | -1.687 | 1.00 | 86.06 |
| 18649 | OE1 | GLU | D | 71 | -119.589 | -26.533 | -2.591 | 1.00 | 86.19 |
| 18650 | OE2 | GLU | D | 71 | -118.128 | -28.037 | -1.917 | 1.00 | 86.29 |
| 18651 | C   | GLU | D | 71 | -118.344 | -24.713 |  1.336 | 1.00 | 84.10 |
| 18652 | O   | GLU | D | 71 | -118.526 | -24.449 |  0.145 | 1.00 | 84.10 |
| 18653 | N   | PHE | D | 72 | -118.336 | -23.782 |  2.282 | 1.00 | 83.66 |
| 18654 | CA  | PHE | D | 72 | -118.477 | -22.371 |  1.949 | 1.00 | 83.21 |
| 18655 | CB  | PHE | D | 72 | -119.472 | -21.669 |  2.881 | 1.00 | 83.47 |
| 18656 | CG  | PHE | D | 72 | -118.846 | -21.054 |  4.094 | 1.00 | 83.83 |

FIGURE 3 NB

| A | B | C | D | E | F | G | H | I | J |
|---|---|---|---|---|---|---|---|---|---|
| 18657 | CD1 | PHE | D | 72 | -118.310 | -21.847 | 5.093 | 1.00 | 84.40 |
| 18658 | CE1 | PHE | D | 72 | -117.737 | -21.277 | 6.210 | 1.00 | 84.80 |
| 18659 | CZ | PHE | D | 72 | -117.695 | -19.901 | 6.341 | 1.00 | 84.99 |
| 18660 | CE2 | PHE | D | 72 | -118.229 | -19.100 | 5.352 | 1.00 | 84.80 |
| 18661 | CD2 | PHE | D | 72 | -118.803 | -19.677 | 4.239 | 1.00 | 84.27 |
| 18662 | C | PHE | D | 72 | -117.093 | -21.715 | 1.967 | 1.00 | 82.57 |
| 18663 | O | PHE | D | 72 | -116.947 | -20.506 | 1.754 | 1.00 | 82.33 |
| 18664 | N | GLY | D | 73 | -116.085 | -22.544 | 2.238 | 1.00 | 81.88 |
| 18665 | CA | GLY | D | 73 | -114.693 | -22.138 | 2.155 | 1.00 | 80.90 |
| 18666 | C | GLY | D | 73 | -113.908 | -21.819 | 3.414 | 1.00 | 80.12 |
| 18667 | O | GLY | D | 73 | -112.691 | -22.018 | 3.447 | 1.00 | 80.16 |
| 18668 | N | HIS | D | 74 | -114.571 | -21.317 | 4.448 | 1.00 | 79.14 |
| 18669 | CA | HIS | D | 74 | -113.844 | -20.912 | 5.644 | 1.00 | 78.20 |
| 18670 | CB | HIS | D | 74 | -113.872 | -19.391 | 5.784 | 1.00 | 78.23 |
| 18671 | CG | HIS | D | 74 | -113.674 | -18.651 | 4.494 | 1.00 | 78.28 |
| 18672 | ND1 | HIS | D | 74 | -112.450 | -18.146 | 4.105 | 1.00 | 78.33 |
| 18673 | CE1 | HIS | D | 74 | -112.579 | -17.529 | 2.944 | 1.00 | 78.17 |
| 18674 | NE2 | HIS | D | 74 | -113.843 | -17.608 | 2.568 | 1.00 | 77.82 |
| 18675 | CD2 | HIS | D | 74 | -114.549 | -18.304 | 3.519 | 1.00 | 78.10 |
| 18676 | C | HIS | D | 74 | -114.389 | -21.552 | 6.910 | 1.00 | 77.45 |
| 18677 | O | HIS | D | 74 | -115.388 | -22.264 | 6.872 | 1.00 | 77.60 |
| 18678 | N | SER | D | 75 | -113.716 | -21.316 | 8.031 | 1.00 | 76.48 |
| 18679 | CA | SER | D | 75 | -114.196 | -21.825 | 9.312 | 1.00 | 75.42 |
| 18680 | CB | SER | D | 75 | -113.045 | -22.173 | 10.250 | 1.00 | 75.46 |
| 18681 | OG | SER | D | 75 | -113.531 | -22.861 | 11.388 | 1.00 | 74.94 |
| 18682 | C | SER | D | 75 | -115.089 | -20.760 | 9.931 | 1.00 | 74.71 |
| 18683 | O | SER | D | 75 | -114.994 | -19.584 | 9.575 | 1.00 | 74.71 |
| 18684 | N | ILE | D | 76 | -115.956 | -21.163 | 10.853 | 1.00 | 73.61 |
| 18685 | CA | ILE | D | 76 | -116.908 | -20.220 | 11.426 | 1.00 | 72.53 |
| 18686 | CB | ILE | D | 76 | -118.347 | -20.638 | 11.075 | 1.00 | 72.60 |
| 18687 | CG1 | ILE | D | 76 | -118.484 | -20.801 | 9.561 | 1.00 | 72.56 |
| 18688 | CD1 | ILE | D | 76 | -119.863 | -21.200 | 9.099 | 1.00 | 71.45 |
| 18689 | CG2 | ILE | D | 76 | -119.346 | -19.612 | 11.601 | 1.00 | 72.53 |
| 18690 | C | ILE | D | 76 | -116.747 | -20.017 | 12.931 | 1.00 | 71.73 |
| 18691 | O | ILE | D | 76 | -117.134 | -20.869 | 13.741 | 1.00 | 71.52 |
| 18692 | N | ASN | D | 77 | -116.181 | -18.871 | 13.292 | 1.00 | 70.56 |
| 18693 | CA | ASN | D | 77 | -115.957 | -18.530 | 14.689 | 1.00 | 69.44 |
| 18694 | CB | ASN | D | 77 | -114.990 | -17.352 | 14.805 | 1.00 | 69.52 |
| 18695 | CG | ASN | D | 77 | -114.734 | -16.953 | 16.241 | 1.00 | 69.69 |
| 18696 | OD1 | ASN | D | 77 | -114.420 | -17.798 | 17.078 | 1.00 | 70.75 |
| 18697 | ND2 | ASN | D | 77 | -114.881 | -15.666 | 16.541 | 1.00 | 69.22 |
| 18698 | C | ASN | D | 77 | -117.255 | -18.202 | 15.407 | 1.00 | 68.57 |
| 18699 | O | ASN | D | 77 | -117.593 | -18.819 | 16.414 | 1.00 | 68.24 |
| 18700 | N | ASP | D | 78 | -117.986 | -17.226 | 14.881 | 1.00 | 67.69 |
| 18701 | CA | ASP | D | 78 | -119.234 | -16.817 | 15.507 | 1.00 | 66.94 |
| 18702 | CB | ASP | D | 78 | -119.013 | -15.598 | 16.398 | 1.00 | 66.72 |
| 18703 | CG | ASP | D | 78 | -119.851 | -15.638 | 17.657 | 1.00 | 66.78 |
| 18704 | OD1 | ASP | D | 78 | -120.937 | -16.258 | 17.648 | 1.00 | 65.33 |
| 18705 | OD2 | ASP | D | 78 | -119.495 | -15.079 | 18.717 | 1.00 | 68.20 |
| 18706 | C | ASP | D | 78 | -120.286 | -16.494 | 14.469 | 1.00 | 66.38 |
| 18707 | O | ASP | D | 78 | -119.969 | -16.197 | 13.318 | 1.00 | 66.58 |

FIGURE 3 NC

| A | B | C | D | E | F | G | H | I | J |
|---|---|---|---|---|---|---|---|---|---|
| 18708 | N | TYR | D | 79 | -121.542 | -16.537 | 14.890 | 1.00 | 65.60 |
| 18709 | CA | TYR | D | 79 | -122.648 | -16.235 | 14.007 | 1.00 | 65.15 |
| 18710 | CB | TYR | D | 79 | -123.374 | -17.520 | 13.612 | 1.00 | 65.19 |
| 18711 | CG | TYR | D | 79 | -124.214 | -18.068 | 14.734 | 1.00 | 65.06 |
| 18712 | CD1 | TYR | D | 79 | -123.661 | -18.893 | 15.705 | 1.00 | 64.87 |
| 18713 | CE1 | TYR | D | 79 | -124.429 | -19.383 | 16.740 | 1.00 | 64.97 |
| 18714 | CZ | TYR | D | 79 | -125.765 | -19.041 | 16.816 | 1.00 | 65.33 |
| 18715 | OH | TYR | D | 79 | -126.555 | -19.514 | 17.842 | 1.00 | 65.81 |
| 18716 | CE2 | TYR | D | 79 | -126.326 | -18.218 | 15.868 | 1.00 | 65.17 |
| 18717 | CD2 | TYR | D | 79 | -125.553 | -17.735 | 14.841 | 1.00 | 64.78 |
| 18718 | C | TYR | D | 79 | -123.620 | -15.327 | 14.729 | 1.00 | 64.70 |
| 18719 | O | TYR | D | 79 | -123.613 | -15.245 | 15.948 | 1.00 | 64.70 |
| 18720 | N | SER | D | 80 | -124.461 | -14.647 | 13.966 | 1.00 | 64.24 |
| 18721 | CA | SER | D | 80 | -125.489 | -13.801 | 14.539 | 1.00 | 63.93 |
| 18722 | CB | SER | D | 80 | -125.011 | -12.353 | 14.643 | 1.00 | 64.13 |
| 18723 | OG | SER | D | 80 | -126.094 | -11.481 | 14.935 | 1.00 | 64.06 |
| 18724 | C | SER | D | 80 | -126.739 | -13.888 | 13.674 | 1.00 | 63.70 |
| 18725 | O | SER | D | 80 | -126.727 | -13.531 | 12.498 | 1.00 | 63.51 |
| 18726 | N | ILE | D | 81 | -127.818 | -14.381 | 14.259 | 1.00 | 63.43 |
| 18727 | CA | ILE | D | 81 | -129.068 | -14.490 | 13.536 | 1.00 | 63.30 |
| 18728 | CB | ILE | D | 81 | -129.919 | -15.648 | 14.109 | 1.00 | 63.41 |
| 18729 | CG1 | ILE | D | 81 | -131.067 | -15.998 | 13.172 | 1.00 | 63.41 |
| 18730 | CD1 | ILE | D | 81 | -132.395 | -15.522 | 13.681 | 1.00 | 64.28 |
| 18731 | CG2 | ILE | D | 81 | -130.482 | -15.281 | 15.471 | 1.00 | 63.53 |
| 18732 | C | ILE | D | 81 | -129.814 | -13.164 | 13.608 | 1.00 | 63.27 |
| 18733 | O | ILE | D | 81 | -129.892 | -12.537 | 14.670 | 1.00 | 63.14 |
| 18734 | N | SER | D | 82 | -130.330 | -12.723 | 12.466 | 1.00 | 63.18 |
| 18735 | CA | SER | D | 82 | -131.118 | -11.502 | 12.402 | 1.00 | 63.33 |
| 18736 | CB | SER | D | 82 | -131.666 | -11.315 | 10.985 | 1.00 | 63.49 |
| 18737 | OG | SER | D | 82 | -133.021 | -10.893 | 11.001 | 1.00 | 64.27 |
| 18738 | C | SER | D | 82 | -132.255 | -11.598 | 13.418 | 1.00 | 63.16 |
| 18739 | O | SER | D | 82 | -132.758 | -12.683 | 13.683 | 1.00 | 63.06 |
| 18740 | N | PRO | D | 83 | -132.644 | -10.472 | 14.002 | 1.00 | 63.18 |
| 18741 | CA | PRO | D | 83 | -133.703 | -10.453 | 15.018 | 1.00 | 63.33 |
| 18742 | CB | PRO | D | 83 | -133.758 | -8.980 | 15.438 | 1.00 | 63.18 |
| 18743 | CG | PRO | D | 83 | -132.471 | -8.414 | 15.001 | 1.00 | 63.17 |
| 18744 | CD | PRO | D | 83 | -132.095 | -9.132 | 13.747 | 1.00 | 63.09 |
| 18745 | C | PRO | D | 83 | -135.070 | -10.882 | 14.481 | 1.00 | 63.62 |
| 18746 | O | PRO | D | 83 | -135.923 | -11.318 | 15.263 | 1.00 | 63.80 |
| 18747 | N | ASP | D | 84 | -135.284 | -10.754 | 13.173 | 1.00 | 63.53 |
| 18748 | CA | ASP | D | 84 | -136.564 | -11.137 | 12.586 | 1.00 | 63.36 |
| 18749 | CB | ASP | D | 84 | -136.971 | -10.178 | 11.466 | 1.00 | 63.39 |
| 18750 | CG | ASP | D | 84 | -136.091 | -10.295 | 10.248 | 1.00 | 63.23 |
| 18751 | OD1 | ASP | D | 84 | -135.357 | -11.301 | 10.130 | 1.00 | 62.23 |
| 18752 | OD2 | ASP | D | 84 | -136.072 | -9.421 | 9.356 | 1.00 | 63.40 |
| 18753 | C | ASP | D | 84 | -136.539 | -12.569 | 12.083 | 1.00 | 63.32 |
| 18754 | O | ASP | D | 84 | -137.450 | -13.010 | 11.392 | 1.00 | 63.35 |
| 18755 | N | GLY | D | 85 | -135.474 | -13.284 | 12.424 | 1.00 | 63.38 |
| 18756 | CA | GLY | D | 85 | -135.340 | -14.685 | 12.077 | 1.00 | 63.24 |
| 18757 | C | GLY | D | 85 | -135.015 | -14.989 | 10.630 | 1.00 | 63.26 |
| 18758 | O | GLY | D | 85 | -134.825 | -16.151 | 10.277 | 1.00 | 63.30 |

FIGURE 3 ND

| A | B | C | D | E | F | G | H | I | J |
|---|---|---|---|---|---|---|---|---|---|
| 18759 | N | GLN | D | 86 | -134.934 | -13.961 | 9.792 | 1.00 | 63.30 |
| 18760 | CA | GLN | D | 86 | -134.673 | -14.169 | 8.368 | 1.00 | 63.43 |
| 18761 | CB | GLN | D | 86 | -135.209 | -12.998 | 7.541 | 1.00 | 63.52 |
| 18762 | CG | GLN | D | 86 | -136.733 | -12.951 | 7.521 | 1.00 | 64.35 |
| 18763 | CD | GLN | D | 86 | -137.282 | -11.754 | 6.778 | 1.00 | 65.38 |
| 18764 | OE1 | GLN | D | 86 | -137.961 | -10.912 | 7.372 | 1.00 | 65.62 |
| 18765 | NE2 | GLN | D | 86 | -137.002 | -11.675 | 5.476 | 1.00 | 65.65 |
| 18766 | C | GLN | D | 86 | -133.218 | -14.475 | 8.008 | 1.00 | 63.32 |
| 18767 | O | GLN | D | 86 | -132.924 | -15.501 | 7.397 | 1.00 | 63.52 |
| 18768 | N | PHE | D | 87 | -132.304 | -13.593 | 8.392 | 1.00 | 63.19 |
| 18769 | CA | PHE | D | 87 | -130.907 | -13.772 | 8.021 | 1.00 | 62.76 |
| 18770 | CB | PHE | D | 87 | -130.344 | -12.466 | 7.482 | 1.00 | 62.99 |
| 18771 | CG | PHE | D | 87 | -131.043 | -11.970 | 6.262 | 1.00 | 63.91 |
| 18772 | CD1 | PHE | D | 87 | -130.733 | -12.487 | 5.014 | 1.00 | 64.41 |
| 18773 | CE1 | PHE | D | 87 | -131.373 | -12.027 | 3.877 | 1.00 | 64.88 |
| 18774 | CZ | PHE | D | 87 | -132.336 | -11.043 | 3.981 | 1.00 | 65.49 |
| 18775 | CE2 | PHE | D | 87 | -132.657 | -10.518 | 5.228 | 1.00 | 65.49 |
| 18776 | CD2 | PHE | D | 87 | -132.011 | -10.984 | 6.358 | 1.00 | 64.68 |
| 18777 | C | PHE | D | 87 | -129.996 | -14.282 | 9.132 | 1.00 | 62.35 |
| 18778 | O | PHE | D | 87 | -130.378 | -14.352 | 10.300 | 1.00 | 62.63 |
| 18779 | N | ILE | D | 88 | -128.786 | -14.656 | 8.736 | 1.00 | 61.42 |
| 18780 | CA | ILE | D | 88 | -127.760 | -15.054 | 9.673 | 1.00 | 60.54 |
| 18781 | CB | ILE | D | 88 | -127.588 | -16.577 | 9.741 | 1.00 | 60.82 |
| 18782 | CG1 | ILE | D | 88 | -126.251 | -16.918 | 10.413 | 1.00 | 60.96 |
| 18783 | CD1 | ILE | D | 88 | -126.024 | -18.405 | 10.653 | 1.00 | 62.14 |
| 18784 | CG2 | ILE | D | 88 | -127.633 | -17.170 | 8.368 | 1.00 | 60.40 |
| 18785 | C | ILE | D | 88 | -126.462 | -14.419 | 9.241 | 1.00 | 59.79 |
| 18786 | O | ILE | D | 88 | -126.043 | -14.541 | 8.087 | 1.00 | 59.64 |
| 18787 | N | LEU | D | 89 | -125.842 | -13.711 | 10.175 | 1.00 | 58.71 |
| 18788 | CA | LEU | D | 89 | -124.556 | -13.117 | 9.923 | 1.00 | 57.45 |
| 18789 | CB | LEU | D | 89 | -124.316 | -11.987 | 10.909 | 1.00 | 57.41 |
| 18790 | CG | LEU | D | 89 | -123.070 | -11.161 | 10.622 | 1.00 | 57.49 |
| 18791 | CD1 | LEU | D | 89 | -122.988 | -10.017 | 11.608 | 1.00 | 57.05 |
| 18792 | CD2 | LEU | D | 89 | -123.098 | -10.650 | 9.191 | 1.00 | 56.64 |
| 18793 | C | LEU | D | 89 | -123.532 | -14.215 | 10.128 | 1.00 | 56.69 |
| 18794 | O | LEU | D | 89 | -123.682 | -15.044 | 11.029 | 1.00 | 56.50 |
| 18795 | N | LEU | D | 90 | -122.513 | -14.254 | 9.277 | 1.00 | 55.64 |
| 18796 | CA | LEU | D | 90 | -121.441 | -15.228 | 9.447 | 1.00 | 54.69 |
| 18797 | CB | LEU | D | 90 | -121.392 | -16.246 | 8.306 | 1.00 | 54.88 |
| 18798 | CG | LEU | D | 90 | -122.565 | -17.225 | 8.179 | 1.00 | 55.57 |
| 18799 | CD1 | LEU | D | 90 | -122.482 | -18.002 | 6.863 | 1.00 | 55.72 |
| 18800 | CD2 | LEU | D | 90 | -122.642 | -18.193 | 9.369 | 1.00 | 56.14 |
| 18801 | C | LEU | D | 90 | -120.106 | -14.514 | 9.612 | 1.00 | 53.74 |
| 18802 | O | LEU | D | 90 | -119.693 | -13.708 | 8.777 | 1.00 | 53.63 |
| 18803 | N | GLU | D | 91 | -119.452 | -14.821 | 10.720 | 1.00 | 52.71 |
| 18804 | CA | GLU | D | 91 | -118.185 | -14.228 | 11.089 | 1.00 | 51.54 |
| 18805 | CB | GLU | D | 91 | -118.241 | -13.849 | 12.569 | 1.00 | 51.93 |
| 18806 | CG | GLU | D | 91 | -117.111 | -12.974 | 13.083 | 1.00 | 52.01 |
| 18807 | CD | GLU | D | 91 | -117.414 | -12.450 | 14.471 | 1.00 | 52.71 |
| 18808 | OE1 | GLU | D | 91 | -117.001 | -13.103 | 15.455 | 1.00 | 53.26 |
| 18809 | OE2 | GLU | D | 91 | -118.089 | -11.402 | 14.574 | 1.00 | 52.28 |

FIGURE 3 NE

| A | B | C | D | E | F | G | H | I | J |
|---|---|---|---|---|---|---|---|---|---|
| 18810 | C | GLU | D | 91 | -117.083 | -15.244 | 10.879 | 1.00 | 50.56 |
| 18811 | O | GLU | D | 91 | -117.157 | -16.374 | 11.378 | 1.00 | 50.30 |
| 18812 | N | TYR | D | 92 | -116.055 | -14.837 | 10.149 | 1.00 | 49.43 |
| 18813 | CA | TYR | D | 92 | -114.918 | -15.707 | 9.899 | 1.00 | 48.37 |
| 18814 | CB | TYR | D | 92 | -115.196 | -16.650 | 8.724 | 1.00 | 48.77 |
| 18815 | CG | TYR | D | 92 | -115.437 | -15.951 | 7.407 | 1.00 | 47.98 |
| 18816 | CD1 | TYR | D | 92 | -116.603 | -15.238 | 7.186 | 1.00 | 48.58 |
| 18817 | CE1 | TYR | D | 92 | -116.833 | -14.598 | 5.977 | 1.00 | 50.05 |
| 18818 | CZ | TYR | D | 92 | -115.884 | -14.676 | 4.976 | 1.00 | 49.53 |
| 18819 | OH | TYR | D | 92 | -116.112 | -14.035 | 3.780 | 1.00 | 50.03 |
| 18820 | CE2 | TYR | D | 92 | -114.713 | -15.384 | 5.180 | 1.00 | 48.92 |
| 18821 | CD2 | TYR | D | 92 | -114.500 | -16.016 | 6.386 | 1.00 | 47.76 |
| 18822 | C | TYR | D | 92 | -113.695 | -14.847 | 9.642 | 1.00 | 47.68 |
| 18823 | O | TYR | D | 92 | -113.818 | -13.648 | 9.395 | 1.00 | 47.18 |
| 18824 | N | ASN | D | 93 | -112.521 | -15.463 | 9.692 | 1.00 | 47.05 |
| 18825 | CA | ASN | D | 93 | -111.272 | -14.721 | 9.583 | 1.00 | 47.12 |
| 18826 | CB | ASN | D | 93 | -111.129 | -14.065 | 8.215 | 1.00 | 47.56 |
| 18827 | CG | ASN | D | 93 | -110.728 | -15.063 | 7.146 | 1.00 | 49.03 |
| 18828 | OD1 | ASN | D | 93 | -110.356 | -16.200 | 7.458 | 1.00 | 50.33 |
| 18829 | ND2 | ASN | D | 93 | -110.797 | -14.648 | 5.883 | 1.00 | 48.85 |
| 18830 | C | ASN | D | 93 | -111.119 | -13.720 | 10.737 | 1.00 | 46.43 |
| 18831 | O | ASN | D | 93 | -110.718 | -12.555 | 10.561 | 1.00 | 45.96 |
| 18832 | N | TYR | D | 94 | -111.456 | -14.214 | 11.920 | 1.00 | 45.67 |
| 18833 | CA | TYR | D | 94 | -111.351 | -13.459 | 13.165 | 1.00 | 45.50 |
| 18834 | CB | TYR | D | 94 | -111.980 | -14.277 | 14.298 | 1.00 | 45.58 |
| 18835 | CG | TYR | D | 94 | -111.609 | -13.851 | 15.704 | 1.00 | 46.25 |
| 18836 | CD1 | TYR | D | 94 | -112.362 | -12.902 | 16.388 | 1.00 | 45.76 |
| 18837 | CE1 | TYR | D | 94 | -112.043 | -12.534 | 17.679 | 1.00 | 45.45 |
| 18838 | CZ | TYR | D | 94 | -110.962 | -13.119 | 18.305 | 1.00 | 46.65 |
| 18839 | OH | TYR | D | 94 | -110.629 | -12.765 | 19.597 | 1.00 | 45.85 |
| 18840 | CE2 | TYR | D | 94 | -110.210 | -14.076 | 17.649 | 1.00 | 46.49 |
| 18841 | CD2 | TYR | D | 94 | -110.535 | -14.435 | 16.364 | 1.00 | 46.48 |
| 18842 | C | TYR | D | 94 | -109.911 | -13.129 | 13.546 | 1.00 | 44.63 |
| 18843 | O | TYR | D | 94 | -109.115 | -14.026 | 13.806 | 1.00 | 44.39 |
| 18844 | N | VAL | D | 95 | -109.573 | -11.846 | 13.554 | 1.00 | 43.64 |
| 18845 | CA | VAL | D | 95 | -108.281 | -11.437 | 14.087 | 1.00 | 43.01 |
| 18846 | CB | VAL | D | 95 | -107.334 | -10.815 | 13.034 | 1.00 | 43.31 |
| 18847 | CG1 | VAL | D | 95 | -106.030 | -10.381 | 13.700 | 1.00 | 42.61 |
| 18848 | CG2 | VAL | D | 95 | -107.039 | -11.808 | 11.898 | 1.00 | 42.96 |
| 18849 | C | VAL | D | 95 | -108.511 | -10.473 | 15.250 | 1.00 | 42.24 |
| 18850 | O | VAL | D | 95 | -108.874 | -9.311 | 15.059 | 1.00 | 42.07 |
| 18851 | N | LYS | D | 96 | -108.299 | -10.986 | 16.458 | 1.00 | 41.35 |
| 18852 | CA | LYS | D | 96 | -108.477 | -10.235 | 17.696 | 1.00 | 39.85 |
| 18853 | CB | LYS | D | 96 | -108.243 | -11.162 | 18.886 | 1.00 | 40.10 |
| 18854 | CG | LYS | D | 96 | -108.004 | -10.449 | 20.204 | 1.00 | 40.77 |
| 18855 | CD | LYS | D | 96 | -107.842 | -11.437 | 21.357 | 1.00 | 41.13 |
| 18856 | CE | LYS | D | 96 | -107.905 | -10.718 | 22.701 | 1.00 | 41.42 |
| 18857 | NZ | LYS | D | 96 | -106.968 | -9.565 | 22.765 | 1.00 | 40.32 |
| 18858 | C | LYS | D | 96 | -107.534 | -9.051 | 17.817 | 1.00 | 38.99 |
| 18859 | O | LYS | D | 96 | -106.360 | -9.162 | 17.482 | 1.00 | 38.20 |
| 18860 | N | GLN | D | 97 | -108.062 | -7.921 | 18.294 | 1.00 | 37.80 |

FIGURE 3 NF

| A | B | C | D | E | F | G | H | I | J |
|---|---|---|---|---|---|---|---|---|---|
| 18861 | CA | GLN | D | 97 | -107.241 | -6.753 | 18.574 | 1.00 | 36.98 |
| 18862 | CB | GLN | D | 97 | -107.837 | -5.459 | 18.007 | 1.00 | 37.03 |
| 18863 | CG | GLN | D | 97 | -106.787 | -4.329 | 17.891 | 1.00 | 39.86 |
| 18864 | CD | GLN | D | 97 | -107.361 | -2.993 | 17.384 | 1.00 | 43.93 |
| 18865 | OE1 | GLN | D | 97 | -106.611 | -2.128 | 16.904 | 1.00 | 45.44 |
| 18866 | NE2 | GLN | D | 97 | -108.674 | -2.818 | 17.509 | 1.00 | 43.75 |
| 18867 | C | GLN | D | 97 | -107.045 | -6.660 | 20.089 | 1.00 | 35.89 |
| 18868 | O | GLN | D | 97 | -106.176 | -7.333 | 20.644 | 1.00 | 34.79 |
| 18869 | N | TRP | D | 98 | -107.872 | -5.858 | 20.757 | 1.00 | 34.86 |
| 18870 | CA | TRP | D | 98 | -107.759 | -5.713 | 22.200 | 1.00 | 34.39 |
| 18871 | CB | TRP | D | 98 | -107.954 | -4.259 | 22.622 | 1.00 | 33.78 |
| 18872 | CG | TRP | D | 98 | -107.147 | -3.306 | 21.804 | 1.00 | 31.88 |
| 18873 | CD1 | TRP | D | 98 | -107.574 | -2.115 | 21.269 | 1.00 | 29.98 |
| 18874 | NE1 | TRP | D | 98 | -106.553 | -1.509 | 20.578 | 1.00 | 29.57 |
| 18875 | CE2 | TRP | D | 98 | -105.434 | -2.303 | 20.655 | 1.00 | 30.00 |
| 18876 | CD2 | TRP | D | 98 | -105.776 | -3.446 | 21.416 | 1.00 | 29.79 |
| 18877 | CE3 | TRP | D | 98 | -104.796 | -4.421 | 21.632 | 1.00 | 29.20 |
| 18878 | CZ3 | TRP | D | 98 | -103.539 | -4.238 | 21.089 | 1.00 | 28.94 |
| 18879 | CH2 | TRP | D | 98 | -103.232 | -3.095 | 20.339 | 1.00 | 28.53 |
| 18880 | CZ2 | TRP | D | 98 | -104.167 | -2.121 | 20.107 | 1.00 | 28.56 |
| 18881 | C | TRP | D | 98 | -108.675 | -6.669 | 22.964 | 1.00 | 34.42 |
| 18882 | O | TRP | D | 98 | -108.842 | -7.810 | 22.564 | 1.00 | 34.63 |
| 18883 | N | ARG | D | 99 | -109.239 | -6.229 | 24.076 | 1.00 | 34.58 |
| 18884 | CA | ARG | D | 99 | -110.052 | -7.129 | 24.888 | 1.00 | 34.95 |
| 18885 | CB | ARG | D | 99 | -110.304 | -6.549 | 26.278 | 1.00 | 34.75 |
| 18886 | CG | ARG | D | 99 | -110.866 | -7.562 | 27.244 | 1.00 | 35.56 |
| 18887 | CD | ARG | D | 99 | -111.431 | -6.975 | 28.536 | 1.00 | 37.79 |
| 18888 | NE | ARG | D | 99 | -110.423 | -6.374 | 29.400 | 1.00 | 38.21 |
| 18889 | CZ | ARG | D | 99 | -109.616 | -7.060 | 30.224 | 1.00 | 39.10 |
| 18890 | NH1 | ARG | D | 99 | -109.682 | -8.383 | 30.263 | 1.00 | 37.89 |
| 18891 | NH2 | ARG | D | 99 | -108.736 | -6.420 | 31.009 | 1.00 | 35.22 |
| 18892 | C | ARG | D | 99 | -111.388 | -7.497 | 24.267 | 1.00 | 35.24 |
| 18893 | O | ARG | D | 99 | -111.866 | -8.617 | 24.461 | 1.00 | 35.09 |
| 18894 | N | HIS | D | 100 | -112.005 | -6.549 | 23.561 | 1.00 | 35.52 |
| 18895 | CA | HIS | D | 100 | -113.302 | -6.797 | 22.928 | 1.00 | 36.27 |
| 18896 | CB | HIS | D | 100 | -114.357 | -5.800 | 23.427 | 1.00 | 36.19 |
| 18897 | CG | HIS | D | 100 | -114.434 | -5.688 | 24.915 | 1.00 | 36.00 |
| 18898 | ND1 | HIS | D | 100 | -115.035 | -6.645 | 25.704 | 1.00 | 36.53 |
| 18899 | CE1 | HIS | D | 100 | -114.950 | -6.282 | 26.973 | 1.00 | 35.21 |
| 18900 | NE2 | HIS | D | 100 | -114.307 | -5.130 | 27.031 | 1.00 | 34.64 |
| 18901 | CD2 | HIS | D | 100 | -113.976 | -4.736 | 25.760 | 1.00 | 34.03 |
| 18902 | C | HIS | D | 100 | -113.184 | -6.623 | 21.421 | 1.00 | 37.21 |
| 18903 | O | HIS | D | 100 | -113.886 | -7.279 | 20.650 | 1.00 | 36.96 |
| 18904 | N | SER | D | 101 | -112.299 | -5.710 | 21.025 | 1.00 | 38.32 |
| 18905 | CA | SER | D | 101 | -112.084 | -5.386 | 19.638 | 1.00 | 39.66 |
| 18906 | CB | SER | D | 101 | -111.213 | -4.137 | 19.477 | 1.00 | 39.82 |
| 18907 | OG | SER | D | 101 | -110.019 | -4.237 | 20.223 | 1.00 | 39.55 |
| 18908 | C | SER | D | 101 | -111.464 | -6.525 | 18.886 | 1.00 | 40.65 |
| 18909 | O | SER | D | 101 | -110.700 | -7.313 | 19.428 | 1.00 | 40.80 |
| 18910 | N | TYR | D | 102 | -111.847 | -6.594 | 17.621 | 1.00 | 42.09 |
| 18911 | CA | TYR | D | 102 | -111.339 | -7.556 | 16.677 | 1.00 | 43.32 |

FIGURE 3 NG

| A | B | C | D | E | F | G | H | I | J |
|---|---|---|---|---|---|---|---|---|---|
| 18912 | CB | TYR | D | 102 | -111.758 | -8.988 | 17.015 | 1.00 | 43.40 |
| 18913 | CG | TYR | D | 102 | -113.246 | -9.306 | 16.979 | 1.00 | 43.83 |
| 18914 | CD1 | TYR | D | 102 | -113.883 | -9.621 | 15.780 | 1.00 | 44.25 |
| 18915 | CE1 | TYR | D | 102 | -115.236 | -9.945 | 15.744 | 1.00 | 43.98 |
| 18916 | CZ | TYR | D | 102 | -115.967 | -9.973 | 16.922 | 1.00 | 44.41 |
| 18917 | OH | TYR | D | 102 | -117.311 | -10.301 | 16.887 | 1.00 | 43.54 |
| 18918 | CE2 | TYR | D | 102 | -115.351 | -9.681 | 18.129 | 1.00 | 43.06 |
| 18919 | CD2 | TYR | D | 102 | -113.996 | -9.358 | 18.151 | 1.00 | 43.54 |
| 18920 | C | TYR | D | 102 | -111.796 | -7.152 | 15.285 | 1.00 | 44.34 |
| 18921 | O | TYR | D | 102 | -112.540 | -6.185 | 15.093 | 1.00 | 43.86 |
| 18922 | N | THR | D | 103 | -111.320 | -7.907 | 14.317 | 1.00 | 45.77 |
| 18923 | CA | THR | D | 103 | -111.582 | -7.634 | 12.930 | 1.00 | 47.06 |
| 18924 | CB | THR | D | 103 | -110.303 | -7.059 | 12.321 | 1.00 | 47.16 |
| 18925 | OG1 | THR | D | 103 | -110.625 | -6.135 | 11.278 | 1.00 | 47.95 |
| 18926 | CG2 | THR | D | 103 | -109.486 | -8.139 | 11.646 | 1.00 | 47.43 |
| 18927 | C | THR | D | 103 | -111.937 | -8.981 | 12.336 | 1.00 | 47.65 |
| 18928 | O | THR | D | 103 | -111.437 | -10.007 | 12.796 | 1.00 | 47.29 |
| 18929 | N | ALA | D | 104 | -112.835 | -8.988 | 11.356 | 1.00 | 49.01 |
| 18930 | CA | ALA | D | 104 | -113.252 | -10.239 | 10.717 | 1.00 | 50.41 |
| 18931 | CB | ALA | D | 104 | -114.139 | -11.057 | 11.657 | 1.00 | 49.90 |
| 18932 | C | ALA | D | 104 | -113.959 | -10.039 | 9.377 | 1.00 | 51.59 |
| 18933 | O | ALA | D | 104 | -114.330 | -8.918 | 8.999 | 1.00 | 51.48 |
| 18934 | N | SER | D | 105 | -114.118 | -11.141 | 8.655 | 1.00 | 52.93 |
| 18935 | CA | SER | D | 105 | -114.872 | -11.131 | 7.414 | 1.00 | 54.56 |
| 18936 | CB | SER | D | 105 | -114.257 | -12.071 | 6.374 | 1.00 | 54.31 |
| 18937 | OG | SER | D | 105 | -113.328 | -11.387 | 5.553 | 1.00 | 54.83 |
| 18938 | C | SER | D | 105 | -116.273 | -11.591 | 7.763 | 1.00 | 55.67 |
| 18939 | O | SER | D | 105 | -116.462 | -12.339 | 8.729 | 1.00 | 55.62 |
| 18940 | N | TYR | D | 106 | -117.247 | -11.139 | 6.977 | 1.00 | 57.16 |
| 18941 | CA | TYR | D | 106 | -118.649 | -11.469 | 7.221 | 1.00 | 58.72 |
| 18942 | CB | TYR | D | 106 | -119.347 | -10.313 | 7.952 | 1.00 | 58.66 |
| 18943 | CG | TYR | D | 106 | -118.833 | -10.020 | 9.355 | 1.00 | 58.17 |
| 18944 | CD1 | TYR | D | 106 | -117.882 | -9.029 | 9.584 | 1.00 | 57.42 |
| 18945 | CE1 | TYR | D | 106 | -117.422 | -8.759 | 10.864 | 1.00 | 57.44 |
| 18946 | CZ | TYR | D | 106 | -117.926 | -9.485 | 11.925 | 1.00 | 57.96 |
| 18947 | OH | TYR | D | 106 | -117.499 | -9.248 | 13.211 | 1.00 | 57.93 |
| 18948 | CE2 | TYR | D | 106 | -118.870 | -10.463 | 11.714 | 1.00 | 58.05 |
| 18949 | CD2 | TYR | D | 106 | -119.315 | -10.723 | 10.443 | 1.00 | 57.40 |
| 18950 | C | TYR | D | 106 | -119.430 | -11.785 | 5.942 | 1.00 | 59.84 |
| 18951 | O | TYR | D | 106 | -119.341 | -11.074 | 4.942 | 1.00 | 59.99 |
| 18952 | N | ASP | D | 107 | -120.195 | -12.865 | 5.983 | 1.00 | 61.24 |
| 18953 | CA | ASP | D | 107 | -121.074 | -13.208 | 4.881 | 1.00 | 62.79 |
| 18954 | CB | ASP | D | 107 | -120.627 | -14.489 | 4.177 | 1.00 | 62.64 |
| 18955 | CG | ASP | D | 107 | -119.475 | -14.259 | 3.225 | 1.00 | 63.77 |
| 18956 | OD1 | ASP | D | 107 | -119.417 | -13.167 | 2.614 | 1.00 | 64.55 |
| 18957 | OD2 | ASP | D | 107 | -118.575 | -15.110 | 3.030 | 1.00 | 64.76 |
| 18958 | C | ASP | D | 107 | -122.459 | -13.388 | 5.467 | 1.00 | 63.71 |
| 18959 | O | ASP | D | 107 | -122.614 | -13.966 | 6.538 | 1.00 | 63.78 |
| 18960 | N | ILE | D | 108 | -123.463 | -12.866 | 4.778 | 1.00 | 65.01 |
| 18961 | CA | ILE | D | 108 | -124.833 | -13.012 | 5.233 | 1.00 | 66.28 |
| 18962 | CB | ILE | D | 108 | -125.633 | -11.744 | 4.919 | 1.00 | 66.20 |

FIGURE 3 NH

| A | B | C | D | E | F | G | H | I | J |
|---|---|---|---|---|---|---|---|---|---|
| 18963 | CG1 | ILE | D | 108 | -124.917 | -10.522 | 5.487 | 1.00 | 65.90 |
| 18964 | CD1 | ILE | D | 108 | -125.322 | -9.229 | 4.838 | 1.00 | 65.83 |
| 18965 | CG2 | ILE | D | 108 | -127.044 | -11.853 | 5.467 | 1.00 | 66.26 |
| 18966 | C | ILE | D | 108 | -125.450 | -14.210 | 4.533 | 1.00 | 67.30 |
| 18967 | O | ILE | D | 108 | -125.363 | -14.334 | 3.318 | 1.00 | 67.32 |
| 18968 | N | TYR | D | 109 | -126.053 | -15.105 | 5.302 | 1.00 | 68.69 |
| 18969 | CA | TYR | D | 109 | -126.697 | -16.266 | 4.718 | 1.00 | 69.84 |
| 18970 | CB | TYR | D | 109 | -126.303 | -17.535 | 5.456 | 1.00 | 69.90 |
| 18971 | CG | TYR | D | 109 | -127.208 | -18.719 | 5.197 | 1.00 | 71.09 |
| 18972 | CD1 | TYR | D | 109 | -127.045 | -19.519 | 4.071 | 1.00 | 71.85 |
| 18973 | CE1 | TYR | D | 109 | -127.871 | -20.613 | 3.849 | 1.00 | 72.41 |
| 18974 | CZ | TYR | D | 109 | -128.867 | -20.912 | 4.761 | 1.00 | 72.30 |
| 18975 | OH | TYR | D | 109 | -129.701 | -21.990 | 4.565 | 1.00 | 73.12 |
| 18976 | CE2 | TYR | D | 109 | -129.040 | -20.133 | 5.878 | 1.00 | 72.36 |
| 18977 | CD2 | TYR | D | 109 | -128.215 | -19.049 | 6.091 | 1.00 | 71.87 |
| 18978 | C | TYR | D | 109 | -128.195 | -16.058 | 4.754 | 1.00 | 70.68 |
| 18979 | O | TYR | D | 109 | -128.742 | -15.532 | 5.725 | 1.00 | 70.66 |
| 18980 | N | ASP | D | 110 | -128.852 | -16.462 | 3.675 | 1.00 | 71.68 |
| 18981 | CA | ASP | D | 110 | -130.283 | -16.284 | 3.539 | 1.00 | 72.51 |
| 18982 | CB | ASP | D | 110 | -130.622 | -16.051 | 2.066 | 1.00 | 72.59 |
| 18983 | CG | ASP | D | 110 | -131.776 | -15.096 | 1.874 | 1.00 | 72.74 |
| 18984 | OD1 | ASP | D | 110 | -132.882 | -15.387 | 2.377 | 1.00 | 72.74 |
| 18985 | OD2 | ASP | D | 110 | -131.667 | -14.028 | 1.231 | 1.00 | 72.64 |
| 18986 | C | ASP | D | 110 | -130.973 | -17.541 | 4.032 | 1.00 | 73.04 |
| 18987 | O | ASP | D | 110 | -130.631 | -18.644 | 3.610 | 1.00 | 73.06 |
| 18988 | N | LEU | D | 111 | -131.935 | -17.387 | 4.935 | 1.00 | 73.76 |
| 18989 | CA | LEU | D | 111 | -132.669 | -18.549 | 5.415 | 1.00 | 74.52 |
| 18990 | CB | LEU | D | 111 | -133.836 | -18.139 | 6.306 | 1.00 | 74.64 |
| 18991 | CG | LEU | D | 111 | -133.705 | -18.587 | 7.761 | 1.00 | 74.93 |
| 18992 | CD1 | LEU | D | 111 | -134.969 | -18.249 | 8.531 | 1.00 | 75.05 |
| 18993 | CD2 | LEU | D | 111 | -133.428 | -20.093 | 7.815 | 1.00 | 75.00 |
| 18994 | C | LEU | D | 111 | -133.193 | -19.360 | 4.242 | 1.00 | 74.88 |
| 18995 | O | LEU | D | 111 | -133.080 | -20.590 | 4.220 | 1.00 | 74.88 |
| 18996 | N | ASN | D | 112 | -133.743 | -18.650 | 3.259 | 1.00 | 75.22 |
| 18997 | CA | ASN | D | 112 | -134.343 | -19.280 | 2.084 | 1.00 | 75.36 |
| 18998 | CB | ASN | D | 112 | -135.066 | -18.231 | 1.217 | 1.00 | 75.30 |
| 18999 | CG | ASN | D | 112 | -134.287 | -17.841 | -0.031 | 1.00 | 75.30 |
| 19000 | OD1 | ASN | D | 112 | -133.863 | -18.698 | -0.807 | 1.00 | 76.06 |
| 19001 | ND2 | ASN | D | 112 | -134.131 | -16.540 | -0.249 | 1.00 | 74.06 |
| 19002 | C | ASN | D | 112 | -133.389 | -20.158 | 1.256 | 1.00 | 75.42 |
| 19003 | O | ASN | D | 112 | -132.166 | -20.069 | 1.381 | 1.00 | 75.54 |
| 19004 | N | LEU | D | 116 | -127.026 | -18.276 | 0.911 | 1.00 | 72.76 |
| 19005 | CA | LEU | D | 116 | -125.797 | -17.461 | 1.077 | 1.00 | 72.77 |
| 19006 | CB | LEU | D | 116 | -124.547 | -18.284 | 0.774 | 1.00 | 72.85 |
| 19007 | CG | LEU | D | 116 | -123.241 | -17.815 | 1.421 | 1.00 | 73.32 |
| 19008 | CD1 | LEU | D | 116 | -123.052 | -18.509 | 2.758 | 1.00 | 73.79 |
| 19009 | CD2 | LEU | D | 116 | -122.045 | -18.083 | 0.515 | 1.00 | 73.55 |
| 19010 | C | LEU | D | 116 | -125.860 | -16.283 | 0.131 | 1.00 | 72.74 |
| 19011 | O | LEU | D | 116 | -126.359 | -16.389 | -0.987 | 1.00 | 72.77 |
| 19012 | N | ILE | D | 117 | -125.354 | -15.148 | 0.582 | 1.00 | 72.64 |
| 19013 | CA | ILE | D | 117 | -125.358 | -13.960 | -0.251 | 1.00 | 72.25 |

FIGURE 3 NI

| A | B | C | D | E | F | G | H | I | J |
|---|---|---|---|---|---|---|---|---|---|
| 19014 | CB | ILE | D | 117 | -125.816 | -12.745 | 0.548 | 1.00 | 72.24 |
| 19015 | CG1 | ILE | D | 117 | -127.255 | -12.953 | 1.012 | 1.00 | 72.43 |
| 19016 | CD1 | ILE | D | 117 | -127.974 | -11.664 | 1.332 | 1.00 | 72.87 |
| 19017 | CG2 | ILE | D | 117 | -125.718 | -11.486 | -0.289 | 1.00 | 72.17 |
| 19018 | C | ILE | D | 117 | -123.974 | -13.761 | -0.844 | 1.00 | 72.07 |
| 19019 | O | ILE | D | 117 | -122.968 | -14.129 | -0.226 | 1.00 | 72.23 |
| 19020 | N | THR | D | 118 | -123.934 | -13.193 | -2.049 | 1.00 | 71.58 |
| 19021 | CA | THR | D | 118 | -122.689 | -13.025 | -2.789 | 1.00 | 71.02 |
| 19022 | CB | THR | D | 118 | -122.687 | -13.981 | -3.968 | 1.00 | 71.07 |
| 19023 | OG1 | THR | D | 118 | -123.715 | -13.584 | -4.886 | 1.00 | 71.10 |
| 19024 | CG2 | THR | D | 118 | -123.124 | -15.369 | -3.517 | 1.00 | 71.27 |
| 19025 | C | THR | D | 118 | -122.537 | -11.615 | -3.327 | 1.00 | 70.60 |
| 19026 | O | THR | D | 118 | -121.457 | -11.214 | -3.762 | 1.00 | 70.73 |
| 19027 | N | GLU | D | 119 | -123.626 | -10.863 | -3.303 | 1.00 | 69.83 |
| 19028 | CA | GLU | D | 119 | -123.605 | -9.515 | -3.838 | 1.00 | 69.16 |
| 19029 | CB | GLU | D | 119 | -124.845 | -9.268 | -4.699 | 1.00 | 69.35 |
| 19030 | CG | GLU | D | 119 | -125.182 | -7.797 | -4.846 | 1.00 | 69.93 |
| 19031 | CD | GLU | D | 119 | -125.356 | -7.382 | -6.290 | 1.00 | 70.41 |
| 19032 | OE1 | GLU | D | 119 | -126.374 | -7.766 | -6.908 | 1.00 | 69.96 |
| 19033 | OE2 | GLU | D | 119 | -124.467 | -6.668 | -6.801 | 1.00 | 70.62 |
| 19034 | C | GLU | D | 119 | -123.471 | -8.424 | -2.779 | 1.00 | 68.55 |
| 19035 | O | GLU | D | 119 | -124.180 | -8.409 | -1.770 | 1.00 | 68.12 |
| 19036 | N | GLU | D | 120 | -122.546 | -7.505 | -3.031 | 1.00 | 67.97 |
| 19037 | CA | GLU | D | 120 | -122.332 | -6.389 | -2.137 | 1.00 | 67.25 |
| 19038 | CB | GLU | D | 120 | -123.639 | -5.599 | -2.023 | 1.00 | 67.27 |
| 19039 | CG | GLU | D | 120 | -123.479 | -4.091 | -2.106 | 1.00 | 67.86 |
| 19040 | CD | GLU | D | 120 | -122.505 | -3.657 | -3.187 | 1.00 | 68.83 |
| 19041 | OE1 | GLU | D | 120 | -122.954 | -3.364 | -4.314 | 1.00 | 69.63 |
| 19042 | OE2 | GLU | D | 120 | -121.287 | -3.600 | -2.904 | 1.00 | 68.90 |
| 19043 | C | GLU | D | 120 | -121.867 | -6.911 | -0.771 | 1.00 | 66.58 |
| 19044 | O | GLU | D | 120 | -122.200 | -6.336 | 0.265 | 1.00 | 66.55 |
| 19045 | N | ARG | D | 121 | -121.087 | -7.994 | -0.785 | 1.00 | 65.55 |
| 19046 | CA | ARG | D | 121 | -120.622 | -8.649 | 0.442 | 1.00 | 64.67 |
| 19047 | CB | ARG | D | 121 | -119.613 | -9.765 | 0.131 | 1.00 | 64.99 |
| 19048 | CG | ARG | D | 121 | -120.208 | -11.019 | -0.472 | 1.00 | 65.62 |
| 19049 | CD | ARG | D | 121 | -119.162 | -12.018 | -0.942 | 1.00 | 67.66 |
| 19050 | NE | ARG | D | 121 | -118.595 | -12.808 | 0.150 | 1.00 | 68.80 |
| 19051 | CZ | ARG | D | 121 | -117.338 | -13.233 | 0.188 | 1.00 | 70.07 |
| 19052 | NH1 | ARG | D | 121 | -116.508 | -12.931 | -0.800 | 1.00 | 70.63 |
| 19053 | NH2 | ARG | D | 121 | -116.907 | -13.961 | 1.212 | 1.00 | 70.91 |
| 19054 | C | ARG | D | 121 | -120.016 | -7.676 | 1.446 | 1.00 | 63.70 |
| 19055 | O | ARG | D | 121 | -119.550 | -6.590 | 1.079 | 1.00 | 63.62 |
| 19056 | N | ILE | D | 122 | -120.032 | -8.069 | 2.719 | 1.00 | 62.24 |
| 19057 | CA | ILE | D | 122 | -119.464 | -7.225 | 3.767 | 1.00 | 60.81 |
| 19058 | CB | ILE | D | 122 | -119.882 | -7.716 | 5.169 | 1.00 | 60.82 |
| 19059 | CG1 | ILE | D | 122 | -121.350 | -7.371 | 5.431 | 1.00 | 60.51 |
| 19060 | CD1 | ILE | D | 122 | -121.985 | -8.143 | 6.584 | 1.00 | 60.01 |
| 19061 | CG2 | ILE | D | 122 | -119.035 | -7.057 | 6.228 | 1.00 | 60.74 |
| 19062 | C | ILE | D | 122 | -117.958 | -7.232 | 3.603 | 1.00 | 59.48 |
| 19063 | O | ILE | D | 122 | -117.360 | -8.292 | 3.438 | 1.00 | 59.65 |
| 19064 | N | PRO | D | 123 | -117.347 | -6.054 | 3.636 | 1.00 | 58.43 |

FIGURE 3 NJ

| A | B | C | D | E | F | G | H | I | J |
|---|---|---|---|---|---|---|---|---|---|
| 19065 | CA | PRO | D | 123 | -115.900 | -5.925 | 3.424 | 1.00 | 57.67 |
| 19066 | CB | PRO | D | 123 | -115.632 | -4.443 | 3.697 | 1.00 | 57.56 |
| 19067 | CG | PRO | D | 123 | -116.930 | -3.768 | 3.545 | 1.00 | 57.74 |
| 19068 | CD | PRO | D | 123 | -117.991 | -4.759 | 3.907 | 1.00 | 58.33 |
| 19069 | C | PRO | D | 123 | -115.091 | -6.757 | 4.400 | 1.00 | 57.15 |
| 19070 | O | PRO | D | 123 | -115.505 | -6.943 | 5.543 | 1.00 | 56.86 |
| 19071 | N | ASN | D | 124 | -113.954 | -7.271 | 3.947 | 1.00 | 56.83 |
| 19072 | CA | ASN | D | 124 | -113.045 | -7.962 | 4.843 | 1.00 | 56.33 |
| 19073 | CB | ASN | D | 124 | -111.920 | -8.643 | 4.069 | 1.00 | 56.81 |
| 19074 | CG | ASN | D | 124 | -112.432 | -9.582 | 3.011 | 1.00 | 58.53 |
| 19075 | OD1 | ASN | D | 124 | -112.759 | -10.738 | 3.295 | 1.00 | 58.70 |
| 19076 | ND2 | ASN | D | 124 | -112.509 | -9.092 | 1.771 | 1.00 | 63.09 |
| 19077 | C | ASN | D | 124 | -112.459 | -6.898 | 5.750 | 1.00 | 55.47 |
| 19078 | O | ASN | D | 124 | -112.560 | -5.700 | 5.456 | 1.00 | 55.37 |
| 19079 | N | ASN | D | 125 | -111.847 | -7.330 | 6.847 | 1.00 | 54.44 |
| 19080 | CA | ASN | D | 125 | -111.243 | -6.405 | 7.793 | 1.00 | 53.40 |
| 19081 | CB | ASN | D | 125 | -110.092 | -5.644 | 7.128 | 1.00 | 53.69 |
| 19082 | CG | ASN | D | 125 | -108.980 | -6.576 | 6.639 | 1.00 | 54.78 |
| 19083 | OD1 | ASN | D | 125 | -108.700 | -6.657 | 5.438 | 1.00 | 55.43 |
| 19084 | ND2 | ASN | D | 125 | -108.341 | -7.284 | 7.574 | 1.00 | 55.14 |
| 19085 | C | ASN | D | 125 | -112.278 | -5.448 | 8.383 | 1.00 | 52.51 |
| 19086 | O | ASN | D | 125 | -111.966 | -4.307 | 8.731 | 1.00 | 52.05 |
| 19087 | N | THR | D | 126 | -113.517 | -5.920 | 8.482 | 1.00 | 51.47 |
| 19088 | CA | THR | D | 126 | -114.582 | -5.121 | 9.061 | 1.00 | 50.59 |
| 19089 | CB | THR | D | 126 | -115.957 | -5.638 | 8.610 | 1.00 | 50.76 |
| 19090 | OG1 | THR | D | 126 | -116.178 | -5.246 | 7.242 | 1.00 | 51.43 |
| 19091 | CG2 | THR | D | 126 | -117.081 | -4.929 | 9.371 | 1.00 | 49.95 |
| 19092 | C | THR | D | 126 | -114.424 | -5.106 | 10.585 | 1.00 | 50.03 |
| 19093 | O | THR | D | 126 | -114.283 | -6.148 | 11.227 | 1.00 | 49.49 |
| 19094 | N | GLN | D | 127 | -114.438 | -3.905 | 11.149 | 1.00 | 49.48 |
| 19095 | CA | GLN | D | 127 | -114.150 | -3.703 | 12.565 | 1.00 | 48.83 |
| 19096 | CB | GLN | D | 127 | -113.690 | -2.274 | 12.783 | 1.00 | 48.55 |
| 19097 | CG | GLN | D | 127 | -112.395 | -1.968 | 12.076 | 1.00 | 48.02 |
| 19098 | CD | GLN | D | 127 | -112.246 | -0.505 | 11.773 | 1.00 | 47.42 |
| 19099 | OE1 | GLN | D | 127 | -111.215 | 0.101 | 12.073 | 1.00 | 47.05 |
| 19100 | NE2 | GLN | D | 127 | -113.273 | 0.073 | 11.175 | 1.00 | 47.63 |
| 19101 | C | GLN | D | 127 | -115.300 | -4.025 | 13.497 | 1.00 | 48.68 |
| 19102 | O | GLN | D | 127 | -115.085 | -4.349 | 14.666 | 1.00 | 48.22 |
| 19103 | N | TRP | D | 128 | -116.520 | -3.943 | 12.985 | 1.00 | 48.58 |
| 19104 | CA | TRP | D | 128 | -117.686 | -4.236 | 13.804 | 1.00 | 48.57 |
| 19105 | CB | TRP | D | 128 | -117.785 | -3.224 | 14.941 | 1.00 | 48.61 |
| 19106 | CG | TRP | D | 128 | -118.920 | -3.469 | 15.859 | 1.00 | 48.73 |
| 19107 | CD1 | TRP | D | 128 | -120.091 | -2.772 | 15.920 | 1.00 | 49.51 |
| 19108 | NE1 | TRP | D | 128 | -120.898 | -3.293 | 16.903 | 1.00 | 50.23 |
| 19109 | CE2 | TRP | D | 128 | -120.251 | -4.346 | 17.495 | 1.00 | 49.20 |
| 19110 | CD2 | TRP | D | 128 | -119.004 | -4.483 | 16.861 | 1.00 | 49.16 |
| 19111 | CE3 | TRP | D | 128 | -118.146 | -5.497 | 17.292 | 1.00 | 49.46 |
| 19112 | CZ3 | TRP | D | 128 | -118.550 | -6.319 | 18.315 | 1.00 | 49.93 |
| 19113 | CH2 | TRP | D | 128 | -119.795 | -6.157 | 18.922 | 1.00 | 49.45 |
| 19114 | CZ2 | TRP | D | 128 | -120.657 | -5.176 | 18.528 | 1.00 | 49.26 |
| 19115 | C | TRP | D | 128 | -118.967 | -4.198 | 12.999 | 1.00 | 48.57 |

FIGURE 3 NK

| A | B | C | D | E | F | G | H | I | J |
|---|---|---|---|---|---|---|---|---|---|
| 19116 | O | TRP | D | 128 | -119.195 | -3.286 | 12.215 | 1.00 | 48.33 |
| 19117 | N | VAL | D | 129 | -119.810 | -5.195 | 13.193 | 1.00 | 49.01 |
| 19118 | CA | VAL | D | 129 | -121.094 | -5.208 | 12.515 | 1.00 | 49.67 |
| 19119 | CB | VAL | D | 129 | -121.119 | -6.213 | 11.356 | 1.00 | 49.72 |
| 19120 | CG1 | VAL | D | 129 | -120.447 | -7.495 | 11.762 | 1.00 | 49.39 |
| 19121 | CG2 | VAL | D | 129 | -122.557 | -6.454 | 10.889 | 1.00 | 49.71 |
| 19122 | C | VAL | D | 129 | -122.209 | -5.509 | 13.502 | 1.00 | 49.93 |
| 19123 | O | VAL | D | 129 | -122.088 | -6.404 | 14.337 | 1.00 | 49.80 |
| 19124 | N | THR | D | 130 | -123.296 | -4.754 | 13.395 | 1.00 | 50.50 |
| 19125 | CA | THR | D | 130 | -124.420 | -4.922 | 14.296 | 1.00 | 51.14 |
| 19126 | CB | THR | D | 130 | -124.385 | -3.833 | 15.364 | 1.00 | 51.17 |
| 19127 | OG1 | THR | D | 130 | -125.549 | -3.945 | 16.191 | 1.00 | 51.18 |
| 19128 | CG2 | THR | D | 130 | -124.541 | -2.472 | 14.713 | 1.00 | 51.04 |
| 19129 | C | THR | D | 130 | -125.767 | -4.868 | 13.589 | 1.00 | 51.70 |
| 19130 | O | THR | D | 130 | -126.021 | -3.986 | 12.766 | 1.00 | 51.85 |
| 19131 | N | TRP | D | 131 | -126.628 | -5.821 | 13.929 | 1.00 | 52.17 |
| 19132 | CA | TRP | D | 131 | -127.992 | -5.862 | 13.425 | 1.00 | 52.29 |
| 19133 | CB | TRP | D | 131 | -128.630 | -7.222 | 13.728 | 1.00 | 52.28 |
| 19134 | CG | TRP | D | 131 | -128.260 | -8.344 | 12.812 | 1.00 | 51.72 |
| 19135 | CD1 | TRP | D | 131 | -127.645 | -9.507 | 13.156 | 1.00 | 52.54 |
| 19136 | NE1 | TRP | D | 131 | -127.487 | -10.310 | 12.050 | 1.00 | 51.98 |
| 19137 | CE2 | TRP | D | 131 | -128.016 | -9.670 | 10.961 | 1.00 | 51.62 |
| 19138 | CD2 | TRP | D | 131 | -128.521 | -8.432 | 11.406 | 1.00 | 51.68 |
| 19139 | CE3 | TRP | D | 131 | -129.123 | -7.582 | 10.469 | 1.00 | 50.91 |
| 19140 | CZ3 | TRP | D | 131 | -129.193 | -7.988 | 9.150 | 1.00 | 50.91 |
| 19141 | CH2 | TRP | D | 131 | -128.684 | -9.223 | 8.745 | 1.00 | 51.06 |
| 19142 | CZ2 | TRP | D | 131 | -128.094 | -10.077 | 9.633 | 1.00 | 51.33 |
| 19143 | C | TRP | D | 131 | -128.822 | -4.804 | 14.133 | 1.00 | 52.55 |
| 19144 | O | TRP | D | 131 | -128.423 | -4.278 | 15.175 | 1.00 | 52.62 |
| 19145 | N | SER | D | 132 | -129.975 | -4.491 | 13.548 | 1.00 | 52.94 |
| 19146 | CA | SER | D | 132 | -130.971 | -3.617 | 14.152 | 1.00 | 52.94 |
| 19147 | CB | SER | D | 132 | -132.122 | -3.375 | 13.171 | 1.00 | 53.12 |
| 19148 | OG | SER | D | 132 | -131.735 | -2.586 | 12.071 | 1.00 | 53.77 |
| 19149 | C | SER | D | 132 | -131.543 | -4.395 | 15.317 | 1.00 | 52.84 |
| 19150 | O | SER | D | 132 | -131.464 | -5.620 | 15.336 | 1.00 | 52.63 |
| 19151 | N | PRO | D | 133 | -132.139 | -3.703 | 16.276 | 1.00 | 52.97 |
| 19152 | CA | PRO | D | 133 | -132.754 | -4.378 | 17.420 | 1.00 | 53.51 |
| 19153 | CB | PRO | D | 133 | -133.206 | -3.221 | 18.317 | 1.00 | 53.54 |
| 19154 | CG | PRO | D | 133 | -132.435 | -2.035 | 17.837 | 1.00 | 53.15 |
| 19155 | CD | PRO | D | 133 | -132.264 | -2.240 | 16.358 | 1.00 | 53.16 |
| 19156 | C | PRO | D | 133 | -133.945 | -5.193 | 16.933 | 1.00 | 54.07 |
| 19157 | O | PRO | D | 133 | -134.241 | -6.255 | 17.482 | 1.00 | 54.04 |
| 19158 | N | VAL | D | 134 | -134.615 | -4.681 | 15.901 | 1.00 | 54.63 |
| 19159 | CA | VAL | D | 134 | -135.711 | -5.383 | 15.241 | 1.00 | 54.97 |
| 19160 | CB | VAL | D | 134 | -137.041 | -4.623 | 15.383 | 1.00 | 55.20 |
| 19161 | CG1 | VAL | D | 134 | -137.425 | -4.443 | 16.859 | 1.00 | 56.05 |
| 19162 | CG2 | VAL | D | 134 | -136.956 | -3.278 | 14.683 | 1.00 | 55.03 |
| 19163 | C | VAL | D | 134 | -135.406 | -5.481 | 13.747 | 1.00 | 54.97 |
| 19164 | O | VAL | D | 134 | -134.654 | -4.676 | 13.208 | 1.00 | 54.98 |
| 19165 | N | GLY | D | 135 | -135.988 | -6.466 | 13.076 | 1.00 | 54.98 |
| 19166 | CA | GLY | D | 135 | -135.831 | -6.577 | 11.635 | 1.00 | 55.15 |

FIGURE 3 NL

| A | B | C | D | E | F | G | H | I | J |
|---|---|---|---|---|---|---|---|---|---|
| 19167 | C | GLY | D | 135 | -134.533 | -7.189 | 11.139 | 1.00 | 55.05 |
| 19168 | O | GLY | D | 135 | -134.098 | -8.238 | 11.632 | 1.00 | 55.19 |
| 19169 | N | HIS | D | 136 | -133.922 | -6.547 | 10.145 | 1.00 | 54.59 |
| 19170 | CA | HIS | D | 136 | -132.689 | -7.068 | 9.566 | 1.00 | 54.42 |
| 19171 | CB | HIS | D | 136 | -132.984 | -8.200 | 8.573 | 1.00 | 54.83 |
| 19172 | CG | HIS | D | 136 | -133.761 | -7.766 | 7.368 | 1.00 | 55.85 |
| 19173 | ND1 | HIS | D | 136 | -135.036 | -8.217 | 7.107 | 1.00 | 56.99 |
| 19174 | CE1 | HIS | D | 136 | -135.472 | -7.675 | 5.984 | 1.00 | 56.89 |
| 19175 | NE2 | HIS | D | 136 | -134.525 | -6.890 | 5.505 | 1.00 | 57.44 |
| 19176 | CD2 | HIS | D | 136 | -133.443 | -6.929 | 6.352 | 1.00 | 56.44 |
| 19177 | C | HIS | D | 136 | -131.812 | -6.014 | 8.903 | 1.00 | 53.87 |
| 19178 | O | HIS | D | 136 | -131.034 | -6.334 | 8.005 | 1.00 | 53.71 |
| 19179 | N | LYS | D | 137 | -131.944 | -4.763 | 9.327 | 1.00 | 53.46 |
| 19180 | CA | LYS | D | 137 | -131.046 | -3.721 | 8.848 | 1.00 | 53.39 |
| 19181 | CB | LYS | D | 137 | -131.518 | -2.345 | 9.298 | 1.00 | 53.41 |
| 19182 | CG | LYS | D | 137 | -132.872 | -1.994 | 8.752 | 1.00 | 53.27 |
| 19183 | CD | LYS | D | 137 | -133.505 | -0.854 | 9.498 | 1.00 | 53.95 |
| 19184 | CE | LYS | D | 137 | -132.758 | 0.448 | 9.304 | 1.00 | 53.85 |
| 19185 | NZ | LYS | D | 137 | -133.705 | 1.591 | 9.518 | 1.00 | 54.00 |
| 19186 | C | LYS | D | 137 | -129.660 | -4.031 | 9.407 | 1.00 | 53.29 |
| 19187 | O | LYS | D | 137 | -129.525 | -4.865 | 10.304 | 1.00 | 52.90 |
| 19188 | N | LEU | D | 138 | -128.636 | -3.363 | 8.885 | 1.00 | 53.28 |
| 19189 | CA | LEU | D | 138 | -127.267 | -3.692 | 9.262 | 1.00 | 53.28 |
| 19190 | CB | LEU | D | 138 | -126.714 | -4.705 | 8.252 | 1.00 | 53.54 |
| 19191 | CG | LEU | D | 138 | -125.875 | -5.902 | 8.701 | 1.00 | 54.30 |
| 19192 | CD1 | LEU | D | 138 | -126.255 | -6.391 | 10.088 | 1.00 | 54.55 |
| 19193 | CD2 | LEU | D | 138 | -126.046 | -7.019 | 7.695 | 1.00 | 55.20 |
| 19194 | C | LEU | D | 138 | -126.366 | -2.465 | 9.313 | 1.00 | 52.93 |
| 19195 | O | LEU | D | 138 | -126.380 | -1.644 | 8.404 | 1.00 | 53.28 |
| 19196 | N | ALA | D | 139 | -125.600 | -2.330 | 10.390 | 1.00 | 52.47 |
| 19197 | CA | ALA | D | 139 | -124.610 | -1.264 | 10.494 | 1.00 | 51.88 |
| 19198 | CB | ALA | D | 139 | -124.991 | -0.252 | 11.555 | 1.00 | 51.86 |
| 19199 | C | ALA | D | 139 | -123.274 | -1.913 | 10.820 | 1.00 | 51.49 |
| 19200 | O | ALA | D | 139 | -123.201 | -2.811 | 11.654 | 1.00 | 51.73 |
| 19201 | N | TYR | D | 140 | -122.223 | -1.481 | 10.139 | 1.00 | 50.77 |
| 19202 | CA | TYR | D | 140 | -120.905 | -2.043 | 10.367 | 1.00 | 50.11 |
| 19203 | CB | TYR | D | 140 | -120.615 | -3.162 | 9.362 | 1.00 | 50.32 |
| 19204 | CG | TYR | D | 140 | -120.595 | -2.693 | 7.924 | 1.00 | 51.56 |
| 19205 | CD1 | TYR | D | 140 | -119.491 | -2.030 | 7.412 | 1.00 | 52.15 |
| 19206 | CE1 | TYR | D | 140 | -119.461 | -1.595 | 6.108 | 1.00 | 52.91 |
| 19207 | CZ | TYR | D | 140 | -120.546 | -1.811 | 5.284 | 1.00 | 53.56 |
| 19208 | OH | TYR | D | 140 | -120.493 | -1.357 | 3.978 | 1.00 | 53.81 |
| 19209 | CE2 | TYR | D | 140 | -121.661 | -2.471 | 5.765 | 1.00 | 52.68 |
| 19210 | CD2 | TYR | D | 140 | -121.683 | -2.907 | 7.080 | 1.00 | 51.80 |
| 19211 | C | TYR | D | 140 | -119.869 | -0.938 | 10.271 | 1.00 | 49.24 |
| 19212 | O | TYR | D | 140 | -120.156 | 0.137 | 9.750 | 1.00 | 49.17 |
| 19213 | N | VAL | D | 141 | -118.676 | -1.186 | 10.805 | 1.00 | 48.39 |
| 19214 | CA | VAL | D | 141 | -117.602 | -0.202 | 10.738 | 1.00 | 47.57 |
| 19215 | CB | VAL | D | 141 | -117.171 | 0.300 | 12.142 | 1.00 | 47.62 |
| 19216 | CG1 | VAL | D | 141 | -118.347 | 0.930 | 12.868 | 1.00 | 46.94 |
| 19217 | CG2 | VAL | D | 141 | -116.027 | 1.311 | 12.041 | 1.00 | 47.46 |

FIGURE 3 NM

| A | B | C | D | E | F | G | H | I | J |
|---|---|---|---|---|---|---|---|---|---|
| 19218 | C | VAL | D | 141 | -116.423 | -0.792 | 9.976 | 1.00 | 47.21 |
| 19219 | O | VAL | D | 141 | -116.019 | -1.925 | 10.219 | 1.00 | 46.92 |
| 19220 | N | TRP | D | 142 | -115.904 | -0.025 | 9.024 | 1.00 | 46.99 |
| 19221 | CA | TRP | D | 142 | -114.798 | -0.466 | 8.190 | 1.00 | 46.91 |
| 19222 | CB | TRP | D | 142 | -115.311 | -1.002 | 6.859 | 1.00 | 47.22 |
| 19223 | CG | TRP | D | 142 | -114.223 | -1.473 | 5.930 | 1.00 | 48.90 |
| 19224 | CD1 | TRP | D | 142 | -113.537 | -2.650 | 6.001 | 1.00 | 49.87 |
| 19225 | NE1 | TRP | D | 142 | -112.625 | -2.732 | 4.976 | 1.00 | 50.83 |
| 19226 | CE2 | TRP | D | 142 | -112.712 | -1.595 | 4.216 | 1.00 | 51.60 |
| 19227 | CD2 | TRP | D | 142 | -113.713 | -0.783 | 4.786 | 1.00 | 49.90 |
| 19228 | CE3 | TRP | D | 142 | -113.993 | 0.450 | 4.186 | 1.00 | 51.17 |
| 19229 | CZ3 | TRP | D | 142 | -113.285 | 0.825 | 3.053 | 1.00 | 51.25 |
| 19230 | CH2 | TRP | D | 142 | -112.296 | -0.004 | 2.513 | 1.00 | 52.35 |
| 19231 | CZ2 | TRP | D | 142 | -111.997 | -1.218 | 3.073 | 1.00 | 52.69 |
| 19232 | C | TRP | D | 142 | -113.885 | 0.725 | 7.981 | 1.00 | 46.62 |
| 19233 | O | TRP | D | 142 | -114.353 | 1.822 | 7.653 | 1.00 | 46.66 |
| 19234 | N | ASN | D | 143 | -112.591 | 0.514 | 8.200 | 1.00 | 46.03 |
| 19235 | CA | ASN | D | 143 | -111.612 | 1.596 | 8.142 | 1.00 | 45.74 |
| 19236 | CB | ASN | D | 143 | -111.260 | 1.978 | 6.700 | 1.00 | 46.35 |
| 19237 | CG | ASN | D | 143 | -110.210 | 1.057 | 6.091 | 1.00 | 48.02 |
| 19238 | OD1 | ASN | D | 143 | -109.817 | 1.227 | 4.940 | 1.00 | 52.57 |
| 19239 | ND2 | ASN | D | 143 | -109.756 | 0.075 | 6.860 | 1.00 | 48.41 |
| 19240 | C | ASN | D | 143 | -112.093 | 2.802 | 8.920 | 1.00 | 44.61 |
| 19241 | O | ASN | D | 143 | -112.108 | 3.924 | 8.416 | 1.00 | 44.48 |
| 19242 | N | ASN | D | 144 | -112.520 | 2.544 | 10.148 | 1.00 | 43.39 |
| 19243 | CA | ASN | D | 144 | -112.984 | 3.596 | 11.046 | 1.00 | 42.57 |
| 19244 | CB | ASN | D | 144 | -111.816 | 4.505 | 11.452 | 1.00 | 42.15 |
| 19245 | CG | ASN | D | 144 | -110.758 | 3.772 | 12.268 | 1.00 | 40.44 |
| 19246 | OD1 | ASN | D | 144 | -109.975 | 4.389 | 12.977 | 1.00 | 39.55 |
| 19247 | ND2 | ASN | D | 144 | -110.742 | 2.453 | 12.174 | 1.00 | 38.08 |
| 19248 | C | ASN | D | 144 | -114.173 | 4.423 | 10.544 | 1.00 | 42.38 |
| 19249 | O | ASN | D | 144 | -114.345 | 5.577 | 10.952 | 1.00 | 42.50 |
| 19250 | N | ASP | D | 145 | -114.984 | 3.845 | 9.663 | 1.00 | 41.79 |
| 19251 | CA | ASP | D | 145 | -116.189 | 4.525 | 9.193 | 1.00 | 41.96 |
| 19252 | CB | ASP | D | 145 | -116.037 | 5.058 | 7.772 | 1.00 | 41.95 |
| 19253 | CG | ASP | D | 145 | -115.429 | 6.420 | 7.736 | 1.00 | 41.04 |
| 19254 | OD1 | ASP | D | 145 | -114.538 | 6.630 | 6.895 | 1.00 | 42.43 |
| 19255 | OD2 | ASP | D | 145 | -115.768 | 7.342 | 8.504 | 1.00 | 41.45 |
| 19256 | C | ASP | D | 145 | -117.432 | 3.655 | 9.290 | 1.00 | 41.86 |
| 19257 | O | ASP | D | 145 | -117.357 | 2.427 | 9.228 | 1.00 | 41.53 |
| 19258 | N | ILE | D | 146 | -118.570 | 4.316 | 9.451 | 1.00 | 42.16 |
| 19259 | CA | ILE | D | 146 | -119.843 | 3.638 | 9.641 | 1.00 | 43.35 |
| 19260 | CB | ILE | D | 146 | -120.714 | 4.435 | 10.651 | 1.00 | 43.25 |
| 19261 | CG1 | ILE | D | 146 | -119.979 | 4.562 | 11.989 | 1.00 | 43.13 |
| 19262 | CD1 | ILE | D | 146 | -120.669 | 5.444 | 12.985 | 1.00 | 42.36 |
| 19263 | CG2 | ILE | D | 146 | -122.079 | 3.786 | 10.834 | 1.00 | 42.53 |
| 19264 | C | ILE | D | 146 | -120.598 | 3.458 | 8.329 | 1.00 | 44.18 |
| 19265 | O | ILE | D | 146 | -120.713 | 4.387 | 7.543 | 1.00 | 43.72 |
| 19266 | N | TYR | D | 147 | -121.108 | 2.253 | 8.110 | 1.00 | 45.80 |
| 19267 | CA | TYR | D | 147 | -121.886 | 1.946 | 6.919 | 1.00 | 47.62 |
| 19268 | CB | TYR | D | 147 | -121.134 | 0.986 | 6.000 | 1.00 | 47.70 |

FIGURE 3 NN

| A | B | C | D | E | F | G | H | I | J |
|---|---|---|---|---|---|---|---|---|---|
| 19269 | CG | TYR | D | 147 | -119.868 | 1.515 | 5.372 | 1.00 | 49.63 |
| 19270 | CD1 | TYR | D | 147 | -119.894 | 2.148 | 4.140 | 1.00 | 51.43 |
| 19271 | CE1 | TYR | D | 147 | -118.737 | 2.619 | 3.549 | 1.00 | 51.99 |
| 19272 | CZ | TYR | D | 147 | -117.530 | 2.443 | 4.185 | 1.00 | 53.08 |
| 19273 | OH | TYR | D | 147 | -116.372 | 2.912 | 3.605 | 1.00 | 54.67 |
| 19274 | CE2 | TYR | D | 147 | -117.473 | 1.802 | 5.404 | 1.00 | 52.35 |
| 19275 | CD2 | TYR | D | 147 | -118.638 | 1.340 | 5.989 | 1.00 | 50.98 |
| 19276 | C | TYR | D | 147 | -123.210 | 1.285 | 7.309 | 1.00 | 48.25 |
| 19277 | O | TYR | D | 147 | -123.256 | 0.458 | 8.224 | 1.00 | 48.03 |
| 19278 | N | VAL | D | 148 | -124.277 | 1.623 | 6.592 | 1.00 | 49.17 |
| 19279 | CA | VAL | D | 148 | -125.575 | 1.023 | 6.870 | 1.00 | 50.14 |
| 19280 | CB | VAL | D | 148 | -126.579 | 2.060 | 7.410 | 1.00 | 50.11 |
| 19281 | CG1 | VAL | D | 148 | -127.927 | 1.416 | 7.638 | 1.00 | 49.82 |
| 19282 | CG2 | VAL | D | 148 | -126.068 | 2.679 | 8.707 | 1.00 | 49.73 |
| 19283 | C | VAL | D | 148 | -126.199 | 0.339 | 5.662 | 1.00 | 51.12 |
| 19284 | O | VAL | D | 148 | -126.381 | 0.959 | 4.613 | 1.00 | 51.21 |
| 19285 | N | LYS | D | 149 | -126.504 | -0.948 | 5.814 | 1.00 | 52.15 |
| 19286 | CA | LYS | D | 149 | -127.238 | -1.696 | 4.795 | 1.00 | 53.34 |
| 19287 | CB | LYS | D | 149 | -126.630 | -3.081 | 4.568 | 1.00 | 53.22 |
| 19288 | CG | LYS | D | 149 | -125.433 | -3.103 | 3.635 | 1.00 | 54.73 |
| 19289 | CD | LYS | D | 149 | -125.032 | -4.528 | 3.269 | 1.00 | 56.28 |
| 19290 | CE | LYS | D | 149 | -124.096 | -4.518 | 2.068 | 1.00 | 58.45 |
| 19291 | NZ | LYS | D | 149 | -123.459 | -3.167 | 1.889 | 1.00 | 59.46 |
| 19292 | C | LYS | D | 149 | -128.681 | -1.865 | 5.265 | 1.00 | 53.90 |
| 19293 | O | LYS | D | 149 | -128.930 | -2.407 | 6.348 | 1.00 | 54.32 |
| 19294 | N | ILE | D | 150 | -129.638 | -1.383 | 4.481 | 1.00 | 54.47 |
| 19295 | CA | ILE | D | 150 | -131.030 | -1.574 | 4.860 | 1.00 | 54.83 |
| 19296 | CB | ILE | D | 150 | -131.948 | -0.562 | 4.198 | 1.00 | 54.84 |
| 19297 | CG1 | ILE | D | 150 | -132.012 | 0.732 | 5.014 | 1.00 | 55.22 |
| 19298 | CD1 | ILE | D | 150 | -130.687 | 1.265 | 5.454 | 1.00 | 57.03 |
| 19299 | CG2 | ILE | D | 150 | -133.353 | -1.140 | 4.117 | 1.00 | 54.79 |
| 19300 | C | ILE | D | 150 | -131.438 | -2.977 | 4.463 | 1.00 | 55.15 |
| 19301 | O | ILE | D | 150 | -132.313 | -3.587 | 5.084 | 1.00 | 55.26 |
| 19302 | N | GLU | D | 151 | -130.771 | -3.491 | 3.433 | 1.00 | 55.67 |
| 19303 | CA | GLU | D | 151 | -131.050 | -4.822 | 2.915 | 1.00 | 56.17 |
| 19304 | CB | GLU | D | 151 | -131.914 | -4.725 | 1.652 | 1.00 | 56.22 |
| 19305 | CG | GLU | D | 151 | -133.279 | -4.082 | 1.856 | 1.00 | 56.08 |
| 19306 | CD | GLU | D | 151 | -134.211 | -4.936 | 2.692 | 1.00 | 56.08 |
| 19307 | OE1 | GLU | D | 151 | -133.987 | -6.160 | 2.756 | 1.00 | 56.09 |
| 19308 | OE2 | GLU | D | 151 | -135.167 | -4.389 | 3.285 | 1.00 | 56.41 |
| 19309 | C | GLU | D | 151 | -129.755 | -5.558 | 2.595 | 1.00 | 56.55 |
| 19310 | O | GLU | D | 151 | -128.898 | -5.057 | 1.875 | 1.00 | 56.69 |
| 19311 | N | PRO | D | 152 | -129.634 | -6.771 | 3.104 | 1.00 | 57.10 |
| 19312 | CA | PRO | D | 152 | -128.405 | -7.556 | 2.956 | 1.00 | 57.89 |
| 19313 | CB | PRO | D | 152 | -128.844 | -8.953 | 3.382 | 1.00 | 57.70 |
| 19314 | CG | PRO | D | 152 | -129.949 | -8.704 | 4.339 | 1.00 | 57.44 |
| 19315 | CD | PRO | D | 152 | -130.686 | -7.500 | 3.830 | 1.00 | 57.04 |
| 19316 | C | PRO | D | 152 | -127.846 | -7.592 | 1.535 | 1.00 | 58.84 |
| 19317 | O | PRO | D | 152 | -126.626 | -7.619 | 1.365 | 1.00 | 59.09 |
| 19318 | N | ASN | D | 153 | -128.720 | -7.594 | 0.535 | 1.00 | 59.72 |
| 19319 | CA | ASN | D | 153 | -128.285 | -7.696 | -0.852 | 1.00 | 60.60 |

FIGURE 3 NO

| A | B | C | D | E | F | G | H | I | J |
|---|---|---|---|---|---|---|---|---|---|
| 19320 | CB | ASN | D | 153 | -129.319 | -8.488 | -1.666 | 1.00 | 60.74 |
| 19321 | CG | ASN | D | 153 | -128.679 | -9.390 | -2.733 | 1.00 | 62.12 |
| 19322 | OD1 | ASN | D | 153 | -127.457 | -9.598 | -2.754 | 1.00 | 62.65 |
| 19323 | ND2 | ASN | D | 153 | -129.513 | -9.935 | -3.619 | 1.00 | 62.19 |
| 19324 | C | ASN | D | 153 | -128.033 | -6.338 | -1.502 | 1.00 | 60.92 |
| 19325 | O | ASN | D | 153 | -127.583 | -6.269 | -2.644 | 1.00 | 61.11 |
| 19326 | N | LEU | D | 154 | -128.296 | -5.261 | -0.770 | 1.00 | 61.44 |
| 19327 | CA | LEU | D | 154 | -128.196 | -3.912 | -1.337 | 1.00 | 61.99 |
| 19328 | CB | LEU | D | 154 | -129.433 | -3.093 | -0.973 | 1.00 | 61.89 |
| 19329 | CG | LEU | D | 154 | -130.733 | -3.545 | -1.639 | 1.00 | 62.88 |
| 19330 | CD1 | LEU | D | 154 | -130.479 | -4.018 | -3.071 | 1.00 | 63.19 |
| 19331 | CD2 | LEU | D | 154 | -131.773 | -2.425 | -1.603 | 1.00 | 63.11 |
| 19332 | C | LEU | D | 154 | -126.936 | -3.135 | -0.963 | 1.00 | 62.40 |
| 19333 | O | LEU | D | 154 | -126.287 | -3.425 | 0.042 | 1.00 | 62.58 |
| 19334 | N | PRO | D | 155 | -126.618 | -2.129 | -1.778 | 1.00 | 62.71 |
| 19335 | CA | PRO | D | 155 | -125.437 | -1.279 | -1.585 | 1.00 | 62.86 |
| 19336 | CB | PRO | D | 155 | -125.663 | -0.153 | -2.604 | 1.00 | 62.88 |
| 19337 | CG | PRO | D | 155 | -127.126 | -0.249 | -2.911 | 1.00 | 62.68 |
| 19338 | CD | PRO | D | 155 | -127.373 | -1.721 | -2.974 | 1.00 | 62.65 |
| 19339 | C | PRO | D | 155 | -125.346 | -0.684 | -0.186 | 1.00 | 62.91 |
| 19340 | O | PRO | D | 155 | -126.345 | -0.600 | 0.528 | 1.00 | 62.98 |
| 19341 | N | SER | D | 156 | -124.147 | -0.239 | 0.176 | 1.00 | 62.87 |
| 19342 | CA | SER | D | 156 | -123.904 | 0.301 | 1.501 | 1.00 | 62.90 |
| 19343 | CB | SER | D | 156 | -122.579 | -0.225 | 2.033 | 1.00 | 63.05 |
| 19344 | OG | SER | D | 156 | -122.680 | -0.457 | 3.420 | 1.00 | 64.11 |
| 19345 | C | SER | D | 156 | -123.905 | 1.821 | 1.549 | 1.00 | 62.65 |
| 19346 | O | SER | D | 156 | -123.365 | 2.493 | 0.667 | 1.00 | 62.59 |
| 19347 | N | TYR | D | 157 | -124.506 | 2.369 | 2.598 | 1.00 | 62.27 |
| 19348 | CA | TYR | D | 157 | -124.555 | 3.818 | 2.757 | 1.00 | 61.78 |
| 19349 | CB | TYR | D | 157 | -125.901 | 4.267 | 3.317 | 1.00 | 62.14 |
| 19350 | CG | TYR | D | 157 | -127.060 | 4.081 | 2.376 | 1.00 | 63.55 |
| 19351 | CD1 | TYR | D | 157 | -127.490 | 5.121 | 1.553 | 1.00 | 65.01 |
| 19352 | CE1 | TYR | D | 157 | -128.557 | 4.947 | 0.694 | 1.00 | 66.14 |
| 19353 | CZ | TYR | D | 157 | -129.203 | 3.722 | 0.658 | 1.00 | 66.09 |
| 19354 | OH | TYR | D | 157 | -130.268 | 3.516 | -0.184 | 1.00 | 66.86 |
| 19355 | CE2 | TYR | D | 157 | -128.794 | 2.685 | 1.467 | 1.00 | 65.51 |
| 19356 | CD2 | TYR | D | 157 | -127.734 | 2.869 | 2.317 | 1.00 | 64.70 |
| 19357 | C | TYR | D | 157 | -123.455 | 4.328 | 3.674 | 1.00 | 60.96 |
| 19358 | O | TYR | D | 157 | -123.386 | 3.942 | 4.838 | 1.00 | 61.11 |
| 19359 | N | ARG | D | 158 | -122.603 | 5.197 | 3.139 | 1.00 | 59.75 |
| 19360 | CA | ARG | D | 158 | -121.532 | 5.802 | 3.911 | 1.00 | 58.41 |
| 19361 | CB | ARG | D | 158 | -120.521 | 6.473 | 2.980 | 1.00 | 58.83 |
| 19362 | CG | ARG | D | 158 | -119.328 | 5.616 | 2.557 | 1.00 | 59.53 |
| 19363 | CD | ARG | D | 158 | -118.062 | 5.897 | 3.359 | 1.00 | 61.65 |
| 19364 | NE | ARG | D | 158 | -116.839 | 5.483 | 2.675 | 1.00 | 62.55 |
| 19365 | CZ | ARG | D | 158 | -115.660 | 6.077 | 2.844 | 1.00 | 63.50 |
| 19366 | NH1 | ARG | D | 158 | -115.539 | 7.100 | 3.684 | 1.00 | 62.39 |
| 19367 | NH2 | ARG | D | 158 | -114.597 | 5.643 | 2.182 | 1.00 | 64.32 |
| 19368 | C | ARG | D | 158 | -122.132 | 6.852 | 4.826 | 1.00 | 57.27 |
| 19369 | O | ARG | D | 158 | -122.639 | 7.883 | 4.352 | 1.00 | 56.83 |
| 19370 | N | ILE | D | 159 | -122.099 | 6.590 | 6.131 | 1.00 | 55.59 |

FIGURE 3 NP

| A | B | C | D | E | F | G | H | I | J |
|---|---|---|---|---|---|---|---|---|---|
| 19371 | CA | ILE | D | 159 | -122.573 | 7.572 | 7.084 | 1.00 | 53.90 |
| 19372 | CB | ILE | D | 159 | -123.031 | 6.926 | 8.387 | 1.00 | 54.00 |
| 19373 | CG1 | ILE | D | 159 | -124.297 | 6.118 | 8.173 | 1.00 | 53.91 |
| 19374 | CD1 | ILE | D | 159 | -124.039 | 4.683 | 7.912 | 1.00 | 55.57 |
| 19375 | CG2 | ILE | D | 159 | -123.294 | 7.993 | 9.432 | 1.00 | 53.93 |
| 19376 | C | ILE | D | 159 | -121.452 | 8.551 | 7.374 | 1.00 | 52.93 |
| 19377 | O | ILE | D | 159 | -121.678 | 9.754 | 7.485 | 1.00 | 52.51 |
| 19378 | N | THR | D | 160 | -120.235 | 8.034 | 7.504 | 1.00 | 52.05 |
| 19379 | CA | THR | D | 160 | -119.096 | 8.894 | 7.824 | 1.00 | 51.01 |
| 19380 | CB | THR | D | 160 | -118.529 | 8.603 | 9.246 | 1.00 | 50.81 |
| 19381 | OG1 | THR | D | 160 | -118.337 | 7.191 | 9.421 | 1.00 | 49.35 |
| 19382 | CG2 | THR | D | 160 | -119.545 | 8.970 | 10.293 | 1.00 | 50.05 |
| 19383 | C | THR | D | 160 | -117.982 | 8.816 | 6.807 | 1.00 | 50.79 |
| 19384 | O | THR | D | 160 | -117.764 | 7.787 | 6.175 | 1.00 | 50.59 |
| 19385 | N | TRP | D | 161 | -117.265 | 9.920 | 6.692 | 1.00 | 51.02 |
| 19386 | CA | TRP | D | 161 | -116.172 | 10.050 | 5.747 | 1.00 | 51.50 |
| 19387 | CB | TRP | D | 161 | -116.579 | 11.048 | 4.656 | 1.00 | 51.88 |
| 19388 | CG | TRP | D | 161 | -117.716 | 10.579 | 3.817 | 1.00 | 52.73 |
| 19389 | CD1 | TRP | D | 161 | -119.048 | 10.661 | 4.107 | 1.00 | 53.73 |
| 19390 | NE1 | TRP | D | 161 | -119.789 | 10.116 | 3.084 | 1.00 | 54.35 |
| 19391 | CE2 | TRP | D | 161 | -118.936 | 9.675 | 2.106 | 1.00 | 54.33 |
| 19392 | CD2 | TRP | D | 161 | -117.623 | 9.950 | 2.538 | 1.00 | 54.16 |
| 19393 | CE3 | TRP | D | 161 | -116.557 | 9.595 | 1.706 | 1.00 | 55.05 |
| 19394 | CZ3 | TRP | D | 161 | -116.828 | 8.983 | 0.501 | 1.00 | 55.45 |
| 19395 | CH2 | TRP | D | 161 | -118.142 | 8.721 | 0.102 | 1.00 | 55.33 |
| 19396 | CZ2 | TRP | D | 161 | -119.207 | 9.060 | 0.886 | 1.00 | 54.84 |
| 19397 | C | TRP | D | 161 | -114.914 | 10.562 | 6.441 | 1.00 | 51.28 |
| 19398 | O | TRP | D | 161 | -113.918 | 10.849 | 5.784 | 1.00 | 51.69 |
| 19399 | N | THR | D | 162 | -114.960 | 10.675 | 7.765 | 1.00 | 50.76 |
| 19400 | CA | THR | D | 162 | -113.838 | 11.225 | 8.523 | 1.00 | 50.57 |
| 19401 | CB | THR | D | 162 | -114.353 | 12.097 | 9.699 | 1.00 | 50.82 |
| 19402 | OG1 | THR | D | 162 | -115.450 | 11.443 | 10.361 | 1.00 | 49.95 |
| 19403 | CG2 | THR | D | 162 | -114.983 | 13.397 | 9.165 | 1.00 | 51.04 |
| 19404 | C | THR | D | 162 | -112.805 | 10.214 | 9.027 | 1.00 | 50.33 |
| 19405 | O | THR | D | 162 | -111.738 | 10.605 | 9.473 | 1.00 | 50.51 |
| 19406 | N | GLY | D | 163 | -113.111 | 8.925 | 8.933 | 1.00 | 50.05 |
| 19407 | CA | GLY | D | 163 | -112.219 | 7.881 | 9.410 | 1.00 | 49.47 |
| 19408 | C | GLY | D | 163 | -110.746 | 7.944 | 9.026 | 1.00 | 49.18 |
| 19409 | O | GLY | D | 163 | -110.382 | 8.061 | 7.857 | 1.00 | 49.48 |
| 19410 | N | LYS | D | 164 | -109.886 | 7.852 | 10.032 | 1.00 | 48.57 |
| 19411 | CA | LYS | D | 164 | -108.447 | 7.826 | 9.815 | 1.00 | 47.59 |
| 19412 | CB | LYS | D | 164 | -107.862 | 9.237 | 9.799 | 1.00 | 48.00 |
| 19413 | CG | LYS | D | 164 | -106.443 | 9.303 | 9.252 | 1.00 | 48.18 |
| 19414 | CD | LYS | D | 164 | -105.899 | 10.721 | 9.351 | 1.00 | 50.62 |
| 19415 | CE | LYS | D | 164 | -104.506 | 10.842 | 8.722 | 1.00 | 51.69 |
| 19416 | NZ | LYS | D | 164 | -103.882 | 12.164 | 9.030 | 1.00 | 52.29 |
| 19417 | C | LYS | D | 164 | -107.802 | 6.989 | 10.909 | 1.00 | 46.77 |
| 19418 | O | LYS | D | 164 | -107.955 | 7.280 | 12.098 | 1.00 | 46.34 |
| 19419 | N | GLU | D | 165 | -107.088 | 5.949 | 10.482 | 1.00 | 45.96 |
| 19420 | CA | GLU | D | 165 | -106.421 | 4.992 | 11.358 | 1.00 | 45.15 |
| 19421 | CB | GLU | D | 165 | -105.426 | 4.156 | 10.550 | 1.00 | 45.79 |

FIGURE 3 NQ

| A | B | C | D | E | F | G | H | I | J |
|---|---|---|---|---|---|---|---|---|---|
| 19422 | CG | GLU | D | 165 | -104.424 | 3.379 | 11.389 | 1.00 | 48.11 |
| 19423 | CD | GLU | D | 165 | -103.887 | 2.158 | 10.660 | 1.00 | 50.89 |
| 19424 | OE1 | GLU | D | 165 | -103.038 | 2.325 | 9.751 | 1.00 | 52.11 |
| 19425 | OE2 | GLU | D | 165 | -104.324 | 1.033 | 10.990 | 1.00 | 50.88 |
| 19426 | C | GLU | D | 165 | -105.723 | 5.672 | 12.520 | 1.00 | 43.98 |
| 19427 | O | GLU | D | 165 | -104.946 | 6.603 | 12.313 | 1.00 | 43.28 |
| 19428 | N | ASN | D | 166 | -106.035 | 5.215 | 13.738 | 1.00 | 42.69 |
| 19429 | CA | ASN | D | 166 | -105.470 | 5.765 | 14.970 | 1.00 | 41.42 |
| 19430 | CB | ASN | D | 166 | -103.945 | 5.589 | 15.006 | 1.00 | 41.08 |
| 19431 | CG | ASN | D | 166 | -103.490 | 4.134 | 14.826 | 1.00 | 40.59 |
| 19432 | OD1 | ASN | D | 166 | -104.158 | 3.181 | 15.230 | 1.00 | 39.05 |
| 19433 | ND2 | ASN | D | 166 | -102.314 | 3.973 | 14.244 | 1.00 | 41.57 |
| 19434 | C | ASN | D | 166 | -105.799 | 7.242 | 15.248 | 1.00 | 41.24 |
| 19435 | O | ASN | D | 166 | -105.270 | 7.822 | 16.189 | 1.00 | 41.55 |
| 19436 | N | ILE | D | 167 | -106.656 | 7.873 | 14.453 | 1.00 | 40.53 |
| 19437 | CA | ILE | D | 167 | -106.919 | 9.300 | 14.680 | 1.00 | 39.73 |
| 19438 | CB | ILE | D | 167 | -106.313 | 10.183 | 13.545 | 1.00 | 40.06 |
| 19439 | CG1 | ILE | D | 167 | -104.794 | 10.065 | 13.511 | 1.00 | 40.35 |
| 19440 | CD1 | ILE | D | 167 | -104.307 | 8.928 | 12.682 | 1.00 | 42.19 |
| 19441 | CG2 | ILE | D | 167 | -106.646 | 11.659 | 13.734 | 1.00 | 40.09 |
| 19442 | C | ILE | D | 167 | -108.400 | 9.599 | 14.884 | 1.00 | 38.82 |
| 19443 | O | ILE | D | 167 | -108.779 | 10.248 | 15.855 | 1.00 | 38.90 |
| 19444 | N | ILE | D | 168 | -109.233 | 9.122 | 13.968 | 1.00 | 37.79 |
| 19445 | CA | ILE | D | 168 | -110.668 | 9.321 | 14.060 | 1.00 | 36.40 |
| 19446 | CB | ILE | D | 168 | -111.190 | 10.247 | 12.920 | 1.00 | 36.61 |
| 19447 | CG1 | ILE | D | 168 | -110.993 | 11.711 | 13.300 | 1.00 | 35.98 |
| 19448 | CD1 | ILE | D | 168 | -109.627 | 12.174 | 13.119 | 1.00 | 36.15 |
| 19449 | CG2 | ILE | D | 168 | -112.676 | 10.035 | 12.686 | 1.00 | 35.01 |
| 19450 | C | ILE | D | 168 | -111.368 | 7.990 | 13.999 | 1.00 | 36.30 |
| 19451 | O | ILE | D | 168 | -111.141 | 7.221 | 13.073 | 1.00 | 35.83 |
| 19452 | N | TYR | D | 169 | -112.229 | 7.721 | 14.985 | 1.00 | 35.99 |
| 19453 | CA | TYR | D | 169 | -112.982 | 6.471 | 15.026 | 1.00 | 35.20 |
| 19454 | CB | TYR | D | 169 | -112.652 | 5.639 | 16.288 | 1.00 | 34.82 |
| 19455 | CG | TYR | D | 169 | -111.196 | 5.355 | 16.631 | 1.00 | 32.44 |
| 19456 | CD1 | TYR | D | 169 | -110.329 | 6.378 | 17.005 | 1.00 | 31.54 |
| 19457 | CE1 | TYR | D | 169 | -109.019 | 6.126 | 17.342 | 1.00 | 28.27 |
| 19458 | CZ | TYR | D | 169 | -108.549 | 4.839 | 17.324 | 1.00 | 30.04 |
| 19459 | OH | TYR | D | 169 | -107.231 | 4.592 | 17.663 | 1.00 | 30.23 |
| 19460 | CE2 | TYR | D | 169 | -109.389 | 3.788 | 16.966 | 1.00 | 29.76 |
| 19461 | CD2 | TYR | D | 169 | -110.706 | 4.055 | 16.634 | 1.00 | 30.34 |
| 19462 | C | TYR | D | 169 | -114.474 | 6.798 | 15.090 | 1.00 | 35.54 |
| 19463 | O | TYR | D | 169 | -114.918 | 7.446 | 16.033 | 1.00 | 36.06 |
| 19464 | N | ASN | D | 170 | -115.256 | 6.347 | 14.116 | 1.00 | 35.04 |
| 19465 | CA | ASN | D | 170 | -116.698 | 6.540 | 14.183 | 1.00 | 34.53 |
| 19466 | CB | ASN | D | 170 | -117.302 | 7.095 | 12.868 | 1.00 | 34.47 |
| 19467 | CG | ASN | D | 170 | -116.540 | 8.269 | 12.308 | 1.00 | 33.96 |
| 19468 | OD1 | ASN | D | 170 | -115.718 | 8.100 | 11.415 | 1.00 | 36.18 |
| 19469 | ND2 | ASN | D | 170 | -116.806 | 9.466 | 12.822 | 1.00 | 32.81 |
| 19470 | C | ASN | D | 170 | -117.309 | 5.185 | 14.426 | 1.00 | 34.53 |
| 19471 | O | ASN | D | 170 | -117.001 | 4.220 | 13.719 | 1.00 | 34.47 |
| 19472 | N | GLY | D | 171 | -118.192 | 5.099 | 15.406 | 1.00 | 34.24 |

FIGURE 3 NR

| A | B | C | D | E | F | G | H | I | J |
|---|---|---|---|---|---|---|---|---|---|
| 19473 | CA  | GLY | D | 171 | -118.867 | 3.844  | 15.650 | 1.00 | 33.95 |
| 19474 | C   | GLY | D | 171 | -118.020 | 2.800  | 16.328 | 1.00 | 33.67 |
| 19475 | O   | GLY | D | 171 | -118.525 | 1.738  | 16.662 | 1.00 | 33.71 |
| 19476 | N   | ILE | D | 172 | -116.734 | 3.074  | 16.512 | 1.00 | 33.28 |
| 19477 | CA  | ILE | D | 172 | -115.905 | 2.165  | 17.299 | 1.00 | 33.21 |
| 19478 | CB  | ILE | D | 172 | -115.021 | 1.258  | 16.435 | 1.00 | 33.11 |
| 19479 | CG1 | ILE | D | 172 | -114.167 | 2.086  | 15.480 | 1.00 | 33.64 |
| 19480 | CD1 | ILE | D | 172 | -113.038 | 1.297  | 14.870 | 1.00 | 33.35 |
| 19481 | CG2 | ILE | D | 172 | -115.857 | 0.212  | 15.707 | 1.00 | 32.71 |
| 19482 | C   | ILE | D | 172 | -115.065 | 2.935  | 18.305 | 1.00 | 32.77 |
| 19483 | O   | ILE | D | 172 | -114.861 | 4.138  | 18.168 | 1.00 | 33.08 |
| 19484 | N   | THR | D | 173 | -114.589 | 2.246  | 19.327 | 1.00 | 32.04 |
| 19485 | CA  | THR | D | 173 | -113.801 | 2.912  | 20.364 | 1.00 | 31.62 |
| 19486 | CB  | THR | D | 173 | -114.030 | 2.199  | 21.703 | 1.00 | 31.51 |
| 19487 | OG1 | THR | D | 173 | -113.962 | 0.781  | 21.506 | 1.00 | 28.76 |
| 19488 | CG2 | THR | D | 173 | -115.471 | 2.414  | 22.168 | 1.00 | 32.28 |
| 19489 | C   | THR | D | 173 | -112.312 | 2.926  | 20.076 | 1.00 | 31.35 |
| 19490 | O   | THR | D | 173 | -111.811 | 2.095  | 19.323 | 1.00 | 31.72 |
| 19491 | N   | ASP | D | 174 | -111.598 | 3.878  | 20.666 | 1.00 | 31.24 |
| 19492 | CA  | ASP | D | 174 | -110.140 | 3.835  | 20.639 | 1.00 | 30.80 |
| 19493 | CB  | ASP | D | 174 | -109.544 | 5.223  | 20.855 | 1.00 | 30.93 |
| 19494 | CG  | ASP | D | 174 | -109.758 | 5.732  | 22.268 | 1.00 | 31.81 |
| 19495 | OD1 | ASP | D | 174 | -109.046 | 6.675  | 22.701 | 1.00 | 32.93 |
| 19496 | OD2 | ASP | D | 174 | -110.608 | 5.229  | 23.028 | 1.00 | 32.28 |
| 19497 | C   | ASP | D | 174 | -109.736 | 2.887  | 21.786 | 1.00 | 30.67 |
| 19498 | O   | ASP | D | 174 | -110.598 | 2.265  | 22.415 | 1.00 | 30.57 |
| 19499 | N   | TRP | D | 175 | -108.449 | 2.770  | 22.077 | 1.00 | 29.77 |
| 19500 | CA  | TRP | D | 175 | -108.038 | 1.874  | 23.156 | 1.00 | 29.76 |
| 19501 | CB  | TRP | D | 175 | -106.501 | 1.832  | 23.324 | 1.00 | 28.86 |
| 19502 | CG  | TRP | D | 175 | -106.079 | 0.702  | 24.180 | 1.00 | 27.03 |
| 19503 | CD1 | TRP | D | 175 | -105.674 | -0.533 | 23.762 | 1.00 | 26.23 |
| 19504 | NE1 | TRP | D | 175 | -105.372 | -1.326 | 24.841 | 1.00 | 23.65 |
| 19505 | CE2 | TRP | D | 175 | -105.586 | -0.613 | 25.990 | 1.00 | 24.67 |
| 19506 | CD2 | TRP | D | 175 | -106.044 | 0.669  | 25.609 | 1.00 | 24.92 |
| 19507 | CE3 | TRP | D | 175 | -106.352 | 1.593  | 26.614 | 1.00 | 24.73 |
| 19508 | CZ3 | TRP | D | 175 | -106.187 | 1.227  | 27.944 | 1.00 | 23.72 |
| 19509 | CH2 | TRP | D | 175 | -105.738 | -0.057 | 28.292 | 1.00 | 23.52 |
| 19510 | CZ2 | TRP | D | 175 | -105.436 | -0.993 | 27.331 | 1.00 | 24.29 |
| 19511 | C   | TRP | D | 175 | -108.700 | 2.130  | 24.524 | 1.00 | 29.64 |
| 19512 | O   | TRP | D | 175 | -109.288 | 1.214  | 25.112 | 1.00 | 29.33 |
| 19513 | N   | VAL | D | 176 | -108.585 | 3.351  | 25.047 | 1.00 | 29.99 |
| 19514 | CA  | VAL | D | 176 | -109.146 | 3.623  | 26.384 | 1.00 | 29.86 |
| 19515 | CB  | VAL | D | 176 | -108.826 | 5.014  | 26.946 | 1.00 | 30.01 |
| 19516 | CG1 | VAL | D | 176 | -108.403 | 5.962  | 25.878 | 1.00 | 30.79 |
| 19517 | CG2 | VAL | D | 176 | -107.824 | 4.921  | 28.065 | 1.00 | 29.46 |
| 19518 | C   | VAL | D | 176 | -110.646 | 3.519  | 26.503 | 1.00 | 29.80 |
| 19519 | O   | VAL | D | 176 | -111.170 | 3.202  | 27.582 | 1.00 | 30.14 |
| 19520 | N   | TYR | D | 177 | -111.359 | 3.828  | 25.434 | 1.00 | 29.56 |
| 19521 | CA  | TYR | D | 177 | -112.802 | 3.758  | 25.518 | 1.00 | 29.29 |
| 19522 | CB  | TYR | D | 177 | -113.455 | 4.559  | 24.402 | 1.00 | 29.80 |
| 19523 | CG  | TYR | D | 177 | -113.873 | 5.942  | 24.830 | 1.00 | 28.67 |

FIGURE 3 NS

| A | B | C | D | E | F | G | H | I | J |
|---|---|---|---|---|---|---|---|---|---|
| 19524 | CD1 | TYR | D | 177 | -112.994 | 6.999 | 24.757 | 1.00 | 28.83 |
| 19525 | CE1 | TYR | D | 177 | -113.377 | 8.265 | 25.148 | 1.00 | 28.90 |
| 19526 | CZ | TYR | D | 177 | -114.655 | 8.478 | 25.621 | 1.00 | 28.47 |
| 19527 | OH | TYR | D | 177 | -115.028 | 9.744 | 25.996 | 1.00 | 31.30 |
| 19528 | CE2 | TYR | D | 177 | -115.546 | 7.439 | 25.727 | 1.00 | 27.03 |
| 19529 | CD2 | TYR | D | 177 | -115.153 | 6.180 | 25.330 | 1.00 | 28.91 |
| 19530 | C | TYR | D | 177 | -113.238 | 2.316 | 25.508 | 1.00 | 29.00 |
| 19531 | O | TYR | D | 177 | -114.196 | 1.947 | 26.167 | 1.00 | 29.66 |
| 19532 | N | GLU | D | 178 | -112.509 | 1.491 | 24.780 | 1.00 | 28.93 |
| 19533 | CA | GLU | D | 178 | -112.802 | 0.073 | 24.745 | 1.00 | 28.98 |
| 19534 | CB | GLU | D | 178 | -111.969 | -0.641 | 23.673 | 1.00 | 28.58 |
| 19535 | CG | GLU | D | 178 | -112.344 | -2.112 | 23.565 | 1.00 | 28.40 |
| 19536 | CD | GLU | D | 178 | -111.427 | -2.912 | 22.672 | 1.00 | 30.67 |
| 19537 | OE1 | GLU | D | 178 | -111.338 | -4.168 | 22.869 | 1.00 | 31.95 |
| 19538 | OE2 | GLU | D | 178 | -110.795 | -2.297 | 21.779 | 1.00 | 30.39 |
| 19539 | C | GLU | D | 178 | -112.558 | -0.594 | 26.117 | 1.00 | 28.96 |
| 19540 | O | GLU | D | 178 | -113.420 | -1.282 | 26.652 | 1.00 | 28.96 |
| 19541 | N | GLU | D | 179 | -111.377 | -0.389 | 26.675 | 1.00 | 28.96 |
| 19542 | CA | GLU | D | 179 | -111.020 | -1.063 | 27.910 | 1.00 | 29.14 |
| 19543 | CB | GLU | D | 179 | -109.493 | -1.062 | 28.101 | 1.00 | 29.35 |
| 19544 | CG | GLU | D | 179 | -109.017 | -1.695 | 29.415 | 1.00 | 30.88 |
| 19545 | CD | GLU | D | 179 | -109.394 | -3.165 | 29.534 | 1.00 | 31.98 |
| 19546 | OE1 | GLU | D | 179 | -109.736 | -3.805 | 28.508 | 1.00 | 32.59 |
| 19547 | OE2 | GLU | D | 179 | -109.349 | -3.688 | 30.658 | 1.00 | 31.84 |
| 19548 | C | GLU | D | 179 | -111.691 | -0.511 | 29.161 | 1.00 | 29.26 |
| 19549 | O | GLU | D | 179 | -112.152 | -1.278 | 29.976 | 1.00 | 28.64 |
| 19550 | N | GLU | D | 180 | -111.768 | 0.813 | 29.285 | 1.00 | 29.60 |
| 19551 | CA | GLU | D | 180 | -112.125 | 1.441 | 30.556 | 1.00 | 30.72 |
| 19552 | CB | GLU | D | 180 | -111.065 | 2.483 | 30.932 | 1.00 | 29.57 |
| 19553 | CG | GLU | D | 180 | -109.648 | 1.973 | 30.883 | 1.00 | 30.51 |
| 19554 | CD | GLU | D | 180 | -109.369 | 0.924 | 31.956 | 1.00 | 30.74 |
| 19555 | OE1 | GLU | D | 180 | -110.315 | 0.533 | 32.702 | 1.00 | 28.94 |
| 19556 | OE2 | GLU | D | 180 | -108.199 | 0.501 | 32.043 | 1.00 | 29.25 |
| 19557 | C | GLU | D | 180 | -113.464 | 2.135 | 30.655 | 1.00 | 31.90 |
| 19558 | O | GLU | D | 180 | -113.957 | 2.385 | 31.745 | 1.00 | 31.57 |
| 19559 | N | VAL | D | 181 | -114.049 | 2.487 | 29.526 | 1.00 | 34.06 |
| 19560 | CA | VAL | D | 181 | -115.288 | 3.228 | 29.590 | 1.00 | 35.25 |
| 19561 | CB | VAL | D | 181 | -115.227 | 4.463 | 28.703 | 1.00 | 35.11 |
| 19562 | CG1 | VAL | D | 181 | -116.408 | 5.358 | 28.982 | 1.00 | 34.70 |
| 19563 | CG2 | VAL | D | 181 | -113.918 | 5.199 | 28.948 | 1.00 | 34.10 |
| 19564 | C | VAL | D | 181 | -116.439 | 2.365 | 29.167 | 1.00 | 36.48 |
| 19565 | O | VAL | D | 181 | -117.418 | 2.236 | 29.888 | 1.00 | 37.25 |
| 19566 | N | PHE | D | 182 | -116.306 | 1.752 | 28.005 | 1.00 | 37.81 |
| 19567 | CA | PHE | D | 182 | -117.401 | 0.997 | 27.435 | 1.00 | 38.93 |
| 19568 | CB | PHE | D | 182 | -117.570 | 1.348 | 25.963 | 1.00 | 39.29 |
| 19569 | CG | PHE | D | 182 | -118.052 | 2.736 | 25.727 | 1.00 | 40.33 |
| 19570 | CD1 | PHE | D | 182 | -118.630 | 3.458 | 26.737 | 1.00 | 43.17 |
| 19571 | CE1 | PHE | D | 182 | -119.087 | 4.740 | 26.514 | 1.00 | 44.23 |
| 19572 | CZ | PHE | D | 182 | -118.965 | 5.303 | 25.271 | 1.00 | 43.23 |
| 19573 | CE2 | PHE | D | 182 | -118.396 | 4.594 | 24.259 | 1.00 | 43.26 |
| 19574 | CD2 | PHE | D | 182 | -117.944 | 3.315 | 24.485 | 1.00 | 42.22 |

FIGURE 3 NT

| A | B | C | D | E | F | G | H | I | J |
|---|---|---|---|---|---|---|---|---|---|
| 19575 | C | PHE | D | 182 | -117.213 | -0.497 | 27.542 | 1.00 | 39.66 |
| 19576 | O | PHE | D | 182 | -118.157 | -1.242 | 27.312 | 1.00 | 40.63 |
| 19577 | N | SER | D | 183 | -116.009 | -0.957 | 27.874 | 1.00 | 39.53 |
| 19578 | CA | SER | D | 183 | -115.806 | -2.387 | 27.949 | 1.00 | 38.87 |
| 19579 | CB | SER | D | 183 | -116.412 | -2.979 | 29.227 | 1.00 | 39.11 |
| 19580 | OG | SER | D | 183 | -115.868 | -2.364 | 30.399 | 1.00 | 36.26 |
| 19581 | C | SER | D | 183 | -116.473 | -2.974 | 26.726 | 1.00 | 39.22 |
| 19582 | O | SER | D | 183 | -117.203 | -3.955 | 26.813 | 1.00 | 39.70 |
| 19583 | N | ALA | D | 184 | -116.229 | -2.342 | 25.582 | 1.00 | 39.15 |
| 19584 | CA | ALA | D | 184 | -116.721 | -2.815 | 24.301 | 1.00 | 39.26 |
| 19585 | CB | ALA | D | 184 | -118.223 | -2.687 | 24.212 | 1.00 | 39.44 |
| 19586 | C | ALA | D | 184 | -116.065 | -2.015 | 23.204 | 1.00 | 39.26 |
| 19587 | O | ALA | D | 184 | -115.707 | -0.859 | 23.403 | 1.00 | 39.65 |
| 19588 | N | TYR | D | 185 | -115.883 | -2.648 | 22.054 | 1.00 | 39.34 |
| 19589 | CA | TYR | D | 185 | -115.337 | -1.991 | 20.875 | 1.00 | 39.33 |
| 19590 | CB | TYR | D | 185 | -114.984 | -3.055 | 19.850 | 1.00 | 39.13 |
| 19591 | CG | TYR | D | 185 | -114.116 | -2.605 | 18.701 | 1.00 | 39.22 |
| 19592 | CD1 | TYR | D | 185 | -114.103 | -3.319 | 17.518 | 1.00 | 38.30 |
| 19593 | CE1 | TYR | D | 185 | -113.312 | -2.945 | 16.470 | 1.00 | 37.37 |
| 19594 | CZ | TYR | D | 185 | -112.515 | -1.853 | 16.578 | 1.00 | 37.94 |
| 19595 | OH | TYR | D | 185 | -111.729 | -1.523 | 15.503 | 1.00 | 41.08 |
| 19596 | CE2 | TYR | D | 185 | -112.496 | -1.108 | 17.733 | 1.00 | 37.73 |
| 19597 | CD2 | TYR | D | 185 | -113.293 | -1.492 | 18.800 | 1.00 | 38.47 |
| 19598 | C | TYR | D | 185 | -116.402 | -1.094 | 20.269 | 1.00 | 39.38 |
| 19599 | O | TYR | D | 185 | -116.116 | 0.007 | 19.793 | 1.00 | 39.52 |
| 19600 | N | SER | D | 186 | -117.637 | -1.578 | 20.314 | 1.00 | 39.62 |
| 19601 | CA | SER | D | 186 | -118.770 | -0.920 | 19.673 | 1.00 | 40.05 |
| 19602 | CB | SER | D | 186 | -120.014 | -1.793 | 19.756 | 1.00 | 40.06 |
| 19603 | OG | SER | D | 186 | -121.065 | -1.176 | 19.036 | 1.00 | 42.12 |
| 19604 | C | SER | D | 186 | -119.124 | 0.420 | 20.248 | 1.00 | 39.96 |
| 19605 | O | SER | D | 186 | -119.230 | 0.583 | 21.462 | 1.00 | 40.18 |
| 19606 | N | ALA | D | 187 | -119.322 | 1.383 | 19.361 | 1.00 | 40.02 |
| 19607 | CA | ALA | D | 187 | -119.751 | 2.714 | 19.765 | 1.00 | 39.89 |
| 19608 | CB | ALA | D | 187 | -118.604 | 3.695 | 19.672 | 1.00 | 39.01 |
| 19609 | C | ALA | D | 187 | -120.923 | 3.121 | 18.872 | 1.00 | 39.75 |
| 19610 | O | ALA | D | 187 | -121.025 | 4.254 | 18.422 | 1.00 | 39.42 |
| 19611 | N | LEU | D | 188 | -121.800 | 2.156 | 18.626 | 1.00 | 40.42 |
| 19612 | CA | LEU | D | 188 | -122.968 | 2.331 | 17.777 | 1.00 | 41.23 |
| 19613 | CB | LEU | D | 188 | -122.858 | 1.421 | 16.543 | 1.00 | 41.42 |
| 19614 | CG | LEU | D | 188 | -122.038 | 2.006 | 15.406 | 1.00 | 41.93 |
| 19615 | CD1 | LEU | D | 188 | -122.343 | 1.318 | 14.081 | 1.00 | 40.35 |
| 19616 | CD2 | LEU | D | 188 | -122.372 | 3.476 | 15.346 | 1.00 | 42.22 |
| 19617 | C | LEU | D | 188 | -124.226 | 1.965 | 18.545 | 1.00 | 41.55 |
| 19618 | O | LEU | D | 188 | -124.309 | 0.880 | 19.133 | 1.00 | 41.55 |
| 19619 | N | TRP | D | 189 | -125.215 | 2.846 | 18.516 | 1.00 | 41.91 |
| 19620 | CA | TRP | D | 189 | -126.449 | 2.589 | 19.246 | 1.00 | 43.18 |
| 19621 | CB | TRP | D | 189 | -126.504 | 3.439 | 20.524 | 1.00 | 42.79 |
| 19622 | CG | TRP | D | 189 | -125.345 | 3.180 | 21.435 | 1.00 | 43.11 |
| 19623 | CD1 | TRP | D | 189 | -125.248 | 2.200 | 22.380 | 1.00 | 42.61 |
| 19624 | NE1 | TRP | D | 189 | -124.030 | 2.272 | 23.010 | 1.00 | 42.77 |
| 19625 | CE2 | TRP | D | 189 | -123.309 | 3.302 | 22.466 | 1.00 | 42.51 |

FIGURE 3 NU

| A | B | C | D | E | F | G | H | I | J |
|---|---|---|---|---|---|---|---|---|---|
| 19626 | CD2 | TRP | D | 189 | -124.106 | 3.894 | 21.471 | 1.00 | 41.74 |
| 19627 | CE3 | TRP | D | 189 | -123.589 | 4.981 | 20.760 | 1.00 | 40.87 |
| 19628 | CZ3 | TRP | D | 189 | -122.332 | 5.433 | 21.058 | 1.00 | 40.77 |
| 19629 | CH2 | TRP | D | 189 | -121.559 | 4.823 | 22.049 | 1.00 | 41.77 |
| 19630 | CZ2 | TRP | D | 189 | -122.031 | 3.755 | 22.765 | 1.00 | 41.90 |
| 19631 | C | TRP | D | 189 | -127.721 | 2.791 | 18.414 | 1.00 | 43.78 |
| 19632 | O | TRP | D | 189 | -128.164 | 3.915 | 18.201 | 1.00 | 43.52 |
| 19633 | N | TRP | D | 190 | -128.287 | 1.677 | 17.959 | 1.00 | 44.99 |
| 19634 | CA | TRP | D | 190 | -129.548 | 1.665 | 17.226 | 1.00 | 46.13 |
| 19635 | CB | TRP | D | 190 | -129.875 | 0.247 | 16.747 | 1.00 | 45.99 |
| 19636 | CG | TRP | D | 190 | -129.246 | -0.242 | 15.478 | 1.00 | 47.26 |
| 19637 | CD1 | TRP | D | 190 | -128.410 | -1.317 | 15.343 | 1.00 | 47.79 |
| 19638 | NE1 | TRP | D | 190 | -128.060 | -1.484 | 14.026 | 1.00 | 47.56 |
| 19639 | CE2 | TRP | D | 190 | -128.686 | -0.526 | 13.277 | 1.00 | 47.82 |
| 19640 | CD2 | TRP | D | 190 | -129.448 | 0.268 | 14.158 | 1.00 | 47.61 |
| 19641 | CE3 | TRP | D | 190 | -130.185 | 1.325 | 13.628 | 1.00 | 49.11 |
| 19642 | CZ3 | TRP | D | 190 | -130.143 | 1.549 | 12.265 | 1.00 | 49.94 |
| 19643 | CH2 | TRP | D | 190 | -129.380 | 0.740 | 11.421 | 1.00 | 49.15 |
| 19644 | CZ2 | TRP | D | 190 | -128.644 | -0.297 | 11.908 | 1.00 | 48.54 |
| 19645 | C | TRP | D | 190 | -130.686 | 2.039 | 18.164 | 1.00 | 46.49 |
| 19646 | O | TRP | D | 190 | -130.698 | 1.639 | 19.328 | 1.00 | 46.91 |
| 19647 | N | SER | D | 191 | -131.658 | 2.783 | 17.651 | 1.00 | 46.78 |
| 19648 | CA | SER | D | 191 | -132.861 | 3.051 | 18.416 | 1.00 | 46.91 |
| 19649 | CB | SER | D | 191 | -133.702 | 4.149 | 17.760 | 1.00 | 46.85 |
| 19650 | OG | SER | D | 191 | -134.208 | 3.721 | 16.508 | 1.00 | 46.27 |
| 19651 | C | SER | D | 191 | -133.599 | 1.713 | 18.449 | 1.00 | 47.19 |
| 19652 | O | SER | D | 191 | -133.267 | 0.796 | 17.695 | 1.00 | 47.05 |
| 19653 | N | PRO | D | 192 | -134.572 | 1.583 | 19.337 | 1.00 | 47.51 |
| 19654 | CA | PRO | D | 192 | -135.280 | 0.313 | 19.522 | 1.00 | 48.10 |
| 19655 | CB | PRO | D | 192 | -136.323 | 0.656 | 20.582 | 1.00 | 48.31 |
| 19656 | CG | PRO | D | 192 | -135.743 | 1.822 | 21.306 | 1.00 | 47.57 |
| 19657 | CD | PRO | D | 192 | -135.040 | 2.627 | 20.261 | 1.00 | 47.53 |
| 19658 | C | PRO | D | 192 | -135.948 | -0.272 | 18.268 | 1.00 | 49.00 |
| 19659 | O | PRO | D | 192 | -136.024 | -1.498 | 18.146 | 1.00 | 48.81 |
| 19660 | N | ASN | D | 193 | -136.422 | 0.563 | 17.350 | 1.00 | 49.60 |
| 19661 | CA | ASN | D | 193 | -137.098 | 0.006 | 16.185 | 1.00 | 50.51 |
| 19662 | CB | ASN | D | 193 | -138.478 | 0.636 | 15.970 | 1.00 | 51.04 |
| 19663 | CG | ASN | D | 193 | -138.438 | 1.863 | 15.094 | 1.00 | 53.09 |
| 19664 | OD1 | ASN | D | 193 | -137.624 | 1.966 | 14.176 | 1.00 | 55.03 |
| 19665 | ND2 | ASN | D | 193 | -139.347 | 2.795 | 15.355 | 1.00 | 57.82 |
| 19666 | C | ASN | D | 193 | -136.253 | 0.027 | 14.920 | 1.00 | 50.46 |
| 19667 | O | ASN | D | 193 | -136.710 | -0.364 | 13.843 | 1.00 | 50.56 |
| 19668 | N | GLY | D | 194 | -135.018 | 0.495 | 15.056 | 1.00 | 49.91 |
| 19669 | CA | GLY | D | 194 | -134.109 | 0.520 | 13.931 | 1.00 | 49.23 |
| 19670 | C | GLY | D | 194 | -134.142 | 1.811 | 13.145 | 1.00 | 48.71 |
| 19671 | O | GLY | D | 194 | -133.450 | 1.945 | 12.141 | 1.00 | 48.79 |
| 19672 | N | THR | D | 195 | -134.929 | 2.773 | 13.601 | 1.00 | 48.01 |
| 19673 | CA | THR | D | 195 | -135.044 | 4.026 | 12.874 | 1.00 | 47.27 |
| 19674 | CB | THR | D | 195 | -136.232 | 4.839 | 13.394 | 1.00 | 47.08 |
| 19675 | OG1 | THR | D | 195 | -137.433 | 4.309 | 12.830 | 1.00 | 48.15 |
| 19676 | CG2 | THR | D | 195 | -136.196 | 6.249 | 12.852 | 1.00 | 46.07 |

FIGURE 3 NV

| A | B | C | D | E | F | G | H | I | J |
|---|---|---|---|---|---|---|---|---|---|
| 19677 | C | THR | D | 195 | -133.760 | 4.845 | 12.909 | 1.00 | 46.80 |
| 19678 | O | THR | D | 195 | -133.205 | 5.191 | 11.863 | 1.00 | 46.65 |
| 19679 | N | PHE | D | 196 | -133.293 | 5.163 | 14.109 | 1.00 | 46.15 |
| 19680 | CA | PHE | D | 196 | -132.081 | 5.956 | 14.240 | 1.00 | 45.58 |
| 19681 | CB | PHE | D | 196 | -132.231 | 7.004 | 15.336 | 1.00 | 46.02 |
| 19682 | CG | PHE | D | 196 | -133.336 | 7.998 | 15.097 | 1.00 | 46.92 |
| 19683 | CD1 | PHE | D | 196 | -133.112 | 9.140 | 14.349 | 1.00 | 47.46 |
| 19684 | CE1 | PHE | D | 196 | -134.129 | 10.070 | 14.155 | 1.00 | 48.60 |
| 19685 | CZ | PHE | D | 196 | -135.372 | 9.861 | 14.712 | 1.00 | 47.47 |
| 19686 | CE2 | PHE | D | 196 | -135.602 | 8.732 | 15.460 | 1.00 | 48.00 |
| 19687 | CD2 | PHE | D | 196 | -134.586 | 7.807 | 15.655 | 1.00 | 47.89 |
| 19688 | C | PHE | D | 196 | -130.871 | 5.106 | 14.559 | 1.00 | 44.71 |
| 19689 | O | PHE | D | 196 | -130.977 | 4.020 | 15.132 | 1.00 | 44.70 |
| 19690 | N | LEU | D | 197 | -129.710 | 5.607 | 14.173 | 1.00 | 43.96 |
| 19691 | CA | LEU | D | 197 | -128.456 | 4.965 | 14.515 | 1.00 | 42.62 |
| 19692 | CB | LEU | D | 197 | -127.728 | 4.458 | 13.286 | 1.00 | 42.73 |
| 19693 | CG | LEU | D | 197 | -126.345 | 3.877 | 13.547 | 1.00 | 42.17 |
| 19694 | CD1 | LEU | D | 197 | -125.787 | 3.269 | 12.290 | 1.00 | 42.13 |
| 19695 | CD2 | LEU | D | 197 | -126.392 | 2.829 | 14.644 | 1.00 | 43.28 |
| 19696 | C | LEU | D | 197 | -127.661 | 6.061 | 15.137 | 1.00 | 42.15 |
| 19697 | O | LEU | D | 197 | -127.332 | 7.040 | 14.475 | 1.00 | 41.99 |
| 19698 | N | ALA | D | 198 | -127.394 | 5.933 | 16.428 | 1.00 | 41.38 |
| 19699 | CA | ALA | D | 198 | -126.609 | 6.934 | 17.113 | 1.00 | 40.24 |
| 19700 | CB | ALA | D | 198 | -127.203 | 7.248 | 18.468 | 1.00 | 40.45 |
| 19701 | C | ALA | D | 198 | -125.245 | 6.319 | 17.251 | 1.00 | 39.57 |
| 19702 | O | ALA | D | 198 | -125.113 | 5.104 | 17.350 | 1.00 | 39.36 |
| 19703 | N | TYR | D | 199 | -124.221 | 7.148 | 17.240 | 1.00 | 38.64 |
| 19704 | CA | TYR | D | 199 | -122.880 | 6.618 | 17.341 | 1.00 | 38.12 |
| 19705 | CB | TYR | D | 199 | -122.369 | 6.224 | 15.951 | 1.00 | 38.38 |
| 19706 | CG | TYR | D | 199 | -122.292 | 7.377 | 14.963 | 1.00 | 38.47 |
| 19707 | CD1 | TYR | D | 199 | -121.131 | 8.132 | 14.842 | 1.00 | 37.96 |
| 19708 | CE1 | TYR | D | 199 | -121.046 | 9.172 | 13.924 | 1.00 | 39.86 |
| 19709 | CZ | TYR | D | 199 | -122.140 | 9.480 | 13.115 | 1.00 | 40.01 |
| 19710 | OH | TYR | D | 199 | -122.045 | 10.525 | 12.210 | 1.00 | 39.99 |
| 19711 | CE2 | TYR | D | 199 | -123.298 | 8.736 | 13.209 | 1.00 | 38.52 |
| 19712 | CD2 | TYR | D | 199 | -123.370 | 7.689 | 14.130 | 1.00 | 39.04 |
| 19713 | C | TYR | D | 199 | -121.994 | 7.667 | 17.964 | 1.00 | 37.29 |
| 19714 | O | TYR | D | 199 | -122.393 | 8.820 | 18.089 | 1.00 | 37.12 |
| 19715 | N | ALA | D | 200 | -120.800 | 7.262 | 18.374 | 1.00 | 36.49 |
| 19716 | CA | ALA | D | 200 | -119.840 | 8.204 | 18.920 | 1.00 | 35.72 |
| 19717 | CB | ALA | D | 200 | -119.360 | 7.752 | 20.284 | 1.00 | 35.51 |
| 19718 | C | ALA | D | 200 | -118.675 | 8.257 | 17.955 | 1.00 | 35.40 |
| 19719 | O | ALA | D | 200 | -118.445 | 7.308 | 17.211 | 1.00 | 35.07 |
| 19720 | N | GLN | D | 201 | -117.948 | 9.365 | 17.967 | 1.00 | 34.67 |
| 19721 | CA | GLN | D | 201 | -116.767 | 9.482 | 17.150 | 1.00 | 34.64 |
| 19722 | CB | GLN | D | 201 | -116.972 | 10.478 | 16.018 | 1.00 | 34.58 |
| 19723 | CG | GLN | D | 201 | -115.677 | 11.025 | 15.456 | 1.00 | 34.47 |
| 19724 | CD | GLN | D | 201 | -115.919 | 12.212 | 14.546 | 1.00 | 35.82 |
| 19725 | OE1 | GLN | D | 201 | -115.841 | 13.357 | 14.987 | 1.00 | 36.79 |
| 19726 | NE2 | GLN | D | 201 | -116.238 | 11.944 | 13.287 | 1.00 | 32.06 |
| 19727 | C | GLN | D | 201 | -115.637 | 9.957 | 18.033 | 1.00 | 34.24 |

FIGURE 3 NW

| A | B | C | D | E | F | G | H | I | J |
|---|---|---|---|---|---|---|---|---|---|
| 19728 | O | GLN | D | 201 | -115.740 | 10.998 | 18.670 | 1.00 | 34.35 |
| 19729 | N | PHE | D | 202 | -114.553 | 9.202 | 18.070 | 1.00 | 33.60 |
| 19730 | CA | PHE | D | 202 | -113.443 | 9.606 | 18.916 | 1.00 | 33.94 |
| 19731 | CB | PHE | D | 202 | -113.003 | 8.450 | 19.835 | 1.00 | 33.79 |
| 19732 | CG | PHE | D | 202 | -114.159 | 7.783 | 20.547 | 1.00 | 33.26 |
| 19733 | CD1 | PHE | D | 202 | -114.561 | 8.211 | 21.806 | 1.00 | 33.46 |
| 19734 | CE1 | PHE | D | 202 | -115.625 | 7.630 | 22.444 | 1.00 | 32.35 |
| 19735 | CZ | PHE | D | 202 | -116.325 | 6.618 | 21.833 | 1.00 | 33.18 |
| 19736 | CE2 | PHE | D | 202 | -115.952 | 6.193 | 20.566 | 1.00 | 33.55 |
| 19737 | CD2 | PHE | D | 202 | -114.873 | 6.776 | 19.934 | 1.00 | 32.40 |
| 19738 | C | PHE | D | 202 | -112.299 | 10.170 | 18.095 | 1.00 | 33.79 |
| 19739 | O | PHE | D | 202 | -112.011 | 9.726 | 16.993 | 1.00 | 32.93 |
| 19740 | N | ASN | D | 203 | -111.673 | 11.186 | 18.656 | 1.00 | 34.99 |
| 19741 | CA | ASN | D | 203 | -110.561 | 11.860 | 18.023 | 1.00 | 35.89 |
| 19742 | CB | ASN | D | 203 | -110.922 | 13.334 | 17.871 | 1.00 | 36.02 |
| 19743 | CG | ASN | D | 203 | -109.938 | 14.088 | 17.025 | 1.00 | 37.77 |
| 19744 | OD1 | ASN | D | 203 | -108.770 | 13.721 | 16.933 | 1.00 | 38.31 |
| 19745 | ND2 | ASN | D | 203 | -110.403 | 15.162 | 16.400 | 1.00 | 43.95 |
| 19746 | C | ASN | D | 203 | -109.300 | 11.704 | 18.879 | 1.00 | 36.16 |
| 19747 | O | ASN | D | 203 | -109.211 | 12.277 | 19.966 | 1.00 | 36.27 |
| 19748 | N | ASP | D | 204 | -108.327 | 10.944 | 18.382 | 1.00 | 36.54 |
| 19749 | CA | ASP | D | 204 | -107.086 | 10.710 | 19.106 | 1.00 | 37.36 |
| 19750 | CB | ASP | D | 204 | -106.746 | 9.215 | 19.127 | 1.00 | 37.61 |
| 19751 | CG | ASP | D | 204 | -107.684 | 8.421 | 20.006 | 1.00 | 37.75 |
| 19752 | OD1 | ASP | D | 204 | -108.911 | 8.614 | 19.878 | 1.00 | 38.80 |
| 19753 | OD2 | ASP | D | 204 | -107.293 | 7.582 | 20.842 | 1.00 | 36.60 |
| 19754 | C | ASP | D | 204 | -105.903 | 11.467 | 18.532 | 1.00 | 37.87 |
| 19755 | O | ASP | D | 204 | -104.751 | 11.155 | 18.835 | 1.00 | 38.21 |
| 19756 | N | THR | D | 205 | -106.164 | 12.464 | 17.707 | 1.00 | 38.14 |
| 19757 | CA | THR | D | 205 | -105.053 | 13.195 | 17.097 | 1.00 | 38.26 |
| 19758 | CB | THR | D | 205 | -105.506 | 14.549 | 16.520 | 1.00 | 38.05 |
| 19759 | OG1 | THR | D | 205 | -106.361 | 14.327 | 15.393 | 1.00 | 39.01 |
| 19760 | CG2 | THR | D | 205 | -104.314 | 15.265 | 15.918 | 1.00 | 37.32 |
| 19761 | C | THR | D | 205 | -103.852 | 13.418 | 18.019 | 1.00 | 38.03 |
| 19762 | O | THR | D | 205 | -102.714 | 13.100 | 17.660 | 1.00 | 37.78 |
| 19763 | N | GLU | D | 206 | -104.087 | 13.997 | 19.188 | 1.00 | 37.62 |
| 19764 | CA | GLU | D | 206 | -102.953 | 14.292 | 20.059 | 1.00 | 37.50 |
| 19765 | CB | GLU | D | 206 | -103.048 | 15.711 | 20.608 | 1.00 | 38.21 |
| 19766 | CG | GLU | D | 206 | -102.484 | 16.761 | 19.670 | 1.00 | 41.63 |
| 19767 | CD | GLU | D | 206 | -102.929 | 18.150 | 20.052 | 1.00 | 45.92 |
| 19768 | OE1 | GLU | D | 206 | -102.040 | 18.998 | 20.322 | 1.00 | 48.17 |
| 19769 | OE2 | GLU | D | 206 | -104.166 | 18.381 | 20.093 | 1.00 | 46.94 |
| 19770 | C | GLU | D | 206 | -102.711 | 13.313 | 21.208 | 1.00 | 36.08 |
| 19771 | O | GLU | D | 206 | -101.979 | 13.617 | 22.142 | 1.00 | 35.60 |
| 19772 | N | VAL | D | 207 | -103.313 | 12.142 | 21.177 | 1.00 | 34.78 |
| 19773 | CA | VAL | D | 207 | -102.956 | 11.236 | 22.252 | 1.00 | 34.13 |
| 19774 | CB | VAL | D | 207 | -104.118 | 10.309 | 22.686 | 1.00 | 34.28 |
| 19775 | CG1 | VAL | D | 207 | -103.765 | 8.857 | 22.537 | 1.00 | 34.90 |
| 19776 | CG2 | VAL | D | 207 | -105.406 | 10.705 | 21.988 | 1.00 | 34.08 |
| 19777 | C | VAL | D | 207 | -101.638 | 10.519 | 21.923 | 1.00 | 32.63 |
| 19778 | O | VAL | D | 207 | -101.434 | 10.002 | 20.822 | 1.00 | 31.99 |

FIGURE 3 NX

| A | B | C | D | E | F | G | H | I | J |
|---|---|---|---|---|---|---|---|---|---|
| 19779 | N | PRO | D | 208 | -100.712 | 10.557 | 22.867 | 1.00 | 31.85 |
| 19780 | CA | PRO | D | 208 | -99.409 | 9.936 | 22.650 | 1.00 | 31.33 |
| 19781 | CB | PRO | D | 208 | -98.680 | 10.182 | 23.966 | 1.00 | 31.40 |
| 19782 | CG | PRO | D | 208 | -99.388 | 11.391 | 24.576 | 1.00 | 31.21 |
| 19783 | CD | PRO | D | 208 | -100.832 | 11.187 | 24.199 | 1.00 | 31.62 |
| 19784 | C | PRO | D | 208 | -99.597 | 8.456 | 22.371 | 1.00 | 31.19 |
| 19785 | O | PRO | D | 208 | -100.636 | 7.883 | 22.720 | 1.00 | 31.26 |
| 19786 | N | LEU | D | 209 | -98.629 | 7.847 | 21.703 | 1.00 | 30.84 |
| 19787 | CA | LEU | D | 209 | -98.740 | 6.426 | 21.395 | 1.00 | 30.98 |
| 19788 | CB | LEU | D | 209 | -98.521 | 6.159 | 19.891 | 1.00 | 31.17 |
| 19789 | CG | LEU | D | 209 | -99.343 | 6.966 | 18.873 | 1.00 | 31.32 |
| 19790 | CD1 | LEU | D | 209 | -100.116 | 6.064 | 17.943 | 1.00 | 32.28 |
| 19791 | CD2 | LEU | D | 209 | -98.445 | 7.864 | 18.085 | 1.00 | 33.81 |
| 19792 | C | LEU | D | 209 | -97.782 | 5.581 | 22.239 | 1.00 | 30.34 |
| 19793 | O | LEU | D | 209 | -96.652 | 5.996 | 22.519 | 1.00 | 31.03 |
| 19794 | N | ILE | D | 210 | -98.248 | 4.420 | 22.683 | 1.00 | 29.33 |
| 19795 | CA | ILE | D | 210 | -97.363 | 3.504 | 23.391 | 1.00 | 28.55 |
| 19796 | CB | ILE | D | 210 | -98.128 | 2.609 | 24.366 | 1.00 | 27.87 |
| 19797 | CG1 | ILE | D | 210 | -97.194 | 1.600 | 25.046 | 1.00 | 26.81 |
| 19798 | CD1 | ILE | D | 210 | -95.991 | 2.195 | 25.727 | 1.00 | 25.03 |
| 19799 | CG2 | ILE | D | 210 | -99.226 | 1.859 | 23.631 | 1.00 | 28.10 |
| 19800 | C | ILE | D | 210 | -96.771 | 2.678 | 22.291 | 1.00 | 28.18 |
| 19801 | O | ILE | D | 210 | -97.500 | 2.229 | 21.427 | 1.00 | 27.53 |
| 19802 | N | GLU | D | 211 | -95.449 | 2.532 | 22.289 | 1.00 | 28.37 |
| 19803 | CA | GLU | D | 211 | -94.792 | 1.697 | 21.298 | 1.00 | 28.97 |
| 19804 | CB | GLU | D | 211 | -93.779 | 2.484 | 20.445 | 1.00 | 29.20 |
| 19805 | CG | GLU | D | 211 | -94.073 | 3.960 | 20.253 | 1.00 | 31.46 |
| 19806 | CD | GLU | D | 211 | -93.308 | 4.564 | 19.080 | 1.00 | 34.06 |
| 19807 | OE1 | GLU | D | 211 | -93.946 | 5.132 | 18.183 | 1.00 | 37.28 |
| 19808 | OE2 | GLU | D | 211 | -92.070 | 4.492 | 19.045 | 1.00 | 35.21 |
| 19809 | C | GLU | D | 211 | -94.058 | 0.559 | 21.997 | 1.00 | 28.84 |
| 19810 | O | GLU | D | 211 | -93.430 | 0.752 | 23.040 | 1.00 | 28.04 |
| 19811 | N | TYR | D | 212 | -94.121 | -0.620 | 21.395 | 1.00 | 28.90 |
| 19812 | CA | TYR | D | 212 | -93.392 | -1.767 | 21.893 | 1.00 | 29.35 |
| 19813 | CB | TYR | D | 212 | -94.152 | -2.481 | 23.018 | 1.00 | 29.57 |
| 19814 | CG | TYR | D | 212 | -95.564 | -2.794 | 22.675 | 1.00 | 28.88 |
| 19815 | CD1 | TYR | D | 212 | -95.896 | -3.972 | 22.027 | 1.00 | 29.65 |
| 19816 | CE1 | TYR | D | 212 | -97.200 | -4.258 | 21.706 | 1.00 | 28.84 |
| 19817 | CZ | TYR | D | 212 | -98.188 | -3.353 | 22.015 | 1.00 | 28.00 |
| 19818 | OH | TYR | D | 212 | -99.501 | -3.630 | 21.698 | 1.00 | 28.52 |
| 19819 | CE2 | TYR | D | 212 | -97.879 | -2.177 | 22.645 | 1.00 | 28.71 |
| 19820 | CD2 | TYR | D | 212 | -96.572 | -1.900 | 22.971 | 1.00 | 29.20 |
| 19821 | C | TYR | D | 212 | -93.124 | -2.709 | 20.757 | 1.00 | 29.59 |
| 19822 | O | TYR | D | 212 | -93.786 | -2.661 | 19.707 | 1.00 | 30.24 |
| 19823 | N | SER | D | 213 | -92.138 | -3.567 | 20.961 | 1.00 | 29.61 |
| 19824 | CA | SER | D | 213 | -91.752 | -4.527 | 19.948 | 1.00 | 29.47 |
| 19825 | CB | SER | D | 213 | -90.337 | -5.027 | 20.203 | 1.00 | 28.66 |
| 19826 | OG | SER | D | 213 | -89.418 | -3.945 | 20.118 | 1.00 | 29.20 |
| 19827 | C | SER | D | 213 | -92.709 | -5.699 | 19.880 | 1.00 | 29.72 |
| 19828 | O | SER | D | 213 | -93.221 | -6.148 | 20.900 | 1.00 | 30.07 |
| 19829 | N | PHE | D | 214 | -92.977 | -6.155 | 18.661 | 1.00 | 29.60 |

FIGURE 3 NY

| A | B | C | D | E | F | G | H | I | J |
|---|---|---|---|---|---|---|---|---|---|
| 19830 | CA | PHE | D | 214 | -93.727 | -7.379 | 18.445 | 1.00 | 30.26 |
| 19831 | CB | PHE | D | 214 | -95.054 | -7.141 | 17.751 | 1.00 | 30.16 |
| 19832 | CG | PHE | D | 214 | -95.995 | -8.303 | 17.869 | 1.00 | 31.47 |
| 19833 | CD1 | PHE | D | 214 | -96.002 | -9.301 | 16.913 | 1.00 | 30.09 |
| 19834 | CE1 | PHE | D | 214 | -96.836 | -10.358 | 17.020 | 1.00 | 29.10 |
| 19835 | CZ | PHE | D | 214 | -97.692 | -10.464 | 18.089 | 1.00 | 29.87 |
| 19836 | CE2 | PHE | D | 214 | -97.703 | -9.494 | 19.051 | 1.00 | 31.23 |
| 19837 | CD2 | PHE | D | 214 | -96.854 | -8.414 | 18.949 | 1.00 | 31.10 |
| 19838 | C | PHE | D | 214 | -92.831 | -8.263 | 17.597 | 1.00 | 30.20 |
| 19839 | O | PHE | D | 214 | -92.446 | -7.891 | 16.490 | 1.00 | 30.05 |
| 19840 | N | TYR | D | 215 | -92.509 | -9.437 | 18.121 | 1.00 | 30.18 |
| 19841 | CA | TYR | D | 215 | -91.502 | -10.275 | 17.501 | 1.00 | 30.12 |
| 19842 | CB | TYR | D | 215 | -90.724 | -11.052 | 18.578 | 1.00 | 29.28 |
| 19843 | CG | TYR | D | 215 | -90.102 | -10.062 | 19.523 | 1.00 | 27.33 |
| 19844 | CD1 | TYR | D | 215 | -90.713 | -9.748 | 20.732 | 1.00 | 23.82 |
| 19845 | CE1 | TYR | D | 215 | -90.170 | -8.828 | 21.567 | 1.00 | 22.15 |
| 19846 | CZ | TYR | D | 215 | -89.009 | -8.176 | 21.207 | 1.00 | 22.23 |
| 19847 | OH | TYR | D | 215 | -88.487 | -7.237 | 22.038 | 1.00 | 21.18 |
| 19848 | CE2 | TYR | D | 215 | -88.391 | -8.440 | 20.010 | 1.00 | 22.82 |
| 19849 | CD2 | TYR | D | 215 | -88.950 | -9.378 | 19.170 | 1.00 | 25.51 |
| 19850 | C | TYR | D | 215 | -92.036 | -11.136 | 16.387 | 1.00 | 31.07 |
| 19851 | O | TYR | D | 215 | -91.324 | -11.411 | 15.414 | 1.00 | 31.32 |
| 19852 | N | SER | D | 216 | -93.290 | -11.542 | 16.534 | 1.00 | 32.24 |
| 19853 | CA | SER | D | 216 | -93.977 | -12.331 | 15.523 | 1.00 | 33.25 |
| 19854 | CB | SER | D | 216 | -93.906 | -11.654 | 14.144 | 1.00 | 33.12 |
| 19855 | OG | SER | D | 216 | -94.802 | -12.287 | 13.238 | 1.00 | 32.97 |
| 19856 | C | SER | D | 216 | -93.357 | -13.704 | 15.449 | 1.00 | 33.82 |
| 19857 | O | SER | D | 216 | -92.623 | -14.108 | 16.353 | 1.00 | 33.58 |
| 19858 | N | ASP | D | 217 | -93.659 | -14.408 | 14.362 | 1.00 | 34.88 |
| 19859 | CA | ASP | D | 217 | -93.144 | -15.744 | 14.128 | 1.00 | 35.87 |
| 19860 | CB | ASP | D | 217 | -93.836 | -16.411 | 12.919 | 1.00 | 36.72 |
| 19861 | CG | ASP | D | 217 | -95.301 | -16.822 | 13.222 | 1.00 | 40.47 |
| 19862 | OD1 | ASP | D | 217 | -95.515 | -17.742 | 14.060 | 1.00 | 42.47 |
| 19863 | OD2 | ASP | D | 217 | -96.298 | -16.280 | 12.670 | 1.00 | 42.44 |
| 19864 | C | ASP | D | 217 | -91.658 | -15.623 | 13.886 | 1.00 | 36.06 |
| 19865 | O | ASP | D | 217 | -91.157 | -14.561 | 13.516 | 1.00 | 36.00 |
| 19866 | N | GLU | D | 218 | -90.956 | -16.722 | 14.104 | 1.00 | 36.36 |
| 19867 | CA | GLU | D | 218 | -89.523 | -16.775 | 13.912 | 1.00 | 36.81 |
| 19868 | CB | GLU | D | 218 | -89.059 | -18.214 | 14.114 | 1.00 | 37.14 |
| 19869 | CG | GLU | D | 218 | -87.604 | -18.453 | 13.807 | 1.00 | 40.56 |
| 19870 | CD | GLU | D | 218 | -87.200 | -19.893 | 14.038 | 1.00 | 44.21 |
| 19871 | OE1 | GLU | D | 218 | -86.058 | -20.230 | 13.649 | 1.00 | 45.99 |
| 19872 | OE2 | GLU | D | 218 | -88.015 | -20.676 | 14.601 | 1.00 | 43.55 |
| 19873 | C | GLU | D | 218 | -89.096 | -16.244 | 12.539 | 1.00 | 36.39 |
| 19874 | O | GLU | D | 218 | -88.002 | -15.715 | 12.402 | 1.00 | 36.03 |
| 19875 | N | SER | D | 219 | -89.963 | -16.362 | 11.533 | 1.00 | 36.00 |
| 19876 | CA | SER | D | 219 | -89.633 | -15.898 | 10.179 | 1.00 | 35.98 |
| 19877 | CB | SER | D | 219 | -90.638 | -16.439 | 9.163 | 1.00 | 36.02 |
| 19878 | OG | SER | D | 219 | -91.961 | -16.148 | 9.556 | 1.00 | 36.24 |
| 19879 | C | SER | D | 219 | -89.514 | -14.373 | 10.000 | 1.00 | 36.12 |
| 19880 | O | SER | D | 219 | -88.973 | -13.910 | 8.995 | 1.00 | 35.86 |

FIGURE 3 NZ

| A | B | C | D | E | F | G | H | I | J |
|---|---|---|---|---|---|---|---|---|---|
| 19881 | N | LEU | D | 220 | -90.024 | -13.588 | 10.949 | 1.00 | 35.55 |
| 19882 | CA | LEU | D | 220 | -89.922 | -12.145 | 10.820 | 1.00 | 35.01 |
| 19883 | CB | LEU | D | 220 | -90.835 | -11.446 | 11.811 | 1.00 | 34.74 |
| 19884 | CG | LEU | D | 220 | -91.625 | -10.236 | 11.315 | 1.00 | 35.21 |
| 19885 | CD1 | LEU | D | 220 | -91.666 | -9.135 | 12.401 | 1.00 | 29.79 |
| 19886 | CD2 | LEU | D | 220 | -91.099 | -9.711 | 9.972 | 1.00 | 32.56 |
| 19887 | C | LEU | D | 220 | -88.483 | -11.772 | 11.113 | 1.00 | 35.13 |
| 19888 | O | LEU | D | 220 | -88.003 | -12.017 | 12.217 | 1.00 | 35.41 |
| 19889 | N | GLN | D | 221 | -87.804 | -11.173 | 10.142 | 1.00 | 34.37 |
| 19890 | CA | GLN | D | 221 | -86.396 | -10.850 | 10.297 | 1.00 | 34.60 |
| 19891 | CB | GLN | D | 221 | -85.708 | -10.670 | 8.931 | 1.00 | 34.28 |
| 19892 | CG | GLN | D | 221 | -84.268 | -10.179 | 9.005 | 1.00 | 36.05 |
| 19893 | CD | GLN | D | 221 | -83.468 | -10.432 | 7.711 | 1.00 | 38.63 |
| 19894 | OE1 | GLN | D | 221 | -82.371 | -10.994 | 7.755 | 1.00 | 38.23 |
| 19895 | NE2 | GLN | D | 221 | -84.017 | -10.010 | 6.569 | 1.00 | 38.62 |
| 19896 | C | GLN | D | 221 | -86.218 | -9.625 | 11.180 | 1.00 | 34.16 |
| 19897 | O | GLN | D | 221 | -85.342 | -9.575 | 12.025 | 1.00 | 33.56 |
| 19898 | N | TYR | D | 222 | -87.061 | -8.631 | 10.983 | 1.00 | 34.08 |
| 19899 | CA | TYR | D | 222 | -86.981 | -7.448 | 11.808 | 1.00 | 33.86 |
| 19900 | CB | TYR | D | 222 | -86.860 | -6.195 | 10.945 | 1.00 | 33.19 |
| 19901 | CG | TYR | D | 222 | -85.502 | -6.002 | 10.315 | 1.00 | 32.55 |
| 19902 | CD1 | TYR | D | 222 | -84.581 | -5.148 | 10.884 | 1.00 | 30.98 |
| 19903 | CE1 | TYR | D | 222 | -83.343 | -4.958 | 10.319 | 1.00 | 29.73 |
| 19904 | CZ | TYR | D | 222 | -83.007 | -5.614 | 9.168 | 1.00 | 30.36 |
| 19905 | OH | TYR | D | 222 | -81.754 | -5.386 | 8.628 | 1.00 | 27.90 |
| 19906 | CE2 | TYR | D | 222 | -83.909 | -6.472 | 8.573 | 1.00 | 29.02 |
| 19907 | CD2 | TYR | D | 222 | -85.146 | -6.659 | 9.141 | 1.00 | 30.28 |
| 19908 | C | TYR | D | 222 | -88.234 | -7.358 | 12.662 | 1.00 | 34.09 |
| 19909 | O | TYR | D | 222 | -89.335 | -7.502 | 12.160 | 1.00 | 34.31 |
| 19910 | N | PRO | D | 223 | -88.065 | -7.112 | 13.952 | 1.00 | 34.14 |
| 19911 | CA | PRO | D | 223 | -89.207 | -6.944 | 14.847 | 1.00 | 34.27 |
| 19912 | CB | PRO | D | 223 | -88.550 | -6.573 | 16.174 | 1.00 | 33.88 |
| 19913 | CG | PRO | D | 223 | -87.203 | -7.171 | 16.080 | 1.00 | 34.68 |
| 19914 | CD | PRO | D | 223 | -86.786 | -6.987 | 14.659 | 1.00 | 33.87 |
| 19915 | C | PRO | D | 223 | -90.065 | -5.797 | 14.381 | 1.00 | 34.22 |
| 19916 | O | PRO | D | 223 | -89.557 | -4.819 | 13.859 | 1.00 | 34.41 |
| 19917 | N | LYS | D | 224 | -91.359 | -5.918 | 14.617 | 1.00 | 34.36 |
| 19918 | CA | LYS | D | 224 | -92.327 | -4.910 | 14.246 | 1.00 | 34.39 |
| 19919 | CB | LYS | D | 224 | -93.581 | -5.644 | 13.787 | 1.00 | 34.71 |
| 19920 | CG | LYS | D | 224 | -94.691 | -4.779 | 13.283 | 1.00 | 37.46 |
| 19921 | CD | LYS | D | 224 | -95.775 | -5.674 | 12.694 | 1.00 | 41.70 |
| 19922 | CE | LYS | D | 224 | -96.832 | -6.090 | 13.725 | 1.00 | 43.67 |
| 19923 | NZ | LYS | D | 224 | -98.161 | -5.463 | 13.412 | 1.00 | 44.44 |
| 19924 | C | LYS | D | 224 | -92.630 | -4.016 | 15.452 | 1.00 | 33.72 |
| 19925 | O | LYS | D | 224 | -92.751 | -4.491 | 16.566 | 1.00 | 34.71 |
| 19926 | N | THR | D | 225 | -92.731 | -2.719 | 15.243 | 1.00 | 32.82 |
| 19927 | CA | THR | D | 225 | -93.053 | -1.816 | 16.325 | 1.00 | 31.33 |
| 19928 | CB | THR | D | 225 | -92.217 | -0.546 | 16.220 | 1.00 | 31.33 |
| 19929 | OG1 | THR | D | 225 | -90.834 | -0.888 | 16.378 | 1.00 | 28.29 |
| 19930 | CG2 | THR | D | 225 | -92.513 | 0.401 | 17.408 | 1.00 | 29.29 |
| 19931 | C | THR | D | 225 | -94.539 | -1.479 | 16.295 | 1.00 | 31.74 |

FIGURE 3 OA

| A | B | C | D | E | F | G | H | I | J |
|---|---|---|---|---|---|---|---|---|---|
| 19932 | O | THR | D | 225 | -95.032 | -0.894 | 15.335 | 1.00 | 32.38 |
| 19933 | N | VAL | D | 226 | -95.250 | -1.885 | 17.337 | 1.00 | 31.14 |
| 19934 | CA | VAL | D | 226 | -96.664 | -1.612 | 17.453 | 1.00 | 30.16 |
| 19935 | CB | VAL | D | 226 | -97.355 | -2.626 | 18.379 | 1.00 | 30.16 |
| 19936 | CG1 | VAL | D | 226 | -98.778 | -2.192 | 18.694 | 1.00 | 29.53 |
| 19937 | CG2 | VAL | D | 226 | -97.313 | -4.040 | 17.779 | 1.00 | 28.64 |
| 19938 | C | VAL | D | 226 | -96.749 | -0.249 | 18.085 | 1.00 | 30.36 |
| 19939 | O | VAL | D | 226 | -96.000 | 0.067 | 19.033 | 1.00 | 30.18 |
| 19940 | N | ARG | D | 227 | -97.663 | 0.558 | 17.566 | 1.00 | 29.90 |
| 19941 | CA | ARG | D | 227 | -97.847 | 1.911 | 18.031 | 1.00 | 29.68 |
| 19942 | CB | ARG | D | 227 | -97.330 | 2.892 | 16.965 | 1.00 | 30.45 |
| 19943 | CG | ARG | D | 227 | -95.833 | 2.741 | 16.607 | 1.00 | 31.29 |
| 19944 | CD | ARG | D | 227 | -95.266 | 3.880 | 15.753 | 1.00 | 33.74 |
| 19945 | NE | ARG | D | 227 | -93.794 | 3.932 | 15.704 | 1.00 | 38.15 |
| 19946 | CZ | ARG | D | 227 | -93.013 | 3.212 | 14.876 | 1.00 | 37.63 |
| 19947 | NH1 | ARG | D | 227 | -93.548 | 2.339 | 14.025 | 1.00 | 39.45 |
| 19948 | NH2 | ARG | D | 227 | -91.696 | 3.363 | 14.902 | 1.00 | 34.26 |
| 19949 | C | ARG | D | 227 | -99.336 | 2.089 | 18.265 | 1.00 | 29.49 |
| 19950 | O | ARG | D | 227 | -100.131 | 1.899 | 17.356 | 1.00 | 29.57 |
| 19951 | N | VAL | D | 228 | -99.740 | 2.411 | 19.491 | 1.00 | 29.10 |
| 19952 | CA | VAL | D | 228 | -101.166 | 2.580 | 19.753 | 1.00 | 28.12 |
| 19953 | CB | VAL | D | 228 | -101.834 | 1.313 | 20.377 | 1.00 | 28.67 |
| 19954 | CG1 | VAL | D | 228 | -102.402 | 1.590 | 21.760 | 1.00 | 29.84 |
| 19955 | CG2 | VAL | D | 228 | -100.896 | 0.113 | 20.397 | 1.00 | 27.52 |
| 19956 | C | VAL | D | 228 | -101.419 | 3.833 | 20.581 | 1.00 | 27.61 |
| 19957 | O | VAL | D | 228 | -100.664 | 4.139 | 21.501 | 1.00 | 27.98 |
| 19958 | N | PRO | D | 229 | -102.451 | 4.596 | 20.223 | 1.00 | 26.71 |
| 19959 | CA | PRO | D | 229 | -102.738 | 5.827 | 20.950 | 1.00 | 26.21 |
| 19960 | CB | PRO | D | 229 | -103.858 | 6.482 | 20.128 | 1.00 | 26.21 |
| 19961 | CG | PRO | D | 229 | -103.905 | 5.721 | 18.827 | 1.00 | 26.12 |
| 19962 | CD | PRO | D | 229 | -103.407 | 4.357 | 19.133 | 1.00 | 26.51 |
| 19963 | C | PRO | D | 229 | -103.235 | 5.366 | 22.297 | 1.00 | 25.46 |
| 19964 | O | PRO | D | 229 | -104.206 | 4.619 | 22.355 | 1.00 | 25.44 |
| 19965 | N | TYR | D | 230 | -102.563 | 5.802 | 23.353 | 1.00 | 24.72 |
| 19966 | CA | TYR | D | 230 | -102.862 | 5.379 | 24.705 | 1.00 | 23.40 |
| 19967 | CB | TYR | D | 230 | -101.962 | 4.177 | 25.017 | 1.00 | 23.36 |
| 19968 | CG | TYR | D | 230 | -102.160 | 3.472 | 26.344 | 1.00 | 22.61 |
| 19969 | CD1 | TYR | D | 230 | -102.622 | 2.147 | 26.394 | 1.00 | 22.13 |
| 19970 | CE1 | TYR | D | 230 | -102.777 | 1.497 | 27.585 | 1.00 | 20.23 |
| 19971 | CZ | TYR | D | 230 | -102.459 | 2.164 | 28.763 | 1.00 | 20.96 |
| 19972 | OH | TYR | D | 230 | -102.615 | 1.556 | 29.985 | 1.00 | 19.64 |
| 19973 | CE2 | TYR | D | 230 | -101.996 | 3.468 | 28.732 | 1.00 | 19.94 |
| 19974 | CD2 | TYR | D | 230 | -101.847 | 4.104 | 27.537 | 1.00 | 19.59 |
| 19975 | C | TYR | D | 230 | -102.548 | 6.559 | 25.612 | 1.00 | 23.32 |
| 19976 | O | TYR | D | 230 | -101.403 | 7.006 | 25.713 | 1.00 | 23.98 |
| 19977 | N | PRO | D | 231 | -103.554 | 7.097 | 26.272 | 1.00 | 23.36 |
| 19978 | CA | PRO | D | 231 | -103.316 | 8.211 | 27.185 | 1.00 | 23.64 |
| 19979 | CB | PRO | D | 231 | -104.667 | 8.905 | 27.264 | 1.00 | 22.98 |
| 19980 | CG | PRO | D | 231 | -105.628 | 8.016 | 26.512 | 1.00 | 24.01 |
| 19981 | CD | PRO | D | 231 | -104.969 | 6.708 | 26.228 | 1.00 | 23.69 |
| 19982 | C | PRO | D | 231 | -102.936 | 7.662 | 28.562 | 1.00 | 24.12 |

FIGURE 3 OB

| A | B | C | D | E | F | G | H | I | J |
|---|---|---|---|---|---|---|---|---|---|
| 19983 | O | PRO | D | 231 | -103.731 | 6.996 | 29.240 | 1.00 | 24.04 |
| 19984 | N | LYS | D | 232 | -101.693 | 7.905 | 28.944 | 1.00 | 24.54 |
| 19985 | CA | LYS | D | 232 | -101.222 | 7.566 | 30.262 | 1.00 | 24.86 |
| 19986 | CB | LYS | D | 232 | -99.696 | 7.447 | 30.252 | 1.00 | 24.86 |
| 19987 | CG | LYS | D | 232 | -99.215 | 6.189 | 29.506 | 1.00 | 24.09 |
| 19988 | CD | LYS | D | 232 | -97.715 | 6.177 | 29.268 | 1.00 | 23.88 |
| 19989 | CE | LYS | D | 232 | -97.232 | 4.834 | 28.657 | 1.00 | 23.84 |
| 19990 | NZ | LYS | D | 232 | -97.246 | 3.661 | 29.615 | 1.00 | 22.47 |
| 19991 | C | LYS | D | 232 | -101.735 | 8.666 | 31.182 | 1.00 | 25.31 |
| 19992 | O | LYS | D | 232 | -102.104 | 9.744 | 30.727 | 1.00 | 25.47 |
| 19993 | N | ALA | D | 233 | -101.791 | 8.377 | 32.470 | 1.00 | 26.01 |
| 19994 | CA | ALA | D | 233 | -102.283 | 9.325 | 33.462 | 1.00 | 26.13 |
| 19995 | CB | ALA | D | 233 | -101.862 | 8.877 | 34.834 | 1.00 | 25.92 |
| 19996 | C | ALA | D | 233 | -101.795 | 10.740 | 33.220 | 1.00 | 26.28 |
| 19997 | O | ALA | D | 233 | -100.604 | 10.985 | 33.215 | 1.00 | 25.80 |
| 19998 | N | GLY | D | 234 | -102.724 | 11.667 | 33.021 | 1.00 | 26.56 |
| 19999 | CA | GLY | D | 234 | -102.359 | 13.054 | 32.846 | 1.00 | 27.38 |
| 20000 | C | GLY | D | 234 | -102.013 | 13.518 | 31.438 | 1.00 | 28.02 |
| 20001 | O | GLY | D | 234 | -101.698 | 14.693 | 31.241 | 1.00 | 28.33 |
| 20002 | N | ALA | D | 235 | -102.064 | 12.621 | 30.465 | 1.00 | 28.27 |
| 20003 | CA | ALA | D | 235 | -101.693 | 12.967 | 29.096 | 1.00 | 29.15 |
| 20004 | CB | ALA | D | 235 | -101.160 | 11.740 | 28.350 | 1.00 | 28.71 |
| 20005 | C | ALA | D | 235 | -102.931 | 13.463 | 28.422 | 1.00 | 30.05 |
| 20006 | O | ALA | D | 235 | -104.018 | 13.432 | 29.016 | 1.00 | 30.41 |
| 20007 | N | VAL | D | 236 | -102.806 | 13.893 | 27.169 | 1.00 | 30.38 |
| 20008 | CA | VAL | D | 236 | -104.001 | 14.369 | 26.517 | 1.00 | 30.22 |
| 20009 | CB | VAL | D | 236 | -103.722 | 15.366 | 25.346 | 1.00 | 30.88 |
| 20010 | CG1 | VAL | D | 236 | -103.802 | 14.675 | 24.009 | 1.00 | 31.62 |
| 20011 | CG2 | VAL | D | 236 | -102.401 | 16.090 | 25.552 | 1.00 | 30.21 |
| 20012 | C | VAL | D | 236 | -104.842 | 13.177 | 26.125 | 1.00 | 30.03 |
| 20013 | O | VAL | D | 236 | -104.346 | 12.157 | 25.637 | 1.00 | 30.27 |
| 20014 | N | ASN | D | 237 | -106.134 | 13.324 | 26.349 | 1.00 | 30.09 |
| 20015 | CA | ASN | D | 237 | -107.107 | 12.274 | 26.141 | 1.00 | 30.11 |
| 20016 | CB | ASN | D | 237 | -108.166 | 12.387 | 27.241 | 1.00 | 29.80 |
| 20017 | CG | ASN | D | 237 | -107.940 | 11.424 | 28.392 | 1.00 | 30.52 |
| 20018 | OD1 | ASN | D | 237 | -106.952 | 10.678 | 28.422 | 1.00 | 30.25 |
| 20019 | ND2 | ASN | D | 237 | -108.872 | 11.429 | 29.352 | 1.00 | 30.08 |
| 20020 | C | ASN | D | 237 | -107.796 | 12.434 | 24.797 | 1.00 | 30.85 |
| 20021 | O | ASN | D | 237 | -107.814 | 13.515 | 24.235 | 1.00 | 31.48 |
| 20022 | N | PRO | D | 238 | -108.363 | 11.361 | 24.279 | 1.00 | 30.78 |
| 20023 | CA | PRO | D | 238 | -109.156 | 11.441 | 23.069 | 1.00 | 31.29 |
| 20024 | CB | PRO | D | 238 | -109.615 | 9.993 | 22.877 | 1.00 | 31.14 |
| 20025 | CG | PRO | D | 238 | -109.534 | 9.419 | 24.278 | 1.00 | 31.07 |
| 20026 | CD | PRO | D | 238 | -108.274 | 9.985 | 24.799 | 1.00 | 31.04 |
| 20027 | C | PRO | D | 238 | -110.369 | 12.330 | 23.361 | 1.00 | 32.20 |
| 20028 | O | PRO | D | 238 | -110.814 | 12.427 | 24.522 | 1.00 | 32.07 |
| 20029 | N | THR | D | 239 | -110.874 | 13.017 | 22.344 | 1.00 | 32.48 |
| 20030 | CA | THR | D | 239 | -112.070 | 13.809 | 22.548 | 1.00 | 32.85 |
| 20031 | CB | THR | D | 239 | -111.966 | 15.207 | 21.951 | 1.00 | 32.83 |
| 20032 | OG1 | THR | D | 239 | -111.503 | 15.123 | 20.597 | 1.00 | 33.97 |
| 20033 | CG2 | THR | D | 239 | -110.909 | 16.031 | 22.676 | 1.00 | 31.34 |

FIGURE 3 OC

| A | B | C | D | E | F | G | H | I | J |
|---|---|---|---|---|---|---|---|---|---|
| 20034 | C | THR | D | 239 | -113.163 | 13.024 | 21.885 | 1.00 | 33.35 |
| 20035 | O | THR | D | 239 | -112.897 | 12.187 | 21.029 | 1.00 | 34.01 |
| 20036 | N | VAL | D | 240 | -114.395 | 13.269 | 22.294 | 1.00 | 33.86 |
| 20037 | CA | VAL | D | 240 | -115.500 | 12.513 | 21.748 | 1.00 | 34.02 |
| 20038 | CB | VAL | D | 240 | -116.100 | 11.566 | 22.826 | 1.00 | 33.91 |
| 20039 | CG1 | VAL | D | 240 | -117.224 | 10.719 | 22.255 | 1.00 | 32.87 |
| 20040 | CG2 | VAL | D | 240 | -116.573 | 12.356 | 24.030 | 1.00 | 32.74 |
| 20041 | C | VAL | D | 240 | -116.582 | 13.443 | 21.231 | 1.00 | 34.58 |
| 20042 | O | VAL | D | 240 | -116.815 | 14.520 | 21.780 | 1.00 | 34.31 |
| 20043 | N | LYS | D | 241 | -117.222 | 13.025 | 20.154 | 1.00 | 35.43 |
| 20044 | CA | LYS | D | 241 | -118.380 | 13.733 | 19.648 | 1.00 | 37.05 |
| 20045 | CB | LYS | D | 241 | -118.088 | 14.372 | 18.300 | 1.00 | 36.97 |
| 20046 | CG | LYS | D | 241 | -117.967 | 15.870 | 18.361 | 1.00 | 38.64 |
| 20047 | CD | LYS | D | 241 | -116.536 | 16.337 | 18.583 | 1.00 | 42.01 |
| 20048 | CE | LYS | D | 241 | -116.249 | 17.594 | 17.744 | 1.00 | 42.56 |
| 20049 | NZ | LYS | D | 241 | -116.606 | 17.384 | 16.306 | 1.00 | 41.46 |
| 20050 | C | LYS | D | 241 | -119.506 | 12.727 | 19.526 | 1.00 | 37.27 |
| 20051 | O | LYS | D | 241 | -119.251 | 11.540 | 19.347 | 1.00 | 37.51 |
| 20052 | N | PHE | D | 242 | -120.746 | 13.194 | 19.631 | 1.00 | 38.06 |
| 20053 | CA | PHE | D | 242 | -121.895 | 12.300 | 19.539 | 1.00 | 38.80 |
| 20054 | CB | PHE | D | 242 | -122.654 | 12.258 | 20.868 | 1.00 | 38.44 |
| 20055 | CG | PHE | D | 242 | -123.665 | 11.153 | 20.943 | 1.00 | 37.10 |
| 20056 | CD1 | PHE | D | 242 | -123.261 | 9.842 | 21.131 | 1.00 | 36.86 |
| 20057 | CE1 | PHE | D | 242 | -124.193 | 8.804 | 21.184 | 1.00 | 35.84 |
| 20058 | CZ | PHE | D | 242 | -125.535 | 9.087 | 21.051 | 1.00 | 35.22 |
| 20059 | CE2 | PHE | D | 242 | -125.947 | 10.399 | 20.856 | 1.00 | 35.00 |
| 20060 | CD2 | PHE | D | 242 | -125.015 | 11.418 | 20.796 | 1.00 | 35.38 |
| 20061 | C | PHE | D | 242 | -122.837 | 12.664 | 18.388 | 1.00 | 39.90 |
| 20062 | O | PHE | D | 242 | -123.058 | 13.831 | 18.097 | 1.00 | 40.25 |
| 20063 | N | PHE | D | 243 | -123.406 | 11.660 | 17.738 | 1.00 | 41.32 |
| 20064 | CA | PHE | D | 243 | -124.248 | 11.917 | 16.582 | 1.00 | 43.02 |
| 20065 | CB | PHE | D | 243 | -123.416 | 11.794 | 15.279 | 1.00 | 43.24 |
| 20066 | CG | PHE | D | 243 | -122.235 | 12.736 | 15.200 | 1.00 | 44.45 |
| 20067 | CD1 | PHE | D | 243 | -120.989 | 12.360 | 15.705 | 1.00 | 45.86 |
| 20068 | CE1 | PHE | D | 243 | -119.893 | 13.226 | 15.635 | 1.00 | 45.64 |
| 20069 | CZ | PHE | D | 243 | -120.037 | 14.474 | 15.050 | 1.00 | 46.41 |
| 20070 | CE2 | PHE | D | 243 | -121.281 | 14.857 | 14.541 | 1.00 | 44.75 |
| 20071 | CD2 | PHE | D | 243 | -122.364 | 13.985 | 14.616 | 1.00 | 43.97 |
| 20072 | C | PHE | D | 243 | -125.411 | 10.938 | 16.490 | 1.00 | 43.55 |
| 20073 | O | PHE | D | 243 | -125.351 | 9.839 | 17.032 | 1.00 | 43.91 |
| 20074 | N | VAL | D | 244 | -126.477 | 11.341 | 15.810 | 1.00 | 44.19 |
| 20075 | CA | VAL | D | 244 | -127.517 | 10.374 | 15.447 | 1.00 | 44.95 |
| 20076 | CB | VAL | D | 244 | -128.725 | 10.343 | 16.413 | 1.00 | 44.90 |
| 20077 | CG1 | VAL | D | 244 | -128.985 | 11.706 | 17.015 | 1.00 | 45.24 |
| 20078 | CG2 | VAL | D | 244 | -129.953 | 9.803 | 15.706 | 1.00 | 44.23 |
| 20079 | C | VAL | D | 244 | -127.951 | 10.583 | 13.995 | 1.00 | 45.46 |
| 20080 | O | VAL | D | 244 | -128.018 | 11.711 | 13.503 | 1.00 | 45.39 |
| 20081 | N | VAL | D | 245 | -128.199 | 9.490 | 13.294 | 1.00 | 46.23 |
| 20082 | CA | VAL | D | 245 | -128.586 | 9.601 | 11.906 | 1.00 | 47.38 |
| 20083 | CB | VAL | D | 245 | -127.457 | 9.099 | 10.966 | 1.00 | 47.64 |
| 20084 | CG1 | VAL | D | 245 | -127.261 | 7.594 | 11.094 | 1.00 | 47.24 |

FIGURE 3 OD

| A | B | C | D | E | F | G | H | I | J |
|---|---|---|---|---|---|---|---|---|---|
| 20085 | CG2 | VAL | D | 245 | -127.733 | 9.503 | 9.517 | 1.00 | 47.82 |
| 20086 | C | VAL | D | 245 | -129.876 | 8.834 | 11.671 | 1.00 | 48.10 |
| 20087 | O | VAL | D | 245 | -130.081 | 7.766 | 12.252 | 1.00 | 47.57 |
| 20088 | N | ASN | D | 246 | -130.760 | 9.401 | 10.849 | 1.00 | 49.41 |
| 20089 | CA | ASN | D | 246 | -131.999 | 8.712 | 10.484 | 1.00 | 50.73 |
| 20090 | CB | ASN | D | 246 | -133.079 | 9.699 | 10.034 | 1.00 | 50.45 |
| 20091 | CG | ASN | D | 246 | -134.456 | 9.055 | 9.936 | 1.00 | 50.52 |
| 20092 | OD1 | ASN | D | 246 | -134.581 | 7.842 | 9.740 | 1.00 | 50.04 |
| 20093 | ND2 | ASN | D | 246 | -135.498 | 9.867 | 10.084 | 1.00 | 50.52 |
| 20094 | C | ASN | D | 246 | -131.702 | 7.738 | 9.368 | 1.00 | 51.63 |
| 20095 | O | ASN | D | 246 | -131.362 | 8.147 | 8.259 | 1.00 | 52.34 |
| 20096 | N | THR | D | 247 | -131.831 | 6.450 | 9.649 | 1.00 | 52.85 |
| 20097 | CA | THR | D | 247 | -131.547 | 5.447 | 8.639 | 1.00 | 54.16 |
| 20098 | CB | THR | D | 247 | -131.096 | 4.137 | 9.282 | 1.00 | 54.08 |
| 20099 | OG1 | THR | D | 247 | -132.190 | 3.562 | 10.006 | 1.00 | 53.60 |
| 20100 | CG2 | THR | D | 247 | -130.025 | 4.401 | 10.339 | 1.00 | 54.01 |
| 20101 | C | THR | D | 247 | -132.746 | 5.168 | 7.751 | 1.00 | 55.42 |
| 20102 | O | THR | D | 247 | -132.698 | 4.272 | 6.901 | 1.00 | 55.55 |
| 20103 | N | ASP | D | 248 | -133.831 | 5.903 | 7.956 | 1.00 | 56.81 |
| 20104 | CA | ASP | D | 248 | -135.011 | 5.697 | 7.126 | 1.00 | 58.51 |
| 20105 | CB | ASP | D | 248 | -136.302 | 5.904 | 7.923 | 1.00 | 58.44 |
| 20106 | CG | ASP | D | 248 | -136.734 | 4.656 | 8.675 | 1.00 | 59.37 |
| 20107 | OD1 | ASP | D | 248 | -136.255 | 3.544 | 8.332 | 1.00 | 58.59 |
| 20108 | OD2 | ASP | D | 248 | -137.555 | 4.699 | 9.625 | 1.00 | 60.59 |
| 20109 | C | ASP | D | 248 | -134.962 | 6.649 | 5.944 | 1.00 | 59.26 |
| 20110 | O | ASP | D | 248 | -135.639 | 6.444 | 4.941 | 1.00 | 59.45 |
| 20111 | N | SER | D | 249 | -134.135 | 7.682 | 6.062 | 1.00 | 60.19 |
| 20112 | CA | SER | D | 249 | -134.041 | 8.689 | 5.017 | 1.00 | 60.95 |
| 20113 | CB | SER | D | 249 | -134.411 | 10.050 | 5.586 | 1.00 | 60.84 |
| 20114 | OG | SER | D | 249 | -133.802 | 10.221 | 6.844 | 1.00 | 61.32 |
| 20115 | C | SER | D | 249 | -132.661 | 8.750 | 4.371 | 1.00 | 61.45 |
| 20116 | O | SER | D | 249 | -132.178 | 9.829 | 4.013 | 1.00 | 61.57 |
| 20117 | N | LEU | D | 250 | -132.020 | 7.597 | 4.233 | 1.00 | 61.85 |
| 20118 | CA | LEU | D | 250 | -130.735 | 7.550 | 3.555 | 1.00 | 62.45 |
| 20119 | CB | LEU | D | 250 | -129.936 | 6.313 | 3.962 | 1.00 | 62.30 |
| 20120 | CG | LEU | D | 250 | -129.092 | 6.365 | 5.241 | 1.00 | 61.93 |
| 20121 | CD1 | LEU | D | 250 | -129.486 | 5.252 | 6.201 | 1.00 | 60.56 |
| 20122 | CD2 | LEU | D | 250 | -129.126 | 7.752 | 5.897 | 1.00 | 60.62 |
| 20123 | C | LEU | D | 250 | -130.960 | 7.534 | 2.047 | 1.00 | 62.96 |
| 20124 | O | LEU | D | 250 | -131.732 | 6.717 | 1.537 | 1.00 | 62.64 |
| 20125 | N | SER | D | 251 | -130.281 | 8.429 | 1.338 | 1.00 | 63.68 |
| 20126 | CA | SER | D | 251 | -130.415 | 8.513 | -0.110 | 1.00 | 64.43 |
| 20127 | CB | SER | D | 251 | -130.642 | 9.960 | -0.538 | 1.00 | 64.42 |
| 20128 | OG | SER | D | 251 | -131.250 | 10.721 | 0.496 | 1.00 | 65.65 |
| 20129 | C | SER | D | 251 | -129.157 | 7.995 | -0.783 | 1.00 | 64.62 |
| 20130 | O | SER | D | 251 | -128.049 | 8.255 | -0.318 | 1.00 | 64.77 |
| 20131 | N | SER | D | 252 | -129.330 | 7.281 | -1.890 | 1.00 | 65.08 |
| 20132 | CA | SER | D | 252 | -128.195 | 6.760 | -2.641 | 1.00 | 65.27 |
| 20133 | CB | SER | D | 252 | -128.664 | 5.782 | -3.724 | 1.00 | 65.35 |
| 20134 | OG | SER | D | 252 | -129.605 | 4.846 | -3.222 | 1.00 | 65.60 |
| 20135 | C | SER | D | 252 | -127.450 | 7.921 | -3.288 | 1.00 | 65.29 |

FIGURE 3 OE

| A | B | C | D | E | F | G | H | I | J |
|---|---|---|---|---|---|---|---|---|---|
| 20136 | O | SER | D | 252 | -126.265 | 7.814 | -3.610 | 1.00 | 65.25 |
| 20137 | N | VAL | D | 253 | -128.148 | 9.041 | -3.452 | 1.00 | 65.23 |
| 20138 | CA | VAL | D | 253 | -127.591 | 10.195 | -4.152 | 1.00 | 65.31 |
| 20139 | CB | VAL | D | 253 | -128.521 | 10.634 | -5.295 | 1.00 | 65.51 |
| 20140 | CG1 | VAL | D | 253 | -129.757 | 11.329 | -4.738 | 1.00 | 65.51 |
| 20141 | CG2 | VAL | D | 253 | -128.913 | 9.432 | -6.154 | 1.00 | 65.72 |
| 20142 | C | VAL | D | 253 | -127.292 | 11.409 | -3.276 | 1.00 | 65.14 |
| 20143 | O | VAL | D | 253 | -127.042 | 12.502 | -3.781 | 1.00 | 65.12 |
| 20144 | N | THR | D | 254 | -127.329 | 11.240 | -1.963 | 1.00 | 64.89 |
| 20145 | CA | THR | D | 254 | -126.983 | 12.357 | -1.088 | 1.00 | 64.61 |
| 20146 | CB | THR | D | 254 | -128.189 | 13.277 | -0.840 | 1.00 | 64.72 |
| 20147 | OG1 | THR | D | 254 | -128.277 | 13.575 | 0.559 | 1.00 | 65.14 |
| 20148 | CG2 | THR | D | 254 | -129.486 | 12.547 | -1.126 | 1.00 | 65.20 |
| 20149 | C | THR | D | 254 | -126.346 | 11.912 | 0.224 | 1.00 | 64.05 |
| 20150 | O | THR | D | 254 | -126.770 | 10.929 | 0.830 | 1.00 | 64.17 |
| 20151 | N | ASN | D | 255 | -125.316 | 12.639 | 0.647 | 1.00 | 63.32 |
| 20152 | CA | ASN | D | 255 | -124.585 | 12.276 | 1.853 | 1.00 | 62.59 |
| 20153 | CB | ASN | D | 255 | -123.325 | 13.137 | 2.017 | 1.00 | 62.76 |
| 20154 | CG | ASN | D | 255 | -122.100 | 12.516 | 1.358 | 1.00 | 63.08 |
| 20155 | OD1 | ASN | D | 255 | -122.011 | 11.298 | 1.225 | 1.00 | 62.12 |
| 20156 | ND2 | ASN | D | 255 | -121.146 | 13.356 | 0.951 | 1.00 | 66.29 |
| 20157 | C | ASN | D | 255 | -125.433 | 12.296 | 3.122 | 1.00 | 61.81 |
| 20158 | O | ASN | D | 255 | -126.110 | 13.280 | 3.427 | 1.00 | 61.42 |
| 20159 | N | ALA | D | 256 | -125.388 | 11.178 | 3.841 | 1.00 | 60.91 |
| 20160 | CA | ALA | D | 256 | -126.077 | 11.021 | 5.110 | 1.00 | 59.91 |
| 20161 | CB | ALA | D | 256 | -125.513 | 9.831 | 5.849 | 1.00 | 59.96 |
| 20162 | C | ALA | D | 256 | -125.938 | 12.274 | 5.962 | 1.00 | 59.39 |
| 20163 | O | ALA | D | 256 | -124.894 | 12.933 | 5.974 | 1.00 | 59.13 |
| 20164 | N | THR | D | 257 | -126.997 | 12.615 | 6.675 | 1.00 | 58.66 |
| 20165 | CA | THR | D | 257 | -126.920 | 13.772 | 7.547 | 1.00 | 58.14 |
| 20166 | CB | THR | D | 257 | -128.047 | 14.774 | 7.223 | 1.00 | 58.28 |
| 20167 | OG1 | THR | D | 257 | -128.258 | 15.656 | 8.336 | 1.00 | 58.82 |
| 20168 | CG2 | THR | D | 257 | -129.378 | 14.045 | 7.060 | 1.00 | 58.70 |
| 20169 | C | THR | D | 257 | -126.930 | 13.318 | 9.008 | 1.00 | 57.32 |
| 20170 | O | THR | D | 257 | -127.872 | 12.682 | 9.472 | 1.00 | 57.48 |
| 20171 | N | SER | D | 258 | -125.848 | 13.610 | 9.715 | 1.00 | 56.10 |
| 20172 | CA | SER | D | 258 | -125.742 | 13.228 | 11.110 | 1.00 | 54.93 |
| 20173 | CB | SER | D | 258 | -124.360 | 12.647 | 11.411 | 1.00 | 54.90 |
| 20174 | OG | SER | D | 258 | -124.260 | 11.321 | 10.925 | 1.00 | 54.88 |
| 20175 | C | SER | D | 258 | -126.005 | 14.443 | 11.971 | 1.00 | 54.33 |
| 20176 | O | SER | D | 258 | -125.424 | 15.506 | 11.763 | 1.00 | 54.02 |
| 20177 | N | ILE | D | 259 | -126.907 | 14.293 | 12.929 | 1.00 | 53.54 |
| 20178 | CA | ILE | D | 259 | -127.223 | 15.392 | 13.815 | 1.00 | 53.01 |
| 20179 | CB | ILE | D | 259 | -128.711 | 15.356 | 14.211 | 1.00 | 53.02 |
| 20180 | CG1 | ILE | D | 259 | -129.598 | 15.420 | 12.966 | 1.00 | 53.18 |
| 20181 | CD1 | ILE | D | 259 | -129.184 | 16.476 | 11.957 | 1.00 | 52.80 |
| 20182 | CG2 | ILE | D | 259 | -129.040 | 16.487 | 15.170 | 1.00 | 52.69 |
| 20183 | C | ILE | D | 259 | -126.336 | 15.247 | 15.037 | 1.00 | 52.78 |
| 20184 | O | ILE | D | 259 | -126.327 | 14.200 | 15.685 | 1.00 | 52.90 |
| 20185 | N | GLN | D | 260 | -125.577 | 16.289 | 15.343 | 1.00 | 52.39 |
| 20186 | CA | GLN | D | 260 | -124.690 | 16.233 | 16.488 | 1.00 | 52.17 |

FIGURE 3 OF

| A | B | C | D | E | F | G | H | I | J |
|---|---|---|---|---|---|---|---|---|---|
| 20187 | CB | GLN | D | 260 | -123.464 | 17.128 | 16.296 | 1.00 | 52.18 |
| 20188 | CG | GLN | D | 260 | -122.292 | 16.735 | 17.200 | 1.00 | 52.37 |
| 20189 | CD | GLN | D | 260 | -121.170 | 17.750 | 17.197 | 1.00 | 53.04 |
| 20190 | OE1 | GLN | D | 260 | -121.019 | 18.519 | 16.245 | 1.00 | 52.54 |
| 20191 | NE2 | GLN | D | 260 | -120.378 | 17.761 | 18.267 | 1.00 | 52.48 |
| 20192 | C | GLN | D | 260 | -125.408 | 16.611 | 17.771 | 1.00 | 51.82 |
| 20193 | O | GLN | D | 260 | -126.126 | 17.616 | 17.832 | 1.00 | 51.67 |
| 20194 | N | ILE | D | 261 | -125.227 | 15.793 | 18.800 | 1.00 | 51.04 |
| 20195 | CA | ILE | D | 261 | -125.777 | 16.138 | 20.088 | 1.00 | 50.27 |
| 20196 | CB | ILE | D | 261 | -126.433 | 14.940 | 20.751 | 1.00 | 49.94 |
| 20197 | CG1 | ILE | D | 261 | -127.515 | 14.372 | 19.846 | 1.00 | 49.61 |
| 20198 | CD1 | ILE | D | 261 | -128.618 | 13.668 | 20.593 | 1.00 | 46.90 |
| 20199 | CG2 | ILE | D | 261 | -127.076 | 15.354 | 22.049 | 1.00 | 50.39 |
| 20200 | C | ILE | D | 261 | -124.620 | 16.668 | 20.905 | 1.00 | 50.03 |
| 20201 | O | ILE | D | 261 | -123.684 | 15.946 | 21.222 | 1.00 | 50.14 |
| 20202 | N | THR | D | 262 | -124.659 | 17.949 | 21.221 | 1.00 | 49.68 |
| 20203 | CA | THR | D | 262 | -123.566 | 18.522 | 21.974 | 1.00 | 49.18 |
| 20204 | CB | THR | D | 262 | -123.579 | 20.049 | 21.885 | 1.00 | 49.33 |
| 20205 | OG1 | THR | D | 262 | -122.251 | 20.542 | 22.099 | 1.00 | 49.03 |
| 20206 | CG2 | THR | D | 262 | -124.385 | 20.653 | 23.044 | 1.00 | 49.98 |
| 20207 | C | THR | D | 262 | -123.640 | 18.063 | 23.422 | 1.00 | 48.87 |
| 20208 | O | THR | D | 262 | -124.658 | 17.528 | 23.868 | 1.00 | 48.87 |
| 20209 | N | ALA | D | 263 | -122.553 | 18.281 | 24.146 | 1.00 | 47.91 |
| 20210 | CA | ALA | D | 263 | -122.459 | 17.867 | 25.527 | 1.00 | 47.07 |
| 20211 | CB | ALA | D | 263 | -121.045 | 17.352 | 25.827 | 1.00 | 46.67 |
| 20212 | C | ALA | D | 263 | -122.806 | 19.023 | 26.445 | 1.00 | 46.38 |
| 20213 | O | ALA | D | 263 | -122.577 | 20.183 | 26.116 | 1.00 | 46.72 |
| 20214 | N | PRO | D | 264 | -123.352 | 18.693 | 27.603 | 1.00 | 45.49 |
| 20215 | CA | PRO | D | 264 | -123.705 | 19.687 | 28.608 | 1.00 | 44.96 |
| 20216 | CB | PRO | D | 264 | -123.808 | 18.854 | 29.887 | 1.00 | 44.78 |
| 20217 | CG | PRO | D | 264 | -124.261 | 17.544 | 29.424 | 1.00 | 45.48 |
| 20218 | CD | PRO | D | 264 | -123.676 | 17.327 | 28.038 | 1.00 | 45.73 |
| 20219 | C | PRO | D | 264 | -122.591 | 20.706 | 28.767 | 1.00 | 44.18 |
| 20220 | O | PRO | D | 264 | -121.407 | 20.364 | 28.782 | 1.00 | 43.79 |
| 20221 | N | ALA | D | 265 | -122.988 | 21.960 | 28.890 | 1.00 | 43.13 |
| 20222 | CA | ALA | D | 265 | -122.042 | 23.037 | 29.069 | 1.00 | 42.51 |
| 20223 | CB | ALA | D | 265 | -122.793 | 24.338 | 29.347 | 1.00 | 42.62 |
| 20224 | C | ALA | D | 265 | -121.076 | 22.739 | 30.209 | 1.00 | 41.58 |
| 20225 | O | ALA | D | 265 | -119.896 | 23.040 | 30.107 | 1.00 | 41.21 |
| 20226 | N | SER | D | 266 | -121.591 | 22.155 | 31.291 | 1.00 | 40.80 |
| 20227 | CA | SER | D | 266 | -120.781 | 21.887 | 32.486 | 1.00 | 40.09 |
| 20228 | CB | SER | D | 266 | -121.655 | 21.455 | 33.672 | 1.00 | 39.70 |
| 20229 | OG | SER | D | 266 | -122.396 | 20.300 | 33.344 | 1.00 | 39.99 |
| 20230 | C | SER | D | 266 | -119.694 | 20.850 | 32.207 | 1.00 | 39.33 |
| 20231 | O | SER | D | 266 | -118.737 | 20.732 | 32.965 | 1.00 | 38.97 |
| 20232 | N | MET | D | 267 | -119.861 | 20.124 | 31.106 | 1.00 | 38.50 |
| 20233 | CA | MET | D | 267 | -118.891 | 19.159 | 30.633 | 1.00 | 38.27 |
| 20234 | CB | MET | D | 267 | -119.604 | 18.030 | 29.889 | 1.00 | 37.83 |
| 20235 | CG | MET | D | 267 | -120.343 | 17.102 | 30.817 | 1.00 | 37.74 |
| 20236 | SD | MET | D | 267 | -119.194 | 16.089 | 31.788 | 1.00 | 39.60 |
| 20237 | CE | MET | D | 267 | -120.079 | 15.964 | 33.348 | 1.00 | 38.25 |

FIGURE 3 OG

| A | B | C | D | E | F | G | H | I | J |
|---|---|---|---|---|---|---|---|---|---|
| 20238 | C | MET | D | 267 | -117.883 | 19.811 | 29.700 | 1.00 | 38.44 |
| 20239 | O | MET | D | 267 | -116.689 | 19.525 | 29.750 | 1.00 | 38.63 |
| 20240 | N | LEU | D | 268 | -118.368 | 20.700 | 28.846 | 1.00 | 38.48 |
| 20241 | CA | LEU | D | 268 | -117.510 | 21.337 | 27.864 | 1.00 | 38.50 |
| 20242 | CB | LEU | D | 268 | -118.349 | 22.071 | 26.820 | 1.00 | 38.67 |
| 20243 | CG | LEU | D | 268 | -119.297 | 21.189 | 26.016 | 1.00 | 38.57 |
| 20244 | CD1 | LEU | D | 268 | -120.371 | 22.037 | 25.344 | 1.00 | 38.62 |
| 20245 | CD2 | LEU | D | 268 | -118.534 | 20.314 | 24.997 | 1.00 | 37.83 |
| 20246 | C | LEU | D | 268 | -116.518 | 22.290 | 28.483 | 1.00 | 38.46 |
| 20247 | O | LEU | D | 268 | -115.599 | 22.734 | 27.817 | 1.00 | 38.96 |
| 20248 | N | ILE | D | 269 | -116.700 | 22.623 | 29.751 | 1.00 | 38.42 |
| 20249 | CA | ILE | D | 269 | -115.759 | 23.521 | 30.405 | 1.00 | 38.59 |
| 20250 | CB | ILE | D | 269 | -116.273 | 23.896 | 31.798 | 1.00 | 38.86 |
| 20251 | CG1 | ILE | D | 269 | -115.503 | 25.095 | 32.348 | 1.00 | 40.56 |
| 20252 | CD1 | ILE | D | 269 | -116.039 | 26.428 | 31.878 | 1.00 | 43.56 |
| 20253 | CG2 | ILE | D | 269 | -116.139 | 22.719 | 32.745 | 1.00 | 40.22 |
| 20254 | C | ILE | D | 269 | -114.348 | 22.906 | 30.502 | 1.00 | 37.84 |
| 20255 | O | ILE | D | 269 | -113.385 | 23.609 | 30.794 | 1.00 | 38.38 |
| 20256 | N | GLY | D | 270 | -114.225 | 21.603 | 30.249 | 1.00 | 36.77 |
| 20257 | CA | GLY | D | 270 | -112.932 | 20.932 | 30.309 | 1.00 | 35.46 |
| 20258 | C | GLY | D | 270 | -112.956 | 19.568 | 29.643 | 1.00 | 34.32 |
| 20259 | O | GLY | D | 270 | -113.880 | 19.259 | 28.891 | 1.00 | 34.07 |
| 20260 | N | ASP | D | 271 | -111.944 | 18.747 | 29.903 | 1.00 | 33.67 |
| 20261 | CA | ASP | D | 271 | -111.924 | 17.389 | 29.350 | 1.00 | 33.32 |
| 20262 | CB | ASP | D | 271 | -110.607 | 16.681 | 29.681 | 1.00 | 33.79 |
| 20263 | CG | ASP | D | 271 | -109.419 | 17.359 | 29.086 | 1.00 | 35.02 |
| 20264 | OD1 | ASP | D | 271 | -108.276 | 16.885 | 29.328 | 1.00 | 35.95 |
| 20265 | OD2 | ASP | D | 271 | -109.533 | 18.378 | 28.366 | 1.00 | 37.23 |
| 20266 | C | ASP | D | 271 | -113.050 | 16.582 | 29.971 | 1.00 | 32.51 |
| 20267 | O | ASP | D | 271 | -113.351 | 16.734 | 31.161 | 1.00 | 32.49 |
| 20268 | N | HIS | D | 272 | -113.637 | 15.687 | 29.197 | 1.00 | 31.91 |
| 20269 | CA | HIS | D | 272 | -114.741 | 14.884 | 29.697 | 1.00 | 32.19 |
| 20270 | CB | HIS | D | 272 | -116.041 | 15.678 | 29.568 | 1.00 | 32.11 |
| 20271 | CG | HIS | D | 272 | -116.228 | 16.270 | 28.208 | 1.00 | 32.35 |
| 20272 | ND1 | HIS | D | 272 | -115.644 | 17.463 | 27.835 | 1.00 | 32.50 |
| 20273 | CE1 | HIS | D | 272 | -115.948 | 17.718 | 26.573 | 1.00 | 34.67 |
| 20274 | NE2 | HIS | D | 272 | -116.697 | 16.730 | 26.113 | 1.00 | 33.22 |
| 20275 | CD2 | HIS | D | 272 | -116.877 | 15.804 | 27.115 | 1.00 | 31.47 |
| 20276 | C | HIS | D | 272 | -114.846 | 13.621 | 28.862 | 1.00 | 32.29 |
| 20277 | O | HIS | D | 272 | -114.106 | 13.449 | 27.903 | 1.00 | 32.69 |
| 20278 | N | TYR | D | 273 | -115.778 | 12.750 | 29.218 | 1.00 | 32.52 |
| 20279 | CA | TYR | D | 273 | -115.986 | 11.522 | 28.475 | 1.00 | 33.29 |
| 20280 | CB | TYR | D | 273 | -115.498 | 10.302 | 29.281 | 1.00 | 33.12 |
| 20281 | CG | TYR | D | 273 | -114.110 | 10.379 | 29.864 | 1.00 | 31.73 |
| 20282 | CD1 | TYR | D | 273 | -112.994 | 10.182 | 29.067 | 1.00 | 30.36 |
| 20283 | CE1 | TYR | D | 273 | -111.727 | 10.238 | 29.590 | 1.00 | 31.17 |
| 20284 | CZ | TYR | D | 273 | -111.546 | 10.479 | 30.938 | 1.00 | 29.98 |
| 20285 | OH | TYR | D | 273 | -110.276 | 10.517 | 31.445 | 1.00 | 28.23 |
| 20286 | CE2 | TYR | D | 273 | -112.637 | 10.675 | 31.767 | 1.00 | 30.64 |
| 20287 | CD2 | TYR | D | 273 | -113.916 | 10.613 | 31.225 | 1.00 | 31.15 |
| 20288 | C | TYR | D | 273 | -117.464 | 11.296 | 28.248 | 1.00 | 34.20 |

FIGURE 3 OH

| A | B | C | D | E | F | G | H | I | J |
|---|---|---|---|---|---|---|---|---|---|
| 20289 | O | TYR | D | 273 | -118.312 | 11.815 | 28.980 | 1.00 | 34.77 |
| 20290 | N | LEU | D | 274 | -117.778 | 10.491 | 27.247 | 1.00 | 34.83 |
| 20291 | CA | LEU | D | 274 | -119.139 | 10.032 | 27.073 | 1.00 | 34.79 |
| 20292 | CB | LEU | D | 274 | -119.461 | 9.828 | 25.592 | 1.00 | 34.45 |
| 20293 | CG | LEU | D | 274 | -120.756 | 9.043 | 25.315 | 1.00 | 35.09 |
| 20294 | CD1 | LEU | D | 274 | -122.002 | 9.840 | 25.764 | 1.00 | 34.24 |
| 20295 | CD2 | LEU | D | 274 | -120.873 | 8.607 | 23.841 | 1.00 | 34.39 |
| 20296 | C | LEU | D | 274 | -119.106 | 8.702 | 27.808 | 1.00 | 35.39 |
| 20297 | O | LEU | D | 274 | -118.335 | 7.821 | 27.449 | 1.00 | 35.10 |
| 20298 | N | CYS | D | 275 | -119.908 | 8.548 | 28.854 | 1.00 | 36.04 |
| 20299 | CA | CYS | D | 275 | -119.845 | 7.315 | 29.628 | 1.00 | 36.43 |
| 20300 | CB | CYS | D | 275 | -119.626 | 7.592 | 31.117 | 1.00 | 36.48 |
| 20301 | SG | CYS | D | 275 | -120.887 | 8.631 | 31.904 | 1.00 | 38.06 |
| 20302 | C | CYS | D | 275 | -121.021 | 6.383 | 29.437 | 1.00 | 36.83 |
| 20303 | O | CYS | D | 275 | -120.890 | 5.191 | 29.672 | 1.00 | 37.45 |
| 20304 | N | ASP | D | 276 | -122.170 | 6.895 | 29.018 | 1.00 | 37.00 |
| 20305 | CA | ASP | D | 276 | -123.293 | 5.994 | 28.803 | 1.00 | 37.55 |
| 20306 | CB | ASP | D | 276 | -124.038 | 5.739 | 30.109 | 1.00 | 37.78 |
| 20307 | CG | ASP | D | 276 | -125.085 | 4.659 | 29.975 | 1.00 | 39.17 |
| 20308 | OD1 | ASP | D | 276 | -124.723 | 3.465 | 30.035 | 1.00 | 41.65 |
| 20309 | OD2 | ASP | D | 276 | -126.302 | 4.898 | 29.807 | 1.00 | 42.31 |
| 20310 | C | ASP | D | 276 | -124.294 | 6.456 | 27.750 | 1.00 | 37.47 |
| 20311 | O | ASP | D | 276 | -124.621 | 7.635 | 27.660 | 1.00 | 37.06 |
| 20312 | N | VAL | D | 277 | -124.773 | 5.503 | 26.962 | 1.00 | 37.44 |
| 20313 | CA | VAL | D | 277 | -125.808 | 5.772 | 25.992 | 1.00 | 37.51 |
| 20314 | CB | VAL | D | 277 | -125.306 | 5.705 | 24.530 | 1.00 | 37.76 |
| 20315 | CG1 | VAL | D | 277 | -126.319 | 6.388 | 23.616 | 1.00 | 37.24 |
| 20316 | CG2 | VAL | D | 277 | -123.955 | 6.356 | 24.373 | 1.00 | 37.23 |
| 20317 | C | VAL | D | 277 | -126.907 | 4.728 | 26.161 | 1.00 | 37.85 |
| 20318 | O | VAL | D | 277 | -126.650 | 3.525 | 26.096 | 1.00 | 37.12 |
| 20319 | N | THR | D | 278 | -128.127 | 5.206 | 26.395 | 1.00 | 38.53 |
| 20320 | CA | THR | D | 278 | -129.295 | 4.344 | 26.496 | 1.00 | 39.41 |
| 20321 | CB | THR | D | 278 | -129.676 | 4.161 | 27.975 | 1.00 | 39.65 |
| 20322 | OG1 | THR | D | 278 | -128.606 | 3.517 | 28.693 | 1.00 | 41.23 |
| 20323 | CG2 | THR | D | 278 | -130.834 | 3.197 | 28.100 | 1.00 | 38.74 |
| 20324 | C | THR | D | 278 | -130.491 | 4.969 | 25.761 | 1.00 | 40.15 |
| 20325 | O | THR | D | 278 | -130.845 | 6.122 | 26.017 | 1.00 | 40.47 |
| 20326 | N | TRP | D | 279 | -131.111 | 4.232 | 24.846 | 1.00 | 40.72 |
| 20327 | CA | TRP | D | 279 | -132.348 | 4.720 | 24.239 | 1.00 | 41.37 |
| 20328 | CB | TRP | D | 279 | -132.661 | 3.973 | 22.946 | 1.00 | 41.57 |
| 20329 | CG | TRP | D | 279 | -131.807 | 4.394 | 21.810 | 1.00 | 42.65 |
| 20330 | CD1 | TRP | D | 279 | -130.682 | 3.765 | 21.342 | 1.00 | 42.53 |
| 20331 | NE1 | TRP | D | 279 | -130.158 | 4.465 | 20.282 | 1.00 | 43.68 |
| 20332 | CE2 | TRP | D | 279 | -130.945 | 5.564 | 20.041 | 1.00 | 44.02 |
| 20333 | CD2 | TRP | D | 279 | -131.993 | 5.547 | 20.987 | 1.00 | 43.93 |
| 20334 | CE3 | TRP | D | 279 | -132.942 | 6.572 | 20.950 | 1.00 | 45.59 |
| 20335 | CZ3 | TRP | D | 279 | -132.820 | 7.564 | 19.984 | 1.00 | 47.26 |
| 20336 | CH2 | TRP | D | 279 | -131.767 | 7.550 | 19.059 | 1.00 | 46.13 |
| 20337 | CZ2 | TRP | D | 279 | -130.827 | 6.555 | 19.070 | 1.00 | 44.83 |
| 20338 | C | TRP | D | 279 | -133.491 | 4.531 | 25.235 | 1.00 | 41.48 |
| 20339 | O | TRP | D | 279 | -133.561 | 3.507 | 25.908 | 1.00 | 41.96 |

FIGURE 3 OI

| A | B | C | D | E | F | G | H | I | J |
|---|---|---|---|---|---|---|---|---|---|
| 20340 | N | ALA | D | 280 | -134.372 | 5.521 | 25.332 | 1.00 | 41.41 |
| 20341 | CA | ALA | D | 280 | -135.516 | 5.479 | 26.241 | 1.00 | 41.43 |
| 20342 | CB | ALA | D | 280 | -135.746 | 6.848 | 26.825 | 1.00 | 41.35 |
| 20343 | C | ALA | D | 280 | -136.768 | 5.024 | 25.496 | 1.00 | 41.92 |
| 20344 | O | ALA | D | 280 | -137.494 | 4.133 | 25.943 | 1.00 | 41.19 |
| 20345 | N | THR | D | 281 | -137.005 | 5.671 | 24.356 | 1.00 | 42.20 |
| 20346 | CA | THR | D | 281 | -138.124 | 5.376 | 23.486 | 1.00 | 42.77 |
| 20347 | CB | THR | D | 281 | -139.229 | 6.414 | 23.659 | 1.00 | 42.73 |
| 20348 | OG1 | THR | D | 281 | -138.795 | 7.646 | 23.064 | 1.00 | 42.34 |
| 20349 | CG2 | THR | D | 281 | -139.449 | 6.762 | 25.122 | 1.00 | 42.31 |
| 20350 | C | THR | D | 281 | -137.617 | 5.536 | 22.069 | 1.00 | 43.54 |
| 20351 | O | THR | D | 281 | -136.468 | 5.946 | 21.853 | 1.00 | 43.78 |
| 20352 | N | GLN | D | 282 | -138.494 | 5.252 | 21.106 | 1.00 | 43.58 |
| 20353 | CA | GLN | D | 282 | -138.169 | 5.374 | 19.687 | 1.00 | 43.34 |
| 20354 | CB | GLN | D | 282 | -139.431 | 5.195 | 18.845 | 1.00 | 43.27 |
| 20355 | CG | GLN | D | 282 | -140.158 | 3.909 | 19.121 | 1.00 | 43.95 |
| 20356 | CD | GLN | D | 282 | -139.309 | 2.709 | 18.820 | 1.00 | 44.66 |
| 20357 | OE1 | GLN | D | 282 | -138.206 | 2.849 | 18.278 | 1.00 | 47.30 |
| 20358 | NE2 | GLN | D | 282 | -139.802 | 1.522 | 19.170 | 1.00 | 43.65 |
| 20359 | C | GLN | D | 282 | -137.590 | 6.725 | 19.355 | 1.00 | 42.89 |
| 20360 | O | GLN | D | 282 | -136.854 | 6.873 | 18.389 | 1.00 | 42.72 |
| 20361 | N | GLU | D | 283 | -137.924 | 7.720 | 20.158 | 1.00 | 42.79 |
| 20362 | CA | GLU | D | 283 | -137.516 | 9.074 | 19.839 | 1.00 | 42.95 |
| 20363 | CB | GLU | D | 283 | -138.734 | 9.865 | 19.349 | 1.00 | 43.48 |
| 20364 | CG | GLU | D | 283 | -139.167 | 9.566 | 17.906 | 1.00 | 45.44 |
| 20365 | CD | GLU | D | 283 | -140.418 | 10.348 | 17.491 | 1.00 | 48.85 |
| 20366 | OE1 | GLU | D | 283 | -141.304 | 9.755 | 16.816 | 1.00 | 49.34 |
| 20367 | OE2 | GLU | D | 283 | -140.522 | 11.551 | 17.845 | 1.00 | 46.90 |
| 20368 | C | GLU | D | 283 | -136.835 | 9.811 | 20.986 | 1.00 | 42.50 |
| 20369 | O | GLU | D | 283 | -136.660 | 11.021 | 20.926 | 1.00 | 42.35 |
| 20370 | N | ARG | D | 284 | -136.450 | 9.086 | 22.031 | 1.00 | 42.30 |
| 20371 | CA | ARG | D | 284 | -135.792 | 9.710 | 23.173 | 1.00 | 41.72 |
| 20372 | CB | ARG | D | 284 | -136.735 | 9.763 | 24.368 | 1.00 | 42.06 |
| 20373 | CG | ARG | D | 284 | -136.136 | 10.438 | 25.583 | 1.00 | 43.16 |
| 20374 | CD | ARG | D | 284 | -137.154 | 10.734 | 26.671 | 1.00 | 45.69 |
| 20375 | NE | ARG | D | 284 | -138.146 | 11.706 | 26.221 | 1.00 | 46.17 |
| 20376 | CZ | ARG | D | 284 | -139.431 | 11.660 | 26.544 | 1.00 | 46.79 |
| 20377 | NH1 | ARG | D | 284 | -140.261 | 12.587 | 26.083 | 1.00 | 45.42 |
| 20378 | NH2 | ARG | D | 284 | -139.886 | 10.691 | 27.335 | 1.00 | 46.32 |
| 20379 | C | ARG | D | 284 | -134.514 | 8.990 | 23.568 | 1.00 | 40.91 |
| 20380 | O | ARG | D | 284 | -134.515 | 7.788 | 23.805 | 1.00 | 40.62 |
| 20381 | N | ILE | D | 285 | -133.421 | 9.731 | 23.656 | 1.00 | 40.02 |
| 20382 | CA | ILE | D | 285 | -132.170 | 9.109 | 24.036 | 1.00 | 39.17 |
| 20383 | CB | ILE | D | 285 | -131.208 | 9.053 | 22.818 | 1.00 | 39.17 |
| 20384 | CG1 | ILE | D | 285 | -130.025 | 8.132 | 23.089 | 1.00 | 39.43 |
| 20385 | CD1 | ILE | D | 285 | -129.076 | 8.043 | 21.909 | 1.00 | 39.70 |
| 20386 | CG2 | ILE | D | 285 | -130.727 | 10.426 | 22.424 | 1.00 | 39.53 |
| 20387 | C | ILE | D | 285 | -131.540 | 9.805 | 25.229 | 1.00 | 38.69 |
| 20388 | O | ILE | D | 285 | -131.601 | 11.023 | 25.339 | 1.00 | 38.19 |
| 20389 | N | SER | D | 286 | -130.971 | 9.027 | 26.155 | 1.00 | 37.96 |
| 20390 | CA | SER | D | 286 | -130.228 | 9.644 | 27.246 | 1.00 | 37.07 |

FIGURE 3 OJ

| A | B | C | D | E | F | G | H | I | J |
|---|---|---|---|---|---|---|---|---|---|
| 20391 | CB | SER | D | 286 | -130.787 | 9.287 | 28.631 | 1.00 | 36.91 |
| 20392 | OG | SER | D | 286 | -130.305 | 8.049 | 29.100 | 1.00 | 36.51 |
| 20393 | C | SER | D | 286 | -128.742 | 9.325 | 27.121 | 1.00 | 36.39 |
| 20394 | O | SER | D | 286 | -128.344 | 8.215 | 26.757 | 1.00 | 36.15 |
| 20395 | N | LEU | D | 287 | -127.940 | 10.336 | 27.404 | 1.00 | 35.78 |
| 20396 | CA | LEU | D | 287 | -126.498 | 10.248 | 27.327 | 1.00 | 35.18 |
| 20397 | CB | LEU | D | 287 | -125.957 | 11.283 | 26.338 | 1.00 | 35.62 |
| 20398 | CG | LEU | D | 287 | -125.957 | 11.077 | 24.822 | 1.00 | 35.97 |
| 20399 | CD1 | LEU | D | 287 | -126.134 | 12.431 | 24.182 | 1.00 | 36.47 |
| 20400 | CD2 | LEU | D | 287 | -127.031 | 10.140 | 24.357 | 1.00 | 36.95 |
| 20401 | C | LEU | D | 287 | -125.994 | 10.652 | 28.683 | 1.00 | 34.51 |
| 20402 | O | LEU | D | 287 | -126.520 | 11.597 | 29.279 | 1.00 | 34.09 |
| 20403 | N | GLN | D | 288 | -124.984 | 9.944 | 29.177 | 1.00 | 33.47 |
| 20404 | CA | GLN | D | 288 | -124.341 | 10.347 | 30.420 | 1.00 | 32.77 |
| 20405 | CB | GLN | D | 288 | -124.354 | 9.230 | 31.461 | 1.00 | 33.02 |
| 20406 | CG | GLN | D | 288 | -125.640 | 9.149 | 32.265 | 1.00 | 33.25 |
| 20407 | CD | GLN | D | 288 | -125.781 | 7.848 | 33.036 | 1.00 | 33.72 |
| 20408 | OE1 | GLN | D | 288 | -126.381 | 6.890 | 32.546 | 1.00 | 34.15 |
| 20409 | NE2 | GLN | D | 288 | -125.253 | 7.818 | 34.247 | 1.00 | 34.08 |
| 20410 | C | GLN | D | 288 | -122.924 | 10.786 | 30.121 | 1.00 | 32.53 |
| 20411 | O | GLN | D | 288 | -122.161 | 10.118 | 29.412 | 1.00 | 32.11 |
| 20412 | N | TRP | D | 289 | -122.580 | 11.937 | 30.656 | 1.00 | 32.67 |
| 20413 | CA | TRP | D | 289 | -121.262 | 12.465 | 30.478 | 1.00 | 32.77 |
| 20414 | CB | TRP | D | 289 | -121.336 | 13.869 | 29.878 | 1.00 | 32.94 |
| 20415 | CG | TRP | D | 289 | -121.977 | 13.907 | 28.527 | 1.00 | 33.67 |
| 20416 | CD1 | TRP | D | 289 | -123.315 | 13.991 | 28.255 | 1.00 | 34.03 |
| 20417 | NE1 | TRP | D | 289 | -123.517 | 14.015 | 26.897 | 1.00 | 35.17 |
| 20418 | CE2 | TRP | D | 289 | -122.303 | 13.945 | 26.265 | 1.00 | 35.17 |
| 20419 | CD2 | TRP | D | 289 | -121.312 | 13.878 | 27.264 | 1.00 | 34.12 |
| 20420 | CE3 | TRP | D | 289 | -119.970 | 13.802 | 26.870 | 1.00 | 35.13 |
| 20421 | CZ3 | TRP | D | 289 | -119.670 | 13.792 | 25.519 | 1.00 | 35.56 |
| 20422 | CH2 | TRP | D | 289 | -120.683 | 13.851 | 24.550 | 1.00 | 35.24 |
| 20423 | CZ2 | TRP | D | 289 | -122.001 | 13.920 | 24.901 | 1.00 | 35.14 |
| 20424 | C | TRP | D | 289 | -120.600 | 12.501 | 31.843 | 1.00 | 32.64 |
| 20425 | O | TRP | D | 289 | -121.267 | 12.632 | 32.862 | 1.00 | 32.65 |
| 20426 | N | LEU | D | 290 | -119.276 | 12.433 | 31.835 | 1.00 | 32.23 |
| 20427 | CA | LEU | D | 290 | -118.480 | 12.396 | 33.035 | 1.00 | 31.50 |
| 20428 | CB | LEU | D | 290 | -117.977 | 10.954 | 33.193 | 1.00 | 31.05 |
| 20429 | CG | LEU | D | 290 | -117.433 | 10.401 | 34.510 | 1.00 | 31.54 |
| 20430 | CD1 | LEU | D | 290 | -116.676 | 9.076 | 34.307 | 1.00 | 28.56 |
| 20431 | CD2 | LEU | D | 290 | -116.554 | 11.423 | 35.166 | 1.00 | 33.60 |
| 20432 | C | LEU | D | 290 | -117.293 | 13.336 | 32.802 | 1.00 | 31.41 |
| 20433 | O | LEU | D | 290 | -116.667 | 13.265 | 31.745 | 1.00 | 30.88 |
| 20434 | N | ARG | D | 291 | -116.978 | 14.203 | 33.764 | 1.00 | 31.88 |
| 20435 | CA | ARG | D | 291 | -115.771 | 15.045 | 33.667 | 1.00 | 32.91 |
| 20436 | CB | ARG | D | 291 | -115.707 | 16.094 | 34.777 | 1.00 | 32.88 |
| 20437 | CG | ARG | D | 291 | -116.716 | 17.216 | 34.692 | 1.00 | 35.43 |
| 20438 | CD | ARG | D | 291 | -116.485 | 18.321 | 35.708 | 1.00 | 37.01 |
| 20439 | NE | ARG | D | 291 | -117.415 | 19.416 | 35.493 | 1.00 | 41.05 |
| 20440 | CZ | ARG | D | 291 | -117.945 | 20.154 | 36.461 | 1.00 | 42.21 |
| 20441 | NH1 | ARG | D | 291 | -118.791 | 21.128 | 36.159 | 1.00 | 41.92 |

FIGURE 3 OK

| A | B | C | D | E | F | G | H | I | J |
|---|---|---|---|---|---|---|---|---|---|
| 20442 | NH2 | ARG | D | 291 | -117.630 | 19.919 | 37.725 | 1.00 | 42.53 |
| 20443 | C | ARG | D | 291 | -114.535 | 14.167 | 33.825 | 1.00 | 32.92 |
| 20444 | O | ARG | D | 291 | -114.645 | 13.026 | 34.262 | 1.00 | 33.01 |
| 20445 | N | ARG | D | 292 | -113.363 | 14.723 | 33.515 | 1.00 | 32.96 |
| 20446 | CA | ARG | D | 292 | -112.110 | 13.990 | 33.596 | 1.00 | 32.38 |
| 20447 | CB | ARG | D | 292 | -110.986 | 14.716 | 32.858 | 1.00 | 32.31 |
| 20448 | CG | ARG | D | 292 | -109.677 | 13.916 | 32.806 | 1.00 | 30.46 |
| 20449 | CD | ARG | D | 292 | -108.648 | 14.447 | 31.837 | 1.00 | 28.09 |
| 20450 | NE | ARG | D | 292 | -107.460 | 13.621 | 31.878 | 1.00 | 29.22 |
| 20451 | CZ | ARG | D | 292 | -106.444 | 13.701 | 31.032 | 1.00 | 27.77 |
| 20452 | NH1 | ARG | D | 292 | -105.420 | 12.880 | 31.189 | 1.00 | 25.10 |
| 20453 | NH2 | ARG | D | 292 | -106.445 | 14.600 | 30.048 | 1.00 | 26.35 |
| 20454 | C | ARG | D | 292 | -111.774 | 13.762 | 35.063 | 1.00 | 32.53 |
| 20455 | O | ARG | D | 292 | -111.109 | 12.787 | 35.435 | 1.00 | 32.20 |
| 20456 | N | ILE | D | 293 | -112.217 | 14.686 | 35.893 | 1.00 | 32.32 |
| 20457 | CA | ILE | D | 293 | -112.211 | 14.435 | 37.318 | 1.00 | 32.41 |
| 20458 | CB | ILE | D | 293 | -112.136 | 15.741 | 38.079 | 1.00 | 32.54 |
| 20459 | CG1 | ILE | D | 293 | -110.732 | 16.327 | 37.879 | 1.00 | 32.98 |
| 20460 | CD1 | ILE | D | 293 | -110.643 | 17.819 | 38.099 | 1.00 | 36.74 |
| 20461 | CG2 | ILE | D | 293 | -112.359 | 15.518 | 39.559 | 1.00 | 32.59 |
| 20462 | C | ILE | D | 293 | -113.535 | 13.701 | 37.448 | 1.00 | 32.41 |
| 20463 | O | ILE | D | 293 | -114.598 | 14.297 | 37.340 | 1.00 | 33.13 |
| 20464 | N | GLN | D | 294 | -113.466 | 12.385 | 37.591 | 1.00 | 32.20 |
| 20465 | CA | GLN | D | 294 | -114.659 | 11.551 | 37.500 | 1.00 | 32.03 |
| 20466 | CB | GLN | D | 294 | -114.275 | 10.138 | 37.029 | 1.00 | 31.78 |
| 20467 | CG | GLN | D | 294 | -113.344 | 10.123 | 35.810 | 1.00 | 29.87 |
| 20468 | CD | GLN | D | 294 | -112.862 | 8.725 | 35.449 | 1.00 | 28.26 |
| 20469 | OE1 | GLN | D | 294 | -113.610 | 7.741 | 35.563 | 1.00 | 27.79 |
| 20470 | NE2 | GLN | D | 294 | -111.624 | 8.633 | 35.010 | 1.00 | 25.11 |
| 20471 | C | GLN | D | 294 | -115.556 | 11.475 | 38.744 | 1.00 | 32.55 |
| 20472 | O | GLN | D | 294 | -116.094 | 10.409 | 39.052 | 1.00 | 32.15 |
| 20473 | N | ASN | D | 295 | -115.727 | 12.599 | 39.432 | 1.00 | 33.11 |
| 20474 | CA | ASN | D | 295 | -116.619 | 12.665 | 40.587 | 1.00 | 34.47 |
| 20475 | CB | ASN | D | 295 | -115.913 | 13.277 | 41.791 | 1.00 | 34.41 |
| 20476 | CG | ASN | D | 295 | -115.469 | 14.704 | 41.537 | 1.00 | 36.21 |
| 20477 | OD1 | ASN | D | 295 | -115.681 | 15.248 | 40.448 | 1.00 | 35.00 |
| 20478 | ND2 | ASN | D | 295 | -114.846 | 15.320 | 42.542 | 1.00 | 41.71 |
| 20479 | C | ASN | D | 295 | -117.848 | 13.507 | 40.267 | 1.00 | 34.82 |
| 20480 | O | ASN | D | 295 | -118.524 | 13.998 | 41.176 | 1.00 | 34.45 |
| 20481 | N | TYR | D | 296 | -118.137 | 13.664 | 38.975 | 1.00 | 35.06 |
| 20482 | CA | TYR | D | 296 | -119.256 | 14.488 | 38.543 | 1.00 | 35.12 |
| 20483 | CB | TYR | D | 296 | -118.833 | 15.954 | 38.571 | 1.00 | 35.37 |
| 20484 | CG | TYR | D | 296 | -119.946 | 16.957 | 38.360 | 1.00 | 37.19 |
| 20485 | CD1 | TYR | D | 296 | -120.609 | 17.530 | 39.444 | 1.00 | 38.39 |
| 20486 | CE1 | TYR | D | 296 | -121.626 | 18.465 | 39.259 | 1.00 | 40.01 |
| 20487 | CZ | TYR | D | 296 | -121.976 | 18.838 | 37.978 | 1.00 | 41.13 |
| 20488 | OH | TYR | D | 296 | -122.980 | 19.757 | 37.780 | 1.00 | 42.62 |
| 20489 | CE2 | TYR | D | 296 | -121.324 | 18.285 | 36.889 | 1.00 | 40.09 |
| 20490 | CD2 | TYR | D | 296 | -120.314 | 17.356 | 37.084 | 1.00 | 37.55 |
| 20491 | C | TYR | D | 296 | -119.709 | 14.127 | 37.136 | 1.00 | 35.16 |
| 20492 | O | TYR | D | 296 | -118.988 | 14.337 | 36.162 | 1.00 | 34.80 |

FIGURE 3 OL

| A | B | C | D | E | F | G | H | I | J |
|---|---|---|---|---|---|---|---|---|---|
| 20493 | N | SER | D | 297 | -120.908 | 13.582 | 37.025 | 1.00 | 35.38 |
| 20494 | CA | SER | D | 297 | -121.451 | 13.263 | 35.721 | 1.00 | 36.16 |
| 20495 | CB | SER | D | 297 | -121.494 | 11.762 | 35.502 | 1.00 | 35.37 |
| 20496 | OG | SER | D | 297 | -122.413 | 11.168 | 36.377 | 1.00 | 35.55 |
| 20497 | C | SER | D | 297 | -122.849 | 13.858 | 35.561 | 1.00 | 37.14 |
| 20498 | O | SER | D | 297 | -123.520 | 14.191 | 36.538 | 1.00 | 37.05 |
| 20499 | N | VAL | D | 298 | -123.275 | 13.993 | 34.312 | 1.00 | 38.56 |
| 20500 | CA | VAL | D | 298 | -124.569 | 14.571 | 34.001 | 1.00 | 39.87 |
| 20501 | CB | VAL | D | 298 | -124.418 | 15.988 | 33.414 | 1.00 | 39.92 |
| 20502 | CG1 | VAL | D | 298 | -123.878 | 16.937 | 34.446 | 1.00 | 39.22 |
| 20503 | CG2 | VAL | D | 298 | -125.762 | 16.485 | 32.869 | 1.00 | 40.40 |
| 20504 | C | VAL | D | 298 | -125.279 | 13.735 | 32.960 | 1.00 | 40.81 |
| 20505 | O | VAL | D | 298 | -124.680 | 13.363 | 31.960 | 1.00 | 40.95 |
| 20506 | N | MET | D | 299 | -126.545 | 13.417 | 33.211 | 1.00 | 42.07 |
| 20507 | CA | MET | D | 299 | -127.357 | 12.754 | 32.209 | 1.00 | 43.04 |
| 20508 | CB | MET | D | 299 | -128.318 | 11.730 | 32.814 | 1.00 | 43.12 |
| 20509 | CG | MET | D | 299 | -129.343 | 11.197 | 31.808 | 1.00 | 42.96 |
| 20510 | SD | MET | D | 299 | -130.440 | 9.940 | 32.496 | 1.00 | 44.48 |
| 20511 | CE | MET | D | 299 | -130.314 | 10.360 | 34.181 | 1.00 | 46.63 |
| 20512 | C | MET | D | 299 | -128.151 | 13.805 | 31.439 | 1.00 | 44.09 |
| 20513 | O | MET | D | 299 | -128.743 | 14.720 | 32.020 | 1.00 | 43.89 |
| 20514 | N | ASP | D | 300 | -128.134 | 13.662 | 30.122 | 1.00 | 45.17 |
| 20515 | CA | ASP | D | 300 | -128.873 | 14.510 | 29.221 | 1.00 | 46.32 |
| 20516 | CB | ASP | D | 300 | -127.955 | 15.027 | 28.120 | 1.00 | 46.52 |
| 20517 | CG | ASP | D | 300 | -127.772 | 16.516 | 28.173 | 1.00 | 47.88 |
| 20518 | OD1 | ASP | D | 300 | -126.715 | 17.002 | 27.725 | 1.00 | 50.30 |
| 20519 | OD2 | ASP | D | 300 | -128.635 | 17.287 | 28.628 | 1.00 | 50.64 |
| 20520 | C | ASP | D | 300 | -129.926 | 13.643 | 28.589 | 1.00 | 47.06 |
| 20521 | O | ASP | D | 300 | -129.624 | 12.575 | 28.062 | 1.00 | 47.36 |
| 20522 | N | ILE | D | 301 | -131.170 | 14.090 | 28.641 | 1.00 | 48.02 |
| 20523 | CA | ILE | D | 301 | -132.242 | 13.358 | 28.006 | 1.00 | 48.60 |
| 20524 | CB | ILE | D | 301 | -133.408 | 13.185 | 28.991 | 1.00 | 48.50 |
| 20525 | CG1 | ILE | D | 301 | -132.894 | 12.408 | 30.212 | 1.00 | 48.51 |
| 20526 | CD1 | ILE | D | 301 | -133.961 | 11.793 | 31.083 | 1.00 | 48.21 |
| 20527 | CG2 | ILE | D | 301 | -134.562 | 12.441 | 28.345 | 1.00 | 48.06 |
| 20528 | C | ILE | D | 301 | -132.583 | 14.133 | 26.738 | 1.00 | 49.46 |
| 20529 | O | ILE | D | 301 | -132.856 | 15.328 | 26.786 | 1.00 | 49.71 |
| 20530 | N | CYS | D | 302 | -132.521 | 13.457 | 25.600 | 1.00 | 50.41 |
| 20531 | CA | CYS | D | 302 | -132.647 | 14.130 | 24.315 | 1.00 | 51.74 |
| 20532 | CB | CYS | D | 302 | -131.331 | 14.004 | 23.536 | 1.00 | 51.94 |
| 20533 | SG | CYS | D | 302 | -129.912 | 14.700 | 24.420 | 1.00 | 53.42 |
| 20534 | C | CYS | D | 302 | -133.813 | 13.662 | 23.463 | 1.00 | 52.24 |
| 20535 | O | CYS | D | 302 | -133.946 | 12.472 | 23.163 | 1.00 | 52.21 |
| 20536 | N | ASP | D | 303 | -134.642 | 14.619 | 23.061 | 1.00 | 53.09 |
| 20537 | CA | ASP | D | 303 | -135.832 | 14.334 | 22.271 | 1.00 | 54.23 |
| 20538 | CB | ASP | D | 303 | -137.057 | 15.022 | 22.887 | 1.00 | 54.39 |
| 20539 | CG | ASP | D | 303 | -137.524 | 14.344 | 24.169 | 1.00 | 54.66 |
| 20540 | OD1 | ASP | D | 303 | -136.697 | 14.174 | 25.088 | 1.00 | 55.54 |
| 20541 | OD2 | ASP | D | 303 | -138.692 | 13.945 | 24.347 | 1.00 | 54.11 |
| 20542 | C | ASP | D | 303 | -135.692 | 14.734 | 20.807 | 1.00 | 54.70 |
| 20543 | O | ASP | D | 303 | -135.141 | 15.778 | 20.474 | 1.00 | 54.30 |

FIGURE 3 OM

| A | B | C | D | E | F | G | H | I | J |
|---|---|---|---|---|---|---|---|---|---|
| 20544 | N | TYR | D | 304 | -136.200 | 13.888 | 19.930 | 1.00 | 56.01 |
| 20545 | CA | TYR | D | 304 | -136.153 | 14.183 | 18.515 | 1.00 | 57.68 |
| 20546 | CB | TYR | D | 304 | -136.262 | 12.906 | 17.695 | 1.00 | 57.57 |
| 20547 | CG | TYR | D | 304 | -136.301 | 13.173 | 16.209 | 1.00 | 58.83 |
| 20548 | CD1 | TYR | D | 304 | -135.197 | 13.707 | 15.553 | 1.00 | 59.38 |
| 20549 | CE1 | TYR | D | 304 | -135.228 | 13.966 | 14.196 | 1.00 | 59.37 |
| 20550 | CZ | TYR | D | 304 | -136.370 | 13.693 | 13.475 | 1.00 | 59.89 |
| 20551 | OH | TYR | D | 304 | -136.397 | 13.941 | 12.118 | 1.00 | 59.96 |
| 20552 | CE2 | TYR | D | 304 | -137.480 | 13.162 | 14.102 | 1.00 | 59.92 |
| 20553 | CD2 | TYR | D | 304 | -137.445 | 12.913 | 15.462 | 1.00 | 59.06 |
| 20554 | C | TYR | D | 304 | -137.267 | 15.143 | 18.109 | 1.00 | 58.63 |
| 20555 | O | TYR | D | 304 | -138.422 | 14.745 | 18.012 | 1.00 | 58.68 |
| 20556 | N | ASP | D | 305 | -136.922 | 16.407 | 17.887 | 1.00 | 59.92 |
| 20557 | CA | ASP | D | 305 | -137.902 | 17.361 | 17.395 | 1.00 | 61.44 |
| 20558 | CB | ASP | D | 305 | -137.400 | 18.795 | 17.523 | 1.00 | 61.67 |
| 20559 | CG | ASP | D | 305 | -138.430 | 19.803 | 17.065 | 1.00 | 62.80 |
| 20560 | OD1 | ASP | D | 305 | -138.633 | 20.826 | 17.764 | 1.00 | 62.88 |
| 20561 | OD2 | ASP | D | 305 | -139.087 | 19.637 | 16.012 | 1.00 | 63.63 |
| 20562 | C | ASP | D | 305 | -138.175 | 16.999 | 15.938 | 1.00 | 61.97 |
| 20563 | O | ASP | D | 305 | -137.269 | 16.973 | 15.113 | 1.00 | 61.92 |
| 20564 | N | GLU | D | 306 | -139.429 | 16.708 | 15.627 | 1.00 | 63.01 |
| 20565 | CA | GLU | D | 306 | -139.767 | 16.182 | 14.310 | 1.00 | 63.99 |
| 20566 | CB | GLU | D | 306 | -141.091 | 15.429 | 14.356 | 1.00 | 64.23 |
| 20567 | CG | GLU | D | 306 | -141.119 | 14.228 | 13.434 | 1.00 | 66.05 |
| 20568 | CD | GLU | D | 306 | -142.517 | 13.673 | 13.237 | 1.00 | 68.18 |
| 20569 | OE1 | GLU | D | 306 | -143.390 | 13.927 | 14.101 | 1.00 | 68.46 |
| 20570 | OE2 | GLU | D | 306 | -142.739 | 12.980 | 12.216 | 1.00 | 68.71 |
| 20571 | C | GLU | D | 306 | -139.802 | 17.239 | 13.222 | 1.00 | 64.19 |
| 20572 | O | GLU | D | 306 | -139.649 | 16.924 | 12.045 | 1.00 | 64.14 |
| 20573 | N | SER | D | 307 | -140.012 | 18.487 | 13.621 | 1.00 | 64.69 |
| 20574 | CA | SER | D | 307 | -140.004 | 19.595 | 12.680 | 1.00 | 65.06 |
| 20575 | CB | SER | D | 307 | -140.691 | 20.821 | 13.282 | 1.00 | 65.19 |
| 20576 | OG | SER | D | 307 | -141.988 | 20.490 | 13.763 | 1.00 | 65.21 |
| 20577 | C | SER | D | 307 | -138.549 | 19.896 | 12.355 | 1.00 | 65.21 |
| 20578 | O | SER | D | 307 | -138.081 | 19.586 | 11.258 | 1.00 | 65.60 |
| 20579 | N | SER | D | 308 | -137.835 | 20.461 | 13.332 | 1.00 | 65.02 |
| 20580 | CA | SER | D | 308 | -136.411 | 20.789 | 13.207 | 1.00 | 64.38 |
| 20581 | CB | SER | D | 308 | -135.793 | 21.013 | 14.589 | 1.00 | 64.52 |
| 20582 | OG | SER | D | 308 | -135.747 | 22.393 | 14.902 | 1.00 | 65.23 |
| 20583 | C | SER | D | 308 | -135.606 | 19.724 | 12.489 | 1.00 | 63.76 |
| 20584 | O | SER | D | 308 | -134.656 | 20.036 | 11.773 | 1.00 | 63.76 |
| 20585 | N | GLY | D | 309 | -135.979 | 18.466 | 12.698 | 1.00 | 63.19 |
| 20586 | CA | GLY | D | 309 | -135.275 | 17.345 | 12.100 | 1.00 | 62.51 |
| 20587 | C | GLY | D | 309 | -134.091 | 16.932 | 12.959 | 1.00 | 62.07 |
| 20588 | O | GLY | D | 309 | -133.438 | 15.915 | 12.696 | 1.00 | 62.28 |
| 20589 | N | ARG | D | 310 | -133.826 | 17.718 | 13.997 | 1.00 | 61.04 |
| 20590 | CA | ARG | D | 310 | -132.707 | 17.455 | 14.883 | 1.00 | 60.56 |
| 20591 | CB | ARG | D | 310 | -131.809 | 18.692 | 14.970 | 1.00 | 61.19 |
| 20592 | CG | ARG | D | 310 | -132.446 | 19.896 | 15.631 | 1.00 | 62.68 |
| 20593 | CD | ARG | D | 310 | -131.544 | 21.129 | 15.652 | 1.00 | 65.34 |
| 20594 | NE | ARG | D | 310 | -131.768 | 22.029 | 14.520 | 1.00 | 66.16 |

FIGURE 3 ON

| A | B | C | D | E | F | G | H | I | J |
|---|---|---|---|---|---|---|---|---|---|
| 20595 | CZ | ARG | D | 310 | -131.081 | 21.998 | 13.380 | 1.00 | 67.31 |
| 20596 | NH1 | ARG | D | 310 | -131.357 | 22.870 | 12.413 | 1.00 | 66.51 |
| 20597 | NH2 | ARG | D | 310 | -130.119 | 21.097 | 13.201 | 1.00 | 67.36 |
| 20598 | C | ARG | D | 310 | -133.123 | 16.973 | 16.283 | 1.00 | 59.42 |
| 20599 | O | ARG | D | 310 | -134.267 | 16.569 | 16.497 | 1.00 | 59.28 |
| 20600 | N | TRP | D | 311 | -132.182 | 17.011 | 17.227 | 1.00 | 58.05 |
| 20601 | CA | TRP | D | 311 | -132.417 | 16.522 | 18.586 | 1.00 | 56.38 |
| 20602 | CB | TRP | D | 311 | -131.471 | 15.371 | 18.886 | 1.00 | 55.45 |
| 20603 | CG | TRP | D | 311 | -131.778 | 14.187 | 18.077 | 1.00 | 51.45 |
| 20604 | CD1 | TRP | D | 311 | -131.477 | 13.993 | 16.772 | 1.00 | 48.75 |
| 20605 | NE1 | TRP | D | 311 | -131.945 | 12.771 | 16.353 | 1.00 | 48.27 |
| 20606 | CE2 | TRP | D | 311 | -132.569 | 12.155 | 17.404 | 1.00 | 47.06 |
| 20607 | CD2 | TRP | D | 311 | -132.488 | 13.027 | 18.505 | 1.00 | 47.70 |
| 20608 | CE3 | TRP | D | 311 | -133.062 | 12.631 | 19.711 | 1.00 | 44.75 |
| 20609 | CZ3 | TRP | D | 311 | -133.677 | 11.410 | 19.779 | 1.00 | 44.35 |
| 20610 | CH2 | TRP | D | 311 | -133.744 | 10.567 | 18.670 | 1.00 | 44.07 |
| 20611 | CZ2 | TRP | D | 311 | -133.197 | 10.921 | 17.473 | 1.00 | 45.46 |
| 20612 | C | TRP | D | 311 | -132.254 | 17.579 | 19.658 | 1.00 | 56.90 |
| 20613 | O | TRP | D | 311 | -131.300 | 18.362 | 19.636 | 1.00 | 56.98 |
| 20614 | N | ASN | D | 312 | -133.177 | 17.596 | 20.615 | 1.00 | 56.96 |
| 20615 | CA | ASN | D | 312 | -133.102 | 18.574 | 21.695 | 1.00 | 57.11 |
| 20616 | CB | ASN | D | 312 | -134.315 | 19.508 | 21.671 | 1.00 | 57.41 |
| 20617 | CG | ASN | D | 312 | -134.052 | 20.792 | 20.885 | 1.00 | 58.91 |
| 20618 | OD1 | ASN | D | 312 | -132.897 | 21.208 | 20.709 | 1.00 | 59.51 |
| 20619 | ND2 | ASN | D | 312 | -135.128 | 21.434 | 20.420 | 1.00 | 58.89 |
| 20620 | C | ASN | D | 312 | -132.954 | 17.948 | 23.070 | 1.00 | 56.68 |
| 20621 | O | ASN | D | 312 | -133.574 | 16.930 | 23.370 | 1.00 | 56.68 |
| 20622 | N | CYS | D | 313 | -132.133 | 18.569 | 23.906 | 1.00 | 56.20 |
| 20623 | CA | CYS | D | 313 | -131.908 | 18.078 | 25.255 | 1.00 | 55.75 |
| 20624 | CB | CYS | D | 313 | -130.443 | 17.686 | 25.445 | 1.00 | 55.84 |
| 20625 | SG | CYS | D | 313 | -129.763 | 16.705 | 24.092 | 1.00 | 55.50 |
| 20626 | C | CYS | D | 313 | -132.268 | 19.163 | 26.246 | 1.00 | 55.52 |
| 20627 | O | CYS | D | 313 | -131.425 | 19.987 | 26.599 | 1.00 | 55.53 |
| 20628 | N | LEU | D | 314 | -133.519 | 19.162 | 26.694 | 1.00 | 55.08 |
| 20629 | CA | LEU | D | 314 | -133.976 | 20.158 | 27.651 | 1.00 | 54.79 |
| 20630 | CB | LEU | D | 314 | -135.447 | 19.942 | 28.018 | 1.00 | 55.02 |
| 20631 | CG | LEU | D | 314 | -136.506 | 20.571 | 27.104 | 1.00 | 55.62 |
| 20632 | CD1 | LEU | D | 314 | -137.176 | 19.536 | 26.206 | 1.00 | 55.79 |
| 20633 | CD2 | LEU | D | 314 | -135.908 | 21.728 | 26.288 | 1.00 | 56.04 |
| 20634 | C | LEU | D | 314 | -133.129 | 20.177 | 28.915 | 1.00 | 54.45 |
| 20635 | O | LEU | D | 314 | -132.995 | 19.167 | 29.608 | 1.00 | 54.22 |
| 20636 | N | VAL | D | 315 | -132.569 | 21.345 | 29.199 | 1.00 | 53.93 |
| 20637 | CA | VAL | D | 315 | -131.762 | 21.569 | 30.386 | 1.00 | 53.93 |
| 20638 | CB | VAL | D | 315 | -131.346 | 23.042 | 30.470 | 1.00 | 53.93 |
| 20639 | CG1 | VAL | D | 315 | -130.998 | 23.423 | 31.888 | 1.00 | 54.90 |
| 20640 | CG2 | VAL | D | 315 | -130.176 | 23.314 | 29.524 | 1.00 | 54.82 |
| 20641 | C | VAL | D | 315 | -132.478 | 21.187 | 31.679 | 1.00 | 53.48 |
| 20642 | O | VAL | D | 315 | -131.846 | 20.806 | 32.663 | 1.00 | 53.58 |
| 20643 | N | ALA | D | 316 | -133.799 | 21.295 | 31.672 | 1.00 | 53.18 |
| 20644 | CA | ALA | D | 316 | -134.602 | 20.967 | 32.837 | 1.00 | 52.74 |
| 20645 | CB | ALA | D | 316 | -135.996 | 21.530 | 32.684 | 1.00 | 52.92 |

FIGURE 3 OO

| A | B | C | D | E | F | G | H | I | J |
|---|---|---|---|---|---|---|---|---|---|
| 20646 | C | ALA | D | 316 | -134.666 | 19.460 | 33.030 | 1.00 | 52.37 |
| 20647 | O | ALA | D | 316 | -135.096 | 18.972 | 34.077 | 1.00 | 52.77 |
| 20648 | N | ARG | D | 317 | -134.247 | 18.717 | 32.016 | 1.00 | 51.33 |
| 20649 | CA | ARG | D | 317 | -134.253 | 17.274 | 32.135 | 1.00 | 50.77 |
| 20650 | CB | ARG | D | 317 | -134.882 | 16.631 | 30.901 | 1.00 | 51.02 |
| 20651 | CG | ARG | D | 317 | -136.108 | 17.366 | 30.428 | 1.00 | 52.18 |
| 20652 | CD | ARG | D | 317 | -137.318 | 16.497 | 30.194 | 1.00 | 53.70 |
| 20653 | NE | ARG | D | 317 | -137.391 | 15.960 | 28.842 | 1.00 | 54.03 |
| 20654 | CZ | ARG | D | 317 | -138.480 | 16.017 | 28.084 | 1.00 | 54.06 |
| 20655 | NH1 | ARG | D | 317 | -138.470 | 15.493 | 26.864 | 1.00 | 53.60 |
| 20656 | NH2 | ARG | D | 317 | -139.579 | 16.600 | 28.547 | 1.00 | 52.91 |
| 20657 | C | ARG | D | 317 | -132.858 | 16.717 | 32.399 | 1.00 | 49.84 |
| 20658 | O | ARG | D | 317 | -132.619 | 15.529 | 32.209 | 1.00 | 49.58 |
| 20659 | N | GLN | D | 318 | -131.942 | 17.577 | 32.836 | 1.00 | 48.91 |
| 20660 | CA | GLN | D | 318 | -130.589 | 17.139 | 33.137 | 1.00 | 48.44 |
| 20661 | CB | GLN | D | 318 | -129.603 | 18.306 | 33.094 | 1.00 | 48.44 |
| 20662 | CG | GLN | D | 318 | -128.828 | 18.456 | 31.790 | 1.00 | 48.19 |
| 20663 | CD | GLN | D | 318 | -127.857 | 19.628 | 31.827 | 1.00 | 48.03 |
| 20664 | OE1 | GLN | D | 318 | -127.772 | 20.396 | 30.870 | 1.00 | 49.25 |
| 20665 | NE2 | GLN | D | 318 | -127.131 | 19.774 | 32.935 | 1.00 | 48.01 |
| 20666 | C | GLN | D | 318 | -130.544 | 16.478 | 34.512 | 1.00 | 48.18 |
| 20667 | O | GLN | D | 318 | -131.259 | 16.883 | 35.438 | 1.00 | 48.50 |
| 20668 | N | HIS | D | 319 | -129.713 | 15.455 | 34.648 | 1.00 | 46.99 |
| 20669 | CA | HIS | D | 319 | -129.576 | 14.803 | 35.937 | 1.00 | 46.42 |
| 20670 | CB | HIS | D | 319 | -130.256 | 13.442 | 35.930 | 1.00 | 46.33 |
| 20671 | CG | HIS | D | 319 | -131.735 | 13.531 | 35.743 | 1.00 | 47.19 |
| 20672 | ND1 | HIS | D | 319 | -132.617 | 13.596 | 36.801 | 1.00 | 47.10 |
| 20673 | CE1 | HIS | D | 319 | -133.850 | 13.688 | 36.335 | 1.00 | 47.18 |
| 20674 | NE2 | HIS | D | 319 | -133.799 | 13.696 | 35.016 | 1.00 | 47.10 |
| 20675 | CD2 | HIS | D | 319 | -132.487 | 13.612 | 34.620 | 1.00 | 47.64 |
| 20676 | C | HIS | D | 319 | -128.118 | 14.714 | 36.332 | 1.00 | 45.70 |
| 20677 | O | HIS | D | 319 | -127.283 | 14.184 | 35.598 | 1.00 | 45.25 |
| 20678 | N | ILE | D | 320 | -127.831 | 15.288 | 37.490 | 1.00 | 44.95 |
| 20679 | CA | ILE | D | 320 | -126.497 | 15.329 | 38.023 | 1.00 | 44.45 |
| 20680 | CB | ILE | D | 320 | -126.261 | 16.630 | 38.766 | 1.00 | 44.62 |
| 20681 | CG1 | ILE | D | 320 | -126.225 | 17.804 | 37.796 | 1.00 | 44.89 |
| 20682 | CD1 | ILE | D | 320 | -126.136 | 19.134 | 38.510 | 1.00 | 47.11 |
| 20683 | CG2 | ILE | D | 320 | -124.967 | 16.542 | 39.555 | 1.00 | 43.94 |
| 20684 | C | ILE | D | 320 | -126.268 | 14.192 | 38.992 | 1.00 | 44.24 |
| 20685 | O | ILE | D | 320 | -127.088 | 13.934 | 39.878 | 1.00 | 43.73 |
| 20686 | N | GLU | D | 321 | -125.144 | 13.516 | 38.801 | 1.00 | 43.70 |
| 20687 | CA | GLU | D | 321 | -124.720 | 12.461 | 39.697 | 1.00 | 43.55 |
| 20688 | CB | GLU | D | 321 | -124.890 | 11.095 | 39.051 | 1.00 | 43.54 |
| 20689 | CG | GLU | D | 321 | -124.672 | 9.948 | 40.019 | 1.00 | 44.31 |
| 20690 | CD | GLU | D | 321 | -124.872 | 8.607 | 39.356 | 1.00 | 44.06 |
| 20691 | OE1 | GLU | D | 321 | -125.701 | 8.539 | 38.425 | 1.00 | 44.82 |
| 20692 | OE2 | GLU | D | 321 | -124.198 | 7.632 | 39.756 | 1.00 | 43.52 |
| 20693 | C | GLU | D | 321 | -123.259 | 12.749 | 40.018 | 1.00 | 43.27 |
| 20694 | O | GLU | D | 321 | -122.401 | 12.727 | 39.141 | 1.00 | 43.00 |
| 20695 | N | MET | D | 322 | -123.013 | 13.091 | 41.274 | 1.00 | 42.93 |
| 20696 | CA | MET | D | 322 | -121.685 | 13.406 | 41.758 | 1.00 | 42.92 |

FIGURE 3 OP

| A | B | C | D | E | F | G | H | I | J |
|---|---|---|---|---|---|---|---|---|---|
| 20697 | CB | MET | D | 322 | -121.601 | 14.891 | 42.095 | 1.00 | 43.71 |
| 20698 | CG | MET | D | 322 | -122.219 | 15.230 | 43.448 | 1.00 | 46.97 |
| 20699 | SD | MET | D | 322 | -122.326 | 17.005 | 43.743 | 1.00 | 55.22 |
| 20700 | CE | MET | D | 322 | -123.151 | 17.545 | 42.282 | 1.00 | 52.68 |
| 20701 | C | MET | D | 322 | -121.385 | 12.600 | 43.019 | 1.00 | 41.70 |
| 20702 | O | MET | D | 322 | -122.237 | 11.876 | 43.538 | 1.00 | 41.07 |
| 20703 | N | SER | D | 323 | -120.154 | 12.722 | 43.486 | 1.00 | 40.83 |
| 20704 | CA | SER | D | 323 | -119.723 | 12.116 | 44.737 | 1.00 | 40.38 |
| 20705 | CB | SER | D | 323 | -119.042 | 10.760 | 44.517 | 1.00 | 40.42 |
| 20706 | OG | SER | D | 323 | -118.401 | 10.332 | 45.706 | 1.00 | 41.01 |
| 20707 | C | SER | D | 323 | -118.757 | 13.073 | 45.407 | 1.00 | 39.86 |
| 20708 | O | SER | D | 323 | -117.988 | 13.763 | 44.747 | 1.00 | 39.03 |
| 20709 | N | THR | D | 324 | -118.806 | 13.115 | 46.728 | 1.00 | 39.80 |
| 20710 | CA | THR | D | 324 | -117.933 | 13.991 | 47.480 | 1.00 | 39.64 |
| 20711 | CB | THR | D | 324 | -118.738 | 14.687 | 48.567 | 1.00 | 40.55 |
| 20712 | OG1 | THR | D | 324 | -119.514 | 13.702 | 49.269 | 1.00 | 41.35 |
| 20713 | CG2 | THR | D | 324 | -119.809 | 15.607 | 47.921 | 1.00 | 41.21 |
| 20714 | C | THR | D | 324 | -116.840 | 13.185 | 48.123 | 1.00 | 38.69 |
| 20715 | O | THR | D | 324 | -115.885 | 13.748 | 48.634 | 1.00 | 39.17 |
| 20716 | N | THR | D | 325 | -116.988 | 11.865 | 48.113 | 1.00 | 37.53 |
| 20717 | CA | THR | D | 325 | -115.999 | 10.993 | 48.729 | 1.00 | 36.20 |
| 20718 | CB | THR | D | 325 | -116.679 | 9.974 | 49.665 | 1.00 | 36.26 |
| 20719 | OG1 | THR | D | 325 | -117.738 | 9.296 | 48.968 | 1.00 | 34.46 |
| 20720 | CG2 | THR | D | 325 | -117.390 | 10.688 | 50.802 | 1.00 | 36.13 |
| 20721 | C | THR | D | 325 | -115.165 | 10.236 | 47.708 | 1.00 | 35.74 |
| 20722 | O | THR | D | 325 | -114.194 | 9.591 | 48.069 | 1.00 | 35.67 |
| 20723 | N | GLY | D | 326 | -115.542 | 10.292 | 46.436 | 1.00 | 34.80 |
| 20724 | CA | GLY | D | 326 | -114.782 | 9.552 | 45.447 | 1.00 | 34.05 |
| 20725 | C | GLY | D | 326 | -115.213 | 9.764 | 44.014 | 1.00 | 33.13 |
| 20726 | O | GLY | D | 326 | -115.473 | 10.883 | 43.595 | 1.00 | 33.76 |
| 20727 | N | TRP | D | 327 | -115.278 | 8.686 | 43.253 | 1.00 | 32.05 |
| 20728 | CA | TRP | D | 327 | -115.703 | 8.779 | 41.856 | 1.00 | 31.00 |
| 20729 | CB | TRP | D | 327 | -114.857 | 7.848 | 40.999 | 1.00 | 30.19 |
| 20730 | CG | TRP | D | 327 | -114.915 | 6.432 | 41.450 | 1.00 | 28.25 |
| 20731 | CD1 | TRP | D | 327 | -115.692 | 5.446 | 40.930 | 1.00 | 26.84 |
| 20732 | NE1 | TRP | D | 327 | -115.468 | 4.266 | 41.598 | 1.00 | 27.93 |
| 20733 | CE2 | TRP | D | 327 | -114.541 | 4.480 | 42.585 | 1.00 | 26.83 |
| 20734 | CD2 | TRP | D | 327 | -114.166 | 5.830 | 42.519 | 1.00 | 27.33 |
| 20735 | CE3 | TRP | D | 327 | -113.220 | 6.301 | 43.437 | 1.00 | 27.06 |
| 20736 | CZ3 | TRP | D | 327 | -112.683 | 5.415 | 44.363 | 1.00 | 24.99 |
| 20737 | CH2 | TRP | D | 327 | -113.075 | 4.090 | 44.402 | 1.00 | 24.28 |
| 20738 | CZ2 | TRP | D | 327 | -114.006 | 3.601 | 43.525 | 1.00 | 27.40 |
| 20739 | C | TRP | D | 327 | -117.184 | 8.419 | 41.732 | 1.00 | 30.82 |
| 20740 | O | TRP | D | 327 | -117.816 | 8.040 | 42.716 | 1.00 | 30.21 |
| 20741 | N | VAL | D | 328 | -117.746 | 8.538 | 40.534 | 1.00 | 30.73 |
| 20742 | CA | VAL | D | 328 | -119.154 | 8.176 | 40.359 | 1.00 | 30.65 |
| 20743 | CB | VAL | D | 328 | -119.951 | 9.245 | 39.588 | 1.00 | 31.06 |
| 20744 | CG1 | VAL | D | 328 | -119.170 | 9.744 | 38.408 | 1.00 | 32.04 |
| 20745 | CG2 | VAL | D | 328 | -121.314 | 8.693 | 39.146 | 1.00 | 31.44 |
| 20746 | C | VAL | D | 328 | -119.312 | 6.813 | 39.711 | 1.00 | 30.16 |
| 20747 | O | VAL | D | 328 | -118.665 | 6.510 | 38.732 | 1.00 | 30.08 |

FIGURE 3 OQ

| A | B | C | D | E | F | G | H | I | J |
|---|---|---|---|---|---|---|---|---|---|
| 20748 | N | GLY | D | 329 | -120.186 | 5.987 | 40.274 | 1.00 | 30.55 |
| 20749 | CA | GLY | D | 329 | -120.400 | 4.643 | 39.775 | 1.00 | 30.09 |
| 20750 | C | GLY | D | 329 | -119.382 | 3.717 | 40.402 | 1.00 | 29.88 |
| 20751 | O | GLY | D | 329 | -118.482 | 4.163 | 41.079 | 1.00 | 29.62 |
| 20752 | N | ARG | D | 330 | -119.529 | 2.421 | 40.190 | 1.00 | 30.44 |
| 20753 | CA | ARG | D | 330 | -118.546 | 1.486 | 40.709 | 1.00 | 31.33 |
| 20754 | CB | ARG | D | 330 | -119.112 | 0.062 | 40.728 | 1.00 | 31.52 |
| 20755 | CG | ARG | D | 330 | -120.301 | -0.028 | 41.688 | 1.00 | 34.59 |
| 20756 | CD | ARG | D | 330 | -120.522 | -1.386 | 42.369 | 1.00 | 36.97 |
| 20757 | NE | ARG | D | 330 | -121.713 | -1.953 | 41.798 | 1.00 | 40.76 |
| 20758 | CZ | ARG | D | 330 | -122.793 | -2.312 | 42.475 | 1.00 | 40.18 |
| 20759 | NH1 | ARG | D | 330 | -123.830 | -2.786 | 41.799 | 1.00 | 40.28 |
| 20760 | NH2 | ARG | D | 330 | -122.828 | -2.238 | 43.798 | 1.00 | 37.97 |
| 20761 | C | ARG | D | 330 | -117.284 | 1.636 | 39.864 | 1.00 | 31.13 |
| 20762 | O | ARG | D | 330 | -116.205 | 1.879 | 40.394 | 1.00 | 30.90 |
| 20763 | N | PHE | D | 331 | -117.454 | 1.558 | 38.548 | 1.00 | 31.06 |
| 20764 | CA | PHE | D | 331 | -116.374 | 1.766 | 37.602 | 1.00 | 31.27 |
| 20765 | CB | PHE | D | 331 | -116.087 | 0.487 | 36.823 | 1.00 | 30.73 |
| 20766 | CG | PHE | D | 331 | -115.403 | -0.544 | 37.647 | 1.00 | 29.04 |
| 20767 | CD1 | PHE | D | 331 | -114.038 | -0.506 | 37.807 | 1.00 | 26.39 |
| 20768 | CE1 | PHE | D | 331 | -113.394 | -1.437 | 38.585 | 1.00 | 26.15 |
| 20769 | CZ | PHE | D | 331 | -114.124 | -2.394 | 39.256 | 1.00 | 24.63 |
| 20770 | CE2 | PHE | D | 331 | -115.499 | -2.430 | 39.114 | 1.00 | 26.77 |
| 20771 | CD2 | PHE | D | 331 | -116.132 | -1.501 | 38.324 | 1.00 | 26.70 |
| 20772 | C | PHE | D | 331 | -116.749 | 2.890 | 36.664 | 1.00 | 32.13 |
| 20773 | O | PHE | D | 331 | -115.879 | 3.477 | 36.007 | 1.00 | 31.91 |
| 20774 | N | ARG | D | 332 | -118.054 | 3.171 | 36.627 | 1.00 | 32.56 |
| 20775 | CA | ARG | D | 332 | -118.651 | 4.236 | 35.823 | 1.00 | 33.59 |
| 20776 | CB | ARG | D | 332 | -118.594 | 3.913 | 34.328 | 1.00 | 33.84 |
| 20777 | CG | ARG | D | 332 | -119.441 | 2.731 | 33.895 | 1.00 | 35.39 |
| 20778 | CD | ARG | D | 332 | -119.112 | 2.215 | 32.492 | 1.00 | 40.50 |
| 20779 | NE | ARG | D | 332 | -118.171 | 1.088 | 32.510 | 1.00 | 44.31 |
| 20780 | CZ | ARG | D | 332 | -116.870 | 1.169 | 32.764 | 1.00 | 44.10 |
| 20781 | NH1 | ARG | D | 332 | -116.299 | 2.332 | 33.022 | 1.00 | 44.56 |
| 20782 | NH2 | ARG | D | 332 | -116.135 | 0.069 | 32.762 | 1.00 | 45.36 |
| 20783 | C | ARG | D | 332 | -120.109 | 4.435 | 36.233 | 1.00 | 34.05 |
| 20784 | O | ARG | D | 332 | -120.723 | 3.563 | 36.855 | 1.00 | 33.55 |
| 20785 | N | PRO | D | 333 | -120.662 | 5.598 | 35.912 | 1.00 | 34.68 |
| 20786 | CA | PRO | D | 333 | -122.069 | 5.862 | 36.203 | 1.00 | 34.94 |
| 20787 | CB | PRO | D | 333 | -122.335 | 7.136 | 35.409 | 1.00 | 35.03 |
| 20788 | CG | PRO | D | 333 | -121.037 | 7.855 | 35.513 | 1.00 | 34.75 |
| 20789 | CD | PRO | D | 333 | -119.997 | 6.769 | 35.314 | 1.00 | 34.69 |
| 20790 | C | PRO | D | 333 | -122.946 | 4.706 | 35.747 | 1.00 | 35.45 |
| 20791 | O | PRO | D | 333 | -122.688 | 4.066 | 34.737 | 1.00 | 35.18 |
| 20792 | N | SER | D | 334 | -123.960 | 4.403 | 36.539 | 1.00 | 36.54 |
| 20793 | CA | SER | D | 334 | -124.877 | 3.333 | 36.206 | 1.00 | 37.66 |
| 20794 | CB | SER | D | 334 | -125.754 | 2.999 | 37.404 | 1.00 | 37.96 |
| 20795 | OG | SER | D | 334 | -126.055 | 1.611 | 37.410 | 1.00 | 40.76 |
| 20796 | C | SER | D | 334 | -125.771 | 3.720 | 35.025 | 1.00 | 38.00 |
| 20797 | O | SER | D | 334 | -125.977 | 4.901 | 34.737 | 1.00 | 37.76 |
| 20798 | N | GLU | D | 335 | -126.302 | 2.711 | 34.354 | 1.00 | 38.11 |

FIGURE 3 OR

| A | B | C | D | E | F | G | H | I | J |
|---|---|---|---|---|---|---|---|---|---|
| 20799 | CA | GLU | D | 335 | -127.172 | 2.939 | 33.225 | 1.00 | 38.83 |
| 20800 | CB | GLU | D | 335 | -126.944 | 1.848 | 32.169 | 1.00 | 39.12 |
| 20801 | CG | GLU | D | 335 | -127.591 | 0.498 | 32.460 | 1.00 | 39.81 |
| 20802 | CD | GLU | D | 335 | -126.907 | -0.270 | 33.582 | 1.00 | 42.25 |
| 20803 | OE1 | GLU | D | 335 | -125.751 | 0.067 | 33.959 | 1.00 | 42.39 |
| 20804 | OE2 | GLU | D | 335 | -127.537 | -1.220 | 34.092 | 1.00 | 42.00 |
| 20805 | C | GLU | D | 335 | -128.647 | 2.999 | 33.649 | 1.00 | 39.02 |
| 20806 | O | GLU | D | 335 | -129.097 | 2.264 | 34.537 | 1.00 | 38.91 |
| 20807 | N | PRO | D | 336 | -129.416 | 3.857 | 32.996 | 1.00 | 39.27 |
| 20808 | CA | PRO | D | 336 | -130.832 | 4.004 | 33.339 | 1.00 | 39.37 |
| 20809 | CB | PRO | D | 336 | -131.230 | 5.306 | 32.641 | 1.00 | 39.23 |
| 20810 | CG | PRO | D | 336 | -130.280 | 5.445 | 31.511 | 1.00 | 39.21 |
| 20811 | CD | PRO | D | 336 | -129.014 | 4.724 | 31.878 | 1.00 | 39.11 |
| 20812 | C | PRO | D | 336 | -131.668 | 2.885 | 32.775 | 1.00 | 39.43 |
| 20813 | O | PRO | D | 336 | -131.364 | 2.369 | 31.712 | 1.00 | 39.27 |
| 20814 | N | HIS | D | 337 | -132.711 | 2.509 | 33.505 | 1.00 | 40.02 |
| 20815 | CA | HIS | D | 337 | -133.705 | 1.581 | 33.002 | 1.00 | 40.01 |
| 20816 | CB | HIS | D | 337 | -133.788 | 0.347 | 33.889 | 1.00 | 39.87 |
| 20817 | CG | HIS | D | 337 | -132.543 | -0.481 | 33.843 | 1.00 | 39.02 |
| 20818 | ND1 | HIS | D | 337 | -132.445 | -1.640 | 33.106 | 1.00 | 38.52 |
| 20819 | CE1 | HIS | D | 337 | -131.227 | -2.136 | 33.223 | 1.00 | 36.68 |
| 20820 | NE2 | HIS | D | 337 | -130.525 | -1.329 | 33.992 | 1.00 | 36.50 |
| 20821 | CD2 | HIS | D | 337 | -131.320 | -0.279 | 34.385 | 1.00 | 37.82 |
| 20822 | C | HIS | D | 337 | -135.009 | 2.353 | 32.920 | 1.00 | 40.66 |
| 20823 | O | HIS | D | 337 | -135.621 | 2.685 | 33.935 | 1.00 | 41.07 |
| 20824 | N | PHE | D | 338 | -135.405 | 2.675 | 31.693 | 1.00 | 41.13 |
| 20825 | CA | PHE | D | 338 | -136.603 | 3.464 | 31.431 | 1.00 | 41.27 |
| 20826 | CB | PHE | D | 338 | -136.482 | 4.185 | 30.079 | 1.00 | 40.88 |
| 20827 | CG | PHE | D | 338 | -135.505 | 5.331 | 30.083 | 1.00 | 39.25 |
| 20828 | CD1 | PHE | D | 338 | -134.185 | 5.135 | 29.723 | 1.00 | 36.83 |
| 20829 | CE1 | PHE | D | 338 | -133.297 | 6.175 | 29.725 | 1.00 | 35.88 |
| 20830 | CZ | PHE | D | 338 | -133.709 | 7.434 | 30.093 | 1.00 | 37.30 |
| 20831 | CE2 | PHE | D | 338 | -135.023 | 7.652 | 30.441 | 1.00 | 37.67 |
| 20832 | CD2 | PHE | D | 338 | -135.915 | 6.602 | 30.432 | 1.00 | 38.38 |
| 20833 | C | PHE | D | 338 | -137.887 | 2.653 | 31.436 | 1.00 | 42.05 |
| 20834 | O | PHE | D | 338 | -137.921 | 1.475 | 31.058 | 1.00 | 42.03 |
| 20835 | N | THR | D | 339 | -138.956 | 3.301 | 31.872 | 1.00 | 43.22 |
| 20836 | CA | THR | D | 339 | -140.281 | 2.714 | 31.779 | 1.00 | 44.21 |
| 20837 | CB | THR | D | 339 | -141.266 | 3.557 | 32.566 | 1.00 | 44.18 |
| 20838 | OG1 | THR | D | 339 | -140.957 | 4.942 | 32.356 | 1.00 | 45.08 |
| 20839 | CG2 | THR | D | 339 | -141.018 | 3.391 | 34.056 | 1.00 | 44.83 |
| 20840 | C | THR | D | 339 | -140.621 | 2.769 | 30.300 | 1.00 | 44.64 |
| 20841 | O | THR | D | 339 | -140.049 | 3.565 | 29.565 | 1.00 | 44.48 |
| 20842 | N | LEU | D | 340 | -141.544 | 1.929 | 29.859 | 1.00 | 45.84 |
| 20843 | CA | LEU | D | 340 | -141.910 | 1.885 | 28.451 | 1.00 | 46.69 |
| 20844 | CB | LEU | D | 340 | -143.196 | 1.089 | 28.250 | 1.00 | 46.97 |
| 20845 | CG | LEU | D | 340 | -143.203 | 0.251 | 26.964 | 1.00 | 48.22 |
| 20846 | CD1 | LEU | D | 340 | -142.944 | -1.233 | 27.257 | 1.00 | 49.71 |
| 20847 | CD2 | LEU | D | 340 | -142.182 | 0.783 | 25.975 | 1.00 | 47.97 |
| 20848 | C | LEU | D | 340 | -142.050 | 3.280 | 27.841 | 1.00 | 46.96 |
| 20849 | O | LEU | D | 340 | -141.341 | 3.626 | 26.890 | 1.00 | 47.27 |

FIGURE 3 OS

| A | B | C | D | E | F | G | H | I | J |
|---|---|---|---|---|---|---|---|---|---|
| 20850 | N | ASP | D | 341 | -142.942 | 4.086 | 28.402 | 1.00 | 47.11 |
| 20851 | CA | ASP | D | 341 | -143.190 | 5.430 | 27.884 | 1.00 | 47.34 |
| 20852 | CB | ASP | D | 341 | -144.350 | 6.100 | 28.632 | 1.00 | 47.48 |
| 20853 | CG | ASP | D | 341 | -144.042 | 6.333 | 30.099 | 1.00 | 49.18 |
| 20854 | OD1 | ASP | D | 341 | -145.000 | 6.577 | 30.873 | 1.00 | 49.68 |
| 20855 | OD2 | ASP | D | 341 | -142.878 | 6.292 | 30.570 | 1.00 | 50.47 |
| 20856 | C | ASP | D | 341 | -141.972 | 6.331 | 27.952 | 1.00 | 46.95 |
| 20857 | O | ASP | D | 341 | -141.967 | 7.411 | 27.368 | 1.00 | 47.08 |
| 20858 | N | GLY | D | 342 | -140.960 | 5.910 | 28.701 | 1.00 | 46.48 |
| 20859 | CA | GLY | D | 342 | -139.740 | 6.683 | 28.824 | 1.00 | 45.70 |
| 20860 | C | GLY | D | 342 | -139.868 | 7.998 | 29.566 | 1.00 | 45.41 |
| 20861 | O | GLY | D | 342 | -139.019 | 8.880 | 29.432 | 1.00 | 45.37 |
| 20862 | N | ASN | D | 343 | -140.917 | 8.159 | 30.360 | 1.00 | 45.22 |
| 20863 | CA | ASN | D | 343 | -141.043 | 9.411 | 31.106 | 1.00 | 44.83 |
| 20864 | CB | ASN | D | 343 | -142.503 | 9.846 | 31.210 | 1.00 | 45.19 |
| 20865 | CG | ASN | D | 343 | -143.140 | 10.063 | 29.847 | 1.00 | 46.90 |
| 20866 | OD1 | ASN | D | 343 | -142.536 | 10.666 | 28.960 | 1.00 | 48.47 |
| 20867 | ND2 | ASN | D | 343 | -144.363 | 9.564 | 29.671 | 1.00 | 48.14 |
| 20868 | C | ASN | D | 343 | -140.353 | 9.333 | 32.477 | 1.00 | 43.86 |
| 20869 | O | ASN | D | 343 | -140.230 | 10.321 | 33.204 | 1.00 | 43.78 |
| 20870 | N | SER | D | 344 | -139.891 | 8.149 | 32.827 | 1.00 | 42.61 |
| 20871 | CA | SER | D | 344 | -139.156 | 8.011 | 34.070 | 1.00 | 42.35 |
| 20872 | CB | SER | D | 344 | -140.093 | 7.952 | 35.291 | 1.00 | 41.77 |
| 20873 | OG | SER | D | 344 | -141.020 | 6.891 | 35.185 | 1.00 | 42.32 |
| 20874 | C | SER | D | 344 | -138.243 | 6.800 | 33.961 | 1.00 | 41.77 |
| 20875 | O | SER | D | 344 | -138.322 | 6.038 | 32.991 | 1.00 | 41.99 |
| 20876 | N | PHE | D | 345 | -137.370 | 6.627 | 34.945 | 1.00 | 41.31 |
| 20877 | CA | PHE | D | 345 | -136.408 | 5.538 | 34.893 | 1.00 | 40.19 |
| 20878 | CB | PHE | D | 345 | -135.244 | 5.900 | 33.964 | 1.00 | 39.91 |
| 20879 | CG | PHE | D | 345 | -134.382 | 7.017 | 34.473 | 1.00 | 38.04 |
| 20880 | CD1 | PHE | D | 345 | -133.315 | 6.760 | 35.316 | 1.00 | 37.16 |
| 20881 | CE1 | PHE | D | 345 | -132.519 | 7.787 | 35.775 | 1.00 | 36.17 |
| 20882 | CZ | PHE | D | 345 | -132.778 | 9.077 | 35.392 | 1.00 | 34.87 |
| 20883 | CE2 | PHE | D | 345 | -133.830 | 9.339 | 34.545 | 1.00 | 35.78 |
| 20884 | CD2 | PHE | D | 345 | -134.622 | 8.319 | 34.092 | 1.00 | 35.52 |
| 20885 | C | PHE | D | 345 | -135.865 | 5.134 | 36.247 | 1.00 | 40.24 |
| 20886 | O | PHE | D | 345 | -136.029 | 5.839 | 37.247 | 1.00 | 39.97 |
| 20887 | N | TYR | D | 346 | -135.213 | 3.974 | 36.246 | 1.00 | 40.03 |
| 20888 | CA | TYR | D | 346 | -134.591 | 3.418 | 37.413 | 1.00 | 40.01 |
| 20889 | CB | TYR | D | 346 | -135.129 | 2.016 | 37.656 | 1.00 | 40.29 |
| 20890 | CG | TYR | D | 346 | -136.615 | 1.958 | 37.902 | 1.00 | 41.07 |
| 20891 | CD1 | TYR | D | 346 | -137.119 | 2.044 | 39.184 | 1.00 | 39.92 |
| 20892 | CE1 | TYR | D | 346 | -138.467 | 1.984 | 39.418 | 1.00 | 42.29 |
| 20893 | CZ | TYR | D | 346 | -139.342 | 1.837 | 38.364 | 1.00 | 43.21 |
| 20894 | OH | TYR | D | 346 | -140.693 | 1.778 | 38.616 | 1.00 | 42.09 |
| 20895 | CE2 | TYR | D | 346 | -138.865 | 1.752 | 37.065 | 1.00 | 42.81 |
| 20896 | CD2 | TYR | D | 346 | -137.511 | 1.809 | 36.844 | 1.00 | 41.55 |
| 20897 | C | TYR | D | 346 | -133.087 | 3.327 | 37.186 | 1.00 | 40.23 |
| 20898 | O | TYR | D | 346 | -132.629 | 3.013 | 36.074 | 1.00 | 39.81 |
| 20899 | N | LYS | D | 347 | -132.318 | 3.632 | 38.226 | 1.00 | 39.63 |
| 20900 | CA | LYS | D | 347 | -130.878 | 3.421 | 38.167 | 1.00 | 39.76 |

FIGURE 3 OT

| A | B | C | D | E | F | G | H | I | J |
|---|---|---|---|---|---|---|---|---|---|
| 20901 | CB | LYS | D | 347 | -130.147 | 4.386 | 37.211 | 1.00 | 39.79 |
| 20902 | CG | LYS | D | 347 | -129.986 | 5.789 | 37.683 | 1.00 | 39.95 |
| 20903 | CD | LYS | D | 347 | -128.535 | 6.088 | 37.930 | 1.00 | 41.81 |
| 20904 | CE | LYS | D | 347 | -127.839 | 6.780 | 36.751 | 1.00 | 40.24 |
| 20905 | NZ | LYS | D | 347 | -126.343 | 6.794 | 36.995 | 1.00 | 37.48 |
| 20906 | C | LYS | D | 347 | -130.264 | 3.386 | 39.556 | 1.00 | 39.41 |
| 20907 | O | LYS | D | 347 | -130.791 | 3.966 | 40.510 | 1.00 | 39.41 |
| 20908 | N | ILE | D | 348 | -129.164 | 2.658 | 39.647 | 1.00 | 38.65 |
| 20909 | CA | ILE | D | 348 | -128.466 | 2.465 | 40.888 | 1.00 | 38.14 |
| 20910 | CB | ILE | D | 348 | -127.664 | 1.167 | 40.798 | 1.00 | 37.90 |
| 20911 | CG1 | ILE | D | 348 | -128.572 | 0.058 | 40.260 | 1.00 | 36.13 |
| 20912 | CD1 | ILE | D | 348 | -127.878 | -1.248 | 40.028 | 1.00 | 34.90 |
| 20913 | CG2 | ILE | D | 348 | -127.068 | 0.819 | 42.155 | 1.00 | 37.06 |
| 20914 | C | ILE | D | 348 | -127.538 | 3.621 | 41.156 | 1.00 | 38.53 |
| 20915 | O | ILE | D | 348 | -126.674 | 3.938 | 40.337 | 1.00 | 39.14 |
| 20916 | N | ILE | D | 349 | -127.734 | 4.257 | 42.302 | 1.00 | 38.29 |
| 20917 | CA | ILE | D | 349 | -126.870 | 5.317 | 42.759 | 1.00 | 37.95 |
| 20918 | CB | ILE | D | 349 | -127.530 | 6.679 | 42.605 | 1.00 | 38.25 |
| 20919 | CG1 | ILE | D | 349 | -128.665 | 6.828 | 43.609 | 1.00 | 38.68 |
| 20920 | CD1 | ILE | D | 349 | -129.020 | 8.269 | 43.923 | 1.00 | 39.44 |
| 20921 | CG2 | ILE | D | 349 | -128.003 | 6.898 | 41.177 | 1.00 | 38.73 |
| 20922 | C | ILE | D | 349 | -126.587 | 5.053 | 44.229 | 1.00 | 37.73 |
| 20923 | O | ILE | D | 349 | -127.292 | 4.278 | 44.876 | 1.00 | 37.75 |
| 20924 | N | SER | D | 350 | -125.536 | 5.671 | 44.747 | 1.00 | 37.22 |
| 20925 | CA | SER | D | 350 | -125.188 | 5.486 | 46.133 | 1.00 | 37.43 |
| 20926 | CB | SER | D | 350 | -123.757 | 5.952 | 46.391 | 1.00 | 37.24 |
| 20927 | OG | SER | D | 350 | -123.712 | 7.367 | 46.324 | 1.00 | 39.73 |
| 20928 | C | SER | D | 350 | -126.163 | 6.328 | 46.922 | 1.00 | 36.70 |
| 20929 | O | SER | D | 350 | -126.408 | 7.479 | 46.562 | 1.00 | 36.34 |
| 20930 | N | ASN | D | 351 | -126.743 | 5.757 | 47.975 | 1.00 | 36.35 |
| 20931 | CA | ASN | D | 351 | -127.699 | 6.523 | 48.782 | 1.00 | 36.49 |
| 20932 | CB | ASN | D | 351 | -128.791 | 5.650 | 49.423 | 1.00 | 35.93 |
| 20933 | CG | ASN | D | 351 | -128.255 | 4.665 | 50.461 | 1.00 | 36.10 |
| 20934 | OD1 | ASN | D | 351 | -127.105 | 4.750 | 50.903 | 1.00 | 35.57 |
| 20935 | ND2 | ASN | D | 351 | -129.109 | 3.725 | 50.866 | 1.00 | 33.75 |
| 20936 | C | ASN | D | 351 | -127.004 | 7.410 | 49.798 | 1.00 | 36.80 |
| 20937 | O | ASN | D | 351 | -125.790 | 7.622 | 49.724 | 1.00 | 36.43 |
| 20938 | N | GLU | D | 352 | -127.775 | 7.933 | 50.736 | 1.00 | 37.42 |
| 20939 | CA | GLU | D | 352 | -127.230 | 8.849 | 51.720 | 1.00 | 38.62 |
| 20940 | CB | GLU | D | 352 | -128.349 | 9.455 | 52.568 | 1.00 | 39.24 |
| 20941 | CG | GLU | D | 352 | -128.946 | 8.502 | 53.600 | 1.00 | 42.95 |
| 20942 | CD | GLU | D | 352 | -129.651 | 7.298 | 52.982 | 1.00 | 47.08 |
| 20943 | OE1 | GLU | D | 352 | -129.544 | 6.204 | 53.585 | 1.00 | 47.83 |
| 20944 | OE2 | GLU | D | 352 | -130.318 | 7.442 | 51.911 | 1.00 | 48.18 |
| 20945 | C | GLU | D | 352 | -126.189 | 8.181 | 52.612 | 1.00 | 38.18 |
| 20946 | O | GLU | D | 352 | -125.279 | 8.840 | 53.104 | 1.00 | 38.32 |
| 20947 | N | GLU | D | 353 | -126.310 | 6.871 | 52.795 | 1.00 | 37.68 |
| 20948 | CA | GLU | D | 353 | -125.397 | 6.154 | 53.658 | 1.00 | 37.20 |
| 20949 | CB | GLU | D | 353 | -126.138 | 5.092 | 54.501 | 1.00 | 37.96 |
| 20950 | CG | GLU | D | 353 | -127.264 | 4.362 | 53.789 | 1.00 | 41.29 |
| 20951 | CD | GLU | D | 353 | -127.688 | 3.060 | 54.474 | 1.00 | 46.35 |

FIGURE 3 OU

| A | B | C | D | E | F | G | H | I | J |
|---|---|---|---|---|---|---|---|---|---|
| 20952 | OE1 | GLU | D | 353 | -127.325 | 2.860 | 55.670 | 1.00 | 47.37 |
| 20953 | OE2 | GLU | D | 353 | -128.383 | 2.232 | 53.808 | 1.00 | 46.05 |
| 20954 | C | GLU | D | 353 | -124.210 | 5.553 | 52.892 | 1.00 | 36.18 |
| 20955 | O | GLU | D | 353 | -123.335 | 4.912 | 53.489 | 1.00 | 35.36 |
| 20956 | N | GLY | D | 354 | -124.186 | 5.770 | 51.577 | 1.00 | 35.03 |
| 20957 | CA | GLY | D | 354 | -123.124 | 5.260 | 50.724 | 1.00 | 33.33 |
| 20958 | C | GLY | D | 354 | -123.372 | 3.874 | 50.161 | 1.00 | 32.88 |
| 20959 | O | GLY | D | 354 | -122.454 | 3.244 | 49.633 | 1.00 | 32.29 |
| 20960 | N | TYR | D | 355 | -124.602 | 3.380 | 50.283 | 1.00 | 32.37 |
| 20961 | CA | TYR | D | 355 | -124.930 | 2.069 | 49.739 | 1.00 | 32.40 |
| 20962 | CB | TYR | D | 355 | -125.689 | 1.188 | 50.740 | 1.00 | 32.12 |
| 20963 | CG | TYR | D | 355 | -124.851 | 0.734 | 51.906 | 1.00 | 32.12 |
| 20964 | CD1 | TYR | D | 355 | -124.691 | 1.537 | 53.026 | 1.00 | 31.66 |
| 20965 | CE1 | TYR | D | 355 | -123.924 | 1.128 | 54.105 | 1.00 | 31.91 |
| 20966 | CZ | TYR | D | 355 | -123.299 | -0.102 | 54.070 | 1.00 | 34.47 |
| 20967 | OH | TYR | D | 355 | -122.525 | -0.514 | 55.145 | 1.00 | 35.16 |
| 20968 | CE2 | TYR | D | 355 | -123.449 | -0.929 | 52.966 | 1.00 | 33.95 |
| 20969 | CD2 | TYR | D | 355 | -124.219 | -0.504 | 51.890 | 1.00 | 33.48 |
| 20970 | C | TYR | D | 355 | -125.719 | 2.231 | 48.453 | 1.00 | 32.36 |
| 20971 | O | TYR | D | 355 | -126.611 | 3.074 | 48.355 | 1.00 | 32.46 |
| 20972 | N | ARG | D | 356 | -125.366 | 1.415 | 47.468 | 1.00 | 32.22 |
| 20973 | CA | ARG | D | 356 | -125.976 | 1.480 | 46.145 | 1.00 | 32.23 |
| 20974 | CB | ARG | D | 356 | -124.989 | 0.944 | 45.094 | 1.00 | 32.13 |
| 20975 | CG | ARG | D | 356 | -123.887 | 1.975 | 44.815 | 1.00 | 32.43 |
| 20976 | CD | ARG | D | 356 | -122.617 | 1.473 | 44.134 | 1.00 | 32.47 |
| 20977 | NE | ARG | D | 356 | -121.497 | 2.343 | 44.491 | 1.00 | 31.76 |
| 20978 | CZ | ARG | D | 356 | -121.250 | 3.533 | 43.940 | 1.00 | 30.21 |
| 20979 | NH1 | ARG | D | 356 | -122.022 | 4.006 | 42.967 | 1.00 | 29.24 |
| 20980 | NH2 | ARG | D | 356 | -120.218 | 4.249 | 44.363 | 1.00 | 29.43 |
| 20981 | C | ARG | D | 356 | -127.349 | 0.811 | 46.066 | 1.00 | 31.78 |
| 20982 | O | ARG | D | 356 | -127.493 | -0.386 | 46.273 | 1.00 | 31.54 |
| 20983 | N | HIS | D | 357 | -128.357 | 1.612 | 45.760 | 1.00 | 31.98 |
| 20984 | CA | HIS | D | 357 | -129.733 | 1.128 | 45.714 | 1.00 | 31.67 |
| 20985 | CB | HIS | D | 357 | -130.457 | 1.465 | 47.018 | 1.00 | 30.76 |
| 20986 | CG | HIS | D | 357 | -130.002 | 0.621 | 48.158 | 1.00 | 29.54 |
| 20987 | ND1 | HIS | D | 357 | -130.369 | -0.697 | 48.287 | 1.00 | 26.68 |
| 20988 | CE1 | HIS | D | 357 | -129.787 | -1.209 | 49.355 | 1.00 | 26.99 |
| 20989 | NE2 | HIS | D | 357 | -129.026 | -0.278 | 49.901 | 1.00 | 27.44 |
| 20990 | CD2 | HIS | D | 357 | -129.133 | 0.873 | 49.166 | 1.00 | 27.84 |
| 20991 | C | HIS | D | 357 | -130.501 | 1.658 | 44.520 | 1.00 | 31.96 |
| 20992 | O | HIS | D | 357 | -130.075 | 2.603 | 43.875 | 1.00 | 31.35 |
| 20993 | N | ILE | D | 358 | -131.623 | 1.017 | 44.224 | 1.00 | 33.06 |
| 20994 | CA | ILE | D | 358 | -132.426 | 1.430 | 43.096 | 1.00 | 34.50 |
| 20995 | CB | ILE | D | 358 | -133.421 | 0.356 | 42.695 | 1.00 | 34.42 |
| 20996 | CG1 | ILE | D | 358 | -132.706 | -0.982 | 42.472 | 1.00 | 34.74 |
| 20997 | CD1 | ILE | D | 358 | -133.628 | -2.206 | 42.569 | 1.00 | 34.80 |
| 20998 | CG2 | ILE | D | 358 | -134.182 | 0.824 | 41.448 | 1.00 | 33.43 |
| 20999 | C | ILE | D | 358 | -133.176 | 2.708 | 43.417 | 1.00 | 35.42 |
| 21000 | O | ILE | D | 358 | -133.907 | 2.791 | 44.408 | 1.00 | 34.47 |
| 21001 | N | CYS | D | 359 | -132.985 | 3.707 | 42.569 | 1.00 | 36.85 |
| 21002 | CA | CYS | D | 359 | -133.674 | 4.960 | 42.762 | 1.00 | 38.92 |

FIGURE 3 OV

| A | B | C | D | E | F | G | H | I | J |
|---|---|---|---|---|---|---|---|---|---|
| 21003 | CB | CYS | D | 359 | -132.691 | 6.097 | 43.006 | 1.00 | 39.01 |
| 21004 | SG | CYS | D | 359 | -133.467 | 7.398 | 43.960 | 1.00 | 43.67 |
| 21005 | C | CYS | D | 359 | -134.542 | 5.238 | 41.548 | 1.00 | 39.33 |
| 21006 | O | CYS | D | 359 | -134.168 | 4.922 | 40.421 | 1.00 | 39.71 |
| 21007 | N | TYR | D | 360 | -135.709 | 5.818 | 41.787 | 1.00 | 40.18 |
| 21008 | CA | TYR | D | 360 | -136.653 | 6.101 | 40.725 | 1.00 | 41.13 |
| 21009 | CB | TYR | D | 360 | -138.042 | 5.660 | 41.159 | 1.00 | 41.22 |
| 21010 | CG | TYR | D | 360 | -139.166 | 6.012 | 40.211 | 1.00 | 40.71 |
| 21011 | CD1 | TYR | D | 360 | -140.043 | 7.046 | 40.504 | 1.00 | 41.69 |
| 21012 | CE1 | TYR | D | 360 | -141.079 | 7.362 | 39.658 | 1.00 | 41.04 |
| 21013 | CZ | TYR | D | 360 | -141.259 | 6.625 | 38.509 | 1.00 | 41.55 |
| 21014 | OH | TYR | D | 360 | -142.305 | 6.928 | 37.670 | 1.00 | 43.38 |
| 21015 | CE2 | TYR | D | 360 | -140.409 | 5.590 | 38.197 | 1.00 | 40.33 |
| 21016 | CD2 | TYR | D | 360 | -139.372 | 5.288 | 39.048 | 1.00 | 40.26 |
| 21017 | C | TYR | D | 360 | -136.644 | 7.585 | 40.394 | 1.00 | 41.84 |
| 21018 | O | TYR | D | 360 | -136.754 | 8.425 | 41.275 | 1.00 | 41.85 |
| 21019 | N | PHE | D | 361 | -136.485 | 7.897 | 39.116 | 1.00 | 42.94 |
| 21020 | CA | PHE | D | 361 | -136.450 | 9.275 | 38.665 | 1.00 | 43.88 |
| 21021 | CB | PHE | D | 361 | -135.155 | 9.578 | 37.894 | 1.00 | 43.94 |
| 21022 | CG | PHE | D | 361 | -133.895 | 9.448 | 38.703 | 1.00 | 43.65 |
| 21023 | CD1 | PHE | D | 361 | -133.156 | 10.578 | 39.038 | 1.00 | 43.59 |
| 21024 | CE1 | PHE | D | 361 | -131.985 | 10.466 | 39.784 | 1.00 | 43.67 |
| 21025 | CZ | PHE | D | 361 | -131.534 | 9.222 | 40.177 | 1.00 | 42.46 |
| 21026 | CE2 | PHE | D | 361 | -132.258 | 8.088 | 39.839 | 1.00 | 43.24 |
| 21027 | CD2 | PHE | D | 361 | -133.429 | 8.204 | 39.101 | 1.00 | 42.70 |
| 21028 | C | PHE | D | 361 | -137.572 | 9.475 | 37.679 | 1.00 | 44.95 |
| 21029 | O | PHE | D | 361 | -137.972 | 8.539 | 36.977 | 1.00 | 44.82 |
| 21030 | N | GLN | D | 362 | -138.062 | 10.708 | 37.620 | 1.00 | 46.06 |
| 21031 | CA | GLN | D | 362 | -139.001 | 11.116 | 36.594 | 1.00 | 47.40 |
| 21032 | CB | GLN | D | 362 | -140.239 | 11.791 | 37.189 | 1.00 | 47.36 |
| 21033 | CG | GLN | D | 362 | -141.040 | 10.943 | 38.162 | 1.00 | 48.74 |
| 21034 | CD | GLN | D | 362 | -142.243 | 11.700 | 38.711 | 1.00 | 51.25 |
| 21035 | OE1 | GLN | D | 362 | -143.331 | 11.614 | 38.153 | 1.00 | 53.12 |
| 21036 | NE2 | GLN | D | 362 | -142.042 | 12.461 | 39.783 | 1.00 | 51.45 |
| 21037 | C | GLN | D | 362 | -138.242 | 12.105 | 35.715 | 1.00 | 48.00 |
| 21038 | O | GLN | D | 362 | -137.580 | 13.015 | 36.215 | 1.00 | 47.59 |
| 21039 | N | ILE | D | 363 | -138.328 | 11.903 | 34.408 | 1.00 | 49.43 |
| 21040 | CA | ILE | D | 363 | -137.646 | 12.751 | 33.437 | 1.00 | 50.89 |
| 21041 | CB | ILE | D | 363 | -138.367 | 12.644 | 32.077 | 1.00 | 50.91 |
| 21042 | CG1 | ILE | D | 363 | -138.066 | 11.290 | 31.444 | 1.00 | 51.01 |
| 21043 | CD1 | ILE | D | 363 | -136.852 | 10.613 | 32.006 | 1.00 | 49.39 |
| 21044 | CG2 | ILE | D | 363 | -137.957 | 13.739 | 31.136 | 1.00 | 51.62 |
| 21045 | C | ILE | D | 363 | -137.547 | 14.203 | 33.890 | 1.00 | 51.81 |
| 21046 | O | ILE | D | 363 | -136.458 | 14.781 | 33.911 | 1.00 | 51.94 |
| 21047 | N | ASP | D | 364 | -138.676 | 14.776 | 34.295 | 1.00 | 53.26 |
| 21048 | CA | ASP | D | 364 | -138.744 | 16.195 | 34.652 | 1.00 | 54.63 |
| 21049 | CB | ASP | D | 364 | -140.059 | 16.794 | 34.133 | 1.00 | 55.08 |
| 21050 | CG | ASP | D | 364 | -139.984 | 17.194 | 32.661 | 1.00 | 57.13 |
| 21051 | OD1 | ASP | D | 364 | -139.101 | 18.014 | 32.315 | 1.00 | 58.88 |
| 21052 | OD2 | ASP | D | 364 | -140.764 | 16.755 | 31.780 | 1.00 | 57.86 |
| 21053 | C | ASP | D | 364 | -138.566 | 16.573 | 36.132 | 1.00 | 55.15 |

FIGURE 3 OW

| A | B | C | D | E | F | G | H | I | J |
|---|---|---|---|---|---|---|---|---|---|
| 21054 | O | ASP | D | 364 | -138.963 | 17.669 | 36.535 | 1.00 | 55.15 |
| 21055 | N | LYS | D | 365 | -137.984 | 15.697 | 36.948 | 1.00 | 55.72 |
| 21056 | CA | LYS | D | 365 | -137.769 | 16.058 | 38.353 | 1.00 | 56.38 |
| 21057 | CB | LYS | D | 365 | -138.896 | 15.533 | 39.259 | 1.00 | 56.83 |
| 21058 | CG | LYS | D | 365 | -138.517 | 14.404 | 40.224 | 1.00 | 58.36 |
| 21059 | CD | LYS | D | 365 | -139.686 | 14.082 | 41.174 | 1.00 | 60.14 |
| 21060 | CE | LYS | D | 365 | -139.278 | 13.174 | 42.340 | 1.00 | 60.85 |
| 21061 | NZ | LYS | D | 365 | -138.816 | 11.802 | 41.920 | 1.00 | 60.80 |
| 21062 | C | LYS | D | 365 | -136.390 | 15.655 | 38.866 | 1.00 | 56.32 |
| 21063 | O | LYS | D | 365 | -135.920 | 14.538 | 38.636 | 1.00 | 56.59 |
| 21064 | N | LYS | D | 366 | -135.741 | 16.576 | 39.562 | 1.00 | 56.14 |
| 21065 | CA | LYS | D | 366 | -134.393 | 16.336 | 40.054 | 1.00 | 55.94 |
| 21066 | CB | LYS | D | 366 | -133.793 | 17.628 | 40.616 | 1.00 | 56.24 |
| 21067 | CG | LYS | D | 366 | -134.448 | 18.115 | 41.896 | 1.00 | 57.54 |
| 21068 | CD | LYS | D | 366 | -133.819 | 19.422 | 42.372 | 1.00 | 59.43 |
| 21069 | CE | LYS | D | 366 | -134.168 | 19.709 | 43.827 | 1.00 | 60.48 |
| 21070 | NZ | LYS | D | 366 | -135.641 | 19.679 | 44.075 | 1.00 | 60.65 |
| 21071 | C | LYS | D | 366 | -134.320 | 15.228 | 41.103 | 1.00 | 55.23 |
| 21072 | O | LYS | D | 366 | -133.440 | 14.363 | 41.050 | 1.00 | 55.28 |
| 21073 | N | ASP | D | 367 | -135.246 | 15.241 | 42.051 | 1.00 | 54.04 |
| 21074 | CA | ASP | D | 367 | -135.168 | 14.285 | 43.143 | 1.00 | 52.89 |
| 21075 | CB | ASP | D | 367 | -135.850 | 14.821 | 44.396 | 1.00 | 53.20 |
| 21076 | CG | ASP | D | 367 | -134.996 | 15.825 | 45.113 | 1.00 | 55.19 |
| 21077 | OD1 | ASP | D | 367 | -135.382 | 17.009 | 45.151 | 1.00 | 58.14 |
| 21078 | OD2 | ASP | D | 367 | -133.909 | 15.526 | 45.658 | 1.00 | 58.60 |
| 21079 | C | ASP | D | 367 | -135.706 | 12.930 | 42.762 | 1.00 | 51.23 |
| 21080 | O | ASP | D | 367 | -136.645 | 12.824 | 41.994 | 1.00 | 51.45 |
| 21081 | N | CYS | D | 368 | -135.092 | 11.892 | 43.307 | 1.00 | 49.15 |
| 21082 | CA | CYS | D | 368 | -135.492 | 10.543 | 42.984 | 1.00 | 47.27 |
| 21083 | CB | CYS | D | 368 | -134.342 | 9.810 | 42.294 | 1.00 | 46.98 |
| 21084 | SG | CYS | D | 368 | -133.021 | 9.288 | 43.413 | 1.00 | 45.43 |
| 21085 | C | CYS | D | 368 | -135.843 | 9.847 | 44.277 | 1.00 | 46.24 |
| 21086 | O | CYS | D | 368 | -135.321 | 10.190 | 45.330 | 1.00 | 46.58 |
| 21087 | N | THR | D | 369 | -136.728 | 8.870 | 44.223 | 1.00 | 44.70 |
| 21088 | CA | THR | D | 369 | -137.032 | 8.175 | 45.449 | 1.00 | 43.62 |
| 21089 | CB | THR | D | 369 | -138.550 | 8.155 | 45.725 | 1.00 | 43.82 |
| 21090 | OG1 | THR | D | 369 | -139.124 | 6.964 | 45.188 | 1.00 | 44.95 |
| 21091 | CG2 | THR | D | 369 | -139.239 | 9.272 | 44.967 | 1.00 | 43.26 |
| 21092 | C | THR | D | 369 | -136.434 | 6.778 | 45.429 | 1.00 | 42.15 |
| 21093 | O | THR | D | 369 | -136.496 | 6.065 | 44.427 | 1.00 | 41.55 |
| 21094 | N | PHE | D | 370 | -135.820 | 6.406 | 46.539 | 1.00 | 40.33 |
| 21095 | CA | PHE | D | 370 | -135.249 | 5.084 | 46.648 | 1.00 | 39.06 |
| 21096 | CB | PHE | D | 370 | -134.193 | 5.065 | 47.736 | 1.00 | 39.01 |
| 21097 | CG | PHE | D | 370 | -132.869 | 5.591 | 47.284 | 1.00 | 38.24 |
| 21098 | CD1 | PHE | D | 370 | -132.082 | 4.851 | 46.425 | 1.00 | 36.86 |
| 21099 | CE1 | PHE | D | 370 | -130.850 | 5.339 | 46.006 | 1.00 | 38.06 |
| 21100 | CZ | PHE | D | 370 | -130.416 | 6.581 | 46.447 | 1.00 | 38.00 |
| 21101 | CE2 | PHE | D | 370 | -131.208 | 7.329 | 47.288 | 1.00 | 37.11 |
| 21102 | CD2 | PHE | D | 370 | -132.423 | 6.833 | 47.705 | 1.00 | 36.95 |
| 21103 | C | PHE | D | 370 | -136.321 | 4.045 | 46.931 | 1.00 | 38.31 |
| 21104 | O | PHE | D | 370 | -137.207 | 4.276 | 47.764 | 1.00 | 38.16 |

FIGURE 3 OX

| A | B | C | D | E | F | G | H | I | J |
|---|---|---|---|---|---|---|---|---|---|
| 21105 | N | ILE | D | 371 | -136.240 | 2.917 | 46.230 | 1.00 | 37.20 |
| 21106 | CA | ILE | D | 371 | -137.180 | 1.816 | 46.422 | 1.00 | 36.77 |
| 21107 | CB | ILE | D | 371 | -137.987 | 1.519 | 45.138 | 1.00 | 37.01 |
| 21108 | CG1 | ILE | D | 371 | -137.074 | 1.012 | 44.018 | 1.00 | 35.43 |
| 21109 | CD1 | ILE | D | 371 | -137.820 | 0.462 | 42.837 | 1.00 | 36.70 |
| 21110 | CG2 | ILE | D | 371 | -138.800 | 2.760 | 44.735 | 1.00 | 36.00 |
| 21111 | C | ILE | D | 371 | -136.523 | 0.547 | 46.981 | 1.00 | 36.79 |
| 21112 | O | ILE | D | 371 | -137.205 | -0.458 | 47.188 | 1.00 | 36.99 |
| 21113 | N | THR | D | 372 | -135.201 | 0.598 | 47.178 | 1.00 | 36.34 |
| 21114 | CA | THR | D | 372 | -134.463 | -0.395 | 47.972 | 1.00 | 36.04 |
| 21115 | CB | THR | D | 372 | -133.588 | -1.382 | 47.132 | 1.00 | 36.42 |
| 21116 | OG1 | THR | D | 372 | -132.577 | -0.668 | 46.400 | 1.00 | 35.44 |
| 21117 | CG2 | THR | D | 372 | -134.422 | -2.105 | 46.067 | 1.00 | 35.39 |
| 21118 | C | THR | D | 372 | -133.574 | 0.376 | 48.943 | 1.00 | 35.99 |
| 21119 | O | THR | D | 372 | -133.235 | 1.539 | 48.698 | 1.00 | 36.01 |
| 21120 | N | LYS | D | 373 | -133.232 | -0.251 | 50.062 | 1.00 | 35.71 |
| 21121 | CA | LYS | D | 373 | -132.320 | 0.342 | 51.037 | 1.00 | 35.84 |
| 21122 | CB | LYS | D | 373 | -132.988 | 1.458 | 51.828 | 1.00 | 36.44 |
| 21123 | CG | LYS | D | 373 | -134.476 | 1.226 | 52.094 | 1.00 | 38.82 |
| 21124 | CD | LYS | D | 373 | -134.836 | 1.498 | 53.548 | 1.00 | 41.22 |
| 21125 | CE | LYS | D | 373 | -134.428 | 2.895 | 53.983 | 1.00 | 43.73 |
| 21126 | NZ | LYS | D | 373 | -134.720 | 3.181 | 55.429 | 1.00 | 45.05 |
| 21127 | C | LYS | D | 373 | -131.843 | -0.723 | 51.984 | 1.00 | 35.25 |
| 21128 | O | LYS | D | 373 | -132.353 | -1.838 | 51.978 | 1.00 | 35.89 |
| 21129 | N | GLY | D | 374 | -130.876 | -0.374 | 52.819 | 1.00 | 34.90 |
| 21130 | CA | GLY | D | 374 | -130.309 | -1.310 | 53.769 | 1.00 | 33.91 |
| 21131 | C | GLY | D | 374 | -128.803 | -1.356 | 53.581 | 1.00 | 33.63 |
| 21132 | O | GLY | D | 374 | -128.269 | -0.778 | 52.634 | 1.00 | 33.52 |
| 21133 | N | THR | D | 375 | -128.109 | -2.039 | 54.480 | 1.00 | 33.26 |
| 21134 | CA | THR | D | 375 | -126.653 | -2.159 | 54.384 | 1.00 | 32.63 |
| 21135 | CB | THR | D | 375 | -126.040 | -2.305 | 55.781 | 1.00 | 32.98 |
| 21136 | OG1 | THR | D | 375 | -126.429 | -3.572 | 56.321 | 1.00 | 34.19 |
| 21137 | CG2 | THR | D | 375 | -126.673 | -1.306 | 56.754 | 1.00 | 32.80 |
| 21138 | C | THR | D | 375 | -126.245 | -3.349 | 53.518 | 1.00 | 31.50 |
| 21139 | O | THR | D | 375 | -125.699 | -4.329 | 54.010 | 1.00 | 31.37 |
| 21140 | N | TRP | D | 376 | -126.510 | -3.236 | 52.225 | 1.00 | 30.27 |
| 21141 | CA | TRP | D | 376 | -126.162 | -4.251 | 51.237 | 1.00 | 29.82 |
| 21142 | CB | TRP | D | 376 | -127.086 | -5.479 | 51.284 | 1.00 | 29.57 |
| 21143 | CG | TRP | D | 376 | -128.550 | -5.157 | 51.340 | 1.00 | 29.97 |
| 21144 | CD1 | TRP | D | 376 | -129.298 | -4.950 | 52.460 | 1.00 | 31.52 |
| 21145 | NE1 | TRP | D | 376 | -130.600 | -4.668 | 52.117 | 1.00 | 33.29 |
| 21146 | CE2 | TRP | D | 376 | -130.715 | -4.688 | 50.753 | 1.00 | 31.81 |
| 21147 | CD2 | TRP | D | 376 | -129.441 | -4.988 | 50.229 | 1.00 | 31.04 |
| 21148 | CE3 | TRP | D | 376 | -129.295 | -5.079 | 48.836 | 1.00 | 30.24 |
| 21149 | CZ3 | TRP | D | 376 | -130.386 | -4.847 | 48.034 | 1.00 | 30.33 |
| 21150 | CH2 | TRP | D | 376 | -131.652 | -4.560 | 48.586 | 1.00 | 31.76 |
| 21151 | CZ2 | TRP | D | 376 | -131.833 | -4.473 | 49.938 | 1.00 | 32.25 |
| 21152 | C | TRP | D | 376 | -126.329 | -3.507 | 49.933 | 1.00 | 29.40 |
| 21153 | O | TRP | D | 376 | -126.797 | -2.374 | 49.941 | 1.00 | 28.79 |
| 21154 | N | GLU | D | 377 | -125.952 | -4.118 | 48.816 | 1.00 | 29.03 |
| 21155 | CA | GLU | D | 377 | -126.019 | -3.384 | 47.549 | 1.00 | 28.80 |

FIGURE 3 OY

| A | B | C | D | E | F | G | H | I | J |
|---|---|---|---|---|---|---|---|---|---|
| 21156 | CB | GLU | D | 377 | -124.599 | -2.991 | 47.099 | 1.00 | 28.09 |
| 21157 | CG | GLU | D | 377 | -123.911 | -2.015 | 48.046 | 1.00 | 27.76 |
| 21158 | CD | GLU | D | 377 | -122.815 | -1.214 | 47.377 | 1.00 | 28.36 |
| 21159 | OE1 | GLU | D | 377 | -122.572 | -0.067 | 47.780 | 1.00 | 29.76 |
| 21160 | OE2 | GLU | D | 377 | -122.193 | -1.719 | 46.434 | 1.00 | 30.38 |
| 21161 | C | GLU | D | 377 | -126.736 | -4.089 | 46.404 | 1.00 | 28.45 |
| 21162 | O | GLU | D | 377 | -126.595 | -5.289 | 46.214 | 1.00 | 28.24 |
| 21163 | N | VAL | D | 378 | -127.495 | -3.331 | 45.626 | 1.00 | 29.21 |
| 21164 | CA | VAL | D | 378 | -128.045 | -3.871 | 44.395 | 1.00 | 29.24 |
| 21165 | CB | VAL | D | 378 | -129.146 | -2.978 | 43.833 | 1.00 | 29.41 |
| 21166 | CG1 | VAL | D | 378 | -129.580 | -3.458 | 42.426 | 1.00 | 28.44 |
| 21167 | CG2 | VAL | D | 378 | -130.343 | -2.924 | 44.807 | 1.00 | 28.31 |
| 21168 | C | VAL | D | 378 | -126.878 | -3.964 | 43.422 | 1.00 | 30.44 |
| 21169 | O | VAL | D | 378 | -126.092 | -3.033 | 43.294 | 1.00 | 29.80 |
| 21170 | N | ILE | D | 379 | -126.746 | -5.100 | 42.750 | 1.00 | 32.28 |
| 21171 | CA | ILE | D | 379 | -125.628 | -5.307 | 41.840 | 1.00 | 33.52 |
| 21172 | CB | ILE | D | 379 | -125.220 | -6.788 | 41.831 | 1.00 | 33.68 |
| 21173 | CG1 | ILE | D | 379 | -124.879 | -7.260 | 43.244 | 1.00 | 33.80 |
| 21174 | CD1 | ILE | D | 379 | -123.922 | -6.369 | 43.973 | 1.00 | 33.48 |
| 21175 | CG2 | ILE | D | 379 | -124.049 | -7.015 | 40.887 | 1.00 | 34.15 |
| 21176 | C | ILE | D | 379 | -126.015 | -4.856 | 40.445 | 1.00 | 34.25 |
| 21177 | O | ILE | D | 379 | -125.215 | -4.251 | 39.725 | 1.00 | 34.43 |
| 21178 | N | GLY | D | 380 | -127.248 | -5.155 | 40.062 | 1.00 | 34.97 |
| 21179 | CA | GLY | D | 380 | -127.748 | -4.709 | 38.778 | 1.00 | 36.19 |
| 21180 | C | GLY | D | 380 | -129.244 | -4.880 | 38.609 | 1.00 | 36.82 |
| 21181 | O | GLY | D | 380 | -129.809 | -5.825 | 39.117 | 1.00 | 37.70 |
| 21182 | N | ILE | D | 381 | -129.890 | -3.944 | 37.921 | 1.00 | 37.55 |
| 21183 | CA | ILE | D | 381 | -131.277 | -4.109 | 37.545 | 1.00 | 37.88 |
| 21184 | CB | ILE | D | 381 | -131.877 | -2.772 | 37.160 | 1.00 | 38.08 |
| 21185 | CG1 | ILE | D | 381 | -132.109 | -1.923 | 38.413 | 1.00 | 38.21 |
| 21186 | CD1 | ILE | D | 381 | -132.224 | -0.427 | 38.137 | 1.00 | 37.59 |
| 21187 | CG2 | ILE | D | 381 | -133.182 | -2.981 | 36.381 | 1.00 | 36.96 |
| 21188 | C | ILE | D | 381 | -131.256 | -5.024 | 36.330 | 1.00 | 38.84 |
| 21189 | O | ILE | D | 381 | -130.627 | -4.711 | 35.317 | 1.00 | 38.87 |
| 21190 | N | GLU | D | 382 | -131.941 | -6.155 | 36.427 | 1.00 | 39.49 |
| 21191 | CA | GLU | D | 382 | -131.914 | -7.145 | 35.365 | 1.00 | 40.28 |
| 21192 | CB | GLU | D | 382 | -131.826 | -8.554 | 35.971 | 1.00 | 40.16 |
| 21193 | CG | GLU | D | 382 | -130.637 | -8.763 | 36.888 | 1.00 | 40.99 |
| 21194 | CD | GLU | D | 382 | -129.303 | -8.422 | 36.241 | 1.00 | 42.81 |
| 21195 | OE1 | GLU | D | 382 | -129.076 | -8.797 | 35.068 | 1.00 | 43.56 |
| 21196 | OE2 | GLU | D | 382 | -128.479 | -7.764 | 36.908 | 1.00 | 43.93 |
| 21197 | C | GLU | D | 382 | -133.100 | -7.061 | 34.407 | 1.00 | 40.86 |
| 21198 | O | GLU | D | 382 | -132.973 | -7.374 | 33.225 | 1.00 | 41.14 |
| 21199 | N | ALA | D | 383 | -134.259 | -6.657 | 34.913 | 1.00 | 41.59 |
| 21200 | CA | ALA | D | 383 | -135.447 | -6.544 | 34.064 | 1.00 | 41.83 |
| 21201 | CB | ALA | D | 383 | -136.094 | -7.913 | 33.851 | 1.00 | 41.83 |
| 21202 | C | ALA | D | 383 | -136.479 | -5.576 | 34.615 | 1.00 | 42.32 |
| 21203 | O | ALA | D | 383 | -136.538 | -5.296 | 35.825 | 1.00 | 41.93 |
| 21204 | N | LEU | D | 384 | -137.313 | -5.095 | 33.703 | 1.00 | 42.65 |
| 21205 | CA | LEU | D | 384 | -138.372 | -4.178 | 34.032 | 1.00 | 43.03 |
| 21206 | CB | LEU | D | 384 | -137.961 | -2.777 | 33.617 | 1.00 | 42.90 |

FIGURE 3 OZ

| A | B | C | D | E | F | G | H | I | J |
|---|---|---|---|---|---|---|---|---|---|
| 21207 | CG | LEU | D | 384 | -138.924 | -1.652 | 33.979 | 1.00 | 42.15 |
| 21208 | CD1 | LEU | D | 384 | -139.173 | -1.634 | 35.484 | 1.00 | 41.21 |
| 21209 | CD2 | LEU | D | 384 | -138.338 | -0.343 | 33.531 | 1.00 | 41.42 |
| 21210 | C | LEU | D | 384 | -139.614 | -4.564 | 33.262 | 1.00 | 43.77 |
| 21211 | O | LEU | D | 384 | -139.553 | -4.837 | 32.076 | 1.00 | 44.19 |
| 21212 | N | THR | D | 385 | -140.747 | -4.621 | 33.939 | 1.00 | 44.51 |
| 21213 | CA | THR | D | 385 | -142.009 | -4.822 | 33.251 | 1.00 | 44.99 |
| 21214 | CB | THR | D | 385 | -142.612 | -6.190 | 33.558 | 1.00 | 45.20 |
| 21215 | OG1 | THR | D | 385 | -142.895 | -6.281 | 34.960 | 1.00 | 45.54 |
| 21216 | CG2 | THR | D | 385 | -141.596 | -7.305 | 33.304 | 1.00 | 44.70 |
| 21217 | C | THR | D | 385 | -142.891 | -3.722 | 33.785 | 1.00 | 45.45 |
| 21218 | O | THR | D | 385 | -142.424 | -2.877 | 34.542 | 1.00 | 45.63 |
| 21219 | N | SER | D | 386 | -144.161 | -3.699 | 33.401 | 1.00 | 46.00 |
| 21220 | CA | SER | D | 386 | -145.027 | -2.641 | 33.912 | 1.00 | 46.09 |
| 21221 | CB | SER | D | 386 | -146.253 | -2.430 | 33.010 | 1.00 | 46.35 |
| 21222 | OG | SER | D | 386 | -146.907 | -3.659 | 32.748 | 1.00 | 47.43 |
| 21223 | C | SER | D | 386 | -145.439 | -2.985 | 35.338 | 1.00 | 45.73 |
| 21224 | O | SER | D | 386 | -145.896 | -2.118 | 36.083 | 1.00 | 45.55 |
| 21225 | N | ASP | D | 387 | -145.253 | -4.251 | 35.710 | 1.00 | 45.25 |
| 21226 | CA | ASP | D | 387 | -145.595 | -4.715 | 37.046 | 1.00 | 45.10 |
| 21227 | CB | ASP | D | 387 | -146.446 | -5.976 | 36.958 | 1.00 | 45.39 |
| 21228 | CG | ASP | D | 387 | -147.721 | -5.776 | 36.151 | 1.00 | 45.79 |
| 21229 | OD1 | ASP | D | 387 | -148.334 | -4.682 | 36.233 | 1.00 | 44.47 |
| 21230 | OD2 | ASP | D | 387 | -148.181 | -6.676 | 35.410 | 1.00 | 45.75 |
| 21231 | C | ASP | D | 387 | -144.397 | -5.010 | 37.960 | 1.00 | 45.22 |
| 21232 | O | ASP | D | 387 | -144.522 | -4.927 | 39.187 | 1.00 | 45.43 |
| 21233 | N | TYR | D | 388 | -143.242 | -5.345 | 37.380 | 1.00 | 44.50 |
| 21234 | CA | TYR | D | 388 | -142.109 | -5.781 | 38.187 | 1.00 | 43.85 |
| 21235 | CB | TYR | D | 388 | -142.089 | -7.300 | 38.221 | 1.00 | 44.23 |
| 21236 | CG | TYR | D | 388 | -143.153 | -7.910 | 39.090 | 1.00 | 46.90 |
| 21237 | CD1 | TYR | D | 388 | -144.206 | -8.626 | 38.533 | 1.00 | 48.02 |
| 21238 | CE1 | TYR | D | 388 | -145.177 | -9.190 | 39.331 | 1.00 | 49.82 |
| 21239 | CZ | TYR | D | 388 | -145.108 | -9.039 | 40.702 | 1.00 | 51.59 |
| 21240 | OH | TYR | D | 388 | -146.076 | -9.596 | 41.510 | 1.00 | 53.43 |
| 21241 | CE2 | TYR | D | 388 | -144.068 | -8.339 | 41.279 | 1.00 | 50.92 |
| 21242 | CD2 | TYR | D | 388 | -143.099 | -7.779 | 40.473 | 1.00 | 49.24 |
| 21243 | C | TYR | D | 388 | -140.715 | -5.330 | 37.760 | 1.00 | 42.89 |
| 21244 | O | TYR | D | 388 | -140.366 | -5.372 | 36.580 | 1.00 | 43.06 |
| 21245 | N | LEU | D | 389 | -139.916 | -4.942 | 38.753 | 1.00 | 41.19 |
| 21246 | CA | LEU | D | 389 | -138.507 | -4.614 | 38.567 | 1.00 | 39.23 |
| 21247 | CB | LEU | D | 389 | -138.156 | -3.339 | 39.334 | 1.00 | 39.32 |
| 21248 | CG | LEU | D | 389 | -136.716 | -2.789 | 39.446 | 1.00 | 39.19 |
| 21249 | CD1 | LEU | D | 389 | -135.648 | -3.859 | 39.256 | 1.00 | 38.76 |
| 21250 | CD2 | LEU | D | 389 | -136.476 | -1.627 | 38.500 | 1.00 | 36.57 |
| 21251 | C | LEU | D | 389 | -137.727 | -5.792 | 39.132 | 1.00 | 37.99 |
| 21252 | O | LEU | D | 389 | -137.870 | -6.117 | 40.310 | 1.00 | 37.64 |
| 21253 | N | TYR | D | 390 | -136.944 | -6.454 | 38.284 | 1.00 | 36.44 |
| 21254 | CA | TYR | D | 390 | -136.096 | -7.572 | 38.702 | 1.00 | 35.27 |
| 21255 | CB | TYR | D | 390 | -136.120 | -8.667 | 37.640 | 1.00 | 35.32 |
| 21256 | CG | TYR | D | 390 | -137.462 | -9.355 | 37.489 | 1.00 | 35.78 |
| 21257 | CD1 | TYR | D | 390 | -137.705 | -10.594 | 38.077 | 1.00 | 35.03 |

FIGURE 3 PA

| A | B | C | D | E | F | G | H | I | J |
|---|---|---|---|---|---|---|---|---|---|
| 21258 | CE1 | TYR | D | 390 | -138.926 | -11.219 | 37.931 | 1.00 | 35.62 |
| 21259 | CZ | TYR | D | 390 | -139.923 | -10.606 | 37.194 | 1.00 | 36.94 |
| 21260 | OH | TYR | D | 390 | -141.154 | -11.213 | 37.040 | 1.00 | 38.72 |
| 21261 | CE2 | TYR | D | 390 | -139.700 | -9.386 | 36.600 | 1.00 | 36.15 |
| 21262 | CD2 | TYR | D | 390 | -138.479 | -8.768 | 36.752 | 1.00 | 34.64 |
| 21263 | C | TYR | D | 390 | -134.640 | -7.111 | 38.932 | 1.00 | 34.37 |
| 21264 | O | TYR | D | 390 | -134.089 | -6.366 | 38.121 | 1.00 | 33.74 |
| 21265 | N | TYR | D | 391 | -134.021 | -7.532 | 40.032 | 1.00 | 33.78 |
| 21266 | CA | TYR | D | 391 | -132.633 | -7.111 | 40.295 | 1.00 | 33.57 |
| 21267 | CB | TYR | D | 391 | -132.588 | -5.786 | 41.050 | 1.00 | 32.67 |
| 21268 | CG | TYR | D | 391 | -133.038 | -5.874 | 42.493 | 1.00 | 33.02 |
| 21269 | CD1 | TYR | D | 391 | -132.119 | -6.026 | 43.522 | 1.00 | 31.65 |
| 21270 | CE1 | TYR | D | 391 | -132.527 | -6.097 | 44.841 | 1.00 | 32.39 |
| 21271 | CZ | TYR | D | 391 | -133.875 | -6.002 | 45.149 | 1.00 | 31.55 |
| 21272 | OH | TYR | D | 391 | -134.297 | -6.080 | 46.457 | 1.00 | 29.40 |
| 21273 | CE2 | TYR | D | 391 | -134.806 | -5.850 | 44.144 | 1.00 | 31.36 |
| 21274 | CD2 | TYR | D | 391 | -134.389 | -5.783 | 42.829 | 1.00 | 33.04 |
| 21275 | C | TYR | D | 391 | -131.789 | -8.142 | 41.027 | 1.00 | 33.49 |
| 21276 | O | TYR | D | 391 | -132.321 | -9.035 | 41.686 | 1.00 | 33.47 |
| 21277 | N | ILE | D | 392 | -130.472 | -8.009 | 40.879 | 1.00 | 33.22 |
| 21278 | CA | ILE | D | 392 | -129.503 | -8.860 | 41.554 | 1.00 | 33.32 |
| 21279 | CB | ILE | D | 392 | -128.368 | -9.250 | 40.586 | 1.00 | 33.70 |
| 21280 | CG1 | ILE | D | 392 | -128.870 | -10.182 | 39.476 | 1.00 | 33.03 |
| 21281 | CD1 | ILE | D | 392 | -129.221 | -11.532 | 39.945 | 1.00 | 33.23 |
| 21282 | CG2 | ILE | D | 392 | -127.203 | -9.887 | 41.356 | 1.00 | 33.89 |
| 21283 | C | ILE | D | 392 | -128.886 | -8.067 | 42.698 | 1.00 | 33.31 |
| 21284 | O | ILE | D | 392 | -128.479 | -6.910 | 42.518 | 1.00 | 33.78 |
| 21285 | N | SER | D | 393 | -128.806 | -8.669 | 43.876 | 1.00 | 32.64 |
| 21286 | CA | SER | D | 393 | -128.183 | -7.981 | 45.004 | 1.00 | 32.76 |
| 21287 | CB | SER | D | 393 | -129.201 | -7.144 | 45.790 | 1.00 | 32.51 |
| 21288 | OG | SER | D | 393 | -129.875 | -7.933 | 46.759 | 1.00 | 33.92 |
| 21289 | C | SER | D | 393 | -127.472 | -8.960 | 45.915 | 1.00 | 32.29 |
| 21290 | O | SER | D | 393 | -127.584 | -10.171 | 45.738 | 1.00 | 31.99 |
| 21291 | N | ASN | D | 394 | -126.719 | -8.431 | 46.872 | 1.00 | 32.51 |
| 21292 | CA | ASN | D | 394 | -126.000 | -9.274 | 47.830 | 1.00 | 32.69 |
| 21293 | CB | ASN | D | 394 | -124.527 | -8.862 | 47.970 | 1.00 | 32.26 |
| 21294 | CG | ASN | D | 394 | -124.338 | -7.384 | 48.325 | 1.00 | 31.57 |
| 21295 | OD1 | ASN | D | 394 | -125.295 | -6.636 | 48.589 | 1.00 | 31.30 |
| 21296 | ND2 | ASN | D | 394 | -123.085 | -6.951 | 48.298 | 1.00 | 29.02 |
| 21297 | C | ASN | D | 394 | -126.683 | -9.279 | 49.189 | 1.00 | 33.36 |
| 21298 | O | ASN | D | 394 | -126.095 | -9.652 | 50.198 | 1.00 | 32.50 |
| 21299 | N | GLU | D | 395 | -127.944 | -8.867 | 49.199 | 1.00 | 34.75 |
| 21300 | CA | GLU | D | 395 | -128.707 | -8.829 | 50.436 | 1.00 | 36.34 |
| 21301 | CB | GLU | D | 395 | -130.149 | -8.415 | 50.169 | 1.00 | 36.30 |
| 21302 | CG | GLU | D | 395 | -130.976 | -8.423 | 51.443 | 1.00 | 36.61 |
| 21303 | CD | GLU | D | 395 | -132.358 | -7.840 | 51.268 | 1.00 | 37.91 |
| 21304 | OE1 | GLU | D | 395 | -132.893 | -7.322 | 52.260 | 1.00 | 39.02 |
| 21305 | OE2 | GLU | D | 395 | -132.913 | -7.897 | 50.148 | 1.00 | 39.24 |
| 21306 | C | GLU | D | 395 | -128.726 | -10.124 | 51.253 | 1.00 | 37.08 |
| 21307 | O | GLU | D | 395 | -128.535 | -10.103 | 52.471 | 1.00 | 37.83 |
| 21308 | N | TYR | D | 396 | -128.954 | -11.245 | 50.589 | 1.00 | 37.66 |

FIGURE 3 PB

| A | B | C | D | E | F | G | H | I | J |
|---|---|---|---|---|---|---|---|---|---|
| 21309 | CA  | TYR | D | 396 | -129.164 | -12.497 | 51.302 | 1.00 | 38.42 |
| 21310 | CB  | TYR | D | 396 | -129.319 | -13.671 | 50.332 | 1.00 | 39.08 |
| 21311 | CG  | TYR | D | 396 | -129.903 | -14.891 | 50.993 | 1.00 | 40.75 |
| 21312 | CD1 | TYR | D | 396 | -129.281 | -16.121 | 50.894 | 1.00 | 42.10 |
| 21313 | CE1 | TYR | D | 396 | -129.813 | -17.229 | 51.500 | 1.00 | 43.64 |
| 21314 | CZ  | TYR | D | 396 | -130.974 | -17.117 | 52.235 | 1.00 | 44.50 |
| 21315 | OH  | TYR | D | 396 | -131.491 | -18.226 | 52.849 | 1.00 | 45.67 |
| 21316 | CE2 | TYR | D | 396 | -131.611 | -15.909 | 52.359 | 1.00 | 43.32 |
| 21317 | CD2 | TYR | D | 396 | -131.070 | -14.801 | 51.739 | 1.00 | 42.76 |
| 21318 | C   | TYR | D | 396 | -128.115 | -12.822 | 52.335 | 1.00 | 38.41 |
| 21319 | O   | TYR | D | 396 | -126.949 | -13.019 | 52.001 | 1.00 | 39.06 |
| 21320 | N   | LYS | D | 397 | -128.554 | -12.879 | 53.594 | 1.00 | 38.17 |
| 21321 | CA  | LYS | D | 397 | -127.717 | -13.254 | 54.735 | 1.00 | 37.76 |
| 21322 | CB  | LYS | D | 397 | -127.140 | -14.660 | 54.554 | 1.00 | 38.02 |
| 21323 | CG  | LYS | D | 397 | -128.178 | -15.777 | 54.569 | 1.00 | 39.40 |
| 21324 | CD  | LYS | D | 397 | -127.545 | -17.152 | 54.746 | 1.00 | 41.15 |
| 21325 | CE  | LYS | D | 397 | -128.568 | -18.272 | 54.523 | 1.00 | 44.14 |
| 21326 | NZ  | LYS | D | 397 | -127.948 | -19.634 | 54.367 | 1.00 | 44.91 |
| 21327 | C   | LYS | D | 397 | -126.603 | -12.263 | 55.024 | 1.00 | 37.22 |
| 21328 | O   | LYS | D | 397 | -125.683 | -12.557 | 55.783 | 1.00 | 37.28 |
| 21329 | N   | GLY | D | 398 | -126.682 | -11.087 | 54.417 | 1.00 | 36.41 |
| 21330 | CA  | GLY | D | 398 | -125.646 | -10.092 | 54.606 | 1.00 | 35.51 |
| 21331 | C   | GLY | D | 398 | -124.273 | -10.549 | 54.137 | 1.00 | 34.64 |
| 21332 | O   | GLY | D | 398 | -123.281 | -10.208 | 54.746 | 1.00 | 34.99 |
| 21333 | N   | MET | D | 399 | -124.225 | -11.309 | 53.050 | 1.00 | 34.17 |
| 21334 | CA  | MET | D | 399 | -122.972 | -11.811 | 52.483 | 1.00 | 33.91 |
| 21335 | CB  | MET | D | 399 | -123.074 | -13.312 | 52.149 | 1.00 | 34.02 |
| 21336 | CG  | MET | D | 399 | -123.071 | -14.227 | 53.385 | 1.00 | 36.12 |
| 21337 | SD  | MET | D | 399 | -123.734 | -15.905 | 53.097 | 1.00 | 40.58 |
| 21338 | CE  | MET | D | 399 | -122.457 | -16.617 | 52.072 | 1.00 | 37.49 |
| 21339 | C   | MET | D | 399 | -122.693 | -11.029 | 51.223 | 1.00 | 33.24 |
| 21340 | O   | MET | D | 399 | -123.348 | -11.219 | 50.197 | 1.00 | 33.54 |
| 21341 | N   | PRO | D | 400 | -121.733 | -10.127 | 51.296 | 1.00 | 32.85 |
| 21342 | CA  | PRO | D | 400 | -121.428 |  -9.258 | 50.157 | 1.00 | 31.96 |
| 21343 | CB  | PRO | D | 400 | -120.303 |  -8.368 | 50.689 | 1.00 | 32.56 |
| 21344 | CG  | PRO | D | 400 | -120.388 |  -8.488 | 52.219 | 1.00 | 32.56 |
| 21345 | CD  | PRO | D | 400 | -120.877 |  -9.856 | 52.469 | 1.00 | 32.49 |
| 21346 | C   | PRO | D | 400 | -120.966 | -10.075 | 48.959 | 1.00 | 31.41 |
| 21347 | O   | PRO | D | 400 | -121.032 |  -9.603 | 47.806 | 1.00 | 31.06 |
| 21348 | N   | GLY | D | 401 | -120.535 | -11.304 | 49.232 | 1.00 | 30.39 |
| 21349 | CA  | GLY | D | 401 | -120.019 | -12.185 | 48.206 | 1.00 | 29.98 |
| 21350 | C   | GLY | D | 401 | -121.033 | -13.138 | 47.618 | 1.00 | 29.92 |
| 21351 | O   | GLY | D | 401 | -120.681 | -14.059 | 46.869 | 1.00 | 29.59 |
| 21352 | N   | GLY | D | 402 | -122.296 | -12.925 | 47.965 | 1.00 | 30.03 |
| 21353 | CA  | GLY | D | 402 | -123.380 | -13.709 | 47.412 | 1.00 | 30.76 |
| 21354 | C   | GLY | D | 402 | -124.202 | -12.877 | 46.444 | 1.00 | 31.24 |
| 21355 | O   | GLY | D | 402 | -124.129 | -11.646 | 46.459 | 1.00 | 31.82 |
| 21356 | N   | ARG | D | 403 | -124.983 | -13.540 | 45.601 | 1.00 | 31.17 |
| 21357 | CA  | ARG | D | 403 | -125.805 | -12.856 | 44.605 | 1.00 | 31.79 |
| 21358 | CB  | ARG | D | 403 | -125.148 | -12.876 | 43.215 | 1.00 | 31.66 |
| 21359 | CG  | ARG | D | 403 | -123.788 | -12.221 | 43.092 | 1.00 | 33.33 |

FIGURE 3 PC

| A | B | C | D | E | F | G | H | I | J |
|---|---|---|---|---|---|---|---|---|---|
| 21360 | CD | ARG | D | 403 | -123.842 | -10.718 | 43.121 | 1.00 | 34.68 |
| 21361 | NE | ARG | D | 403 | -122.545 | -10.099 | 42.887 | 1.00 | 36.17 |
| 21362 | CZ | ARG | D | 403 | -121.648 | -9.857 | 43.845 | 1.00 | 37.00 |
| 21363 | NH1 | ARG | D | 403 | -120.497 | -9.260 | 43.545 | 1.00 | 35.90 |
| 21364 | NH2 | ARG | D | 403 | -121.900 | -10.215 | 45.103 | 1.00 | 35.24 |
| 21365 | C | ARG | D | 403 | -127.128 | -13.579 | 44.459 | 1.00 | 31.84 |
| 21366 | O | ARG | D | 403 | -127.160 | -14.784 | 44.254 | 1.00 | 31.02 |
| 21367 | N | ASN | D | 404 | -128.222 | -12.831 | 44.529 | 1.00 | 32.69 |
| 21368 | CA | ASN | D | 404 | -129.536 | -13.416 | 44.293 | 1.00 | 33.04 |
| 21369 | CB | ASN | D | 404 | -130.216 | -13.788 | 45.605 | 1.00 | 32.99 |
| 21370 | CG | ASN | D | 404 | -129.598 | -14.992 | 46.222 | 1.00 | 34.62 |
| 21371 | OD1 | ASN | D | 404 | -128.764 | -14.886 | 47.133 | 1.00 | 38.55 |
| 21372 | ND2 | ASN | D | 404 | -129.935 | -16.148 | 45.692 | 1.00 | 34.43 |
| 21373 | C | ASN | D | 404 | -130.398 | -12.492 | 43.494 | 1.00 | 33.01 |
| 21374 | O | ASN | D | 404 | -130.138 | -11.290 | 43.448 | 1.00 | 33.01 |
| 21375 | N | LEU | D | 405 | -131.420 | -13.069 | 42.863 | 1.00 | 32.93 |
| 21376 | CA | LEU | D | 405 | -132.376 | -12.328 | 42.045 | 1.00 | 32.18 |
| 21377 | CB | LEU | D | 405 | -132.739 | -13.130 | 40.792 | 1.00 | 32.03 |
| 21378 | CG | LEU | D | 405 | -133.891 | -12.620 | 39.926 | 1.00 | 31.61 |
| 21379 | CD1 | LEU | D | 405 | -133.548 | -11.250 | 39.356 | 1.00 | 29.59 |
| 21380 | CD2 | LEU | D | 405 | -134.244 | -13.622 | 38.801 | 1.00 | 30.33 |
| 21381 | C | LEU | D | 405 | -133.635 | -12.052 | 42.857 | 1.00 | 32.74 |
| 21382 | O | LEU | D | 405 | -134.217 | -12.949 | 43.495 | 1.00 | 31.85 |
| 21383 | N | TYR | D | 406 | -134.040 | -10.794 | 42.836 | 1.00 | 32.97 |
| 21384 | CA | TYR | D | 406 | -135.212 | -10.364 | 43.546 | 1.00 | 33.88 |
| 21385 | CB | TYR | D | 406 | -134.825 | -9.373 | 44.648 | 1.00 | 33.78 |
| 21386 | CG | TYR | D | 406 | -133.946 | -9.942 | 45.738 | 1.00 | 32.63 |
| 21387 | CD1 | TYR | D | 406 | -134.439 | -10.130 | 47.023 | 1.00 | 32.00 |
| 21388 | CE1 | TYR | D | 406 | -133.630 | -10.635 | 48.044 | 1.00 | 31.50 |
| 21389 | CZ | TYR | D | 406 | -132.316 | -10.963 | 47.770 | 1.00 | 30.89 |
| 21390 | OH | TYR | D | 406 | -131.510 | -11.476 | 48.773 | 1.00 | 32.49 |
| 21391 | CE2 | TYR | D | 406 | -131.804 | -10.779 | 46.501 | 1.00 | 30.49 |
| 21392 | CD2 | TYR | D | 406 | -132.614 | -10.266 | 45.493 | 1.00 | 31.07 |
| 21393 | C | TYR | D | 406 | -136.124 | -9.678 | 42.553 | 1.00 | 34.67 |
| 21394 | O | TYR | D | 406 | -135.686 | -9.284 | 41.481 | 1.00 | 35.49 |
| 21395 | N | LYS | D | 407 | -137.395 | -9.547 | 42.903 | 1.00 | 35.65 |
| 21396 | CA | LYS | D | 407 | -138.341 | -8.803 | 42.074 | 1.00 | 36.67 |
| 21397 | CB | LYS | D | 407 | -139.286 | -9.734 | 41.295 | 1.00 | 36.90 |
| 21398 | CG | LYS | D | 407 | -140.233 | -10.547 | 42.178 | 1.00 | 38.89 |
| 21399 | CD | LYS | D | 407 | -140.922 | -11.691 | 41.423 | 1.00 | 40.76 |
| 21400 | CE | LYS | D | 407 | -142.154 | -11.240 | 40.640 | 1.00 | 44.41 |
| 21401 | NZ | LYS | D | 407 | -143.256 | -12.282 | 40.629 | 1.00 | 43.08 |
| 21402 | C | LYS | D | 407 | -139.127 | -7.853 | 42.971 | 1.00 | 36.78 |
| 21403 | O | LYS | D | 407 | -139.624 | -8.234 | 44.042 | 1.00 | 36.66 |
| 21404 | N | ILE | D | 408 | -139.195 | -6.600 | 42.547 | 1.00 | 37.10 |
| 21405 | CA | ILE | D | 408 | -139.922 | -5.596 | 43.293 | 1.00 | 37.04 |
| 21406 | CB | ILE | D | 408 | -139.204 | -4.256 | 43.236 | 1.00 | 36.23 |
| 21407 | CG1 | ILE | D | 408 | -137.831 | -4.326 | 43.878 | 1.00 | 36.01 |
| 21408 | CD1 | ILE | D | 408 | -137.158 | -2.960 | 43.957 | 1.00 | 33.49 |
| 21409 | CG2 | ILE | D | 408 | -140.016 | -3.229 | 43.938 | 1.00 | 36.26 |
| 21410 | C | ILE | D | 408 | -141.289 | -5.394 | 42.684 | 1.00 | 37.65 |

FIGURE 3 PD

| A | B | C | D | E | F | G | H | I | J |
|---|---|---|---|---|---|---|---|---|---|
| 21411 | O | ILE | D | 408 | -141.401 | -5.034 | 41.515 | 1.00 | 37.20 |
| 21412 | N | GLN | D | 409 | -142.330 | -5.598 | 43.485 | 1.00 | 38.31 |
| 21413 | CA | GLN | D | 409 | -143.691 | -5.350 | 43.029 | 1.00 | 38.57 |
| 21414 | CB | GLN | D | 409 | -144.674 | -5.848 | 44.083 | 1.00 | 38.78 |
| 21415 | CG | GLN | D | 409 | -146.009 | -6.289 | 43.538 | 1.00 | 40.54 |
| 21416 | CD | GLN | D | 409 | -147.113 | -6.202 | 44.568 | 1.00 | 42.55 |
| 21417 | OE1 | GLN | D | 409 | -147.261 | -7.089 | 45.414 | 1.00 | 44.19 |
| 21418 | NE2 | GLN | D | 409 | -147.893 | -5.131 | 44.504 | 1.00 | 43.30 |
| 21419 | C | GLN | D | 409 | -143.829 | -3.842 | 42.820 | 1.00 | 38.57 |
| 21420 | O | GLN | D | 409 | -143.724 | -3.063 | 43.765 | 1.00 | 38.39 |
| 21421 | N | LEU | D | 410 | -144.045 | -3.418 | 41.581 | 1.00 | 38.83 |
| 21422 | CA | LEU | D | 410 | -144.096 | -1.990 | 41.286 | 1.00 | 39.17 |
| 21423 | CB | LEU | D | 410 | -144.019 | -1.742 | 39.778 | 1.00 | 39.59 |
| 21424 | CG | LEU | D | 410 | -142.621 | -1.439 | 39.217 | 1.00 | 40.31 |
| 21425 | CD1 | LEU | D | 410 | -141.515 | -1.972 | 40.122 | 1.00 | 38.99 |
| 21426 | CD2 | LEU | D | 410 | -142.484 | -1.970 | 37.789 | 1.00 | 40.56 |
| 21427 | C | LEU | D | 410 | -145.308 | -1.285 | 41.883 | 1.00 | 39.46 |
| 21428 | O | LEU | D | 410 | -145.281 | -0.070 | 42.101 | 1.00 | 39.25 |
| 21429 | N | SER | D | 411 | -146.374 | -2.039 | 42.144 | 1.00 | 39.59 |
| 21430 | CA | SER | D | 411 | -147.547 | -1.454 | 42.777 | 1.00 | 39.90 |
| 21431 | CB | SER | D | 411 | -148.790 | -2.339 | 42.590 | 1.00 | 40.21 |
| 21432 | OG | SER | D | 411 | -148.800 | -3.468 | 43.458 | 1.00 | 40.00 |
| 21433 | C | SER | D | 411 | -147.274 | -1.167 | 44.252 | 1.00 | 40.10 |
| 21434 | O | SER | D | 411 | -147.932 | -0.325 | 44.839 | 1.00 | 40.37 |
| 21435 | N | ASP | D | 412 | -146.292 | -1.858 | 44.839 | 1.00 | 40.45 |
| 21436 | CA | ASP | D | 412 | -145.877 | -1.625 | 46.239 | 1.00 | 40.64 |
| 21437 | CB | ASP | D | 412 | -146.788 | -2.349 | 47.233 | 1.00 | 40.63 |
| 21438 | CG | ASP | D | 412 | -146.538 | -1.916 | 48.686 | 1.00 | 41.97 |
| 21439 | OD1 | ASP | D | 412 | -147.314 | -2.347 | 49.573 | 1.00 | 40.00 |
| 21440 | OD2 | ASP | D | 412 | -145.599 | -1.142 | 49.029 | 1.00 | 41.57 |
| 21441 | C | ASP | D | 412 | -144.443 | -2.098 | 46.413 | 1.00 | 40.30 |
| 21442 | O | ASP | D | 412 | -144.197 | -3.287 | 46.546 | 1.00 | 40.84 |
| 21443 | N | TYR | D | 413 | -143.489 | -1.172 | 46.419 | 1.00 | 40.08 |
| 21444 | CA | TYR | D | 413 | -142.079 | -1.567 | 46.427 | 1.00 | 39.51 |
| 21445 | CB | TYR | D | 413 | -141.158 | -0.426 | 45.969 | 1.00 | 39.27 |
| 21446 | CG | TYR | D | 413 | -141.130 | 0.781 | 46.862 | 1.00 | 37.33 |
| 21447 | CD1 | TYR | D | 413 | -140.282 | 0.833 | 47.949 | 1.00 | 35.88 |
| 21448 | CE1 | TYR | D | 413 | -140.229 | 1.934 | 48.757 | 1.00 | 34.67 |
| 21449 | CZ | TYR | D | 413 | -141.029 | 3.004 | 48.492 | 1.00 | 36.06 |
| 21450 | OH | TYR | D | 413 | -140.968 | 4.095 | 49.318 | 1.00 | 35.92 |
| 21451 | CE2 | TYR | D | 413 | -141.892 | 2.988 | 47.412 | 1.00 | 36.35 |
| 21452 | CD2 | TYR | D | 413 | -141.931 | 1.883 | 46.602 | 1.00 | 36.60 |
| 21453 | C | TYR | D | 413 | -141.575 | -2.211 | 47.709 | 1.00 | 39.83 |
| 21454 | O | TYR | D | 413 | -140.532 | -2.869 | 47.699 | 1.00 | 39.86 |
| 21455 | N | THR | D | 414 | -142.317 | -2.056 | 48.803 | 1.00 | 39.71 |
| 21456 | CA | THR | D | 414 | -141.943 | -2.718 | 50.046 | 1.00 | 39.23 |
| 21457 | CB | THR | D | 414 | -142.774 | -2.186 | 51.223 | 1.00 | 39.42 |
| 21458 | OG1 | THR | D | 414 | -144.175 | -2.462 | 51.014 | 1.00 | 38.38 |
| 21459 | CG2 | THR | D | 414 | -142.691 | -0.664 | 51.277 | 1.00 | 38.32 |
| 21460 | C | THR | D | 414 | -142.164 | -4.211 | 49.868 | 1.00 | 39.68 |
| 21461 | O | THR | D | 414 | -141.595 | -5.033 | 50.584 | 1.00 | 40.05 |

FIGURE 3 PE

| A | B | C | D | E | F | G | H | I | J |
|---|---|---|---|---|---|---|---|---|---|
| 21462 | N | LYS | D | 415 | -142.979 | -4.567 | 48.886 | 1.00 | 39.61 |
| 21463 | CA | LYS | D | 415 | -143.232 | -5.969 | 48.623 | 1.00 | 40.20 |
| 21464 | CB | LYS | D | 415 | -144.658 | -6.174 | 48.103 | 1.00 | 40.65 |
| 21465 | CG | LYS | D | 415 | -145.753 | -5.943 | 49.167 | 1.00 | 42.91 |
| 21466 | CD | LYS | D | 415 | -147.143 | -6.165 | 48.571 | 1.00 | 48.34 |
| 21467 | CE | LYS | D | 415 | -148.267 | -5.526 | 49.405 | 1.00 | 51.00 |
| 21468 | NZ | LYS | D | 415 | -149.436 | -5.087 | 48.543 | 1.00 | 52.41 |
| 21469 | C | LYS | D | 415 | -142.173 | -6.514 | 47.657 | 1.00 | 39.99 |
| 21470 | O | LYS | D | 415 | -142.234 | -6.288 | 46.453 | 1.00 | 39.69 |
| 21471 | N | VAL | D | 416 | -141.206 | -7.239 | 48.206 | 1.00 | 39.55 |
| 21472 | CA | VAL | D | 416 | -140.078 | -7.713 | 47.432 | 1.00 | 39.65 |
| 21473 | CB | VAL | D | 416 | -138.763 | -7.049 | 47.913 | 1.00 | 39.43 |
| 21474 | CG1 | VAL | D | 416 | -137.575 | -7.558 | 47.097 | 1.00 | 38.91 |
| 21475 | CG2 | VAL | D | 416 | -138.866 | -5.545 | 47.842 | 1.00 | 38.33 |
| 21476 | C | VAL | D | 416 | -139.905 | -9.201 | 47.605 | 1.00 | 40.16 |
| 21477 | O | VAL | D | 416 | -139.900 | -9.697 | 48.730 | 1.00 | 40.54 |
| 21478 | N | THR | D | 417 | -139.730 | -9.917 | 46.502 | 1.00 | 40.19 |
| 21479 | CA | THR | D | 417 | -139.552 | -11.352 | 46.594 | 1.00 | 40.73 |
| 21480 | CB | THR | D | 417 | -140.654 | -12.083 | 45.815 | 1.00 | 40.89 |
| 21481 | OG1 | THR | D | 417 | -141.943 | -11.584 | 46.207 | 1.00 | 41.38 |
| 21482 | CG2 | THR | D | 417 | -140.671 | -13.551 | 46.219 | 1.00 | 40.34 |
| 21483 | C | THR | D | 417 | -138.212 | -11.819 | 46.064 | 1.00 | 41.14 |
| 21484 | O | THR | D | 417 | -137.792 | -11.447 | 44.972 | 1.00 | 40.93 |
| 21485 | N | CYS | D | 418 | -137.548 | -12.667 | 46.824 | 1.00 | 42.11 |
| 21486 | CA | CYS | D | 418 | -136.319 | -13.233 | 46.333 | 1.00 | 43.37 |
| 21487 | CB | CYS | D | 418 | -135.368 | -13.576 | 47.462 | 1.00 | 43.62 |
| 21488 | SG | CYS | D | 418 | -133.740 | -13.959 | 46.802 | 1.00 | 44.90 |
| 21489 | C | CYS | D | 418 | -136.656 | -14.483 | 45.557 | 1.00 | 43.93 |
| 21490 | O | CYS | D | 418 | -137.248 | -15.411 | 46.101 | 1.00 | 44.60 |
| 21491 | N | LEU | D | 419 | -136.277 | -14.502 | 44.284 | 1.00 | 44.37 |
| 21492 | CA | LEU | D | 419 | -136.554 | -15.628 | 43.405 | 1.00 | 44.48 |
| 21493 | CB | LEU | D | 419 | -136.660 | -15.136 | 41.961 | 1.00 | 44.17 |
| 21494 | CG | LEU | D | 419 | -137.709 | -14.031 | 41.779 | 1.00 | 44.46 |
| 21495 | CD1 | LEU | D | 419 | -137.792 | -13.568 | 40.331 | 1.00 | 43.74 |
| 21496 | CD2 | LEU | D | 419 | -139.069 | -14.517 | 42.271 | 1.00 | 42.94 |
| 21497 | C | LEU | D | 419 | -135.520 | -16.743 | 43.474 | 1.00 | 45.00 |
| 21498 | O | LEU | D | 419 | -135.784 | -17.866 | 43.037 | 1.00 | 45.47 |
| 21499 | N | SER | D | 420 | -134.343 | -16.458 | 44.013 | 1.00 | 45.42 |
| 21500 | CA | SER | D | 420 | -133.297 | -17.472 | 44.001 | 1.00 | 45.66 |
| 21501 | CB | SER | D | 420 | -132.104 | -17.002 | 43.159 | 1.00 | 45.76 |
| 21502 | OG | SER | D | 420 | -131.376 | -15.995 | 43.835 | 1.00 | 45.05 |
| 21503 | C | SER | D | 420 | -132.817 | -17.872 | 45.379 | 1.00 | 45.89 |
| 21504 | O | SER | D | 420 | -132.446 | -19.029 | 45.602 | 1.00 | 45.56 |
| 21505 | N | CYS | D | 421 | -132.827 | -16.922 | 46.304 | 1.00 | 46.29 |
| 21506 | CA | CYS | D | 421 | -132.279 | -17.182 | 47.629 | 1.00 | 47.17 |
| 21507 | CB | CYS | D | 421 | -132.876 | -16.234 | 48.664 | 1.00 | 47.16 |
| 21508 | SG | CYS | D | 421 | -132.521 | -14.509 | 48.309 | 1.00 | 47.80 |
| 21509 | C | CYS | D | 421 | -132.507 | -18.599 | 48.090 | 1.00 | 47.61 |
| 21510 | O | CYS | D | 421 | -131.597 | -19.270 | 48.577 | 1.00 | 47.82 |
| 21511 | N | GLU | D | 422 | -133.728 | -19.071 | 47.916 | 1.00 | 48.19 |
| 21512 | CA | GLU | D | 422 | -134.098 | -20.349 | 48.500 | 1.00 | 48.46 |

FIGURE 3 PF

| A | B | C | D | E | F | G | H | I | J |
|---|---|---|---|---|---|---|---|---|---|
| 21513 | CB | GLU | D | 422 | -135.454 | -20.191 | 49.179 | 1.00 | 48.73 |
| 21514 | CG | GLU | D | 422 | -135.466 | -20.669 | 50.606 | 1.00 | 50.61 |
| 21515 | CD | GLU | D | 422 | -134.709 | -19.725 | 51.495 | 1.00 | 52.80 |
| 21516 | OE1 | GLU | D | 422 | -133.838 | -20.187 | 52.279 | 1.00 | 53.41 |
| 21517 | OE2 | GLU | D | 422 | -134.994 | -18.515 | 51.391 | 1.00 | 53.84 |
| 21518 | C | GLU | D | 422 | -134.134 | -21.547 | 47.560 | 1.00 | 47.86 |
| 21519 | O | GLU | D | 422 | -134.444 | -22.642 | 47.997 | 1.00 | 47.92 |
| 21520 | N | LEU | D | 423 | -133.826 | -21.359 | 46.283 | 1.00 | 47.66 |
| 21521 | CA | LEU | D | 423 | -133.895 | -22.482 | 45.340 | 1.00 | 47.50 |
| 21522 | CB | LEU | D | 423 | -133.505 | -22.062 | 43.928 | 1.00 | 46.72 |
| 21523 | CG | LEU | D | 423 | -134.432 | -21.064 | 43.237 | 1.00 | 46.71 |
| 21524 | CD1 | LEU | D | 423 | -133.861 | -20.714 | 41.865 | 1.00 | 45.47 |
| 21525 | CD2 | LEU | D | 423 | -135.879 | -21.585 | 43.131 | 1.00 | 44.66 |
| 21526 | C | LEU | D | 423 | -133.075 | -23.702 | 45.742 | 1.00 | 47.55 |
| 21527 | O | LEU | D | 423 | -133.505 | -24.831 | 45.525 | 1.00 | 48.17 |
| 21528 | N | ASN | D | 424 | -131.904 | -23.468 | 46.318 | 1.00 | 47.60 |
| 21529 | CA | ASN | D | 424 | -130.973 | -24.525 | 46.690 | 1.00 | 47.92 |
| 21530 | CB | ASN | D | 424 | -130.413 | -25.192 | 45.437 | 1.00 | 47.81 |
| 21531 | CG | ASN | D | 424 | -129.955 | -26.611 | 45.692 | 1.00 | 49.37 |
| 21532 | OD1 | ASN | D | 424 | -129.435 | -26.929 | 46.764 | 1.00 | 49.33 |
| 21533 | ND2 | ASN | D | 424 | -130.155 | -27.481 | 44.704 | 1.00 | 51.05 |
| 21534 | C | ASN | D | 424 | -129.836 | -23.901 | 47.503 | 1.00 | 47.90 |
| 21535 | O | ASN | D | 424 | -128.681 | -23.873 | 47.083 | 1.00 | 47.55 |
| 21536 | N | PRO | D | 425 | -130.191 | -23.443 | 48.694 | 1.00 | 47.98 |
| 21537 | CA | PRO | D | 425 | -129.311 | -22.654 | 49.567 | 1.00 | 48.03 |
| 21538 | CB | PRO | D | 425 | -130.123 | -22.569 | 50.868 | 1.00 | 48.10 |
| 21539 | CG | PRO | D | 425 | -131.064 | -23.736 | 50.765 | 1.00 | 48.04 |
| 21540 | CD | PRO | D | 425 | -131.498 | -23.696 | 49.323 | 1.00 | 47.95 |
| 21541 | C | PRO | D | 425 | -127.924 | -23.227 | 49.870 | 1.00 | 48.20 |
| 21542 | O | PRO | D | 425 | -127.037 | -22.452 | 50.238 | 1.00 | 48.51 |
| 21543 | N | GLU | D | 426 | -127.737 | -24.537 | 49.754 | 1.00 | 47.89 |
| 21544 | CA | GLU | D | 426 | -126.446 | -25.129 | 50.076 | 1.00 | 47.79 |
| 21545 | CB | GLU | D | 426 | -126.594 | -26.585 | 50.536 | 1.00 | 48.56 |
| 21546 | CG | GLU | D | 426 | -127.339 | -26.801 | 51.843 | 1.00 | 50.73 |
| 21547 | CD | GLU | D | 426 | -127.464 | -28.279 | 52.171 | 1.00 | 54.79 |
| 21548 | OE1 | GLU | D | 426 | -126.586 | -28.803 | 52.894 | 1.00 | 56.18 |
| 21549 | OE2 | GLU | D | 426 | -128.432 | -28.924 | 51.692 | 1.00 | 56.61 |
| 21550 | C | GLU | D | 426 | -125.526 | -25.102 | 48.877 | 1.00 | 46.74 |
| 21551 | O | GLU | D | 426 | -124.343 | -24.816 | 49.004 | 1.00 | 46.76 |
| 21552 | N | ARG | D | 427 | -126.065 | -25.427 | 47.707 | 1.00 | 45.40 |
| 21553 | CA | ARG | D | 427 | -125.240 | -25.467 | 46.519 | 1.00 | 44.20 |
| 21554 | CB | ARG | D | 427 | -125.727 | -26.551 | 45.546 | 1.00 | 44.04 |
| 21555 | CG | ARG | D | 427 | -125.723 | -26.080 | 44.107 | 1.00 | 44.50 |
| 21556 | CD | ARG | D | 427 | -125.038 | -26.983 | 43.086 | 1.00 | 43.76 |
| 21557 | NE | ARG | D | 427 | -125.908 | -28.054 | 42.638 | 1.00 | 42.34 |
| 21558 | CZ | ARG | D | 427 | -125.861 | -28.639 | 41.452 | 1.00 | 42.26 |
| 21559 | NH1 | ARG | D | 427 | -126.715 | -29.615 | 41.190 | 1.00 | 45.11 |
| 21560 | NH2 | ARG | D | 427 | -124.995 | -28.263 | 40.521 | 1.00 | 40.08 |
| 21561 | C | ARG | D | 427 | -125.173 | -24.128 | 45.798 | 1.00 | 43.49 |
| 21562 | O | ARG | D | 427 | -124.241 | -23.877 | 45.031 | 1.00 | 43.01 |
| 21563 | N | CYS | D | 428 | -126.138 | -23.259 | 46.078 | 1.00 | 42.43 |

FIGURE 3 PG

| A | B | C | D | E | F | G | H | I | J |
|---|---|---|---|---|---|---|---|---|---|
| 21564 | CA | CYS | D | 428 | -126.316 | -22.075 | 45.261 | 1.00 | 41.60 |
| 21565 | CB | CYS | D | 428 | -127.509 | -22.311 | 44.340 | 1.00 | 41.72 |
| 21566 | SG | CYS | D | 428 | -127.122 | -23.466 | 43.014 | 1.00 | 42.76 |
| 21567 | C | CYS | D | 428 | -126.529 | -20.771 | 45.990 | 1.00 | 40.66 |
| 21568 | O | CYS | D | 428 | -127.604 | -20.527 | 46.522 | 1.00 | 40.59 |
| 21569 | N | GLN | D | 429 | -125.523 | -19.903 | 45.984 | 1.00 | 39.42 |
| 21570 | CA | GLN | D | 429 | -125.729 | -18.605 | 46.588 | 1.00 | 38.59 |
| 21571 | CB | GLN | D | 429 | -125.367 | -18.610 | 48.088 | 1.00 | 38.58 |
| 21572 | CG | GLN | D | 429 | -123.947 | -18.912 | 48.379 | 1.00 | 40.51 |
| 21573 | CD | GLN | D | 429 | -123.720 | -19.460 | 49.771 | 1.00 | 43.04 |
| 21574 | OE1 | GLN | D | 429 | -124.587 | -20.127 | 50.344 | 1.00 | 44.99 |
| 21575 | NE2 | GLN | D | 429 | -122.540 | -19.206 | 50.309 | 1.00 | 42.87 |
| 21576 | C | GLN | D | 429 | -125.122 | -17.462 | 45.759 | 1.00 | 37.72 |
| 21577 | O | GLN | D | 429 | -125.005 | -16.334 | 46.225 | 1.00 | 37.52 |
| 21578 | N | TYR | D | 430 | -124.799 | -17.759 | 44.501 | 1.00 | 36.84 |
| 21579 | CA | TYR | D | 430 | -124.289 | -16.762 | 43.564 | 1.00 | 36.29 |
| 21580 | CB | TYR | D | 430 | -122.778 | -16.910 | 43.408 | 1.00 | 36.15 |
| 21581 | CG | TYR | D | 430 | -122.035 | -15.707 | 42.852 | 1.00 | 35.36 |
| 21582 | CD1 | TYR | D | 430 | -122.065 | -15.387 | 41.501 | 1.00 | 34.99 |
| 21583 | CE1 | TYR | D | 430 | -121.359 | -14.288 | 41.012 | 1.00 | 34.16 |
| 21584 | CZ | TYR | D | 430 | -120.606 | -13.530 | 41.890 | 1.00 | 34.72 |
| 21585 | OH | TYR | D | 430 | -119.880 | -12.448 | 41.470 | 1.00 | 34.97 |
| 21586 | CE2 | TYR | D | 430 | -120.556 | -13.848 | 43.215 | 1.00 | 34.00 |
| 21587 | CD2 | TYR | D | 430 | -121.264 | -14.918 | 43.686 | 1.00 | 35.44 |
| 21588 | C | TYR | D | 430 | -124.948 | -16.973 | 42.207 | 1.00 | 36.15 |
| 21589 | O | TYR | D | 430 | -124.584 | -17.900 | 41.484 | 1.00 | 36.07 |
| 21590 | N | TYR | D | 431 | -125.888 | -16.102 | 41.848 | 1.00 | 35.64 |
| 21591 | CA | TYR | D | 431 | -126.613 | -16.241 | 40.589 | 1.00 | 35.47 |
| 21592 | CB | TYR | D | 431 | -128.108 | -16.294 | 40.856 | 1.00 | 35.49 |
| 21593 | CG | TYR | D | 431 | -128.639 | -17.525 | 41.507 | 1.00 | 36.37 |
| 21594 | CD1 | TYR | D | 431 | -129.229 | -18.524 | 40.751 | 1.00 | 37.01 |
| 21595 | CE1 | TYR | D | 431 | -129.747 | -19.658 | 41.347 | 1.00 | 36.29 |
| 21596 | CZ | TYR | D | 431 | -129.695 | -19.780 | 42.702 | 1.00 | 35.52 |
| 21597 | OH | TYR | D | 431 | -130.217 | -20.892 | 43.297 | 1.00 | 36.69 |
| 21598 | CE2 | TYR | D | 431 | -129.115 | -18.794 | 43.482 | 1.00 | 36.76 |
| 21599 | CD2 | TYR | D | 431 | -128.603 | -17.674 | 42.886 | 1.00 | 36.41 |
| 21600 | C | TYR | D | 431 | -126.505 | -15.076 | 39.635 | 1.00 | 35.33 |
| 21601 | O | TYR | D | 431 | -126.292 | -13.936 | 40.032 | 1.00 | 35.64 |
| 21602 | N | SER | D | 432 | -126.710 | -15.381 | 38.368 | 1.00 | 35.27 |
| 21603 | CA | SER | D | 432 | -126.946 | -14.371 | 37.354 | 1.00 | 35.96 |
| 21604 | CB | SER | D | 432 | -125.799 | -14.267 | 36.358 | 1.00 | 35.30 |
| 21605 | OG | SER | D | 432 | -125.588 | -15.515 | 35.744 | 1.00 | 35.72 |
| 21606 | C | SER | D | 432 | -128.229 | -14.841 | 36.655 | 1.00 | 36.30 |
| 21607 | O | SER | D | 432 | -128.697 | -15.970 | 36.871 | 1.00 | 36.14 |
| 21608 | N | VAL | D | 433 | -128.791 | -13.985 | 35.821 | 1.00 | 36.82 |
| 21609 | CA | VAL | D | 433 | -130.037 | -14.311 | 35.163 | 1.00 | 37.56 |
| 21610 | CB | VAL | D | 433 | -131.196 | -13.678 | 35.930 | 1.00 | 37.90 |
| 21611 | CG1 | VAL | D | 433 | -131.030 | -12.169 | 35.935 | 1.00 | 36.95 |
| 21612 | CG2 | VAL | D | 433 | -132.543 | -14.108 | 35.341 | 1.00 | 38.37 |
| 21613 | C | VAL | D | 433 | -130.087 | -13.836 | 33.706 | 1.00 | 38.13 |
| 21614 | O | VAL | D | 433 | -129.519 | -12.800 | 33.344 | 1.00 | 37.79 |

FIGURE 3 PH

| A | B | C | D | E | F | G | H | I | J |
|---|---|---|---|---|---|---|---|---|---|
| 21615 | N | SER | D | 434 | -130.744 | -14.629 | 32.870 | 1.00 | 38.99 |
| 21616 | CA | SER | D | 434 | -130.968 | -14.265 | 31.479 | 1.00 | 40.18 |
| 21617 | CB | SER | D | 434 | -130.234 | -15.215 | 30.536 | 1.00 | 40.13 |
| 21618 | OG | SER | D | 434 | -130.388 | -14.789 | 29.191 | 1.00 | 41.55 |
| 21619 | C | SER | D | 434 | -132.477 | -14.283 | 31.216 | 1.00 | 40.75 |
| 21620 | O | SER | D | 434 | -133.128 | -15.330 | 31.301 | 1.00 | 40.69 |
| 21621 | N | PHE | D | 435 | -133.034 | -13.115 | 30.924 | 1.00 | 41.85 |
| 21622 | CA | PHE | D | 435 | -134.469 | -12.993 | 30.702 | 1.00 | 43.32 |
| 21623 | CB | PHE | D | 435 | -134.993 | -11.682 | 31.292 | 1.00 | 43.21 |
| 21624 | CG | PHE | D | 435 | -135.297 | -11.755 | 32.753 | 1.00 | 43.92 |
| 21625 | CD1 | PHE | D | 435 | -134.322 | -11.471 | 33.690 | 1.00 | 44.21 |
| 21626 | CE1 | PHE | D | 435 | -134.599 | -11.536 | 35.036 | 1.00 | 44.76 |
| 21627 | CZ | PHE | D | 435 | -135.863 | -11.887 | 35.466 | 1.00 | 45.46 |
| 21628 | CE2 | PHE | D | 435 | -136.843 | -12.176 | 34.543 | 1.00 | 45.16 |
| 21629 | CD2 | PHE | D | 435 | -136.556 | -12.111 | 33.191 | 1.00 | 44.63 |
| 21630 | C | PHE | D | 435 | -134.872 | -13.051 | 29.237 | 1.00 | 44.20 |
| 21631 | O | PHE | D | 435 | -134.188 | -12.488 | 28.370 | 1.00 | 44.32 |
| 21632 | N | SER | D | 436 | -135.992 | -13.721 | 28.971 | 1.00 | 45.14 |
| 21633 | CA | SER | D | 436 | -136.565 | -13.726 | 27.629 | 1.00 | 46.32 |
| 21634 | CB | SER | D | 436 | -137.775 | -14.657 | 27.536 | 1.00 | 46.16 |
| 21635 | OG | SER | D | 436 | -138.793 | -14.300 | 28.455 | 1.00 | 45.63 |
| 21636 | C | SER | D | 436 | -136.939 | -12.285 | 27.313 | 1.00 | 47.45 |
| 21637 | O | SER | D | 436 | -137.091 | -11.474 | 28.234 | 1.00 | 47.31 |
| 21638 | N | LYS | D | 437 | -137.110 | -11.976 | 26.027 | 1.00 | 48.89 |
| 21639 | CA | LYS | D | 437 | -137.283 | -10.595 | 25.575 | 1.00 | 50.52 |
| 21640 | CB | LYS | D | 437 | -137.419 | -10.494 | 24.042 | 1.00 | 50.79 |
| 21641 | CG | LYS | D | 437 | -138.798 | -10.738 | 23.462 | 1.00 | 52.70 |
| 21642 | CD | LYS | D | 437 | -138.760 | -10.584 | 21.936 | 1.00 | 55.69 |
| 21643 | CE | LYS | D | 437 | -140.158 | -10.610 | 21.304 | 1.00 | 56.82 |
| 21644 | NZ | LYS | D | 437 | -140.888 | -11.882 | 21.586 | 1.00 | 58.40 |
| 21645 | C | LYS | D | 437 | -138.298 | -9.724 | 26.319 | 1.00 | 51.23 |
| 21646 | O | LYS | D | 437 | -138.068 | -8.526 | 26.491 | 1.00 | 51.25 |
| 21647 | N | GLU | D | 438 | -139.412 | -10.294 | 26.759 | 1.00 | 52.30 |
| 21648 | CA | GLU | D | 438 | -140.339 | -9.499 | 27.565 | 1.00 | 53.37 |
| 21649 | CB | GLU | D | 438 | -141.729 | -9.380 | 26.932 | 1.00 | 53.96 |
| 21650 | CG | GLU | D | 438 | -142.041 | -7.988 | 26.383 | 1.00 | 57.23 |
| 21651 | CD | GLU | D | 438 | -141.751 | -7.856 | 24.898 | 1.00 | 61.31 |
| 21652 | OE1 | GLU | D | 438 | -140.599 | -8.124 | 24.485 | 1.00 | 63.06 |
| 21653 | OE2 | GLU | D | 438 | -142.683 | -7.495 | 24.141 | 1.00 | 62.55 |
| 21654 | C | GLU | D | 438 | -140.408 | -10.017 | 28.995 | 1.00 | 53.07 |
| 21655 | O | GLU | D | 438 | -141.348 | -9.726 | 29.736 | 1.00 | 53.48 |
| 21656 | N | ALA | D | 439 | -139.399 | -10.795 | 29.367 | 1.00 | 52.51 |
| 21657 | CA | ALA | D | 439 | -139.267 | -11.291 | 30.732 | 1.00 | 51.94 |
| 21658 | CB | ALA | D | 439 | -139.268 | -10.130 | 31.722 | 1.00 | 52.12 |
| 21659 | C | ALA | D | 439 | -140.318 | -12.318 | 31.117 | 1.00 | 51.46 |
| 21660 | O | ALA | D | 439 | -140.627 | -12.481 | 32.297 | 1.00 | 51.35 |
| 21661 | N | LYS | D | 440 | -140.858 | -13.004 | 30.116 | 1.00 | 50.81 |
| 21662 | CA | LYS | D | 440 | -141.808 | -14.087 | 30.333 | 1.00 | 50.15 |
| 21663 | CB | LYS | D | 440 | -142.288 | -14.646 | 28.991 | 1.00 | 50.59 |
| 21664 | CG | LYS | D | 440 | -143.716 | -14.293 | 28.585 | 1.00 | 52.48 |
| 21665 | CD | LYS | D | 440 | -144.161 | -15.176 | 27.408 | 1.00 | 54.74 |

FIGURE 3 PI

| A | B | C | D | E | F | G | H | I | J |
|---|---|---|---|---|---|---|---|---|---|
| 21666 | CE | LYS | D | 440 | -145.640 | -15.003 | 27.069 | 1.00 | 56.58 |
| 21667 | NZ | LYS | D | 440 | -145.904 | -13.744 | 26.309 | 1.00 | 56.63 |
| 21668 | C | LYS | D | 440 | -141.121 | -15.205 | 31.085 | 1.00 | 49.03 |
| 21669 | O | LYS | D | 440 | -141.705 | -15.838 | 31.947 | 1.00 | 48.80 |
| 21670 | N | TYR | D | 441 | -139.873 | -15.460 | 30.733 | 1.00 | 48.21 |
| 21671 | CA | TYR | D | 441 | -139.120 | -16.517 | 31.374 | 1.00 | 47.74 |
| 21672 | CB | TYR | D | 441 | -138.895 | -17.673 | 30.406 | 1.00 | 47.94 |
| 21673 | CG | TYR | D | 441 | -140.137 | -18.159 | 29.711 | 1.00 | 50.35 |
| 21674 | CD1 | TYR | D | 441 | -140.543 | -17.597 | 28.510 | 1.00 | 51.56 |
| 21675 | CE1 | TYR | D | 441 | -141.671 | -18.038 | 27.865 | 1.00 | 53.50 |
| 21676 | CZ | TYR | D | 441 | -142.412 | -19.062 | 28.409 | 1.00 | 53.86 |
| 21677 | OH | TYR | D | 441 | -143.537 | -19.496 | 27.753 | 1.00 | 54.95 |
| 21678 | CE2 | TYR | D | 441 | -142.035 | -19.642 | 29.603 | 1.00 | 53.67 |
| 21679 | CD2 | TYR | D | 441 | -140.897 | -19.190 | 30.247 | 1.00 | 51.95 |
| 21680 | C | TYR | D | 441 | -137.762 | -16.009 | 31.776 | 1.00 | 46.81 |
| 21681 | O | TYR | D | 441 | -137.343 | -14.930 | 31.354 | 1.00 | 46.48 |
| 21682 | N | TYR | D | 442 | -137.062 | -16.810 | 32.574 | 1.00 | 45.97 |
| 21683 | CA | TYR | D | 442 | -135.684 | -16.495 | 32.914 | 1.00 | 44.89 |
| 21684 | CB | TYR | D | 442 | -135.590 | -15.490 | 34.064 | 1.00 | 44.45 |
| 21685 | CG | TYR | D | 442 | -136.242 | -15.889 | 35.363 | 1.00 | 43.39 |
| 21686 | CD1 | TYR | D | 442 | -137.520 | -15.445 | 35.680 | 1.00 | 41.55 |
| 21687 | CE1 | TYR | D | 442 | -138.116 | -15.778 | 36.871 | 1.00 | 39.53 |
| 21688 | CZ | TYR | D | 442 | -137.433 | -16.544 | 37.783 | 1.00 | 39.57 |
| 21689 | OH | TYR | D | 442 | -138.045 | -16.872 | 38.963 | 1.00 | 40.52 |
| 21690 | CE2 | TYR | D | 442 | -136.159 | -16.992 | 37.516 | 1.00 | 40.25 |
| 21691 | CD2 | TYR | D | 442 | -135.560 | -16.655 | 36.308 | 1.00 | 42.45 |
| 21692 | C | TYR | D | 442 | -134.801 | -17.712 | 33.162 | 1.00 | 44.37 |
| 21693 | O | TYR | D | 442 | -135.222 | -18.700 | 33.765 | 1.00 | 44.44 |
| 21694 | N | GLN | D | 443 | -133.581 | -17.648 | 32.649 | 1.00 | 43.41 |
| 21695 | CA | GLN | D | 443 | -132.625 | -18.688 | 32.944 | 1.00 | 42.92 |
| 21696 | CB | GLN | D | 443 | -131.656 | -18.931 | 31.785 | 1.00 | 42.69 |
| 21697 | CG | GLN | D | 443 | -130.544 | -19.908 | 32.162 | 1.00 | 42.04 |
| 21698 | CD | GLN | D | 443 | -129.411 | -19.954 | 31.152 | 1.00 | 42.81 |
| 21699 | OE1 | GLN | D | 443 | -128.810 | -21.009 | 30.948 | 1.00 | 43.87 |
| 21700 | NE2 | GLN | D | 443 | -129.120 | -18.825 | 30.519 | 1.00 | 41.23 |
| 21701 | C | GLN | D | 443 | -131.858 | -18.224 | 34.174 | 1.00 | 42.66 |
| 21702 | O | GLN | D | 443 | -131.360 | -17.099 | 34.223 | 1.00 | 42.28 |
| 21703 | N | LEU | D | 444 | -131.783 | -19.088 | 35.172 | 1.00 | 42.18 |
| 21704 | CA | LEU | D | 444 | -131.056 | -18.772 | 36.371 | 1.00 | 41.84 |
| 21705 | CB | LEU | D | 444 | -131.813 | -19.301 | 37.580 | 1.00 | 41.66 |
| 21706 | CG | LEU | D | 444 | -132.168 | -18.325 | 38.705 | 1.00 | 41.03 |
| 21707 | CD1 | LEU | D | 444 | -132.217 | -16.883 | 38.224 | 1.00 | 38.47 |
| 21708 | CD2 | LEU | D | 444 | -133.492 | -18.738 | 39.336 | 1.00 | 38.99 |
| 21709 | C | LEU | D | 444 | -129.730 | -19.488 | 36.225 | 1.00 | 42.26 |
| 21710 | O | LEU | D | 444 | -129.691 | -20.644 | 35.759 | 1.00 | 42.21 |
| 21711 | N | ARG | D | 445 | -128.647 | -18.800 | 36.586 | 1.00 | 42.14 |
| 21712 | CA | ARG | D | 445 | -127.309 | -19.385 | 36.527 | 1.00 | 42.28 |
| 21713 | CB | ARG | D | 445 | -126.464 | -18.679 | 35.471 | 1.00 | 42.67 |
| 21714 | CG | ARG | D | 445 | -124.990 | -19.098 | 35.433 | 1.00 | 44.72 |
| 21715 | CD | ARG | D | 445 | -124.049 | -17.909 | 35.576 | 1.00 | 48.07 |
| 21716 | NE | ARG | D | 445 | -122.828 | -17.971 | 34.777 | 1.00 | 48.95 |

FIGURE 3 PJ

| A | B | C | D | E | F | G | H | I | J |
|---|---|---|---|---|---|---|---|---|---|
| 21717 | CZ | ARG | D | 445 | -122.216 | -16.885 | 34.304 | 1.00 | 50.04 |
| 21718 | NH1 | ARG | D | 445 | -121.096 | -16.994 | 33.596 | 1.00 | 51.55 |
| 21719 | NH2 | ARG | D | 445 | -122.720 | -15.680 | 34.554 | 1.00 | 47.93 |
| 21720 | C | ARG | D | 445 | -126.636 | -19.293 | 37.903 | 1.00 | 42.16 |
| 21721 | O | ARG | D | 445 | -126.298 | -18.204 | 38.374 | 1.00 | 41.53 |
| 21722 | N | CYS | D | 446 | -126.456 | -20.450 | 38.534 | 1.00 | 41.65 |
| 21723 | CA | CYS | D | 446 | -125.851 | -20.554 | 39.848 | 1.00 | 41.54 |
| 21724 | CB | CYS | D | 446 | -126.619 | -21.589 | 40.651 | 1.00 | 41.64 |
| 21725 | SG | CYS | D | 446 | -125.705 | -22.405 | 41.978 | 1.00 | 46.47 |
| 21726 | C | CYS | D | 446 | -124.361 | -20.924 | 39.741 | 1.00 | 40.75 |
| 21727 | O | CYS | D | 446 | -123.999 | -21.988 | 39.211 | 1.00 | 40.72 |
| 21728 | N | SER | D | 447 | -123.497 | -20.052 | 40.252 | 1.00 | 39.17 |
| 21729 | CA | SER | D | 447 | -122.068 | -20.271 | 40.124 | 1.00 | 38.14 |
| 21730 | CB | SER | D | 447 | -121.359 | -18.974 | 39.706 | 1.00 | 38.31 |
| 21731 | OG | SER | D | 447 | -121.675 | -18.644 | 38.361 | 1.00 | 38.49 |
| 21732 | C | SER | D | 447 | -121.380 | -20.888 | 41.346 | 1.00 | 37.06 |
| 21733 | O | SER | D | 447 | -120.213 | -21.269 | 41.267 | 1.00 | 36.73 |
| 21734 | N | GLY | D | 448 | -122.087 | -20.995 | 42.464 | 1.00 | 35.95 |
| 21735 | CA | GLY | D | 448 | -121.483 | -21.548 | 43.666 | 1.00 | 34.88 |
| 21736 | C | GLY | D | 448 | -122.336 | -21.332 | 44.886 | 1.00 | 34.41 |
| 21737 | O | GLY | D | 448 | -123.344 | -20.628 | 44.820 | 1.00 | 34.38 |
| 21738 | N | PRO | D | 449 | -121.900 | -21.843 | 46.032 | 1.00 | 34.18 |
| 21739 | CA | PRO | D | 449 | -120.606 | -22.503 | 46.199 | 1.00 | 34.35 |
| 21740 | CB | PRO | D | 449 | -120.456 | -22.511 | 47.714 | 1.00 | 34.42 |
| 21741 | CG | PRO | D | 449 | -121.830 | -22.751 | 48.151 | 1.00 | 34.59 |
| 21742 | CD | PRO | D | 449 | -122.637 | -21.785 | 47.301 | 1.00 | 33.81 |
| 21743 | C | PRO | D | 449 | -120.477 | -23.949 | 45.701 | 1.00 | 34.75 |
| 21744 | O | PRO | D | 449 | -119.353 | -24.445 | 45.712 | 1.00 | 34.04 |
| 21745 | N | GLY | D | 450 | -121.570 | -24.618 | 45.329 | 1.00 | 34.83 |
| 21746 | CA | GLY | D | 450 | -121.467 | -25.974 | 44.826 | 1.00 | 35.54 |
| 21747 | C | GLY | D | 450 | -121.216 | -25.904 | 43.328 | 1.00 | 36.40 |
| 21748 | O | GLY | D | 450 | -120.901 | -24.833 | 42.820 | 1.00 | 36.56 |
| 21749 | N | LEU | D | 451 | -121.375 | -27.019 | 42.619 | 1.00 | 37.17 |
| 21750 | CA | LEU | D | 451 | -121.167 | -27.035 | 41.171 | 1.00 | 38.36 |
| 21751 | CB | LEU | D | 451 | -121.264 | -28.450 | 40.599 | 1.00 | 38.29 |
| 21752 | CG | LEU | D | 451 | -120.316 | -29.497 | 41.169 | 1.00 | 39.47 |
| 21753 | CD1 | LEU | D | 451 | -118.947 | -28.897 | 41.404 | 1.00 | 42.20 |
| 21754 | CD2 | LEU | D | 451 | -120.222 | -30.691 | 40.226 | 1.00 | 39.59 |
| 21755 | C | LEU | D | 451 | -122.192 | -26.164 | 40.489 | 1.00 | 38.94 |
| 21756 | O | LEU | D | 451 | -123.328 | -26.094 | 40.929 | 1.00 | 38.53 |
| 21757 | N | PRO | D | 452 | -121.793 | -25.512 | 39.405 | 1.00 | 39.85 |
| 21758 | CA | PRO | D | 452 | -122.686 | -24.601 | 38.692 | 1.00 | 40.73 |
| 21759 | CB | PRO | D | 452 | -121.879 | -24.214 | 37.443 | 1.00 | 40.68 |
| 21760 | CG | PRO | D | 452 | -120.463 | -24.420 | 37.829 | 1.00 | 40.65 |
| 21761 | CD | PRO | D | 452 | -120.460 | -25.592 | 38.784 | 1.00 | 40.03 |
| 21762 | C | PRO | D | 452 | -123.984 | -25.284 | 38.294 | 1.00 | 41.76 |
| 21763 | O | PRO | D | 452 | -123.955 | -26.413 | 37.795 | 1.00 | 41.77 |
| 21764 | N | LEU | D | 453 | -125.104 | -24.589 | 38.489 | 1.00 | 42.72 |
| 21765 | CA | LEU | D | 453 | -126.409 | -25.132 | 38.142 | 1.00 | 44.01 |
| 21766 | CB | LEU | D | 453 | -127.171 | -25.472 | 39.421 | 1.00 | 43.65 |
| 21767 | CG | LEU | D | 453 | -128.654 | -25.818 | 39.330 | 1.00 | 44.43 |

FIGURE 3 PK

| A | B | C | D | E | F | G | H | I | J |
|---|---|---|---|---|---|---|---|---|---|
| 21768 | CD1 | LEU | D | 453 | -128.878 | -27.054 | 38.482 | 1.00 | 45.71 |
| 21769 | CD2 | LEU | D | 453 | -129.205 | -26.022 | 40.733 | 1.00 | 43.84 |
| 21770 | C | LEU | D | 453 | -127.218 | -24.183 | 37.243 | 1.00 | 44.57 |
| 21771 | O | LEU | D | 453 | -127.478 | -23.038 | 37.599 | 1.00 | 45.35 |
| 21772 | N | TYR | D | 454 | -127.615 | -24.658 | 36.072 | 1.00 | 45.35 |
| 21773 | CA | TYR | D | 454 | -128.392 | -23.839 | 35.144 | 1.00 | 45.92 |
| 21774 | CB | TYR | D | 454 | -127.792 | -23.924 | 33.745 | 1.00 | 45.73 |
| 21775 | CG | TYR | D | 454 | -126.402 | -23.350 | 33.654 | 1.00 | 45.75 |
| 21776 | CD1 | TYR | D | 454 | -126.179 | -22.131 | 33.033 | 1.00 | 45.46 |
| 21777 | CE1 | TYR | D | 454 | -124.913 | -21.598 | 32.943 | 1.00 | 45.32 |
| 21778 | CZ | TYR | D | 454 | -123.845 | -22.278 | 33.479 | 1.00 | 44.31 |
| 21779 | OH | TYR | D | 454 | -122.596 | -21.729 | 33.374 | 1.00 | 42.66 |
| 21780 | CE2 | TYR | D | 454 | -124.028 | -23.497 | 34.100 | 1.00 | 44.72 |
| 21781 | CD2 | TYR | D | 454 | -125.306 | -24.029 | 34.182 | 1.00 | 46.13 |
| 21782 | C | TYR | D | 454 | -129.851 | -24.285 | 35.112 | 1.00 | 46.43 |
| 21783 | O | TYR | D | 454 | -130.134 | -25.451 | 34.886 | 1.00 | 46.58 |
| 21784 | N | THR | D | 455 | -130.774 | -23.356 | 35.343 | 1.00 | 47.08 |
| 21785 | CA | THR | D | 455 | -132.193 | -23.690 | 35.367 | 1.00 | 47.64 |
| 21786 | CB | THR | D | 455 | -132.713 | -23.740 | 36.813 | 1.00 | 47.54 |
| 21787 | OG1 | THR | D | 455 | -132.289 | -22.567 | 37.508 | 1.00 | 47.64 |
| 21788 | CG2 | THR | D | 455 | -132.039 | -24.851 | 37.592 | 1.00 | 47.78 |
| 21789 | C | THR | D | 455 | -133.045 | -22.730 | 34.539 | 1.00 | 47.80 |
| 21790 | O | THR | D | 455 | -132.574 | -21.687 | 34.105 | 1.00 | 48.21 |
| 21791 | N | LEU | D | 456 | -134.306 | -23.097 | 34.332 | 1.00 | 48.04 |
| 21792 | CA | LEU | D | 456 | -135.245 | -22.295 | 33.550 | 1.00 | 48.05 |
| 21793 | CB | LEU | D | 456 | -135.546 | -22.994 | 32.223 | 1.00 | 48.01 |
| 21794 | CG | LEU | D | 456 | -135.875 | -22.155 | 30.989 | 1.00 | 47.55 |
| 21795 | CD1 | LEU | D | 456 | -137.272 | -22.447 | 30.468 | 1.00 | 47.66 |
| 21796 | CD2 | LEU | D | 456 | -135.672 | -20.683 | 31.245 | 1.00 | 46.82 |
| 21797 | C | LEU | D | 456 | -136.526 | -22.093 | 34.342 | 1.00 | 48.19 |
| 21798 | O | LEU | D | 456 | -137.050 | -23.031 | 34.929 | 1.00 | 47.89 |
| 21799 | N | HIS | D | 457 | -137.034 | -20.864 | 34.352 | 1.00 | 48.72 |
| 21800 | CA | HIS | D | 457 | -138.213 | -20.543 | 35.142 | 1.00 | 48.94 |
| 21801 | CB | HIS | D | 457 | -137.789 | -19.790 | 36.408 | 1.00 | 48.74 |
| 21802 | CG | HIS | D | 457 | -136.662 | -20.441 | 37.143 | 1.00 | 47.92 |
| 21803 | ND1 | HIS | D | 457 | -136.837 | -21.096 | 38.344 | 1.00 | 47.19 |
| 21804 | CE1 | HIS | D | 457 | -135.677 | -21.581 | 38.751 | 1.00 | 46.29 |
| 21805 | NE2 | HIS | D | 457 | -134.759 | -21.274 | 37.852 | 1.00 | 47.36 |
| 21806 | CD2 | HIS | D | 457 | -135.348 | -20.558 | 36.838 | 1.00 | 47.16 |
| 21807 | C | HIS | D | 457 | -139.197 | -19.682 | 34.381 | 1.00 | 49.53 |
| 21808 | O | HIS | D | 457 | -138.798 | -18.879 | 33.538 | 1.00 | 49.59 |
| 21809 | N | SER | D | 458 | -140.487 | -19.847 | 34.674 | 1.00 | 50.26 |
| 21810 | CA | SER | D | 458 | -141.500 | -18.966 | 34.102 | 1.00 | 50.88 |
| 21811 | CB | SER | D | 458 | -142.767 | -19.726 | 33.713 | 1.00 | 50.96 |
| 21812 | OG | SER | D | 458 | -143.549 | -20.052 | 34.849 | 1.00 | 51.17 |
| 21813 | C | SER | D | 458 | -141.812 | -17.902 | 35.145 | 1.00 | 51.50 |
| 21814 | O | SER | D | 458 | -142.068 | -18.221 | 36.306 | 1.00 | 50.79 |
| 21815 | N | SER | D | 459 | -141.764 | -16.640 | 34.730 | 1.00 | 52.70 |
| 21816 | CA | SER | D | 459 | -141.974 | -15.522 | 35.642 | 1.00 | 54.05 |
| 21817 | CB | SER | D | 459 | -141.491 | -14.211 | 35.016 | 1.00 | 54.13 |
| 21818 | OG | SER | D | 459 | -141.658 | -14.227 | 33.618 | 1.00 | 54.49 |

FIGURE 3 PL

| A | B | C | D | E | F | G | H | I | J |
|---|---|---|---|---|---|---|---|---|---|
| 21819 | C | SER | D | 459 | -143.408 | -15.385 | 36.140 | 1.00 | 54.93 |
| 21820 | O | SER | D | 459 | -143.638 | -14.942 | 37.261 | 1.00 | 55.05 |
| 21821 | N | VAL | D | 460 | -144.364 | -15.778 | 35.310 | 1.00 | 56.06 |
| 21822 | CA | VAL | D | 460 | -145.769 | -15.728 | 35.691 | 1.00 | 57.14 |
| 21823 | CB | VAL | D | 460 | -146.599 | -16.732 | 34.878 | 1.00 | 57.09 |
| 21824 | CG1 | VAL | D | 460 | -148.034 | -16.753 | 35.373 | 1.00 | 57.72 |
| 21825 | CG2 | VAL | D | 460 | -146.546 | -16.377 | 33.396 | 1.00 | 57.91 |
| 21826 | C | VAL | D | 460 | -145.969 | -16.006 | 37.181 | 1.00 | 57.62 |
| 21827 | O | VAL | D | 460 | -146.490 | -15.164 | 37.909 | 1.00 | 57.81 |
| 21828 | N | ASN | D | 461 | -145.563 | -17.192 | 37.624 | 1.00 | 58.27 |
| 21829 | CA | ASN | D | 461 | -145.685 | -17.576 | 39.021 | 1.00 | 58.95 |
| 21830 | CB | ASN | D | 461 | -146.436 | -18.902 | 39.147 | 1.00 | 59.48 |
| 21831 | CG | ASN | D | 461 | -147.945 | -18.738 | 39.068 | 1.00 | 60.70 |
| 21832 | OD1 | ASN | D | 461 | -148.521 | -17.831 | 39.679 | 1.00 | 62.63 |
| 21833 | ND2 | ASN | D | 461 | -148.594 | -19.627 | 38.326 | 1.00 | 61.00 |
| 21834 | C | ASN | D | 461 | -144.319 | -17.718 | 39.688 | 1.00 | 59.24 |
| 21835 | O | ASN | D | 461 | -144.211 | -17.653 | 40.914 | 1.00 | 59.41 |
| 21836 | N | ASP | D | 462 | -143.288 | -17.931 | 38.873 | 1.00 | 59.20 |
| 21837 | CA | ASP | D | 462 | -141.924 | -18.130 | 39.353 | 1.00 | 59.12 |
| 21838 | CB | ASP | D | 462 | -141.595 | -17.211 | 40.532 | 1.00 | 59.07 |
| 21839 | CG | ASP | D | 462 | -141.596 | -15.763 | 40.144 | 1.00 | 58.94 |
| 21840 | OD1 | ASP | D | 462 | -142.050 | -14.930 | 40.955 | 1.00 | 57.44 |
| 21841 | OD2 | ASP | D | 462 | -141.167 | -15.370 | 39.037 | 1.00 | 60.22 |
| 21842 | C | ASP | D | 462 | -141.668 | -19.568 | 39.752 | 1.00 | 59.26 |
| 21843 | O | ASP | D | 462 | -141.084 | -19.831 | 40.804 | 1.00 | 59.45 |
| 21844 | N | LYS | D | 463 | -142.099 | -20.511 | 38.923 | 1.00 | 59.18 |
| 21845 | CA | LYS | D | 463 | -141.795 | -21.907 | 39.216 | 1.00 | 59.00 |
| 21846 | CB | LYS | D | 463 | -143.052 | -22.776 | 39.243 | 1.00 | 59.52 |
| 21847 | CG | LYS | D | 463 | -143.458 | -23.162 | 40.667 | 1.00 | 60.85 |
| 21848 | CD | LYS | D | 463 | -142.289 | -23.831 | 41.401 | 1.00 | 62.85 |
| 21849 | CE | LYS | D | 463 | -142.425 | -23.690 | 42.922 | 1.00 | 64.92 |
| 21850 | NZ | LYS | D | 463 | -142.345 | -22.260 | 43.400 | 1.00 | 65.38 |
| 21851 | C | LYS | D | 463 | -140.748 | -22.497 | 38.289 | 1.00 | 58.46 |
| 21852 | O | LYS | D | 463 | -140.526 | -22.010 | 37.181 | 1.00 | 58.19 |
| 21853 | N | GLY | D | 464 | -140.093 | -23.544 | 38.769 | 1.00 | 57.94 |
| 21854 | CA | GLY | D | 464 | -139.066 | -24.202 | 38.001 | 1.00 | 57.62 |
| 21855 | C | GLY | D | 464 | -139.659 | -24.968 | 36.846 | 1.00 | 57.48 |
| 21856 | O | GLY | D | 464 | -140.497 | -25.846 | 37.035 | 1.00 | 57.38 |
| 21857 | N | LEU | D | 465 | -139.238 | -24.621 | 35.640 | 1.00 | 57.33 |
| 21858 | CA | LEU | D | 465 | -139.677 | -25.347 | 34.464 | 1.00 | 57.18 |
| 21859 | CB | LEU | D | 465 | -139.479 | -24.516 | 33.198 | 1.00 | 57.23 |
| 21860 | CG | LEU | D | 465 | -140.300 | -23.225 | 33.212 | 1.00 | 56.97 |
| 21861 | CD1 | LEU | D | 465 | -140.474 | -22.677 | 31.814 | 1.00 | 57.14 |
| 21862 | CD2 | LEU | D | 465 | -141.658 | -23.480 | 33.839 | 1.00 | 57.78 |
| 21863 | C | LEU | D | 465 | -138.870 | -26.634 | 34.431 | 1.00 | 57.04 |
| 21864 | O | LEU | D | 465 | -139.441 | -27.728 | 34.406 | 1.00 | 57.23 |
| 21865 | N | ARG | D | 466 | -137.545 | -26.501 | 34.451 | 1.00 | 56.48 |
| 21866 | CA | ARG | D | 466 | -136.669 | -27.665 | 34.516 | 1.00 | 55.99 |
| 21867 | CB | ARG | D | 466 | -136.913 | -28.611 | 33.332 | 1.00 | 56.46 |
| 21868 | CG | ARG | D | 466 | -135.962 | -28.458 | 32.155 | 1.00 | 57.71 |
| 21869 | CD | ARG | D | 466 | -136.392 | -27.429 | 31.135 | 1.00 | 59.67 |

FIGURE 3 PM

| A | B | C | D | E | F | G | H | I | J |
|---|---|---|---|---|---|---|---|---|---|
| 21870 | NE  | ARG | D | 466 | -137.825 | -27.484 | 30.892 | 1.00 | 61.10 |
| 21871 | CZ  | ARG | D | 466 | -138.436 | -26.808 | 29.934 | 1.00 | 61.87 |
| 21872 | NH1 | ARG | D | 466 | -139.750 | -26.900 | 29.786 | 1.00 | 61.82 |
| 21873 | NH2 | ARG | D | 466 | -137.729 | -26.038 | 29.118 | 1.00 | 63.21 |
| 21874 | C   | ARG | D | 466 | -135.183 | -27.321 | 34.629 | 1.00 | 55.20 |
| 21875 | O   | ARG | D | 466 | -134.778 | -26.172 | 34.471 | 1.00 | 54.90 |
| 21876 | N   | VAL | D | 467 | -134.387 | -28.348 | 34.911 | 1.00 | 54.30 |
| 21877 | CA  | VAL | D | 467 | -132.940 | -28.235 | 35.016 | 1.00 | 53.21 |
| 21878 | CB  | VAL | D | 467 | -132.379 | -29.388 | 35.855 | 1.00 | 53.42 |
| 21879 | CG1 | VAL | D | 467 | -130.866 | -29.275 | 35.982 | 1.00 | 53.35 |
| 21880 | CG2 | VAL | D | 467 | -133.048 | -29.425 | 37.222 | 1.00 | 53.85 |
| 21881 | C   | VAL | D | 467 | -132.279 | -28.300 | 33.638 | 1.00 | 52.47 |
| 21882 | O   | VAL | D | 467 | -132.426 | -29.303 | 32.921 | 1.00 | 52.40 |
| 21883 | N   | LEU | D | 468 | -131.548 | -27.239 | 33.279 | 1.00 | 50.89 |
| 21884 | CA  | LEU | D | 468 | -130.846 | -27.163 | 31.995 | 1.00 | 49.70 |
| 21885 | CB  | LEU | D | 468 | -130.698 | -25.708 | 31.543 | 1.00 | 49.44 |
| 21886 | CG  | LEU | D | 468 | -132.023 | -25.027 | 31.199 | 1.00 | 49.27 |
| 21887 | CD1 | LEU | D | 468 | -131.810 | -23.567 | 30.840 | 1.00 | 48.79 |
| 21888 | CD2 | LEU | D | 468 | -132.738 | -25.778 | 30.060 | 1.00 | 49.05 |
| 21889 | C   | LEU | D | 468 | -129.482 | -27.862 | 31.995 | 1.00 | 49.07 |
| 21890 | O   | LEU | D | 468 | -129.169 | -28.622 | 31.084 | 1.00 | 48.54 |
| 21891 | N   | GLU | D | 469 | -128.664 | -27.578 | 33.007 | 1.00 | 48.58 |
| 21892 | CA  | GLU | D | 469 | -127.357 | -28.220 | 33.139 | 1.00 | 47.89 |
| 21893 | CB  | GLU | D | 469 | -126.288 | -27.444 | 32.375 | 1.00 | 47.67 |
| 21894 | CG  | GLU | D | 469 | -124.891 | -28.041 | 32.469 | 1.00 | 47.41 |
| 21895 | CD  | GLU | D | 469 | -124.799 | -29.453 | 31.914 | 1.00 | 45.94 |
| 21896 | OE1 | GLU | D | 469 | -124.655 | -30.393 | 32.725 | 1.00 | 45.51 |
| 21897 | OE2 | GLU | D | 469 | -124.838 | -29.618 | 30.671 | 1.00 | 44.03 |
| 21898 | C   | GLU | D | 469 | -127.012 | -28.323 | 34.623 | 1.00 | 47.83 |
| 21899 | O   | GLU | D | 469 | -127.058 | -27.328 | 35.358 | 1.00 | 48.11 |
| 21900 | N   | ASP | D | 470 | -126.679 | -29.522 | 35.079 | 1.00 | 47.04 |
| 21901 | CA  | ASP | D | 470 | -126.422 | -29.701 | 36.501 | 1.00 | 46.35 |
| 21902 | CB  | ASP | D | 470 | -127.510 | -30.573 | 37.110 | 1.00 | 46.59 |
| 21903 | CG  | ASP | D | 470 | -127.258 | -32.053 | 36.895 | 1.00 | 47.45 |
| 21904 | OD1 | ASP | D | 470 | -127.874 | -32.856 | 37.625 | 1.00 | 49.16 |
| 21905 | OD2 | ASP | D | 470 | -126.466 | -32.507 | 36.034 | 1.00 | 47.48 |
| 21906 | C   | ASP | D | 470 | -125.043 | -30.270 | 36.854 | 1.00 | 45.48 |
| 21907 | O   | ASP | D | 470 | -124.777 | -30.538 | 38.010 | 1.00 | 45.18 |
| 21908 | N   | ASN | D | 471 | -124.189 | -30.480 | 35.857 | 1.00 | 45.37 |
| 21909 | CA  | ASN | D | 471 | -122.825 | -30.972 | 36.093 | 1.00 | 45.03 |
| 21910 | CB  | ASN | D | 471 | -122.002 | -29.909 | 36.820 | 1.00 | 44.74 |
| 21911 | CG  | ASN | D | 471 | -121.718 | -28.741 | 35.955 | 1.00 | 43.13 |
| 21912 | OD1 | ASN | D | 471 | -121.105 | -28.887 | 34.912 | 1.00 | 43.43 |
| 21913 | ND2 | ASN | D | 471 | -122.199 | -27.572 | 36.347 | 1.00 | 43.86 |
| 21914 | C   | ASN | D | 471 | -122.713 | -32.284 | 36.850 | 1.00 | 45.61 |
| 21915 | O   | ASN | D | 471 | -121.718 | -32.519 | 37.555 | 1.00 | 45.32 |
| 21916 | N   | SER | D | 472 | -123.725 | -33.135 | 36.712 | 1.00 | 45.97 |
| 21917 | CA  | SER | D | 472 | -123.686 | -34.434 | 37.358 | 1.00 | 46.60 |
| 21918 | CB  | SER | D | 472 | -124.987 | -35.216 | 37.114 | 1.00 | 46.83 |
| 21919 | OG  | SER | D | 472 | -125.225 | -35.407 | 35.734 | 1.00 | 45.94 |
| 21920 | C   | SER | D | 472 | -122.487 | -35.202 | 36.830 | 1.00 | 46.97 |

FIGURE 3 PN

| A | B | C | D | E | F | G | H | I | J |
|---|---|---|---|---|---|---|---|---|---|
| 21921 | O | SER | D | 472 | -121.896 | -36.014 | 37.537 | 1.00 | 46.85 |
| 21922 | N | ALA | D | 473 | -122.121 | -34.932 | 35.585 | 1.00 | 47.64 |
| 21923 | CA | ALA | D | 473 | -120.978 | -35.600 | 34.986 | 1.00 | 48.90 |
| 21924 | CB | ALA | D | 473 | -120.887 | -35.269 | 33.506 | 1.00 | 48.66 |
| 21925 | C | ALA | D | 473 | -119.685 | -35.206 | 35.712 | 1.00 | 49.86 |
| 21926 | O | ALA | D | 473 | -118.893 | -36.065 | 36.113 | 1.00 | 49.97 |
| 21927 | N | LEU | D | 474 | -119.479 | -33.904 | 35.887 | 1.00 | 50.76 |
| 21928 | CA | LEU | D | 474 | -118.289 | -33.433 | 36.567 | 1.00 | 51.58 |
| 21929 | CB | LEU | D | 474 | -118.187 | -31.907 | 36.495 | 1.00 | 51.66 |
| 21930 | CG | LEU | D | 474 | -117.148 | -31.285 | 37.433 | 1.00 | 51.70 |
| 21931 | CD1 | LEU | D | 474 | -115.768 | -31.859 | 37.156 | 1.00 | 51.48 |
| 21932 | CD2 | LEU | D | 474 | -117.137 | -29.783 | 37.282 | 1.00 | 52.13 |
| 21933 | C | LEU | D | 474 | -118.329 | -33.884 | 38.010 | 1.00 | 52.25 |
| 21934 | O | LEU | D | 474 | -117.316 | -34.287 | 38.563 | 1.00 | 52.55 |
| 21935 | N | ASP | D | 475 | -119.510 | -33.843 | 38.613 | 1.00 | 53.48 |
| 21936 | CA | ASP | D | 475 | -119.647 | -34.187 | 40.018 | 1.00 | 54.86 |
| 21937 | CB | ASP | D | 475 | -121.095 | -34.027 | 40.483 | 1.00 | 54.92 |
| 21938 | CG | ASP | D | 475 | -121.202 | -33.806 | 41.979 | 1.00 | 55.85 |
| 21939 | OD1 | ASP | D | 475 | -121.574 | -34.748 | 42.713 | 1.00 | 56.95 |
| 21940 | OD2 | ASP | D | 475 | -120.918 | -32.714 | 42.517 | 1.00 | 57.34 |
| 21941 | C | ASP | D | 475 | -119.215 | -35.606 | 40.264 | 1.00 | 55.98 |
| 21942 | O | ASP | D | 475 | -118.685 | -35.926 | 41.330 | 1.00 | 56.18 |
| 21943 | N | LYS | D | 476 | -119.457 | -36.456 | 39.269 | 1.00 | 57.23 |
| 21944 | CA | LYS | D | 476 | -119.158 | -37.876 | 39.380 | 1.00 | 58.53 |
| 21945 | CB | LYS | D | 476 | -119.741 | -38.661 | 38.190 | 1.00 | 58.87 |
| 21946 | CG | LYS | D | 476 | -119.473 | -40.166 | 38.263 | 1.00 | 60.86 |
| 21947 | CD | LYS | D | 476 | -119.859 | -40.902 | 36.975 | 1.00 | 63.70 |
| 21948 | CE | LYS | D | 476 | -121.293 | -41.443 | 37.037 | 1.00 | 65.24 |
| 21949 | NZ | LYS | D | 476 | -121.512 | -42.417 | 38.155 | 1.00 | 65.26 |
| 21950 | C | LYS | D | 476 | -117.668 | -38.111 | 39.478 | 1.00 | 58.65 |
| 21951 | O | LYS | D | 476 | -117.174 | -38.640 | 40.478 | 1.00 | 58.69 |
| 21952 | N | MET | D | 477 | -116.949 | -37.705 | 38.439 | 1.00 | 59.23 |
| 21953 | CA | MET | D | 477 | -115.508 | -37.926 | 38.402 | 1.00 | 59.66 |
| 21954 | CB | MET | D | 477 | -114.940 | -37.608 | 37.026 | 1.00 | 59.96 |
| 21955 | CG | MET | D | 477 | -115.338 | -36.270 | 36.493 | 1.00 | 60.64 |
| 21956 | SD | MET | D | 477 | -115.119 | -36.282 | 34.726 | 1.00 | 63.61 |
| 21957 | CE | MET | D | 477 | -113.501 | -37.031 | 34.565 | 1.00 | 63.14 |
| 21958 | C | MET | D | 477 | -114.762 | -37.165 | 39.485 | 1.00 | 59.47 |
| 21959 | O | MET | D | 477 | -113.581 | -37.411 | 39.712 | 1.00 | 59.77 |
| 21960 | N | LEU | D | 478 | -115.464 | -36.265 | 40.164 | 1.00 | 59.19 |
| 21961 | CA | LEU | D | 478 | -114.884 | -35.493 | 41.256 | 1.00 | 58.93 |
| 21962 | CB | LEU | D | 478 | -115.536 | -34.109 | 41.325 | 1.00 | 58.81 |
| 21963 | CG | LEU | D | 478 | -114.692 | -32.859 | 41.069 | 1.00 | 58.86 |
| 21964 | CD1 | LEU | D | 478 | -115.604 | -31.684 | 40.734 | 1.00 | 58.24 |
| 21965 | CD2 | LEU | D | 478 | -113.647 | -33.065 | 39.981 | 1.00 | 58.27 |
| 21966 | C | LEU | D | 478 | -115.003 | -36.159 | 42.623 | 1.00 | 58.92 |
| 21967 | O | LEU | D | 478 | -114.307 | -35.776 | 43.564 | 1.00 | 58.54 |
| 21968 | N | GLN | D | 479 | -115.877 | -37.152 | 42.751 | 1.00 | 59.09 |
| 21969 | CA | GLN | D | 479 | -116.070 | -37.774 | 44.062 | 1.00 | 59.11 |
| 21970 | CB | GLN | D | 479 | -117.383 | -38.561 | 44.155 | 1.00 | 59.76 |
| 21971 | CG | GLN | D | 479 | -118.090 | -38.372 | 45.501 | 1.00 | 61.97 |

21972  CD   GLN  D  479  -119.030  -39.524  45.872  1.00  65.23
  21973  OE1  GLN  D  479  -119.557  -40.221  44.998  1.00  66.31
  21974  NE2  GLN  D  479  -119.239  -39.718  47.175  1.00  66.00
  21975  C    GLN  D  479  -114.879  -38.627  44.491  1.00  58.36
  21976  O    GLN  D  479  -114.691  -38.874  45.688  1.00  58.00
  21977  N    ASN  D  480  -114.082  -39.087  43.528  1.00  57.24
  21978  CA   ASN  D  480  -112.867  -39.798  43.901  1.00  56.76
  21979  CB   ASN  D  480  -112.788  -41.226  43.325  1.00  57.18
  21980  CG   ASN  D  480  -112.287  -41.266  41.893  1.00  59.21
  21981  OD1  ASN  D  480  -111.793  -42.301  41.428  1.00  60.24
  21982  ND2  ASN  D  480  -112.408  -40.138  41.181  1.00  61.22
  21983  C    ASN  D  480  -111.606  -38.965  43.648  1.00  55.75
  21984  O    ASN  D  480  -110.628  -39.431  43.069  1.00  55.51
  21985  N    VAL  D  481  -111.675  -37.706  44.067  1.00  54.57
  21986  CA   VAL  D  481  -110.523  -36.817  44.069  1.00  53.34
  21987  CB   VAL  D  481  -110.428  -35.930  42.802  1.00  53.46
  21988  CG1  VAL  D  481  -111.781  -35.649  42.243  1.00  54.08
  21989  CG2  VAL  D  481  -109.673  -34.652  43.080  1.00  53.22
  21990  C    VAL  D  481  -110.594  -36.009  45.353  1.00  52.30
  21991  O    VAL  D  481  -111.662  -35.561  45.759  1.00  52.13
  21992  N    GLN  D  482  -109.462  -35.884  46.029  1.00  51.18
  21993  CA   GLN  D  482  -109.410  -35.154  47.283  1.00  49.86
  21994  CB   GLN  D  482  -108.156  -35.547  48.058  1.00  49.82
  21995  CG   GLN  D  482  -108.002  -37.060  48.243  1.00  49.57
  21996  CD   GLN  D  482  -106.867  -37.426  49.179  1.00  49.43
  21997  OE1  GLN  D  482  -107.077  -37.558  50.384  1.00  50.82
  21998  NE2  GLN  D  482  -105.659  -37.583  48.632  1.00  48.75
  21999  C    GLN  D  482  -109.440  -33.651  47.000  1.00  49.29
  22000  O    GLN  D  482  -108.401  -32.975  46.982  1.00  49.35
  22001  N    MET  D  483  -110.645  -33.144  46.758  1.00  47.92
  22002  CA   MET  D  483  -110.854  -31.737  46.467  1.00  46.56
  22003  CB   MET  D  483  -112.204  -31.537  45.790  1.00  46.16
  22004  CG   MET  D  483  -112.260  -32.154  44.444  1.00  45.99
  22005  SD   MET  D  483  -111.154  -31.322  43.334  1.00  45.71
  22006  CE   MET  D  483  -112.226  -30.069  42.717  1.00  43.82
  22007  C    MET  D  483  -110.806  -30.911  47.732  1.00  45.76
  22008  O    MET  D  483  -111.243  -31.360  48.796  1.00  45.75
  22009  N    PRO  D  484  -110.291  -29.692  47.605  1.00  44.73
  22010  CA   PRO  D  484  -110.197  -28.767  48.737  1.00  44.12
  22011  CB   PRO  D  484  -109.288  -27.666  48.201  1.00  44.11
  22012  CG   PRO  D  484  -109.485  -27.686  46.732  1.00  43.89
  22013  CD   PRO  D  484  -109.759  -29.113  46.361  1.00  44.68
  22014  C    PRO  D  484  -111.550  -28.172  49.044  1.00  43.51
  22015  O    PRO  D  484  -112.436  -28.225  48.197  1.00  43.84
  22016  N    SER  D  485  -111.722  -27.612  50.231  1.00  42.90
  22017  CA   SER  D  485  -112.970  -26.908  50.509  1.00  42.75
  22018  CB   SER  D  485  -113.632  -27.391  51.812  1.00  42.78
  22019  OG   SER  D  485  -113.176  -26.684  52.952  1.00  43.62
  22020  C    SER  D  485  -112.750  -25.386  50.498  1.00  42.19
  22021  O    SER  D  485  -111.632  -24.893  50.312  1.00  41.86
  22022  N    LYS  D  486  -113.827  -24.640  50.693  1.00  41.74
```

FIGURE 3 PP

| A | B | C | D | E | F | G | H | I | J |
|---|---|---|---|---|---|---|---|---|---|
| 22023 | CA | LYS | D | 486 | -113.741 | -23.195 | 50.686 | 1.00 | 40.78 |
| 22024 | CB | LYS | D | 486 | -114.442 | -22.654 | 49.452 | 1.00 | 40.90 |
| 22025 | CG | LYS | D | 486 | -113.909 | -21.320 | 48.975 | 1.00 | 41.55 |
| 22026 | CD | LYS | D | 486 | -115.021 | -20.426 | 48.472 | 1.00 | 40.25 |
| 22027 | CE | LYS | D | 486 | -114.611 | -19.660 | 47.244 | 1.00 | 39.87 |
| 22028 | NZ | LYS | D | 486 | -115.636 | -18.663 | 46.873 | 1.00 | 39.43 |
| 22029 | C | LYS | D | 486 | -114.405 | -22.643 | 51.925 | 1.00 | 40.36 |
| 22030 | O | LYS | D | 486 | -115.550 | -22.959 | 52.210 | 1.00 | 41.08 |
| 22031 | N | LYS | D | 487 | -113.690 | -21.828 | 52.674 | 1.00 | 39.57 |
| 22032 | CA | LYS | D | 487 | -114.273 | -21.202 | 53.839 | 1.00 | 39.62 |
| 22033 | CB | LYS | D | 487 | -113.408 | -21.440 | 55.084 | 1.00 | 39.82 |
| 22034 | CG | LYS | D | 487 | -113.183 | -20.201 | 55.917 | 1.00 | 41.25 |
| 22035 | CD | LYS | D | 487 | -113.978 | -20.210 | 57.219 | 1.00 | 43.92 |
| 22036 | CE | LYS | D | 487 | -113.064 | -20.381 | 58.418 | 1.00 | 45.08 |
| 22037 | NZ | LYS | D | 487 | -113.720 | -19.919 | 59.680 | 1.00 | 46.72 |
| 22038 | C | LYS | D | 487 | -114.409 | -19.720 | 53.518 | 1.00 | 39.47 |
| 22039 | O | LYS | D | 487 | -113.460 | -19.069 | 53.073 | 1.00 | 39.19 |
| 22040 | N | LEU | D | 488 | -115.612 | -19.204 | 53.694 | 1.00 | 39.33 |
| 22041 | CA | LEU | D | 488 | -115.901 | -17.821 | 53.388 | 1.00 | 39.38 |
| 22042 | CB | LEU | D | 488 | -116.982 | -17.730 | 52.315 | 1.00 | 38.75 |
| 22043 | CG | LEU | D | 488 | -117.483 | -16.321 | 52.013 | 1.00 | 38.45 |
| 22044 | CD1 | LEU | D | 488 | -116.420 | -15.484 | 51.271 | 1.00 | 35.08 |
| 22045 | CD2 | LEU | D | 488 | -118.762 | -16.400 | 51.225 | 1.00 | 35.39 |
| 22046 | C | LEU | D | 488 | -116.371 | -17.176 | 54.670 | 1.00 | 40.14 |
| 22047 | O | LEU | D | 488 | -117.465 | -17.446 | 55.153 | 1.00 | 39.95 |
| 22048 | N | ASP | D | 489 | -115.528 | -16.332 | 55.236 | 1.00 | 40.97 |
| 22049 | CA | ASP | D | 489 | -115.842 | -15.747 | 56.514 | 1.00 | 42.21 |
| 22050 | CB | ASP | D | 489 | -115.194 | -16.578 | 57.625 | 1.00 | 42.33 |
| 22051 | CG | ASP | D | 489 | -116.020 | -16.614 | 58.877 | 1.00 | 43.32 |
| 22052 | OD1 | ASP | D | 489 | -115.962 | -17.644 | 59.590 | 1.00 | 46.30 |
| 22053 | OD2 | ASP | D | 489 | -116.772 | -15.677 | 59.223 | 1.00 | 43.96 |
| 22054 | C | ASP | D | 489 | -115.302 | -14.331 | 56.543 | 1.00 | 42.65 |
| 22055 | O | ASP | D | 489 | -114.798 | -13.834 | 55.547 | 1.00 | 42.81 |
| 22056 | N | PHE | D | 490 | -115.384 | -13.692 | 57.697 | 1.00 | 43.33 |
| 22057 | CA | PHE | D | 490 | -114.902 | -12.341 | 57.811 | 1.00 | 44.25 |
| 22058 | CB | PHE | D | 490 | -116.082 | -11.381 | 57.802 | 1.00 | 44.26 |
| 22059 | CG | PHE | D | 490 | -117.097 | -11.679 | 58.855 | 1.00 | 45.55 |
| 22060 | CD1 | PHE | D | 490 | -118.185 | -12.488 | 58.574 | 1.00 | 46.52 |
| 22061 | CE1 | PHE | D | 490 | -119.128 | -12.771 | 59.548 | 1.00 | 47.79 |
| 22062 | CZ | PHE | D | 490 | -118.981 | -12.250 | 60.831 | 1.00 | 47.73 |
| 22063 | CE2 | PHE | D | 490 | -117.895 | -11.451 | 61.124 | 1.00 | 48.42 |
| 22064 | CD2 | PHE | D | 490 | -116.956 | -11.167 | 60.133 | 1.00 | 47.31 |
| 22065 | C | PHE | D | 490 | -114.130 | -12.170 | 59.097 | 1.00 | 44.63 |
| 22066 | O | PHE | D | 490 | -114.258 | -12.977 | 60.012 | 1.00 | 44.70 |
| 22067 | N | ILE | D | 491 | -113.310 | -11.125 | 59.150 | 1.00 | 45.06 |
| 22068 | CA | ILE | D | 491 | -112.630 | -10.758 | 60.380 | 1.00 | 45.82 |
| 22069 | CB | ILE | D | 491 | -111.106 | -10.848 | 60.269 | 1.00 | 45.63 |
| 22070 | CG1 | ILE | D | 491 | -110.586 | -9.894 | 59.195 | 1.00 | 44.97 |
| 22071 | CD1 | ILE | D | 491 | -109.118 | -9.597 | 59.301 | 1.00 | 44.84 |
| 22072 | CG2 | ILE | D | 491 | -110.678 | -12.279 | 60.010 | 1.00 | 45.05 |
| 22073 | C | ILE | D | 491 | -113.051 | -9.339 | 60.668 | 1.00 | 46.97 |

FIGURE 3 PQ

| A | B | C | D | E | F | G | H | I | J |
|---|---|---|---|---|---|---|---|---|---|
| 22074 | O | ILE | D | 491 | -113.623 | -8.662 | 59.805 | 1.00 | 47.13 |
| 22075 | N | ILE | D | 492 | -112.785 | -8.880 | 61.878 | 1.00 | 48.24 |
| 22076 | CA | ILE | D | 492 | -113.196 | -7.539 | 62.257 | 1.00 | 49.65 |
| 22077 | CB | ILE | D | 492 | -114.083 | -7.594 | 63.515 | 1.00 | 49.69 |
| 22078 | CG1 | ILE | D | 492 | -115.388 | -8.340 | 63.227 | 1.00 | 50.20 |
| 22079 | CD1 | ILE | D | 492 | -116.570 | -7.802 | 64.028 | 1.00 | 51.67 |
| 22080 | CG2 | ILE | D | 492 | -114.407 | -6.194 | 63.986 | 1.00 | 50.11 |
| 22081 | C | ILE | D | 492 | -111.975 | -6.650 | 62.469 | 1.00 | 50.37 |
| 22082 | O | ILE | D | 492 | -111.155 | -6.918 | 63.349 | 1.00 | 50.50 |
| 22083 | N | LEU | D | 493 | -111.854 | -5.601 | 61.652 | 1.00 | 51.54 |
| 22084 | CA | LEU | D | 493 | -110.694 | -4.701 | 61.712 | 1.00 | 52.52 |
| 22085 | CB | LEU | D | 493 | -110.184 | -4.341 | 60.317 | 1.00 | 52.24 |
| 22086 | CG | LEU | D | 493 | -108.912 | -5.146 | 60.058 | 1.00 | 52.45 |
| 22087 | CD1 | LEU | D | 493 | -108.680 | -5.458 | 58.593 | 1.00 | 51.55 |
| 22088 | CD2 | LEU | D | 493 | -108.969 | -6.428 | 60.879 | 1.00 | 53.26 |
| 22089 | C | LEU | D | 493 | -110.868 | -3.466 | 62.603 | 1.00 | 53.48 |
| 22090 | O | LEU | D | 493 | -110.905 | -3.595 | 63.823 | 1.00 | 53.92 |
| 22091 | N | ASN | D | 494 | -110.922 | -2.258 | 62.057 | 1.00 | 54.20 |
| 22092 | CA | ASN | D | 494 | -111.136 | -1.164 | 62.993 | 1.00 | 54.48 |
| 22093 | CB | ASN | D | 494 | -111.206 | 0.200 | 62.314 | 1.00 | 55.01 |
| 22094 | CG | ASN | D | 494 | -109.883 | 0.958 | 62.401 | 1.00 | 56.92 |
| 22095 | OD1 | ASN | D | 494 | -109.450 | 1.342 | 63.490 | 1.00 | 59.72 |
| 22096 | ND2 | ASN | D | 494 | -109.236 | 1.170 | 61.260 | 1.00 | 58.60 |
| 22097 | C | ASN | D | 494 | -112.398 | -1.541 | 63.762 | 1.00 | 54.11 |
| 22098 | O | ASN | D | 494 | -112.324 | -2.095 | 64.861 | 1.00 | 54.46 |
| 22099 | N | GLU | D | 495 | -113.557 | -1.298 | 63.174 | 1.00 | 53.65 |
| 22100 | CA | GLU | D | 495 | -114.784 | -1.772 | 63.787 | 1.00 | 53.11 |
| 22101 | CB | GLU | D | 495 | -115.612 | -0.612 | 64.336 | 1.00 | 54.09 |
| 22102 | CG | GLU | D | 495 | -116.551 | -1.027 | 65.455 | 1.00 | 56.83 |
| 22103 | CD | GLU | D | 495 | -115.815 | -1.225 | 66.764 | 1.00 | 60.74 |
| 22104 | OE1 | GLU | D | 495 | -115.353 | -0.204 | 67.326 | 1.00 | 62.68 |
| 22105 | OE2 | GLU | D | 495 | -115.693 | -2.390 | 67.228 | 1.00 | 62.25 |
| 22106 | C | GLU | D | 495 | -115.573 | -2.506 | 62.726 | 1.00 | 51.60 |
| 22107 | O | GLU | D | 495 | -116.674 | -2.987 | 62.984 | 1.00 | 51.96 |
| 22108 | N | THR | D | 496 | -114.997 | -2.607 | 61.532 | 1.00 | 49.33 |
| 22109 | CA | THR | D | 496 | -115.736 | -3.155 | 60.404 | 1.00 | 46.76 |
| 22110 | CB | THR | D | 496 | -115.643 | -2.205 | 59.174 | 1.00 | 46.89 |
| 22111 | OG1 | THR | D | 496 | -114.334 | -2.268 | 58.610 | 1.00 | 47.10 |
| 22112 | CG2 | THR | D | 496 | -115.760 | -0.750 | 59.604 | 1.00 | 46.58 |
| 22113 | C | THR | D | 496 | -115.414 | -4.596 | 60.007 | 1.00 | 44.94 |
| 22114 | O | THR | D | 496 | -114.310 | -5.103 | 60.190 | 1.00 | 44.71 |
| 22115 | N | LYS | D | 497 | -116.432 | -5.229 | 59.450 | 1.00 | 42.85 |
| 22116 | CA | LYS | D | 497 | -116.389 | -6.584 | 58.954 | 1.00 | 40.72 |
| 22117 | CB | LYS | D | 497 | -117.838 | -7.010 | 58.705 | 1.00 | 41.43 |
| 22118 | CG | LYS | D | 497 | -118.239 | -8.401 | 59.150 | 1.00 | 43.19 |
| 22119 | CD | LYS | D | 497 | -119.544 | -8.317 | 59.940 | 1.00 | 44.70 |
| 22120 | CE | LYS | D | 497 | -120.511 | -9.436 | 59.581 | 1.00 | 46.88 |
| 22121 | NZ | LYS | D | 497 | -121.826 | -9.209 | 60.266 | 1.00 | 47.14 |
| 22122 | C | LYS | D | 497 | -115.664 | -6.549 | 57.618 | 1.00 | 38.35 |
| 22123 | O | LYS | D | 497 | -116.027 | -5.783 | 56.745 | 1.00 | 38.22 |
| 22124 | N | PHE | D | 498 | -114.630 | -7.357 | 57.464 | 1.00 | 35.89 |

FIGURE 3 PR

| A | B | C | D | E | F | G | H | I | J |
|---|---|---|---|---|---|---|---|---|---|
| 22125 | CA | PHE | D | 498 | -113.940 | -7.479 | 56.194 | 1.00 | 33.69 |
| 22126 | CB | PHE | D | 498 | -112.538 | -6.882 | 56.251 | 1.00 | 33.54 |
| 22127 | CG | PHE | D | 498 | -112.530 | -5.388 | 56.233 | 1.00 | 33.09 |
| 22128 | CD1 | PHE | D | 498 | -112.820 | -4.705 | 55.075 | 1.00 | 32.69 |
| 22129 | CE1 | PHE | D | 498 | -112.833 | -3.315 | 55.052 | 1.00 | 32.08 |
| 22130 | CZ | PHE | D | 498 | -112.555 | -2.609 | 56.197 | 1.00 | 33.54 |
| 22131 | CE2 | PHE | D | 498 | -112.269 | -3.286 | 57.373 | 1.00 | 32.77 |
| 22132 | CD2 | PHE | D | 498 | -112.263 | -4.665 | 57.386 | 1.00 | 32.47 |
| 22133 | C | PHE | D | 498 | -113.892 | -8.949 | 55.889 | 1.00 | 32.73 |
| 22134 | O | PHE | D | 498 | -113.480 | -9.749 | 56.735 | 1.00 | 32.65 |
| 22135 | N | TRP | D | 499 | -114.311 | -9.299 | 54.681 | 1.00 | 31.63 |
| 22136 | CA | TRP | D | 499 | -114.424 | -10.691 | 54.261 | 1.00 | 31.01 |
| 22137 | CB | TRP | D | 499 | -115.607 | -10.847 | 53.308 | 1.00 | 31.14 |
| 22138 | CG | TRP | D | 499 | -116.912 | -10.612 | 53.987 | 1.00 | 31.28 |
| 22139 | CD1 | TRP | D | 499 | -117.454 | -9.408 | 54.333 | 1.00 | 30.35 |
| 22140 | NE1 | TRP | D | 499 | -118.661 | -9.597 | 54.962 | 1.00 | 31.03 |
| 22141 | CE2 | TRP | D | 499 | -118.916 | -10.944 | 55.037 | 1.00 | 32.13 |
| 22142 | CD2 | TRP | D | 499 | -117.832 | -11.610 | 54.434 | 1.00 | 31.56 |
| 22143 | CE3 | TRP | D | 499 | -117.848 | -13.007 | 54.390 | 1.00 | 33.17 |
| 22144 | CZ3 | TRP | D | 499 | -118.930 | -13.683 | 54.927 | 1.00 | 32.84 |
| 22145 | CH2 | TRP | D | 499 | -119.996 | -12.986 | 55.513 | 1.00 | 32.25 |
| 22146 | CZ2 | TRP | D | 499 | -120.010 | -11.625 | 55.573 | 1.00 | 31.84 |
| 22147 | C | TRP | D | 499 | -113.190 | -11.274 | 53.607 | 1.00 | 30.65 |
| 22148 | O | TRP | D | 499 | -112.428 | -10.574 | 52.949 | 1.00 | 30.69 |
| 22149 | N | TYR | D | 500 | -113.016 | -12.580 | 53.789 | 1.00 | 30.45 |
| 22150 | CA | TYR | D | 500 | -111.914 | -13.302 | 53.214 | 1.00 | 30.20 |
| 22151 | CB | TYR | D | 500 | -110.790 | -13.445 | 54.234 | 1.00 | 30.96 |
| 22152 | CG | TYR | D | 500 | -111.094 | -14.361 | 55.402 | 1.00 | 30.58 |
| 22153 | CD1 | TYR | D | 500 | -110.852 | -15.720 | 55.309 | 1.00 | 31.42 |
| 22154 | CE1 | TYR | D | 500 | -111.109 | -16.571 | 56.357 | 1.00 | 32.91 |
| 22155 | CZ | TYR | D | 500 | -111.616 | -16.073 | 57.542 | 1.00 | 34.02 |
| 22156 | OH | TYR | D | 500 | -111.857 | -16.968 | 58.578 | 1.00 | 34.89 |
| 22157 | CE2 | TYR | D | 500 | -111.865 | -14.708 | 57.673 | 1.00 | 31.52 |
| 22158 | CD2 | TYR | D | 500 | -111.603 | -13.863 | 56.600 | 1.00 | 31.02 |
| 22159 | C | TYR | D | 500 | -112.409 | -14.666 | 52.843 | 1.00 | 30.46 |
| 22160 | O | TYR | D | 500 | -113.439 | -15.104 | 53.346 | 1.00 | 30.38 |
| 22161 | N | GLN | D | 501 | -111.685 | -15.327 | 51.943 | 1.00 | 30.25 |
| 22162 | CA | GLN | D | 501 | -111.965 | -16.706 | 51.593 | 1.00 | 29.73 |
| 22163 | CB | GLN | D | 501 | -112.640 | -16.824 | 50.227 | 1.00 | 29.03 |
| 22164 | CG | GLN | D | 501 | -111.724 | -16.668 | 49.024 | 1.00 | 26.43 |
| 22165 | CD | GLN | D | 501 | -112.467 | -16.885 | 47.703 | 1.00 | 23.64 |
| 22166 | OE1 | GLN | D | 501 | -113.668 | -16.622 | 47.614 | 1.00 | 21.69 |
| 22167 | NE2 | GLN | D | 501 | -111.759 | -17.360 | 46.689 | 1.00 | 19.81 |
| 22168 | C | GLN | D | 501 | -110.653 | -17.494 | 51.648 | 1.00 | 30.51 |
| 22169 | O | GLN | D | 501 | -109.569 | -16.928 | 51.534 | 1.00 | 30.08 |
| 22170 | N | MET | D | 502 | -110.766 | -18.797 | 51.877 | 1.00 | 31.53 |
| 22171 | CA | MET | D | 502 | -109.622 | -19.682 | 51.953 | 1.00 | 32.54 |
| 22172 | CB | MET | D | 502 | -109.324 | -20.061 | 53.404 | 1.00 | 32.70 |
| 22173 | CG | MET | D | 502 | -108.513 | -19.042 | 54.188 | 1.00 | 34.45 |
| 22174 | SD | MET | D | 502 | -108.298 | -19.546 | 55.914 | 1.00 | 35.68 |
| 22175 | CE | MET | D | 502 | -107.112 | -18.330 | 56.520 | 1.00 | 34.73 |

FIGURE 3 PS

| A | B | C | D | E | F | G | H | I | J |
|---|---|---|---|---|---|---|---|---|---|
| 22176 | C | MET | D | 502 | -109.930 | -20.951 | 51.188 | 1.00 | 33.44 |
| 22177 | O | MET | D | 502 | -110.969 | -21.568 | 51.401 | 1.00 | 33.39 |
| 22178 | N | ILE | D | 503 | -109.043 | -21.321 | 50.276 | 1.00 | 34.24 |
| 22179 | CA | ILE | D | 503 | -109.140 | -22.600 | 49.625 | 1.00 | 35.32 |
| 22180 | CB | ILE | D | 503 | -108.522 | -22.555 | 48.237 | 1.00 | 35.54 |
| 22181 | CG1 | ILE | D | 503 | -109.022 | -21.318 | 47.470 | 1.00 | 35.46 |
| 22182 | CD1 | ILE | D | 503 | -110.530 | -21.194 | 47.404 | 1.00 | 34.04 |
| 22183 | CG2 | ILE | D | 503 | -108.834 | -23.835 | 47.467 | 1.00 | 34.63 |
| 22184 | C | ILE | D | 503 | -108.339 | -23.510 | 50.541 | 1.00 | 36.69 |
| 22185 | O | ILE | D | 503 | -107.110 | -23.450 | 50.581 | 1.00 | 36.53 |
| 22186 | N | LEU | D | 504 | -109.044 | -24.332 | 51.313 | 1.00 | 38.09 |
| 22187 | CA | LEU | D | 504 | -108.397 | -25.207 | 52.279 | 1.00 | 38.64 |
| 22188 | CB | LEU | D | 504 | -109.299 | -25.379 | 53.491 | 1.00 | 38.53 |
| 22189 | CG | LEU | D | 504 | -109.571 | -24.066 | 54.222 | 1.00 | 38.04 |
| 22190 | CD1 | LEU | D | 504 | -110.703 | -24.193 | 55.242 | 1.00 | 36.84 |
| 22191 | CD2 | LEU | D | 504 | -108.285 | -23.587 | 54.884 | 1.00 | 38.21 |
| 22192 | C | LEU | D | 504 | -108.071 | -26.551 | 51.688 | 1.00 | 39.40 |
| 22193 | O | LEU | D | 504 | -108.885 | -27.132 | 50.983 | 1.00 | 39.88 |
| 22194 | N | PRO | D | 505 | -106.857 | -27.021 | 51.937 | 1.00 | 40.67 |
| 22195 | CA | PRO | D | 505 | -106.436 | -28.366 | 51.525 | 1.00 | 41.89 |
| 22196 | CB | PRO | D | 505 | -105.048 | -28.497 | 52.153 | 1.00 | 41.89 |
| 22197 | CG | PRO | D | 505 | -104.568 | -27.097 | 52.306 | 1.00 | 41.09 |
| 22198 | CD | PRO | D | 505 | -105.777 | -26.277 | 52.611 | 1.00 | 40.38 |
| 22199 | C | PRO | D | 505 | -107.348 | -29.432 | 52.129 | 1.00 | 43.15 |
| 22200 | O | PRO | D | 505 | -107.765 | -29.284 | 53.282 | 1.00 | 42.92 |
| 22201 | N | PRO | D | 506 | -107.661 | -30.471 | 51.359 | 1.00 | 44.38 |
| 22202 | CA | PRO | D | 506 | -108.512 | -31.576 | 51.821 | 1.00 | 45.63 |
| 22203 | CB | PRO | D | 506 | -108.338 | -32.628 | 50.713 | 1.00 | 45.81 |
| 22204 | CG | PRO | D | 506 | -107.133 | -32.141 | 49.920 | 1.00 | 44.97 |
| 22205 | CD | PRO | D | 506 | -107.248 | -30.661 | 49.959 | 1.00 | 44.76 |
| 22206 | C | PRO | D | 506 | -108.060 | -32.138 | 53.167 | 1.00 | 46.50 |
| 22207 | O | PRO | D | 506 | -106.859 | -32.206 | 53.420 | 1.00 | 46.58 |
| 22208 | N | HIS | D | 507 | -109.010 | -32.515 | 54.019 | 1.00 | 47.48 |
| 22209 | CA | HIS | D | 507 | -108.696 | -33.051 | 55.351 | 1.00 | 48.38 |
| 22210 | CB | HIS | D | 507 | -107.775 | -34.271 | 55.253 | 1.00 | 48.50 |
| 22211 | CG | HIS | D | 507 | -108.183 | -35.249 | 54.192 | 1.00 | 49.31 |
| 22212 | ND1 | HIS | D | 507 | -109.479 | -35.702 | 54.053 | 1.00 | 49.86 |
| 22213 | CE1 | HIS | D | 507 | -109.546 | -36.537 | 53.031 | 1.00 | 50.44 |
| 22214 | NE2 | HIS | D | 507 | -108.339 | -36.645 | 52.503 | 1.00 | 50.57 |
| 22215 | CD2 | HIS | D | 507 | -107.468 | -35.851 | 53.211 | 1.00 | 49.82 |
| 22216 | C | HIS | D | 507 | -108.062 | -31.971 | 56.218 | 1.00 | 48.86 |
| 22217 | O | HIS | D | 507 | -107.338 | -32.255 | 57.172 | 1.00 | 49.17 |
| 22218 | N | PHE | D | 508 | -108.343 | -30.722 | 55.873 | 1.00 | 49.26 |
| 22219 | CA | PHE | D | 508 | -107.828 | -29.590 | 56.615 | 1.00 | 49.25 |
| 22220 | CB | PHE | D | 508 | -108.662 | -28.344 | 56.310 | 1.00 | 49.03 |
| 22221 | CG | PHE | D | 508 | -108.251 | -27.149 | 57.094 | 1.00 | 48.15 |
| 22222 | CD1 | PHE | D | 508 | -106.923 | -26.739 | 57.106 | 1.00 | 47.86 |
| 22223 | CE1 | PHE | D | 508 | -106.521 | -25.648 | 57.837 | 1.00 | 46.02 |
| 22224 | CZ | PHE | D | 508 | -107.452 | -24.943 | 58.556 | 1.00 | 48.39 |
| 22225 | CE2 | PHE | D | 508 | -108.790 | -25.342 | 58.553 | 1.00 | 48.71 |
| 22226 | CD2 | PHE | D | 508 | -109.178 | -26.443 | 57.828 | 1.00 | 47.35 |

FIGURE 3 PT

| A | B | C | D | E | F | G | H | I | J |
|---|---|---|---|---|---|---|---|---|---|
| 22227 | C | PHE | D | 508 | -107.857 | -29.910 | 58.101 | 1.00 | 49.48 |
| 22228 | O | PHE | D | 508 | -108.861 | -30.396 | 58.617 | 1.00 | 49.51 |
| 22229 | N | ASP | D | 509 | -106.754 | -29.620 | 58.780 | 1.00 | 49.87 |
| 22230 | CA | ASP | D | 509 | -106.582 | -29.939 | 60.196 | 1.00 | 50.47 |
| 22231 | CB | ASP | D | 509 | -105.602 | -31.119 | 60.309 | 1.00 | 50.55 |
| 22232 | CG | ASP | D | 509 | -105.216 | -31.460 | 61.747 | 1.00 | 50.89 |
| 22233 | OD1 | ASP | D | 509 | -105.729 | -30.849 | 62.708 | 1.00 | 51.30 |
| 22234 | OD2 | ASP | D | 509 | -104.389 | -32.353 | 62.003 | 1.00 | 50.81 |
| 22235 | C | ASP | D | 509 | -106.055 | -28.715 | 60.937 | 1.00 | 50.61 |
| 22236 | O | ASP | D | 509 | -104.914 | -28.329 | 60.762 | 1.00 | 51.02 |
| 22237 | N | LYS | D | 510 | -106.884 | -28.115 | 61.778 | 1.00 | 51.30 |
| 22238 | CA | LYS | D | 510 | -106.497 | -26.912 | 62.511 | 1.00 | 51.94 |
| 22239 | CB | LYS | D | 510 | -107.683 | -26.370 | 63.308 | 1.00 | 52.13 |
| 22240 | CG | LYS | D | 510 | -108.946 | -26.229 | 62.476 | 1.00 | 53.76 |
| 22241 | CD | LYS | D | 510 | -109.630 | -27.587 | 62.196 | 1.00 | 55.82 |
| 22242 | CE | LYS | D | 510 | -110.779 | -27.432 | 61.182 | 1.00 | 56.53 |
| 22243 | NZ | LYS | D | 510 | -111.306 | -28.726 | 60.657 | 1.00 | 56.25 |
| 22244 | C | LYS | D | 510 | -105.274 | -27.117 | 63.414 | 1.00 | 51.89 |
| 22245 | O | LYS | D | 510 | -104.624 | -26.139 | 63.823 | 1.00 | 52.13 |
| 22246 | N | SER | D | 511 | -104.987 | -28.385 | 63.718 | 1.00 | 51.76 |
| 22247 | CA | SER | D | 511 | -103.810 | -28.790 | 64.483 | 1.00 | 51.57 |
| 22248 | CB | SER | D | 511 | -103.806 | -30.326 | 64.722 | 1.00 | 51.56 |
| 22249 | OG | SER | D | 511 | -104.808 | -30.721 | 65.636 | 1.00 | 52.43 |
| 22250 | C | SER | D | 511 | -102.566 | -28.441 | 63.678 | 1.00 | 50.79 |
| 22251 | O | SER | D | 511 | -101.568 | -27.977 | 64.221 | 1.00 | 50.95 |
| 22252 | N | LYS | D | 512 | -102.631 | -28.712 | 62.376 | 1.00 | 49.63 |
| 22253 | CA | LYS | D | 512 | -101.477 | -28.545 | 61.486 | 1.00 | 48.88 |
| 22254 | CB | LYS | D | 512 | -101.690 | -29.310 | 60.170 | 1.00 | 48.91 |
| 22255 | CG | LYS | D | 512 | -101.353 | -30.796 | 60.237 | 1.00 | 49.94 |
| 22256 | CD | LYS | D | 512 | -101.394 | -31.479 | 58.853 | 1.00 | 50.87 |
| 22257 | CE | LYS | D | 512 | -100.707 | -32.853 | 58.905 | 1.00 | 52.87 |
| 22258 | NZ | LYS | D | 512 | -101.267 | -33.870 | 57.941 | 1.00 | 54.85 |
| 22259 | C | LYS | D | 512 | -101.101 | -27.094 | 61.188 | 1.00 | 47.84 |
| 22260 | O | LYS | D | 512 | -101.847 | -26.163 | 61.472 | 1.00 | 47.97 |
| 22261 | N | LYS | D | 513 | -99.920 | -26.902 | 60.627 | 1.00 | 46.79 |
| 22262 | CA | LYS | D | 513 | -99.504 | -25.558 | 60.251 | 1.00 | 45.61 |
| 22263 | CB | LYS | D | 513 | -98.282 | -25.121 | 61.044 | 1.00 | 45.55 |
| 22264 | CG | LYS | D | 513 | -98.603 | -24.846 | 62.497 | 1.00 | 46.64 |
| 22265 | CD | LYS | D | 513 | -97.743 | -23.746 | 63.075 | 1.00 | 46.94 |
| 22266 | CE | LYS | D | 513 | -98.316 | -23.259 | 64.399 | 1.00 | 49.00 |
| 22267 | NZ | LYS | D | 513 | -98.235 | -21.737 | 64.532 | 1.00 | 49.85 |
| 22268 | C | LYS | D | 513 | -99.255 | -25.524 | 58.757 | 1.00 | 44.59 |
| 22269 | O | LYS | D | 513 | -98.264 | -26.061 | 58.267 | 1.00 | 44.12 |
| 22270 | N | TYR | D | 514 | -100.171 | -24.908 | 58.020 | 1.00 | 43.69 |
| 22271 | CA | TYR | D | 514 | -100.033 | -24.916 | 56.570 | 1.00 | 43.23 |
| 22272 | CB | TYR | D | 514 | -101.392 | -25.021 | 55.892 | 1.00 | 43.28 |
| 22273 | CG | TYR | D | 514 | -102.168 | -26.271 | 56.231 | 1.00 | 43.54 |
| 22274 | CD1 | TYR | D | 514 | -102.218 | -27.332 | 55.351 | 1.00 | 43.92 |
| 22275 | CE1 | TYR | D | 514 | -102.933 | -28.470 | 55.649 | 1.00 | 45.73 |
| 22276 | CZ | TYR | D | 514 | -103.620 | -28.556 | 56.841 | 1.00 | 45.89 |
| 22277 | OH | TYR | D | 514 | -104.330 | -29.691 | 57.133 | 1.00 | 46.74 |

FIGURE 3 PU

| A | B | C | D | E | F | G | H | I | J |
|---|---|---|---|---|---|---|---|---|---|
| 22278 | CE2 | TYR | D | 514 | -103.587 | -27.518 | 57.736 | 1.00 | 45.40 |
| 22279 | CD2 | TYR | D | 514 | -102.862 | -26.379 | 57.427 | 1.00 | 44.60 |
| 22280 | C | TYR | D | 514 | -99.290 | -23.724 | 56.006 | 1.00 | 42.59 |
| 22281 | O | TYR | D | 514 | -99.398 | -22.611 | 56.514 | 1.00 | 42.05 |
| 22282 | N | PRO | D | 515 | -98.513 | -23.982 | 54.960 | 1.00 | 42.36 |
| 22283 | CA | PRO | D | 515 | -97.865 | -22.922 | 54.202 | 1.00 | 42.34 |
| 22284 | CB | PRO | D | 515 | -97.008 | -23.697 | 53.213 | 1.00 | 42.20 |
| 22285 | CG | PRO | D | 515 | -97.773 | -24.933 | 53.041 | 1.00 | 42.49 |
| 22286 | CD | PRO | D | 515 | -98.160 | -25.310 | 54.438 | 1.00 | 42.14 |
| 22287 | C | PRO | D | 515 | -98.949 | -22.201 | 53.431 | 1.00 | 42.45 |
| 22288 | O | PRO | D | 515 | -100.132 | -22.569 | 53.429 | 1.00 | 41.35 |
| 22289 | OXT | PRO | D | 515 | -98.641 | -21.219 | 52.766 | 1.00 | 43.57 |
| 22290 | N | LEU | D | 516 | -98.960 | -20.077 | 53.844 | 1.00 | 31.95 |
| 22291 | CA | LEU | D | 516 | -100.197 | -19.740 | 53.113 | 1.00 | 30.92 |
| 22292 | CB | LEU | D | 516 | -101.122 | -18.957 | 54.031 | 1.00 | 31.48 |
| 22293 | CG | LEU | D | 516 | -102.410 | -18.366 | 53.469 | 1.00 | 32.65 |
| 22294 | CD1 | LEU | D | 516 | -102.137 | -16.938 | 53.024 | 1.00 | 34.39 |
| 22295 | CD2 | LEU | D | 516 | -103.453 | -18.376 | 54.569 | 1.00 | 33.16 |
| 22296 | C | LEU | D | 516 | -99.794 | -18.924 | 51.899 | 1.00 | 30.86 |
| 22297 | O | LEU | D | 516 | -98.681 | -18.396 | 51.840 | 1.00 | 30.71 |
| 22298 | N | LEU | D | 517 | -100.685 | -18.880 | 50.912 | 1.00 | 29.90 |
| 22299 | CA | LEU | D | 517 | -100.508 | -18.081 | 49.728 | 1.00 | 28.83 |
| 22300 | CB | LEU | D | 517 | -100.500 | -18.953 | 48.473 | 1.00 | 28.59 |
| 22301 | CG | LEU | D | 517 | -100.426 | -18.150 | 47.174 | 1.00 | 29.21 |
| 22302 | CD1 | LEU | D | 517 | -100.439 | -19.035 | 45.925 | 1.00 | 27.67 |
| 22303 | CD2 | LEU | D | 517 | -99.206 | -17.196 | 47.170 | 1.00 | 28.21 |
| 22304 | C | LEU | D | 517 | -101.673 | -17.098 | 49.668 | 1.00 | 28.95 |
| 22305 | O | LEU | D | 517 | -102.843 | -17.503 | 49.539 | 1.00 | 28.88 |
| 22306 | N | LEU | D | 518 | -101.349 | -15.810 | 49.777 | 1.00 | 28.01 |
| 22307 | CA | LEU | D | 518 | -102.338 | -14.745 | 49.681 | 1.00 | 27.58 |
| 22308 | CB | LEU | D | 518 | -101.879 | -13.519 | 50.470 | 1.00 | 27.31 |
| 22309 | CG | LEU | D | 518 | -102.951 | -12.446 | 50.616 | 1.00 | 28.02 |
| 22310 | CD1 | LEU | D | 518 | -104.293 | -13.056 | 51.060 | 1.00 | 27.01 |
| 22311 | CD2 | LEU | D | 518 | -102.494 | -11.371 | 51.585 | 1.00 | 29.52 |
| 22312 | C | LEU | D | 518 | -102.589 | -14.375 | 48.211 | 1.00 | 27.23 |
| 22313 | O | LEU | D | 518 | -101.708 | -13.849 | 47.524 | 1.00 | 26.48 |
| 22314 | N | ASP | D | 519 | -103.794 | -14.677 | 47.733 | 1.00 | 27.06 |
| 22315 | CA | ASP | D | 519 | -104.181 | -14.391 | 46.350 | 1.00 | 27.13 |
| 22316 | CB | ASP | D | 519 | -105.190 | -15.442 | 45.858 | 1.00 | 27.78 |
| 22317 | CG | ASP | D | 519 | -105.558 | -15.257 | 44.394 | 1.00 | 29.59 |
| 22318 | OD1 | ASP | D | 519 | -106.065 | -16.214 | 43.791 | 1.00 | 26.91 |
| 22319 | OD2 | ASP | D | 519 | -105.351 | -14.191 | 43.764 | 1.00 | 33.79 |
| 22320 | C | ASP | D | 519 | -104.808 | -13.000 | 46.324 | 1.00 | 26.13 |
| 22321 | O | ASP | D | 519 | -105.915 | -12.827 | 46.806 | 1.00 | 25.43 |
| 22322 | N | VAL | D | 520 | -104.094 | -12.008 | 45.787 | 1.00 | 25.46 |
| 22323 | CA | VAL | D | 520 | -104.589 | -10.646 | 45.858 | 1.00 | 24.15 |
| 22324 | CB | VAL | D | 520 | -103.584 | -9.692 | 46.605 | 1.00 | 24.63 |
| 22325 | CG1 | VAL | D | 520 | -102.264 | -9.584 | 45.883 | 1.00 | 24.11 |
| 22326 | CG2 | VAL | D | 520 | -104.178 | -8.316 | 46.774 | 1.00 | 23.64 |
| 22327 | C | VAL | D | 520 | -104.935 | -9.991 | 44.553 | 1.00 | 23.88 |
| 22328 | O | VAL | D | 520 | -104.271 | -10.204 | 43.532 | 1.00 | 23.79 |

FIGURE 3 PV

| A | B | C | D | E | F | G | H | I | J |
|---|---|---|---|---|---|---|---|---|---|
| 22329 | N | TYR | D | 521 | -105.996 | -9.187 | 44.585 | 1.00 | 23.58 |
| 22330 | CA | TYR | D | 521 | -106.262 | -8.275 | 43.485 | 1.00 | 22.82 |
| 22331 | CB | TYR | D | 521 | -107.542 | -8.584 | 42.725 | 1.00 | 23.10 |
| 22332 | CG | TYR | D | 521 | -107.669 | -7.674 | 41.510 | 1.00 | 24.19 |
| 22333 | CD1 | TYR | D | 521 | -108.651 | -6.681 | 41.453 | 1.00 | 22.84 |
| 22334 | CE1 | TYR | D | 521 | -108.755 | -5.837 | 40.348 | 1.00 | 25.15 |
| 22335 | CZ | TYR | D | 521 | -107.842 | -5.969 | 39.300 | 1.00 | 25.26 |
| 22336 | OH | TYR | D | 521 | -107.905 | -5.133 | 38.220 | 1.00 | 26.53 |
| 22337 | CE2 | TYR | D | 521 | -106.864 | -6.943 | 39.333 | 1.00 | 25.44 |
| 22338 | CD2 | TYR | D | 521 | -106.773 | -7.787 | 40.441 | 1.00 | 24.42 |
| 22339 | C | TYR | D | 521 | -106.306 | -6.906 | 44.122 | 1.00 | 22.83 |
| 22340 | O | TYR | D | 521 | -105.392 | -6.084 | 43.946 | 1.00 | 23.01 |
| 22341 | N | ALA | D | 522 | -107.371 | -6.662 | 44.863 | 1.00 | 22.47 |
| 22342 | CA | ALA | D | 522 | -107.460 | -5.494 | 45.727 | 1.00 | 22.89 |
| 22343 | CB | ALA | D | 522 | -106.274 | -5.457 | 46.713 | 1.00 | 22.69 |
| 22344 | C | ALA | D | 522 | -107.590 | -4.161 | 45.031 | 1.00 | 23.27 |
| 22345 | O | ALA | D | 522 | -107.339 | -3.122 | 45.656 | 1.00 | 23.27 |
| 22346 | N | GLY | D | 523 | -107.964 | -4.179 | 43.754 | 1.00 | 23.25 |
| 22347 | CA | GLY | D | 523 | -108.228 | -2.941 | 43.044 | 1.00 | 23.46 |
| 22348 | C | GLY | D | 523 | -109.525 | -2.363 | 43.562 | 1.00 | 23.53 |
| 22349 | O | GLY | D | 523 | -110.302 | -3.045 | 44.218 | 1.00 | 24.01 |
| 22350 | N | PRO | D | 524 | -109.779 | -1.101 | 43.270 | 1.00 | 23.81 |
| 22351 | CA | PRO | D | 524 | -111.034 | -0.464 | 43.701 | 1.00 | 23.35 |
| 22352 | CB | PRO | D | 524 | -110.958 | 0.924 | 43.088 | 1.00 | 22.72 |
| 22353 | CG | PRO | D | 524 | -109.504 | 1.158 | 42.890 | 1.00 | 23.47 |
| 22354 | CD | PRO | D | 524 | -108.893 | -0.175 | 42.545 | 1.00 | 23.33 |
| 22355 | C | PRO | D | 524 | -112.257 | -1.215 | 43.206 | 1.00 | 23.56 |
| 22356 | O | PRO | D | 524 | -112.310 | -1.632 | 42.045 | 1.00 | 22.25 |
| 22357 | N | CYS | D | 525 | -113.213 | -1.396 | 44.123 | 1.00 | 23.85 |
| 22358 | CA | CYS | D | 525 | -114.442 | -2.133 | 43.883 | 1.00 | 24.64 |
| 22359 | CB | CYS | D | 525 | -115.325 | -1.457 | 42.816 | 1.00 | 24.68 |
| 22360 | SG | CYS | D | 525 | -117.079 | -1.893 | 42.910 | 1.00 | 27.11 |
| 22361 | C | CYS | D | 525 | -114.201 | -3.605 | 43.551 | 1.00 | 24.37 |
| 22362 | O | CYS | D | 525 | -115.053 | -4.260 | 43.009 | 1.00 | 25.04 |
| 22363 | N | SER | D | 526 | -113.047 | -4.137 | 43.884 | 1.00 | 24.74 |
| 22364 | CA | SER | D | 526 | -112.831 | -5.541 | 43.611 | 1.00 | 25.47 |
| 22365 | CB | SER | D | 526 | -111.353 | -5.879 | 43.649 | 1.00 | 25.00 |
| 22366 | OG | SER | D | 526 | -110.870 | -5.697 | 44.965 | 1.00 | 26.65 |
| 22367 | C | SER | D | 526 | -113.539 | -6.373 | 44.674 | 1.00 | 25.58 |
| 22368 | O | SER | D | 526 | -114.006 | -5.853 | 45.694 | 1.00 | 25.12 |
| 22369 | N | GLN | D | 527 | -113.597 | -7.665 | 44.408 | 1.00 | 25.65 |
| 22370 | CA | GLN | D | 527 | -114.135 | -8.629 | 45.318 | 1.00 | 26.62 |
| 22371 | CB | GLN | D | 527 | -115.634 | -8.825 | 45.097 | 1.00 | 26.82 |
| 22372 | CG | GLN | D | 527 | -116.280 | -9.642 | 46.207 | 1.00 | 27.95 |
| 22373 | CD | GLN | D | 527 | -117.803 | -9.657 | 46.152 | 1.00 | 28.44 |
| 22374 | OE1 | GLN | D | 527 | -118.407 | -10.192 | 45.204 | 1.00 | 28.61 |
| 22375 | NE2 | GLN | D | 527 | -118.424 | -9.077 | 47.166 | 1.00 | 27.33 |
| 22376 | C | GLN | D | 527 | -113.434 | -9.907 | 44.989 | 1.00 | 27.21 |
| 22377 | O | GLN | D | 527 | -113.576 | -10.406 | 43.888 | 1.00 | 27.15 |
| 22378 | N | LYS | D | 528 | -112.661 | -10.430 | 45.934 | 1.00 | 28.38 |
| 22379 | CA | LYS | D | 528 | -111.977 | -11.690 | 45.740 | 1.00 | 29.21 |

FIGURE 3 PW

| A | B | C | D | E | F | G | H | I | J |
|---|---|---|---|---|---|---|---|---|---|
| 22380 | CB | LYS | D | 528 | -110.469 | -11.517 | 45.892 | 1.00 | 29.88 |
| 22381 | CG | LYS | D | 528 | -109.811 | -10.599 | 44.854 | 1.00 | 31.00 |
| 22382 | CD | LYS | D | 528 | -109.819 | -11.175 | 43.455 | 1.00 | 29.85 |
| 22383 | CE | LYS | D | 528 | -109.210 | -12.545 | 43.375 | 1.00 | 32.75 |
| 22384 | NZ | LYS | D | 528 | -107.963 | -12.709 | 44.124 | 1.00 | 32.18 |
| 22385 | C | LYS | D | 528 | -112.482 | -12.710 | 46.743 | 1.00 | 29.69 |
| 22386 | O | LYS | D | 528 | -112.047 | -13.844 | 46.746 | 1.00 | 28.93 |
| 22387 | N | ALA | D | 529 | -113.362 | -12.293 | 47.641 | 1.00 | 31.26 |
| 22388 | CA | ALA | D | 529 | -113.948 | -13.252 | 48.571 | 1.00 | 32.56 |
| 22389 | CB | ALA | D | 529 | -113.970 | -12.708 | 49.973 | 1.00 | 32.17 |
| 22390 | C | ALA | D | 529 | -115.357 | -13.498 | 48.054 | 1.00 | 33.38 |
| 22391 | O | ALA | D | 529 | -116.234 | -12.672 | 48.299 | 1.00 | 33.84 |
| 22392 | N | ASP | D | 530 | -115.536 | -14.607 | 47.319 | 1.00 | 34.00 |
| 22393 | CA | ASP | D | 530 | -116.783 | -14.967 | 46.606 | 1.00 | 35.36 |
| 22394 | CB | ASP | D | 530 | -116.490 | -15.349 | 45.126 | 1.00 | 35.29 |
| 22395 | CG | ASP | D | 530 | -115.969 | -14.213 | 44.287 | 1.00 | 38.56 |
| 22396 | OD1 | ASP | D | 530 | -116.423 | -14.084 | 43.138 | 1.00 | 41.15 |
| 22397 | OD2 | ASP | D | 530 | -115.062 | -13.420 | 44.632 | 1.00 | 45.19 |
| 22398 | C | ASP | D | 530 | -117.403 | -16.253 | 47.157 | 1.00 | 34.96 |
| 22399 | O | ASP | D | 530 | -116.764 | -16.985 | 47.886 | 1.00 | 35.34 |
| 22400 | N | THR | D | 531 | -118.630 | -16.553 | 46.741 | 1.00 | 34.45 |
| 22401 | CA | THR | D | 531 | -119.231 | -17.849 | 47.016 | 1.00 | 34.17 |
| 22402 | CB | THR | D | 531 | -120.712 | -17.756 | 47.493 | 1.00 | 34.07 |
| 22403 | OG1 | THR | D | 531 | -121.523 | -17.144 | 46.477 | 1.00 | 34.32 |
| 22404 | CG2 | THR | D | 531 | -120.866 | -16.824 | 48.689 | 1.00 | 33.95 |
| 22405 | C | THR | D | 531 | -119.205 | -18.586 | 45.695 | 1.00 | 34.05 |
| 22406 | O | THR | D | 531 | -120.026 | -19.455 | 45.466 | 1.00 | 33.61 |
| 22407 | N | VAL | D | 532 | -118.288 | -18.198 | 44.807 | 1.00 | 33.97 |
| 22408 | CA | VAL | D | 532 | -118.193 | -18.819 | 43.487 | 1.00 | 33.24 |
| 22409 | CB | VAL | D | 532 | -117.643 | -17.840 | 42.418 | 1.00 | 33.74 |
| 22410 | CG1 | VAL | D | 532 | -117.397 | -18.559 | 41.073 | 1.00 | 31.82 |
| 22411 | CG2 | VAL | D | 532 | -118.593 | -16.654 | 42.224 | 1.00 | 32.78 |
| 22412 | C | VAL | D | 532 | -117.344 | -20.082 | 43.507 | 1.00 | 33.28 |
| 22413 | O | VAL | D | 532 | -116.378 | -20.193 | 44.268 | 1.00 | 32.79 |
| 22414 | N | PHE | D | 533 | -117.723 | -21.039 | 42.667 | 1.00 | 33.08 |
| 22415 | CA | PHE | D | 533 | -116.998 | -22.291 | 42.566 | 1.00 | 32.91 |
| 22416 | CB | PHE | D | 533 | -117.936 | -23.465 | 42.297 | 1.00 | 33.19 |
| 22417 | CG | PHE | D | 533 | -117.209 | -24.742 | 42.033 | 1.00 | 33.43 |
| 22418 | CD1 | PHE | D | 533 | -116.675 | -25.468 | 43.079 | 1.00 | 33.91 |
| 22419 | CE1 | PHE | D | 533 | -115.974 | -26.632 | 42.848 | 1.00 | 33.49 |
| 22420 | CZ | PHE | D | 533 | -115.793 | -27.068 | 41.569 | 1.00 | 33.77 |
| 22421 | CE2 | PHE | D | 533 | -116.305 | -26.341 | 40.509 | 1.00 | 35.32 |
| 22422 | CD2 | PHE | D | 533 | -116.999 | -25.180 | 40.743 | 1.00 | 33.72 |
| 22423 | C | PHE | D | 533 | -116.028 | -22.207 | 41.428 | 1.00 | 32.73 |
| 22424 | O | PHE | D | 533 | -116.404 | -21.924 | 40.304 | 1.00 | 32.88 |
| 22425 | N | ARG | D | 534 | -114.773 | -22.493 | 41.703 | 1.00 | 33.21 |
| 22426 | CA | ARG | D | 534 | -113.764 | -22.376 | 40.675 | 1.00 | 33.45 |
| 22427 | CB | ARG | D | 534 | -112.917 | -21.111 | 40.906 | 1.00 | 34.03 |
| 22428 | CG | ARG | D | 534 | -113.685 | -19.780 | 40.894 | 1.00 | 33.35 |
| 22429 | CD | ARG | D | 534 | -112.769 | -18.543 | 40.923 | 1.00 | 33.39 |
| 22430 | NE | ARG | D | 534 | -113.530 | -17.303 | 40.775 | 1.00 | 32.63 |

FIGURE 3 PX

| A | B | C | D | E | F | G | H | I | J |
|---|---|---|---|---|---|---|---|---|---|
| 22431 | CZ | ARG | D | 534 | -114.159 | -16.700 | 41.771 | 1.00 | 30.97 |
| 22432 | NH1 | ARG | D | 534 | -114.862 | -15.592 | 41.543 | 1.00 | 30.56 |
| 22433 | NH2 | ARG | D | 534 | -114.100 | -17.216 | 42.991 | 1.00 | 27.55 |
| 22434 | C | ARG | D | 534 | -112.844 | -23.578 | 40.649 | 1.00 | 33.45 |
| 22435 | O | ARG | D | 534 | -112.604 | -24.228 | 41.670 | 1.00 | 33.84 |
| 22436 | N | LEU | D | 535 | -112.347 | -23.869 | 39.459 | 1.00 | 32.92 |
| 22437 | CA | LEU | D | 535 | -111.330 | -24.873 | 39.276 | 1.00 | 32.75 |
| 22438 | CB | LEU | D | 535 | -111.794 | -25.967 | 38.330 | 1.00 | 33.22 |
| 22439 | CG | LEU | D | 535 | -113.001 | -26.703 | 38.907 | 1.00 | 34.43 |
| 22440 | CD1 | LEU | D | 535 | -113.453 | -27.749 | 37.909 | 1.00 | 36.11 |
| 22441 | CD2 | LEU | D | 535 | -112.653 | -27.322 | 40.271 | 1.00 | 32.76 |
| 22442 | C | LEU | D | 535 | -110.201 | -24.092 | 38.668 | 1.00 | 32.22 |
| 22443 | O | LEU | D | 535 | -110.243 | -23.712 | 37.493 | 1.00 | 30.98 |
| 22444 | N | ASN | D | 536 | -109.206 | -23.810 | 39.498 | 1.00 | 32.18 |
| 22445 | CA | ASN | D | 536 | -108.085 | -23.001 | 39.066 | 1.00 | 31.90 |
| 22446 | CB | ASN | D | 536 | -108.384 | -21.536 | 39.359 | 1.00 | 31.60 |
| 22447 | CG | ASN | D | 536 | -108.677 | -21.291 | 40.818 | 1.00 | 31.90 |
| 22448 | OD1 | ASN | D | 536 | -108.304 | -22.105 | 41.678 | 1.00 | 31.63 |
| 22449 | ND2 | ASN | D | 536 | -109.340 | -20.161 | 41.122 | 1.00 | 29.42 |
| 22450 | C | ASN | D | 536 | -106.775 | -23.425 | 39.704 | 1.00 | 31.71 |
| 22451 | O | ASN | D | 536 | -106.671 | -24.492 | 40.296 | 1.00 | 31.78 |
| 22452 | N | TRP | D | 537 | -105.768 | -22.577 | 39.566 | 1.00 | 31.71 |
| 22453 | CA | TRP | D | 537 | -104.455 | -22.868 | 40.092 | 1.00 | 31.28 |
| 22454 | CB | TRP | D | 537 | -103.569 | -21.655 | 39.873 | 1.00 | 30.97 |
| 22455 | CG | TRP | D | 537 | -102.151 | -21.917 | 40.133 | 1.00 | 28.42 |
| 22456 | CD1 | TRP | D | 537 | -101.437 | -23.003 | 39.750 | 1.00 | 26.24 |
| 22457 | NE1 | TRP | D | 537 | -100.129 | -22.874 | 40.147 | 1.00 | 26.79 |
| 22458 | CE2 | TRP | D | 537 | -99.987 | -21.686 | 40.814 | 1.00 | 26.24 |
| 22459 | CD2 | TRP | D | 537 | -101.244 | -21.054 | 40.813 | 1.00 | 28.24 |
| 22460 | CE3 | TRP | D | 537 | -101.368 | -19.802 | 41.436 | 1.00 | 26.92 |
| 22461 | CZ3 | TRP | D | 537 | -100.275 | -19.248 | 42.025 | 1.00 | 26.67 |
| 22462 | CH2 | TRP | D | 537 | -99.035 | -19.898 | 42.002 | 1.00 | 28.13 |
| 22463 | CZ2 | TRP | D | 537 | -98.874 | -21.117 | 41.396 | 1.00 | 27.01 |
| 22464 | C | TRP | D | 537 | -104.551 | -23.137 | 41.575 | 1.00 | 31.39 |
| 22465 | O | TRP | D | 537 | -103.943 | -24.065 | 42.098 | 1.00 | 32.11 |
| 22466 | N | ALA | D | 538 | -105.315 | -22.298 | 42.255 | 1.00 | 31.48 |
| 22467 | CA | ALA | D | 538 | -105.494 | -22.417 | 43.683 | 1.00 | 31.67 |
| 22468 | CB | ALA | D | 538 | -106.381 | -21.287 | 44.196 | 1.00 | 31.61 |
| 22469 | C | ALA | D | 538 | -106.073 | -23.783 | 44.057 | 1.00 | 31.89 |
| 22470 | O | ALA | D | 538 | -105.707 | -24.346 | 45.077 | 1.00 | 32.15 |
| 22471 | N | THR | D | 539 | -106.983 | -24.306 | 43.241 | 1.00 | 32.44 |
| 22472 | CA | THR | D | 539 | -107.528 | -25.635 | 43.487 | 1.00 | 33.01 |
| 22473 | CB | THR | D | 539 | -108.526 | -26.049 | 42.393 | 1.00 | 32.91 |
| 22474 | OG1 | THR | D | 539 | -109.510 | -25.030 | 42.220 | 1.00 | 32.56 |
| 22475 | CG2 | THR | D | 539 | -109.365 | -27.234 | 42.861 | 1.00 | 33.33 |
| 22476 | C | THR | D | 539 | -106.371 | -26.625 | 43.536 | 1.00 | 33.42 |
| 22477 | O | THR | D | 539 | -106.253 | -27.407 | 44.467 | 1.00 | 33.41 |
| 22478 | N | TYR | D | 540 | -105.504 | -26.569 | 42.533 | 1.00 | 33.82 |
| 22479 | CA | TYR | D | 540 | -104.343 | -27.452 | 42.482 | 1.00 | 34.43 |
| 22480 | CB | TYR | D | 540 | -103.574 | -27.267 | 41.166 | 1.00 | 34.19 |
| 22481 | CG | TYR | D | 540 | -102.083 | -27.408 | 41.334 | 1.00 | 35.99 |

FIGURE 3 PY

| A | B | C | D | E | F | G | H | I | J |
|---|---|---|---|---|---|---|---|---|---|
| 22482 | CD1 | TYR | D | 540 | -101.239 | -26.291 | 41.266 | 1.00 | 36.53 |
| 22483 | CE1 | TYR | D | 540 | -99.870 | -26.416 | 41.430 | 1.00 | 36.80 |
| 22484 | CZ | TYR | D | 540 | -99.321 | -27.666 | 41.678 | 1.00 | 39.13 |
| 22485 | OH | TYR | D | 540 | -97.947 | -27.817 | 41.841 | 1.00 | 39.63 |
| 22486 | CE2 | TYR | D | 540 | -100.144 | -28.783 | 41.756 | 1.00 | 38.20 |
| 22487 | CD2 | TYR | D | 540 | -101.512 | -28.647 | 41.583 | 1.00 | 36.76 |
| 22488 | C | TYR | D | 540 | -103.403 | -27.263 | 43.674 | 1.00 | 34.61 |
| 22489 | O | TYR | D | 540 | -102.846 | -28.227 | 44.187 | 1.00 | 35.20 |
| 22490 | N | LEU | D | 541 | -103.220 | -26.030 | 44.125 | 1.00 | 34.49 |
| 22491 | CA | LEU | D | 541 | -102.306 | -25.801 | 45.246 | 1.00 | 34.30 |
| 22492 | CB | LEU | D | 541 | -101.986 | -24.305 | 45.422 | 1.00 | 33.43 |
| 22493 | CG | LEU | D | 541 | -101.287 | -23.566 | 44.280 | 1.00 | 33.62 |
| 22494 | CD1 | LEU | D | 541 | -101.321 | -22.060 | 44.528 | 1.00 | 33.14 |
| 22495 | CD2 | LEU | D | 541 | -99.857 | -24.053 | 44.067 | 1.00 | 30.95 |
| 22496 | C | LEU | D | 541 | -102.816 | -26.372 | 46.568 | 1.00 | 34.23 |
| 22497 | O | LEU | D | 541 | -102.043 | -26.919 | 47.365 | 1.00 | 34.14 |
| 22498 | N | ALA | D | 542 | -104.107 | -26.211 | 46.820 | 1.00 | 34.20 |
| 22499 | CA | ALA | D | 542 | -104.689 | -26.682 | 48.067 | 1.00 | 34.60 |
| 22500 | CB | ALA | D | 542 | -106.072 | -26.089 | 48.250 | 1.00 | 34.08 |
| 22501 | C | ALA | D | 542 | -104.774 | -28.210 | 48.081 | 1.00 | 35.01 |
| 22502 | O | ALA | D | 542 | -104.430 | -28.873 | 49.069 | 1.00 | 34.56 |
| 22503 | N | SER | D | 543 | -105.207 | -28.740 | 46.945 | 1.00 | 35.36 |
| 22504 | CA | SER | D | 543 | -105.488 | -30.145 | 46.784 | 1.00 | 36.01 |
| 22505 | CB | SER | D | 543 | -106.223 | -30.344 | 45.461 | 1.00 | 36.05 |
| 22506 | OG | SER | D | 543 | -106.513 | -31.706 | 45.239 | 1.00 | 38.51 |
| 22507 | C | SER | D | 543 | -104.241 | -30.982 | 46.806 | 1.00 | 36.06 |
| 22508 | O | SER | D | 543 | -104.138 | -31.932 | 47.576 | 1.00 | 35.64 |
| 22509 | N | THR | D | 582 | -103.278 | -30.613 | 45.964 | 1.00 | 36.46 |
| 22510 | CA | THR | D | 544 | -102.064 | -31.412 | 45.797 | 1.00 | 36.40 |
| 22511 | CB | THR | D | 544 | -101.614 | -31.355 | 44.335 | 1.00 | 36.34 |
| 22512 | OG1 | THR | D | 544 | -102.676 | -31.788 | 43.484 | 1.00 | 37.72 |
| 22513 | CG2 | THR | D | 544 | -100.522 | -32.366 | 44.053 | 1.00 | 37.38 |
| 22514 | C | THR | D | 544 | -100.911 | -30.964 | 46.683 | 1.00 | 36.54 |
| 22515 | O | THR | D | 544 | -100.186 | -31.800 | 47.239 | 1.00 | 36.92 |
| 22516 | N | GLU | D | 545 | -100.729 | -29.649 | 46.816 | 1.00 | 35.81 |
| 22517 | CA | GLU | D | 545 | -99.558 | -29.141 | 47.515 | 1.00 | 35.27 |
| 22518 | CB | GLU | D | 545 | -98.870 | -28.052 | 46.674 | 1.00 | 34.96 |
| 22519 | CG | GLU | D | 545 | -98.775 | -28.409 | 45.193 | 1.00 | 34.43 |
| 22520 | CD | GLU | D | 545 | -97.587 | -29.292 | 44.853 | 1.00 | 33.89 |
| 22521 | OE1 | GLU | D | 545 | -97.339 | -29.558 | 43.650 | 1.00 | 32.37 |
| 22522 | OE2 | GLU | D | 545 | -96.881 | -29.715 | 45.787 | 1.00 | 35.41 |
| 22523 | C | GLU | D | 545 | -99.892 | -28.671 | 48.921 | 1.00 | 34.78 |
| 22524 | O | GLU | D | 545 | -99.077 | -28.076 | 49.611 | 1.00 | 35.19 |
| 22525 | N | ASN | D | 546 | -101.101 | -28.971 | 49.347 | 1.00 | 34.51 |
| 22526 | CA | ASN | D | 546 | -101.558 | -28.603 | 50.678 | 1.00 | 34.11 |
| 22527 | CB | ASN | D | 546 | -101.163 | -29.679 | 51.695 | 1.00 | 34.57 |
| 22528 | CG | ASN | D | 546 | -101.851 | -31.001 | 51.413 | 1.00 | 36.54 |
| 22529 | OD1 | ASN | D | 546 | -101.307 | -31.860 | 50.719 | 1.00 | 40.92 |
| 22530 | ND2 | ASN | D | 546 | -103.064 | -31.159 | 51.920 | 1.00 | 38.06 |
| 22531 | C | ASN | D | 546 | -101.198 | -27.195 | 51.136 | 1.00 | 33.35 |
| 22532 | O | ASN | D | 546 | -100.691 | -26.979 | 52.240 | 1.00 | 33.38 |

FIGURE 3 PZ

| A | B | C | D | E | F | G | H | I | J |
|---|---|---|---|---|---|---|---|---|---|
| 22533 | N | ILE | D | 547 | -101.497 | -26.236 | 50.269 | 1.00 | 32.27 |
| 22534 | CA | ILE | D | 547 | -101.311 | -24.827 | 50.545 | 1.00 | 30.72 |
| 22535 | CB | ILE | D | 547 | -100.623 | -24.155 | 49.330 | 1.00 | 31.08 |
| 22536 | CG1 | ILE | D | 547 | -99.209 | -24.719 | 49.142 | 1.00 | 29.43 |
| 22537 | CD1 | ILE | D | 547 | -98.621 | -24.443 | 47.817 | 1.00 | 24.93 |
| 22538 | CG2 | ILE | D | 547 | -100.610 | -22.626 | 49.482 | 1.00 | 30.21 |
| 22539 | C | ILE | D | 547 | -102.654 | -24.157 | 50.779 | 1.00 | 30.22 |
| 22540 | O | ILE | D | 547 | -103.548 | -24.256 | 49.950 | 1.00 | 30.31 |
| 22541 | N | ILE | D | 548 | -102.822 | -23.489 | 51.913 | 1.00 | 29.75 |
| 22542 | CA | ILE | D | 548 | -104.013 | -22.695 | 52.083 | 1.00 | 29.56 |
| 22543 | CB | ILE | D | 548 | -104.159 | -22.187 | 53.502 | 1.00 | 29.32 |
| 22544 | CG1 | ILE | D | 548 | -104.299 | -23.339 | 54.498 | 1.00 | 30.97 |
| 22545 | CD1 | ILE | D | 548 | -104.571 | -22.855 | 55.948 | 1.00 | 28.15 |
| 22546 | CG2 | ILE | D | 548 | -105.390 | -21.294 | 53.614 | 1.00 | 28.75 |
| 22547 | C | ILE | D | 548 | -103.874 | -21.491 | 51.156 | 1.00 | 29.79 |
| 22548 | O | ILE | D | 548 | -102.842 | -20.840 | 51.140 | 1.00 | 29.92 |
| 22549 | N | VAL | D | 549 | -104.887 | -21.195 | 50.360 | 1.00 | 29.75 |
| 22550 | CA | VAL | D | 549 | -104.787 | -19.987 | 49.572 | 1.00 | 29.97 |
| 22551 | CB | VAL | D | 549 | -104.492 | -20.228 | 48.067 | 1.00 | 29.86 |
| 22552 | CG1 | VAL | D | 549 | -104.788 | -21.627 | 47.679 | 1.00 | 31.52 |
| 22553 | CG2 | VAL | D | 549 | -105.192 | -19.204 | 47.198 | 1.00 | 30.60 |
| 22554 | C | VAL | D | 549 | -105.961 | -19.073 | 49.867 | 1.00 | 29.65 |
| 22555 | O | VAL | D | 549 | -107.125 | -19.410 | 49.628 | 1.00 | 29.74 |
| 22556 | N | ALA | D | 550 | -105.619 | -17.925 | 50.439 | 1.00 | 28.34 |
| 22557 | CA | ALA | D | 550 | -106.589 | -16.984 | 50.927 | 1.00 | 27.71 |
| 22558 | CB | ALA | D | 550 | -106.215 | -16.562 | 52.346 | 1.00 | 27.73 |
| 22559 | C | ALA | D | 550 | -106.675 | -15.750 | 50.054 | 1.00 | 27.36 |
| 22560 | O | ALA | D | 550 | -105.756 | -15.418 | 49.324 | 1.00 | 26.91 |
| 22561 | N | SER | D | 551 | -107.790 | -15.053 | 50.172 | 1.00 | 27.51 |
| 22562 | CA | SER | D | 551 | -107.961 | -13.810 | 49.461 | 1.00 | 28.01 |
| 22563 | CB | SER | D | 551 | -108.754 | -14.007 | 48.189 | 1.00 | 27.25 |
| 22564 | OG | SER | D | 551 | -107.986 | -14.798 | 47.310 | 1.00 | 28.09 |
| 22565 | C | SER | D | 551 | -108.707 | -13.001 | 50.433 | 1.00 | 27.68 |
| 22566 | O | SER | D | 551 | -109.465 | -13.565 | 51.223 | 1.00 | 28.39 |
| 22567 | N | PHE | D | 552 | -108.489 | -11.691 | 50.382 | 1.00 | 26.99 |
| 22568 | CA | PHE | D | 552 | -109.076 | -10.779 | 51.336 | 1.00 | 26.50 |
| 22569 | CB | PHE | D | 552 | -108.028 | -10.455 | 52.408 | 1.00 | 26.23 |
| 22570 | CG | PHE | D | 552 | -108.509 | -9.514 | 53.464 | 1.00 | 26.10 |
| 22571 | CD1 | PHE | D | 552 | -109.320 | -9.962 | 54.495 | 1.00 | 26.43 |
| 22572 | CE1 | PHE | D | 552 | -109.764 | -9.081 | 55.477 | 1.00 | 26.53 |
| 22573 | CZ | PHE | D | 552 | -109.404 | -7.758 | 55.425 | 1.00 | 25.63 |
| 22574 | CE2 | PHE | D | 552 | -108.595 | -7.310 | 54.418 | 1.00 | 25.99 |
| 22575 | CD2 | PHE | D | 552 | -108.145 | -8.190 | 53.439 | 1.00 | 25.54 |
| 22576 | C | PHE | D | 552 | -109.546 | -9.506 | 50.650 | 1.00 | 26.56 |
| 22577 | O | PHE | D | 552 | -108.831 | -8.934 | 49.849 | 1.00 | 26.45 |
| 22578 | N | ASP | D | 553 | -110.764 | -9.073 | 50.967 | 1.00 | 26.84 |
| 22579 | CA | ASP | D | 553 | -111.307 | -7.826 | 50.451 | 1.00 | 25.94 |
| 22580 | CB | ASP | D | 553 | -112.769 | -7.996 | 50.036 | 1.00 | 25.66 |
| 22581 | CG | ASP | D | 553 | -112.948 | -8.942 | 48.858 | 1.00 | 25.92 |
| 22582 | OD1 | ASP | D | 553 | -112.023 | -9.073 | 48.032 | 1.00 | 22.66 |
| 22583 | OD2 | ASP | D | 553 | -113.995 | -9.605 | 48.682 | 1.00 | 27.52 |

FIGURE 3 QA

| A | B | C | D | E | F | G | H | I | J |
|---|---|---|---|---|---|---|---|---|---|
| 22584 | C | ASP | D | 553 | -111.244 | -6.789 | 51.553 | 1.00 | 26.12 |
| 22585 | O | ASP | D | 553 | -112.113 | -6.762 | 52.432 | 1.00 | 26.68 |
| 22586 | N | GLY | D | 554 | -110.234 | -5.928 | 51.516 | 1.00 | 25.48 |
| 22587 | CA | GLY | D | 554 | -110.116 | -4.893 | 52.521 | 1.00 | 25.03 |
| 22588 | C | GLY | D | 554 | -110.654 | -3.556 | 52.057 | 1.00 | 24.97 |
| 22589 | O | GLY | D | 554 | -111.596 | -3.502 | 51.273 | 1.00 | 25.10 |
| 22590 | N | ARG | D | 555 | -110.063 | -2.468 | 52.546 | 1.00 | 24.82 |
| 22591 | CA | ARG | D | 555 | -110.487 | -1.142 | 52.127 | 1.00 | 24.46 |
| 22592 | CB | ARG | D | 555 | -109.787 | -0.067 | 52.952 | 1.00 | 24.30 |
| 22593 | CG | ARG | D | 555 | -110.429 | 0.147 | 54.341 | 1.00 | 24.14 |
| 22594 | CD | ARG | D | 555 | -109.582 | 0.985 | 55.282 | 1.00 | 23.12 |
| 22595 | NE | ARG | D | 555 | -108.311 | 0.342 | 55.614 | 1.00 | 22.67 |
| 22596 | CZ | ARG | D | 555 | -107.446 | 0.851 | 56.473 | 1.00 | 23.02 |
| 22597 | NH1 | ARG | D | 555 | -107.718 | 2.010 | 57.046 | 1.00 | 22.64 |
| 22598 | NH2 | ARG | D | 555 | -106.318 | 0.212 | 56.764 | 1.00 | 22.47 |
| 22599 | C | ARG | D | 555 | -110.262 | -0.957 | 50.615 | 1.00 | 24.24 |
| 22600 | O | ARG | D | 555 | -109.253 | -1.424 | 50.068 | 1.00 | 23.62 |
| 22601 | N | GLY | D | 556 | -111.209 | -0.285 | 49.959 | 1.00 | 23.17 |
| 22602 | CA | GLY | D | 556 | -111.192 | -0.154 | 48.514 | 1.00 | 23.85 |
| 22603 | C | GLY | D | 556 | -112.076 | -1.209 | 47.838 | 1.00 | 24.14 |
| 22604 | O | GLY | D | 556 | -112.551 | -1.008 | 46.727 | 1.00 | 23.54 |
| 22605 | N | SER | D | 557 | -112.309 | -2.330 | 48.519 | 1.00 | 24.74 |
| 22606 | CA | SER | D | 557 | -113.092 | -3.431 | 47.949 | 1.00 | 25.59 |
| 22607 | CB | SER | D | 557 | -112.978 | -4.696 | 48.811 | 1.00 | 25.61 |
| 22608 | OG | SER | D | 557 | -113.803 | -4.610 | 49.962 | 1.00 | 27.57 |
| 22609 | C | SER | D | 557 | -114.547 | -3.020 | 47.697 | 1.00 | 25.30 |
| 22610 | O | SER | D | 557 | -115.020 | -2.030 | 48.250 | 1.00 | 25.68 |
| 22611 | N | GLY | D | 558 | -115.246 | -3.759 | 46.840 | 1.00 | 25.65 |
| 22612 | CA | GLY | D | 558 | -116.579 | -3.350 | 46.401 | 1.00 | 25.83 |
| 22613 | C | GLY | D | 558 | -117.793 | -3.985 | 47.056 | 1.00 | 26.02 |
| 22614 | O | GLY | D | 558 | -117.668 | -4.868 | 47.898 | 1.00 | 26.32 |
| 22615 | N | TYR | D | 559 | -118.969 | -3.502 | 46.673 | 1.00 | 26.34 |
| 22616 | CA | TYR | D | 559 | -120.250 | -4.099 | 47.058 | 1.00 | 27.19 |
| 22617 | CB | TYR | D | 559 | -120.344 | -5.531 | 46.482 | 1.00 | 27.45 |
| 22618 | CG | TYR | D | 559 | -119.810 | -5.588 | 45.074 | 1.00 | 27.95 |
| 22619 | CD1 | TYR | D | 559 | -118.562 | -6.141 | 44.799 | 1.00 | 27.49 |
| 22620 | CE1 | TYR | D | 559 | -118.066 | -6.172 | 43.501 | 1.00 | 27.94 |
| 22621 | CZ | TYR | D | 559 | -118.813 | -5.618 | 42.471 | 1.00 | 28.56 |
| 22622 | OH | TYR | D | 559 | -118.323 | -5.599 | 41.188 | 1.00 | 27.38 |
| 22623 | CE2 | TYR | D | 559 | -120.029 | -5.035 | 42.731 | 1.00 | 28.45 |
| 22624 | CD2 | TYR | D | 559 | -120.514 | -5.011 | 44.029 | 1.00 | 28.47 |
| 22625 | C | TYR | D | 559 | -120.591 | -4.091 | 48.549 | 1.00 | 27.37 |
| 22626 | O | TYR | D | 559 | -121.465 | -4.850 | 48.983 | 1.00 | 27.51 |
| 22627 | N | GLN | D | 560 | -119.953 | -3.204 | 49.311 | 1.00 | 27.31 |
| 22628 | CA | GLN | D | 560 | -120.146 | -3.101 | 50.759 | 1.00 | 27.23 |
| 22629 | CB | GLN | D | 560 | -118.908 | -3.625 | 51.489 | 1.00 | 27.77 |
| 22630 | CG | GLN | D | 560 | -118.519 | -5.043 | 51.134 | 1.00 | 28.91 |
| 22631 | CD | GLN | D | 560 | -117.054 | -5.331 | 51.357 | 1.00 | 31.26 |
| 22632 | OE1 | GLN | D | 560 | -116.624 | -5.576 | 52.491 | 1.00 | 31.80 |
| 22633 | NE2 | GLN | D | 560 | -116.280 | -5.344 | 50.268 | 1.00 | 30.98 |
| 22634 | C | GLN | D | 560 | -120.366 | -1.645 | 51.151 | 1.00 | 27.53 |

FIGURE 3 QB

| A | B | C | D | E | F | G | H | I | J |
|---|---|---|---|---|---|---|---|---|---|
| 22635 | O | GLN | D | 560 | -120.236 | -1.267 | 52.321 | 1.00 | 27.86 |
| 22636 | N | GLY | D | 561 | -120.679 | -0.817 | 50.161 | 1.00 | 27.89 |
| 22637 | CA | GLY | D | 561 | -120.889 | 0.602 | 50.395 | 1.00 | 27.38 |
| 22638 | C | GLY | D | 561 | -119.659 | 1.477 | 50.206 | 1.00 | 27.11 |
| 22639 | O | GLY | D | 561 | -118.524 | 1.008 | 50.263 | 1.00 | 26.62 |
| 22640 | N | ASP | D | 562 | -119.892 | 2.767 | 49.995 | 1.00 | 27.30 |
| 22641 | CA | ASP | D | 562 | -118.812 | 3.709 | 49.753 | 1.00 | 28.31 |
| 22642 | CB | ASP | D | 562 | -119.365 | 5.051 | 49.321 | 1.00 | 28.36 |
| 22643 | CG | ASP | D | 562 | -120.046 | 4.988 | 47.983 | 1.00 | 29.39 |
| 22644 | OD1 | ASP | D | 562 | -119.845 | 3.988 | 47.236 | 1.00 | 30.55 |
| 22645 | OD2 | ASP | D | 562 | -120.815 | 5.894 | 47.610 | 1.00 | 29.84 |
| 22646 | C | ASP | D | 562 | -117.812 | 3.926 | 50.880 | 1.00 | 28.85 |
| 22647 | O | ASP | D | 562 | -116.637 | 4.191 | 50.616 | 1.00 | 29.41 |
| 22648 | N | LYS | D | 563 | -118.249 | 3.850 | 52.127 | 1.00 | 29.56 |
| 22649 | CA | LYS | D | 563 | -117.301 | 4.043 | 53.225 | 1.00 | 30.60 |
| 22650 | CB | LYS | D | 563 | -117.917 | 3.696 | 54.573 | 1.00 | 31.11 |
| 22651 | CG | LYS | D | 563 | -116.916 | 3.688 | 55.720 | 1.00 | 34.21 |
| 22652 | CD | LYS | D | 563 | -116.706 | 5.123 | 56.259 | 1.00 | 41.16 |
| 22653 | CE | LYS | D | 563 | -115.530 | 5.204 | 57.255 | 1.00 | 43.33 |
| 22654 | NZ | LYS | D | 563 | -115.058 | 6.615 | 57.450 | 1.00 | 44.62 |
| 22655 | C | LYS | D | 563 | -116.087 | 3.165 | 52.984 | 1.00 | 30.00 |
| 22656 | O | LYS | D | 563 | -114.957 | 3.612 | 53.094 | 1.00 | 30.15 |
| 22657 | N | ILE | D | 564 | -116.328 | 1.906 | 52.642 | 1.00 | 29.49 |
| 22658 | CA | ILE | D | 564 | -115.235 | 0.996 | 52.373 | 1.00 | 28.53 |
| 22659 | CB | ILE | D | 564 | -115.717 | -0.469 | 52.546 | 1.00 | 29.28 |
| 22660 | CG1 | ILE | D | 564 | -115.851 | -0.832 | 54.031 | 1.00 | 27.78 |
| 22661 | CD1 | ILE | D | 564 | -116.449 | -2.225 | 54.258 | 1.00 | 26.22 |
| 22662 | CG2 | ILE | D | 564 | -114.757 | -1.466 | 51.812 | 1.00 | 27.48 |
| 22663 | C | ILE | D | 564 | -114.642 | 1.180 | 50.973 | 1.00 | 28.08 |
| 22664 | O | ILE | D | 564 | -113.441 | 1.096 | 50.794 | 1.00 | 28.14 |
| 22665 | N | MET | D | 565 | -115.471 | 1.426 | 49.971 | 1.00 | 27.98 |
| 22666 | CA | MET | D | 565 | -114.939 | 1.458 | 48.603 | 1.00 | 27.61 |
| 22667 | CB | MET | D | 565 | -116.057 | 1.360 | 47.561 | 1.00 | 27.73 |
| 22668 | CG | MET | D | 565 | -115.550 | 1.349 | 46.129 | 1.00 | 26.07 |
| 22669 | SD | MET | D | 565 | -116.862 | 1.094 | 44.933 | 1.00 | 27.30 |
| 22670 | CE | MET | D | 565 | -117.601 | 2.652 | 44.824 | 1.00 | 25.23 |
| 22671 | C | MET | D | 565 | -114.088 | 2.672 | 48.333 | 1.00 | 27.63 |
| 22672 | O | MET | D | 565 | -113.015 | 2.559 | 47.745 | 1.00 | 27.09 |
| 22673 | N | HIS | D | 566 | -114.578 | 3.830 | 48.773 | 1.00 | 27.52 |
| 22674 | CA | HIS | D | 566 | -113.881 | 5.093 | 48.577 | 1.00 | 27.65 |
| 22675 | CB | HIS | D | 566 | -114.865 | 6.269 | 48.626 | 1.00 | 27.68 |
| 22676 | CG | HIS | D | 566 | -115.793 | 6.303 | 47.457 | 1.00 | 26.99 |
| 22677 | ND1 | HIS | D | 566 | -116.939 | 7.066 | 47.429 | 1.00 | 28.50 |
| 22678 | CE1 | HIS | D | 566 | -117.567 | 6.871 | 46.281 | 1.00 | 28.97 |
| 22679 | NE2 | HIS | D | 566 | -116.873 | 5.999 | 45.569 | 1.00 | 26.95 |
| 22680 | CD2 | HIS | D | 566 | -115.766 | 5.620 | 46.290 | 1.00 | 27.38 |
| 22681 | C | HIS | D | 566 | -112.754 | 5.329 | 49.555 | 1.00 | 27.89 |
| 22682 | O | HIS | D | 566 | -112.116 | 6.376 | 49.526 | 1.00 | 28.02 |
| 22683 | N | ALA | D | 567 | -112.488 | 4.358 | 50.418 | 1.00 | 28.19 |
| 22684 | CA | ALA | D | 567 | -111.425 | 4.533 | 51.401 | 1.00 | 28.18 |
| 22685 | CB | ALA | D | 567 | -111.348 | 3.320 | 52.332 | 1.00 | 28.22 |

FIGURE 3 QC

| A | B | C | D | E | F | G | H | I | J |
|---|---|---|---|---|---|---|---|---|---|
| 22686 | C | ALA | D | 567 | -110.071 | 4.789 | 50.740 | 1.00 | 28.08 |
| 22687 | O | ALA | D | 567 | -109.205 | 5.449 | 51.328 | 1.00 | 27.85 |
| 22688 | N | ILE | D | 568 | -109.874 | 4.259 | 49.528 | 1.00 | 27.58 |
| 22689 | CA | ILE | D | 568 | -108.598 | 4.447 | 48.850 | 1.00 | 27.06 |
| 22690 | CB | ILE | D | 568 | -108.082 | 3.124 | 48.203 | 1.00 | 27.60 |
| 22691 | CG1 | ILE | D | 568 | -109.113 | 2.479 | 47.291 | 1.00 | 26.85 |
| 22692 | CD1 | ILE | D | 568 | -109.901 | 3.443 | 46.432 | 1.00 | 29.00 |
| 22693 | CG2 | ILE | D | 568 | -107.640 | 2.107 | 49.293 | 1.00 | 28.00 |
| 22694 | C | ILE | D | 568 | -108.593 | 5.594 | 47.844 | 1.00 | 27.07 |
| 22695 | O | ILE | D | 568 | -107.677 | 5.697 | 47.015 | 1.00 | 26.67 |
| 22696 | N | ASN | D | 569 | -109.608 | 6.456 | 47.920 | 1.00 | 26.74 |
| 22697 | CA | ASN | D | 569 | -109.717 | 7.583 | 46.997 | 1.00 | 26.98 |
| 22698 | CB | ASN | D | 569 | -110.934 | 8.450 | 47.337 | 1.00 | 26.81 |
| 22699 | CG | ASN | D | 569 | -111.215 | 9.499 | 46.277 | 1.00 | 29.08 |
| 22700 | OD1 | ASN | D | 569 | -111.277 | 10.699 | 46.570 | 1.00 | 31.62 |
| 22701 | ND2 | ASN | D | 569 | -111.367 | 9.058 | 45.034 | 1.00 | 28.47 |
| 22702 | C | ASN | D | 569 | -108.458 | 8.435 | 47.024 | 1.00 | 27.29 |
| 22703 | O | ASN | D | 569 | -108.073 | 8.946 | 48.075 | 1.00 | 26.42 |
| 22704 | N | ARG | D | 570 | -107.791 | 8.544 | 45.877 | 1.00 | 27.75 |
| 22705 | CA | ARG | D | 570 | -106.620 | 9.405 | 45.760 | 1.00 | 28.44 |
| 22706 | CB | ARG | D | 570 | -106.924 | 10.792 | 46.346 | 1.00 | 28.62 |
| 22707 | CG | ARG | D | 570 | -107.950 | 11.571 | 45.559 | 1.00 | 30.72 |
| 22708 | CD | ARG | D | 570 | -108.236 | 12.971 | 46.119 | 1.00 | 36.07 |
| 22709 | NE | ARG | D | 570 | -107.033 | 13.789 | 46.249 | 1.00 | 38.04 |
| 22710 | CZ | ARG | D | 570 | -106.550 | 14.551 | 45.282 | 1.00 | 39.15 |
| 22711 | NH1 | ARG | D | 570 | -107.167 | 14.596 | 44.108 | 1.00 | 39.37 |
| 22712 | NH2 | ARG | D | 570 | -105.448 | 15.267 | 45.483 | 1.00 | 40.48 |
| 22713 | C | ARG | D | 570 | -105.439 | 8.805 | 46.473 | 1.00 | 28.36 |
| 22714 | O | ARG | D | 570 | -104.361 | 9.397 | 46.559 | 1.00 | 27.76 |
| 22715 | N | ARG | D | 571 | -105.618 | 7.595 | 46.964 | 1.00 | 28.89 |
| 22716 | CA | ARG | D | 571 | -104.562 | 7.056 | 47.778 | 1.00 | 29.67 |
| 22717 | CB | ARG | D | 571 | -104.861 | 7.341 | 49.256 | 1.00 | 29.49 |
| 22718 | CG | ARG | D | 571 | -103.669 | 7.967 | 49.989 | 1.00 | 34.40 |
| 22719 | CD | ARG | D | 571 | -103.706 | 9.481 | 50.211 | 1.00 | 37.34 |
| 22720 | NE | ARG | D | 571 | -103.697 | 10.225 | 48.963 | 1.00 | 40.61 |
| 22721 | CZ | ARG | D | 571 | -103.474 | 11.525 | 48.868 | 1.00 | 41.04 |
| 22722 | NH1 | ARG | D | 571 | -103.490 | 12.103 | 47.672 | 1.00 | 40.49 |
| 22723 | NH2 | ARG | D | 571 | -103.233 | 12.248 | 49.960 | 1.00 | 41.29 |
| 22724 | C | ARG | D | 571 | -104.290 | 5.589 | 47.472 | 1.00 | 29.13 |
| 22725 | O | ARG | D | 571 | -104.166 | 4.748 | 48.366 | 1.00 | 29.48 |
| 22726 | N | LEU | D | 572 | -104.165 | 5.290 | 46.186 | 1.00 | 28.53 |
| 22727 | CA | LEU | D | 572 | -103.865 | 3.918 | 45.770 | 1.00 | 28.13 |
| 22728 | CB | LEU | D | 572 | -103.815 | 3.814 | 44.246 | 1.00 | 27.82 |
| 22729 | CG | LEU | D | 572 | -105.077 | 3.332 | 43.525 | 1.00 | 28.58 |
| 22730 | CD1 | LEU | D | 572 | -105.174 | 3.831 | 42.088 | 1.00 | 25.84 |
| 22731 | CD2 | LEU | D | 572 | -106.344 | 3.628 | 44.310 | 1.00 | 28.27 |
| 22732 | C | LEU | D | 572 | -102.534 | 3.495 | 46.372 | 1.00 | 27.64 |
| 22733 | O | LEU | D | 572 | -101.662 | 4.323 | 46.605 | 1.00 | 28.39 |
| 22734 | N | GLY | D | 573 | -102.379 | 2.210 | 46.640 | 1.00 | 26.99 |
| 22735 | CA | GLY | D | 573 | -101.137 | 1.711 | 47.178 | 1.00 | 25.65 |
| 22736 | C | GLY | D | 573 | -100.985 | 2.031 | 48.656 | 1.00 | 25.59 |

FIGURE 3 QD

| A | B | C | D | E | F | G | H | I | J |
|---|---|---|---|---|---|---|---|---|---|
| 22737 | O | GLY | D | 573 | -99.872 | 2.088 | 49.158 | 1.00 | 25.01 |
| 22738 | N | THR | D | 574 | -102.089 | 2.271 | 49.358 | 1.00 | 25.02 |
| 22739 | CA | THR | D | 574 | -101.978 | 2.512 | 50.798 | 1.00 | 24.80 |
| 22740 | CB | THR | D | 574 | -102.403 | 3.932 | 51.175 | 1.00 | 24.60 |
| 22741 | OG1 | THR | D | 574 | -103.769 | 4.133 | 50.788 | 1.00 | 25.11 |
| 22742 | CG2 | THR | D | 574 | -101.624 | 4.977 | 50.361 | 1.00 | 24.02 |
| 22743 | C | THR | D | 574 | -102.786 | 1.507 | 51.618 | 1.00 | 24.68 |
| 22744 | O | THR | D | 574 | -102.291 | 0.453 | 51.957 | 1.00 | 23.86 |
| 22745 | N | PHE | D | 575 | -104.039 | 1.843 | 51.913 | 1.00 | 25.42 |
| 22746 | CA | PHE | D | 575 | -104.884 | 1.037 | 52.786 | 1.00 | 26.24 |
| 22747 | CB | PHE | D | 575 | -106.212 | 1.749 | 53.005 | 1.00 | 26.92 |
| 22748 | CG | PHE | D | 575 | -106.088 | 3.074 | 53.724 | 1.00 | 28.29 |
| 22749 | CD1 | PHE | D | 575 | -105.145 | 3.260 | 54.707 | 1.00 | 28.72 |
| 22750 | CE1 | PHE | D | 575 | -105.050 | 4.475 | 55.390 | 1.00 | 30.07 |
| 22751 | CZ | PHE | D | 575 | -105.896 | 5.510 | 55.090 | 1.00 | 29.21 |
| 22752 | CE2 | PHE | D | 575 | -106.848 | 5.335 | 54.106 | 1.00 | 31.74 |
| 22753 | CD2 | PHE | D | 575 | -106.949 | 4.113 | 53.435 | 1.00 | 29.53 |
| 22754 | C | PHE | D | 575 | -105.167 | -0.374 | 52.291 | 1.00 | 26.80 |
| 22755 | O | PHE | D | 575 | -105.347 | -1.297 | 53.094 | 1.00 | 27.14 |
| 22756 | N | GLU | D | 576 | -105.226 | -0.541 | 50.973 | 1.00 | 26.67 |
| 22757 | CA | GLU | D | 576 | -105.526 | -1.825 | 50.386 | 1.00 | 26.70 |
| 22758 | CB | GLU | D | 576 | -106.059 | -1.656 | 48.953 | 1.00 | 27.22 |
| 22759 | CG | GLU | D | 576 | -104.999 | -1.536 | 47.850 | 1.00 | 28.25 |
| 22760 | CD | GLU | D | 576 | -104.397 | -0.138 | 47.693 | 1.00 | 29.97 |
| 22761 | OE1 | GLU | D | 576 | -104.224 | 0.603 | 48.695 | 1.00 | 29.55 |
| 22762 | OE2 | GLU | D | 576 | -104.064 | 0.213 | 46.544 | 1.00 | 31.10 |
| 22763 | C | GLU | D | 576 | -104.284 | -2.701 | 50.463 | 1.00 | 27.03 |
| 22764 | O | GLU | D | 576 | -104.381 | -3.921 | 50.618 | 1.00 | 27.54 |
| 22765 | N | VAL | D | 577 | -103.113 | -2.082 | 50.372 | 1.00 | 27.44 |
| 22766 | CA | VAL | D | 577 | -101.849 | -2.797 | 50.534 | 1.00 | 27.86 |
| 22767 | CB | VAL | D | 577 | -100.634 | -1.902 | 50.144 | 1.00 | 28.09 |
| 22768 | CG1 | VAL | D | 577 | -100.673 | -1.570 | 48.673 | 1.00 | 27.66 |
| 22769 | CG2 | VAL | D | 577 | -99.293 | -2.566 | 50.504 | 1.00 | 26.74 |
| 22770 | C | VAL | D | 577 | -101.729 | -3.218 | 52.006 | 1.00 | 28.75 |
| 22771 | O | VAL | D | 577 | -101.523 | -4.386 | 52.314 | 1.00 | 27.76 |
| 22772 | N | GLU | D | 578 | -101.889 | -2.244 | 52.900 | 1.00 | 29.84 |
| 22773 | CA | GLU | D | 578 | -101.814 | -2.454 | 54.348 | 1.00 | 31.68 |
| 22774 | CB | GLU | D | 578 | -102.010 | -1.110 | 55.089 | 1.00 | 32.26 |
| 22775 | CG | GLU | D | 578 | -100.801 | -0.173 | 54.957 | 1.00 | 37.82 |
| 22776 | CD | GLU | D | 578 | -101.117 | 1.320 | 55.116 | 1.00 | 45.04 |
| 22777 | OE1 | GLU | D | 578 | -100.809 | 2.100 | 54.163 | 1.00 | 47.10 |
| 22778 | OE2 | GLU | D | 578 | -101.632 | 1.736 | 56.196 | 1.00 | 46.15 |
| 22779 | C | GLU | D | 578 | -102.811 | -3.519 | 54.825 | 1.00 | 31.53 |
| 22780 | O | GLU | D | 578 | -102.450 | -4.412 | 55.596 | 1.00 | 31.88 |
| 22781 | N | ASP | D | 579 | -104.052 | -3.450 | 54.345 | 1.00 | 31.09 |
| 22782 | CA | ASP | D | 579 | -105.054 | -4.420 | 54.764 | 1.00 | 30.71 |
| 22783 | CB | ASP | D | 579 | -106.443 | -4.034 | 54.266 | 1.00 | 31.02 |
| 22784 | CG | ASP | D | 579 | -107.014 | -2.810 | 54.984 | 1.00 | 32.48 |
| 22785 | OD1 | ASP | D | 579 | -106.396 | -2.324 | 55.962 | 1.00 | 33.16 |
| 22786 | OD2 | ASP | D | 579 | -108.090 | -2.261 | 54.632 | 1.00 | 33.82 |
| 22787 | C | ASP | D | 579 | -104.679 | -5.863 | 54.361 | 1.00 | 30.02 |

FIGURE 3 QE

| A | B | C | D | E | F | G | H | I | J |
|---|---|---|---|---|---|---|---|---|---|
| 22788 | O | ASP | D | 579 | -104.980 | -6.809 | 55.085 | 1.00 | 29.35 |
| 22789 | N | GLN | D | 580 | -104.007 | -6.037 | 53.229 | 1.00 | 29.15 |
| 22790 | CA | GLN | D | 580 | -103.561 | -7.375 | 52.844 | 1.00 | 28.97 |
| 22791 | CB | GLN | D | 580 | -102.978 | -7.394 | 51.428 | 1.00 | 28.42 |
| 22792 | CG | GLN | D | 580 | -103.972 | -7.130 | 50.322 | 1.00 | 27.58 |
| 22793 | CD | GLN | D | 580 | -104.992 | -8.242 | 50.155 | 1.00 | 27.11 |
| 22794 | OE1 | GLN | D | 580 | -104.625 | -9.400 | 50.001 | 1.00 | 25.81 |
| 22795 | NE2 | GLN | D | 580 | -106.280 | -7.883 | 50.161 | 1.00 | 25.38 |
| 22796 | C | GLN | D | 580 | -102.512 | -7.896 | 53.828 | 1.00 | 29.53 |
| 22797 | O | GLN | D | 580 | -102.454 | -9.095 | 54.117 | 1.00 | 29.69 |
| 22798 | N | ILE | D | 581 | -101.661 | -7.002 | 54.321 | 1.00 | 29.77 |
| 22799 | CA | ILE | D | 581 | -100.649 | -7.403 | 55.272 | 1.00 | 30.78 |
| 22800 | CB | ILE | D | 581 | -99.610 | -6.280 | 55.453 | 1.00 | 30.83 |
| 22801 | CG1 | ILE | D | 581 | -98.635 | -6.234 | 54.267 | 1.00 | 30.50 |
| 22802 | CD1 | ILE | D | 581 | -98.115 | -4.801 | 54.003 | 1.00 | 29.32 |
| 22803 | CG2 | ILE | D | 581 | -98.837 | -6.434 | 56.772 | 1.00 | 30.88 |
| 22804 | C | ILE | D | 581 | -101.318 | -7.778 | 56.599 | 1.00 | 31.22 |
| 22805 | O | ILE | D | 581 | -101.019 | -8.815 | 57.185 | 1.00 | 31.08 |
| 22806 | N | GLU | D | 582 | -102.229 | -6.925 | 57.052 | 1.00 | 31.70 |
| 22807 | CA | GLU | D | 582 | -102.977 | -7.160 | 58.286 | 1.00 | 32.63 |
| 22808 | CB | GLU | D | 582 | -103.890 | -5.968 | 58.609 | 1.00 | 32.27 |
| 22809 | CG | GLU | D | 582 | -104.750 | -6.176 | 59.838 | 1.00 | 33.99 |
| 22810 | CD | GLU | D | 582 | -103.925 | -6.299 | 61.114 | 1.00 | 38.62 |
| 22811 | OE1 | GLU | D | 582 | -104.472 | -6.791 | 62.124 | 1.00 | 38.76 |
| 22812 | OE2 | GLU | D | 582 | -102.734 | -5.891 | 61.114 | 1.00 | 40.20 |
| 22813 | C | GLU | D | 582 | -103.801 | -8.444 | 58.194 | 1.00 | 32.47 |
| 22814 | O | GLU | D | 582 | -103.972 | -9.158 | 59.183 | 1.00 | 33.17 |
| 22815 | N | ALA | D | 583 | -104.292 | -8.740 | 57.002 | 1.00 | 32.20 |
| 22816 | CA | ALA | D | 583 | -105.040 | -9.974 | 56.783 | 1.00 | 32.77 |
| 22817 | CB | ALA | D | 583 | -105.639 | -10.020 | 55.371 | 1.00 | 32.21 |
| 22818 | C | ALA | D | 583 | -104.140 | -11.171 | 57.008 | 1.00 | 32.51 |
| 22819 | O | ALA | D | 583 | -104.515 | -12.108 | 57.702 | 1.00 | 32.29 |
| 22820 | N | ALA | D | 584 | -102.961 | -11.134 | 56.399 | 1.00 | 32.95 |
| 22821 | CA | ALA | D | 584 | -101.987 | -12.207 | 56.561 | 1.00 | 34.06 |
| 22822 | CB | ALA | D | 584 | -100.776 | -11.936 | 55.745 | 1.00 | 33.46 |
| 22823 | C | ALA | D | 584 | -101.625 | -12.358 | 58.038 | 1.00 | 35.08 |
| 22824 | O | ALA | D | 584 | -101.484 | -13.473 | 58.540 | 1.00 | 35.25 |
| 22825 | N | ARG | D | 585 | -101.504 | -11.231 | 58.729 | 1.00 | 36.40 |
| 22826 | CA | ARG | D | 585 | -101.232 | -11.240 | 60.155 | 1.00 | 38.09 |
| 22827 | CB | ARG | D | 585 | -101.007 | -9.819 | 60.693 | 1.00 | 38.45 |
| 22828 | CG | ARG | D | 585 | -99.588 | -9.293 | 60.510 | 1.00 | 37.61 |
| 22829 | CD | ARG | D | 585 | -99.263 | -8.106 | 61.400 | 1.00 | 38.68 |
| 22830 | NE | ARG | D | 585 | -98.920 | -6.886 | 60.672 | 1.00 | 40.40 |
| 22831 | CZ | ARG | D | 585 | -97.673 | -6.482 | 60.453 | 1.00 | 40.67 |
| 22832 | NH1 | ARG | D | 585 | -96.654 | -7.202 | 60.898 | 1.00 | 41.73 |
| 22833 | NH2 | ARG | D | 585 | -97.438 | -5.360 | 59.799 | 1.00 | 39.47 |
| 22834 | C | ARG | D | 585 | -102.342 | -11.921 | 60.942 | 1.00 | 39.12 |
| 22835 | O | ARG | D | 585 | -102.058 | -12.724 | 61.816 | 1.00 | 39.64 |
| 22836 | N | GLN | D | 586 | -103.599 | -11.622 | 60.630 | 1.00 | 40.11 |
| 22837 | CA | GLN | D | 586 | -104.709 | -12.224 | 61.360 | 1.00 | 41.16 |
| 22838 | CB | GLN | D | 586 | -106.025 | -11.492 | 61.091 | 1.00 | 41.10 |

FIGURE 3 QF

| A | B | C | D | E | F | G | H | I | J |
|---|---|---|---|---|---|---|---|---|---|
| 22839 | CG | GLN | D | 586 | -106.123 | -10.079 | 61.682 | 1.00 | 42.90 |
| 22840 | CD | GLN | D | 586 | -106.715 | -10.060 | 63.075 | 1.00 | 45.95 |
| 22841 | OE1 | GLN | D | 586 | -107.124 | -9.015 | 63.566 | 1.00 | 47.36 |
| 22842 | NE2 | GLN | D | 586 | -106.773 | -11.226 | 63.711 | 1.00 | 48.11 |
| 22843 | C | GLN | D | 586 | -104.861 | -13.705 | 61.031 | 1.00 | 41.99 |
| 22844 | O | GLN | D | 586 | -105.377 | -14.474 | 61.847 | 1.00 | 42.30 |
| 22845 | N | PHE | D | 587 | -104.427 | -14.101 | 59.836 | 1.00 | 42.89 |
| 22846 | CA | PHE | D | 587 | -104.498 | -15.503 | 59.426 | 1.00 | 43.33 |
| 22847 | CB | PHE | D | 587 | -104.241 | -15.677 | 57.921 | 1.00 | 42.71 |
| 22848 | CG | PHE | D | 587 | -105.281 | -15.049 | 57.037 | 1.00 | 41.34 |
| 22849 | CD1 | PHE | D | 587 | -106.572 | -14.834 | 57.493 | 1.00 | 40.20 |
| 22850 | CE1 | PHE | D | 587 | -107.521 | -14.254 | 56.671 | 1.00 | 38.14 |
| 22851 | CZ | PHE | D | 587 | -107.187 | -13.895 | 55.376 | 1.00 | 37.46 |
| 22852 | CE2 | PHE | D | 587 | -105.919 | -14.116 | 54.912 | 1.00 | 36.54 |
| 22853 | CD2 | PHE | D | 587 | -104.971 | -14.685 | 55.735 | 1.00 | 38.81 |
| 22854 | C | PHE | D | 587 | -103.440 | -16.252 | 60.226 | 1.00 | 44.39 |
| 22855 | O | PHE | D | 587 | -103.657 | -17.389 | 60.638 | 1.00 | 44.74 |
| 22856 | N | SER | D | 588 | -102.292 | -15.606 | 60.430 | 1.00 | 45.69 |
| 22857 | CA | SER | D | 588 | -101.217 | -16.161 | 61.258 | 1.00 | 47.02 |
| 22858 | CB | SER | D | 588 | -100.030 | -15.195 | 61.361 | 1.00 | 47.26 |
| 22859 | OG | SER | D | 588 | -99.056 | -15.433 | 60.351 | 1.00 | 48.72 |
| 22860 | C | SER | D | 588 | -101.720 | -16.455 | 62.663 | 1.00 | 47.44 |
| 22861 | O | SER | D | 588 | -101.435 | -17.517 | 63.217 | 1.00 | 47.74 |
| 22862 | N | LYS | D | 589 | -102.472 | -15.524 | 63.238 | 1.00 | 47.68 |
| 22863 | CA | LYS | D | 589 | -102.988 | -15.726 | 64.586 | 1.00 | 48.75 |
| 22864 | CB | LYS | D | 589 | -103.438 | -14.397 | 65.214 | 1.00 | 48.90 |
| 22865 | CG | LYS | D | 589 | -102.318 | -13.665 | 65.968 | 1.00 | 51.80 |
| 22866 | CD | LYS | D | 589 | -101.415 | -12.829 | 65.027 | 1.00 | 56.24 |
| 22867 | CE | LYS | D | 589 | -100.144 | -12.316 | 65.741 | 1.00 | 58.28 |
| 22868 | NZ | LYS | D | 589 | -99.516 | -11.165 | 65.007 | 1.00 | 60.63 |
| 22869 | C | LYS | D | 589 | -104.093 | -16.788 | 64.665 | 1.00 | 48.47 |
| 22870 | O | LYS | D | 589 | -104.526 | -17.158 | 65.759 | 1.00 | 49.01 |
| 22871 | N | MET | D | 590 | -104.539 | -17.283 | 63.515 | 1.00 | 47.95 |
| 22872 | CA | MET | D | 590 | -105.591 | -18.293 | 63.503 | 1.00 | 47.45 |
| 22873 | CB | MET | D | 590 | -106.346 | -18.303 | 62.171 | 1.00 | 47.08 |
| 22874 | CG | MET | D | 590 | -107.438 | -17.267 | 62.106 | 1.00 | 46.07 |
| 22875 | SD | MET | D | 590 | -108.073 | -17.158 | 60.449 | 1.00 | 44.94 |
| 22876 | CE | MET | D | 590 | -109.348 | -15.990 | 60.659 | 1.00 | 45.88 |
| 22877 | C | MET | D | 590 | -105.095 | -19.711 | 63.865 | 1.00 | 47.12 |
| 22878 | O | MET | D | 590 | -105.898 | -20.636 | 64.054 | 1.00 | 47.49 |
| 22879 | N | GLY | D | 591 | -103.776 | -19.890 | 63.940 | 1.00 | 46.11 |
| 22880 | CA | GLY | D | 591 | -103.200 | -21.150 | 64.388 | 1.00 | 44.74 |
| 22881 | C | GLY | D | 591 | -102.758 | -22.185 | 63.369 | 1.00 | 44.10 |
| 22882 | O | GLY | D | 591 | -101.780 | -22.897 | 63.599 | 1.00 | 44.53 |
| 22883 | N | PHE | D | 592 | -103.471 | -22.294 | 62.254 | 1.00 | 42.57 |
| 22884 | CA | PHE | D | 592 | -103.126 | -23.294 | 61.258 | 1.00 | 40.76 |
| 22885 | CB | PHE | D | 592 | -104.397 | -23.899 | 60.674 | 1.00 | 41.08 |
| 22886 | CG | PHE | D | 592 | -105.425 | -22.884 | 60.306 | 1.00 | 40.63 |
| 22887 | CD1 | PHE | D | 592 | -106.558 | -22.719 | 61.075 | 1.00 | 41.45 |
| 22888 | CE1 | PHE | D | 592 | -107.511 | -21.772 | 60.727 | 1.00 | 40.92 |
| 22889 | CZ | PHE | D | 592 | -107.322 | -20.993 | 59.602 | 1.00 | 39.45 |

FIGURE 3 QG

| A | B | C | D | E | F | G | H | I | J |
|---|---|---|---|---|---|---|---|---|---|
| 22890 | CE2 | PHE | D | 592 | -106.197 | -21.156 | 58.839 | 1.00 | 38.64 |
| 22891 | CD2 | PHE | D | 592 | -105.257 | -22.087 | 59.188 | 1.00 | 39.90 |
| 22892 | C | PHE | D | 592 | -102.241 | -22.752 | 60.135 | 1.00 | 39.98 |
| 22893 | O | PHE | D | 592 | -102.193 | -23.327 | 59.035 | 1.00 | 39.38 |
| 22894 | N | VAL | D | 593 | -101.536 | -21.658 | 60.409 | 1.00 | 38.64 |
| 22895 | CA | VAL | D | 593 | -100.630 | -21.083 | 59.411 | 1.00 | 37.58 |
| 22896 | CB | VAL | D | 593 | -101.005 | -19.628 | 59.041 | 1.00 | 37.59 |
| 22897 | CG1 | VAL | D | 593 | -99.801 | -18.892 | 58.427 | 1.00 | 36.42 |
| 22898 | CG2 | VAL | D | 593 | -102.186 | -19.618 | 58.087 | 1.00 | 36.64 |
| 22899 | C | VAL | D | 593 | -99.170 | -21.140 | 59.809 | 1.00 | 37.12 |
| 22900 | O | VAL | D | 593 | -98.782 | -20.674 | 60.884 | 1.00 | 37.47 |
| 22901 | N | ASP | D | 594 | -98.353 | -21.720 | 58.943 | 1.00 | 36.52 |
| 22902 | CA | ASP | D | 594 | -96.923 | -21.728 | 59.187 | 1.00 | 36.38 |
| 22903 | CB | ASP | D | 594 | -96.230 | -22.810 | 58.354 | 1.00 | 35.77 |
| 22904 | CG | ASP | D | 594 | -94.731 | -22.758 | 58.494 | 1.00 | 35.39 |
| 22905 | OD1 | ASP | D | 594 | -94.008 | -23.515 | 57.802 | 1.00 | 35.89 |
| 22906 | OD2 | ASP | D | 594 | -94.181 | -21.980 | 59.292 | 1.00 | 34.16 |
| 22907 | C | ASP | D | 594 | -96.374 | -20.345 | 58.830 | 1.00 | 36.57 |
| 22908 | O | ASP | D | 594 | -96.181 | -20.044 | 57.650 | 1.00 | 37.17 |
| 22909 | N | ASN | D | 595 | -96.160 | -19.507 | 59.840 | 1.00 | 36.30 |
| 22910 | CA | ASN | D | 595 | -95.634 | -18.148 | 59.656 | 1.00 | 36.78 |
| 22911 | CB | ASN | D | 595 | -95.377 | -17.491 | 61.018 | 1.00 | 37.54 |
| 22912 | CG | ASN | D | 595 | -96.649 | -17.078 | 61.699 | 1.00 | 41.48 |
| 22913 | OD1 | ASN | D | 595 | -97.746 | -17.471 | 61.280 | 1.00 | 45.39 |
| 22914 | ND2 | ASN | D | 595 | -96.526 | -16.287 | 62.760 | 1.00 | 43.93 |
| 22915 | C | ASN | D | 595 | -94.352 | -18.036 | 58.835 | 1.00 | 35.85 |
| 22916 | O | ASN | D | 595 | -93.994 | -16.953 | 58.370 | 1.00 | 35.40 |
| 22917 | N | LYS | D | 596 | -93.648 | -19.143 | 58.675 | 1.00 | 34.72 |
| 22918 | CA | LYS | D | 596 | -92.413 | -19.119 | 57.920 | 1.00 | 34.21 |
| 22919 | CB | LYS | D | 596 | -91.435 | -20.128 | 58.507 | 1.00 | 34.17 |
| 22920 | CG | LYS | D | 596 | -91.250 | -19.909 | 60.041 | 1.00 | 36.54 |
| 22921 | CD | LYS | D | 596 | -90.150 | -20.773 | 60.662 | 1.00 | 37.81 |
| 22922 | CE | LYS | D | 596 | -90.308 | -22.227 | 60.276 | 1.00 | 40.13 |
| 22923 | NZ | LYS | D | 596 | -91.635 | -22.778 | 60.686 | 1.00 | 41.92 |
| 22924 | C | LYS | D | 596 | -92.651 | -19.320 | 56.417 | 1.00 | 33.28 |
| 22925 | O | LYS | D | 596 | -91.740 | -19.205 | 55.602 | 1.00 | 33.31 |
| 22926 | N | ARG | D | 597 | -93.889 | -19.597 | 56.049 | 1.00 | 32.32 |
| 22927 | CA | ARG | D | 597 | -94.202 | -19.812 | 54.644 | 1.00 | 31.94 |
| 22928 | CB | ARG | D | 597 | -94.289 | -21.301 | 54.364 | 1.00 | 32.07 |
| 22929 | CG | ARG | D | 597 | -92.965 | -21.992 | 54.619 | 1.00 | 34.21 |
| 22930 | CD | ARG | D | 597 | -92.971 | -23.463 | 54.314 | 1.00 | 34.83 |
| 22931 | NE | ARG | D | 597 | -93.720 | -24.207 | 55.309 | 1.00 | 36.28 |
| 22932 | CZ | ARG | D | 597 | -94.198 | -25.416 | 55.095 | 1.00 | 38.14 |
| 22933 | NH1 | ARG | D | 597 | -94.010 | -25.999 | 53.911 | 1.00 | 38.90 |
| 22934 | NH2 | ARG | D | 597 | -94.860 | -26.040 | 56.049 | 1.00 | 37.79 |
| 22935 | C | ARG | D | 597 | -95.474 | -19.093 | 54.193 | 1.00 | 30.69 |
| 22936 | O | ARG | D | 597 | -96.473 | -19.730 | 53.857 | 1.00 | 30.79 |
| 22937 | N | ILE | D | 598 | -95.442 | -17.768 | 54.225 | 1.00 | 29.08 |
| 22938 | CA | ILE | D | 598 | -96.571 | -16.980 | 53.737 | 1.00 | 27.73 |
| 22939 | CB | ILE | D | 598 | -97.092 | -15.999 | 54.803 | 1.00 | 27.92 |
| 22940 | CG1 | ILE | D | 598 | -97.392 | -16.759 | 56.110 | 1.00 | 26.82 |

FIGURE 3 QH

| A | B | C | D | E | F | G | H | I | J |
|---|---|---|---|---|---|---|---|---|---|
| 22941 | CD1 | ILE | D | 598 | -97.873 | -15.890 | 57.219 | 1.00 | 25.20 |
| 22942 | CG2 | ILE | D | 598 | -98.342 | -15.300 | 54.329 | 1.00 | 25.89 |
| 22943 | C | ILE | D | 598 | -96.084 | -16.276 | 52.488 | 1.00 | 27.30 |
| 22944 | O | ILE | D | 598 | -95.021 | -15.649 | 52.471 | 1.00 | 26.65 |
| 22945 | N | ALA | D | 599 | -96.846 | -16.448 | 51.419 | 1.00 | 26.51 |
| 22946 | CA | ALA | D | 599 | -96.491 | -15.902 | 50.144 | 1.00 | 25.08 |
| 22947 | CB | ALA | D | 599 | -96.186 | -17.014 | 49.175 | 1.00 | 25.13 |
| 22948 | C | ALA | D | 599 | -97.655 | -15.086 | 49.669 | 1.00 | 25.14 |
| 22949 | O | ALA | D | 599 | -98.724 | -15.064 | 50.295 | 1.00 | 24.14 |
| 22950 | N | ILE | D | 600 | -97.444 | -14.383 | 48.563 | 1.00 | 24.78 |
| 22951 | CA | ILE | D | 600 | -98.485 | -13.536 | 48.032 | 1.00 | 23.69 |
| 22952 | CB | ILE | D | 600 | -98.459 | -12.153 | 48.722 | 1.00 | 24.06 |
| 22953 | CG1 | ILE | D | 600 | -99.587 | -11.273 | 48.193 | 1.00 | 23.71 |
| 22954 | CD1 | ILE | D | 600 | -99.725 | -9.971 | 48.917 | 1.00 | 21.11 |
| 22955 | CG2 | ILE | D | 600 | -97.081 | -11.463 | 48.559 | 1.00 | 22.54 |
| 22956 | C | ILE | D | 600 | -98.274 | -13.440 | 46.548 | 1.00 | 23.68 |
| 22957 | O | ILE | D | 600 | -97.149 | -13.503 | 46.049 | 1.00 | 23.70 |
| 22958 | N | TRP | D | 601 | -99.369 | -13.334 | 45.818 | 1.00 | 23.86 |
| 22959 | CA | TRP | D | 601 | -99.271 | -13.281 | 44.376 | 1.00 | 22.92 |
| 22960 | CB | TRP | D | 601 | -99.091 | -14.680 | 43.784 | 1.00 | 22.51 |
| 22961 | CG | TRP | D | 601 | -100.342 | -15.316 | 43.245 | 1.00 | 22.42 |
| 22962 | CD1 | TRP | D | 601 | -101.266 | -15.997 | 43.949 | 1.00 | 21.34 |
| 22963 | NE1 | TRP | D | 601 | -102.258 | -16.458 | 43.121 | 1.00 | 22.82 |
| 22964 | CE2 | TRP | D | 601 | -101.970 | -16.092 | 41.834 | 1.00 | 23.85 |
| 22965 | CD2 | TRP | D | 601 | -100.767 | -15.365 | 41.874 | 1.00 | 23.54 |
| 22966 | CE3 | TRP | D | 601 | -100.250 | -14.863 | 40.673 | 1.00 | 23.20 |
| 22967 | CZ3 | TRP | D | 601 | -100.937 | -15.104 | 39.498 | 1.00 | 24.27 |
| 22968 | CH2 | TRP | D | 601 | -102.146 | -15.832 | 39.492 | 1.00 | 23.52 |
| 22969 | CZ2 | TRP | D | 601 | -102.674 | -16.331 | 40.646 | 1.00 | 22.15 |
| 22970 | C | TRP | D | 601 | -100.514 | -12.627 | 43.843 | 1.00 | 22.66 |
| 22971 | O | TRP | D | 601 | -101.545 | -12.651 | 44.493 | 1.00 | 22.09 |
| 22972 | N | GLY | D | 602 | -100.389 | -12.044 | 42.656 | 1.00 | 22.24 |
| 22973 | CA | GLY | D | 602 | -101.468 | -11.332 | 42.015 | 1.00 | 21.84 |
| 22974 | C | GLY | D | 602 | -101.087 | -10.926 | 40.603 | 1.00 | 21.79 |
| 22975 | O | GLY | D | 602 | -99.926 | -11.006 | 40.198 | 1.00 | 22.06 |
| 22976 | N | TRP | D | 603 | -102.071 | -10.438 | 39.872 | 1.00 | 22.68 |
| 22977 | CA | TRP | D | 603 | -101.951 | -10.131 | 38.455 | 1.00 | 23.29 |
| 22978 | CB | TRP | D | 603 | -102.806 | -11.160 | 37.719 | 1.00 | 23.27 |
| 22979 | CG | TRP | D | 603 | -102.592 | -11.304 | 36.278 | 1.00 | 25.73 |
| 22980 | CD1 | TRP | D | 603 | -102.670 | -10.327 | 35.335 | 1.00 | 27.22 |
| 22981 | NE1 | TRP | D | 603 | -102.409 | -10.852 | 34.090 | 1.00 | 28.83 |
| 22982 | CE2 | TRP | D | 603 | -102.166 | -12.196 | 34.209 | 1.00 | 28.70 |
| 22983 | CD2 | TRP | D | 603 | -102.284 | -12.520 | 35.574 | 1.00 | 28.46 |
| 22984 | CE3 | TRP | D | 603 | -102.069 | -13.852 | 35.967 | 1.00 | 29.49 |
| 22985 | CZ3 | TRP | D | 603 | -101.772 | -14.801 | 34.994 | 1.00 | 29.73 |
| 22986 | CH2 | TRP | D | 603 | -101.676 | -14.442 | 33.640 | 1.00 | 28.93 |
| 22987 | CZ2 | TRP | D | 603 | -101.877 | -13.150 | 33.232 | 1.00 | 28.88 |
| 22988 | C | TRP | D | 603 | -102.542 | -8.750 | 38.254 | 1.00 | 23.40 |
| 22989 | O | TRP | D | 603 | -103.594 | -8.463 | 38.792 | 1.00 | 23.07 |
| 22990 | N | SER | D | 604 | -101.873 | -7.886 | 37.494 | 1.00 | 24.27 |
| 22991 | CA | SER | D | 604 | -102.407 | -6.535 | 37.222 | 1.00 | 24.66 |

FIGURE 3 QI

| A | B | C | D | E | F | G | H | I | J |
|---|---|---|---|---|---|---|---|---|---|
| 22992 | CB | SER | D | 604 | -103.789 | -6.615 | 36.568 | 1.00 | 24.77 |
| 22993 | OG | SER | D | 604 | -104.070 | -5.413 | 35.859 | 1.00 | 26.90 |
| 22994 | C | SER | D | 604 | -102.422 | -5.670 | 38.486 | 1.00 | 23.41 |
| 22995 | O | SER | D | 604 | -101.372 | -5.445 | 39.058 | 1.00 | 23.95 |
| 22996 | N | TYR | D | 605 | -103.579 | -5.193 | 38.931 | 1.00 | 23.03 |
| 22997 | CA | TYR | D | 605 | -103.631 | -4.467 | 40.203 | 1.00 | 22.68 |
| 22998 | CB | TYR | D | 605 | -105.054 | -4.018 | 40.581 | 1.00 | 22.87 |
| 22999 | CG | TYR | D | 605 | -105.036 | -2.841 | 41.583 | 1.00 | 24.08 |
| 23000 | CD1 | TYR | D | 605 | -105.355 | -1.549 | 41.178 | 1.00 | 21.68 |
| 23001 | CE1 | TYR | D | 605 | -105.338 | -0.482 | 42.061 | 1.00 | 21.13 |
| 23002 | CZ | TYR | D | 605 | -104.977 | -0.696 | 43.366 | 1.00 | 23.44 |
| 23003 | OH | TYR | D | 605 | -104.941 | 0.359 | 44.218 | 1.00 | 23.36 |
| 23004 | CE2 | TYR | D | 605 | -104.645 | -1.964 | 43.817 | 1.00 | 24.51 |
| 23005 | CD2 | TYR | D | 605 | -104.660 | -3.032 | 42.921 | 1.00 | 24.94 |
| 23006 | C | TYR | D | 605 | -103.053 | -5.407 | 41.267 | 1.00 | 22.70 |
| 23007 | O | TYR | D | 605 | -102.310 | -4.995 | 42.169 | 1.00 | 22.81 |
| 23008 | N | GLY | D | 606 | -103.356 | -6.687 | 41.112 | 1.00 | 21.85 |
| 23009 | CA | GLY | D | 606 | -102.812 | -7.697 | 41.981 | 1.00 | 21.79 |
| 23010 | C | GLY | D | 606 | -101.293 | -7.751 | 41.985 | 1.00 | 21.22 |
| 23011 | O | GLY | D | 606 | -100.695 | -8.008 | 43.023 | 1.00 | 20.85 |
| 23012 | N | GLY | D | 607 | -100.662 | -7.548 | 40.835 | 1.00 | 20.80 |
| 23013 | CA | GLY | D | 607 | -99.208 | -7.534 | 40.794 | 1.00 | 20.33 |
| 23014 | C | GLY | D | 607 | -98.629 | -6.308 | 41.505 | 1.00 | 21.15 |
| 23015 | O | GLY | D | 607 | -97.564 | -6.384 | 42.123 | 1.00 | 21.69 |
| 23016 | N | TYR | D | 608 | -99.325 | -5.172 | 41.394 | 1.00 | 21.32 |
| 23017 | CA | TYR | D | 608 | -98.955 | -3.955 | 42.075 | 1.00 | 21.05 |
| 23018 | CB | TYR | D | 608 | -99.920 | -2.870 | 41.644 | 1.00 | 21.75 |
| 23019 | CG | TYR | D | 608 | -99.789 | -1.561 | 42.412 | 1.00 | 19.88 |
| 23020 | CD1 | TYR | D | 608 | -100.839 | -1.076 | 43.171 | 1.00 | 18.29 |
| 23021 | CE1 | TYR | D | 608 | -100.738 | 0.144 | 43.831 | 1.00 | 19.02 |
| 23022 | CZ | TYR | D | 608 | -99.576 | 0.867 | 43.738 | 1.00 | 18.01 |
| 23023 | OH | TYR | D | 608 | -99.460 | 2.076 | 44.406 | 1.00 | 19.81 |
| 23024 | CE2 | TYR | D | 608 | -98.518 | 0.382 | 42.994 | 1.00 | 16.72 |
| 23025 | CD2 | TYR | D | 608 | -98.639 | -0.802 | 42.326 | 1.00 | 16.68 |
| 23026 | C | TYR | D | 608 | -99.033 | -4.139 | 43.592 | 1.00 | 21.56 |
| 23027 | O | TYR | D | 608 | -98.074 | -3.875 | 44.301 | 1.00 | 21.04 |
| 23028 | N | VAL | D | 609 | -100.173 | -4.617 | 44.090 | 1.00 | 21.97 |
| 23029 | CA | VAL | D | 609 | -100.330 | -4.835 | 45.529 | 1.00 | 22.43 |
| 23030 | CB | VAL | D | 609 | -101.749 | -5.254 | 45.905 | 1.00 | 22.62 |
| 23031 | CG1 | VAL | D | 609 | -101.836 | -5.550 | 47.428 | 1.00 | 22.40 |
| 23032 | CG2 | VAL | D | 609 | -102.699 | -4.105 | 45.568 | 1.00 | 22.38 |
| 23033 | C | VAL | D | 609 | -99.312 | -5.822 | 46.066 | 1.00 | 23.00 |
| 23034 | O | VAL | D | 609 | -98.640 | -5.546 | 47.077 | 1.00 | 23.05 |
| 23035 | N | THR | D | 610 | -99.167 | -6.943 | 45.356 | 1.00 | 23.22 |
| 23036 | CA | THR | D | 610 | -98.195 | -7.967 | 45.702 | 1.00 | 23.21 |
| 23037 | CB | THR | D | 610 | -98.125 | -9.072 | 44.599 | 1.00 | 22.93 |
| 23038 | OG1 | THR | D | 610 | -99.203 | -9.996 | 44.777 | 1.00 | 22.62 |
| 23039 | CG2 | THR | D | 610 | -96.871 | -9.962 | 44.779 | 1.00 | 22.26 |
| 23040 | C | THR | D | 610 | -96.834 | -7.352 | 45.873 | 1.00 | 23.38 |
| 23041 | O | THR | D | 610 | -96.152 | -7.606 | 46.865 | 1.00 | 23.59 |
| 23042 | N | SER | D | 611 | -96.431 | -6.556 | 44.887 | 1.00 | 23.59 |

FIGURE 3 QJ

| A | B | C | D | E | F | G | H | I | J |
|---|---|---|---|---|---|---|---|---|---|
| 23043 | CA | SER | D | 611 | -95.111 | -5.923 | 44.880 | 1.00 | 23.09 |
| 23044 | CB | SER | D | 611 | -94.866 | -5.263 | 43.533 | 1.00 | 23.14 |
| 23045 | OG | SER | D | 611 | -94.870 | -6.221 | 42.488 | 1.00 | 23.80 |
| 23046 | C | SER | D | 611 | -94.981 | -4.878 | 45.993 | 1.00 | 23.31 |
| 23047 | O | SER | D | 611 | -93.948 | -4.797 | 46.667 | 1.00 | 23.41 |
| 23048 | N | MET | D | 612 | -96.041 | -4.089 | 46.177 | 1.00 | 22.64 |
| 23049 | CA | MET | D | 612 | -96.097 | -3.081 | 47.219 | 1.00 | 21.73 |
| 23050 | CB | MET | D | 612 | -97.403 | -2.311 | 47.109 | 1.00 | 21.27 |
| 23051 | CG | MET | D | 612 | -97.449 | -1.400 | 45.874 | 1.00 | 20.75 |
| 23052 | SD | MET | D | 612 | -96.138 | -0.132 | 45.962 | 1.00 | 22.54 |
| 23053 | CE | MET | D | 612 | -96.942 | 0.982 | 47.037 | 1.00 | 20.15 |
| 23054 | C | MET | D | 612 | -95.945 | -3.743 | 48.593 | 1.00 | 22.23 |
| 23055 | O | MET | D | 612 | -95.235 | -3.233 | 49.474 | 1.00 | 21.46 |
| 23056 | N | VAL | D | 613 | -96.611 | -4.889 | 48.753 | 1.00 | 21.78 |
| 23057 | CA | VAL | D | 613 | -96.542 | -5.669 | 49.981 | 1.00 | 21.13 |
| 23058 | CB | VAL | D | 613 | -97.625 | -6.782 | 49.969 | 1.00 | 21.05 |
| 23059 | CG1 | VAL | D | 613 | -97.274 | -7.913 | 50.941 | 1.00 | 21.49 |
| 23060 | CG2 | VAL | D | 613 | -99.002 | -6.207 | 50.242 | 1.00 | 19.63 |
| 23061 | C | VAL | D | 613 | -95.142 | -6.282 | 50.115 | 1.00 | 21.21 |
| 23062 | O | VAL | D | 613 | -94.525 | -6.234 | 51.180 | 1.00 | 22.38 |
| 23063 | N | LEU | D | 614 | -94.598 | -6.833 | 49.041 | 1.00 | 21.20 |
| 23064 | CA | LEU | D | 614 | -93.247 | -7.387 | 49.152 | 1.00 | 21.30 |
| 23065 | CB | LEU | D | 614 | -92.854 | -8.140 | 47.900 | 1.00 | 20.29 |
| 23066 | CG | LEU | D | 614 | -93.636 | -9.428 | 47.666 | 1.00 | 19.95 |
| 23067 | CD1 | LEU | D | 614 | -93.462 | -10.439 | 48.841 | 1.00 | 19.35 |
| 23068 | CD2 | LEU | D | 614 | -93.206 | -10.047 | 46.380 | 1.00 | 15.59 |
| 23069 | C | LEU | D | 614 | -92.170 | -6.344 | 49.497 | 1.00 | 22.17 |
| 23070 | O | LEU | D | 614 | -91.159 | -6.684 | 50.102 | 1.00 | 22.67 |
| 23071 | N | GLY | D | 615 | -92.377 | -5.083 | 49.126 | 1.00 | 22.27 |
| 23072 | CA | GLY | D | 615 | -91.395 | -4.061 | 49.410 | 1.00 | 22.40 |
| 23073 | C | GLY | D | 615 | -91.726 | -3.183 | 50.605 | 1.00 | 23.25 |
| 23074 | O | GLY | D | 615 | -91.081 | -2.134 | 50.848 | 1.00 | 23.33 |
| 23075 | N | SER | D | 616 | -92.711 | -3.629 | 51.376 | 1.00 | 23.60 |
| 23076 | CA | SER | D | 616 | -93.200 | -2.904 | 52.534 | 1.00 | 23.70 |
| 23077 | CB | SER | D | 616 | -94.596 | -3.413 | 52.874 | 1.00 | 23.88 |
| 23078 | OG | SER | D | 616 | -94.509 | -4.694 | 53.490 | 1.00 | 25.47 |
| 23079 | C | SER | D | 616 | -92.343 | -3.029 | 53.790 | 1.00 | 24.16 |
| 23080 | O | SER | D | 616 | -92.471 | -2.208 | 54.698 | 1.00 | 25.00 |
| 23081 | N | GLY | D | 617 | -91.498 | -4.049 | 53.870 | 1.00 | 24.13 |
| 23082 | CA | GLY | D | 617 | -90.726 | -4.287 | 55.080 | 1.00 | 24.51 |
| 23083 | C | GLY | D | 617 | -91.497 | -4.875 | 56.253 | 1.00 | 25.66 |
| 23084 | O | GLY | D | 617 | -91.042 | -4.815 | 57.394 | 1.00 | 26.49 |
| 23085 | N | SER | D | 618 | -92.654 | -5.477 | 55.997 | 1.00 | 25.95 |
| 23086 | CA | SER | D | 618 | -93.486 | -5.940 | 57.090 | 1.00 | 26.12 |
| 23087 | CB | SER | D | 618 | -94.913 | -6.191 | 56.618 | 1.00 | 25.79 |
| 23088 | OG | SER | D | 618 | -94.958 | -7.356 | 55.822 | 1.00 | 25.11 |
| 23089 | C | SER | D | 618 | -92.940 | -7.214 | 57.721 | 1.00 | 27.16 |
| 23090 | O | SER | D | 618 | -93.216 | -7.500 | 58.885 | 1.00 | 27.72 |
| 23091 | N | GLY | D | 619 | -92.197 | -7.991 | 56.950 | 1.00 | 26.87 |
| 23092 | CA | GLY | D | 619 | -91.651 | -9.226 | 57.467 | 1.00 | 27.32 |
| 23093 | C | GLY | D | 619 | -92.606 | -10.409 | 57.474 | 1.00 | 27.28 |

FIGURE 3 QK

| A | B | C | D | E | F | G | H | I | J |
|---|---|---|---|---|---|---|---|---|---|
| 23094 | O | GLY | D | 619 | -92.235 | -11.504 | 57.864 | 1.00 | 27.63 |
| 23095 | N | VAL | D | 620 | -93.816 | -10.215 | 56.990 | 1.00 | 26.98 |
| 23096 | CA | VAL | D | 620 | -94.823 | -11.272 | 57.054 | 1.00 | 26.82 |
| 23097 | CB | VAL | D | 620 | -96.215 | -10.663 | 57.128 | 1.00 | 27.10 |
| 23098 | CG1 | VAL | D | 620 | -97.299 | -11.735 | 57.065 | 1.00 | 27.01 |
| 23099 | CG2 | VAL | D | 620 | -96.327 | -9.803 | 58.398 | 1.00 | 25.69 |
| 23100 | C | VAL | D | 620 | -94.751 | -12.234 | 55.886 | 1.00 | 26.89 |
| 23101 | O | VAL | D | 620 | -95.068 | -13.412 | 56.022 | 1.00 | 27.36 |
| 23102 | N | PHE | D | 621 | -94.293 | -11.741 | 54.743 | 1.00 | 26.24 |
| 23103 | CA | PHE | D | 621 | -94.230 | -12.554 | 53.554 | 1.00 | 25.32 |
| 23104 | CB | PHE | D | 621 | -94.896 | -11.806 | 52.380 | 1.00 | 25.19 |
| 23105 | CG | PHE | D | 621 | -96.339 | -11.424 | 52.653 | 1.00 | 23.16 |
| 23106 | CD1 | PHE | D | 621 | -96.642 | -10.280 | 53.349 | 1.00 | 20.70 |
| 23107 | CE1 | PHE | D | 621 | -97.964 | -9.940 | 53.621 | 1.00 | 19.37 |
| 23108 | CZ | PHE | D | 621 | -98.987 | -10.744 | 53.191 | 1.00 | 20.10 |
| 23109 | CE2 | PHE | D | 621 | -98.703 | -11.898 | 52.500 | 1.00 | 19.43 |
| 23110 | CD2 | PHE | D | 621 | -97.385 | -12.233 | 52.228 | 1.00 | 21.78 |
| 23111 | C | PHE | D | 621 | -92.809 | -12.976 | 53.230 | 1.00 | 25.90 |
| 23112 | O | PHE | D | 621 | -91.863 | -12.192 | 53.302 | 1.00 | 26.42 |
| 23113 | N | LYS | D | 622 | -92.658 | -14.231 | 52.874 | 1.00 | 26.12 |
| 23114 | CA | LYS | D | 622 | -91.356 | -14.759 | 52.530 | 1.00 | 27.08 |
| 23115 | CB | LYS | D | 622 | -91.336 | -16.265 | 52.812 | 1.00 | 26.96 |
| 23116 | CG | LYS | D | 622 | -89.995 | -16.936 | 52.586 | 1.00 | 28.63 |
| 23117 | CD | LYS | D | 622 | -90.086 | -18.436 | 52.926 | 1.00 | 30.58 |
| 23118 | CE | LYS | D | 622 | -88.716 | -19.103 | 52.885 | 1.00 | 33.11 |
| 23119 | NZ | LYS | D | 622 | -88.146 | -19.197 | 51.521 | 1.00 | 34.13 |
| 23120 | C | LYS | D | 622 | -91.074 | -14.517 | 51.048 | 1.00 | 26.97 |
| 23121 | O | LYS | D | 622 | -89.949 | -14.222 | 50.655 | 1.00 | 26.68 |
| 23122 | N | CYS | D | 623 | -92.114 | -14.624 | 50.228 | 1.00 | 27.32 |
| 23123 | CA | CYS | D | 623 | -91.939 | -14.514 | 48.789 | 1.00 | 27.63 |
| 23124 | CB | CYS | D | 623 | -91.486 | -15.855 | 48.239 | 1.00 | 28.04 |
| 23125 | SG | CYS | D | 623 | -92.673 | -17.133 | 48.612 | 1.00 | 32.49 |
| 23126 | C | CYS | D | 623 | -93.240 | -14.143 | 48.116 | 1.00 | 26.28 |
| 23127 | O | CYS | D | 623 | -94.290 | -14.113 | 48.749 | 1.00 | 26.71 |
| 23128 | N | GLY | D | 624 | -93.169 | -13.870 | 46.823 | 1.00 | 24.98 |
| 23129 | CA | GLY | D | 624 | -94.353 | -13.530 | 46.069 | 1.00 | 23.48 |
| 23130 | C | GLY | D | 624 | -94.092 | -13.437 | 44.577 | 1.00 | 23.30 |
| 23131 | O | GLY | D | 624 | -92.936 | -13.432 | 44.120 | 1.00 | 22.53 |
| 23132 | N | ILE | D | 625 | -95.188 | -13.372 | 43.822 | 1.00 | 22.21 |
| 23133 | CA | ILE | D | 625 | -95.137 | -13.374 | 42.385 | 1.00 | 21.40 |
| 23134 | CB | ILE | D | 625 | -95.706 | -14.692 | 41.842 | 1.00 | 21.55 |
| 23135 | CG1 | ILE | D | 625 | -95.026 | -15.905 | 42.472 | 1.00 | 21.25 |
| 23136 | CD1 | ILE | D | 625 | -95.620 | -17.199 | 41.976 | 1.00 | 22.46 |
| 23137 | CG2 | ILE | D | 625 | -95.572 | -14.742 | 40.327 | 1.00 | 20.26 |
| 23138 | C | ILE | D | 625 | -96.022 | -12.264 | 41.865 | 1.00 | 21.62 |
| 23139 | O | ILE | D | 625 | -97.201 | -12.201 | 42.211 | 1.00 | 20.79 |
| 23140 | N | ALA | D | 626 | -95.466 | -11.399 | 41.024 | 1.00 | 21.33 |
| 23141 | CA | ALA | D | 626 | -96.262 | -10.317 | 40.453 | 1.00 | 21.56 |
| 23142 | CB | ALA | D | 626 | -95.638 | -8.956 | 40.754 | 1.00 | 21.64 |
| 23143 | C | ALA | D | 626 | -96.331 | -10.525 | 38.960 | 1.00 | 21.03 |
| 23144 | O | ALA | D | 626 | -95.311 | -10.566 | 38.290 | 1.00 | 21.70 |

FIGURE 3 QL

| A | B | C | D | E | F | G | H | I | J |
|---|---|---|---|---|---|---|---|---|---|
| 23145 | N | VAL | D | 627 | -97.534 | -10.641 | 38.434 | 1.00 | 20.44 |
| 23146 | CA | VAL | D | 627 | -97.698 | -10.876 | 37.010 | 1.00 | 19.92 |
| 23147 | CB | VAL | D | 627 | -98.638 | -12.074 | 36.779 | 1.00 | 19.63 |
| 23148 | CG1 | VAL | D | 627 | -98.779 | -12.364 | 35.328 | 1.00 | 19.32 |
| 23149 | CG2 | VAL | D | 627 | -98.121 | -13.277 | 37.526 | 1.00 | 19.10 |
| 23150 | C | VAL | D | 627 | -98.270 | -9.636 | 36.336 | 1.00 | 19.71 |
| 23151 | O | VAL | D | 627 | -99.321 | -9.147 | 36.741 | 1.00 | 20.98 |
| 23152 | N | ALA | D | 628 | -97.564 | -9.119 | 35.334 | 1.00 | 19.16 |
| 23153 | CA | ALA | D | 628 | -97.994 | -7.944 | 34.606 | 1.00 | 19.09 |
| 23154 | CB | ALA | D | 628 | -99.125 | -8.313 | 33.667 | 1.00 | 19.00 |
| 23155 | C | ALA | D | 628 | -98.443 | -6.846 | 35.563 | 1.00 | 19.80 |
| 23156 | O | ALA | D | 628 | -99.564 | -6.318 | 35.442 | 1.00 | 20.29 |
| 23157 | N | PRO | D | 629 | -97.596 | -6.499 | 36.524 | 1.00 | 19.51 |
| 23158 | CA | PRO | D | 629 | -97.984 | -5.513 | 37.533 | 1.00 | 19.62 |
| 23159 | CB | PRO | D | 629 | -96.889 | -5.669 | 38.584 | 1.00 | 19.78 |
| 23160 | CG | PRO | D | 629 | -95.679 | -5.993 | 37.730 | 1.00 | 20.27 |
| 23161 | CD | PRO | D | 629 | -96.236 | -7.022 | 36.749 | 1.00 | 19.35 |
| 23162 | C | PRO | D | 629 | -97.927 | -4.088 | 37.040 | 1.00 | 20.11 |
| 23163 | O | PRO | D | 629 | -97.120 | -3.718 | 36.174 | 1.00 | 20.33 |
| 23164 | N | VAL | D | 630 | -98.806 | -3.274 | 37.594 | 1.00 | 20.35 |
| 23165 | CA | VAL | D | 630 | -98.654 | -1.844 | 37.453 | 1.00 | 20.36 |
| 23166 | CB | VAL | D | 630 | -99.956 | -1.119 | 37.858 | 1.00 | 20.44 |
| 23167 | CG1 | VAL | D | 630 | -99.658 | 0.296 | 38.468 | 1.00 | 19.91 |
| 23168 | CG2 | VAL | D | 630 | -100.903 | -1.027 | 36.674 | 1.00 | 19.46 |
| 23169 | C | VAL | D | 630 | -97.512 | -1.548 | 38.458 | 1.00 | 20.76 |
| 23170 | O | VAL | D | 630 | -97.420 | -2.207 | 39.502 | 1.00 | 19.76 |
| 23171 | N | SER | D | 631 | -96.628 | -0.601 | 38.138 | 1.00 | 20.86 |
| 23172 | CA | SER | D | 631 | -95.524 | -0.284 | 39.027 | 1.00 | 21.41 |
| 23173 | CB | SER | D | 631 | -94.183 | -0.668 | 38.404 | 1.00 | 21.58 |
| 23174 | OG | SER | D | 631 | -93.908 | 0.098 | 37.254 | 1.00 | 22.64 |
| 23175 | C | SER | D | 631 | -95.514 | 1.186 | 39.452 | 1.00 | 21.56 |
| 23176 | O | SER | D | 631 | -95.023 | 1.506 | 40.528 | 1.00 | 20.61 |
| 23177 | N | ARG | D | 632 | -96.002 | 2.066 | 38.579 | 1.00 | 21.04 |
| 23178 | CA | ARG | D | 632 | -96.184 | 3.465 | 38.917 | 1.00 | 22.20 |
| 23179 | CB | ARG | D | 632 | -94.932 | 4.341 | 38.755 | 1.00 | 23.16 |
| 23180 | CG | ARG | D | 632 | -94.545 | 4.709 | 37.399 | 1.00 | 25.77 |
| 23181 | CD | ARG | D | 632 | -94.066 | 6.140 | 37.276 | 1.00 | 30.32 |
| 23182 | NE | ARG | D | 632 | -93.188 | 6.556 | 38.351 | 1.00 | 32.43 |
| 23183 | CZ | ARG | D | 632 | -92.553 | 7.733 | 38.389 | 1.00 | 35.70 |
| 23184 | NH1 | ARG | D | 632 | -91.777 | 8.011 | 39.428 | 1.00 | 34.00 |
| 23185 | NH2 | ARG | D | 632 | -92.684 | 8.632 | 37.395 | 1.00 | 34.81 |
| 23186 | C | ARG | D | 632 | -97.372 | 3.964 | 38.133 | 1.00 | 21.99 |
| 23187 | O | ARG | D | 632 | -97.580 | 3.572 | 36.982 | 1.00 | 21.10 |
| 23188 | N | TRP | D | 633 | -98.195 | 4.759 | 38.808 | 1.00 | 21.72 |
| 23189 | CA | TRP | D | 633 | -99.493 | 5.143 | 38.269 | 1.00 | 22.29 |
| 23190 | CB | TRP | D | 633 | -100.405 | 5.680 | 39.393 | 1.00 | 22.18 |
| 23191 | CG | TRP | D | 633 | -100.858 | 4.501 | 40.246 | 1.00 | 22.76 |
| 23192 | CD1 | TRP | D | 633 | -100.506 | 4.231 | 41.540 | 1.00 | 20.58 |
| 23193 | NE1 | TRP | D | 633 | -101.080 | 3.053 | 41.947 | 1.00 | 20.97 |
| 23194 | CE2 | TRP | D | 633 | -101.825 | 2.535 | 40.916 | 1.00 | 21.34 |
| 23195 | CD2 | TRP | D | 633 | -101.691 | 3.410 | 39.822 | 1.00 | 20.22 |

FIGURE 3 QM

| A | B | C | D | E | F | G | H | I | J |
|---|---|---|---|---|---|---|---|---|---|
| 23196 | CE3 | TRP | D | 633 | -102.353 | 3.095 | 38.629 | 1.00 | 20.65 |
| 23197 | CZ3 | TRP | D | 633 | -103.099 | 1.934 | 38.560 | 1.00 | 20.30 |
| 23198 | CH2 | TRP | D | 633 | -103.204 | 1.076 | 39.662 | 1.00 | 20.21 |
| 23199 | CZ2 | TRP | D | 633 | -102.558 | 1.344 | 40.840 | 1.00 | 19.01 |
| 23200 | C | TRP | D | 633 | -99.452 | 6.006 | 37.031 | 1.00 | 22.40 |
| 23201 | O | TRP | D | 633 | -100.365 | 5.963 | 36.230 | 1.00 | 23.36 |
| 23202 | N | GLU | D | 634 | -98.373 | 6.737 | 36.832 | 1.00 | 23.31 |
| 23203 | CA | GLU | D | 634 | -98.252 | 7.551 | 35.634 | 1.00 | 24.08 |
| 23204 | CB | GLU | D | 634 | -97.082 | 8.534 | 35.714 | 1.00 | 24.74 |
| 23205 | CG | GLU | D | 634 | -97.298 | 9.664 | 36.714 | 1.00 | 26.01 |
| 23206 | CD | GLU | D | 634 | -96.482 | 9.460 | 37.972 | 1.00 | 31.66 |
| 23207 | OE1 | GLU | D | 634 | -95.612 | 10.335 | 38.201 | 1.00 | 32.18 |
| 23208 | OE2 | GLU | D | 634 | -96.691 | 8.419 | 38.703 | 1.00 | 30.86 |
| 23209 | C | GLU | D | 634 | -98.114 | 6.703 | 34.391 | 1.00 | 23.69 |
| 23210 | O | GLU | D | 634 | -98.362 | 7.200 | 33.303 | 1.00 | 23.35 |
| 23211 | N | TYR | D | 635 | -97.718 | 5.434 | 34.537 | 1.00 | 23.21 |
| 23212 | CA | TYR | D | 635 | -97.615 | 4.548 | 33.372 | 1.00 | 22.82 |
| 23213 | CB | TYR | D | 635 | -96.723 | 3.345 | 33.640 | 1.00 | 22.54 |
| 23214 | CG | TYR | D | 635 | -95.283 | 3.663 | 33.966 | 1.00 | 24.14 |
| 23215 | CD1 | TYR | D | 635 | -94.726 | 4.898 | 33.641 | 1.00 | 23.13 |
| 23216 | CE1 | TYR | D | 635 | -93.418 | 5.183 | 33.938 | 1.00 | 23.12 |
| 23217 | CZ | TYR | D | 635 | -92.646 | 4.231 | 34.583 | 1.00 | 24.31 |
| 23218 | OH | TYR | D | 635 | -91.347 | 4.502 | 34.892 | 1.00 | 23.90 |
| 23219 | CE2 | TYR | D | 635 | -93.173 | 3.005 | 34.923 | 1.00 | 24.61 |
| 23220 | CD2 | TYR | D | 635 | -94.480 | 2.723 | 34.611 | 1.00 | 24.33 |
| 23221 | C | TYR | D | 635 | -98.959 | 3.976 | 32.978 | 1.00 | 22.64 |
| 23222 | O | TYR | D | 635 | -99.123 | 3.441 | 31.878 | 1.00 | 22.13 |
| 23223 | N | TYR | D | 636 | -99.927 | 4.025 | 33.876 | 1.00 | 22.22 |
| 23224 | CA | TYR | D | 636 | -101.162 | 3.352 | 33.526 | 1.00 | 22.38 |
| 23225 | CB | TYR | D | 636 | -101.788 | 2.660 | 34.727 | 1.00 | 21.80 |
| 23226 | CG | TYR | D | 636 | -102.788 | 1.640 | 34.286 | 1.00 | 19.84 |
| 23227 | CD1 | TYR | D | 636 | -102.417 | 0.625 | 33.436 | 1.00 | 18.32 |
| 23228 | CE1 | TYR | D | 636 | -103.335 | -0.316 | 32.998 | 1.00 | 20.41 |
| 23229 | CZ | TYR | D | 636 | -104.628 | -0.238 | 33.413 | 1.00 | 20.72 |
| 23230 | OH | TYR | D | 636 | -105.537 | -1.174 | 32.967 | 1.00 | 24.19 |
| 23231 | CE2 | TYR | D | 636 | -105.030 | 0.781 | 34.259 | 1.00 | 20.82 |
| 23232 | CD2 | TYR | D | 636 | -104.113 | 1.723 | 34.673 | 1.00 | 18.74 |
| 23233 | C | TYR | D | 636 | -102.146 | 4.258 | 32.778 | 1.00 | 22.84 |
| 23234 | O | TYR | D | 636 | -101.933 | 5.461 | 32.700 | 1.00 | 23.58 |
| 23235 | N | ASP | D | 637 | -103.179 | 3.680 | 32.178 | 1.00 | 23.34 |
| 23236 | CA | ASP | D | 637 | -104.079 | 4.478 | 31.365 | 1.00 | 24.69 |
| 23237 | CB | ASP | D | 637 | -105.030 | 3.616 | 30.523 | 1.00 | 24.97 |
| 23238 | CG | ASP | D | 637 | -106.145 | 3.012 | 31.328 | 1.00 | 25.70 |
| 23239 | OD1 | ASP | D | 637 | -106.957 | 3.784 | 31.853 | 1.00 | 26.97 |
| 23240 | OD2 | ASP | D | 637 | -106.313 | 1.778 | 31.453 | 1.00 | 26.60 |
| 23241 | C | ASP | D | 637 | -104.798 | 5.545 | 32.178 | 1.00 | 25.32 |
| 23242 | O | ASP | D | 637 | -104.842 | 5.495 | 33.411 | 1.00 | 25.23 |
| 23243 | N | SER | D | 638 | -105.354 | 6.522 | 31.474 | 1.00 | 25.73 |
| 23244 | CA | SER | D | 638 | -105.904 | 7.694 | 32.132 | 1.00 | 25.90 |
| 23245 | CB | SER | D | 638 | -105.934 | 8.843 | 31.140 | 1.00 | 25.38 |
| 23246 | OG | SER | D | 638 | -106.815 | 8.506 | 30.101 | 1.00 | 26.53 |

FIGURE 3 QN

| A | B | C | D | E | F | G | H | I | J |
|---|---|---|---|---|---|---|---|---|---|
| 23247 | C | SER | D | 638 | -107.281 | 7.516 | 32.777 | 1.00 | 25.91 |
| 23248 | O | SER | D | 638 | -107.500 | 7.960 | 33.897 | 1.00 | 25.61 |
| 23249 | N | VAL | D | 639 | -108.218 | 6.863 | 32.103 | 1.00 | 26.51 |
| 23250 | CA | VAL | D | 639 | -109.543 | 6.834 | 32.699 | 1.00 | 27.09 |
| 23251 | CB | VAL | D | 639 | -110.686 | 6.551 | 31.688 | 1.00 | 27.52 |
| 23252 | CG1 | VAL | D | 639 | -111.496 | 5.339 | 32.069 | 1.00 | 29.06 |
| 23253 | CG2 | VAL | D | 639 | -110.168 | 6.505 | 30.248 | 1.00 | 28.47 |
| 23254 | C | VAL | D | 639 | -109.596 | 5.992 | 33.977 | 1.00 | 26.75 |
| 23255 | O | VAL | D | 639 | -110.272 | 6.357 | 34.932 | 1.00 | 26.42 |
| 23256 | N | TYR | D | 640 | -108.832 | 4.905 | 34.014 | 1.00 | 26.18 |
| 23257 | CA | TYR | D | 640 | -108.798 | 4.075 | 35.205 | 1.00 | 25.96 |
| 23258 | CB | TYR | D | 640 | -108.168 | 2.719 | 34.893 | 1.00 | 25.44 |
| 23259 | CG | TYR | D | 640 | -108.145 | 1.767 | 36.066 | 1.00 | 24.92 |
| 23260 | CD1 | TYR | D | 640 | -109.119 | 0.787 | 36.205 | 1.00 | 24.01 |
| 23261 | CE1 | TYR | D | 640 | -109.100 | -0.084 | 37.269 | 1.00 | 21.51 |
| 23262 | CZ | TYR | D | 640 | -108.096 | 0.010 | 38.227 | 1.00 | 22.81 |
| 23263 | OH | TYR | D | 640 | -108.097 | -0.872 | 39.286 | 1.00 | 23.49 |
| 23264 | CE2 | TYR | D | 640 | -107.130 | 0.967 | 38.134 | 1.00 | 21.03 |
| 23265 | CD2 | TYR | D | 640 | -107.149 | 1.846 | 37.050 | 1.00 | 24.50 |
| 23266 | C | TYR | D | 640 | -108.032 | 4.762 | 36.337 | 1.00 | 25.42 |
| 23267 | O | TYR | D | 640 | -108.579 | 5.006 | 37.400 | 1.00 | 25.71 |
| 23268 | N | THR | D | 641 | -106.769 | 5.067 | 36.080 | 1.00 | 25.09 |
| 23269 | CA | THR | D | 641 | -105.878 | 5.672 | 37.052 | 1.00 | 25.10 |
| 23270 | CB | THR | D | 641 | -104.534 | 5.962 | 36.403 | 1.00 | 24.83 |
| 23271 | OG1 | THR | D | 641 | -103.960 | 4.743 | 35.940 | 1.00 | 26.06 |
| 23272 | CG2 | THR | D | 641 | -103.534 | 6.479 | 37.441 | 1.00 | 24.57 |
| 23273 | C | THR | D | 641 | -106.408 | 6.976 | 37.630 | 1.00 | 25.18 |
| 23274 | O | THR | D | 641 | -106.429 | 7.163 | 38.848 | 1.00 | 24.41 |
| 23275 | N | GLU | D | 642 | -106.830 | 7.872 | 36.749 | 1.00 | 24.77 |
| 23276 | CA | GLU | D | 642 | -107.304 | 9.174 | 37.187 | 1.00 | 25.52 |
| 23277 | CB | GLU | D | 642 | -107.435 | 10.125 | 35.991 | 1.00 | 25.53 |
| 23278 | CG | GLU | D | 642 | -106.086 | 10.541 | 35.424 | 1.00 | 25.78 |
| 23279 | CD | GLU | D | 642 | -106.193 | 11.254 | 34.090 | 1.00 | 26.46 |
| 23280 | OE1 | GLU | D | 642 | -107.337 | 11.592 | 33.676 | 1.00 | 23.00 |
| 23281 | OE2 | GLU | D | 642 | -105.122 | 11.473 | 33.469 | 1.00 | 27.43 |
| 23282 | C | GLU | D | 642 | -108.606 | 9.070 | 37.976 | 1.00 | 25.69 |
| 23283 | O | GLU | D | 642 | -108.879 | 9.886 | 38.858 | 1.00 | 26.67 |
| 23284 | N | ARG | D | 643 | -109.400 | 8.053 | 37.686 | 1.00 | 25.27 |
| 23285 | CA | ARG | D | 643 | -110.625 | 7.839 | 38.437 | 1.00 | 25.75 |
| 23286 | CB | ARG | D | 643 | -111.233 | 6.507 | 38.014 | 1.00 | 26.11 |
| 23287 | CG | ARG | D | 643 | -112.604 | 6.225 | 38.580 | 1.00 | 26.46 |
| 23288 | CD | ARG | D | 643 | -113.448 | 5.411 | 37.619 | 1.00 | 30.50 |
| 23289 | NE | ARG | D | 643 | -112.919 | 4.068 | 37.485 | 1.00 | 32.80 |
| 23290 | CZ | ARG | D | 643 | -112.837 | 3.381 | 36.360 | 1.00 | 31.23 |
| 23291 | NH1 | ARG | D | 643 | -112.334 | 2.160 | 36.397 | 1.00 | 31.11 |
| 23292 | NH2 | ARG | D | 643 | -113.239 | 3.895 | 35.214 | 1.00 | 30.58 |
| 23293 | C | ARG | D | 643 | -110.356 | 7.800 | 39.963 | 1.00 | 25.90 |
| 23294 | O | ARG | D | 643 | -111.142 | 8.302 | 40.767 | 1.00 | 24.71 |
| 23295 | N | TYR | D | 644 | -109.234 | 7.184 | 40.332 | 1.00 | 25.76 |
| 23296 | CA | TYR | D | 644 | -108.868 | 7.006 | 41.723 | 1.00 | 26.45 |
| 23297 | CB | TYR | D | 644 | -108.476 | 5.531 | 41.957 | 1.00 | 26.40 |

FIGURE 3 QO

| A | B | C | D | E | F | G | H | I | J |
|---|---|---|---|---|---|---|---|---|---|
| 23298 | CG | TYR | D | 644 | -109.364 | 4.543 | 41.220 | 1.00 | 25.41 |
| 23299 | CD1 | TYR | D | 644 | -110.679 | 4.338 | 41.610 | 1.00 | 25.27 |
| 23300 | CE1 | TYR | D | 644 | -111.490 | 3.447 | 40.952 | 1.00 | 24.47 |
| 23301 | CZ | TYR | D | 644 | -111.002 | 2.750 | 39.857 | 1.00 | 25.81 |
| 23302 | OH | TYR | D | 644 | -111.812 | 1.859 | 39.198 | 1.00 | 25.64 |
| 23303 | CE2 | TYR | D | 644 | -109.713 | 2.942 | 39.432 | 1.00 | 25.89 |
| 23304 | CD2 | TYR | D | 644 | -108.897 | 3.847 | 40.123 | 1.00 | 26.08 |
| 23305 | C | TYR | D | 644 | -107.705 | 7.905 | 42.130 | 1.00 | 26.93 |
| 23306 | O | TYR | D | 644 | -107.502 | 8.189 | 43.308 | 1.00 | 27.89 |
| 23307 | N | MET | D | 645 | -106.933 | 8.371 | 41.165 | 1.00 | 27.11 |
| 23308 | CA | MET | D | 645 | -105.748 | 9.118 | 41.523 | 1.00 | 27.40 |
| 23309 | CB | MET | D | 645 | -104.524 | 8.520 | 40.829 | 1.00 | 26.37 |
| 23310 | CG | MET | D | 645 | -104.119 | 7.185 | 41.357 | 1.00 | 26.82 |
| 23311 | SD | MET | D | 645 | -103.523 | 7.225 | 43.053 | 1.00 | 28.13 |
| 23312 | CE | MET | D | 645 | -101.827 | 7.877 | 42.790 | 1.00 | 24.04 |
| 23313 | C | MET | D | 645 | -105.807 | 10.586 | 41.198 | 1.00 | 27.88 |
| 23314 | O | MET | D | 645 | -104.871 | 11.308 | 41.506 | 1.00 | 28.19 |
| 23315 | N | GLY | D | 646 | -106.880 | 11.040 | 40.562 | 1.00 | 28.54 |
| 23316 | CA | GLY | D | 646 | -106.888 | 12.418 | 40.121 | 1.00 | 28.79 |
| 23317 | C | GLY | D | 646 | -105.752 | 12.594 | 39.113 | 1.00 | 29.56 |
| 23318 | O | GLY | D | 646 | -105.264 | 11.621 | 38.514 | 1.00 | 29.39 |
| 23319 | N | LEU | D | 647 | -105.303 | 13.827 | 38.936 | 1.00 | 29.71 |
| 23320 | CA | LEU | D | 647 | -104.274 | 14.117 | 37.944 | 1.00 | 30.13 |
| 23321 | CB | LEU | D | 647 | -104.607 | 15.454 | 37.282 | 1.00 | 30.79 |
| 23322 | CG | LEU | D | 647 | -105.479 | 15.373 | 36.022 | 1.00 | 32.03 |
| 23323 | CD1 | LEU | D | 647 | -106.021 | 13.998 | 35.837 | 1.00 | 32.06 |
| 23324 | CD2 | LEU | D | 647 | -106.609 | 16.389 | 36.060 | 1.00 | 33.49 |
| 23325 | C | LEU | D | 647 | -102.884 | 14.158 | 38.572 | 1.00 | 29.81 |
| 23326 | O | LEU | D | 647 | -102.739 | 14.593 | 39.702 | 1.00 | 30.86 |
| 23327 | N | PRO | D | 648 | -101.863 | 13.686 | 37.869 | 1.00 | 29.42 |
| 23328 | CA | PRO | D | 648 | -100.499 | 13.715 | 38.400 | 1.00 | 29.27 |
| 23329 | CB | PRO | D | 648 | -99.788 | 12.641 | 37.569 | 1.00 | 29.19 |
| 23330 | CG | PRO | D | 648 | -100.474 | 12.645 | 36.284 | 1.00 | 28.08 |
| 23331 | CD | PRO | D | 648 | -101.919 | 13.047 | 36.542 | 1.00 | 29.14 |
| 23332 | C | PRO | D | 648 | -99.792 | 15.061 | 38.210 | 1.00 | 29.74 |
| 23333 | O | PRO | D | 648 | -98.744 | 15.100 | 37.580 | 1.00 | 29.58 |
| 23334 | N | THR | D | 649 | -100.363 | 16.136 | 38.740 | 1.00 | 30.57 |
| 23335 | CA | THR | D | 649 | -99.763 | 17.472 | 38.651 | 1.00 | 31.80 |
| 23336 | CB | THR | D | 649 | -100.702 | 18.440 | 37.937 | 1.00 | 31.39 |
| 23337 | OG1 | THR | D | 649 | -101.944 | 18.494 | 38.654 | 1.00 | 33.99 |
| 23338 | CG2 | THR | D | 649 | -101.101 | 17.906 | 36.591 | 1.00 | 31.18 |
| 23339 | C | THR | D | 649 | -99.533 | 18.010 | 40.050 | 1.00 | 32.36 |
| 23340 | O | THR | D | 649 | -100.146 | 17.548 | 41.010 | 1.00 | 32.49 |
| 23341 | N | PRO | D | 650 | -98.683 | 19.020 | 40.173 | 1.00 | 33.18 |
| 23342 | CA | PRO | D | 650 | -98.400 | 19.602 | 41.489 | 1.00 | 33.36 |
| 23343 | CB | PRO | D | 650 | -97.313 | 20.651 | 41.200 | 1.00 | 33.52 |
| 23344 | CG | PRO | D | 650 | -96.782 | 20.316 | 39.830 | 1.00 | 33.60 |
| 23345 | CD | PRO | D | 650 | -97.962 | 19.701 | 39.080 | 1.00 | 33.10 |
| 23346 | C | PRO | D | 650 | -99.652 | 20.244 | 42.100 | 1.00 | 34.02 |
| 23347 | O | PRO | D | 650 | -99.718 | 20.423 | 43.307 | 1.00 | 33.80 |
| 23348 | N | GLU | D | 651 | -100.651 | 20.577 | 41.292 | 1.00 | 34.80 |

FIGURE 3 QP

| A | B | C | D | E | F | G | H | I | J |
|---|---|---|---|---|---|---|---|---|---|
| 23349 | CA  | GLU | D | 651 | -101.858 | 21.125 | 41.903 | 1.00 | 35.73 |
| 23350 | CB  | GLU | D | 651 | -102.394 | 22.357 | 41.159 | 1.00 | 36.27 |
| 23351 | CG  | GLU | D | 651 | -102.305 | 22.323 | 39.650 | 1.00 | 38.03 |
| 23352 | CD  | GLU | D | 651 | -100.901 | 22.573 | 39.124 | 1.00 | 39.96 |
| 23353 | OE1 | GLU | D | 651 | -100.606 | 22.074 | 38.006 | 1.00 | 39.36 |
| 23354 | OE2 | GLU | D | 651 | -100.109 | 23.270 | 39.807 | 1.00 | 39.77 |
| 23355 | C   | GLU | D | 651 | -102.954 | 20.091 | 42.211 | 1.00 | 35.65 |
| 23356 | O   | GLU | D | 651 | -103.973 | 20.423 | 42.834 | 1.00 | 35.50 |
| 23357 | N   | ASP | D | 652 | -102.725 | 18.829 | 41.827 | 1.00 | 35.10 |
| 23358 | CA  | ASP | D | 652 | -103.686 | 17.778 | 42.146 | 1.00 | 34.67 |
| 23359 | CB  | ASP | D | 652 | -104.341 | 17.182 | 40.884 | 1.00 | 35.01 |
| 23360 | CG  | ASP | D | 652 | -105.584 | 16.345 | 41.200 | 1.00 | 36.32 |
| 23361 | OD1 | ASP | D | 652 | -106.426 | 16.135 | 40.285 | 1.00 | 39.06 |
| 23362 | OD2 | ASP | D | 652 | -105.814 | 15.854 | 42.332 | 1.00 | 36.42 |
| 23363 | C   | ASP | D | 652 | -103.070 | 16.695 | 43.027 | 1.00 | 33.99 |
| 23364 | O   | ASP | D | 652 | -103.006 | 16.851 | 44.240 | 1.00 | 34.82 |
| 23365 | N   | ASN | D | 653 | -102.588 | 15.603 | 42.445 | 1.00 | 32.68 |
| 23366 | CA  | ASN | D | 653 | -102.123 | 14.520 | 43.299 | 1.00 | 31.77 |
| 23367 | CB  | ASN | D | 653 | -103.154 | 13.387 | 43.280 | 1.00 | 30.55 |
| 23368 | CG  | ASN | D | 653 | -103.142 | 12.555 | 44.552 | 1.00 | 29.09 |
| 23369 | OD1 | ASN | D | 653 | -102.564 | 12.946 | 45.573 | 1.00 | 26.00 |
| 23370 | ND2 | ASN | D | 653 | -103.815 | 11.404 | 44.504 | 1.00 | 26.65 |
| 23371 | C   | ASN | D | 653 | -100.730 | 13.976 | 43.006 | 1.00 | 31.49 |
| 23372 | O   | ASN | D | 653 | -100.435 | 12.850 | 43.358 | 1.00 | 31.75 |
| 23373 | N   | LEU | D | 654 |  -99.863 | 14.774 | 42.390 | 1.00 | 31.54 |
| 23374 | CA  | LEU | D | 654 |  -98.547 | 14.264 | 42.003 | 1.00 | 30.92 |
| 23375 | CB  | LEU | D | 654 |  -97.725 | 15.319 | 41.292 | 1.00 | 31.00 |
| 23376 | CG  | LEU | D | 654 |  -96.359 | 14.774 | 40.877 | 1.00 | 31.08 |
| 23377 | CD1 | LEU | D | 654 |  -95.323 | 15.888 | 40.781 | 1.00 | 32.92 |
| 23378 | CD2 | LEU | D | 654 |  -96.457 | 14.000 | 39.578 | 1.00 | 27.02 |
| 23379 | C   | LEU | D | 654 |  -97.708 | 13.657 | 43.124 | 1.00 | 30.82 |
| 23380 | O   | LEU | D | 654 |  -96.990 | 12.690 | 42.904 | 1.00 | 30.53 |
| 23381 | N   | ASP | D | 655 |  -97.764 | 14.218 | 44.318 | 1.00 | 30.70 |
| 23382 | CA  | ASP | D | 655 |  -96.947 | 13.652 | 45.376 | 1.00 | 31.26 |
| 23383 | CB  | ASP | D | 655 |  -96.979 | 14.507 | 46.637 | 1.00 | 31.48 |
| 23384 | CG  | ASP | D | 655 |  -96.491 | 15.922 | 46.383 | 1.00 | 34.42 |
| 23385 | OD1 | ASP | D | 655 |  -95.630 | 16.118 | 45.483 | 1.00 | 34.31 |
| 23386 | OD2 | ASP | D | 655 |  -96.934 | 16.900 | 47.029 | 1.00 | 38.79 |
| 23387 | C   | ASP | D | 655 |  -97.355 | 12.210 | 45.668 | 1.00 | 30.63 |
| 23388 | O   | ASP | D | 655 |  -96.499 | 11.338 | 45.813 | 1.00 | 30.49 |
| 23389 | N   | HIS | D | 656 |  -98.648 | 11.934 | 45.743 | 1.00 | 29.83 |
| 23390 | CA  | HIS | D | 656 |  -98.994 | 10.550 | 46.002 | 1.00 | 29.73 |
| 23391 | CB  | HIS | D | 656 | -100.438 | 10.328 | 46.446 | 1.00 | 29.65 |
| 23392 | CG  | HIS | D | 656 | -100.671 |  8.920 | 46.884 | 1.00 | 30.71 |
| 23393 | ND1 | HIS | D | 656 |  -99.932 |  8.331 | 47.889 | 1.00 | 30.42 |
| 23394 | CE1 | HIS | D | 656 | -100.300 |  7.072 | 48.021 | 1.00 | 30.17 |
| 23395 | NE2 | HIS | D | 656 | -101.242 |  6.816 | 47.131 | 1.00 | 28.07 |
| 23396 | CD2 | HIS | D | 656 | -101.478 |  7.952 | 46.394 | 1.00 | 30.82 |
| 23397 | C   | HIS | D | 656 |  -98.630 |  9.638 | 44.819 | 1.00 | 28.97 |
| 23398 | O   | HIS | D | 656 |  -98.252 |  8.501 | 45.036 | 1.00 | 28.51 |
| 23399 | N   | TYR | D | 657 |  -98.718 | 10.147 | 43.588 | 1.00 | 28.14 |

FIGURE 3 QQ

| A | B | C | D | E | F | G | H | I | J |
|---|---|---|---|---|---|---|---|---|---|
| 23400 | CA | TYR | D | 657 | -98.286 | 9.375 | 42.424 | 1.00 | 28.19 |
| 23401 | CB | TYR | D | 657 | -98.376 | 10.193 | 41.139 | 1.00 | 27.67 |
| 23402 | CG | TYR | D | 657 | -99.674 | 10.121 | 40.365 | 1.00 | 26.53 |
| 23403 | CD1 | TYR | D | 657 | -99.802 | 9.308 | 39.255 | 1.00 | 24.07 |
| 23404 | CE1 | TYR | D | 657 | -100.986 | 9.275 | 38.524 | 1.00 | 23.58 |
| 23405 | CZ | TYR | D | 657 | -102.041 | 10.075 | 38.907 | 1.00 | 24.30 |
| 23406 | OH | TYR | D | 657 | -103.245 | 10.065 | 38.206 | 1.00 | 20.81 |
| 23407 | CE2 | TYR | D | 657 | -101.912 | 10.903 | 40.001 | 1.00 | 23.39 |
| 23408 | CD2 | TYR | D | 657 | -100.743 | 10.935 | 40.701 | 1.00 | 25.39 |
| 23409 | C | TYR | D | 657 | -96.831 | 8.985 | 42.554 | 1.00 | 28.74 |
| 23410 | O | TYR | D | 657 | -96.433 | 7.886 | 42.167 | 1.00 | 28.89 |
| 23411 | N | ARG | D | 658 | -96.024 | 9.899 | 43.077 | 1.00 | 29.24 |
| 23412 | CA | ARG | D | 658 | -94.595 | 9.664 | 43.158 | 1.00 | 29.78 |
| 23413 | CB | ARG | D | 658 | -93.843 | 10.986 | 43.273 | 1.00 | 29.78 |
| 23414 | CG | ARG | D | 658 | -93.840 | 11.758 | 41.990 | 1.00 | 30.49 |
| 23415 | CD | ARG | D | 658 | -93.500 | 10.875 | 40.774 | 1.00 | 33.83 |
| 23416 | NE | ARG | D | 658 | -93.915 | 11.491 | 39.519 | 1.00 | 32.92 |
| 23417 | CZ | ARG | D | 658 | -93.256 | 12.469 | 38.929 | 1.00 | 33.21 |
| 23418 | NH1 | ARG | D | 658 | -92.145 | 12.928 | 39.478 | 1.00 | 33.18 |
| 23419 | NH2 | ARG | D | 658 | -93.701 | 12.980 | 37.786 | 1.00 | 33.18 |
| 23420 | C | ARG | D | 658 | -94.269 | 8.807 | 44.344 | 1.00 | 30.14 |
| 23421 | O | ARG | D | 658 | -93.181 | 8.244 | 44.439 | 1.00 | 30.68 |
| 23422 | N | ASN | D | 659 | -95.218 | 8.731 | 45.257 | 1.00 | 30.69 |
| 23423 | CA | ASN | D | 659 | -95.044 | 7.998 | 46.496 | 1.00 | 31.33 |
| 23424 | CB | ASN | D | 659 | -95.796 | 8.704 | 47.625 | 1.00 | 32.34 |
| 23425 | CG | ASN | D | 659 | -94.874 | 9.237 | 48.681 | 1.00 | 36.48 |
| 23426 | OD1 | ASN | D | 659 | -94.189 | 10.246 | 48.469 | 1.00 | 41.41 |
| 23427 | ND2 | ASN | D | 659 | -94.811 | 8.542 | 49.827 | 1.00 | 39.55 |
| 23428 | C | ASN | D | 659 | -95.549 | 6.578 | 46.444 | 1.00 | 30.22 |
| 23429 | O | ASN | D | 659 | -95.230 | 5.802 | 47.316 | 1.00 | 30.45 |
| 23430 | N | SER | D | 660 | -96.362 | 6.248 | 45.444 | 1.00 | 28.90 |
| 23431 | CA | SER | D | 660 | -96.971 | 4.929 | 45.403 | 1.00 | 27.43 |
| 23432 | CB | SER | D | 660 | -98.493 | 5.075 | 45.292 | 1.00 | 27.34 |
| 23433 | OG | SER | D | 660 | -98.852 | 5.896 | 44.191 | 1.00 | 26.77 |
| 23434 | C | SER | D | 660 | -96.400 | 3.989 | 44.318 | 1.00 | 26.29 |
| 23435 | O | SER | D | 660 | -97.068 | 3.064 | 43.845 | 1.00 | 25.76 |
| 23436 | N | THR | D | 661 | -95.155 | 4.221 | 43.941 | 1.00 | 24.89 |
| 23437 | CA | THR | D | 661 | -94.514 | 3.377 | 42.960 | 1.00 | 23.90 |
| 23438 | CB | THR | D | 661 | -93.373 | 4.143 | 42.316 | 1.00 | 24.52 |
| 23439 | OG1 | THR | D | 661 | -92.362 | 4.347 | 43.308 | 1.00 | 25.03 |
| 23440 | CG2 | THR | D | 661 | -93.800 | 5.542 | 41.940 | 1.00 | 23.39 |
| 23441 | C | THR | D | 661 | -93.891 | 2.180 | 43.653 | 1.00 | 22.71 |
| 23442 | O | THR | D | 661 | -93.467 | 2.280 | 44.804 | 1.00 | 21.58 |
| 23443 | N | VAL | D | 662 | -93.778 | 1.054 | 42.961 | 1.00 | 21.39 |
| 23444 | CA | VAL | D | 662 | -93.064 | -0.028 | 43.610 | 1.00 | 20.70 |
| 23445 | CB | VAL | D | 662 | -93.480 | -1.500 | 43.158 | 1.00 | 20.31 |
| 23446 | CG1 | VAL | D | 662 | -94.804 | -1.542 | 42.414 | 1.00 | 17.64 |
| 23447 | CG2 | VAL | D | 662 | -92.383 | -2.269 | 42.485 | 1.00 | 16.38 |
| 23448 | C | VAL | D | 662 | -91.563 | 0.236 | 43.600 | 1.00 | 21.43 |
| 23449 | O | VAL | D | 662 | -90.860 | -0.163 | 44.525 | 1.00 | 22.11 |
| 23450 | N | MET | D | 663 | -91.078 | 0.929 | 42.569 | 1.00 | 22.18 |

FIGURE 3 QR

| A | B | C | D | E | F | G | H | I | J |
|---|---|---|---|---|---|---|---|---|---|
| 23451 | CA | MET | D | 663 | -89.658 | 1.265 | 42.469 | 1.00 | 22.22 |
| 23452 | CB | MET | D | 663 | -89.362 | 2.125 | 41.223 | 1.00 | 22.16 |
| 23453 | CG | MET | D | 663 | -89.309 | 1.330 | 39.884 | 1.00 | 20.41 |
| 23454 | SD | MET | D | 663 | -90.971 | 0.820 | 39.315 | 1.00 | 20.24 |
| 23455 | CE | MET | D | 663 | -91.665 | 2.361 | 38.782 | 1.00 | 17.95 |
| 23456 | C | MET | D | 663 | -89.071 | 1.930 | 43.709 | 1.00 | 23.01 |
| 23457 | O | MET | D | 663 | -87.908 | 1.695 | 44.039 | 1.00 | 24.00 |
| 23458 | N | SER | D | 664 | -89.840 | 2.751 | 44.409 | 1.00 | 23.37 |
| 23459 | CA | SER | D | 664 | -89.273 | 3.427 | 45.571 | 1.00 | 24.66 |
| 23460 | CB | SER | D | 664 | -90.184 | 4.544 | 46.035 | 1.00 | 25.02 |
| 23461 | OG | SER | D | 664 | -91.461 | 4.013 | 46.338 | 1.00 | 27.47 |
| 23462 | C | SER | D | 664 | -89.039 | 2.465 | 46.740 | 1.00 | 25.06 |
| 23463 | O | SER | D | 664 | -88.336 | 2.799 | 47.696 | 1.00 | 24.70 |
| 23464 | N | ARG | D | 665 | -89.614 | 1.268 | 46.649 | 1.00 | 24.56 |
| 23465 | CA | ARG | D | 665 | -89.456 | 0.284 | 47.700 | 1.00 | 24.85 |
| 23466 | CB | ARG | D | 665 | -90.798 | -0.369 | 47.999 | 1.00 | 24.78 |
| 23467 | CG | ARG | D | 665 | -91.809 | 0.640 | 48.551 | 1.00 | 25.88 |
| 23468 | CD | ARG | D | 665 | -93.214 | 0.129 | 48.642 | 1.00 | 26.79 |
| 23469 | NE | ARG | D | 665 | -94.129 | 1.112 | 49.216 | 1.00 | 26.35 |
| 23470 | CZ | ARG | D | 665 | -95.170 | 0.782 | 49.957 | 1.00 | 27.60 |
| 23471 | NH1 | ARG | D | 665 | -95.418 | -0.496 | 50.206 | 1.00 | 28.66 |
| 23472 | NH2 | ARG | D | 665 | -95.967 | 1.715 | 50.455 | 1.00 | 29.38 |
| 23473 | C | ARG | D | 665 | -88.441 | -0.766 | 47.343 | 1.00 | 24.22 |
| 23474 | O | ARG | D | 665 | -88.350 | -1.778 | 48.011 | 1.00 | 24.33 |
| 23475 | N | ALA | D | 666 | -87.675 | -0.518 | 46.292 | 1.00 | 24.52 |
| 23476 | CA | ALA | D | 666 | -86.732 | -1.511 | 45.771 | 1.00 | 24.78 |
| 23477 | CB | ALA | D | 666 | -85.950 | -0.935 | 44.627 | 1.00 | 24.85 |
| 23478 | C | ALA | D | 666 | -85.784 | -2.118 | 46.790 | 1.00 | 25.15 |
| 23479 | O | ALA | D | 666 | -85.509 | -3.314 | 46.751 | 1.00 | 25.19 |
| 23480 | N | GLU | D | 667 | -85.271 | -1.302 | 47.697 | 1.00 | 25.94 |
| 23481 | CA | GLU | D | 667 | -84.308 | -1.783 | 48.683 | 1.00 | 26.94 |
| 23482 | CB | GLU | D | 667 | -83.817 | -0.616 | 49.578 | 1.00 | 27.70 |
| 23483 | CG | GLU | D | 667 | -82.794 | -0.998 | 50.658 | 1.00 | 31.37 |
| 23484 | CD | GLU | D | 667 | -81.432 | -1.370 | 50.083 | 1.00 | 34.98 |
| 23485 | OE1 | GLU | D | 667 | -80.668 | -2.100 | 50.756 | 1.00 | 36.00 |
| 23486 | OE2 | GLU | D | 667 | -81.123 | -0.940 | 48.947 | 1.00 | 37.23 |
| 23487 | C | GLU | D | 667 | -84.913 | -2.892 | 49.526 | 1.00 | 26.63 |
| 23488 | O | GLU | D | 667 | -84.239 | -3.830 | 49.896 | 1.00 | 26.96 |
| 23489 | N | ASN | D | 668 | -86.197 | -2.792 | 49.819 | 1.00 | 26.69 |
| 23490 | CA | ASN | D | 668 | -86.852 | -3.772 | 50.677 | 1.00 | 26.46 |
| 23491 | CB | ASN | D | 668 | -88.185 | -3.209 | 51.165 | 1.00 | 27.48 |
| 23492 | CG | ASN | D | 668 | -87.996 | -2.144 | 52.216 | 1.00 | 29.06 |
| 23493 | OD1 | ASN | D | 668 | -87.017 | -2.174 | 52.925 | 1.00 | 33.18 |
| 23494 | ND2 | ASN | D | 668 | -88.918 | -1.209 | 52.315 | 1.00 | 31.95 |
| 23495 | C | ASN | D | 668 | -87.082 | -5.133 | 50.049 | 1.00 | 25.84 |
| 23496 | O | ASN | D | 668 | -87.401 | -6.095 | 50.757 | 1.00 | 25.33 |
| 23497 | N | PHE | D | 669 | -86.965 | -5.228 | 48.727 | 1.00 | 24.32 |
| 23498 | CA | PHE | D | 669 | -87.143 | -6.540 | 48.109 | 1.00 | 23.47 |
| 23499 | CB | PHE | D | 669 | -87.296 | -6.454 | 46.589 | 1.00 | 22.54 |
| 23500 | CG | PHE | D | 669 | -88.684 | -6.046 | 46.141 | 1.00 | 21.60 |
| 23501 | CD1 | PHE | D | 669 | -89.139 | -4.736 | 46.343 | 1.00 | 19.42 |

FIGURE 3 QS

| A | B | C | D | E | F | G | H | I | J |
|---|---|---|---|---|---|---|---|---|---|
| 23502 | CE1 | PHE | D | 669 | -90.390 | -4.342 | 45.956 | 1.00 | 17.25 |
| 23503 | CZ | PHE | D | 669 | -91.226 | -5.259 | 45.316 | 1.00 | 20.42 |
| 23504 | CE2 | PHE | D | 669 | -90.779 | -6.576 | 45.097 | 1.00 | 21.06 |
| 23505 | CD2 | PHE | D | 669 | -89.519 | -6.958 | 45.517 | 1.00 | 19.03 |
| 23506 | C | PHE | D | 669 | -85.971 | -7.442 | 48.512 | 1.00 | 23.35 |
| 23507 | O | PHE | D | 669 | -85.915 | -8.609 | 48.140 | 1.00 | 22.93 |
| 23508 | N | LYS | D | 670 | -85.031 | -6.894 | 49.271 | 1.00 | 23.33 |
| 23509 | CA | LYS | D | 670 | -83.916 | -7.711 | 49.740 | 1.00 | 24.37 |
| 23510 | CB | LYS | D | 670 | -82.838 | -6.849 | 50.393 | 1.00 | 24.38 |
| 23511 | CG | LYS | D | 670 | -82.002 | -6.077 | 49.413 | 1.00 | 27.50 |
| 23512 | CD | LYS | D | 670 | -80.915 | -5.305 | 50.156 | 1.00 | 29.30 |
| 23513 | CE | LYS | D | 670 | -80.001 | -4.606 | 49.181 | 1.00 | 30.53 |
| 23514 | NZ | LYS | D | 670 | -79.113 | -3.649 | 49.894 | 1.00 | 33.24 |
| 23515 | C | LYS | D | 670 | -84.438 | -8.656 | 50.789 | 1.00 | 23.62 |
| 23516 | O | LYS | D | 670 | -83.792 | -9.608 | 51.129 | 1.00 | 23.80 |
| 23517 | N | GLN | D | 671 | -85.614 | -8.347 | 51.309 | 1.00 | 23.78 |
| 23518 | CA | GLN | D | 671 | -86.205 | -9.097 | 52.402 | 1.00 | 23.50 |
| 23519 | CB | GLN | D | 671 | -86.968 | -8.115 | 53.317 | 1.00 | 22.86 |
| 23520 | CG | GLN | D | 671 | -86.097 | -6.988 | 53.845 | 1.00 | 20.84 |
| 23521 | CD | GLN | D | 671 | -86.860 | -5.953 | 54.653 | 1.00 | 24.55 |
| 23522 | OE1 | GLN | D | 671 | -87.885 | -5.420 | 54.196 | 1.00 | 23.77 |
| 23523 | NE2 | GLN | D | 671 | -86.355 | -5.644 | 55.859 | 1.00 | 24.62 |
| 23524 | C | GLN | D | 671 | -87.126 | -10.233 | 51.921 | 1.00 | 23.80 |
| 23525 | O | GLN | D | 671 | -87.734 | -10.937 | 52.735 | 1.00 | 23.47 |
| 23526 | N | VAL | D | 672 | -87.218 | -10.421 | 50.606 | 1.00 | 23.40 |
| 23527 | CA | VAL | D | 672 | -88.134 | -11.417 | 50.071 | 1.00 | 23.33 |
| 23528 | CB | VAL | D | 672 | -89.474 | -10.786 | 49.606 | 1.00 | 23.68 |
| 23529 | CG1 | VAL | D | 672 | -90.161 | -10.038 | 50.732 | 1.00 | 22.21 |
| 23530 | CG2 | VAL | D | 672 | -89.225 | -9.834 | 48.423 | 1.00 | 23.11 |
| 23531 | C | VAL | D | 672 | -87.559 | -12.051 | 48.850 | 1.00 | 23.60 |
| 23532 | O | VAL | D | 672 | -86.540 | -11.638 | 48.338 | 1.00 | 23.50 |
| 23533 | N | GLU | D | 673 | -88.239 | -13.080 | 48.389 | 1.00 | 24.36 |
| 23534 | CA | GLU | D | 673 | -87.898 | -13.736 | 47.151 | 1.00 | 24.88 |
| 23535 | CB | GLU | D | 673 | -87.811 | -15.243 | 47.384 | 1.00 | 25.87 |
| 23536 | CG | GLU | D | 673 | -86.707 | -15.589 | 48.378 | 1.00 | 31.11 |
| 23537 | CD | GLU | D | 673 | -87.158 | -16.595 | 49.427 | 1.00 | 38.23 |
| 23538 | OE1 | GLU | D | 673 | -87.836 | -17.584 | 49.062 | 1.00 | 40.78 |
| 23539 | OE2 | GLU | D | 673 | -86.823 | -16.405 | 50.622 | 1.00 | 42.84 |
| 23540 | C | GLU | D | 673 | -89.035 | -13.357 | 46.201 | 1.00 | 23.74 |
| 23541 | O | GLU | D | 673 | -90.220 | -13.564 | 46.513 | 1.00 | 23.16 |
| 23542 | N | TYR | D | 674 | -88.668 | -12.803 | 45.051 | 1.00 | 23.00 |
| 23543 | CA | TYR | D | 674 | -89.626 | -12.190 | 44.129 | 1.00 | 22.63 |
| 23544 | CB | TYR | D | 674 | -89.299 | -10.702 | 44.023 | 1.00 | 22.84 |
| 23545 | CG | TYR | D | 674 | -90.225 | -9.782 | 43.251 | 1.00 | 21.85 |
| 23546 | CD1 | TYR | D | 674 | -91.612 | -9.768 | 43.463 | 1.00 | 22.71 |
| 23547 | CE1 | TYR | D | 674 | -92.441 | -8.860 | 42.771 | 1.00 | 22.21 |
| 23548 | CZ | TYR | D | 674 | -91.850 | -7.946 | 41.874 | 1.00 | 22.62 |
| 23549 | OH | TYR | D | 674 | -92.605 | -7.034 | 41.173 | 1.00 | 23.00 |
| 23550 | CE2 | TYR | D | 674 | -90.498 | -7.951 | 41.672 | 1.00 | 20.57 |
| 23551 | CD2 | TYR | D | 674 | -89.696 | -8.862 | 42.357 | 1.00 | 21.62 |
| 23552 | C | TYR | D | 674 | -89.562 | -12.775 | 42.754 | 1.00 | 22.26 |

FIGURE 3 QT

| A | B | C | D | E | F | G | H | I | J |
|---|---|---|---|---|---|---|---|---|---|
| 23553 | O | TYR | D | 674 | -88.478 | -13.015 | 42.221 | 1.00 | 21.96 |
| 23554 | N | LEU | D | 675 | -90.735 | -12.993 | 42.177 | 1.00 | 22.14 |
| 23555 | CA | LEU | D | 675 | -90.822 | -13.490 | 40.818 | 1.00 | 22.26 |
| 23556 | CB | LEU | D | 675 | -91.456 | -14.890 | 40.762 | 1.00 | 22.37 |
| 23557 | CG | LEU | D | 675 | -91.857 | -15.441 | 39.383 | 1.00 | 21.98 |
| 23558 | CD1 | LEU | D | 675 | -90.692 | -15.466 | 38.445 | 1.00 | 19.90 |
| 23559 | CD2 | LEU | D | 675 | -92.388 | -16.824 | 39.538 | 1.00 | 22.13 |
| 23560 | C | LEU | D | 675 | -91.652 | -12.466 | 40.076 | 1.00 | 22.02 |
| 23561 | O | LEU | D | 675 | -92.773 | -12.181 | 40.469 | 1.00 | 21.37 |
| 23562 | N | LEU | D | 676 | -91.071 | -11.905 | 39.014 | 1.00 | 22.03 |
| 23563 | CA | LEU | D | 676 | -91.705 | -10.848 | 38.242 | 1.00 | 21.86 |
| 23564 | CB | LEU | D | 676 | -90.812 | -9.612 | 38.225 | 1.00 | 21.78 |
| 23565 | CG | LEU | D | 676 | -91.271 | -8.438 | 37.356 | 1.00 | 20.70 |
| 23566 | CD1 | LEU | D | 676 | -90.127 | -7.441 | 37.272 | 1.00 | 20.09 |
| 23567 | CD2 | LEU | D | 676 | -92.502 | -7.791 | 37.931 | 1.00 | 17.32 |
| 23568 | C | LEU | D | 676 | -91.934 | -11.337 | 36.823 | 1.00 | 21.76 |
| 23569 | O | LEU | D | 676 | -90.991 | -11.737 | 36.122 | 1.00 | 21.74 |
| 23570 | N | ILE | D | 677 | -93.186 | -11.292 | 36.396 | 1.00 | 21.49 |
| 23571 | CA | ILE | D | 677 | -93.536 | -11.854 | 35.119 | 1.00 | 21.70 |
| 23572 | CB | ILE | D | 677 | -94.364 | -13.092 | 35.387 | 1.00 | 21.59 |
| 23573 | CG1 | ILE | D | 677 | -93.534 | -14.087 | 36.228 | 1.00 | 21.36 |
| 23574 | CD1 | ILE | D | 677 | -94.300 | -15.327 | 36.633 | 1.00 | 19.60 |
| 23575 | CG2 | ILE | D | 677 | -94.893 | -13.706 | 34.073 | 1.00 | 21.51 |
| 23576 | C | ILE | D | 677 | -94.317 | -10.856 | 34.275 | 1.00 | 22.38 |
| 23577 | O | ILE | D | 677 | -95.221 | -10.179 | 34.786 | 1.00 | 22.88 |
| 23578 | N | HIS | D | 678 | -94.009 | -10.782 | 32.982 | 1.00 | 21.54 |
| 23579 | CA | HIS | D | 678 | -94.726 | -9.840 | 32.138 | 1.00 | 21.73 |
| 23580 | CB | HIS | D | 678 | -94.148 | -8.434 | 32.355 | 1.00 | 21.41 |
| 23581 | CG | HIS | D | 678 | -95.136 | -7.339 | 32.116 | 1.00 | 20.87 |
| 23582 | ND1 | HIS | D | 678 | -95.326 | -6.308 | 33.007 | 1.00 | 18.16 |
| 23583 | CE1 | HIS | D | 678 | -96.270 | -5.504 | 32.547 | 1.00 | 20.39 |
| 23584 | NE2 | HIS | D | 678 | -96.688 | -5.973 | 31.383 | 1.00 | 21.36 |
| 23585 | CD2 | HIS | D | 678 | -96.004 | -7.127 | 31.096 | 1.00 | 18.42 |
| 23586 | C | HIS | D | 678 | -94.686 | -10.199 | 30.650 | 1.00 | 21.66 |
| 23587 | O | HIS | D | 678 | -93.671 | -10.653 | 30.156 | 1.00 | 21.22 |
| 23588 | N | GLY | D | 679 | -95.805 | -10.005 | 29.954 | 1.00 | 22.01 |
| 23589 | CA | GLY | D | 679 | -95.882 | -10.236 | 28.526 | 1.00 | 21.96 |
| 23590 | C | GLY | D | 679 | -95.293 | -9.048 | 27.790 | 1.00 | 22.74 |
| 23591 | O | GLY | D | 679 | -95.645 | -7.917 | 28.089 | 1.00 | 23.15 |
| 23592 | N | THR | D | 680 | -94.417 | -9.278 | 26.811 | 1.00 | 23.16 |
| 23593 | CA | THR | D | 680 | -93.796 | -8.153 | 26.109 | 1.00 | 23.51 |
| 23594 | CB | THR | D | 680 | -92.580 | -8.620 | 25.306 | 1.00 | 23.74 |
| 23595 | OG1 | THR | D | 680 | -93.010 | -9.481 | 24.236 | 1.00 | 24.46 |
| 23596 | CG2 | THR | D | 680 | -91.691 | -9.502 | 26.175 | 1.00 | 20.99 |
| 23597 | C | THR | D | 680 | -94.746 | -7.353 | 25.212 | 1.00 | 24.43 |
| 23598 | O | THR | D | 680 | -94.414 | -6.251 | 24.781 | 1.00 | 24.65 |
| 23599 | N | ALA | D | 681 | -95.936 | -7.894 | 24.960 | 1.00 | 24.82 |
| 23600 | CA | ALA | D | 681 | -96.895 | -7.250 | 24.087 | 1.00 | 25.27 |
| 23601 | CB | ALA | D | 681 | -97.225 | -8.162 | 22.879 | 1.00 | 25.14 |
| 23602 | C | ALA | D | 681 | -98.159 | -6.900 | 24.862 | 1.00 | 25.79 |
| 23603 | O | ALA | D | 681 | -99.280 | -6.920 | 24.325 | 1.00 | 26.71 |

FIGURE 3 QU

| A | B | C | D | E | F | G | H | I | J |
|---|---|---|---|---|---|---|---|---|---|
| 23604 | N | ASP | D | 682 | -97.976 | -6.599 | 26.140 | 1.00 | 25.58 |
| 23605 | CA | ASP | D | 682 | -99.081 | -6.214 | 26.986 | 1.00 | 24.26 |
| 23606 | CB | ASP | D | 682 | -98.642 | -6.316 | 28.432 | 1.00 | 24.03 |
| 23607 | CG | ASP | D | 682 | -99.783 | -6.199 | 29.387 | 1.00 | 23.05 |
| 23608 | OD1 | ASP | D | 682 | -99.778 | -6.903 | 30.430 | 1.00 | 23.38 |
| 23609 | OD2 | ASP | D | 682 | -100.740 | -5.433 | 29.174 | 1.00 | 21.88 |
| 23610 | C | ASP | D | 682 | -99.418 | -4.779 | 26.622 | 1.00 | 24.58 |
| 23611 | O | ASP | D | 682 | -98.620 | -3.862 | 26.879 | 1.00 | 24.35 |
| 23612 | N | ASP | D | 683 | -100.589 | -4.593 | 26.023 | 1.00 | 24.45 |
| 23613 | CA | ASP | D | 683 | -101.022 | -3.300 | 25.515 | 1.00 | 24.69 |
| 23614 | CB | ASP | D | 683 | -101.995 | -3.509 | 24.372 | 1.00 | 24.67 |
| 23615 | CG | ASP | D | 683 | -103.120 | -4.386 | 24.752 | 1.00 | 24.79 |
| 23616 | OD1 | ASP | D | 683 | -102.890 | -5.615 | 24.805 | 1.00 | 25.70 |
| 23617 | OD2 | ASP | D | 683 | -104.267 | -3.960 | 25.029 | 1.00 | 24.84 |
| 23618 | C | ASP | D | 683 | -101.746 | -2.507 | 26.568 | 1.00 | 24.92 |
| 23619 | O | ASP | D | 683 | -102.032 | -1.309 | 26.402 | 1.00 | 24.30 |
| 23620 | N | ASN | D | 684 | -102.060 | -3.212 | 27.647 | 1.00 | 24.70 |
| 23621 | CA | ASN | D | 684 | -102.800 | -2.669 | 28.750 | 1.00 | 23.71 |
| 23622 | CB | ASN | D | 684 | -103.704 | -3.753 | 29.307 | 1.00 | 23.67 |
| 23623 | CG | ASN | D | 684 | -104.729 | -3.216 | 30.259 | 1.00 | 23.03 |
| 23624 | OD1 | ASN | D | 684 | -105.777 | -3.811 | 30.444 | 1.00 | 26.22 |
| 23625 | ND2 | ASN | D | 684 | -104.430 | -2.102 | 30.878 | 1.00 | 22.01 |
| 23626 | C | ASN | D | 684 | -101.798 | -2.178 | 29.780 | 1.00 | 23.32 |
| 23627 | O | ASN | D | 684 | -101.558 | -0.971 | 29.901 | 1.00 | 22.78 |
| 23628 | N | VAL | D | 685 | -101.231 | -3.088 | 30.563 | 1.00 | 22.67 |
| 23629 | CA | VAL | D | 685 | -100.132 | -2.629 | 31.411 | 1.00 | 21.98 |
| 23630 | CB | VAL | D | 685 | -100.272 | -2.932 | 32.943 | 1.00 | 22.73 |
| 23631 | CG1 | VAL | D | 685 | -101.492 | -3.787 | 33.262 | 1.00 | 21.21 |
| 23632 | CG2 | VAL | D | 685 | -98.970 | -3.382 | 33.583 | 1.00 | 22.59 |
| 23633 | C | VAL | D | 685 | -98.850 | -2.986 | 30.716 | 1.00 | 21.40 |
| 23634 | O | VAL | D | 685 | -98.478 | -4.154 | 30.543 | 1.00 | 21.30 |
| 23635 | N | HIS | D | 686 | -98.211 | -1.932 | 30.251 | 1.00 | 20.86 |
| 23636 | CA | HIS | D | 686 | -97.066 | -2.037 | 29.370 | 1.00 | 20.94 |
| 23637 | CB | HIS | D | 686 | -96.757 | -0.652 | 28.814 | 1.00 | 19.78 |
| 23638 | CG | HIS | D | 686 | -97.954 | -0.024 | 28.173 | 1.00 | 19.37 |
| 23639 | ND1 | HIS | D | 686 | -98.243 | 1.321 | 28.263 | 1.00 | 16.50 |
| 23640 | CE1 | HIS | D | 686 | -99.368 | 1.567 | 27.612 | 1.00 | 19.38 |
| 23641 | NE2 | HIS | D | 686 | -99.818 | 0.430 | 27.105 | 1.00 | 19.51 |
| 23642 | CD2 | HIS | D | 686 | -98.956 | -0.579 | 27.447 | 1.00 | 17.66 |
| 23643 | C | HIS | D | 686 | -95.876 | -2.723 | 30.006 | 1.00 | 21.02 |
| 23644 | O | HIS | D | 686 | -95.616 | -2.539 | 31.179 | 1.00 | 21.72 |
| 23645 | N | PHE | D | 687 | -95.189 | -3.558 | 29.237 | 1.00 | 21.34 |
| 23646 | CA | PHE | D | 687 | -93.983 | -4.225 | 29.739 | 1.00 | 20.81 |
| 23647 | CB | PHE | D | 687 | -93.244 | -4.885 | 28.596 | 1.00 | 20.15 |
| 23648 | CG | PHE | D | 687 | -92.055 | -5.702 | 29.028 | 1.00 | 18.91 |
| 23649 | CD1 | PHE | D | 687 | -92.217 | -7.006 | 29.439 | 1.00 | 17.67 |
| 23650 | CE1 | PHE | D | 687 | -91.120 | -7.771 | 29.831 | 1.00 | 17.81 |
| 23651 | CZ | PHE | D | 687 | -89.870 | -7.232 | 29.792 | 1.00 | 16.78 |
| 23652 | CE2 | PHE | D | 687 | -89.687 | -5.931 | 29.380 | 1.00 | 18.33 |
| 23653 | CD2 | PHE | D | 687 | -90.776 | -5.168 | 28.992 | 1.00 | 16.92 |
| 23654 | C | PHE | D | 687 | -93.085 | -3.212 | 30.435 | 1.00 | 21.54 |

FIGURE 3 QV

| A | B | C | D | E | F | G | H | I | J |
|---|---|---|---|---|---|---|---|---|---|
| 23655 | O | PHE | D | 687 | -92.386 | -3.546 | 31.398 | 1.00 | 22.37 |
| 23656 | N | GLN | D | 688 | -93.123 | -1.969 | 29.957 | 1.00 | 21.62 |
| 23657 | CA | GLN | D | 688 | -92.382 | -0.853 | 30.573 | 1.00 | 21.99 |
| 23658 | CB | GLN | D | 688 | -92.986 | 0.489 | 30.082 | 1.00 | 21.49 |
| 23659 | CG | GLN | D | 688 | -92.732 | 1.696 | 30.977 | 1.00 | 21.34 |
| 23660 | CD | GLN | D | 688 | -93.623 | 2.891 | 30.629 | 1.00 | 20.42 |
| 23661 | OE1 | GLN | D | 688 | -94.790 | 2.715 | 30.353 | 1.00 | 21.30 |
| 23662 | NE2 | GLN | D | 688 | -93.062 | 4.094 | 30.637 | 1.00 | 18.03 |
| 23663 | C | GLN | D | 688 | -92.478 | -0.932 | 32.088 | 1.00 | 21.77 |
| 23664 | O | GLN | D | 688 | -91.512 | -0.778 | 32.831 | 1.00 | 22.49 |
| 23665 | N | GLN | D | 689 | -93.687 | -1.173 | 32.537 | 1.00 | 21.98 |
| 23666 | CA | GLN | D | 689 | -93.997 | -1.200 | 33.953 | 1.00 | 22.02 |
| 23667 | CB | GLN | D | 689 | -95.476 | -1.525 | 34.049 | 1.00 | 21.84 |
| 23668 | CG | GLN | D | 689 | -96.174 | -1.035 | 35.257 | 1.00 | 25.01 |
| 23669 | CD | GLN | D | 689 | -97.016 | 0.225 | 35.060 | 1.00 | 23.27 |
| 23670 | OE1 | GLN | D | 689 | -96.955 | 1.084 | 35.896 | 1.00 | 26.17 |
| 23671 | NE2 | GLN | D | 689 | -97.831 | 0.299 | 34.008 | 1.00 | 22.99 |
| 23672 | C | GLN | D | 689 | -93.082 | -2.182 | 34.720 | 1.00 | 22.00 |
| 23673 | O | GLN | D | 689 | -92.516 | -1.843 | 35.763 | 1.00 | 22.48 |
| 23674 | N | SER | D | 690 | -92.908 | -3.398 | 34.203 | 1.00 | 21.84 |
| 23675 | CA | SER | D | 690 | -92.023 | -4.356 | 34.849 | 1.00 | 21.13 |
| 23676 | CB | SER | D | 690 | -92.373 | -5.796 | 34.438 | 1.00 | 21.43 |
| 23677 | OG | SER | D | 690 | -93.582 | -6.212 | 35.034 | 1.00 | 21.44 |
| 23678 | C | SER | D | 690 | -90.574 | -4.068 | 34.496 | 1.00 | 20.96 |
| 23679 | O | SER | D | 690 | -89.685 | -4.366 | 35.275 | 1.00 | 21.48 |
| 23680 | N | ALA | D | 691 | -90.328 | -3.507 | 33.312 | 1.00 | 20.62 |
| 23681 | CA | ALA | D | 691 | -88.970 | -3.153 | 32.913 | 1.00 | 20.80 |
| 23682 | CB | ALA | D | 691 | -88.936 | -2.595 | 31.467 | 1.00 | 20.67 |
| 23683 | C | ALA | D | 691 | -88.351 | -2.152 | 33.884 | 1.00 | 20.77 |
| 23684 | O | ALA | D | 691 | -87.137 | -2.145 | 34.095 | 1.00 | 21.27 |
| 23685 | N | GLN | D | 692 | -89.183 | -1.296 | 34.457 | 1.00 | 20.70 |
| 23686 | CA | GLN | D | 692 | -88.725 | -0.311 | 35.438 | 1.00 | 20.86 |
| 23687 | CB | GLN | D | 692 | -89.684 | 0.888 | 35.491 | 1.00 | 21.00 |
| 23688 | CG | GLN | D | 692 | -89.700 | 1.747 | 34.223 | 1.00 | 22.12 |
| 23689 | CD | GLN | D | 692 | -88.435 | 2.575 | 34.012 | 1.00 | 23.01 |
| 23690 | OE1 | GLN | D | 692 | -87.472 | 2.468 | 34.770 | 1.00 | 26.51 |
| 23691 | NE2 | GLN | D | 692 | -88.439 | 3.405 | 32.976 | 1.00 | 24.59 |
| 23692 | C | GLN | D | 692 | -88.592 | -0.944 | 36.822 | 1.00 | 20.78 |
| 23693 | O | GLN | D | 692 | -87.705 | -0.588 | 37.583 | 1.00 | 20.62 |
| 23694 | N | ILE | D | 693 | -89.467 | -1.888 | 37.158 | 1.00 | 20.68 |
| 23695 | CA | ILE | D | 693 | -89.302 | -2.574 | 38.445 | 1.00 | 20.87 |
| 23696 | CB | ILE | D | 693 | -90.428 | -3.603 | 38.736 | 1.00 | 20.42 |
| 23697 | CG1 | ILE | D | 693 | -91.712 | -2.880 | 39.093 | 1.00 | 19.89 |
| 23698 | CD1 | ILE | D | 693 | -92.905 | -3.825 | 39.351 | 1.00 | 16.39 |
| 23699 | CG2 | ILE | D | 693 | -90.035 | -4.495 | 39.924 | 1.00 | 20.06 |
| 23700 | C | ILE | D | 693 | -87.976 | -3.285 | 38.476 | 1.00 | 20.52 |
| 23701 | O | ILE | D | 693 | -87.219 | -3.168 | 39.422 | 1.00 | 21.24 |
| 23702 | N | SER | D | 694 | -87.693 | -4.037 | 37.422 | 1.00 | 21.10 |
| 23703 | CA | SER | D | 694 | -86.468 | -4.818 | 37.370 | 1.00 | 20.77 |
| 23704 | CB | SER | D | 694 | -86.467 | -5.707 | 36.129 | 1.00 | 21.03 |
| 23705 | OG | SER | D | 694 | -86.308 | -4.942 | 34.945 | 1.00 | 21.23 |

FIGURE 3 QW

| A | B | C | D | E | F | G | H | I | J |
|---|---|---|---|---|---|---|---|---|---|
| 23706 | C | SER | D | 694 | -85.218 | -3.962 | 37.384 | 1.00 | 20.65 |
| 23707 | O | SER | D | 694 | -84.209 | -4.374 | 37.913 | 1.00 | 20.94 |
| 23708 | N | LYS | D | 695 | -85.267 | -2.792 | 36.754 | 1.00 | 20.75 |
| 23709 | CA | LYS | D | 695 | -84.109 | -1.912 | 36.703 | 1.00 | 20.30 |
| 23710 | CB | LYS | D | 695 | -84.316 | -0.806 | 35.647 | 1.00 | 20.51 |
| 23711 | CG | LYS | D | 695 | -83.226 | 0.253 | 35.635 | 1.00 | 19.10 |
| 23712 | CD | LYS | D | 695 | -83.052 | 0.919 | 34.260 | 1.00 | 18.50 |
| 23713 | CE | LYS | D | 695 | -84.301 | 1.678 | 33.807 | 1.00 | 19.63 |
| 23714 | NZ | LYS | D | 695 | -84.671 | 2.888 | 34.658 | 1.00 | 23.49 |
| 23715 | C | LYS | D | 695 | -83.891 | -1.308 | 38.078 | 1.00 | 20.61 |
| 23716 | O | LYS | D | 695 | -82.785 | -1.113 | 38.509 | 1.00 | 20.27 |
| 23717 | N | ALA | D | 696 | -84.957 | -1.016 | 38.788 | 1.00 | 21.51 |
| 23718 | CA | ALA | D | 696 | -84.772 | -0.475 | 40.119 | 1.00 | 23.18 |
| 23719 | CB | ALA | D | 696 | -86.082 | 0.086 | 40.647 | 1.00 | 22.96 |
| 23720 | C | ALA | D | 696 | -84.196 | -1.546 | 41.064 | 1.00 | 24.04 |
| 23721 | O | ALA | D | 696 | -83.400 | -1.233 | 41.946 | 1.00 | 25.62 |
| 23722 | N | LEU | D | 697 | -84.584 | -2.801 | 40.877 | 1.00 | 24.70 |
| 23723 | CA | LEU | D | 697 | -84.048 | -3.893 | 41.711 | 1.00 | 25.61 |
| 23724 | CB | LEU | D | 697 | -84.843 | -5.186 | 41.515 | 1.00 | 25.69 |
| 23725 | CG | LEU | D | 697 | -86.288 | -5.178 | 42.048 | 1.00 | 26.26 |
| 23726 | CD1 | LEU | D | 697 | -86.968 | -6.530 | 41.876 | 1.00 | 26.82 |
| 23727 | CD2 | LEU | D | 697 | -86.304 | -4.787 | 43.504 | 1.00 | 28.62 |
| 23728 | C | LEU | D | 697 | -82.583 | -4.140 | 41.404 | 1.00 | 25.90 |
| 23729 | O | LEU | D | 697 | -81.772 | -4.330 | 42.309 | 1.00 | 26.11 |
| 23730 | N | VAL | D | 698 | -82.237 | -4.134 | 40.121 | 1.00 | 26.07 |
| 23731 | CA | VAL | D | 698 | -80.851 | -4.304 | 39.735 | 1.00 | 25.49 |
| 23732 | CB | VAL | D | 698 | -80.704 | -4.237 | 38.207 | 1.00 | 25.71 |
| 23733 | CG1 | VAL | D | 698 | -79.244 | -4.082 | 37.820 | 1.00 | 23.66 |
| 23734 | CG2 | VAL | D | 698 | -81.313 | -5.488 | 37.555 | 1.00 | 24.81 |
| 23735 | C | VAL | D | 698 | -80.042 | -3.171 | 40.336 | 1.00 | 26.30 |
| 23736 | O | VAL | D | 698 | -78.927 | -3.355 | 40.865 | 1.00 | 26.31 |
| 23737 | N | ASP | D | 699 | -80.606 | -1.974 | 40.255 | 1.00 | 26.42 |
| 23738 | CA | ASP | D | 699 | -79.901 | -0.815 | 40.735 | 1.00 | 27.19 |
| 23739 | CB | ASP | D | 699 | -80.598 | 0.455 | 40.281 | 1.00 | 27.83 |
| 23740 | CG | ASP | D | 699 | -80.334 | 0.748 | 38.820 | 1.00 | 31.61 |
| 23741 | OD1 | ASP | D | 699 | -80.873 | 1.747 | 38.312 | 1.00 | 34.02 |
| 23742 | OD2 | ASP | D | 699 | -79.614 | 0.011 | 38.094 | 1.00 | 35.99 |
| 23743 | C | ASP | D | 699 | -79.538 | -0.802 | 42.231 | 1.00 | 26.39 |
| 23744 | O | ASP | D | 699 | -78.557 | -0.188 | 42.596 | 1.00 | 26.84 |
| 23745 | N | VAL | D | 700 | -80.302 | -1.480 | 43.083 | 1.00 | 25.93 |
| 23746 | CA | VAL | D | 700 | -79.959 | -1.529 | 44.515 | 1.00 | 25.70 |
| 23747 | CB | VAL | D | 700 | -81.141 | -1.142 | 45.464 | 1.00 | 25.71 |
| 23748 | CG1 | VAL | D | 700 | -81.578 | 0.292 | 45.252 | 1.00 | 24.57 |
| 23749 | CG2 | VAL | D | 700 | -82.323 | -2.091 | 45.296 | 1.00 | 26.35 |
| 23750 | C | VAL | D | 700 | -79.419 | -2.902 | 44.905 | 1.00 | 25.77 |
| 23751 | O | VAL | D | 700 | -79.240 | -3.190 | 46.069 | 1.00 | 25.50 |
| 23752 | N | GLY | D | 701 | -79.180 | -3.753 | 43.915 | 1.00 | 26.22 |
| 23753 | CA | GLY | D | 701 | -78.559 | -5.044 | 44.146 | 1.00 | 26.35 |
| 23754 | C | GLY | D | 701 | -79.447 | -6.124 | 44.743 | 1.00 | 26.80 |
| 23755 | O | GLY | D | 701 | -78.981 | -6.948 | 45.535 | 1.00 | 26.86 |
| 23756 | N | VAL | D | 702 | -80.727 | -6.127 | 44.413 | 1.00 | 26.80 |

FIGURE 3 QX

| A | B | C | D | E | F | G | H | I | J |
|---|---|---|---|---|---|---|---|---|---|
| 23757 | CA | VAL | D | 702 | -81.542 | -7.235 | 44.879 | 1.00 | 27.14 |
| 23758 | CB | VAL | D | 702 | -82.865 | -6.825 | 45.543 | 1.00 | 27.17 |
| 23759 | CG1 | VAL | D | 702 | -82.988 | -5.322 | 45.630 | 1.00 | 27.53 |
| 23760 | CG2 | VAL | D | 702 | -84.064 | -7.518 | 44.885 | 1.00 | 27.60 |
| 23761 | C | VAL | D | 702 | -81.731 | -8.279 | 43.806 | 1.00 | 26.77 |
| 23762 | O | VAL | D | 702 | -82.007 | -7.965 | 42.649 | 1.00 | 27.38 |
| 23763 | N | ASP | D | 703 | -81.519 | -9.522 | 44.204 | 1.00 | 26.53 |
| 23764 | CA | ASP | D | 703 | -81.709 | -10.650 | 43.329 | 1.00 | 27.21 |
| 23765 | CB | ASP | D | 703 | -80.837 | -11.838 | 43.754 | 1.00 | 27.73 |
| 23766 | CG | ASP | D | 703 | -80.774 | -12.911 | 42.670 | 1.00 | 28.68 |
| 23767 | OD1 | ASP | D | 703 | -81.055 | -14.081 | 42.993 | 1.00 | 30.69 |
| 23768 | OD2 | ASP | D | 703 | -80.499 | -12.661 | 41.465 | 1.00 | 25.48 |
| 23769 | C | ASP | D | 703 | -83.169 | -11.052 | 43.358 | 1.00 | 26.90 |
| 23770 | O | ASP | D | 703 | -83.814 | -11.018 | 44.407 | 1.00 | 27.76 |
| 23771 | N | PHE | D | 704 | -83.688 | -11.420 | 42.199 | 1.00 | 26.19 |
| 23772 | CA | PHE | D | 704 | -85.078 | -11.811 | 42.067 | 1.00 | 25.30 |
| 23773 | CB | PHE | D | 704 | -85.953 | -10.575 | 41.857 | 1.00 | 25.19 |
| 23774 | CG | PHE | D | 704 | -85.616 | -9.791 | 40.615 | 1.00 | 24.20 |
| 23775 | CD1 | PHE | D | 704 | -86.372 | -9.940 | 39.462 | 1.00 | 23.72 |
| 23776 | CE1 | PHE | D | 704 | -86.070 | -9.213 | 38.310 | 1.00 | 24.12 |
| 23777 | CZ | PHE | D | 704 | -85.002 | -8.309 | 38.306 | 1.00 | 21.64 |
| 23778 | CE2 | PHE | D | 704 | -84.252 | -8.150 | 39.435 | 1.00 | 22.32 |
| 23779 | CD2 | PHE | D | 704 | -84.556 | -8.894 | 40.600 | 1.00 | 23.35 |
| 23780 | C | PHE | D | 704 | -85.166 | -12.718 | 40.866 | 1.00 | 25.50 |
| 23781 | O | PHE | D | 704 | -84.166 | -12.925 | 40.160 | 1.00 | 25.56 |
| 23782 | N | GLN | D | 705 | -86.348 | -13.278 | 40.634 | 1.00 | 25.49 |
| 23783 | CA | GLN | D | 705 | -86.545 | -14.123 | 39.478 | 1.00 | 25.80 |
| 23784 | CB | GLN | D | 705 | -87.227 | -15.434 | 39.868 | 1.00 | 26.41 |
| 23785 | CG | GLN | D | 705 | -86.449 | -16.305 | 40.838 | 1.00 | 31.23 |
| 23786 | CD | GLN | D | 705 | -84.996 | -16.436 | 40.468 | 1.00 | 37.91 |
| 23787 | OE1 | GLN | D | 705 | -84.110 | -16.189 | 41.296 | 1.00 | 43.51 |
| 23788 | NE2 | GLN | D | 705 | -84.736 | -16.806 | 39.234 | 1.00 | 39.39 |
| 23789 | C | GLN | D | 705 | -87.417 | -13.375 | 38.472 | 1.00 | 24.92 |
| 23790 | O | GLN | D | 705 | -88.367 | -12.701 | 38.858 | 1.00 | 24.88 |
| 23791 | N | ALA | D | 706 | -87.095 | -13.494 | 37.192 | 1.00 | 23.71 |
| 23792 | CA | ALA | D | 706 | -87.899 | -12.868 | 36.155 | 1.00 | 23.59 |
| 23793 | CB | ALA | D | 706 | -87.135 | -11.717 | 35.509 | 1.00 | 22.50 |
| 23794 | C | ALA | D | 706 | -88.372 | -13.858 | 35.067 | 1.00 | 23.75 |
| 23795 | O | ALA | D | 706 | -87.830 | -14.963 | 34.896 | 1.00 | 23.51 |
| 23796 | N | MET | D | 707 | -89.393 | -13.443 | 34.336 | 1.00 | 23.38 |
| 23797 | CA | MET | D | 707 | -89.810 | -14.180 | 33.164 | 1.00 | 23.04 |
| 23798 | CB | MET | D | 707 | -90.678 | -15.378 | 33.533 | 1.00 | 23.25 |
| 23799 | CG | MET | D | 707 | -91.241 | -16.082 | 32.322 | 1.00 | 24.57 |
| 23800 | SD | MET | D | 707 | -89.962 | -16.899 | 31.331 | 1.00 | 26.76 |
| 23801 | CE | MET | D | 707 | -89.257 | -18.031 | 32.519 | 1.00 | 22.19 |
| 23802 | C | MET | D | 707 | -90.606 | -13.275 | 32.259 | 1.00 | 22.67 |
| 23803 | O | MET | D | 707 | -91.645 | -12.765 | 32.654 | 1.00 | 22.28 |
| 23804 | N | TRP | D | 708 | -90.100 | -13.059 | 31.050 | 1.00 | 22.64 |
| 23805 | CA | TRP | D | 708 | -90.846 | -12.327 | 30.044 | 1.00 | 22.61 |
| 23806 | CB | TRP | D | 708 | -89.895 | -11.449 | 29.221 | 1.00 | 21.99 |
| 23807 | CG | TRP | D | 708 | -89.120 | -12.216 | 28.185 | 1.00 | 22.43 |

FIGURE 3 QY

| A | B | C | D | E | F | G | H | I | J |
|---|---|---|---|---|---|---|---|---|---|
| 23808 | CD1 | TRP | D | 708 | -89.596 | -12.706 | 26.987 | 1.00 | 24.21 |
| 23809 | NE1 | TRP | D | 708 | -88.599 | -13.382 | 26.324 | 1.00 | 23.29 |
| 23810 | CE2 | TRP | D | 708 | -87.451 | -13.313 | 27.072 | 1.00 | 23.65 |
| 23811 | CD2 | TRP | D | 708 | -87.746 | -12.594 | 28.245 | 1.00 | 21.39 |
| 23812 | CE3 | TRP | D | 708 | -86.736 | -12.429 | 29.190 | 1.00 | 21.74 |
| 23813 | CZ3 | TRP | D | 708 | -85.491 | -12.934 | 28.929 | 1.00 | 22.63 |
| 23814 | CH2 | TRP | D | 708 | -85.228 | -13.637 | 27.764 | 1.00 | 23.46 |
| 23815 | CZ2 | TRP | D | 708 | -86.190 | -13.839 | 26.823 | 1.00 | 23.70 |
| 23816 | C | TRP | D | 708 | -91.550 | -13.377 | 29.151 | 1.00 | 22.38 |
| 23817 | O | TRP | D | 708 | -91.024 | -14.476 | 28.951 | 1.00 | 23.23 |
| 23818 | N | TYR | D | 709 | -92.724 | -13.051 | 28.643 | 1.00 | 21.87 |
| 23819 | CA | TYR | D | 709 | -93.463 | -13.930 | 27.722 | 1.00 | 22.29 |
| 23820 | CB | TYR | D | 709 | -94.837 | -14.327 | 28.265 | 1.00 | 21.63 |
| 23821 | CG | TYR | D | 709 | -94.689 | -15.448 | 29.240 | 1.00 | 23.13 |
| 23822 | CD1 | TYR | D | 709 | -94.370 | -16.730 | 28.809 | 1.00 | 23.03 |
| 23823 | CE1 | TYR | D | 709 | -94.181 | -17.766 | 29.719 | 1.00 | 24.34 |
| 23824 | CZ | TYR | D | 709 | -94.292 | -17.511 | 31.064 | 1.00 | 24.60 |
| 23825 | OH | TYR | D | 709 | -94.110 | -18.520 | 31.982 | 1.00 | 23.02 |
| 23826 | CE2 | TYR | D | 709 | -94.590 | -16.241 | 31.502 | 1.00 | 24.89 |
| 23827 | CD2 | TYR | D | 709 | -94.774 | -15.219 | 30.596 | 1.00 | 23.35 |
| 23828 | C | TYR | D | 709 | -93.597 | -13.210 | 26.406 | 1.00 | 22.46 |
| 23829 | O | TYR | D | 709 | -94.368 | -12.263 | 26.268 | 1.00 | 22.19 |
| 23830 | N | THR | D | 710 | -92.755 | -13.612 | 25.478 | 1.00 | 23.10 |
| 23831 | CA | THR | D | 710 | -92.679 | -12.985 | 24.181 | 1.00 | 24.34 |
| 23832 | CB | THR | D | 710 | -91.715 | -13.792 | 23.325 | 1.00 | 24.78 |
| 23833 | OG1 | THR | D | 710 | -90.418 | -13.773 | 23.935 | 1.00 | 25.52 |
| 23834 | CG2 | THR | D | 710 | -91.523 | -13.116 | 21.986 | 1.00 | 24.41 |
| 23835 | C | THR | D | 710 | -94.007 | -12.947 | 23.460 | 1.00 | 24.60 |
| 23836 | O | THR | D | 710 | -94.601 | -14.000 | 23.195 | 1.00 | 24.62 |
| 23837 | N | ASP | D | 711 | -94.443 | -11.733 | 23.132 | 1.00 | 25.02 |
| 23838 | CA | ASP | D | 711 | -95.653 | -11.486 | 22.346 | 1.00 | 25.41 |
| 23839 | CB | ASP | D | 711 | -95.652 | -12.268 | 21.029 | 1.00 | 25.30 |
| 23840 | CG | ASP | D | 711 | -94.688 | -11.684 | 20.013 | 1.00 | 27.89 |
| 23841 | OD1 | ASP | D | 711 | -94.501 | -12.313 | 18.929 | 1.00 | 30.31 |
| 23842 | OD2 | ASP | D | 711 | -94.074 | -10.600 | 20.202 | 1.00 | 27.02 |
| 23843 | C | ASP | D | 711 | -96.957 | -11.705 | 23.069 | 1.00 | 25.14 |
| 23844 | O | ASP | D | 711 | -98.024 | -11.540 | 22.468 | 1.00 | 24.79 |
| 23845 | N | GLU | D | 712 | -96.893 | -12.086 | 24.343 | 1.00 | 24.54 |
| 23846 | CA | GLU | D | 712 | -98.129 | -12.243 | 25.092 | 1.00 | 24.67 |
| 23847 | CB | GLU | D | 712 | -97.945 | -13.177 | 26.291 | 1.00 | 24.69 |
| 23848 | CG | GLU | D | 712 | -97.697 | -14.640 | 25.904 | 1.00 | 26.15 |
| 23849 | CD | GLU | D | 712 | -98.864 | -15.265 | 25.148 | 1.00 | 28.70 |
| 23850 | OE1 | GLU | D | 712 | -98.685 | -15.605 | 23.955 | 1.00 | 32.99 |
| 23851 | OE2 | GLU | D | 712 | -99.954 | -15.436 | 25.729 | 1.00 | 28.16 |
| 23852 | C | GLU | D | 712 | -98.662 | -10.871 | 25.525 | 1.00 | 24.90 |
| 23853 | O | GLU | D | 712 | -97.894 | -9.908 | 25.710 | 1.00 | 24.40 |
| 23854 | N | ASP | D | 713 | -99.977 | -10.766 | 25.677 | 1.00 | 25.38 |
| 23855 | CA | ASP | D | 713 | -100.541 | -9.490 | 26.086 | 1.00 | 26.35 |
| 23856 | CB | ASP | D | 713 | -101.709 | -9.066 | 25.204 | 1.00 | 26.45 |
| 23857 | CG | ASP | D | 713 | -102.948 | -9.944 | 25.385 | 1.00 | 28.52 |
| 23858 | OD1 | ASP | D | 713 | -103.943 | -9.689 | 24.664 | 1.00 | 32.19 |

FIGURE 3 QZ

| A | B | C | D | E | F | G | H | I | J |
|---|---|---|---|---|---|---|---|---|---|
| 23859 | OD2 | ASP | D | 713 | -103.044 | -10.866 | 26.221 | 1.00 | 27.60 |
| 23860 | C | ASP | D | 713 | -100.891 | -9.553 | 27.562 | 1.00 | 25.89 |
| 23861 | O | ASP | D | 713 | -100.273 | -10.324 | 28.296 | 1.00 | 26.04 |
| 23862 | N | HIS | D | 714 | -101.868 | -8.774 | 28.008 | 1.00 | 25.24 |
| 23863 | CA | HIS | D | 714 | -102.177 | -8.773 | 29.429 | 1.00 | 25.39 |
| 23864 | CB | HIS | D | 714 | -103.164 | -7.671 | 29.790 | 1.00 | 24.41 |
| 23865 | CG | HIS | D | 714 | -103.016 | -7.192 | 31.193 | 1.00 | 24.80 |
| 23866 | ND1 | HIS | D | 714 | -101.806 | -6.777 | 31.708 | 1.00 | 24.09 |
| 23867 | CE1 | HIS | D | 714 | -101.964 | -6.433 | 32.973 | 1.00 | 22.22 |
| 23868 | NE2 | HIS | D | 714 | -103.232 | -6.603 | 33.296 | 1.00 | 23.96 |
| 23869 | CD2 | HIS | D | 714 | -103.911 | -7.090 | 32.206 | 1.00 | 25.30 |
| 23870 | C | HIS | D | 714 | -102.679 | -10.104 | 29.948 | 1.00 | 25.99 |
| 23871 | O | HIS | D | 714 | -102.518 | -10.408 | 31.123 | 1.00 | 26.72 |
| 23872 | N | GLY | D | 715 | -103.277 | -10.911 | 29.076 | 1.00 | 26.76 |
| 23873 | CA | GLY | D | 715 | -103.860 | -12.168 | 29.492 | 1.00 | 27.06 |
| 23874 | C | GLY | D | 715 | -102.894 | -13.334 | 29.578 | 1.00 | 28.15 |
| 23875 | O | GLY | D | 715 | -103.189 | -14.317 | 30.269 | 1.00 | 28.12 |
| 23876 | N | ILE | D | 716 | -101.738 | -13.226 | 28.916 | 1.00 | 28.62 |
| 23877 | CA | ILE | D | 716 | -100.816 | -14.350 | 28.828 | 1.00 | 29.13 |
| 23878 | CB | ILE | D | 716 | -99.971 | -14.457 | 30.096 | 1.00 | 29.10 |
| 23879 | CG1 | ILE | D | 716 | -99.493 | -13.050 | 30.505 | 1.00 | 28.03 |
| 23880 | CD1 | ILE | D | 716 | -98.224 | -13.034 | 31.308 | 1.00 | 26.15 |
| 23881 | CG2 | ILE | D | 716 | -98.794 | -15.432 | 29.879 | 1.00 | 26.30 |
| 23882 | C | ILE | D | 716 | -101.699 | -15.567 | 28.663 | 1.00 | 30.53 |
| 23883 | O | ILE | D | 716 | -101.572 | -16.553 | 29.377 | 1.00 | 30.93 |
| 23884 | N | ALA | D | 717 | -102.581 | -15.488 | 27.676 | 1.00 | 31.90 |
| 23885 | CA | ALA | D | 717 | -103.652 | -16.452 | 27.527 | 1.00 | 32.82 |
| 23886 | CB | ALA | D | 717 | -104.971 | -15.701 | 27.359 | 1.00 | 32.77 |
| 23887 | C | ALA | D | 717 | -103.468 | -17.466 | 26.411 | 1.00 | 33.53 |
| 23888 | O | ALA | D | 717 | -104.297 | -18.345 | 26.225 | 1.00 | 34.26 |
| 23889 | N | SER | D | 718 | -102.414 | -17.337 | 25.631 | 1.00 | 34.51 |
| 23890 | CA | SER | D | 718 | -102.149 | -18.369 | 24.648 | 1.00 | 34.89 |
| 23891 | CB | SER | D | 718 | -100.813 | -18.117 | 23.966 | 1.00 | 35.09 |
| 23892 | OG | SER | D | 718 | -100.861 | -16.872 | 23.278 | 1.00 | 38.42 |
| 23893 | C | SER | D | 718 | -102.138 | -19.699 | 25.406 | 1.00 | 34.66 |
| 23894 | O | SER | D | 718 | -101.737 | -19.773 | 26.560 | 1.00 | 34.70 |
| 23895 | N | SER | D | 719 | -102.597 | -20.754 | 24.763 | 1.00 | 34.36 |
| 23896 | CA | SER | D | 719 | -102.646 | -22.033 | 25.429 | 1.00 | 33.70 |
| 23897 | CB | SER | D | 719 | -103.188 | -23.106 | 24.485 | 1.00 | 33.97 |
| 23898 | OG | SER | D | 719 | -103.222 | -24.340 | 25.165 | 1.00 | 35.36 |
| 23899 | C | SER | D | 719 | -101.266 | -22.419 | 25.974 | 1.00 | 32.72 |
| 23900 | O | SER | D | 719 | -101.151 | -22.841 | 27.119 | 1.00 | 32.25 |
| 23901 | N | THR | D | 720 | -100.218 | -22.252 | 25.175 | 1.00 | 31.69 |
| 23902 | CA | THR | D | 720 | -98.884 | -22.618 | 25.653 | 1.00 | 31.34 |
| 23903 | CB | THR | D | 720 | -97.878 | -22.741 | 24.491 | 1.00 | 31.31 |
| 23904 | OG1 | THR | D | 720 | -97.765 | -21.487 | 23.807 | 1.00 | 30.08 |
| 23905 | CG2 | THR | D | 720 | -98.408 | -23.750 | 23.417 | 1.00 | 31.67 |
| 23906 | C | THR | D | 720 | -98.321 | -21.702 | 26.751 | 1.00 | 31.24 |
| 23907 | O | THR | D | 720 | -97.699 | -22.181 | 27.701 | 1.00 | 31.39 |
| 23908 | N | ALA | D | 721 | -98.542 | -20.397 | 26.632 | 1.00 | 30.79 |
| 23909 | CA | ALA | D | 721 | -97.983 | -19.459 | 27.599 | 1.00 | 30.63 |

FIGURE 3 RA

| A | B | C | D | E | F | G | H | I | J |
|---|---|---|---|---|---|---|---|---|---|
| 23910 | CB | ALA | D | 721 | -98.069 | -18.010 | 27.084 | 1.00 | 30.07 |
| 23911 | C | ALA | D | 721 | -98.715 | -19.615 | 28.901 | 1.00 | 30.47 |
| 23912 | O | ALA | D | 721 | -98.129 | -19.542 | 29.969 | 1.00 | 30.41 |
| 23913 | N | HIS | D | 722 | -100.011 | -19.859 | 28.800 | 1.00 | 30.82 |
| 23914 | CA | HIS | D | 722 | -100.831 | -20.075 | 29.982 | 1.00 | 31.21 |
| 23915 | CB | HIS | D | 722 | -102.294 | -20.280 | 29.581 | 1.00 | 31.42 |
| 23916 | CG | HIS | D | 722 | -103.150 | -20.822 | 30.680 | 1.00 | 32.76 |
| 23917 | ND1 | HIS | D | 722 | -103.602 | -20.045 | 31.721 | 1.00 | 34.01 |
| 23918 | CE1 | HIS | D | 722 | -104.335 | -20.781 | 32.537 | 1.00 | 34.22 |
| 23919 | NE2 | HIS | D | 722 | -104.363 | -22.014 | 32.070 | 1.00 | 35.08 |
| 23920 | CD2 | HIS | D | 722 | -103.629 | -22.068 | 30.908 | 1.00 | 34.44 |
| 23921 | C | HIS | D | 722 | -100.311 | -21.270 | 30.771 | 1.00 | 31.02 |
| 23922 | O | HIS | D | 722 | -100.170 | -21.216 | 32.002 | 1.00 | 31.48 |
| 23923 | N | GLN | D | 723 | -100.019 | -22.360 | 30.077 | 1.00 | 30.29 |
| 23924 | CA | GLN | D | 723 | -99.473 | -23.517 | 30.769 | 1.00 | 29.72 |
| 23925 | CB | GLN | D | 723 | -99.444 | -24.737 | 29.836 | 1.00 | 29.79 |
| 23926 | CG | GLN | D | 723 | -100.808 | -25.099 | 29.260 | 1.00 | 31.78 |
| 23927 | CD | GLN | D | 723 | -100.717 | -26.195 | 28.215 | 1.00 | 34.32 |
| 23928 | OE1 | GLN | D | 723 | -100.201 | -27.290 | 28.495 | 1.00 | 36.17 |
| 23929 | NE2 | GLN | D | 723 | -101.196 | -25.906 | 27.010 | 1.00 | 31.59 |
| 23930 | C | GLN | D | 723 | -98.063 | -23.233 | 31.296 | 1.00 | 28.87 |
| 23931 | O | GLN | D | 723 | -97.680 | -23.717 | 32.361 | 1.00 | 28.62 |
| 23932 | N | HIS | D | 724 | -97.283 | -22.482 | 30.531 | 1.00 | 28.25 |
| 23933 | CA | HIS | D | 724 | -95.901 | -22.186 | 30.909 | 1.00 | 28.61 |
| 23934 | CB | HIS | D | 724 | -95.137 | -21.579 | 29.730 | 1.00 | 28.69 |
| 23935 | CG | HIS | D | 724 | -93.650 | -21.580 | 29.904 | 1.00 | 29.79 |
| 23936 | ND1 | HIS | D | 724 | -92.995 | -20.699 | 30.738 | 1.00 | 29.17 |
| 23937 | CE1 | HIS | D | 724 | -91.693 | -20.935 | 30.687 | 1.00 | 29.96 |
| 23938 | NE2 | HIS | D | 724 | -91.482 | -21.936 | 29.850 | 1.00 | 29.22 |
| 23939 | CD2 | HIS | D | 724 | -92.688 | -22.354 | 29.344 | 1.00 | 30.80 |
| 23940 | C | HIS | D | 724 | -95.776 | -21.298 | 32.152 | 1.00 | 28.58 |
| 23941 | O | HIS | D | 724 | -94.914 | -21.534 | 32.987 | 1.00 | 28.75 |
| 23942 | N | ILE | D | 725 | -96.655 | -20.304 | 32.293 | 1.00 | 28.58 |
| 23943 | CA | ILE | D | 725 | -96.589 | -19.408 | 33.439 | 1.00 | 28.30 |
| 23944 | CB | ILE | D | 725 | -97.407 | -18.092 | 33.204 | 1.00 | 28.22 |
| 23945 | CG1 | ILE | D | 725 | -97.166 | -17.107 | 34.359 | 1.00 | 26.66 |
| 23946 | CD1 | ILE | D | 725 | -97.987 | -15.800 | 34.259 | 1.00 | 23.69 |
| 23947 | CG2 | ILE | D | 725 | -98.897 | -18.358 | 33.041 | 1.00 | 26.98 |
| 23948 | C | ILE | D | 725 | -96.989 | -20.095 | 34.739 | 1.00 | 28.65 |
| 23949 | O | ILE | D | 725 | -96.267 | -20.017 | 35.746 | 1.00 | 28.07 |
| 23950 | N | TYR | D | 726 | -98.124 | -20.798 | 34.723 | 1.00 | 28.74 |
| 23951 | CA | TYR | D | 726 | -98.563 | -21.472 | 35.933 | 1.00 | 28.23 |
| 23952 | CB | TYR | D | 726 | -99.999 | -21.975 | 35.803 | 1.00 | 28.51 |
| 23953 | CG | TYR | D | 726 | -101.012 | -20.863 | 35.981 | 1.00 | 28.99 |
| 23954 | CD1 | TYR | D | 726 | -101.532 | -20.187 | 34.888 | 1.00 | 28.65 |
| 23955 | CE1 | TYR | D | 726 | -102.433 | -19.151 | 35.048 | 1.00 | 27.20 |
| 23956 | CZ | TYR | D | 726 | -102.819 | -18.786 | 36.318 | 1.00 | 27.84 |
| 23957 | OH | TYR | D | 726 | -103.729 | -17.770 | 36.494 | 1.00 | 26.17 |
| 23958 | CE2 | TYR | D | 726 | -102.326 | -19.456 | 37.420 | 1.00 | 27.71 |
| 23959 | CD2 | TYR | D | 726 | -101.417 | -20.470 | 37.250 | 1.00 | 28.75 |
| 23960 | C | TYR | D | 726 | -97.574 | -22.560 | 36.336 | 1.00 | 28.21 |

FIGURE 3 RB

| A | B | C | D | E | F | G | H | I | J |
|---|---|---|---|---|---|---|---|---|---|
| 23961 | O | TYR | D | 726 | -97.392 | -22.827 | 37.521 | 1.00 | 28.14 |
| 23962 | N | THR | D | 727 | -96.908 | -23.155 | 35.352 | 1.00 | 28.24 |
| 23963 | CA | THR | D | 727 | -95.906 | -24.182 | 35.612 | 1.00 | 28.34 |
| 23964 | CB | THR | D | 727 | -95.452 | -24.871 | 34.283 | 1.00 | 28.52 |
| 23965 | OG1 | THR | D | 727 | -96.575 | -25.509 | 33.654 | 1.00 | 30.62 |
| 23966 | CG2 | THR | D | 727 | -94.527 | -26.045 | 34.558 | 1.00 | 27.79 |
| 23967 | C | THR | D | 727 | -94.723 | -23.522 | 36.307 | 1.00 | 28.16 |
| 23968 | O | THR | D | 727 | -94.266 | -23.982 | 37.344 | 1.00 | 28.00 |
| 23969 | N | HIS | D | 728 | -94.249 | -22.417 | 35.746 | 1.00 | 28.34 |
| 23970 | CA | HIS | D | 728 | -93.129 | -21.693 | 36.342 | 1.00 | 27.90 |
| 23971 | CB | HIS | D | 728 | -92.708 | -20.536 | 35.456 | 1.00 | 27.93 |
| 23972 | CG | HIS | D | 728 | -91.256 | -20.190 | 35.569 | 1.00 | 28.71 |
| 23973 | ND1 | HIS | D | 728 | -90.807 | -19.043 | 36.190 | 1.00 | 26.94 |
| 23974 | CE1 | HIS | D | 728 | -89.492 | -18.995 | 36.118 | 1.00 | 26.25 |
| 23975 | NE2 | HIS | D | 728 | -89.069 | -20.066 | 35.471 | 1.00 | 27.15 |
| 23976 | CD2 | HIS | D | 728 | -90.153 | -20.826 | 35.114 | 1.00 | 27.68 |
| 23977 | C | HIS | D | 728 | -93.513 | -21.177 | 37.709 | 1.00 | 27.60 |
| 23978 | O | HIS | D | 728 | -92.732 | -21.260 | 38.642 | 1.00 | 27.81 |
| 23979 | N | MET | D | 729 | -94.736 | -20.680 | 37.854 | 1.00 | 27.20 |
| 23980 | CA | MET | D | 729 | -95.142 | -20.148 | 39.151 | 1.00 | 27.30 |
| 23981 | CB | MET | D | 729 | -96.461 | -19.383 | 39.044 | 1.00 | 27.41 |
| 23982 | CG | MET | D | 729 | -96.356 | -18.089 | 38.223 | 1.00 | 27.80 |
| 23983 | SD | MET | D | 729 | -97.799 | -17.045 | 38.474 | 1.00 | 31.32 |
| 23984 | CE | MET | D | 729 | -98.988 | -17.959 | 37.603 | 1.00 | 28.58 |
| 23985 | C | MET | D | 729 | -95.234 | -21.217 | 40.227 | 1.00 | 27.58 |
| 23986 | O | MET | D | 729 | -94.988 | -20.946 | 41.415 | 1.00 | 26.14 |
| 23987 | N | SER | D | 730 | -95.599 | -22.426 | 39.790 | 1.00 | 28.27 |
| 23988 | CA | SER | D | 730 | -95.763 | -23.574 | 40.675 | 1.00 | 29.26 |
| 23989 | CB | SER | D | 730 | -96.461 | -24.733 | 39.940 | 1.00 | 29.36 |
| 23990 | OG | SER | D | 730 | -97.801 | -24.388 | 39.604 | 1.00 | 30.37 |
| 23991 | C | SER | D | 730 | -94.415 | -24.006 | 41.220 | 1.00 | 29.27 |
| 23992 | O | SER | D | 730 | -94.272 | -24.254 | 42.412 | 1.00 | 29.22 |
| 23993 | N | HIS | D | 731 | -93.429 | -24.070 | 40.341 | 1.00 | 30.11 |
| 23994 | CA | HIS | D | 731 | -92.050 | -24.371 | 40.740 | 1.00 | 31.48 |
| 23995 | CB | HIS | D | 731 | -91.110 | -24.302 | 39.527 | 1.00 | 31.75 |
| 23996 | CG | HIS | D | 731 | -91.168 | -25.502 | 38.635 | 1.00 | 36.02 |
| 23997 | ND1 | HIS | D | 731 | -91.333 | -26.785 | 39.120 | 1.00 | 40.04 |
| 23998 | CE1 | HIS | D | 731 | -91.335 | -27.636 | 38.108 | 1.00 | 41.67 |
| 23999 | NE2 | HIS | D | 731 | -91.175 | -26.955 | 36.986 | 1.00 | 39.65 |
| 24000 | CD2 | HIS | D | 731 | -91.063 | -25.619 | 37.288 | 1.00 | 38.27 |
| 24001 | C | HIS | D | 731 | -91.555 | -23.364 | 41.769 | 1.00 | 31.01 |
| 24002 | O | HIS | D | 731 | -90.973 | -23.743 | 42.788 | 1.00 | 31.43 |
| 24003 | N | PHE | D | 732 | -91.796 | -22.077 | 41.498 | 1.00 | 30.94 |
| 24004 | CA | PHE | D | 732 | -91.300 | -20.990 | 42.351 | 1.00 | 30.28 |
| 24005 | CB | PHE | D | 732 | -91.692 | -19.624 | 41.791 | 1.00 | 29.78 |
| 24006 | CG | PHE | D | 732 | -91.248 | -18.468 | 42.645 | 1.00 | 27.75 |
| 24007 | CD1 | PHE | D | 732 | -89.946 | -17.998 | 42.572 | 1.00 | 27.19 |
| 24008 | CE1 | PHE | D | 732 | -89.533 | -16.942 | 43.358 | 1.00 | 28.30 |
| 24009 | CZ | PHE | D | 732 | -90.446 | -16.323 | 44.213 | 1.00 | 28.28 |
| 24010 | CE2 | PHE | D | 732 | -91.744 | -16.781 | 44.279 | 1.00 | 25.45 |
| 24011 | CD2 | PHE | D | 732 | -92.131 | -17.853 | 43.509 | 1.00 | 25.81 |

FIGURE 3 RC

| A | B | C | D | E | F | G | H | I | J |
|---|---|---|---|---|---|---|---|---|---|
| 24012 | C | PHE | D | 732 | -91.851 | -21.104 | 43.732 | 1.00 | 30.64 |
| 24013 | O | PHE | D | 732 | -91.116 | -20.985 | 44.717 | 1.00 | 30.47 |
| 24014 | N | ILE | D | 733 | -93.158 | -21.329 | 43.786 | 1.00 | 31.23 |
| 24015 | CA | ILE | D | 733 | -93.880 | -21.476 | 45.034 | 1.00 | 32.24 |
| 24016 | CB | ILE | D | 733 | -95.393 | -21.564 | 44.756 | 1.00 | 32.28 |
| 24017 | CG1 | ILE | D | 733 | -95.881 | -20.241 | 44.184 | 1.00 | 33.24 |
| 24018 | CD1 | ILE | D | 733 | -95.741 | -19.063 | 45.155 | 1.00 | 34.28 |
| 24019 | CG2 | ILE | D | 733 | -96.178 | -21.875 | 46.030 | 1.00 | 31.60 |
| 24020 | C | ILE | D | 733 | -93.393 | -22.700 | 45.795 | 1.00 | 33.05 |
| 24021 | O | ILE | D | 733 | -93.043 | -22.584 | 46.960 | 1.00 | 33.10 |
| 24022 | N | LYS | D | 734 | -93.366 | -23.859 | 45.127 | 1.00 | 34.12 |
| 24023 | CA | LYS | D | 734 | -92.894 | -25.111 | 45.732 | 1.00 | 35.44 |
| 24024 | CB | LYS | D | 734 | -92.634 | -26.209 | 44.671 | 1.00 | 35.53 |
| 24025 | CG | LYS | D | 734 | -93.742 | -26.483 | 43.666 | 1.00 | 37.56 |
| 24026 | CD | LYS | D | 734 | -94.685 | -27.595 | 44.080 | 1.00 | 40.97 |
| 24027 | CE | LYS | D | 734 | -94.023 | -28.977 | 43.982 | 1.00 | 41.85 |
| 24028 | NZ | LYS | D | 734 | -95.014 | -30.045 | 43.641 | 1.00 | 42.68 |
| 24029 | C | LYS | D | 734 | -91.569 | -24.850 | 46.411 | 1.00 | 35.69 |
| 24030 | O | LYS | D | 734 | -91.380 | -25.172 | 47.579 | 1.00 | 35.50 |
| 24031 | N | GLN | D | 735 | -90.649 | -24.283 | 45.636 | 1.00 | 36.31 |
| 24032 | CA | GLN | D | 735 | -89.291 | -23.998 | 46.081 | 1.00 | 37.37 |
| 24033 | CB | GLN | D | 735 | -88.466 | -23.428 | 44.915 | 1.00 | 38.00 |
| 24034 | CG | GLN | D | 735 | -87.112 | -24.133 | 44.683 | 1.00 | 42.23 |
| 24035 | CD | GLN | D | 735 | -86.882 | -24.498 | 43.214 | 1.00 | 46.36 |
| 24036 | OE1 | GLN | D | 735 | -87.676 | -24.120 | 42.353 | 1.00 | 49.07 |
| 24037 | NE2 | GLN | D | 735 | -85.804 | -25.243 | 42.930 | 1.00 | 48.29 |
| 24038 | C | GLN | D | 735 | -89.287 | -23.048 | 47.280 | 1.00 | 37.22 |
| 24039 | O | GLN | D | 735 | -88.546 | -23.262 | 48.235 | 1.00 | 37.42 |
| 24040 | N | CYS | D | 736 | -90.138 | -22.027 | 47.249 | 1.00 | 36.65 |
| 24041 | CA | CYS | D | 736 | -90.209 | -21.069 | 48.348 | 1.00 | 36.80 |
| 24042 | CB | CYS | D | 736 | -91.071 | -19.857 | 47.957 | 1.00 | 36.66 |
| 24043 | SG | CYS | D | 736 | -91.706 | -18.832 | 49.313 | 1.00 | 38.36 |
| 24044 | C | CYS | D | 736 | -90.746 | -21.720 | 49.617 | 1.00 | 36.81 |
| 24045 | O | CYS | D | 736 | -90.331 | -21.367 | 50.731 | 1.00 | 36.68 |
| 24046 | N | PHE | D | 737 | -91.663 | -22.669 | 49.436 | 1.00 | 36.64 |
| 24047 | CA | PHE | D | 737 | -92.305 | -23.362 | 50.541 | 1.00 | 36.62 |
| 24048 | CB | PHE | D | 737 | -93.752 | -23.694 | 50.182 | 1.00 | 35.97 |
| 24049 | CG | PHE | D | 737 | -94.676 | -22.524 | 50.260 | 1.00 | 34.35 |
| 24050 | CD1 | PHE | D | 737 | -94.253 | -21.335 | 50.826 | 1.00 | 30.83 |
| 24051 | CE1 | PHE | D | 737 | -95.095 | -20.256 | 50.904 | 1.00 | 28.86 |
| 24052 | CZ | PHE | D | 737 | -96.377 | -20.344 | 50.422 | 1.00 | 29.88 |
| 24053 | CE2 | PHE | D | 737 | -96.820 | -21.523 | 49.838 | 1.00 | 30.99 |
| 24054 | CD2 | PHE | D | 737 | -95.968 | -22.604 | 49.754 | 1.00 | 31.96 |
| 24055 | C | PHE | D | 737 | -91.582 | -24.653 | 50.887 | 1.00 | 37.46 |
| 24056 | O | PHE | D | 737 | -91.996 | -25.381 | 51.782 | 1.00 | 37.47 |
| 24057 | N | SER | D | 738 | -90.513 | -24.949 | 50.165 | 1.00 | 38.74 |
| 24058 | CA | SER | D | 738 | -89.768 | -26.170 | 50.419 | 1.00 | 40.18 |
| 24059 | CB | SER | D | 738 | -89.240 | -26.211 | 51.858 | 1.00 | 39.94 |
| 24060 | OG | SER | D | 738 | -88.089 | -25.409 | 51.986 | 1.00 | 39.67 |
| 24061 | C | SER | D | 738 | -90.633 | -27.390 | 50.153 | 1.00 | 41.31 |
| 24062 | O | SER | D | 738 | -90.620 | -28.342 | 50.937 | 1.00 | 41.36 |

24063     N    LEU D 739     -91.380  -27.352   49.051  1.00  42.72
24064     CA   LEU D 739     -92.192  -28.484   48.624  1.00  44.17
24065     CB   LEU D 739     -93.565  -28.034   48.154  1.00  43.93
24066     CG   LEU D 739     -94.462  -27.445   49.231  1.00  44.34
24067     CD1  LEU D 739     -95.808  -27.149   48.641  1.00  44.64
24068     CD2  LEU D 739     -94.583  -28.407   50.404  1.00  45.57
24069     C    LEU D 739     -91.507  -29.224   47.495  1.00  45.39
24070     O    LEU D 739     -91.217  -28.656   46.445  1.00  45.92
24071     N    PRO D 740     -91.231  -30.498   47.716  1.00  46.58
24072     CA   PRO D 740     -90.596  -31.337   46.698  1.00  47.17
24073     CB   PRO D 740     -90.074  -32.527   47.508  1.00  47.54
24074     CG   PRO D 740     -90.252  -32.109   48.972  1.00  48.06
24075     CD   PRO D 740     -91.471  -31.223   48.974  1.00  46.94
24076     C    PRO D 740     -91.607  -31.811   45.662  1.00  47.45
24077     O    PRO D 740     -92.806  -31.592   45.868  1.00  47.85
24078     O7   NAG D1621    -115.658  -10.108    1.065  1.00  73.42
24079     C7   NAG D1621    -115.594   -9.096    0.380  1.00  72.75
24080     C8   NAG D1621    -116.631   -8.018    0.445  1.00  73.32
24081     N2   NAG D1621    -114.567   -8.812   -0.414  1.00  71.98
24082     C2   NAG D1621    -113.456   -9.726   -0.607  1.00  71.93
24083     C1   NAG D1621    -112.792  -10.113    0.713  1.00  70.01
24084     C3   NAG D1621    -113.935  -10.979   -1.334  1.00  72.45
24085     O3   NAG D1621    -114.520  -10.646   -2.610  1.00  71.12
24086     C4   NAG D1621    -112.786  -11.977   -1.491  1.00  72.47
24087     O4   NAG D1621    -113.351  -13.258   -1.775  1.00  72.94
24088     C5   NAG D1621    -111.914  -12.131   -0.238  1.00  72.76
24089     O5   NAG D1621    -111.628  -10.885    0.412  1.00  72.16
24090     C6   NAG D1621    -110.598  -12.825   -0.601  1.00  73.05
24091     O6   NAG D1621    -109.961  -13.377    0.560  1.00  72.80
24092     O7   NAG D2311    -143.486    2.005   13.260  1.00  74.38
24093     C7   NAG D2311    -142.386    1.558   12.963  1.00  73.58
24094     C8   NAG D2311    -142.247    0.199   12.336  1.00  73.63
24095     N2   NAG D2311    -141.263    2.274   13.096  1.00  71.98
24096     C2   NAG D2311    -141.288    3.609   13.680  1.00  70.62
24097     C1   NAG D2311    -140.106    3.832   14.614  1.00  67.00
24098     C3   NAG D2311    -141.303    4.679   12.596  1.00  70.50
24099     O3   NAG D2311    -142.506    4.535   11.840  1.00  71.38
24100     C4   NAG D2311    -141.254    6.070   13.217  1.00  70.31
24101     O4   NAG D2311    -141.099    7.052   12.181  1.00  70.47
24102     C5   NAG D2311    -140.104    6.171   14.219  1.00  69.91
24103     O5   NAG D2311    -140.196    5.133   15.192  1.00  69.16
24104     C6   NAG D2311    -140.111    7.517   14.934  1.00  70.22
24105     O6   NAG D2311    -141.207    7.570   15.854  1.00  70.09
24106     O7   NAG D2411    -112.694   16.675   14.251  1.00  58.29
24107     C7   NAG D2411    -111.936   16.037   13.545  1.00  58.41
24108     C8   NAG D2411    -112.422   15.169   12.422  1.00  57.84
24109     N2   NAG D2411    -110.619   16.110   13.681  1.00  58.33
24110     C2   NAG D2411    -110.033   16.919   14.722  1.00  58.50
24111     C1   NAG D2411    -109.372   16.035   15.770  1.00  55.27
24112     C3   NAG D2411    -109.003   17.855   14.113  1.00  60.36
24113     O3   NAG D2411    -109.616   18.724   13.147  1.00  61.58
```

FIGURE 3 RE

| A | B | C | D E | F | G | H | I | J |
|---|---|---|---|---|---|---|---|---|
| 24114 | C4 | NAG | D2411 | -108.359 | 18.664 | 15.225 | 1.00 | 61.57 |
| 24115 | O4 | NAG | D2411 | -107.303 | 19.448 | 14.664 | 1.00 | 67.27 |
| 24116 | C5 | NAG | D2411 | -107.807 | 17.736 | 16.309 | 1.00 | 60.81 |
| 24117 | O5 | NAG | D2411 | -108.833 | 16.866 | 16.793 | 1.00 | 58.82 |
| 24118 | C6 | NAG | D2411 | -107.256 | 18.518 | 17.490 | 1.00 | 60.30 |
| 24119 | O6 | NAG | D2411 | -106.648 | 17.593 | 18.392 | 1.00 | 61.16 |
| 24120 | O7 | NAG | D2412 | -102.963 | 19.045 | 15.946 | 1.00 | 79.63 |
| 24121 | C7 | NAG | D2412 | -103.800 | 19.396 | 15.139 | 1.00 | 78.83 |
| 24122 | C8 | NAG | D2412 | -103.934 | 18.788 | 13.771 | 1.00 | 79.00 |
| 24123 | N2 | NAG | D2412 | -104.689 | 20.321 | 15.489 | 1.00 | 78.34 |
| 24124 | C2 | NAG | D2412 | -105.721 | 20.814 | 14.606 | 1.00 | 78.56 |
| 24125 | C1 | NAG | D2412 | -107.094 | 20.684 | 15.246 | 1.00 | 76.22 |
| 24126 | C3 | NAG | D2412 | -105.386 | 22.271 | 14.309 | 1.00 | 79.46 |
| 24127 | O3 | NAG | D2412 | -104.278 | 22.311 | 13.399 | 1.00 | 80.11 |
| 24128 | C4 | NAG | D2412 | -106.553 | 23.048 | 13.709 | 1.00 | 79.88 |
| 24129 | O4 | NAG | D2412 | -106.301 | 24.453 | 13.835 | 1.00 | 80.18 |
| 24130 | C5 | NAG | D2412 | -107.870 | 22.718 | 14.397 | 1.00 | 79.65 |
| 24131 | O5 | NAG | D2412 | -108.051 | 21.305 | 14.391 | 1.00 | 78.94 |
| 24132 | C6 | NAG | D2412 | -109.038 | 23.397 | 13.689 | 1.00 | 79.99 |
| 24133 | O6 | NAG | D2412 | -109.050 | 23.024 | 12.305 | 1.00 | 80.18 |
| 24134 | O7 | NAG | D2931 | -121.810 | 14.605 | -2.718 | 1.00 | 80.29 |
| 24135 | C7 | NAG | D2931 | -121.748 | 13.389 | -2.736 | 1.00 | 80.24 |
| 24136 | C8 | NAG | D2931 | -122.652 | 12.560 | -3.606 | 1.00 | 80.94 |
| 24137 | N2 | NAG | D2931 | -120.825 | 12.713 | -2.050 | 1.00 | 78.56 |
| 24138 | C2 | NAG | D2931 | -119.878 | 13.395 | -1.190 | 1.00 | 77.00 |
| 24139 | C1 | NAG | D2931 | -119.943 | 12.829 | 0.230 | 1.00 | 74.54 |
| 24140 | C3 | NAG | D2931 | -118.494 | 13.252 | -1.814 | 1.00 | 77.06 |
| 24141 | O3 | NAG | D2931 | -118.432 | 14.006 | -3.035 | 1.00 | 77.42 |
| 24142 | C4 | NAG | D2931 | -117.406 | 13.711 | -0.852 | 1.00 | 76.73 |
| 24143 | O4 | NAG | D2931 | -116.121 | 13.393 | -1.397 | 1.00 | 76.18 |
| 24144 | C5 | NAG | D2931 | -117.569 | 13.022 | 0.496 | 1.00 | 76.47 |
| 24145 | O5 | NAG | D2931 | -118.861 | 13.321 | 1.025 | 1.00 | 76.20 |
| 24146 | C6 | NAG | D2931 | -116.517 | 13.547 | 1.462 | 1.00 | 76.51 |
| 24147 | O6 | NAG | D2931 | -116.850 | 14.893 | 1.819 | 1.00 | 76.40 |
| 24148 | O7 | NAG | D3331 | -116.219 | 16.951 | 45.963 | 1.00 | 62.90 |
| 24149 | C7 | NAG | D3331 | -116.733 | 17.154 | 44.869 | 1.00 | 62.34 |
| 24150 | C8 | NAG | D3331 | -118.215 | 17.287 | 44.684 | 1.00 | 61.90 |
| 24151 | N2 | NAG | D3331 | -115.991 | 17.361 | 43.789 | 1.00 | 61.79 |
| 24152 | C2 | NAG | D3331 | -114.552 | 17.254 | 43.909 | 1.00 | 61.67 |
| 24153 | C1 | NAG | D3331 | -113.957 | 16.496 | 42.730 | 1.00 | 57.43 |
| 24154 | C3 | NAG | D3331 | -113.878 | 18.612 | 44.037 | 1.00 | 62.68 |
| 24155 | O3 | NAG | D3331 | -114.391 | 19.283 | 45.188 | 1.00 | 63.18 |
| 24156 | C4 | NAG | D3331 | -112.380 | 18.387 | 44.208 | 1.00 | 63.31 |
| 24157 | O4 | NAG | D3331 | -111.696 | 19.642 | 44.179 | 1.00 | 64.30 |
| 24158 | C5 | NAG | D3331 | -111.827 | 17.472 | 43.110 | 1.00 | 62.90 |
| 24159 | O5 | NAG | D3331 | -112.580 | 16.260 | 43.023 | 1.00 | 62.27 |
| 24160 | C6 | NAG | D3331 | -110.382 | 17.098 | 43.394 | 1.00 | 63.76 |
| 24161 | O6 | NAG | D3331 | -110.097 | 15.863 | 42.731 | 1.00 | 65.10 |
| 24162 | O | HOH | W    1 | -70.047 | -9.621 | 78.744 | 1.00 | 22.57 |
| 24163 | O | HOH | W    2 | -34.851 | -4.814 | 99.378 | 1.00 | 19.43 |
| 24164 | O | HOH | W    3 | -62.319 | -2.336 | 82.776 | 1.00 | 15.33 |

24165    O   HOH  W    4    -105.925   -3.902   37.241  1.00  21.48
  24166    O   HOH  W    5     -52.287   -3.318   87.258  1.00  18.54
  24167    O   HOH  W    6     -91.285  -16.061   25.538  1.00  22.18
  24168    O   HOH  W    7     -33.478    6.291   87.322  1.00  21.61
  24169    O   HOH  W    8     -32.644   -5.923   92.690  1.00  16.83
  24170    O   HOH  W    9     -83.500   -4.860   34.516  1.00  20.17
  24171    O   HOH  W   10     -95.846   -3.672   26.390  1.00  22.63
  24172    O   HOH  W   11     -38.585   -8.808   81.793  1.00  32.00
  24173    O   HOH  W   12    -131.539    3.310   49.749  1.00  24.07
  24174    O   HOH  W   13     -89.602   -6.431   24.528  1.00  31.49
  24175    O   HOH  W   14     -22.191   19.290   81.198  1.00  29.71
  24176    O   HOH  W   15    -103.695   -7.177   26.708  1.00  23.52
  24177    O   HOH  W   16     -48.011   -6.164   76.557  1.00  19.02
  24178    O   HOH  W   17     -61.410  -18.972   74.744  1.00  17.60
  24179    O   HOH  W   18     -87.151   -5.568   66.326  1.00  30.46
  24180    O   HOH  W   19     -44.226   22.424   76.402  1.00  28.91
  24181    O   HOH  W   20     -83.027   -8.609   67.599  1.00  25.69
  24182    O   HOH  W   21    -105.924  -19.170   40.951  1.00  25.71
  24183    O   HOH  W   22     -79.666   -0.305   31.865  1.00  24.81
  24184    O   HOH  W   23     -70.178   -9.767   91.982  1.00  15.50
  24185    O   HOH  W   24    -120.299    1.315   46.762  1.00  32.88
  24186    O   HOH  W   25    -126.417  -15.760   32.836  1.00  35.97
  24187    O   HOH  W   26    -107.622   -9.077   46.909  1.00  19.86
  24188    O   HOH  W   27     -88.087   -4.550   25.498  1.00  19.45
  24189    O   HOH  W   28     -82.329    4.434   33.892  1.00  20.74
  24190    O   HOH  W   29     -71.620  -24.011   85.413  1.00  25.43
  24191    O   HOH  W   30     -46.730   -8.233   84.956  1.00  25.87
  24192    O   HOH  W   31     -98.497  -11.196   73.755  1.00  26.51
  24193    O   HOH  W   32     -87.168   -5.170   18.974  1.00  26.01
  24194    O   HOH  W   33     -62.091  -12.323   84.142  1.00  23.87
  24195    O   HOH  W   34     -50.927   -6.839   93.390  1.00  26.48
  24196    O   HOH  W   35     -70.656   -3.379   73.593  1.00  20.18
  24197    O   HOH  W   36     -84.552   -6.501   19.825  1.00  24.45
  24198    O   HOH  W   37    -117.602  -11.619   43.383  1.00  29.61
  24199    O   HOH  W   38    -109.448   -3.153   38.603  1.00  19.00
  24200    O   HOH  W   39     -77.633  -16.012   77.912  1.00  18.39
  24201    O   HOH  W   40     -37.628   -8.094   86.503  1.00  24.21
  24202    O   HOH  W   41     -68.908   -6.239   89.490  1.00  30.06
  24203    O   HOH  W   42     -93.574  -16.006   55.747  1.00  20.92
  24204    O   HOH  W   43    -128.507    1.119   37.053  1.00  23.40
  24205    O   HOH  W   44     -53.377  -22.267   85.437  1.00  24.95
  24206    O   HOH  W   45     -27.348    7.987   74.856  1.00  33.09
  24207    O   HOH  W   46     -33.504    8.245   79.353  1.00  22.40
  24208    O   HOH  W   47     -63.275   -0.369   56.167  1.00  20.34
  24209    O   HOH  W   48     -60.051  -20.691   77.439  1.00  29.91
  24210    O   HOH  W   49    -103.083   -7.671   22.880  1.00  20.83
  24211    O   HOH  W   50     -55.646    5.935   84.874  1.00  16.39
  24212    O   HOH  W   51     -20.326   16.802   88.348  1.00  29.49
  24213    O   HOH  W   52     -31.662    6.373   71.432  1.00  25.55
  24214    O   HOH  W   53     -82.079    3.469   31.545  1.00  27.19
  24215    O   HOH  W   54     -71.278  -25.643   91.236  1.00  30.95
```

FIGURE 3 RG

| A | B | C | D | E | F | G | H | I | J |
|---|---|---|---|---|---|---|---|---|---|
| 24216 | O | HOH | W | 55 | -113.642 | 1.100 | 40.912 | 1.00 | 20.06 |
| 24217 | O | HOH | W | 56 | -106.400 | -10.823 | 48.758 | 1.00 | 23.65 |
| 24218 | O | HOH | W | 57 | -72.098 | -27.755 | 94.347 | 1.00 | 21.93 |
| 24219 | O | HOH | W | 58 | -81.485 | -2.961 | 34.163 | 1.00 | 20.94 |
| 24220 | O | HOH | W | 59 | -104.853 | -11.330 | 41.012 | 1.00 | 22.49 |
| 24221 | O | HOH | W | 60 | -50.143 | -21.292 | 15.918 | 1.00 | 46.06 |
| 24222 | O | HOH | W | 61 | -75.243 | -14.549 | 84.035 | 1.00 | 22.74 |
| 24223 | O | HOH | W | 62 | -42.523 | -4.657 | 66.681 | 1.00 | 32.51 |
| 24224 | O | HOH | W | 63 | -65.231 | -15.648 | 33.609 | 1.00 | 31.65 |
| 24225 | O | HOH | W | 64 | -108.948 | -3.717 | 25.649 | 1.00 | 29.83 |
| 24226 | O | HOH | W | 65 | -92.950 | -6.028 | 69.562 | 1.00 | 30.87 |
| 24227 | O | HOH | W | 66 | -86.814 | 5.040 | 47.700 | 1.00 | 39.21 |
| 24228 | O | HOH | W | 67 | -116.041 | -8.699 | 50.305 | 1.00 | 23.70 |
| 24229 | O | HOH | W | 68 | -93.123 | 10.711 | 28.131 | 1.00 | 26.08 |
| 24230 | O | HOH | W | 69 | -50.985 | 3.640 | 72.696 | 1.00 | 20.48 |
| 24231 | O | HOH | W | 70 | -70.198 | -10.686 | 80.787 | 1.00 | 27.69 |
| 24232 | O | HOH | W | 71 | -114.830 | -7.412 | 52.563 | 1.00 | 26.83 |
| 24233 | O | HOH | W | 72 | -75.102 | -0.276 | 9.886 | 1.00 | 28.92 |
| 24234 | O | HOH | W | 73 | -23.734 | -17.727 | 89.694 | 1.00 | 28.78 |
| 24235 | O | HOH | W | 74 | -61.665 | 13.073 | 82.553 | 1.00 | 23.56 |
| 24236 | O | HOH | W | 75 | -71.182 | -9.402 | 3.784 | 1.00 | 35.36 |
| 24237 | O | HOH | W | 76 | -24.540 | -4.350 | 67.423 | 1.00 | 43.77 |
| 24238 | O | HOH | W | 77 | -61.200 | -3.647 | 93.365 | 1.00 | 19.38 |
| 24239 | O | HOH | W | 78 | -121.220 | 15.557 | 20.341 | 1.00 | 39.85 |
| 24240 | O | HOH | W | 79 | -72.505 | 5.898 | 75.027 | 1.00 | 28.20 |
| 24241 | O | HOH | W | 80 | -53.615 | -1.972 | 65.458 | 1.00 | 25.36 |
| 24242 | O | HOH | W | 81 | -23.316 | 8.408 | 68.632 | 1.00 | 27.79 |
| 24243 | O | HOH | W | 82 | -40.295 | -8.810 | 86.500 | 1.00 | 19.14 |
| 24244 | O | HOH | W | 83 | -66.594 | -4.239 | 87.795 | 1.00 | 24.11 |
| 24245 | O | HOH | W | 84 | -75.182 | -13.009 | 69.585 | 1.00 | 18.25 |
| 24246 | O | HOH | W | 85 | -96.392 | -18.489 | 23.392 | 1.00 | 36.31 |
| 24247 | O | HOH | W | 86 | -112.774 | 15.956 | 26.499 | 1.00 | 26.80 |
| 24248 | O | HOH | W | 87 | -91.217 | -10.713 | 67.871 | 1.00 | 16.07 |
| 24249 | O | HOH | W | 88 | -12.985 | -15.845 | 110.350 | 1.00 | 29.91 |
| 24250 | O | HOH | W | 89 | -59.754 | -17.919 | 67.217 | 1.00 | 33.41 |
| 24251 | O | HOH | W | 90 | -87.120 | -23.809 | 79.247 | 1.00 | 25.99 |
| 24252 | O | HOH | W | 91 | -17.496 | -5.037 | 62.417 | 1.00 | 35.92 |
| 24253 | O | HOH | W | 92 | -82.662 | -5.201 | 21.440 | 1.00 | 28.79 |
| 24254 | O | HOH | W | 93 | -15.946 | -17.219 | 90.181 | 1.00 | 35.57 |
| 24255 | O | HOH | W | 94 | -106.041 | -23.904 | 32.595 | 1.00 | 27.36 |
| 24256 | O | HOH | W | 95 | -64.891 | -38.163 | 13.838 | 1.00 | 49.31 |
| 24257 | O | HOH | W | 96 | -68.673 | -3.377 | 89.485 | 1.00 | 28.59 |
| 24258 | O | HOH | W | 97 | -73.127 | 4.487 | 72.673 | 1.00 | 24.48 |
| 24259 | O | HOH | W | 98 | -75.506 | 0.140 | 23.056 | 1.00 | 30.81 |
| 24260 | O | HOH | W | 99 | -59.199 | 11.468 | 76.763 | 1.00 | 25.49 |
| 24261 | O | HOH | W | 100 | -66.041 | 3.566 | -5.385 | 1.00 | 33.28 |
| 24262 | O | HOH | W | 101 | -11.881 | 3.367 | 91.642 | 1.00 | 21.04 |
| 24263 | O | HOH | W | 102 | -85.203 | -18.621 | 66.788 | 1.00 | 27.38 |
| 24264 | O | HOH | W | 103 | -109.289 | 4.117 | 56.380 | 1.00 | 33.61 |
| 24265 | O | HOH | W | 104 | -106.928 | -5.336 | 50.716 | 1.00 | 28.54 |
| 24266 | O | HOH | W | 105 | -81.989 | -10.473 | 65.120 | 1.00 | 20.82 |

FIGURE 3 RH

| A | B | C | D | E | F | G | H | I | J |
|---|---|---|---|---|---:|---:|---:|---:|---:|
| 24267 | O | HOH | W | 106 | -41.840 | 13.381 | 94.446 | 1.00 | 35.97 |
| 24268 | O | HOH | W | 107 | -106.501 | -2.782 | 35.295 | 1.00 | 28.25 |
| 24269 | O | HOH | W | 108 | -72.388 | 10.526 | 80.061 | 1.00 | 31.33 |
| 24270 | O | HOH | W | 109 | -53.562 | 5.264 | 73.907 | 1.00 | 22.21 |
| 24271 | O | HOH | W | 110 | -57.971 | 6.214 | 86.387 | 1.00 | 23.64 |
| 24272 | O | HOH | W | 111 | -100.805 | -7.622 | 22.042 | 1.00 | 23.65 |
| 24273 | O | HOH | W | 112 | -48.478 | -3.003 | 92.083 | 1.00 | 23.36 |
| 24274 | O | HOH | W | 113 | -85.465 | -25.300 | 72.872 | 1.00 | 29.44 |
| 24275 | O | HOH | W | 114 | -20.282 | 8.882 | 79.786 | 1.00 | 35.92 |
| 24276 | O | HOH | W | 115 | -45.959 | 2.886 | 103.777 | 1.00 | 26.29 |
| 24277 | O | HOH | W | 116 | -36.141 | -11.677 | 74.345 | 1.00 | 28.93 |
| 24278 | O | HOH | W | 117 | -84.832 | -6.458 | 67.180 | 1.00 | 23.67 |
| 24279 | O | HOH | W | 118 | -110.885 | -3.063 | 36.123 | 1.00 | 17.59 |
| 24280 | O | HOH | W | 119 | -76.548 | 1.210 | 67.123 | 1.00 | 23.27 |
| 24281 | O | HOH | W | 120 | -90.282 | -6.048 | 52.777 | 1.00 | 21.84 |
| 24282 | O | HOH | W | 121 | -29.693 | 4.046 | 86.322 | 1.00 | 34.98 |
| 24283 | O | HOH | W | 122 | -28.902 | -9.734 | 109.602 | 1.00 | 31.65 |
| 24284 | O | HOH | W | 123 | -4.352 | -3.743 | 90.634 | 1.00 | 32.59 |
| 24285 | O | HOH | W | 124 | -91.781 | -4.447 | 83.572 | 1.00 | 25.21 |
| 24286 | O | HOH | W | 125 | -67.717 | -16.914 | 28.754 | 1.00 | 40.36 |
| 24287 | O | HOH | W | 126 | -119.211 | 0.651 | 53.546 | 1.00 | 26.42 |
| 24288 | O | HOH | W | 127 | -91.301 | -28.429 | 34.790 | 1.00 | 40.78 |
| 24289 | O | HOH | W | 128 | -76.632 | -4.861 | 41.174 | 1.00 | 30.89 |
| 24290 | O | HOH | W | 129 | -99.483 | 0.770 | 31.171 | 1.00 | 21.46 |
| 24291 | O | HOH | W | 130 | -40.577 | 25.458 | 71.322 | 1.00 | 31.89 |
| 24292 | O | HOH | W | 131 | -54.460 | -3.811 | 88.792 | 1.00 | 26.57 |
| 24293 | O | HOH | W | 132 | -73.347 | -26.780 | 96.594 | 1.00 | 25.31 |
| 24294 | O | HOH | W | 133 | -101.846 | -12.191 | 22.857 | 1.00 | 29.80 |
| 24295 | O | HOH | W | 134 | -13.225 | -4.460 | 115.839 | 1.00 | 40.97 |
| 24296 | O | HOH | W | 135 | -68.912 | -5.769 | 86.997 | 1.00 | 22.23 |
| 24297 | O | HOH | W | 136 | -22.275 | 9.258 | 67.096 | 1.00 | 30.00 |
| 24298 | O | HOH | W | 137 | -44.839 | -3.193 | 88.802 | 1.00 | 24.93 |
| 24299 | O | HOH | W | 138 | -65.755 | -7.053 | 37.884 | 1.00 | 28.79 |
| 24300 | O | HOH | W | 139 | -58.404 | -6.772 | 87.209 | 1.00 | 23.49 |
| 24301 | O | HOH | W | 140 | -80.628 | -9.548 | 77.028 | 1.00 | 24.08 |
| 24302 | O | HOH | W | 141 | -99.414 | 17.192 | 45.081 | 1.00 | 30.93 |
| 24303 | O | HOH | W | 142 | -25.663 | 9.914 | 92.244 | 1.00 | 34.26 |
| 24304 | O | HOH | W | 143 | -36.543 | -4.504 | 86.323 | 1.00 | 26.15 |
| 24305 | O | HOH | W | 144 | -50.670 | -5.118 | 86.081 | 1.00 | 28.13 |
| 24306 | O | HOH | W | 145 | -14.817 | 1.884 | 76.189 | 1.00 | 31.05 |
| 24307 | O | HOH | W | 146 | -90.085 | 4.557 | 31.021 | 1.00 | 23.04 |
| 24308 | O | HOH | W | 147 | -92.788 | -23.311 | 32.998 | 1.00 | 35.23 |
| 24309 | O | HOH | W | 148 | -73.899 | -11.308 | 78.406 | 1.00 | 20.27 |
| 24310 | O | HOH | W | 149 | -44.776 | -13.606 | 80.500 | 1.00 | 26.73 |
| 24311 | O | HOH | W | 150 | -82.733 | -15.307 | 90.077 | 1.00 | 52.62 |
| 24312 | O | HOH | W | 151 | -27.565 | -1.561 | 63.745 | 1.00 | 37.01 |
| 24313 | O | HOH | W | 152 | -59.931 | -24.626 | 91.317 | 1.00 | 27.37 |
| 24314 | O | HOH | W | 153 | -48.630 | -13.831 | 69.969 | 1.00 | 25.35 |
| 24315 | O | HOH | W | 154 | -56.434 | -22.590 | 87.803 | 1.00 | 28.54 |
| 24316 | O | HOH | W | 155 | -97.391 | 5.405 | 41.148 | 1.00 | 28.63 |
| 24317 | O | HOH | W | 156 | -111.072 | 13.637 | 28.834 | 1.00 | 29.36 |

FIGURE 3 RI

| A | B | C | D | E | F | G | H | I | J |
|---|---|---|---|---|---|---|---|---|---|
| 24318 | O | HOH | W | 157 | -70.170 | -26.212 | 93.886 | 1.00 | 21.97 |
| 24319 | O | HOH | W | 158 | -40.421 | -9.872 | 83.798 | 1.00 | 25.90 |
| 24320 | O | HOH | W | 159 | -124.981 | -6.802 | 54.015 | 1.00 | 32.00 |
| 24321 | O | HOH | W | 160 | -14.089 | 3.959 | 80.977 | 1.00 | 28.94 |
| 24322 | O | HOH | W | 161 | -75.785 | -11.368 | 76.575 | 1.00 | 16.09 |
| 24323 | O | HOH | W | 162 | -85.426 | -18.016 | 6.302 | 1.00 | 35.99 |
| 24324 | O | HOH | W | 163 | -79.395 | 2.382 | 31.405 | 1.00 | 35.95 |
| 24325 | O | HOH | W | 164 | -80.145 | 2.786 | 36.094 | 1.00 | 28.98 |
| 24326 | O | HOH | W | 165 | -54.849 | -0.234 | 3.626 | 1.00 | 52.60 |
| 24327 | O | HOH | W | 166 | -106.634 | -5.311 | 26.057 | 1.00 | 27.44 |
| 24328 | O | HOH | W | 167 | -62.637 | 0.167 | 91.371 | 1.00 | 24.04 |
| 24329 | O | HOH | W | 168 | -72.863 | 22.007 | 67.554 | 1.00 | 38.64 |
| 24330 | O | HOH | W | 169 | -114.985 | 13.055 | 45.357 | 1.00 | 40.11 |
| 24331 | O | HOH | W | 170 | -71.027 | -10.565 | 83.882 | 1.00 | 39.02 |
| 24332 | O | HOH | W | 171 | -71.902 | -4.399 | 21.029 | 1.00 | 31.18 |
| 24333 | O | HOH | W | 172 | -48.422 | 1.924 | 102.299 | 1.00 | 32.51 |
| 24334 | O | HOH | W | 173 | -48.339 | -3.859 | 75.038 | 1.00 | 24.54 |
| 24335 | O | HOH | W | 174 | -107.907 | -2.609 | 32.422 | 1.00 | 22.99 |
| 24336 | O | HOH | W | 175 | -104.620 | -18.098 | 43.567 | 1.00 | 35.88 |
| 24337 | O | HOH | W | 176 | -90.642 | 0.177 | 20.961 | 1.00 | 22.61 |
| 24338 | O | HOH | W | 177 | -110.363 | 10.007 | 42.496 | 1.00 | 33.78 |
| 24339 | O | HOH | W | 178 | -85.410 | -18.015 | 73.273 | 1.00 | 17.91 |
| 24340 | O | HOH | W | 179 | -57.482 | 7.441 | 93.816 | 1.00 | 23.43 |
| 24341 | O | HOH | W | 180 | -35.275 | -15.110 | 99.309 | 1.00 | 32.53 |
| 24342 | O | HOH | W | 181 | -12.734 | -3.318 | 78.965 | 1.00 | 34.77 |
| 24343 | O | HOH | W | 182 | -118.291 | 5.612 | 43.221 | 1.00 | 24.78 |
| 24344 | O | HOH | W | 183 | -58.998 | -24.547 | 94.104 | 1.00 | 39.07 |
| 24345 | O | HOH | W | 184 | -68.221 | 4.700 | 81.326 | 1.00 | 21.62 |
| 24346 | O | HOH | W | 185 | -55.744 | -25.024 | 77.689 | 1.00 | 38.78 |
| 24347 | O | HOH | W | 186 | -51.734 | -8.919 | 92.077 | 1.00 | 24.62 |
| 24348 | O | HOH | W | 187 | -59.944 | 8.112 | 87.649 | 1.00 | 32.98 |
| 24349 | O | HOH | W | 188 | -76.414 | -19.148 | 58.805 | 1.00 | 46.32 |
| 24350 | O | HOH | W | 189 | -50.989 | 14.314 | 75.971 | 1.00 | 34.01 |
| 24351 | O | HOH | W | 190 | 1.782 | 15.783 | 87.688 | 1.00 | 56.92 |
| 24352 | O | HOH | W | 191 | -74.202 | -3.438 | 22.570 | 1.00 | 29.82 |
| 24353 | O | HOH | W | 192 | -32.236 | 1.525 | 89.838 | 1.00 | 25.96 |
| 24354 | O | HOH | W | 193 | -75.647 | 0.161 | 28.354 | 1.00 | 29.82 |
| 24355 | O | HOH | W | 194 | -92.262 | -14.808 | 91.578 | 1.00 | 30.64 |
| 24356 | O | HOH | W | 195 | -83.298 | -11.345 | 4.255 | 1.00 | 38.28 |
| 24357 | O | HOH | W | 196 | -37.338 | 3.161 | 59.048 | 1.00 | 20.67 |
| 24358 | O | HOH | W | 197 | -59.182 | -7.885 | 99.202 | 1.00 | 36.33 |
| 24359 | O | HOH | W | 198 | -30.676 | 15.551 | 78.119 | 1.00 | 28.90 |
| 24360 | O | HOH | W | 199 | -77.000 | -8.976 | 77.246 | 1.00 | 30.29 |
| 24361 | O | HOH | W | 200 | -62.592 | -2.234 | 91.528 | 1.00 | 22.49 |
| 24362 | O | HOH | W | 201 | -84.788 | -15.542 | 74.412 | 1.00 | 22.56 |
| 24363 | O | HOH | W | 202 | -75.385 | -10.834 | 68.001 | 1.00 | 24.89 |
| 24364 | O | HOH | W | 203 | -77.662 | -8.241 | 26.170 | 1.00 | 21.16 |
| 24365 | O | HOH | W | 204 | -64.771 | 1.570 | 90.052 | 1.00 | 33.62 |
| 24366 | O | HOH | W | 205 | -81.699 | -10.155 | 47.063 | 1.00 | 36.98 |
| 24367 | O | HOH | W | 206 | -20.231 | -36.910 | 75.605 | 1.00 | 36.29 |
| 24368 | O | HOH | W | 207 | -25.961 | -27.837 | 99.022 | 1.00 | 38.88 |

FIGURE 3 RJ

| A | B | C | D | E | F | G | H | I | J |
|---|---|---|---|---|---|---|---|---|---|
| 24369 | O | HOH | W | 208 | -96.006 | -14.048 | 18.095 | 1.00 | 28.04 |
| 24370 | O | HOH | W | 209 | -58.469 | 5.269 | 93.487 | 1.00 | 23.13 |
| 24371 | O | HOH | W | 210 | -74.325 | -6.822 | 68.883 | 1.00 | 20.73 |
| 24372 | O | HOH | W | 211 | -89.567 | -12.790 | 68.569 | 1.00 | 25.44 |
| 24373 | O | HOH | W | 212 | -37.674 | 0.666 | 58.639 | 1.00 | 25.90 |
| 24374 | O | HOH | W | 213 | -68.643 | -16.312 | 26.182 | 1.00 | 34.79 |
| 24375 | O | HOH | W | 214 | -30.927 | 5.755 | 102.928 | 1.00 | 32.95 |
| 24376 | O | HOH | W | 215 | -79.481 | -1.250 | 35.367 | 1.00 | 26.75 |
| 24377 | O | HOH | W | 216 | -92.377 | -0.377 | 25.088 | 1.00 | 25.39 |
| 24378 | O | HOH | W | 217 | -83.520 | -15.613 | 70.403 | 1.00 | 24.33 |
| 24379 | O | HOH | W | 218 | -72.696 | -23.309 | 102.427 | 1.00 | 27.73 |
| 24380 | O | HOH | W | 219 | -77.396 | -4.105 | -0.654 | 1.00 | 32.28 |
| 24381 | O | HOH | W | 220 | -117.083 | -11.246 | 50.304 | 1.00 | 31.59 |
| 24382 | O | HOH | W | 221 | -97.187 | -16.296 | 65.596 | 1.00 | 36.87 |
| 24383 | O | HOH | W | 222 | -85.942 | -11.587 | 45.311 | 1.00 | 26.63 |
| 24384 | O | HOH | W | 223 | -41.219 | -10.073 | 88.257 | 1.00 | 19.26 |
| 24385 | O | HOH | W | 224 | -77.785 | -29.179 | 76.237 | 1.00 | 27.76 |
| 24386 | O | HOH | W | 225 | -55.141 | -17.302 | 92.534 | 1.00 | 36.22 |
| 24387 | O | HOH | W | 226 | -89.051 | -3.976 | 58.563 | 1.00 | 31.85 |
| 24388 | O | HOH | W | 227 | -133.159 | 5.245 | 4.407 | 1.00 | 35.71 |
| 24389 | O | HOH | W | 228 | -64.438 | -15.995 | 30.706 | 1.00 | 31.36 |
| 24390 | O | HOH | W | 229 | -95.735 | -25.318 | 29.954 | 1.00 | 34.97 |
| 24391 | O | HOH | W | 230 | -73.488 | -8.008 | 80.339 | 1.00 | 34.43 |
| 24392 | O | HOH | W | 231 | -111.130 | -3.552 | 40.809 | 1.00 | 23.31 |
| 24393 | O | HOH | W | 232 | -110.233 | -1.951 | 33.979 | 1.00 | 21.17 |
| 24394 | O | HOH | W | 233 | -114.918 | 6.101 | 34.185 | 1.00 | 22.47 |
| 24395 | O | HOH | W | 234 | -122.726 | -5.394 | 51.238 | 1.00 | 26.82 |
| 24396 | O | HOH | W | 235 | -122.574 | -1.404 | 39.114 | 1.00 | 40.17 |
| 24397 | O | HOH | W | 236 | -73.267 | -25.867 | 81.292 | 1.00 | 29.46 |
| 24398 | O | HOH | W | 237 | -84.409 | -1.101 | 26.394 | 1.00 | 29.29 |
| 24399 | O | HOH | W | 238 | -91.341 | -16.988 | 84.578 | 1.00 | 25.96 |
| 24400 | O | HOH | W | 239 | -39.470 | -12.050 | 73.075 | 1.00 | 37.03 |
| 24401 | O | HOH | W | 240 | -2.061 | -8.117 | 106.954 | 1.00 | 34.50 |
| 24402 | O | HOH | W | 241 | -59.827 | -16.337 | 6.625 | 1.00 | 34.16 |
| 24403 | O | HOH | W | 242 | -87.331 | 4.980 | 43.006 | 1.00 | 39.82 |
| 24404 | O | HOH | W | 243 | -96.863 | -28.277 | 33.742 | 1.00 | 44.85 |
| 24405 | O | HOH | W | 244 | -104.593 | -13.702 | 41.488 | 1.00 | 19.51 |
| 24406 | O | HOH | W | 245 | -73.417 | -11.509 | 83.254 | 1.00 | 26.05 |
| 24407 | O | HOH | W | 246 | -75.722 | 2.349 | 69.359 | 1.00 | 29.25 |
| 24408 | O | HOH | W | 247 | -24.578 | 1.538 | 70.024 | 1.00 | 39.78 |
| 24409 | O | HOH | W | 248 | -46.998 | -3.845 | 101.005 | 1.00 | 32.06 |
| 24410 | O | HOH | W | 249 | -92.617 | -13.851 | 9.018 | 1.00 | 42.28 |
| 24411 | O | HOH | W | 250 | -61.764 | -8.020 | 59.987 | 1.00 | 26.98 |
| 24412 | O | HOH | W | 251 | -100.091 | 14.397 | 26.529 | 1.00 | 33.05 |
| 24413 | O | HOH | W | 252 | -42.633 | -6.822 | 68.502 | 1.00 | 24.40 |
| 24414 | O | HOH | W | 253 | -7.181 | 8.932 | 64.612 | 1.00 | 53.64 |
| 24415 | O | HOH | W | 254 | -27.720 | 14.073 | 82.527 | 1.00 | 30.70 |
| 24416 | O | HOH | W | 255 | -24.177 | 14.802 | 60.014 | 1.00 | 34.48 |
| 24417 | O | HOH | W | 256 | -119.569 | -12.532 | 51.495 | 1.00 | 34.93 |
| 24418 | O | HOH | W | 257 | -79.324 | -19.664 | 11.988 | 1.00 | 34.52 |
| 24419 | O | HOH | W | 258 | -23.137 | 8.077 | 85.725 | 1.00 | 30.90 |

FIGURE 3 RK

| A | B | C | D | E | F | G | H | I | J |
|---|---|---|---|---|---|---|---|---|---|
| 24420 | O | HOH | W | 259 | -112.359 | -5.953 | 39.910 | 1.00 | 23.57 |
| 24421 | O | HOH | W | 260 | -87.105 | -12.094 | 63.902 | 1.00 | 34.92 |
| 24422 | O | HOH | W | 261 | -62.976 | 1.555 | 93.915 | 1.00 | 36.04 |
| 24423 | O | HOH | W | 262 | -53.812 | -0.539 | 59.667 | 1.00 | 37.46 |
| 24424 | O | HOH | W | 263 | -34.031 | -2.761 | 87.089 | 1.00 | 29.06 |
| 24425 | O | HOH | W | 264 | -6.705 | -3.338 | 96.833 | 1.00 | 39.74 |
| 24426 | O | HOH | W | 265 | -74.896 | 5.360 | 95.271 | 1.00 | 56.40 |
| 24427 | O | HOH | W | 266 | -59.460 | -24.880 | 84.398 | 1.00 | 40.62 |
| 24428 | O | HOH | W | 267 | -76.631 | -8.476 | 69.740 | 1.00 | 26.98 |
| 24429 | O | HOH | W | 268 | -89.995 | -1.453 | 18.972 | 1.00 | 30.42 |
| 24430 | O | HOH | W | 269 | -32.602 | -12.208 | 2.518 | 1.00 | 61.33 |
| 24431 | O | HOH | W | 270 | -77.030 | -19.598 | 85.298 | 1.00 | 19.19 |
| 24432 | O | HOH | W | 271 | -41.014 | -1.534 | 63.232 | 1.00 | 27.69 |
| 24433 | O | HOH | W | 272 | -10.257 | -6.964 | 64.268 | 1.00 | 45.43 |
| 24434 | O | HOH | W | 273 | -100.633 | 14.121 | 46.413 | 1.00 | 22.88 |
| 24435 | O | HOH | W | 274 | -90.144 | 6.000 | 42.386 | 1.00 | 26.82 |
| 24436 | O | HOH | W | 275 | -43.139 | -10.647 | 75.949 | 1.00 | 41.26 |
| 24437 | O | HOH | W | 276 | -79.138 | -27.021 | 101.715 | 1.00 | 38.78 |
| 24438 | O | HOH | W | 277 | -90.782 | -17.156 | 28.326 | 1.00 | 24.37 |
| 24439 | O | HOH | W | 278 | -119.652 | -0.976 | 45.322 | 1.00 | 29.90 |
| 24440 | O | HOH | W | 279 | -56.269 | -8.617 | 86.422 | 1.00 | 24.42 |
| 24441 | O | HOH | W | 280 | -121.228 | -17.863 | 25.690 | 1.00 | 42.06 |
| 24442 | O | HOH | W | 281 | -83.963 | -10.204 | 47.551 | 1.00 | 29.91 |
| 24443 | O | HOH | W | 282 | -106.283 | -7.787 | 25.072 | 1.00 | 19.72 |
| 24444 | O | HOH | W | 283 | -26.442 | 5.106 | 111.640 | 1.00 | 26.93 |
| 24445 | O | HOH | W | 284 | -30.160 | -24.628 | 79.920 | 1.00 | 31.03 |
| 24446 | O | HOH | W | 285 | -53.610 | 11.401 | 97.883 | 1.00 | 33.98 |
| 24447 | O | HOH | W | 286 | -83.509 | 1.590 | 42.769 | 1.00 | 26.82 |
| 24448 | O | HOH | W | 287 | -87.278 | -6.046 | 78.528 | 1.00 | 52.68 |
| 24449 | O | HOH | W | 288 | -72.847 | 5.572 | -1.336 | 1.00 | 40.58 |
| 24450 | O | HOH | W | 289 | -111.385 | -17.904 | 9.313 | 1.00 | 42.55 |
| 24451 | O | HOH | W | 290 | -41.612 | -8.792 | 66.548 | 1.00 | 33.68 |
| 24452 | O | HOH | W | 291 | -56.140 | 16.815 | 76.688 | 1.00 | 32.39 |
| 24453 | O | HOH | W | 292 | -111.586 | -16.824 | 12.088 | 1.00 | 37.33 |
| 24454 | O | HOH | W | 293 | -63.913 | -12.750 | 109.046 | 1.00 | 39.21 |
| 24455 | O | HOH | W | 294 | -52.563 | -15.484 | 82.996 | 1.00 | 24.79 |
| 24456 | O | HOH | W | 295 | -74.928 | -10.977 | 81.127 | 1.00 | 25.93 |
| 24457 | O | HOH | W | 296 | -71.856 | -3.869 | 0.862 | 1.00 | 39.40 |
| 24458 | O | HOH | W | 297 | -92.388 | 7.474 | 22.287 | 1.00 | 36.88 |
| 24459 | O | HOH | W | 298 | -113.255 | -22.248 | 37.416 | 1.00 | 32.99 |
| 24460 | O | HOH | W | 299 | -56.624 | -21.871 | 66.601 | 1.00 | 62.21 |
| 24461 | O | HOH | W | 300 | -69.526 | -9.432 | 19.901 | 1.00 | 42.19 |
| 24462 | O | HOH | W | 301 | -85.865 | 7.711 | 63.285 | 1.00 | 42.58 |
| 24463 | O | HOH | W | 302 | -91.267 | -14.271 | 84.352 | 1.00 | 26.57 |
| 24464 | O | HOH | W | 303 | -95.271 | 15.524 | 82.843 | 1.00 | 40.52 |
| 24465 | O | HOH | W | 304 | -109.080 | -5.733 | 48.972 | 1.00 | 21.15 |
| 24466 | O | HOH | W | 305 | -19.924 | -6.058 | 62.090 | 1.00 | 33.77 |
| 24467 | O | HOH | W | 306 | -131.353 | -12.524 | 54.607 | 1.00 | 39.97 |
| 24468 | O | HOH | W | 307 | -82.761 | -15.268 | 82.570 | 1.00 | 22.77 |
| 24469 | O | HOH | W | 308 | -120.711 | -19.867 | 51.546 | 1.00 | 29.54 |
| 24470 | O | HOH | W | 309 | -100.641 | -16.744 | 72.476 | 1.00 | 36.27 |

FIGURE 3 RL

| A | B | C | D | E | F | G | H | I | J |
|---|---|---|---|---|---|---|---|---|---|
| 24471 | O | HOH | W | 310 | -80.240 | -17.209 | 39.758 | 1.00 | 33.90 |
| 24472 | O | HOH | W | 311 | -31.708 | -9.641 | 95.238 | 1.00 | 29.12 |
| 24473 | O | HOH | W | 312 | -83.814 | -16.154 | 5.680 | 1.00 | 53.05 |
| 24474 | O | HOH | W | 313 | -37.232 | -6.563 | 80.302 | 1.00 | 36.17 |
| 24475 | O | HOH | W | 314 | -70.622 | -1.977 | 88.167 | 1.00 | 27.88 |
| 24476 | O | HOH | W | 315 | -84.119 | -4.252 | 74.137 | 1.00 | 31.96 |
| 24477 | O | HOH | W | 316 | -77.295 | -10.541 | 81.836 | 1.00 | 32.42 |
| 24478 | O | HOH | W | 317 | -101.238 | -14.498 | 72.963 | 1.00 | 45.28 |
| 24479 | O | HOH | W | 318 | -24.754 | 5.854 | 86.018 | 1.00 | 31.66 |
| 24480 | O | HOH | W | 319 | -73.523 | -10.444 | 44.877 | 1.00 | 29.80 |
| 24481 | O | HOH | W | 320 | -59.557 | 13.895 | 78.345 | 1.00 | 26.20 |
| 24482 | O | HOH | W | 321 | -109.292 | -3.190 | 47.869 | 1.00 | 23.62 |
| 24483 | O | HOH | W | 322 | -91.160 | -8.045 | 54.116 | 1.00 | 23.32 |
| 24484 | O | HOH | W | 323 | -25.913 | 8.917 | 82.854 | 1.00 | 29.76 |
| 24485 | O | HOH | W | 324 | -45.682 | -7.725 | 76.713 | 1.00 | 28.57 |
| 24486 | O | HOH | W | 325 | -29.382 | 0.836 | 55.856 | 1.00 | 39.66 |
| 24487 | O | HOH | W | 326 | -32.152 | -26.155 | 78.159 | 1.00 | 37.39 |
| 24488 | O | HOH | W | 327 | -114.146 | 5.928 | 52.894 | 1.00 | 33.72 |
| 24489 | O | HOH | W | 328 | -78.027 | -8.774 | 43.048 | 1.00 | 21.47 |
| 24490 | O | HOH | W | 329 | -124.215 | 5.256 | 39.406 | 1.00 | 37.84 |
| 24491 | O | HOH | W | 330 | -114.276 | -0.923 | 34.147 | 1.00 | 29.79 |
| 24492 | O | HOH | W | 331 | -86.349 | -13.850 | 81.041 | 1.00 | 34.32 |
| 24493 | O | HOH | W | 332 | -48.933 | 4.882 | 102.460 | 1.00 | 25.22 |
| 24494 | O | HOH | W | 333 | -144.631 | 1.048 | 44.554 | 1.00 | 40.54 |
| 24495 | O | HOH | W | 334 | -78.844 | -2.914 | 102.492 | 1.00 | 34.39 |
| 24496 | O | HOH | W | 335 | -82.073 | -8.908 | 53.475 | 1.00 | 34.72 |
| 24497 | O | HOH | W | 336 | -132.571 | -12.045 | 51.216 | 1.00 | 43.39 |
| 24498 | O | HOH | W | 337 | -113.484 | 15.595 | 18.318 | 1.00 | 43.50 |
| 24499 | O | HOH | W | 338 | -80.286 | 5.452 | 15.760 | 1.00 | 42.84 |
| 24500 | O | HOH | W | 339 | -94.063 | 4.582 | 23.976 | 1.00 | 23.62 |
| 24501 | O | HOH | W | 340 | -123.795 | 9.308 | 48.657 | 1.00 | 34.25 |
| 24502 | O | HOH | W | 341 | -8.269 | -4.453 | 84.606 | 1.00 | 44.86 |
| 24503 | O | HOH | W | 342 | -137.812 | -28.700 | 21.377 | 1.00 | 49.37 |
| 24504 | O | HOH | W | 343 | -70.782 | -7.957 | 90.513 | 1.00 | 23.76 |
| 24505 | O | HOH | W | 344 | -51.640 | -3.177 | 62.800 | 1.00 | 28.14 |
| 24506 | O | HOH | W | 345 | -107.294 | 19.998 | 28.517 | 1.00 | 34.16 |
| 24507 | O | HOH | W | 346 | -75.391 | -31.741 | 89.888 | 1.00 | 34.52 |
| 24508 | O | HOH | W | 347 | -28.729 | 4.880 | 89.134 | 1.00 | 29.64 |
| 24509 | O | HOH | W | 348 | -94.866 | 8.220 | 22.666 | 1.00 | 37.15 |
| 24510 | O | HOH | W | 349 | -47.619 | 5.635 | 68.767 | 1.00 | 31.79 |
| 24511 | O | HOH | W | 350 | -32.001 | -5.017 | 90.310 | 1.00 | 28.26 |
| 24512 | O | HOH | W | 351 | -117.983 | -20.729 | 54.852 | 1.00 | 39.53 |
| 24513 | O | HOH | W | 352 | -45.251 | 5.119 | 19.195 | 1.00 | 47.31 |
| 24514 | O | HOH | W | 353 | -93.949 | -1.603 | 27.037 | 1.00 | 28.43 |
| 24515 | O | HOH | W | 354 | 11.481 | 9.358 | 86.657 | 1.00 | 48.62 |
| 24516 | O | HOH | W | 355 | -60.019 | 14.574 | 67.773 | 1.00 | 47.66 |
| 24517 | O | HOH | W | 356 | -45.557 | -15.018 | 78.497 | 1.00 | 25.05 |
| 24518 | O | HOH | W | 357 | -76.943 | -0.688 | 70.818 | 1.00 | 40.91 |
| 24519 | O | HOH | W | 358 | -60.725 | -1.346 | 55.724 | 1.00 | 44.13 |
| 24520 | O | HOH | W | 359 | -90.931 | -11.002 | 62.749 | 1.00 | 37.87 |
| 24521 | O | HOH | W | 360 | -103.687 | 19.110 | 45.842 | 1.00 | 40.74 |

FIGURE 3 RM

| A | B | C | D | E | F | G | H | I | J |
|---|---|---|---|---|---:|---:|---:|---:|---:|
| 24522 | O | HOH | W | 361 | -103.447 | 1.555 | 58.425 | 1.00 | 44.32 |
| 24523 | O | HOH | W | 362 | -62.424 | -33.596 | 14.361 | 1.00 | 42.09 |
| 24524 | O | HOH | W | 363 | -142.610 | 6.528 | 48.843 | 1.00 | 35.58 |
| 24525 | O | HOH | W | 364 | -50.711 | -7.054 | 8.397 | 1.00 | 49.26 |
| 24526 | O | HOH | W | 365 | -32.087 | -3.255 | 68.786 | 1.00 | 29.39 |
| 24527 | O | HOH | W | 366 | -78.082 | 0.405 | 23.933 | 1.00 | 31.59 |
| 24528 | O | HOH | W | 367 | -30.102 | 14.289 | 80.546 | 1.00 | 28.45 |
| 24529 | O | HOH | W | 368 | -84.631 | -31.154 | 102.920 | 1.00 | 45.04 |
| 24530 | O | HOH | W | 369 | -73.753 | -25.119 | 77.110 | 1.00 | 23.89 |
| 24531 | O | HOH | W | 370 | -30.399 | 14.616 | 102.905 | 1.00 | 46.03 |
| 24532 | O | HOH | W | 371 | -46.946 | 22.032 | 80.247 | 1.00 | 28.87 |
| 24533 | O | HOH | W | 372 | -86.341 | 13.219 | 86.877 | 1.00 | 47.17 |
| 24534 | O | HOH | W | 373 | -19.006 | -2.210 | 116.881 | 1.00 | 33.56 |
| 24535 | O | HOH | W | 374 | -76.017 | -7.389 | 42.389 | 1.00 | 31.21 |
| 24536 | O | HOH | W | 375 | -66.602 | -6.591 | 17.190 | 1.00 | 38.69 |
| 24537 | O | HOH | W | 376 | -88.752 | -13.509 | 66.146 | 1.00 | 32.00 |
| 24538 | O | HOH | W | 377 | -55.062 | -14.282 | 90.703 | 1.00 | 26.99 |
| 24539 | O | HOH | W | 378 | -78.048 | -9.519 | 45.392 | 1.00 | 24.96 |
| 24540 | O | HOH | W | 379 | -46.272 | -14.689 | 60.543 | 1.00 | 46.39 |
| 24541 | O | HOH | W | 380 | -104.895 | 17.465 | 31.690 | 1.00 | 52.28 |
| 24542 | O | HOH | W | 381 | -90.097 | -5.431 | 81.500 | 1.00 | 29.16 |
| 24543 | O | HOH | W | 382 | -35.670 | -1.759 | 75.500 | 1.00 | 33.60 |
| 24544 | O | HOH | W | 383 | -27.003 | 8.111 | 68.489 | 1.00 | 29.54 |
| 24545 | O | HOH | W | 384 | -115.888 | -9.266 | 25.040 | 1.00 | 38.52 |
| 24546 | O | HOH | W | 385 | -27.613 | -1.659 | 68.433 | 1.00 | 34.39 |
| 24547 | O | HOH | W | 386 | -71.527 | -25.637 | 101.416 | 1.00 | 36.97 |
| 24548 | O | HOH | W | 387 | -140.064 | 9.912 | 23.260 | 1.00 | 42.90 |
| 24549 | O | HOH | W | 388 | -40.301 | -8.785 | 104.462 | 1.00 | 40.87 |
| 24550 | O | HOH | W | 389 | -64.273 | 1.125 | 23.882 | 1.00 | 39.29 |
| 24551 | O | HOH | W | 390 | -92.220 | -5.490 | 23.328 | 1.00 | 25.87 |
| 24552 | O | HOH | W | 391 | -34.229 | 1.672 | 112.166 | 1.00 | 32.95 |
| 24553 | O | HOH | W | 392 | -4.121 | -6.162 | 88.781 | 1.00 | 46.28 |
| 24554 | O | HOH | W | 393 | -55.972 | -24.423 | 84.033 | 1.00 | 48.43 |
| 24555 | O | HOH | W | 394 | -56.995 | 8.367 | 70.948 | 1.00 | 29.49 |
| 24556 | O | HOH | W | 395 | -126.333 | -7.814 | 37.963 | 1.00 | 37.37 |
| 24557 | O | HOH | W | 396 | -48.948 | 3.852 | 66.990 | 1.00 | 37.01 |
| 24558 | O | HOH | W | 397 | -46.749 | -1.825 | 90.667 | 1.00 | 27.00 |
| 24559 | O | HOH | W | 398 | -106.804 | 0.856 | 6.978 | 1.00 | 47.53 |
| 24560 | O | HOH | W | 399 | -66.287 | -18.360 | 33.203 | 1.00 | 36.53 |
| 24561 | O | HOH | W | 400 | -61.116 | -8.337 | 36.977 | 1.00 | 45.12 |
| 24562 | O | HOH | W | 401 | -96.847 | -20.236 | 62.448 | 1.00 | 49.72 |
| 24563 | O | HOH | W | 402 | -27.539 | -32.416 | 74.701 | 1.00 | 45.14 |
| 24564 | O | HOH | W | 403 | -27.859 | 8.977 | 87.605 | 1.00 | 23.08 |
| 24565 | O | HOH | W | 404 | -113.552 | -6.130 | 38.217 | 1.00 | 34.04 |
| 24566 | O | HOH | W | 405 | -41.959 | 22.786 | 70.496 | 1.00 | 27.28 |
| 24567 | O | HOH | W | 406 | -43.248 | 24.044 | 98.232 | 1.00 | 47.89 |
| 24568 | O | HOH | W | 407 | -98.090 | 3.948 | 48.778 | 1.00 | 36.98 |
| 24569 | O | HOH | W | 408 | -117.722 | -1.339 | 49.192 | 1.00 | 33.13 |
| 24570 | O | HOH | W | 409 | -97.186 | 23.891 | 38.877 | 1.00 | 37.04 |
| 24571 | O | HOH | W | 410 | -54.077 | -21.256 | 87.483 | 1.00 | 31.67 |
| 24572 | O | HOH | W | 411 | -26.540 | -7.257 | 58.482 | 1.00 | 35.63 |

FIGURE 3 RN

| A | B | C | D | E | F | G | H | I | J |
|---|---|---|---|---|---|---|---|---|---|
| 24573 | O | HOH | W | 412 | -59.189 | 15.902 | 76.884 | 1.00 | 28.37 |
| 24574 | O | HOH | W | 413 | -106.052 | -19.912 | 38.113 | 1.00 | 37.83 |
| 24575 | O | HOH | W | 414 | -38.457 | -5.391 | 64.442 | 1.00 | 36.51 |
| 24576 | O | HOH | W | 415 | -81.281 | -16.478 | 41.821 | 1.00 | 28.20 |
| 24577 | O | HOH | W | 416 | -62.592 | 15.864 | 83.338 | 1.00 | 41.79 |
| 24578 | O | HOH | W | 417 | -90.440 | -7.959 | 81.659 | 1.00 | 33.84 |
| 24579 | O | HOH | W | 418 | -109.276 | -4.084 | 65.347 | 1.00 | 45.60 |
| 24580 | O | HOH | W | 419 | -69.006 | -12.524 | 47.891 | 1.00 | 34.51 |
| 24581 | O | HOH | W | 420 | -61.674 | 13.685 | 79.885 | 1.00 | 22.82 |
| 24582 | O | HOH | W | 421 | -77.977 | 6.047 | 70.046 | 1.00 | 24.17 |
| 24583 | O | HOH | W | 422 | -79.914 | -36.956 | 84.165 | 1.00 | 44.36 |
| 24584 | O | HOH | W | 423 | -75.416 | -3.338 | 43.412 | 1.00 | 28.37 |
| 24585 | O | HOH | W | 424 | -18.933 | 12.928 | 89.742 | 1.00 | 25.94 |
| 24586 | O | HOH | W | 425 | -94.178 | 3.382 | 47.428 | 1.00 | 36.17 |
| 24587 | O | HOH | W | 426 | -52.330 | 5.800 | 71.979 | 1.00 | 21.85 |
| 24588 | O | HOH | W | 427 | -88.551 | -11.856 | 14.969 | 1.00 | 34.68 |
| 24589 | O | HOH | W | 428 | -85.645 | -17.986 | 37.895 | 1.00 | 33.59 |
| 24590 | O | HOH | W | 429 | -132.669 | -7.587 | 47.834 | 1.00 | 36.03 |
| 24591 | O | HOH | W | 430 | -108.763 | -1.321 | 24.408 | 1.00 | 28.53 |
| 24592 | O | HOH | W | 431 | -88.217 | -9.065 | 82.661 | 1.00 | 30.48 |
| 24593 | O | HOH | W | 432 | -56.817 | -21.493 | 13.134 | 1.00 | 42.34 |
| 24594 | O | HOH | W | 433 | -85.022 | 5.402 | 37.016 | 1.00 | 28.68 |
| 24595 | O | HOH | W | 434 | -73.814 | -5.264 | 66.747 | 1.00 | 21.12 |
| 24596 | O | HOH | W | 435 | -28.261 | 13.058 | 71.895 | 1.00 | 30.19 |
| 24597 | O | HOH | W | 436 | -28.806 | 16.105 | 86.546 | 1.00 | 23.64 |
| 24598 | O | HOH | W | 437 | -67.417 | -16.186 | 93.767 | 1.00 | 23.93 |
| 24599 | O | HOH | W | 438 | -48.439 | -5.879 | 87.312 | 1.00 | 25.91 |
| 24600 | O | HOH | W | 439 | -64.299 | -28.634 | 72.041 | 1.00 | 33.74 |
| 24601 | O | HOH | W | 440 | -51.532 | -5.766 | 89.351 | 1.00 | 34.47 |
| 24602 | O | HOH | W | 441 | -93.787 | -8.401 | 22.095 | 1.00 | 32.88 |
| 24603 | O | HOH | W | 442 | -71.406 | 3.880 | 14.002 | 1.00 | 33.45 |
| 24604 | O | HOH | W | 443 | -98.429 | -9.433 | 30.498 | 1.00 | 29.14 |
| 24605 | O | HOH | W | 444 | -70.817 | -10.368 | 96.315 | 1.00 | 27.94 |
| 24606 | O | HOH | W | 445 | -97.517 | 13.369 | 26.783 | 1.00 | 33.43 |
| 24607 | O | HOH | W | 446 | -89.969 | -3.182 | 22.808 | 1.00 | 35.56 |
| 24608 | O | HOH | W | 447 | -22.398 | -7.403 | 112.204 | 1.00 | 36.75 |
| 24609 | O | HOH | W | 448 | -54.199 | -9.603 | 88.145 | 1.00 | 21.39 |
| 24610 | O | HOH | W | 449 | -9.727 | -30.093 | 71.057 | 1.00 | 39.70 |
| 24611 | O | HOH | W | 450 | -33.216 | 5.161 | 88.968 | 1.00 | 31.92 |
| 24612 | O | HOH | W | 451 | -71.338 | 7.377 | 0.357 | 1.00 | 56.63 |
| 24613 | O | HOH | W | 452 | -65.276 | -2.999 | 91.373 | 1.00 | 31.95 |
| 24614 | O | HOH | W | 453 | -93.385 | 9.333 | 34.303 | 1.00 | 30.73 |
| 24615 | O | HOH | W | 454 | -88.266 | -21.163 | 92.334 | 1.00 | 34.41 |
| 24616 | O | HOH | W | 455 | 7.452 | 15.404 | 87.259 | 1.00 | 48.25 |
| 24617 | O | HOH | W | 456 | -78.495 | -10.661 | 40.980 | 1.00 | 29.54 |
| 24618 | O | HOH | W | 457 | -29.277 | -0.034 | 109.864 | 1.00 | 41.20 |
| 24619 | O | HOH | W | 458 | -84.933 | -22.922 | 78.703 | 1.00 | 29.22 |
| 24620 | O | HOH | W | 459 | -67.783 | -18.157 | 61.639 | 1.00 | 59.22 |
| 24621 | O | HOH | W | 460 | -87.054 | -3.611 | 13.871 | 1.00 | 35.20 |
| 24622 | O | HOH | W | 461 | -106.268 | 3.822 | 20.597 | 1.00 | 40.04 |
| 24623 | O | HOH | W | 462 | -14.798 | -27.138 | 95.307 | 1.00 | 42.14 |

FIGURE 3 RO

| A | B | C | D | E | F | G | H | I | J |
|---|---|---|---|---|---|---|---|---|---|
| 24624 | O | HOH | W | 463 | -106.608 | -0.853 | 14.325 | 1.00 | 44.75 |
| 24625 | O | HOH | W | 464 | -12.037 | 19.585 | 82.638 | 1.00 | 34.50 |
| 24626 | O | HOH | W | 465 | -9.799 | 0.222 | 61.269 | 1.00 | 37.92 |
| 24627 | O | HOH | W | 466 | -20.392 | 5.445 | 93.033 | 1.00 | 25.96 |
| 24628 | O | HOH | W | 467 | -109.907 | 10.806 | 33.777 | 1.00 | 42.21 |
| 24629 | O | HOH | W | 468 | -72.446 | -27.810 | 77.689 | 1.00 | 40.27 |
| 24630 | O | HOH | W | 469 | -42.426 | -12.230 | 79.608 | 1.00 | 32.72 |
| 24631 | O | HOH | W | 470 | -71.414 | 0.070 | 15.776 | 1.00 | 39.43 |
| 24632 | O | HOH | W | 471 | -9.422 | 11.591 | 79.064 | 1.00 | 45.89 |
| 24633 | O | HOH | W | 472 | -99.297 | -8.426 | 65.422 | 1.00 | 34.72 |
| 24634 | O | HOH | W | 473 | -86.247 | -3.322 | 24.107 | 1.00 | 27.75 |
| 24635 | O | HOH | W | 474 | -33.420 | 7.924 | 76.871 | 1.00 | 35.27 |
| 24636 | O | HOH | W | 475 | -84.558 | -15.993 | 84.177 | 1.00 | 25.38 |
| 24637 | O | HOH | W | 476 | -110.008 | -7.611 | 47.215 | 1.00 | 32.50 |
| 24638 | O | HOH | W | 477 | -87.610 | -29.622 | 80.099 | 1.00 | 41.19 |
| 24639 | O | HOH | W | 478 | -63.868 | 15.881 | 75.751 | 1.00 | 32.12 |
| 24640 | O | HOH | W | 479 | -102.368 | 13.617 | 82.403 | 1.00 | 51.21 |
| 24641 | O | HOH | W | 480 | -93.676 | -8.304 | 53.421 | 1.00 | 22.95 |
| 24642 | O | HOH | W | 481 | -65.038 | -2.900 | 54.046 | 1.00 | 29.86 |
| 24643 | O | HOH | W | 482 | -92.189 | -12.262 | 66.212 | 1.00 | 33.84 |
| 24644 | O | HOH | W | 483 | -34.202 | -6.218 | 86.179 | 1.00 | 26.53 |
| 24645 | O | HOH | W | 484 | -96.451 | 9.670 | 20.995 | 1.00 | 36.39 |
| 24646 | O | HOH | W | 485 | -95.374 | -17.291 | 106.485 | 1.00 | 52.48 |
| 24647 | O | HOH | W | 486 | -73.322 | -2.828 | 74.671 | 1.00 | 32.65 |
| 24648 | O | HOH | W | 487 | -64.306 | 10.964 | 88.902 | 1.00 | 36.83 |
| 24649 | O | HOH | W | 488 | -51.433 | 10.267 | 65.577 | 1.00 | 49.74 |
| 24650 | O | HOH | W | 489 | -94.223 | 11.434 | 50.644 | 1.00 | 58.39 |
| 24651 | O | HOH | W | 490 | -111.244 | 11.678 | 38.858 | 1.00 | 40.23 |
| 24652 | O | HOH | W | 491 | -84.214 | -35.551 | 92.737 | 1.00 | 32.32 |
| 24653 | O | HOH | W | 492 | -51.608 | -18.135 | 89.834 | 1.00 | 26.53 |
| 24654 | O | HOH | W | 493 | -17.440 | -25.419 | 66.465 | 1.00 | 49.15 |
| 24655 | O | HOH | W | 494 | -39.111 | 10.312 | 9.299 | 1.00 | 46.57 |
| 24656 | O | HOH | W | 495 | -41.021 | -0.734 | 82.999 | 1.00 | 20.17 |
| 24657 | O | HOH | W | 496 | -104.466 | -16.137 | 89.994 | 1.00 | 29.53 |
| 24658 | O | HOH | W | 497 | -36.737 | -9.547 | 83.254 | 1.00 | 37.47 |
| 24659 | O | HOH | W | 498 | -118.554 | -7.113 | 14.480 | 1.00 | 47.45 |
| 24660 | O | HOH | W | 499 | -70.907 | -0.954 | 72.707 | 1.00 | 24.78 |
| 24661 | O | HOH | W | 500 | -4.235 | 14.513 | 79.624 | 1.00 | 45.58 |
| 24662 | O | HOH | W | 501 | -90.181 | -15.231 | 97.552 | 1.00 | 44.18 |
| 24663 | O | HOH | W | 502 | -76.085 | -25.892 | 68.489 | 1.00 | 33.89 |
| 24664 | O | HOH | W | 503 | -56.259 | 29.758 | 0.366 | 1.00 | 40.78 |
| 24665 | O | HOH | W | 504 | -59.106 | -24.485 | 86.538 | 1.00 | 34.68 |
| 24666 | O | HOH | W | 505 | -131.342 | -22.325 | 2.291 | 1.00 | 51.62 |
| 24667 | O | HOH | W | 506 | -42.230 | 0.815 | 61.632 | 1.00 | 46.95 |
| 24668 | O | HOH | W | 507 | -127.706 | -12.085 | 47.862 | 1.00 | 37.48 |
| 24669 | O | HOH | W | 508 | -114.497 | 13.233 | 17.975 | 1.00 | 37.97 |
| 24670 | O | HOH | W | 509 | -66.706 | -11.810 | 102.856 | 1.00 | 31.99 |
| 24671 | O | HOH | W | 510 | -90.702 | -5.881 | 10.694 | 1.00 | 36.99 |
| 24672 | O | HOH | W | 511 | -62.647 | -27.901 | 89.640 | 1.00 | 48.60 |
| 24673 | O | HOH | W | 512 | -65.472 | -1.994 | 94.134 | 1.00 | 32.99 |
| 24674 | O | HOH | W | 513 | -112.605 | -8.249 | 41.550 | 1.00 | 37.12 |

FIGURE 3 RP

| A | B | C | D | E | F | G | H | I | J |
|---|---|---|---|---|---|---|---|---|---|
| 24675 | O | HOH | W | 514 | -73.619 | -33.358 | 33.610 | 1.00 | 41.94 |
| 24676 | O | HOH | W | 515 | -110.412 | 14.693 | 25.941 | 1.00 | 34.88 |
| 24677 | O | HOH | W | 516 | -127.324 | -18.406 | 28.670 | 1.00 | 37.34 |
| 24678 | O | HOH | W | 517 | -92.072 | 11.787 | 30.309 | 1.00 | 38.67 |
| 24679 | O | HOH | W | 518 | -109.533 | 13.252 | 42.283 | 1.00 | 43.87 |
| 24680 | O | HOH | W | 519 | -96.204 | -22.107 | 73.396 | 1.00 | 40.68 |
| 24681 | O | HOH | W | 520 | -70.511 | 1.201 | -1.688 | 1.00 | 43.61 |
| 24682 | O | HOH | W | 521 | -85.422 | 2.630 | 44.519 | 1.00 | 32.34 |
| 24683 | O | HOH | W | 522 | -89.796 | -10.794 | 54.215 | 1.00 | 26.05 |
| 24684 | O | HOH | W | 523 | -52.252 | -9.767 | -7.150 | 1.00 | 49.69 |
| 24685 | O | HOH | W | 524 | -106.923 | 5.441 | 23.606 | 1.00 | 26.09 |
| 24686 | O | HOH | W | 525 | -70.347 | -0.883 | 1.599 | 1.00 | 33.59 |
| 24687 | O | HOH | W | 526 | -13.852 | 2.537 | 82.735 | 1.00 | 25.71 |
| 24688 | O | HOH | W | 527 | -69.051 | -23.282 | 65.079 | 1.00 | 57.35 |
| 24689 | O | HOH | W | 528 | -15.736 | -24.504 | 64.200 | 1.00 | 55.61 |
| 24690 | O | HOH | W | 529 | -83.151 | -7.369 | 35.490 | 1.00 | 23.48 |
| 24691 | O | HOH | W | 530 | -100.263 | -10.055 | 21.332 | 1.00 | 29.03 |
| 24692 | O | HOH | W | 531 | -84.428 | -15.621 | 36.762 | 1.00 | 30.89 |
| 24693 | O | HOH | W | 532 | -70.991 | -7.964 | 81.724 | 1.00 | 39.87 |
| 24694 | O | HOH | W | 533 | -29.394 | 7.216 | 88.291 | 1.00 | 30.48 |
| 24695 | O | HOH | W | 534 | -90.281 | 11.278 | 38.196 | 1.00 | 37.25 |
| 24696 | O | HOH | W | 535 | -94.916 | -15.110 | 93.283 | 1.00 | 40.87 |
| 24697 | O | HOH | W | 536 | -130.036 | 2.039 | 24.303 | 1.00 | 38.64 |
| 24698 | O | HOH | W | 537 | -89.215 | -0.334 | 55.254 | 1.00 | 42.59 |
| 24699 | O | HOH | W | 538 | -35.758 | -8.081 | 98.639 | 1.00 | 31.72 |
| 24700 | O | HOH | W | 539 | -45.965 | 18.844 | 63.606 | 1.00 | 40.59 |
| 24701 | O | HOH | W | 540 | -78.761 | 1.016 | 34.849 | 1.00 | 41.00 |
| 24702 | O | HOH | W | 541 | -36.879 | 12.264 | 110.190 | 1.00 | 40.17 |
| 24703 | O | HOH | W | 542 | -77.805 | 0.921 | 26.516 | 1.00 | 32.58 |
| 24704 | O | HOH | W | 543 | -51.413 | -5.972 | -11.885 | 1.00 | 55.29 |
| 24705 | O | HOH | W | 544 | -106.420 | 2.514 | 16.392 | 1.00 | 36.42 |
| 24706 | O | HOH | W | 545 | -23.108 | 12.851 | 58.766 | 1.00 | 29.95 |
| 24707 | O | HOH | W | 546 | -21.284 | -34.324 | 68.964 | 1.00 | 34.79 |
| 24708 | O | HOH | W | 547 | -115.873 | -5.662 | 40.853 | 1.00 | 33.89 |
| 24709 | O | HOH | W | 548 | -0.851 | -16.521 | 99.863 | 1.00 | 49.84 |
| 24710 | O | HOH | W | 549 | -125.713 | -12.405 | 49.897 | 1.00 | 29.65 |
| 24711 | O | HOH | W | 550 | -3.397 | 8.350 | 105.410 | 1.00 | 51.21 |
| 24712 | O | HOH | W | 551 | -50.077 | 28.979 | 29.651 | 1.00 | 56.94 |
| 24713 | O | HOH | W | 552 | -106.082 | -6.054 | 28.376 | 1.00 | 35.22 |
| 24714 | O | HOH | W | 553 | -28.271 | 8.354 | 109.470 | 1.00 | 41.13 |
| 24715 | O | HOH | W | 554 | -58.943 | 16.159 | 74.242 | 1.00 | 37.16 |
| 24716 | O | HOH | W | 555 | -110.483 | 11.853 | 49.320 | 1.00 | 38.28 |
| 24717 | O | HOH | W | 556 | -18.014 | -2.864 | 70.527 | 1.00 | 38.46 |
| 24718 | O | HOH | W | 557 | -99.379 | 8.025 | 74.323 | 1.00 | 57.48 |
| 24719 | O | HOH | W | 558 | -85.516 | 1.960 | 94.847 | 1.00 | 45.62 |
| 24720 | O | HOH | W | 559 | -42.903 | -15.679 | 81.707 | 1.00 | 33.93 |
| 24721 | O | HOH | W | 560 | -32.359 | -5.151 | 83.993 | 1.00 | 35.77 |
| 24722 | O | HOH | W | 561 | -124.818 | -32.042 | 29.691 | 1.00 | 41.61 |
| 24723 | O | HOH | W | 562 | -90.150 | -3.668 | 85.593 | 1.00 | 35.28 |
| 24724 | O | HOH | W | 563 | -45.572 | -2.969 | 63.207 | 1.00 | 35.77 |
| 24725 | O | HOH | W | 564 | -96.431 | 13.752 | 89.323 | 1.00 | 42.58 |

FIGURE 3 RQ

| A | B | C | D | E | F | G | H | I | J |
|---|---|---|---|---|---|---|---|---|---|
| 24726 | O | HOH | W | 565 | -11.676 | -29.828 | 73.906 | 1.00 | 43.24 |
| 24727 | O | HOH | W | 566 | -60.965 | -6.210 | 58.917 | 1.00 | 34.35 |
| 24728 | O | HOH | W | 567 | -96.938 | -2.743 | 13.419 | 1.00 | 46.03 |
| 24729 | O | HOH | W | 568 | -80.239 | 7.394 | 76.783 | 1.00 | 38.39 |
| 24730 | O | HOH | W | 569 | -72.035 | 0.429 | 75.999 | 1.00 | 75.60 |
| 24731 | O | HOH | W | 570 | -31.996 | 2.959 | 71.230 | 1.00 | 35.73 |
| 24732 | O | HOH | W | 571 | -44.954 | -18.106 | 77.973 | 1.00 | 50.86 |
| 24733 | O | HOH | W | 572 | -74.601 | -20.462 | 112.735 | 1.00 | 37.33 |
| 24734 | O | HOH | W | 573 | -28.559 | 4.412 | 25.975 | 1.00 | 77.51 |
| 24735 | O | HOH | W | 574 | -77.646 | 3.638 | 70.347 | 1.00 | 23.91 |
| 24736 | O | HOH | W | 575 | -86.584 | 1.876 | 37.295 | 1.00 | 24.00 |
| 24737 | O | HOH | W | 576 | -89.287 | 0.922 | 78.981 | 1.00 | 45.18 |
| 24738 | O | HOH | W | 577 | -76.583 | -27.839 | 98.387 | 1.00 | 30.42 |
| 24739 | O | HOH | W | 578 | -25.542 | 4.659 | 45.516 | 1.00 | 51.05 |
| 24740 | O | HOH | W | 579 | -48.522 | -16.842 | 76.321 | 1.00 | 29.73 |
| 24741 | O | HOH | W | 580 | -53.049 | 17.187 | 76.352 | 1.00 | 37.90 |
| 24742 | O | HOH | W | 581 | -56.312 | 23.501 | 14.352 | 1.00 | 44.49 |
| 24743 | O | HOH | W | 582 | -30.649 | 1.419 | 106.878 | 1.00 | 28.92 |
| 24744 | O | HOH | W | 583 | -12.526 | -25.497 | 64.032 | 1.00 | 52.61 |
| 24745 | O | HOH | W | 584 | -28.109 | -6.042 | 112.750 | 1.00 | 38.18 |
| 24746 | O | HOH | W | 585 | -91.405 | 1.063 | 84.825 | 1.00 | 51.44 |
| 24747 | O | HOH | W | 586 | -32.497 | -0.763 | 55.223 | 1.00 | 48.90 |
| 24748 | O | HOH | W | 587 | -58.966 | -7.611 | 58.385 | 1.00 | 33.24 |
| 24749 | O | HOH | W | 588 | -69.798 | -31.805 | 89.201 | 1.00 | 36.09 |
| 24750 | O | HOH | W | 589 | -56.322 | -1.069 | 89.915 | 1.00 | 30.05 |
| 24751 | O | HOH | W | 590 | -129.557 | -26.903 | 49.312 | 1.00 | 50.67 |
| 24752 | O | HOH | W | 591 | -20.910 | -34.039 | 75.885 | 1.00 | 36.76 |
| 24753 | O | HOH | W | 592 | 6.899 | 4.829 | 91.810 | 1.00 | 41.51 |
| 24754 | O | HOH | W | 593 | -29.936 | -10.926 | 86.256 | 1.00 | 29.42 |
| 24755 | O | HOH | W | 594 | -99.662 | -26.933 | 76.105 | 1.00 | 40.22 |
| 24756 | O | HOH | W | 595 | -110.859 | -21.903 | 59.586 | 1.00 | 51.32 |
| 24757 | O | HOH | W | 596 | -46.604 | 28.337 | 23.745 | 1.00 | 45.45 |
| 24758 | O | HOH | W | 597 | -43.405 | -9.922 | 78.639 | 1.00 | 28.65 |
| 24759 | O | HOH | W | 598 | -110.346 | -15.092 | 42.303 | 1.00 | 44.63 |
| 24760 | O | HOH | W | 599 | -89.685 | -7.210 | 85.731 | 1.00 | 41.15 |
| 24761 | O | HOH | W | 600 | -89.542 | -3.812 | 79.240 | 1.00 | 35.87 |
| 24762 | O | HOH | W | 601 | -39.602 | -12.554 | 95.565 | 1.00 | 61.57 |
| 24763 | O | HOH | W | 602 | -51.722 | 6.270 | 32.500 | 1.00 | 43.89 |
| 24764 | O | HOH | W | 603 | -126.789 | 19.632 | 20.809 | 1.00 | 50.98 |
| 24765 | O | HOH | W | 604 | -106.338 | 20.953 | 20.414 | 1.00 | 55.07 |
| 24766 | O | HOH | W | 605 | -127.649 | -1.043 | 18.844 | 1.00 | 39.90 |
| 24767 | O | HOH | W | 606 | -58.955 | 3.126 | 98.167 | 1.00 | 38.14 |
| 24768 | O | HOH | W | 607 | -0.440 | 16.530 | 101.154 | 1.00 | 45.04 |
| 24769 | O | HOH | W | 608 | -84.789 | -35.574 | 95.888 | 1.00 | 42.44 |
| 24770 | O | HOH | W | 609 | -79.558 | 9.193 | 79.177 | 1.00 | 42.96 |
| 24771 | O | HOH | W | 610 | -146.635 | -4.053 | 40.233 | 1.00 | 44.67 |
| 24772 | O | HOH | W | 611 | -65.285 | 2.197 | 87.705 | 1.00 | 41.91 |
| 24773 | O | HOH | W | 612 | -119.625 | 0.329 | 36.959 | 1.00 | 28.70 |
| 24774 | O | HOH | W | 613 | -14.215 | 4.590 | 62.943 | 1.00 | 39.95 |
| 24775 | O | HOH | W | 614 | -73.078 | 19.826 | 10.249 | 1.00 | 61.27 |
| 24776 | O | HOH | W | 615 | -90.907 | -28.279 | 41.301 | 1.00 | 53.05 |

FIGURE 3 RR

| A | B | C | D | E | F | G | H | I | J |
|---|---|---|---|---|---|---|---|---|---|
| 24777 | O | HOH | W | 616 | -85.475 | 10.018 | 30.278 | 1.00 | 36.42 |
| 24778 | O | HOH | W | 617 | -28.134 | 4.099 | 73.726 | 1.00 | 34.99 |
| 24779 | O | HOH | W | 618 | -50.459 | 3.930 | 95.597 | 1.00 | 22.62 |
| 24780 | O | HOH | W | 619 | -114.113 | 26.603 | 29.382 | 1.00 | 57.35 |
| 24781 | O | HOH | W | 620 | -94.588 | -6.059 | 71.538 | 1.00 | 32.20 |
| 24782 | O | HOH | W | 621 | -82.752 | 13.037 | 62.201 | 1.00 | 30.48 |
| 24783 | O | HOH | W | 622 | -20.926 | -18.909 | 86.095 | 1.00 | 43.77 |
| 24784 | O | HOH | W | 623 | -17.970 | 26.324 | 71.920 | 1.00 | 46.83 |
| 24785 | O | HOH | W | 624 | -44.230 | -14.175 | 75.931 | 1.00 | 44.88 |
| 24786 | O | HOH | W | 625 | -52.806 | -16.627 | 92.395 | 1.00 | 42.51 |
| 24787 | O | HOH | W | 626 | -28.023 | 24.410 | 94.321 | 1.00 | 46.13 |
| 24788 | O | HOH | W | 627 | -120.609 | 28.705 | 21.356 | 1.00 | 63.07 |
| 24789 | O | HOH | W | 628 | -27.577 | 3.545 | 93.373 | 1.00 | 32.85 |
| 24790 | O | HOH | W | 629 | -26.459 | 7.138 | 85.369 | 1.00 | 41.44 |
| 24791 | O | HOH | W | 630 | 0.858 | -25.653 | 75.756 | 1.00 | 59.25 |
| 24792 | O | HOH | W | 631 | -55.884 | -21.067 | 81.597 | 1.00 | 37.94 |
| 24793 | O | HOH | W | 632 | -38.896 | 29.659 | 75.935 | 1.00 | 36.05 |
| 24794 | O | HOH | W | 633 | -84.032 | -15.701 | 93.299 | 1.00 | 32.55 |
| 24795 | O | HOH | W | 634 | -11.874 | -8.228 | 80.656 | 1.00 | 35.54 |
| 24796 | O | HOH | W | 635 | -75.434 | -30.259 | 103.613 | 1.00 | 38.35 |
| 24797 | O | HOH | W | 636 | -74.032 | -33.431 | 88.035 | 1.00 | 34.09 |
| 24798 | O | HOH | W | 637 | -33.404 | -22.472 | 87.965 | 1.00 | 40.49 |
| 24799 | O | HOH | W | 638 | -26.251 | 4.032 | 49.144 | 1.00 | 38.80 |
| 24800 | O | HOH | W | 639 | -108.473 | -41.961 | 44.645 | 1.00 | 66.35 |
| 24801 | O | HOH | W | 640 | -53.820 | 27.469 | 30.231 | 1.00 | 37.74 |
| 24802 | O | HOH | W | 641 | -87.240 | -17.214 | 35.785 | 1.00 | 38.56 |
| 24803 | O | HOH | W | 642 | -100.591 | -21.427 | 22.177 | 1.00 | 31.00 |
| 24804 | O | HOH | W | 643 | -87.956 | -22.906 | 109.676 | 1.00 | 36.03 |
| 24805 | O | HOH | W | 644 | -60.617 | 5.321 | 92.127 | 1.00 | 33.95 |
| 24806 | O | HOH | W | 645 | -24.513 | 5.013 | 38.231 | 1.00 | 47.59 |
| 24807 | O | HOH | W | 646 | -85.583 | -14.622 | 9.202 | 1.00 | 53.67 |
| 24808 | O | HOH | W | 647 | -46.151 | 23.506 | 78.086 | 1.00 | 36.42 |
| 24809 | O | HOH | W | 648 | -15.981 | -11.309 | 72.077 | 1.00 | 46.74 |
| 24810 | O | HOH | W | 649 | -59.801 | -4.749 | 52.778 | 1.00 | 43.98 |
| 24811 | O | HOH | W | 650 | -87.978 | -33.619 | 102.487 | 1.00 | 63.13 |
| 24812 | O | HOH | W | 651 | -11.361 | -7.818 | 97.878 | 1.00 | 37.51 |
| 24813 | O | HOH | W | 652 | -103.706 | -31.490 | 55.381 | 1.00 | 51.71 |
| 24814 | O | HOH | W | 653 | -101.710 | 13.544 | 98.967 | 1.00 | 74.04 |
| 24815 | O | HOH | W | 654 | -84.966 | -38.282 | 96.823 | 1.00 | 41.06 |
| 24816 | O | HOH | W | 655 | -78.472 | -6.737 | 96.586 | 1.00 | 40.72 |
| 24817 | O | HOH | W | 656 | -135.228 | 16.826 | 26.286 | 1.00 | 46.08 |
| 24818 | O | HOH | W | 657 | -31.731 | -0.414 | 108.386 | 1.00 | 30.69 |
| 24819 | O | HOH | W | 658 | -103.774 | -37.385 | 41.953 | 1.00 | 41.27 |
| 24820 | O | HOH | W | 659 | -77.960 | -28.996 | 100.030 | 1.00 | 30.02 |
| 24821 | O | HOH | W | 660 | -27.317 | 8.162 | 38.469 | 1.00 | 49.74 |
| 24822 | O | HOH | W | 661 | -93.111 | -25.539 | 30.845 | 1.00 | 34.26 |
| 24823 | O | HOH | W | 662 | -73.120 | -23.584 | 94.120 | 1.00 | 31.89 |
| 24824 | O | HOH | W | 663 | -19.345 | 2.573 | 76.802 | 1.00 | 47.99 |
| 24825 | O | HOH | W | 664 | -13.696 | -9.570 | 63.137 | 1.00 | 47.91 |
| 24826 | O | HOH | W | 665 | -50.334 | -10.047 | -5.032 | 1.00 | 55.35 |
| 24827 | O | HOH | W | 666 | -128.631 | -29.688 | 43.934 | 1.00 | 42.09 |

FIGURE 3 RS

| A | B | C | D | E | F | G | H | I | J |
|---|---|---|---|---|---:|---:|---:|---:|---:|
| 24828 | O | HOH | W | 667 | 1.998 | 0.931 | 108.640 | 1.00 | 48.09 |
| 24829 | O | HOH | W | 668 | -81.286 | 2.028 | 48.266 | 1.00 | 37.17 |
| 24830 | O | HOH | W | 669 | -134.035 | 1.327 | 29.428 | 1.00 | 34.53 |
| 24831 | O | HOH | W | 670 | -73.399 | -1.276 | -4.487 | 1.00 | 46.20 |
| 24832 | O | HOH | W | 671 | -78.675 | 11.945 | 0.336 | 1.00 | 32.94 |
| 24833 | O | HOH | W | 672 | -109.777 | -18.384 | 39.041 | 1.00 | 40.69 |
| 24834 | O | HOH | W | 673 | -84.206 | -2.279 | 2.801 | 1.00 | 42.50 |
| 24835 | O | HOH | W | 674 | 0.084 | 2.944 | 107.715 | 1.00 | 57.24 |
| 24836 | O | HOH | W | 675 | -13.542 | -1.107 | 101.848 | 1.00 | 37.88 |
| 24837 | O | HOH | W | 676 | -52.682 | -4.437 | 23.976 | 1.00 | 42.73 |
| 24838 | O | HOH | W | 677 | -43.449 | -1.946 | 40.836 | 1.00 | 55.57 |
| 24839 | O | HOH | W | 678 | -31.729 | -25.134 | 88.262 | 1.00 | 42.24 |
| 24840 | O | HOH | W | 679 | -112.636 | 6.306 | 54.952 | 1.00 | 43.73 |
| 24841 | O | HOH | W | 680 | -81.712 | -14.940 | 93.610 | 1.00 | 41.18 |
| 24842 | O | HOH | W | 681 | -136.487 | 12.605 | 39.278 | 1.00 | 45.29 |
| 24843 | O | HOH | W | 682 | -52.351 | -17.893 | 71.059 | 1.00 | 34.40 |
| 24844 | O | HOH | W | 683 | -139.268 | 2.638 | 26.004 | 1.00 | 45.18 |
| 24845 | O | HOH | W | 684 | -51.980 | -5.968 | 99.949 | 1.00 | 34.09 |
| 24846 | O | HOH | W | 685 | -36.644 | -14.622 | 121.379 | 1.00 | 39.41 |
| 24847 | O | HOH | W | 686 | -66.136 | -27.337 | 92.346 | 1.00 | 36.84 |
| 24848 | O | HOH | W | 687 | -70.260 | 3.464 | 78.817 | 1.00 | 35.84 |
| 24849 | O | HOH | W | 688 | -115.054 | -14.780 | 38.963 | 1.00 | 51.42 |
| 24850 | O | HOH | W | 689 | -67.762 | 9.167 | 89.828 | 1.00 | 41.06 |
| 24851 | O | HOH | W | 690 | -76.205 | -19.114 | 45.994 | 1.00 | 42.06 |
| 24852 | O | HOH | W | 691 | -37.718 | -20.124 | 103.859 | 1.00 | 39.08 |
| 24853 | O | HOH | W | 692 | -87.393 | 11.388 | 31.561 | 1.00 | 31.42 |
| 24854 | O | HOH | W | 693 | -84.992 | 17.386 | 67.200 | 1.00 | 39.64 |
| 24855 | O | HOH | W | 694 | -8.499 | 9.237 | 107.160 | 1.00 | 47.35 |
| 24856 | O | HOH | W | 695 | -30.407 | 7.050 | 79.655 | 1.00 | 39.41 |
| 24857 | O | HOH | W | 696 | -66.142 | 18.511 | -3.885 | 1.00 | 53.83 |
| 24858 | O | HOH | W | 697 | -80.694 | 14.083 | 113.091 | 1.00 | 51.24 |
| 24859 | O | HOH | W | 698 | -55.899 | 10.509 | 71.595 | 1.00 | 29.76 |
| 24860 | O | HOH | W | 699 | -11.718 | 0.478 | 82.914 | 1.00 | 45.46 |
| 24861 | O | HOH | W | 700 | -144.057 | 9.602 | 12.139 | 1.00 | 51.96 |
| 24862 | O | HOH | W | 701 | -123.957 | -8.933 | 61.691 | 1.00 | 48.53 |
| 24863 | O | HOH | W | 702 | -109.921 | -40.014 | 51.188 | 1.00 | 51.41 |
| 24864 | O | HOH | W | 703 | -92.687 | 21.608 | 78.741 | 1.00 | 40.56 |
| 24865 | O | HOH | W | 704 | -122.013 | -5.018 | 53.612 | 1.00 | 38.40 |
| 24866 | O | HOH | W | 705 | -101.530 | -38.287 | 46.008 | 1.00 | 51.23 |
| 24867 | O | HOH | W | 706 | -27.454 | -12.186 | 5.720 | 1.00 | 51.47 |
| 24868 | O | HOH | W | 707 | -104.938 | -16.722 | 34.407 | 1.00 | 48.66 |
| 24869 | O | HOH | W | 708 | -26.418 | -14.256 | 81.064 | 1.00 | 46.60 |
| 24870 | O | HOH | W | 709 | -75.934 | -33.496 | 39.841 | 1.00 | 39.00 |
| 24871 | O | HOH | W | 710 | -64.836 | -17.007 | 63.963 | 1.00 | 43.38 |
| 24872 | O | HOH | W | 711 | -95.062 | -4.239 | 89.125 | 1.00 | 47.20 |
| 24873 | O | HOH | W | 712 | -62.552 | -12.299 | 31.956 | 1.00 | 45.49 |
| 24874 | O | HOH | W | 713 | -57.917 | -9.120 | 60.550 | 1.00 | 32.79 |
| 24875 | O | HOH | W | 714 | 1.093 | -5.090 | 108.362 | 1.00 | 45.91 |
| 24876 | O | HOH | W | 715 | -86.973 | -15.905 | 64.055 | 1.00 | 22.71 |
| 24877 | O | HOH | W | 716 | -15.870 | 6.898 | 59.992 | 1.00 | 42.80 |
| 24878 | O | HOH | W | 717 | -6.846 | 16.966 | 94.233 | 1.00 | 42.44 |

FIGURE 3 RT

| A | B | C | D | E | F | G | H | I | J |
|---|---|---|---|---|---|---|---|---|---|
| 24879 | O | HOH | W | 718 | -47.295 | -3.374 | 97.326 | 1.00 | 34.39 |
| 24880 | O | HOH | W | 719 | -18.800 | -5.666 | 55.781 | 1.00 | 37.89 |
| 24881 | O | HOH | W | 720 | -127.641 | 11.225 | 36.633 | 1.00 | 51.23 |
| 24882 | O | HOH | W | 721 | -38.590 | -16.155 | 110.676 | 1.00 | 51.60 |
| 24883 | O | HOH | W | 722 | -39.858 | -0.432 | 59.614 | 1.00 | 50.04 |
| 24884 | O | HOH | W | 723 | -74.314 | -15.994 | 44.707 | 1.00 | 55.03 |
| 24885 | O | HOH | W | 724 | -9.960 | 11.652 | 74.565 | 1.00 | 34.71 |
| 24886 | O | HOH | W | 725 | -107.173 | -17.836 | 33.511 | 1.00 | 38.18 |
| 24887 | O | HOH | W | 726 | -99.868 | -20.443 | 112.442 | 1.00 | 57.29 |
| 24888 | O | HOH | W | 727 | -106.173 | -14.260 | 36.662 | 1.00 | 35.53 |
| 24889 | O | HOH | W | 728 | -119.801 | -15.962 | 37.710 | 1.00 | 45.13 |
| 24890 | O | HOH | W | 729 | -61.611 | 18.551 | 65.794 | 1.00 | 50.39 |
| 24891 | O | HOH | W | 730 | 0.191 | -19.913 | 75.954 | 1.00 | 63.30 |
| 24892 | O | HOH | W | 731 | -94.042 | -24.147 | 61.231 | 1.00 | 53.28 |
| 24893 | O | HOH | W | 732 | -34.003 | -4.912 | 88.410 | 1.00 | 42.19 |
| 24894 | O | HOH | W | 733 | -77.079 | 15.127 | 76.919 | 1.00 | 37.67 |
| 24895 | O | HOH | W | 734 | -25.059 | -32.925 | 97.348 | 1.00 | 45.80 |
| 24896 | O | HOH | W | 735 | -76.693 | -30.862 | 101.322 | 1.00 | 45.34 |
| 24897 | O | HOH | W | 736 | -18.491 | 5.856 | 86.005 | 1.00 | 40.76 |
| 24898 | O | HOH | W | 737 | -108.341 | 2.644 | 7.825 | 1.00 | 62.16 |
| 24899 | O | HOH | W | 738 | -109.993 | 0.738 | 91.620 | 1.00 | 48.60 |
| 24900 | O | HOH | W | 739 | -121.856 | 1.010 | 35.985 | 1.00 | 27.42 |
| 24901 | O | HOH | W | 740 | -92.668 | -13.134 | 63.232 | 1.00 | 40.50 |
| 24902 | O | HOH | W | 741 | -106.480 | 1.723 | 60.044 | 1.00 | 49.04 |
| 24903 | O | HOH | W | 742 | -95.293 | 15.288 | 74.820 | 1.00 | 44.19 |
| 24904 | O | HOH | W | 743 | -113.061 | -15.331 | 19.125 | 1.00 | 51.17 |
| 24905 | O | HOH | W | 744 | -22.958 | -4.870 | 113.055 | 1.00 | 33.35 |
| 24906 | O | HOH | W | 745 | -89.973 | -2.565 | 11.396 | 1.00 | 42.40 |
| 24907 | O | HOH | W | 746 | -79.987 | 1.872 | 22.457 | 1.00 | 23.89 |
| 24908 | O | HOH | W | 747 | -110.181 | -15.573 | 44.474 | 1.00 | 54.44 |
| 24909 | O | HOH | W | 748 | -50.713 | -20.930 | 74.519 | 1.00 | 52.49 |
| 24910 | O | HOH | W | 749 | -73.658 | -24.704 | 68.371 | 1.00 | 34.36 |
| 24911 | O | HOH | W | 750 | -19.437 | -24.855 | 65.220 | 1.00 | 42.91 |
| 24912 | O | HOH | W | 751 | -91.197 | 3.357 | 89.107 | 1.00 | 39.95 |
| 24913 | O | HOH | W | 752 | -118.127 | -5.114 | 55.243 | 1.00 | 36.74 |
| 24914 | O | HOH | W | 753 | -27.171 | 8.632 | 70.946 | 1.00 | 33.58 |
| 24915 | O | HOH | W | 754 | -76.243 | -31.139 | 41.991 | 1.00 | 40.07 |
| 24916 | O | HOH | W | 755 | -39.397 | 8.095 | 56.388 | 1.00 | 56.79 |
| 24917 | O | HOH | W | 756 | -104.200 | -11.227 | 22.065 | 1.00 | 31.85 |
| 24918 | O | HOH | W | 757 | -3.554 | -9.778 | 111.146 | 1.00 | 32.29 |
| 24919 | O | HOH | W | 758 | -74.006 | 1.863 | 72.442 | 1.00 | 30.98 |
| 24920 | O | HOH | W | 759 | -54.405 | 33.925 | 16.062 | 1.00 | 47.19 |
| 24921 | O | HOH | W | 760 | -31.003 | 12.521 | 32.845 | 1.00 | 60.68 |
| 24922 | O | HOH | W | 761 | -78.699 | 2.560 | 97.572 | 1.00 | 46.62 |
| 24923 | O | HOH | W | 762 | -105.963 | -25.020 | 88.669 | 1.00 | 46.06 |
| 24924 | O | HOH | W | 763 | -137.286 | -10.278 | 49.944 | 1.00 | 48.34 |
| 24925 | O | HOH | W | 764 | -54.755 | 10.426 | 94.112 | 1.00 | 25.91 |
| 24926 | O | HOH | W | 765 | -18.367 | 21.230 | 89.592 | 1.00 | 43.75 |
| 24927 | O | HOH | W | 766 | -74.917 | -2.071 | 28.904 | 1.00 | 52.00 |
| 24928 | O | HOH | W | 767 | -75.041 | 1.291 | 37.100 | 1.00 | 48.59 |
| 24929 | O | HOH | W | 768 | -17.797 | 4.843 | 115.745 | 1.00 | 55.35 |

FIGURE 3 RU

| A | B | C | D | E | F | G | H | I | J |
|---|---|---|---|---|---|---|---|---|---|
| 24930 | O | HOH | W | 769 | -97.728 | 13.775 | 22.123 | 1.00 | 47.55 |
| 24931 | O | HOH | W | 770 | -50.927 | -21.661 | 72.392 | 1.00 | 47.05 |
| 24932 | O | HOH | W | 771 | -23.468 | -5.973 | 60.726 | 1.00 | 38.19 |
| 24933 | O | HOH | W | 772 | -123.433 | 0.675 | 33.643 | 1.00 | 45.22 |
| 24934 | O | HOH | W | 773 | -134.913 | -4.283 | 6.958 | 1.00 | 66.68 |
| 24935 | O | HOH | W | 774 | -127.179 | -32.498 | 40.865 | 1.00 | 43.85 |
| 24936 | O | HOH | W | 775 | -17.092 | 16.175 | 76.945 | 1.00 | 45.34 |
| 24937 | O | HOH | W | 776 | -56.377 | 21.256 | 87.338 | 1.00 | 43.00 |
| 24938 | O | HOH | W | 777 | -24.439 | -41.333 | 73.696 | 1.00 | 37.81 |
| 24939 | O | HOH | W | 778 | -73.463 | -30.933 | 86.327 | 1.00 | 33.66 |
| 24940 | O | HOH | W | 779 | -70.281 | -28.784 | 105.005 | 1.00 | 48.94 |
| 24941 | O | HOH | W | 780 | -93.115 | -0.754 | 94.056 | 1.00 | 38.17 |
| 24942 | O | HOH | W | 781 | -31.661 | 5.608 | 75.797 | 1.00 | 36.73 |
| 24943 | O | HOH | W | 782 | -63.429 | 12.258 | 19.239 | 1.00 | 53.46 |
| 24944 | O | HOH | W | 783 | -97.261 | 18.287 | 79.139 | 1.00 | 43.88 |
| 24945 | O | HOH | W | 784 | -71.802 | 2.252 | 35.264 | 1.00 | 40.62 |
| 24946 | O | HOH | W | 785 | -32.081 | 5.748 | 112.046 | 1.00 | 35.75 |
| 24947 | O | HOH | W | 786 | -139.810 | -29.449 | 22.820 | 1.00 | 67.64 |
| 24948 | O | HOH | W | 787 | -101.321 | -18.153 | 113.123 | 1.00 | 44.05 |
| 24949 | O | HOH | W | 788 | -40.760 | -5.156 | 64.114 | 1.00 | 35.05 |
| 24950 | O | HOH | W | 789 | -127.905 | 6.566 | -6.359 | 1.00 | 76.46 |
| 24951 | O | HOH | W | 790 | -59.533 | -26.677 | 90.322 | 1.00 | 34.19 |
| 24952 | O | HOH | W | 791 | -91.799 | 15.065 | 42.251 | 1.00 | 50.36 |
| 24953 | O | HOH | W | 792 | -49.855 | -0.090 | 102.999 | 1.00 | 40.48 |
| 24954 | O | HOH | W | 793 | -52.079 | -22.176 | 70.000 | 1.00 | 45.53 |
| 24955 | O | HOH | W | 794 | -23.004 | -8.624 | 61.058 | 1.00 | 39.84 |
| 24956 | O | HOH | W | 795 | -112.487 | 0.818 | 34.335 | 1.00 | 26.14 |
| 24957 | O | HOH | W | 796 | -140.190 | -8.344 | 52.019 | 1.00 | 56.96 |
| 24958 | O | HOH | W | 797 | -138.528 | -21.185 | 40.068 | 1.00 | 40.97 |
| 24959 | O | HOH | W | 798 | -49.656 | -23.877 | 72.094 | 1.00 | 42.03 |
| 24960 | O | HOH | W | 799 | -119.419 | -3.074 | 56.028 | 1.00 | 32.43 |
| 24961 | O | HOH | W | 800 | -32.508 | 4.018 | 77.065 | 1.00 | 45.49 |
| 24962 | O | HOH | W | 801 | -21.869 | -33.688 | 78.387 | 1.00 | 36.26 |
| 24963 | O | HOH | W | 802 | -60.786 | 17.372 | 73.043 | 1.00 | 51.46 |
| 24964 | O | HOH | W | 803 | -43.068 | 22.317 | 78.859 | 1.00 | 33.81 |
| 24965 | O | HOH | W | 804 | -35.321 | -9.622 | 96.413 | 1.00 | 44.83 |
| 24966 | O | HOH | W | 805 | -87.823 | -13.792 | 52.605 | 1.00 | 36.21 |
| 24967 | O | HOH | W | 806 | -106.590 | -15.054 | 38.915 | 1.00 | 45.67 |
| 24968 | O | HOH | W | 807 | -75.239 | 4.136 | 14.225 | 1.00 | 39.44 |
| 24969 | O | HOH | W | 808 | -18.177 | 13.978 | 67.515 | 1.00 | 58.12 |
| 24970 | O | HOH | W | 809 | 3.469 | -3.273 | 99.678 | 1.00 | 51.02 |
| 24971 | O | HOH | W | 810 | 7.206 | 16.098 | 84.307 | 1.00 | 51.62 |
| 24972 | O | HOH | W | 811 | -134.347 | -10.174 | 26.411 | 1.00 | 53.44 |
| 24973 | O | HOH | W | 812 | -45.444 | 8.802 | -3.602 | 1.00 | 46.81 |
| 24974 | O | HOH | W | 813 | -79.673 | -23.515 | 67.461 | 1.00 | 41.63 |
| 24975 | O | HOH | W | 814 | -45.083 | 23.312 | 87.433 | 1.00 | 52.94 |
| 24976 | O | HOH | W | 815 | -129.550 | -20.361 | -0.338 | 1.00 | 57.31 |
| 24977 | O | HOH | W | 816 | -7.865 | 0.634 | 71.449 | 1.00 | 33.31 |
| 24978 | O | HOH | W | 817 | -92.944 | 4.828 | 65.491 | 1.00 | 70.96 |
| 24979 | O | HOH | W | 818 | -108.298 | 15.720 | 25.185 | 1.00 | 31.68 |
| 24980 | O | HOH | W | 819 | -87.642 | -1.995 | 79.866 | 1.00 | 35.55 |

FIGURE 3 RV

| A | B | C | D | E | F | G | H | I | J |
|---|---|---|---|---|---|---|---|---|---|
| 24981 | O | HOH | W | 820 | -53.129 | -20.624 | 68.121 | 1.00 | 43.18 |
| 24982 | O | HOH | W | 821 | -46.676 | 8.360 | 99.471 | 1.00 | 53.54 |
| 24983 | O | HOH | W | 822 | -82.863 | 6.721 | 17.883 | 1.00 | 47.89 |
| 24984 | O | HOH | W | 823 | -73.495 | 24.656 | 60.445 | 1.00 | 61.86 |
| 24985 | O | HOH | W | 824 | -76.996 | 10.130 | 78.452 | 1.00 | 41.39 |
| 24986 | O | HOH | W | 825 | -72.752 | 8.722 | 115.201 | 1.00 | 41.56 |
| 24987 | O | HOH | W | 826 | -78.867 | -18.768 | 51.533 | 1.00 | 39.31 |
| 24988 | O | HOH | W | 827 | -64.933 | -6.274 | 14.923 | 1.00 | 37.00 |
| 24989 | O | HOH | W | 828 | -108.611 | -11.029 | 92.203 | 1.00 | 69.08 |
| 24990 | O | HOH | W | 829 | -60.555 | -17.772 | 32.874 | 1.00 | 36.50 |
| 24991 | O | HOH | W | 830 | -32.549 | 1.337 | 80.308 | 1.00 | 41.41 |
| 24992 | O | HOH | W | 831 | -113.710 | -25.902 | 32.716 | 1.00 | 49.83 |
| 24993 | O | HOH | W | 832 | -73.968 | -11.280 | 65.674 | 1.00 | 28.56 |
| 24994 | O | HOH | W | 833 | -42.493 | -11.248 | 66.170 | 1.00 | 40.32 |
| 24995 | O | HOH | W | 834 | -96.113 | -9.205 | 61.778 | 1.00 | 46.43 |
| 24996 | O | HOH | W | 835 | -65.152 | -23.619 | 25.368 | 1.00 | 34.26 |
| 24997 | O | HOH | W | 836 | -39.194 | -23.222 | 4.776 | 1.00 | 55.34 |
| 24998 | O | HOH | W | 837 | -36.238 | 2.699 | 9.340 | 1.00 | 62.31 |
| 24999 | O | HOH | W | 838 | -87.425 | 10.700 | 68.799 | 1.00 | 50.27 |
| 25000 | O | HOH | W | 839 | -66.256 | 2.049 | 96.807 | 1.00 | 35.47 |
| 25001 | O | HOH | W | 840 | -89.474 | -22.916 | 65.158 | 1.00 | 45.39 |
| 25002 | O | HOH | W | 841 | -27.948 | 6.269 | 81.342 | 1.00 | 43.67 |
| 25003 | O | HOH | W | 842 | -67.887 | 18.469 | 72.523 | 1.00 | 31.79 |
| 25004 | O | HOH | W | 843 | -120.465 | 7.696 | 45.684 | 1.00 | 38.52 |
| 25005 | O | HOH | W | 844 | -71.060 | -29.982 | 95.335 | 1.00 | 34.81 |
| 25006 | O | HOH | W | 845 | -44.934 | -9.421 | 59.671 | 1.00 | 50.92 |
| 25007 | O | HOH | W | 846 | -136.026 | -17.992 | 47.402 | 1.00 | 44.99 |
| 25008 | O | HOH | W | 847 | -107.725 | -11.728 | 40.368 | 1.00 | 34.40 |
| 25009 | O | HOH | W | 848 | -83.287 | 2.905 | 48.594 | 1.00 | 47.83 |
| 25010 | O | HOH | W | 849 | -95.896 | -8.203 | 11.164 | 1.00 | 46.14 |
| 25011 | O | HOH | W | 850 | -54.155 | 0.876 | -7.757 | 1.00 | 53.90 |
| 25012 | O | HOH | W | 851 | -9.851 | -32.699 | 93.749 | 1.00 | 51.16 |
| 25013 | O | HOH | W | 852 | -104.348 | 12.704 | 99.534 | 1.00 | 63.26 |
| 25014 | O | HOH | W | 853 | -87.422 | -4.549 | 113.517 | 1.00 | 48.99 |
| 25015 | O | HOH | W | 854 | -2.158 | -6.450 | 64.851 | 1.00 | 64.74 |
| 25016 | O | HOH | W | 855 | -18.363 | 6.447 | 83.250 | 1.00 | 46.03 |
| 25017 | O | HOH | W | 856 | -7.083 | 21.878 | 86.321 | 1.00 | 52.99 |
| 25018 | O | HOH | W | 857 | -141.370 | -13.344 | 38.226 | 1.00 | 47.02 |
| 25019 | O | HOH | W | 858 | -18.676 | 23.769 | 88.306 | 1.00 | 36.60 |
| 25020 | O | HOH | W | 859 | -3.232 | -4.531 | 62.613 | 1.00 | 53.78 |
| 25021 | O | HOH | W | 860 | -57.543 | 18.385 | 78.029 | 1.00 | 64.06 |
| 25022 | O | HOH | W | 861 | -107.309 | 16.795 | 22.170 | 1.00 | 48.15 |
| 25023 | O | HOH | W | 862 | -87.861 | 16.821 | 79.674 | 1.00 | 41.12 |
| 25024 | O | HOH | W | 863 | -85.693 | -7.204 | 77.392 | 1.00 | 33.57 |
| 25025 | O | HOH | W | 864 | -62.946 | 10.907 | 53.948 | 1.00 | 46.59 |
| 25026 | O | HOH | W | 865 | -36.828 | -32.372 | 89.420 | 1.00 | 59.66 |
| 25027 | O | HOH | W | 866 | -130.269 | -31.081 | 42.575 | 1.00 | 58.44 |
| 25028 | O | HOH | W | 867 | -84.428 | -28.018 | 97.755 | 1.00 | 45.22 |
| 25029 | O | HOH | W | 868 | -96.603 | -15.449 | 95.970 | 1.00 | 50.05 |
| 25030 | O | HOH | W | 869 | -84.309 | -3.507 | 53.654 | 1.00 | 52.40 |
| 25031 | O | HOH | W | 870 | -85.488 | -9.485 | 79.996 | 1.00 | 34.93 |

FIGURE 3 RW

| A | B | C | D | E | F | G | H | I | J |
|---|---|---|---|---|---|---|---|---|---|
| 25032 | O | HOH | W | 871 | -14.231 | -18.199 | 83.212 | 1.00 | 65.94 |
| 25033 | O | HOH | W | 872 | -41.548 | 6.888 | 12.114 | 1.00 | 57.29 |
| 25034 | O | HOH | W | 873 | -86.723 | -21.494 | 68.143 | 1.00 | 40.01 |
| 25035 | O | HOH | W | 874 | -13.321 | -0.552 | 86.509 | 1.00 | 46.17 |
| 25036 | O | HOH | W | 875 | -102.575 | 21.776 | 36.735 | 1.00 | 35.79 |
| 25037 | O | HOH | W | 876 | -21.013 | 12.921 | 96.471 | 1.00 | 41.55 |
| 25038 | O | HOH | W | 877 | -54.981 | -25.534 | 41.222 | 1.00 | 51.79 |
| 25039 | O | HOH | W | 878 | -84.913 | -24.984 | 68.610 | 1.00 | 38.41 |
| 25040 | O | HOH | W | 879 | -11.882 | -16.848 | 84.504 | 1.00 | 40.57 |
| 25041 | O | HOH | W | 880 | -65.886 | -14.938 | 26.150 | 1.00 | 39.74 |
| 25042 | O | HOH | W | 881 | -43.445 | -13.300 | 94.973 | 1.00 | 47.16 |
| 25043 | O | HOH | W | 882 | -86.575 | 3.908 | 39.235 | 1.00 | 35.06 |
| 25044 | O | HOH | W | 883 | -42.935 | -14.460 | 101.664 | 1.00 | 46.33 |
| 25045 | O | HOH | W | 884 | -102.862 | 4.225 | 59.670 | 1.00 | 63.42 |
| 25046 | O | HOH | W | 885 | -37.621 | 27.775 | 64.018 | 1.00 | 42.56 |
| 25047 | O | HOH | W | 886 | -123.005 | 4.627 | 56.211 | 1.00 | 44.90 |
| 25048 | O | HOH | W | 887 | -44.650 | -16.244 | 101.376 | 1.00 | 45.20 |
| 25049 | O | HOH | W | 888 | -8.862 | 20.234 | 91.644 | 1.00 | 38.30 |
| 25050 | O | HOH | W | 889 | -123.766 | -17.360 | 38.390 | 1.00 | 46.84 |
| 25051 | O | HOH | W | 890 | -103.157 | -0.399 | 72.982 | 1.00 | 46.81 |
| 25052 | O | HOH | W | 891 | -105.777 | 14.631 | 20.611 | 1.00 | 66.24 |
| 25053 | O | HOH | W | 892 | -24.023 | 9.502 | 65.466 | 1.00 | 46.04 |
| 25054 | O | HOH | W | 893 | -28.285 | -3.488 | 113.000 | 1.00 | 45.11 |
| 25055 | O | HOH | W | 894 | -25.898 | 2.662 | 91.394 | 1.00 | 37.86 |
| 25056 | O | HOH | W | 895 | -76.562 | -34.369 | 33.493 | 1.00 | 57.61 |
| 25057 | O | HOH | W | 896 | -22.712 | 3.824 | 76.835 | 1.00 | 44.17 |
| 25058 | O | HOH | W | 897 | -48.565 | -19.330 | 89.549 | 1.00 | 35.12 |
| 25059 | O | HOH | W | 898 | -63.475 | -15.102 | 11.755 | 1.00 | 40.72 |
| 25060 | O | HOH | W | 899 | -30.645 | 31.637 | 80.113 | 1.00 | 48.97 |
| 25061 | O | HOH | W | 900 | -25.243 | 4.993 | 98.133 | 1.00 | 36.36 |
| 25062 | O | HOH | W | 901 | -87.702 | -35.472 | 100.703 | 1.00 | 48.87 |
| 25063 | O | HOH | W | 902 | -93.587 | -10.177 | 61.052 | 1.00 | 58.57 |
| 25064 | O | HOH | W | 903 | -97.756 | 16.026 | 29.825 | 1.00 | 48.85 |
| 25065 | O | HOH | W | 904 | -20.115 | -3.404 | 74.768 | 1.00 | 44.90 |
| 25066 | O | HOH | W | 905 | -15.016 | 18.829 | 99.081 | 1.00 | 58.91 |
| 25067 | O | HOH | W | 906 | -91.419 | -31.458 | 38.390 | 1.00 | 39.28 |
| 25068 | O | HOH | W | 907 | -85.162 | -30.223 | 38.252 | 1.00 | 60.78 |
| 25069 | O | HOH | W | 908 | -31.527 | 17.665 | 31.472 | 1.00 | 60.01 |
| 25070 | O | HOH | W | 909 | -77.299 | -14.987 | 49.080 | 1.00 | 41.20 |
| 25071 | O | HOH | W | 910 | -70.003 | 4.960 | 113.532 | 1.00 | 54.43 |
| 25072 | O | HOH | W | 911 | -70.496 | 5.623 | 116.492 | 1.00 | 44.56 |
| 25073 | O | HOH | W | 912 | -72.335 | 7.240 | 119.566 | 1.00 | 52.72 |
| 25074 | O | HOH | W | 913 | -67.577 | 8.642 | 116.472 | 1.00 | 53.27 |
| 25075 | O | HOH | W | 914 | -102.314 | 24.937 | 12.816 | 1.00 | 56.03 |
| 25076 | O | HOH | W | 915 | -97.900 | 28.228 | 14.950 | 1.00 | 44.18 |
| 25077 | O | HOH | W | 916 | -110.808 | 20.471 | 46.849 | 1.00 | 72.10 |

FIGURE 3 RX

| A | B | C | D | E | F | G | H | I | J |
|---|---|---|---|---|---|---|---|---|---|
| 25078 | O | HOH | W | 917 | -38.511 | -5.038 | 127.327 | 1.00 | 64.38 |
| 25079 | O | HOH | W | 918 | -110.204 | -15.447 | -2.899 | 1.00 | 67.44 |
| 25080 | O | HOH | W | 919 | 7.037 | -20.430 | 68.754 | 1.00 | 55.24 |
| 25081 | O | HOH | W | 920 | -110.374 | 13.235 | 102.576 | 1.00 | 57.48 |
| 25082 | O | HOH | W | 921 | -107.848 | 12.664 | 99.863 | 1.00 | 52.86 |
| 25083 | O | HOH | W | 922 | -105.429 | 10.964 | 104.942 | 1.00 | 64.95 |
| 25084 | O | HOH | W | 923 | -107.566 | 15.872 | 103.930 | 1.00 | 49.98 |

FIGURE 3 RY

| A | B | C | D | E | F | G | H | I | J |
|---|---|---|---|---|---|---|---|---|---|
| 22380 | CB | LYS | D | 528 | -110.469 | -11.517 | 45.892 | 1.00 | 29.88 |
| 22381 | CG | LYS | D | 528 | -109.811 | -10.599 | 44.854 | 1.00 | 31.00 |
| 22382 | CD | LYS | D | 528 | -109.819 | -11.175 | 43.455 | 1.00 | 29.85 |
| 22383 | CE | LYS | D | 528 | -109.210 | -12.545 | 43.375 | 1.00 | 32.75 |
| 22384 | NZ | LYS | D | 528 | -107.963 | -12.709 | 44.124 | 1.00 | 32.18 |
| 22385 | C | LYS | D | 528 | -112.482 | -12.710 | 46.743 | 1.00 | 29.69 |
| 22386 | O | LYS | D | 528 | -112.047 | -13.844 | 46.746 | 1.00 | 28.93 |
| 22387 | N | ALA | D | 529 | -113.362 | -12.293 | 47.641 | 1.00 | 31.26 |
| 22388 | CA | ALA | D | 529 | -113.948 | -13.252 | 48.571 | 1.00 | 32.56 |
| 22389 | CB | ALA | D | 529 | -113.970 | -12.708 | 49.973 | 1.00 | 32.17 |
| 22390 | C | ALA | D | 529 | -115.357 | -13.498 | 48.054 | 1.00 | 33.38 |
| 22391 | O | ALA | D | 529 | -116.234 | -12.672 | 48.299 | 1.00 | 33.84 |
| 22392 | N | ASP | D | 530 | -115.536 | -14.607 | 47.319 | 1.00 | 34.00 |
| 22393 | CA | ASP | D | 530 | -116.783 | -14.967 | 46.606 | 1.00 | 35.36 |
| 22394 | CB | ASP | D | 530 | -116.490 | -15.349 | 45.126 | 1.00 | 35.29 |
| 22395 | CG | ASP | D | 530 | -115.969 | -14.213 | 44.287 | 1.00 | 38.56 |
| 22396 | OD1 | ASP | D | 530 | -116.423 | -14.084 | 43.138 | 1.00 | 41.15 |
| 22397 | OD2 | ASP | D | 530 | -115.062 | -13.420 | 44.632 | 1.00 | 45.19 |
| 22398 | C | ASP | D | 530 | -117.403 | -16.253 | 47.157 | 1.00 | 34.96 |
| 22399 | O | ASP | D | 530 | -116.764 | -16.985 | 47.886 | 1.00 | 35.34 |
| 22400 | N | THR | D | 531 | -118.630 | -16.553 | 46.741 | 1.00 | 34.45 |
| 22401 | CA | THR | D | 531 | -119.231 | -17.849 | 47.016 | 1.00 | 34.17 |
| 22402 | CB | THR | D | 531 | -120.712 | -17.756 | 47.493 | 1.00 | 34.07 |
| 22403 | OG1 | THR | D | 531 | -121.523 | -17.144 | 46.477 | 1.00 | 34.32 |
| 22404 | CG2 | THR | D | 531 | -120.866 | -16.824 | 48.689 | 1.00 | 33.95 |
| 22405 | C | THR | D | 531 | -119.205 | -18.586 | 45.695 | 1.00 | 34.05 |
| 22406 | O | THR | D | 531 | -120.026 | -19.455 | 45.466 | 1.00 | 33.61 |
| 22407 | N | VAL | D | 532 | -118.288 | -18.198 | 44.807 | 1.00 | 33.97 |
| 22408 | CA | VAL | D | 532 | -118.193 | -18.819 | 43.487 | 1.00 | 33.24 |
| 22409 | CB | VAL | D | 532 | -117.643 | -17.840 | 42.418 | 1.00 | 33.74 |
| 22410 | CG1 | VAL | D | 532 | -117.397 | -18.559 | 41.073 | 1.00 | 31.82 |
| 22411 | CG2 | VAL | D | 532 | -118.593 | -16.654 | 42.224 | 1.00 | 32.78 |
| 22412 | C | VAL | D | 532 | -117.344 | -20.082 | 43.507 | 1.00 | 33.28 |
| 22413 | O | VAL | D | 532 | -116.378 | -20.193 | 44.268 | 1.00 | 32.79 |
| 22414 | N | PHE | D | 533 | -117.723 | -21.039 | 42.667 | 1.00 | 33.08 |
| 22415 | CA | PHE | D | 533 | -116.998 | -22.291 | 42.566 | 1.00 | 32.91 |
| 22416 | CB | PHE | D | 533 | -117.936 | -23.465 | 42.297 | 1.00 | 33.19 |
| 22417 | CG | PHE | D | 533 | -117.209 | -24.742 | 42.033 | 1.00 | 33.43 |
| 22418 | CD1 | PHE | D | 533 | -116.675 | -25.468 | 43.079 | 1.00 | 33.91 |
| 22419 | CE1 | PHE | D | 533 | -115.974 | -26.632 | 42.848 | 1.00 | 33.49 |
| 22420 | CZ | PHE | D | 533 | -115.793 | -27.068 | 41.569 | 1.00 | 33.77 |
| 22421 | CE2 | PHE | D | 533 | -116.305 | -26.341 | 40.509 | 1.00 | 35.32 |
| 22422 | CD2 | PHE | D | 533 | -116.999 | -25.180 | 40.743 | 1.00 | 33.72 |
| 22423 | C | PHE | D | 533 | -116.028 | -22.207 | 41.428 | 1.00 | 32.73 |
| 22424 | O | PHE | D | 533 | -116.404 | -21.924 | 40.304 | 1.00 | 32.88 |
| 22425 | N | ARG | D | 534 | -114.773 | -22.493 | 41.703 | 1.00 | 33.21 |
| 22426 | CA | ARG | D | 534 | -113.764 | -22.376 | 40.675 | 1.00 | 33.45 |
| 22427 | CB | ARG | D | 534 | -112.917 | -21.111 | 40.906 | 1.00 | 34.03 |
| 22428 | CG | ARG | D | 534 | -113.685 | -19.780 | 40.894 | 1.00 | 33.35 |
| 22429 | CD | ARG | D | 534 | -112.769 | -18.543 | 40.923 | 1.00 | 33.39 |
| 22430 | NE | ARG | D | 534 | -113.530 | -17.303 | 40.775 | 1.00 | 32.63 |

FIGURE 3 RZ

| A | B | C | D | E | F | G | H | I | J |
|---|---|---|---|---|---|---|---|---|---|
| 22431 | CZ | ARG | D | 534 | -114.159 | -16.700 | 41.771 | 1.00 | 30.97 |
| 22432 | NH1 | ARG | D | 534 | -114.862 | -15.592 | 41.543 | 1.00 | 30.56 |
| 22433 | NH2 | ARG | D | 534 | -114.100 | -17.216 | 42.991 | 1.00 | 27.55 |
| 22434 | C | ARG | D | 534 | -112.844 | -23.578 | 40.649 | 1.00 | 33.45 |
| 22435 | O | ARG | D | 534 | -112.604 | -24.228 | 41.670 | 1.00 | 33.84 |
| 22436 | N | LEU | D | 535 | -112.347 | -23.869 | 39.459 | 1.00 | 32.92 |
| 22437 | CA | LEU | D | 535 | -111.330 | -24.873 | 39.276 | 1.00 | 32.75 |
| 22438 | CB | LEU | D | 535 | -111.794 | -25.967 | 38.330 | 1.00 | 33.22 |
| 22439 | CG | LEU | D | 535 | -113.001 | -26.703 | 38.907 | 1.00 | 34.43 |
| 22440 | CD1 | LEU | D | 535 | -113.453 | -27.749 | 37.909 | 1.00 | 36.11 |
| 22441 | CD2 | LEU | D | 535 | -112.653 | -27.322 | 40.271 | 1.00 | 32.76 |
| 22442 | C | LEU | D | 535 | -110.201 | -24.092 | 38.668 | 1.00 | 32.22 |
| 22443 | O | LEU | D | 535 | -110.243 | -23.712 | 37.493 | 1.00 | 30.98 |
| 22444 | N | ASN | D | 536 | -109.206 | -23.810 | 39.498 | 1.00 | 32.18 |
| 22445 | CA | ASN | D | 536 | -108.085 | -23.001 | 39.066 | 1.00 | 31.90 |
| 22446 | CB | ASN | D | 536 | -108.384 | -21.536 | 39.359 | 1.00 | 31.60 |
| 22447 | CG | ASN | D | 536 | -108.677 | -21.291 | 40.818 | 1.00 | 31.90 |
| 22448 | OD1 | ASN | D | 536 | -108.304 | -22.105 | 41.678 | 1.00 | 31.63 |
| 22449 | ND2 | ASN | D | 536 | -109.340 | -20.161 | 41.122 | 1.00 | 29.42 |
| 22450 | C | ASN | D | 536 | -106.775 | -23.425 | 39.704 | 1.00 | 31.71 |
| 22451 | O | ASN | D | 536 | -106.671 | -24.492 | 40.296 | 1.00 | 31.78 |
| 22452 | N | TRP | D | 537 | -105.768 | -22.577 | 39.566 | 1.00 | 31.71 |
| 22453 | CA | TRP | D | 537 | -104.455 | -22.868 | 40.092 | 1.00 | 31.28 |
| 22454 | CB | TRP | D | 537 | -103.569 | -21.655 | 39.873 | 1.00 | 30.97 |
| 22455 | CG | TRP | D | 537 | -102.151 | -21.917 | 40.133 | 1.00 | 28.42 |
| 22456 | CD1 | TRP | D | 537 | -101.437 | -23.003 | 39.750 | 1.00 | 26.24 |
| 22457 | NE1 | TRP | D | 537 | -100.129 | -22.874 | 40.147 | 1.00 | 26.79 |
| 22458 | CE2 | TRP | D | 537 | -99.987 | -21.686 | 40.814 | 1.00 | 26.24 |
| 22459 | CD2 | TRP | D | 537 | -101.244 | -21.054 | 40.813 | 1.00 | 28.24 |
| 22460 | CE3 | TRP | D | 537 | -101.368 | -19.802 | 41.436 | 1.00 | 26.92 |
| 22461 | CZ3 | TRP | D | 537 | -100.275 | -19.248 | 42.025 | 1.00 | 26.67 |
| 22462 | CH2 | TRP | D | 537 | -99.035 | -19.898 | 42.002 | 1.00 | 28.13 |
| 22463 | CZ2 | TRP | D | 537 | -98.874 | -21.117 | 41.396 | 1.00 | 27.01 |
| 22464 | C | TRP | D | 537 | -104.551 | -23.137 | 41.575 | 1.00 | 31.39 |
| 22465 | O | TRP | D | 537 | -103.943 | -24.065 | 42.098 | 1.00 | 32.11 |
| 22466 | N | ALA | D | 538 | -105.315 | -22.298 | 42.255 | 1.00 | 31.48 |
| 22467 | CA | ALA | D | 538 | -105.494 | -22.417 | 43.683 | 1.00 | 31.67 |
| 22468 | CB | ALA | D | 538 | -106.381 | -21.287 | 44.196 | 1.00 | 31.61 |
| 22469 | C | ALA | D | 538 | -106.073 | -23.783 | 44.057 | 1.00 | 31.89 |
| 22470 | O | ALA | D | 538 | -105.707 | -24.346 | 45.077 | 1.00 | 32.15 |
| 22471 | N | THR | D | 539 | -106.983 | -24.306 | 43.241 | 1.00 | 32.44 |
| 22472 | CA | THR | D | 539 | -107.528 | -25.635 | 43.487 | 1.00 | 33.01 |
| 22473 | CB | THR | D | 539 | -108.526 | -26.049 | 42.393 | 1.00 | 32.91 |
| 22474 | OG1 | THR | D | 539 | -109.510 | -25.030 | 42.220 | 1.00 | 32.56 |
| 22475 | CG2 | THR | D | 539 | -109.365 | -27.234 | 42.861 | 1.00 | 33.33 |
| 22476 | C | THR | D | 539 | -106.371 | -26.625 | 43.536 | 1.00 | 33.42 |
| 22477 | O | THR | D | 539 | -106.253 | -27.407 | 44.467 | 1.00 | 33.41 |
| 22478 | N | TYR | D | 540 | -105.504 | -26.569 | 42.533 | 1.00 | 33.82 |
| 22479 | CA | TYR | D | 540 | -104.343 | -27.452 | 42.482 | 1.00 | 34.43 |
| 22480 | CB | TYR | D | 540 | -103.574 | -27.267 | 41.166 | 1.00 | 34.19 |
| 22481 | CG | TYR | D | 540 | -102.083 | -27.408 | 41.334 | 1.00 | 35.99 |

FIGURE 3 SA

| A | B | C | D | E | F | G | H | I | J |
|---|---|---|---|---|---|---|---|---|---|
| 22482 | CD1 | TYR | D | 540 | -101.239 | -26.291 | 41.266 | 1.00 | 36.53 |
| 22483 | CE1 | TYR | D | 540 | -99.870 | -26.416 | 41.430 | 1.00 | 36.80 |
| 22484 | CZ | TYR | D | 540 | -99.321 | -27.666 | 41.678 | 1.00 | 39.13 |
| 22485 | OH | TYR | D | 540 | -97.947 | -27.817 | 41.841 | 1.00 | 39.63 |
| 22486 | CE2 | TYR | D | 540 | -100.144 | -28.783 | 41.756 | 1.00 | 38.20 |
| 22487 | CD2 | TYR | D | 540 | -101.512 | -28.647 | 41.583 | 1.00 | 36.76 |
| 22488 | C | TYR | D | 540 | -103.403 | -27.263 | 43.674 | 1.00 | 34.61 |
| 22489 | O | TYR | D | 540 | -102.846 | -28.227 | 44.187 | 1.00 | 35.20 |
| 22490 | N | LEU | D | 541 | -103.220 | -26.030 | 44.125 | 1.00 | 34.49 |
| 22491 | CA | LEU | D | 541 | -102.306 | -25.801 | 45.246 | 1.00 | 34.30 |
| 22492 | CB | LEU | D | 541 | -101.986 | -24.305 | 45.422 | 1.00 | 33.43 |
| 22493 | CG | LEU | D | 541 | -101.287 | -23.566 | 44.280 | 1.00 | 33.62 |
| 22494 | CD1 | LEU | D | 541 | -101.321 | -22.060 | 44.528 | 1.00 | 33.14 |
| 22495 | CD2 | LEU | D | 541 | -99.857 | -24.053 | 44.067 | 1.00 | 30.95 |
| 22496 | C | LEU | D | 541 | -102.816 | -26.372 | 46.568 | 1.00 | 34.23 |
| 22497 | O | LEU | D | 541 | -102.043 | -26.919 | 47.365 | 1.00 | 34.14 |
| 22498 | N | ALA | D | 542 | -104.107 | -26.211 | 46.820 | 1.00 | 34.20 |
| 22499 | CA | ALA | D | 542 | -104.689 | -26.682 | 48.067 | 1.00 | 34.60 |
| 22500 | CB | ALA | D | 542 | -106.072 | -26.089 | 48.250 | 1.00 | 34.08 |
| 22501 | C | ALA | D | 542 | -104.774 | -28.210 | 48.081 | 1.00 | 35.01 |
| 22502 | O | ALA | D | 542 | -104.430 | -28.873 | 49.069 | 1.00 | 34.56 |
| 22503 | N | SER | D | 543 | -105.207 | -28.740 | 46.945 | 1.00 | 35.36 |
| 22504 | CA | SER | D | 543 | -105.488 | -30.145 | 46.784 | 1.00 | 36.01 |
| 22505 | CB | SER | D | 543 | -106.223 | -30.344 | 45.461 | 1.00 | 36.05 |
| 22506 | OG | SER | D | 543 | -106.513 | -31.706 | 45.239 | 1.00 | 38.51 |
| 22507 | C | SER | D | 543 | -104.241 | -30.982 | 46.806 | 1.00 | 36.06 |
| 22508 | O | SER | D | 543 | -104.138 | -31.932 | 47.576 | 1.00 | 35.64 |
| 22509 | N | THR | D | 582 | -103.278 | -30.613 | 45.964 | 1.00 | 36.46 |
| 22510 | CA | THR | D | 544 | -102.064 | -31.412 | 45.797 | 1.00 | 36.40 |
| 22511 | CB | THR | D | 544 | -101.614 | -31.355 | 44.335 | 1.00 | 36.34 |
| 22512 | OG1 | THR | D | 544 | -102.676 | -31.788 | 43.484 | 1.00 | 37.72 |
| 22513 | CG2 | THR | D | 544 | -100.522 | -32.366 | 44.053 | 1.00 | 37.38 |
| 22514 | C | THR | D | 544 | -100.911 | -30.964 | 46.683 | 1.00 | 36.54 |
| 22515 | O | THR | D | 544 | -100.186 | -31.800 | 47.239 | 1.00 | 36.92 |
| 22516 | N | GLU | D | 545 | -100.729 | -29.649 | 46.816 | 1.00 | 35.81 |
| 22517 | CA | GLU | D | 545 | -99.558 | -29.141 | 47.515 | 1.00 | 35.27 |
| 22518 | CB | GLU | D | 545 | -98.870 | -28.052 | 46.674 | 1.00 | 34.96 |
| 22519 | CG | GLU | D | 545 | -98.775 | -28.409 | 45.193 | 1.00 | 34.43 |
| 22520 | CD | GLU | D | 545 | -97.587 | -29.292 | 44.853 | 1.00 | 33.89 |
| 22521 | OE1 | GLU | D | 545 | -97.339 | -29.558 | 43.650 | 1.00 | 32.37 |
| 22522 | OE2 | GLU | D | 545 | -96.881 | -29.715 | 45.787 | 1.00 | 35.41 |
| 22523 | C | GLU | D | 545 | -99.892 | -28.671 | 48.921 | 1.00 | 34.78 |
| 22524 | O | GLU | D | 545 | -99.077 | -28.076 | 49.611 | 1.00 | 35.19 |
| 22525 | N | ASN | D | 546 | -101.101 | -28.971 | 49.347 | 1.00 | 34.51 |
| 22526 | CA | ASN | D | 546 | -101.558 | -28.603 | 50.678 | 1.00 | 34.11 |
| 22527 | CB | ASN | D | 546 | -101.163 | -29.679 | 51.695 | 1.00 | 34.57 |
| 22528 | CG | ASN | D | 546 | -101.851 | -31.001 | 51.413 | 1.00 | 36.54 |
| 22529 | OD1 | ASN | D | 546 | -101.307 | -31.860 | 50.719 | 1.00 | 40.92 |
| 22530 | ND2 | ASN | D | 546 | -103.064 | -31.159 | 51.920 | 1.00 | 38.06 |
| 22531 | C | ASN | D | 546 | -101.198 | -27.195 | 51.136 | 1.00 | 33.35 |
| 22532 | O | ASN | D | 546 | -100.691 | -26.979 | 52.240 | 1.00 | 33.38 |

FIGURE 3 SB

| A | B | C | D | E | F | G | H | I | J |
|---|---|---|---|---|---|---|---|---|---|
| 22533 | N | ILE | D | 547 | -101.497 | -26.236 | 50.269 | 1.00 | 32.27 |
| 22534 | CA | ILE | D | 547 | -101.311 | -24.827 | 50.545 | 1.00 | 30.72 |
| 22535 | CB | ILE | D | 547 | -100.623 | -24.155 | 49.330 | 1.00 | 31.08 |
| 22536 | CG1 | ILE | D | 547 | -99.209 | -24.719 | 49.142 | 1.00 | 29.43 |
| 22537 | CD1 | ILE | D | 547 | -98.621 | -24.443 | 47.817 | 1.00 | 24.93 |
| 22538 | CG2 | ILE | D | 547 | -100.610 | -22.626 | 49.482 | 1.00 | 30.21 |
| 22539 | C | ILE | D | 547 | -102.654 | -24.157 | 50.779 | 1.00 | 30.22 |
| 22540 | O | ILE | D | 547 | -103.548 | -24.256 | 49.950 | 1.00 | 30.31 |
| 22541 | N | ILE | D | 548 | -102.822 | -23.489 | 51.913 | 1.00 | 29.75 |
| 22542 | CA | ILE | D | 548 | -104.013 | -22.695 | 52.083 | 1.00 | 29.56 |
| 22543 | CB | ILE | D | 548 | -104.159 | -22.187 | 53.502 | 1.00 | 29.32 |
| 22544 | CG1 | ILE | D | 548 | -104.299 | -23.339 | 54.498 | 1.00 | 30.97 |
| 22545 | CD1 | ILE | D | 548 | -104.571 | -22.855 | 55.948 | 1.00 | 28.15 |
| 22546 | CG2 | ILE | D | 548 | -105.390 | -21.294 | 53.614 | 1.00 | 28.75 |
| 22547 | C | ILE | D | 548 | -103.874 | -21.491 | 51.156 | 1.00 | 29.79 |
| 22548 | O | ILE | D | 548 | -102.842 | -20.840 | 51.140 | 1.00 | 29.92 |
| 22549 | N | VAL | D | 549 | -104.887 | -21.195 | 50.360 | 1.00 | 29.75 |
| 22550 | CA | VAL | D | 549 | -104.787 | -19.987 | 49.572 | 1.00 | 29.97 |
| 22551 | CB | VAL | D | 549 | -104.492 | -20.228 | 48.067 | 1.00 | 29.86 |
| 22552 | CG1 | VAL | D | 549 | -104.788 | -21.627 | 47.679 | 1.00 | 31.52 |
| 22553 | CG2 | VAL | D | 549 | -105.192 | -19.204 | 47.198 | 1.00 | 30.60 |
| 22554 | C | VAL | D | 549 | -105.961 | -19.073 | 49.867 | 1.00 | 29.65 |
| 22555 | O | VAL | D | 549 | -107.125 | -19.410 | 49.628 | 1.00 | 29.74 |
| 22556 | N | ALA | D | 550 | -105.619 | -17.925 | 50.439 | 1.00 | 28.34 |
| 22557 | CA | ALA | D | 550 | -106.589 | -16.984 | 50.927 | 1.00 | 27.71 |
| 22558 | CB | ALA | D | 550 | -106.215 | -16.562 | 52.346 | 1.00 | 27.73 |
| 22559 | C | ALA | D | 550 | -106.675 | -15.750 | 50.054 | 1.00 | 27.36 |
| 22560 | O | ALA | D | 550 | -105.756 | -15.418 | 49.324 | 1.00 | 26.91 |
| 22561 | N | SER | D | 551 | -107.790 | -15.053 | 50.172 | 1.00 | 27.51 |
| 22562 | CA | SER | D | 551 | -107.961 | -13.810 | 49.461 | 1.00 | 28.01 |
| 22563 | CB | SER | D | 551 | -108.754 | -14.007 | 48.189 | 1.00 | 27.25 |
| 22564 | OG | SER | D | 551 | -107.986 | -14.798 | 47.310 | 1.00 | 28.09 |
| 22565 | C | SER | D | 551 | -108.707 | -13.001 | 50.433 | 1.00 | 27.68 |
| 22566 | O | SER | D | 551 | -109.465 | -13.565 | 51.223 | 1.00 | 28.39 |
| 22567 | N | PHE | D | 552 | -108.489 | -11.691 | 50.382 | 1.00 | 26.99 |
| 22568 | CA | PHE | D | 552 | -109.076 | -10.779 | 51.336 | 1.00 | 26.50 |
| 22569 | CB | PHE | D | 552 | -108.028 | -10.455 | 52.408 | 1.00 | 26.23 |
| 22570 | CG | PHE | D | 552 | -108.509 | -9.514 | 53.464 | 1.00 | 26.10 |
| 22571 | CD1 | PHE | D | 552 | -109.320 | -9.962 | 54.495 | 1.00 | 26.43 |
| 22572 | CE1 | PHE | D | 552 | -109.764 | -9.081 | 55.477 | 1.00 | 26.53 |
| 22573 | CZ | PHE | D | 552 | -109.404 | -7.758 | 55.425 | 1.00 | 25.63 |
| 22574 | CE2 | PHE | D | 552 | -108.595 | -7.310 | 54.418 | 1.00 | 25.99 |
| 22575 | CD2 | PHE | D | 552 | -108.145 | -8.190 | 53.439 | 1.00 | 25.54 |
| 22576 | C | PHE | D | 552 | -109.546 | -9.506 | 50.650 | 1.00 | 26.56 |
| 22577 | O | PHE | D | 552 | -108.831 | -8.934 | 49.849 | 1.00 | 26.45 |
| 22578 | N | ASP | D | 553 | -110.764 | -9.073 | 50.967 | 1.00 | 26.84 |
| 22579 | CA | ASP | D | 553 | -111.307 | -7.826 | 50.451 | 1.00 | 25.94 |
| 22580 | CB | ASP | D | 553 | -112.769 | -7.996 | 50.036 | 1.00 | 25.66 |
| 22581 | CG | ASP | D | 553 | -112.948 | -8.942 | 48.858 | 1.00 | 25.92 |
| 22582 | OD1 | ASP | D | 553 | -112.023 | -9.073 | 49.032 | 1.00 | 22.66 |
| 22583 | OD2 | ASP | D | 553 | -113.995 | -9.605 | 48.682 | 1.00 | 27.52 |

FIGURE 3 SC

| A | B | C | D | E | F | G | H | I | J |
|---|---|---|---|---|---|---|---|---|---|
| 22584 | C | ASP | D | 553 | -111.244 | -6.789 | 51.553 | 1.00 | 26.12 |
| 22585 | O | ASP | D | 553 | -112.113 | -6.762 | 52.432 | 1.00 | 26.68 |
| 22586 | N | GLY | D | 554 | -110.234 | -5.928 | 51.516 | 1.00 | 25.48 |
| 22587 | CA | GLY | D | 554 | -110.116 | -4.893 | 52.521 | 1.00 | 25.03 |
| 22588 | C | GLY | D | 554 | -110.654 | -3.556 | 52.057 | 1.00 | 24.97 |
| 22589 | O | GLY | D | 554 | -111.596 | -3.502 | 51.273 | 1.00 | 25.10 |
| 22590 | N | ARG | D | 555 | -110.063 | -2.468 | 52.546 | 1.00 | 24.82 |
| 22591 | CA | ARG | D | 555 | -110.487 | -1.142 | 52.127 | 1.00 | 24.46 |
| 22592 | CB | ARG | D | 555 | -109.787 | -0.067 | 52.952 | 1.00 | 24.30 |
| 22593 | CG | ARG | D | 555 | -110.429 | 0.147 | 54.341 | 1.00 | 24.14 |
| 22594 | CD | ARG | D | 555 | -109.582 | 0.985 | 55.282 | 1.00 | 23.12 |
| 22595 | NE | ARG | D | 555 | -108.311 | 0.342 | 55.614 | 1.00 | 22.67 |
| 22596 | CZ | ARG | D | 555 | -107.446 | 0.851 | 56.473 | 1.00 | 23.02 |
| 22597 | NH1 | ARG | D | 555 | -107.718 | 2.010 | 57.046 | 1.00 | 22.64 |
| 22598 | NH2 | ARG | D | 555 | -106.318 | 0.212 | 56.764 | 1.00 | 22.47 |
| 22599 | C | ARG | D | 555 | -110.262 | -0.957 | 50.615 | 1.00 | 24.24 |
| 22600 | O | ARG | D | 555 | -109.253 | -1.424 | 50.068 | 1.00 | 23.62 |
| 22601 | N | GLY | D | 556 | -111.209 | -0.285 | 49.959 | 1.00 | 23.17 |
| 22602 | CA | GLY | D | 556 | -111.192 | -0.154 | 48.514 | 1.00 | 23.85 |
| 22603 | C | GLY | D | 556 | -112.076 | -1.209 | 47.838 | 1.00 | 24.14 |
| 22604 | O | GLY | D | 556 | -112.551 | -1.008 | 46.727 | 1.00 | 23.54 |
| 22605 | N | SER | D | 557 | -112.309 | -2.330 | 48.519 | 1.00 | 24.74 |
| 22606 | CA | SER | D | 557 | -113.092 | -3.431 | 47.949 | 1.00 | 25.59 |
| 22607 | CB | SER | D | 557 | -112.978 | -4.696 | 48.811 | 1.00 | 25.61 |
| 22608 | OG | SER | D | 557 | -113.803 | -4.610 | 49.962 | 1.00 | 27.57 |
| 22609 | C | SER | D | 557 | -114.547 | -3.020 | 47.697 | 1.00 | 25.30 |
| 22610 | O | SER | D | 557 | -115.020 | -2.030 | 48.250 | 1.00 | 25.68 |
| 22611 | N | GLY | D | 558 | -115.246 | -3.759 | 46.840 | 1.00 | 25.65 |
| 22612 | CA | GLY | D | 558 | -116.579 | -3.350 | 46.401 | 1.00 | 25.83 |
| 22613 | C | GLY | D | 558 | -117.793 | -3.985 | 47.056 | 1.00 | 26.02 |
| 22614 | O | GLY | D | 558 | -117.668 | -4.868 | 47.898 | 1.00 | 26.32 |
| 22615 | N | TYR | D | 559 | -118.969 | -3.502 | 46.673 | 1.00 | 26.34 |
| 22616 | CA | TYR | D | 559 | -120.250 | -4.099 | 47.058 | 1.00 | 27.19 |
| 22617 | CB | TYR | D | 559 | -120.344 | -5.531 | 46.482 | 1.00 | 27.45 |
| 22618 | CG | TYR | D | 559 | -119.810 | -5.588 | 45.074 | 1.00 | 27.95 |
| 22619 | CD1 | TYR | D | 559 | -118.562 | -6.141 | 44.799 | 1.00 | 27.49 |
| 22620 | CE1 | TYR | D | 559 | -118.066 | -6.172 | 43.501 | 1.00 | 27.94 |
| 22621 | CZ | TYR | D | 559 | -118.813 | -5.618 | 42.471 | 1.00 | 28.56 |
| 22622 | OH | TYR | D | 559 | -118.323 | -5.599 | 41.188 | 1.00 | 27.38 |
| 22623 | CE2 | TYR | D | 559 | -120.029 | -5.035 | 42.731 | 1.00 | 28.45 |
| 22624 | CD2 | TYR | D | 559 | -120.514 | -5.011 | 44.029 | 1.00 | 28.47 |
| 22625 | C | TYR | D | 559 | -120.591 | -4.091 | 48.549 | 1.00 | 27.37 |
| 22626 | O | TYR | D | 559 | -121.465 | -4.850 | 48.983 | 1.00 | 27.51 |
| 22627 | N | GLN | D | 560 | -119.953 | -3.204 | 49.311 | 1.00 | 27.31 |
| 22628 | CA | GLN | D | 560 | -120.146 | -3.101 | 50.759 | 1.00 | 27.23 |
| 22629 | CB | GLN | D | 560 | -118.908 | -3.625 | 51.489 | 1.00 | 27.77 |
| 22630 | CG | GLN | D | 560 | -118.519 | -5.043 | 51.134 | 1.00 | 28.91 |
| 22631 | CD | GLN | D | 560 | -117.054 | -5.331 | 51.357 | 1.00 | 31.26 |
| 22632 | OE1 | GLN | D | 560 | -116.624 | -6.576 | 52.491 | 1.00 | 31.80 |
| 22633 | NE2 | GLN | D | 560 | -116.280 | -5.344 | 50.268 | 1.00 | 30.99 |
| 22634 | C | GLN | D | 560 | -120.366 | -1.645 | 51.151 | 1.00 | 27.53 |

FIGURE 3 SD

| A | B | C | D | E | F | G | H | I | J |
|---|---|---|---|---|---|---|---|---|---|
| 22635 | C | GLN | D | 560 | -120.236 | -1.267 | 52.321 | 1.00 | 27.86 |
| 22636 | N | GLY | D | 561 | -120.679 | -0.817 | 50.161 | 1.00 | 27.89 |
| 22637 | CA | GLY | D | 561 | -120.889 | 0.602 | 50.395 | 1.00 | 27.38 |
| 22638 | C | GLY | D | 561 | -119.659 | 1.477 | 50.206 | 1.00 | 27.11 |
| 22639 | O | GLY | D | 561 | -118.524 | 1.008 | 50.263 | 1.00 | 26.62 |
| 22640 | N | ASP | D | 562 | -119.892 | 2.767 | 49.995 | 1.00 | 27.30 |
| 22641 | CA | ASP | D | 562 | -118.812 | 3.709 | 49.753 | 1.00 | 28.31 |
| 22642 | CB | ASP | D | 562 | -119.365 | 5.051 | 49.321 | 1.00 | 28.36 |
| 22643 | CG | ASP | D | 562 | -120.046 | 4.988 | 47.983 | 1.00 | 29.39 |
| 22644 | OD1 | ASP | D | 562 | -119.845 | 3.988 | 47.236 | 1.00 | 30.55 |
| 22645 | OD2 | ASP | D | 562 | -120.815 | 5.894 | 47.610 | 1.00 | 29.84 |
| 22646 | C | ASP | D | 562 | -117.812 | 3.926 | 50.880 | 1.00 | 28.85 |
| 22647 | O | ASP | D | 562 | -116.637 | 4.191 | 50.616 | 1.00 | 29.41 |
| 22648 | N | LYS | D | 563 | -118.249 | 3.850 | 52.127 | 1.00 | 29.56 |
| 22649 | CA | LYS | D | 563 | -117.301 | 4.043 | 53.225 | 1.00 | 30.60 |
| 22650 | CB | LYS | D | 563 | -117.917 | 3.696 | 54.573 | 1.00 | 31.11 |
| 22651 | CG | LYS | D | 563 | -116.916 | 3.688 | 55.720 | 1.00 | 34.21 |
| 22652 | CD | LYS | D | 563 | -116.706 | 5.123 | 56.259 | 1.00 | 41.16 |
| 22653 | CE | LYS | D | 563 | -115.530 | 5.204 | 57.255 | 1.00 | 43.33 |
| 22654 | NZ | LYS | D | 563 | -115.058 | 6.615 | 57.450 | 1.00 | 44.62 |
| 22655 | C | LYS | D | 563 | -116.087 | 3.165 | 52.984 | 1.00 | 30.00 |
| 22656 | O | LYS | D | 563 | -114.957 | 3.612 | 53.094 | 1.00 | 30.15 |
| 22657 | N | ILE | D | 564 | -116.328 | 1.906 | 52.642 | 1.00 | 29.49 |
| 22658 | CA | ILE | D | 564 | -115.235 | 0.996 | 52.373 | 1.00 | 28.53 |
| 22659 | CB | ILE | D | 564 | -115.717 | -0.469 | 52.546 | 1.00 | 29.28 |
| 22660 | CG1 | ILE | D | 564 | -115.851 | -0.832 | 54.031 | 1.00 | 27.78 |
| 22661 | CD1 | ILE | D | 564 | -116.449 | -2.225 | 54.258 | 1.00 | 26.22 |
| 22662 | CG2 | ILE | D | 564 | -114.757 | -1.466 | 51.812 | 1.00 | 27.48 |
| 22663 | C | ILE | D | 564 | -114.642 | 1.180 | 50.973 | 1.00 | 28.08 |
| 22664 | O | ILE | D | 564 | -113.441 | 1.096 | 50.794 | 1.00 | 28.14 |
| 22665 | N | MET | D | 565 | -115.471 | 1.426 | 49.971 | 1.00 | 27.98 |
| 22666 | CA | MET | D | 565 | -114.939 | 1.458 | 48.603 | 1.00 | 27.61 |
| 22667 | CB | MET | D | 565 | -116.057 | 1.360 | 47.561 | 1.00 | 27.73 |
| 22668 | CG | MET | D | 565 | -115.550 | 1.349 | 46.129 | 1.00 | 26.07 |
| 22669 | SD | MET | D | 565 | -116.862 | 1.094 | 44.933 | 1.00 | 27.30 |
| 22670 | CE | MET | D | 565 | -117.601 | 2.652 | 44.824 | 1.00 | 25.23 |
| 22671 | C | MET | D | 565 | -114.088 | 2.672 | 48.333 | 1.00 | 27.63 |
| 22672 | O | MET | D | 565 | -113.015 | 2.559 | 47.745 | 1.00 | 27.09 |
| 22673 | N | HIS | D | 566 | -114.578 | 3.830 | 48.773 | 1.00 | 27.52 |
| 22674 | CA | HIS | D | 566 | -113.881 | 5.093 | 48.577 | 1.00 | 27.65 |
| 22675 | CB | HIS | D | 566 | -114.865 | 6.269 | 48.626 | 1.00 | 27.68 |
| 22676 | CG | HIS | D | 566 | -115.793 | 6.303 | 47.457 | 1.00 | 26.99 |
| 22677 | ND1 | HIS | D | 566 | -116.939 | 7.066 | 47.429 | 1.00 | 28.50 |
| 22678 | CE1 | HIS | D | 566 | -117.567 | 6.871 | 46.281 | 1.00 | 28.97 |
| 22679 | NE2 | HIS | D | 566 | -116.873 | 5.999 | 45.569 | 1.00 | 26.95 |
| 22680 | CD2 | HIS | D | 566 | -115.766 | 5.620 | 46.290 | 1.00 | 27.38 |
| 22681 | C | HIS | D | 566 | -112.754 | 5.329 | 49.555 | 1.00 | 27.89 |
| 22682 | O | HIS | D | 566 | -112.116 | 6.376 | 49.526 | 1.00 | 28.02 |
| 22683 | N | ALA | D | 567 | -112.488 | 4.358 | 50.418 | 1.00 | 28.19 |
| 22684 | CA | ALA | D | 567 | -111.425 | 4.533 | 51.401 | 1.00 | 28.18 |
| 22685 | CB | ALA | D | 567 | -111.348 | 3.320 | 52.332 | 1.00 | 28.22 |

FIGURE 3 SE

| A | B | C | D | E | F | G | H | I | J |
|---|---|---|---|---|---|---|---|---|---|
| 22686 | C | ALA | D | 567 | -110.071 | 4.789 | 50.740 | 1.00 | 28.08 |
| 22687 | O | ALA | D | 567 | -109.205 | 5.449 | 51.328 | 1.00 | 27.85 |
| 22688 | N | ILE | D | 568 | -109.874 | 4.259 | 49.528 | 1.00 | 27.58 |
| 22689 | CA | ILE | D | 568 | -108.598 | 4.447 | 48.850 | 1.00 | 27.06 |
| 22690 | CB | ILE | D | 568 | -108.082 | 3.124 | 48.203 | 1.00 | 27.60 |
| 22691 | CG1 | ILE | D | 568 | -109.113 | 2.479 | 47.291 | 1.00 | 26.85 |
| 22692 | CD1 | ILE | D | 568 | -109.901 | 3.443 | 46.432 | 1.00 | 29.00 |
| 22693 | CG2 | ILE | D | 568 | -107.640 | 2.107 | 49.293 | 1.00 | 28.00 |
| 22694 | C | ILE | D | 568 | -108.593 | 5.594 | 47.844 | 1.00 | 27.07 |
| 22695 | O | ILE | D | 568 | -107.677 | 5.697 | 47.015 | 1.00 | 26.67 |
| 22696 | N | ASN | D | 569 | -109.608 | 6.456 | 47.920 | 1.00 | 26.74 |
| 22697 | CA | ASN | D | 569 | -109.717 | 7.583 | 46.997 | 1.00 | 26.98 |
| 22698 | CB | ASN | D | 569 | -110.934 | 8.450 | 47.337 | 1.00 | 26.81 |
| 22699 | CG | ASN | D | 569 | -111.215 | 9.499 | 46.277 | 1.00 | 29.08 |
| 22700 | OD1 | ASN | D | 569 | -111.277 | 10.699 | 46.570 | 1.00 | 31.62 |
| 22701 | ND2 | ASN | D | 569 | -111.367 | 9.058 | 45.034 | 1.00 | 28.47 |
| 22702 | C | ASN | D | 569 | -108.458 | 8.435 | 47.024 | 1.00 | 27.29 |
| 22703 | O | ASN | D | 569 | -108.073 | 8.946 | 48.075 | 1.00 | 26.42 |
| 22704 | N | ARG | D | 570 | -107.791 | 8.544 | 45.877 | 1.00 | 27.75 |
| 22705 | CA | ARG | D | 570 | -106.620 | 9.405 | 45.760 | 1.00 | 28.44 |
| 22706 | CB | ARG | D | 570 | -106.924 | 10.792 | 46.346 | 1.00 | 28.62 |
| 22707 | CG | ARG | D | 570 | -107.950 | 11.571 | 45.559 | 1.00 | 30.72 |
| 22708 | CD | ARG | D | 570 | -108.236 | 12.971 | 46.119 | 1.00 | 36.07 |
| 22709 | NE | ARG | D | 570 | -107.033 | 13.789 | 46.249 | 1.00 | 38.04 |
| 22710 | CZ | ARG | D | 570 | -106.550 | 14.551 | 45.282 | 1.00 | 39.15 |
| 22711 | NH1 | ARG | D | 570 | -107.167 | 14.596 | 44.108 | 1.00 | 39.37 |
| 22712 | NH2 | ARG | D | 570 | -105.448 | 15.267 | 45.483 | 1.00 | 40.48 |
| 22713 | C | ARG | D | 570 | -105.439 | 8.805 | 46.473 | 1.00 | 28.36 |
| 22714 | O | ARG | D | 570 | -104.361 | 9.397 | 46.559 | 1.00 | 27.76 |
| 22715 | N | ARG | D | 571 | -105.618 | 7.595 | 46.964 | 1.00 | 28.89 |
| 22716 | CA | ARG | D | 571 | -104.562 | 7.056 | 47.778 | 1.00 | 29.67 |
| 22717 | CB | ARG | D | 571 | -104.861 | 7.341 | 49.256 | 1.00 | 29.49 |
| 22718 | CG | ARG | D | 571 | -103.669 | 7.967 | 49.989 | 1.00 | 34.40 |
| 22719 | CD | ARG | D | 571 | -103.706 | 9.481 | 50.211 | 1.00 | 37.34 |
| 22720 | NE | ARG | D | 571 | -103.697 | 10.225 | 48.963 | 1.00 | 40.61 |
| 22721 | CZ | ARG | D | 571 | -103.474 | 11.525 | 48.868 | 1.00 | 41.04 |
| 22722 | NH1 | ARG | D | 571 | -103.490 | 12.103 | 47.672 | 1.00 | 40.49 |
| 22723 | NH2 | ARG | D | 571 | -103.233 | 12.248 | 49.960 | 1.00 | 41.29 |
| 22724 | C | ARG | D | 571 | -104.290 | 5.589 | 47.472 | 1.00 | 29.13 |
| 22725 | O | ARG | D | 571 | -104.166 | 4.748 | 48.366 | 1.00 | 29.48 |
| 22726 | N | LEU | D | 572 | -104.165 | 5.290 | 46.186 | 1.00 | 28.53 |
| 22727 | CA | LEU | D | 572 | -103.865 | 3.918 | 45.770 | 1.00 | 28.13 |
| 22728 | CB | LEU | D | 572 | -103.815 | 3.814 | 44.246 | 1.00 | 27.82 |
| 22729 | CG | LEU | D | 572 | -105.077 | 3.332 | 43.525 | 1.00 | 28.58 |
| 22730 | CD1 | LEU | D | 572 | -105.174 | 3.831 | 42.088 | 1.00 | 25.84 |
| 22731 | CD2 | LEU | D | 572 | -106.344 | 3.628 | 44.310 | 1.00 | 28.27 |
| 22732 | C | LEU | D | 572 | -102.534 | 3.495 | 46.372 | 1.00 | 27.64 |
| 22733 | O | LEU | D | 572 | -101.662 | 4.323 | 46.605 | 1.00 | 28.39 |
| 22734 | N | GLY | D | 573 | -102.379 | 2.210 | 46.640 | 1.00 | 26.99 |
| 22735 | CA | GLY | D | 573 | -101.137 | 1.711 | 47.178 | 1.00 | 25.65 |
| 22736 | C | GLY | D | 573 | -100.985 | 2.031 | 48.656 | 1.00 | 25.59 |

FIGURE 3 SF

| A | B | C | D | E | F | G | H | I | J |
|---|---|---|---|---|---|---|---|---|---|
| 22737 | O | GLY | D | 573 | -99.872 | 2.088 | 49.158 | 1.00 | 25.01 |
| 22738 | N | THR | D | 574 | -102.089 | 2.271 | 49.358 | 1.00 | 25.02 |
| 22739 | CA | THR | D | 574 | -101.978 | 2.512 | 50.798 | 1.00 | 24.80 |
| 22740 | CB | THR | D | 574 | -102.403 | 3.932 | 51.175 | 1.00 | 24.60 |
| 22741 | OG1 | THR | D | 574 | -103.769 | 4.133 | 50.788 | 1.00 | 25.11 |
| 22742 | CG2 | THR | D | 574 | -101.624 | 4.977 | 50.361 | 1.00 | 24.02 |
| 22743 | C | THR | D | 574 | -102.786 | 1.507 | 51.618 | 1.00 | 24.68 |
| 22744 | O | THR | D | 574 | -102.291 | 0.453 | 51.957 | 1.00 | 23.86 |
| 22745 | N | PHE | D | 575 | -104.039 | 1.843 | 51.913 | 1.00 | 25.42 |
| 22746 | CA | PHE | D | 575 | -104.884 | 1.037 | 52.786 | 1.00 | 26.24 |
| 22747 | CB | PHE | D | 575 | -106.212 | 1.749 | 53.005 | 1.00 | 26.92 |
| 22748 | CG | PHE | D | 575 | -106.088 | 3.074 | 53.724 | 1.00 | 28.29 |
| 22749 | CD1 | PHE | D | 575 | -105.145 | 3.260 | 54.707 | 1.00 | 28.72 |
| 22750 | CE1 | PHE | D | 575 | -105.050 | 4.475 | 55.390 | 1.00 | 30.07 |
| 22751 | CZ | PHE | D | 575 | -105.896 | 5.510 | 55.090 | 1.00 | 29.21 |
| 22752 | CE2 | PHE | D | 575 | -106.848 | 5.335 | 54.106 | 1.00 | 31.74 |
| 22753 | CD2 | PHE | D | 575 | -106.949 | 4.113 | 53.435 | 1.00 | 29.53 |
| 22754 | C | PHE | D | 575 | -105.167 | -0.374 | 52.291 | 1.00 | 26.80 |
| 22755 | O | PHE | D | 575 | -105.347 | -1.297 | 53.094 | 1.00 | 27.14 |
| 22756 | N | GLU | D | 576 | -105.226 | -0.541 | 50.973 | 1.00 | 26.67 |
| 22757 | CA | GLU | D | 576 | -105.526 | -1.825 | 50.386 | 1.00 | 26.70 |
| 22758 | CB | GLU | D | 576 | -106.059 | -1.656 | 48.953 | 1.00 | 27.22 |
| 22759 | CG | GLU | D | 576 | -104.999 | -1.536 | 47.850 | 1.00 | 28.25 |
| 22760 | CD | GLU | D | 576 | -104.397 | -0.139 | 47.693 | 1.00 | 29.97 |
| 22761 | OE1 | GLU | D | 576 | -104.224 | 0.603 | 48.695 | 1.00 | 29.55 |
| 22762 | OE2 | GLU | D | 576 | -104.064 | 0.213 | 46.544 | 1.00 | 31.10 |
| 22763 | C | GLU | D | 576 | -104.284 | -2.701 | 50.463 | 1.00 | 27.03 |
| 22764 | O | GLU | D | 576 | -104.381 | -3.921 | 50.618 | 1.00 | 27.54 |
| 22765 | N | VAL | D | 577 | -103.113 | -2.082 | 50.372 | 1.00 | 27.44 |
| 22766 | CA | VAL | D | 577 | -101.849 | -2.797 | 50.534 | 1.00 | 27.86 |
| 22767 | CB | VAL | D | 577 | -100.634 | -1.902 | 50.144 | 1.00 | 28.09 |
| 22768 | CG1 | VAL | D | 577 | -100.673 | -1.570 | 48.673 | 1.00 | 27.66 |
| 22769 | CG2 | VAL | D | 577 | -99.293 | -2.566 | 50.504 | 1.00 | 26.74 |
| 22770 | C | VAL | D | 577 | -101.729 | -3.218 | 52.006 | 1.00 | 28.75 |
| 22771 | O | VAL | D | 577 | -101.523 | -4.386 | 52.314 | 1.00 | 27.76 |
| 22772 | N | GLU | D | 578 | -101.889 | -2.244 | 52.900 | 1.00 | 29.84 |
| 22773 | CA | GLU | D | 578 | -101.814 | -2.454 | 54.348 | 1.00 | 31.68 |
| 22774 | CB | GLU | D | 578 | -102.010 | -1.110 | 55.089 | 1.00 | 32.26 |
| 22775 | CG | GLU | D | 578 | -100.801 | -0.173 | 54.957 | 1.00 | 37.82 |
| 22776 | CD | GLU | D | 578 | -101.117 | 1.320 | 55.116 | 1.00 | 45.04 |
| 22777 | OE1 | GLU | D | 578 | -100.809 | 2.100 | 54.163 | 1.00 | 47.10 |
| 22778 | OE2 | GLU | D | 578 | -101.632 | 1.736 | 56.196 | 1.00 | 46.15 |
| 22779 | C | GLU | D | 578 | -102.811 | -3.519 | 54.825 | 1.00 | 31.53 |
| 22780 | O | GLU | D | 578 | -102.450 | -4.412 | 55.596 | 1.00 | 31.88 |
| 22781 | N | ASP | D | 579 | -104.052 | -3.450 | 54.345 | 1.00 | 31.09 |
| 22782 | CA | ASP | D | 579 | -105.054 | -4.420 | 54.764 | 1.00 | 30.71 |
| 22783 | CB | ASP | D | 579 | -106.443 | -4.034 | 54.266 | 1.00 | 31.02 |
| 22784 | CG | ASP | D | 579 | -107.014 | -2.810 | 54.984 | 1.00 | 32.48 |
| 22785 | OD1 | ASP | D | 579 | -106.396 | -2.324 | 55.962 | 1.00 | 33.16 |
| 22786 | OD2 | ASP | D | 579 | -108.090 | -2.261 | 54.632 | 1.00 | 33.82 |
| 22787 | C | ASP | D | 579 | -104.679 | -5.863 | 54.361 | 1.00 | 30.02 |

FIGURE 3 SG

| A | B | C | D | E | F | G | H | I | J |
|---|---|---|---|---|---|---|---|---|---|
| 22788 | O | ASP | D | 579 | -104.980 | -6.809 | 55.085 | 1.00 | 29.35 |
| 22789 | N | GLN | D | 580 | -104.007 | -6.037 | 53.229 | 1.00 | 29.15 |
| 22790 | CA | GLN | D | 580 | -103.561 | -7.375 | 52.844 | 1.00 | 28.97 |
| 22791 | CB | GLN | D | 580 | -102.978 | -7.394 | 51.428 | 1.00 | 28.42 |
| 22792 | CG | GLN | D | 580 | -103.972 | -7.130 | 50.322 | 1.00 | 27.58 |
| 22793 | CD | GLN | D | 580 | -104.992 | -8.242 | 50.155 | 1.00 | 27.11 |
| 22794 | OE1 | GLN | D | 580 | -104.625 | -9.400 | 50.001 | 1.00 | 25.81 |
| 22795 | NE2 | GLN | D | 580 | -106.280 | -7.883 | 50.161 | 1.00 | 25.38 |
| 22796 | C | GLN | D | 580 | -102.512 | -7.896 | 53.828 | 1.00 | 29.53 |
| 22797 | O | GLN | D | 580 | -102.454 | -9.095 | 54.117 | 1.00 | 29.69 |
| 22798 | N | ILE | D | 581 | -101.661 | -7.002 | 54.321 | 1.00 | 29.77 |
| 22799 | CA | ILE | D | 581 | -100.649 | -7.403 | 55.272 | 1.00 | 30.78 |
| 22800 | CB | ILE | D | 581 | -99.610 | -6.280 | 55.453 | 1.00 | 30.83 |
| 22801 | CG1 | ILE | D | 581 | -98.635 | -6.234 | 54.267 | 1.00 | 30.50 |
| 22802 | CD1 | ILE | D | 581 | -98.115 | -4.801 | 54.003 | 1.00 | 29.32 |
| 22803 | CG2 | ILE | D | 581 | -98.837 | -6.434 | 56.772 | 1.00 | 30.88 |
| 22804 | C | ILE | D | 581 | -101.318 | -7.778 | 56.599 | 1.00 | 31.22 |
| 22805 | O | ILE | D | 581 | -101.019 | -8.815 | 57.185 | 1.00 | 31.08 |
| 22806 | N | GLU | D | 582 | -102.229 | -6.925 | 57.052 | 1.00 | 31.70 |
| 22807 | CA | GLU | D | 582 | -102.977 | -7.160 | 58.286 | 1.00 | 32.63 |
| 22808 | CB | GLU | D | 582 | -103.890 | -5.968 | 58.609 | 1.00 | 32.27 |
| 22809 | CG | GLU | D | 582 | -104.750 | -6.176 | 59.838 | 1.00 | 33.99 |
| 22810 | CD | GLU | D | 582 | -103.925 | -6.299 | 61.114 | 1.00 | 38.62 |
| 22811 | OE1 | GLU | D | 582 | -104.472 | -6.791 | 62.124 | 1.00 | 38.76 |
| 22812 | OE2 | GLU | D | 582 | -102.734 | -5.891 | 61.114 | 1.00 | 40.20 |
| 22813 | C | GLU | D | 582 | -103.801 | -8.444 | 58.194 | 1.00 | 32.47 |
| 22814 | O | GLU | D | 582 | -103.972 | -9.158 | 59.183 | 1.00 | 33.17 |
| 22815 | N | ALA | D | 583 | -104.292 | -8.740 | 57.002 | 1.00 | 32.20 |
| 22816 | CA | ALA | D | 583 | -105.040 | -9.974 | 56.783 | 1.00 | 32.77 |
| 22817 | CB | ALA | D | 583 | -105.639 | -10.020 | 55.371 | 1.00 | 32.21 |
| 22818 | C | ALA | D | 583 | -104.140 | -11.171 | 57.008 | 1.00 | 32.51 |
| 22819 | O | ALA | D | 583 | -104.515 | -12.108 | 57.702 | 1.00 | 32.29 |
| 22820 | N | ALA | D | 584 | -102.961 | -11.134 | 56.399 | 1.00 | 32.95 |
| 22821 | CA | ALA | D | 584 | -101.987 | -12.207 | 56.561 | 1.00 | 34.06 |
| 22822 | CB | ALA | D | 584 | -100.776 | -11.936 | 55.745 | 1.00 | 33.46 |
| 22823 | C | ALA | D | 584 | -101.625 | -12.358 | 58.038 | 1.00 | 35.08 |
| 22824 | O | ALA | D | 584 | -101.484 | -13.473 | 58.540 | 1.00 | 35.25 |
| 22825 | N | ARG | D | 585 | -101.504 | -11.231 | 58.729 | 1.00 | 36.40 |
| 22826 | CA | ARG | D | 585 | -101.232 | -11.240 | 60.155 | 1.00 | 38.09 |
| 22827 | CB | ARG | D | 585 | -101.007 | -9.819 | 60.693 | 1.00 | 38.45 |
| 22828 | CG | ARG | D | 585 | -99.588 | -9.293 | 60.510 | 1.00 | 37.61 |
| 22829 | CD | ARG | D | 585 | -99.263 | -8.106 | 61.400 | 1.00 | 38.68 |
| 22830 | NE | ARG | D | 585 | -98.920 | -6.886 | 60.672 | 1.00 | 40.40 |
| 22831 | CZ | ARG | D | 585 | -97.673 | -6.482 | 60.453 | 1.00 | 40.67 |
| 22832 | NH1 | ARG | D | 585 | -96.654 | -7.202 | 60.898 | 1.00 | 41.73 |
| 22833 | NH2 | ARG | D | 585 | -97.438 | -5.360 | 59.799 | 1.00 | 39.47 |
| 22834 | C | ARG | D | 585 | -102.342 | -11.921 | 60.942 | 1.00 | 39.12 |
| 22835 | O | ARG | D | 585 | -102.058 | -12.724 | 61.816 | 1.00 | 39.64 |
| 22836 | N | GLN | D | 586 | -103.599 | -11.622 | 60.630 | 1.00 | 40.11 |
| 22837 | CA | GLN | D | 586 | -104.709 | -12.224 | 61.360 | 1.00 | 41.16 |
| 22838 | CB | GLN | D | 586 | -106.025 | -11.492 | 61.091 | 1.00 | 41.10 |

FIGURE 3 SH

| A | B | C | D | E | F | G | H | I | J |
|---|---|---|---|---|---|---|---|---|---|
| 22839 | CG | GLN | D | 586 | -106.123 | -10.079 | 61.682 | 1.00 | 42.90 |
| 22840 | CD | GLN | D | 586 | -106.715 | -10.060 | 63.075 | 1.00 | 45.95 |
| 22841 | OE1 | GLN | D | 586 | -107.124 | -9.015 | 63.566 | 1.00 | 47.36 |
| 22842 | NE2 | GLN | D | 586 | -106.773 | -11.226 | 63.711 | 1.00 | 48.11 |
| 22843 | C | GLN | D | 586 | -104.861 | -13.705 | 61.031 | 1.00 | 41.99 |
| 22844 | O | GLN | D | 586 | -105.377 | -14.474 | 61.847 | 1.00 | 42.30 |
| 22845 | N | PHE | D | 587 | -104.427 | -14.101 | 59.836 | 1.00 | 42.89 |
| 22846 | CA | PHE | D | 587 | -104.498 | -15.503 | 59.426 | 1.00 | 43.33 |
| 22847 | CB | PHE | D | 587 | -104.241 | -15.677 | 57.921 | 1.00 | 42.71 |
| 22848 | CG | PHE | D | 587 | -105.281 | -15.049 | 57.037 | 1.00 | 41.34 |
| 22849 | CD1 | PHE | D | 587 | -106.572 | -14.834 | 57.493 | 1.00 | 40.20 |
| 22850 | CE1 | PHE | D | 587 | -107.521 | -14.254 | 56.671 | 1.00 | 38.14 |
| 22851 | CZ | PHE | D | 587 | -107.187 | -13.895 | 55.376 | 1.00 | 37.46 |
| 22852 | CE2 | PHE | D | 587 | -105.919 | -14.116 | 54.912 | 1.00 | 36.54 |
| 22853 | CD2 | PHE | D | 587 | -104.971 | -14.685 | 55.735 | 1.00 | 38.81 |
| 22854 | C | PHE | D | 587 | -103.440 | -16.252 | 60.226 | 1.00 | 44.39 |
| 22855 | O | PHE | D | 587 | -103.657 | -17.389 | 60.638 | 1.00 | 44.74 |
| 22856 | N | SER | D | 588 | -102.292 | -15.606 | 60.430 | 1.00 | 45.69 |
| 22857 | CA | SER | D | 588 | -101.217 | -16.161 | 61.258 | 1.00 | 47.02 |
| 22858 | CB | SER | D | 588 | -100.030 | -15.195 | 61.361 | 1.00 | 47.26 |
| 22859 | OG | SER | D | 588 | -99.056 | -15.433 | 60.351 | 1.00 | 48.72 |
| 22860 | C | SER | D | 588 | -101.720 | -16.455 | 62.663 | 1.00 | 47.44 |
| 22861 | O | SER | D | 588 | -101.435 | -17.517 | 63.217 | 1.00 | 47.74 |
| 22862 | N | LYS | D | 589 | -102.472 | -15.524 | 63.238 | 1.00 | 47.68 |
| 22863 | CA | LYS | D | 589 | -102.988 | -15.726 | 64.586 | 1.00 | 48.75 |
| 22864 | CB | LYS | D | 589 | -103.438 | -14.397 | 65.214 | 1.00 | 48.90 |
| 22865 | CG | LYS | D | 589 | -102.318 | -13.665 | 65.968 | 1.00 | 51.80 |
| 22866 | CD | LYS | D | 589 | -101.415 | -12.829 | 65.027 | 1.00 | 56.24 |
| 22867 | CE | LYS | D | 589 | -100.144 | -12.316 | 65.741 | 1.00 | 58.28 |
| 22868 | NZ | LYS | D | 589 | -99.516 | -11.165 | 65.007 | 1.00 | 60.63 |
| 22869 | C | LYS | D | 589 | -104.093 | -16.788 | 64.665 | 1.00 | 48.47 |
| 22870 | O | LYS | D | 589 | -104.526 | -17.158 | 65.759 | 1.00 | 49.01 |
| 22871 | N | MET | D | 590 | -104.539 | -17.283 | 63.515 | 1.00 | 47.95 |
| 22872 | CA | MET | D | 590 | -105.591 | -18.293 | 63.503 | 1.00 | 47.45 |
| 22873 | CB | MET | D | 590 | -106.346 | -18.303 | 62.171 | 1.00 | 47.08 |
| 22874 | CG | MET | D | 590 | -107.438 | -17.267 | 62.106 | 1.00 | 46.07 |
| 22875 | SD | MET | D | 590 | -108.073 | -17.158 | 60.449 | 1.00 | 44.94 |
| 22876 | CE | MET | D | 590 | -109.348 | -15.990 | 60.659 | 1.00 | 45.88 |
| 22877 | C | MET | D | 590 | -105.095 | -19.711 | 63.865 | 1.00 | 47.12 |
| 22878 | O | MET | D | 590 | -105.898 | -20.636 | 64.054 | 1.00 | 47.49 |
| 22879 | N | GLY | D | 591 | -103.776 | -19.890 | 63.940 | 1.00 | 46.11 |
| 22880 | CA | GLY | D | 591 | -103.200 | -21.150 | 64.388 | 1.00 | 44.74 |
| 22881 | C | GLY | D | 591 | -102.758 | -22.185 | 63.369 | 1.00 | 44.10 |
| 22882 | O | GLY | D | 591 | -101.780 | -22.897 | 63.599 | 1.00 | 44.53 |
| 22883 | N | PHE | D | 592 | -103.471 | -22.294 | 62.254 | 1.00 | 42.57 |
| 22884 | CA | PHE | D | 592 | -103.126 | -23.294 | 61.258 | 1.00 | 40.76 |
| 22885 | CB | PHE | D | 592 | -104.397 | -23.899 | 60.674 | 1.00 | 41.08 |
| 22886 | CG | PHE | D | 592 | -105.425 | -22.884 | 60.306 | 1.00 | 40.63 |
| 22887 | CD1 | PHE | D | 592 | -106.558 | -22.719 | 61.075 | 1.00 | 41.45 |
| 22888 | CE1 | PHE | D | 592 | -107.511 | -21.772 | 60.727 | 1.00 | 40.92 |
| 22889 | CZ | PHE | D | 592 | -107.322 | -20.993 | 59.602 | 1.00 | 39.45 |

FIGURE 3 SI

| A | B | C | D | E | F | G | H | I | J |
|---|---|---|---|---|---|---|---|---|---|
| 22890 | CE2 | PHE | D | 592 | -106.197 | -21.156 | 58.839 | 1.00 | 38.64 |
| 22891 | CD2 | PHE | D | 592 | -105.257 | -22.087 | 59.188 | 1.00 | 39.90 |
| 22892 | C | PHE | D | 592 | -102.241 | -22.752 | 60.135 | 1.00 | 39.98 |
| 22893 | O | PHE | D | 592 | -102.193 | -23.327 | 59.035 | 1.00 | 39.38 |
| 22894 | N | VAL | D | 593 | -101.536 | -21.658 | 60.409 | 1.00 | 38.64 |
| 22895 | CA | VAL | D | 593 | -100.630 | -21.083 | 59.411 | 1.00 | 37.58 |
| 22896 | CB | VAL | D | 593 | -101.005 | -19.628 | 59.041 | 1.00 | 37.59 |
| 22897 | CG1 | VAL | D | 593 | -99.801 | -18.892 | 58.427 | 1.00 | 36.42 |
| 22898 | CG2 | VAL | D | 593 | -102.186 | -19.618 | 58.087 | 1.00 | 36.64 |
| 22899 | C | VAL | D | 593 | -99.170 | -21.140 | 59.809 | 1.00 | 37.12 |
| 22900 | O | VAL | D | 593 | -98.782 | -20.674 | 60.884 | 1.00 | 37.47 |
| 22901 | N | ASP | D | 594 | -98.353 | -21.720 | 58.943 | 1.00 | 36.52 |
| 22902 | CA | ASP | D | 594 | -96.923 | -21.728 | 59.187 | 1.00 | 36.38 |
| 22903 | CB | ASP | D | 594 | -96.230 | -22.810 | 58.354 | 1.00 | 35.77 |
| 22904 | CG | ASP | D | 594 | -94.731 | -22.758 | 58.494 | 1.00 | 35.39 |
| 22905 | OD1 | ASP | D | 594 | -94.008 | -23.515 | 57.802 | 1.00 | 35.89 |
| 22906 | OD2 | ASP | D | 594 | -94.181 | -21.980 | 59.292 | 1.00 | 34.16 |
| 22907 | C | ASP | D | 594 | -96.374 | -20.345 | 58.830 | 1.00 | 36.57 |
| 22908 | O | ASP | D | 594 | -96.181 | -20.044 | 57.650 | 1.00 | 37.17 |
| 22909 | N | ASN | D | 595 | -96.160 | -19.507 | 59.840 | 1.00 | 36.30 |
| 22910 | CA | ASN | D | 595 | -95.634 | -18.148 | 59.656 | 1.00 | 36.78 |
| 22911 | CB | ASN | D | 595 | -95.377 | -17.491 | 61.018 | 1.00 | 37.54 |
| 22912 | CG | ASN | D | 595 | -96.649 | -17.078 | 61.699 | 1.00 | 41.48 |
| 22913 | OD1 | ASN | D | 595 | -97.746 | -17.471 | 61.280 | 1.00 | 45.39 |
| 22914 | ND2 | ASN | D | 595 | -96.526 | -16.287 | 62.760 | 1.00 | 43.93 |
| 22915 | C | ASN | D | 595 | -94.352 | -18.036 | 58.835 | 1.00 | 35.85 |
| 22916 | O | ASN | D | 595 | -93.994 | -16.953 | 58.370 | 1.00 | 35.40 |
| 22917 | N | LYS | D | 596 | -93.648 | -19.143 | 58.675 | 1.00 | 34.72 |
| 22918 | CA | LYS | D | 596 | -92.413 | -19.119 | 57.920 | 1.00 | 34.21 |
| 22919 | CB | LYS | D | 596 | -91.435 | -20.128 | 58.507 | 1.00 | 34.17 |
| 22920 | CG | LYS | D | 596 | -91.250 | -19.909 | 60.041 | 1.00 | 36.54 |
| 22921 | CD | LYS | D | 596 | -90.150 | -20.773 | 60.662 | 1.00 | 37.81 |
| 22922 | CE | LYS | D | 596 | -90.308 | -22.227 | 60.276 | 1.00 | 40.13 |
| 22923 | NZ | LYS | D | 596 | -91.635 | -22.778 | 60.686 | 1.00 | 41.92 |
| 22924 | C | LYS | D | 596 | -92.651 | -19.320 | 56.417 | 1.00 | 33.28 |
| 22925 | O | LYS | D | 596 | -91.740 | -19.205 | 55.602 | 1.00 | 33.31 |
| 22926 | N | ARG | D | 597 | -93.889 | -19.597 | 56.049 | 1.00 | 32.32 |
| 22927 | CA | ARG | D | 597 | -94.202 | -19.812 | 54.644 | 1.00 | 31.94 |
| 22928 | CB | ARG | D | 597 | -94.289 | -21.301 | 54.364 | 1.00 | 32.07 |
| 22929 | CG | ARG | D | 597 | -92.965 | -21.992 | 54.619 | 1.00 | 34.21 |
| 22930 | CD | ARG | D | 597 | -92.971 | -23.463 | 54.314 | 1.00 | 34.83 |
| 22931 | NE | ARG | D | 597 | -93.720 | -24.207 | 55.309 | 1.00 | 36.28 |
| 22932 | CZ | ARG | D | 597 | -94.198 | -25.416 | 55.095 | 1.00 | 38.14 |
| 22933 | NH1 | ARG | D | 597 | -94.010 | -25.999 | 53.911 | 1.00 | 38.90 |
| 22934 | NH2 | ARG | D | 597 | -94.860 | -26.040 | 56.049 | 1.00 | 37.79 |
| 22935 | C | ARG | D | 597 | -95.474 | -19.093 | 54.193 | 1.00 | 30.69 |
| 22936 | O | ARG | D | 597 | -96.473 | -19.730 | 53.857 | 1.00 | 30.79 |
| 22937 | N | ILE | D | 598 | -95.442 | -17.768 | 54.225 | 1.00 | 29.08 |
| 22938 | CA | ILE | D | 598 | -96.571 | -16.980 | 53.737 | 1.00 | 27.73 |
| 22939 | CB | ILE | D | 598 | -97.092 | -15.999 | 54.803 | 1.00 | 27.92 |
| 22940 | CG1 | ILE | D | 598 | -97.392 | -16.759 | 56.110 | 1.00 | 26.82 |

FIGURE 3 SJ

| A | B | C | D | E | F | G | H | I | J |
|---|---|---|---|---|---|---|---|---|---|
| 22941 | CD1 | ILE | D | 598 | -97.873 | -15.890 | 57.219 | 1.00 | 25.20 |
| 22942 | CG2 | ILE | D | 598 | -98.342 | -15.300 | 54.329 | 1.00 | 25.89 |
| 22943 | C | ILE | D | 598 | -96.084 | -16.276 | 52.486 | 1.00 | 27.30 |
| 22944 | O | ILE | D | 598 | -95.021 | -15.649 | 52.471 | 1.00 | 26.65 |
| 22945 | N | ALA | D | 599 | -96.846 | -16.448 | 51.419 | 1.00 | 26.51 |
| 22946 | CA | ALA | D | 599 | -96.491 | -15.902 | 50.144 | 1.00 | 25.08 |
| 22947 | CB | ALA | D | 599 | -96.186 | -17.014 | 49.175 | 1.00 | 25.13 |
| 22948 | C | ALA | D | 599 | -97.655 | -15.086 | 49.669 | 1.00 | 25.14 |
| 22949 | O | ALA | D | 599 | -98.724 | -15.064 | 50.295 | 1.00 | 24.14 |
| 22950 | N | ILE | D | 600 | -97.444 | -14.383 | 48.563 | 1.00 | 24.78 |
| 22951 | CA | ILE | D | 600 | -98.485 | -13.536 | 48.032 | 1.00 | 23.69 |
| 22952 | CB | ILE | D | 600 | -98.459 | -12.153 | 48.722 | 1.00 | 24.06 |
| 22953 | CG1 | ILE | D | 600 | -99.587 | -11.273 | 48.193 | 1.00 | 23.71 |
| 22954 | CD1 | ILE | D | 600 | -99.725 | -9.971 | 48.917 | 1.00 | 21.11 |
| 22955 | CG2 | ILE | D | 600 | -97.081 | -11.463 | 48.559 | 1.00 | 22.54 |
| 22956 | C | ILE | D | 600 | -98.274 | -13.440 | 46.548 | 1.00 | 23.68 |
| 22957 | O | ILE | D | 600 | -97.149 | -13.503 | 46.049 | 1.00 | 23.70 |
| 22958 | N | TRP | D | 601 | -99.369 | -13.334 | 45.818 | 1.00 | 23.86 |
| 22959 | CA | TRP | D | 601 | -99.271 | -13.281 | 44.376 | 1.00 | 22.92 |
| 22960 | CB | TRP | D | 601 | -99.091 | -14.680 | 43.784 | 1.00 | 22.51 |
| 22961 | CG | TRP | D | 601 | -100.342 | -15.316 | 43.245 | 1.00 | 22.42 |
| 22962 | CD1 | TRP | D | 601 | -101.266 | -15.997 | 43.949 | 1.00 | 21.34 |
| 22963 | NE1 | TRP | D | 601 | -102.258 | -16.458 | 43.121 | 1.00 | 22.82 |
| 22964 | CE2 | TRP | D | 601 | -101.970 | -16.092 | 41.834 | 1.00 | 23.85 |
| 22965 | CD2 | TRP | D | 601 | -100.767 | -15.365 | 41.874 | 1.00 | 23.54 |
| 22966 | CE3 | TRP | D | 601 | -100.250 | -14.863 | 40.673 | 1.00 | 23.20 |
| 22967 | CZ3 | TRP | D | 601 | -100.937 | -15.104 | 39.498 | 1.00 | 24.27 |
| 22968 | CH2 | TRP | D | 601 | -102.146 | -15.832 | 39.492 | 1.00 | 23.52 |
| 22969 | CZ2 | TRP | D | 601 | -102.674 | -16.331 | 40.646 | 1.00 | 22.15 |
| 22970 | C | TRP | D | 601 | -100.514 | -12.627 | 43.843 | 1.00 | 22.66 |
| 22971 | O | TRP | D | 601 | -101.545 | -12.651 | 44.493 | 1.00 | 22.09 |
| 22972 | N | GLY | D | 602 | -100.389 | -12.044 | 42.656 | 1.00 | 22.24 |
| 22973 | CA | GLY | D | 602 | -101.468 | -11.332 | 42.015 | 1.00 | 21.84 |
| 22974 | C | GLY | D | 602 | -101.087 | -10.926 | 40.603 | 1.00 | 21.79 |
| 22975 | O | GLY | D | 602 | -99.926 | -11.006 | 40.198 | 1.00 | 22.06 |
| 22976 | N | TRP | D | 603 | -102.071 | -10.438 | 39.872 | 1.00 | 22.68 |
| 22977 | CA | TRP | D | 603 | -101.951 | -10.131 | 38.455 | 1.00 | 23.29 |
| 22978 | CB | TRP | D | 603 | -102.806 | -11.160 | 37.719 | 1.00 | 23.27 |
| 22979 | CG | TRP | D | 603 | -102.592 | -11.304 | 36.278 | 1.00 | 25.73 |
| 22980 | CD1 | TRP | D | 603 | -102.670 | -10.327 | 35.335 | 1.00 | 27.22 |
| 22981 | NE1 | TRP | D | 603 | -102.409 | -10.852 | 34.090 | 1.00 | 28.83 |
| 22982 | CE2 | TRP | D | 603 | -102.166 | -12.196 | 34.209 | 1.00 | 28.70 |
| 22983 | CD2 | TRP | D | 603 | -102.284 | -12.520 | 35.574 | 1.00 | 28.46 |
| 22984 | CE3 | TRP | D | 603 | -102.069 | -13.852 | 35.967 | 1.00 | 29.49 |
| 22985 | CZ3 | TRP | D | 603 | -101.772 | -14.801 | 34.994 | 1.00 | 29.73 |
| 22986 | CH2 | TRP | D | 603 | -101.676 | -14.442 | 33.640 | 1.00 | 28.93 |
| 22987 | CZ2 | TRP | D | 603 | -101.877 | -13.150 | 33.232 | 1.00 | 28.89 |
| 22988 | C | TRP | D | 603 | -102.542 | -8.750 | 38.254 | 1.00 | 23.40 |
| 22989 | O | TRP | D | 603 | -103.594 | -8.463 | 38.792 | 1.00 | 23.07 |
| 22990 | N | SER | D | 604 | -101.873 | -7.886 | 37.494 | 1.00 | 24.27 |
| 22991 | CA | SER | D | 604 | -102.407 | -6.535 | 37.222 | 1.00 | 24.66 |

FIGURE 3 SK

| A | B | C | D | E | F | G | H | I | J |
|---|---|---|---|---|---|---|---|---|---|
| 22992 | CB | SER | D | 604 | -103.789 | -6.615 | 36.568 | 1.00 | 24.77 |
| 22993 | OG | SER | D | 604 | -104.070 | -5.413 | 35.859 | 1.00 | 26.90 |
| 22994 | C | SER | D | 604 | -102.422 | -5.670 | 38.486 | 1.00 | 23.41 |
| 22995 | O | SER | D | 604 | -101.372 | -5.445 | 39.058 | 1.00 | 23.95 |
| 22996 | N | TYR | D | 605 | -103.579 | -5.193 | 38.931 | 1.00 | 23.03 |
| 22997 | CA | TYR | D | 605 | -103.631 | -4.467 | 40.203 | 1.00 | 22.68 |
| 22998 | CB | TYR | D | 605 | -105.054 | -4.018 | 40.581 | 1.00 | 22.87 |
| 22999 | CG | TYR | D | 605 | -105.036 | -2.841 | 41.583 | 1.00 | 24.08 |
| 23000 | CD1 | TYR | D | 605 | -105.355 | -1.549 | 41.178 | 1.00 | 21.68 |
| 23001 | CE1 | TYR | D | 605 | -105.338 | -0.482 | 42.061 | 1.00 | 21.13 |
| 23002 | CZ | TYR | D | 605 | -104.977 | -0.696 | 43.366 | 1.00 | 23.44 |
| 23003 | OH | TYR | D | 605 | -104.941 | 0.359 | 44.218 | 1.00 | 23.36 |
| 23004 | CE2 | TYR | D | 605 | -104.645 | -1.964 | 43.817 | 1.00 | 24.51 |
| 23005 | CD2 | TYR | D | 605 | -104.660 | -3.032 | 42.921 | 1.00 | 24.94 |
| 23006 | C | TYR | D | 605 | -103.053 | -5.407 | 41.267 | 1.00 | 22.70 |
| 23007 | O | TYR | D | 605 | -102.310 | -4.995 | 42.169 | 1.00 | 22.81 |
| 23008 | N | GLY | D | 606 | -103.356 | -6.687 | 41.112 | 1.00 | 21.85 |
| 23009 | CA | GLY | D | 606 | -102.812 | -7.697 | 41.981 | 1.00 | 21.79 |
| 23010 | C | GLY | D | 606 | -101.293 | -7.751 | 41.985 | 1.00 | 21.22 |
| 23011 | O | GLY | D | 606 | -100.695 | -8.008 | 43.023 | 1.00 | 20.85 |
| 23012 | N | GLY | D | 607 | -100.662 | -7.548 | 40.835 | 1.00 | 20.80 |
| 23013 | CA | GLY | D | 607 | -99.208 | -7.534 | 40.794 | 1.00 | 20.33 |
| 23014 | C | GLY | D | 607 | -98.629 | -6.308 | 41.505 | 1.00 | 21.15 |
| 23015 | O | GLY | D | 607 | -97.564 | -6.384 | 42.123 | 1.00 | 21.69 |
| 23016 | N | TYR | D | 608 | -99.325 | -5.172 | 41.394 | 1.00 | 21.32 |
| 23017 | CA | TYR | D | 608 | -98.955 | -3.955 | 42.075 | 1.00 | 21.05 |
| 23018 | CB | TYR | D | 608 | -99.920 | -2.870 | 41.644 | 1.00 | 21.75 |
| 23019 | CG | TYR | D | 608 | -99.789 | -1.561 | 42.412 | 1.00 | 19.88 |
| 23020 | CD1 | TYR | D | 608 | -100.839 | -1.076 | 43.171 | 1.00 | 18.29 |
| 23021 | CE1 | TYR | D | 608 | -100.738 | 0.144 | 43.831 | 1.00 | 19.02 |
| 23022 | CZ | TYR | D | 608 | -99.576 | 0.867 | 43.738 | 1.00 | 18.01 |
| 23023 | OH | TYR | D | 608 | -99.460 | 2.076 | 44.406 | 1.00 | 19.81 |
| 23024 | CE2 | TYR | D | 608 | -98.518 | 0.382 | 42.994 | 1.00 | 16.72 |
| 23025 | CD2 | TYR | D | 608 | -98.639 | -0.802 | 42.326 | 1.00 | 16.68 |
| 23026 | C | TYR | D | 608 | -99.033 | -4.139 | 43.592 | 1.00 | 21.56 |
| 23027 | O | TYR | D | 608 | -98.074 | -3.875 | 44.301 | 1.00 | 21.04 |
| 23028 | N | VAL | D | 609 | -100.173 | -4.617 | 44.090 | 1.00 | 21.97 |
| 23029 | CA | VAL | D | 609 | -100.330 | -4.835 | 45.529 | 1.00 | 22.43 |
| 23030 | CB | VAL | D | 609 | -101.749 | -5.254 | 45.905 | 1.00 | 22.62 |
| 23031 | CG1 | VAL | D | 609 | -101.836 | -5.550 | 47.428 | 1.00 | 22.40 |
| 23032 | CG2 | VAL | D | 609 | -102.699 | -4.105 | 45.568 | 1.00 | 22.38 |
| 23033 | C | VAL | D | 609 | -99.312 | -5.822 | 46.066 | 1.00 | 23.00 |
| 23034 | O | VAL | D | 609 | -98.640 | -5.546 | 47.077 | 1.00 | 23.05 |
| 23035 | N | THR | D | 610 | -99.167 | -6.943 | 45.356 | 1.00 | 23.22 |
| 23036 | CA | THR | D | 610 | -98.195 | -7.967 | 45.702 | 1.00 | 23.21 |
| 23037 | CB | THR | D | 610 | -98.125 | -9.072 | 44.599 | 1.00 | 22.93 |
| 23038 | OG1 | THR | D | 610 | -99.203 | -9.996 | 44.777 | 1.00 | 22.62 |
| 23039 | CG2 | THR | D | 610 | -96.871 | -9.962 | 44.779 | 1.00 | 22.26 |
| 23040 | C | THR | D | 610 | -96.834 | -7.352 | 45.873 | 1.00 | 23.38 |
| 23041 | O | THR | D | 610 | -96.152 | -7.606 | 46.865 | 1.00 | 23.59 |
| 23042 | N | SER | D | 611 | -96.431 | -6.556 | 44.887 | 1.00 | 23.59 |

FIGURE 3 SL

| A | B | C | D | E | F | G | H | I | J |
|---|---|---|---|---|---|---|---|---|---|
| 23043 | CA | SER | D | 611 | -95.111 | -5.923 | 44.880 | 1.00 | 23.09 |
| 23044 | CB | SER | D | 611 | -94.866 | -5.263 | 43.533 | 1.00 | 23.14 |
| 23045 | OG | SER | D | 611 | -94.870 | -6.221 | 42.488 | 1.00 | 23.80 |
| 23046 | C | SER | D | 611 | -94.981 | -4.878 | 45.993 | 1.00 | 23.31 |
| 23047 | O | SER | D | 611 | -93.948 | -4.797 | 46.667 | 1.00 | 23.41 |
| 23048 | N | MET | D | 612 | -96.041 | -4.089 | 46.177 | 1.00 | 22.64 |
| 23049 | CA | MET | D | 612 | -96.097 | -3.081 | 47.219 | 1.00 | 21.73 |
| 23050 | CB | MET | D | 612 | -97.403 | -2.311 | 47.109 | 1.00 | 21.27 |
| 23051 | CG | MET | D | 612 | -97.449 | -1.400 | 45.874 | 1.00 | 20.75 |
| 23052 | SD | MET | D | 612 | -96.138 | -0.132 | 45.962 | 1.00 | 22.54 |
| 23053 | CE | MET | D | 612 | -96.942 | 0.982 | 47.037 | 1.00 | 20.15 |
| 23054 | C | MET | D | 612 | -95.945 | -3.743 | 48.593 | 1.00 | 22.23 |
| 23055 | O | MET | D | 612 | -95.235 | -3.233 | 49.474 | 1.00 | 21.46 |
| 23056 | N | VAL | D | 613 | -96.611 | -4.889 | 48.753 | 1.00 | 21.78 |
| 23057 | CA | VAL | D | 613 | -96.542 | -5.669 | 49.981 | 1.00 | 21.13 |
| 23058 | CB | VAL | D | 613 | -97.625 | -6.782 | 49.969 | 1.00 | 21.05 |
| 23059 | CG1 | VAL | D | 613 | -97.274 | -7.913 | 50.941 | 1.00 | 21.49 |
| 23060 | CG2 | VAL | D | 613 | -99.002 | -6.207 | 50.242 | 1.00 | 19.63 |
| 23061 | C | VAL | D | 613 | -95.142 | -6.282 | 50.115 | 1.00 | 21.21 |
| 23062 | O | VAL | D | 613 | -94.525 | -6.234 | 51.180 | 1.00 | 22.38 |
| 23063 | N | LEU | D | 614 | -94.598 | -6.833 | 49.041 | 1.00 | 21.20 |
| 23064 | CA | LEU | D | 614 | -93.247 | -7.387 | 49.152 | 1.00 | 21.30 |
| 23065 | CB | LEU | D | 614 | -92.854 | -8.140 | 47.900 | 1.00 | 20.29 |
| 23066 | CG | LEU | D | 614 | -93.636 | -9.428 | 47.666 | 1.00 | 19.95 |
| 23067 | CD1 | LEU | D | 614 | -93.462 | -10.439 | 48.841 | 1.00 | 19.35 |
| 23068 | CD2 | LEU | D | 614 | -93.206 | -10.047 | 46.380 | 1.00 | 15.59 |
| 23069 | C | LEU | D | 614 | -92.170 | -6.344 | 49.497 | 1.00 | 22.17 |
| 23070 | O | LEU | D | 614 | -91.159 | -6.684 | 50.102 | 1.00 | 22.67 |
| 23071 | N | GLY | D | 615 | -92.377 | -5.083 | 49.126 | 1.00 | 22.27 |
| 23072 | CA | GLY | D | 615 | -91.395 | -4.061 | 49.410 | 1.00 | 22.40 |
| 23073 | C | GLY | D | 615 | -91.726 | -3.183 | 50.605 | 1.00 | 23.25 |
| 23074 | O | GLY | D | 615 | -91.081 | -2.134 | 50.848 | 1.00 | 23.33 |
| 23075 | N | SER | D | 616 | -92.711 | -3.629 | 51.376 | 1.00 | 23.60 |
| 23076 | CA | SER | D | 616 | -93.200 | -2.904 | 52.534 | 1.00 | 23.70 |
| 23077 | CB | SER | D | 616 | -94.596 | -3.413 | 52.874 | 1.00 | 23.88 |
| 23078 | OG | SER | D | 616 | -94.509 | -4.694 | 53.490 | 1.00 | 25.47 |
| 23079 | C | SER | D | 616 | -92.343 | -3.029 | 53.790 | 1.00 | 24.16 |
| 23080 | O | SER | D | 616 | -92.471 | -2.208 | 54.698 | 1.00 | 25.00 |
| 23081 | N | GLY | D | 617 | -91.498 | -4.049 | 53.870 | 1.00 | 24.13 |
| 23082 | CA | GLY | D | 617 | -90.726 | -4.287 | 55.080 | 1.00 | 24.51 |
| 23083 | C | GLY | D | 617 | -91.497 | -4.875 | 56.253 | 1.00 | 25.66 |
| 23084 | O | GLY | D | 617 | -91.042 | -4.815 | 57.394 | 1.00 | 26.49 |
| 23085 | N | SER | D | 618 | -92.654 | -5.477 | 55.997 | 1.00 | 25.95 |
| 23086 | CA | SER | D | 618 | -93.486 | -5.940 | 57.090 | 1.00 | 26.12 |
| 23087 | CB | SER | D | 618 | -94.913 | -6.191 | 56.618 | 1.00 | 25.79 |
| 23088 | OG | SER | D | 618 | -94.958 | -7.356 | 55.822 | 1.00 | 25.11 |
| 23089 | C | SER | D | 618 | -92.940 | -7.214 | 57.721 | 1.00 | 27.16 |
| 23090 | O | SER | D | 618 | -93.216 | -7.500 | 58.885 | 1.00 | 27.72 |
| 23091 | N | GLY | D | 619 | -92.197 | -7.991 | 56.950 | 1.00 | 26.87 |
| 23092 | CA | GLY | D | 619 | -91.651 | -9.226 | 57.467 | 1.00 | 27.32 |
| 23093 | C | GLY | D | 619 | -92.606 | -10.409 | 57.474 | 1.00 | 27.28 |

FIGURE 3 SM

| A | B | C | D | E | F | G | H | I | J |
|---|---|---|---|---|---|---|---|---|---|
| 23094 | O | GLY | D | 619 | -92.235 | -11.504 | 57.864 | 1.00 | 27.63 |
| 23095 | N | VAL | D | 620 | -93.816 | -10.215 | 56.990 | 1.00 | 26.98 |
| 23096 | CA | VAL | D | 620 | -94.823 | -11.272 | 57.054 | 1.00 | 26.82 |
| 23097 | CB | VAL | D | 620 | -96.215 | -10.663 | 57.128 | 1.00 | 27.10 |
| 23098 | CG1 | VAL | D | 620 | -97.299 | -11.735 | 57.065 | 1.00 | 27.01 |
| 23099 | CG2 | VAL | D | 620 | -96.327 | -9.803 | 58.398 | 1.00 | 25.69 |
| 23100 | C | VAL | D | 620 | -94.751 | -12.234 | 55.886 | 1.00 | 26.89 |
| 23101 | O | VAL | D | 620 | -95.068 | -13.412 | 56.022 | 1.00 | 27.36 |
| 23102 | N | PHE | D | 621 | -94.293 | -11.741 | 54.743 | 1.00 | 26.24 |
| 23103 | CA | PHE | D | 621 | -94.230 | -12.554 | 53.554 | 1.00 | 25.32 |
| 23104 | CB | PHE | D | 621 | -94.896 | -11.806 | 52.380 | 1.00 | 25.19 |
| 23105 | CG | PHE | D | 621 | -96.339 | -11.424 | 52.653 | 1.00 | 23.16 |
| 23106 | CD1 | PHE | D | 621 | -96.642 | -10.280 | 53.349 | 1.00 | 20.70 |
| 23107 | CE1 | PHE | D | 621 | -97.964 | -9.940 | 53.621 | 1.00 | 19.37 |
| 23108 | CZ | PHE | D | 621 | -98.987 | -10.744 | 53.191 | 1.00 | 20.10 |
| 23109 | CE2 | PHE | D | 621 | -98.703 | -11.898 | 52.500 | 1.00 | 19.43 |
| 23110 | CD2 | PHE | D | 621 | -97.385 | -12.233 | 52.228 | 1.00 | 21.78 |
| 23111 | C | PHE | D | 621 | -92.809 | -12.976 | 53.230 | 1.00 | 25.90 |
| 23112 | O | PHE | D | 621 | -91.863 | -12.192 | 53.302 | 1.00 | 26.42 |
| 23113 | N | LYS | D | 622 | -92.658 | -14.231 | 52.874 | 1.00 | 26.12 |
| 23114 | CA | LYS | D | 622 | -91.356 | -14.759 | 52.530 | 1.00 | 27.08 |
| 23115 | CB | LYS | D | 622 | -91.336 | -16.265 | 52.812 | 1.00 | 26.96 |
| 23116 | CG | LYS | D | 622 | -89.995 | -16.936 | 52.586 | 1.00 | 28.63 |
| 23117 | CD | LYS | D | 622 | -90.086 | -18.436 | 52.926 | 1.00 | 30.58 |
| 23118 | CE | LYS | D | 622 | -88.716 | -19.103 | 52.885 | 1.00 | 33.11 |
| 23119 | NZ | LYS | D | 622 | -88.146 | -19.197 | 51.521 | 1.00 | 34.13 |
| 23120 | C | LYS | D | 622 | -91.074 | -14.517 | 51.048 | 1.00 | 26.97 |
| 23121 | O | LYS | D | 622 | -89.949 | -14.222 | 50.655 | 1.00 | 26.68 |
| 23122 | N | CYS | D | 623 | -92.114 | -14.624 | 50.228 | 1.00 | 27.32 |
| 23123 | CA | CYS | D | 623 | -91.939 | -14.514 | 48.789 | 1.00 | 27.63 |
| 23124 | CB | CYS | D | 623 | -91.486 | -15.855 | 48.239 | 1.00 | 28.04 |
| 23125 | SG | CYS | D | 623 | -92.673 | -17.133 | 48.612 | 1.00 | 32.49 |
| 23126 | C | CYS | D | 623 | -93.240 | -14.143 | 48.116 | 1.00 | 26.28 |
| 23127 | O | CYS | D | 623 | -94.290 | -14.113 | 48.749 | 1.00 | 26.71 |
| 23128 | N | GLY | D | 624 | -93.169 | -13.870 | 46.823 | 1.00 | 24.98 |
| 23129 | CA | GLY | D | 624 | -94.353 | -13.530 | 46.069 | 1.00 | 23.49 |
| 23130 | C | GLY | D | 624 | -94.092 | -13.437 | 44.577 | 1.00 | 23.30 |
| 23131 | O | GLY | D | 624 | -92.936 | -13.432 | 44.120 | 1.00 | 22.53 |
| 23132 | N | ILE | D | 625 | -95.188 | -13.372 | 43.822 | 1.00 | 22.21 |
| 23133 | CA | ILE | D | 625 | -95.137 | -13.374 | 42.385 | 1.00 | 21.40 |
| 23134 | CB | ILE | D | 625 | -95.706 | -14.692 | 41.842 | 1.00 | 21.55 |
| 23135 | CG1 | ILE | D | 625 | -95.026 | -15.905 | 42.472 | 1.00 | 21.25 |
| 23136 | CD1 | ILE | D | 625 | -95.620 | -17.199 | 41.976 | 1.00 | 22.46 |
| 23137 | CG2 | ILE | D | 625 | -95.572 | -14.742 | 40.327 | 1.00 | 20.26 |
| 23138 | C | ILE | D | 625 | -96.022 | -12.264 | 41.865 | 1.00 | 21.62 |
| 23139 | O | ILE | D | 625 | -97.201 | -12.201 | 42.211 | 1.00 | 20.79 |
| 23140 | N | ALA | D | 626 | -95.466 | -11.399 | 41.024 | 1.00 | 21.33 |
| 23141 | CA | ALA | D | 626 | -96.262 | -10.317 | 40.453 | 1.00 | 21.56 |
| 23142 | CB | ALA | D | 626 | -95.638 | -8.956 | 40.754 | 1.00 | 21.64 |
| 23143 | C | ALA | D | 626 | -96.331 | -10.525 | 38.960 | 1.00 | 21.03 |
| 23144 | O | ALA | D | 626 | -95.311 | -10.566 | 38.290 | 1.00 | 21.70 |

FIGURE 3 SN

| A | B | C | D | E | F | G | H | I | J |
|---|---|---|---|---|---|---|---|---|---|
| 23145 | N | VAL | D | 627 | -97.534 | -10.641 | 38.434 | 1.00 | 20.44 |
| 23146 | CA | VAL | D | 627 | -97.698 | -10.876 | 37.010 | 1.00 | 19.92 |
| 23147 | CB | VAL | D | 627 | -98.638 | -12.074 | 36.779 | 1.00 | 19.63 |
| 23148 | CG1 | VAL | D | 627 | -98.779 | -12.364 | 35.328 | 1.00 | 19.32 |
| 23149 | CG2 | VAL | D | 627 | -98.121 | -13.277 | 37.526 | 1.00 | 19.10 |
| 23150 | C | VAL | D | 627 | -98.270 | -9.636 | 36.336 | 1.00 | 19.71 |
| 23151 | O | VAL | D | 627 | -99.321 | -9.147 | 36.741 | 1.00 | 20.98 |
| 23152 | N | ALA | D | 628 | -97.564 | -9.119 | 35.334 | 1.00 | 19.16 |
| 23153 | CA | ALA | D | 628 | -97.994 | -7.944 | 34.606 | 1.00 | 19.09 |
| 23154 | CB | ALA | D | 628 | -99.125 | -8.313 | 33.667 | 1.00 | 19.00 |
| 23155 | C | ALA | D | 628 | -98.443 | -6.846 | 35.563 | 1.00 | 19.80 |
| 23156 | O | ALA | D | 628 | -99.564 | -6.318 | 35.442 | 1.00 | 20.29 |
| 23157 | N | PRO | D | 629 | -97.596 | -6.499 | 36.524 | 1.00 | 19.51 |
| 23158 | CA | PRO | D | 629 | -97.984 | -5.513 | 37.533 | 1.00 | 19.62 |
| 23159 | CB | PRO | D | 629 | -96.889 | -5.669 | 38.584 | 1.00 | 19.78 |
| 23160 | CG | PRO | D | 629 | -95.679 | -5.993 | 37.730 | 1.00 | 20.27 |
| 23161 | CD | PRO | D | 629 | -96.236 | -7.022 | 36.749 | 1.00 | 19.35 |
| 23162 | C | PRO | D | 629 | -97.927 | -4.088 | 37.040 | 1.00 | 20.11 |
| 23163 | O | PRO | D | 629 | -97.120 | -3.718 | 36.174 | 1.00 | 20.33 |
| 23164 | N | VAL | D | 630 | -98.806 | -3.274 | 37.594 | 1.00 | 20.35 |
| 23165 | CA | VAL | D | 630 | -98.654 | -1.844 | 37.453 | 1.00 | 20.36 |
| 23166 | CB | VAL | D | 630 | -99.956 | -1.119 | 37.858 | 1.00 | 20.44 |
| 23167 | CG1 | VAL | D | 630 | -99.658 | 0.296 | 38.468 | 1.00 | 19.91 |
| 23168 | CG2 | VAL | D | 630 | -100.903 | -1.027 | 36.674 | 1.00 | 19.46 |
| 23169 | C | VAL | D | 630 | -97.512 | -1.548 | 38.458 | 1.00 | 20.76 |
| 23170 | O | VAL | D | 630 | -97.420 | -2.207 | 39.502 | 1.00 | 19.76 |
| 23171 | N | SER | D | 631 | -96.628 | -0.601 | 38.138 | 1.00 | 20.86 |
| 23172 | CA | SER | D | 631 | -95.524 | -0.284 | 39.027 | 1.00 | 21.41 |
| 23173 | CB | SER | D | 631 | -94.183 | -0.668 | 38.404 | 1.00 | 21.58 |
| 23174 | OG | SER | D | 631 | -93.908 | 0.098 | 37.254 | 1.00 | 22.64 |
| 23175 | C | SER | D | 631 | -95.514 | 1.186 | 39.452 | 1.00 | 21.56 |
| 23176 | O | SER | D | 631 | -95.023 | 1.506 | 40.528 | 1.00 | 20.61 |
| 23177 | N | ARG | D | 632 | -96.002 | 2.066 | 38.579 | 1.00 | 21.04 |
| 23178 | CA | ARG | D | 632 | -96.184 | 3.465 | 38.917 | 1.00 | 22.20 |
| 23179 | CB | ARG | D | 632 | -94.932 | 4.341 | 38.755 | 1.00 | 23.16 |
| 23180 | CG | ARG | D | 632 | -94.545 | 4.709 | 37.399 | 1.00 | 25.77 |
| 23181 | CD | ARG | D | 632 | -94.066 | 6.140 | 37.276 | 1.00 | 30.32 |
| 23182 | NE | ARG | D | 632 | -93.188 | 6.556 | 38.351 | 1.00 | 32.43 |
| 23183 | CZ | ARG | D | 632 | -92.553 | 7.733 | 38.389 | 1.00 | 35.70 |
| 23184 | NH1 | ARG | D | 632 | -91.777 | 8.011 | 39.428 | 1.00 | 34.00 |
| 23185 | NH2 | ARG | D | 632 | -92.684 | 8.632 | 37.395 | 1.00 | 34.81 |
| 23186 | C | ARG | D | 632 | -97.372 | 3.964 | 38.133 | 1.00 | 21.99 |
| 23187 | O | ARG | D | 632 | -97.580 | 3.572 | 36.982 | 1.00 | 21.10 |
| 23188 | N | TRP | D | 633 | -98.195 | 4.759 | 38.808 | 1.00 | 21.72 |
| 23189 | CA | TRP | D | 633 | -99.493 | 5.143 | 38.269 | 1.00 | 22.29 |
| 23190 | CB | TRP | D | 633 | -100.405 | 5.680 | 39.393 | 1.00 | 22.18 |
| 23191 | CG | TRP | D | 633 | -100.858 | 4.501 | 40.246 | 1.00 | 22.76 |
| 23192 | CD1 | TRP | D | 633 | -100.506 | 4.231 | 41.540 | 1.00 | 20.58 |
| 23193 | NE1 | TRP | D | 633 | -101.080 | 3.053 | 41.947 | 1.00 | 20.97 |
| 23194 | CE2 | TRP | D | 633 | -101.825 | 2.535 | 40.916 | 1.00 | 21.34 |
| 23195 | CD2 | TRP | D | 633 | -101.691 | 3.410 | 39.822 | 1.00 | 20.22 |

FIGURE 3 SO

| A | B | C | D | E | F | G | H | I | J |
|---|---|---|---|---|---|---|---|---|---|
| 23196 | CE3 | TRP | D | 633 | -102.353 | 3.095 | 38.629 | 1.00 | 20.65 |
| 23197 | CZ3 | TRP | D | 633 | -103.099 | 1.934 | 38.560 | 1.00 | 20.30 |
| 23198 | CH2 | TRP | D | 633 | -103.204 | 1.076 | 39.662 | 1.00 | 20.21 |
| 23199 | CZ2 | TRP | D | 633 | -102.558 | 1.344 | 40.840 | 1.00 | 19.01 |
| 23200 | C | TRP | D | 633 | -99.452 | 6.006 | 37.031 | 1.00 | 22.40 |
| 23201 | O | TRP | D | 633 | -100.365 | 5.963 | 36.230 | 1.00 | 23.36 |
| 23202 | N | GLU | D | 634 | -98.373 | 6.737 | 36.832 | 1.00 | 23.31 |
| 23203 | CA | GLU | D | 634 | -98.252 | 7.551 | 35.634 | 1.00 | 24.08 |
| 23204 | CB | GLU | D | 634 | -97.082 | 8.534 | 35.714 | 1.00 | 24.74 |
| 23205 | CG | GLU | D | 634 | -97.298 | 9.664 | 36.714 | 1.00 | 26.01 |
| 23206 | CD | GLU | D | 634 | -96.482 | 9.460 | 37.972 | 1.00 | 31.66 |
| 23207 | OE1 | GLU | D | 634 | -95.612 | 10.335 | 38.201 | 1.00 | 32.18 |
| 23208 | OE2 | GLU | D | 634 | -96.691 | 8.419 | 38.703 | 1.00 | 30.86 |
| 23209 | C | GLU | D | 634 | -98.114 | 6.703 | 34.391 | 1.00 | 23.69 |
| 23210 | O | GLU | D | 634 | -98.362 | 7.200 | 33.303 | 1.00 | 23.35 |
| 23211 | N | TYR | D | 635 | -97.718 | 5.434 | 34.537 | 1.00 | 23.21 |
| 23212 | CA | TYR | D | 635 | -97.615 | 4.548 | 33.372 | 1.00 | 22.92 |
| 23213 | CB | TYR | D | 635 | -96.723 | 3.345 | 33.640 | 1.00 | 22.54 |
| 23214 | CG | TYR | D | 635 | -95.263 | 3.663 | 33.966 | 1.00 | 24.14 |
| 23215 | CD1 | TYR | D | 635 | -94.726 | 4.898 | 33.641 | 1.00 | 23.13 |
| 23216 | CE1 | TYR | D | 635 | -93.418 | 5.183 | 33.938 | 1.00 | 23.12 |
| 23217 | CZ | TYR | D | 635 | -92.646 | 4.231 | 34.583 | 1.00 | 24.31 |
| 23218 | OH | TYR | D | 635 | -91.347 | 4.502 | 34.892 | 1.00 | 23.90 |
| 23219 | CE2 | TYR | D | 635 | -93.173 | 3.005 | 34.923 | 1.00 | 24.61 |
| 23220 | CD2 | TYR | D | 635 | -94.480 | 2.723 | 34.611 | 1.00 | 24.33 |
| 23221 | C | TYR | D | 635 | -98.959 | 3.976 | 32.979 | 1.00 | 22.64 |
| 23222 | O | TYR | D | 635 | -99.123 | 3.441 | 31.878 | 1.00 | 22.13 |
| 23223 | N | TYR | D | 636 | -99.927 | 4.025 | 33.876 | 1.00 | 22.22 |
| 23224 | CA | TYR | D | 636 | -101.162 | 3.352 | 33.526 | 1.00 | 22.38 |
| 23225 | CB | TYR | D | 636 | -101.788 | 2.660 | 34.727 | 1.00 | 21.80 |
| 23226 | CG | TYR | D | 636 | -102.788 | 1.640 | 34.286 | 1.00 | 19.84 |
| 23227 | CD1 | TYR | D | 636 | -102.417 | 0.625 | 33.436 | 1.00 | 18.32 |
| 23228 | CE1 | TYR | D | 636 | -103.335 | -0.316 | 32.998 | 1.00 | 20.41 |
| 23229 | CZ | TYR | D | 636 | -104.628 | -0.238 | 33.413 | 1.00 | 20.72 |
| 23230 | OH | TYR | D | 636 | -105.537 | -1.174 | 32.967 | 1.00 | 24.19 |
| 23231 | CE2 | TYR | D | 636 | -105.030 | 0.781 | 34.259 | 1.00 | 20.82 |
| 23232 | CD2 | TYR | D | 636 | -104.113 | 1.723 | 34.673 | 1.00 | 18.74 |
| 23233 | C | TYR | D | 636 | -102.146 | 4.258 | 32.778 | 1.00 | 22.84 |
| 23234 | O | TYR | D | 636 | -101.933 | 5.461 | 32.700 | 1.00 | 23.58 |
| 23235 | N | ASP | D | 637 | -103.179 | 3.680 | 32.178 | 1.00 | 23.34 |
| 23236 | CA | ASP | D | 637 | -104.079 | 4.478 | 31.365 | 1.00 | 24.69 |
| 23237 | CB | ASP | D | 637 | -105.030 | 3.616 | 30.523 | 1.00 | 24.97 |
| 23238 | CG | ASP | D | 637 | -106.145 | 3.012 | 31.328 | 1.00 | 25.70 |
| 23239 | OD1 | ASP | D | 637 | -106.957 | 3.784 | 31.853 | 1.00 | 26.97 |
| 23240 | OD2 | ASP | D | 637 | -106.313 | 1.778 | 31.453 | 1.00 | 26.60 |
| 23241 | C | ASP | D | 637 | -104.798 | 5.545 | 32.178 | 1.00 | 25.32 |
| 23242 | O | ASP | D | 637 | -104.842 | 5.495 | 33.411 | 1.00 | 25.23 |
| 23243 | N | SER | D | 638 | -105.354 | 6.522 | 31.474 | 1.00 | 25.73 |
| 23244 | CA | SER | D | 638 | -105.904 | 7.694 | 32.132 | 1.00 | 25.90 |
| 23245 | CB | SER | D | 638 | -105.934 | 8.843 | 31.140 | 1.00 | 25.38 |
| 23246 | OG | SER | D | 638 | -106.815 | 8.506 | 30.101 | 1.00 | 26.53 |

FIGURE 3 SP

| A | B | C | D | E | F | G | H | I | J |
|---|---|---|---|---|---|---|---|---|---|
| 23247 | C | SER | D | 638 | -107.281 | 7.516 | 32.777 | 1.00 | 25.91 |
| 23248 | O | SER | D | 638 | -107.500 | 7.960 | 33.897 | 1.00 | 25.61 |
| 23249 | N | VAL | D | 639 | -108.218 | 6.863 | 32.103 | 1.00 | 26.51 |
| 23250 | CA | VAL | D | 639 | -109.543 | 6.834 | 32.699 | 1.00 | 27.09 |
| 23251 | CB | VAL | D | 639 | -110.686 | 6.551 | 31.688 | 1.00 | 27.52 |
| 23252 | CG1 | VAL | D | 639 | -111.496 | 5.339 | 32.069 | 1.00 | 29.06 |
| 23253 | CG2 | VAL | D | 639 | -110.168 | 6.505 | 30.248 | 1.00 | 28.47 |
| 23254 | C | VAL | D | 639 | -109.596 | 5.992 | 33.977 | 1.00 | 26.75 |
| 23255 | O | VAL | D | 639 | -110.272 | 6.357 | 34.932 | 1.00 | 26.42 |
| 23256 | N | TYR | D | 640 | -108.832 | 4.905 | 34.014 | 1.00 | 26.18 |
| 23257 | CA | TYR | D | 640 | -108.798 | 4.075 | 35.205 | 1.00 | 25.96 |
| 23258 | CB | TYR | D | 640 | -108.168 | 2.719 | 34.893 | 1.00 | 25.44 |
| 23259 | CG | TYR | D | 640 | -108.145 | 1.767 | 36.066 | 1.00 | 24.92 |
| 23260 | CD1 | TYR | D | 640 | -109.119 | 0.787 | 36.205 | 1.00 | 24.01 |
| 23261 | CE1 | TYR | D | 640 | -109.100 | -0.084 | 37.269 | 1.00 | 21.51 |
| 23262 | CZ | TYR | D | 640 | -108.096 | 0.010 | 38.227 | 1.00 | 22.81 |
| 23263 | OH | TYR | D | 640 | -108.097 | -0.872 | 39.286 | 1.00 | 23.49 |
| 23264 | CE2 | TYR | D | 640 | -107.130 | 0.967 | 38.134 | 1.00 | 21.03 |
| 23265 | CD2 | TYR | D | 640 | -107.149 | 1.846 | 37.050 | 1.00 | 24.50 |
| 23266 | C | TYR | D | 640 | -108.032 | 4.762 | 36.337 | 1.00 | 25.42 |
| 23267 | O | TYR | D | 640 | -108.579 | 5.006 | 37.400 | 1.00 | 25.71 |
| 23268 | N | THR | D | 641 | -106.769 | 5.067 | 36.080 | 1.00 | 25.09 |
| 23269 | CA | THR | D | 641 | -105.878 | 5.672 | 37.052 | 1.00 | 25.10 |
| 23270 | CB | THR | D | 641 | -104.534 | 5.962 | 36.403 | 1.00 | 24.83 |
| 23271 | OG1 | THR | D | 641 | -103.960 | 4.743 | 35.940 | 1.00 | 26.06 |
| 23272 | CG2 | THR | D | 641 | -103.534 | 6.479 | 37.441 | 1.00 | 24.57 |
| 23273 | C | THR | D | 641 | -106.408 | 6.976 | 37.630 | 1.00 | 25.18 |
| 23274 | O | THR | D | 641 | -106.429 | 7.163 | 38.848 | 1.00 | 24.41 |
| 23275 | N | GLU | D | 642 | -106.830 | 7.872 | 36.749 | 1.00 | 24.77 |
| 23276 | CA | GLU | D | 642 | -107.304 | 9.174 | 37.187 | 1.00 | 25.52 |
| 23277 | CB | GLU | D | 642 | -107.435 | 10.125 | 35.991 | 1.00 | 25.53 |
| 23278 | CG | GLU | D | 642 | -106.086 | 10.541 | 35.424 | 1.00 | 25.78 |
| 23279 | CD | GLU | D | 642 | -106.193 | 11.254 | 34.090 | 1.00 | 26.46 |
| 23280 | OE1 | GLU | D | 642 | -107.337 | 11.592 | 33.676 | 1.00 | 23.00 |
| 23281 | OE2 | GLU | D | 642 | -105.122 | 11.473 | 33.469 | 1.00 | 27.43 |
| 23282 | C | GLU | D | 642 | -108.606 | 9.070 | 37.976 | 1.00 | 25.69 |
| 23283 | O | GLU | D | 642 | -108.879 | 9.886 | 38.858 | 1.00 | 26.67 |
| 23284 | N | ARG | D | 643 | -109.400 | 8.053 | 37.686 | 1.00 | 25.27 |
| 23285 | CA | ARG | D | 643 | -110.625 | 7.839 | 38.437 | 1.00 | 25.75 |
| 23286 | CB | ARG | D | 643 | -111.233 | 6.507 | 38.014 | 1.00 | 26.11 |
| 23287 | CG | ARG | D | 643 | -112.604 | 6.225 | 38.580 | 1.00 | 26.46 |
| 23288 | CD | ARG | D | 643 | -113.448 | 5.411 | 37.619 | 1.00 | 30.50 |
| 23289 | NE | ARG | D | 643 | -112.919 | 4.068 | 37.485 | 1.00 | 32.80 |
| 23290 | CZ | ARG | D | 643 | -112.837 | 3.381 | 36.360 | 1.00 | 31.23 |
| 23291 | NH1 | ARG | D | 643 | -112.334 | 2.160 | 36.397 | 1.00 | 31.11 |
| 23292 | NH2 | ARG | D | 643 | -113.239 | 3.895 | 35.214 | 1.00 | 30.58 |
| 23293 | C | ARG | D | 643 | -110.356 | 7.800 | 39.963 | 1.00 | 25.90 |
| 23294 | O | ARG | D | 643 | -111.142 | 8.302 | 40.767 | 1.00 | 24.71 |
| 23295 | N | TYR | D | 644 | -109.234 | 7.184 | 40.332 | 1.00 | 25.76 |
| 23296 | CA | TYR | D | 644 | -108.868 | 7.006 | 41.723 | 1.00 | 26.45 |
| 23297 | CB | TYR | D | 644 | -108.476 | 5.531 | 41.957 | 1.00 | 26.40 |

FIGURE 3 SQ

| A | B | C | D | E | F | G | H | I | J |
|---|---|---|---|---|---|---|---|---|---|
| 23298 | CG | TYR | D | 644 | -109.364 | 4.543 | 41.220 | 1.00 | 25.41 |
| 23299 | CD1 | TYR | D | 644 | -110.679 | 4.338 | 41.610 | 1.00 | 25.27 |
| 23300 | CE1 | TYR | D | 644 | -111.490 | 3.447 | 40.952 | 1.00 | 24.47 |
| 23301 | CZ | TYR | D | 644 | -111.002 | 2.750 | 39.857 | 1.00 | 25.81 |
| 23302 | OH | TYR | D | 644 | -111.812 | 1.859 | 39.198 | 1.00 | 25.64 |
| 23303 | CE2 | TYR | D | 644 | -109.713 | 2.942 | 39.432 | 1.00 | 25.89 |
| 23304 | CD2 | TYR | D | 644 | -108.897 | 3.847 | 40.123 | 1.00 | 26.08 |
| 23305 | C | TYR | D | 644 | -107.705 | 7.905 | 42.130 | 1.00 | 26.93 |
| 23306 | O | TYR | D | 644 | -107.502 | 8.189 | 43.308 | 1.00 | 27.89 |
| 23307 | N | MET | D | 645 | -106.933 | 8.371 | 41.165 | 1.00 | 27.11 |
| 23308 | CA | MET | D | 645 | -105.748 | 9.118 | 41.523 | 1.00 | 27.40 |
| 23309 | CB | MET | D | 645 | -104.524 | 8.520 | 40.829 | 1.00 | 26.37 |
| 23310 | CG | MET | D | 645 | -104.119 | 7.185 | 41.357 | 1.00 | 26.82 |
| 23311 | SD | MET | D | 645 | -103.523 | 7.225 | 43.053 | 1.00 | 28.13 |
| 23312 | CE | MET | D | 645 | -101.827 | 7.877 | 42.790 | 1.00 | 24.04 |
| 23313 | C | MET | D | 645 | -105.807 | 10.586 | 41.198 | 1.00 | 27.88 |
| 23314 | O | MET | D | 645 | -104.871 | 11.308 | 41.506 | 1.00 | 28.19 |
| 23315 | N | GLY | D | 646 | -106.880 | 11.040 | 40.562 | 1.00 | 28.54 |
| 23316 | CA | GLY | D | 646 | -106.888 | 12.418 | 40.121 | 1.00 | 28.79 |
| 23317 | C | GLY | D | 646 | -105.752 | 12.594 | 39.113 | 1.00 | 29.56 |
| 23318 | O | GLY | D | 646 | -105.264 | 11.621 | 38.514 | 1.00 | 29.39 |
| 23319 | N | LEU | D | 647 | -105.303 | 13.827 | 38.936 | 1.00 | 29.71 |
| 23320 | CA | LEU | D | 647 | -104.274 | 14.117 | 37.944 | 1.00 | 30.13 |
| 23321 | CB | LEU | D | 647 | -104.607 | 15.454 | 37.282 | 1.00 | 30.79 |
| 23322 | CG | LEU | D | 647 | -105.479 | 15.373 | 36.022 | 1.00 | 32.03 |
| 23323 | CD1 | LEU | D | 647 | -106.021 | 13.998 | 35.837 | 1.00 | 32.06 |
| 23324 | CD2 | LEU | D | 647 | -106.609 | 16.389 | 36.060 | 1.00 | 33.49 |
| 23325 | C | LEU | D | 647 | -102.884 | 14.158 | 38.572 | 1.00 | 29.81 |
| 23326 | O | LEU | D | 647 | -102.739 | 14.593 | 39.702 | 1.00 | 30.86 |
| 23327 | N | PRO | D | 648 | -101.863 | 13.686 | 37.869 | 1.00 | 29.42 |
| 23328 | CA | PRO | D | 648 | -100.499 | 13.715 | 38.400 | 1.00 | 29.27 |
| 23329 | CB | PRO | D | 648 | -99.788 | 12.641 | 37.569 | 1.00 | 29.19 |
| 23330 | CG | PRO | D | 648 | -100.474 | 12.645 | 36.284 | 1.00 | 28.08 |
| 23331 | CD | PRO | D | 648 | -101.919 | 13.047 | 36.542 | 1.00 | 29.14 |
| 23332 | C | PRO | D | 648 | -99.792 | 15.061 | 38.210 | 1.00 | 29.74 |
| 23333 | O | PRO | D | 648 | -98.744 | 15.100 | 37.580 | 1.00 | 29.58 |
| 23334 | N | THR | D | 649 | -100.363 | 16.136 | 38.740 | 1.00 | 30.57 |
| 23335 | CA | THR | D | 649 | -99.763 | 17.472 | 38.651 | 1.00 | 31.80 |
| 23336 | CB | THR | D | 649 | -100.702 | 18.440 | 37.937 | 1.00 | 31.39 |
| 23337 | OG1 | THR | D | 649 | -101.944 | 18.494 | 38.654 | 1.00 | 33.99 |
| 23338 | CG2 | THR | D | 649 | -101.101 | 17.906 | 36.591 | 1.00 | 31.18 |
| 23339 | C | THR | D | 649 | -99.533 | 18.010 | 40.050 | 1.00 | 32.36 |
| 23340 | O | THR | D | 649 | -100.146 | 17.548 | 41.010 | 1.00 | 32.49 |
| 23341 | N | PRO | D | 650 | -98.683 | 19.020 | 40.173 | 1.00 | 33.18 |
| 23342 | CA | PRO | D | 650 | -98.400 | 19.602 | 41.489 | 1.00 | 33.36 |
| 23343 | CB | PRO | D | 650 | -97.313 | 20.651 | 41.200 | 1.00 | 33.52 |
| 23344 | CG | PRO | D | 650 | -96.782 | 20.316 | 39.830 | 1.00 | 33.60 |
| 23345 | CD | PRO | D | 650 | -97.962 | 19.701 | 39.080 | 1.00 | 33.10 |
| 23346 | C | PRO | D | 650 | -99.652 | 20.244 | 42.100 | 1.00 | 34.02 |
| 23347 | O | PRO | D | 650 | -99.718 | 20.423 | 43.307 | 1.00 | 33.80 |
| 23348 | N | GLU | D | 651 | -100.651 | 20.577 | 41.292 | 1.00 | 34.80 |

FIGURE 3 SR

| A | B | C | D | E | F | G | H | I | J |
|---|---|---|---|---|---|---|---|---|---|
| 23349 | CA | GLU | D | 651 | -101.858 | 21.125 | 41.903 | 1.00 | 35.73 |
| 23350 | CB | GLU | D | 651 | -102.394 | 22.357 | 41.159 | 1.00 | 36.27 |
| 23351 | CG | GLU | D | 651 | -102.305 | 22.323 | 39.650 | 1.00 | 38.03 |
| 23352 | CD | GLU | D | 651 | -100.901 | 22.573 | 39.124 | 1.00 | 39.96 |
| 23353 | OE1 | GLU | D | 651 | -100.606 | 22.074 | 38.006 | 1.00 | 39.36 |
| 23354 | OE2 | GLU | D | 651 | -100.109 | 23.270 | 39.807 | 1.00 | 39.77 |
| 23355 | C | GLU | D | 651 | -102.954 | 20.091 | 42.211 | 1.00 | 35.65 |
| 23356 | O | GLU | D | 651 | -103.973 | 20.423 | 42.834 | 1.00 | 35.50 |
| 23357 | N | ASP | D | 652 | -102.725 | 18.829 | 41.827 | 1.00 | 35.10 |
| 23358 | CA | ASP | D | 652 | -103.686 | 17.778 | 42.146 | 1.00 | 34.67 |
| 23359 | CB | ASP | D | 652 | -104.341 | 17.182 | 40.884 | 1.00 | 35.01 |
| 23360 | CG | ASP | D | 652 | -105.584 | 16.345 | 41.200 | 1.00 | 36.32 |
| 23361 | OD1 | ASP | D | 652 | -106.426 | 16.135 | 40.285 | 1.00 | 39.06 |
| 23362 | OD2 | ASP | D | 652 | -105.814 | 15.854 | 42.332 | 1.00 | 36.42 |
| 23363 | C | ASP | D | 652 | -103.070 | 16.695 | 43.027 | 1.00 | 33.99 |
| 23364 | O | ASP | D | 652 | -103.006 | 16.851 | 44.240 | 1.00 | 34.82 |
| 23365 | N | ASN | D | 653 | -102.588 | 15.603 | 42.445 | 1.00 | 32.68 |
| 23366 | CA | ASN | D | 653 | -102.123 | 14.520 | 43.299 | 1.00 | 31.77 |
| 23367 | CB | ASN | D | 653 | -103.154 | 13.387 | 43.280 | 1.00 | 30.55 |
| 23368 | CG | ASN | D | 653 | -103.142 | 12.555 | 44.552 | 1.00 | 29.09 |
| 23369 | OD1 | ASN | D | 653 | -102.564 | 12.946 | 45.573 | 1.00 | 26.00 |
| 23370 | ND2 | ASN | D | 653 | -103.815 | 11.404 | 44.504 | 1.00 | 26.65 |
| 23371 | C | ASN | D | 653 | -100.730 | 13.976 | 43.006 | 1.00 | 31.49 |
| 23372 | O | ASN | D | 653 | -100.435 | 12.850 | 43.358 | 1.00 | 31.75 |
| 23373 | N | LEU | D | 654 | -99.863 | 14.774 | 42.390 | 1.00 | 31.54 |
| 23374 | CA | LEU | D | 654 | -98.547 | 14.264 | 42.003 | 1.00 | 30.92 |
| 23375 | CB | LEU | D | 654 | -97.725 | 15.319 | 41.292 | 1.00 | 31.00 |
| 23376 | CG | LEU | D | 654 | -96.359 | 14.774 | 40.877 | 1.00 | 31.08 |
| 23377 | CD1 | LEU | D | 654 | -95.323 | 15.888 | 40.781 | 1.00 | 32.92 |
| 23378 | CD2 | LEU | D | 654 | -96.457 | 14.000 | 39.578 | 1.00 | 27.02 |
| 23379 | C | LEU | D | 654 | -97.708 | 13.657 | 43.124 | 1.00 | 30.82 |
| 23380 | O | LEU | D | 654 | -96.990 | 12.690 | 42.904 | 1.00 | 30.53 |
| 23381 | N | ASP | D | 655 | -97.764 | 14.218 | 44.318 | 1.00 | 30.70 |
| 23382 | CA | ASP | D | 655 | -96.947 | 13.652 | 45.376 | 1.00 | 31.26 |
| 23383 | CB | ASP | D | 655 | -96.979 | 14.507 | 46.637 | 1.00 | 31.48 |
| 23384 | CG | ASP | D | 655 | -96.491 | 15.922 | 46.383 | 1.00 | 34.42 |
| 23385 | OD1 | ASP | D | 655 | -95.630 | 16.118 | 45.483 | 1.00 | 34.31 |
| 23386 | OD2 | ASP | D | 655 | -96.934 | 16.900 | 47.029 | 1.00 | 38.79 |
| 23387 | C | ASP | D | 655 | -97.355 | 12.210 | 45.668 | 1.00 | 30.63 |
| 23388 | O | ASP | D | 655 | -96.499 | 11.338 | 45.813 | 1.00 | 30.49 |
| 23389 | N | HIS | D | 656 | -98.648 | 11.934 | 45.743 | 1.00 | 29.83 |
| 23390 | CA | HIS | D | 656 | -98.994 | 10.550 | 46.002 | 1.00 | 29.73 |
| 23391 | CB | HIS | D | 656 | -100.438 | 10.328 | 46.446 | 1.00 | 29.65 |
| 23392 | CG | HIS | D | 656 | -100.671 | 8.920 | 46.884 | 1.00 | 30.71 |
| 23393 | ND1 | HIS | D | 656 | -99.932 | 8.331 | 47.889 | 1.00 | 30.42 |
| 23394 | CE1 | HIS | D | 656 | -100.300 | 7.072 | 48.021 | 1.00 | 30.17 |
| 23395 | NE2 | HIS | D | 656 | -101.242 | 6.816 | 47.131 | 1.00 | 28.07 |
| 23396 | CD2 | HIS | D | 656 | -101.478 | 7.952 | 46.394 | 1.00 | 30.82 |
| 23397 | C | HIS | D | 656 | -98.630 | 9.638 | 44.819 | 1.00 | 28.97 |
| 23398 | O | HIS | D | 656 | -98.252 | 8.501 | 45.036 | 1.00 | 28.51 |
| 23399 | N | TYR | D | 657 | -98.718 | 10.147 | 43.588 | 1.00 | 28.14 |

FIGURE 3 SS

| A | B | C | D | E | F | G | H | I | J |
|---|---|---|---|---|---|---|---|---|---|
| 23400 | CA | TYR | D | 657 | -98.286 | 9.375 | 42.424 | 1.00 | 28.19 |
| 23401 | CB | TYR | D | 657 | -98.376 | 10.193 | 41.139 | 1.00 | 27.67 |
| 23402 | CG | TYR | D | 657 | -99.674 | 10.121 | 40.365 | 1.00 | 26.53 |
| 23403 | CD1 | TYR | D | 657 | -99.802 | 9.308 | 39.255 | 1.00 | 24.07 |
| 23404 | CE1 | TYR | D | 657 | -100.986 | 9.275 | 38.524 | 1.00 | 23.58 |
| 23405 | CZ | TYR | D | 657 | -102.041 | 10.075 | 38.907 | 1.00 | 24.30 |
| 23406 | OH | TYR | D | 657 | -103.245 | 10.065 | 38.206 | 1.00 | 20.81 |
| 23407 | CE2 | TYR | D | 657 | -101.912 | 10.903 | 40.001 | 1.00 | 23.39 |
| 23408 | CD2 | TYR | D | 657 | -100.743 | 10.935 | 40.701 | 1.00 | 25.39 |
| 23409 | C | TYR | D | 657 | -96.831 | 8.985 | 42.554 | 1.00 | 28.74 |
| 23410 | O | TYR | D | 657 | -96.433 | 7.886 | 42.167 | 1.00 | 28.89 |
| 23411 | N | ARG | D | 658 | -96.024 | 9.899 | 43.077 | 1.00 | 29.24 |
| 23412 | CA | ARG | D | 658 | -94.595 | 9.664 | 43.158 | 1.00 | 29.78 |
| 23413 | CB | ARG | D | 658 | -93.843 | 10.986 | 43.273 | 1.00 | 29.78 |
| 23414 | CG | ARG | D | 658 | -93.840 | 11.758 | 41.990 | 1.00 | 30.49 |
| 23415 | CD | ARG | D | 658 | -93.500 | 10.875 | 40.774 | 1.00 | 33.83 |
| 23416 | NE | ARG | D | 658 | -93.915 | 11.491 | 39.519 | 1.00 | 32.92 |
| 23417 | CZ | ARG | D | 658 | -93.256 | 12.469 | 38.929 | 1.00 | 33.21 |
| 23418 | NH1 | ARG | D | 658 | -92.145 | 12.928 | 39.478 | 1.00 | 33.18 |
| 23419 | NH2 | ARG | D | 658 | -93.701 | 12.980 | 37.786 | 1.00 | 33.18 |
| 23420 | C | ARG | D | 658 | -94.269 | 8.807 | 44.344 | 1.00 | 30.14 |
| 23421 | O | ARG | D | 658 | -93.181 | 8.244 | 44.439 | 1.00 | 30.68 |
| 23422 | N | ASN | D | 659 | -95.218 | 8.731 | 45.257 | 1.00 | 30.69 |
| 23423 | CA | ASN | D | 659 | -95.044 | 7.998 | 46.496 | 1.00 | 31.33 |
| 23424 | CB | ASN | D | 659 | -95.796 | 8.704 | 47.625 | 1.00 | 32.34 |
| 23425 | CG | ASN | D | 659 | -94.874 | 9.237 | 48.681 | 1.00 | 36.48 |
| 23426 | OD1 | ASN | D | 659 | -94.189 | 10.246 | 48.469 | 1.00 | 41.41 |
| 23427 | ND2 | ASN | D | 659 | -94.811 | 8.542 | 49.827 | 1.00 | 39.55 |
| 23428 | C | ASN | D | 659 | -95.549 | 6.578 | 46.444 | 1.00 | 30.22 |
| 23429 | O | ASN | D | 659 | -95.230 | 5.802 | 47.316 | 1.00 | 30.45 |
| 23430 | N | SER | D | 660 | -96.362 | 6.248 | 45.444 | 1.00 | 28.90 |
| 23431 | CA | SER | D | 660 | -96.971 | 4.929 | 45.403 | 1.00 | 27.43 |
| 23432 | CB | SER | D | 660 | -98.493 | 5.075 | 45.292 | 1.00 | 27.34 |
| 23433 | OG | SER | D | 660 | -98.852 | 5.896 | 44.191 | 1.00 | 26.77 |
| 23434 | C | SER | D | 660 | -96.400 | 3.989 | 44.318 | 1.00 | 26.29 |
| 23435 | O | SER | D | 660 | -97.068 | 3.064 | 43.845 | 1.00 | 25.76 |
| 23436 | N | THR | D | 661 | -95.155 | 4.221 | 43.941 | 1.00 | 24.89 |
| 23437 | CA | THR | D | 661 | -94.514 | 3.377 | 42.960 | 1.00 | 23.90 |
| 23438 | CB | THR | D | 661 | -93.373 | 4.143 | 42.316 | 1.00 | 24.52 |
| 23439 | OG1 | THR | D | 661 | -92.362 | 4.347 | 43.308 | 1.00 | 25.03 |
| 23440 | CG2 | THR | D | 661 | -93.800 | 5.542 | 41.940 | 1.00 | 23.39 |
| 23441 | C | THR | D | 661 | -93.891 | 2.180 | 43.653 | 1.00 | 22.71 |
| 23442 | O | THR | D | 661 | -93.467 | 2.280 | 44.804 | 1.00 | 21.58 |
| 23443 | N | VAL | D | 662 | -93.778 | 1.054 | 42.961 | 1.00 | 21.39 |
| 23444 | CA | VAL | D | 662 | -93.064 | -0.028 | 43.610 | 1.00 | 20.70 |
| 23445 | CB | VAL | D | 662 | -93.480 | -1.500 | 43.158 | 1.00 | 20.31 |
| 23446 | CG1 | VAL | D | 662 | -94.804 | -1.542 | 42.414 | 1.00 | 17.64 |
| 23447 | CG2 | VAL | D | 662 | -92.383 | -2.269 | 42.485 | 1.00 | 16.38 |
| 23448 | C | VAL | D | 662 | -91.563 | 0.236 | 43.600 | 1.00 | 21.43 |
| 23449 | O | VAL | D | 662 | -90.860 | -0.163 | 44.525 | 1.00 | 22.11 |
| 23450 | N | MET | D | 663 | -91.078 | 0.929 | 42.569 | 1.00 | 22.18 |

FIGURE 3 ST

| A | B | C | D | E | F | G | H | I | J |
|---|---|---|---|---|---|---|---|---|---|
| 23451 | CA | MET | D | 663 | -89.658 | 1.265 | 42.469 | 1.00 | 22.22 |
| 23452 | CB | MET | D | 663 | -89.362 | 2.125 | 41.223 | 1.00 | 22.16 |
| 23453 | CG | MET | D | 663 | -89.309 | 1.330 | 39.884 | 1.00 | 20.41 |
| 23454 | SD | MET | D | 663 | -90.971 | 0.820 | 39.315 | 1.00 | 20.24 |
| 23455 | CE | MET | D | 663 | -91.665 | 2.361 | 38.782 | 1.00 | 17.95 |
| 23456 | C | MET | D | 663 | -89.071 | 1.930 | 43.709 | 1.00 | 23.01 |
| 23457 | O | MET | D | 663 | -87.908 | 1.695 | 44.039 | 1.00 | 24.00 |
| 23458 | N | SER | D | 664 | -89.840 | 2.751 | 44.409 | 1.00 | 23.37 |
| 23459 | CA | SER | D | 664 | -89.273 | 3.427 | 45.571 | 1.00 | 24.66 |
| 23460 | CB | SER | D | 664 | -90.184 | 4.544 | 46.035 | 1.00 | 25.02 |
| 23461 | OG | SER | D | 664 | -91.461 | 4.013 | 46.338 | 1.00 | 27.47 |
| 23462 | C | SER | D | 664 | -89.039 | 2.465 | 46.740 | 1.00 | 25.06 |
| 23463 | O | SER | D | 664 | -88.336 | 2.799 | 47.696 | 1.00 | 24.70 |
| 23464 | N | ARG | D | 665 | -89.614 | 1.268 | 46.649 | 1.00 | 24.56 |
| 23465 | CA | ARG | D | 665 | -89.456 | 0.284 | 47.700 | 1.00 | 24.85 |
| 23466 | CB | ARG | D | 665 | -90.798 | -0.369 | 47.999 | 1.00 | 24.78 |
| 23467 | CG | ARG | D | 665 | -91.809 | 0.640 | 48.551 | 1.00 | 25.88 |
| 23468 | CD | ARG | D | 665 | -93.214 | 0.129 | 48.642 | 1.00 | 26.79 |
| 23469 | NE | ARG | D | 665 | -94.129 | 1.112 | 49.216 | 1.00 | 26.35 |
| 23470 | CZ | ARG | D | 665 | -95.170 | 0.782 | 49.957 | 1.00 | 27.60 |
| 23471 | NH1 | ARG | D | 665 | -95.418 | -0.496 | 50.206 | 1.00 | 28.66 |
| 23472 | NH2 | ARG | D | 665 | -95.967 | 1.715 | 50.455 | 1.00 | 29.38 |
| 23473 | C | ARG | D | 665 | -88.441 | -0.766 | 47.343 | 1.00 | 24.22 |
| 23474 | O | ARG | D | 665 | -88.350 | -1.778 | 48.011 | 1.00 | 24.33 |
| 23475 | N | ALA | D | 666 | -87.675 | -0.518 | 46.292 | 1.00 | 24.52 |
| 23476 | CA | ALA | D | 666 | -86.732 | -1.511 | 45.771 | 1.00 | 24.78 |
| 23477 | CB | ALA | D | 666 | -85.950 | -0.935 | 44.627 | 1.00 | 24.85 |
| 23478 | C | ALA | D | 666 | -85.784 | -2.118 | 46.790 | 1.00 | 25.15 |
| 23479 | O | ALA | D | 666 | -85.509 | -3.314 | 46.751 | 1.00 | 25.19 |
| 23480 | N | GLU | D | 667 | -85.271 | -1.302 | 47.697 | 1.00 | 25.94 |
| 23481 | CA | GLU | D | 667 | -84.308 | -1.783 | 48.683 | 1.00 | 26.94 |
| 23482 | CB | GLU | D | 667 | -83.817 | -0.616 | 49.578 | 1.00 | 27.70 |
| 23483 | CG | GLU | D | 667 | -82.794 | -0.998 | 50.658 | 1.00 | 31.37 |
| 23484 | CD | GLU | D | 667 | -81.432 | -1.370 | 50.083 | 1.00 | 34.98 |
| 23485 | OE1 | GLU | D | 667 | -80.668 | -2.100 | 50.756 | 1.00 | 36.00 |
| 23486 | OE2 | GLU | D | 667 | -81.123 | -0.940 | 48.947 | 1.00 | 37.23 |
| 23487 | C | GLU | D | 667 | -84.913 | -2.892 | 49.526 | 1.00 | 26.63 |
| 23488 | O | GLU | D | 667 | -84.239 | -3.830 | 49.896 | 1.00 | 26.96 |
| 23489 | N | ASN | D | 668 | -86.197 | -2.792 | 49.819 | 1.00 | 26.69 |
| 23490 | CA | ASN | D | 668 | -86.852 | -3.772 | 50.677 | 1.00 | 26.46 |
| 23491 | CB | ASN | D | 668 | -88.185 | -3.209 | 51.165 | 1.00 | 27.48 |
| 23492 | CG | ASN | D | 668 | -87.996 | -2.144 | 52.216 | 1.00 | 29.06 |
| 23493 | OD1 | ASN | D | 668 | -87.017 | -2.174 | 52.925 | 1.00 | 33.18 |
| 23494 | ND2 | ASN | D | 668 | -88.918 | -1.209 | 52.315 | 1.00 | 31.95 |
| 23495 | C | ASN | D | 668 | -87.082 | -5.133 | 50.049 | 1.00 | 25.84 |
| 23496 | O | ASN | D | 668 | -87.401 | -6.095 | 50.757 | 1.00 | 25.33 |
| 23497 | N | PHE | D | 669 | -86.965 | -5.228 | 48.727 | 1.00 | 24.32 |
| 23498 | CA | PHE | D | 669 | -87.143 | -6.540 | 48.109 | 1.00 | 23.47 |
| 23499 | CB | PHE | D | 669 | -87.296 | -6.454 | 46.589 | 1.00 | 22.54 |
| 23500 | CG | PHE | D | 669 | -88.684 | -6.046 | 46.141 | 1.00 | 21.60 |
| 23501 | CD1 | PHE | D | 669 | -89.139 | -4.736 | 46.343 | 1.00 | 19.42 |

FIGURE 3 SU

| A | B | C | D | E | F | G | H | I | J |
|---|---|---|---|---|---|---|---|---|---|
| 23502 | CE1 | PHE | D | 669 | -90.390 | -4.342 | 45.956 | 1.00 | 17.25 |
| 23503 | CZ | PHE | D | 669 | -91.226 | -5.259 | 45.316 | 1.00 | 20.42 |
| 23504 | CE2 | PHE | D | 669 | -90.779 | -6.576 | 45.097 | 1.00 | 21.06 |
| 23505 | CD2 | PHE | D | 669 | -89.519 | -6.958 | 45.517 | 1.00 | 19.03 |
| 23506 | C | PHE | D | 669 | -85.971 | -7.442 | 48.512 | 1.00 | 23.35 |
| 23507 | O | PHE | D | 669 | -85.915 | -8.609 | 48.140 | 1.00 | 22.93 |
| 23508 | N | LYS | D | 670 | -85.031 | -6.894 | 49.271 | 1.00 | 23.33 |
| 23509 | CA | LYS | D | 670 | -83.916 | -7.711 | 49.740 | 1.00 | 24.37 |
| 23510 | CB | LYS | D | 670 | -82.838 | -6.849 | 50.393 | 1.00 | 24.38 |
| 23511 | CG | LYS | D | 670 | -82.002 | -6.077 | 49.413 | 1.00 | 27.50 |
| 23512 | CD | LYS | D | 670 | -80.915 | -5.305 | 50.156 | 1.00 | 29.30 |
| 23513 | CE | LYS | D | 670 | -80.001 | -4.606 | 49.181 | 1.00 | 30.53 |
| 23514 | NZ | LYS | D | 670 | -79.113 | -3.649 | 49.894 | 1.00 | 33.24 |
| 23515 | C | LYS | D | 670 | -84.438 | -8.656 | 50.789 | 1.00 | 23.62 |
| 23516 | O | LYS | D | 670 | -83.792 | -9.608 | 51.129 | 1.00 | 23.80 |
| 23517 | N | GLN | D | 671 | -85.614 | -8.347 | 51.309 | 1.00 | 23.78 |
| 23518 | CA | GLN | D | 671 | -86.205 | -9.097 | 52.402 | 1.00 | 23.50 |
| 23519 | CB | GLN | D | 671 | -86.968 | -8.115 | 53.317 | 1.00 | 22.86 |
| 23520 | CG | GLN | D | 671 | -86.097 | -6.988 | 53.845 | 1.00 | 20.84 |
| 23521 | CD | GLN | D | 671 | -86.860 | -5.953 | 54.653 | 1.00 | 24.55 |
| 23522 | OE1 | GLN | D | 671 | -87.885 | -5.420 | 54.196 | 1.00 | 23.77 |
| 23523 | NE2 | GLN | D | 671 | -86.355 | -5.644 | 55.859 | 1.00 | 24.62 |
| 23524 | C | GLN | D | 671 | -87.126 | -10.233 | 51.921 | 1.00 | 23.80 |
| 23525 | O | GLN | D | 671 | -87.734 | -10.937 | 52.735 | 1.00 | 23.47 |
| 23526 | N | VAL | D | 672 | -87.218 | -10.421 | 50.606 | 1.00 | 23.40 |
| 23527 | CA | VAL | D | 672 | -88.134 | -11.417 | 50.071 | 1.00 | 23.33 |
| 23528 | CB | VAL | D | 672 | -89.474 | -10.786 | 49.606 | 1.00 | 23.68 |
| 23529 | CG1 | VAL | D | 672 | -90.161 | -10.038 | 50.732 | 1.00 | 22.21 |
| 23530 | CG2 | VAL | D | 672 | -89.225 | -9.834 | 48.423 | 1.00 | 23.11 |
| 23531 | C | VAL | D | 672 | -87.559 | -12.051 | 48.850 | 1.00 | 23.60 |
| 23532 | O | VAL | D | 672 | -86.540 | -11.638 | 48.339 | 1.00 | 23.50 |
| 23533 | N | GLU | D | 673 | -88.239 | -13.080 | 48.389 | 1.00 | 24.36 |
| 23534 | CA | GLU | D | 673 | -87.898 | -13.736 | 47.151 | 1.00 | 24.68 |
| 23535 | CB | GLU | D | 673 | -87.811 | -15.243 | 47.384 | 1.00 | 25.87 |
| 23536 | CG | GLU | D | 673 | -86.707 | -15.589 | 48.378 | 1.00 | 31.11 |
| 23537 | CD | GLU | D | 673 | -87.158 | -16.595 | 49.427 | 1.00 | 38.23 |
| 23538 | OE1 | GLU | D | 673 | -87.836 | -17.584 | 49.062 | 1.00 | 40.78 |
| 23539 | OE2 | GLU | D | 673 | -86.823 | -16.405 | 50.622 | 1.00 | 42.84 |
| 23540 | C | GLU | D | 673 | -89.035 | -13.357 | 46.201 | 1.00 | 23.74 |
| 23541 | O | GLU | D | 673 | -90.220 | -13.564 | 46.513 | 1.00 | 23.16 |
| 23542 | N | TYR | D | 674 | -88.668 | -12.803 | 45.051 | 1.00 | 23.00 |
| 23543 | CA | TYR | D | 674 | -89.626 | -12.190 | 44.129 | 1.00 | 22.63 |
| 23544 | CB | TYR | D | 674 | -89.299 | -10.702 | 44.023 | 1.00 | 22.84 |
| 23545 | CG | TYR | D | 674 | -90.225 | -9.782 | 43.251 | 1.00 | 21.85 |
| 23546 | CD1 | TYR | D | 674 | -91.612 | -9.768 | 43.463 | 1.00 | 22.71 |
| 23547 | CE1 | TYR | D | 674 | -92.441 | -8.860 | 42.771 | 1.00 | 22.21 |
| 23548 | CZ | TYR | D | 674 | -91.850 | -7.946 | 41.874 | 1.00 | 22.62 |
| 23549 | OH | TYR | D | 674 | -92.605 | -7.034 | 41.173 | 1.00 | 23.00 |
| 23550 | CE2 | TYR | D | 674 | -90.498 | -7.951 | 41.672 | 1.00 | 20.57 |
| 23551 | CD2 | TYR | D | 674 | -89.696 | -8.862 | 42.357 | 1.00 | 21.62 |
| 23552 | C | TYR | D | 674 | -89.562 | -12.775 | 42.754 | 1.00 | 22.26 |

FIGURE 3 SV

| A | B | C | D | E | F | G | H | I | J |
|---|---|---|---|---|---|---|---|---|---|
| 23553 | O | TYR | D | 674 | -88.478 | -13.015 | 42.221 | 1.00 | 21.96 |
| 23554 | N | LEU | D | 675 | -90.735 | -12.993 | 42.177 | 1.00 | 22.14 |
| 23555 | CA | LEU | D | 675 | -90.822 | -13.490 | 40.818 | 1.00 | 22.26 |
| 23556 | CB | LEU | D | 675 | -91.456 | -14.890 | 40.762 | 1.00 | 22.37 |
| 23557 | CG | LEU | D | 675 | -91.857 | -15.441 | 39.383 | 1.00 | 21.98 |
| 23558 | CD1 | LEU | D | 675 | -90.692 | -15.466 | 38.445 | 1.00 | 19.90 |
| 23559 | CD2 | LEU | D | 675 | -92.388 | -16.824 | 39.538 | 1.00 | 22.13 |
| 23560 | C | LEU | D | 675 | -91.652 | -12.466 | 40.076 | 1.00 | 22.02 |
| 23561 | O | LEU | D | 675 | -92.773 | -12.181 | 40.469 | 1.00 | 21.37 |
| 23562 | N | LEU | D | 676 | -91.071 | -11.905 | 39.014 | 1.00 | 22.03 |
| 23563 | CA | LEU | D | 676 | -91.705 | -10.848 | 38.242 | 1.00 | 21.86 |
| 23564 | CB | LEU | D | 676 | -90.812 | -9.612 | 38.225 | 1.00 | 21.78 |
| 23565 | CG | LEU | D | 676 | -91.271 | -8.438 | 37.356 | 1.00 | 20.70 |
| 23566 | CD1 | LEU | D | 676 | -90.127 | -7.441 | 37.272 | 1.00 | 20.09 |
| 23567 | CD2 | LEU | D | 676 | -92.502 | -7.791 | 37.931 | 1.00 | 17.32 |
| 23568 | C | LEU | D | 676 | -91.934 | -11.337 | 36.823 | 1.00 | 21.76 |
| 23569 | O | LEU | D | 676 | -90.991 | -11.737 | 36.122 | 1.00 | 21.74 |
| 23570 | N | ILE | D | 677 | -93.186 | -11.292 | 36.396 | 1.00 | 21.49 |
| 23571 | CA | ILE | D | 677 | -93.536 | -11.854 | 35.119 | 1.00 | 21.70 |
| 23572 | CB | ILE | D | 677 | -94.364 | -13.092 | 35.387 | 1.00 | 21.59 |
| 23573 | CG1 | ILE | D | 677 | -93.534 | -14.087 | 36.228 | 1.00 | 21.36 |
| 23574 | CD1 | ILE | D | 677 | -94.300 | -15.327 | 36.633 | 1.00 | 19.60 |
| 23575 | CG2 | ILE | D | 677 | -94.893 | -13.706 | 34.073 | 1.00 | 21.51 |
| 23576 | C | ILE | D | 677 | -94.317 | -10.856 | 34.275 | 1.00 | 22.38 |
| 23577 | O | ILE | D | 677 | -95.221 | -10.179 | 34.786 | 1.00 | 22.88 |
| 23578 | N | HIS | D | 678 | -94.009 | -10.782 | 32.982 | 1.00 | 21.54 |
| 23579 | CA | HIS | D | 678 | -94.726 | -9.840 | 32.138 | 1.00 | 21.73 |
| 23580 | CB | HIS | D | 678 | -94.148 | -8.434 | 32.355 | 1.00 | 21.41 |
| 23581 | CG | HIS | D | 678 | -95.136 | -7.339 | 32.116 | 1.00 | 20.87 |
| 23582 | ND1 | HIS | D | 678 | -95.326 | -6.308 | 33.007 | 1.00 | 18.16 |
| 23583 | CE1 | HIS | D | 678 | -96.270 | -5.504 | 32.547 | 1.00 | 20.39 |
| 23584 | NE2 | HIS | D | 678 | -96.688 | -5.973 | 31.383 | 1.00 | 21.36 |
| 23585 | CD2 | HIS | D | 678 | -96.004 | -7.127 | 31.096 | 1.00 | 18.42 |
| 23586 | C | HIS | D | 678 | -94.686 | -10.199 | 30.650 | 1.00 | 21.66 |
| 23587 | O | HIS | D | 678 | -93.671 | -10.653 | 30.156 | 1.00 | 21.22 |
| 23588 | N | GLY | D | 679 | -95.805 | -10.005 | 29.954 | 1.00 | 22.01 |
| 23589 | CA | GLY | D | 679 | -95.882 | -10.236 | 28.526 | 1.00 | 21.96 |
| 23590 | C | GLY | D | 679 | -95.293 | -9.048 | 27.790 | 1.00 | 22.74 |
| 23591 | O | GLY | D | 679 | -95.645 | -7.917 | 28.089 | 1.00 | 23.15 |
| 23592 | N | THR | D | 680 | -94.417 | -9.278 | 26.811 | 1.00 | 23.16 |
| 23593 | CA | THR | D | 680 | -93.796 | -8.153 | 26.109 | 1.00 | 23.51 |
| 23594 | CB | THR | D | 680 | -92.580 | -8.620 | 25.306 | 1.00 | 23.74 |
| 23595 | OG1 | THR | D | 680 | -93.010 | -9.481 | 24.236 | 1.00 | 24.46 |
| 23596 | CG2 | THR | D | 680 | -91.691 | -9.502 | 26.175 | 1.00 | 20.99 |
| 23597 | C | THR | D | 680 | -94.746 | -7.353 | 25.212 | 1.00 | 24.43 |
| 23598 | O | THR | D | 680 | -94.414 | -6.251 | 24.781 | 1.00 | 24.65 |
| 23599 | N | ALA | D | 681 | -95.936 | -7.894 | 24.960 | 1.00 | 24.82 |
| 23600 | CA | ALA | D | 681 | -96.895 | -7.250 | 24.087 | 1.00 | 25.27 |
| 23601 | CB | ALA | D | 681 | -97.225 | -8.162 | 22.879 | 1.00 | 25.14 |
| 23602 | C | ALA | D | 681 | -98.159 | -6.900 | 24.862 | 1.00 | 25.79 |
| 23603 | O | ALA | D | 681 | -99.280 | -6.920 | 24.325 | 1.00 | 26.71 |

FIGURE 3 SW

| A | B | C | D | E | F | G | H | I | J |
|---|---|---|---|---|---|---|---|---|---|
| 23604 | N | ASP | D | 682 | -97.976 | -6.599 | 26.140 | 1.00 | 25.58 |
| 23605 | CA | ASP | D | 682 | -99.081 | -6.214 | 26.986 | 1.00 | 24.26 |
| 23606 | CB | ASP | D | 682 | -98.642 | -6.316 | 28.432 | 1.00 | 24.03 |
| 23607 | CG | ASP | D | 682 | -99.783 | -6.199 | 29.387 | 1.00 | 23.05 |
| 23608 | OD1 | ASP | D | 682 | -99.778 | -6.903 | 30.430 | 1.00 | 23.38 |
| 23609 | OD2 | ASP | D | 682 | -100.740 | -5.433 | 29.174 | 1.00 | 21.88 |
| 23610 | C | ASP | D | 682 | -99.418 | -4.779 | 26.622 | 1.00 | 24.58 |
| 23611 | O | ASP | D | 682 | -98.620 | -3.862 | 26.879 | 1.00 | 24.35 |
| 23612 | N | ASP | D | 683 | -100.589 | -4.593 | 26.023 | 1.00 | 24.45 |
| 23613 | CA | ASP | D | 683 | -101.022 | -3.300 | 25.515 | 1.00 | 24.69 |
| 23614 | CB | ASP | D | 683 | -101.995 | -3.509 | 24.372 | 1.00 | 24.67 |
| 23615 | CG | ASP | D | 683 | -103.120 | -4.386 | 24.752 | 1.00 | 24.79 |
| 23616 | OD1 | ASP | D | 683 | -102.890 | -5.615 | 24.805 | 1.00 | 25.70 |
| 23617 | OD2 | ASP | D | 683 | -104.267 | -3.960 | 25.029 | 1.00 | 24.84 |
| 23618 | C | ASP | D | 683 | -101.746 | -2.507 | 26.568 | 1.00 | 24.92 |
| 23619 | O | ASP | D | 683 | -102.032 | -1.309 | 26.402 | 1.00 | 24.30 |
| 23620 | N | ASN | D | 684 | -102.060 | -3.212 | 27.647 | 1.00 | 24.70 |
| 23621 | CA | ASN | D | 684 | -102.800 | -2.669 | 28.750 | 1.00 | 23.71 |
| 23622 | CB | ASN | D | 684 | -103.704 | -3.753 | 29.307 | 1.00 | 23.67 |
| 23623 | CG | ASN | D | 684 | -104.729 | -3.216 | 30.259 | 1.00 | 23.03 |
| 23624 | OD1 | ASN | D | 684 | -105.777 | -3.811 | 30.444 | 1.00 | 26.22 |
| 23625 | ND2 | ASN | D | 684 | -104.430 | -2.102 | 30.878 | 1.00 | 22.01 |
| 23626 | C | ASN | D | 684 | -101.798 | -2.178 | 29.780 | 1.00 | 23.32 |
| 23627 | O | ASN | D | 684 | -101.558 | -0.971 | 29.901 | 1.00 | 22.78 |
| 23628 | N | VAL | D | 685 | -101.231 | -3.088 | 30.563 | 1.00 | 22.67 |
| 23629 | CA | VAL | D | 685 | -100.132 | -2.629 | 31.411 | 1.00 | 21.98 |
| 23630 | CB | VAL | D | 685 | -100.272 | -2.932 | 32.943 | 1.00 | 22.73 |
| 23631 | CG1 | VAL | D | 685 | -101.492 | -3.787 | 33.262 | 1.00 | 21.21 |
| 23632 | CG2 | VAL | D | 685 | -98.970 | -3.382 | 33.583 | 1.00 | 22.59 |
| 23633 | C | VAL | D | 685 | -98.850 | -2.986 | 30.716 | 1.00 | 21.40 |
| 23634 | O | VAL | D | 685 | -98.478 | -4.154 | 30.543 | 1.00 | 21.30 |
| 23635 | N | HIS | D | 686 | -98.211 | -1.932 | 30.251 | 1.00 | 20.86 |
| 23636 | CA | HIS | D | 686 | -97.066 | -2.037 | 29.370 | 1.00 | 20.94 |
| 23637 | CB | HIS | D | 686 | -96.757 | -0.652 | 28.814 | 1.00 | 19.78 |
| 23638 | CG | HIS | D | 686 | -97.954 | -0.024 | 28.173 | 1.00 | 19.37 |
| 23639 | ND1 | HIS | D | 686 | -98.243 | 1.321 | 28.263 | 1.00 | 16.50 |
| 23640 | CE1 | HIS | D | 686 | -99.368 | 1.567 | 27.612 | 1.00 | 19.38 |
| 23641 | NE2 | HIS | D | 686 | -99.818 | 0.430 | 27.105 | 1.00 | 19.51 |
| 23642 | CD2 | HIS | D | 686 | -98.956 | -0.579 | 27.447 | 1.00 | 17.66 |
| 23643 | C | HIS | D | 686 | -95.876 | -2.723 | 30.006 | 1.00 | 21.02 |
| 23644 | O | HIS | D | 686 | -95.616 | -2.539 | 31.179 | 1.00 | 21.72 |
| 23645 | N | PHE | D | 687 | -95.189 | -3.558 | 29.237 | 1.00 | 21.34 |
| 23646 | CA | PHE | D | 687 | -93.983 | -4.225 | 29.739 | 1.00 | 20.81 |
| 23647 | CB | PHE | D | 687 | -93.244 | -4.885 | 28.596 | 1.00 | 20.15 |
| 23648 | CG | PHE | D | 687 | -92.055 | -5.702 | 29.028 | 1.00 | 18.91 |
| 23649 | CD1 | PHE | D | 687 | -92.217 | -7.006 | 29.439 | 1.00 | 17.67 |
| 23650 | CE1 | PHE | D | 687 | -91.120 | -7.771 | 29.831 | 1.00 | 17.81 |
| 23651 | CZ | PHE | D | 687 | -89.870 | -7.232 | 29.792 | 1.00 | 16.78 |
| 23652 | CE2 | PHE | D | 687 | -89.687 | -5.931 | 29.380 | 1.00 | 18.33 |
| 23653 | CD2 | PHE | D | 687 | -90.776 | -5.168 | 28.992 | 1.00 | 16.92 |
| 23654 | C | PHE | D | 687 | -93.085 | -3.212 | 30.435 | 1.00 | 21.54 |

FIGURE 3 SX

| A | B | C | D | E | F | G | H | I | J |
|---|---|---|---|---|---|---|---|---|---|
| 23655 | O | PHE | D | 687 | -92.386 | -3.546 | 31.398 | 1.00 | 22.37 |
| 23656 | N | GLN | D | 688 | -93.123 | -1.969 | 29.957 | 1.00 | 21.62 |
| 23657 | CA | GLN | D | 688 | -92.382 | -0.853 | 30.573 | 1.00 | 21.99 |
| 23658 | CB | GLN | D | 688 | -92.986 | 0.489 | 30.082 | 1.00 | 21.49 |
| 23659 | CG | GLN | D | 688 | -92.732 | 1.696 | 30.977 | 1.00 | 21.34 |
| 23660 | CD | GLN | D | 688 | -93.623 | 2.891 | 30.629 | 1.00 | 20.42 |
| 23661 | OE1 | GLN | D | 688 | -94.790 | 2.715 | 30.353 | 1.00 | 21.30 |
| 23662 | NE2 | GLN | D | 688 | -93.062 | 4.094 | 30.637 | 1.00 | 18.03 |
| 23663 | C | GLN | D | 688 | -92.478 | -0.932 | 32.086 | 1.00 | 21.77 |
| 23664 | O | GLN | D | 688 | -91.512 | -0.778 | 32.831 | 1.00 | 22.49 |
| 23665 | N | GLN | D | 689 | -93.687 | -1.173 | 32.537 | 1.00 | 21.98 |
| 23666 | CA | GLN | D | 689 | -93.997 | -1.200 | 33.953 | 1.00 | 22.02 |
| 23667 | CB | GLN | D | 689 | -95.476 | -1.525 | 34.049 | 1.00 | 21.84 |
| 23668 | CG | GLN | D | 689 | -96.174 | -1.035 | 35.257 | 1.00 | 25.01 |
| 23669 | CD | GLN | D | 689 | -97.016 | 0.225 | 35.060 | 1.00 | 23.27 |
| 23670 | OE1 | GLN | D | 689 | -96.955 | 1.084 | 35.896 | 1.00 | 26.17 |
| 23671 | NE2 | GLN | D | 689 | -97.831 | 0.299 | 34.008 | 1.00 | 22.99 |
| 23672 | C | GLN | D | 689 | -93.082 | -2.182 | 34.720 | 1.00 | 22.00 |
| 23673 | O | GLN | D | 689 | -92.516 | -1.843 | 35.763 | 1.00 | 22.48 |
| 23674 | N | SER | D | 690 | -92.908 | -3.398 | 34.203 | 1.00 | 21.84 |
| 23675 | CA | SER | D | 690 | -92.023 | -4.356 | 34.849 | 1.00 | 21.13 |
| 23676 | CB | SER | D | 690 | -92.373 | -5.796 | 34.438 | 1.00 | 21.43 |
| 23677 | OG | SER | D | 690 | -93.582 | -6.212 | 35.034 | 1.00 | 21.44 |
| 23678 | C | SER | D | 690 | -90.574 | -4.068 | 34.496 | 1.00 | 20.96 |
| 23679 | O | SER | D | 690 | -89.685 | -4.366 | 35.275 | 1.00 | 21.48 |
| 23680 | N | ALA | D | 691 | -90.328 | -3.507 | 33.312 | 1.00 | 20.62 |
| 23681 | CA | ALA | D | 691 | -88.970 | -3.153 | 32.913 | 1.00 | 20.80 |
| 23682 | CB | ALA | D | 691 | -88.936 | -2.595 | 31.467 | 1.00 | 20.67 |
| 23683 | C | ALA | D | 691 | -88.351 | -2.152 | 33.884 | 1.00 | 20.77 |
| 23684 | O | ALA | D | 691 | -87.137 | -2.145 | 34.095 | 1.00 | 21.27 |
| 23685 | N | GLN | D | 692 | -89.183 | -1.296 | 34.457 | 1.00 | 20.70 |
| 23686 | CA | GLN | D | 692 | -88.725 | -0.311 | 35.438 | 1.00 | 20.86 |
| 23687 | CB | GLN | D | 692 | -89.684 | 0.888 | 35.491 | 1.00 | 21.00 |
| 23688 | CG | GLN | D | 692 | -89.700 | 1.747 | 34.223 | 1.00 | 22.12 |
| 23689 | CD | GLN | D | 692 | -88.435 | 2.575 | 34.012 | 1.00 | 23.01 |
| 23690 | OE1 | GLN | D | 692 | -87.472 | 2.468 | 34.770 | 1.00 | 26.51 |
| 23691 | NE2 | GLN | D | 692 | -88.439 | 3.405 | 32.976 | 1.00 | 24.59 |
| 23692 | C | GLN | D | 692 | -88.592 | -0.944 | 36.822 | 1.00 | 20.78 |
| 23693 | O | GLN | D | 692 | -87.705 | -0.588 | 37.583 | 1.00 | 20.62 |
| 23694 | N | ILE | D | 693 | -89.467 | -1.888 | 37.158 | 1.00 | 20.68 |
| 23695 | CA | ILE | D | 693 | -89.302 | -2.574 | 38.445 | 1.00 | 20.87 |
| 23696 | CB | ILE | D | 693 | -90.428 | -3.603 | 38.736 | 1.00 | 20.42 |
| 23697 | CG1 | ILE | D | 693 | -91.712 | -2.880 | 39.093 | 1.00 | 19.89 |
| 23698 | CD1 | ILE | D | 693 | -92.905 | -3.825 | 39.351 | 1.00 | 16.39 |
| 23699 | CG2 | ILE | D | 693 | -90.035 | -4.495 | 39.924 | 1.00 | 20.06 |
| 23700 | C | ILE | D | 693 | -87.976 | -3.285 | 38.476 | 1.00 | 20.52 |
| 23701 | O | ILE | D | 693 | -87.219 | -3.168 | 39.422 | 1.00 | 21.24 |
| 23702 | N | SER | D | 694 | -87.693 | -4.037 | 37.422 | 1.00 | 21.10 |
| 23703 | CA | SER | D | 694 | -86.468 | -4.818 | 37.370 | 1.00 | 20.77 |
| 23704 | CB | SER | D | 694 | -86.467 | -5.707 | 36.129 | 1.00 | 21.03 |
| 23705 | OG | SER | D | 694 | -86.308 | -4.942 | 34.945 | 1.00 | 21.23 |

FIGURE 3 SY

| A | B | C | D | E | F | G | H | I | J |
|---|---|---|---|---|---|---|---|---|---|
| 23706 | C | SER | D | 694 | -85.218 | -3.962 | 37.384 | 1.00 | 20.65 |
| 23707 | O | SER | D | 694 | -84.209 | -4.374 | 37.913 | 1.00 | 20.94 |
| 23708 | N | LYS | D | 695 | -85.267 | -2.792 | 36.754 | 1.00 | 20.75 |
| 23709 | CA | LYS | D | 695 | -84.109 | -1.912 | 36.703 | 1.00 | 20.30 |
| 23710 | CB | LYS | D | 695 | -84.316 | -0.806 | 35.647 | 1.00 | 20.51 |
| 23711 | CG | LYS | D | 695 | -83.226 | 0.253 | 35.635 | 1.00 | 19.10 |
| 23712 | CD | LYS | D | 695 | -83.052 | 0.919 | 34.260 | 1.00 | 18.50 |
| 23713 | CE | LYS | D | 695 | -84.301 | 1.678 | 33.807 | 1.00 | 19.63 |
| 23714 | NZ | LYS | D | 695 | -84.671 | 2.888 | 34.658 | 1.00 | 23.49 |
| 23715 | C | LYS | D | 695 | -83.891 | -1.308 | 38.078 | 1.00 | 20.61 |
| 23716 | O | LYS | D | 695 | -82.785 | -1.113 | 38.509 | 1.00 | 20.27 |
| 23717 | N | ALA | D | 696 | -84.957 | -1.016 | 38.788 | 1.00 | 21.51 |
| 23718 | CA | ALA | D | 696 | -84.772 | -0.475 | 40.119 | 1.00 | 23.18 |
| 23719 | CB | ALA | D | 696 | -86.082 | 0.086 | 40.647 | 1.00 | 22.96 |
| 23720 | C | ALA | D | 696 | -84.196 | -1.546 | 41.064 | 1.00 | 24.04 |
| 23721 | O | ALA | D | 696 | -83.400 | -1.233 | 41.946 | 1.00 | 25.62 |
| 23722 | N | LEU | D | 697 | -84.584 | -2.801 | 40.877 | 1.00 | 24.70 |
| 23723 | CA | LEU | D | 697 | -84.048 | -3.893 | 41.711 | 1.00 | 25.61 |
| 23724 | CB | LEU | D | 697 | -84.843 | -5.186 | 41.515 | 1.00 | 25.69 |
| 23725 | CG | LEU | D | 697 | -86.288 | -5.178 | 42.048 | 1.00 | 26.26 |
| 23726 | CD1 | LEU | D | 697 | -86.968 | -6.530 | 41.876 | 1.00 | 26.82 |
| 23727 | CD2 | LEU | D | 697 | -86.304 | -4.787 | 43.504 | 1.00 | 28.62 |
| 23728 | C | LEU | D | 697 | -82.583 | -4.140 | 41.404 | 1.00 | 25.90 |
| 23729 | O | LEU | D | 697 | -81.772 | -4.330 | 42.309 | 1.00 | 26.11 |
| 23730 | N | VAL | D | 698 | -82.237 | -4.134 | 40.121 | 1.00 | 26.07 |
| 23731 | CA | VAL | D | 698 | -80.851 | -4.304 | 39.735 | 1.00 | 25.49 |
| 23732 | CB | VAL | D | 698 | -80.704 | -4.237 | 38.207 | 1.00 | 25.71 |
| 23733 | CG1 | VAL | D | 698 | -79.244 | -4.082 | 37.820 | 1.00 | 23.66 |
| 23734 | CG2 | VAL | D | 698 | -81.313 | -5.488 | 37.555 | 1.00 | 24.81 |
| 23735 | C | VAL | D | 698 | -80.042 | -3.171 | 40.336 | 1.00 | 26.30 |
| 23736 | O | VAL | D | 698 | -78.927 | -3.355 | 40.865 | 1.00 | 26.31 |
| 23737 | N | ASP | D | 699 | -80.606 | -1.974 | 40.255 | 1.00 | 26.42 |
| 23738 | CA | ASP | D | 699 | -79.901 | -0.815 | 40.735 | 1.00 | 27.19 |
| 23739 | CB | ASP | D | 699 | -80.598 | 0.455 | 40.281 | 1.00 | 27.83 |
| 23740 | CG | ASP | D | 699 | -80.334 | 0.748 | 38.820 | 1.00 | 31.61 |
| 23741 | OD1 | ASP | D | 699 | -80.873 | 1.747 | 38.312 | 1.00 | 34.02 |
| 23742 | OD2 | ASP | D | 699 | -79.614 | 0.011 | 38.094 | 1.00 | 35.99 |
| 23743 | C | ASP | D | 699 | -79.538 | -0.802 | 42.231 | 1.00 | 26.39 |
| 23744 | O | ASP | D | 699 | -78.557 | -0.188 | 42.596 | 1.00 | 26.84 |
| 23745 | N | VAL | D | 700 | -80.302 | -1.480 | 43.083 | 1.00 | 25.93 |
| 23746 | CA | VAL | D | 700 | -79.959 | -1.529 | 44.515 | 1.00 | 25.70 |
| 23747 | CB | VAL | D | 700 | -81.141 | -1.142 | 45.464 | 1.00 | 25.71 |
| 23748 | CG1 | VAL | D | 700 | -81.578 | 0.292 | 45.252 | 1.00 | 24.57 |
| 23749 | CG2 | VAL | D | 700 | -82.323 | -2.091 | 45.296 | 1.00 | 26.35 |
| 23750 | C | VAL | D | 700 | -79.419 | -2.902 | 44.905 | 1.00 | 25.77 |
| 23751 | O | VAL | D | 700 | -79.240 | -3.190 | 46.069 | 1.00 | 25.50 |
| 23752 | N | GLY | D | 701 | -79.180 | -3.753 | 43.915 | 1.00 | 26.22 |
| 23753 | CA | GLY | D | 701 | -78.559 | -5.044 | 44.146 | 1.00 | 26.35 |
| 23754 | C | GLY | D | 701 | -79.447 | -6.124 | 44.743 | 1.00 | 26.80 |
| 23755 | O | GLY | D | 701 | -78.981 | -6.948 | 45.535 | 1.00 | 26.86 |
| 23756 | N | VAL | D | 702 | -80.727 | -6.127 | 44.413 | 1.00 | 26.80 |

FIGURE 3 SZ

| A | B | C | D | E | F | G | H | I | J |
|---|---|---|---|---|---|---|---|---|---|
| 23757 | CA | VAL | D | 702 | -81.542 | -7.235 | 44.879 | 1.00 | 27.14 |
| 23758 | CB | VAL | D | 702 | -82.865 | -6.825 | 45.543 | 1.00 | 27.17 |
| 23759 | CG1 | VAL | D | 702 | -82.988 | -5.322 | 45.630 | 1.00 | 27.53 |
| 23760 | CG2 | VAL | D | 702 | -84.064 | -7.518 | 44.885 | 1.00 | 27.60 |
| 23761 | C | VAL | D | 702 | -81.731 | -8.279 | 43.806 | 1.00 | 26.77 |
| 23762 | O | VAL | D | 702 | -82.007 | -7.965 | 42.649 | 1.00 | 27.38 |
| 23763 | N | ASP | D | 703 | -81.519 | -9.522 | 44.204 | 1.00 | 26.53 |
| 23764 | CA | ASP | D | 703 | -81.709 | -10.650 | 43.329 | 1.00 | 27.21 |
| 23765 | CB | ASP | D | 703 | -80.837 | -11.838 | 43.754 | 1.00 | 27.73 |
| 23766 | CG | ASP | D | 703 | -80.774 | -12.911 | 42.670 | 1.00 | 28.68 |
| 23767 | OD1 | ASP | D | 703 | -81.055 | -14.081 | 42.993 | 1.00 | 30.69 |
| 23768 | OD2 | ASP | D | 703 | -80.499 | -12.661 | 41.465 | 1.00 | 25.48 |
| 23769 | C | ASP | D | 703 | -83.169 | -11.052 | 43.358 | 1.00 | 26.90 |
| 23770 | O | ASP | D | 703 | -83.814 | -11.018 | 44.407 | 1.00 | 27.76 |
| 23771 | N | PHE | D | 704 | -83.688 | -11.420 | 42.199 | 1.00 | 26.19 |
| 23772 | CA | PHE | D | 704 | -85.078 | -11.811 | 42.067 | 1.00 | 25.30 |
| 23773 | CB | PHE | D | 704 | -85.953 | -10.575 | 41.857 | 1.00 | 25.19 |
| 23774 | CG | PHE | D | 704 | -85.616 | -9.791 | 40.615 | 1.00 | 24.20 |
| 23775 | CD1 | PHE | D | 704 | -86.372 | -9.940 | 39.462 | 1.00 | 23.72 |
| 23776 | CE1 | PHE | D | 704 | -86.070 | -9.213 | 38.310 | 1.00 | 24.12 |
| 23777 | CZ | PHE | D | 704 | -85.002 | -8.309 | 38.306 | 1.00 | 21.64 |
| 23778 | CE2 | PHE | D | 704 | -84.252 | -8.150 | 39.435 | 1.00 | 22.32 |
| 23779 | CD2 | PHE | D | 704 | -84.556 | -8.894 | 40.600 | 1.00 | 23.35 |
| 23780 | C | PHE | D | 704 | -85.166 | -12.718 | 40.866 | 1.00 | 25.50 |
| 23781 | O | PHE | D | 704 | -84.166 | -12.925 | 40.160 | 1.00 | 25.56 |
| 23782 | N | GLN | D | 705 | -86.348 | -13.278 | 40.634 | 1.00 | 25.49 |
| 23783 | CA | GLN | D | 705 | -86.545 | -14.123 | 39.478 | 1.00 | 25.80 |
| 23784 | CB | GLN | D | 705 | -87.227 | -15.434 | 39.868 | 1.00 | 26.41 |
| 23785 | CG | GLN | D | 705 | -86.449 | -16.305 | 40.838 | 1.00 | 31.23 |
| 23786 | CD | GLN | D | 705 | -84.996 | -16.436 | 40.468 | 1.00 | 37.91 |
| 23787 | OE1 | GLN | D | 705 | -84.110 | -16.189 | 41.296 | 1.00 | 43.51 |
| 23788 | NE2 | GLN | D | 705 | -84.736 | -16.806 | 39.234 | 1.00 | 39.39 |
| 23789 | C | GLN | D | 705 | -87.417 | -13.375 | 38.472 | 1.00 | 24.92 |
| 23790 | O | GLN | D | 705 | -88.367 | -12.701 | 38.858 | 1.00 | 24.68 |
| 23791 | N | ALA | D | 706 | -87.095 | -13.494 | 37.192 | 1.00 | 23.71 |
| 23792 | CA | ALA | D | 706 | -87.899 | -12.868 | 36.155 | 1.00 | 23.59 |
| 23793 | CB | ALA | D | 706 | -87.135 | -11.717 | 35.509 | 1.00 | 22.50 |
| 23794 | C | ALA | D | 706 | -88.372 | -13.858 | 35.067 | 1.00 | 23.75 |
| 23795 | O | ALA | D | 706 | -87.830 | -14.963 | 34.896 | 1.00 | 23.51 |
| 23796 | N | MET | D | 707 | -89.393 | -13.443 | 34.336 | 1.00 | 23.38 |
| 23797 | CA | MET | D | 707 | -89.810 | -14.180 | 33.164 | 1.00 | 23.04 |
| 23798 | CB | MET | D | 707 | -90.678 | -15.378 | 33.533 | 1.00 | 23.25 |
| 23799 | CG | MET | D | 707 | -91.241 | -16.082 | 32.322 | 1.00 | 24.57 |
| 23800 | SD | MET | D | 707 | -89.962 | -16.899 | 31.331 | 1.00 | 26.76 |
| 23801 | CE | MET | D | 707 | -89.257 | -18.031 | 32.519 | 1.00 | 22.19 |
| 23802 | C | MET | D | 707 | -90.606 | -13.275 | 32.259 | 1.00 | 22.67 |
| 23803 | O | MET | D | 707 | -91.645 | -12.765 | 32.654 | 1.00 | 22.28 |
| 23804 | N | TRP | D | 708 | -90.100 | -13.059 | 31.050 | 1.00 | 22.64 |
| 23805 | CA | TRP | D | 708 | -90.846 | -12.327 | 30.044 | 1.00 | 22.61 |
| 23806 | CB | TRP | D | 708 | -89.895 | -11.449 | 29.221 | 1.00 | 21.99 |
| 23807 | CG | TRP | D | 708 | -89.120 | -12.216 | 28.185 | 1.00 | 22.43 |

FIGURE 3 TA

| A | B | C | D | E | F | G | H | I | J |
|---|---|---|---|---|---|---|---|---|---|
| 23808 | CD1 | TRP | D | 708 | -89.596 | -12.706 | 26.987 | 1.00 | 24.21 |
| 23809 | NE1 | TRP | D | 708 | -88.599 | -13.382 | 26.324 | 1.00 | 23.29 |
| 23810 | CE2 | TRP | D | 708 | -87.451 | -13.313 | 27.072 | 1.00 | 23.65 |
| 23811 | CD2 | TRP | D | 708 | -87.746 | -12.594 | 28.245 | 1.00 | 21.39 |
| 23812 | CE3 | TRP | D | 708 | -86.736 | -12.429 | 29.190 | 1.00 | 21.74 |
| 23813 | CZ3 | TRP | D | 708 | -85.491 | -12.934 | 28.929 | 1.00 | 22.63 |
| 23814 | CH2 | TRP | D | 708 | -85.228 | -13.637 | 27.764 | 1.00 | 23.46 |
| 23815 | CZ2 | TRP | D | 708 | -86.190 | -13.839 | 26.823 | 1.00 | 23.70 |
| 23816 | C | TRP | D | 708 | -91.550 | -13.377 | 29.151 | 1.00 | 22.38 |
| 23817 | O | TRP | D | 708 | -91.024 | -14.476 | 28.951 | 1.00 | 23.23 |
| 23818 | N | TYR | D | 709 | -92.724 | -13.051 | 28.643 | 1.00 | 21.87 |
| 23819 | CA | TYR | D | 709 | -93.463 | -13.930 | 27.722 | 1.00 | 22.29 |
| 23820 | CB | TYR | D | 709 | -94.837 | -14.327 | 28.265 | 1.00 | 21.63 |
| 23821 | CG | TYR | D | 709 | -94.689 | -15.448 | 29.240 | 1.00 | 23.13 |
| 23822 | CD1 | TYR | D | 709 | -94.370 | -16.730 | 28.809 | 1.00 | 23.03 |
| 23823 | CE1 | TYR | D | 709 | -94.181 | -17.766 | 29.719 | 1.00 | 24.34 |
| 23824 | CZ | TYR | D | 709 | -94.292 | -17.511 | 31.064 | 1.00 | 24.60 |
| 23825 | OH | TYR | D | 709 | -94.110 | -18.520 | 31.982 | 1.00 | 23.02 |
| 23826 | CE2 | TYR | D | 709 | -94.590 | -16.241 | 31.502 | 1.00 | 24.89 |
| 23827 | CD2 | TYR | D | 709 | -94.774 | -15.219 | 30.596 | 1.00 | 23.35 |
| 23828 | C | TYR | D | 709 | -93.597 | -13.210 | 26.406 | 1.00 | 22.46 |
| 23829 | O | TYR | D | 709 | -94.368 | -12.263 | 26.268 | 1.00 | 22.19 |
| 23830 | N | THR | D | 710 | -92.755 | -13.612 | 25.478 | 1.00 | 23.10 |
| 23831 | CA | THR | D | 710 | -92.679 | -12.985 | 24.181 | 1.00 | 24.34 |
| 23832 | CB | THR | D | 710 | -91.715 | -13.792 | 23.325 | 1.00 | 24.78 |
| 23833 | OG1 | THR | D | 710 | -90.418 | -13.773 | 23.935 | 1.00 | 25.52 |
| 23834 | CG2 | THR | D | 710 | -91.523 | -13.116 | 21.986 | 1.00 | 24.41 |
| 23835 | C | THR | D | 710 | -94.007 | -12.947 | 23.460 | 1.00 | 24.60 |
| 23836 | O | THR | D | 710 | -94.601 | -14.000 | 23.195 | 1.00 | 24.62 |
| 23837 | N | ASP | D | 711 | -94.443 | -11.733 | 23.132 | 1.00 | 25.02 |
| 23838 | CA | ASP | D | 711 | -95.653 | -11.486 | 22.346 | 1.00 | 25.41 |
| 23839 | CB | ASP | D | 711 | -95.652 | -12.268 | 21.029 | 1.00 | 25.30 |
| 23840 | CG | ASP | D | 711 | -94.688 | -11.684 | 20.013 | 1.00 | 27.89 |
| 23841 | OD1 | ASP | D | 711 | -94.501 | -12.313 | 18.929 | 1.00 | 30.31 |
| 23842 | OD2 | ASP | D | 711 | -94.074 | -10.600 | 20.202 | 1.00 | 27.02 |
| 23843 | C | ASP | D | 711 | -96.957 | -11.705 | 23.069 | 1.00 | 25.14 |
| 23844 | O | ASP | D | 711 | -98.024 | -11.540 | 22.468 | 1.00 | 24.79 |
| 23845 | N | GLU | D | 712 | -96.893 | -12.086 | 24.343 | 1.00 | 24.54 |
| 23846 | CA | GLU | D | 712 | -98.129 | -12.243 | 25.092 | 1.00 | 24.67 |
| 23847 | CB | GLU | D | 712 | -97.945 | -13.177 | 26.291 | 1.00 | 24.69 |
| 23848 | CG | GLU | D | 712 | -97.697 | -14.640 | 25.904 | 1.00 | 26.15 |
| 23849 | CD | GLU | D | 712 | -98.864 | -15.265 | 25.148 | 1.00 | 28.70 |
| 23850 | OE1 | GLU | D | 712 | -98.685 | -15.605 | 23.955 | 1.00 | 32.99 |
| 23851 | OE2 | GLU | D | 712 | -99.954 | -15.436 | 25.729 | 1.00 | 28.16 |
| 23852 | C | GLU | D | 712 | -98.662 | -10.871 | 25.525 | 1.00 | 24.90 |
| 23853 | O | GLU | D | 712 | -97.894 | -9.908 | 25.710 | 1.00 | 24.40 |
| 23854 | N | ASP | D | 713 | -99.977 | -10.766 | 25.677 | 1.00 | 25.38 |
| 23855 | CA | ASP | D | 713 | -100.541 | -9.490 | 26.086 | 1.00 | 26.35 |
| 23856 | CB | ASP | D | 713 | -101.709 | -9.066 | 25.204 | 1.00 | 26.45 |
| 23857 | CG | ASP | D | 713 | -102.948 | -9.944 | 25.385 | 1.00 | 28.52 |
| 23858 | OD1 | ASP | D | 713 | -103.943 | -9.689 | 24.664 | 1.00 | 32.19 |

FIGURE 3 TB

| A | B | C | D | E | F | G | H | I | J |
|---|---|---|---|---|---|---|---|---|---|
| 23859 | OD2 | ASP | D | 713 | -103.044 | -10.866 | 26.221 | 1.00 | 27.60 |
| 23860 | C | ASP | D | 713 | -100.891 | -9.553 | 27.562 | 1.00 | 25.89 |
| 23861 | O | ASP | D | 713 | -100.273 | -10.324 | 28.296 | 1.00 | 26.04 |
| 23862 | N | HIS | D | 714 | -101.868 | -8.774 | 28.008 | 1.00 | 25.24 |
| 23863 | CA | HIS | D | 714 | -102.177 | -8.773 | 29.429 | 1.00 | 25.39 |
| 23864 | CB | HIS | D | 714 | -103.164 | -7.671 | 29.790 | 1.00 | 24.41 |
| 23865 | CG | HIS | D | 714 | -103.016 | -7.192 | 31.193 | 1.00 | 24.80 |
| 23866 | ND1 | HIS | D | 714 | -101.806 | -6.777 | 31.708 | 1.00 | 24.09 |
| 23867 | CE1 | HIS | D | 714 | -101.964 | -6.433 | 32.973 | 1.00 | 22.22 |
| 23868 | NE2 | HIS | D | 714 | -103.232 | -6.603 | 33.296 | 1.00 | 23.96 |
| 23869 | CD2 | HIS | D | 714 | -103.911 | -7.090 | 32.206 | 1.00 | 25.30 |
| 23870 | C | HIS | D | 714 | -102.679 | -10.104 | 29.948 | 1.00 | 25.99 |
| 23871 | O | HIS | D | 714 | -102.518 | -10.408 | 31.123 | 1.00 | 26.72 |
| 23872 | N | GLY | D | 715 | -103.277 | -10.911 | 29.076 | 1.00 | 26.76 |
| 23873 | CA | GLY | D | 715 | -103.860 | -12.168 | 29.492 | 1.00 | 27.06 |
| 23874 | C | GLY | D | 715 | -102.894 | -13.334 | 29.578 | 1.00 | 28.15 |
| 23875 | O | GLY | D | 715 | -103.189 | -14.317 | 30.269 | 1.00 | 28.12 |
| 23876 | N | ILE | D | 716 | -101.738 | -13.226 | 28.916 | 1.00 | 28.62 |
| 23877 | CA | ILE | D | 716 | -100.816 | -14.350 | 28.828 | 1.00 | 29.13 |
| 23878 | CB | ILE | D | 716 | -99.971 | -14.457 | 30.096 | 1.00 | 29.10 |
| 23879 | CG1 | ILE | D | 716 | -99.493 | -13.050 | 30.505 | 1.00 | 28.03 |
| 23880 | CD1 | ILE | D | 716 | -98.224 | -13.034 | 31.308 | 1.00 | 26.15 |
| 23881 | CG2 | ILE | D | 716 | -98.794 | -15.432 | 29.879 | 1.00 | 26.30 |
| 23882 | C | ILE | D | 716 | -101.699 | -15.567 | 28.663 | 1.00 | 30.53 |
| 23883 | O | ILE | D | 716 | -101.572 | -16.553 | 29.377 | 1.00 | 30.93 |
| 23884 | N | ALA | D | 717 | -102.581 | -15.488 | 27.676 | 1.00 | 31.90 |
| 23885 | CA | ALA | D | 717 | -103.652 | -16.452 | 27.527 | 1.00 | 32.82 |
| 23886 | CB | ALA | D | 717 | -104.971 | -15.701 | 27.359 | 1.00 | 32.77 |
| 23887 | C | ALA | D | 717 | -103.468 | -17.466 | 26.411 | 1.00 | 33.53 |
| 23888 | O | ALA | D | 717 | -104.297 | -18.345 | 26.225 | 1.00 | 34.26 |
| 23889 | N | SER | D | 718 | -102.414 | -17.337 | 25.631 | 1.00 | 34.51 |
| 23890 | CA | SER | D | 718 | -102.149 | -18.369 | 24.648 | 1.00 | 34.89 |
| 23891 | CB | SER | D | 718 | -100.813 | -18.117 | 23.966 | 1.00 | 35.09 |
| 23892 | OG | SER | D | 718 | -100.861 | -16.872 | 23.278 | 1.00 | 38.42 |
| 23893 | C | SER | D | 718 | -102.138 | -19.699 | 25.406 | 1.00 | 34.66 |
| 23894 | O | SER | D | 718 | -101.737 | -19.773 | 26.560 | 1.00 | 34.70 |
| 23895 | N | SER | D | 719 | -102.597 | -20.754 | 24.763 | 1.00 | 34.36 |
| 23896 | CA | SER | D | 719 | -102.646 | -22.033 | 25.429 | 1.00 | 33.70 |
| 23897 | CB | SER | D | 719 | -103.188 | -23.106 | 24.485 | 1.00 | 33.97 |
| 23898 | OG | SER | D | 719 | -103.222 | -24.340 | 25.165 | 1.00 | 35.36 |
| 23899 | C | SER | D | 719 | -101.266 | -22.419 | 25.974 | 1.00 | 32.72 |
| 23900 | O | SER | D | 719 | -101.151 | -22.841 | 27.119 | 1.00 | 32.25 |
| 23901 | N | THR | D | 720 | -100.218 | -22.252 | 25.175 | 1.00 | 31.69 |
| 23902 | CA | THR | D | 720 | -98.884 | -22.618 | 25.653 | 1.00 | 31.34 |
| 23903 | CB | THR | D | 720 | -97.878 | -22.741 | 24.491 | 1.00 | 31.31 |
| 23904 | OG1 | THR | D | 720 | -97.765 | -21.487 | 23.807 | 1.00 | 30.08 |
| 23905 | CG2 | THR | D | 720 | -98.408 | -23.750 | 23.417 | 1.00 | 31.67 |
| 23906 | C | THR | D | 720 | -98.321 | -21.702 | 26.751 | 1.00 | 31.24 |
| 23907 | O | THR | D | 720 | -97.699 | -22.181 | 27.701 | 1.00 | 31.39 |
| 23908 | N | ALA | D | 721 | -98.542 | -20.397 | 26.632 | 1.00 | 30.79 |
| 23909 | CA | ALA | D | 721 | -97.983 | -19.459 | 27.599 | 1.00 | 30.63 |

FIGURE 3 TC

| A | B | C | D | E | F | G | H | I | J |
|---|---|---|---|---|---|---|---|---|---|
| 23910 | CB | ALA | D | 721 | -98.069 | -18.010 | 27.084 | 1.00 | 30.07 |
| 23911 | C | ALA | D | 721 | -98.715 | -19.615 | 28.901 | 1.00 | 30.47 |
| 23912 | O | ALA | D | 721 | -98.129 | -19.542 | 29.969 | 1.00 | 30.41 |
| 23913 | N | HIS | D | 722 | -100.011 | -19.859 | 28.800 | 1.00 | 30.82 |
| 23914 | CA | HIS | D | 722 | -100.831 | -20.075 | 29.982 | 1.00 | 31.21 |
| 23915 | CB | HIS | D | 722 | -102.294 | -20.280 | 29.581 | 1.00 | 31.42 |
| 23916 | CG | HIS | D | 722 | -103.150 | -20.822 | 30.680 | 1.00 | 32.76 |
| 23917 | ND1 | HIS | D | 722 | -103.602 | -20.045 | 31.721 | 1.00 | 34.01 |
| 23918 | CE1 | HIS | D | 722 | -104.335 | -20.781 | 32.537 | 1.00 | 34.22 |
| 23919 | NE2 | HIS | D | 722 | -104.363 | -22.014 | 32.070 | 1.00 | 35.08 |
| 23920 | CD2 | HIS | D | 722 | -103.629 | -22.068 | 30.908 | 1.00 | 34.44 |
| 23921 | C | HIS | D | 722 | -100.311 | -21.270 | 30.771 | 1.00 | 31.02 |
| 23922 | O | HIS | D | 722 | -100.170 | -21.216 | 32.002 | 1.00 | 31.48 |
| 23923 | N | GLN | D | 723 | -100.019 | -22.360 | 30.077 | 1.00 | 30.29 |
| 23924 | CA | GLN | D | 723 | -99.473 | -23.517 | 30.769 | 1.00 | 29.72 |
| 23925 | CB | GLN | D | 723 | -99.444 | -24.737 | 29.836 | 1.00 | 29.79 |
| 23926 | CG | GLN | D | 723 | -100.808 | -25.099 | 29.260 | 1.00 | 31.78 |
| 23927 | CD | GLN | D | 723 | -100.717 | -26.195 | 28.215 | 1.00 | 34.32 |
| 23928 | OE1 | GLN | D | 723 | -100.201 | -27.290 | 28.495 | 1.00 | 36.17 |
| 23929 | NE2 | GLN | D | 723 | -101.196 | -25.906 | 27.010 | 1.00 | 31.59 |
| 23930 | C | GLN | D | 723 | -98.063 | -23.233 | 31.296 | 1.00 | 28.87 |
| 23931 | O | GLN | D | 723 | -97.680 | -23.717 | 32.361 | 1.00 | 28.62 |
| 23932 | N | HIS | D | 724 | -97.283 | -22.482 | 30.531 | 1.00 | 28.25 |
| 23933 | CA | HIS | D | 724 | -95.901 | -22.186 | 30.909 | 1.00 | 28.61 |
| 23934 | CB | HIS | D | 724 | -95.137 | -21.579 | 29.730 | 1.00 | 28.69 |
| 23935 | CG | HIS | D | 724 | -93.650 | -21.580 | 29.904 | 1.00 | 29.79 |
| 23936 | ND1 | HIS | D | 724 | -92.995 | -20.699 | 30.738 | 1.00 | 29.17 |
| 23937 | CE1 | HIS | D | 724 | -91.693 | -20.935 | 30.687 | 1.00 | 29.96 |
| 23938 | NE2 | HIS | D | 724 | -91.482 | -21.936 | 29.850 | 1.00 | 29.22 |
| 23939 | CD2 | HIS | D | 724 | -92.688 | -22.354 | 29.344 | 1.00 | 30.80 |
| 23940 | C | HIS | D | 724 | -95.776 | -21.298 | 32.152 | 1.00 | 28.58 |
| 23941 | O | HIS | D | 724 | -94.914 | -21.534 | 32.987 | 1.00 | 28.75 |
| 23942 | N | ILE | D | 725 | -96.655 | -20.304 | 32.293 | 1.00 | 28.58 |
| 23943 | CA | ILE | D | 725 | -96.589 | -19.408 | 33.439 | 1.00 | 28.30 |
| 23944 | CB | ILE | D | 725 | -97.407 | -18.092 | 33.204 | 1.00 | 28.22 |
| 23945 | CG1 | ILE | D | 725 | -97.166 | -17.107 | 34.359 | 1.00 | 26.66 |
| 23946 | CD1 | ILE | D | 725 | -97.987 | -15.800 | 34.259 | 1.00 | 23.69 |
| 23947 | CG2 | ILE | D | 725 | -98.897 | -18.358 | 33.041 | 1.00 | 26.98 |
| 23948 | C | ILE | D | 725 | -96.989 | -20.095 | 34.739 | 1.00 | 28.65 |
| 23949 | O | ILE | D | 725 | -96.267 | -20.017 | 35.746 | 1.00 | 28.07 |
| 23950 | N | TYR | D | 726 | -98.124 | -20.798 | 34.723 | 1.00 | 28.74 |
| 23951 | CA | TYR | D | 726 | -98.563 | -21.472 | 35.933 | 1.00 | 28.23 |
| 23952 | CB | TYR | D | 726 | -99.999 | -21.975 | 35.803 | 1.00 | 28.51 |
| 23953 | CG | TYR | D | 726 | -101.012 | -20.863 | 35.981 | 1.00 | 28.99 |
| 23954 | CD1 | TYR | D | 726 | -101.532 | -20.187 | 34.888 | 1.00 | 28.65 |
| 23955 | CE1 | TYR | D | 726 | -102.433 | -19.151 | 35.048 | 1.00 | 27.20 |
| 23956 | CZ | TYR | D | 726 | -102.819 | -18.786 | 36.318 | 1.00 | 27.84 |
| 23957 | OH | TYR | D | 726 | -103.729 | -17.770 | 36.494 | 1.00 | 26.17 |
| 23958 | CE2 | TYR | D | 726 | -102.326 | -19.456 | 37.420 | 1.00 | 27.71 |
| 23959 | CD2 | TYR | D | 726 | -101.417 | -20.470 | 37.250 | 1.00 | 28.75 |
| 23960 | C | TYR | D | 726 | -97.574 | -22.560 | 36.336 | 1.00 | 28.21 |

FIGURE 3 TD

| A | B | C | D | E | F | G | H | I | J |
|---|---|---|---|---|---|---|---|---|---|
| 23961 | O | TYR | D | 726 | -97.392 | -22.827 | 37.521 | 1.00 | 28.14 |
| 23962 | N | THR | D | 727 | -96.908 | -23.155 | 35.352 | 1.00 | 28.24 |
| 23963 | CA | THR | D | 727 | -95.906 | -24.182 | 35.612 | 1.00 | 28.34 |
| 23964 | CB | THR | D | 727 | -95.452 | -24.871 | 34.283 | 1.00 | 28.52 |
| 23965 | OG1 | THR | D | 727 | -96.575 | -25.509 | 33.654 | 1.00 | 30.62 |
| 23966 | CG2 | THR | D | 727 | -94.527 | -26.045 | 34.558 | 1.00 | 27.79 |
| 23967 | C | THR | D | 727 | -94.723 | -23.522 | 36.307 | 1.00 | 28.16 |
| 23968 | O | THR | D | 727 | -94.266 | -23.982 | 37.344 | 1.00 | 28.00 |
| 23969 | N | HIS | D | 728 | -94.249 | -22.417 | 35.746 | 1.00 | 28.34 |
| 23970 | CA | HIS | D | 728 | -93.129 | -21.693 | 36.342 | 1.00 | 27.90 |
| 23971 | CB | HIS | D | 728 | -92.708 | -20.536 | 35.456 | 1.00 | 27.93 |
| 23972 | CG | HIS | D | 728 | -91.256 | -20.190 | 35.569 | 1.00 | 28.71 |
| 23973 | ND1 | HIS | D | 728 | -90.807 | -19.043 | 36.190 | 1.00 | 26.94 |
| 23974 | CE1 | HIS | D | 728 | -89.492 | -18.995 | 36.118 | 1.00 | 26.25 |
| 23975 | NE2 | HIS | D | 728 | -89.069 | -20.066 | 35.471 | 1.00 | 27.15 |
| 23976 | CD2 | HIS | D | 728 | -90.153 | -20.826 | 35.114 | 1.00 | 27.68 |
| 23977 | C | HIS | D | 728 | -93.513 | -21.177 | 37.709 | 1.00 | 27.60 |
| 23978 | O | HIS | D | 728 | -92.732 | -21.260 | 38.642 | 1.00 | 27.81 |
| 23979 | N | MET | D | 729 | -94.736 | -20.680 | 37.854 | 1.00 | 27.20 |
| 23980 | CA | MET | D | 729 | -95.142 | -20.148 | 39.151 | 1.00 | 27.30 |
| 23981 | CB | MET | D | 729 | -96.461 | -19.383 | 39.044 | 1.00 | 27.41 |
| 23982 | CG | MET | D | 729 | -96.356 | -18.089 | 38.223 | 1.00 | 27.80 |
| 23983 | SD | MET | D | 729 | -97.799 | -17.045 | 38.474 | 1.00 | 31.32 |
| 23984 | CE | MET | D | 729 | -98.988 | -17.959 | 37.603 | 1.00 | 28.58 |
| 23985 | C | MET | D | 729 | -95.234 | -21.217 | 40.227 | 1.00 | 27.58 |
| 23986 | O | MET | D | 729 | -94.988 | -20.946 | 41.415 | 1.00 | 26.14 |
| 23987 | N | SER | D | 730 | -95.599 | -22.426 | 39.790 | 1.00 | 28.27 |
| 23988 | CA | SER | D | 730 | -95.763 | -23.574 | 40.675 | 1.00 | 29.26 |
| 23989 | CB | SER | D | 730 | -96.461 | -24.733 | 39.940 | 1.00 | 29.36 |
| 23990 | OG | SER | D | 730 | -97.801 | -24.388 | 39.604 | 1.00 | 30.37 |
| 23991 | C | SER | D | 730 | -94.415 | -24.006 | 41.220 | 1.00 | 29.27 |
| 23992 | O | SER | D | 730 | -94.272 | -24.254 | 42.412 | 1.00 | 29.22 |
| 23993 | N | HIS | D | 731 | -93.429 | -24.070 | 40.341 | 1.00 | 30.11 |
| 23994 | CA | HIS | D | 731 | -92.050 | -24.371 | 40.740 | 1.00 | 31.48 |
| 23995 | CB | HIS | D | 731 | -91.110 | -24.302 | 39.527 | 1.00 | 31.75 |
| 23996 | CG | HIS | D | 731 | -91.168 | -25.502 | 38.635 | 1.00 | 36.02 |
| 23997 | ND1 | HIS | D | 731 | -91.333 | -26.785 | 39.120 | 1.00 | 40.04 |
| 23998 | CE1 | HIS | D | 731 | -91.335 | -27.636 | 38.108 | 1.00 | 41.67 |
| 23999 | NE2 | HIS | D | 731 | -91.175 | -26.955 | 36.986 | 1.00 | 39.65 |
| 24000 | CD2 | HIS | D | 731 | -91.063 | -25.619 | 37.288 | 1.00 | 38.27 |
| 24001 | C | HIS | D | 731 | -91.555 | -23.364 | 41.769 | 1.00 | 31.01 |
| 24002 | O | HIS | D | 731 | -90.973 | -23.743 | 42.788 | 1.00 | 31.43 |
| 24003 | N | PHE | D | 732 | -91.796 | -22.077 | 41.498 | 1.00 | 30.94 |
| 24004 | CA | PHE | D | 732 | -91.300 | -20.990 | 42.351 | 1.00 | 30.28 |
| 24005 | CB | PHE | D | 732 | -91.692 | -19.624 | 41.791 | 1.00 | 29.78 |
| 24006 | CG | PHE | D | 732 | -91.248 | -18.468 | 42.645 | 1.00 | 27.75 |
| 24007 | CD1 | PHE | D | 732 | -89.946 | -17.998 | 42.572 | 1.00 | 27.19 |
| 24008 | CE1 | PHE | D | 732 | -89.533 | -16.942 | 43.358 | 1.00 | 28.30 |
| 24009 | CZ | PHE | D | 732 | -90.446 | -16.323 | 44.213 | 1.00 | 28.28 |
| 24010 | CE2 | PHE | D | 732 | -91.744 | -16.781 | 44.279 | 1.00 | 25.45 |
| 24011 | CD2 | PHE | D | 732 | -92.131 | -17.853 | 43.509 | 1.00 | 25.81 |

FIGURE 3 TE

| A | B | C | D | E | F | G | H | I | J |
|---|---|---|---|---|---|---|---|---|---|
| 24012 | C | PHE | D | 732 | -91.851 | -21.104 | 43.732 | 1.00 | 30.64 |
| 24013 | O | PHE | D | 732 | -91.116 | -20.985 | 44.717 | 1.00 | 30.47 |
| 24014 | N | ILE | D | 733 | -93.158 | -21.329 | 43.786 | 1.00 | 31.23 |
| 24015 | CA | ILE | D | 733 | -93.880 | -21.476 | 45.034 | 1.00 | 32.24 |
| 24016 | CB | ILE | D | 733 | -95.393 | -21.564 | 44.756 | 1.00 | 32.28 |
| 24017 | CG1 | ILE | D | 733 | -95.881 | -20.241 | 44.184 | 1.00 | 33.24 |
| 24018 | CD1 | ILE | D | 733 | -95.741 | -19.063 | 45.155 | 1.00 | 34.28 |
| 24019 | CG2 | ILE | D | 733 | -96.178 | -21.875 | 46.030 | 1.00 | 31.60 |
| 24020 | C | ILE | D | 733 | -93.393 | -22.700 | 45.795 | 1.00 | 33.05 |
| 24021 | O | ILE | D | 733 | -93.043 | -22.584 | 46.960 | 1.00 | 33.10 |
| 24022 | N | LYS | D | 734 | -93.366 | -23.859 | 45.127 | 1.00 | 34.12 |
| 24023 | CA | LYS | D | 734 | -92.894 | -25.111 | 45.732 | 1.00 | 35.44 |
| 24024 | CB | LYS | D | 734 | -92.634 | -26.209 | 44.671 | 1.00 | 35.53 |
| 24025 | CG | LYS | D | 734 | -93.742 | -26.483 | 43.666 | 1.00 | 37.56 |
| 24026 | CD | LYS | D | 734 | -94.685 | -27.595 | 44.080 | 1.00 | 40.97 |
| 24027 | CE | LYS | D | 734 | -94.023 | -28.977 | 43.982 | 1.00 | 41.85 |
| 24028 | NZ | LYS | D | 734 | -95.014 | -30.045 | 43.641 | 1.00 | 42.68 |
| 24029 | C | LYS | D | 734 | -91.569 | -24.850 | 46.411 | 1.00 | 35.69 |
| 24030 | O | LYS | D | 734 | -91.380 | -25.172 | 47.579 | 1.00 | 35.50 |
| 24031 | N | GLN | D | 735 | -90.649 | -24.283 | 45.636 | 1.00 | 36.31 |
| 24032 | CA | GLN | D | 735 | -89.291 | -23.998 | 46.081 | 1.00 | 37.37 |
| 24033 | CB | GLN | D | 735 | -88.466 | -23.428 | 44.915 | 1.00 | 38.00 |
| 24034 | CG | GLN | D | 735 | -87.112 | -24.133 | 44.683 | 1.00 | 42.23 |
| 24035 | CD | GLN | D | 735 | -86.882 | -24.498 | 43.214 | 1.00 | 46.36 |
| 24036 | OE1 | GLN | D | 735 | -87.676 | -24.120 | 42.353 | 1.00 | 49.07 |
| 24037 | NE2 | GLN | D | 735 | -85.804 | -25.243 | 42.930 | 1.00 | 48.29 |
| 24038 | C | GLN | D | 735 | -89.287 | -23.048 | 47.280 | 1.00 | 37.22 |
| 24039 | O | GLN | D | 735 | -88.546 | -23.262 | 48.235 | 1.00 | 37.42 |
| 24040 | N | CYS | D | 736 | -90.138 | -22.027 | 47.249 | 1.00 | 36.65 |
| 24041 | CA | CYS | D | 736 | -90.209 | -21.069 | 48.348 | 1.00 | 36.80 |
| 24042 | CB | CYS | D | 736 | -91.071 | -19.857 | 47.957 | 1.00 | 36.66 |
| 24043 | SG | CYS | D | 736 | -91.706 | -18.832 | 49.313 | 1.00 | 38.36 |
| 24044 | C | CYS | D | 736 | -90.746 | -21.720 | 49.617 | 1.00 | 36.81 |
| 24045 | O | CYS | D | 736 | -90.331 | -21.367 | 50.731 | 1.00 | 36.68 |
| 24046 | N | PHE | D | 737 | -91.663 | -22.669 | 49.436 | 1.00 | 36.64 |
| 24047 | CA | PHE | D | 737 | -92.305 | -23.362 | 50.541 | 1.00 | 36.62 |
| 24048 | CB | PHE | D | 737 | -93.752 | -23.694 | 50.182 | 1.00 | 35.97 |
| 24049 | CG | PHE | D | 737 | -94.676 | -22.524 | 50.260 | 1.00 | 34.35 |
| 24050 | CD1 | PHE | D | 737 | -94.253 | -21.335 | 50.826 | 1.00 | 30.83 |
| 24051 | CE1 | PHE | D | 737 | -95.095 | -20.256 | 50.904 | 1.00 | 28.86 |
| 24052 | CZ | PHE | D | 737 | -96.377 | -20.344 | 50.422 | 1.00 | 29.88 |
| 24053 | CE2 | PHE | D | 737 | -96.820 | -21.523 | 49.838 | 1.00 | 30.99 |
| 24054 | CD2 | PHE | D | 737 | -95.968 | -22.604 | 49.754 | 1.00 | 31.96 |
| 24055 | C | PHE | D | 737 | -91.582 | -24.653 | 50.887 | 1.00 | 37.46 |
| 24056 | O | PHE | D | 737 | -91.996 | -25.381 | 51.782 | 1.00 | 37.47 |
| 24057 | N | SER | D | 738 | -90.513 | -24.949 | 50.165 | 1.00 | 38.74 |
| 24058 | CA | SER | D | 738 | -89.768 | -26.170 | 50.419 | 1.00 | 40.18 |
| 24059 | CB | SER | D | 738 | -89.240 | -26.211 | 51.858 | 1.00 | 39.94 |
| 24060 | OG | SER | D | 738 | -88.089 | -25.409 | 51.986 | 1.00 | 39.67 |
| 24061 | C | SER | D | 738 | -90.633 | -27.390 | 50.153 | 1.00 | 41.31 |
| 24062 | O | SER | D | 738 | -90.620 | -28.342 | 50.937 | 1.00 | 41.36 |

FIGURE 3 TF

| A | B | C | D | E | F | G | H | I | J |
|---|---|---|---|---|---|---|---|---|---|
| 24063 | N | LEU | D | 739 | -91.380 | -27.352 | 49.051 | 1.00 | 42.72 |
| 24064 | CA | LEU | D | 739 | -92.192 | -28.484 | 48.624 | 1.00 | 44.17 |
| 24065 | CB | LEU | D | 739 | -93.565 | -28.034 | 48.154 | 1.00 | 43.93 |
| 24066 | CG | LEU | D | 739 | -94.462 | -27.445 | 49.231 | 1.00 | 44.34 |
| 24067 | CD1 | LEU | D | 739 | -95.808 | -27.149 | 48.641 | 1.00 | 44.64 |
| 24068 | CD2 | LEU | D | 739 | -94.583 | -28.407 | 50.404 | 1.00 | 45.57 |
| 24069 | C | LEU | D | 739 | -91.507 | -29.224 | 47.495 | 1.00 | 45.39 |
| 24070 | O | LEU | D | 739 | -91.217 | -28.656 | 46.445 | 1.00 | 45.92 |
| 24071 | N | PRO | D | 740 | -91.231 | -30.498 | 47.716 | 1.00 | 46.58 |
| 24072 | CA | PRO | D | 740 | -90.596 | -31.337 | 46.698 | 1.00 | 47.17 |
| 24073 | CB | PRO | D | 740 | -90.074 | -32.527 | 47.508 | 1.00 | 47.54 |
| 24074 | CG | PRO | D | 740 | -90.252 | -32.109 | 48.972 | 1.00 | 48.06 |
| 24075 | CD | PRO | D | 740 | -91.471 | -31.223 | 48.974 | 1.00 | 46.94 |
| 24076 | C | PRO | D | 740 | -91.607 | -31.811 | 45.662 | 1.00 | 47.45 |
| 24077 | O | PRO | D | 740 | -92.806 | -31.592 | 45.868 | 1.00 | 47.85 |
| 24078 | O7 | NAG | D1621 | | -115.658 | -10.108 | 1.065 | 1.00 | 73.42 |
| 24079 | C7 | NAG | D1621 | | -115.594 | -9.096 | 0.380 | 1.00 | 72.75 |
| 24080 | C8 | NAG | D1621 | | -116.631 | -8.018 | 0.445 | 1.00 | 73.32 |
| 24081 | N2 | NAG | D1621 | | -114.567 | -8.812 | -0.414 | 1.00 | 71.98 |
| 24082 | C2 | NAG | D1621 | | -113.456 | -9.726 | -0.607 | 1.00 | 71.93 |
| 24083 | C1 | NAG | D1621 | | -112.792 | -10.113 | 0.713 | 1.00 | 70.01 |
| 24084 | C3 | NAG | D1621 | | -113.935 | -10.979 | -1.334 | 1.00 | 72.45 |
| 24085 | O3 | NAG | D1621 | | -114.520 | -10.646 | -2.610 | 1.00 | 71.12 |
| 24086 | C4 | NAG | D1621 | | -112.786 | -11.977 | -1.491 | 1.00 | 72.47 |
| 24087 | O4 | NAG | D1621 | | -113.351 | -13.258 | -1.775 | 1.00 | 72.94 |
| 24088 | C5 | NAG | D1621 | | -111.914 | -12.131 | -0.238 | 1.00 | 72.76 |
| 24089 | O5 | NAG | D1621 | | -111.628 | -10.885 | 0.412 | 1.00 | 72.16 |
| 24090 | C6 | NAG | D1621 | | -110.598 | -12.825 | -0.601 | 1.00 | 73.05 |
| 24091 | O6 | NAG | D1621 | | -109.961 | -13.377 | 0.560 | 1.00 | 72.80 |
| 24092 | O7 | NAG | D2311 | | -143.486 | 2.005 | 13.260 | 1.00 | 74.38 |
| 24093 | C7 | NAG | D2311 | | -142.386 | 1.558 | 12.963 | 1.00 | 73.58 |
| 24094 | C8 | NAG | D2311 | | -142.247 | 0.199 | 12.336 | 1.00 | 73.63 |
| 24095 | N2 | NAG | D2311 | | -141.263 | 2.274 | 13.096 | 1.00 | 71.98 |
| 24096 | C2 | NAG | D2311 | | -141.288 | 3.609 | 13.680 | 1.00 | 70.62 |
| 24097 | C1 | NAG | D2311 | | -140.106 | 3.832 | 14.614 | 1.00 | 67.00 |
| 24098 | C3 | NAG | D2311 | | -141.303 | 4.679 | 12.596 | 1.00 | 70.50 |
| 24099 | O3 | NAG | D2311 | | -142.506 | 4.535 | 11.840 | 1.00 | 71.38 |
| 24100 | C4 | NAG | D2311 | | -141.254 | 6.070 | 13.217 | 1.00 | 70.31 |
| 24101 | O4 | NAG | D2311 | | -141.099 | 7.052 | 12.181 | 1.00 | 70.47 |
| 24102 | C5 | NAG | D2311 | | -140.104 | 6.171 | 14.219 | 1.00 | 69.91 |
| 24103 | O5 | NAG | D2311 | | -140.196 | 5.133 | 15.192 | 1.00 | 69.16 |
| 24104 | C6 | NAG | D2311 | | -140.111 | 7.517 | 14.934 | 1.00 | 70.22 |
| 24105 | O6 | NAG | D2311 | | -141.207 | 7.570 | 15.854 | 1.00 | 70.09 |
| 24106 | O7 | NAG | D2411 | | -112.694 | 16.675 | 14.251 | 1.00 | 58.29 |
| 24107 | C7 | NAG | D2411 | | -111.936 | 16.037 | 13.545 | 1.00 | 58.41 |
| 24108 | C8 | NAG | D2411 | | -112.422 | 15.169 | 12.422 | 1.00 | 57.84 |
| 24109 | N2 | NAG | D2411 | | -110.619 | 16.110 | 13.681 | 1.00 | 58.33 |
| 24110 | C2 | NAG | D2411 | | -110.033 | 16.919 | 14.722 | 1.00 | 58.50 |
| 24111 | C1 | NAG | D2411 | | -109.372 | 16.035 | 15.770 | 1.00 | 55.27 |
| 24112 | C3 | NAG | D2411 | | -109.003 | 17.655 | 14.113 | 1.00 | 60.36 |
| 24113 | O3 | NAG | D2411 | | -109.616 | 18.724 | 13.147 | 1.00 | 61.59 |

FIGURE 3 TG

| A | B | C | D | E | F | G | H | I | J |
|---|---|---|---|---|---|---|---|---|---|
| 24114 | C4 | NAG | D2411 | | -108.359 | 18.664 | 15.225 | 1.00 | 61.57 |
| 24115 | O4 | NAG | D2411 | | -107.303 | 19.448 | 14.664 | 1.00 | 67.27 |
| 24116 | C5 | NAG | D2411 | | -107.607 | 17.736 | 16.309 | 1.00 | 60.81 |
| 24117 | O5 | NAG | D2411 | | -108.833 | 16.866 | 16.793 | 1.00 | 58.82 |
| 24118 | C6 | NAG | D2411 | | -107.256 | 18.518 | 17.490 | 1.00 | 60.30 |
| 24119 | O6 | NAG | D2411 | | -106.648 | 17.593 | 18.392 | 1.00 | 61.16 |
| 24120 | O7 | NAG | D2412 | | -102.963 | 19.045 | 15.946 | 1.00 | 79.63 |
| 24121 | C7 | NAG | D2412 | | -103.800 | 19.396 | 15.139 | 1.00 | 78.83 |
| 24122 | C8 | NAG | D2412 | | -103.934 | 18.788 | 13.771 | 1.00 | 79.00 |
| 24123 | N2 | NAG | D2412 | | -104.689 | 20.321 | 15.489 | 1.00 | 78.34 |
| 24124 | C2 | NAG | D2412 | | -105.721 | 20.814 | 14.606 | 1.00 | 78.56 |
| 24125 | C1 | NAG | D2412 | | -107.094 | 20.684 | 15.246 | 1.00 | 76.22 |
| 24126 | C3 | NAG | D2412 | | -105.386 | 22.271 | 14.309 | 1.00 | 79.46 |
| 24127 | O3 | NAG | D2412 | | -104.278 | 22.311 | 13.399 | 1.00 | 80.11 |
| 24128 | C4 | NAG | D2412 | | -106.553 | 23.048 | 13.709 | 1.00 | 79.88 |
| 24129 | O4 | NAG | D2412 | | -106.301 | 24.453 | 13.835 | 1.00 | 80.18 |
| 24130 | C5 | NAG | D2412 | | -107.870 | 22.718 | 14.397 | 1.00 | 79.65 |
| 24131 | O5 | NAG | D2412 | | -108.051 | 21.305 | 14.391 | 1.00 | 78.94 |
| 24132 | C6 | NAG | D2412 | | -109.038 | 23.397 | 13.689 | 1.00 | 79.99 |
| 24133 | O6 | NAG | D2412 | | -109.050 | 23.024 | 12.305 | 1.00 | 80.18 |
| 24134 | O7 | NAG | D2931 | | -121.810 | 14.605 | -2.718 | 1.00 | 80.29 |
| 24135 | C7 | NAG | D2931 | | -121.748 | 13.389 | -2.736 | 1.00 | 80.24 |
| 24136 | C8 | NAG | D2931 | | -122.652 | 12.560 | -3.606 | 1.00 | 80.94 |
| 24137 | N2 | NAG | D2931 | | -120.825 | 12.713 | -2.050 | 1.00 | 78.56 |
| 24138 | C2 | NAG | D2931 | | -119.878 | 13.395 | -1.190 | 1.00 | 77.00 |
| 24139 | C1 | NAG | D2931 | | -119.943 | 12.829 | 0.230 | 1.00 | 74.54 |
| 24140 | C3 | NAG | D2931 | | -118.494 | 13.252 | -1.814 | 1.00 | 77.06 |
| 24141 | O3 | NAG | D2931 | | -118.432 | 14.006 | -3.035 | 1.00 | 77.42 |
| 24142 | C4 | NAG | D2931 | | -117.406 | 13.711 | -0.852 | 1.00 | 76.73 |
| 24143 | O4 | NAG | D2931 | | -116.121 | 13.393 | -1.397 | 1.00 | 76.18 |
| 24144 | C5 | NAG | D2931 | | -117.569 | 13.022 | 0.496 | 1.00 | 76.47 |
| 24145 | O5 | NAG | D2931 | | -118.861 | 13.321 | 1.025 | 1.00 | 76.20 |
| 24146 | C6 | NAG | D2931 | | -116.517 | 13.547 | 1.462 | 1.00 | 76.51 |
| 24147 | O6 | NAG | D2931 | | -116.850 | 14.893 | 1.819 | 1.00 | 76.40 |
| 24148 | O7 | NAG | D3331 | | -116.219 | 16.951 | 45.963 | 1.00 | 62.90 |
| 24149 | C7 | NAG | D3331 | | -116.733 | 17.154 | 44.869 | 1.00 | 62.34 |
| 24150 | C8 | NAG | D3331 | | -118.215 | 17.287 | 44.684 | 1.00 | 61.90 |
| 24151 | N2 | NAG | D3331 | | -115.991 | 17.361 | 43.789 | 1.00 | 61.79 |
| 24152 | C2 | NAG | D3331 | | -114.552 | 17.254 | 43.909 | 1.00 | 61.67 |
| 24153 | C1 | NAG | D3331 | | -113.957 | 16.496 | 42.730 | 1.00 | 57.43 |
| 24154 | C3 | NAG | D3331 | | -113.878 | 18.612 | 44.037 | 1.00 | 62.68 |
| 24155 | O3 | NAG | D3331 | | -114.391 | 19.283 | 45.188 | 1.00 | 63.18 |
| 24156 | C4 | NAG | D3331 | | -112.380 | 18.387 | 44.208 | 1.00 | 63.31 |
| 24157 | O4 | NAG | D3331 | | -111.696 | 19.642 | 44.179 | 1.00 | 64.30 |
| 24158 | C5 | NAG | D3331 | | -111.827 | 17.472 | 43.110 | 1.00 | 62.90 |
| 24159 | O5 | NAG | D3331 | | -112.580 | 16.260 | 43.023 | 1.00 | 62.27 |
| 24160 | C6 | NAG | D3331 | | -110.382 | 17.098 | 43.394 | 1.00 | 63.76 |
| 24161 | O6 | NAG | D3331 | | -110.097 | 15.863 | 42.731 | 1.00 | 65.10 |
| 24162 | O | HOH | W | 1 | -70.047 | -9.621 | 78.744 | 1.00 | 22.57 |
| 24163 | O | HOH | W | 2 | -34.851 | -4.814 | 99.378 | 1.00 | 19.43 |
| 24164 | O | HOH | W | 3 | -62.319 | -2.336 | 82.776 | 1.00 | 15.33 |

FIGURE 3 TH

| A | B | C | D | E | F | G | H | I | J |
|---|---|---|---|---|---|---|---|---|---|
| 24165 | O | HOH | W | 4 | -105.925 | -3.902 | 37.241 | 1.00 | 21.48 |
| 24166 | O | HOH | W | 5 | -52.287 | -3.318 | 87.258 | 1.00 | 18.54 |
| 24167 | O | HOH | W | 6 | -91.285 | -16.061 | 25.538 | 1.00 | 22.18 |
| 24168 | O | HOH | W | 7 | -33.478 | 6.291 | 87.322 | 1.00 | 21.61 |
| 24169 | O | HOH | W | 8 | -32.644 | -5.923 | 92.690 | 1.00 | 16.83 |
| 24170 | O | HOH | W | 9 | -83.500 | -4.860 | 34.516 | 1.00 | 20.17 |
| 24171 | O | HOH | W | 10 | -95.846 | -3.672 | 26.390 | 1.00 | 22.63 |
| 24172 | O | HOH | W | 11 | -38.585 | -8.808 | 81.793 | 1.00 | 32.00 |
| 24173 | O | HOH | W | 12 | -131.539 | 3.310 | 49.749 | 1.00 | 24.07 |
| 24174 | O | HOH | W | 13 | -89.602 | -6.431 | 24.528 | 1.00 | 31.49 |
| 24175 | O | HOH | W | 14 | -22.191 | 19.290 | 81.198 | 1.00 | 29.71 |
| 24176 | O | HOH | W | 15 | -103.695 | -7.177 | 26.708 | 1.00 | 23.52 |
| 24177 | O | HOH | W | 16 | -48.011 | -6.164 | 76.557 | 1.00 | 19.02 |
| 24178 | O | HOH | W | 17 | -61.410 | -18.972 | 74.744 | 1.00 | 17.60 |
| 24179 | O | HOH | W | 18 | -87.151 | -5.568 | 66.326 | 1.00 | 30.46 |
| 24180 | O | HOH | W | 19 | -44.226 | 22.424 | 76.402 | 1.00 | 28.91 |
| 24181 | O | HOH | W | 20 | -83.027 | -8.609 | 67.599 | 1.00 | 25.69 |
| 24182 | O | HOH | W | 21 | -105.924 | -19.170 | 40.951 | 1.00 | 25.71 |
| 24183 | O | HOH | W | 22 | -79.666 | -0.305 | 31.865 | 1.00 | 24.81 |
| 24184 | O | HOH | W | 23 | -70.178 | -9.767 | 91.982 | 1.00 | 15.50 |
| 24185 | O | HOH | W | 24 | -120.299 | 1.315 | 46.762 | 1.00 | 32.88 |
| 24186 | O | HOH | W | 25 | -126.417 | -15.760 | 32.836 | 1.00 | 35.97 |
| 24187 | O | HOH | W | 26 | -107.622 | -9.077 | 46.909 | 1.00 | 19.86 |
| 24188 | O | HOH | W | 27 | -88.087 | -4.550 | 25.498 | 1.00 | 19.45 |
| 24189 | O | HOH | W | 28 | -82.329 | 4.434 | 33.892 | 1.00 | 20.74 |
| 24190 | O | HOH | W | 29 | -71.620 | -24.011 | 85.413 | 1.00 | 25.43 |
| 24191 | O | HOH | W | 30 | -46.730 | -8.233 | 84.956 | 1.00 | 25.87 |
| 24192 | O | HOH | W | 31 | -98.497 | -11.196 | 73.755 | 1.00 | 26.51 |
| 24193 | O | HOH | W | 32 | -87.168 | -5.170 | 18.974 | 1.00 | 26.01 |
| 24194 | O | HOH | W | 33 | -62.091 | -12.323 | 84.142 | 1.00 | 23.87 |
| 24195 | O | HOH | W | 34 | -50.927 | -6.839 | 93.390 | 1.00 | 26.48 |
| 24196 | O | HOH | W | 35 | -70.656 | -3.379 | 73.593 | 1.00 | 20.18 |
| 24197 | O | HOH | W | 36 | -84.552 | -6.501 | 19.825 | 1.00 | 24.45 |
| 24198 | O | HOH | W | 37 | -117.602 | -11.619 | 43.383 | 1.00 | 29.61 |
| 24199 | O | HOH | W | 38 | -109.448 | -3.153 | 38.603 | 1.00 | 19.00 |
| 24200 | O | HOH | W | 39 | -77.633 | -16.012 | 77.912 | 1.00 | 18.39 |
| 24201 | O | HOH | W | 40 | -37.628 | -8.094 | 86.503 | 1.00 | 24.21 |
| 24202 | O | HOH | W | 41 | -68.908 | -6.239 | 89.490 | 1.00 | 30.06 |
| 24203 | O | HOH | W | 42 | -93.574 | -16.006 | 55.747 | 1.00 | 20.92 |
| 24204 | O | HOH | W | 43 | -128.507 | 1.119 | 37.053 | 1.00 | 23.40 |
| 24205 | O | HOH | W | 44 | -53.377 | -22.267 | 85.437 | 1.00 | 24.95 |
| 24206 | O | HOH | W | 45 | -27.348 | 7.987 | 74.856 | 1.00 | 33.09 |
| 24207 | O | HOH | W | 46 | -33.504 | 8.245 | 79.353 | 1.00 | 22.40 |
| 24208 | O | HOH | W | 47 | -63.275 | -0.369 | 56.167 | 1.00 | 20.34 |
| 24209 | O | HOH | W | 48 | -60.051 | -20.691 | 77.439 | 1.00 | 29.91 |
| 24210 | O | HOH | W | 49 | -103.083 | -7.671 | 22.880 | 1.00 | 20.83 |
| 24211 | O | HOH | W | 50 | -55.646 | 5.935 | 84.874 | 1.00 | 16.39 |
| 24212 | O | HOH | W | 51 | -20.326 | 16.802 | 88.348 | 1.00 | 29.49 |
| 24213 | O | HOH | W | 52 | -31.662 | 6.373 | 71.432 | 1.00 | 25.55 |
| 24214 | O | HOH | W | 53 | -82.079 | 3.469 | 31.545 | 1.00 | 27.19 |
| 24215 | O | HOH | W | 54 | -71.278 | -25.643 | 91.236 | 1.00 | 30.95 |

FIGURE 3 TI

| A | B | C | D | E | F | G | H | I | J |
|---|---|---|---|---|---|---|---|---|---|
| 24216 | O | HOH | W | 55 | -113.642 | 1.100 | 40.912 | 1.00 | 20.06 |
| 24217 | O | HOH | W | 56 | -106.400 | -10.823 | 48.758 | 1.00 | 23.65 |
| 24218 | O | HOH | W | 57 | -72.098 | -27.755 | 94.347 | 1.00 | 21.93 |
| 24219 | O | HOH | W | 58 | -81.485 | -2.961 | 34.163 | 1.00 | 20.94 |
| 24220 | O | HOH | W | 59 | -104.853 | -11.330 | 41.012 | 1.00 | 22.49 |
| 24221 | O | HOH | W | 60 | -50.143 | -21.292 | 15.918 | 1.00 | 46.06 |
| 24222 | O | HOH | W | 61 | -75.243 | -14.549 | 84.035 | 1.00 | 22.74 |
| 24223 | O | HOH | W | 62 | -42.523 | -4.657 | 66.681 | 1.00 | 32.51 |
| 24224 | O | HOH | W | 63 | -65.231 | -15.648 | 33.609 | 1.00 | 31.65 |
| 24225 | O | HOH | W | 64 | -108.948 | -3.717 | 25.649 | 1.00 | 29.83 |
| 24226 | O | HOH | W | 65 | -92.950 | -6.028 | 69.562 | 1.00 | 30.87 |
| 24227 | O | HOH | W | 66 | -86.814 | 5.040 | 47.700 | 1.00 | 39.21 |
| 24228 | O | HOH | W | 67 | -116.041 | -8.699 | 50.305 | 1.00 | 23.70 |
| 24229 | O | HOH | W | 68 | -93.123 | 10.711 | 28.131 | 1.00 | 26.08 |
| 24230 | O | HOH | W | 69 | -50.985 | 3.640 | 72.696 | 1.00 | 20.48 |
| 24231 | O | HOH | W | 70 | -70.198 | -10.686 | 80.787 | 1.00 | 27.69 |
| 24232 | O | HOH | W | 71 | -114.830 | -7.412 | 52.563 | 1.00 | 26.83 |
| 24233 | O | HOH | W | 72 | -75.102 | -0.276 | 9.886 | 1.00 | 28.92 |
| 24234 | O | HOH | W | 73 | -23.734 | -17.727 | 89.694 | 1.00 | 28.78 |
| 24235 | O | HOH | W | 74 | -61.665 | 13.073 | 82.553 | 1.00 | 23.56 |
| 24236 | O | HOH | W | 75 | -71.182 | -9.402 | 3.784 | 1.00 | 35.36 |
| 24237 | O | HOH | W | 76 | -24.540 | -4.350 | 67.423 | 1.00 | 43.77 |
| 24238 | O | HOH | W | 77 | -61.200 | -3.647 | 93.365 | 1.00 | 19.38 |
| 24239 | O | HOH | W | 78 | -121.220 | 15.557 | 20.341 | 1.00 | 39.85 |
| 24240 | O | HOH | W | 79 | -72.505 | 5.899 | 75.027 | 1.00 | 28.20 |
| 24241 | O | HOH | W | 80 | -53.615 | -1.972 | 65.458 | 1.00 | 25.36 |
| 24242 | O | HOH | W | 81 | -23.316 | 8.408 | 68.632 | 1.00 | 27.79 |
| 24243 | O | HOH | W | 82 | -40.295 | -8.810 | 86.500 | 1.00 | 19.14 |
| 24244 | O | HOH | W | 83 | -66.594 | -4.239 | 87.795 | 1.00 | 24.11 |
| 24245 | O | HOH | W | 84 | -75.182 | -13.009 | 69.585 | 1.00 | 18.25 |
| 24246 | O | HOH | W | 85 | -96.392 | -18.489 | 23.392 | 1.00 | 36.31 |
| 24247 | O | HOH | W | 86 | -112.774 | 15.956 | 26.499 | 1.00 | 26.80 |
| 24248 | O | HOH | W | 87 | -91.217 | -10.713 | 67.871 | 1.00 | 16.07 |
| 24249 | O | HOH | W | 88 | -12.985 | -15.845 | 110.350 | 1.00 | 29.91 |
| 24250 | O | HOH | W | 89 | -59.754 | -17.919 | 67.217 | 1.00 | 33.41 |
| 24251 | O | HOH | W | 90 | -87.120 | -23.809 | 79.247 | 1.00 | 25.99 |
| 24252 | O | HOH | W | 91 | -17.496 | -5.037 | 62.417 | 1.00 | 35.92 |
| 24253 | O | HOH | W | 92 | -82.662 | -5.201 | 21.440 | 1.00 | 28.79 |
| 24254 | O | HOH | W | 93 | -15.946 | -17.219 | 90.181 | 1.00 | 35.57 |
| 24255 | O | HOH | W | 94 | -106.041 | -23.904 | 32.595 | 1.00 | 27.36 |
| 24256 | O | HOH | W | 95 | -64.891 | -38.163 | 13.838 | 1.00 | 49.31 |
| 24257 | O | HOH | W | 96 | -68.673 | -3.377 | 89.495 | 1.00 | 28.59 |
| 24258 | O | HOH | W | 97 | -73.127 | 4.487 | 72.673 | 1.00 | 24.48 |
| 24259 | O | HOH | W | 98 | -75.506 | 0.140 | 23.056 | 1.00 | 30.81 |
| 24260 | O | HOH | W | 99 | -59.199 | 11.468 | 76.763 | 1.00 | 25.49 |
| 24261 | O | HOH | W | 100 | -66.041 | 3.566 | -5.385 | 1.00 | 33.28 |
| 24262 | O | HOH | W | 101 | -11.881 | 3.367 | 91.642 | 1.00 | 21.04 |
| 24263 | O | HOH | W | 102 | -85.203 | -18.621 | 66.788 | 1.00 | 27.38 |
| 24264 | O | HOH | W | 103 | -109.289 | 4.117 | 56.380 | 1.00 | 33.61 |
| 24265 | O | HOH | W | 104 | -106.928 | -5.336 | 50.716 | 1.00 | 28.54 |
| 24266 | O | HOH | W | 105 | -81.989 | -10.473 | 65.120 | 1.00 | 20.82 |

FIGURE 3 TJ

| A | B | C | D | E | F | G | H | I | J |
|---|---|---|---|---|---|---|---|---|---|
| 24267 | O | HOH | W | 106 | -41.840 | 13.381 | 94.446 | 1.00 | 35.97 |
| 24268 | O | HOH | W | 107 | -106.501 | -2.782 | 35.295 | 1.00 | 28.25 |
| 24269 | O | HOH | W | 108 | -72.388 | 10.526 | 80.061 | 1.00 | 31.33 |
| 24270 | O | HOH | W | 109 | -53.562 | 5.264 | 73.907 | 1.00 | 22.21 |
| 24271 | O | HOH | W | 110 | -57.971 | 6.214 | 86.387 | 1.00 | 23.64 |
| 24272 | O | HOH | W | 111 | -100.805 | -7.622 | 22.042 | 1.00 | 23.65 |
| 24273 | O | HOH | W | 112 | -48.478 | -3.003 | 92.083 | 1.00 | 23.36 |
| 24274 | O | HOH | W | 113 | -85.465 | -25.300 | 72.872 | 1.00 | 29.44 |
| 24275 | O | HOH | W | 114 | -20.282 | 8.882 | 79.786 | 1.00 | 35.92 |
| 24276 | O | HOH | W | 115 | -45.959 | 2.886 | 103.777 | 1.00 | 26.29 |
| 24277 | O | HOH | W | 116 | -36.141 | -11.677 | 74.345 | 1.00 | 28.93 |
| 24278 | O | HOH | W | 117 | -84.832 | -6.458 | 67.180 | 1.00 | 23.67 |
| 24279 | O | HOH | W | 118 | -110.885 | -3.063 | 36.123 | 1.00 | 17.59 |
| 24280 | O | HOH | W | 119 | -76.548 | 1.210 | 67.123 | 1.00 | 23.27 |
| 24281 | O | HOH | W | 120 | -90.282 | -6.048 | 52.777 | 1.00 | 21.84 |
| 24282 | O | HOH | W | 121 | -29.693 | 4.046 | 86.322 | 1.00 | 34.99 |
| 24283 | O | HOH | W | 122 | -28.902 | -9.734 | 109.602 | 1.00 | 31.65 |
| 24284 | O | HOH | W | 123 | -4.352 | -3.743 | 90.634 | 1.00 | 32.59 |
| 24285 | O | HOH | W | 124 | -91.781 | -4.447 | 83.572 | 1.00 | 25.21 |
| 24286 | O | HOH | W | 125 | -67.717 | -16.914 | 28.754 | 1.00 | 40.36 |
| 24287 | O | HOH | W | 126 | -119.211 | 0.651 | 53.546 | 1.00 | 26.42 |
| 24288 | O | HOH | W | 127 | -91.301 | -28.429 | 34.790 | 1.00 | 40.78 |
| 24289 | O | HOH | W | 128 | -76.632 | -4.861 | 41.174 | 1.00 | 30.89 |
| 24290 | O | HOH | W | 129 | -99.483 | 0.770 | 31.171 | 1.00 | 21.46 |
| 24291 | O | HOH | W | 130 | -40.577 | 25.458 | 71.322 | 1.00 | 31.89 |
| 24292 | O | HOH | W | 131 | -54.460 | -3.811 | 88.792 | 1.00 | 26.57 |
| 24293 | O | HOH | W | 132 | -73.347 | -26.780 | 96.594 | 1.00 | 25.31 |
| 24294 | O | HOH | W | 133 | -101.846 | -12.191 | 22.857 | 1.00 | 29.80 |
| 24295 | O | HOH | W | 134 | -13.225 | -4.460 | 115.839 | 1.00 | 40.97 |
| 24296 | O | HOH | W | 135 | -68.912 | -5.769 | 86.997 | 1.00 | 22.23 |
| 24297 | O | HOH | W | 136 | -22.275 | 9.258 | 67.096 | 1.00 | 30.00 |
| 24298 | O | HOH | W | 137 | -44.839 | -3.193 | 88.802 | 1.00 | 24.93 |
| 24299 | O | HOH | W | 138 | -65.755 | -7.053 | 37.884 | 1.00 | 28.79 |
| 24300 | O | HOH | W | 139 | -58.404 | -6.772 | 87.209 | 1.00 | 23.49 |
| 24301 | O | HOH | W | 140 | -80.628 | -9.548 | 77.028 | 1.00 | 24.08 |
| 24302 | O | HOH | W | 141 | -99.414 | 17.192 | 45.081 | 1.00 | 30.93 |
| 24303 | O | HOH | W | 142 | -25.663 | 9.914 | 92.244 | 1.00 | 34.26 |
| 24304 | O | HOH | W | 143 | -36.543 | -4.504 | 66.323 | 1.00 | 26.15 |
| 24305 | O | HOH | W | 144 | -50.670 | -5.118 | 86.081 | 1.00 | 28.13 |
| 24306 | O | HOH | W | 145 | -14.817 | 1.884 | 76.189 | 1.00 | 31.05 |
| 24307 | O | HOH | W | 146 | -90.085 | 4.557 | 31.021 | 1.00 | 23.04 |
| 24308 | O | HOH | W | 147 | -92.788 | -23.311 | 32.998 | 1.00 | 35.23 |
| 24309 | O | HOH | W | 148 | -73.899 | -11.308 | 78.406 | 1.00 | 20.27 |
| 24310 | O | HOH | W | 149 | -44.776 | -13.606 | 80.500 | 1.00 | 26.73 |
| 24311 | O | HOH | W | 150 | -82.733 | -15.307 | 90.077 | 1.00 | 52.62 |
| 24312 | O | HOH | W | 151 | -27.565 | -1.561 | 63.745 | 1.00 | 37.01 |
| 24313 | O | HOH | W | 152 | -59.931 | -24.626 | 91.317 | 1.00 | 27.37 |
| 24314 | O | HOH | W | 153 | -48.630 | -13.831 | 69.969 | 1.00 | 25.35 |
| 24315 | O | HOH | W | 154 | -56.434 | -22.590 | 87.803 | 1.00 | 28.54 |
| 24316 | O | HOH | W | 155 | -97.391 | 5.405 | 41.148 | 1.00 | 28.63 |
| 24317 | O | HOH | W | 156 | -111.072 | 13.637 | 28.834 | 1.00 | 29.36 |

FIGURE 3 TK

| A | B | C | D | E | F | G | H | I | J |
|---|---|---|---|---|---|---|---|---|---|
| 24318 | O | HOH | W | 157 | -70.170 | -26.212 | 93.886 | 1.00 | 21.97 |
| 24319 | O | HOH | W | 158 | -40.421 | -9.872 | 83.798 | 1.00 | 25.90 |
| 24320 | O | HOH | W | 159 | -124.981 | -6.802 | 54.015 | 1.00 | 32.00 |
| 24321 | O | HOH | W | 160 | -14.089 | 3.959 | 80.977 | 1.00 | 28.94 |
| 24322 | O | HOH | W | 161 | -75.785 | -11.368 | 76.575 | 1.00 | 16.09 |
| 24323 | O | HOH | W | 162 | -85.426 | -18.016 | 6.302 | 1.00 | 35.99 |
| 24324 | O | HOH | W | 163 | -79.395 | 2.382 | 31.405 | 1.00 | 35.95 |
| 24325 | O | HOH | W | 164 | -80.145 | 2.786 | 36.094 | 1.00 | 28.98 |
| 24326 | O | HOH | W | 165 | -54.849 | -0.234 | 3.626 | 1.00 | 52.60 |
| 24327 | O | HOH | W | 166 | -106.634 | -5.311 | 26.057 | 1.00 | 27.44 |
| 24328 | O | HOH | W | 167 | -62.637 | 0.167 | 91.371 | 1.00 | 24.04 |
| 24329 | O | HOH | W | 168 | -72.863 | 22.007 | 67.554 | 1.00 | 38.64 |
| 24330 | O | HOH | W | 169 | -114.985 | 13.055 | 45.357 | 1.00 | 40.11 |
| 24331 | O | HOH | W | 170 | -71.027 | -10.565 | 83.882 | 1.00 | 39.02 |
| 24332 | O | HOH | W | 171 | -71.902 | -4.399 | 21.029 | 1.00 | 31.18 |
| 24333 | O | HOH | W | 172 | -48.422 | 1.924 | 102.299 | 1.00 | 32.51 |
| 24334 | O | HOH | W | 173 | -48.339 | -3.859 | 75.038 | 1.00 | 24.54 |
| 24335 | O | HOH | W | 174 | -107.907 | -2.609 | 32.422 | 1.00 | 22.99 |
| 24336 | O | HOH | W | 175 | -104.620 | -18.098 | 43.567 | 1.00 | 35.88 |
| 24337 | O | HOH | W | 176 | -90.642 | 0.177 | 20.961 | 1.00 | 22.61 |
| 24338 | O | HOH | W | 177 | -110.363 | 10.007 | 42.496 | 1.00 | 33.78 |
| 24339 | O | HOH | W | 178 | -85.410 | -18.015 | 73.273 | 1.00 | 17.91 |
| 24340 | O | HOH | W | 179 | -57.482 | 7.441 | 93.816 | 1.00 | 23.43 |
| 24341 | O | HOH | W | 180 | -35.275 | -15.110 | 99.309 | 1.00 | 32.53 |
| 24342 | O | HOH | W | 181 | -12.734 | -3.318 | 78.965 | 1.00 | 34.77 |
| 24343 | O | HOH | W | 182 | -118.291 | 5.612 | 43.221 | 1.00 | 24.78 |
| 24344 | O | HOH | W | 183 | -58.998 | -24.547 | 94.104 | 1.00 | 39.07 |
| 24345 | O | HOH | W | 184 | -68.221 | 4.700 | 81.326 | 1.00 | 21.62 |
| 24346 | O | HOH | W | 185 | -55.744 | -25.024 | 77.689 | 1.00 | 38.78 |
| 24347 | O | HOH | W | 186 | -51.734 | -8.919 | 92.077 | 1.00 | 24.62 |
| 24348 | O | HOH | W | 187 | -59.944 | 8.112 | 87.649 | 1.00 | 32.98 |
| 24349 | O | HOH | W | 188 | -76.414 | -19.148 | 58.805 | 1.00 | 46.32 |
| 24350 | O | HOH | W | 189 | -50.989 | 14.314 | 75.971 | 1.00 | 34.01 |
| 24351 | O | HOH | W | 190 | 1.782 | 15.783 | 87.688 | 1.00 | 56.92 |
| 24352 | O | HOH | W | 191 | -74.202 | -3.438 | 22.570 | 1.00 | 29.82 |
| 24353 | O | HOH | W | 192 | -32.236 | 1.625 | 89.839 | 1.00 | 25.96 |
| 24354 | O | HOH | W | 193 | -75.647 | 0.161 | 28.354 | 1.00 | 29.82 |
| 24355 | O | HOH | W | 194 | -92.262 | -14.808 | 91.578 | 1.00 | 30.64 |
| 24356 | O | HOH | W | 195 | -83.298 | -11.345 | 4.255 | 1.00 | 38.28 |
| 24357 | O | HOH | W | 196 | -37.338 | 3.161 | 59.048 | 1.00 | 20.67 |
| 24358 | O | HOH | W | 197 | -59.182 | -7.885 | 99.202 | 1.00 | 36.33 |
| 24359 | O | HOH | W | 198 | -30.676 | 15.551 | 78.119 | 1.00 | 28.90 |
| 24360 | O | HOH | W | 199 | -77.000 | -8.976 | 77.246 | 1.00 | 30.29 |
| 24361 | O | HOH | W | 200 | -62.592 | -2.234 | 91.528 | 1.00 | 22.49 |
| 24362 | O | HOH | W | 201 | -84.788 | -15.542 | 74.412 | 1.00 | 22.56 |
| 24363 | O | HOH | W | 202 | -75.385 | -10.834 | 68.001 | 1.00 | 24.89 |
| 24364 | O | HOH | W | 203 | -77.662 | -8.241 | 26.170 | 1.00 | 21.16 |
| 24365 | O | HOH | W | 204 | -64.771 | 1.570 | 90.052 | 1.00 | 33.62 |
| 24366 | O | HOH | W | 205 | -81.699 | -10.155 | 47.063 | 1.00 | 36.98 |
| 24367 | O | HOH | W | 206 | -20.231 | -36.910 | 75.605 | 1.00 | 36.29 |
| 24368 | O | HOH | W | 207 | -25.961 | -27.837 | 99.022 | 1.00 | 38.88 |

FIGURE 3 TL

| A | B | C | D | E | F | G | H | I | J |
|---|---|---|---|---|---|---|---|---|---|
| 24369 | O | HOH | W | 208 | -96.006 | -14.048 | 18.095 | 1.00 | 28.04 |
| 24370 | O | HOH | W | 209 | -58.469 | 5.269 | 93.487 | 1.00 | 23.13 |
| 24371 | O | HOH | W | 210 | -74.325 | -6.822 | 68.883 | 1.00 | 20.73 |
| 24372 | O | HOH | W | 211 | -89.567 | -12.790 | 68.569 | 1.00 | 25.44 |
| 24373 | O | HOH | W | 212 | -37.674 | 0.666 | 58.639 | 1.00 | 25.90 |
| 24374 | O | HOH | W | 213 | -68.643 | -16.312 | 26.182 | 1.00 | 34.79 |
| 24375 | O | HOH | W | 214 | -30.927 | 5.755 | 102.928 | 1.00 | 32.95 |
| 24376 | O | HOH | W | 215 | -79.481 | -1.250 | 35.367 | 1.00 | 26.75 |
| 24377 | O | HOH | W | 216 | -92.377 | -0.377 | 25.088 | 1.00 | 25.39 |
| 24378 | O | HOH | W | 217 | -83.520 | -15.613 | 70.403 | 1.00 | 24.33 |
| 24379 | O | HOH | W | 218 | -72.696 | -23.309 | 102.427 | 1.00 | 27.73 |
| 24380 | O | HOH | W | 219 | -77.396 | -4.105 | -0.654 | 1.00 | 32.28 |
| 24381 | O | HOH | W | 220 | -117.083 | -11.246 | 50.304 | 1.00 | 31.59 |
| 24382 | O | HOH | W | 221 | -97.187 | -16.296 | 65.596 | 1.00 | 36.87 |
| 24383 | O | HOH | W | 222 | -85.942 | -11.587 | 45.311 | 1.00 | 26.63 |
| 24384 | O | HOH | W | 223 | -41.219 | -10.073 | 88.257 | 1.00 | 19.26 |
| 24385 | O | HOH | W | 224 | -77.785 | -29.179 | 76.237 | 1.00 | 27.76 |
| 24386 | O | HOH | W | 225 | -55.141 | -17.302 | 92.534 | 1.00 | 36.22 |
| 24387 | O | HOH | W | 226 | -89.051 | -3.976 | 58.563 | 1.00 | 31.85 |
| 24388 | O | HOH | W | 227 | -133.159 | 5.245 | 4.407 | 1.00 | 35.71 |
| 24389 | O | HOH | W | 228 | -64.438 | -15.995 | 30.706 | 1.00 | 31.36 |
| 24390 | O | HOH | W | 229 | -95.735 | -25.318 | 29.954 | 1.00 | 34.97 |
| 24391 | O | HOH | W | 230 | -73.488 | -8.008 | 80.339 | 1.00 | 34.43 |
| 24392 | O | HOH | W | 231 | -111.130 | -3.552 | 40.809 | 1.00 | 23.31 |
| 24393 | O | HOH | W | 232 | -110.233 | -1.951 | 33.979 | 1.00 | 21.17 |
| 24394 | O | HOH | W | 233 | -114.918 | 6.101 | 34.185 | 1.00 | 22.47 |
| 24395 | O | HOH | W | 234 | -122.726 | -5.394 | 51.238 | 1.00 | 26.82 |
| 24396 | O | HOH | W | 235 | -122.574 | -1.404 | 39.114 | 1.00 | 40.17 |
| 24397 | O | HOH | W | 236 | -73.267 | -25.867 | 81.292 | 1.00 | 29.46 |
| 24398 | O | HOH | W | 237 | -84.409 | -1.101 | 26.394 | 1.00 | 29.29 |
| 24399 | O | HOH | W | 238 | -91.341 | -16.988 | 84.578 | 1.00 | 25.96 |
| 24400 | O | HOH | W | 239 | -39.470 | -12.050 | 73.075 | 1.00 | 37.03 |
| 24401 | O | HOH | W | 240 | -2.061 | -8.117 | 106.954 | 1.00 | 34.50 |
| 24402 | O | HOH | W | 241 | -59.827 | -16.337 | 6.625 | 1.00 | 34.16 |
| 24403 | O | HOH | W | 242 | -87.331 | 4.980 | 43.006 | 1.00 | 39.82 |
| 24404 | O | HOH | W | 243 | -96.863 | -28.277 | 33.742 | 1.00 | 44.85 |
| 24405 | O | HOH | W | 244 | -104.593 | -13.702 | 41.488 | 1.00 | 19.51 |
| 24406 | O | HOH | W | 245 | -73.417 | -11.509 | 83.254 | 1.00 | 26.05 |
| 24407 | O | HOH | W | 246 | -75.722 | 2.349 | 69.359 | 1.00 | 29.25 |
| 24408 | O | HOH | W | 247 | -24.578 | 1.538 | 70.024 | 1.00 | 39.78 |
| 24409 | O | HOH | W | 248 | -46.998 | -3.845 | 101.005 | 1.00 | 32.06 |
| 24410 | O | HOH | W | 249 | -92.617 | -13.851 | 9.018 | 1.00 | 42.28 |
| 24411 | O | HOH | W | 250 | -61.764 | -8.020 | 59.987 | 1.00 | 26.98 |
| 24412 | O | HOH | W | 251 | -100.091 | 14.397 | 26.529 | 1.00 | 33.05 |
| 24413 | O | HOH | W | 252 | -42.633 | -6.822 | 68.502 | 1.00 | 24.40 |
| 24414 | O | HOH | W | 253 | -7.181 | 8.932 | 64.612 | 1.00 | 53.64 |
| 24415 | O | HOH | W | 254 | -27.720 | 14.073 | 82.527 | 1.00 | 30.70 |
| 24416 | O | HOH | W | 255 | -24.177 | 14.802 | 60.014 | 1.00 | 34.48 |
| 24417 | O | HOH | W | 256 | -119.569 | -12.532 | 51.495 | 1.00 | 34.93 |
| 24418 | O | HOH | W | 257 | -79.324 | -19.664 | 11.988 | 1.00 | 34.52 |
| 24419 | O | HOH | W | 258 | -23.137 | 8.077 | 85.725 | 1.00 | 30.90 |

FIGURE 3 TM

| A | B | C | D | E | F | G | H | I | J |
|---|---|---|---|---|---|---|---|---|---|
| 24420 | O | HOH | W | 259 | -112.359 | -5.953 | 39.910 | 1.00 | 23.57 |
| 24421 | O | HOH | W | 260 | -87.105 | -12.094 | 63.902 | 1.00 | 34.92 |
| 24422 | O | HOH | W | 261 | -62.976 | 1.555 | 93.915 | 1.00 | 36.04 |
| 24423 | O | HOH | W | 262 | -53.812 | -0.539 | 59.667 | 1.00 | 37.46 |
| 24424 | O | HOH | W | 263 | -34.031 | -2.761 | 87.089 | 1.00 | 29.06 |
| 24425 | O | HOH | W | 264 | -6.705 | -3.338 | 96.833 | 1.00 | 39.74 |
| 24426 | O | HOH | W | 265 | -74.896 | 5.360 | 95.271 | 1.00 | 56.40 |
| 24427 | O | HOH | W | 266 | -59.460 | -24.880 | 84.398 | 1.00 | 40.62 |
| 24428 | O | HOH | W | 267 | -76.631 | -8.476 | 69.740 | 1.00 | 26.98 |
| 24429 | O | HOH | W | 268 | -89.995 | -1.453 | 18.972 | 1.00 | 30.42 |
| 24430 | O | HOH | W | 269 | -32.602 | -12.208 | 2.518 | 1.00 | 61.33 |
| 24431 | O | HOH | W | 270 | -77.030 | -19.598 | 85.298 | 1.00 | 19.19 |
| 24432 | O | HOH | W | 271 | -41.014 | -1.534 | 63.232 | 1.00 | 27.69 |
| 24433 | O | HOH | W | 272 | -10.257 | -6.964 | 64.268 | 1.00 | 45.43 |
| 24434 | O | HOH | W | 273 | -100.633 | 14.121 | 46.413 | 1.00 | 22.88 |
| 24435 | O | HOH | W | 274 | -90.144 | 6.000 | 42.386 | 1.00 | 26.82 |
| 24436 | O | HOH | W | 275 | -43.139 | -10.647 | 75.949 | 1.00 | 41.26 |
| 24437 | O | HOH | W | 276 | -79.138 | -27.021 | 101.715 | 1.00 | 38.78 |
| 24438 | O | HOH | W | 277 | -90.782 | -17.156 | 28.326 | 1.00 | 24.37 |
| 24439 | O | HOH | W | 278 | -119.652 | -0.976 | 45.322 | 1.00 | 29.90 |
| 24440 | O | HOH | W | 279 | -56.269 | -8.617 | 86.422 | 1.00 | 24.42 |
| 24441 | O | HOH | W | 280 | -121.228 | -17.863 | 25.690 | 1.00 | 42.06 |
| 24442 | O | HOH | W | 281 | -83.963 | -10.204 | 47.551 | 1.00 | 29.91 |
| 24443 | O | HOH | W | 282 | -106.283 | -7.787 | 25.072 | 1.00 | 19.72 |
| 24444 | O | HOH | W | 283 | -26.442 | 5.106 | 111.640 | 1.00 | 26.93 |
| 24445 | O | HOH | W | 284 | -30.160 | -24.628 | 79.920 | 1.00 | 31.03 |
| 24446 | O | HOH | W | 285 | -53.610 | 11.401 | 97.883 | 1.00 | 33.98 |
| 24447 | O | HOH | W | 286 | -83.509 | 1.590 | 42.769 | 1.00 | 26.82 |
| 24448 | O | HOH | W | 287 | -87.279 | -6.046 | 78.528 | 1.00 | 52.68 |
| 24449 | O | HOH | W | 288 | -72.847 | 5.572 | -1.336 | 1.00 | 40.58 |
| 24450 | O | HOH | W | 289 | -111.385 | -17.904 | 9.313 | 1.00 | 42.55 |
| 24451 | O | HOH | W | 290 | -41.612 | -8.792 | 66.548 | 1.00 | 33.68 |
| 24452 | O | HOH | W | 291 | -56.140 | 16.815 | 76.688 | 1.00 | 32.39 |
| 24453 | O | HOH | W | 292 | -111.586 | -16.824 | 12.088 | 1.00 | 37.33 |
| 24454 | O | HOH | W | 293 | -63.913 | -12.750 | 109.046 | 1.00 | 39.21 |
| 24455 | O | HOH | W | 294 | -52.563 | -15.484 | 82.996 | 1.00 | 24.79 |
| 24456 | O | HOH | W | 295 | -74.928 | -10.977 | 81.127 | 1.00 | 25.93 |
| 24457 | O | HOH | W | 296 | -71.856 | -3.869 | 0.862 | 1.00 | 39.40 |
| 24458 | O | HOH | W | 297 | -92.388 | 7.474 | 22.287 | 1.00 | 36.88 |
| 24459 | O | HOH | W | 298 | -113.255 | -22.248 | 37.416 | 1.00 | 32.99 |
| 24460 | O | HOH | W | 299 | -56.624 | -21.871 | 66.601 | 1.00 | 62.21 |
| 24461 | O | HOH | W | 300 | -69.526 | -9.432 | 19.901 | 1.00 | 42.19 |
| 24462 | O | HOH | W | 301 | -85.865 | 7.711 | 63.285 | 1.00 | 42.58 |
| 24463 | O | HOH | W | 302 | -91.267 | -14.271 | 84.352 | 1.00 | 26.57 |
| 24464 | O | HOH | W | 303 | -95.271 | 15.524 | 82.843 | 1.00 | 40.52 |
| 24465 | O | HOH | W | 304 | -109.080 | -5.733 | 48.972 | 1.00 | 21.15 |
| 24466 | O | HOH | W | 305 | -19.924 | -6.058 | 62.090 | 1.00 | 33.77 |
| 24467 | O | HOH | W | 306 | -131.353 | -12.524 | 54.607 | 1.00 | 39.97 |
| 24468 | O | HOH | W | 307 | -82.761 | -15.268 | 82.570 | 1.00 | 22.77 |
| 24469 | O | HOH | W | 308 | -120.711 | -19.867 | 51.546 | 1.00 | 29.54 |
| 24470 | O | HOH | W | 309 | -100.641 | -16.744 | 72.476 | 1.00 | 36.27 |

FIGURE 3 TN

| A | B | C | D | E | F | G | H | I | J |
|---|---|---|---|---|---|---|---|---|---|
| 24471 | O | HOH | W | 310 | -80.240 | -17.209 | 39.758 | 1.00 | 33.90 |
| 24472 | O | HOH | W | 311 | -31.708 | -9.641 | 95.238 | 1.00 | 29.12 |
| 24473 | O | HOH | W | 312 | -83.814 | -16.154 | 5.680 | 1.00 | 53.05 |
| 24474 | O | HOH | W | 313 | -37.232 | -6.563 | 80.302 | 1.00 | 36.17 |
| 24475 | O | HOH | W | 314 | -70.622 | -1.977 | 88.167 | 1.00 | 27.88 |
| 24476 | O | HOH | W | 315 | -84.119 | -4.252 | 74.137 | 1.00 | 31.96 |
| 24477 | O | HOH | W | 316 | -77.295 | -10.541 | 81.836 | 1.00 | 32.42 |
| 24478 | O | HOH | W | 317 | -101.238 | -14.498 | 72.963 | 1.00 | 45.28 |
| 24479 | O | HOH | W | 318 | -24.754 | 5.854 | 86.018 | 1.00 | 31.66 |
| 24480 | O | HOH | W | 319 | -73.523 | -10.444 | 44.877 | 1.00 | 29.80 |
| 24481 | O | HOH | W | 320 | -59.557 | 13.895 | 78.345 | 1.00 | 26.20 |
| 24482 | O | HOH | W | 321 | -109.292 | -3.190 | 47.869 | 1.00 | 23.62 |
| 24483 | O | HOH | W | 322 | -91.160 | -8.045 | 54.116 | 1.00 | 23.32 |
| 24484 | O | HOH | W | 323 | -25.913 | 8.917 | 82.854 | 1.00 | 29.76 |
| 24485 | O | HOH | W | 324 | -45.682 | -7.725 | 76.713 | 1.00 | 28.57 |
| 24486 | O | HOH | W | 325 | -29.382 | 0.836 | 55.856 | 1.00 | 39.66 |
| 24487 | O | HOH | W | 326 | -32.152 | -26.155 | 78.159 | 1.00 | 37.39 |
| 24488 | O | HOH | W | 327 | -114.146 | 5.928 | 52.894 | 1.00 | 33.72 |
| 24489 | O | HOH | W | 328 | -78.027 | -8.774 | 43.048 | 1.00 | 21.47 |
| 24490 | O | HOH | W | 329 | -124.215 | 5.256 | 39.406 | 1.00 | 37.84 |
| 24491 | O | HOH | W | 330 | -114.276 | -0.923 | 34.147 | 1.00 | 29.79 |
| 24492 | O | HOH | W | 331 | -86.349 | -13.850 | 81.041 | 1.00 | 34.32 |
| 24493 | O | HOH | W | 332 | -48.933 | 4.882 | 102.460 | 1.00 | 25.22 |
| 24494 | O | HOH | W | 333 | -144.631 | 1.048 | 44.554 | 1.00 | 40.54 |
| 24495 | O | HOH | W | 334 | -78.844 | -2.914 | 102.492 | 1.00 | 34.39 |
| 24496 | O | HOH | W | 335 | -82.073 | -8.908 | 53.475 | 1.00 | 34.72 |
| 24497 | O | HOH | W | 336 | -132.571 | -12.045 | 51.216 | 1.00 | 43.39 |
| 24498 | O | HOH | W | 337 | -113.484 | 15.595 | 18.318 | 1.00 | 43.50 |
| 24499 | O | HOH | W | 338 | -80.286 | 5.452 | 15.760 | 1.00 | 42.84 |
| 24500 | O | HOH | W | 339 | -94.063 | 4.582 | 23.976 | 1.00 | 23.62 |
| 24501 | O | HOH | W | 340 | -123.795 | 9.308 | 48.657 | 1.00 | 34.25 |
| 24502 | O | HOH | W | 341 | -8.269 | -4.453 | 84.606 | 1.00 | 44.86 |
| 24503 | O | HOH | W | 342 | -137.812 | -28.700 | 21.377 | 1.00 | 49.37 |
| 24504 | O | HOH | W | 343 | -70.782 | -7.957 | 90.513 | 1.00 | 23.76 |
| 24505 | O | HOH | W | 344 | -51.640 | -3.177 | 62.800 | 1.00 | 28.14 |
| 24506 | O | HOH | W | 345 | -107.294 | 19.998 | 28.517 | 1.00 | 34.16 |
| 24507 | O | HOH | W | 346 | -75.391 | -31.741 | 89.888 | 1.00 | 34.52 |
| 24508 | O | HOH | W | 347 | -28.729 | 4.980 | 89.134 | 1.00 | 29.64 |
| 24509 | O | HOH | W | 348 | -94.866 | 8.220 | 22.666 | 1.00 | 37.15 |
| 24510 | O | HOH | W | 349 | -47.619 | 5.635 | 68.767 | 1.00 | 31.79 |
| 24511 | O | HOH | W | 350 | -32.001 | -5.017 | 90.310 | 1.00 | 28.26 |
| 24512 | O | HOH | W | 351 | -117.983 | -20.729 | 54.852 | 1.00 | 39.53 |
| 24513 | O | HOH | W | 352 | -45.251 | 5.119 | 19.195 | 1.00 | 47.31 |
| 24514 | O | HOH | W | 353 | -93.949 | -1.603 | 27.037 | 1.00 | 28.43 |
| 24515 | O | HOH | W | 354 | 11.481 | 9.358 | 86.657 | 1.00 | 48.62 |
| 24516 | O | HOH | W | 355 | -60.019 | 14.574 | 67.773 | 1.00 | 47.66 |
| 24517 | O | HOH | W | 356 | -45.557 | -15.018 | 78.497 | 1.00 | 25.05 |
| 24518 | O | HOH | W | 357 | -76.943 | -0.688 | 70.818 | 1.00 | 40.91 |
| 24519 | O | HOH | W | 358 | -60.725 | -1.346 | 55.724 | 1.00 | 44.13 |
| 24520 | O | HOH | W | 359 | -90.931 | -11.002 | 62.749 | 1.00 | 37.87 |
| 24521 | O | HOH | W | 360 | -103.687 | 19.110 | 45.842 | 1.00 | 40.74 |

FIGURE 3 TO

| A | B | C | D | E | F | G | H | I | J |
|---|---|---|---|---|---|---|---|---|---|
| 24522 | O | HOH | W | 361 | -103.447 | 1.555 | 58.425 | 1.00 | 44.32 |
| 24523 | O | HOH | W | 362 | -62.424 | -33.596 | 14.361 | 1.00 | 42.09 |
| 24524 | O | HOH | W | 363 | -142.610 | 6.528 | 48.843 | 1.00 | 35.58 |
| 24525 | O | HOH | W | 364 | -50.711 | -7.054 | 8.397 | 1.00 | 49.26 |
| 24526 | O | HOH | W | 365 | -32.087 | -3.255 | 68.786 | 1.00 | 29.39 |
| 24527 | O | HOH | W | 366 | -78.082 | 0.405 | 23.933 | 1.00 | 31.59 |
| 24528 | O | HOH | W | 367 | -30.102 | 14.289 | 80.546 | 1.00 | 28.45 |
| 24529 | O | HOH | W | 368 | -84.631 | -31.154 | 102.920 | 1.00 | 45.04 |
| 24530 | O | HOH | W | 369 | -73.753 | -25.119 | 77.110 | 1.00 | 23.89 |
| 24531 | O | HOH | W | 370 | -30.399 | 14.616 | 102.905 | 1.00 | 46.03 |
| 24532 | O | HOH | W | 371 | -46.946 | 22.032 | 80.247 | 1.00 | 28.87 |
| 24533 | O | HOH | W | 372 | -86.341 | 13.219 | 86.877 | 1.00 | 47.17 |
| 24534 | O | HOH | W | 373 | -19.006 | -2.210 | 116.881 | 1.00 | 33.56 |
| 24535 | O | HOH | W | 374 | -76.017 | -7.389 | 42.389 | 1.00 | 31.21 |
| 24536 | O | HOH | W | 375 | -66.602 | -6.591 | 17.190 | 1.00 | 38.69 |
| 24537 | O | HOH | W | 376 | -88.752 | -13.509 | 66.146 | 1.00 | 32.00 |
| 24538 | O | HOH | W | 377 | -55.062 | -14.282 | 90.703 | 1.00 | 26.99 |
| 24539 | O | HOH | W | 378 | -78.048 | -9.519 | 45.392 | 1.00 | 24.96 |
| 24540 | O | HOH | W | 379 | -46.272 | -14.689 | 60.543 | 1.00 | 46.39 |
| 24541 | O | HOH | W | 380 | -104.895 | 17.465 | 31.690 | 1.00 | 52.28 |
| 24542 | O | HOH | W | 381 | -90.097 | -5.431 | 81.500 | 1.00 | 29.16 |
| 24543 | O | HOH | W | 382 | -35.670 | -1.759 | 75.500 | 1.00 | 33.60 |
| 24544 | O | HOH | W | 383 | -27.003 | 8.111 | 68.489 | 1.00 | 29.54 |
| 24545 | O | HOH | W | 384 | -115.888 | -9.266 | 25.040 | 1.00 | 38.52 |
| 24546 | O | HOH | W | 385 | -27.613 | -1.659 | 68.433 | 1.00 | 34.39 |
| 24547 | O | HOH | W | 386 | -71.527 | -25.637 | 101.416 | 1.00 | 36.97 |
| 24548 | O | HOH | W | 387 | -140.064 | 9.912 | 23.260 | 1.00 | 42.90 |
| 24549 | O | HOH | W | 388 | -40.301 | -8.785 | 104.462 | 1.00 | 40.87 |
| 24550 | O | HOH | W | 389 | -64.273 | 1.125 | 23.882 | 1.00 | 39.29 |
| 24551 | O | HOH | W | 390 | -92.220 | -5.490 | 23.328 | 1.00 | 25.87 |
| 24552 | O | HOH | W | 391 | -34.229 | 1.672 | 112.166 | 1.00 | 32.95 |
| 24553 | O | HOH | W | 392 | -4.121 | -6.162 | 88.781 | 1.00 | 46.28 |
| 24554 | O | HOH | W | 393 | -55.972 | -24.423 | 84.033 | 1.00 | 48.43 |
| 24555 | O | HOH | W | 394 | -56.995 | 8.367 | 70.948 | 1.00 | 29.49 |
| 24556 | O | HOH | W | 395 | -126.333 | -7.814 | 37.963 | 1.00 | 37.37 |
| 24557 | O | HOH | W | 396 | -48.948 | 3.852 | 66.990 | 1.00 | 37.01 |
| 24558 | O | HOH | W | 397 | -46.749 | -1.825 | 90.667 | 1.00 | 27.00 |
| 24559 | O | HOH | W | 398 | -106.804 | 0.856 | 6.978 | 1.00 | 47.53 |
| 24560 | O | HOH | W | 399 | -66.287 | -18.360 | 33.203 | 1.00 | 36.53 |
| 24561 | O | HOH | W | 400 | -61.116 | -8.337 | 36.977 | 1.00 | 45.12 |
| 24562 | O | HOH | W | 401 | -96.847 | -20.236 | 62.448 | 1.00 | 49.72 |
| 24563 | O | HOH | W | 402 | -27.539 | -32.416 | 74.701 | 1.00 | 45.14 |
| 24564 | O | HOH | W | 403 | -27.859 | 8.977 | 87.605 | 1.00 | 23.06 |
| 24565 | O | HOH | W | 404 | -113.552 | -6.130 | 38.217 | 1.00 | 34.04 |
| 24566 | O | HOH | W | 405 | -41.959 | 22.786 | 70.496 | 1.00 | 27.28 |
| 24567 | O | HOH | W | 406 | -43.248 | 24.044 | 98.232 | 1.00 | 47.89 |
| 24568 | O | HOH | W | 407 | -98.090 | 3.948 | 48.778 | 1.00 | 36.98 |
| 24569 | O | HOH | W | 408 | -117.722 | -1.339 | 49.192 | 1.00 | 33.13 |
| 24570 | O | HOH | W | 409 | -97.186 | 23.891 | 38.877 | 1.00 | 37.04 |
| 24571 | O | HOH | W | 410 | -54.077 | -21.256 | 87.483 | 1.00 | 31.67 |
| 24572 | O | HOH | W | 411 | -26.540 | -7.257 | 58.482 | 1.00 | 35.63 |

FIGURE 3 TP

| A | B | C | D | E | F | G | H | I | J |
|---|---|---|---|---|---|---|---|---|---|
| 24573 | O | HOH | W | 412 | -59.189 | 15.902 | 76.884 | 1.00 | 28.37 |
| 24574 | O | HOH | W | 413 | -106.052 | -19.912 | 38.113 | 1.00 | 37.83 |
| 24575 | O | HOH | W | 414 | -38.457 | -5.391 | 64.442 | 1.00 | 36.51 |
| 24576 | O | HOH | W | 415 | -81.281 | -16.478 | 41.821 | 1.00 | 28.20 |
| 24577 | O | HOH | W | 416 | -62.592 | 15.864 | 83.338 | 1.00 | 41.79 |
| 24578 | O | HOH | W | 417 | -90.440 | -7.959 | 81.659 | 1.00 | 33.84 |
| 24579 | O | HOH | W | 418 | -109.276 | -4.084 | 65.347 | 1.00 | 45.60 |
| 24580 | O | HOH | W | 419 | -69.006 | -12.524 | 47.891 | 1.00 | 34.51 |
| 24581 | O | HOH | W | 420 | -61.674 | 13.685 | 79.885 | 1.00 | 22.82 |
| 24582 | O | HOH | W | 421 | -77.977 | 6.047 | 70.046 | 1.00 | 24.17 |
| 24583 | O | HOH | W | 422 | -79.914 | -36.956 | 84.165 | 1.00 | 44.36 |
| 24584 | O | HOH | W | 423 | -75.416 | -3.338 | 43.412 | 1.00 | 28.37 |
| 24585 | O | HOH | W | 424 | -18.933 | 12.928 | 89.742 | 1.00 | 25.94 |
| 24586 | O | HOH | W | 425 | -94.178 | 3.382 | 47.428 | 1.00 | 36.17 |
| 24587 | O | HOH | W | 426 | -52.330 | 5.800 | 71.979 | 1.00 | 21.85 |
| 24588 | O | HOH | W | 427 | -88.551 | -11.856 | 14.969 | 1.00 | 34.68 |
| 24589 | O | HOH | W | 428 | -85.645 | -17.986 | 37.895 | 1.00 | 33.59 |
| 24590 | O | HOH | W | 429 | -132.669 | -7.587 | 47.834 | 1.00 | 36.03 |
| 24591 | O | HOH | W | 430 | -108.763 | -1.321 | 24.408 | 1.00 | 28.53 |
| 24592 | O | HOH | W | 431 | -88.217 | -9.065 | 82.661 | 1.00 | 30.48 |
| 24593 | O | HOH | W | 432 | -56.817 | -21.493 | 13.134 | 1.00 | 42.34 |
| 24594 | O | HOH | W | 433 | -85.022 | 5.402 | 37.016 | 1.00 | 28.68 |
| 24595 | O | HOH | W | 434 | -73.814 | -5.264 | 66.747 | 1.00 | 21.12 |
| 24596 | O | HOH | W | 435 | -28.261 | 13.058 | 71.895 | 1.00 | 30.19 |
| 24597 | O | HOH | W | 436 | -28.806 | 16.105 | 86.546 | 1.00 | 23.64 |
| 24598 | O | HOH | W | 437 | -67.417 | -16.186 | 93.767 | 1.00 | 23.93 |
| 24599 | O | HOH | W | 438 | -48.439 | -5.879 | 87.312 | 1.00 | 25.91 |
| 24600 | O | HOH | W | 439 | -64.299 | -28.634 | 72.041 | 1.00 | 33.74 |
| 24601 | O | HOH | W | 440 | -51.532 | -5.766 | 89.351 | 1.00 | 34.47 |
| 24602 | O | HOH | W | 441 | -93.787 | -8.401 | 22.095 | 1.00 | 32.88 |
| 24603 | O | HOH | W | 442 | -71.406 | 3.880 | 14.002 | 1.00 | 33.45 |
| 24604 | O | HOH | W | 443 | -98.429 | -9.433 | 30.498 | 1.00 | 29.14 |
| 24605 | O | HOH | W | 444 | -70.817 | -10.368 | 96.315 | 1.00 | 27.94 |
| 24606 | O | HOH | W | 445 | -97.517 | 13.369 | 26.783 | 1.00 | 33.43 |
| 24607 | O | HOH | W | 446 | -89.969 | -3.182 | 22.808 | 1.00 | 35.56 |
| 24608 | O | HOH | W | 447 | -22.398 | -7.403 | 112.204 | 1.00 | 36.75 |
| 24609 | O | HOH | W | 448 | -54.199 | -9.603 | 88.145 | 1.00 | 21.39 |
| 24610 | O | HOH | W | 449 | -9.727 | -30.093 | 71.057 | 1.00 | 39.70 |
| 24611 | O | HOH | W | 450 | -33.216 | 5.161 | 88.968 | 1.00 | 31.92 |
| 24612 | O | HOH | W | 451 | -71.338 | 7.377 | 0.357 | 1.00 | 56.63 |
| 24613 | O | HOH | W | 452 | -65.276 | -2.999 | 91.373 | 1.00 | 31.95 |
| 24614 | O | HOH | W | 453 | -93.385 | 9.333 | 34.303 | 1.00 | 30.73 |
| 24615 | O | HOH | W | 454 | -88.266 | -21.163 | 92.334 | 1.00 | 34.41 |
| 24616 | O | HOH | W | 455 | 7.452 | 15.404 | 87.259 | 1.00 | 48.25 |
| 24617 | O | HOH | W | 456 | -78.495 | -10.661 | 40.980 | 1.00 | 29.54 |
| 24618 | O | HOH | W | 457 | -29.277 | -0.034 | 109.864 | 1.00 | 41.20 |
| 24619 | O | HOH | W | 458 | -84.933 | -22.922 | 78.703 | 1.00 | 29.22 |
| 24620 | O | HOH | W | 459 | -67.783 | -18.157 | 61.639 | 1.00 | 59.22 |
| 24621 | O | HOH | W | 460 | -87.054 | -3.611 | 13.871 | 1.00 | 35.20 |
| 24622 | O | HOH | W | 461 | -106.268 | 3.822 | 20.597 | 1.00 | 40.04 |
| 24623 | O | HOH | W | 462 | -14.798 | -27.138 | 95.307 | 1.00 | 42.14 |

FIGURE 3 TQ

| A | B | C | D | E | F | G | H | I | J |
|---|---|---|---|---|---|---|---|---|---|
| 24624 | O | HOH | W | 463 | -106.608 | -0.853 | 14.325 | 1.00 | 44.75 |
| 24625 | O | HOH | W | 464 | -12.037 | 19.585 | 82.638 | 1.00 | 34.50 |
| 24626 | O | HOH | W | 465 | -9.799 | 0.222 | 61.269 | 1.00 | 37.92 |
| 24627 | O | HOH | W | 466 | -20.392 | 5.445 | 93.033 | 1.00 | 25.96 |
| 24628 | O | HOH | W | 467 | -109.907 | 10.806 | 33.777 | 1.00 | 42.21 |
| 24629 | O | HOH | W | 468 | -72.446 | -27.810 | 77.689 | 1.00 | 40.27 |
| 24630 | O | HOH | W | 469 | -42.426 | -12.230 | 79.608 | 1.00 | 32.72 |
| 24631 | O | HOH | W | 470 | -71.414 | 0.070 | 15.776 | 1.00 | 39.43 |
| 24632 | O | HOH | W | 471 | -9.422 | 11.591 | 79.064 | 1.00 | 45.89 |
| 24633 | O | HOH | W | 472 | -99.297 | -8.426 | 65.422 | 1.00 | 34.72 |
| 24634 | O | HOH | W | 473 | -86.247 | -3.322 | 24.107 | 1.00 | 27.75 |
| 24635 | O | HOH | W | 474 | -33.420 | 7.924 | 76.871 | 1.00 | 35.27 |
| 24636 | O | HOH | W | 475 | -84.558 | -15.993 | 84.177 | 1.00 | 25.38 |
| 24637 | O | HOH | W | 476 | -110.008 | -7.611 | 47.215 | 1.00 | 32.50 |
| 24638 | O | HOH | W | 477 | -87.610 | -29.622 | 80.099 | 1.00 | 41.19 |
| 24639 | O | HOH | W | 478 | -63.868 | 15.881 | 75.751 | 1.00 | 32.12 |
| 24640 | O | HOH | W | 479 | -102.368 | 13.617 | 82.403 | 1.00 | 51.21 |
| 24641 | O | HOH | W | 480 | -93.676 | -8.304 | 53.421 | 1.00 | 22.95 |
| 24642 | O | HOH | W | 481 | -65.038 | -2.900 | 54.046 | 1.00 | 29.86 |
| 24643 | O | HOH | W | 482 | -92.189 | -12.262 | 66.212 | 1.00 | 33.84 |
| 24644 | O | HOH | W | 483 | -34.202 | -6.218 | 86.179 | 1.00 | 26.53 |
| 24645 | O | HOH | W | 484 | -96.451 | 9.670 | 20.995 | 1.00 | 36.39 |
| 24646 | O | HOH | W | 485 | -95.374 | -17.291 | 106.485 | 1.00 | 52.48 |
| 24647 | O | HOH | W | 486 | -73.322 | -2.828 | 74.671 | 1.00 | 32.65 |
| 24648 | O | HOH | W | 487 | -64.306 | 10.964 | 88.902 | 1.00 | 36.83 |
| 24649 | O | HOH | W | 488 | -51.433 | 10.267 | 65.577 | 1.00 | 49.74 |
| 24650 | O | HOH | W | 489 | -94.223 | 11.434 | 50.644 | 1.00 | 58.39 |
| 24651 | O | HOH | W | 490 | -111.244 | 11.678 | 38.858 | 1.00 | 40.23 |
| 24652 | O | HOH | W | 491 | -84.214 | -35.551 | 92.737 | 1.00 | 32.32 |
| 24653 | O | HOH | W | 492 | -51.608 | -18.135 | 89.834 | 1.00 | 26.53 |
| 24654 | O | HOH | W | 493 | -17.440 | -25.419 | 66.465 | 1.00 | 49.15 |
| 24655 | O | HOH | W | 494 | -39.111 | 10.312 | 9.299 | 1.00 | 46.57 |
| 24656 | O | HOH | W | 495 | -41.021 | -0.734 | 82.999 | 1.00 | 20.17 |
| 24657 | O | HOH | W | 496 | -104.466 | -16.137 | 89.994 | 1.00 | 29.53 |
| 24658 | O | HOH | W | 497 | -36.737 | -9.547 | 83.254 | 1.00 | 37.47 |
| 24659 | O | HOH | W | 498 | -118.554 | -7.113 | 14.480 | 1.00 | 47.45 |
| 24660 | O | HOH | W | 499 | -70.907 | -0.954 | 72.707 | 1.00 | 24.78 |
| 24661 | O | HOH | W | 500 | -4.235 | 14.513 | 79.624 | 1.00 | 45.58 |
| 24662 | O | HOH | W | 501 | -90.181 | -15.231 | 97.552 | 1.00 | 44.18 |
| 24663 | O | HOH | W | 502 | -76.085 | -25.892 | 68.489 | 1.00 | 33.89 |
| 24664 | O | HOH | W | 503 | -56.259 | 29.758 | 0.366 | 1.00 | 40.78 |
| 24665 | O | HOH | W | 504 | -59.106 | -24.485 | 86.538 | 1.00 | 34.68 |
| 24666 | O | HOH | W | 505 | -131.342 | -22.325 | 2.291 | 1.00 | 51.62 |
| 24667 | O | HOH | W | 506 | -42.230 | 0.815 | 61.632 | 1.00 | 46.95 |
| 24668 | O | HOH | W | 507 | -127.706 | -12.085 | 47.862 | 1.00 | 37.48 |
| 24669 | O | HOH | W | 508 | -114.497 | 13.233 | 17.975 | 1.00 | 37.97 |
| 24670 | O | HOH | W | 509 | -66.706 | -11.810 | 102.856 | 1.00 | 31.99 |
| 24671 | O | HOH | W | 510 | -90.702 | -5.881 | 10.694 | 1.00 | 36.99 |
| 24672 | O | HOH | W | 511 | -62.647 | -27.901 | 89.640 | 1.00 | 48.60 |
| 24673 | O | HOH | W | 512 | -65.472 | -1.994 | 94.134 | 1.00 | 32.99 |
| 24674 | O | HOH | W | 513 | -112.605 | -8.249 | 41.550 | 1.00 | 37.12 |

FIGURE 3 TR

| A | B | C | D | E | F | G | H | I | J |
|---|---|---|---|---|---|---|---|---|---|
| 24675 | O | HOH | W | 514 | -73.619 | -33.358 | 33.610 | 1.00 | 41.94 |
| 24676 | O | HOH | W | 515 | -110.412 | 14.693 | 25.941 | 1.00 | 34.88 |
| 24677 | O | HOH | W | 516 | -127.324 | -18.406 | 28.670 | 1.00 | 37.34 |
| 24678 | O | HOH | W | 517 | -92.072 | 11.787 | 30.309 | 1.00 | 38.67 |
| 24679 | O | HOH | W | 518 | -109.533 | 13.252 | 42.283 | 1.00 | 43.87 |
| 24680 | O | HOH | W | 519 | -96.204 | -22.107 | 73.396 | 1.00 | 40.68 |
| 24681 | O | HOH | W | 520 | -70.511 | 1.201 | -1.688 | 1.00 | 43.61 |
| 24682 | O | HOH | W | 521 | -85.422 | 2.630 | 44.519 | 1.00 | 32.34 |
| 24683 | O | HOH | W | 522 | -89.796 | -10.794 | 54.215 | 1.00 | 26.05 |
| 24684 | O | HOH | W | 523 | -52.252 | -9.767 | -7.150 | 1.00 | 49.69 |
| 24685 | O | HOH | W | 524 | -106.923 | 5.441 | 23.606 | 1.00 | 26.09 |
| 24686 | O | HOH | W | 525 | -70.347 | -0.883 | 1.599 | 1.00 | 33.59 |
| 24687 | O | HOH | W | 526 | -13.852 | 2.537 | 82.735 | 1.00 | 25.71 |
| 24688 | O | HOH | W | 527 | -69.051 | -23.282 | 65.079 | 1.00 | 57.35 |
| 24689 | O | HOH | W | 528 | -15.736 | -24.504 | 64.200 | 1.00 | 55.61 |
| 24690 | O | HOH | W | 529 | -83.151 | -7.369 | 35.490 | 1.00 | 23.48 |
| 24691 | O | HOH | W | 530 | -100.263 | -10.055 | 21.332 | 1.00 | 29.03 |
| 24692 | O | HOH | W | 531 | -84.428 | -15.621 | 36.762 | 1.00 | 30.89 |
| 24693 | O | HOH | W | 532 | -70.991 | -7.964 | 81.724 | 1.00 | 39.87 |
| 24694 | O | HOH | W | 533 | -29.394 | 7.216 | 88.291 | 1.00 | 30.48 |
| 24695 | O | HOH | W | 534 | -90.281 | 11.278 | 38.196 | 1.00 | 37.25 |
| 24696 | O | HOH | W | 535 | -94.916 | -15.110 | 93.283 | 1.00 | 40.87 |
| 24697 | O | HOH | W | 536 | -130.036 | 2.039 | 24.303 | 1.00 | 38.64 |
| 24698 | O | HOH | W | 537 | -89.215 | -0.334 | 55.254 | 1.00 | 42.59 |
| 24699 | O | HOH | W | 538 | -35.758 | -8.081 | 98.639 | 1.00 | 31.72 |
| 24700 | O | HOH | W | 539 | -45.965 | 18.844 | 63.606 | 1.00 | 40.59 |
| 24701 | O | HOH | W | 540 | -78.761 | 1.016 | 34.849 | 1.00 | 41.00 |
| 24702 | O | HOH | W | 541 | -36.879 | 12.264 | 110.190 | 1.00 | 40.17 |
| 24703 | O | HOH | W | 542 | -77.805 | 0.921 | 26.516 | 1.00 | 32.58 |
| 24704 | O | HOH | W | 543 | -51.413 | -5.972 | -11.885 | 1.00 | 55.29 |
| 24705 | O | HOH | W | 544 | -106.420 | 2.514 | 16.392 | 1.00 | 36.42 |
| 24706 | O | HOH | W | 545 | -23.108 | 12.851 | 58.766 | 1.00 | 29.95 |
| 24707 | O | HOH | W | 546 | -21.284 | -34.324 | 68.964 | 1.00 | 34.79 |
| 24708 | O | HOH | W | 547 | -115.873 | -5.662 | 40.853 | 1.00 | 33.89 |
| 24709 | O | HOH | W | 548 | -0.851 | -16.521 | 99.863 | 1.00 | 49.84 |
| 24710 | O | HOH | W | 549 | -125.713 | -12.405 | 49.897 | 1.00 | 29.65 |
| 24711 | O | HOH | W | 550 | -3.397 | 8.350 | 105.410 | 1.00 | 51.21 |
| 24712 | O | HOH | W | 551 | -50.077 | 28.979 | 29.651 | 1.00 | 56.94 |
| 24713 | O | HOH | W | 552 | -106.082 | -6.054 | 28.376 | 1.00 | 35.22 |
| 24714 | O | HOH | W | 553 | -28.271 | 8.354 | 109.470 | 1.00 | 41.13 |
| 24715 | O | HOH | W | 554 | -58.943 | 16.159 | 74.242 | 1.00 | 37.16 |
| 24716 | O | HOH | W | 555 | -110.483 | 11.853 | 49.320 | 1.00 | 38.28 |
| 24717 | O | HOH | W | 556 | -18.014 | -2.864 | 70.527 | 1.00 | 38.46 |
| 24718 | O | HOH | W | 557 | -99.379 | 8.025 | 74.323 | 1.00 | 57.48 |
| 24719 | O | HOH | W | 558 | -85.516 | 1.960 | 94.847 | 1.00 | 45.62 |
| 24720 | O | HOH | W | 559 | -42.903 | -15.679 | 81.707 | 1.00 | 33.93 |
| 24721 | O | HOH | W | 560 | -32.359 | -5.151 | 83.993 | 1.00 | 35.77 |
| 24722 | O | HOH | W | 561 | -124.818 | -32.042 | 29.691 | 1.00 | 41.61 |
| 24723 | O | HOH | W | 562 | -90.150 | -3.668 | 85.593 | 1.00 | 35.28 |
| 24724 | O | HOH | W | 563 | -45.572 | -2.969 | 63.207 | 1.00 | 35.77 |
| 24725 | O | HOH | W | 564 | -96.431 | 13.752 | 89.323 | 1.00 | 42.58 |

FIGURE 3 TS

| A | B | C | D | E | F | G | H | I | J |
|---|---|---|---|---|---|---|---|---|---|
| 24726 | O | HOH | W | 565 | -11.676 | -29.828 | 73.906 | 1.00 | 43.24 |
| 24727 | O | HOH | W | 566 | -60.965 | -6.210 | 58.917 | 1.00 | 34.35 |
| 24728 | O | HOH | W | 567 | -96.938 | -2.743 | 13.419 | 1.00 | 46.03 |
| 24729 | O | HOH | W | 568 | -80.239 | 7.394 | 76.783 | 1.00 | 38.39 |
| 24730 | O | HOH | W | 569 | -72.035 | 0.429 | 75.999 | 1.00 | 75.60 |
| 24731 | O | HOH | W | 570 | -31.996 | 2.959 | 71.230 | 1.00 | 35.73 |
| 24732 | O | HOH | W | 571 | -44.954 | -18.106 | 77.973 | 1.00 | 50.86 |
| 24733 | O | HOH | W | 572 | -74.601 | -20.462 | 112.735 | 1.00 | 37.33 |
| 24734 | O | HOH | W | 573 | -28.559 | 4.412 | 25.975 | 1.00 | 77.51 |
| 24735 | O | HOH | W | 574 | -77.646 | 3.638 | 70.347 | 1.00 | 23.91 |
| 24736 | O | HOH | W | 575 | -86.584 | 1.876 | 37.295 | 1.00 | 24.00 |
| 24737 | O | HOH | W | 576 | -89.287 | 0.922 | 78.981 | 1.00 | 45.18 |
| 24738 | O | HOH | W | 577 | -76.583 | -27.839 | 98.387 | 1.00 | 30.42 |
| 24739 | O | HOH | W | 578 | -25.542 | 4.659 | 45.516 | 1.00 | 51.05 |
| 24740 | O | HOH | W | 579 | -48.522 | -16.842 | 76.321 | 1.00 | 29.73 |
| 24741 | O | HOH | W | 580 | -53.049 | 17.187 | 76.352 | 1.00 | 37.90 |
| 24742 | O | HOH | W | 581 | -56.312 | 23.501 | 14.352 | 1.00 | 44.49 |
| 24743 | O | HOH | W | 582 | -30.649 | 1.419 | 106.878 | 1.00 | 28.92 |
| 24744 | O | HOH | W | 583 | -12.526 | -25.497 | 64.032 | 1.00 | 52.61 |
| 24745 | O | HOH | W | 584 | -28.109 | -6.042 | 112.750 | 1.00 | 38.18 |
| 24746 | O | HOH | W | 585 | -91.405 | 1.063 | 84.825 | 1.00 | 51.44 |
| 24747 | O | HOH | W | 586 | -32.497 | -0.763 | 55.223 | 1.00 | 48.90 |
| 24748 | O | HOH | W | 587 | -58.966 | -7.611 | 58.385 | 1.00 | 33.24 |
| 24749 | O | HOH | W | 588 | -69.798 | -31.805 | 89.201 | 1.00 | 36.09 |
| 24750 | O | HOH | W | 589 | -56.322 | -1.069 | 89.915 | 1.00 | 30.05 |
| 24751 | O | HOH | W | 590 | -129.557 | -26.903 | 49.312 | 1.00 | 50.67 |
| 24752 | O | HOH | W | 591 | -20.910 | -34.039 | 75.685 | 1.00 | 36.76 |
| 24753 | O | HOH | W | 592 | 6.899 | 4.829 | 91.810 | 1.00 | 41.51 |
| 24754 | O | HOH | W | 593 | -29.936 | -10.926 | 86.256 | 1.00 | 29.42 |
| 24755 | O | HOH | W | 594 | -99.662 | -26.933 | 76.105 | 1.00 | 40.22 |
| 24756 | O | HOH | W | 595 | -110.859 | -21.903 | 59.586 | 1.00 | 51.32 |
| 24757 | O | HOH | W | 596 | -46.604 | 28.337 | 23.745 | 1.00 | 45.45 |
| 24758 | O | HOH | W | 597 | -43.405 | -9.922 | 78.639 | 1.00 | 28.65 |
| 24759 | O | HOH | W | 598 | -110.346 | -15.092 | 42.303 | 1.00 | 44.63 |
| 24760 | O | HOH | W | 599 | -89.685 | -7.210 | 85.731 | 1.00 | 41.15 |
| 24761 | O | HOH | W | 600 | -89.542 | -3.812 | 79.240 | 1.00 | 35.87 |
| 24762 | O | HOH | W | 601 | -39.602 | -12.554 | 95.565 | 1.00 | 61.57 |
| 24763 | O | HOH | W | 602 | -51.722 | 6.270 | 32.500 | 1.00 | 43.89 |
| 24764 | O | HOH | W | 603 | -126.789 | 19.632 | 20.809 | 1.00 | 50.98 |
| 24765 | O | HOH | W | 604 | -106.338 | 20.953 | 20.414 | 1.00 | 55.07 |
| 24766 | O | HOH | W | 605 | -127.649 | -1.043 | 18.844 | 1.00 | 39.90 |
| 24767 | O | HOH | W | 606 | -58.955 | 3.126 | 98.167 | 1.00 | 38.14 |
| 24768 | O | HOH | W | 607 | -0.440 | 16.530 | 101.154 | 1.00 | 45.04 |
| 24769 | O | HOH | W | 608 | -84.789 | -35.574 | 95.888 | 1.00 | 42.44 |
| 24770 | O | HOH | W | 609 | -79.558 | 9.193 | 79.177 | 1.00 | 42.96 |
| 24771 | O | HOH | W | 610 | -146.635 | -4.053 | 40.233 | 1.00 | 44.67 |
| 24772 | O | HOH | W | 611 | -65.285 | 2.197 | 87.705 | 1.00 | 41.91 |
| 24773 | O | HOH | W | 612 | -119.625 | 0.329 | 36.959 | 1.00 | 28.70 |
| 24774 | O | HOH | W | 613 | -14.215 | 4.590 | 62.943 | 1.00 | 39.95 |
| 24775 | O | HOH | W | 614 | -73.078 | 19.826 | 10.249 | 1.00 | 61.27 |
| 24776 | O | HOH | W | 615 | -90.907 | -28.279 | 41.301 | 1.00 | 53.05 |

FIGURE 3 TT

| A | B | C | D | E | F | G | H | I | J |
|---|---|---|---|---|---|---|---|---|---|
| 24777 | O | HOH | W | 616 | -85.475 | 10.018 | 30.278 | 1.00 | 36.42 |
| 24778 | O | HOH | W | 617 | -28.134 | 4.099 | 73.726 | 1.00 | 34.99 |
| 24779 | O | HOH | W | 618 | -50.459 | 3.930 | 95.597 | 1.00 | 22.62 |
| 24780 | O | HOH | W | 619 | -114.113 | 26.603 | 29.382 | 1.00 | 57.35 |
| 24781 | O | HOH | W | 620 | -94.588 | -6.059 | 71.538 | 1.00 | 32.20 |
| 24782 | O | HOH | W | 621 | -82.752 | 13.037 | 62.201 | 1.00 | 30.48 |
| 24783 | O | HOH | W | 622 | -20.926 | -18.909 | 86.095 | 1.00 | 43.77 |
| 24784 | O | HOH | W | 623 | -17.970 | 26.324 | 71.920 | 1.00 | 46.83 |
| 24785 | O | HOH | W | 624 | -44.230 | -14.175 | 75.931 | 1.00 | 44.88 |
| 24786 | O | HOH | W | 625 | -52.806 | -16.627 | 92.395 | 1.00 | 42.51 |
| 24787 | O | HOH | W | 626 | -28.023 | 24.410 | 94.321 | 1.00 | 46.13 |
| 24788 | O | HOH | W | 627 | -120.609 | 28.705 | 21.356 | 1.00 | 63.07 |
| 24789 | O | HOH | W | 628 | -27.577 | 3.545 | 93.373 | 1.00 | 32.85 |
| 24790 | O | HOH | W | 629 | -26.459 | 7.138 | 85.369 | 1.00 | 41.44 |
| 24791 | O | HOH | W | 630 | 0.858 | -25.653 | 75.756 | 1.00 | 59.25 |
| 24792 | O | HOH | W | 631 | -55.884 | -21.067 | 81.597 | 1.00 | 37.94 |
| 24793 | O | HOH | W | 632 | -38.896 | 29.659 | 75.935 | 1.00 | 36.05 |
| 24794 | O | HOH | W | 633 | -84.032 | -15.701 | 93.299 | 1.00 | 32.55 |
| 24795 | O | HOH | W | 634 | -11.874 | -8.228 | 80.656 | 1.00 | 35.54 |
| 24796 | O | HOH | W | 635 | -75.434 | -30.259 | 103.613 | 1.00 | 38.35 |
| 24797 | O | HOH | W | 636 | -74.032 | -33.431 | 88.035 | 1.00 | 34.09 |
| 24798 | O | HOH | W | 637 | -33.404 | -22.472 | 87.965 | 1.00 | 40.49 |
| 24799 | O | HOH | W | 638 | -26.251 | 4.032 | 49.144 | 1.00 | 38.80 |
| 24800 | O | HOH | W | 639 | -108.473 | -41.961 | 44.645 | 1.00 | 66.35 |
| 24801 | O | HOH | W | 640 | -53.820 | 27.469 | 30.231 | 1.00 | 37.74 |
| 24802 | O | HOH | W | 641 | -87.240 | -17.214 | 35.785 | 1.00 | 38.56 |
| 24803 | O | HOH | W | 642 | -100.591 | -21.427 | 22.177 | 1.00 | 31.00 |
| 24804 | O | HOH | W | 643 | -87.956 | -22.906 | 109.676 | 1.00 | 36.03 |
| 24805 | O | HOH | W | 644 | -60.617 | 5.321 | 92.127 | 1.00 | 33.95 |
| 24806 | O | HOH | W | 645 | -24.513 | 5.013 | 38.231 | 1.00 | 47.59 |
| 24807 | O | HOH | W | 646 | -85.583 | -14.622 | 9.202 | 1.00 | 53.67 |
| 24808 | O | HOH | W | 647 | -46.151 | 23.506 | 78.086 | 1.00 | 36.42 |
| 24809 | O | HOH | W | 648 | -15.981 | -11.309 | 72.077 | 1.00 | 46.74 |
| 24810 | O | HOH | W | 649 | -59.801 | -4.749 | 52.778 | 1.00 | 43.98 |
| 24811 | O | HOH | W | 650 | -87.978 | -33.619 | 102.487 | 1.00 | 63.13 |
| 24812 | O | HOH | W | 651 | -11.361 | -7.818 | 97.878 | 1.00 | 37.51 |
| 24813 | O | HOH | W | 652 | -103.706 | -31.490 | 55.381 | 1.00 | 51.71 |
| 24814 | O | HOH | W | 653 | -101.710 | 13.544 | 98.967 | 1.00 | 74.04 |
| 24815 | O | HOH | W | 654 | -84.966 | -38.282 | 96.823 | 1.00 | 41.06 |
| 24816 | O | HOH | W | 655 | -78.472 | -6.737 | 96.586 | 1.00 | 40.72 |
| 24817 | O | HOH | W | 656 | -135.228 | 16.826 | 26.286 | 1.00 | 46.08 |
| 24818 | O | HOH | W | 657 | -31.731 | -0.414 | 108.386 | 1.00 | 30.69 |
| 24819 | O | HOH | W | 658 | -103.774 | -37.385 | 41.953 | 1.00 | 41.27 |
| 24820 | O | HOH | W | 659 | -77.960 | -28.996 | 100.030 | 1.00 | 30.02 |
| 24821 | O | HOH | W | 660 | -27.317 | 8.162 | 38.469 | 1.00 | 49.74 |
| 24822 | O | HOH | W | 661 | -93.111 | -26.539 | 30.845 | 1.00 | 34.26 |
| 24823 | O | HOH | W | 662 | -73.120 | -23.584 | 94.120 | 1.00 | 31.89 |
| 24824 | O | HOH | W | 663 | -19.345 | 2.573 | 76.802 | 1.00 | 47.99 |
| 24825 | O | HOH | W | 664 | -13.696 | -9.570 | 63.137 | 1.00 | 47.91 |
| 24826 | O | HOH | W | 665 | -50.334 | -10.047 | -5.032 | 1.00 | 55.35 |
| 24827 | O | HOH | W | 666 | -128.631 | -29.688 | 43.934 | 1.00 | 42.09 |

FIGURE 3 TU

| A | B | C | D | E | F | G | H | I | J |
|---|---|---|---|---|---|---|---|---|---|
| 24828 | O | HOH | W | 667 | 1.998 | 0.931 | 108.640 | 1.00 | 48.09 |
| 24829 | O | HOH | W | 668 | -81.286 | 2.028 | 48.266 | 1.00 | 37.17 |
| 24830 | O | HOH | W | 669 | -134.035 | 1.327 | 29.428 | 1.00 | 34.53 |
| 24831 | O | HOH | W | 670 | -73.399 | -1.276 | -4.487 | 1.00 | 46.20 |
| 24832 | O | HOH | W | 671 | -78.675 | 11.945 | 0.336 | 1.00 | 32.94 |
| 24833 | O | HOH | W | 672 | -109.777 | -18.384 | 39.041 | 1.00 | 40.69 |
| 24834 | O | HOH | W | 673 | -84.206 | -2.279 | 2.801 | 1.00 | 42.50 |
| 24835 | O | HOH | W | 674 | 0.084 | 2.944 | 107.715 | 1.00 | 57.24 |
| 24836 | O | HOH | W | 675 | -13.542 | -1.107 | 101.848 | 1.00 | 37.88 |
| 24837 | O | HOH | W | 676 | -52.682 | -4.437 | 23.976 | 1.00 | 42.73 |
| 24838 | O | HOH | W | 677 | -43.449 | -1.946 | 40.836 | 1.00 | 55.57 |
| 24839 | O | HOH | W | 678 | -31.729 | -25.134 | 88.262 | 1.00 | 42.24 |
| 24840 | O | HOH | W | 679 | -112.636 | 6.306 | 54.952 | 1.00 | 43.73 |
| 24841 | O | HOH | W | 680 | -81.712 | -14.940 | 93.610 | 1.00 | 41.18 |
| 24842 | O | HOH | W | 681 | -136.487 | 12.605 | 39.278 | 1.00 | 45.29 |
| 24843 | O | HOH | W | 682 | -52.351 | -17.893 | 71.059 | 1.00 | 34.40 |
| 24844 | O | HOH | W | 683 | -139.268 | 2.638 | 26.004 | 1.00 | 45.18 |
| 24845 | O | HOH | W | 684 | -51.980 | -5.968 | 99.949 | 1.00 | 34.09 |
| 24846 | O | HOH | W | 685 | -36.644 | -14.622 | 121.379 | 1.00 | 39.41 |
| 24847 | O | HOH | W | 686 | -66.136 | -27.337 | 92.346 | 1.00 | 36.84 |
| 24848 | O | HOH | W | 687 | -70.260 | 3.464 | 78.817 | 1.00 | 35.84 |
| 24849 | O | HOH | W | 688 | -115.054 | -14.780 | 38.963 | 1.00 | 51.42 |
| 24850 | O | HOH | W | 689 | -67.762 | 9.167 | 89.828 | 1.00 | 41.06 |
| 24851 | O | HOH | W | 690 | -76.205 | -19.114 | 45.994 | 1.00 | 42.06 |
| 24852 | O | HOH | W | 691 | -37.718 | -20.124 | 103.859 | 1.00 | 39.08 |
| 24853 | O | HOH | W | 692 | -87.393 | 11.388 | 31.561 | 1.00 | 31.42 |
| 24854 | O | HOH | W | 693 | -84.992 | 17.386 | 67.200 | 1.00 | 39.64 |
| 24855 | O | HOH | W | 694 | -8.499 | 9.237 | 107.160 | 1.00 | 47.35 |
| 24856 | O | HOH | W | 695 | -30.407 | 7.050 | 79.655 | 1.00 | 39.41 |
| 24857 | O | HOH | W | 696 | -66.142 | 18.511 | -3.885 | 1.00 | 53.83 |
| 24858 | O | HOH | W | 697 | -80.694 | 14.083 | 113.091 | 1.00 | 51.24 |
| 24859 | O | HOH | W | 698 | -55.899 | 10.509 | 71.595 | 1.00 | 29.76 |
| 24860 | O | HOH | W | 699 | -11.718 | 0.478 | 82.914 | 1.00 | 45.46 |
| 24861 | O | HOH | W | 700 | -144.057 | 9.602 | 12.139 | 1.00 | 51.96 |
| 24862 | O | HOH | W | 701 | -123.957 | -8.933 | 61.691 | 1.00 | 48.53 |
| 24863 | O | HOH | W | 702 | -109.921 | -40.014 | 51.188 | 1.00 | 51.41 |
| 24864 | O | HOH | W | 703 | -92.687 | 21.608 | 78.741 | 1.00 | 40.56 |
| 24865 | O | HOH | W | 704 | -122.013 | -5.018 | 53.612 | 1.00 | 38.40 |
| 24866 | O | HOH | W | 705 | -101.530 | -38.287 | 46.008 | 1.00 | 51.23 |
| 24867 | O | HOH | W | 706 | -27.454 | -12.186 | 5.720 | 1.00 | 51.47 |
| 24868 | O | HOH | W | 707 | -104.938 | -16.722 | 34.407 | 1.00 | 48.66 |
| 24869 | O | HOH | W | 708 | -26.418 | -14.256 | 81.064 | 1.00 | 46.60 |
| 24870 | O | HOH | W | 709 | -75.934 | -33.496 | 39.841 | 1.00 | 39.00 |
| 24871 | O | HOH | W | 710 | -64.836 | -17.007 | 63.963 | 1.00 | 43.38 |
| 24872 | O | HOH | W | 711 | -95.062 | -4.239 | 89.125 | 1.00 | 47.20 |
| 24873 | O | HOH | W | 712 | -62.552 | -12.299 | 31.956 | 1.00 | 45.49 |
| 24874 | O | HOH | W | 713 | -57.917 | -9.120 | 60.550 | 1.00 | 32.79 |
| 24875 | O | HOH | W | 714 | 1.093 | -5.090 | 108.362 | 1.00 | 45.91 |
| 24876 | O | HOH | W | 715 | -86.973 | -15.905 | 64.055 | 1.00 | 22.71 |
| 24877 | O | HOH | W | 716 | -15.870 | 6.898 | 59.992 | 1.00 | 42.80 |
| 24878 | O | HOH | W | 717 | -6.846 | 16.966 | 94.233 | 1.00 | 42.44 |

FIGURE 3 TV

| A | B | C | D | E | F | G | H | I | J |
|---|---|---|---|---|---|---|---|---|---|
| 24879 | O | HOH | W | 718 | -47.295 | -3.374 | 97.326 | 1.00 | 34.39 |
| 24880 | O | HOH | W | 719 | -18.800 | -5.666 | 55.781 | 1.00 | 37.89 |
| 24881 | O | HOH | W | 720 | -127.641 | 11.225 | 36.633 | 1.00 | 51.23 |
| 24882 | O | HOH | W | 721 | -38.590 | -16.155 | 110.676 | 1.00 | 51.60 |
| 24883 | O | HOH | W | 722 | -39.858 | -0.432 | 59.614 | 1.00 | 50.04 |
| 24884 | O | HOH | W | 723 | -74.314 | -15.994 | 44.707 | 1.00 | 55.03 |
| 24885 | O | HOH | W | 724 | -9.960 | 11.652 | 74.565 | 1.00 | 34.71 |
| 24886 | O | HOH | W | 725 | -107.173 | -17.836 | 33.511 | 1.00 | 38.18 |
| 24887 | O | HOH | W | 726 | -99.868 | -20.443 | 112.442 | 1.00 | 57.29 |
| 24888 | O | HOH | W | 727 | -106.173 | -14.260 | 36.662 | 1.00 | 35.53 |
| 24889 | O | HOH | W | 728 | -119.801 | -15.962 | 37.710 | 1.00 | 45.13 |
| 24890 | O | HOH | W | 729 | -61.611 | 18.551 | 65.794 | 1.00 | 50.39 |
| 24891 | O | HOH | W | 730 | 0.191 | -19.913 | 75.954 | 1.00 | 63.30 |
| 24892 | O | HOH | W | 731 | -94.042 | -24.147 | 61.231 | 1.00 | 53.28 |
| 24893 | O | HOH | W | 732 | -34.003 | -4.912 | 88.410 | 1.00 | 42.19 |
| 24894 | O | HOH | W | 733 | -77.079 | 15.127 | 76.919 | 1.00 | 37.67 |
| 24895 | O | HOH | W | 734 | -25.059 | -32.925 | 97.348 | 1.00 | 45.80 |
| 24896 | O | HOH | W | 735 | -76.693 | -30.862 | 101.322 | 1.00 | 45.34 |
| 24897 | O | HOH | W | 736 | -18.491 | 5.856 | 86.005 | 1.00 | 40.76 |
| 24898 | O | HOH | W | 737 | -108.341 | 2.644 | 7.825 | 1.00 | 62.16 |
| 24899 | O | HOH | W | 738 | -109.993 | 0.738 | 91.620 | 1.00 | 48.60 |
| 24900 | O | HOH | W | 739 | -121.856 | 1.010 | 35.985 | 1.00 | 27.42 |
| 24901 | O | HOH | W | 740 | -92.668 | -13.134 | 63.232 | 1.00 | 40.50 |
| 24902 | O | HOH | W | 741 | -106.480 | 1.723 | 60.044 | 1.00 | 49.04 |
| 24903 | O | HOH | W | 742 | -95.293 | 15.288 | 74.820 | 1.00 | 44.19 |
| 24904 | O | HOH | W | 743 | -113.061 | -15.331 | 19.125 | 1.00 | 51.17 |
| 24905 | O | HOH | W | 744 | -22.958 | -4.870 | 113.055 | 1.00 | 33.35 |
| 24906 | O | HOH | W | 745 | -89.973 | -2.565 | 11.396 | 1.00 | 42.40 |
| 24907 | O | HOH | W | 746 | -79.987 | 1.872 | 22.457 | 1.00 | 23.89 |
| 24908 | O | HOH | W | 747 | -110.181 | -15.573 | 44.474 | 1.00 | 54.44 |
| 24909 | O | HOH | W | 748 | -50.713 | -20.930 | 74.519 | 1.00 | 52.49 |
| 24910 | O | HOH | W | 749 | -73.658 | -24.704 | 68.371 | 1.00 | 34.36 |
| 24911 | O | HOH | W | 750 | -19.437 | -24.855 | 65.220 | 1.00 | 42.91 |
| 24912 | O | HOH | W | 751 | -91.197 | 3.357 | 89.107 | 1.00 | 39.95 |
| 24913 | O | HOH | W | 752 | -118.127 | -5.114 | 55.243 | 1.00 | 36.74 |
| 24914 | O | HOH | W | 753 | -27.171 | 8.632 | 70.946 | 1.00 | 33.58 |
| 24915 | O | HOH | W | 754 | -76.243 | -31.139 | 41.991 | 1.00 | 40.07 |
| 24916 | O | HOH | W | 755 | -39.397 | 8.095 | 56.388 | 1.00 | 56.79 |
| 24917 | O | HOH | W | 756 | -104.200 | -11.227 | 22.065 | 1.00 | 31.85 |
| 24918 | O | HOH | W | 757 | -3.554 | -9.778 | 111.146 | 1.00 | 32.29 |
| 24919 | O | HOH | W | 758 | -74.006 | 1.863 | 72.442 | 1.00 | 30.98 |
| 24920 | O | HOH | W | 759 | -54.405 | 33.925 | 16.062 | 1.00 | 47.19 |
| 24921 | O | HOH | W | 760 | -31.003 | 12.521 | 32.845 | 1.00 | 60.68 |
| 24922 | O | HOH | W | 761 | -78.699 | 2.560 | 97.572 | 1.00 | 46.62 |
| 24923 | O | HOH | W | 762 | -105.963 | -25.020 | 88.669 | 1.00 | 46.06 |
| 24924 | O | HOH | W | 763 | -137.286 | -10.278 | 49.944 | 1.00 | 48.34 |
| 24925 | O | HOH | W | 764 | -54.755 | 10.426 | 94.112 | 1.00 | 25.91 |
| 24926 | O | HOH | W | 765 | -18.367 | 21.230 | 89.592 | 1.00 | 43.75 |
| 24927 | O | HOH | W | 766 | -74.917 | -2.071 | 28.904 | 1.00 | 52.00 |
| 24928 | O | HOH | W | 767 | -75.041 | 1.291 | 37.100 | 1.00 | 48.59 |
| 24929 | O | HOH | W | 768 | -17.797 | 4.843 | 115.745 | 1.00 | 55.35 |

FIGURE 3 TW

| A | B | C | D | E | F | G | H | I | J |
|---|---|---|---|---|---|---|---|---|---|
| 24930 | O | HOH | W | 769 | -97.728 | 13.775 | 22.123 | 1.00 | 47.55 |
| 24931 | O | HOH | W | 770 | -50.927 | -21.661 | 72.392 | 1.00 | 47.05 |
| 24932 | O | HOH | W | 771 | -23.468 | -5.973 | 60.726 | 1.00 | 38.19 |
| 24933 | O | HOH | W | 772 | -123.433 | 0.675 | 33.643 | 1.00 | 45.22 |
| 24934 | O | HOH | W | 773 | -134.913 | -4.283 | 6.958 | 1.00 | 66.68 |
| 24935 | O | HOH | W | 774 | -127.179 | -32.498 | 40.865 | 1.00 | 43.85 |
| 24936 | O | HOH | W | 775 | -17.092 | 16.175 | 76.945 | 1.00 | 45.34 |
| 24937 | O | HOH | W | 776 | -56.377 | 21.256 | 87.338 | 1.00 | 43.00 |
| 24938 | O | HOH | W | 777 | -24.439 | -41.333 | 73.696 | 1.00 | 37.81 |
| 24939 | O | HOH | W | 778 | -73.463 | -30.933 | 86.327 | 1.00 | 33.66 |
| 24940 | O | HOH | W | 779 | -70.281 | -28.784 | 105.005 | 1.00 | 48.94 |
| 24941 | O | HOH | W | 780 | -93.115 | -0.754 | 94.056 | 1.00 | 38.17 |
| 24942 | O | HOH | W | 781 | -31.661 | 5.608 | 75.797 | 1.00 | 36.73 |
| 24943 | O | HOH | W | 782 | -63.429 | 12.258 | 19.239 | 1.00 | 53.46 |
| 24944 | O | HOH | W | 783 | -97.261 | 18.287 | 79.139 | 1.00 | 43.88 |
| 24945 | O | HOH | W | 784 | -71.802 | 2.252 | 35.264 | 1.00 | 40.62 |
| 24946 | O | HOH | W | 785 | -32.081 | 5.748 | 112.046 | 1.00 | 35.75 |
| 24947 | O | HOH | W | 786 | -139.810 | -29.449 | 22.820 | 1.00 | 67.64 |
| 24948 | O | HOH | W | 787 | -101.321 | -18.153 | 113.123 | 1.00 | 44.05 |
| 24949 | O | HOH | W | 788 | -40.760 | -5.156 | 64.114 | 1.00 | 35.05 |
| 24950 | O | HOH | W | 789 | -127.905 | 6.566 | -6.359 | 1.00 | 76.46 |
| 24951 | O | HOH | W | 790 | -59.533 | -26.677 | 90.322 | 1.00 | 34.19 |
| 24952 | O | HOH | W | 791 | -91.799 | 15.065 | 42.251 | 1.00 | 50.36 |
| 24953 | O | HOH | W | 792 | -49.855 | -0.090 | 102.999 | 1.00 | 40.48 |
| 24954 | O | HOH | W | 793 | -52.079 | -22.176 | 70.000 | 1.00 | 45.53 |
| 24955 | O | HOH | W | 794 | -23.004 | -8.624 | 61.058 | 1.00 | 39.84 |
| 24956 | O | HOH | W | 795 | -112.487 | 0.818 | 34.335 | 1.00 | 26.14 |
| 24957 | O | HOH | W | 796 | -140.190 | -8.344 | 52.019 | 1.00 | 56.96 |
| 24958 | O | HOH | W | 797 | -138.528 | -21.185 | 40.068 | 1.00 | 40.97 |
| 24959 | O | HOH | W | 798 | -49.656 | -23.877 | 72.094 | 1.00 | 42.03 |
| 24960 | O | HOH | W | 799 | -119.419 | -3.074 | 56.028 | 1.00 | 32.43 |
| 24961 | O | HOH | W | 800 | -32.508 | 4.018 | 77.065 | 1.00 | 45.49 |
| 24962 | O | HOH | W | 801 | -21.869 | -33.688 | 78.387 | 1.00 | 36.26 |
| 24963 | O | HOH | W | 802 | -60.786 | 17.372 | 73.043 | 1.00 | 51.46 |
| 24964 | O | HOH | W | 803 | -43.068 | 22.317 | 78.859 | 1.00 | 33.81 |
| 24965 | O | HOH | W | 804 | -35.321 | -9.622 | 96.413 | 1.00 | 44.83 |
| 24966 | O | HOH | W | 805 | -87.823 | -13.792 | 52.605 | 1.00 | 36.21 |
| 24967 | O | HOH | W | 806 | -106.590 | -15.054 | 38.915 | 1.00 | 45.67 |
| 24968 | O | HOH | W | 807 | -75.239 | 4.136 | 14.225 | 1.00 | 39.44 |
| 24969 | O | HOH | W | 808 | -18.177 | 13.978 | 67.515 | 1.00 | 58.12 |
| 24970 | O | HOH | W | 809 | 3.469 | -3.273 | 99.676 | 1.00 | 51.02 |
| 24971 | O | HOH | W | 810 | 7.206 | 16.098 | 84.307 | 1.00 | 51.62 |
| 24972 | O | HOH | W | 811 | -134.347 | -10.174 | 26.411 | 1.00 | 53.44 |
| 24973 | O | HOH | W | 812 | -45.444 | 8.802 | -3.602 | 1.00 | 46.81 |
| 24974 | O | HOH | W | 813 | -79.673 | -23.515 | 67.461 | 1.00 | 41.63 |
| 24975 | O | HOH | W | 814 | -45.083 | 23.312 | 87.433 | 1.00 | 52.94 |
| 24976 | O | HOH | W | 815 | -129.550 | -20.361 | -0.338 | 1.00 | 57.31 |
| 24977 | O | HOH | W | 816 | -7.865 | 0.634 | 71.449 | 1.00 | 33.31 |
| 24978 | O | HOH | W | 817 | -92.944 | 4.828 | 65.491 | 1.00 | 70.96 |
| 24979 | O | HOH | W | 818 | -108.298 | 15.720 | 25.185 | 1.00 | 31.68 |
| 24980 | O | HOH | W | 819 | -87.642 | -1.995 | 79.866 | 1.00 | 35.55 |

FIGURE 3 TX

| A | B | C | D | E | F | G | H | I | J |
|---|---|---|---|---|---|---|---|---|---|
| 24981 | O | HOH | W | 820 | -53.129 | -20.624 | 68.121 | 1.00 | 43.18 |
| 24982 | O | HOH | W | 821 | -46.676 | 8.360 | 99.471 | 1.00 | 53.54 |
| 24983 | O | HOH | W | 822 | -82.863 | 6.721 | 17.883 | 1.00 | 47.89 |
| 24984 | O | HOH | W | 823 | -73.495 | 24.656 | 60.445 | 1.00 | 61.86 |
| 24985 | O | HOH | W | 824 | -76.996 | 10.130 | 78.452 | 1.00 | 41.39 |
| 24986 | O | HOH | W | 825 | -72.752 | 8.722 | 115.201 | 1.00 | 41.56 |
| 24987 | O | HOH | W | 826 | -78.867 | -18.768 | 51.533 | 1.00 | 39.31 |
| 24988 | O | HOH | W | 827 | -64.933 | -6.274 | 14.923 | 1.00 | 37.00 |
| 24989 | O | HOH | W | 828 | -108.611 | -11.029 | 92.203 | 1.00 | 69.08 |
| 24990 | O | HOH | W | 829 | -60.555 | -17.772 | 32.874 | 1.00 | 36.50 |
| 24991 | O | HOH | W | 830 | -32.549 | 1.337 | 80.308 | 1.00 | 41.41 |
| 24992 | O | HOH | W | 831 | -113.710 | -25.902 | 32.716 | 1.00 | 49.83 |
| 24993 | O | HOH | W | 832 | -73.968 | -11.280 | 65.674 | 1.00 | 28.56 |
| 24994 | O | HOH | W | 833 | -42.493 | -11.248 | 66.170 | 1.00 | 40.32 |
| 24995 | O | HOH | W | 834 | -96.113 | -9.205 | 61.778 | 1.00 | 46.43 |
| 24996 | O | HOH | W | 835 | -65.152 | -23.619 | 25.368 | 1.00 | 34.26 |
| 24997 | O | HOH | W | 836 | -39.194 | -23.222 | 4.776 | 1.00 | 55.34 |
| 24998 | O | HOH | W | 837 | -36.238 | 2.699 | 9.340 | 1.00 | 62.31 |
| 24999 | O | HOH | W | 838 | -87.425 | 10.700 | 68.799 | 1.00 | 50.27 |
| 25000 | O | HOH | W | 839 | -66.256 | 2.049 | 96.807 | 1.00 | 35.47 |
| 25001 | O | HOH | W | 840 | -89.474 | -22.916 | 65.158 | 1.00 | 45.39 |
| 25002 | O | HOH | W | 841 | -27.948 | 6.269 | 81.342 | 1.00 | 43.67 |
| 25003 | O | HOH | W | 842 | -67.887 | 18.469 | 72.523 | 1.00 | 31.79 |
| 25004 | O | HOH | W | 843 | -120.465 | 7.696 | 45.684 | 1.00 | 38.52 |
| 25005 | O | HOH | W | 844 | -71.060 | -29.982 | 95.335 | 1.00 | 34.81 |
| 25006 | O | HOH | W | 845 | -44.934 | -9.421 | 59.671 | 1.00 | 50.92 |
| 25007 | O | HOH | W | 846 | -136.026 | -17.992 | 47.402 | 1.00 | 44.99 |
| 25008 | O | HOH | W | 847 | -107.725 | -11.728 | 40.368 | 1.00 | 34.40 |
| 25009 | O | HOH | W | 848 | -83.287 | 2.905 | 48.594 | 1.00 | 47.83 |
| 25010 | O | HOH | W | 849 | -95.896 | -8.203 | 11.164 | 1.00 | 46.14 |
| 25011 | O | HOH | W | 850 | -54.155 | 0.876 | -7.757 | 1.00 | 53.90 |
| 25012 | O | HOH | W | 851 | -9.851 | -32.699 | 93.749 | 1.00 | 51.16 |
| 25013 | O | HOH | W | 852 | -104.348 | 12.704 | 99.534 | 1.00 | 63.26 |
| 25014 | O | HOH | W | 853 | -87.422 | -4.549 | 113.517 | 1.00 | 48.99 |
| 25015 | O | HOH | W | 854 | -2.158 | -6.450 | 64.851 | 1.00 | 64.74 |
| 25016 | O | HOH | W | 855 | -18.363 | 6.447 | 83.250 | 1.00 | 46.03 |
| 25017 | O | HOH | W | 856 | -7.083 | 21.878 | 86.321 | 1.00 | 52.99 |
| 25018 | O | HOH | W | 857 | -141.370 | -13.344 | 38.226 | 1.00 | 47.02 |
| 25019 | O | HOH | W | 858 | -18.676 | 23.769 | 88.306 | 1.00 | 36.60 |
| 25020 | O | HOH | W | 859 | -3.232 | -4.531 | 62.613 | 1.00 | 53.78 |
| 25021 | O | HOH | W | 860 | -57.543 | 18.385 | 78.029 | 1.00 | 64.06 |
| 25022 | O | HOH | W | 861 | -107.309 | 16.795 | 22.170 | 1.00 | 48.15 |
| 25023 | O | HOH | W | 862 | -87.861 | 16.821 | 79.674 | 1.00 | 41.12 |
| 25024 | O | HOH | W | 863 | -85.693 | -7.204 | 77.392 | 1.00 | 33.57 |
| 25025 | O | HOH | W | 864 | -62.946 | 10.907 | 53.948 | 1.00 | 46.59 |
| 25026 | O | HOH | W | 865 | -36.829 | -32.372 | 89.420 | 1.00 | 59.66 |
| 25027 | O | HOH | W | 866 | -130.269 | -31.081 | 42.575 | 1.00 | 58.44 |
| 25028 | O | HOH | W | 867 | -84.428 | -28.018 | 97.755 | 1.00 | 45.22 |
| 25029 | O | HOH | W | 868 | -96.603 | -15.449 | 95.970 | 1.00 | 50.05 |
| 25030 | O | HOH | W | 869 | -84.309 | -3.507 | 53.654 | 1.00 | 52.40 |
| 25031 | O | HOH | W | 870 | -85.488 | -9.485 | 79.996 | 1.00 | 34.93 |

FIGURE 3 TY

| A | B | C | D | E | F | G | H | I | J |
|---|---|---|---|---|---|---|---|---|---|
| 25032 | O | HOH | W | 871 | -14.231 | -18.199 | 83.212 | 1.00 | 65.94 |
| 25033 | O | HOH | W | 872 | -41.546 | 6.888 | 12.114 | 1.00 | 57.29 |
| 25034 | O | HOH | W | 873 | -86.723 | -21.494 | 68.143 | 1.00 | 40.01 |
| 25035 | O | HOH | W | 874 | -13.321 | -0.552 | 86.509 | 1.00 | 46.17 |
| 25036 | O | HOH | W | 875 | -102.575 | 21.776 | 36.735 | 1.00 | 35.79 |
| 25037 | O | HOH | W | 876 | -21.013 | 12.921 | 96.471 | 1.00 | 41.55 |
| 25038 | O | HOH | W | 877 | -54.981 | -25.534 | 41.222 | 1.00 | 51.79 |
| 25039 | O | HOH | W | 878 | -84.913 | -24.984 | 68.610 | 1.00 | 38.41 |
| 25040 | O | HOH | W | 879 | -11.882 | -16.848 | 84.504 | 1.00 | 40.57 |
| 25041 | O | HOH | W | 880 | -65.886 | -14.938 | 26.150 | 1.00 | 39.74 |
| 25042 | O | HOH | W | 881 | -43.445 | -13.300 | 94.973 | 1.00 | 47.16 |
| 25043 | O | HOH | W | 882 | -86.575 | 3.908 | 39.235 | 1.00 | 35.06 |
| 25044 | O | HOH | W | 883 | -42.935 | -14.460 | 101.664 | 1.00 | 46.33 |
| 25045 | O | HOH | W | 884 | -102.862 | 4.225 | 59.670 | 1.00 | 63.42 |
| 25046 | O | HOH | W | 885 | -37.621 | 27.775 | 64.018 | 1.00 | 42.56 |
| 25047 | O | HOH | W | 886 | -123.005 | 4.627 | 56.211 | 1.00 | 44.90 |
| 25048 | O | HOH | W | 887 | -44.650 | -16.244 | 101.376 | 1.00 | 45.20 |
| 25049 | O | HOH | W | 888 | -8.862 | 20.234 | 91.644 | 1.00 | 38.30 |
| 25050 | O | HOH | W | 889 | -123.766 | -17.360 | 38.390 | 1.00 | 46.84 |
| 25051 | O | HOH | W | 890 | -103.157 | -0.399 | 72.982 | 1.00 | 46.81 |
| 25052 | O | HOH | W | 891 | -105.777 | 14.631 | 20.611 | 1.00 | 66.24 |
| 25053 | O | HOH | W | 892 | -24.023 | 9.502 | 65.466 | 1.00 | 46.04 |
| 25054 | O | HOH | W | 893 | -28.285 | -3.489 | 113.000 | 1.00 | 45.11 |
| 25055 | O | HOH | W | 894 | -25.898 | 2.662 | 91.394 | 1.00 | 37.86 |
| 25056 | O | HOH | W | 895 | -76.562 | -34.369 | 33.493 | 1.00 | 57.61 |
| 25057 | O | HOH | W | 896 | -22.712 | 3.824 | 76.835 | 1.00 | 44.17 |
| 25058 | O | HOH | W | 897 | -48.565 | -19.330 | 89.549 | 1.00 | 35.12 |
| 25059 | O | HOH | W | 898 | -63.475 | -15.102 | 11.755 | 1.00 | 40.72 |
| 25060 | O | HOH | W | 899 | -30.645 | 31.637 | 80.113 | 1.00 | 48.97 |
| 25061 | O | HOH | W | 900 | -25.243 | 4.993 | 98.133 | 1.00 | 36.36 |
| 25062 | O | HOH | W | 901 | -87.702 | -35.472 | 100.703 | 1.00 | 48.87 |
| 25063 | O | HOH | W | 902 | -93.587 | -10.177 | 61.052 | 1.00 | 58.57 |
| 25064 | O | HOH | W | 903 | -97.756 | 16.026 | 29.825 | 1.00 | 48.85 |
| 25065 | O | HOH | W | 904 | -20.115 | -3.404 | 74.768 | 1.00 | 44.90 |
| 25066 | O | HOH | W | 905 | -15.016 | 18.829 | 99.081 | 1.00 | 58.91 |
| 25067 | O | HOH | W | 906 | -91.419 | -31.458 | 38.390 | 1.00 | 39.28 |
| 25068 | O | HOH | W | 907 | -85.162 | -30.223 | 38.252 | 1.00 | 60.78 |
| 25069 | O | HOH | W | 908 | -31.527 | 17.665 | 31.472 | 1.00 | 60.01 |
| 25070 | O | HOH | W | 909 | -77.299 | -14.987 | 49.080 | 1.00 | 41.20 |
| 25071 | O | HOH | W | 910 | -70.003 | 4.960 | 113.532 | 1.00 | 54.43 |
| 25072 | O | HOH | W | 911 | -70.496 | 5.623 | 116.492 | 1.00 | 44.56 |
| 25073 | O | HOH | W | 912 | -72.335 | 7.240 | 119.566 | 1.00 | 52.72 |
| 25074 | O | HOH | W | 913 | -67.577 | 8.642 | 116.472 | 1.00 | 53.27 |
| 25075 | O | HOH | W | 914 | -102.314 | 24.937 | 12.816 | 1.00 | 56.03 |
| 25076 | O | HOH | W | 915 | -97.900 | 28.228 | 14.950 | 1.00 | 44.18 |
| 25077 | O | HOH | W | 916 | -110.808 | 20.471 | 46.849 | 1.00 | 72.10 |

FIGURE 3 TZ

| A | B | C | D | E | F | G | H | I | J |
|---|---|---|---|---|---|---|---|---|---|
| 25078 | O | HOH | W | 917 | -38.511 | -5.038 | 127.327 | 1.00 | 64.38 |
| 25079 | O | HOH | W | 918 | -110.204 | -15.447 | -2.899 | 1.00 | 67.44 |
| 25080 | O | HOH | W | 919 | 7.037 | -20.430 | 68.754 | 1.00 | 55.24 |
| 25081 | O | HOH | W | 920 | -110.374 | 13.235 | 102.576 | 1.00 | 57.48 |
| 25082 | O | HOH | W | 921 | -107.848 | 12.664 | 99.863 | 1.00 | 52.86 |
| 25083 | O | HOH | W | 922 | -105.429 | 10.964 | 104.942 | 1.00 | 64.95 |
| 25084 | O | HOH | W | 923 | -107.566 | 15.872 | 103.930 | 1.00 | 49.98 | ns
CRYSTALLIZATION OF DIPEPTIDYL PEPTIDASE IV (DPPIV)

RELATED APPLICATION

This application claims the benefit of U.S. Provisional Application No. 60/409,206, filed Sep. 9, 2002, which is incorporated herein by reference.

FIELD OF THE INVENTION

The present invention relates to a member of the S9 family of human proteases known as Dipeptidyl Peptidases (DPP) and more specifically to a particular dipeptidyl peptidase known as dipeptidyl peptidase IV (DPPIV). Provided is DPPIV in crystalline form, methods of forming crystals comprising DPPIV, methods of using crystals comprising DPPIV, a crystal structure of DPPIV, and methods of using the crystal structure.

BACKGROUND OF THE INVENTION

A general approach to designing inhibitors that are selective for a given protein is to determine how a putative inhibitor interacts with a three dimensional structure of that protein. For this reason it is useful to obtain the protein in crystalline form and perform X-ray diffraction techniques to determine the protein's three-dimensional structure coordinates. Various methods for preparing crystalline proteins are known in the art.

Once protein crystals are produced, crystallographic data can be generated using the crystals to provide useful structural information that assists in the design of small molecules that bind to the active site of the protein and inhibit the protein's activity in vivo. If the protein is crystallized as a complex with a ligand, one can determine both the shape of the protein's binding pocket when bound to the ligand, as well as the amino acid residues that are capable of close contact with the ligand. By knowing the shape and amino acid residues comprised in the binding pocket, one may design new ligands that will interact favorably with the protein. With such structural information, available computational methods may be used to predict how strong the ligand binding interaction will be. Such methods aid in the design of inhibitors that bind strongly, as well as selectively to the protein.

SUMMARY OF THE INVENTION

The present invention is directed to crystals comprising DPPIV and particularly crystals comprising DPPIV that have sufficient size and quality to obtain useful information about the structural properties of DPPIV and molecules or complexes that may associate with DPPIV.

In one embodiment, a composition is provided that comprises a protein in crystalline form wherein the protein has 65%, 70%, 80%, 90%, 95% or greater identity with residues 13-740 of SEQ ID NO:3.

In one variation, the protein has activity characteristic of DPPIV. For example, the protein may optionally be inhibited by inhibitors of wild type DPPIV.

The protein may also diffract X-rays for a determination of structure coordinates to a resolution of 4 Å, 3 Å, 2.5 Å, 2 Å or less.

In one variation, the protein crystal has a crystal lattice in a $P2_1$ space group. The protein crystal may also have a crystal lattice having unit cell dimensions, +/−5%, of a=121.53 Å b=124.11 Å and c=144.42 Å, $\alpha=\gamma=90°$, $\beta=114.6°$.

The present invention is also directed to crystallizing DPPIV. The present invention is also directed to the conditions useful for crystallizing DPPIV. It should be recognized that a wide variety of crystallization methods can be used in combination with the crystallization conditions to form crystals comprising DPPIV including, but not limited to, vapor diffusion, batch, and dialysis.

In one embodiment, a method is provided for forming crystals of a protein comprising: forming a crystallization volume comprising: a protein that has at least 65%, 70%, 80%, 90%, 95% identity with residues 13-740 of SEQ ID NO:3 in a concentration between 1 mg/ml and 50 mg/ml; 5-50% w/v of precipitant wherein the precipitant comprises one or more members of the group consisting of PEG MME having a molecular weight range between 300-10000, and PEG having a molecular weight range between 100-10000; optionally 0.05 to 0.8M additives wherein the additives comprises sarcosine or 0.5 to 25% additives wherein the additives comprises xylitrol; and wherein the crystallization volume has a pH between pH 5 and pH 9; and storing the crystallization volume under conditions suitable for crystal formation. The method optionally further comprises using 0.05-0.2M buffers selected from the group consisting of tris-HCl, bicine and combinations thereof. The method also optionally further includes performing the crystallization at a temperature between 1° C.-25° C.

The method may optionally further comprise forming a protein crystal that has a crystal lattice in a $P2_1$ space group. The method also optionally further comprises forming a protein crystal that has a crystal lattice having unit cell dimensions, +/−5%, of a=121.53 Å b=1124.11 Å and c=144.42 Å, $\alpha=\gamma=90°$, $\beta=114.6°$. The invention also relates to protein crystals formed by these methods.

The present invention is also directed to structure coordinates for DPPIV as well as structure coordinates that are comparatively similar to these structure coordinates. It is noted that these comparatively similar structure coordinates may encompass proteins with similar sequences and/or structures, such as other members of the S9 protease family. For example, machine-readable data storage media is provided having data storage material encoded with machine-readable data that comprises structure coordinates that are comparatively similar to the structure coordinates of DPPIV. The present invention is also directed to a machine readable data storage medium having data storage material encoded with machine readable data, which, when read by an appropriate machine, can display a three dimensional representation of all or a portion of a structure of DPPIV or a model that is comparatively similar to the structure of all or a portion of DPPIV.

In one embodiment, machine readable data storage medium is provided having data storage material encoded with machine readable data, the machine readable data comprising: structure coordinates that have a root mean square deviation of alpha-carbon atoms of less than 3 Å when superimposed on alpha-carbon atoms positions of corresponding atomic coordinates of FIG. 3, the root mean square deviation being calculated based only on those alpha-carbon atoms of amino acid residues in the structure coordinates that are also present in residues 13-740 of SEQ ID NO:3.

In another embodiment, machine readable data storage medium is provided having data storage material encoded with machine readable data, the machine readable data comprising: structure coordinates that have a root mean square deviation of alpha-carbon atoms of less than 3 Å when superimposed on alpha-carbon atom positions of corresponding atomic coordinates of FIG. 3, the root mean square deviation being calculated based only on those alpha-carbon atoms of amino acid residues in the structure coordinates that are also present in Tables 1, 2, 3 and/or 4.

It is noted in regard to these embodiments that the root mean square deviation calculation may optionally be based on a comparison of main-chain atoms, non-hydrogen atoms or a comparison of all atoms where the same type of amino acid residue is present. Also, the root mean square deviation of alpha-carbon atoms, main-chain atoms, non-hydrogen atoms or all atoms may optionally be less than 2.7 Å, 2.5 Å, 2.0 Å, 1.5 Å, 1 Å, 0.5 Å, or less.

The present invention is also directed to a three-dimensional structure of all or a portion of DPPIV. This three-dimensional structure may be used to identify binding sites, to provide mutants having desirable binding properties, and ultimately, to design, characterize, or identify ligands capable of interacting with DPPIV. Ligands that interact with DPPIV may be any type of atom, compound, protein or chemical group that binds to or otherwise associates with the protein. Examples of types of ligands include natural substrates for DPPIV, inhibitors of DPPIV, and heavy atoms.

In one embodiment, a method is provided for displaying, a three dimensional representation of a structure of a protein comprising: taking machine readable data comprising structure coordinates that have a root mean square deviation of alpha-carbon atoms of less than 3 Å when superimposed on alpha-carbon atom positions of corresponding atomic coordinates of FIG. 3., the root mean square deviation being calculated based only on those alpha-carbon atoms of amino acid residues in the structure coordinates that are also present in residues shown in Tables 1, 2, 3 and/or 4 or residues 13-740 of SEQ D NO:3; computing a three dimensional representation of a structure based on the structure coordinates; and displaying the three dimensional representation.

In another embodiment, a method is provided for displaying a three dimensional representation of a structure of a protein comprising: displaying a computer model for a protein binding pocket, at least a portion of the computer model having a surface contour that has a root mean square deviation of less than 3 Å when superimposed on a surface contour defined by atomic coordinates of FIG. 3, the root mean square deviation being calculated based only on alpha-carbon atoms in the structure coordinates of FIG. 3 that are present in residues shown in Tables 1, 2, 3 and/or 4 or residues 13-740 of SEQ ID NO:3.

It is again noted in regard to these embodiments that the root mean square deviation calculation may optionally be based on a comparison of main-chain atoms, non-hydrogen atoms or a comparison of all atoms where the same type of amino acid residue is present. Also, the root mean square deviation of alpha-carbon atoms, non-hydrogen atoms or all atoms may optionally be less than 2.7 Å, 2.5 Å, 2.0 Å, 1.5 Å, 1 Å, 0.5 Å, or less.

The present invention is also directed to a method for solving a three-dimensional crystal structure of a target protein using the structure of DPPIV.

In one embodiment, a computational method is provided comprising taking machine readable data comprising structure coordinates that have a root mean square deviation of alpha-carbon atoms of less than 3 Å when superimposed on alpha-carbon atom positions of corresponding atomic coordinates of FIG. 3, the root mean square deviation being calculated based only on those alpha-carbon atoms of amino acid residues in the structure coordinates that are also present in residues shown in Tables 1, 2, 3 and/or 4 or residues 13-740 of SEQ ID NO:3; computing phases based on the structural coordinates; computing an electron density map based on the computed phases; and determining a three-dimensional crystal structure based on the computed electron density map.

In another embodiment, a computational method is provided comprising: taking an X-ray diffraction pattern of a crystal of the target protein; and computing a three-dimensional electron density map from the X-ray diffraction pattern by molecular replacement, wherein structure coordinates used as a molecular replacement model comprise structure coordinates that have a root mean square deviation of alpha-carbon atoms of less than 3 Å when superimposed on alpha-carbon atom positions of corresponding atomic coordinates of FIG. 3, the root mean square deviation being calculated based only on those alpha-carbon atoms of amino acid residues in the structure coordinates that are also present in residues shown in Tables 1, 2, 3 and/or 4 or residues 13-740 of SEQ ID NO:3. This method may optionally further comprise determining a three-dimensional crystal structure based upon the computed three-dimensional electron density map.

It is again noted in regard to these embodiments that the root mean square deviation calculation may optionally be based on a comparison of main-chain atoms, non-hydrogen atoms or a comparison of all atoms where the same type of amino acid residue is present. Also, the root mean square deviation of alpha-carbon atoms, main-chain atoms, non-hydrogen atoms or all atoms may optionally be less than 2.7 Å, 2.5 Å, 2.0 Å, 1.5 Å, 1 Å, 0.5 Å, or less.

The present invention is also directed to using a crystal structure of DPPIV, in particular the structure coordinates of DPPIV and the surface contour defined by them, in methods for screening, designing, or optimizing molecules or other chemical entities that interact with and preferably inhibit DPPIV.

One skilled in the art will appreciate the numerous uses of the inventions described herein, particularly in the areas of drug design, screening and optimization of drug candidates, as well as in determining additional unknown crystal structures. For example, a further aspect of the present invention relates to using a three-dimensional crystal structure of all or a portion of DPPIV and/or its structure coordinates to evaluate the ability of entities to associate with DPPIV. The entities may be any entity that may function as a ligand and thus may be any type of atom, compound, protein (such as antibodies) or chemical group that can bind to or otherwise associate with a protein.

In one embodiment, a method is provided for evaluating a potential of an entity to associate with a protein comprising: creating a computer model of a protein structure using structure coordinates that comprise structure coordinates that have a root mean square deviation of alpha-carbon atoms of less than 3 Å when superimposed on alpha-carbon atom positions of corresponding atomic coordinates of FIG. 3, the root mean square deviation being calculated based only on those alpha-carbon atoms of amino acid residues in the structure coordinates that are also present in residues shown in Tables 1, 2, 3 and/or 4 or residues 13-740 of SEQ ID NO:3. 1; performing a fitting operation between the entity and the computer model; and analyzing results of the fitting operation to quantify an association between the entity and the model.

In another embodiment, a method is provided for evaluating a potential of an entity to associate with a protein comprising: computing a computer model for a protein binding pocket, at least a portion of the computer model having a surface contour that has a root mean square deviation of less than 3 Å when superimposed on a surface contour defined by atomic coordinates of FIG. 3, the root mean square deviation being calculated based only on alpha-carbon atoms in the structure coordinates that are present in residues shown in Tables 1, 2, 3 and/or 4 or residues 13-740 of SEQ ID NO:3; evaluating a potential of an entity to associate with the surface contour by performing a fitting operation between the entity and the surface contour; and analyzing results of the fitting operation to quantify an association between the entity and the computer model.

In another embodiment, a method is provided for identifying entities that can associate with a protein comprising: generating a three-dimensional structure of a protein using structure coordinates that comprise structure coordinates that have a root mean square deviation of alpha-carbon atoms of less than 3 Å when superimposed on alpha-carbon atom positions of corresponding atomic coordinates of FIG. 3 the root mean square deviation being calculated based only on those alpha-carbon atoms of amino acid residues in the structure coordinates that are also present in residues shown in Tables 1, 2, 3 and/or 4 or residues 13-740 of SEQ ID NO:3; employing the three-dimensional structure to design or select an entity that can associate with the protein; and contacting the entity with a protein having at least 65% identity with residues 13-740 of SEQ ID NO:3.

In another embodiment, a method is provided for identifying entities that can associate with a protein comprising: computing a computer model for a protein binding pocket, at least a portion of the computer model having a surface contour that has a root mean square deviation of less than 3 Å when superimposed on a surface contour defined by atomic coordinates of FIG. 3, the root mean square deviation being calculated based only on alpha-carbon atoms in the structure coordinates that are present in residues shown in Tables 1, 2, 3 and/or 4 or residues 13-740 of SEQ ID NO:3; employing the computer model to design or select an entity that can associate with the protein; and contacting the entity with a protein having at least 65%, 70, 80, 90, 95% identity with residues 13-740 of SEQ ID NO:3.

In another embodiment, a method is provided for evaluating the ability of an entity to associate with a protein, the method comprising: constructing a computer model defined by structure coordinates that comprise structure coordinates that have a root mean square deviation of alpha-carbon atoms of less than 3 Å when superimposed on alpha-carbon atom positions of corresponding atomic coordinates of FIG. 3, the root mean square deviation being calculated only on those alpha-carbon atoms of amino acid residues in the structure coordinates that are also present in residues shown in Tables 1, 2, 3 and/or 4 or residues 13-740 of SEQ ID NO:3; selecting an entity to be evaluated by a method selected from the group consisting of (i) assembling molecular fragments into the entity (ii) selecting an entity from a small molecule database, (iii) de novo ligand design of the entity, and (iv) modifying a known ligand for DPPIV, or a portion thereof; performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the binding pocket.

In another embodiment, a method for evaluating the ability of an entity to associate with a protein, the method comprising: computing a computer model for a protein binding pocket, at least a portion of the computer model having a surface contour that has a root mean square deviation of less than 3 Å when superimposed on a surface contour defined by atomic coordinates of FIG. 3, the root mean square deviation being calculated based only on alpha-carbon atoms in the structure coordinates that are present in residues shown in Tables 1, 2, 3 and/or 4 or residues 13-740 of SEQ ID NO:3: selecting an entity to be evaluated by a method selected from the group consisting of (i) assembling molecular fragments into the entity, (ii) selecting an entity from a small molecule database, (iii) de novo ligand design of the entity, and (iv) modifying a known ligand for an DPPIV, or a portion thereof; performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the said binding pocket.

It is again noted in regard to these embodiments that the root mean square deviation calculation may optionally be based on a comparison of main-chain atoms, non-hydrogen atoms or a comparison of all atoms where the same type of amino acid residue is present. Also, the root mean square deviation of alpha-carbon atoms, non-hydrogen atoms or all atoms may optionally be less than 2.7 Å, 2.5 Å, 2.0 Å, 1.5 Å, 1 Å, 0.5 Å, or less.

Also in regard to each of these embodiments, the protein may optionally have activity characteristic of DPPIV. For example, the protein may optionally be inhibited by inhibitors of wild type DPPIV.

In another embodiment, a method is provided for identifying an entity that associates with a protein comprising: taking structure coordinates from diffraction data obtained from a crystal of a protein that has at least 65%, 70%, 80%, 90%, 95% or more identity with the residues 13-740 of SEQ ID NO:3 and performing rational drug design using a three dimensional structure that is based on the obtained structure coordinates. The protein crystals may optionally have a crystal lattice having unit cell dimensions, +/−5%, of a=121.53 Å b=124.11 Å and c=144.42 Å, α=γ=90°, β=114.6°). The method may optionally further comprise selecting one or more entities based on the rational drug design and contacting the selected entities with the protein. The method may also optionally further comprise measuring an activity of the protein when contacted with the one or more entities. The method also may optionally further comprise comparing activity of the protein in a presence of and in the absence of the one or more entities; and selecting entities where activity of the protein changes depending whether a particular entity is present. The method also may a optionally further comprise contacting cells expressing the protein with the one or more entities and detecting a change in a phenotype of the cells when a particular entity is present.

BRIEF DESCRIPTION OF THE FIGURES

FIG. 1 illustrates SEQ. ID Nos. 1, 2 and 3 referred to in this application.

FIG. 3 lists a set of atomic structure coordinates for DPPIV (SEQ ID NO:3 as derived by X-ray crystallography from a crystal that comprises the protein. The following abbreviations are used in FIG. 3: "X, Y, Z" crystallographically define the atomic position of the element measured; "B" is a thermal factor that measures movement of the atom around its atomic center: "Occ" is an occupancy factor that refers to the fraction of the molecules in which each atom occupies the position specified by the coordinates (a value of "1" indicates that each atom has the same conformation, i.e., the same position, in all molecules of the crystal). "NAG" stands for N-Acetylglucosamine.

DETAILED DESCRIPTION OF THE INVENTION

Figure 2:
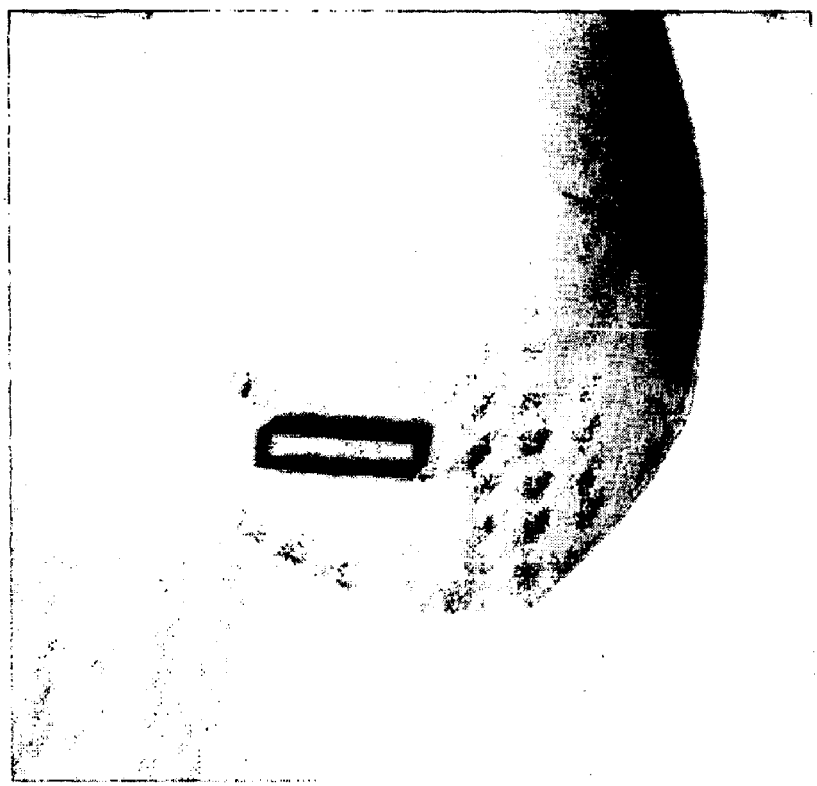
FIG. 2 illustrates a crystal of DPPIV complex.

The present invention relates to a member of the S9 family of human proteases known as dipeptidyl peptidase IV (DPPIV) (SEQ ID NO:1) More specifically, the present invention relates to DPPIV in crystalline form, methods of forming crystals comprising DPPIV, methods of using crystals comprising DPPIV, structure coordinates and a crystal structure of DPPIV, and methods of using the structure coordinates and crystal structure.

In describing protein structure and function herein, reference is made to amino acids comprising the protein. The amino acids may also be referred to by their conventional abbreviations; A=Ala=Alanine; T=Thr=Threonine; V=Val=Valine; C=Cys=Cysteine; L=Leu=Leucine; Y=Tyr=Tyrosine; I=Ile=Isoleucine; N=Asn=Asparagine; P=Pro=Proline; Q=Gln=Glutamine; F=Phe=Phenylalanine; D=Asp=Aspartic Acid; W=Trp=Tryptophan; E=Glu=Glutamic Acid; M=Met=Methionine; K=Lys=Lysine; G=Gly=Glycine; R=Arg=Arginine; S=Ser=Serine; and H=His=Histidine.

1. DPPIV

Dipeptidyl Peptidase IV (DPPIV) (SEQ ID NO:1) is a serine protease of Clan SC family S9. DPPIV is a 240 kDa homodimeric, multi-functional type-II membrane bound glycoprotein, widely distributed in all mammalian tissues, but highly expressed in kidney, liver and endothelium. DPPIV is also known as DPP4, CD26, adenosine deaminase complexing protein 2 or adenosine deaminase binding protein (ADAbp). DPPIV consists of a short cytoplasmic domain of six amino acids, followed by a hydrophobic transmembrane domain (amino acids 7-28) and an extracellular sequence of 739 amino acids.

DPPIV is a highly specific aminopeptidase and releases dipeptides from the amino terminus of peptides with a Pro or Ala in the penultimate position. N-terminal degradation of the substrate peptides may result in the activation, inactivation or modulation of their activity. Besides its well-known exopeptidase activity, DPPIV also exhibits endopeptidase activity towards denatured collagen. Expression of DPPIV is tightly associated with cell adhesion and is a co-stimulant during T-cell activation and proliferation.

The nature of its substrates, together with its regulated expression and non-enzymatic interactions characterize active participation of DPPIV in the immune, nerve and endocrine networks in human physiology. Among the substrates of DPPIV are glucagon-like peptide 1 (GLP-1) and glucose-dependent insulinotropic polypeptide (GIP), two hormones important for glucose regulation. Degradation and concomitantly inactivation of GLP-1 and GIP by DPPIV reduces insulin secretion.

It should be understood that the methods and compositions provided relating to DPPIV are not intended to be limited to the wild type, full length form of DPPIV. Instead, the present invention also relates to fragments and variants of DPPIV as described herein. Further, the present invention has applicability to other S9 proteases whose sequence and/or structure are comparatively similar to DPPIV.

In one embodiment, DPPIV comprises the wild-type form of full length DPPIV, set forth herein as SEQ. ID No. 1 (GenBank Accession Number NM_001935; "Dipeptidyl peptidase IV (CD 26) gene expression in enterocyte-like colon cancer cell lines HT-29 and Caco-2. Cloning of the complete human coding sequence and changes of dipeptidyl peptidase IV mRNA levels during cell differentiation", Darmoul, D., Lacasa, M., Baricault, L., Marguet, D., Sapin, C., Trotot, P., Barbat, A. and Trugnan, G., *J. Biol. Chem.* 267 (7), 4824-4833, 1992.

In another embodiment, DPPIV comprises residues 13-740 of SEQ ID NO:3 which comprises the active site domain of wild-type DPPIV that is represented in the set of structural coordinates shown in FIG. 3.

It should be recognized that the invention may be readily extended to various variants of wild-type DPPIV and variants of fragments thereof. In another embodiment, DPPIV comprises a sequence that has at least 65% identity, preferably at least 70%, 80%, 90%, 95% or higher identity with SEQ. ID No. 1.

It is also noted that the above sequences of DPPIV are also intended to encompass isoforms, mutants and fusion proteins of these sequences. An example of a fusion protein is provided by SEQ. ID No. 3, which includes a 12 residue N-terminal tag (6 residues of which are histidine) that may be used to facilitate purification of the protein.

With the crystal structure provided herein, where amino acid residues are positioned in the structure are now known. As a result, the impact of different substitutions can be more easily predicted and understood.

For example, based on the crystal structure, applicants have determined that the DPPIV amino acids shown in Table 1 encompass a 4-Angstrom radius around the DPPIV active site and thus likely to interact with any active site inhibitor of DPPIV. Applicants have also determined that the amino acids of Table 2 encompass a 7-Angstrom radius around the DPPIV active site. Further it has been determined that the amino acids of Table 3 encompass a 10-Angstrom radius around the DPPIV active site. It is noted that there are four different DPPIV molecules in the asymmetric unit, referred to as chains A, B, C and D. As a result, four sets of structure coordinates were obtained for each amino acid. There are two dimers formed in the asymmetric unit; one dimer is formed between molecules A and B and the other with molecules C and D. Applicants have also determined that amino acids of Table 4 encompass a 5-Angstrom radius around the DPPIV amino acids that interact at the AB and CD dimerization interfaces. The A, B, C and D sets of structural coordinates appear in FIG. 3. It is noted that the sequence and structure of the residues in the active site and dimerization interface may also be conserved and hence pertinent to other S9 proteases.

One or more of the sets of amino acids set forth in the tables is preferably conserved in a variant of DPPIV. Hence, DPPIV may optionally comprise a sequence that has at least 65% identity, preferably at least 70%, 80%, 90%, 95% or higher identity with any one of the above sequences (e.g., all of SEQ ID NO:3 or residues 13-740 of SEQ ID NO:3) where at least the residues shown in tables 1, 2, 3 and/or 4 are conserved with the exception of 0, 2, 3 or 4 residues. It should be recognized that one might optionally vary some of the binding site residues in order to determine the effect such changes have on structure or activity.

TABLE 1

Amino Acids encompassed by a 4-Angstrom radius around the DPPIV active site (SEQ ID NO:3).

| ARG | 99 | TYR | 521 | TYR | 640 |
|-----|-----|-----|-----|-----|-----|
| GLU | 179 | SER | 604 | ASN | 684 |
| GLU | 180 | TYR | 605 | HIS | 714 |
| SER | 183 | VAL | 630 | ASP | 682 |
| PHE | 331 | TYR | 636 | | |

TABLE 2

Amino Acids encompassed by a 7-Angstrom radius around the DPPIV active site (SEQ ID NO:3).

| ARG | 99 | TYR | 521 | TRP | 633 |
|-----|-----|-----|-----|-----|-----|
| HIS | 100 | GLY | 523 | TYR | 636 |
| TRP | 175 | PRO | 524 | ASP | 637 |
| GLU | 178 | TYR | 559 | TYR | 640 |
| GLU | 179 | TRP | 603 | THR | 641 |
| GLU | 180 | SER | 604 | ARG | 643 |
| VAL | 181 | TYR | 605 | TYR | 644 |
| PHE | 182 | GLY | 606 | ASN | 684 |
| SER | 183 | TYR | 608 | VAL | 685 |
| ARG | 330 | ALA | 628 | HIS | 714 |
| PHE | 331 | PRO | 629 | ASP | 682 |
| ARG | 332 | VAL | 630 | | |

TABLE 3

Amino Acids encompassed by a 10-Angstrom radius around the DPPIV active site (SEQ ID NO:3).

| ARG | 99 | ILE | 379 | SER | 631 |
|-----|-----|-----|-----|-----|-----|
| HIS | 100 | VAL | 520 | ARG | 632 |
| TRP | 175 | TYR | 521 | TRP | 633 |
| VAL | 176 | ALA | 522 | TYR | 635 |
| TYR | 177 | GLY | 523 | TYR | 636 |
| GLU | 178 | PRO | 524 | ASP | 637 |
| GLU | 179 | CYS | 525 | SER | 638 |
| GLU | 180 | SER | 526 | VAL | 639 |
| VAL | 181 | TYR | 559 | TYR | 640 |
| PHE | 182 | MET | 565 | THR | 641 |
| SER | 183 | LEU | 572 | GLU | 642 |
| ALA | 184 | GLU | 576 | ARG | 643 |
| TYR | 230 | GLY | 602 | TYR | 644 |
| CYS | 275 | TRP | 603 | MET | 645 |
| GLN | 294 | SER | 604 | HIS | 678 |
| TRP | 327 | TYR | 605 | ASP | 682 |
| VAL | 328 | GLY | 606 | ASP | 683 |
| GLY | 329 | GLY | 607 | ASN | 684 |
| ARG | 330 | TYR | 608 | VAL | 685 |
| PHE | 331 | VAL | 609 | HIS | 686 |
| ARG | 332 | VAL | 627 | GLN | 689 |
| PRO | 333 | ALA | 628 | HIS | 714 |
| SER | 334 | PRO | 629 | GLY | 715 |
| GLU | 335 | VAL | 630 | | |

TABLE 4

Amino Acids encompassed by a 5-Angstrom radius around the AB and CD dimerization interfaces (SEQ ID NO:3).

| Chain A | | Chain B | | Chain C | | Chain D | |
|---------|-----|---------|-----|---------|-----|---------|-----|
| SER A | 213 | PRO B | 208 | PRO C | 208 | LEU D | 209 |
| TYR A | 215 | ILE B | 210 | LEU C | 209 | ILE D | 210 |
| SER A | 216 | GLU B | 211 | ILE C | 210 | GLU D | 211 |
| ASP A | 217 | TYR B | 212 | GLU C | 211 | TYR D | 212 |
| GLU A | 218 | SER B | 213 | TYR C | 212 | SER D | 213 |
| LEU A | 220 | TYR B | 215 | TYR C | 215 | SER D | 216 |
| GLN A | 221 | SER B | 216 | SER C | 216 | ASP D | 217 |
| TYR A | 222 | ASP B | 217 | ASP C | 217 | GLU D | 218 |
| PRO A | 223 | GLU B | 218 | GLU C | 218 | SER D | 219 |
| LYS A | 224 | SER B | 219 | SER C | 219 | LEU D | 220 |
| THR A | 225 | TYR B | 222 | LEU C | 220 | GLN D | 221 |
| ARG A | 227 | THR B | 225 | GLN C | 221 | TYR D | 222 |
| TYR A | 230 | ARG B | 227 | TYR C | 222 | PRO D | 223 |
| LYS A | 232 | GLN B | 688 | PRO C | 223 | THR D | 225 |
| ALA A | 233 | ALA B | 691 | THR C | 225 | ARG D | 227 |
| SER A | 694 | GLN B | 692 | TYR C | 230 | LYS D | 232 |
| LYS A | 695 | LYS B | 695 | PRO C | 231 | ALA D | 233 |
| LEU A | 697 | LEU B | 697 | LYS C | 232 | ALA D | 235 |
| VAL A | 698 | VAL B | 698 | GLU C | 634 | TYR D | 635 |
| ASP A | 699 | ASP B | 699 | THR C | 661 | MET D | 663 |
| GLY A | 701 | GLY B | 701 | LEU C | 676 | HIS D | 678 |
| VAL A | 702 | VAL B | 702 | PHE C | 687 | GLN D | 688 |
| PHE A | 704 | ASP B | 703 | GLN C | 688 | SER D | 690 |
| GLN A | 705 | PHE B | 704 | SER C | 690 | GLN D | 692 |
| MET A | 707 | GLN B | 705 | GLN C | 692 | SER D | 694 |
| TRP A | 708 | ALA B | 706 | LEU C | 697 | ASP D | 699 |
| TYR A | 709 | | | VAL C | 698 | VAL D | 702 |
| THR A | 710 | | | ASP C | 699 | ASP D | 703 |
| ASP A | 711 | | | GLY C | 701 | PHE D | 704 |
| | | | | VAL C | 702 | GLN D | 705 |
| | | | | ASP C | 703 | ALA D | 706 |
| | | | | PHE C | 704 | MET D | 707 |
| | | | | GLN C | 705 | TRP D | 708 |
| | | | | ALA C | 706 | TYR D | 709 |
| | | | | MET C | 707 | THR D | 710 |
| | | | | TRP C | 708 | | |
| | | | | TYR C | 709 | | |

With the benefit of the crystal structure and guidance provided by Tables 1, 2, 3 and 4, a wide variety of DPPIV variants (e.g., insertions, deletions, substitutions, etc.) that fall within the above specified identity ranges may be designed and manufactured utilizing recombinant DNA techniques well known to those skilled in the art, particularly in view of the knowledge of the crystal structure provided herein. These modifications can be used in a number of combinations to produce the variants. The present invention is useful for crystallizing and then solving the structure of the range of variants of DPPIV.

Variants of DPPIV may be insertional variants in which one or more amino acid residues are introduced into a predetermined site in the DPPIV sequence. For instance, insertional variants can be fusions of heterologous proteins or polypeptides to the amino or carboxyl terminus of the subunits.

Variants of DPPIV also may be substitutional variants in which at least one residue has been removed and a different residue inserted in its place. Non-natural amino acids (i.e. amino acids not normally found in native proteins), as well as isosteric analogs (amino acid or otherwise) may optionally be employed in substitutional variants. Examples of suitable substitutions are well known in the art, such as the Glu→sp, Ser→Cys, Cys→Ser, and His→Ala for example.

Another class of variants is deletional variants, which are characterized by the removal of one or more amino acid residues from the DPPIV sequence.

Other variants may be produced by chemically modifying amino acids of the native protein (e.g., diethylpyrocarbonate treatment that modifies histidine residues). Preferred are chemical modifications that are specific for certain amino acid side chains. Specificity may also be achieved by blocking other side chains with antibodies directed to the side chains to be protected. Chemical modification includes such reactions as oxidation, reduction, amidation, deamidation, or substitution of bulky groups such as polysaccharides or polyethylene glycol.

Exemplary modifications include the modification of lysinyl and amino terminal residues by reaction with succinic or other carboxylic acid anhydrides. Modification with these agents has the effect of reversing the charge of the lysinyl residues. Other suitable reagents for modifying amino-containing residues include imidoesters such as methyl picolinimidate; pyridoxal phosphate; pyridoxal chloroborohydride; trinitrobenzenesulfonic acid; 0-methylisourea, 2,4-pentanedione; and transaminaseN: talyzed reaction with glyoxylate, and N-hydroxysuccinamide esters of polyethylene glycol or other bulky substitutions.

Arginyl residues may be modified by reaction with a number of reagents, including phenylglyoxal, 2,3-butanedione, 1,2-cyclohexanedione, and ninhydrin. Modification of arginine residues requires that the reaction be performed in alkaline conditions because of the high $pK_a$, of the guanidine functional group. Furthermore, these reagents may react with the groups of lysine as well as the arginine epsilon-amino group.

Tyrosyl residues may also be modified to introduce spectral labels into tyrosyl residues by reaction with aromatic diazonium compounds or tetranitromethane, forming 0-acetyl tyrosyl species and 3-nitro derivatives, respectively. Tyrosyl residues may also be iodinated using $^{125}I$ or $^{131}I$, to prepare labeled proteins for use in radioimmunoassays.

Carboxyl side groups (aspartyl or glutamyl) may be selectively modified by reaction with carbodiimides or they may be converted to asparaginyl and glutaminyl residues by reaction with ammonium ions. Conversely, asparaginyl and glutaminyl residues may be deamidated to the corresponding aspartyl or glutamyl residues, respectively, under mildly acidic conditions. Either form of these residues falls within the scope of this invention.

Other modifications that may be formed include the hydroxylation of proline and lysine, phosphorylation of hydroxyl groups of seryl or threonyl groups of lysine, arginine and histidine side chains (T. E. Creighton, *Proteins. Structure and Molecular Properties*, W.H. Freeman & Co., San Francisco, pp. 79-86, 1983), acetylation of the N-terminal amine and amidation of any C-terminal carboxyl group.

As can be seen, modifications of the nucleic sequence encoding DPPIV may be accomplished by a variety of well-known techniques, such as site-directed mutagenesis (see, Gillman and Smith, *Gene* 8:81-97 (1979) and Roberts, S. et al., *Nature* 328:731-734 (1987)). When modifications are made, these modifications may optionally be evaluated for there affect on a variety of different properties including, for example, solubility, crystallizability and a modification to the protein's structure and activity.

In one variation, the variant and/or fragment of wild-type DPPIV is functional in the sense that the resulting protein is capable of associating with at least one same chemical entity that is also capable of selectively associating with a protein comprising the wild-type DPPIV (e.g., residues 39-766 of SEQ. ID No. 1) since this common associative ability evidences that at least a portion of the native structure has been conserved. That chemical entity may optionally be glucagon-like peptide 1 (GLP-1), glucagon-like peptide 2 (GLP-2), glucose-dependent, insulinotropic polypeptide (GIP), growth hormone releasing factor, SDF-1α, β-Casomorphin, TNF-α, Peptide YY or Substance P.

It is noted the activity of the native protein need not necessarily be conserved. Rather, amino acid substitutions, additions or deletions that interfere with native activity but which do not significantly alter the three-dimensional structure of the domain are specifically contemplated by the invention. Crystals comprising such variants of DPPIV, and the atomic structure coordinates obtained there from, can be used to identify compounds that bind to the native domain. These compounds may affect the activity of the native domain.

Amino acid substitutions, deletions and additions that do not significantly interfere with the three-dimensional structure of DPPIV will depend, in part, on the region where the substitution, addition or deletion occurs in the crystal structure. These modifications to the protein can now be made far more intelligently with the crystal structure information provided herein. In highly variable regions of the molecule, non-conservative substitutions as well as conservative substitutions may be tolerated without significantly disrupting the three-dimensional structure of the molecule. In highly conserved regions, or regions containing significant secondary structure, conservative amino acid substitutions are preferred.

Conservative amino acid substitutions are well known in the art, and include substitutions made on the basis of similarity in polarity, charge, solubility, hydrophobicity, hydrophilicity and/or the amphipathic nature of the amino acid residues involved. For example, negatively charged amino acids include aspartic acid and glutamic acid; positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine. Other conservative amino acid substitutions are well known in the art.

It should be understood that the protein may be produced in whole or in part by chemical synthesis. As a result, the selection of amino acids available for substitution or addition is not limited to the genetically encoded amino acids. Indeed, mutants may optionally contain non-genetically encoded amino acids. Conservative amino acid substitutions for many of the commonly known non-genetically encoded amino acids are well known in the art. Conservative substitutions for other amino acids can be determined based on their physical properties as compared to the properties of the genetically encoded amino acids.

In some instances, it may be particularly advantageous or convenient to substitute, delete and/or add amino acid residues in order to provide convenient cloning sites in cDNA encoding the polypeptide, to aid in purification of the polypeptide, etc. Such substitutions, deletions and/or additions which do not substantially alter the three dimensional structure of DPPIV will be apparent to those having skills in the art, particularly in view of the three dimensional structure of DPPIV provided herein.

2. Cloning, Expression and Purification of DPPIV

The gene encoding DPPIV can be isolated from RNA, cDNA or cDNA libraries. In this case, the portion of the gene encoding amino acid residues 39-766 (SEQ. ID No. 1), corresponding to the catalytic domain of human DPPIV, was isolated and is shown as SEQ. ID No. 2.

Construction of expression vectors and recombinant proteins from the DNA sequence encoding DPPIV may be performed by various methods well known in the art. For example, these techniques may be performed according to Sambrook et al., Molecular Cloning-A Laboratory Manual, Cold Spring Harbor, N.Y. (1989), and Kriegler, M., Gene Transfer and Expression, A Laboratory Manual, Stockton Press, New York (1990).

A variety of expression systems and hosts may be used for the expression of DPPIV. Example 1 provides one such expression system.

Once expressed, purification steps are employed to produce DPPIV in a relatively homogeneous state. In general, a higher purity solution of a protein increases the likelihood that the protein will crystallize. Typical purification methods include the use of centrifugation, partial fractionation, using salt or organic compounds, dialysis, conventional column chromatography, (such as ion exchange, molecular sizing chromatography, etc.), high performance liquid chromatography (HPLC), and gel electrophoresis methods (see, e.g., Deutcher, "Guide to Protein Purification" in Methods in Enzymology (1990), Academic Press, Berkeley, Calif.).

DPPIV may optionally be affinity labeled during cloning, preferably with an N-terminal six-histidine tag, in order to facilitate purification. With the use of an affinity label, it is possible to perform a one-step purification process on a purification column that has a unique affinity for the label. The affinity label may be optionally removed after purification. These and other purification methods are known and will be apparent to one of skill in the art.

3. Crystallization and Crystals Comprising DPPIV

One aspect of the present invention relates to methods for forming crystals comprising DPPIV as well as crystals comprising DPPIV.

In one embodiment, a method for forming crystals comprising DPPIV is provided comprising forming a crystallization volume comprising DPPIV, one or more precipitants, optionally a buffer, optionally a monovalent and/or divalent salt and optionally an organic solvent; and storing the crystallization volume under conditions suitable for crystal formation.

In yet another embodiment, a method for forming crystals comprising DPPIV is provided comprising forming a crystallization volume comprising DPPIV in solution comprising the components shown in Table 5; and storing the crystallization volume under conditions suitable for crystal formation.

TABLE 5

Precipitant 5-50% w/v of precipitant wherein the precipitant comprises one or more members of the group consisting of PEG MME having a molecular weight range between 300-10000, and PEG having a molecular weight range between 100-10000 pH pH 5-9. Buffers that may be used include, but are not limited to tris, bicine, cacodylate, acetate, citrate, MES and combinations thereof.

Additives optionally 0.05 to 0.8 M additives wherein the additives comprises sarcosine or 0.5 to 25% additives wherein the additives comprises xylitrol Protein Concentration 1 mg/ml-50 mg/ml Temperature

1° C.-25° C.

In yet another embodiment, a method for forming crystals comprising DPPIV is provided comprising forming a crystallization volume comprising DPPIV; introducing crystals comprising DPPIV as nucleation sites, and storing the crystallization volume under conditions suitable for crystal formation.

Crystallization experiments may optionally be performed in volumes commonly used in the art, for example typically 15, 10, 5, 2 microliters or less. It is noted that the crystallization volume optionally has a volume of less than 1 microliter, optionally 500, 250, 150, 100, 50 or less nanoliters.

It is also noted that crystallization may be performed by any crystallization method including, but not limited to batch, dialysis and vapor diffusion (e.g., sitting drop and hanging drop) methods. Micro and/or macro seeding of crystals may also be performed to facilitate crystallization.

It should be understood that forming crystals comprising DPPIV and crystals comprising DPPIV according to the invention are not intended to be limited to the wild type, full length DPPIV shown in SEQ. ID No. 1 and to fragments comprising residues 39-766 of SEQ. ID No. 1. Rather, it should be recognized that the invention may be extended to various other fragments and variants of wild-type DPPIV as described above.

It should also be understood that forming crystals comprising DPPIV and crystals comprising DPPIV according to the invention may be such that DPPIV is optionally complexed with one or more ligands and one or more copies of the same ligand. The ligand used to form the complex may be any ligand capable of binding to DPPIV. In one variation, the ligand is a natural substrate. In another variation, the ligand is an inhibitor.

In one particular embodiment, DPPIV crystals have a crystal lattice in the $P2_1$ space group. DPPIV crystals may also optionally have unit cell dimensions, +/−5%, of a=121.53 Å b=124.11 Å and c=144.42 Å, $\alpha=\gamma=90°$, $\beta=114.6°$. DPPIV crystals also preferably are capable of diffracting X-rays for determination of atomic coordinates to a resolution of 4 Å, 3 Å, 2.5 Å, 2 Å or better.

Crystals comprising DPPIV may be formed by a variety of different methods known in the art. For example, crystallizations may be performed by batch, dialysis, and vapor diffusion (sitting drop and hanging drop) methods. A detailed description of basic protein crystallization setups may be found in McRee, D. and David. P., Practical Protein Crystallography, $2^{nd}$ Ed. (1999), Academic Press Inc. Further descriptions regarding performing crystallization experiments are provided in Stevens, et al. (2000) Curr. Opin. Struct. Biol.: 10(5):558-63, and U.S. Pat. Nos. 6,296,673, 5,419,278, and 5,096,676.

In one variation, crystals comprising DPPIV are formed by mixing substantially pure DPPIV with an aqueous buffer containing a precipitant at a concentration just below a concentration necessary to precipitate the protein. One suitable precipitant for crystallizing DPPIV is polyethylene glycol (PEG), which combines some of the characteristics of the salts and other organic precipitants (see, for example, Ward et al., J. Mol. Biol. 98:161, 1975, and McPherson, J. Biol. Chem. 251:6300, 1976.

During a crystallization experiment, water is removed by diffusion or evaporation to increase the concentration of the precipitant, thus creating precipitating conditions for the protein. In one particular variation, crystals are grown by vapor diffusion in hanging drops or sitting drops. According to these methods, a protein/precipitant solution is formed and then allowed to equilibrate in a closed container with a larger aqueous reservoir having a precipitant concentration for producing crystals. The protein/precipitant solution continues to equilibrate until crystals grow.

By performing submicroliter volume sized crystallization experiments, as detailed in U.S. Pat. No. 6,296,673, effective crystallization conditions for forming crystals of a DPPIV complex were obtained. In order to accomplish this, systematic broad screen crystallization trials were performed on a DPPIV complex using the sitting drop technique. Over 1000 individual trials were performed in which pH, temperature and precipitants were varied. In each experiment, a 100 nL mixture of DPPIV complex and precipitant was placed on a platform positioned over a well containing 100 µL of the precipitating solution. Precipitate and crystal formation was detected in the sitting drops. Fine screening was then carried out for those crystallization conditions that appeared to produce precipitate and/or crystal in the drops.

Based on the crystallization experiments that were performed, a thorough understanding of how different crystallization conditions affect DPPIV crystallization was obtained. Based on this understanding, a series of crystallization conditions were identified that may be used to form crystals comprising DPPIV. These conditions are summarized in Table 5. A particular example of crystallization conditions that may be used to form diffraction quality crystals of the DPPIV complex is detailed in Example 2. FIG. 2 illustrates crystals of the DPPIV complex formed using the crystallization conditions provided in Table 5.

One skilled in the art will recognize that the crystallization conditions provided in Table 5 and Example 2 can be varied and still yield protein crystals comprising DPPIV. For example, it is noted that variations on the crystallization conditions described herein can be readily determined by taking the conditions provided in Table 5 and performing fine screens around those conditions by varying the type and concentration of the components in order to determine additional suitable conditions for crystallizing DPPIV, variants of DPPIV, and ligand complexes thereof.

Crystals comprising DPPIV have a wide range of uses. For example, now that crystals comprising DPPIV have been produced, it is noted that crystallizations may be performed using such crystals as a nucleation site within a concentrated protein solution. According to this variation, a concentrated protein solution is prepared and crystalline material (microcrystals) are used to 'seed' the protein solution to assist nucleation for crystal growth. If the concentrations of the protein and any precipitants are optimal for crystal growth, the seed crystal will provide a nucleation site around which a larger crystal forms. Given the ability to form crystals comprising DPPIV according to the present invention, the crystals so formed can be used by this crystallization technique to initiate crystal growth of other DPPIV comprising crystals, including DPPIV complexed to other ligands.

As will be described herein in greater detail, crystals may also be used to perform X-ray or neutron diffraction analysis in order to determine the three-dimensional structure of DPPIV and, in particular, to assist in the identification of its active site. Knowledge of the binding site region allows rational design and construction of ligands including inhibitors. Crystallization and structural determination of DPPIV mutants having altered bioactivity allows the evaluation of whether such changes are caused by general structure deformation or by side chain alterations at the substitution site.

4. X-Ray Data Collection and Structure Determination

Crystals comprising DPPIV may be obtained as described above in Section 3. As described herein, these crystals may then be used to perform x-ray data collection and for structure determination.

In one embodiment, described in Example 2, crystals of a DPPIV complex were obtained where DPPIV has the sequence of residues shown in SEQ. ID No. 3. These particular crystals were used to determine the three dimensional structure of DPPIV. However, it is noted that other crystals comprising DPPIV including different DPPIV variants, fragments, and complexes thereof may also be used.

The structure of DPPIV was solved by a combination of heavy-atom derivatives and Seleno-Methionine (Se-Met) phasing in conjunction with non-crystallographic averaging. Heavy atom derivatives were obtained by soaking native DPPIV crystals in heavy atom solutions made using the crystallization solution. The concentration of heavy atom derivative and time of soaking varied between 0.5 mM to 10 mM and 1 to 15 days, respectively. An extensive array of heavy atom derivatives were individually soaked into DPPIV crystals and analyzed. Two heavy atom derivatives were used to determine the phases: di-m-iodobis (ethylene-diamine)-di-platinum (II) nitrate (PIP) and ethyl mercuric thiosalicylic acid sodium salt (EMTS). Data from crystals of apo DPPIV, Se-Met-DPPIV, PIP-DPPIV and EMTS-DPPIV were collected from cryocooled crystals (100K) at the Stanford Synchrotron Radiation Laboratory (SSRL) beam lines 9-1, 9-2 and 11-1 and the Advanced Light Source (ALS) beam lines 5.0.2 and 5.0.3 both using an ADSC Quantum CCD detector. The diffraction pattern of the DPPIV crystals displayed symmetry consistent with space group $P2_1$ with unit cell dimensions a=121.53 Å=124.11 Å and c=144.42 Å, $\alpha=\gamma=90°$, $\beta=114.6°$ (+/−5%). Data were collected and integrated to 2.3 Å with MOSFLM (or HKL2000) and scaled with SCALA (or Scalepack) (CCP4 Study Weekend, Eds. Sawyer, L., Isaacs, N. & Bailey, S. 56-62, SERC Daresbury Laboratory, England, 1993).

All crystallographic calculations were performed using the CCP4 program package (Collaborative Computational Project, N. The CCP4 Suite: Programs for Protein Crystallography. Acta Cryst. D50, 760-763 (1994)).

Positions for the Platinum atoms of the PIP derivative were located using the direct method search program, SHELXD. The heavy atom parameters of the PIP derivative were refined using the program SHARP. The refined parameters were used to compute phases and locate the Mercury atom positions of the EMTS derivative. The heavy atom parameters of both derivatives were refined using SHARP. Initial solvent flattened maps using the phases from both heavy atom derivatives were of reasonable quality and helped identifying parts of the secondary structure elements of DPPIV. Due to low incorporation of Selenium (Se) in the baculovirus expressed protein, solving Se positions using MAD data was not successful. However, using the phases from the two heavy atom derivatives and cross phasing on to the peak data of the Se-Met derivative of DPPIV allowed for locating all 52 Se atoms of the four subunits of the Se-Met-DPPIV crystal. A final refinement of both the heavy atom derivatives, including the Se atoms, was carried out using SHARP. The resulting phases with solvent flattening and non-crystallographic averaging using DM resulted in an interpretable electron density map. The model was built into the electron density map using Xfit. Refinement continued with iterative map/model/phase improvement using ARP_WARP map (Perrakis, A., Morris, R. J. & Lamzin, V. S.). This was followed by alternating cycles of manual rebuilding of the model with Xfit (McRee, D. E. XtalView/Xfit-A versatile program for manipulating atomic coordinates and electron density J. Struct. Biol. 125, 156-65 (1999)), ARP_WARP map improvement (Perrakis, A., Morris, R. J. & Lamzin, V. S. Automated protein model building combined with iterative structure refinement) and geometrically restrained refinement against a maximum likelihood target function as implemented in REFMAC(CCP4) until the refinement reached convergence. All stages of model refinement were carried with bulk solvent correction and anisotropic scaling. The data collection and data refinement statistics are given in Table 6.

TABLE 6

| Crystal data | |
|---|---|
| Space group | $P2_1$ |
| Unit cell dimensions | a = 121.53 Å |
| | b = 124.11 Å and |
| | c = 144.42 Å, |
| | $\alpha = \gamma = 90°$, |
| | $\beta = 114.6°$ |
| Data collection | |
| X-ray source | ALS: BL5.0.2; BL5.0.3; SSRL: BL9-1; BL9-2; BL11-1 |
| Wavelength [Å] | 0.90 to 1.25 |
| Resolution [Å] | 2.30 |
| Observations (unique) | 183144 |
| Redundancy | 2.8 |
| Completeness overall (outer shell) | 98 (97.6)% |
| I/σ (I) overall (outer shell) | 8.6 (1.9) |
| $R_{symm}^1$ overall (outer shell) | 8.2 (51.6)% |
| Refinement | |
| Reflections used | 159715 |
| R-factor | 22.7% |
| $R_{free}$ | 28.3% |
| r.m.s bonds | 0.009 Å |
| r.m.s angles | 1.432° |

During structure determination, where the unit cell dimensions were a=121.53 Å b=124.11 Å and c=144.42 Å, $\alpha=\gamma=90°$, $\beta=114.6°$, it was realized that each unit cell comprised four DPPIV molecules. Structure coordinates were determined for this complex and the resultant set of structural coordinates from the refinement are presented in FIG. 3.

It is noted that the sequence of the structure coordinates presented in FIG. 3 differ in some regards from the sequence shown in SEQ. ID No. 1. Structure coordinates are not reported for some residues because the electron density obtained was insufficient to identify the position of these residues. For FIG. 3, structure coordinates for residues 151-153 (chains C and D) and 97-99 (chain D) are not reported.

Those of skill in the art understand that a set of structure coordinates (such as those in FIG. 3) for a protein or a protein-complex or a portion thereof, is a relative set of points that define a shape in three dimensions. Thus, it is possible that an entirely different set of structure coordinates could define a similar or identical shape. Moreover, slight variations in the individual coordinates may have little effect on overall shape. In terms of binding pockets, these variations would not be expected to significantly alter the nature of ligands that could associate with those pockets. The term "binding pocket" as used herein refers to a region of the protein that, as a result of its shape, favorably associates with a ligand.

These variations in coordinates may be generated because of mathematical manipulations of the DPPIV structure coordinates. For example, the sets of structure coordinates shown in FIG. 3 could be manipulated by crystallographic permutations of the structure coordinates, fractionalization of the structure coordinates, application of a rotation matrix, integer additions or subtractions to sets of the structure coordinates, inversion of the structure coordinates or any combination of the above.

Alternatively, modifications in the crystal structure due to mutations, additions, substitutions, and/or deletions of amino acids or other changes in any of the components that make up the crystal could also account for variations in structure coordinates. If such variations are within an acceptable standard error as compared to the original coordinates, the resulting three-dimensional shape should be considered to be the same. Thus, for example, a ligand that bound to the active site binding pocket of DPPIV would also be expected to bind to another binding pocket whose structure coordinates defined a shape that fell within the acceptable error.

Various computational analyses may be used to determine whether structure coordinates for a protein or a portion thereof is similar to the structure coordinates of DPPIV provided herein, or a portion thereof. Such analyses may be carried out in well known software applications, such as the Molecular Similarity application of QUANTA (Molecular Simulations Inc., San Diego, Calif.) version 4.1, and as described in the accompanying User's Guide. For the purpose of this invention, a rigid fitting method shall be used to compare protein structures.

For the purpose of this invention, any set of structure coordinates for a protein from any source having a root mean square deviation of alpha-carbon atoms of less than 3 Å when superimposed on the alpha-carbon atom positions of the corresponding atomic coordinates of FIG. 3 shall be considered identical. It is noted that the root mean square deviation is intended to be limited to only those alpha-carbon atoms of amino acid residues that are common to both the protein fragment represented in FIG. 3 and the protein whose structure coordinates are being compared to the coordinates shown in FIG. 3.

It is noted that mutants and variants of DPPIV as well as other S9 proteases are likely to have similar structures despite having different sequences. For example, the binding pockets of these related proteins are likely to have similar contours. Accordingly, it should be recognized that the structure coordinates and binding pocket models provided herein have utility for these other related proteins.

Accordingly, in one embodiment, the invention relates to data, computer readable media comprising data, and uses of the data where the data comprises all or a portion of the structure coordinates shown in FIG. 3 or structure coordinates having a root mean square deviation of alpha-carbon atoms of less than 3 Å when superimposed on the alpha-carbon atom positions of the corresponding atomic coordinates of FIG. 3. Again, it is noted that the root mean square deviation is intended to be limited to only those alpha-carbon atoms of amino acid residues that are common to both the protein fragment represented in FIG. 3 and the protein whose structure coordinates are being compared to the coordinates shown in FIG. 3.

As noted, there are many different ways to express the surface contours of the DPPIV structure other than by using the structure coordinates provided in FIG. 3. Accordingly, it is noted that the present invention is also directed to any data, computer readable media comprising data, and uses of the data where the data defines a computer model for a protein binding pocket, at least a portion of the computer model having a surface contour that has a root mean square deviation of less than 3 Å when superimposed on a surface contour defined by atomic coordinates of FIG. 3, the root mean square deviation being calculated based only on alpha-carbon atoms in the structure coordinates of FIG. 3 that are present in residues shown in SEQ. ID No. 1.

In regard to these embodiments, it is noted that the root mean square deviation calculation may optionally be based on a comparison of main-chain atoms or non-hydrogen atoms. Also, the root mean square deviation of alpha-carbon atoms, main-chain atoms or non-hydrogen atoms may optionally be less than 2.7 Å, 2.5 Å, 2.0 Å, 1.5 Å, 1 Å, 0.5 Å, or less.

5. DPPIV Structure

The present invention is also directed to a three-dimensional crystal structure of DPPIV. This crystal structure may be used to identify binding sites, to provide mutants having desirable binding properties, and ultimately, to design, characterize, or identify ligands that interact with DPPIV as well as other S9 proteases.

The three-dimensional crystal structure of DPPIV may be generated, as is known in the art, from the structure coordinates shown in FIG. 3 and similar such coordinates.

During the course of structure solution it became evident that the wild type apo crystals of DPPIV of the present invention contained four nearly identical copies in the asymmetric unit. The final coordinates for each one of these molecules, referred to as chains A, B, C and D, are given in FIG. 3. The variations between the chains are described below.

Chain A includes amino acid residues 40-766 and four amino acid residues have covalently linked sugar molecules (FIG. 3). Chain B includes amino acid residues 39-766 and also includes 4 histidine residues of the N-terminal polyhistidine tag (residues 35-38). Five amino acid residues of chain B have covalently linked sugar molecules (FIG. 3). Chain C includes amino acid residues 40-766 and five of the amino acid residues are covalently linked to sugar molecules. Chain D includes amino acid residues 39-766 with five sugar-linked amino acid residues. In addition, chains C and D have no density for amino acid residues 139, 140, and 141 and hence coordinates for these residues are not included in FIG. 3. Similarly, coordinates for amino acid residues 85, 86. and 87 of chain D are not included in FIG. 3. The coordinate set additionally includes 928 solvent molecules modeled as water.

Figure 4A:
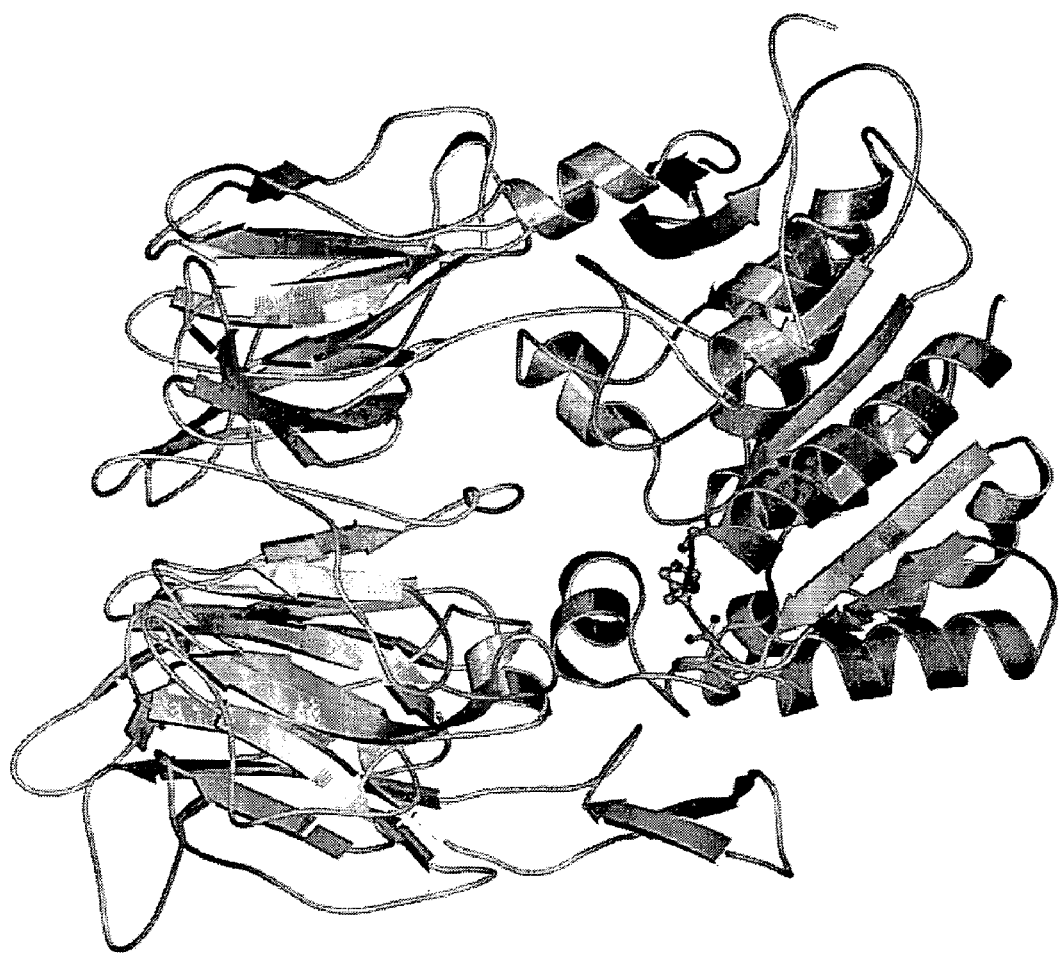
FIG. 4A illustrates a ribbon diagram overview of the structure of DPPIV, highlighting secondary structural elements of the protein.

FIG. 4A illustrates a ribbon diagram overview of the structure of DPPIV, highlighting secondary structural elements of the protein. DPPIV is a cylindrical shaped molecule with an approximate height of 70 Å and a diameter of 60 Å (FIG. 4A). The catalytic triad of DPPIV (Ser 630, Asp 708 and His 740) is illustrated in the center of FIG. 4A by a "ball and stick" representation. This triad of amino acids is located in the peptidase domain or catalytic domain of DPPIV. The catalytic domain is covalently linked to the β-propeller domain (FIG. 4A).

The catalytic domain of DPPIV includes residues 39-55 and 499-766. Since, the structure of the present invention does not contain the first 46 residues (Chain B of FIG. 3) it is presumed that the N-terminal residues of the catalytic domain adopt a random structure with a short double turn α-helix formed by residues 44 to 51. The catalytic domain of DPPIV adopts a characteristic α/β hydrolase fold. The core of this domain contains an 8-stranded β-sheet with all strands being parallel except one (FIG. 4A). The β-sheet is significantly twisted and is flanked by three α-helices on one side and five α-helices on the other. The topology of the β-strands is 1, 2, −1x, 2x and (1x) (J. S. Richardson: The anatomy and taxonomy of protein structure; (1981) *Adv. Protein Chem.* 269, 15076-15084.).

Figure 4B:
FIG. 4B illustrates another ribbon diagram overview of the structure of DPPIV, highlighting additional secondary structural elements of the protein.

FIG. 4B illustrates the remaining residues 56-498 that form the non-catalytic domain of DPPIV. This domain is also known as β-propeller domain (FIG. 4B). The β-propeller domain is a 7-fold repeat of four-stranded antiparallel β-sheets (FIG. 4B). The sheets are twisted and arranged around a central tunnel as seen in case of Prolyl Oligopeptidase. Further, the β-sheets pack face-to-face and are stabilized predominantly by hydrophobic interactions. The β-propeller is linked to the catalytic domain by two polypeptide chains, one involving the N-terminal residues and the other consisting of the C-terminal residues 499-508 which also form an α-helix.

Figure 5:
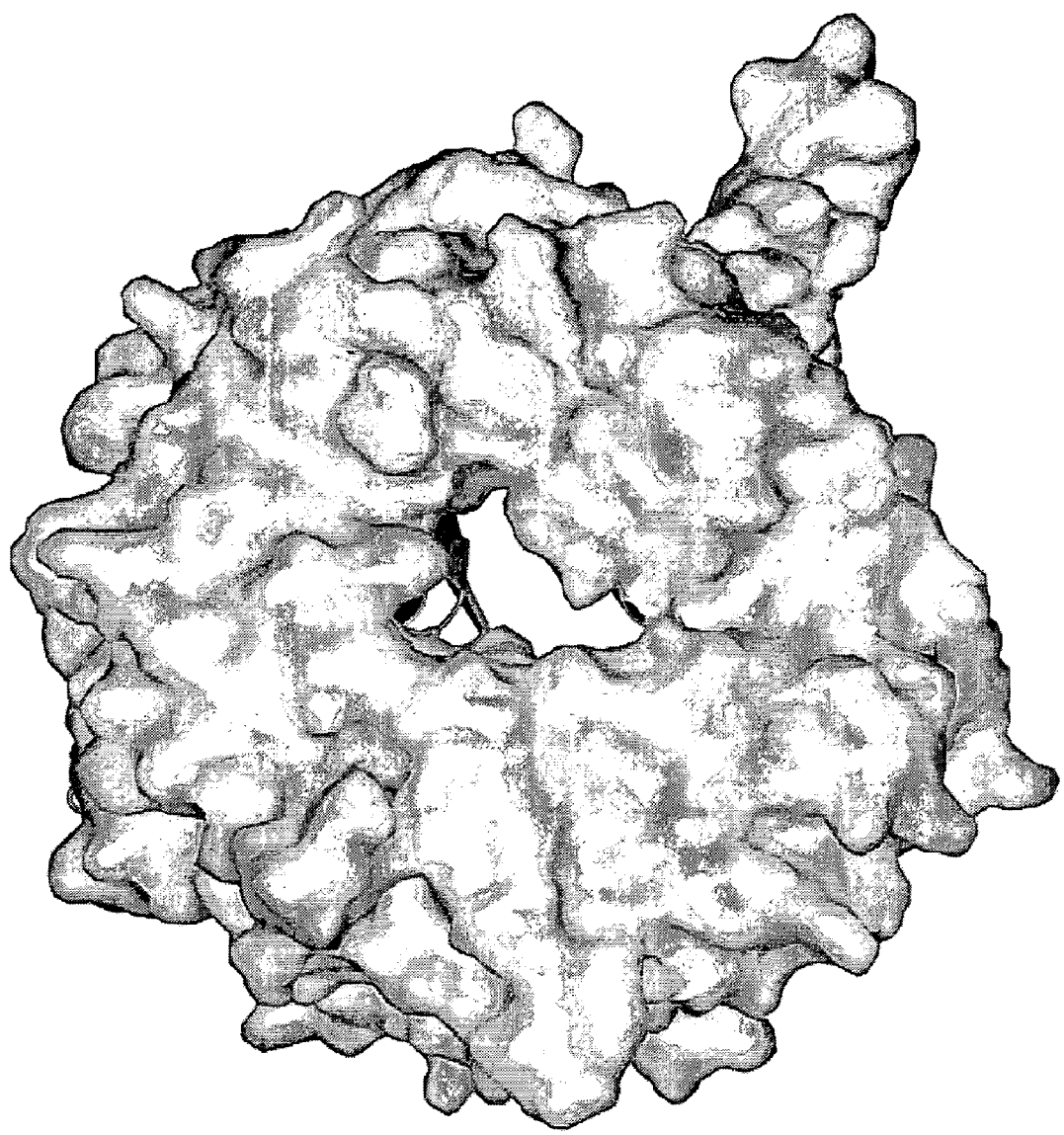
FIG. 5 illustrates the DPPIV binding site of DPPIV based on the determined crystal structure for the molecule in the asymmetric unit corresponding to the coordinates shown in FIG. 3.

FIG. 5 illustrates the binding site of DPPIV based on the determined crystal structure corresponding to the coordinates shown in FIG. 3.

6. DPPIV Active Site and Ligand Interaction

The term "binding site" or "binding pocket", as the terms are used herein, refers to a region of a protein that, as a result of its shape, favorably associates with a ligand or substrate. The term "DPPIV-like binding pocket" refers to a portion of a molecule or molecular complex whose shape is sufficiently similar to the DPPIV binding pockets as to bind common ligands. This commonality of shape may be quantitatively defined based on a comparison to a reference point, that reference point being the structure coordinates provided herein. For example the commonality of shape may be quantitatively defined based on a root mean square deviation (rmsd) from the structure coordinates of the backbone atoms of the amino acids that make up the binding pockets in DPPIV (as set forth in FIG. 3).

The "active site binding pockets" or "active site" of DPPIV refers to the area on the surface of DPPIV where the substrate binds.

FIG. 5 illustrates the inhibitor-binding site of DPPIV based on the determined crystal structure (coordinates shown in FIG. 3). The active site containing the catalytic triad (Ser 630, Asp 708 and His 740), is located in a large cavity (FIG. 5) at the interface of the catalytic and the β-propeller domains. Ser 630 is located on a sharp turn that connects an α-helix to a β-strand. The positioning of this active site Serine residue is referred to as a nucleophile elbow and is characteristic of an α/β type hydrolase (D. J. Ollis et al., The α/β hydrolase fold; (1992) *Protein Eng.* 5, 197-211). In DPPIV, the active-site serine is surrounded by hydrophobic residues, which include the large aromatic residues Trp 629 and Tyr 631. The hydroxyl group of the active site serine is exposed and involved in hydrogen bonding with the imidazole group of the active site His 740 (OH————————NH distance 2.7 Å). His 740 is located on the middle of a loop that connects a β-strand to an α-helix. The other nitrogen atom of the imidazole ring of His 740 forms a hydrogen bond with the side chain oxygen of the third active site residue (Asp 708) of the catalytic triad. Asp 708 is also located on a loop connecting a β-strand and an α-helix. The second oxygen atom of the side chain carboxylate of Asp 708 forms two hydrogen bonded interactions with the main-chain amide of residues (Asn 710 and Val 711). The hydrogen bonding interactions of the catalytic triad is similar to those observed for prolyl oligopeptidase.

Based on sequence alignments and structural comparisons with prolyl oligopeptidase, the residues that form the DPPIV active site pocket can be predicted with a high degree of probability. The binding pocket appears to be formed by a pocket of hydrophobic residues (Phe 357, Tyr 631, Tyr 662, Tyr 666, Tyr 547 and Val 711). In addition to the catalytic triad a large number of polar residues are also present in this hydrophobic environment (Arg 125, Glu 205, Glu 206 and Asp 663).

In resolving the crystal structure of DPPIV, applicants determined that DPPIV amino acids shown in Table 1 (above) are encompassed within a 4-Angstrom radius around the DPPIV active site and therefore are likely close enough to interact with an active site inhibitor of DPPIV. Applicants have also determined that the amino acids shown in Table 2 (above) are encompassed within a 7-Angstrom radius around the DPPIV active site. Further, the amino acids shown in Table 3 (above) are encompassed within a 10-Angstrom radius around the DPPIV active site. Due to their proximity to the active site, the amino acids in the 4, 7, and/or 10 Angstroms sets are preferably conserved in variants of DPPIV. While it is desirable to largely conserve these residues, it should be recognized however that variants may also involve varying 1, 2, 3, 4 or more of the residues set forth in Tables 1, 2, and 3 in order to evaluate the roles these amino acids play in the binding pocket. Applicants have also determined that amino acids shown in Table 4 (above) are encompassed within a 5-Angstrom radius around the DPPIV dimerization interface (AB and CD dimers).

With the knowledge of the DPPIV crystal structure provided herein, Applicants are able to know the contour of a DPPIV binding pocket as a binding pocket where the relative positioning of the 4, 7, and/or 10 Angstroms sets of amino acids. In addition, Applicants are able to know the contour of a dimerization interface (AB and CD dimers) based on the relative positions of the α-carbon residues in Table 4. Again, it is noted that it may be desirable to form variants where 1, 2, 3, 4 or more of the residues set forth in Tables 1, 2, and 3 are varied in order to evaluate the roles these amino acids play in the binding pocket. Accordingly, any set of structure coordinates for a protein from any source having a root mean square deviation of non-hydrogen atoms of less than 3 Å when superimposed on the non-hydrogen atom positions of the corresponding atomic coordinates of FIG. 3 for the 4, 7, and/or 10 Angstroms sets of amino acids and/or those amino acids of the dimerization interface shall be considered identical. As noted previously, the root mean square deviation is intended to be limited to only those non-hydrogen atoms of amino acid residues that are common to both the protein fragment represented in FIG. 3 and the protein whose structure coordinates are being compared to the coordinates shown in FIG. 3 since the sequence of the protein may be varied somewhat.

Accordingly, in one embodiment, the invention relates to data, computer readable media comprising data, and uses of the data where the data comprises the structure coordinates shown in FIG. 3 or structure coordinates having a root mean square deviation of non-hydrogen atoms of less than 3 Å when superimposed on the non-hydrogen atom positions of the corresponding atomic coordinates of FIG. 3 for the 4, 7, and/or 10 Angstroms sets of amino acids and/or the residues listed in Table 4.

Again, it is noted that the root mean square deviation is intended to be limited to only those non-hydrogen atoms of amino acid residues that are common to both the protein fragment represented in one or more of the tables and the protein whose structure coordinates are being compared to the coordinates shown in FIG. 3.

As noted above, there are many different ways to express the surface contours of the DPPIV structure other than by using the structure coordinates provided in FIG. 3. Accordingly, it is noted that the present invention is also directed to any data, computer readable media comprising data, and uses of the data where the data defines a computer model for a protein binding pocket, at least a portion of the computer model having a surface contour that has a root mean square deviation of less than 3 Å when superimposed on a surface contour defined by atomic coordinates of FIG. 3, the root mean square deviation being calculated based only on non-hydrogen atoms in the structure coordinates of FIG. 3 that are present in residues shown in Tables 1, 2, 3 and/or 4.

Optionally, the root mean square deviation of non-hydrogen atoms is less than 1.5 Å, 1 Å, 0.5 Å, or less.

It will be readily apparent to those of skill in the art that the numbering of amino acids in other isoforms of DPPIV may be different than that set forth for DPPIV. Corresponding amino acids in other isoforms of DPPIV are easily identified by visual inspection of the amino acid sequences or by using commercially available homology software programs, as further described below.

7. System For Displaying the Three Dimensional Structure of DPPIV

The present invention is also directed to machine-readable data storage media having data storage material encoded with machine-readable data that comprises structure coordinates for DPPIV. The present invention is also directed to a machine readable data storage media having data storage material encoded with machine readable data, which, when read by an appropriate machine, can display a three dimensional representation of a structure of DPPIV.

All or a portion of the DPPIV coordinate data shown in FIG. 3, when used in conjunction with a computer programmed with software to translate those coordinates into the three-dimensional structure of DPPIV may be used for a variety of purposes, especially for purposes relating to drug discovery. Softwares for generating three-dimensional graphical representations are known and commercially available. The ready use of the coordinate data requires that it be stored in a computer-readable format. Thus, in accordance with the present invention, data capable of being displayed as the three-dimensional structure of DPPIV and/ or portions thereof and/or their structurally similar variants may be stored in a machine-readable storage medium, which is capable of displaying a graphical three-dimensional representation of the structure.

For example, in one embodiment, a computer is provided for producing a three-dimensional representation of at least an DPPIV-like binding pocket, the computer comprising: machine readable data storage medium comprising a data storage material encoded with machine-readable data, the machine readable data comprising structure coordinates that have a root mean square deviation of less than 3 Angstroms when compared to structure coordinates appearing in FIG. 3, the comparison being based on alpha-carbon atoms of amino acid residues present in both the set of structure coordinates shown in FIG. 3 and the structure coordinates being compared, the comparison being further limited to residues of DPPIV appearing in Tables 1, 2, 3 and/or 4; a working memory for storing instructions for processing the machine-readable data; a central-processing unit coupled to the working memory and to the machine-readable data storage medium, for processing the machine-readable data into the three-dimensional representation; and an output hardware coupled to the central processing unit, for receiving the three Dimensional representation.

Another embodiment of this invention provides a machine-readable data storage medium, comprising a data storage material encoded with machine readable data which, when used by a machine programmed with instructions for using said data, displays a graphical three-dimensional representation comprising DPPIV or a portion or variant thereof.

In one variation, the machine readable data comprises data for representing a protein based on structure coordinates having a root mean square deviation of alpha-carbon atoms of less than 3 Å when superimposed on the alpha-carbon atom positions of the corresponding atomic coordinates of FIG. 3 for all of the amino acids in FIG. 3.

In another variation, the machine readable data comprises data for representing a protein based on structure coordinates having a root mean square deviation of alpha-carbon atoms of less than 3 Å when superimposed on the alpha-carbon atom positions of the corresponding atomic coordinates of FIG. 3 for the amino acids listed in Tables 1, 2, 3 and/or 4.

It is again noted that the root mean square deviation calculation may optionally be based on a comparison of main-chain atoms or non-hydrogen atoms. Also, the root mean square deviation of alpha-carbon atoms, main-chain atoms or non-hydrogen atoms may optionally be less than 2.7 Å, 2.5 Å, 2.0 Å, 1.5 Å, 1 Å, 0.5 Å, or less.

According to another embodiment, the machine-readable data storage medium comprises a data storage material encoded with a first set of machine readable data which comprises the Fourier transform of the structure coordinates set forth in FIG. 3, and which, when using a machine programmed with instructions for using said data, can be combined with a second set of machine readable data comprising the X-ray diffraction pattern of another molecule or molecular complex to determine at least a portion of the structure coordinates corresponding to the second set of machine readable data. For example, the Fourier transform of the structure coordinates set forth in FIG. 3 may be used to determine at least a portion of the structure coordinates of other DPPIV-like enzymes, and isoforms of DPPIV.

Optionally, a computer system is provided in combination with the machine-readable data storage medium provided herein. In one embodiment, the computer system comprises a working memory for storing instructions for processing the machine-readable data; a processing unit coupled to the working memory and to the machine-readable data storage medium, for processing the machine-readable data into the three-dimensional representation; and an output hardware coupled to the processing unit, for receiving the three-dimensional representation.

Figure 6:
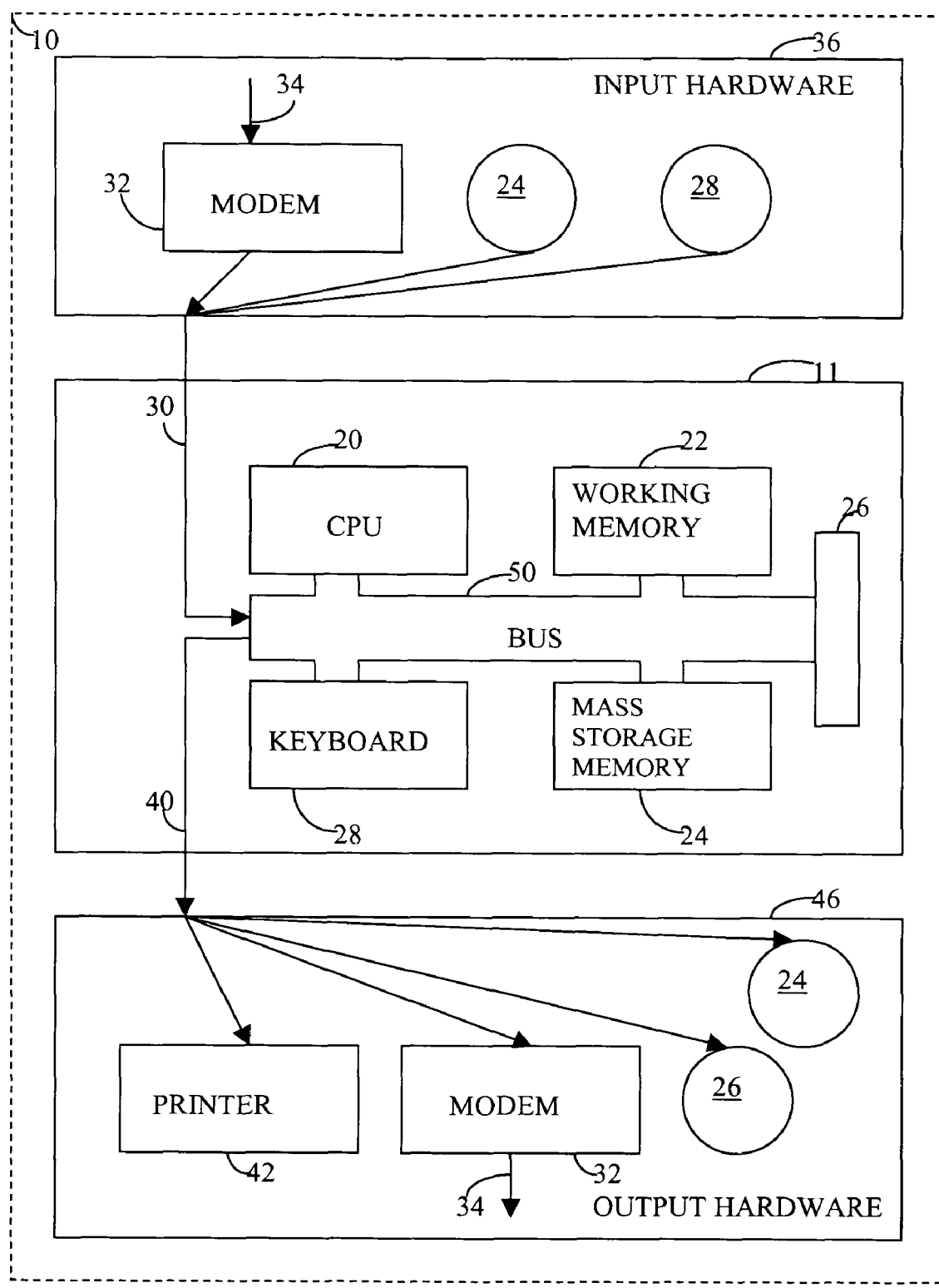
FIG. 6 illustrates a system that may be used to carry out instructions for displaying a crystal structure of DPPIV encoded on a storage medium.

FIG. 6 illustrates an example of a computer system that may be used in combination with storage media according to the present invention. As illustrated, the computer system 10 includes a computer 11 comprising a central processing unit ("CPU") 20, a working memory 22 which may be, e.g., RAM (random-access memory) or "core" memory, mass storage memory 24 (such as one or more disk drives or CD-ROM drives), one or more cathode-ray tube ("CRT") display terminals 26, one or more keyboards 28, one or more input lines 30, and one or more output lines 40, all of which are interconnected by a conventional bi-directional system bus 50.

Input hardware 36, coupled to computer 11 by input lines 30, may be implemented in a variety of ways. For example, machine-readable data of this invention may be inputted via the use of a modem or modems 32 connected by a telephone line or dedicated data line 34. Alternatively or additionally, the input hardware 36 may comprise CD-ROM drives or disk drives 24. In conjunction with display terminal 26, keyboard 28 may also be used as an input device.

Conventional devices may, similarly implement output hardware 46, coupled to computer 11 by output lines 40. By way of example, output hardware 46 may include CRT display terminal 26 for displaying a graphical representation of a binding pocket of this invention using a program such as QUANTA as described herein. Output hardware might also include a printer 42, so that hard copy output may be produced, or a disk drive 24, to store system output for later use.

In operation, CPU 20 coordinates the use of the various input and output devices 36, 46 coordinates data accesses from mass storage 24 and accesses to and from working memory 22, and determines the sequence of data processing steps. A number of programs may be used to process the machine-readable data of this invention. Such programs are discussed in reference to using the three dimensional structure of DPPIV described herein.

The storage medium encoded with machine-readable data according to the present invention can be any conventional data storage device known in the art. For example, the storage medium can be a conventional floppy diskette or hard disk. The storage medium can also be an optically-readable data storage medium, such as a CD-ROM or a DVD-ROM, or a rewritable medium such as a magneto-optical disk that is optically readable and magneto-optically writable.

8. Uses of the Three Dimensional Structure of DPPIV

The three-dimensional crystal structure of the present invention may be used to identify DPPIV binding sites, be used as a molecular replacement model to solve the structure of unknown crystallized proteins, to design mutants having desirable binding properties, and ultimately, to design, characterize, identify entities capable of interacting with DPPIV and other S9 proteases, as well as other uses that would be recognized by one of ordinary skill in the art. Such entities may be chemical entities or proteins. The term "chemical entity", as used herein, refers to chemical compounds, complexes of at least two chemical compounds, and fragments of such compounds.

The DPPIV structure coordinates provided herein are useful for screening and identifying drugs that inhibit DPPIV and other proteases. For example, the structure encoded by the data may be computationally evaluated for its ability to associate with putative substrates or ligands. Such compounds that associate with DPPIV may inhibit DPPIV, and are potential drug candidates. Additionally or alternatively, the structure encoded by the data may be displayed in a graphical three-dimensional representation on a computer screen. This allows visual inspection of the structure, as well as visual inspection of the structure's association with the compounds.

Thus, according to another embodiment of the present invention, a method is provided for evaluating the potential of an entity to associate with DPPIV or a fragment or variant thereof by using all or a portion of the structure coordinates provided in FIG. 3. A method is also provided for evaluating the potential of an entity to associate with DPPIV or a fragment or variant thereof by using structure coordinates similar to all or a portion of the structure coordinates provided in FIG. 3. For example, the structure coordinates used may have a root mean square deviation of alpha-carbon atoms of less than 3 Å when superimposed on the alpha-carbon atom positions of the corresponding atomic coordinates of FIG. 3.

It is again noted in regard to these embodiments that the root mean square deviation calculation may optionally be based on a comparison of main-chain atoms or non-hydrogen atoms. Also, the root mean square deviation of alpha-carbon atoms or non-hydrogen atoms may optionally be less than 2.7 Å, 2.5 Å, 2.0 Å, 1.5 Å, 1 Å, 0.5 Å, or less.

The method may optionally comprise the steps of: creating a computer model of all or a portion of a protein structure (e.g., a binding pocket) using structure coordinates according to the present invention; performing a fitting operation between the entity and the computer model; and analyzing the results of the fitting operation to quantify the association between the entity and the model. The portion of the protein structure used optionally comprises all of the amino acids listed in Tables 1, 2, 3 and/or 4 that are present in the structure coordinates being used.

It is noted that the computer model may not necessarily directly use the structure coordinates. Rather, a computer model can be formed that defines a surface contour that is the same or similar to the surface contour defined by the structure coordinates.

The structure coordinates provided herein can also be utilized in a method for identifying a ligand (e.g., entities capable of associating with a protein) of a protein comprising a DPPIV-like binding pocket. One embodiment of the method comprises: using all or a portion of the structure coordinates provided herein to generate a three-dimensional structure of a DPPIV-like binding pocket; employing the three-dimensional structure to design or select a potential ligand; synthesizing the potential ligand; and contacting the synthesized potential ligand with a protein comprising an DPPIV-like binding pocket to determine the ability of the potential ligand to interact with protein. According to this method, the structure coordinates used may have a root mean square deviation of alpha-carbon atoms of less than 3 Å when superimposed on the alpha-carbon atom positions of the corresponding atomic coordinates of FIG. 3. The portion of the protein structure used optionally comprises all of the amino acids listed in Tables 1, 2, 3 and/or 4 that are present.

As noted previously, the three-dimensional structure of a DPPIV-like binding pocket need not be generated directly from structure coordinates. Rather, a computer model can be formed that defines a surface contour that is the same or similar to the surface contour defined by the structure coordinates.

It is again noted that the root mean square deviation calculation may optionally be based on a comparison of main-chain or non-hydrogen atoms. Also, the root mean square deviation of alpha-carbon atoms or non-hydrogen atoms may optionally be less than 2.7 Å, 2.5 Å, 2.0 Å, 1.5 Å, 1 Å, 0.5 Å, or less.

A method is also provided for evaluating the ability of an entity, such as a compound or a protein to associate with a DPPIV-like binding pocket, the method comprising: constructing a computer model of a binding pocket defined by structure coordinates that have a root mean square deviation of less than 3.0 Å when compared to structure coordinates appearing in FIG. 3, the comparison being based on alpha-carbon atoms present in both sets of structure coordinates, the comparison also being limited to residues of DPPIV appearing in Tables 1, 2, 3 and/or 4 that are present; selecting an entity to be evaluated by a method selected from the group consisting of (i) assembling molecular fragments into the entity, (ii) selecting an entity from a small molecule database, (iii) de novo ligand design of the entity, and (iv) modifying a known ligand for DPPIV, or a portion thereof; performing a fitting program operation between computer models of the entity to be evaluated and the binding pocket in order to provide an energy-minimized configuration of the entity in the binding pocket; and evaluating the results of the fitting operation to quantify the association between the entity and the binding pocket model in order to evaluate the ability of the entity to associate with the said binding pocket.

The computer model of a binding pocket used in this embodiment need not be generated directly from structure coordinates. Rather, a computer model can be formed that defines a surface contour that is the same or similar to the surface contour defined by the structure coordinates.

According to the method, the root mean square deviation calculation may optionally be based on a comparison of main-chain atoms or non-hydrogen atoms. Also, the root mean square deviation of alpha-carbon atoms or non-hydrogen atoms may optionally be less than 2.7 Å, 2.5 Å, 2.0 Å, 1.5 Å, 1 Å, 0.5 Å, or less.

Also according to the method, the method may further include synthesizing the entity; and contacting a protein having a DPPIV-like binding pocket with the synthesized entity.

With the structure provided herein, the present invention for the first time permits the use of molecular design techniques to identify, select or design potential inhibitors of DPPIV, based on the structure of a DPPIV-like binding pocket. Such a predictive model is valuable in light of the high costs associated with the preparation and testing of the many diverse compounds that may possibly bind to the DPPIV protein.

According to this invention, a potential DPPIV inhibitor may now be evaluated for its ability to bind a DPPIV-like binding pocket prior to its actual synthesis and testing. If a proposed entity is predicted to have insufficient interaction or association with the binding pocket, preparation and testing of the entity can be obviated. However, if the computer modeling indicates a strong interaction, the entity may then be obtained and tested for its ability to bind.

A potential inhibitor of a DPPIV-like binding pocket may be computationally evaluated using a series of steps in which chemical entities or fragments are screened and selected for their ability to associate with the DPPIV-like binding pockets.

One skilled in the art may use one of several methods to screen entities (whether chemical or protein) for their ability to associate with a DPPIV-like binding pocket. This process may begin by visual inspection of, for example, a DPPIV-like binding pocket on a computer screen based on the DPPIV structure coordinates in FIG. 3 or other coordinates which define a similar shape generated from the machine-readable storage medium. Selected fragments or chemical entities may then be positioned in a variety of orientations, or docked, within that binding pocket as defined above. Docking may be accomplished using software such as Quanta and Sybyl, followed by energy minimization and molecular dynamics with standard molecular mechanics force fields, such as CHARMM and AMBER.

Specialized computer programs may also assist in the process of selecting entities. These include: GRID (P. J. Goodford, "A Computational Procedure for Determining Energetically Favorable Binding Sites on Biologically Important Macromolecules", J. Med. Chem., 28, pp. 849-857 (1985)). GRID is available from Oxford University, Oxford, UK; MCSS (A. Miranker et al., "Functionality Maps of Binding Sites: A Multiple Copy Simultaneous Search Method." Proteins: Structure, Function and Genetics, 11, pp. 29-34 (1991)). MCSS is available from Molecular Simulations, San Diego, Calif.; AUTODOCK (D. S. Goodsell et al., "Automated Docking of Substrates to Proteins by Simulated Annealing", Proteins: Structure, Function, and Genetics, 8, pp. 195-202 (1990)). AUTODOCK is available from Scripps Research Institute, La Jolla, Calif.; & DOCK (I. D. Kuntz et al., "A Geometric Approach to Macromolecule-Ligand Interactions", J. Mol. Biol., 161, pp. 269-288 (1982)). DOCK is available from University of California, San Francisco, Calif.

Once suitable entities have been selected, they can be designed or assembled. Assembly may be preceded by visual inspection of the relationship of the fragments to each other on the three-dimensional image displayed on a computer screen in relation to the structure coordinates of DPPIV. This may then be followed by manual model building using software such as Quanta or Sybyl [Tripos Associates, St. Louis, Mo].

Useful programs to aid one of skill in the art in connecting the individual chemical entities or fragments include: CAVEAT (P. A. Bartlett et al, "CAVEAT: A Program to Facilitate the Structure-Derived Design of Biologically Active Molecules", in "Molecular Recognition in Chemical and Biological Problems", Special Pub., Royal Chem. Soc., 78, pp. 182-196 (1989); G. Lauri and P. A. Bartlett, "CAVEAT: a Program to Facilitate the Design of Organic Molecules", J. Comput. Aided Mol. Des., 8, pp. 51-66 (1994)). CAVEAT is available from the University of California, Berkeley, Calif.; 3D Database systems such as ISIS (MDL Information Systems, San Leandro, Calif.). This area is reviewed in Y. C. Martin, "3D Database Searching in Drug Design", J. Med. Chem., 35, pp. 2145-2154 (1992); HOOK (M. B. Eisen et al, "HOOK; A Program for Finding Novel Molecular Architectures that Satisfy the Chemical and Steric Requirements of a Macromolecule Binding Site", Proteins: Struct., Funct., Genet., 19, pp. 199-221 (1994). HOOK is available from Molecular Simulations, San Diego, Calif.

Instead of proceeding to build an inhibitor of a DPPIV-like binding pocket in a step-wise fashion one fragment or entity at a time as described above, inhibitory or other DPPIV binding compounds may be designed as a whole or "de novo" using either an empty binding site or optionally including some portion(s) of a known inhibitor(s). There are many de novo ligand design methods including: LUDI (H.-J. Bohm, "The Computer Program LUDI: A New Method for the De Novo Design of Enzyme Inhibitors", J. Comp. Aid. Molec. Design, 6, pp. 61-78 (1992)). LUDI is available from Molecular Simulations Incorporated, San Diego, Calif.; LEGEND (Y. Nishibata et al., Tetrahedron, 47, p. 8985 (1991)). LEGEND is available from Molecular Simulations Incorporated, San Diego, Calif.; LEAPFROG (available from Tripos Associates, St. Louis, Mo.); & SPROUT (V. Gillet et al, "SPROUT: A Program for Structure Generation)", J. Comput. Aided Mol. Design, 7, pp. 127-153 (1993)). SPROUT is available from the University of Leeds, UK.

Other molecular modeling techniques may also be employed in accordance with this invention (see, e.g., Cohen et al., "Molecular Modeling Software and Methods for Medicinal Chemistry, J. Med. Chem., 33, pp. 883-894 (1990); see also, M. A. Navia and M. A. Murcko, "The Use of Structural Information in Drug Design", Current Opinions in Structural Biology, 2, pp. 202-210 (1992); L. M. Balbes et al., "A Perspective of Modern Methods in Computer-Aided Drug Design", in Reviews in Computational Chemistry, Vol. 5, K. B. Lipkowitz and D. B. Boyd, Eds., VCH, New York, pp. 337-380 (1994); see also, W. C. Guida, "Software For Structure-Based Drug Design", Curr. Opin. Struct. Biology, 4, pp. 777-781 (1994)).

Once an entity has been designed or selected, for example, by the above methods, the efficiency with which that entity may bind to a DPPIV binding pocket may be tested and optimized by computational evaluation. For example, an effective DPPIV binding pocket inhibitor preferably demonstrates a relatively small difference in energy between its bound and free states (i.e., a small deformation energy of binding). Thus, the most efficient DPPIV binding pocket inhibitors should preferably be designed with deformation energy of binding of not greater than about 10 kcal/mole, more preferably, not greater than 7 kcal/mole. DPPIV binding pocket inhibitors may interact with the binding pocket in more than one of multiple conformations that are similar in overall binding energy. In those cases, the deformation energy of binding is taken to be the difference between the energy of the free entity and the average energy of the conformations observed when the inhibitor binds to the protein.

An entity designed or selected as binding to a DPPIV binding pocket may be further computationally optimized so that in its bound state it would preferably lack repulsive electrostatic interaction with the target enzyme and with the surrounding water molecules. Such non-complementary electrostatic interactions include repulsive charge-charge, dipole-dipole and charge-dipole interactions.

Specific computer software is available in the art to evaluate compound deformation energy and electrostatic interactions. Examples of programs designed for such uses include: Gaussian 94, revision C (M. J. Frisch, Gaussian, Inc., Pittsburgh, Pa. .COPYRGT.1995); AMBER, version 4.1 (P. A. Kollman, University of California at San Francisco, COPYRGT 1995); QUANTA/CHARMM (Molecular Simulations, Inc., San Diego, Calif. COPYRGT.1995); Insight II/Discover (Molecular Simulations, Inc., San Diego, Calif. COPYRGT.1995); DelPhi (Molecular Simulations, Inc., San Diego, Calif. COPYRGT.1995); and AMSOL (Quantum Chemistry Program Exchange, Indiana University). These programs may be implemented, for instance, using a Silicon Graphics workstation such as an Indigo.sup.2 with "IMPACT" graphics. Other hardware systems and software packages will be known to those skilled in the art.

Another approach provided by this invention, is the computational screening of small molecule databases for chemical entities or compounds that can bind in whole, or in part, to a DPPIV binding pocket. In this screening, the quality of fit of such entities to the binding site may be judged either by shape complementarities or by estimated interaction energy [E. C. Meng et al., J. Comp. Chem., 13, 505-524 (1992)].

According to another embodiment, the invention provides compounds that associate with a DPPIV—like binding pocket produced or identified by various methods set forth above.

The structure coordinates set forth in FIG. 3 can also be used to aid in obtaining structural information about another crystallized molecule or molecular complex. This may be achieved by any of a number of well-known techniques, including molecular replacement.

For example, a method is also provided for utilizing molecular replacement to obtain structural information about a protein whose structure is unknown comprising the steps of: generating an X-ray diffraction pattern of a crystal of the protein whose structure is unknown; generating a three-dimensional electron density map of the protein whose structure is unknown from the X-ray diffraction pattern by using at least a portion of the structure coordinates set forth in FIG. 3 as a molecular replacement model.

By using molecular replacement, all or part of the structure coordinates of the DPPIV provided by this invention (and set forth in FIG. 3) can be used to determine the structure of another crystallized molecule or molecular complex more quickly and efficiently than attempting an ab initio structure determination. One particular use includes use with other S9 proteases. Molecular replacement provides an accurate estimation of the phases for an unknown structure. Phases are a factor in equations used to solve crystal structures that cannot be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure provide a satisfactory estimate of the phases for the unknown structure.

Thus, this method involves generating a preliminary model of a molecule or molecular complex whose structure coordinates are unknown, by orienting and positioning the relevant portion of DPPIV according to FIG. 3 within the unit cell of the crystal of the unknown molecule or molecular complex so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex [E. Lattman, "Use of the Rotation and Translation Functions", in Meth. Enzymol., 115, pp. 55-77 (1985); M. G. Rossmann, ed., "The Molecular Replacement Method", Int. Sci. Rev. Ser., No. 13, Gordon & Breach, New York (1972)].

The structure of any portion of any crystallized molecule or molecular complex that is sufficiently homologous to any portion of DPPIV can be resolved by this method.

In one embodiment, the method of molecular replacement is utilized to obtain structural information about the present invention and any other DPPIV-like molecule. The structure coordinates of DPPIV, as provided by this invention, are particularly useful in solving the structure of other isoforms of DPPIV or DPPIV complexes.

The structure coordinates of DPPIV as provided by this invention are useful in solving the structure of DPPIV variants that have amino acid substitutions, additions and/or deletions (referred to collectively as "DPPIV mutants", as compared to naturally occurring DPPIV). These DPPIV mutants may optionally be crystallized in co-complex with a ligand, such as an inhibitor, substrate analogue or a suicide substrate. The crystal structures of a series of such complexes may then be solved by molecular replacement and compared with that of DPPIV. Potential sites for modification within the various binding sites of the enzyme may thus be identified. This information provides an additional tool for determining the most efficient binding interactions such as, for example, increased hydrophobic interactions, between DPPIV and a ligand. It is noted that the ligand may be the protein's natural ligand or may be a potential agonist or antagonist of a protein.

All of the complexes referred to above may be studied using well-known X-ray diffraction techniques and may be refined versus 1.5-3 Å resolution X-ray data to an R value of about 0.22 or less using computer software, such as X-PLOR [Yale University, COPYRGT.1992, distributed by Molecular Simulations, Inc.; see, e.g., Blundell & Johnson, supra; Meth. Enzymol., Vol. 114 & 115, H. W. Wyckoff et al., eds., Academic Press (1985)]. This information may thus be used to optimize known DPPIV inhibitors, and more importantly, to design new DPPIV inhibitors.

The structure coordinates described above may also be used to derive the dihedral angles, phi and psi, that define the conformation of the amino acids in the protein backbone. As will be understood by those skilled in the art, the $phi_n$ angle refers to the rotation around the bond between the alpha-carbon and the nitrogen, and the $psi_n$ angle refers to the rotation around the bond between the carbonyl carbon and the alpha-carbon. The subscript "n" identifies the amino acid whose conformation is being described [for a general reference, see Blundell and Johnson, Protein Crystallography, Academic Press, London, 1976].

9. Uses of the Crystal and Diffraction Pattern of DPPIV

Crystals, crystallization conditions and the diffraction pattern of DPPIV that can be generated from the crystals also have a range of uses. One particular use relates to screening entities that are not known ligands of DPPIV for their ability to bind to DPPIV. For example, with the availability of crystallization conditions, crystals and diffraction patterns of DPPIV provided according to the present invention, it is possible to take a crystal of DPPIV; expose the crystal to one or more entities that may be a ligand of DPPIV; and determine whether a ligand/DPPIV complex is formed. The crystals of DPPIV may be exposed to potential ligands by various methods, including but not limited to, soaking a crystal in a solution of one or more potential ligands or co-crystallizing DPPIV in the presence of one or more potential ligands. Given the structure coordinates provided herein, once a ligand complex is formed, the structure coordinates can be used as a model in molecular replacement in order to determine the structure of the ligand complex.

Once one or more ligands are identified, structural information from the ligand/DPPIV complex(es) may be used to design new ligands that bind tighter, bind more specifically, have better biological activity or have better safety profile than known ligands.

In one embodiment, a method is provided for identifying a ligand that binds to DPPIV comprising: (a) attempting to crystallize a protein that comprises a sequence with 70, 80, 90, 95% or greater identity with SEQ. ID No. 1 in the presence of one or more entities; (b) if crystals of the protein are obtained in step (a), obtaining an X-ray diffraction pattern of the protein crystal; and (c) determining whether a ligand/protein complex was formed by comparing an X-ray diffraction pattern of a crystal of the protein formed in the absence of the one or more entities to the crystal formed in the presence of the one or more entities.

In another embodiment, a method is provided for identifying a ligand that binds to DPPIV comprising: soaking a crystal of a protein that comprises a sequence with 70, 80, 90, 95% or greater identity with SEQ. ID No. 1 with one or more entities; determining whether a ligand/protein complex was formed by comparing an X-ray diffraction pattern of a crystal of the protein that has not been soaked with the one or more entities to the crystal that has been soaked with the one or more entities.

Optionally, the method may further comprise converting the diffraction patterns into electron density maps using phases of the protein crystal and comparing the electron density maps.

Libraries of "shape-diverse" compounds may optionally be used to allow direct identification of the ligand-receptor complex even when the ligand is exposed as part of a mixture. According to this variation, the need for time-consuming de-convolution of a hit from the mixture is avoided. More specifically, the calculated electron density function reveals the binding event, identifies the bound compound and provides a detailed 3-D structure of the ligand-receptor complex. Once a hit is found, one may optionally also screen a number of analogs or derivatives of the hit for tighter binding or better biological activity by traditional screening methods. The hit and information about the structure of the target may also be used to develop analogs or derivatives with tighter binding or better biological activity. It is noted that the ligand-DPPIV complex may optionally be exposed to additional iterations of potential ligands so that two or more hits can be linked together to make a more potent ligand. Screening for potential ligands by co-crystallization and/or soaking is further described in U.S. Pat. No. 6,297,021, which is incorporated herein by reference.

EXAMPLES

Example 1

Expression and Purification of DPPIV

This example describes the expression of DPPIV. It should be noted that a variety of other expression systems and hosts are also suitable for the expression of DPPIV, as would be readily appreciated by one of skill in the art.

The portion of the gene encoding residues 39-766 (from SEQ. ID No. 1), which corresponds to the extracellular portion of human DPPIV, was isolated by PCR from spleen cDNA and cloned into the BamH I and Hind III sites of a modified pFastBacHTb vector. This vector encodes a baculovirus glycoprotein gp67 signal peptide sequence followed by a 6x-histidine tag sequence followed by the DPPIV sequence. Expression in this vector allowed for the production of secreted recombinant DPPIV with part of a gp67 signal sequence and a 6x-histidine tag, the sequence of which is shown in FIG. 1 (part of a gp67 signal sequence and 6x-histidine tag sequence underlined) (SEQ. ID No. 3).

Recombinant baculovirus genomic DNAs incorporating the DPPIV cDNA sequences were generated by transposition using the Bac-to-Bac system (Gibco-BRL). Infectious extracellular virus particles were obtained by transfection of a 2 ml adherent culture of *Spodoptera frugiperda* S Sf9 insect cells with the recombinant viral genomic DNA. Growth in ESF 921 protein free medium (Expression Systems) was for 3 days at 27° C. The resulting passage 1 viral supernatant was used to obtain passage 2 high titer viral stock (HTS) by infection of a 2 ml adherent culture of *Spodoptera frugiperda* Sf9 insect cells grown under similar conditions. Passage 2 HTS was used in turn to infect a 100 ml suspension culture of *Spodoptera frugiperda* Sf9 insect cells in order to generate passage 3 HTS. The production of recombinant DPPIV proteins was carried out by using the passage 3 HTS at a multiplicity of infection (MOI) of approximately 5 to infect 0.5-5 liter cultures of *Trichoplusia ni* Hi5 insect cells (InVitrogen) at a cell density of (1,5–8)× $10^6$ cells/ml (grown in ESF 921 protein free medium). Infected cell cultures were grown in both shake flasks and in Wave Bioreactors (Wave Biotech) for 48 hours at 27° C. prior to harvest. In some instances infected cultures of *Spodoptera frugiperda* Sf9 insect cells were used to produce recombinant DPPIV under similar conditions. Following harvest, the cell cultures were centrifuged to pellet whole cells.

The secreted glycosylated recombinant protein was isolated from the cell culture medium by diafiltration using cross-flow ultrafiltration, followed by passage over a nickel chelate resin and optionally polished by size exclusion chromatography.

In a typical batch prep, 5 L of cell culture supernatant was concentrated to 0.1 L on a 10 kDa NMWCO Omega Ultrasette (Pall Life Sciences) using a Masterflex L/S pump fitted with PharMed #15 tubing at a cross flow of approximately 1 L/minute and an inlet feed pressure of 1.5 to 2.0 bar, generating an initial permeate flow of up to 70 ml/minute. The retentate was diluted two to three fold by adding 25 mM Tris/HCl pH 7.9, 0.4 M NaCl and reconcentrated to 0.1 L. This process was repeated at least twice, after which the concentrate was quantitatively removed from the system, centrifuged when necessary (15 minutes at 4000 rpm in an Allegra (Beckman) centrifuge) and added to approximately 8 ml of a preconditioned 50% slurry of Probond (Invitrogen) divided over three or four 50 ml conical tubes. The tubes were rotated for at least 1 hour, after which the resin was washed with 10 resin volumes of 50 mM Potassium Phosphate pH 7.9, 0.4 M NaCl, 0.25 mM Tris (2-carboxyethyl)phosphine hydrochloride (TCEP). The resin is poured into 1 cm ID glass columns (Omnifit) and washed with 50 column volumes of 50 mM Potassium Phosphate pH 7.9, 0.4 M NaCl, 20 mM imidazole, 0.25 mM TCEP. After a wash with 5 column volumes of 50 mM Tris pH 7.9, 0.4 M NaCl, 0.25 mM TCEP, the product is eluted with 4 column volumes of 50 mM Tris pH 7.9, 0.4 M NaCl, 200 mM imidazole, 0.25 mM TCEP.

It is noted that the polyhistidine tags may optionally be removed; however in this instance, the polyhistidine tag was left as a fusion. It is also noted that for the purification of non-secreted proteins, leupeptin is added to all the buffers used during the immobilized metal affinity purification (IMAC) process at 1 mg/L and that for simplicity reasons the same is sometimes done when purifying DPPIV.

After concentrating to 7.5 mg/ml or higher by centrifugal ultrafiltration (10 kDa NMWCO, VivaScience), DPPIV was purified over a BioSep Sec S3000 column (200 mm×21.2 mm, Phenomenex) at 8 ml/minute to remove oligomeric forms. The column was set up in a Summit HPLC system (Dionex) managed by Chromeleon software (Dionex) and equilibrated with 25 mM Tris pH 7.6, 150 to 250 mM NaCl (optionally with 0.25 mM TCEP and 1 mM EDTA). In cases when the size exclusion step was omitted, centrifugal ultrafiltration (10 kDa NMWCO) was used for the buffer exchange to the required formulation buffer. The process was carried out at 2-10° C. and DPPIV was stored at the same temperature. For long-term storage, it was kept at −80° C. The purity of DPPIV was estimated by SDS-PAGE and IEF to be at least 95%. Glycosylation was confirmed by a molecular mass shift, determined by SDS-PAGE, following treatment with endo-beta-N acetyl glucosaminidases F (Endo-F1 enzyme), and by carbohydrate analysis.

DPPIV with seleno-L-methionine substitution was prepared as follows: two 5 liter Wave Bioreactor cultures of *Trichoplusia ni* Hi5 insect cells in ESF 921 Protein Free medium were infected and grown for 16 hours at 27° C. At that time the cells were pelleted by centrifugation at 480 g and 20° C. for 15 minutes. The supernatant was discarded and the cells resuspended in 2×5 liters of ESF 921 Protein Free Methionine-Free medium (Expression Systems). The resuspended cells were placed in two new 5 liter Wave Bioreactors and growth continued for 4 h at 27° C. Seleno-L-methionine (prepared as a 25 mg/ml solution in water and sterile-filtered) was then added to each culture to a final concentration of 50 mg/l. Cell growth was continued for a further 48 h prior to harvest. Purification of the protein was as described above and included the size exclusion chromatography step. Mass spectrogram peptide analysis was used to estimate the seleno-L-methionine substitution of methionine residues at approximately 34%.

Example 2

Crystallization of DPPIV

This example describes the crystallization of DPPIV (SEQ ID NO:3). It is noted that the precise crystallization conditions used may be further varied, for example by performing a fine screen based on these crystallization conditions.

Crystals were obtained after an extensive and broad screen of conditions, followed by optimization. Diffraction quality crystals were grown in 100 nL sitting droplets using the vapor diffusion method. 50 nL comprising the apo DPPIV complex (SEQ ID NO:3) (between 8 and 30 mg/ml) was mixed with 50 nL from a reservoir solution (100 µL) comprising: 0.1M Tris-HCl, pH=7.5; 27% MPEG 2000; and 0.35M sarcosine/10% xylitrol. The resulting solution was incubated over a period of two weeks at 4° C.

Crystals typically appeared after 3-5 days and grew to a maximum size within 7-10 days. Single crystals were transferred, briefly, into a cryoprotecting solution containing the reservoir solution supplemented with 25% v/v ethylene glycol. Crystals were then flash frozen by immersion in liquid nitrogen and then stored under liquid nitrogen. A crystal of apo DPPIV (SEQ ID NO:3) produced as described is illustrated in FIG. 2.

While the present invention is disclosed with reference to certain embodiments and examples detailed above, it is to be understood that these embodiments and examples are intended to be illustrative rather than limiting, as it is contemplated that modifications will readily occur to those skilled in the art, which modifications are intended to be within the scope of the invention and the appended claims. All patents, papers, and books cited in this application are incorporated herein in their entirety.

SEQUENCE LISTING

```
<160> NUMBER OF SEQ ID NOS: 3

<210> SEQ ID NO 1
<211> LENGTH: 766
<212> TYPE: PRT
<213> ORGANISM: Homo sapiens
<220> FEATURE:
<221> NAME/KEY: Amino acid sequence for full-length human wild type
      DPPIV
<222> LOCATION: (1)..(766)
<300> PUBLICATION INFORMATION:
<308> DATABASE ACCESSION NUMBER: Genbank/NP_001926
<309> DATABASE ENTRY DATE: 2002-02-19
<313> RELEVANT RESIDUES: (1)..(766)

<400> SEQUENCE: 1

Met Lys Thr Pro Trp Lys Val Leu Leu Gly Leu Leu Gly Ala Ala Ala
1               5                   10                  15

Leu Val Thr Ile Ile Thr Val Pro Val Val Leu Leu Asn Lys Gly Thr
            20                  25                  30

Asp Asp Ala Thr Ala Asp Ser Arg Lys Thr Tyr Thr Leu Thr Asp Tyr
        35                  40                  45

Leu Lys Asn Thr Tyr Arg Leu Lys Leu Tyr Ser Leu Arg Trp Ile Ser
    50                  55                  60

Asp His Glu Tyr Leu Tyr Lys Gln Glu Asn Asn Ile Leu Val Phe Asn
65                  70                  75                  80

Ala Glu Tyr Gly Asn Ser Ser Val Phe Leu Glu Asn Ser Thr Phe Asp
                85                  90                  95

Glu Phe Gly His Ser Ile Asn Asp Tyr Ser Ile Ser Pro Asp Gly Gln
            100                 105                 110

Phe Ile Leu Leu Glu Tyr Asn Tyr Val Lys Gln Trp Arg His Ser Tyr
        115                 120                 125

Thr Ala Ser Tyr Asp Ile Tyr Asp Leu Asn Lys Arg Gln Leu Ile Thr
    130                 135                 140

Glu Glu Arg Ile Pro Asn Asn Thr Gln Trp Val Thr Trp Ser Pro Val
145                 150                 155                 160

Gly His Lys Leu Ala Tyr Val Trp Asn Asn Asp Ile Tyr Val Lys Ile
                165                 170                 175
```

-continued

Glu Pro Asn Leu Pro Ser Tyr Arg Ile Thr Trp Thr Gly Lys Glu Asp
                180                 185                 190

Ile Ile Tyr Asn Gly Ile Thr Asp Trp Val Tyr Glu Glu Val Phe
            195                 200                 205

Ser Ala Tyr Ser Ala Leu Trp Trp Ser Pro Asn Gly Thr Phe Leu Ala
        210                 215                 220

Tyr Ala Gln Phe Asn Asp Thr Glu Val Pro Leu Ile Glu Tyr Ser Phe
225                 230                 235                 240

Tyr Ser Asp Glu Ser Leu Gln Tyr Pro Lys Thr Val Arg Val Pro Tyr
                245                 250                 255

Pro Lys Ala Gly Ala Val Asn Pro Thr Val Lys Phe Phe Val Val Asn
                260                 265                 270

Thr Asp Ser Leu Ser Ser Val Thr Asn Ala Thr Ser Ile Gln Ile Thr
            275                 280                 285

Ala Pro Ala Ser Met Leu Ile Gly Asp His Tyr Leu Cys Asp Val Thr
        290                 295                 300

Trp Ala Thr Gln Glu Arg Ile Ser Leu Gln Trp Leu Arg Arg Ile Gln
305                 310                 315                 320

Asn Tyr Ser Val Met Asp Ile Cys Asp Tyr Asp Glu Ser Ser Gly Arg
                325                 330                 335

Trp Asn Cys Leu Val Ala Arg Gln His Ile Glu Met Ser Thr Thr Gly
                340                 345                 350

Trp Val Gly Arg Phe Arg Pro Ser Glu Pro His Phe Thr Leu Asp Gly
            355                 360                 365

Asn Ser Phe Tyr Lys Ile Ile Ser Asn Glu Glu Gly Tyr Arg His Ile
        370                 375                 380

Cys Tyr Phe Gln Ile Asp Lys Lys Asp Cys Thr Phe Ile Thr Lys Gly
385                 390                 395                 400

Thr Trp Glu Val Ile Gly Ile Glu Ala Leu Thr Ser Asp Tyr Leu Tyr
                405                 410                 415

Tyr Ile Ser Asn Glu Tyr Lys Gly Met Pro Gly Gly Arg Asn Leu Tyr
                420                 425                 430

Lys Ile Gln Leu Ser Asp Tyr Thr Lys Val Thr Cys Leu Ser Cys Glu
            435                 440                 445

Leu Asn Pro Glu Arg Cys Gln Tyr Tyr Ser Val Ser Phe Ser Lys Glu
        450                 455                 460

Ala Lys Tyr Tyr Gln Leu Arg Cys Ser Gly Pro Gly Leu Pro Leu Tyr
465                 470                 475                 480

Thr Leu His Ser Ser Val Asn Asp Lys Gly Leu Arg Val Leu Glu Asp
                485                 490                 495

Asn Ser Ala Leu Asp Lys Met Leu Gln Asn Val Gln Met Pro Ser Lys
            500                 505                 510

Lys Leu Asp Phe Ile Ile Leu Asn Glu Thr Lys Phe Trp Tyr Gln Met
        515                 520                 525

Ile Leu Pro Pro His Phe Asp Lys Ser Lys Tyr Pro Leu Leu Leu
530                 535                 540

Asp Val Tyr Ala Gly Pro Cys Ser Gln Lys Ala Asp Thr Val Phe Arg
545                 550                 555                 560

Leu Asn Trp Ala Thr Tyr Leu Ala Ser Thr Glu Asn Ile Ile Val Ala
                565                 570                 575

Ser Phe Asp Gly Arg Gly Ser Gly Tyr Gln Gly Asp Lys Ile Met His
            580                 585                 590

-continued

```
Ala Ile Asn Arg Arg Leu Gly Thr Phe Glu Val Glu Asp Gln Ile Glu
        595                 600                 605

Ala Ala Arg Gln Phe Ser Lys Met Gly Phe Val Asp Asn Lys Arg Ile
    610                 615                 620

Ala Ile Trp Gly Trp Ser Tyr Gly Gly Tyr Val Thr Ser Met Val Leu
625                 630                 635                 640

Gly Ser Gly Ser Gly Val Phe Lys Cys Gly Ile Ala Val Ala Pro Val
                645                 650                 655

Ser Arg Trp Glu Tyr Tyr Asp Ser Val Tyr Thr Glu Arg Tyr Met Gly
            660                 665                 670

Leu Pro Thr Pro Glu Asp Asn Leu Asp His Tyr Arg Asn Ser Thr Val
        675                 680                 685

Met Ser Arg Ala Glu Asn Phe Lys Gln Val Glu Tyr Leu Leu Ile His
    690                 695                 700

Gly Thr Ala Asp Asp Asn Val His Phe Gln Gln Ser Ala Gln Ile Ser
705                 710                 715                 720

Lys Ala Leu Val Asp Val Gly Val Asp Phe Gln Ala Met Trp Tyr Thr
                725                 730                 735

Asp Glu Asp His Gly Ile Ala Ser Ser Thr Ala His Gln His Ile Tyr
            740                 745                 750

Thr His Met Ser His Phe Ile Lys Gln Cys Phe Ser Leu Pro
        755                 760                 765
```

<210> SEQ ID NO 2
<211> LENGTH: 2184
<212> TYPE: DNA
<213> ORGANISM: Homo sapiens
<220> FEATURE:
<221> NAME/KEY: Human cDNA sequence encoding residues 39-766 of DPPIV
<222> LOCATION: (1)..(2184)

<400> SEQUENCE: 2

```
agtcgcaaaa cttacactct aactgattac ttaaaaaata cttatagact gaagttatac      60
tccttaagat ggatttcaga tcatgaatat ctctacaaac aagaaaataa tatcttggta     120
ttcaatgctg aatatggaaa cagctcagtt ttcttggaga acagtacatt tgatgagttt     180
ggacattcta tcaatgatta ttcaatatct cctgatgggc agtttattct cttagaatac     240
aactacgtga agcaatggag gcattcctac acagcttcat atgacattta tgatttaaat     300
aaaaggcagc tgattacaga agagaggatt ccaaacaaca cacagtgggt cacatggtca     360
ccagtgggtc ataaattggc atatgtttgg aacaatgaca tttatgttaa aattgaacca     420
aatttaccaa gttacagaat cacatggacg gggaaagaag atataatata taatggaata     480
actgactggg tttatgaaga ggaagtcttc agtgcctact ctgctctgtg gtggtctcca     540
aacggcactt ttttagcata tgcccaattt aacgacacag aagtcccact tattgaatac     600
tccttctact ctgatgagtc actgcagtac ccaaagacta cgggttcc atatccaaag      660 gcaggagctg tgaatccaac tgtaaagttc tttgttgtaa atacagactc tctcagctca     720
gtcaccaatg caacttccat acaaatcact gctcctgctt ctatgttgat agggatcac     780 tacttgtgtg atgtgacatg gcaacacaa gaaagaattt cttgcagtg gctcaggagg      840 attcagaact attcggtcat ggatatttgt gactatgatg aatccagtgg aagatggaac     900
tgcttagtgg cacggcaaca cattgaaatg agtactactg ctgggttgg aagatttagg     960 ccttcagaac ctcattttac ccttgatggt aatagcttct acaagatcat cagcaatgaa    1020
gaaggttaca gacacatttg ctatttccaa atagataaaa aagactgcac atttattaca    1080
```

-continued

```
aaaggcacct gggaagtcat cgggatagaa gctctaacca gtgattatct atactacatt    1140
agtaatgaat ataaggaat gccaggagga aggaatcttt ataaaatcca acttattgac     1200
tatacaaaag tgacatgcct cagttgtgag ctgaatccgg aaaggtgtca gtactattct    1260
gtgtcattca gtaaagaggc gaagtattat cagctgagat gttccggtcc tggtctgccc    1320
ctctatactc tacacagcag cgtgaatgat aaagggctga gagtcctgga agacaattca    1380
gctttggata aatgctgca gaatgtccag atgccctcca aaaaactgga cttcattatt     1440
ttgaatgaaa caaatttttg gtatcagatg atcttgcctc ctcattttga taaatccaag    1500
aaatatcctc tactattaga tgtgtatgca ggcccatgta gtcaaaaagc agacactgtc    1560
ttcagactga actgggccac ttaccttgca agcacagaaa acattatagt agctagcttt    1620
gatggcagag gaagtggtta ccaaggagat aagatcatgc atgcaatcaa cagaagactg    1680
ggaacatttg aagttgaaga tcaaattgaa gcagccagac aattttcaaa aatgggattt    1740
gtggacaaca aacgaattgc aatttgggc tggtcatatg gagggtacgt aacctcaatg     1800
gtcctgggat cgggaagtgg cgtgttcaag tgtggaatag ccgtggcgcc tgtatcccgg    1860
tgggagtact atgactcagt gtacacagaa cgttacatgg gtctcccaac tccagaagac    1920
aaccttgacc attacagaaa ttcaacagtc atgagcagag ctgaaaattt taaacaagtt    1980
gagtacctcc ttattcatgg aacagcagat gataacgttc actttcagca gtcagctcag    2040
atctccaaag ccctggtcga tgttggagtg gatttccagg caatgtggta tactgatgaa    2100
gaccatggaa tagctagcag cacagcacac caacatatat atacccacat gagccacttc    2160
ataaaacaat gtttctcttt acct                                          2184
```

<210> SEQ ID NO 3
<211> LENGTH: 740
<212> TYPE: PRT
<213> ORGANISM: Homo sapiens
<220> FEATURE:
<221> NAME/KEY: N-terminal tag including a partial gp67 signal sequence
      and 6x-histidine
<222> LOCATION: (1)..(12)
<220> FEATURE:
<221> NAME/KEY: Amino acid sequence for residues 39-766 of DPPIV with an
      N-terminal tag
<222> LOCATION: (13)..(740)

<400> SEQUENCE: 3

Ala Asp Pro Gly Gly Ser His His His His His His Ser Arg Lys Thr
1               5                   10                  15

Tyr Thr Leu Thr Asp Tyr Leu Lys Asn Thr Tyr Arg Leu Lys Leu Tyr
                20                  25                  30

Ser Leu Arg Trp Ile Ser Asp His Glu Tyr Leu Tyr Lys Gln Glu Asn
            35                  40                  45

Asn Ile Leu Val Phe Asn Ala Glu Tyr Gly Asn Ser Ser Val Phe Leu
        50                  55                  60

Glu Asn Ser Thr Phe Asp Glu Phe Gly His Ser Ile Asn Asp Tyr Ser
65                  70                  75                  80

Ile Ser Pro Asp Gly Gln Phe Ile Leu Leu Glu Tyr Asn Tyr Val Lys
                85                  90                  95

Gln Trp Arg His Ser Tyr Thr Ala Ser Tyr Asp Ile Tyr Asp Leu Asn
            100                 105                 110

Lys Arg Gln Leu Ile Thr Glu Glu Arg Ile Pro Asn Asn Thr Gln Trp
        115                 120                 125

-continued

Val Thr Trp Ser Pro Val Gly His Lys Leu Ala Tyr Val Trp Asn Asn
130             135             140

Asp Ile Tyr Val Lys Ile Glu Pro Asn Leu Pro Ser Tyr Arg Ile Thr
145             150             155             160

Trp Thr Gly Lys Glu Asp Ile Ile Tyr Asn Gly Ile Thr Asp Trp Val
                165             170             175

Tyr Glu Glu Glu Val Phe Ser Ala Tyr Ser Ala Leu Trp Trp Ser Pro
                180             185             190

Asn Gly Thr Phe Leu Ala Tyr Ala Gln Phe Asn Asp Thr Glu Val Pro
            195             200             205

Leu Ile Glu Tyr Ser Phe Tyr Ser Asp Glu Ser Leu Gln Tyr Pro Lys
210             215             220

Thr Val Arg Val Pro Tyr Pro Lys Ala Gly Ala Val Asn Pro Thr Val
225             230             235             240

Lys Phe Phe Val Val Asn Thr Asp Ser Leu Ser Ser Val Thr Asn Ala
                245             250             255

Thr Ser Ile Gln Ile Thr Ala Pro Ala Ser Met Leu Ile Gly Asp His
            260             265             270

Tyr Leu Cys Asp Val Thr Trp Ala Thr Gln Glu Arg Ile Ser Leu Gln
        275             280             285

Trp Leu Arg Arg Ile Gln Asn Tyr Ser Val Met Asp Ile Cys Asp Tyr
290             295             300

Asp Glu Ser Ser Gly Arg Trp Asn Cys Leu Val Ala Arg Gln His Ile
305             310             315             320

Glu Met Ser Thr Thr Gly Trp Val Gly Arg Phe Arg Pro Ser Glu Pro
                325             330             335

His Phe Thr Leu Asp Gly Asn Ser Phe Tyr Lys Ile Ile Ser Asn Glu
            340             345             350

Glu Gly Tyr Arg His Ile Cys Tyr Phe Gln Ile Asp Lys Lys Asp Cys
        355             360             365

Thr Phe Ile Thr Lys Gly Thr Trp Glu Val Ile Gly Ile Glu Ala Leu
370             375             380

Thr Ser Asp Tyr Leu Tyr Tyr Ile Ser Asn Glu Tyr Lys Gly Met Pro
385             390             395             400

Gly Gly Arg Asn Leu Tyr Lys Ile Gln Leu Ser Asp Tyr Thr Lys Val
                405             410             415

Thr Cys Leu Ser Cys Glu Leu Asn Pro Glu Arg Cys Gln Tyr Tyr Ser
            420             425             430

Val Ser Phe Ser Lys Glu Ala Lys Tyr Tyr Gln Leu Arg Cys Ser Gly
        435             440             445

Pro Gly Leu Pro Leu Tyr Thr Leu His Ser Ser Val Asn Asp Lys Gly
450             455             460

Leu Arg Val Leu Glu Asp Asn Ser Ala Leu Asp Lys Met Leu Gln Asn
465             470             475             480

Val Gln Met Pro Ser Lys Lys Leu Asp Phe Ile Ile Leu Asn Glu Thr
                485             490             495

Lys Phe Trp Tyr Gln Met Ile Leu Pro Pro His Phe Asp Lys Ser Lys
            500             505             510

Lys Tyr Pro Leu Leu Leu Asp Val Tyr Ala Gly Pro Cys Ser Gln Lys
        515             520             525

Ala Asp Thr Val Phe Arg Leu Asn Trp Ala Thr Tyr Leu Ala Ser Thr
530             535             540

Glu Asn Ile Ile Val Ala Ser Phe Asp Gly Arg Gly Ser Gly Tyr Gln

-continued

```
         545                 550                 555                 560
Gly Asp Lys Ile Met His Ala Ile Asn Arg Arg Leu Gly Thr Phe Glu
                565                 570                 575
Val Glu Asp Gln Ile Glu Ala Ala Arg Gln Phe Ser Lys Met Gly Phe
            580                 585                 590
Val Asp Asn Lys Arg Ile Ala Ile Trp Gly Trp Ser Tyr Gly Gly Tyr
        595                 600                 605
Val Thr Ser Met Val Leu Gly Ser Gly Ser Gly Val Phe Lys Cys Gly
        610                 615                 620
Ile Ala Val Ala Pro Val Ser Arg Trp Glu Tyr Tyr Asp Ser Val Tyr
625                 630                 635                 640
Thr Glu Arg Tyr Met Gly Leu Pro Thr Pro Glu Asp Asn Leu Asp His
                645                 650                 655
Tyr Arg Asn Ser Thr Val Met Ser Arg Ala Glu Asn Phe Lys Gln Val
                660                 665                 670
Glu Tyr Leu Leu Ile His Gly Thr Ala Asp Asp Asn Val His Phe Gln
            675                 680                 685
Gln Ser Ala Gln Ile Ser Lys Ala Leu Val Asp Val Gly Val Asp Phe
        690                 695                 700
Gln Ala Met Trp Tyr Thr Asp Glu Asp His Gly Ile Ala Ser Ser Thr
705                 710                 715                 720
Ala His Gln His Ile Tyr Thr His Met Ser His Phe Ile Lys Gln Cys
                725                 730                 735
Phe Ser Leu Pro
            740
```

We claim:

1. A composition comprising a protein in crystalline form, wherein the protein consists of SEQ ID NO:3, and wherein the protein crystal has a crystal lattice in a P2$_1$ space group and unit cell dimensions, +/−5%, of a=121.53 Å b=124.11 Å and c=144.42 Å, α=γ=90°, β=114.6°.

2. A composition according to claim 1 wherein the protein crystal diffracts X-rays for a determination of structure coordinates to a resolution less than 3.0 Angstroms.

3. A method for forming a crystal of a protein comprising:
   forming a crystallization volume comprising a precipitant solution and a protein that consists of SEQ ID NO:3, and wherein the protein crystal has a crystal lattice in a P2$_1$ space group and unit cell dimensions, +/−5%, of a=121.53 Å b=124.11 Å and c=144.42 Å, α=γ=90°, β=114.6°; and
   storing the crystallization volume under conditions suitable for crystal formation of the protein.

4. A method according to claim 3 wherein is expressed from a nucleic acid molecule that comprises SEQ ID NO:2.

5. A method according to claim 3 wherein the protein crystal diffracts X-rays for a determination of structure coordinates to a resolution less than 3.0 Angstroms.

6. A non-crystalline protein consisting of SEQ ID NO:3.

7. A protein according to claim 6 where the protein is expressed from a nucleic acid molecule that comprises SEQ ID NO:2.

8. A non-crystalline protein consisting of residues 39-766 of SEQ ID NO. 1.

9. The protein according to claim 8 wherein the protein is expressed from a nucleic acid molecule that consists of SEQ ID NO:2.

10. An isolated non-crystalline protein consisting of residues 39-766 of SEQ ID NO:1.

11. An isolated non-crystalline protein consisting of SEQ ID NO:3.

12. A method of obtaining the three-dimensional structure of the protein of SEQ ID NO: 3:
   (a) Crystallize a protein consisting of SEQ ID NO: 3 to obtain a protein crystal having a crystal lattice in a P2$_1$ space group and unit cell dimensions, +/−5%, of a=121.53 Å, b=124.11 Å, and c=144.42 Å, α=γ=90°, and β=114.6;
   (b) Use the crystal of (a) to obtain an X-ray diffraction pattern; and
   (c) Solve the three-dimensional structure of the protein from the diffraction pattern, and thereby obtain the three-dimensional structure.

* * * * *